United States Patent
Crew et al.

(10) Patent No.: US 10,723,717 B2
(45) Date of Patent: Jul. 28, 2020

(54) COMPOUNDS AND METHODS FOR THE TARGETED DEGRADATION OF RAPIDLY ACCELERATED FIBROSARCOMA POLYPEPTIDES

(71) Applicants: Arvinas, Inc., New Haven, CT (US); Yale University, New Haven, CT (US)

(72) Inventors: Andrew P. Crew, Guilford, CT (US); Keith R. Hornberger, Southbury, CT (US); Jing Wang, Milford, CT (US); Hanqing Dong, Madison, CT (US); Yimin Qian, Plainsboro, NJ (US); Craig M. Crews, New Haven, CT (US); Saul Jaime-Figueroa, Morris Plains, NJ (US)

(73) Assignees: ARVINAS OPERATIONS, INC., New Haven, CT (US); YALE UNIVERSITY, New Haven, CT (US)

( * ) Notice: Subject to any disclaimer, the term of this patent is extended or adjusted under 35 U.S.C. 154(b) by 0 days.

(21) Appl. No.: 15/853,166

(22) Filed: Dec. 22, 2017

(65) Prior Publication Data
US 2018/0179183 A1 Jun. 28, 2018

Related U.S. Application Data

(60) Provisional application No. 62/582,698, filed on Nov. 7, 2017, provisional application No. 62/438,803, filed on Dec. 23, 2016.

(51) Int. Cl.

| | |
|---|---|
| *C07D 519/00* | (2006.01) |
| *C07D 401/14* | (2006.01) |
| *C07D 401/04* | (2006.01) |
| *A61K 31/4439* | (2006.01) |
| *C07D 417/14* | (2006.01) |
| *A61K 31/4545* | (2006.01) |
| *C07D 487/04* | (2006.01) |
| *A61P 9/00* | (2006.01) |
| *C07D 471/04* | (2006.01) |
| *A61K 31/437* | (2006.01) |
| *A61K 45/06* | (2006.01) |
| *A61P 35/00* | (2006.01) |
| *A61P 43/00* | (2006.01) |
| *A61P 25/00* | (2006.01) |
| *A61K 31/4188* | (2006.01) |
| *A61K 47/54* | (2017.01) |
| *A61K 47/55* | (2017.01) |

(52) U.S. Cl.
CPC ........ *C07D 401/14* (2013.01); *A61K 31/4188* (2013.01); *A61K 31/437* (2013.01); *A61K 31/4439* (2013.01); *A61K 31/4545* (2013.01); *A61K 45/06* (2013.01); *A61K 47/55* (2017.08); *A61K 47/555* (2017.08); *A61P 9/00* (2018.01); *A61P 25/00* (2018.01); *A61P 35/00* (2018.01); *A61P 43/00* (2018.01); *C07D 401/04* (2013.01); *C07D 417/14* (2013.01); *C07D 471/04* (2013.01); *C07D 487/04* (2013.01)

(58) Field of Classification Search
CPC .................................................... C07D 519/00
See application file for complete search history.

(56) References Cited

U.S. PATENT DOCUMENTS

| | | | |
|---|---|---|---|
| 6,268,391 B1 | 7/2001 | Dickerson et al. |
| 6,306,663 B1 | 10/2001 | Kenten et al. |
| 6,670,348 B1 | 12/2003 | Rosen et al. |
| 7,030,141 B2 | 4/2006 | Bigge et al. |
| 7,041,298 B2 | 5/2006 | Deshaies et al. |
| 7,208,157 B2 | 4/2007 | Sakamoto et al. |
| 7,244,851 B2 | 7/2007 | Cohen et al. |
| 7,345,081 B2 | 3/2008 | Cohen et al. |
| 7,419,975 B2 | 9/2008 | Palermo et al. |

(Continued)

FOREIGN PATENT DOCUMENTS

| | | |
|---|---|---|
| CN | 1844118 A | 10/2006 |
| CN | 103688176 A | 3/2014 |

(Continued)

OTHER PUBLICATIONS

Grasso et al. (ACS Chemical Biology (2016), 11(10), 2876-2888).*
Ahn, et al., "HIF-1alpha peptide derivatives with modifications at the hydroxyproline residue as activators of HIF-1alpha", Bioorg Med Chem Lett. 19(15), 2009, 4403-4405.
Ardecky, Rj, et al., "Design, synthesis and evaluation of inhibitor of apoptosis protein (IAP) antagonists that are highly selective for the BIR2 domain of XIAP", Bioorg. Med. Chem., 23(14): 4253-4257 (2013).

(Continued)

*Primary Examiner* — Bruck Kifle
(74) *Attorney, Agent, or Firm* — Bryan D. Zerhusen, Esq.; Nicholas R. Herrel, Esq.; Cantor Colburn LLP

(57) ABSTRACT

The present disclosure relates to bifunctional compounds, which find utility as modulators of Rapidly Accelerated Fibrosarcoma (RAF, such as c-RAF, A-RAF and/or B-RAF; the target protein). In particular, the present disclosure is directed to bifunctional compounds, which contain on one end a Von Hippel-Lindau, cereblon, Inhibitors of Apotosis Proteins or mouse double-minute homolog 2 ligand which binds to the respective E3 ubiquitin ligase and on the other end a moiety which binds the target protein RAF, such that the target protein is placed in proximity to the ubiquitin ligase to effect degradation (and inhibition) of target protein. The present disclosure exhibits a broad range of pharmacological activities associated with degradation/inhibition of target protein. Diseases or disorders that result from aggregation or accumulation of the target protein, or the constitutive activation of the target protein, are treated or prevented with compounds and compositions of the present disclosure.

44 Claims, 113 Drawing Sheets

(56) References Cited

U.S. PATENT DOCUMENTS

| | | | |
|---|---|---|---|
| 7,517,906 | B2 | 4/2009 | Condon et al. |
| 7,915,293 | B2 | 3/2011 | Ramesh |
| 9,500,653 | B2 | 11/2016 | Crews et al. |
| 9,632,089 | B2 | 4/2017 | Crews et al. |
| 2006/0128632 | A1 | 6/2006 | Sharma et al. |
| 2008/0051432 | A1 | 2/2008 | Zhang |
| 2008/0214501 | A1 | 9/2008 | Pan et al. |
| 2008/0269140 | A1 | 10/2008 | Wang et al. |
| 2010/0203012 | A1 | 8/2010 | Laurent et al. |
| 2011/0195043 | A1 | 8/2011 | Sun et al. |
| 2012/0270800 | A1 | 10/2012 | Verdine et al. |
| 2013/0029993 | A1 | 1/2013 | Stadtmueller |
| 2014/0088143 | A1 | 3/2014 | Jain |
| 2014/0235629 | A1 | 8/2014 | Bartberger et al. |
| 2014/0243372 | A1 | 8/2014 | Rew |
| 2014/0302523 | A1 | 10/2014 | Crews et al. |
| 2014/0356322 | A1 | 12/2014 | Crews et al. |
| 2015/0119435 | A1 | 4/2015 | Crews et al. |
| 2015/0141470 | A1 | 5/2015 | Garraway et al. |
| 2015/0259288 | A1 | 9/2015 | Nam et al. |
| 2015/0291562 | A1 | 10/2015 | Crew et al. |
| 2015/0344473 | A1 | 10/2015 | Du et al. |
| 2016/0022642 | A1 | 1/2016 | Crews et al. |
| 2016/0045607 | A1 | 2/2016 | Crew et al. |
| 2016/0058872 | A1 | 3/2016 | Crew et al. |
| 2016/0136230 | A1 | 5/2016 | Campos et al. |
| 2016/0214972 | A1 | 7/2016 | Jin et al. |
| 2016/0243247 | A1 | 8/2016 | Bradner et al. |
| 2016/0272639 | A1 | 9/2016 | Crew et al. |
| 2016/0368911 | A1 | 12/2016 | Campus et al. |
| 2017/0008904 | A1 | 1/2017 | Crew et al. |
| 2017/0037004 | A1 | 2/2017 | Crew et al. |
| 2017/0065719 | A1 | 3/2017 | Qian et al. |
| 2017/0121321 | A1 | 5/2017 | Crews et al. |
| 2017/0281784 | A1 | 10/2017 | Wang et al. |
| 2017/0307614 | A1 | 10/2017 | Crews et al. |
| 2017/0327469 | A1 | 11/2017 | Crew et al. |
| 2018/0015087 | A1 | 1/2018 | Liu et al. |
| 2018/0072711 | A1 | 3/2018 | Crew et al. |
| 2018/0099940 | A1 | 4/2018 | Crew et al. |
| 2018/0125821 | A1 | 5/2018 | Crew et al. |
| 2018/0147202 | A1 | 5/2018 | Crew et al. |
| 2018/0155322 | A1 | 6/2018 | Crew et al. |
| 2018/0177750 | A1 | 6/2018 | Crew et al. |
| 2018/0179183 | A1 | 6/2018 | Crew et al. |
| 2018/0193470 | A1 | 7/2018 | Crew et al. |
| 2018/0215731 | A1 | 8/2018 | Crew et al. |
| 2018/0228907 | A1 | 8/2018 | Crew et al. |
| 2018/0237418 | A1 | 8/2018 | Crew et al. |
| 2018/0256586 | A1 | 9/2018 | Crew et al. |

FOREIGN PATENT DOCUMENTS

| | | |
|---|---|---|
| EP | 2985285 | 2/2016 |
| JP | A 2004-525889 | 8/2004 |
| JP | A 2010-502627 | 1/2010 |
| RU | 2008112221 A | 10/2009 |
| RU | 2418800 | 5/2011 |
| RU | 2448101 C2 | 4/2012 |
| RU | 2011121567 A | 10/2012 |
| RU | 2012138709 A | 3/2014 |
| WO | WO 1998/003502 | 1/1998 |
| WO | WO 2000/066119 | 11/2000 |
| WO | WO 2002/066512 | 8/2002 |
| WO | WO 2002/100845 | 12/2002 |
| WO | WO 2005/097791 | 10/2005 |
| WO | WO 2006/069063 | 6/2006 |
| WO | WO 2006/113942 | 10/2006 |
| WO | WO 2007/101347 | 9/2007 |
| WO | WO 2007/106670 | 9/2007 |
| WO | WO 2007/130626 | 11/2007 |
| WO | WO 2008/011392 | 1/2008 |
| WO | WO 2008/014236 | 1/2008 |
| WO | WO 2008/109057 | 9/2008 |
| WO | WO 2008/128121 | 10/2008 |
| WO | WO 2008/128171 | 10/2008 |
| WO | WO 2008/134679 | 11/2008 |
| WO | WO 2009/015254 | 1/2009 |
| WO | WO 2009/060292 | 5/2009 |
| WO | WO 2010/107485 | 9/2010 |
| WO | WO 2010/141805 | 12/2010 |
| WO | WO 2011/008260 | 1/2011 |
| WO | WO 2012/003281 | 1/2012 |
| WO | WO 2012/040527 | 3/2012 |
| WO | WO 2012/078559 | 6/2012 |
| WO | WO 2012/090104 | 7/2012 |
| WO | WO 2013/071035 | 5/2013 |
| WO | WO 2013/071039 | 5/2013 |
| WO | WO 2013/097224 | 7/2013 |
| WO | WO 2013/106643 | 7/2013 |
| WO | WO 2013/106646 | 7/2013 |
| WO | WO 2013/170147 | 11/2013 |
| WO | WO 2013/175417 | 11/2013 |
| WO | WO 2013/178570 | 12/2013 |
| WO | WO 2014/011712 | 1/2014 |
| WO | WO 2014/020502 | 2/2014 |
| WO | WO 2014/025759 | 2/2014 |
| WO | WO 2014/038606 | 3/2014 |
| WO | WO 2014/047024 | 3/2014 |
| WO | WO 2014/055461 | 4/2014 |
| WO | WO 2014/074658 | 5/2014 |
| WO | WO 2014/100065 | 6/2014 |
| WO | WO 2014/100071 | 6/2014 |
| WO | WO 2014/107713 | 7/2014 |
| WO | WO 2014/108452 | 7/2014 |
| WO | WO 2014/123418 | 8/2014 |
| WO | WO 2014/134201 | 9/2014 |
| WO | WO 2014/151863 | 9/2014 |
| WO | WO 2015/000868 | 1/2015 |
| WO | WO 2015/006524 | 1/2015 |
| WO | WO 2015/160845 | 10/2015 |
| WO | WO 2016/105518 | 6/2016 |
| WO | WO 2016/118666 | 7/2016 |
| WO | WO 2016/146985 | 9/2016 |
| WO | WO 2016/169989 | 10/2016 |
| WO | WO 2016/172134 | 10/2016 |
| WO | WO 2016/197114 | 12/2016 |
| WO | WO 2017/007612 | 1/2017 |
| WO | WO 2017/011590 | 1/2017 |
| WO | WO 2017/024317 | 2/2017 |
| WO | WO 2017/024318 A1 | 2/2017 |
| WO | WO 2017/024319 A1 | 2/2017 |
| WO | WO 2017/030814 | 2/2017 |
| WO | WO 2017/046036 | 3/2017 |
| WO | WO 2017/079267 | 5/2017 |
| WO | WO 2017/161119 | 9/2017 |
| WO | WO 2017/185036 | 10/2017 |
| WO | WO 2017/197051 | 11/2017 |
| WO | WO 2018/098280 | 5/2018 |
| WO | WO 2018/148440 | 8/2018 |
| WO | WO 2018/200981 | 11/2018 |

OTHER PUBLICATIONS

Asano M, et al., "Design, sterioselective synthesis, and biological evaluation of novel tri-cyclic compounds as inhibitor of apoptosis proteins (IAP) antagonists", Bioorg. Med. Chem., 21(18): 5725-5737 (2013).

Bargagna-Mohan, et al., "Use of PROTACS as molecular probes of angiogenesis", Bioorg Med Chem Left. 15(11) 2005, 2724-2727.

Bondeson, et al., (2017) "Targeted Protein Degradation by Small Molecules." *Annu Rev Pharmacol Toxicol* 57:107-123.

Bondeson, et al., "Catalytic in vivo protein knockdown by small-molecule PROTACS", National Chem Biol. 11(8) Aug. 2015, 611-617.

Buckley, et al., "HaloPROTACs: use of small molecule PROTACS to induce degradation of HaloTag fusion proteins", ACS Chem Biol. 10(8), 2015, 1831-1837.

Buckley, et al., "Small-molecule inhibitors of the interaction between the E3 ligase VHL and HIF1a", Angew Chem Int Ed Engl.51(46), Nov. 12, 2012, 11463-11467.

Buckley, et al., "Targeting the von Hippel-Lindau E3 ubiquitin ligase using small molecules to disrupt the VHL/HIF-1α interac-

(56) References Cited

OTHER PUBLICATIONS tion", Journal of the American Chemical Society, Feb. 27, 2012, 134(10): 4465-4468.
Burslem, et al., (2017) "Small-Molecule Modulation of Protein Homeostasis." Chem Rev 117(17):11269-11301.
Capitosti, S., et al., "Thalidomide analogues demonstrate dual inhibition of both angiogenesis and prostate cancer", Bioorganic & Medicinal Chemistry 12, (2004) 327-336.
Carmony, KC, et al., "PROTAC-Induced Proteolytic Targeting", Methods Mol. Biol., 2012, vol. 832, pp. 627-638.
Cas Registry No. 1004933-70-3, which entered STN on Feb. 21, 2008.
Cas Registry No. 871986-52-6 entered STN Jan 16, 2006.
Chene, P., et al., "Inhibiting the p53-MDM2 interaction: an important target for cancer therapy" Nat. Rev. Cancer (2003), 3, 102-109.
Cohen, F, et al., "Orally bioavailable antagonists of inhibitor of apoptosis proteins based on an azabicyclooctane scaffold", J. Med. Chem., 52(6), 1723-1730 (2009).
Cohen, F. et al., "Antogonists of inhibitors of apoptosis proteins based on thiazole amide isosteres", Bioorg. Med. Chem. Lett., 20(7), 2229-2233 (2010).
Contino-Pepin, Christiane, et al., "Preliminary biological evaluations of new thalidomide analogues for multiple sclerosis application", Bioorganic & Medicinal Chemistry Letter 19 (2009), 878-881.
Corson, et al., "Design and applications of bifunctional small molecules: why two heads are better than one", ACS Chemical Biology vol. 3 No. 11, pp. 677-692; Nov. 21, 2008.
Crews, C. M., "Targeting the undruggable proteome: the small molecules of my dreams", Chem Biol 17, 551-555, doi:S1074-5521(10)00196-1 [pii] 10.1016/j.chembiol.2010.05.011 (2010).
Cromm, et al., (2017) "Targeted Protein Degradation: from Chemical Biology to Drug Discovery." Cell Chem Biol 24(9):1181-1190.
Cyrus, et al., "Jostling for position: optimizing linker location in the design of estrogen receptor-targeting PROTACs", Chem Med Chem. 5(7), Jul. 5, 2010, 979-985.
Cyrus, K. et al, "Impact of Linker Length on the Activity of PROTACs," Mol. Biosyst., 2011, vol. 7, No. 2, pp. 359-364.
Cyrus, K. et al, "Two-Headed PROTAC: An Effective New Tool for Targeted Protein Degradation," Chembiochem., 2010, vol. 11, pp. 1531-1534.
Di, J et al. "Reactivation of p53 by inhibiting Mdm2 E3 Ligase: a novel antitumor approach", Current Cancer Drug Targets (2011), 11(8), 987-994.
Ding, Q, et al., "Discovery of RG7388, a potent and selective p53-MDM2 inhibitor in clinical development", J Med Chem. Jul. 25, 2013; 56(14):5979-83. doi: 10.1021/jm400487c. Epub Jul. 16, 2013. PubMed Pmid: 23808545 (J. Med. Chem. (2013) 56, 5979-5983 Ding, et al.
Dixon, S. J. et al., "Identifying druggable disease-modifying gene products",. Curr Opin Chem Biol 13, 549-555, doi:S1367-5931(09)00107-0 [pii] 10.1016/j.cbpa.2009.08.003 (2009).
Fischer, et al., "Structure of the DDB1-DRBN E3 Ubiquitin ligase in complex with thalidomide", Nature, vol. 000, pp. 1-5 (2014).
Flygare, J.A., et al "Small-molecule pan-IAP antagonists: a patent review", Expert Opin. Ther. Pat., 20 (2), 251-267 ( 2010).
Gadd, M.S., et al., "Structural basis of PROTAC cooperative recognition for selective protein degradation", Nat Chem Biol 13, 514-521 (2017).
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.
Golub, et al., "Molecular classification of cancer: class discovery and class prediction by gene expression monitoring", Science 286, 531-537 (1991).
Gosink, M et al., "Redirecting the specificity of ubiquitination by modifying ubiquitin-conjugating enzymes", Pro. Natl. Acad Sci, vol. 92, pp. 9117-9121, 1995.

Graves, Lee M., et al, "The dynamic nature of the kinome", Biochemical Journal, Feb. 15; 450(1), 1-8 (2013).
Haupt, Y. et al., "Mdm2 promotes the rapid degradation of p53", Nature 387, 296-299 (1997).
Hennessy, EJ, et al., "Discovery of aminopiperidine-based Smac mimetics as IAP antagonists", Bioorg. Med. Chem. Lett., 22(4), 1690-1694 (2012).
Hines, J., et al., "Posttranslational protein knockdown coupled to receptor tyrosine kinase activation with phosphoPROTACs", Proc Natl Acad Sci USA 110, 8942-8947 (2013).
Hird, AW, et al., "Structure-based design and synthesis of tricyclic IAP (Inhibitors of Apoptosis Proteins) inhibitors", Bioorg. Med. Chem. Lett., 24(7): 1820-1824 (2014).
Hon, et al., "Structural basis for the recognition of hydroxyproline in Hlf-1 alpha by pVHL", Nature 417, Jun. 27, 2002, 975-978.
Huang, et al., (2016) "Drugging the undruggables: exploring the ubiquitin system for drug development." Cell Res 26(4):484-498.
Hughes, et al., (2017) "Molecular recognition of ternary complexes: a new dimension in the structure-guided design of chemical degraders." Essays Biochem 61(5):505-516.
Ishikawa, T. et al., "Design and synthesis of novel human epidermal growth factor receptor 2 (HER2)/epidermal growth factor receptor (EGFR) dual inhibitors bearing a pyrrolo[3,2-d]pyrimidine scaffold", Journal of Medicinal Chemistry 2011, 54 (23), 8030-8050.
Ivan, M., et al., "HIFa Targeted for VHL-Mediated Destruction by Proline Hydroxylation: Implications for O2 Sensing", Science, vol. 292, No. 5516, pp. 464-468, 2001.
Jang, E.R. et al., "Targeted Degradation of Proteins by PROTACs," Curr. Protoc. Chem. Biol., 2010, vol. 2, No. 2, pp. 71-87.
Kim, K.S., "Discovery of tetrahydroisoquinoline-based bivalent heterodimeric IAP antagonists", Bioorg. Med. Chem. Lett. 24(21), 5022-5029 (2014).
Knott, Edward (1955). "Compounds containing sulphur chromophores. Part I. The action of bases on heterocyclic sulphide quarternary salts", Journal of the Chemical Society 10.1039/jr9550000916. 949-954.
Kronke, et al, "Lenalidomide Causes Selective Degradation of IKZF1 and IKZF3 in Multiple Myeloma Cells", Science 343, 301-305 (2014).
Lackey, K. et al., "The discovery of potent cRafl kinase inhibitors", Bioorganic and Medicinal Chemistry Letters, 10 (2000), 223-226.
Lai, A.C., et al., "Modular PROTAC Design for the Degradation of Oncogenic BCR-ABL", Angew Chem Int Ed Engl 55, 807-810 (2016).
Lai, et al., (2017) "Induced protein degradation: an emerging drug discovery paradigm." Nat Rev Drug Discov 16(2):101-114.
Lala, et al., "Role of nitric oxide in tumor progression: Lessons from experimental tumors", Cancer and Metastasis Reviews 17:91-106 (1998).
Lebraud, H., et al., "Protein Degradation by In-Cell Self-Assembly of Proteolysis Targeting Chimeras", ACS Central Science, 2, 927-934 (2016).
Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, Nov. 23, 2007.
Levine, et al., Targeting the androgen receptor with steroid conjugates, J. Med. Chem., vol. 57., No. 20. pp. 8224-8237, (2014).
Li, Yan, et al., "Single polymer-drug conjugate carrying two drugs for fixed-dose co-delivery", Medicinal Chemistry, 2014, vol. 4(10): 676-683.
Liu, K., et al., "Design and biological characterization of hybrid compounds of curcumin and thalidomide for multiple myeloma", Org. Biomol. Chem. 2013, 11, 4757-4763.
Lopez-Girona, A. et al., Cereblon is a direct protein target for immunomodulatory and antiproliferative activities of lenalidomide and pomalidomide, Leukemia 26: 2326-2335, 2012.
Lu, et al., "Hijacking the E3 ubiquitin ligase cereblon to efficiently target BRD4", Chem Biol 22(6), 2015, 755-763.
Lu, et al., "The myeloma drug lenalidomide promotes the cereblon-dependent destruction of ikaros proteins", Science 343, 305-309 (2014).
Mahalingam, D., et al., "Targeting HSP90 for cancer therapy", Br J Cancer 100, 1523-1529 (2009).

(56) References Cited

OTHER PUBLICATIONS

Maniaci C, et al. (2017) "Homo-PROTACs: bivalent small-molecule dimerizers of the VHL E3 ubiquitin ligase to induce self-degradation." Nat Commun 8(1):830 1-13.

Mannhold, R., et al., "IAP antagonists: promising candidates for cancer therapy", Drug Discov. Today, 15 (5-6), 210-219 (2010).

Medline Plus Trusted Health Information for You, www.nlm.nih.gov/medlineplus/cancer.html pp. 1-10, (2007).

Min, Jung-hyun, et al., "Structure of an HIV-1-alpha—pVHL complex: hydroxyproline recognition in signaling", Jun. 7, 2002, 296: 1886-1889.

Miyazaki, M., et al., "Discovery of DS-5272 as a promising candidate: a potent and orally active p53-MDM2 interaction inhibitor", Bioorg. Med. Chem. Lett. (2015) 23, 2360-2367.

Muller, G., et al., "Amino-Substituted Thalodomide Analogs: Potent Inhibitors of TNF-$\alpha$ Production", Bioorganic & Medicinal Chemistry Letters 9 (1999) 1625-1630.

Ndubaku, C, et al., "Antagonism of c-IAP and XIAP proteins is required for efficient induction of cell death by small-molecule Iap antagonists", ACS Chem Biol. Jul. 17, 2009;4(7):557-566.

Neklesa, T.K., et al., "Chemical biology: Greasy tags for protein removal", Nature 487, 308-309 (2012).

Neklesa, Targeted protein degradation by PROTACs. Pharmacology & Therapeutics 174, 138-144 (2017).

Nikolovska-Coleska, et al., "Interaction of a cyclic, Bivalent Smac Mimetic with the X-linked inhibitor of apoptosis protein", Biochemistry, 2008, 47(37), pp. 9811-9824.

Ohoka, N. et al. Sniper(TACC3) induces cytoplasmic vacuolization and sensitizes cancer cells to Bortezomib. Cancer Sci. 108, 1032-1041 (2017).

Oost, T.K. et al., "Discovery of potent antagonists of the antiapoptotic protein XIAP for the treatment of cancer", Journal of Medicinal Chemistry 2004, 47, 4417-4426.

Ottis P, et al. (2017) "Assessing Different E3 Ligases for Small Molecule Induced Protein Ubiquitination and Degradation." ACS Chem Biol 12(10):2570-2578.

Ottis, et al., (2017) "Proteolysis-Targeting Chimeras: Induced Protein Degradation as a Therapeutic Strategy." ACS Chem Biol 12(4):892-898.

Perez, HL," Discovery of potent heterodimeric antagonists of inhibitor of apoptosis proteins (IAPs) with sustained antitumor activity", J. Med. Chem. 58(3), 1556-1562 (2015).

Poulikakos, P. I., Zhang, C., Bollag, G., Shokat, K. M. & Rosen, N. RAF inhibitors transactivate RAF dimers and ERK signalling in cells with wild-type BRAF. Nature 464, 427-430 (2010).

Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.

Raina, et al., (2017) "Targeted protein knockdown using small molecule degraders." Curr Opin Chem Biol 39:46-53.

Raina, K., et al., "PROTAC-induced BET protein degradation as a therapy for castration-resistant prostate cancer", Proc Natl Acad Sci USA 113, 7124-7129 (2016).

Remillard D, et al. (2017) "Degradation of the BAF Complex Factor BRD9 by Heterobifunctional Ligands." Angew Chem Int Ed Engl 56(21):5738-5743.

Rew, Y, et al., "Discovery of AM-7209, a potent and selective 4-amidobenzoic acid inhibitor of the MDM2-p53 interaction", J Med Chem. Dec. 26, 2014;57(24):10499-10511. doi: 10.1021/jm501550p. Epub Dec. 4, 2014. PubMed PMID: 25384157.

Rodriguez-Gonzalez, et al., "Targeting steroid hormone receptors for ubiquitination and degradation in breast and prostate cancer", Oncogene. 27(57), Dec. 4, 2008, 7201-7211.

Rotili, D., et al., "Photoactivable peptides for identifying enzyme-substrate and protein-protein interactions", Chem Commun (Carob) 47(5), Feb. 2011, 1488-1490.

Ruchelman, A., et al., "Isosteric analogs of lenalidominde and pomalidomide: Synthesis and biological activity", Bioorganic & Medicinal Chemistry Letters 23 (2013) 360-365.

Sakamoto, et al., "Development of Protacs to target cancer-promoting proteins for ubiquitination and degradation", Mol Cell Proteomics. 2(12), Dec. 2003, 1350-1358.

Sakamoto, et al., "Protacs: chimeric molecules that target proteins to the Skp 1-Cullin-F box complex for ubiquitination and degradation", Proc Natl Acad Sci U S A.98(15), Jul. 17, 2001, 8554-8559.

Salami, J. & Crews, C. M. Waste disposal—An attractive strategy for cancer therapy. Science 355, 1163-1167 (2017).

Schiedel, M., et al., "Chemically Induced Degradation of Sirtuin 2 (Sirt2) by a Proteolysis Targeting Chimera (PROTAC) Based on Sirtuin Rearranging Ligands (SirReals)", J Med Chem. (2017), 61:482-491.

Schneekloth, et al., "Chemical Genetic Control of Protein Levels: Selective in Vivo Targeted Degradation", J Am Chem Soc. 126(12), Mar. 31, 2004, 3748-3754.

Schneekloth, et al., Targeted intracellular protein degradation induced by a small molecule: En route to chemical proteomics, Bioorg. Med. Chem. Lett. 18 (2008) 5904-5908.

Smith, et al., "Targeted Intracellular Protein Degradation Induced by a Small Molecule: En Route to Chemical Proteomics", Bioorg Med Chem Lett. 18(22), Nov. 15, 2008, 5904-5908.

Stewart, Scott G., et al., "Efforts toward elucidating Thalidomide's molecular target: An Expedient Synthesis of the first Thalidomide Biotin Analogue" Org. Biomol., Chem., 2010, 8, 4059-4062.

STN transcript excerpt Nov. 24, 2017 "Compounds containing sulfur Chromophores v. Complex cyanines".

Stoppler, Melissa Conrad., Endometriosis [online], "Endometriosis Definition and Facts" URL http://www.medicinenet.com/endometriosis/article.htm, retrieved on Apr. 5, 2017.

Stoppler, Melissa Conrad., Endometriosis [online], "What about surgery for Endometriosis?" URL http://www.medicinenet.com/endometriosis/article.htm, retrieved on Apr. 5, 2017.

Sun, D, et al., "Discovery of AMG 232, a potent, selective, and orally bioavailable MDM2-p53 inhibitor in clinical development", J Med Chem. Feb. 27, 2014;57(4):1454-72. doi: 10.1021/jm401753e. Epub Feb. 5, 2014. PubMed PMID: 24456472.

Sun, et al., "Potent bivalent Smac mimetics: effect of the linker on binding to inhibitor apoptosis proteins (IAPs) and anticancer activity", J. Med. Chem. 53, 3306-3318 (2011).

Takeuchi, et al., "Receptor Tyrosine Kinases and Targeted Cancer Therapeutics", Biol Pharm Bull 34, 1774-1780 (2011).

Toure, et al., (2016) "Small-Molecule PROTACS: New Approaches to Protein Degradation." Angew Chem Int Ed Engl 55(6):1966-1973.

Turk, B. E., "Binding of thalidomide to alphal-acid glycoprotein may be involved in its inhibition of tumor necrosis factor alpha production", Proc. Natl. Acad. Sci. U.S.A. 1996, 93, 7552-7556.

Vallee, et al., "Tricyclic Series of Heat Shock Protein 90 (HSP90) Inhibitors Part I: Discovery of Tricyclic Imidazo [4,5-c] Pyridines as Potent Inhibitors of the Hsp90 Molecular Chaperone", J Med Chem. 54(20), Oct. 27, 2011, 7206-7219.

Vamos M., et al., "Expedient synthesis of highly potent antagonists of inhibitor of apoptosis proteins (IAPs) with unique selectivity for ML-IAP", ACS Chem. Biol., 8(4), 725-732 (2013).

Van Molle, et al., "Dissecting fragment-based lead discovery at the von Hippel-Lindau protein:hypoxia inducible factor 1a protein-protein interface", Chem Biol. 19(10), Oct. 26, 2012, 1300-1312.

Vassilev, et al., "In vivo activation of the p53 pathway by small-molecule antagonists of MDM2", Science 303, Feb. 6, 2004, 844-848.

Vazquez, A. et al., "The genetics of the p53 pathway, apoptosis and cancer therapy", Nat. Rev. Drug. Dis., 7, 979-982 (2008).

Vu, B. et al. "Discovery of RG7112: a small-molecule MDM2 inhibitor in clinical development", ACS Med. Chem. Lett. (2013) 4, 466-469.

Wang J, et al., "Discovery of novel second mitochondrial-derived activator of caspase mimetics as selective inhibitor or apoptosis protein inhibitors", J. Pharmacol. Exp. Ther., 349(2): 319-29 (2014).

Wang, S., et al. "Small-molecule inhibitors of the MDM2-p53 protein-protein interaction (MDM2 inhibitors) in clinical trials for cancer treatment", J. Med. Chem. (2015) 58, 1038-1052.

(56) References Cited

OTHER PUBLICATIONS

Wang, S., et al. "Temporal activation of p53 by a specific MDM2 inhibitor is selectively toxic to tumors and leads to complete tumor growth inhabitation", PNAS USA (2008) 105, 3933-3938.

Winter, et al., "Phthalimide Conjugation as a strategy for in vivo target protein degradation", Science, 2015 vol. 348 (6241), pp. 1376-1381 [Pub online: May 21, 2015].

Yao, Z. et al. BRAF Mutants Evade ERK-Dependent Feedback by Different Mechanisms that Determine Their Sensitivity to Pharmacologic Inhibition. Cancer Cell 28, 370-383 (2015).

Yao, Z. et al. Tumors with class 3 BRAF mutants are sensitive to the inhibition of activated RAS. Nature 548, 234-238 (2017).

Zengerle, et al., "Selective Small Molecule Induced Degradation of the BET Bromodomain Protein BRD4" ACS Chemical Biology, Jun. 2, 2015, vol. 10, pp. 1770-1777.

Zhang B.et al., "Small-molecule MDM2-p53 inhibitors: recent advances", Future Med. Chem. (2015) 7, 631-645.

Zhang, D. et al., "Targeted Degradation of Proteins by Small Molecules: A Novel Tool for Functional Proteomics," comb Chem. High Throughput Screen., 2004, vol. 7, No. 7, pp. 689-697.

International Search Report and Written Opinion for PCT/US2019/050114, dated Jan. 2, 2020.

\* cited by examiner

FIG. 2

Table 42. Exemplary protein targeting moieties and compounds of the present disclosure.

| No. | Structure | Compound Name | MH+ | Synthetic Scheme |
|---|---|---|---|---|
| 86 | 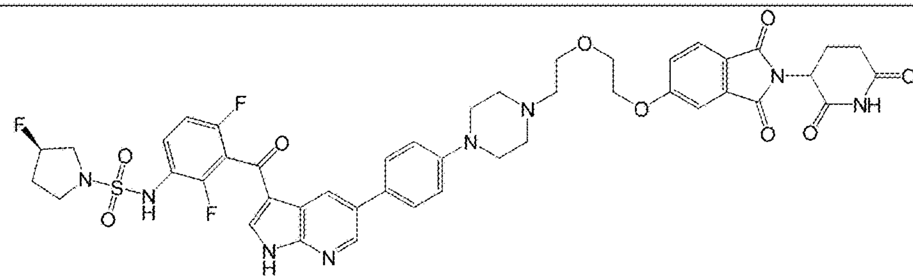 | (3R)-N-(3-(5-(4-(4-(2-(2-(2-(2,6-dioxopiperidin-3-yl)-1,3-dioxoisoindolin-5-yl)oxy)ethoxy)ethyl)piperazin-1-yl)phenyl)-1H-pyrrolo[2,3-b]pyridine-3-carbonyl)-2,4-difluorophenyl)-3-fluoropyrrolidine-1-sulfonamide | 929.23 | 1 |
| 87 | 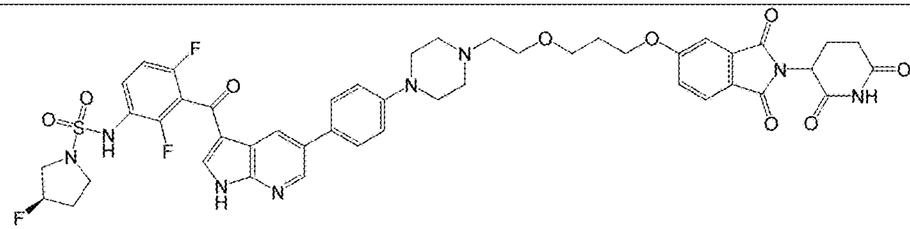 | (3R)-N-(3-(5-(4-(4-(2-(3-((2-(2,6-dioxopiperidin-3-yl)-1,3-dioxoisoindolin-5-yl)oxy)propoxy)ethyl)piperazin-1-yl)phenyl)-1H-pyrrolo[2,3-b]pyridine-3-carbonyl)-2,4-difluorophenyl)-3-fluoropyrrolidine-1-sulfonamide | 943.18 | 1 |
| 88 | 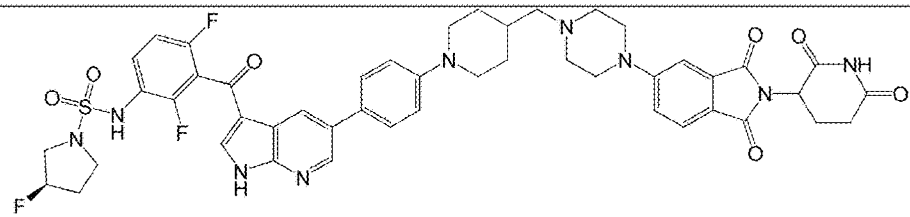 | (3R)-N-(3-(5-(4-(4-((4-(2-(2,6-dioxopiperidin-3-yl)-1,3-dioxoisoindolin-5-yl)piperazin-1-yl)methyl)piperidin-1-yl)phenyl)-1H-pyrrolo[2,3-b]pyridine-3-carbonyl)-2,4-difluorophenyl)-3-fluoropyrrolidine-1-sulfonamide | 938.57 | 1 |

FIG. 2. Continued

| | | | |
|---|---|---|---|
| 89 | [structure] | (3R)-N-(3-(5-(4-(4-(4-((2-(2,6-dioxopiperidin-3-yl)-1,3-dioxoisoindolin-5-yl)oxy)butyl)piperazin-1-yl)phenyl)-1H-pyrrolo[2,3-b]pyridine-3-carbonyl)-2,4-difluorophenyl)-3-fluoropyrrolidine-1-sulfonamide | 913.53 | 1 |
| 90 | [structure] | (3R)-N-(3-(5-(4-(4-(3-((2-(2,6-dioxopiperidin-3-yl)-1,3-dioxoisoindolin-5-yl)oxy)propyl)piperazin-1-yl)phenyl)-1H-pyrrolo[2,3-b]pyridine-3-carbonyl)-2,4-difluorophenyl)-3-fluoropyrrolidine-1-sulfonamide | 899.51 | 1 |
| 91 | [structure] | (3R)-N-(3-(5-(4-(2-(2-(4-(2-(2,6-dioxopiperidin-3-yl)-1,3-dioxoisoindolin-5-yl)piperazin-1-yl)ethoxy)ethoxy)phenyl)-1H-pyrrolo[2,3-b]pyridine-3-carbonyl)-2,4-difluorophenyl)-3-fluoropyrrolidine-1-sulfonamide | 929.15 | 2 |

FIG. 2. Continued

| | | | |
|---|---|---|---|
| 92 | 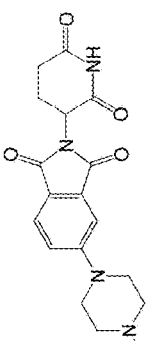 | (3R)-N-(3-(5-(4-((5-(4-(2-(2,6-dioxopiperidin-3-yl)-1,3-dioxoisoindolin-5-yl)piperazin-1-yl)pentyl)oxy)phenyl)-1H-pyrrolo[2,3-b]pyridine-3-carbonyl)-2,4-difluorophenyl)-3-fluoropyrrolidine-1-sulfonamide | 927.55 | 2 |
| 93 | 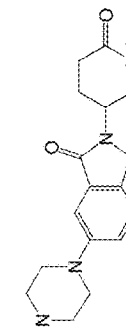 | (3R)-N-(3-(5-(4-((6-(4-(2-(2,6-dioxopiperidin-3-yl)-1,3-dioxoisoindolin-5-yl)piperazin-1-yl)hexyl)oxy)phenyl)-1H-pyrrolo[2,3-b]pyridine-3-carbonyl)-2,4-difluorophenyl)-3-fluoropyrrolidine-1-sulfonamide | 941.57 | 2 |
| 94 | 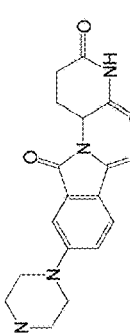 | (3R)-N-(3-(5-(4-(3-(2-(4-(2-(2,6-dioxopiperidin-3-yl)-1,3-dioxoisoindolin-5-yl)piperazin-1-yl)ethoxy)propoxy)phenyl)-1H-pyrrolo[2,3-b]pyridine-3-carbonyl)-2,4-difluorophenyl)-3-fluoropyrrolidine-1-sulfonamide | 943.55 | 2 |

FIG. 2. Continued

| | | | |
|---|---|---|---|
| 95 | 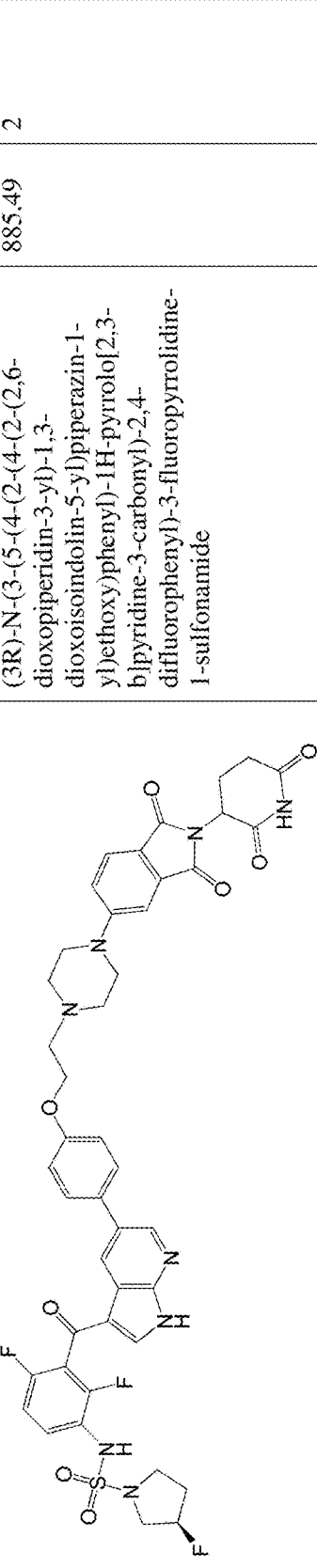 | (3R)-N-(3-(5-(4-(2-(4-(2-(2,6-dioxopiperidin-3-yl)-1,3-dioxoisoindolin-5-yl)piperazin-1-yl)ethoxy)phenyl)-1H-pyrrolo[2,3-b]pyridine-3-carbonyl)-2,4-difluorophenyl)-3-fluoropyrrolidine-1-sulfonamide | 885.49 | 2 |
| 96 | 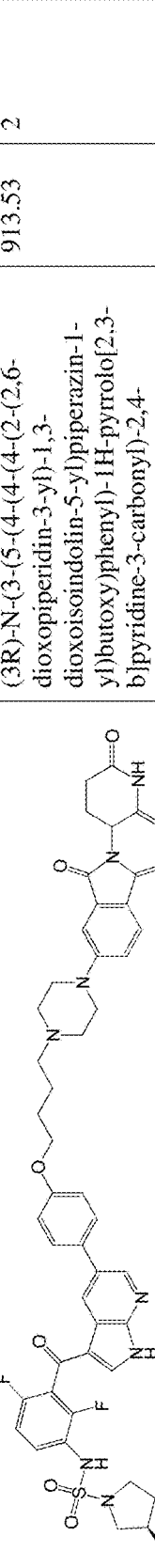 | (3R)-N-(3-(5-(4-(4-(2-(2,6-dioxopiperidin-3-yl)-1,3-dioxoisoindolin-5-yl)piperazin-1-yl)butoxy)phenyl)-1H-pyrrolo[2,3-b]pyridine-3-carbonyl)-2,4-difluorophenyl)-3-fluoropyrrolidine-1-sulfonamide | 913.53 | 2 |
| 97 | 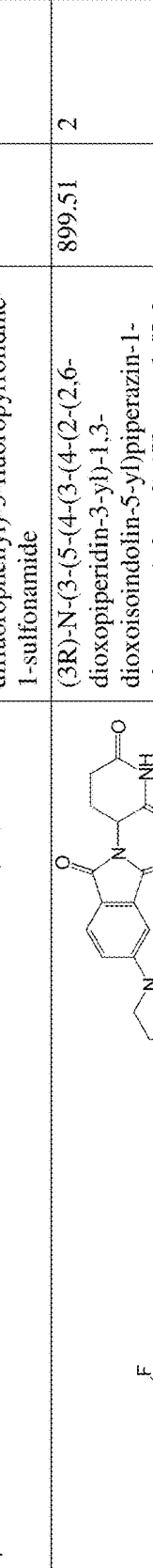 | (3R)-N-(3-(5-(4-(3-(4-(2-(2,6-dioxopiperidin-3-yl)-1,3-dioxoisoindolin-5-yl)piperazin-1-yl)propoxy)phenyl)-1H-pyrrolo[2,3-b]pyridine-3-carbonyl)-2,4-difluorophenyl)-3-fluoropyrrolidine-1-sulfonamide | 899.51 | 2 |

FIG. 2. Continued

| | | | |
|---|---|---|---|
| 98 | [structure] | (2S,4R)-1-((S)-2-(2-(4-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethyl)piperazin-1-yl)acetamido)-3,3-dimethylbutanoyl)-4-hydroxy-N-(4-(4-methylthiazol-5-yl)benzyl)pyrrolidine-2-carboxamide | 1099.37 | 3 |
| 99 | [structure] | (2S,4R)-1-((S)-2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)acetamido)-3,3-dimethylbutanoyl)-4-hydroxy-N-(4-(4-methylthiazol-5-yl)benzyl)pyrrolidine-2-carboxamide | 1099.68 | 3 |
| 100 | [structure] | (2S,4R)-1-((S)-2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propoxy)acetamido)-3,3-dimethylbutanoyl)-4-hydroxy-N-(4-(4-methylthiazol-5-yl)benzyl)pyrrolidine-2-carboxamide | 1113.38 | 3 |

| | | | |
|---|---|---|---|
| 101 |  | (2S,4R)-1-((S)-2-(2-(4-(3-(4-(3-(2,6-difluoro-3-(((R)-3-fluoropyrrolidine)-1-sulfonamido)benzoyl)-1H-pyrrolo[2,3-b]pyridin-5-yl)phenoxy)propyl)piperazin-1-yl)acetamido)-3,3-dimethylbutanoyl)-4-hydroxy-N-(4-(4-methylthiazol-5-yl)benzyl)pyrrolidine-2-carboxamide | 1113.36 | 3 |
| 193 |  | (3R)-N-(3-(5-(4-(3-((2-(2,6-dioxopiperidin-3-yl)-1,3-dioxoisoindolin-5-yl)oxy)propoxy)phenyl)-1H-pyrrolo[2,3-b]pyridine-3-carbonyl)-2,4-difluorophenyl)-3-fluoropyrrolidine-1-sulfonamide | 831.43 | 12 |

FIG. 2. Continued

| | | | | |
|---|---|---|---|---|
| 194 | 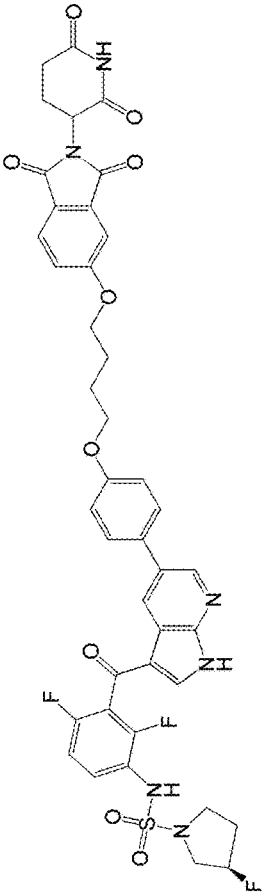 | (3R)-N-(3-(5-(4-(4-((2-(2,6-dioxopiperidin-3-yl)-1,3-dioxoisoindolin-5-yl)oxy)butoxy)phenyl)-1H-pyrrolo[2,3-b]pyridine-3-carbonyl)-2,4-difluorophenyl)-3-fluoropyrrolidine-1-sulfonamide | 845.45 | 12 |
| 102 | 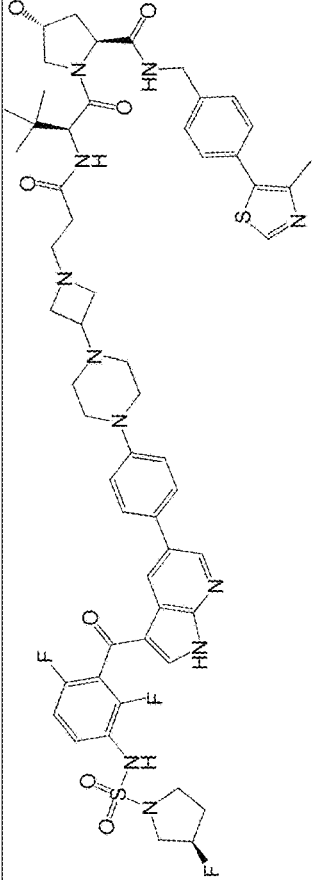 | (2S,4R)-1-((S)-2-(3-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)propanamido)-3,3-dimethylbutanoyl)-4-hydroxy-N-(4-methylthiazol-5-yl)benzyl)pyrrolidine-2-carboxamide | 1124.73 | 3 |
| 195 | 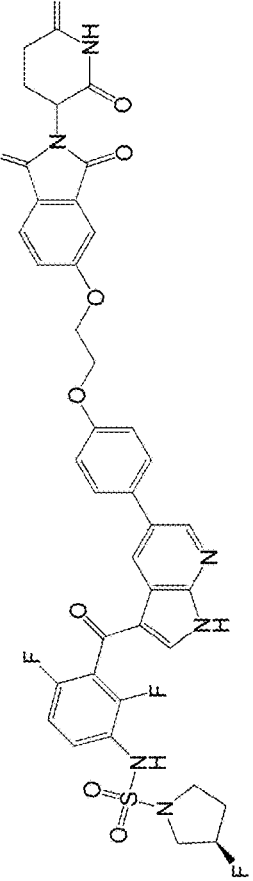 | (3R)-N-(3-(5-(4-(2-((2-(2,6-dioxopiperidin-3-yl)-1,3-dioxoisoindolin-5-yl)oxy)ethoxy)phenyl)-1H-pyrrolo[2,3-b]pyridine-3-carbonyl)-2,4-difluorophenyl)-3-fluoropyrrolidine-1-sulfonamide | 817.41 | 12 |

FIG. 2. Continued

| | | | |
|---|---|---|---|
| 103 | 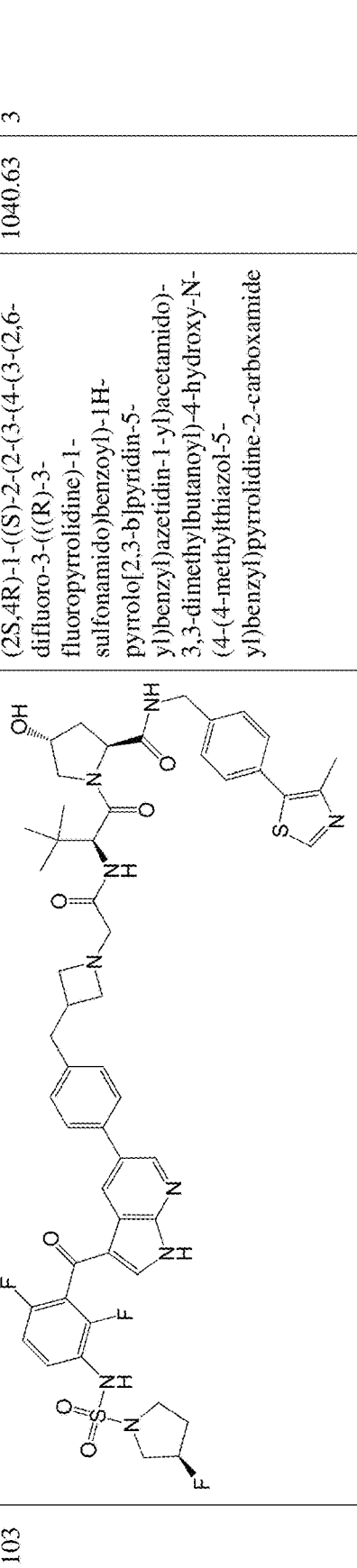 | (2S,4R)-1-((S)-2-(2-(3-(4-(3-(2,6-difluoro-3-(((R)-3-fluoropyrrolidine)-1-sulfonamido)benzoyl)-1H-pyrrolo[2,3-b]pyridin-5-yl)benzyl)azetidin-1-yl)acetamido)-3,3-dimethylbutanoyl)-4-hydroxy-N-(4-(4-methylthiazol-5-yl)benzyl)pyrrolidine-2-carboxamide | 1040.63 | 3 |
| 104 | 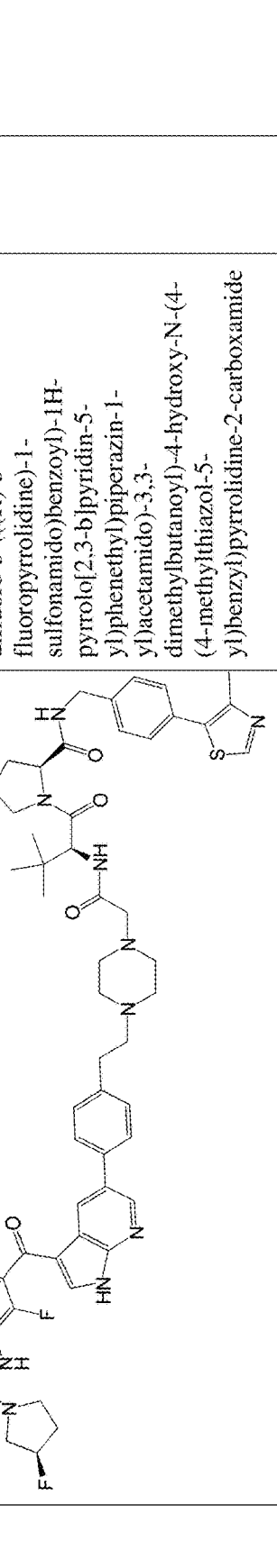 | (2S,4R)-1-((S)-2-(2-(4-(4-(3-(2,6-difluoro-3-(((R)-3-fluoropyrrolidine)-1-sulfonamido)benzoyl)-1H-pyrrolo[2,3-b]pyridin-5-yl)phenethyl)piperazin-1-yl)acetamido)-3,3-dimethylbutanoyl)-4-hydroxy-N-(4-(4-methylthiazol-5-yl)benzyl)pyrrolidine-2-carboxamide | 1083.68 | 3 |

FIG. 2. Continued

| | | | |
|---|---|---|---|
| 105 | 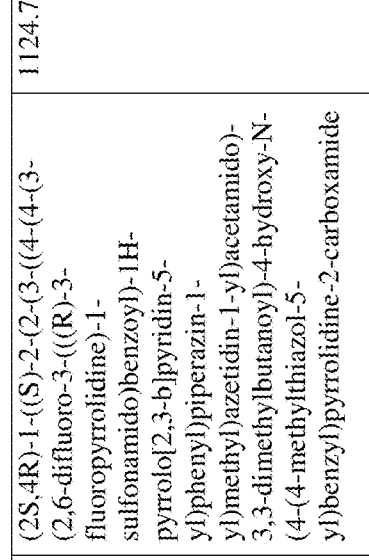 | (2S,4R)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)azetidin-1-yl)acetamido)-3,3-dimethylbutanoyl)-4-hydroxy-N-(4-(4-methylthiazol-5-yl)benzyl)pyrrolidine-2-carboxamide | 1124.72 | 3 |
| 106 | 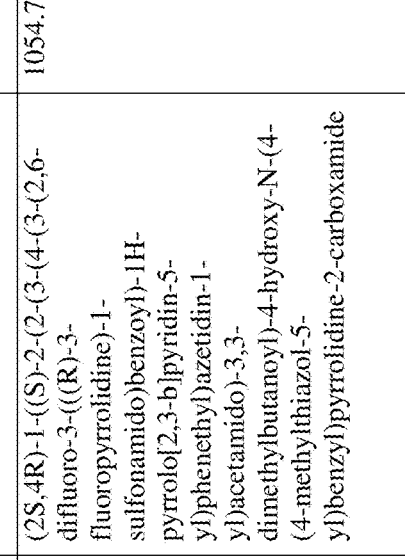 | (2S,4R)-1-((S)-2-(2-(3-(4-(3-(2,6-difluoro-3-(((R)-3-fluoropyrrolidine)-1-sulfonamido)benzoyl)-1H-pyrrolo[2,3-b]pyridin-5-yl)phenethyl)azetidin-1-yl)acetamido)-3,3-dimethylbutanoyl)-4-hydroxy-N-(4-(4-methylthiazol-5-yl)benzyl)pyrrolidine-2-carboxamide | 1054.7 | 3 |

FIG. 2. Continued

| | | | |
|---|---|---|---|
| 107 | 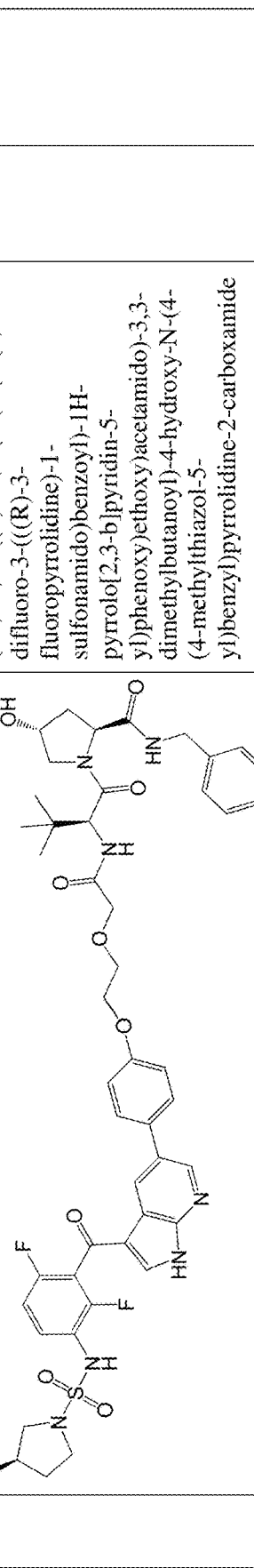 | (2S,4R)-1-((S)-2-(2-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)acetamido)-3,3-dimethylbutanoyl)-4-hydroxy-N-(4-(4-methylthiazol-5-yl)benzyl)pyrrolidine-2-carboxamide | 1031.30 | 4 |
| 108 | 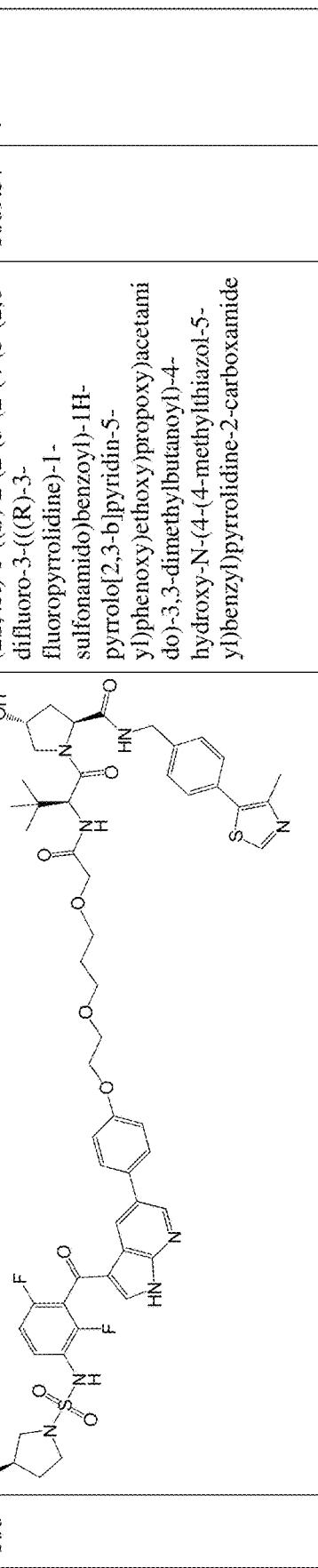 | (2S,4R)-1-((S)-2-(2-(3-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)propoxy)acetamido)-3,3-dimethylbutanoyl)-4-hydroxy-N-(4-(4-methylthiazol-5-yl)benzyl)pyrrolidine-2-carboxamide | 1089.37 | 4 |

FIG. 2. Continued

| 109 | 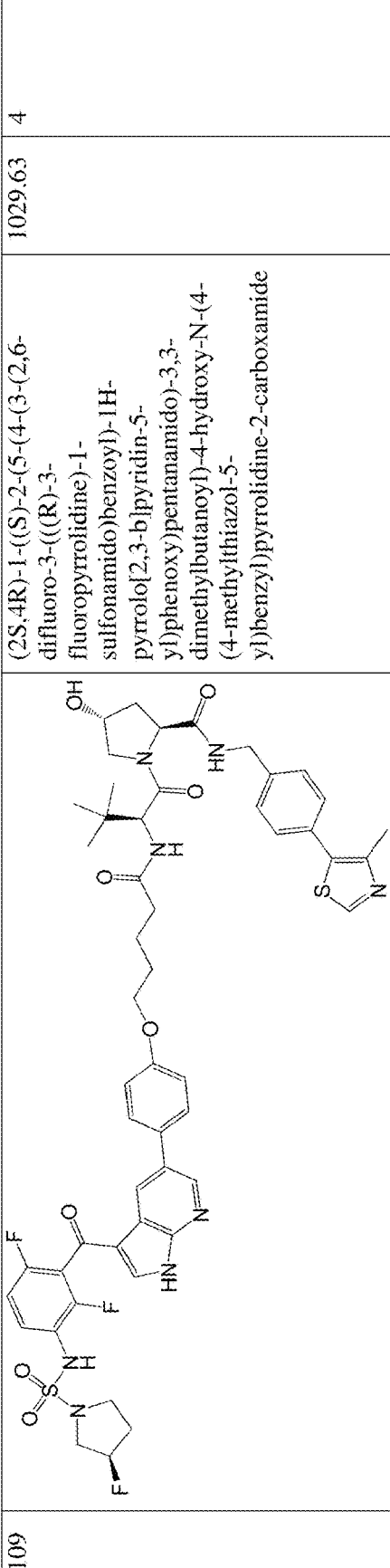 | (2S,4R)-1-((S)-2-(5-(4-(3-(2,6-difluoro-3-(((R)-3-fluoropyrrolidine)-1-sulfonamido)benzoyl)-1H-pyrrolo[2,3-b]pyridin-5-yl)phenoxy)pentanamido)-3,3-dimethylbutanoyl)-4-hydroxy-N-(4-(4-methylthiazol-5-yl)benzyl)pyrrolidine-2-carboxamide | 1029.63 | 4 |
| 110 | 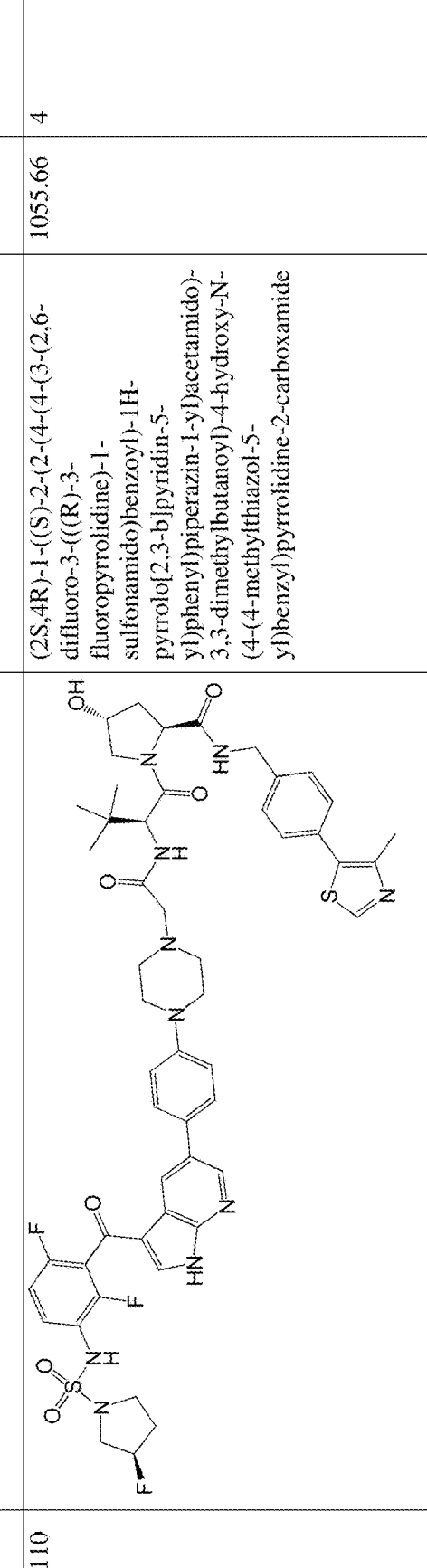 | (2S,4R)-1-((S)-2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)acetamido)-3,3-dimethylbutanoyl)-4-hydroxy-N-(4-(4-methylthiazol-5-yl)benzyl)pyrrolidine-2-carboxamide | 1055.66 | 4 |

FIG. 2. Continued

| | | | |
|---|---|---|---|
| 111 | (structure) | (2S,4R)-1-((S)-2-(4-(4-(3-(2,6-difluoro-3-(((R)-3-fluoropyrrolidine)-1-sulfonamido)benzoyl)-1H-pyrrolo[2,3-b]pyridin-5-yl)phenoxy)butanamido)-3,3-dimethylbutanoyl)-4-hydroxy-N-(4-(4-methylthiazol-5-yl)benzyl)pyrrolidine-2-carboxamide | 1015.6 | 4 |
| 112 | (structure) | (2S,4R)-1-((S)-2-(5-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)pentanamido)-3,3-dimethylbutanoyl)-4-hydroxy-N-(4-(4-methylthiazol-5-yl)benzyl)pyrrolidine-2-carboxamide | 1097.7 | 4 |
| 113 | (structure) | (2S,4R)-1-((S)-2-(6-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)hexanamido)-3,3-dimethylbutanoyl)-4-hydroxy-N-(4-(4-methylthiazol-5-yl)benzyl)pyrrolidine-2-carboxamide | 1111.73 | 4 |

FIG. 2. Continued

| | | | |
|---|---|---|---|
| 114 | 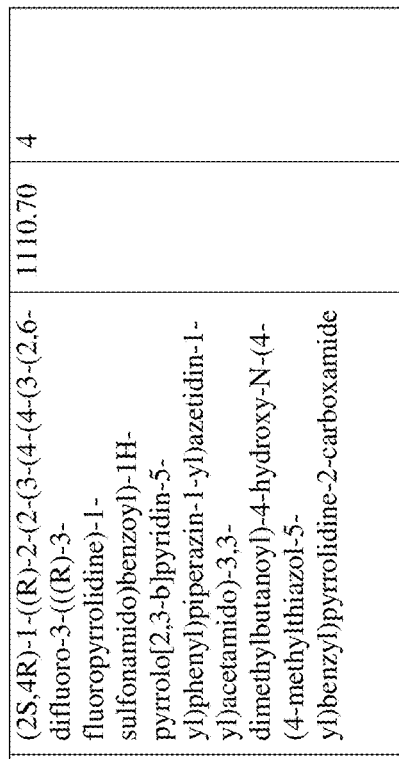 | (2S,4R)-1-((R)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-4-hydroxy-N-(4-(4-methylthiazol-5-yl)benzyl)pyrrolidine-2-carboxamide | 1110.70 | 4 |
| 115 | 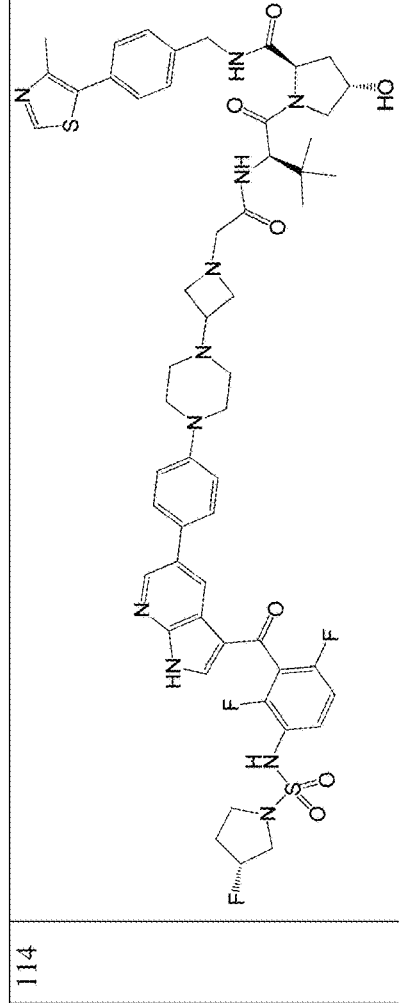 | (2S,4R)-1-((S)-2-(2-(4-((4-(3-(2,6-difluoro-3-(((R)-3-fluoropyrrolidine)-1-sulfonamido)benzoyl)-1H-pyrrolo[2,3-b]pyridin-5-yl)phenoxy)methyl)piperidin-1-yl)acetamido)-3,3-dimethylbutanoyl)-4-hydroxy-N-(4-(4-methylthiazol-5-yl)benzyl)pyrrolidine-2-carboxamide | 1084.7 | 4 |

FIG. 2. Continued

| | | | |
|---|---|---|---|
| 116 | 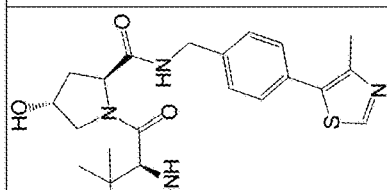 | (2S,4R)-1-((S)-2-(2-(4-(3-(4-(3-(2,6-difluoro-3-(((R)-3-fluoropyrrolidine)-1-sulfonamido)benzoyl)-1H-pyrrolo[2,3-b]pyridin-5-yl)phenyl)azetidin-1-yl)piperidin-1-yl)acetamido)-3,3-dimethylbutanoyl)-4-hydroxy-N-(4-(4-methylthiazol-5-yl)benzyl)pyrrolidine-2-carboxamide | 1109.7 | 4 |
| 117 | 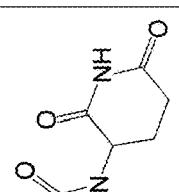 | (E)-2-(2,6-dioxopiperidin-3-yl)-5-(4-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione | 707.47 | 5 |
| 118 | 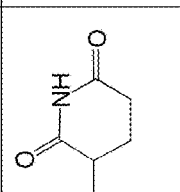 | 2-(2,6-dioxopiperidin-3-yl)-5-(3-(4-(4-(1-(hydroxyimino)-2,3-dihydro-1H-inden-5-yl)-3-(pyridin-4-yl)-1H-pyrazol-1-yl)benzyl)azetidin-1-yl)isoindoline-1,3-dione | 692.45 | 5 |

FIG. 2. Continued

| | | | |
|---|---|---|---|
| 119 | [structure] | (E)-2-(2,6-dioxopiperidin-3-yl)-5-(3-(4-(4-(1-(hydroxyimino)-2,3-dihydro-1H-inden-5-yl)-3-(pyridin-4-yl)-1H-pyrazol-1-yl)phenoxy)azetidin-1-yl)isoindoline-1,3-dione | 694.43 | 5 |
| 120 | [structure] | 2-(2,6-dioxopiperidin-3-yl)-5-((R)-3-(4-(4-((E)-1-(hydroxyimino)-2,3-dihydro-1H-inden-5-yl)-3-(pyridin-4-yl)-1H-pyrazol-1-yl)phenoxy)pyrrolidin-1-yl)isoindoline-1,3-dione | 708.45 | 5 |
| 121 | [structure] | (E)-2-(2,6-dioxopiperidin-3-yl)-5-(3-(4-(4-(1-(hydroxyimino)-2,3-dihydro-1H-inden-5-yl)-3-(pyridin-4-yl)-1H-pyrazol-1-yl)phenyl)pyrrolidin-1-yl)isoindoline-1,3-dione | 692.45 | 5 |

FIG. 2. Continued

| | | | |
|---|---|---|---|
| 122 | (structure) | (E)-2-(2,6-dioxopiperidin-3-yl)-4-(4-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione | 707.46 | 5 |
| 123 | (structure) | (E)-2-(2,6-dioxopiperidin-3-yl)-5-(4-(3-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione | 707.47 | 5 |
| 124 | (structure) | (E)-2-(2,6-dioxopiperidin-3-yl)-5-(4-(4-(1-(hydroxyimino)-2,3-dihydro-1H-inden-5-yl)-3-(pyridin-4-yl)-1H-pyrazol-1-yl)phenyl)-1,4-diazepan-1-yl)isoindoline-1,3-dione | 721.48 | 5 |

| | | | | |
|---|---|---|---|---|
| 125 |  | (E)-2-(2,6-dioxopiperidin-3-yl)-5-(4-(4-(4-(1-(hydroxyimino)-2,3-dihydro-1H-inden-5-yl)-3-(pyridin-4-yl)-1H-pyrazol-1-yl)phenethyl)piperazin-1-yl)isoindoline-1,3-dione | 735.5 | 5 |
| 126 |  | (E)-2-(2,6-dioxopiperidin-3-yl)-5-(4-(4-(4-(1-(hydroxyimino)-2,3-dihydro-1H-inden-5-yl)-3-(pyridin-4-yl)-1H-pyrazol-1-yl)benzyl)piperazin-1-yl)isoindoline-1,3-dione | 721.48 | 5 |
| 127 |  | (E)-2-(2,6-dioxopiperidin-3-yl)-5-(4-(4-(1-(hydroxyimino)-2,3-dihydro-1H-inden-5-yl)-3-(pyridin-4-yl)-1H-pyrazol-1-yl)phenyl)piperidin-1-yl)isoindoline-1,3-dione | 706.47 | 5 |

FIG. 2. Continued

| | | | |
|---|---|---|---|
| 128 | 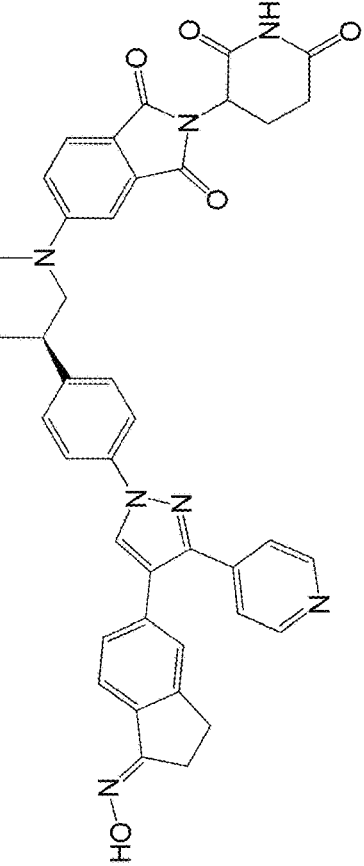 | 2-(2,6-dioxopiperidin-3-yl)-5-((R)-3-(4-(4-((E)-1-(hydroxyimino)-2,3-dihydro-1H-inden-5-yl)-3-(pyridin-4-yl)-1H-pyrazol-1-yl)phenyl)piperidin-1-yl)isoindoline-1,3-dione | 706.46 | 5 |
| 129 | 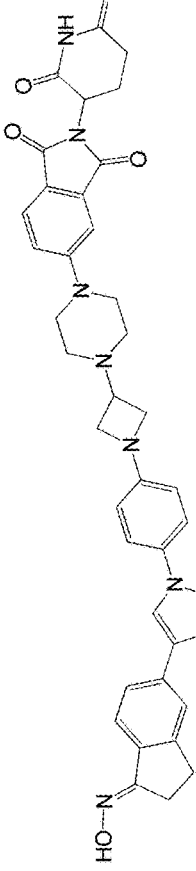 | (E)-2-(2,6-dioxopiperidin-3-yl)-5-(4-(1-(4-(4-(1-(hydroxyimino)-2,3-dihydro-1H-inden-5-yl)-3-(pyridin-4-yl)-1H-pyrazol-1-yl)phenyl)azetidin-3-yl)piperazin-1-yl)isoindoline-1,3-dione | 762.52 | 5 |
| 130 | 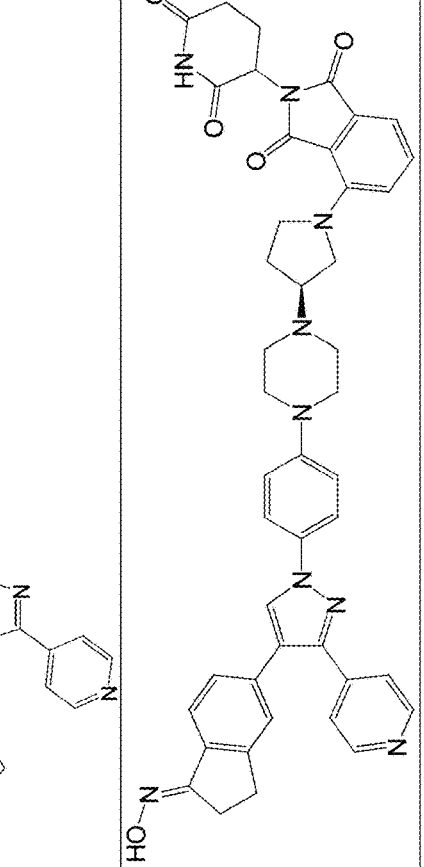 | 2-(2,6-dioxopiperidin-3-yl)-4-((S)-3-(4-(4-(1-(hydroxyimino)-2,3-dihydro-1H-inden-5-yl)-3-(pyridin-4-yl)-1H-pyrazol-1-yl)phenyl)piperazin-1-yl)pyrrolidin-1-yl)isoindoline-1,3-dione | 776.53 | 5 |

FIG. 2. Continued

| | | | | |
|---|---|---|---|---|
| 131 | 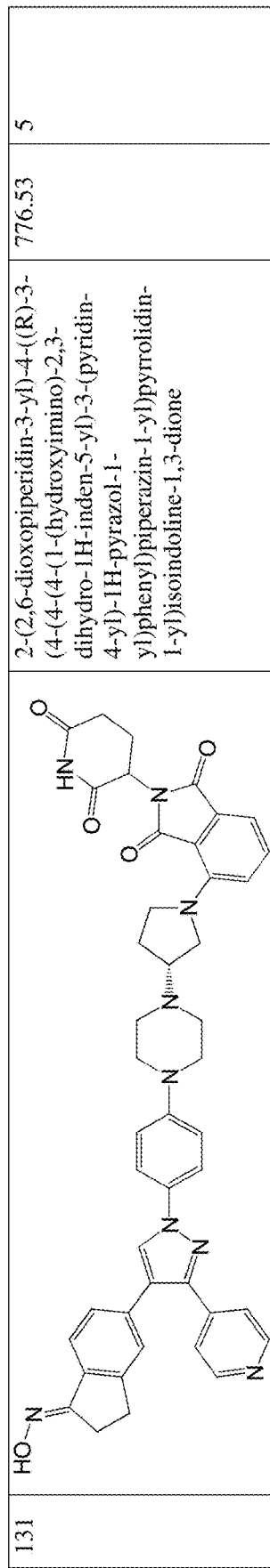 | 2-(2,6-dioxopiperidin-3-yl)-4-((R)-3-(4-(4-(1-(hydroxyimino)-2,3-dihydro-1H-inden-5-yl)-3-(pyridin-4-yl)-1H-pyrazol-1-yl)phenyl)piperazin-1-yl)pyrrolidin-1-yl)isoindoline-1,3-dione | 776.53 | 5 |
| 132 | 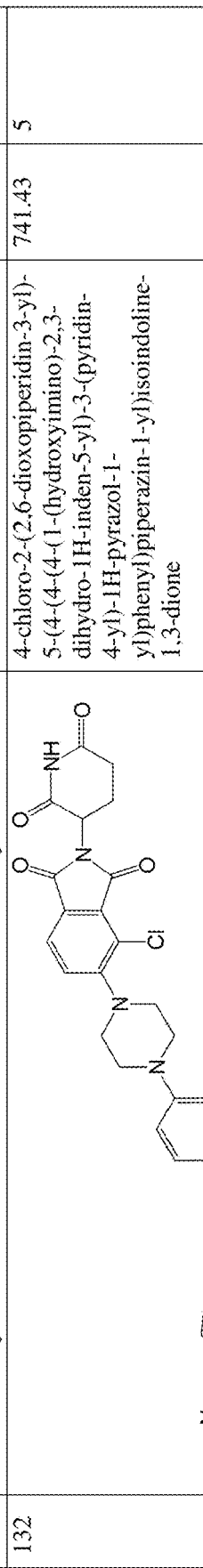 | 4-chloro-2-(2,6-dioxopiperidin-3-yl)-5-(4-(4-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione | 741.43 | 5 |
| 133 | 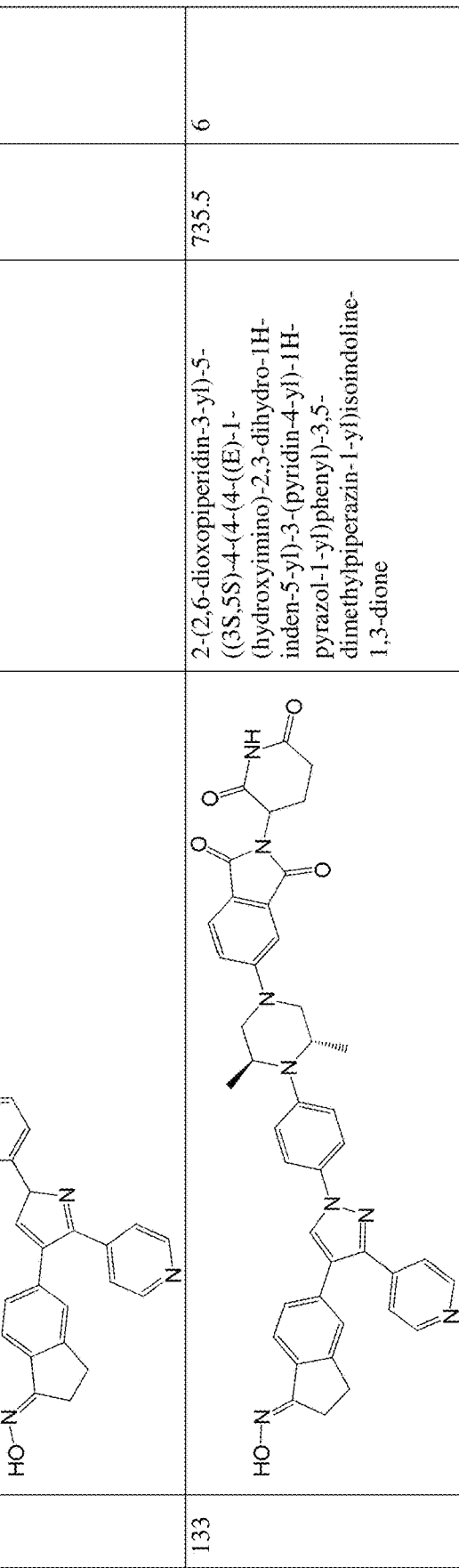 | 2-(2,6-dioxopiperidin-3-yl)-5-((3S,5S)-4-(4-(4-((E)-1-(hydroxyimino)-2,3-dihydro-1H-inden-5-yl)-3-(pyridin-4-yl)-1H-pyrazol-1-yl)phenyl)-3,5-dimethylpiperazin-1-yl)isoindoline-1,3-dione | 735.5 | 6 |

FIG. 2. Continued

| | | | |
|---|---|---|---|
| 134 | 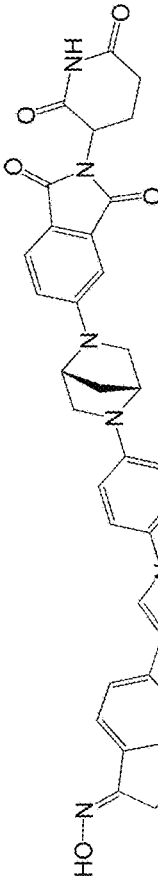 | 2-(2,6-dioxopiperidin-3-yl)-5-((1R,4R)-5-(4-(4-((E)-1-(hydroxyimino)-2,3-dihydro-1H-inden-5-yl)-3-(pyridin-4-yl)-1H-pyrazol-1-yl)phenyl)-2,5-diazabicyclo[2.2.1]heptan-2-yl)isoindoline-1,3-dione | 719.46 | 6 |
| 135 | 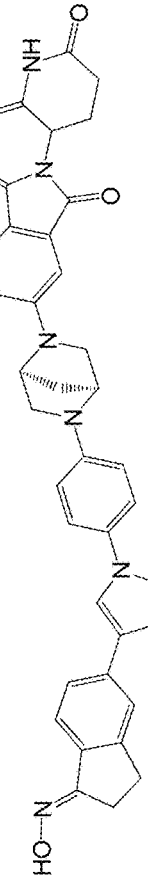 | 2-(2,6-dioxopiperidin-3-yl)-5-((1S,4S)-5-(4-(4-((E)-1-(hydroxyimino)-2,3-dihydro-1H-inden-5-yl)-3-(pyridin-4-yl)-1H-pyrazol-1-yl)phenyl)-2,5-diazabicyclo[2.2.1]heptan-2-yl)isoindoline-1,3-dione | 719.46 | 6 |
| 136 | 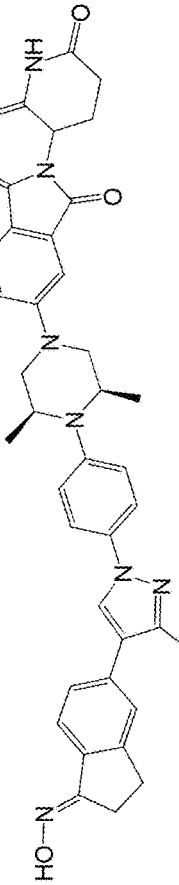 | 2-(2,6-dioxopiperidin-3-yl)-5-((3R,5S)-4-(4-(4-((E)-1-(hydroxyimino)-2,3-dihydro-1H-inden-5-yl)-3-(pyridin-4-yl)-1H-pyrazol-1-yl)phenyl)-3,5-dimethylpiperazin-1-yl)isoindoline-1,3-dione | 735.5 | 6 |

FIG. 2. Continued

| | | | |
|---|---|---|---|
| 137 | [structure] | (E)-2-(2,6-dioxopiperidin-3-yl)-5-((2-(4-(4-(1-(hydroxyimino)-2,3-dihydro-1H-inden-5-yl)-3-(pyridin-4-yl)-1H-pyrazol-1-yl)phenoxy)ethyl)(methyl)amino)isoindoline-1,3-dione | 696.45 | 6 |
| 138 | [structure] | (E)-2-(2,6-dioxopiperidin-3-yl)-4-(4-(4-(4-(1-(hydroxyimino)-2,3-dihydro-1H-inden-5-yl)-3-(pyridin-4-yl)-1H-pyrazol-1-yl)phenethyl)piperazin-1-yl)isoindoline-1,3-dione | 735.5 | 6 |
| 139 | [structure] | N-(7-(1-(4-(4-(2-(2,6-dioxopiperidin-3-yl)-1,3-dioxoisoindolin-5-yl)piperazin-1-yl)phenyl)-3-(pyridin-4-yl)-1H-pyrazol-4-yl)quinolin-4-yl)propane-1-sulfonamide | 810.49 | 6 |

| 140 | N-(3-(1-(4-(4-(2-(2,6-dioxopiperidin-3-yl)-1,3-dioxoisoindolin-5-yl)piperazin-1-yl)phenyl)-3-(pyridin-4-yl)-1H-pyrazol-4-yl)quinolin-8-yl)propane-1-sulfonamide | 810.49 | 6 |
| --- | --- | --- | --- |
| 141 | (E)-2-(2,6-dioxopiperidin-3-yl)-4-(4-(3-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione | 707.46 | 6 |

| | | | | |
|---|---|---|---|---|
| 142 |  | (E)-2-(2,6-dioxopiperidin-3-yl)-4-(4-(4-(4-(1-(hydroxyimino)-2,3-dihydro-1H-inden-5-yl)-3-(pyridin-4-yl)-1H-pyrazol-1-yl)benzyl)piperazin-1-yl)isoindoline-1,3-dione | 721.48 | 6 |
| 143 |  | (E)-2-(2,6-dioxopiperidin-3-yl)-5-fluoro-6-(4-(4-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione | 725.45 | 6 |
| 144 |  | (E)-2-(2,6-dioxopiperidin-3-yl)-5-(3-(2-(4-(4-(1-(hydroxyimino)-2,3-dihydro-1H-inden-5-yl)-3-(pyridin-4-yl)-1H-pyrazol-1-yl)phenoxy)ethyl)azetidin-1-yl)isoindoline-1,3-dione | 722.47 | 6 |

FIG. 2. Continued

| | | | |
|---|---|---|---|
| 145 | (structure) | (E)-2-(2,6-dioxopiperidin-3-yl)-5-(3-(3-(4-(4-(1-(hydroxyimino)-2,3-dihydro-1H-inden-5-yl)-3-(pyridin-4-yl)-1H-pyrazol-1-yl)phenoxy)propyl)azetidin-1-yl)isoindoline-1,3-dione | 736.48 | 6 |
| 146 | (structure) | 2-(2,6-dioxopiperidin-3-yl)-5-(((1s,3s)-3-(4-(4-((E)-1-(hydroxyimino)-2,3-dihydro-1H-inden-5-yl)-3-(pyridin-4-yl)-1H-pyrazol-1-yl)phenoxy)cyclobutyl)(methyl)amino)isoindoline-1,3-dione | 722.46 | 6 |
| 147 | (structure) | 2-(2,6-dioxopiperidin-3-yl)-5-((((1r,3r)-3-(4-(4-((E)-1-(hydroxyimino)-2,3-dihydro-1H-inden-5-yl)-3-(pyridin-4-yl)-1H-pyrazol-1-yl)phenoxy)cyclobutyl)(methyl)amino)isoindoline-1,3-dione | 722.46 | 6 |

FIG. 2. Continued

| | | | |
|---|---|---|---|
| 148 | 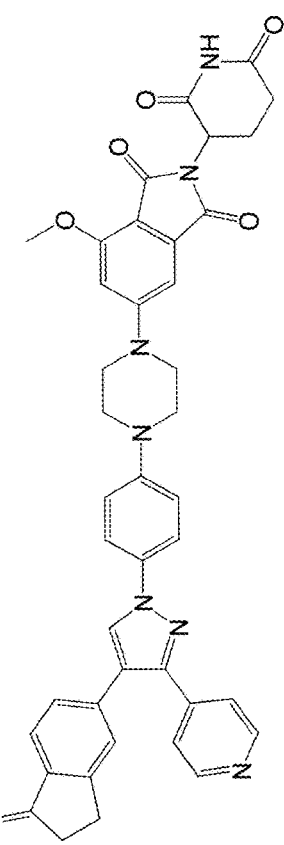 | (E)-2-(2,6-dioxopiperidin-3-yl)-6-(4-(4-(4-(1-(hydroxyimino)-2,3-dihydro-1H-inden-5-yl)-3-(pyridin-4-yl)-1H-pyrazol-1-yl)phenyl)piperazin-1-yl)-4-methoxyisoindoline-1,3-dione | 737.48 | 6 |
| 149 | 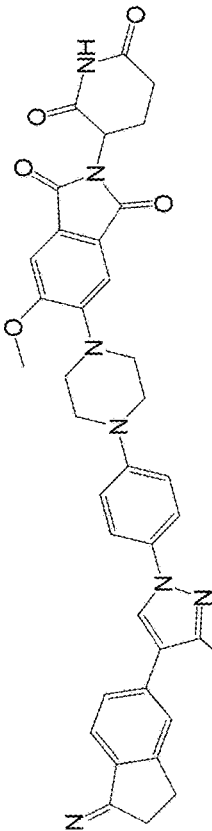 | (E)-2-(2,6-dioxopiperidin-3-yl)-5-(4-(4-(4-(1-(hydroxyimino)-2,3-dihydro-1H-inden-5-yl)-3-(pyridin-4-yl)-1H-pyrazol-1-yl)phenyl)piperazin-1-yl)-6-methoxyisoindoline-1,3-dione | 737.48 | 6 |
| 150 | 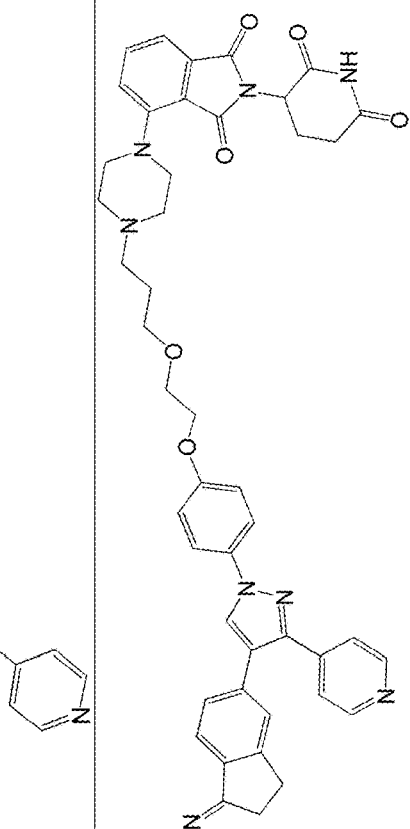 | (E)-2-(2,6-dioxopiperidin-3-yl)-4-(3-(2-(4-(4-(1-(hydroxyimino)-2,3-dihydro-1H-inden-5-yl)-3-(pyridin-4-yl)-1H-pyrazol-1-yl)phenoxy)ethoxy)propyl)piperazin-1-yl)isoindoline-1,3-dione | 809.57 | 7 |

| | | | |
|---|---|---|---|
| 151 | 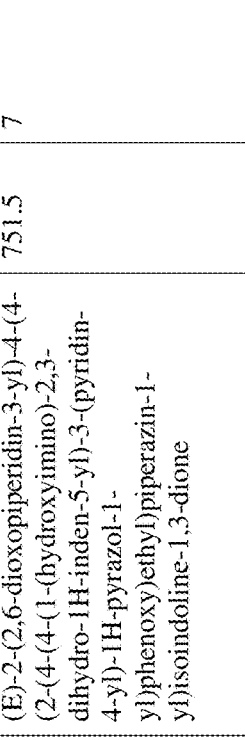 | (E)-2-(2,6-dioxopiperidin-3-yl)-4-(4-(2-(4-(4-(1-(hydroxyimino)-2,3-dihydro-1H-inden-5-yl)-3-(pyridin-4-yl)-1H-pyrazol-1-yl)phenoxy)ethyl)piperazin-1-yl)isoindoline-1,3-dione | 751.5 | 7 |
| 152 | 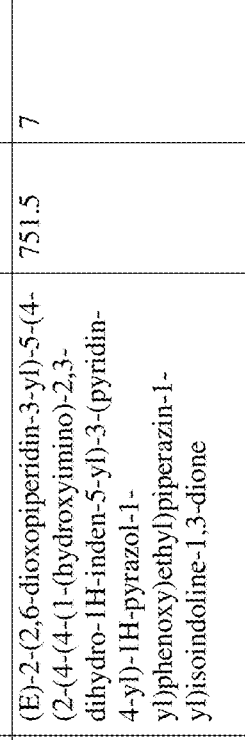 | (E)-2-(2,6-dioxopiperidin-3-yl)-5-(4-(2-(4-(4-(1-(hydroxyimino)-2,3-dihydro-1H-inden-5-yl)-3-(pyridin-4-yl)-1H-pyrazol-1-yl)phenoxy)ethyl)piperazin-1-yl)isoindoline-1,3-dione | 751.5 | 7 |
| 153 | 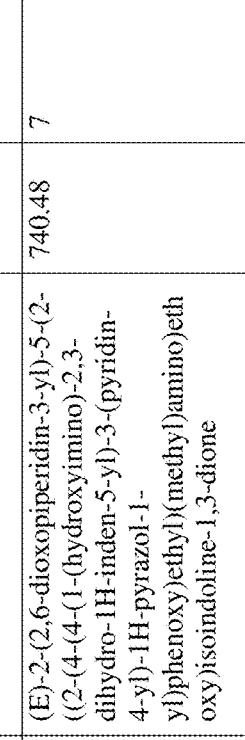 | (E)-2-(2,6-dioxopiperidin-3-yl)-5-(2-((2-(4-(4-(1-(hydroxyimino)-2,3-dihydro-1H-inden-5-yl)-3-(pyridin-4-yl)-1H-pyrazol-1-yl)phenoxy)ethyl)(methyl)amino)ethoxy)isoindoline-1,3-dione | 740.48 | 7 |

| | | | |
|---|---|---|---|
| 154 | (structure) | (E)-2-(2,6-dioxopiperidin-3-yl)-5-(4-(2-(3-(4-(1-(hydroxyimino)-2,3-dihydro-1H-inden-5-yl)-3-(pyridin-4-yl)-1H-pyrazol-1-yl)phenoxy)ethyl)piperazin-1-yl)isoindoline-1,3-dione | 751.5 / 7 |
| 155 | (structure) | N-(3-(1-(4-(2-(2-(2-(4-(2-(2,6-dioxopiperidin-3-yl)-1,3-dioxoisoindolin-5-yl)piperazin-1-yl)ethoxy)ethoxy)phenyl)-3-(pyridin-4-yl)-1H-pyrazol-4-yl)quinolin-8-yl)propane-1-sulfonamide | 942.6 / 7 |
| 156 | (structure) | N-(7-(1-(4-(2-(4-(2-(2,6-dioxoisoindolin-5-yl)piperazin-1-yl)ethoxy)phenyl)-3-(pyridin-4-yl)-1H-pyrazol-4-yl)quinolin-4-yl)propane-1-sulfonamide | 854.53 / 7 |
| 157 | (structure) | N-(7-(1-(4-(2-(2-(4-(2-(2,6-dioxopiperidin-3-yl)-1,3-dioxoisoindolin-5-yl)piperazin-1-yl)ethoxy)phenyl)-1H-pyrazol-4-yl)(pyridin-4-yl)-1H-pyrazol-4-yl)quinolin-4-yl)propane-1-sulfonamide | 898.56 / 7 |

FIG. 2. Continued

| # | Structure | Name | | |
|---|---|---|---|---|
| 158 | 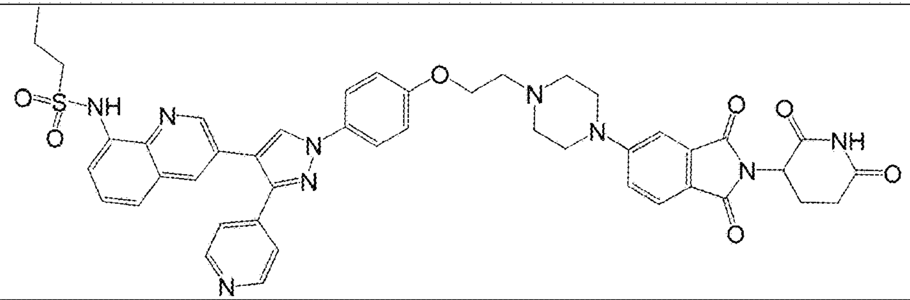 | N-(3-(1-(4-(2-(4-(2-(2,6-dioxopiperidin-3-yl)-1,3-dioxoisoindolin-5-yl)piperazin-1-yl)ethoxy)phenyl)-3-(pyridin-4-yl)-1H-pyrazol-4-yl)quinolin-8-yl)propane-1-sulfonamide | 854.53 | 7 |
| 159 | 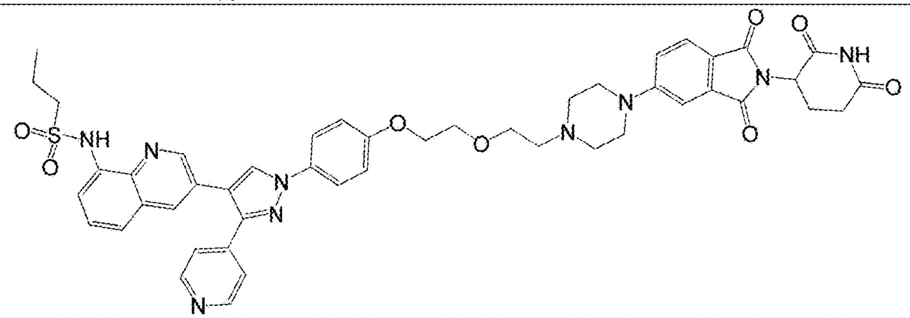 | N-(3-(1-(4-(2-(2-(4-(2-(2,6-dioxopiperidin-3-yl)-1,3-dioxoisoindolin-5-yl)piperazin-1-yl)ethoxy)ethoxy)phenyl)-3-(pyridin-4-yl)-1H-pyrazol-4-yl)quinolin-8-yl)propane-1-sulfonamide | 898.56 | 7 |
| 160 | 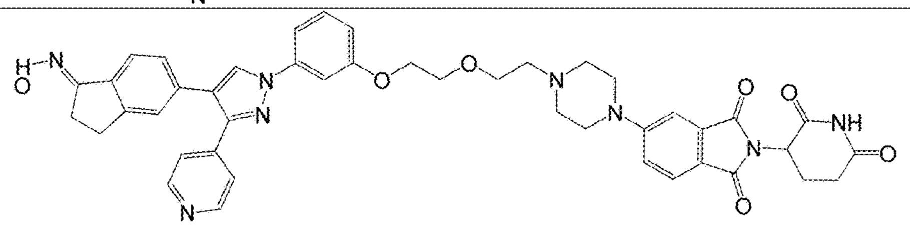 | (E)-2-(2,6-dioxopiperidin-3-yl)-5-(4-(2-(2-(3-(4-(1-(hydroxyimino)-2,3-dihydro-1H-inden-5-yl)-3-(pyridin-4-yl)-1H-pyrazol-1-yl)phenoxy)ethoxy)ethyl)piperazin-1-yl)isoindoline-1,3-dione | 795.53 | 7 |
| 161 | 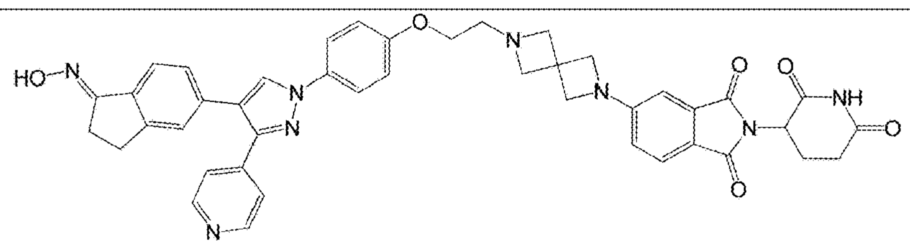 | (E)-2-(2,6-dioxopiperidin-3-yl)-5-(6-(2-(4-(4-(1-(hydroxyimino)-2,3-dihydro-1H-inden-5-yl)-3-(pyridin-4-yl)-1H-pyrazol-1-yl)phenoxy)ethyl)-2,6-diazaspiro[3.3]heptan-2-yl)isoindoline-1,3-dione | 763.5 | 7 |

FIG. 2. Continued

| | | | |
|---|---|---|---|
| 162 | [structure] | (E)-2-(2,6-dioxopiperidin-3-yl)-4-(4-(4-(4-(1-(hydroxyimino)-2,3-dihydro-1H-inden-5-yl)-3-(pyridin-4-yl)-1H-pyrazol-1-yl)phenoxy)butyl)piperazin-1-yl)isoindoline-1,3-dione | 779.53 | 7 |
| 163 | [structure] | (E)-2-(2,6-dioxopiperidin-3-yl)-4-(3-(4-(4-(1-(hydroxyimino)-2,3-dihydro-1H-inden-5-yl)-3-(pyridin-4-yl)-1H-pyrazol-1-yl)phenoxy)propyl)piperazin-1-yl)isoindoline-1,3-dione | 765.52 | 7 |
| 164 | [structure] | (E)-2-(2,6-dioxopiperidin-3-yl)-5-(4-(3-(4-(4-(1-(hydroxyimino)-2,3-dihydro-1H-inden-5-yl)-3-(pyridin-4-yl)-1H-pyrazol-1-yl)phenoxy)propyl)piperazin-1-yl)isoindoline-1,3-dione | 765.51 | 7 |

FIG. 2. Continued

| 165 | [structure] | (E)-2-(2,6-dioxopiperidin-3-yl)-5-(4-(4-(4-(1-(hydroxyimino)-2,3-dihydro-1H-inden-5-yl)-3-(pyridin-4-yl)-1H-pyrazol-1-yl)phenoxy)butyl)piperazin-1-yl)isoindoline-1,3-dione | 779.53 | 7 |
| 166 | [structure] | (E)-2-(2,6-dioxopiperidin-3-yl)-5-(4-((1-(4-(4-(1-(hydroxyimino)-2,3-dihydro-1H-inden-5-yl)-3-(pyridin-4-yl)-1H-pyrazol-1-yl)phenyl)piperidin-4-yl)methyl)piperazin-1-yl)isoindoline-1,3-dione | 804.57 | 7 |
| 167 | [structure] | (E)-2-(2,6-dioxopiperidin-3-yl)-5-(4-(1-(2-(4-(4-(1-(hydroxyimino)-2,3-dihydro-1H-inden-5-yl)-3-(pyridin-4-yl)-1H-pyrazol-1-yl)phenoxy)ethyl)azetidin-3-yl)piperidin-1-yl)isoindoline-1,3-dione | 805.55 | 7 |

FIG. 2. Continued

| | | | |
|---|---|---|---|
| 168 | (E)-3-(5-(4-(2-(4-(4-(1-(hydroxyimino)-2,3-dihydro-1H-inden-5-yl)-3-(pyridin-4-yl)-1H-pyrazol-1-yl)phenoxy)ethyl)piperazin-1-yl)-1-oxoisoindolin-2-yl)piperidine-2,6-dione | 737.51 | 7 |
| 169 | (E)-2-(2,6-dioxopiperidin-3-yl)-5-(4-(2-(1-(4-(4-(1-(hydroxyimino)-2,3-dihydro-1H-inden-5-yl)-3-(pyridin-4-yl)-1H-pyrazol-1-yl)phenyl)piperidin-4-yl)ethyl)piperazin-1-yl)isoindoline-1,3-dione | 818.59 | 7 |
| 170 | (E)-2-(2,6-dioxopiperidin-3-yl)-5-(((1-(2-(4-(4-(1-(hydroxyimino)-2,3-dihydro-1H-inden-5-yl)-3-(pyridin-4-yl)-1H-pyrazol-1-yl)phenoxy)ethyl)piperidin-4-yl)oxy)isoindoline-1,3-dione | 766.5 | 7 |
| 171 | (E)-2-(2,6-dioxopiperidin-3-yl)-5-(((1-(2-(4-(4-(1-(hydroxyimino)-2,3-dihydro-1H-inden-5-yl)-3-(pyridin-4-yl)-1H-pyrazol-1-yl)phenoxy)ethyl)piperidin-4-yl)methoxy)isoindoline-1,3-dione | 780.51 | 7 |

FIG. 2. Continued

| | | | |
|---|---|---|---|
| 172 | [structure] | (E)-2-(2,6-dioxopiperidin-3-yl)-5-(2-(4-(2-(4-(4-(1-(hydroxyimino)-2,3-dihydro-1H-inden-5-yl)-3-(pyridin-4-yl)-1H-pyrazol-1-yl)phenoxy)ethyl)piperazin-1-yl)ethoxy)isoindoline-1,3-dione | 795.53 | 7 |
| 173 | [structure] | (E)-2-(2,6-dioxopiperidin-3-yl)-4-(2-(4-(4-(1-(hydroxyimino)-2,3-dihydro-1H-inden-5-yl)-3-(pyridin-4-yl)-1H-pyrazol-1-yl)phenyl)piperazin-1-yl)ethoxy)isoindoline-1,3-dione | 751.5 | 8 |
| 174 | [structure] | (E)-2-(2,6-dioxopiperidin-3-yl)-4-(4-(4-(4-(1-(hydroxyimino)-2,3-dihydro-1H-inden-5-yl)-3-(pyridin-4-yl)-1H-pyrazol-1-yl)phenyl)piperazin-1-yl)butoxy)isoindoline-1,3-dione | 779.53 | 8 |

FIG. 2. Continued

| 175 | (E)-2-(2,6-dioxopiperidin-3-yl)-4-(3-(4-(4-(4-(1-(hydroxyimino)-2,3-dihydro-1H-inden-5-yl)-3-(pyridin-4-yl)-1H-pyrazol-1-yl)phenyl)piperazin-1-yl)azetidin-1-yl)isoindoline-1,3-dione | 762.51 | 8 |
| --- | --- | --- | --- |
| 176 | (E)-2-(2,6-dioxopiperidin-3-yl)-4-(3-((4-(4-(4-(1-(hydroxyimino)-2,3-dihydro-1H-inden-5-yl)-3-(pyridin-4-yl)-1H-pyrazol-1-yl)phenyl)piperidin-1-yl)methyl)azetidin-1-yl)isoindoline-1,3-dione | 776.53 | 8 |
| 177 | (E)-2-(2,6-dioxopiperidin-3-yl)-5-(3-(4-(4-(4-(1-(hydroxyimino)-2,3-dihydro-1H-inden-5-yl)-3-(pyridin-4-yl)-1H-pyrazol-1-yl)phenyl)piperidin-1-yl)azetidin-1-yl)isoindoline-1,3-dione | 761.52 | 8 |

FIG. 2. Continued

| | | | |
|---|---|---|---|
| 178 | [structure] | (E)-2-(2,6-dioxopiperidin-3-yl)-4-(3-((3-(4-(4-(1-(hydroxyimino)-2,3-dihydro-1H-inden-5-yl)-3-(pyridin-4-yl)-1H-pyrazol-1-yl)phenyl)azetidin-1-yl)methyl)azetidin-1-yl)isoindoline-1,3-dione | 747.5 | 8 |
| 179 | [structure] | (E)-2-(2,6-dioxopiperidin-3-yl)-5-(3-((3-(4-(4-(1-(hydroxyimino)-2,3-dihydro-1H-inden-5-yl)-3-(pyridin-4-yl)-1H-pyrazol-1-yl)phenyl)azetidin-1-yl)methyl)azetidin-1-yl)isoindoline-1,3-dione | 747.5 | 8 |
| 180 | [structure] | (E)-2-(2,6-dioxopiperidin-3-yl)-4-(3-(3-(4-(4-(1-(hydroxyimino)-2,3-dihydro-1H-inden-5-yl)-3-(pyridin-4-yl)-1H-pyrazol-1-yl)phenyl)azetidin-1-yl)propoxy)isoindoline-1,3-dione | 736.48 | 8 |

FIG. 2. Continued

| | | | |
|---|---|---|---|
| 181 | [structure] | (E)-2-(2,6-dioxopiperidin-3-yl)-4-(4-(3-(4-(4-(1-(hydroxyimino)-2,3-dihydro-1H-inden-5-yl)-3-(pyridin-4-yl)-1H-pyrazol-1-yl)phenyl)azetidin-1-yl)butoxy)isoindoline-1,3-dione | 750.5 | 8 |
| 182 | [structure] | N-(3-(5-((1-(2-(2,6-dioxopiperidin-3-yl)-1,3-dioxoisoindolin-4-yl)piperidin-4-yl)(methyl)amino)-3-(pyrimidin-5-yl)-1H-pyrrolo[3,2-b]pyridin-1-yl)-2,4-difluorophenyl)propane-1-sulfonamide | 798.47 | 9 |
| 183 | [structure] | N-(3-(5-((1-(2-(2,6-dioxopiperidin-3-yl)-1,3-dioxoisoindolin-5-yl)piperidin-4-yl)(methyl)amino)-3-(pyrimidin-5-yl)-1H-pyrrolo[3,2-b]pyridin-1-yl)-2,4-difluorophenyl)propane-1-sulfonamide | 798.47 | 9 |

FIG. 2. Continued

| | | | |
|---|---|---|---|
| 184 | [structure] | N-(3-(5-((1-(2-(2-(2,6-dioxopiperidin-3-yl))-1,3-dioxoisoindolin-4-yl)oxy)ethyl)piperidin-4-yl)(methyl)amino)-3-(pyrimidin-5-yl)-1H-pyrrolo[3,2-b]pyridin-1-yl)-2,4-difluorophenyl)propane-1-sulfonamide | 842.51 | 10 |
| 185 | [structure] | N-(3-(5-((1-(2-(2-(2-(2,6-dioxopiperidin-3-yl))-1,3-dioxoisoindolin-5-yl)oxy)ethoxy)ethyl)piperidin-4-yl)(methyl)amino)-3-(pyrimidin-5-yl)-1H-pyrrolo[3,2-b]pyridin-1-yl)-2,4-difluorophenyl)propane-1-sulfonamide | 886.54 | 10 |
| 186 | [structure] | N-(3-(5-((1-(2-(2-(2,6-dioxopiperidin-3-yl))-1,3-dioxoisoindolin-5-yl)oxy)ethyl)piperidin-4-yl)(methyl)amino)-3-(pyrimidin-5-yl)-1H-pyrrolo[3,2-b]pyridin-1-yl)-2,4-difluorophenyl)propane-1-sulfonamide | 842.51 | 10 |

FIG. 2. Continued

| | | | |
|---|---|---|---|
| 187 | [structure] | N-(3-(5-((1-(2-(2-((2-(2,6-dioxopiperidin-3-yl)-1,3-dioxoisoindolin-4-yl)oxy)ethoxy)ethyl)piperidin-4-yl)(methyl)amino)-3-(pyrimidin-5-yl)-1H-pyrrolo[3,2-b]pyridin-1-yl)-2,4-difluorophenyl)propane-1-sulfonamide | 886.54 | 10 |
| 188 | [structure] | N-(3-(5-((1-(2-(2-(2-(2-(2,6-dioxopiperidin-3-yl)-1,3-dioxoisoindolin-5-yl)oxy)ethoxy)ethyl)piperidin-4-yl)(methyl)amino)-3-(pyrimidin-5-yl)-1H-pyrrolo[3,2-b]pyridin-1-yl)-2,4-difluorophenyl)propane-1-sulfonamide | 930.58 | 10 |
| 189 | [structure] | N-(3-(5-((1-(2-(2-(2-(2-(2,6-dioxopiperidin-3-yl)-1,3-dioxoisoindolin-4-yl)oxy)ethoxy)ethyl)piperidin-4-yl)(methyl)amino)-3-(pyrimidin-5-yl)-1H-pyrrolo[3,2-b]pyridin-1-yl)-2,4-difluorophenyl)propane-1-sulfonamide | 930.57 | 10 |

FIG. 2. Continued

| | | | |
|---|---|---|---|
| 190 | 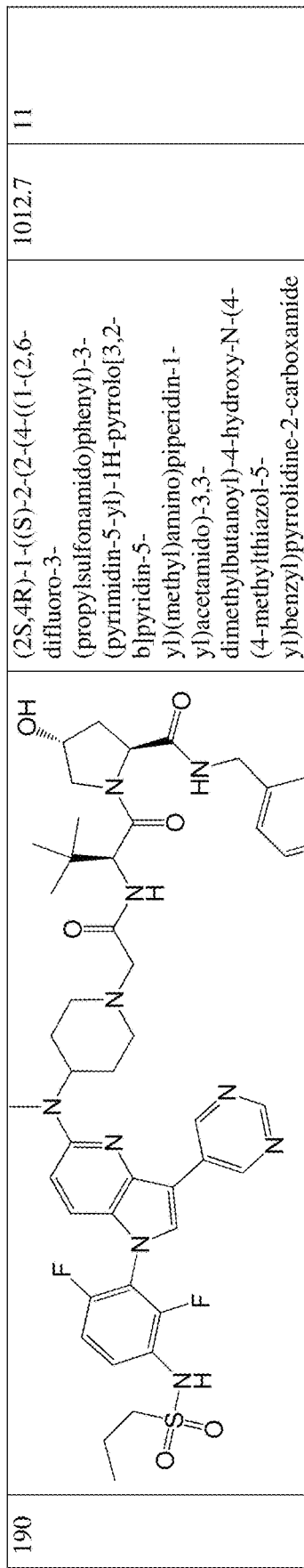 | (2S,4R)-1-((S)-2-(2-(4-((1-(2,6-difluoro-3-(propylsulfonamido)phenyl)-3-(pyrimidin-5-yl)-1H-pyrrolo[3,2-b]pyridin-5-yl)(methyl)amino)piperidin-1-yl)acetamido)-3,3-dimethylbutanoyl)-4-hydroxy-N-(4-(4-methylthiazol-5-yl)benzyl)pyrrolidine-2-carboxamide | 1012.7 | 11 |
| 191 | 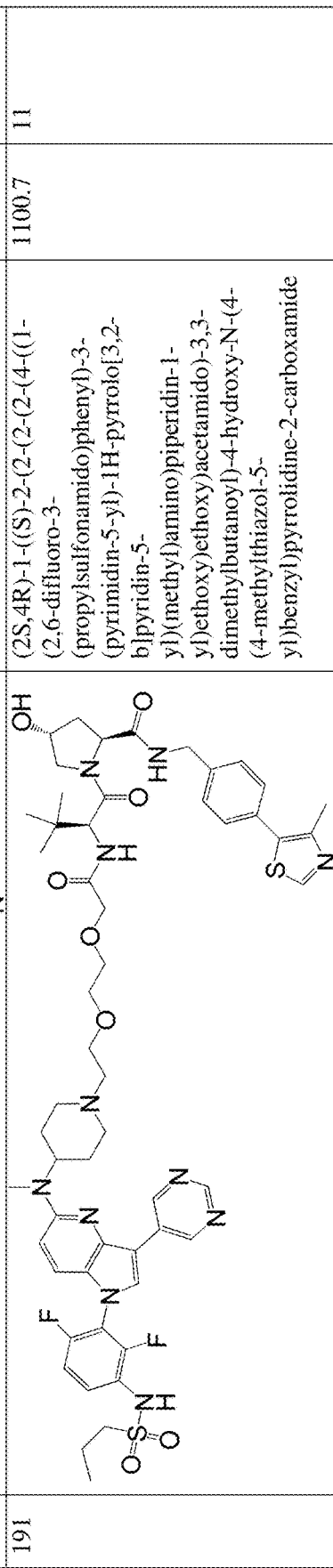 | (2S,4R)-1-((S)-2-(2-(2-(4-((1-(2,6-difluoro-3-(propylsulfonamido)phenyl)-3-(pyrimidin-5-yl)-1H-pyrrolo[3,2-b]pyridin-5-yl)(methyl)amino)piperidin-1-yl)ethoxy)ethoxy)acetamido)-3,3-dimethylbutanoyl)-4-hydroxy-N-(4-(4-methylthiazol-5-yl)benzyl)pyrrolidine-2-carboxamide | 1100.7 | 11 |

FIG. 2. Continued

| | | | |
|---|---|---|---|
| 192 | 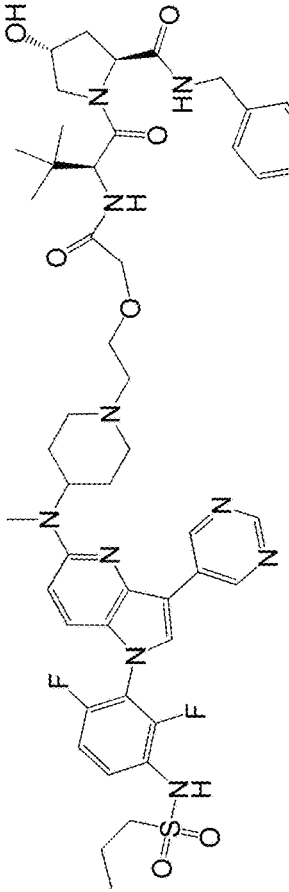 | (2S,4R)-1-((S)-2-(2-(2-(4-((1-(2,6-difluoro-3-(propylsulfonamido)phenyl)-3-(pyrimidin-5-yl)-1H-pyrrolo[3,2-b]pyridin-5-yl)(methyl)amino)piperidin-1-yl)ethoxy)acetamido)-3,3-dimethylbutanoyl)-4-hydroxy-N-(4-(4-methylthiazol-5-yl)benzyl)pyrrolidine-2-carboxamide | 1056.69 | 11 |
| 196 | 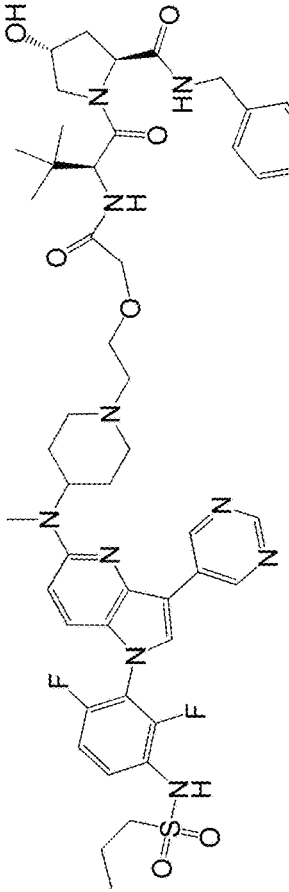 | (E)-2-(2,6-dioxopiperidin-3-yl)-5-(3-(4-(4-(1-(hydroxyimino)-2,3-dihydro-1H-inden-5-yl)-3-(pyridin-4-yl)-1H-pyrazol-1-yl)phenoxy)butoxy)phenyl)isoindoline-1,3-dione | 787.26 | Custom |
| 197 | 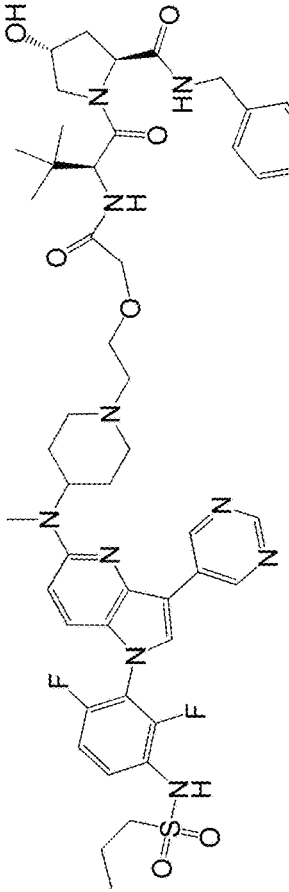 | (E)-2-(2,6-dioxopiperidin-3-yl)-5-(4-(2-(2-(4-(4-(1-(hydroxyimino)-2,3-dihydro-1H-inden-5-yl)-3-(pyridin-4-yl)-1H-pyrazol-1-yl)phenoxy)ethoxy)ethyl)piperazin-1-yl)isoindoline-1,3-dione | 795.28 | Custom |

FIG. 2. Continued

| | | | |
|---|---|---|---|
| 198 | [structure] | (E)-2-(2,6-dioxopiperidin-3-yl)-5-(2-(2-(4-(4-(1-(hydroxyimino)-2,3-dihydro-1H-inden-5-yl)-3-(pyridin-4-yl)-1H-pyrazol-1-yl)phenyl)piperazin-1-yl)ethoxy)ethoxy)isoindoline-1,3-dione | 795.28 | Custom |
| 199 | [structure] | (E)-2-(2,6-dioxopiperidin-3-yl)-4-(3-(4-(4-(1-(hydroxyimino)-2,3-dihydro-1H-inden-5-yl)-3-(pyridin-4-yl)-1H-pyrazol-1-yl)phenyl)piperazin-1-yl)propoxy)isoindoline-1,3-dione | 765.52 | Custom |
| 200 | [structure] | (E)-2-(2,6-dioxopiperidin-3-yl)-4-(3-(4-(4-(1-(hydroxyimino)-2,3-dihydro-1H-inden-5-yl)-3-(pyridin-4-yl)-1H-pyrazol-1-yl)phenoxy)propoxy)phenyl)isoindoline-1,3-dione | 773.16 | Custom |
| 201 | [structure] | (E)-5-(4-(4-(4-(1-(hydroxyimino)-2,3-dihydro-1H-inden-5-yl)-3-(pyridin-4-yl)-1H-pyrazol-1-yl)phenyl)piperazin-1-yl)-2-(1-methyl-2,6-dioxopiperidin-3-yl)isoindoline-1,3-dione | 721.49 | Custom |

FIG. 2. Continued

| # | Structure | Name | MW | Source |
|---|---|---|---|---|
| 202 | 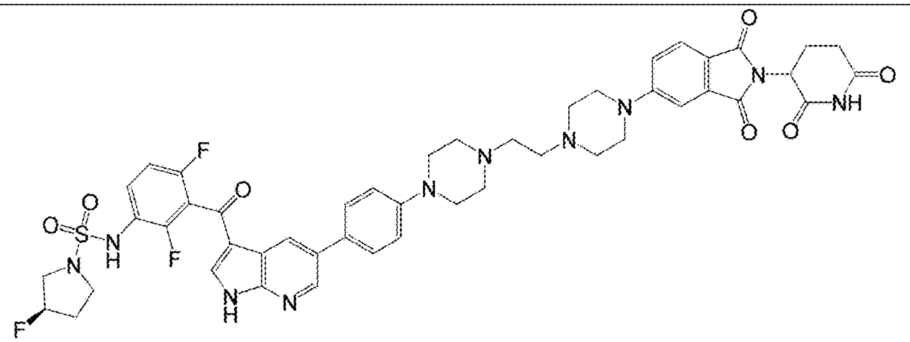 | (3R)-N-(3-(5-(4-(4-(2-(4-(2-(2,6-dioxopiperidin-3-yl)-1,3-dioxoisoindolin-5-yl)piperazin-1-yl)ethyl)piperazin-1-yl)phenyl)-1H-pyrrolo[2,3-b]pyridine-3-carbonyl)-2,4-difluorophenyl)-3-fluoropyrrolidine-1-sulfonamide | 953.58 | Custom |
| 203 | 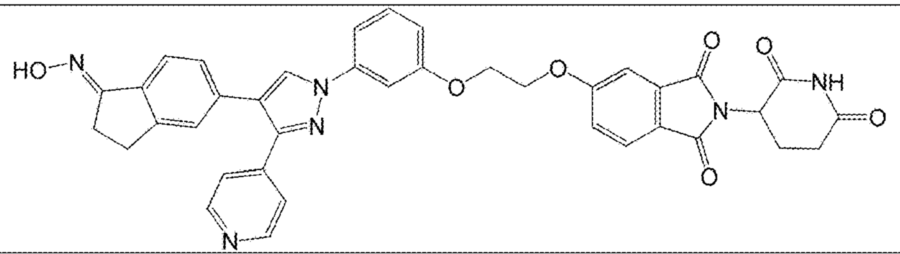 | (E)-2-(2,6-dioxopiperidin-3-yl)-5-(2-(3-(4-(1-(hydroxyimino)-2,3-dihydro-1H-inden-5-yl)-3-(pyridin-4-yl)-1H-pyrazol-1-yl)phenoxy)ethoxy)isoindoline-1,3-dione | 683.41 | Custom |
| 204 | 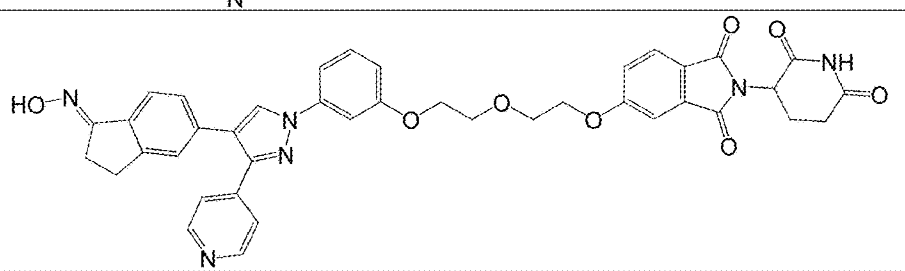 | (E)-2-(2,6-dioxopiperidin-3-yl)-5-(2-(2-(3-(4-(1-(hydroxyimino)-2,3-dihydro-1H-inden-5-yl)-3-(pyridin-4-yl)-1H-pyrazol-1-yl)phenoxy)ethoxy)isoindoline-1,3-dione | 727.45 | Custom |
| 205 | 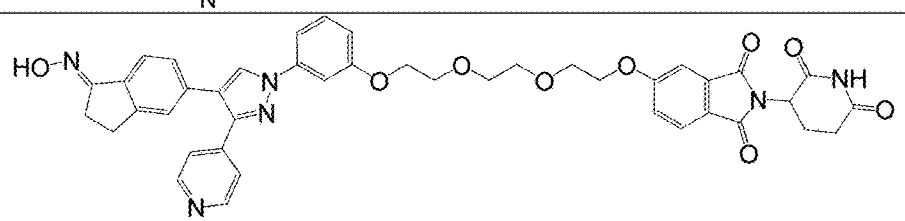 | (E)-2-(2,6-dioxopiperidin-3-yl)-5-(2-(2-(3-(4-(1-(hydroxyimino)-2,3-dihydro-1H-inden-5-yl)-3-(pyridin-4-yl)-1H-pyrazol-1-yl)phenoxy)ethoxy)ethoxy)isoindoline-1,3-dione | 771.48 | Custom |

FIG. 2. Continued

| 206 | [structure] | (E)-2-(2,6-dioxopiperidin-3-yl)-5-(2-(4-(4-(1-(hydroxyimino)-2,3-dihydro-1H-inden-5-yl)-3-(pyridin-4-yl)-1H-pyrazol-1-yl)piperidin-1-yl)ethoxy)isoindoline-1,3-dione | 674.47 | Custom |
| --- | --- | --- | --- | --- |
| 207 | [structure] | (E)-2-(2,6-dioxopiperidin-3-yl)-5-(4-(4-(1-(hydroxyimino)-2,3-dihydro-1H-inden-5-yl)-3-(pyridin-4-yl)-1H-pyrazol-1-yl)-[1,4'-bipiperidin]-1'-yl)isoindoline-1,3-dione | 713.51 | Custom |
| 208 | [structure] | (3R)-N-(3-(5-(4-(2-(2-(2-(4-(2-(2,6-dioxopiperidin-3-yl)-1,3-dioxoisoindolin-5-yl)piperazin-1-yl)ethoxy)ethoxy)ethoxy)phenyl)-1H-pyrrolo[2,3-b]pyridine-3-carbonyl)-2,4-difluorophenyl)-3-fluoropyrrolidine-1-sulfonamide | 1017.59 | Custom |

| | | | |
|---|---|---|---|
| 209 |  | 2-(2,6-dioxopiperidin-3-yl)-5-(4-((((1S,3R)-3-(4-((E)-1-(hydroxyimino)-2,3-dihydro-1H-inden-5-yl)-3-(pyridin-4-yl)-1H-pyrazol-1-yl)cyclohexyl)oxy)piperidin-1-yl)isoindoline-1,3-dione | 728.51 | Custom |
| 210 |  | 2-(2,6-dioxopiperidin-3-yl)-5-(4-((((1R,3R)-3-(4-((E)-1-(hydroxyimino)-2,3-dihydro-1H-inden-5-yl)-3-(pyridin-4-yl)-1H-pyrazol-1-yl)cyclohexyl)oxy)piperidin-1-yl)isoindoline-1,3-dione | 728.51 | Custom |

FIG. 2. Continued

| | | | |
|---|---|---|---|
| 211 | [structure] | (E)-2-(2,6-dioxopiperidin-3-yl)-5-(3-(1-(2-(4-(4-(1-(hydroxyimino)-2,3-dihydro-1H-inden-5-yl)-3-(pyridin-4-yl)-1H-pyrazol-1-yl)phenoxy)ethyl)piperidin-4-yl)azetidin-1-yl)isoindoline-1,3-dione | 805.56 | Custom |
| 212 | [structure] | (E)-2-(2,6-dioxopiperidin-3-yl)-4-(2-(2-(3-(2-(4-(4-(1-(hydroxyimino)-2,3-dihydro-1H-inden-5-yl)-3-(pyridin-4-yl)-1H-pyrazol-1-yl)phenoxy)ethoxy)phenoxy)ethoxy)isoindoline-1,3-dione | 863.53 | Custom 1 |
| 213 | [structure] | (E)-2-(2,6-dioxopiperidin-3-yl)-4-(3-(2-(2-((4-(4-(1-(hydroxyimino)-2,3-dihydro-1H-inden-5-yl)-3-(pyridin-4-yl)-1H-pyrazol-1-yl)phenoxy)methyl)phenoxy)ethoxy)propoxy)isoindoline-1,3-dione | 847.53 | Custom 1 |
| 214 | [structure] | (E)-2-(2,6-dioxopiperidin-3-yl)-4-(3-((4'-(4-(1-(hydroxyimino)-2,3-dihydro-1H-inden-5-yl)-3-(pyridin-4-yl)-1H-pyrazol-1-yl)-[1,1'-biphenyl]-3-yl)oxy)propoxy)isoindoline-1,3-dione | 773.16 | Custom 2 |

FIG. 2. Continued

| | Structure | Name | Mass | Activity |
|---|---|---|---|---|
| 215 | 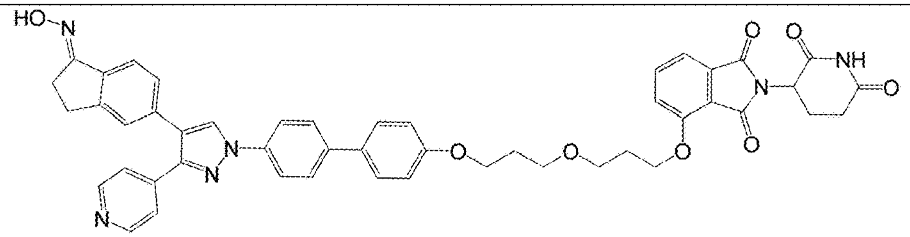 | (E)-2-(2,6-dioxopiperidin-3-yl)-4-(3-(3-((4'-(4-(1-(hydroxyimino)-2,3-dihydro-1H-inden-5-yl)-3-(pyridin-4-yl)-1H-pyrazol-1-yl)-[1,1'-biphenyl]-4-yl)oxy)propoxy)propoxy)isoindoline-1,3-dione | 831.54 | Custom 2 |
| 216 | 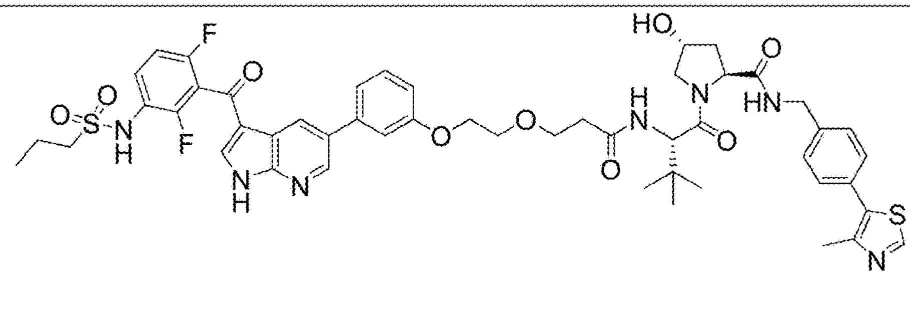 | (2S,4R)-1-((S)-2-(3-(2-(3-(3-(2,6-difluoro-3-(propylsulfonamido)benzoyl)-1H-pyrrolo[2,3-b]pyridin-5-yl)phenoxy)ethoxy)propanamido)-3,3-dimethylbutanoyl)-4-hydroxy-N-(4-(4-methylthiazol-5-yl)benzyl)pyrrolidine-2-carboxamide | 1000.35 | |
| 217 | 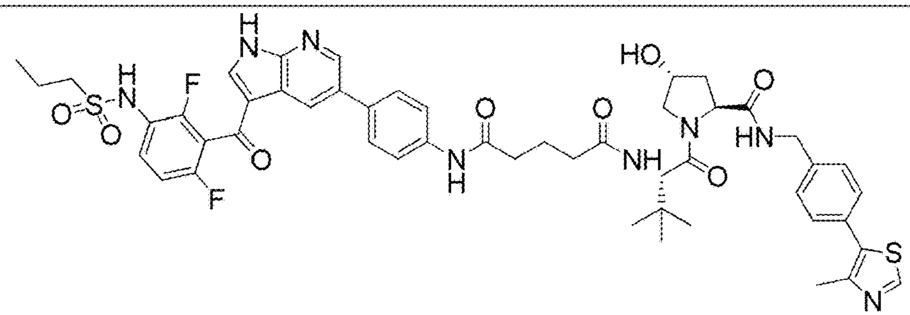 | N1-(4-(3-(2,6-difluoro-3-(propylsulfonamido)benzoyl)-1H-pyrrolo[2,3-b]pyridin-5-yl)phenyl)-N5-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide. | 997.35 | B |

FIG. 2. Continued

| | | | |
|---|---|---|---|
| 218 | [structure] | (2S,4R)-1-((S)-2-(5-(4-(3-(2,6-difluoro-3-(propylsulfonamido)benzoyl)-1H-pyrrolo[2,3-b]pyridin-5-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide | 990.38 | C |
| 219 | [structure] | (2S,4R)-1-((S)-2-(4-(4-(3-(2,6-difluoro-3-(propylsulfonamido)benzoyl)-1H-pyrrolo[2,3-b]pyridin-5-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide | 976.37 | C |
| 220 | [structure] | N1-(4-(3-(2,6-difluoro-3-(propylsulfonamido)benzoyl)-1H-pyrrolo[2,3-b]pyridin-5-yl)phenyl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-succinamide | 983.36 | B |

FIG. 2. Continued

| # | Structure | Name | Mass | Activity |
|---|---|---|---|---|
| 221 | 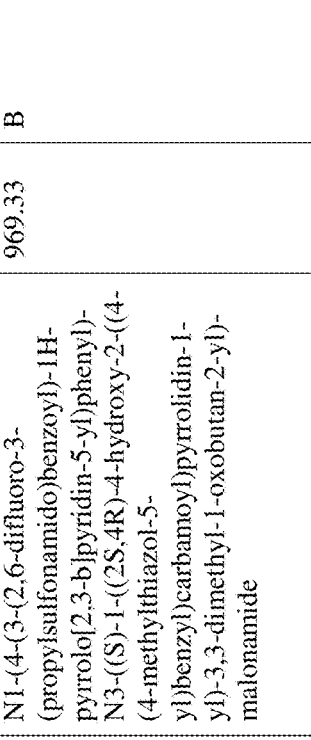 | N1-(4-(3-(2,6-difluoro-3-(propylsulfonamido)benzoyl)-1H-pyrrolo[2,3-b]pyridin-5-yl)phenyl)-N3-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-malonamide | 969.33 | B |
| 222 | 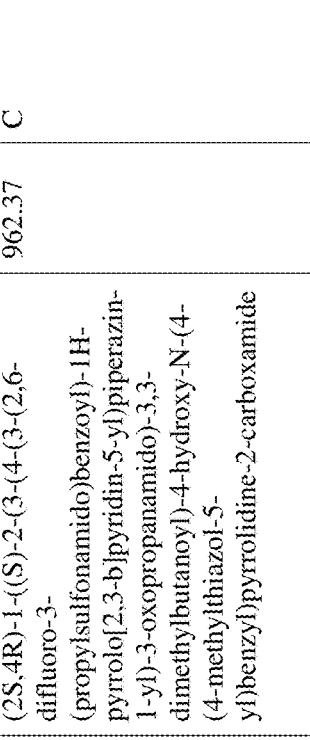 | (2S,4R)-1-((S)-2-(3-(4-(3-(2,6-difluoro-3-(propylsulfonamido)benzoyl)-1H-pyrrolo[2,3-b]pyridin-5-yl)piperazin-1-yl)-3-oxopropanamido)-3,3-dimethylbutanoyl)-4-hydroxy-N-(4-(4-methylthiazol-5-yl)benzyl)pyrrolidine-2-carboxamide | 962.37 | C |
| 223 | 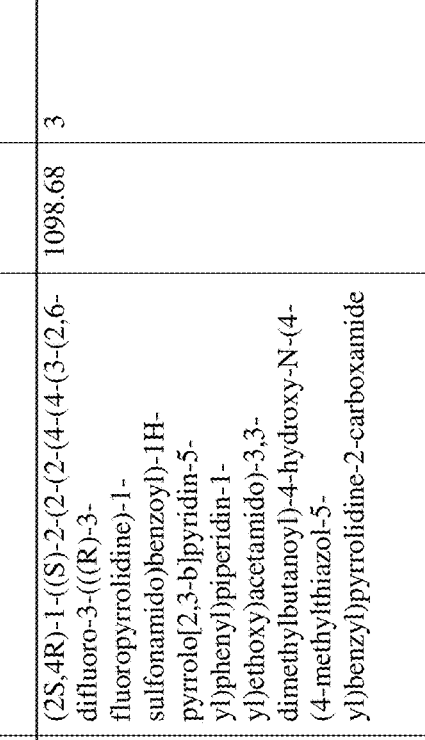 | (2S,4R)-1-((S)-2-(2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-1-yl)ethoxy)acetamido)-3,3-dimethylbutanoyl)-4-hydroxy-N-(4-(4-methylthiazol-5-yl)benzyl)pyrrolidine-2-carboxamide | 1098.68 | 3 |

FIG. 2. Continued

| | | | |
|---|---|---|---|
| 224 | 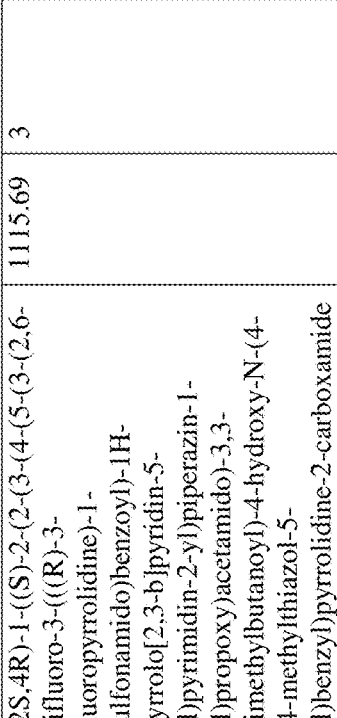 | (2S,4R)-1-((S)-2-(2-(3-(4-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)piperazin-1-yl)propoxy)acetamido)-3,3-dimethylbutanoyl)-4-hydroxy-N-(4-(4-methylthiazol-5-yl)benzyl)pyrrolidine-2-carboxamide | 1115.69 | 3 |
| 225 | 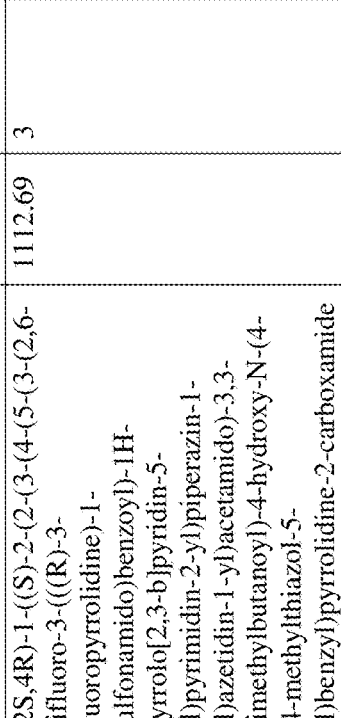 | (2S,4R)-1-((S)-2-(2-(3-(4-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)piperazin-1-yl)azetidin-1-yl)acetamido)-3,3-dimethylbutanoyl)-4-hydroxy-N-(4-(4-methylthiazol-5-yl)benzyl)pyrrolidine-2-carboxamide | 1112.69 | 3 |
| 226 | 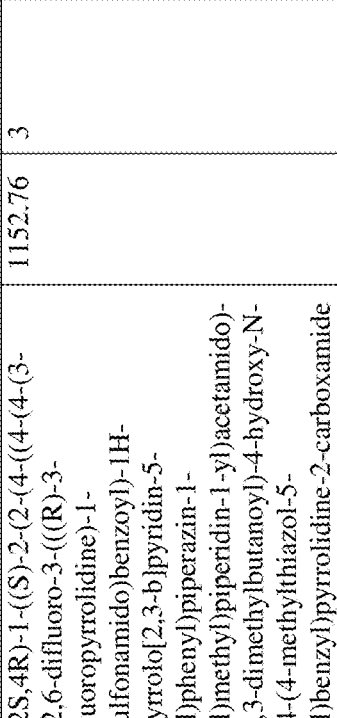 | (2S,4R)-1-((S)-2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide | 1152.76 | 3 |

FIG. 2. Continued

| | | | |
|---|---|---|---|
| 227 | 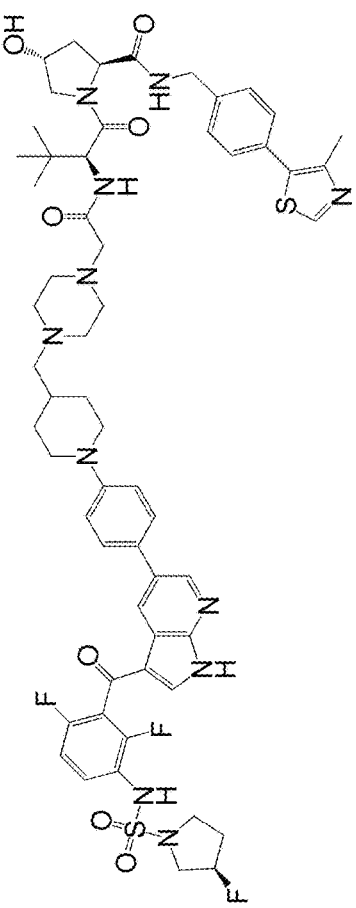 | (2S,4R)-1-((S)-2-(2-(4-((1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N-(4-(4-methylthiazol-5-yl)benzyl)pyrrolidine-2-carboxamide | 1152.80 | 3 |
| 228 | 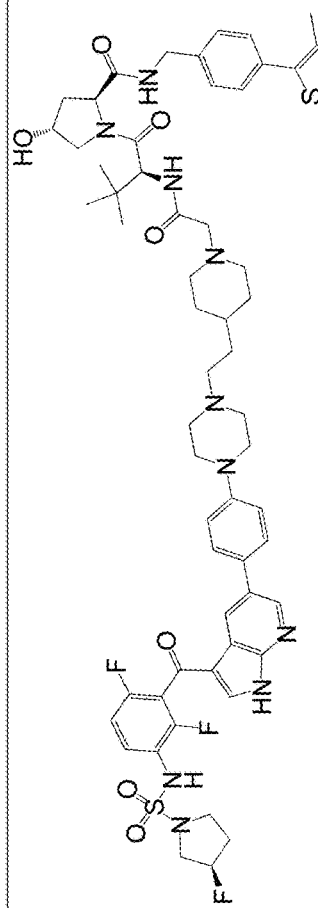 | (2S,4R)-1-((S)-2-(2-(4-(2-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-1-yl)ethyl)piperazin-1-yl)acetamido)-3,3-dimethylbutanoyl)-4-hydroxy-N-(4-(4-methylthiazol-5-yl)benzyl)pyrrolidine-2-carboxamide | 1166.80 | 3 |
| 229 | 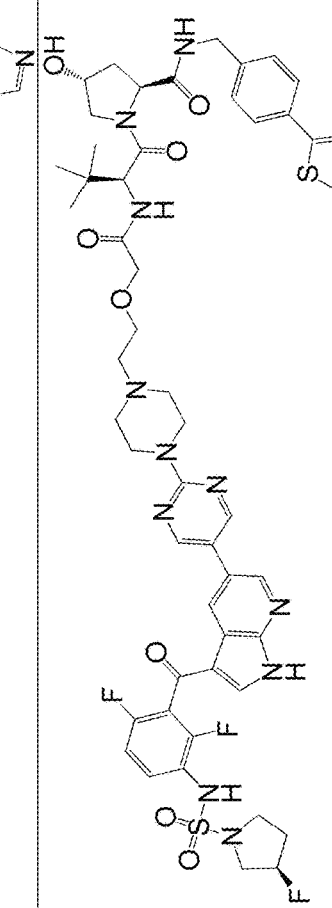 | (2S,4R)-1-((S)-2-(2-(4-(5-(2-(4-(3-(2,6-difluoro-3-(((R)-3-fluoropyrrolidine)-1-sulfonamido)benzoyl)-1H-pyrrolo[2,3-b]pyrimidin-2-yl)pyrimidin-5-yl)piperazin-1-yl)ethoxy)acetamido)-3,3-dimethylbutanoyl)-4-hydroxy-N-(4-(4-methylthiazol-5-yl)benzyl)pyrrolidine-2-carboxamide | 1101.67 | 3 |

FIG. 2. Continued

| # | Structure | Name | MW | n |
|---|---|---|---|---|
| 230 | 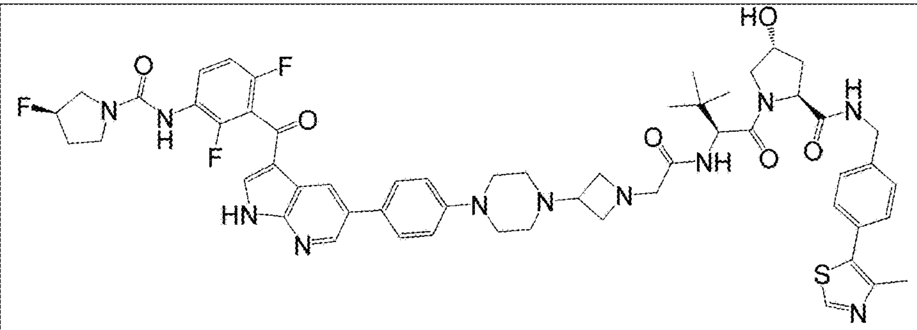 | (R)-N-(2,4-difluoro-3-(5-(4-(4-(1-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)azetidin-3-yl)piperazin-1-yl)phenyl)-1H-pyrrolo[2,3-b]pyridin-3-carbonyl)phenyl)-3-fluoropyrrolidine-1-carboxamide | 1074.72 | 3 |
| 231 | 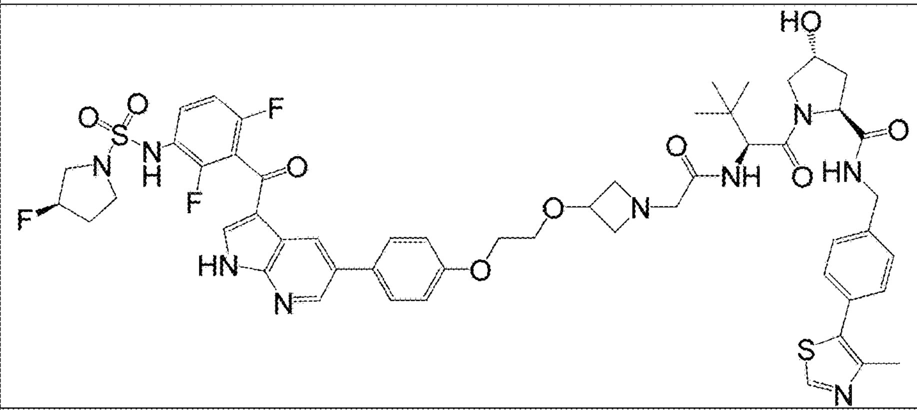 | (2S,4R)-1-((S)-2-(2-(3-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethoxy)azetidin-1-yl)acetamido)-3,3-dimethylbutanoyl)-4-hydroxy-N-(4-(4-methylthiazol-5-yl)benzyl)pyrrolidine-2-carboxamide | 1086.65 | 3 |
| 232 | 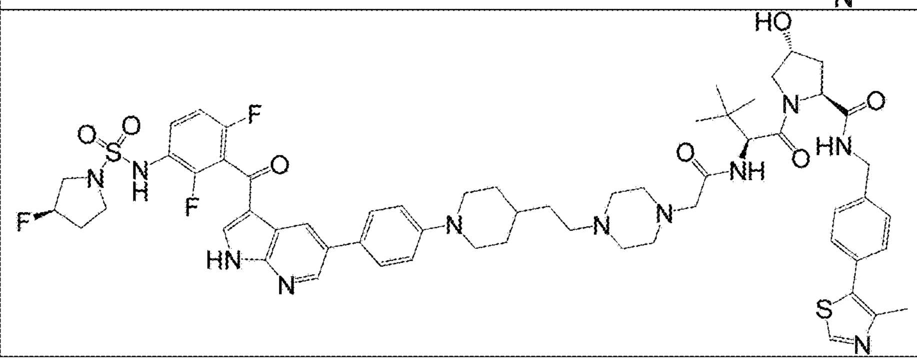 | (2S,4R)-1-((S)-2-(2-(4-(2-(1-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-4-yl)ethyl)piperazin-1-yl)acetamido)-3,3-dimethylbutanoyl)-4-hydroxy-N-(4-(4-methylthiazol-5-yl)benzyl)pyrrolidine-2-carboxamide | 1166.78 | 3 |

FIG. 2. Continued

| | | | |
|---|---|---|---|
| 233 | 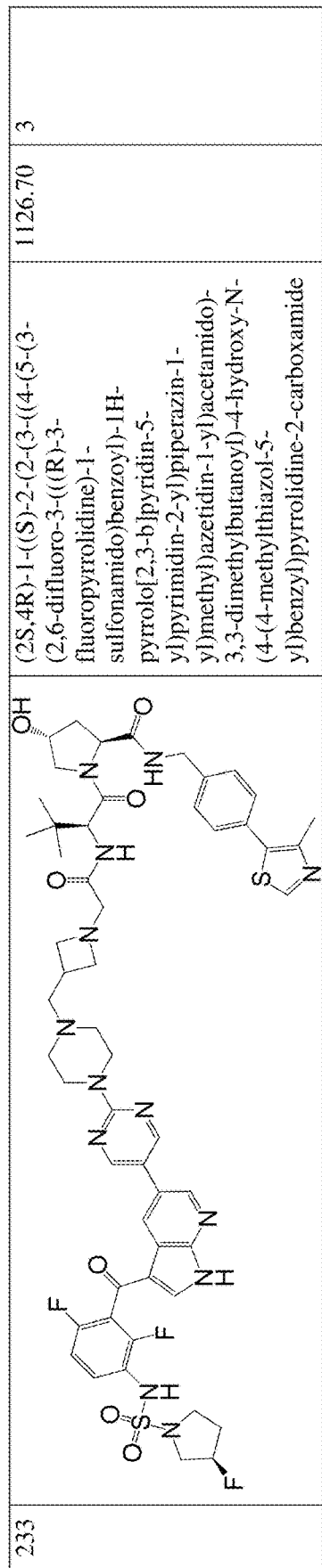 | (2S,4R)-1-((S)-2-(2-(3-((4-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)piperazin-1-yl)methyl)azetidin-1-yl)acetamido)-3,3-dimethylbutanoyl)-4-hydroxy-N-(4-(4-methylthiazol-5-yl)benzyl)pyrrolidine-2-carboxamide | 1126.70 3 |
| 234 | 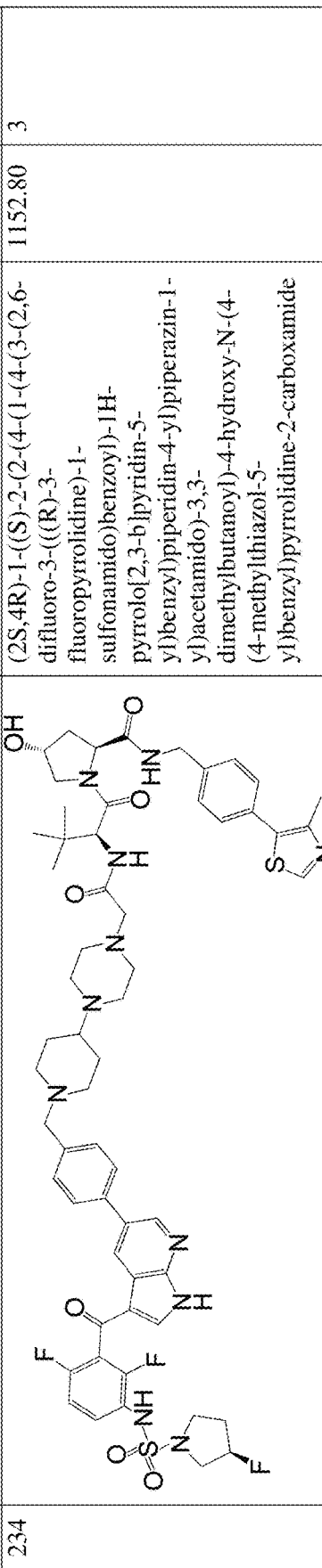 | (2S,4R)-1-((S)-2-(2-(4-(1-(4-(3-(2,6-difluoro-3-(((R)-3-fluoropyrrolidine)-1-sulfonamido)benzoyl)-1H-pyrrolo[2,3-b]pyridin-5-yl)benzyl)piperidin-4-yl)piperazin-1-yl)acetamido)-3,3-dimethylbutanoyl)-4-hydroxy-N-(4-(4-methylthiazol-5-yl)benzyl)pyrrolidine-2-carboxamide | 1152.80 3 |
| 235 | 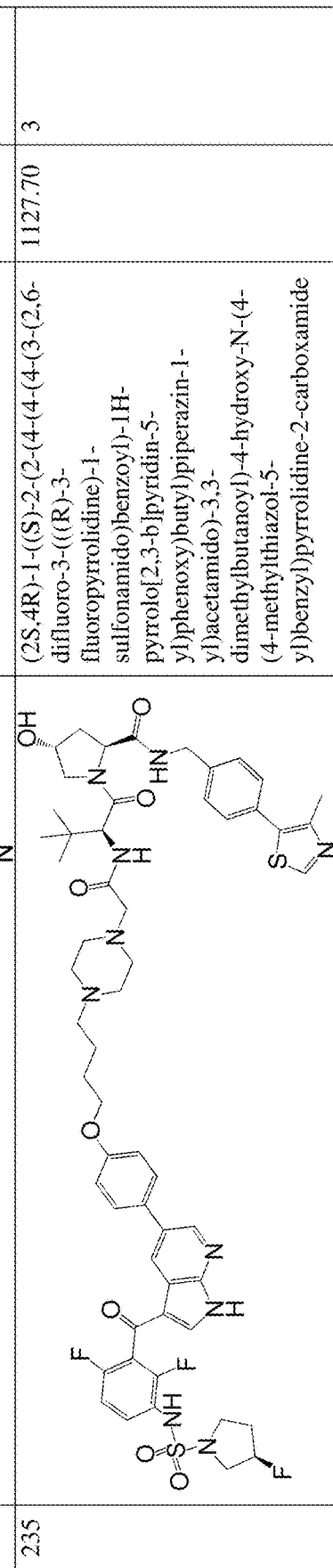 | (2S,4R)-1-((S)-2-(2-(4-(4-(3-(2,6-difluoro-3-(((R)-3-fluoropyrrolidine)-1-sulfonamido)benzoyl)-1H-pyrrolo[2,3-b]pyridin-5-yl)phenoxy)butyl)piperazin-1-yl)acetamido)-3,3-dimethylbutanoyl)-4-hydroxy-N-(4-(4-methylthiazol-5-yl)benzyl)pyrrolidine-2-carboxamide | 1127.70 3 |

FIG. 2. Continued

| | | | | |
|---|---|---|---|---|
| 236 | (structure) | (2S,4R)-1-((S)-2-(2-(6-(4-(3-(2,6-difluoro-3-(((R)-3-fluoropyrrolidine)-1-sulfonamido)benzoyl)-1H-pyrrolo[2,3-b]pyridin-5-yl)phenethyl)-2,6-diazaspiro[3.3]heptan-2-yl)acetamido)-3,3-dimethylbutanoyl)-4-hydroxy-N-(4-(4-methylthiazol-5-yl)benzyl)pyrrolidine-2-carboxamide | 1095.70 | 3 |
| 237 | (structure) | (2S,4R)-1-((S)-2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide | 1151.80 | 3 |
| 238 | (structure) | (2S,4R)-1-((S)-2-(2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)acetamido)-3,3-dimethylbutanoyl)-4-hydroxy-N-((S)-1-(4-(4-methylthiazol-5-yl)phenyl)ethyl)pyrrolidine-2-carboxamide | 1113.70 | 3 |

FIG. 2. Continued

| | | | |
|---|---|---|---|
| 239 | 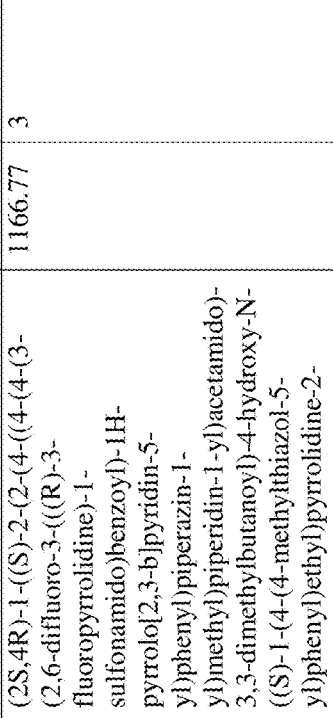 | (2S,4R)-1-((S)-2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1166.77 | 3 |
| 240 | 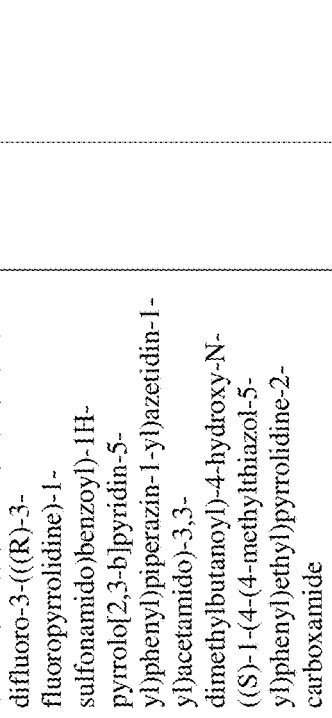 | (2S,4R)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1124.71 | 3 |
| 241 | 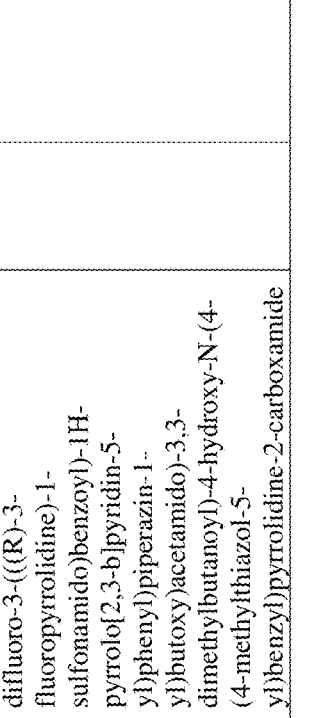 | (2S,4R)-1-((S)-2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)butoxy)acetamido)-3,3-dimethylbutanoyl)-4-hydroxy-N-(4-(4-methylthiazol-5-yl)benzyl)pyrrolidine-2-carboxamide | 1127.72 | 3 |

FIG. 2. Continued

| | | | |
|---|---|---|---|
| 242 | [structure] | (2S,4R)-1-((S)-2-(2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)acetamido)-3,3-dimethylbutanoyl)-4-hydroxy-N-((R)-2-hydroxy-1-(4-(4-methylthiazol-5-yl)phenyl)ethyl)pyrrolidine-2-carboxamide | 1129.70 | 3 |
| 243 | [structure] | (2S,4R)-1-((S)-2-(2-(4-(4-((R)-3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-((R)-2-hydroxy-1-(4-(4-methylthiazol-5-yl)phenyl)ethyl)pyrrolidine-2-carboxamide | 1182.77 | 3 |

FIG. 2. Continued

| | | | |
|---|---|---|---|
| 244 | [structure] | (2S,4R)-1-((S)-2-(2-(3-(4-(4-(3-(2,6-difluoropyrrolidine)-3-(((R)-3-fluoropyrrolidine)-1-sulfonamido)benzoyl)-1H-pyrrolo[2,3-b]pyridin-5-yl)phenyl)piperazin-1-yl)propoxy)acetamido)-3,3-dimethylbutanoyl)-4-hydroxy-N-((S)-1-(4-(4-methylthiazol-5-yl)phenyl)ethyl)pyrrolidine-2-carboxamide | 1127.71 | 3 |
| 245 | [structure] | (2S,4R)-1-((S)-2-(2-(3-(4-(4-(3-(2,6-difluoropyrrolidine)-3-(((R)-3-fluoropyrrolidine)-1-sulfonamido)benzoyl)-1H-pyrrolo[2,3-b]pyridin-5-yl)phenyl)piperazin-1-yl)propoxy)acetamido)-3,3-dimethylbutanoyl)-4-hydroxy-N-((R)-2-hydroxy-1-(4-(4-methylthiazol-5-yl)phenyl)ethyl)pyrrolidine-2-carboxamide | 1143.71 | 3 |
| 246 | [structure] | (2S,4R)-1-((S)-2-(2-(4-(4-(3-((2-(dimethylamino)ethyl)sulfonamido)-2,6-difluorobenzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide | 1136.76 | 3 |

FIG. 2. Continued

| | | | |
|---|---|---|---|
| 247 | [structure] | (2S,4R)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-4-hydroxy-N-((R)-2-hydroxy-1-(4-(4-methylthiazol-5-yl)phenyl)ethyl)pyrrolidine-2-carboxamide | 1140.71 | 3 |
| 248 | [structure] | (2S,4R)-1-((S)-2-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazine-1-carbonyl)piperidin-1-yl)acetamido)-3,3-dimethylbutanoyl)-4-hydroxy-N-(4-(4-methylthiazol-5-yl)benzyl)pyrrolidine-2-carboxamide | 1166.70 | 3 |
| 249 | [structure] | (2S,4R)-1-((2S)-2-(2-(4-(4-(4-(3-(3-((2,3-dihydroxypropyl)sulfonamido)-2,6-difluorobenzoyl)-1H-pyrrolo[2,3-b]pyridin-5-yl)phenyl)piperidin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide | 1139.70 | 3 |

FIG. 2. Continued

| | | | |
|---|---|---|---|
| 250 | 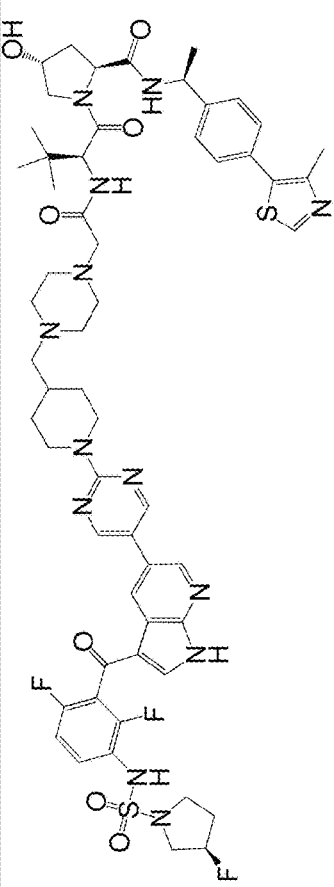 | (2S,4R)-1-((S)-2-(2-(4-((1-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)piperidin-4-yl)methyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1168.76 | 3 |
| 251 | 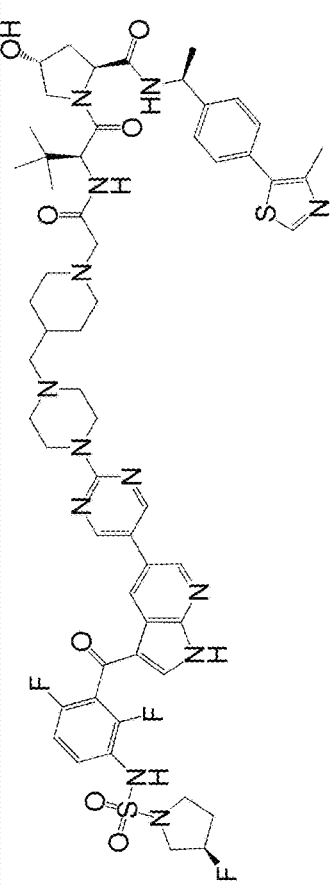 | (2S,4R)-1-((S)-2-(2-(4-((4-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)methyl)piperidin-1-yl)methyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide | 1168.76 | 3 |
| 252 | 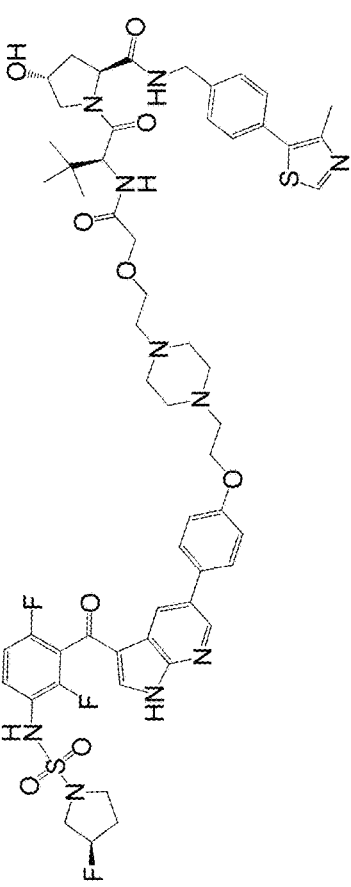 | (2S,4R)-1-((S)-2-(2-(2-(4-(2-(4-(3-(2,6-difluoro-3-(((R)-3-fluoropyrrolidine)-1-sulfonamido)benzoyl)-1H-pyrrolo[2,3-b]pyridin-5-yl)phenoxy)ethyl)piperazin-1-yl)ethoxy)acetamido)-3,3-dimethylbutanoyl)-4-hydroxy-N-(4-methylthiazol-5-yl)benzyl)pyrrolidine-2-carboxamide | 1143.71 | 3 |

FIG. 2. Continued

| 253 | 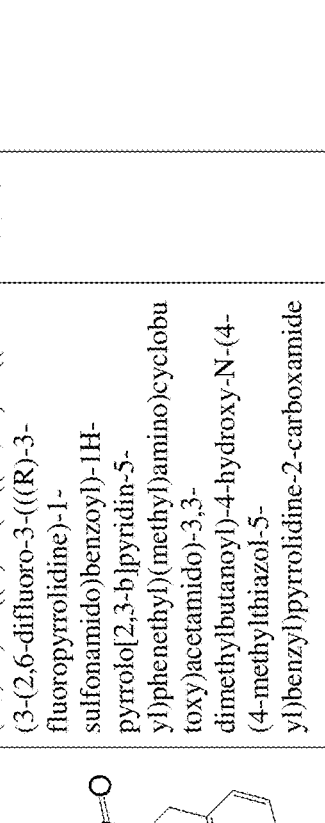 | (2S,4R)-1-((S)-2-(2-(2-((1r,3S)-3-((4-(3-(2,6-difluoro-3-(((R)-3-fluoropyrrolidine)-1-sulfonamido)benzoyl)-1H-pyrrolo[2,3-b]pyridin-5-yl)phenethyl)(methyl)amino)cyclobutoxy)acetamido)-3,3-dimethylbutanoyl)-4-hydroxy-N-(4-(4-methylthiazol-5-yl)benzyl)pyrrolidine-2-carboxamide | 1098.69 | 4 |
| 254 | 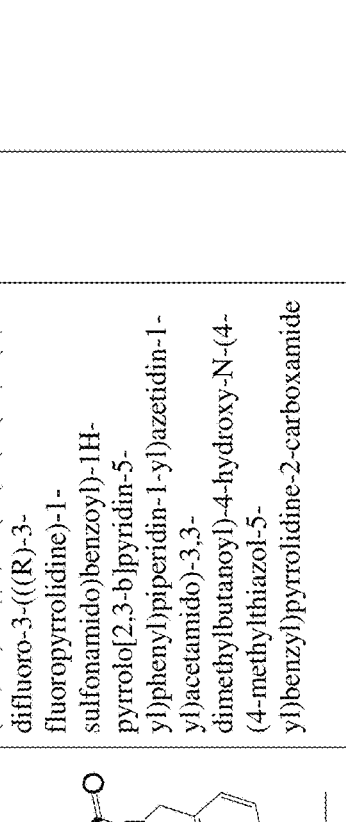 | (2S,4R)-1-((S)-2-(2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperidin-1-yl)azetidin-1-yl)acetamido)-3,3-dimethylbutanoyl)-4-hydroxy-N-(4-(4-methylthiazol-5-yl)benzyl)pyrrolidine-2-carboxamide | 1109.70 | 4 |

| | | | |
|---|---|---|---|
| 255 | | (2S,4R)-1-((S)-2-(2-((1r,3S)-3-((4-(3-(2,6-difluoro-3-(((R)-3-fluoropyrrolidine)-1-sulfonamido)benzoyl)-1H-pyrrolo[2,3-b]pyridin-5-yl)benzyl)(methyl)amino)cyclobutoxy)acetamido)-3,3-dimethylbutanoyl)-4-hydroxy-N-(4-(4-methylthiazol-5-yl)benzyl)pyrrolidine-2-carboxamide | 1084.70 | 4 |
| 256 | | (2S,4R)-1-((S)-2-(2-(4-((4-(5-(3-(2,6-difluoro-3-(((R)-3-fluoropyrrolidine)-1-sulfonamido)benzoyl)-1H-pyrrolo[2,3-b]pyridin-5-yl)pyrimidin-2-yl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide | 1154.70 | 4 |
| 257 | | (2S,4R)-1-((S)-2-(2-(3-(4-(3-(2,6-difluoro-3-(((R)-3-fluoropyrrolidine)-1-sulfonamido)benzoyl)-1H-pyrrolo[2,3-b]pyridin-5-yl)phenoxy)propoxy)azetidin-1-yl)acetamido)-3,3-dimethylbutanoyl)-4-hydroxy-N-(4-(4-methylthiazol-5-yl)benzyl)pyrrolidine-2-carboxamide | 1100.70 | 4 |

FIG. 2. Continued

| | | | |
|---|---|---|---|
| 258 | 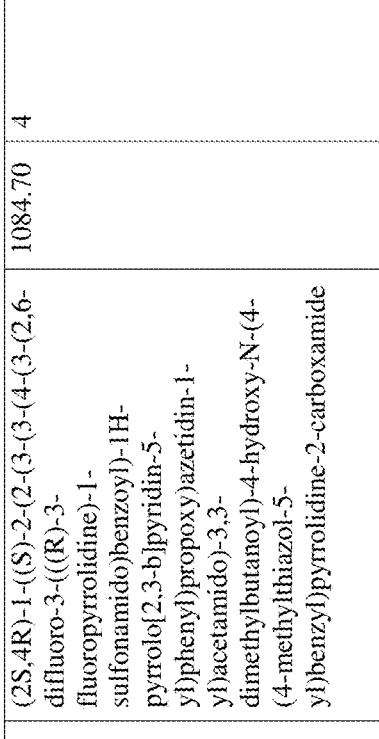 | (2S,4R)-1-((S)-2-(2-(3-(4-(3-(2,6-difluoro-3-(((R)-3-fluoropyrrolidine)-1-sulfonamido)benzoyl)-1H-pyrrolo[2,3-b]pyridin-5-yl)phenyl)propoxy)azetidin-1-yl)acetamido)-3,3-dimethylbutanoyl)-4-hydroxy-N-(4-(4-methylthiazol-5-yl)benzyl)pyrrolidine-2-carboxamide | 1084.70 | 4 |
| 259 | 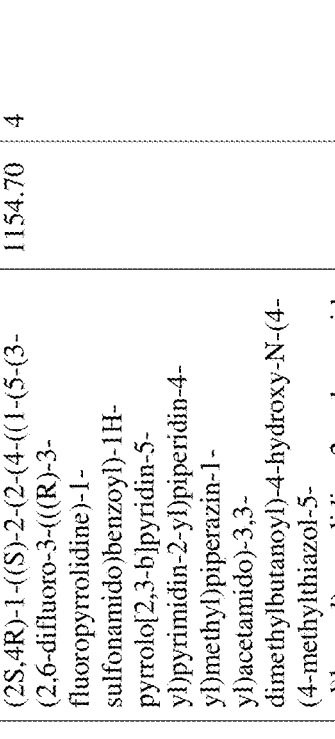 | (2S,4R)-1-((S)-2-(2-(4-((1-(5-(2,6-difluoro-3-(((R)-3-fluoropyrrolidine)-1-sulfonamido)benzoyl)-1H-pyrrolo[2,3-b]pyridin-5-yl)pyrimidin-2-yl)piperidin-4-yl)methyl)piperazin-1-yl)acetamido)-3,3-dimethylbutanoyl)-4-hydroxy-N-(4-(4-methylthiazol-5-yl)benzyl)pyrrolidine-2-carboxamide | 1154.70 | 4 |
| 260 | 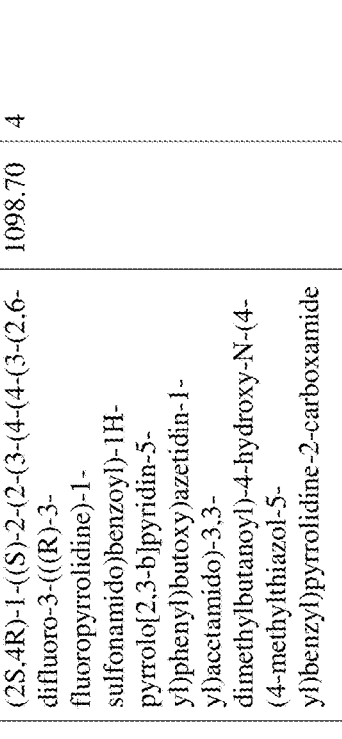 | (2S,4R)-1-((S)-2-(2-(3-(4-(3-(2,6-difluoro-3-(((R)-3-fluoropyrrolidine)-1-sulfonamido)benzoyl)-1H-pyrrolo[2,3-b]pyridin-5-yl)phenyl)butoxy)azetidin-1-yl)acetamido)-3,3-dimethylbutanoyl)-4-hydroxy-N-(4-(4-methylthiazol-5-yl)benzyl)pyrrolidine-2-carboxamide | 1098.70 | 4 |

FIG. 2. Continued

| | | | |
|---|---|---|---|
| 261 | 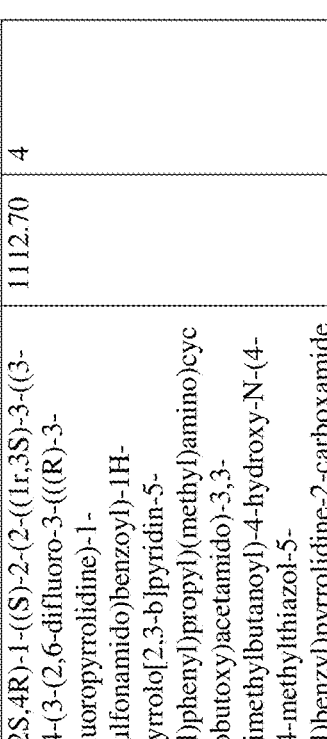 | (2S,4R)-1-((S)-2-(2-((1r,3S)-3-((3-(4-(3-(2,6-difluoro-3-(((R)-3-fluoropyrrolidine)-1-sulfonamido)benzoyl)-1H-pyrrolo[2,3-b]pyridin-5-yl)phenyl)(methyl)amino)cyclobutoxy)acetamido)-3,3-dimethylbutanoyl)-4-hydroxy-N-(4-(4-methylthiazol-5-yl)benzyl)pyrrolidine-2-carboxamide | 1112.70 | 4 |
| 262 | 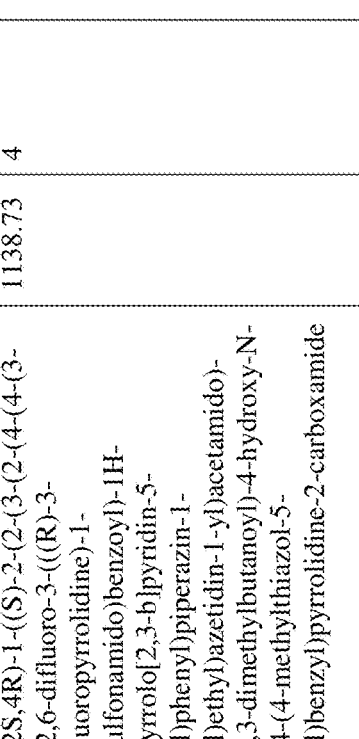 | (2S,4R)-1-((S)-2-(2-(3-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethyl)azetidin-1-yl)acetamido)-3,3-dimethylbutanoyl)-4-hydroxy-N-(4-(4-methylthiazol-5-yl)benzyl)pyrrolidine-2-carboxamide | 1138.73 | 4 |
| 263 | 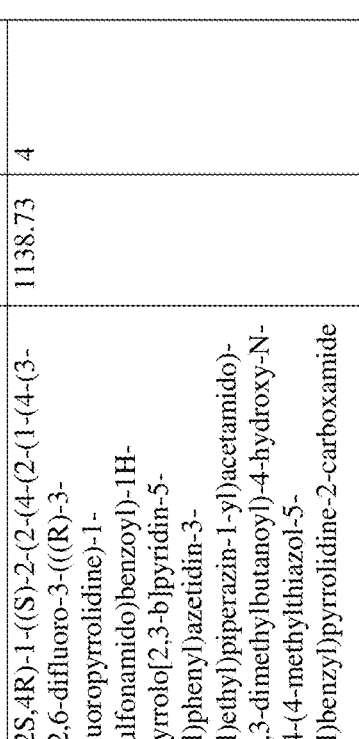 | (2S,4R)-1-((S)-2-(2-(4-(2-(1-(4-(3-(2,6-difluoro-3-(((R)-3-fluoropyrrolidine)-1-sulfonamido)benzoyl)-1H-pyrrolo[2,3-b]pyridin-5-yl)phenyl)azetidin-3-yl)ethyl)piperazin-1-yl)acetamido)-3,3-dimethylbutanoyl)-4-hydroxy-N-(4-(4-methylthiazol-5-yl)benzyl)pyrrolidine-2-carboxamide | 1138.73 | 4 |

FIG. 2. Continued

| | | | |
|---|---|---|---|
| 264 | [structure] | (2S,4R)-1-((S)-2-(2-(4-((4-(5-(3-(2,6-difluoro-3-(((R)-3-fluoropyrrolidine)-1-sulfonamido)benzoyl)-1H-pyrrolo[2,3-b]pyridin-5-yl)pyridin-2-yl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide | 1153.74 | 4 |
| 265 | [structure] | (2S,4R)-1-((S)-2-(2-(4-((4-(6-(3-(2,6-difluoro-3-(((R)-3-fluoropyrrolidine)-1-sulfonamido)benzoyl)-1H-pyrrolo[2,3-b]pyridin-5-yl)pyridazin-3-yl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide | 1154.73 | 4 |
| 266 | [structure] | (2S,4R)-1-((S)-2-(2-(4-((4-(6-(3-(2,6-difluoro-3-(((R)-3-fluoropyrrolidine)-1-sulfonamido)benzoyl)-1H-pyrrolo[2,3-b]pyridin-5-yl)pyridin-3-yl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide | 1153.74 | 4 |

FIG. 2. Continued

| | | | |
|---|---|---|---|
| 267 | 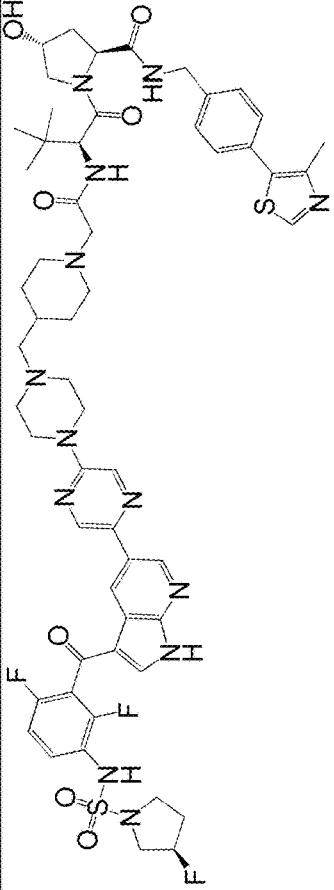 | (2S,4R)-1-((S)-2-(2-(4-((4-(5-(3-(2,6-difluoro-3-(((R)-3-fluoropyrrolidine)-1-sulfonamido)benzoyl)-1H-pyrrolo[2,3-b]pyridin-5-yl)pyrazin-2-yl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide | 1154.74 | 4 |
| 268 | 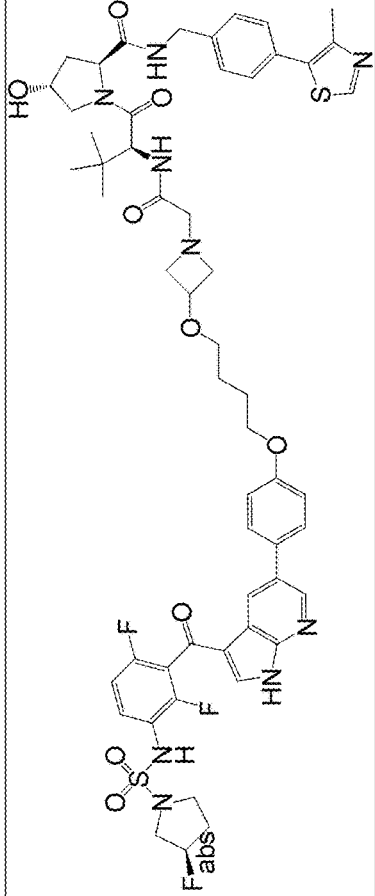 | (2S,4R)-1-((S)-2-(2-(3-(4-(3-(2,6-difluoro-3-(((R)-3-fluoropyrrolidine)-1-sulfonamido)benzoyl)-1H-pyrrolo[2,3-b]pyridin-5-yl)phenoxy)butoxy)azetidin-1-yl)acetamido)-3,3-dimethylbutanoyl)-4-hydroxy-N-(4-(4-methylthiazol-5-yl)benzyl)pyrrolidine-2-carboxamide | 1114.68 | 4 |
| 269 | 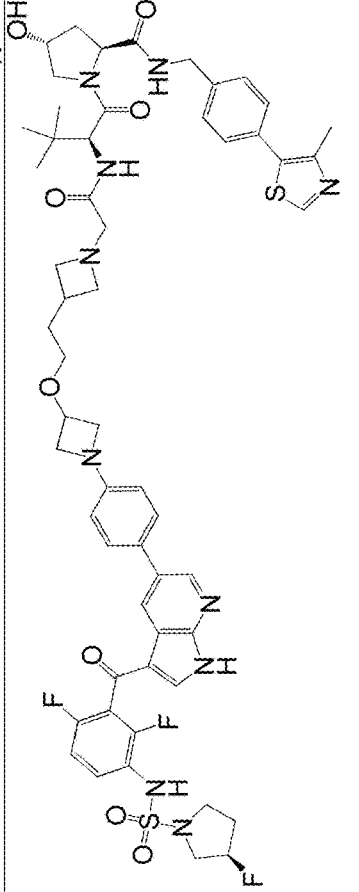 | (2S,4R)-1-((S)-2-(2-(3-(2-((1-(4-(3-(2,6-difluoro-3-(((R)-3-fluoropyrrolidine)-1-sulfonamido)benzoyl)-1H-pyrrolo[2,3-b]pyridin-5-yl)phenyl)azetidin-3-yl)oxy)ethyl)azetidin-1-yl)acetamido)-3,3-dimethylbutanoyl)-4-hydroxy-N-(4-(4-methylthiazol-5-yl)benzyl)pyrrolidine-2-carboxamide | 1125.70 | 4 |

FIG. 2. Continued

| 271 | [structure] | (E)-4-(cyclobutylmethoxy)-2-(2,6-dioxopiperidin-3-yl)-6-(4-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione | 791.54 | 5 |
| --- | --- | --- | --- | --- |
| 273 | [structure] | (E)-2-(2,6-dioxopiperidin-3-yl)-5-(fluoromethoxy)-6-(4-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione | 755.47 | 6 |
| 274 | [structure] | (E)-2-(2,6-dioxopiperidin-3-yl)-4-ethoxy-6-(4-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione | 751.50 | 6 |

FIG. 2. Continued

| | | | | |
|---|---|---|---|---|
| 275 | 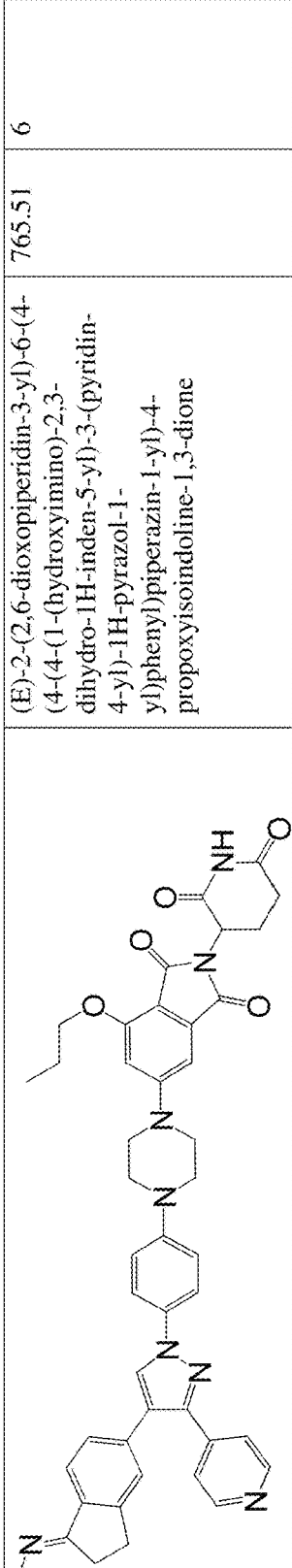 | (E)-2-(2,6-dioxopiperidin-3-yl)-6-(4-(4-(4-(1-(hydroxyimino)-2,3-dihydro-1H-inden-5-yl)-3-(pyridin-4-yl)-1H-pyrazol-1-yl)phenyl)piperazin-1-yl)-4-propoxyisoindoline-1,3-dione | 765.51 | 6 |
| 276 | 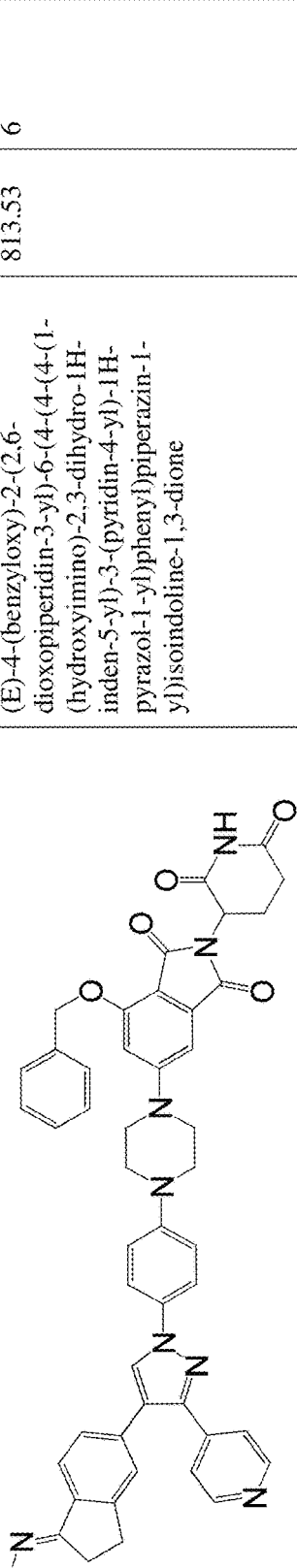 | (E)-4-(benzyloxy)-2-(2,6-dioxopiperidin-3-yl)-6-(4-(4-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione | 813.53 | 6 |
| 277 | 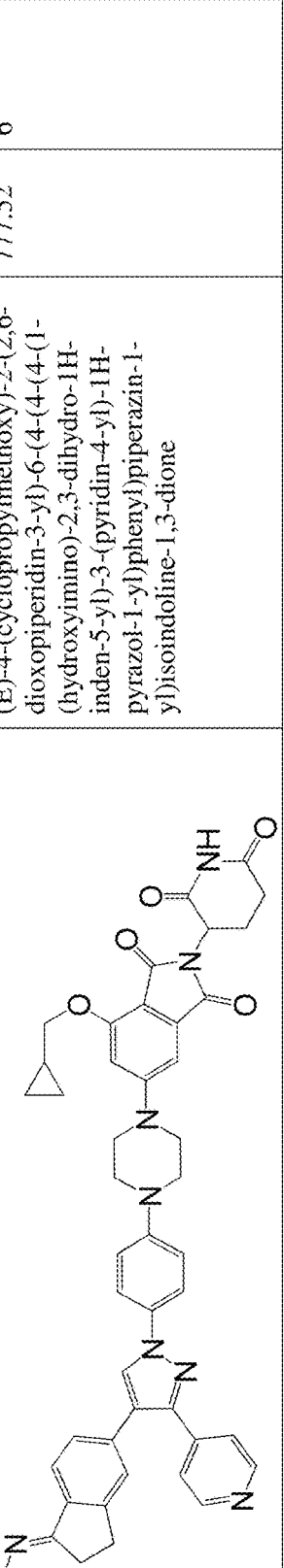 | (E)-4-(cyclopropylmethoxy)-2-(2,6-dioxopiperidin-3-yl)-6-(4-(4-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione | 777.52 | 6 |

FIG. 2. Continued

| # | Structure | Name | MW | |
|---|---|---|---|---|
| 278 | 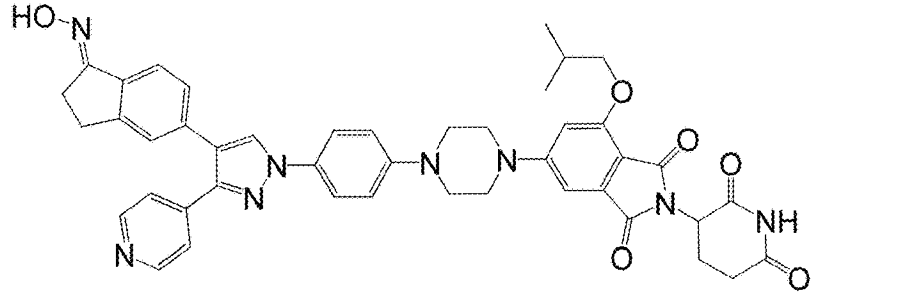 | (E)-2-(2,6-dioxopiperidin-3-yl)-6-(4-(4-(4-(1-(hydroxyimino)-2,3-dihydro-1H-inden-5-yl)-3-(pyridin-4-yl)-1H-pyrazol-1-yl)phenyl)piperazin-1-yl)-4-isobutoxyisoindoline-1,3-dione | 779.53 | 6 |
| 279 | 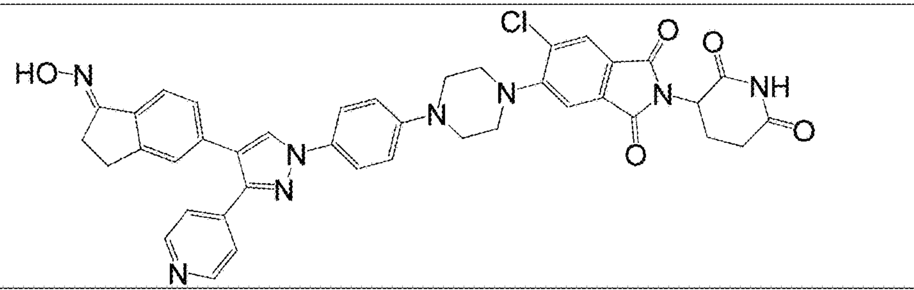 | (E)-5-chloro-2-(2,6-dioxopiperidin-3-yl)-6-(4-(4-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione | 741.43 | 6 |
| 280 | 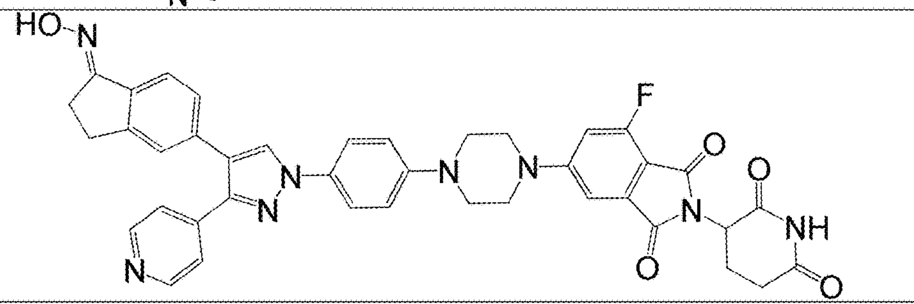 | (E)-2-(2,6-dioxopiperidin-3-yl)-4-fluoro-6-(4-(4-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione | 725.46 | 6 |

FIG. 2. Continued

| | | | |
|---|---|---|---|
| 281 | | (E)-2-(2,6-dioxopiperidin-3-yl)-6-fluoro-4-(4-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione | 725.46 | 6 |
| 282 | | (E)-2-(2,6-dioxopiperidin-3-yl)-5-(4-((1-(4-(4-(1-(hydroxyimino)-2,3-dihydro-1H-inden-5-yl)-3-(pyridin-4-yl)-1H-pyrazol-1-yl)phenyl)azetidin-3-yl)methyl)piperazin-1-yl)isoindoline-1,3-dione | 776.53 | 7 |
| 283 | | (E)-3-(5-(4-(4-(4-(1-(hydroxyimino)-2,3-dihydro-1H-inden-5-yl)-3-(pyridin-4-yl)-1H-pyrazol-1-yl)phenethyl)piperazin-1-yl)-1-oxoisoindolin-2-yl)piperidine-2,6-dione | 721.51 | 7 |

FIG. 2. Continued

| | | | |
|---|---|---|---|
| 284 | [structure] | 2-(2,6-dioxopiperidin-3-yl)-5-(((1r,3r)-3-((4-(4-((E)-1-(hydroxyimino)-2,3-dihydro-1H-inden-5-yl)-3-(pyridin-4-yl)-1H-pyrazol-1-yl)phenethyl)(methyl)amino)cyclobutoxy)isoindoline-1,3-dione | 750.51 | 7 |
| 285 | [structure] | (2S,4R)-1-((S)-2-(3-(2-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide | 1095.70 | 13 |
| 286 | [structure] | (2S,4R)-1-((R)-2-(3-(2-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide | 1095.70 | 13 |

FIG. 2. Continued

| | | | |
|---|---|---|---|
| 287 | | (2S,4R)-1-((S)-2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propoxy)isoxazol-5-yl)-3-methylbutanoyl)-4-hydroxy-N-(4-(4-methylthiazol-5-yl)benzyl)pyrrolidine-2-carboxamide | 1109.67 | 13 |
| 288 | | (2S,4R)-1-((R)-2-(3-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)propoxy)isoxazol-5-yl)-3-methylbutanoyl)-4-hydroxy-N-(4-(4-methylthiazol-5-yl)benzyl)pyrrolidine-2-carboxamide | 1109.67 | 13 |
| 289 | | (2S,4R)-4-hydroxy-1-((S)-2-(2-(2-(2-(4-(4-((E)-1-(hydroxyimino)-2,3-dihydro-1H-inden-5-yl)-3-(pyridin-4-yl)-1H-pyrazol-1-yl)phenoxy)ethoxy)acetamido)-3,3-dimethylbutanoyl)-N-(4-(4-methylthiazol-5-yl)benzyl)pyrrolidine-2-carboxamide | 941.64 | 14 |

| 290 |  | (2S,4R)-1-((S)-2-(tert-butyl)-14-(4-(4-((E)-1-(hydroxyimino)-2,3-dihydro-1H-inden-5-yl)-3-(pyridin-4-yl)-1H-pyrazol-1-yl)phenoxy)-4-oxo-6,9,12-trioxa-3-azatetradecanoyl)-4-hydroxy-N-(4-(4-methylthiazol-5-yl)benzyl)pyrrolidine-2-carboxamide | 985.67 | 14 | |
| 291 |  | (2S,4R)-4-hydroxy-1-((S)-2-(2-(4-(4-((E)-1-(hydroxyimino)-2,3-dihydro-1H-inden-5-yl)-3-(pyridin-4-yl)-1H-pyrazol-1-yl)phenoxy)ethoxy)acetamido)-3,3-dimethylbutanoyl)-N-(4-(4-methylthiazol-5-yl)benzyl)pyrrolidine-2-carboxamide | 897.60 | 14 | |

FIG. 2. Continued

| | | | |
|---|---|---|---|
| 292 | 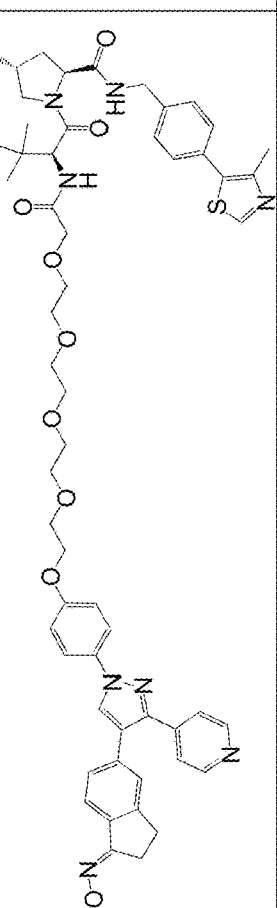 | (2S,4R)-1-((S)-2-(tert-butyl)-17-(4-(4-((E)-1-(hydroxyimino)-2,3-dihydro-1H-inden-5-yl)-3-(pyridin-4-yl)-1H-pyrazol-1-yl)phenoxy)-4-oxo-6,9,12,15-tetraoxa-3-azaheptadecanoyl)-4-hydroxy-N-(4-(4-methylthiazol-5-yl)benzyl)pyrrolidine-2-carboxamide | 1029.71 | 14 |
| 293 | 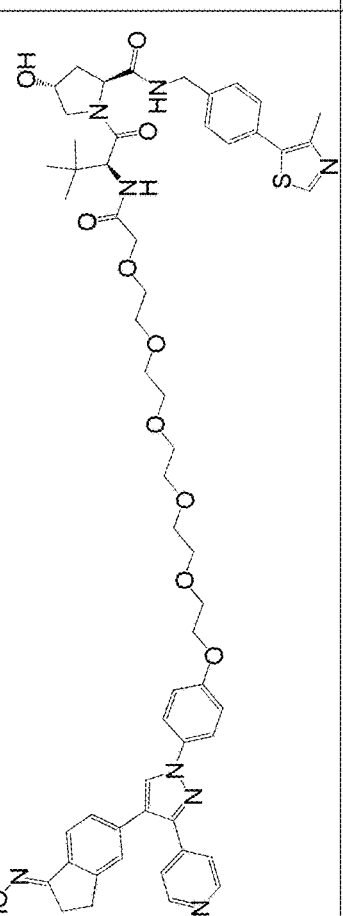 | (2S,4R)-1-((S)-2-(tert-butyl)-20-(4-(4-((E)-1-(hydroxyimino)-2,3-dihydro-1H-inden-5-yl)-3-(pyridin-4-yl)-1H-pyrazol-1-yl)phenoxy)-4-oxo-6,9,12,15,18-pentaoxa-3-azaicosanoyl)-4-hydroxy-N-(4-(4-methylthiazol-5-yl)benzyl)pyrrolidine-2-carboxamide | 1073.74 | 14 |
| 294 | 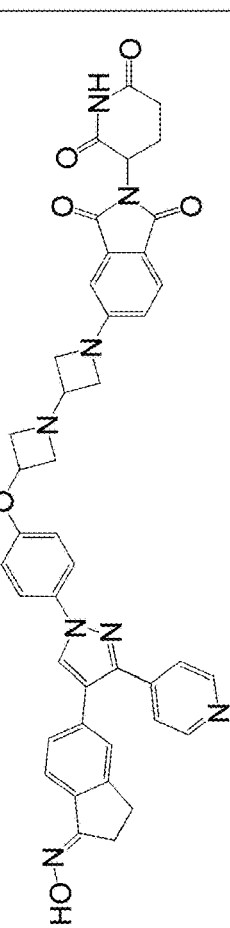 | (E)-2-(2,6-dioxopiperidin-3-yl)-5-(3-(4-(4-(1-(hydroxyimino)-2,3-dihydro-1H-inden-5-yl)-3-(pyridin-4-yl)-1H-pyrazol-1-yl)phenoxy)[1,3'-biazetidin]-1'-yl)isoindoline-1,3-dione | 749.48 | Custom synthesis provided |

FIG. 2. Continued

| | | | |
|---|---|---|---|
| 295 | [structure] | (2S,4R)-1-((S)-2-(2-(4-((4-(4-(3-(2,6-difluoro-3-(((3S,4S)-3-fluoro-4-hydroxypyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide | 1168.75 | Custom synthesis provided |
| 298 | [structure] | (2S,4R)-1-((S)-2-(2-(4-(3-(2,6-difluoro-3-(propylsulfonamido)benzoyl)-1H-pyrrolo[2,3-b]pyridin-5-yl)phenoxy)acetamido)-3,3-dimethylbutanoyl)-4-hydroxy-N-(4-(4-methylthiazol-5-yl)benzyl)pyrrolidine-2-carboxamide | 942.31 | A |
| 299 | [structure] | (2S,4R)-1-((S)-2-(4-(3-(2,6-difluoro-3-(propylsulfonamido)benzoyl)-1H-pyrrolo[2,3-b]pyridin-5-yl)phenoxy)butanamido)-3,3-dimethylbutanoyl)-4-hydroxy-N-(4-(4-methylthiazol-5-yl)benzyl)pyrrolidine-2-carboxamide | 970.37 | A |

FIG. 2. Continued

| | | | |
|---|---|---|---|
| 300 | [structure] | (2S,4R)-1-((S)-2-(2-(2-(3-(3-(2,6-difluoro-3-(propylsulfonamido)benzoyl)-1H-pyrrolo[2,3-b]pyridin-5-yl)phenoxy)ethoxy)acetamido)-3,3-dimethylbutanoyl)-4-hydroxy-N-(4-(4-methylthiazol-5-yl)benzyl)pyrrolidine-2-carboxamide | 986.36 | A |
| 301 | [structure] | (2S,4R)-1-((S)-2-(4-(3-butyramido-2,6-difluorobenzoyl)-1H-pyrrolo[2,3-b]pyridin-5-yl)phenoxy)butanamido)-3,3-dimethylbutanoyl)-4-hydroxy-N-(4-(4-methylthiazol-5-yl)benzyl)pyrrolidine-2-carboxamide | 934.26 | A |
| 302 | [structure] | (2S,4R)-1-((S)-2-(4-(4-(3-(3-amino-2,6-difluorobenzoyl)-1H-pyrrolo[2,3-b]pyridin-5-yl)phenoxy)butanamido)-3,3-dimethylbutanoyl)-4-hydroxy-N-(4-(4-methylthiazol-5-yl)benzyl)pyrrolidine-2-carboxamide | 864.34 | A |

FIG. 2. Continued

| | | | |
|---|---|---|---|
| 303 | [structure] | (2S,4R)-1-((S)-2-(4-(4-(3-(2,6-difluorobenzoyl)-1H-pyrrolo[2,3-b]pyridin-5-yl)phenoxy)butanamido)-3,3-dimethylbutanoyl)-4-hydroxy-N-(4-(4-methylthiazol-5-yl)benzyl)pyrrolidine-2-carboxamide | 849.33 | A |
| 304 | [structure] | (2S,4R)-1-((S)-2-(4-(4-(3-(2,6-difluoro-3-(propylsulfonamido)benzoyl)-1H-pyrrolo[2,3-b]pyridin-5-yl)piperazin-1-yl)butanamido)-3,3-dimethylbutanoyl)-4-hydroxy-N-(4-(4-methylthiazol-5-yl)benzyl)pyrrolidine-2-carboxamide | 962.39 | C |
| 305 | [structure] | (2S,4R)-1-((S)-2-(4-(4-(3-benzoyl-1H-pyrrolo[2,3-b]pyridin-5-yl)phenoxy)butanamido)-3,3-dimethylbutanoyl)-4-hydroxy-N-(4-(4-methylthiazol-5-yl)benzyl)pyrrolidine-2-carboxamide | 813.34 | A |

| 306 |  | (2S,4R)-1-((S)-2-(2-(2-(4-(3-(2,6-difluoro-3-(propylsulfonamido)benzoyl)-1H-pyrrolo[2,3-b]pyridin-5-yl)piperazin-1-yl)ethoxy)acetamido)-3,3-dimethylbutanoyl)-4-hydroxy-N-(4-(4-methylthiazol-5-yl)benzyl)pyrrolidine-2-carboxamide | 978.39 | C |

FIG. 3

Table 43. Data of exemplary protein targeting moieties and compounds of the present disclosure.

| Ex. No. | BRafV600E DC50 (nM) | BRafV600E Dmax (%) | NMR Transcript |
|---|---|---|---|
| 7 | D | A | |
| 9 | D | A | |
| 18 | D | C | |
| 19 | D | A | |
| 23 | D | C | |
| 29 | D | B | |
| 35 | D | C | |
| 37 | D | B | |
| 38 | D | B | |
| 39 | D | B | |
| 41 | D | C | |
| 42 | D | C | |
| 43 | D | B | |
| 45 | D | B | |
| 46 | C | C | |
| 48 | D | C | |
| 49 | D | C | |
| 50 | D | C | |
| 51 | D | C | |
| 52 | D | C | |
| 53 | D | C | |
| 54 | D | B | |
| 55 | D | B | |
| 56 | C | C | |

FIG. 3. Continued

| | | | |
|---|---|---|---|
| 57 | B | C | 1H NMR (400 MHz, CD3OD): δ 8.80 (s, 1H), 8.65 (s, 1H), 7.88 (s, 1H), 7.73-7.75 (m, 1H), 7.41-7.43 (m, 2H), 7.35-7.37 (m, 2H), 7.32-7.34 (m, 2H), 7.11-7.15 (m, 1H), 7.05 (d, J = 4.8 Hz, 2H), 5.29 (s, 0.5H), 5.15 (s, 0.5H), 4.70 (s, 1H), 4.51-4.58 (m, 4H), 4.31-4.35 (m, 1H), 4.21-4.23 (m, 2H), 4.06-4.07 (m, 2H), 3.85-3.91 (m, 3H), 3.76-3.79 (m, 5H), 3.42-3.57 (m, 4H), 2.41 (s, 3H), 1.98-2.30 (m, 4H), 1.05 (s, 9H). Chemical Formula: C52H57F3N8O10S2; Molecular Weight: 1074.36 LC-MS: (ES+): m/z 1075.2 [M+H] +; tR =3.94 min |
| 58 | C | C | |
| 59 | D | A | |
| 61 | B | C | 1H NMR (400 MHz, CDCl3): δ 9.68 (s, 1H), 9.35 (s, 1H), 8.10 (s, 1H), 7.76—7.52 (m, 4H), 7.31—7.20 (m, 3H), 7.18—6.89 (m, 3H), 5.30—5.17 (m, 1H), 5.00 (s, 1H), 4.22—4.15 (m, 4H), 3.93—3.79 (m, 8H), 3.66—3.46 (m, 5H), 2.86—2.76 (m, 4H), 2.27—2.00 (m, 6H). Chemical Formula: C43H39F3N6O11S; Molecular Weight: 904.86 LC-MS: (ES+): m/z 905.1 [M+H] +, tR = 4.06 min |
| 62 | D | C | |
| 63 | C | C | |
| 64 | C | C | |
| 65 | C | C | |
| 67 | D | C | |
| 69 | B | A | |
| 70 | C | C | |
| 71 | D | C | |
| 72 | A | C | |
| 73 | A | B | |
| 74 | C | B | |
| 75 | A | B | |
| 76 | A | B | |
| 77 | B | B | |

FIG. 3. Continued

| | | | |
|---|---|---|---|
| 78 | B | B | |
| 79 | D | C | |
| 80 | D | C | |
| 84 | C | C | |
| 85 | D | B | |
| 86 | C | C | 1H NMR (400 MHz, DMSO-d6) δ 1.95-2.10 (3H, m), 2.53-2.59 (8H, m), 3.18-3.23 (4H, m), 3.24-3.31 (2H, m), 3.36-3.39 (2H, m), 3.47 (1H, s), 3.64 (2H, t, J = 6.0 Hz), 3.80 (2H, t, J = 4.0 Hz), 4.35 (2H, t, J = 4.0 Hz), 5.12 (1H, dd, J = 5.6, 9.6 Hz), 5.29 (1H, d, J = 12.8 Hz), 7.05 (2H, d, J = 8.8 Hz), 7.26 (1H, d, J = 8.8 Hz), 7.39 (1H, dd, J = 2.0, 8.4 Hz), 7.48 (1H, d, J = 2.4 Hz), 7.58-7.65 (3H, m), 7.85 (1H, d, J = 8.4 Hz), 8.07 (1H, s), 8.53 (1H, d, J = 2.4 Hz), 8.65 (1H, d, J = 2.4 Hz), 9.85 (1H, brs), 11.1 (1H, s), 12.9 (1H, s). |
| 87 | B | B | 1H NMR (400 MHz, DMSO-d6) δ 1.96-2.11 (5H, m), 2.51-2.58 (7H, m), 2.82-2.91 (1H, m), 3.12-3.13 (4H, m), 3.25-3.32 (2H, m), 3.37-3.43 (2H, m), 3.48 (1H, s), 3.57 (4H, dd, J = 11.2, 6.4 Hz), 4.26 (2H, t, J = 6.4 Hz), 5.13 (1H, dd, J = 12.8, 6.4 Hz), 5.30 (1H, d, J = 52.0 Hz), 7.01 (2H, d, J = 9.2 Hz), 7.26 (1H, t, J = 8.0 Hz), 7.38 (1H, dd, J = 8.0, 2.4 Hz), 7.45 (1H, d, J = 2.4 Hz), 7.57-7.65 (3H, m), 7.85 (1H, d, J = 8.4 Hz), 8.08 (1H, s), 8.54 (1H, d, J = 2.4 Hz), 9.88 (1H, brs), 11.12 (1H, s), 12.92 (1H, brs). |
| 88 | B | B | 1H NMR (400 MHz, DMSO-d6) δ 1.22-1.30 (2H, m), 1.74-1.86 (3H, m), 1.96-2.11 (3H, m), 2.24 (2H, d, J = 6.8 Hz), 2.54-2.68 (6H, m), 2.75 (2H, t, J = 12.0 Hz), 2.84-2.92 (1H, m), 3.26-3.31 (1H, m), 3.37-3.50 (7H, m), 3.80 (2H, d, J = 12.4 Hz), 5.08 (1H, dd, J = 12.8, 5.2 Hz), 5.35 (1H, d, J = 140.0 Hz), 7.07 (2H, d, J = 8.8 Hz), 7.25-7.28 (2H, m), 7.35 (1H, s), 7.58-7.65 (3H, m), 7.69 (1H, d, J = 8.8 Hz), 8.07 (1H, s), 8.55 (1H, brs), 8.65 (1H, d, J = 2.4 Hz), 9.84 (1H, brs), 11.09 (1H, s), 12.91 (1H, brs). |
| 89 | C | C | 1H NMR (400 MHz, DMSO-d6) δ 1.65 (2H, t, J = 6.8 Hz), 1.80-1.84 (2H, m), 2.02-2.11 (3H, m), 2.40-2.44 (3H, m), 2.54-2.67 (5H, m), 2.86-2.89 (1H, m), 3.21-3.28 (5H, m), 3.37-3.40 (2H, m), 3.47 (1H, s), 4.23 (2H, t, J = 6.4 Hz), 5.12 (1H, dd, J = 12.8, 5.2 Hz), 5.30 (1H, d, J = 52.0 Hz), 7.07 (2H, d, J = 8.8 Hz), 7.26 (1H, t, J = 8.8 Hz), 7.37 (1H, dd, J = 8.4, 2.0 Hz), 7.45 (1H, d, J = 2.0 Hz), 7.59-7.63 (3H, m), 7.84 (1H, d, J = 8.4 Hz), 8.07 (1H, s), 8.53 (1H, s), 8.64 (1H, d, J = 2.0 Hz), 9.85 (1H, s), 11.11 (1H, s), 12.90 (1H, s). |
| 90 | C | C | 1H NMR (400 MHz, DMSO-d6) δ 1.97-2.32 (5H, m), 2.54-2.69 (8H, m), 2.86-2.90 (1H, m), 3.19-3.28 (4H, m), 3.32-3.47 (4H, m), 4.27 (2H, t, J = 6.4 Hz), 5.12 (1H, dd, J = 12.8, 5.6 Hz), 5.28 (1H, d, J = 56.0 Hz), 7.08 (2H, d, J = 8.8 Hz), 7.28 (1H, t, J = 8.8 Hz), 7.37 (1H, dd, J = 8.4, 2.0 Hz), |

FIG. 3. Continued

| | | |
|---|---|---|
| | | 7.46 (1H, d, J = 2.0 Hz), 7.59-7.65 (3H, m), 7.84 (1H, d, J = 8.4 Hz), 8.07 (1H, s), 8.54 (1H, s), 8.65 (1H, d, J = 2.4 Hz), 9.86 (1H, s), 11.12 (1H, s), 12.91 (1H, s). |
| 91 | B | 1H NMR (400 MHz, DMSO-d6) δ 1.96-2.13 (3H, m), 2.58 (7H, s), 2.83-2.92 (1H, m), 3.26-3.30 (2H, m), 3.40-3.43 (6H, m), 3.48 (1H, s), 3.63-3.67 (2H, m), 3.76-3.80 (2H, m), 4.17-4.19 (2H, m), 5.05-5.09 (1H, m), 5.23-5.36 (1H, m), 7.11 (2H, d, J = 8.4 Hz), 7.24-7.29 (2H, m), 7.34 (1H, s), 7.60-7.69 (4H, m), 8.10 (1H, s), 8.57 (1H, brs), 8.66 (1H, d, J = 2.4 Hz), 9.88 (1H, s), 11.09 (1H, s), 12.95 (1H, s). |
| 92 | B | 1H NMR (400 MHz, DMSO-d6) δ 1.49-1.55 (5H, m), 1.75-2.11 (6H, m), 2.33-2.38 (3H, m), 2.54-2.60 (1H, m), 2.83-2.92 (1H, m), 3.25-3.31 (2H, m), 3.36-3.47 (8H, m), 4.05 (2H, t, J = 6.4 Hz), 5.07 (1H, dd, J = 13.2, 6.4 Hz), 5.29 (1H, d, J = 12.4 Hz), 7.07-7.09 (2H, m), 7.24-7.28 (2H, m), 7.35 (1H, d, J = 1.6 Hz), 7.59-7.68 (4H, m), 8.10 (1H, s), 8.56 (1H, brs), 8.66 (1H, d, J = 2.4 Hz), 9.86 (1H, s), 11.1 (1H, s), 12.9 (1H, s). |
| 93 | C | 1H NMR (400 MHz, DMSO-d6) δ 1.35-1.39 (2H, m), 1.44-1.51 (4H, m), 1.73-1.78 (2H, m), 1.98-2.12 (3H, m), 2.31-2.35 (3H, m), 2.54-2.67 (2H, m), 2.85-2.89 (1H, m), 3.25-3.30 (4H, m), 3.37-3.48 (7H, m), 4.04 (2H, t, J = 6.0 Hz), 5.04-5.09 (1H, m), 5.23-5.37 (1H, m), 7.08 (2H, d, J = 8.8 Hz), 7.24-7.29 (2H, m), 7.34 (1H, s), 7.59-7.68 (4H, m), 8.10 (1H, s), 8.54-8.56 (1H, m), 8.65 (1H, d, J = 2.0 Hz), 9.88 (1H, s), 11.10 (1H, s), 12.95 (1H, s). |
| 94 | D | 1H NMR (400 MHz, DMSO-d6) δ 1.95-2.01 (3H, m), 2.03-2.10 (2H, m), 2.54-2.61 (7H, m), 2.84-2.88 (1H, m), 3.23-3.30 (2H, m), 3.36-3.41 (6H, m), 3.45 (1H, s), 3.58 (4H, dd, J = 12.8, 6.4 Hz), 4.11 (2H, t, J = 6.4 Hz), 5.05 (1H, dd, J = 12.8, 6.4 Hz), 5.30 (1H, d, J = 52.0 Hz), 7.09 (2H, d, J = 8.8 Hz), 7.18-7.23 (2H, m), 7.30 (1H, d, J = 1.6 Hz), 7.57-7.64 (2H, m), 7.67 (2H, d, J = 8.0 Hz), 8.08 (1H, s), 8.55 (1H, brs), 8.64 (1H, d, J = 3.0 Hz), 9.88 (1H, s), 11.09 (1H, s), 12.92 (1H, brs). |
| 95 | B | 1H NMR (400 MHz, DMSO-d6) δ 1.99-2.13 (3H, m), 2.54-2.61 (3H, m), 2.67 (4H, s), 2.80-2.88 (2H, m), 3.28-3.30 (2H, m), 3.37-3.40 (2H, m), 3.48 (4H, s), 4.21 (2H, t, J = 5.6 Hz), 5.06-5.10 (1H, m), 5.23-5.37 (1H, m), 7.12 (2H, d, J = 8.4 Hz), 7.25-7.29 (2H, m), 7.37 (1H, d, J = 1.2 Hz), 7.59-7.70 (4H, m), 8.10 (1H, s), 8.57 (1H, brs), 8.67 (1H, d, J = 2.4 Hz), 8.86 (1H, brs), 11.09 (1H, s), 12.95 (1H, s). |
| 96 | B | 1H NMR (400 MHz, DMSO-d6) δ 1.62-1.69 (2H, m), 1.77-1.82 (2H, m), 1.96-2.11 (3H, m), 2.40-2.44 (3H, m), 2.51-2.61 (4H, m), 2.84-2.93 (1H, m), 3.26-3.30 (2H, m), 3.36-3.48 (7H, m), 4.08 (2H, t, J = 6.4 Hz), 5.05-5.09 (1H, m), 5.23-5.36 (1H, m), 7.09 (2H, d, J = 8.8 Hz), 7.25-7.29 (2H, m), 7.35 (1H, s), 7.60-7.64 (1H, m), 7.66-7.69 (3H, m), 8.10 (1H, s), 8.54 (1H, brs), 8.66 (1H, d, J = 2.0 Hz), 9.86 (1H, s), 11.08 (1H, s), 12.94 (1H, s). |
| 97 | B | 1H NMR (400 MHz, DMSO-d6) δ 1.94-2.14 (6H, m), 2.55-2.61 (6H, m), 2.85-2.89 (1H, m), 3.26- |

FIG. 3. Continued

| | | |
|---|---|---|
| 98 | B | 3.30 (1H, m), 3.36-3.40 (2H, m), 3.43-3.47 (6H, m), 4.11 (2H, t, J = 6.4 Hz), 5.05-5.10 (1H, m), 5.23-5.36 (1H, m), 7.09 (2H, d, J = 8.8 Hz), 7.24-7.29 (2H, m), 7.35 (1H, s), 7.59-7.69 (4H, m), 8.09 (1H, s), 8.56 (1H, brs), 8.66 (1H, d, J = 2.0 Hz), 9.86 (1H, s), 11.08 (1H, s), 12.94 (1H, s) |
| 99 | B | 1H NMR (400 MHz, CD3OD): δ 8.84 (s, 1H), 8.70 (s, 1H), 8.57 (d, J = 2.0 Hz, 1H), 7.89 (s, 1H), 7.73 (m, 1H), 7.61 (d, J = 8.8 Hz, 2H), 7.40-7.48 (m, 4H), 7.07-7.11 (m, 3H), 5.30 (s, 0.5H), 5.14 (s, 0.5H), 4.47-4.65 (m, 4H), 4.34-4.38 (m, 1H), 4.21 (t, J = 5.2 Hz, 2H), 3.81-3.87 (m, 2H), 3.36-3.64 (m, 5H), 3.10 (m, 2H), 2.60-2.92 (m, 10H), 2.45 (s, 3H), 2.03-2.28 (m, 4H), 1.05 (s, 9H). |
| 100 | B | 1H NMR (400 MHz, CD3OD): δ 8.80 (s, 1H), 8.65 (s, 1H), 8.56 (s, 1H), 7.89 (s, 1H), 7.73 (m, 1H), 7.54 (d, J = 8.8 Hz, 2H), 7.44 (d, J = 7.6 Hz, 2H), 7.36 (d, J = 8.0 Hz, 2H), 7.07-7.14 (m, 3H), 5.13 – 5.30 (m, 1H), 4.71 (s, 1H), 4.50 - 4.65 (m, 4H), 4.34 (d, J = 15.6 Hz, 1H), 4.12 (m, 2H), 3.78-3.95 (m, 4H), 3.40-3.65 (m, 6H), 2.42 (s, 3H), 2.00-2.30 (m, 4H), 1.04 (s, 9H). |
| 101 | C | 1H NMR (400 MHz, CD3OD): δ 8.82 (s, 1H), 8.65 (s, 1H), 8.59 (s, 1H), 7.89 (s, 1H), 7.74 (m, 1H), 7.59 (d, J = 8.8 Hz, 2H), 7.30-7.50 (m, 4H), 7.07-7.20 (m, 3H), 5.15 - 5.30 (m, 1H), 4.62 (s, 1H), 4.50 - 4.60 (m, 3H), 4.30 (d, J = 7.8 Hz, 1H), 4.12 (m, 2H), 3.78-3.95 (m, 2H), 3.40-3.80 (m, 14H), 3.10 (m, 5H), 2.42 (s, 3H), 1.98-2.30 (m, 8H), 1.03 (s, 9H). |
| 193 | C | 1H NMR (400 MHz, CD3OD): δ 8.89 (s, 1H), 8.70 (s, 1H), 8.58 (s, 1H), 7.89 (s, 1H), 7.71-7.74 (m, 1H), 7.60 (d, J = 8.4 Hz, 2H), 7.38-7.47 (m, 4H), 7.04-7.12 (m, 3H), 5.29 (s, 0.5H), 5.15 (s, 0.5H), 4.50-4.65 (m, 4H), 4.34-4.38 (m, 1H), 4.07-4.10 (m, 2H), 3.76-3.92 (m, 2H), 3.34-3.56 (m, 5H), 3.07 (m, 2H), 2.63 (s, 10H), 2.46 (s, 3H), 1.96-2.25 (m, 7H), 1.05 (s, 9H). |
| 194 | C | 1H NMR (400 MHz, DMSO-d6) δ 2.03-2.11 (3H, m), 2.27 (2H, t, J = 6.0 Hz), 2.54-2.61 (2H, m), 2.83-2.95 (1H, m), 3.26-3.30 (1H, m), 3.38-3.46 (3H, m), 4.23 (2H, t, J = 6.0 Hz), 4.39 (2H, t, J = 6.0 Hz), 5.12 (1H, dd, J = 12.8, 5.2 Hz), 5.29 (1H, d, J = 54.4 Hz), 7.11 (2H, d, J = 8.4 Hz), 7.24 (1H, t, J = 8.4 Hz), 7.40-7.43 (1H, m), 7.49 (1H, d, J = 2.0 Hz), 7.60-7.62 (1H, m), 7.67 (2H, d, J = 8.8 Hz), 7.85 (1H, d, J = 8.4 Hz), 8.09 (1H, s), 8.55 (1H, s), 8.66 (1H, d, J = 2.4 Hz), 9.87 (1H, brs), 11.13 (1H, brs), 12.95 (1H, brs). |
| 102 | D | 1H NMR (400 MHz, DMSO-d6) δ 2.01-2.04 (4H, m), 2.06-2.11 (3H, m), 2.55-2.61 (2H, m), 2.86-2.89 (1H, m), 3.28-3.30 (1H, m), 3.40-3.48 (3H, m), 4.13 (2H, t, J = 6.0 Hz), 4.28 (2H, t, J = 6.0 Hz), 5.12 (1H, dd, J = 12.8, 5.2 Hz), 5.29 (1H, d, J = 52.0 Hz), 7.09 (2H, d, J = 8.8 Hz), 7.27 (1H, t, J = 8.8 Hz), 7.37 (1H, dd, J = 8.4, 2.0 Hz), 7.47 (1H, d, J = 2.0 Hz), 7.59-7.64 (1H, m), 7.67 (2H, d, J = 8.4 Hz), 7.84 (1H, d, J = 8.4 Hz), 8.10 (1H, s), 8.56 (1H, s), 8.66 (1H, d, J = 2.0 Hz), 9.87 (1H, s), 11.13 (1H, s), 12.95 (1H, s). |
| | D | 1H NMR (400 MHz. CD3OD): δ 8.84(s, 1H), 8.64 (s, 1H), 8.54 (s, 1H), 7.89 (s, 1H), 7.57-7.64 (m, 4H), 7.34-7.48 (m, 4H), 7.08(d, J = 7.6 Hz, 2H), 6.87 (s, 1H), 5.25 (s, 0.5H), 5.15 (s, 0.5H), 4.50- |

FIG. 3. Continued

| | | |
|---|---|---|
| 195 | D | 4.61 (m, 5H), 4.34-4.38 (m, 2H), 3.91 (d, J = 7.2 Hz, 1H), 3.57-3.59 (m, 4H), 3.40 (s, 1H), 3.35 (s, 1H), 3.07 (br, 4H), 2.78 (br, 3H), 2.46-2.54 (m, 7H), 2.20(s, 1H), 2.06-2.12(m, 4H), 1.06 (s, 9H). |
| 103 | B | 1H NMR (400 MHz, DMSO-d6) δ 2.06-2.09 (3H, m), 2.55-2.62 (2H, m), 2.85-2.93 (1H, m), 3.24-3.27 (1H, m), 3.38-3.50 (3H, m), 4.42-4.46 (2H, m), 4.58-4.62 (2H, m). 5.12-5.16 (1H, m), 5.23-5.36 (1H, m), 7.15 (2H, d, J = 8.8 Hz), 7.25 (1H, t, J = 8.8 Hz), 7.45 (1H, dd, J = 2.4, 8.4 Hz), 7.55 (1H, d, J = 2.0 Hz), 7.59-7.63 (1H, m), 7.70 (2H, d, J = 8.4 Hz), 7.87 (1H, d, J = 8.4 Hz), 8.10 (1H, s), 8.58 (1H, d, J = 2.4 Hz), 8.68 (1H, s), 9.89 (1H, brs.), 11.14 (1H, s), 12.96 (1H, brs.). |
| 104 | C | 1H NMR (400 MHz, CD3OD) 8.83 (s, 1H), 8.70 (s, 1H), 8.59 (s, 1H), 7.90 (s, 1H), 7.75-7.74 (m, 1H), 7.59-7.57 (m, 2H), 7.47-7.32 (m, 6H), 7.15-7.2 (m, 1H), 5.30-5.15 (m, 1H), 4.64 (s, 1H), 4.59-4.54 (m, 3H), 4.36-4.32 (m, 1H), 3.86-3.81 (m, 2H), 3.56-3.52 (m, 6H), 3.31-3.23 (m, 4H), 3.11-2.99 (m, 2H), 2.97-2.95 (m, 1H), 2.43 (s, 3H), 2.44-2.04 (m, 4H), 1.01 (m, 9H) |
| 105 | C | 1H NMR (300 MHz, DMSO-d6): δ 12.95 (s, 1H), 8.92 (s, 1H), 8.75-8.53 (m, 3H), 8.08 (s, 1H), 7.79-7.20 (m, 12H), 5.35-5.12 (m, 2H), 4.50-4.20 (m, 6H), 3.66-3.52 (m, 6H), 3.05-2.74( m, 7H), 2.55-2.51(m, 6H) 2.42-1.87 (m, 6H), 1.20 (s, 1H), 0.92 (s, 9H) |
| 106 | C | 1H NMR (300 MHz, DMSO-d6): δ 9.00 (s, 1H), 8.68-8.65 (m, 2H), 8.55 (brs, 1H), 8.08 (s, 1H), 7.70-7.56 (m, 5H), 7.43 (s, 5H), 7.26 (t, J = 8.7 Hz, 1H), 7.06 (d, J = 8.5 Hz, 2H), 5.40-5.10 (m, 2H), 4.63-4.11 (m, 6H), 3.75-3.45 (m, 8H), 3.37-3.06 (m, 8H), 3.05-2.95 (m, 3H), 2.75-2.70 (m, 1H), 2.63-2.45 (m, 4H), 2.25-1.76 (m, 5H), 0.95 (s, 9H) |
| 107 | A | 1H NMR (400 MHz, CD3OD) 8.82 (s, 1H), 8.70 (s, 1H), 8.59 (s, 1H), 7.90 (s, 1H), 7.75-7.74 (m, 1H), 7.58-7.56 (m, 2H), 7.46-7.31 (m, 6H), 7.15-7.2 (m, 1H), 5.30-5.15 (m, 1H), 4.64-4.36 (m, 4H), 4.36-4.32 (m, 1H), 3.86-3.81 (m, 2H), 3.56-3.52 (m, 6H), 3.30 (m, 2H), 3.02-2.98 (m, 2H), 2.66-2.64 (m, 2H), 2.63-2.62 (m, 1H), 2.43 (s, 3H), 2.44-2.04 (m, 6H), 1.01 (s, 9H) |
| 108 | C | 1H NMR (400 MHz, CD3OD) 8.82 (s, 1H), 8.60 (s, 1H), 8.47 (s, 1H), 7.88 (s, 1H), 7.74-7.76 (m, 2H), 7.43-7.47 (m, 4H), 7.30-7.32 (m, 2H), 7.13-7.18 (m, 3H), 5.29 (s, 0.5H), 5.16 (s, 0.5H), 4.76 (d, J = 8.8 Hz, 1H), 4.59-4.65 (m, 2H), 4.51 (s, 1H), 4.24-4.32 (m, 3H), 4.13 (s, 2H), 3.83-3.95 (m, 4H), 3.34-3.58 (m, 4H), 2.32 (s, 3H), 2.03-2.22 (m, 4H), 1.06 (s, 9H). |
| 109 | D | 1H NMR (400 MHz, CD3OD): δ 8.83 (s, 1H), 8.68 (s, 2H), 8.57 (s, 1H), 7.89 (s, 1H), 7.72-7.75 (m, 1H), 7.58-7.60 (m, 3H), 7.37-7.44 (m, 4H), 7.05-7.13 (m, 3H), 5.28 (s, 0.5H), 5.17 (s, 0.5H), 4.70 (d, J = 9.6 Hz, 1H), 4.51-4.58 (m, 3H), 4.31-4.38 (m, 1H), 4.16-4.18 (m, 2H), 3.96-4.02 (m, 2H), 3.81-3.86 (m, 4H), 3.66-3.72 (m, 4H), 3.40-3.57 (m, 5H), 2.44 (s, 3H), 2.02-2.38 (m, 4H), 1.93 (t, J = 6.4 Hz, 2H), 1.03 (s, 9H). |
| | B | 1H NMR (400 MHz, CD3OD): δ 8.84 (s, 1H), 8.59 – 8.67 (m, 2H), 8.58 (s, 1H), 7.88 (s, 2H), 7.74 |

FIG. 3. Continued

| | | |
|---|---|---|
| | | —7.76 (m, 1H), 7.60 (q, J = 8.4 Hz, 1H), 7.38—7.45 (m, 4H), 7.13 (t, J = 8.8 Hz, 1H), 7.06 (d, J = 8.8 Hz, 1H), 5.29 (s, 0.5H), 5.16 (s, 0.5H), 4.65 (d, J = 9.2 Hz, 1H), 4.50—4.59 (m, 4H), 4.28—4.37 (m, 1H), 4.07 (s, 2H), 3.91—3.95 (m, 1H), 3.77—3.82 (m, 1H), 3.42—3.57 (m, 5H), 2.45 (s, 3H), 2.37—2.41 (m, 2H), 2.03—2.21 (m, 5H), 1.84 (s, 4H), 1.31 (d, J = 17.6 Hz, 1H), 1.05 (s, 9H). |
| 110 | C | 1H NMR (400 MHz, CD3OD): δ 8.90 (s, 1H), 8.70-8.75 (m, 2H), 8.60 (s, 1H), 7.90 (s, 1H), 7.71-7.75 (m, 1H), 7.60-7.63 (m, 2H), 7.37-7.45 (m, 4H), 7.12-7.25 (m, 3H), 5.29 (s, 0.5H), 5.15 (s, 0.5H), 4.52-4.55 (m, 3H), 4.32-4.40 (m, 1H), 4.02-4.20 (m, 2H), 3.90-3.95 (m, 1H), 3.80-3.82 (m, 1H), 3.34-3.56 (m, 6H), 3.10-3.15 (m, 4H), 2.47 (s, 3H), 2.04-2.30 (m, 6H), 1.08 (s, 9H). |
| 111 | C | 1H NMR (400 MHz, CD3OD): δ 8.70 (s, 1H), 8.60 (s, 1H), 8.47 (s, 1H), 7.88 (s, 1H), 7.74—7.76 (m, 1H), 7.61—7.43 (m, 2H), 7.43—7.47 (m, 2H), 7.30—7.32 (m, 2H), 7.11—7.15 (m, 1H), 7.05—7.08 (m, 1H), 5.29 (s, 0.5H), 5.16 (s, 0.5H), 4.66—4.67 (m, 1H), 4.50—4.65 (m, 2H), 4.32—4.36 (m, 1H), 4.03—4.09 (m, 2H), 3.92—3.95 (m, 1H), 3.80—3.83 (m, 1H), 3.37—3.59 (m, 4H), 2.41—2.57 (m, 2H), 2.05—2.31 (m, 7H), 1.06 (s, 9H). |
| 112 | C | 1H NMR (400 MHz, CD3OD): δ 8.90 (s, 1H), 8.70 (s, 1H), 8.61 (s, 1H), 7.85 (s, 1H), 7.75 (m, 1H), 7.65 (m, 2H), 7.40 (m, 4H), 7.15 (m, 3H), 5.29 (s, 0.64H), 5.15 (s, 0.64H), 4.62 (m, 5H), 4.20 (m, 1H), 3.85 (m, 1H), 3.80 (m, 1H), 3.5 (m,8H), 2.90 (s. 3H), 2.70 (s, 2H), 2.45 (s, 3H), 2.35 (m, 2H), 2.15 (m, 6H), 1.70 (s, 4H), 1.12 (s, 9H) |
| 113 | B | 1H NMR (400 MHz, DMSO-d6): δ 12.99 (s, 1H), 9.95 (s, 1H), 9.00 (s, 1H), 8.70 (s, 1H), 8.60 (m, 2H), 8.10 (s, 1H), 7.80 (d, J = 6.0 Hz, 1H), 7.63 (m, 3H), 7. 51(m, 4H), 7.37 (t, J = 4.8 Hz, 1H), 7.10 (d, J = 6.0 Hz, 2H), 5.23-5.36 (m, 1H), 5.14 (d, J = 3.2 Hz, 1H), 4.55 (d, J = 9.6 Hz, 1H), 4.19-4.47 (m, 4H), 3.67 (m, 2H), 3.21-3.48 (m, 10H), 1.90-2.46 (m, 13H), 1.10-1.31 (m, 5H), 1.01(s, 9H). |
| 114 | A | 1H NMR (300 MHz, DMSO-d6): δ 12.89 (s, 1H), 8.94 (s, 1H), 8.70-8.36 (m, 3H), 8.13 (s, 1H), 8.04 (s, 1H), 7.57 (dd, J = 9.0, 5.1 Hz, 4H), 7.38 (s, 4H), 7.22 (td, J = 8.8, 1.6 Hz, 1H), 7.03 (d, J = 8.7 Hz, 2H), 5.26 (d, J = 53.1 Hz, 2H), 4.54-4.16 (m, 5H), 3.68-3.50 (m, 3H), 3.42 (d, J = 19.4 Hz, 2H), 3.30 (dt, J = 25.7, 4.6 Hz, 2H), 3.15 (d, J = 18.7 Hz, 7H), 3.01 (s, 3H), 2.40 (d, J = 8.0 Hz, 7H), 2.16-1.78 (m, 4H), 1.37 (s, 1H), 0.91 (s, 9H). |
| 115 | B | 1H NMR (400 MHz, CD3OD): δ 8.80 (s, 1H), 8.67 (s, 1H), 8.57 (s, 1H), 7.89 (s, 1H), 7.75 (q, J = 6.0 Hz, 1H), 7.56 (d, J = 8.4 Hz, 2H), 7.39-7.47 (m, 4H), 7.13 (t, J = 8.2 Hz, 1H), 7.01 (d, J = 8.8 Hz, 2H), 5.29 (s, 0.5H), 5.15 (m, 0.5 H), 4.52-4.59 (m, 5H), 4.31-4.37 (m, 1H), 3.82-3.89 (m, 4H), 3.51-3.58 (m, 4H), 3.06 (s, 2H), 2.44 (s, 3H), 2.89-3.01 (m, 2H), 2.09-2.30 (m, 7H), 1.85-1.88 (m, 3H), 1.05(s, 9H). |

FIG. 3. Continued

| | | |
|---|---|---|
| 116 | B | 1H NMR (400 MHz, CD3OD): δ 8.88(s, 1H), 8.74(s, 1H), 8.65(s, 1H), 7.94(s, 1H), 7.69-7.80 (m, 3H), 7.38-7.51 (m, 7H), 7.15(t, J = 4.0 Hz, 1H), 5.50 (s, 2H), 5.28-5.37 (m, 1.5H), 5.18 (s, 0.5H), 4.40 (d, J = 8.2 Hz, 2H), 4.00-4.15 (m, 5H), 3.87-3.97 (m, 2H), 3.79-3.83 (m, 1H), 3.10 (s, 2H), 2.95 (s, 3H), 2.62 (s, 2H), 2.48 (s, 3H), 2.15-2.34 (m, 7H), 1.97 (s, 4H), 1.07 (s, 9H) |
| 117 | C | 1H NMR (400 MHz, DMSO-d6): δ 11.08 (s, 1H), 10.88 (s, 1H), 8.72 (s, 1H), 8.58-8.57 (m, 2H), 7.83 (d, J = 8.8 Hz, 2H), 7.73 (d, J = 8.4 Hz, 1H), 7.55 (d, J = 8.0 Hz, 1H), 7.49-7.48 (m, 2H), 7.43-7.41 (m, 2H), 7.35-7.33 (m, 1H), 7.25-7.21 (m, 1H), 7.16 (d, J = 9.2 Hz, 2H), 5.11-5.06 (m, 1H), 3.67-3.64 (m, 4H), 3.42-3.39 (m, 4H), 3.02-2.99 (m, 2H), 2.90-2.80 (m, 3H), 2.61-2.55 (m, 2H), 2.04-2.02 (br, 1H). |
| 118 | C | 1H NMR (400 MHz, DMSO-d6): δ 11.06 (s, 1H), 10.96 (s, 1H), 8.90(s, 1H), 8.71(d, J = 7.2 Hz, 2H), 7.92(d, J = 7.2 Hz, 2H), 7.71 (d, J = 7.6 Hz, 1H), 7.68 (d, J = 7.2 Hz, 1H), 7.41-7.52 (m, 5H), 7.22(t, J = 4.8 Hz, 1H), 6.79-6.81 (m, 1H), 6.66-6.69 (m, 1H), 5.03-5.09(m, 1H), 4.11-4.17 (m, 2 H), 3.80-3.83 (m, 2H), 2.77-3.26 (m, 8H), 2.56-2.57(m, 1H), 2.01-2.04(m, 1H). |
| 119 | B | 1H NMR (400 MHz, DMSO-d6): δ 11.09 (s, 1H), 10.91 (s, 1H), 8.58 (s, 1H), 8.78 (s, 1H), 8.58 (d, J = 4.0 Hz, 2H), 7.92 (d, J = 8.0 Hz, 2H), 7.58 (d, J = 8.0 Hz,1H), 7.53 (d, J = 8.4 Hz, 1H), 7.50 (d, J = 8.4 Hz, 2H), 7.42 (s, 1H), 7.21 (d, J = 8.0 Hz, 1H), 7.08 (d, J = 8.8 Hz, 2H), 6.91 (s, 1H), 6.77 (q, J = 4.0 Hz, 1H), 5.29—5.33 (m, 1H), 5.05—5.11 (m, 1H), 4.54—4.58 (m, 2H), 4.07—4.10 (m, 2H). 2.97 —3.01 (m, 2H), 2.81—2.83 (m, 3H), 2.53—2.61 (m, 2H), 1.99—2.03 (m. 2H). |
| 120 | B | 1H NMR (400 MHz, DMSO-d6): δ 11.09 (s, 1H), 10.91 (s, 1H), 8.76 (s, 1H), 8.58 (d, J = 5.6 Hz, 2H), 7.90 (d, J = 8.8 Hz, 2H), 7.67 (d, J = 8.4 Hz, 1H), 7.57 (d, J = 8.4 Hz, 1H), 7.50 (d, J = 5.6 Hz, 2H), 7.41 (s, 1H), 7.17—7.23 (m, 3H), 7.00 (s, 1H), 6.90 (d, J = 8.8 Hz, 1H), 5.31 (s. 1H), 5.05—5.10 (m, 1H), 3.86—3.89 (m, 1H), 3.58—3.64 (m, 3H), 2.82—3.02 (m, 6H), 2.51—2.62 (m, 3H), 2.32—2.41 (m, 2H), 2.02—2.04 (m, 1H). |
| 121 | A | 1H NMR (400 MHz, DMSO-d6): δ 11.08 (s, 1H), 10.91 (s, 1H), 8.86 (s, 1H), 8.59 (s, 2H), 7.94—7.96 (m, 2H), 7.68 (d, J = 8.0 Hz, 1H), 7.42—7.58 (m, 6H), 7.23 (d, J = 7.6 Hz. 1H), 7.02 (s, 1H), 6.91 (d, J = 7.2 Hz, 1H), 5.06—5.08 (m, 1H), 3.97 (s, 1H), 3.67 (s, 2H), 3.46—3.57 (m, 4H), 3.01 (s, 2H), 2.83—2.91 (m, 3H), 2.18—2.21 (m, 1H), 2.02—2.03 (m, 1H). |
| 122 | A | 1H NMR- (400 MHz, DMSO-d6): δ 11.10 (s, 1H), 10.89 (s, 1H), 8.73 (s, 1H), 8.57 (d, J = 6.0 Hz, 2H), 7.82 (d, J = 9.2 Hz, 2H), 7.74 (t, J = 5.2 Hz, 1H), 7.55 (d, J = 8.0 Hz, 1H), 7.49 (d, J = 6.0 Hz, 2H), 7.40 (m, 3H), 7.20 (m, 3H), 5.12 (m, 1H), 3.45 (m, 8H), 2.50-3.10 (m, 7H). |
| 123 | A | 1H NMR (400 MHz, DMSO-d6) δ 2.02-2.04 (1H, m), 2.55-2.61 (2H, m), 2.81-2.86 (2H, m), 2.89-2.90 (1H, m), 3.00-3.03 (2H, m), 3.46 (4H, s), 3.67 (4H, s), 5.07-5.11 (1H, m), 6.99-7.02 (1H, m), |

FIG. 3. Continued

| | | |
|---|---|---|
| 124 | C | 7.22 (1H, d, J = 8.4 Hz), 7.33-7.36 (1H, m), 7.40-7.43 (4H, m), 7.50-7.58 (4H, m), 7.73 (1H, d, J = 8.4 Hz), 8.59 (2H, dd, J = 1.6, 4.4 Hz), 8.90 (1H, s), 10.91 (1H, s), 11.09 (1H, s). |
| | A | 1H NMR (400 MHz, DMSO-d6) δ 1.97-2.02 (3H, m), 2.51-2.68 (2H, m), 2.80-2.87 (3H, m), 2.98-3.01 (2H, m), 3.44-3.60 (4H, m), 3.74 (2H, s), 3.85 (2H, s), 5.05 (1H, dd, J = 13.2, 5.6 Hz), 6.91 (2H, d, J = 9.2 Hz), 7.11 (1H, d, J = 8.0 Hz), 7.20 (2H, d, J = 9.6 Hz), 7.39 (1H, s), 7.47 (2H, d, J = 6.0 Hz), 7.55 (1H, d, J = 8.0 Hz), 7.64 (1H, d, J = 8.8 Hz), 7.70 (2H, d, J = 8.8 Hz), 8.56 (2H, d, J = 5.6 Hz), 8.62 (1H, s), 10.89 (1H, s), 11.07 (1H, s). |
| 125 | A | 1H NMR (400 MHz, DMSO-d6): δ 11.07 (s, 1H), 10.89 (s, 1H), 8.81 (s, 1H), 8.58 (d, J = 6.0 Hz, 2H), 7.88 (d, J = 8.4 Hz, 2H), 7.68 (d, J = 8.8 Hz, 1H), 7.56 (d, J = 8.0 Hz, 1H), 7.49 (d, J = 6.0 Hz, 2H), 7.41 —7.45 (m, 3H), 7.36 (s, 1H), 7.28 (d, J = 8.4 Hz, 1H), 7.22 (d, J = 8.0 Hz, 1H), 5.05—5.10 (m, 1H), 3.46 (s, 4H), 2.98—3.01 (m, 2H), 2.82—2.85 (m, 5H), 2.53—2.62 (m, 8H), 1.99—2.03 (m, 1H). |
| 126 | B | 1H NMR (400 MHz, DMSO-d6) δ 2.00-2.03 (1H, m), 2.55-2.74 (6H, m), 2.84-3.01 (5H, m), 3.48-3.60 (6H, m), 5.07 (1H, dd, J = 12.8, 4.8 Hz), 7.24 (2H, dd, J = 13.6, 8.0 Hz), 7.35 (1H, s), 7.42 (1H, s), 7.51-7.63 (5H, m), 7.68 (1H, d, J = 8.4 Hz), 7.95 (2H, d, J = 7.6 Hz), 8.59 (2H, d, J = 4.0 Hz), 8.85 (1H, s), 10.91 (1H, s), 11.08 (1H, s). |
| 127 | B | 1H NMR (400 MHz, DMSO-d6): δ 11.07 (s, 1H), 10.89 (s, 1H), 8.81 (s, 1H), 8.59 (d, J = 5.2 Hz, 2H), 7.90 (d, J = 5.2 Hz, 2H), 7.70 (d, J = 8.4 Hz, 1H), 7.57 (d, J = 8.0 Hz, 1H), 7.50 (d, J = 5.2 Hz, 2H), 7.47 (d, J = 8.4 Hz, 2H), 7.41 (d, J = 4.8 Hz, 2H), 7.33 (d, J = 8.8 Hz, 1H), 7.23 (d, J = 7.6 Hz, 1H), 5.09 (dd, J = 4.4 Hz, J = 12.4 Hz,1H), 4.25 (d, J = 12.4 Hz, 2H), 3.15 (t, J = 12.0 Hz, J = 20.4 Hz, 2H), 3.02-2.99 (m, 2H), 2.94-2.90 (m, 2H), 2.84-2.81 (m, 2H), 2.67-2.57 (m, 2H), 2.04-2.01 (m, 1H), 1.95 (d, J = 11.6 Hz, 2H), 1.79-1.74 (m, 2H). |
| 128 | B | 1H NMR (400 MHz, CDCl3): δ 8.58(d, J = 4.8 Hz, 2H), 8.14 (s, 1H), 8.03 (s, 1H), 7.77 (d, J = 8.4 Hz, 2H), 7.69 (t, J = 8.0 Hz, 2H), 7.52 (d, J = 4.8 Hz, 2H), 7.41-7.38 (m, 3H), 7.31 (d, J = 6.4 Hz, 2H), 7.25 (s, 1H), 7.09(d, J = 8.0 Hz 1H), 4.97-4.93 (m, 1H), 4.04 (d, J = 8.8 Hz, 2H), 3.12-3.00 (m, 6H), 2.96 -2.73 (m, 4H), 2.14-2.12 (m, 2H), 2.00-1.95 (m, 1H), 1.81 (t, J = 10 Hz, 2H). |
| 129 | B | 1H NMR (400 MHz, CDCl3): δ 8.55 (s, 2H), 8.18 (s, 1H), 7.89 (s, 1H), 7.71 (d, J = 8.5 Hz, 1H), 7.60 (t, J = 9.2 Hz, 2H), 7.52 (d, J = 3.9 Hz, 2H), 7.29 (d, J = 12.0 Hz, 2H), 7.22 (s, 1H), 7.09 (d, J = 8.4 Hz, 1H), 6.55 (d, J = 8.3 Hz, 2H), 4.90 – 4.97 (m, 1H), 4.09 (t, J = 6.9 Hz, 2H), 3.83 (t, J = 5.7 Hz, 2H), 3.48 (s, 4H), 3.37 – 3.44 (m, 1H), 3.02 (m, 4H), 2.88 (s, 4H), 2.63 (s, 4H), 2.08 – 2.17 (m, 1H). |
| 130 | B | 1H NMR (400 MHz, DMSO-d6) δ 11.06 (s, 1H), 10.88 (s, 1H), 8.70 (s, 1H), 8.60- 8.53 (m, 2H), 7.80-7.78 (d, J = 8.8 Hz, 2H), 7.60 - 7.58 (m, 2H), 7.56 - 7.54 (m, 1H), 7.41 (s, 1H), 7.22-7.20 (d, J |

FIG. 3. Continued

| | | |
|---|---|---|
| | | = 8.0 Hz, 1H), 7.16-7.10 (m, 4H), 5.09-5.06 (m, 1H), 3.72-3.69 (m, 3H), 3.58-3.55 (m, 1H), 3.29-3.25 (m, 4H), 3.04 - 2.96 (m, 4H), 2.86 -2.78 (m, 2H), 2.74 -2.66 (m, 2H), 2.64- 2.55 (m, 4H), 2.25-2.21 (m, 1H), 2.02-2.01 (m, 1H). 1.86-1.85 (m, 1H) |
| 131 | B | 1H NMR (300 MHz, DMSO-d6) δ 11.07 (s, 1H), 10.89 (s, 1H), 8.72 (s, 1H), 8.58- 8.56 (d, J = 8.1 Hz, 2H), 7.80-7.77 (d, J = 8.8 Hz, 2H), 7.61-7.50 (m, 2H), 7.49-7.47 (d, J = 5.8 Hz, 2H), 7.40 (s, 1H), 7.20-7.09 (m, 5H), 5.12–5.06 (m, 1H), 3.67-3.60 (m, 3H), 3.57-3.54 (m, 1H), 3.33-3.25 (m, 4H), 3.00 –2.90 (m, 4H), 2.86 – 2.75 (m, 2H), 2.67- 2.56 (m, 6H), 2.26-2.21 (m, 1H), 2.03-2.00 (m, 1H), 1.89-1.85 (m. 1H) |
| 132 | D | 1H NMR (400 MHz, DMSO-d6): δ 11.13 (s, 1H), 10.90 (s, 1H), 8.73 (s, 1H), 8.57 (d, J = 6.0 Hz, 2H), 7.84 (t, J = 8.4 Hz, 3H), 7.59-7.55 (m, 2H), 7.49 (d, J = 6.0 Hz, 2H), 7.41 (s, 1H), 7.23-7.18 (m, 3H), 5.16-5.11 (m, 1H), 3.56-3.42 (m, 8H), 3.02-2.99 (m, 2H), 2.95-2.81 (m, 3H), 2.68-2.55 (m, 2H), 2.08-2.02 (m, 1H). |
| 133 | C | 1H NMR (400 MHz, DMSO-d6): δ 11.10 (s, 1H), 10.91 (s, 1H), 8.79 (s, 1H), 8.58 (d, J = 6.0 Hz, 2H), 7.89 (d, J = 8.8 Hz, 2H), 7.71 (d, J = 8.4 Hz, 1H), 7.56 (d, J = 8.0 Hz, 1H), 7.35-7.50 (m, 5H), 7.26 (d, J = 8.8 Hz, 2H), 7.22 (d, J = 8.4 Hz, 1H), 5.06-5.11 (m, 1H), 3.92 (d, J = 10.4 Hz, 2H), 3.49 (m, 2H), 3.18-3.24 (m, 2H), 2.81-3.02 (m, 5H), 2.60 (m, 2H), 2.05 (m, 1H), 0.94 (d, J = 6.0 Hz, 6H). |
| 134 | A | 1H NMR (400 MHz, CDCl3): δ 8.55-8.54 (d, J = 4.2 Hz, 2H), 8.01 (s, 1H), 7.87 (s, 1H), 7.65-7.63 (d, J = 8.0 Hz, 2H), 7.60-7.57(d, J = 8.8 Hz, 2H), 7.51-7.48 (m, 2H), 7.28 (s, 1H), 7.23-7.20 (m, 1H), 7.15 (s, 1H), 6.97 (s, 1H), 6.71-6.69 (d. J = 8.8 Hz, 1H), 6.64-6.62 (d, J = 8.8 Hz, 2H), 4.94-4.90 (m, 1H), 4.67 (s, 1H), 4.63 (s, 1H), 3.78-3.72 (m, 2H), 3.44-3.42 (d, J = 9.6 Hz, 1H), 3.26-3.24 (d, J = 8.8 Hz, 1H), 3.08-2.95 (m, 4H), 2.92-2.70 (m, 3H), 2.31-2.19 (m, 2H), 2.15-2.07 (br, 1H). |
| 135 | B | 1H NMR (400 MHz, CDCl3): δ 8.55 (s, 2H), 8.10 (s, 1H), 7.87 (s, 1H), 7.64 (d, J = 8.4 Hz, 2H), 7.58 (d, J = 8.8 Hz, 2H), 7.50 (d, J = 4.7 Hz, 2H), 7.32 – 7.39 (m, 1H), 7.22 (d, J = 7.6 Hz, 1H), 6.97 (s, 1H), 6.71 (s, 1H), 6.63 (d, J = 9.0 Hz, 2H), 4.92 (dd, J = 12.6, 5.5 Hz, 1H), 4.65 (d, J = 19.2 Hz, 2H), 3.67 – 3.80 (m, 2H), 3.43 (d, J = 9.0 Hz, 1H), 3.25 (d, J = 8.5 Hz, 1H), 3.02 (d, J = 11.6 Hz, 3H), 2.65 – 2.93 (m, 4H), 2.24 (dd, J = 25.7, 8.1 Hz, 2H), 2.06 – 2.15 (m, 1H). |
| 136 | C | 1H NMR (400 MHz, DMSO-d6): δ 11.10 (s, 1H), 10.90 (s, 1H), 8.92 (s, 1H), 8.59 (d, J = 5.6 Hz, 2H), 7.63-7.72 (m, 3H), 7.43-7.57 (m, 6H), 7.36 (d, J = 8.8 Hz, 1H), 7.21 (d, J = 8.0 Hz, 1H), 7.08 (d, J = 8.0 Hz, 1H), 5.07-5.11 (m, 1H), 3.89 (d, J = 10.4 Hz, 2H), 3.60 (m, 2H), 3.18-3.25 (m, 2H), 2.82-3.01 (m, 6H), 2.05 (m, 1H), 0.99 (d, J = 6.0 Hz, 6H). |
| 137 | A | 1H NMR (400 MHz, CDCl3): δ 8.56 (d, J = 4.0 Hz, 2H), 8.16 (s, 1H), 7.94 (s, 1H), 7.66 – 7.72 (m, |

FIG. 3. Continued

| | | |
|---|---|---|
| 138 | D B | 4H), 7.50 (d, J = 4.8 Hz, 2H), 7.43 (s, 1H), 7.29 (s, 1H), 7.19 – 7.26 (m, 2H), 6.93 – 6.98 (m, 3H), 4.92 – 4.96 (m, 1H), 4.24 (t, J = 4.8 Hz, 2H), 3.94 (t, J =10 Hz, 2H), 3.23 (s, 3H), 3.00 – 3.04 (m, 4H), 2.77 – 2.92 (m, 4H), 2.12 – 2.15 (d, J =8.4 Hz, 1H). |
| 139 | | 1H NMR (400 MHz, DMSO-d6): δ 11.07 (s, 1H), 10.89 (s, 1H), 8.81 (s, 1H), 8.60 (s, 2H), 7.89 (d, J = 8.4 Hz, 2H), 7.71 (t, J = 7.6 Hz, 1H), 7.57 (d, J = 8.0 Hz, 1H), 7.52 (s, 2H), 7.42-7.46 (m, 3H), 7.35-7.37 (m, 2H), 7.23 (d, J = 7.6 Hz, 1H), 5.08-5.12 (m, 1H), 3.43-3.47 (m, 2H), 3.02-3.03 (m, 2H), 2.92-3.00 (m, 4H), 2.82-2.87 (m, 8H), 2.56-2.68 (m, 3H), 2.02-2.04 (m, 1H). |
| 140 | D | 1H NMR (400 MHz, DMSO-d6): δ 11.09 (s, 1H), 8.90 (s, 1H), 8.60 (s, 2H), 8.39 (d, J = 8.8 Hz, 1H), 8.12(d, J = 7.2 Hz, 1H), 7.86 (d, J = 8.4 Hz, 2H), 7.73 (d, J = 8.8 Hz, 1H),7.59 (s, 1H), 7.51-7.50 (m, 3H), 7.44 (s, 1H), 7.35 (d, J = 10 Hz, 1H), 7.18 (d, J = 8.4 Hz, 2H), 7.10 (d, J = 7.2 Hz, 1H), 5.11-5.07 (m, 1H), 3.67 (s, 4H), 3.41 (s, 4H), 3.03 (t, J = 7.6 Hz, 2H), 2.90-2.86 (m, 1H), 2.68 (br, 2H), 2.05-1.98(m, 1H), 1.87-1.79(m, 2H), 1.02 (t, J = 7.6 Hz, 3H). |
| 141 | B | 1H NMR (400 MHz, CDCl3): δ 8.90 (s, 1H), 8.60-8.53 (m, 3H), 8.11-8.09 (m, 2H), 8.00 (s, 1H), 7.76-7.71 (m, 4H), 7.62-7.60 (m, 1H), 7.50 (s,2H), 7.35 (s, 1H), 7.13 (d, J = 8.4 Hz, 1H), 7.07 (d, J = 8.4 Hz, 2H), 6.66 (s, 1H), 4.98-4.94 (m, 2H),3.64 (s, 4H), 3.45 (s, 4H), 3.13-3.10 (m, 2H), 2.93-2.71 (m, 3H), 2.16-2.13 (m, 1H), 1.94-1.88(m, 2H), 1.06 (t, J = 7.2 Hz, 1H). |
| 142 | C | 1H NMR (400 MHz, DMSO-d6): δ 11.08 (s, 1H), 10.88 (s, 1H), 8.90 (s, 1H), 8.58 (d, J = 5.2 Hz, 2H), 7.75 (t, J = 8.0 Hz, 1H), 7.52–7.57 (m, 4H), 7.42-7.50 (m, 5H), 7.22 ( d, J = 7.6 Hz, 1H), 7.03–7.04 (m, 1H), 5.10–5.14 (m, 1H), 3.57 (s, 8H), 3.00 (t, J = 5.6 Hz, 2H), 2.81–2.89 (m, 3H), 2.50–2.56 (m, 2H), 2.03–2.06 (m, 1H). |
| 143 | D | 1H NMR (400 MHz, DMSO-d6): δ 11.85 (s, 1H), 10.91 (s, 1H), 8.84 (s, 1H), 8.59 (d, J = 5.2 Hz, 2H), 7.94—7.96 (m, 2H), 7.70 (t, J = 8.0 Hz, 1H), 7.49—7.58 (m, 5H), 7.42 (s, 1H), 7.34—7.37 (m, 2H), 7.23 (d, J = 7.6 Hz, 1H), 5.07—5.11 (m, 1H), 3.63 (s, 2H), 3.43—3.45 (m, 4H), 2.99—3.02 (m, 2H), 2.81—2.84 (m, 3H), 2.54—2.60 (m, 6H), 1.99—2.03 (m, 1H). |
| 144 | C | 1H NMR (400 MHz, DMSO-d6): δ 11.12 (s, 1H), 10.94 (s, 1H), 8.74-8.82 (m, 3H), 7.77-7.88 (m, 5H), 7.54-7.61 (m, 2H), 7.46 (s, 1H), 7.28 (d, J = 8.0 Hz, 1H), 7.19 (d, J = 8.8 Hz, 2H), 5.10-5.15 (m, 1H), 3.30 (s, 8H), 3.01-3.04 (m, 2H), 2.83-2.90 (m, 2H), 2.54-2.63 (m, 3H), 2.04-2.06 (m, 1H). |
| | C | 1H NMR (400 MHz, DMSO-d6): δ 11.08 (s, 1H), 10.91 (s, 1H), 8.73 (s, 1H), 8.57 (d, J = 6.0 Hz, 2H), 7.87(d, J = 8.8 Hz, 2H), 7.64 (d, J = 8.0 Hz, 1H), 7.56 (d, J = 8.0 Hz, 1H), 7.48 (d, J = 6.0 Hz, 1H), 7.40 (s, 1H), 7.21 (d, J = 8.0 Hz, 1H), 7.12(d, J = 8.8 Hz, 2H), 6.78 (s, 1H), 6.65-6.62 (m, 1H), 5.08-5.04 (m, 1H), 4.20 (t, J = 8.0 Hz, 2H), 4.09 (t, J = 6.0 Hz, 2H), 3.80 (t, J = 6.0 Hz, 2H), 3.01-2.92 (m, 3H), 2.88-2.78 (m, 3H), 2.61-2.54 (m, 2H), 2.13-2.12 (m, 2H), 2.02-1.99 (m, 1H). |
| 145 | D B | 1H NMR(400 MHz, DMSO-d6): δ: 11.05(s, 1H), 10.89(s, 1H), 8.74(s, 1H), 8.59(d, J = 5.2 Hz, |

FIG. 3. Continued

| | | |
|---|---|---|
| 146 | B | 2H), 7.87(d, J = 8.8 Hz, 2H), 7.64(d, J = 8.0 Hz, 1H), 7.52-7.57(m, 3H), 7.41(s, 1H), 7.23(s, 1H), 7.12(d, J = 9.2 Hz, 2H), 6.77(s, 1H), 6.65(s, 1H), 5.01-5.09(m, 1H), 4.17(t, J = 8.0 Hz, 2H), 4.02-4.08(m, 2H), 3.70(t, J = 6.0 Hz, 2H), 3.00(t, J = 6.0 Hz, 2H), 2.81-2.87(m, 4H), 2.54-2.60(m, 2H), 1.79(s, 4H). |
| 147 | C | 1H NMR (400 MHz, CDCl3) δ 8.51-8.49 (d, J = 6.0 Hz, 2 H), 7.93-7.90 (m, 2 H), 7.65-7.58 (m, 5 H), 7.24-7.19 (m, 2 H), 7.08 (s, 1 H), 6.93-6.82 (m, 3 H), 4.93-4.83 (m, 1 H), 4.81-4.77 (m, 1 H), 4.65-4.61 (m, 1 H), 3.03-2.96 (m, 6 H), 2.95-2.59 (m, 7 H), 2.11-2.00 (m, 1 H), 1.96-1.92 (m, 1 H) |
| 148 | A | 1H NMR (400 MHz, CDCl3) δ 8.50-8.49 (d, J = 5.6 Hz, 2 H), 7.93-7.90 (m, 2 H), 7.69-7.45 (m, 5 H), 7.45-7.24 (m, 2 H), 7.09 (s, 1 H), 6.93-6.84 (m, 3 H), 4.90-4.86 (m, 1 H), 4.48-4.47 (m, 1 H), 4.04-3.99 (m, 1 H), 3.04-2.97 (m, 8 H), 2.95-2.71 (m, 3 H), 2.33-2.31 (m, 2 H), 2.09-2.04 (m, 2 H) |
| 149 | A | 1H NMR (400 MHz, DMSO-d6): δ 11.04 (s, 1H), 10.88 (s, 1H), 8.72 (s, 1H), 8.57 (d, J = 2.0 Hz, 2H), 7.83 (d, J = 8.4 Hz, 2H), 7.49-7.57 (m, 3H), 7.42 (s, 1H), 7.15-7.23 (m, 3H), 7.04 (s, 1H), 6.77 (s, 1H), 5.00-5.04 (m, 1H), 3.97 (s, 3H), 3.70 (s, 4H), 3.35-3.41 (m, 4H), 3.01-3.02 (m, 2H), 2.81-2.88 (m, 2H), 2.34-2.68 (m, 3H), 1.98-2.02 (m, 1H). |
| 150 | D | 1H NMR (400 MHz, DMSO-d6): δ 11.08 (s, 1H), 10.88 (s, 1H), 8.72 (s, 1H), 8.56 (d, J = 6.0Hz ,2H), 7.82 (d, J = 9.2 Hz, 2H), 7.37-7.56 (m, 6H), 7.16-7.23 (m, 3H), 5.07-5.11 (m, 1H), 4.01 (s, 3H), 3.31-3.50 (m, 8H), 2.99-3.02 (m, 2H), 2.80-2.83 (m, 3H), 2.51-2.55 (m, 2H), 1.98-2.10 (m, 1H). |
| 151 | C | 1H NMR (400 MHz, DMSO-d6): δ 8.56 (d, J = 5.6 Hz, 2H), 8.37 (s, 1H), 7.94 (s, 1H), 7.68 (d, J = 9.2 Hz, 3H), 7.55 — 7.57 (m, 1H), 7.51 (d, J = 5.6 Hz, 2H), 7.38 — 7.40 (m, 1H), 7.21 — 7.28 (m, 2H), 7.15 (d, J = 8.4 Hz, 1H), 7.04 (d, J = 8.8 Hz, 2H), 4.91 — 4.98 (m, 1H), 4.18 (d, J = 4.8 Hz, 2H), 3.82 — 3.84 (m, 2H), 3.63 (d, J = 6.4 Hz, 2H), 3.49 (s, 2H), 3.36 — 3.38 (m, 4H), 3.02 (d, J = 10.8 Hz, 4H), 2.69 — 2.87 (m, 8H), 2.52 — 2.56 (m, 2H), 1.85 — 1.88 (m, 1H). |
| 152 | B | 1H NMR (400 MHz, DMSO-d6): δ 11.08 (s, 1H), 10.89 (s, 1H), 8.75 (s, 1H), 8.58-8.57 (d, J = 5.2 Hz, 2H), 7.89-7.86 (d, J = 8.8 Hz, 2H), 7.73-7.69 (t, J = 8.0 Hz, 1H), 7.57-7.55 (d, J = 8.0 Hz, 1H), 7.49-7.48 (d, J = 5.2 Hz, 2H), 7.41 (s, 1H), 7.37-7.34 (m, 2H), 7.22-7.20 (d, J = 8.0 Hz, 1H), 7.16-7.14 (d, J = 8.8 Hz, 2H), 5.12-5.07 (m, 1H), 4.25-4.17 (m, 2H), 3.05-2.96 (m, 2H), 2.95-2.86 (m, 1H), 2.86-2.78 (m, 4H), 2.77-2.65 (m, 8H), 2.52 — 2.56 (m, 2H), 2.64-2.52 (m, 5H), 2.08-1.97 (m, 1H). |
| 153 | D | 1H NMR (400 MHz, CDCl3): δ 8.75 (s, 1H), 8.56 (d, J = 5.2 Hz, 2H), 8.45 (m, 1H), 7.94 (m, 1H), 2H), 7.87 (d, J = 8.8 Hz, 2H), 7.68 (d, J = 8.4 Hz, 1H), 7.55 (d, J = 8.0 Hz, 1H), 7.48 (d, J = 4.4 Hz, 2H), 7.20-7.41 (m, 4H), 7.14 (d, J = 9.2 Hz, 2H), 5.08 (m, 1H), 4.21 (t, J = 5.6 Hz, 2H), 3.47 (m, 4H), 2.67-3.02 (m, 10H), 2.05 (m, 1H). |

FIG. 3. Continued

| | | |
|---|---|---|
| | | 7.75 (d, J = 8.0 Hz, 1H), 7.65-7.69 (m, 3H), 7.51 (d, J = 4.8 Hz, 2H), 7.36 (m, 1H), 7.18-7.23 (m, 2H), 6.98 (d, J = 8.8 Hz, 2H), 4.94 (m, 1H), 4.24 (t, J = 5.2 Hz, 2H), 4.16 (t, J = 5.2 Hz, 2H), 2.90-3.04 (m, 8H), 2.62-2.86 (m, 4H), 2.52 (s, 3H), 2.12 (m, 1H). |
| 154 | B | 1H NMR (400 MHz, DMSO-d6): δ 11.07 (s, 1H), 10.90 (s, 1H), 8.90 (s, 1H), 8.58 (d, J = 6.0 Hz, 2H), 7.68 (d, J = 8.4 Hz, 1H), 7.42—7.57 (m, 7H), 7.35 (s, 1H), 6.99—7.28 (m, 2H), 6.97 (d, J = 4.8 Hz, 1H), 5.06—5.09 (m, 1H), 4.25 (t, J = 5.2 Hz, 2H), 3.47 (s, 5H), 2.98—2.31 (m, 2H), 2.81—2.88 (m, 5H), 2.56—2.67 (m, 5H), 1.97—2.03 (m, 1H). |
| 155 | | 1H NMR (400 MHz, CDCl3) δ 8.92 (s, 1H), 8.63 – 8.57 (m, 1H), 8.54 (d, J = 5.9 Hz, 2H), 8.31 – 8.24 (m, 1H), 8.10 (s, 1H), 8.09 – 8.00 (m, 1H), 7.73 (m, 3H), 7.44 (d, J = 5.9 Hz, 2H), 7.34 – 7.29 (m, 1H), 7.17 – 7.12 (m, 1H), 7.07 (d, J = 9.0 Hz, 2H), 5.04 – 4.94 (m, 1H), 4.20 (s, 2H), 3.91 (s, 2H), 3.76 (d, J = 4.5 Hz, 2H), 3.74 – 3.61 (m, 4H), 3.26 (s, 4H), 3.06 – 2.98 (m, 2H), 2.88 – 2.72 (m, 3H), 2.68 (s, 5H), 2.09 – 2.00 (m, 1H), 1.88 – 1.77 (m, 3H), 1.01 (t, J = 7.5 Hz, 3H). |
| 156 | D | 1H NMR (400 MHz, DMSO-d6): δ 11.14 (s, 1H), 8.98 (s, 1H), 8.66 (d, J = 6.0 Hz, 2H), 8.39 (d, J = 8.4 Hz, 1H), 8.18 (d, J = 7.2 Hz, 1H), 7.96 (d, J = 8.8 Hz, 2H), 7.74 (d, J = 8.4 Hz, 1H), 7.65 (s, 1H), 7.55-7.59 (m, 3H), 7.42 (s, 1H), 7.34 (s, 1H), 7.22 (d, J = 8.8 Hz, 2H), 7.16 (d, J = 7.2 Hz, 1H), 5.05-5.18 (m, 1H), 4.27 (s, 2H), 3.41-3.54 (m, 8H), 3.07-3.11 (m, 2H), 2.80-3.00 (m, 4H), 2.02-2.14 (m, 2H), 1.87-1.95 (m, 2H), 1.07 (t, J = 7.6 Hz, 3H). |
| 157 | | 1H NMR (400 MHz, CDCl3): δ 11.18 – 11.00 (m, 1H), 8.50 (s, 2H), 8.47 – 8.34 (m, 2H), 8.11 (s, 1H), 7.71 (d, J = 9.0 Hz, 2H), 7.58 (d, J = 8.5 Hz, 1H), 7.49 (d, J = 5.2 Hz, 2H), 7.45 – 7.40 (m, 1H), 7.33 (s, 2H), 7.23 (s, 2H), 7.05 (d, J = 9.0 Hz, 2H), 6.97 – 6.91 (m, 1H), 4.94 – 4.88 (m, 1H), 4.23 (s, 2H), 3.87 (s, 2H), 3.75 (s, 2H), 3.36 (s, 3H), 3.20 (s, 2H), 2.67 – 2.74 (m, 8H), 2.26 – 2.18 (m, 1H), 2.03 (d, J = 7.9 Hz, 4H), 1.10 (t, J = 7.4 Hz, 3H). |
| 158 | | 1H NMR (400 MHz, DMSO-d6): δ 11.07 (s, 1H), 8.88-8.92 (m, 2H), 8.70 (s, 1H), 8.56 (d, J = 4.8 Hz, 2H), 7.77-7.93 (m, 3H), 7.68-7.75 (m, 2H), 7.59 (d, J = 7.6 Hz, 1H), 7.51 (d, J = 5.2 Hz, 2H), 7.36 (s, 1H), 7.28 (d, J = 8.4 Hz, 1H), 7.17 (d, J = 8.8 Hz, 2H), 5.05-5.10 (m, 1H), 4.22 (s, 2H), 3.48 (m, 6H), 3.00-3.11 (m, 3H), 2.68-2.90 (m, 8H), 2.02-2.14 (m, 1H), 1.60-1.75 (m, 2H), 0.97 (t, J = 7.6 Hz, 3H). |
| 159 | | 1H NMR (400 MHz, CDCl3): δ 8.92 (s, 1H), 8.56 (d, J = 5.3 Hz, 2H), 8.18 (s, 1H), 8.04 – 8.14 (m, 2H), 7.72 (t, J = 7.4 Hz, 3H), 7.65 (d, J = 7.4 Hz, 1H), 7.55 (d, J = 8.5 Hz, 1H), 7.47 (d, J = 4.8 Hz, 2H), 7.23 (s, 1H), 7.06 (d, J = 8.7 Hz, 2H), 6.94 (d, J = 8.2 Hz, 1H), 4.91-4.95 (m, 1H), 4.23 (s, 2H), 3.88 (s, 2H), 3.77 (s, 4H), 3.37 (s, 4H), 3.03 – 3.13 (m, 2H), 2.71 (m, 10H), 2.08 (s, 1H), 1.88 (q, J = 7.6 Hz, 2H), 1.04 (t, J = 7.4 Hz, 3H). |
| 160 | B | 1H NMR (400 MHz, DMSO-d6): δ 11.07 (s, 1H), 10.89 (s, 1H), 8.89 (s, 1H), 8.57 (dd, J = 1.2 Hz, |

FIG. 3. Continued

| | | |
|---|---|---|
| 161 | B | 4.4 Hz, 2H), 7.40–7.64 (m, 8H), 7.30 (s, 1H), 7.19–7.21 (d, J = 8.0 Hz, 2H), 6.96 (t, J = 2.0 Hz, 1H), 5.06 (t, J = 7.2 Hz, 1H), 4.21–4.23 (m, 2H), 3.78–3.79 (m, 2H), 3.65 (t, J = 6.0 Hz, 2H), 3.38–3.39 (m, 4H), 2.98–3.02 (m, 2H), 2.78–2.80 (m, 2H), 2.56 (s, 9H), 1.98–2.01 (m, 1H). |
| 161 | B | 1H NMR (400 MHz, DMSO-d6): δ 11.07 (s, 1H), 10.90 (s, 1H), 8.74 (s, 1H), 8.57 (d, J = 6.0 Hz, 2H), 7.86 (d, J = 8.8 Hz, 2H), 7.64 (d, J = 8.4 Hz, 1H), 7.56 (d, J = 8.0 Hz, 1H), 7.49 (d, J = 6.0 Hz, 2H), 7.41 (s, 1H), 7.21 (d, J = 8.4 Hz, 1H), 7.10 (d, J = 9.2 Hz, 2H), 6.79 (s, 1H), 6.66-6.64 (m, 1H), 5.08-5.03 (m, 1H), 4.13(s, 4H), 4.03-4.02 (m, 2H),3.60 (t, J = 6.4 Hz, 1H), 3.43 (s, 2H), 3.02-2.99 (m, 2H), 2.91-2.78 (m, 5H), 2.60-2.55 (m, 3H), 2.02-1.99 (m, 1H). |
| 162 | C | 1H NMR (400 MHz, DMSO-d6): δ 11.07 (s, 1H), 10.88 (s, 1H), 8.73 (s, 1H), 8.57 (d, J = 5.6 Hz, 2H), 7.86 (d, J = 8.4 Hz, 2H), 7.69 (t, J = 4.2 Hz, 1H), 7.56(d, J = 8.0 Hz, 1H), 7.48 (d, J = 6.0 Hz, 2H), 7.40 (s, 1H), 7.34 (t, J = 7.2 Hz, 2H), 7.22 (d, J = 4.0 Hz, 1H), 7.11 (d, J = 8.8 Hz, 2H), 5.04-5.13 (m, 1H), 4.06-4.15 (m, 3H), 3.17(d, J = 5.2 Hz, 2H), 2.96-3.05 (m, 2H), 2.82-2.84 (m, 2H), 2.57-2.60 (m, 7H), 2.43 (s, 2H), 1.76-1.85 (m, 2H), 1.61-1.70 (m, 2H), 1.50 (d, J = 5.2 Hz, 2H). |
| 163 | D | 1H NMR (400 MHz, DMSO-d6): δ 11.08 (s, 1H), 10.90 (s, 1H), 8.73 (s, 1H), 8.57 (d, J = 6.4 Hz, 2H), 7.86(d, J = 8.8 Hz, 2H), 7.70 (t, J = 8.0 Hz, 1H), 7.55 (d, J = 8.0 Hz, 1H), 7.48 (d, J = 6.4 Hz, 2H), 7.40 (s, 1H), 7.37-7.34 (m, 2H), 7.21 (d, J = 7.6 Hz, 1H), 7.12(d, J = 8.8 Hz, 2H), 5.11-5.07 (m, 1H),4.11-4.09 (m, 2H), 3.50-3.45 (m, 4H), 3.00-2.98 (m, 2H), 2.91-2.80 (m, 3H), 2.68-2.57 (m, 8H), 2.04-1.96 (m, 3H). |
| 164 | B | 1H NMR (400 MHz, DMSO-d6): δ 11.07 (s, 1H), 10.89 (s, 1H), 8.73 (s, 1H), 8.57 (d, J = 6.0 Hz, 2H), 7.86 (d, J = 8.8 Hz, 2H), 7.68 (d, J = 8.4 Hz, 1H), 7.55 (d, J = 8.0 Hz, 1H), 7.48 (d, J = 6.0 Hz, 2H), 7.40 (s, 1H), 7.34 (s, 1H), 7.26 (d, J = 8.0 Hz, 1H), 7.21 (d, J = 8.0 Hz, 1H), 7.12 (d, J = 9.2 Hz), 5.09-5.05 (m, 1H), 4.12-4.09(m, 2H), 3.46 (s, 6H),3.01-2.99 (m, 2H), 2.88-2.81 (m, 3H), 2.61-2.54 (m, 6H), 2.03-1.94 (m, 3H). |
| 165 | C | 1H NMR (400 MHz, DMSO-d6): δ11.07 (s, 1H), 10.88 (s, 1H), 8.73 (s, 1H), 8.57 (d, J = 5.2Hz, 2H), 7.86 (d, J = 8.8Hz, 2H), 7.68 (d, J = 8.8Hz, 1H), 7.56 (d, J = 8.0Hz, 1H), 7.48 (d, J = 5.6Hz, 2H), 7.40 (s, 1H), 7.34 (s, 1H), 7.19-7.28 (m, 2H), 7.11 (d, J = 9.2Hz, 2H), 5.04-5.13 (m, 1H), 4.06-4.15 (m, 2H), 3.44 (s, 4H), 3.17 (d, J = 5.2Hz, 1H), 2.99-3.02 (m, 2H), 2.78-2.91 (m, 3H), 2.60 (s, 2H), 2.42 (t, J = 4.2Hz, 2H), 1.97-2.05 (m, 1H), 1.76-1.85 (m, 2H), 1.62-1.66 (m, 2H), 1.52 (d, J = 12Hz, 3H). |
| 166 | C | 1H NMR (400 MHz, CD3OD): δ 8.70 (bs, 2H), 8.44 (s, 1H), 8.15 (s, 2H), 7.77–7.83 (m, 3H), 7.71 (d, J = 8.0 Hz, 1H), 7.50 (s, 1H), 7.44 (s, 1H), 7.38 (d, J = 2.0 Hz, 1H), 7.31 (d, J = 8.4 Hz, 1H), 7.16 (d, J = 9.2 Hz, 2H), 4.71–4.75 (m, 2H), 3.86 (d, J = 12.0 Hz, 2H), 3.40–3.60 (m, 7H), 3.21–3.23 (m, 2H), 3.09–3.10 (m, 2H), 2.87–2.95 (m, 5H), 2.73–2.77 (m, 2H), 2.10–2.12 (m, 2H), 1.97– |

FIG. 3. Continued

| | | |
|---|---|---|
| | | 2.00 (m, 2H), 1.52–1.55 (m, 2H). |
| 167 | B | 1H NMR (400 MHz, DMSO-d6): δ 11.08 (s, 1H), 10.91 (s, 1H), 8.73 (s, 1H), 8.57 (d, J = 5.6 Hz, 2H), 7.85 (d, J = 8.8 Hz, 2H), 7.64 (d, J = 8.4 Hz, 1H), 7.55 (d, J = 8.0 Hz, 1H), 7.48 (d, J = 5.6 Hz, 2H), 7.40 (s, 1H), 7.30 (s, 1H), 7.21 (d, J = 7.2 Hz, 2H), 7.08 (d, J = 8.8 Hz, 2H), 5.00-5.10 (m, 1H), 3.95-4.15 (m, 4H), 3.55-3.70 (m, 4H), 3.17 (s, 1H), 2.75-3.05 (m, 12H), 2.50-2.65 (m, 2H), 1.95-2.20 (m, 2H), 1.00-1.15 (m, 2H). |
| 168 | A | 1HNMR (400 MHz, DMSO-d6): δ 10.95 (s, 1H), 10.91 (s, 1H), 8.75 (s, 1H), 8.57 (d, J = 5.6 Hz, 2H), 7.87 (d, J = 8.8 Hz, 2H), 7.48-7.57 (m, 4H), 7.41 (s, 1H), 7.21 (d, J = 8.0 Hz, 1H), 7.14 (d, J = 8.8 Hz, 2H), 7.00-7.09 (m, 2H), 5.00-5.10 (m, 1H), 4.15-4.40 (m, 4H), 2.95-3.05 (m, 2H), 2.75-2.95 (m, 4H), 2.55-2.75 (m, 7H), 2.30-2.45 (m, 1H), 1.90-2.05 (m, 4H). |
| 169 | D | 1H NMR (400 MHz, DMSO-d6): δ11.07 (s, 1H), 10.88 (s, 1H), 8.68 (s, 1H), 8.56 (d, J = 5.2 Hz, 2H), 7.75 (d, J = 8.4 Hz, 2H), 7.68 (d, J = 8.4 Hz, 1H), 7.55 (d, J = 8.0Hz, 1H), 7.47 (d, J = 5.2Hz, 1H), 7.40 (s, 1H), 7.34 (s, 1H), 7.20-7.27 (m, 2H), 7.07(d, J = 8.4 Hz, 2H), 5.05-5.08 (m, 1H), 3.76 (d, J =12.0 Hz, 2H), 3.44 (s, 7H), 3.00 (s, 2H), 2.84 (s, 3H), 2.71 (t, J =12.4Hz, 2H), 2.60 (s, 3H), 2.39 (s, 3H), 1.99-2.03 (m, 2H), 1.80 (d, J =11.2 Hz, 2H), 1.47 (s, 3H) |
| 170 | C | 1H NMR (400 MHz, CDCl3): δ 8.56 (d, J = 5.6 Hz, 2H), 8.12 (s, 1H), 7.94 (s, 1H), 7.78 (d, J = 8.4 Hz, 1H), 7.64-7.70 (m, 3H), 7.51 (d, J = 6.0 Hz, 2H), 7.29-7.34 (m, 3H), 7.19-7.22 (m, 2H), 7.03 (d, J = 8.8 Hz, 2H), 4.92-4.97 (m, 1H), 4.52-4.57 (m, 1H), 4.20 (t, J = 5.2 Hz, 2H), 3.00-3.06 (m, 4H), 2.89-2.93 (m, 8H), 2.58-2.59 (m, 2H), 2.12-2.15 (m, 2H), 2.00-2.02 (m, 2H). |
| 171 | D | 1H NMR (400 MHz, DMSO-d6): δ 11.11 (s, 1H), 10.90 (s, 1H), 8.74 (s, 1H), 8.58 (d, J = 5.2 Hz, 2H), 7.82-7.88 (m, 3H), 7.35-7.57 (m, 6H), 7.21 (d, J = 8.0 Hz, 2H), 7.13 (d, J = 8.8 Hz, 2H), 5.06-5.11 (m, 1H), 4.14-4.16 (m, 2H), 4.06 (d, J = 5.6 Hz, 2H), 2.99-3.01 (m, 4H), 2.72-2.84 (m, 5H), 2.58-2.62 (m, 2H), 2.06-2.12 (m, 3H), 1.76-1.79 (m, 3H), 1.34-1.37 (m, 1H). |
| 172 | C | 1H NMR (400 MHz, DMSO-d6): δ 11.10 (s, 1H), 10.89 (s, 1H), 8.74 (s, 1H), 8.58 (d, J = 5.3 Hz, 2H), 8.21 (s, 1H), 7.85 (dd, J = 12.7, 8.6 Hz, 3H), 7.56 (d, J = 7.9 Hz, 1H), 7.45 – 7.51 (m, 3H), 7.41 (s, 1H), 7.37 (d, J = 8.4 Hz, 1H), 7.22 (d, J = 7.7 Hz, 1H), 7.12 (d, J = 8.9 Hz, 2H), 5.12 (m, 1H), 4.30 (t, J = 5.3 Hz, 2H), 4.14 (t, J = 5.5 Hz, 2H), 3.30 (m, 4H), 3.00 (d, J = 6.8 Hz, 2H), 2.89 (s, 1H), 2.84 (m, 2H), 2.73 – 2.64 (m, 6H), 2.08 (s, 1H). |
| 173 | C | 1H NMR: (400 MHz, DMSO-d6): δ 11.04 (s, 1H), 10.82 (s, 1H), 8.62 (s, 1H), 8.50-8.48 (m, 2H), 7.78-7.70 (m, 3H), 7.52-7.47 (m, 2H), 7.42-7.39 (m, 3H), 7.33 (s, 1H), 7.15-7.13 (m, 1H), 7.04-7.01 (d, J = 9.2 Hz, 2H), 5.05-5.00 (m, 1H), 4.37-4.27 (m, 2H), 3.15 (s, 4H), 2.97-2.89 (m, 2H), 2.85-2.73 (m, 5H), 2.72-2.59 (m, 4H), 2.56-2.47 (m, 2H), 2.00-1.94 (m, 1H). |
| 174 | B | 1H NMR (400 MHz, DMSO-d6): δ 11.11 (s, 1H), 10.88 (d, J = 3.6 Hz, 1H), 8.69 (s, 1H), 8.56 (m, |

FIG. 3. Continued

| | | |
|---|---|---|
| 175 | D | 2H), 7.81 (m, 3H), 7.35-7.62 (m, 6H), 7.20 (s, 1H), 7.09 (m, 2H), 5.10 (m, 1H), 4.25 (t, J = 6.4 Hz, 2H), 3.32 (m, 4H), 3.19 (m, 4H), 2.75-3.05 (m, 5H), 2.40 (m, 2H), 1.60-2.10 (m, 8H). |
| 176 | B | 1H NMR (400 MHz, CDCl3): δ 8.56 (d, J = 4.9 Hz, 2H), 8.16 – 8.23 (m, 1H), 7.93 (s, 1H), 7.61 – 7.69 (m, 2H), 7.51 (d, J = 5.3 Hz, 2H), 7.43 – 7.49 (m, 1H), 7.29 (s, 1H), 7.19 (d, J = 7.1 Hz, 2H), 7.02 (d, J = 8.9 Hz, 2H), 6.59 – 6.66 (m, 1H), 4.88 – 4.98 (m, 1H), 4.37 – 4.46 (m, 2H), 4.08 – 4.19 (m, 2H), 3.29 (s, 5H), 3.03 (m, 4H), 2.67 – 2.92 (m, 4H), 2.63 (s, 4H), 2.07 – 2.16 (m, 1H). |
| 177 | B | 1H NMR (400 MHz, DMSO-d6): δ 11.06 (s, 1H), 10.90 (s, 1H), 9.61 (s, 1H), 8.76 (s, 1H), 8.65 (s, 1H), 7.86 (d, J = 8.8 Hz, 2H), 7.63 (d, J = 6.4 Hz, 2H), 7.60 – 7.54 (m, 1H), 7.43 (s, 1H), 7.27 – 7.22 (m, 1H), 7.20 (d, J = 8.2 Hz, 2H), 6.85 – 6.78 (m, 1H), 5.11 – 5.01 (m, 1H), 4.51 – 4.35 (m, 2H), 4.12 – 3.90 (m, 4H), 3.50 (s, 4 H), 3.33 – 3.17 (m, 4H), 3.01 (s, 4H), 2.84 (d, J = 4.1 Hz, 3H), 2.70 – 2.60 (m, 2H), 2.37 – 2.29 (m, 1H), 2.07 – 1.95 (m, 1H). |
| 178 | B | 1H NMR (400 MHz, DMSO-d6): δ 11.07 (s, 1H), 10.89 (s, 1H), 8.80 (s, 1H), 8.57 (d, J = 5.6Hz ,2H), 7.88 (d, J = 8.0Hz ,2H), 7.55 (d, J = 8.0Hz ,1H),7.40-7.50 (m, 6H), 7.21 (d, J = 8.0Hz ,1H), 6.82 (s, 1H), 6.60-6.68 (m, 1H), 5.05-5.08 (m, 1H), 4.13-4.15 (m, 2H), 3.86-3.89 (m, 2H), 2.95-3.02 (m, 4H), 2.85-2.90 (m, 3H), 2.50-2.70 (m, 3H), 1.95-2.10 (m, 4H), 1.80-1.90 (m, 2H), 1.70-1.79 (m, 2H). |
| 179 | A | 1H NMR (400 MHz, DMSO-d6): δ 11.05 (s, 1H), 10.89 (s, 1H), 8.82 (s, 1H), 8.58 (d, J=4.0 Hz, 2H), 7.81 (d, J=8.1 Hz, 2H), 7.49-7.57 (m, 6H), 7.41 (s, 1H), 7.22 (d, J=8.1 Hz, 1H), 7.10 (d, J=8 Hz, 1H), 6.79 (d, J=8 Hz, 1H), 5.02-5.07 (m, 1H), 4.28-4.32 (m, 2H), 3.87-3.91 (m, 2H), 3.69 (s, 3H), 3.17-3.19 (m, 3H), 2.99-3.01 (m, 2H), 2.56-2.87 (m, 7H), 1.95-2.03 (m, 2H). |
| 180 | D | 1H NMR (400 MHz, DMSO-d6): δ 11.06 (s, 1H), 10.90 (s, 1H), 8.82 (s, 1H), 8.59 (d, J = 4.0 Hz, 2H), 7.92 (d, J = 8.0 Hz, 2H), 7.64 (d, J = 8.0 Hz, 2H), 7.49-7.58 (m, 5H), 7.42 (s, 1H), 7.22 (d, J = 8.0 Hz, 1H), 6.78 (s, 1H), 6.65 (d, J = 8.4 Hz, 1H), 5.03-5.07 (m, 1H), 4.16-4.18 (m, 2H), 3.70-3.72 (m, 6H), 3.19 (s, 3H), 3.01 (s, 2H), 2.76-2.84 (m, 6H), 1.99-2.02 (m, 1H). |
| 181 | B | 1H NMR (400 MHz, CD3OD): δ 8.54 (s, 3H), 7.94 (d, J = 8.4Hz, 2H), 7.82 (t, J = 8.4Hz, 1H). 7.55-7.69 (m, 5H), 7.47-7.54 (m, 2H), 7.39 (s, 1H), 7.27 (d, J = 7.6Hz, 1H), 5.33 (t, J = 3.2Hz, 1H), 4.55 (s, 4H), 4.33-4.52 (m, 3H), 4.17-4.30 (m, 1H), 3.50-3.68 (m, 1H), 3.02-3.12 (m, 2H), 2.93-2.96 (m, 1H), 2.82-2.88 (m, 1H), 2.69-2.78 (m, 1H), 2.10-2.22 (m, 4H). |
| 182 | A | 1H NMR (400 MHz, DMSO-d6): δ 11.08 (s, 1H), 10.89 (s, 1H), 8.83 (s, 1H), 8.58 (d, J = 4.2 Hz, 2H), 7.92(d, J = 8.0 Hz, 2H), 7.82 (t, J = 8.0 Hz, 1H), 7.57-7.41 (m, 8H), 7.21 (d, J = 8.0 Hz, 1H), 5.10-5.05 (m, 1H), 4.25 (t, J = 6.0 Hz, 2H), 3.18-3.16 (m, 4H), 3.02-2.99 (m, 3H), 2.92-2.77 (m, 4H), 2.67-2.56 (m, 2H), 2.08-1.97 (m, 2H), 1.84-1.81 (m, 2H), 1.62-1.53 (br, 2H). |
| | A | 1H NMR (400 MHz, CDCl3): δ 9.58 (s, 1H), 9.10(s, 1H), 8.03 (s, 1H), 7.67-7.59 (m, 2H), 7.42 (d. |

FIG. 3. Continued

| | | |
|---|---|---|
| 183 | B | J = 7.2 Hz, 1H), 7.34 (d, J = 8 Hz, 1H), 7.23-7.18 (m, 1H), 6.66 (d, J = 12 Hz, 1H), 5.02-4.81 (m, 1H), 3.90-3.89 (m, 1H), 3.18-3.14 (m, 3H), 3.05 (s, 2H), 2.96-2.87 (m, 3H), 2.13(dd, J =2.8 Hz, 4 Hz, 2 H), 2.00-1.90 (m, 3H), 1.30 (s, 8H), 1.09 (t, J =12.0 Hz, 3H), 0.84-.088(m, 4H). |
| | B | 1H NMR (400 MHz, CDCl3): δ 9.56 (s, 1H), 9.10 (s, 1H), 8.06 (s, 1H), 7.66-7.71 (m, 3H), 7.33-7.35 (m, 2H), 7.19-7.26 (m, 1H), 7.10-7.11 (m, 1H), 6.64 (d, J = 11.2 Hz, 2H), 4.93-4.98 (m, 2H), 4.12-4.15 (m, 2H), 3.14-3.24 (m, 4H), 2.97 (s, 3H), 2.87-2.89 (m, 4H), 2.11-2.18 (m, 1H), 1.86-1.98 (m, 5H), 1.09 (t, J = 7.2 Hz, 3H). |
| 184 | D | 1H NMR (400 MHz, DMSO-d6) δ 11.07 (s, 1H), 9.80 – 10.02 (m, 1H), 9.66 (s, 1H), 9.01 (s, 1H), 8.40 (s, 1H), 7.80 – 7.89 (m, 1H), 7.61-7.63 (m, 2H), 7.44-7.48 (m, 2H), 6.76 (d, J = 9.3 Hz, 1H), 5.08 (dd, J = 12.9, 5.2 Hz, 1H), 4.33 – 4.49 (m, 3H), 3.45 (s, 6H), 3.06 – 3.25 (m, 3H), 2.94 (s, 2H), 2.83 (s, 2H), 2.55 – 2.73 (m, 4H), 2.29 (d, J = 10.3 Hz, 2H), 1.77 (m, 2H), 1.68 (d, J = 10.1 Hz, 2H), 0.99 (t, J = 7.4 Hz, 3H). |
| | B | |
| 185 | B | 1H NMR (400 MHz, DMSO-d6): δ 11.09 (s, 1H), 9.65 (s, 2H), 8.39 (s, 1H), 7.83 (d, J = 8.0 Hz, 1H), 7.45-7.47 (m, 1H), 7.37-7.43 (m, 4H), 6.74 (d, J = 8.8 Hz, 1H), 5.08-5.12 (m, 1H), 4.35-4.40 (m, 3H), 3.78-3.80 (m, 2H), 3.61-3.64 (m, 2H), 2.89-2.92(m, 2H), 2.80-3.20 (m, 7H), 2.51-2.53(m, 2H), 2.15-2.20 (m, 2H), 2.01-2.04 (m, 2H), 1.65-1.79 (m, 6H), 0.97-1.01 (m, 3H). |
| 186 | D | 1H NMR (400 MHz, CDCl3): δ9.56 (s, 2H), 9.11 (s, 1H), 8.04 (s, 1H), 7.80 (d, J = 8.4Hz, 1H), 7.64-7.80 (m, 2H), 7.41 (s, 1H), 7.25-7.31 (m, 2H), 7.19 (t, J = 9.6Hz, 1H), 6.62 (d, J = 9.6 Hz, 1H), 4.92-5.00 (m, 1H), 4.52-4.61 (m, 1H), 4.24-4.28 (m, 2H), 3.14-3.18 (m, 4H), 3.01 (s, 3H), 2.78-2.92 (m, 6H), 2.40 (t, J = 8.6 Hz, 2H), 2.12-2.21 (m, 2H), 1.84-1.96(m,4H), 1.09 (t, J = 7.6 Hz, 3H). |
| | A | |
| 187 | C | 1H NMR (400 MHz, CDCl3): δ 9.54 (s, 2H), 9.12 (s, 1H), 7.62 – 7.69 (m, 3H), 7.45 (d, J = 7.3 Hz, 1H), 7.29 (s, 1H), 7.18 (d, J = 9.2 Hz, 1H), 6.59 (d, J = 9.2 Hz, 1H), 4.82 – 4.82 (m, 1H), 4.55 – 4.74 (m, 1H), 4.38 (d, J = 4.4 Hz, 2H), 3.94 (s, 2H), 3.74 – 3.86 (m, 1H), 3.20 (s, 1H), 3.07 – 3.17 (m, 2H), 2.96 (s, 3H), 2.75 (m, 6H), 2.35 (s, 4H), 2.05 (d, J = 7.4 Hz, 2H), 1.88 – 1.98 (m, 3H), 1.77 (s, 2H), 1.08 (t, J = 7.4 Hz, 3H). |
| | B | |
| 188 | B | 1H NMR (400 MHz, DMSO-d6): δ 11.09 (s, 1H), 9.89 (s, 1H), 9.65 (s, 2H), 9.03 (s, 1H), 8.40 (s, 1H), 7.80 – 7.82 (m, 1H), 7.52 – 7.60 (m, 1H), 7.45 – 7.46 (m, 3H), 7.35 – 7.37 (m, 1H), 6.74 (d, J = 9.2 Hz, 1H), 5.08 – 5.12 (m, 1H), 4.36 – 4.47 (m, 1H), 4.31 (s, 2H), 3.81 (s, 2H), 3.57 – 3.63 (m, 7H), 3.09 – 3.19 (m, 4H), 2.93 (s, 3H), 2.58 – 2.63 (m, 4H), 2.23 – 2.32 (m, 2H), 2.01 (s, 1H), 1.93 – 2.02 (m, 2H), 1.67 – 1.82 (m, 4H), 0.99 (t, J = 7.6 Hz, 3H). |
| 189 | D | 1H NMR (400 MHz, DMSO-d6) δ 11.09 (s, 1H), 9.65 (s, 2H), 9.02 (s, 1H), 8.40 (s, 1H), 7.77 (d, J = 7.6 Hz, 1H), 7.56 – 7.63 (m, 1H), 7.53 (d, J = 8.5 Hz, 1H), 7.43-7.46 m, 2H), 6.73 (d, J = 9.2 Hz, |
| | C | |

FIG. 3. Continued

| | | |
|---|---|---|
| | | 1H), 5.01 – 5.13 (m, 1H), 4.35 (s, 3H), 3.83 (d, J = 4.5 Hz, 2H), 3.63 – 3.72 (m, 2H), 3.53-3.56(m, 4H), 3.19 – 3.11 (m, 2H), 3.03 (d, J = 9.5 Hz, 2H), 2.92 (s, 3H), 2.80 – 2.88 (m, 1H), 2.53 – 2.71 (m, 5H), 2.16 (s, 2H), 1.95 – 2.06 (m, 2H), 1.74-1.79 (m, 4H), 1.66 (s, 2H), 0.99 (t, J = 7.4 Hz, 3H). |
| 190 | D | 1H NMR (400 MHz, CDCl3): δ 9.46 (s, 2H), 9.00 (s, 1H), 8.58 (s, 1H), 7.80 (d, J = 8.4 Hz, 1H), 7.58-7.59 (m, 2H), 7.25-7.27 (m, 2H), 7.19-7.23 (m, 2H), 7.10 (m, 1H), 6.50 (d, J = 9.2 Hz, 1H), 4.66-4.68 (m, 1H), 4.34-4.49 (m, 5H), 4.12-4.14 (m, 1H), 3.45-3.50 (m, 1H), 3.06-3.08 (m, 2H), 2.97 (s, 2H), 2.81-2.88 (m, 5H), 2.42 (s, 3H), 2.41-2.43 (m, 1H), 2.32-2.34 (m, 2H), 1.82-1.86 (m, 1H), 1.70-1.75 (m, 7H), 1.00 (t, J = 7.2 Hz, 3H), 0.92 (s, 9H). |
| 191 | D | 1H NMR (400 MHz, DMSO-d6): δ 9.65 (s, 2H), 9.02 (s, 1H), 8.94 (s, 1H), 8.57 (t, J = 4.8 Hz, 1H), 8.40 (m, 1H), 7.55-7.65 (m, 1H), 7.35-7.50 (m, 7H), 6.74 (d, J = 9.2 Hz, 1H), 4.57 (d, J = 9.6 Hz, 1H), 4.20-4.50 (m, 5H), 4.00 (s, 2H), 3.50-3.70 (m, 2H), 3.00-3.20 (m, 7H), 2.93 (s, 3H), 2.50-2.70 (m, 4H), 2.43 (s, 3H), 1.60-2.25 (m, 13H), 0.90-1.05 (m, 12H). |
| | C | |
| 192 | D | 1H NMR (400 MHz, DMSO-d6): δ 9.66 (s, 2H), 9.02 (s, 1H), 8.90 (s, 1H), 8.59 (t, J = 6.0 Hz, 1H), 8.40 (s, 1H), 8.17 (s, 1H), 7.63-7.57 (m, 1H), 7.46-7.43 (m, 3H), 7.40-7.35 (m, 3H), 6.71 (d, J = 9.2 Hz, 1H), 5.17 (br, 1H), 4.58 (d, J = 9.6 Hz, 1H), 4.47-4.35 (m, 4H), 4.28-4.26 (m, 1H), 3.3.99-3.98(m, 2H), 3.67-3.60 (m, 4H), 3.11-3.06 (m, 3H), 2.92 (s, 3H), 2.61-2.54 (m, 2H), 2.41 (s, 3H), 2.2.-2.19 (m, 2H), 2.08-1.97 (m, 2H), 1.93-1.72 (m, 6H), 1.68-1.65 (m, 2H), 1.00-0.94 (m, 12H). |
| 196 | | 1H NMR (400 MHz, CDCl3): δ 8.47 – 8.86 (m, 3H), 8.27 (s, 1H), 8.09 (s, 1H), 7.94 (d, J = 4.9 Hz, 3H), 7.68 (d, J = 8.7 Hz, 3H), 7.52 (s, 2H), 7.36 – 7.47 (m, 2H), 7.29 (s, 1H), 7.21 (s, 1H), 7.15 (s, 1H), 7.02 (d, J = 8.4 Hz, 3H), 4.97 – 5.04(m, 1H), 4.13 (s, 4H), 2.74 – 3.12 (m, 8H), 2.21 (d, J = 7.7 Hz, 2H), 2.01 – 2.09 (m, 3H). |
| 197 | D | 1H NMR (400 MHz, DMSO-d6): δ 11.09 (s, 1H), 10.93 (s, 1H), 9.93 (br, 1H), 8.79 (s, 1H), 8.68 (s, 2H), 7.91 (d, J = 8.4 Hz, 2H), 7.65-7.80 (m, 3H), 7.58 (d, J = 8.0 Hz, 1H), 7.49 (s, 1H), 7.44 (s, 1H), 7.34 (d, J = 8.4 Hz, 1H), 7.25 (d, J = 8.0 Hz, 1H), 7.16 (d, J = 8.8 Hz, 2H), 5.09 (m, 1H), 4.25 (m, 4H), 3.88 (m, 4H), 3.01 (m, 2H), 2.86 (m, 3H), 2.50 (m, 3H), 2.03 (m, 1H). |
| 198 | C | 1H NMR (400 MHz, CDCl3): δ 8.55 (s, 2H), 8.04 (s, 1H), 7.94 (s, 1H), 7.79 (d, J = 8.0 Hz, 1H), 7.65 (d, J = 8.8 Hz, 3H), 7.39 (s, 2H), 7.30 (s, 2H), 7.23 (s, 1H), 7.01 (d, J = 8.8 Hz, 2H), 4.98-4.93 (m, 1H), 4.27 (s, 2H), 3.90 (s, 2H), 3.77 (s, 2H), 3.28 (s, 4H), 3.06-3.01 (m, 4H), 2.93-2.81 (m, 2H), 2.74 (s, 7H), 2.17-2.13 (br, 1H). |
| 199 | B | 1H NMR (400 MHz, DMSO-d6): δ 11.11 (s, 1H), 10.90 (s, 1H), 8.70 (s, 1H), 8.57-8.56 (m, 2H), 7.85-7.77 (m, 3H), 7.56 (d, J = 8.0 Hz, 2H), 7.49-7.45 (m, 3H), 7.41 (s, 1H), 7.22 (d, J = 8.0 Hz, 1H), 7.10-7.08 (m, 2H), 5.12-5.08 (m, 1H), 4.32-4.28 (m, 2H), 3.22 (s, 5H), 3.03-2.97 (m, 2H), |

FIG. 3. Continued

| | | |
|---|---|---|
| | | 2.89-2.80 (m, 3H), 2.62-2.57 (m, 7H), 2.06-1.99 (m, 3H). |
| 200 | B | 1H NMR (400 MHz, DMSO-d6): δ 11.09 (s, 1H), 10.89 (s, 1H), 8.73 (s, 1H), 8.57 (d, J = 5.2 Hz, 2H), 7.82 —7.92 (m, 5H), 7.56 (d, J = 8.0 Hz, 1H), 7.48 (d, J = 4.8 Hz, 2), 7.37 —7.41 (m, 2), 7.09 —7.23 (m, 6H), 5.05 —5.10 (m, 1H), 4.22 —4.29 (m, 4H), 4.10 (s, 1H), 3.17 (d, J = 4.8 Hz, 1H), 2.99 —3.01 (m, 2H), 2.81 —2.84 (m, 3H), 2.22 —2.54 (m, 1H), 2.02 —2.08 (m, 1H). |
| 201 | A | 1H NMR (400 MHz, DMSO-d6): δ 10.90 (s, 1H), 8.73 (s, 1H), 8.58-8.56 (d, J = 8.0 Hz, 2H), 7.84-7.82(d, J = 8.8 Hz, 2H), 7.74-7.72 (d, J = 8.4 Hz, 1H), 7.56-7.55 (d, J = 8.4 Hz, 1H), 7.49-7.48 (m, 2H), 7.43-7.41 (m, 2H), 7.36-7.34 (m, 1H), 7.22-7.21 (d, J = 8.0 Hz, 1H), 7.17-7.15 (d, J = 10 Hz, 2H), 5.18-5.14 (m, 1H), 3.66 (s, 4H), 3.42 (s, 4H), 3.02-2.91 (m, 6H), 2.85-2.74 (m, 3H), 2.60-2.53 (m, 1H), 2.09-2.00 (br, 1H). |
| 202 | A | 1H NMR (400 MHz, DMSO-d6) δ 1.99-2.17 (4H, m), 2.54-2.72 (11H, m), 2.84-2.89 (2H, m), 3.19-3.28 (4H, m), 3.40-3.42 (3H, m), 3.47-3.51 (5H, m), 4.88-4.90 (1H, m), 5.06-5.10 (1H, m), 5.23-5.36 (1H, m), 7.09 (2H, d, J = 8.8 Hz), 7.27-7.30 (2H, m), 7.36 (1H, s), 7.60-7.66 (3H, m), 7.69 (1H, d, J = 8.4 Hz), 8.09 (1H, s), 8.55 (1H, brs), 8.65 (1H, d, J = 2.0 Hz), 11.07-11.10 (2H, m), 12.92 (1H, d, J = 5.6 Hz). |
| 203 | B | 1H NMR (400 MHz, CDCl3): δ 8.58 (s, 2H), 8.04 (s, 2H), 7.83-7.81 (d, J = 8.4 Hz, 1H), 7.68-7.66 (d, J = 7.6 Hz, 1H), 7.52(m, 2H), 7.48 (m, 1H),7.44-7.43 (m, 2H), 7.41-7.36 (m, 2H), 7.30 (s, 2H), 7.23(s, 2H), 4.99-4.94(m, 1H), 4.49(s, 4H), 3.05-2.94(m. 4H), 2.90-2.73(m, 3H), 2.04-2.00(m, 1H). |
| 204 | B | 1H NMR (400 MHz, DMSO-d6): δ 11.12 (s, 1H), 10.92 (s, 1H), 8.88 (s, 1H), 8.58 (d, J = 5.6 Hz, 2H), 7.80 (d, J = 8.4 Hz, 1H), 7.77 (d, J = 8.4 Hz, 1H), 7.34-7.57 (m, 9H), 7.21 (d, J = 7.6 Hz, 1H), 6.94 (d, J = 7.2 Hz, 1H), 4.36 (t, J = 4.4 Hz, 2H), 4.24 (d, J = 4.4 Hz, 2H), 3.89 (m, 4H), 2.80-3.05 (m, 5H), 2.53 (m, 2H), 2.05 (m. 1H). |
| 205 | B | 1H NMR (400 MHz, CDCl3) δ 9.75 (s, 1H), 8.58 (d, J = 5.0 Hz, 2H), 8.50 (s, 1H), 8.03 (s, 1H), 7.86 (d, J = 8.0 Hz, 1H), 7.77 (d, J = 8.3 Hz, 1H), 7.53 (d, J = 5.9 Hz, 2H), 7.46 (d, J = 9.0 Hz, 1H), 7.37 (dd, J = 9.5, 6.7 Hz, 2H), 7.31 (d, J = 8.3 Hz. 1H), 7.17 —7.24 (m, 2H), 6.87 (d, J = 6.6 Hz, 1H), 4.96 (dd, J = 12.5, 5.3 Hz, 1H), 4.26 (s, 2H), 4.19 — 4.24 (m, 2H), 3.91 (dd, J = 9.1, 4.5 Hz, 4H), 3.77 (s, 4H), 3.00 (s, 4H), 2.70 -- 2.94 (m, 3H), 2.17 (d, J = 10.3 Hz, 1H). |
| 206 | | 1H NMR (400 MHz, DMSO-d6) δ 2.03-2.11 (5H, m), 2.25-2.30 (2H, m), 2.50-2.62 (2H, m), 2.78-2.86 (5H, m), 2.88-2.99 (2H, m), 3.08-3.11 (2H, m), 4.22-4.28 (1H, m), 4.33 (2H, t, J = 5.2 Hz), 5.12 (1H, dd, J = 12.8, 5.2 Hz), 7.12 (1H, d, J = 8.0 Hz), 7.30 (1H, s), 7.38-7.40 (3H, m), 7.49-7.52 (2H, m), 7.84 (1H, d, J = 8.4 Hz), 8.14 (1H, s), 8.50 (2H, dd, J = 4.4, 1.6 Hz), 10.86 (1H, s), 11.10 (1H. s). |

FIG. 3. Continued

| | | |
|---|---|---|
| 207 | D | 1H NMR (400 MHz, DMSO-d6) δ 1.51-1.53 (2H, m), 1.84-1.87 (2H, m), 1.97-2.03 (3H, m), 2.09-2.11 (2H, m), 2.32-2.37 (2H, m), 2.57-2.67 (2H, m), 2.78-2.89 (3H, m), 2.90-2.99 (6H, m), 4.11 (2H, d, J = 12.8 Hz), 4.20-4.22 (1H, m), 5.06 (1H, dd, J = 12.8, 5.6 Hz), 7.12 (1H, d, J = 8.8 Hz), 7.25 (1H, d, J = 6.0 Hz), 7.27 (1H, s), 7.30 (1H, s), 7.38 (2H, dd, J = 4.8, 1.2 Hz), 7.50 (1H, d, J = 8.0 Hz), 7.56 (1H, d, J = 8.8 Hz), 8.13 (1H, s), 8.24 (1H, s), 8.50 (2H, dd, J = 4.8, 1.6, Hz), 10.86 (1H, s), 11.08 (1H, s). | B |
| 208 | D | 1H NMR (400 MHz, CDCl3): δ 11.23 (bs, 1H), 10.56 (s, 1H), 8.73 (s, 1H), 8.54 (s, 1H), 7.68-7.62 (m, 3H), 7.44 (s, 1H), 7.28 (s, 1H), 7.09 (d, J = 8.8 Hz, 2H), 7.01 (t, J = 8.8 Hz, 2H), 6.84 (s, 1H), 6.54 (d, J = 7.6 Hz, 1H), 5.17 (s, 1H), 5.11-4.95 (m, 1H), 4.23 (s, 2H), 3.92 (s, 2H), 3.77-3.76 (m, 2H), 3.69-3.67 (m, 4H), 3.64-3.57 (m, 4H), 3.54-3.51 (m, 2H), 3.42-3.39 (m, 2H), 3.13 (s, 4H), 2.93 (s, 3H), 2.50-2.35 (m, 6H), 2.10 (s, 2H). | C |
| 209 | | 1H NMR (400 MHz, CDCl3) δ 1.73-2.08 (12H, m), 2.17-2.19 (1H, m), 2.51-2.53 (1H, m), 2.66-2.96 (7H, m), 3.17-3.23 (2H, m), 3.48-354 (1H, m), 3.61-3.73 (3H, m), 4.16-4.22 (1H, m), 4.84-4.89 (1H, m), 6.98 (1H, dd, J = 8.4, 2.0 Hz), 7.09 (1H, d, J = 8.0 Hz), 7.15 (1H, s), 7.21 (1H, d, J = 4.8 2.4 Hz), 7.45-7.51 (3H, m), 7.59 (2H, t, J = 8.8 Hz), 8.14 (1H, d, J = 12.8 Hz), 8.46 (1H, d, J = 4.8 Hz). | |
| 210 | | 1H NMR (400 MHz, CDCl3) δ 1.81-2.08 (11H, m), 2.14-2.15 (1H, m), 2.24-2.27 (1H, m), 2.65-2.95 (8H, m), 3.23-3.28 (2H, m), 3.65 (3H, m), 3.97 (1H, s), 4.52 (1H, brs), 4.85-4.89 (1H, m), 6.98-7.01(1H, m), 7.10 (1H, d, J = 8.0 Hz), 7.15 (1H, s), 7.22 (1H, d, J = 2.0 Hz), 7.42 (2H, d, J = 4.0 Hz), 7.48 (1H, s), 7.57 (1H. dd, J = 8.0, 2.4 Hz), 7.61 (1H, d, J = 8.4 Hz), 8.19-8.29 (1H, m), 8.43-8.46 (2H, m). | |
| 211 | B | 1H NMR (400 MHz, DMSO-d6): δ 11.07 (s, 1H), 10.91 (s, 1H), 8.75 (s, 1H), 8.57 (d, J = 5.6 Hz, 2H), 7.87 (d, J = 8.8 Hz, 2H), 7.65 (d, J = 4.8 Hz, 1H), 7.55 (d, J = 4.8 Hz, 1H), 7.49 (d, J = 5.6 Hz, 2H), 7.41 (s, 1H), 7.21 (d, J = 4.8 Hz, 1H), 7.12 (d, J = 9.2 Hz, 2H), 6.77 (s, 1H), 6.63 (d, J = 4.4 Hz, 1H), 5.00-5.10 (m, 1H), 4.05-4.20 (m, 4H), 3.70-3.80 (m, 2H), 2.70-3.10 (m, 7H), 2.55-2.65 (m, 4H), 1.70-2.05 (m, 10H). | C |
| 212 | B | 1H NMR (400 MHz, DMSO-d6): δ11.11(s, 1H), 10.90(s, 1H), 8.78(s, 1H), 8.59 (d, J = 4.4 Hz. 2H), 7.90 (d, J = 8.8 Hz, 2H), 7.79-7.81(m, 1H), 7.42-7.58(m, 6H), 7.16-7.23(m, 4H), 6.56(t, J = 8.0 Hz, 3H), 5.07-5.11(m, 1H), 4.33-4.38(m, 6H), 4.11(s, 2H), 3.88(s, 4H), 3.18(s, 1H), 3.01(s, 2H), 2.84-2.85(m, 2H), 2.02-2.04(m, 2H), 1.51-1.54(m, 2H). | B |
| 213 | D | 1H NMR (400 MHz, CDCl3): δ 8.57-8.56 (m, 2H), 8.32 (s, 1H), 7.93 (s, 1H), 7.69-7.63 (m, 3H), 7.57-7.51(m, 3H), 7.43-7.41 (m, 1H),7.38-7.36 (d, J = 7.2Hz, 1H), 7.28 (s, 2H), 7.23 (s, 2H), 7.15-7.13(d, J = 7.6Hz, 1H), 7.08-7.06(m, 2H), 7.00-6.97(m, 1H), 6.91-6.89(d, J = 7.6Hz, 1H), 5.15(s , | A |

FIG. 3. Continued

| | | |
|---|---|---|
| 214 | | 2H), 4.92-4.88(m, 1H), 4.26-4.23(t, J = 6.4 Hz, 2H), 4.20-4.17(t, J = 4.4Hz, 2H), 3.86-3.84(t, J = 4.8Hz, 2H), 3.79-3.76(t, J = 6.0Hz, 2H), 3.08-2.96(m, 4H), 2.90-2.82(m, 1H), 2.81-2.66(m, 2H), 2.16-2.05(m, 3H). |
| 215 | D | 1H NMR (400 MHz, CDCl3): δ 8.58 (d, J = 5.2 Hz, 2H), 8.40 (br, 1H), 8.08 (s, 1H), 7.84 (d, J = 8.4 Hz, 2H), 7.68 (m, 4H), 7.54 (d, J = 5.2 Hz, 2H), 7.46 (d, J = 7.2 Hz, 1H), 7.15-7.45 (m, 4H), 6.94 (d, J = 8.0 Hz, 1H), 4.93 (m, 1H), 4.41 (t, J = 5.6 Hz, 2H), 4.33 (t, J = 5.6 Hz, 2H), 3.05 (m, 4H), 3.65-3.90 (m, 3H), 3.05 (m, 2H), 2.40 (m, 2H), 1.50-2.20 (m, 4H). |
| | A | 1H NMR (400 MHz, DMSO-d6): δ 11.09 (s, 1H), 10.90 (s, 1H), 8.90 (s, 1H), 8.59 (d, J = 5.6 Hz, 2H), 8.02 (d, J = 8.4 Hz, 2H), 7.79 (m, 3H), 7.38 – 7.70 (m, 8H), 7.25 (d, J = 6.0 Hz, 1H), 6.98 (d, J = 8.8 Hz, 2H), 5.09 (m, 1H), 4.26 (m, 2H), 4.05 (m, 2H), 3.60 (m, 4H), 3.05 (m, 2H), 2.86 (m, 3H), 2.50 (m, 3H), 2.03 (m, 5H). |
| 216 | | 1H NMR (500 MHz, DMSO-d6) δ 13.00 (bs, 1H), 9.78 (bs, 1H), 8.96 (s, 1H), 8.71 (s, 1H), 8.62 (s, 1H), 8.55 (t, J = 5.5 Hz, 1H), 8.23 (s, 1H), 7.96 (d, J = 9.2 Hz, 1H), 7.59 (q, J = 8.3 Hz, 1H), 7.52 – 7.18 (m, 8H), 6.99 (d, J = 8.2 Hz, 1H), 5.13 (d, J = 3.8 Hz, 1H), 4.57 (d, J = 9.4 Hz, 1H), 4.48 – 4.32 (m, 3H), 4.23 (d, J = 5.5 Hz, 1H), 4.19 (t, J = 5.1 Hz, 2H), 3.86 – 3.57 (m, 6H), 3.19 – 3.06 (m, 2H), 2.61 (m, 1H), 2.43 (s, 3H), 2.43 – 2.37 (m, 1H), 2.08 – 2.00 (m, 1H), 1.95 – 1.87 (m, 1H), 1.80 – 1.69 (m, 2H), 0.94 (s, 9H), 0.95 (t, 3H). 13C NMR (151 MHz, dmso) δ 180.64, 171.95, 169.97, 169.57, 159.10, 156.03 (dd, J = 246.6, 6.9 Hz), 152.34 (dd, J = 249.6, 8.4 Hz), 151.42, 148.97, 147.72, 144.17, 139.67, 139.50, 138.81, 131.46, 131.17, 130.28, 129.64, 128.94 – 128.71 (m), 128.64, 127.42, 127.17, 121.98 (dd, J = 13.6, 3.4 Hz), 119.57, 118.54 – 117.84 (m), 117.47, 115.72, 113.74, 113.11, 112.53 – 112.23 (m), 68.91, 68.69, 67.13, 58.74, 56.37, 53.46, 41.68, 37.97, 35.37, 26.36, 16.86, 15.95, 12.63. |
| 217 | | 1H NMR (500 MHz, DMSO-d6) δ 10.02 (s, 1H), 8.97 (s, 1H), 8.68 (d, 1H), 8.64 – 8.52 (m, 2H), 8.21 (s, 1H), 7.95 (d, J = 9.2 Hz, 1H), 7.72 (dd, J = 36.7, 8.5 Hz, 4H), 7.62 – 7.54 (m, 1H), 7.40 (dd, 4H), 7.28 (t, J = 8.7 Hz, 1H), 5.16 (d, 2H), 4.56 (d, J = 9.3 Hz, 1H), 4.50 – 4.40 (m, 2H), 4.40 – 4.33 (m, 1H), 4.22 (dd, J = 15.8, 5.3 Hz, 1H), 3.76 – 3.62 (m, 2H), 3.16 – 3.05 (m, 2H), 2.44 (s, 3H), 2.41 – 2.17 (m, 4H), 2.09 – 2.01 (m, 1H), 1.98 – 1.80 (m, 3H), 1.74 (dq, J = 14.9, 7.4 Hz, 2H), 0.96 (s, 9H), 0.95 (t, 3H). 13C NMR (151 MHz, dmso) δ 181.06, 172.39, 172.17, 171.46, 170.15, 156.37 (dd, J = 246.6, 6.3 Hz), 152.73 (dd, J = 249.4, 8.1 Hz), 151.86, 149.05, 148.13, 144.19, 139.91, 139.37, 139.13, 132.97, 131.64, 131.59, 130.05, 129.22 (d, J = 14.7 Hz), 129.06, 127.84, 127.74, 126.89, 122.47 (d, J = 14.1 Hz), 120.07, 119.02 – 118.20 (m), 117.95, 116.06, 112.75 (dd, J = 23.4, 2.8 Hz), 69.34, 59.15, 56.90, 56.81, 53.87, 42.08, 38.38, 36.36, 35.63, 34.63, 26.85, 21.91, 17.27, 16.37, 13.04. |

FIG. 3. Continued

| | | |
|---|---|---|
| 218 | | ¹H NMR (500 MHz, DMSO-d6) δ 12.64 (bs, 1H), 9.74 (bs, 1H), 8.97 (s, 1H), 8.62 – 8.52 (m, 3H), 8.28 (d, J = 2.0 Hz, 1H), 8.00 (s, 1H), 7.95 (bs, 1H), 7.90 (d, J = 9.2 Hz, 1H), 7.59 – 7.49 (m, 1H), 7.47 – 7.27 (m, 4H), 7.20 (t, J = 8.7 Hz, 1H), 5.13 (bs, 1H), 4.56 (d, J = 9.3 Hz, 1H), 4.48 – 4.32 (m, 3H), 4.22 (dd, J = 15.8, 5.3 Hz, 1H), 3.75 – 3.57 (m, 5H), 3.23 – 3.02 (m, 7H), 2.44 (s, 3H), 2.41 – 2.17 (m, 4H), 2.07 – 2.01 (m, 1H), 1.96 – 1.87 (m, 1H), 1.81 – 1.66 (m, 4H), 0.95 (s, 9H), 0.94 (t, 3H). ¹³C NMR (151 MHz, dmso) δ 180.70, 171.99, 171.92, 170.44, 169.75, 155.24 (dd, J = 248.1, 5.5 Hz), 152.12 (dd, J = 248.8, 8.5 Hz), 151.47, 147.73, 144.63, 144.31, 139.52, 138.02, 137.75, 131.19, 129.65, 128.65, 127.98 – 127.64 (m), 127.44, 123.91 – 123.09 (m), 118.86 – 117.72 (m), 117.60, 115.50, 115.23, 112.02 (dd, J = 22.6, 3.2 Hz), 68.92, 58.74, 56.47, 56.43, 53.44, 50.31, 50.18, 48.63, 44.86, 41.68, 41.00, 37.99, 34.28, 31.80, 26.43, 21.36, 16.99, 15.97, 12.72 |
| 219 | | ¹H NMR (500 MHz, DMSO-d6) δ 12.66 (bs, 1H), 9.45 (bs, 1H), 8.98 (s, 1H), 8.29 (s, 1H), 8.04 (s, 1H), 8.01 – 7.88 (m, 2H), 7.62 – 7.49 (m, 1H), 7.40 (q, J = 8.0 Hz, 4H), 7.26 (t, J = 8.8 Hz, 1H), 5.15 (d, J = 3.5 Hz, 1H), 4.54 (d, J = 9.3 Hz, 1H), 4.49 – 4.31 (m, 3H), 4.22 (dd, J = 16.1, 5.6 Hz, 1H), 3.81 – 3.53 (m, 6H), 3.26 – 3.03 (m, 6H), 2.73 – 2.52 (m, 3H), 2.44 (s, 3H), 2.42 – 2.33 (m, 1H), 2.09 – 1.98 (m, 1H), 1.95 – 1.84 (m, 1H), 1.74 (q, J = 7.5 Hz, 2H), 0.96 (t, 3H), 0.94 (s, 9H). ¹³C NMR (126 MHz, dmso) δ 180.45, 172.02, 171.35, 170.07, 169.64, 156.00 (dd, J = 245.9, 6.5 Hz), 152.34 (dd, J = 249.7, 8.3 Hz), 151.52, 147.75, 144.70, 144.30, 139.55, 138.08, 137.91, 131.22, 129.66, 128.69, 128.53 (d, J = 2.4 Hz), 127.46, 121.96 (d, J = 14.1 Hz), 118.61 – 117.82 (m), 117.60, 115.44, 115.20, 112.32 (dd, J = 23.0, 3.3 Hz), 68.95, 58.78, 56.50, 56.39, 53.46, 50.25, 50.13, 44.76, 41.69, 41.17, 37.99, 35.43, 30.18, 28.05, 26.44, 16.89, 16.00, 12.67. |
| 220 | | 1H NMR (500 MHz, DMSO-d6) δ 12.97 (bs, 1H), 10.11 (s, 1H), 9.79 (bs, 1H), 8.98 (d, J = 2.3 Hz, 0H), 8.69 (s, 1H), 8.66 – 8.49 (m, 2H), 8.23 (s, 1H), 8.02 (d, J = 9.0 Hz, 1H), 7.84 – 7.64 (m, 4H), 7.63 – 7.53 (m, 1H), 7.51 – 7.33 (m, 4H), 7.29 (t, J = 8.4 Hz, 1H), 5.17 (s, 1H), 4.56 (d, J = 7.8 Hz, 1H), 4.50 – 4.39 (m, 2H), 4.40 – 4.31 (m, 1H), 4.26 – 4.16 (m, 1H), 3.66 (q, J = 10.1 Hz, 2H), 3.19 – 3.06 (m, 2H), 2.72 – 2.52 (m, 4H), 2.44 (s, 3H), 2.12 – 1.97 (m, 1H), 1.96 – 1.84 (m, 1H), 1.74 (dq, J = 13.2, 8.3, 7.3 Hz, 2H), 0.96 (t, 3H), 0.95 (s, 9H). 13C NMR (126 MHz, dmso) δ 180.66, 172.02, 171.24, 170.67, 169.64, 156.05 (dd, J = 246.9, 7.0 Hz), 152.37 (dd, J = 249.3, 8.1 Hz), 151.49, 148.66, 147.75, 143.82, 139.53, 139.00, 138.70, 132.54, 131.27, 131.22, 129.68, 129.22 – 128.38 (m), 128.69, 127.47, 127.39, 126.53, 121.99 (dd, J = 12.9, 4.5 Hz), 119.59, 118.72 – 117.87 (m), 117.57, 115.68, 112.90 – 112.05 (m), 68.95, 58.79, 56.56, 56.41, 53.51, 41.71, 37.98, 35.45, 31.98, 30.14, 26.43, 16.88, 15.99, 12.65. |
| 221 | B | 1H NMR (400 MHz, DMSO-d6) δ 12.96 (bs, 1H), 10.23 (s, 1H), 9.75 (bs, 1H), 8.97 (s, 1H), 8.69 |

FIG. 3. Continued

| | | |
|---|---|---|
| | | (s, 1H), 8.66 – 8.51 (m, 2H), 8.26 (d, J = 9.1 Hz, 1H), 8.22 (s, 1H), 7.73 (dd, J = 8.5 Hz, 4H), 7.59 (q, J = 8.6 Hz, 1H), 7.41 (dd, J = 8.0 Hz, 4H), 7.28 (t, J = 8.7 Hz, 1H), 5.16 (d, 1H), 4.59 (d, J = 9.2 Hz, 1H), 4.52 – 4.33 (m, 3H), 4.24 (dd, J = 15.7, 5.0 Hz, 1H), 3.68 (q, J = 10.6 Hz, 2H), 3.44 (q, 2H), 3.20 – 3.05 (m, 2H), 2.45 (s, 3H), 2.10 – 2.01 (m, 1H), 1.96 – 1.89 (m, 1H), 1.74 (dq, J = 14.8, 7.3 Hz, 2H), 0.98 (s, 9H), 0.97 (t, J = 8.3 Hz, 3H). 13C NMR (101 MHz, dmso) δ 180.62, 171.91, 169.34, 166.16, 166.03, 156.02 (dd, J = 246.8, 7.1 Hz), 152.34 (dd, J = 249.4, 8.1 Hz), 151.43, 148.69, 147.73, 143.79, 139.50, 138.69, 138.54, 132.98, 131.17, 131.13, 129.68, 129.11 – 128.65 (m), 128.67, 128.01, 127.45, 126.53, 122.21 – 121.73 (m), 119.70, 118.63 – 117.89 (m), 117.54, 115.66, 112.35 (dd, J = 23.5, 3.0 Hz), 68.93, 58.79, 56.66, 56.52, 53.49, 44.32, 41.70, 37.97, 35.60, 26.33, 16.85, 15.96, 12.62. |
| 222 | D | 1H NMR (500 MHz, DMSO-d6) δ 12.71 (bs, 1H), 9.74 (bs, 1H), 8.98 (s, 1H), 8.59 (t, J = 5.7 Hz, 1H), 8.29 (s, 1H), 8.26 (d, J = 9.1 Hz, 1H), 8.03 (s, 1H), 7.96 (bs, 1H), 7.57 (q, J = 7.4, 6.3 Hz, 1H), 7.41 (dd, J = 8.0 Hz, 4H), 7.26 (t, J = 8.7 Hz, 1H), 5.22 – 5.05 (m, 1H), 4.58 (d, J = 9.3 Hz, 1H), 4.51 – 4.32 (m, 3H), 4.23 (dd, J = 15.8, 5.3 Hz, 1H), 3.67 (q, J = 12.3, 10.6 Hz, 8H), 3.52 (dd, J = 53.7, 15.5 Hz, 2H), 3.27 – 3.05 (m, 6H), 2.45 (s, 3H), 2.09 – 2.00 (m, 1H), 1.96 – 1.86 (m, 1H), 1.74 (h, J = 7.3 Hz, 2H), 0.97 (s, 9H), 0.96 (t, 3H). 13C NMR (101 MHz, dmso) δ 180.41, 171.91, 169.38, 166.32, 166.06, 156.01 (dd, J = 246.5, 6.7 Hz), 152.34 (dd, J = 249.2, 8.3 Hz), 151.44, 147.73, 144.60, 144.28, 139.50, 138.06. 137.84, 131.17, 129.66, 128.75 (d, J = 8.0 Hz), 128.65, 127.43, 121.86 (dd, J = 13.5, 3.5 Hz), 118.34 (m), 117.58, 115.42, 115.18, 112.28 (dd, J = 23.1, 3.5 Hz), 68.89, 58.75, 56.54, 56.43, 53.49, 50.10, 45.56, 41.68, 41.19, 40.95, 37.95, 35.52, 26.36, 16.85, 15.96, 12.62. |
| 223 | C | 1H NMR (400 MHz, CD3OD): δ 8.81 (s, 1H), 8.70 (s, 1H), 8.59 (s, 1H), 7.91 (s, 1H), 7.75 (q, J = 6.0 Hz, 1H), 7.62 (d, J = 8.0 Hz, 2H), 7.35-7.44 (m, 6H), 7.14 (t, J = 8.2 Hz, 1H), 5.33-5.35 (m, 0.5H), 5.29-5.31 (m, 0.5H), 5.16 (br, 1H), 4.69-4.72 (m, 4H), 4.54 (s, 1H), 4.32-4.36 (m, 1H), 4.11-4.14 (m, 1H), 3.84-3.88 (m, 3H), 3.43-3.58 (m, 6H), 3.09-3.18 (m, 2H), 2.65 (br, 2H), 2.42 (s, 3H), 2.03-2.21 (m, 9H), 1.07(s, 9H) |
| 224 | A | 1H NMR (300 MHz, DMSO-d6) δ 13.01 (s, 1H), 9.87 (s, 1H), 8.98 (s, 1H), 8.77 (d, J = 3.5 Hz, 2H), 8.71 – 8.54 (m, 3H), 8.13 (s, 1H), 7.71 – 7.57 (m, 1H), 7.42 (d, J = 1.0 Hz, 5H), 7.29 (t, J = 8.9 Hz, 1H), 5.40 (s. 1H), 5.26 – 5.14 (m, 2H), 4.58 (d, J = 9.5 Hz, 2H), 4.53 – 4.35 (m, 3H), 4.27 (dd, J = 15.7, 5.6 Hz, 1H), 3.97 (s, 2H), 3.80 (s, 4H), 3.75 – 3.48 (m, 4H), 3.28 (d, J = 9.5 Hz, 1H), 2.45 (s, 3H), 2.11 (d, J = 15.8 Hz, 7H), 1.94 (d, J = 12.9 Hz, 4H), 1.80 (s, 2H), 0.97 (s, 9H) |
| 225 | A | 1H NMR (300 MHz, DMSO-d6) δ 12.97 (s, 1H),9.85(s,1H), 8.95 (s, 1H), 8.73 (s, 2H), 8.67 – 8.50 (m, 3H), 8.09 (s, 1H), 7.67 – 7.52 (m, 2H), 7.39 (s, 4H), 7.23 (t, J = 8.7 Hz, 1H), 5.22 – 5.10 (m, |

FIG. 3. Continued

| | | |
|---|---|---|
| 226 | A | 2H), 4.55 – 4.17 (m, 5H), 3.78 (s, 4H), 3.66- 3.13 (s, 7H), 3.01 (s, 5H), 2.43 (s, 3H), 2.32 (s, 5H), 2.07 (d, J = 18.9 Hz, 4H), 0.92 (s, 9H) |
| 227 | A | 1H NMR (400 MHz, CD3OD): δ 8.77 (s, 1H), 8.59 (s, 1H), 8.49 (s, 1H), 7.79 (s, 1H), 7.61-7.69 (m, 1H), 7.49 (d, J = 8.8 Hz, 2H), 7.31-7.39 (m, 4H), 6.98-7.04 (m, 3H), 5.18 (s, 0.5H), 5.02 (s, 0.5H), 4.56 (s, 1H), 4.41-4.53 (m, 2H), 4.22-4.29 (m, 1H), 3.76-3.81 (m, 1H), 3.68-3.73 (m, 1H), 3.23-3.52 (m, 4H), 3.16 (s, 4H), 2.94 (s, 2H), 2.90 (s, 1H), 2.72 – 2.81 (m, 2H), 2.50 (br, 4H), 2.38 (s, 3H), 1.92-2.20 (m, 10H), 1.66-1.79 (m, 2H), 0.95 (s, 9H) |
| 228 | A | 1H NMR (400 MHz, CD3OD): δ 8.89 (s, 1H), 8.70 (s, 1H), 8.61 (s, 1H), 7.91 (s, 1H), 7.71-7.80 (m, 1H), 7.60 (d, J = 8.4 Hz, 2H), 7.43-7.50 (m, 4H), 7.12-7.16 (m, 3H), 5.23 (s, 0.5H), 5.18 (s, 0.5H), 4.56 (s, 1H), 4.53-4.66 (m, 4H), 4.35-4.41 (m, 1H), 3.79-3.90 (m, 4H), 3.44-3.60 (m, 6H), 3.08-3.19 (m, 2H), 2.72-2.81 (m, 10H), 2.50 (s, 3H), 2.03-2.25 (m, 5H), 1.87-1.92 (m, 3H), 1.04 (s, 9H) |
| 229 | C | 1H NMR (400 MHz, DMSO-d6): δ 8.99(s, 1H), 8.66(s, 1H), 8.54-8.59(m, 2H), 8.15(s, 1H), 8.06(s, 1H), 7.85(d, J = 9.6 Hz, 1H), 7.60-7.66(m, 3H), 7.42(q, J = 8.0 Hz, 4H), 7.27(t, J = 8.8 Hz, 1H), 7.08(d, J = 8.4 Hz, 2H), 5.30(d, J = 52.8 Hz, 1H), 4.25-4.54(m, 6H), 2.90-3.08(m, 8H), 2.85(s, 2H), 2.57(s, 4H), 2.46(s, 3H), 2.42(s, 2H), 1.90-2.22(m, 8H), 1.71(t, J = 11.6 Hz, 2H), 1.43(s, 2H), 1.24(s, 3H), 0.95(s, 9H) |
| 230 | B | 1H NMR (300 MHz, DMSO-d6) δ 13.01 (s, 1H), 9.87 (s, 1H), 8.80 – 8.60 (m, 5H), 8.55 (s, 1H), 8.12 (s, 1H), 7.71 – 7.56 (m, 1H), 7.50 – 7.34 (m, 5H), 7.27 (t, J = 8.9 Hz, 1H), 5.40 (s, 1H), 5.26 – 5.14 (m, 1H), 4.60 (d, J = 9.5 Hz, 3H), 4.54 – 4.36 (m, 2H), 4.26 (dd, J = 16.0, 5.5 Hz, 2H), 4.01 (d, J = 2.8 Hz, 4H), 3.84 (s, 4H), 3.67 (d, J = 6.9 Hz, 3H), 3.27 (d, J = 9.5 Hz, 1H), 2.59 (d, J = 13.9 Hz, 6H), 2.42 (s, 3H), 2.10 (d, J = 17.1 Hz, 4H), 1.25 (s, 0H), 0.98 (s, 9H) |
| 231 | D | 1H NMR (400 MHz, Methanol-d4): δ 8.89 (d, J = 11.9 Hz, 1H), 8.77 (s, 1H), 8.61 (d, J = 2.2 Hz, 1H), 8.00 (s, 1H), 7.65-7.62 (m, 3H), 7.52-7.46 (m, 2H), 7.46-7.40 (m, 2H), 7.16-7.12 (m, 3H), 5.43-5.25 (m, 1H), 4.69-4.49 (m, 4H), 4.39 (t, J = 15.7 Hz, 1H), 3.94-3.85 (m, 3H), 3.85-3.78 (m, 2H), 3.78-3.68 (m, 2H),3.66-3.47 (m, 6H), 3.25 (t, J = 6.6 Hz, 3H), 2.61 (d, J = 5.5 Hz, 4H), 2.48 (s, 3H), 2.39-2.20 (m, 3H), 2.10-2.03 (m, 2H), 1.05 (d, J = 11.1 Hz, 9H) |
| 232 | B | 1H NMR (400 MHz, MeOD-d4): δ: 8.85 (s, 1H), 8.69 (s, 1H), 8.58 (d, J = 2.0 Hz, 1H), 7.90 (s, 1H), 7.76-7.74 (m, 1H), 7.62 (d, J = 8.4 Hz, 2H), 7.46-7.44 (m, 2H), 7.41-7.39 (m, 2H), 7.13-7.08 (m, 3H), 5.30 (s, 0.5H), 5.15 (s, 0.5H), 4.63 (s, 1H), 4.56-4.52 (m, 4H), 4.49-4.33 (m, 2H), 4.19 (t, J = 4.0 Hz, 2H), 3.98 (s, 2H), 3.85-3.80 (m, 4H), 3.58-3.40 (m, 9H), 2.45 (s, 3H), 2.21-1.99 (m, 5H), 1.03 (s, 9H) |
| | C | 1H NMR (400 MHz, CDCl3): δ 8.84(s, 1H), 8.67(s, 1H), 8.57(s, 1H), 7.82(d, J = 8.0 Hz, 1H), |

FIG. 3. Continued

| | | |
|---|---|---|
| 233 | B | 7.68-7.74(m, 2H), 7.53(d, J = 7.6 Hz, 3H), 7.32(s, 4H), 6.99-7.01(m, 3H), 5.21(d, J = 52.8 Hz, 1H), 4.77(s, 1H), 4.32-4.58(m, 4H), 4.16(d, J = 10.6 Hz, 1H), 3.45-3.73(m, 9H), 2.8-2.30(m 3H), 2.69(t, J = 8.4 Hz, 3H), 2.50-2.55(m, 8H), 2.37(s, 2H), 2.15-2.26(m, 4H), 1.74(d, J = 9.6 Hz, 2H), 1.44(s, 4H), 0.97(s, 9H) |
| 234 | C | 1H NMR (400 MHz, CD3OD): δ 8.88 (s, 1H), 8.72-8.64 (m, 3H), 8.58 (d, J = 2.2 Hz, 1H), 7.93 (s, 1H), 7.80-7.75 (m, 1H), 7.52-7.50(m, 2H), 7.48-7.45 (m, 2H), 7.19-7.09 (m, 1H), 5.31 (d, J = 3.6 Hz, 1H), 4.66 (s, 1H), 4.64-4.47 (m, 3H), 4.37 (d, J = 15.5 Hz, 1H), 3.93-3.77 (m, 6H), 3.75-3.60 (m, 2H), 3.60-3.40 (m, 4H), 3.32-3.26 (m, 2H), 3.19-3.05 (m, 2H), 2.89-2.82(m, 1H), 2.70-2.60(m, 2H), 2.55-2.50(m, 4H), 2.50-2.40(m, 3H), 2.30-2.00 (m, 4H), 1.06-1.00 (m, 9H) |
| 235 | D | 1H NMR (400 MHz, DMSO-d6): δ: 13.04(s, 1H), 9.84(s, 1H), 8.99(s, 1H), 8.77(s, 1H), 8.71(s, 1H), 8.53(s, 1H), 8.16(d, J = 2.4 Hz, 1H), 7.91(d, J = 7.2 Hz, 2H), 7.65-7.67(m, 3H), 7.38-7.41(m, 4H), 7.29(t, J = 7.6 Hz, 1H), 5.28(d, J = 52.8 Hz, 1H), 4.58(s, 1H), 4.39-4.45(m, 6H), 3.67(s, 3H), 3.59(s, 6H), 3.28-3.33(m, 5H), 3.10-3.12 (m, 4H), 2.45-2.69(m, 7H), 1.93-2.17(m, 9H), 0.97(s, 9H) |
| 236 | B | 1H NMR (400 MHz, DMSO-d6): δ 12.95 (s, 1H), 9.84 (s, 1H), 8.99 (s, 1H), 8.67 (s, 1H), 8.66-8.55(m, 2H), 8.09 (s, 1H), 8.02 (s, 1H), 7.69 (d, J = 8.4 Hz, 2H), 7.63-7.62(m, 1H), 7.40 (s, 4H), 7.29-7.27(m, 1H), 7.09 (d, J = 8.4 Hz, 2H), 5.37-5.24(m, 1H), 4.55 (d, J = 9.6 Hz, 3H), 4.42-4.25(m, 4H), 4.08 (s, 2H), 3.49 (s, 6H), 3.41 (s, 6H), 3.38-3.26(m, 3H), 3.17 (s, 6H), 2.45 (s, 3H), 1.80 (s, 4H), 0.96 (s, 9H) |
| 237 | D | 1H NMR (400 MHz, DMSO-d6): δ 13.01 (s, 1H), 9.84 (s, 1H), 8.99(s, 1H), 8.70-8.56 (m, 4H), 8.11 (s, 1H), 7.76-7.74 (m, 2H), 7.63-7.62 (m, 1H), 7.43-7.39 (m, 6H), 7.29-7.27 (m, 1H), 5.36-5.23 (m, 1H), 4.57-4.54 (m, 2H), 4.57-4.29(m, 9H), 3.70-3.68(m, 2H), 3.58-3.55(m, 2H), 3.49-3.29 (m, 6H), 2.88(s, 2H), 2.49 (s, 3H), 2.12-2.03 (m, 5H), 0.95 (s, 9H) |
| 238 | A | 1H NMR (400 MHz, DMSO-d6): δ 13.00 (s, 1H), 9.85 (s, 1H), 9.60-9.80 (m, 1H), 9.25-9.45 (m, 1H), 9.00 (s, 1H), 8.55-8.80 (m, 4H), 8.12 (s, 1H), 7.74-7.76 (m, 2H), 7.60-7.70 (m, 1H), 7.35-7.55 (m, 6H), 7.23-7.32 (m, 1H), 5.20-5.40 (m, 1H), 4.60-4.70 (m, 1H), 4.35-4.50 (m, 3H), 4.20-4.30 (m, 2H), 4.00-4.10 (m, 3H), 3.70-3.85 (m, 5H), 3.25-3.40 (m, 4H), 2.90-3.15 (m, 6H), 2.45 (s, 3H), 1.90-2.20 (m, 11H), 1.50-1.70 (m, 2H), 0.99 (s, 9H) |
| | A | 1H NMR (400 MHz, DMSO-d6): δ 12.89 (brs, 1H), 9.87 (brs, 1H), 8.97 (s, 1H), 8.64 (s, 1H), 8.61-8.52 (m, 1H), 8.45 (d, J = 7.7 Hz, 1H), 8.05 (s, 1H), 7.66-7.56 (m, 3H), 7.49-7.33 (m, 5H), 7.26-7.17 (m, 1H), 7.07 (d, J = 8.7 Hz, 2H), 5.35-5.21 (m, 1H), 5.19-5.13 (m, 1H), 4.95-4.85 (m, 1H), 4.56 (d, J = 9.6 Hz, 1H), 4.51-4.40 (m, 1H), 4.29-4.27 (m, 1H), 4.06-3.90 (m, 2H), 3.75-3.63 (m, 2H), 3.61-3.52 (m, 2H), 3.49-3.45 (m, 1H), 3.41-3.28 (m, 2H), 3.28-3.20 (m, 6H), 2.72-2.55 (m, 6H), 2.47-2.40 (m, 3H), 2.11-2.01 (m, 2H), 1.84-1.72 (m, 1H), 1.54-1.27 (m, 3H), 0.95 (s, 9H) |

FIG. 3. Continued

| | | |
|---|---|---|
| 239 | A | 1H NMR (400 MHz, DMSO-d6): δ 12.93 (s, 1H), 9.85 (s, 1H), 8.55 (s, 1H), 8.46 (d, J = 7.5 Hz, 1H), 8.08 (s, 1H), 7.78 (s, 1H), 7.62 (s, 4H), 7.48-7.34 (m, 2H), 7.27 (t, J = 8.7 Hz, 1H), 7.07 (d, J = 8.4 Hz, 2H), 5.38-5.21 (m, 1H), 4.91 (d, J = 8.8 Hz, 1H), 4.55-4.42 (m, 2H), 4.28 (s, 1H), 3.58 (s, 3H), 3.48 (s, 2H), 3.22 (s, 5H), 2.95-2.83 (m, 5H), 2.48-2.42 (m, 4H), 2.26-2.22 (m, 3H), 2.12-2.07 (m, 4H), 1.76 (s, 3H), 1.39-1.35 (m, 3H), 1.20-1.18 (m, 3H), 0.94 (s, 9H) |
| 240 | A | 1H NMR (300 MHz, DMSO-d6): δ12.8 (brs, 1H), 9.8 (brs, 1H), 9.00 (s, 1H), 8.67 (d, J = 2.2 Hz, 1H), 8.59-8.43 (m, 2H), 8.08 (s, 1H), 7.65-7.60 (m, 4H), 7.51-7.35 (m, 4H), 7.25 (t, J = 8.6 Hz, 1H), 7.09 (d, J = 8.4 Hz, 2H), 5.31 (d, J = 54.1 Hz, 1H), 5.16 (d, J = 3.5 Hz, 1H), 4.93 (t, J = 7.2 Hz, 1H), 4.51-4.46 (m, 2H), 4.32-4.30 (m, 1H), 3.62-3.46 (m, 5H), 3.38-3.34 (m, 3H), 3.28-3.00 (m, 9H), 2.49-2.46 (m, 7H), 2.11-2.07 (m, 3H), 1.81-1.78 (m, 1H), 1.46-1.40 (m, 3H), 0.96 (s, 9H) |
| 241 | C | 1H NMR (300 MHz, DMSO-d6) δ 12.90 (s, 1H), 9.84 (s, 1H), 8.94 (s, 1H), 8.63-8.52 (m, 3H), 8.05 (s, 1H), 7.63-7.55 (m, 3H), 7.41-7.31 (m, 5H), 7.28-7.22 (m, 1H), 7.10-6.81 (m, 2H), 5.44-5.11 (m, 2H), 4.65-4.12 (m, 5H), 4.02-3.78 (m, 2H), 3.74- 3.36 (m, 7H), 3.24- 3.09 (m, 5H), 2.43-2.33 (m, 8H), 2.14-1.78 (m, 4H), 1.66-1.40 (m, 4H), 0.94 (m, 10H) |
| 242 | C | 1H NMR (300 MHz, DMSO): δ 8.98 (s, 1H), 8.68-6.66 (m, 1H), 8.60-8.55 (m, 1H), 8.50-8.46 (m, 1H), 8.10 (s, 1H), 7.70-7.61 (m, 3H), 7.51-7.43 (m, 5H), 7.32-7.24 (m, 1H), 7.15-7.08 (m, 2H), 5.40-5.38 (m, 1H), 5.24-5.13 (m, 1H), 4.93-4.73 (m, 2H), 4.62-4.45 (m, 2H), 4.30-4.26 (m, 1H), 4.05-3.96 (m, 2H), 3.70-3.58 (m, 6H), 3.51-3.48 (m, 1H), 3.29-3.18 (s, 5H), 2.73-2.61 (m, 7H), 2.51-2.41 (m, 4H), 2.14-2.01 (m, 3H), 1.93-1.76 (m, 1H), 0.96 (s, 9H) |
| 243 | | 1H NMR (300 MHz, DMSO-d6) δ 12.90 (br, 1H), 9.85 (br, 1H), 8.99 (s, 1H), 8.66 (s, 1H), 8.53 (br, 1H), 8.43 (d, J = 9Hz, 1H), 8.07 (br, 1H), 7.75 (d, J = 9Hz, 1H), 7.63-7.58 (m, 3H), 7.46-7.37 (m, 4H), 7.28-7.25 (m, 1H), 7.07 (d, J = 9Hz, 2H), 5.38 (br, 1H), 5.13-5.12 (m, 1H), 4.86-4.81 (m, 2H), 4.53-4.50 (m, 2H), 4.29 (br, 1H), 3.64-3.61 (m, 4H), 3.48-3.38 (m, 3H), 3.32-3.21 (m, 5H), 3.07-3.01 (m, 1H), 2.91-2.83 (m, 3H), 2.59-2.51 (m, 4H), 2.46 (s, 3H), 2.24-2.04 (m, 7H), 1.79-1.75 (m, 3H), 1.60-1.52 (m, 1H), 1.21-1.05 (m, 2H), 0.95 (s, 9H) |
| 244 | | 1H NMR (300 MHz, DMSO-d6) δ 12.90 (s, 1H), 9.84 (b, 1H), 8.97 (s, 1H), 8.65-8.43 (m, 3H), 8.06 (s, 1H), 7.61-7.58 (m, 3H), 7.45-7.22 (m, 6H), 7.08-7.05 (m, 2H), 5.38-5.13 (m, 2H), 4.93-4.91 (m, 1H), 4.56-4.53 (m, 2H), 4.48-4.29 (m, 1H), 3.94 (s, 2H), 3.58- 3.21(m, 11H), 2.55-2.45 (m, 11H), 2.13-2.05 (m, 2H), 1.77-1.76 (m, 3H), 1.39 (d, J = 9 Hz, 3H), 0.96 (s, 9H) |
| 245 | | 1H NMR (300 MHz, CD3OD) δ 8.85 (s, 1H), 8.83 (s, 1H), 8.67 (s, 1H), 7.88 (s, 1H), 7.75-7.73 (m, 1H), 7.59 (d, J = 9 Hz, 2H), 7.43 (s, 4H), 7.16-7.10 (m, 3H), 5.30-4.85 (m, 3H), 4.69-4.46 (m, 3H), 4.05-4.00 (m, 2H), 3.85-3.80 (m, 3H), 3.66-3.58 (m, 2H), 3.50-3.39 (m, 6H), 2.84-2.70 (m, |

FIG. 3. Continued

| | |
|---|---|
| | 6H), 2.52 (s, 2H), 2.43 (s, 3H), 2.21-2.10 (m, 4H), 2.03-1.96 (m, 2H), 1.04 (s, 9H) |
| 246 | 1H NMR (300 MHz, DMSO-d6) δ 8.98 (s, 1H), 8.67 – 8.50 (m, 3H), 8.14 (s, 1H), 7.80 (d, J = 9.6 Hz, 1H), 7.67-7.56 (m, 3H), 7.47-7.32 (m, 5H), 7.19 (t, J = 8.8 Hz, 1H), 7.09-7.01 (d, J = 8.6 Hz, 2H), 5.14 (s, 1H), 4.54 -4.46 (m, 1H), 4.45 -4.31 (m, 3H), 4.25 (m, 1H), 3.78-3.61 (m, 2H), 3.25-3.15 (m, 5H), 3.02-2.76 (m, 4H), 2.75-2.65 (m, 2H), 2.45-2.40 (m, 4H), 2.29-2.00 (m, 10H), 1.99-1.82 (m, 1H), 1.81-1.68 (m, 2H), 1.68-1.49 (m, 1H), 1.22-1.05 (m, 2H), 1.10-0.81 (m, 13H) |
| 247 | 1H NMR (300 MHz, DMSO-d6): δ 13.20 (brs, 1H), 10.08 (brs, 1H), 9.08-8.61 (m, 2H), 8.61-8.38 (m, 2H), 8.05 (s, 1H), 7.65-7.35 (m, 8H), 7.30-7.15 (m, 1H), 7.15-7.01 (m, 2H), 5.42-5.11 (m, 2H), 4.92-4.75 (m, 2H), 4.60-4.50 (m, 2H), 4.40-4.10 (m, 1H), 3.69-3.53 (m, 5H), 3.51-3.48 (m, 2H), 3.39-3.36 (m, 3H), 3.30-3.20 (m, 5H), 3.15 (s, 2H), 3.12-3.01 (m, 3H), 2.50-2.40 (m, 5H), 2.33-1.95 (m, 4H), 1.75-1.83 (m, 1H), 1.10 (s, 9H) |
| 248 | 1H NMR (400 MHz, DMSO-d6): δ 12.90 (brs, 1H), 9.84 (brs, 1H), 8.99-8.98 (m, 1H), 8.66 (d, J = 2.3 Hz, 1H), 8.63-8.52 (m, 2H), 8.06-8.04 (m, 1H), 7.79 (d, J = 9.7 Hz, 1H), 7.67-7.60 (m, 3H), 7.45-7.41 (m, 3H), 7.25-7.20 (m, 1H), 7.10-7.02 (m, 2H), 5.23-5.13 (m, 2H), 4.55-4.41 (m, 2H), 4.40-4.33 (m, 2H), 4.32-4.22(m, 1H), 3.62 (m, 6H), 3.47-3.45 (m, 4H), 3.39-3.19 (m, 5H), 3.08-3.05 (m, 1H), 3.03-2.92 (m, 1H), 2.86-2.70 (m, 2H), 2.45 (s, 3H), 2.26 -2.15 (m, 2H), 2.11-1.80 (m, 5H), 1.73-1.60 (m, 4H), 0.94 (d, J = 7.0 Hz, 9H) |
| 249 | 1H NMR (300 MHz, DMSO-d6): δ 12.92 (s, 1H), 9.68 (b, 2H), 8.97 (s, 1H), 8.64-8.56 (m, 4H), 8.11 (s, 1H), 7.63-7.57 (m, 4H), 7.44-7.39 (m, 5H), 7.28-7.23 (m, 1H), 7.10-7.07 (m, 2H), 5.15-4.79 (m, 3H), 4.55-4.26 (m, 6H), 3.97 (s, 2H), 3.69-3.58 (m, 4H), 3.38-3.29 (m, 4H), 3.08-3.04 (m, 3H), 2.52-2.43 (m, 4H), 2.51-2.02 (m, 2H), 1.89-1.86 (m, 5H), 1.38-1.20 (m, 2H), 1.21-1.10 (m, 12H) |
| 250 | 1H NMR (300 MHz, DMSO): δ 9.80-9.20 (m, 2H), 8.99 (s, 1H), 8.73 (s, 2H), 8.67-8.62 (m, 1H), 8.55-8.40 (m, 2H), 8.05 (s, 1H), 7.73 (d, J = 9.6 Hz, 1H), 7.62-7.51 (m, 1H), 7.51-7.31 (m, 4H), 7.13-7.02 (m, 1H), 5.40-5.07 (m, 2H), 5.02-4.85 (m, 1H), 4.80-4.66 (m, 2H), 4.56-4.37 (m, 2H), 4.32-4.22 (m, 1H), 3.68-3.50 (m, 2H), 3.46-3.36 (m, 2H), 3.29-3.13 (m, 4H), 3.10-2.87 (m, 4H), 2.45-2.33 (m, 8H), 2.23-2.15 (m, 2H), 2.12-1.68 (m, 8H), 1.52-1.35 (m, 3H), 1.15-1.06 (m, 2H), 0.95 (s, 9H) |
| 251 | 1H NMR (400 MHz, CD3OD): δ 8.89 (s, 1H), 8.75-8.70 (m, 3H), 8.60 (s, 1H), 7.95 (s, 1H), 7.81-7.76 (m, 1H), 7.48-7.36 (m, 4H), 7.15-7.10 (m, 1H), 5.32-5.19 (m, 1H), 5.08-5.00 (m, 1H), 4.68-4.64 (m, 1H), 4.60-4.58 (m, 1H), 4.51-4.46 (m, 1H), 3.95-3.80 (m, 5H), 3.79-3.75 (m, 1H), 3.62-3.48 (m, 5H), 3.10-3.05 (m, 2H), 3.01-2.85 (m, 2H), 2.57-2.51(m, 4H), 2.50-2.47 (m, 2H), 2.32-2.11(m, 6H), 2.10-1.95 (m, 2H), 1.88-1.80 (m, 2H), 1.71-1.67 (m, 1H), 1.63-1.51 (m, 3H), 1.45- |

FIG. 3. Continued

| | | |
|---|---|---|
| 252 | | 1.37 (m, 2H), 1.10(s, 9H) |
| 253 | D | 1H NMR (300 MHz, DMSO-d6): δ 12.92 (s, 1H), 9.81-9.22 (m, 2H), 8.95 (s, 1H), 8.64-8.55 (m, 3H), 8.17-8.03 (m, 1H), 7.82-7.53 (m, 4H), 7.37-7.30 (m, 4H), 7.25 (t, J = 8.7 Hz, 1H), 7.11-6.97 (m, 2H), 5.37-5.10 (m, 2H), 4.57-4.05 (m, 10H), 3.87-3.38 (m, 11H), 3.14-2.70 (m, 5H), 2.42 (s, 3H), 2.09-1.83 (m, 5H), 1.21-1.06 (m, 1H), 0.93 (s, 9H) |
| 254 | B | 1H NMR (400 MHz, DMSO-d6): δ 13.03 (s, 1H), 9.91 (s, 1H), 9.85 (br, 1H), 9.02 (s, 1H), 8.65-8.77(m, 2H), 8.35 (s, 1H), 7.79-7.81. (m, 3H), 7.68(m, 1H), 7.53-7.54 (m, 4H), 7.38-7.39 (m, 4H), 6.70 (br, 1H), 5.40 (s, 0.5H), 5.38(s, 0.5H), 4.72 (s, 3H), 4.61-4.66 (m, 2H), 4.44-4.52 (m, 2H), 4.24-4.33 (m, 2H), 3.92-4.10 (m, 4H), 3.81-3.85 (m, 2H), 3.72-3.76 (m, 2H), 3.21-3.25(m, 2H), 3.10-3.12(m, 2H), 2.53 (s, 3H), 1.97-2.03 (m, 6H), 1.51-1.53(m, 2H), 1.02 (s, 9H) |
| 255 | B | 1H NMR (400 MHz, DMSO-d6): δ 13.00 (br, 1H), 8.99 (s, 1H), 8.69 (s, 1H), 8.61 (t, J = 7.0 Hz, 2H), 8.11 (s, 1H), 7.63-7.69 (m, 3H), 7.35-7.50 (m, 6H), 7.28-7.39 (m, 1H), 7.03 (d, J = 9.2 Hz, 2H), 5.18-5.42 (m, 2H), 4.54 (d, J = 9.2 Hz, 2H), 4.25-4.47 (m, 5H), 3.60-3.80 (m, 7H), 2.85-3.10 (m, 3H), 2.46 (s, 3H), 1.70-2.15 (m, 12H), 1.40-1.60 (m, 2H), 0.96 (s, 9H) |
| 256 | A | 1H NMR (400 MHz, CDCl3): δ 8.97 (s, 1H), 8.70 (d, J = 4 Hz, 1H), 8.60 (s, 2H), 7.68 (d, J = 8 Hz, 2H), 7.63-7.61 (m, 2H), 7.67-7.59 (m, 2H), 7.44-7.41 (m, 8H), 7.25 (s, 1H), 5.36-5.23 (m, 1H), 5.16 (s, 1H), 4.57 (d, J = 9.6 Hz, 1H), 4.48-4.37 (m, 4H), 4.28 (d, J = 1.6 Hz, 1H), 4.15 (s, 2H), 3.89 (s, 2H), 3.67-3.60 (m, 4H), 3.12-3.09 (m, 2H), 2.66 (s, 2H), 2.44 (s, 3H), 2.44-2.07 (m, 8H), 0.96 (s, 9H) |
| 257 | B | 1H NMR (400 MHz, MeOD-d4): δ 8.92 (s, 1H), 8.81 (s, 2H), 8.80 (s, 1H), 8.62 — 8.76 (m, 2H), 7.96 (s, 1H), 7.72 — 7.79 (m, 1H), 7.42 — 7.51 (m, 4H), 7.49 (t, J = 6.0 Hz, 1H), 5.33 — 5.38 (m, 0.5H), 5.17 — 5.20 (m, 0.5H), 4.55 — 4.67 (m, 4H), 4.32 — 4.47 (m, 2H), 3.91 — 4.09 (m, 4H), 3.80 — 3.87 (m, 1H), 3.43 — 3.74 (m, 10H), 3.22 — 3.24 (m, 3H), 2.50 (s, 3H), 2.04 — 2.23 (m, 9H), 1.62 — 1.77 (m, 3H), 1.09 (s, 9H) |
| 258 | B | 1H NMR (400 MHz, DMSO-d6): δ 12.94 (s, 1H), 9.84 (s, 1H), 8.99(s, 1H), 8.68 (s, 2H), 8.66 (s, 2H), 8.09 (s, 1H), 7.69-7.62 (m, 3H), 7.43-7.37 (m, 4H), 7.29-7.25 (m, 1H), 7.10-7.07 (m, 2H), 5.24 (m, 1H), 4.55 (d, J=9.2Hz, 2H), 4.44-4.40(m, 7H), 3.70-3.67 (m, 2H), 3.59-3.56 (m, 4H), 3.49(s, 1H), 3.40-3.38 (m, 2H), 3.31-3.28 (m, 2H), 3.24 (s, 5H), 2.02-1.99 (m, 6H), 1.23 (s, 1H), 0.95 (s, 9H) |
| | B | 1H NMR (400 MHz, DMSO-d6): δ: 12.97 (s, 1H), 9.83 (s, 1H), 8.98 (s, 1H), 8.58-8.69 (m, 4H), 8.11 (d, J = 2.4 Hz, 1H), 7.62-7.87 (m, 3H), 7.36-7.43 (m, 3H), 7.27 (t, J = 5.6 Hz, 1H), 5.36 (s, 0.5H), 5.21 (s, 0.5H), 4.57 (d, J = 10.0 Hz, 1H), 4.37-4.40 (m, 5H), 4.19-4.24 (m, 4H), 3.91-4.13 (m, 4H), 3.30-3.38 (m, 6H), 2.67-2.71 (m, 2H), 2.49 (s, 3H), 1.87-2.07(m, 8H), 0.96 (s, 9H), 0.93 |

FIG. 3. Continued

| | | (s, 1H) |
|---|---|---|
| 259 | A | 1H NMR (400 MHz, DMSO-d6): δ 13.00 (s, 1H), 9.84 (s, 1H), 9.00 (s, 1H), 8.76 (s, 2H), 8.66 (s, 1H), 8.50-8.60 (m, 2H), 8.11 (s, 1H), 7.60-7.70 (m, 1H), 7.35-7.50 (m, 4H), 7.20-7.30 (m, 1H), 5.20-5.40 (m, 1H), 4.70-4.80 (m, 2H), 4.56 (d, J = 9.2 Hz, 1H), 4.35-4.50 (m, 4H), 4.20-4.30 (m, 3H), 2.90-3.10 (m, 5H), 3.25-3.35 (m, 2H), 3.35-3.55 (m, 6H), 3.55-3.70 (m, 4H), 2.45 (s, 3H), 1.80-2.20 (m, 8H), 1.15-1.25 (m, 2H), 0.94 (s, 9H) |
| 260 | C | 1HNMR (400 MHz, DMSO-d6): δ: 8.98 (s, 1H), 8.69 (s, 1H), 8.58-8.89 (m, 2H), 8.15 (s, 1H), 8.10 (s, 1H), 7.60-7.66 (m, 4H), 7.33-7.40 (m, 6H), 7.27 (t, J = 6.4 Hz, 1H), 5.21 (s, 0.5H), 5.36 (s, 0.5H), 4.51 (d, J = 9.6 Hz, 1H), 4.36-4.43 (m, 4H), 4.11 (t, J = 5.6 Hz, 1H), 3.59-3.67 (m, 4H), 3.48 (s, 1H), 3.26-3.41 (m, 6H), 2.95-3.16 (m, 4H), 2.65 (t, J = 7.2 Hz, 2H), 2.44 (s, 3H), 1.86-2.15 (m, 4H), 1.53-1.65 (m, 4H), 0.93 (s, 9H) |
| 261 | C | 1H NMR (400 MHz, CDCl3): δ 13.02 (s, 1H), 8.99 (s, 1H), 8.70-8.62(m, 3H), 8.15-8.12 (m, 1H), 7.71-7.63 (m, 3H), 7.51-7.40 (m, 7H), 7.30-7.26 (m, 1H), 5.37-5.12 (m, 2H), 4.59-4.57 (m, 1H), 4.45-4.37 (m, 3H), 4.28-4.26 (m, 1H), 4.16 (s, 1H), 3.94-3.92 (m, 3H), 3.66-3.50 (m, 3H), 3.36 (s, 4H), 2.98-2.93 (m, 2H), 2.71-2.66(m, 5H), 2.45 (s, 3H), 2.34 (s, 3H), 2.18-2.10 (m, 7H), 0.96 (s, 9H) |
| 262 | D | 1H NMR (400 MHz, DMSO-d6): δ 12.97 (s, 1H), 9.83 (s, 1H), 8.95-8.99 (m, 3H), 8.69-8.71 (m, 1H), 8.59 (s, 1H), 8.09 (s, 1H), 7.69-7.71 (m, 1H), 7.62-7.63 (m, 2H), 7.38-7.44 (m, 3H), 7.27 (t, J = 5.6 Hz, 2H), 7.19 (d, J = 8.4 Hz, 1H), 5.37 (s, 0.5H), 5.24 (s, 0.5H), 4.57 (d, J = 7.2 Hz, 1H), 4.40-4.45 (m, 3H), 4.23-4.25 (m, 2H), 3.89-3.94 (m, 6H), 3.61-3.78 (m, 8H), 3.41-3.49 (m, 4H), 3.32-3.37 (m, 4H), 2.77 (br, 2H), 2.45 (s, 3H), 1.97-2.01 (m, 6H), 0.99 (s, 9H) |
| 263 | C | 1HNMR (400 MHz, DMSO-d6): δ: 8.99 (s, 1H), 8.60 (s, 1H), 8.55 (t, J = 6.0 Hz, 1H), 8.48 (s, 1H), 8.23 (br, 1H), 8.02 (s, 1H), 7.75 (d, J = 9.2 Hz, 1H), 7.50-7.59 (m, 3H), 741-7.45 (m, 4H), 7.15 (t, J = 8.0 Hz, 1H), 6.76 (d, J = 8.0 Hz, 2H), 6.04 (s, 1H), 5.28 (s, 0.5H), 5.21 (s, 0.5H), 4.55 (d, J = 9.6 Hz, 1H), 4.27-4.45 (m, 4H), 3.92 (t, J = 10.0 Hz, 1H), 3.61-3.70 (m, 6H), 3.49-3.56 (m, 2H), 3.21-3.25 (m, 6H), 2.87 (s, 4H), 2.45 (s, 3H), 2.29-2.33 (m, 3H), 1.91-2.09 (m, 7H), 1.24-1.31 (m, 1H), 0.96 (s, 9H) |
| 264 | A | 1H NMR (400 MHz, DMSO-d6): δ 13.05 (s, 1H), 9.70-9.90 (m, 2H), 9.00 (s, 1H), 8.75 (d, J = 8.0 Hz, 1H), 8.70 (s, 1H), 8.50-8.65 (m, 3H), 8.00-8.10 (m, 2H), 7.60-7.70 (m, 1H), 7.35-7.50 (m, 4H), 7.28 (t, J = 4.8 Hz, 1H), 7.15 (t, J = 8.8 Hz, 1H), 5.20-5.40 (m, 1H), 4.60 (d, J = 9.2 Hz, 1H), 4.35-4.50 (m, 5H), 4.20-4.30 (m, 2H), 4.00-4.15 (m, 3H), 3.50-3.60 (m, 3H), 3.40-3.50 (m, 3H), 3.20-3.33 (m, 3H), 3.05-3.18 (m, 4H), 2.05-2.23 (m, 4H), 1.90-2.05 (m, 4H), 1.55-1.62 (m, 2H), 0.95 (s, 9H) |

FIG. 3. Continued

| | | |
|---|---|---|
| 265 | C | 1H NMR (400 MHz, DMSO-d6): δ: 9.41-8.99 (m, 3H), 8.60 (s, 1H), 8.07-8.05 (m, 2H), 7.80 (s, J = 10.0 Hz, 1H), 7.72-7.69 (m, 1H), 7.44-7.37 (m, 6H), 7.12-7.09 (m, 1H), 5.33 (s, 0.5H), 5.14 (s, 0.5H), 5.13 (s, 1H), 4.51 (d, J = 8.4 Hz, 1H), 4.49-4.38 (m, 3H), 4.29-4.26 (m, 1H), 3.64-3.61 (m, 6H), 3.37-3.35 (m, 2H), 3.22-3.20 (m, 2H), 3.04-2.99 (m, 1H), 2.92-2.83 (m, 3H), 2.45 (s, 3H), 2.20-1.98 (m, 9H), 1.95-1.90 (m, 2H), 1.82-1.74 (m, 2H), 1.60 (s, 2H), 1.23-1.18 (m, 4), 1.14 (s, 9H) |
| 266 | A | 1H NMR (400 MHz, CDCl3): δ 12.90 (s, 1H), 9.03 (s, 2H), 8.99 (s, 1H), 8.44 (s, 1H), 8.14 (s, 1H), 8.06 (s, 1H), 7.92-7.90 (m, 2H), 7.44-7.42 (m, 1H), 7.41-7.39 (m, 6H), 7.26 (t, J = 4 Hz, 1H), 5.37-5.24 (m, 1H), 5.12 (s, 1H), 4.15 (d, J = 10 Hz, 1H), 4.44-4.28 (m, 5H), 3.66-3.59 (m, 4H), 3.48 (s, 2H), 3.01-2.84 (m, 8H), 2.43 (s, 3H), 2.22-1.99 (m, 8H), 1.97-1.90 (m, 4H), 1.75-1.72 (m, 2H), 0.95 (s, 9H) |
| 267 | A | 1H NMR (400 MHz, DMSO-d6): δ 13.08 (s, 1H), 9.80-10.00 (m, 2H), 9.00-9.10 (m, 3H), 8.88 (s, 1H), 8.75 (d, J = 7.6 Hz, 1H), 8.55-8.65 (m, 2H), 8.09 (s, 1H), 7.60-7.70 (m, 1H), 7.32-7.50 (m, 4H), 7.28 (t, J = 4.8 Hz, 1H), 5.20-5.40 (m, 1H), 4.55-4.65 (m, 2H), 4.35-4.50 (m, 4H), 4.20-4.30 (m, 2H), 4.00-4.15 (m, 3H), 3.25-3.40 (m, 10H), 3.00-3.18 (m, 4H), 2.46 (s, 3H), 2.05-2.20 (m, 3H),1.90-2.05 (m, 4H), 1.50-1.65 (m, 3H), 0.95 (s, 9H) |
| 268 | | 1H NMR (400 MHz, DMSO-d6): δ: 12.94 (s, 1H), 9.83 (s, 1H), 8.98 (s, 1H), 8.66-8.68 (m, 2H), 8.58 (s, 2H), 8.09 (s, 1H), 7.61-7.68 (m, 3H), 7.37-7.43 (m, 4H), 7.27 (t, J = 6.4 Hz, 1H), 7.08 (d, J = 8.0 Hz, 2H), 5.21 (s, 0.5H), 5.36 (s, 0.5H), 4.56-4.58 (m, 3H), 4.46-4.55 (m, 8H), 4.24-4.44 (m, 4H), 4.19-4.23 (m, 4H), 3.52-3.60 (m, 2H), 2.44 (s, 3H), 1.62-2.11 (m, 9H), 0.96 (s, 9H) |
| 269 | | 1H NMR (400 MHz, CDCl3): δ 8.85 (s, 1H), 8.55 (s, 1H), 8.54 (s, 1H), 7.87 (s, 1H), 8.70 (d, J = 4 Hz, 1H), 8.60 (s, 2H), 7.72-7.69 (m, 1H), 7.48 (d, J = 6.8 Hz, 2H), 7.43-7.37 (m, 4H), 7.13 (t, J = 4.4 Hz, 1H), 6.62 (d, J = 8.4 Hz, 2H), 5.27-5.17 (m, 1H), 4.61 (s, 1H), 4.52 (d, J = 8 Hz, 4H), 4.38-4.35 (m, 2H), 4.16 (t, J = 6.8 Hz, 2H), 3.86-3.85 (m, 3H), 3.79-3.70 (m, 1H), 3.67 (q, J = 4.4 Hz, 2H), 3.57 (s, 2H), 3.54-3.42 (m, 8H), 2.82-2.75 (m, 1H), 2.45 (s, 3H), 2.44-2.20 (m, 4H), 1.93-1.92 (m, 2H), 1.02 (s, 9H) |
| 271 | B | 1H NMR (400 MHz, DMSO-d6): δ 11.05 (s, 1H), 10.89 (s, 1H), 8.71 (s, 1H), 8.57 (d, J = 6.0 Hz, 2H), 7.83 (d, J = 8.8 Hz, 2H), 7.56 (d, J = 6.4 Hz, 1H), 7.49 (d, J = 6.0 Hz, 2H), 7.41 (s, 1H), 7.22 (d, J = 8.0 Hz, 1H), 7.15 (d, J = 9.2 Hz, 2H), 7.03 (s, 1H), 6.76 (s, 1H), 5.03-4.99 (m, 1H), 4.18 (d, J = 6.4 Hz, 2H), 3.68 (s, 4H), 3.60-3.50 (m, 4H), 3.02-2.99 (m, 2H), 2.87-2.74 (m, 3H), 2.60-2.56 (m, 2H), 2.08-2.06 (m, 2H), 2.01-1.99 (m, 6H) |
| 273 | C | 1H NMR (400 MHz, DMSO-d6): δ 11.15 (bs, 1H), 8.72 (s, 1H), 8.57 (d, J = 5.6Hz, 2H), 7.83 (d, J = 8.8 Hz, 2H), 7.77 (s, 1H), 7.49-7.57 (m, 4H), 7.41 (s, 1H), 7.17-7.30 (m, 3H), |

FIG. 3. Continued

| | | |
|---|---|---|
| 274 | B | 5.09-5.13 (m, 1H), 3.20-3.35 (m, 8H), 2.80-3.12 (m, 6H), 2.52-2.75 (m, 3H), 1.90-2.12 (m, 2H) |
| | C | 1H NMR (400 MHz, DMSO-d6): δ 11.05 (s, 1H), 10.89 (s, 1H), 8.72 (s, 1H), 8.58 (d, J = 5.2 Hz, 2H), 7.83 (d, J = 8.8 Hz, 2H), 7.56 (d, J = 8.0 Hz, 1H), 8.48 (d, J = 5.2 Hz, 2H), 7.42 (s, 1H), 7.22 (d, J = 8.4 Hz, 1H), 7.16 (d, J = 8.8 Hz, 2H), 7.04 (s, 1H), 6.75 (s, 1H), 4.99-5.01 (m, 1H), 4.25-4.30 (m, 2H), 3.68 (s, 4H), 3.18 (d, J = 5.2 Hz, 1H), 3.01-3.03 (m, 2H), 2.82-2.88 (m, 3H), 2.56-2.60 (m, 4H), 1.98-2.02 (m, 2H), 1.38 (t, J = 7.2 Hz, 3H) |
| 275 | B | |
| | C | 1H NMR (400 MHz, DMSO-d6): δ 11.09 (br, 1H), 10.90 (s, 1H), 8.71 (s, 1H), 8.57 (d, J = 5.2 Hz, 2H), 7.83 (d, J = 9.2 Hz, 2H), 7.56 (d, J = 8.0 Hz, 1H), 7.49 (d, J = 5.6 Hz, 2H), 7.41 (s, 1H), 7.15-7.23 (m, 3H), 7.03 (s, 1H), 6.75 (s, 1H), 5.00-5.05 (m, 1H), 4.16 (t, J = 6.4 Hz, 2H), 3.80 (br, 4H), 3.30(br, 4H), 2.80-3.10 (m, 5H), 2.55(m, 2H), 1.95-2.05 (m, 1H), 1.75-1.85 (m, 2H), 1.00-1.05 (m, 3H) |
| 276 | B | 1H NMR (400 MHz, DMSO-d6): δ 11.02 (s, 1H), 10.93 (s, 1H), 8.71 (s, 1H), 8.57 (d, J = 5.2 Hz, 2H), 7.83 (d, J = 8.8 Hz, 2H), 7.53-7.57 (m, 5H), 7.42-7.50 (m, 3H), 7.36-7.38 (m, 1H), 7.21-7.23 (m, 1H), 7.15-7.17 (m, 2H), 7.01 (s, 1H), 6.88 (s, 1H), 5.37 (s, 2H), 5.00-5.05 (m, 1H), 3.68 (s, 4H), 3.18 (s, 3H), 2.81-3.01 (m, 4H), 2.57-2.68 (m, 4H), 1.99-2.04 (m, 1H) |
| 277 | B | 1H NMR (400 MHz, DMSO-d6): δ 11.06 (br, 1H), 10.91 (s, 1H), 8.73 (s, 1H), 8.57 (d, J = 4.4 Hz, 2H), 7.82 (d, J = 8.4 Hz, 2H), 7.56 (d, J = 7.6 Hz, 1H), 7.48 (d, J = 5.2 Hz, 2H), 7.41 (s, 1H), 7.14-7.23 (m, 3H), 7.03 (s, 1H), 6.73 (s, 1H), 5.00-5.03 (m, 1H), 4.07-4.14 (m, 2H), 3.66 (s, 4H), 3.30 (br, 4H), 2.80-3.10 (m, 5H), 2.51-2.55 (m, 2H), 1.95-2.05 (m, 1H), 0.86-0.90 (m, 2H), 0.60 (d, J = 6.8 Hz, 2H), 0.40 (d, J = 6.4 Hz, 2H) |
| 278 | B | 1H NMR (400 MHz, DMSO-d6): δ 11.06 (s, 1H), 10.93 (s, 1H), 8.73 (s, 1H), 8.64 (d, J = 4.8 Hz, 2H), 7.84 (d, J = 8.8 Hz, 2H), 7.65 (d, J = 5.6 Hz, 2H), 7.57 (d, J = 8.0 Hz, 1H), 7.43 (s, 1H), 7.24 (d, J = 8.0 Hz, 1H), 7.15 (d, J = 8.8 Hz, 2H), 7.02 (s, 1H), 6.74 (s, 1H), 5.00-5.03 (m, 1H), 3.98 (d, J = 6.4 Hz, 2H), 3.67 (s, 4H), 3.33 (br, 4H), 2.80 -3.10 (m, 5H), 2.51-2.55 (m, 2H), 1.95-2.10 (m, 2H), 1.03 (d, J = 6.8 Hz, 6H) |
| 279 | D | 1H NMR (400 MHz, DMSO-d6): δ 11.13 (s, 1H), 10.93 (s, 1H), 8.72-8.80 (m, 4H), 8.02 (s, 1H), 7.86 (d, J = 9.2 Hz, 2H), 7.83 (d, J = 5.6 Hz, 2H), 6.66 (s, 1H), 6.59 (d, J = 8.0 Hz, 1H), 7.46 (s, 1H), 7.19-7.29 (m, 3H), 5.12-5.17 (m, 1H), 4.56-4.58 (m, 1H), 3.38-3.43 (m, 8H), 3.01-3.04 (m, 2H), 2.82-2.92 (m, 3H), 2.01-2.07 (m, 2H), 1.51-1.53 (m, 1H) |
| 280 | C | 1H NMR (400 MHz, CDCl3): δ 10.88 (s, 1H), 8.72 (s, 1H), 8.57 (d, J = 6.4 Hz, 2H), 7.82 (d, J = 9.2 Hz, 2H), 7.49 (d, J = 5.2 Hz, 2H), 7.47 (s, 2H), 7.41(s, 1H), 7.34 (s, 1H), 7.21 (d, J = 8.4 Hz, 1H), 7.16-7.12(m, 3H), 5.08 (m, 1H), 3.72 (s, 4H), 3.38 (s, 4H), 3.00-2.98 (m, 2H), 2.85-2.83 (m, 2H), 2.81 (d, J = 6.4 Hz, 2H), 2.04-1.97(m, 2H) |

FIG. 3. Continued

| | | |
|---|---|---|
| 281 | | 1H NMR (400 MHz, CDCl3): δ 11.10 (s, 1H), 10.91 (s, 1H), 8.77 (s, 1H), 8.69 (s, 2H),7.85 (d, J = 9.2 Hz, 2H), 7.76 (d, J = 5.2 Hz, 2H), 7.58 (d, J = 4.4 Hz, 1H), 7.45 (s, 1H), 7.27-7.18(m, 4H), 5.12 (m, 1H), 4.58-4.56(m, 1H), 3.52 (s, 4H), 3.43 (s, 4H), 3.06-3.00 (m, 2H), 2.88-2.82 (m, 2H), 2.67-2.58(m, 2H), 2.06-1.99(m, 2H) |
| 282 | B | 1H NMR (400 MHz, DMSO-d6): δ 11.08 (s, 1H), 10.89 (s, 1H), 8.63 (s, 1H), 8.56 (s, 2H), 7.74 (d, J = 8.8 Hz, 2H), 7.70 (s, 1H), 7.55 (d, J = 8.0 Hz, 2H), 7.48 (d, J = 4.0 Hz. 2H), 7.39 (s, 1H), 7.30 (d, J = 8.0 Hz, 1H), 7.21 (d, J = 8.0 Hz, 1H), 6.57 (d, J = 8.0 Hz, 2H), 5.10-5.06 (m, 1H), 4.04 (s, 2H), 3.58 (s, 4H), 3.03 (m, 4H), 3.00-2.98 (m, 2H), 2.88-2.82 (m, 6H), 2.62-2.54 (m, 4H), 2.03-1.99 (m, 2H). |
| 283 | B | 1H NMR (400 MHz, DMSO-d6): δ 10.95 (s, 1H), 10.91 (s, 1H), 8.75 (s, 1H), 8.57 (d, J = 5.6 Hz, 2H), 7.87 (d, J = 8.8 Hz, 2H), 7.48-7.57 (m, 4H), 7.41 (s, 1H), 7.21 (d, J = 8.0 Hz, 1H), 7.14 (d, J = 8.8 Hz, 2H), 7.00-7.09 (m, 2H), 5.00-5.10 (m, 1H), 4.15-4.40 (m, 4H), 2.95-3.05 (m, 2H), 2.75-2.95 (m, 4H), 2.55-2.75 (m, 7H), 2.30-2.45 (m, 1H), 1.90-2.05 (m, 4H) |
| 284 | A | 1H NMR (400 MHz, CDCl3): δ 8.55 (br, 2H), 8.01 (s, 1H), 7.71-7.76 (m, 3H), 7.66 (d, J = 8.0 Hz, 1H), 7.52 (s, 2H), 7.34 (d, J = 8.0 Hz, 2H), 7.29 (s, 1H), 7.23-7.25 (m, 1H), 7.18 (s, 1H), 7.09 (d, J = 4.8 Hz, 1H), 5.30-5.40 (m, 2H), 4.90-5.00 (m, 1H), 4.80-4.88 (m, 1H), 3.65-3.80 (m, 1H), 3.20-3.30 (m, 1H), 2.98-3.10 (m, 4H), 2.70-2.90 (m, 4H), 2.40-2.50 (m, 2H), 2.25-2.35 (m, 4H), 2.18-2.24 (m, 2H), 2.10-2.15 (m, 2H) |
| 285 | D | 1H NMR (300 MHz, DMSO-d6): δ9.10-8.97 (m, 1H), 8.65 (d, J = 2.0 Hz, 1H), 8.60-8.53 (m, 2H), 8.10-8.07 (m, 1H), 7.70-7.56 (m, 3H), 7.51-7.21 (m, 5H), 7.18-7.07 (m, 2H), 6.18-6.12 (m, 1H), 5.38-5.21 (m, 1H), 4.44-4.31 (m, 6H), 3.78 (d, J = 8.6 Hz, 1H), 3.62-3.45 (m, 4H), 3.32-3.01(m, 8H), 2.98-2.60 (m, 4H), 2.55-2.43 (m, 3H), 2.34-1.82 (m, 6H), 0.97-0.62 (m, 6H) |
| 286 | B | 1H NMR (300 MHz, DMSO-d6): δ12.90 (brs, 1H), 9.84 (brs, 1H), 8.99-8.95 (m, 1H), 8.69-8.66 (m, 1H), 8.60-8.53 (m, 2H), 8.07 (s, 1H), 7.70-7.61 (m, 3H), 7.54-7.39 (m, 4H), 7.387.30 (m, 1H), 7.21-7.08 (m, 2H), 6.18-5.80 (m, 1H), 5.40-5.15 (m, 1H), 4.74-4.28 (m, 6H), 3.90-3.62 (m ,6H),3.41-3.22 (m, 7H), 3.21-2.81(m, 5H) 2.45-2.42(m, 3H), 2.32-2.20 (m, 1H), 2.17-1.80 (m, 4H), 0.95 (d, J = 6.5 Hz, 3H), 0.81 (d, J = 6.7 Hz, 3H) |
| 287 | A | 1H NMR (400 MHz, CD3OD): δ8.88 (d, J = 3.1 Hz, 1H), 8.70-8.68 (m, 1H), 8.60 (d, J = 2.2 Hz, 1H), 7.90 (s, 1H), 7.80-7.71 (m, 1H), 7.62-7.51 (m, 2H), 7.55-7.37 (m, 4H), 7.20-7.07 (m, 3H), 6.01 (s, 1H), 5.30-5.14 (m, 1H), 4.65-4.54 (m, 1H), 4.53-4.50 (m, 1H), 4.44-4.42 (m, 2H), 4.31-4.22 (m, 2H), 3.80-3.78 (m, 1H), 3.76-3.74 (m, 1H), 3.68-3.36 (m, 4H), 3.31-3.20 (m, 3H), 2.73-2.64 (m, 4H), 3.63-2.56 (m, 2H), 2.49-2.42 (m, 3H), 3.41-2.38 (m, 1H), 2.31 -1.94 (m, 6H), 1.40-1.31 (m, 2H), 1.10-0.87 (m, 6H) |

FIG. 3. Continued

| | | |
|---|---|---|
| 288 | | 1H NMR (400 MHz, CD3OD): δ8.88 (d, J = 2.6 Hz, 1H), 8.72-8.67 (m, 1H), 8.61 (d, J = 2.2 Hz, 1H), 7.90-7.88 (m, 1H), 7.76-7.70 (m, 5.7 Hz, 1H), 7.66-7.55 (m, 2H), 7.51-7.43 (m, 4H), 7.20-7.06 (m, 3H), 6.03-6.01 (m, 1H), 5.44-5.10 (m, 1H), 4.57-4.43 (m, 3H), 4.32-4.21 (m, 2H), 3.91-3.84 (m, 1H), 3.83-3.36 (m, 6H), 3.29-3.26 (m, 2H), 2.80-2.54 (m, 6H), 2.52-2.31 (m, 3H), 2.44-2.34 (m, 1H), 2.32-1.95 (m, 6H), 1.40-1.31 (m, 3H), 1.10-1.01 (m, 3H), 0.97-0.88 (m, 3H) |
| 289 | C | 1H NMR (400 MHz, DMSO-d6): δ 10.89 (s, 1H), 8.95 (s, 1H), 8.71 (s, 1H), 8.55-8.57 (m, 3H), 7.83 (d, J = 8.8 Hz, 2H), 7.54 (d, J = 8.4 Hz, 1H), 7.37-7.48 (m, 8H), 7.20 (d, J = 4.8 Hz, 1H), 7.09 (d, J = 9.2 Hz, 2H), 5.15 (m, 1H), 4.58 (d, J = 9.6 Hz, 1H), 4.17-4.45 (m, 6H), 4.00 (s, 2H), 3.81-3.83 (m, 2H), 3.60-3.72 (m, 6H), 2.95-3.05 (m, 2H), 2.80-2.90 (m, 2H), 2.42 (s, 3H), 1.90-2.10 (m, 2H), 0.95 (s, 9H) |
| 290 | B | 1H NMR (400 MHz, DMSO-d6): δ 10.89 (s, 1H), 8.97 (s, 1H), 8.72 (s, 1H), 8.57(m, 3H), 7.86 (d, J = 8.8 Hz, 2H), 7.49-7.57 (m, 3H), 7.39 (m, 6H), 7.09-7.12 (m, 2H), 5.17(m, 1H), 4.52-4.65 (m, 1H), 4.32-4.50 (m, 3H), 4.08-4.29(s, 4H), 3.95-4.05(m, 2H), 3.73-3.82 (m, 2H), 3.56-3.70 (m, 10H), 2.95-3.08 (m, 2H), 2.76-2.85 (s, 2H), 2.40-2.51 (m, 3H), 1.87-2.16 (s, 1H), 0.91-1.07 (s, 9H) |
| 291 | B | 1H NMR (400 MHz, DMSO-d6): δ 10.89 (s, 1H), 8.97 (s, 1H), 8.72 (s, 1H), 8.56- 8.58 (m, 3H), 7.86(d, J = 8.4 Hz, 2H), 7.49-7.57 (m, 3H), 7.39 (m, 6H), 7.22 (s, 1H), 7.09-7.12 (m, 2H), 5.17(m, 1H), 4.52-4.65 (m, 1H), 4.32-4.50 (m, 3H), 4.08-4.29(s, 4H), 3.95-4.05 (m, 2H), 3.73-3.82(m, 2H), 3.56-3.70 (m, 2H), 2.95-3.08 (m, 2H), 2.76-2.85 (s, 2H), 2.40-2.51 (m, 3H), 1.87-2.16 (s, 1H), 0.91-1.07 (s, 9H) |
| 292 | D | 1H NMR (400 MHz, DMSO-d6): δ 10.89 (s, 1H), 8.97 (s, 1H), 8.72 (s, 1H), 8.56- 8.58 (m, 3H), 7.86(d, J = 8.8 Hz, 2H), 7.49-7.57 (m, 3H), 7.39 (m, 6H), 7.22 (s, 1H), 7.09-7.12 (m, 2H), 5.17(m, 1H), 4.52-4.65 (m, 1H), 4.32-4.50 (m, 3H), 4.08-4.29(s, 4H), 3.95-4.05 (m, 2H), 3.73-3.82(m, 2H), 3.56-3.70 (m, 14H), 2.95-3.08 (m, 2H), 2.76-2.85 (s, 2H), 2.40-2.51 (m, 3H), 1.87-2.16 (s, 1H), 0.91-1.07 (s, 9H) |
| 293 | D | 1H NMR (400 MHz, DMSO-d6): δ 10.89 (s, 1H), 8.97 (s, 1H), 8.72 (s, 1H), 8.56- 8.58 (s, 3H), 7.86 (d, J = 8.8 Hz, 2H), 7.49-7.57 (m, 3H), 7.39 (m, 6H), 7.22 (s, 1H), 7.09-7.12 (m, 2H), 5.17(m, 1H), 4.52-4.65 (m, 1H), 4.32-4.29 (s, 4H), 4.08-4.29 (s, 4H), 3.95-4.05 (m, 2H), 3.73-3.82(m, 2H), 3.56-3.70 (m, 18H), 2.95-3.08 (m, 2H), 2.76-2.85 (s, 2H), 2.40-2.51 (m, 3H), 1.87-2.16 (s, 1H), 0.91-1.07 (s, 9H) |
| 294 | A | 1H NMR (400 MHz, CDCl3): δ: 11.06 (s, 1H), 10.89 (s, 1H), 8.73 (s, 1H), 8.57 (d, J = 4.8 Hz, 1H), 7.87 (d, J = 8.8 Hz, 2H), 7.65 (d, J = 8.0 Hz, 1H), 7.56 (d, J = 8.0 Hz, 1H), 7.48 (d, J = 4.8 Hz, 2H), 7.40 (s, 1H), 7.22 (d, J=8.0Hz, 1H), 7.03 (d, J = 8.8 Hz, 2H), 6.80 (s, 1H), 6.68 (d, J = 8.4 Hz, |

FIG. 3. Continued

| | |
|---|---|
| 295 | 1H), 5.02-5.07 (m, 1H), 4.96 (t, J = 2.4 Hz, 1H), 4.09 (t, J = 8.4 Hz, 2H), 3.80-3.87 (m, 4H), 3.73 (s, 1H), 3.22 (s, 4H), 3.01 (d, J = 5.2 Hz, 2H), 2.84 (d, J = 5.6 Hz, 2H), 2.01 (d, J = 9.2 Hz, 2H) |
| 298 | 1H NMR (400 MHz, CD3OD ) δ 8.87 (s, 1H), 8.69 (s, 1H), 8.58 (s, 1H), 7.89 (s, 1H), 7.73-7.72 (m, 1H), 7.58 (d, J = 8.8 Hz, 2H), 7.48-7.40 (m, 4H), 7.10-7.05 (m, 3H), 4.93 (s, 1H), 4.63 (s, 1H), 4.57 (d, J = 6 Hz, 1H), 4.52-4.50 (m, 1H), 4.38-4.34 (m, 2H), 3.87-3.86 (m, 1H), 3.82-3.81 (m, 1H), 3.57-3.50 (m, 3H), 3.36-3.33 (m, 1H), 3.31-3.20 (m, 5H), 3.02 (s, 2H), 3.01-2.90 (m, 2H), 2.56 (s, 3H), 2.74 (s, 3H), 2.26-2.20 (m, 4H), 2.10-2.01 (m, 1H), 1.82-1.71 (m, 2H), 1.67-1.61 (m, 3H), 1.44-1.28 (m, 2H), 1.05-1.02 (m, 9H) |
| 299 | 1H NMR (500 MHz, DMSO-d6) δ 12.88 (s, 1H), 9.67 (s, 1H), 8.98 (s, 1H), 8.76 – 8.50 (m, 3H), 8.23 (s, 1H), 7.98 (d, J = 9.4 Hz, 1H), 7.69 (d, J = 8.6 Hz, 2H), 7.59 (td, J = 9.0, 5.8 Hz, 1H), 7.49 – 7.34 (m, 4H), 7.33 – 7.20 (m, 1H), 7.10 (d, J = 8.7 Hz, 2H), 5.20 (d, J = 3.3 Hz, 1H), 4.72 (s, 2H), 4.62 (d, J = 9.4 Hz, 1H), 4.54 – 4.34 (m, 3H), 4.25 (dd, J = 15.9, 5.5 Hz, 1H), 3.74 – 3.59 (m, 2H), 3.19 – 3.07 (m, 2H), 2.44 (s, 3H), 2.07 (dd, J = 12.9, 7.7 Hz, 1H), 1.91 (ddd, J = 12.8, 8.8, 4.5 Hz, 1H), 1.80 – 1.65 (m, 2H), 0.96 (s, 9H), 0.94 (t, 3H). 13C NMR (151 MHz, dmso) δ 180.62, 171.82, 169.13, 167.11, 157.51, 156.02 (dd, J = 246.1, 7.0 Hz), 152.34 (dd, J = 249.6, 8.5 Hz), 151.45, 148.60, 147.74, 143.80, 139.47, 138.70, 131.16, 129.70, 129.00 – 128.42 (m), 128.81, 128.69, 128.31, 128.00, 127.48, 126.53, 121.96 (dd, J = 13.6, 3.5 Hz), 118.61 – 117.85 (m), 117.53, 115.63, 115.34, 112.34 (dd, J = 22.4, 3.4 Hz), 68.91, 66.58, 58.80, 56.17, 53.45, 41.69, 37.95, 35.79, 26.28, 16.85, 15.96, 12.63 |
| 299 | 1H NMR (500 MHz, DMSO-d6) δ 12.97 (bs, 1H), 9.72 (bs, 1H), 8.97 (s, 1H), 8.71 (d, J = 2.1 Hz, 1H), 8.61 (s, 2H), 8.56 (t, J = 6.0 Hz, 2H), 8.23 (s, 1H), 7.99 (d, J = 9.3 Hz, 1H), 7.59 (td, J = 9.0, 5.9 Hz, 1H), 7.50 – 7.16 (m, 8H), 6.98 (d, J = 8.2 Hz, 1H), 5.13 (d, J = 3.4 Hz, 1H), 4.58 (d, J = 9.3 Hz, 1H), 4.48 – 4.40 (m, 2H), 4.35 (s, 1H), 4.22 (dd, J = 15.9, 5.5 Hz, 1H), 4.08 (ddt, J = 9.6, 7.1, 3.2 Hz, 2H), 3.74 – 3.62 (m, 2H), 3.15 – 3.06 (m, 2H), 2.50 – 2.45 (m, 1H), 2.44 (s, 3H), 2.41 – 2.33 (m, 1H), 2.09 – 1.86 (m, 4H), 1.79 – 1.67 (m, 2H), 0.97 (t, 3H), 0.94 (s, 9H). 13C NMR (151 MHz, dmso) δ 181.05, 172.38, 172.05, 170.09, 159.63, 156.44 (dd, J = 246.5, 6.8 Hz), 152.74 (dd, J = 249.6, 8.6 Hz), 151.86, 149.36, 148.13, 140.05, 139.92, 139.24, 131.87, 131.59, 130.71, 130.05, 129.20 (t, J = 5.0 Hz), 129.06, 127.84, 127.52, 122.37 (dd, J = 13.5, 3.5 Hz), 119.87, 118.95 – 118.24 (m), 117.88, 116.11, 114.12, 113.60, 112.91 – 112.65 (m), 69.32, 67.53, 59.14, 56.88, 56.83, 53.86, 42.08, 38.38, 35.67, 31.76, 26.80, 25.52, 17.26, 16.37, 13.04 |
| 300 | 1H NMR (400 MHz, DMSO-d6) δ 12.95 (bs, 1H), 9.74 (bs, 1H), 8.91 (s, 1H), 8.67 (d, J = 2.0 Hz, 1H), 8.55 (dd, J = 12.8, 6.8 Hz, 2H), 8.19 (s, 1H), 7.56 (td, J = 9.0, 6.0 Hz, 1H), 7.49 (d, J = 9.5 Hz, 1H), 7.42 – 7.20 (m, 8H), 7.07 – 7.00 (m, 1H), 5.13 (d, J = 3.5 Hz, 1H), 4.58 (d, J = 9.6 Hz, 1H), |

FIG. 3. Continued

| | |
|---|---|
| 301 | 4.44 (t, J = 8.1 Hz, 1H), 4.36 (dd, J = 15.8, 6.2 Hz, 2H), 4.30 – 4.16 (m, 3H), 4.06 (s, 2H), 3.86 (t, J = 4.3 Hz, 2H), 3.13 – 3.04 (m, 2H), 2.37 (s, 3H), 2.07 – 1.99 (m, 1H), 1.94 – 1.83 (m, 1H), 1.78 – 1.64 (m, 2H), 0.94 (t, 3H), 0.93 (s, 9H). 13C NMR (126 MHz, dmso) δ 181.03, 172.20, 169.60, 168.98, 159.52, 156.46 (dd, J = 246.7, 7.1 Hz), 152.75 (dd), 151.81, 149.36, 148.14, 144.59, 140.08, 139.80, 139.21, 131.85, 131.56, 130.66, 130.08, 129.62 – 128.89 (m), 129.08, 127.82, 122.38 (dd, J = 13.5, 3.6 Hz),, 120.09, 118.98 – 118.30 (m), 117.89, 116.15, 114.40, 113.50, 112.78 (dd, J = 22.9, 3.8 Hz), 70.05, 70.00, 69.34, 67.49, 59.18, 57.04, 56.16, 53.89, 42.12, 38.34, 36.22, 26.65, 17.28, 16.32, 13.05 |
| 302 | 1H NMR (400 MHz, DMSO-d6) δ 12.91 (bs, 1H), 9.79 (s, 1H), 8.97 (s, 1H), 8.65 (d, J = 2.2 Hz, 1H), 8.62 – 8.47 (m, 2H), 8.15 (s, 1H), 8.06 – 7.89 (m, 2H), 7.67 (d, J = 8.7 Hz, 2H), 7.40 (dd, J = 8.3, 4H), 7.23 (t, J = 8.8 Hz, 1H), 7.07 (d, J = 8.8 Hz, 2H), 5.14 (d, J = 3.5 Hz, 1H), 4.58 (d, J = 9.3 Hz, 1H), 4.49 – 4.40 (m, 2H), 4.37 (bs, 1H), 4.22 (dd, J = 15.9, 5.4 Hz, 1H), 4.03 (t, J = 7.2 Hz, 2H), 3.77 – 3.62 (m, 2H), 2.44 (s, 3H), 2.43 – 2.30 (m, 4H), 2.09 – 1.87 (m, 4H), 1.61 (h, J = 7.4 Hz, 2H), 0.96 (s, 9H), 0.92 (t, J = 7.4 Hz, 3H). 13C NMR (151 MHz, dmso) δ 180.92, 171.97, 171.67, 171.61, 169.68, 158.33, 154.61 (dd, J = 244.6, 7.1 Hz), 151.44, 150.34 (dd, J = 248.8, 8.2 Hz), 148.52, 147.72, 143.71, 139.52, 138.48, 131.17, 130.42, 129.64, 128.65, 128.28, 127.43, 126.50, 126.06 (d, J = 10.1 Hz), 123.23 (dd, J = 12.4, 3.6 Hz), 118.47 – 117.44 (m), 117.55, 115.65, 115.18, 111.60 (d, J = 25.0 Hz), 68.92, 67.13, 58.74, 56.48, 56.42, 41.67, 37.99, 37.57, 35.26, 31.32, 26.41, 25.07, 18.56, 15.96, 13.57 |
| 303 | 1H NMR (500 MHz, DMSO-d6) δ 12.68 (bs, 1H), 8.97 (s, 1H), 8.64 (d, J = 2.2 Hz, 1H), 8.61 – 8.47 (m, 2H), 8.06 (s, 1H), 8.00 (d, J = 9.3 Hz, 1H), 7.65 (d, J = 8.6 Hz, 2H), 7.40 (dd, 4H), 7.07 (d, J = 8.7 Hz, 2H), 6.99 – 6.82 (m, 2H), 5.21 (s, 2H), 5.15 (d, J = 3.6 Hz, 1H), 4.58 (d, J = 9.3 Hz, 1H), 4.50 – 4.40 (m, 2H), 4.37 (bs, 1H), 4.23 (dd, J = 15.8, 5.3 Hz, 1H), 4.10 – 3.93 (m, 2H), 3.78 – 3.54 (m, 2H), 2.58 – 2.26 (m, 2H), 2.44 (s, 3H), 2.11 – 1.82 (m, 4H), 0.94 (s, 9H). 13C NMR (126 MHz, dmso) δ 182.20, 171.97, 171.63, 169.69, 158.31, 151.43.149.20 (dd, J = 234.8, 6.5 Hz), 148.45, 147.72, 146.01 (dd, J = 241.2, 7.9 Hz), 143.55, 139.51, 137.92, 133.42 (dd, J = 12.9, 2.4 Hz), 131.18, 130.49, 129.65, 128.65, 128.24, 127.44, 126.47, 118.32 – 117.22 (m), 117.57, 116.91 – 116.23 (m), 115.84, 115.19, 111.36 (dd, J = 22.3, 2.9 Hz), 68.92, 67.14, 58.74, 56.50, 56.41, 41.68, 37.97, 35.25, 31.33, 26.41, 25.07, 15.95 |
| | 1H NMR (500 MHz, DMSO-d6) δ 12.89 (bs, 1H), 8.97 (s, 1H), 8.65 (d, J = 1.9 Hz, 1H), 8.62 – 8.54 (m, 2H), 8.13 (s, 1H), 8.00 (d, J = 9.3 Hz, 1H), 7.75 – 7.55 (m, 3H), 7.43 (d, J = 8.1 Hz, 3H), 7.38 (d, J = 8.1 Hz, 2H), 7.28 (t, J = 7.9 Hz, 2H), 7.07 (d, J = 8.6 Hz, 2H), 5.15 (d, J = 3.3 Hz, 1H), 4.59 (d, J = 9.3 Hz, 1H), 4.49 – 4.40 (m, 2H), 4.39 – 4.33 (m, 1H), 4.23 (dd, J = 15.9, 5.4 Hz, 1H), |

FIG. 3. Continued

| | |
|---|---|
| | 4.09 – 3.97 (m, 2H), 3.77 – 3.61 (m, 2H), 1H NMR (500 MHz, DMSO-d6) δ 2.48 – 2.31 (m, 2H), 2.44 (s, 3H), 2.11 – 1.86 (m, 4H), 0.96 (s, 9H). 13C NMR (151 MHz, dmso) δ 181.30, 171.97, 171.61, 169.68, 158.80 (dd, J = 247.2, 7.9 Hz), 158.33, 151.44, 148.52, 147.72, 143.70, 139.51, 138.38, 132.14 (t, J = 9.9 Hz), 131.30, 131.17, 130.44, 129.64, 128.64, 128.27, 127.43, 126.48, 117.76 (t, J = 23.3 Hz), 117.54, 115.78, 115.18, 112.29 (dd, J = 21.0, 4.2 Hz), 68.92, 67.13, 58.74, 56.48, 56.42, 41.67, 37.98, 35.26, 31.32, 26.41, 25.06, 15.96 |
| 304 | 1H NMR (500 MHz, DMSO-d6) δ 12.66 (bs, 1H), 9.73 (bs, 1H), 8.96 (s, 1H), 8.61 – 8.50 (m, 1H), 8.25 (s, 1H), 8.00 (s, 1H), 7.93 (bs, 1H), 7.88 (d, J = 9.1 Hz, 1H), 7.63 – 7.49 (m, 1H), 7.40 (dd, 4H), 7.25 (t, J = 8.7 Hz, 1H), 5.14 (s, 1H), 4.56 (d, J = 9.1 Hz, 1H), 4.46 – 4.34 (m, 3H), 4.22 (dd, J = 15.8, 4.7 Hz, 1H), 3.75 – 3.60 (m, 2H), 3.23 – 3.14 (m, 4H), 3.13 – 3.08 (m, 2H), 2.65 – 2.53 (m, 4H), 2.43 (s, 3H), 2.38 – 2.31 (m, 2H), 2.31 – 2.25 (m, 1H), 2.24 – 2.16 (m, 1H), 2.07 – 1.99 (m, 1H), 1.95 – 1.87 (m, 1H), 1.72 (dq, J = 16.3, 10.5, 8.9 Hz, 4H), 0.95 (t, J = 5.3 Hz, 3H), 0.95 (s, 9H). 13C NMR (151 MHz, DMSO-d6) δ 180.77, 172.43, 172.39, 170.12, 156.38 (dd, J = 246.2, 7.1 Hz), 152.75 (dd, J = 249.8, 9.0 Hz), 151.87, 148.13, 145.23, 144.35, 139.92, 138.09, 137.78, 131.59, 130.05, 129.21 – 128.76 (m), 127.84, 122.32 (d, J = 13.1 Hz), 119.83 – 118.25 (m), 118.03, 115.53, 114.96, 112.68 (d, J = 22.7 Hz), 69.30, 59.13, 57.62, 56.79, 55.33, 53.88, 53.06, 50.11, 42.07, 38.38, 35.68, 33.27, 26.83, 23.09, 17.26, 16.37, 13.04 |
| 305 | 1H NMR (400 MHz, DMSO-d6) δ 12.70 (s, 1H), 8.97 (s, 1H), 8.68 (d, J = 2.2 Hz, 1H), 8.62 (d, J = 2.3 Hz, 1H), 8.60 – 8.51 (m, 1H), 8.12 (s, 1H), 8.00 (d, J = 9.3 Hz, 1H), 7.90 – 7.77 (m, 1H), 7.72 – 7.51 (m, 5H), 7.48 – 7.29 (m, 4H), 7.07 (d, J = 8.7 Hz, 2H), 5.15 (d, J = 3.5 Hz, 1H), 4.59 (d, J = 9.3 Hz, 1H), 4.50 – 4.32 (m, 3H), 4.22 (dd, J = 15.9, 5.4 Hz, 1H), 4.03 (td, J = 6.5, 2.6 Hz, 2H), 3.80 – 3.60 (m, 2H), 2.44 (s, 3H), 2.48 – 2.28 (m, 5H), 2.13 – 1.84 (m, 4H), 0.96 (s, 9H). 13C NMR (101 MHz, dmso) δ 189.87, 172.00, 171.63, 169.69, 158.23, 151.48, 148.29, 147.73, 143.29, 139.64, 139.53, 136.54, 131.52, 131.19, 130.74, 129.65, 128.66, 128.58, 128.55, 128.21, 127.44, 127.05, 118.81, 115.19, 113.74, 68.93, 67.13, 58.75, 56.47, 48.64, 41.68, 38.01, 35.29, 31.33, 26.43, 25.08, 15.99 |
| 306 | 1H NMR (500 MHz, DMSO-d6) δ 12.66 (bs, 1H), 9.72 (bs, 1H), 8.93 (s, 1H), 8.59 (bs, 1H), 8.22 (s, 1H), 7.99 (s, 1H), 7.89 (bs, 1H), 7.56 (dh, J = 9.1, 3.4, 2.9 Hz, 1H), 7.51 – 7.31 (m, 5H), 7.25 (t, J = 8.6 Hz, 1H), 5.17 (s, 1H), 4.57 (dd, J = 9.7, 2.4 Hz, 1H), 4.50 – 4.33 (m, 3H), 4.28 – 4.19 (m, 1H), 4.07 – 3.92 (m, 2H), 3.65 (d, J = 15.4 Hz, 4H), 3.22 – 3.05 (m, 6H), 2.64 (d, J = 21.6 Hz, 6H), 2.42 (s, 3H), 2.11 – 2.03 (m, 1H), 1.91 (dd, J = 13.3, 5.8 Hz, 1H), 1.80 – 1.67 (m, 2H), 0.96 (s/t overlapping, 12H). 13C NMR (151 MHz, DMSO-d6) δ 180.38, 171.80, 169.18, 168.58, 156.01 (dd, J = 246.2, 6.8 Hz), 152.34 (dd, J = 249.1, 8.7 Hz), 151.39, 147.73, 144.79, 143.97, 139.43, |

FIG. 3. Continued

| |
|---|
| 137.73, 137.38, 131.16, 129.70, 128.68, 128.60 (d), 127.47, 121.93 (dd, J = 13.8, 3.7 Hz), 118.89 – 118.05 (m), 117.64, 115.15, 114.62, 112.29 (dd, J = 22.2, 3.2 Hz), 69.65, 68.94, 68.76, 58.81, 57.13, 56.64, 55.73, 53.09, 49.72, 41.71, 37.93, 35.87, 26.24, 16.88, 15.95, 12.65 |

$DC_{50}$ Categories: A: <10
B: <=50 and >=10
C: <=100 and >50
D: >100

Dmax Categories: A: <50
B: <=70 and >=50
C: >70

COMPOUNDS AND METHODS FOR THE TARGETED DEGRADATION OF RAPIDLY ACCELERATED FIBROSARCOMA POLYPEPTIDES

CROSS-REFERENCE TO RELATED APPLICATIONS

The present disclosure claims priority to U.S. Provisional Application No. 62/438,803, filed 23 Dec. 2016 and U.S. Provisional Application No. 62/582,698, filed 7 Nov. 2017, both of which are incorporated herein by reference in their entirities.

INCORPORATION BY REFERENCE

U.S. patent application Ser. No. 15/230,354, filed on Aug. 5, 2016; and U.S. patent application Ser. No. 15/206,497 filed 11 Jul. 2016; and U.S. patent application Ser. No. 15/209,648 filed 13 Jul. 2016; and U.S. Patent Application Ser. No. 62/406,888, filed on Oct. 11, 2016; and U.S. patent application Ser. No. 14/686,640, filed on Apr. 14, 2015, published as U.S. Patent Application Publication No. 2015/0291562; and U.S. patent application Ser. No. 14/792,414, filed on Jul. 6, 2015, published as U.S. Patent Application Publication No. 2016/0058872; and U.S. patent application Ser. No. 14/371,956, filed on Jul. 11, 2014, published as U.S. Patent Application Publication No. 2014/0356322; and U.S. patent application Ser. No. 15/074,820, filed on Mar. 18, 2016, published as U.S. Patent Application Publication No. 2016/0272639, are incorporated herein by reference in their entirety. Furthermore, all references cited herein are incorporated by reference herein in their entirety.

STATEMENT REGARDING FEDERALLY FUNDED RESEARCH

This invention was made with government support under grant number NIH R35CA197589, as issued by the National Institutes of Health. The government has certain rights in the invention.

FIELD OF THE INVENTION

The description provides bifunctional compounds comprising a target protein binding moiety and an E3 ubiquitin ligase binding moiety, and associated methods of use. The bifunctional compounds are useful as modulators of targeted ubiquitination, especially with respect to Rapidly Accelerated Fibrosarcoma (RAF) proteins, which are degraded and/or otherwise inhibited by bifunctional compounds according to the present disclosure.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of nutlins, the first small molecule E3 ligase inhibitors, additional compounds have been reported that target E3 ligases but the field remains underdeveloped. For example, since the discovery of Nutlins, the first small molecule E3 ligase mouse double minute 2 homolog (MDM2) inhibitors, additional compounds have been reported that target MDM2 (i.e., human double minute 2 or HDM2) E3 ligases (J. Di, et al. *Current Cancer Drug Targets* (2011), 11(8), 987-994).

Tumor suppressor gene p53 plays an important role in cell growth arrest and apoptosis in response to DNA damage or stress (A. Vazquez, et al. *Nat. Rev. Drug. Dis.* (2008), 7, 979-982), and inactivation of p53 has been suggested as one of the major pathway for tumor cell survival (A. J. Levine, et al. *Nature* (2000), 408, 307-310). In cancer patients, about 50% were found with p53 mutation (M. Hollstein, et al. *Science* (1991), 233, 49-53), while patients with wild type p53 were often found p53 down regulation by MDM2 through the protein-protein interaction of p53 and MDM2 (P. Chene, et al. *Nat. Rev. Cancer* (2003), 3, 102-109). Under normal cell condition without oncogenic stress signal, MDM2 keeps p53 at low concentration. In response to DNA damage or cellular stress, p53 level increases, and that also causes increase in MDM2 due to the feedback loop from p53/MDM2 auto regulatory system. In other words, p53 regulates MDM2 at the transcription level, and MDM2 regulates p53 at its activity level (A. J. Levine, et al. *Genes Dev.* (1993) 7, 1126-1132).

Several mechanisms can explain p53 down regulation by MDM2. First, MDM2 binds to N-terminal domain of p53 and blocks expression of p53-responsive genes (J. Momand, et al. *Cell* (1992), 69, 1237-1245). Second, MDM2 shuttles p53 from nucleus to cytoplasm to facilitate proteolytic degradation (J. Roth, et al. *EMBO J.* (1998), 17, 554-564). Lastly, MDM2 carries intrinsic E3 ligase activity of conjugating ubiquitin to p53 for degradation through ubiquitin-dependent 26s proteasome system (UPS) (Y. Haupt, et al. *Nature* (1997) 387, 296-299). As such, because MDM2 functions as E3 ligase, recruiting MDM2 to a disease causing protein and effectuating its ubiquitination and degradation is an approach of high interest for drug discovery.

One E3 ligase with exciting therapeutic potential is the von Hippel-Lindau (VHL) tumor suppressor, the substrate recognition subunit of the E3 ligase complex VCB, which also consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. The first small molecule ligands of Von Hippel Lindau (VHL) to the substrate recognition subunit of the E3 ligase were generated, and crystal structures were obtained confirming that the compound mimics the binding mode of the transcription factor HIF-1α, the major substrate of VHL.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Inhibitors of Apotosis Proteins (IAPs) are a protein family involved in suppressing apoptosis, i.e. cell death. The human IAP family includes 8 members, and numerous other organisms contain IAP homologs. IAPs contain an E3 ligase specific domain and baculoviral IAP repeat (BIR) domains that recognize substrates, and promote their ubiquitination. IAPs promote ubiquitination and can directly bind and inhibit caspases. Caspases are proteases (e.g. caspase-3, caspase-7 and caspace-9) that implement apoptosis. As such, through the binding of caspases, IAPs inhibit cell death. However, pro-apoptotic stimuli can result in the release of mitochondrial proteins DIABLO (also known as second mitrochondria-derived activator of caspases or SMAC) and HTRA2 (also known as Omi). Binding of DIABLO and HTRA2 appears to block IAP activity.

SMAC interacts with essentially all known IAPB including XIAP, c-IAP1, c-IAP2, NIL-IAP, Bruce, and survivin. The first four amino acids (AVPI) of mature SMAC bind to a portion of IAPs, which is believed to be essential for blocking the anti-apoptotic effects of IAPs.

Bifunctional compounds such as those that are described in U.S. Patent Application Publications 2015-0291562 and 2014-0356322 (incorporated herein by reference), function to recruit endogenous proteins to an E3 ubiquiuin ligase for degradation. In particular, the publications describe bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds.

An ongoing need exists in the art for effective treatments for disease associated with overexpression or aggregation of Rapidly Accelerated Fibrosarcoma (RAF), or the overactivation of RAF (such as constitutively active RAF). For example, current BRaf inhibitors (such as, vemurafenib and dabrafenib) only target V600 mutant BRaf. Thus, a need exists for diseases or disorders (such as, melanoma, lung cancer, pancreatic cancer, and/or colorectal cancers) that have different BRaf mutations that are insensitive to currently marketed agents. Furthermore, resistance mutations can emerge in response to BRaf/MEK inhibitor therapy. For example, the p61 splice variant can emerge in melanoma patients treated with BRaf/MEK inhibitor therapy, which leaves these patients with no clinical options. Currently marketed agents also bind to and cause paradoxical activation of wild-type BRaf, which results in clinical complications. In addition, the family of hypoactive Class III BRaf mutants that signal through heterodimerization with CRaf, constitute 40% of BRaf mutations in non-small cell lung cancer (NSCLC), and also appear sporadically across other cancers, cannot be targeted with any currently approved or clinical-stage BRaf inhibitors.

Thus, non-specific effects and the inability to target and modulate RAF, remain an obstacle to the development of effective treatments. As such, small-molecule therapeutic agents that effectively targets RAF (e.g., effectively inhibiting and/or degrading mutant forms of BRaf, while sparing wild-type BRaf) and that leverage or potentiate VHL's, cereblon's, MDM2's, and IAPs' substrate specificity would be very useful.

SUMMARY

The present disclosure describes bifunctional compounds which function to recruit endogenous proteins to an E3 ubiquitin ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer (e.g., renal cell carcinoma, pancreatic cancer, colorectal cancer, lung cancer, ovarian cancer, thyroid cancer, pilocytic astrocytoma, prostate cancer, gastric cancer, hepatocellular carcinoma, and melanoma), cardiofaciocutaneous syndrome, neurofibromatosis type 1, Costello syndrome, Noonan Syndrome, LEOPARD (Lentigo, Electrocardiographic abnormalities, Ocular hypertelorism, Pulmonary stenosis, Abnormal genitalia, Retarded growth, Deafness) syndrome.

As such, in one aspect the disclosure provides bifunctional or PROTAC compounds, which comprise an E3 ubiquitin ligase binding moiety (i.e., a ligand for an E3 ubiquitin ligase or "ULM" group), and a moiety that binds a target protein (i.e., a protein/polypeptide targeting ligand or "PTM" group) such that the target protein/polypeptide is placed in proximity to the ubiquitin ligase to effect degradation (and inhibition) of that protein. In a preferred embodiment, the ULM (ubiquitination ligase modulator) can be Von Hippel-Lindau E3 ubiquitin ligase (VHL) binding moiety (VLM), or a cereblon E3 ubiquitin ligase binding moiety (CLM), or a mouse double miniute 2 homolog (MDM2) E3 ubiquitin ligase binding moiety (MLM), or an IAP E3 ubiquitin ligase binding moiety (i.e., a "ILM"). For example, the structure of the bifunctional compound can be depicted as:

The respective positions of the PTM and ULM moieties (e.g., VLM, CLM, MLM or ILM) as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as:

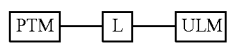

where PTM is a protein/polypeptide targeting moiety, L is a linker, e.g., a bond or a chemical group coupling PTM to ULM, and ULM is a IAP E3 ubiquitin ligase binding moiety, or a Von Hippel-Lindau E3 ubiquitin ligase (VHL) binding moiety (VLM), or a cereblon E3 ubiquitin ligase binding moiety (CLM), or a mouse double minute 2 homolog (MDM2) E3 ubiquitin ligase binding moiety (MLM).

For example, the structure of the bifunctional compound can be depicted as:

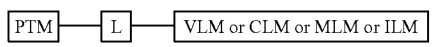

wherein: PTM is a protein/polypeptide targeting moiety; "L" is a linker (e.g. a bond or a chemical linker group) coupling the PTM and at least one of VLM, CLM, MLM, ILM, or a combination thereof; VLM is Von Hippel-Lindau E3 ubiquitin ligase binding moiety that binds to VHL E3 ligase; CLM is cereblon E3 ubiquitin ligase binding moiety that binds to cereblon; MLM is an MDM2 E3 ubiquitin ligase binding moiety; and ILM is a IAP binding moiety which binds to IAP.

In certain preferred embodiments, the ILM is an AVPI tetrapeptide fragment. As such, in certain additional embodiments, the ILM of the bifunctional compound comprises the amino acids alanine (A), valine (V), proline (P), and isoleucine (I) or their unnatural mimetics, respectively. In additional embodiments, the amino acids of the AVPI tetrapeptide fragment are connected to each other through amide bonds (i.e., —C(O)NH— or —NHC(O)—).

In certain embodiments, the compounds as described herein comprise multiple independently selected ULMs, multiple PTMs, multiple chemical linkers or a combination thereof.

In certain embodiments, ILM comprises chemical moieties such as those described herein.

In additional embodiments, VLM can be hydroxyproline or a derivative thereof. Furthermore, other contemplated VLMs are included in U.S. Patent Application Publication No. 2014/03022523, which as discussed above, is incorporated herein in its entirety.

In an embodiment, the CLM comprises a chemical group derived from an imide, a thioimide, an amide, or a thioamide. In a particular embodiment, the chemical group is a phthalimido group, or an analog or derivative thereof. In a certain embodiment, the CLM is thalidomide, lenalidomide, pomalidomide, analogs thereof, isosteres thereof, or derivatives thereof. Other contemplated CLMs are described in U.S. Patent Application Publication No. 2015/0291562, which is incorporated herein in its entirety.

In certain embodiments, MLM can be nutlin or a derivative thereof. Furthermore, other contemplated MLMs are included in U.S. patent application Ser. No. 15/206,497 filed 11 Jul. 2016, which as discussed above, is incorporated herein in its entirety. In certain additional embodiments, the MLM of the bifunctional compound comprises chemical moieties such as substituted imidazolines, substituted spiroindolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In certain embodiments, "L" is a bond. In additional embodiments, the linker "L" is a connector with a linear non-hydrogen atom number in the range of 1 to 20. The connector "L" can contain, but not limited to the functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic and tricyclic moieties. Substitution with halogen, such as Cl, F, Br and I can be included in the linker. In the case of fluorine substitution, single or multiple fluorines can be included.

In certain embodiments, VLM is a derivative of trans-3-hydroxyproline, where both nitrogen and carboxylic acid in trans-3-hydroxyproline are functionalized as amides.

In certain embodiments, CLM is a derivative of piperidine-2,6-dione, where piperidine-2,6-dione can be substituted at the 3-position, and the 3-substitution can be bicyclic hetero-aromatics with the linkage as C—N bond or C—C bond. Examples of CLM can be, but not limited to, pomalidomide, lenalidomide and thalidomide and their derivatives.

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer. In yet another aspect, the present disclosure provides a method of ubiquitinating/degrading a target protein in a cell. In certain embodiments, the method comprises administering a bifunctional compound as described herein comprising an ILM and a PTM, a PTM and a VLM, or a PTM and a CLM, or a PTM and a MLM, preferably linked through a linker moiety, as otherwise described herein, wherein the VLM/ILM/CLM/MLM is coupled to the PTM through a linker to target protein that binds to PTM for degradation. Similarly, the PTM can be coupled to VLM or CLM or MLM or ILM through a linker to target a protein or polypeptide for degradation. Degradation of the target protein will occur when the target protein is placed in proximity to the E3 ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In still another aspect, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present disclosure.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional aspects and embodiments are expressly included within the scope of the present disclosure. The publications and other materials used herein to illuminate the background of the disclosure, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating an embodiment of the disclosure and are not to be construed as limiting the disclosure. Further objects, features and advantages of the disclosure will become apparent from the following detailed description taken in conjunction with the accompanying figures showing illustrative embodiments of the disclosure, in which:

FIG. 3. Table 43. Data of exemplary protein targeting moieties and compounds of the present disclosure.

DETAILED DESCRIPTION

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Figures 1A, 1B:
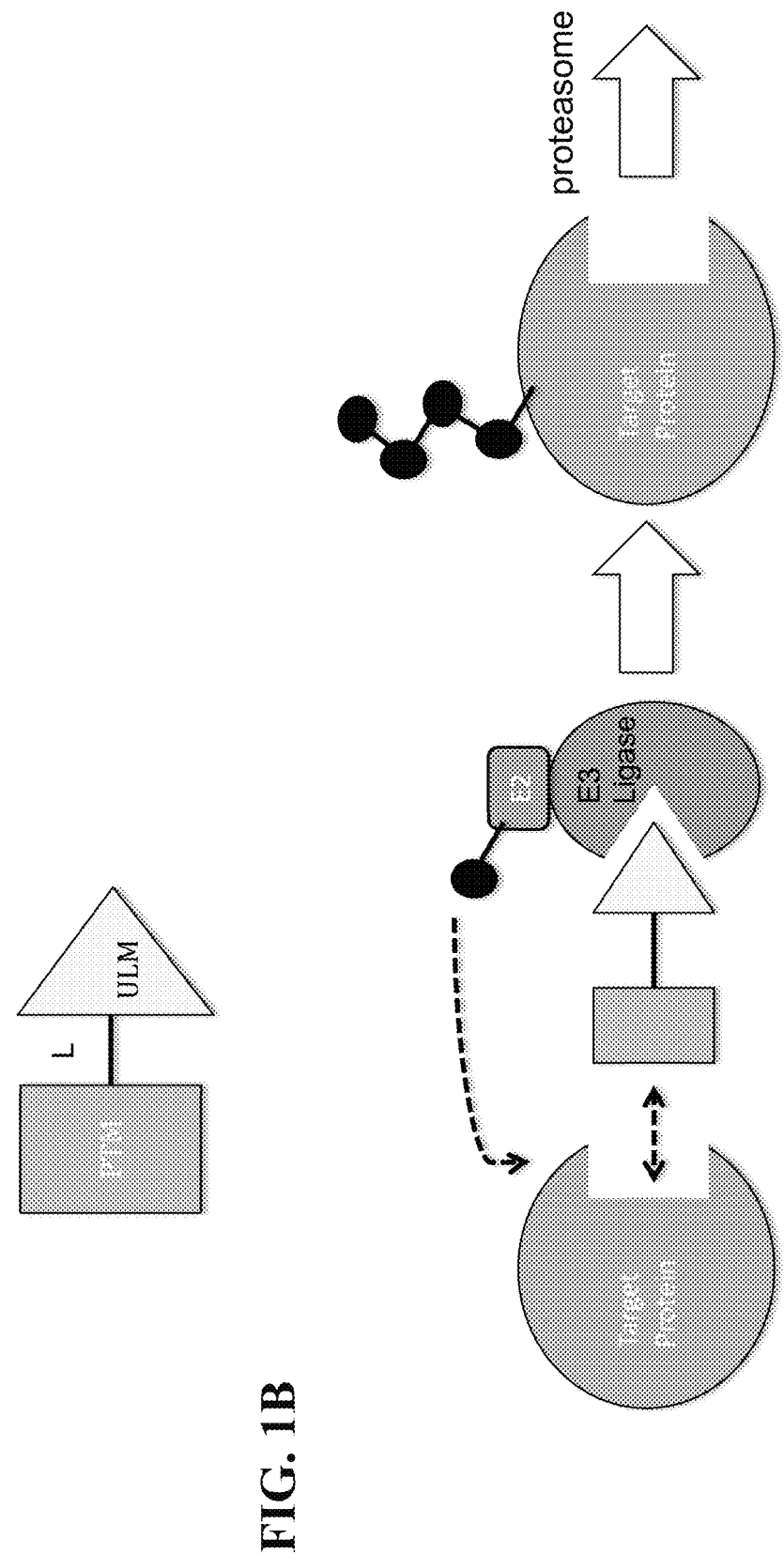
FIGS. 1A and 1B. Illustration of general principle for PROTAC function. (A) Exemplary PROTACs comprise a protein targeting moiety (PTM; darkly shaded rectangle), a ubiquitin ligase binding moiety (ULM; lightly shaded triangle), and optionally a linker moiety (L; black line) coupling or tethering the PTM to the ULM. (B) Illustrates the functional use of the PROTACs as described herein. Briefly, the ULM recognizes and binds to a specific E3 ubiquitin ligase, and the PTM binds and recruits a target protein bringing it into close proximity to the E3 ubiquitin ligase. Typically, the E3 ubiquitin ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degradation by the proteosomal machinery of the cell.

Presently described are compositions and methods that relate to the surprising and unexpected discovery that an E3 ubiquitin ligase protein (e.g., inhibitors of apoptosis proteins (IAP), a Von Hippel-Lindau E3 ubiquitin ligase (VHL), a cereblon E3 ubiquitin ligase, or a mouse double minute 2 homolog (MDM2) E3 ubiquitin ligase) ubiquitinates a target protein once it and the target protein are placed in proximity by a bifunctional or chimeric construct that binds the E3 ubiquitin ligase protein and the target protein. Accordingly the present disclosure provides such compounds and compositions comprising an E3 ubiquintin ligase binding moiety ("ULM") coupled to a protein target binding moiety ("PTM"), which result in the ubiquitination of a chosen target protein, which leads to degradation of the target protein by the proteasome (see FIG. 1). The present disclosure also provides a library of compositions and the use thereof.

In certain aspects, the present disclosure provides compounds which comprise a ligand, e.g., a small molecule ligand (i.e., having a molecular weight of below 2,000, 1,000, 500, or 200 Daltons), which is capable of binding to a ubiquitin ligase, such as IAP, VHL, MDM2, or cereblon. The compounds also comprise a moiety that is capable of binding to target protein, in such a way that the target protein is placed in proximity to the ubiquitin ligase to effect degradation (and/or inhibition) of that protein. Small molecule can mean, in addition to the above, that the molecule is non-peptidyl, that is, it is not generally considered a peptide, e.g., comprises fewer than 4, 3, or 2 amino acids. In accordance with the present description, the PTM, ULM or PROTAC molecule can be a small molecule.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or"

as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented or understood within the context of the compound shown and well-known rules for valence interactions.

The term "ubiquitin ligase" refers to a family of proteins that facilitate the transfer of ubiquitin to a specific substrate protein, targeting the substrate protein for degradation. For example, TAP an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

Compounds and Compositions

In one aspect, the description provides compounds comprising an E3 ubiquitin ligase binding moiety ("ULM") that is an IAP E3 ubiquitin ligase binding moiety (an "ILM"), a cereblon E3 ubiquitin ligase binding moiety (a "CLM"), a Von Hippel-Lindae E3 ubiquitin ligase (VHL) binding moiety (VLM), and/or a mouse double minute 2 homologue (MDM2) E3 ubiquitin ligase binding moiety (MLM). In an exemplary embodiment, the ULM is coupled to a target protein binding moiety (PTM) via a chemical linker (L) according to the structure:

(A) PTM-L-ULM wherein L is a bond or a chemical linker group, ULM is a E3 ubiquitin ligase binding moiety, and PTM is a target protein binding moiety. The number and/or relative positions of the moieties in the compounds illustrated herein is provided by way of example only. As would be understood by the skilled artisan, compounds described herein can be synthesized with any desired number and/or relative position of the respective functional moieties.

The terms ULM, ILM, VLM, MLM, and CLM are used in their inclusive sense unless the context indicates otherwise. For example, the term ULM is inclusive of all ULMs, including those that bind IAP (i.e., ILMs), MDM2 (i.e., MLM), cereblon (i.e., CLM), and VHL (i.e., VLM). Further, the term ILM is inclusive of all possible IAP E3 ubiquitin ligase binding moieties, the term MLM is inclusive of all possible MDM2 E3 ubiquitin ligase binding moieties, the term VLM is inclusive of all possible VHL binding moieties, and the term CLM is inclusive of all cereblon binding moieties.

In another aspect, the present disclosure provides bifunctional or multifunctional compounds (e.g., PROTACs) useful for regulating protein activity by inducing the degradation of a target protein. In certain embodiments, the compound comprises an ILM or a VLM or a CLM or a MLM coupled, e.g., linked covalently, directly or indirectly, to a moiety that binds a target protein (i.e., a protein targeting moiety or a "PTM"). In certain embodiments, the ILM/VLM/CLM/MLM and PTM are joined or coupled via a chemical linker (L). The ILM binds the IAP E3 ubiquitin ligase, the VLM binds VHL, CLM binds the cereblon E3 ubiquitin ligase, and MLM binds the MDM2 E3 ubiquitin ligase, and the PTM recognizes a target protein and the interaction of the respective moieties with their targets facilitates the degradation of the target protein by placing the target protein in proximity to the ubiquitin ligase protein. An exemplary bifunctional compound can be depicted as:

(B) PTM-ILM
(C) PTM-CLM
(D) PTM-VLM
(E) PTM-MLM

In certain embodiments, the bifunctional compound further comprises a chemical linker ("L"). For example, the bifunctional compound can be depicted as:

(F) PTM-L-ILM
(G) PTM-L-CLM
(H) PTM-L-VLM
(I) PTM-L-MLM wherein the PTM is a protein/polypeptide targeting moiety, the L is a chemical linker, the ILM is a IAP E3 ubiquitin ligase binding moiety, the CLM is a cereblon E3 ubiquitin ligase binding moiety, the VLM is a VHL binding moiety, and the MLM is a MDM2 E3 ubiquitin ligase binding moiety.

In certain embodiments, the ULM (e.g., a ILM, a CLM, a VLM, or a MLM) shows activity or binds to the E3 ubiquitin ligase (e.g., IAP E3 ubiquitin ligase, cereblon E3 ubiquitin ligase, VHL, or MDM2 E3 ubiquitin ligase) with an $IC_{50}$ of less than about 200 µM. The $IC_{50}$ can be determined according to any method known in the art, e.g., a fluorescent polarization assay.

In certain additional embodiments, the bifunctional compounds described herein demonstrate an activity with an $IC_{50}$ of less than about 100, 50, 10, 1, 0.5, 0.1, 0.05, 0.01, 0.005, 0.001 mM, or less than about 100, 50, 10, 1, 0.5, 0.1, 0.05, 0.01, 0.005, 0.001 µM, or less than about 100, 50, 10, 1, 0.5, 0.1, 0.05, 0.01, 0.005, 0.001 nM, or less than about 100, 50, 10, 1, 0.5, 0.1, 0.05, 0.01, 0.005, 0.001 pM.

In certain embodiments, the compounds as described herein comprise multiple PTMs (targeting the same or different protein targets), multiple ULMs, one or more ULMs (i.e., moieties that bind specifically to multiple/ different E3 ubiquitin ligase, e.g., VHL, IAP, cereblon, and/or MDM2) or a combination thereof. In any of the aspects or embodiments described herein, the PTMs and ULMs (e.g., ILM, VLM, CLM, and/or MLM) can be coupled directly or via one or more chemical linkers or a combination thereof. In additional embodiments, where a compound has multiple ULMs, the ULMs can be for the same E3 ubiquintin ligase or each respective ULM can bind specifically to a different E3 ubiquitin ligase. In still further embodiments, where a compound has multiple PTMs, the PTMs can bind the same target protein or each respective PTM can bind specifically to a different target protein.

In certain embodiments, where the compound comprises multiple ULMs, the ULMs are identical. In additional embodiments, the compound comprising a plurality of ULMs (e.g., ULM, ULM', etc.), at least one PTM coupled to a ULM directly or via a chemical linker (L) or both. In certain additional embodiments, the compound comprising a plurality of ULMs further comprises multiple PTMs. In still additional embodiments, the PTMs are the same or, optionally, different. In still further embodiments, wherein the PTMs are different, the respective PTMs may bind the same protein target or bind specifically to a different protein target.

In certain embodiments, the compound may comprise a plurality of ULMs and/or a plurality of ULM's. In further embodiments, the compound comprising at least two different ULMs, a plurality of ULMs, and/or a plurality of ULM's further comprises at least one PTM coupled to a ULM or a ULM' directly or via a chemical linker or both. In any of the embodiments described herein, a compound comprising at least two different ILMs can further comprise multiple PTMs. In still additional embodiments, the PTMs are the same or, optionally, different. In still further embodiments, wherein the PTMs are different the respective PTMs may bind the same protein target or bind specifically to a different protein target. In still further embodiments, the PTM itself is a ULM (or ULM'), such as an ILM, a VLM, a CLM, a MLM, an ILM', a VLM', a CLM', and/or a MLM'.

In additional embodiments, the description provides the compounds as described herein including their enantiomers, diastereomers, solvates and polymorphs, including pharmaceutically acceptable salt forms thereof, e.g., acid and base salt forms.

Exemplary ILMs
AVPI Tetrapeptide Fragments

In any of the compounds described herein, the ILM can comprise an alanine-valine-proline-isoleucine (AVPI) tetrapeptide fragment or an unnatural mimetic thereof. In certain embodiments, the ILM is selected from the group consisting of chemical structures represented by Formulas (I), (II), (III), (IV), and (V):

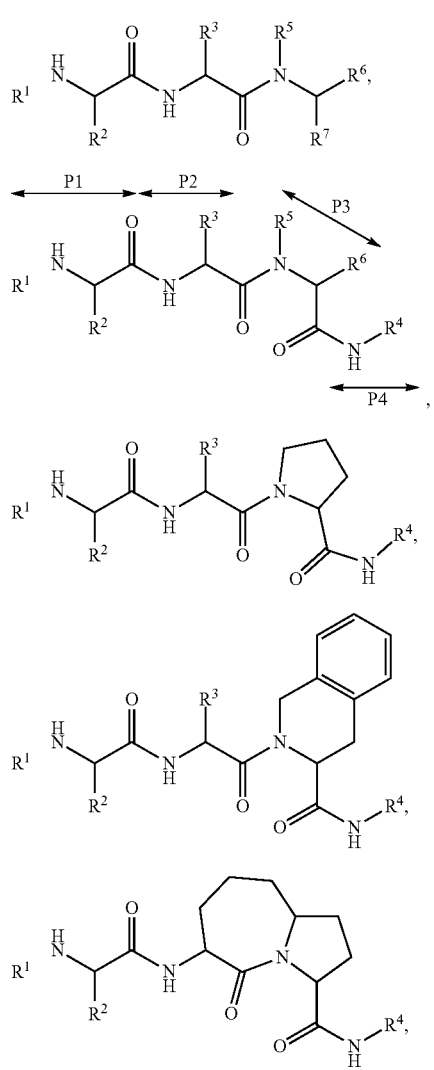

wherein:
- $R^1$ for Formulas (I), (II), (III), (IV), and (V) is selected from H or alkyl;
- $R^2$ for Formulas (I), (II), (III), (IV), and (V) is selected from H or alkyl;
- $R^3$ for Formulas (I), (II), (III), (IV), and (V) is selected from H, alkyl, cycloalkyl and heterocycloalkyl;
- $R^5$ and $R^6$ for Formulas (I), (II), (III), (IV), and (V) are independently selected from H, alkyl, cycloalkyl, heterocycloalkyl, or more preferably, $R^5$ and $R^6$ taken together for Formulas (I), (II), (III), (IV), and (V) form a pyrrolidine or a piperidine ring further optionally fused to 1-2 cycloalkyl, heterocycloalkyl, aryl or heteroaryl rings, each of which can then be further fused to another cycloalkyl, heterocycloalkyl, aryl or heteroaryl ring;
- $R^3$ and $R^5$ for Formulas (I), (II), (III), (IV), and (V) taken together can form a 5-8-membered ring further optionally fused to 1-2 cycloalkyl, heterocycloalkyl, aryl or heteroaryl rings;
- $R^7$ for Formulas (I), (II), (III), (IV), and (V) is selected from cycloalkyl, cycloalkylalkyl, heterocycloalkyl, heterocycloalkylalkyl, aryl, arylalkyl, heteroaryl or heteroarylalkyl, each one further optionally substituted with 1-3 substituents selected from halogen, alkyl, haloalkyl, hydroxyl, alkoxy, cyano, (hetero)cycloalkyl or (hetero)aryl, or $R^7$ is $-C(O)NH-R^4$; and
- $R^4$ is selected from alkyl, cycloalkyl, heterocycloalkyl, cycloalkylalkyl, heterocycloalkylalkyl, aryl, arylalkyl, heteroaryl, heteroarylalkyl, further optionally substituted with 1-3 substituents as described above.

As shown above, P1, P2, P3, and P4 of Formula (II) correlate with A, V, P, and I, respectively, of the AVPI tetrapeptide fragment or an unnatural mimetic thereof. Similarly, each of Formulas (I) and (III) through (V) have portions correlating with A, V, P, and I of the AVPI tetrapeptide fragment or an unnatural mimetic thereof.

In any of the compounds described herein, the ILM can have the structure of Formula (VI), which is a derivative of IAP antagonists described in WO Pub. No. 2008/014236, or an unnatural mimetic thereof:

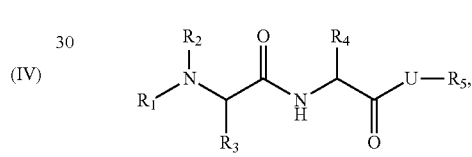

wherein:
- $R_1$ of Formula (VI) is, independently selected from H, $C_1$-$C_4$ alky, $C_1$-$C_4$ alkenyl, $C_1$-$C_4$-alkynyl or $C_3$-$C_{10}$-cycloalkyl which are unsubstituted or substituted;
- $R_2$ of Formula (VI) is, independently selected from H, alkenyl, $C_4$alkynyl or $C_3$-$C_{10}$-cycloalkyl which are unsubstituted or substituted;
- $R_3$ of Formula (VI) is, independently selected from H, $-CF_3$, $-C_2H_5$, $-C_1$-$C_4$-alkyl, $C_1$-$C_4$-alkenyl, $C_1$-$C_4$ alkynyl, $-CH_2-Z$ or any $R_2$ and $R_3$ together form a heterocyclic ring;
- each Z of Formula (VI) is, independently selected from H, $-OH$, F, Cl, $-CH_3$, $-CF_3$, $-CH_2Cl$, $-CH_2F$ or $-CH_2OH$;
- $R_4$ of Formula (VI) is, independently selected from $C_1$-$C_{16}$ straight or branched alkyl, $C_1$-$C_{16}$-alkenyl, $C_1$-$C_{16}$-alkynyl, $C_3$-$C_{10}$-cycloalkyl, $-(CH_2)_{0-6}-Z_1$, $-(CH_2)_{0-6}$-aryl, and $-(CH_2)_{0-6}$-het, wherein alkyl, cycloalkyl, and phenyl are unsubstituted or substituted;
- $R_5$ of Formula (VI) is, independently selected from H, $C_{1-10}$-alkyl, aryl, phenyl, $C_{3-7}$-cycloalkyl, $-(CH_2)_{1-6}-C_{3-7}$-cycloalkyl, $-C_{1-10}$-alkyl-aryl, $-(CH_2)_{0-6}-C_{3-7}$-cycloalkyl-$(CH_2)_{0-6}$-phenyl, $-(CH_2)_{0-4}-CH[(CH_2)_{1-4}$-phenyl]$_2$, indanyl, $-C(O)-C_{1-10}$-alkyl, $-C(O)-(CH_2)_{1-6}-C_{3-7}$-cycloalkyl, $-C(O)-(CH_2)_{0-6}$-phenyl, $-(CH_2)_{0-6}-C(O)$-phenyl, $-(CH_2)_{0-6}$-het, $-C(O)-(CH_2)_{1-6}$-het, or R is selected from a residue of an amino acid, wherein the alkyl, cycloalkyl, phenyl, and aryl substituents are unsubstituted or substituted;

$Z_1$ of Formula (VI) is, independently selected from —N($R_{10}$)—C(O)—$C_{1-10}$-alkyl, —N($R_{10}$)—C(O)—(CH$_2$)$_{0-6}$—$C_{3-7}$-cycloalkyl, —N($R_{10}$)—C(O)—(CH$_2$)$_{0-6}$-phenyl, —N($R_{10}$)—C(O)(CH$_2$)$_{1-6}$-het, —C(O)—N($R_{11}$)($R_{12}$), —C(O)—O—$C_{1-10}$-alkyl, —C(O)—O—(CH$_2$)$_{1-6}$—$C_{3-7}$-cycloalkyl, —C(O)—O—(CH$_2$)$_{0-6}$-phenyl, —C(O)—O—(CH$_2$)$_{1-6}$-het, —O—C(O)—$C_{1-10}$-alkyl, —O—C(O)—(CH$_2$)$_{1-6}$—$C_{3-7}$-cycloalkyl, —O—C(O)—(CH$_2$)$_{0-6}$-phenyl, —O—C(O)—(CH$_2$)$_{1-6}$-het, wherein alkyl, cycloalkyl, and phenyl are unsubstituted or substituted;

het of Formula (VI) is, independently selected from a 5-7 member heterocyclic ring containing 1-4 heteroatoms selected from N, O, and S, or an 8-12 member fused ring system including at least one 5-7 member heterocyclic ring containing 1, 2, or 3 heteroatoms selected from N, O, and S, which heterocyclic ring or fused ring system is unsubstituted or substituted on a carbon or nitrogen atom;

$R_{10}$ of Formula (VI) is selected from H, —CH$_3$, —CF$_3$, —CH$_2$OH, or —CH$_2$Cl;

$R_{11}$ and $R_{12}$ of Formula (VI) are independently selected from H, $C_{1-4}$-alkyl, $C_{3-7}$-cycloalkyl, —(CH$_2$)$_{1-6}$-$C_{3-7}$-cycloakyl, (CH$_2$)$_{0-6}$-phenyl, wherein alkyl, cycloalkyl, and phenyl are unsubstituted or substituted; or $R_{11}$ and $R_{12}$ together with the nitrogen form het, and U of Formula (VI) is, independently, as shown in Formula (VII):

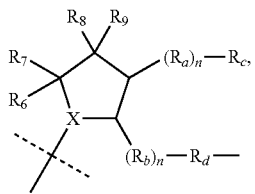

(VII)

wherein:
each n of Formula (VII) is, independently selected from 0 to 5;
X of Formula (VII) is selected from the group —CH and N;
$R_a$ and $R_b$, of Formula (VII) are independently selected from the group O, S, or N atom or $C_{0-8}$-alkyl wherein one or more of the carbon atoms in the alkyl chain are optionally replaced by a heteroatom selected from O, S, or N, and where each alkyl is, independently, either unsubstituted or substituted;
$R_d$ of Formula (VII) is selected from the group Re-Q-($R_f$)$_p$ ($R_g$)$_q$, and Ar$_1$-D-Ar$_2$;
$R_c$ of Formula (VII) is selected from the group H or any $R_c$ and $R_d$ together form a cycloalkyl or het; where if $R_c$ and $R_d$ form a cycloalkyl or het, $R_5$ is attached to the formed ring at a C or N atom;
p and q of Formula (VII) are independently selected from 0 or 1;
$R_e$ of Formula (VII) is selected from the group $C_{1-8}$-alkyl and alkylidene, and each Re is either unsubstituted or substituted;
Q is selected from the group N, O, S, S(O), and S(O)$_2$;
Ar$_1$ and Ar$_2$ of Formula (VII) are independently selected from the group of substituted or unsubstituted aryl and het;

$R_f$ and $R_g$ of Formula (VII) are independently selected from H, —C1-10-alkyl, $C_{1-10}$-alkylaryl, —OH, —O—$C_{1-10}$-alkyl, (CH$_2$)$_{0-6}$—$C_{3-7}$-cycloalky, —O—(CH$_2$)$_{0-6}$-aryl, phenyl, aryl, phenyl-phenyl, —(CH$_2$)$_{1-6}$-het, —O—(CH$_2$)$_{1-6}$-het, —OR$_{13}$, —C(0)-R$_{13}$, —C(O)—N(R$_{13}$)(R$_{14}$), —N(R$_{13}$)(R$_{14}$), —S—R$_{13}$, —S(O)—R$_{13}$, —S(O)$_2$—R$_{13}$, —S(O)$_2$—NR$_{13}$R$_{14}$, —NR$_{13}$—S(O)$_2$—R$_{14}$, —S—$C_{1-10}$-alkyl, aryl-$C_{1-4}$-alkyl, or het-$C_{1-4}$-alkyl, wherein alkyl, cycloalkyl, het, and aryl are unsubstituted or substituted, —SO$_2$—$C_{1-2}$-alkyl, —SO$_2$—$C_{1-2}$-alkylphenyl, —O—$C_{1-4}$-alkyl, or any $R_g$ and $R_f$ together form a ring selected from het or aryl;

D of Formula (VII) is selected from the group —CO—, —C(O)—$C_{1-7}$-alkylene or arylene, —CF$_2$—, —O—, —S(O), where r is 0-2,1,3-dioxalane, or $C_{1-7}$-alkyl-OH; where alkyl, alkylene, or arylene are unsubstituted or substituted with one or more halogens, OH, —O—$C_{1-6}$-alkyl, —S—$C_{1-6}$-alkyl, or —CF$_3$; or each D is, independently selected from N(R$_h$);

Rh is selected from the group H, unsubstituted or substituted $C_{1-7}$-alkyl, aryl, unsubstituted or substituted —O—($C_{1-7}$-cycloalkyl), —C(O)—$C_{1-10}$-alkyl, —C(O)—$C_{0-10}$-alkyl-aryl, to alkyl, —C—O—$C_{0-10}$-alkyl-aryl, —SO$_2$—$C_{1-10}$-alkyl, or —SO$_2$—($C_{0-10}$-alkylaryl);

$R_6$, $R_7$, and $R_9$ of Formula (WI) are, independently, selected from the group H, —$C_{1-10}$-alkyl, —$C_{1-10}$-alkoxy, aryl-$C_{1-10}$-alkoxy, —OH, —O—$C_{1-10}$-alkyl, —(CH$_2$)$_{0-6}$—$C_{3-7}$-cycloalkyl, —O—(CH$_2$)$_{0-6}$-aryl, phenyl, —(CH$_2$)$_{1-6}$-het, —O—(CH$_2$)$_{1-6}$-het, —OR$_{13}$, —C(O)—R$_{13}$, —C(O)—N(R$_{13}$)(R$_{14}$), —N(R$_{13}$)(R$_{14}$), —S—R$_{13}$, —S(O)—R$_{13}$, —S(O)$_2$—NR$_{13}$R$_{14}$, or —NR$_{13}$—S(O)$_2$—R$_{14}$; wherein each alkyl, cycloalkyl, and aryl is unsubstituted or substituted; and any $R_6$, $R_7$, $R_8$, and $R_9$ optionally together form a ring system;

$R_{13}$ and $R_{14}$ of Formula (VII) are independently selected from the group H, $C_{1-10}$-alkyl, —(CH$_2$)$_{0-6}$—$C_{3-7}$-cycloalkyl, —(CH$_2$)$^{0-6}$—(CH)$_{0-1}$-(aryl)$_{1-2}$, —C(O)—$C_{1-10}$-alkyl, —C(O)—(CH$_2$)$_{1-6}$—$C_{3-7}$-cycloalkyl, —C(O)—O—(CH$_2$)$_{0-6}$-aryl, —C(O)—(CH$_2$)$_{0-6}$—O-fluorenyl, —C(O)—NH—(CH$_2$)$_{0-6}$-aryl, —C(O)—(CH$_2$)$_{0-6}$-aryl, —C(O)—(CH$_2$)$_{0-6}$-het, —C(S)—($C_{1-10}$-alkyl, —C(S)—(CH$_2$)$_{1-6}$—$C_{3-7}$-cycloalkyl, —C(S)—O—(CH$_2$)$_{0-6}$-aryl, —C(S)—(CH$_2$)$_{0-6}$—O-fluorenyl, —C(S)—NH—(CH$_2$)$_{0-6}$-aryl, —C(S)—(CH$_2$)$_{0-6}$-aryl, or —C(S)—(CH$_2$)$_{1-6}$-het, wherein each alkyl, cycloalkyl, and aryl is unsubstituted or substituted: or any $R_{13}$ and $R_{14}$ together with a nitrogen atom form het; wherein alkyl substituents of $R_{13}$ and $R_{14}$ of Formula (VII) are unsubstituted or substituted and when substituted, are substituted by one or more substituents selected from $C_{1-10}$-alkyl, halogen, OH, —O—$C_{1-6}$-alkyl, —S—$C_{1-6}$-alkyl, and —CF$_3$; and substituted phenyl or aryl of $R_{13}$ and $R_{14}$ are substituted by one or more substituents selected from halogen, hydroxyl. $C_{1-4}$-alkyl, $C_{1-4}$-alkoxy, nitro, —CN, —O—C(O)—$C_{1-4}$-alkyl, and —C(O)—O—$C_{1-4}$-aryl; or a pharmaceutically acceptable salt or hydrate thereof.

In certain embodiments, the compound further comprises an independently selected second ILM attached to the ILM of Formula (VI), or an unnatural mimetic thereof, by way of at least one additional independently selected linker group. In an embodiment, the second ILM is a derivative of Formula (VI), or an unnatural mimetic thereof. In a certain embodiment, the at least one additional independently selected linker group comprises two additional independently selected linker groups chemically linking the ILM and the second ILM. In an embodiment, the at least one additional linker group for an ILM of the Formula (VI), or an unnatural mimetic thereof, chemically links groups selected from $R_4$ and $R_5$. For example, an ILM of Formula (VI) and a second ILM of Formula (VI), or an unnatural mimetic thereof, can be linked as shown below:

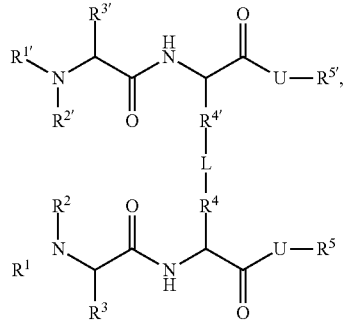
(A)

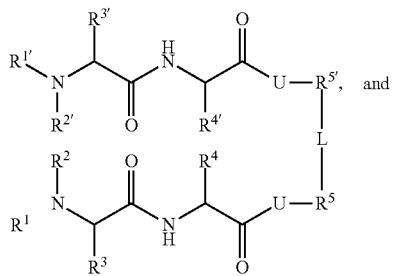
(B)

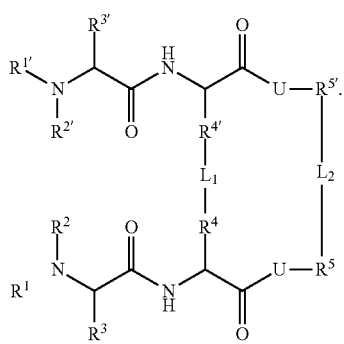
(C)

In certain embodiments, the ILM, the at least one additional independently selected linker group L, and the second ILM has a structure selected from the group consisting of:

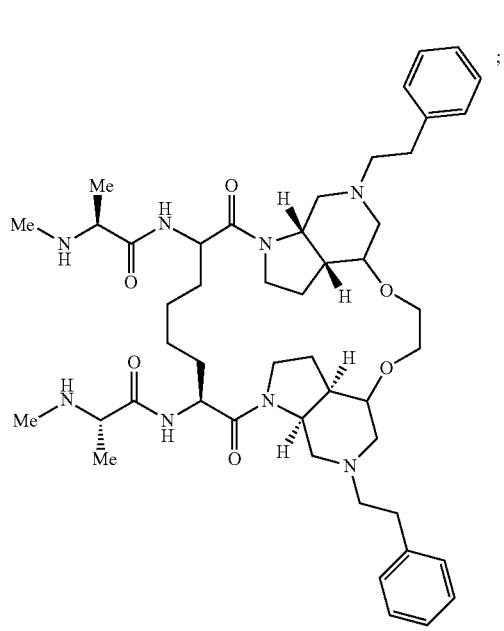
(A)

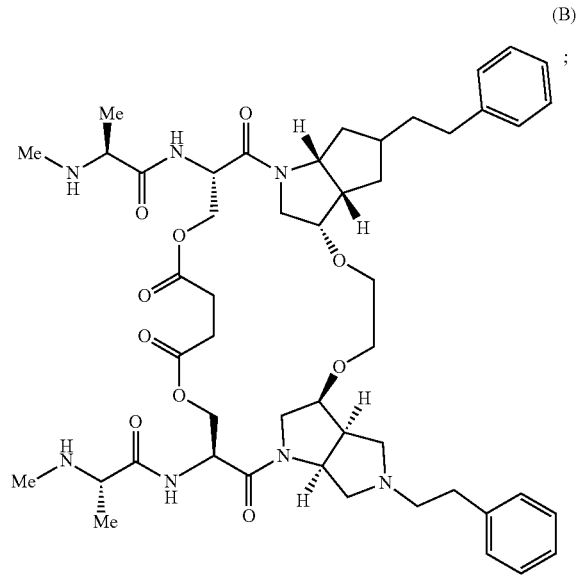
(B)

-continued
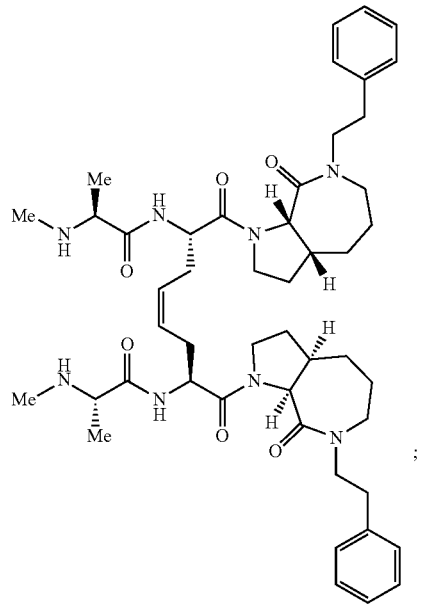
(C)
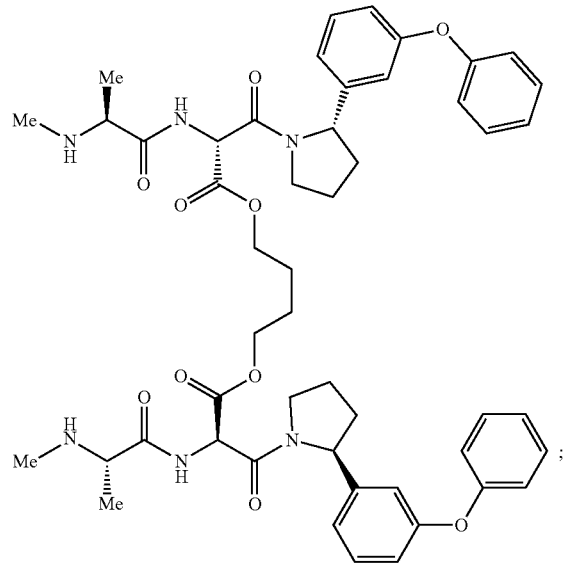
(D)
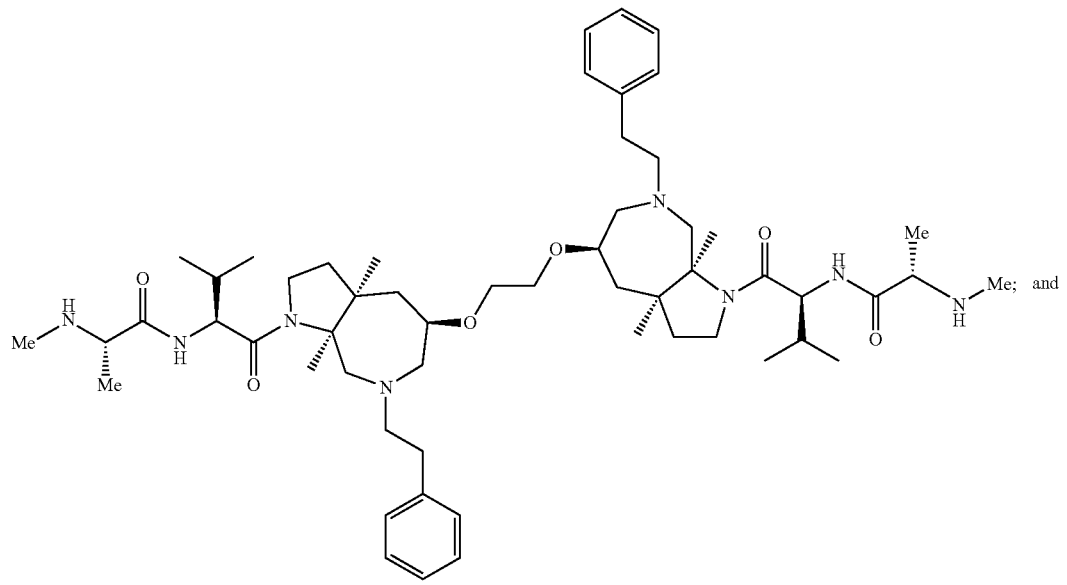
(E)
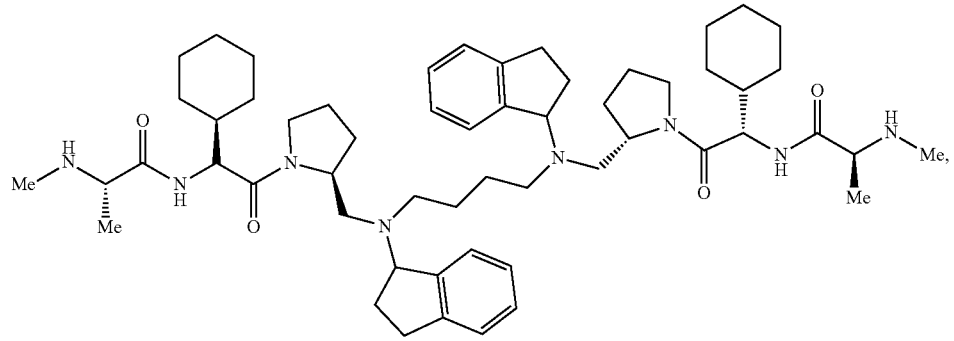
(F)
which are derivatives of IAP antagonists described in WO Pub. No. 2008/014236.

In any of the compounds described herein, the ILM can have the structure of Formula (VIII), which is based on the IAP ligrands described in Ndubaku, C., et al. Antagonism of c-IAP and XIAP proteins is required for efficient induction of cell death by small-molecule IAP antagonists, *ACS Chem. Biol.*, 557-566, 4 (7) (2009), or an unnatural mimetic thereof:

(VIII)

wherein each of A1 and A2 of Formula (VIII) is independently selected from optionally substituted monocyclic, fused rings, aryls and hetoroaryls; and R of Formula (VIII) is selected from H or Me.

In a particular embodiment, the linker group L is attached to A1 of Formula (VIII). In another embodiment, the linker group L is attached to A2 of Formula (VIII).

In a particular embodiment, the ILM is selected from the group consisting of (A)

(B)

In any of the compounds described herein, the ILM can have the structure of Formula (IX), which is derived from the chemotypes cross-referenced in Mannhold, R., et al. IAP antagonists: promising candidates for cancer therapy, *Drug Discov. Today,* 15 (5-6), 210-9 (2010), or an unnatural mimetic thereof:

(IX)

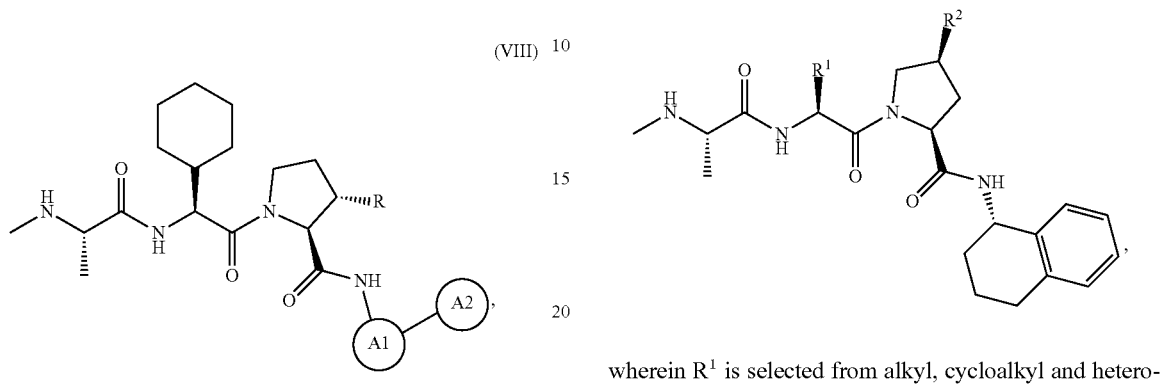

wherein $R^1$ is selected from alkyl, cycloalkyl and heterocycloalkyl and, most preferably, from isopropyl, tert-butyl, cyclohexyl and tetrahydropyranyl, and $R^2$ of Formula (IX) is selected from —OPh or H.

In any of the compounds described herein, the ILM can have the structure of Formula (X), which is derived from the chemotypes cross-referenced in Mannhold, R., et al. IAP antagonists: promising candidates for cancer therapy, *Drug Discov. Today,* 15 (5-6), 210-9 (2010), or an unnatural mimetic thereof:

(X)

n = 1, 2, 3 wherein:

$R^1$ of Formula (X) is selected from H, —CH$_2$OH, —CH$_2$CH$_2$OH, —CH$_2$NH$_2$, —CH$_2$CH$_2$NH$_2$;

X of Formula (X) is selected from S or CH$_2$;

$R^2$ of Formula (X) is selected from:

-continued

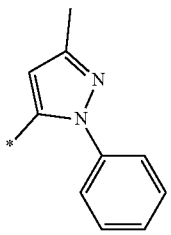

R³ and R⁴ of Formula (X) are independently selected from H or Me

In any of the compounds described herein, the ILM can have the structure of Formula (XI), which is derived from the chemotypes cross-referenced in Mannhold, R., et al. IAP antagonists: promising candidates for cancer therapy, *Drug Discov. Today*, 15 (5-6), 210-9 (2010), or an unnatural mimetic thereof:

(XI)

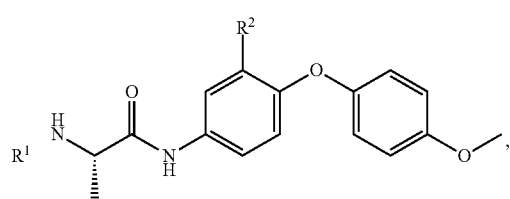

wherein R¹ of Formula (XI) is selected from H or Me, and R² of Formula (XI) is selected from H or

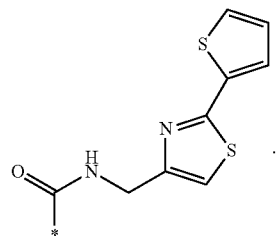 [SMILES: *C(=O)NCc1csc(-c2cccs2)n1]

In any of the compounds described herein, the ILM can have the structure of Formula (XII), which is derived from the chemotypes cross-referenced in Mannhold, R., et al. IAP antagonists: promising candidates for cancer therapy, *Drug Discov. Today*, 15 (5-6), 210-9 (2010), or an unnatural mimetic thereof:

(XII)

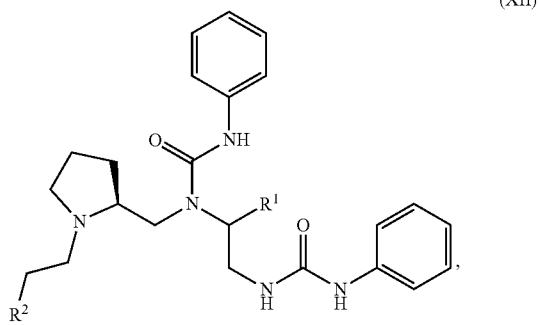

wherein:
R¹ of Formula (XII) is selected from:

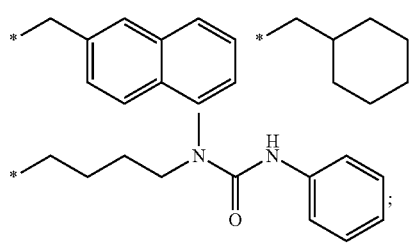

and R² of Formula (XII) is selected from:

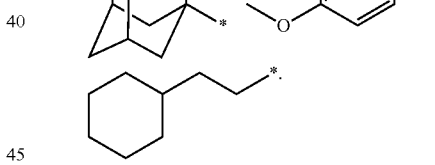

In any of the compounds described herein, the IAP E3 ubiquitin ligase binding moiety is selected from the group consisting of:

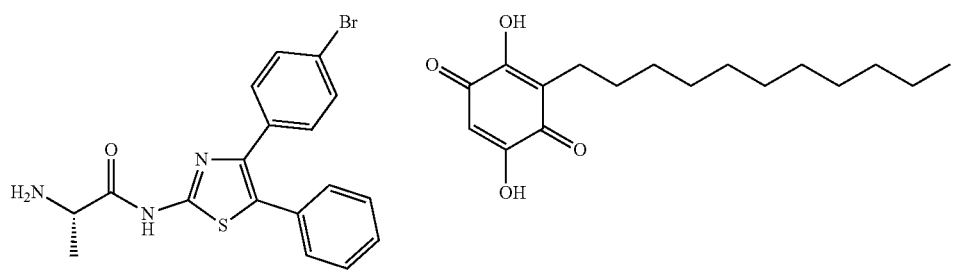

-continued
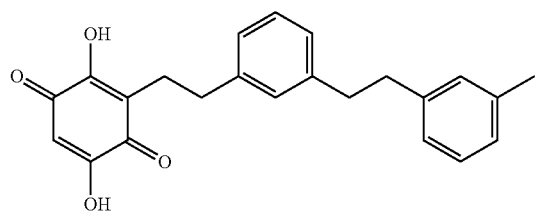
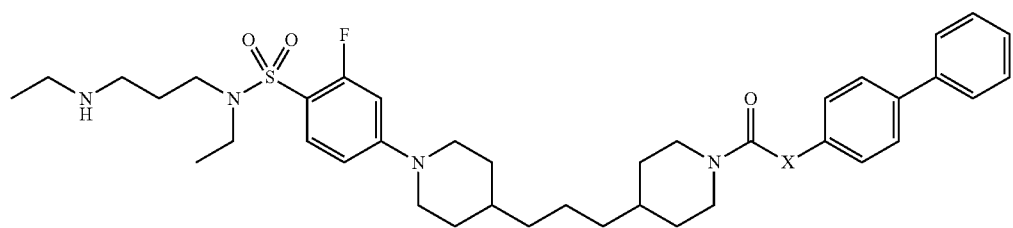
X = NH, bond
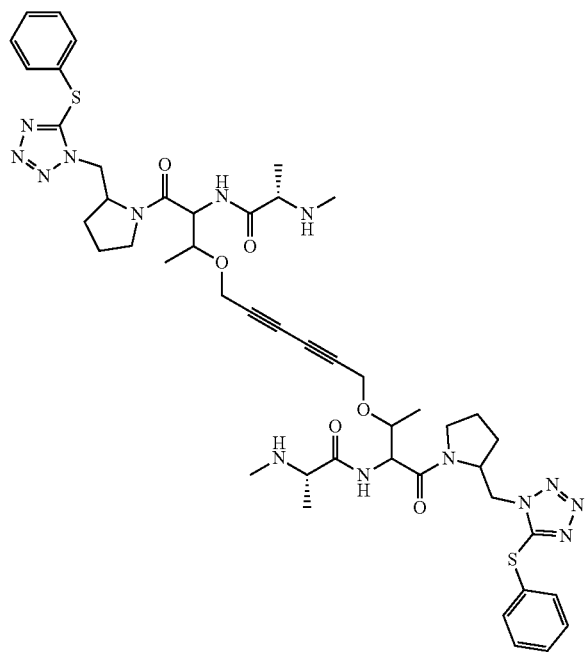

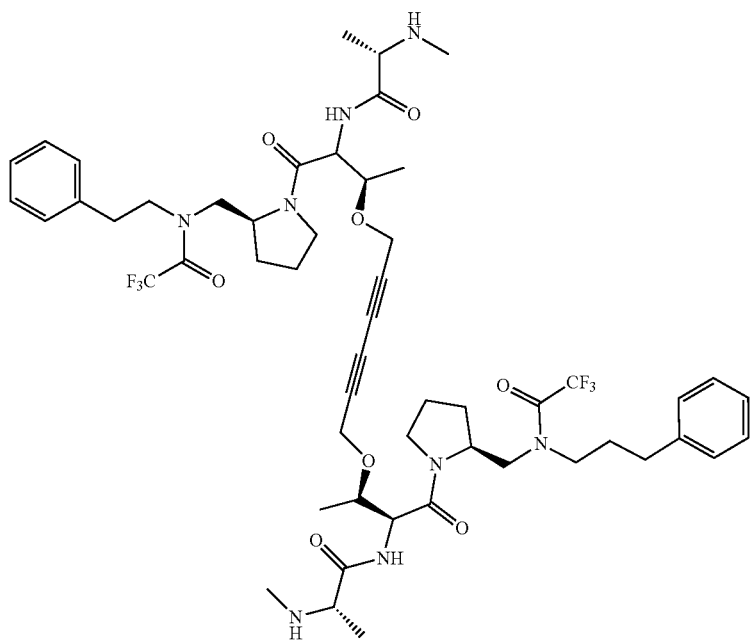
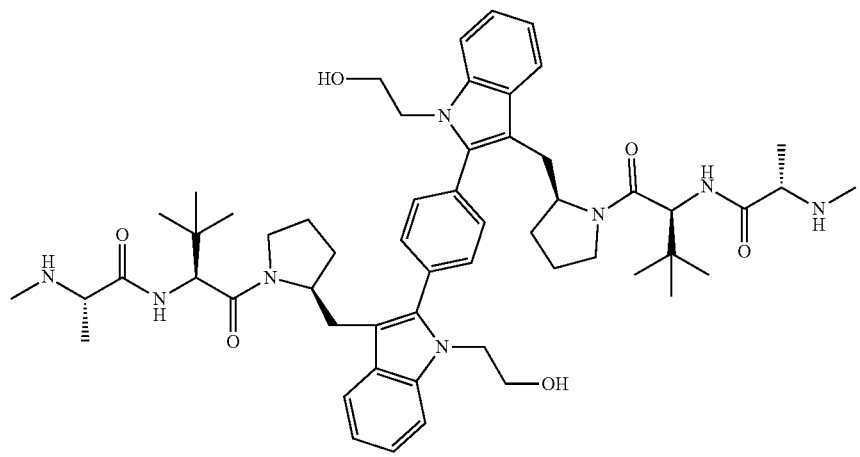
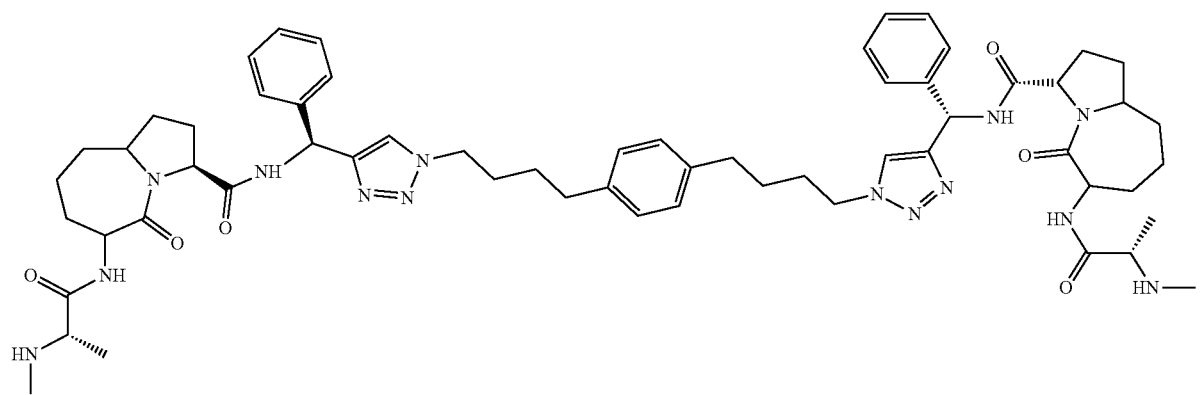

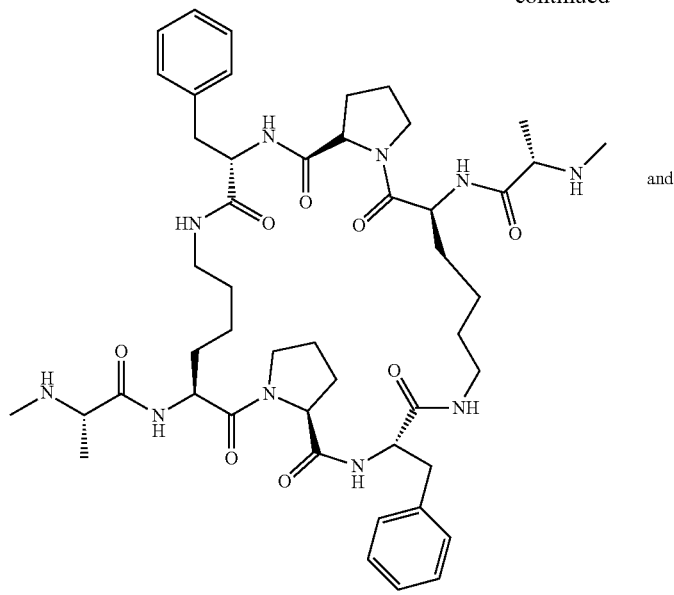
and
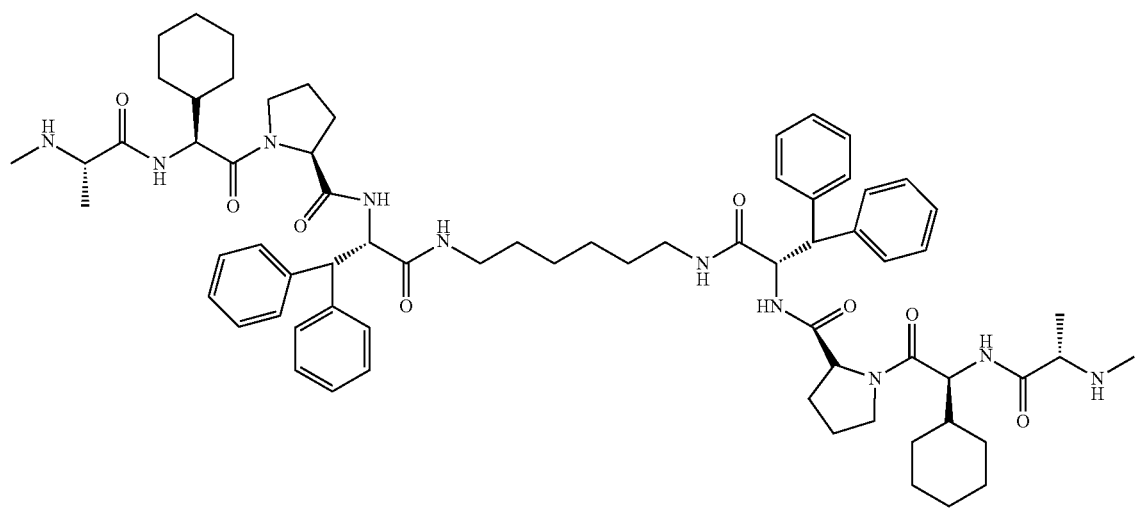
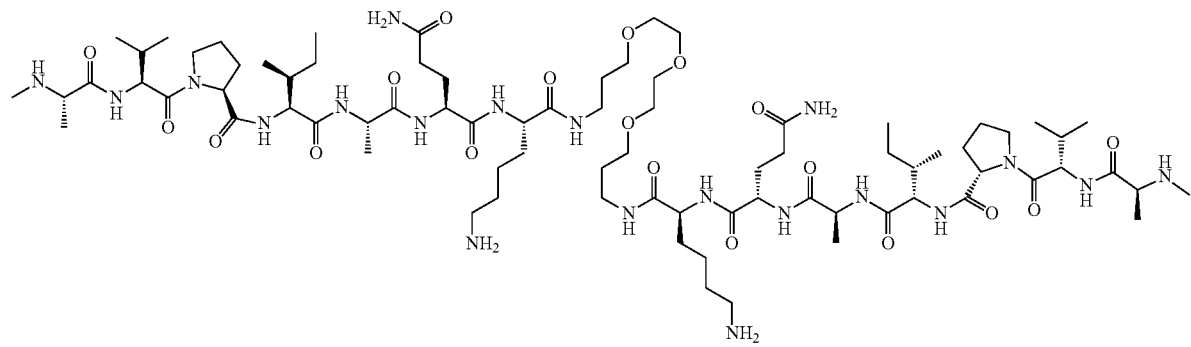
In any of the compounds described herein, the ILM can have the structure of Formula (XIII), which is based on the IAP ligands summarized in Flygare, J. A., et al. Small-molecule pan-IAP antagonists: a patent review, *Expert Opin. Ther. Pat.*, 20 (2), 251-67 (2010), or an unnatural mimetic thereof:

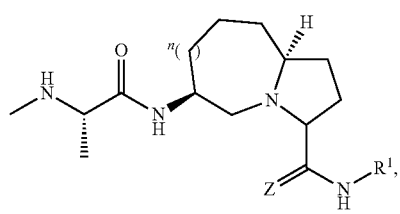

(XIII)

n = 0, 2 or, preferably, 1 wherein:

Z of Formula (XIII) is absent or O;

R¹ of Formula (XIII) is selected from:

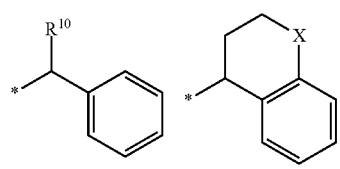

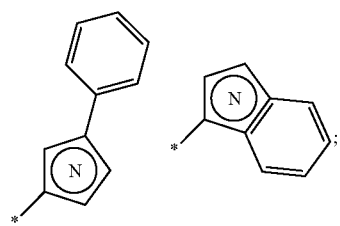

R$^{10}$ of

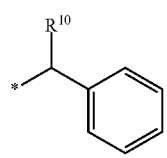

is selected from H, alkyl, or aryl;

X is selected from CH2 and O; and

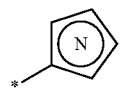

is a nitrogen-containing heteroaryl.

In any of the compounds described herein, the ILM can have the structure of Formula (XIV), which is based on the IAP ligands summarized in Flygare, J. A., et al. Small-molecule pan-IAP antagonists: a patent review, *Expert Opin. Ther. Pat.*, 20 (2), 251-67 (2010), or an unnatural mimetic thereof:

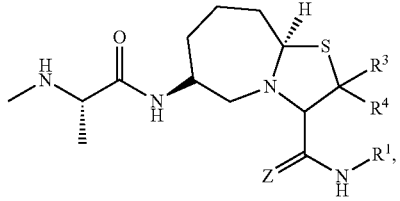

(XIV)

wherein:

Z of Formula (XIV) is absent or O;

R³ and R⁴ of Formula (XIV) are independently selected from H or Me;

R¹ of Formula (XIV) is selected from:

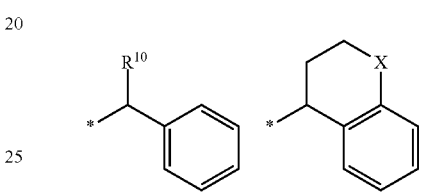

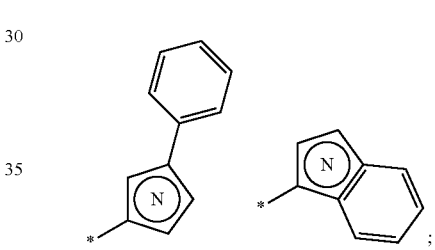

R$^{10}$ of

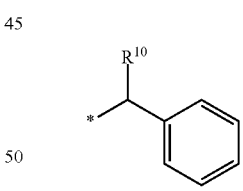

is selected from H, alkyl, or aryl;

X of

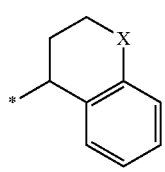

is selected from CH2 and O; and

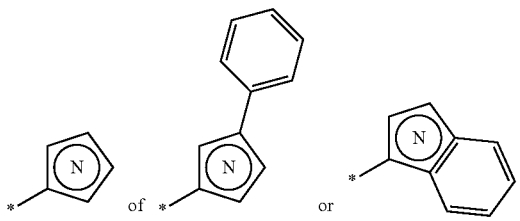

of or is a nitrogen-containing heteraryl.

In any of the compounds described herein, the ILM is selected from the group consisting of:

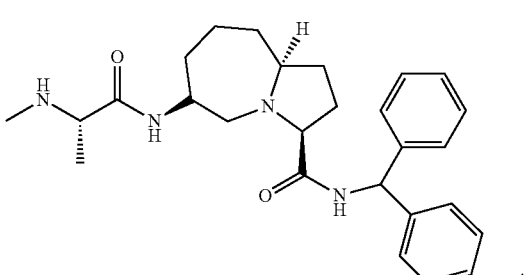

and

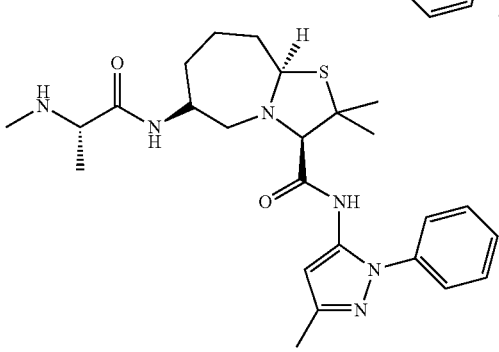

, which are derivatives of ligands disclose in US Patent Pub. No. 2008/0269140 and U.S. Pat. No. 7,244,851.

In any of the compounds described herein, the ILM can have the structure of Formula (XV), which was a derivative of the IAP ligand described in WO Pub. No. 2008/128171, or an unnatural mimetic thereof:

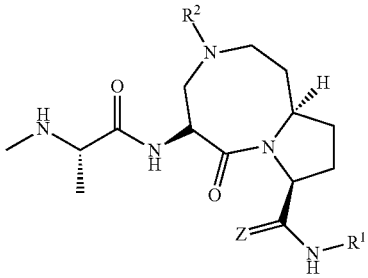

(XV)

wherein:
Z of Formula (XV) is absent or O;

$R^1$ of Formula (XV) is selected from:

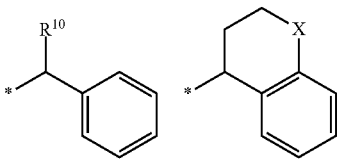

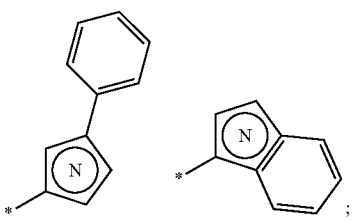

;

$R^{10}$ of

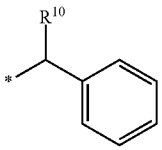

is selected from H, alkyl, or aryl;

X of

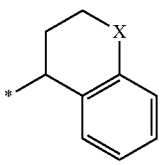

is selected from CH2 and O; and

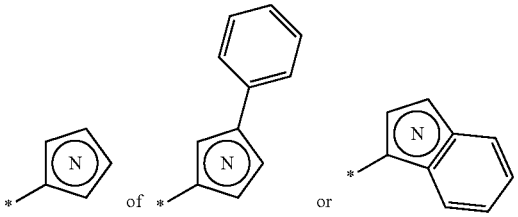

of or is a nitrogen-containing heteraryl; and $R^2$ of Formula (XV) selected from H, alkyl, or acyl;

In a particular embodiment, the ILM has the following structure:

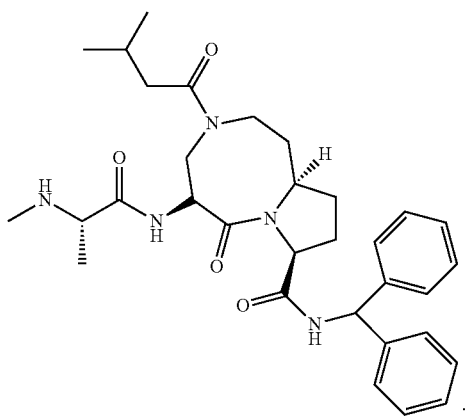

In any of the compounds described herein, the ILM can have the structure of Formula (XVI), which is based on the IAP ligand described in WO Pub. No. 2006/069063, or an unnatural mimetic thereof:

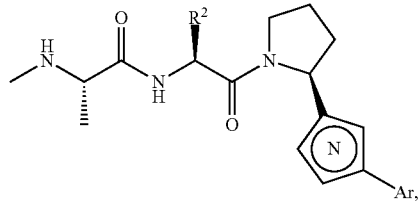

(XVI)

wherein:

R² of Formula (XVI) is selected from alkyl, cycloalkyl and heterocycloalkyl; more preferably, from isopropyl, tert-butyl, cyclohexyl and tetrahydropyranyl, most preferably from cyclohexyl;

of Formula (XVI) is a 5- or 6-membered nitrogen-containing heteroaryl; more preferably, 5-membered nitrogen-containing heteroaryl, and most preferably thiazole; and Ar of Formula (XVI) is an aryl or a heteroaryl.

In any of the compounds described herein, the ILM can have the structure of Formula (XVII), which is based on the IAP ligands described in Cohen, F. et al., Antogonists of inhibitors of apoptosis proteins based on thiazole amide isosteres, Bioorg. Med. Chem. Lett., 20(7), 2229-33 (2010), or an unnatural mimetic thereof:

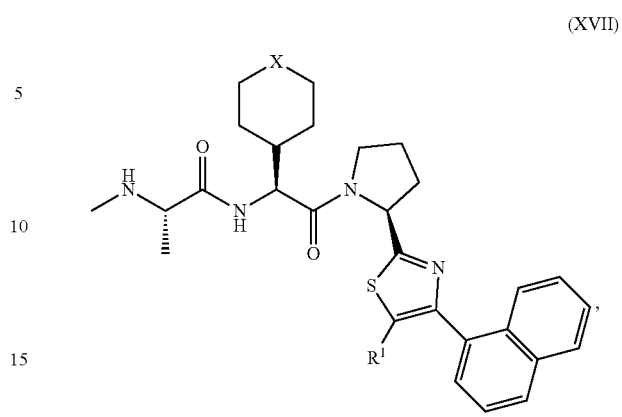

(XVII)

wherein:

R¹ of Formula (XVII) is selected from to group halogen (e.g. fluorine), cyano,

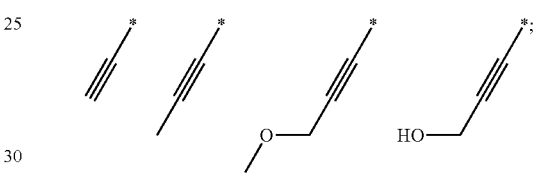

X of Formula (XVII) is selected from the group O or CH2.

In any of the compounds described herein, the ILM can have the structure of Formula (XVIII), which is based on the IAP ligands described in Cohen, F. et al., Antogonists of inhibitors of apoptosis proteins based on thiazole amide isosteres, Bioorg. Med. Chem. Lett., 20(7), 2229-33 (2010), or an unnatural mimetic thereof:

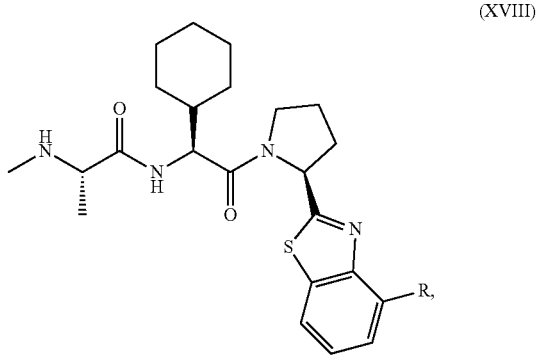

(XVIII)

wherein R of Formula (XVIII) is selected from alkyl, aryl, heteroaryl, arylalkyl, heteroarylalkyl or halogen (in variable substitution position).

In any of the compounds described herein, the ILM can have the structure of Formula (XIX), which is based on the IAP ligands described in Cohen, F. et al., *Antogonists of inhibitors of apoptosis proteins based on thiazole amide isosteres*, Bioorg. Med. Chem. Lett., 20(7), 2229-33 (2010), or an unnatural mimetic thereof:

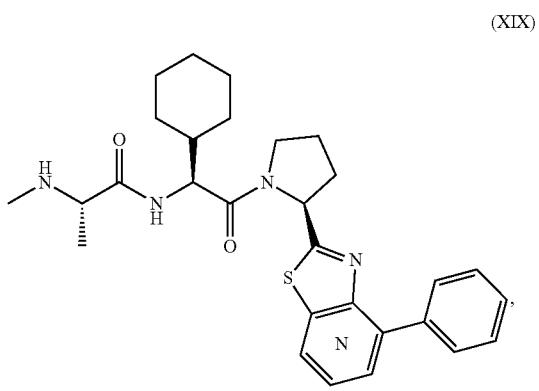
(XIX)

wherein

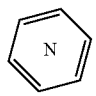

is a 6-member nitrogen heteroaryl.

In a certain embodiment, the ILM of the composition is selected from the group consisting of:

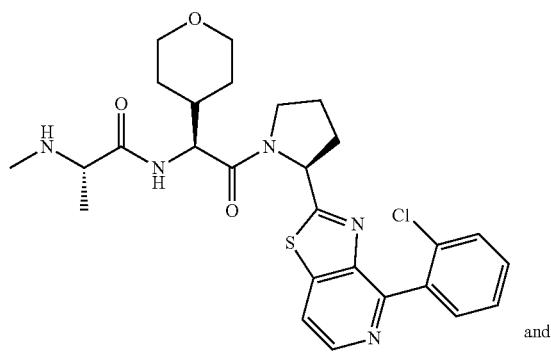

and

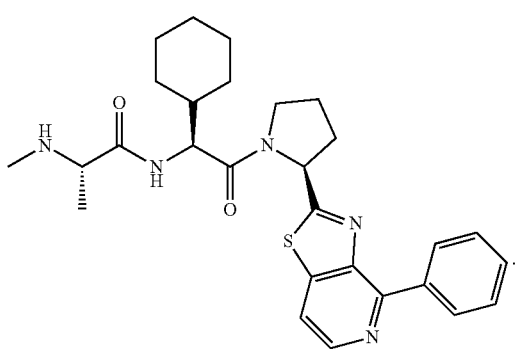

In certain embodiments, the ILM of the composition is selected from the group consisting of:

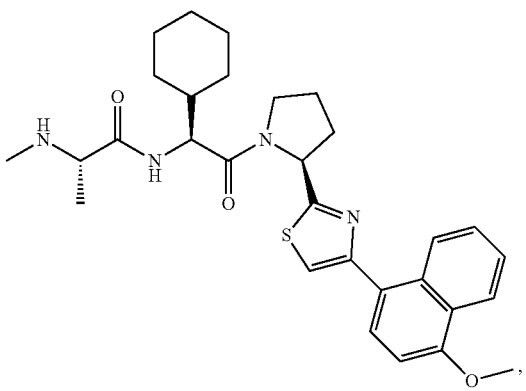

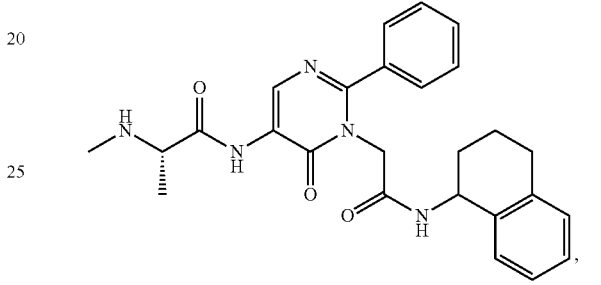

and

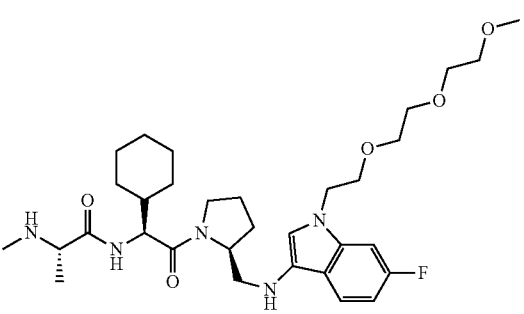

In any of the compounds described herein, the ILM can have the structure of Formula (XX), which is based on the IAP ligands described in WO Pub. No. 2007/101347, or an unnatural mimetic thereof:

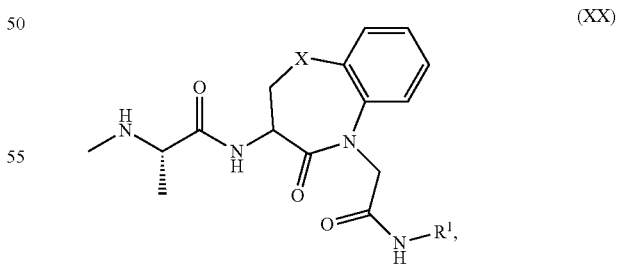
(XX)

wherein X of Formula (XX) is selected from $CH_2$, O, NH, or S.

In any of the compounds described herein, the ILM can have the structure of Formula (XXI), which is based on the IAP ligands described in U.S. Pat. Nos. 7,345,081 and 7,419,975, or an unnatural mimetic thereof:

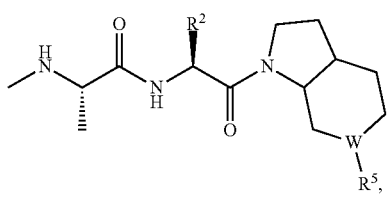

(XXI)

wherein:

R² of Formula (XXI) is selected from:

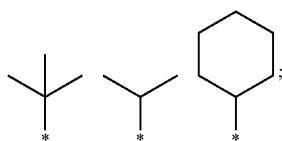

R⁵ of Formula (XXI) is selected from:

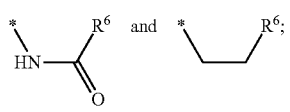

and

W of Formula (XXI) is selected from CH or N; and R⁶ of

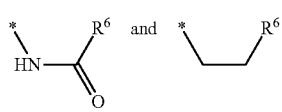

are independently a mono- or bicyclic fused aryl or heteroaryl.

In certain embodiments, the ILM of the compound is selected from the group consisting of:

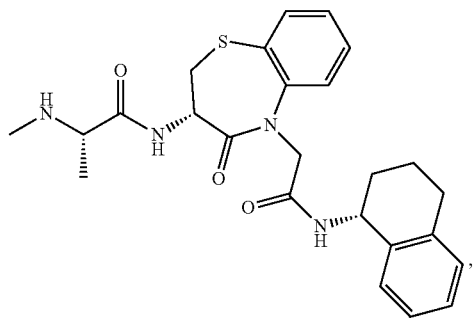

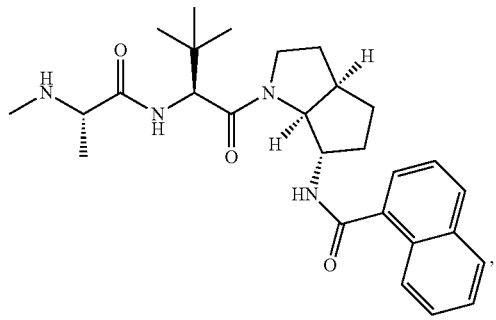

and 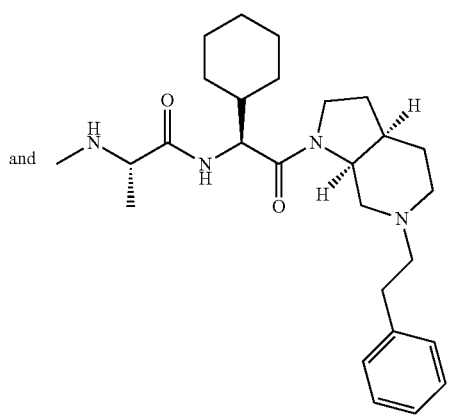

In certain embodiments, the ILM of the compound is selected from the group consisting of:

41
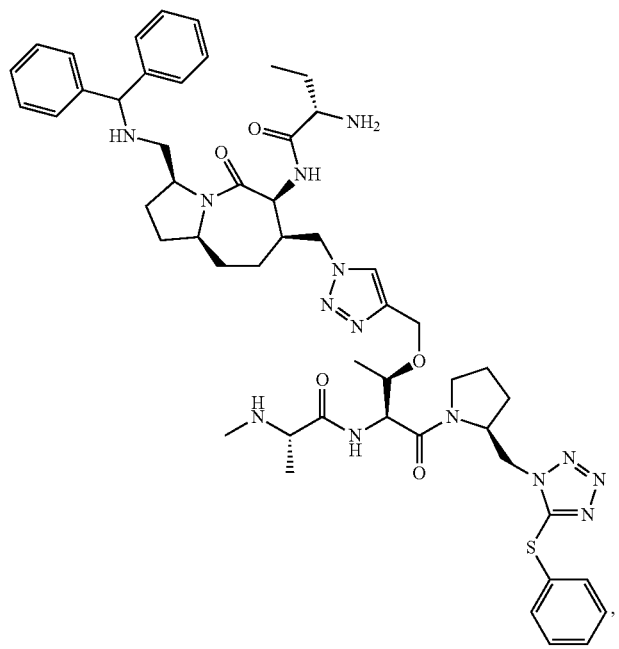
,
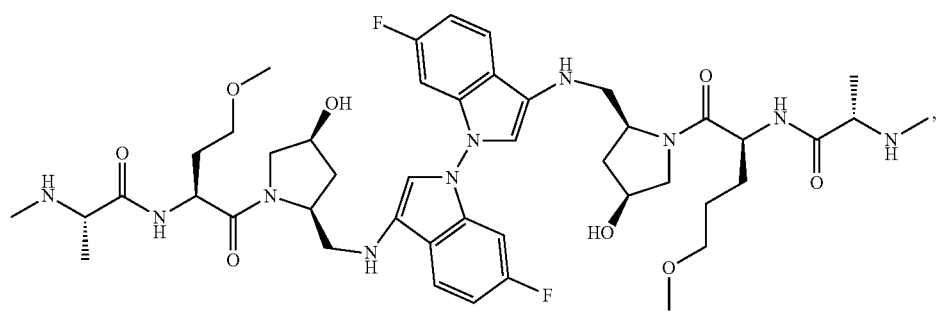
,
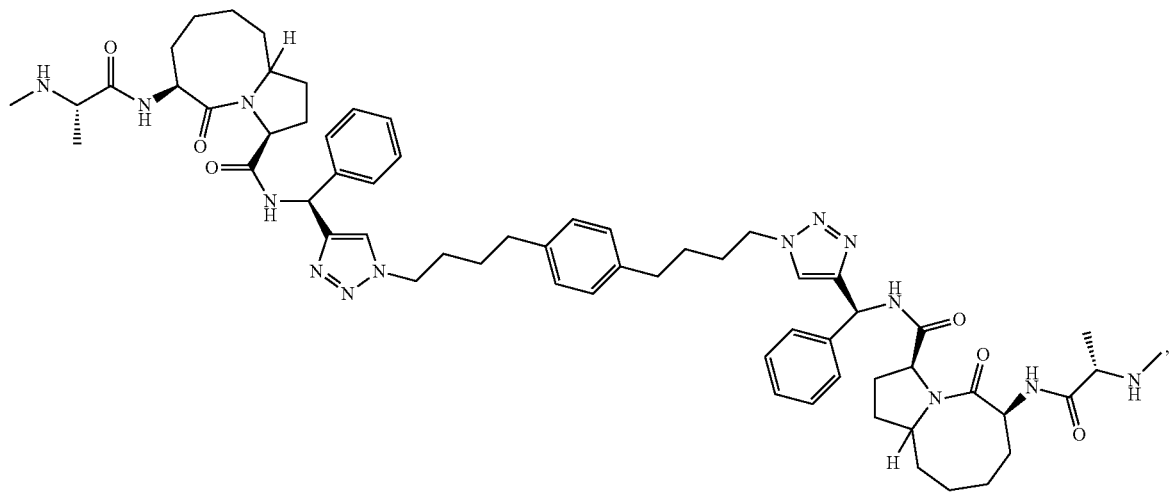

-continued

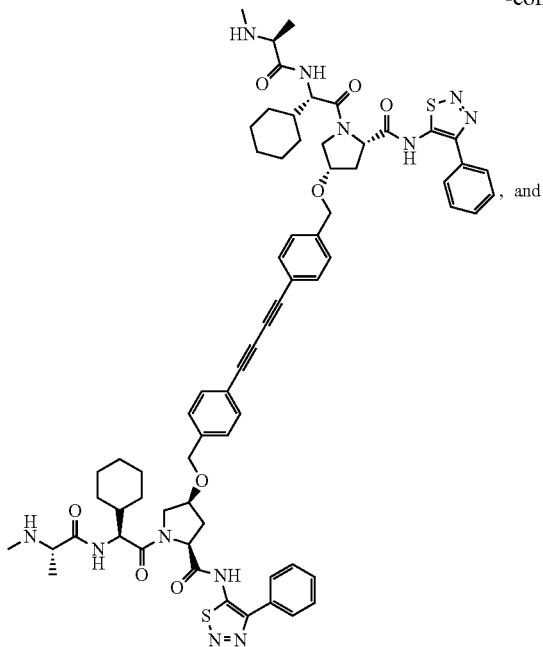

, and

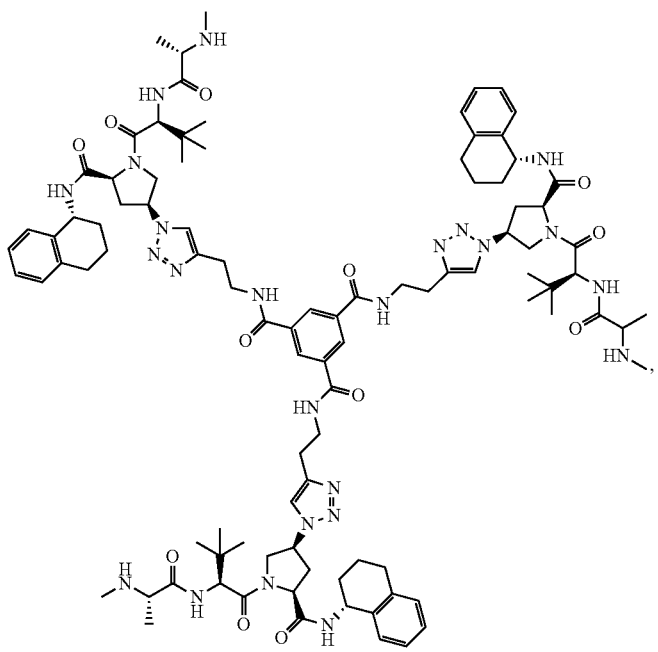

which are described in WO Pub. No. 2009/060292, U.S. Pat. No. 7,517,906, WO Pub. No. 2008/134679, WO Pub. No. 2007/130626, and WO Pub. No. 2008/128121.

In any of the compounds described herein, the ILM can have the structure of Formula (XXII) or (XXIII), which are derived from the IAP ligands described in WO Pub. No. 2015/006524 and Perez H L, *Discovery of potent heterodimeric antagonists of inhibitor of apoptosis proteins (IAPs) with sustained antitumor activity*. J. Med. Chem. 58(3), 1556-62 (2015), or an unnatural mimetic thereof:

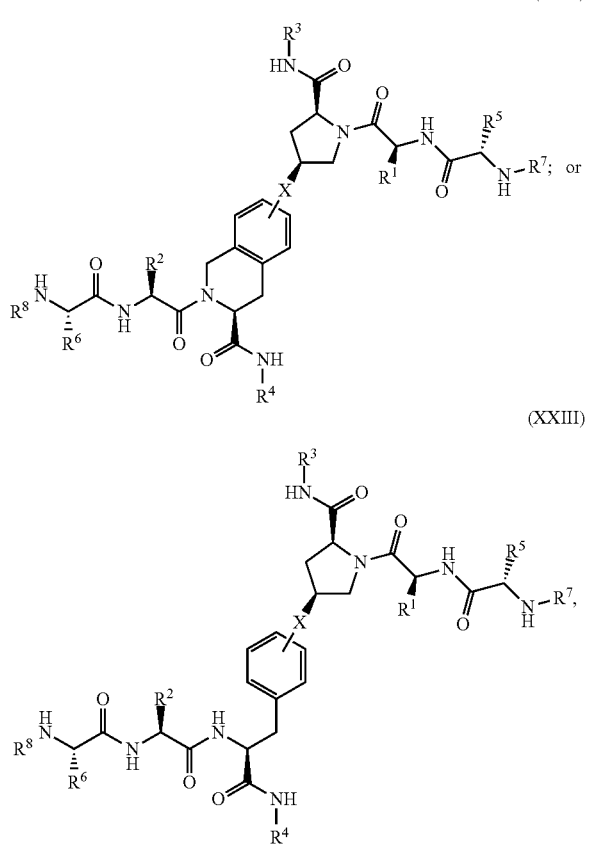

(XXII)

(XXIII)

wherein:
- R¹ of Formula (XXII) or (XXIII) is optionally substituted alkyl, optionally substituted cycloalkyl, optionally substituted cycloalkylalkyl, optionally substituted heterocyclyl, optionally substituted arylalkyl or optionally substituted aryl;
- R² of Formula (XXII) or (XXIII) is optionally substituted alkyl, optionally substituted cycloalkyl, optionally substituted cycloalkylalkyl, optionally substituted heterocyclyl, optionally substituted arylalkyl or optionally substituted aryl;
- or alternatively, R¹ and R² of Formula (XXII) or (XXIII) are independently optionally substituted thioalkyl wherein the substituents attached to the S atom of the thioalkyl are optionally substituted alkyl, optionally substituted branched alkyl, optionally substituted heterocyclyl, —(CH$_2$)$_v$COR$^{20}$, —CH$_2$CHR$^{21}$COR$^{22}$ or —CH$_2$R$^{23}$;

wherein:
- v is an integer from 1-3;
- R$^{20}$ and R$^{22}$ of —(CH$_2$)$_v$COR$^{20}$ and —CH$_2$R$^{23}$ are independently selected from OH, NR$^{24}$R$^{25}$ or OR$^{26}$;
- R$^{21}$ of —CH$_2$CHR$^{21}$COR$^2$ is selected from the group NR$^{24}$R$^{25}$;
- R$^{23}$ of —CH$_2$R$^{23}$ is selected from optionally substituted aryl or optionally substituted heterocyclyl, where the optional substituents include alkyl and halogen;
- R$^{24}$ of NR$^{24}$R$^{25}$ is selected from hydrogen or optionally substituted alkyl;
- R$^{25}$ of NR$^{24}$R$^{25}$ is selected from hydrogen, optionally substituted alkyl, optionally substituted branched alkyl, optionally substituted arylalkyl, optionally substituted heterocyclyl, —CH$_2$(OCH$_2$CH$_2$O)$_m$CH$_3$, or a polyamine chain, such as spermine or spermidine;
- R$^{26}$ of OR$^{26}$ is selected from optionally substituted alkyl, wherein the optional substituents are OH, halogen or NH$_2$; and
- m is an integer from 1-8;
- R³ and R⁴ of Formula (XXII) or (XXIII) are independently selected from optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;
- R⁵, R⁶, R⁷ and R⁸ of Formula (XXII) or (XXIII) are independently selected from hydrogen, optionally substituted alkyl or optionally substituted cycloalkyl; and
- X is selected from a bond or a chemical linker group, and/or a pharmaceutically acceptable salt, tautomer or stereoisomer thereof.

In certain embodiments, X is a bond or is selected from the group consisting of:

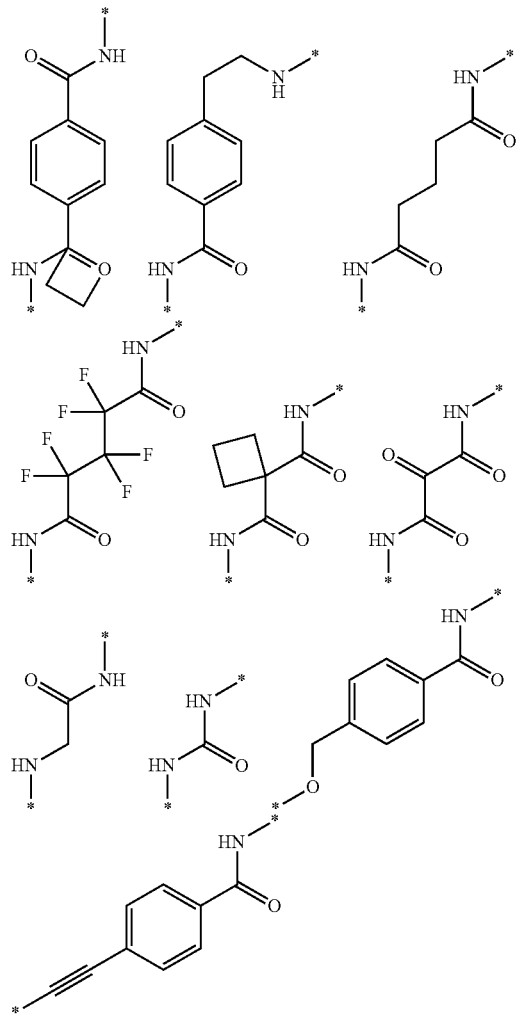

-continued

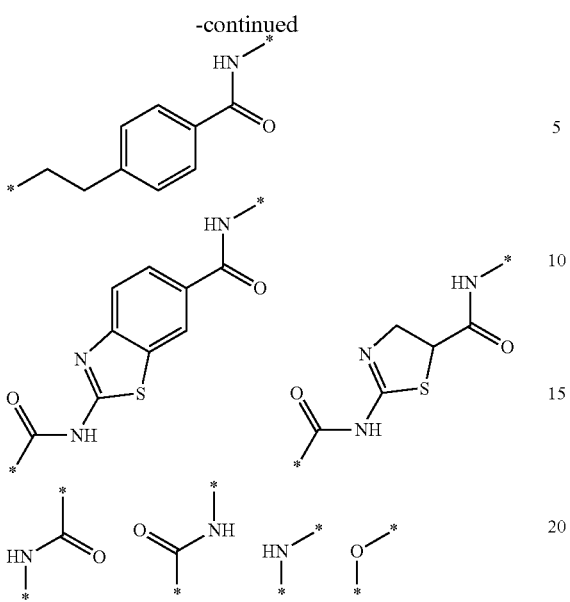

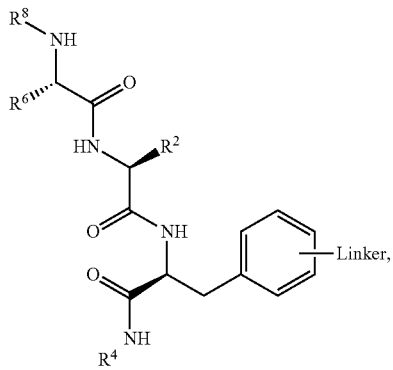

(XXVI)

wherein "*" is the point of attachment of a PTM, L or ULM, e.g., an ILM.

In any of the compounds described herein, the ILM can have the structure of Formula (XXIV) or (XXVI), which are derived from the IAP ligands described in WO Pub. No. 2015/006524 and Perez H L, *Discovery of potent heterodimeric antagonists of inhibitor of apoptosis proteins (IAPs) with sustained antitumor activity.* J. Med. Chem. 58(3), 1556-62 (2015), or an unnatural mimetic thereof, and the chemical linker to linker group L as shown:

(XXIV)

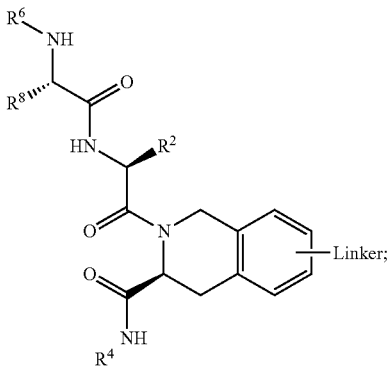

(XXV)

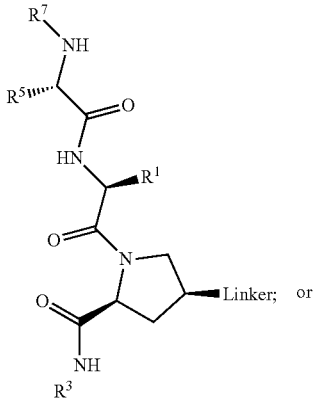

wherein:
R$^1$ of Formula (XXIV), (XXV) or (XXVI) is selected from optionally substituted alkyl, optionally substituted cycloalkyl, optionally substituted cycloalkylalkyl, optionally substituted heterocyclyl, optionally substituted arylalkyl or optionally substituted aryl;

R$^2$ of Formula (XXIV), (XXV) or (XXVI) is selected from optionally substituted alkyl, optionally substituted cycloalkyl, optionally substituted cycloalkylalkyl, optionally substituted heterocyclyl, optionally substituted arylalkyl or optionally substituted aryl;

or alternatively,

R$^1$ and R$^2$ of Formula (XXIV), (XXV) or (XXVI) are independently selected from optionally substituted thioalkyl wherein the substituents attached to the S atom of the thioalkyl are optionally substituted alkyl, optionally substituted branched alkyl, optionally substituted heterocyclyl, —(CH$_2$)$_v$COR$^{20}$, —CH$_2$CHR$^{21}$COR$^{22}$ or —CH$_2$R$^{23}$, wherein:
v is an integer from 1-3;
R$^{20}$ and R$^{22}$ of —(CH$_2$)$_v$COR$^{20}$ and —CH$_2$R$^{23}$ are independently selected from OH, NR$^{24}$R$^{25}$ or OR$^{26}$;
R$^{21}$ of —CH$_2$CHR$^{21}$COR$^2$ is selected from NR$^{24}$R$^{25}$;
R$^{23}$ of —CH$_2$R$^{23}$ is selected from optionally substituted aryl or optionally substituted heterocyclyl, wherein the optional substituents include alkyl and halogen;
R$^{24}$ of NR$^{24}$R$^{25}$ is selected from hydrogen or optionally substituted alkyl;
R$^{25}$ of NR$^{24}$R$^{25}$ is selected from hydrogen, optionally substituted alkyl, optionally substituted branched alkyl, optionally substituted arylalkyl, optionally substituted heterocyclyl, —CH$_2$(OCH$_2$CH$_2$O)$_m$CH$_3$, or a polyamine chain, such as spermine or spermidine;
R$^{26}$ of OR$^{26}$ is selected from optionally substituted alkyl, wherein the optional substituents are OH, halogen or NH$_2$; and
m is an integer from 1-8;

R$^3$ and R$^4$ of Formula (XXIV), (XXV) or (XXVI) are independently optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

R⁵, R⁶, R⁷ and R⁸ of Formula (XXIV), (XXV) or (XXVI) are independently hydrogen, optionally substituted alkyl or optionally substituted cycloalkyl; and/or a pharmaceutically acceptable salt, tautomer or stereoisomer thereof.

In a particular embodiment, the ILM according to Formulas (XXII) through (XXVI):

R⁷ and R⁸ are selected from the H or Me;

R⁵ and R⁶ are selected from the group comprising:

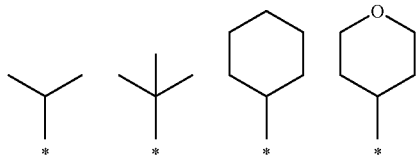

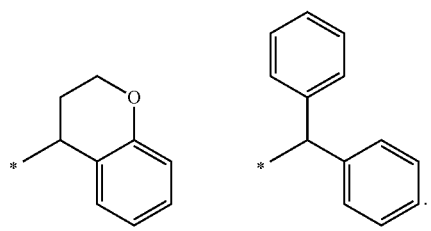

In any of the compounds described herein, the ILM can have the structure of Formula (XXVII) or (XXVII), which are derived from the IAP ligands described in WO Pub. No. 2014/055461 and Kim, K S, *Discovery of tetrahydroisoquinoline-based bivalent heterodimeric IAP antagonists.* Bioorg. Med. Chem. Lett. 24(21), 5022-9 (2014), or an unnatural mimetic thereof:

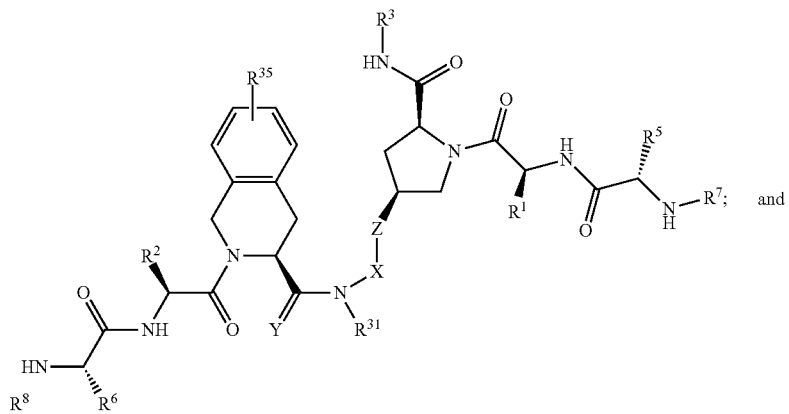

(XXVII)

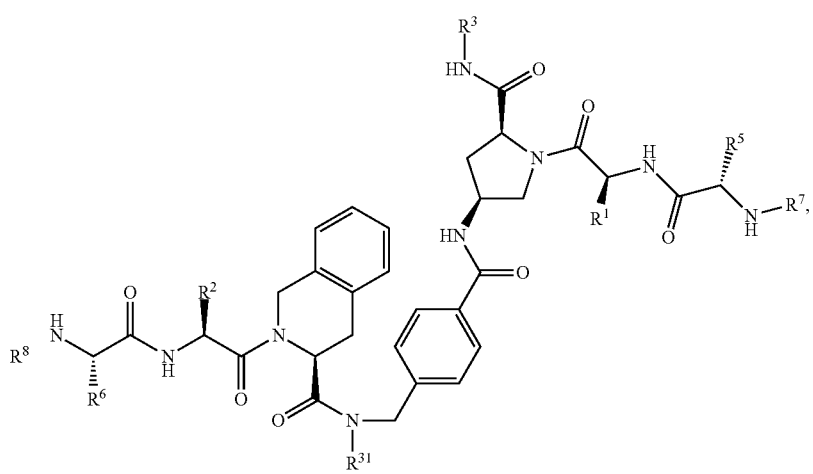

(XXVIII)

R³ and R⁴ are selected from the group comprising:

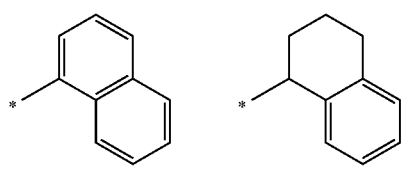

wherein:
R³⁵ is 1-2 substituents selected from alkyl, halogen, alkoxy, cyano and haloalkoxy;
R¹ of Formula (XXVII) and (XXVIII) is selected from H or an optionally substituted alkyl, optionally substituted cycloalkyl, optionally substituted cycloalkylalkyl, optionally substituted heterocyclyl, optionally substituted arylalkyl or optionally substituted aryl;

R² of Formula (XXVII) and (XXVIII) is selected from H or an optionally substituted alkyl, optionally substituted cycloalkyl, optionally substituted cycloalkylalkyl, optionally substituted heterocyclyl, optionally substituted arylalkyl or optionally substituted aryl;

or alternatively,

R¹ and R² of Formula (XXVII) and (XXVIII) are independently selected from an optionally substituted thioalkyl —CR⁶⁰R⁶¹SR⁷⁰, wherein R⁶⁰ and R⁶¹ are selected from H or methyl, and R⁷⁰ is selected from an optionally substituted alkyl, optionally substituted branched alkyl, optionally substituted heterocyclyl, —(CH₂)ᵥCOR²⁰, —CH₂CHR²¹COR²² or —CH₂R²³, wherein:
v is an integer from 1-3;
R²⁰ and R²² of —(CH₂)ᵥCOR²⁰ and —CH₂CHR²¹COR²² are independently selected from OH, NR²⁴R²⁵ or OR²⁶;
R²¹ of —CH₂CHR²¹COR²² is selected from NR²⁴R²⁵;
R²³ of —CH₂R²³ is selected from an optionally substituted aryl or optionally substituted heterocyclyl, where the optional substituents include alkyl and halogen;
R²⁴ of NR²⁴R²⁵ is selected from hydrogen or optionally substituted alkyl;
R²⁵ of NR²⁴R²⁵ is selected from hydrogen, optionally substituted alkyl, optionally substituted branched alkyl, optionally substituted arylalkyl, optionally substituted heterocyclyl, —CH₂CH₂(OCH₂CH₂)ₘCH₃, or a polyamine chain —[CH₂CH₂(CH₂)δNH]ψ, CH₂CH₂(CH₂)ω̄NH₂, such as spermine or spermidine;
wherein δ=0-2, ψ=1-3, ω̄=0-2;
R²⁶ of OR²⁶ is an optionally substituted alkyl, wherein the optional substituents are OH, halogen or NH₂; and
m is an integer from 1-8, R³ and R⁴ of Formula (XXVII) and (XXVIII) are independently selected from an optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

R⁵, R⁶, R⁷ and R⁸ of Formula (XXVII) and (XXVIII) are independently selected from hydrogen, optionally substituted alkyl or optionally substituted cycloalkyl;

R³¹ of Formulas (XXVII) and (XXVIII) is selected from alkyl, aryl, arylalkyl, heteroaryl or heteroarylalkyl optionally further substituted, preferably selected form the group consisting of:

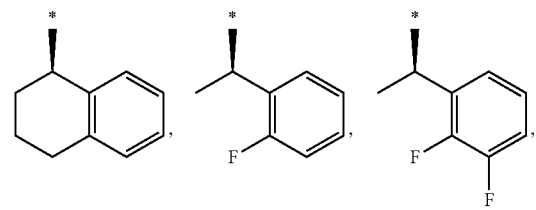

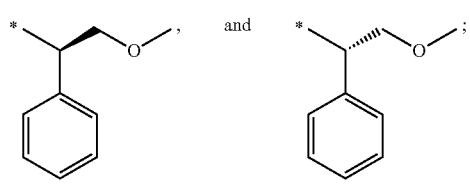

X of Formulas (XXVII) and (XXVIII) is selected from —(CR⁸¹R⁸²)ₘ—, optionally substituted heteroaryl or heterocyclyl,

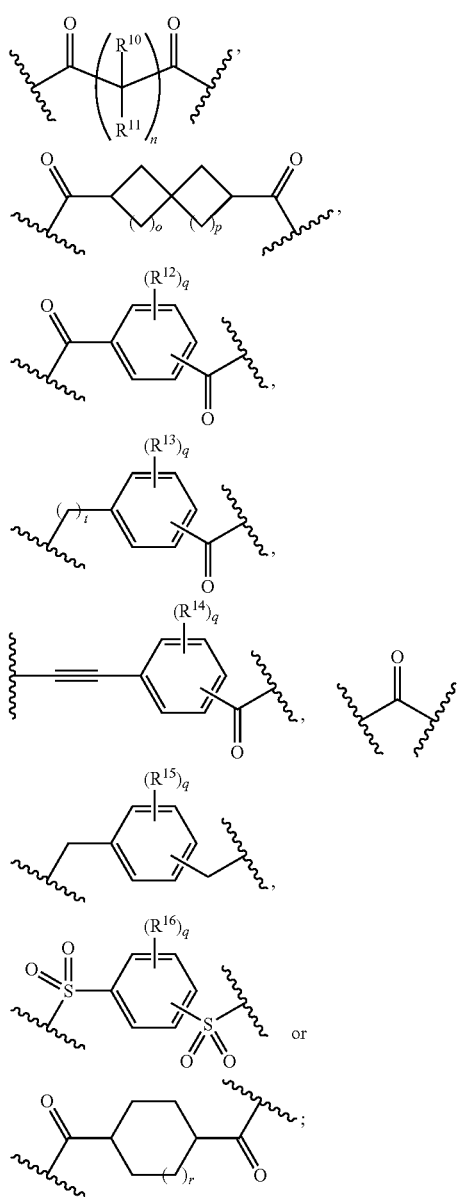

Z of Formulas (XXVII) is selected from C=O, —O—, —NR, —CONH—, —NHCO—, or may be absent;

R⁸¹ and R⁸² of —(CR⁸¹R⁸²)ₘ— are independently selected from hydrogen, halogen, alkyl or cycloalkyl, or R⁸¹ and R⁸² can be taken together to form a carbocyclic ring;

$R^{10}$ and $R^{11}$ of

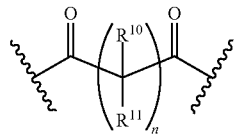

are independently selected from hydrogen, halogen or alkyl;

$R^{12}$, $R^{13}$, $R^{14}$, $R^{15}$ and $R^{16}$ of

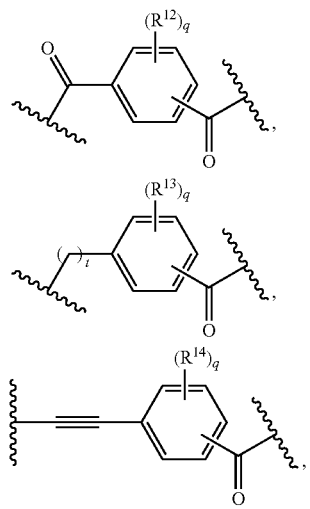

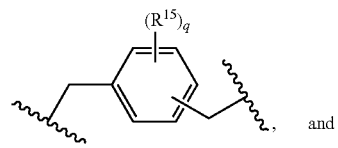

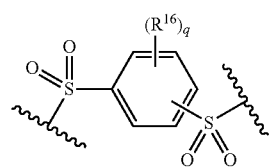

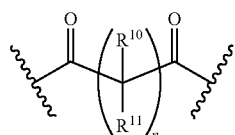

are independently selected from hydrogen, halogen or optionally substituted alkyl or $OR^{17}$;

$R^{17}$ is selected from hydrogen, optionally substituted alkyl or optionally substituted cycloalkyl;

m and n of $-(CR^{21}R^{22})_m-$ and

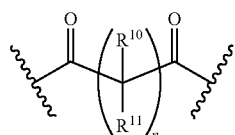

are independently 0, 1, 2, 3, or 4;

o and p of

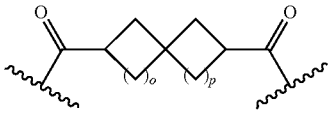

are independently 0, 1, 2 or 3;

q and t of

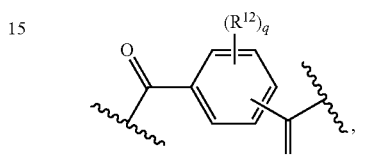

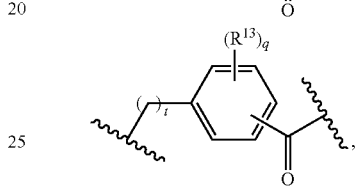

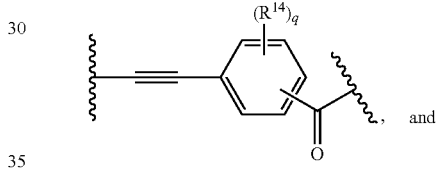

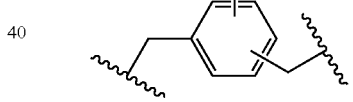

are independently 0, 1, 2, 3, or 4;

r of

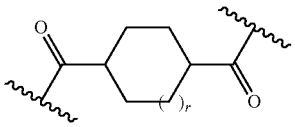

is 0 or 1;

and/or a pharmaceutically acceptable salt, tautomer or stereoisomer thereof.

In any of the compounds described herein, the ILM can have the structure of Formula (XXIX), (XXX), (XXXI), or (XXXII), which are derived from the IAP ligands described in WO Pub. No. 2014/055461 and Kim, K S, *Discovery of tetrahydroisoquinoline-based bivalent heterodimeric IAP antagonists*. Bioorg. Med. Chem. Lett. 24(21), 5022-9 (2014), or an unnatural mimetic thereof, and the chemical linker to linker group L as shown:

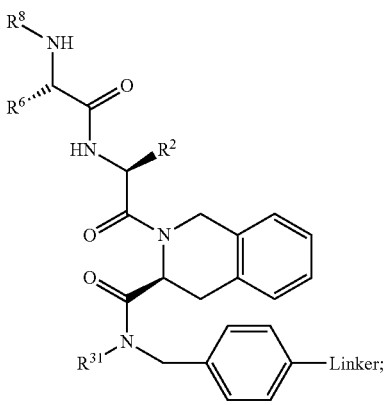

(XXIX)

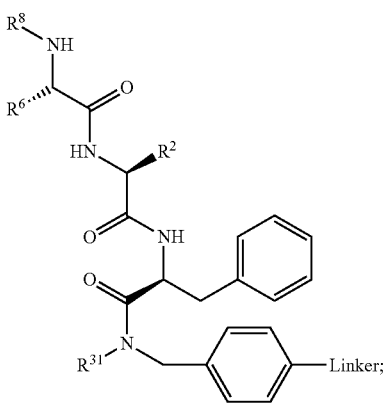

(XXX)

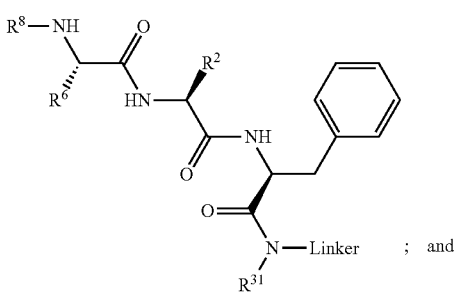

(XXXI)

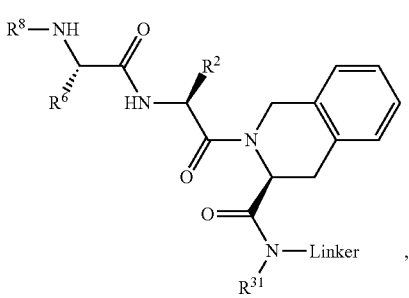

(XXXII)

wherein:

$R^2$ of Formula (XXIX) through (XXXII) is selected from H, an optionally substituted alkyl, optionally substituted cycloalkyl, optionally substituted cycloalkylalkyl, optionally substituted heterocyclyl, optionally substituted arylalkyl or optionally substituted aryl;

or alternatively;

$R^1$ and $R^2$ of Formula (XXVII) and (XXVIII) are independently selected from H, an optionally substituted thioalkyl —$CR^{60}R^{61}SR^{70}$ wherein $R^{60}$ and $R^{61}$ are selected from H or methyl, and $R^{70}$ is an optionally substituted alkyl, optionally substituted branched alkyl, optionally substituted heterocyclyl, —$(CH_2)_vCOR^{20}$, —$CH_2CHR^{21}COR^{22}$ or —$CH_2R^{23}$;

wherein:

v is an integer from 1-3;

$R^{20}$ and $R^{22}$ of —$(CH_2)_vCOR^{20}$ and —$CH_2CHR^{21}COR^{22}$ are independently selected from OH, $NR^{24}R^{25}$ or $OR^{26}$;

$R^{21}$ of —$CH_2CHR^{21}COR^{22}$ is selected from $NR^{24}R^{25}$;

$R^{23}$ of —$CH_2R^{23}$ is selected from an optionally substituted aryl or optionally substituted heterocyclyl, where the optional substituents include alkyl and halogen;

$R^{24}$ of $NR^{24}R^{25}$ is selected from hydrogen or optionally substituted alkyl;

$R^{25}$ of $NR^{24}R^{25}$ is selected from hydrogen, optionally substituted alkyl, optionally substituted branched alkyl, optionally substituted arylalkyl, optionally substituted heterocyclyl, —$CH_2CH_2(OCH_2CH_2)_mCH_3$, or a polyamine chain —$[CH_2CH_2(CH_2)_\delta NH]_\psi CH_2CH_2(CH_2)_{\bar\omega_r}NH_2$, such as spermine or spermidine, wherein $\delta$=0-2, $\psi$=1-3, $\bar\omega$=0-2;

$R^{26}$ of $OR^{26}$ is an optionally substituted alkyl, wherein the optional substituents are OH, halogen or $NH_2$, m is an integer from 1-8;

$R^6$ and $R^8$ of Formula (XXIX) through (XXXII) are independently selected from hydrogen, optionally substituted alkyl or optionally substituted cycloalkyl; and $R^{31}$ of Formulas (XXIX) through (XXXII) is selected from alkyl, aryl, arylalkyl, heteroaryl or heteroarylalkyl optionally further substituted, preferably selected form the group consisting of:

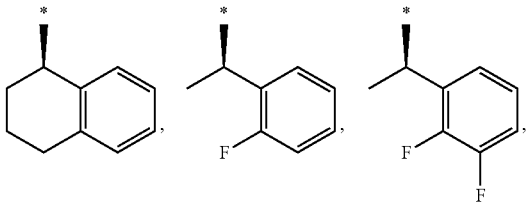

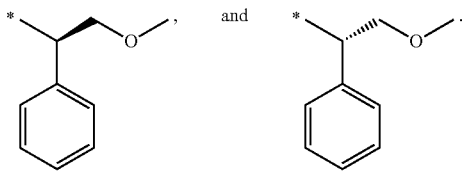

In certain embodiments, the ILM of the compound is:

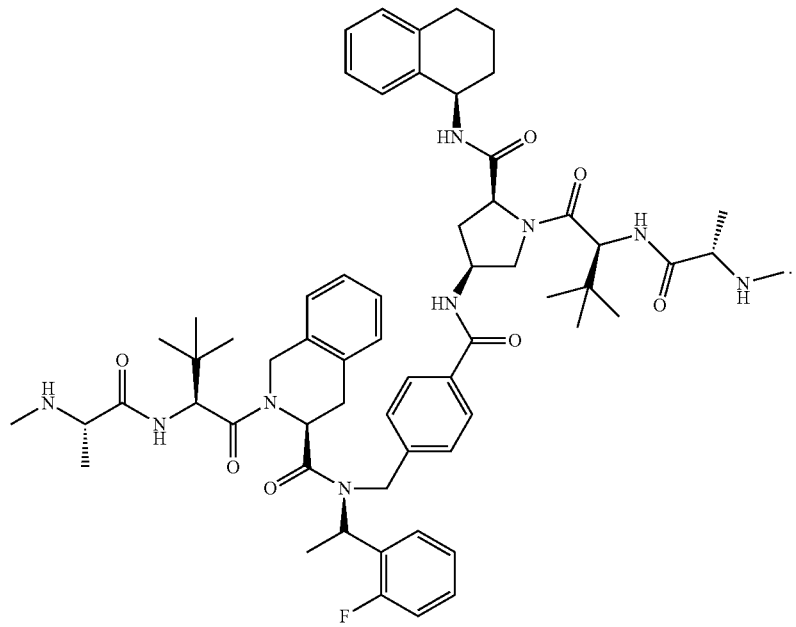

In any of the compounds described herein, the ILM can have the structure of Formula (XXXIII), which are derived from the IAP ligands described in WO Pub. No. 2014/074658 and WO Pub. No. 2013/071035, or an unnatural mimetic thereof:

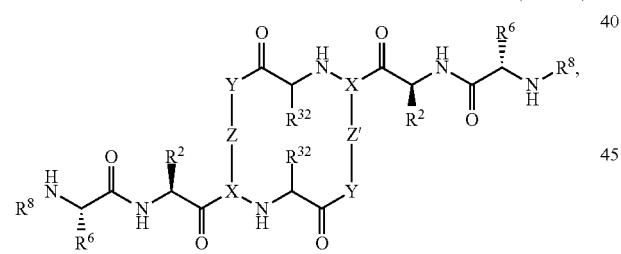
(XXXIII)

wherein:
  $R^2$ of Formula (XXXIII) is selected from H, an optionally substituted alkyl, optionally substituted cycloalkyl, optionally substituted cycloalkylalkyl, optionally substituted heterocyclyl, optionally substituted arylalkyl or optionally substituted aryl;
  $R^6$ and $R^8$ of Formula (XXXIII) are independently selected from hydrogen, optionally substituted alkyl or optionally substituted cycloalkyl;
  $R^{32}$ of Formula (XXXIII) is selected from (C1-C4 alkylene)-$R^{33}$ wherein $R^{33}$ is selected from hydrogen, aryl, heteroaryl or cycloalkyl optionally further substituted;

X of Formula (XXXIII) is selected from:

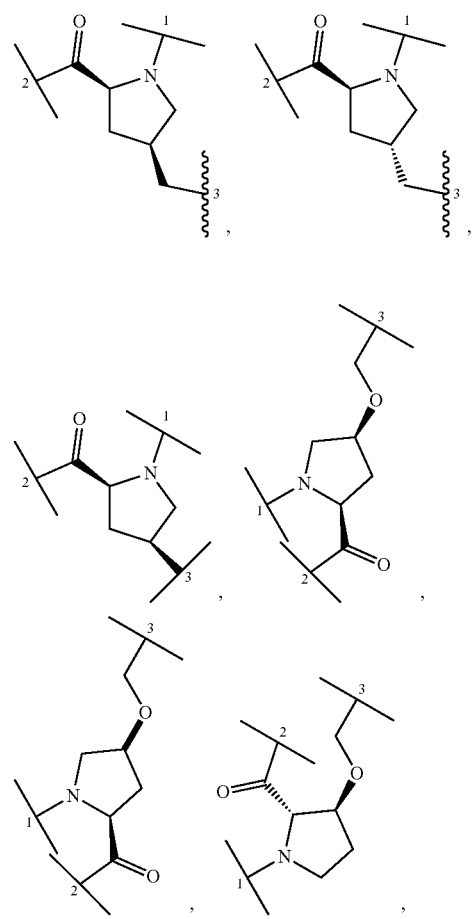

-continued
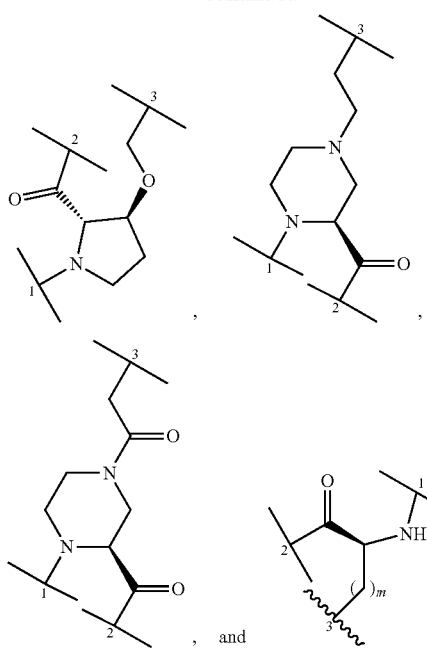,
Z and Z' of Formula (XXXIII) are independently selected from:
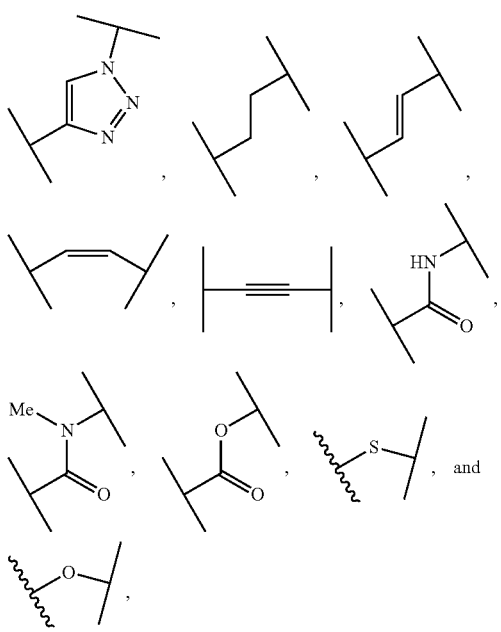
wherein each
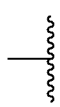
represents a point of attachment to the compound, and Z and Z' cannot both be
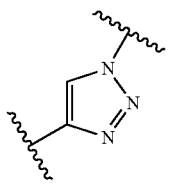 [SMILES: *c1cn(*)nn1]
in any given compound;
Y of Formula (XXXIII) is selected from:
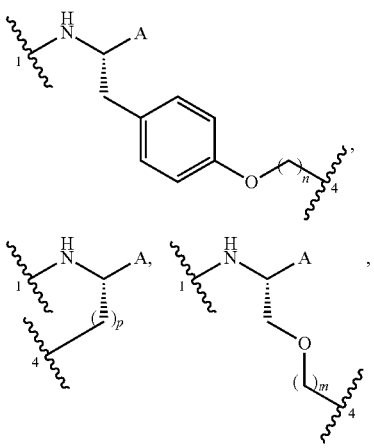
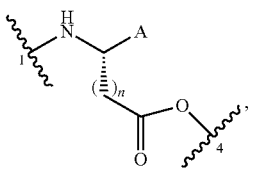
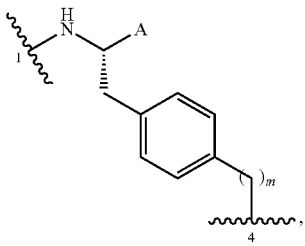
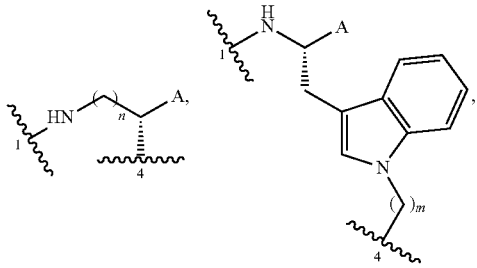

-continued
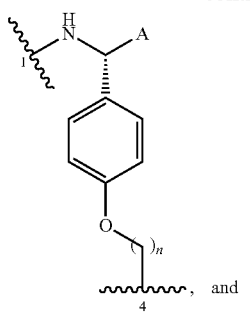
, and
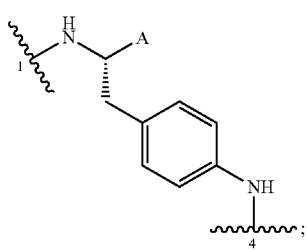
;
wherein Z and Z' of Formula (XXXIII) are the same and Z is
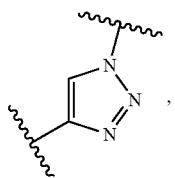 [SMILES: *c1cn(*)nn1 ; ","]
,
wherein each
represents a point of attachment to the compound, X is selected from:
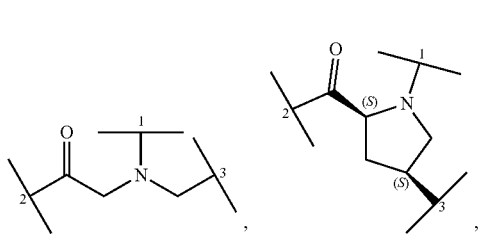
-continued
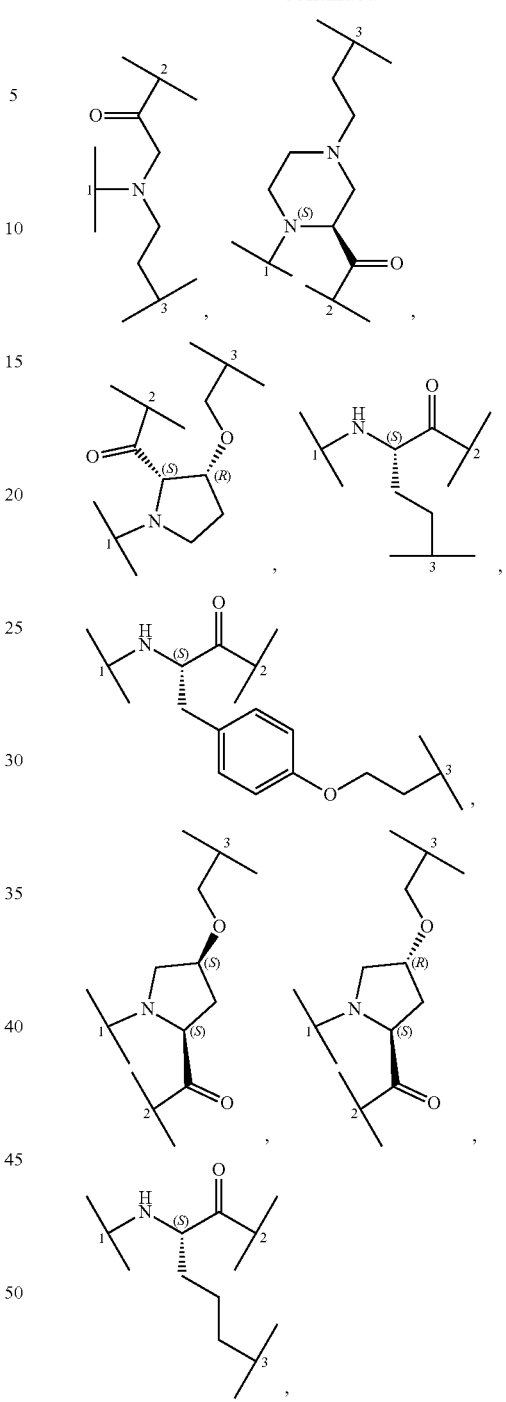
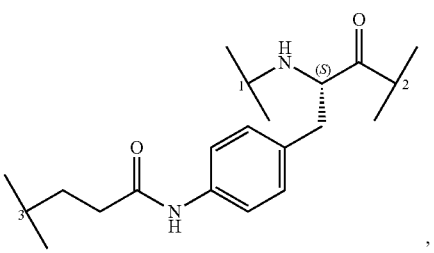
, -continued
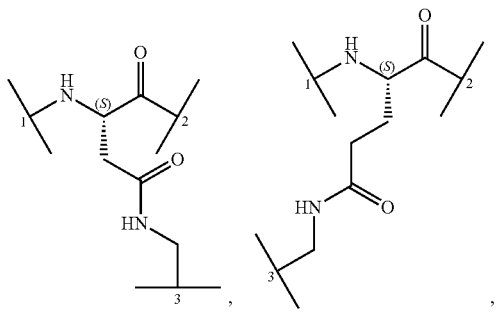
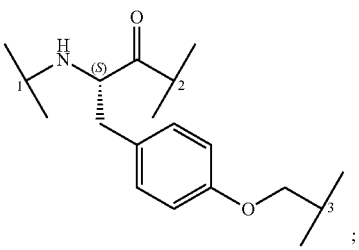
and Y of Formula (XXXIII) is independently selected from:
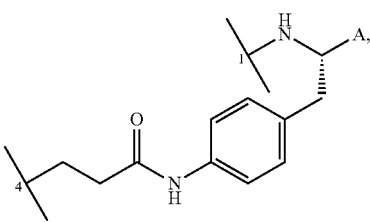
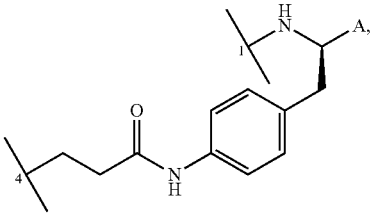
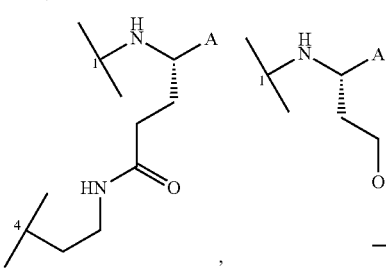
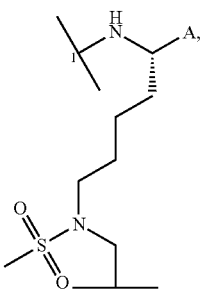 and
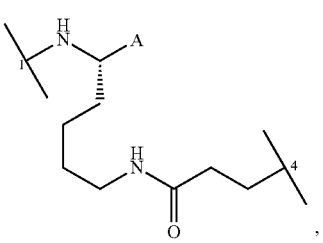

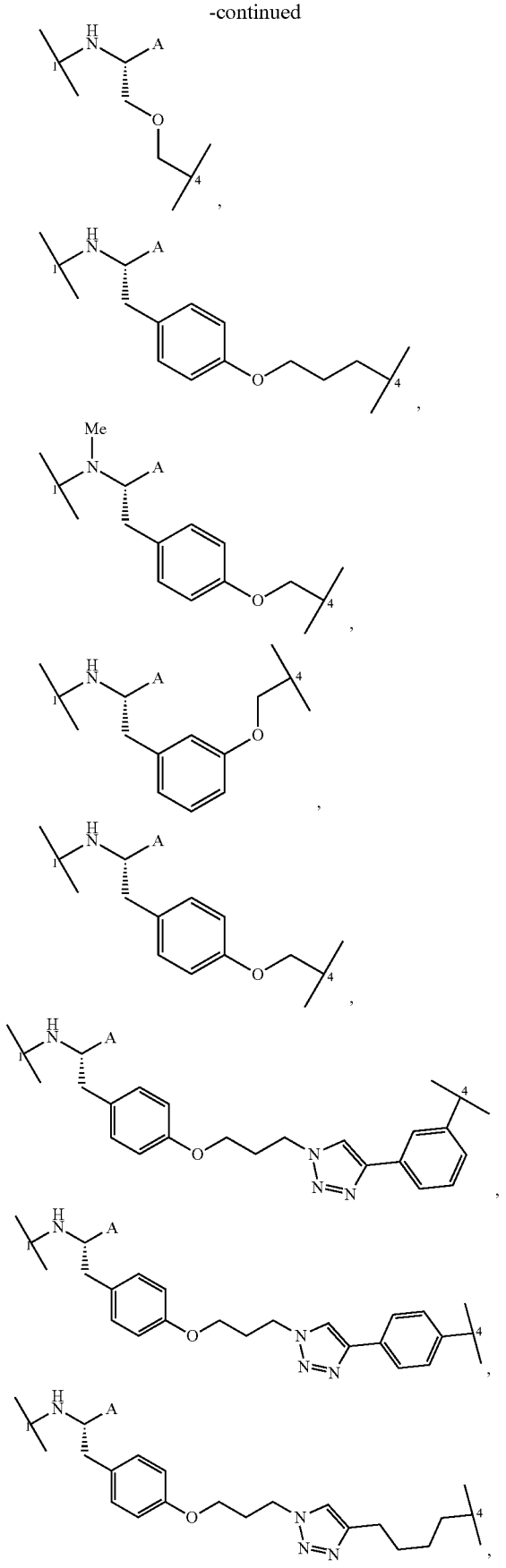
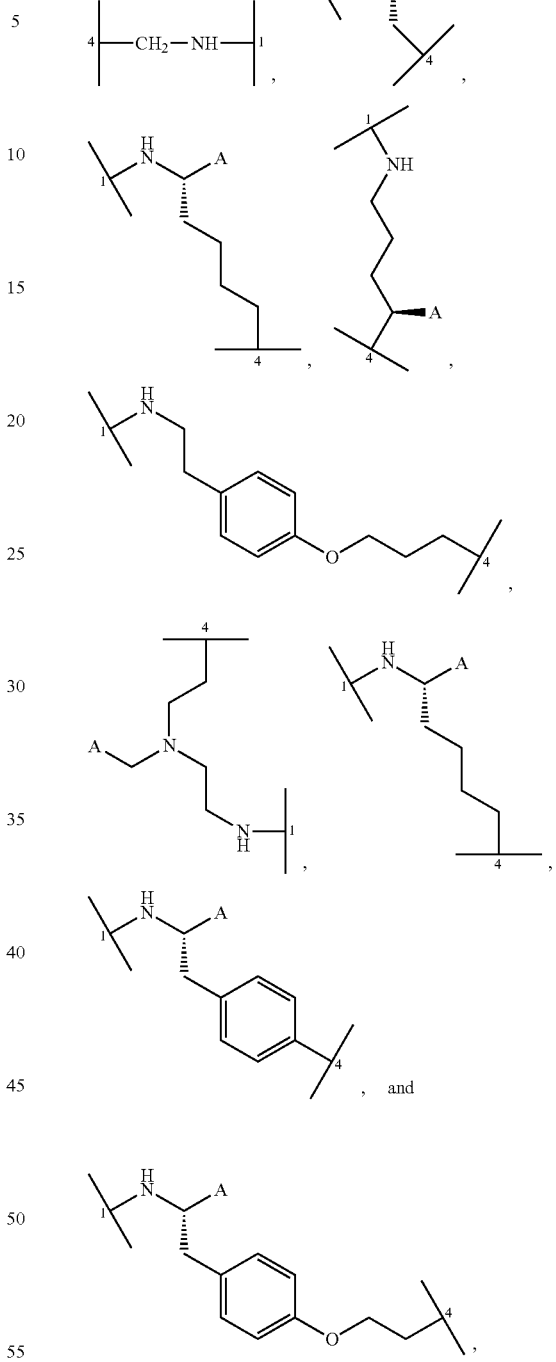
wherein:
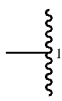
represents a point of attachment to a —C═O portion of the compound;

represents a point of attachment to a —NH portion of the compound;

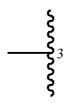

represents a first point of attachment to Z;

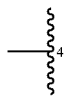

represents a second point of attachment to Z;

m is an integer from 0-3;
n is an integer from 1-3;
p is an integer from 0-4; and
A is —C(O)R$^3$;
R$^3$ is selected from —C(O)R$^3$ is OH, NHCN, NHSO$_2$R$^{10}$, NHOR$^{11}$ or N(R$^{12}$)(R$^{13}$);
R$^{10}$ and F$^{11}$ of NHSO$_2$R$^{10}$ and NHOR$^{11}$ are independently selected from hydrogen, optionally substituted —C$_1$-C$_4$ alkyl, cycloalkyl, aryl, heteroaryl, heterocyclyl or heterocycloalkyl;
R$^{12}$ and R$^{13}$ of N(R$^{12}$)(R$^{13}$) are independently selected from hydrogen, —C$_1$-C$_4$ alkyl, —(C$_1$-C$_4$) alkylene)-NH—(C$_1$-C$_4$ alkyl), and —(C$_1$-C$_4$ alkylene)-O—(C$_1$-C$_4$ hydroxyalkyl), or R$^{12}$ and R$^{13}$ taken together with the nitrogen atom to which they are commonly bound to form a saturated heterocyclyl optionally comprising one additional heteroatom selected from N, O and S, and wherein the saturated heterocycle is optionally substituted with methyl.

In any of the compounds described herein, the ILM can have the structure of Formula (XXXIV) or (XXXV), which are derived from the IAP ligands described in WO Pub. No. 2014/047024, or an unnatural mimetic thereof:

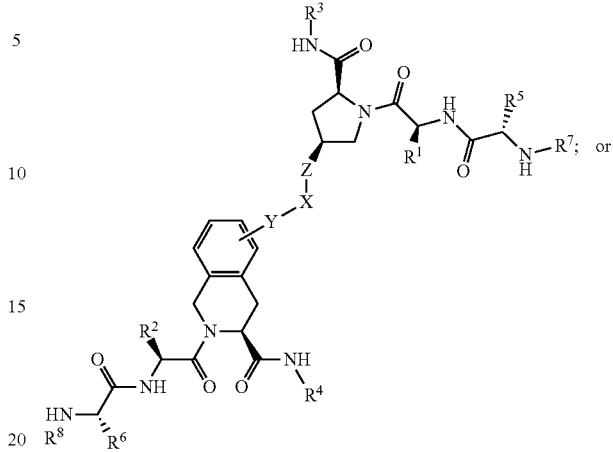

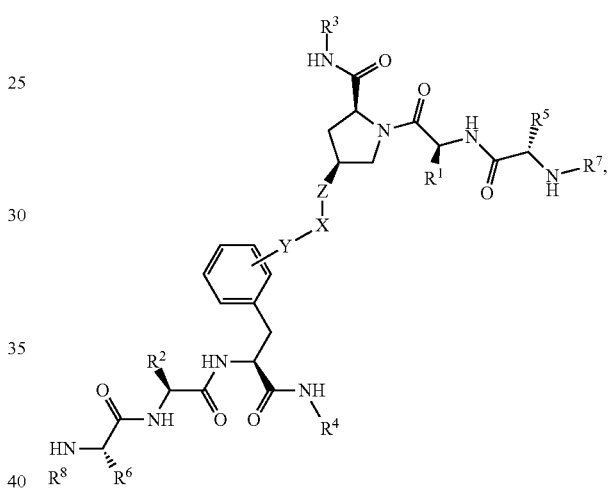

wherein:
X of Formula (XXXIV) or (XXXV) is absent or a group selected from —(CR$^{10}$R$^{11}$)$_m$—, optionally substituted heteroaryl or optionally substituted heterocyclyl,

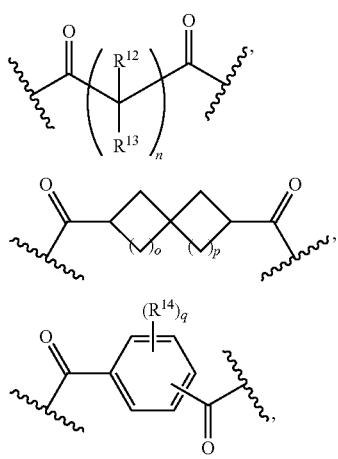

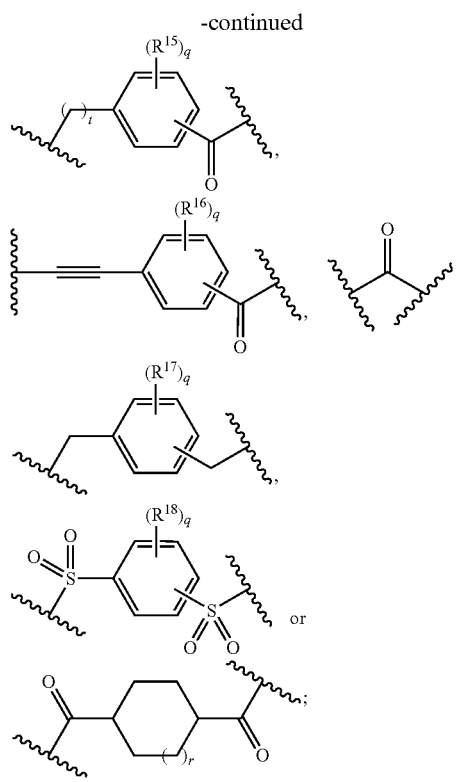

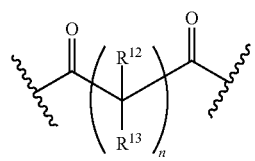

Y and Z of Formula (XXXIV) or (XXXV) are independently selected from C=O, -O-, —NR$^9$—, —CONH—, —NHCO— or may be absent;

R$^1$ and R$^2$ of Formula (XXXIV) or (XXXV) are independently selected from an optionally substituted alkyl, optionally substituted cycloalkyl, optionally substituted cycloalkylalkyl, optionally substituted arylalkyl, optionally substituted aryl, or R$^1$ and R$^2$ of Formula (XXXIV) or (XXXV) are independently selected from optionally substituted thioalkyl wherein the substituents attached to the S atom of the thioalkyl are optionally substituted alkyl, optionally substituted branched alkyl, optionally substituted heterocyclyl, —(CH$_2$)$_v$COR$^{20}$, —CH$_2$CHR$^{21}$COR$^{22}$ or —CH$_2$R$^{23}$; wherein v is an integer from 1-3;

R$^{20}$ and R$^{22}$ of —(CH$_2$)$_v$COR$^{20}$ and —CH$_2$CHR$^{21}$COR$^{22}$ are independently selected from OH, NR$^{24}$R$^{25}$ or OR$^{26}$;

R$^{21}$ of —CH$_2$CHR$^{21}$COR$^{22}$ is selected from NR$^{24}$R$^{25}$;

R$^{23}$ of —CH$_2$R$^{23}$ are selected from an optionally substituted aryl or optionally substituted heterocyclyl, where the optional substituents include alkyl and halogen;

R$^{24}$ of NR$^{24}$R$^{25}$ is selected from hydrogen or optionally substituted alkyl;

R$^{25}$ of NR$^{24}$R$^{25}$ is selected from hydrogen, optionally substituted alkyl, optionally substituted branched alkyl, optionally substituted arylalkyl, optionally substituted heterocyclyl, —CH$_2$(OCH$_2$CH$^{20}$)mCH3, or a polyamine chain;

R$^{26}$ is an optionally substituted alkyl, wherein the optional substituents are OH, halogen or NH$_2$;

m of —(CR$^{10}$R$^{11}$)$_m$— is an integer from 1-8;

R$^3$ and R$^4$ of Formula (XXXIV) or (XXXV) are independently selected from optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

R$^5$, R$^6$, R$^7$ and R$^8$ of Formula (XXXIV) or (XXXV) are independently selected from hydrogen, optionally substituted alkyl or optionally substituted cycloalkyl;

R$^{10}$ and R$^{11}$ of —(CR$^{10}$R$^{11}$)$_m$— are independently selected from hydrogen, halogen or optionally substituted alkyl;

R$^{12}$ and R$^{13}$ of

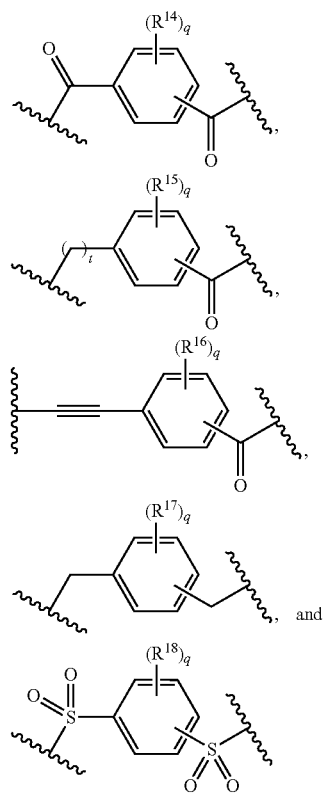

are independently selected from hydrogen, halogen or optionally substituted alkyl, or R$^{12}$ and R$^{13}$ can be taken together to form a carbocyclic ring;

R$^{14}$, R$^{15}$, R$^{16}$, R$^{17}$ and R$^{18}$ of are independently selected from hydrogen, halogen, optionally substituted alkyl or OR$^{19}$;

R$^{19}$ of OR$^{19}$ is selected from hydrogen, optionally substituted alkyl or optionally substituted cycloalkyl;

m and n of —(CR$^{10}$R$^{11}$) are independently 0, 1, 2, 3, or 4;

o and p of —(CR$^{10}$R$^{11}$)$_m$— are independently 0, 1, 2 or 3;

q of —(CR$^{10}$R$^{11}$)$_m$— is 0, 1, 2, 3, or 4; r is 0 or 1;

t of —(CR$^{10}$R$^{11}$)$_m$— is 1, 2, or 3; and/or a pharmaceutically acceptable salt, tautomer or stereoisomer thereof.

In any of the compounds described herein, the ILM can have the structure of Formula (XXXVI), which are derived from the IAP ligands described in WO Pub. No. 2014/025759, or an unnatural mimetic thereof:

(XXXVI)

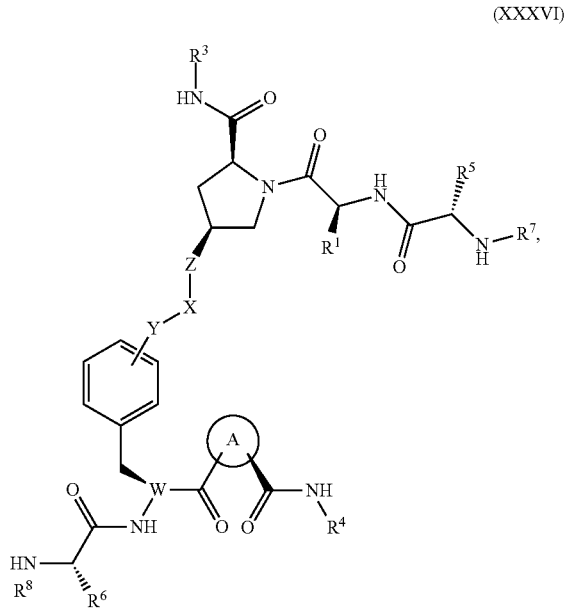

where:

A of Formula (XXXVI) is selected from:

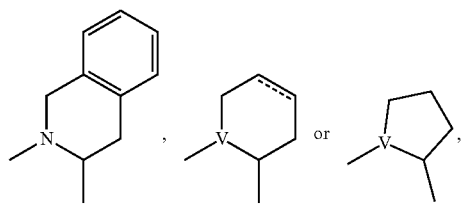

where the dotted line represents an optional double bond;

X of Formula (XXXVI) is selected from: —(CR$^{21}$R$^{22}$)$_m$—,

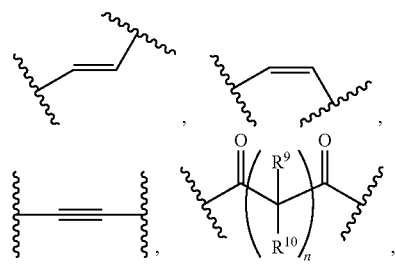

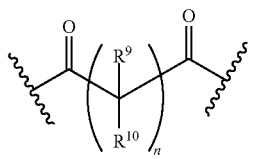

Y and Z of Formula (XXXVI) are independently selected from -O-, —NR$^6$— or are absent;

V of Formula (XXXVI) is selected from —N— or —CH—;

W of Formula (XXXVI) is selected from —CH— or —N—;

R$^1$ of Formula (XXXVI) is selected from an optionally substituted alkyl, optionally substituted cycloalkyl, optionally substituted cycloalkylalkyl, optionally substituted arylalkyl or optionally substituted aryl;

R$^3$ and R$^4$ of Formula (XXXVI) are independently selected from optionally substituted alkyl, optionally substituted cycloalkyl, optionally substituted aryl, optionally substituted heteroaryl, optionally substituted heterocyclyl, optionally substituted arylalkyl, optionally substituted heteroarylalkyl or optionally substituted heterocycloalkyl;

R$^5$, R$^6$, R$^7$ and R$^8$ of Formula (XXIV), (XXV) or (XXVI) are independently selected from hydrogen, optionally substituted alkyl or optionally substituted cycloalkyl, or preferably methyl;

R$^9$ and R$^{10}$ of are independently selected from hydrogen, halogen or optionally substituted alkyl, or R$^9$ and R$^{10}$ can be taken together to form a ring;

$R^{11}$, $R^{12}$, $R^{13}$ and $R^{14}$ of

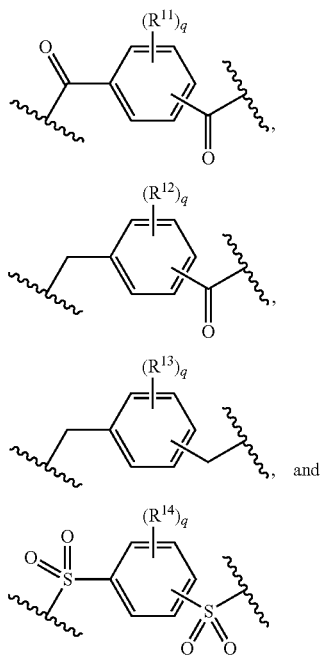

are independently selected from hydrogen, halogen, optionally substituted alkyl or $OR^{15}$;

$R^{15}$ of $OR^{15}$ is selected from hydrogen, optionally substituted alkyl or optionally substituted cycloalkyl;

m and n of —$(CR^{21}R^{22})_m$— and

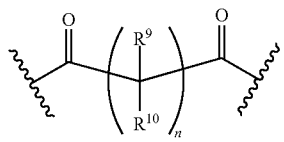

are independently selected from 0, 1, 2, 3, or 4;

o and p of

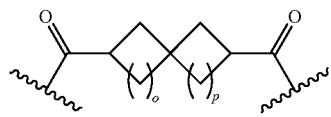

and are independently selected from 0, 1, 2 or 3;

q of

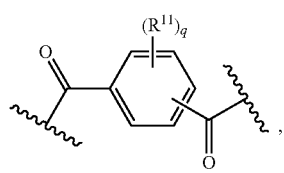

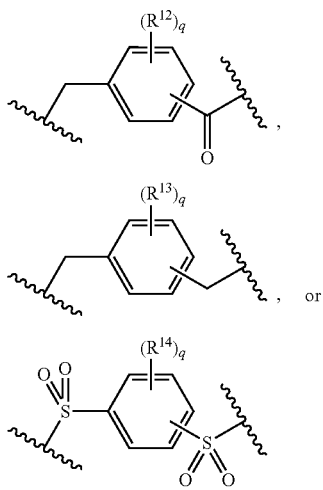

is selected from 0, 1, 2, 3, or 4;

r of

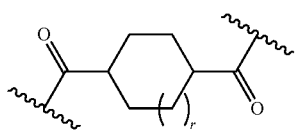

is selected from 0 or 1, and/or or a pharmaceutically acceptable salt, tautomer or stereoisomer thereof.

In any of the compounds described herein, the ILM can have the structure of Formula (XXXVII) or (XXXVIII), which are derived from the IAP ligands described in WO Pub. No. 2014/011712, or an unnatural mimetic thereof:

(XXXVII)

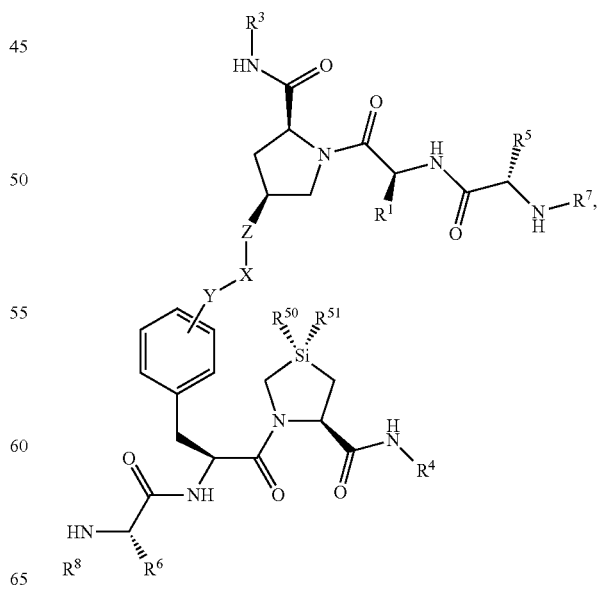

(XXXVIII)

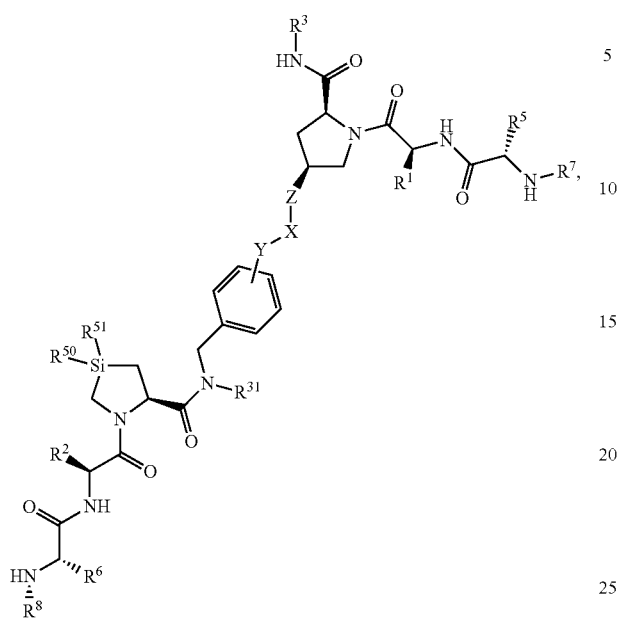

wherein:

X of Formulas (XXXVII) and (XXXVIII) is —(CR$^{16}$R$^{17}$)$_m$—,

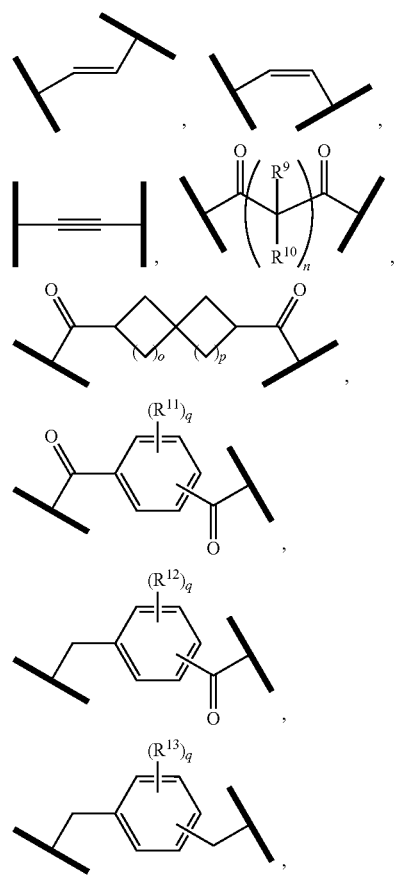

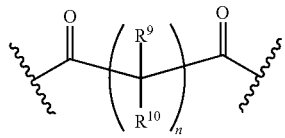

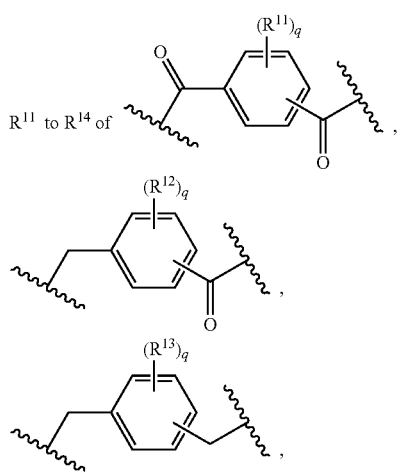

or absent;

Y and Z of Formula (XXXVII) and (XXXVIII) are independently selected from -O-, C=O, NR$^6$ or are absent;

R$^1$ and R$^2$ of Formula (XXXVII) and (XXXVIII) are selected from optionally substituted alkyl, optionally substituted cycloalkyl, optionally substituted alkylaryl or optionally substituted aryl;

R$^3$ and R$^4$ of Formula (XXXVII) and (XXXVIII) are independently selected from optionally substituted alkyl, optionally substituted cycloalkyl, optionally substituted cycloalkylalkyl, optionally substituted arylalkyl or optionally substituted aryl;

R$^5$ and R$^6$ of Formula (XXXVII) and (XXXVIII) are independently selected from optionally substituted alkyl or optionally substituted cycloalkyl;

R$^7$ and R$^8$ of Formula (XXXVII) and (XXXVIII) are independently selected from hydrogen, optionally substituted alkyl or optionally substituted cycloalkyl, or preferably methyl;

R$^9$ and R$^{10}$ of are independently selected from hydrogen, optionally substituted alkyl, or R$^9$ and R$^{10}$ may be taken together to form a ring;

R$^{11}$ to R$^{14}$ of

-continued

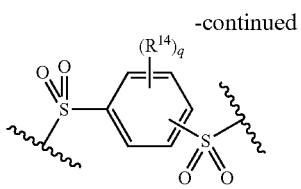

are independently selected from hydrogen, halogen, optionally substituted alkyl or $OR^{15}$;
  $R^{15}$ of $OR^{15}$ is selected from hydrogen, optionally substituted alkyl or optionally substituted cycloalkyl;
  $R^{16}$ and $R^{17}$ of $-(CR^{16}R^{17})_m-$ are independently selected from hydrogen, halogen or optionally substituted alkyl;
  $R^{50}$ and $R^{51}$ of Formula (XXXVII) and (XXXVIII) are independently selected from optionally substituted alkyl, or $R^{50}$ and $R^{51}$ are taken together to form a ring;
  m and n of $-(CR^{16}R^{17})_m-$ and

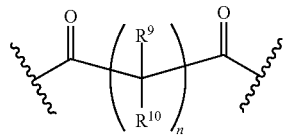

are independently an integer from 0-4;
o and p of

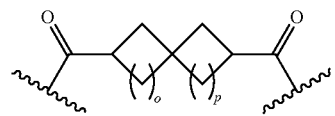

are independently an integer from 0-3;
q of

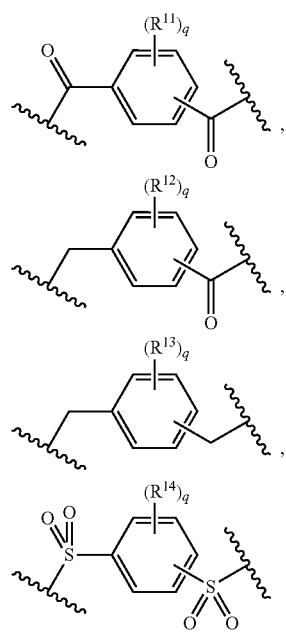

is an integer from 0-4; and
r of

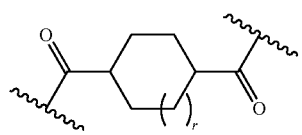

is an integer from 0-1;
or a pharmaceutically acceptable salt, tautomer or stereoisomer thereof.

In an embodiment, $R^1$ and $R^2$ of the ILM of Formula (XXXVII) or (XXXVIII) are t-butyl and $R^3$ and $R^4$ of the ILM of Formula (XXXVII) or (XXXVIII) are tetrahydronaphtalene.

In any of the compounds described herein, the ILM can have the structure of Formula (XXXIX) or (XL), which are derived from the IAP ligands described in WO Pub. No. 2013/071039, or an unnatural mimetic thereof:

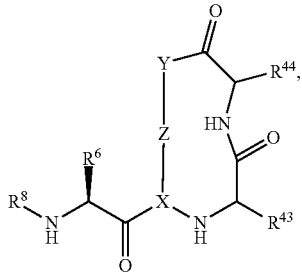

(XXXIX)

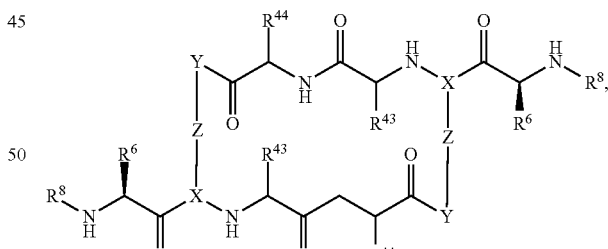

(XL)

wherein:
  $R^{43}$ and $R^{44}$ of Formulas (XXXIX) and (XL) are independently selected from hydrogen, alkyl, aryl, arylalkyl, heteroaryl, heteroarylalkyl, cycloalkyl, cycloalkylalkyl further optionally substituted, and
  $R^6$ and $R^8$ of Formula (XXXIX) and (XL) are independently selected from hydrogen, optionally substituted alkyl or optionally substituted cycloalkyl.
  each X of Formulas (XXXIX) and (XL) is independently selected from:

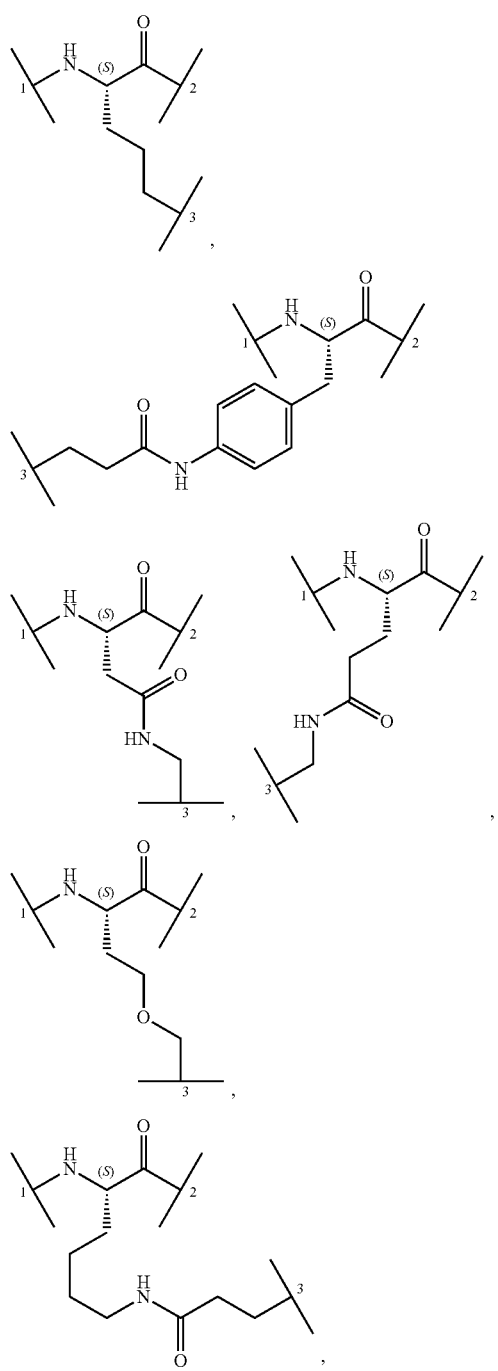
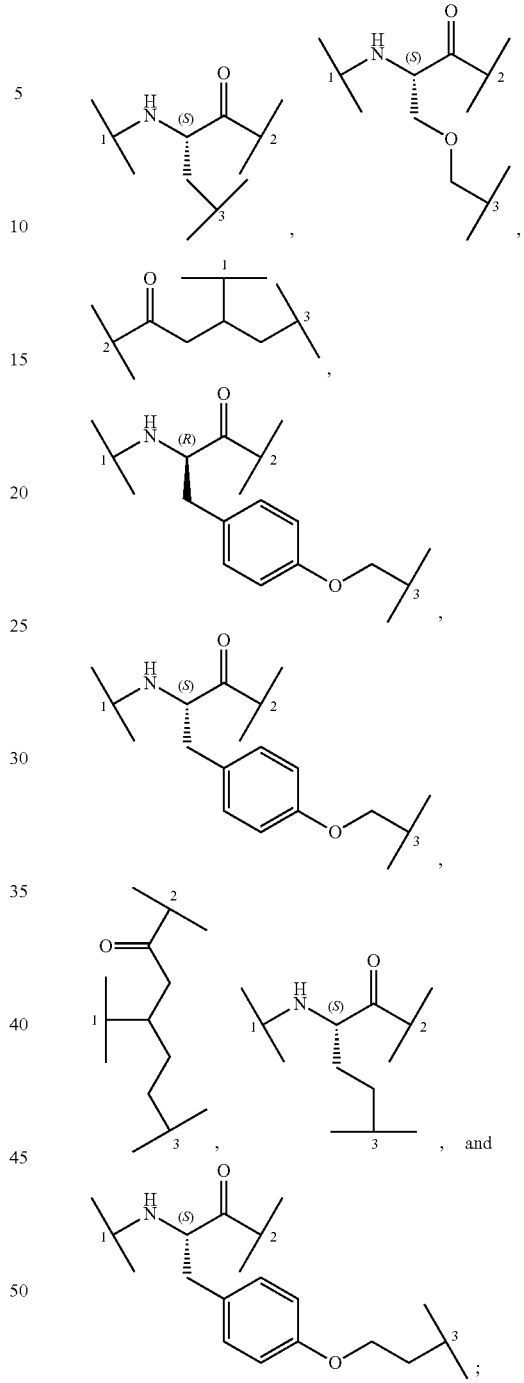
each Z of Formulas (XXXIX) and (XL) is selected from
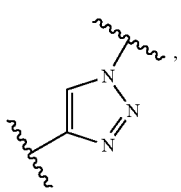 [SMILES: *c1cn(*)nn1]

wherein each
represents a point of attachment to the compound; and each Y is selected from:
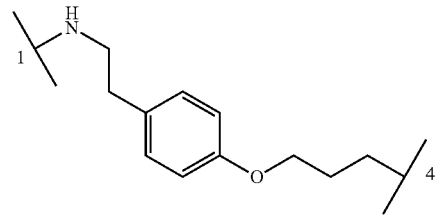
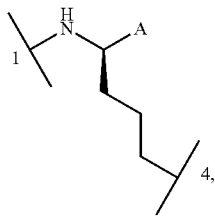
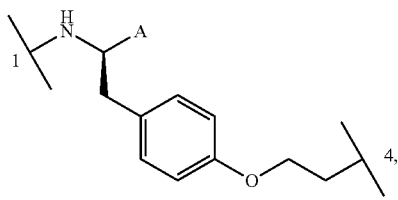
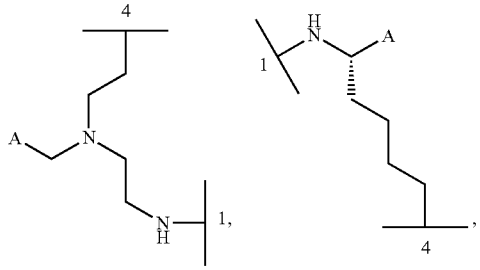
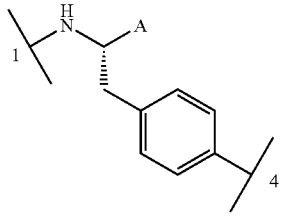
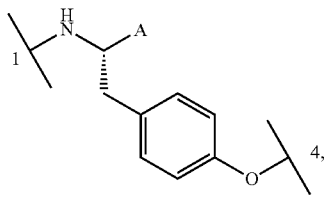
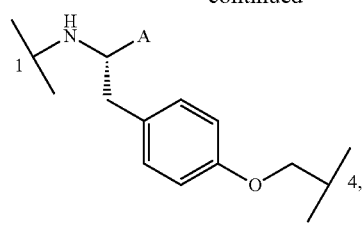
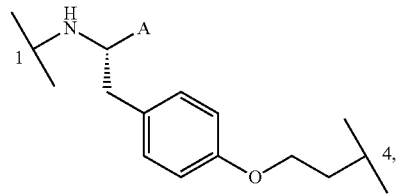
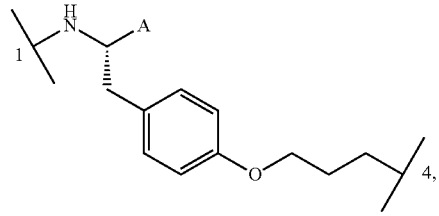
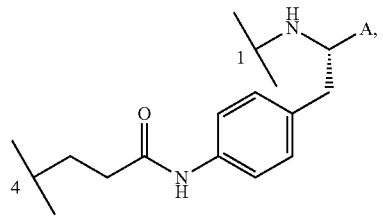
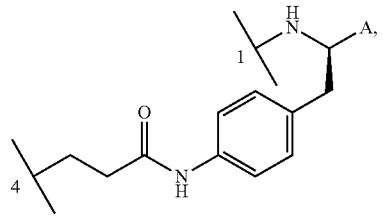
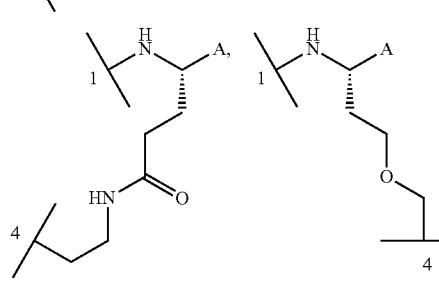
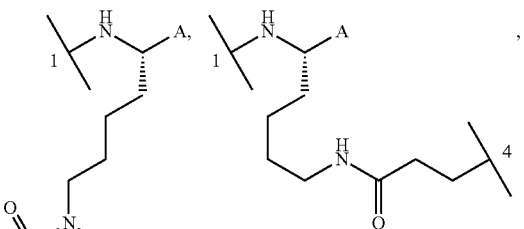

-continued

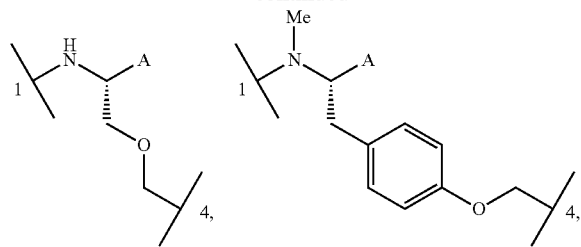
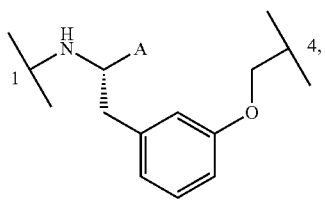
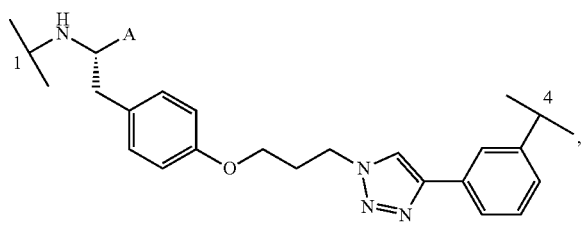
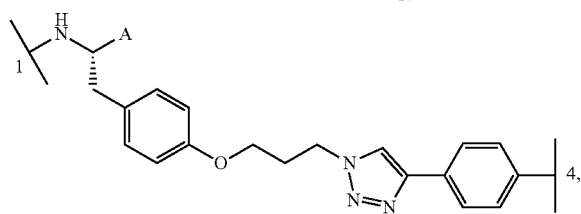
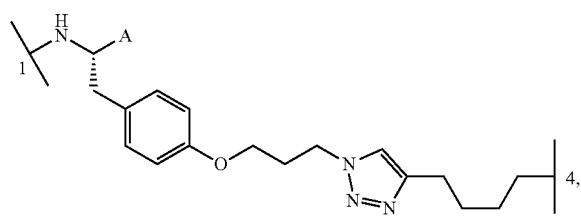
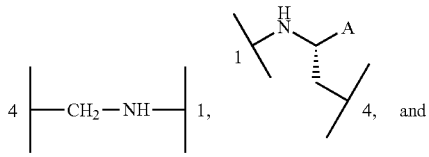

wherein:

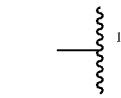

represents a point of attachment to a —C=O portion of the compound;

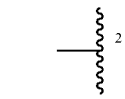

represents a point of attachment to an amino portion of the compound;

represents a first point of attachment to Z;

represents a second point of attachment to Z; and
A is selected from —C(O)R$^3$ or

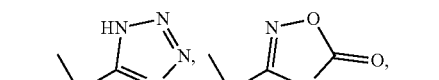
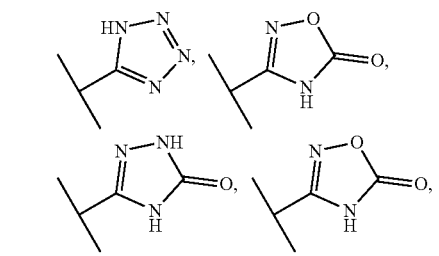
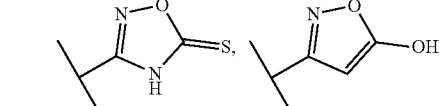
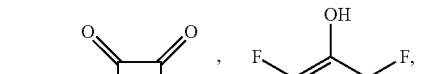
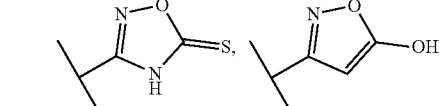
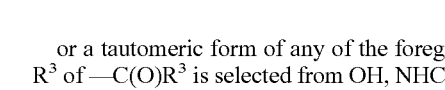
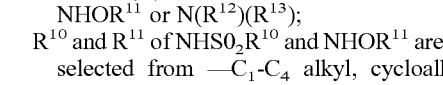
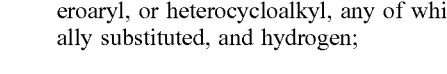

or a tautomeric form of any of the foregoing, wherein:
R$^3$ of —C(O)R$^3$ is selected from OH, NHCN, NHSO$_2$R$^{10}$, NHOR$^{11}$ or N(R$^{12}$)(R$^{13}$);
R$^{10}$ and R$^{11}$ of NHSO$_2$R$^{10}$ and NHOR$^{11}$ are independently selected from —C$_1$-C$_4$ alkyl, cycloalkyl, aryl, heteroaryl, or heterocycloalkyl, any of which are optionally substituted, and hydrogen;

each of $R^{12}$ and $R^{13}$ of $N(R^{12})(R^{13})$ are independently selected from hydrogen, —$C_1$-$C_4$ alkyl, —($C_1$-$C_4$ alkylene)-NH—($C_1$-$C_4$ alkyl), benzyl, —($C_1$-$C_4$ alkylene)-C(O)OH, —($C_1$-$C_4$alkylene)-C(O)CH$_3$, —CH(benzyl)-COOH, —$C_1$-$C_4$ alkoxy, and —($C_1$-$C_4$ alkylene)-O—($C_1$-$C_4$ hydroxyalkyl); or $R^{12}$ and $R^{13}$ of $N(R^{12})(R^{13})$ are taken together with the nitrogen atom to which they are commonly bound to form a saturated heterocyclyl optionally comprising one additional heteroatom selected from N, O and S, and wherein the saturated heterocycle is optionally substituted with methyl.

In any of the compounds described herein, the ILM can have the structure of Formula (XLI), which are derived from the IAP ligands described in WO Pub. No. 2013/071039, or an unnatural mimetic thereof:

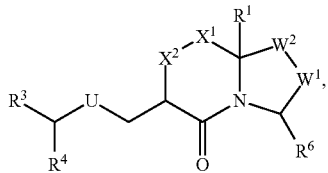

(XLI)

wherein:
$W^1$ of Formula (XLI) is selected from O, S, N—$R^A$, or $C(R^{8a})(R^{8b})$;
$W^2$ of Formula (XLI) is selected from O, S, N—$R^A$, or $C(R^{8c})(R^{8d})$; provided that $W^1$ and $W^2$ are not both O, or both S;
$R^1$ of Formula (XLI) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);
when $X^1$ is selected from O, N—$R^A$, S, S(O), or S(O)$_2$, then $X^2$ is $C(R^{2a}R^{2b})$;
or:
$X^1$ of Formula (XLI) is selected from $CR^{2c}R^{2d}$ and $X^2$ is $CR^{2a}R^{2b}$, and $R^{2c}$ and $R^{2a}$ together form a bond;
or:
$X^1$ and $X^2$ of Formula (XLI) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring;
or:
$X^1$ of Formula (XLI) is selected from CH$_2$ and $X^2$ is C=O, C=C($R^C$)$_2$, or C=N$R^C$; where each $R^c$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl- (substituted or unsubstituted aryl), or —$C_1$-$C_6$alkyl-(substituted or unsubstituted heteroaryl);
$R^A$ of N—$R^A$ is selected from H, $C_1$-$C_6$alkyl, —C(=O) $C_1$-$C_2$alkyl, substituted or unsubstituted aryl, or substituted or unsubstituted heteroaryl;
$R^{2a}$, $R^{2b}$, $R^{2c}$, $R^{2d}$ of $CR^{2c}R^{2d}$ of $CR^{2c}R^{2d}$ and $CR^{2a}R^{2b}$ are independently selected from H, substituted or unsubstituted C1-C6alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl- (substituted or unsubstituted aryl), —$C_1$-$C_6$alkyl-(substituted or unsubstituted heteroaryl) and —C(=O)$R^B$;
$R^B$ of —C(=O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl- (substituted or unsubstituted aryl), —$C_1$-$C_6$alkyl-(substituted or unsubstituted heteroaryl), or —NR$^D$R$^E$;
$R^D$ and $R^E$ of NR$^D$R$^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl- (substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl- (substituted or unsubstituted heteroaryl);
m of Formula (XLI) is selected from 0, 1 or 2;
—U— of Formula (XLI) is selected from —NHC(=O)—, —C(=O)NH—, —NHS(=O)$_2$—, —S(=O)$_2$ NH—, —NHC(=O)NH—, —NH(C=O)O—, —O(C=O)NH—, or —NHS(=O)$_2$NH—;
$R^3$ of Formula (XLI) is selected from $C_1$-$C_3$alkyl, or $C_1$-$C_3$fluoroalkyl;
$R^4$ of Formula (XLI) is selected from —NHR5, —N($R^5$)2, —N+($R^5$)3 or —O$R^5$;
each $R^5$ of —NHR$^5$, —N($R^5$)2, —N+($R^5$)3 and —O$R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);
or:
$R^3$ and $R^5$ of Formula (XLI) together with the atoms to which they are attached form a substituted or unsubstituted 5-7 membered ring;
or:
$R^3$ of Formula (XLI) is bonded to a nitrogen atom of U to form a substituted or unsubstituted 5-7 membered ring;
$R^6$ of Formula (XLI) is selected from —NHC(=O)$R^7$, —C(=O)NHR$^7$, —NHS(=O)2$R^7$, —S(=O)$_2$NHR$^7$; —NHC(=O)NHR$^7$, —NHS(=O)$_2$NHR$^7$, —($C_1$-$C_3$alkyl)-NHC(=O)$R^7$, —($C_1$-$C_3$alkyl)-C(=O)NHR$^7$, —($C_1$-$C_3$alkyl)-NHS(=O)2$R^7$, —($C_1$-$C_3$alkyl)-S(=O)2NHR$^7$; —($C_1$-$C_3$alkyl)-NHC(=O)NHR$^7$, —($C_1$-$C_3$alkyl)-NHS(=O)2NHR$^7$, substituted or unsubstituted $C_2$-$C_{10}$heterocycloalkyl, or substituted or unsubstituted heteroaryl;

each R⁷ of —NHC(=O)R⁷, —C(=O)NHR⁷, —NHS(=O)2R⁷, —S(=O)₂NHR⁷; —NHC(=O)NHR⁷, —NHS(=O)₂NHR⁷, —(C₁-C₃alkyl)-NHC(=O)R⁷, —(C₁-C₃alkyl)-C(=O)NHR⁷, —(C₁-C₃alkyl)-NHS(=O)2R⁷, —(C₁-C₃alkyl)-S(=O)2NHR⁷; —(C₁-C₃alkyl)-NHC(=O)NHR⁷, —(C₁-C₃alkyl)-NHS(=O)2NHR⁷ is independently selected from C₁-C₆alkyl, C₁-C₆haloalkyl, C₁-C₆heteroalkyl, a substituted or unsubstituted C3-C10cycloalkyl, a substituted or unsubstituted C₂-C₁₀heterocycloalkyl, a substituted or unsubstituted aryl, a substituted or unsubstituted heteroaryl, —C₁-C₆alkyl-(substituted or unsubstituted C₃-C₁₀cycloalkyl), —C₁-C₆alkyl- (substituted or unsubstituted C2-C10heterocyclo alkyl, —C1-C6alkyl-(substituted or unsubstituted aryl), —C₁-C₆alkyl-(substituted or unsubstituted heteroaryl), —(CH2)p-CH(substituted or unsubstituted aryl)2, —(CH₂)ₚ—CH(substituted or unsubstituted heteroaryl)2, —(CH₂)ₚ—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of R⁷ is selected from 0, 1 or 2;

$R^{8a}$, $R^{8b}$, $R^{8c}$, and $R^{8d}$ of $C(R^{8a})(R^{8b})$ and $C(R^{8c})(R^{8d})$ are independently selected from H, C₁-C₆alkyl, C₁-C₆fluoroalkyl, C₁-C₆ alkoxy, C₁-C₆heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 R⁹; and each R⁹ of $R^{8a}$, $R^{8b}$, $R^{8c}$ and $R^{8d}$ is independently selected from halogen, —OH, —SH, (C=O), CN, C₁-C₄alkyl, C1-C4fluoroalkyl, C₁-C₄ alkoxy, C₁-C₄ fluoroalkoxy, —NH₂, —NH(C₁-C₄alkyl), —NH(C₁-C₄alkyl)₂, —C(=O)OH, —C(=0)NH₂, —C(=O)C₁-C₃alkyl, —S(=O)₂CH₃, —NH(C₁-C₄alkyl)-OH, —NH(C₁-C₄alkyl)-O—(C—C₄alkyl), —O(C₁-C₄alkyl)-NH2; —O(C₁-C₄alkyl)-NH—(C₁-C₄alkyl), and —O(C₁-C₄alkyl)-N—(C₁-C₄alkyl)₂, or two R⁹ together with the atoms to which they are attached form a methylene dioxy or ethylene dioxy ring substituted or unsubstituted with halogen, —OH, or C₁-C₃alkyl.

In any of the compounds described herein, the ILM can have the structure of Formula (XLII), which are derived from the IAP ligands described in WO Pub. No. 2013/071039, or an unnatural mimetic thereof:

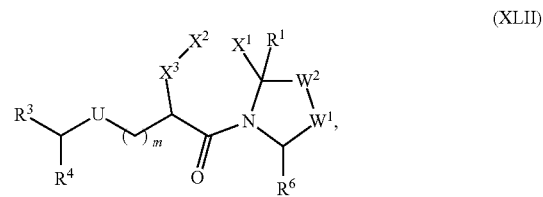

(XLII)

wherein:
W¹ of Formula (XLII) is O, S, N—$R^A$, or $C(R^{8a})(R^{8b})$;
W² of Formula (XLII) is O, S, N—$R^A$, or $C(R^{8c})(R^{8d})$; provided that W¹ and W² are not both O, or both S;
R¹ of Formula (XLII) is selected from H, C₁-C₆alkyl, C₃-C₆cycloalkyl, —C₁-C₆alkyl-(substituted or unsubstituted C₃-C₆cycloalkyl), substituted or unsubstituted aryl, substituted or unsubstituted heteroaryl, —C₁-C₆alkyl-(substituted or unsubstituted aryl), or —C₁-C₆alkyl-(substituted or unsubstituted heteroaryl);
when X¹ of Formula (XLII) is N—$R^A$, then X² is C=O, or $CR^{2c}R^{2d}$, and X³ is $CR^{2a}R^{2b}$;

or:

when X¹ of Formula (XLII) is selected from S, S(O), or S(O)₂, then X² is $CR^{2c}R^{2d}$, and X³ is $CR^{2a}R^{2b}$;

or:

when X¹ of Formula (XLII) is O, then X² is $CR^{2c}R^{2d}$ and N—$R^A$ and X³ is $CR^{2a}R^{2b}$;

or:

when X¹ of Formula (XLII) is CH₃, then X² is selected from O, N—$R^A$, S, S(O), or S(O)₂, and X³ is $CR^{2a}R^{2b}$;
when X¹ of Formula (XLII) is $CR^{2e}R^{2f}$ and X2 is $CR^{2c}R^{2d}$; and $R^{2e}$ and $R^{2c}$ together form a bond, and X³ of Formula (VLII) is $CR^{2a}R^{2b}$;

or:

X¹ and X³ of Formula (XLII) are both CH₂ and X² of Formula (XLII) is C=0, C=C($R^C$)2, or C=N$R^C$; where each $R^C$ is independently selected from H, —CN, —OH, alkoxy, substituted or unsubstituted C1-C6alkyl, substituted or unsubstituted C₃-C₆cycloalkyl, substituted or unsubstituted C₂-C₅heterocycloalkyl, substituted or unsubstituted aryl, substituted or unsubstituted heteroaryl, —C₁-C₆alkyl-(substituted or unsubstituted C₃-C₆cycloalkyl), —C₁-C₆alkyl-(substituted or unsubstituted C₂-C₅heterocycloalkyl), —C₁-C₆alkyl-(substituted or unsubstituted aryl), or —C₁-C₆alkyl- (substituted or unsubstituted heteroaryl);

or:

X¹ and X² of Formula (XLII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;

or:

$X^2$ and $X^3$ of Formula (XLII) are independently selected from C and N, and are embers of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (VLII) is $CR^{2e}R^{2f}$;

$R^A$ of N—$R^A$ is selected from H, $C_1$-$C_6$alkyl, —C(=O) $C_1$-$C_2$alkyl, substituted or unsubstituted aryl, or substituted or unsubstituted heteroaryl;

$R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{2f}$ are independently selected from H, substituted or unsubstituted C1-C6alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ of —C(=O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl- (substituted or unsubstituted aryl), —$C_1$-$C_6$alkyl-(substituted or unsubstituted heteroaryl), or —$NR^DR^E$;

$R^D$ and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl- (substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl- (substituted or unsubstituted heteroaryl);

m of Formula (XLII) is selected from 0, 1 or 2;

—U— of Formula (XLII) is selected from —NHC(=O)—, —C(=O)NH—, —NHS(=O)$_2$—, —S(=O)$_2$ NH—, —NHC(=O)NH—, —NH(C=O)O—, —O(C=O)NH—, or —NHS(=O)$_2$NH—;

$R^3$ of Formula (XLII) is selected from $C_1$-$C_3$alkyl, or $C_1$-$C_3$fluoroalkyl;

$R^4$ of Formula (XLII) is selected from —$NHR^5$, —$N(R^5)_2$, —$N+(R^5)_3$ or —$OR^5$;

each $R^5$ of —$NHR^5$, —$N(R^5)_2$, —$N+(R^5)_3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ of Formula (XLII) together with the atoms to which they are attached form a substituted or unsubstituted 5-7 membered ring;

or:

$R^3$ of Formula (XLII) is bonded to a nitrogen atom of U to form a substituted or unsubstituted 5-7 membered ring;

$R^6$ of Formula (XLII) is selected from —NHC(=O)$R^7$, —C(=O)NH$R^7$, —NHS(=O)2$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)$_2$$R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;

each $R^7$ of —NHC(=O)$R^7$, —C(=O)NH$R^7$, —NHS(=O)2$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)2$R^7$, —($C_1$-$C_3$alkyl)-S(=O)2NH$R^7$; —($C_1$-$C_3$alkyl)-NHC(=O)NH$R^7$, —($C_1$-$C_3$alkyl)-NHS(=O)2NH$R^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl- (substituted or unsubstituted C2-C10heterocycloalkyl, —C1-C6alkyl-(substituted or unsubstituted aryl), —$C_1$-$C_6$alkyl-(substituted or unsubstituted heteroaryl), —(CH2)p-CH(substituted or unsubstituted aryl)2, —(CH$_2$)$_p$—CH(substituted or unsubstituted heteroaryl)2, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is selected from 0, 1 or 2;

$R^{8a}$, $R^{8b}$, $R^{8c}$, and $R^{8d}$ of $C(R^{8a})(R^{8b})$ and $C(R^{8c})(R^{8d})$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;
where each substituted alkyl, heteroalkyl, fused ring, spirocycle, heterospirocycle, cycloalkyl, heterocycloalkyl, aryl or heteroaryl is substituted with 1-3 $R^9$; and
each $R^9$ of $R^{8a}$, $R^{8b}$, $R^{8c}$ and $R^{8d}$ is independently selected from halogen, —OH, —SH, (C═O), CN, $C_1$-$C_4$alkyl, C1-C4fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(═O)OH, —C(═O)NH$_2$, —C(0)$C_1$-$C_3$alkyl, —S(═O)$_2$CH$_3$, —NH($C_1$-$C_4$alkyl)-OH, —NH($C_1$-$C_4$alkyl)-O—(C—$C_4$alkyl), —O($C_1$-$C_4$alkyl)-NH2; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XLIII), which is derived from the IAP ligands described in WO Pub. No. 2013/071039, or an unnatural mimetic thereof:

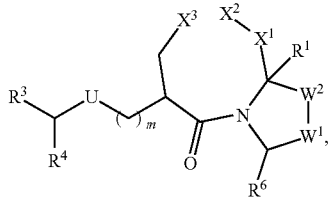

(XLIII)

wherein:
$W^1$ of Formula (XLIII) is selected from O, S, N—$R^A$, or C($R^{8a}$)($R^{8b}$);
$W^2$ of Formula (XLIII) is selected from O, S, N—$R^A$, or C($R^{8c}$)($R^{8d}$); provided that $W^1$ and $W^2$ are not both O, or both S;
$R^1$ of Formula (XLIII) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);
when $X^1$ of Formula (XLIII) is selected from N—$R^A$, S, S(O), or S(O)$_2$, then $X^2$ of Formula (XLIII) is $CR^{2c}R^{2d}$; and $X^3$ of Formula (XLIII) is $CR^{2a}R^{2b}$;
or:
when $X^1$ of Formula (XLIII) is O, then $X^2$ of Formula (XLIII) is selected from O, N—$R^A$, S, S(O), or S(O)$_2$, and $X^3$ of Formula (XLIII) is $CR^{2a}R^{2b}$;
or:
when $X^1$ of Formula (XLIII) is $CR^{2e}R^{2f}$ and $X^2$ of Formula (XLIII) is $CR^{2c}R^{2d}$, and $R^{2e}$ and $R^{2c}$ together form a bond, and $X^3$ of Formula (XLIII) is $CR^{2a}R^{2b}$;
or:
$X^1$ and $X^2$ of Formula (XLIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ of Formula (XLIII) is $CR^{2a}R^{2b}$;
or:
$X^2$ and $X^3$ of Formula (XLIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (VLII) is $CR^{2e}R^{2f}$;
$R^A$ of N—$R^A$ is H, $C_1$-$C_6$alkyl, —C(═O)$C_1$-$C_2$alkyl, substituted or unsubstituted aryl, or substituted or unsubstituted heteroaryl;
$R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(═O)$R^B$;
$R^B$ of —C(═O)$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocyclo alkyl), —$C_1$-$C_6$alkyl- (substituted or unsubstituted aryl), —$C_1$-$C_6$alkyl-(substituted or unsubstituted heteroaryl), or —NR$^D$R$^E$;
$R^D$ and $R^E$ of NR$^D$R$^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl- (substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl- (substituted or unsubstituted heteroaryl);
m of Formula (XLIII) is 0, 1 or 2;
—U— of Formula (XLIII) is —NHC(═O)—, —C(═O)NH—, —NHS(═O)$_2$—, —S(═O)$_2$NH—, —NHC(═O)NH—, —NH(C═O)O—, —O(C═O)NH—, or —NHS(═O)$_2$NH—;
$R^3$ of Formula (XLIII) is $C_1$-$C_3$alkyl, or $C_1$-$C_3$fluoroalkyl;
$R^4$ of Formula (XLIII) is —NHR$^5$, —N(R$^5$)$_2$, —N+(R$^5$)$_3$ or —OR$^5$;
each $R^5$ of —NHR$^5$, —N(R$^5$)$_2$, —N+(R$^5$)$_3$ and —OR$^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);
or:
$R^3$ and $R^5$ of Formula (XLIII) together with the atoms to which they are attached form a substituted or unsubstituted 5-7 membered ring;
or:
$R^3$ of Formula (XLIII) is bonded to a nitrogen atom of U to form a substituted or unsubstituted 5-7 membered ring;
$R^6$ of Formula (XLIII) is selected from —NHC(═O)R$^7$, —C(═O)NHR$^7$, —NHS(═O)2R$^7$, —S(═O)$_2$NHR$^7$;

—NHC(=O)NHR$^7$, —NHS(=O)$_2$NHR$^7$, —(C$_1$-C$_3$alkyl)-NHC(=O)R$^7$, —(C$_1$-C$_3$alkyl)-C(=O)NHR$^7$, —(C$_1$-C$_3$alkyl)-NHS(=O)$_2$R$^7$, —(C$_1$-C$_3$alkyl)-S(=O)$_2$NHR$^7$; —(C$_1$-C$_3$alkyl)-NHC(=O)NHR$^7$, —(C$_1$-C$_3$alkyl)-NHS(=O)$_2$NHR$^7$, substituted or unsubstituted C$_2$-C$_{10}$heterocycloalkyl, or substituted or unsubstituted heteroaryl;

each R$^7$ of —NHC(=O)R$^7$, —C(=O)NHR$^7$, —NHS(=O)2R$^7$, —S(=O)$_2$NHR$^7$; —NHC(=O)NHR$^7$, —NHS(=O)$_2$NHR$^7$, —(C$_1$-C$_3$alkyl)-NHC(=O)R$^7$, —(C$_1$-C$_3$alkyl)-C(=O)NHR$^7$, —(C$_1$-C$_3$alkyl)-NHS(=O)2R$^7$, —(C$_1$-C$_3$alkyl)-S(=O)2NHR$^7$; —(C$_1$-C$_3$alkyl)-NHC(=O)NHR$^7$, —(C$_1$-C$_3$alkyl)-NHS(=O)2NHR$^7$ is independently selected from C$_1$-C$_6$alkyl, C$_1$-C$_6$haloalkyl, C$_1$-C$_6$heteroalkyl, a substituted or unsubstituted C3-C10cycloalkyl, a substituted or unsubstituted C$_2$-C$_{10}$heterocycloalkyl, a substituted or unsubstituted aryl, a substituted or unsubstituted heteroaryl, —C$_1$-C$_6$alkyl-(substituted or unsubstituted C$_3$-C$_{10}$cyclo alkyl), —C$_1$-C$_6$alkyl- (substituted or unsubstituted C2-C10heterocycloalkyl, —C1-C6alkyl-(substituted or unsubstituted aryl), —C$_1$-C$_6$alkyl-(substituted or unsubstituted heteroaryl), —(CH2)p-CH (substituted or unsubstituted aryl)2, —(CH$_2$)$_p$—CH (substituted or unsubstituted heteroaryl)2, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of R$^7$ is 0, 1 or 2;

R$^{8a}$, R$^{8b}$, R$^{8c}$, and R$^{8d}$ of C(R$^{8a}$)(R$^{8b}$) and C(R$^{8c}$)(R$^{8d}$) are independently selected from H, C$_1$-C$_6$alkyl, C$_1$-C$_6$fluoroalkyl, C$_1$-C$_6$ alkoxy, C$_1$-C$_6$heteroalkyl, and substituted or unsubstituted aryl;

or:

R$^{8a}$ and R$^{8d}$ are as defined above, and R$^{8b}$ and R$^{8c}$ together form a bond;

or:

R$^{8a}$ and R$^{8d}$ are as defined above, and R$^{8b}$ and R$^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

R$^{8c}$ and R$^{8d}$ are as defined above, and R$^{8a}$ and R$^{8b}$ together with the atoms to which they are attached form a substituted or unsubstituted saturated, or partially saturated 3-7 membered spirocycle or heterospirocycle comprising 1-3 heteroatoms selected from S, O and N;

or:

R$^{8a}$ and R$^{8b}$ are as defined above, and R$^{8c}$ and R$^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 R$^9$; and each R$^9$ of R$^{8a}$, R$^{8b}$, R$^{8c}$ and R$^{8d}$ is independently selected from halogen, —OH, —SH, (C=O), CN, C$_1$-C$_4$alkyl, C1-C4fluoroalkyl, C$_1$-C$_4$ alkoxy, C$_1$-C$_4$ fluoroalkoxy, —NH$_2$, —NH(C$_1$-C$_4$alkyl), —NH(C$_1$-C$_4$alkyl)$_2$, —C(=O)OH, —C(=0)NH$_2$, —C(=O)C$_1$-C$_3$alkyl, —S(=O)$_2$CH$_3$, —NH(C$_1$-C$_4$alkyl)-OH, —NH(C$_1$-C$_4$alkyl)-O—(C—C$_4$alkyl), —O(C$_1$-C$_4$alkyl)-NH2; —O(C$_1$-C$_4$alkyl)-NH—(C$_1$-C$_4$alkyl), and —O(C$_1$-C$_4$alkyl)-N—(C$_1$-C$_4$alkyl)$_2$, or two R$^9$ together with the atoms to which they are attached form a methylene dioxy or ethylene dioxy ring substituted or unsubstituted with halogen, —OH, or C$_1$-C$_3$alkyl.

In any of the compounds described herein, the ILM can have the structure of Formula (XLIV), which is derived from the IAP ligands described in WO Pub. No. 2013/071039, or an unnatural mimetic thereof:

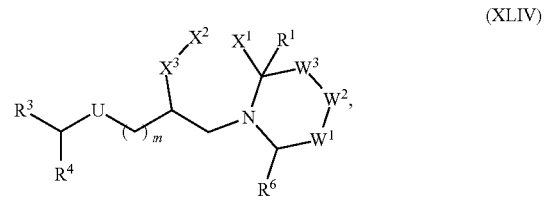

(XLIV)

wherein:

W$^1$ of Formula (XLIV) is selected from O, S, N—R$^A$, or C(R$^{8a}$)(R$^{8b}$);

W$^2$ of Formula (XLIV) is selected from O, S, N—R$^A$, or C(R$^{8c}$)(R$^{8d}$); provided that W$^1$ and W$^2$ are not both O, or both S;

W$^3$ of Formula (XLIV) is selected from O, S, N—R$^A$, or C(R$^{8e}$)(R$^{8f}$), providing that the ring comprising W$^1$, W$^2$, and W$^3$ does not comprise two adjacent oxygen atoms or sulfur atoms;

R$^1$ of Formula (XLIV) is selected from H, C$_1$-C$_6$alkyl, C$_3$-C$_6$cycloalkyl, —C$_1$-C$_6$alkyl-(substituted or unsubstituted C$_3$-C$_6$cycloalkyl), substituted or unsubstituted aryl, substituted or unsubstituted heteroaryl, —C$_1$-C$_6$alkyl-(substituted or unsubstituted aryl), or —C$_1$-C$_6$alkyl-(substituted or unsubstituted heteroaryl);

when X$^1$ of Formula (XLIV) is O, then X$^2$ of Formula (XLIV) is selected from CR$^{2c}$R$^{2d}$ and N—R$^A$, and X$^3$ of Formula (XLIV) is CR$^{2a}$R$^{2b}$;

or:

when X$^1$ of Formula (XLIV) is CH$_2$, then X$^2$ of Formula (XLIV) is selected from O, N—R$^A$, S, S(O), or S(O)$_2$, and X$^3$ of Formula (XLIV) is CR$^{2a}$R$^{2b}$;

or:

when X$^1$ of Formula (XLIV) is CR$^{2e}$R$^{2f}$ and X$^2$ of Formula (XLIV) is CR$^{2c}$R$^{2d}$, and R$^{2e}$ and R$^{2c}$ together form a bond, and X$^3$ of Formula (VLIV) is CR$^{2a}$R$^{2b}$;

or:

X$^1$ and X$^3$ of Formula (XLIV) are both CH$_2$ and X$^2$ of Formula (XLII) is C=0, C=C(R$^C$)2, or C=NR$^C$; where each R$^C$ is independently selected from H, —CN, —OH, alkoxy, substituted or unsubstituted C$_1$-C$_6$alkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), or —$C_1$-$C_6$alkyl- (substituted or unsubstituted heteroaryl);

or:

$X^1$ and $X^2$ of Formula (XLIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ of Formula (XLIV) is $CR^{2a}R^{2b}$;

or:

$X^2$ and $X^3$ of Formula (XLIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (VLIV) is $CR^{2c}R^{2f}$;

$R^A$ of N—$R^A$ is selected from H, $C_1$-$C_6$alkyl, —C(=O) $C_1$-$C_2$alkyl, substituted or unsubstituted aryl, or substituted or unsubstituted heteroaryl;

$R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2c}R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), –$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —$C(=O)R^B$;

$R^B$ of —$C(=O)R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl- (substituted or unsubstituted aryl), —$C_1$-$C_6$alkyl-(substituted or unsubstituted heteroaryl), or —$NR^D R^E$;

$R^D$ and $R^E$ of $NR^D R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl- (substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl- (substituted or unsubstituted heteroaryl);

m of Formula (XLIV) is selected from 0, 1 or 2;

—U— of Formula (XLIV) is selected from —NHC (=O)—, —C(=O)NH—, —NHS(=O)$_2$—, —S(=O)$_2$ NH—, —NHC(=O)NH—, —NH(C=O) O—, —O(C=O)NH—, or —NHS(=O)$_2$NH—;

$R^3$ of Formula (XLIV) is selected from $C_1$-$C_3$alkyl, or $C_1$-$C_3$fluoroalkyl;

$R^4$ of Formula (XLIV) is selected from —$NHR^5$, —N $(R^5)_2$, —N+$(R^5)_3$ or —$OR^5$;

each $R^5$ of —$NHR^5$, —$N(R^5)_2$, —N+$(R^5)_3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ of Formula (XLIV) together with the atoms to which they are attached form a substituted or unsubstituted 5-7 membered ring;

or:

$R^3$ of Formula (XLIII) is bonded to a nitrogen atom of U to form a substituted or unsubstituted 5-7 membered ring;

$R^6$ of Formula (XLIII) is selected from —$NHC(=O)R^7$, —$C(=O)NHR^7$, —$NHS(=O)2R^7$, —$S(=O)_2NHR^7$; —$NHC(=O)NHR^7$, —$NHS(=O)_2NHR^7$, —($C_1$-$C_3$alkyl)-$NHC(=O)R^7$, —($C_1$-$C_3$alkyl)-$C(=O)NHR^7$, —($C_1$-$C_3$alkyl)-$NHS(=O)_2R^7$, —($C_1$-$C_3$alkyl)-S$(=O)_2NHR^7$; —($C_1$-$C_3$alkyl)-$NHC(=O)NHR^7$, —($C_1$-$C_3$alkyl)-NHS $(=O)_2NHR^7$, substituted or unsubstituted $C_2$-$C_{10}$heterocycloalkyl, or substituted or unsubstituted heteroaryl;

each $R^7$ of —$NHC(=O)R^7$, —$C(=O)NHR^7$, —NHS $(=O)2R^7$, —$S(=O)_2NHR^7$; —$NHC(=O)NHR^7$, —$NHS(=O)_2NHR^7$, —($C_1$-$C_3$alkyl)-$NHC(=O)R^7$, —($C_1$-$C_3$alkyl)-$C(=O)NHR^7$, —($C_1$-$C_3$alkyl)-NHS $(=O)_2R^7$, —($C_1$-$C_3$alkyl)-$S(=O)2NHR^7$; —($C_1$-$C_3$alkyl)-$NHC(=O)NHR^7$, —($C_1$-$C_3$alkyl)-NHS $(=O)_2$ $NHR^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cyclo alkyl), —$C_1$-$C_6$alkyl- (substituted or unsubstituted C2-C10heterocycloalkyl, —C1-C6alkyl-(substituted or unsubstituted aryl), —$C_1$-$C_6$alkyl-(substituted or unsubstituted heteroaryl), —(CH2)p-CH(substituted or unsubstituted aryl)2, —(CH$_2$)$_p$—CH(substituted or unsubstituted heteroaryl)2, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is selected from 0, 1 or 2;

$R^{8a}$, $R^{8b}$, $R^{8c}$, $R^{8d}$, $R^{8e}$, and $R^{8f}$ of $C(R^{8a})(R^{8b})$, $C(R^{8c})(R^{8d})$ and $C(R^{8e})(R^{8f})$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$, $R^{8d}$, $R^{8e}$, and $R^{8f}$ of $C(R^{8a})(R^{8b})$, $C(R^{8c})(R^{8d})$ and $C(R^{8e})(R^{8f})$ are as defined above, and $R^{8b}$ and $R^{8c}$ together form a bond;

or:

$R^{8a}$, $R^{8b}$, $R^{8d}$, and $R^{8f}$ of $C(R^{8a})(R^{8b})$, $C(R^{8c})(R^{8d})$ and $C(R^{8e})(R^{8f})$ are as defined above, and $R^{8c}$ and $R^{8e}$ together form a bond;

or:

$R^{8a}$, $R^{8d}$, $R^{8e}$, and $R^{8f}$ of $C(R^{8a})(R^{8b})$, $C(R^{8c})(R^{8d})$ and $C(R^{8e})(R^{8f})$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8a}$, $R^{8b}$, $R^{8d}$, and $R^{8f}$ of $C(R^{8a})(R^{8b})$, $C(R^{8c})(R^{8d})$ and $C(R^{8e})(R^{8f})$ are as defined above, and $R^{8c}$ and $R^{8e}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$, $R^{8d}$, $R^{8e}$, and $R^{8f}$ of $C(R^{8c})(R^{8d})$ and $C(R^{8e})(R^{8f})$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8e}$, and $R^{8f}$ of $C(R^{8a})(R^{8b})$ and $C(R^{8e})(R^{8f})$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8c}$, and $R^{8d}$ of $C(R^{8a})(R^{8b})$ and $C(R^{8c})(R^{8d})$ are as defined above, and $R^{8e}$ and $R^{8f}$ together with the atoms to which they are attached form a substituted or unsubstituted saturated, or partially saturated 3-7 membered spirocycle or heterospirocycle comprising 1-3 heteroatoms selected from S, O and N;

or:

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$, $R^{8d}$, $R^{8e}$, and $R^{8f}$ is independently selected from halogen, —OH, —SH, (C=O), CN, $C_1$-$C_4$alkyl, C1-C4fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—(C—$C_4$alkyl), —O($C_1$-$C_4$alkyl)-NH2; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XLV), (XLVI) or (XLVII), which is derived from the IAP ligands described in Vamos, M., et al., *Expedient synthesis of highly potent antagonists of inhibitor of apoptosis proteins (IAPs) with unique selectivity for ML-IAP*, ACS Chem. Biol., 8(4), 725-32 (2013), or an unnatural mimetic thereof:

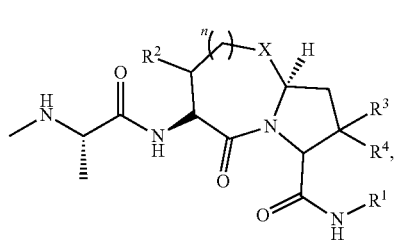

(XLV)

n = 0, 1

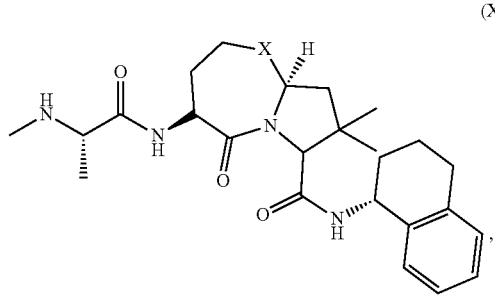

(XLVI)

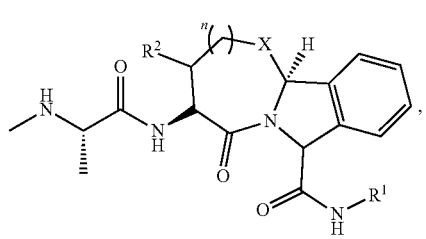

(XLVII)

n = 0, 1 wherein:

$R^2$, $R^3$ and $R^4$ of Formula (XLV) are independently selected from H or ME;

X of Formula (XLV) is independently selected from O or S; and $R^1$ of Formula (XLV) is selected from:

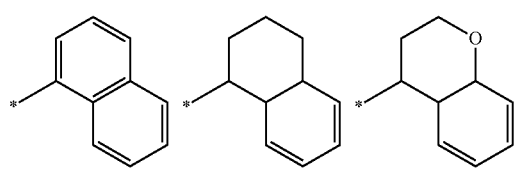

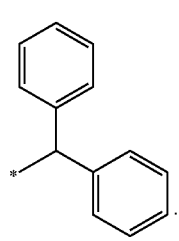

In a particular embodiment, the ILM has a structure according to Formula (XLVIII):

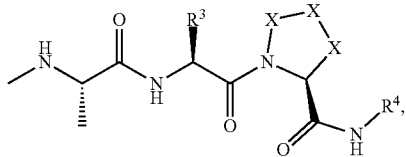
(XLVIII)
wherein R³ and R⁴ of Formula (XLVIII) are independently selected from H or ME;
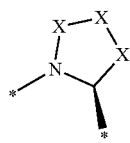
is a 5-member heterocycle selected from:
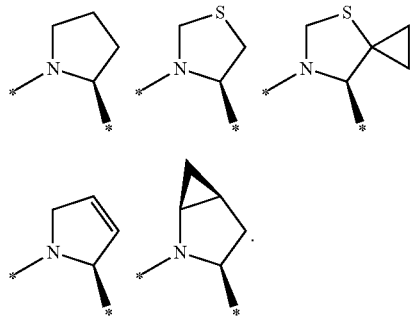
In a particular embodiment, the
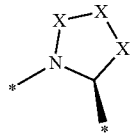
of Formula XLVIII) is
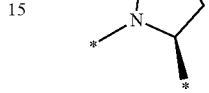
In a particular embodiment, the ILM has a structure and attached to a linker group L as shown below:
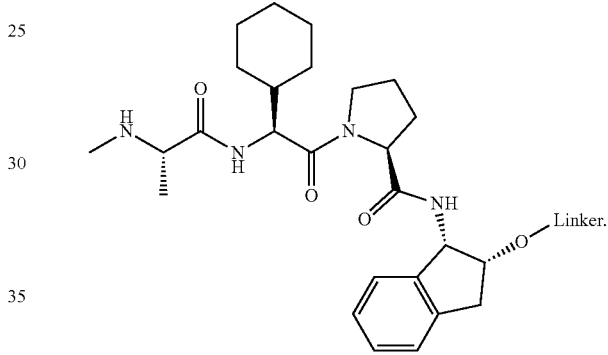
In a particular embodiment, the ILM has a structure according to Formula (XLIX), (L), or (LI):
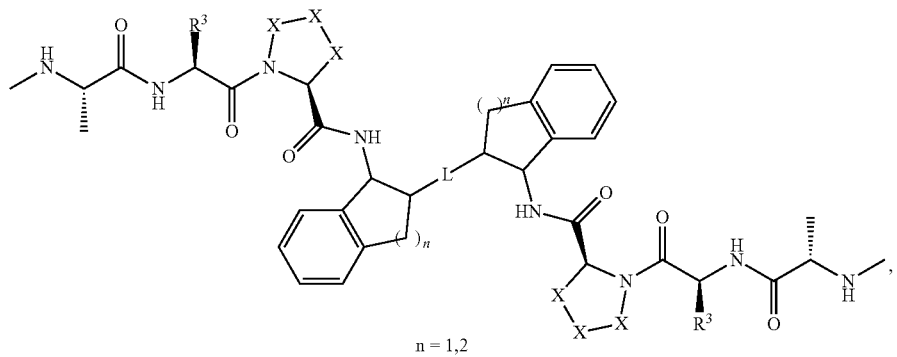
(XLIX)
n = 1,2

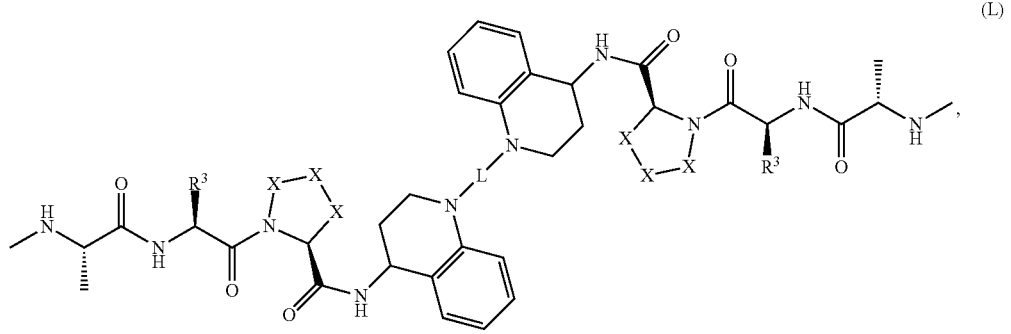
(L)
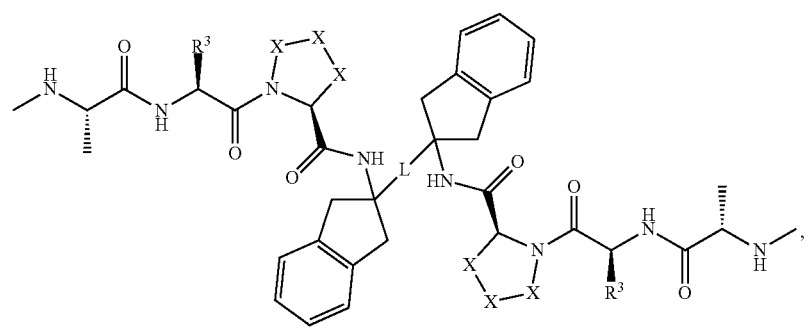
(LI)
wherein:
R³ of Formula (XLIX), (L) or (LI) are independently selected from H or ME;
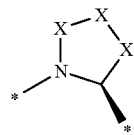
is a 5-member heterocycle selected from:
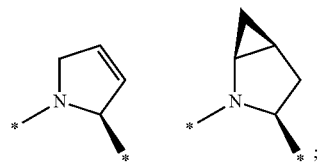
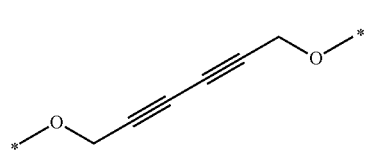
and L of Formula (XLIX), (L) or (LI) is selected from:
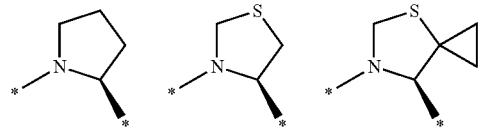
-continued
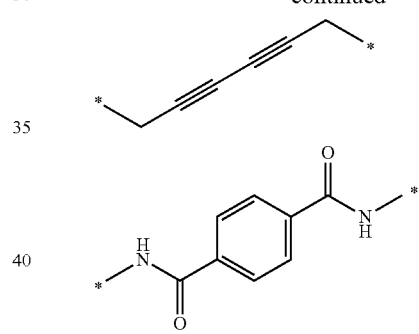
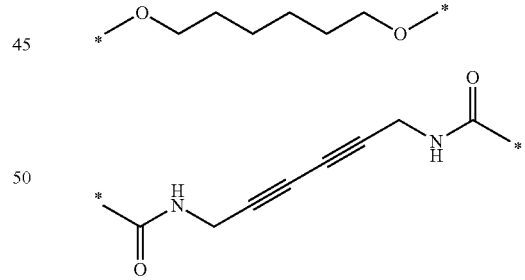
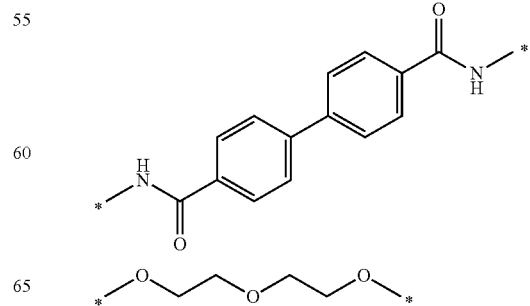

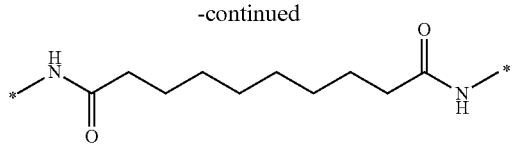

In a particular embodiment, L of Formula (XLIX), (L), or (LI)

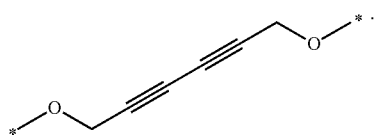

In a particular embodiment, the ILM has a structure according to Formula (LII):

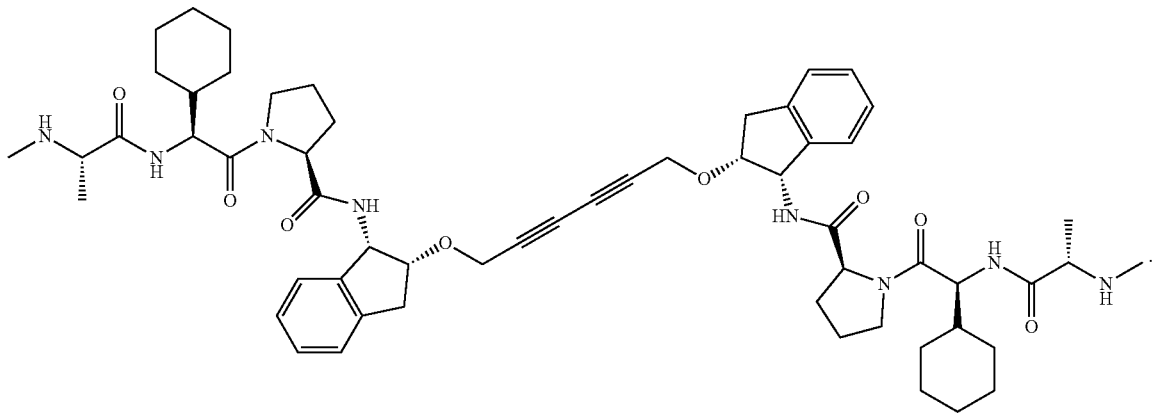

In a particular embodiment, the ILM according to Formula (LII) is chemically linked to the linker group L in the area denoted with

, and as shown below:

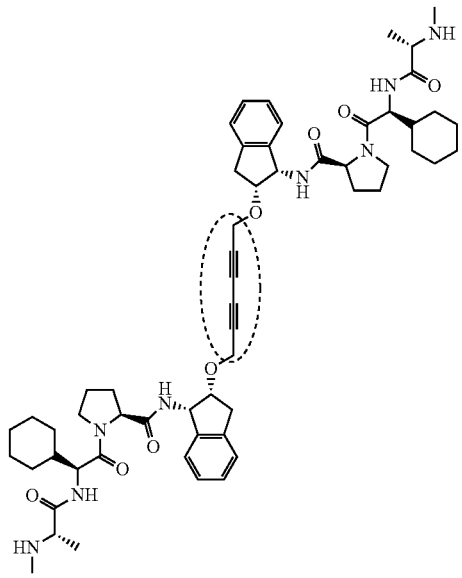 [SMILES: CN[C@@H](C)C(=O)N[C@H](C(=O)N1CCC[C@H]1C(=O)N[C@H]1c2ccccc2C[C@H]1OCC#CC#CCO[C@@H]1Cc2ccccc2[C@@H]1NC(=O)[C@@H]1CCCN1C(=O)[C@@H](NC(=O)[C@H](C)NC)C1CCCCC1)C1CCCCC1]

In any of the compounds described herein, the ILM can have the structure of Formula (LIII) or (LIV), which is based on the IAP ligands described in Hennessy, E J, et al.,

*Discovery of aminopiperidine-based Smac mimetics as IAP antagonists*, Bioorg. Med. Chem. Lett., 22(4), 1960-4 (2012), or an unnatural mimetic thereof:

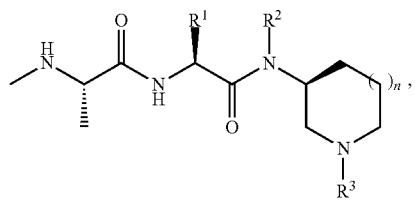

(LIII)

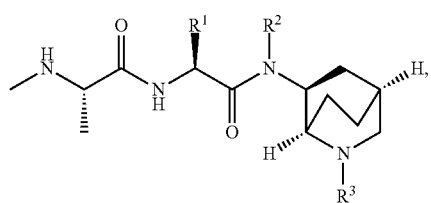

(LIV)

wherein:
$R^1$ of Formulas (LIII) and (LIV) is selected from:

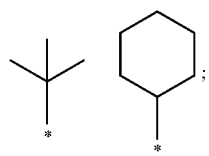

$R^2$ of Formulas (LIII) and (LIV) is selected from H or Me;
$R^3$ of Formulas (LIII) and (LIV) is selected from:

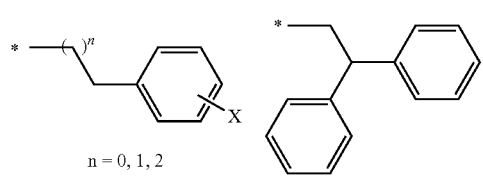

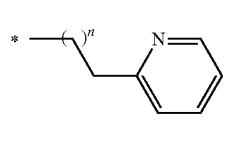

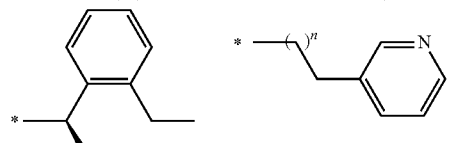

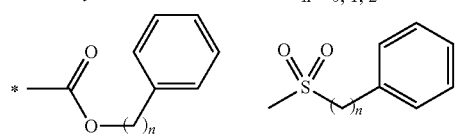

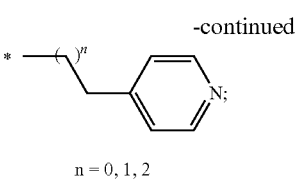

X of is selected from H, halogen, methyl, methoxy, hydroxy, nitro or trifluoromethyl.

In any of the compounds described herein, the ILM can have the structure of and be chemically linked to the linker as shown in Formula (LV) or (LVI), or an unnatural mimetic thereof:

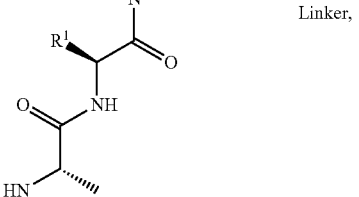

(LV)

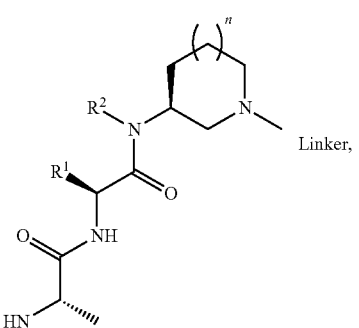

(LVI)

In any of the compounds described herein, the ILM can have the structure of Formula (LVII), which is based on the IAP ligands described in Cohen, F, et al., *Orally bioavailable antagonists of inhibitor of apoptosis proteins based on an azabicyclooctane scaffold*, J. Med. Chem., 52(6), 1723-30 (2009), or an unnatural mimetic thereof:

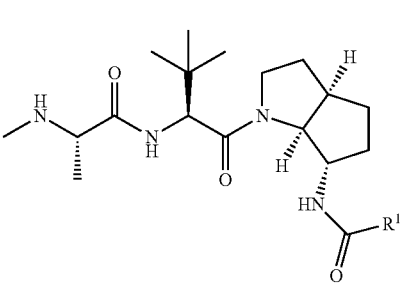

(LVII)

wherein:

R1 of Formulas (LVII) is selected from:

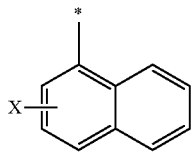 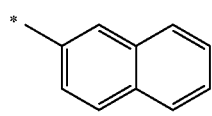

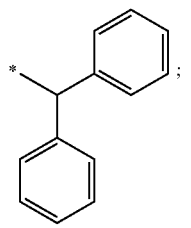

X of

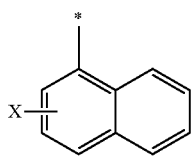

is selected from H, fluoro, methyl or methoxy.

In a particular embodiment, the ILM is represented by the following structure:

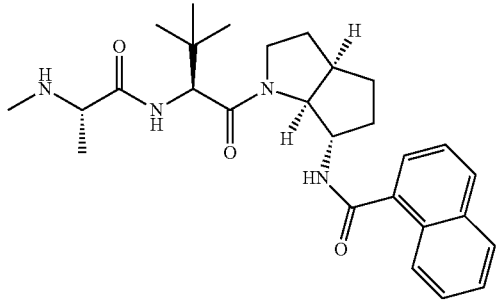

In a particular embodiment, the ILM is selected from the group consisting of, and which the chemical link between the ILM and linker group L is shown:

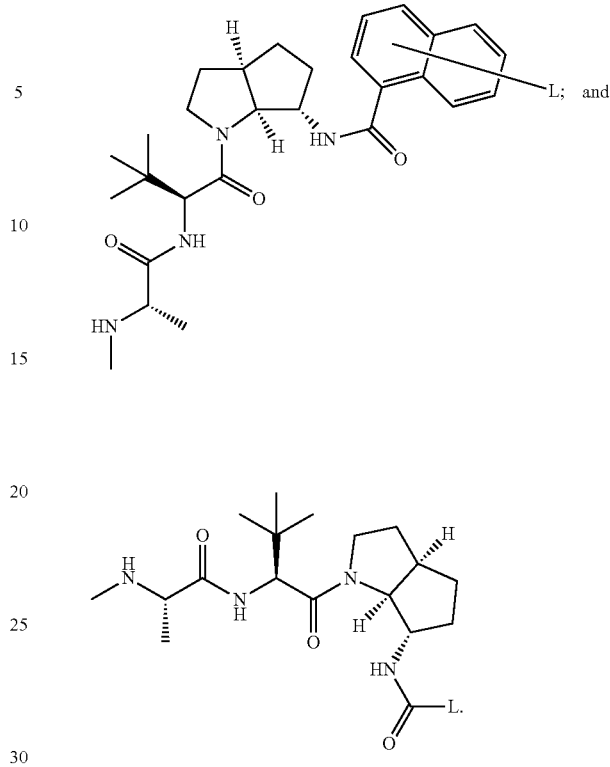

In any of the compounds described herein, the ILM is selected from the group consisting of the structures below, which are based on the IAP ligands described in Asano, M, et al., *Design, sterioselective synthesis, and biological evaluation of novel tri-cyclic compounds as inhibitor of apoptosis proteins (IAP) antagonists*, Bioorg. Med. Chem., 21(18): 5725-37 (2013), or an unnatural mimetic thereof:

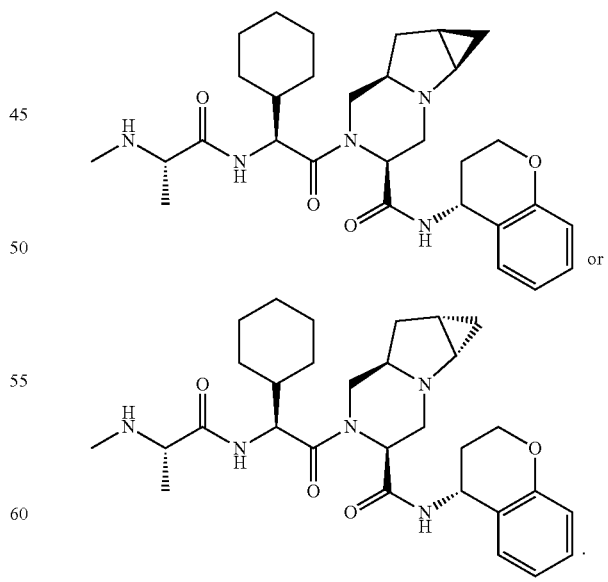

In a particular embodiment, the ILM is selected from the group consisting of, and which the chemical link between the ILM and linker group L is shown:

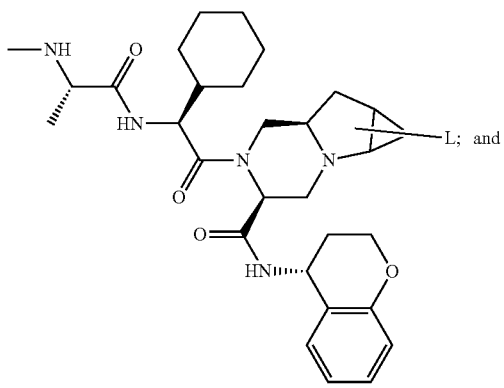

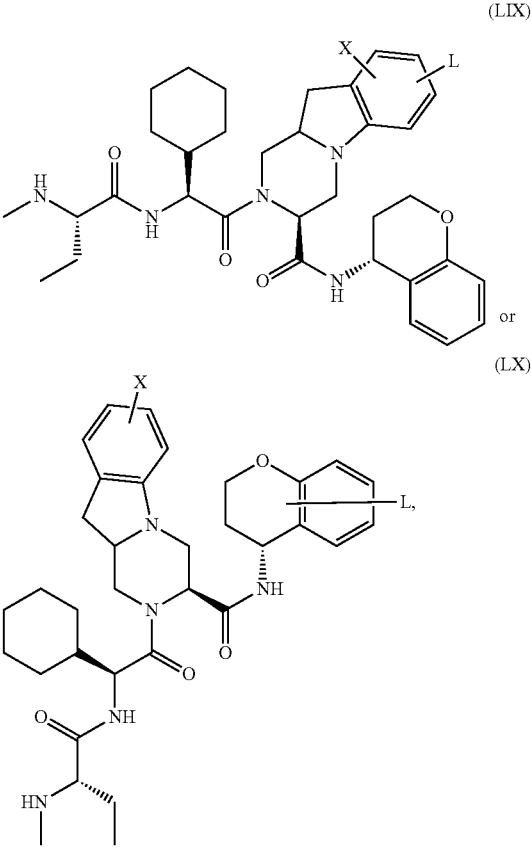

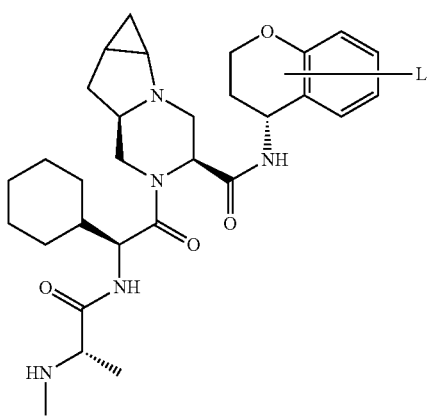

In any of the compounds described herein, the ILM can have the structure of Formula (LVIII), which is based on the IAP ligands described in Asano, M, et al., *Design, sterioselective synthesis, and biological evaluation of novel tricyclic compounds as inhibitor of apoptosis proteins (IAP) antagonists*, Bioorg. Med. Chem., 21(18): 5725-37 (2013), or an unnatural mimetic thereof:

(LVIII)

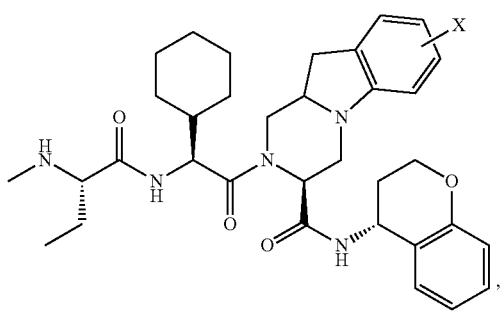

wherein X of Formula (LVIII) is one or two substituents independently selected from H, halogen or cyano.

In any of the compounds described herein, the ILM can have the structure of and be chemically linked to the linker group L as shown in Formula (LIX) or (LX), or an unnatural mimetic thereof:

wherein X of Formula (LIX) and (LX) is one or two substituents independently selected from H, halogen or cyano, and; and L of Formulas (LIX) and (LX) is a linker group as described herein.

In any of the compounds described herein, the ILM can have the structure of Formula (LXI), which is based on the IAP ligands described in Ardecky, R J, et al., *Design, sysnthesis and evaluation of inhibitor of apoptosis (IAP) antagonists that are highly selective for the BIR2 domain of XIAP*, Bioorg. Med. Chem., 23(14): 4253-7 (2013), or an unnatural mimetic thereof:

(LXI)

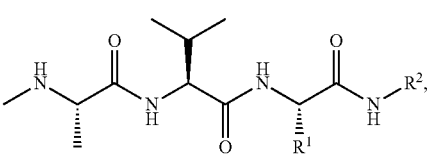

wherein:

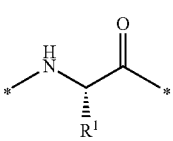

of Formula (LXI) is a natural or unnatural amino acid; and $R^2$ of Formula (LXI) is selected from:

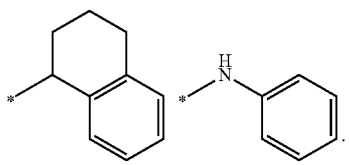

In any of the compounds described herein, the ILM can have the structure of and be chemically linked to the linker group L as shown in Formula (LXII) or (LLXIII), or an unnatural mimetic thereof:

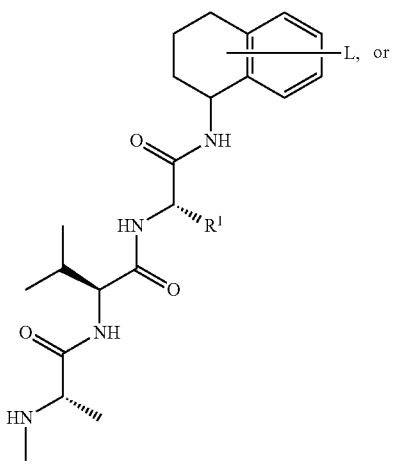

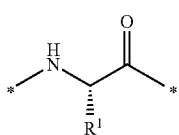

of Formula (LXI) is a natural or unnatural amino acid; and L of Formula (LXI) is a linker group as described herein.

In any of the compounds described herein, the ILM can have the structure selected from the group consisting of, which is based on the IAP ligands described in Wang, J, et al., *Discovery of novel second mitochondrial-derived activator of caspase mimetics as selective inhibitor or apoptosis protein inhibitors*, J. Pharmacol. Exp. Ther., 349(2): 319-29 (2014), or an unnatural mimetic thereof:

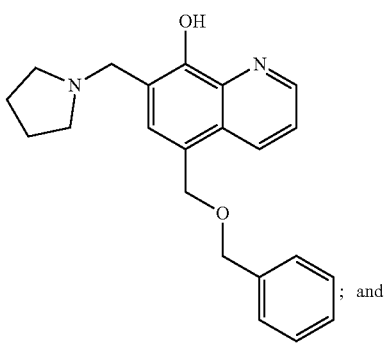

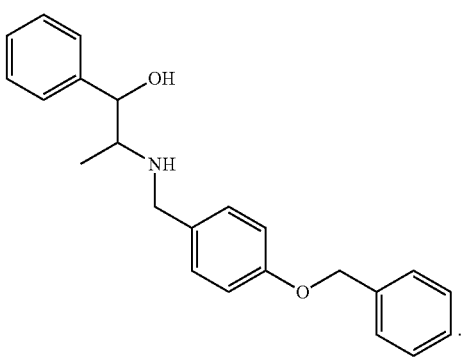

In any of the compounds described herein, the ILM has a structure according to Formula (LXIX), which is based on the IAP ligands described in Hird, A W, et al., Structure-based design and synthesis of tricyclic IAP (Inhibitors *of Apoptosis Proteins*) inhibitors, Bioorg. Med. Chem. Lett., 24(7): 1820-4 (2014), or an unnatural mimetic thereof:

(LXIX)

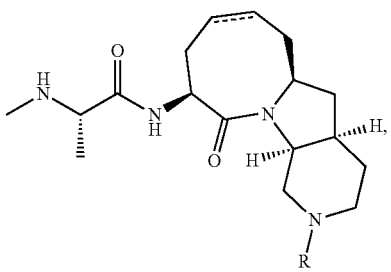

wherein R of Formula LIX is selected from the group consisting of:

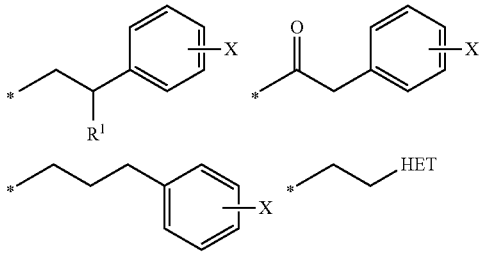

-continued

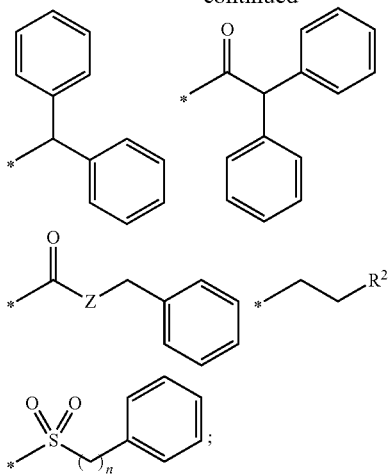

R1 of

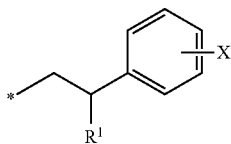

is selected from H or Me;
R2 of

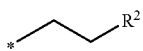

is selected from alkyl or cycloalkyl;
X of

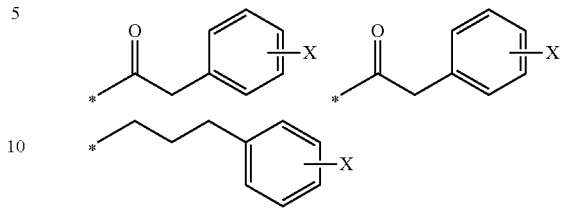

is 1-2 substitutents independently selected from halogen, hydroxy, methoxy, nitro and trifluoromethyl Z of

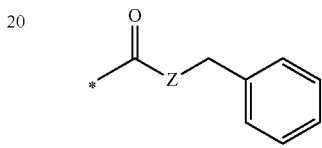

is O or NH;
HET of

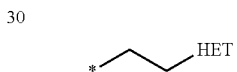

is mono- or fused bicyclic heteroaryl; and
— of Formula (LIX) is an optional double bond.

In a particular embodiment, the ILM of the compound has a chemical structure as represented by:

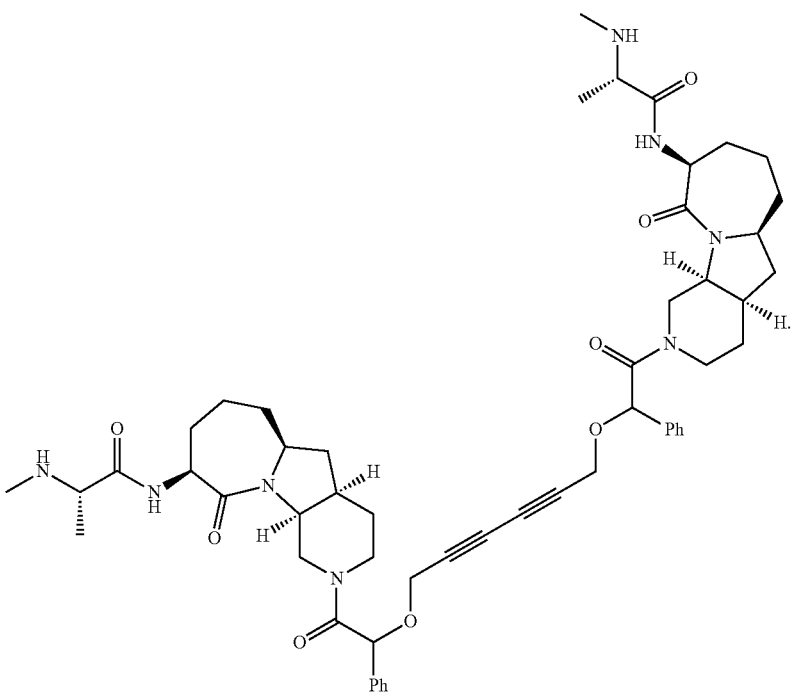

In a particular embodiment, the ILM of the compound has a chemical structure selected from the group consisting of:

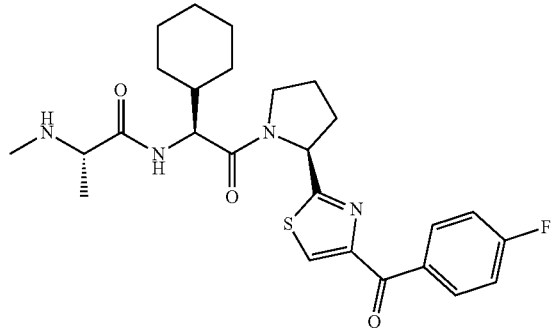

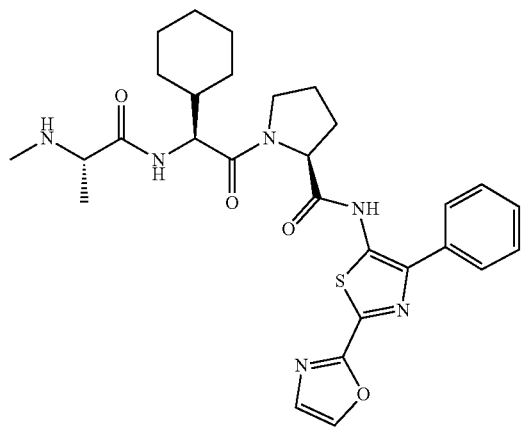

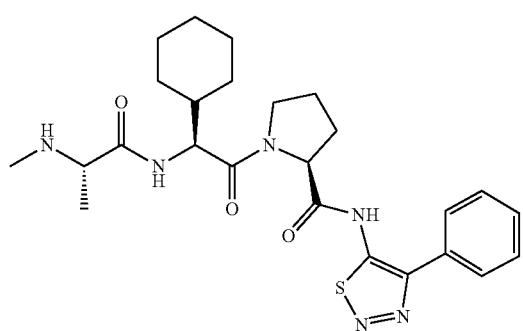

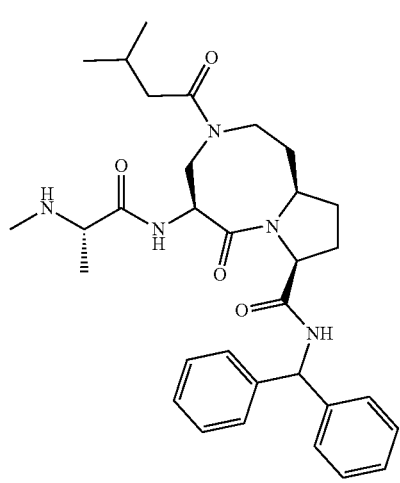

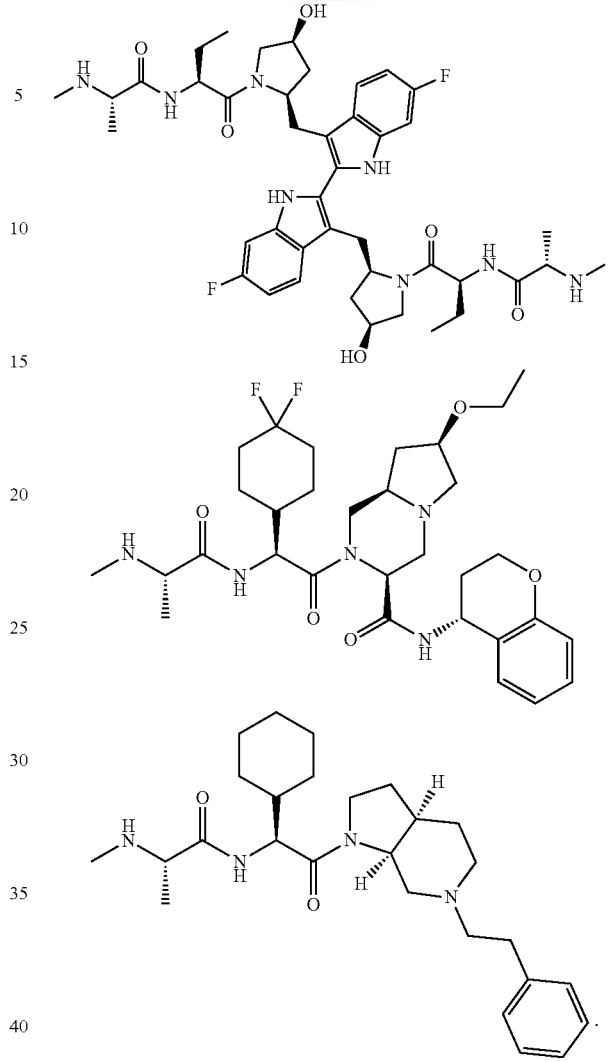

The term "independently" is used herein to indicate that the variable, which is independently applied, varies independently from application to application.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain embodiments, the alkyl group is end-capped with a halogen group (At, Br, Cl, F, or I). In certain preferred embodiments, compounds according to the present disclosure which may be used to covalently bind to dehalogenase enzymes. These compounds generally contain a side chain (often linked through a polyethylene glycol group) which terminates in an alkyl group which has a halogen substituent (often chlorine or bromine) on its distal end which results in covalent binding of the compound containing such a moiety to the protein.

The term "Alkenyl" refers to linear, branch-chained or cyclic $C_2$-$C_{10}$ (preferably $C_2$-$C_6$) hydrocarbon radicals containing at least one C=C bond.

The term "Alkynyl" refers to linear, branch-chained or cyclic $C_2$-$C_{10}$ (preferably $C_2$-$C_6$) hydrocarbon radicals containing at least one CC bond.

The term "alkylene" when used, refers to a —$(CH_2)_n$— group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present disclosure and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteraryl moiety) through an optionally substituted —$(CH_2)_m$— or alternatively an optionally substituted —$(OCH_2)_m$—, —$(OCH_2CH_2)_m$— or —$(CH_2CH_2O)_m$— group, which may be substituted with any one or more of the above-described substituents. Alkylene groups —$(CH_2)_m$— or —$(CH_2)$— groups or other chains such as ethylene glycol chains, as identified above, may be substituted anywhere on the chain. Preferred substitutents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sideshain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ester (oxyester or carbonylester), $C_1$-$C_6$keto, urethane —O—C(O)—$NR_1R_2$ or —N($R_1$)—C(O)—O—$R_1$, nitro, cyano and amine (especially including a $C_1$-$C_6$ alkylene-$NR_1R_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —$(CH_2)_m$— (here, m and n are in context, 1, 2, 3, 4, 5 or 6), —S—, —S(O)—, $SO_2$— or —NH—C(O)—NH—, —$(CH_2)_n$OH, —$(CH_2)_n$SH, —$(CH_2)_n$COOH, $C_1$-$C_6$ alkyl, —$(CH_2)_n$O—($C_1$-$C_6$ alkyl), —$(CH_2)_n$C(O)—($C_1$-$C_6$ alkyl), —$(CH_2)_n$OC(O)—($C_1$-$C_6$ alkyl), —$(CH_2)_n$C(O)O—($C_1$-$C_6$ alkyl), —$(CH_2)$—NHC(O)—$R_1$, —$(CH_2)$—C(O)—$NR_1R_2$, —$(OCH_2)_n$OH, —$(CH_2O)$.COOH, $C_1$-$C_6$ alkyl, —$(OCH_2)_N$O—($C_1$-$C_6$ alkyl), —$(CH_2O)_n$C(O)—($C_1$-$C_6$ alkyl), —$(OCH_2)_n$NHC(O)—$R_1$, —$(CH_2O)_n$C(O)—$NR_1R_2$, —$S(O)_2$—$R_S$, —S(O)—$R_S$ ($R_S$ is $C_1$-$C_6$ alkyl or a —$(CH_2)_m$—$NR_1R_2$ group), $NO_2$, CN or halogen (F, Cl, Br, I, preferably F or Cl), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—$NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —$(CH_2)_n$OH, —$(CH_2)_n$—O—$(C_1$-$C_6)$alkyl, —$(CH_2)_n$—O—$(CH_2)_n$—$(C_1$-$C_6)$alkyl, —$(CH_2)_n$—C(O)($C_0$-$C_6$) alkyl, —$(CH_2)_n$—C(O)O($C_0$-$C_6$) alkyl, —$(CH_2)_n$—OC(O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, CO groups, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably substituted with a linker group attached to a PTM group, including a ULM group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo- (preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

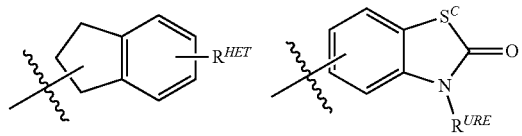

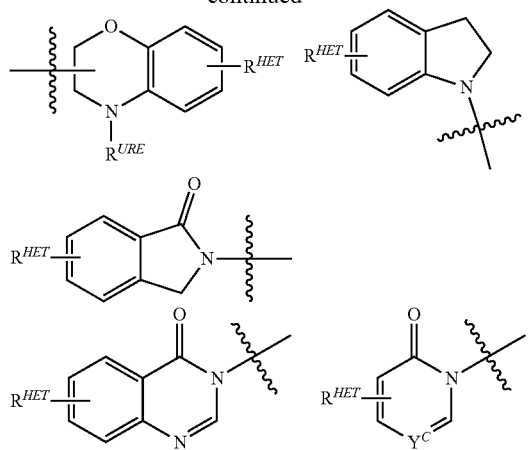

wherein:

$S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl).

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-benzodioxanyl, benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO-heteroaryl, —SO2-alkyl, —SO2-substituted alkyl, —SO2-aryl, oxo (=O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxynitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "independently" is used herein to indicate that the variable, which is independently applied, varies independently from application to application.

The term "lower alkyl" refers to methyl, ethyl or propyl

The term "lower alkoxy" refers to methoxy, ethoxy or propoxy.

In any of the embodiments described herein, the W, X, Y, Z, G, G', R, R', R", Q1-Q4, A, and Rn can independently be covalently coupled to a linker and/or a linker to which is attached one or more PTM, ULM, ILM or ILM' groups.

Exemplary MLMs

In certain additional embodiments, the MLM of the bifunctional compound comprises chemical moieties such as substituted imidazolines, substituted spiro-indolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In still additional embodiments, the MLM comprises part of structural features as in RG7112, RG7388, SAR405838, AMG-232, AM-7209, DS-5272, MK-8242, and NVP-CGM-097, and analogs or derivatives thereof.

In certain preferred embodiments, MLM is a derivative of substituted imidazoline represented as Formula (A-1), or thiazoloimidazoline represented as Formula (A-2), or spiro indolinone represented as Formula (A-3), or pyrollidine represented as Formula (A-4), or piperidinone/morphlinone represented as Formula (A-5), or isoquinolinone represented as Formula (A-6), or pyrollopyrimidine/imidazolopyridine represented as Formula (A-7), or pyrrolopyrrolidinone/imidazolopyrrolidinone represented as Formula (A-8).

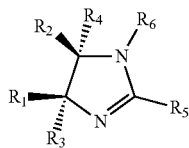

Formula (A-1)

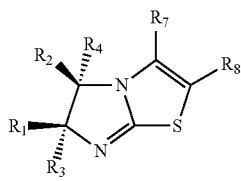

Formula (A-2)

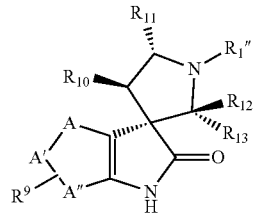

Formula (A-3)

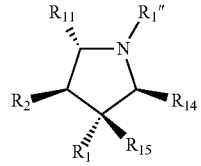

Formula (A-4)

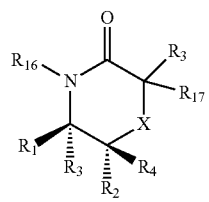

Formula (A-5)

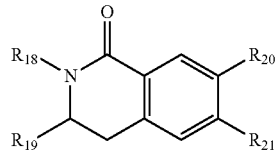

Formula (A-6)

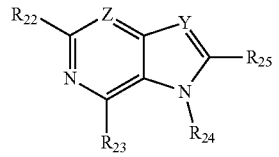

Formula (A-7)

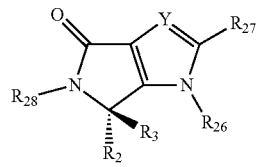

Formula (A-8)

wherein above Formula (A-1) through Formula (A-8),

X of Formula (A-1) through Formula (A-8) is selected from the group consisting of carbon, oxygen, sulfur, sulfoxide, sulfone, and N—$R^a$;

$R^a$ is independently H or an alkyl group with carbon number 1 to 6;

Y and Z of Formula (A-1) through Formula (A-8) are independently carbon or nitrogen;

A, A' and A" of Formula (A-1) through Formula (A-8) are independently selected from C, N, O or S, can also be one or two atoms forming a fused bicyclic ring, or a 6,5- and 5,5-fused aromatic bicyclic group;

$R_1$, $R_2$ of Formula (A-1) through Formula (A-8) are independently selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:

halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, and dialkyl amine with 2 to 6 carbons;

$R_3$, $R_4$ of Formula (A-1) through Formula (A-8) are independently selected from the group consisting of H, methyl and C1 to C6 alkyl;

$R_5$ of Formula (A-1) through Formula (A-8) is selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:

halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, dialkyl amine with 2 to 6 carbons, alkyl ether (C2 to C6), alkyl ketone (C3 to C6), morpholinyl, alkyl ester (C3 to C6), alkyl cyanide (C3 to C6);

$R_6$ of Formula (A-1) through Formula (A-8) is H or —C(=O)$R^b$, wherein $R^b$ of Formula (A-1) through Formula (A-8) is selected from the group consisting of alkyl, cycloalkyl, mono-, di- or tri-substituted aryl or heteroaryl, 4-morpholinyl, 1-(3-oxopiperazunyl), 1-piperidinyl, 4-N—$R^c$-morpholinyl, 4-$R^c$-1-piperidinyl, and 3-$R^c$-1-piperidinyl, wherein $R^c$ of Formula (A-1) through Formula (A-8) is selected from the group consisting of alkyl, fluorine substituted alkyl, cyano alkyl, hydroxyl-substituted alkyl, cycloalkyl, alkoxyalkyl, amide alkyl, alkyl sulfone, alkyl sulfoxide, alkyl amide, aryl, heteroaryl, mono-, bis- and tri-substituted aryl or heteroaryl, CH2CH2$R^d$, and CH2CH2CH2$R^d$, wherein $R^d$ of Formula (A-1) through Formula (A-8) is selected from the group consisting of alkoxy, alkyl sulfone, alkyl sulfoxide, N-substituted carboxamide, —NHC(O)-alkyl, —NH—SO$_2$-alkyl, aryl, substituted aryl, heteroaryl, substituted heteroaryl;

$R_7$ of Formula (A-1) through Formula (A-8) is selected from the group consisting of H, C1 to C6 alkyl, cyclic alkyl, fluorine substituted alkyl, cyano substituted alkyl, 5- or 6-membered hetero aryl or aryl, substituted 5- or 6-membered hetero aryl or aryl;

$R_8$ of Formula (A-1) through Formula (A-8) is selected from the group consisting of —$R^e$—C(O)—$R^f$, —$R^e$-alkoxy, —$R^e$-aryl, —$R^e$-heteroaryl, and —$R^e$—C(O)—$R^f$—C(O)—$R^g$, wherein:

$R^e$ of Formula (A-1) through Formula (A-8) is an alkylene with 1 to 6 carbons, or a bond;

$R^f$ of Formula (A-1) through Formula (A-8) is a substituted 4- to 7-membered heterocycle;

$R^g$ of Formula (A-1) through Formula (A-8) is selected from the group consisting of aryl, hetero aryl, substituted aryl or heteroaryl, and 4- to 7-membered heterocycle;

$R_9$ of Formula (A-1) through Formula (A-8) is selected from the group consisting of a mono-, bis- or tri-substituent on the fused bicyclic aromatic ring in Formula (A-3), wherein the substitutents are independently selected from the group consisting of halogen, alkene, alkyne, alkyl, unsubstituted or substituted with Cl or F;

$R_{10}$ of Formula (A-1) through Formula (A-8) is selected from the group consisting of an aryl or heteroaryl group, wherein the heteroaryl group can contain one or two heteroatoms as sulfur or nitrogen, aryl or heteroaryl group can be mono-cyclic or bi-cyclic, the aryl or heteroaryl group can be unsubstituted or substituted with one to three substituents, including a halogen, F, Cl, —CN, alkene, alkyne, C1 to C6 alkyl group, C1 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons;

$R_{11}$ of Formula (A-1) through Formula (A-8) is —C(O)—N($R^h$)($R^i$), wherein $R^h$ and $R^i$ are selected from groups consisting of the following:

H, C1 to C6 alkyl, alkoxy substituted alkyl, sulfone substituted alkyl, aryl, heterol aryl, mono-, bis- or tri-substituted aryl or hetero aryl, alkyl carboxylic acid, heteroaryl carboxylic acid, alkyl carboxylic acid, fluorine substituted alkyl carboxylic acid, aryl substituted cycloalkyl, hetero aryl substituted cycloalkyl; wherein $R^h$ and $R^i$ of Formula (A-1) through Formula (A-8) are independently selected from the group consisting of H, connected to form a ring, 4-hydroxycyclohehexane; mono- and di-hydroxy substituted alkyl (C3 to C6); 3-hydroxycyclobutane; phenyl-4-carboxylic acid, and substituted phenyl-4-carboxylic acid;

$R_{12}$ and $R_{13}$ of Formula (A-1) through Formula (A-8) are independently selected from H, lower alkyl (C1 to C6), lower alkenyl (C2 to C6), lower alkynyl (C2 to C6), cycloalkyl (4, 5 and 6-membered ring), substituted cycloalkyl, cycloalkenyl, substituted cycloalkenyl, 5- and 6-membered aryl and heteroaryl, R12 and R13 can be connected to form a 5- and 6-membered ring with or without substitution on the ring;

$R_{14}$ of Formula (A-1) through Formula (A-8) is selected from the group consisting of alkyl, substituted alkyl, alkenyl, substituted alkenyl, aryl, substituted aryl, heteroaryl, substituted heteroaryl, heterocycle, substituted heterocycle, cycloalkyl, substituted cycloalkyl, cycloalkenyl and substituted cycloalkenyl;

$R_{15}$ of Formula (A-1) through Formula (A-8) is CN;

$R_{16}$ of Formula (A-1) through Formula (A-8) is selected from the group consisting of C1-6 alkyl, C1-6 cycloalkyl, C2-6 alkenyl, C1-6 alkyl or C3-6 cycloalkyl with one or multiple hydrogens replaced by fluorine, alkyl or cycloalkyl with one CH$_2$ replaced by S(=O), —S, or —S(=O)$_2$, alkyl or cycloalkyl with terminal CH$_3$ replaced by S(=O)$_2$N (alkyl)(alkyl), —C(=O)N(alkyl)(alkyl), —N(alkyl)S (=O)$_2$ (alkyl), —C(=O)2(allkyl), —O(alkyl), C1-6 alkyl or alkyl-cycloalkyl with hydron replaced by hydroxyl group, a 3 to 7 membered cycloalkyl or heterocycloalkyl, optionally containing a —(C=0)-group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halogen, C1-6 alkyl groups, hydroxylated C1-6 alkyl, C1-6 alkyl containing thioether, ether, sulfone, sulfoxide, fluorine substituted ether or cyano group;

$R_{17}$ of Formula (A-1) through Formula (A-8) is selected from the group consisting of (CH$_2$)nC(O)NR$^k$R$^l$, wherein R$^k$ and R$^l$ are independently selected from H, C1-6 alkyl, hydroxylated C1-6 alkyl, C1-6 alkoxy alkyl, C1-6 alkyl with one or multiple hydrogens replaced by fluorine, C1-6 alkyl with one carbon replaced by S(O), S(O)(O), C1-6 alkoxyalkyl with one or multiple hydrogens replaced by fluorine, C1-6 alkyl with hydrogen replaced by a cyano group, 5 and 6 membered aryl or heteroaryl, aklyl aryl with alkyl group containing 1-6 carbons, and alkyl heteroaryl with alkyl group containing 1-6 carbons, wherein the aryl or heteroaryl group can be further substituted;

$R_{18}$ of Formula (A-1) through Formula (A-8) is selected from the group consisting of substituted aryl, heteroaryl, alkyl, cycloalkyl, the substitution is preferably —N(C1-4 alkyl)(cycloalkyl), —N(C1-4 alkyl)alkyl-cycloalkyl, and —N(C1-4 alkyl)[(alkyl)-(heterocycle-substituted)-cycloalkyl];

$R_{19}$ of Formula (A-1) through Formula (A-8) is selected from the group consisting of aryl, heteroaryl, bicyclic heteroaryl, and these aryl or heteroaryl groups can be substituted with halogen, C1-6 alkyl, C1-6 cycloalkyl, $CF_3$, F, CN, alkyne, alkyl sulfone, the halogen substitution can be mon- bis- or tri-substituted;

$R_{20}$ and $R_{21}$ of Formula (A-1) through Formula (A-8) are independently selected from C1-6 alkyl, C1-6 cycloalkyl, C1-6 alkoxy, hydroxylated C1-6 alkoxy, and fluorine substituted C1-6 alkoxy, wherein $R_{20}$ and $R_{21}$ can further be connected to form a 5, 6 and 7-membered cyclic or heterocyclic ring, which can further be substituted;

$R_{22}$ of Formula (A-1) through Formula (A-8) is selected from the group consisting of H, C1-6 alkyl, C1-6 cycloalkyl, carboxylic acid, carboxylic acid ester, amide, reverse amide, sulfonamide, reverse sulfonamide, N-acyl urea, nitrogen-containing 5-membered heterocycle, the 5-membered heterocycles can be further substituted with C1-6 alkyl, alkoxy, fluorine-substituted alkyl, CN, and alkylsulfone;

$R_{23}$ of Formula (A-1) through Formula (A-8) is selected from aryl, heteroaryl, —O-aryl, —O-heteroaryl, —O-alkyl, —O-alkyl-cycloalkyl, —NH-alkyl, —H-alkyl-cycloalkyl, —N(H)-aryl, —N(H)-heteroaryl, —N(alkyl)-aryl, —N(alkyl)-heteroaryl, the aryl or heteroaryl groups can be substituted with halogen, C1-6 alkyl, hydroxylated C1-6 alkyl, cycloalkyl, fluorine-substituted C1-6 alkyl, CN, alkoxy, alkyl sulfone, amide and sulfonamide;

$R_{24}$ of Formula (A-1) through Formula (A-8) is selected from the group consisting of —CH2-(C1-6 alkyl), —CH2-cycloalkyl, —CH2-aryl, CH2-heteroaryl, where alkyl, cycloalkyl, aryl and heteroaryl can be substituted with halogen, alkoxy, hydroxylated alkyl, cyano-substituted alkyl, cycloalyl and substituted cycloalkyl;

$R_{25}$ of Formula (A-1) through Formula (A-8) is selected from the group consisting of C1-6 alkyl, C1-6 alkyl-cycloalkyl, alkoxy-substituted alkyl, hydroxylated alkyl, aryl, heteroaryl, substituted aryl or heteroaryl, 5,6, and 7-membered nitrogen-containing saturated heterocycles, 5,6-fused and 6,6-fused nitrogen-containing saturated heterocycles and these saturated heterocycles can be substituted with C1-6 alkyl, fluorine-substituted C1-6 alkyl, alkoxy, aryl and heteroaryl group;

$R_{26}$ of Formula (A-1) through Formula (A-8) is selected from the group consisting of C1-6 alkyl, C3-6 cycloalkyl, the alkyl or cycloalkyl can be substituted with —OH, alkoxy, fluorine-substituted alkoxy, fluorine-substituted alkyl, —$NH_2$, —NH-alkyl, NH—C(O)alkyl, —NH—S(O)$_2$-alkyl, and —S(O)$_2$-alkyl;

$R_{27}$ of Formula (A-1) through Formula (A-8) is selected from the group consisting of aryl, heteroaryl, bicyclic heteroaryl, wherein the aryl or heteroaryl groups can be substituted with C1-6 alkyl, alkoxy, NH2, NH-alkyl, halogen, or —CN, and the substitution can be independently mono-, bis- and tri-substitution;

$R_{28}$ of Formula (A-1) through Formula (A-8) is selected from the group consisting of aryl, 5 and 6-membered heteroaryl, bicyclic heteroaryl, cycloalkyl, saturated heterocycle such as piperidine, piperidinone, tetrahydropyran, N-acyl-piperidine, wherein the cycloalkyl, saturated heterocycle, aryl or heteroaryl can be further substituted with —OH, alkoxy, mono-, bis- or tri-substitution including halogen, —CN, alkyl sulfone, and fluorine substituted alkyl groups; and $R_{1''}$ of Formula (A-1) through Formula (A-8) is selected from the group consisting of alkyl, aryl substituted alkyl, alkoxy substituted alkyl, cycloalkyl, aryl-substituted cycloalkyl, and alkoxy substituted cycloalkyl.

In certain embodiments, the heterocycles in $R^f$ and $R^g$ of Formula (A-1) through Formula (A-8) are substituted pyrrolidine, substituted piperidine, substituted piperizine.

More specifically, non-limiting examples of MLMs include those shown below as well as those 'hybrid' molecules that arise from the combination of 1 or more of the different features shown in the molecules below.

Using MLM in Formula A-1 through A-8, the following PROTACs can be prepared to target a particular protein for degradation, where 'L' is a connector (i.e. a linker group), and "PTM" is a ligand binding to a target protein.

In certain embodiments, the description provides a bifunctional molecule comprising a structure selected from the group consisting of:

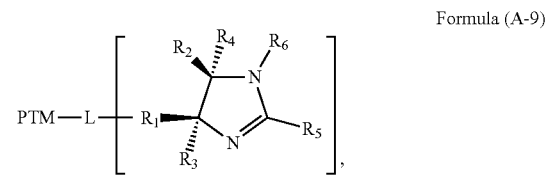

Formula (A-9)

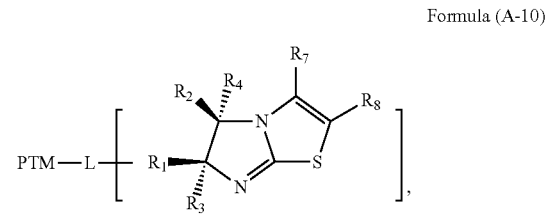

Formula (A-10)

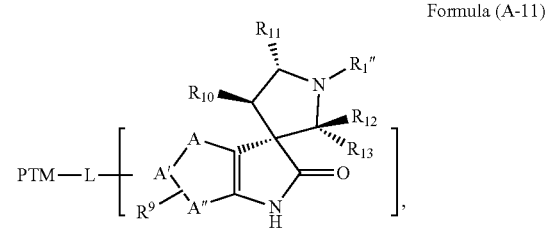

Formula (A-11)

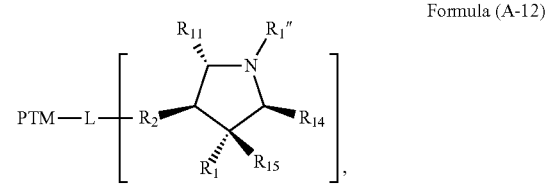

Formula (A-12)

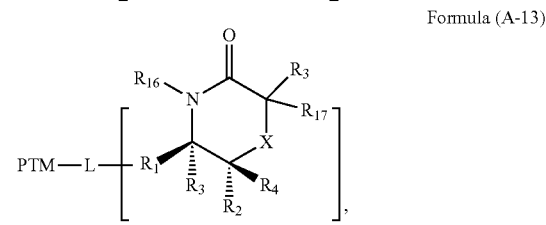

Formula (A-13)

-continued

Formula (A-14)

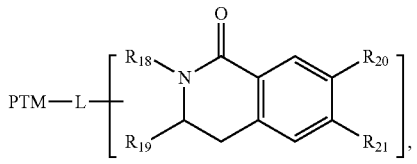

Formula (A-15)


and

Formula (A-16)

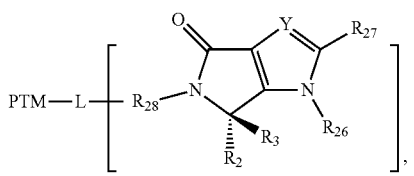

wherein X, $R^a$, Y, Z, A, A', A", $R_1$, $R_2$, $R_3$, $R_4$, $R_5$, $R_6$, $R^b$, $R^e$, $R^d$, $R_7$, $R^e$, $R^f$, $R^g$, $R_9$, $R_{10}$, $R_{11}$, $R_{12}$, $R_{13}$, $R_{14}$, $R_{15}$, $R_{16}$, $R_{17}$, $R^k$, $R^l$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, and $R_{1''}$ are as defined herein with regard to Formulas (A-1) through (A-8).

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-1-1, A-1-2, A-1-3, and A-1-4:

A-1-1

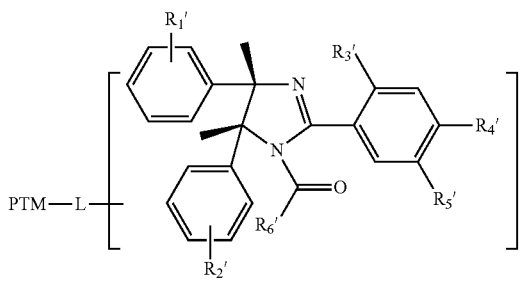

A-1-2

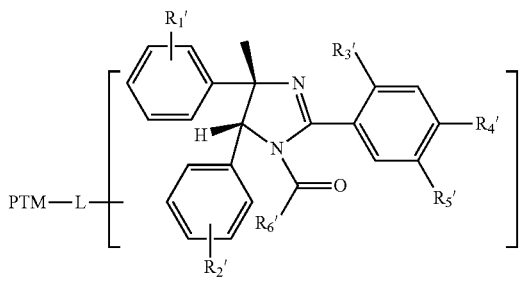

A-1-3

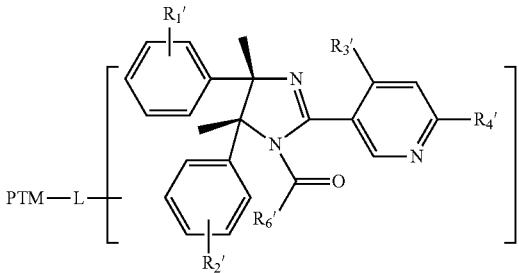

A-1-4

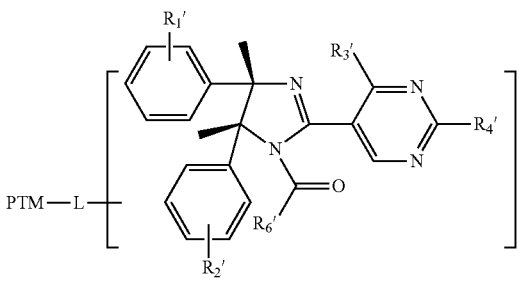

wherein:

R1' and R2' of Formulas A-1-1 through A-1-4 (i.e., A-1-1, A-1-2, A-1-3, and A-1-4) are independently selected from the group consisting of F, Cl, Br, I, acetylene, CN, $CF_3$ and $NO_2$; R3' is selected from the group consisting of —$OCH_3$, —$OCH_2CH_3$, —$OCH_2CH_2F$, —$OCH_2CH_2OCH_3$, and —$OCH(CH_3)_2$;

R4' of Formulas A-1-1 through A-1-4 is selected from the group consisting of H, halogen, —$CH_3$, —$CF_3$, —$OCH_3$, —$C(CH_3)_3$, —$CH(CH_3)_2$, -cyclopropyl, —CN, —$C(CH_3)_2$OH, —$C(CH_3)_2OCH_2CH_3$, —$C(CH_3)_2CH_2OH$, —$C(CH_3)_2$ $CH_2OCH_2CH_3$, —$C(CH_3)_2CH_2OCH_2CH_2OH$, —$C(CH_3)_2$ $CH_2OCH_2CH_3$, —$C(CH_3)_2CN$, —$C(CH_3)_2C(O)CH_3$, —$C(CH_3)_2C(O)NHCH_3$, —$C(CH_3)_2C(O)N(CH_3)_2$, —$SCH_3$, —$SCH_2CH_3$, —$S(O)_2CH_3$, —$S(O_2)CH_2CH_3$, —$NHC(CH_3)_3$, —$N(CH_3)_2$, pyrrolidinyl, and 4-morpholinyl;

R5' of Formulas A-1-1 through A-1-4 is selected from the group consisting of halogen, -cyclopropyl, —$S(O)_2CH_3$, —$S(O)_2CH_2CH_3$, 1-pyrrolidinyl, —$NH_2$, —$N(CH_3)_2$, and —$NHC(CH_3)_3$; and R6' of Formulas A-1-1 through A-1-4 is selected from the structures presented below where the linker connection point is indicated as "*".

Beside R6' as the point for linker attachment, R4' can also serve as the linker attachment position. In the case that R4' is the linker connection site, linker will be connected to the terminal atom of R4' groups shown above.

In certain embodiments, the linker connection position of Formulas A-1-1 through A-1-4 is at least one of R4' or R6' or both.

In certain embodiments, R6' of Formulas A-1-1 through A-1-4 is independently selected from the group consisting of H,

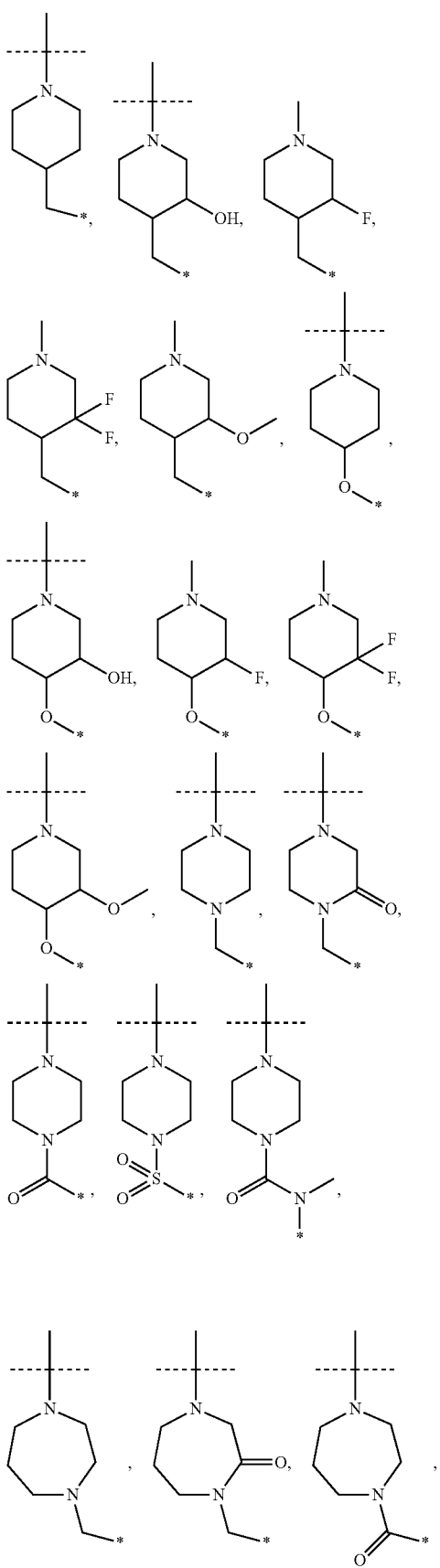
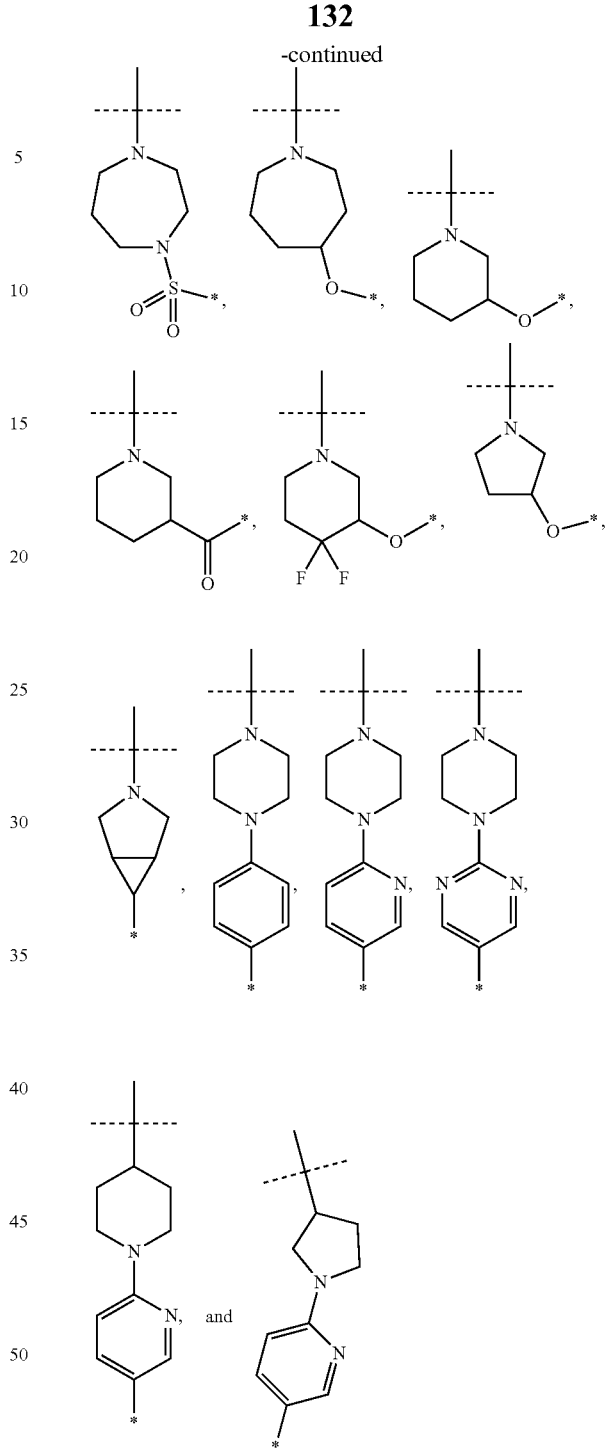

wherein "*" indicates the point of attachment of the linker.

In certain embodiments, the linker of Formula A-4-1 through A-4-6 is attached to at least one of R1', R2', R3', R4', R5', R6', or a combination thereof.

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-4-1, A-4-2, A-4-3, A-4-4, A-4-5, and A-4-6:

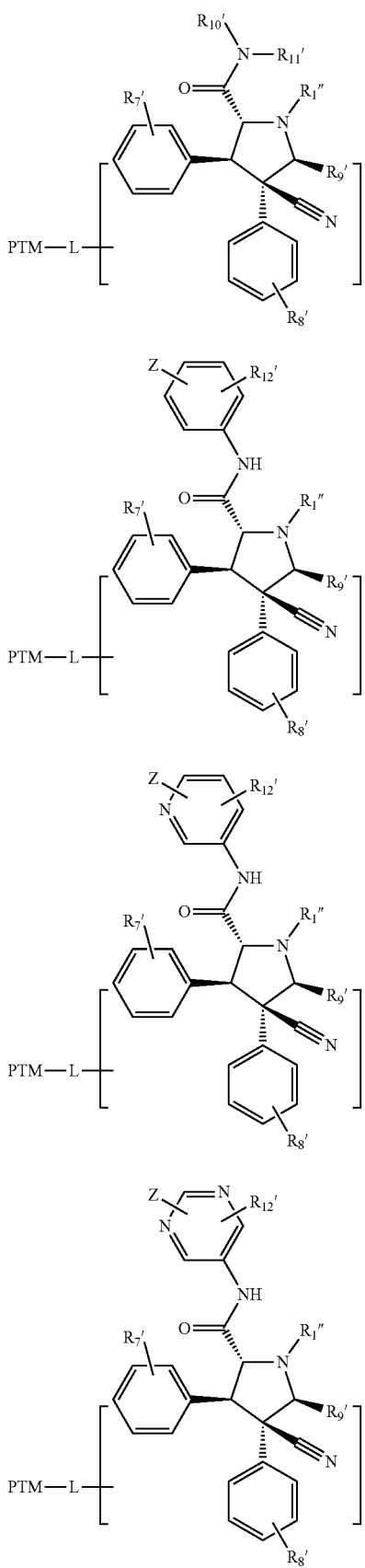

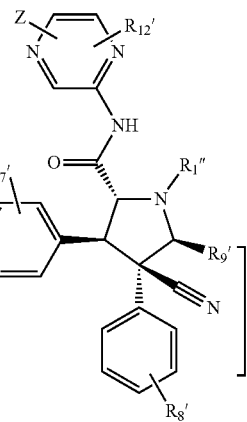

wherein:

R7' of Formula A-4-1 through A-4-6 (i.e., A-4-1, A-4-2, A-4-3, A-4-4, A-4-5, and A-4-6) is a member selected from the group consisting of halogen, mono-, and di- or tri-substituted halogen;

R8' of Formula A-4-1 through A-4-6 is selected from the group consisting of H, —F, —Cl, —Br, —I, —CN, —NO$_2$, ethylnyl, cyclopropyl, methyl, ethyl, isopropyl, vinyl, methoxy, ethoxy, isopropoxy, —OH, other C1-6 alkyl, other C1-6 alkenyl, and C1-6 alkynyl, mono-, di- or tri-substituted; R9' of Formula A-4-1 through A-4-6 is selected from the group consisting of alkyl, substituted alkyl, alkenyl, substituted alkenyl, alkynyl, substituted alkynyl, aryl, substituted aryl, hetero aryl, substituted heteroaryl, cycloalkyl, substituted cycloalkyl, alkenyl, and substituted cycloalkenyl;

Z of Formula A-4-1 through A-4-6 is selected from the group consisting of H, —OCH$_3$, —OCH$_2$CH$_3$, and halogen;
R10' and R11' of Formula A-4-1 through A-4-6 are each independently selected from the group consisting of H, (CH$_2$)$_n$—R', (CH$_2$)$_n$—NR'R", (CH$_2$)$_n$—NR'COR", (CH$_2$)$_n$—NR'SO$_2$R", (CH$_2$)$_n$—COOH, (CH$_2$)$_n$—COOR', (CH)$_n$—CONR'R", (CH$_2$)$_n$—OR', (CH$_2$)$_n$—SR', (CH$_2$)$_n$—SOR', (CH$_2$)$_n$—CH(OH)—R', (CH$_2$)$_n$—COR', (CH$_2$)$_n$—SO$_2$R', (CH$_2$)$_n$—SONR'R", (CH$_2$)$_n$—SO$_2$NR'R", (CH$_2$CH$_2$O)$_m$—(CH$_2$)$_n$—R', (CH$_2$CH$_2$O)$_m$—(CH$_2$)$_n$—OH, (CH$_2$CH$_2$O)$_m$—(CH$_2$)$_n$—OR', (CH$_2$CH$_2$O)$_m$—(CH$_2$)$_n$—NR'R", (CH$_2$CH$_2$O)$_m$—(CH$_2$)$_n$—NR'COR", (CH$_2$CH$_2$O)$_m$(CH$_2$)$_n$—NR'SO$_2$R", (CH$_2$CH$_2$O)$_m$(CH$_2$)$_n$—COOH, (CH$_2$CH$_2$O)$_m$—(CH2)$_n$—CONR'R", (CH$_2$CH$_2$O)$_m$—(CH$_2$)$_n$—SO$_2$R', (CH$_2$CH$_2$O)$_m$—(CH$_2$)$_n$—COR', (CH$_2$CH$_2$O)$_m$—(CH$_2$)$_n$—SONR'R", (CH$_2$CH$_2$O)$_m$—(CH$_2$)$_n$—SO$_2$NR'R", (CH$_2$)$_p$—(CH$_2$CH$_2$O)$_m$—(CH$_2$)$_n$R', (CH$_2$)$_p$—(CH$_2$CH$_2$O)$_m$—(CH$_2$)$_n$—OH, (CH$_2$)$_p$—(CH$_2$CH$_2$O)$_m$—(CH$_2$)n-OR', (CH$_2$)$_p$—(CH$_2$CH$_2$O)$_m$—(CH$_2$)$_n$—NR'R", (CH$_2$)$_p$—(CH$_2$CH$_2$O)$_m$—(CH$_2$)$_n$—NR'COR", (CH$_2$)$_p$—(CH$_2$CH$_2$O)m-(CH$_2$)$_n$—NR'SO$_2$R", (CH$_2$)$_p$—(CH$_2$CH$_2$O)$_m$—(CH$_2$)$_n$—COOH, (CH$_2$)$_p$—(CH$_2$CH$_2$O)$_m$—(CH$_2$)$_n$—COOR', (CH$_2$)$_p$—(CH$_2$CH$_2$O)$_m$—(CH$_2$)$_n$—CONR'R", (CH$_2$)p-(CH$_2$CH$_2$O)$_m$—(CH$_2$)$_n$—SO$_2$R', (CH2)$_p$—(CH$_2$CH$_2$O)$_m$—(CH$_2$)$_n$—COR', (CH$_2$)$_p$—(CH$_2$CH$_2$O)$_m$—(CH$_2$)$_n$—SONR'R", (CH$_2$)$_p$—(CH$_2$CH$_2$O)$_m$—(CH$_2$)$_n$—SO$_2$NR'R", Aryl-(CH$_2$)$_n$—COOH, and heteroaryl-alkyl-CO-alkyl-NR'R"m, wherein the alkyl may be substituted with OR', and heteroaryl-(CH$_2$)$_n$-heterocycle wherein the heterocycle may optionally be substituted with alkyl, hydroxyl, COOR' and COR'; wherein R' and R" are selected from H, alkyl, alkyl substituted with halogen, hydroxyl, NH2, NH(alkyl), N(alkyl)$_2$, oxo, carboxy, clcloalkyl and heteroaryl;
m, n, and p are independently 0 to 6;
R12' of Formula A-4-1 through A-4-6 is selected from the group consisting of —O-(alkyl), —O-(alkyl)-akoxy, —C(O)-(alkyl), —C(OH)-alkyl-alkoxy, —C(O)—NH-(alkyl), —C(O)—N-(alkyl)$_2$, —S(O)-(alkyl), S(O)$_2$-(alkyl), —C(O)-(cyclic amine), and —O-aryl-(alkyl), —O-aryl-(alkoxy);
R1" of Formula A-4-1 through A-4-6 is selected from the group consisting of alkyl, aryl substituted alkyl, aloxy substituted alkyl, cycloalkyl, ary-substituted cycloalkyl, and alkoxy substituted cycloalkyl.

In any of the aspects or embodiments described herein, the alkyl, alkoxy or the like can be a lower alkyl or lower alkoxy.

In certain embodiments, the linker connection position of Formula A-4-1 through A-4-6 is at least one of Z, R8', R9', R10', R11", R12", or R1".

The method used to design chimeric molecules as presented in A-1-1 through A-1-4, A-4-1 through A-4-6 can be applied to MLM with formula A-2, A-3, A-5, A-6, A-7 and A-8, wherein the solvent exposed area in the MLM can be connected to linker "L" which will be attached to target protein ligand "PTM", to construct PROTACs.

Exemplary MDM2 binding moieties include, but not limited to, the following:

The HDM2/MDM2 inhibitors identified in Vassilev, et al., in vivo activation of the p53 pathway by small-molecule antagonists of MDM2, *SCIENCE* vol: 303, pag: 844-848 (2004), and Schneekloth, et al., Targeted intracellular protein degradation induced by a small molecule: En route to chemical proteomics, *Bioorg. Med. Chem. Lett.* 18 (2008) 5904-5908, including (or additionally) the compounds nutlin-3, nutlin-2, and nutlin-1 (derivatized) as described below, as well as all derivatives and analogs thereof:

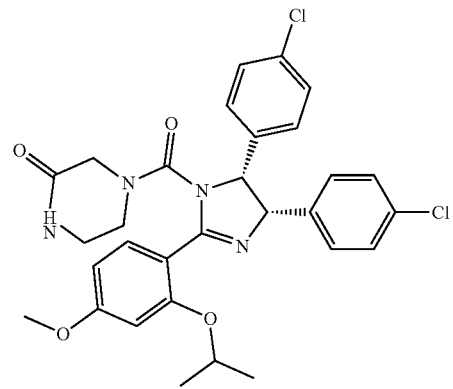 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

(derivatized where a linker group L or a -(L-MLM)group is attached, for example, at the methoxy group or as a hydroxyl group);

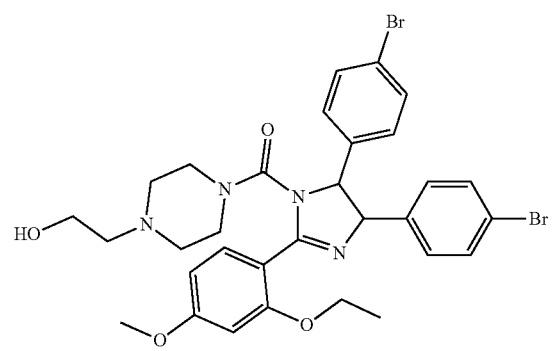 [SMILES: CCOc1cc(OC)ccc1C1=NC(c2ccc(Br)cc2)C(c2ccc(Br)cc2)N1C(=O)N1CCN(CCO)CC1]

(derivatized where a linker group L or a -(L-MLM) group is attached, for example, at the methoxy group or hydroxyl group); and

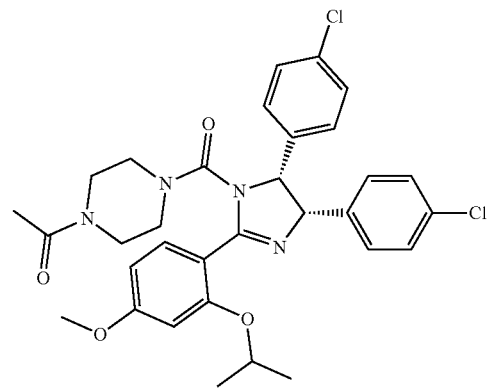 [SMILES: COc1ccc(C2=N[C@@H](c3ccc(Cl)cc3)[C@@H](c3ccc(Cl)cc3)N2C(=O)N2CCN(C(C)=O)CC2)c(OC(C)C)c1]

(derivatized where a linker group L or a -(L-MLM) group is attached, for example, via the methoxy group or as a hydroxyl group).

Exemplary CLMs

Neo-Imide Compounds

In one aspect the description provides compounds useful for binding and/or inhibiting cereblon. In certain embodiments, the compound is selected from the group consisting of chemical structures:

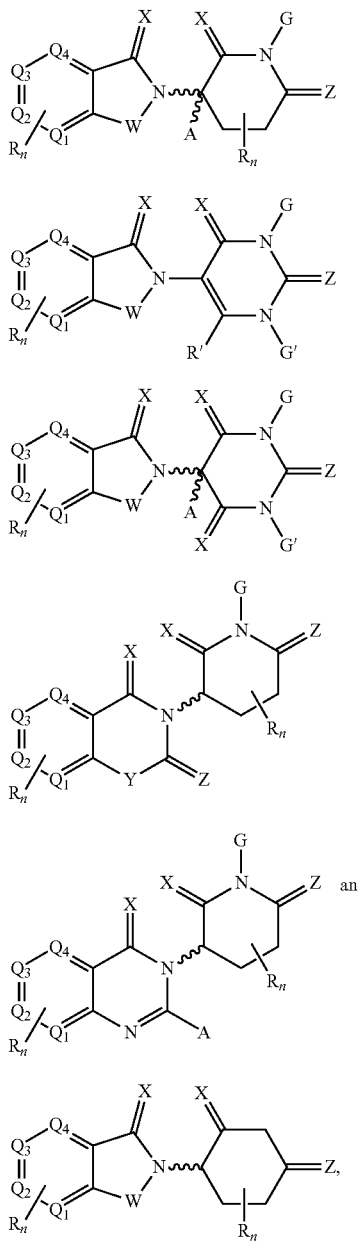

(a)
(b)
(c)
(d)
(e) and
(f)

wherein:
W of Formulas (a) through (e) is independently selected from the group $CH_2$, CHR, C=O, $SO_2$, NH, and N-alkyl;
X of Formulas (a) through (e) is independently selected from the group O, S and $H_2$,
Y of Formulas (a) through (e) is independently selected from the group $CH_2$, —C=CR', NH, N-alkyl, N-aryl, N-hetaryl, N-cycloalkyl, N-heterocyclyl, O, and S;
Z of Formulas (a) through (e) is independently selected from the group O, and S or $H_2$ except that both X and Z cannot be $H_2$,
G and G' of Formulas (a) through (e) are independently selected from the group H, alkyl (linear, branched, optionally substituted), OH, R'OCOOR, R'OCONRR", $CH_2$-heterocyclyl optionally substituted with R', and benzyl optionally substituted with R';

Q1-Q4 of Formulas (a) through (e) represent a carbon C substituted with a group independently selected from R', N or N-oxide;
A of Formulas (a) through (e) is independently selected from the group H, alkyl (linear, branched, optionally substituted), cycloalkyl, Cl and F;
R of Formulas (a) through (e) comprises, but is not limited to: —CONR'R", —OR', —NR'R", —SR', —$SO_2$R', —$SO_2$NR'R", —CR'R"—, —CR'NR'R"—, (—CR'O) nR", -aryl, -hetaryl, -alkyl (linear, branched, optionally substituted), -cycloalkyl, -heterocyclyl, —P(O)(OR') R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(=N—CN) NR'R", —C(=N—CN)NR'R", —NR'C(=N—CN)R", —NR'C(=C—$NO_2$)NR'R", —$SO_2$NR'COR", —$NO_2$, —$CO_2$R', —C(C=N—OR')R", —CR'=CR'R", —CCR', —S(C=O)(C=N—R')R", —$SF_5$ and —$OCF_3$
R' and R" of Formulas (a) through (e) are independently selected from a bond, H, alkyl, cycloalkyl, aryl, heteroaryl, heterocyclic, —C(=O)R, heterocyclyl, each of which is optionally substituted;
n of Formulas (a) through (e) is an integer from 1-10 (e.g., 1-4);
∿ of Formulas (a) through (e) represents a bond that may be stereospecific ((R) or (S)) or non-stereospecific; and
$R_n$ of Formulas (a) through (e) comprises 1-4 independent functional groups, optionally substituted alkoxyl group (e.g., a methoxy, ethoxy, butoxy, propoxy, pentoxy, or hexoxy; wherein the alkoxyl may be substituted with a halogen, a cycloalkyl (e.g., a C3-C6 cycloalkyl), or an aryl (e.g., C5-C7 aryl)), or atoms.

Exemplary CLMs

In any of the compounds described herein, the CLM comprises a chemical structure selected from the group:

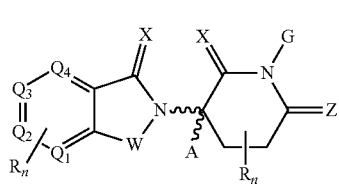
(a)

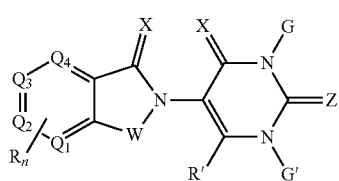
(b)

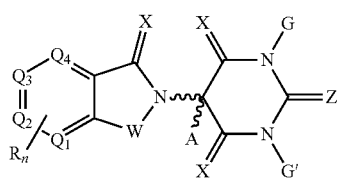
(c)

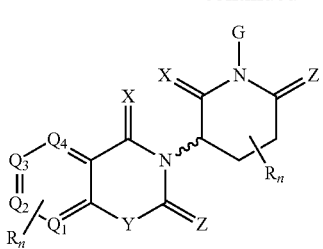
(d)

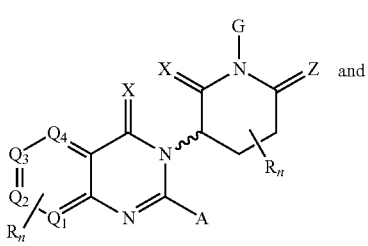
(e) and

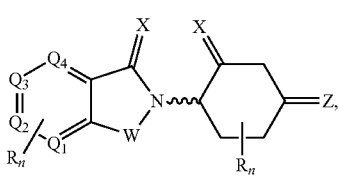
(f)

wherein:
- W of Formulas (a) through (e) is independently selected from the group $CH_2$, CHR, C=O, $SO_2$, NH, and N-alkyl;
- X of Formulas (a) through (e) is independently selected from the group O, S and $H_2$;
- Y of Formulas (a) through (e) is independently selected from the group CH2, —C=CR', NH, N-alkyl, N-aryl, N-hetaryl, N-cycloalkyl, N-heterocyclyl, O, and S;
- Z of Formulas (a) through (e) is independently selected from the group O, and S or H2 except that both X and Z cannot be H2;
- G and G' of Formulas (a) through (e) are independently selected from the group H, alkyl (linear, branched), OH, R'OCOOR, R'OCONRR", $CH_2$-heterocyclyl optionally substituted with R', and benzyl optionally substituted with R';
- Q1-Q4 of Formulas (a) through (e) represent a carbon C substituted with a group independently selected from R', N or N-oxide;
- A of Formulas (a) through (e) is independently selected from the group H, alkyl (linear, branched, optionally substituted), cycloalkyl, Cl and F;
- R of Formulas (a) through (e) comprises, but is not limited to: —CONR'R", —OR', —NR'R", —SR', —SO2R', —SO2NR'R", —CR'R"—, —CR'NR'R"—, -aryl, -hetaryl, -alkyl (linear, branched, optionally substituted), -cycloalkyl, -heterocyclyl, —P(O)(OR')R", —P(O)R'R", —OP(O)(OR')R", —OP(O)R'R", —Cl, —F, —Br, —I, —CF3, —CN, —NR'SO2NR'R", —NR'CONR'R", —CONR'COR", —NR'C(=N—CN)NR'R", —C(=N—CN)NR'R", —NR'C(=N—CN)R", —NR'C(=C—NO2)NR'R", —SO2NR'COR", —NO2, —CO2R', —C(C=N—OR')R", —CR'=CR'R", —CCR', —S(C=O)(C=N—R')R", —SF5 and —OCF3
- R' and R" of Formulas (a) through (e) are independently selected from a bond, H, alkyl, cycloalkyl, aryl, heteroaryl, heterocyclic, —C(=O)R, heterocyclyl, each of which is optionally substituted;
- n of Formulas (a) through (e) is an integer from 1-10 (e.g., 1-4);
- ~~ of Formulas (a) through (e) represents a bond that may be stereospecific ((R) or (S)) or non-stereospecific; and
- Rn of Formulas (a) through (e) comprises 1-4 independent functional groups, optionally substituted alkoxyl group (e.g., a methoxy, ethoxy, butoxy, propoxy, pentoxy, or hexoxy; wherein the alkoxyl may be substituted with a halogen, a cycloalkyl (e.g., a C3-C6 cycloalkyl), or an aryl (e.g., C5-C7 aryl)), or atoms, and optionally, one of which is modified to be covalently joined to a PTM, a chemical linker group (L), a ULM, CLM (or CLM') or combination thereof.

In certain embodiments described herein, the CLM or ULM comprises a chemical structure selected from the group:

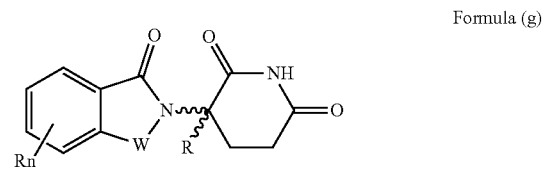
Formula (g)

wherein:
- W of Formula (g) is independently selected from the group $CH_2$, C=O, NH, and N-alkyl;
- R of Formula (g) is independently selected from a H, methyl, alkyl (e.g., a or C1-C6 alkyl (linear, branched, optionally substituted));
- ~~ of Formula (g) represents a bond that may be stereospecific ((R) or (S)) or non-stereospecific; and
- Rn of Formula (g) comprises 1-4 independently selected functional groups, optionally substituted alkoxyl group (e.g., a methoxy, ethoxy, butoxy, propoxy, pentoxy, or hexoxy; wherein the alkoxyl may be substituted with a halogen, a cycloalkyl (e.g., a C3-C6 cycloalkyl), or an aryl (e.g., C5-C7 aryl)), or atoms, and optionally, one of which is modified to be covalently joined to a PTM, a chemical linker group (L), a ULM, CLM (or CLM') or combination thereof.

In any of the embodiments described herein, the W, X, Y, Z, G, G', R, R', R", Q1-Q4, A, and Rn of Formulas (a) through (g) can independently be covalently coupled to a linker and/or a linker to which is attached one or more PTM, ULM, CLM or CLM' groups.

More specifically, non-limiting examples of CLMs include those shown below as well as those "hybrid" molecules that arise from the combination of 1 or more of the different features shown in the molecules below.

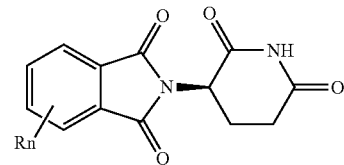

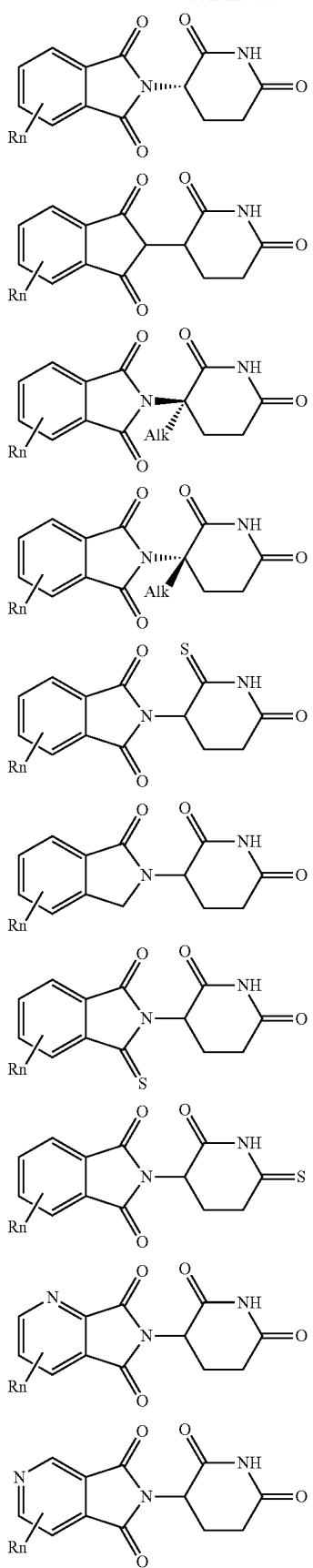
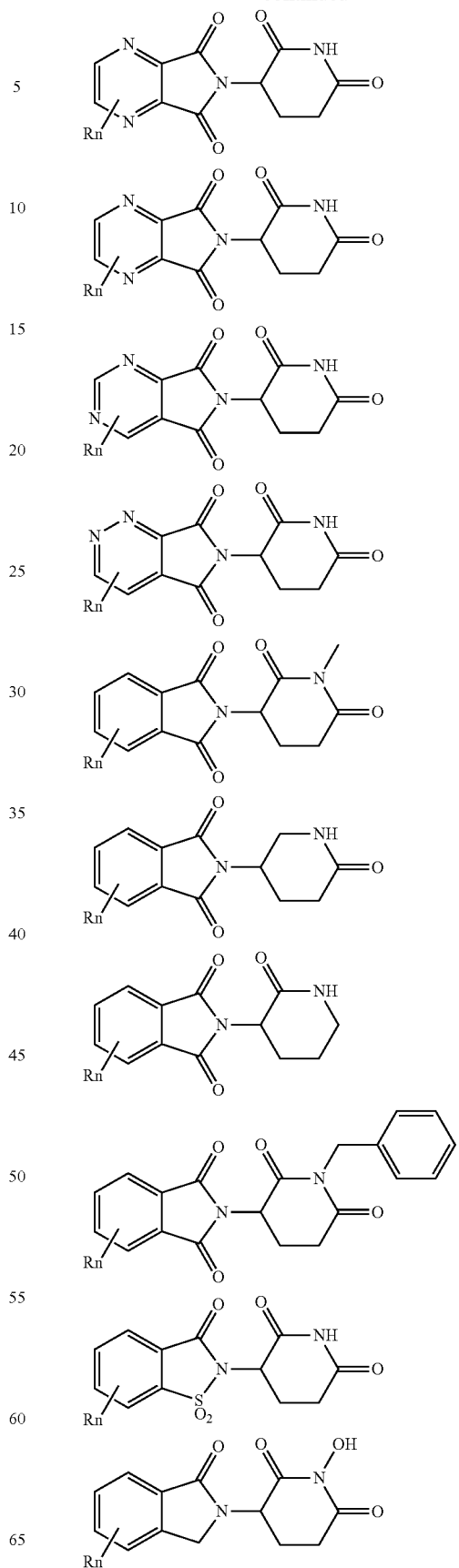

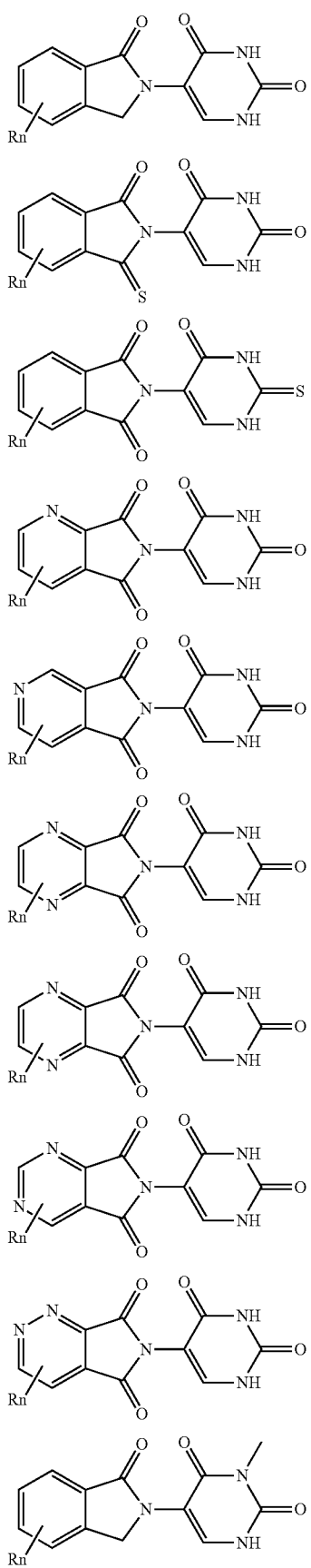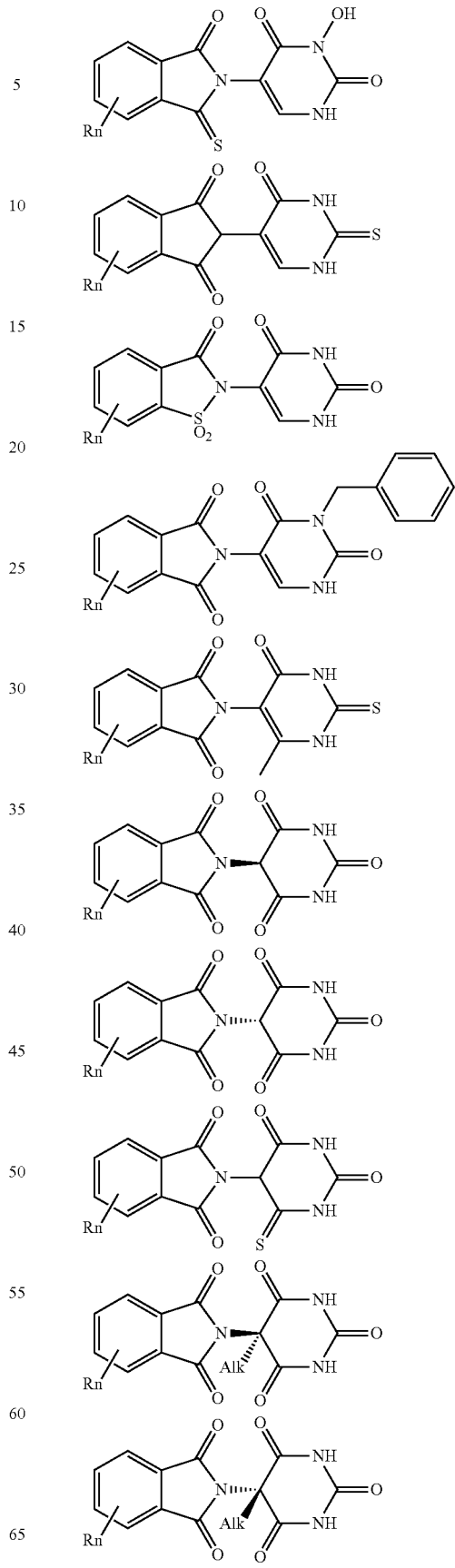

-continued
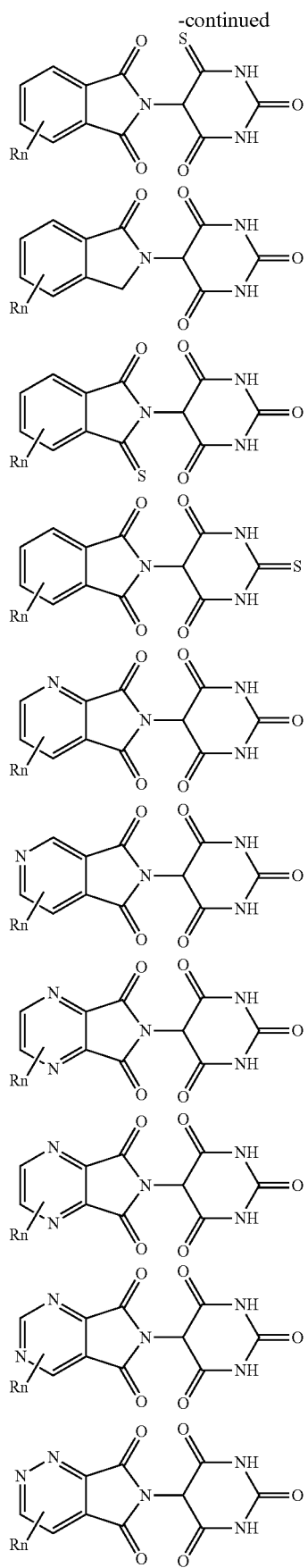
-continued
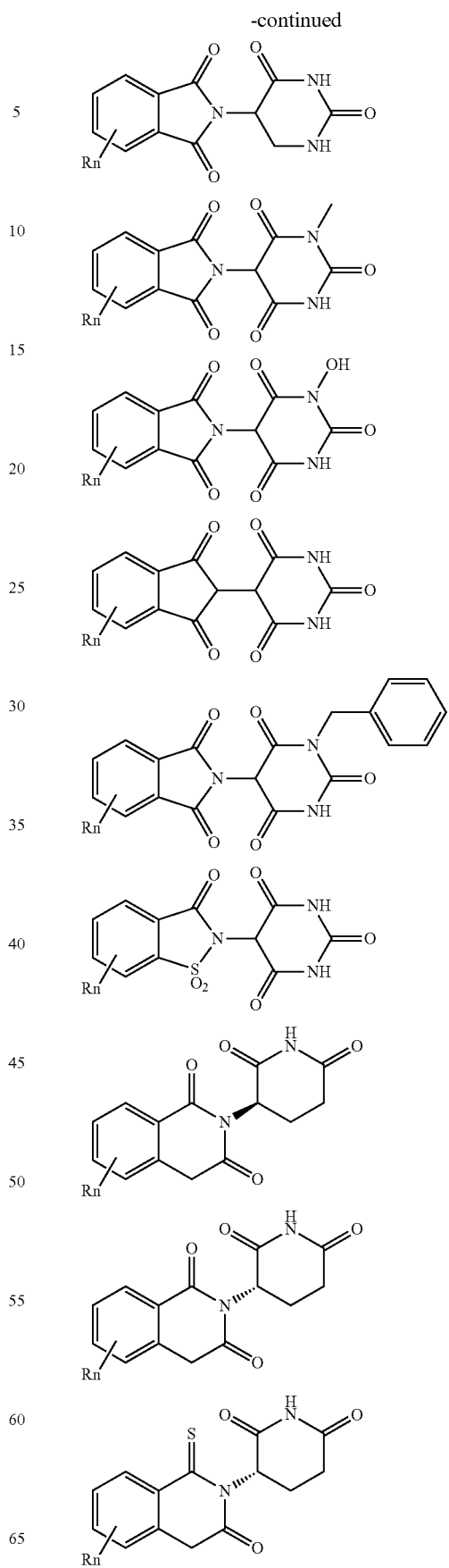

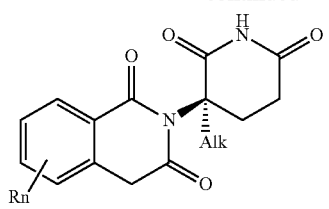
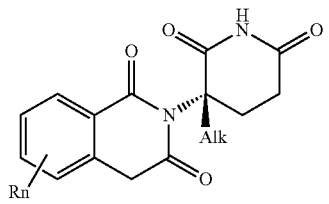
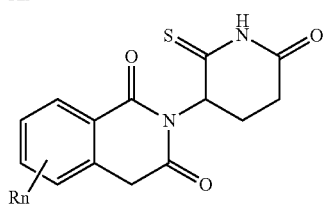
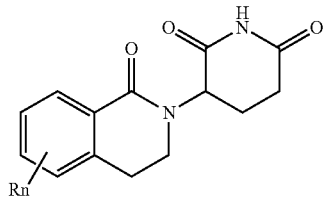
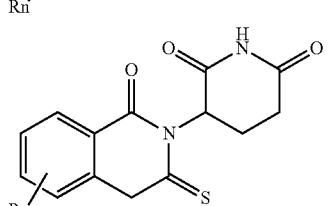
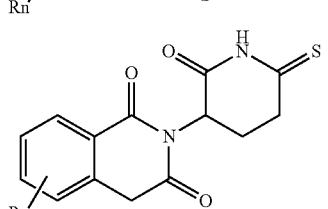
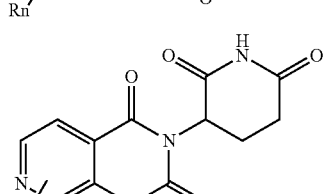
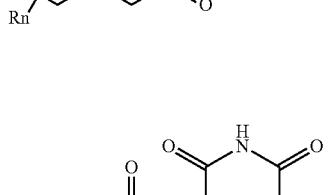
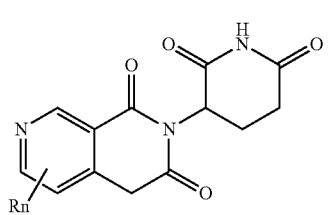
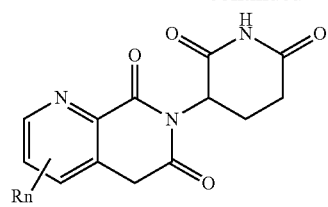
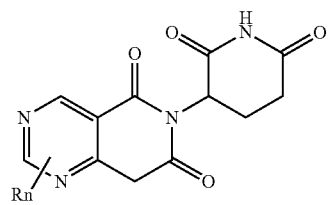
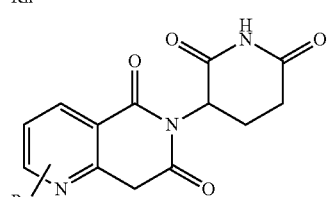
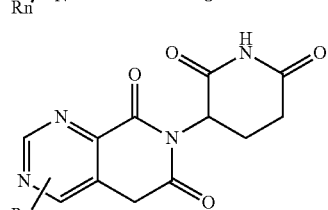
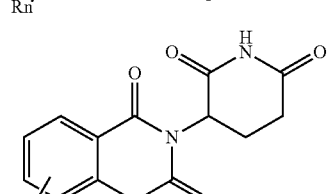
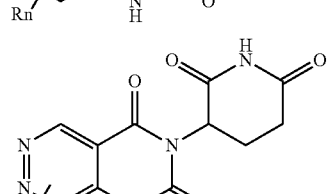
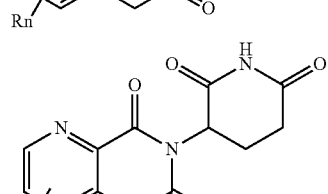
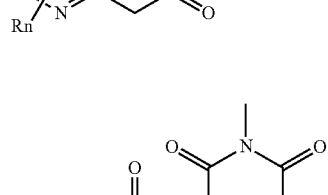
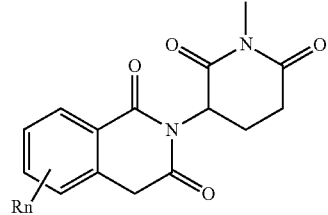

149
-continued
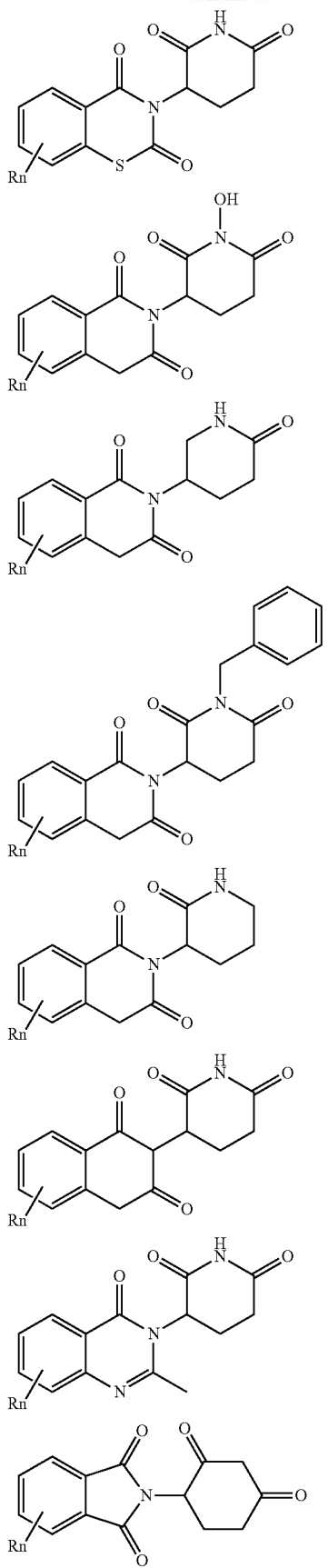
150
-continued
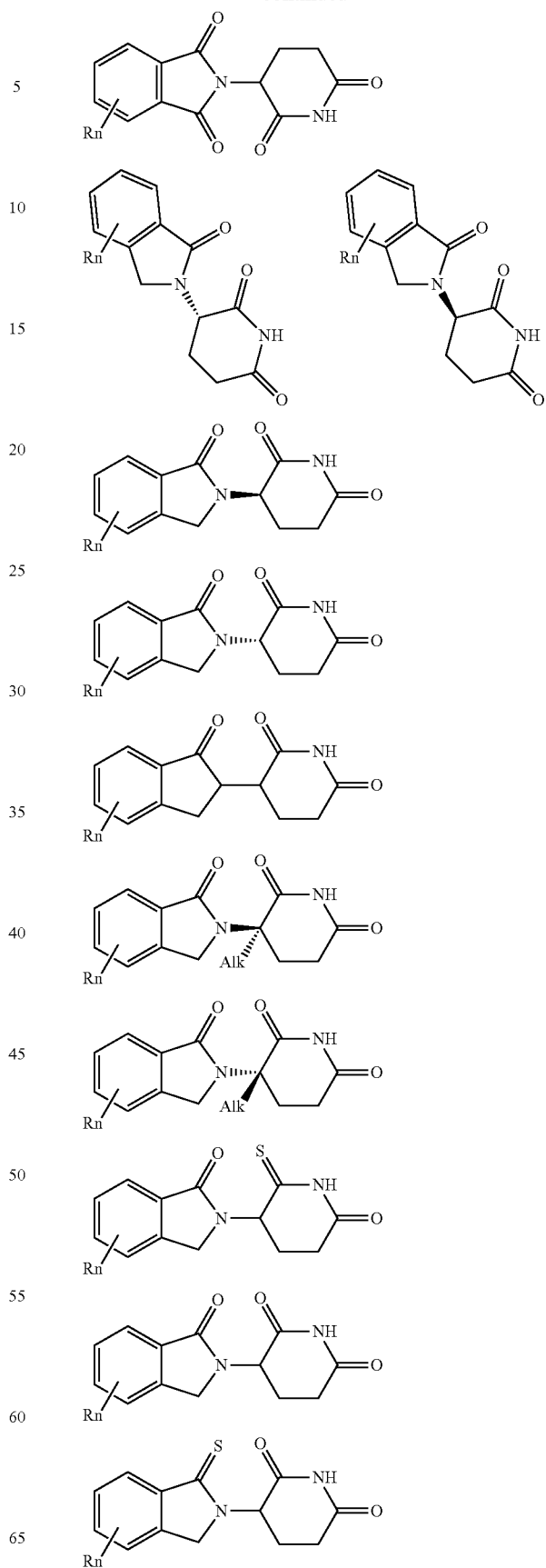

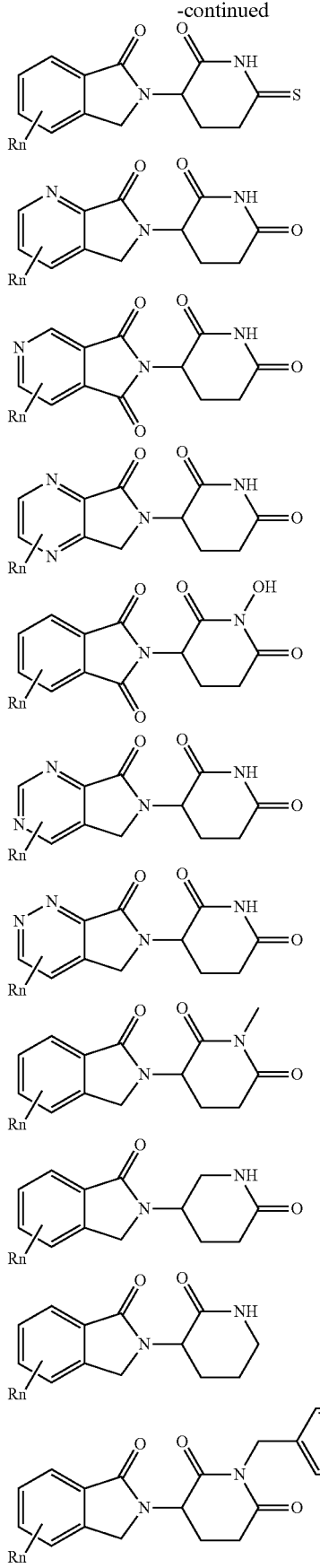
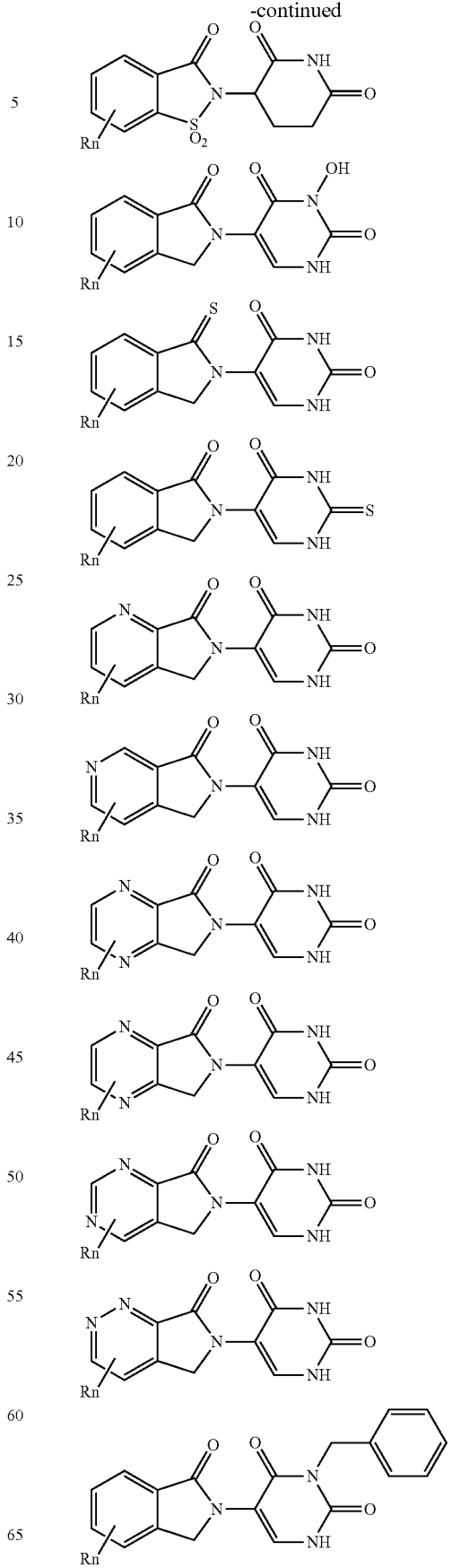

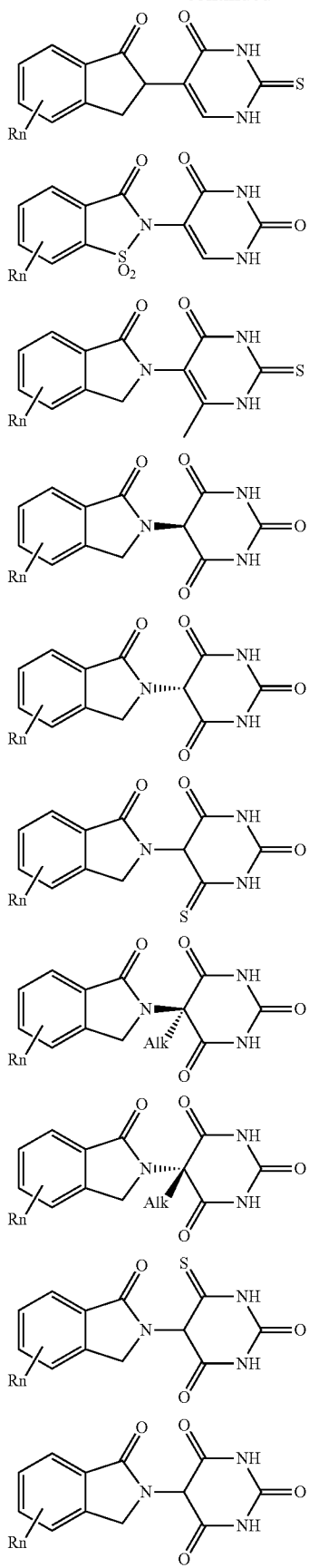
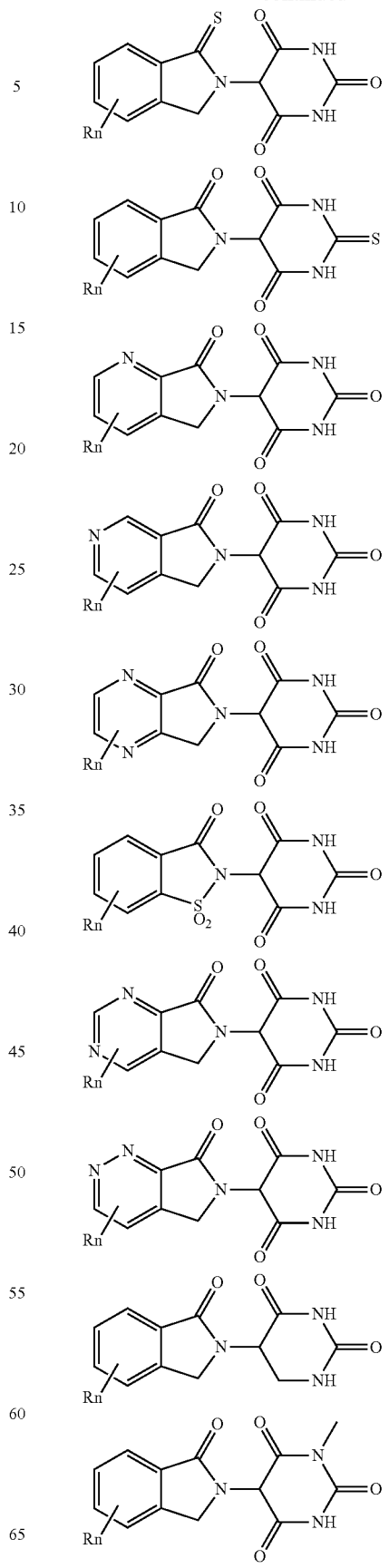

155
-continued
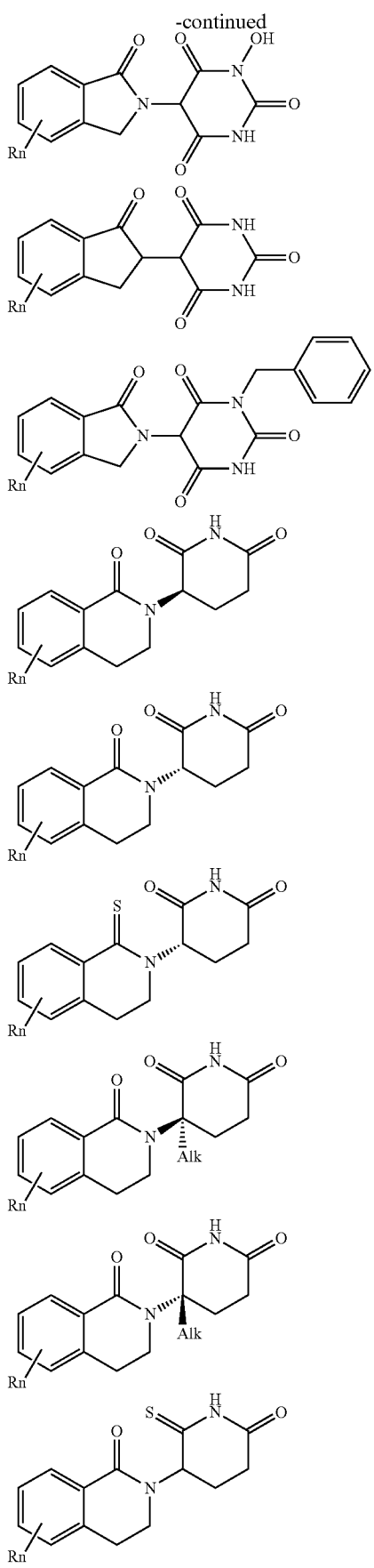
156
-continued
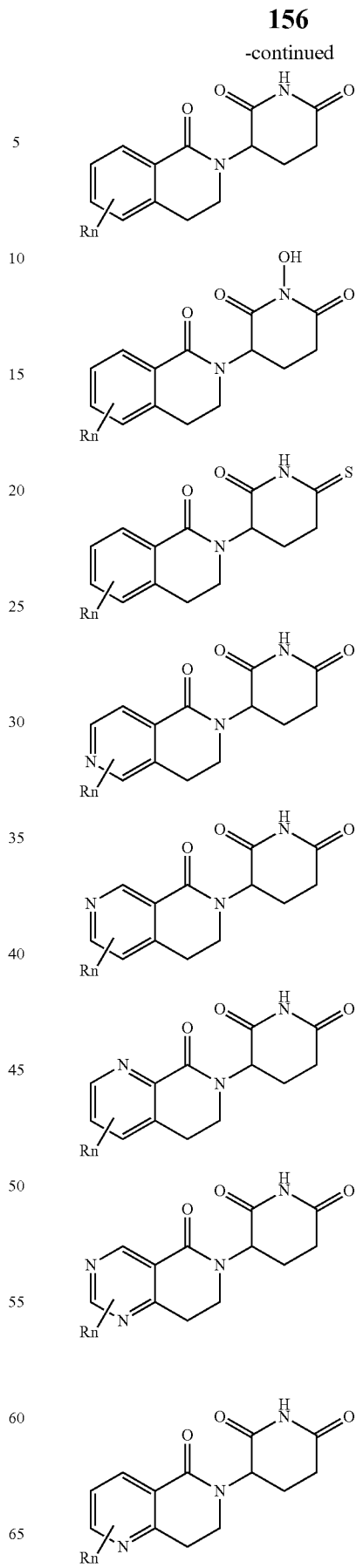

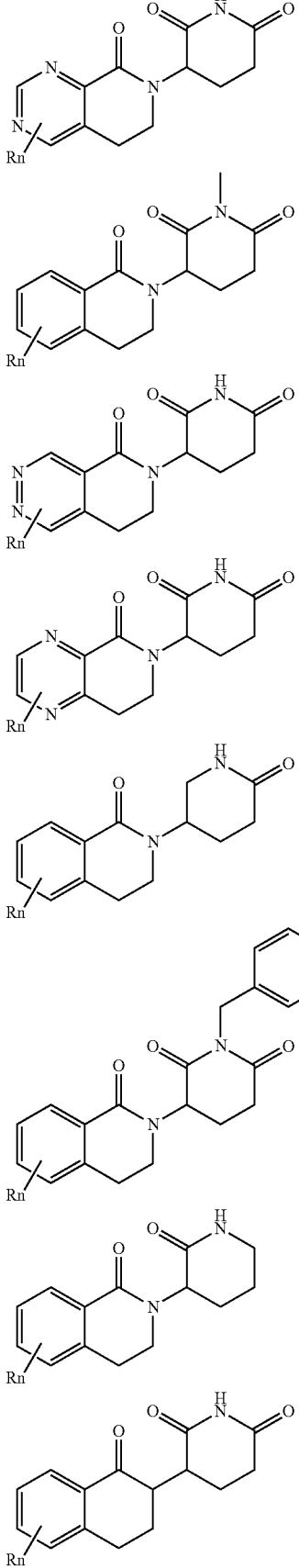
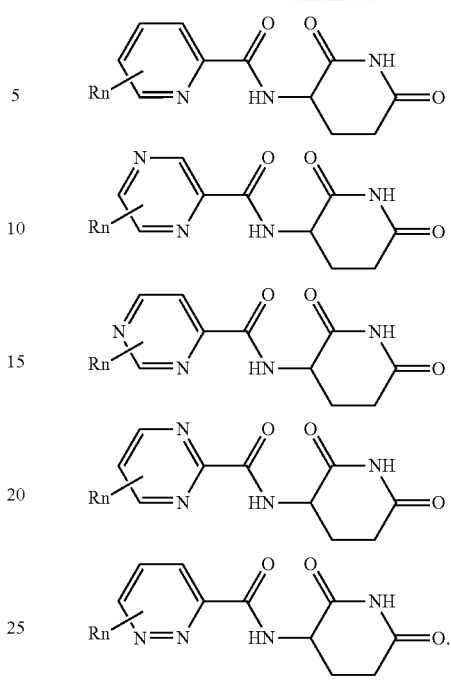
In any of the compounds described herein, the CLM comprises a chemical structure selected from the group:
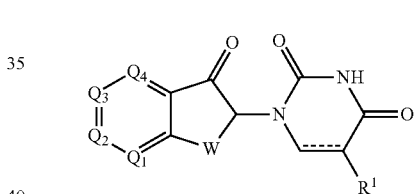
(h)
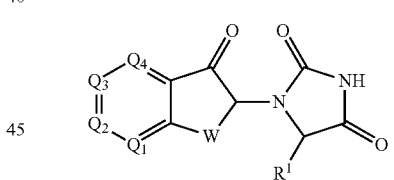
(i)
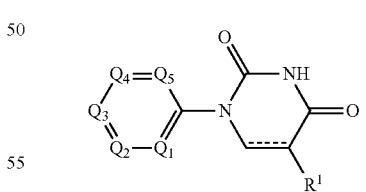
(j)
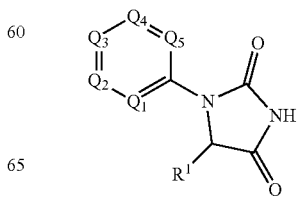
(k)

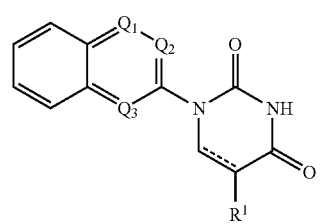 (l)
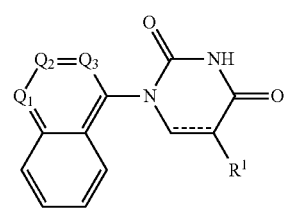 (m)
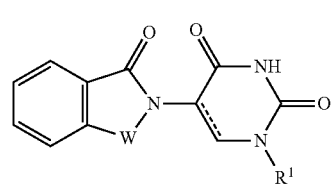 (n)
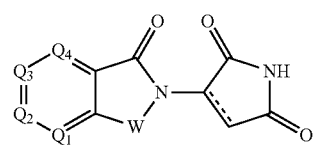 (o)
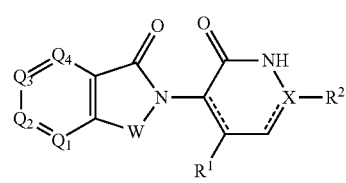 (p)
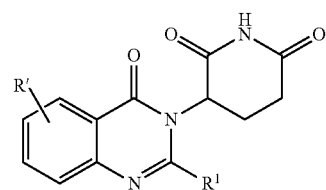 (q)
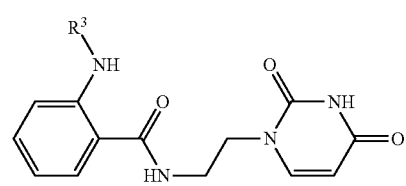 (r)
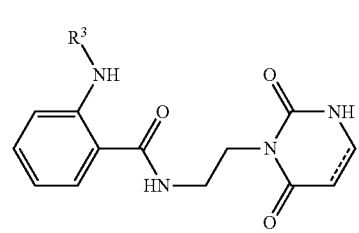 (s)
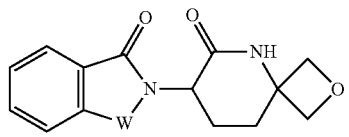 (t)
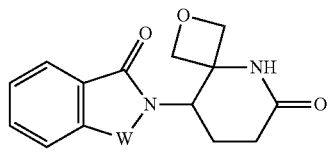 (u)
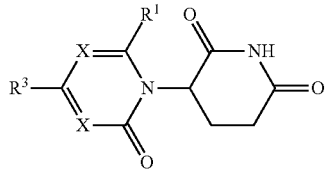 (v)
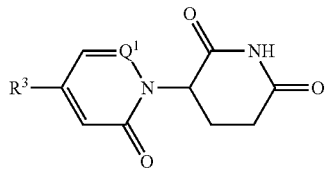 (w)
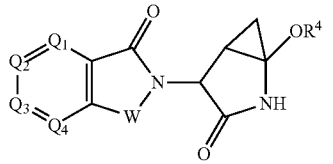 (x)
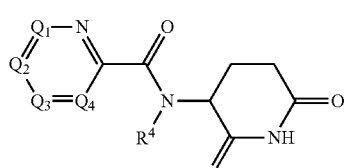 (y)
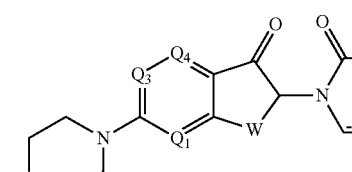 (z)
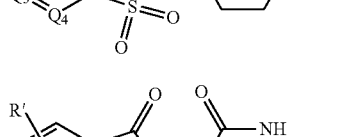 (aa)
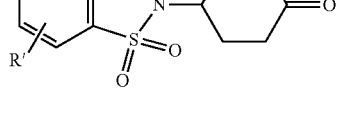 (ab)

wherein:
- W of Formulas (h) through (ab) is independently selected from $CH_2$, CHR, C=O, $SO_2$, NH, and N-alkyl;
- $Q_1$, $Q_2$, $Q_3$, $Q_4$, $Q_5$ of Formulas (h) through (ab) are independently represent a carbon C substituted with a group independently selected from R', N or N-oxide;
- $R^1$ of Formulas (h) through (ab) is selected from H, CN, C1-C3 alkyl;
- $R^2$ of Formulas (h) through (ab) is selected from the group H, CN, C1-C3 alkyl, $CHF_2$, $CF_3$, CHO;
- $R^3$ of Formulas (h) through (ab) is selected from H, alkyl, substituted alkyl, alkoxy, substituted alkoxy;
- $R^4$ of Formulas (h) through (ab) is selected from H, alkyl, substituted alkyl;
- $R^5$ of Formulas (h) through (ab) is H or lower alkyl;
- X of Formulas (h) through (ab) is C, CH or N;
- R' of Formulas (h) through (ab) is selected from H, halogen, alkyl, substituted alkyl, alkoxy, substituted alkoxy;
- R of Formulas (h) through (ab) is H, OH, lower alkyl, lower alkoxy, cyano, halogenated lower alkoxy, or halogenated lower alkyl
- ⫽ of Formulas (h) through (ab) is a single or double bond; and
- the CLM is covalently joined to a PTM, a chemical linker group (L), a ULM, CLM (or CLM') or combination thereof.

In any aspect or embodiment described herein, the CLM or CLM' is covalently joined to a PTM, a chemical linker group (L), a ULM, a CLM, a CLM', or a combination thereof via an R group (such as, R, $R^1$, $R^2$, $R^3$, $R^4$ or R'), W, X, or a Q group (such as, $Q_1$, $Q_2$, $Q_3$, $Q_4$, or $Q_5$) of Formulas (h) through (ab).

In any of the embodiments described herein, the CLM or CLM' is covalently joined to a PTM, a chemical linker group (L), a ULM, a CLM, a CLM', or a combination thereof via W, X, R, $R^1$, $R^2$, $R^3$, $R^4$, $R^5$, R', $Q_1$, $Q_2$, $Q_3$, $Q_4$, and $Q_5$ of Formulas (h) through (ab).

In any of the embodiments described herein, the W, X, $R^1$, $R^2$, $R^3$, $R^4$, R', $Q_1$, $Q_2$, $Q_3$, $Q_4$, and $Q_5$ of Formulas (h) through (ab) can independently be covalently coupled to a linker and/or a linker to which is attached to one or more PTM, ULM, ULM', CLM or CLM' groups.

More specifically, non-limiting examples of CLMs include those shown below as well as "hybrid" molecules or compounds that arise from combining 1 or more features of the following compounds:

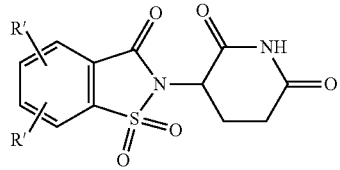

(ac)

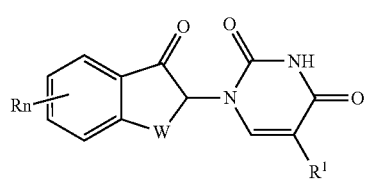

(ad)

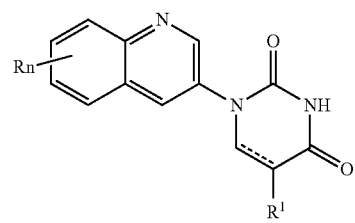

(ae)

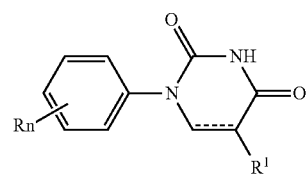

(af)

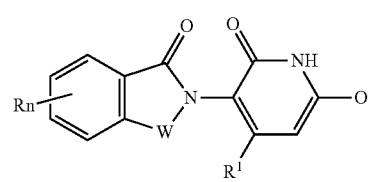

(ag)

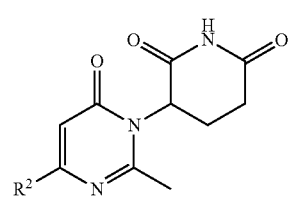

(ah)

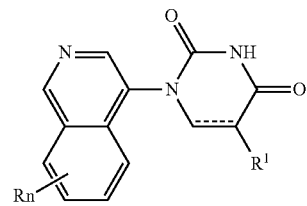

(ai)

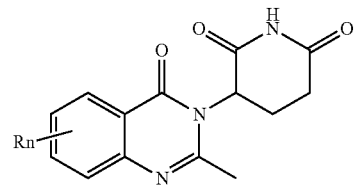

(aj)

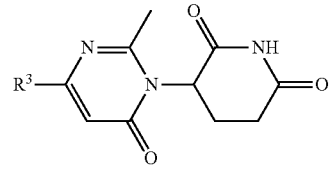

(ak)

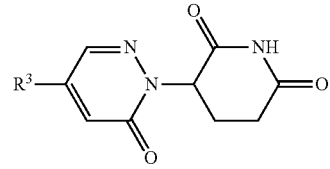

(al)

-continued (am)
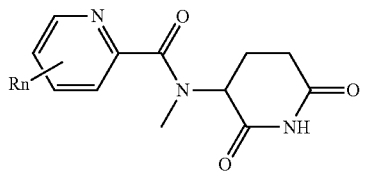

(an)
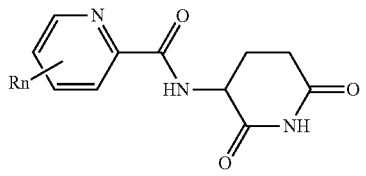

wherein:

W of Formulas (ac) through (an) is independently selected from the group CH$_2$, CHR, C=O, SO$_2$, NH, and N-alkyl;

R$^1$ of Formulas (ac) through (an) is selected from the group H, CN, C1-C3 alkyl;

R$^3$ of Formulas (ac) through (an) is selected from H, alkyl, substituted alkyl, alkoxy, substituted alkoxy;

R of Formulas (ac) through (an) is H;

⇌ is a single or double bond; and

Rn of Formulas (ac) through (an) comprises a functional group or an atom.

In any of the embodiments described herein, the W, R$^1$, R$^2$, Q$_1$, Q$_2$, Q$_3$, Q$_4$, and Rn of Formulas (ac) through (an) can independently be covalently coupled to a linker and/or a linker to which is attached one or more PTM, ULM, ULM', CLM or CLM' groups.

In any of the embodiments described herein, the R$^1$, R$^2$, Q$_1$, Q$_2$, Q$_3$, Q$_4$, and Rn of Formulas (ac) through (an) can independently be covalently coupled to a linker and/or a linker to which is attached one or more PTM, ULM, ULM', CLM or CLM' groups.

In any of the embodiments described herein, the Q$_1$, Q$_2$, Q$_3$, Q$_4$, and Rn of Formulas (ac) through (an) can independently be covalently coupled to a linker and/or a linker to which is attached one or more PTM, ULM, ULM', CLM or CLM' groups.

In any aspect or embodiment described herein, R$_n$ of Formulas (ac) through (an) is modified to be covalently joined to the linker group (L), a PTM, a ULM, a second CLM having the same chemical structure as the CLM, a CLM', a second linker, or any multiple or combination thereof.

In any aspect or embodiment described herein, the CLM is selected from:

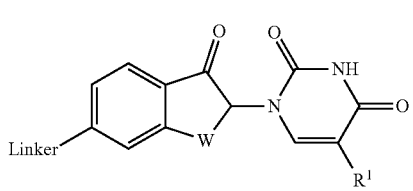

-continued

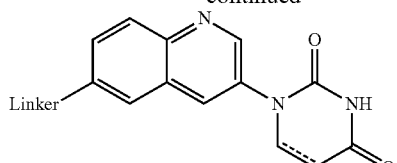

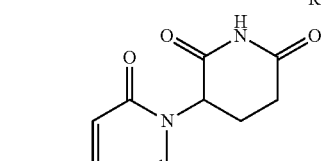

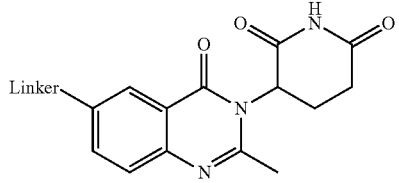

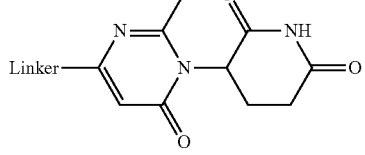

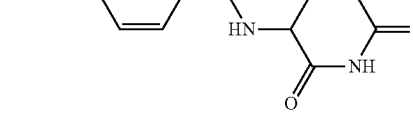

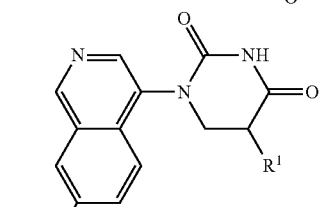

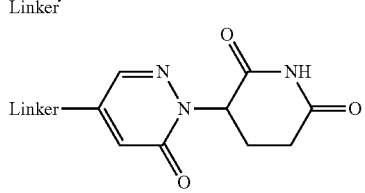

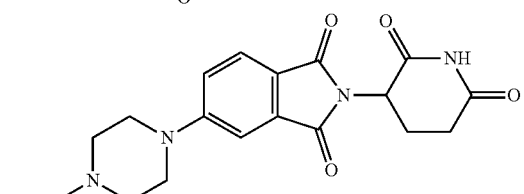

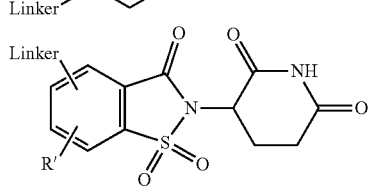

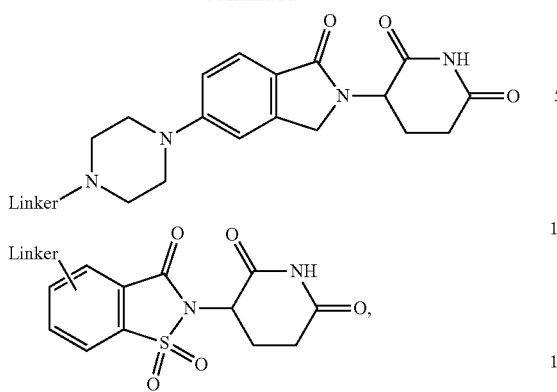

wherein R' is a halogen and $R^1$ is as described above with regard to Formulas (h) through (ab) or (ac) through (an).

In certain cases, the CLM can be imides that bind to cereblon E3 ligase. These imides and linker attachment point can be but not limited to the following structures:

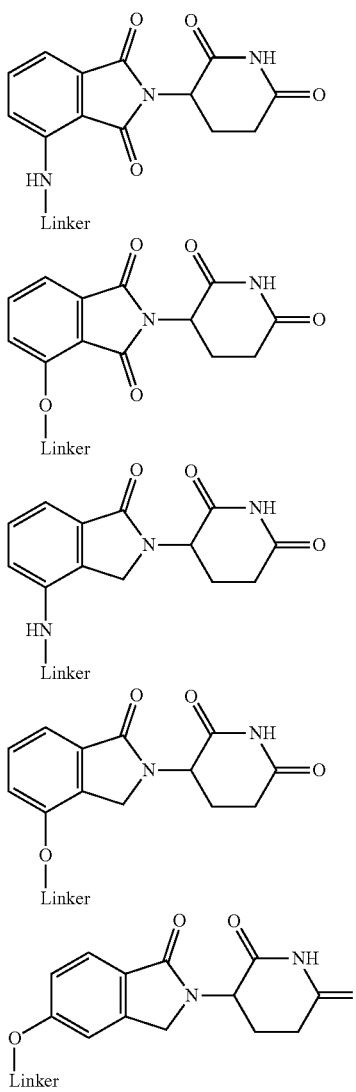

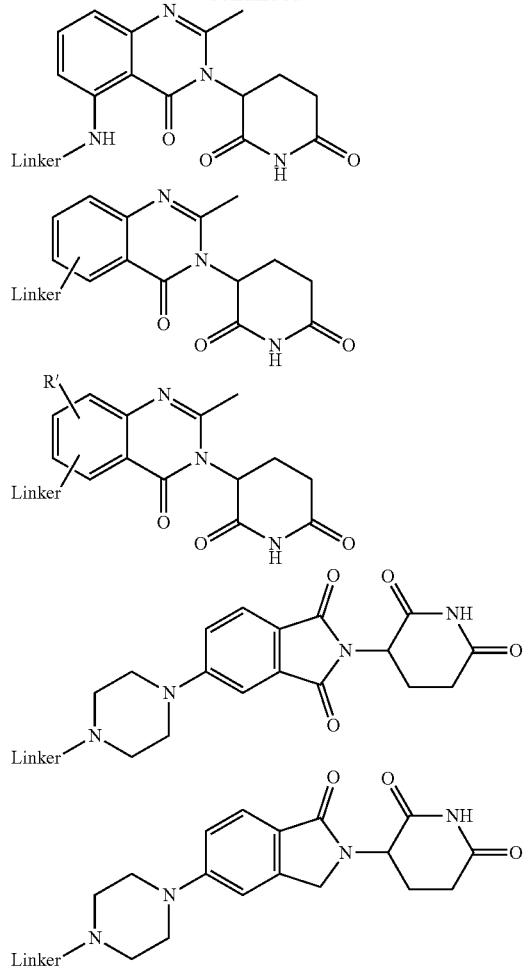

wherein R' is a halogen.

Exemplary VLMs

In certain embodiments of the compounds as described herein, the ULM is a VLM and comprises a chemical structure of ULM-a:

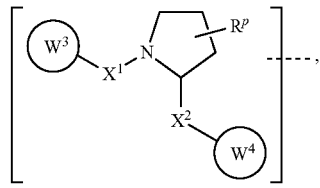

ULM-a wherein:
- a dashed line indicates the attachment of at least one PTM, another ULM or VLM or MLM or ILM or CLM (i.e., ULM' or VLM' or CLM' or ILM' or MLM'), or a chemical linker moiety coupling at least one PTM, a ULM' or a VLM' or a CLM' or a ILM' or a MLM' to the other end of the linker;
- $X^1$, $X^2$ of Formula ULM-a are each independently selected from the group of a bond, O, $NR^{Y3}$, $CR^{Y3}R^{Y4}$, C=O, C=S, SO, and $SO_2$;
- $R^{Y3}$, $R^{Y4}$ of Formula ULM-a are each independently selected from the group of H, linear or branched $C_{1-6}$ alkyl, optionally substituted by 1 or more halo, optionally substituted $C_{1-6}$ alkoxyl (e.g., optionally substituted with 0-3 $R^P$ groups);

$R^P$ of Formula ULM-a is 1, 2, or 3 groups, each independently selected from H, halo, —OH, $C_{1-3}$ alkyl;

$W^3$ of Formula ULM-a is selected from the group of an optionally substituted -T-N($R^{1a}R^{1b}$)$X^3$, optionally substituted -T-N($R^{1a},R^{1b}$) optionally substituted -T-Aryl, an optionally substituted -T-Heteroaryl, an optionally substituted -T-Heterocycle, an optionally substituted —NR$^1$-T-Aryl, an optionally substituted —NR$^1$-T-Heteroaryl or an optionally substituted —NR$^1$-T-Heterocycle;

$X^3$ of Formula ULM-a is C=O, $R^1$, $R^{1a}$, $R^{1b}$;

$R^1$, $R^{1a}$, $R^{1b}$ are each independently selected from the group consisting of H, linear or branched $C_1$-$C_6$ alkyl group optionally substituted by 1 or more halo or —OH groups, $R^{I3}$C=O, $R^{I3}$C=S, $R^{I3}$SO, $R^{I3}$SO$_2$, N($R^{I3}R^{I4}$)C=O, N($R^{I3}R^{I4}$)C=S, N($R^{I3}R^{I4}$)SO, and N$R^{I3}R^{I4}$)SO$_2$;

T of Formula ULM-a is covalently bonded to X1;

$W^4$ of Formula ULM-a is an optionally substituted —NR$^1$-T-Aryl, an optionally substituted —NR$^1$-T-Heteroaryl group or an optionally substituted —NR$^1$-T-Heterocycle, wherein —NR$^1$ is covalently bonded to $X^2$ and $R^1$ is H or CH$^3$, preferably H.

In any of the embodiments described herein, T is selected from the group of an optionally substituted alkyl, —(CH$_2$)— group, wherein each one of the methylene groups is optionally substituted with one or two substituents selected from the group of halogen, methyl, a linear or branched $C_1$-$C_6$ alkyl group optionally substituted by 1 or more halogen or —OH groups or an amino acid side chain optionally substituted; and n is 0 to 6, often 0, 1, 2, or 3, preferably 0 or 1.

In certain embodiments, $W^4$ of Formula ULM-a is

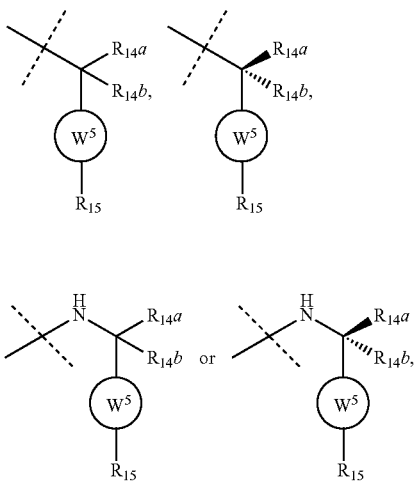

wherein $R_{14a}$, $R_{14b}$, are each independently selected from the group of H, haloalkyl, or optionally substituted alkyl.

In any of the embodiments, $W^5$ of Formula ULM-a is selected from the group of a phenyl or a 5-10 membered heteroaryl, $R_{15}$ of Formula ULM-a is selected from the group of H, halogen, CN, OH, NO$_2$, N $R_{14a}R_{14b}$, OR$_{14a}$, CONR$_{14a}R_{14b}$, NR$_{14a}$COR$_{14b}$, SO$_2$NR$_{14a}R_{14b}$, NR$_{14a}$ SO$_2$R$_{14b}$, optionally substituted alkyl, optionally substituted haloalkyl, optionally substituted haloalkoxy; aryl, heteroaryl, cycloalkyl, or cycloheteroalkyl;

In additional embodiments, $W^4$ substituents for use in the present disclosure also include specifically (and without limitation to the specific compound disclosed) the $W^4$ substituents which are found in the identified compounds disclosed herein. Each of these $W^4$ substituents may be used in conjunction with any number of $W^3$ substituents which are also disclosed herein.

In certain additional embodiments, ULM-a, is optionally substituted by 0-3 $R^P$ groups in the pyrrolidine moiety. Each $R^P$ is independently H, halo, —OH, C1-3alkyl, C=O.

In any of the embodiments described herein, the $W^3$, $W^4$ of Formula ULM-a can independently be covalently coupled to a linker which is attached one or more PTM groups.

and wherein the dashed line indicates the site of attachment of at least one PTM, another ULM (ULM') or a chemical linker moiety coupling at least one PTM or a ULM' or both to ULM.

In certain embodiments, ULM is VHL and is represented by the structure:

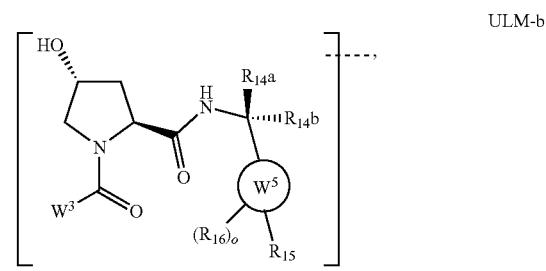

wherein:

$W^3$ of Formula ULM-b is selected from the group of an optionally substituted aryl, optionally substituted heteroaryl, or

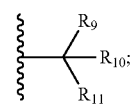

$R_9$ and $R_{10}$ of Formula ULM-b are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ of Formula ULM-b is selected from the group of an optionally substituted heterocyclic, optionally substituted alkoxy, optionally substituted heteroaryl, optionally substituted aryl,

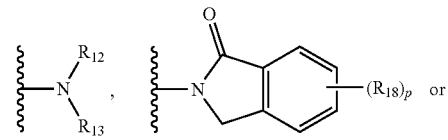

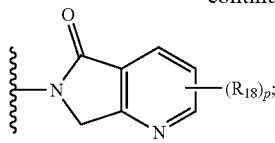

R$_{12}$ of Formula ULM-b is selected from the group of H or optionally substituted alkyl;

R$_{13}$ of Formula ULM-b is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

R$_{14a}$, R$_{14b}$ of Formula ULM-b, are each independently selected from the group of H, haloalkyl, or optionally substituted alkyl;

W$^5$ of Formula ULM-b is selected from the group of a phenyl or a 5-10 membered heteroaryl, R$_{15}$ of Formula ULM-b is selected from the group of H, halogen, CN, OH, NO$_2$, NR$_{14a}$R$_{14b}$, OR$_{14a}$, CONR$_{14a}$R$_{14b}$, NR$_{14a}$COR$_{14b}$, SO$_2$NR$_{14a}$R$_{14b}$, NR$_{14a}$SO$_2$R$_{14b}$, optionally substituted alkyl, optionally substituted haloalkyl, optionally substituted haloalkoxy; aryl, heteroaryl, cycloalkyl, or cycloheteroalkyl; (each optionally substituted);

R$_{16}$ of Formula ULM-b is independently selected from the group of halo, optionally substituted alkyl, optionally substituted haloalkyl, hydroxy, or optionally substituted haloalkoxy;

o of Formula ULM-b is 0, 1, 2, 3, or 4;

R$_{18}$ of Formula ULM-b is independently selected from the group of H, halo, optionally substituted alkoxy, cyano, optionally substituted alkyl, haloalkyl, haloalkoxy or a linker; and p of Formula ULM-b is 0, 1, 2, 3, or 4, and wherein the dashed line indicates the site of attachment of at least one PTM, another ULM (ULM') or a chemical linker moiety coupling at least one PTM or a ULM' or both to ULM.

In certain embodiments, R$_{15}$ of Formula ULM-b is

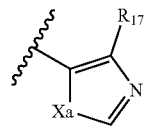

wherein R$_{17}$ is H, halo, optionally substituted C$_{3-6}$cycloalkyl, optionally substituted C$_{1-6}$alkyl, optionally substituted C$_{1-6}$alkenyl, and C$_{1-6}$haloalkyl; and Xa is S or O.

In certain embodiments, R$_{17}$ of Formula ULM-b is selected from the group methyl, ethyl, isopropyl, and cyclopropyl.

In certain additional embodiments, R$_{15}$ of Formula ULM-b is selected from the group consisting of:

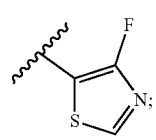 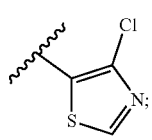 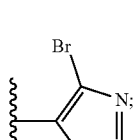

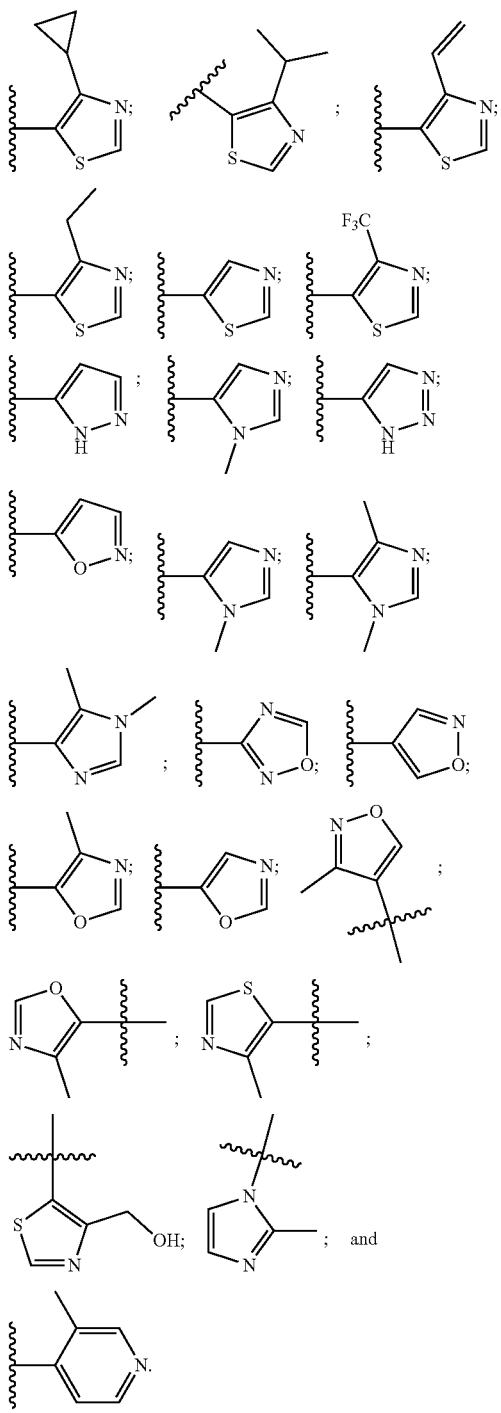

In certain embodiments, R$_{11}$ of Formula ULM-b is selected from the group consisting of:

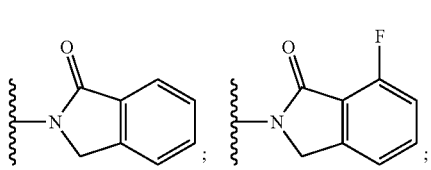

-continued

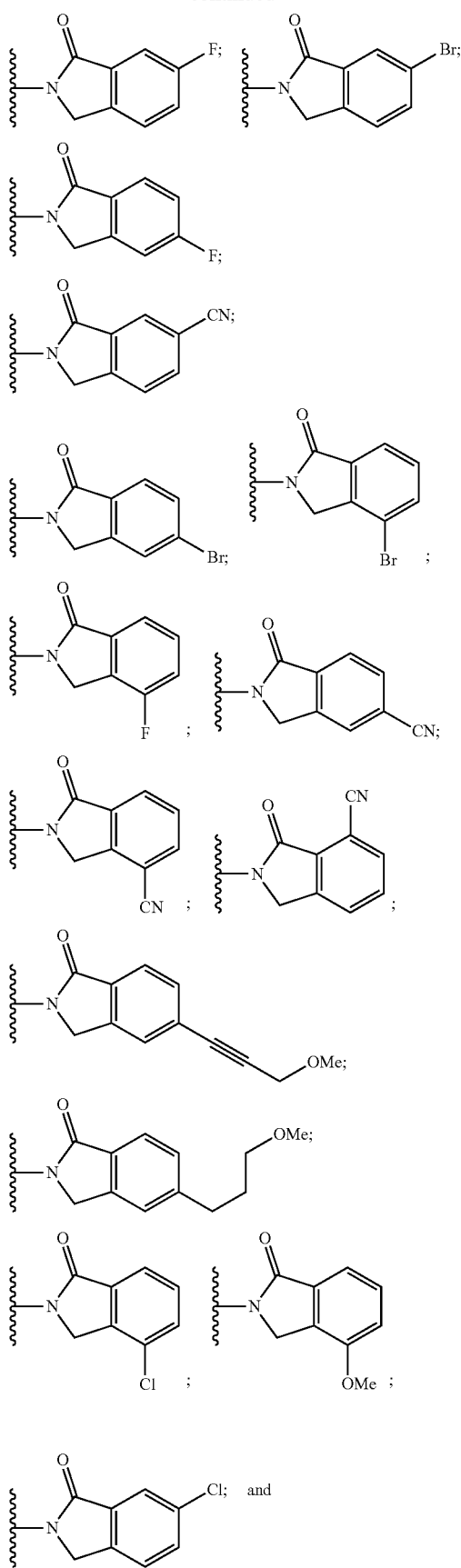

-continued

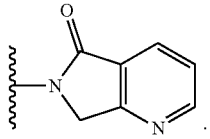

In certain embodiments, ULM has a chemical structure selected from the group of:

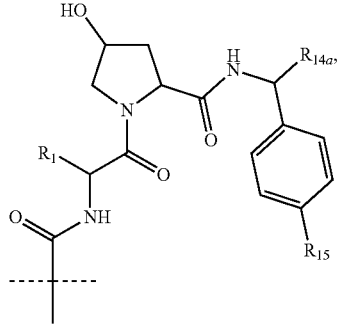
ULM-c

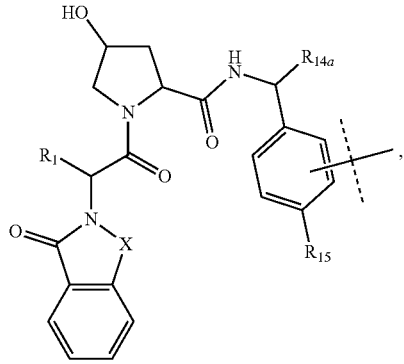
ULM-d

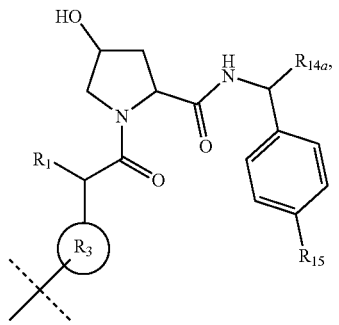
ULM-e wherein:
$R_1$ of Formulas ULM-c, ULM-d, and ULM-e is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;

$R_{14a}$ of Formulas ULM-c, ULM-d, and ULM-e is H, haloalkyl, optionally substituted alkyl, methyl, fluoromethyl, hydroxymethyl, ethyl, isopropyl, or cyclopropyl;

$R_{15}$ of Formulas ULM-c, ULM-d, and ULM-e is selected from the group consisting of H, halogen, CN, OH, $NO_2$, optionally substituted heteroaryl, optionally substituted aryl; optionally substituted alkyl, optionally substituted haloalkyl, optionally substituted haloalkoxy, cycloalkyl, or cycloheteroalkyl;

X of Formulas ULM-c, ULM-d, and ULM-e is C, CH$_2$, or C=O

R$_3$ of Formulas ULM-c, ULM-d, and ULM-e is absent or a bond or an optionally substituted 5 or 6 membered heteroaryl; and wherein the dashed line indicates the site of attachment of at least one PTM, another ULM (ULM') or a chemical linker moiety coupling at least one PTM or a ULM' or both to ULM.

In certain embodiments, ULM comprises a group according to the chemical structure:

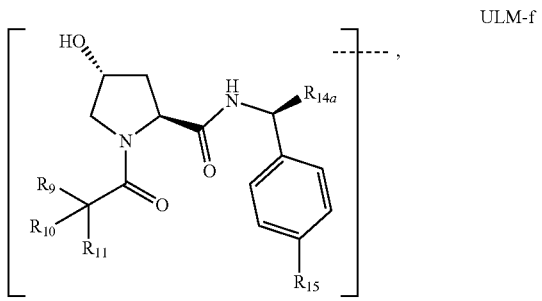

ULM-f wherein:
R$_{14a}$ of Formula ULM-f is H, haloalkyl, optionally substituted alkyl, methyl, fluoromethyl, hydroxymethyl, ethyl, isopropyl, or cyclopropyl;
R$_9$ of Formula ULM-f is H;
R$_{10}$ of Formula ULM-f is H, ethyl, isopropyl, tert-butyl, sec-butyl, cyclopropyl, cyclobutyl, cyclopentyl, or cyclohexyl;
R$_{11}$ of Formula ULM-f is

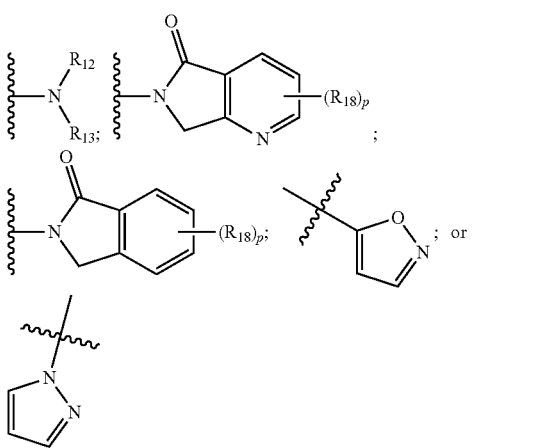

or optionally substituted heteroaryl;
p of Formula ULM-f is 0, 1, 2, 3, or 4;
each R$_{18}$ of Formula ULM-f is independently halo, optionally substituted alkoxy, cyano, optionally substituted alkyl, haloalkyl, haloalkoxy or a linker;
R$_{12}$ of Formula ULM-f is H, C=O;
R$_{13}$ of Formula ULM-f is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl, R$_{15}$ of Formula ULM-f is selected from the group consisting of H, halogen, Cl, CN, OH, NO$_2$, optionally substituted heteroaryl, optionally substituted aryl;

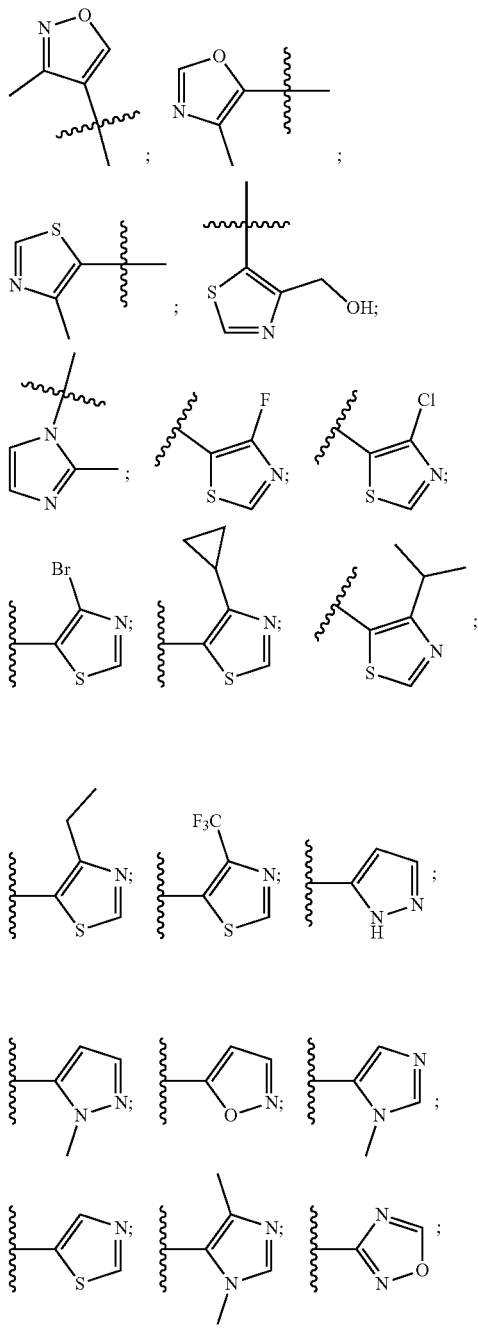

and wherein the dashed line of Formula ULM-f indicates the site of attachment of at least one PTM, another ULM (ULM') or a chemical linker moiety coupling at least one PTM or a ULM' or both to ULM.

In certain embodiments, the ULM is selected from the following structures:

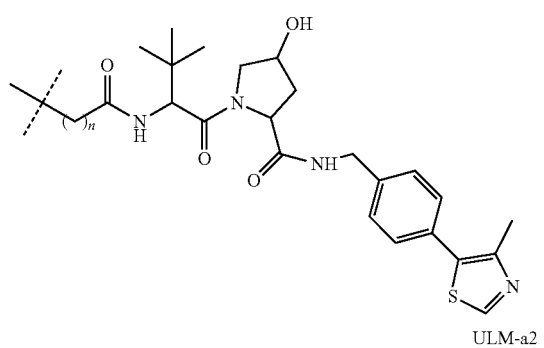
ULM-a2

ULM-a3

ULM-a4
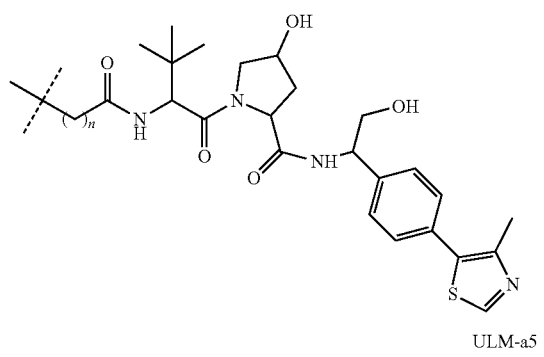
ULM-a5
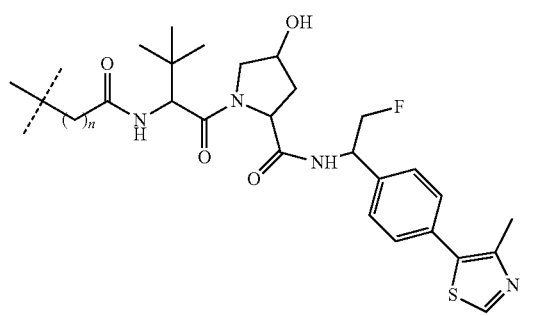
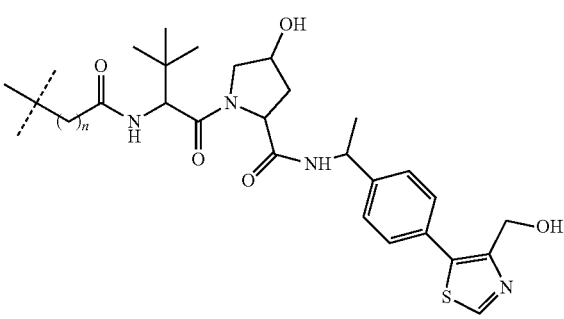
ULM-a6
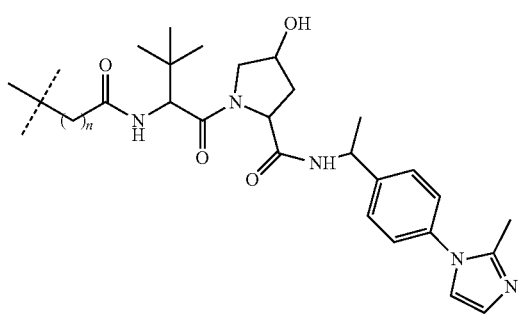
ULM-a7
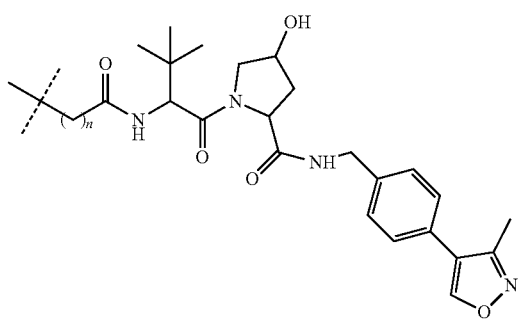
ULM-a8
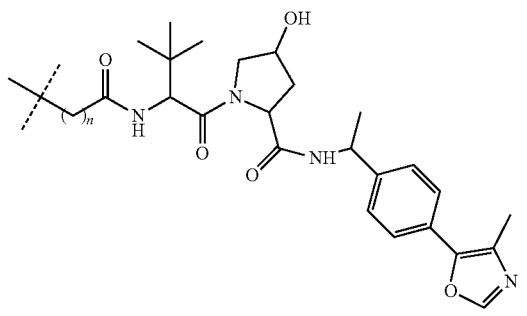
ULM-a9

ULM-a10
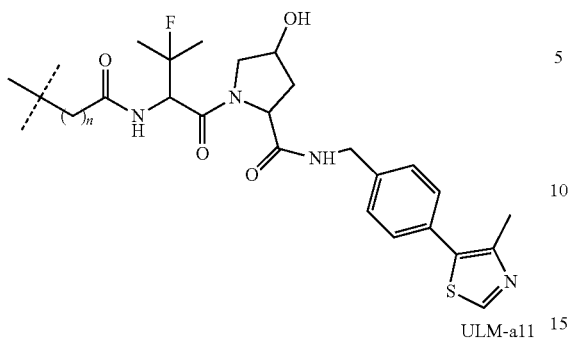
ULM-a11
ULM-a12
ULM-a13
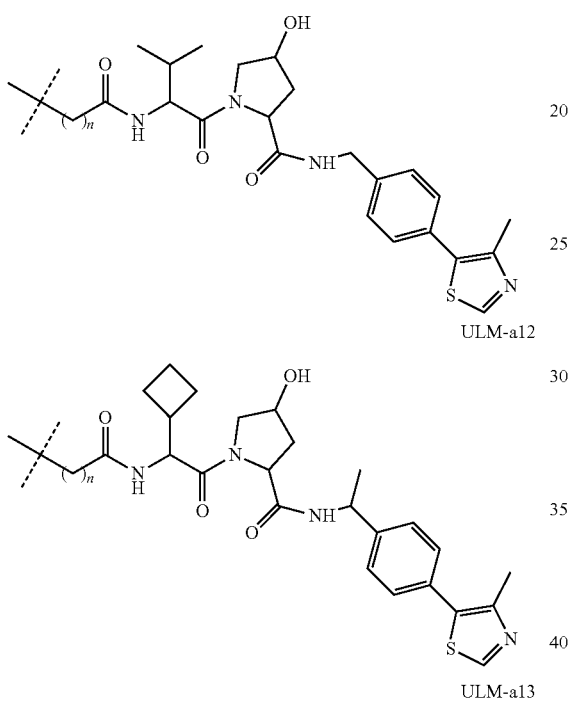
ULM-a14
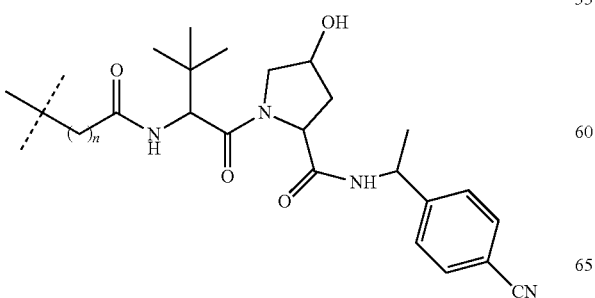
ULM-a15
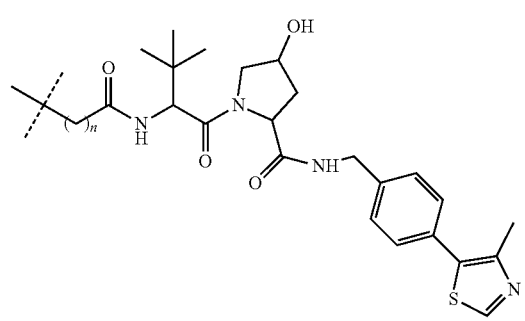
wherein n is 0 or 1.
In certain embodiments, the ULM is selected from the following structures:
ULM-b1
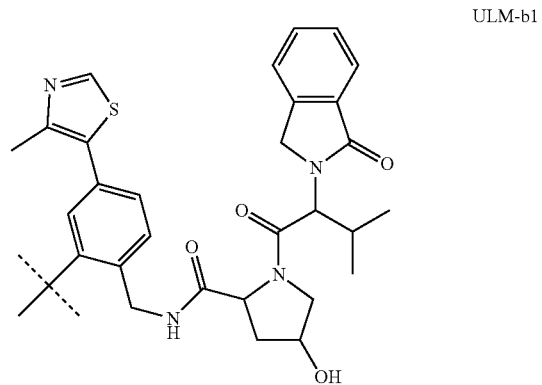
ULM-b2
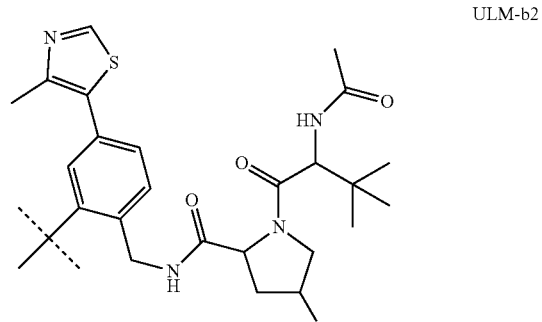
ULM-b3
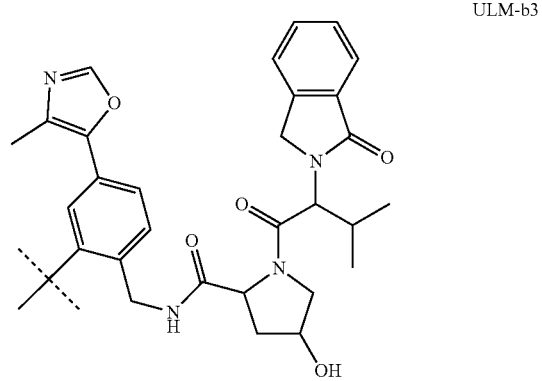

-continued
ULM-b4
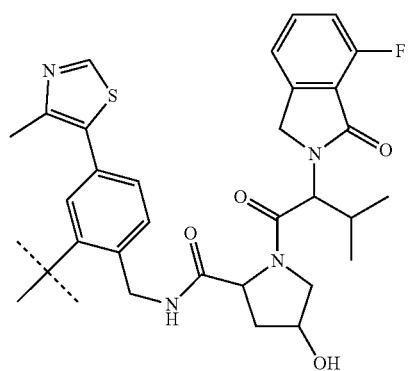
ULM-b5
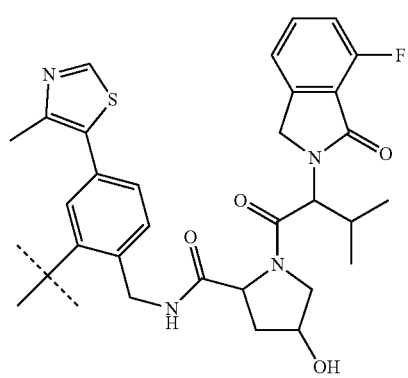
ULM-b6
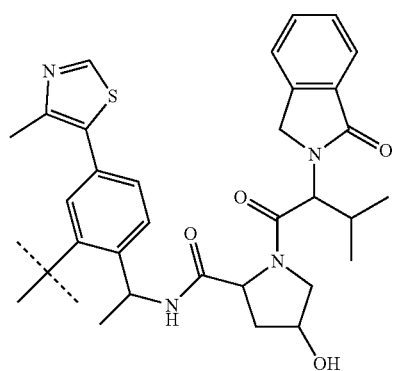
ULM-b7
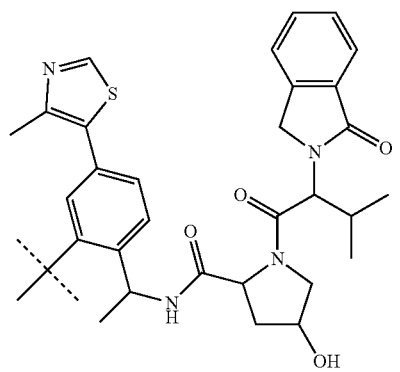
-continued
ULM-b8
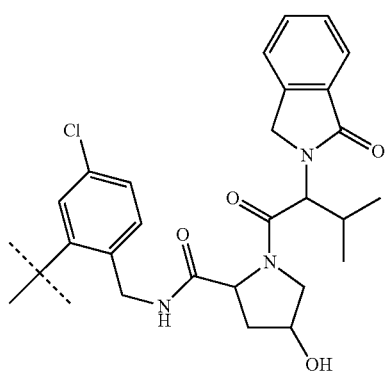
ULM-b9
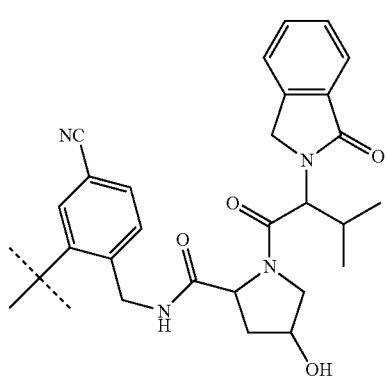
ULM-b10
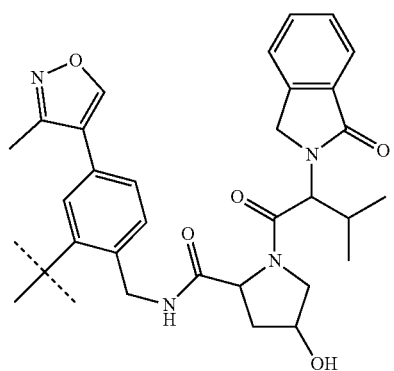
ULM-b11
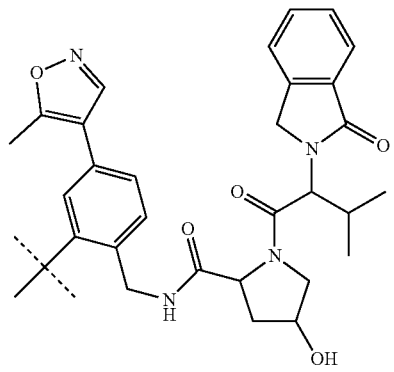

-continued
ULM-b12
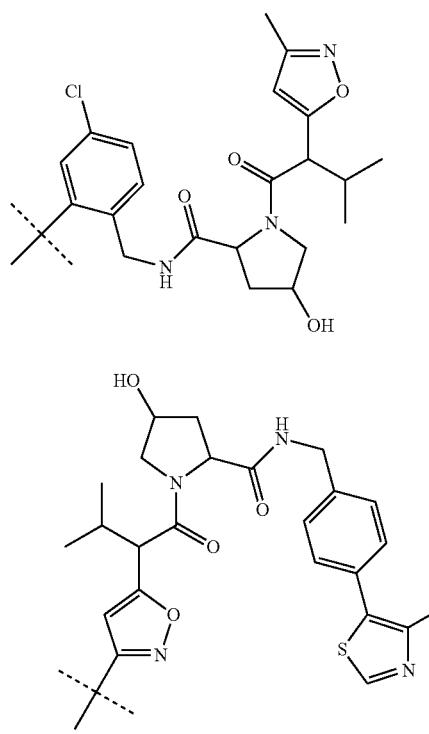
ULM-c1
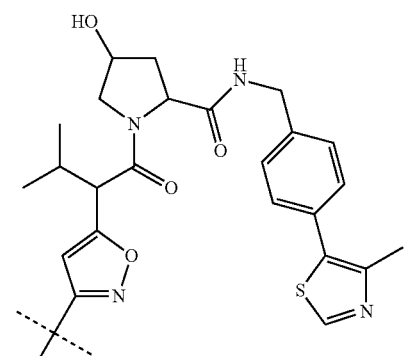
ULM-c2
ULM-c3
-continued
ULM-c4
ULM-c5
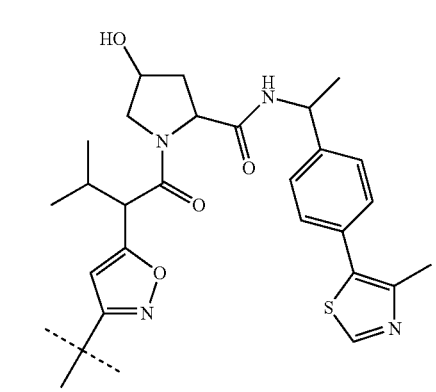
ULM-c6
ULM-c7
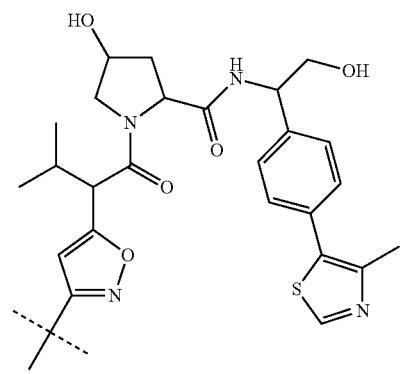

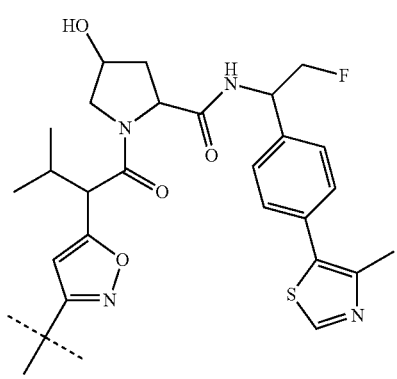
ULM-c8
ULM-c9
ULM-c10
ULM-c11
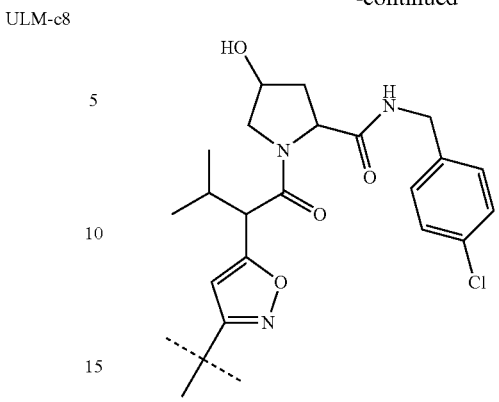
ULM-c12
ULM-c13
ULM-c14
ULM-c15

ULM-d1
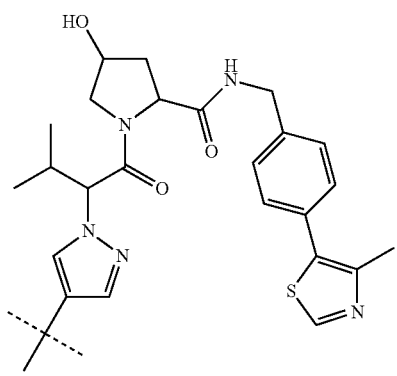
ULM-d5
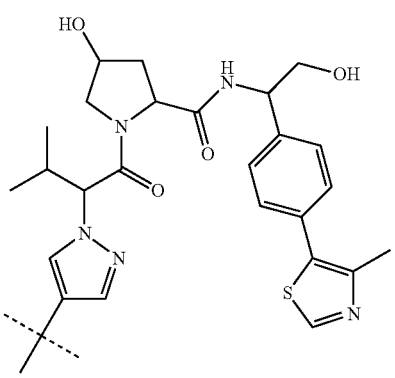
ULM-d2
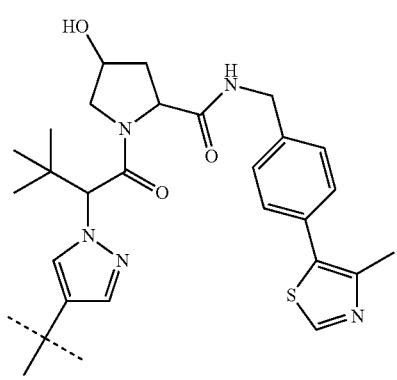
ULM-d6
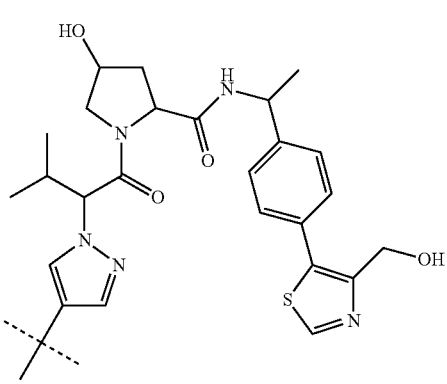
ULM-d3
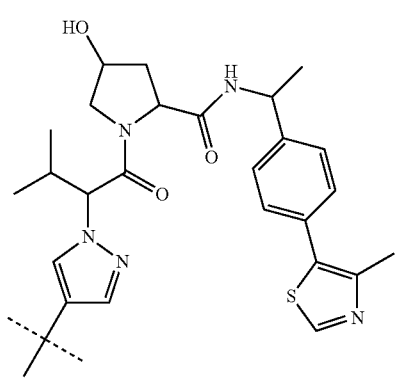
ULM-d7
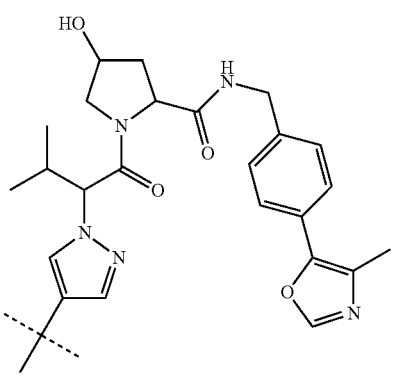
ULM-d4
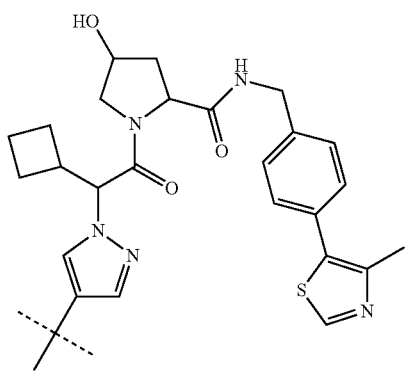
ULM-d8
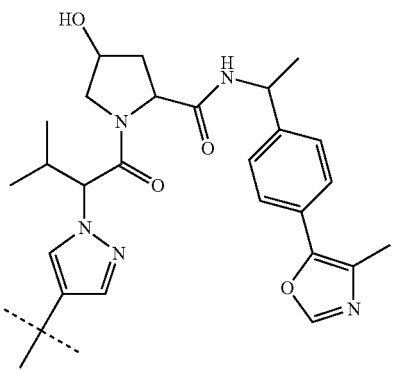

-continued

ULM-d9

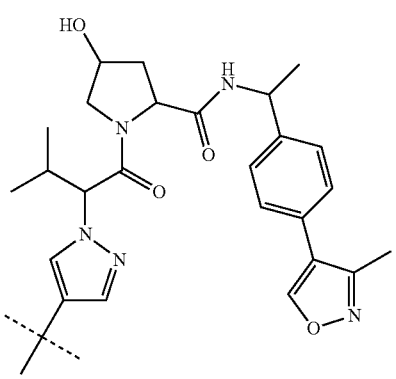

wherein, the phenyl ring in ULM-a1 through ULM -a15, ULM-b1 through ULM-b12, ULM-c1 through ULM-c15 and ULM-d1 through ULM-d9 is optionally substituted with fluorine, lower alkyl and alkoxy groups, and wherein the dashed line indicates the site of attachment of at least one PTM, another ULM (ULM') or a chemical linker moiety coupling at least one PTM or a ULM' or both to ULM-a.

In one embodiment, the phenyl ring in ULM-a1 through ULM-a15, ULM-b1 through ULM-b12, ULM-c1 through ULM-c15 and ULM-d1 through ULM-d9 can be functionalized as the ester to make it a part of the prodrug.

In certain embodiments, the hydroxyl group on the pyrrolidine ring of ULM-a1 through ULM-a15, ULM-b1 through ULM-b12, ULM-c1 through ULM-c15 and ULM-d1 through ULM-d9, respectively, comprises an ester-linked prodrug moiety.

In any of the aspects or embodiments described herein, the ULM and where present, ULM', are each independently a group according to the chemical structure:

ULM-g

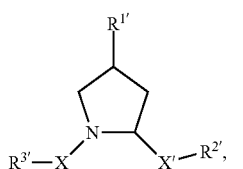

wherein:
R$^{1'}$ of ULM-g is an optionally substituted $C_1$-$C_6$ alkyl group, an optionally substituted —$(CH_2)_n$OH, an optionally substituted —$(CH_2)_n$SH, an optionally substituted $(CH_2)_n$—O—($C_1$-$C_6$)alkyl group, an optionally substituted $(CH_2)_n$—WCOCW-($C_0$-$C_6$)alkyl group containing an epoxide moiety WCOCW where each W is independently H or a $C_1$-$C_3$ alkyl group, an optionally substituted —$(CH_2)_n$COOH, an optionally substituted —$(CH_2)_n$C(O)—($C_1$-$C_6$ alkyl), an optionally substituted —$(CH_2)_n$NHC(O)—$R_1$, an optionally substituted —$(CH_2)_n$C(O)—$NR_1R_2$, an optionally substituted —$(CH_2)_n$OC(O)—$NR_1R_2$, —$(CH_2O)_n$H, an optionally substituted —$(CH_2)_n$OC(O)—($C_1$-$C_6$ alkyl), an optionally substituted —$(CH_2)_n$C(O)—O—($C_1$-$C_6$ alkyl), an optionally substituted —$(CH_2O)_n$COOH, an optionally substituted —$(OCH_2)_n$O—($C_1$-$C_6$ alkyl), an optionally substituted —$(CH_2O)_n$C(O)—($C_1$-$C_6$ alkyl), an optionally substituted —$(OCH_2)_n$NHC(O)—$R_1$, an optionally substituted —$(CH_2O)_n$C(O)—$NR_1R_2$, —$(CH_2CH_2O)_n$H, an optionally substituted —$(CH_2CH_2O)_n$COOH, an optionally substituted —$(OCH_2CH_2)_n$O—($C_1$-$C_6$alkyl), an optionally substituted —$(CH_2CH_2O)_n$C(O)—($C_1$-$C_6$ alkyl), an optionally substituted —$(OCH_2CH_2)_n$NHC(O)—$R_1$, an optionally substituted —$(CH_2CH_2O)_n$C(O)—$NR_1R_2$, an optionally substituted —$SO_2R_S$, an optionally substituted $S(O)R_S$, $NO_2$, CN or halogen (F, Cl, Br, I, preferably F or Cl);

$R_1$ and $R_2$ of ULM-g are each independently H or a $C_1$-$C_6$ alkyl group which may be optionally substituted with one or two hydroxyl groups or up to three halogen groups (preferably fluorine);

$R_S$ of ULM-g is a $C_1$-$C_6$ alkyl group, an optionally substituted aryl, heteroaryl or heterocycle group or a —$(CH_2)_m NR_1R_2$ group;

X and X' of ULM-g are each independently C=O, C=S, —S(O), $S(O)_2$, (preferably X and X' are both C=O);

$R^2$ of ULM-g is an optionally substituted —$(CH_2)_n$—(C=O)$_u$(NR$_1$)$_v$(SO$_2$)$_w$alkyl group, an optionally substituted —$(CH_2)_n$—(C=O)$_u$(NR$_1$)$_v$(SO$_2$)$_w$NR$_{1N}$R$_{2N}$ group, an optionally substituted —$(CH_2)_n$—(C=O)$_u$—(NR$_1$)$_v$(SO$_2$)$_w$-Aryl, an optionally substituted —$(CH_2)_n$—(C=O)$_u$(NR$_1$)$_v$(SO$_2$)$_w$-Heteroaryl, an optionally substituted —$(CH_2)_n$—(C=O)$_v$NR$_1$(SO$_2$)$_w$-Heterocycle, an optionally substituted —NR$^1$—(CH$_2$)$_n$—C(O)$_u$(NR$_1$)$_v$(SO$_2$)$_w$-alkyl, an optionally substituted —NR$^1$—(CH$_2$)$_n$—C(O)$_u$(NR$_1$)$_v$(SO$_2$)$_w$—NR$_{1N}$R$_{2N}$, an optionally substituted —NR$^1$—(CH$_2$)$_n$—C(O)$_u$(NR$_1$)$_v$(SO$_2$)$_w$—NR$_1$C(O)R$_{1N}$, an optionally substituted —NR$^1$—(CH$_2$)$_n$—(C=O)$_u$(NR$_1$)$_v$(SO$_2$)$_w$-Aryl, an optionally substituted —NR$^1$—(CH$_2$)$_n$—(C=O)$_n$(NR$_1$)$_v$(SO$_2$)$_w$-Heteroaryl or an optionally substituted —NR$^1$—(CH$_2$)$_n$—(C=O)$_v$NR$_1$(SO$_2$)$_w$-Heterocycle, an optionally substituted —$X^{R2'}$-alkyl group; an optionally substituted —$X^{R2'}$-Aryl group; an optionally substituted —$X^{R2'}$-Heteroaryl group; an optionally substituted —$X^{R2'}$-Heterocycle group; an optionally substituted;

R$^{3'}$ of ULM-g is an optionally substituted alkyl, an optionally substituted —$(CH_2)_n$—(O)$_u$(NR$_1$)$_v$(SO$_2$)$_w$-alkyl, an optionally substituted —$(CH_2)_n$—C(O)$_u$(NR$_1$)$_v$(SO$_2$)$_w$—NR$_{1N}$R$_{2N}$, an optionally substituted —$(CH_2)_n$—C(O)$_u$(NR$_1$)$_v$(SO$_2$)$_w$—NR$_1$C(O)R$_{1N}$, an optionally substituted —$(CH_2)_n$—C(O)$_u$(NR$_1$)$_v$(SO$_2$)$_w$—C(O)NR$_1$R$_2$, an optionally substituted —$(CH_2)_n$—C(O)—(NR$_1$)$_v$(SO$_2$)$_w$-Aryl, an optionally substituted —$(CH_2)_n$—C(O)$_u$(NR$_1$)$_v$(SO$_2$)$_w$—Heteroaryl, an optionally substituted —$(CH_2)_n$—C(O)$_u$(NR$_1$)$_v$(SO$_2$)$_w$-Heterocycle, an optionally substituted —NR$^1$—(CH$_2$)$_n$—C(O)$_u$(NR$_1$)$_v$(SO$_2$)$_w$-alkyl, an optionally substituted —NR$^1$—(CH$_2$)$_n$—C(O)$_u$(NR$_1$)$_v$(SO$_2$)$_w$—NR$_{1N}$R$_{2N}$, an optionally substituted —NR$^1$—(CH$_2$)$_n$—C(O)$_u$(NR$_1$)$_v$(SO$_2$)$_w$—NR$_1$C(O)R$_{1N}$, an optionally substituted —NR$^1$—(CH$_2$)$_n$—C(O)$_u$(NR$_1$)$_v$(SO$_2$)$_w$-Aryl, an optionally substituted —NR$^1$—(CH$_2$)$_n$—C(O)$_u$ (NR$_1$)$_v$(SO$_2$)$_w$-Heteroaryl, an optionally substituted —NR$^1$—(CH$_2$)$_n$—C(O)$_u$(NR$_1$)$_v$(SO$_2$)$_w$-Heterocycle, an optionally substituted —O—(CH$_2$)n-(C=O)$_u$(NR$_1$)$_v$(SO$_2$)$_w$-alkyl, an optionally substituted —O—(CH$_2$)n-(C=O)$_u$(NR$_1$)$_v$(SO$_2$)$_w$—NR$_{1N}$R$_{2N}$, an optionally substituted —O—(CH$_2$)n-(C=O)$_u$(NR$_1$)$_v$(SO$_2$)$_w$—NR$_1$C(O)R$_{1N}$, an optionally substituted —O—(CH$_2$)n-(C=O)$_u$(NR$_1$)$_v$(SO$_2$)$_w$-Aryl, an optionally substituted —O—(CH$_2$)$_n$—(C=O)$_u$(NR$_1$)$_v$(SO$_2$)$_w$-Heteroaryl or an optionally substituted —O—(CH$_2$)$_n$—(C=O)$_u$(NR$_1$)$_v$(SO$_2$)$_w$-Heterocycle;  —(CH$_2$)$_n$—

$(V)_n$—$(CH_2)_n$—$(V)_{n'}$-alkyl group, an optionally substituted —$(CH_2)_n$—$(V)_{n'}$—$(CH_2)_n$—$(V)_{n'}$-Aryl group, an optionally substituted —$(CH_2)_n$—$(V)_{n'}$—$(CH_2)_n$—$(V)_{n'}$-Heteroaryl group, an optionally substituted —$(CH_2)_n$—$(V)_{n'}$—$(CH_2)_n$—$(V)_{n'}$-Heterocycle group, an optionally substituted —$(CH_2)_n$—$N(R_{1'})(C{=}O)_{m'}$—$(V)_{n'}$-alkyl group, an optionally substituted $\geq (CH_2)_n$—$N(R_{1'})(C{=}O)_{m'}$—$(V)_{n'}$-Aryl group, an optionally substituted —$(CH_2)_n$—$N(R_{1'})(C{=}O)_{m'}$—$(V)_{n'}$-Heteroaryl group, an optionally substituted —$(CH_2)_n$—$N(R_{1'})(C{=}O)_{m'}$—$(V)_{n'}$-Heterocycle group, an optionally substituted —$X^{R3'}$-alkyl group; an optionally substituted —$X^{R3'}$-Aryl group; an optionally substituted —$X^{R3'}$-Heteroaryl group; an optionally substituted —$X^{R3'}$-Heterocycle group; an optionally substituted;

$R_{1N}$ and $R_{2N}$ of ULM-g are each independently H, $C_1$-$C_6$ alkyl which is optionally substituted with one or two hydroxyl groups and up to three halogen groups or an optionally substituted -$(CH_2)_n$-Aryl, —$(CH_2)_n$-Heteroaryl or —$(CH_2)_n$-Heterocycle group;

V of ULM-g is O, S or $NR_1$;

$R_1$ of ULM-g is the same as above;

$R^1$ and $R_{1'}$ of ULM-g are each independently H or a $C_1$-$C_3$ alkyl group;

$X^{R2'}$ and $X^{R3'}$ of ULM-g are each independently an optionally substituted —$CH_2)_n$—, —$(CH_2)_n$—$CH(X_v){=}CH(X_v)$— (cis or trans), —$(CH_2)_n$—$CH{\equiv}CH$—, —$(CH_2CH_2O)_n$— or a $C_3$-$C_6$ cycloalkyl group, where $X_v$ is H, a halo or a $C_1$-$C_3$ alkyl group which is optionally substituted; each m of ULM-g is independently 0, 1, 2, 3, 4, 5, 6;

each m' of ULM-g is independently 0 or 1;

each n of ULM-g is independently 0, 1, 2, 3, 4, 5, 6;

each n' of ULM-g is independently 0 or 1;

each u of ULM-g is independently 0 or 1;

each v of ULM-g is independently 0 or 1;

each w of ULM-g is independently 0 or 1; and any one or more of $R^{1'}$, $R^{2'}$, $R^{3'}$, X and X' of ULM-g is optionally modified to be covalently bonded to the PTM group through a linker group when PTM is not ULM', or when PTM is ULM', any one or more of $R^{1'}$, $R^{2'}$, $R^{3'}$, X and X' of each of ULM and ULM' are optionally modified to be covalently bonded to each other directly or through a linker group, or a pharmaceutically acceptable salt, stereoisomer, solvate or polymorph thereof.

In any of the aspects or embodiments described herein, the ULM and when present, ULM', are each independently a group according to the chemical structure:

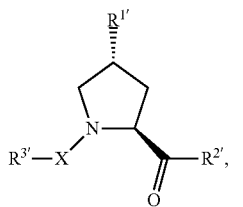

ULM-h wherein:
each of $R^{1'}$, $R^{2'}$ and $R^{3'}$ of ULM-h are the same as above and X is C=O, C=S, —S(O) group or a S(O)$_2$ group, more preferably a C=O group, and
any one or more of $R^{1'}$, $R^{2'}$ and $R^{3'}$ of ULM-h are optionally modified to bind a linker group to which is further covalently bonded to the PTM group when PTM is not ULM', or when PTM is ULM', any one or more of $R^{1'}$, $R^{2'}$, $R^{3'}$ of each of ULM and ULM' are optionally modified to be covalently bonded to each other directly or through a linker group, or a pharmaceutically acceptable salt, enantiomer, diastereomer, solvate or polymorph thereof.

In any of the aspects or embodiments described herein, the ULM, and when present, ULM', are each independently according to the chemical structure:

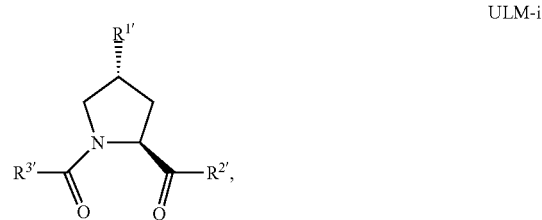

ULM-i wherein:
any one or more of $R^{1'}$, $R^{2'}$ and $R^{3'}$ of ULM-I are optionally modified to bind a linker group to which is further covalently bonded to the PTM group when PTM is not ULM', or when PTM is ULM', any one or more of $R^{1'}$, $R^{2'}$, $R^{3'}$ of each of ULM and ULM' are optionally modified to be covalently bonded to each other directly or through a linker group, or a pharmaceutically acceptable salt, enantiomer, diastereomer, solvate or polymorph thereof.

In further aspects of the disclosure, $R^1$ of ULM-g through ULM-i is preferably a hydroxyl group or a group which may be metabolized to a hydroxyl or carboxylic group, such that the compound represents a prodrug form of an active compound. Exemplary preferred $R^{1'}$ groups include, for example, —$(CH_2)_n$OH, $(CH_2)_n$—O—$(C_1$-$C_6)$alkyl group, —$(CH_2)_n$COOH, —$(CH_2O)_n$H, an optionally substituted —$(CH_2)_n$OC(O)—$(C_1$-$C_6$ alkyl), or an optionally substituted —$(CH_2)_n$C(O)—O—$(C_1$-$C_6$ alkyl), wherein n is 0 or 1. Where $R^{1'}$ is or contains a carboxylic acid group, a hydroxyl group or an amine group, the hydroxyl group, carboxylic acid group or amine (each of which may be optionally substituted), may be further chemically modified to provide a covalent link to a linker group to which the PTM group (including a ULM' group) is bonded;

X and X', where present, of ULM-g and ULM-h are preferably a C=O, C=S, —S(O) group or a S(O)$_2$ group, more preferably a C=O group;

$R^{2'}$ of ULM-g through ULM-i is preferably an optionally substituted —$NR^1$-T-Aryl, an optionally substituted —$NR^1$-T-Heteroaryl group or an optionally substituted —$NR^1$-T-Heterocycle, where $R^1$ is H or $CH_3$, preferably H and T is an optionally substituted —$(CH_2)_n$— group, wherein each one of the methylene groups may be optionally substituted with one or two substituents, preferably selected from halogen, an amino acid sidechain as otherwise described herein or a $C_1$-$C_3$ alkyl group, preferably one or two methyl groups, which may be optionally substituted; and n is 0 to 6 (e.g., 0, 1, 2 or 3, such as 0 or 1). Alternatively, T may also be a —$(CH_2O)_n$— group, a —$(OCH_2)_n$— group, a —$(CH_2CH_2O)_n$— group, a —$(OCH_2CH_2)_n$— group, all of which groups are optionally substituted.

Preferred Aryl groups for $R^{2'}$ of ULM-g through ULM-i include optionally substituted phenyl or naphthyl groups, preferably phenyl groups, wherein the phenyl or naphthyl group is optionally connected to a PTM group via a linker group to which is attached a PTM group (including a ULM' group), a halogen (preferably F or Cl), an amine, monoalkyl- or dialkyl amine (preferably, dimethylamine), F, Cl, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is optionally connected to a PTM via a linker group, including a ULM' group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo- (preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

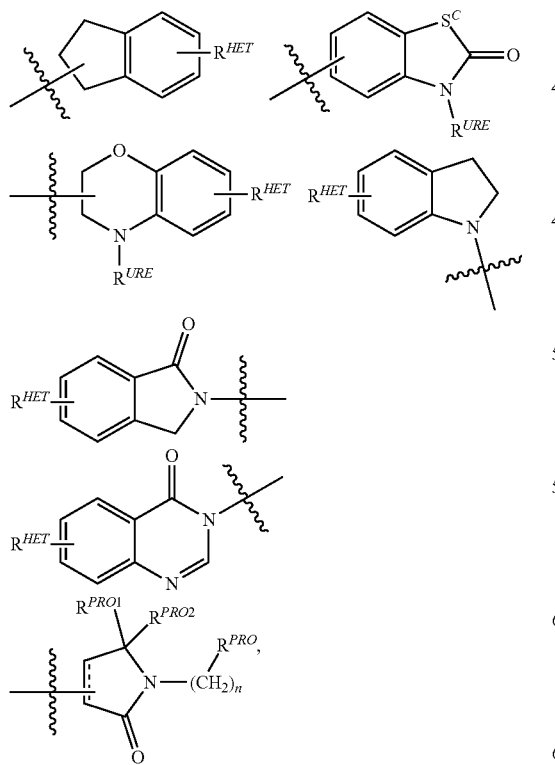

wherein:

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocycle, preferably for example piperidine, morpholine, pyrrolidine, tetrahydrofuran);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-1 are each independently H, an optionally substituted $C_1$-$C_3$ alkyl group or together form a keto group; and each n of ULM-g through ULM-i is independently 0, 1, 2, 3, 4, 5, or 6 (preferably 0 or 1), or an optionally substituted heterocycle, preferably tetrahydrofuran, tetrahydrothiene, piperidine, piperazine or morpholine (each of which groups when substituted, are preferably substituted with a methyl or halo (F, Br, Cl), each of which groups may be optionally connected to a PTM group (including a ULM' group) via a linker group.

In certain preferred aspects,

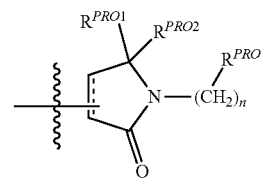

of ULM-g through ULM-i is a

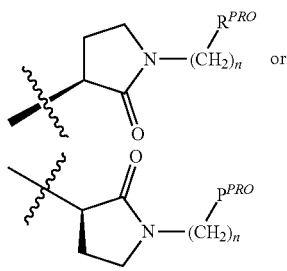

group, where $R^{PRO}$ and n of ULM-g through ULM-i are the same as above.

Preferred heteroaryl groups for $R^2$ of ULM-g through ULM-i include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3-, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

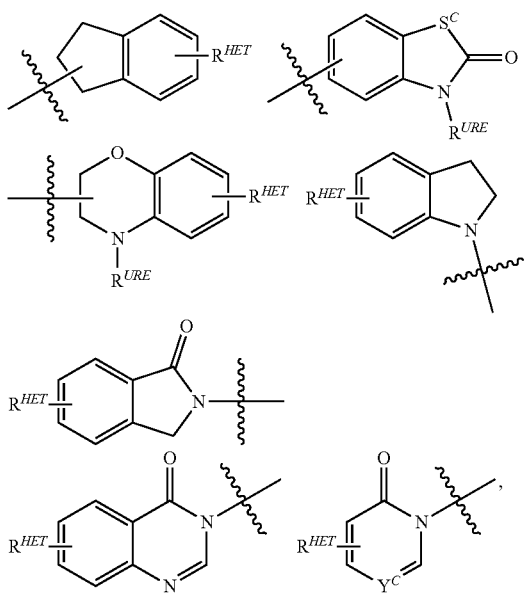

wherein:

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C☐C—

$R_a$ where $R_a$ of ULM-g through ULM-i is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C☐C—$R_a$ where $R_a$ is H or a $C_1$-$C_6$ alkyl group (preferably $C_1$-$C_3$ alkyl), each of which groups may be optionally connected to a PTM group (including a ULM' group) via a linker group.

Preferred heterocycle groups for $R^2$ of ULM-g through ULM-i include tetrahydrofuran, tetrahydrothiene, tetrahydroquinoline, piperidine, piperazine, pyrrolidine, morpholine, oxane or thiane, each of which groups may be optionally substituted, or a group according to the chemical structure:

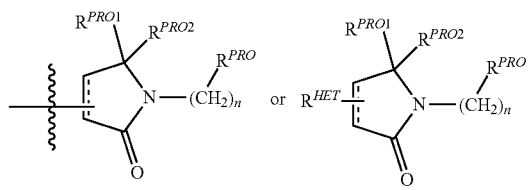

preferably, a

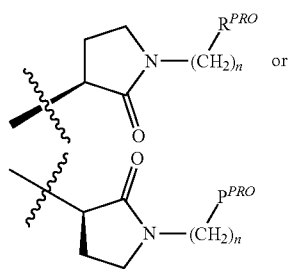

group, wherein:

$R^{PRO}$ of ULM-g through ULM-i is H, optionally substituted $C_1$-$C_6$ alkyl or an optionally substituted aryl, heteroaryl or heterocyclic group;

$R^{PRO1}$ and $R^{PRO2}$ of ULM-g through ULM-i are each independently H, an optionally substituted $C_1$-$C_3$ alkyl group or together form a keto group and each n of ULM-g through ULM-i is independently 0, 1, 2, 3, 4, 5, or 6 (often 0 or 1), each of which groups may be optionally connected to a PTM group (including a ULM' group) via a linker group.

Preferred $R^{2'}$ substituents of ULM-g through ULM-i also include specifically (and without limitation to the specific compound disclosed) the $R^{2'}$ substituents which are found in the identified compounds disclosed herein (which includes the specific compounds which are disclosed in the present specification, and the figures which are attached hereto). Each of these $R^{2'}$ substituents may be used in conjunction with any number of $R^{3'}$ substituents which are also disclosed herein.

$R^{3'}$ of ULM-g through ULM-i is preferably an optionally substituted -T-Aryl, an optionally substituted-T-Heteroaryl, an optionally substituted -T-Heterocycle, an optionally substituted-$NR^1$-T-Aryl, an optionally substituted —$NR^1$-T-Heteroaryl or an optionally substituted-$NR^1$-T-Heterocycle. In a preferred embodiment $R^1$ is H or a $C_1$-$C_3$ alkyl group, preferably H or $CH_3$, T is an optionally substituted —$(CH_2)_n$— group, wherein each one of the methylene groups may be optionally substituted with one or two substituents, preferably selected from halogen, a $C_1$-$C_6$ alkyl group (linear, branched, optionally substituted) or the sidechain of an amino acid as otherwise described herein, preferably methyl, which may be optionally substituted; and n is 0 to 6, e.g. 0, 1, 2, or 3 (such as 0 or 1). Alternatively, T may also be a —($CH_2$O)— group, a —(O$CH_2$)— group, a —($CH_2CH_2$O)— group, a —(O$CH_2CH_2$)— group, each of which groups is optionally substituted.

Preferred aryl groups for $R^3$ of ULM-g through ULM-i include optionally substituted phenyl or naphthyl groups, preferably phenyl groups, wherein the phenyl or naphthyl group is optionally connected to a PTM group (including a ULM' group) via a linker group and/or a halogen (preferably F or Cl), an amine, monoalkyl- or dialkyl amine (preferably, dimethylamine), an amido group (preferably a —$(CH_2)_m$—$NR_1C(O)R_2$ group where m, $R_1$ and $R_2$ are the same as above), a halo (often F or Cl), OH, $CH_3$, $CF_3$, OMe, $OCF_3$, $NO_2$, CN or a $S(O)_2R_S$ group ($R_S$ is a a $C_1$-$C_6$ alkyl group, an optionally substituted aryl, heteroaryl or heterocycle group or a —$(CH_2)_m NR_1 R_2$ group), each of which may be substituted in ortho-, meta- and/or para-positions of the phenyl ring, preferably para-), or an Aryl (preferably phenyl), Heteroaryl or Heterocycle. Preferably said substituent phenyl group is an optionally substituted phenyl group (i.e., the substituent phenyl group itself is preferably substituted with at least one of F, Cl, OH, SH, COOH, $CH_3$, $CF_3$, OMe, $OCF_3$, $NO_2$, CN or a linker group to which is attached a PTM group (including a ULM' group), wherein the substitution occurs in ortho-, meta- and/or para-positions of the phenyl ring, preferably para-), a naphthyl group, which may be optionally substituted including as described above, an optionally substituted heteroaryl (preferably an optionally substituted isoxazole including a methylsubstituted isoxazole, an optionally substituted oxazole including a methylsubstituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo- (preferably, F) or methylsubstitutedpyridine group or an oxapyridine group (where the pyridine group is linked to the phenyl group by an oxygen) or an optionally substituted heterocycle (tetrahydrofuran, tetrahydrothiophene, pyrrolidine, piperidine, morpholine, piperazine, tetrahydroquinoline, oxane or thiane. Each of the aryl, heteroaryl or heterocyclic groups may be optionally connected to a PTM group (including a ULM' group) via a linker group.

Preferred Heteroaryl groups for $R^{3'}$ of ULM-g through ULM-i include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

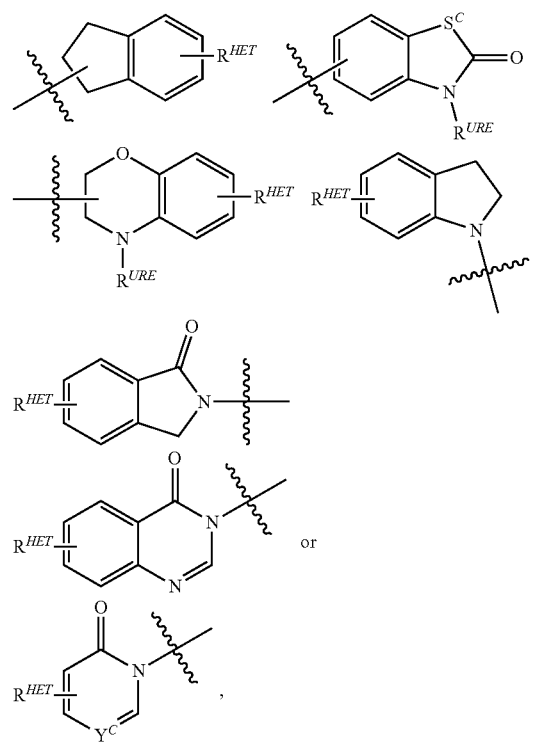

wherein:
$S^c$ of ULM-g through ULM-i is $CHR^{SS}$, $NR^{URE}$, or O;
$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups)

or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl). Each of said heteroaryl groups may be optionally connected to a PTM group (including a ULM' group) via a linker group.

Preferred heterocycle groups for $R^3$ of ULM-g through ULM-i include tetrahydroquinoline, piperidine, piperazine, pyrrollidine, morpholine, tetrahydrofuran, tetrahydrothiophene, oxane and thiane, each of which groups may be optionally substituted or a group according to the chemical structure:

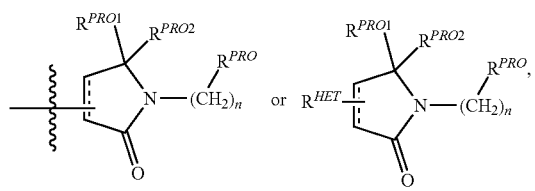

preferably, a

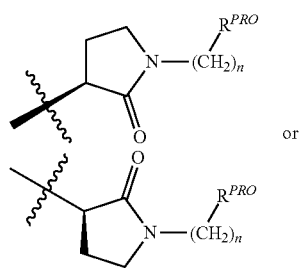

or group,
wherein:
$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group, and each n of ULM-g through ULM-i is 0, 1, 2, 3, 4, 5, or 6 (preferably 0 or 1), wherein each of said Heteocycle groups may be optionally connected to a PTM group (including a ULM' group) via a linker group.

Preferred $R^{3'}$ substituents of ULM-g through ULM-i also include specifically (and without limitation to the specific compound disclosed) the $R^{3'}$ substituents which are found in the identified compounds disclosed herein (which includes the specific compounds which are disclosed in the present specification, and the figures which are attached hereto). Each of these $R^{3'}$ substituents may be used in conjunction with any number of $R^{2'}$ substituents, which are also disclosed herein.

In certain alternative preferred embodiments, $R^{2'}$ of ULM-g through ULM-i is an optionally substituted —$NR_1$—$X^{R2'}$-alkyl group, —$NR_1$—$X^{R2'}$-Aryl group; an optionally substituted —$NR_1$—$X^{R2'}$-HET, an optionally substituted —$NR_1$—$X^{R2'}$-Aryl-HET or an optionally substituted —$NR_1$—$X^{R2'}$-HET-Aryl,
wherein:
$R_1$ of ULM-g through ULM-i is H or a $C_1$-$C_3$ alkyl group (preferably H);

$X^{R2'}$ of ULM-g through ULM-i is an optionally substituted —$CH_2)_n$—, —$(CH_2)_n$—$CH(X_v)$=$CH(X_v)$— (cis or trans), —$(CH_2)_n$—CH≡CH—, —$(CH_2CH_2O)_n$— or a $C_3$-$C_6$ cycloalkyl group; and $X_v$ of ULM-g through ULM-i is H, a halo or a $C_1$-$C_3$ alkyl group which is optionally substituted with one or two hydroxyl groups or up to three halogen groups;

Alkyl of ULM-g through ULM-i is an optionally substituted C1-$C_{10}$ alkyl (preferably a $C_1$-$C_6$ alkyl) group (in certain preferred embodiments, the alkyl group is end-capped with a halo group, often a Cl or Br);

Aryl of ULM-g through ULM-i is an optionally substituted phenyl or naphthyl group (preferably, a phenyl group); and HET of ULM-g through ULM-i is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl) or a group according to the chemical structure:

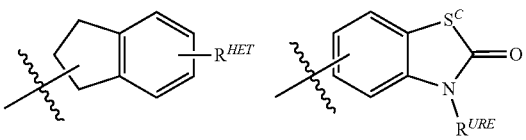

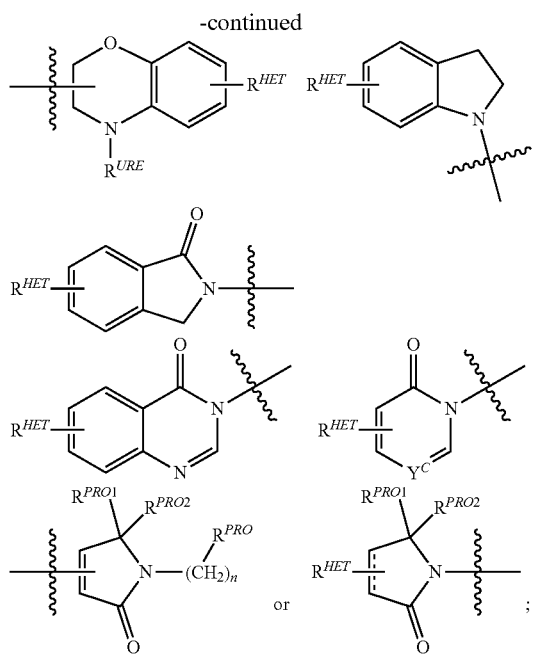

$S^C$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group, and each n of ULM-g through ULM-i is independently 0, 1, 2, 3, 4, 5, or 6 (preferably 0 or 1).

Each of said groups may be optionally connected to a PTM group (including a ULM' group) via a linker group.

In certain alternative embodiments of the present disclosure, $R^{3'}$ of ULM-g through ULM-i is an optionally substituted —$(CH_2)_n$—$(V)_n$—$(CH_2)_n$—$(V)_n$—$R^{3'}$ group, an optionally substituted -$(CH_2)_n$—$N(R_{1'})(C=O)_m$—$(V)_n$—$R^{S3'}$ group, an optionally substituted —$X^{R3'}$-alkyl group, an optionally substituted —$X^{R3'}$-Aryl group; an optionally substituted —$X^{R3'}$-HET group, an optionally substituted —$X^{R3'}$-Aryl-HET group or an optionally substituted —$X^{R3'}$-HET-Aryl group, wherein:

$R^{S3'}$ is an optionally substituted alkyl group ($C_1$-$C_{10}$, preferably $C_1$-$C_6$ alkyl), an optionally substituted Aryl group or a HET group;

$R_{1'}$ is H or a $C_1$-$C_3$ alkyl group (preferably H);

V is O, S or $NR_1$;

$X^{R3'}$ is —$(CH_2)_n$—, —$(CH_2CH_2O)_n$—, —$CH_2)_n$—CH$(X_v)$=CH$(X_v)$— (cis or trans), —$(CH_2)_n$—CH=CH—, or a $C_3$-$C_6$ cycloalkyl group, all optionally substituted;

$X_v$ is H, a halo or a $C_1$-$C_3$ alkyl group which is optionally substituted with one or two hydroxyl groups or up to three halogen groups;

Alkyl is an optionally substituted $C_1$-$C_{10}$ alkyl (preferably a $C_1$-$C_6$ alkyl) group (in certain preferred embodiments, the alkyl group is end-capped with a halo group, often a Cl or Br);

Aryl is an optionally substituted phenyl or napthyl group (preferably, a phenyl group); and HET is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl), or a group according to the chemical structure:

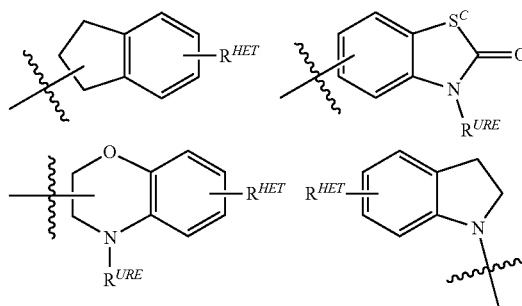

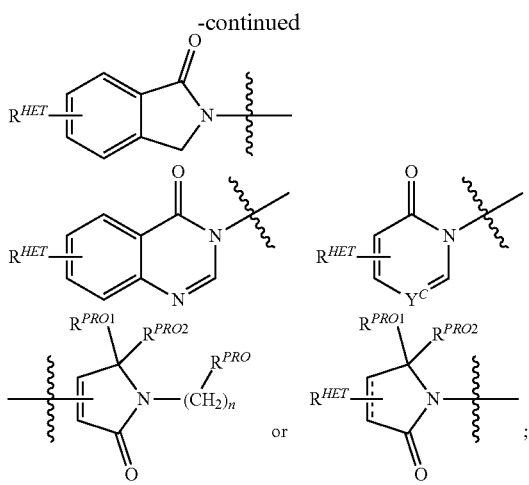

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group;

each n of ULM-g through ULM-i is independently 0, 1, 2, 3, 4, 5, or 6 (preferably 0 or 1);

each m' of ULM-g through ULM-i is 0 or 1; and each n' of ULM-g through ULM-i is 0 or 1;

wherein each of said compounds, preferably on the alkyl, Aryl or Het groups, is optionally connected to a PTM group (including a ULM' group) via a linker group.

In alternative embodiments, $R^{3'}$ of ULM-g through ULM-i is —$(CH_2)_n$-Aryl, —$(CH_2CH_2O)_n$-Aryl, —$(CH_2)_n$-HET or —$(CH_2CH_2O)_n$-HET, wherein:
said Aryl of ULM-g through ULM-i is phenyl which is optionally substituted with one or two substitutents, wherein said substituent(s) is preferably selected from —$(CH_2)_n$OH, $C_1$-$C_6$ alkyl which itself is further optionally substituted with CN, halo (up to three halo groups), OH, —$(CH_2)_nO(C_1$-$C_6)$alkyl, amine, mono- or di-($C_1$-$C_6$ alkyl) amine wherein the alkyl group on the amine is optionally substituted with 1 or 2 hydroxyl groups or up to three halo (preferably F, Cl) groups, or said Aryl group of ULM-g through ULM-i is substituted with —$(CH_2)_n$OH, —$(CH_2)_n$—O—($C_1$-$C_6$)alkyl, —$(CH_2)_n$—O—$(CH_2)_n$—($C_1$-$C_6$)alkyl, —$(CH_2)_n$—C(O)($C_0$-$C_6$) alkyl, —$(CH_2)_n$—C(O)O($C_0$-$C_6$)alkyl, —$(CH_2)_n$—OC(O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, CO groups, CN, $NO_2$, an optionally substituted —$(CH_2)_n$—$(V)_m$—$CH_2)_n$—$(V)_{m'}$—($C_1$-$C_6$)alkyl group, a —$(V)_{m'}$—$(CH_2CH_2O)_n$—$R^{PEG}$ group where V is O, S or $NR_{1'}$, $R_{1'}$ is H or a $C_1$-$C_3$ alkyl group (preferably H) and $R^{PEG}$ is H or a $C_1$-$C_6$ alkyl group which is optionally substituted (including being optionally substituted with a carboxyl group), or said Aryl group of ULM-g through ULM-i is optionally substituted with a heterocycle, including a heteroaryl, selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine, (when substituted each preferably substituted with a $C_1$-$C_3$ alkyl group, preferably methyl or a halo group, preferably F or Cl), or a group according to the chemical structure:

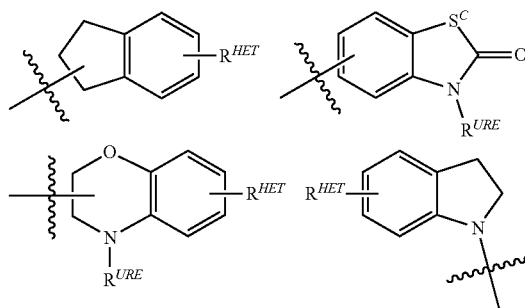

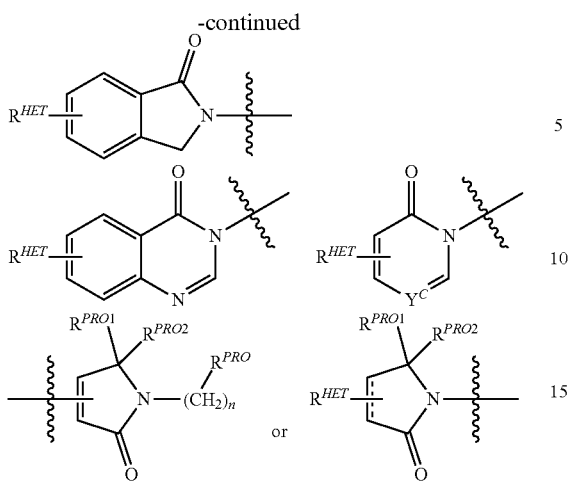

S$^c$ of ULM-g through ULM-i is CHR$^{SS}$, NR$^{URE}$, or O;

R$^{HET}$ of ULM-g through ULM-i is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

R$^{SS}$ of ULM-g through ULM-i is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);

R$^{URE}$ of ULM-g through ULM-i is H, a C$_1$-C$_6$ alkyl (preferably H or C$_1$-C$_3$ alkyl) or a —C(O)(C$_0$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

Y$^C$ of ULM-g through ULM-i is N or C—R$^{YC}$, where R$^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

R$^{PRO}$ of ULM-g through ULM-i is H, optionally substituted C$_1$-C$_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a C$_1$-C$_3$ alkyl group, preferably methyl or a halo group, preferably F or Cl), benzofuran, indole, indolizine, azaindolizine;

R$^{PRO1}$ and R$^{PRO2}$ of ULM-g through ULM-i are each independently H, an optionally substituted C$_1$-C$_3$ alkyl group or together form a keto group;

HET of ULM-g through ULM-i is preferably oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a C$_1$-C$_3$ alkyl group, preferably methyl or a halo group, preferably F or Cl), benzofuran, indole, indolizine, azaindolizine, or a group according to the chemical structure:

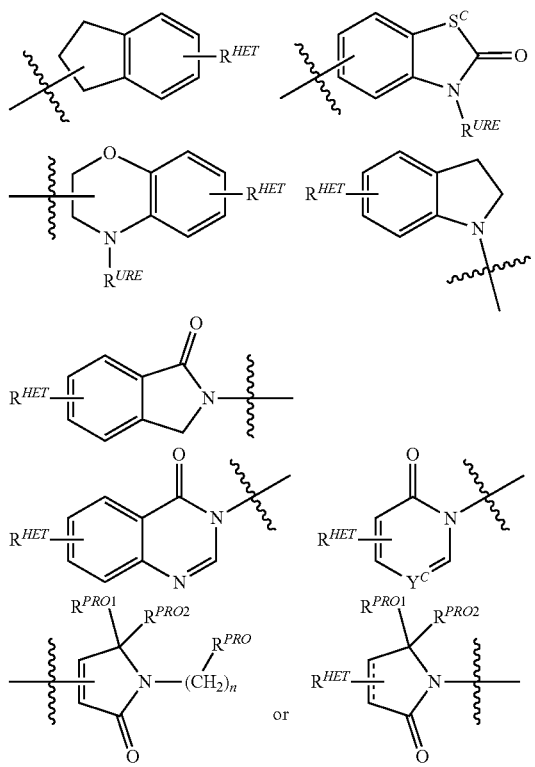

S$^c$ of ULM-g through ULM-i is CHR$^{SS}$, NR$^{URE}$, or O;

R$^{HET}$ of ULM-g through ULM-i is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

R$^{SS}$ of ULM-g through ULM-i is H, CN, NO$_2$, halo (preferably F or CO, optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);

R$^{UBE}$ of ULM-g through ULM-i is H, a C$_1$-C$_6$ alkyl (preferably H or C$_1$-C$_3$ alkyl) or a —C(O)(C$_0$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl, heteroaryl or heterocyclic group;

$R^{PRO1}$ and $R^{PRO2}$ of ULM-g through ULM-i are each independently H, an optionally substituted $C_1$-$C_3$ alkyl group or together form a keto group;

each m' of ULM-g through ULM-i is independently 0 or 1; and each n of ULM-g through ULM-i is independently 0, 1, 2, 3, 4, 5, or 6 (preferably 0 or 1), wherein each of said compounds, preferably on said Aryl or HET groups, is optionally connected to a PTM group (including a ULM' group) via a linker group.

In still additional embodiments, preferred compounds include those according to the chemical structure:

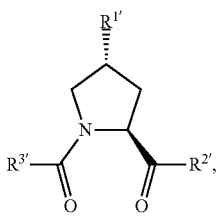

ULM-i wherein:
$R^{1'}$ of ULM-i is OH or a group which is metabolized in a patient or subject to OH;

$R^{2'}$ of ULM-i is a —NH—$CH_2$-Aryl-HET (preferably, a phenyl linked directly to a methyl substituted thiazole);

$R^3$ of ULM-i is a —$CHR^{CR3'}$—NH—C(O)—$R^{3P1}$ group or a —$CHR^{CR3'}$—$R^{3P2}$ group;

$R^{CR3'}$ of ULM-i is a $C_1$-$C_4$ alkyl group, preferably methyl, isopropyl or tert-butyl;

$R^{3P1}$ of ULM-i is $C_1$-$C_3$ alkyl (preferably methyl), an optionally substituted oxetane group (preferably methyl substituted, a —$(CH_2)_n OCH_3$ group where n is 1 or 2 (preferably 2), or a

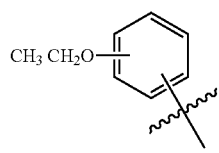

group (the ethyl ether group is preferably meta-substituted on the phenyl moiety), a morpholino group (linked to the carbonyl at the 2- or 3-position;

$R^{3P2}$ of ULM-i is a

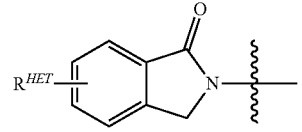

group;
Aryl of ULM-i is phenyl;
HET of ULM-i is an optionally substituted thiazole or isothiazole; and
$R^{HET}$ of ULM-i is H or a halo group (preferably H);
or a pharmaceutically acceptable salt, stereoisomer, solvate or polymorph thereof, wherein each of said compounds is optionally connected to a PTM group (including a ULM' group) via a linker group.

In certain aspects, bifunctional compounds comprising a ubiquitin E3 ligase binding moiety (ULM), wherein ULM is a group according to the chemical structure:

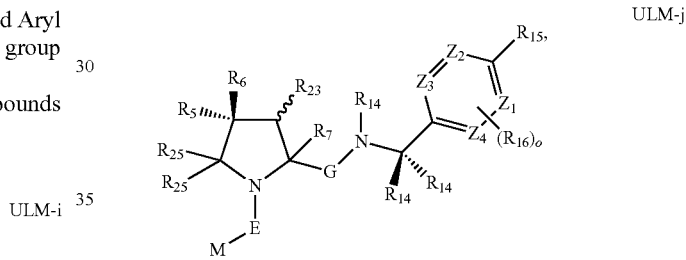

ULM-j wherein:
each $R_5$ and $R_6$ of ULM-j is independently OH, SH, or optionally substituted alkyl or $R_5$, $R_6$, and the carbon atom to which they are attached form a carbonyl;
$R_7$ of ULM-j is H or optionally substituted alkyl;
E of ULM-j is a bond, C=O, or C=S;
G of ULM-j is a bond, optionally substituted alkyl, —COOH or C=J;
J of ULM-j is O or N—$R_8$;
$R_8$ of ULM-j is H, CN, optionally substituted alkyl or optionally substituted alkoxy;
M of ULM-j is optionally substituted aryl, optionally substituted heteroaryl, optionally substituted heterocyclic or

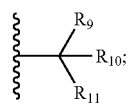

each $R_9$ and $R_{10}$ of ULM-j is independently H; optionally substituted alkyl, optionally substituted cycloalkyl, optionally substituted hydroxyalkyl, optionally substituted thioalkyl, a disulphide linked ULM, optionally substituted heteroaryl, or haloalkyl; or $R_9$, $R_{10}$, and the carbon atom to which they are attached form an optionally substituted cycloalkyl;

$R_{11}$ of ULM-j is optionally substituted heterocyclic, optionally substituted alkoxy, optionally substituted heteroaryl, optionally substituted aryl, or

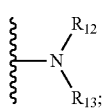

$R_{12}$ of ULM-j is H or optionally substituted alkyl;
$R_{13}$ of ULM-j is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl) carbamate,
each $R_{14}$ of ULM-j is independently H, haloalkyl, optionally substituted cycloalkyl, optionally substituted alkyl or optionally substituted heterocycloalkyl;
$R_{15}$ of ULM-j is H, optionally substituted heteroaryl, haloalkyl, optionally substituted aryl, optionally substituted alkoxy, or optionally substituted heterocyclyl;
each $R_{16}$ of ULM-j is independently halo, optionally substituted alkyl, optionally substituted haloalkyl, CN, or optionally substituted haloalkoxy;
each $R_{25}$ of ULM-j is independently H or optionally substituted alkyl; or both $R_{25}$ groups can be taken together to form an oxo or optionally substituted cycloalkyl group;
$R_{23}$ of ULM-j is H or OH;
$Z_1$, $Z_2$, $Z_3$, and $Z_4$ of ULM-j are independently C or N; and
o of ULM-j is 0, 1, 2, 3, or 4, or a pharmaceutically acceptable salt, stereoisomer, solvate or polymorph thereof.

In certain embodiments, wherein G of ULM-j is C=J, J is O, $R_7$ is H, each $R_{14}$ is H, and o is 0.

In certain embodiments, wherein G of ULM-j is C=J, J is O, $R_7$ is H, each $R_{14}$ is H, $R_{15}$ is optionally substituted heteroaryl, and o is 0. In other instances, E is C=O and M is

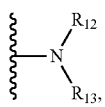

In certain embodiments, wherein E of ULM-j is C=O, $R_{11}$ is optionally substituted heterocyclic or

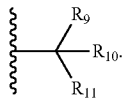

and M is

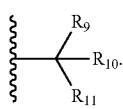

In certain embodiments, wherein E of ULM-j is C=O, M is

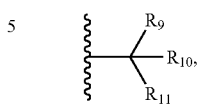

and $R_{11}$ is

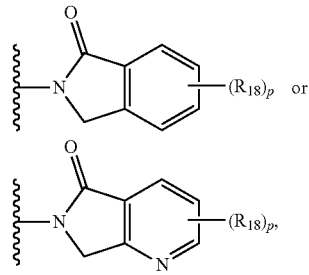

each $R_{18}$ is independently halo, optionally substituted alkoxy, cyano, optionally substituted alkyl, haloalkyl, or haloalkoxy; and p is 0, 1, 2, 3, or 4.

In certain embodiments, ULM and where present, ULM', are each independently a group according to the chemical structure:

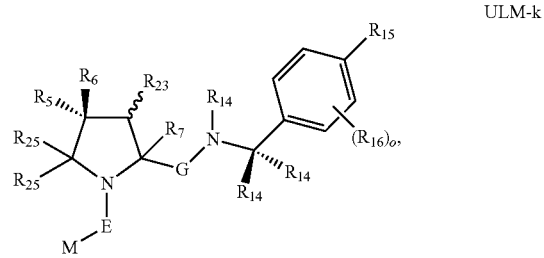

ULM-k wherein:
G of ULM-k is C=J, J is O;
$R_7$ of ULM-k is H;
each $R_{14}$ of ULM-k is H;
o of ULM-k is 0;
$R_{15}$ of ULM-k is

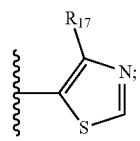

and
$R_{17}$ of ULM-k is H, halo, optionally substituted cycloalkyl, optionally substituted alkyl, optionally substituted alkenyl, and haloalkyl.

In other instances, $R_{17}$ of ULM-k is alkyl (e.g., methyl) or cycloalkyl (e.g., cyclopropyl).

In other embodiments, ULM and where present, ULM', are each independently a group according to the chemical structure:

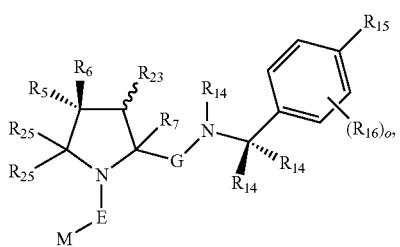

wherein:
G of ULM-k is C=J, J is O;
R₇ of ULM-k is H;
each R₁₄ of ULM-k is H;
o of ULM-k is 0; and
R₁₅ of ULM-k is selected from the group consisting of:

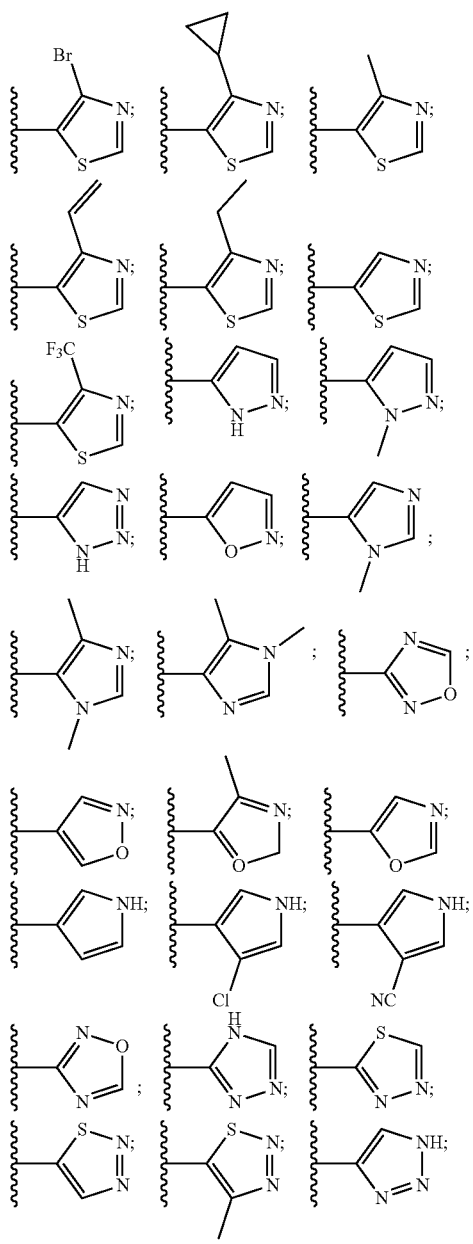

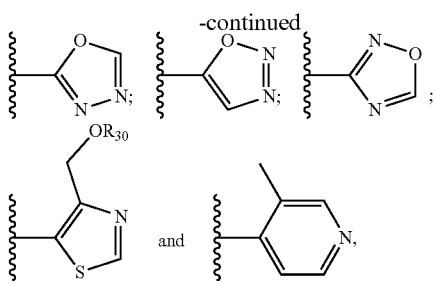

wherein $R_{30}$ of ULM-k is H or an optionally substituted alkyl.

In other embodiments, ULM and where present, ULM', are each independently a group according to the chemical structure:

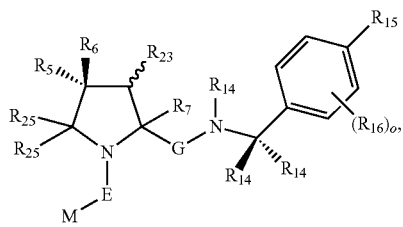

ULM-k wherein:
E of ULM-k is C=O;
M of ULM-k is

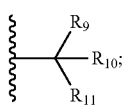

and
$R_{11}$ of ULM-k is selected from the group consisting of:

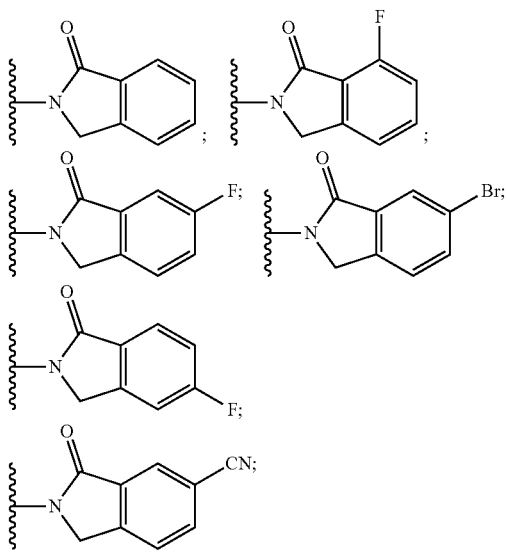

-continued

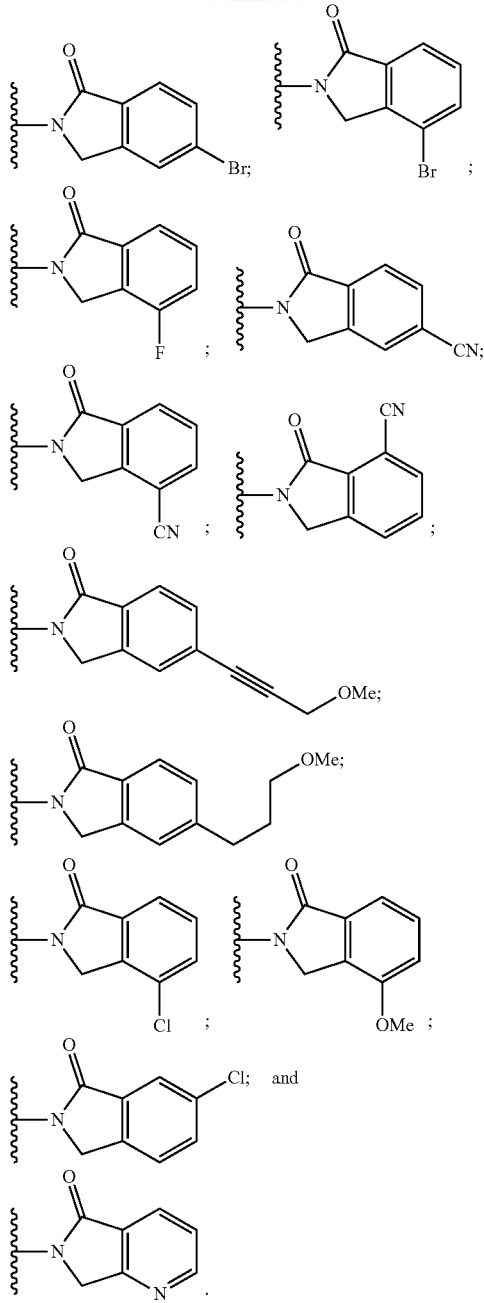

In still other embodiments, a compound of the chemical structure,

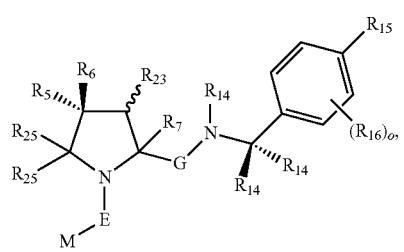
ULM-k wherein E of ULM-k is C=O;
R$_{11}$ of ULM-k is

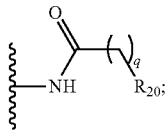

and
M of ULM-k is

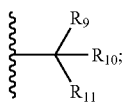

q of ULM-k is 1 or 2;
R$_{20}$ of ULM-k is H, optionally substituted alkyl, optionally substituted cycloalkyl, optionally substituted aryl, or

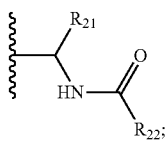

R$_{21}$ of ULM-k is H or optionally substituted alkyl; and
R$_{22}$ of ULM-k is H, optionally substituted alkyl, optionally substituted alkoxy, or haloalkyl.

In any embodiment described herein, R$_{11}$ of ULM-j or ULM-k is selected from the group consisting of:

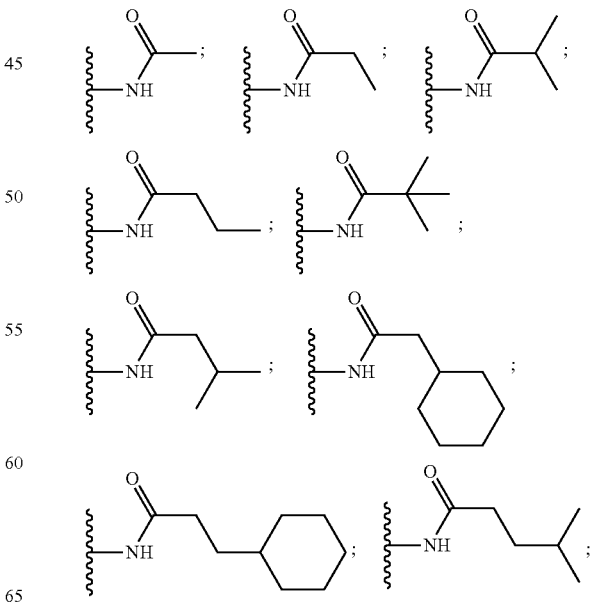

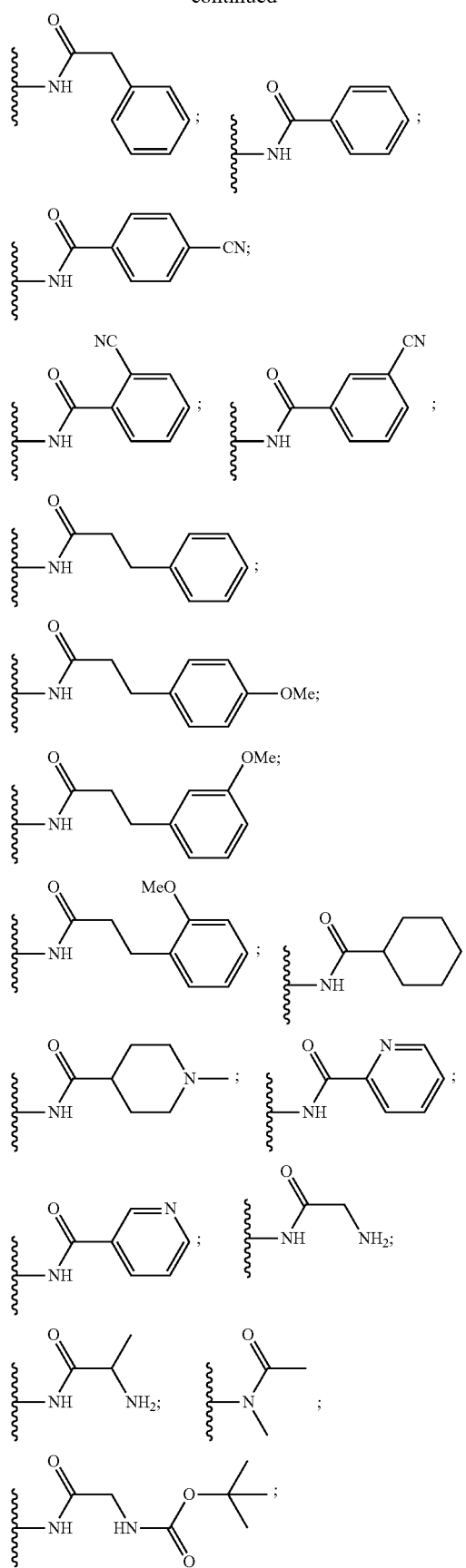
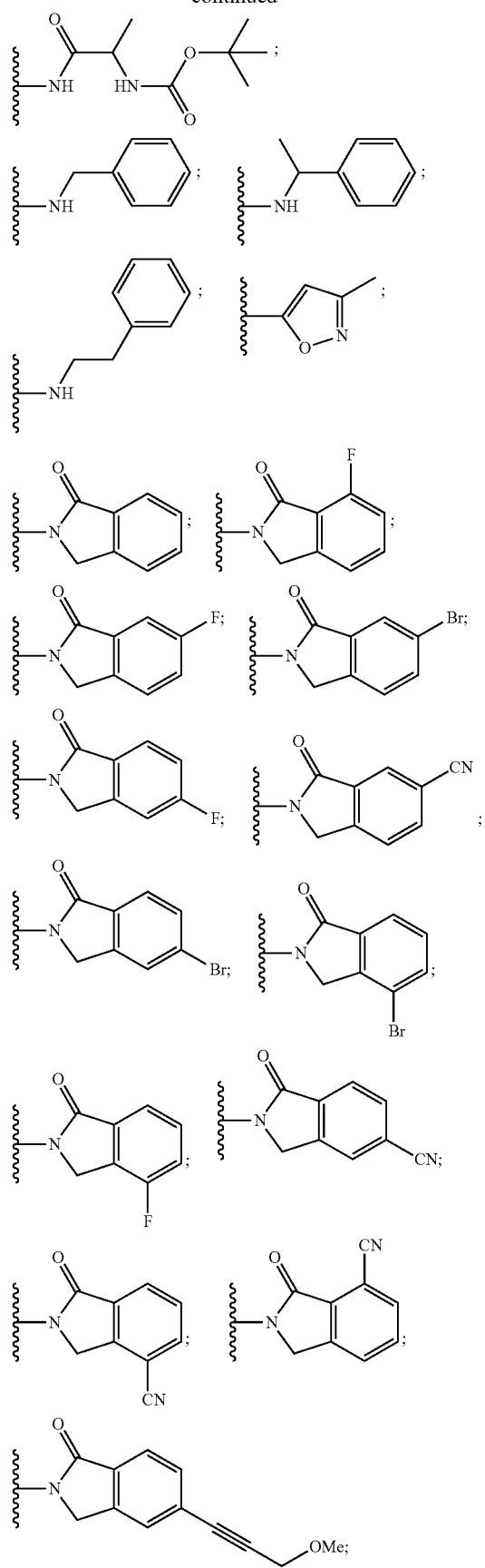

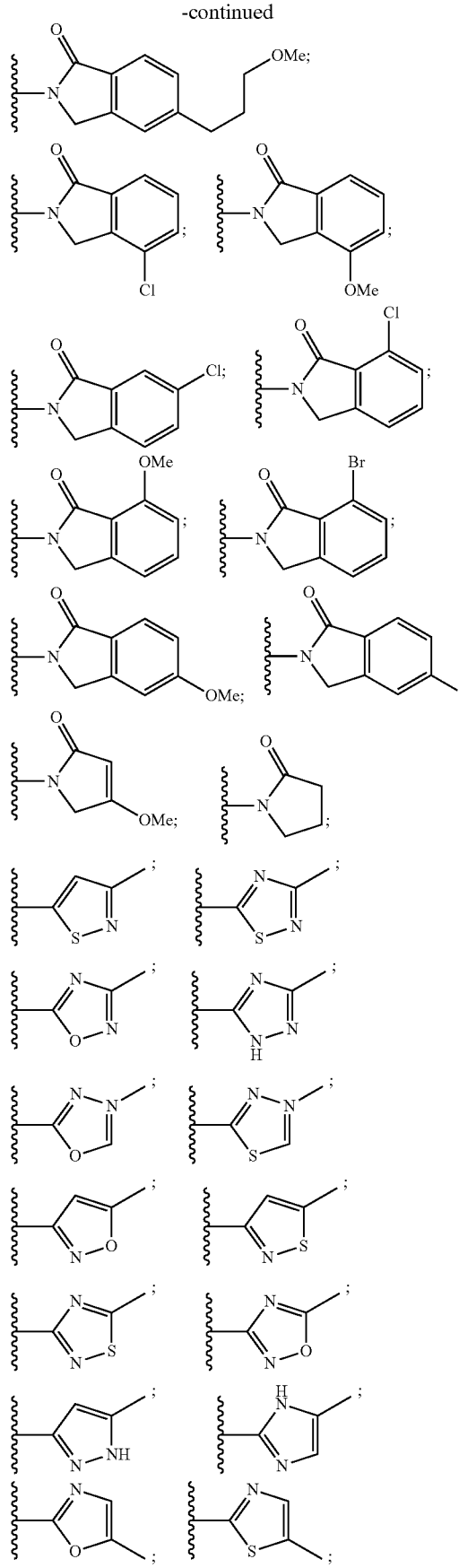
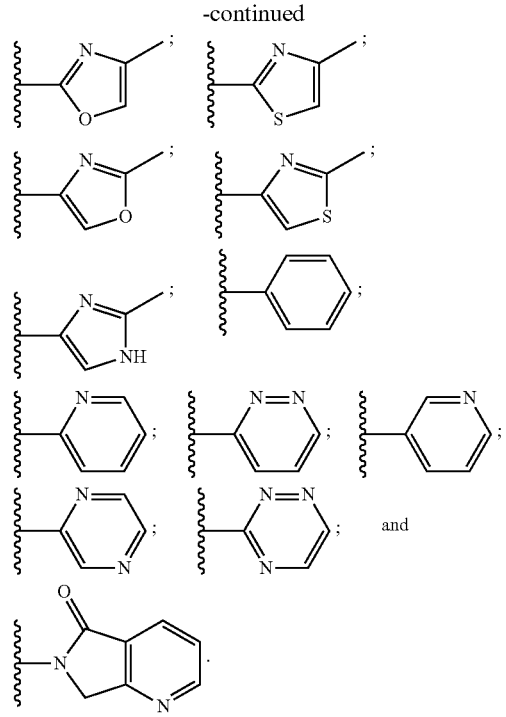
In certain embodiments, $R_{11}$ of ULM-j or ULM-k is selected from the group consisting of:
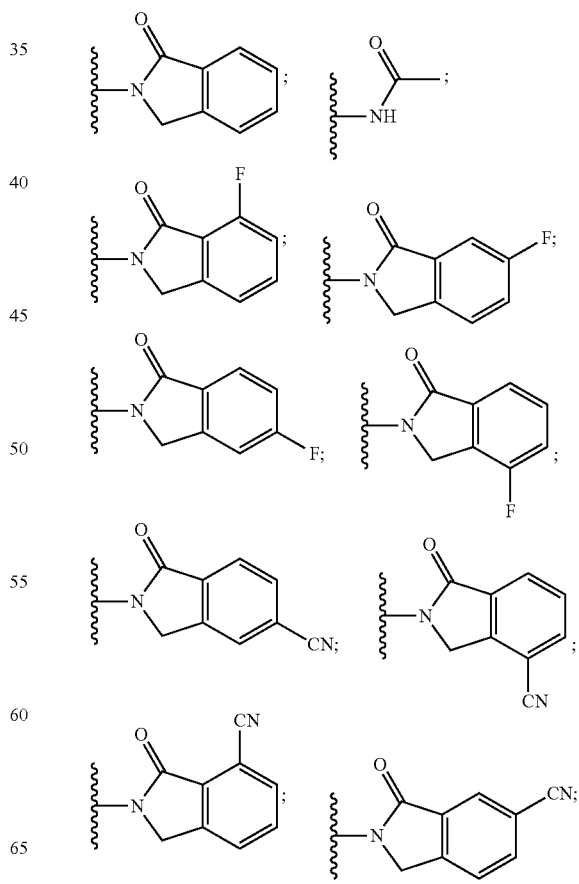

217
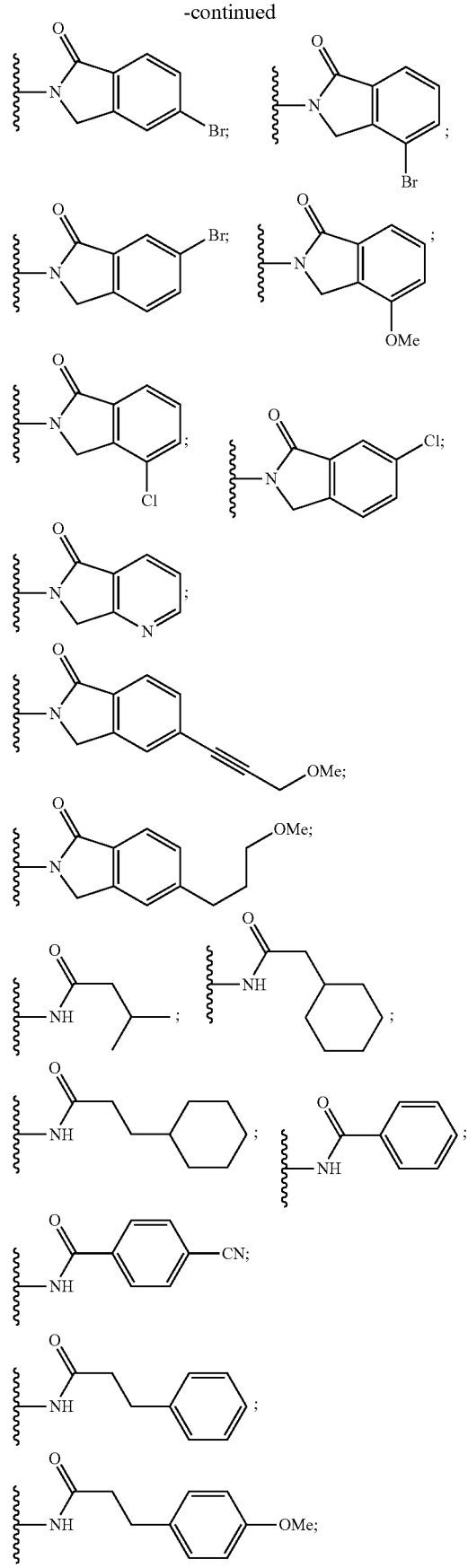
218
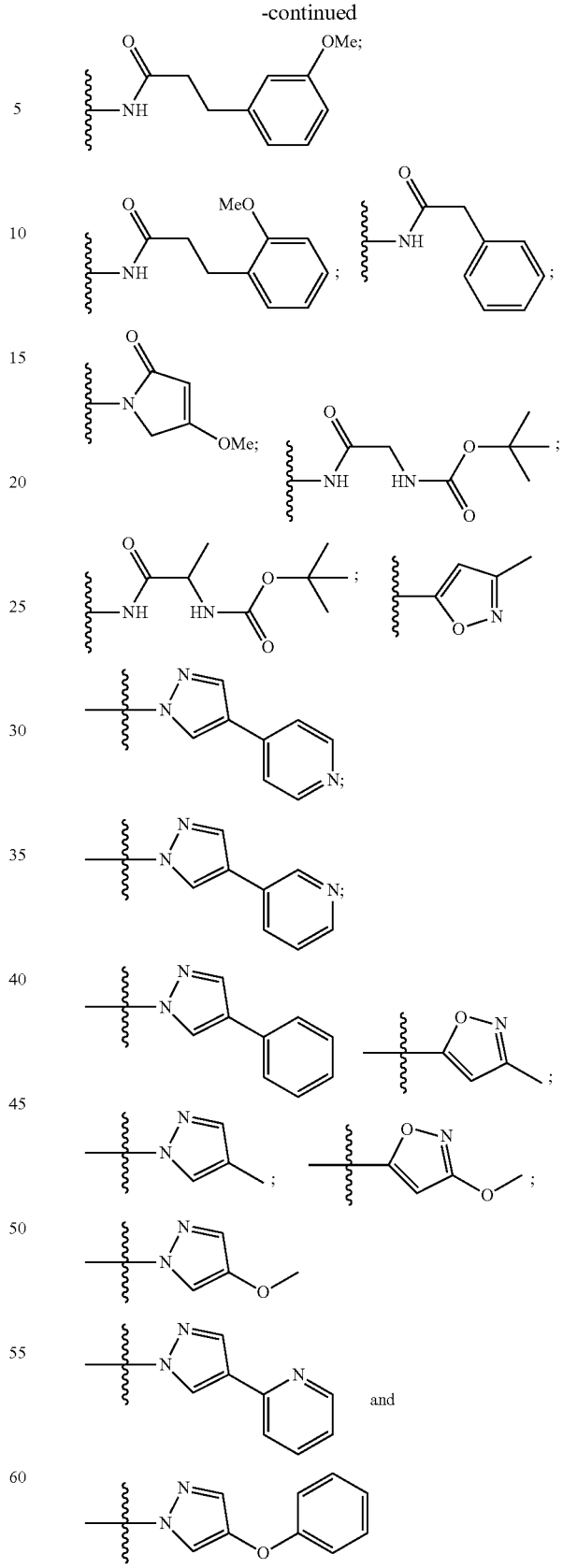
In certain embodiments, ULM (or when present ULM') is a group according to the chemical structure:

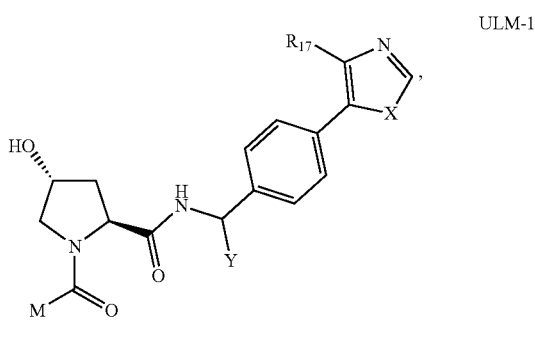

wherein:

X of ULM-1 is O or S;

Y of ULM-1 is H, methyl or ethyl;

$R_{17}$ of ULM-1 is H, methyl, ethyl, hydroxymethyl or cyclopropyl;

M of ULM-1 is is optionally substituted aryl, optionally substituted heteroaryl, or

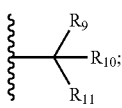

$R_9$ of ULM-1 is H;

$R_{10}$ of ULM-1 is H, optionally substituted alkyl, optionally substituted haloalkyl, optionally substituted heteroaryl, optionally substituted aryl, optionally substituted hydroxyalkyl, optionally substituted thioalkyl or cycloalkyl;

R11 of ULM-1 is optionally substituted heteroaromatic, optionally substituted heterocyclic, optionally substituted aryl or

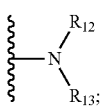

$R_{12}$ of ULM-1 is H or optionally substituted alkyl; and $R_{13}$ of ULM-1 is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate.

In some embodiments, ULM and where present, ULM', are each independently a group according to the chemical structure:

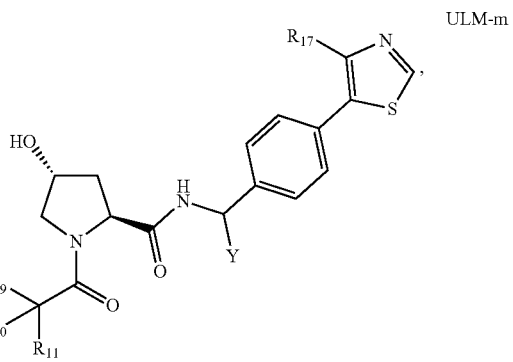

wherein:

Y of ULM-m is H, methyol or ethyl $R_9$ of ULM-m is H;

$R_{10}$ is isopropyl, tert-butyl, sec-butyl, cyclopentyl, or cyclohexyl;

$R_{11}$ of ULM-m is optionally substituted amide, optionally substituted isoindolinone, optionally substituted isooxazole, optionally substituted heterocycles.

In other embodiments of the disclosure, ULM and where present, ULM', are each independently a group according to the chemical structure:

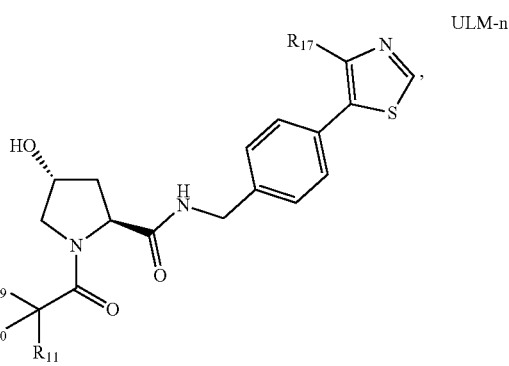

Wherein:

$R_{17}$ of ULM-n is methyl, ethyl, or cyclopropyl; and $R_9$, $R_{10}$, and $R_{11}$ of ULM-n are as defined above. In other instances, $R_9$ is H; and $R_{10}$ of ULM-n is H, alkyl, or or cycloalkyl (preferably, isopropyl, tert-butyl, sec-butyl, cyclopentyl, or cyclohexyl).

In any of the aspects or embodiments described herein, the ULM (or when present, ULM') as described herein may be a pharmaceutically acceptable salt, enantiomer, diastereomer, solvate or polymorph thereof. In addition, in any of the aspects or embodiments described herein, the ULM (or when present, ULM') as described herein may be coupled to a PTM directly via a bond or by a chemical linker.

In certain aspects of the disclosure, the ULM moiety is selected from the group consisting of:

221
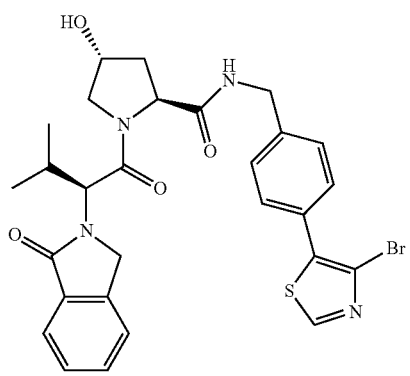
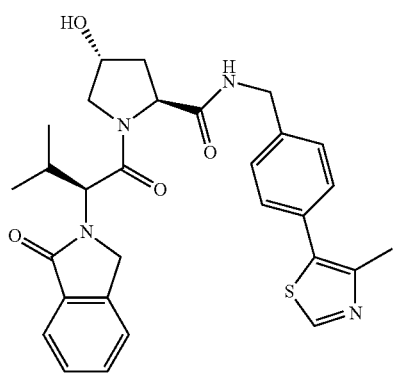
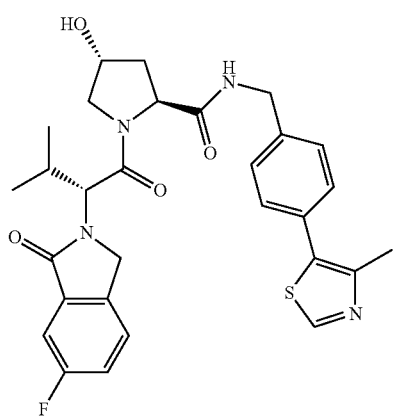
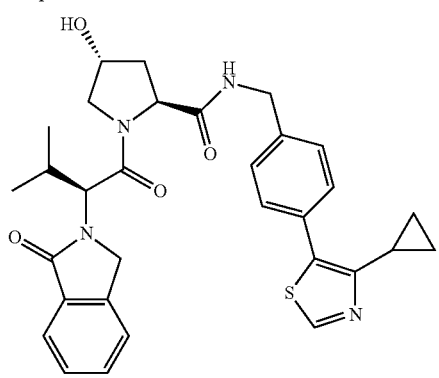
222
-continued
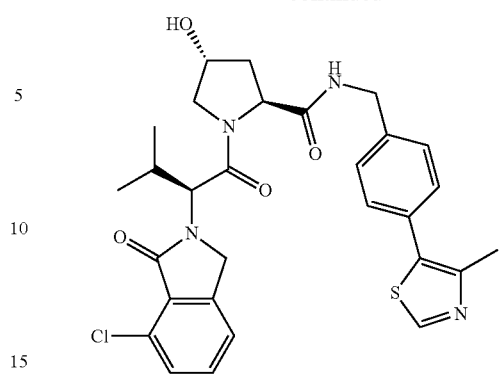
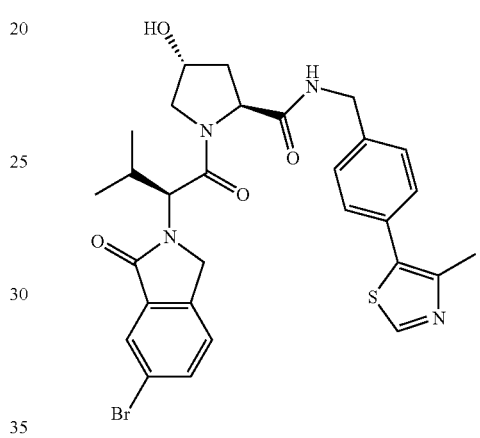
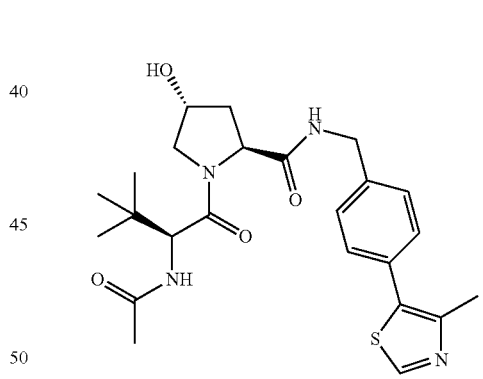
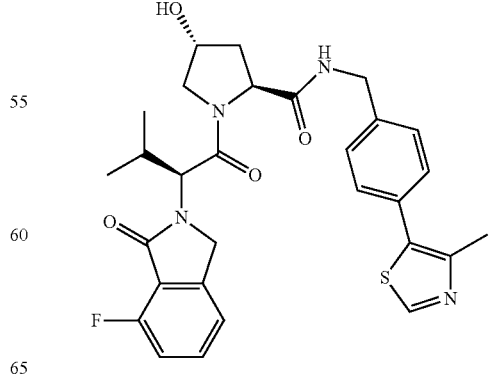

223
-continued
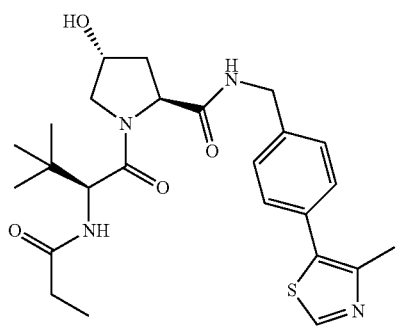
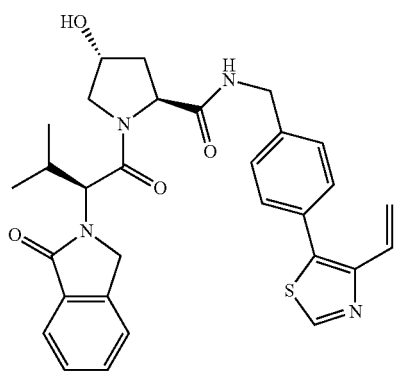
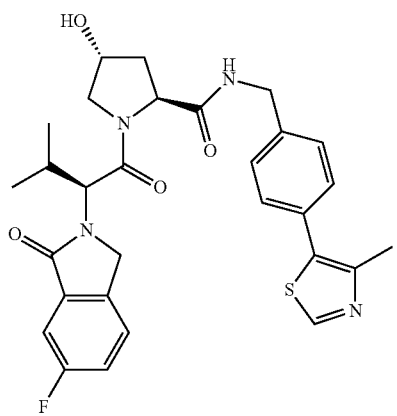
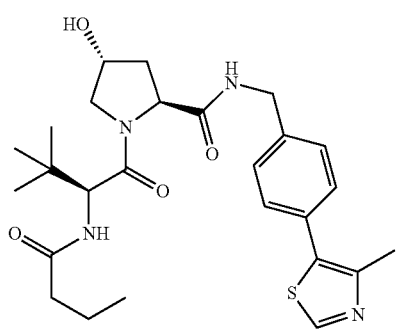
224
-continued
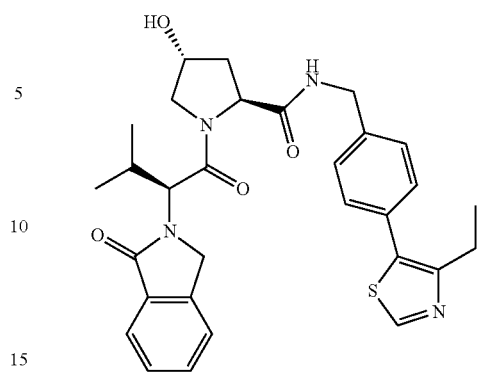
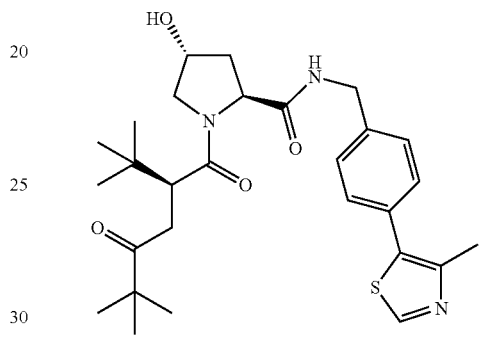
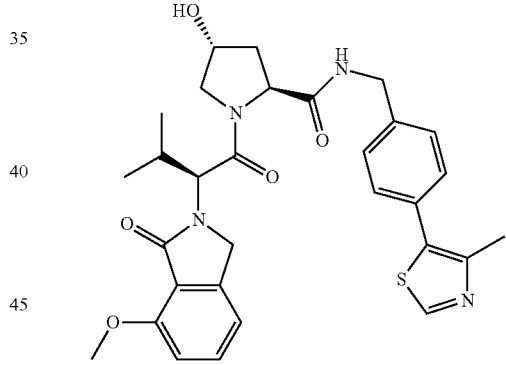
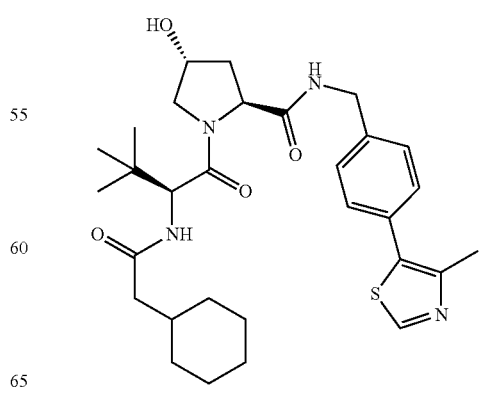

225
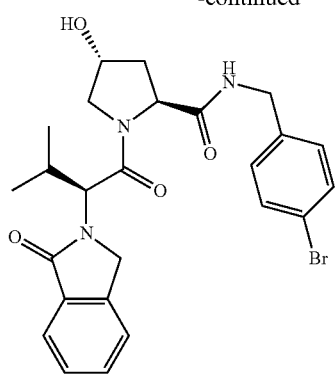
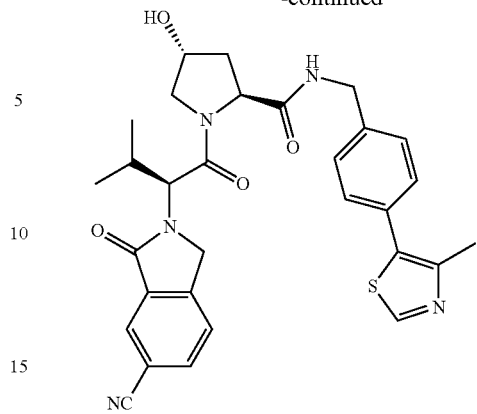
226
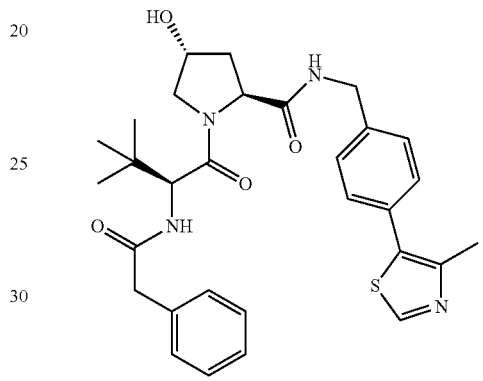
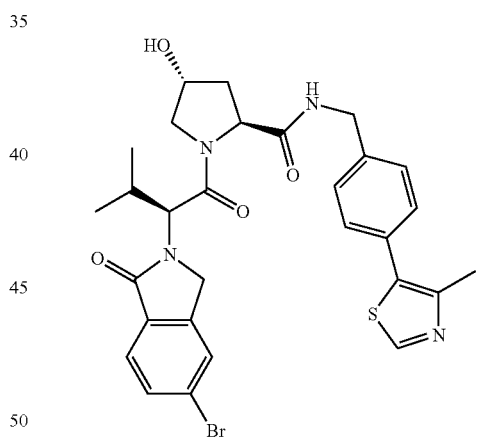
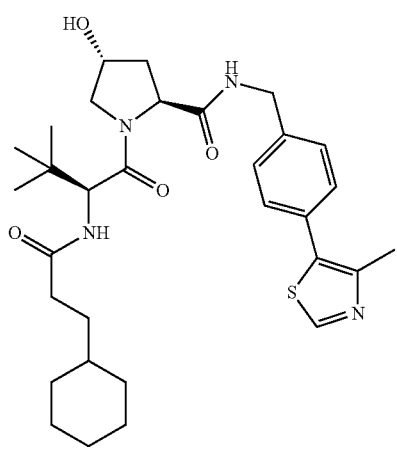
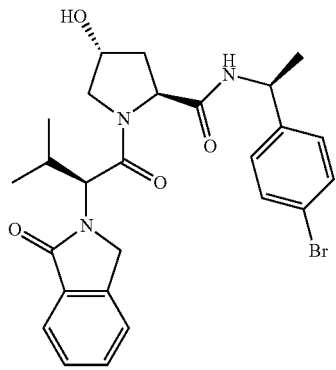
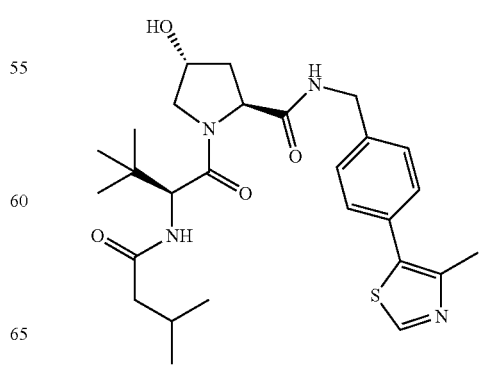

227
-continued
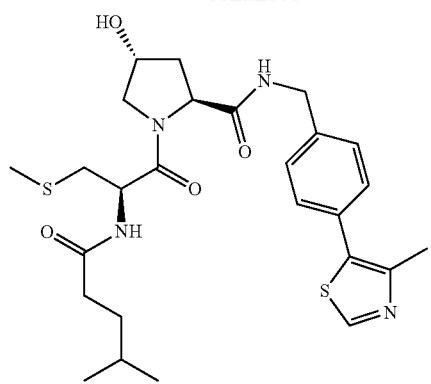
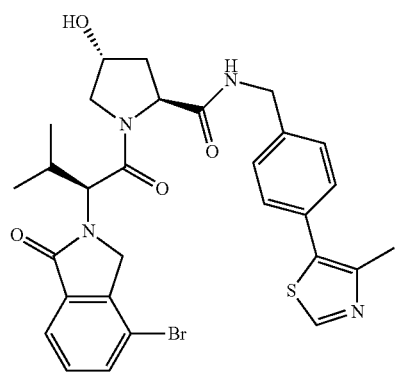
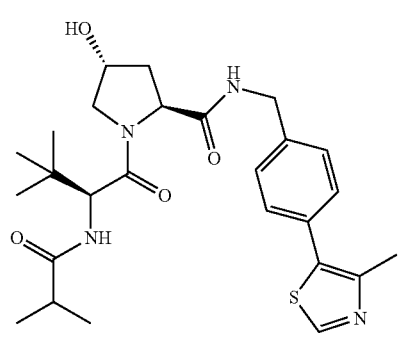
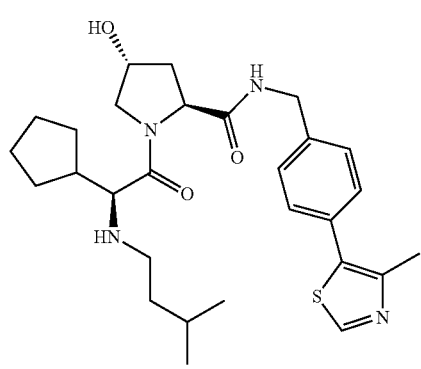
228
-continued
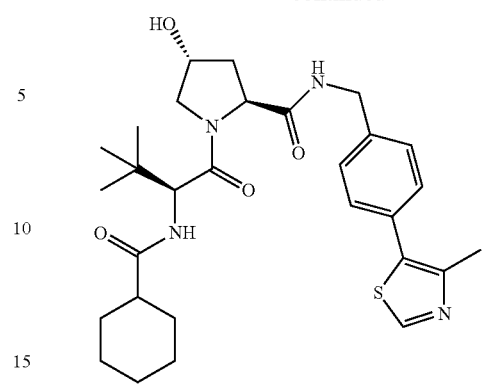
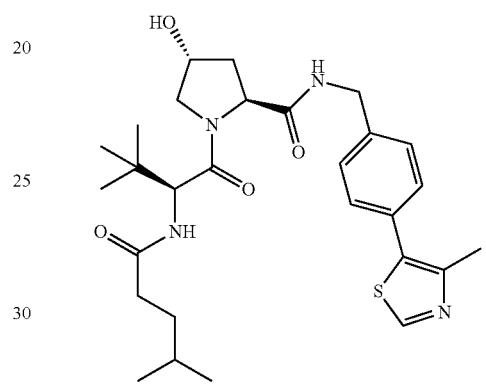
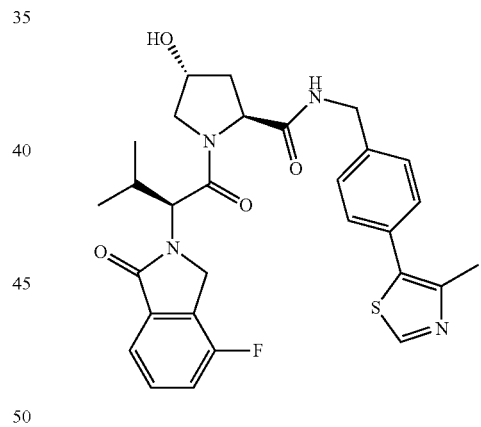
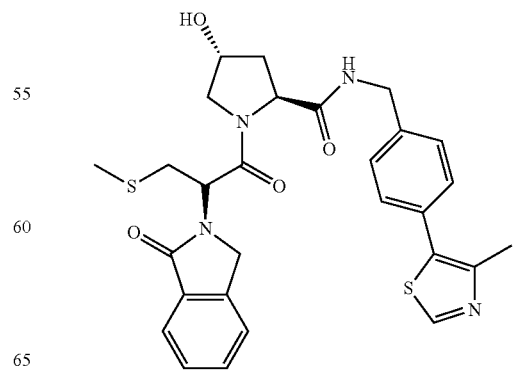

229
-continued
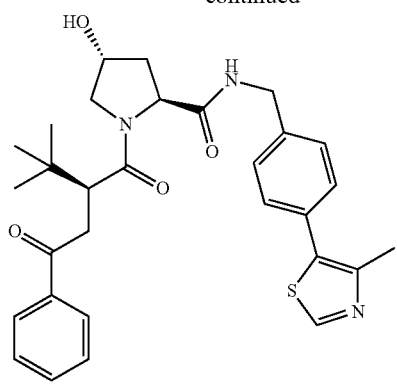
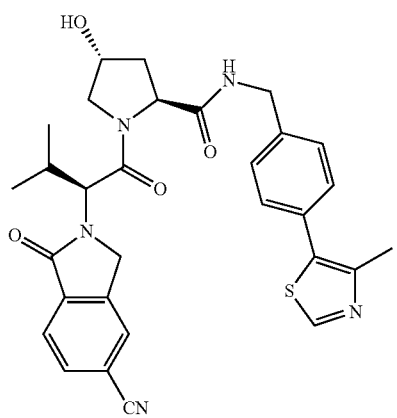
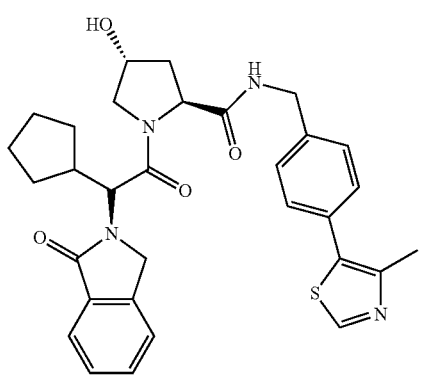
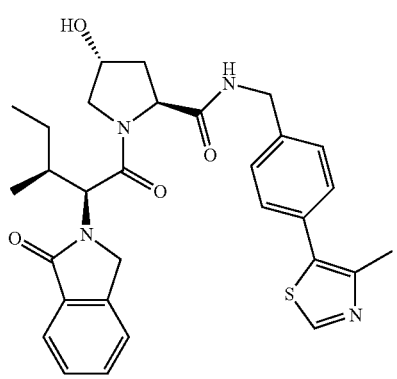
230
-continued
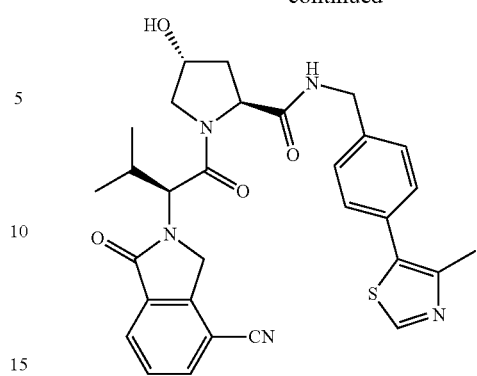
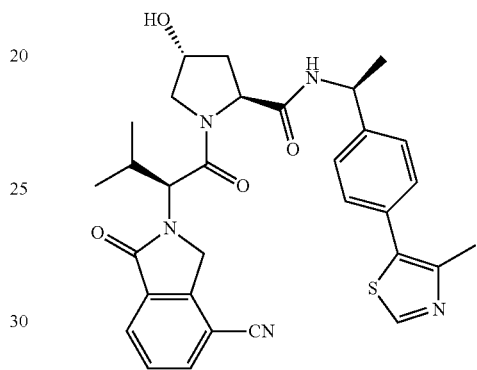
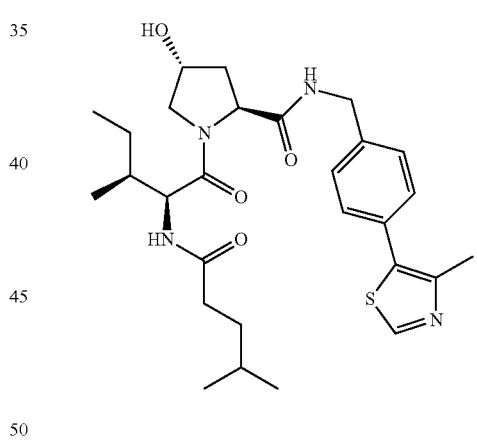
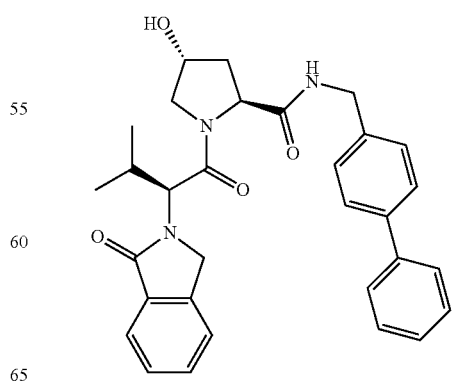

231
-continued
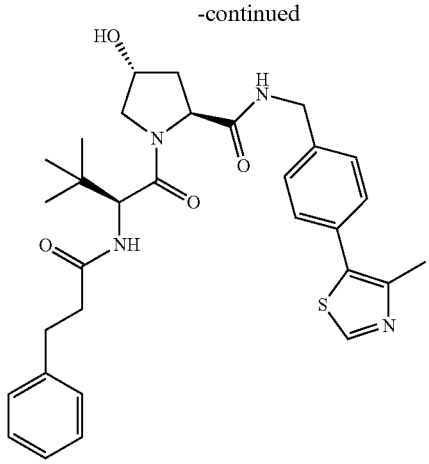
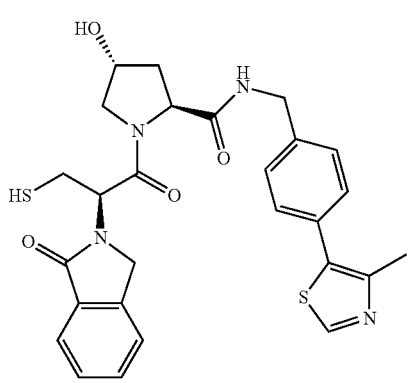
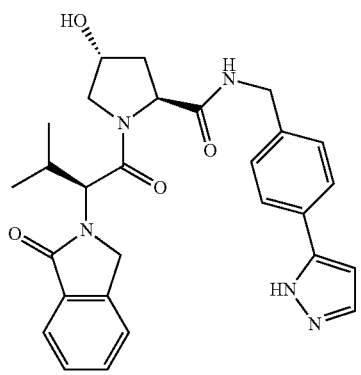
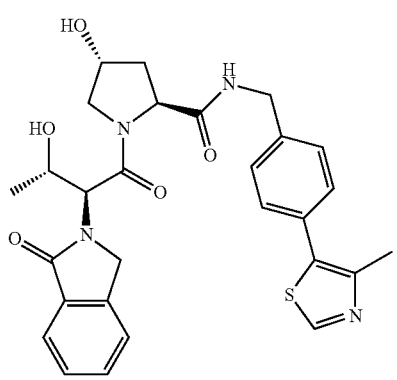
232
-continued
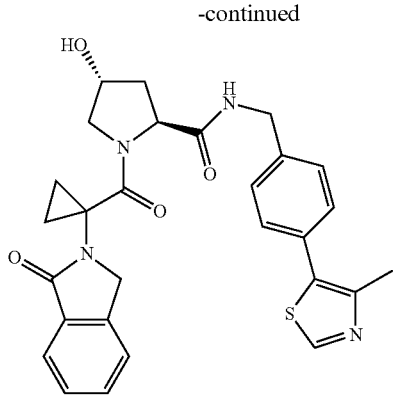
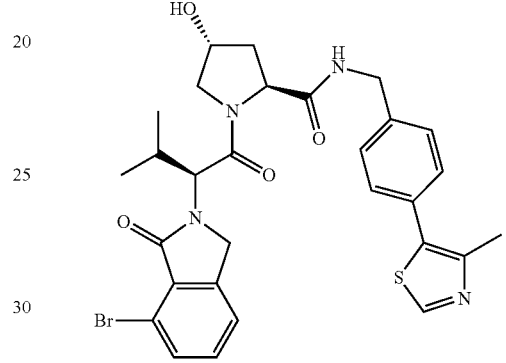
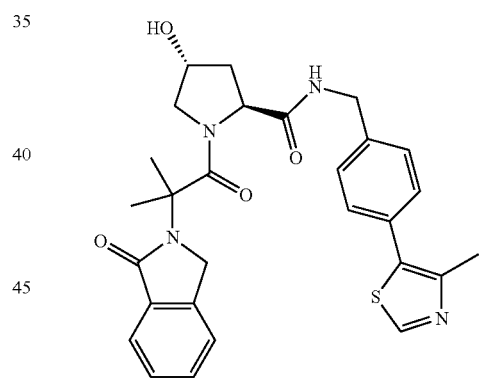
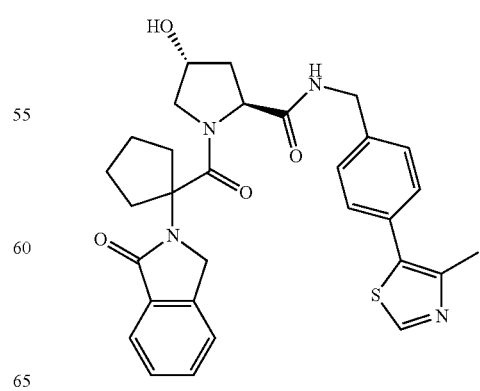

233
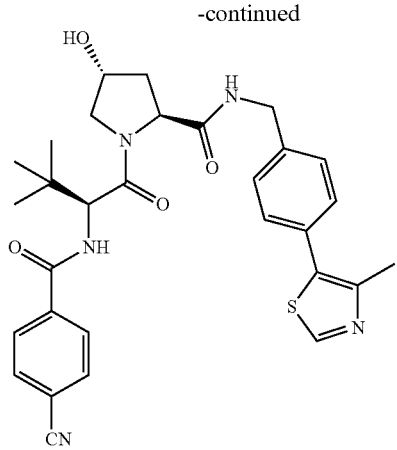
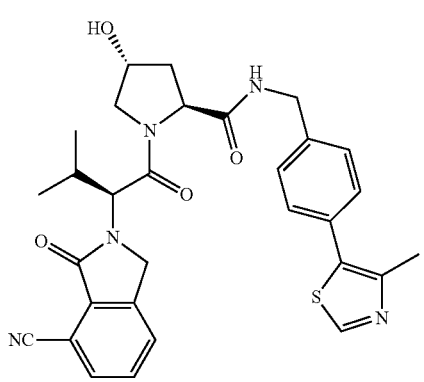
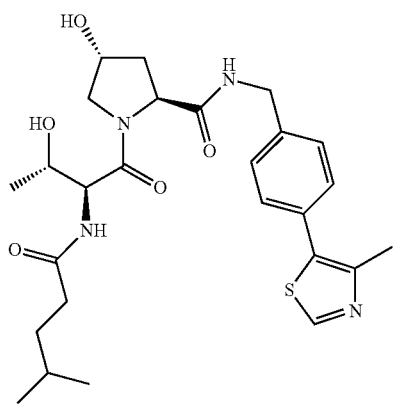
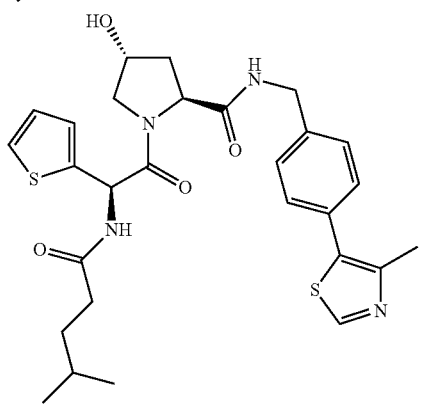
234
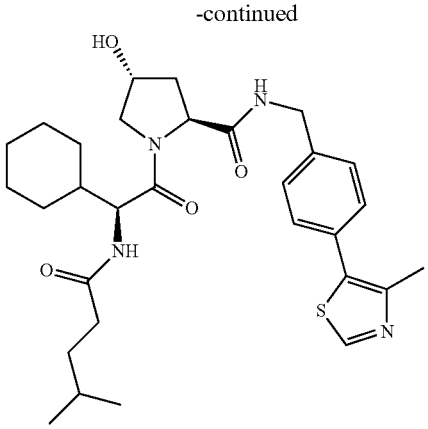
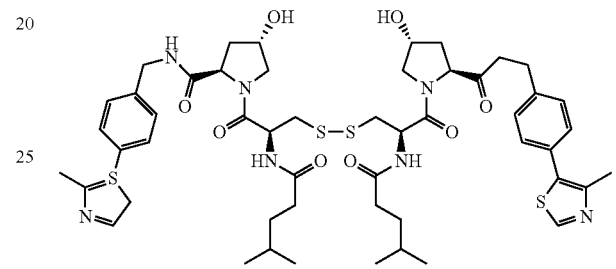
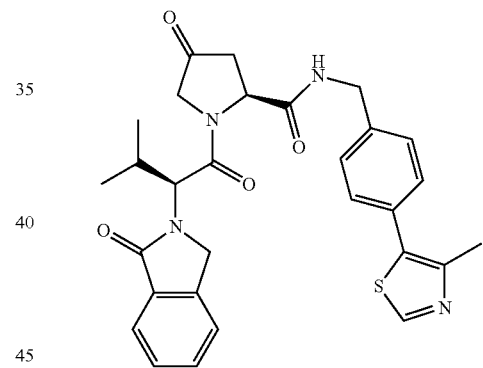
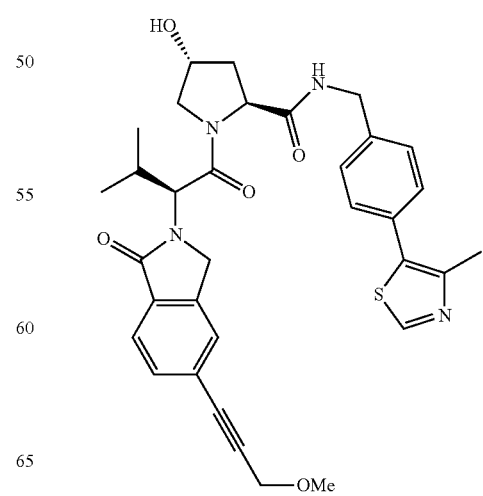

235
-continued
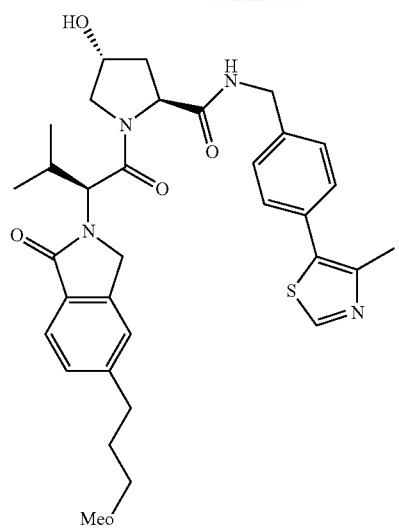
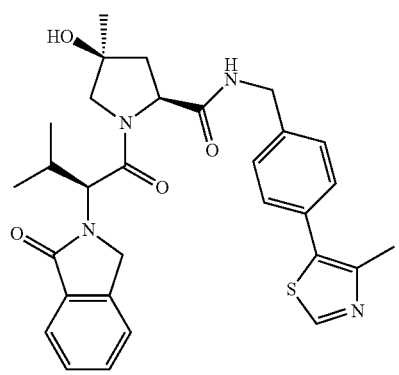
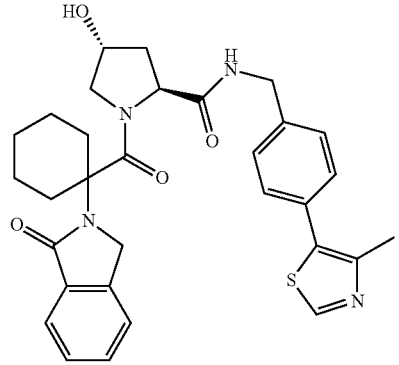
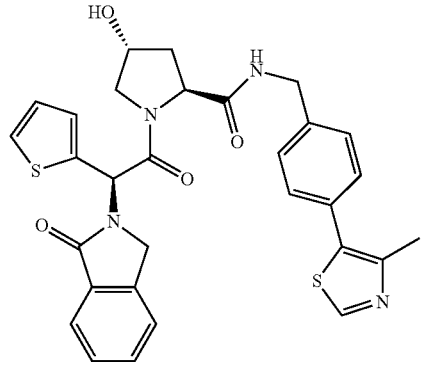
236
-continued
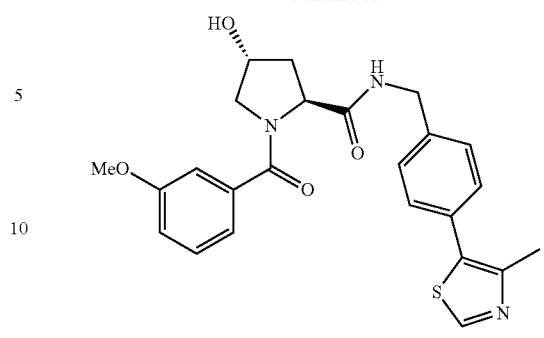
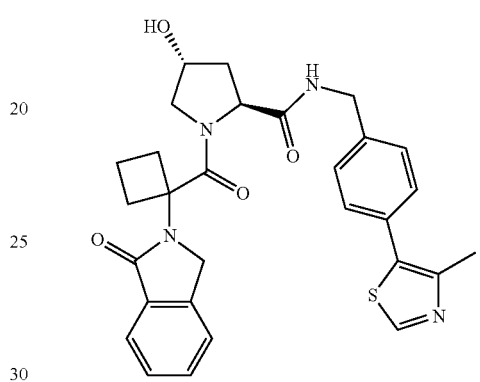
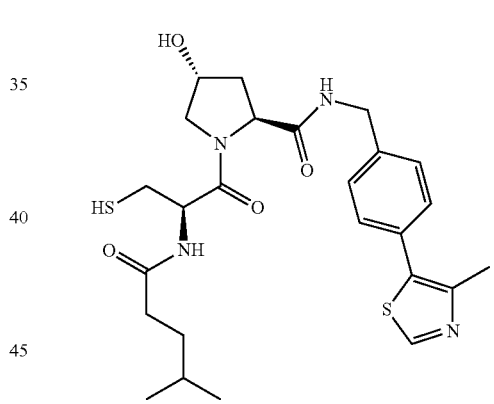
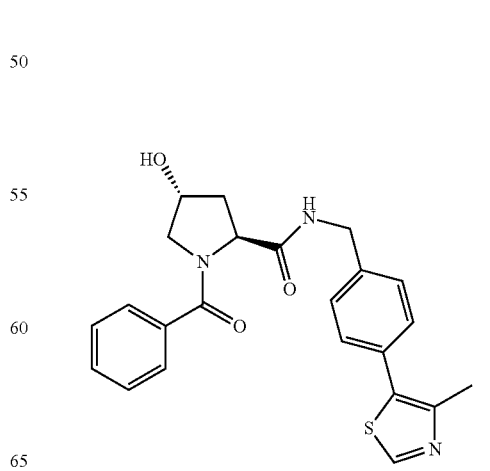

237
-continued
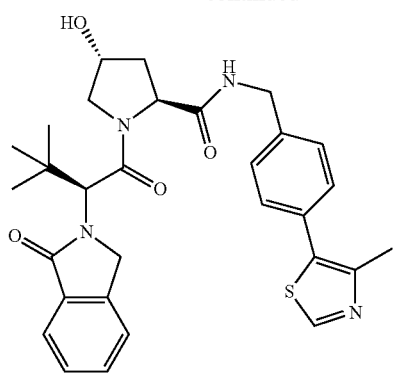
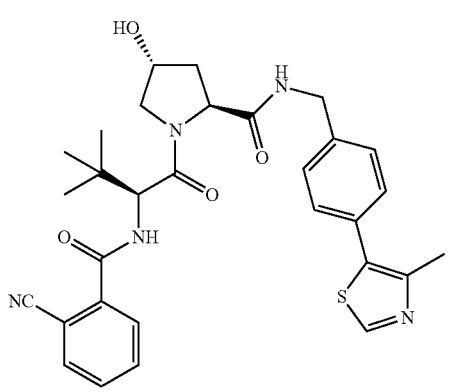
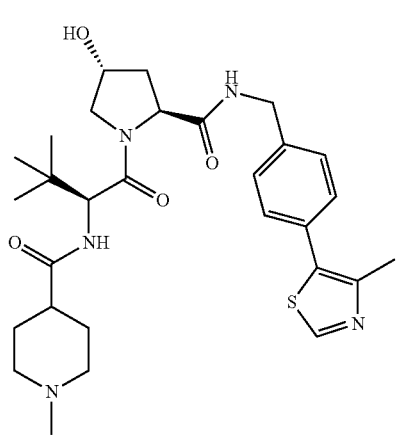
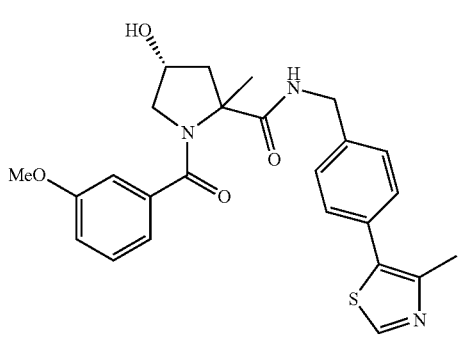
238
-continued
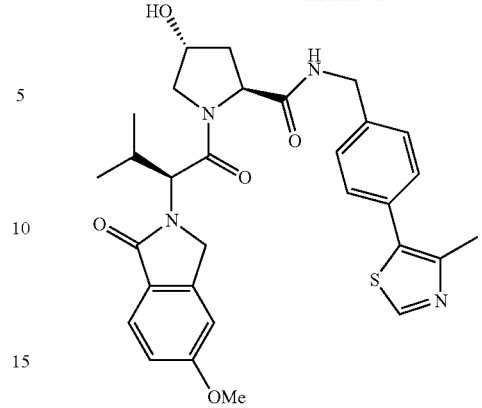
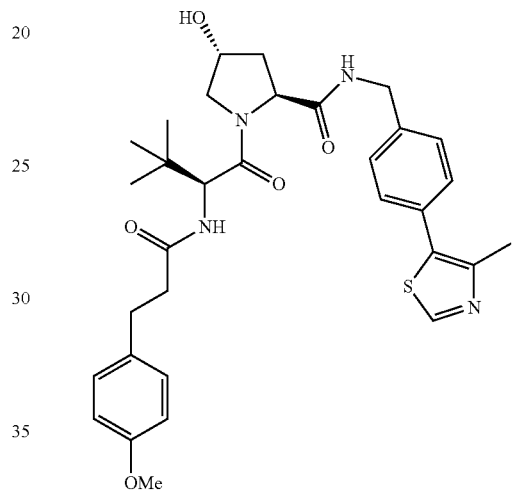
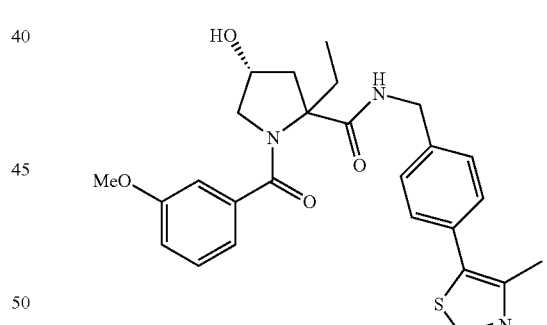
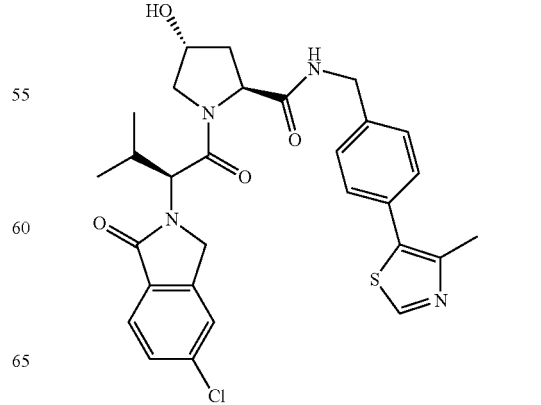

239
-continued
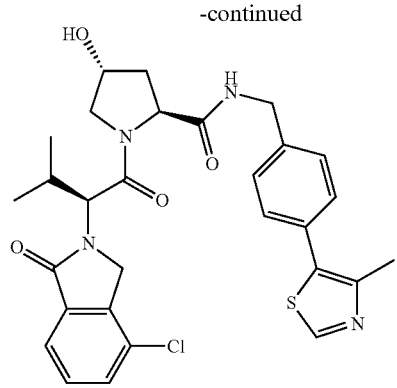
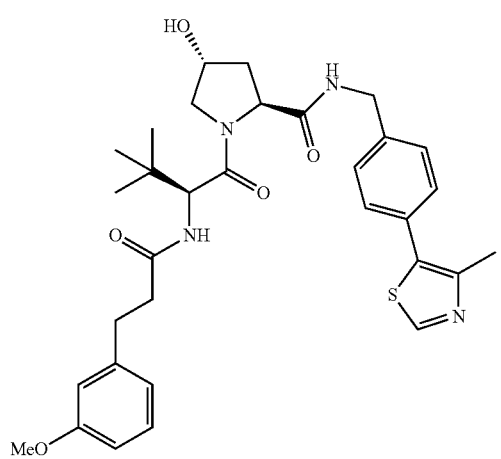
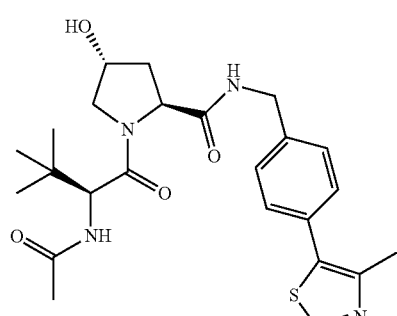
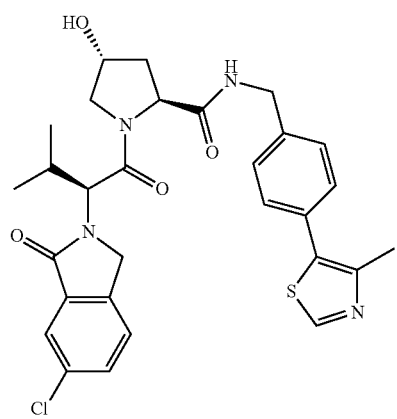
240
-continued
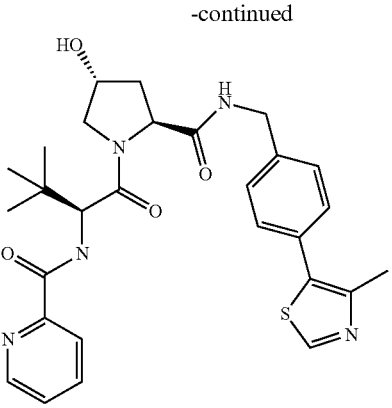
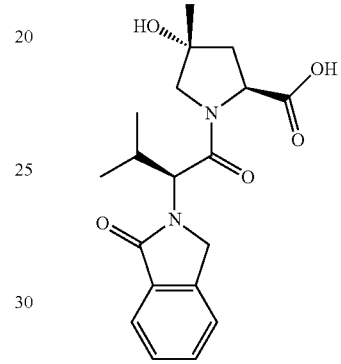
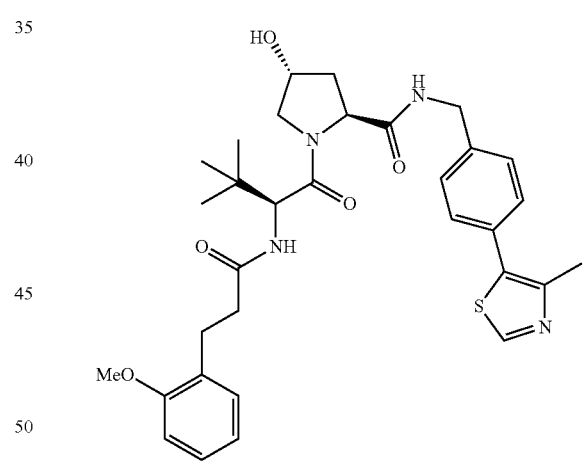
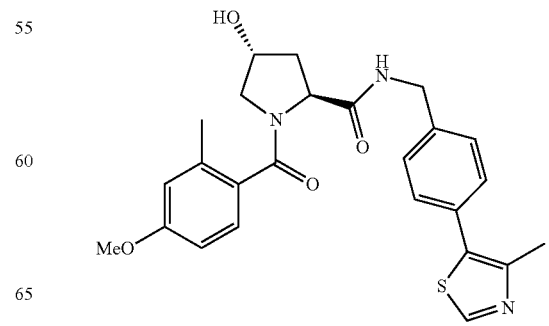

-continued
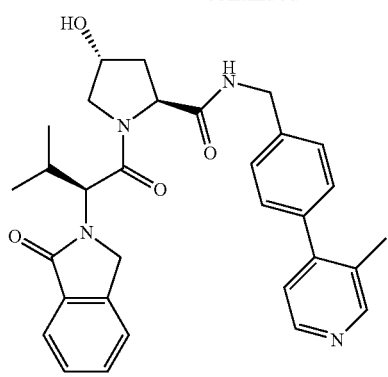
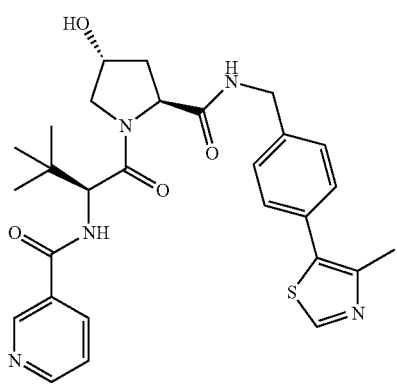
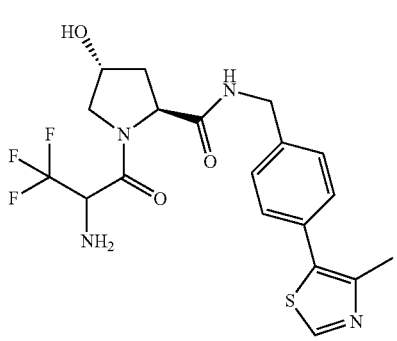
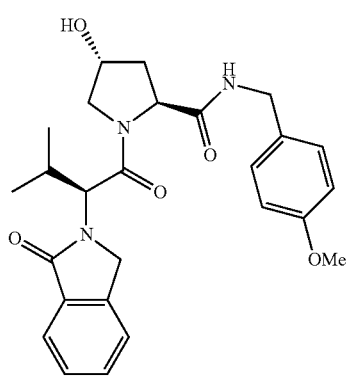
-continued
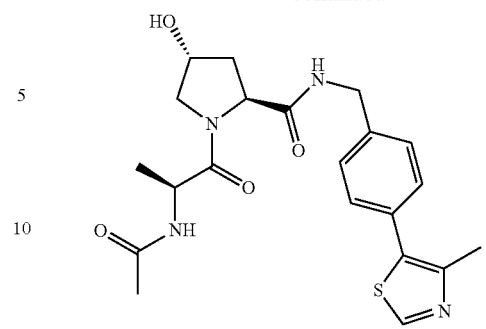
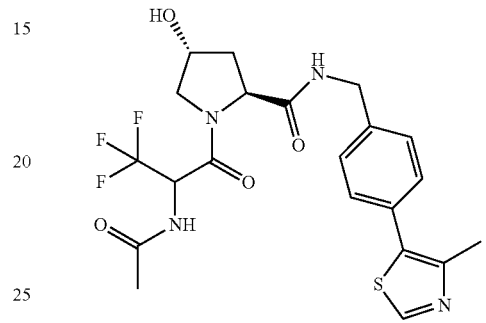
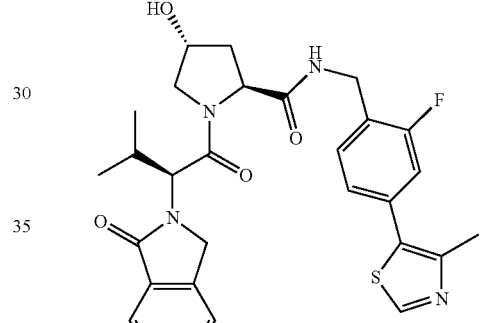
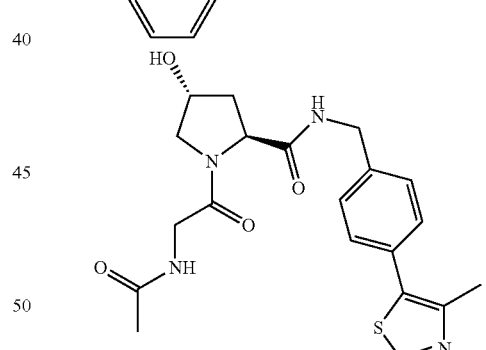
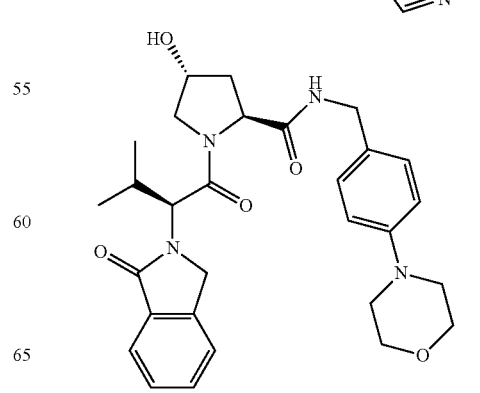

243
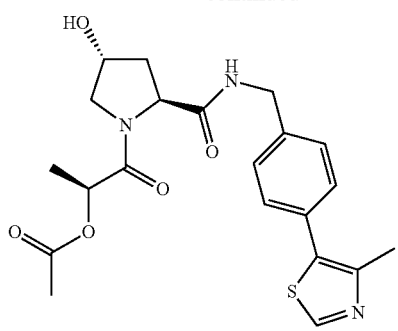
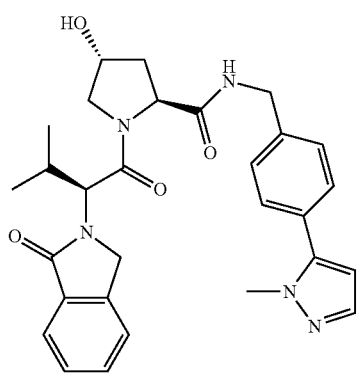
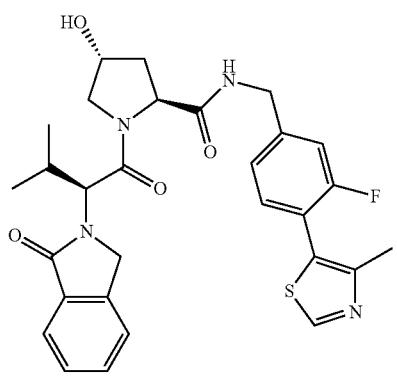
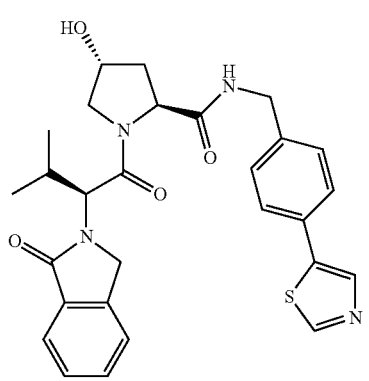
244
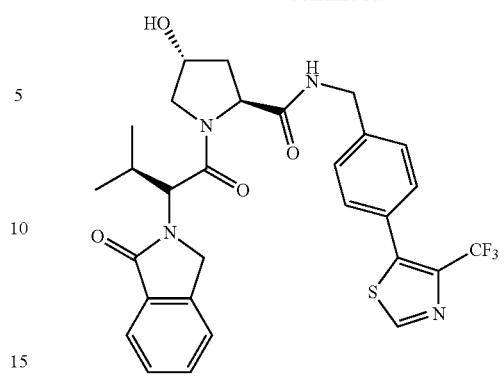
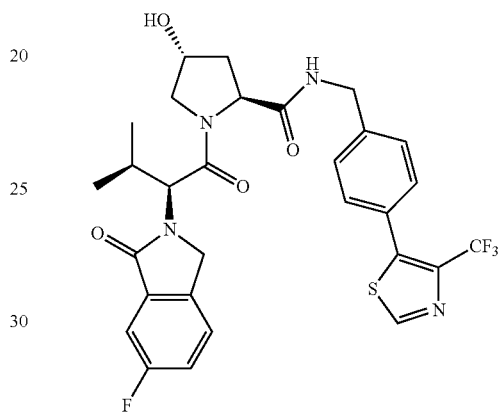
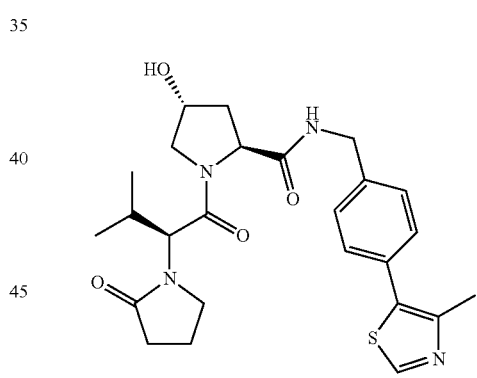
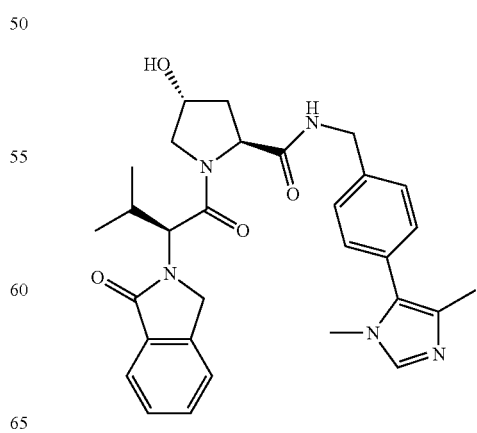

245
-continued
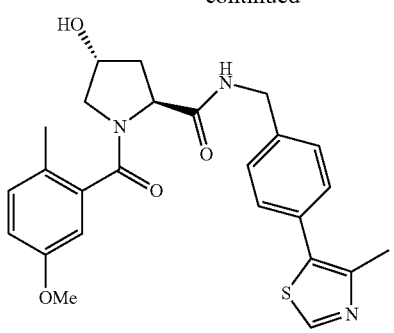
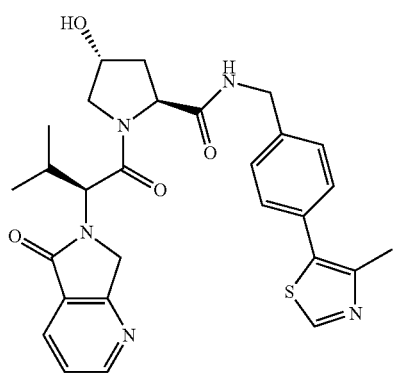
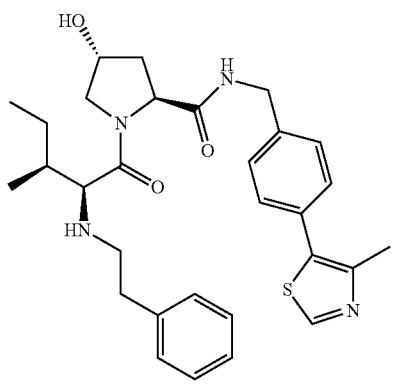
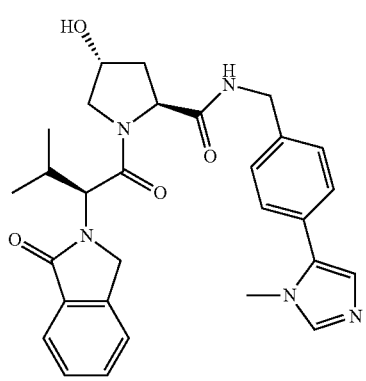
246
-continued
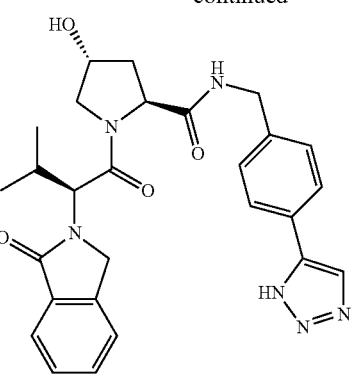
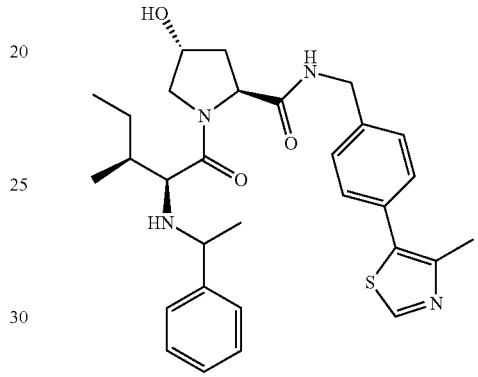
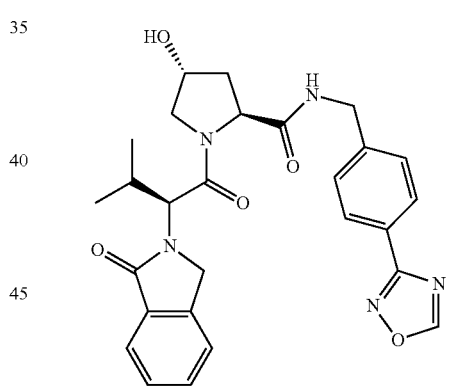

247
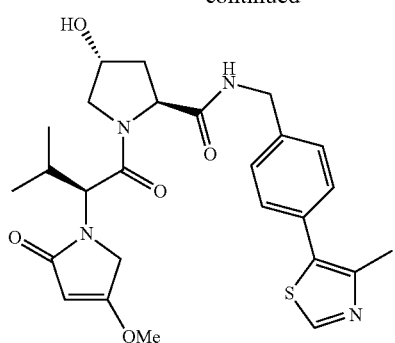
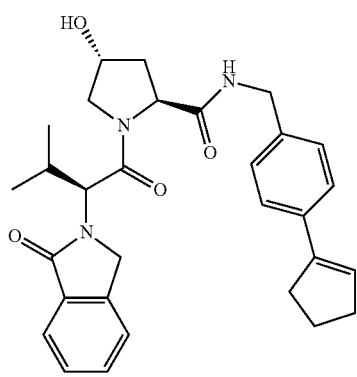
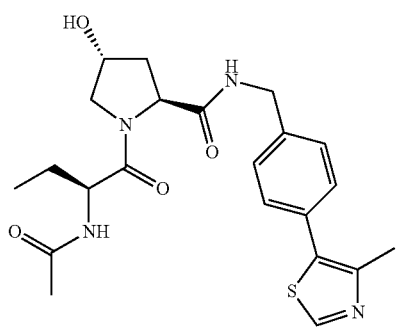
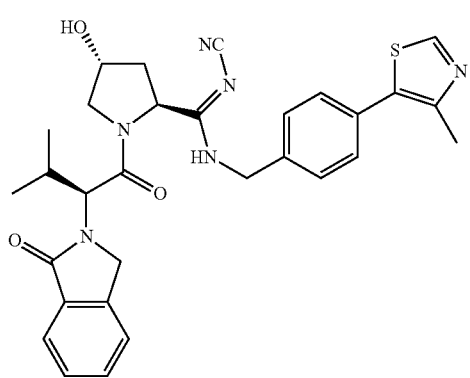
248
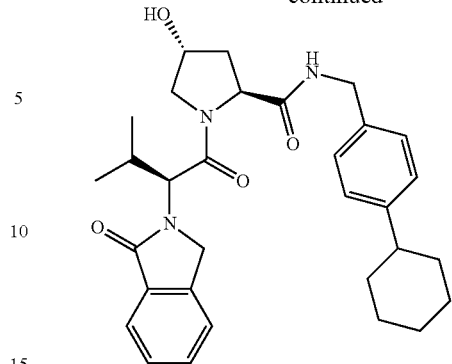
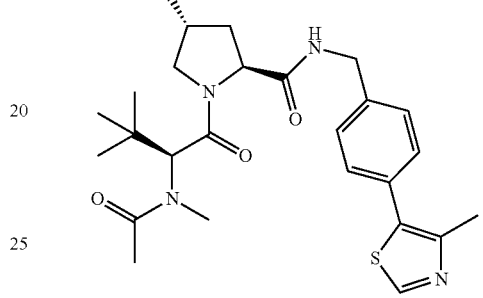
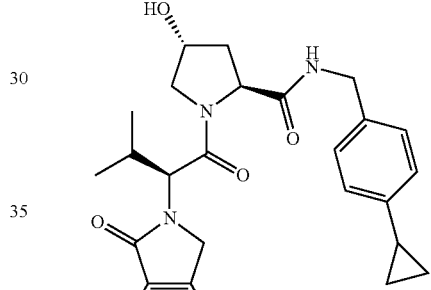
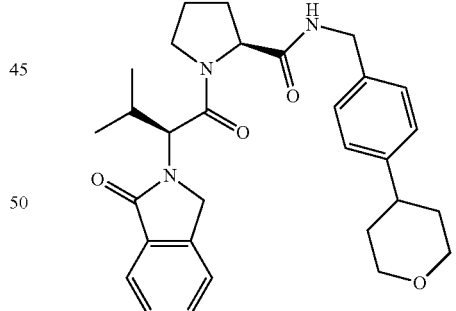
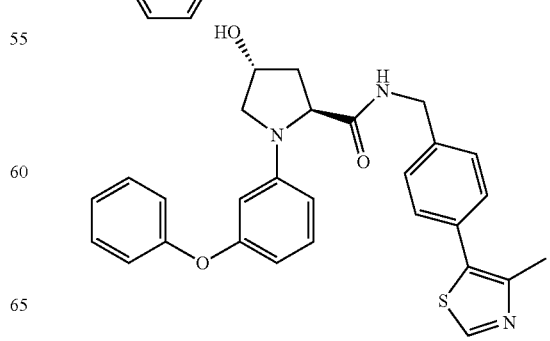

249
-continued
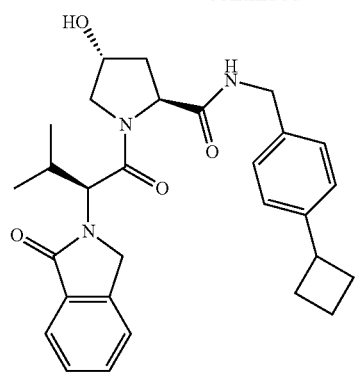
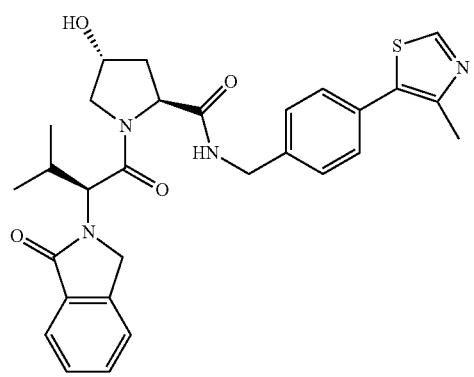
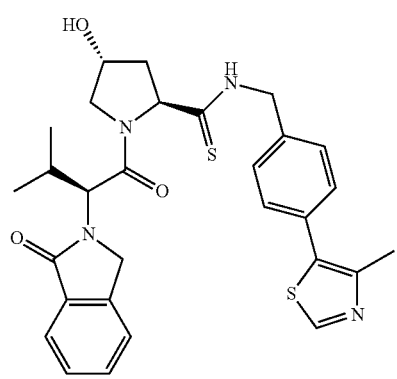
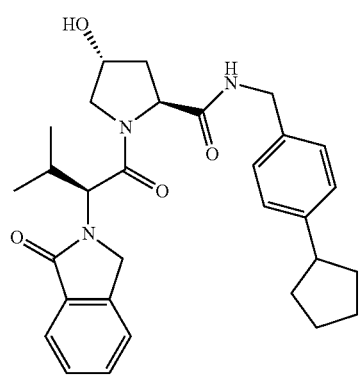
250
-continued
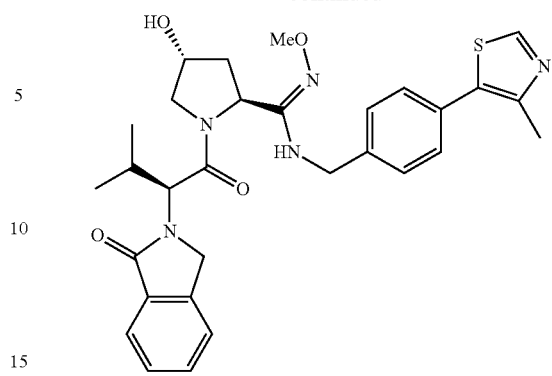
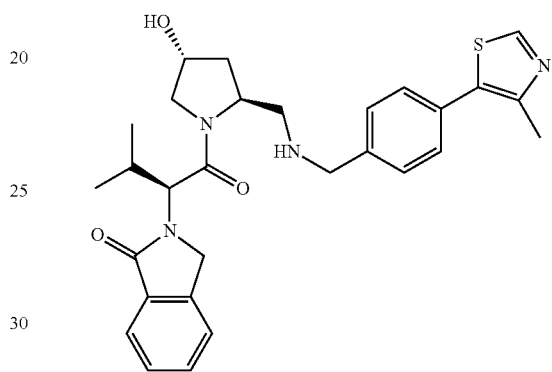
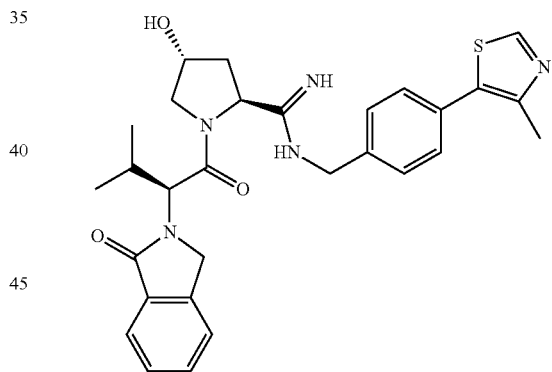
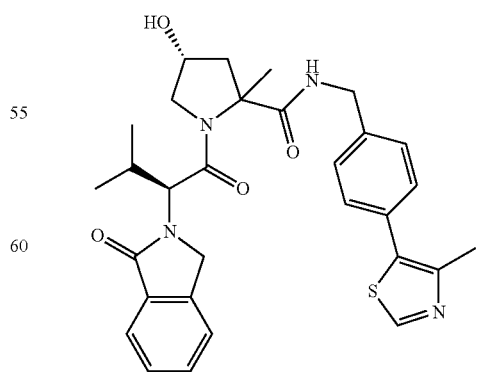

251
-continued
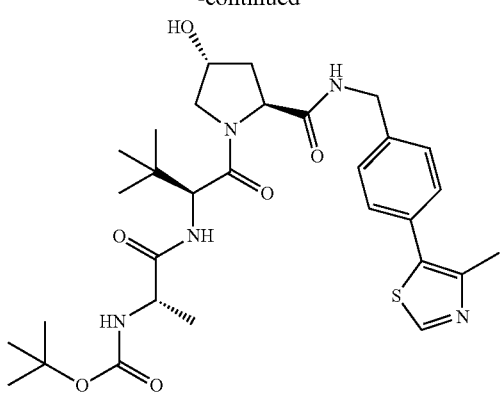
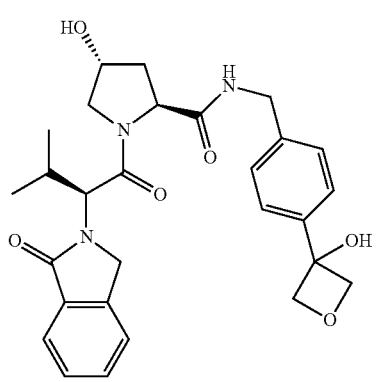
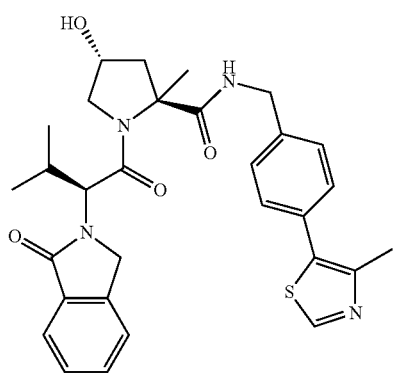
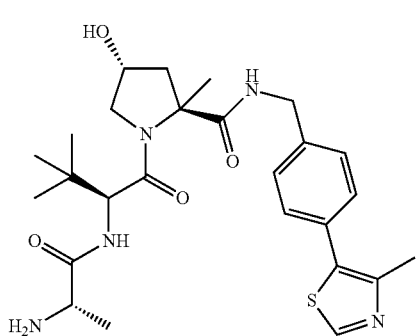
252
-continued
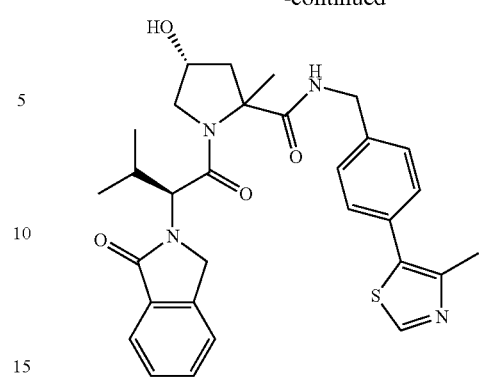
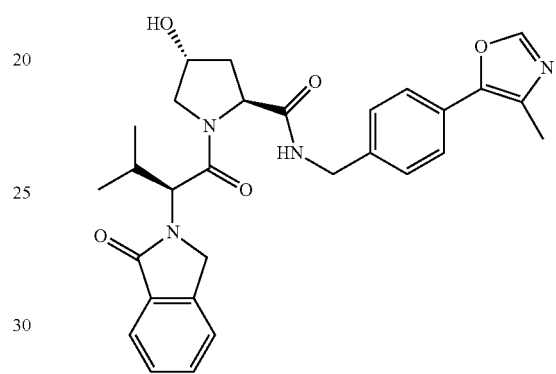
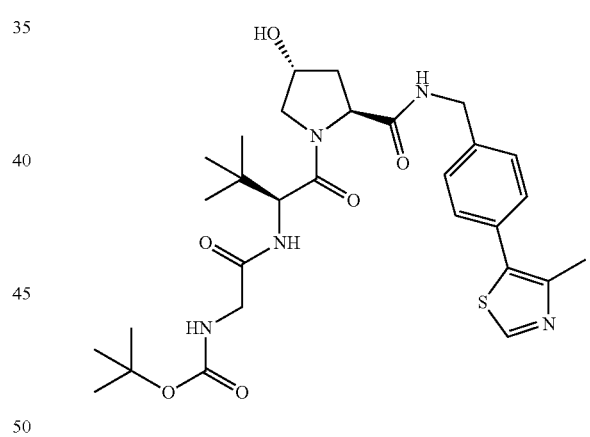
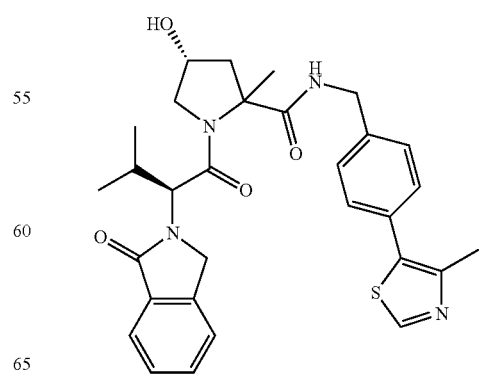

253
-continued
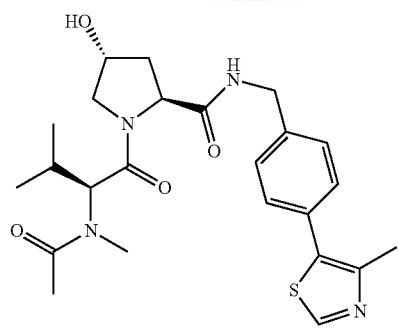
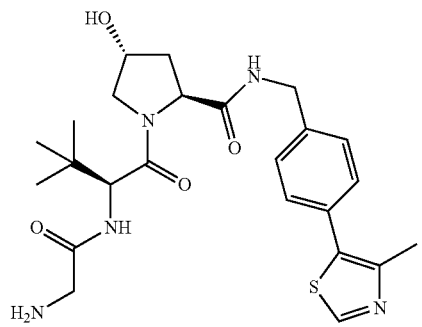
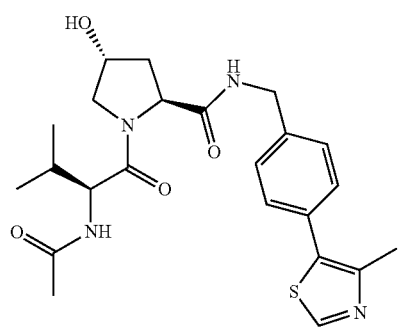
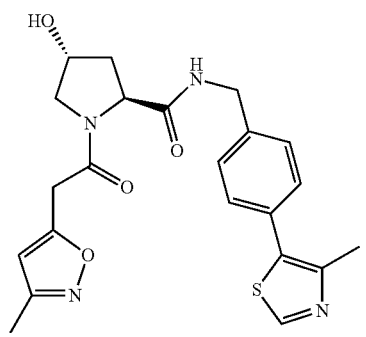
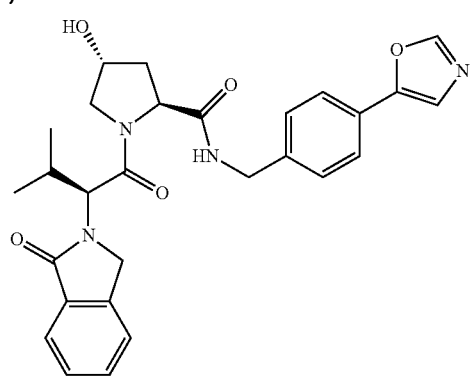
254
-continued
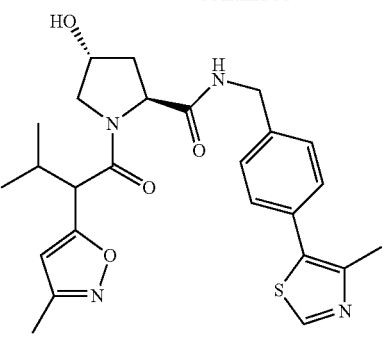
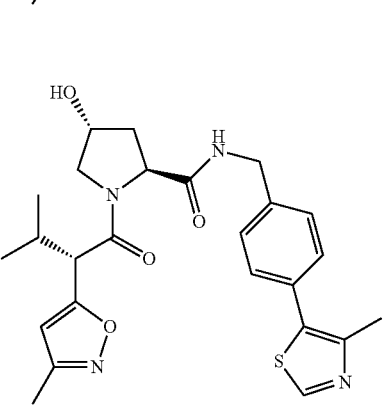
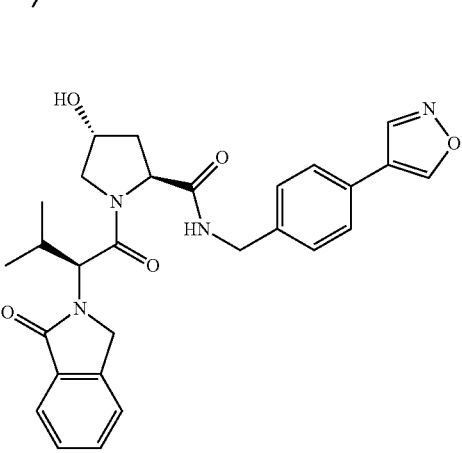
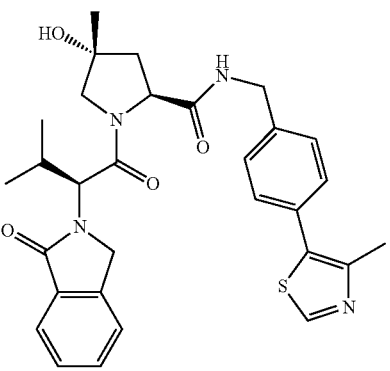

255
-continued
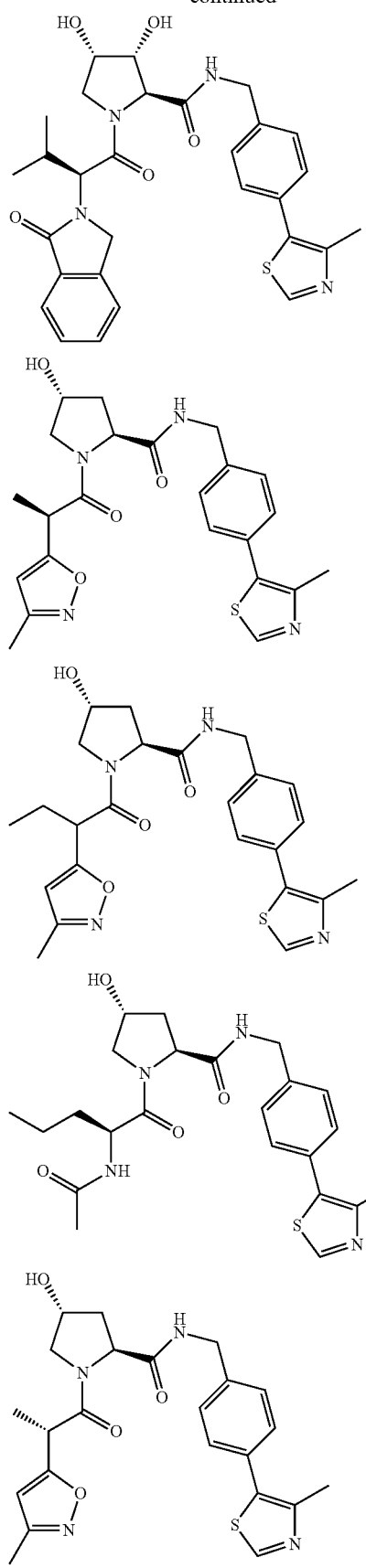
256
-continued
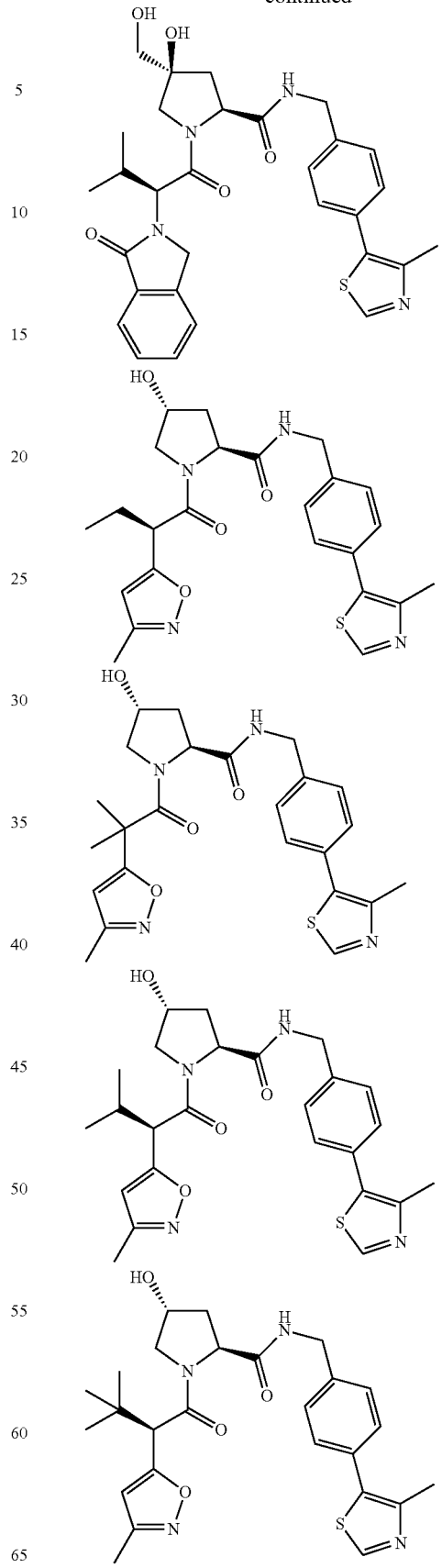

257
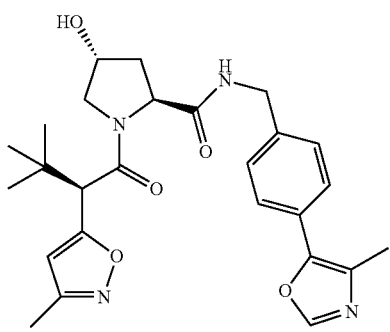
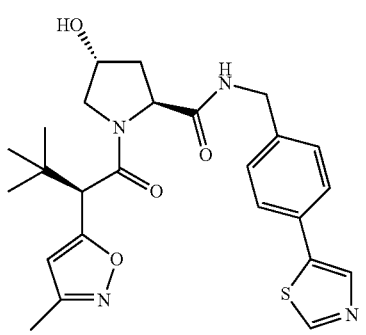
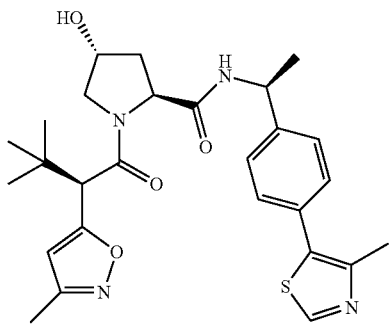
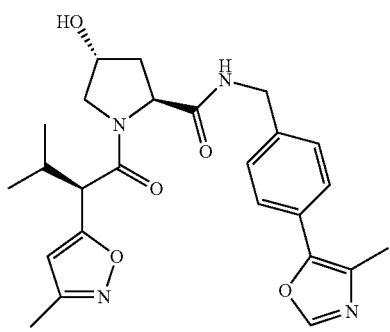
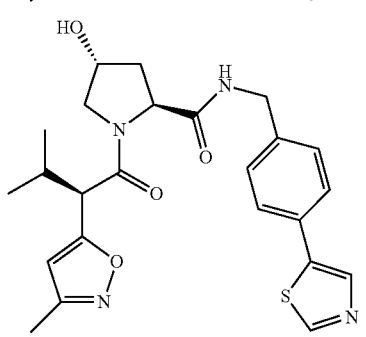
258
-continued
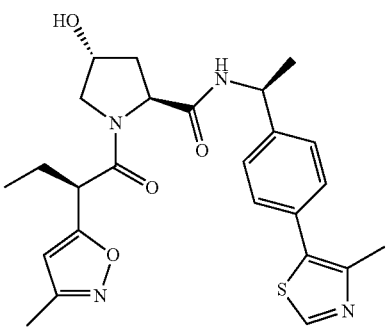
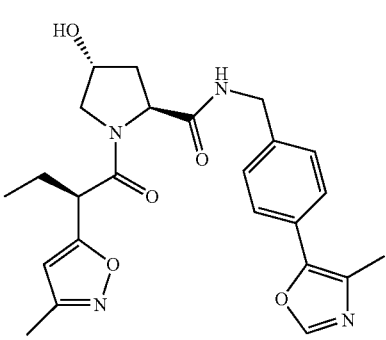
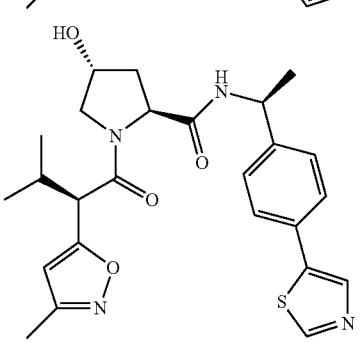
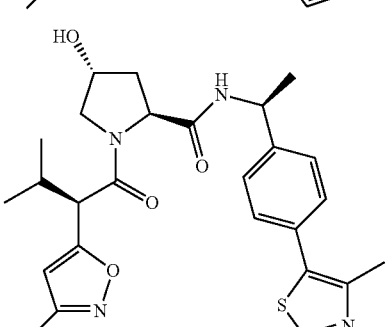
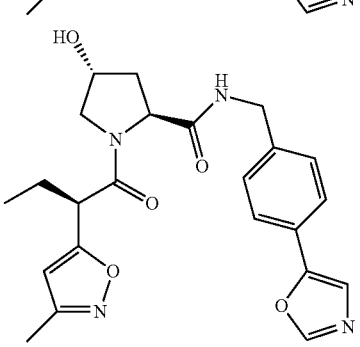

259
-continued
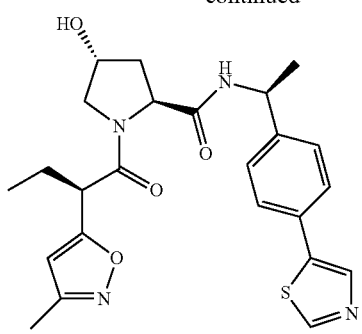
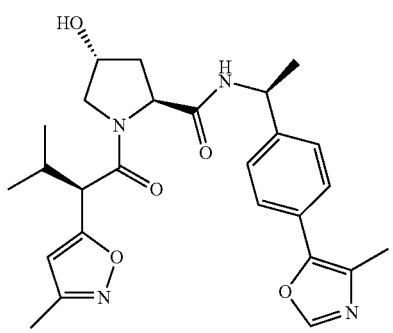
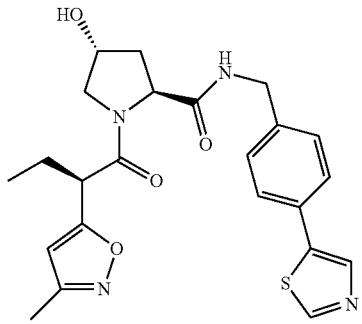
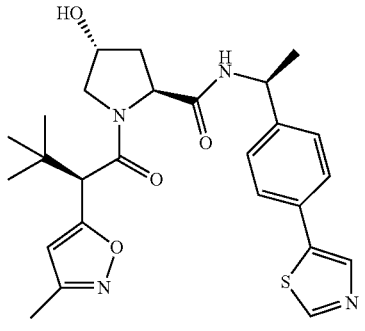
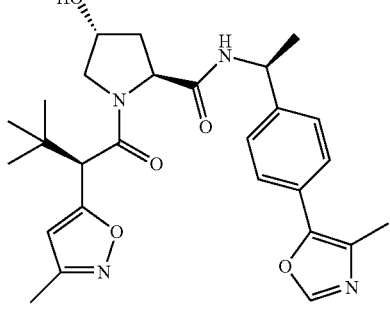
260
-continued
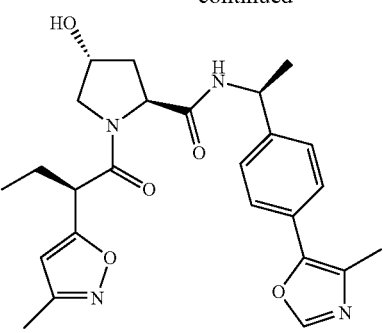
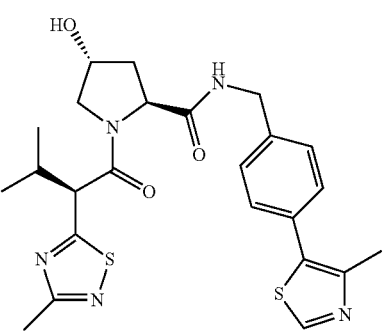
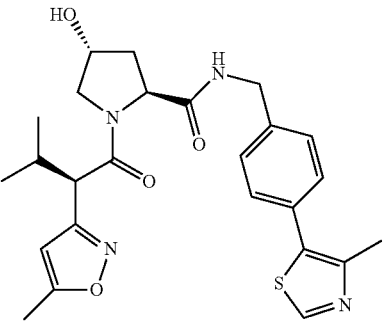
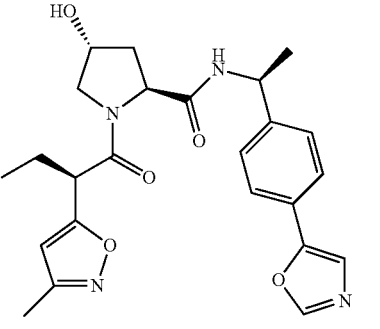
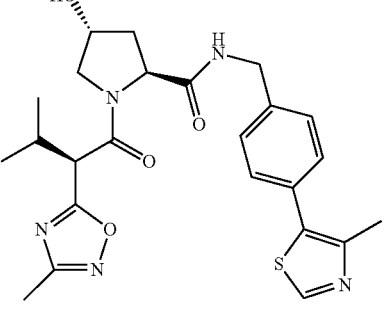

261
-continued
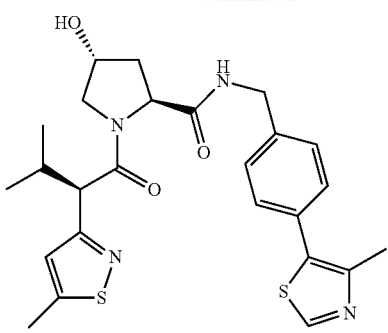
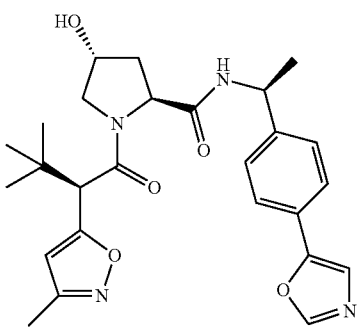
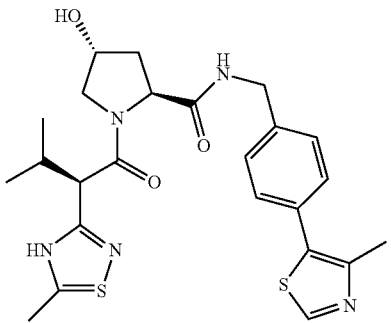
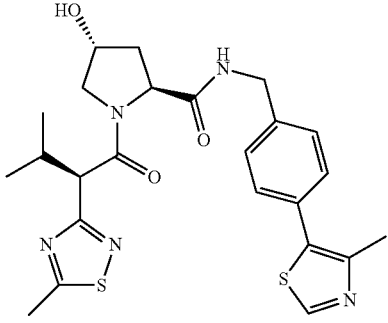
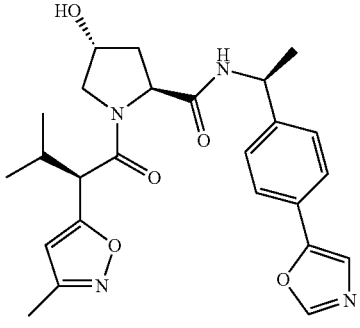
262
-continued
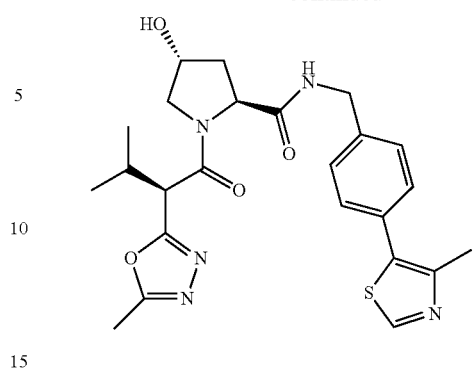
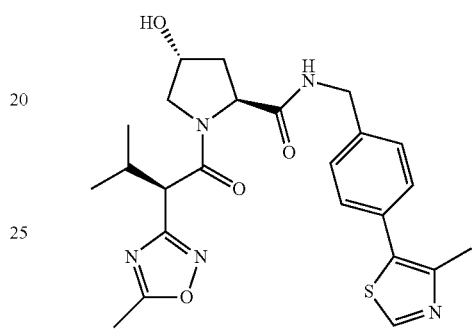

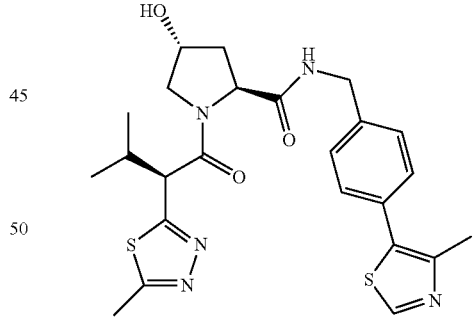
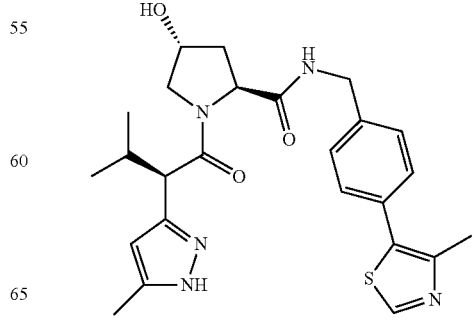

263
-continued
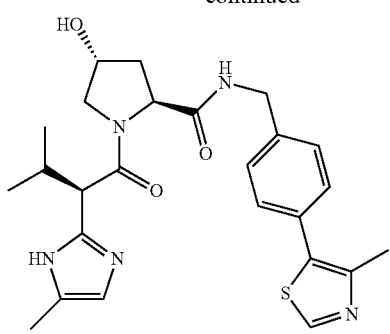
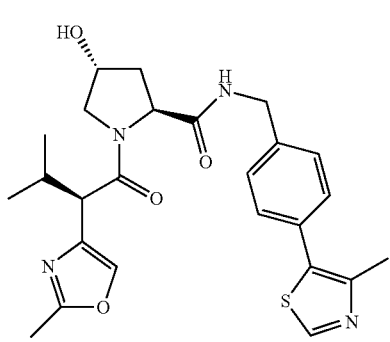
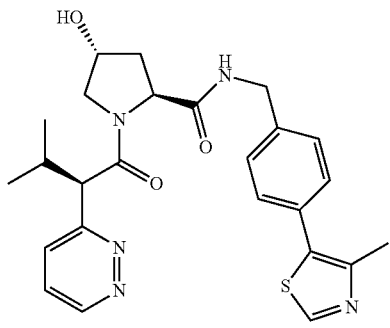
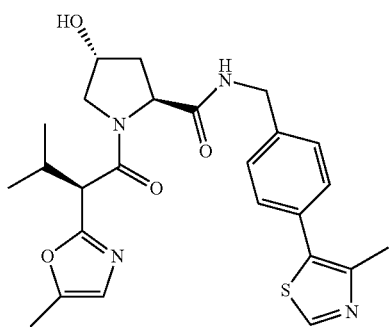
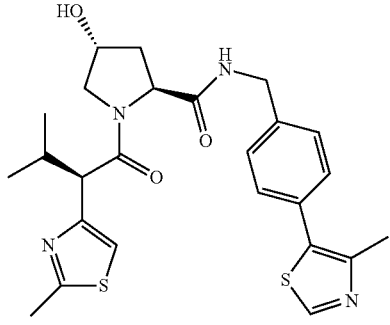
264
-continued
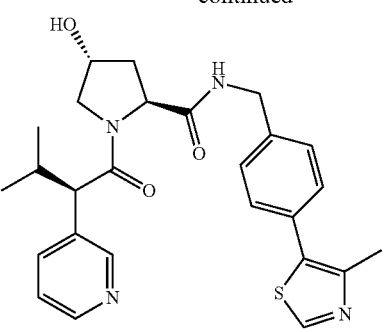
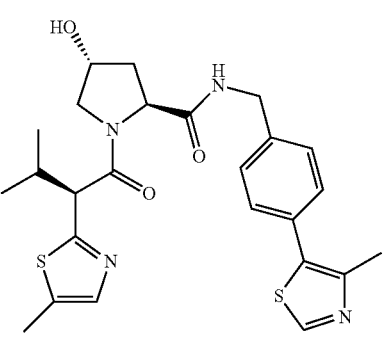
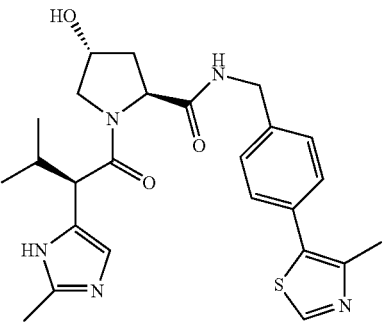
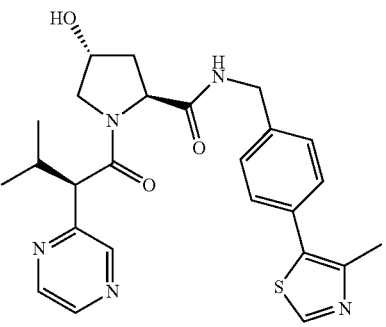
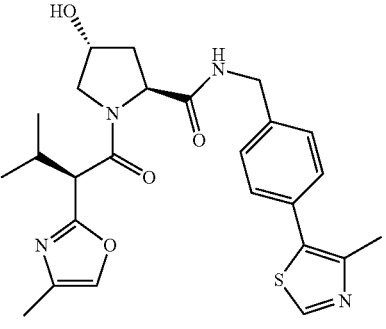

265
-continued
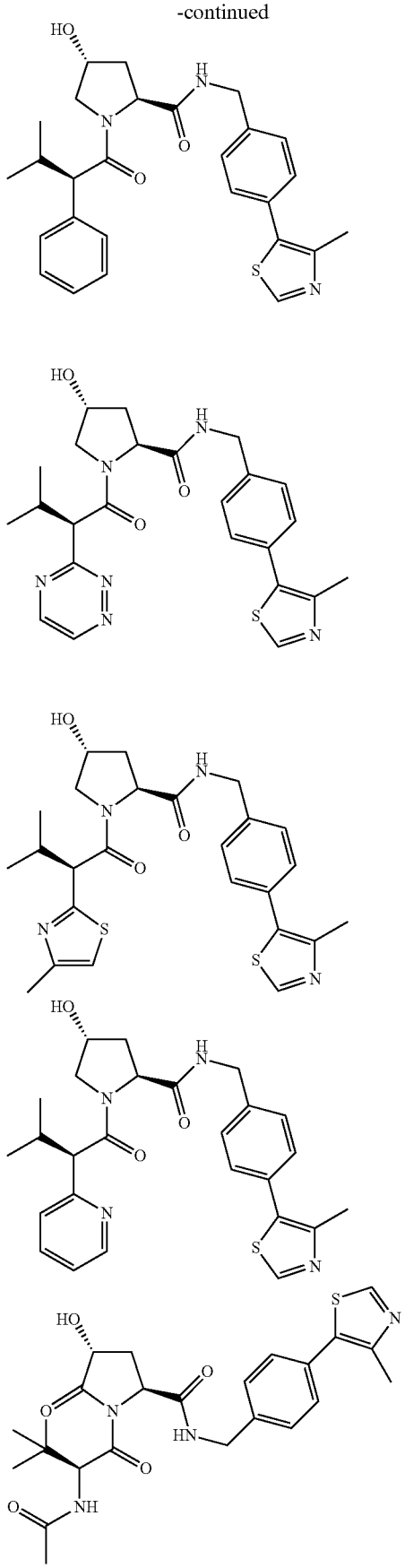
266
-continued
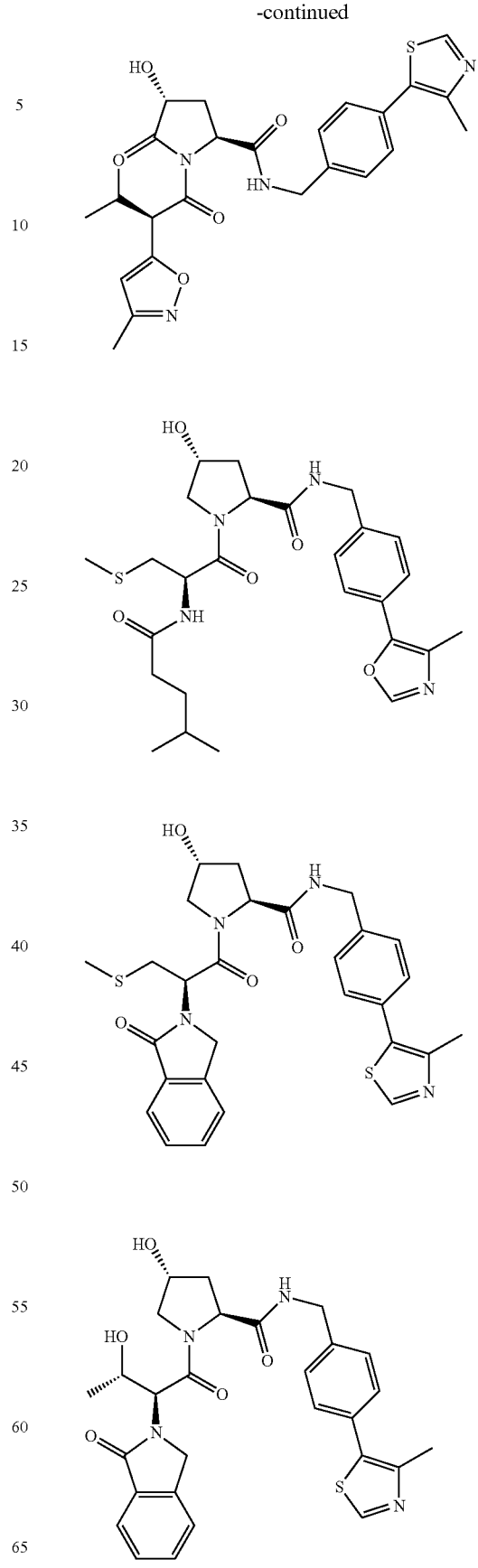

267
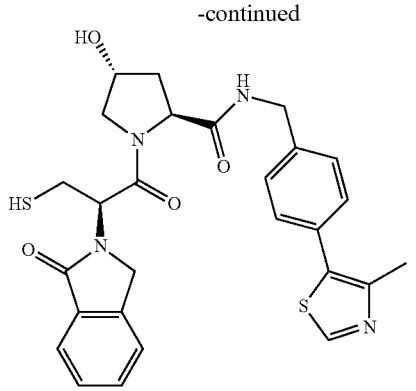
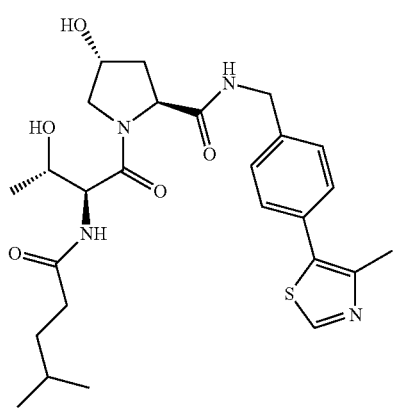
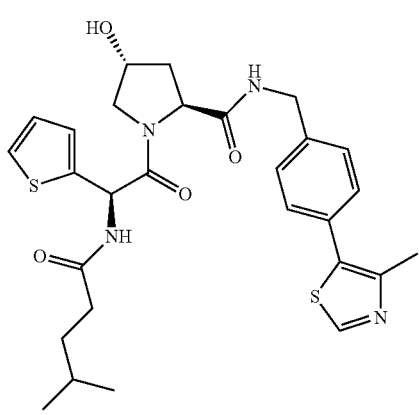
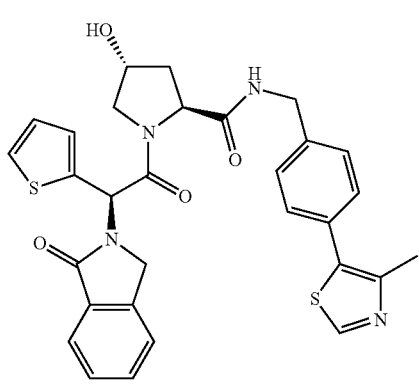
268
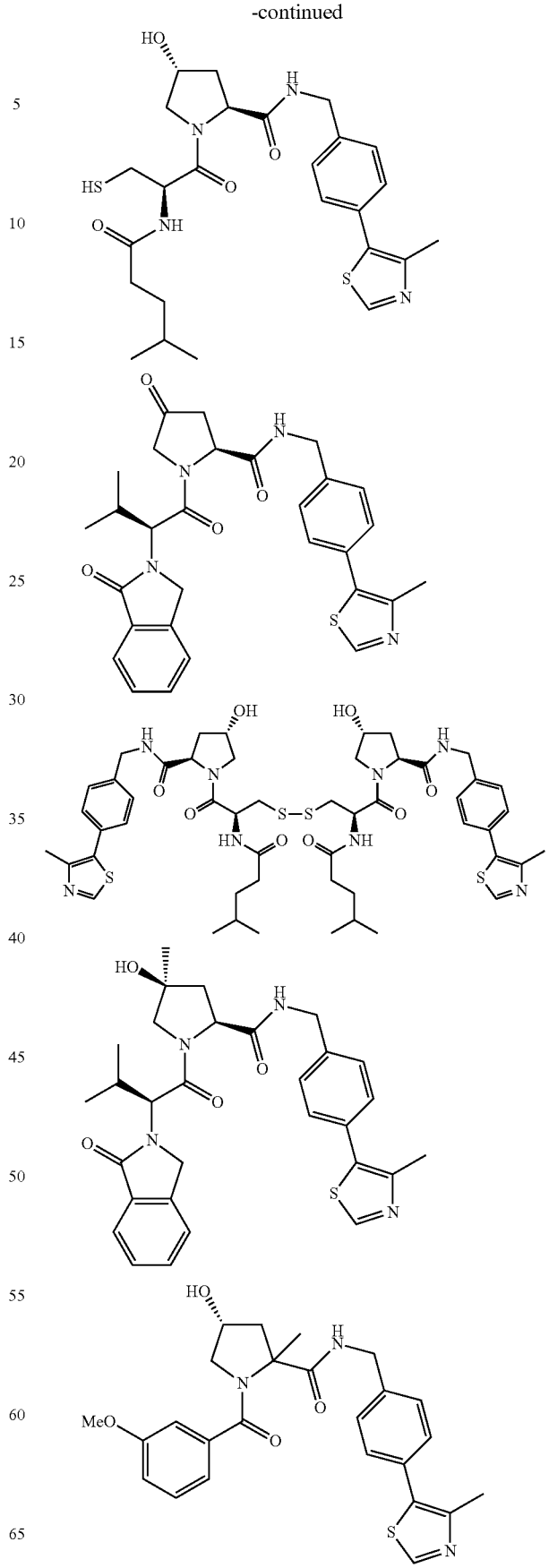

269
-continued
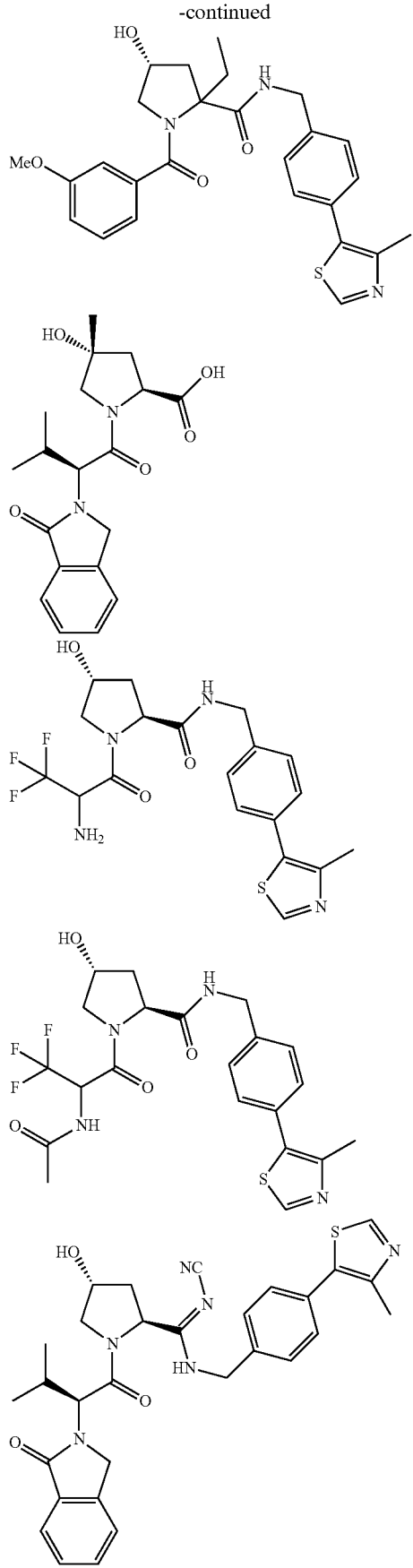
270
-continued
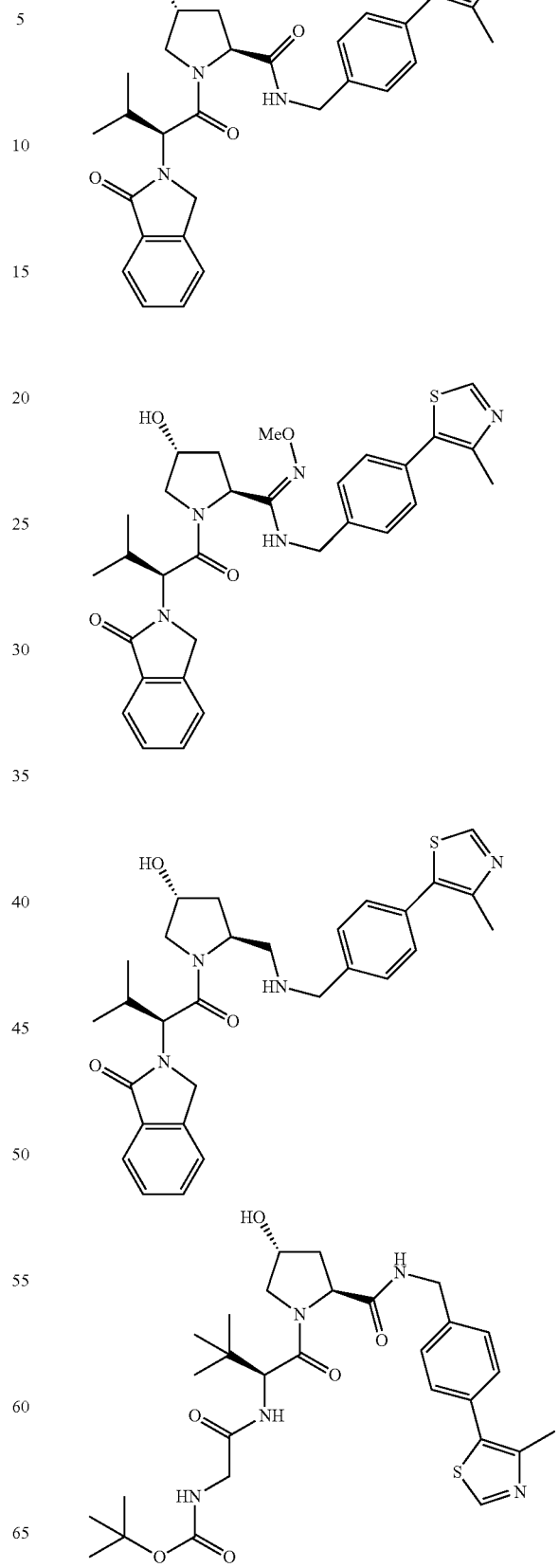

271
-continued
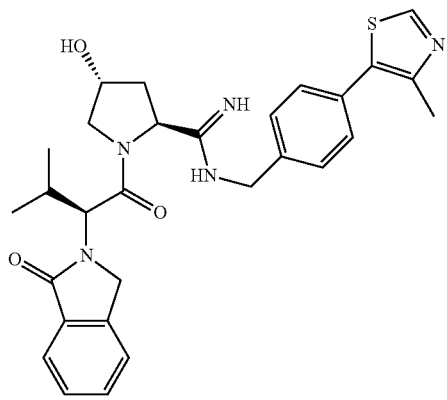
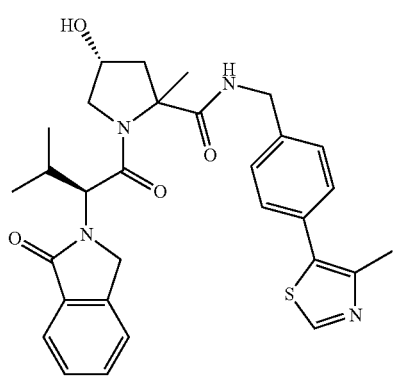
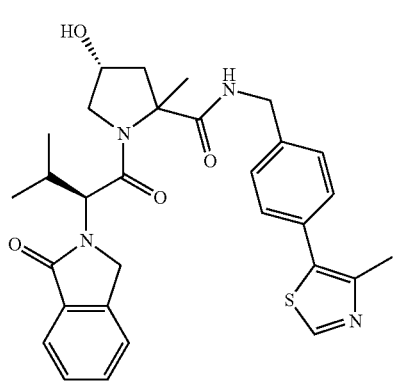
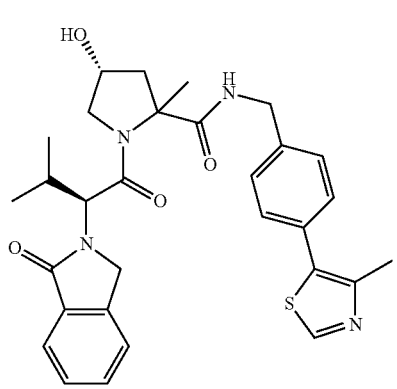
272
-continued
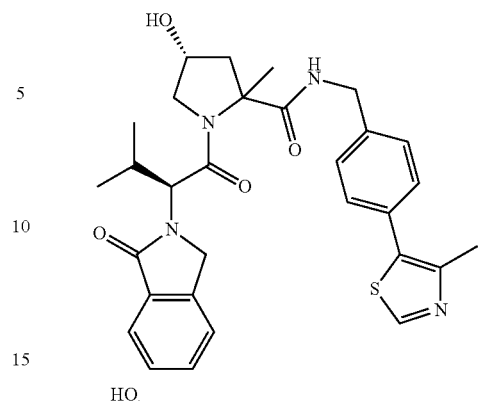
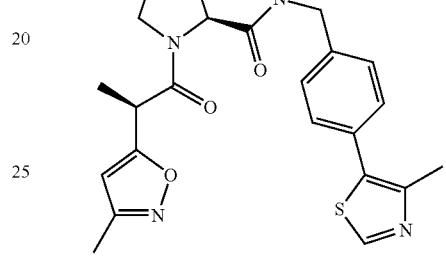
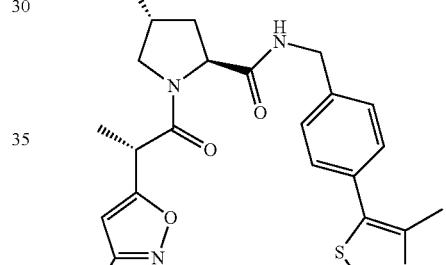
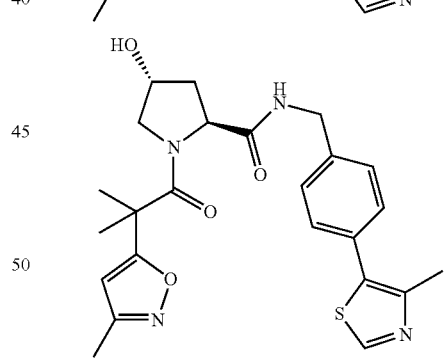
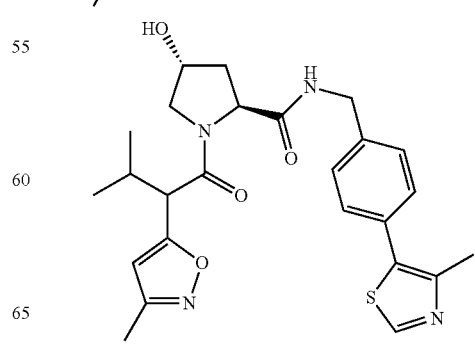

273
-continued
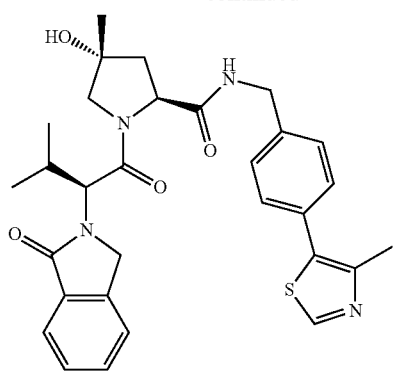
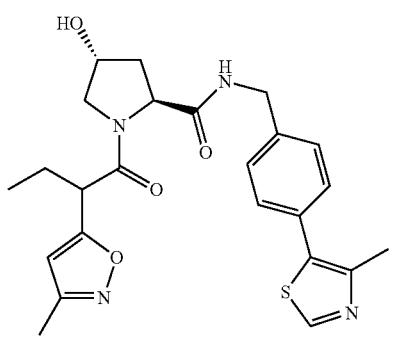
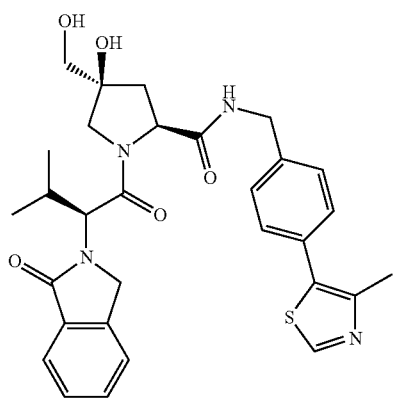
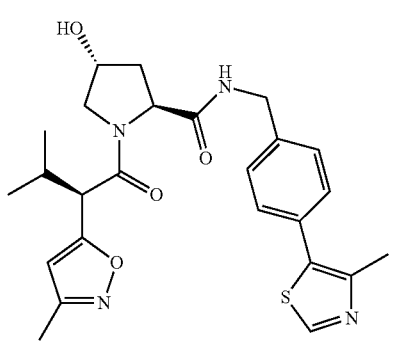
274
-continued
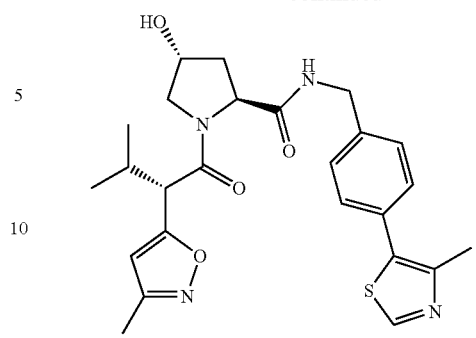
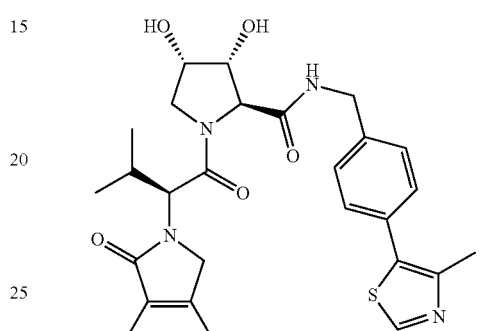
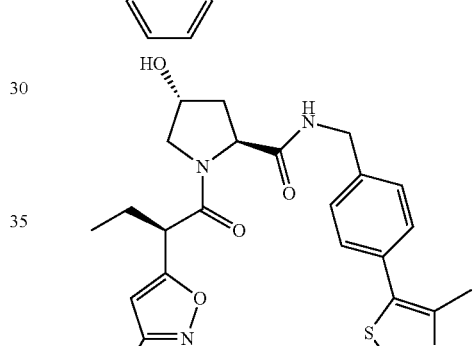
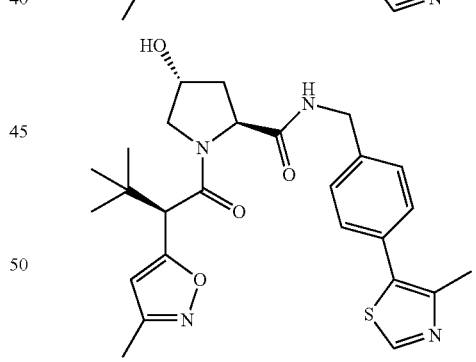
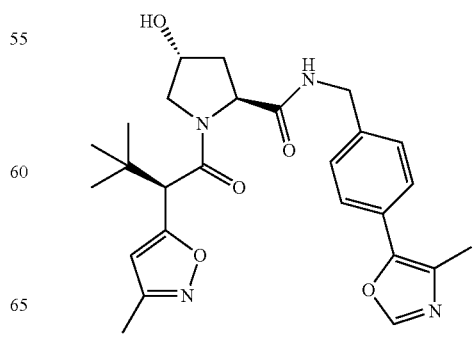

275
-continued
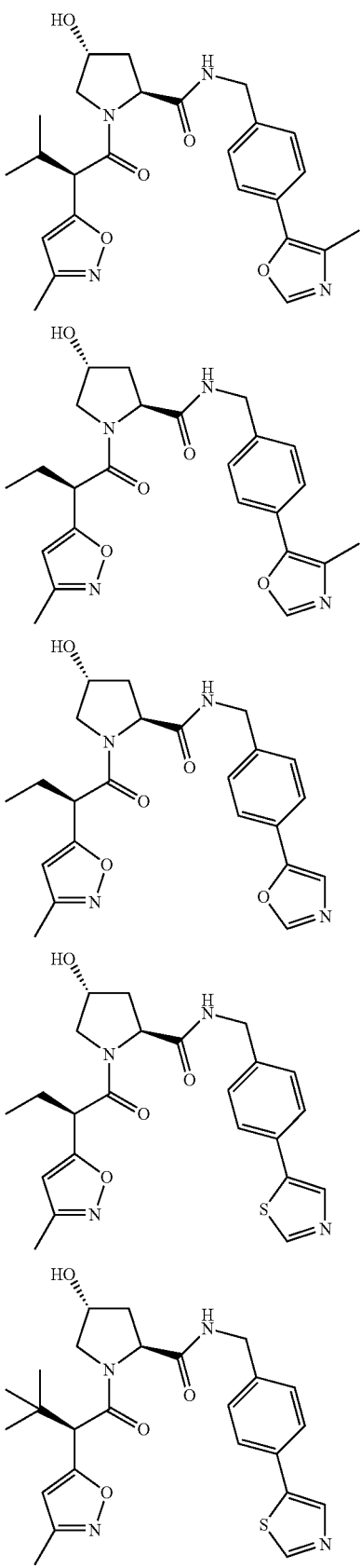
276
-continued
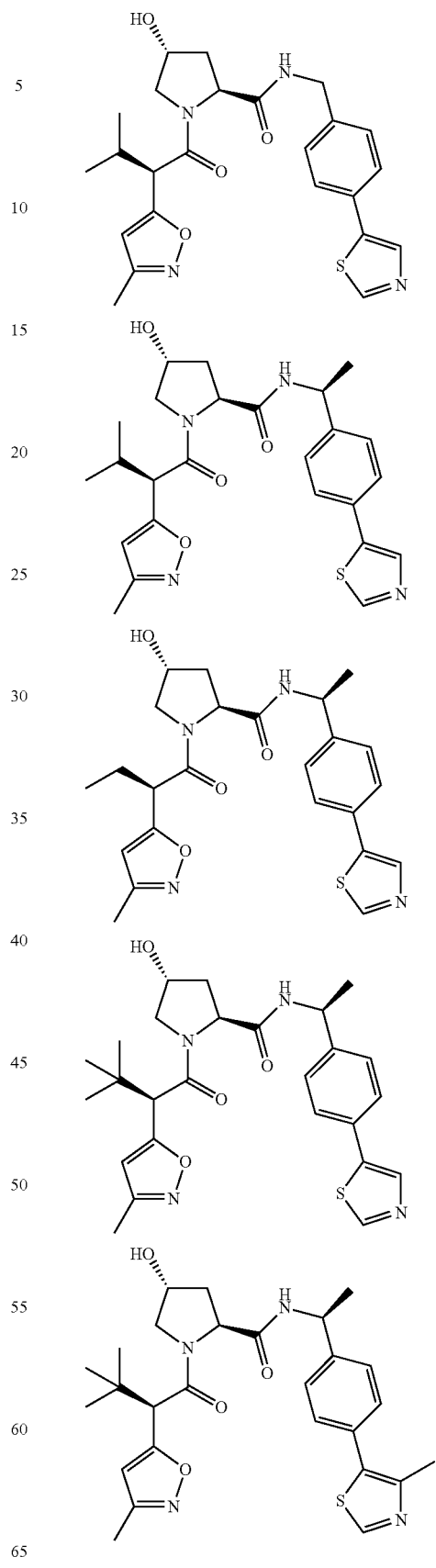

277
-continued
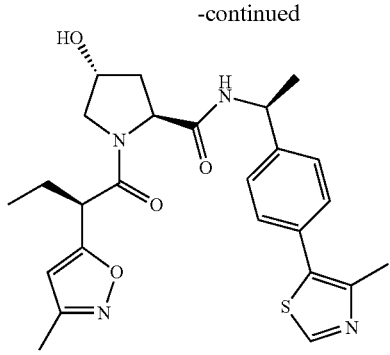
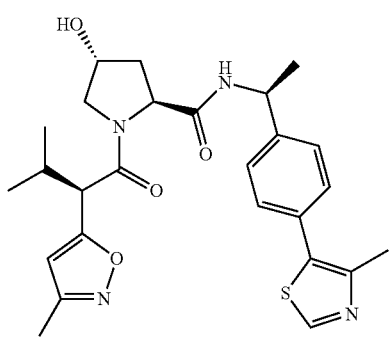
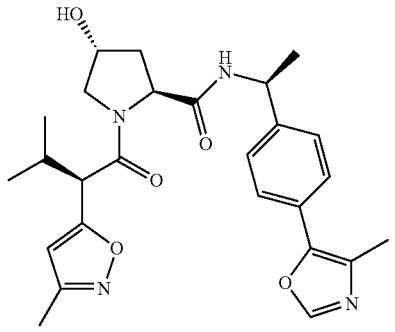
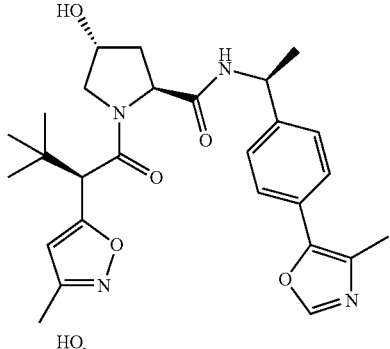
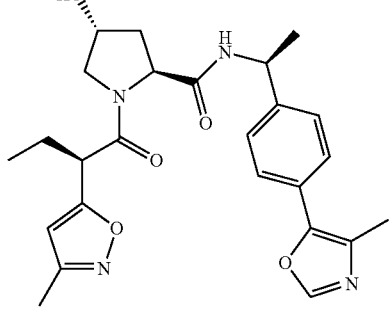
278
-continued
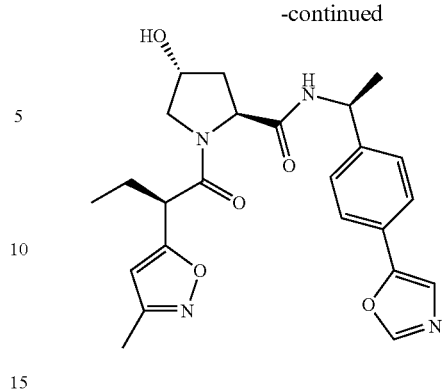
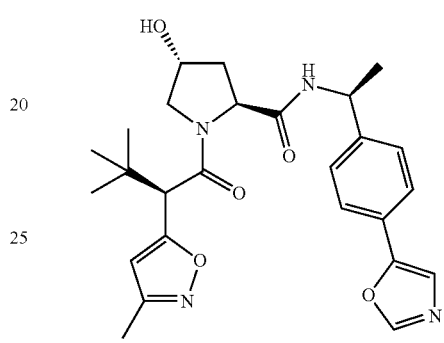
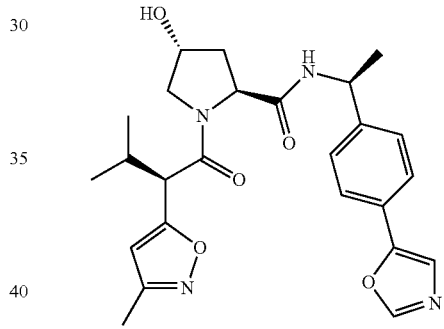
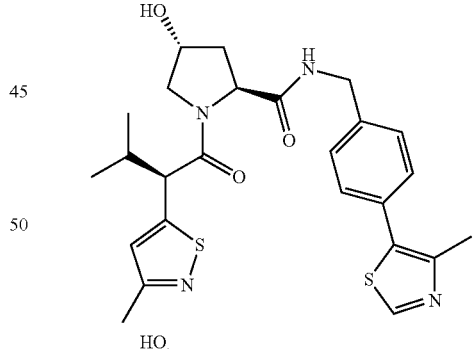
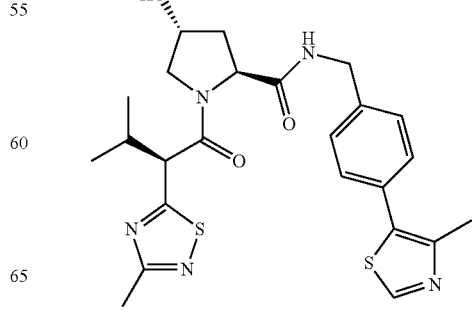

279
-continued
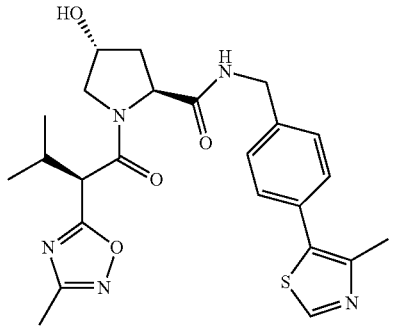
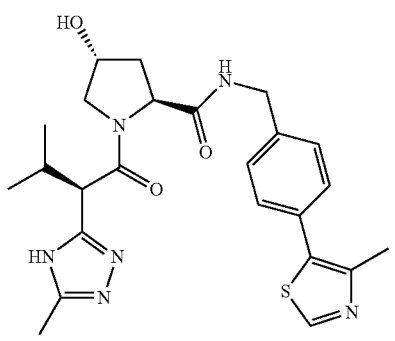
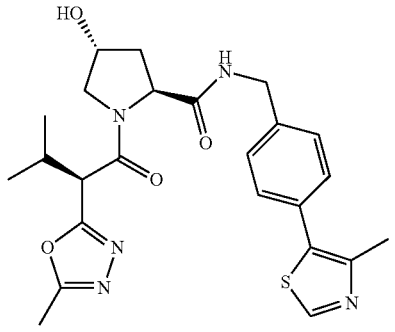
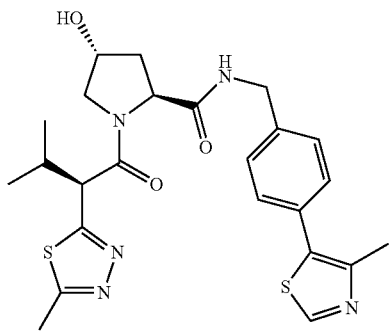
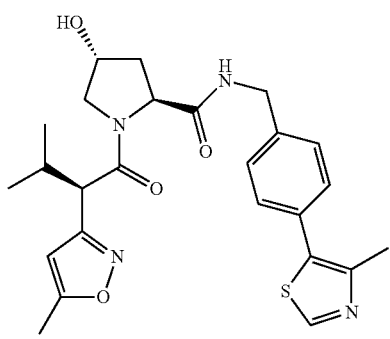
280
-continued
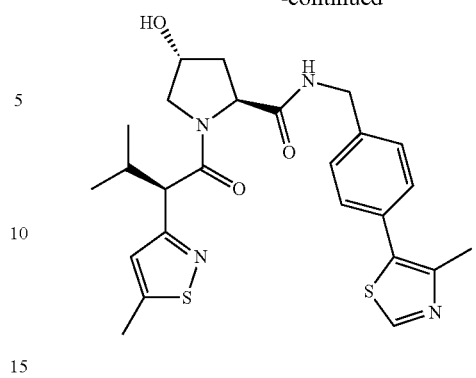
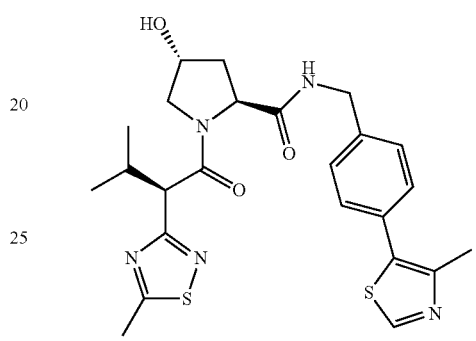
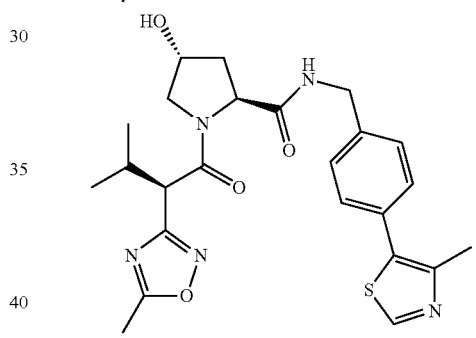
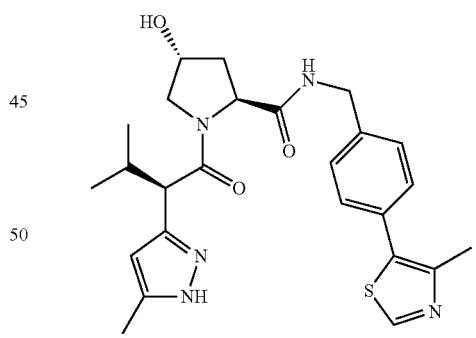
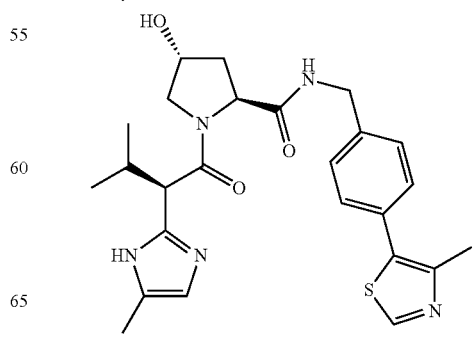

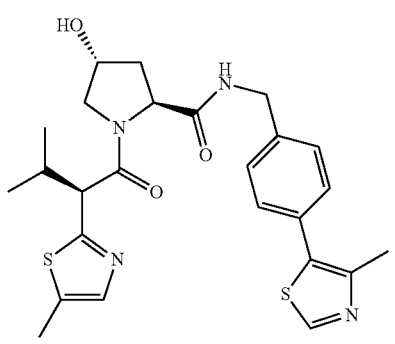
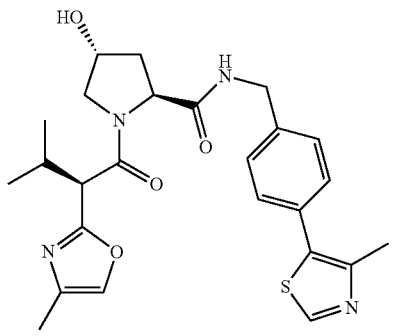
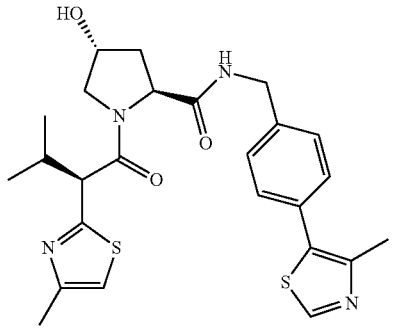
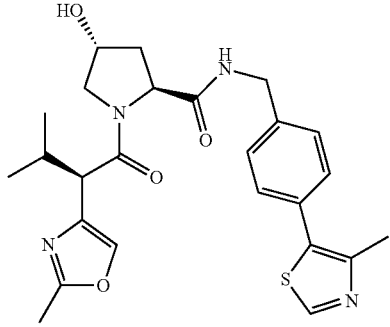
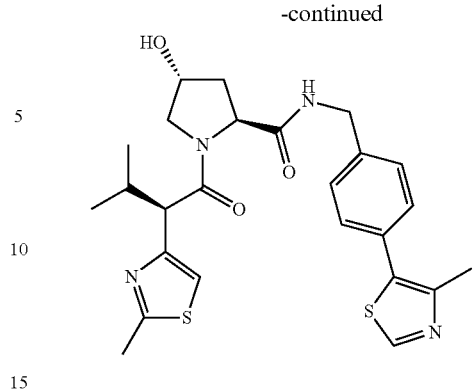
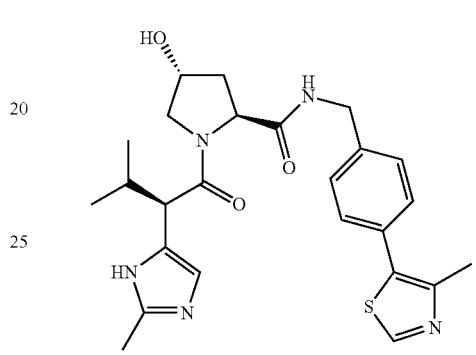
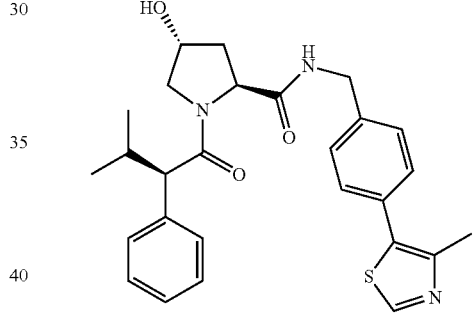
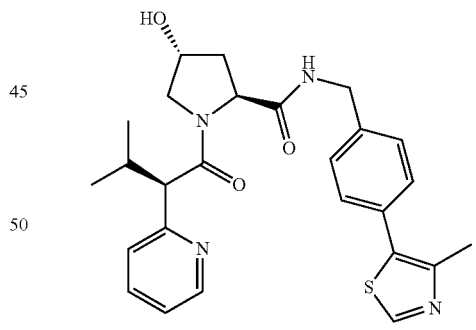
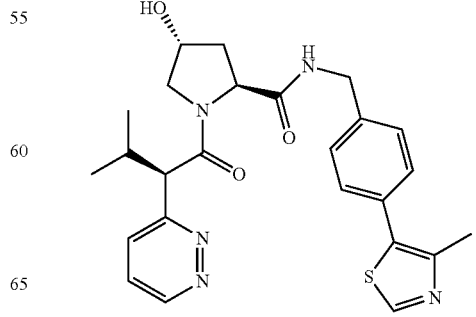

283
-continued
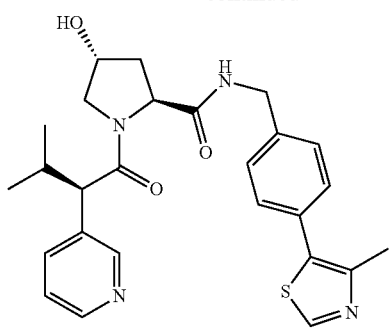
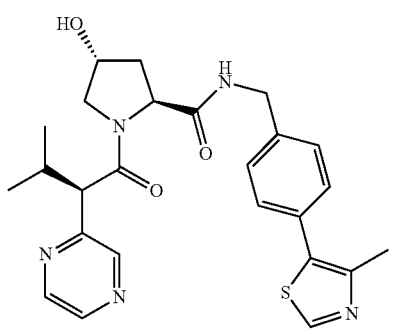
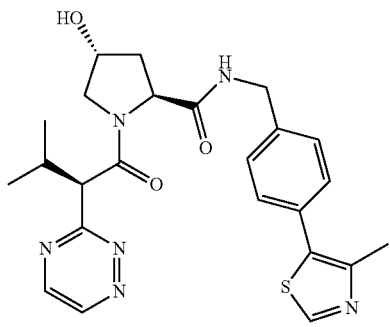
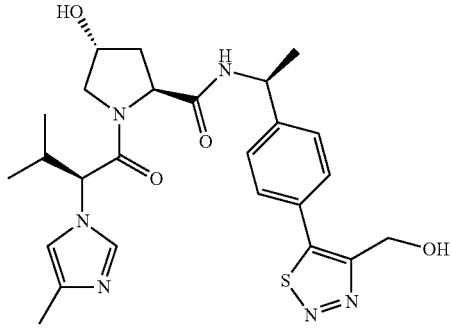
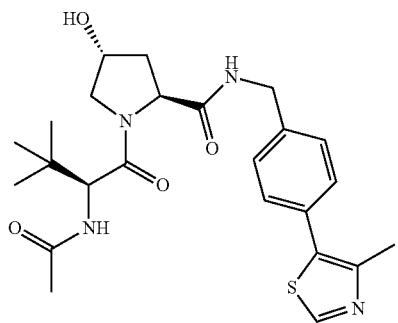
284
-continued
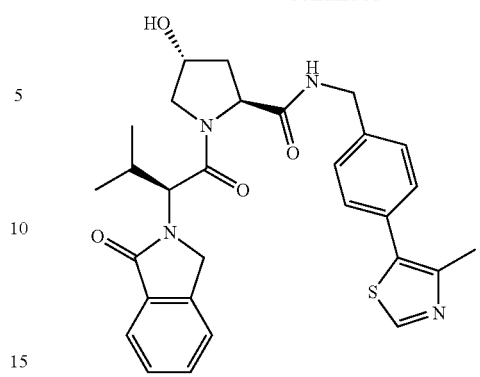
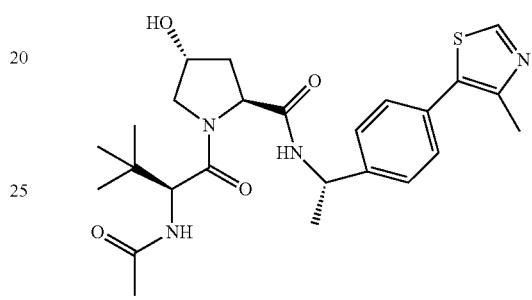
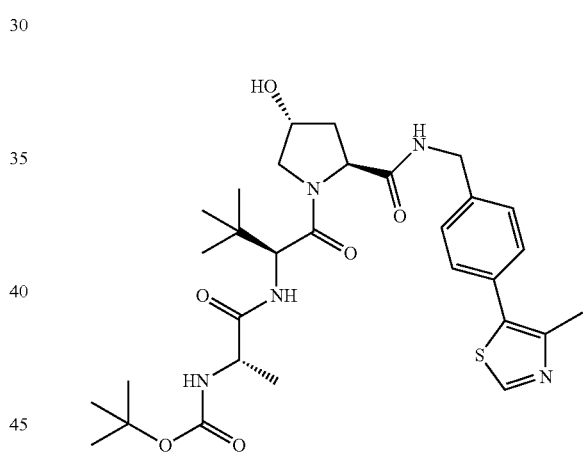
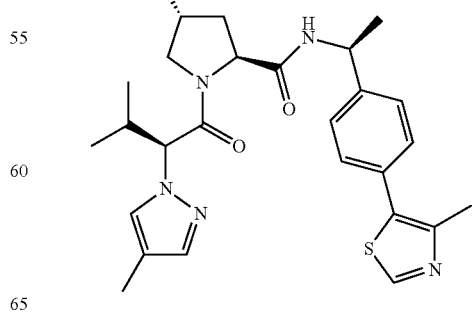

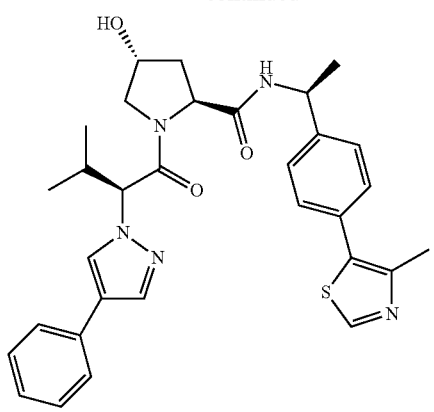
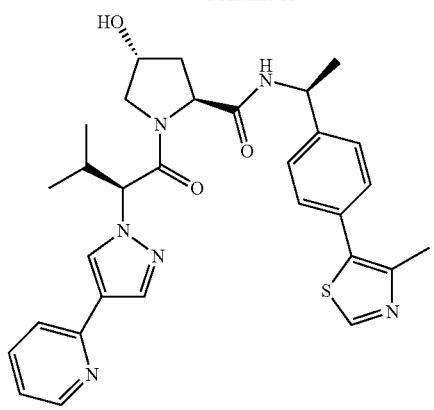
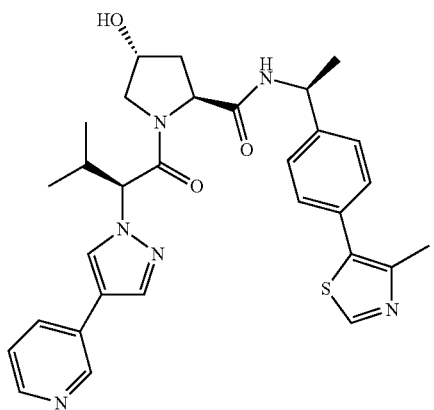
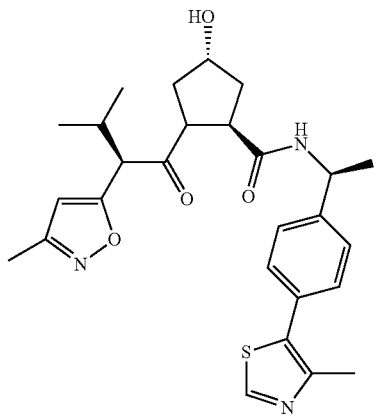
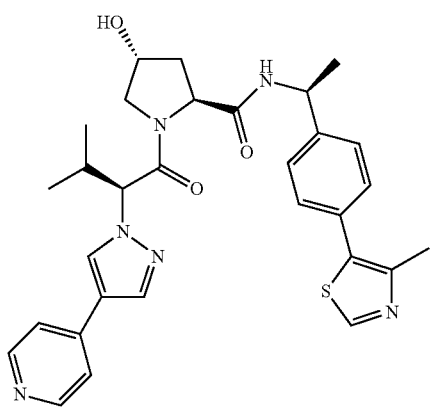
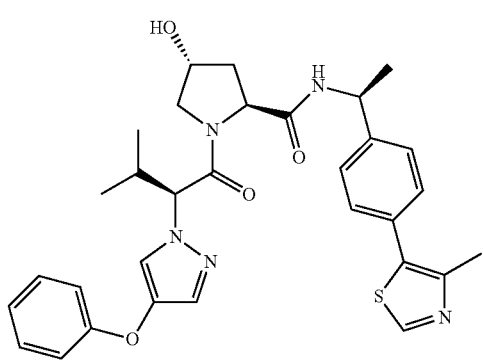
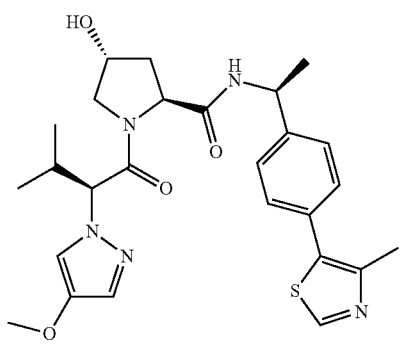
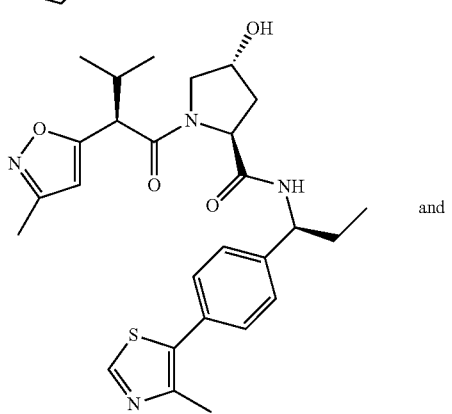
and

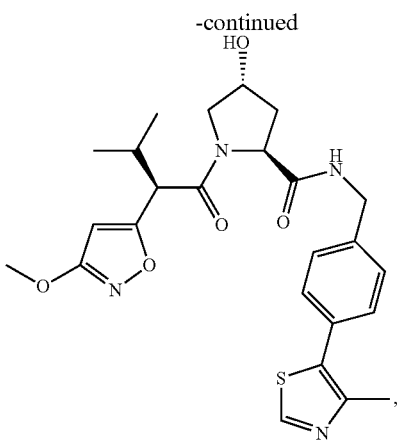

wherein the VLM may be connected to a PTM via a linker, as described herein, at any appropriate location, including, e.g., an aryl, heteroary, phenyl, or phenyl of an indole group, optionally via any appropriate functional group, such as an amine, ester, ether, alkyl, or alkoxy.

Exemplary Linkers

In certain embodiments, the compounds as described herein include one or more PTMs chemically linked or coupled to one or more ULMs (e.g., at least one of CLM, VLM, MLM, ILM, or a combination thereof) via a chemical linker (L). In certain embodiments, the linker group L is a group comprising one or more covalently connected structural units (e.g., $-A^L{}_1 \ldots (A^L)_q-$ or $-(A^L)_q-$), wherein $A_1$ is a group coupled to PTM, and $(A^L)_q$ is a group coupled to ULM.

In certain embodiments, the linker group L is selected from $-(A^L)_q-$:

$(A^L)_q$ is a group which is connected to a ULM moiety, a PTM moiety, or a combination thereof;

q of the linker is an integer greater than or equal to 1;

each $A^L$ is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}=CR^{L2}$, C≡C, $SiR^{L1}R^{L2}$, $P(O)R^{L1}$, $P(O)OR^{L1}$, $NR^{L3}C(=NCN)NR^{L4}$, $NR^{L3}C(=NCN)$, $NR^{L3}C(=CNO_2)NR^{L4}$, $C_{3-11}$cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-11}$heterocyclyl optionally substituted with 0-6 $R^{L1}$ and/or $R^{L2}$ groups, $C_{5-13}$ spiroheterocycloalkyl optionally substituted with 0-8 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}$alkyl$)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}$cycloalkyl$)_2$, $N(C_{1-8}$cycloalkyl)($C_{1-8}$alkyl), OH, $NH_2$, SH, $SO_2C_{1-8}$alkyl, $P(O)(OC_{1-8}$alkyl)($C_{1-8}$alkyl), $P(O)(OC_{1-8}$alkyl$)_2$, $CC-C_{1-8}$alkyl, CCH, $CH=CH(C_{1-8}$alkyl), $C(C_{1-8}$alkyl$)=CH(C_{1-8}$alkyl), $C(C_{1-8}$alkyl$)=C(C_{1-8}$alkyl$)_2$, $Si(OH)_3$, $Si(C_{1-8}$alkyl$)_3$, $Si(OH)(C_{1-8}$alkyl$)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}$alkyl$)_2$, $SONHC_{1-8}$alkyl, $SON(C_{1-8}$alkyl$)_2$, $CONHC_{1-8}$alkyl, $CON(C_{1-8}$alkyl$)_2$, $N(C_{1-8}$alkyl$)CONH(C_{1-8}$alkyl), $N(C_{1-8}$alkyl)$CON(C_{1-8}$alkyl$)_2$, $NHCONH(C_{1-8}$alkyl), NHCON $(C_{1-8}$ alkyl$)_2$, $NHCONH_2$, $N(C_{1-8}$alkyl$)SO_2NH(C_{1-8}$alkyl), $N(C_{1-8}$alkyl) $SO_2N(C_{1-8}$alkyl$)_2$, NH $SO_2NH$ $(C_{1-8}$alkyl), NH $SO_2N(C_{1-8}$alkyl$)_2$, NH $SO_2NH_2$.

In certain embodiments, q of the linker is an integer greater than or equal to 0. In certain embodiments, q is an integer greater than or equal to 1.

In certain embodiments, e.g., where q of the linker is greater than 2, $(A^L)_q$ is a group which is connected to ULM, and $A^L{}_1$ and $(A^L)_q$ are connected via structural units of the linker (L).

In certain embodiments, e.g., where q of the linker is 2, $(A^L)_q$ is a group which is connected to $A^L{}_1$ and to a ULM.

In certain embodiments, e.g., where q of the linker is 1, the structure of the linker group L is $-A^L{}_1-$, and $A^L{}_1$ is a group which is connected to a ULM moiety and a PTM moiety.

In certain embodiments, the linker (L) comprises a group represented by a general structure selected from the group consisting of:

—NR(CH$_2$)$_n$-(lower alkyl)-, —NR(CH$_2$)$_n$-(lower alkoxyl)-, —NR(CH$_2$)$_n$-(lower alkoxyl)-OCH$_2$—, —NR(CH$_2$)$_n$-(lower alkoxyl)-(lower alkyl)-OCH$_2$—, —NR(CH$_2$)$_n$-(cycloalkyl)-(lower alkyl)-OCH$_2$—, —NR(CH$_2$)$_n$-(hetero cycloalkyl)-, —NR(CH$_2$CH$_2$O)$_n$-(lower alkyl)-O—CH$_2$—, —NR(CH$_2$CH$_2$O)$_n$-(hetero cycloalkyl)-O—CH$_2$—, —NR(CH$_2$CH$_2$O)$_n$-Aryl-O—CH$_2$—, —NR(CH$_2$CH$_2$O)$_n$-(hetero aryl)-O—CH$_2$—, —NR(CH$_2$CH$_2$O)$_n$-(cyclo alkyl)-O-(hetero aryl)-O—CH$_2$—, —NR(CH$_2$CH$_2$O)$_n$-(cyclo alkyl)-O-Aryl-O—CH$_2$—, —NR(CH$_2$CH$_2$O)$_n$-(lower alkyl)-NH-Aryl-O—CH$_2$—, —NR(CH$_2$CH$_2$O)$_n$-(lower alkyl)-O-Aryl-CH$_2$, —NR(CH$_2$CH$_2$O)$_n$-cycloalkyl-O-Aryl-, —NR(CH$_2$CH$_2$O)$_n$-cycloalkyl-O-(heteroaryl)l-, —NR(CH$_2$CH$_2$)$_n$-(cycloalkyl)-O-(heterocycle)-CH$_2$, —NR(CH$_2$CH$_2$)$_n$-(heterocycle)-(heterocycle)-CH$_2$, —N(R1R2)-(heterocycle)-CH$_2$; where n of the linker can be 0 to 10;

R of the linker can be H, lower alkyl;

R1 and R2 of the linker can form a ring with the connecting N.

In certain embodiments, the linker (L) comprises a group represented by a general structure selected from the group consisting of:

—N(R)—(CH2)$_m$—O(CH2)$_n$—O(CH2)$_p$—O(CH2)$_p$-O(CH2)$_q$-O(CH2)$_r$-OCH2-,

—O—(CH2)$_m$-O(CH2)$_n$-O(CH2)$_p$-O(CH2)$_p$-O(CH2)$_q$-O(CH2)$_r$-OCH2-,

—O—(CH2)$_m$-O(CH2)$_n$-O(CH2)$_o$-O(CH2)$_p$-O(CH2)$_q$-O(CH2)$_r$-O—;

—N(R)—(CH2)$_m$-O(CH2)$_n$-O(CH2)$_o$-O(CH2)$_p$-O(CH2)$_q$-O(CH2)$_r$-O—;

—(CH2)$_m$-O(CH2)$_n$-O(CH2)$_o$-O(CH2)$_p$-O(CH2)$_q$-O(CH2)$_r$-O—;

—(CH2)$_m$-O(CH2)$_n$-O(CH2)$_o$-O(CH2)$_p$-O(CH2)$_q$-O(CH2)$_r$-OCH2-;

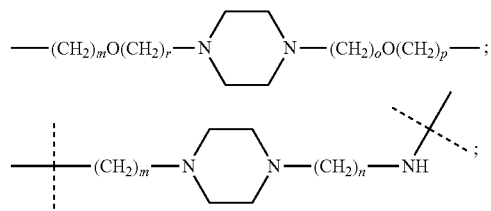

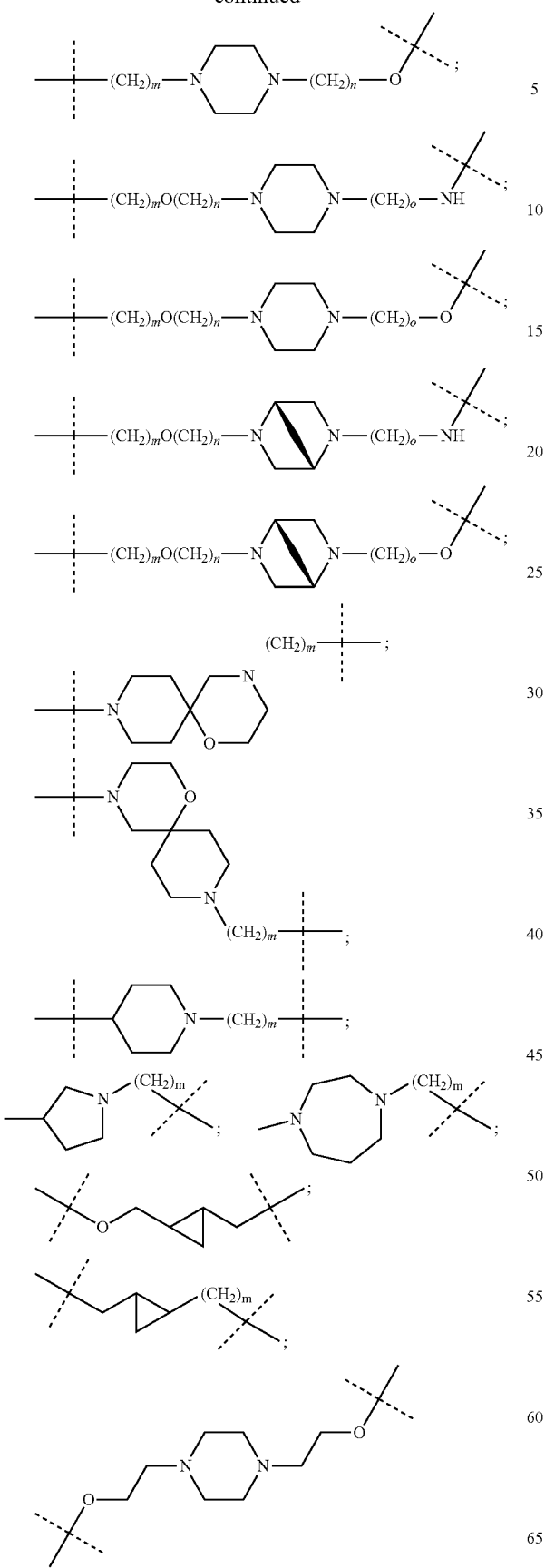
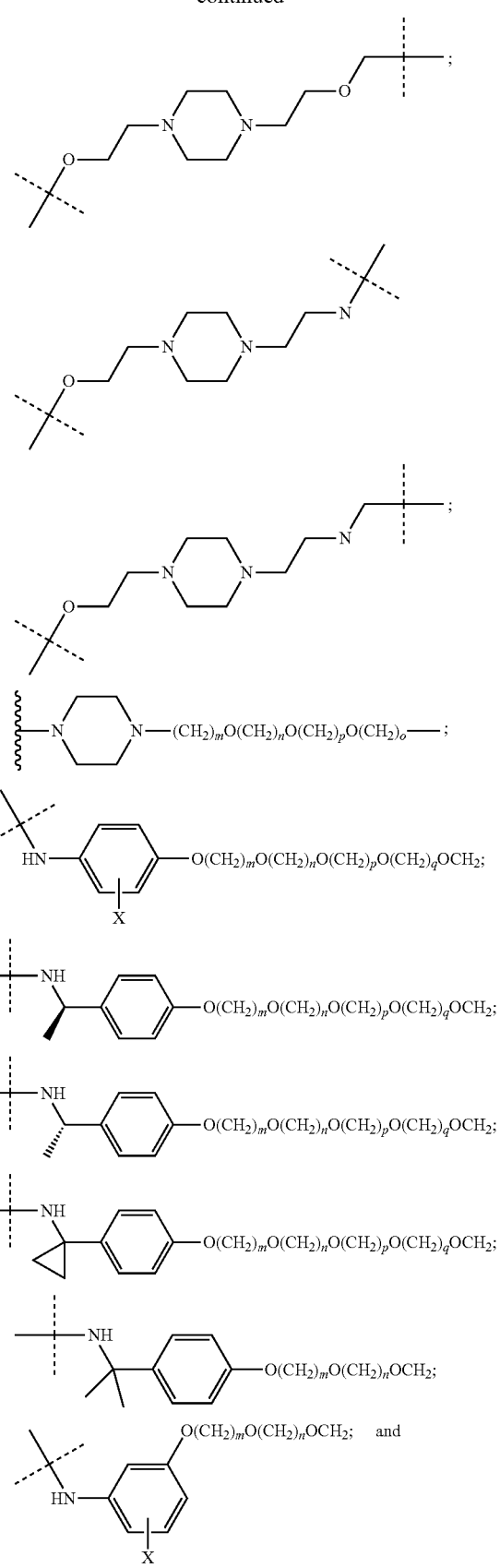

291
-continued
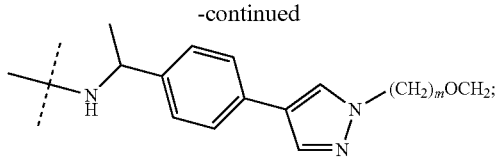
wherein
each m, n, o, p, q, and r of the linker is independently 0, 1, 2, 3, 4, 5, 6;
when the number is zero, there is no N—O or O—O bond
292
R of the linker is H, methyl and ethyl;
X of the linker is H and F
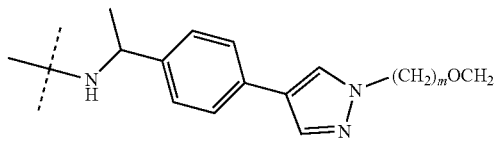
where m of the linker can be 2, 3, 4, 5
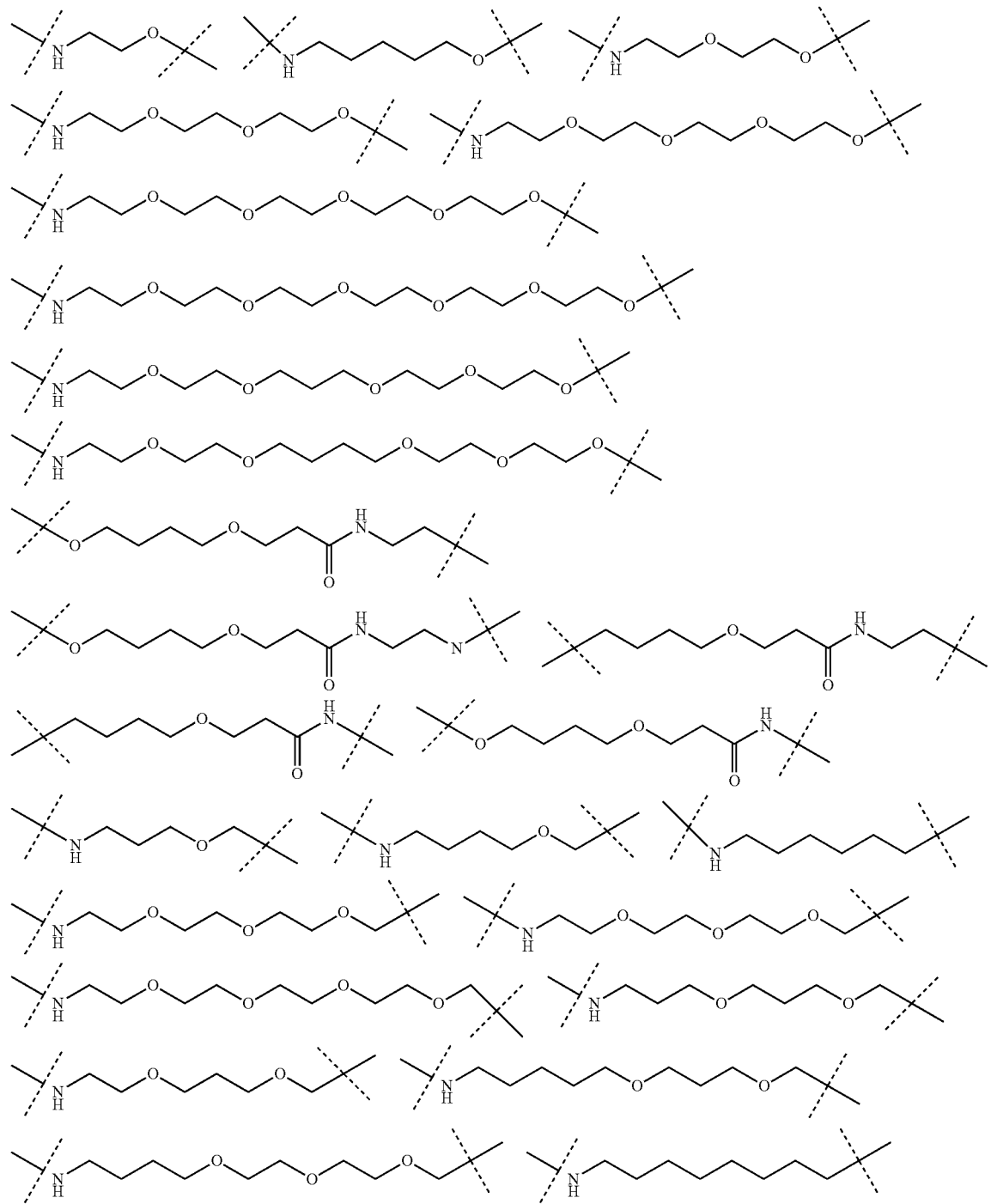

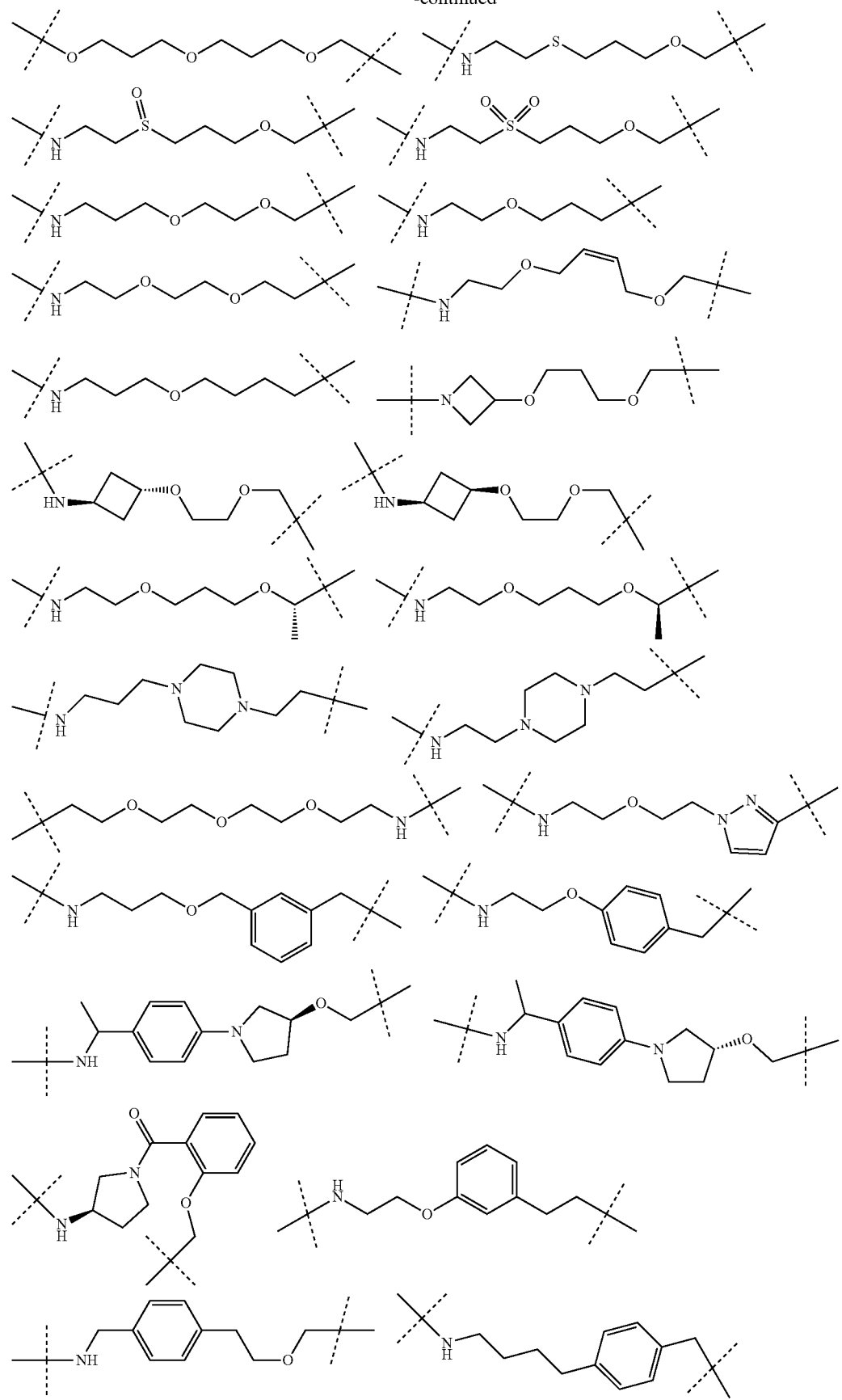

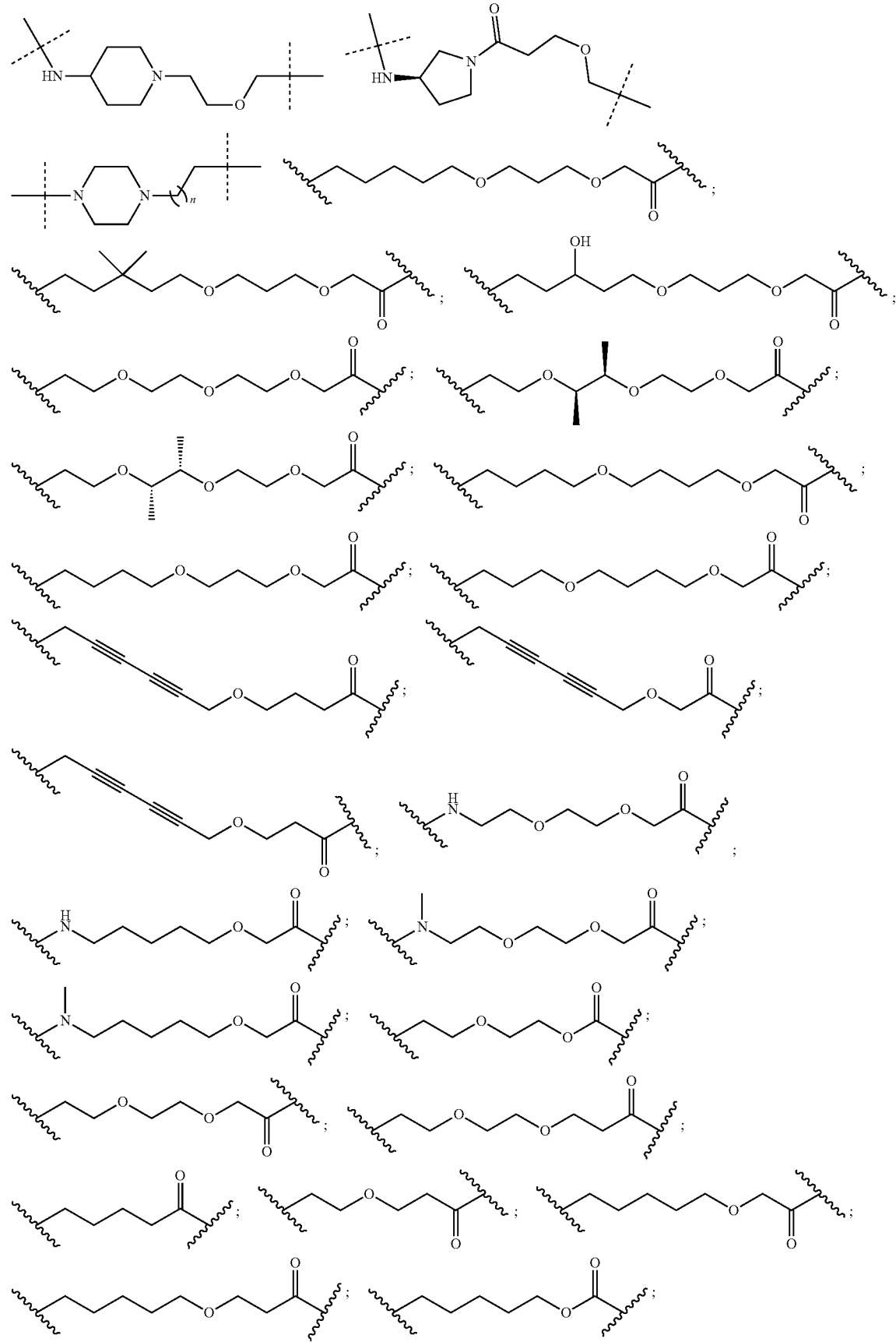

-continued
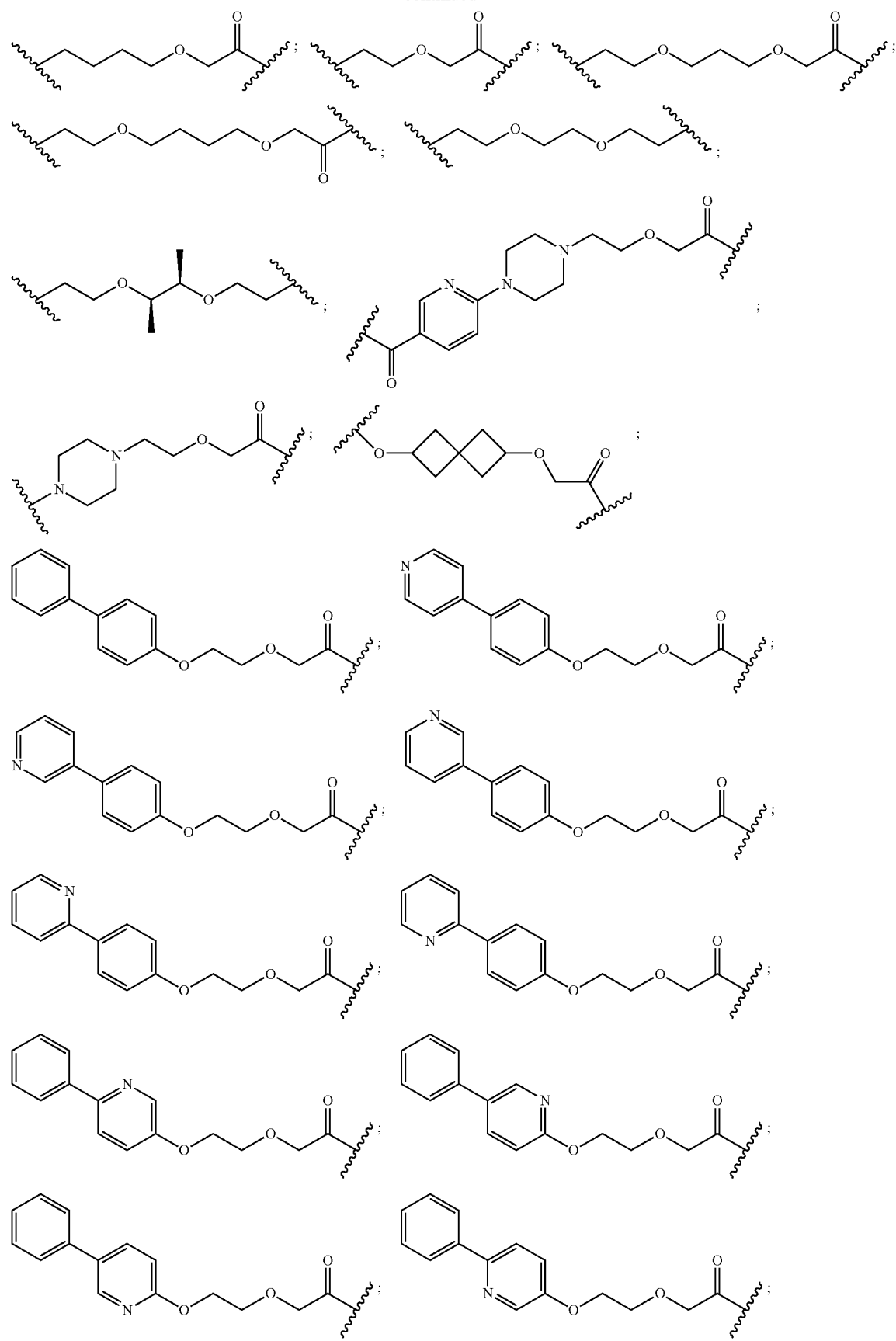

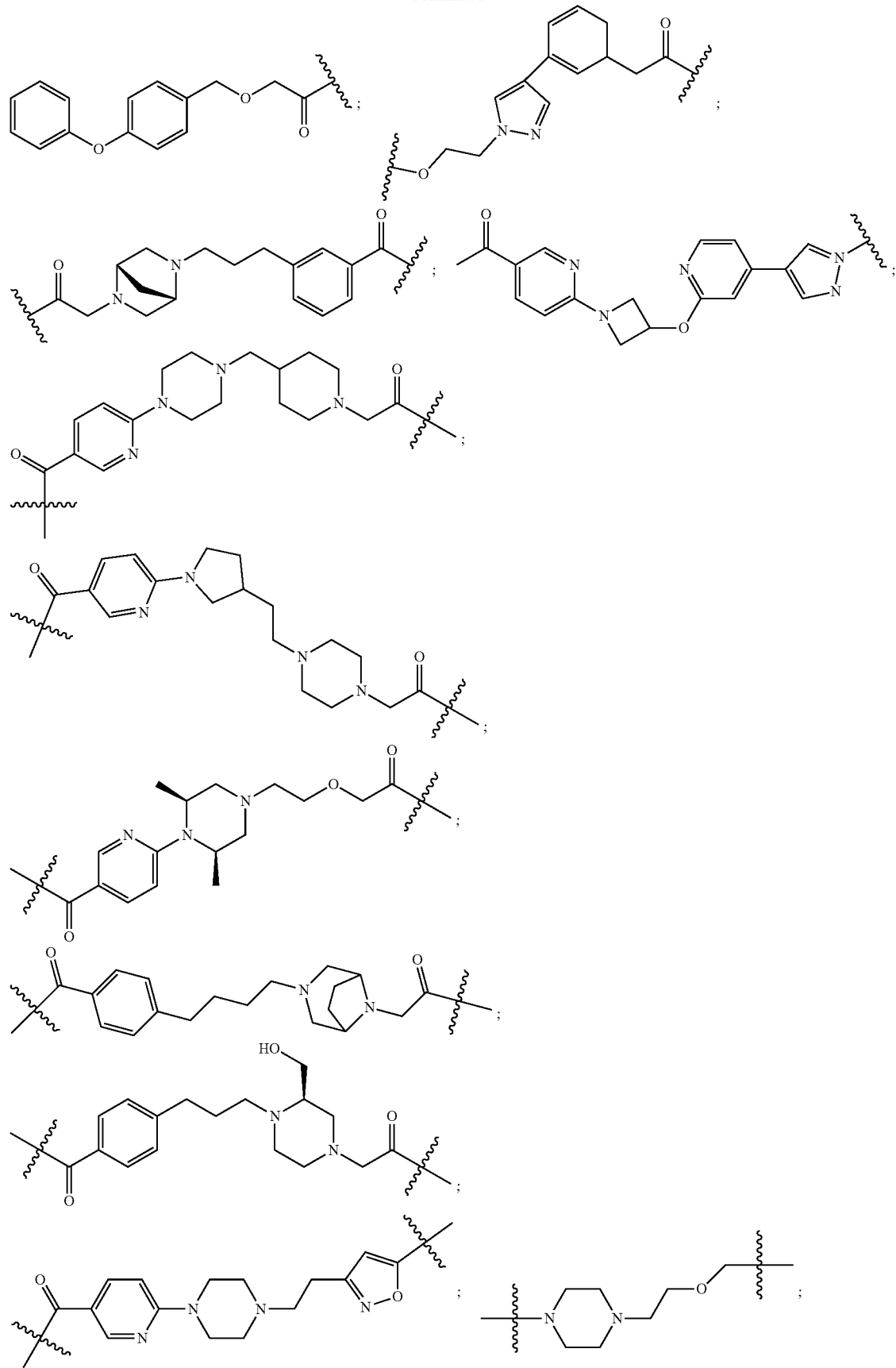

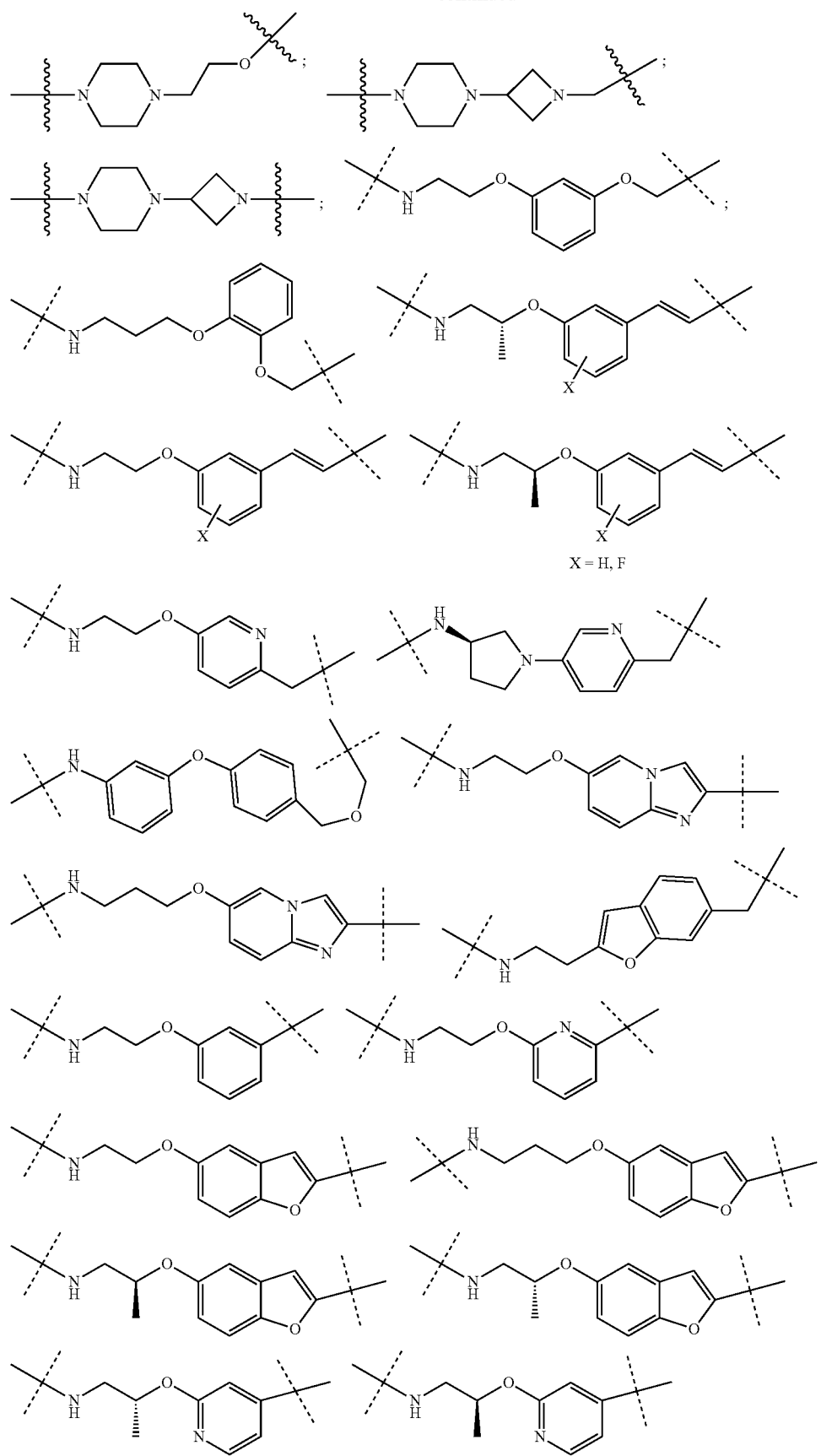

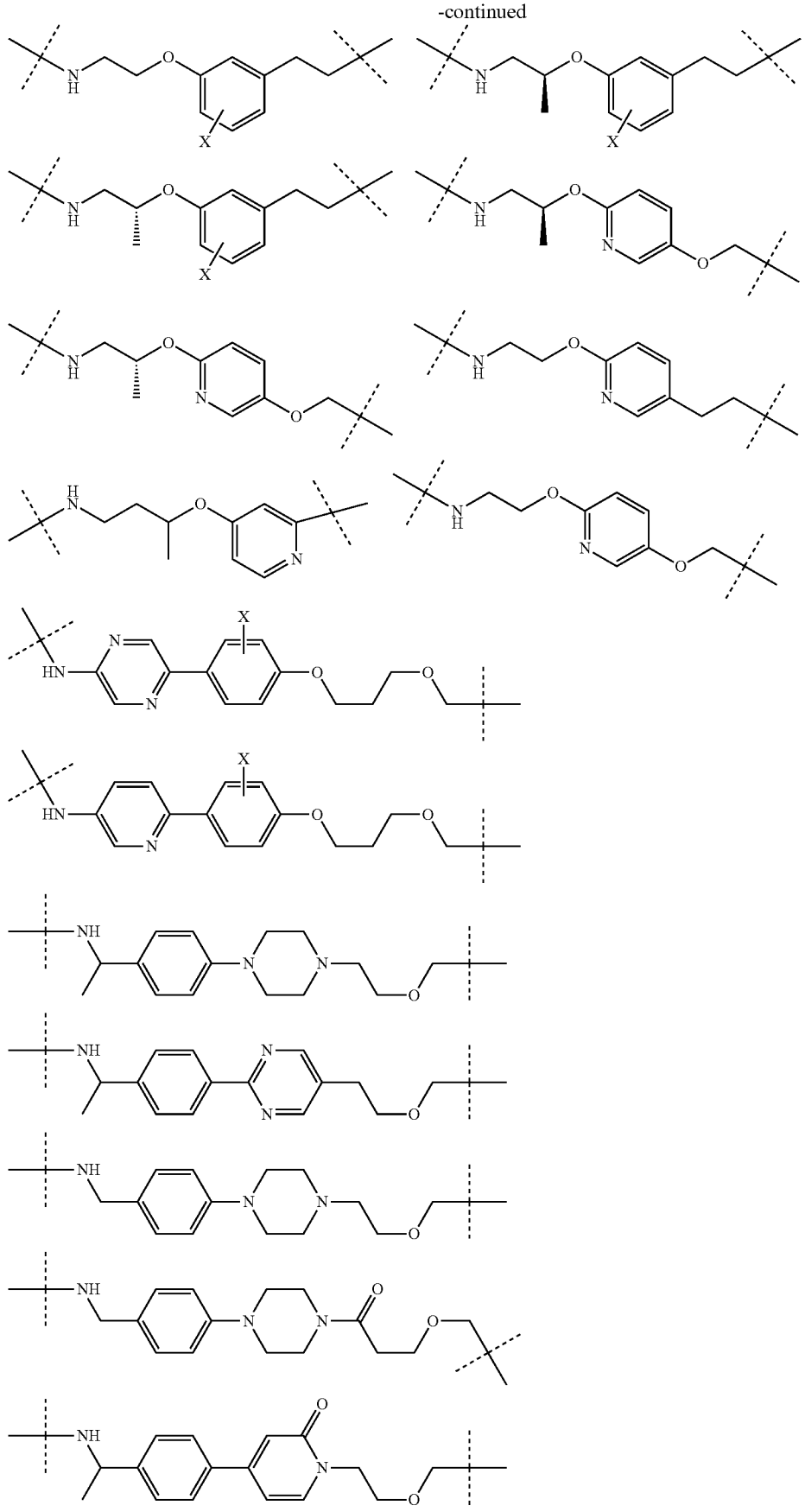

-continued
305
306
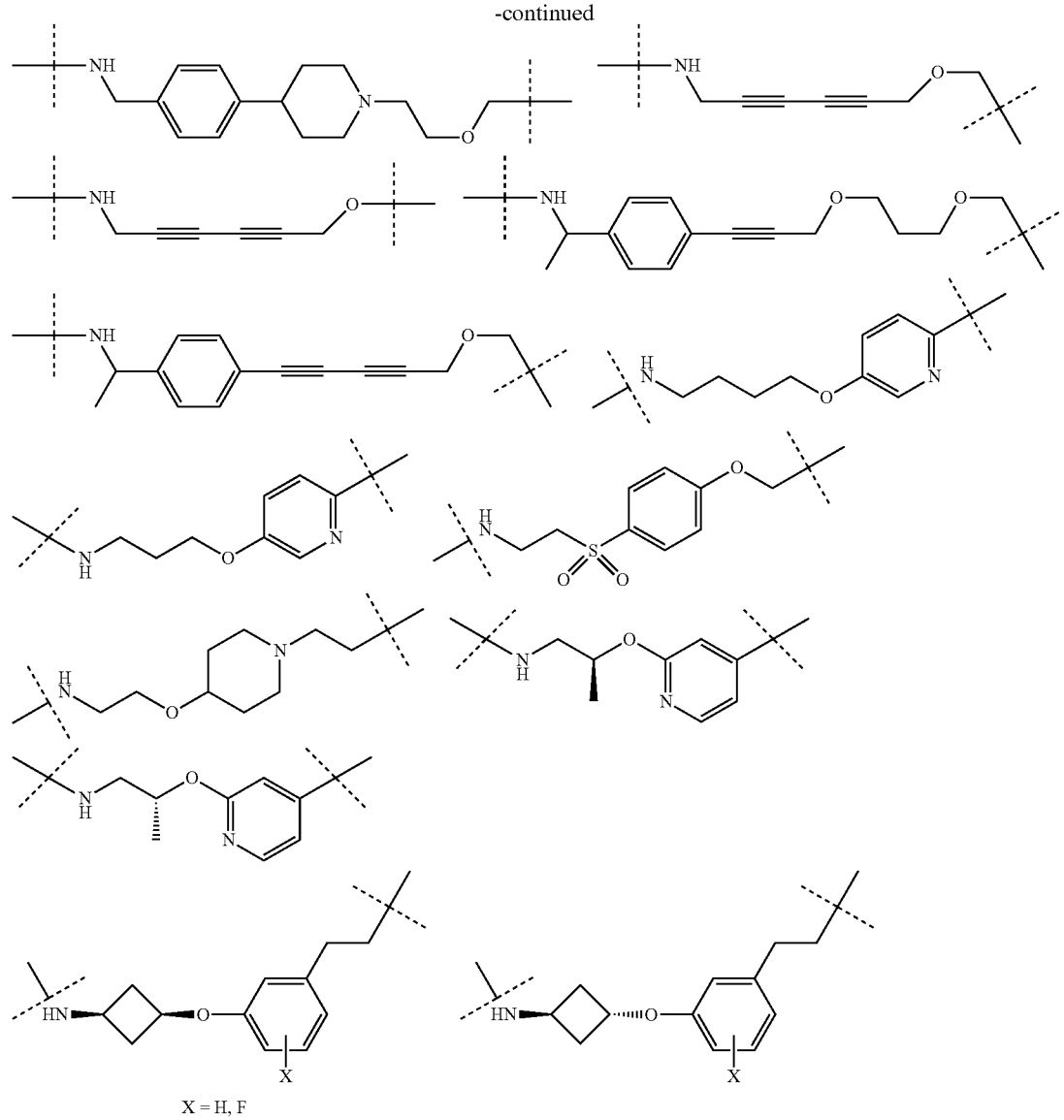
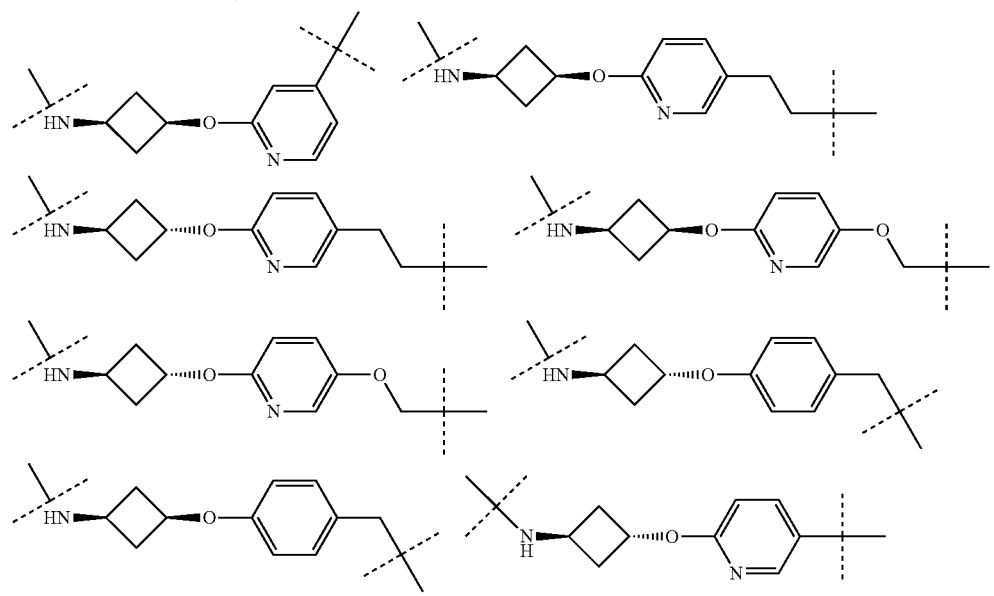

-continued
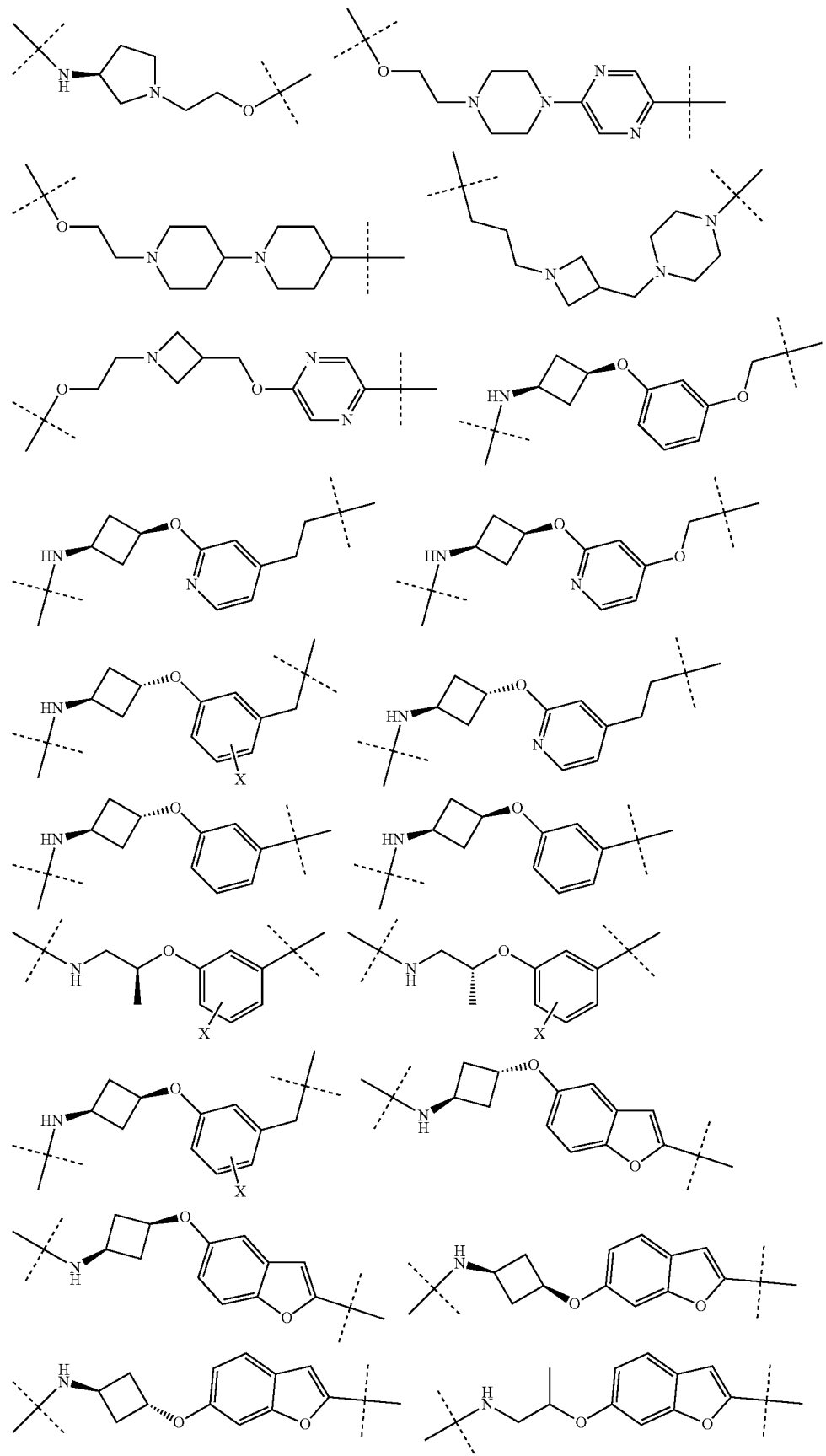

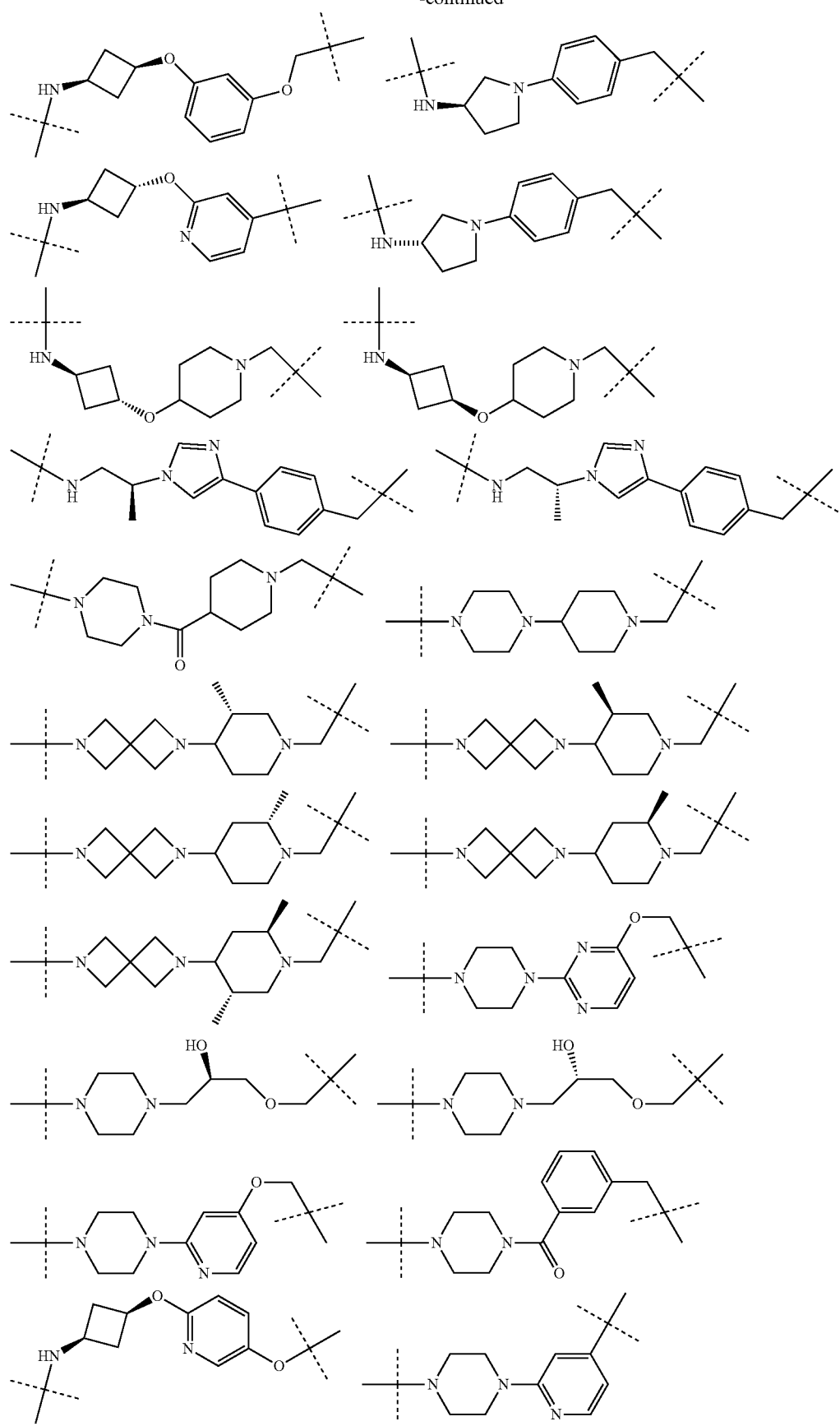

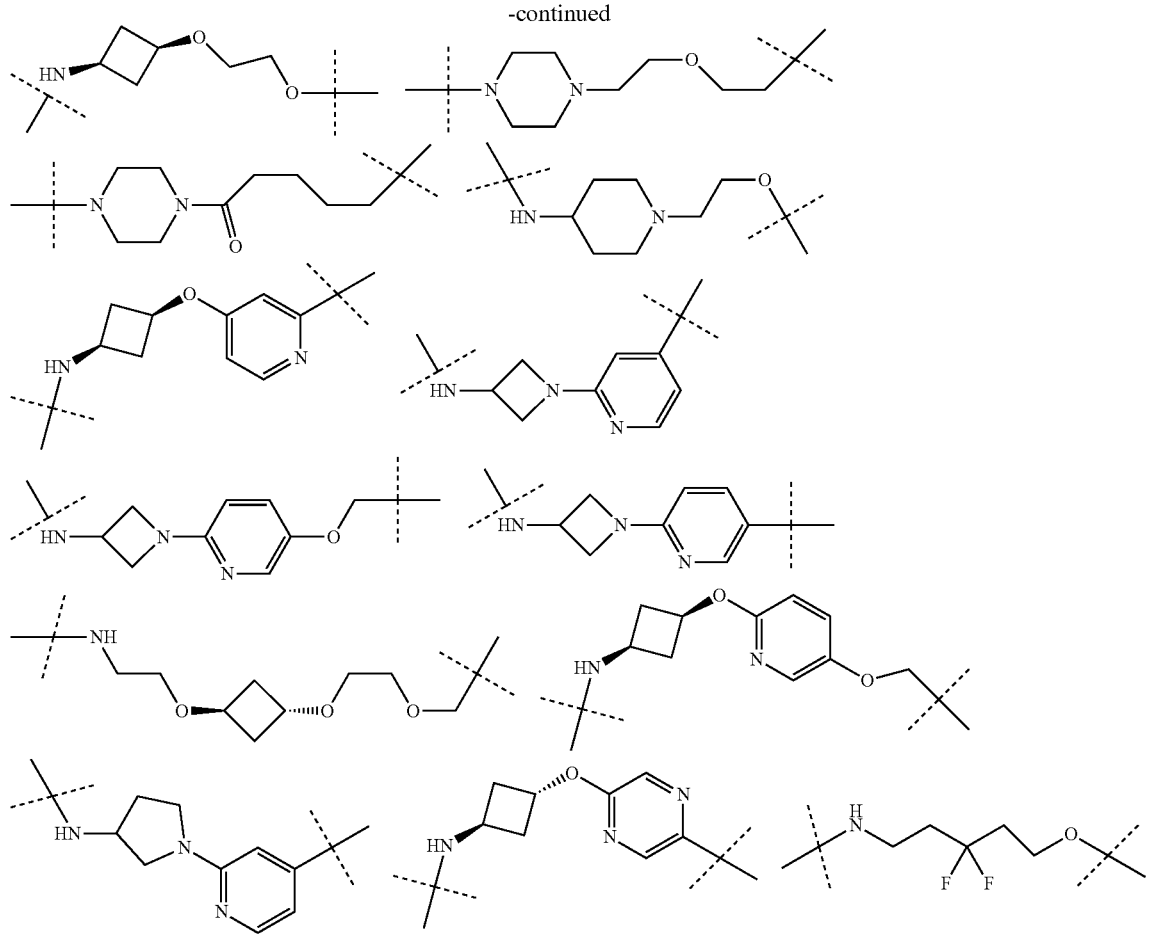
where each n and m of the linker can independently be 0, 1, 2, 3, 4, 5, 6.
In some embodiments, the linker (L) is selected from the group consisting of:
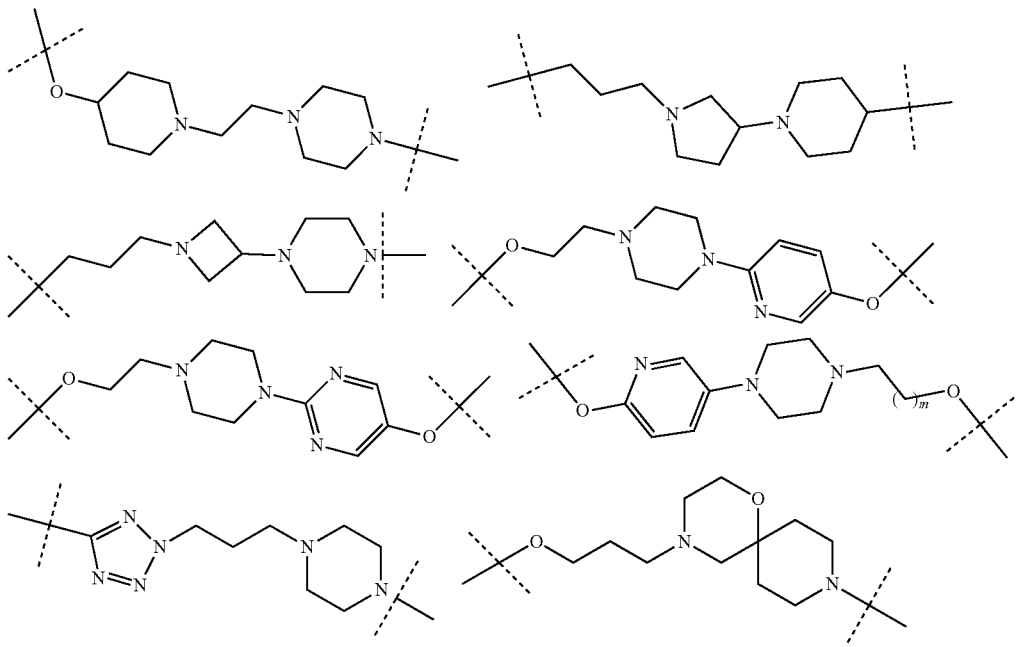

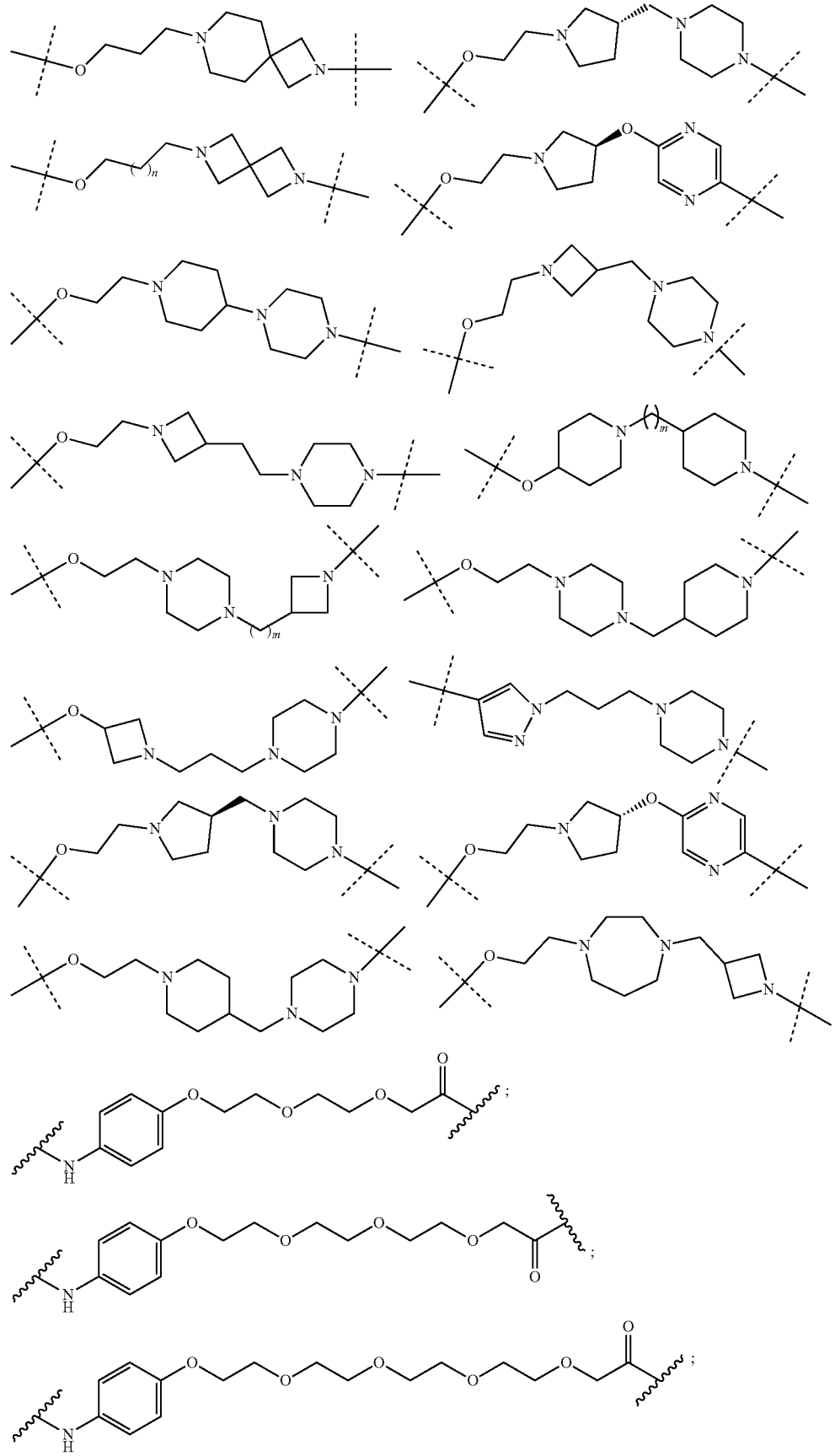

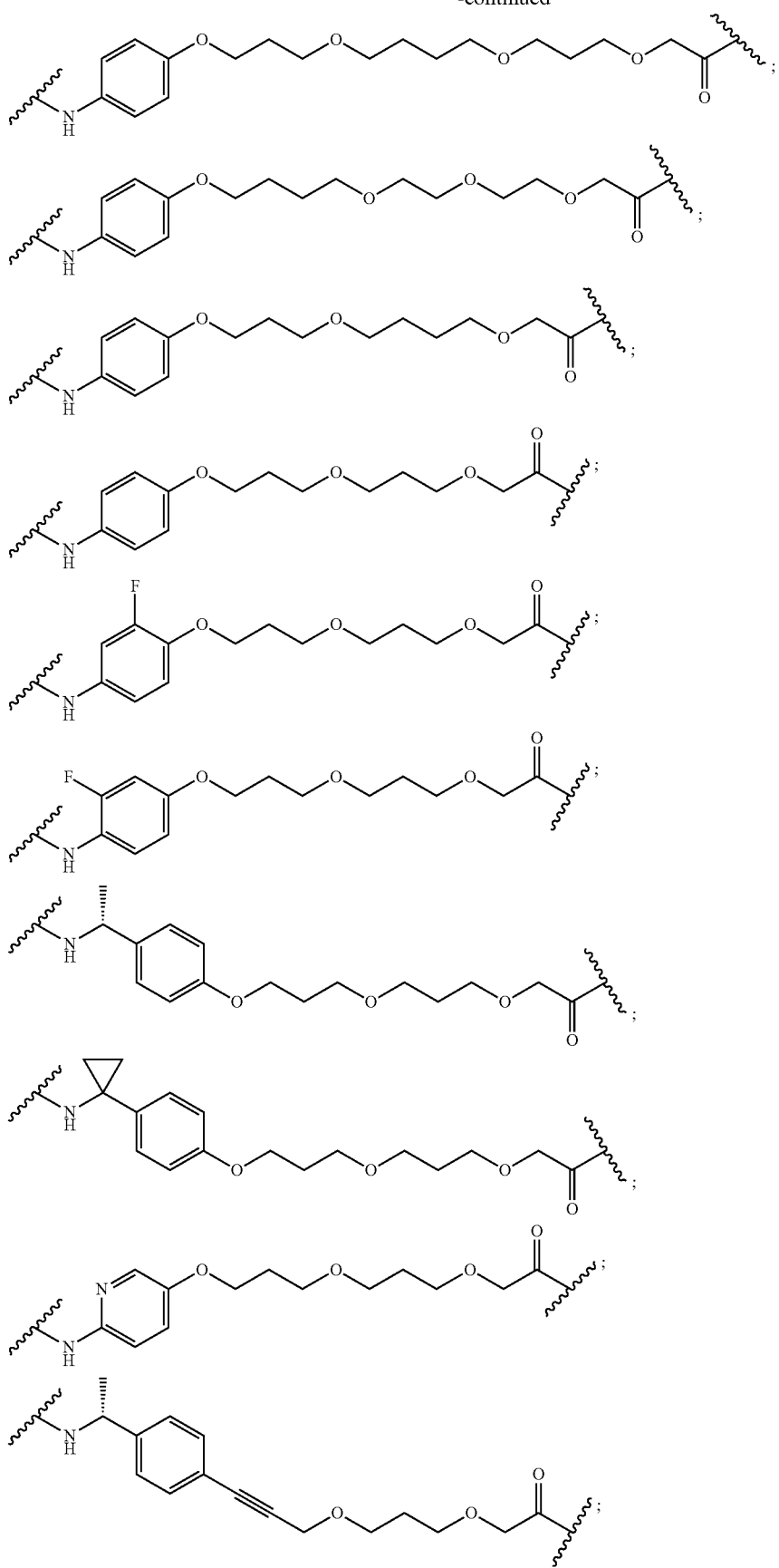

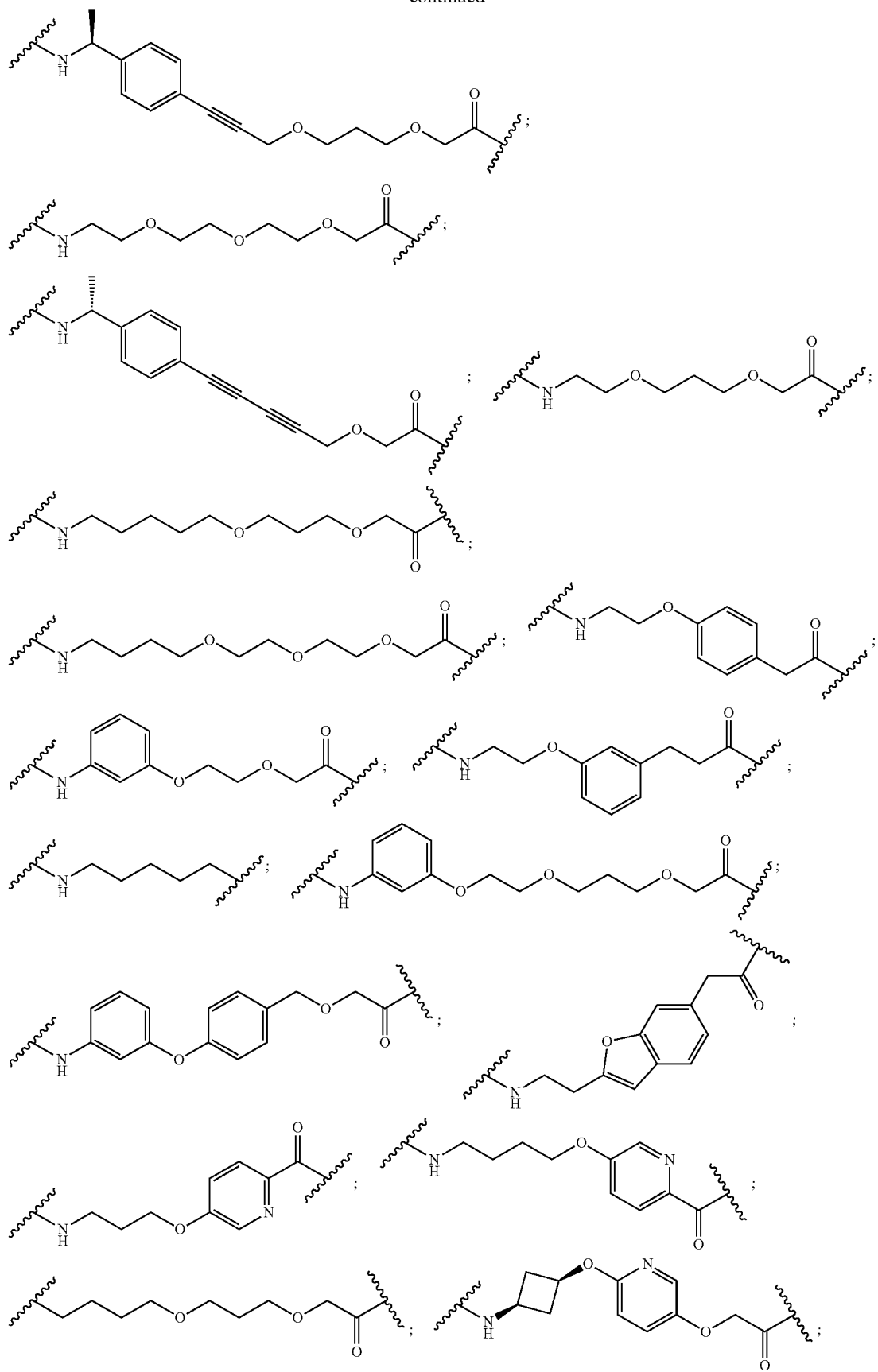

-continued
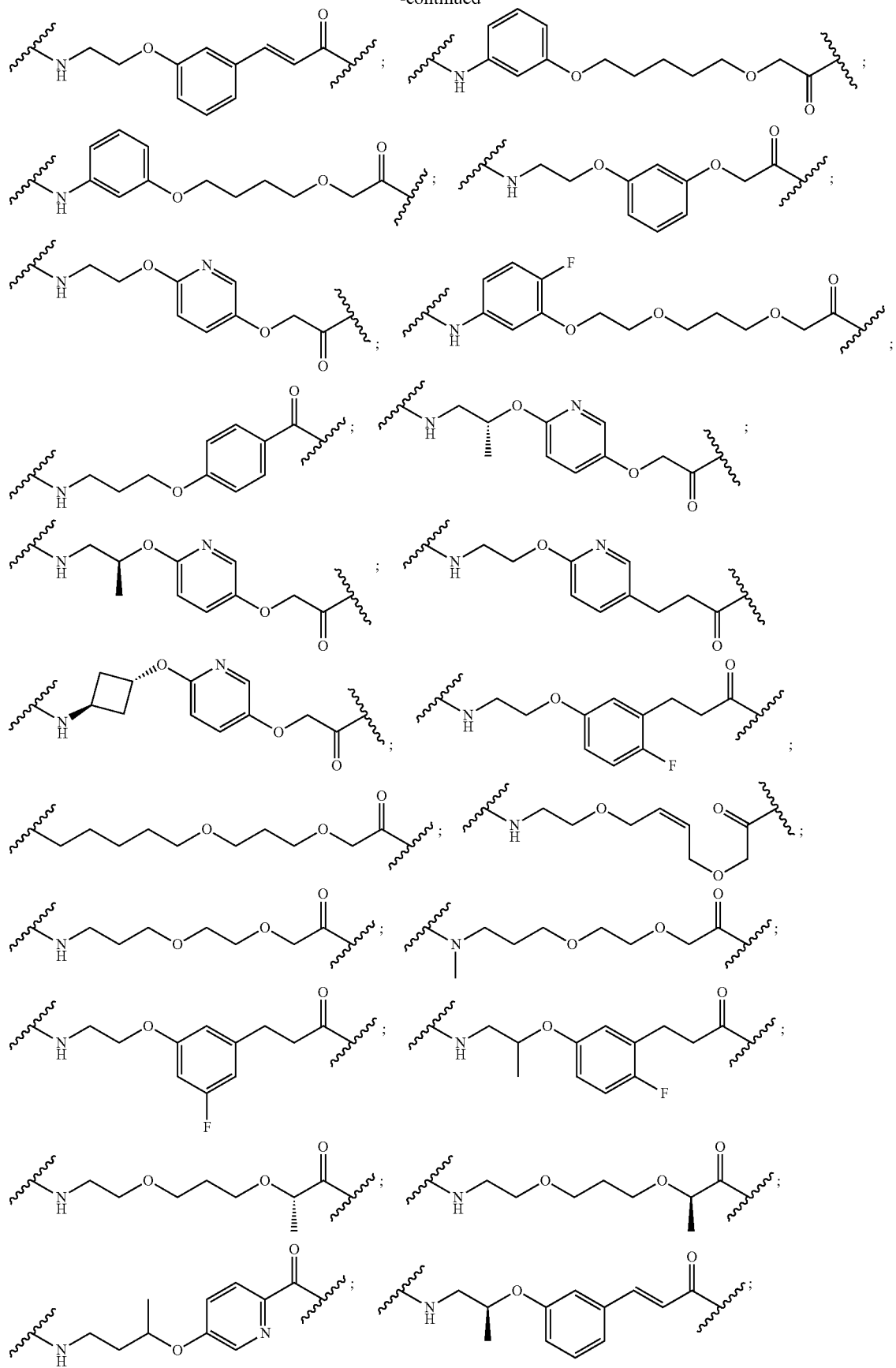

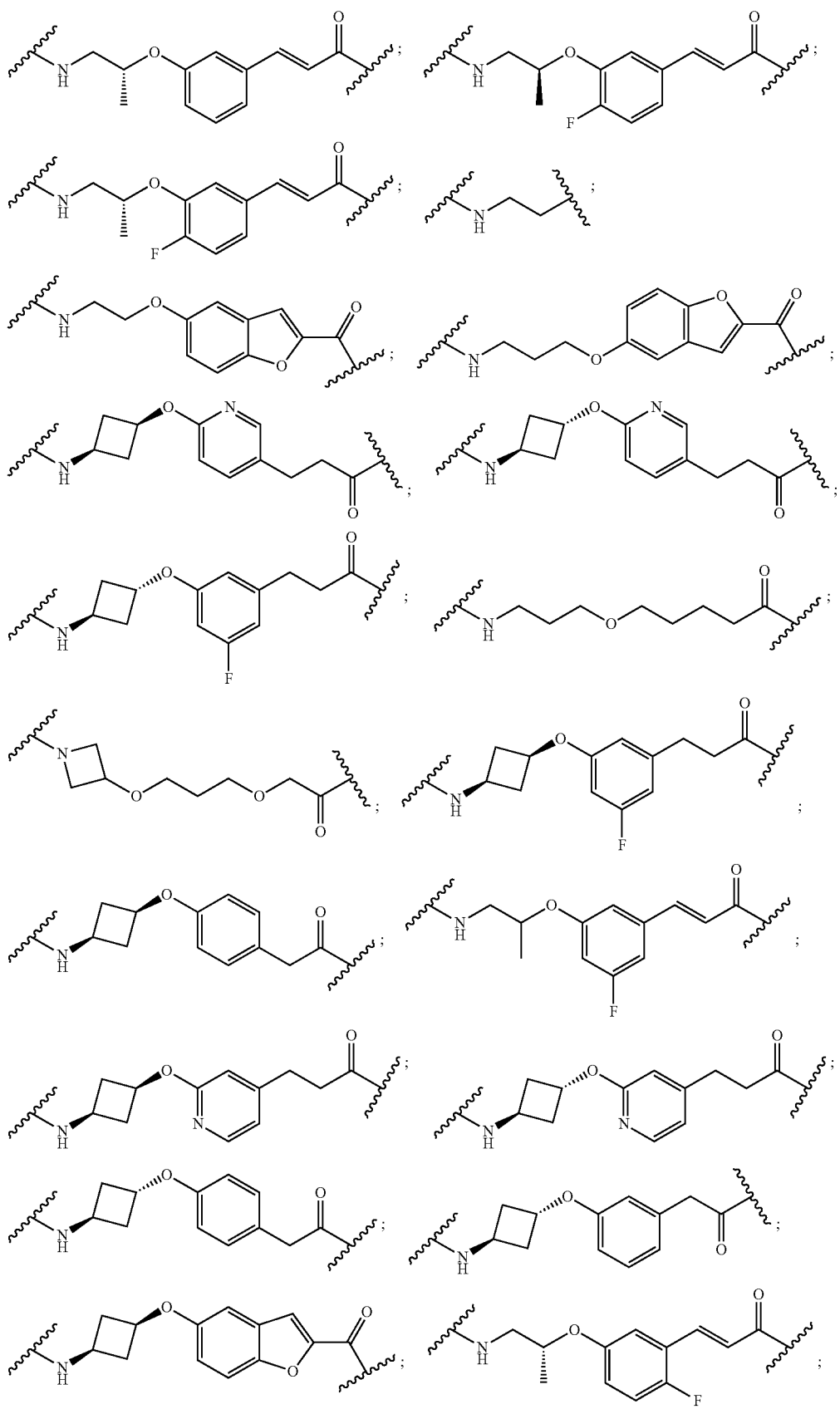

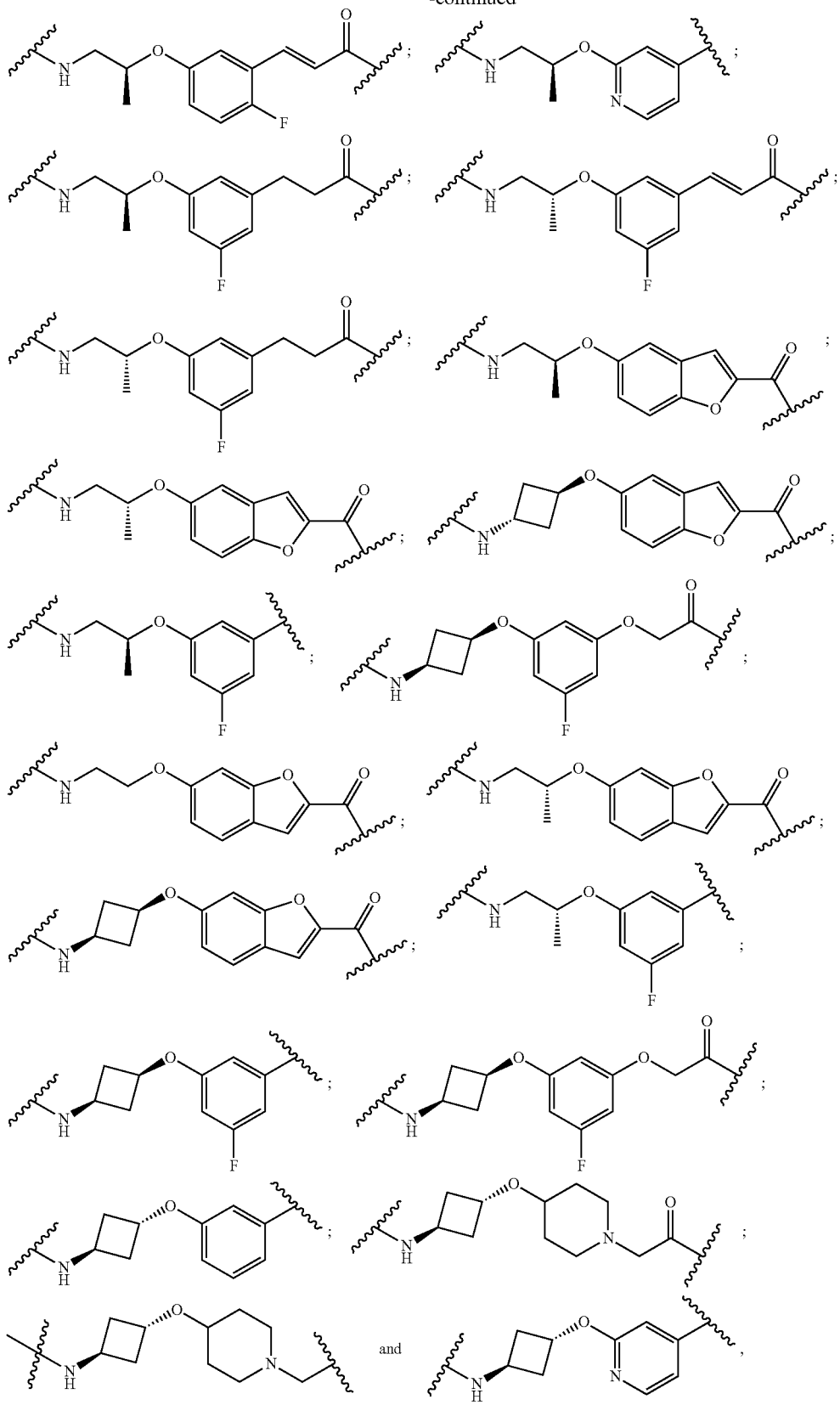
wherein each m and n is independently 0, 1, 2, 3, 4, 5, or 6.

In some embodiments, the linker (L) is selected from the group consisting of:
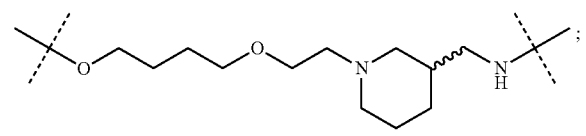
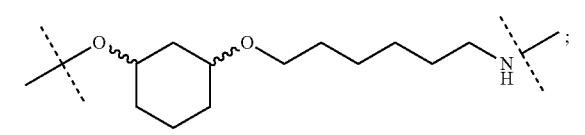
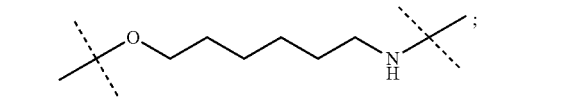
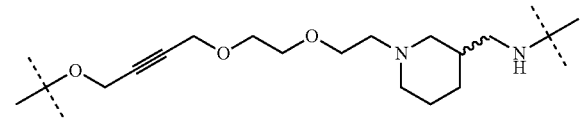
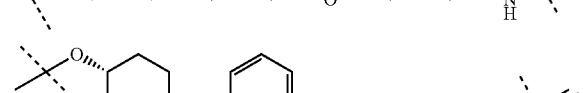
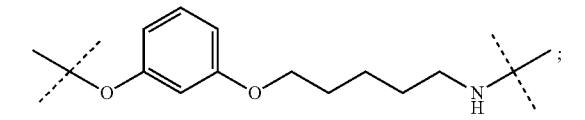
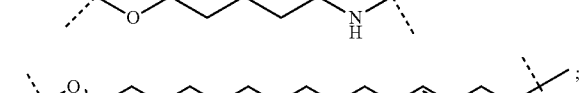
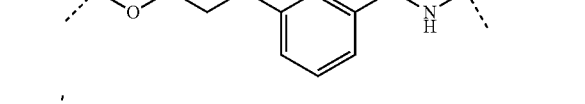
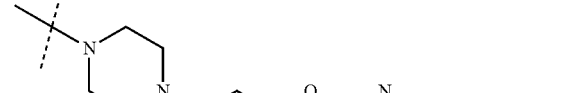

-continued
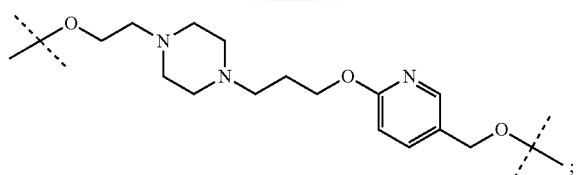
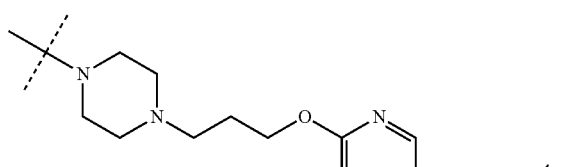
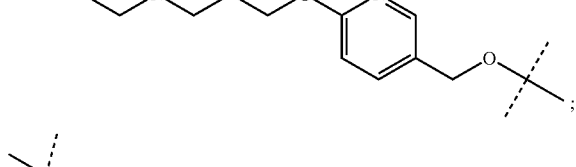
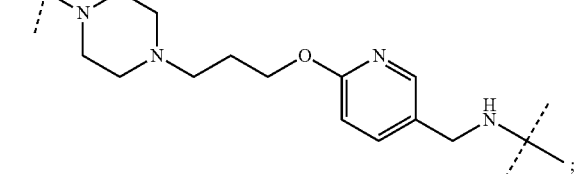
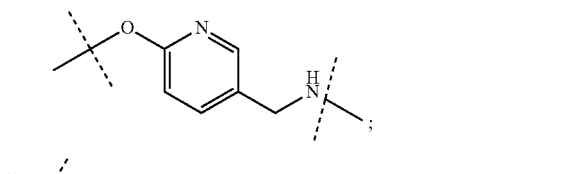
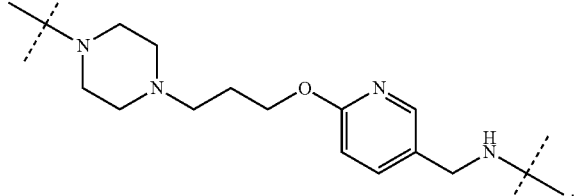
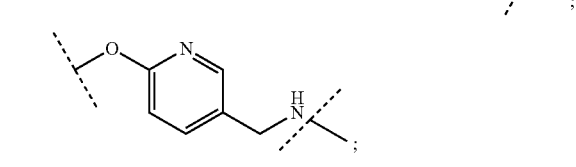
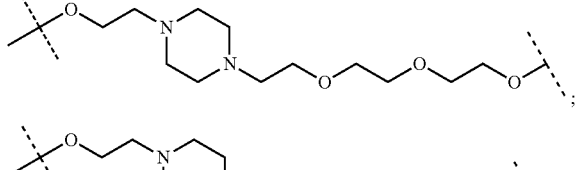
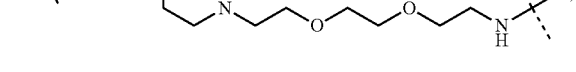

327
-continued
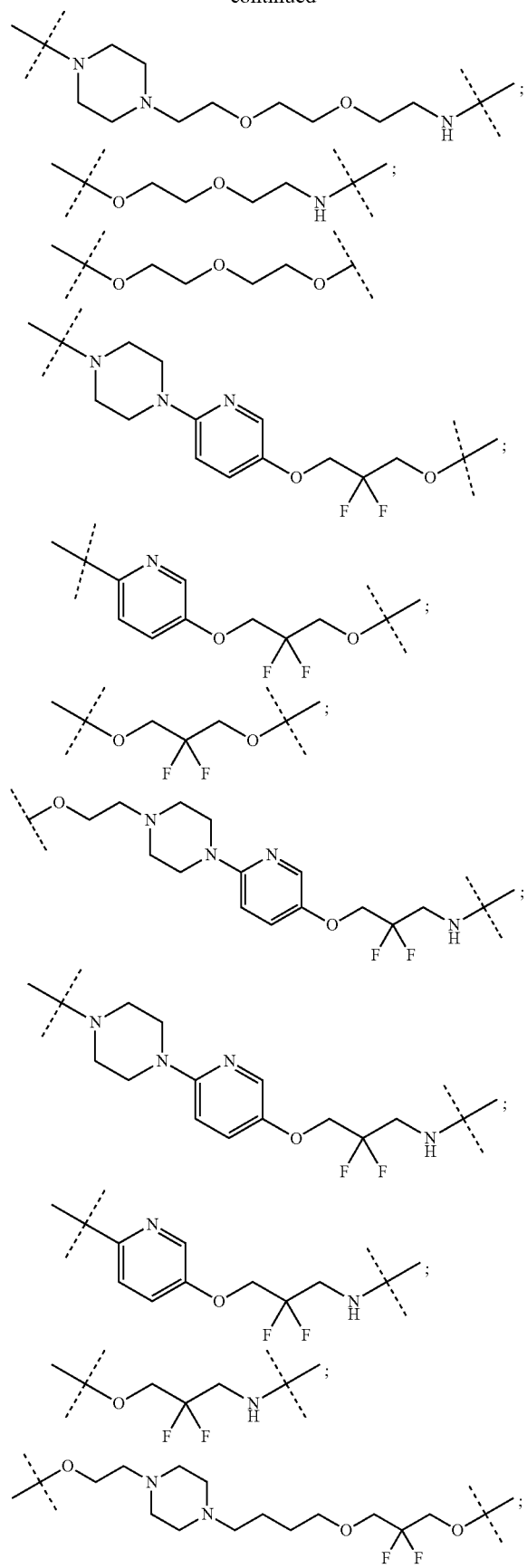
328
-continued
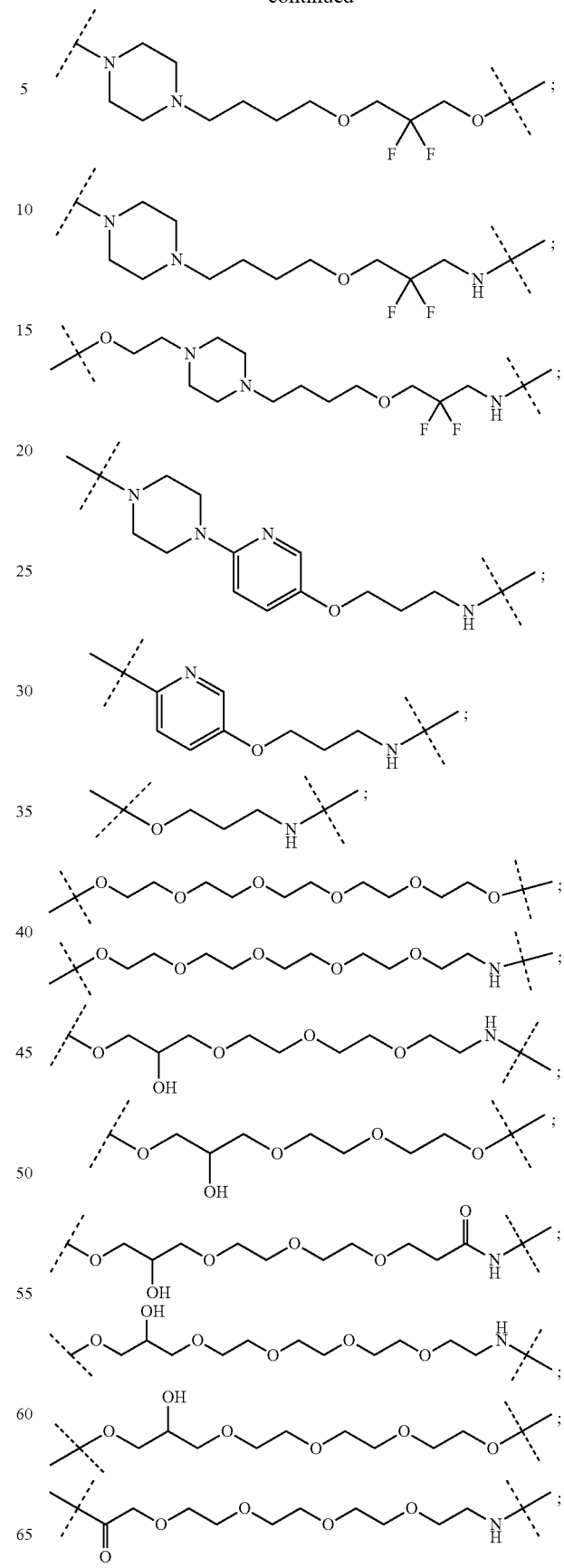

-continued
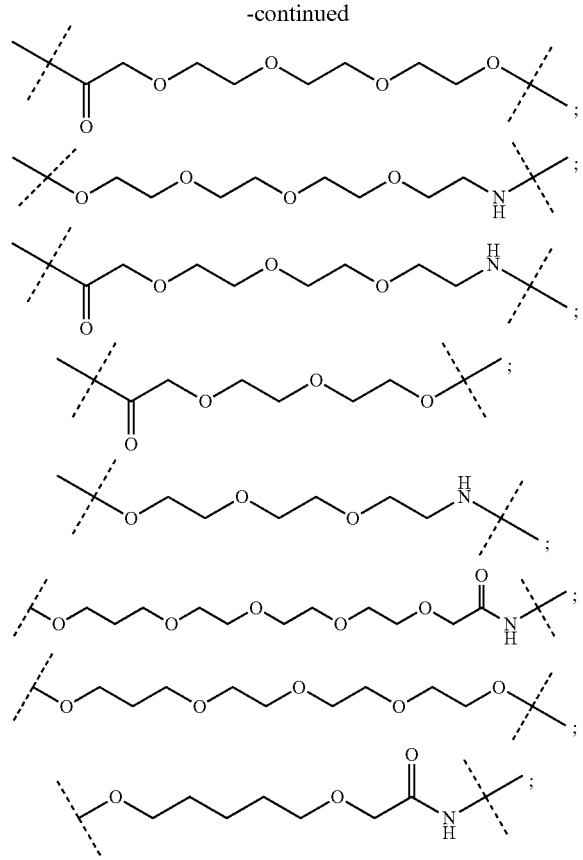
-continued
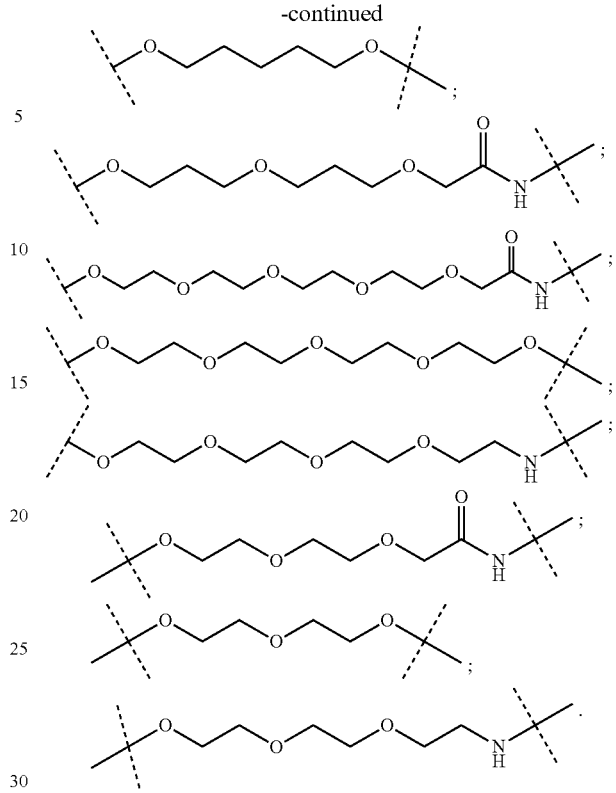
In some embodiments, the linker (L) is selected from the group consisting of:
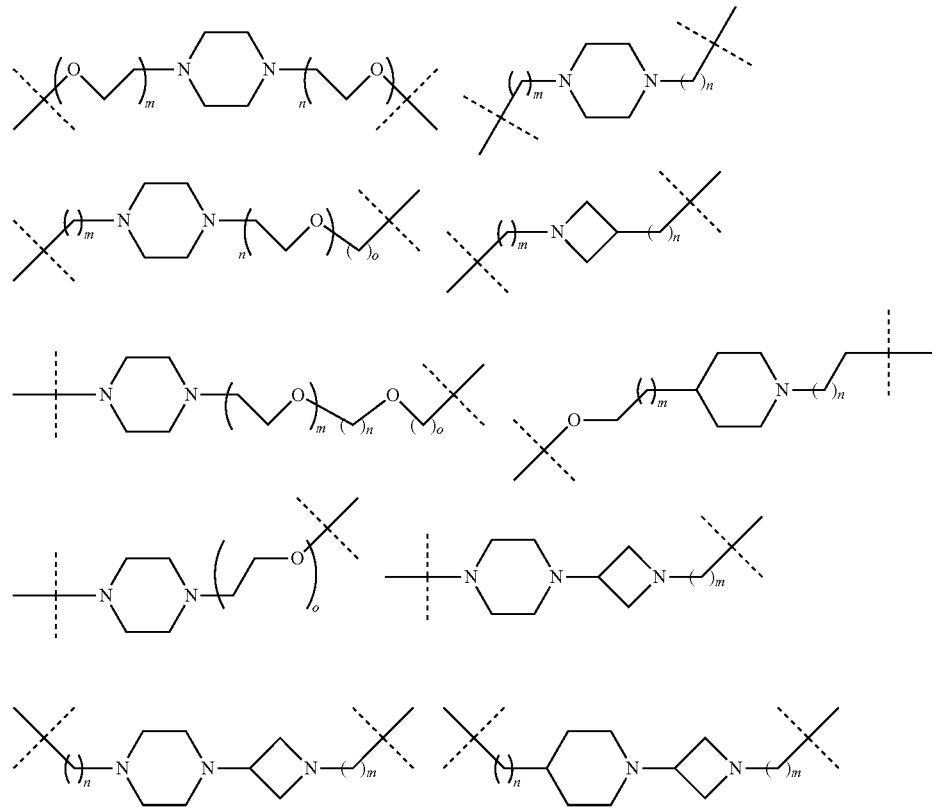

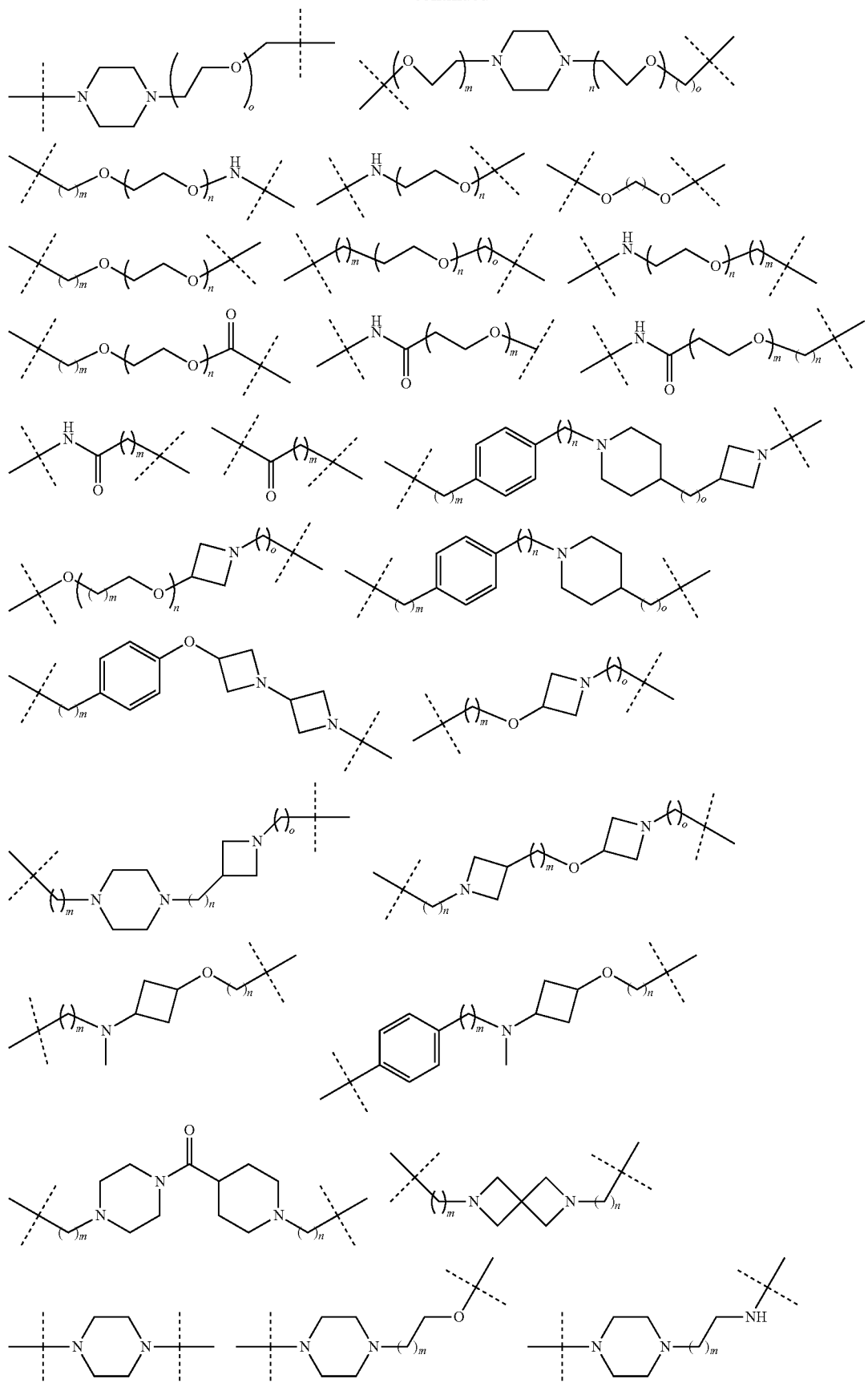

-continued
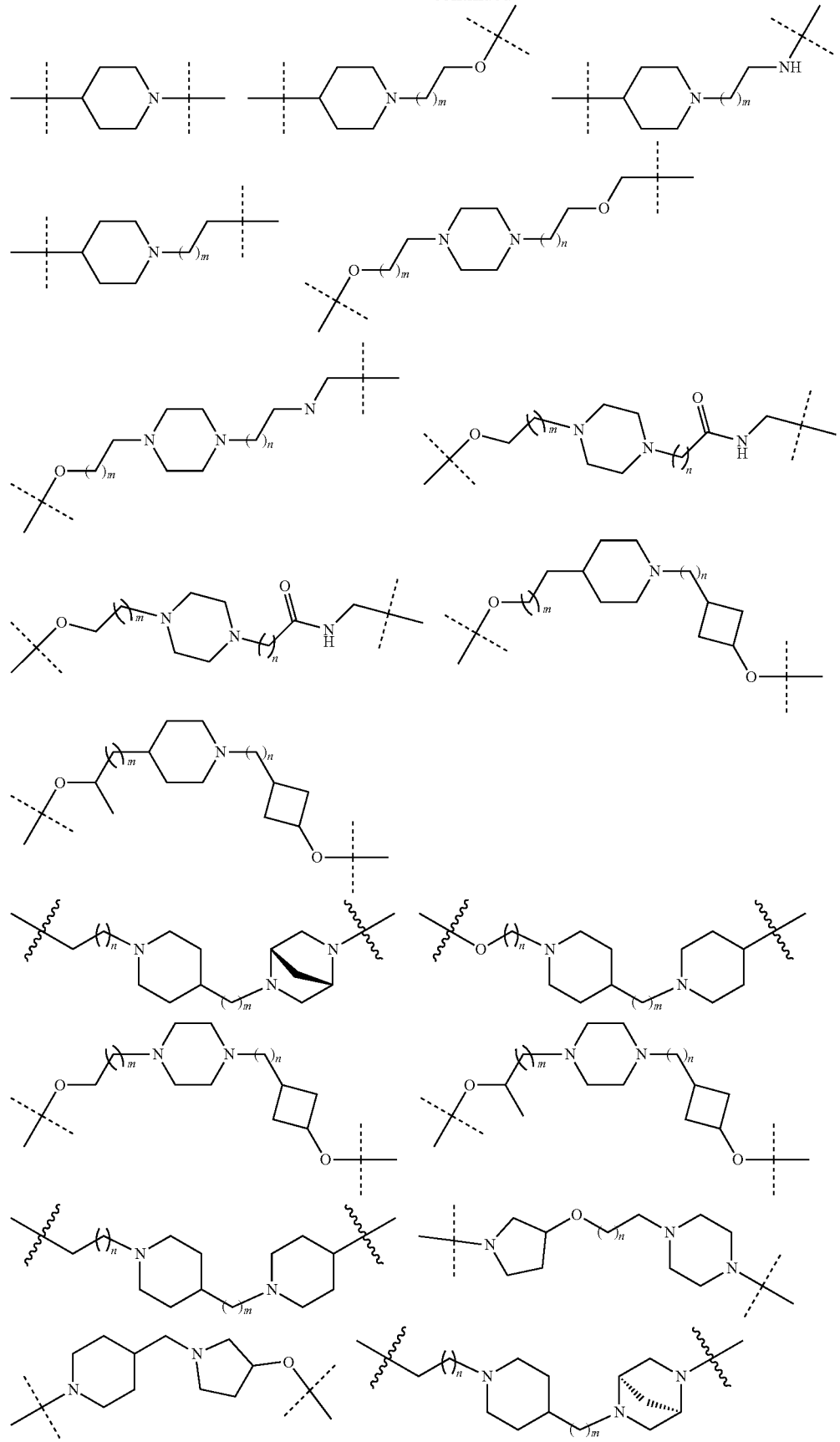

-continued
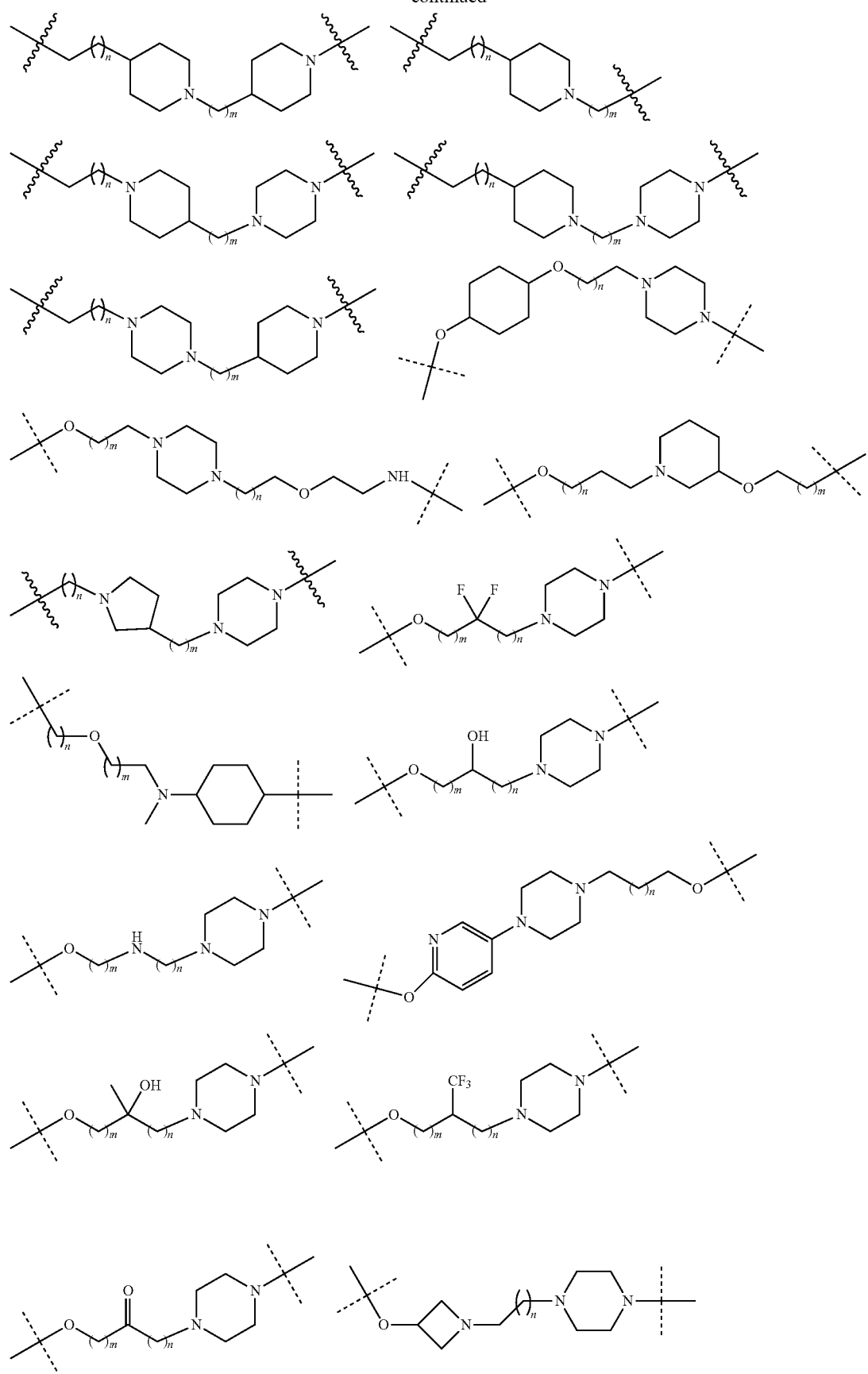

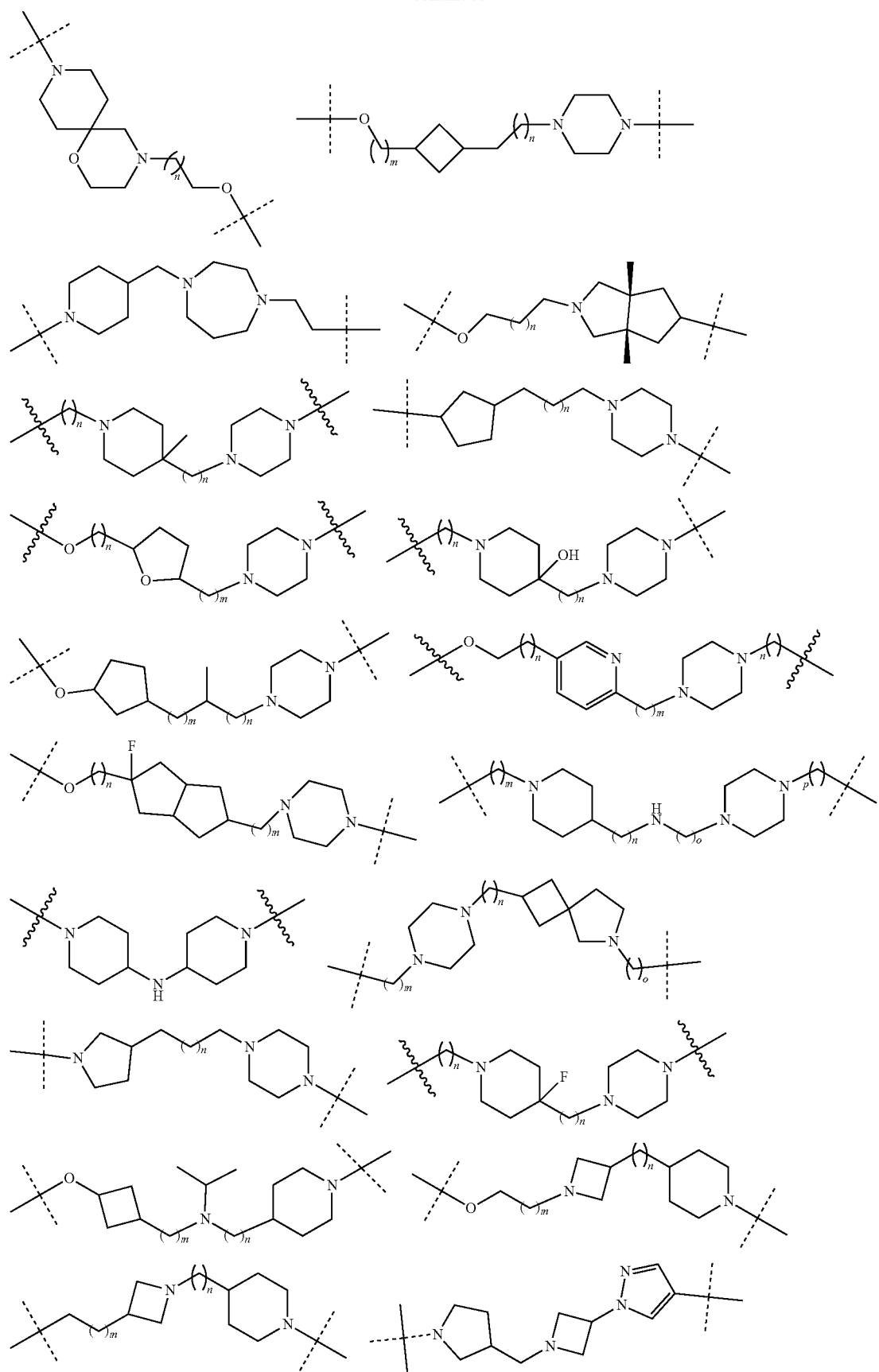

-continued
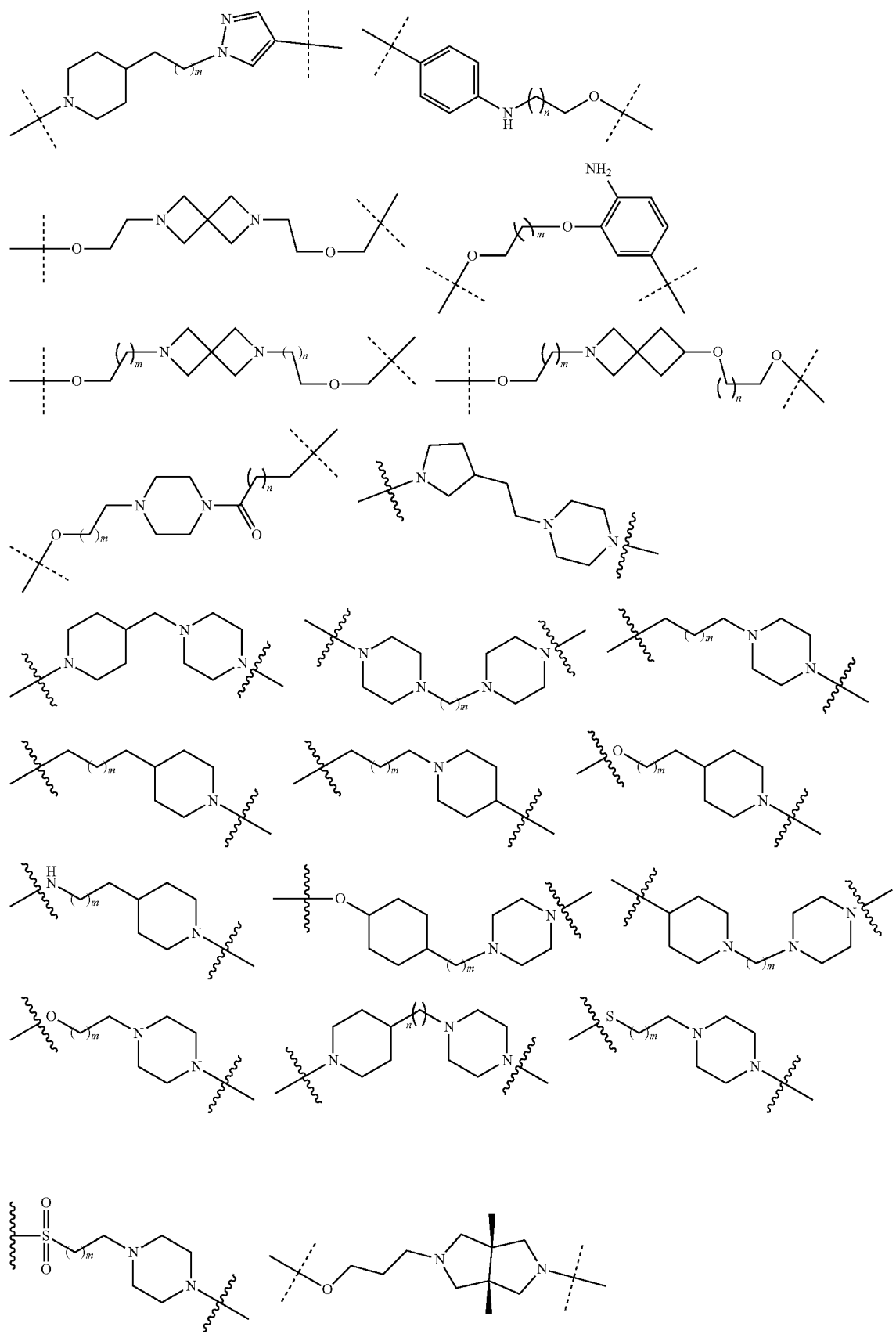

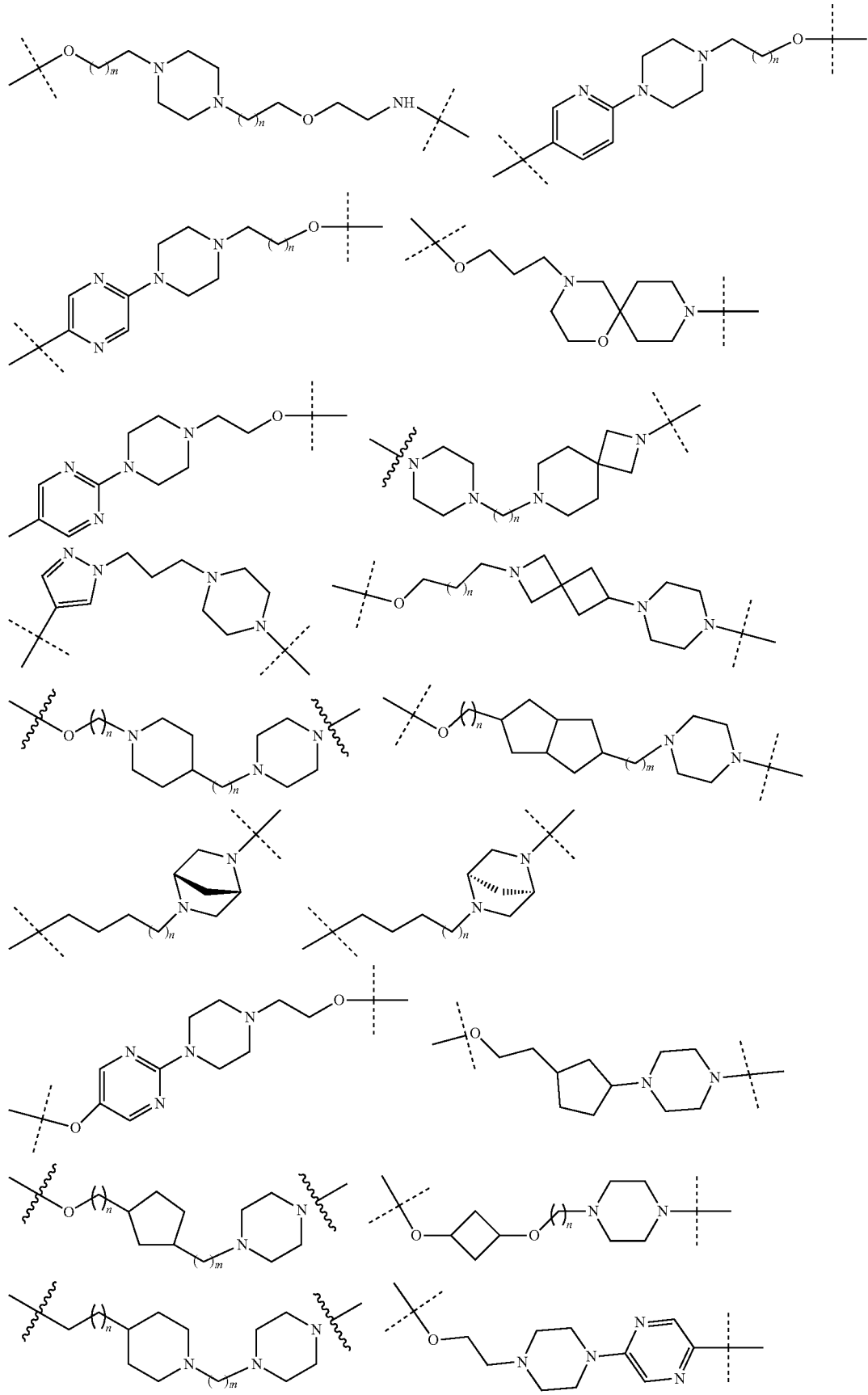

-continued
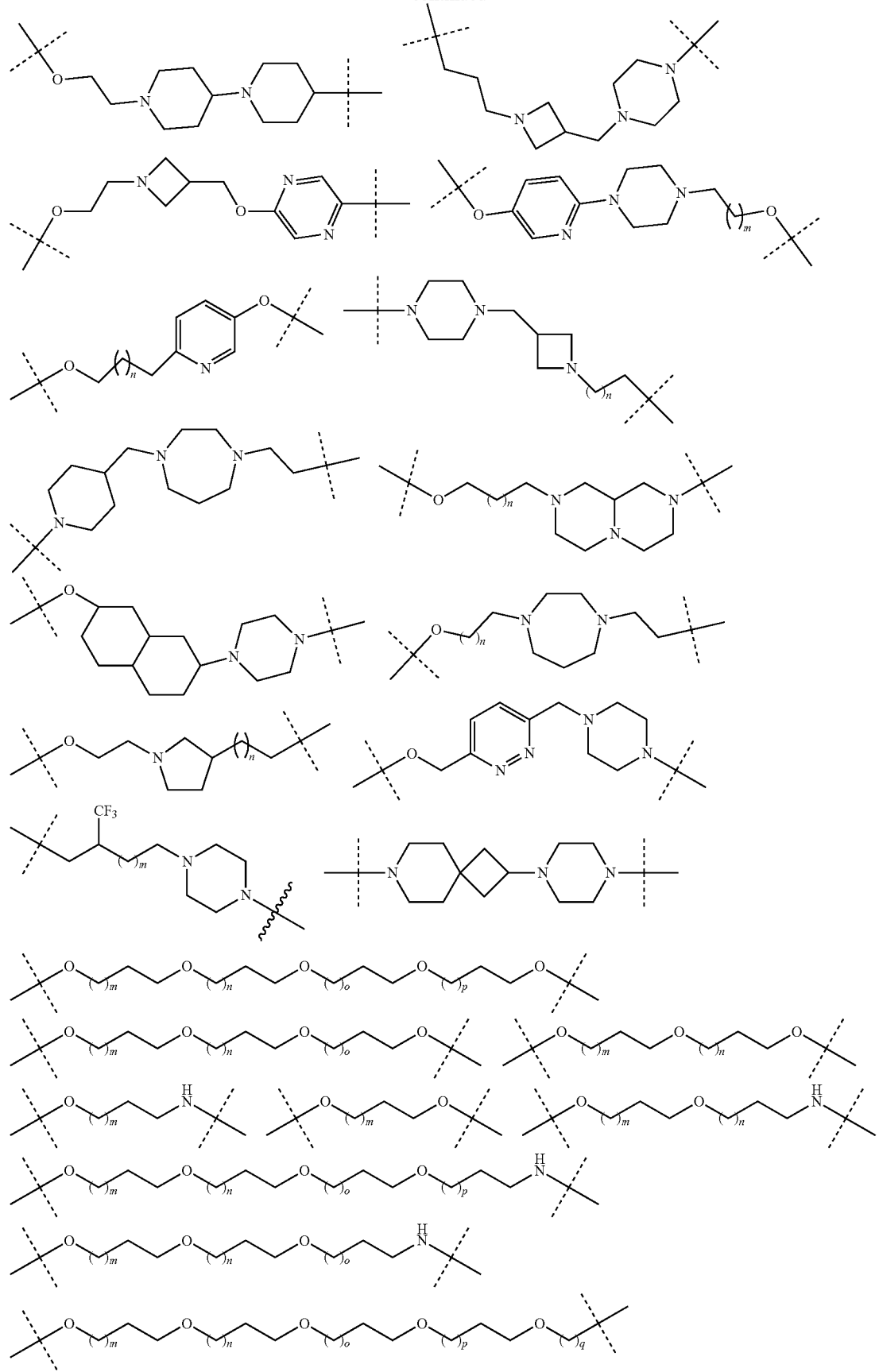

345 346
-continued
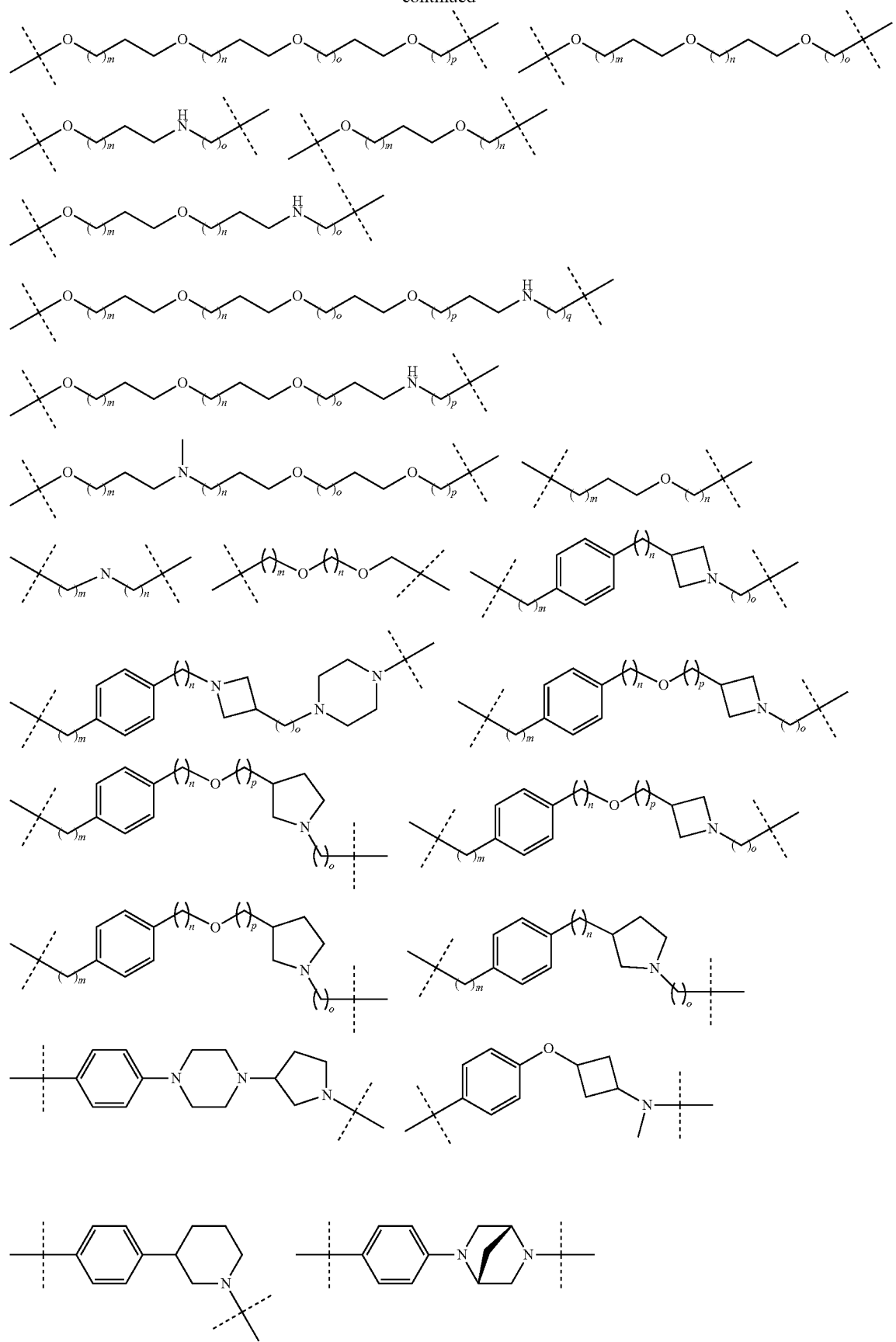

-continued
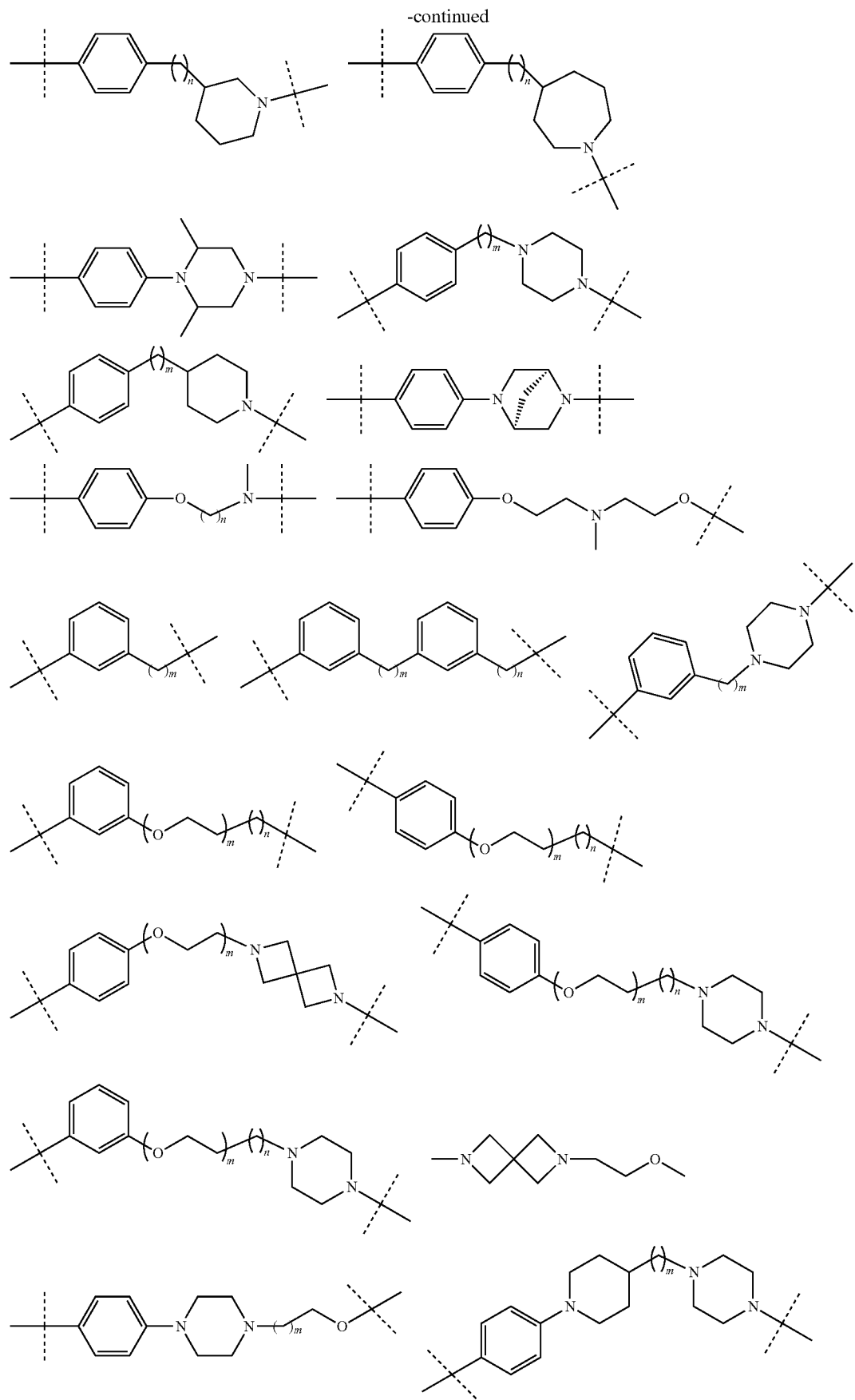

-continued
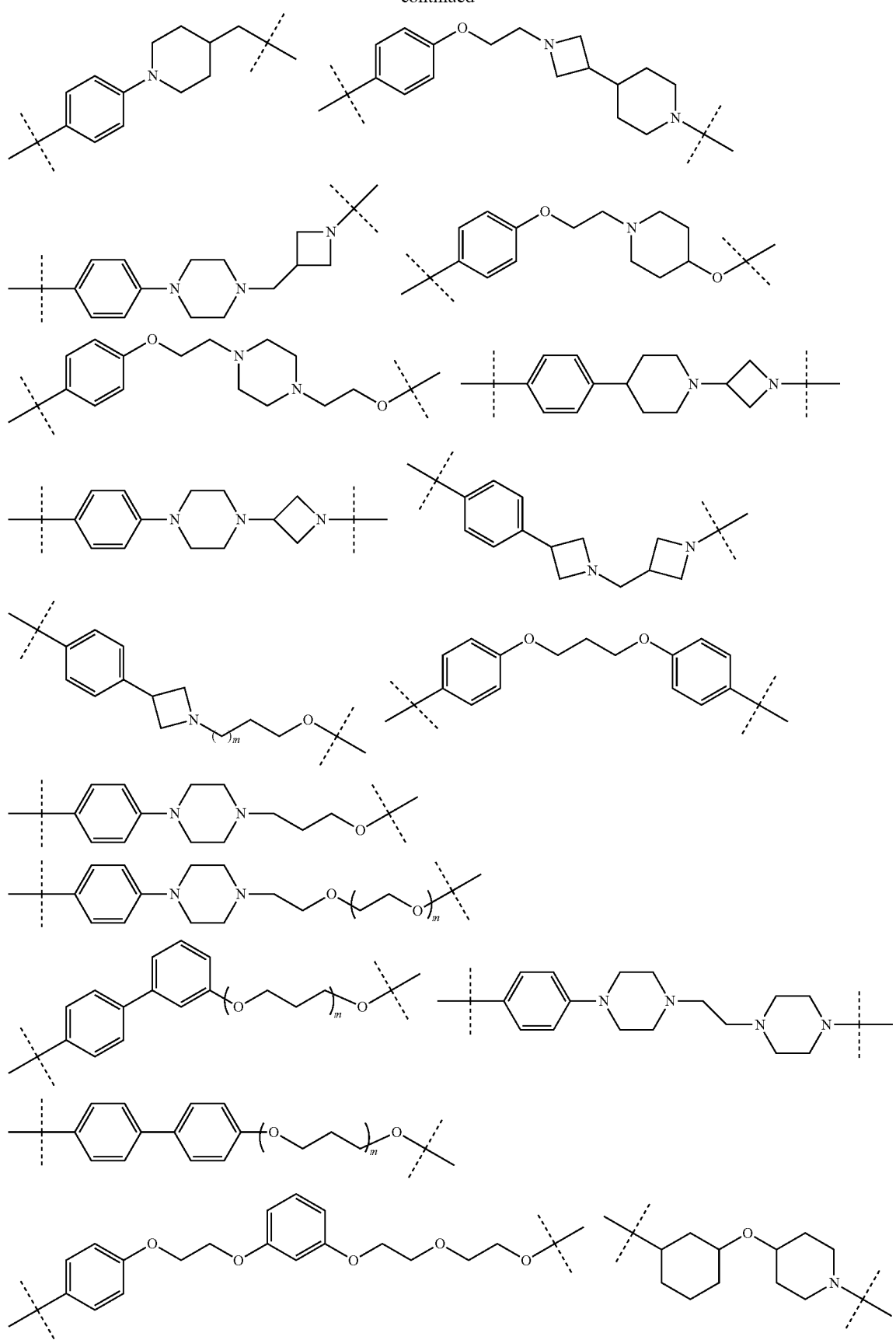

351 352
-continued
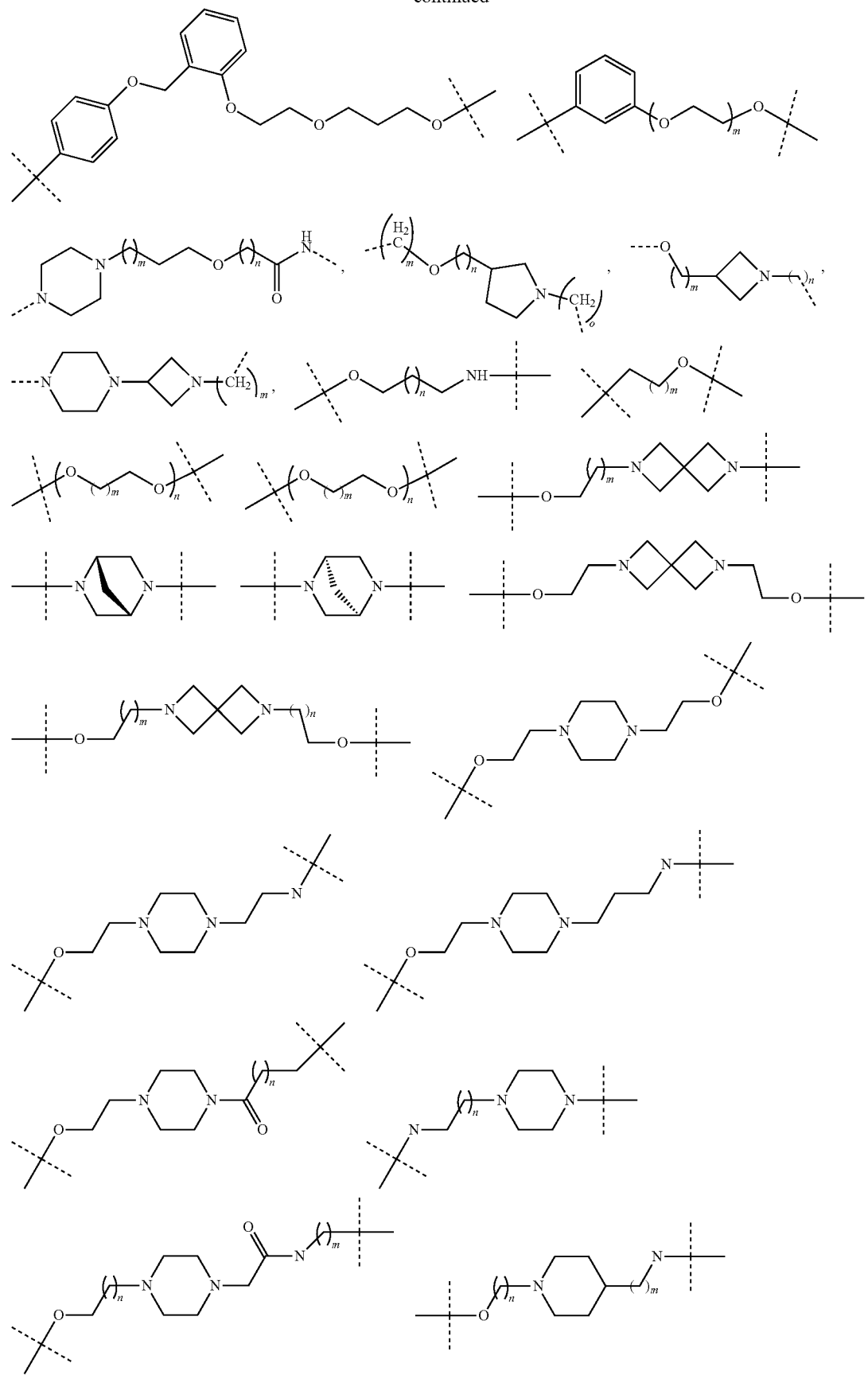

-continued
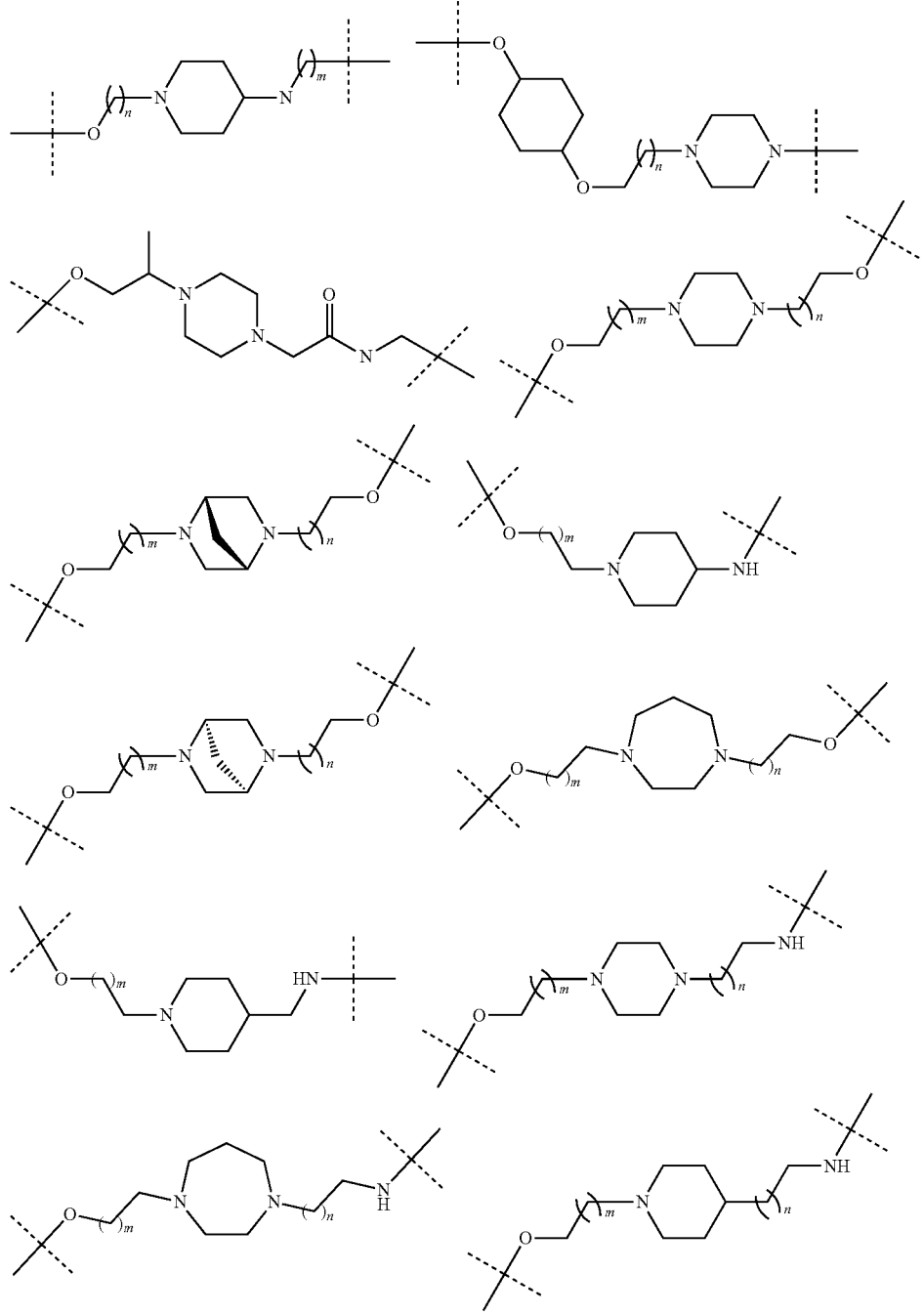
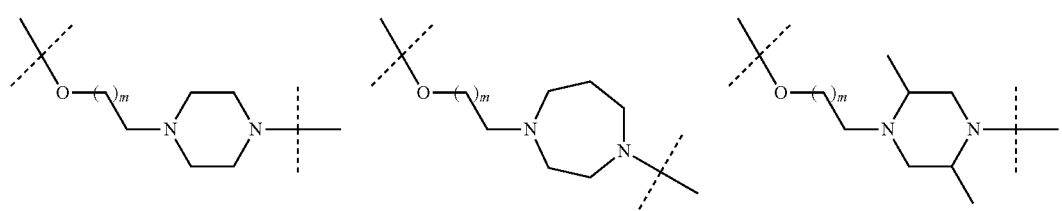

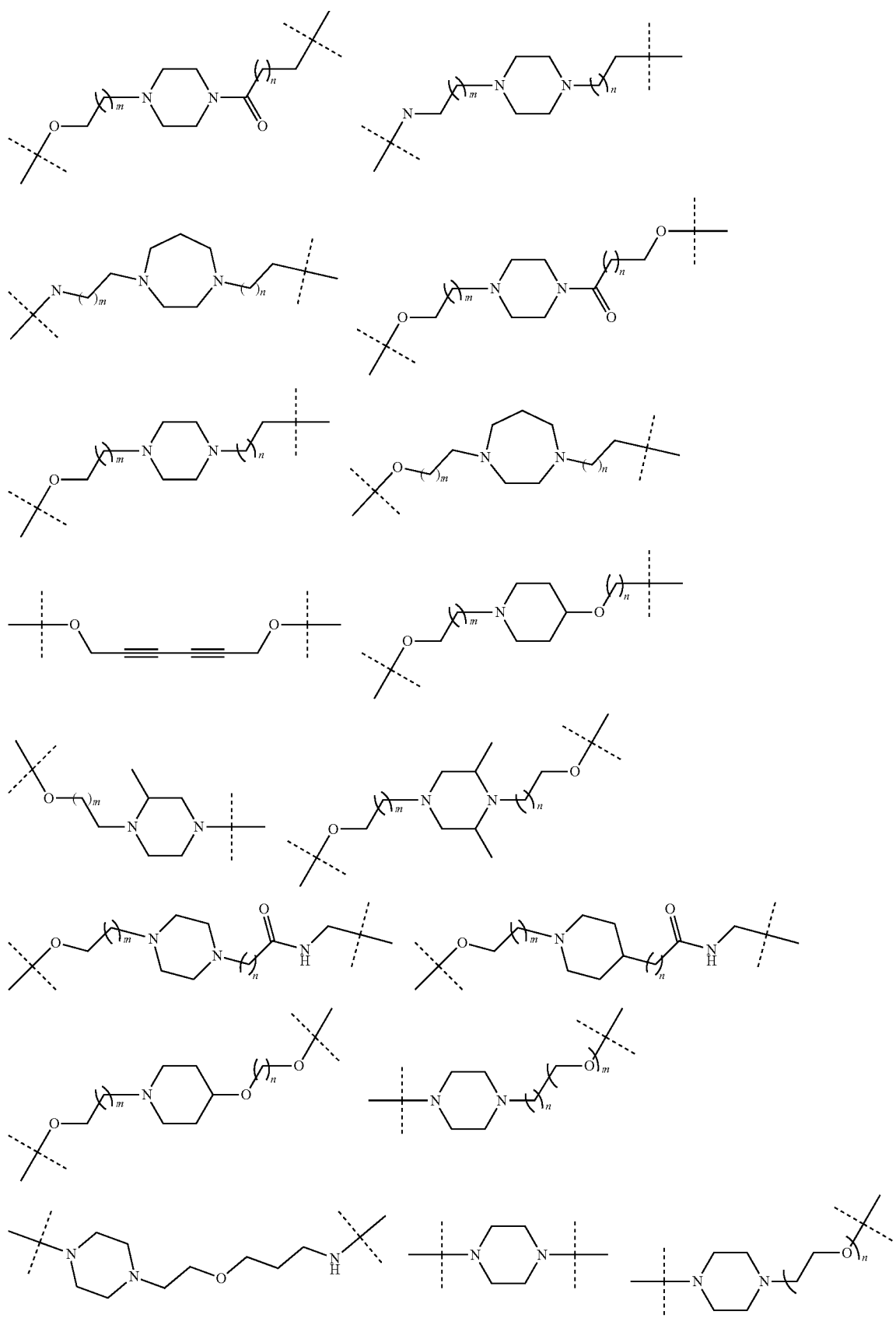

-continued
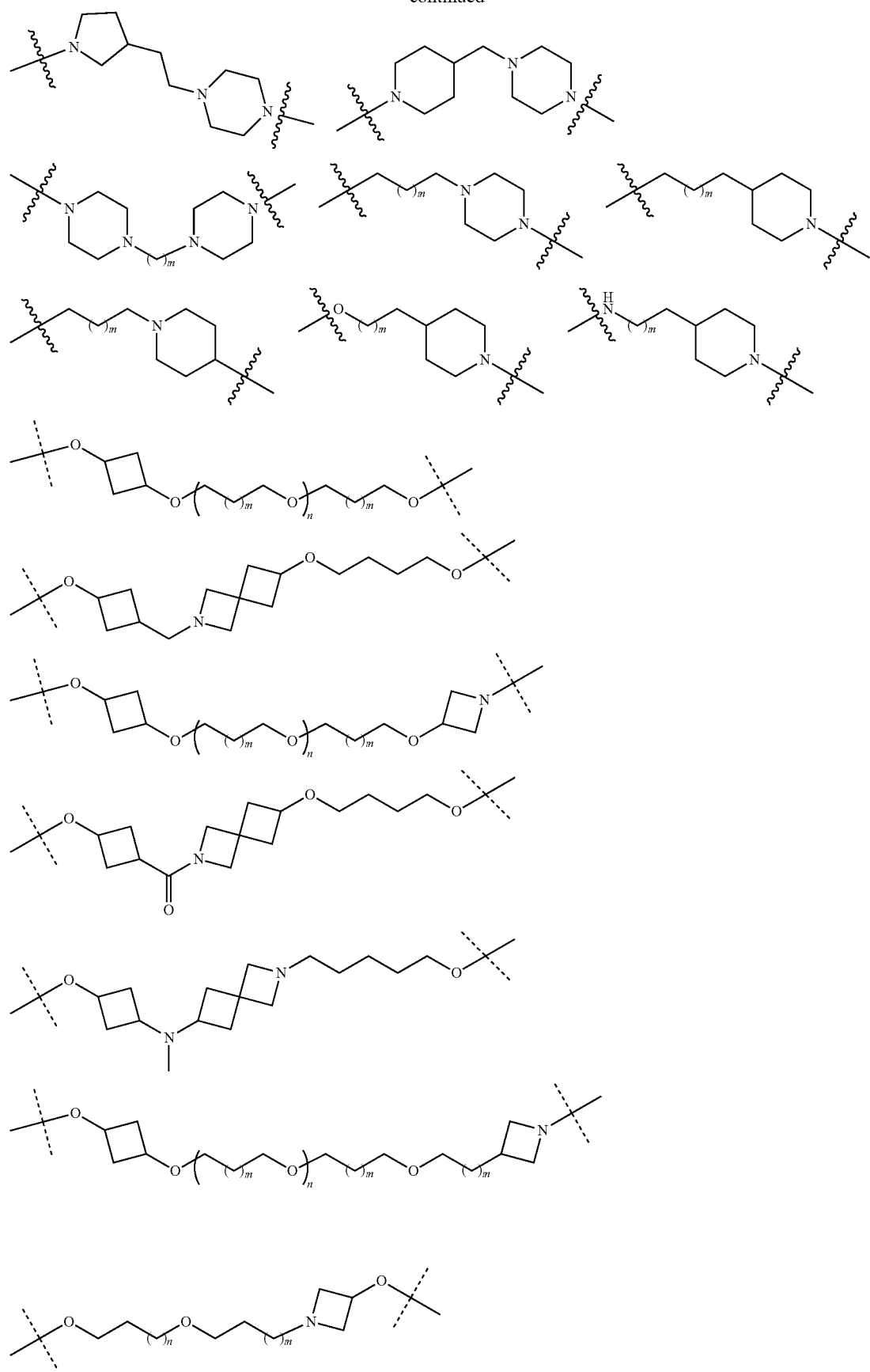

-continued
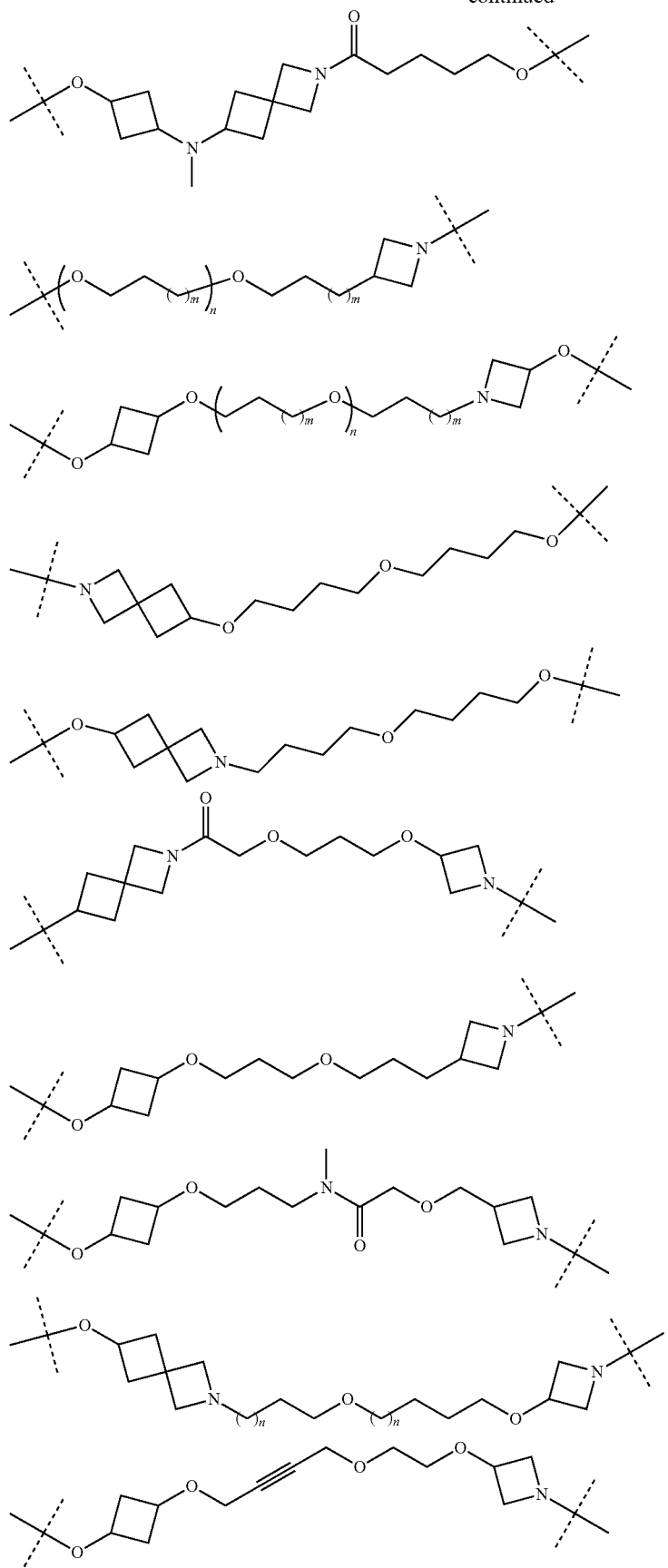

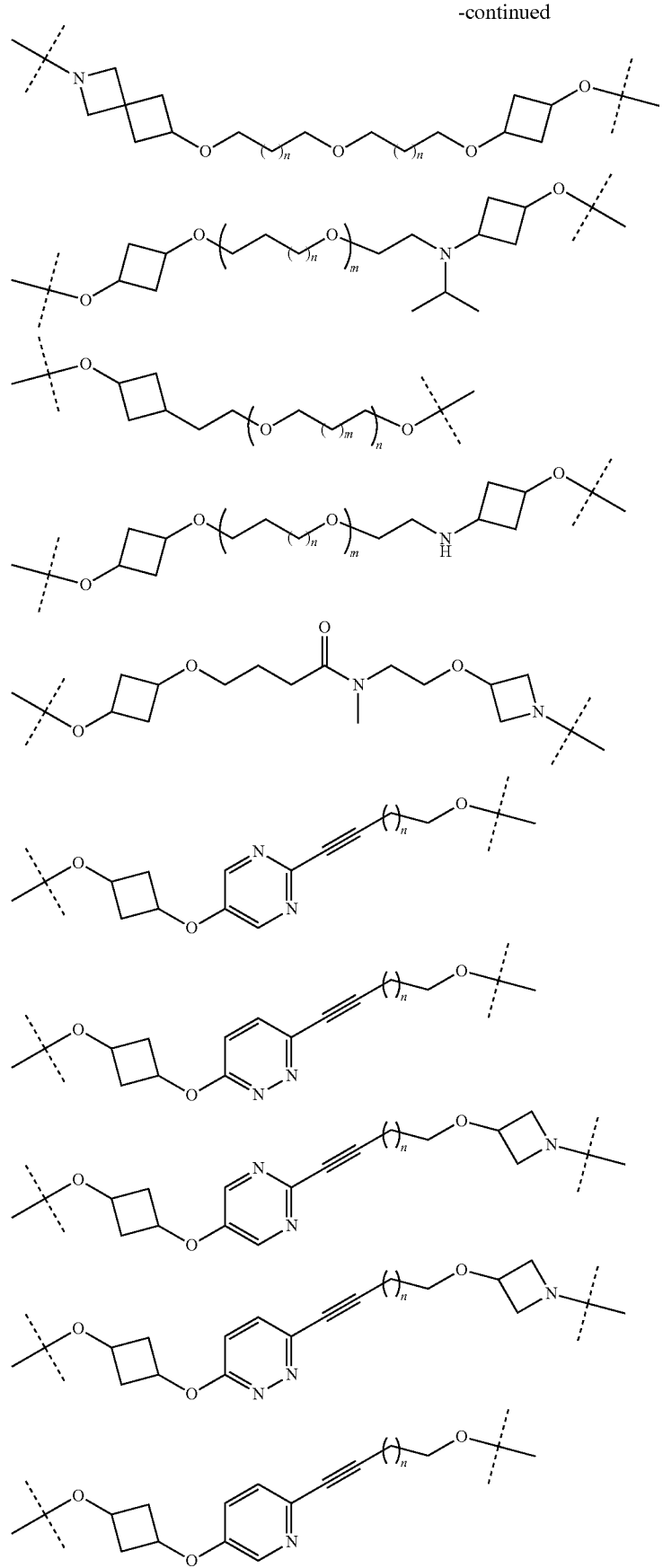

-continued
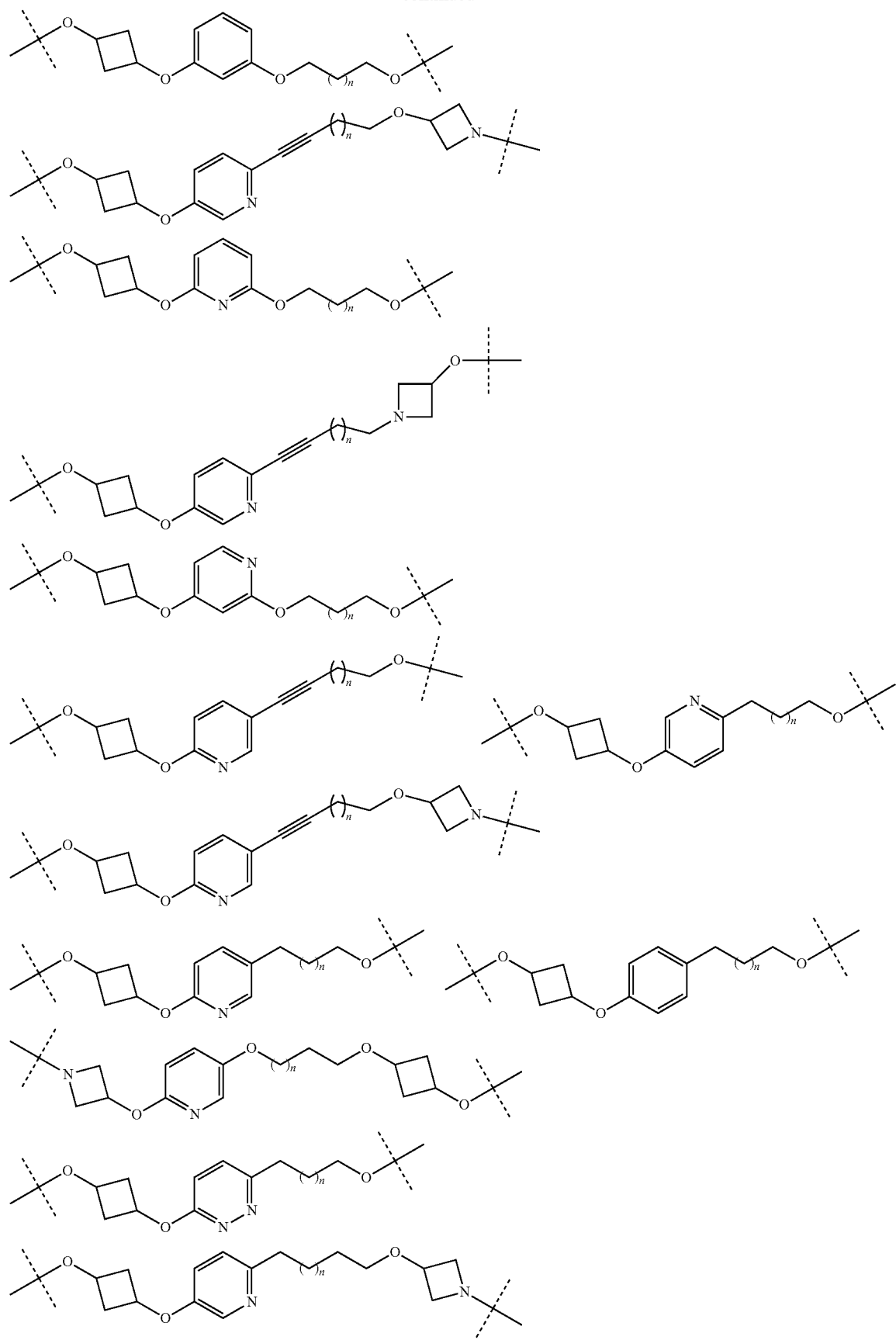

-continued
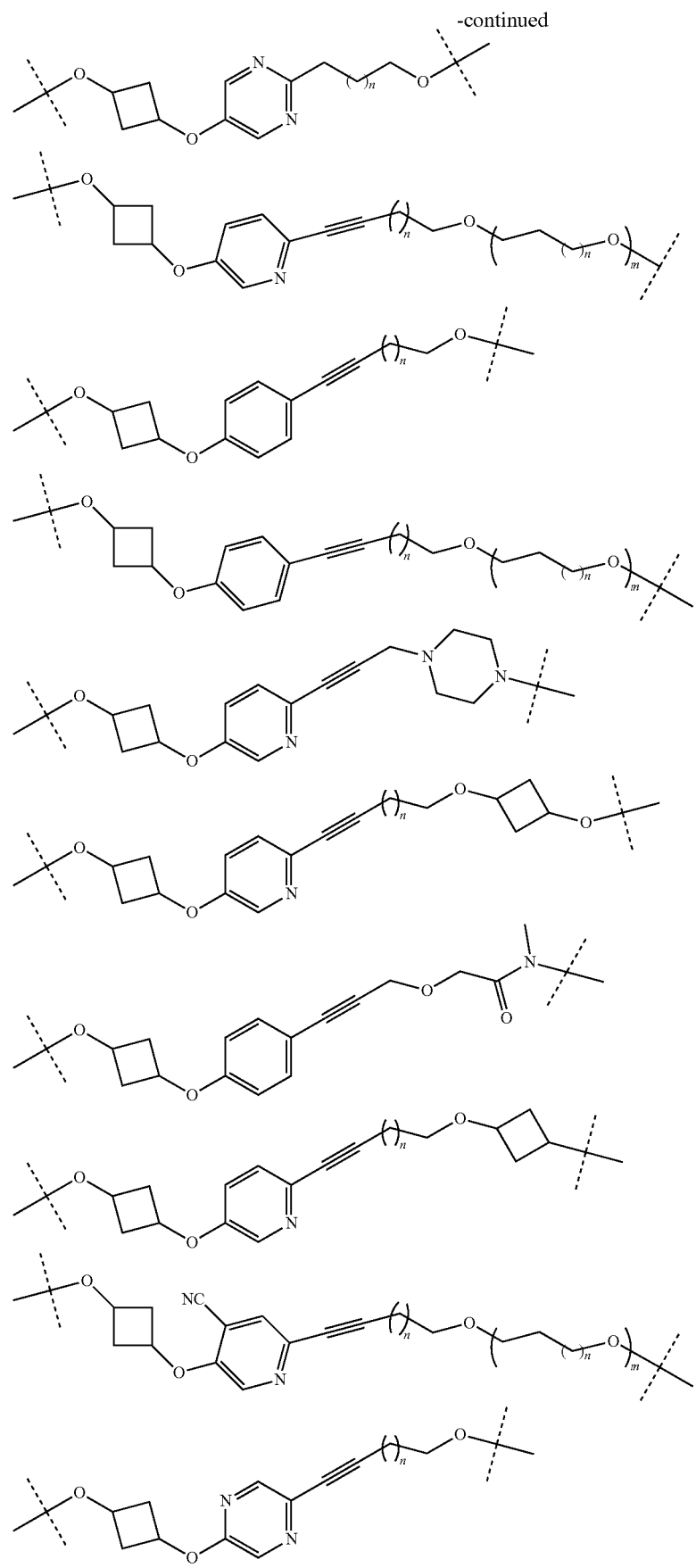

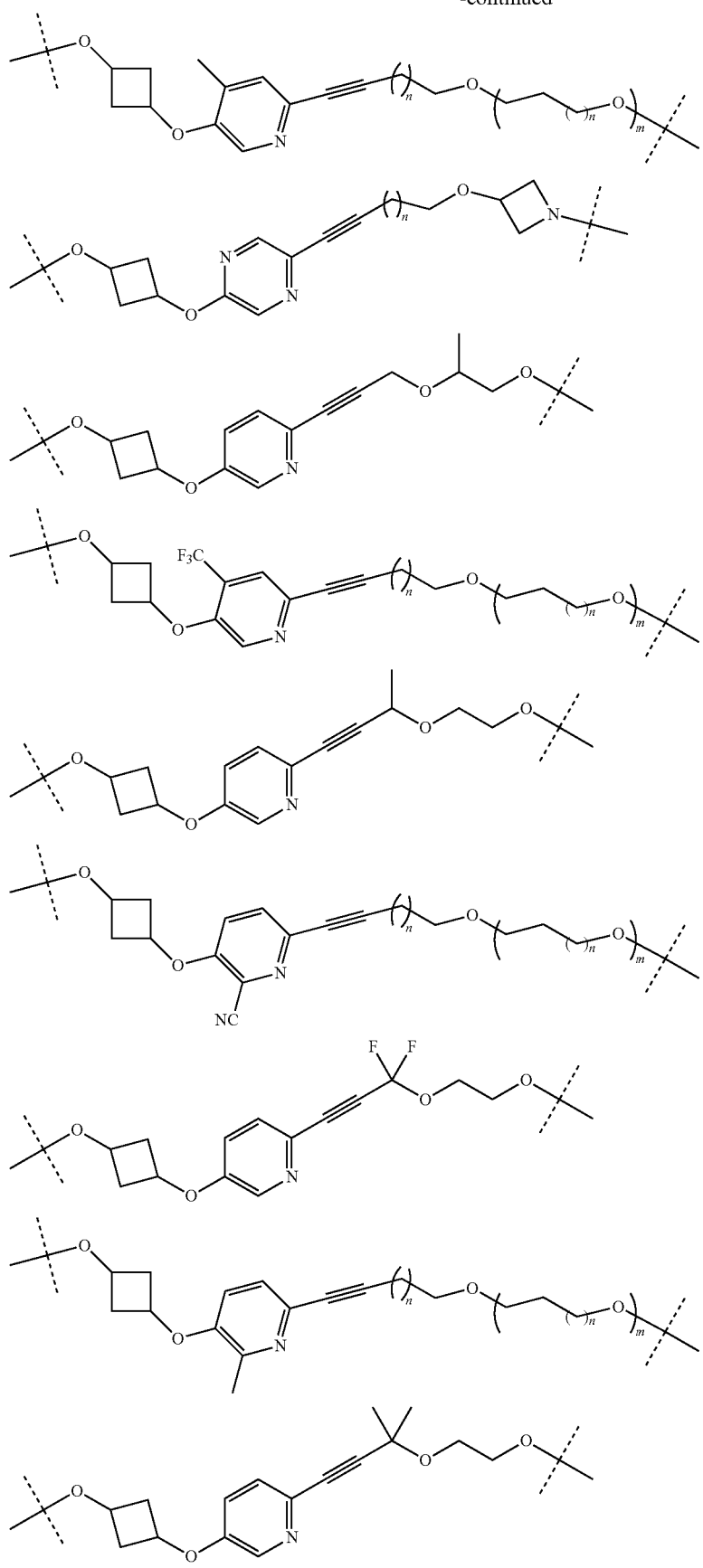

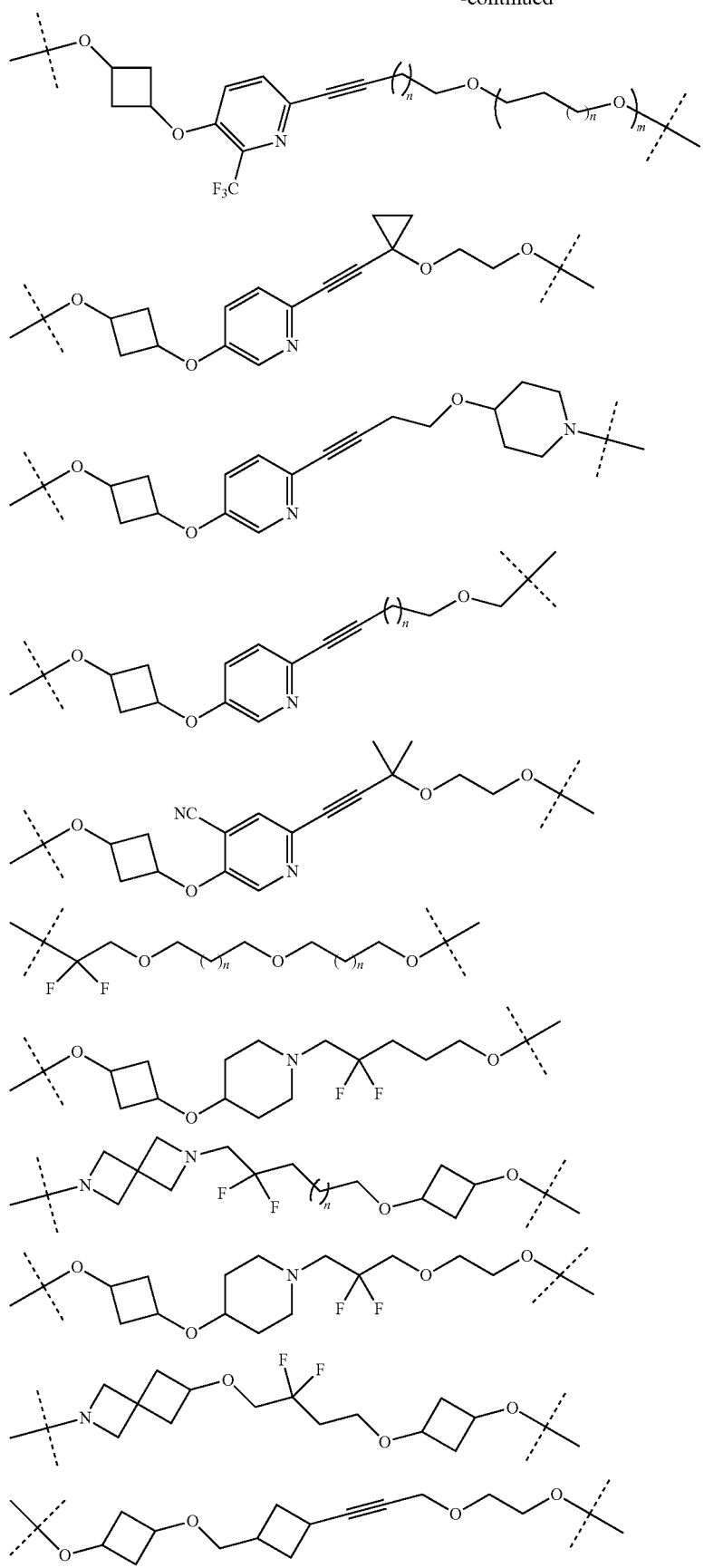

-continued
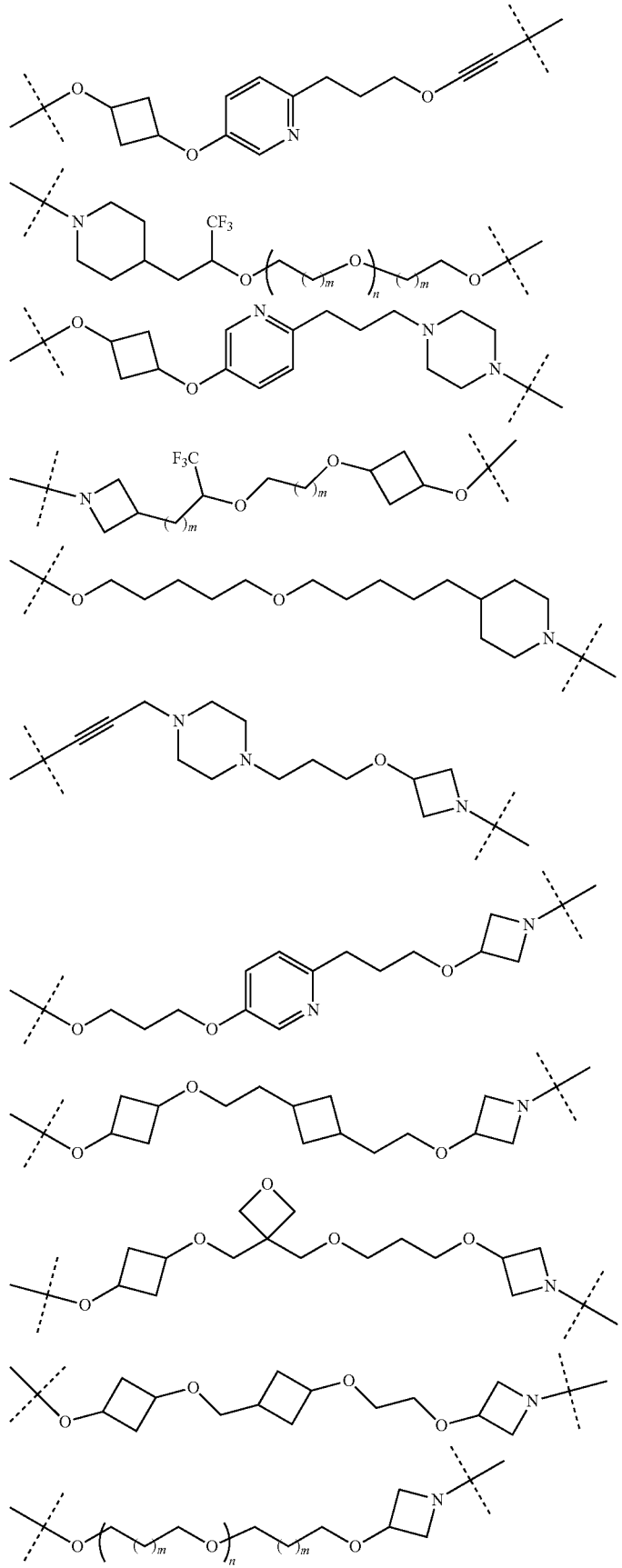

-continued
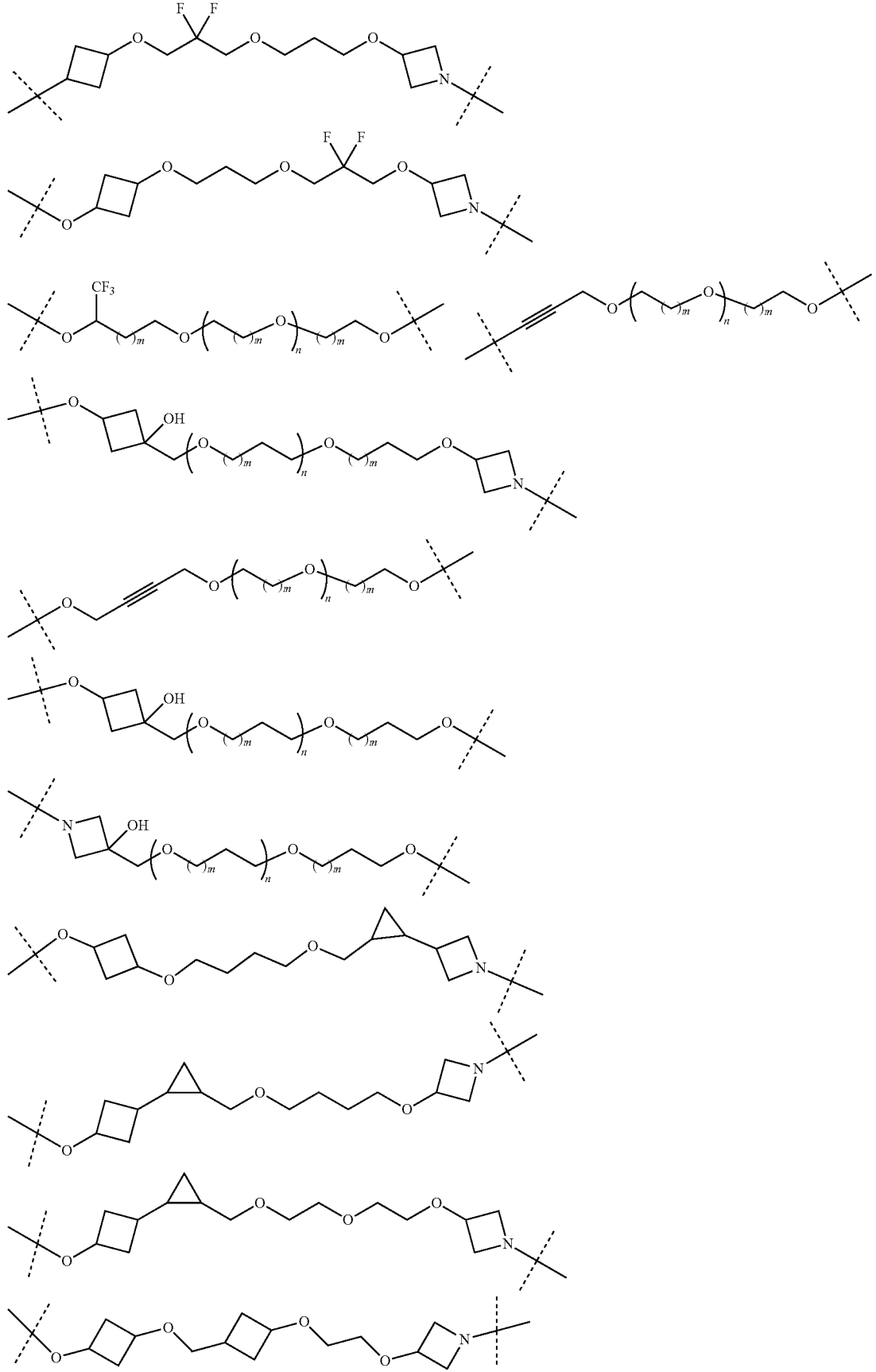

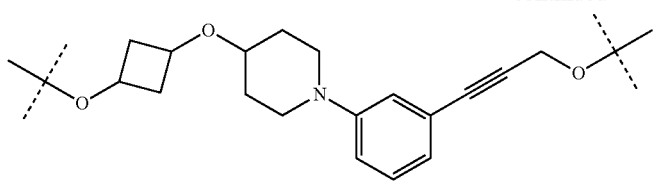
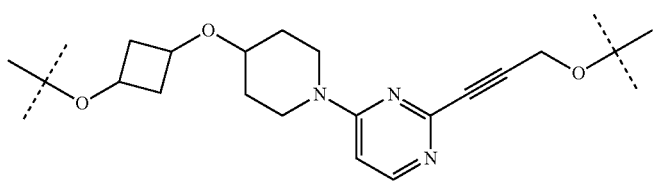
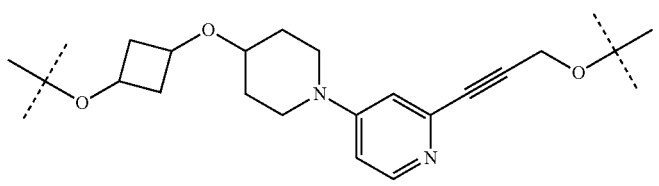
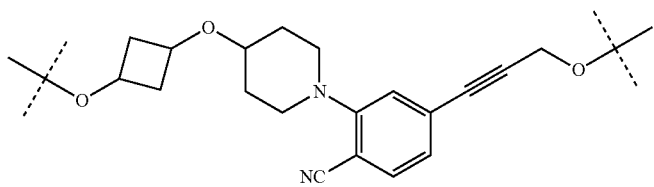
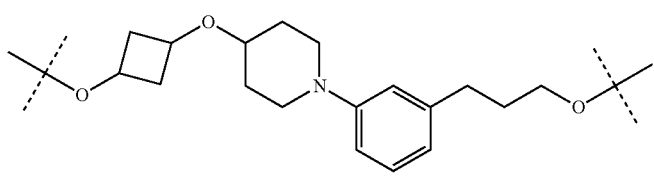
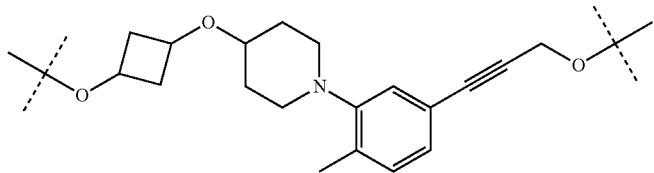
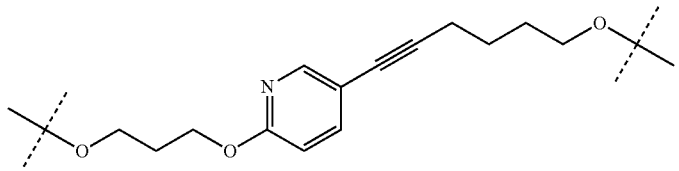
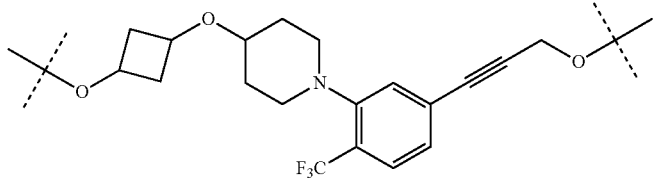
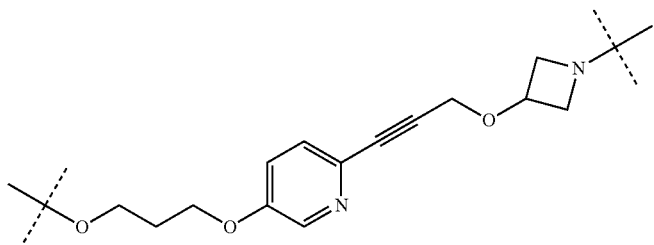

-continued
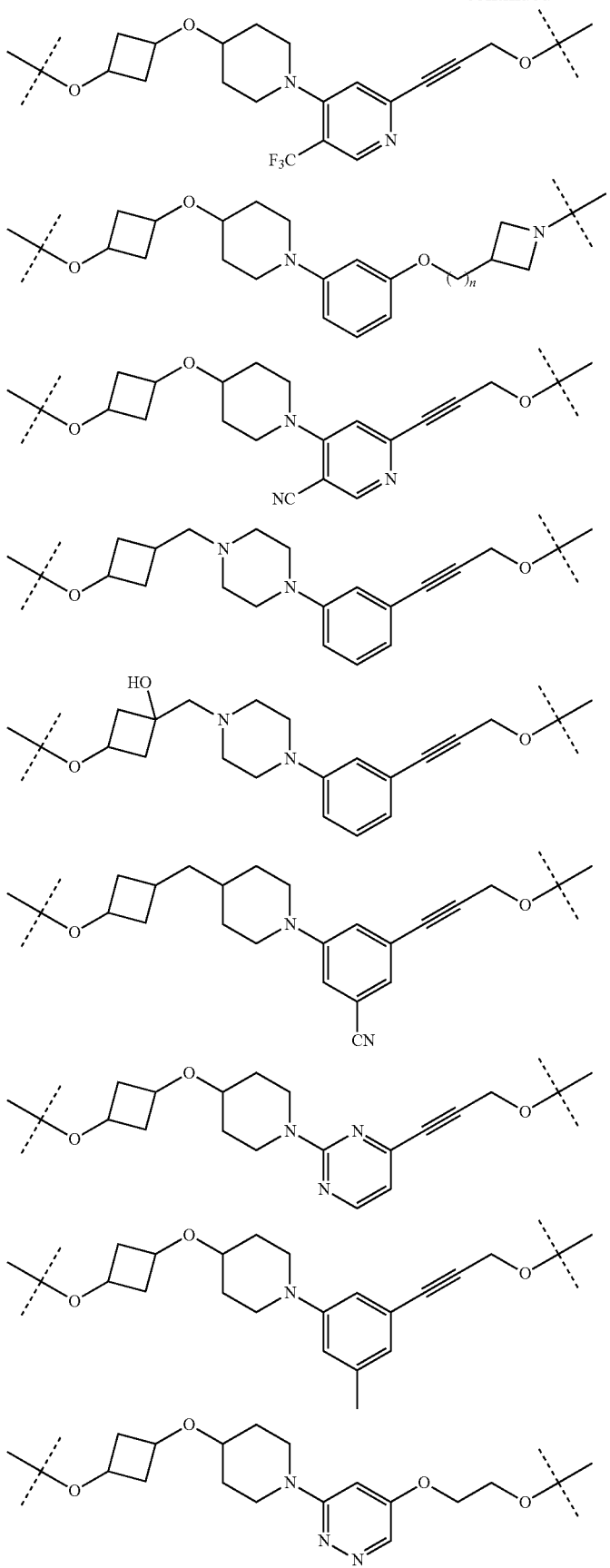

-continued
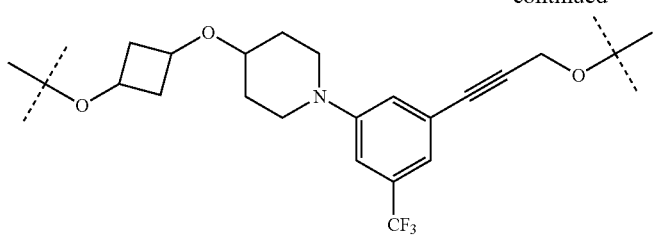
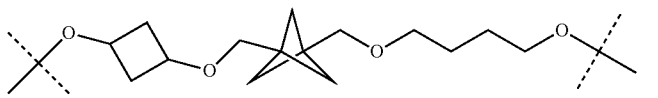
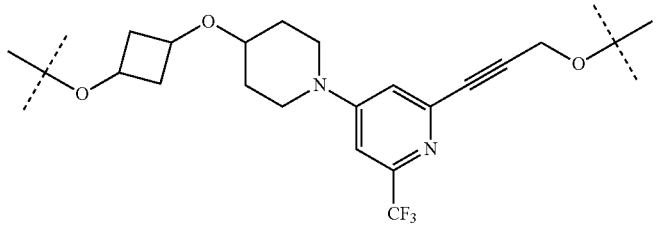
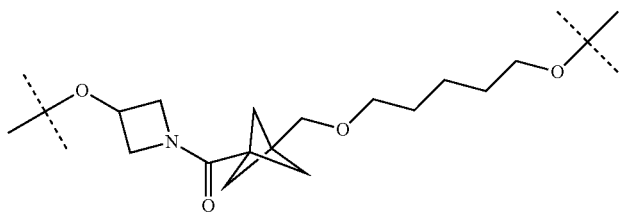
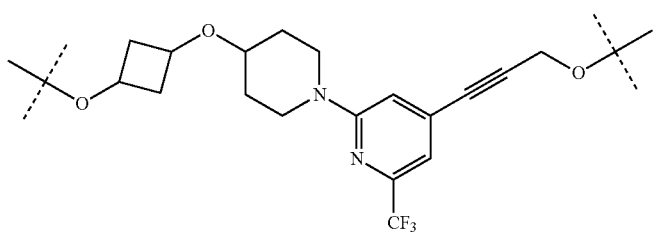
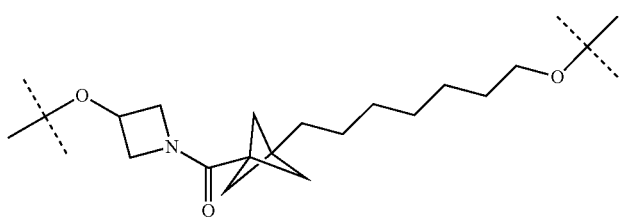
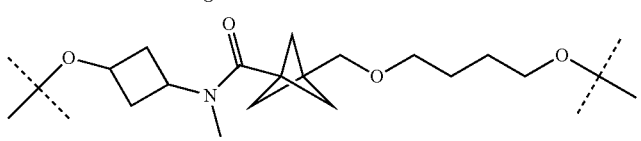
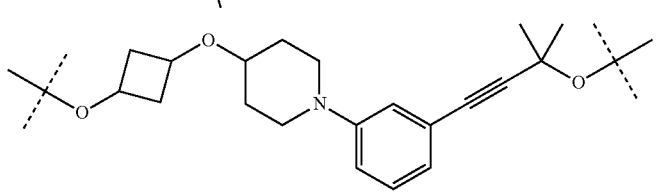
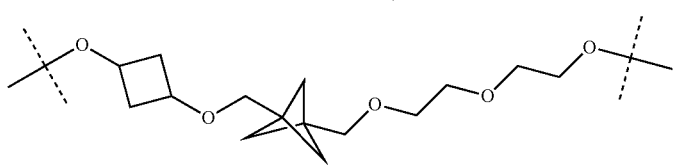

-continued
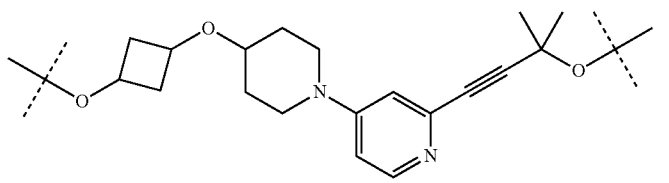
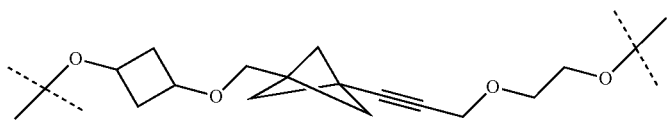
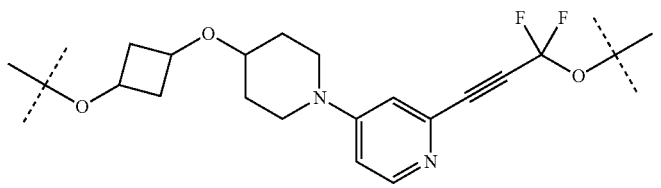
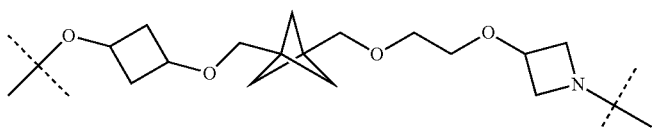
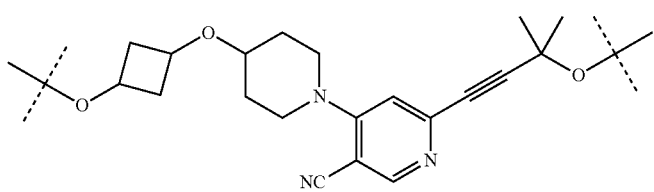
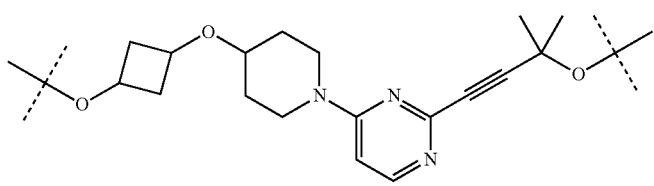
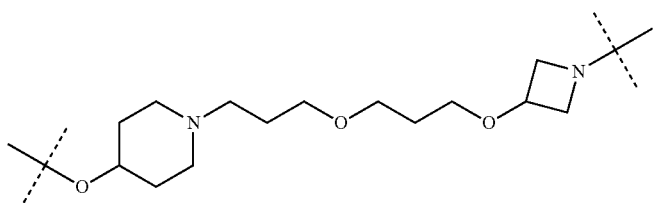
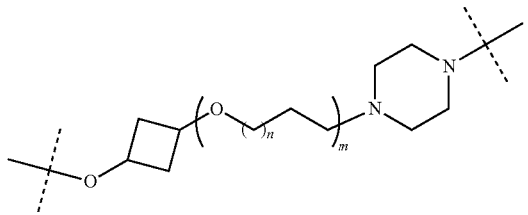
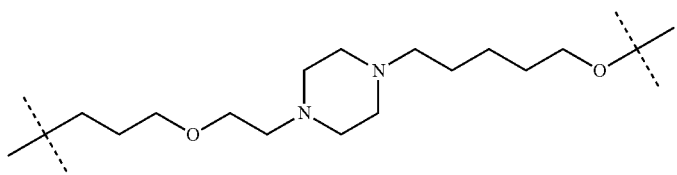

-continued
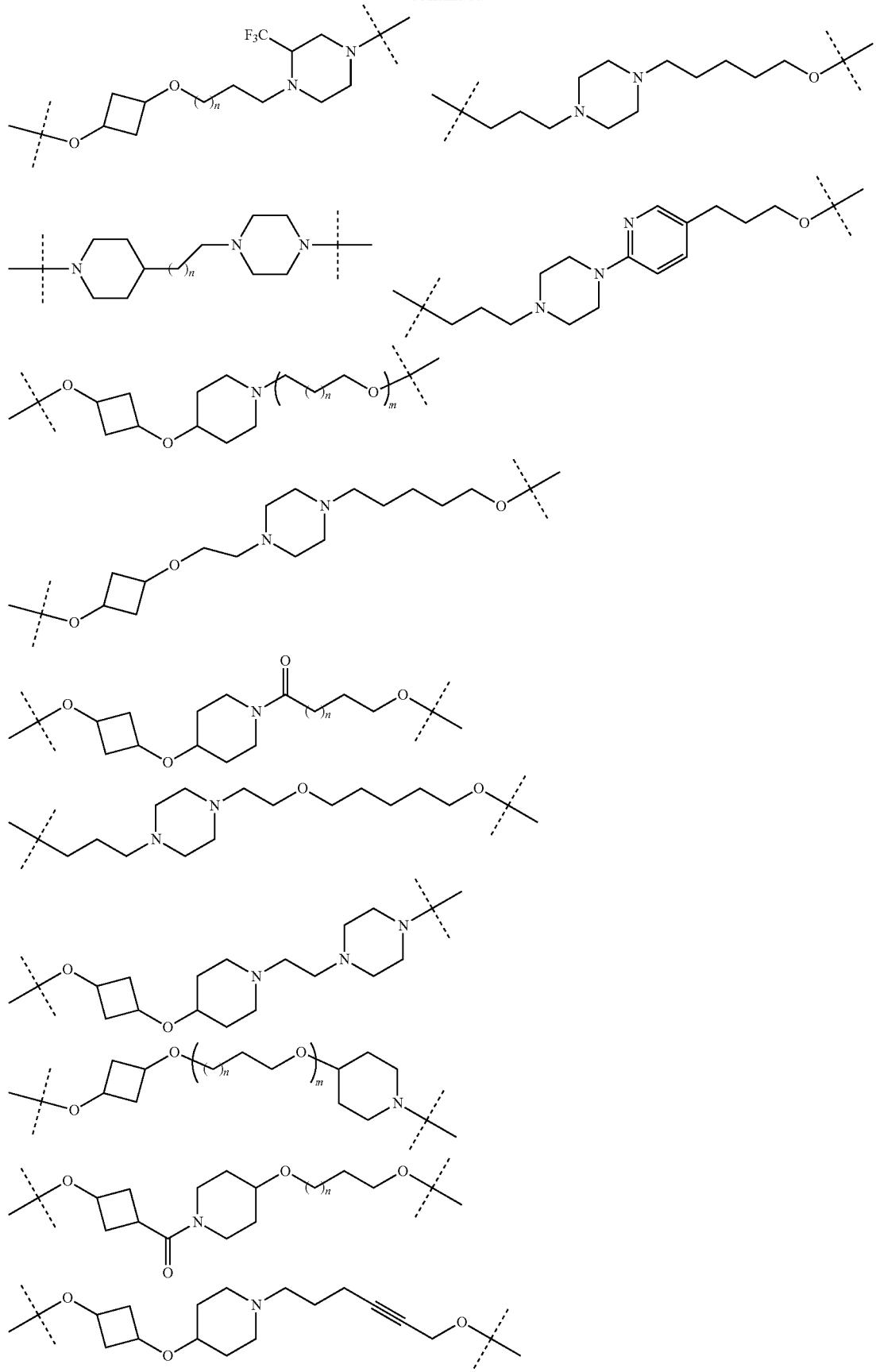

-continued
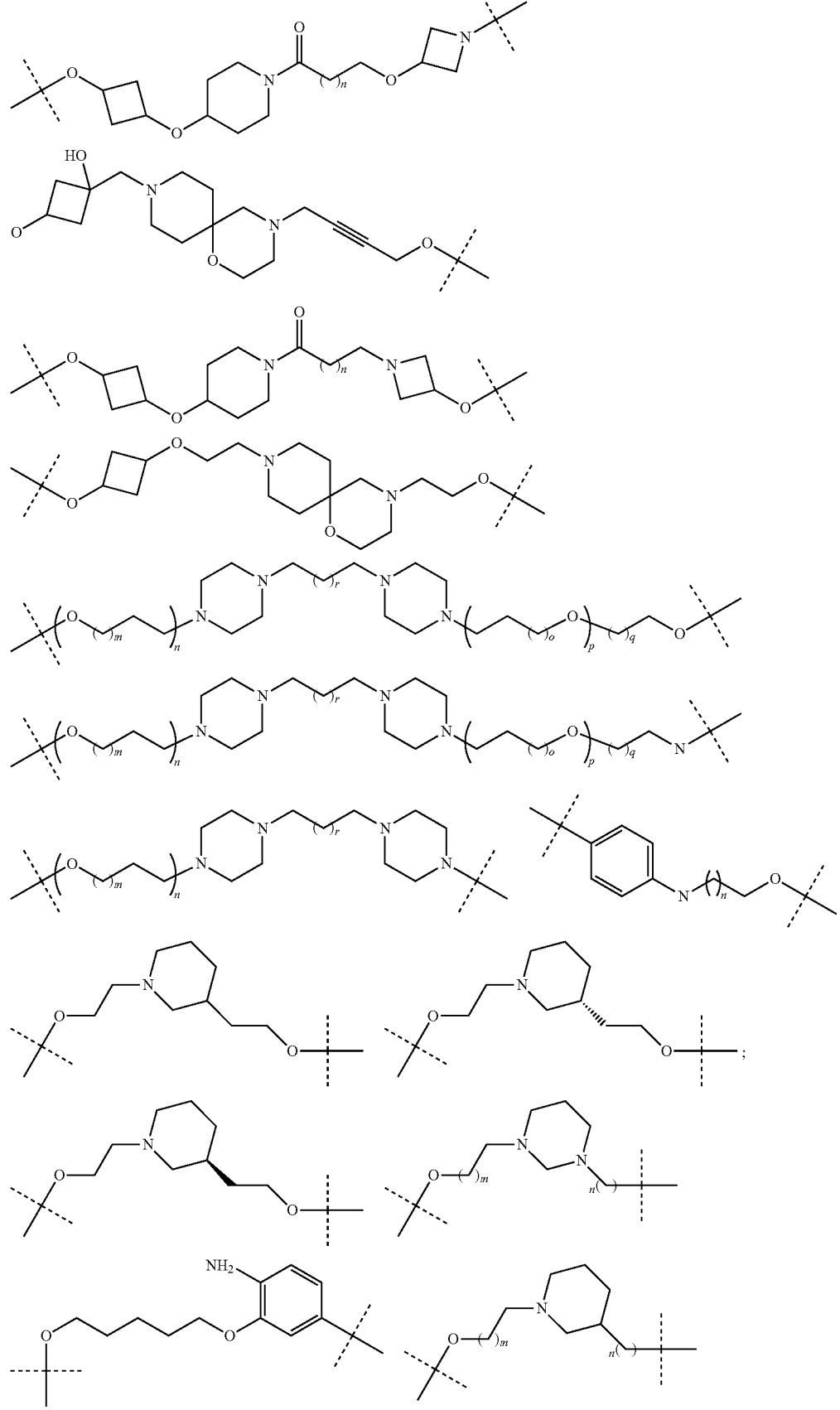

-continued
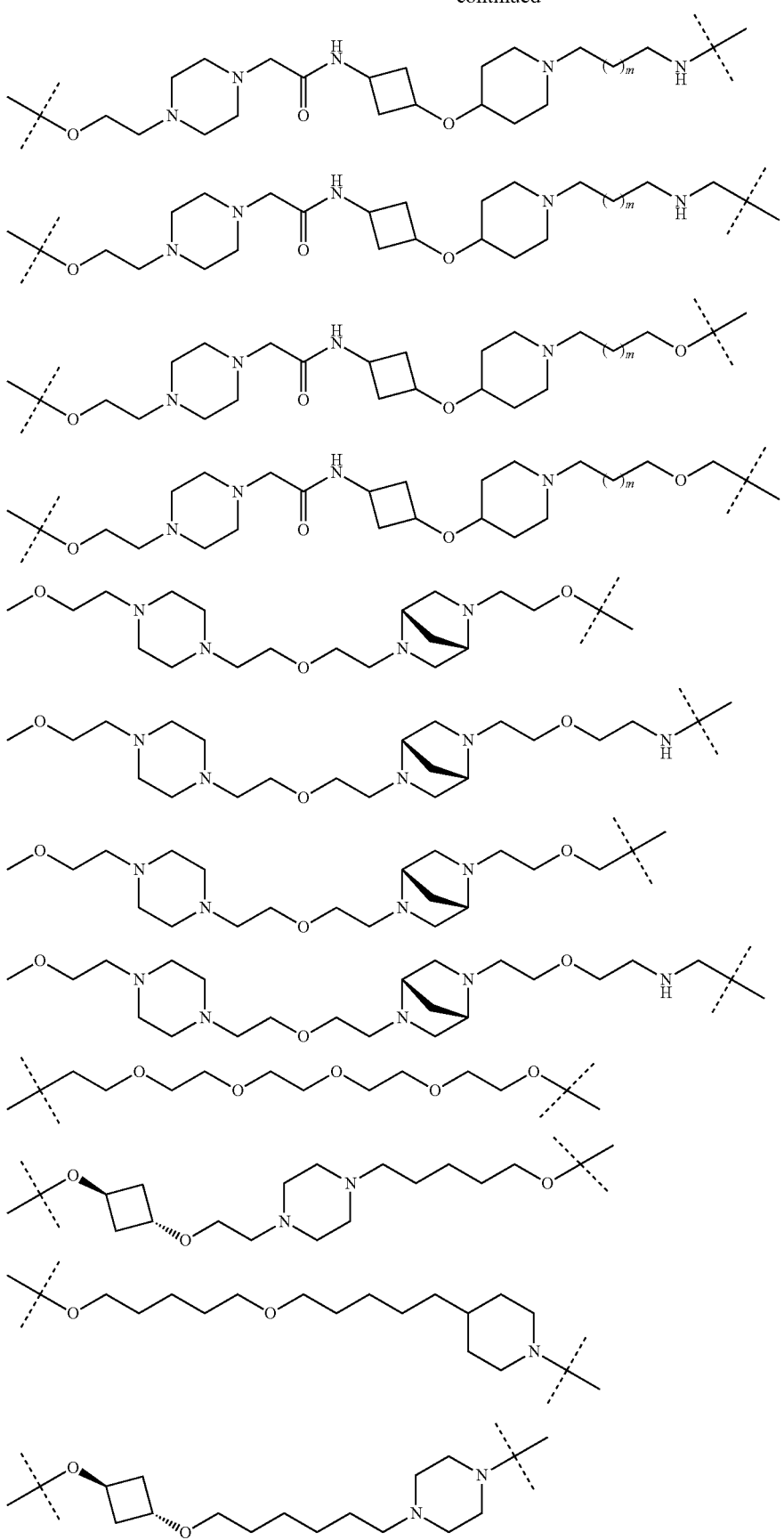

-continued
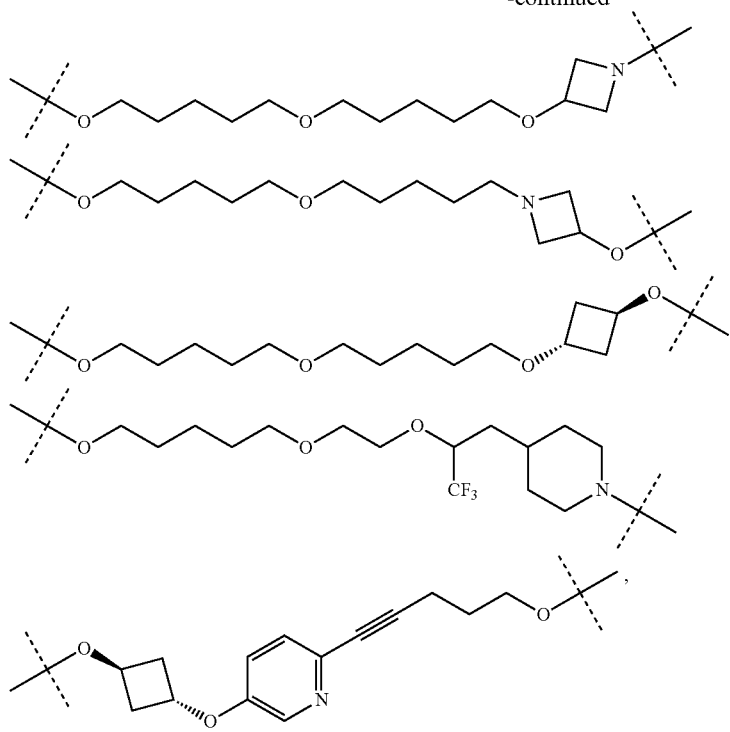
wherein m, n, o, p, q, and r are independently 0, 1, 2, 3, 4, 5, 6, or 7.
In some embodiments, the linker (L) is selected from the group consisting of:
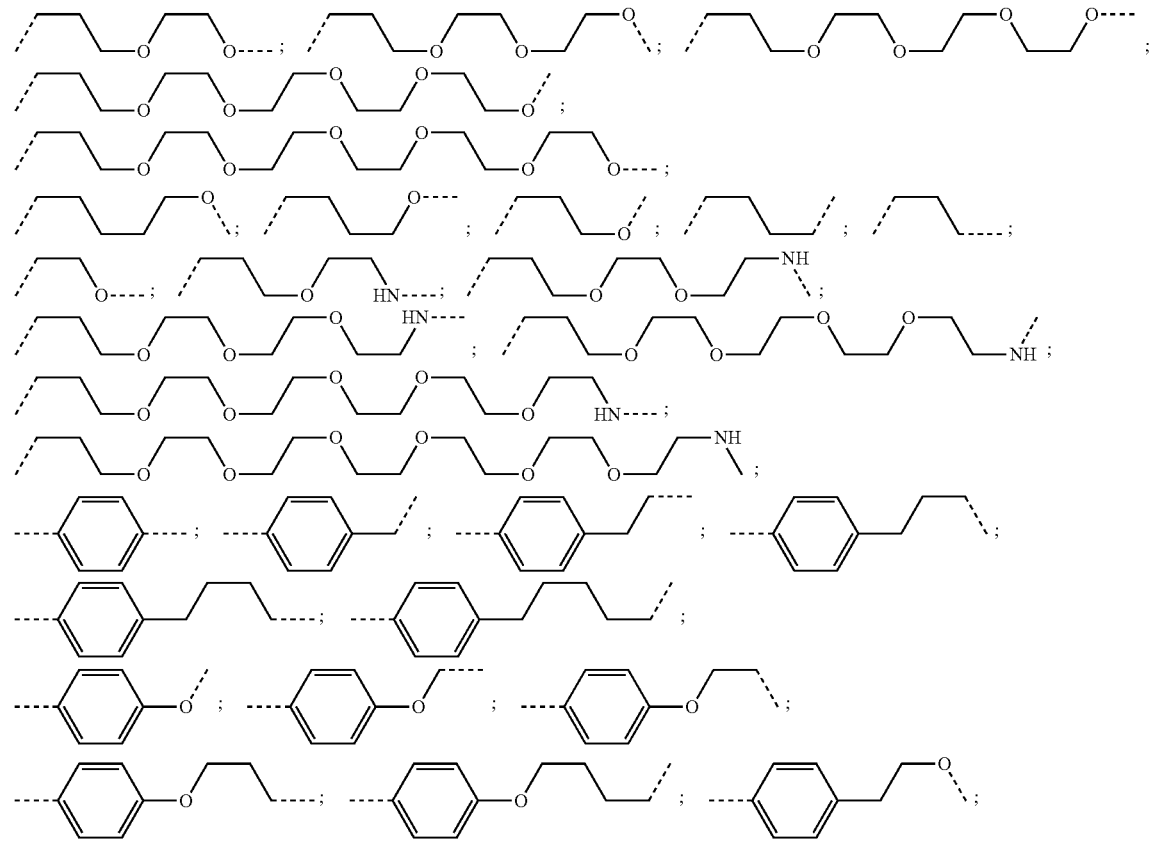

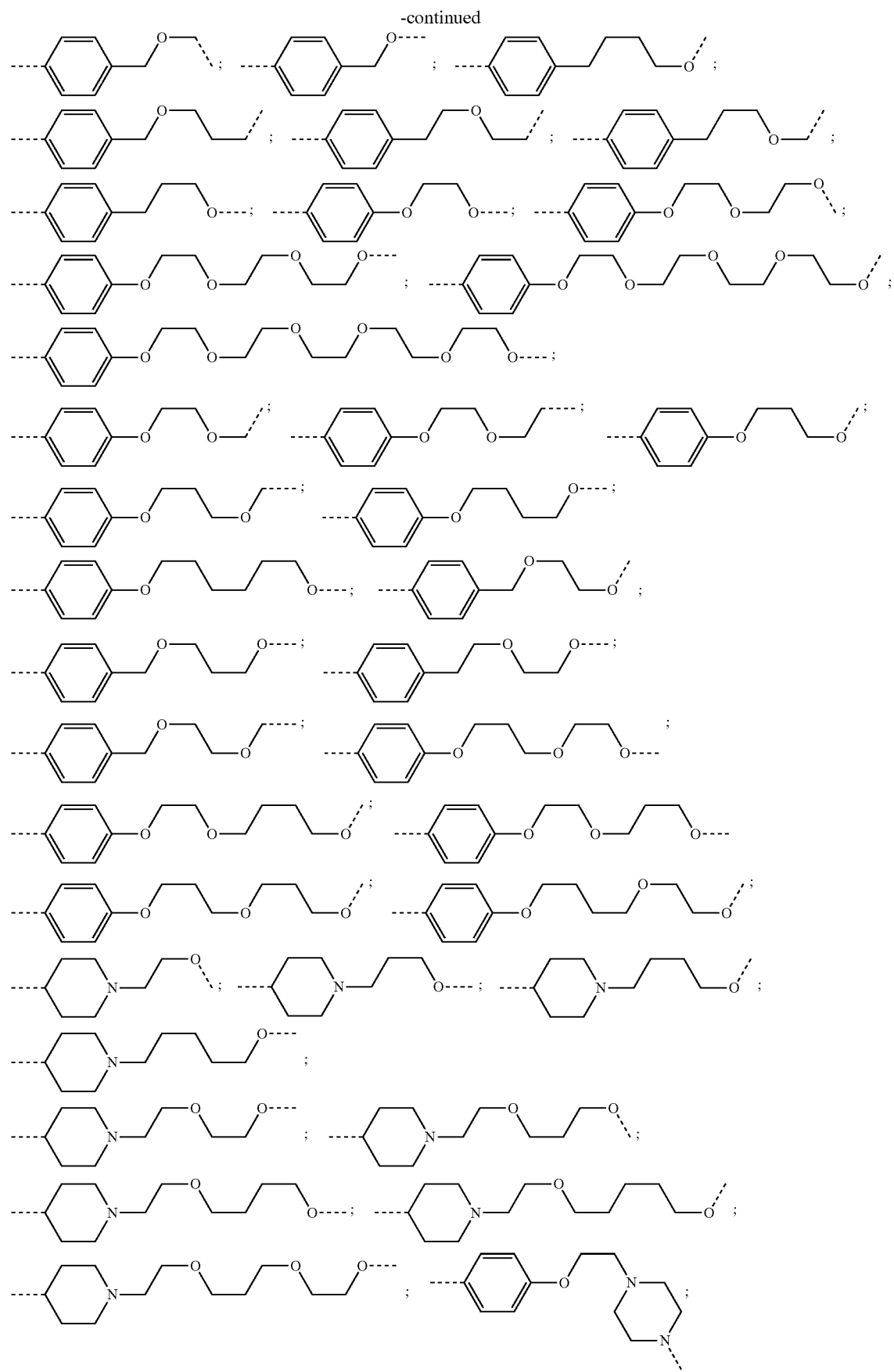

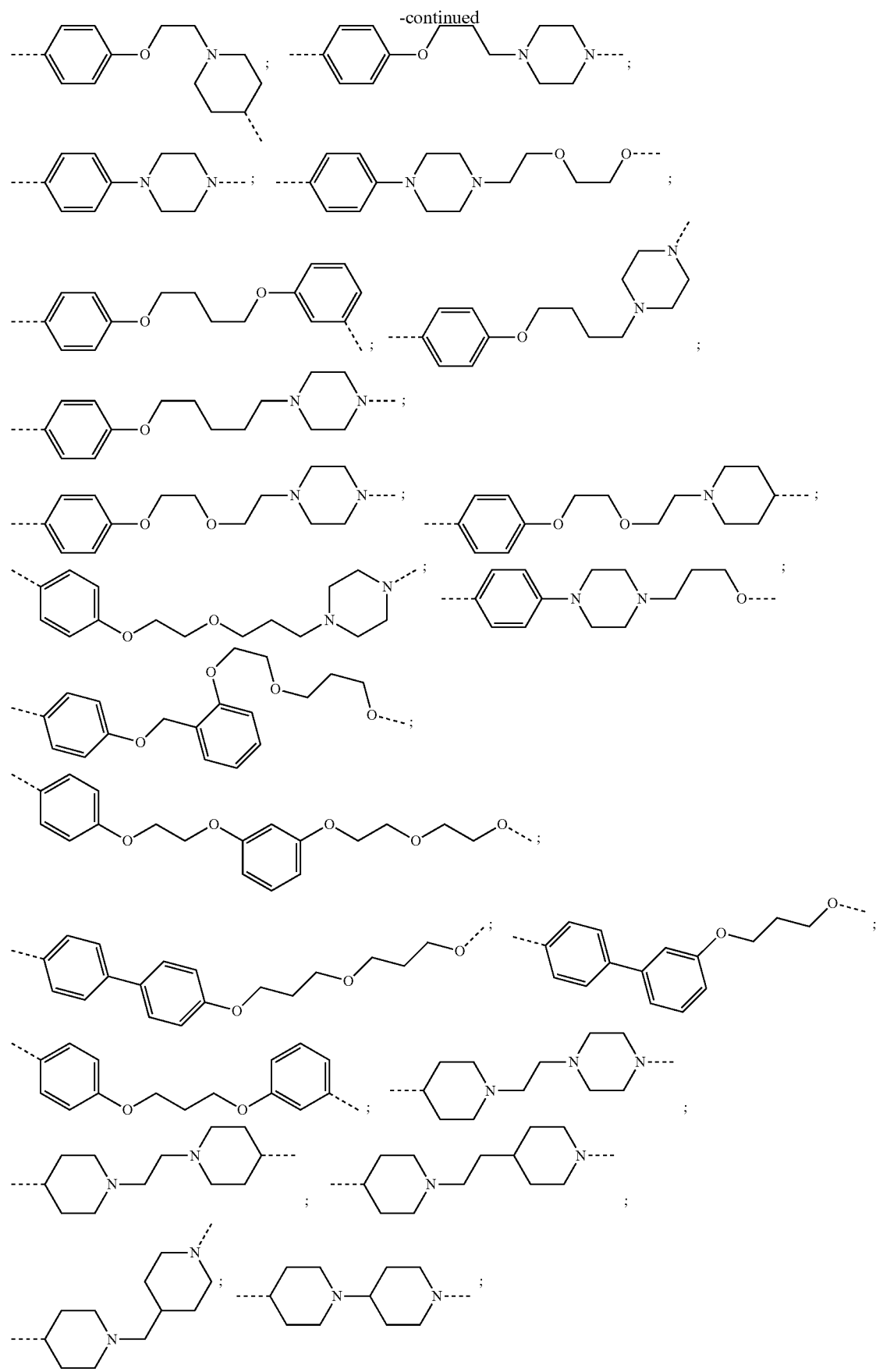

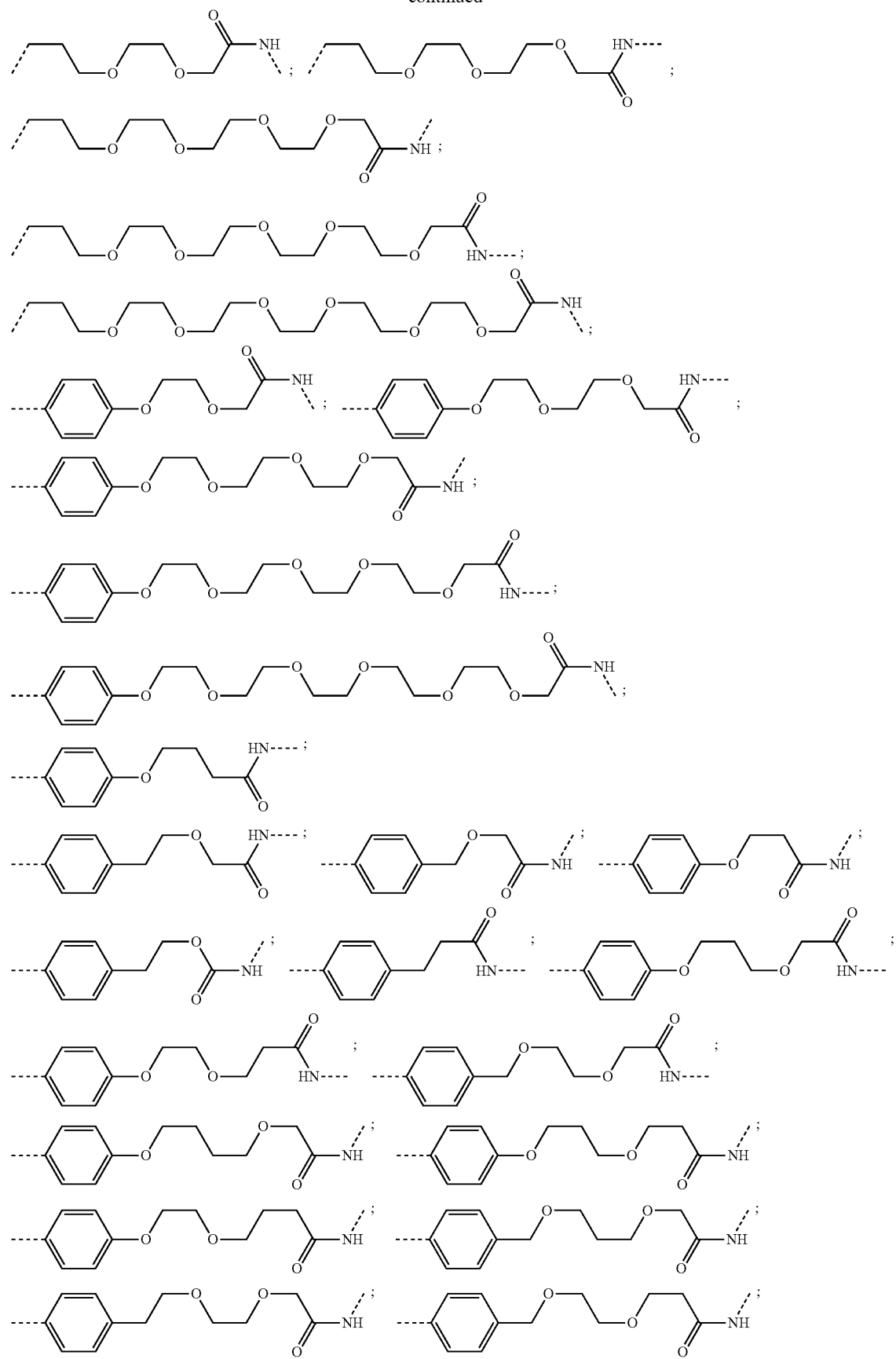

397 398
-continued
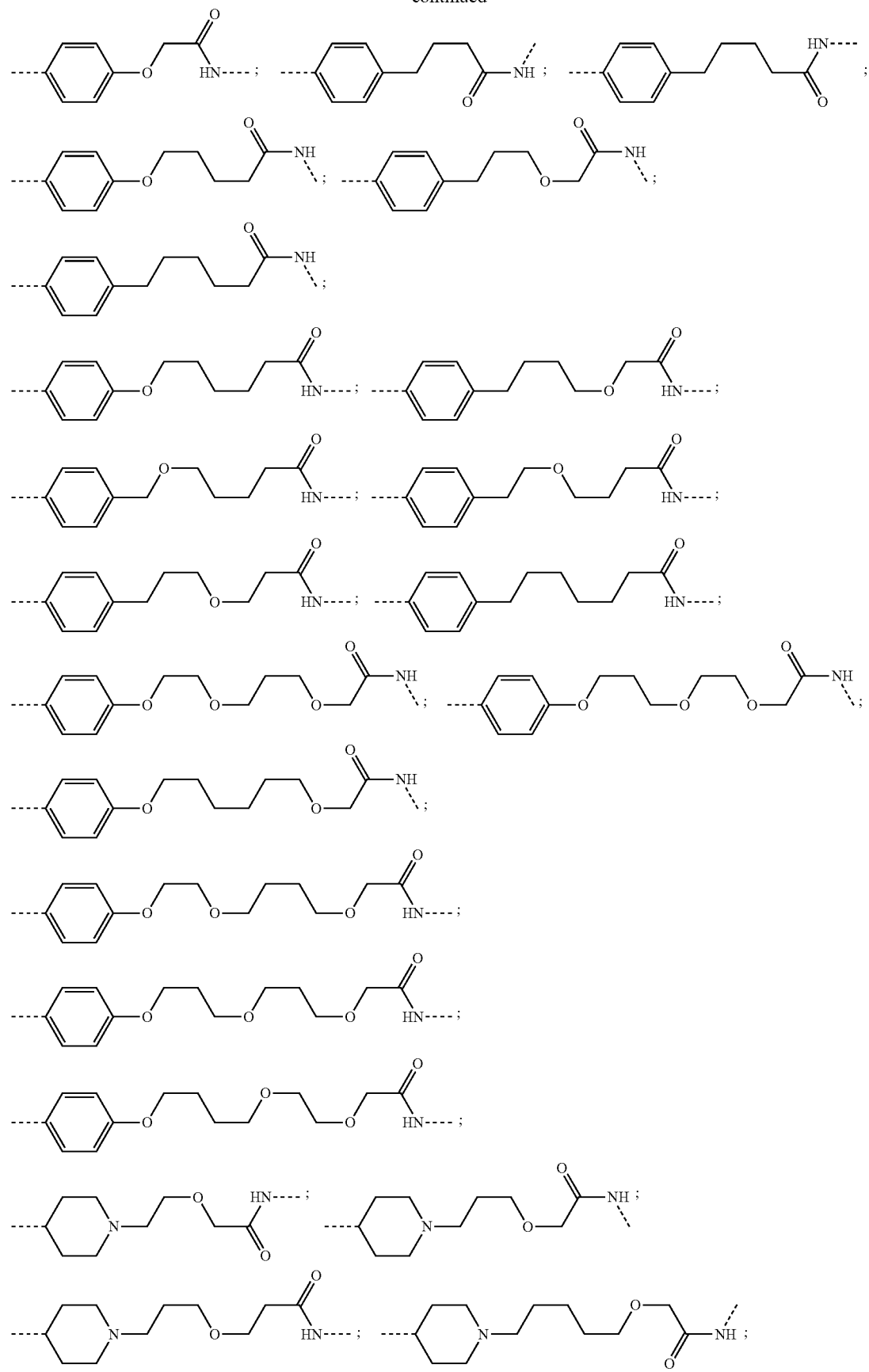

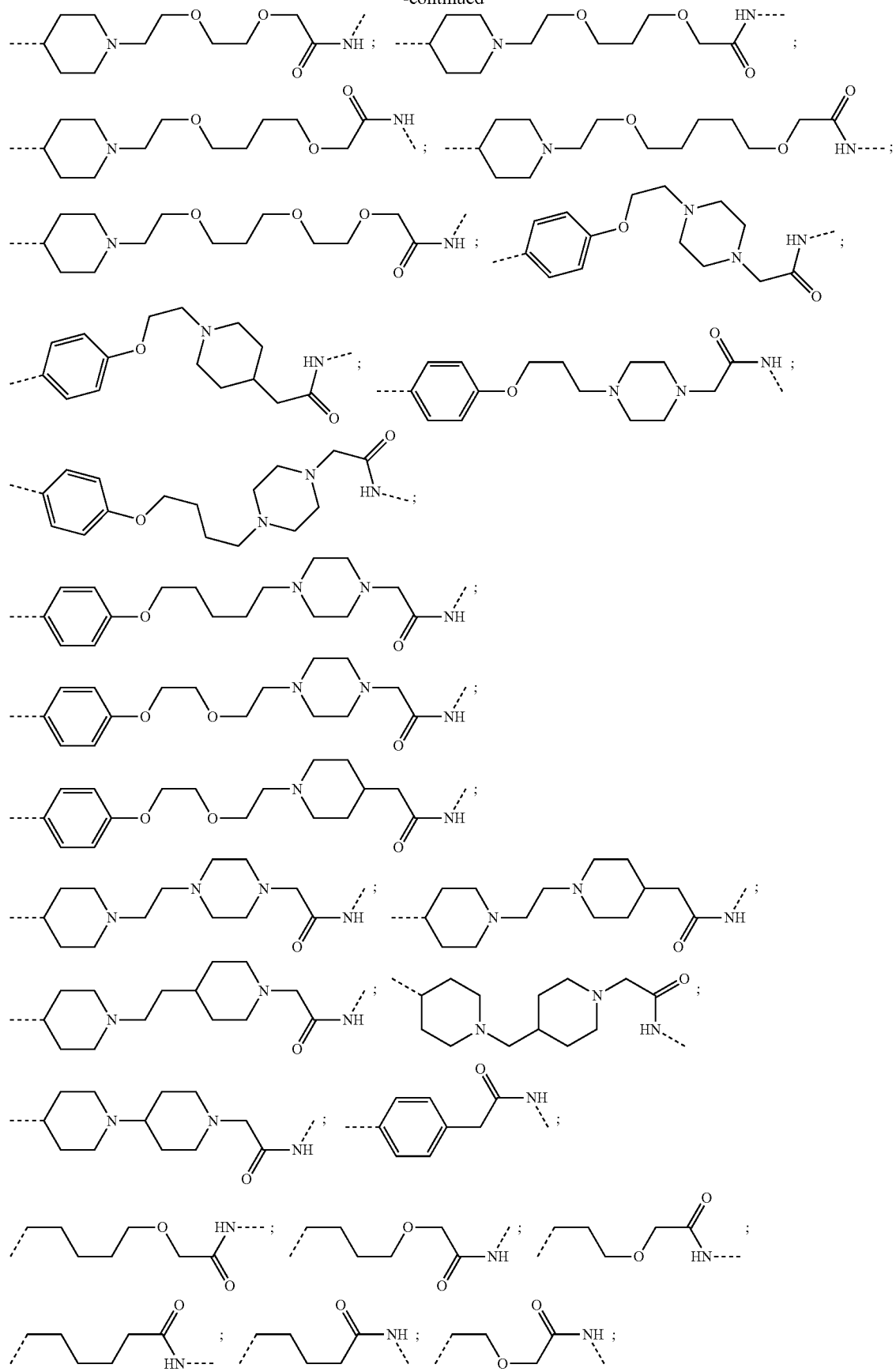

401
402
-continued
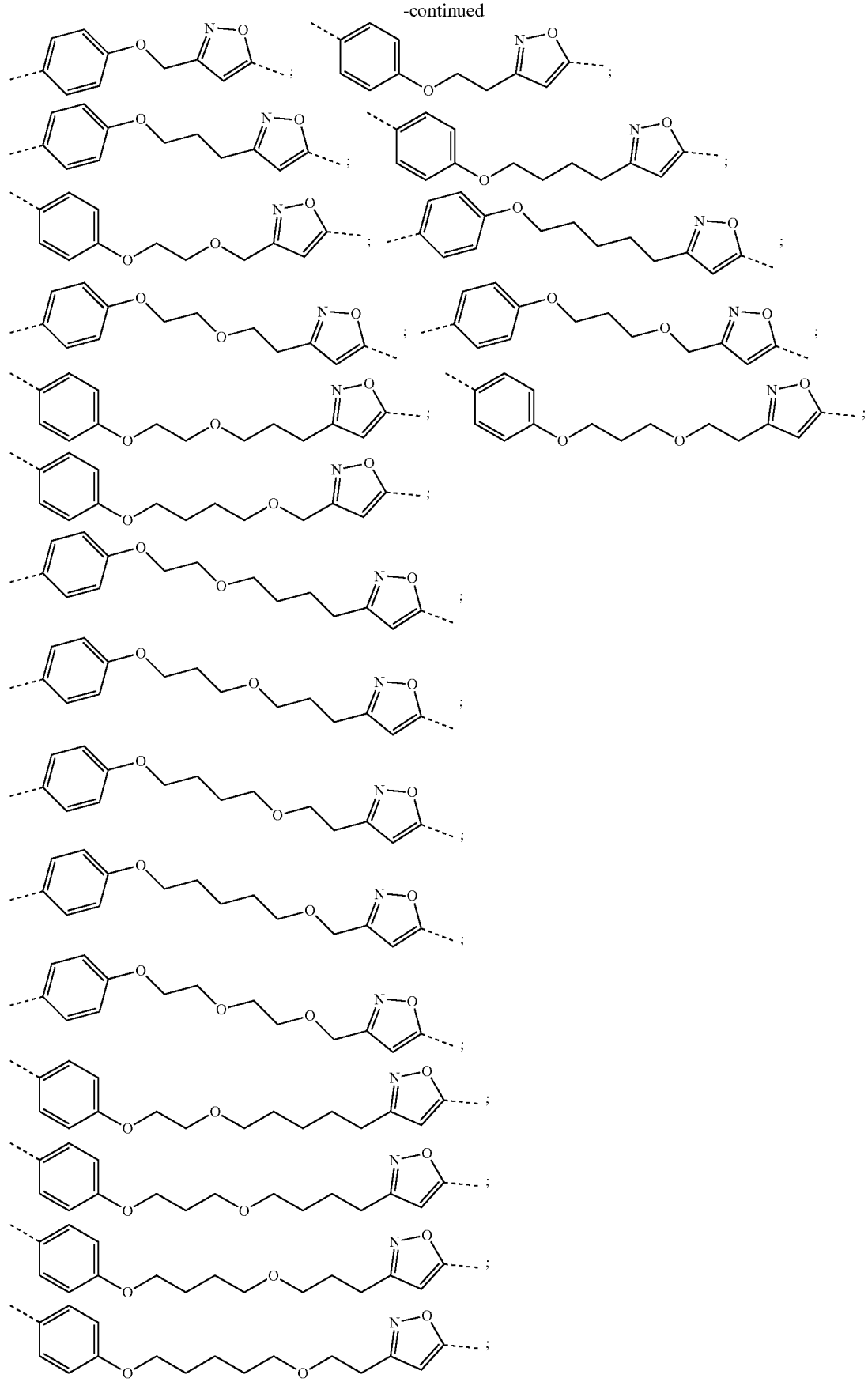

-continued
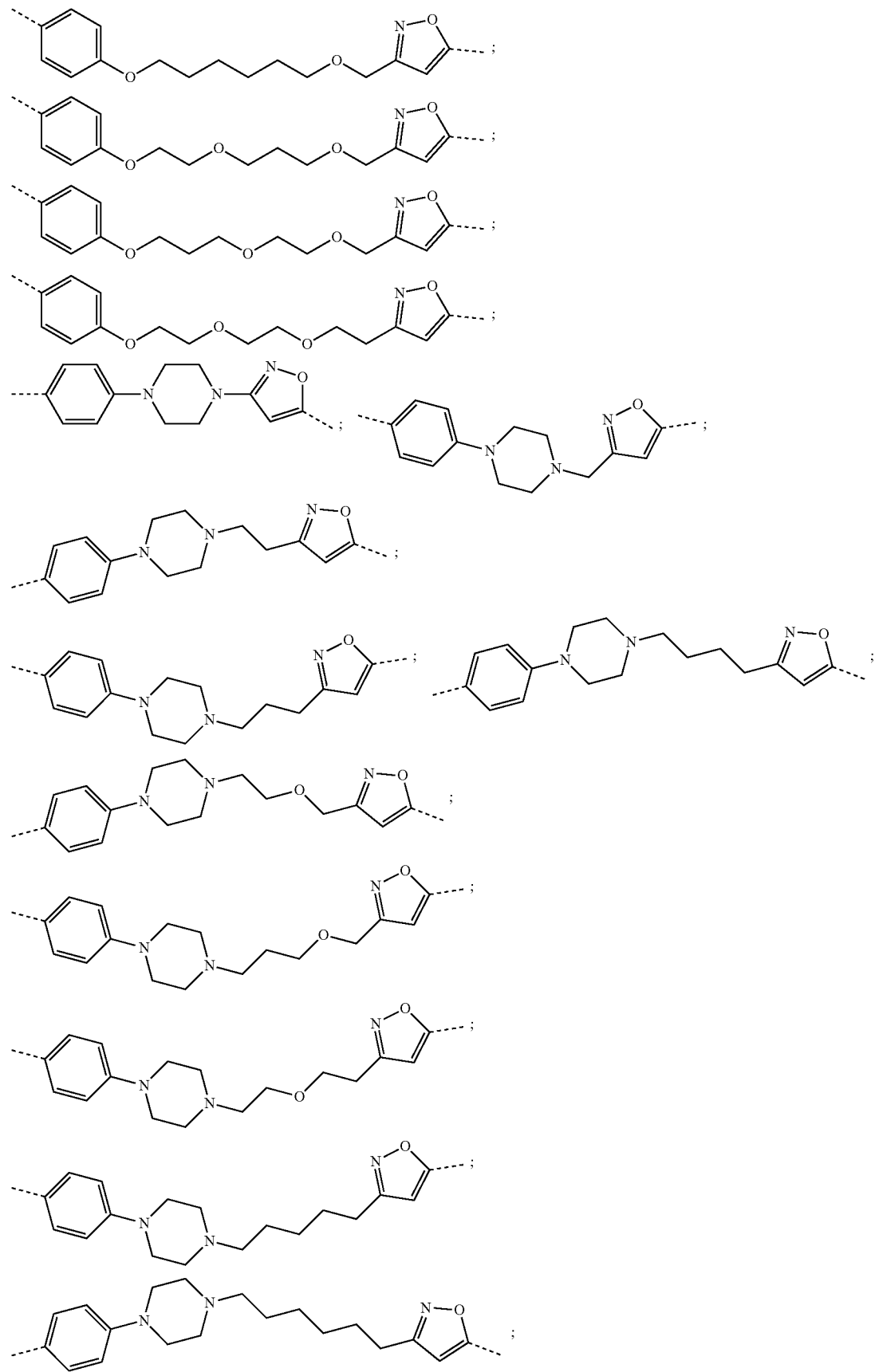

-continued
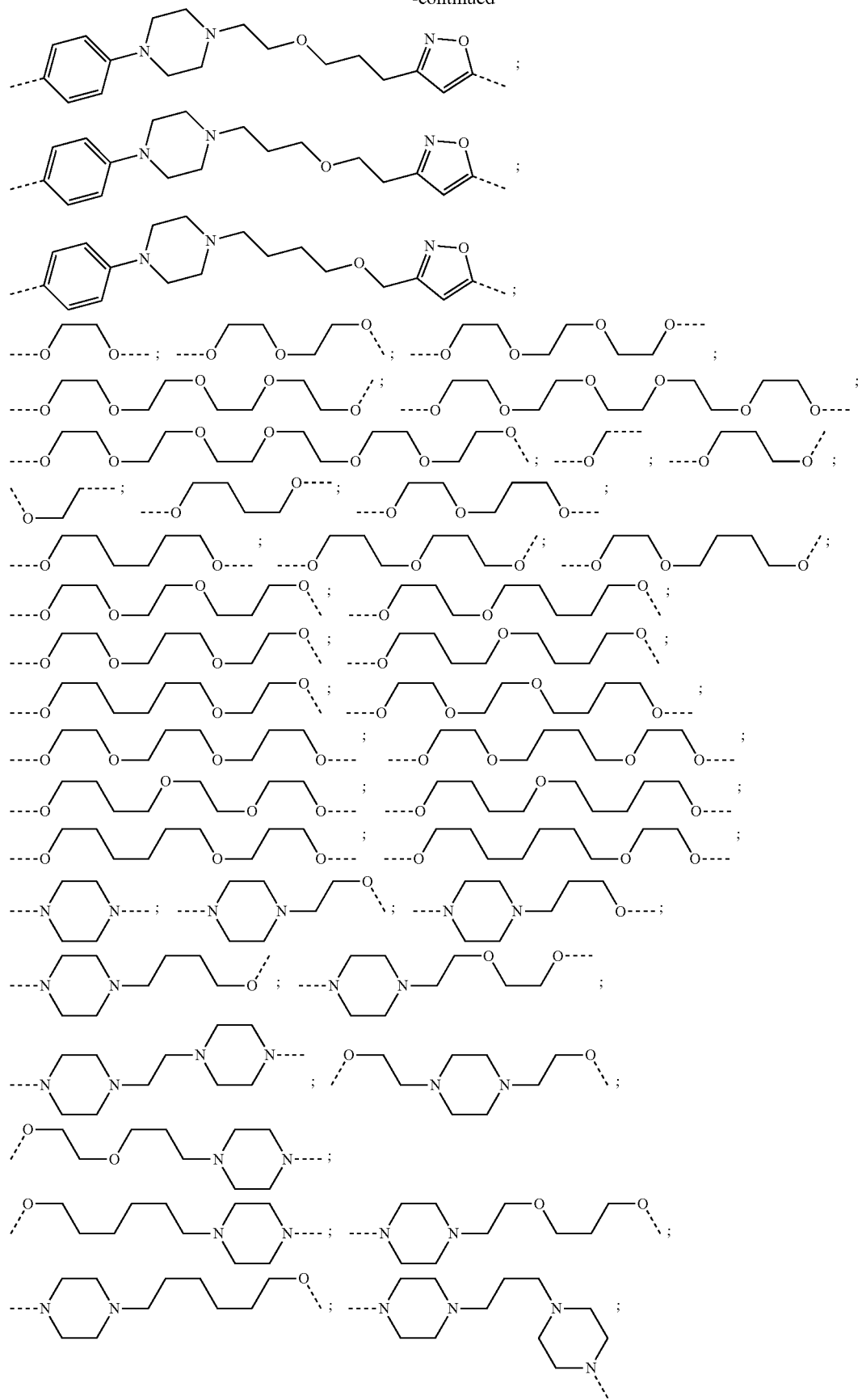

-continued
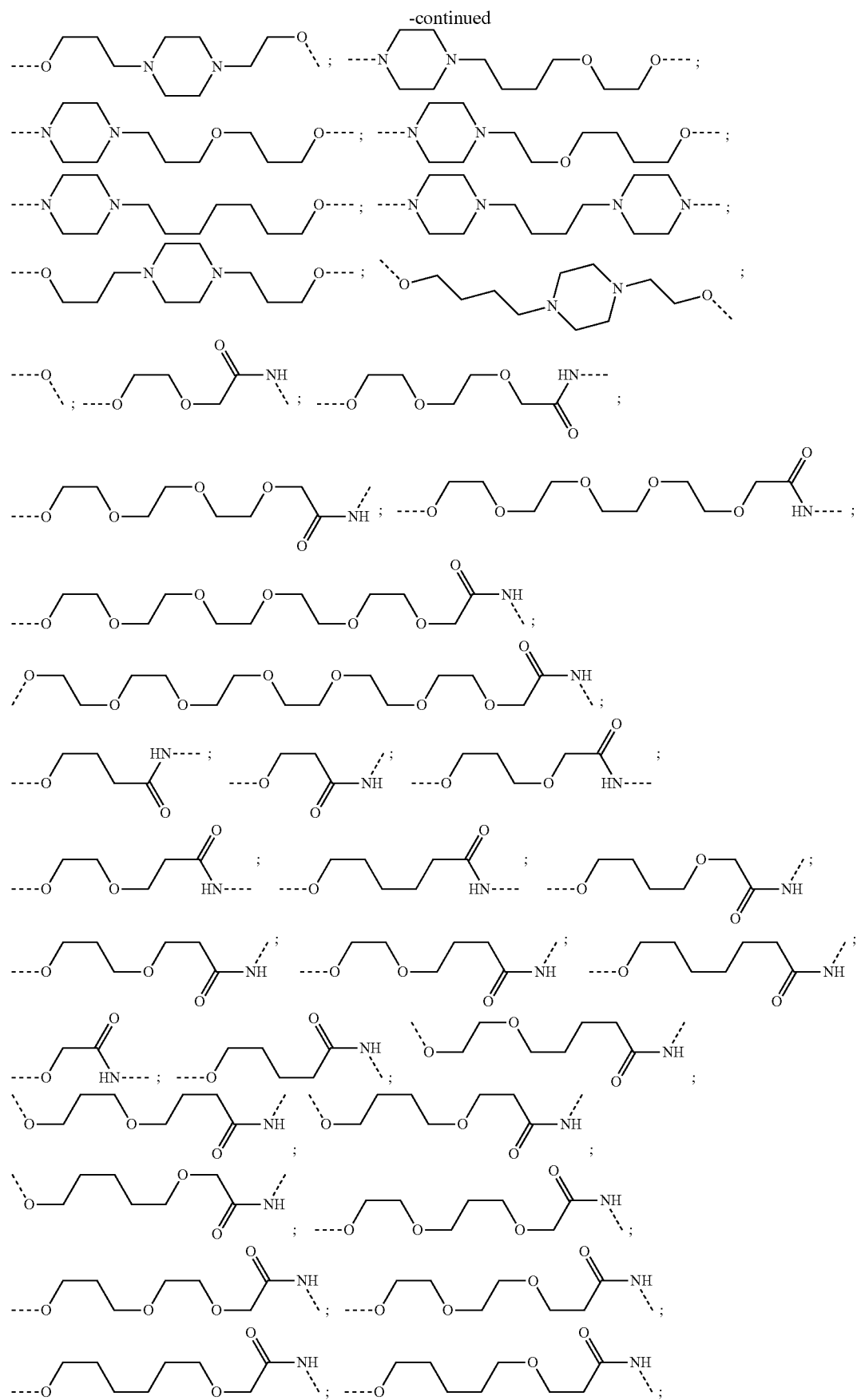

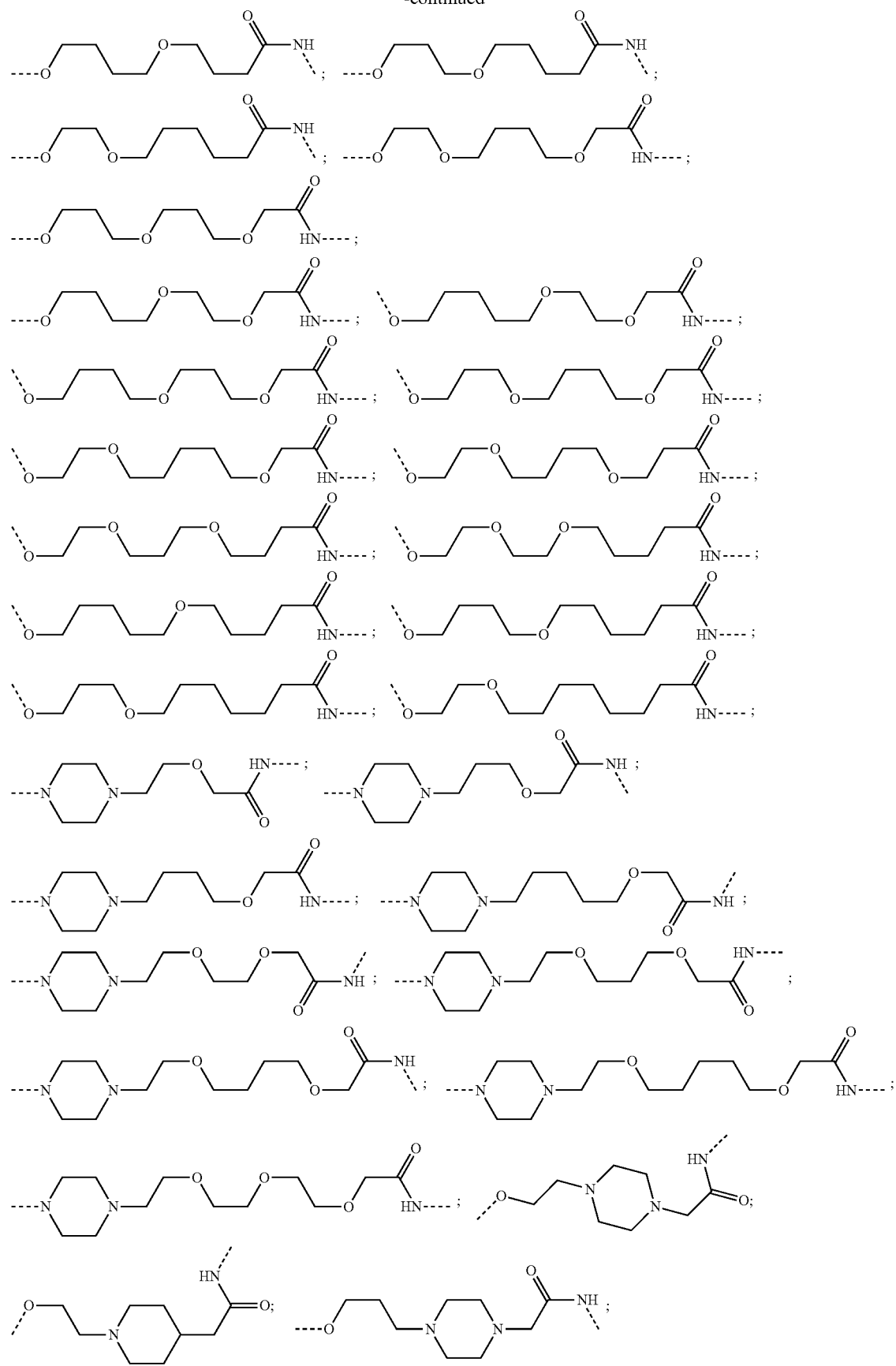

-continued
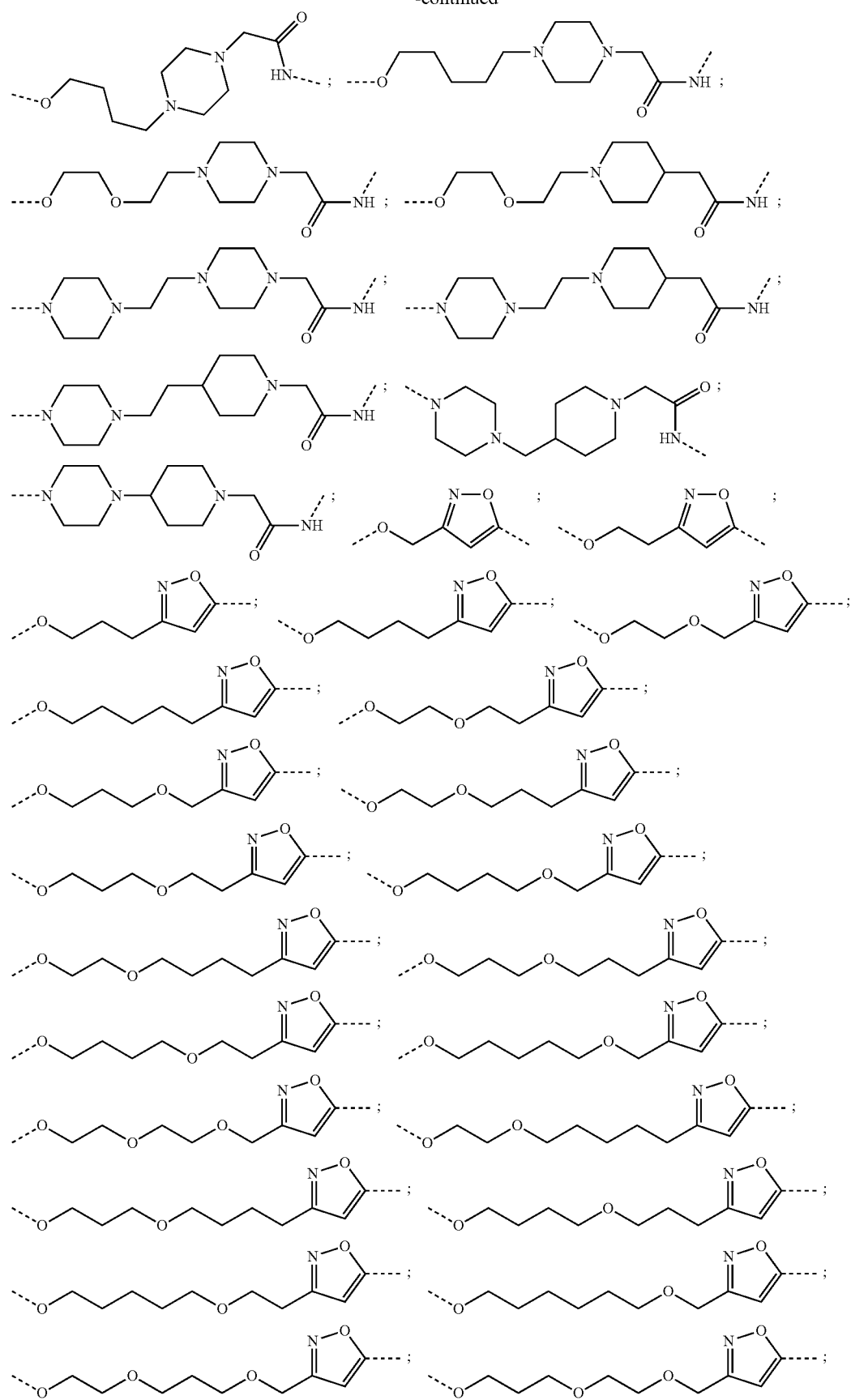

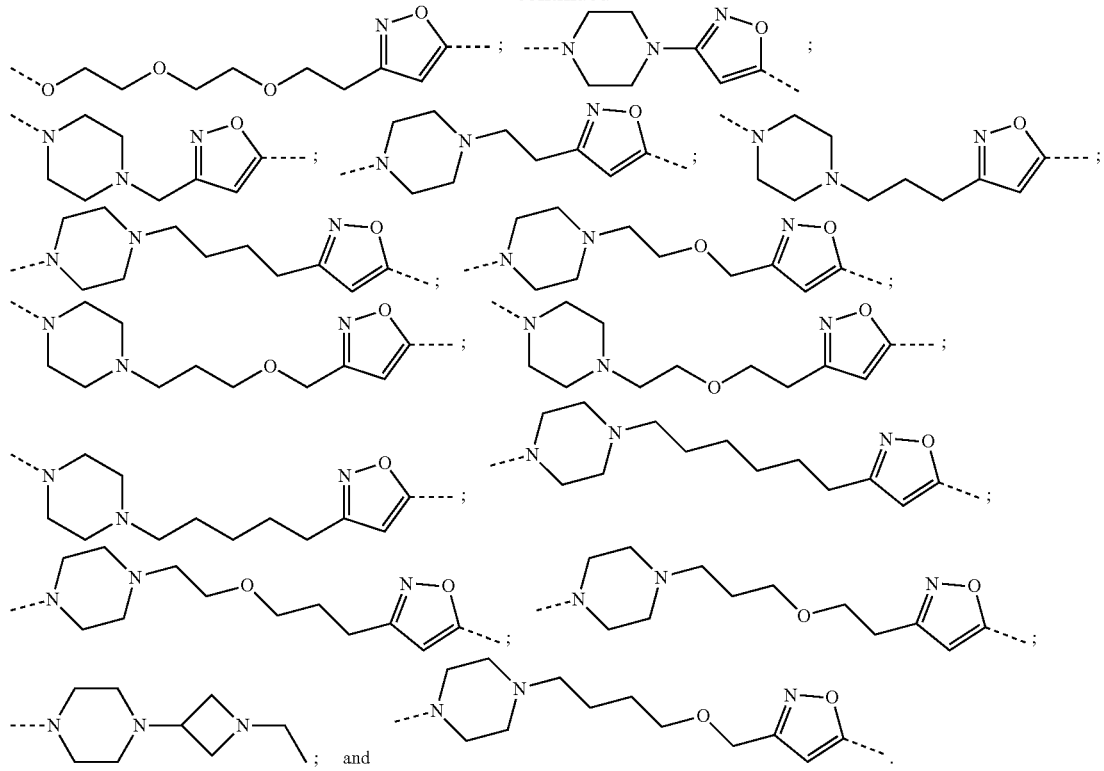

In additional embodiments, the linker (L) comprises a structure selected from, but not limited to the structure shown below, where a dashed line indicates the attachment point to the PTM or ULM moieties.

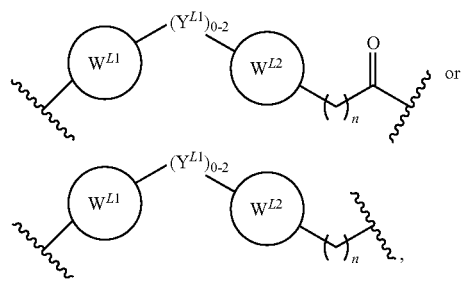

wherein:
W$^{L1}$ and W$^{L2}$ are each independently a 4-8 membered ring with 0-4 heteroatoms, optionally substituted with R$^Q$, each R$^Q$ is independently a H, halo, OH, CN, CF$_3$, C$_1$-C$_6$ alkyl (linear, branched, optionally substituted), C$_1$-C$_6$ alkoxy (linear, branched, optionally substituted), or 2 R$^Q$ groups taken together with the atom they are attached to, form a 4-8 membered ring system containing 0-4 heteroatoms;
Y$^{L1}$ is each independently a bond, C$_1$-C$_6$ alkyl (linear, branched, optionally substituted) and optionally one or more C atoms are replaced with O; or C$_1$-C$_6$ alkoxy (linear, branched, optionally substituted);
n is 0-10; and
a dashed line indicates the attachment point to the PTM or ULM moieties.

In additional embodiments, the linker (L) comprises a structure selected from, but not limited to the structure shown below, where a dashed line indicates the attachment point to the PTM or ULM moieties.

wherein:
W$^{L1}$ and W$^{L2}$ are each independently aryl, heteroaryl, cyclic, heterocyclic, C$_{1-6}$ alkyl, bicyclic, biaryl, biheteroaryl, or biheterocyclic, each optionally substituted with R$^Q$, each R$^Q$ is independently a H, halo, OH, CN, CF$_3$, hydroxyl, nitro, C≡CH, C$_{2-6}$ alkenyl, C$_{2-6}$ alkynyl, C$_1$-C$_6$ alkyl (linear, branched, optionally substituted), C$_1$-C$_6$ alkoxy (linear, branched, optionally substituted), OC$_{1-3}$alkyl (optionally substituted by 1 or more —F), OH, NH$_2$, NR$^{Y1}$R$^{Y2}$, CN, or 2 R$^Q$ groups taken together with the atom they are attached to, form a 4-8 membered ring system containing 0-4 heteroatoms;
Y$^{L1}$ is each independently a bond, NR$^{YL1}$, O, S, NR$^{YL2}$, CR$^{YL1}$R$^{YL2}$, C=O, SO, SO$_2$, C$_1$-C$_6$ alkyl (linear, branched, optionally substituted) and optionally one or more C atoms are replaced with O; $C_1$-$C_6$ alkoxy (linear, branched, optionally substituted);

$Q^L$ is a 3-6 membered alicyclic or aromatic ring with 0-4 heteroatoms, optionally bridged, optionally substituted with 0-6 $R^Q$, each $R^Q$ is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^{YL1}$, $R^{YL2}$ are each independently H, OH, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

n is 0-10; and a dashed line indicates the attachment point to the PTM or ULM moieties.

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In another embodiment, the present disclosure is directed to a compound which comprises a PTM group as described above, which binds to a target protein or polypeptide (e.g., RAF), which is ubiquitinated by an ubiquitin ligase and is chemically linked directly to the ULM group or through a linker moiety L, or PTM is alternatively a ULM' group which is also a ubiquitin ligase binding moiety, which may be the same or different than the ULM group as described above and is linked directly to the ULM group directly or through the linker moiety; and L is a linker moiety as described above which may be present or absent and which chemically (covalently) links ULM to PTM, or a pharmaceutically acceptable salt, enantiomer, stereoisomer, solvate or polymorph thereof.

In certain embodiments, the linker group L is a group comprising one or more covalently connected structural units independently selected from the group consisting of:

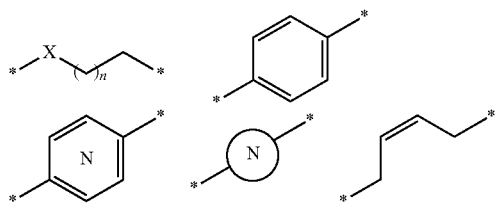

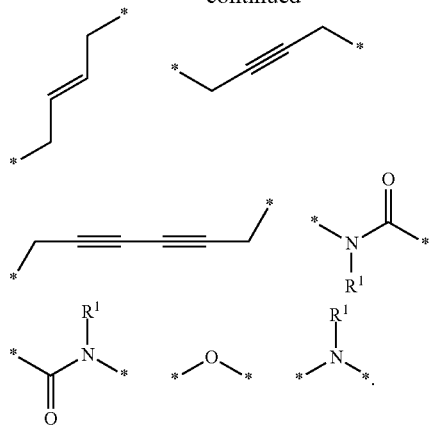

The X is selected from the group consisting of O, N, S, S(O) and $SO_2$; n is integer from 1-5, 5; $R^{L1}$ is hydrogen or alkyl,

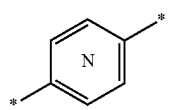

is a mono- or bicyclic aryl or heteroaryl optionally substituted with 1-3 substituents selected from alkyl, halogen, haloalkyl, hydroxy, alkoxy or cyano;

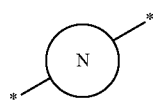

is a mono- or bicyclic cycloalkyl or a heterocycloalkyl optionally substituted with 1-3 substituents selected from alkyl, halogen, haloalkyl, hydroxy, alkoxy or cyano; and the phenyl ring fragment can be optionally substituted with 1, 2 or 3 substituents selected from the group consisting of alkyl, halogen, haloalkyl, hydroxy, alkoxy and cyano. In an embodiment, the linker group L comprises up to 10 covalently connected structural units, as described above.

Although the ULM group and PTM group may be covalently linked to the linker group through any group which is appropriate and stable to the chemistry of the linker, in preferred aspects of the present disclosure, the linker is independently covalently bonded to the ULM group and the PTM group preferably through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the ULM and/or PTM groups.

Exemplary PTMs

In preferred aspects of the disclosure, the PTM group is a group, which binds to target proteins. Targets of the PTM group are numerous in kind and are selected from proteins that are expressed in a cell such that at least a portion of the sequences is found in the cell and may bind to a PTM group. The term "protein" includes oligopeptides and polypeptide sequences of sufficient length that they can bind to a PTM group according to the present disclosure. Any protein in a eukaryotic system or a microbial system, including a virus, bacteria or fungus, as otherwise described herein, are targets for ubiquitination mediated by the compounds according to the present disclosure. Preferably, the target protein is a eukaryotic protein.

PTM groups according to the present disclosure include, for example, any moiety which binds to a protein specifically (binds to a target protein) and includes the following non-limiting examples of small molecule target protein moieties: RAF inhibitors, Hsp90 inhibitors, kinase inhibitors, HDM2 & MDM2 inhibitors, compounds targeting Human BET Bromodomain-containing proteins, HDAC inhibitors, human lysine methyltransferase inhibitors, angiogenesis inhibitors, nuclear hormone receptor compounds, immunosuppressive compounds, and compounds targeting the aryl hydrocarbon receptor (AHR), among numerous others. The compositions described below exemplify some of the members of small molecule target protein binding moieties. Such small molecule target protein binding moieties also include pharmaceutically acceptable salts, enantiomers, solvates and polymorphs of these compositions, as well as other small molecules that may target a protein of interest. These binding moieties are linked to the ubiquitin ligase binding moiety preferably through a linker in order to present a target protein (to which the protein target moiety is bound) in proximity to the ubiquitin ligase for ubiquitination and degradation.

Any protein, which can bind to a protein target moiety or PTM group and acted on or degraded by an ubiquitin ligase (e.g., RAF) is a target protein according to the present disclosure. In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catrabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes (e.g., c-RAF, A-RAF, and/or B-RAF) and prokaryotes including humans as targets for drug therapy, other animals, including domesticated animals, microbials for the determination of targets for antibiotics and other antimicrobials and plants, and even viruses (e.g., v-RAF and/or v-Mil), among numerous others.

The present disclosure may be used to treat a number of disease states and/or conditions, including any disease state and/or condition in which proteins are dysregulated and where a patient would benefit from the degradation of proteins.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer, cardiofaciocutaneous syndrome, neurofibromatosis type 1, Costello syndrome, Noonan Syndrome, LEOPARD syndrome. In certain additional embodiments, the disease is renal cell carcinoma, pancreatic cancer, colorectal cancer, lung cancer, ovarian cancer, thyroid cancer, pilocytic astrocytoma, prostate cancer, gastric cancer, hepatocellular carcinoma, and melanoma.

In alternative aspects, the present disclosure relates to a method for treating a disease state or ameliorating the symptoms of a disease or condition in a subject in need thereof by degrading a protein or polypeptide through which a disease state or condition is modulated comprising administering to said patient or subject an effective amount, e.g., a therapeutically effective amount, of at least one compound as described hereinabove, optionally in combination with a pharmaceutically acceptable carrier, additive or excipient, and optionally an additional bioactive agent, wherein the composition is effective for treating or ameliorating the disease or disorder or symptom thereof in the subject. The method according to the present disclosure may be used to treat a large number of disease states or conditions including cancer, cardiofaciocutaneous syndrome, neurofibromatosis type 1, Costello syndrome, Noonan Syndrome, LEOPARD syndrome, by virtue of the administration of effective amounts of at least one compound described herein. The disease state or condition may be a disease caused by a microbial agent or other exogenous agent such as a virus (e.g., murine retrovirus or avian retrovirus, such as avian retrovirus MH2), bacteria, fungus, protozoa or other microbe or may be a disease state, which is caused by overexpression of a protein and/or the presence of a protein that is constitutively activated, which leads to a disease state and/or condition.

In another aspect, the description provides methods for identifying the effects of the degradation of proteins of interest in a biological system using compounds according to the present disclosure.

The term "target protein" is used to describe a protein or polypeptide, which is a target for binding to a compound according to the present disclosure and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to at least one ULM group (e.g. VLM, CLM, ILM, and/or MLM) through at least one linker group L.

Target proteins, which may be bound to the protein target moiety and degraded by the ligase to which the ubiquitin ligase binding moiety is bound, include any protein or peptide, including fragments thereof, analogues thereof, and/or homologues thereof. Target proteins include proteins and peptides having any biological function or activity including structural, regulatory, hormonal, enzymatic, genetic, immunological, contractile, storage, transportation, and signal transduction. More specifically, a number of drug targets for human therapeutics represent protein targets to which protein target moiety may be bound and incorporated into compounds according to the present disclosure. These include proteins which may be used to restore function in numerous polygenic diseases, including for example B7.1 and B7, TINFR1m, TNFR2, NADPH oxidase, Bc1IBax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+channels, VCAM, VLA-4 integrin, selectins, CD40/CD40L, newokinins and receptors, inosine monophosphate dehydrogenase, p38 MAP Kinase, Ras/Raf/MEK-ERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further target proteins include Acetyl-CoA carboxylase, adenylosuccinate synthetase, protoporphyrinogen oxidase, and enolpyruvylshikimate-phosphate synthase.

These various protein targets may be used in screens that identify compound moieties which bind to the protein and by incorporation of the moiety into compounds according to the present disclosure, the level of activity of the protein may be altered for therapeutic end result.

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. Non-limiting examples of small molecule target protein binding moieties include RAF inhibitors, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of the small molecule target proteins.

Exemplary protein target moieties according to the present disclosure include, RAF inhibitors, haloalkane halogenase inhibitors, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR).

The compositions described below exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. References which are cited herein below are incorporated by reference herein in their entirety.

In any aspect or embodiment described herein, the PTM targets and/or binds RAF. For example, in any aspect or embodiment described herein, the PTM may comprise a chemical group selected from the group of chemical structures consisting of PTM-Ia or PTM-Ib:

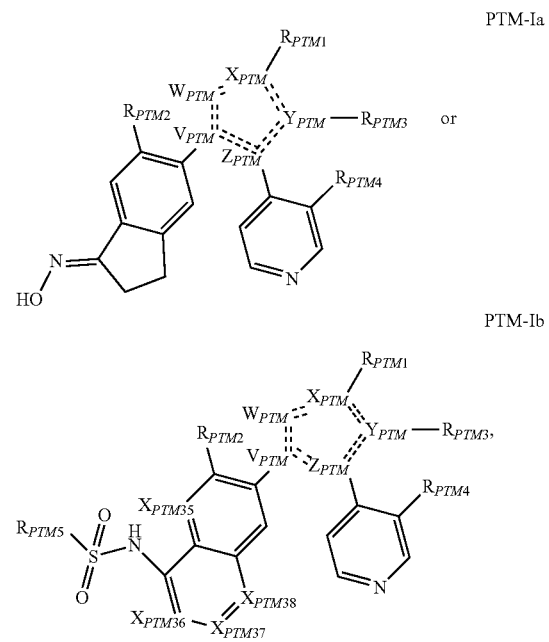

wherein:
double dotted bonds are aromaric bonds;
$V_{PTM}$, $W_{PTM}$, $X_{PTM}$, $Y_{PTM}$, $Z_{PTM}$ is one of the following combinations: C, CH, N, N, C; C, N, N, CH, C; C, O, C, CH, C; C, S, C, CH, C; C, CH, C, O, C; C, CH, C, S, C; C, CH, N, CH, C; N, CH, C, CH, C; C, CH, C, CH, N; N, N, C, CH, C; N, CH, C, N, C; C, CH, C, N, N; C, N, C, CH, N; C, N, C, N, C; and C, N, N, N, C;
$X_{PTM35}$, $X_{PTM36}$, $X_{PTM37}$, and $X_{PTM38}$ are independently selected from CH and N;
$R_{PTM1}$ is covalently joined to a ULM, a chemical linker group (L), a CLM, an ILM, a VLM, MLM, a ULM', a CLM', a ILM', a VLM', a MLM', or combination thereof;

$R_{PTM2}$ is hydrogen, halogen, aryl, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM3}$ is absent, hydrogen, aryl, methyl, ethyl, other alkyl, cyclic alkyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM4}$ is hydrogen, halogen, aryl, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle; and $R_{PTM5}$ is selected from the group consisting of

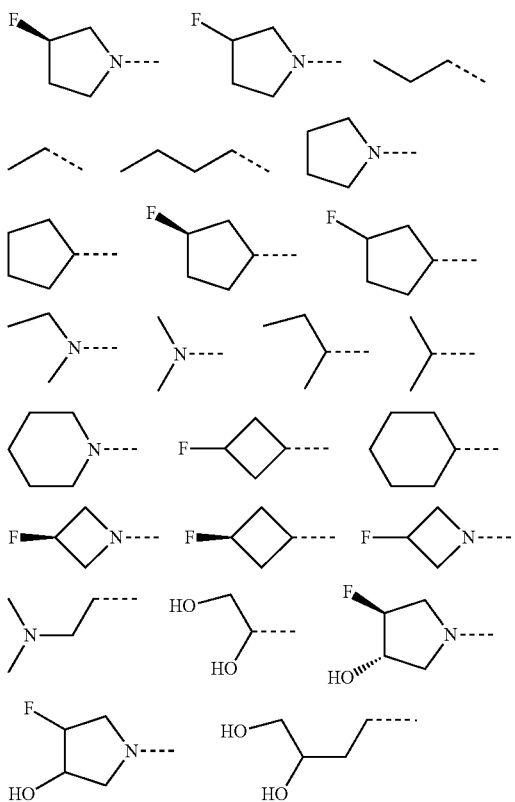

In any aspect or embodiment described herein, the PTM may comprise a chemical group selected from the group of chemical structures consisting of PTM-IIa or PTM-IIb:

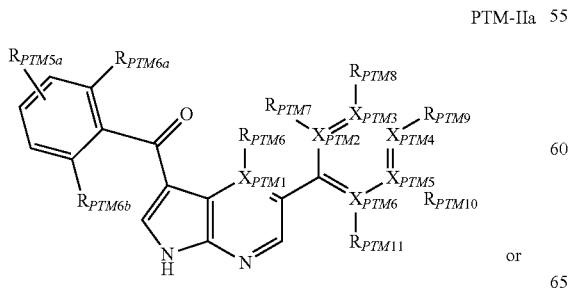

PTM-IIa

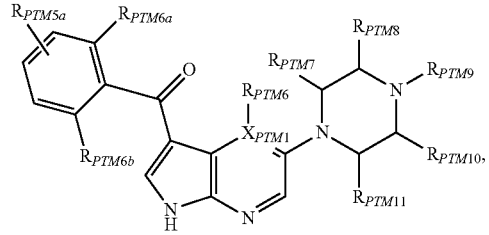

PTM-IIb wherein:

$X_{PTM1}$, $X_{PTM2}$, $X_{PTM3}$, $X_{PTM4}$, $X_{PTM5}$, and $X_{PTM6}$ are independently selected from CH or N; $R_{PTM5a}$ is selected from the group consisting of: bond, optionally substituted amine, optionally substituted amide (e.g., optionally substituted with an alkyl, methyl, ethyl, propyl, or butyl group), H,

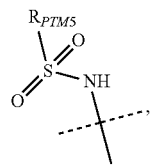

—NHC(O)$R_{PTM5}$;

$R_{PTM5}$ is selected from the group consisting of

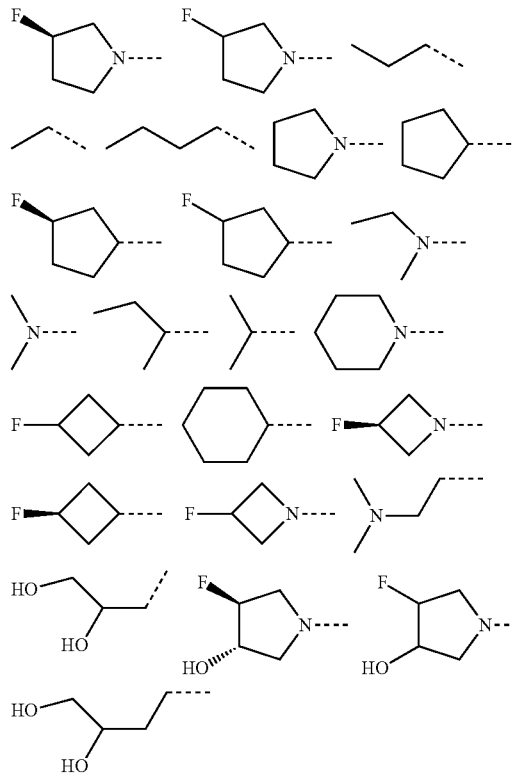

$R_{PTM6a}$ and $R_{PTM6b}$ are each independently selected from hydrogen, halogen, or optionally substituted $C_1$-$C_6$ alkyl (linear, branched, optionally substituted);

$R_{PTM6}$ is absent, hydrogen, halogen, aryl, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM7}$ is absent, hydrogen, halogen, aryl, methyl, ethyl, $OCH_3$, $NHCH_3$ or M1-$CH_2$—$CH_2$-M2, wherein M1 is $CH_2$, O or NH, and M2 is hydrogen, alkyl, cyclic alkyl, aryl or heterocycle;

$R_{PTM8}$, $R_{PTM9}$ or $R_{PTM10}$ are independently selected from the group consisting of absent, hydrogen, halogen, aryl, heteroaryl, alkyl, cycloalkyl, heterocycle, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM11}$ is absent, hydrogen, halogen, methyl, ethyl, $OCH_3$, $NH CH_3$ or M1-$CH_2$—$CH_2$-M2, wherein M1 is $CH_2$, O or NH, and M2 is hydrogen, alkyl, cyclic alkyl, aryl or heterocycle; and at least one of $R_{PTM8}$, $R_{PTM9}$ or $R_{PTM10}$ is modified to be covalently joined to a ULM, a chemical linker group (L), a CLM, an ILM, a VLM, MLM, a ULM', a CLM', a ILM', a VLM', a MLM', or combination thereof.

In certain embodiments, the PTM may comprise a chemical group selected from the group of chemical structures consisting of:

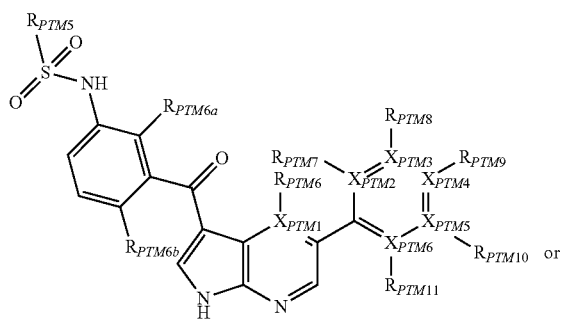

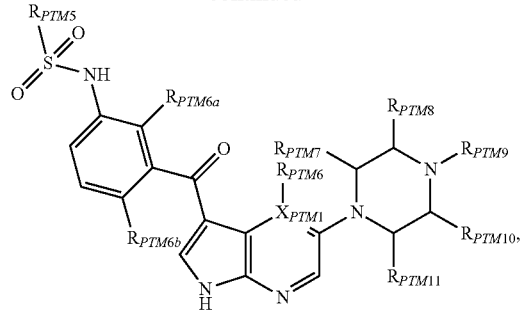

wherein $R_{PTM5}$, $R_{PTM6a}$, $R_{PTM6b}$, $R_{PTM6}$, $R_{PTM7}$, $R_{PTM8}$, $R_{PTM9}$, $R_{PTM10}$, $R_{PTM11}$ are as described herein.

In some embodiments, when $R_{PTM9}$ is the covalently joined position, $R_{PTM7}$ and $R_{PTM8}$ can be connected together via a covalent bond in a way to form a bicyclic group with the ring to which $R_{PTM7}$ and $R_{PTM8}$ are attached.

In other embodiments, when $R_{PTM8}$ is the covalently joined position, $R_{PTM9}$ and $R_{PTM10}$ can be connected together via a covalent bond in a way to form a bicyclic group with the ring to which $R_{PTM9}$ and $R_{PTM10}$ are attached.

In further embodiments, when $R_{PTM10}$ is the covalently joined position, $R_{PTM8}$ and $R_{PTM9}$ can be connected together via a covalent bond in a way to form a bicyclic group with the ring to which $R_{PTM8}$ and $R_{PTM9}$ are attached.

In any aspect or embodiment described herein, the PTM may comprise a chemical group selected from the group of chemical structures consisting of PTM-III:

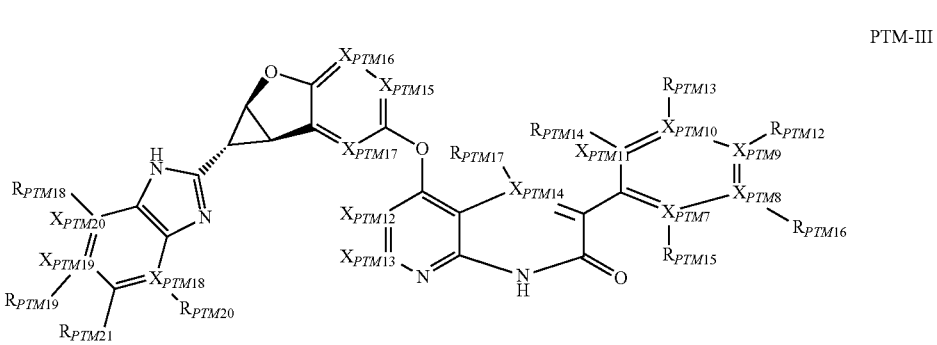

PTM-III wherein:

$X_{PTM7}$, $X_{PTM8}$, $X_{PTM9}$, $X_{PTM10}$, $X_{PTM11}$, $X_{PTM12}$, $X_{PTM13}$, $X_{PTM14}$, $X_{PTM15}$, $X_{PTM16}$, $X_{PTM17}$, $X_{PTM18}$, $X_{PTM19}$, $X_{PTM20}$ are independently CH or N;

$R_{PTM12}$, $R_{PTM13}$, $R_{PTM14}$, $R_{PTM15}$, $R_{PTM16}$, $R_{PTM17}$, $R_{PTM18}$, $R_{PTM19}$ are independently selected from the group consisting of absent, hydrogen, halogen, aryl, heteroaryl, cycloalkyl, heterocycle, methyl, ethyl, other alkyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM20}$ is a small group containing less than four non-hydrogen atoms;

$R_{PTM21}$ is selected from the group consisting of trifluoromethyl, chloro, bromo, fluoro, methyl, ethyl, propyl, isopropyl, tert-butyl, butyl, iso-butyl, cyclopropyl, cyclobutyl, cyclopentyl, cyclohexyl, $OCH_3$, $NHCH_3$, dimethylamino or M1-$CH_2$—$CH_2$-M2, wherein M1 is $CH_2$, O or NH, and M2 is hydrogen, alkyl, cyclic alkyl, aryl or heterocycle; and at least one of $R_{PTM12}$, $R_{PTM13}$ and $R_{PTM16}$ is modified to be covalently joined to a ULM, a chemical linker group (L), a CLM, an ILM, a VLM, MLM, a ULM', a CLM', a ILM', a VLM', a MLM', or combination thereof.

In some embodiments, when $R_{PTM12}$ is the covalently joined position, $R_{PTM13}$ and $R_{PTM14}$ can be connected together via a covalent bond in a way to form a bicyclic group with the ring to which $R_{PTM13}$ and $R_{PTM14}$ are attached; and/or $R_{PTM15}$ and $R_{PTM16}$ can be connected together via a covalent bond in a way to form a bicyclic group with the ring to which $R_{PTM15}$ and $R_{PTM16}$ are attached.

In other embodiments, when $R_{PTM13}$ is the covalently joined position, $R_{PTM12}$ and $R_{PTM16}$ can be connected together via a covalent bond in a way to form a bicyclic group with the ring to which $R_{PTM12}$ and $R_{PTM16}$ are attached; and/or $R_{PTM15}$ and $R_{PTM16}$ can be connected together via a covalent bond in a way to form a bicyclic group with the ring to which $R_{PTM15}$ and $R_{PTM16}$ are attached.

In further embodiments, when $R_{PTM16}$ is the covalently joined position, $R_{PTM12}$ and $R_{PTM13}$ can be connected together via a covalent bond in a way to form a bicyclic group with the ring to which $R_{PTM12}$ and $R_{PTM13}$ are attached; and/or $R_{PTM13}$ and $R_{PTM14}$ can be connected together via a covalent bond in a way to form a bicyclic group with the ring to which $R_{PTM13}$ and $R_{PTM14}$ are attached.

In any aspect or embodiment described herein, the PTM may comprise a chemical group selected from the group of chemical structures consisting of PTM-IVa or PTM-IVb:

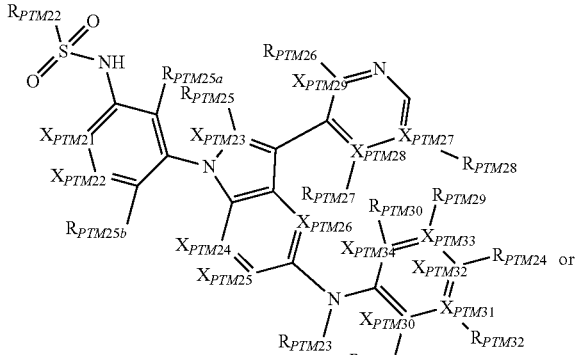

PTM-IVa

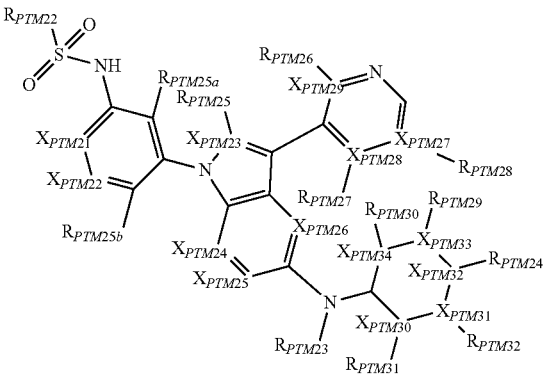

PTM-IVb wherein:

$X_{PTM21}$, $X_{PTM22}$, $X_{PTM23}$, $X_{PTM24}$, $X_{PTM25}$, $X_{PTM26}$, $X_{PTM27}$, $X_{PTM28}$, $X_{PTM29}$, $X_{PTM30}$, $X_{PTM31}$, $X_{PTM32}$, $X_{PTM33}$, $X_{PTM34}$ are independently CH or N;

$R_{PTM22}$ is selected from the group consisting of

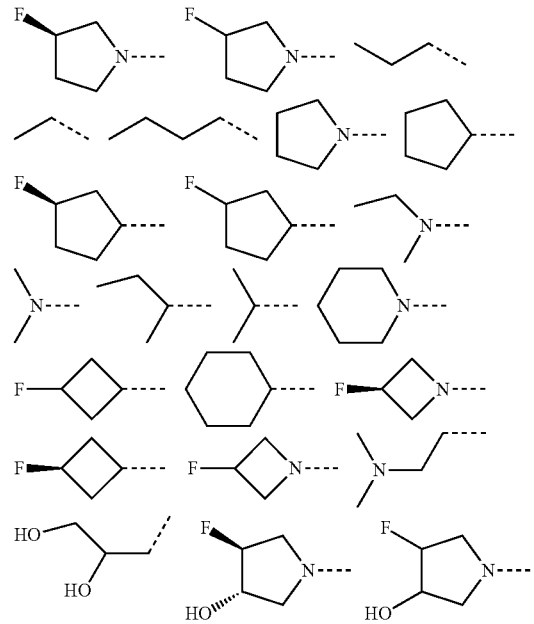

-continued

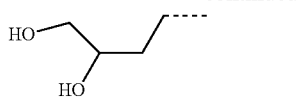

$R_{PTM25a}$ and $R_{PTM25b}$ are each independently selected from hydrogen, halogen, or $C_1$-$C_6$ alkyl (linear, branched, optionally substituted);

$R_{PTM23}$, $R_{PTM24}$, $R_{PTM28}$, $R_{PTM29}$, $R_{PTM30}$, $R_{PTM31}$, $R_{PTM32}$ are independently selected from the group consisting of absent, bond, hydrogen, halogen, aryl (optionally substituted), heteroaryl (optionally substituted), cycloalkyl (optionally substituted), heterocycle (optionally substituted), methyl, ethyl (optionally substituted), other alkyl (linear, branched, optionally substituted), $OCH_3$, $NHCH_3$ or M1-$CH_2$—$CH_2$-M2, wherein M1 is $CH_2$, O and NH, and M2 is hydrogen, alkyl (linear, branched, optionally substituted), cyclic alkyl (optionally substituted), aryl (optionally substituted) or heterocycle (optionally substituted); and $R_{PTM25}$ is absent, hydrogen, halogen, $C_1$-$C_6$ alkyl (linear, branched, optionally substituted), OCH3, $NHCH_3$ or $SCH_3$;

$R_{PTM26}$ is absent, hydrogen, halogen, $C_1$-$C_6$ alkyl (linear, branched, optionally substituted), OCH3, $NHCH_3$ or $SCH_3$;

$R_{PTM27}$ is selected from the group consisting of absent, hydrogen, halogen, $C_1$-$C_6$ alkyl (linear, branched, optionally substituted), $OCH_3$, $NHCH_3$ or $SCH_3$; and at least one of $R_{PTM24}$, $R_{PTM29}$, $R_{PTM32}$ is modified to be covalently joined to a ULM, a chemical linker group (L), a CLM, an ILM, a VLM, MLM, a ULM', a CLM', a ILM', a VLM', a MLM', or combination thereof.

In some embodiments, when $R_{PTM24}$ is the covalently joined position, $R_{PTM31}$ and $R_{PTM32}$ can be connected together via a covalent bond in a way to form a bicyclic group with the ring to which $R_{PTM31}$ and $R_{PTM32}$ are attached; or $R_{PTM29}$ and $R_{PTM30}$ can be connected together via a covalent bond in a way to form a bicyclic group with the ring to which $R_{PTM29}$ and $R_{PTM30}$ are attached.

In other embodiments, when $R_{PTM29}$ is the covalently joined position, $R_{PTM24}$ and $R_{PTM32}$ can be connected together via a covalent bond in a way to form a bicyclic group with the ring to which $R_{PTM24}$ and $R_{PTM32}$ are attached; and/or $R_{PTM31}$ and $R_{PTM32}$ can be connected together via a covalent bond in a way to form a bicyclic group with the ring to which $R_{PTM31}$ and $R_{PTM32}$ are attached.

In further embodiments, when $R_{PTM32}$ is the covalently joined position, $R_{PTM24}$ and $R_{PTM29}$ can be connected together via a covalent bond in a way to form a bicyclic group with the ring to which $R_{PTM24}$ and $R_{PTM29}$ are attached; and/or $R_{PTM29}$ and $R_{PTM30}$ can be connected together via a covalent bond in a way to form a bicyclic group with the ring to which $R_{PTM29}$ and $R_{PTM30}$ are attached.

In any aspect or embodiments described herein, the PTM is selected from the group consisting of chemical structures PTM-1, PTM-2, PTM-3, PTM-4, PTM-5, PTM-6, PTM-7, and PTM-8:

PTM-1

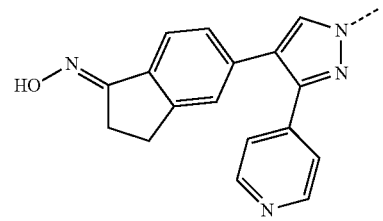

PTM-2

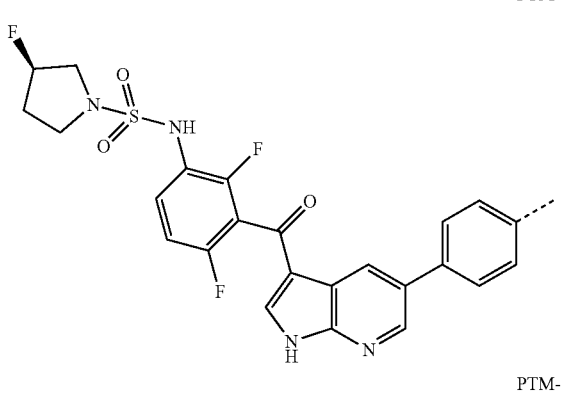

PTM-3

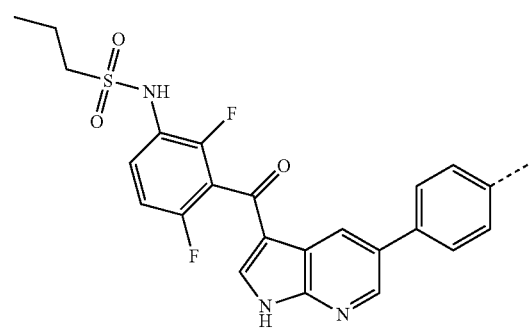

PTM-4

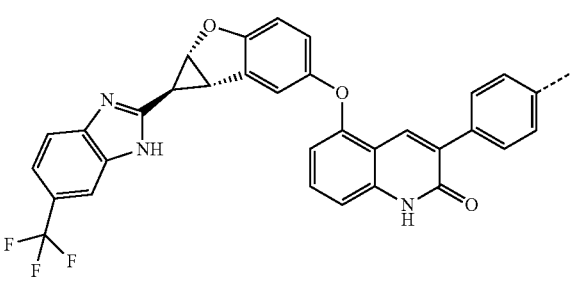

PTM-5

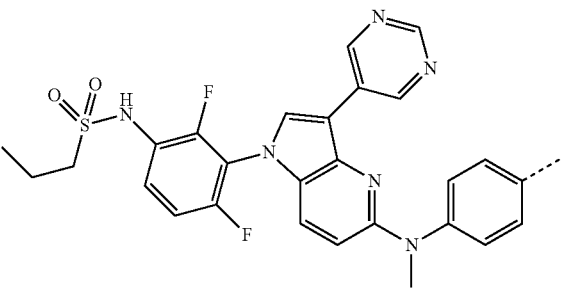

In any aspect or embodiment described herein, the ULM is selected from the group consisting of:
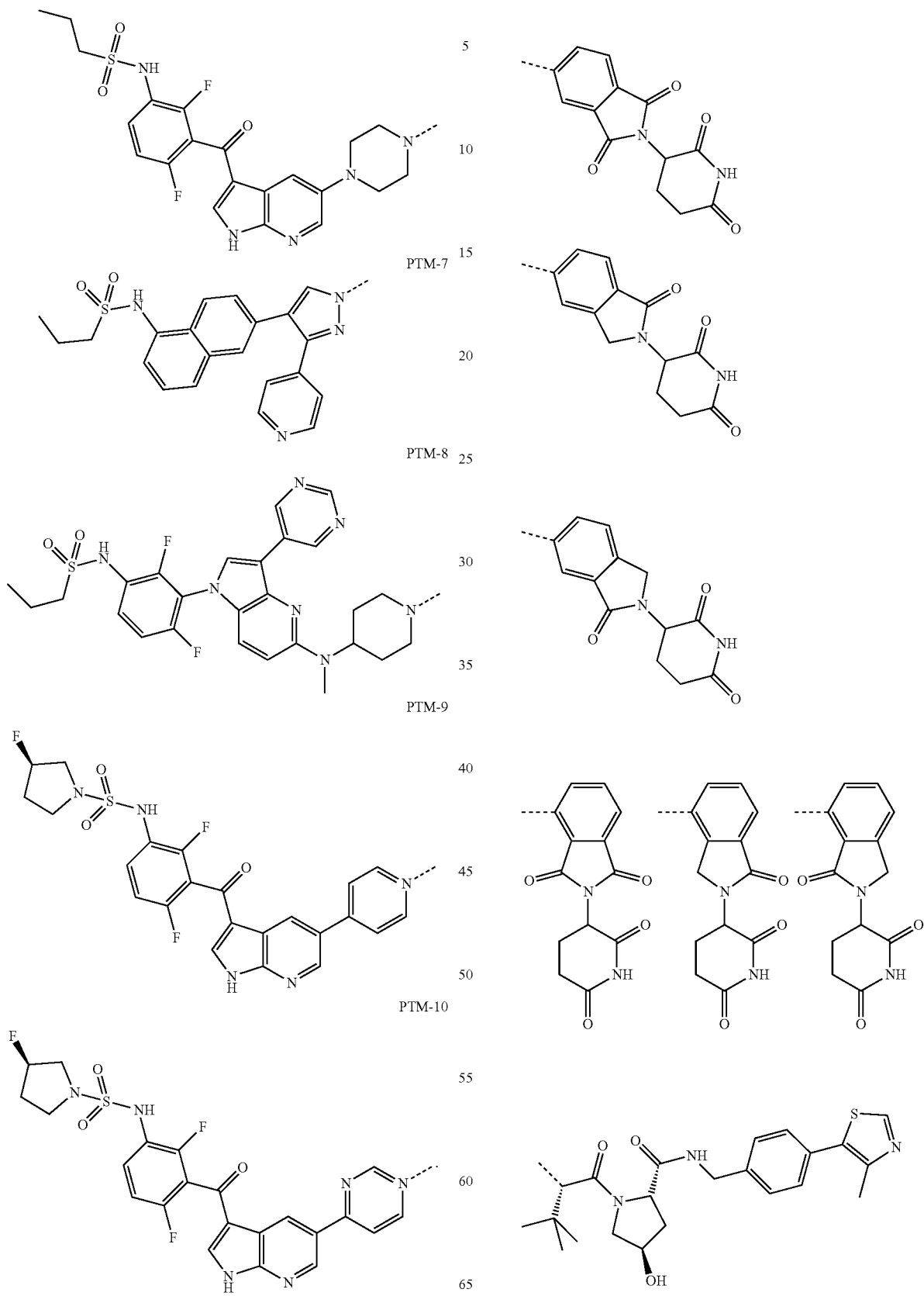

431

-continued

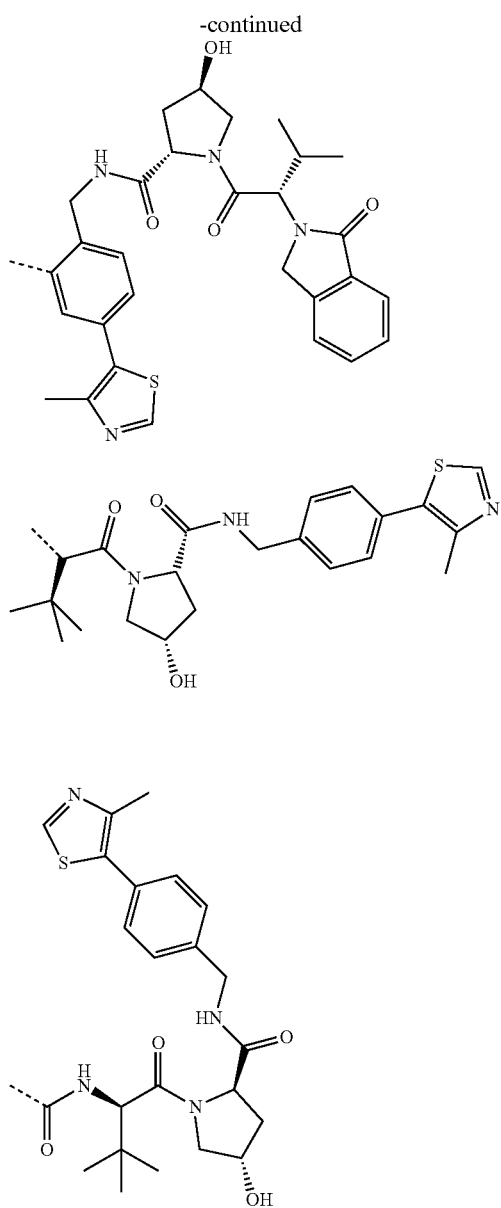

432

-continued

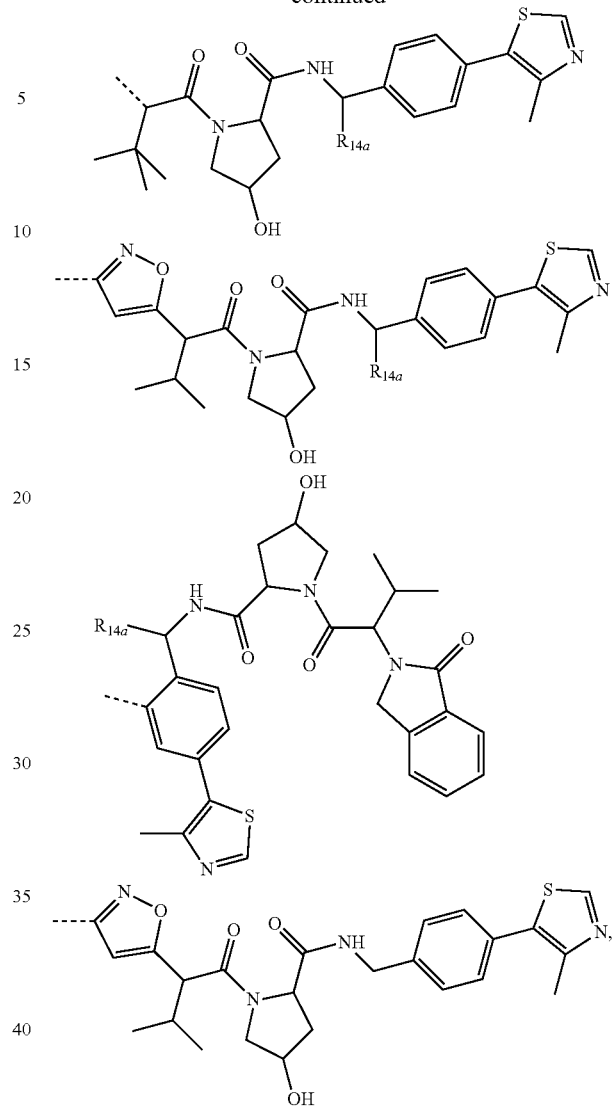

wherein the $R_{14a}$ is a H, methyl or hydroxymethyl.

Therapeutic Compositions

Pharmaceutical compositions comprising combinations of an effective amount of at least one bifunctional compound as described herein, and one or more of the compounds otherwise described herein, all in effective amounts, in combination with a pharmaceutically effective amount of a carrier, additive or excipient, represents a further aspect of the present disclosure.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Hely or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known erythopoiesis stimulating agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as erythropoietin stimulating agents, including EPO and darbapoietin alfa, among others. In certain preferred aspects of the disclosure, one or more compounds according to the present disclosure are coadministered with another bioactive agent, such as an erythropoietin stimulating agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, cardiofaciocutaneous syndrome, neurofibromatosis type 1, Costello syndrome, Noonan Syndrome, LEOPARD (Lentigo, Electrocardiographic abnormalities, Ocular hypertelorism, or Pulmonary stenosis, Abnormal genitalia, Retarded growth, Deafness) syndrome, which may be treated using compounds according to the present disclosure are set forth hereinabove.

The description provides therapeutic compositions as described herein for effectuating the degradation of proteins of interest for the treatment or amelioration of a disease, e.g., cancer, cardiofaciocutaneous syndrome, neurofibromatosis type 1, Costello syndrome, Noonan syndrome, or LEOPARD (Lentigo, Electrocardiographic abnormalities, Ocular hypertelorism, Pulmonary stenosis, Abnormal genitalia, Retarded growth, Deafness) syndrome. In certain additional embodiments, the disease is multiple myeloma. As such, in another aspect, the description provides a method of ubiquitinating/degrading a target protein in a cell. In certain embodiments, the method comprises administering a bifunctional compound as described herein comprising, e.g., a ULM and a PTM, preferably linked through a linker moiety, as otherwise described herein, wherein the ULM is coupled to the PTM and wherein the ULM recognizes a ubiquitin pathway protein (e.g., an ubiquitin ligase, such as an E3 ubiquitin ligase including cereblon, VHL, IAP, and/or MDM2) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cell, e.g., cell of a patient. In certain embodiments, the method comprises administering an effective amount of a compound as described herein, optionally including a pharmaceutically acceptable excipient, carrier, adjuvant, another bioactive agent or combination thereof.

In additional embodiments, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present disclosure.

In another embodiment, the present disclosure is directed to a method of treating a human patient in need for a disease state or condition modulated through a protein where the degradation of that protein will produce a therapeutic effect in the patient, the method comprising administering to a patient in need an effective amount of a compound according to the present disclosure, optionally in combination with another bioactive agent. The disease state or condition may be a disease caused by a microbial agent or other exogenous agent such as a virus, bacteria, fungus, protozoa or other microbe or may be a disease state, which is caused by overexpression and/or overactivation (e.g., a constitutively active) of a protein, which leads to a disease state and/or condition The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states or conditions which may be treated using compounds according to the present disclosure include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4

(PKD2) Prader-Willi syndrome, Sickle-cell disease, Tay-Sachs disease, Turner syndrome.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

The term "bioactive agent" is used to describe an agent, other than a compound according to the present disclosure, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents, anti-retrovirus and anti-HCV agents, antimicrobial agents, antifungal agents, etc.

The term "additional anti-cancer agent" is used to describe an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT- 578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "anti-HIV agent", "anti-retroviral", or "additional anti-HIV agent" includes, for example, nucleoside reverse transcriptase inhibitors (NRTI), other non-nucloeoside reverse transcriptase inhibitors (i.e., those which are not representative of the present disclosure), protease inhibitors, fusion inhibitors, among others, exemplary compounds of which may include, for example, 3TC (Lamivudine), AZT (Zidovudine), (-)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV/anti-retroviual agents which may be used in coadministration with compounds according to the present disclosure include, for example, other NNRTI's (i.e., other than the NNRTI's according to the present disclosure) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC 125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis (methoxycarbonyl)-6,6-diphenylhexenoate), Methyl 3-Bromo-5-(1-5-bromo-4-methoxy-3-(methoxycarbonyl) phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl] piperazine, 1-[3-(Ethylamino)-2-[pyridinyl]-4-[(5-hydroxy-2-indolyl)carbonyl]piperazine, 1-[(6-Formyl-2-indolyl) carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S (1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

General Synthetic Approach

The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way one can identify and optimize ligands for an E3 Ligase, i.e. ULMs/ILMs/VLMs/CLMs/ILMs.

With PTMs and ULMs (e.g. ILMs, VLMs, CLMs, and/or ILMs) in hand, one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

LIST OF ABBREVIATIONS

AcOH, acetic acid
aq., aqueous
BINAP, 2,2'-bis(diphenylphosphino)-1,1'-binaphthalene
Boc, tert-butoxycarbonyl
$Boc_2O$, di-tert-butyl dicarbonate
BOP, (benzotriazol-1-yloxy)tris(dimethylamino)phosphonium hexafluorophosphate
$CDCl_3$, deuteriochloroform
CD3OD, deuteriomethanol
$CH_3CN$, acetonitrile
$CH_3OH$, methanol
CsF, cesium fluoride
$Cs_2CO_3$, cesium carbonate
$Cu(OAc)_2$, copper (II) acetate
$Cy_2NMe$, dicyclohexylmethylamine
DCM, dichloromethane
DIAD, diisopropyl azodicarboxylate
DIEA or DIPEA, diisopropylethylamine
DMAP, N,N-dimethylaminopyridine
DMF, N,N-dimethylformamide
DMSO, dimethylsulfoxide
$DMSO-d_6$, hexadeuterodimethyl sulfoxide
$Et_2NH$, diethylamine
EtOAc or EA, ethyl acetate
HCl, hydrochloric acid
$H_2O$, water
HPLC, high performance liquid chromatography
IBX, 2-iodoxybenzoic acid
KOAc, potassium acetate
LCMS, liquid chromatography/mass spectrometry
LiOH, lithium hydroxide
MeOH, methanol
MsCl, methanesulfonyl chloride
$N_2$, nitrogen
NaH, sodium hydride
$NaBH_3CN$, sodium cyanoborohydride
$NaBH(OAc)_3$, sodium triacetoxyborohydride
NaCl, sodium chloride
$NaHCO_3$, sodium bicarbonate
NaI, sodium iodide
$Na_2SO_4$, sodium sulfate
n-BuLi, n-butyllithium
$NH_3$, ammonia
$NH_4Cl$, ammonium chloride
$NH_2OH$ HCl, hydroxylamine hydrochloride
NMP, N-methylpyrrolidone
NMR, nuclear magnetic resonance
$O_2$, oxygen
$Pd(aMPhos)Cl_2$, bis(di-tert-butyl(4-dimethylaminophenyl)phosphine)dichloropalladium(II)
$Pd_2(dba)_3$, tris(dibenzylideneacetone)dipalladium(O)
$Pd(dppf)Cl_2$, [1,1'-bis(diphenylphosphino)ferrocene]dichloropalladium(II)
$Pd(OH)_2$, palladium hydroxide
$Pd(PPh_3)_4$, tetrakis(triphenylphosphine)palladium(O)
PE, petroleum ether
$Ph_3P$, triphenylphosphine
Py, pyridine
PyB OP, (benzotriazol-1-yloxy)tripyrrolidinophosphonium hexafluorophosphate
rt, room temperature
TBAF, tetra-n-butylammonium fluoride
TBDPSCl, tert-butyldiphenylsilyl chloride
TBS, tert-butyldimethylsilyl
tBuOK, potassium tert-butoxide
$[tBu_3PH]BF_4$, tri-tert-butyl phosphonium tetrafluoroborate
TEA, triethylamine
THF, tetrahydrofuran
TLC, thin layer chromatography
TMS OTf, trimethylsilyl trifluoromethanesulfonate
TsCl, p-toluenesufonyl chloride
TsOH, p-toluenesulfonic acid Scheme 1.

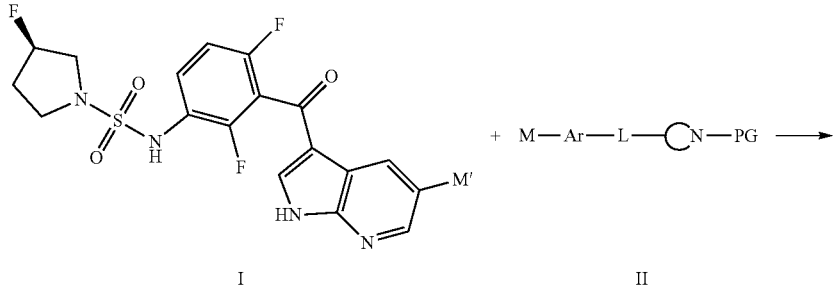

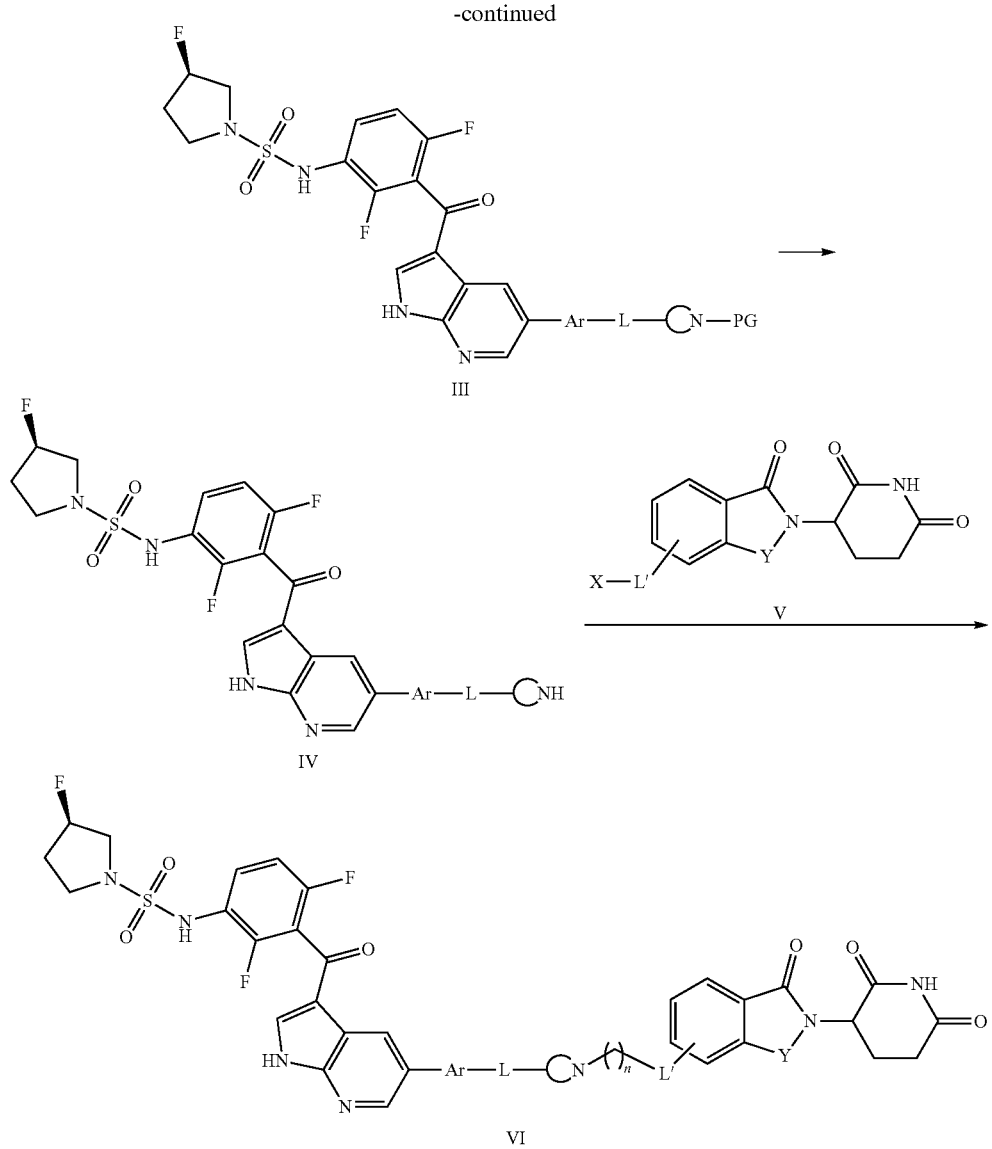

A compound of formula I may be reacted with a reagent II (commercially available or readily prepared using standard reaction techniques known to one skilled in the art) under palladium-catalyzed cross-coupling conditions, e.g. with a suitable palladium catalyst such as bis(di-tert-butyl (4-dimethylaminophenyl)phosphine)dichloropalladium(II), suitable base such as cesium fluoride, suitable solvent such as mixtures of 1,4-dioxane and water, at a suitable temperature such as 100° C., with or without microwave irradiation to produce a compound of formula III. One of M or M' represents a functional group capable of undergoing palladium-catalyzed transmetallation, e.g. a boronic acid, boronic ester, or trialkylstannane; the other of M or M' represents a functional group capable of undergoing palladium-catalyzed oxidative addition, e.g. an iodide, bromide, chloride, or trifluoromethanesulfonate; Ar represents an aromatic or heteroaromatic ring system; L represents an optional linker or portion of a linker, represents a primary or secondary amine, optionally cyclized into a 4 to 8 membered heterocyclic ring, wherein PG represents a suitable protecting group, including but not limited to t-butoxycarbonyl or benzyl. Compounds of formula III may be converted to a compound of formula IV by treatment with a reagent suitable for the removal of PG, e.g. hydrogen chloride in 1,4-dioxane when PG is t-butoxycarbonyl. Compound IV may then be reacted with compound V to produce compound VI, wherein L' represents an optional linker or portion of a linker, Y is $CH_2$ or C=O, and X is either a suitable leaving group (e.g. OMs, OTs, Cl, etc.) or an aldehyde (CHO). When X is a leaving group, n is 0, and suitable reaction conditions are those for an alkylation reaction, e.g. diisopropylethylamine, potassium iodide, DMSO or acetonitrile, 80° C. When X is an aldehyde, n is 1, and suitable reaction conditions are those for a reductive amination reaction, e.g. sodium cyanoborohydride, methanol, dichloromethane, acetic acid, room temperature.

Scheme 2.
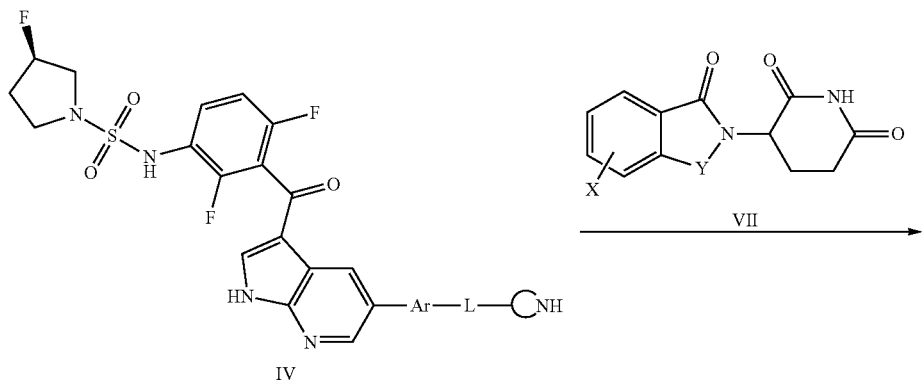
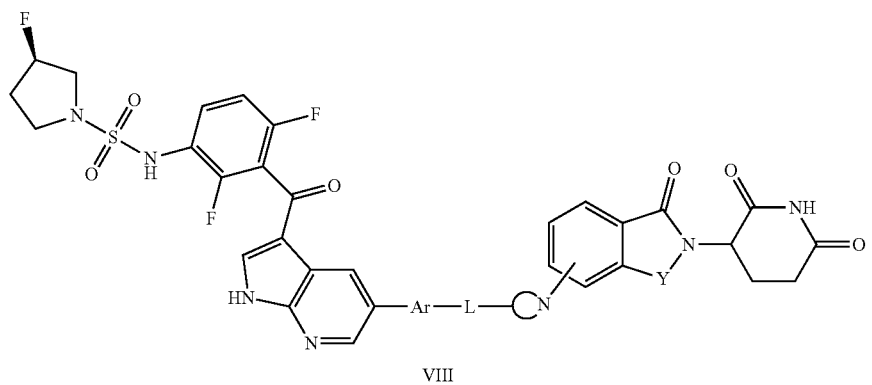
A compound of formula IV may also be reacted with a compound of formula VII to provide compounds of formula VIII, wherein X is a suitable leaving group such as fluorine or chlorine, Y is C=O, and reaction conditions are those for a nucleophilic aromatic substitution, e.g. triethylamine, DMSO, 70° C.
Scheme 3.
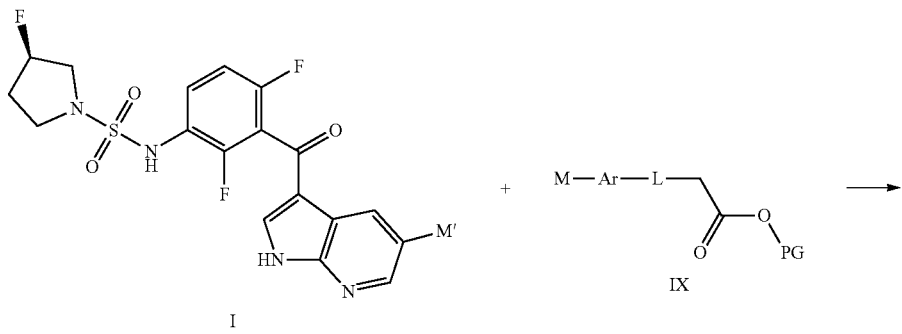

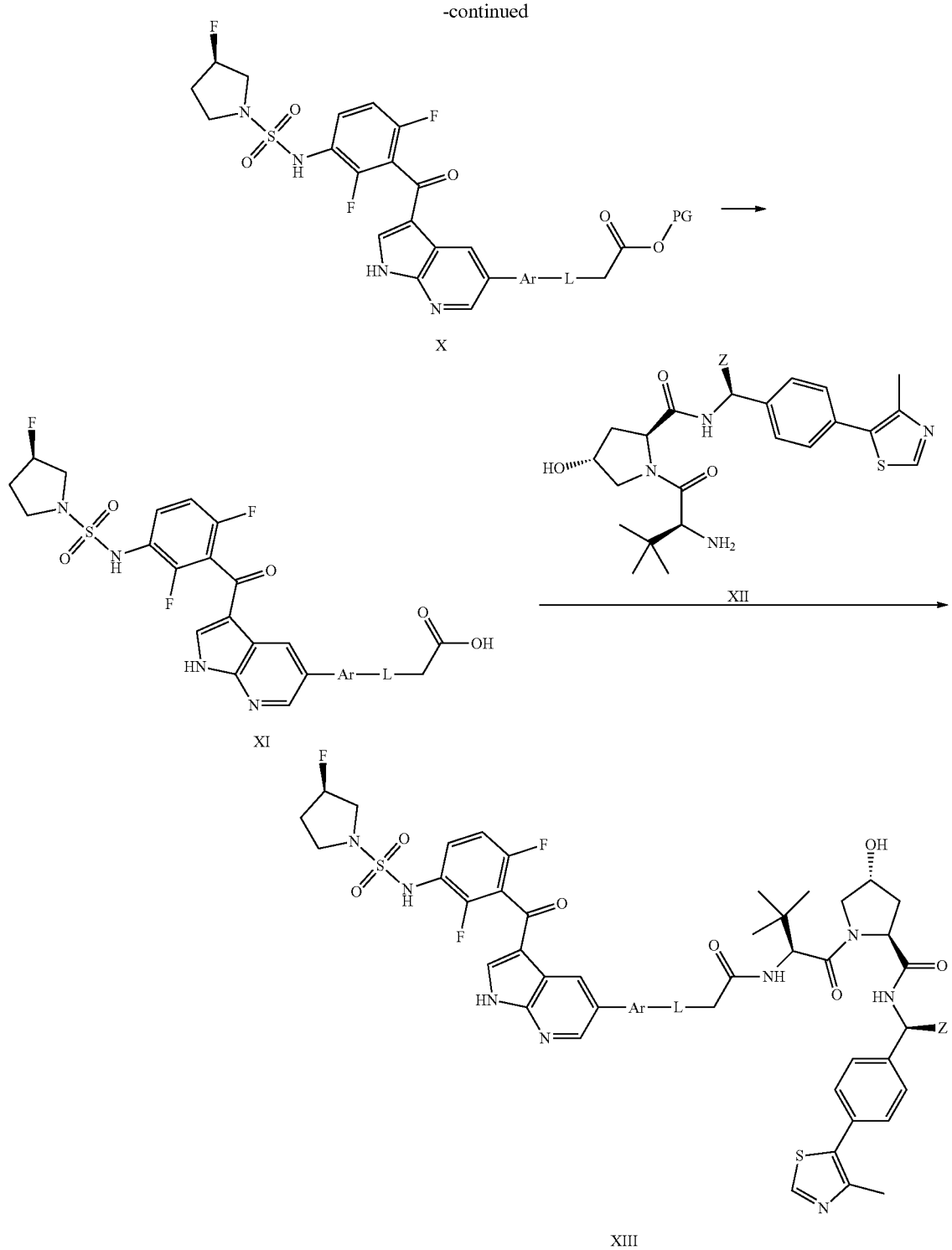

A compound of formula I may be reacted with a reagent IX (commercially available or readily prepared using standard reaction techniques known to one skilled in the art) under palladium-catalyzed cross-coupling conditions, e.g. as shown in Scheme 1, to produce a compound of formula X. One of M or M' represents a functional group capable of undergoing palladium-catalyzed transmetallation, e.g. a boronic acid, boronic ester, or trialkylstannane; the other of M or M' represents a functional group capable of undergoing palladium-catalyzed oxidative addition, e.g. an iodide, bromide, chloride, or trifluoromethanesulfonate; Ar represents an aromatic or heteroaromatic ring system; L represents an optional linker or portion of a linker, and PG represents a suitable ester protecting group, e.g. methyl, ethyl, or t-butyl. Compounds of formula X may be converted to a compound of formula XI by treatment with a reagent suitable for the removal of PG, e.g. hydrogen chloride in 1,4-dioxane when PG is t-butyl. Compound XI may then be reacted with compound XII, wherein Z is an optional substituent, e.g. H, methyl, or hydroxymethyl, to produce compounds of formula XIII under amide formation conditions, e.g. (benzotriazol-1-yloxy)tripyrrolidinophosphonium hexafluorophosphate, diisopropylethylamine, DMF, room temperature.

Scheme 4.

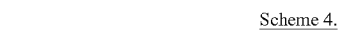

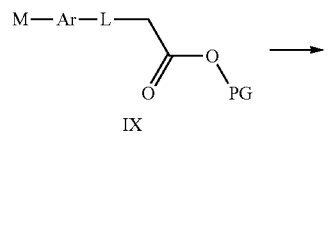

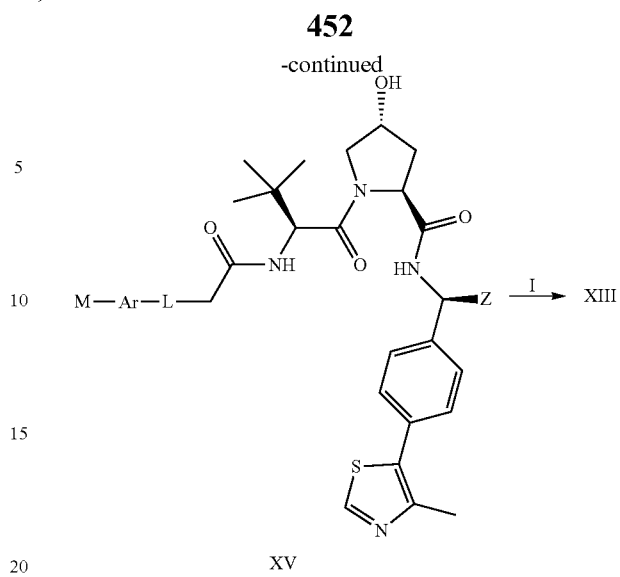

Alternatively, a compound of formula IX may be converted to a compound of formula XIV by using conditions analogous to those for the conversion of X to XI in Scheme 3. A compound of formula XIV may be converted to a compound of formula XV by using conditions analogous to those for the conversion of XI to XIII in Scheme 3. A compound of formula XV may then be converted to a compound of formula XIII by reaction with a compound of formula I using conditions analogous to those for the conversion of I and IX to X in Scheme 3.

Scheme 5.

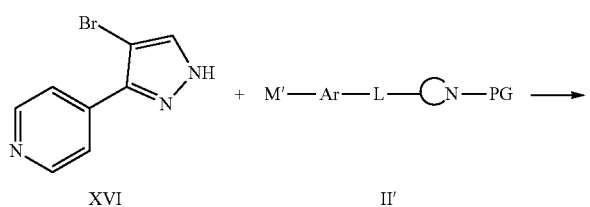

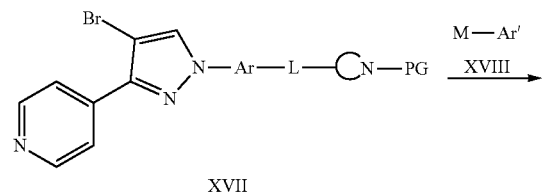

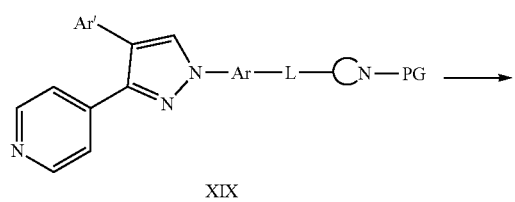

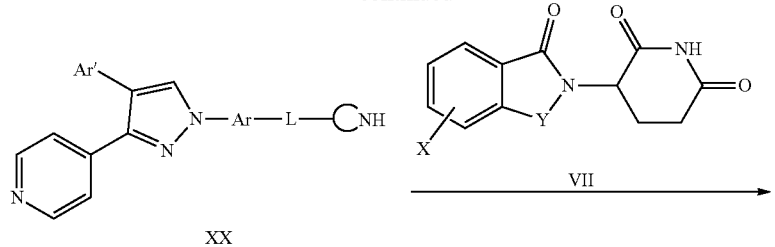

XX

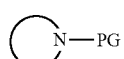

XXI

A compound of formula XVI may be reacted with a reagent II' (commercially available or readily prepared using standard reaction techniques known to one skilled in the art) under Chan-Lam cross-coupling conditions, e.g. copper (II) acetate, pyridine or diethylamine or triethylamine, 100° C., to produce a compound of formula XVII. M' represents a boronic acid or boronic ester; Ar represents an aromatic or heteroaromatic ring system; L represents an optional linker,

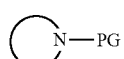

represents a primary or secondary amine, optionally cyclized into a 4 to 8 membered heterocyclic ring, wherein PG represents a suitable protecting group, including but not limited to t-butoxycarbonyl or benzyl. Compounds of formula XVII may be may be reacted with a reagent XVIII under palladium-catalyzed cross-coupling conditions, e.g. [1,1'-bis(diphenylphosphino)ferrocene] dichloropalladium, tri-tert-butylphosphine tetrafluoroborate, cesium fluoride, 1,4-dioxane, 90° C., to produce a compound of formula XIX. M represents a functional group capable of undergoing palladium-catalyzed transmetallation, e.g. a boronic acid, boronic ester, or trialkylstannane and Ar' represents an aromatic or heteroaromatic ring system with optional substituents. A compound of formula XIX may then be converted to a compound of formula XX by treatment with a reagent suitable for the removal of PG, e.g. hydrogen chloride in 1,4-dioxane or methanol when PG is t-butyl. A compound of formula XX may also be reacted with a compound of formula VII to provide compounds of formula XXI, wherein X is a suitable leaving group such as fluorine or chlorine, Y is C=O, the aromatic ring of VII may have further optional substituents, and reaction conditions are those for a nucleophilic aromatic substitution, e.g. triethylamine, DMSO, 80° C. In cases where the group Ar' contains optional substituents, e.g. a ketone, these may undergo further functionalization, e.g. by treatment with hydroxylamine hydrochloride and pyridine at room temperature, to provide further compounds of formula XXI.

Scheme 6.

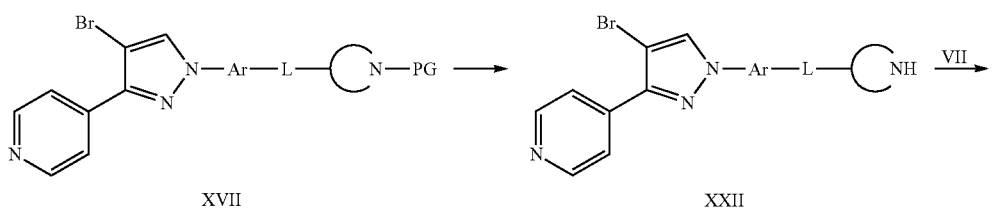

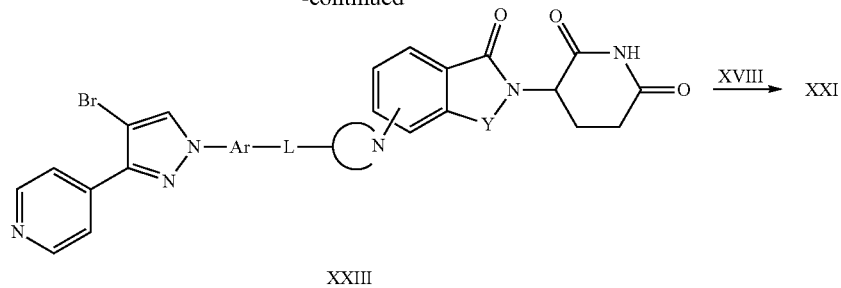

Alternatively, a compound of formula XVII may be converted to a compound of formula XXII by using conditions analogous to those for the conversion of XIX to XX in Scheme 5. A compound of formula XXII may then be treated with a compound of formula VII as defined in Scheme 5 to produce a compound of formula XXIII The compound of formula XXIII may then be treated with a reagent XVIII as defined in Scheme 5 to produce a compound of formula XXI. In cases where the group Ar' contains optional sub- stituents, e.g. a ketone, these may undergo further functionalization, e.g. by treatment with hydroxylamine hydrochloride and pyridine at room temperature, to provide further compounds of formula XXI.

Scheme 7.

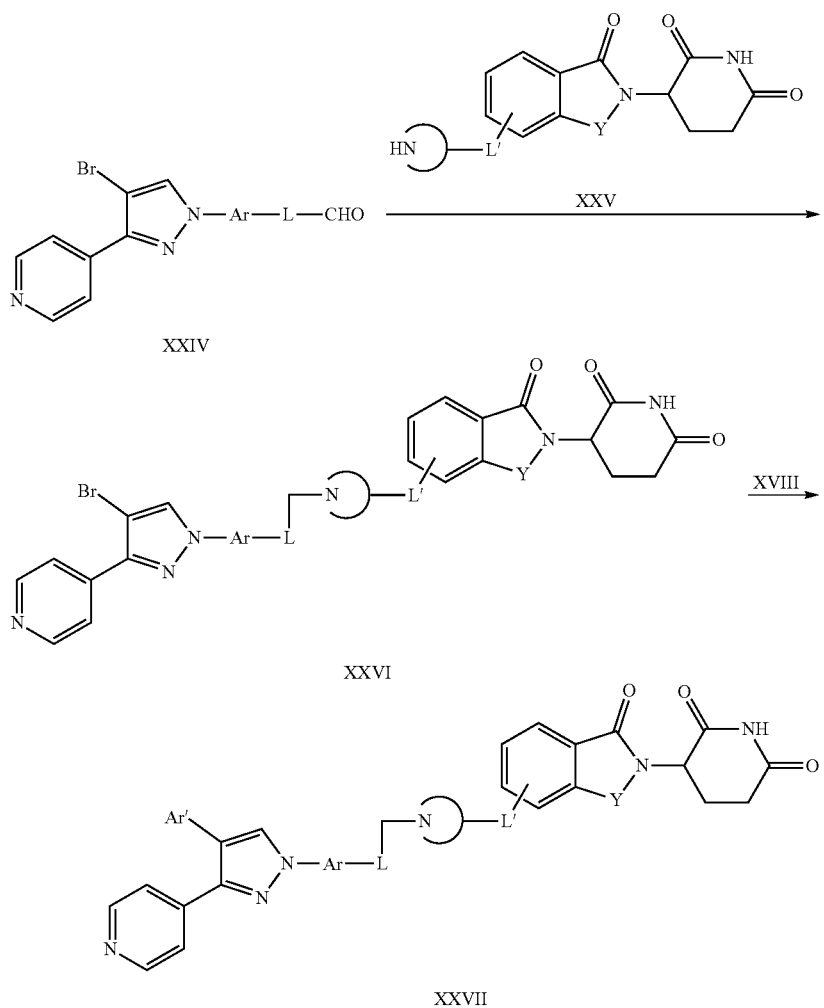

A compound of formula XXIV (prepared in an analogous manner to the preparation of XVII from XVI and II' in Scheme 5, with additional functional group transformations as necessary, which are well known to one skilled in the art) may be reacted with a compound of formula XXV to prepare a compound of formula XXVI under reductive amination conditions, e.g. sodium cyanoborohydride, acetic acid, methanol, room temperature. Herein Ar represents an aromatic or heteroaromatic ring system; L and L' represent an optional linker or portion of a linker, HN⌒ represents a primary or secondary amine, optionally cyclized into a 4 to 8 membered heterocyclic ring, and Y is CH$_2$ or C=O. A compound of formula XXVI may then be treated with a reagent XVIII as defined in Scheme 5 to produce a compound of formula XXVII. In cases where the group Ar' contains optional substituents, e.g. a ketone, these may undergo further functionalization, e.g. by treatment with hydroxylamine hydrochloride and pyridine at room temperature, to provide further compounds of formula XVII.

Alternatively, a compound of formula XXII may be treated with a compound of formula XXVIII under reductive amination conditions, e.g. as in Scheme 7, to provide a compound of formula XXVI'. Herein Ar, L, L', ⌒NH, and Y are defined as in Scheme 7. A compound of formula XXVI' may then be treated with a reagent XVIII as defined in Scheme 5 to produce a compound of formula XXVII'. In cases where the group Ar' contains optional substituents, e.g. a ketone, these may undergo further functionalization, e.g. by treatment with hydroxylamine hydrochloride and pyridine at room temperature, to provide further compounds of formula XVII'.

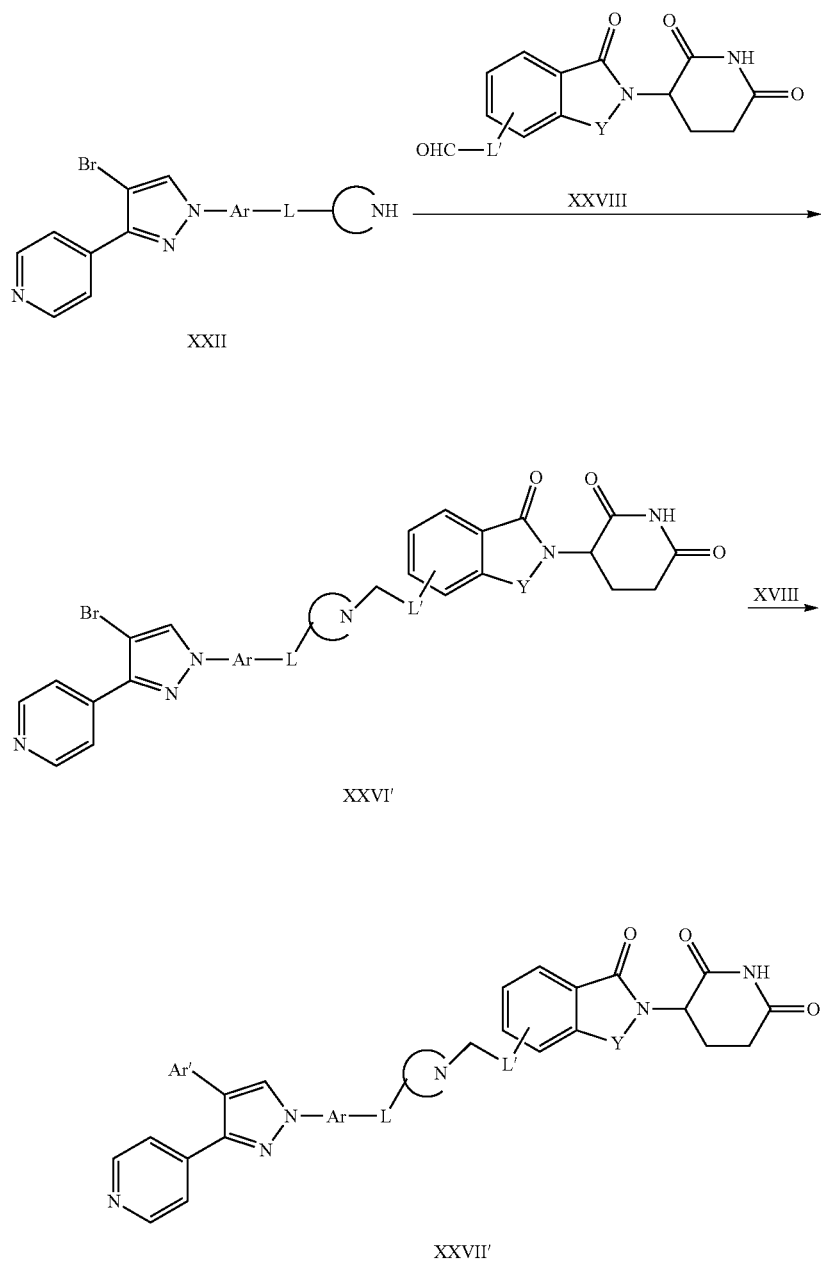

Scheme 9.

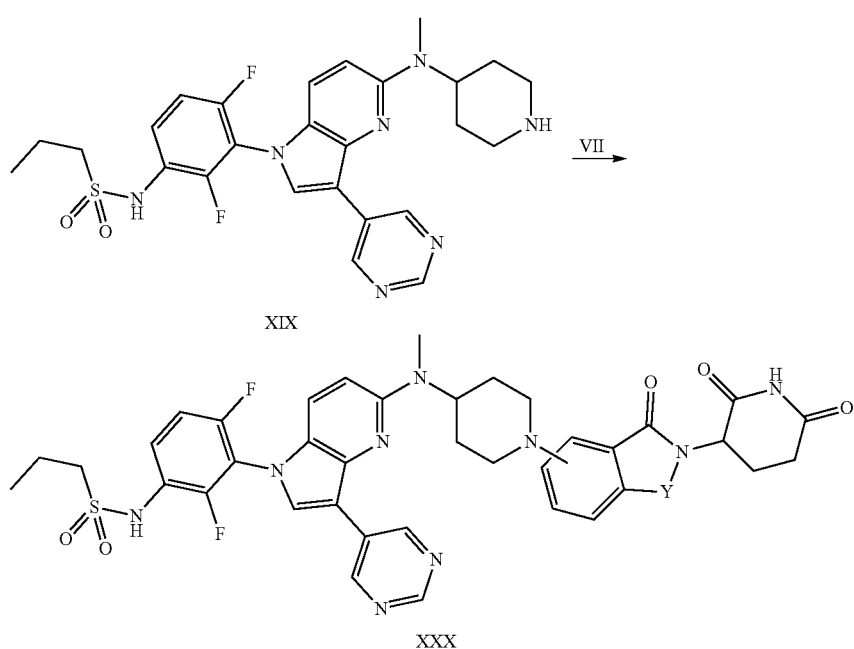

A compound of formula XIX may be reacted with a compound of formula VII to provide compounds of formula XXX, wherein X is a suitable leaving group such as fluorine or chlorine, Y is C=O, the aromatic ring of VII may have further optional substituents, and reaction conditions are those for a nucleophilic aromatic substitution, e.g. diisopropylethylamine, NMP, 130° C., with or without microwave irradiation.

Scheme 10.

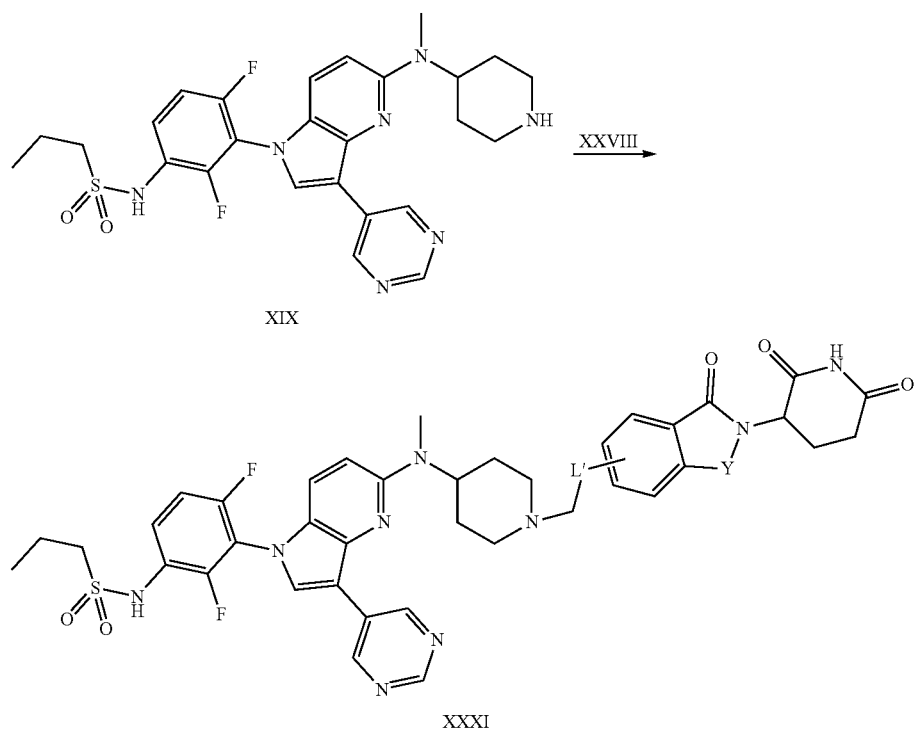

Alternatively, a compound of formula XIX may be treated with a compound of formula XXVIII to provide a compound of formula XXXI under reductive amination conditions, e.g. sodium triacetoxyborohydride, ethanol, dichloromethane, room temperature.

Scheme 11.

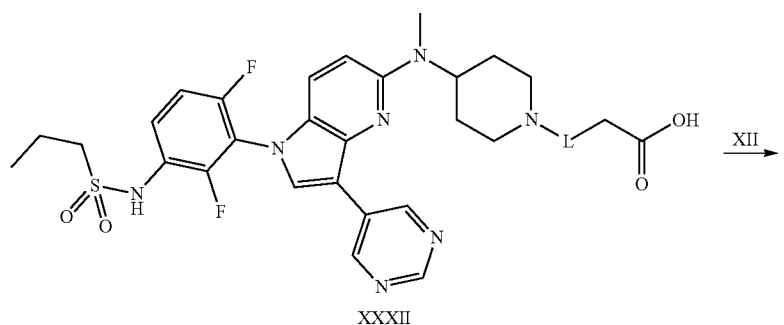

XXXII

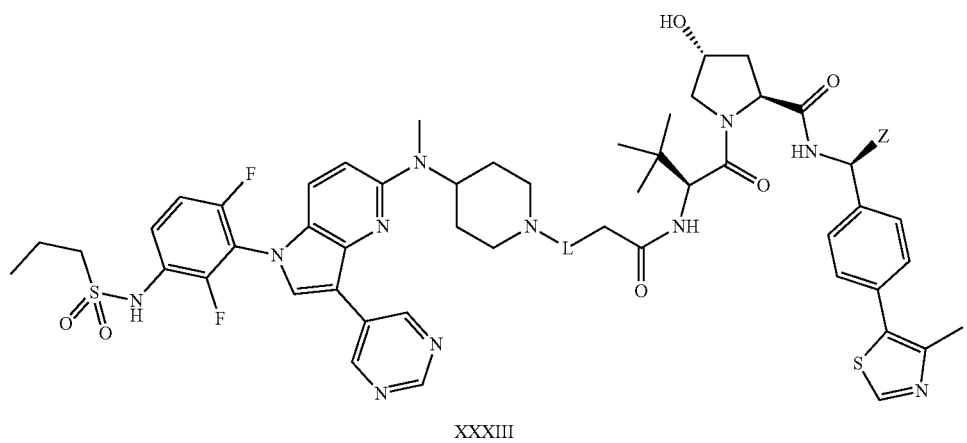

XXXIII

Alternatively, a compound of formula XXXII, prepared from a compound of formula XIX through simple transformations well-known by one skilled in the art, e.g. alkylation or reductive amination, may be reacted with a compound of formula XII to provide a compound of formula XXXIII under amide formation conditions, e.g. (benzotriazol-1-yloxy)tripyrrolidinophosphonium hexafluorophosphate, diisopropylethylamine, DMF, room temperature Scheme 12.

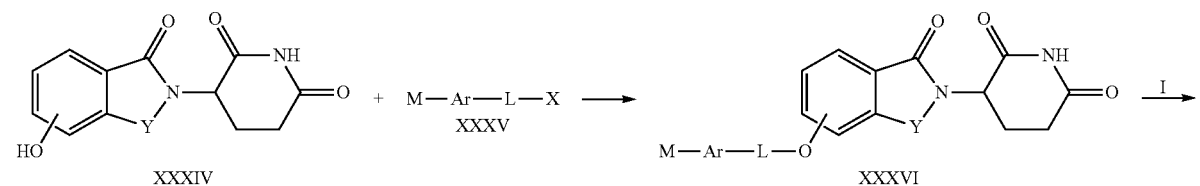

-continued

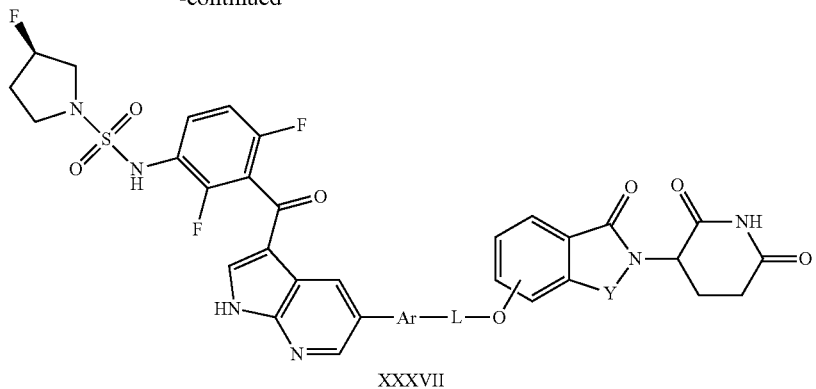

XXXVII

A compound of formula XXXIV may be reacted with a reagent XXXV (commercially available or readily prepared using standard reaction techniques known to one skilled in the art) under nucleophilic substitution conditions, e.g. potassium carbonate, potassium iodide, DMSO, 60° C., to produce a compound of formula XXXVI. Alternatively, the reaction conditions may be those for a Mitsunobu reaction, e.g. triphenylphosphine, diethylazodicarboxylate, THF. Herein Y is CH$_2$ or C=O; one of M or M' represents a functional group capable of undergoing palladium-catalyzed transmetallation, e.g. a boronic acid, boronic ester, or trialkylstannane; the other of M or M' represents a functional group capable of undergoing palladium-catalyzed oxidative addition, e.g. an iodide, bromide, chloride, or trifluoromethanesulfonate; Ar represents an aromatic or heteroaromatic ring system; and L represents a linker. When the reaction is a nucleophilic substitution reaction, X represents a suitable leaving group, e.g. p-toluenesulfonate, methanesulfonate, iodide, bromide, or chloride; when the reaction is a Mitsunobu reaction, X is OH. A compound of formula XXXVI may then be further transformed by reaction with compound I under palladium-catalyzed cross-coupling conditions, e.g. with a suitable palladium catalyst such as bis(di-tert-butyl (4-dimethylaminophenyl)phosphine)dichloropalladium(II), suitable base such as cesium fluoride, suitable solvent such as mixtures of 1,4-dioxane and water, at a suitable temperature such as 100° C., with or without microwave irradiation to produce a compound of formula XXXVII.

Scheme 13.

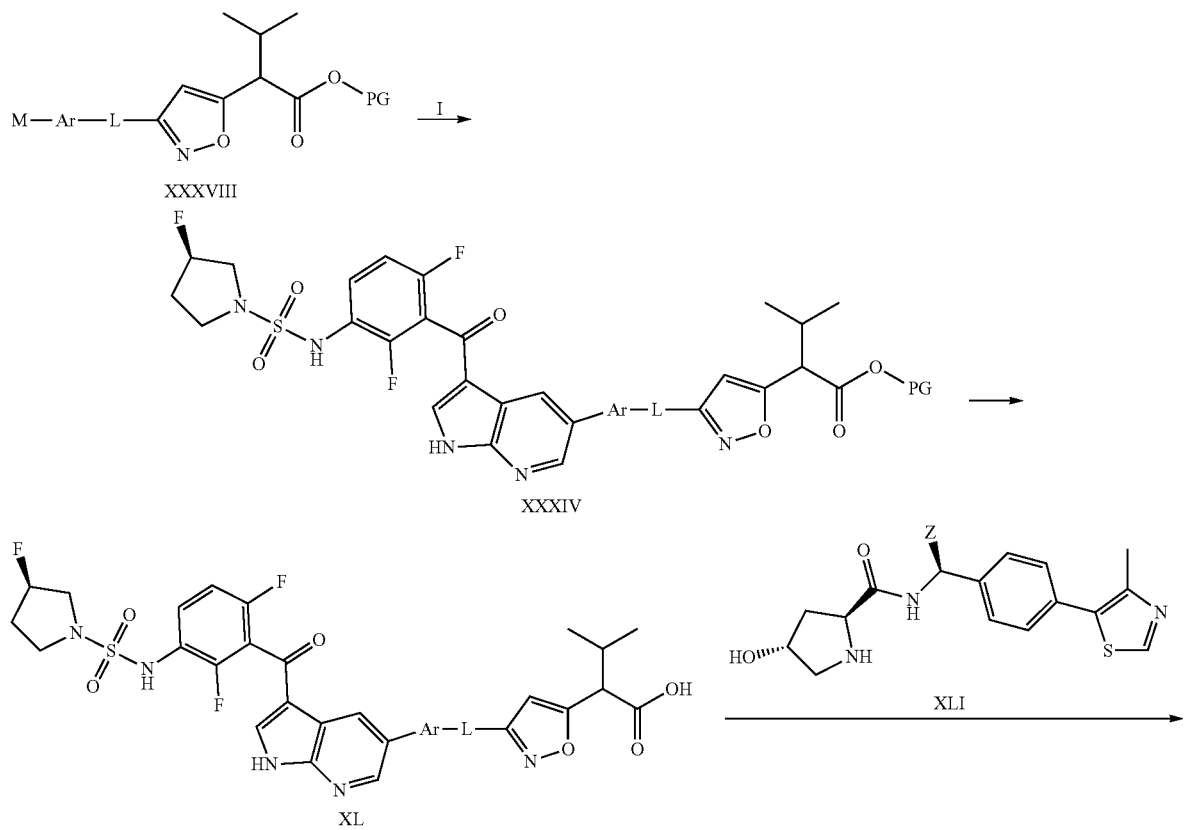

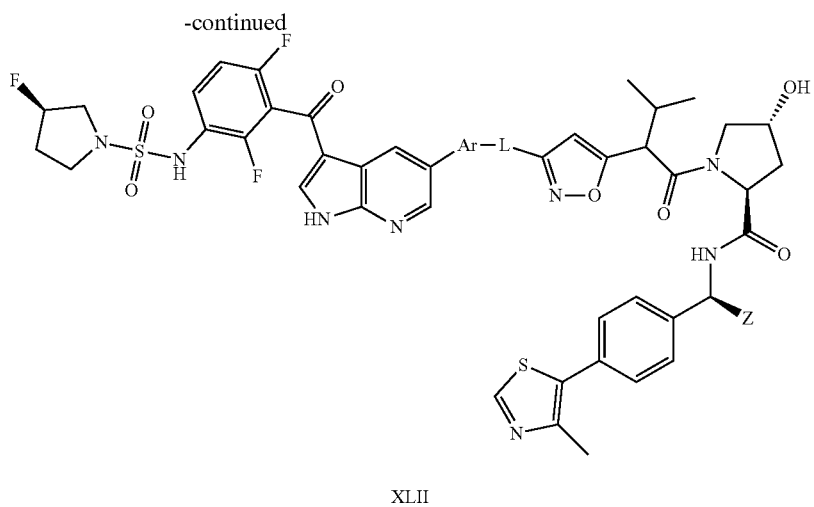

XLII

A compound of formula I may be reacted with a reagent XXXVIII (readily prepared using standard reaction techniques known to one skilled in the art) under palladium-catalyzed cross-coupling conditions, e.g. [1,1'-bis(diphenylphosphino)ferrocene]dichloropalladium(II), sodium carbonate, in a suitable solvent such as 1,4-dioxane/water mixture, at a suitable temperature such as 100° C., with or without microwave heating, to produce a compound of formula XXXIX. One of M or M' represents a functional group capable of undergoing palladium-catalyzed transmetallation, e.g. a boronic acid, boronic ester, or trialkylstannane; the other of M or M' represents a functional group capable of undergoing palladium-catalyzed oxidative addition, e.g. an iodide, bromide, chloride, or trifluoromethanesulfonate; Ar represents an aromatic or heteroaromatic ring system; L represents an optional linker or portion of a linker, and PG represents a suitable ester protecting group, e.g. methyl, ethyl, or t-butyl. Compounds of formula XXXIX may be converted to a compound of formula XL by treatment with a reagent suitable for the removal of PG, e.g. sodium hydroxide in methanol and water at 40° C. when PG is methyl or ethyl. Compound XL may then be reacted with compound XLI, wherein Z is an optional substituent, e.g. H, methyl, or hydroxymethyl, to produce compounds of formula XLII under amide formation conditions, e.g. N-[(dimethylamino)-1H-1,2,3-triazolo-[4,5-b]pyridin-1-ylmethylene]-N-methylmethanaminium hexafluorophosphate N-oxide, diisopropylethylamine, DMF, room temperature.

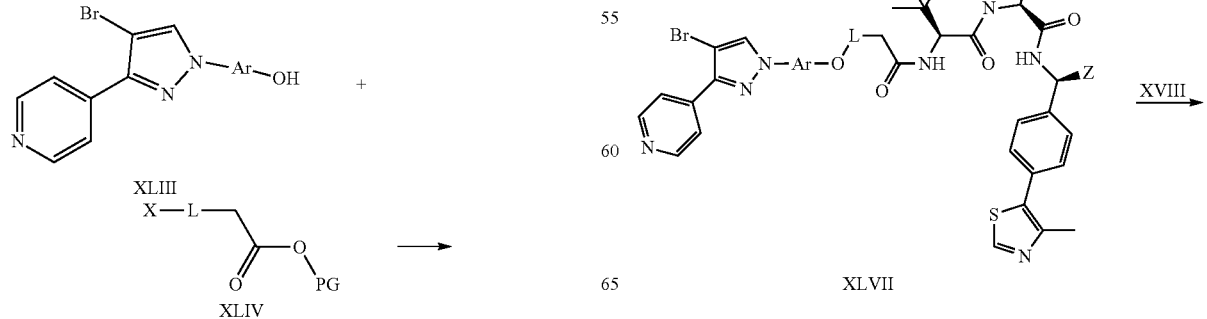

Scheme 14.

-continued

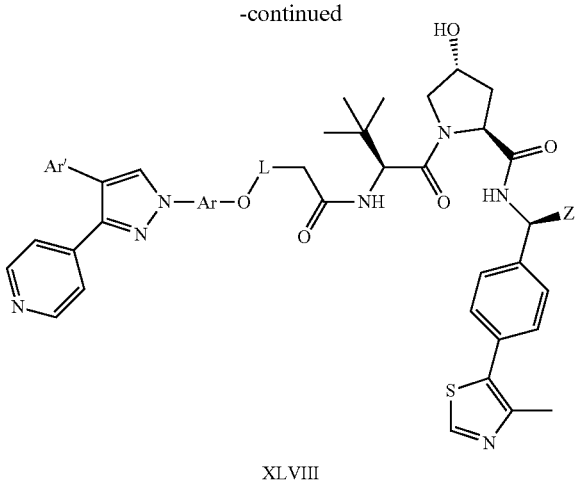

XLVIII

A compound of formula XLIII may be reacted with a reagent XLIV (commercially available or readily prepared using standard reaction techniques known to one skilled in the art) under nucleophilic substitution conditions, e.g. cesium carbonate, DMF, 75° C., to produce a compound of formula XLV. Ar represents an aromatic or heteroaromatic ring system; X represents a suitable leaving group, e.g. p-toluenesulfonate, methanesulfonate, iodide, bromide, or chloride; L represents an optional linker; and PG represents a suitable ester protecting group, e.g. methyl, ethyl, or t-butyl. Compounds of formula XLV may be converted to a compound of formula XLVI by treatment with a reagent suitable for the removal of PG, e.g. 3 N hydrochloric acid in 1,4-dioxane at room temperature when PG is t-butyl. Compound XLVI may then be reacted with compounds XII as defined in Scheme 3 to produce compounds of formula XLVII under amide formation conditions, e.g. (benzotriazol-1-yloxy)tripyrrolidinophosphonium hexafluorophosphate, diisopropylethylamine, DMF, room temperature. The compound of formula XLVII may then be treated with a reagent XVIII as defined in Scheme 5 to produce a compound of formula XLVIII. In cases where the group Ar' contains optional substituents, e.g. a ketone, these may undergo further functionalization, e.g. by treatment with hydroxylamine hydrochloride and pyridine at room temperature, to provide further compounds of formula XLVIII.

Intermediate 1: (3R)—N-[3-([5-bromo-1H-pyrrolo[2,3-b]pyridin-3-yl]carbonyl)-2,4-difluorophenyl]-3-fluoropyrrolidine-1-sulfonamide

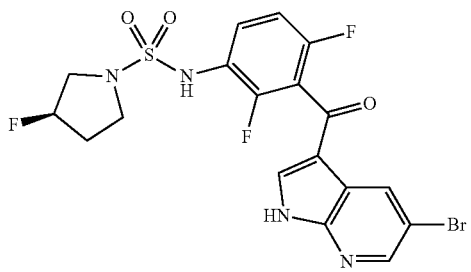 [SMILES: O=C(c1c(F)ccc(NS(=O)(=O)N2CC[C@@H](F)C2)c1F)c1c[nH]c2ncc(Br)cc12]

Step A: 2,6-difluoro-3-nitrobenzoyl Chloride

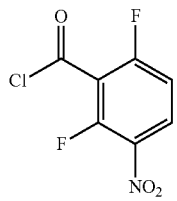 [SMILES: O=C(Cl)c1c(F)ccc([N+](=O)[O-])c1F]

Into a 150-mL round-bottom flask, was placed 2,6-difluoro-3-nitrobenzoic acid (15.0 g, 73.8 mmol, 1.0 equiv), toluene (80 mL), thionyl chloride (80 mL). The resulting mixture was stirred at 80° C. overnight and concentrated under reduced pressure. This resulted in 14.1 g (86%) of 2,6-difluoro-3-nitrobenzoyl chloride as a brown oil.

Step B: 5-bromo-3-[(2,6-difluoro-3-nitrophenyl)carbonyl]-1H-pyrrolo[2,3-b]pyridine

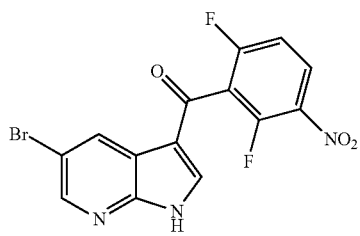 [SMILES: O=C(c1c(F)ccc([N+](=O)[O-])c1F)c1c[nH]c2ncc(Br)cc12]

5-bromo-1H-pyrrolo[2,3-b]pyridine (11.0 g, 55.8 mmol, 1.1 equiv) was mixed with 200 mL of chloromethane and aluminum trichloride (42.0 g, 318.2 mmol, 6.4 equiv) was added portionwise. The reaction was stirred at room temperature for 1 hour and 2,6-difluoro-3-nitrobenzoyl chloride (11.0 g, 49.6 mmol, 1.0 equiv) was added. The reaction was heated at 50° C. overnight, then reaction mixture was cooled to room temperature and poured to ice-water (500 mL), extracted with ethyl acetate (500 mL×3). The combined organic layer was washed with brine (500 mL×2), dried over anhydrous sodium sulfate. The solvent was concentrated to give (5-bromo-1H-pyrrolo[2,3-b]pyridin-3-yl)(2,6-difluoro-3-nitrophenyl) methanone (12.2 g) as a yellow solid, which was directly used to the next step without further purification. LCMS (ES$^+$): m/z 381.30 [M+H]$^+$.

Step C: 3-([5-bromo-1H-pyrrolo[2,3-b]pyridin-3-yl]carbonyl)-2,4-difluoroaniline

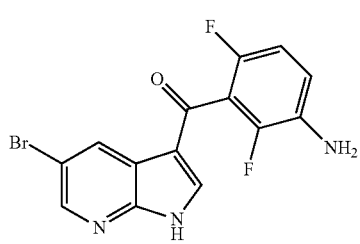

A mixture of (5-bromo-1H-pyrrolo[2,3-b]pyridin-3-yl)(2,6-difluoro-3-nitrophenyl)methanone (7.8 g, 20.4 mmol, 1.0 equiv), iron (5.6 g, 100.2 mmol, 4.9 equiv), ammonium chloride (3.6 g, 68 mmol), hydrochloric acid (25.0 mL) in ethanol (40 mL) and tetrahydrofuran (40 mL) was refluxed overnight. After cooling to room temperature, the mixture was filtered via a pad of Celite. The filtrate was concentrated in vacuo and the residue was purified by column chromatography on silica gel (petroleum ether/ethyl acetate=1/2) to give (3-amino-2,6-difluorophenyl)(5-bromo-1H-pyrrolo[2,3-b]pyridin-3-yl)methanone (4.3 g, 60% yield) as a yellow solid. LCMS (ES+): m/z 351.80 [M+H]+.

Step D: (R)-3-fluoropyrrolidine-1-sulfonyl Chloride

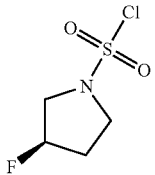

An oven dried flask was charged with (R)-3-fluoropyrrolidine hydrochloride (3.0 g, 24 mmol). tRiethylamine (7.2 g, 72 mmol) and dichloromethane (150 mL). The mixture was stirred for 15 minutes at room temperature and then cooled to about −30° C. in a dryice/acetonitrile bath for 10 minutes. Sulfuryl chloride (6.0 g, 48 mmol) was added dropwise over 10 minutes. The reaction mixture was stirred at about −30° C. for an hour, then stirred at room temperature for 5 hours. The reaction mixture was diluted with aqueous HCl (1 N, 70 mL). The layers were separated and the aqueous layers were extracted with dichloromethane (50 mL×3). The combined organic layer was washed with aqueous HCl (1 N, 50 mL) and brine (50 mL), dried over anhydrous sodium sulfate. The solvent was concentrated to give (R)-3-fluoropyrrolidine-1-sulfonyl chloride (4.5 g) as a white solid, which was directly used to the next step without further purification.

Step E: (3R)—N-[3-([5-bromo-1H-pyrrolo[2,3-b]pyridin-3-yl]carbonyl)-2,4-difluorophenyl]-3-fluoropyrrolidine-1-sulfonamide

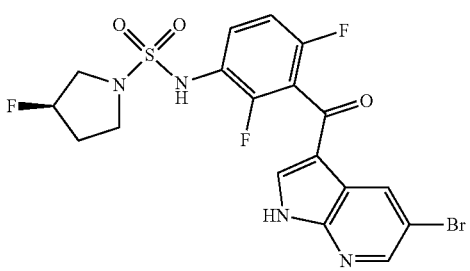 [SMILES: O=C(c1c(F)ccc(NS(=O)(=O)N2CC[C@@H](F)C2)c1F)c1c[nH]c2ncc(Br)cc12]

To a solution of (3-amino-2,6-difluorophenyl)(5-bromo-1H-pyrrolo[2,3-b]pyridin-3-yl)methanone (8.0 g, 22.79 mmol, 1.0 eq) in pyridine (25.0 g) was added (R)-3-fluoropyrrolidine-1-sulfonyl chloride (4.6 g, 24.60 mmol, 1.08 eq) and 4-dimethylaminopyridine (560.0 mg, 4.59 mmol, 0.2 eq). The reaction mixture was stirred for 12 hours at 40° C. The solvent was removed and water (20 mL) was added, adjusted pH=7-8 with aqueous sodium bicarbonate, extracted with ethyl acetate (100 mL×2). The combined organic layer was washed with brine (50 mL×2), dried over anhydrous sodium sulfate. The solvent was removed in vacuo and the residue was purified by column chromatography on silica gel with ethyl acetate/petroleum ether (3:1) to give (R)—N-(3-(5-bromo-1H-pyrrolo[2,3-b]pyridine-3-carbonyl)-2,4-difluorophenyl)-3-fluoropyrrolidine-1-sulfonamide (6.4 g) as a yellow solid LCMS (ES+): m/z 505.05 [M+H]+.

Intermediate 2: (R)—N-(2,4-difluoro-3-(5-(4,4,5,5-tetramethyl-1,3,2-dioxaborolan-2-yl)-1H-pyrrolo[2,3-b]pyridine-3-carbonyl)phenyl)-3-fluoropyrrolidine-1-sulfonamide

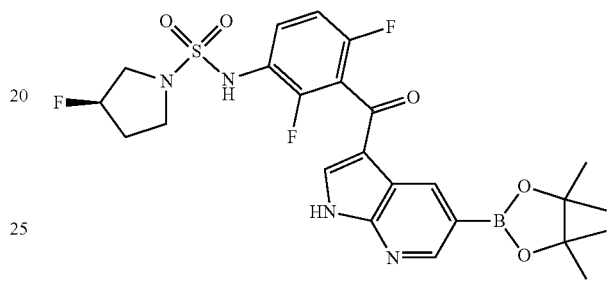

Step A: (R)—N-(2,4-difluoro-3-(5-(4,4,5,5-tetramethyl-1,3,2-dioxaborolan-2-yl)-1H-pyrrolo[2,3-b]pyridine-3-carbonyl)phenyl)-3-fluoropyrrolidine-1-sulfonamide To a solution of (R)—N-(3-(5-bromo-1H-pyrrolo[2,3-b]pyridine-3-carbonyl)-2,4-difluorophenyl)-3-fluoropyrrolidine-1-sulfonamide (1.0 g, 2.0 mmol) in 1,4-dioxane were added KOAc (392.0 mg, 4.0 mmol), Pd(dppf)Cl$_2$ (163.0 mg, 0.2 mmol), and 4,4,4',4',5,5,5',5'-octamethyl-2,2'-bi(1,3,2-dioxaborolane) (1.02 g, 4.0 mmol) subsequently. The resulting solution was heated to 90° C. overnight under N$_2$. After cooling to room temperature, the solvent was removed under reduced pressure. The residue was purified by column chromatography on silica gel eluting with ethyl acetate/petroleum ether (1:1). This resulted in 551.0 mg (50%) (R)—N-(2,4-difluoro-3-(5-(4,4,5,5-tetramethyl-1,3,2-dioxaborolan-2-yl)-1H-pyrrolo[2,3-b]pyridine-3-carbonyl)phenyl)-3-fluoropyrrolidine-1-sulfonamide as a light brown solid. LCMS (ES+): m/z 551.15 [M+H]+.

Intermediate 3: N-(3-[5-bromo-1H-pyrrolo[2,3-b]pyridine-3-carbonyl]-2,4-difluorophenyl)-2-(dimethylamino)ethane-1-sulfonamide

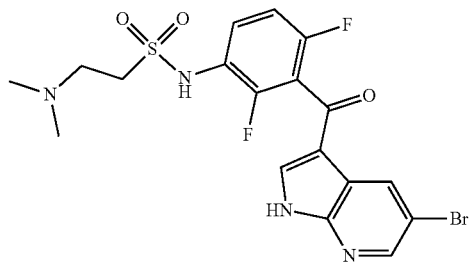 [SMILES: CN(C)CCS(=O)(=O)Nc1ccc(F)c(C(=O)c2c[nH]c3ncc(Br)cc23)c1F]

Step A: N-(3-[5-bromo-1H-pyrrolo[2,3-b]pyridine-3-carbonyl]-2,4-difluorophenyl)ethene-1-sulfonamide

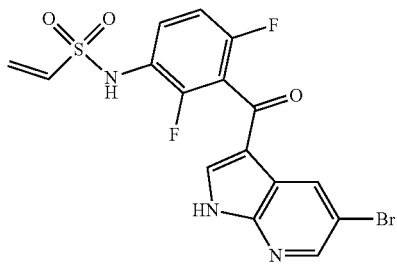 [SMILES: C=CS(=O)(=O)Nc1ccc(F)c(C(=O)c2c[nH]c3ncc(Br)cc23)c1F]

Into a 100 mL round-bottom flask, was placed 3-[5-bromo-1H-pyrrolo[2,3-b]pyridine-3-carbonyl]-2,4-difluoroaniline (500 mg, 1.42 mmol, 1 equiv), pyridine (20 mL, 248.47 mmol, 174.99 equiv), DMAP (35 mg, 0.29 mmol, 0.20 equiv), ethenesulfonyl chloride (360 mg, 2.84 mmol, 2.00 equiv), dichloromethane (20 mL). The resulting solution was stirred for 0.5 hour at room temperature. The reaction mixture was concentrated under reduced pressure. The residue was applied onto a silica gel column eluting with ethyl acetate/petroleum ether (1:1). This resulted in 300 mg (48%) of N-(3-[5-bromo-1H-pyrrolo[2,3-b]pyridine-3-carbonyl]-2,4-difluorophenyl)ethene-1-sulfonamide as a white solid. LCMS (ES$^+$): m/z 443.80[M+H]$^+$.

Step B: N-(3-[5-bromo-1H-pyrrolo[2,3-b]pyridine-3-carbonyl]-2,4-difluorophenyl)-2-(dimethylamino)ethane-1-sulfonamide

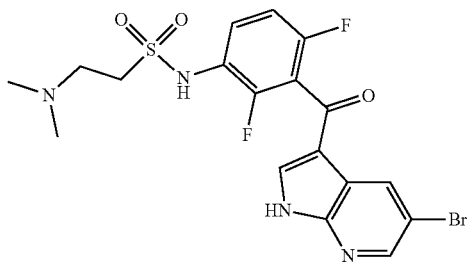 [SMILES: CN(C)CCS(=O)(=O)Nc1ccc(F)c(C(=O)c2c[nH]c3ncc(Br)cc23)c1F]

Into a 100 mL round-bottom flask, was placed N-(3-[5-bromo-1H-pyrrolo[2,3-b]pyridine-3-carbonyl]-2,4-difluorophenyl)ethene-1-sulfonamide (300 mg, 0.68 mmol, 1 equiv), dichloromethane (20 mL), dimethylamine (2.0 mL). The resulting solution was stirred for 2 hours at room temperature. The reaction mixture was concentrated under reduced pressure. This resulted in 360 mg (crude) of N-(3-[5-bromo-1H-pyrrolo[2,3-b]pyridine-3-carbonyl]-2,4-difluorophenyl)-2-(dimethylamino)ethane-1-sulfonamide as a white solid. LCMS (ES$^+$): m/z 488.85 [M+H]$^+$.

Intermediate 4: N-(3-[5-bromo-1H-pyrrolo[2,3-b]pyridine-3-carbonyl]-2,4-difluorophenyl)-2,3-dihydroxypropane-1-sulfonamide

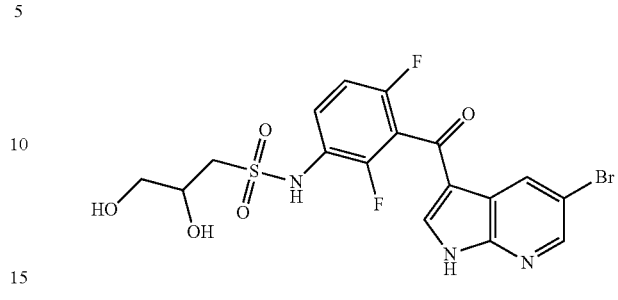

Step A: N-(3-[5-bromo-1H-pyrrolo[2,3-b]pyridine-3-carbonyl]-2,4-difluorophenyl)prop-2-ene-1-sulfonamide

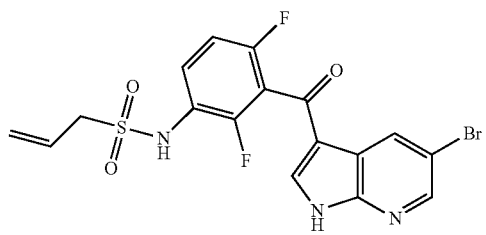 [SMILES: C=CCS(=O)(=O)Nc1ccc(F)c(C(=O)c2c[nH]c3ncc(Br)cc23)c1F]

Into a 25 mL round-bottom flask, was placed 3-[5-bromo-1H-pyrrolo[2,3-b]pyridine-3-carbonyl]-2,4-difluoroaniline (500 mg, 1.42 mmol, 1 equiv), pyridine (2 mL, 15 equiv), prop-2-ene-1-sulfonyl chloride (399.2 mg, 2.84 mmol, 2 equiv), DMAP (52.0 mg, 0.43 mmol, 0.3 equiv). The resulting solution was stirred overnight at 45° C. in an oil bath. The resulting mixture was concentrated. The residue was applied onto a silica gel column eluting with ethyl acetate/petroleum ether (1/1). This resulted in 480 mg (74%) of N-(3-[5-bromo-1H-pyrrolo[2,3-b]pyridine-3-carbonyl]-2,4-difluorophenyl)prop-2-ene-1-sulfonamide as a yellow solid.

Step B: N-(3-[5-bromo-1H-pyrrolo[2,3-b]pyridine-3-carbonyl]-2,4-difluorophenyl)-2,3-dihydroxypropane-1-sulfonamide

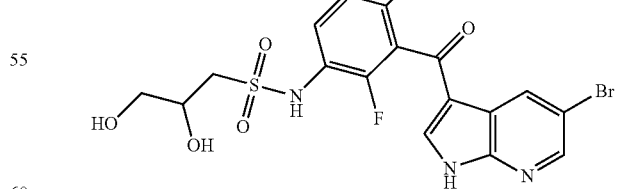

Into a 50 mL round-bottom flask, was placed N-(3-[5-bromo-1H-pyrrolo[2,3-b]pyridine-3-carbonyl]-2,4-difluorophenyl)prop-2-ene-1-sulfonamide (430 mg, 0.94 mmol, 1 equiv), acetone (20 mL), N-methylmorpholine N-oxide (226 mg), water (5 mL), tetraoxoosmium (4 mL). The resulting solution was stirred overnight at room temperature. The reaction was then quenched by the addition of water (20 mL). The resulting solution was extracted with ethyl acetate (30 mL×3). The resulting mixture was washed with brine (20 mL×1), dried over anhydrous sodium sulfate and concentrated under reduced pressure. The residue was applied onto a silica gel column eluting with ethyl acetate/petroleum ether (1/1). This resulted in 377 mg (82%) of N-(3-[5-bromo-1H-pyrrolo[2,3-b]pyridine-3-carbonyl]-2,4-difluorophenyl)-2,3-dihydroxypropane-1-sulfonamide as a white solid.

Intermediate 5: (R)—N-(3-(5-bromo-1H-pyrrolo[2,3-b]pyridine-3-carbonyl)-2,4-difluorophenyl)-3-fluoropyrrolidine-1-carboxamide

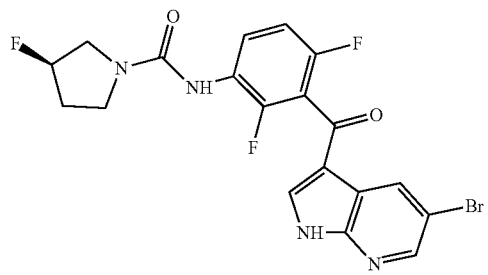 [SMILES: O=C(c1c(F)ccc(NC(=O)N2CC[C@@H](F)C2)c1F)c1c[nH]c2ncc(Br)cc12]

To the solution of (3-amino-2,6-difluorophenyl)(5-bromo-1H-pyrrolo[2,3-b]pyridin-3-yl)methanone(2.0 g, 5.70 mmol, 1.00 equiv), triethylamine (8.6 g, 85.5 mmol, 15.00 equiv) in dichloromethane (80 mL) was slowly added a solution of bis(trichloromethyl) carbonate (2.5 g, 8.55 mmol, 1.50 equiv) in dichloromethane (40 mL), followed by dropwise addition of a solution of (R)-3-fluoropyrrolidine (761.0 mg, 8.55 mmol, 1.50 equiv) in dichloromethane (40 mL) at 0° C. The resulting solution was stirred for 30 minutes at 0° C. in a water/ice bath. The resulting solution was quenched by the aqueous solution of ammonium chloride (40 mL), extracted with dichloromethane (40 mL×2). Then the organic layers were combined and concentrated. The residue was applied onto a silica gel column with chloroform/methanol (10:1). This resulted in 541.0 mg (20%) of (R)—N-(3-(5-bromo-1H-pyrrolo[2,3-b]pyridine-3-carbonyl)-2,4-difluorophenyl)-3-fluoropyrrolidine-1-carboxamide as a tawny solid. LCMS (ES+): m/z 467.10 [M+H]+.

Example Synthesis of Compound 86

Step A: (R)-tert-butyl 4-(4-(3-(2,6-difluoro-3-(3-fluoropyrrolidine-1-sulfonamido)benzoyl)-1H-pyrrolo[2,3-b]pyridin-5-yl)phenyl)piperazine-1-carboxylate

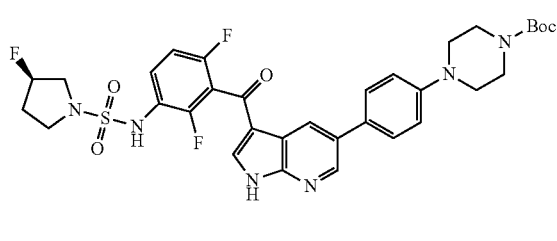

A solution of (R)—N-(3-(5-bromo-1H-pyrrolo[2,3-b]pyridine-3-carbonyl)-2,4-difluorophenyl)-3-fluoropyrrolidine-1-sulfonamide (0.50 g, 1.0 mmol) in 1,4-dioxane/H₂O (20 mL/2 mL), was added tert-butyl 4-(4-(4,4,5,5-tetramethyl-1,3,2-dioxaborolan-2-yl)phenyl)piperazine-1-carboxylate (0.43 g, 1.2 mmol), cesium fluoride (0.23 g, 1.5 mmol) and Pd(aMPhos)Cl₂ (0.11 g, 0.15 mmol) under an argon atmosphere. The mixture was stirred at 100° C. for 3 hours. After being cooled to room temperature, water was added. The aqueous phase was extracted with ethyl acetate (20 mL×3), and the combined organic phases were dried over anhydrous sodium sulfate, filtered, and concentrated in vacuo. The crude product was purified by silica gel (dichloromethane/methanol=12:1) to give compound (R)-tert-butyl 4-(4-(3-(2,6-difluoro-3-(3-fluoropyrrolidine-1-sulfonamido)benzoyl)-1H-pyrrolo[2,3-b]pyridin-5-yl)phenyl)piperazine-1-carboxylate (0.39 g, 57%) as a yellow solid. LCMS: m/z 685.2 [M+H]+; ¹H NMR (400 MHz, DMSO-d₆) δ 1.43 (9H, s), 2.06-2.12 (1H, m), 3.18-3.20 (4H, m), 3.26-3.30 (1H, m), 3.37-3.53 (8H, m), 5.30 (1H, d, J=52.0 Hz), 7.10 (2H, d, J=8.8 Hz), 7.28 (1H, t, J=8.4 Hz), 7.60-7.64 (3H, m), 8.09 (1H, d, J=2.8 Hz), 8.55 (1H, brs.), 8.66 (1H, d, J=2.4 Hz), 9.87 (1H, s), 12.93 (1H, s).

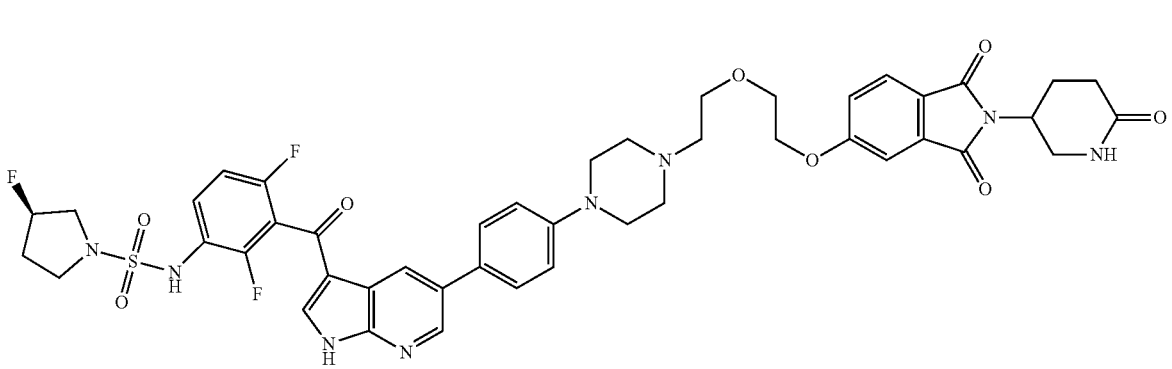 [SMILES: O=C1CCC(N2C(=O)c3ccc(OCCOCCN4CCN(c5ccc(-c6cnc7[nH]cc(C(=O)c8c(F)ccc(NS(=O)(=O)N9CC[C@@H](F)C9)c8F)c7c6)cc5)CC4)cc3C2=O)CN1]

Step B: (R)—N-(2,4-difluoro-3-(5-(4-(piperazin-1-yl)phenyl)-1H-pyrrolo[2,3-b]pyridine-3-carbonyl)phenyl)-3-fluoropyrrolidine-1-sulfonamide

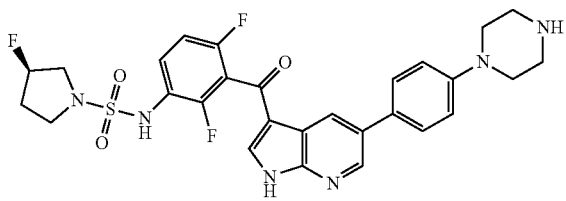 [SMILES: O=C(c1c(F)ccc(NS(=O)(=O)N2CC[C@@H](F)C2)c1F)c1c[nH]c2ncc(-c3ccc(N4CCNCC4)cc3)cc12]

To a solution of (R)-tert-butyl 4-(4-(3-(2,6-difluoro-3-(3-fluoropyrrolidine-1-sulfonamido)benzoyl)-1H-pyrrolo[2,3-b]pyridin-5-yl)phenyl)piperazine-1-carboxylate (0.39 g, 0.57 mmol) in hydrochloric acid/1,4-dioxane (5 mL, 4.0 N) was stirred at room temperature for 3 hours. Then the solvent was directly removed, then water (10 mL) was added and the pH of the mixture was adjusted to 8-9 by saturated sodium bicarbonate. The aqueous phase was extracted with ethyl acetate (10 mL×3), and the combined organic phases were dried over anhydrous sodium sulfate, filtered, and concentrated in vacuo to give (R)—N-(2,4-difluoro-3-(5-(4-(piperazin-1-yl)phenyl)-1H-pyrrolo[2,3-b]pyridine-3-carbonyl)phenyl)-3-fluoropyrrolidine-1-sulfonamide (0.30 g, 91%) as a yellow solid.

Step C: 2-(2-chloroethoxy)ethyl 4-methylbenzenesulfonate

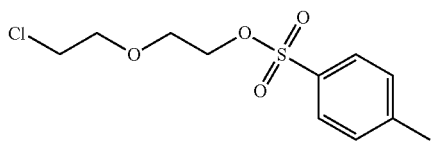 [SMILES: Cc1ccc(S(=O)(=O)OCCOCCCl)cc1]

The mixture of 2-(2-chloroethoxy)ethanol (0.5 g, 4.0 mmol), tosyl chloride (0.8 g, 4.0 mmol) and triethylamine (810 mg, 8.1 mmol) in dichloromethane (10 mL) was stirred at room temperature overnight. The mixture was poured into saturated sodium bicarbonate solution (20 mL) and extracted with dichloromethane (20 mL×3). The combined organic phase was concentrated in vacuo and the residue was purified by column chromatography on silica gel (petroleum ether/ethyl acetate=10/1) to give 2-(2-chloroethoxy)ethyl 4-methylbenzenesulfonate (0.9 g, 80% yield) as colorless oil. LCMS: m/z 279.1 [M+H]$^+$.

Step D: 5-(2-(2-chloroethoxy)ethoxy)-2-(2,6-dioxopiperidin-3-yl)isoindoline-1,3-dione

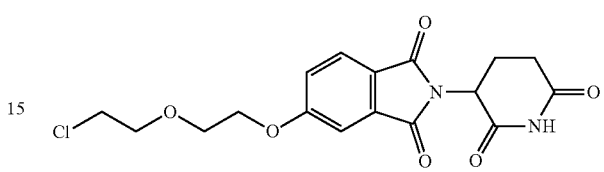

The mixture of 2-(2-chloroethoxy)ethyl 4-methylbenzenesulfonate (100 mg, 0.36 mmol), 2-(2,6-dioxopiperidin-3-yl)-5-hydroxyisoindoline-1,3-dione (98 mg, 0.36 mmol), ethyldiisopropylamine (93 mg, 0.72 mmol) and potassium iodide (59 mg, 0.36 mmol) in dimethyl sulfoxide (5 mL) was heated at 45° C. for 2 hours and then cooled to room temperature. The reaction mixture was poured into water (10 mL) and extracted with dichloromethane (15 mL×3). The combined organic phase was concentrated in vacuo and the residue was purified by column chromatography on silica gel (dichloromethane/methanol=20/1) to give 5-(2-(2-chloroethoxy)ethoxy)-2-(2,6-dioxopiperidin-3-yl)isoindoline-1,3-dione (48 mg, 35% yield) as a white solid. LCMS: m/z 381.2 [M+H]$^+$.

Step E: (3R)—N-(3-(5-(4-(4-(2-(2-(2-(2,6-dioxopiperidin-3-yl)-1,3-dioxoisoindolin-5-yloxy)ethoxy)ethyl)piperazin-1-yl)phenyl)-1H-pyrrolo[2,3-b]pyridine-3-carbonyl)-2,4-difluorophenyl)-3-fluoropyrrolidine-1-sulfonamide

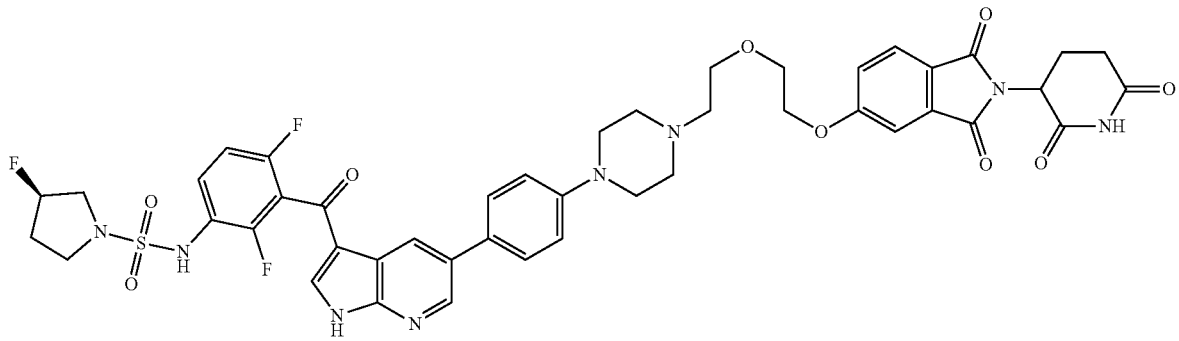 [SMILES: O=C1CCC(N2C(=O)c3ccc(OCCOCCN4CCN(c5ccc(-c6cnc7[nH]cc(C(=O)c8c(F)ccc(NS(=O)(=O)N9CC[C@@H](F)C9)c8F)c7c6)cc5)CC4)cc3C2=O)C(=O)N1]

The mixture of 5-(2-(2-chloroethoxy)ethoxy)-2-(2,6-dioxopiperidin-3-yl)isoindoline-1,3-dione (40 mg, 0.11 mmol), (R)—N-(2,4-difluoro-3-(5-(4-(piperazin-1-yl)phenyl)-1H-pyrrolo[2,3-b]pyridine-3-carbonyl)phenyl)-3-fluoropyrrolidine-1-sulfonamide (61 mg, 0.11 mmol), ethyldiisopropylamine (28 mg, 0.22 mmol) and potassium iodide (18 mg, 0.11 mmol) in dimethyl sulfoxide (5 mL) was heated at 80° C. overnight. The mixture was poured into water (10 mL) and extracted with dichloromethane (10 mL×3). The organic phase was concentrated in vacuo and the residue was purified by pre-HPLC to give (3R)—N-(3-(5-(4-(4-(2-(2-(2-(2,6-dioxopiperidin-3-yl)-1,3-dioxoisoindolin-5-yloxy)ethoxy)ethyl)piperazin-1-yl)phenyl)-1H-pyrrolo[2,3-b]pyridine-3-carbonyl)-2,4-difluorophenyl)-3-fluoropyrrolidine-1-sulfonamide (31 mg, 30% yield) as a yellow solid. LCMS: m/z 929.3 [M+H]⁺; ¹H NMR (400 MHz, DMSO-d₆) δ 1.95-2.10 (3H, m), 2.53-2.59 (8H, m), 3.18-3.23 (4H, m), 3.24-3.31 (2H, m), 3.36-3.39 (2H, m), 3.47 (1H, s), 3.64 (2H, t, J=6.0 Hz), 3.80 (2H, t, J=4.0 Hz), 4.35 (2H, t, J=4.0 Hz), 5.12 (1H, dd, J=5.6, 9.6 Hz), 5.29 (1H, d, J=12.8 Hz), 7.05 (2H, d, J=8.8 Hz), 7.26 (1H, d, J=8.8 Hz), 7.39 (1H, dd, J=2.0, 8.4 Hz), 7.48 (1H, d, J=2.4 Hz), 7.58-7.65 (3H, m), 7.85 (1H, d, J=8.4 Hz), 8.07 (1H, s), 8.53 (1H, d, J=2.4 Hz), 8.65 (1H, d, J=2.4 Hz), 9.85 (1H, brs), 11.1 (1H, s), 12.9 (1H, s).

J=4.8 Hz), 4.10-4.12 (2H, m), 4.62-4.64 (1H, m), 6.93 (2H, d, J=9.2 Hz), 7.60 (2H, d, J=8.4 Hz).

Step B: 2-(2-(4-(4,4,5,5-tetramethyl-1,3,2-dioxaborolan-2-yl)phenoxy)ethoxy)ethyl methanesulfonate

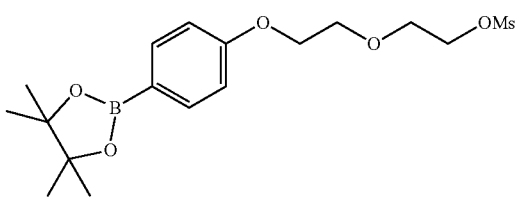

To a solution of 2-(2-(4-(4,4,5,5-tetramethyl-1,3,2-dioxaborolan-2-yl)phenoxy)ethoxy)ethanol (350 mg, 1.14 mmol) in dichloromethane (15.0 mL) was added triethylamine (231 mg, 2.28 mmol) and methanesulfonyl chloride (157 mg, Compounds 87-90 may be prepared in an analogous manner.

Example Synthesis of Compound 91

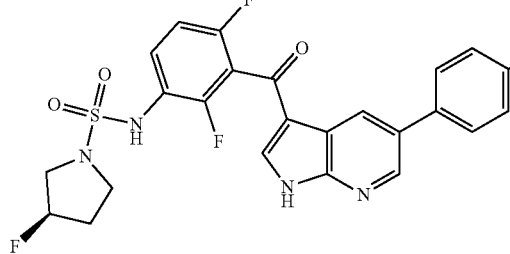

Step A: 2-(2-(4-(4,4,5,5-tetramethyl-1,3,2-dioxaborolan-2-yl)phenoxy)ethoxy)ethanol

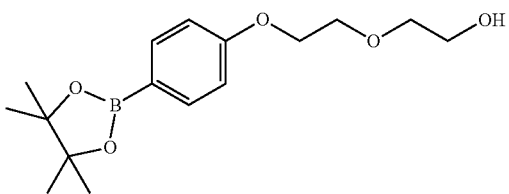 [SMILES: CC1(C)OB(c2ccc(OCCOCCO)cc2)OC1(C)C]

To a solution of 2-(2-chloroethoxy)ethanol (2.0 g, 16.1 mmol) in N,N-dimethylformamide (15.0 mL) was added 4-(4,4,5,5-tetramethyl-1,3,2-dioxaborolan-2-yl)phenol (3.54 g, 16.1 mmol), cesium carbonate (10.5 g, 32.2 mmol) and potassium iodide (267 mg, 1.61 mmol). The reaction mixture was stirred at 60° C. overnight. Then water (50 mL) was added and extracted with ethyl acetate (50 mL×3), washed with brine (5 mL×4). The combined organic phases were dried over anhydrous sodium sulfate, filtered, and concentrated in vacuo. The residue was purified by silica gel (petroleum ether/ethyl acetate=2:1) to give 2-(2-(4-(4,4,5,5-tetramethyl-1,3,2-dioxaborolan-2-yl)phenoxy)ethanol (2.1 g, 42%) as yellow oil. ¹H NMR (400 MHz, DMSO-d₆) δ 1.28 (12H, s), 3.49-3.52 (4H, m), 3.74 (2H, t, 1.37 mmol) under nitrogen. The resulting reaction mixture was stirred at room temperature for 1 hour. Then aq. sodium bicarbonate (20.0 mL) was added and extracted with dichloromethane (20 mL×3), washed by brine, dried and concentrated in vacuo to give crude 2-(2-(4-(4,4,5,5-tetramethyl-1,3,2-dioxaborolan-2-yl)phenoxy)ethoxy)ethyl methanesulfonate as yellow oil, which was used for the next step without further purification. LCMS: m/z 404.2 [M+18]⁺.

Step C: tert-butyl 4-(2-(2-(4-(4,4,5,5-tetramethyl-1,3,2-dioxaborolan-2-yl)phenoxy)ethoxy)ethyl)piperazine-1-carboxylate

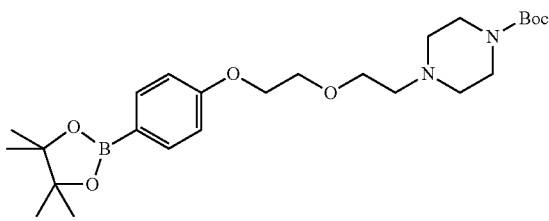 [SMILES: CC(C)(C)OC(=O)N1CCN(CCOCCOc2ccc(B3OC(C)(C)C(C)(C)O3)cc2)CC1]

To a solution of 2-(2-(4-(4,4,5,5-tetramethyl-1,3,2-dioxaborolan-2-yl)phenoxy)ethoxy)ethyl methanesulfonate (1.14 mmol) in acetonitrile (20 mL) was added potassium carbonate (315 mg, 2.28 mmol) and tert-butyl piperazine-1-carboxylate (234 mg, 1.25 mmol). The resulting reaction mixture was stirred at 80° C. overnight. The solvent was concentrated in vacuo. The residue was extracted with ethyl acetate (20 mL×3) and water (20 mL). The organic phase was dried and concentrated in vacuo. The residue was purified by preparative TLC (petroleum ether/ethyl acetate=1:2) to give tert-butyl 4-(2-(2-(4-(4,4,5,5-tetramethyl-1,3,2-dioxaborolan-2-yl)phenoxy)ethoxy)ethyl)piperazine-1-carboxylate (280 mg, 52% for two steps) as a pale yellow solid. $^{1}$H NMR (400 MHz, DMSO-d$_6$) δ 1.27 (12H, s), 1.38 (9H, s), 2.35 (4H, t, J=5.2 Hz), 2.47-2.50 (2H, m), 3.25-3.26 (4H, m), 3.57 (2H, t, J=6.0 Hz), 3.70-3.73 (2H, m), 4.10-4.12 (2H, m), 6.92 (2H, d, J=8.8 Hz), 7.59 (2H, d, J=8.4 Hz).

Step D: (R)-tert-butyl 4-(2-(2-(4-(3-(2,6-difluoro-3-(3-fluoropyrrolidine-1-sulfonamido)benzoyl)-1H-pyrrolo[2,3-b]pyridin-5-yl)phenoxy)ethoxy)ethyl)piperazine-1-carboxylate

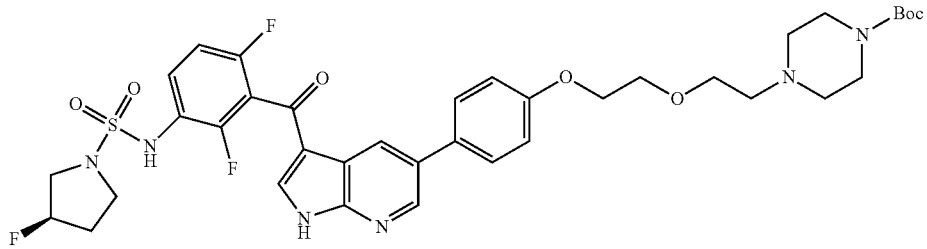 [SMILES: CC(C)(C)OC(=O)N1CCN(CCOCCOc2ccc(-c3cnc4[nH]cc(C(=O)c5c(F)ccc(NS(=O)(=O)N6CC[C@@H](F)C6)c5F)c4c3)cc2)CC1]

To a solution of tert-butyl 4-(2-(2-(4-(4,4,5,5-tetramethyl-1,3,2-dioxaborolan-2-yl)phenoxy)ethoxy)ethyl)piperazine-1-carboxylate (114 mg, 0.238 mmol) in 1,4-dioxane/water (10 mL/1 mL) was added (R)—N-(3-(5-bromo-1H-pyrrolo[2,3-b]pyridine-3-carbonyl)-2,4-difluorophenyl)-3-fluoropyrrolidine-1-sulfonamide (120 mg, 0.238 mmol), cesium fluoride (72.4 mg, 0.476 mmol) and Pd(aMPhos)Cl$_2$ (16.9 mg, 0.0238 mmol). The resulting reaction mixture was stirred at 95° C. for 16 hours. After cooling, water (20 mL) was added and extracted with ethyl acetate (15 mL×3). The organic phase was dried and concentrated in vacuo. The residue was purified by preparative TLC (dichloromethane/methanol=20:1) to give (R)-tert-butyl 4-(2-(2-(4-(3-(2,6-difluoro-3-(3-fluoropyrrolidine-1-sulfonamido)benzoyl)-1H-pyrrolo[2,3-b]pyridin-5-yl)phenoxy)ethoxy)ethyl)piperazine-1-carboxylate (60 mg, 33%) as a pale yellow solid. LCMS: m/z 773.3 [M+H]$^+$.

Step E: (R)—N-(2,4-difluoro-3-(5-(4-(2-(2-(piperazin-1-yl)ethoxy)ethoxy)phenyl)-1H-pyrrolo[2,3-b]pyridine-3-carbonyl)phenyl)-3-fluoropyrrolidine-1-sulfonamide hydrochloride

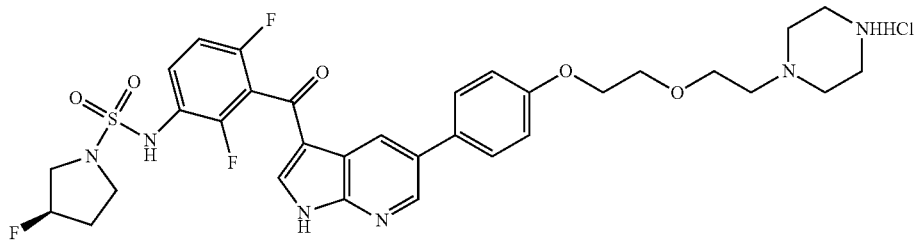

A solution of (R)-tert-butyl 4-(2-(2-(4-(3-(2,6-difluoro-3-(3-fluoropyrrolidine-1-sulfonamido)benzoyl)-1H-pyrrolo[2,3-b]pyridin-5-yl)phenoxy)ethoxy)ethyl)piperazine-1-carboxylate (60 mg, 0.0517 mmol) in hydrochloric acid/1,4-dioxane (5 mL, 4 M) was stirred at room temperature for 1 hour. The solvent was concentrated in vacuo to give compound (R)—N-(2,4-difluoro-3-(5-(4-(2-(2-(piperazin-1-yl)ethoxy)ethoxy)phenyl)-1H-pyrrolo[2,3-b]pyridine-3-carbonyl)phenyl)-3-fluoropyrrolidine-1-sulfonamide hydrochloride as a pale yellow solid, which was used to next step without further purification. LCMS: m/z 673.2 [M+H]$^+$.

Step F: (3R)—N-(3-(5-(4-(2-(2-(4-(2-(2,6-dioxopiperidin-3-yl)-1,3-dioxoisoindolin-5-yl)piperazin-1-yl)ethoxy)ethoxy)phenyl)-1H-pyrrolo[2,3-b]pyridine-3-carbonyl)-2,4-difluorophenyl)-3-fluoropyrrolidine-1-sulfonamide

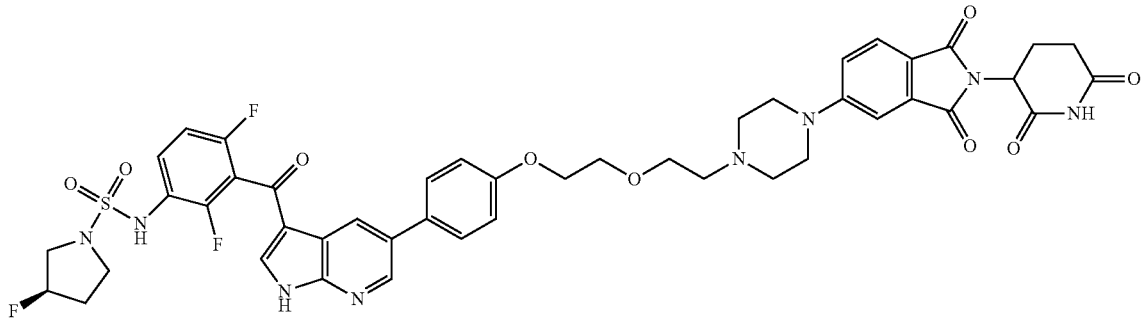 [SMILES: O=C1CCC(N2C(=O)c3ccc(N4CCN(CCOCCOc5ccc(-c6cnc7[nH]cc(C(=O)c8c(F)ccc(NS(=O)(=O)N9CC[C@@H](F)C9)c8F)c7c6)cc5)CC4)cc3C2=O)C(=O)N1]

To a solution of (R)—N-(2,4-difluoro-3-(5-(4-(2-(2-(piperazin-1-yl)ethoxy)ethoxy)phenyl)-1H-pyrrolo[2,3-b]pyridine-3-carbonyl)phenyl)-3-fluoropyrrolidine-1-sulfonamide hydrochloride (0.0517 mmol) in dimethyl sulfoxide (3 mL) was added 2-(2,6-dioxopiperidin-3-yl)-5-fluoroisoindoline-1,3-dione (14.3 mg, 0.0517 mmol) and triethylamine (10.5 mg, 0.104 mmol). The reaction mixture was stirred at 70° C. for 24 hours. After cooling to room temperature, water (10 mL) was added and extracted with ethyl acetate (10.0 mL×3). The combined organic phase was washed with brine (2.0 mL×4), dried over anhydrous sodium sulfate, filtered, and concentrated in vacuo. The residue was purified by preparative TLC (dichloromethane/methanol=20:1) twice to give (3R)—N-(3-(5-(4-(2-(2-(4-(2-(2,6-dioxopiperidin-3-yl)-1,3-dioxoisoindolin-5-yl)piperazin-1-yl)ethoxy)ethoxy)phenyl)-1H-pyrrolo[2,3-b]pyridine-3-carbonyl)-2,4-difluorophenyl)-3-fluoropyrrolidine-1-sulfonamide (6.7 mg, 14%) as a yellow solid. LCMS: m/z 929.3 [M+H]$^+$. $^1$H NMR (400 MHz, DMSO-$d_6$) δ 1.96-2.13 (3H, m), 2.58 (7H, s), 2.83-2.92 (1H, m), 3.26-3.30 (2H, m), 3.40-3.43 (6H, m), 3.48 (1H, s), 3.63-3.67 (2H, m), 3.76-3.80 (2H, m), 4.17-4.19 (2H, m), 5.05-5.09 (1H, m), 5.23-5.36 (1H, m), 7.11 (2H, d, J=8.4 Hz), 7.24-7.29 (2H, m), 7.34 (1H, s), 7.60-7.69 (4H, m), 8.10 (1H, s), 8.57 (1H, brs), 8.66 (1H, d, J=2.4 Hz), 9.88 (1H, s), 11.09 (1H, s), 12.95 (1H, s).

Compounds 92-97 may be prepared in an analogous manner.

Example Synthesis of Compound 99

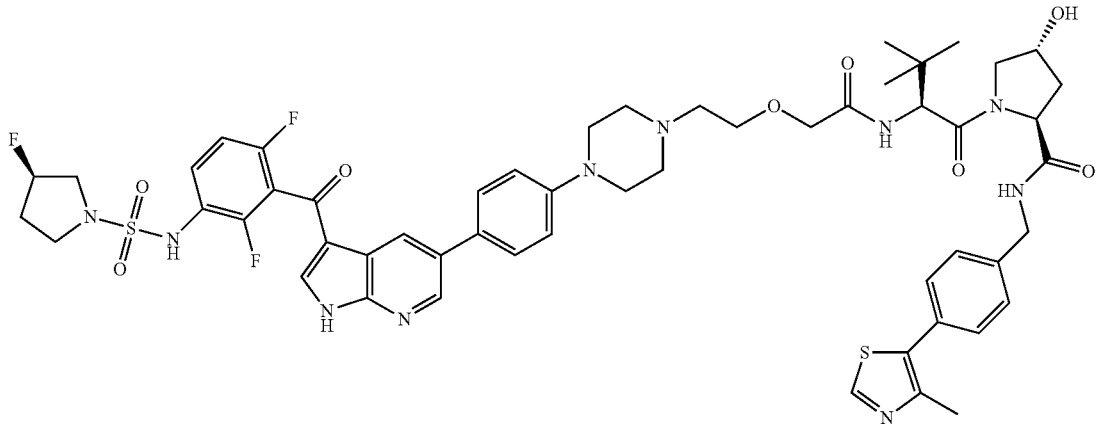 [SMILES: Cc1ncsc1-c1ccc(CNC(=O)[C@@H]2C[C@@H](O)CN2C(=O)[C@@H](NC(=O)COCCN2CCN(c3ccc(-c4cnc5[nH]cc(C(=O)c6c(F)ccc(NS(=O)(=O)N7CC[C@@H](F)C7)c6F)c5c4)cc3)CC2)C(C)(C)C)cc1]

Step A: tert-butyl 4-(4-bromophenyl)piperazine-1-carboxylate

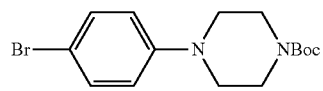 [SMILES: CC(C)(C)OC(=O)N1CCN(c2ccc(Br)cc2)CC1]

To a solution of 1,4-dibromobenzene (5.0 g, 21.2 mmol) in toluene (100 mL) were added tert-butyl piperazine-1-carboxylate (3.04 g, 16.3 mmol), Pd$_2$(dba)$_3$ (485 mg, 0.53 mmol), t-BuOK (5.95 g, 53 mmol) and BINAP (485 mg, 0.53 mmol). The resulting solution was stirred at 90° C. for 3 hours under N$_2$ atmosphere. After cooling to room temperature, the reaction was quenched with H$_2$O (50 mL), and the mixture was extracted with EA. The combined organic layer was dried over anhydrous sodium sulfate, and concentrated in vacuo. The residue was purified by silica gel to afford the desired product (1.2 g, 17% yield) as a white solid. $^1$H NMR (400 MHz, CDCl$_3$): δ 7.35 (d, J=8.8 Hz, 2H), 6.78 (d, J=9.2 Hz, 2H), 3.57 (t, J=4.8 Hz, 4H), 3.09 (t, J=4.8 Hz, 4H), 1.48 (s, 9H).

Step B: tert-butyl 4-(4-(4,4,5,5-tetramethyl-1,3,2-dioxaborolan-2-yl)phenyl)piperazine-1-carboxylate

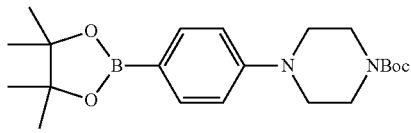 [SMILES: CC(C)(C)OC(=O)N1CCN(c2ccc(B3OC(C)(C)C(C)(C)O3)cc2)CC1]

To a solution of tert-butyl 4-(4-bromophenyl)piperazine-1-carboxylate (1.2 g, 3.53 mmol) in 1,4-dioxane (24 mL) were added 4,4,4',4',5,5,5',5'-octamethyl-2,2'-bi(1,3,2-dioxaborolane) (1.8 g, 7.06 mmol), Pd(dppf)Cl$_2$ (258 mg, 0.35 mmol) and KOAc (1.04 g, 10.59 mmol). The resulting solution was stirred at 90° C. overnight under N$_2$ atmosphere. TLC showed the reaction was completed. After cooled to room temperature, the reaction was diluted with 50 mL of EA, and the mixture was washed with water and brine. The organic phase was dried over anhydrous sodium sulfate. The residue was purified by chromatography column to afford the desired product (1.0 g, 73% yield). LCMS (ES$^+$): m/z 482.0.

Step C: tert-butyl 2-(2-(4-(4-(4,4,5,5-tetramethyl-1,3,2-dioxaborolan-2-yl)phenyl)piperazin-1-yl)ethoxy)acetate

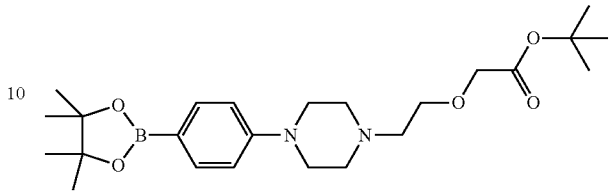

To a solution of tert-butyl 4-(4-(4,4,5,5-tetramethyl-1,3,2-dioxaborolan-2-yl)phenyl)piperazine-1-carboxylate (550 mg, 1.42 mmol) in DCM (5 mL) was added TFA (1.5 mL, 20.2 mmol). The resulting solution was stirred at 5° C. for 2 hours. The solvent was removed under vacuum to afford a residue (547 mg, calculated), which was used directly in next step. To a solution of the residue (547 mg, 1.42 mmol) in dry DMF (5 mL) were added K$_2$CO$_3$ (977 mg, 7.08 mmol), KI (470 mg, 2.83 mmol) and tert-butyl 2-(2-chloroethoxy)acetate (550 mg, 2.83 mmol). The resulting solution was stirred at 90° C. for 3 hours. After cooling to room temperature, the reaction was quenched with 20 mL of saturated NaCl solution, and the mixture was extracted with EA twice. The combined organic layer was concentration in vacuo, and the residue was purified by silica gel to afford the desired product (300 mg, 47% yield in two steps) as oil. $^1$H NMR (400 MHz, CDCl$_3$): δ 7.70 (d, J=8.4 Hz, 2H), 6.88 (d, J=8.8 Hz, 2H), 4.01 (m, 3H), 3.69 (m, 4H), 3.30 (m, 4H), 2.68 (m, 6H), 1.48 (s, 9H), 1.32 (s, 12H).

Step D: (R)-tert-butyl 2-(2-(4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)ethoxy)acetate

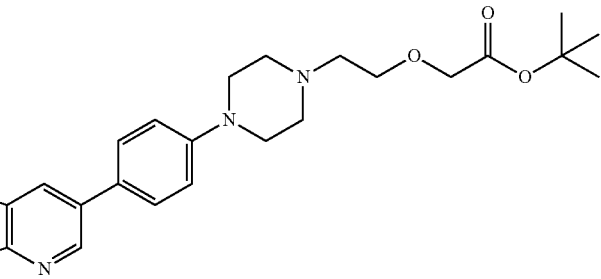

To a solution of tert-butyl 2-(2-(4-(4-(4,4,5,5-tetramethyl-1,3,2-dioxaborolan-2-yl)phenyl)piperazin-1-yl)ethoxy)acetate (100 mg, 0.20 mmol) in 1,4-dioxane/H$_2$O (10 ml/1 mL) were added (3R)—N-[3-([5-bromo-1H-pyrrolo[2,3-b]pyridin-3-yl]carbonyl)-2,4-difluorophenyl]-3-fluoropyrrolidine-1-sulfonamide (134 mg, 0.36 mmol), Pd(aMphos)Cl$_2$ (15 mg, 0.02 mmol) and CsF (121 mg, 0.80 mmol). The resulting solution was stirred at 95° C. for 3 hours under N$_2$ atmosphere. TLC showed the reaction was completed. After cooling to room temperature, the reaction was diluted with 50 mL of EA, and the mixture was washed with water and brine. The organic phase was dried over anhydrous sodium sulfate and concentrated in vacuo. The residue was purified by chromatography column to afford the desired product (100 mg, 66% yield). LCMS (ES$^+$): m/z 743.2 [M+H-16]$^+$.

Step E: (2S,4R)-1-((S)-2-(2-(2-(4-(4-(3-(2,6-difluoro-3-((R)-3-fluoropyrrolidine-1-sulfonamido)benzoyl)-1H-pyrrolo[2,3-b]pyridin-5-yl)phenyl)piperazin-1-yl)ethoxy)acetamido)-3,3-dimethylbutanoyl)-4-hydroxy-N-(4-(4-methylthiazol-5-yl)benzyl)pyrrolidine-2-carboxamide To a solution of (R)-tert-butyl 2-(2-(4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)ethoxy)acetate compound with methanol (100 mg, 0.13 mmol) in 1,4-dioxane (2 mL) was added HCl (g), 1,4-dioxane (1 mL, 8 M). The resulting solution was stirred at 50° C. for 3 hours. TLC showed the reaction was completed. After cooled to room temperature, the reaction mixture was concentrated to afford a crude product (93 mg, 100% yield, calculated), which was used into next reaction. To a solution of crude product (93 mg, 0.13 mmol) in dry NMP (5 mL) were added (2S,4R)—N-(4-(4-methylthiazol-5-yl)benzyl)-1-((S)-2-amino-3,3-dimethylbutanoyl)-4-hydroxypyrrolidine-2-carboxamide hydrochloride (91 mg, 0.19 mmol), DIEA (167 mg, 1.30 mmol) and PyBOP (203 mg, 0.39 mmol) subsequently. The resulting solution was stirred at 10° C. for 1 hour. After the reaction was quenched with brine (20 mL), the mixture was extracted with EA twice. The organic layers was concentrated, and the residue was purified by silica gel and preparative HPLC to afford the desired product (39 mg, 27% yield in two steps) as a yellow solid. $^1$H NMR (400 MHz, CD$_3$OD): δ 8.80 (s, 1H), 8.65 (s, 1H), 8.56 (s, 1H), 7.89 (s, 1H), 7.73 (m, 1H), 7.54 (d, J=8.8 Hz, 2H), 7.44 (d, J=7.6 Hz, 2H), 7.36 (d, J=8.0 Hz, 2H), 7.07-7.14 (m, 3H), 5.13-5.30 (m, 1H), 4.71 (s, 1H), 4.50-4.65 (m, 4H), 4.34 (d, J=15.6 Hz, 1H), 4.12 (m, 2H), 3.78-3.95 (m, 4H), 3.40-3.65 (m, 9H), 3.10 (m, 6H), 2.42 (s, 3H), 2.00-2.30 (m, 4H), 1.04 (s, 9H); LCMS (ES$^+$): m/z 550.3 [M/2+H]$^+$.

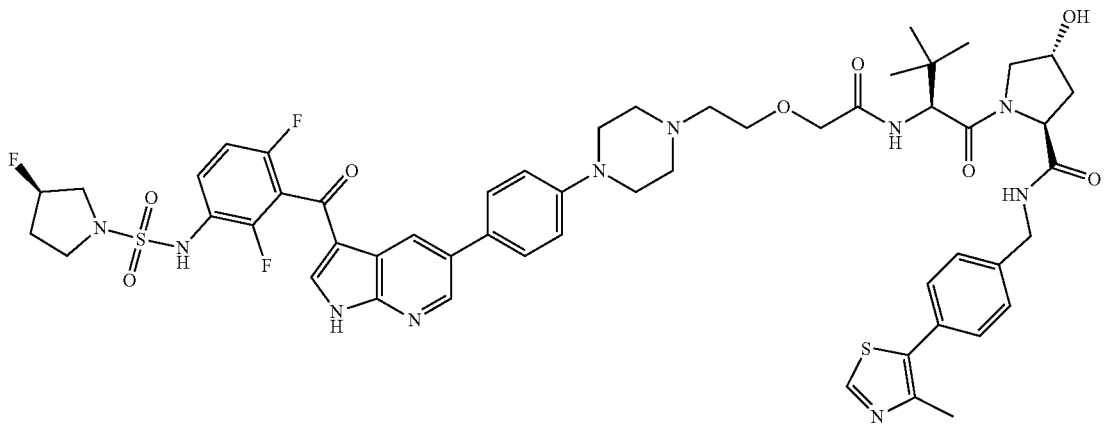 [SMILES: Cc1ncsc1-c1ccc(CNC(=O)[C@@H]2C[C@@H](O)CN2C(=O)[C@@H](NC(=O)COCCN2CCN(c3ccc(-c4cnc5[nH]cc(C(=O)c6c(F)ccc(NS(=O)(=O)N7CC[C@@H](F)C7)c6F)c5c4)cc3)CC2)C(C)(C)C)cc1]

Compounds 98, 100-101, 102, 103-106, and 223-252 may be prepared in an analogous manner.

Example Synthesis of Compound 114

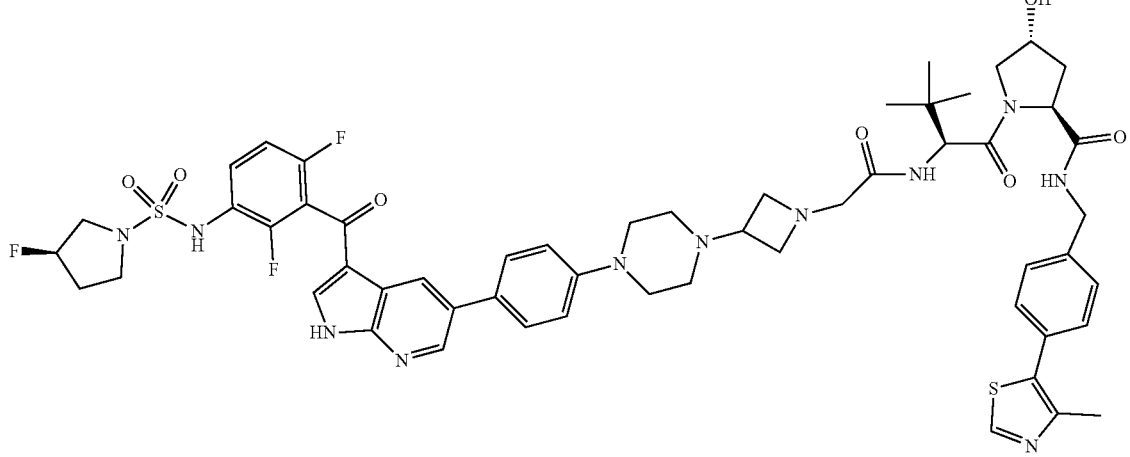

Step A:
1-(azetidin-3-yl)-4-(4-bromophenyl)piperazine hydrochloride

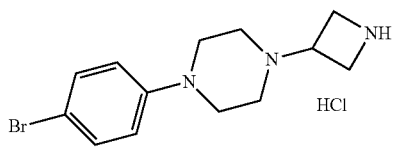 [SMILES: Brc1ccc(N2CCN(C3CNC3)CC2)cc1 ; Cl]

To a solution of 1-(4-bromophenyl)piperazine hydrochloride (2.0 g, 7.21 mmol) in CH₃OH/DCM (v/v=1/1, 30 mL) was added KOAc (1.4 g, 14.4 mmol) and cat. AcOH (0.1 mL) at room temperature. After stirring for 30 minutes, NaBH(OAc)₃ (7.6 g, 36.1 mmol). The mixture was stirred at 30° C. overnight. After the reaction was quenched with aqu.NaHCO₃ (50 mL), the mixture was extracted with DCM (100 mL×2). The combined organic layer was washed with brine (50 mL), dried over anhydrous sodium sulfate and concentrated under vacuum to afford crude the desired product (2.5 g) as a light brown solid, which was used to next step without further purification. To a solution of the above intermediates in methanol (20 mL) was added HCl (g)/CH₃OH (10 mL). The resulting solution was stirred for 2 hours at room temperature. The solvent was removed under vacuum. The residue was triturated with DCM and filtered to afford the desired product 1-(azetidin-3-yl)-4-(4-bromophenyl)piperazine hydrochloride (2.0 g) as a brown solid.

Step B: ethyl 2-(3-(4-(4-bromophenyl)piperazin-1-yl)azetidin-1-yl)acetate

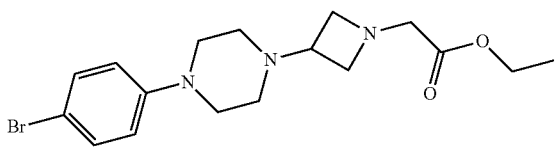 [SMILES: CCOC(=O)CN1CC(N2CCN(c3ccc(Br)cc3)CC2)C1]

To a solution of 1-(azetidin-3-yl)-4-(4-bromophenyl)piperazine hydrochloride (2.0 g, 6.01 mmol) in CH₃OH/DCM (v/v=1/1, 10 mL) was added KOAc (1.2 g, 12.1 mmol) and cat. AcOH (0.1 mL) at room temperature. After stirring for 30 minutes, NaBH(OAc)₃ (6.3 g, 30.1 mmol). The mixture was stirred at 30° C. overnight. After the reaction was quenched with aq. NaHCO₃ (30 mL), the mixture was extracted with DCM (50 mL×3). The combined organic layer was washed with brine (50 mL), dried over anhydrous sodium sulfate and concentrated under vacuum to afford the desired product ethyl 2-(3-(4-(4-bromophenyl)piperazin-1-yl)azetidin-1-yl)acetate (1.0 g, crude) as a light brown solid, which was used to next step without further purification. LCMS (ES⁺): m/z 384.1; 382.1 [M+H]⁺.

Step C: methyl 2-(3-(4-(4-(4,4,5,5-tetramethyl-1,3,2-dioxaborolan-2-yl)phenyl)piperazin-1-yl)azetidin-1-yl)acetate

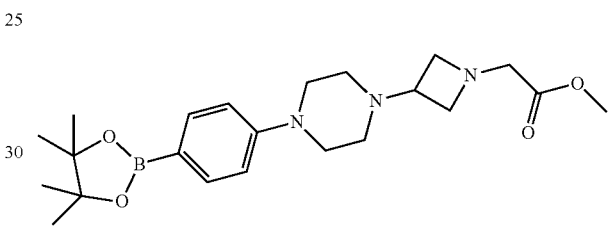

To a solution of ethyl 2-(3-(4-(4-bromophenyl)piperazin-1-yl)azetidin-1-yl) acetate (1.0 g, crude) in methanol (20 mL) was added HCl (g)/CH₃OH (10 mL). The resulting solution was stirred at 60° C. for 2 hours. The solvent was removed under vacuum. The residue was taken up with DCM (100 mL), and the mixture was washed with NaHCO₃ (30 mL×3). The organic phase was concentrated under vacuum. The residue (500 mg) was used into next reaction without further purification. To a solution of the above intermediates (500 mg, 1.4 mmol) in 1,4-dioxane (20 mL) was added KOAc (267 mg, 2.8 mmol), Pd(dppf)Cl₂ (190 mg, 0.14 mmol), 4,4,5,5-tetramethyl-2-(4,4,5,5-tetramethyl-1,3,2-dioxaborolan-2-yl)-1,3,2-dioxaborolane (700 mg, 2.8 mmol). The resulting solution was purged with N₂ at room temperature for 10 minutes to remove the excess O₂. The mixture was stirred at 100° C. overnight. After cooling to room temperature, the reaction was taken up with EtOAc. The organic phase was concentrated under vacuum. The residue was purified by silica gel with PE/EA (10-1/1) to afford the desired product methyl 2-(3-(4-(4-(4,4,5,5-tetramethyl-1,3,2-dioxaborolan-2-yl)phenyl)piperazin-1-yl)azetidin-1-yl)acetate (300 mg) as a brown solid. LCMS (ES⁺): m/z 416.3 [M+H]⁺.

Step D: (2S,4R)—N-(4-(4-methylthiazol-5-yl)benzyl)-1-((S)-3,3-dimethyl-2-(2-(3-(4-(4-(4,4,5,5-tetramethyl-1,3,2-dioxaborolan-2-yl)phenyl)piperazin-1-yl)azetidin-1-yl)acetamido)butanoyl)-4-hydroxypyrrolidine-2-carboxamide

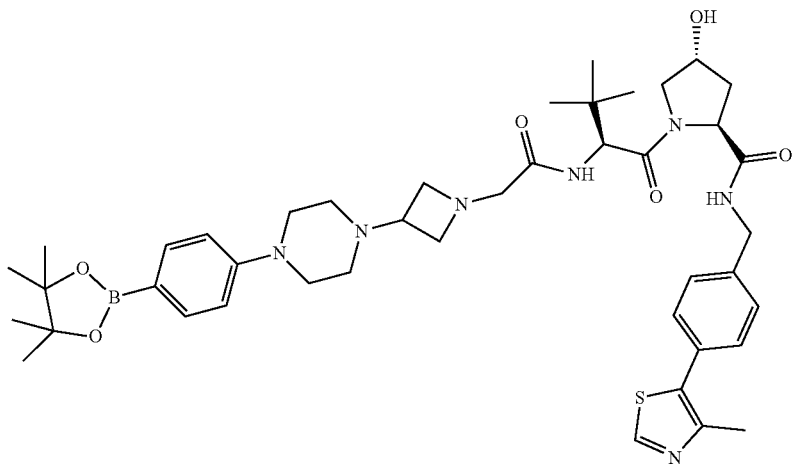 [SMILES: Cc1ncsc1-c1ccc(CNC(=O)[C@@H]2C[C@@H](O)CN2C(=O)[C@@H](NC(=O)CN2CC(N3CCN(c4ccc(B5OC(C)(C)C(C)(C)O5)cc4)CC3)C2)C(C)(C)C)cc1]

To a solution of methyl 2-(3-(4-(4-(4,4,5,5-tetramethyl-1,3,2-dioxaborolan-2-yl)phenyl)piperazin-1-yl)azetidin-1-yl)acetate (300 mg, 0.72 mmol) in H$_2$O/THF (v/v=1/5, 5 mL) was added LiOH (34 mg, 1.5 mmol). The resulting solution was stirred at room temperature for 1 hour. Then the solvent was removed under vacuum. The residue was used into next reaction without further purification. To a solution of the above intermediates in DMF (5.0 mL) were added DIEA (300 mg, 2.2 mmol), (2S,4R)—N-(4-(4-methylthiazol-5-yl)benzyl)-1-((S)-2-amino-3,3-dimethylbutanoyl)-4-hydroxypyrrolidine-2-carboxamide hydrochloride (338 mg, 0.72 mmol) and PyBOP (564 mg, 1.1 mmol) at room temperature. The resulting solution was stirred at 20° C. for 2 hours. The reaction was quenched with H$_2$O (10 mL), and the mixture was extracted with EtOAc (20 mL×3). The combined organic layer was concentrated under vacuum. The residue was purified by preparative TLC with DCM/CH$_3$OH (20/1) to afford the desired product (2S,4R)-1-((S)-3,3-dimethyl-2-(2-(3-(4-(4-(4,4,5,5-tetramethyl-1,3,2-dioxaborolan-2-yl)phenyl)piperazin-1-yl)azetidin-1-yl)acetamido)butanoyl)-4-hydroxy-N-(4-(4-methylthiazol-5-yl)benzyl)pyrrolidine-2-carboxamide (80 mg) as a light brown solid. LCMS (ES$^+$): m/z 814.4 [M+H]$^+$.

Step E: (2S,4R)—N-(4-(4-methylthiazol-5-yl)benzyl)-1-((S)-2-(2-(3-(4-(4-(3-(2,6-difluoro-3-((R)-3-fluoropyrrolidine-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-4-hydroxypyrrolidine-2-carboxamide

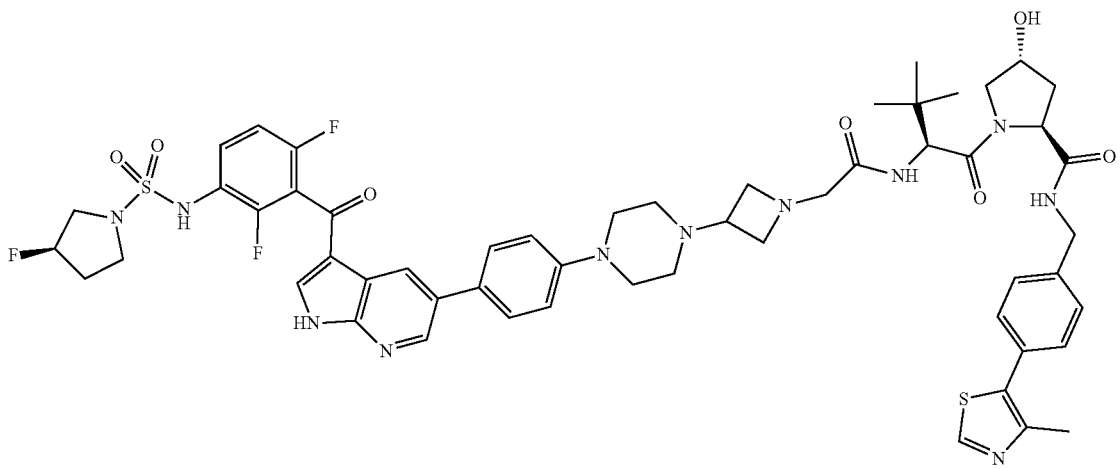 [SMILES: Cc1ncsc1-c1ccc(CNC(=O)[C@@H]2C[C@@H](O)CN2C(=O)[C@@H](NC(=O)CN2CC(N3CCN(c4ccc(-c5cnc6[nH]cc(C(=O)c7c(F)ccc(NS(=O)(=O)N8CC[C@@H](F)C8)c7F)c6c5)cc4)CC3)C2)C(C)(C)C)cc1]

To a solution of (2S,4R)-1-((S)-3,3-dimethyl-2-(2-(3-(4-(4-(4,4,5,5-tetramethyl-1,3,2-dioxaborolan-2-yl)phenyl)piperazin-1-yl)azetidin-1-yl)acetamido)butanoyl)-4-hydroxy-N-(4-(4-methylthiazol-5-yl)benzyl)pyrrolidine-2-carboxamide (80 mg, 0.098 mmol) in H$_2$O/1,4-dioxane (v/v=1/5, 5.0 mL) were added CsF (45 mg, 0.29 mmol), Pd(amphos)Cl$_2$ (8 mg, 0.01 mmol), (R)—N-(3-(5-bromo-1H-pyrrolo[2,3-b]pyridine-3-carbonyl)-2,4-difluorophenyl)-3-fluoropyrrolidine-1-sulfonamide (70 mg, 0.14 mmol) at room temperature. The solution was purged with N₂ at room temperature for 10 minutes to remove the excess O₂. The resulting solution was stirred at 80° C. overnight. After cooling to room temperature, the reaction was taken up with EtOAc. The combined organic layer was concentrated under vacuum. The residue was purified by preparative TLC with DCM/CH₃OH (20/1) to afford the desired product (2S,4R)-1-((S)-2-(2-(3-(4-(4-(3-(2,6-difluoro-3-(((R)-3-fluoro -pyrrolidine)-1-sulfonamido)benzoyl)-1H-pyrrolo[2,3-b]pyridin-5-yl)phenyl)piperazin-1-yl)azetidin-1-yl)acetamido)-3,3-dimethylbutanoyl)-4-hydroxy-N-(4-(4-methylthiazol-5-yl)benzyl)pyrrolidine-2-carboxamide (35 mg) as a light yellow solid. ¹H NMR (400 MHz, DMSO-d₆): δ 9.02 (s, 1H), 8.71-8.75 (m, 2H), 8.68 (br, 1H), 8.12 (s, 1H), 7.61-7.66 (m, 4H), 7.42-7.46 (m, 5H), 7.19-7.21 (m, 2H), 7.06 (d, J=8.0 Hz, 2H), 5.33-5.35 (m, 0.5H), 5.22-5.23 (m, 0.5H), 5.16 (d, J=7.2 Hz, 1H), 4.53 (d, J=9.6 Hz, 1H), 4.34-4.47 (m, 5H), 4.24-4.29 (m, 1H), 4.04 (s, 1H), 3.65-3.66 (m, 3H), 3.51-3.61 (m, 5H), 3.22-3.34 (m, 6H), 3.08 (br, 3H), 2.41-2.47 (m, 3H), 1.93-2.07 (m, 5H), 0.94 (s, 9H); LCMS (ES⁺): m/z 1111.3 [M+H]⁺, 1108.3 [M–H]⁺.

Compounds 107-113, 115, 116, and 253-269 may be prepared in an analogous manner.

Example Synthesis of Compound 117

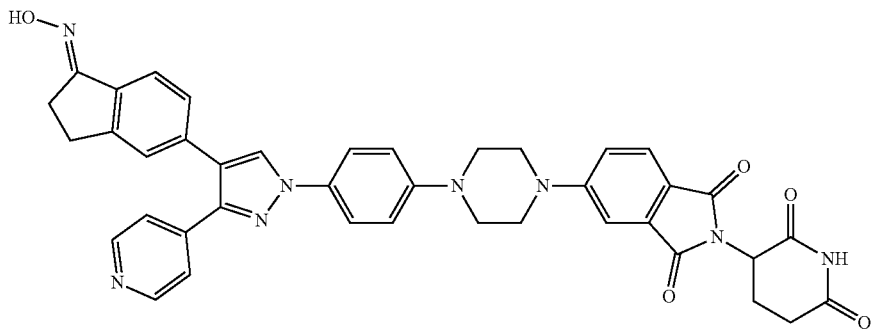 [SMILES: O=C1CCC(N2C(=O)c3ccc(N4CCN(c5ccc(-n6cc(-c7ccc8c(c7)CC/C8=N\O)c(-c7ccncc7)n6)cc5)CC4)cc3C2=O)C(=O)N1]

Step A: tert-butyl 4-(4-(4-bromo-3-(pyridin-4-yl)-1H-pyrazol-1-yl)phenyl)piperazine-1-carboxylate

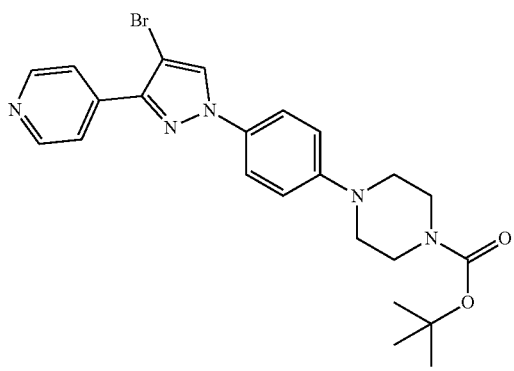 [SMILES: CC(C)(C)OC(=O)N1CCN(c2ccc(-n3cc(Br)c(-c4ccncc4)n3)cc2)CC1]

The mixture of 4-(4-bromo-1H-pyrazol-3-yl)pyridine (5.0 g, 22.3 mmol) (previously described in *Bioorg. Med. Chem. Lett.* 2008, 18, 4692-4695), tert-butyl 4-(4-(4,4,5,5-tetramethyl-1,3,2-dioxaborolan-2-yl)phenyl)piperazine-1-carboxylate (8.7 g, 22.3 mmol) and cupric acetate (4.0 g, 22.3 mmol) in pyridine (30 mL) was stirred at 100° C. overnight. The mixture was concentrated in vacuo and the residue was purified by column chromatography on silica gel (petroleum ether/ethyl acetate=5/1) to give tert-butyl 4-(4-(4-bromo-3-(pyridin-4-yl)-1H-pyrazol-1-yl)phenyl)piperazine-1-carboxylate (10.8 g, 70% yield) as a brown solid.

Step B: tert-butyl 4-(4-(4-(1-oxo-2,3-dihydro-1H-inden-5-yl)-3-(pyridin-4-yl)-1H-pyrazol-1-yl)phenyl)piperazine-1-carboxylate

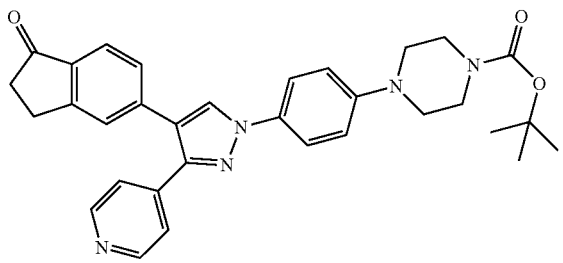 [SMILES: CC(C)(C)OC(=O)N1CCN(c2ccc(-n3cc(-c4ccc5c(c4)CCC5=O)c(-c4ccncc4)n3)cc2)CC1]

The mixture of tert-butyl 4-(4-(4-bromo-3-(pyridin-4-yl)-1H-pyrazol-1-yl)phenyl)piperazine-1-carboxylate (2.4 g, 5.0 mmol), 5-(4,4,5,5-tetramethyl-1,3,2-dioxaborolan-2-yl)-2,3-dihydro-1H-inden-1-one (1.3 g, 5.0 mmol), [1,1'-bis(diphenylphosphino)ferrocene]dichloropalladium (366 mg, 0.5 mmol). tri-tert-butylphosphine tetrafluoroborate (145 mg, 0.5 mmol) and cesium fluoride (2.3 g, 15.0 mmol) in 1,4-dioxane/water (20 mL, 10/1) was stirred at 90° C. overnight. The mixture was poured into water (30 mL) and extracted with dichloromethane (30 mL×3). The combined organic phase was concentrated in vacuo and the residue was purified by column chromatography on silica gel (dichloromethane/methanol=20/1) to give tert-butyl 4-(4-(4-(1-oxo-2,3-dihydro-1H-inden-5-yl)-3-(pyridin-4-yl)-1H-pyrazol-1-yl)phenyl)piperazine-1-carboxylate (1.6 g, 60% yield) as a yellow solid. LCMS: m/z 536.3 [M+H]⁺.

Step C: 5-(1-(4-(piperazin-1-yl)phenyl)-3-(pyridin-4-yl)-1H-pyrazol-4-yl)-2,3-dihydro-1H-inden-1-one hydrochloride

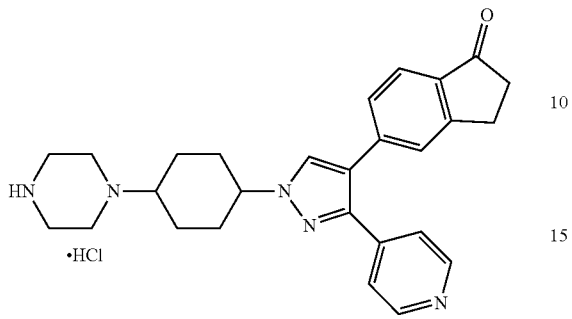

The solution of tert-butyl 4-(4-(4-(1-oxo-2,3-dihydro-1H-inden-5-yl)-3-(pyridin-4-yl)-1H-pyrazol-1-yl)phenyl)piperazine-1-carboxylate (1.6 g, 3.0 mmol) in dry hydrochloride acid/methanol (30 mL, 1.0 M.) was stirred at room temperature overnight. The reaction mixture was concentrated in vacuo to give 5-(1-(4-(piperazin-1-yl)phenyl)-3-(pyridin-4-yl)-1H-pyrazol-4-yl)-2,3-dihydro-1H-inden-1-one hydrochloride (1.0 g, 80% yield) as a white solid, which was directly used to the next step without further purification.

Step D: 2-(2,6-dioxopiperidin-3-yl)-5-(4-(4-(4-(1-oxo-2,3-dihydro-1H-inden-5-yl)-3-(pyridin-4-yl)-1H-pyrazol-1-yl)phenyl)piperazin-1-yl)isoindoline-1,3-dione

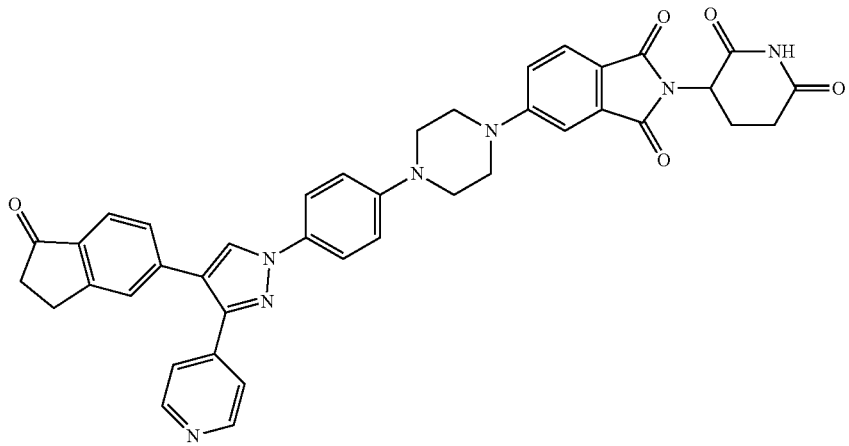 [SMILES: O=C1CCC(N2C(=O)c3ccc(N4CCN(c5ccc(-n6cc(-c7ccc8c(c7)CCC8=O)c(-c7ccncc7)n6)cc5)CC4)cc3C2=O)C(=O)N1]

The mixture of 5-(1-(4-(piperazin-1-yl)phenyl)-3-(pyridin-4-yl)-1H-pyrazol-4-yl)-2,3-dihydro-1H-inden-1-one hydrochloride (1.0 g, 2.3 mmol), 2-(2,6-dioxopiperidin-3-yl)-5-fluoroisoindoline-1,3-dione (635 mg, 2.3 mmol) and triethylamine (697 mg, 6.9 mmol) in dimethyl sulfoxide (10 mL) was stirred at 80° C. overnight. The mixture was poured into water (20 mL) and extracted with ethyl acetate (20 mL×3). The combined organic phase was concentrated in vacuo and the residue was purified by column chromatography on silica gel (dichloromethane/methanol=20/1) to give 2-(2,6-dioxopiperidin-3-yl)-5-(4-(4-(4-(1-oxo-2,3-dihydro-1H-inden-5-yl)-3-(pyridin-4-yl)-1H-pyrazol-1-yl)phenyl)piperazin-1-yl)isoindoline-1,3-dione (1.1 g, 70% yield) as a yellow solid. LCMS: m/z 692.3 [M+H]$^+$.

Step E: (E)-2-(2,6-dioxopiperidin-3-yl)-5-(4-(4-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione

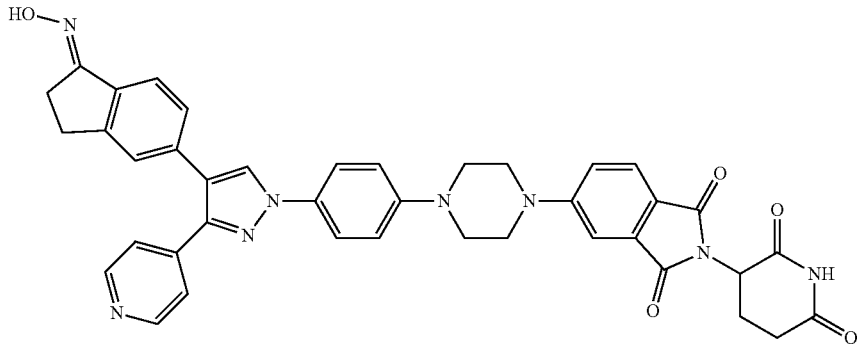 [SMILES: O=C1CCC(N2C(=O)c3ccc(N4CCN(c5ccc(-n6cc(-c7ccc8c(c7)CC/C8=N\O)c(-c7ccncc7)n6)cc5)CC4)cc3C2=O)C(=O)N1]

The mixture of 2-(2,6-dioxopiperidin-3-yl)-5-(4-(4-(4-(1-oxo-2,3-dihydro-1H-inden-5-yl)-3-(pyridin-4-yl)-1H-pyrazol-1-yl)phenyl)piperazin-1-yl)isoindoline-1,3-dione (300 mg, 0.43 mmol) and hydroxylamine hydrochloride (300 mg, 4.3 mmol) in pyridine (10 mL) was stirred at room temperature overnight. The reaction mixture was concentrated in vacuo. The residue was purified by preparative HPLC to give (E)-2-(2,6-dioxopiperidin-3-yl)-5-(4-(4-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione (182 mg, 60% yield) as a yellow solid. LCMS: m/z 707.3 [M+H]$^+$; $^1$H NMR (400 MHz, DMSO-d$_6$) δ 2.01-2.07 (1H, m), 2.54-2.61 (2H, m), 2.80-2.89 (3H, m), 2.98-3.02 (2H, m), 3.39 (4H, brs), 3.66 (4H, brs), 5.06-5.11 (1H, m), 7.16 (2H, d, J=8.8 Hz), 7.21 (1H, d, J=7.6 Hz), 7.33-7.35 (1H, m), 7.42 (2H, d, J=8.0 Hz), 7.47 (2H, dd, J=5.6, 1.6 Hz), 7.55 (1H, J=7.6 Hz), 7.72 (1H, d, J=8.4 Hz), 7.83 (2H, d, J=8.8 Hz), 8.57 (2H, dd, J=4.4, 1.2 Hz), 8.73 (1H, s), 10.9 (1H, s), 11.0-11.1 (1H, m).

Compounds 118-132 and 271 may be prepared in an analogous manner.

Example Synthesis of Compound 137

Step A: tert-butyl (2-(4-(4-bromo-3-(pyridin-4-yl)-1H-pyrazol-1-yl)phenoxy)ethyl)(methyl)carbamate

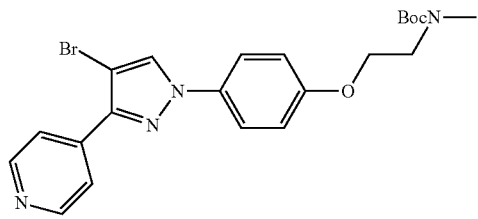

To a solution of tert-butyl methyl(2-(4-(4,4,5,5-tetramethyl-1,3,2-dioxaborolan-2-yl)phenoxy)ethyl)carbamate (3.57 g, 9.47 mmol) and 4-(4-bromo-1H-pyrazol-3-yl)pyridine (2.12 g, 9.47 mmol) in DCM(20 mL) were added Et$_2$NH(6.91 g, 94.72 mmol), Cu(OAc)$_2$(1.72 g, 9.47 mmol). The resulting mixture was stirred at 30° C. for 16 hours under the atmosphere of O$_2$. The mixture was diluted with DCM (30 mL), and then the mixture was washed with NH$_3$—H$_2$O thrice.

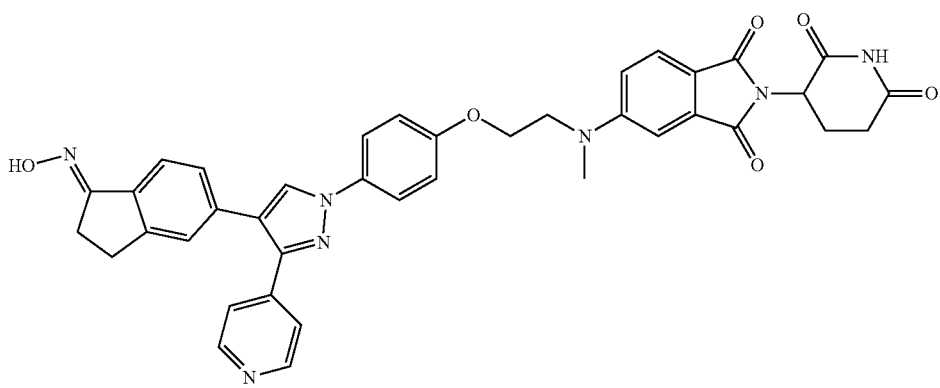 [SMILES: CN(CCOc1ccc(-n2cc(-c3ccc4c(c3)CC/C4=N\O)c(-c3ccncc3)n2)cc1)c1ccc2c(c1)C(=O)N(C1CCC(=O)NC1=O)C2=O]

The organic phase was evaporated under reduced pressure, The residue was purified by silica gel column chromatography on silica gel(DCM/MeOH=80/1) to afford tert-butyl (2-(4-(4-bromo-3-(pyridin-4-yl)-1H-pyrazol-1-yl)phenoxy)ethyl)(methyl)carbamate (3.0 g, 66.9% yield) as a brown oil.

Step B: 2-(4-(4-bromo-3-(pyridin-4-yl)-1H-pyrazol-1-yl)phenoxy)-N-methylethan-1-amine

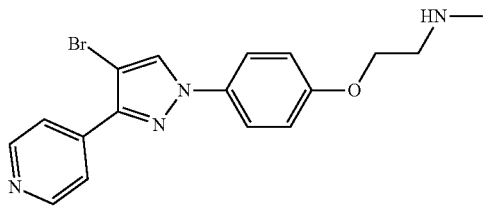 [SMILES: CNCCOc1ccc(-n2cc(Br)c(-c3ccncc3)n2)cc1]

To a solution of tert-butyl (2-(4-(4-bromo-3-(pyridin-4-yl)-1H-pyrazol-1-yl)phenoxy)ethyl)(methyl)carbamate (1.56 g, 3.31 mmol) in MeOH (6 mL) was added HCl/Dioxane(6 N, 10 mL) at room temperature slowly. The mixture was stirred at room temperature for 2 hours. The mixture was evaporated under reduced pressure to afford 2-(4-(4-bromo-3-(pyridin-4-yl)-1H-pyrazol-1-yl)phenoxy)-N-methylethan-1-amine as a colorless solid (1.23 g, 100% yield).

Step C: 5-((2-(4-(4-bromo-3-(pyridin-4-yl)-1H-pyrazol-1-yl)phenoxy)ethyl)(methyl)amino)-2-(2,6-dioxopiperidin-3-yl)isoindoline-1,3-dione

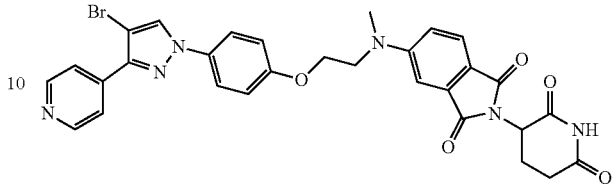

To a solution of 2-(4-(4-bromo-3-(pyridin-4-yl)-1H-pyrazol-1-yl)phenoxy)-N-methylethan-1-amine (400 mg, 1.07 mmol) and 2-(2,6-dioxopiperidin-3-yl)-5-fluoroisoindoline-1,3-dione (591.9 mg, 2.14 mmol) in NMP(2 mL) was added DIPEA(1.38 g, 10.7 mmol). The resulting mixture was stirred at 130° C. for 12 hours under the atmosphere of $N_2$. The mixture was diluted with EA (30 mL), and then the mixture was washed with brine twice. The organic phase was evaporated under reduced pressure, The residue was purified by column chromatography on silica gel (PE/EtOAc=1/3) to afford 5-((2-(4-(4-bromo-3-(pyridin-4-yl)-1H-pyrazol-1-yl)phenoxy)ethyl)(methyl)amino)-2-(2,6-dioxopiperidin-3-yl)isoindoline-1,3-dione (500 mg, 74.1% yield).

Step D: 2-(2,6-dioxopiperidin-3-yl)-5-(methyl(2-(4-(4-(1-oxo-2,3-dihydro-1H-inden-5-yl)-3-(pyridin-4-yl)-1H-pyrazol-1-yl)phenoxy)ethyl)amino)isoindoline-1,3-dione

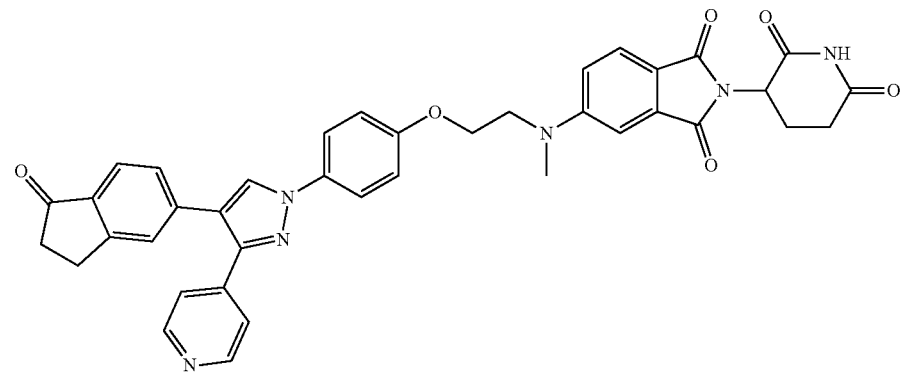 [SMILES: CN(CCOc1ccc(-n2cc(-c3ccc4c(c3)CCC4=O)c(-c3ccncc3)n2)cc1)c1ccc2c(c1)C(=O)N(C1CCC(=O)NC1=O)C2=O]

To a solution of 5-((2-(4-(4-bromo-3-(pyridin-4-yl)-1H-pyrazol-1-yl)phenoxy)ethyl)(methyl)amino)-2-(2,6-dioxopiperidin-3-yl)isoindoline-1,3-dione (500 mg, 0.79 mmol) and 5-(4,4,5,5-tetramethyl-1,3,2-dioxaborolan-2-yl)-2,3-dihydro-1H-inden-1-one (307.6 mg, 1.19 mmol) in 1,4-dioxane/$H_2O$(9 mL, 8:1) were added t-$Bu_3PHBF_4$ (92.2 mg, 0.32 mmol), CsF(483.3 mg, 3.18 mmol), $Cy_2NMe$(5 drop) and $Pd_2(dba)_3$(145.6 mg, 0.16 mmol). The resulting mixture was stirred at 100° C. for 2 hour under the atmosphere of $N_2$. The solvent was evaporated under reduced pressure. The residue was diluted with EA (30 mL), and then the mixture was washed with brine twice. The organic phase was evaporated under reduced pressure, The residue was purified by column chromatography on silica gel (PE/DCM/MeOH=800/200/25) to afford 2-(2,6-dioxopiperidin-3-yl)-5-(methyl(2-(4-(4-(1-oxo-2,3-dihydro-1H-inden-5-yl)-3-(pyridin-4-yl)-1H-pyrazol-1-yl)phenoxy)ethyl)amino)isoindoline-1,3-dione (500 mg, 92.4% yield).

Step E: (E)-2-(2,6-dioxopiperidin-3-yl)-5-((2-(4-(4-(1-(hydroxyimino)-2,3-dihydro-1H-inden-5-yl)-3-(pyridin-4-yl)-1H-pyrazol-1-yl)phenoxy)ethyl)(methyl)amino)isoindoline-1,3-dione To a solution of 2-(2,6-dioxopiperidin-3-yl)-5-(methyl(2-(4-(4-(1-oxo-2,3-dihydro-1H-inden-5-yl)-3-(pyridin-4-yl)-1H-pyrazol-1-yl)phenoxy)ethyl)amino)isoindoline-1,3-dione (200 mg, 0.294 mmol) in CH$_3$CN/Py(3 mL/3 mL) was added NH$_2$OH—HCl (200 mg, 2.877 mmol), the mixture was stirred at 40° C. for 0.5 hour. The mixture was diluted with DCM (30 mL), washed with brine twice. The organic layer was evaporated under reduced pressure. The residue was purified by TLC(DCM/EA/MeOH=50/100/15) to afford (E)-2-(2,6-dioxopiperidin-3-yl)-5-((2-(4-(4-(1-(hydroxyimino)-2,3-dihydro-1H-inden-5-yl)-3-(pyridin-4-yl)-1H-pyrazol-1-yl)phenoxy)ethyl)(methyl)amino)isoindoline-1,3-dione as a yellow-green solid (103 mg, 49.9% yield). $^1$H NMR (400 MHz, CDCl$_3$): δ 8.56 (d, J=4.0 Hz, 2H), 8.16 (s, 1H), 7.94 (s, 1H), 7.66-7.72 (m, 4H), 7.50 (d, J=4.8 Hz, 2H), 7.43 (s, 1H), 7.29 (s, 1H), 7.19-7.26 (m, 2H), 6.93-6.98 (m, 3H), 4.92-4.96 (m, 1H), 4.24 (t, J=4.8 Hz, 2H), 3.94 (t, J=10 Hz, 2H), 3.23 (s, 3H), 3.00-3.04 (m, 4H), 2.77-2.92 (m, 4H), 2.12-2.15 (d, J=8.4 Hz, 1H); LCMS (ES$^+$): m/z 696.2 [M+H]$^+$.

Compounds 133-136, 138-149, and 273-281 may be prepared in an analogous manner.

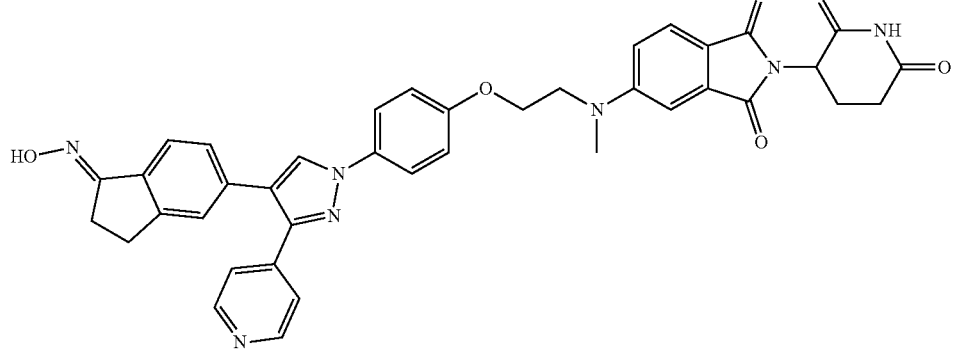

Example Synthesis of Compound 150

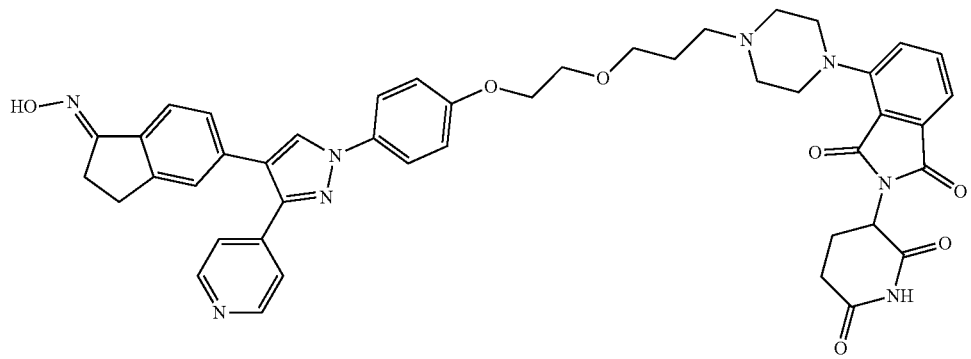 [SMILES: O=C1CCC(N2C(=O)c3cccc(N4CCN(CCCOCCOc5ccc(-n6cc(-c7ccc8c(c7)CC/C8=N\O)c(-c7ccncc7)n6)cc5)CC4)c3C2=O)C(=O)N1]

Step A: 4-(4-bromo-1-(4-(2-(3-((tert-butyldimethylsilyl)oxy)propoxy)ethoxy)phenyl)-1H-pyrazol-3-yl)pyridine

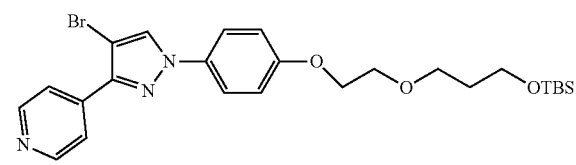 [SMILES: CC(C)(C)[Si](C)(C)OCCCOCCOc1ccc(-n2cc(Br)c(-c3ccncc3)n2)cc1]

To a solution of 2-(3-((tert-butyldimethylsilyl)oxy)propoxy)ethyl4-methylbenzene-esulfonate (420 mg, 1.08 mmol) in dry DMF (10 mL) were added K$_2$CO$_3$ (299 mg, 2.16 mmol) and 4-(4-bromo-1H-pyrazol-3-yl)pyridine (342 mg, 1.08 mmol) subsequently. The resulting solution was stirred at 80° C. for 3 hours. The reaction mixture was diluted with EA (30 mL) and washed with brine. The organic phase was dried over anhydrous sodium sulfate and concentrated under vacuum. The residue was purified to afford the desired product 4-(4-bromo-1-(4-(2-(3-((tert-butyldimethylsilyl)oxy)propoxy) ethoxy) phenyl)-1H-pyrazol-3-yl)pyridine (DCM:MeOH=20:1) (430 mg) as colorless solid. $^1$H NMR (400 MHz, CDCl$_3$): δ 8.66 (br, 2H), 7.89-7.93 (m, 3H), 7.55 (d, J=8.8 Hz, 2H), 6.96-6.98 (m, 2H), 4.04-4.14 (m, 2H), 3.76 (d, J=4.8 Hz, 2H), 3.67 (d, J=6 Hz, 3H), 3.58 (d, J=6.4 Hz, 2H), 1.71-1.79 (m, 2H), 0.84 (s, 9H), 0.0 (s, 6H).

Step B: 3-(2-(4-(4-bromo-3-(pyridin-4-yl)-1H-pyrazol-1-yl)phenoxy)ethoxy)propan-1-ol

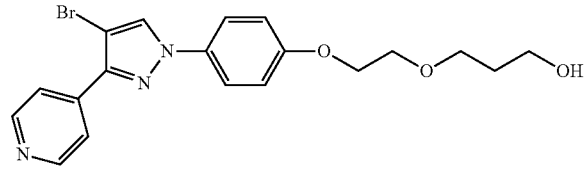 [SMILES: OCCCOCCOc1ccc(-n2cc(Br)c(-c3ccncc3)n2)cc1]

To a solution of 4-(4-bromo-1-(4-(2-(3-((tert-butyldimethylsilyl)oxy) propoxy)ethoxy)phenyl)-1H-pyrazol-3-yl)pyridine (430 mg, 0.808 mmol) in 1,4-dioxane (2 mL) was added 6 M HCl in 1,4-dioxane (4 mL). The resulting solution was stirred at 25° C. for 1 hour. The solvent was removed under reduced pressure to afford crude the desired product 3-(2-(4-(4-bromo-3-(pyridin-4-yl)-1H-pyrazol-1-yl)phenoxy)ethoxy)propan-1-ol (270 mg crude), which was used in next step without further purification. LCMS (ES$^+$): m/z 420.0 [M+H]$^+$.

Step C: 3-(2-(4-(4-bromo-3-(pyridin-4-yl)-1H-pyrazol-1-yl)phenoxy)ethoxy)propanal

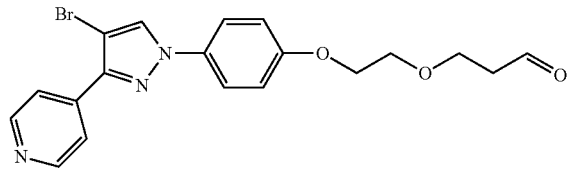 [SMILES: O=CCCOCCOc1ccc(-n2cc(Br)c(-c3ccncc3)n2)cc1]

To a solution of 3-(2-(4-(4-bromo-3-(pyridin-4-yl)-1H-pyrazol-1-yl)phenoxy)ethoxy)propan-1-ol (135 mg, 0.32 mmol), IBX (136 mg, 0.48 mmol) in CH$_3$CN (4 mL) was added at room temperature. The mixture was stirred at 80° C. for 2 hours. After the reaction was completed, the mixture was filtrated. The filtrate was concentrated under vacuum to afford crude desired product 3-(2-(4-(4-bromo-3-(pyridin-4-yl)-1H-pyrazol-1-yl)phenoxy) ethoxy)propanal (140 mg crude), which was used in next step without further purification. LCMS (ES$^+$): m/z 416.0 [M+H]$^+$.

Step D: tert-butyl 4-(2-(2,6-dioxopiperidin-3-yl)-1,3-dioxoisoindolin-4-yl)piperazine-1-carboxylate

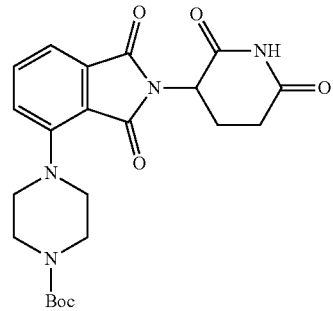 [SMILES: CC(C)(C)OC(=O)N1CCN(c2cccc3c2C(=O)N(C2CCC(=O)NC2=O)C3=O)CC1]

To a solution of tert-butyl piperazine-1-carboxylate (1.35 g, 7.25 mmol) in NMP (10 mL) were added 2-(2,6-dioxopiperidin-3-yl)-4-fluoroisoindoline-1,3-dione (1 g, 3.62 mmol) and DIEA (1.87 g, 14.5 mmol). The resulting solution was stirred at 90° C. under N$_2$ for 4 hours. The reaction mixture was diluted with EA (30 mL) and washed with brine. The organic phase was dried over anhydrous sodium sulfate and concentrated under vacuum. The residue was purified to afford the desired product tert-butyl 4-(2-(2,6-dioxopiperidin-3-yl)-1,3-dioxoisoindolin-4-yl)piperazine-1-carboxylate (DCM:EA=1:1) (1.4 g) as yellow solid. $^1$H NMR (400 MHz, DMSO-d6): δ 7.73 (d, J=7.2 Hz, 1H), 7.35-7.41 (m, 2H), 5.09-5.13 (m, 1H), 3.52 (s, 4H), 3.26 (s, 4H), 2.84-2.89 (m, 1H), 2.56-2.63 (m, 2H), 2.00-2.05 (m, 2H), 1.45 (s, 9H).

Step E: 2-(2,6-Dioxopiperidin-3-yl)-4-(piperazin-1-yl)isoindoline-1,3-dione Hydrochloride

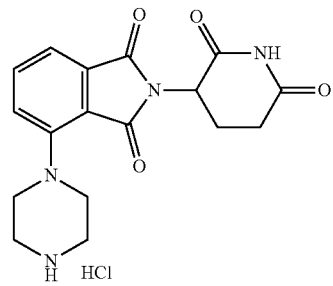 [SMILES: O=C1CCC(N2C(=O)c3cccc(N4CCNCC4)c3C2=O)C(=O)N1 ; Cl]

To a solution of tert-butyl 4-(2-(2,6-dioxopiperidin-3-yl)-1,3-dioxoisoindolin-4-yl)piperazine-1-carboxylate (1.4 g, 3.16 mmol) in 1,4-dioxane (4 mL) was added 6 M HCl in 1,4-dioxane (6 mL). The resulting solution was stirred at 25° C. for 1 hour. The solution was concentrated under reduced pressure. The residue afforded the desired product 2-(2,6-dioxopiperidin-3-yl)-4-(piperazin-1-yl)isoindoline-1,3-dione hydrochloride (1.4 g crude), which was used in next step without further purification. LCMS (ES$^+$): m/z 343.1 [M+H]$^+$.

Step F: 4-(4-(3-(2-(4-(4-bromo-3-(pyridin-4-yl)-1H-pyrazol-1-yl)phenoxy)ethoxy)propyl)piperazin-1-yl)-2-(2,6-dioxopiperidin-3-yl)isoindoline-1,3-dione

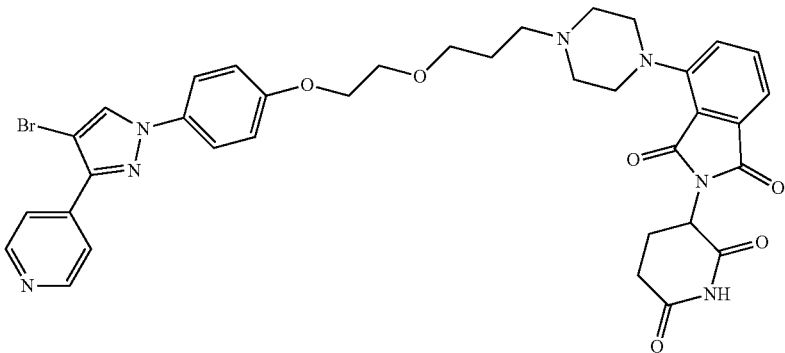 [SMILES: O=C1CCC(N2C(=O)c3cccc(N4CCN(CCCOCCOc5ccc(-n6cc(Br)c(-c7ccncc7)n6)cc5)CC4)c3C2=O)C(=O)N1]

To a solution of 3-(2-(4-(4-bromo-3-(pyridin-4-yl)-1H-pyrazol-1-yl)phenoxy)ethoxy)propanal (140 mg crude, 0.32 mmol), 2-(2,6-dioxopiperidin-3-yl)-4-(piperazin-1-yl)isoindoline-1,3-dione (123 mg, 0.32 mmol), NaBH$_3$CN (41 mg, 0.64 mmol), acetic acid (3.8 mg, 0.062 mmol) in MeOH. The resulting solution was stirred atrt for overnight. The mixture was diluted with EA, washed with water, and brine. The organic phase was dried over anhydrous sodium sulfate and concentrated under vacuum. The residue was purified to afford the desired product 4-(4-(3-(2-(4-(4-bromo-3-(pyridin-4-yl)-1H-pyrazol-1-yl)phenoxy)ethoxy)propyl)piperazin-1-yl)-2-(2,6-dioxopiperidin-3-yl)isoindoline-1,3-dione (DCM:MeOH=15:1) (70 mg) as yellow solid. LCMS (ES$^+$): m/z 742.1 [M+H]$^+$.

Step G: 2-(2,6-dioxopiperidin-3-yl)-4-(4-(3-(2-(4-(4-(1-oxo-2,3-dihydro-1H-inden-5-yl)-3-(pyridin-4-yl)-1H-pyrazol-1-yl)phenoxy)ethoxy)propyl)piperazin-1-yl)isoindoline-1,3-dione To a solution of 4-(4-(3-(2-(4-(4-bromo-3-(pyridin-4-yl)-1H-pyrazol-1-yl)phenoxy)ethoxy)propyl)piperazin-1-yl)-2-(2,6-dioxopiperidin-3-yl)isoindoline-1,3-dione (70 mg, 0.094 mmol), 5-(4,4,5,5-tetramethyl-1,3,2-dioxaborolan-2-yl)-2,3-dihydro-1H-inden-1-one (191 mg, 0.74 mmol), Pd$_2$(dba)$_3$ (181 mg, 0.198 mmol), CsF (300 mg, 1.97 mmol), tri-tert-butylphosphine tetrafluoroborate (115 mg, 0.39 mmol), N,N-dicyclohexylmethylamine (9 mg, 0.047 mmol) in 1,4-dioxane/H2O (6 mL, 10/1). The resulting solution was irradiated at 100° C. with microwave under N$_2$ for 2 hours. After cooling to room temperature, the mixture was diluted with EA, washed with water, and brine. The organic phase was dried over anhydrous sodium sulfate and concentrated under vacuum. The residue was purified to afford the desired product 2-(2,6-dioxopiperidin-3-yl)-4-(4-(3-(2-(4-(4-(1-oxo-2,3-dihydro-1H-inden-5-yl)-3-(pyridin-4-yl)-1H-pyrazol-1-yl)phenoxy)ethoxy)propyl)piperazin-1-yl)isoindoline-1,3-dione (DCM:MeOH=20:1) (33 mg) as yellow solid. LCMS (ES$^+$): m/z 795.3 [M+H]$^+$.

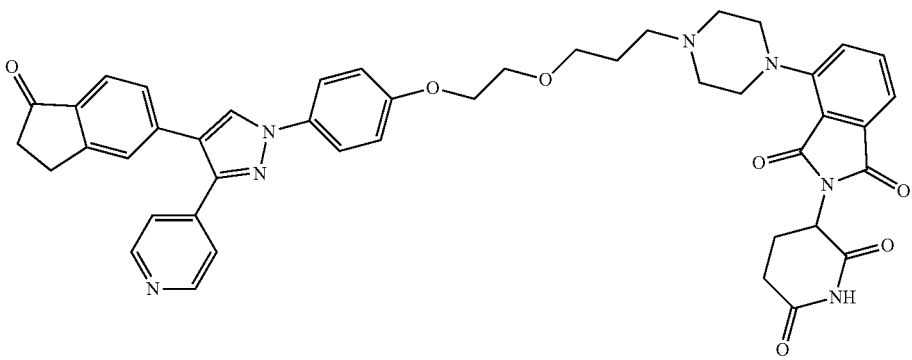 [SMILES: O=C1CCC(N2C(=O)c3cccc(N4CCN(CCCOCCOc5ccc(-n6cc(-c7ccc8c(c7)CCC8=O)c(-c7ccncc7)n6)cc5)CC4)c3C2=O)C(=O)N1]

Step H: (E)-2-(2,6-dioxopiperidin-3-yl)-4-(4-(3-(2-(4-(4-(1-(hydroxyimino)-2,3-dihydro-1H-inden-5-yl)-3-(pyridin-4-yl)-1H-pyrazol-1-yl)phenoxy)ethoxy)propyl)piperazin-1-yl)isoindoline-1,3-dione

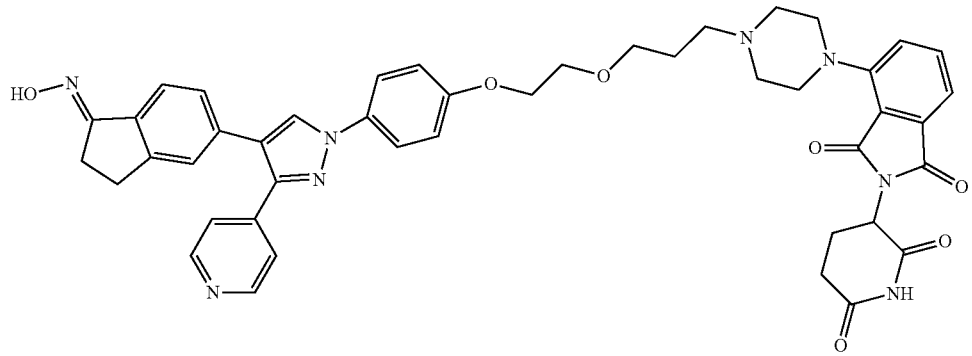 [SMILES: O=C1CCC(N2C(=O)c3cccc(N4CCN(CCCOCCOc5ccc(-n6cc(-c7ccc8c(c7)CC/C8=N\O)c(-c7ccncc7)n6)cc5)CC4)c3C2=O)C(=O)N1]

To a solution of 2-(2,6-dioxopiperidin-3-yl)-4-(4-(3-(2-(4-(4-(1-oxo-2,3-dihydro-1H-inden-5-yl)-3-(pyridin-4-yl)-1H-pyrazol-1-yl)phenoxy)ethoxy)propyl)piperazin-1-yl)isoindoline-1,3-dione (33 mg, 0.042 mmol) in acetonitrile (2 mL) and pyridine (1.5 mL), added hydroxylamine hydrochloride (27 mg, 0.42 mmol). The mixture was stirred at 40° C. for 20 minutes, and it was diluted with DCM 20 mL, washed with brine (10 mL). The organic layer was concentrated and purified by preparative TLC to afford (E)-2-(2,6-dioxopiperidin-3-yl)-4-(4-(3-(2-(4-(4-(1-(hydroxyimino)-2,3-dihydro-1H-inden-5-yl)-3-(pyridin-4-yl)-1H-pyrazol-1-yl)phenoxy)ethoxy)propyl)piperazin-1-yl)isoindoline-1,3-dione (22 mg, 66.6% yield) as yellow solid. $^1$H NMR (400 MHz, CDCl$_3$): δ 8.56 (d, J=5.6 Hz, 2H), 8.37 (s, 1H), 7.94 (s, 1H), 7.68 (d, J=9.2 Hz, 3H), 7.55-7.57 (m, 1H), 7.51 (d, J=5.6 Hz, 2H), 7.38-7.40 (m, 1H), 7.21-7.28 (m, 2H), 7.15 (d, J=8.4 Hz, 1H), 7.04 (d, J=8.8 Hz, 2H), 4.91-4.98 (m, 1H), 4.18 (d, J=4.8 Hz, 2H), 3.82-3.84 (m, 2H), 3.63 (d, J=6.4 Hz, 2H), 3.49 (s, 2H), 3.36-3.38 (m, 4H), 3.02 (d, J=10.8 Hz, 4H), 2.69-2.87 (m, 8H), 2.52-2.56 (m, 2H), 1.85-1.88 (m, 1H); LCMS (ES$^+$): m/z 810.2 [M+H]$^+$.

Compounds 151-172 and 282-284 may be prepared in an analogous manner.

Example Synthesis of Compound 174

Step A: 4-(benzyloxy)butyl 4-methylbenzenesulfonate

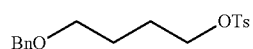

To a solution of 4-(benzyloxy)butyl 4-methylbenzenesulfonate (5 g, 27.76 mmol), DMAP (0.34 g, 2.78 mmol) and TEA (8.4 g, 83.28 mmol) in DCM (50 mL) was added TsCl (7.94 g, 41.64 mmol) batches. The resulting solution was stirred at 15° C. for 2 hours. The reaction was quenched by addition of saturated NH$_4$Cl (50 mL). The mixture was extracted with DCM (50 mL×2). The combined organic layer was dried over anhydrous sodium sulfate, concentrated under vacuum. The residue was purified by silica gel to afford desired product 4-(benzyloxy)butyl 4-methylbenzenesulfonate (5.6 g, 60% yield) as a light yellow oil. $^1$H NMR (400 MHz, CDCl$_3$): δ 7.77 (d, J=8.4 Hz, 2H), 7.26-7.33 (m, 7H), 4.45 (s, 2H), 4.05 (t, J=6.4 Hz, 2H), 3.42 (t, J=6.4 Hz, 2H), 2.44 (s, 3H), 1.59-1.78 (m, 4H).

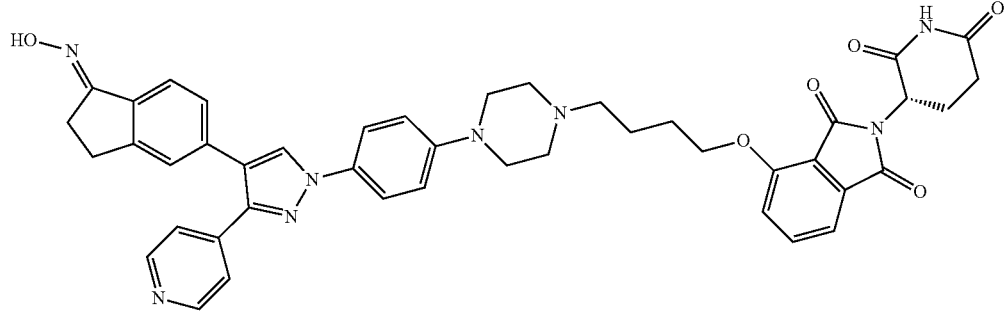 [SMILES: O=C1CC[C@H](N2C(=O)c3cccc(OCCCCN4CCN(c5ccc(-n6cc(-c7ccc8c(c7)CC/C8=N\O)c(-c7ccncc7)n6)cc5)CC4)c3C2=O)C(=O)N1]

Step B: (S)-tert-butyl 5-amino-4-(4-(4-(benzyloxy)butoxy)-1,3-dioxoisoindolin-2-yl)-5-oxopentanoate

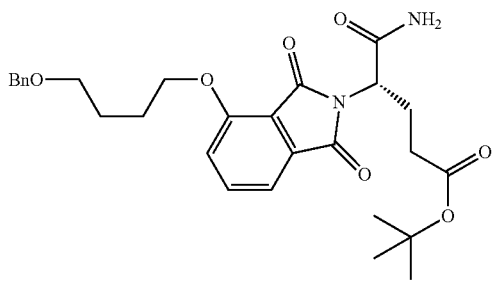 [SMILES: CC(C)(C)OC(=O)CC[C@@H](C(N)=O)N1C(=O)c2cccc(OCCCCOCc3ccccc3)c2C1=O]

To a solution of 4-(benzyloxy)butyl 4-methylbenzenesulfonate (0.63 g, 1.87 mmol) in dry DMF (8.0 mL) was added K$_2$CO$_3$ (0.4 g, 2.88 mmol), tert-butyl (S)-5-amino-4-(4-hydroxy-1,3-dioxoisoindolin-2-yl)-5-oxopentanoate (0.5 g, 1.44 mmol) subsequently. The resulting solution was stirred at 70° C. for 2 hours. After cooling to room temperature, the reaction was quenched with water (30 mL), and the mixture was extracted with EA (40 mL×2). The combined organic layer was washed with brine, dried over anhydrous sodium sulfate, concentrated under vacuum. The residue was purified by silica gel column to afford (S)-tert-butyl 5-amino-4-(4-(4-(benzyloxy)butoxy)-1,3-dioxoisoindolin-2-yl)-5-oxopentanoate (0.4 g, 55% yield). $^1$H NMR (400 MHz, CDCl$_3$): δ 7.63 (t, J=8.4 Hz, 1H), 7.43 (m, 1H), 7.25-7.40 (m, 5H), 7.18 (s, 1H), 6.41 (br, 1H), 5.66 (br, 1H), 4.79 (m, 1H), 4.52 (s, 2H), 4.19 (t, J=6.4 Hz, 2H), 3.58 (t, J=6.4 Hz, 2H), 3.47 (m, 2H), 2.50 (m, 2H), 2.25 (m, 2H), 2.00 (m, 2H), 1.85 (m, 1H), 1.43 (s, 9H).

Step C: (S)-2-(2,6-dioxopiperidin-3-yl)-4-(4-hydroxybutoxy)isoindoline-1,3-dione

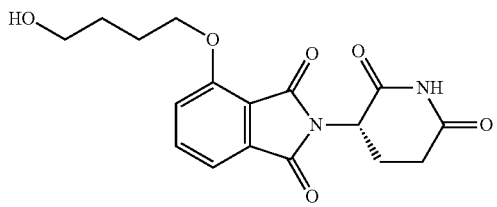 [SMILES: O=C1CC[C@H](N2C(=O)c3cccc(OCCCCO)c3C2=O)C(=O)N1]

To a solution of (S)-Tert-butyl 5-amino-4-(4-(4-(benzyloxy)butoxy)-1,3-dioxoisoindolin-2-yl)-5-oxopentanoate (400 mg, 0.784 mmol) in acetonitrile (5 mL) was added TsOH H$_2$O (1.48 g, 7.84 mmol). The resulting solution was stirred at 80° C. for 2 hours. The reaction was quenched by saturated NaHCO$_3$ and extracted with EA. The organic layer was dried over anhydrous sodium sulfate, concentrated and purified by column to afford (S)-4-(4-(benzyloxy)butoxy)-2-(2,6-dioxopiperidin-3-yl)isoindoline-1,3-dione (370 mg). To a solution of (S)-4-(4-(benzyloxy)butoxy)-2-(2,6-dioxopiperidin-3-yl)isoindoline-1,3-dione (370 mg, 0.85 mmol) in THF/MeOH (4 mL/1 mL) was added Pd(OH)$_2$ (185 mg) and two drops of concentrated HCl. The resulting mixture was stirred at 20° C. for 1 hour under H$_2$ 1 atm. The resulting solution was filtered and evaporated. The residue was purified by preparative TLC to afford the desired product (S)-2-(2,6-dioxopiperidin-3-yl)-4-(4-hydroxybutoxy)isoindoline-1,3-dione (250 mg, 92% yield in two steps). LCMS (ES$^+$, Neg): m/z 345.0 [M−H]$^+$.

Step D: (S)-4-((2-(2,6-Dioxopiperidin-3-yl)-1,3-dioxoisoindolin-4-yl)oxy)butanal

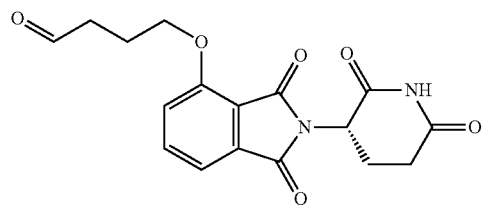 [SMILES: O=CCCCOc1cccc2c1C(=O)N([C@H]1CCC(=O)NC1=O)C2=O]

To a solution of (S)-2-(2,6-dioxopiperidin-3-yl)-4-(4-hydroxybutoxy)isoindoline-1,3-dione (0.25 g, 0.72 mmol) in CH$_3$CN (5 mL) was added IBX (607 mg, 2.16 mmol). The resulting solution was stirred at 75° C. for 1 hour. After cooling to room temperature, the reaction mixture was filtered and concentrated under vacuum to afford crude desired product (240 mg crude, calculated, 100% yield), which was used in next step directly.

Step E: (S)-4-(4-(4-(4-(4-Bromo-3-(pyridin-4-yl)-1H-pyrazol-1-yl)phenyl)piperazin-1-yl)butoxy)-2-(2,6-dioxopiperidin-3-yl)isoindoline-1,3-dione

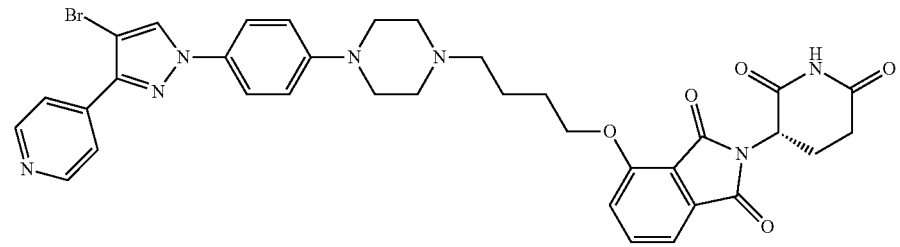 [SMILES: O=C1CC[C@H](N2C(=O)c3cccc(OCCCCN4CCN(c5ccc(-n6cc(Br)c(-c7ccncc7)n6)cc5)CC4)c3C2=O)C(=O)N1]

To a solution of (S)-4-((2-(2,6-dioxopiperidin-3-yl)-1,3-dioxoisoindolin-4-yl)oxy)butanal (240 mg crude, 0.72 mmol) in MeOH (6 mL) was added 1-(4-(4-bromo-3-(pyridin-4-yl)-1H-pyrazol-1-yl)phenyl)piperazine (276 mg, 0.72 mmol) and two drops of AcOH. Then NaBH₃CN (134 mg, 2.16 mmol) was added. The resulting solution was stirred at 18° C. for 2 hours. After quenched with water (30 mL), and the mixture was extracted with EA (40 mL×2). The combined organic layer was dried over anhydrous sodium sulfate and concentrated under vacuum. The residue was applied onto a silica gel column to afford desired product (S)-4-(4-(4-(4-(4-bromo-3-(pyridin-4-yl)-1H-pyrazol-1-yl)phenyl)piperazin-1-yl)butoxy)-2-(2,6-dioxopiperidin-3-yl)isoindoline-1,3-dione (350 mg, 68% yield in two steps). LCMS (ES⁺): m/z 713.1 [M+H]⁺.

Step F: (S)-2-(2,6-Dioxopiperidin-3-yl)-4-(4-(4-(4-(1-oxo-2,3-dihydro-1H-inden-5-yl)-3-(pyridin-4-yl)-1H-pyrazol-1-yl)phenyl)piperazin-1-yl)butoxy)isoindoline-1,3-dione

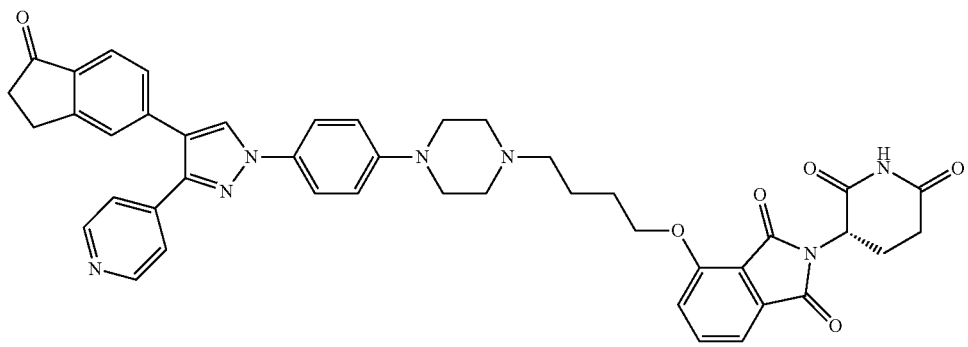 [SMILES: O=C1CC[C@H](N2C(=O)c3cccc(OCCCCN4CCN(c5ccc(-n6cc(-c7ccc8c(c7)CCC8=O)c(-c7ccncc7)n6)cc5)CC4)c3C2=O)C(=O)N1]

To a solution of (S)-4-(4-(4-(4-(4-bromo-3-(pyridin-4-yl)-1H-pyrazol-1-yl)phenyl)piperazin-1-yl)butoxy)-2-(2,6-dioxopiperidin-3-yl)isoindoline-1,3-dione (0.35 g, 0.52 mmol) and 5-(4,4,5,5-tetramethyl-1,3,2-dioxaborolan-2-yl)-2,3-dihydro-1H-inden-1-one (147 mg, 0.57 mmol) in 1,4-dioxane (15 mL)/H₂O (1.5 mL) was added CsF (316 mg, 2.08 mmol), Pd₂(dba)₃ (190 mg, 0.21 mmol). tri-tert-butylphosphine tetrafluoroborate (121 mg, 0.42 mmol) and two drops of N-cyclohexyl-N-methylcyclohexanamine subsequently. The reaction was heated to 100° C. for 2 hour under N₂ atmosphere. After cooling to room temperature, the reaction was quenched with water (20 mL), and the mixture was extracted with ethyl acetate (30 mL×2). The combined organic layer was dried over anhydrous sodium sulfate and concentrated under vacuum. The residue was applied onto a silica gel column to afford desired product (S)-2-(2,6-dioxopiperidin-3-yl)-4-(4-(4-(4-(4-(1-oxo-2,3-dihydro-1H-inden-5-yl)-3-(pyridin-4-yl)-1H-pyrazol-1-yl)phenyl)piperazin-1-yl)butoxy)isoindoline-1,3-dione (0.3 g, 80% yield) as yellow solid. LCMS (ES+): m/z 382.8 [(M+H)/2]⁺.

Step G: (S,E)-2-(2,6-dioxopiperidin-3-yl)-4-(4-(4-(4-(4-(1-(hydroxyimino)-2,3-dihydro-1H-inden-5-yl)-3-(pyridin-4-yl)-1H-pyrazol-1-yl)phenyl)piperazin-1-yl)butoxy)isoindoline-1,3-dione

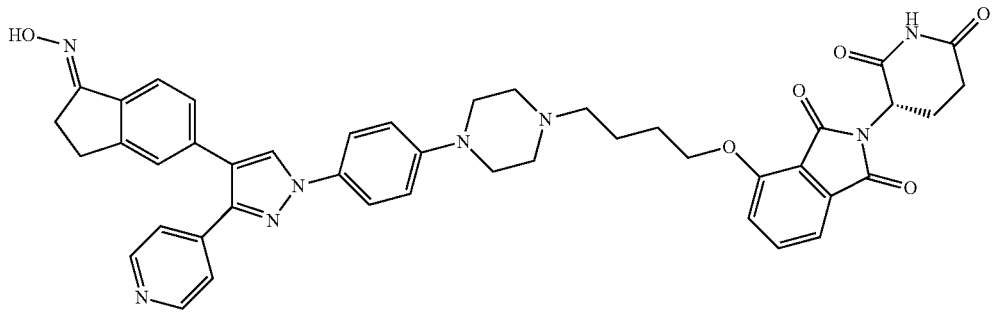 [SMILES: O=C1CC[C@H](N2C(=O)c3cccc(OCCCCN4CCN(c5ccc(-n6cc(-c7ccc8c(c7)CC/C8=N\O)c(-c7ccncc7)n6)cc5)CC4)c3C2=O)C(=O)N1]

To a solution of (S)-2-(2,6-dioxopiperidin-3-yl)-4-(4-(4-(4-(4-(1-oxo-2,3-dihydro-1H-inden-5-yl)-3-(pyridin-4-yl)-1H-pyrazol-1-yl)phenyl)piperazin-1-yl)butoxy)isoindoline-1,3-dione (165 mg, 0.22 mmol) in acetonitrile/pyridine (6 ml/3 ml) was added hydroxylamine hydrochloride (150 mg, 2.16 mmol). The mixture was stirred at 45° C. for 1 hour. The solvent was removed under vacuum, and the residue was purified by preparative TLC with DCM/MeOH (20/1) to afford the desired product (S,E)-2-(2,6-dioxopiperidin-3-yl)-4-(4-(4-(4-(4-(1-(hydroxyimino)-2,3-dihydro-1H-inden-5-yl)-3-(pyridin-4-yl)-1H-pyrazol-1-yl)phenyl)piperazin-1-yl)butoxy)isoindoline-1,3-dione (60 mg, 38% yield) as a white solid. $^1$H NMR (400 MHz, DMSO-d6): δ 11.11 (s, 1H), 10.88 (d, J=3.6 Hz, 1H), 8.69 (s, 1H), 8.56 (m, 2H), 7.81 (m, 3H), 7.35-7.62 (m, 6H), 7.20 (s, 1H), 7.09 (m, 2H), 5.10 (m, 1H), 4.25 (t, J=6.4 Hz, 2H), 3.32 (m, 4H), 3.19 (m, 4H), 2.75-3.05 (m, 5H), 2.40 (m, 2H), 1.60-2.10 (m, 8H); LCMS (ES+): m/z 779.3 [M+H]$^+$.

Compounds 173 and 175-181 may be prepared in an analogous manner.

Example Synthesis of Compound 182

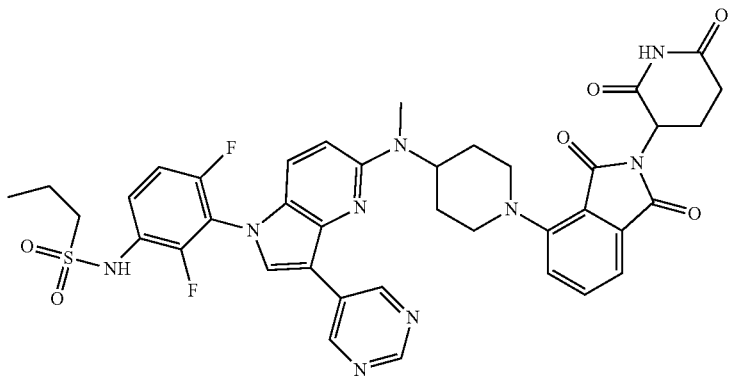 [SMILES: CCCS(=O)(=O)Nc1ccc(F)c(-n2cc(-c3cncnc3)c3nc(N(C)C4CCN(c5cccc6c5C(=O)N(C5CCC(=O)NC5=O)C6=O)CC4)ccc32)c1F]

Step A: N-(3-(5-((1-(2-(2,6-dioxopiperidin-3-yl)-1,3-dioxoisoindolin-4-yl)piperidin-4-yl)(methyl)amino)-3-(pyrimidin-5-yl)-1H-pyrrolo[3,2-b]pyridin-1-yl)-2,4-difluorophenyl)propane-1-sulfonamide

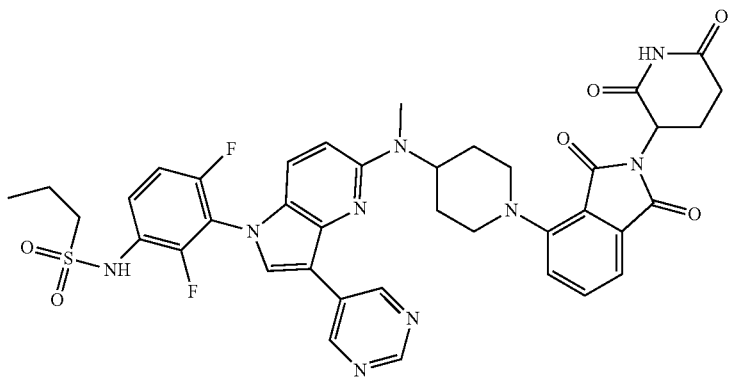 [SMILES: CCCS(=O)(=O)Nc1ccc(F)c(-n2cc(-c3cncnc3)c3nc(N(C)C4CCN(c5cccc6c5C(=O)N(C5CCC(=O)NC5=O)C6=O)CC4)ccc32)c1F]

A mixture of N-(2,4-difluoro-3-(5-(methyl(piperidin-4-yl)amino)-3-(pyrimidin-5-yl)-1H-pyrrolo[3,2-b]pyridin-1-yl)phenyl)propane-1-sulfonamide (100.0 mg, 0.18 mmol) (previously described in WO2012/104388), 2-(2,6-dioxopiperidin-3-yl)-4-fluoroisoindoline-1,3-dione (102 mg, 0.36 mmol), DIEA(239 mg, 1.80 mmol) in anhydrous NMP (2.0 mL) was radiated at 130° C. with microwave for 1 hour. After cooling to room temperature, the reaction was quenched with water, and the mixture was extracted with EA (10 mL×3). The combined organic layer was washed with water (10 mL×3), brine (20 mL), dried over anhydrous sodium sulfate and concentrated under vacuum. The residue was purified by preparative TLC to afford the desired product N-(3-(5-((1-(2-(2,6-dioxopiperidin-3-yl)-1,3-dioxoisoindolin-4-yl)piperidin-4-yl)(methyl)amino)-3-(pyrimidin-5-yl)-1H-pyrrolo[3,2-b]pyridin-1-yl)-2,4-difluorophenyl)propane-1-sulfonamide (DCM:MeOH=10:1) (45 mg, yield=30.6%) as white solid. $^1$H NMR (400 MHz, CDCl$_3$): δ 9.58 (s, 1H), 9.10 (s, 1H), 8.03 (s, 1H), 7.67-7.59 (m, 2H), 7.42 (d, J=7.2 Hz, 1H), 7.34 (d, J=8 Hz, 1H), 7.23-7.18 (m, 1H), 6.66 (d, J=12 Hz, 1H), 5.02-4.81 (m, 1H), 3.90-3.89 (m, 1H), 3.18-3.14 (m, 3H), 3.05 (s, 2H), 2.96-2.87 (m, 3H), 2.13 (dd, J=2.8 Hz, 4 Hz, 2H), 2.00-1.90 (m, 3H), 1.30 (s, 8H), 1.09 (t, J=12.0 Hz, 3H), 0.84-0.088 (m, 4H); LCMS (ES$^+$): m/z 798.2 [M+H]$^+$.

Compound 183 may be prepared in an analogous manner.

Example Synthesis of Compound 184

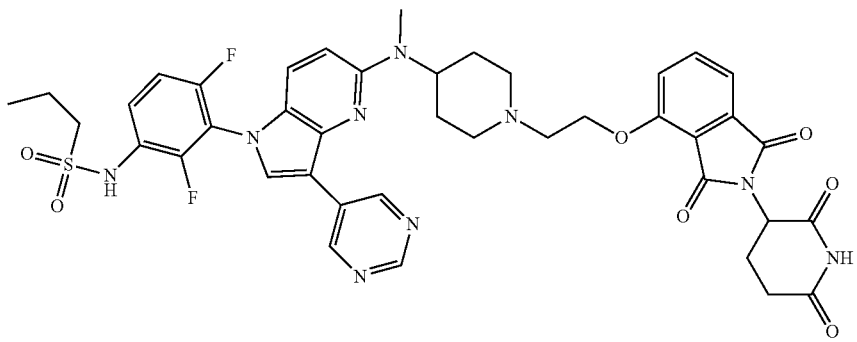 [SMILES: CCCS(=O)(=O)Nc1ccc(F)c(-n2cc(-c3cncnc3)c3nc(N(C)C4CCN(CCOc5cccc6c5C(=O)N(C5CCC(=O)NC5=O)C6=O)CC4)ccc32)c1F]

Step A: tert-butyl (S)-5-amino-4-(4-(2-(benzyloxy)ethoxy)-1,3-dioxoisoindolin-2-yl)-5-oxopentanoate

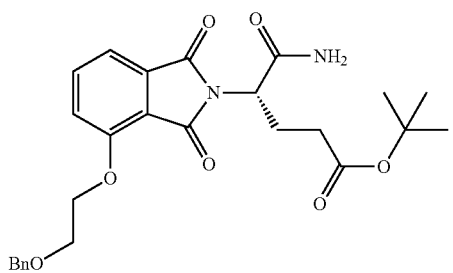 [SMILES: CC(C)(C)OC(=O)CC[C@@H](C(N)=O)N1C(=O)c2cccc(OCCOCc3ccccc3)c2C1=O]

A mixture of tert-butyl (S)-5-amino-4-(4-hydroxy-1,3-dioxoisoindolin-2-yl)-5-oxopentanoate (1.22 g, 3.51 mmol), 2-(benzyloxy)ethyl methanesulfonate (900 mg, 3.91 mmol), K$_2$CO$_3$(1.08 g, 7.83 mmol) in DMF (10 mL) was stirred at 70° C. for 6 hours. After quenched with water, the mixture was extracted with EA. The organic phase was dried over anhydrous sodium sulfate and concentrated under vacuum. The residue was purified to afford the desired product tert-butyl (S)-5-amino-4-(4-(2-(benzyloxy)ethoxy)-1,3-dioxoisoindolin-2-yl)-5-oxopentanoate (PE:EtOAc=1:5) (907 mg).

Step B: (S)-4-(2-(benzyloxy)ethoxy)-2-(2,6-dioxopiperidin-3-yl)isoindoline-1,3-dione

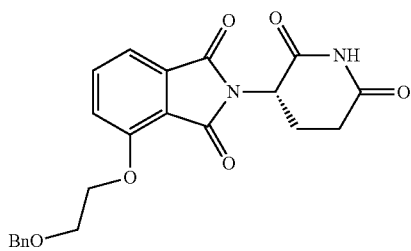 [SMILES: O=C1CC[C@H](N2C(=O)c3cccc(OCCOCc4ccccc4)c3C2=O)C(=O)N1]

To a solution of tert-butyl (S)-5-amino-4-(4-(2-(benzyloxy)ethoxy)-1,3-dioxoisoindolin-2-yl)-5-oxopentanoate (907 mg, 1.88 mmol), p-TsOH (1.5 g, 7.89 mmol) in MeCN (10 mL) was stirred with at 80° C. for 8 hours. After quenched with water, the mixture was diluted with EA, washed with water, brine. The organic phase was dried over anhydrous sodium sulfate and concentrated under vacuum. The residue was purified to afford the desired product (S)-4-(2-(benzyloxy)ethoxy)-2-(2,6-dioxopiperidin-3-yl)isoindoline-1,3-dione (PE:EtOAc=1:1) (1.23 g, crude).

Step C: (S)-2-(2,6-dioxopiperidin-3-yl)-4-(2-hydroxyethoxy)isoindoline-1,3-dione

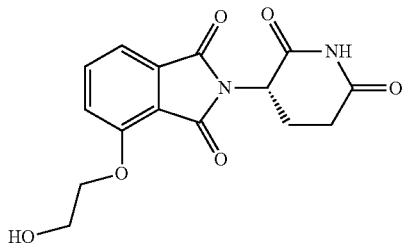 [SMILES: O=C1CC[C@H](N2C(=O)c3cccc(OCCO)c3C2=O)C(=O)N1]

To a solution of (S)-4-(2-(benzyloxy)ethoxy)-2-(2,6-dioxopiperidin-3-yl) isoindoline-1,3-dione (1.23 g, 3.01 mmol), Pd(OH)$_2$/C(0.7 g), HCl/dioxane (6N, 6 drops) in MeOH/EtOAc (1:1, 40 mL) was stirred with at room temperature for 12 hours under H$_2$ 1 atm. The mixture was filtered through Celite and the filtrate was concentrated under vacuum to afford the desired product (S)-2-(2,6-dioxopiperidin-3-yl)-4-(2-hydroxyethoxy)isoindoline-1,3-dione (700 mg, crude).

Step D: (S)-2-((2-(2,6-dioxopiperidin-3-yl)-1,3-dioxoisoindolin-4-yl)oxy)acetaldehyde

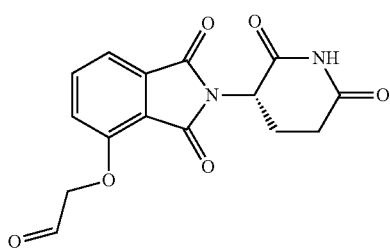 [SMILES: O=CCOc1cccc2c1C(=O)N([C@H]1CCC(=O)NC1=O)C2=O]

To a solution of (S)-2-(2,6-dioxopiperidin-3-yl)-4-(2-hydroxyethoxy)isoindoline-1,3-dione (200 mg, 0.63 mmol) in CH₃CN (10 mL) was added IBX (352 mg, 1.26 mmol). The resulting solution was stirred at 80° C. for 2 hours. After cooling to room temperature, the mixture was filtered, and the filtrate was concentrated under vacuum to afford crude desired product (S)-2-((2-(2,6-dioxopiperidin-3-yl)-1,3-dioxoisoindolin-4-yl)oxy) acetaldehyde (200 mg crude) as yellow solid, which was used into next reaction without further purification.

Step E: N-(3-(5-((1-(2-((2-(2,6-dioxopiperidin-3-yl)-1,3-dioxoisoindolin-4-yl)oxy)ethyl)piperidin-4-yl)(methyl)amino)-3-(pyrimidin-5-yl)-1H-pyrrolo[3,2-b]pyridin-1-yl)-2,4-difluorophenyl)propane-1-sulfonamide

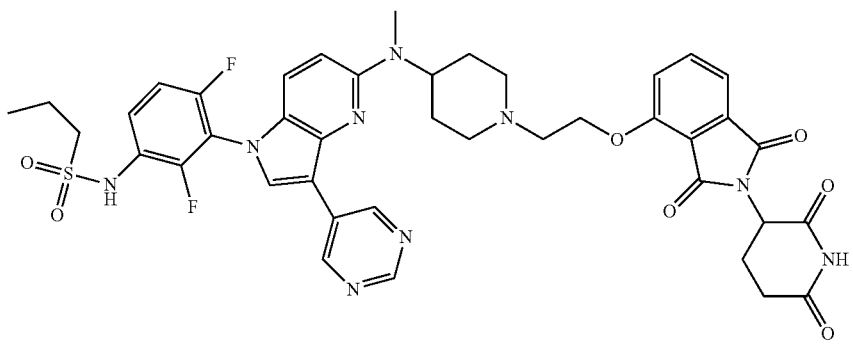 [SMILES: CCCS(=O)(=O)Nc1ccc(F)c(-n2cc(-c3cncnc3)c3nc(N(C)C4CCN(CCOc5cccc6c5C(=O)N(C5CCC(=O)NC5=O)C6=O)CC4)ccc32)c1F]

To a solution of (S)-2-((2-(2,6-dioxopiperidin-3-yl)-1,3-dioxoisoindolin-4-yl)oxy)acetaldehyde (200 mg crude, 0.631 mmol), N-(2,4-difluoro-3-(5-(methyl (piperidin-4-yl) amino)-3-(pyrimidin-5-yl)-1H-pyrrolo[3,2-b]pyridin-1-yl) phenyl)propane-1-sulfonamide hydrochloride (80 mg, 0.148 mmol), CH₃COOH (3.8 mg, 0.062 mmol) in EtOH/DCM (v/v=1/1, 20 mL) was added NaBH(OAc)₃ (400 mg, 1.88 mmol). The resulting solution was stirred at room temperature overnight. After quenched with water, the mixture was extracted with EtOAc. The organic phase was dried over anhydrous sodium sulfate and concentrated under vacuum. The residue was purified by prep-TLC (DCM/EtOAc/MeOH=10/1/1) to afford the desired product (S)—N-(3-(5-((1-(2-((2-(2,6-dioxopiperidin-3-yl)-1,3-dioxoisoindolin-4-yl)-oxy)ethyl)piperidin-4-yl)(methyl)amino)-3-(pyrimidin-5-yl)-1H-pyrrolo[3,2-b]pyridin-1-yl)-2,4-difluorophenyl) propane-1-sulfonamide (20.1 mg) as white solid. ¹H NMR (400 MHz, DMSO-d₆) δ 11.07 (s, 1H), 9.80-10.02 (m, 1H), 9.66 (s, 1H), 9.01 (s, 1H), 8.40 (s, 1H), 7.80-7.89 (m, 1H), 7.61-7.63 (m, 2H), 7.44-7.48 (m, 2H), 6.76 (d, J=9.3 Hz, 1H), 5.08 (dd, J=12.9, 5.2 Hz, 1H), 4.33-4.49 (m, 3H), 3.45 (s, 6H), 3.06-3.25 (m, 3H), 2.94 (s, 2H), 2.83 (s, 2H), 2.55-2.73 (m, 4H), 2.29 (d, J=10.3 Hz, 2H), 1.77 (m, 2H), 1.68 (d, J=10.1 Hz, 2H), 0.99 (t, J=7.4 Hz, 3H); LC-MS: (ES⁺): m/z 842.3 [M+H]⁺.

Compounds 185-189 may be prepared in an analogous manner.

Example Synthesis of Compound 191

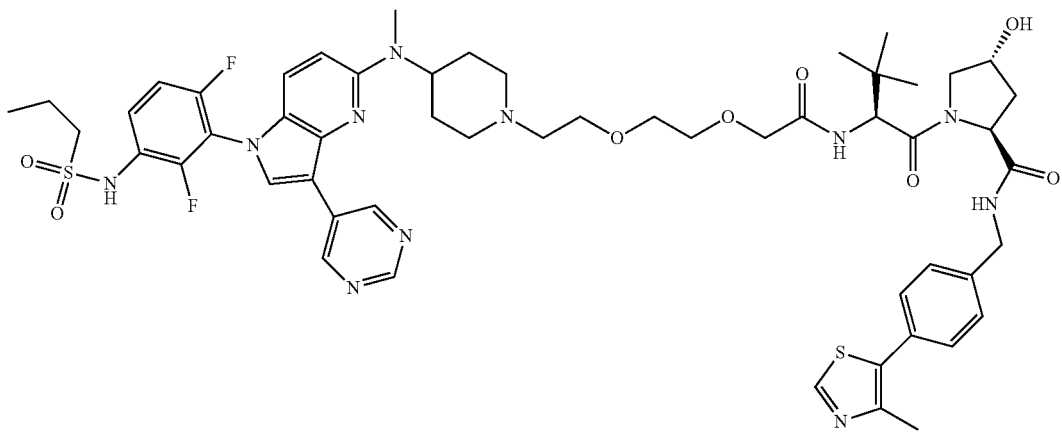 [SMILES: CCCS(=O)(=O)Nc1ccc(F)c(-n2cc(-c3cncnc3)c3nc(N(C)C4CCN(CCOCCOCC(=O)N[C@H](C(=O)N5C[C@H](O)C[C@H]5C(=O)NCc5ccc(-c6scnc6C)cc5)C(C)(C)C)CC4)ccc32)c1F]

Step A: tert-butyl 2-(2-(2-oxoethoxy)ethoxy)acetate

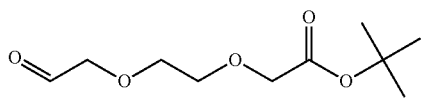

To a solution of tert-butyl 2-(2-(2-hydroxyethoxy)ethoxy)acetate (1 g, 4.55 mmol) in CH$_3$CN (15 mL) was added IBX (3.8 g, 13.64 mmol). The resulting solution was stirred at 75° C. for 1 hour. After cooling to room temperature, the mixture was filtered and the filtrate was concentrated under vacuum to afford crude desired product tert-butyl 2-(2-(2-oxoethoxy)ethoxy)acetate (1 g crude, 100% yield), which was used in next step directly. $^1$H NMR (400 MHz, CDCl$_3$): δ 9.75 (s, 1H), 4.18 (s, 2H), 4.03 (s, 2H), 3.77 (s, 4H), 1.48 (s, 9H).

Step B: tert-butyl-2-(2-(2-(4-((1-(2,6-difluoro-3-(propylsulfonamido)phenyl)-3-(pyrimidin-5-yl)-1H-pyrrolo[3,2-b]pyridin-5-yl)(methyl)amino)piperidin-1-yl)ethoxy)ethoxy)acetate To a solution of tert-butyl 2-(2-(2-oxoethoxy)ethoxy)acetate (181 mg crude, 0.83 mmol) in EtOH/DCM (1/1) was added N-(2,4-difluoro-3-(5-(methyl(piperidin-4-yl)amino)-3-(pyrimidin-5-yl)-1H-pyrrolo[3,2-b]pyridin-1-yl)phenyl) propane-1-sulfonamide hydrochloride (150 mg, 0.28 mmol) and cat. AcOH. KOAc was added if pH was below 5-6. After stirring for 30 minutes, NaBH(OAc)$_3$ (235 mg, 1.11 mmol) was added. The resulting solution was stirred at 30° C. for 1 hour. After quenched with water (20 mL), the mixture was extracted with DCM (30 mL×2). The combined organic layer was dried over anhydrous sodium sulfate and concentrated under vacuum. The residue was applied onto a silica gel column to afford desired product 2-(2-(2-(4-((1-(2,6-difluoro-3-(propylsulfonamido)phenyl)-3-(pyrimidin-5-yl)-1H-pyrrolo[3,2-b]pyridin-5-yl)(methyl)amino)piperidin-1-yl)ethoxy)ethoxy)acetate (120 mg, 58% yield). LCMS: (ES$^+$): m/z 744.3 [M+H]$^+$.

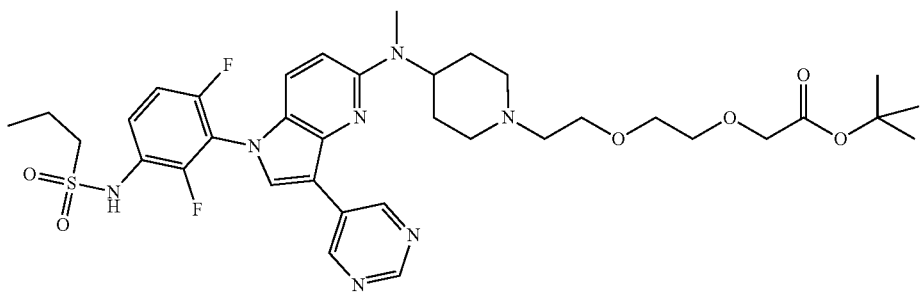 [SMILES: CCCS(=O)(=O)Nc1ccc(F)c(-n2cc(-c3cncnc3)c3nc(N(C)C4CCN(CCOCCOCC(=O)OC(C)(C)C)CC4)ccc32)c1F]

Step C: 2-(2-(2-(4-((1-(2,6-difluoro-3-(propylsulfonamido)phenyl)-3-(pyrimidin-5-yl)-1H-pyrrolo[3,2-b]pyridin-5-yl)(methyl)amino)piperidin-1-yl)ethoxy)ethoxy)acetic acid

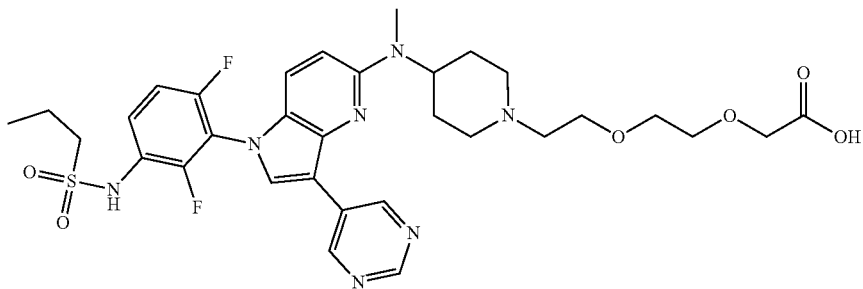 [SMILES: CCCS(=O)(=O)Nc1ccc(F)c(-n2cc(-c3cncnc3)c3nc(N(C)C4CCN(CCOCCOCC(=O)O)CC4)ccc32)c1F]

To a solution of tert-butyl 2-(2-(2-(4-((1-(2,6-difluoro-3-(propylsulfonamido)phenyl)-3-(pyrimidin-5-yl)-1H-pyrrolo[3,2-b]pyridin-5-yl)(methyl)amino)piperidin-1-yl)ethoxy)ethoxy)acetate (0.12 g, 0.16 mmol) in DCM (3 mL) was added TFA (1 mL). The resulting solution was stirred at 30° C. for 1 hour. The solvent was removed under vacuum to afford the desired product 2-(2-(2-(4-((1-(2,6-difluoro-3-(propylsulfonamido)phenyl)-3-(pyrimidin-5-yl)-1H-pyrrolo[3,2-b]pyridin-5-yl)(methyl)amino)piperidin-1-yl)ethoxy)ethoxy)acetic acid (111 mg crude, calculated), which was used into next reaction without further purification. LCMS: (ES+): m/z 688.2 [M+H]+.

Step D: (2S,4R)-1-((S)-2-(2-(2-(2-(4-((1-(2,6-difluoro-3-(propylsulfonamido)phenyl)-3-(pyrimidin-5-yl)-1H-pyrrolo[3,2-b]pyridin-5-yl)(methyl)amino)piperidin-1-yl)ethoxy)ethoxy)acetamido)-3,3-dimethylbutanoyl)-4-hydroxy-N-(4-(4-methylthiazol-5-yl)benzyl)pyrrolidine-2-carboxamide To a solution of 2-(2-(2-(4-((1-(2,6-difluoro-3-(propylsulfonamido)phenyl)-3-(pyrimidin-5-yl)-1H-pyrrolo[3,2-b]pyridin-5-yl)(methyl)amino)piperidin-1-yl)ethoxy)ethoxy)acetic acid (111 mg crude, 0.16 mmol) in DCM (10 mL) was added (2S,4R)-1-((S)-2-amino-3,3-dimethylbutanoyl)-4-hydroxy-N-(4-(4-methylthiazol-5-yl)benzyl)pyrrolidine-2-carboxamide hydrochloride (150 mg, 0.32 mmol), DIPEA (209 mg, 1.62 mmol) and PyBOP (250 mg, 0.48 mmol) subsequently. After stirring at 30° C. for 1 hour, the reaction mixture was diluted with DCM (30 mL), washed with water (10 mL×2), brine (10 mL). The organic phase was dried over anhydrous sodium sulfate and concentrated under vacuum. The residue was purified by column (DCM/MeOH 19/1) first and further purified by prep-HPLC to afford the desired product (2S,4R)-1-((S)-2-(2-(2-(2-(4-((1-(2,6-difluoro-3-(propylsulfonamido)phenyl)-3-(pyrimidin-5-yl)-1H-pyrrolo[3,2-b]pyridin-5-yl)(methyl)amino)piperidin-1-yl)ethoxy)ethoxy)acetamido)-3,3-dimethylbutanoyl)-4-hydroxy-N-(4-(4-methylthiazol-5-yl)benzyl)pyrrolidine-2-carboxamide (55 mg, 31% yield in two steps) as white solid. $^1$H NMR (400 MHz, DMSO-d$_6$): δ 9.65 (s, 2H), 9.02 (s, 1H), 8.94 (s, 1H), 8.57 (t, J=4.8 Hz, 1H), 8.40 (m, 1H), 7.55-7.65 (m, 1H), 7.35-7.50 (m, 7H), 6.74 (d, J=9.2 Hz, 1H), 4.57 (d, J=9.6 Hz, 1H), 4.20-4.50 (m, 5H), 4.00 (s, 2H), 3.50-3.70 (m, 2H), 3.00-3.20 (m, 7H), 2.93 (s, 3H), 2.50-2.70 m, 4H), 2.43 (s, 3H), 1.60-2.25 (m, 13H), 0.90-1.05 (m, 12H); LCMS: (ES+): m/z 1101.4 [M+H]+.

Compounds 190 and 192 may be prepared in an analogous manner.

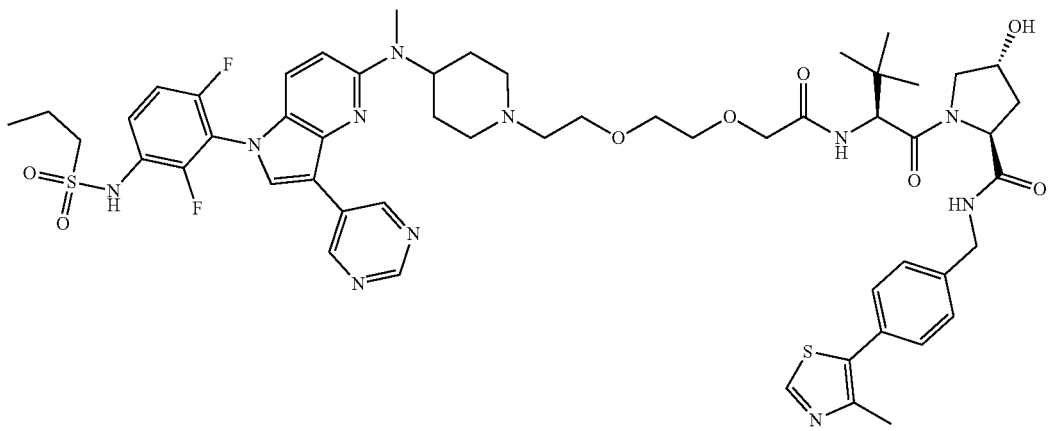 [SMILES: CCCS(=O)(=O)Nc1ccc(F)c(-n2cc(-c3cncnc3)c3nc(N(C)C4CCN(CCOCCOCC(=O)N[C@H](C(=O)N5C[C@H](O)C[C@H]5C(=O)NCc5ccc(-c6scnc6C)cc5)C(C)(C)C)CC4)ccc32)c1F]

Example Synthesis of Compound 195 [(3R)—N-(3-5-(4-(2-(2-(2,6-dioxopiperidin-3-yl)-1,3-dioxoisoindolin-5-yloxy)ethoxy)phenyl)-1H-pyrrolo[2,3-b]pyridine-3-carbonyl)-2,4-difluorophenyl)-3-fluoropyrrolidine-1-sulfonamide]

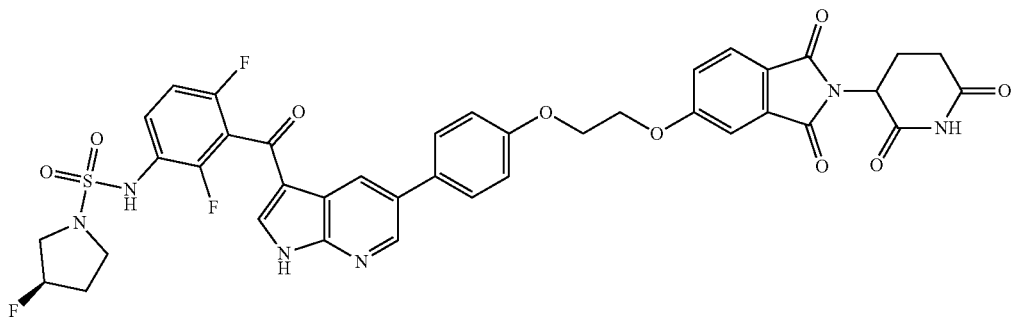 [SMILES: O=C1CCC(N2C(=O)c3ccc(OCCOc4ccc(-c5cnc6[nH]cc(C(=O)c7c(F)ccc(NS(=O)(=O)N8CC[C@@H](F)C8)c7F)c6c5)cc4)cc3C2=O)C(=O)N1]

Step A: ethyl 2-(4-(4,4,5,5-tetramethyl-1,3,2-dioxaborolan-2-yl)phenoxy)acetate

Step B: methyl 2-(4-(4,4,5,5-tetramethyl-1,3,2-dioxaborolan-2-yl)phenoxy)ethanol

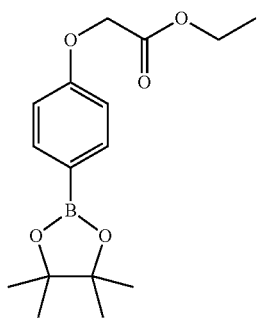 [SMILES: CCOC(=O)COc1ccc(B2OC(C)(C)C(C)(C)O2)cc1]

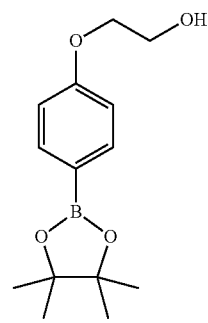 [SMILES: CC1(C)OB(c2ccc(OCCO)cc2)OC1(C)C]

To a solution of 4-(4,4,5,5-tetramethyl-1,3,2-dioxaborolan-2-yl)phenol (5 g, 22.7 mmol) in N,N-dimethylformamide (50 mL) was added ethyl 2-bromoacetate (4.52 g, 27.2 mmol) and potassium carbonate (6.27 g, 45.4 mmol). The mixture was stirred overnight under nitrogen gas. The reaction mixture was added to water (200 mL), and extracted with ethyl acetate (150 mL×3). The organic layer was washed with brine (100 mL×3). The combined organic phases were dried over anhydrous sodium sulfate, filtered, and concentrated in vacuo to give ethyl 2-(4-(4,4,5,5-tetramethyl-1,3,2-dioxaborolan-2-yl)phenoxy)acetate (5.2 g, 75%) as colorless oil.

To a solution of ethyl 2-(4-(4,4,5,5-tetramethyl-1,3,2-dioxaborolan-2-yl)phenoxy)acetate (1 g, 3.27 mmol) in tetrahydrofuran/ethanol (10 mL/10 mL) was added sodium borohydride (124 mg, 3.27 mmol) under ice-water bath. The mixture was allowed to warm to room temperature and stirred for 2 hours. The mixture was partitioned between ethyl acetate (100 mL) and water (50 mL). The organic layer was separated, washed with brine (20 mL×3), dried over anhydrous sodium sulfate, filtered, and concentrated in vacuo to give methyl 2-(4-(4,4,5,5-tetramethyl-1,3,2-dioxaborolan-2-yl)phenoxy)ethanol (0.8 g, 93%) as colorless oil.

Step C: 2-(4-(4,4,5,5-tetramethyl-1,3,2-dioxaborolan-2-yl)phenoxy)ethyl methanesulfonate

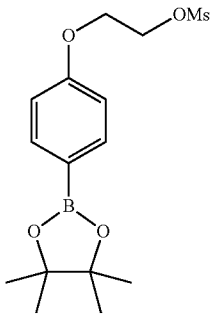 [SMILES: CC1(C)OB(c2ccc(OCCOS(C)(=O)=O)cc2)OC1(C)C]

To a solution of 2-(4-(4,4,5,5-tetramethyl-1,3,2-dioxaborolan-2-yl)phenoxy)ethanol (200 mg, 0.76 mmol) and ehyldiisopropylamine (293 mg, 2.27 mol) in dichloromethane (10.0 mL) was added methanesulfonyl chloride (105 mg, 0.91 mmol) under cooling, and the mixture was stirred at 0° C. for 30 minutes. The mixture was quenched with cold water (10.0 mL), the organic layer was washed with sodium bicarbonate solution (10.0 mL×3) and brine (10.0 mL×3), dried over anhydrous saturated sodium sulfate, filtered and concentrated in vacuo to afford (2-(4-(4,4,5,5-tetramethyl-1,3,2-dioxaborolan-2-yl)phenoxy)ethyl methanesulfonate which was used for next step directly.

Step D: 2-(2,6-dioxopiperidin-3-yl)-5-(2-(4-(4,4,5,5-tetramethyl-1,3,2-dioxaborolan-2-yl)phenoxy)ethoxy)isoindoline-1,3-dione

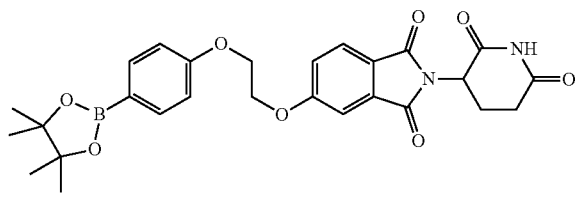 [SMILES: CC1(C)OB(c2ccc(OCCOc3ccc4c(c3)C(=O)N(C3CCC(=O)NC3=O)C4=O)cc2)OC1(C)C]

The mixture of (2-(4-(4,4,5,5-tetramethyl-1,3,2-dioxaborolan-2-yl)phenoxy)ethyl methanesulfonate (260 mg, 0.76 mmol), potassium carbonate (210 mg, 1.52 mol), potassium iodide (126 mg, 0.76 mmol) and 2-(2,6-dioxopiperidin-3-yl)-5-hydroxyisoindoline-1,3-dione (208 mg, 0.76 mmol) in dimethyl sulfoxide (10 mL) was stirred at 60° C. overnight. The resulting mixture was cooled down to room temperature. Water (20 mL) and ethyl acetate (20 mL) was added. The organic layer was separated, washed with brine (10 mL×2), dried over anhydrous sodium sulfate, filtered, and concentrated in vacuo to give the crude product which was purified by pre-TLC(dichloromethane/methanol=20:1) to give 2-(2,6-dioxopiperidin-3-yl)-5-(2-(4-(4,4,5,5-tetramethyl-1,3,2-dioxaborolan-2-yl)phenoxy)ethoxy)isoindoline-1,3-dione (140 mg, 36% two steps) as a white solid. LCMS (ES+): m/z 521.2 [M+H]+, 538.2 [M+18]+.

Step E: (3R)—N-(3-(5-(4-(2-(2-(2,6 dioxopiperidin-3-yl)-1,3-dioxoisoindolin-5-yloxy)ethoxy)phenyl)-1H-pyrrolo[2,3-b]pyridine-3-carbonyl)-2,4-difluorophenyl)-3-fluoropyrrolidine-1-sulfonamide

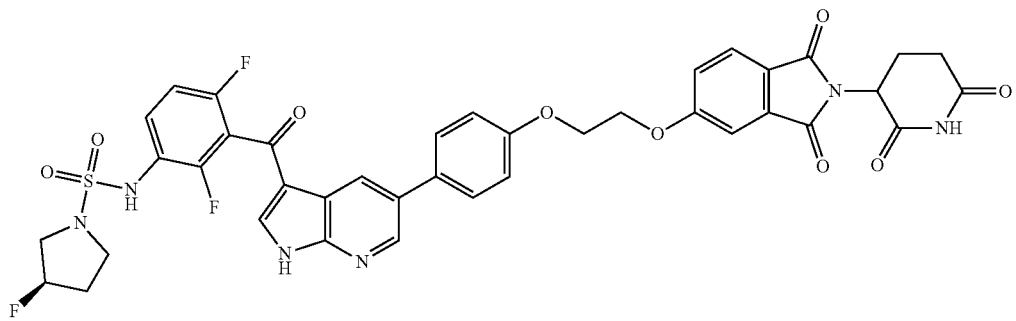 [SMILES: O=C1CCC(N2C(=O)c3ccc(OCCOc4ccc(-c5cnc6[nH]cc(C(=O)c7c(F)ccc(NS(=O)(=O)N8CC[C@@H](F)C8)c7F)c6c5)cc4)cc3C2=O)C(=O)N1]

To a solution of 2-(2,6-dioxopiperidin-3-yl)-5-(2-(4-(4,4,5,5-tetramethyl-1,3,2-dioxaborolan-2-yl)phenoxy)ethoxy)isoindoline-1,3-dione (136 mg, 0.26 mmol), (R)—N-(3-(5-bromo-1H-pyrrolo[2,3-b]pyridine-3-carbonyl)-2,4-difluorophenyl)-3-fluoropyrrolidine-1-sulfonamide (120 mg, 0.24 mmol) and CsF (0.18 mg, 0.012 mmol) in 1,4-dioxane (10 mL) and water (2 mL) was added Pd(aMPhos)Cl₂ (17 mg, 0.024 mmol) under argon atmosphere, and the mixture was stirred at 100° C. for 6 hours. When it was cooled to room temperature, water (20 mL) was added and the resultant mixture was extracted by EA (20 mL×3), washed by brine (10 mL×3), dried over anhydrous sodium sulfate, filtered and concentrated. The residue was purified by pre-HPLC to give (3R)—N-(3-(5-(4-(2-(2-(2,6-dioxopiperidin-3-yl)-1,3-dioxoisoindolin-5-yloxy)ethoxy)phenyl)-1H-pyrrolo[2,3-b]pyridine-3-carbonyl)-2,4-difluorophenyl)-3-fluoropyrrolidine-1-sulfonamide (8.1 mg, 4% yield) as a white solid. LCMS (ES+): m/z 817.2 [M+H]+; ¹H NMR (400 MHz, DMSO-d₆) δ 2.06-2.09 (3H, m), 2.55-2.62 (2H, m), 2.85-2.93 (1H, m), 3.24-3.27 (1H, m), 3.38-3.50 (3H, m), 4.42-4.46 (2H, m), 4.58-4.62 (2H, m), 5.12-5.16 (1H, m), 5.23-5.36 (1H, m), 7.15 (2H, d, J=8.8 Hz), 7.25 (1H, t, J=8.8 Hz), 7.45 (1H, dd, J=2.4, 8.4 Hz), 7.55 (1H, d, J=2.0 Hz), 7.59-7.63 (1H, m), 7.70 (2H, d, J=8.4 Hz), 7.87 (1H, d, J=8.4 Hz), 8.10 (1H, s), 8.58 (1H, s), 8.68 (1H, d, J=2.4 Hz), 9.89 (1H, brs.), 11.14 (1H, s), 12.96 (1H, brs.).

Compounds 194 and 195 may be prepared in an analogous manner.

Example Synthesis of Compound 285 [(2S,4R)-1-((S)-2-(3-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide] and compound 286 [(2S,4R)-1-((R)-2-(3-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide]

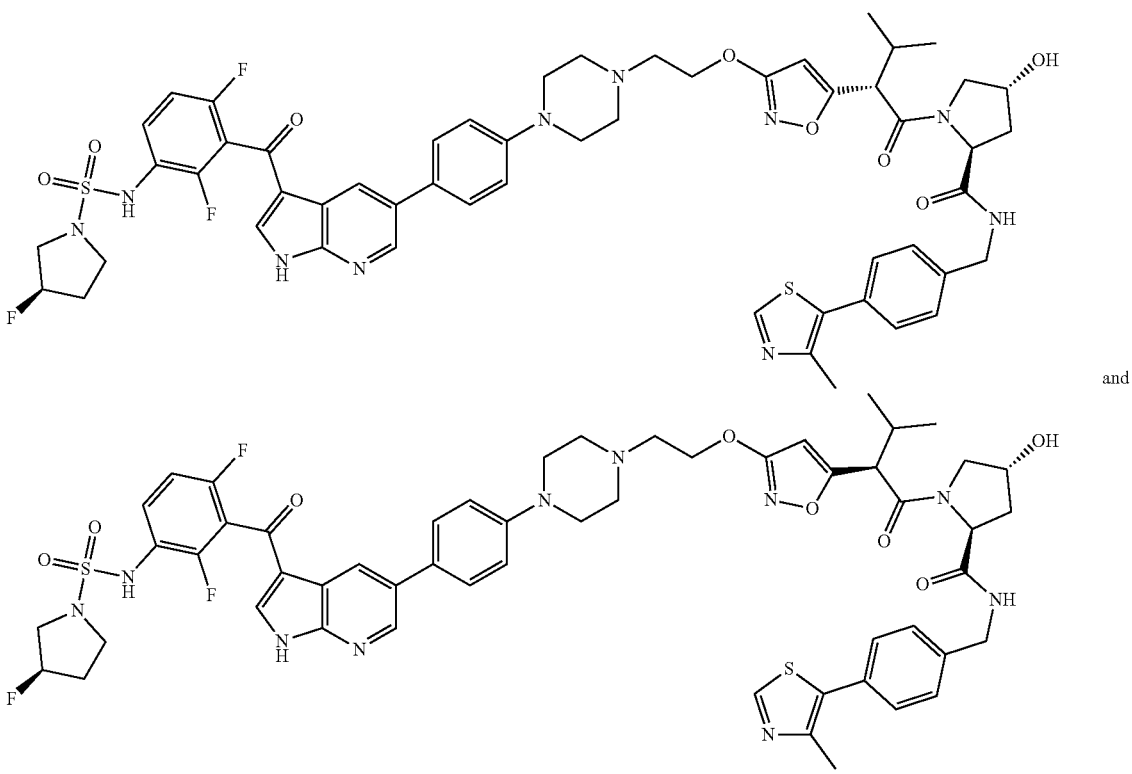

and

Step A:
2-(3-hydroxy-1,2-oxazol-5-yl)-3-methylbutanoic acid

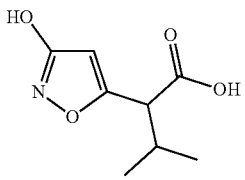

Step B: ethyl 2-(3-hydroxy-1,2-oxazol-5-yl)-3-methylbutanoate

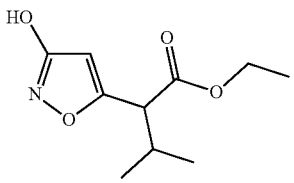

Into a 100 mL round-bottom flask, was placed 2-(3-methoxy-1,2-oxazol-5-yl)-3-methylbutanoic acid (1.0 g, 5.02 mmol, 1.0 equiv) and a solution of hydrobromic acid (11.9 g, 147.07 mmol, 29.30 equiv) in acetic acid (20 mL). The resulting solution was stirred overnight at 60° C. in an oil bath. The reaction mixture was concentrated under reduced pressure. This resulted in 650.0 mg (crude) of 2-(3-hydroxy-1,2-oxazol-5-yl)-3-methylbutanoic acid as a white solid.

LCMS (ES+): m/z 186.05 [M+H]+.

Into a 50 mL round-bottom flask purged and maintained with an inert atmosphere of nitrogen, was placed a solution of 2-(3-hydroxy-1,2-oxazol-5-yl)-3-methylbutanoic acid (650.0 mg, 3.51 mmol, 1.00 equiv) in ethanol (30 mL), sulfuric acid (1 mL). The resulting solution was stirred overnight at 70° C. The reaction mixture was then quenched by the addition of 20 mL water and extracted with ethyl acetate (20 mL×2). The combined organic layer was dried over anhydrous sodium sulfate. Filtered and the filtrate was concentrated under reduced pressure. This resulted in 720.0 mg (96%) of ethyl 2-(3-hydroxy-1,2-oxazol-5-yl)-3-methylbutanoate as light yellow oil.

Step C: ethyl 2-[3-(2-bromoethoxy)-1,2-oxazol-5-yl]-3-methylbutanoate

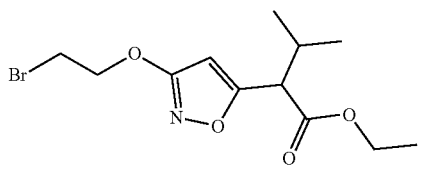 [SMILES: CCOC(=O)C(c1cc(OCCBr)no1)C(C)C]

Into a 50 mL round-bottom flask purged and maintained with an inert atmosphere of nitrogen, was placed a solution of ethyl 2-(3-hydroxy-1,2-oxazol-5-yl)-3-methylbutanoate (380.0 mg, 1.78 mmol, 1.00 equiv) in acetone (15 mL), 1,2-dibromoethane (994.8 mg, 5.30 mmol, 3.00 equiv), $Cs_2CO_3$(1.17 g, 3.59 mmol, 2.00 equiv). The resulting mixture was stirred overnight at room temperature. The reaction mixture was then quenched by the addition of water (15 mL), and extracted with ethyl acetate (20 mL×3). The combined organic layer was dried over anhydrous sodium sulfate and concentrated under reduced pressure. The residue was applied onto a silica gel column eluting with ethyl acetate/petroleum ether (1:5). This resulted in 450.0 mg (79%) of ethyl 2-[3-(2-bromoethoxy)-1,2-oxazol-5-yl]-3-methylbutanoate as a colorless solid.

Step D: 1-[4-(4,4,5,5-tetramethyl-1,3,2-dioxaborolan-2-yl)phenyl]piperazine

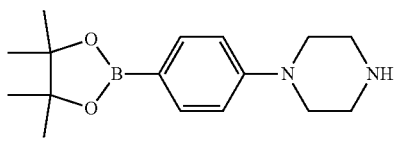 [SMILES: CC1(C)OB(c2ccc(N3CCNCC3)cc2)OC1(C)C]

Into a 100 mL round-bottom flask purged and maintained with an inert atmosphere of nitrogen, was placed a solution of tert-butyl 4-[4-(4,4,5,5-tetramethyl-1,3,2-dioxaborolan-2-yl)phenyl]piperazine-1-carboxylate (1.6 g, 4.12 mmol, 1.00 equiv) in dichloromethane (40 mL), followed by the addition of TMSOTf (1.5 g, 6.75 mmol, 1.60 equiv) dropwise with stirring at 0° C. To the above solution was added 6-dimethylpyridine (132.5 mg, 1.00 mmol, 0.30 equiv). The resulting solution was stirred for 3 hours at room temperature. The reaction was then quenched by the addition of 50 mL of saturated sodium bicarbonate aqueous. The resulting solution was extracted with ethyl acetate (30 mL×3). The combined organic layer was dried over anhydrous sodium sulfate and concentrated under reduced pressure. The residue was applied onto a silica gel column eluting with dichloromethane/methanol (10:1). This resulted in 854.0 mg (72%) of 1-[4-(4,4,5,5-tetramethyl-1,3,2-dioxaborolan-2-yl)phenyl]piperazine as off-white solid. LCMS (ES⁺): m/z 289.15 [M+H]⁺.

Step E: ethyl 3-methyl-2-[3-(2-[4-[4-(tetramethyl-1,3,2-dioxaborolan-2-yl)phenyl]piperazin-1-yl]ethoxy)-1,2-oxazol-5-yl]butanoate

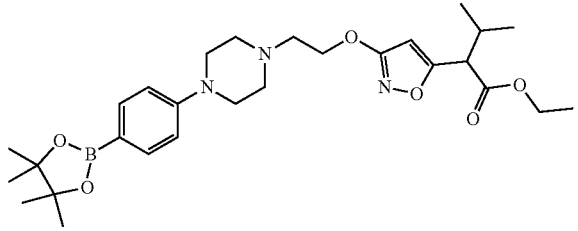 [SMILES: CCOC(=O)C(c1cc(OCCN2CCN(c3ccc(B4OC(C)(C)C(C)(C)O4)cc3)CC2)no1)C(C)C]

Into a 30 mL sealed tube purged and maintained with an inert atmosphere of nitrogen, was placed a solution of ethyl 2-[3-(2-bromoethoxy)-1,2-oxazol-5-yl]3-methylbutanoate (576.0 mg, 1.80 mmol, 1.00 equiv) in N,N-dimethylformamide (6 mL), 1-[4-(tetramethyl-1,3,2-dioxaborolan-2-yl) phenyl]piperazine (624.0 mg, 2.17 mmol, 1.20 equiv), DIEA (17 mL), NaI (20 mg). The resulting solution was stirred for 16 hours at 130° C. The reaction mixture was then quenched by the addition of 30 mL of water. The resulting solution was extracted with ethyl acetate (30 mL×3). The combined organic layer was washed with brine (30 mL×3), dried over anhydrous sodium sulfate and concentrated under reduced pressure. The residue was applied onto a silica gel column eluting with ethyl acetate/petroleum ether (1:2). This resulted in 720.0 mg (76%) of ethyl 3-methyl-2-[3-(2-[4-[4-(tetramethyl-1,3,2-dioxaborolan-2-yl)phenyl]piperazin-1-yl]ethoxy)-1,2-oxazol-5-yl]butanoate as a light yellow solid. LCMS (ES⁺): m/z 528.25 [M+H]⁺.

Step F: ethyl 2-(3-[2-[4-(4-[3-[(2,6-difluoro-3-[[(3R)-3-fluoropyrrolidinesulfonyl]amino]phenyl) carbonyl]-1H-pyrrolo[2,3-b]pyridin-5-yl]phenyl) piperazin-1-yl]ethoxy]-1,2-oxazol-5-yl)-3-methylbutanoate

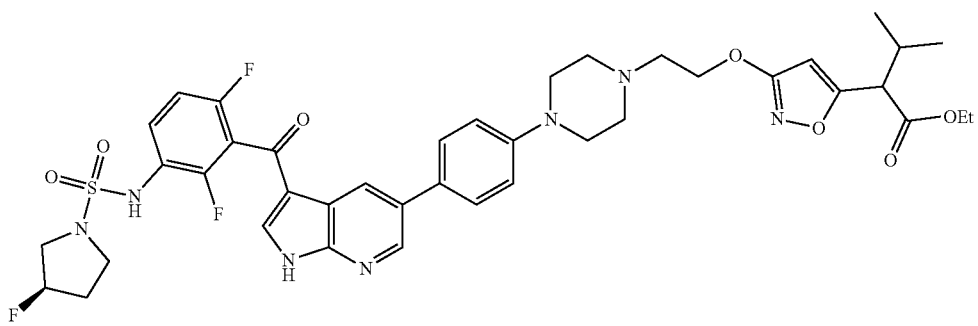 [SMILES: CCOC(=O)C(c1cc(OCCN2CCN(c3ccc(-c4cnc5[nH]cc(C(=O)c6c(F)ccc(NS(=O)(=O)N7CC[C@@H](F)C7)c6F)c5c4)cc3)CC2)no1)C(C)C]

Into a 30 mL sealed tube purged and maintained with an inert atmosphere of nitrogen, was placed a solution of ethyl 3-methyl-2-[3-(2-[4-[4-(tetramethyl-1,3,2-dioxaborolan-2-yl)phenyl]piperazin-1-yl]ethoxy)-1,2-oxazol-5-yl]butanoate (527.0 mg, 1.00 mmol, 1.00 equiv) in 20 mL of 1,4-dioxane/water(4:1), (3R)—N-[3-(5-bromo-1H-pyrrolo[2,3-b]pyridin-3-ylcarbonyl)-2,4-difluorophenyl]-3-fluoropyrrolidine-1-sulfonamide (503.0 mg, 1.00 mmol, 1.00 equiv), sodium carbonate (318.0 mg, 3.00 mmol, 3.00 equiv), Pd(dppf)Cl$_2$ (82.0 mg, 0.10 mmol, 0.10 equiv). The reaction mixture was reacted under microwave radiation for 2 hours at 100° C. The reaction mixture was then quenched by the addition of 20 mL of water. The resulting solution was extracted with ethyl acetate (30 mL×3). The combined organic layer was dried over anhydrous sodium sulfate and concentrated under reduced pressure. The residue was applied onto a silica gel column eluting with dichloromethane/methanol (10:1). This resulted in 460.0 mg (56%) of ethyl 2-(3-[2-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]ethoxy]-1,2-oxazol-5-yl)-3-methylbutanoate as a light yellow solid. LCMS (ES$^+$): m/z 824.15 [M+H]$^+$.

Step G: 2-(3-[2-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]ethoxyl-1,2-oxazol-5-yl)-3-methylbutanoic acid

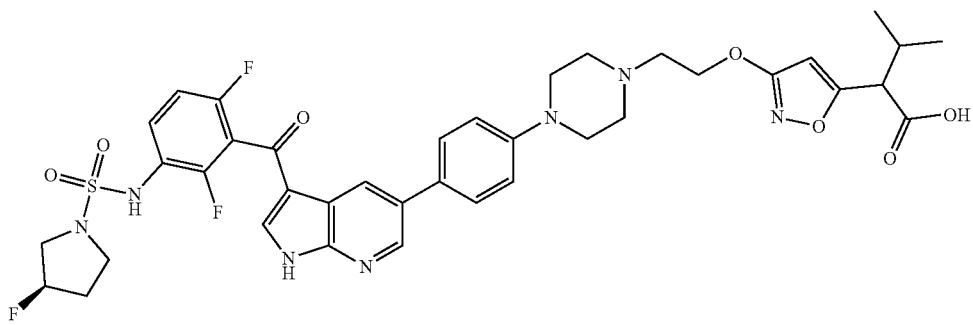 [SMILES: CC(C)C(C(=O)O)c1cc(OCCN2CCN(c3ccc(-c4cnc5[nH]cc(C(=O)c6c(F)ccc(NS(=O)(=O)N7CC[C@@H](F)C7)c6F)c5c4)cc3)CC2)no1]

Into a 50 mL round-bottom flask purged and maintained with an inert atmosphere of nitrogen, was placed a solution of ethyl 2-(3-[2-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]ethoxy]-1,2-oxazol-5-yl)-3-methylbutanoate (420.0 mg, 0.51 mmol, 1.00 equiv) in methanol (10 mL) and then a solution of sodium hydroxide (102.0 mg, 2.55 mmol, 5.00 equiv) in water (2 mL) was added. The resulting solution was stirred at 40° C. for 5 hours. The pH value of the solution was adjusted to pH 6 with hydrogen chloride (1 mol/L). The solids were collected by filtration. The solid was dried in an oven under reduced pressure. This resulted in 366.0 mg (90%) of 2-(3-[2-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]ethoxy]-1,2-oxazol-5-yl)-3-methylbutanoic acid as a solid. LCMS (ES$^+$): m/z 796.10 [M+H]$^+$.

Step H: (2S,4R)-1-[2-(3-[2-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]ethoxy]-1,2-oxazol-5-yl)-3-methylbutanoyl]-4-hydroxy-N-[[4-(4-methyl-1,3-thiazol-5-yl)phenyl-methyl]pyrrolidine-2-carboxamide

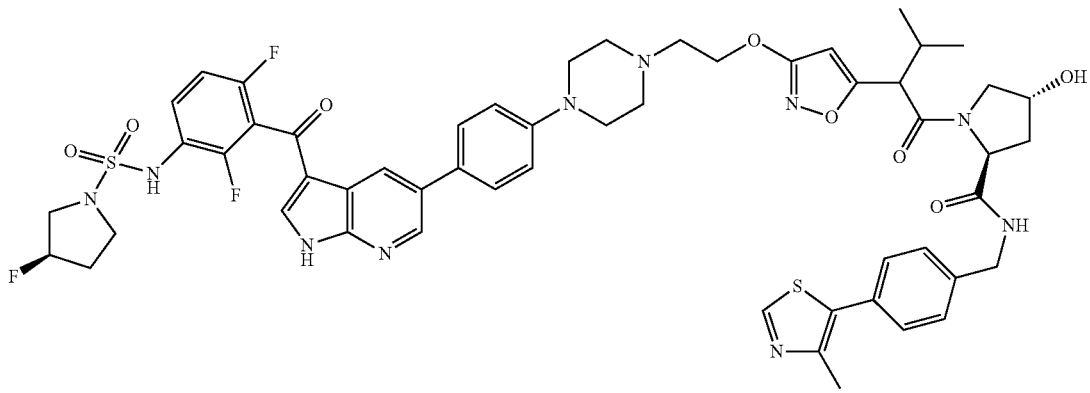 [SMILES: Cc1ncsc1-c1ccc(CNC(=O)[C@@H]2C[C@@H](O)CN2C(=O)C(c2cc(OCCN3CCN(c4ccc(-c5cnc6[nH]cc(C(=O)c7c(F)ccc(NS(=O)(=O)N8CC[C@@H](F)C8)c7F)c6c5)cc4)CC3)no2)C(C)C)cc1]

To a solution of 2-(3-[2-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]ethoxy]-1,2-oxazol-5-yl)-3-methylbutanoic acid (300.0 mg, 0.38 mmol, 1.00 equiv) and (2S,4R)-4-hydroxy-N-[4-(4-methyl-1,3-thiazol-5-yl)phenyl]methylpyrrolidine-2-carboxamide hydrochloride (199.9 mg, 0.56 mmol, 1.50 equiv) in N,N-dimethylformamide (10 mL), was added DIEA (3.0 mL) and BOP (200.3 mg, 0.45 mmol, 1.20 equiv). The resulting mixture was stirred for 1 hour at room temperature. The reaction was then quenched by the addition of 20 mL of water. The resulting solution was extracted with ethyl acetate (30 mL×3). The combined organic layer was washed with brine (30 mL×3), dried over anhydrous sodium sulfate and concentrated under reduced pressure. The residue was applied onto a silica gel column eluting with dichloromethane/methanol (10:1). This resulted in 265.0 mg (64%) of (2S,4R)-1-[2-(3-[2-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]ethoxy]-1,2-oxazol-5-yl)-3-methylbutanoyl]-4-hydroxy-N-[[4-(4-methyl-1,3-thiazol-5-yl)phenyl]methyl]pyrrolidine-2-carboxamide as a solid. LCMS (ES+): m/z 1095.30 [M+H]+.

Step I: (2S,4R)-4-hydroxy-N-[[4-(4-methyl-1,3-thiazol-5-yl)phenyl]methyl]-1-(2-[3-[2-(methylamino)ethoxy]-1,2-oxazol-5-yl]butanoyl)pyrrolidine-2-carboxamide

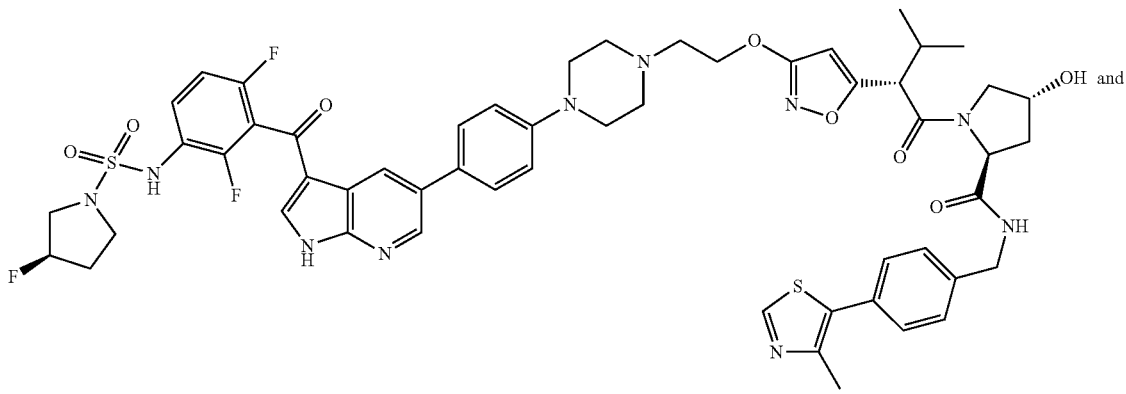

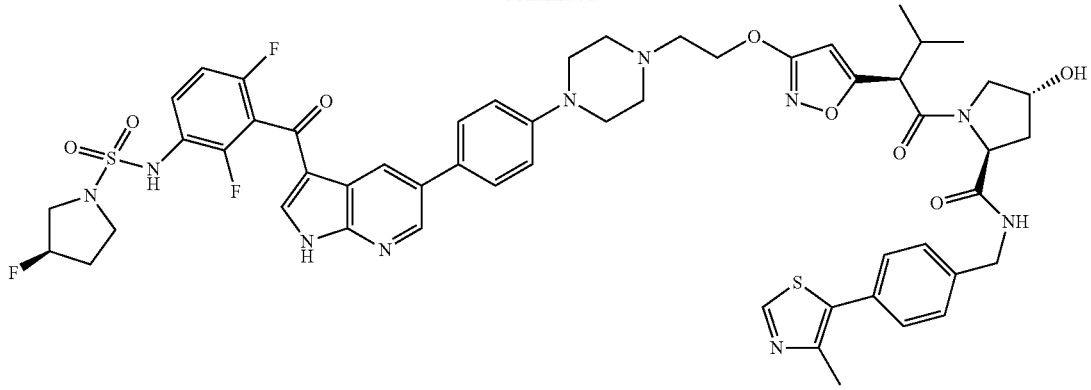

(2S,4R)-1-[2-(3-[2-[4-(4-[3-[(2,6-difluoro-3-[[(3R)-3-fluoropyrrolidine-1-sulfonyl]amino]phenyl)carbonyl]-1H-pyrrolo[2,3-b]pyridin-5-yl]phenyl)piperazin-1-yl]ethoxy]-1,2-oxazol-5-yl)-3-methylbutanoyl]-4-hydroxy-N-[[4-(4-methyl-1,3-thiazol-5-yl)phenyl]methyl]pyrrolidine-2-carboxamide was separated by chiral HPLC resulting in:

25.7 mg (10%) of (2S,4R)-1-((S)-2-(3-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide.
$^1$H NMR (300 MHz, DMSO-d$_6$): δ9.10-8.97 (m, 1H), 8.65 (d, J=2.0 Hz, 1H), 8.60-8.53 (m, 2H), 8.10-8.07 (m, 1H), 7.70-7.56 (m, 3H), 7.51-7.21 (m, 5H), 7.18-7.07 (m, 2H), 6.18-6.12 (m, 1H), 5.38-5.21 (m, 1H), 4.44-4.31 (m, 6H), 3.78 (d, J=8.6 Hz, 1H), 3.62-3.45 (m, 4H), 3.32-3.01 (m, 8H), 2.98-2.60 (m, 4H), 2.55-2.43 (m, 3H), 2.34-1.82 (m, 6H), 0.97-0.62 (m, 6H). LCMS (ES$^+$): m/z 1095.60 [M+H]$^+$.

57.5 mg (22%) of (2S,4R)-1-((R)-2-(3-(2-(4-(4-(3-(2,6-difluoro-3-(((R)-3-fluoropyrrolidine)-1-sulfonamido)benzoyl)-1H-pyrrolo[2,3-b]pyridin-5-yl)phenyl)piperazin-1-yl)ethoxy)isoxazol-5-yl)-3-methylbutanoyl)-4-hydroxy-N-(4-(4-methylthiazol-5-yl)benzyl)pyrrolidine-2-carboxamide.
$^1$H NMR (300 MHz, DMSO-d$_6$): δ12.90 (brs, 1H), 9.84 (brs, 1H), 8.99-8.95 (m, 1H), 8.69-8.66 (m, 1H), 8.60-8.53 (m, 2H), 8.07 (s, 1H), 7.70-7.61 (m, 3H), 7.54-7.39 (m, 4H), 7.387.30 (m, 1H), 7.21-7.08 (m, 2H), 6.18-5.80 (m, 1H), 5.40-5.15 (m, 1H), 4.74-4.28 (m, 6H), 3.90-3.62 (m, 6H), 3.41-3.22 (m, 7H), 3.21-2.81 (m, 5H) 2.45-2.42 (m, 3H), 2.32-2.20 (m, 1H), 2.17-1.80 (m, 4H), 0.95 (d, J=6.5 Hz, 3H), 0.81 (d, J=6.7 Hz, 3H). LCMS (ES$^+$): m/z 1095.60 [M+H]$^+$.

Exemplary compounds 287 and 288 may be prepared in an analogous manner.

Example Synthesis of Compound 291 [(2S,4R)-4-hydroxy-1-((S)-2-(2-(2-(4-(4-((E)-1-(hydroxyimino)-2,3-dihydro-1H-inden-5-yl)-3-(pyridin-4-yl)-1H-pyrazol-1-yl)phenoxy)ethoxy)acetamido)-3,3-dimethylbutanoyl)-N-(4-(4-methylthiazol-5-yl)benzyl)pyrrolidine-2-carboxamide]

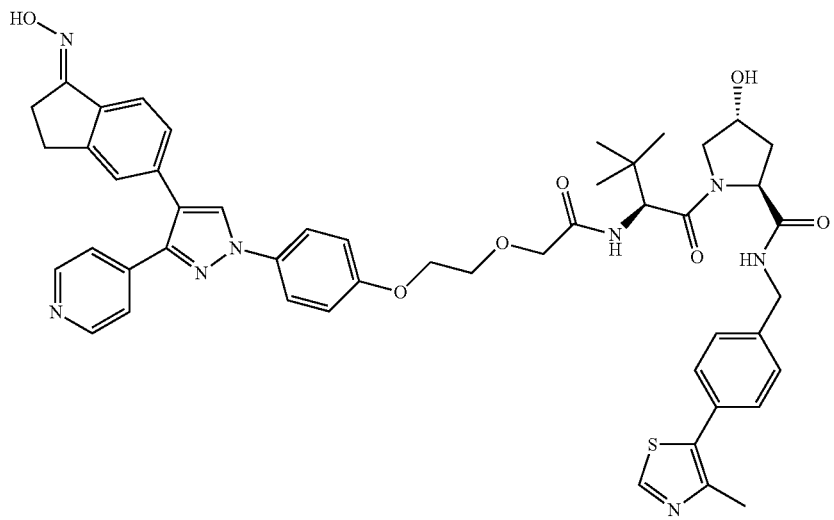 [SMILES: Cc1ncsc1-c1ccc(CNC(=O)[C@@H]2C[C@@H](O)CN2C(=O)[C@@H](NC(=O)COCCOc2ccc(-n3cc(-c4ccc5c(c4)CC/C5=N\O)c(-c4ccncc4)n3)cc2)C(C)(C)C)cc1]

Step A: tert-butyl 2-(2-(4-(4-bromo-3-(pyridin-4-yl)-1H-pyrazol-1-yl)phenoxy)ethoxy)acetatethoxy)acetate

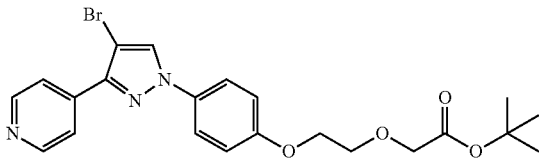 [SMILES: CC(C)(C)OC(=O)COCCOc1ccc(-n2cc(Br)c(-c3ccncc3)n2)cc1]

To a solution of tert-butyl 2-(2-chloroethoxy)acetate (400 mg, 2.06 mmol) and Cs$_2$CO$_3$ in DMF (15 mL) was added tert-butyl 4-(4-bromo-3-(pyridin-4-yl)-1H-pyrazol-1-yl) phenol (525 mg, 1.66 mmol). The mixture was stirred at 75° C. for 3 hours. The solution was diluted with EA (100 mL). The mixture was washed with water, brine. The organic phase was dried over anhydrous sodium sulfate, filtered and concentrated under reduced pressure. The residue was purified by silica gel column chromatography to afford 2-(2-(4-(4-bromo-3-(pyridin-4-yl)-1H-pyrazol-1-yl) phenoxy) ethoxy)acetatethoxy)acetate (290 mg, 0.62 mmol). LCMS (ES$^+$): m/z 475.21 [M+H]$^+$, 476.1 [M+2H]$^+$.

Step B: (2S,4R)-1-((S)-2-(2-(2-(4-(4-bromo-3-(pyridin-4-yl)-1H-pyrazol-1-yl)phenoxy)ethoxy)acetamido)-3,3-dimethylbutanoyl)-4-hydroxy-N-(4-(4-methylthiazol-5-yl)benzyl)pyrrolidine-2-carboxamide

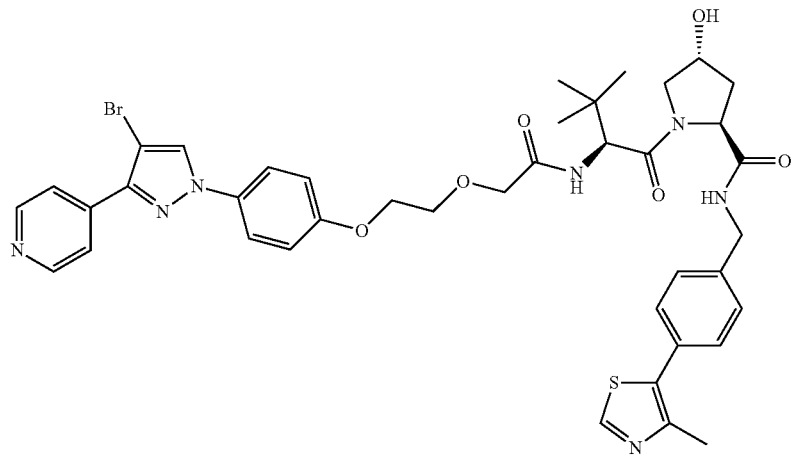 [SMILES: Cc1ncsc1-c1ccc(CNC(=O)[C@@H]2C[C@@H](O)CN2C(=O)[C@@H](NC(=O)COCCOc2ccc(-n3cc(Br)c(-c4ccncc4)n3)cc2)C(C)(C)C)cc1]

To a solution of 2-(2-(4-(4-bromo-3-(pyridin-4-yl)-1H-pyrazol-1-yl) phenoxy)ethoxy)acetatethoxy)acetate (290 mg, 0.61 mmol) in 1,4-dioxane (5 mL) was added HCl (g) in 1,4-dioxane (3 M, 5 mL). The reaction was stirred at room temperature for 2 hours. The solvent was removed under reduced pressure. The residue was dissolved in DCM (20 mL). (2S,4R)-1-((S)-2-amino-3,3-dimethylbutanoyl)-4-hydroxy-N-(4-(4-methylthiazol-5-yl)benzyl)pyrrolidine-2-carboxamide hydrochloride (394 mg, 0.92 mmol), DIPEA (394 mg, 3.05 mmol) and PyBOP (954 g, 1.83 mmol) were added to the solution subsequently. After stirring 30 minutes, it was diluted with DCM (50 mL). The mixture was washed with water, brine. The organic phase was dried over anhydrous sodium sulfate, filtered and concentrated under reduced pressure. The residue was purified by silica gel column chromatography to afford (2S,4R)-1-((S)-2-(2-(2-(4-(4-bromo-3-(pyridin-4-yl)-1H-pyrazol-1-yl)phenoxy)ethoxy) acetamido)-3,3-dimethylbutanoyl)-4-hydroxy-N-(4-(4-methylthiazol-5-yl)benzyl)pyrrolidine-2-carboxamide (390 mg, 0.46 mmol). LCMS (ES$^+$): m/z 830.2 [M+H]$^+$.

Step C: (2S,4R)-1-((S)-3,3-dimethyl-2-(2-(2-(4-(4-(1-oxo-2,3-dihydro-1H-inden-5-yl)-3-(pyridin-4-yl)-1H-pyrazol-1-yl)phenoxy)ethoxy)acetamido)butanoyl)-4-hydroxy-N-(4-(4-methylthiazol-5-yl)benzyl)pyrrolidine-2-carboxamide

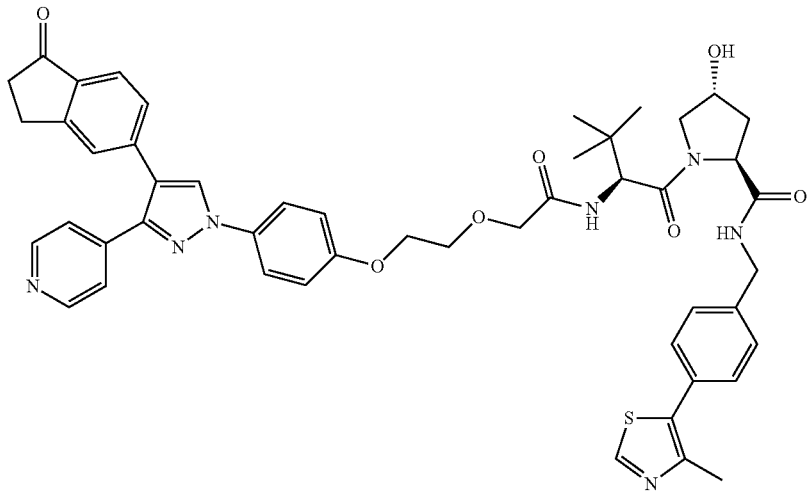 [SMILES: Cc1ncsc1-c1ccc(CNC(=O)[C@@H]2C[C@@H](O)CN2C(=O)[C@@H](NC(=O)COCCOc2ccc(-n3cc(-c4ccc5c(c4)CCC5=O)c(-c4ccncc4)n3)cc2)C(C)(C)C)cc1]

To a solution of (2S,4R)-1-((S)-2-(2-(2-(4-(4-bromo-3-(pyridin-4-yl)-1H-pyrazol-1-yl)phenoxy)ethoxy)acetamido)-3,3-dimethylbutanoyl)-4-hydroxy-N-(4-(4-methylthiazol-5-yl)benzyl)pyrrolidine-2-carboxamide (390 mg, 0.46 mmol) and 5-(4,4,5,5-tetramethyl-1,3,2-dioxaborolan-2-yl)-2,3-dihydro-1H-inden-1-one (248 mg, 0.92 mmol) in 1,4-dioxane/water (20 mL/1 mL) were added Pd(aMPhos)Cl$_2$ (36 mg, 0.046 mmol), CsF (360 mg, 2.30 mmol) subsequently. The reaction mixture was stirred at 90° C. overnight under nitrogen atmosphere. After cooled to room temperature, it was diluted with ethyl acetate (100 mL). The mixture was washed with brine (50 mL×2). The organic phase was dried over anhydrous sodium sulfate, filtered and concentrated under vacuum. The residue was purified by silica gel column chromatography (DCM/MeOH) to afford (2S,4R)-1-((S)-3,3-dimethyl-2-(2-(2-(4-(4-(1-oxo-2,3-dihydro-1H-inden-5-yl)-3-(pyridin-4-yl)-1H-pyrazol-1-yl)phenoxy)ethoxy)acetamido)butanoyl)-4-hydroxy-N-(4-(4-methylthiazol-5-yl)benzyl)pyrrolidine-2-carboxamide (230 mg, 0.26 mmol). LCMS (ES$^+$): m/z 882.3 [M+H]$^+$.

Step D: (2S,4R)-4-hydroxy-1-((S)-2-(2-(2-(4-(4-((E)-1-(hydroxyimino)-2,3-dihydro-1H-inden-5-yl)-3-(pyridin-4-yl)-1H-pyrazol-1-yl)phenoxy)ethoxy)acetamido)-3,3-dimethylbutanoyl)-N-(4-(4-methylthiazol-5-yl)benzyl)pyrrolidine-2-carboxamide

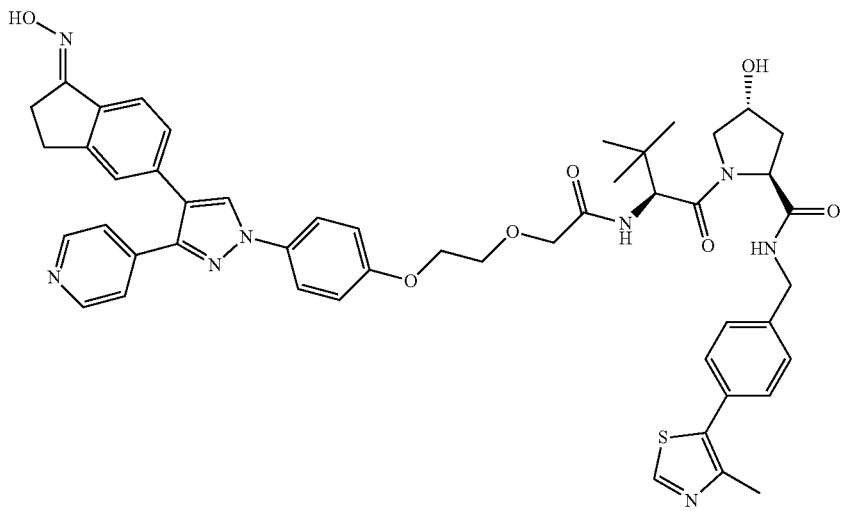 [SMILES: Cc1ncsc1-c1ccc(CNC(=O)[C@@H]2C[C@@H](O)CN2C(=O)[C@@H](NC(=O)COCCOc2ccc(-n3cc(-c4ccc5c(c4)CC/C5=N\O)c(-c4ccncc4)n3)cc2)C(C)(C)C)cc1]

To a solution of (2S,4R)-1-((S)-3,3-dimethyl-2-(2-(2-(4-(4-(1-oxo-2,3-dihydro-1H-inden-5-yl)-3-(pyridin-4-yl)-1H-pyrazol-1-yl)phenoxy)ethoxy)acetamido)butanoyl)-4-hydroxy-N-(4-(4-methylthiazol-5-yl)benzyl)pyrrolidine-2-carboxamide (230 mg, 0.26 mmol) in CH$_3$CN and pyridine (v/v=1/1, 5 mL) was added NH$_2$OH—HCl (179 mg, 2.6 mmol). The solution was stirred at 20° C. for 3 hours. The mixture was filtered through Celite. The filtrate was concentrated under vacuum. The residue was purified by silica gel column chromatography (DCM/MeOH) to afford (2S,4R)-4-hydroxy-1-((S)-2-(2-(2-(4-(4-((E)-1-(hydroxyimino)-2,3-dihydro-1H-inden-5-yl)-3-(pyridin-4-yl)-1H-pyrazol-1-yl)phenoxy)ethoxy)acetamido)-3,3-dimethylbutanoyl)-N-(4-(4-methylthiazol-5-yl)benzyl)pyrrolidine-2-carboxamide (21 mg, 0.023 mmol). $^1$H NMR (400 MHz, DMSO-d$_6$): δ 10.89 (s, 1H), 8.97 (s, 1H), 8.72 (s, 1H), 8.56-8.58 (m, 3H), 7.86 (d, J=8.4 Hz, 2H), 7.49-7.57 (m, 3H), 7.39 (m, 6H), 7.22 (s, 1H), 7.09-7.12 (m, 2H), 5.17 (m, 1H), 4.52-4.65 (m, 1H), 4.32-4.50 (m, 3H), 4.08-4.29 (s, 4H), 3.95-4.05 (m, 2H), 3.73-3.82 (m, 2H), 3.56-3.70 (m, 2H), 2.95-3.08 (m, 2H), 2.76-2.85 (s, 2H), 2.40-2.51 (m, 3H), 1.87-2.16 (s, 1H), 0.91-1.07 (s, 9H). LCMS (ES$^+$): m/z 898.4 [M+H]$^+$.

Exemplary compounds 289, 290, 292, and 293 may be prepared in an analogous manner.

Example 15—Synthetic Scheme A: Compounds 305, 298, 299, 300, 301, 302, and 303

Method A
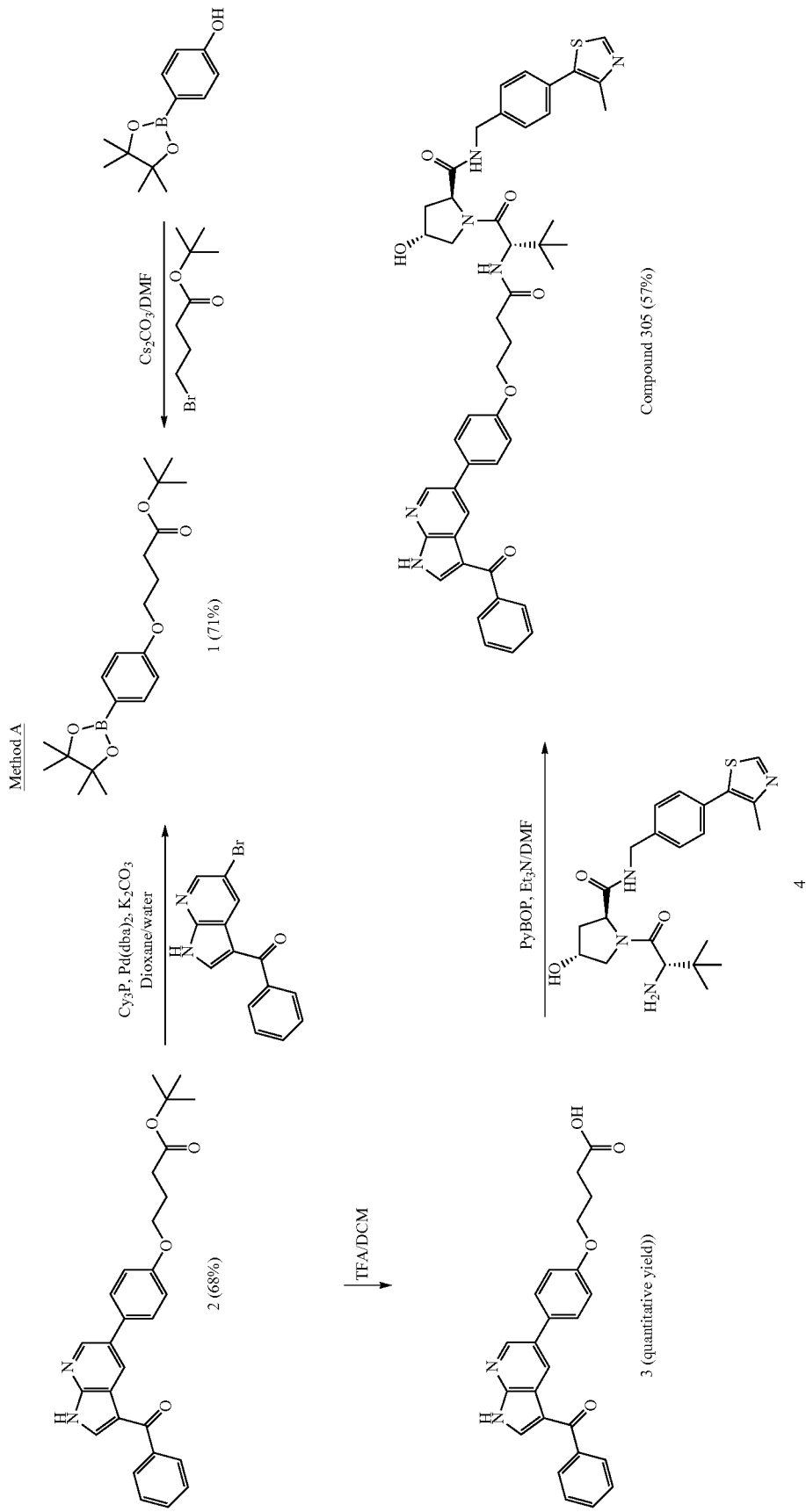

tert-Butyl 4-(4-(4,4,5,5-tetramethyl-1,3,2-dioxaborolan-2-yl)phenoxy)butanoate (1)

To a mixture of 4-(4,4,5,5-tetramethyl-1,3,2-dioxaborolan-2-yl)phenol (209.12 mg, 0.95 mmol) and tert-butyl 4-bromobutanoate (212 mg, 0.95 mmol) in N,N-Dimethylformamide (2 mL) was added $Cs_2CO_3$ (402.47 mg, 1.24 mmol). Reaction mixture was heated at 65° C. for 12 hours (overnight). By TLC small amounts of starting material (Hex:AcOEt, 7:3). Crude product was purified by flash CC ($SiO_2$-25 g, Hex:AcOEt, gradient 9:1 to 4:6) to give 198 mg (57% yield) of product as an oil: $^1$H NMR (500 MHz, DMSO-d6) δ 7.59 (d, J=8.2 Hz, 2H), 6.91 (d, J=7.9 Hz, 2H), 3.99 (t, J=6.3 Hz, 2H), 2.35 (t, J=7.3 Hz, 2H), 1.92 (p, J=6.7 Hz, 2H), 1.39 (s, 9H), 1.27 (s, 12H). $^{13}$C NMR (101 MHz, dmso) δ 172.25, 161.56, 136.66, 114.37, 83.77, 80.12, 66.81, 31.72, 28.20, 25.12, 24.71. LC-MS (ESI); m/z [M+Na]$^+$: Calcd. for $C_{20}H_{31}BO_5Na$, 385.2162. Found 385.2194.

tert-Butyl 4-(4-(3-benzoyl-1H-pyrrolo[2,3-b]pyridin-5-yl)phenoxy)butanoate (2)

To a solution of tert-butyl 4-[4-(4,4,5,5-tetramethyl-1,3,2-dioxaborolan-2-yl)phenoxy]-butanoate (72 mg, 0.2 mmol) and (5-bromo-1H-pyrrolo[2,3-b]pyridin-3-yl)-phenyl-methanone (59.85 mg, 0.2 mmol) in Dioxane (6 mL) was de-gassed under vacuum and purged with argon. Then $K_2CO_3$ (82.4 mg, 0.6 mmol) was added, follow by water (2 mL), the reaction mixture was de-gassed under vacuum and purged with argon again. Tricyclohexylphosphine (5.57 mg, 0.02 mmol) and Pd(dba)$_2$ (5.71 mg, 0.01 mmol) was added into and the reaction mixture and the reaction mixture was de-gassed under vacuum and purged with argon again. Then reaction mixture was heated at 90° C. for 2 hours. By TLC some SM (Hex:AcOEt, 3:7), an additional amounts of Tricyclohexylphosphine (5.57 mg, 0.02 mmol) and Pd(dba)$_2$ (5.71 mg, 0.01 mmol) was added twice and reaction mixture stirred for an additional 2 hours. The reaction mixture was diluted with AcOEt (20 mL), dried ($Na_2SO_4$), and filtered in vacuum over a celite pad, filtrate was dried ($Na_2SO_4$) and concentrated under vacuum. The crude material was diluted in DCM and purified by flash chromatography ($SiO_2$-40 g, gradient Hex:AcOEt, gradient 9:1 to 100% AcOEt) to give 69 mg (68%) of product as off-white solid. $^1$H NMR (500 MHz, DMSO-d6) δ 12.68 (s, 1H), 8.65 (s, 1H), 8.60 (s, 1H), 8.10 (s, 1H), 7.82 (d, J=7.5 Hz, 2H), 7.58 (dt, J=36.0, 7.9 Hz, 5H), 7.04 (d, J=8.1 Hz, 2H), 4.16-3.83 (m, 2H), 2.37 (t, J=6.5 Hz, 2H), 1.95 (dd, J=11.4, 5.5 Hz, 2H), 1.39 (s, 9H). $^{13}$C NMR (126 MHz, dmso) δ 189.81, 171.86, 158.13, 148.26, 143.24, 139.62, 136.43, 131.45, 130.82, 130.66, 128.52, 128.48, 128.16, 127.01, 118.77, 115.13, 113.73, 79.68, 66.63, 31.36, 27.77, 24.37. LC-MS (ESI); m/z: [M+H]$^+$ Calcd. for $C_{28}H_{29}N_2O_4$, 457.2127. Found 457.2156.

4-(4-(3-Benzoyl-1H-pyrrolo[2,3-b]pyridin-5-yl)phenoxy)butanoic Acid (3)

A solution of tert-butyl 4-(4-(3-(2,6-difluorobenzoyl)-1H-pyrrolo[2,3-b]pyridin-5-yl)-phenoxy)butanoate (30 mg, 0.06 mmol) in a mixture of TFA (1 ml, 13.46 mmol) and dichloromethane (3 ml) was stirred for 1 hour. Then the solvent was removed under vacuum and crude product was dried under high vacuum for 2 hours. Crude product was used in the next step without any further purification (26.5 mg, quantitative yield). LC-MS (ESI); m/z: [M+H]$^+$ Calcd. for $C_{24}H_{21}N_2O_4$, 401.1501. Found 401.1420.

(2S,4R)-1-((S)-2-(4-(4-(3-benzoyl-1H-pyrrolo[2,3-b]pyridin-5-yl)phenoxy)butanamido)-3,3-dimethylbutanoyl)-4-hydroxy-N-(4-(4-methylthiazol-5-yl)benzyl)pyrrolidine-2-carboxamide (Compound 305)

To a solution of 4-[4-(3-benzoyl-1H-pyrrolo[2,3-b]pyridin-5-yl)-phenoxy]butanoic acid (26.5 mg, 0.07 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (30.91 mg, 0.07 mmol) in DMF(2 ml) was added TEA (0.2 ml, 1.43 mmol) and PyBOP (37.88 mg, 0.07 mmol) at room temperature. The reaction mixture was stirred for 12 hours (overnight) at the same temperature. TLC (DCM:MeOH:NH$_4$OH, 90:9:1) shows no starting materials. The DMF was removed under high vacuum. Crude product was filtered over a silica-carbonate cartridge (1 g) using DCM:MeOH (9:1) as a eluent. Filtrate was evaporated under vacuum and crude product was purified by PTLC (MeOH:DCM, 9:1), to give 31 mg of product (58% yield). $^1$H NMR (400 MHz, DMSO-d6) δ 12.70 (s, 1H), 8.97 (s, 1H), 8.68 (d, J=2.2 Hz, 1H), 8.62 (d, J=2.3 Hz, 1H), 8.60-8.51 (m, 1H), 8.12 (s, 1H), 8.00 (d, J=9.3 Hz, 1H), 7.90-7.77 (m, 1H), 7.72-7.51 (m, 5H), 7.48-7.29 (m, 4H), 7.07 (d, J=8.7 Hz, 2H), 5.15 (d, J=3.5 Hz, 1H), 4.59 (d, J=9.3 Hz, 1H), 4.50-4.32 (m, 3H), 4.22 (dd, J=15.9, 5.4 Hz, 1H), 4.03 (td, J=6.5, 2.6 Hz, 2H), 3.80-3.60 (m, 2H), 2.44 (s, 3H), 2.48-2.28 (m, 5H), 2.13-1.84 (m, 4H), 0.96 (s, 9H). $^{13}$C NMR (101 MHz, dmso) δ 189.87, 172.00, 171.63, 169.69, 158.23, 151.48, 148.29, 147.73, 143.29, 139.64, 139.53, 136.54, 131.52, 131.19, 130.74, 129.65, 128.66, 128.58, 128.55, 128.21, 127.44, 127.05, 118.81, 115.19, 113.74, 68.93, 67.13, 58.75, 56.47, 48.64, 41.68, 38.01, 35.29, 31.33, 26.43, 25.08, 15.99. LC-MS (ESI); m/z [M+H]$^+$: Calcd. for $C_{46}H_{49}N_6O_6S$, 813.3434. Found 813.3478.

Example 16—Synthetic Scheme B: 217, 220, and 221

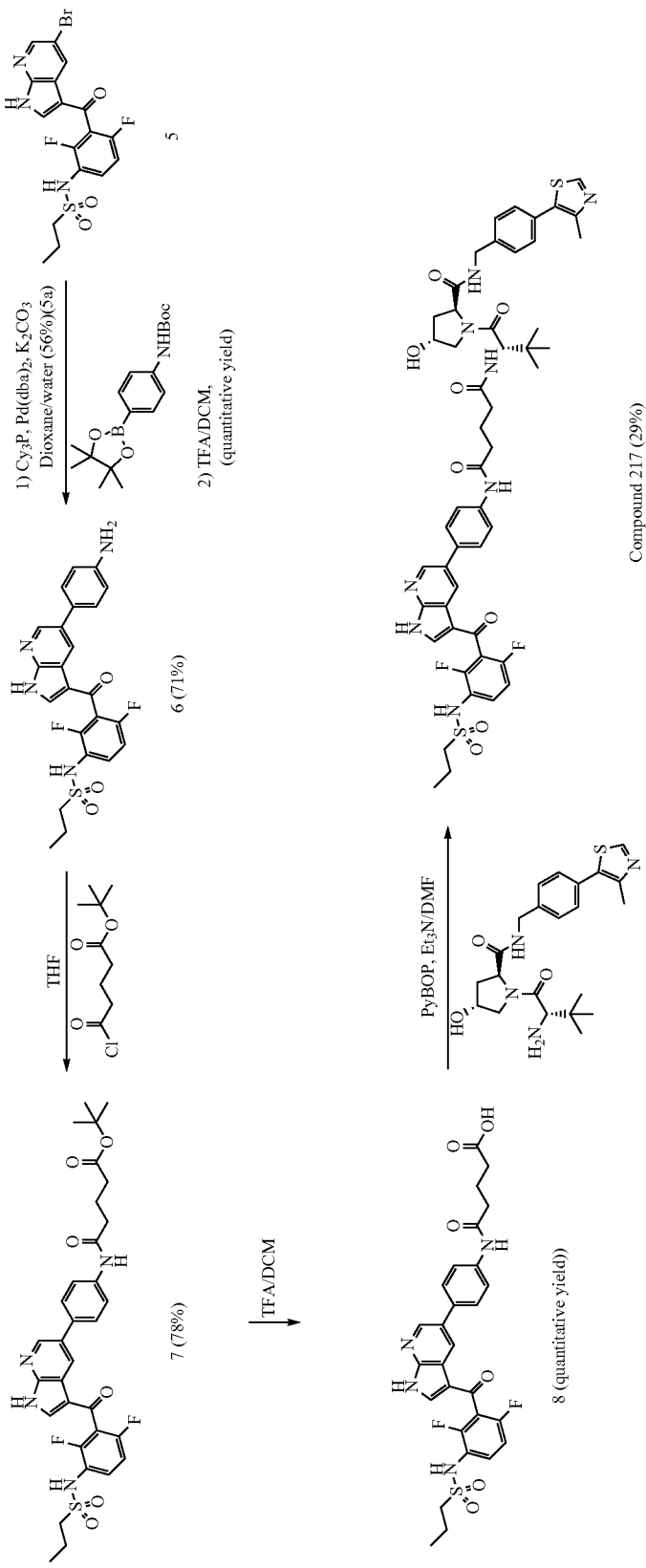

tert-Butyl(4-(3-(2,6-difluoro-3-(propylsulfonamido) benzoyl)-1H-pyrrolo[2,3-b]pyridin-5-yl)phenyl)carbamate (5a)

To a solution of tert-butyl (4-(4,4,5,5-tetramethyl-1,3,2-dioxaborolan-2-yl)phenyl)-carbamate (50.99 mg, 0.16 mmol) in Dioxane (3 ml) was added N-[3-(5-bromo-1-H-pyrrolo[2,3-b]pyridine-3-carbonyl)-2,4-difluoro-phenyl]propane-1-sulfonamide (0.06 ml, 0.13 mmol), $K_2CO_3$ (55.19 mg, 0.4 mmol), Tricyclohexylphosphine (3.73 mg, 0.01 mmol) and water (1 mL). Then the reaction mixture was de-gassed under vacuum and purged with argon, $Pd(dba)_2$ (3.83 mg, 0.01 mmol) was added into and the reaction mixture was heated at 80° C. for 3 hours. By TLC small amounts of SM (Hex:AcOEt, 3:7), the reaction mixture was filtered in vacuum over a celite pad, filtrate was poured onto an aqueous saturated solution of NaCl (20 mL) and the product was extracted with EtOAc (2×20 mL). The EtOAc layers were combined, dried ($Na_2SO_4$) and concentrated in vacuum. The crude material was diluted in DCM and purified by flash chromatography ($SiO_2$-12 g, Hexane:AcOEt, gradient 8:2 to 100% AcOEt) to give 47 mg (56%) of product as a off-white solid. $^1$H NMR (400 MHz, DMSO-d6) δ 12.96 (bs, 1H), 9.77 (bs, 1H), 9.49 (s, 1H), 8.68 (d, J=2.1 Hz, 1H), 8.57 (bs, 1H), 8.21 (s, 1H), 7.79-7.46 (m, 5H), 7.28 (td, J=8.7, 1.5 Hz, 1H), 3.19-3.07 (m, 2H), 1.74 (dq, J=14.9, 7.4 Hz, 2H), 1.50 (s, 9H), 0.96 (t, J=7.4 Hz, 3H). $^{13}$C NMR (151 MHz, dmso) δ 180.61, 156.03 (dd, J=246.5, 7.1 Hz), 152.77, 152.34 (dd, J=249.5, 8.5 Hz), 148.60, 143.76, 139.22, 138.64, 131.66, 131.31, 128.79 (d, J=9.7 Hz), 127.35, 126.38, 121.94 (dd, J=13.7, 3.6 Hz), 118.66, 118.24 (t, J=23.5 Hz), 117.53, 115.63, 112.35 (dd, J=22.6, 3.9 Hz), 79.19, 53.46, 28.15, 16.85, 12.62. LC-MS (ESI); m/z: [M+H]$^+$ Calcd. for $C_{28}H_{29}F_2N_4O_5S$, 571.1826. Found 571.1917.

N-(3-(5-(4-aminophenyl)-1H-pyrrolo[2,3-b]pyridine-3-carbonyl)-2,4-difluorophenyl)propane-1-sulfonamide (6)

To a solution of tert-butyl (4-(3-(2,6-difluoro-3-(propylsulfonamido)benzoyl)-1H-pyrrolo-[2,3-b]pyridin-5-yl)phenyl)carbamate (30 mg, 0.05 mmol) in TFE (2 mL) was heated at 140° C., for 3 hours under microwave assisted conditions. The reaction mixture was evaporated to dryness under vacuum, to give 23 mg of product in quantitative yields. The crude product was used in the next step without any further purification. LC-MS (ESI); m/z: [M+H]$^+$ Calcd. for $C_{23}H_{21}F_2N_4O_3S$, 471.1302. Found 471.1351.

tert-Butyl-5-((4-(3-(2,6-difluoro-3-(propylsulfonamido)benzoyl)-1H-pyrrolo [2,3-b]pyridin-5-yl)phenyl)amino)-5-oxopentanoate (7)

To a solution of tert-butyl 5-chloro-5-oxopentanoate (21.96 mg, 0.11 mmol) in THF (2 mL) was added N-(3-(5-(4-aminophenyl)-1H-pyrrolo[2,3-b]-pyridine-3-carbonyl)-2,4-difluorophenyl)propane-1-sulfonamide (10 mg, 0.02 mmol). The resulting suspension was heated to reflux for 12 hours (overnight). The reaction mixture was evaporated in vacuum and the crude product was purified by PTLC (MB:DCM, 4:6) to give a white powder 10.7 mg (79% yield). $^1$H NMR (500 MHz, DMSO-d6) δ 12.96 (bs, 1H), 10.04 (s, 1H), 9.76 (bs, 1H), 8.69 (d, J=2.2 Hz, 1H), 8.59 (s, 1H), 8.21 (s, 1H), 7.75 (d, J=8.7 Hz, 2H), 7.69 (d, J=8.6 Hz, 2H), 7.59 (td, J=9.0, 5.8 Hz, 1H), 7.28 (t, J=9.2 Hz, 1H), 3.13 (dd, J=8.7, 6.7 Hz, 2H), 2.39 (t, J=7.4 Hz, 2H), 2.28 (t, J=7.4 Hz, 2H), 1.83 (p, J=7.4 Hz, 2H), 1.75 (h, J=7.5 Hz, 2H), 1.41 (s, 9H), 0.96 (t, J=7.4 Hz, 3H). $^{13}$C NMR (101 MHz, dmso) δ 181.01, 172.37, 171.16, 156.02 (dd, J=246.3, 7.0 Hz), 152.34 (dd, J=249.5, 8.5 Hz), 149.05, 144.18, 139.30, 139.05, 133.00, 131.62, 128.77 (d, J=9.5 Hz), 127.75, 126.88, 121.96 (dd, J=13.7, 3.5 Hz), 120.04, 118.74-117.84 (m), 117.94, 116.05, 112.34 (dd, J=22.8, 3.0 Hz), 79.98, 53.89, 35.72, 34.53, 28.20, 20.93, 17.25, 13.02. LC-MS (ESI); m/z: [M+H]$^+$ Calcd. for $C_{32}H_{35}F_2N_4O_6S$, 641.2245. Found 641.2473.

5-((4-(3-(2,6-difluoro-3-(propylsulfonamido)benzoyl)-1H-pyrrolo[2,3-b]pyridin-5-yl)phenyl)amino)-5-oxopentanoic acid (8)

A solution of tert-butyl 5-((4-(3-(2,6-difluoro-3-(propylsulfonamido)benzoyl)-1H-pyrrolo[2,3-b]pyridin-5-yl)phenyl)amino)-5-oxopentanoate (10.7 mg, 0.02 mmol) in a mixture of TFA (1 ml, 13.46 mmol) and Dichloromethane (2 ml) was stirred for 2 hours. Then the solvent was removed under vacuum and crude product was dried under high vacuum for 2 hours. Crude product was used in the next step without any further purification (9.7 mg, quantitative yield). LC-MS (ESI); m/z: [M+H]$^+$ Calcd. for $C_{28}H_{27}F_2N_4O_6S$, 585.1619. Found 585.1636.

N1-(4-(3-(2,6-difluoro-3-(propylsulfonamido)benzoyl)-1H-pyrrolo[2,3-b]pyridin-5-yl)phenyl)-N5-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide (Compound 217)

To a solution of 5-((4-(3-(2,6-difluoro-3-(propylsulfonamido)-benzoyl)-1H-pyrrolo[2,3-b]pyridin-5-yl)phenyl)amino)-5-oxopentanoic acid (9.7 mg, 0.02 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (8.52 mg, 0.02 mmol) in DMF (1 ml) was added TEA (0.1 ml, 0.72 mmol) and PyBOP (9.5 mg, 0.02 mmol) at room temperature. The reaction mixture was stirred for 4 hours at the same temperature. TLC (DCM:MeOH:NH$_4$OH, 90:9:1) shows no starting materials. The reaction mixture was diluted with EtOAc (10 mL) and washed with brine (5 mL, 4×), organic phase was dried (Na$_2$SO$_4$), and evaporated under vacuum. Crude product was purified by PTLC (DCM:MeOH:NH$_4$OH, 90:9:1) to give 4.8 mg of product (29% yield). $^1$H NMR (500 MHz, DMSO-d6) δ 10.02 (s, 1H), 8.97 (s, 1H), 8.68 (d, 1H), 8.64-8.52 (m, 2H), 8.21 (s, 1H), 7.95 (d, J=9.2 Hz, 1H), 7.72 (dd, J=36.7, 8.5 Hz, 4H), 7.62-7.54 (m, 1H), 7.40 (dd, 4H), 7.28 (t, J=8.7 Hz, 1H), 5.16 (d, 2H), 4.56 (d, J=9.3 Hz, 1H), 4.50-4.40 (m, 2H), 4.40-4.33 (m, 1H), 4.22 (dd, J=15.8, 5.3 Hz, 1H), 3.76-3.62 (m, 2H), 3.16-3.05 (m, 2H), 2.44 (s, 3H), 2.41-2.17 (m, 4H), 2.09-2.01 (m, 1H), 1.98-1.80 (m, 3H), 1.74 (dq, J=14.9, 7.4 Hz, 2H), 0.96 (s, 9H), 0.95 (t, 3H). $^{13}$C NMR (151 MHz, dmso) δ 181.06, 172.39, 172.17, 171.46, 170.15, 156.37 (dd, J=246.6, 6.3 Hz), 152.73 (dd, J=249.4, 8.1 Hz), 151.86, 149.05, 148.13, 144.19, 139.91, 139.37, 139.13, 132.97, 131.64, 131.59, 130.05, 129.22 (d, J=14.7 Hz), 129.06, 127.84, 127.74, 126.89, 122.47 (d, J=14.1 Hz), 120.07, 119.02-118.20 (m), 117.95, 116.06, 112.75 (dd, J=23.4, 2.8 Hz), 69.34, 59.15, 56.90, 56.81, 53.87, 42.08, 38.38, 36.36, 35.63, 34.63, 26.85, 21.91, 17.27, 16.37, 13.04. LC-MS (ESI); m/z [M+H]$^+$: Calcd. for $C_{50}H_{55}F_2N_8O_8S_2$, 997.3552. Found 997.3524.

Example 17—Synthetic Scheme C: Compound 218, 219, and 222

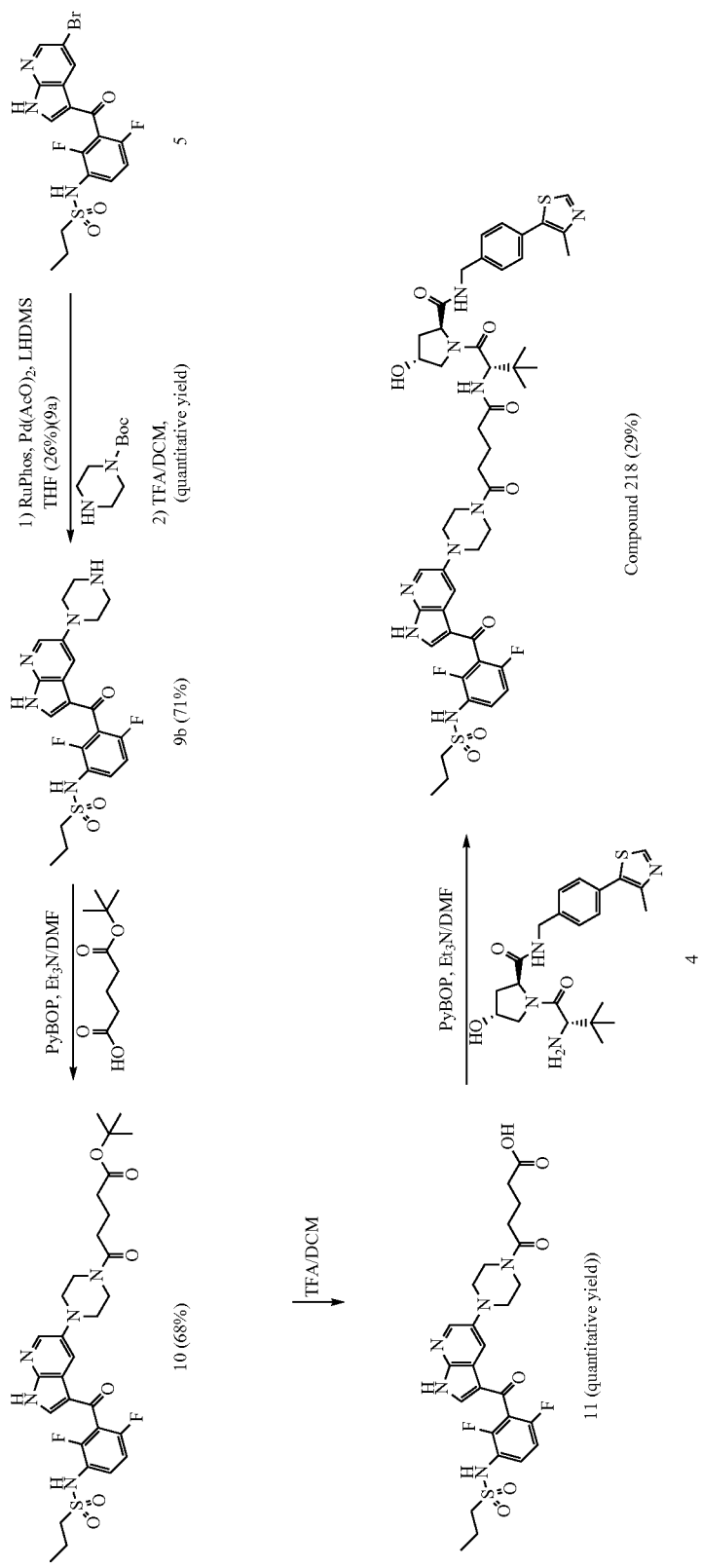

tert-Butyl 4-(3-(2,6-difluoro-3-(propylsulfonamido)benzoyl)-1H-pyrrolo[2,3-b]pyridin-5-yl)piperazine-1-carboxylate (9a)

A solution of N-[3-(5-bromo-1H-pyrrolo[2,3-b]pyridine-3-carbonyl)-2,4-difluoro-phenyl]propane-1-sulfonamide (61 mg, 0.13 mmol) and tert-butyl piperazine-1-carboxylate (37.19 mg, 0.2 mmol) in THF (3 mL) was purged with argon (5×). RuPhos (18.63 mg, 0.04 mmol) and Pd(OAc)$_2$ (2.99 mg, 0.01 mmol) were added followed by 1M LHMDS in THF (0.53 ml) The reaction mixture was heated to 60° C. and stirred for 6 hours. The reaction was cooled and poured into an aqueous solution of oxalic acid (5%, 2 ml), then a saturated aqueous NaHCO3 solution was added (5 ml), the product was extracted with DCM (3×10 ml). Organic extracts were combined, dried (Na2SO4) and evaporated under vacuum. Crude product was purified by PTLC (DCM:MeOH:NH$_4$OH, 90:9:1) (20 mg, 26%). $^1$H NMR (400 MHz, DMSO-d6) δ 12.61 (bs, 1H), 9.73 (bs, 1H), 8.27 (d, J=2.6 Hz, 1H), 8.03 (s, 1H), 7.94 (bs, 1H), 7.57 (td, J=9.0, 5.9 Hz, 1H), 7.26 (td, J=8.7, 1.5 Hz, 1H), 3.63-3.46 (m, 4H), 3.42-3.24 (m, 4H), 3.20-3.06 (m, 2H), 1.74 (dq, J=15.0, 7.4 Hz, 2H), 1.43 (s, 9H), 0.96 (t, J=7.4 Hz, 3H). $^{13}$C NMR (101 MHz, dmso) δ 180.37, 155.96 (dd, J=246.2, 7.2 Hz), 153.87, 152.31 (dd, J=249.1, 8.6 Hz), 144.72, 144.31, 138.06, 137.78, 128.59 (d, J=7.8 Hz), 121.94 (dd, J=13.6, 3.7 Hz), 119.35-117.93 (m), 117.56, 115.58, 115.17, 112.25 (dd, J=22.7, 3.8 Hz), 79.01, 53.49, 50.03, 43.56, 28.07, 16.84, 12.61. LC-MS (ESI); m/z: [M+H]$^+$ Calcd. for C$_{26}$H$_{32}$F$_2$N$_5$O$_5$S, 564.2092. Found 564.2

N-(2,4-difluoro-3-(5-(piperazin-1-yl)-1H-pyrrolo[2,3-b]pyridine-3-carbonyl)phenyl)propane-1-sulfonamide (9b)

A solution of tert-butyl 4-(3-(2,6-difluoro-3-(propylsulfonamido)benzoyl)-1H-pyrrolo-[2,3-b]pyridin-5-yl)piperazine-1-carboxylate (20 mg, 0.04 mmol) in a mixture of DCM:TFA (3 mL:1 mL) was stirred for 1 hour at room temperature. By TLC no more starting material (DCM:MeOH:NH$_4$OH, 90:9:1). 16.4 mg of product (quantitative yield), crude product was used in the next step without any further purification. LC-MS (ESI); m/z [M+H]$^+$: Calcd. for C$_{21}$H$_{24}$F$_2$N$_5$O$_3$S, 464.1567. Found 464.1712.

tert-butyl 5-(4-(3-(2,6-difluoro-3-(propylsulfonamido)benzoyl)-1H-pyrrolo[2,3-b]pyridin-5-yl)piperazin-1-yl)-5-oxopentanoate (10)

To a solution of N-(2,4-difluoro-3-(5-(piperazin-1-yl)-1H-pyrrolo[2,3-b]pyridine-3-carbonyl)-phenyl)propane-1-sulfonamide (16.4 mg, 0.04 mmol) and 5-(tert-butoxy)-5-oxopentanoic acid (7.99 mg, 0.04 mmol) in DMF (2 ml) was added TEA (0.1 ml, 0.72 mmol) and PyBOP (20.25 mg, 0.04 mmol) at room temperature. The reaction mixture was stirred for 3 hours at the same temperature. TLC (DCM:MeOH:NH$_4$OH, 90:9:1) shows no starting materials. The reaction mixture was dissolved in EtOAc (10 mL) and washed with brine/water (3×5 mL). Organic extract was concentrated under vacuum and crude product was purified by PTLC (DCM:MeOH:NH$_4$OH, 90:9:1) to give 15.4 mg of product (69% yield). $^1$H NMR (400 MHz, DMSO-d6) δ 12.67 (bs, 1H), 9.71 (bs, 1H), 8.29 (s, 1H), 8.03 (s, 1H), 7.95 (s, 1H), 7.56 (q, J=8.8 Hz, 1H), 7.26 (t, J=8.7 Hz, 1H), 3.71-3.57 (m, 4H), 3.24-3.06 (m, 6H), 2.39 (t, J=7.3 Hz, 2H), 2.26 (t, J=7.3 Hz, 2H), 1.84-1.66 (m, 4H), 1.40 (s, 9H), 0.96 (t, J=7.4 Hz, 3H). $^{13}$C NMR (101 MHz, dmso) δ 180.79, 172.52, 170.57, 156.37 (dd, J=246.4, 7.1 Hz), 152.72 (dd, J=249.2, 8.7 Hz), 145.03, 144.70, 138.44, 138.20, 129.01 (d, J=10.4 Hz), 122.34 (dd, J=13.7, 3.7 Hz), 119.28-118.29 (m), 117.97, 115.84, 115.58, 112.66 (dd, J=22.8, 3.3 Hz), 79.92, 53.89, 50.66, 45.18, 41.39, 34.57, 31.72, 28.21, 20.83, 17.25, 13.02. LC-MS (ESI); m/z [M+H]$^+$: Calcd. for C$_{30}$H$_{38}$F$_2$N$_5$O$_6$S, 634.2510. Found 634.2621.

5-((4-(3-(2,6-difluoro-3-(propylsulfonamido)benzoyl)-1H-pyrrolo[2,3-b]pyridin-5-yl)phenyl)amino)-5-oxopentanoic acid (11)

A solution of tert-butyl 5-((4-(3-(2,6-difluoro-3-(propylsulfonamido)benzoyl)-1H-pyrrolo[2,3-b]pyridin-5-yl)phenyl)amino)-5-oxopentanoate (10.7 mg, 0.02 mmol) in a mixture of TFA (1 ml, 13.46 mmol) and Dichloromethane (2 ml) was stirred for 2 hours at room temperature. Then the solvent was removed under vacuum and crude product was dried under high vacuum for 2 hours. Crude product was used in the next step without any further purification (9.7 mg, quantitative yield). LC-MS (ESI); m/z: [M+H]$^+$ Calcd. for C$_{28}$H$_{27}$F$_2$N$_4$O$_6$S, 585.1619. Found 585.1636.

(2S,4R)-1-((S)-2-(5-(4-(3-(2,6-difluoro-3-(propylsulfonamido)benzoyl)-1H-pyrrolo[2,3-b]pyridin-5-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide (Compound 218)

To a solution of 5-(4-(3-(2,6-difluoro-3-(propylsulfonamido)-benzoyl)-1H-pyrrolo[2,3-b]pyridin-5-yl)piperazin-1-yl)-5-oxopentanoic acid (9.3 mg, 0.02 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (8.27 mg, 0.018 mmol) in DMF (1 ml) was added TEA (0.1 ml, 0.72 mmol) and PyBOP (9.22 mg, 0.018 mmol) at room temperature. The reaction mixture was stirred for 4 hours at the same temperature. TLC (DCM:MeOH:NH$_4$OH, 90:9:1) shows no starting materials. The reaction mixture was diluted with EtOAc (10 mL) and washed with brine (5 mL, 4×), organic phase was dried (Na$_2$SO$_4$), and evaporated under vacuum. Crude mixture did not show product by TLC, just some VHL starting material (4) (Product is soluble in water). Water extracts were lyophilized for overnight, the solid residue was filtered using a mixture of DCM:MeOH:NH$_4$OH (90:9:1, 30 mL). Filtrate was evaporated to dryness and crude product was purified by PTLC (DCM:MeOH:NH$_4$OH, 90:9:1) to give 13 mg of product (81% yield). $^1$H NMR (500 MHz, DMSO-d6) δ 12.64 (bs, 1H), 9.74 (bs, 1H), 8.97 (s, 1H), 8.62-8.52 (m, 3H), 8.28 (d, J=2.0 Hz, 1H), 8.00 (s, 1H), 7.95 (bs, 1H), 7.90 (d, J=9.2 Hz, 1H), 7.59-7.49 (m, 1H), 7.47-7.27 (m, 4H), 7.20 (t, J=8.7 Hz, 1H), 5.13 (bs, 1H), 4.56 (d, J=9.3 Hz, 1H), 4.48-4.32 (m, 3H), 4.22 (dd, J=15.8, 5.3 Hz, 1H), 3.75-3.57 (m, 5H), 3.23-3.02 (m, 7H), 2.44 (s, 3H), 2.41-2.17 (m, 4H), 2.07-2.01 (m, 1H), 1.96-1.87 (m, 1H), 1.81-1.66 (m, 4H), 0.95 (s, 9H), 0.94 (t, 3H). $^{13}$C NMR (151 MHz, dmso) δ 180.70, 171.99, 171.92, 170.44, 169.75, 155.24 (dd, J=248.1, 5.5 Hz), 152.12 (dd, J=248.8, 8.5 Hz), 151.47, 147.73, 144.63, 144.31, 139.52, 138.02, 137.75, 131.19, 129.65, 128.65, 127.98-127.64 (m), 127.44, 123.91-123.09 (m), 118.86-117.72 (m), 117.60, 115.50, 115.23, 112.02 (dd, J=22.6, 3.2 Hz), 68.92, 58.74, 56.47, 56.43, 53.44, 50.31, 50.18, 48.63, 44.86, 41.68, 41.00, 37.99, 34.28, 31.80, 26.43, 21.36, 16.99, 15.97, 12.72. LC-MS (ESI); m/z [M+H]$^+$: Calcd. for $C_{48}H_{58}F_2N_9O_8S_2$, 990.3817. Found 990.3889.

Example 18—Synthetic Scheme C: Compound 304, and 306

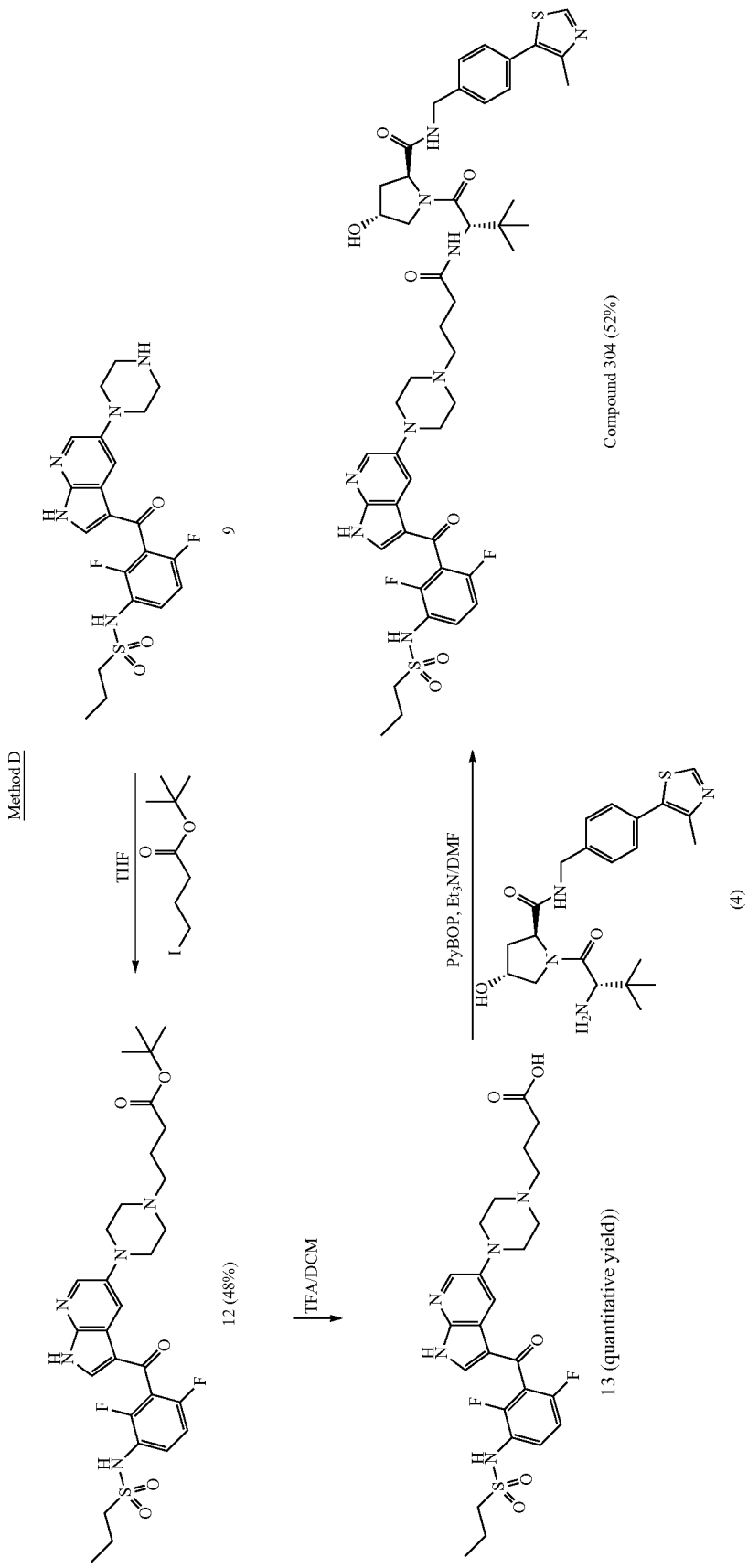

tert-Butyl 4-[4-[3-[2,6-difluoro-3-(propylsulfonylamino)benzoyl]-1H-pyrrolo[2,3-b]pyridin-5-yl]piperazin-1-yl]butanoate (12)

To a solution of methyl N-[2,4-difluoro-3-(5-piperazin-1-yl-1H-pyrrolo[2,3-b]-pyridine-3-carbonyl)phenyl]propane-1-sulfonamide; 2,2,2-trifluoroacetic acid (17.4 mg, 0.03 mmol) and tert-butyl 4-iodobutanoate (8.95 mg, 0.03 mmol) in DMF (1 ml) was added TEA (0.03 ml, 0.15 mmol), the resulting solution stirred for 16 hours at 50° C. (overnight). The solvent was evaporated under high vacuum and the residue was filtered over a silica-carbonate cartridge (1 g) using DCM:MeOH (9:1) as a eluent. Filtrate was evaporated under vacuum and crude product was purified by PTLC (DCM:MeOH:NH$_4$OH, 90:9:1), to give 8.8 mg of product (48% yield). $^1$H NMR (400 MHz, DMSO-d6) δ 12.63 (bs, 1H), 9.73 (bs, 1H), 8.25 (d, J=2.7 Hz, 1H), 8.00 (s, 1H), 7.89 (bs, 1H), 7.56 (td, J=9.0, 6.0 Hz, 2H), 7.34-7.16 (m, 1H), 3.25-3.04 (m, 6H), 2.68-2.52 (m, 4H), 2.34 (t, J=7.1 Hz, 2H), 2.24 (t, J=7.2 Hz, 2H), 1.85-1.61 (m, 4H), 1.40 (s, 9H), 0.96 (t, J=7.4 Hz, 3H). $^{13}$C NMR (151 MHz, DMSO-d6) δ 180.34, 172.23, 155.99 (dd, J=246.1, 7.0 Hz), 152.31 (dd, J=249.3, 8.6 Hz), 144.80, 143.96, 137.64, 137.36, 128.60 (d, J=9.9 Hz), 121.91 (dd, J=13.6, 3.7 Hz), 118.41 (t, J=23.8 Hz), 117.63, 115.12, 114.54, 112.26 (dd, J=22.8, 3.7 Hz), 56.95, 53.47, 52.70, 49.72, 32.69, 27.83, 21.79, 16.86, 12.63. LC-MS (ESI); m/z: [M+H]$^+$ Calcd. for C$_{29}$H$_{38}$F$_2$N$_5$O$_5$S, 606.2561. Found 606.2504.

4-[4-[3-[2,6-Difluoro-3-(propylsulfonylamino)benzoyl]-1H-pyrrolo[2,3-b]pyridin-5-yl]piperazin-1-yl]butanoic Acid (13)

A solution of tert-butyl 4-[4-[3-[2,6-difluoro-3-(propylsulfonylamino)benzoyl]-1H-pyrrolo[2,3-b]pyridin-5-yl]piperazin-1-yl]butanoate (8.8 mg, 0.01 mmol) in a mixture of TFA (1 ml, 13.46 mmol) and Dichloromethane (3 ml) was stirred for 1 hour. Then the solvent was removed under vacuum and crude product was dried under high vacuum for 2 hours. Crude product was used in the next step without any further purification (7.9 mg, quantitative yield). LC-MS (ESI); m/z: [M+H]+ Calcd. for C$_{25}$H$_{30}$F$_2$N$_5$O$_5$S, 550.1936. Found 550.1865.

(2S,4R)-1-((S)-2-(4-(4-(3-(2,6-difluoro-3-(propylsulfonamido)benzoyl)-1H-pyrrolo[2,3-b]pyridin-5-yl)piperazin-1-yl)butanamido)-3,3-dimethylbutanoyl)-4-hydroxy-N-(4-(4-methylthiazol-5-yl)benzyl)pyrrolidine-2-carboxamide (Compound 304)

To a solution of 4-[4-[3-[2,6-difluoro-3-(propylsulfonylamino)benzoyl]-1H-pyrrolo[2,3-b]pyridin-5-yl]butanoic acid (7.9 mg, 0.01 mmol) and (2S,4R)-1-[(2S)-2-amino-3,3-dimethyl-butanoyl]-4-hydroxy-N-[[4-(4-methylthiazo-1-5-yl)phenyl]methyl]pyrrolidine-2-carboxamide; hydrochloride (7.38 mg, 0.02 mmol) in DMF (1 ml) was added TEA (0.1 ml, 0.72 mmol) and PyBOP (8.23 mg, 0.02 mmol) at room temperature. The reaction mixture was stirred for 12 hours (overnight) at the same temperature. TLC (DCM:MeOH:NH$_4$OH, 90:9:1) shows no starting materials. The reaction mixture was evaporated to dryness. Crude product was filtered over a silica-carbonate cartridge (1 g) using DCM:MeOH (9:1) as eluent (washed a few times, product has high affinity for the stationary phase). Filtrate was evaporated under vacuum and crude product was purified by PTLC (DCM:MeOH, 9:1) to give 7.2 mg of product (52% yield). $^1$H NMR (500 MHz, DMSO-d6) δ 12.66 (bs, 1H), 9.73 (bs, 1H), 8.96 (s, 1H), 8.61-8.50 (m, 1H), 8.25 (s, 1H), 8.00 (s, 1H), 7.93 (bs, 1H), 7.88 (d, J=9.1 Hz, 1H), 7.63-7.49 (m, 1H), 7.40 (dd, 4H), 7.25 (t, J=8.7 Hz, 1H), 5.14 (s, 1H), 4.56 (d, J=9.1 Hz, 1H), 4.46-4.34 (m, 3H), 4.22 (dd, J=15.8, 4.7 Hz, 1H), 3.75-3.60 (m, 2H), 3.23-3.14 (m, 4H), 3.13-3.08 (m, 2H), 2.65-2.53 (m, 4H), 2.43 (s, 3H), 2.38-2.31 (m, 2H), 2.31-2.25 (m, 1H), 2.24-2.16 (m, 1H), 2.07-1.99 (m, 1H), 1.95-1.87 (m, 1H), 1.72 (dq, J=16.3, 10.5, 8.9 Hz, 4H), 0.95 (t, J=5.3 Hz, 3H), 0.95 (s, 9H). $^{13}$C NMR (151 MHz, DMSO-d6) δ 180.77, 172.43, 172.39, 170.12, 156.38 (dd, J=246.2, 7.1 Hz), 152.75 (dd, J=249.8, 9.0 Hz), 151.87, 148.13, 145.23, 144.35, 139.92, 138.09, 137.78, 131.59, 130.05, 129.21-128.76 (m), 127.84, 122.32 (d, J=13.1 Hz), 119.83-118.25 (m), 118.03, 115.53, 114.96, 112.68 (d, J=22.7 Hz), 69.30, 59.13, 57.62, 56.79, 55.33, 53.88, 53.06, 50.11, 42.07, 38.38, 35.68, 33.27, 26.83, 23.09, 17.26, 16.37, 13.04. LC-MS (ESI); m/z [M+H]$^+$: Calcd. for C$_{47}$H$_{58}$F$_2$N$_9$O$_7$S$_2$, 962.3868. Found 962.3986.

Example Synthesis of Compound 196: (Z)-2-(2,6-Dioxopiperidin-3-yl)-5-(3-(4-(4-(4-(1-(hydroxyimino)-2,3-dihydro-1H-inden-5-yl)-3-(pyridin-4-yl)-1H-pyrazol-1-yl)phenoxy)butoxy)phenyl)isoindoline-1,3-dione

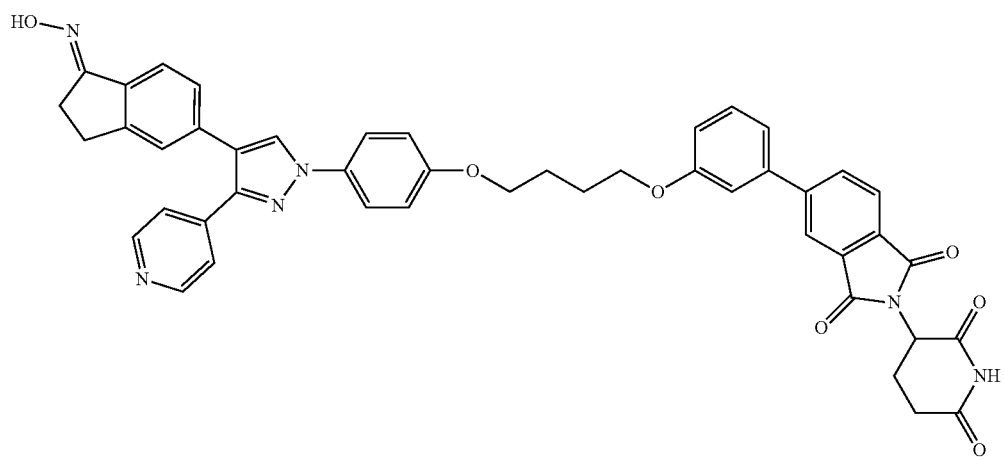 [SMILES: O=C1CCC(N2C(=O)c3ccc(-c4cccc(OCCCCOc5ccc(-n6cc(-c7ccc8c(c7)CC/C8=N\O)c(-c7ccncc7)n6)cc5)c4)cc3C2=O)C(=O)N1]

Step A: 5-(1-(4-(4-hydroxybutoxy)phenyl)-3-(pyridin-4-yl)-1H-pyrazol-4-yl)-2,3-dihydro-1H-inden-1-one

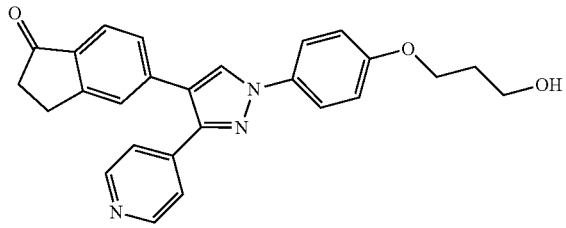 [SMILES: O=C1CCc2cc(-c3cn(-c4ccc(OCCCO)cc4)nc3-c3ccncc3)ccc21]

To a solution of 4-(4-(4-bromo-3-(pyridin-4-yl)-1H-pyrazol-1-yl)phenoxy)butan-1-ol (150 mg, 0.39 mmol) and 5-(4,4,5,5-tetramethyl-1,3,2-dioxaborolan-2-yl)-2,3-dihydroinden-1-one (120 mg, 0.46 mmol) in 1,4-dioxane/H$_2$O (10 mL, v/v=10/1) were added t-Bu$_3$PHBF$_4$ (44.8 mg, 0.15 mmol), CsF (234.9 mg, 1.54 mmol), Cy$_2$NCH$_3$ (5 drops) and Pd$_2$(dba)$_3$ (70.7 mg, 0.077 mmol). The resulting solution was stirred at 100° C. for 2 hours under N$_2$. The solvent was evaporated under reduced pressure. The residue was diluted with EA (30 mL), and the mixture was washed with brine. The organic phase was evaporated under reduced pressure, and the residue was purified by silica gel column chromatography on silica gel (DCM/MeOH=80/1) to afford the desired product (140 mg, 82.4% yield) as a colorless oil.

Step B: tert-butyl 5-(3-(pyridin-4-yl)-1-(4-(4-(3-(4,4,5,5-tetramethyl-1,3,2-dioxaborolan-2-yl)phenoxy)butoxy)phenyl)-1H-pyrazol-4-yl)-2,3-dihydro-1H-inden-1-one

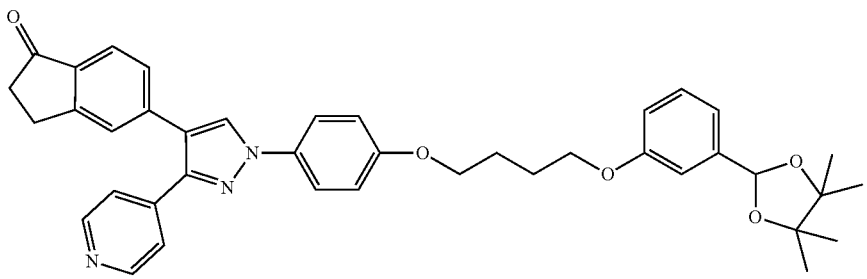 [SMILES: CC1(C)OC(c2cccc(OCCCCOc3ccc(-n4cc(-c5ccc6c(c5)CCC6=O)c(-c5ccncc5)n4)cc3)c2)OC1(C)C]

To a solution of 5-(1-(4-(4-hydroxybutoxy)phenyl)-3-(pyridin-4-yl)-1H-pyrazol-4-yl)-2,3-dihydro-1H-inden-1-one (140 mg, 0.32 mmol) and triethylamine (96.8 mg, 0.96 mmol) in DCM (10 mL) was added MsCl (43.8 mg, 0.38 mmol) at 0° C. After stirring at 30° C. for 1 hour, the solvent was removed under vacuum. The residue was diluted with EA (30 mL), and the mixture was washed with brine. The organic phase was concentrated to give the intermediate mesylate (180 mg, 0.34 mmol, 109%). To a solution of mesylate (90 mg, 0.17 mmol) in dry DMF (10 mL) were added 3-(4,4,5,5-tetramethyl-1,3,2-dioxaborolan-2-yl)phenol (449.7 mg, 0.22 mmol) and K$_2$CO$_3$ (47.9 mg, 0.34 mmol). The resulting mixture was stirred at 68° C. for 4 hours. The mixture was diluted by EtOAc (40 mL), and the mixture was washed with brine, and dried over anhydrous sodium sulfate. The organic phase was concentrated under reduced pressure. The residue was purified by preparative TLC (PE/EtOAc=1/3) to afford the desired product (80 mg, 71.7% yield). $^1$H NMR (400 MHz, CDCl$_3$): δ 8.65-8.55 (m, 2H), 8.00 (s, 1H), 7.76 (d, J=7.7 Hz, 1H), 7.68 (d, J=9.1 Hz, 2H), 7.51 (s, 2H), 7.44 (s, 1H), 7.29-7.41 (m, 4H), 7.02 (d, J=7.0 Hz, 3H), 4.12 (dd, J=14.0, 6.9 Hz, 4H), 3.60-3.67 (m, 1H), 3.13 (s, 2H), 2.74 (s, 2H), 2.01 (s, 2H), 1.34 (s, 12H).

Step C: tert-butyl 2-(2,6-dioxopiperidin-3-yl)-5-(3-(4-(4-(4-(1-oxo-2,3-dihydro-1H-inden-5-yl)-3-(pyridin-4-yl)-1H-pyrazol-1-yl)phenoxy)butoxy)phenyl)isoindoline-1,3-dione

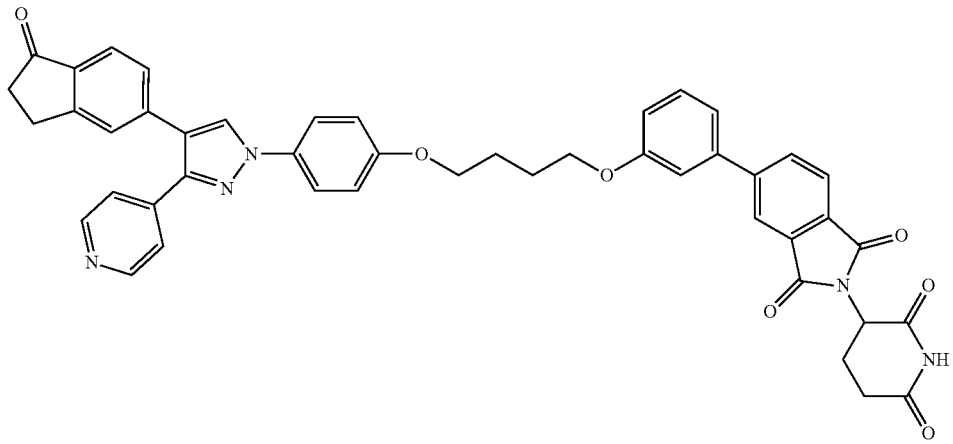 [SMILES: O=C1CCC(N2C(=O)c3ccc(-c4cccc(OCCCCOc5ccc(-n6cc(-c7ccc8c(c7)CCC8=O)c(-c7ccncc7)n6)cc5)c4)cc3C2=O)C(=O)N1]

To a solution of tert-butyl 5-(3-(pyridin-4-yl)-1-(4-(4-(3-(4,4,5,5-tetramethyl-1,3,2-dioxaborolan-2-yl)phenoxy)butoxy)phenyl)-1H-pyrazol-4-yl)-2,3-dihydro-1H-inden-1-one (80 mg, 0.12 mmol) and 5-(3-bromophenyl)-2-(2,6-dioxopiperidin-3-yl)isoindoline-1,3-dione (46.3 mg, 0.14 mmol) in 1,4-dioxane/H$_2$O (9 mL, 8:1) were added t-Bu$_3$PHBF$_4$ (14.5 mg, 0.050 mmol), CsF (75.8 mg, 0.50 mmol), Cy$_2$NMe (1 drop) and Pd$_2$(dba)$_3$ (22.8 mg, 0.025 mmol). The resulting mixture was stirred at 100° C. for 2 hours under N$_2$. The solvent was evaporated under reduced pressure. The residue was diluted with EA (30 mL), and the mixture was washed with brine. The organic phase was evaporated under reduced pressure. The residue was purified by TLC (PE/EtOAc=1/8) to afford the desired product (40 mg, 41.5% yield).

Step D: (Z)-2-(2,6-Dioxopiperidin-3-yl)-5-(3-(4-(4-(4-(1-(hydroxyimino)-2,3-dihydro-1H-inden-5-yl)-3-(pyridin-4-yl)-1H-pyrazol-1-yl)phenoxy)butoxy)phenyl)isoindoline-1,3-dione To a solution of tert-butyl 2-(2,6-dioxopiperidin-3-yl)-5-(3-(4-(4-(4-(1-oxo-2,3-dihydro-1H-inden-5-yl)-3-(pyridin-4-yl)-1H-pyrazol-1-yl)phenoxy)butoxy)phenyl)isoindoline-1,3-dione (40 mg, 0052 mmol) in CH$_3$CN/Py (5 mL/2 mL) was added NH$_2$OH.HCl (40 mg, 0.57 mmol). The reaction was stirred at 40° C. for 0.5 hours. The mixture was diluted with EtOAc (30 mL), and washed with brine twice. The organic layer was evaporated under reduced pressure. The residue was purified by preparative HPLC to afford the desired product as a white solid (13.5 mg, 8.6% yield). $^1$H NMR (400 MHz, CDCl$_3$): δ 8.47-8.86 (m, 3H), 8.27 (s, 1H), 8.09 (s, 1H), 7.94 (d, J=4.9 Hz, 3H), 7.68 (d, J=8.7 Hz, 3H), 7.52 (s, 2H), 7.36-7.47 (m, 2H), 7.29 (s, 1H), 7.21 (s, 1H), 7.15 (s, 1H), 7.02 (d, J=8.4 Hz, 3H), 4.97-5.04 (m, 1H), 4.13 (s, 4H), 2.74-3.12 (m, 8H), 2.21 (d, J=7.7 Hz, 2H), 2.01-2.09 (m, 3H). LCMS (ES$^+$): m/z 787.2 [M+H]$^+$.

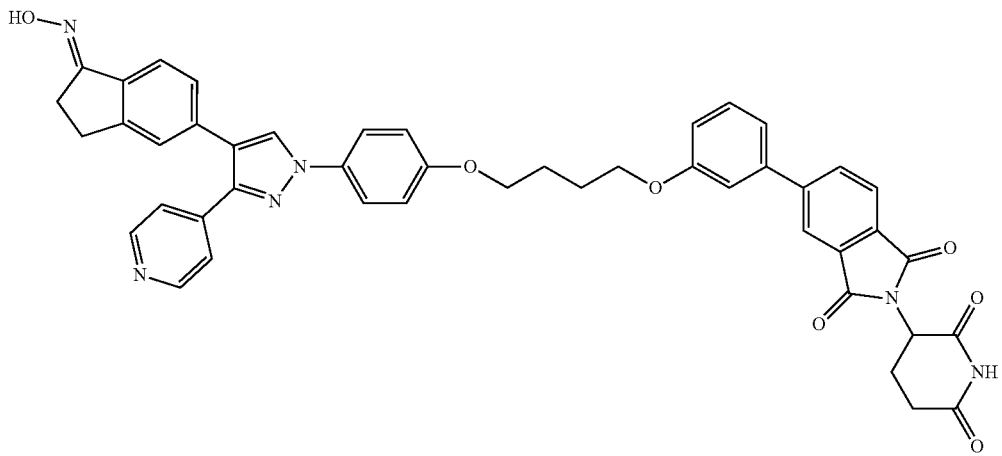 [SMILES: O=C1CCC(N2C(=O)c3ccc(-c4cccc(OCCCCOc5ccc(-n6cc(-c7ccc8c(c7)CC/C8=N\O)c(-c7ccncc7)n6)cc5)c4)cc3C2=O)C(=O)N1]

Example Synthesis of Compound 197: (E)-2-(2,6-Dioxopiperidin-3-yl)-5-(4-(2-(2-(4-(4-(1-(hydroxyimino)-2,3-dihydro-1H-inden-5-yl)-3-(pyridin-4-yl)-1H-pyrazol-1-yl)phenoxy)ethoxy)ethyl)piperazin-1-yl)isoindoline-1,3-dione

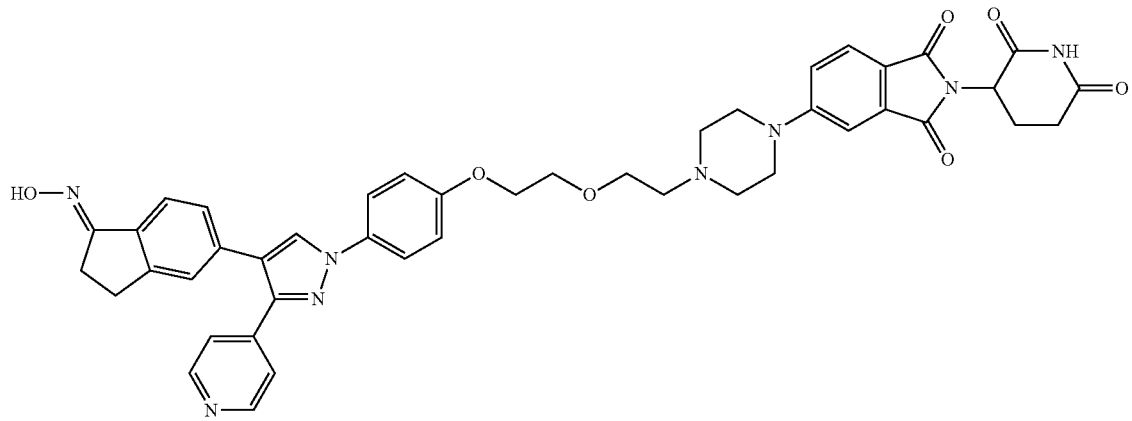 [SMILES: O=C1CCC(N2C(=O)c3ccc(N4CCN(CCOCCOc5ccc(-n6cc(-c7ccc8c(c7)CC/C8=N\O)c(-c7ccncc7)n6)cc5)CC4)cc3C2=O)C(=O)N1]

Step A: 2-(2-(4-(4-bromo-3-(pyridin-4-yl)-1H-pyrazol-1-yl)phenoxy)ethoxy)ethanol

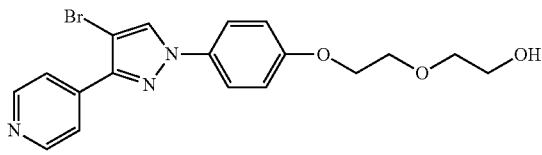 [SMILES: OCCOCCOc1ccc(-n2cc(Br)c(-c3ccncc3)n2)cc1]

To a solution of 4-(4-bromo-3-(pyridin-4-yl)-1H-pyrazol-1-yl)phenol (500 mg, 1.58 mmol) in dry DMF (5 mL) were added $Cs_2CO_3$ (1.55 g, 4.75 mmol) and 2-(2-hydroxyethoxy)ethyl 4-methylbenzenesulfonate (1.23 g, 4.75 mmol) subsequently. The resulting solution was stirred at 70° C. for 3 hours. After cooling to room temperature, the reaction was quenched with water (20 mL), and the mixture was extracted with EtOAc (20 mL×3). The combined organic layer was dried over anhydrous sodium sulfate and concentrated under vacuum. The residue was purified by silica gel column to afford the desired product (500 mg, 78% yield) as a yellow solid. $^1$H NMR (400 MHz, $CDCl_3$): δ 8.69 (s, 2H), 7.91-7.96 (m, 3H), 7.62 (d, J=8.8 Hz, 2H), 7.05 (d, J=8.4 Hz, 2H), 4.19 (t, J=4.4 Hz, 2H), 3.90 (t, J=4.0 Hz, 2H), 3.78 (t, J=4.8 Hz, 2H), 3.70 (t, J=4.4 Hz, 2H).

Step B: 2-(2-(4-(4-bromo-3-(pyridin-4-yl)-1H-pyrazol-1-yl)phenoxy)ethoxy)ethyl methanesulfonate

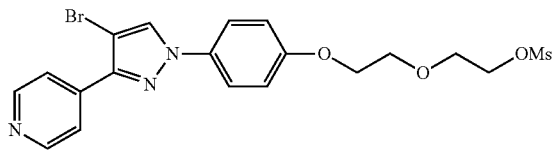 [SMILES: CS(=O)(=O)OCCOCCOc1ccc(-n2cc(Br)c(-c3ccncc3)n2)cc1]

To a solution of 2-(2-(4-(4-bromo-3-(pyridin-4-yl)-1H-pyrazol-1-yl)phenoxy)ethoxy)ethanol (500 mg, 1.24 mmol) and TEA (249 mg, 2.47 mmol) in DCM (5 mL) was added MsCl (169 mg, 1.48 mmol) dropwise at 0° C. The resulting solution was stirred at 5° C. for 0.5 hours. After it was quenched with saturated $NaHCO_3$ (20 mL), the mixture was extracted with DCM (20 mL×2). The combined organic layer was dried over anhydrous sodium sulfate and concentrated to afford the desired product (550 mg crude, calculated) as oil, which was used in next step directly. LCMS (ES+): m/z 482.0 $[M+H]^+$.

Step C: tert-butyl 4-(2-(2-(4-(4-bromo-3-(pyridin-4-yl)-1H-pyrazol-1-yl)phenoxy)ethoxy)ethyl)piperazine-1-carboxylate

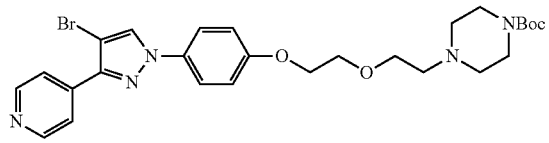 [SMILES: CC(C)(C)OC(=O)N1CCN(CCOCCOc2ccc(-n3cc(Br)c(-c4ccncc4)n3)cc2)CC1]

To a solution of 2-(2-(4-(4-bromo-3-(pyridin-4-yl)-1H-pyrazol-1-yl)phenoxy)ethoxy)ethyl methanesulfonate (0.5 g, 1.04 mmol) and tert-butyl piperazine-1-carboxylate (385 mg, 2.08 mmol) in DMF (5 mL) were added $K_2CO_3$ (715 mg, 5.20 mmol) and KI (860 mg, 5.20 mmol) subsequently. The resulting solution was stirred at 75° C. for 3 hours. After cooling to room temperature, the reaction was quenched with water (20 mL), and the mixture was extracted with ethyl acetate (30 mL×2). The combined organic layer was dried over anhydrous sodium sulfate and concentrated under vacuum. The residue was applied onto a silica gel column to afford desired product (0.4 g, 56% yield in two steps) as brown oil. $^1$H NMR (400 MHz, $CDCl_3$): δ 8.69 (d, J=4.8 Hz, 2H), 7.97 (m, 3H), 7.61 (d, J=9.2 Hz, 2H), 7.01 (d, J=8.8 Hz, 2H), 4.05-4.20 (m, 3H), 3.84 (t, J=4.8 Hz, 2H), 3.71 (t, J=5.6 Hz, 2H), 3.44 (m, 4H), 2.63 (t, J=5.6 Hz, 2H), 2.45 (m, 4H), 1.46 (s, 9H).

Step D: tert-butyl 4-(2-(2-(4-(4-(1-oxo-2,3-dihydro-1H-inden-5-yl)-3-(pyridin-4-yl)-1H-pyrazol-1-yl)phenoxy)ethoxy)ethyl)piperazine-1-carboxylate

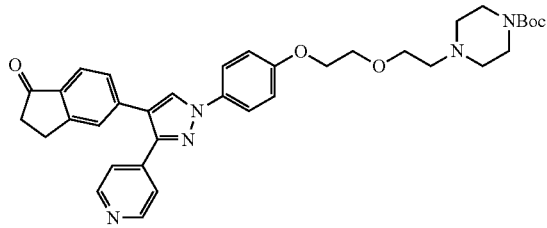 [SMILES: CC(C)(C)OC(=O)N1CCN(CCOCCOc2ccc(-n3cc(-c4ccc5c(c4)CCC5=O)c(-c4ccncc4)n3)cc2)CC1]

To a solution of tert-butyl 4-(2-(2-(4-(4-bromo-3-(pyridin-4-yl)-1H-pyrazol-1-yl)phenoxy)ethoxy)ethyl)piperazine-1-carboxylate (0.4 g, 0.70 mmol) and 5-(4,4,5,5-tetramethyl-1,3,2-dioxaborolan-2-yl)-2,3-dihydro-1H-inden-1-one (271 mg, 1.05 mmol) in 1,4-dioxane (15 mL)/H$_2$O (1.5 mL) were added CsF (425 mg, 2.80 mmol), Pd$_2$ (dba)$_3$ (256 mg, 0.28 mmol). tri-tert-butylphosphine tetrafluoroborate (162 mg, 0.56 mmol) and cat. N-cyclohexyl-N-methylcyclohexanamine subsequently. The reaction was heated to 100° C. for 2 h under N$_2$ atmosphere. After cooling to room temperature, the reaction was quenched with water (20 mL), and the mixture was extracted with ethyl acetate (30 mL×2). The combined organic layer was dried over anhydrous sodium sulfate and concentrated under vacuum. The residue was applied onto a silica gel column to afford desired product (0.4 g crude) as brown oil. LCMS (ES$^+$): m/z 624.7 [M+H]+.

Step E: 2-(2,6-dioxopiperidin-3-yl)-5-(4-(2-(2-(4-(4-(1-oxo-2,3-dihydro-1H-inden-5-yl)-3-(pyridin-4-yl)-1H-pyrazol-1-yl)phenoxy)ethoxy)ethyl)piperazin-1-yl)isoindoline-1,3-dione

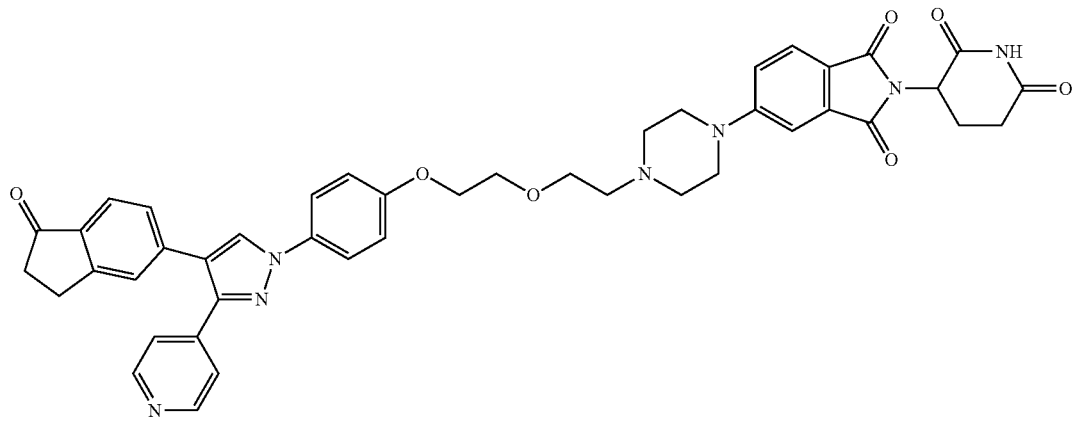 [SMILES: O=C1CCC(N2C(=O)c3ccc(N4CCN(CCOCCOc5ccc(-n6cc(-c7ccc8c(c7)CCC8=O)c(-c7ccncc7)n6)cc5)CC4)cc3C2=O)C(=O)N1]

To a solution of tert-butyl 4-(2-(2-(4-(4-(1-oxo-2,3-dihydro-1H-inden-5-yl)-3-(pyridin-4-yl)-1H-pyrazol-1-yl)phenoxy)ethoxy)ethyl)piperazine-1-carboxylate (400 mg, 0.64 mmol) in MeOH (5 mL) was added HCl in 1,4-dioxane (5 mL, 8 mol/L). The resulting solution was stirred at 10° C. for 1 hours. The solvent was removed under vacuum to afford the desired product (359 mg, calculated), which was used directly in next step. To a solution of crude product (359 mg, 0.64 mmol) in NMP (5 mL) were added DIEA (825 mg, 6.40 mmol) and 2-(2,6-dioxopiperidin-3-yl)-5-fluoroisoindoline-1,3-dione (530 mg, 1.92 mmol) subsequently. The reaction was irritated to 150° C. with microwave for 60 minutes. After cooling to room temperature, the reaction was quenched with water (20 mL), and the mixture was extracted with ethyl acetate (30 mL×2). The combined organic layer was dried over anhydrous sodium sulfate and concentrated under vacuum. The residue was applied onto a silica gel column to afford desired product (3 g crude, NMP included) as brown oil. LCMS (ES+): m/z 780.8 [M+H]$^+$.

Step F: (E)-2-(2,6-Dioxopiperidin-3-yl)-5-(4-(2-(2-(4-(4-(1-(hydroxyimino)-2,3-dihydro-1H-inden-5-yl)-3-(pyridin-4-yl)-1H-pyrazol-1-yl)phenoxy)ethoxy)ethyl)piperazin-1-yl)isoindoline-1,3-dione

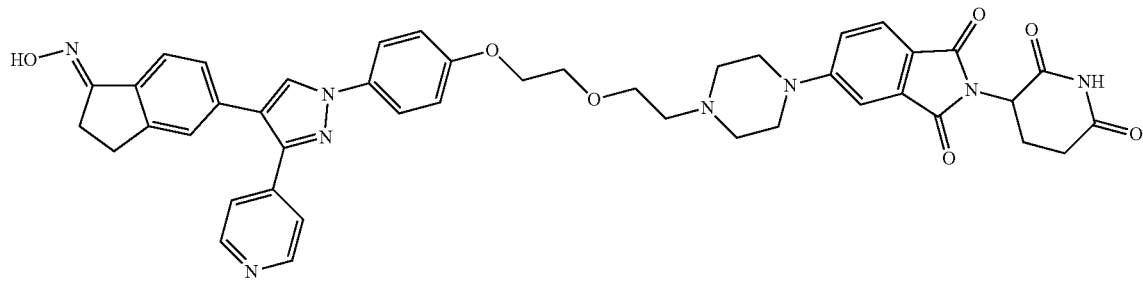 [SMILES: O=C1CCC(N2C(=O)c3ccc(N4CCN(CCOCCOc5ccc(-n6cc(-c7ccc8c(c7)CC/C8=N\O)c(-c7ccncc7)n6)cc5)CC4)cc3C2=O)C(=O)N1]

To a solution of 2-(2,6-dioxopiperidin-3-yl)-5-(4-(2-(2-(4-(4-(1-oxo-2,3-dihydro-1H-inden-5-yl)-3-(pyridin-4-yl)-1H-pyrazol-1-yl)phenoxy)ethoxy)ethyl)piperazin-1-yl)isoindoline-1,3-dione (625 mg, 0.64 mmol, calculated) and hydroxylamine hydrochloride (667 mg, 9.60 mmol) in MeOH/DCM (4 mL/1 mL) was added NaHCO$_3$ (1.21 g, 14.4 mmol) at 50° C. The mixture was stirred at 50° C. for 10 minutes. The residue was purified by preparative TLC with DCM/MeOH=20/1, and then it was further purified by preparative HPLC to afford the desired product (34 mg) as a yellow solid. $^1$H NMR (400 MHz, DMSO-d$_6$): δ 11.09 (s, 1H), 10.93 (s, 1H), 9.93 (br, 1H), 8.79 (s, 1H), 8.68 (s, 2H), 7.91 (d, J=8.4 Hz, 2H), 7.65-7.80 (m, 3H), 7.58 (d, J=8.0 Hz, 1H), 7.49 (s, 1H), 7.44 (s, 1H), 7.34 (d, J=8.4 Hz, 1H), 7.25 (d, J=8.0 Hz, 1H), 7.16 (d, J=8.8 Hz, 2H), 5.09 (m, 1H), 4.25 (m, 4H), 3.88 (m, 4H), 3.01 (m, 2H), 2.86 (m, 3H), 2.50 (m, 3H), 2.03 (m, 1H); LCMS (ES+): m/z 796.3 [M+H]$^+$.

Example Synthesis of Compound 198: (E)-2-(2,6-Dioxopiperidin-3-yl)-5-(2-(2-(4-(4-(4-(1-(hydroxyimino)-2,3-dihydro-1H-inden-5-yl)-3-(pyridin-4-yl)-1H-pyrazol-1-yl)phenyl)piperazin-1-yl)ethoxy)ethoxy)isoindoline-1,3-dione Step A: 5-(1-(4-(4-(2-(2 hydroxyethoxy)ethyl)piperazin-1-yl)phenyl)-3-(pyridin-4-yl)-1H-pyrazol-4-yl)-2,3-dihydro-1H-inden-1-one

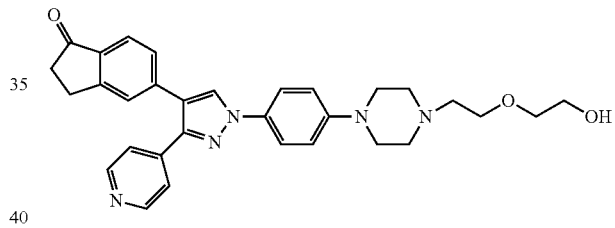

To a solution of tert-butyl 4-(4-(4-(1-oxo-2,3-dihydro-1H-inden-5-yl)-3-(pyridin-4-yl)-1H-pyrazol-1-yl)phenyl)piperazine-1-carboxylate (200 mg, 0.37 mmol) in MeOH (3 mL) was added 6 M HCl (g) in 1,4-dioxane (1 mL). The resulting solution was stirred at 25° C. for 1 hour. The solvent was removed under vacuum. The residue was diluted with 20 mL DCM, and the pH was adjusted to around 9 by progressively adding NaHCO$_3$ aqueous solution. The mixture was extracted with DCM. The combined organic layer

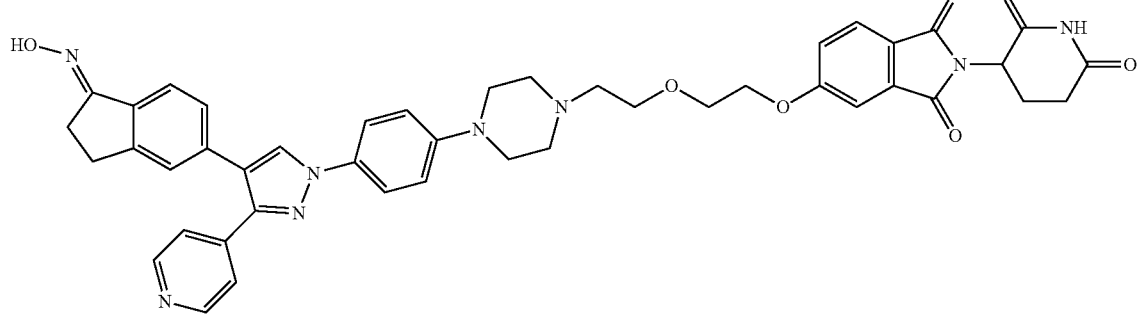

was dried over Na$_2$SO$_4$, filtered and concentrated under reduced pressure to give the desired product, which was used directly in next step. To a solution of above intermediate (180 mg crude, 0.37 mmol) in DMF (3 mL) were added 2-(2-hydroxyethoxy)ethyl 4-methylbenzenesulfonate (194 mg, 0.75 mmol) and K$_2$CO$_3$ (153.2 mg, 1.11 mmol). The resultant solution was stirred at 70° C. for 2 hours. After cooling to room temperature, the reaction was diluted with DCM (20 mL), and the mixture was washed with brine. The organic phase was dried over Na$_2$SO$_4$, filtered and concentrated under reduced pressure. The residue was purified by preparative TLC to afford the desired product (53 mg, 27.2% yield) as a yellow solid. LCMS (ES$^+$): m/z 524.2 [M+H]$^+$.

Step B: tert-butyl 2-(2,6-dioxopiperidin-3-yl)-5-(2-(2-(4-(4-(4-(1-oxo-2,3-dihydro-1H-inden-5-yl)-3-(pyridin-4-yl)-1H-pyrazol-1-yl)phenyl)piperazin-1-yl)ethoxy)ethoxy)isoindoline-1,3-dione

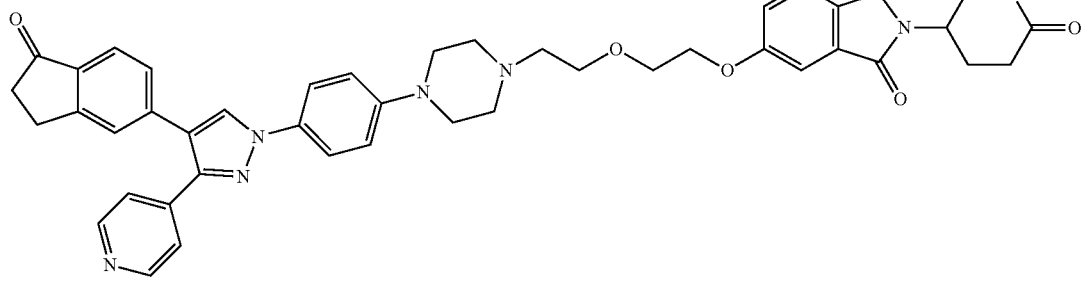

To a solution of 5-(1-(4-(4-(2-(2-hydroxyethoxy)ethyl)piperazin-1-yl)phenyl)-3-(pyridin-4-yl)-1H-pyrazol-4-yl)-2,3-dihydro-1H-inden-1-one (53 mg, 0.10 mmol), Ph$_3$P (78.7 mg, 0.3 mmol) and 2-(2,6-dioxopiperidin-3-yl)-5-fluoroisoindoline-1,3-dione (41.1 mg, 0.15 mmol) in dry THF (3.0 mL) was added DIAD (60.7 mg, 0.3 mmol) dropwise under N$_2$. The mixture was stirred at 20° C. for 1.5 hours. After it was quenched with H$_2$O (20 mL), the mixture was extracted with DCM (20 mL×3). The combined organic layer was washed with brine, dried over Na$_2$SO$_4$, and concentrated under vacuum. The residue was purified by preparative TLC to afford the desired product (crude, 45 mg, 34.7% yield) as a yellow solid. LCMS (ES$^+$): m/z 780.3 [M+H]$^+$.

Step C: (E)-2-(2,6-dioxopiperidin-3-yl)-5-(2-(2-(4-(4-(4-(1-(hydroxyimino)-2,3-dihydro-1H-inden-5-yl)-3-(pyridin-4-yl)-1H-pyrazol-1-yl)phenyl)piperazin-1-yl)ethoxy)ethoxy)isoindoline-1,3-dione

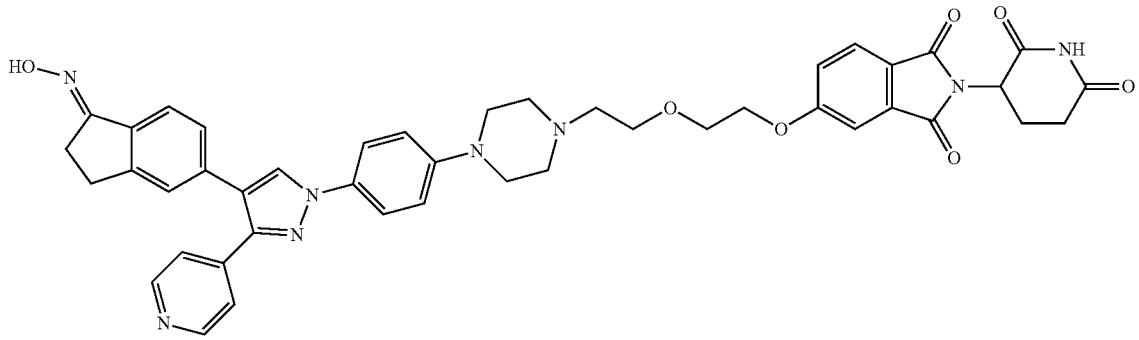 [SMILES: O=C1CCC(N2C(=O)c3ccc(OCCOCCN4CCN(c5ccc(-n6cc(-c7ccc8c(c7)CC/C8=N\O)c(-c7ccncc7)n6)cc5)CC4)cc3C2=O)C(=O)N1]

To a solution of tert-butyl 2-(2,6-dioxopiperidin-3-yl)-5-(2-(2-(4-(4-(4-(1-oxo-2,3-dihydro-1H-inden-5-yl)-3-(pyridin-4-yl)-1H-pyrazol-1-yl)phenyl)piperazin-1-yl)ethoxy)ethoxy)isoindoline-1,3-dione (45 mg, 0.058 mmol) in CH$_3$CN/pyridine (3.0 mL, v/v=2/1) was added hydroxylamine hydrochloride (40.1 mg, 0.58 mmol). The mixture was stirred at 40° C. for 20 minutes. Then the reaction was diluted with DCM (20 mL), and the mixture was washed with brine (10 mL×3). The combined organic layer was removed under vacuum, and the residue was purified by preparative TLC and preparative HPLC to afford the desired product (5.5 mg, 12% yield) as a yellow solid. $^1$H NMR (400 MHz, CDCl$_3$): δ 8.55 (s, 2H), 8.04 (s, 1H), 7.94 (s, 1H), 7.79 (d, J=8.0 Hz, 1H), 7.65 (d, J=8.8 Hz, 3H), 7.39 (s, 2H), 7.30 (s, 1H), 7.23 (s, 1H), 7.01 (d, J=8.8 Hz, 2H), 4.98-4.93 (m, 1H), 4.27 (s, 2H), 3.90 (s, 2H), 3.77 (s, 2H), 3.28 (s, 4H), 3.06-3.01 (m, 4H), 2.93-2.81 (m, 2H), 2.74 (s, 7H), 2.17-2.13 (br, 1H). LCMS (ES$^+$): m/z 795.3 [M+H]$^+$.

Example Synthesis of Compound 199: (E)-2-(2,6-dioxopiperidin-3-yl)-4-(3-(4-(4-(4-(1-(hydroxyimino)-2,3-dihydro-1H-inden-5-yl)-3-(pyridin-4-yl)-1H-pyrazol-1-yl)phenyl)piperazin-1-yl)propoxy)isoindoline-1,3-dione

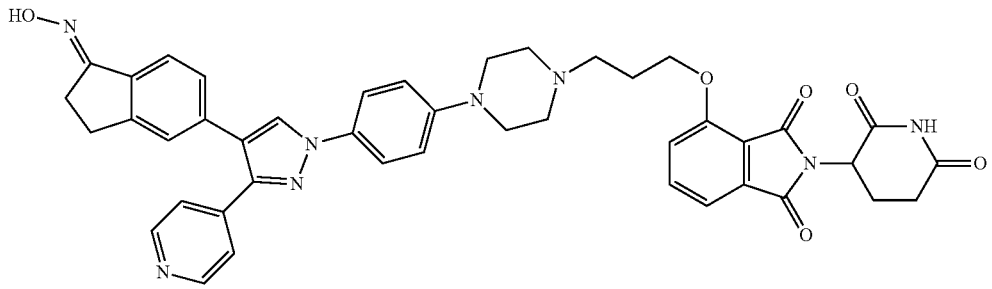 [SMILES: O=C1CCC(N2C(=O)c3cccc(OCCCN4CCN(c5ccc(-n6cc(-c7ccc8c(c7)CC/C8=N\O)c(-c7ccncc7)n6)cc5)CC4)c3C2=O)C(=O)N1]

Step A: 5-(1-(4-(4-(3-hydroxypropyl)piperazin-1-yl)phenyl)-3-(pyridin-4-yl)-1H-pyrazol-4-yl)-2,3-dihydro-1H-inden-1-one

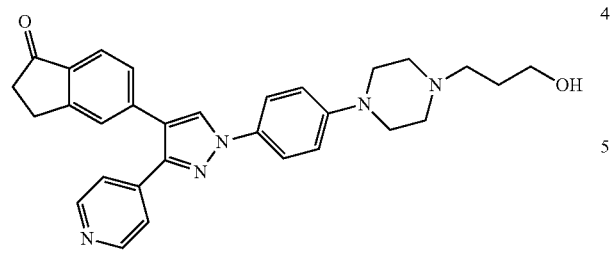

To a solution of tert-butyl 4-(4-(4-(1-oxo-2,3-dihydro-1H-inden-5-yl)-3-(pyridin-4-yl)-1H-pyrazol-1-yl)phenyl)piperazine-1-carboxylate (270 mg, 0.50 mmol) in MeOH (5 mL) was added 6 M HCl in 1,4-dioxane (1 mL). The resulting solution was stirred at 25° C. for 1 hour. The solvent was removed in vacuo. The residue was diluted with 20 mL DCM, and the pH was adjusted to ~9 by addition of NaHCO$_3$ aqueous. The mixture was extracted with DCM. The combined organic layer was dried over Na$_2$SO$_4$, filtered and concentrated under reduced pressure. The residue (240 mg crude) was used directly in next step without further purification.

To a solution of above intermediate (240 mg crude, 0.50 mmol) in DMF (5 mL) was added 3-hydroxypropyl 4-methylbenzenesulfonate (230 mg, 1 mmol) and $K_2CO_3$ (207 mg, 1.5 mmol). The resulting solution was stirred at 70° C. for 2 hours. After cooling to room temperature, the reaction was diluted with DCM (20 mL). The mixture was washed with brine, dried over $Na_2SO_4$. The solution was filtered and concentrated under reduced pressure. The residue was purified by preparative TLC to afford the desired product (100 mg, 30.5% yield) as a yellow solid. LCMS ($ES^+$): m/z 494.3 $[M+H]^+$.

Step B: tert-butyl 5-amino-4-(1,3-dioxo-4-(3-(4-(4-(4-(1-oxo-2,3-dihydro-1H-inden-5-yl)-3-(pyridin-4-yl)-1H-pyrazol-1-yl)phenyl)piperazin-1-yl)propoxy)isoindolin-2-yl)-5-oxopentanoate

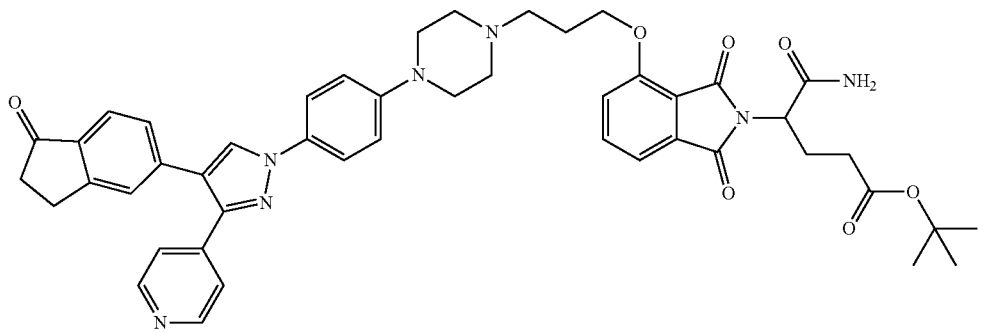 [SMILES: CC(C)(C)OC(=O)CCC(C(N)=O)N1C(=O)c2cccc(OCCCN3CCN(c4ccc(-n5cc(-c6ccc7c(c6)CCC7=O)c(-c6ccncc6)n5)cc4)CC3)c2C1=O]

To a solution of 5-(1-(4-(4-(3-hydroxypropyl)piperazin-1-yl)phenyl)-3-(pyridin-4-yl)-1H-pyrazol-4-yl)-2,3-dihydro-1H-inden-1-one (100 mg, 0.20 mmol) triphenylphosphine (157.2 mg, 0.60 mmol), and tert-butyl 5-amino-4-(4-hydroxy-1,3-dioxoisoindolin-2-yl)-5-oxopentanoate (104.4 mg, 0.30 mmol) in dry THF (5.0 mL) was added DIAD (121.2 mg, 0.60 mmol) dropwise under $N_2$. The mixture was stirred at 20° C. for 1.5 hours. The reaction was quenched with DCM (20 mL), and the mixture was washed with brine (10 mL×3). The organic phase was concentrated under vacuum. The residue was purified by preparative TLC to afford the desired product (120 mg, 43.1% yield) as a yellow solid. LCMS ($ES^+$): m/z 824.3 $[M+H]^+$.

Step C: 2-(2,6-dioxopiperidin-3-yl)-4-(3-(4-(4-(4-(1-oxo-2,3-dihydro-1H-inden-5-yl)-3-(pyridin-4-yl)-1H-pyrazol-1-yl)phenyl)piperazin-1-yl)propoxy)isoindoline-1,3-dione

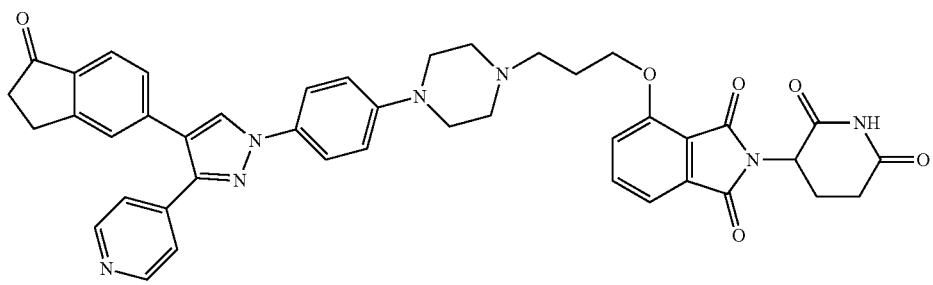 [SMILES: O=C1CCC(N2C(=O)c3cccc(OCCCN4CCN(c5ccc(-n6cc(-c7ccc8c(c7)CCC8=O)c(-c7ccncc7)n6)cc5)CC4)c3C2=O)C(=O)N1]

To a solution of tert-butyl 5-amino-4-(1,3-dioxo-4-(3-(4-(4-(4-(1-oxo-2,3-dihydro-1H-inden-5-yl)-3-(pyridin-4-yl)-1H-pyrazol-1-yl)phenyl)piperazin-1-yl)propoxy)isoindolin-2-yl)-5-oxopentanoate (crude 120 mg, 0.087 mmol) in acetonitrile (5 mL) was added p-toluenesulfonic acid (45.2 mg, 0.26 mmol). The mixture was stirred at 80° C. for 3 hours. After cooling to room temperature, the reaction was diluted with DCM (30 mL), and the mixture was washed with brine (10 mL×2). The organic phase was dried over $Na_2SO_4$, and concentrated under vacuum. The residue was purified by preparative TLC to afford the desired product (40 mg, 61.1% yield) as a yellow solid. LCMS (ES$^+$): m/z 750.3 [M+H]$^+$.

Step D: (E)-2-(2,6-dioxopiperidin-3-yl)-4-(3-(4-(4-(4-(1-(hydroxyimino)-2,3-dihydro-1H-inden-5-yl)-3-(pyridin-4-yl)-1H-pyrazol-1-yl)phenyl)piperazin-1-yl)propoxy)isoindoline-1,3-dione

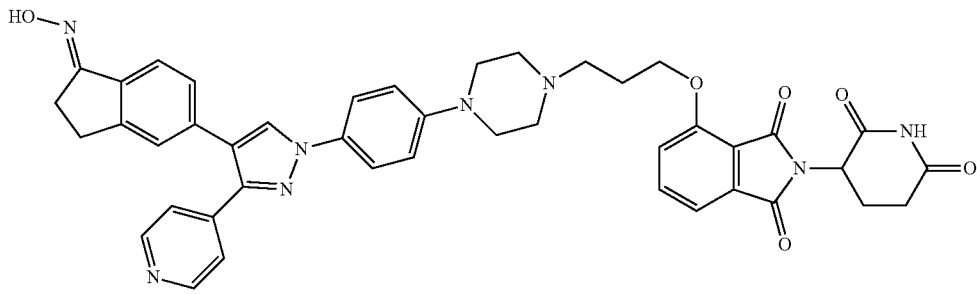 [SMILES: O=C1CCC(N2C(=O)c3cccc(OCCCN4CCN(c5ccc(-n6cc(-c7ccc8c(c7)CC/C8=N\O)c(-c7ccncc7)n6)cc5)CC4)c3C2=O)C(=O)N1]

To a solution of 2-(2,6-dioxopiperidin-3-yl)-4-(3-(4-(4-(4-(1-oxo-2,3-dihydro-1H-inden-5-yl)-3-(pyridin-4-yl)-1H-pyrazol-1-yl)phenyl)piperazin-1-yl)propoxy)isoindoline-1,3-dione (40 mg, 0.053 mmol) in acetonitrile/pyridine (v/v=3/1, 4 mL) was added hydroxylamine hydrochloride (36.8 mg, 0.53 mmol). The mixture was stirred at 40° C. for 20 minutes, and then it was diluted with DCM (20 mL). The mixture was washed with brine (10 mL×2). The organic phase was dried over $Na_2SO_4$, and concentrated under vacuum. The residue was purified by preparative TLC and preparative HPLC to afford the desired product (7.5 mg, 18.4% yield) as yellow solid. $^1$H NMR (400 MHz, DMSO-$d_6$): δ 11.11 (s, 1H), 10.90 (s, 1H), 8.70 (s, 1H), 8.57-8.56 (m, 2H), 7.85-7.77 (m, 3H), 7.56 (d, J=8.0 Hz, 2H), 7.49-7.45 (m, 3H), 7.41 (s, 1H), 7.22 (d, J=8.0 Hz, 1H), 7.10-7.08 (m, 2H), 5.12-5.08 (m, 1H), 4.32-4.28 (m, 2H), 3.22 (s, 5H), 3.03-2.97 (m, 2H), 2.89-2.80 (m, 3H), 2.62-2.57 (m, 7H), 2.06-1.99 (m, 3H). LCMS (ES$^+$): m/z 765.2 [M+H]$^+$.

Example Synthesis of Compound 200: (E)-2-(2,6-Dioxopiperidin-3-yl)-4-(3-(3-(4-(4-(1-(hydroxyimino)-2,3-dihydro-1H-inden-5-yl)-3-(pyridin-4-yl)-1H-pyrazol-1-yl)phenoxy)propoxy)phenyl)isoindoline-1,3-dione

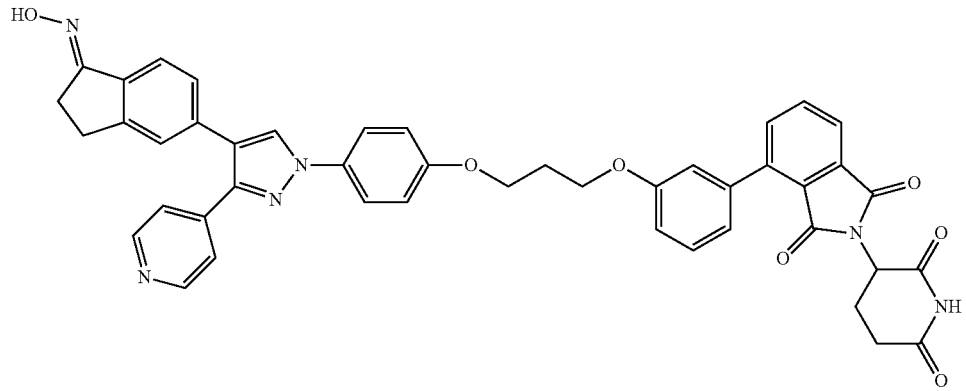 [SMILES: O=C1CCC(N2C(=O)c3cccc(-c4cccc(OCCCOc5ccc(-n6cc(-c7ccc8c(c7)CC/C8=N\O)c(-c7ccncc7)n6)cc5)c4)c3C2=O)C(=O)N1]

Step A: 3-(4-(4-bromo-3-(pyridin-4-yl)-1H-pyrazol-1-yl)phenoxy)propan-1-ol

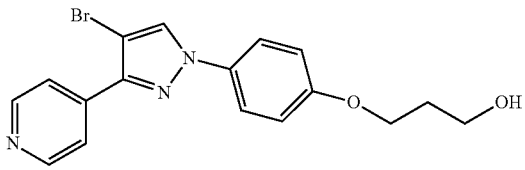 [SMILES: OCCCOc1ccc(-n2cc(Br)c(-c3ccncc3)n2)cc1]

To a solution of 4-(4-bromo-1H-pyrazol-3-yl) pyridine (500 mg, 1.58 mmol) in dry DMF (10.0 mL) were added K₂CO₃ (434 mg, 3.16 mmol) and 3-hydroxypropyl 4-methylbenzenesulfonate (400 mg, 1.74 mmol) subsequently. The resulting solution was stirred at 80° C. for 3 hours. The reaction mixture was diluted with EA (30 mL) and washed with brine. The organic phase was dried over anhydrous sodium sulfate and concentrated under vacuum. The residue was purified to afford the desired product 3-(4-(4-bromo-3-(pyridin-4-yl)-1H-pyrazol-1-yl)phenoxy)propan-1-ol (PE: EA=1:1) (400 mg, 67% yield) as light yellow oil. LCMS (ES⁺): m/z 376.0 [M+H]⁺.

Step B: 3-(4-(4-bromo-3-(pyridin-4-yl)-1H-pyrazol-1-yl)phenoxy)propan-1-ol

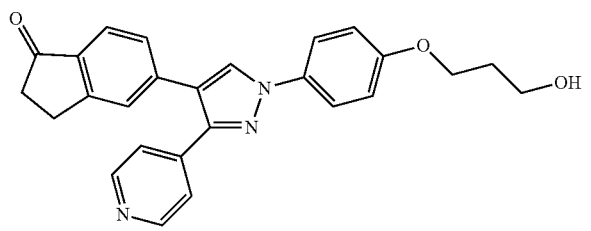 [SMILES: O=C1CCc2cc(-c3cn(-c4ccc(OCCCO)cc4)nc3-c3ccncc3)ccc21]

To a solution of 3-(4-(4-bromo-3-(pyridin-4-yl)-1H-pyrazol-1-yl)phenoxy) propan-1-ol (400 mg, 1.07 mmol), 5-(4,4,5,5-tetramethyl-1,3,2-dioxaborolan-2-yl)-2,3-dihydro-1H-inden-1-one (414 mg, 1.6 mmol), Pd₂ (dba)₃ (392 mg, 0.427 mmol), CsF (650 mg, 4.28 mmol). tri-tert-butylphosphine tetrafluoroborate (248 mg, 0.855 mmol), N,N-dicyclohexylmethylamine (9.0 mg, 0.047 mmol) in a mixture of 10% of water in 1,4-dioxane (10 mL) was irradiated with at 100° C. with microwave under N₂ for 2 hours. The mixture was cooled to room temperature and quenched with water. The mixture was diluted with EA and washed with water, and brine. The organic phase was dried over anhydrous sodium sulfate and concentrated under vacuum. The residue was purified to afford the desired product 3-(4-(4-bromo-3-(pyridin-4-yl)-1H-pyrazol-1-yl)phenoxy) propan-1-ol (DCM:MeOH=50:1) (450 mg, 87% yield) as yellow solid. LCMS (ES⁺): m/z 426.1 [M+H]⁺.

Step C: 5-(3-(pyridin-4-yl)-1-(4-(3-(3-(4,4,5,5-tetramethyl-1,3,2-dioxaborolan-2-yl)phenoxy)propoxy)phenyl)-1H-pyrazol-4-yl)-2,3-dihydro-1H-inden-1-one

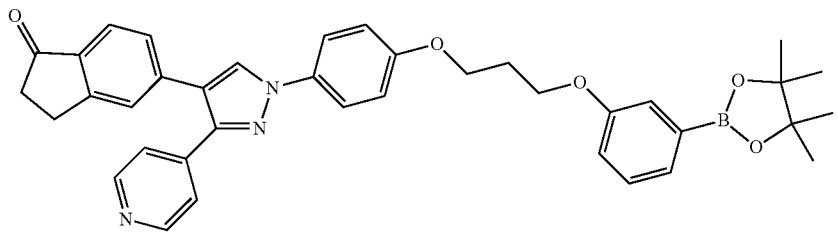 [SMILES: CC1(C)OB(c2cccc(OCCCOc3ccc(-n4cc(-c5ccc6c(c5)CCC6=O)c(-c5ccncc5)n4)cc3)c2)OC1(C)C]

To a solution of 3-(4-(4-bromo-3-(pyridin-4-yl)-1H-pyrazol-1-yl)phenoxy) propan-1-ol (450 mg, 1.06 mmol) and TEA (214 mg, 2.12 mmol) in DCM (10.0 mL) was added MsCl (145 mg, 1.27 mmol) dropwise at 0° C. The resulting solution was stirred at 25° C. for 1 hours. The solvent was evaporated and the residue was diluted with EA (50 mL). The solution was washed with saturated NaHCO₃ and brine. The organic layer was dried over anhydrous sodium sulfate. The solvent was removed under vacuum to afford crude desired product (520 mg crude), which was used in next step directly. To a solution of above desired product (520 mg, 1.03 mmol) in dry DMF (10 mL) were added K₂CO₃ (285 mg, 2.07 mmol) and 3-(4,4,5,5-tetramethyl-1,3,2-dioxaborolan-2-yl)phenol (341 mg, 1.55 mmol). The resulting solution was stirred at 70° C. overnight. After cooling to room temperature, the reaction mixture was diluted with EA (50 mL), and the mixture was washed with water, brine. The organic layer was dried over anhydrous sodium sulfate. The residue was purified by chromatography column to afford 5-(3-(pyridin-4-yl)-1-(4-(3-(3-(4,4,5,5-tetramethyl-1,3,2-dioxaborolan-2-yl)phenoxy)propoxy)phenyl)-1H-pyrazol-4-yl)-2,3-dihydro-1H-inden-1-one (200 g, 32% yield in two steps). ¹H NMR (400 MHz, CDCl₃): δ 8.62 (d, J=6 Hz, 2H), 8.00 (s, 1H), 7.76 (d, J=7.6 Hz, 1H), 7.68 (d, J=7.6 Hz, 2H), 7.51 (d, J=4.4 Hz, 2H), 7.27-7.44 (m, 4H), 7.02-7.04 (m, 3H), 4.15-4.22 (m, 3H), 4.11-4.13 (m, 4H), 3.12-3.14 (m, 2H), 2.72-2.75 (m, 2H), 2.10 (s, 1H), 1.34 (s, 11H), 2.83 (s, 1H).

Step D: 2-(2,6-dioxopiperidin-3-yl)-4-(3-(3-(4-(4-(1-oxo-2,3-dihydro-1H-inden-5-yl)-3-(pyridin-4-yl)-1H-pyrazol-1-yl)phenoxy)propoxy)phenyl)isoindoline-1,3-dione

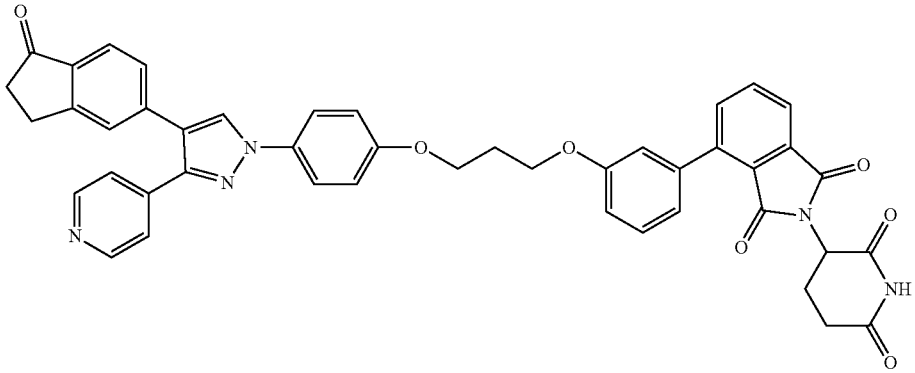 [SMILES: O=C1CCC(N2C(=O)c3cccc(-c4cccc(OCCCOc5ccc(-n6cc(-c7ccc8c(c7)CCC8=O)c(-c7ccncc7)n6)cc5)c4)c3C2=O)C(=O)N1]

To a solution of 4-chloro-2-(2,6-dioxopiperidin-3-yl)isoindoline-1,3-dione (47 mg, 0.159 mmol) and 5-(3-(pyridin-4-yl)-1-(4-(3-(3-(4,4,5,5-tetramethyl-1,3,2-dioxaborolan-2-yl)phenoxy)propoxy)phenyl)-1H-pyrazol-4-yl)-2,3-dihydro-1H-inden-1-one (47 mg, 0.159 mmol) in dioxane (5 mL)/H$_2$O (0.5 mL) were added CsF (97 mg, 0.64 mmol), Pd(aMphos)Cl$_2$ (12 mg, 0.016 mmol). After stirring at 100° C. for 2 hours under nitrogen atmosphere, the reaction mixture was diluted with 30 mL of ethyl acetate, and the solution was washed with brine (10 mL×3). The organic phase was dried over anhydrous sodium sulfate and concentrated under vacuum. The residue was purified by preparative TLC (DCM/MeOH=20/1) to afford the desired product 2-(2,6-dioxopiperidin-3-yl)-4-(3-(3-(4-(4-(1-oxo-2,3-dihydro-1H-inden-5-yl)-3-(pyridin-4-yl)-1H-pyrazol-1-yl)phenoxy)propoxy)phenyl)isoindoline-1,3-dione (50 mg, 40% yield) as yellow solid. LCMS (ES$^+$): m/z 758.2 [M+H]$^+$.

Step E: (E)-2-(2,6-dioxopiperidin-3-yl)-4-(3-(3-(4-(4-(1-(hydroxyimino)-2,3-dihydro-1H-inden-5-yl)-3-(pyridin-4-yl)-1H-pyrazol-1-yl)phenoxy)propoxy)phenyl)isoindoline-1,3-dione To a solution of 2-(2,6-dioxopiperidin-3-yl)-4-(3-(3-(4-(4-(1-oxo-2,3-dihydro-1H-inden-5-yl)-3-(pyridin-4-yl)-1H-pyrazol-1-yl)phenoxy)propoxy) phenyl)isoindoline-1,3-dione (50 mg, 0.053 mmol) in acetonitrile (2 mL) and pyridine (1 mL) was added hydroxylamine hydrochloride (34 mg, 0.53 mmol). After stirring 20 minutes at 40° C., the reaction was diluted with DCM (20 mL), and the mixture was washed with brine (10 mL×2). The organic phase was dried over Na$_2$SO$_4$, and concentrated under vacuum, The residue was purified by preparative TLC to afford (E)-2-(2,6-dioxopiperidin-3-yl)-4-(3-(3-(4-(4-(1-(hydroxyimino)-2,3-dihydro-1H-inden-5-yl)-3-(pyridin-4-yl)-1H-pyrazol-1-yl) phenoxy)propoxy) phenyl)isoindolin-e-1,3-dione (26 mg, 51% yield) as yellow solid. $^1$H NMR (400 MHz, DMSO-d6): δ 11.09 (s, 1H), 10.89 (s, 1H), 8.73 (s, 1H), 8.57 (d, J=5.2 Hz, 2H), 7.82-7.92 (m, 5H), 7.56 (d, J=8.0 Hz, 1H), 7.48 (d, J=4.8 Hz, 2), 7.37-7.41 (m, 2), 7.09-7.23 (m, 6H), 5.05-5.10 (m, 1H), 4.22-4.29 (m, 4H), 4.10 (s, 1H), 3.17 (d, J=4.8 Hz, 1H), 2.99-3.01 (m, 2H), 2.81-2.84 (m, 3H), 2.22-2.54 (m, 1H), 2.02-2.08 (m, 1H); LCMS (ES$^+$): m/z 773.2 [M+H]$^+$.

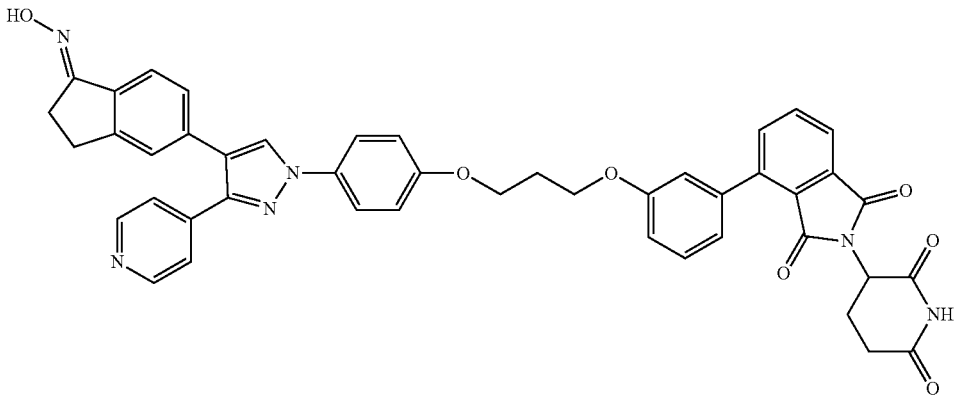 [SMILES: O=C1CCC(N2C(=O)c3cccc(-c4cccc(OCCCOc5ccc(-n6cc(-c7ccc8c(c7)CC/C8=N\O)c(-c7ccncc7)n6)cc5)c4)c3C2=O)C(=O)N1]

Example Synthesis of Compound 201

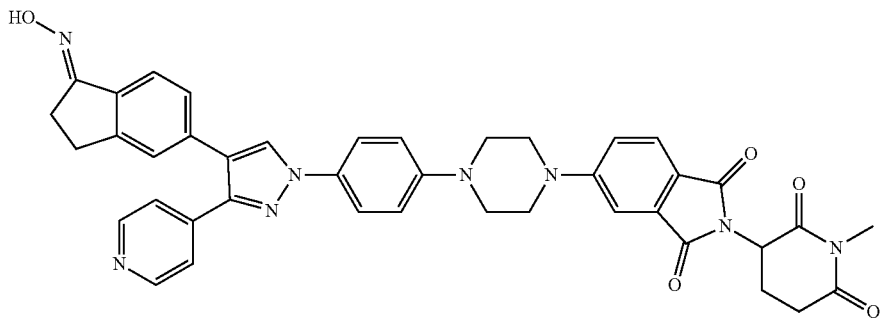 [SMILES: CN1C(=O)CCC(N2C(=O)c3ccc(N4CCN(c5ccc(-n6cc(-c7ccc8c(c7)CC/C8=N\O)c(-c7ccncc7)n6)cc5)CC4)cc3C2=O)C1=O]

Step A: 5-fluoro-2-(1-methyl-2,6-dioxopiperidin-3-yl)isoindoline-1,3-dione

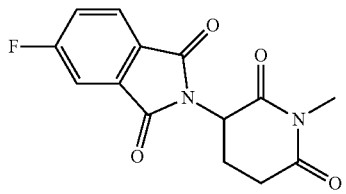 [SMILES: CN1C(=O)CCC(N2C(=O)c3ccc(F)cc3C2=O)C1=O]

To a solution of 2-(2,6-dioxopiperidin-3-yl)-5-fluoroisoindoline-1,3-dione (500 mg, 1.81 mmol) in dry DMF (10.0 mL) was added NaH (145 mg, 3.62 mmol) at 0° C. After stirring for 0.5 h, CH$_3$I (513.7 mg, 3.62 mmol) was added at 0° C. The resulting solution was stirred for 2 hours. After quenched with NH$_4$Cl aq., the mixture was diluted with 30 mL EA, and washed with brine (20 mL×3). The organic phase was dried over Na$_2$SO$_4$, concentrated to afford 5-Fluoro-2-(1-methyl-2,6-dioxopiperidin-3-yl)isoindoline-1,3-dione (500 mg, 95.2% yield) as brown solid, which was used next step directly. LCMS (ES$^+$): m/z 291.1 [M+H]$^+$.

Step B: 2-(1-methyl-2,6-dioxopiperidin-3-yl)-5-(4-(4-(4-(1-oxo-2,3-dihydro-1H-inden-5-yl)-3-(pyridin-4-yl)-1H-pyrazol-1-yl)phenyl)piperazin-1-yl)isoindoline-1,3-dione To a solution of tert-butyl 4-(4-(4-(1-oxo-2,3-dihydro-1H-inden-5-yl)-3-(pyridin-4-yl)-1H-pyrazol-1-yl)phenyl)piperazine-1-carboxylate (100 mg, 0.19 mmol) in MeOH (3 mL) was added 6 M HCl in 1,4-dioxane (1 mL). The resulting solution was stirred at 25° C. for 1 hour. The solution was concentrated and diluted with 20 mL DCM, added NaHCO$_3$ aq. to pH>7. The mixture was extracted with DCM. The organic layer was dried over Na$_2$SO$_4$, filtered and concentrated under reduced pressure which was used directly in next step. To a solution of above intermediate (90 mg crude, 0.19 mmol) in NMP (5 mL) was added 5-fluoro-2-(1-methyl-2,6-dioxopiperidin-3-yl)isoindoline-1,3-dione (100 mg, 0.29 mmol) and DIEA (245.1 mg, 1.9 mmol). The resulting solution was irradiated at 150° C. with microwave for 2 hours. After cooling to room temperature, it was diluted with DCM (20 mL), and the mixture was washed with brine. The organic phase was dried over Na$_2$SO$_4$, filtered and concentrated under reduced pressure. The residue was purified by silica gel column to afford 2-(1-methyl-2,6-dioxopiperidin-3-yl)-5-(4-(4-(4-(1-oxo-2,3-dihydro-1H-inden-5-yl)-3-(pyridin-4-yl)-1H-pyrazol-1-yl)phenyl)piperazin-1-yl)isoindoline-1,3-dione (43 mg, 26.5% yield). LCMS (ES$^+$): m/z 706.3 [M+H]$^+$.

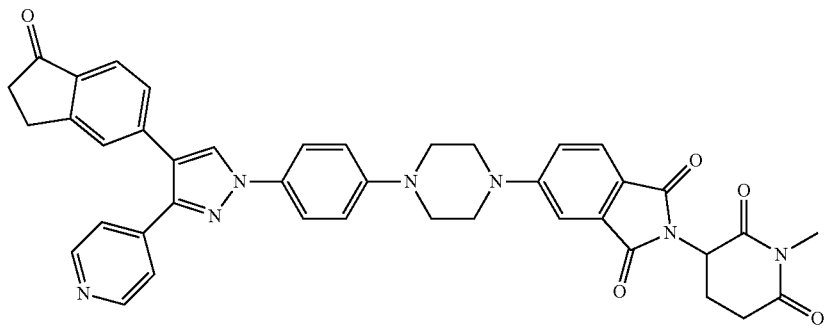 [SMILES: CN1C(=O)CCC(N2C(=O)c3ccc(N4CCN(c5ccc(-n6cc(-c7ccc8c(c7)CCC8=O)c(-c7ccncc7)n6)cc5)CC4)cc3C2=O)C1=O]

Step C: (E)-2-(2,6-dioxopiperidin-3-yl)-5-(4-(4-(4-(1-(hydroxyimino)-2,3-dihydro-1H-inden-5-yl)-3-(pyridin-4-yl)-1H-pyrazol-1-yl)phenyl)piperazin-1-yl)isoindoline-1,3-dione

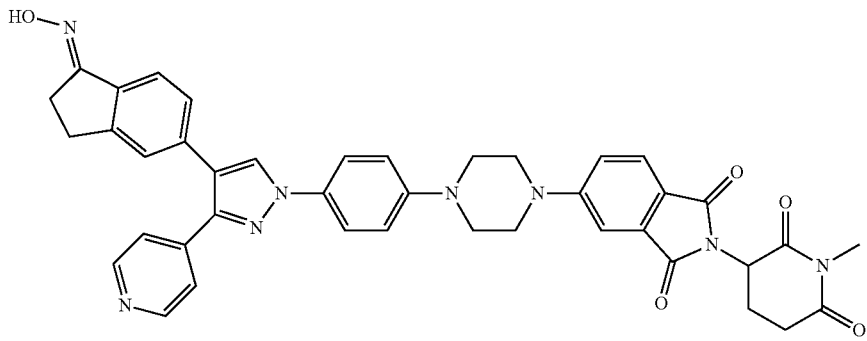 [SMILES: CN1C(=O)CCC(N2C(=O)c3ccc(N4CCN(c5ccc(-n6cc(-c7ccc8c(c7)CC/C8=N\O)c(-c7ccncc7)n6)cc5)CC4)cc3C2=O)C1=O]

To a solution of 2-(1-methyl-2,6-dioxopiperidin-3-yl)-5-(4-(4-(4-(1-oxo-2,3-dihydro-1H-inden-5-yl)-3-(pyridin-4-yl)-1H-pyrazol-1-yl)phenyl)piperazin-1-yl)isoindoline-1,3-dione (43 mg, 0.061 mmol) in acetonitrile/pyridine (3 mL, v/v=2/1) was added hydroxylamine hydrochloride (42.4 mg, 0.61 mmol) at room temperature. The mixture was heated to 40° C. for 40 minutes. After cooling to room temperature, it was diluted with DCM (20 mL), washed with brine (10 mL). The organic phase was concentrated under vacuum. The residue was purified by preparative TLC to afford (E)-2-(2, 6-dioxopiperidin-3-yl)-5-(4-(4-(4-(1-(hydroxyimino)-2,3-dihydro-1H-inden-5-yl)-3-(pyridin-4-yl)-1H-pyrazol-1-yl) phenyl)piperazin-1-yl)isoindoline-1,3-dione (23 mg, 52.3% yield) as a yellow solid. $^1$H NMR (400 MHz, DMSO-d6): δ 10.90 (s, 1H), 8.73 (s, 1H), 8.58-8.56 (d, J=8.0 Hz, 2H), 7.84-7.82 (d, J=8.8 Hz, 2H), 7.74-7.72 (d, J=8.4 Hz, 1H), 7.56-7.55 (d, J=8.4 Hz, 1H), 7.49-7.48 (m, 2H), 7.43-7.41 (m, 2H), 7.36-7.34 (m, 1H), 7.22-7.21 (d, J=8.0 Hz, 1H), 7.17-7.15 (d, J=10 Hz, 2H), 5.18-5.14 (m, 1H), 3.66 (s, 4H), 3.42 (s, 4H), 3.02-2.91 (m, 6H), 2.85-2.74 (m, 3H), 2.60-2.53 (m, 1H), 2.09-2.00 (br, 1H). LCMS (ES$^+$): m/z 721.3 [M+H]$^+$.

Example Synthesis of Compound 202: (3R)—N-(3-(5-(4-(4-(2-(4-(2-(2,6-Dioxopiperidin-3-yl)-1,3-dioxoisoindolin-5-yl)piperazin-1-yl)ethyl)piperazin-1-yl)phenyl)-1H-pyrrolo[2,3-b]pyridine-3-carbonyl)-2,4-difluorophenyl)-3-fluoropyrrolidine-1-sulfonamide

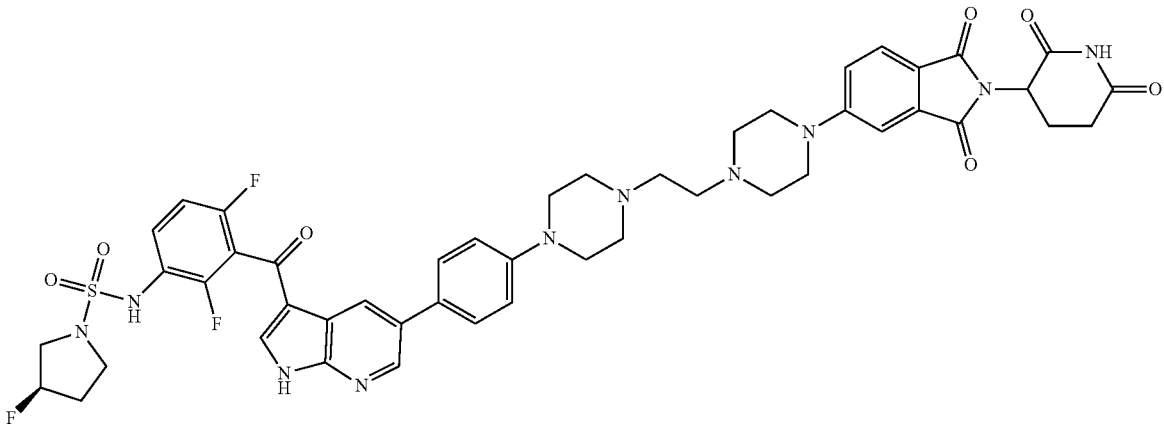 [SMILES: O=C1CCC(N2C(=O)c3ccc(N4CCN(CCN5CCN(c6ccc(-c7cnc8[nH]cc(C(=O)c9c(F)ccc(NS(=O)(=O)N%10CC[C@@H](F)C%10)c9F)c8c7)cc6)CC5)CC4)cc3C2=O)C(=O)N1]

Step A: 1-(4-bromophenyl)-4-(2,2-diethoxyethyl)piperazine

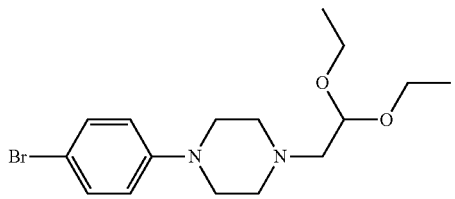 [SMILES: CCOC(CN1CCN(c2ccc(Br)cc2)CC1)OCC]

To a solution of 1-(4-bromophenyl)piperazine (5 g, 20.8 mmol) in dry DMF (50 ml) was added 2-bromo-1,1-diethoxyethane (4.1 g, 20.8 mmol) and $K_2CO_3$ (8.6 g, 62.4 mmol). The resulting solution was stirred at 90° C. for 16 hours. The reaction was diluted with EA (50 mL) and the mixture was washed (20 mL×2). The organic layer was dried over anhydrous sodium sulfate and concentrated under vacuum. The residue was applied onto a silica gel column to afford desired product (6 g, 81% yield) as oil.

$^1$H NMR (400 MHz, $CDCl_3$): δ 7.32 (d, J=9.2 Hz, 2H), 6.77 (d, J=8.8 Hz, 2H), 4.67 (t, J=5.2 Hz, 1H), 3.69-3.72 (m, 2H), 3.54-3.58 (m, 2H), 3.15 (m, 4H), 2.68-2.71 (m, 4H), 2.60 (d, J=5.2 Hz, 2H), 1.22 (t, J=7.2 Hz, 6H).

Step B: 1-(2,2-diethoxyethyl)-4-(4-(4,4,5,5-tetramethyl-1,3,2-dioxaborolan-2-yl)phenyl) piperazine

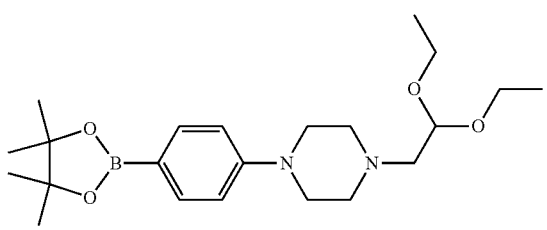 [SMILES: CCOC(CN1CCN(c2ccc(B3OC(C)(C)C(C)(C)O3)cc2)CC1)OCC]

To a solution of 1-(4-bromophenyl)-4-(2,2-diethoxyethyl)piperazine (7.8 g crude, 21.9 mmol) in 1,4-dioxane (70 mL) were added 4,4,4',4',5,5,5',5'-octamethyl-2,2'-bi(1,3,2-dioxaborolane) (8.3 g, 32.8 mmol), Pd(dppf)Cl$_2$ (1.6 g, 2.2 mmol) and KOAc (6.4 g, 65.6 mmol). The resulting solution was stirred overnight at 90° C. under N$_2$ atmosphere. TLC showed completion of the reaction. After cooled to room temperature, the reaction mixture was concentrated and purified by chromatography column to afford 1-(2,2-diethoxyethyl)-4-(4-(4,4,5,5-tetramethyl-1,3,2-dioxaborolan-2-yl)phenyl)piperazine (5 g, 74% yield). $^1$H NMR (400 MHz, CDCl$_3$): δ 7.69 (d, J=8.4 Hz, 2H), 6.87 (d, J=8.4 Hz, 2H), 4.70 (m, 1H), 3.50-3.72 (m, 4H), 3.26 (m, 4H), 2.72 (m, 4H), 2.60 (d, J=5.2 Hz, 2H), 1.32 (s, 12H), 1.22 (t, J=7.2 Hz, 6H).

Step C: (R)—N-(3-(5-(4-(4-(2,2-diethoxyethyl)piperazin-1-yl)phenyl)-1H-pyrrolo[2,3-b]pyridine-3-carbonyl)-2,4-difluorophenyl)-3-fluoropyrrolidine-1-sulfonamide

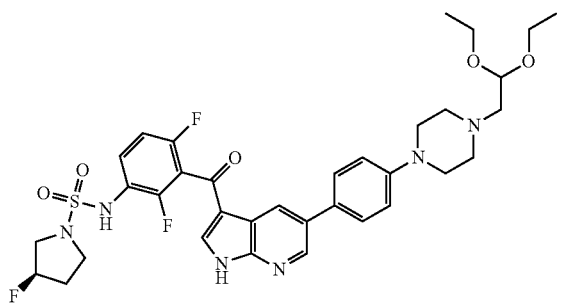 [SMILES: CCOC(CN1CCN(c2ccc(-c3cnc4[nH]cc(C(=O)c5c(F)ccc(NS(=O)(=O)N6CC[C@@H](F)C6)c5F)c4c3)cc2)CC1)OCC]

To a solution of (R)—N-(3-(5-bromo-1H-pyrrolo[2,3-b]pyridine-3-carbonyl)-2,4-difluorophenyl)-3-fluoropyrrolidine-1-sulfonamide (300 mg, 0.60 mmol) in 1,4-dioxane/H$_2$O (10 mL/2 mL) was added 1-(2,2-diethoxyethyl)-4-(4-(4,4,5,5-tetramethyl-1,3,2-dioxaborolan-2-yl)phenyl) piperazine (726 mg, 1.80 mmol), Pd(aMphos)Cl$_2$ (42 mg, 0.06 mmol) and CsF (363 mg, 3.20 mmol). The resulting solution was stirred at 95° C. for 3 hours under N$_2$ atmosphere. TLC showed completion of the reaction. After cooling to room temperature, the reaction mixture was diluted with EA (50 mL), washed with water and brine. The organic layer was dried over anhydrous sodium sulfate. The residue was purified by chromatography column to afford (R)—N-(3-(5-(4-(4-(2,2-Diethoxyethyl)piperazin-1-yl)phenyl)-1H-pyrrolo[2,3-b]pyridine-3-carbonyl)-2,4-difluorophenyl)-3-fluoropyrrolidine-1-sulfonamide (350 mg, 70% yield). LCMS (ES$^+$): m/z 701.3 [M+H]$^+$.

Step D: (R)—N-(2,4-difluoro-3-(5-(4-(4-(2-oxoethyl)piperazin-1-yl)phenyl)-1H-pyrrolo[2,3-b]pyridine-3-carbonyl)phenyl)-3-fluoropyrrolidine-1-sulfonamide

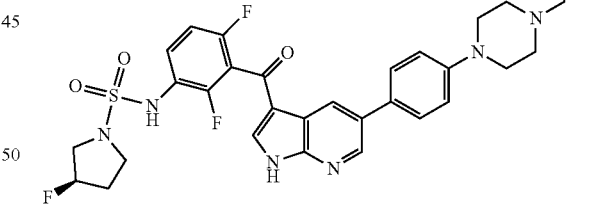

To a solution of (R)—N-(3-(5-(4-(4-(2,2-diethoxyethyl)piperazin-1-yl)phenyl)-1H-pyrrolo[2,3-b]pyridine-3-carbonyl)-2,4-difluorophenyl)-3-fluoropyrrolidine-1-sulfonamide (350 mg, 0.50 mmol) in CH$_3$CN (10 mL) was added concentrated HCl (3 mL, which was diluted with 9 mL H$_2$O). The resulting solution was stirred at 55° C. for 16 hours. After cooled to room temperature, the reaction mixture was added sat. NaHCO$_3$ to adjust pH to 7-8. Lots of solid was observed. The suspension was extracted by DCM. The organic phase was dried over anhydrous sodium sulfate and concentrated to afford (R)—N-(2,4-Difluoro-3-(5-(4-(4-(2-oxoethyl)piperazin-1-yl)phenyl)-1H-pyrrolo[2,3-b]pyridine-3-carbonyl)phenyl)-3-fluoropyrrolidine-1-sulfonamide (490 mg, crude). LCMS (ES$^+$): m/z 645.2 [M+H+18]$^+$.

Step E: (3R)—N-(3-(5-(4-(4-(2-(4-(2-(2,6-Dioxopi-
peridin-3-yl)-1,3-dioxoisoindolin-5-yl)piperazin-1-
yl)ethyl)piperazin-1-yl)phenyl)-1H-pyrrolo[2,3-b]
pyridine-3-carbonyl)-2,4-difluorophenyl)-3-
fluoropyrrolidine-1-sulfonamide

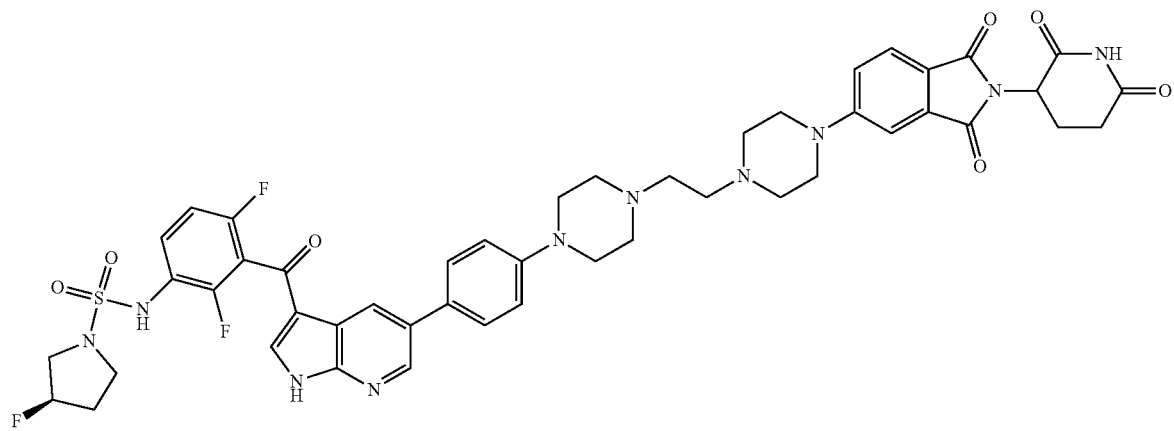 [SMILES: O=C1CCC(N2C(=O)c3ccc(N4CCN(CCN5CCN(c6ccc(-c7cnc8[nH]cc(C(=O)c9c(F)ccc(NS(=O)(=O)N%10CC[C@@H](F)C%10)c9F)c8c7)cc6)CC5)CC4)cc3C2=O)C(=O)N1]

To a solution of (R)—N-(2,4-difluoro-3-(5-(4-(4-(2-oxo-ethyl)piperazin-1-yl)phenyl)-1H-pyrrolo[2,3-b]pyridine-3-carbonyl)phenyl)-3-fluoropyrrolidine-1-sulfonamide (490 mg crude, 0.80 mmol) in THF/MeOH/DMSO (15 mL, 1/1/1) was added 2-(2,6-dioxopiperidin-3-yl)-5-(piperazin-1-yl) isoindoline-1,3-dione hydrochloride (364 mg, 0.96 mmol) and two drops of AcOH. Then NaBH$_3$CN (248 mg, 4.00 mmol) was added. The resultant solution was stirred at 20° C. for 2 hours. The reaction mixture was diluted with 20 mL of saturated NaCl solution and extracted with DCM. The organic phase was dried over anhydrous sodium sulfate and concentrated. Crude was applied onto a silica gel column first and then by preparative HPLC to afford desired product (3R)—N-(3-(5-(4-(4-(2-(4-(2-(2,6-Dioxopiperidin-3-yl)-1, 3-dioxoisoindolin-5-yl)piperazin-1-yl)ethyl)piperazin-1-yl) phenyl)-1H-pyrrolo[2,3-b]pyridine-3-carbonyl)-2,4-difluo-rophenyl)-3-fluoropyrrolidine-1-sulfonamide (75 mg, 16% yield in two steps) as yellow solid. $^1$H NMR (400 MHz, DMSO-d6): δ 12.92 (s, 1H), 11.08 (s, 1H), 9.80 (br, 1H), 8.54-8.66 (m, 2H), 8.07 (s, 1H), 7.59-7.69 (m, 4H), 7.25-7.35 (m, 3H), 7.07 (d, J=8.4 Hz, 2H), 5.05-5.36 (m, 2H), 3.22-3.48 (m, 14H), 2.55-3.00 (m, 14H), 1.90-2.20 (m, 4H); LCMS (ES$^+$): m/z 954.3 [M+H]$^+$.

Example Synthesis of Compound 203: (E)-2-(2,6-
Dioxopiperidin-3-yl)-5-(2-(3-(4-(1-(hydroxyimino)-
2,3-dihydro-1H-inden-5-yl)-3-(pyridin-4-yl)-1H-
pyrazol-1-yl)phenoxy)ethoxy)isoindoline-1,3-dione

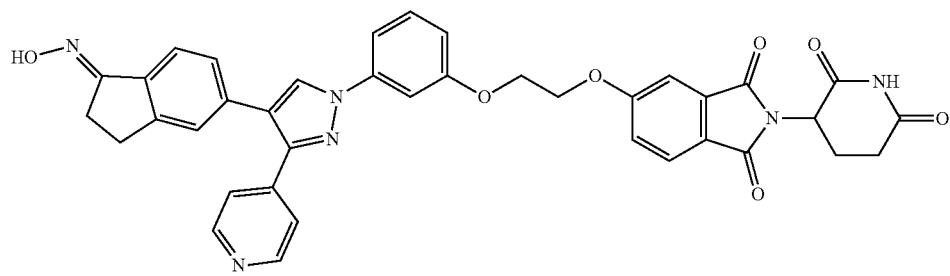 [SMILES: O=C1CCC(N2C(=O)c3ccc(OCCOc4cccc(-n5cc(-c6ccc7c(c6)CC/C7=N\O)c(-c6ccncc6)n5)c4)cc3C2=O)C(=O)N1]

Step A: 4-(1-(3-(2-(benzyloxy)ethoxy)phenyl)-4-bromo-1H-pyrazol-3-yl)pyridine

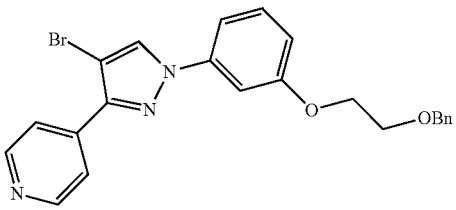 [SMILES: Brc1cn(-c2cccc(OCCOCc3ccccc3)c2)nc1-c1ccncc1]

To a solution of 2-(3-(2-(benzyloxy)ethoxy)phenyl)-4,4,5,5-tetramethyl-1,3,2-
Dioxaborolane (1.2 g, 3.39 mmol) in DCM (50 mL) was added 4-(4-bromo-1H-pyrazol-3-yl)pyridine (831.53 mg, 3.73 mmol), Cu(OAc)$_2$ (615.6 mg, 3.39 mmol), Et$_2$NH(2.47 g, 33.9 mmol) subsequently. The resulting solution was stirred at 30° C. overnight. The mixture was washed with ammonium hydroxide (30 mL×3). The organic phase was dried over and concentrated under vacuum. The residue was purified by silica gel column with PE/EA to afford desired product 4-(1-(3-(2-(benzyloxy)ethoxy)phenyl)-4-bromo-1H-pyrazol-3-yl)pyridine (900 mg, 59% yield) as purple solid. LCMS (ES$^+$): m/z 450.1 [M+H]$^+$.

Step B: 5-(1-(3-(2-(Benzyloxy)ethoxy)phenyl)-3-(pyridin-4-yl)-1H-pyrazol-4-yl)-2,3-dihydro-1H-inden-1-one

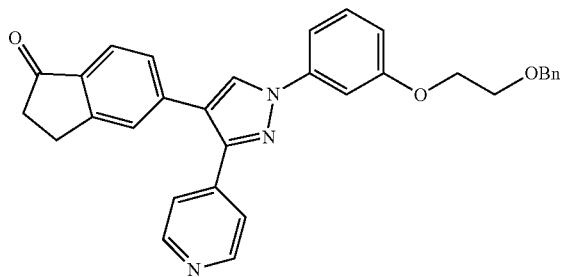 [SMILES: O=C1CCc2cc(-c3cn(-c4cccc(OCCOCc5ccccc5)c4)nc3-c3ccncc3)ccc21]

To a solution of 4-(1-(3-(2-(benzyloxy)ethoxy)phenyl)-4-bromo-1H-pyrazol-3-yl)pyridine (900 mg, 2.0 mmol) in 1,4-dioxane/H$_2$O (20 mL, v/v=10/1) were added 5-(4,4,5,5-tetramethyl-1,3,2-dioxaborolan-2-yl)-2,3-dihydro-1H-inden-1-one (774 mg, 3.0 mmol), Pd$_2$(dba)$_3$(183.14 mg, 0.2 mmol), CsF(3.14 g, 20.64 mmol) [(t-Bu)$_3$PH]BF$_4$ (609 mg, 2.1 mmol), N,N-dicyclohexylmethylamine (503 mg, 2.58 mmol) subsequently. The resulting solution was stirred at 100° C. for 2 hours under N$_2$. After cooling to room temperature, the reaction was diluted with EA (50 mL), washed with water and brine. The organic layer was dried over anhydrous sodium sulfate, concentrated under vacuum. The residue was purified by silica gel column to afford 5-(1-(3-(2-(benzyloxy)ethoxy)phenyl)-3-(pyridin-4-yl)-1H-pyrazol-4-yl)-2,3-dihydro-1H-inden-1-one (750 mg, 74.9% yield) as yellow solid. LCMS (ES$^+$): m/z 502.2 [M+H]$^{++}$.

Step C: 5-(1-(3-(2-hydroxyethoxy)phenyl)-3-(pyridin-4-yl)-1H-pyrazol-4-yl)-2,3-dihydro-1H-inden-1-one

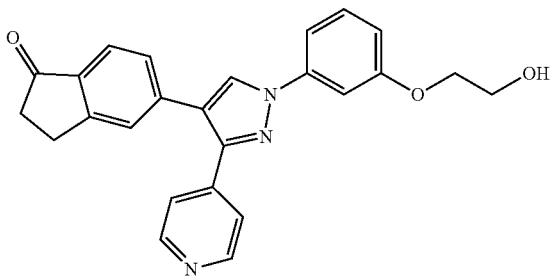 [SMILES: O=C1CCc2cc(-c3cn(-c4cccc(OCCO)c4)nc3-c3ccncc3)ccc21]

To a solution of 5-(1-(3-(2-(benzyloxy)ethoxy)phenyl)-3-(pyridin-4-yl)-1H-pyrazol-4-yl)-2,3-dihydro-1H-inden-1-one (750 mg, 1.50 mmol) in DCM (10 mL), was added BBr$_3$ (1.13 g, 4.50 mmol) in DCM (5 mL) dropwised at −60° C. under N$_2$. After stirred for 1 hour, the mixture was diluted with DCM (20 mL) and washed with brine (10 ml×2). The organic phaser was concentrated and purified by silica gel column to afford 5-(1-(3-(2-hydroxyethoxy)phenyl)-3-(pyridin-4-yl)-1H-pyrazol-4-yl)-2,3-dihydro-1H-inden-1-one (150 mg, 24.4% yield) as yellow solid. LCMS (ES$^+$): m/z 412.1 [M+H]$^+$.

Step D: 2-(2,6-dioxopiperidin-3-yl)-5-(2-(3-(4-(1-oxo-2,3-dihydro-1H-inden-5-yl)-3-(pyridin-4-yl)-1H-pyrazol-1-yl)phenoxy)ethoxy)isoindoline-1,3-dione

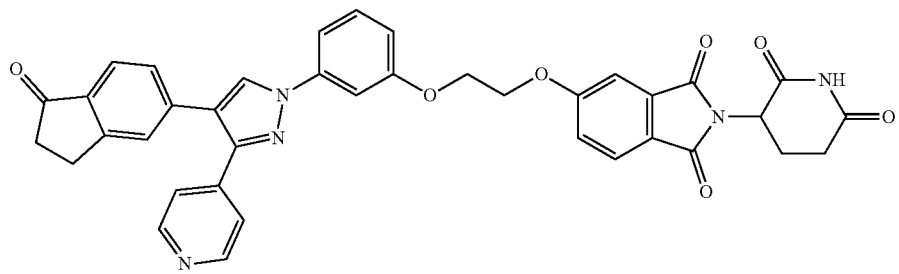 [SMILES: O=C1CCC(N2C(=O)c3ccc(OCCOc4cccc(-n5cc(-c6ccc7c(c6)CCC7=O)c(-c6ccncc6)n5)c4)cc3C2=O)C(=O)N1]

To a solution of 5-(1-(3-(2-hydroxyethoxy)phenyl)-3-(pyridin-4-yl)-1H-pyrazol-4-yl)-2,3-dihydro-1H-inden-1-one (150 mg, 0.36 mmol) in DCM (10 mL) and TEA (109.08 mg, 1.08 mmol) was added MsCl (61.56 mg, 0.54 mmol)

dropwise at 0° C. The resulting solution was stirred at 25° C. for 0.5 hours. Then water was added and extracted with DCM. The organic layer was washed with water and brine, dried over anhydrous sodium sulfate and concentrated to afford crude desired product (170 mg crude, 95.5% yield) as yellow oil, which was used in next step directly. To a solution of above desired product (170 mg, 0.35 mmol) in DMF (10 ml) were added $K_2CO_3$ (144.9 mg, 1.05 mmol), 2-(2,6-dioxopiperidin-3-yl)-5-hydroxyisoindoline-1,3-dione (191.8 mg, 0.70 mmol). The resulting solution was stirred at 70° C. for 2 hours. After quenched with water, the mixture was extracted with EA (30 mL), washed with water and brine. The organic phase was dried over anhydrous sodium sulfate, concentrated and purified by silica gel column to afford 2-(2,6-dioxopiperidin-3-yl)-5-(2-(3-(4-(1-oxo-2,3-dihydro-1H-inden-5-yl)-3-(pyridin-4-yl)-1H-pyrazol-1-yl)phenoxy)ethoxy)isoindoline-1,3-dione (60 mg, 25.9% yield) as white solid. LCMS (ES+): m/z 668.2 [M+H]+.

Step E: (E)-2-(2,6-Dioxopiperidin-3-yl)-5-(2-(3-(4-(1-(hydroxyimino)-2,3-dihydro-1H-inden-5-yl)-3-(pyridin-4-yl)-1H-pyrazol-1-yl)phenoxy)ethoxy)isoindoline-1,3-dione

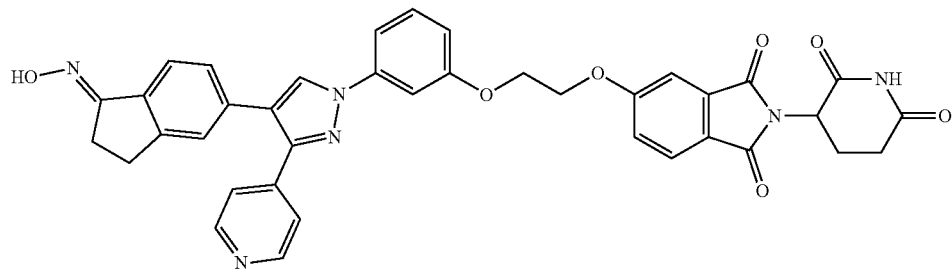 [SMILES: O=C1CCC(N2C(=O)c3ccc(OCCOc4cccc(-n5cc(-c6ccc7c(c6)CC/C7=N\O)c(-c6ccncc6)n5)c4)cc3C2=O)C(=O)N1]

To a solution of S2-(2,6-dioxopiperidin-3-yl)-5-(2-(3-(4-(1-oxo-2,3-dihydro-1H-inden-5-yl)-3-(pyridin-4-yl)-1H-pyrazol-1-yl)phenoxy)ethoxy)isoindoline-1,3-dione (60 mg, 0.090 mmol) in acetonitrile/pyridine (3.0 mL, v/v=2/1) was added hydroxylamine hydrochloride (58.41 mg, 0.90 mmol). The mixture was stirred at 40° C. for 20 minutes. Then it was diluted with DCM (20 mL), and washed with brine (10 mL). The organic phase was concentrated and purified by preparative HPLC to afford (E)-2-(2,6-dioxopiperidin-3-yl)-5-(2-(3-(4-(1-(hydroxyimino)-2,3-dihydro-1H-inden-5-yl)-3-(pyridin-4-yl)-1H-pyrazol-1-yl)phenoxy)ethoxy)isoindoline-1,3-dione (8 mg, 65.6% yield) as white solid. $^1$H NMR (400 MHz, CDCl3): δ 8.58 (s, 2H), 8.04 (s, 2H), 7.83-7.81 (d, J=8.4 Hz, 1H), 7.68-7.66 (d, J=7.6 Hz, 1H), 7.52 (m, 2H), 7.48 (m, 1H), 7.44-7.43 (m, 2H), 7.41-7.36 (m, 2H), 7.30 (s, 2H), 7.23 (s, 2H), 4.99-4.94 (m, 1H), 4.49 (s, 4H), 3.05-2.94 (m, 4H), 2.90-2.73 (m, 3H), 2.04-2.00 (m, 1H); LCMS:(ES+):m/z 683.2 [M+H]+.

Compounds 204 and 205 may be prepared in a manner analogous to compound 203.

Example Synthesis of Compound 206: (E)-2-(2,6-dioxopiperidin-3-yl)-5-(2-(4-(4-(1-(hydroxyimino)-2,3-dihydro-1H-inden-5-yl)-3-(pyridin-4-yl)-1H-pyrazol-1-yl)piperidin-1-yl)ethoxy)isoindoline-1,3-dione

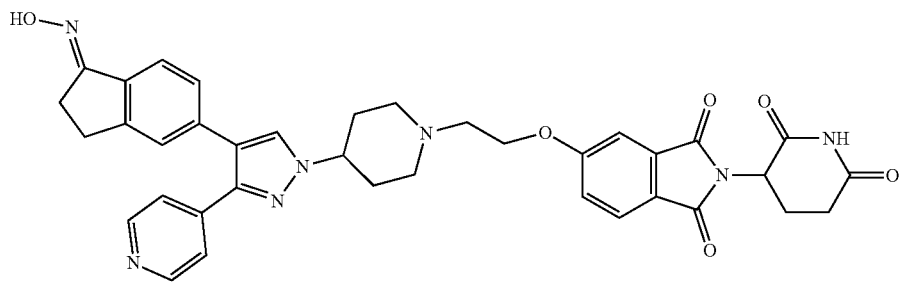 [SMILES: O=C1CCC(N2C(=O)c3ccc(OCCN4CCC(n5cc(-c6ccc7c(c6)CC/C7=N\O)c(-c6ccncc6)n5)CC4)cc3C2=O)C(=O)N1]

Step A: tert-butyl 4-(4-bromo-3-(pyridin-4-yl)-1H-pyrazol-1-yl)piperidine-1-carboxylate

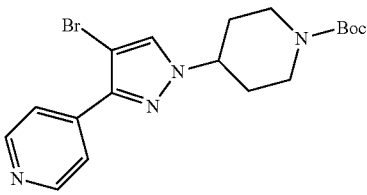 [SMILES: CC(C)(C)OC(=O)N1CCC(n2cc(Br)c(-c3ccncc3)n2)CC1]

The solution of 4-(4-bromo-1H-pyrazol-3-yl)pyridine (5.0 g, 22.4 mmol), tert-butyl 4-bromopiperidine-1-carboxylate (7.1 g, 26.9 mmol) and Cs$_2$CO$_3$ (11.0 g, 33.6 mmol) in DMF (50 mL) was stirred at 55° C. overnight. When it was cooled to room temperature, water (50 mL) was added. The resultant mixture was extracted by ethyl acetate (20 mL×3) and the combined organic layer was washed by brine (20 mL×3), dried over anhydrous sodium sulfate, filtered and concentrated. The residue was purified by column chromatography on silica (petroleum ether/ethyl acetate=1/1) to give tert-butyl 4-(4-bromo-3-(pyridin-4-yl)-1H-pyrazol-1-yl)piperidine-1-carboxylate (3.7 g, 41% yield) as brown oil. LCMS: m/z 407.1 [M+H]$^+$.

Step B: tert-butyl 4-(4-(1-oxo-2,3-dihydro-1H-inden-5-yl)-3-(pyridin-4-yl)-1H-pyrazol-1-yl)piperidine-1-carboxylate

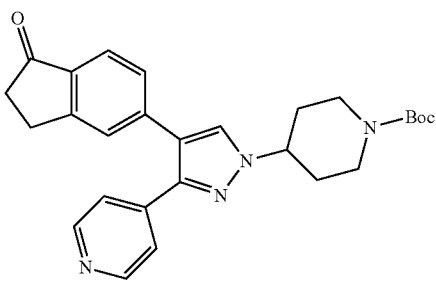 [SMILES: CC(C)(C)OC(=O)N1CCC(n2cc(-c3ccc4c(c3)CCC4=O)c(-c3ccncc3)n2)CC1]

To a solution of tert-butyl 4-(4-bromo-3-(pyridin-4-yl)-1H-pyrazol-1-yl)piperidine-1-carboxylate (2.0 g, 4.9 mmol), 5-(4,4,5,5-tetramethyl-1,3,2-dioxaborolan-2-yl)-2,3-dihydro-1H-inden-1-one (1.4 g, 5.4 mmol) and K$_2$CO$_3$ (1.4 g, 9.8 mmol) in 1,4-dioxane (40 mL) and water (8 mL) was added Pd(PPh$_3$)$_4$ (200 mg) under Ar atmosphere, and the mixture was stirred at 80° C. for 2 hours. When it was cooled to room temperature, the mixture was extracted by ethyl acetate (20 mL×3) and the combined organic layer was washed by brine (20 mL×3), dried over anhydrous sodium sulfate, filtered, and concentrated in vacuo. The residue was purified by flash column chromatography (petroleum ether/ethyl acetate=1/10) to give tert-butyl 4-(4-(1-oxo-2,3-dihydro-1H-inden-5-yl)-3-(pyridin-4-yl)-1H-pyrazol-1-yl)piperidine-1-carboxylate (1.9 g, 84% yield) as yellow oil. LCMS: m/z 459.3 [M+H]$^+$.

Step C: 5-(1-(piperidin-4-yl)-3-(pyridin-4-yl)-1H-pyrazol-4-yl)-2,3-dihydro-1H-inden-1-one

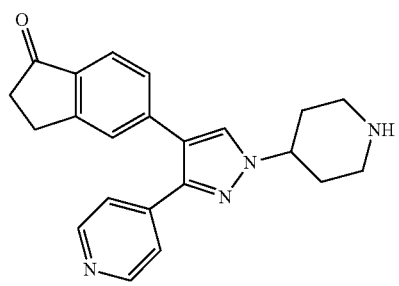 [SMILES: O=C1CCc2cc(-c3cn(C4CCNCC4)nc3-c3ccncc3)ccc21]

A mixture of tert-butyl 4-(4-(1-oxo-2,3-dihydro-1H-inden-5-yl)-3-(pyridin-4-yl)-1H-pyrazol-1-yl)piperidine-1-carboxylate (1.9 g, 4.1 mmol) in HCl/1,4-dioxane (20 mL) was stirred at room temperature for 2 hours. Then the solvent was directly removed in vacuum, and the crude product (1.6 g, 100% yield) was obtained as hydrochloride salt, which was directly used to the next step without further purification.

Step D: 2-(2,6-dioxopiperidin-3-yl)-5-(2-(4-(4-(1-oxo-2,3-dihydro-1H-inden-5-yl)-3-(pyridin-4-yl)-1H-pyrazol-1-yl)piperidin-1-yl)ethoxy)isoindoline-1,3-dione

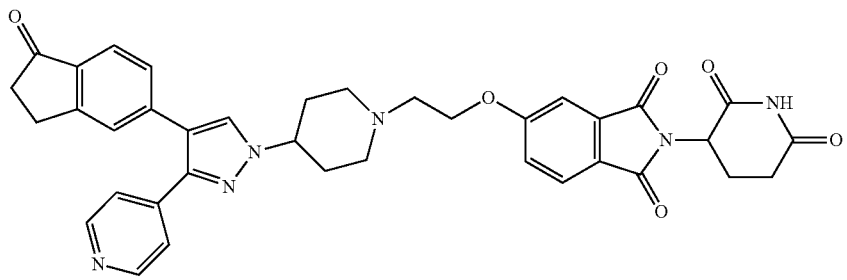 [SMILES: O=C1CCC(N2C(=O)c3ccc(OCCN4CCC(n5cc(-c6ccc7c(c6)CCC7=O)c(-c6ccncc6)n5)CC4)cc3C2=O)C(=O)N1]

A solution of 5-(1-(piperidin-4-yl)-3-(pyridin-4-yl)-1H-pyrazol-4-yl)-2,3-dihydro-1H-inden-1-one (440 mg, 1.2 mmol), 5-(2-chloroethoxy)-2-(2,6-dioxopiperidin-3-yl)isoindoline-1,3-dione (410 mg, 1.2 mmol), KI (304 mg, 1.8 mmol) and DIPEA (476 mg, 3.6 mmol) in DMSO (8 mL) was stirred at 100° C. overnight. When it was cooled to room temperature, water (10 mL) was added and the mixture was extracted by ethyl acetate (5 mL×3) and the combined organic layer was washed by brine (5 mL×3), dried over anhydrous sodium sulfate, filtered, and concentrated. The residue was purified by preparative TLC (DCM/MeOH=10/1) to give 2-(2,6-dioxopiperidin-3-yl)-5-(2-(4-(4-(1-oxo-2,3-dihydro-1H-inden-5-yl)-3-(pyridin-4-yl)-1H-pyrazol-1-yl)piperidin-1-yl)ethoxy)isoindoline-1,3-dione (180 mg, 22% yield) as a white solid. LCMS: m/z 659.3 [M+H]$^+$.

Step E: (E)-2-(2,6-dioxopiperidin-3-yl)-5-(2-(4-(4-(1-(hydroxyimino)-2,3-dihydro-1H-inden-5-yl)-3-(pyridin-4-yl)-1H-pyrazol-1-yl)piperidin-1-yl)ethoxy)isoindoline-1,3-dione

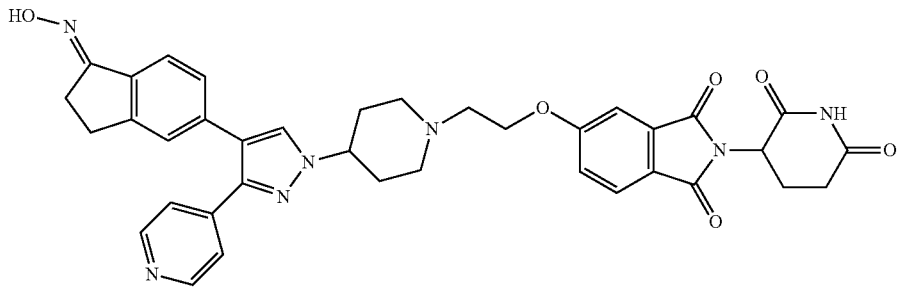 [SMILES: O=C1CCC(N2C(=O)c3ccc(OCCN4CCC(n5cc(-c6ccc7c(c6)CC/C7=N\O)c(-c6ccncc6)n5)CC4)cc3C2=O)C(=O)N1]

To a solution of 2-(2,6-dioxopiperidin-3-yl)-5-(2-(4-(4-(1-oxo-2,3-dihydro-1H-inden-5-yl)-3-(pyridin-4-yl)-1H-pyrazol-1-yl)piperidin-1-yl)ethoxy)isoindoline-1,3-dione (120 mg, 0.2 mmol) in pyridine (2 mL) was added hydroxylamine hydrochloride (126 mg, 1.8 mmol), and the mixture was stirred at room temperature for 2 hours. Then the solvent was removed in vacuo and the residue was purified by Preparative HPLC to give (E)-2-(2,6-dioxopiperidin-3-yl)-5-(2-(4-(4-(1-(hydroxyimino)-2,3-dihydro-1H-inden-5-yl)-3-(pyridin-4-yl)-1H-pyrazol-1-yl)piperidin-1-yl)ethoxy)isoindoline-1,3-dione (52 mg, 42% yield). LCMS: m/z 674.2 [M+H]$^+$; $^1$H NMR (400 MHz, DMSO-d$_6$) δ 2.03-2.11 (5H, m), 2.25-2.30 (2H, m), 2.50-2.62 (2H, m), 2.78-2.86 (5H, m), 2.88-2.99 (2H, m), 3.08-3.11 (2H, m), 4.22-4.28 (1H, m), 4.33 (2H, t, J=5.2 Hz), 5.12 (1H, dd, J=12.8, 5.2 Hz), 7.12 (1H, d, J=8.0 Hz), 7.30 (1H, s), 7.38-7.40 (3H, m), 7.49-7.52 (2H, m), 7.84 (1H, d, J=8.4 Hz), 8.14 (1H, s), 8.50 (2H, dd, J=4.4, 1.6 Hz), 10.86 (1H, s), 11.10 (1H, s).

Example Synthesis of Compound 207: (E)-2-(2,6-dioxopiperidin-3-yl)-5-(4-(4-(1-(hydroxyimino)-2,3-dihydro-1H-inden-5-yl)-3-(pyridin-4-yl)-1H-pyrazol-1-yl)-1,4'-bipiperidin-1'-yl)isoindoline-1,3-dione Step A: tert-butyl 4-(4-(1-oxo-2,3-dihydro-1H-inden-5-yl)-3-(pyridin-4-yl)-1H-pyrazol-1-yl)-1,4'-bipiperidine-1'-carboxylate

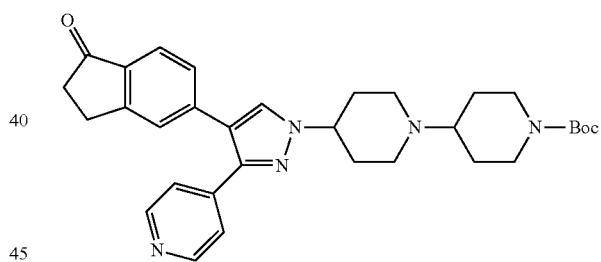

The solution of 5-(1-(piperidin-4-yl)-3-(pyridin-4-yl)-1H-pyrazol-4-yl)-2,3-dihydro-1H-inden-1-one (2.5 g, 7.0 mmol), tert-butyl 4-bromopiperidine-1-carboxylate (2.0 g, 7.7 mmol), KI (1.2 g, 7.0 mmol) and K$_2$CO$_3$ (2.9 g, 20.9 mmol) in DMF (20 mL) was stirred at 110° C. overnight. When it was cooled to room temperature, water (30 mL) was added. The resultant mixture was extracted by ethyl acetate

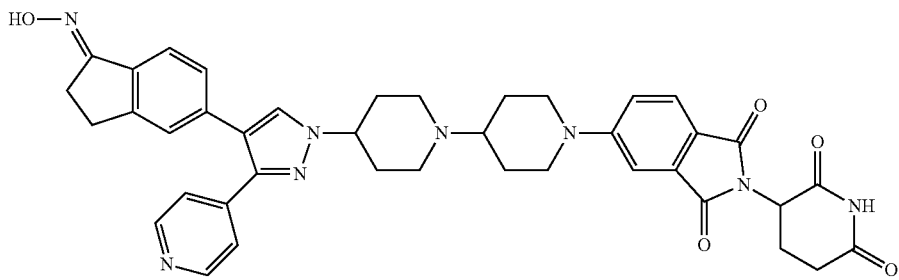 [SMILES: O=C1CCC(N2C(=O)c3ccc(N4CCC(N5CCC(n6cc(-c7ccc8c(c7)CC/C8=N\O)c(-c7ccncc7)n6)CC5)CC4)cc3C2=O)C(=O)N1]

(20 mL×3) and the combined organic layer was washed by brine (20 mL×3), dried over anhydrous sodium sulfate, filtered and concentrated. The residue was purified by column chromatography on silica (DCM/MeOH=20/1) to give tert-butyl 4-(4-(1-oxo-2,3-dihydro-1H-inden-5-yl)-3-(pyridin-4-yl)-1H-pyrazol-1-yl)-1,4'-bipiperidine-1'-carboxylate (360 mg, 10% yield) as brown oil. LCMS: m/z 542.3 [M+H]⁺.

Step B: 5-(1-(1,4'-bipiperidin-4-yl)-3-(pyridin-4-yl)-1H-pyrazol-4-yl)-2,3-dihydro-1H-inden-1-one

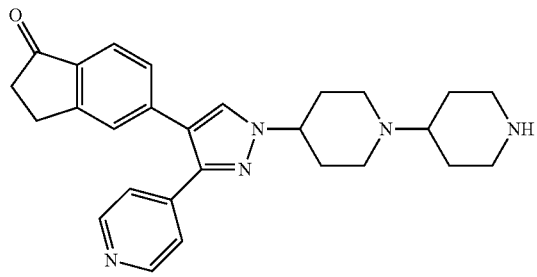 [SMILES: O=C1CCc2cc(-c3cn(C4CCN(C5CCNCC5)CC4)nc3-c3ccncc3)ccc21]

A mixture of tert-butyl 4-(4-(1-oxo-2,3-dihydro-1H-inden-5-yl)-3-(pyridin-4-yl)-1H-pyrazol-1-yl)-1,4'-bipiperidine-1'-carboxylate (360 mg, 0.7 mmol) in HCl/1,4-dioxane (10 mL) was stirred at room temperature for 30 minutes. Then the solvent was directly removed in vacuum, and the crude product (300 mg, 100% yield) was obtained as hydrochloride salt, which was directly used to the next step without further purification.

Step C: 2-(2,6-dioxopiperidin-3-yl)-5-(4-(4-(1-oxo-2,3-dihydro-1H-inden-5-yl)-3-(pyridin-4-yl)-1H-pyrazol-1-yl)-1,4'-bipiperidin-1'-yl)isoindoline-1,3-dione

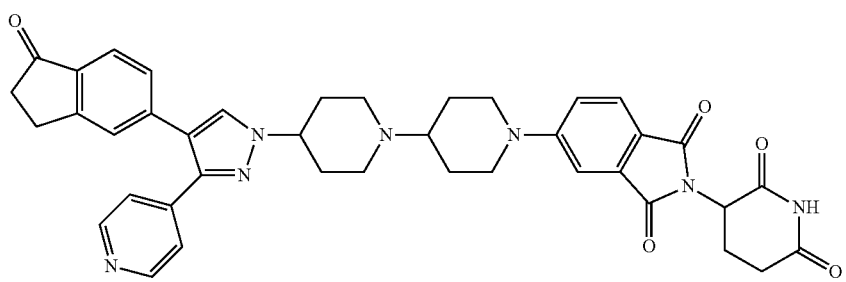 [SMILES: O=C1CCC(N2C(=O)c3ccc(N4CCC(N5CCC(n6cc(-c7ccc8c(c7)CCC8=O)c(-c7ccncc7)n6)CC5)CC4)cc3C2=O)C(=O)N1]

A solution of 5-(1-(1,4'-bipiperidin-4-yl)-3-(pyridin-4-yl)-1H-pyrazol-4-yl)-2,3-dihydro-1H-inden-1-one (290 mg, 0.7 mmol), 2-(2,6-dioxopiperidin-3-yl)-5-fluoroisoindoline-1,3-dione (183 mg, 0.7 mmol), and Et₃N (336 mg, 3.3 mmol) in DMSO (5 mL) was stirred at 80° C. overnight. When it was cooled to room temperature, water (10 mL) was added and the mixture was extracted by ethyl acetate (5 mL×3) and the combined organic layer was washed by brine (5 mL×3), dried over anhydrous sodium sulfate, filtered, and concentrated. The residue was purified by preparative TLC (DCM/MeOH=20/1) to give 2-(2,6-dioxopiperidin-3-yl)-5-(4-(4-(1-oxo-2,3-dihydro-1H-inden-5-yl)-3-(pyridin-4-yl)-1H-pyrazol-1-yl)-1,4'-bipiperidin-1'-yl)isoindoline-1,3-dione (195 mg, 42% yield) as a white solid. LCMS: m/z 698.3 [M+H]⁺.

Step D: (E)-2-(2,6-dioxopiperidin-3-yl)-5-(4-(4-(1-(hydroxyimino)-2,3-dihydro-1H-inden-5-yl)-3-(pyridin-4-yl)-1H-pyrazol-1-yl)-1,4'-bipiperidin-1'-yl)isoindoline-1,3-dione

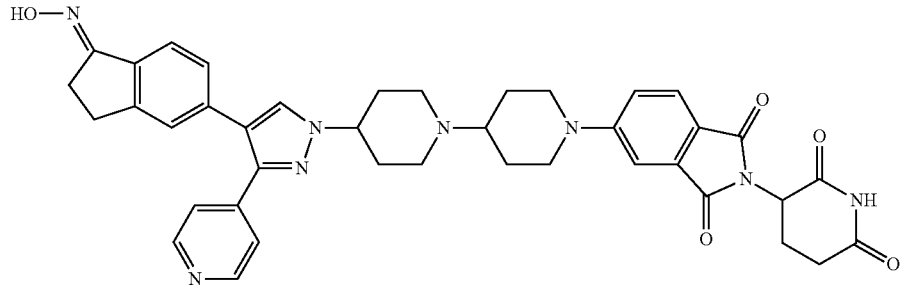 [SMILES: O=C1CCC(N2C(=O)c3ccc(N4CCC(N5CCC(n6cc(-c7ccc8c(c7)CC/C8=N\O)c(-c7ccncc7)n6)CC5)CC4)cc3C2=O)C(=O)N1]

To a solution of 2-(2,6-dioxopiperidin-3-yl)-5-(4-(4-(1-oxo-2,3-dihydro-1H-inden-5-yl)-3-(pyridin-4-yl)-1H-pyrazol-1-yl)-1,4'-bipiperidin-1'-yl)isoindoline-1,3-dione (95 mg, 0.1 mmol) in pyridine (2 mL) was added hydroxylamine hydrochloride (94 mg, 1.3 mmol), and the mixture was stirred at room temperature for 2 hours. Then the solvent was removed in vacuo and the residue was purified by preparative HPLC to give (E)-2-(2,6-dioxopiperidin-3-yl)-5-(4-(4-(1-(hydroxyimino)-2,3-dihydro-1H-inden-5-yl)-3-(pyridin-4-yl)-1H-pyrazol-1-yl)-1,4'-bipiperidin-1'-yl)isoindoline-1,3-dione (53 mg, 55% yield). LCMS: m/z 713.4 [M+H]$^+$; $^1$H NMR (400 MHz, DMSO-$d_6$) δ 1.51-1.53 (2H, m), 1.84-1.87 (2H, m), 1.97-2.03 (3H, m), 2.09-2.11 (2H, m), 2.32-2.37 (2H, m), 2.57-2.67 (2H, m), 2.78-2.89 (3H, m), 2.90-2.99 (6H, m), 4.11 (2H, d, J=12.8 Hz), 4.20-4.22 (1H, m), 5.06 (1H, dd, J=12.8, 5.6 Hz), 7.12 (1H, d, J=8.8 Hz), 7.25 (1H, d, J=6.0 Hz), 7.27 (1H, s), 7.30 (1H, s), 7.38 (2H, dd, J=4.8, 1.2 Hz), 7.50 (1H, d, J=8.0 Hz), 7.56 (1H, d, J=8.8 Hz), 8.13 (1H, s), 8.24 (1H, s), 8.50 (2H, dd, J=4.8, 1.6, Hz), 10.86 (1H, s), 11.08 (1H, s).

Example Synthesis of Compound 208: (3R)—N-(3-(5-(4-(2-(2-(2-(2-(4-(2-(2,6-Dioxopiperidin-3-yl)-1,3-dioxoisoindolin-5-yl)piperazin-1-yl) ethoxy)ethoxy)ethoxy)ethoxy)phenyl)-1H-pyrrolo[2,3-b]pyridine-3-carbonyl)-2,4-difluorophenyl)-3-fluoropyrrolidine-1-sulfonamide Step A: 2-(2-(2-(2-(4-bromophenoxy)ethoxy)ethoxy)ethoxy)acetaldehyde

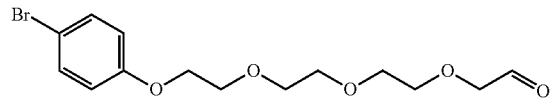

To a solution of 2-(2-(2-(2-(4-bromophenoxy)ethoxy)ethoxy)ethoxy)ethan-1-ol (3.1 g, 8.90 mmol) in acetonitrile (30 mL), was added IBX (3.7 g, 13.40 mmol). The mixture was heated to 80° C. for 1 hour. After cooling to room temperature, the mixture was filtered through Celite, and concentrated to afford crude desired product 2-(2-(2-(2-(4-bromophenoxy)ethoxy)ethoxy)ethoxy)acetaldehyde (3.2 g, crude) as oil.

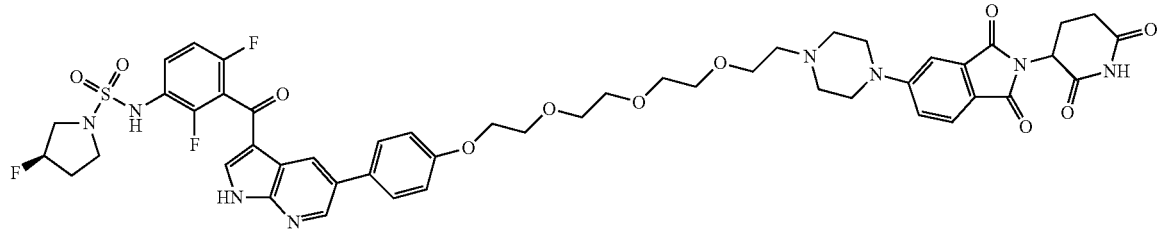 [SMILES: O=C1CCC(N2C(=O)c3ccc(N4CCN(CCOCCOCCOCCOc5ccc(-c6cnc7[nH]cc(C(=O)c8c(F)ccc(NS(=O)(=O)N9CC[C@@H](F)C9)c8F)c7c6)cc5)CC4)cc3C2=O)C(=O)N1]

Step B: 5-(4-(2-(2-(2-(2-(4-bromophenoxy)ethoxy)ethoxy)ethoxy)ethyl)piperazin-1-yl)-2-(2,6-dioxopiperidin-3-yl)isoindoline-1,3-dione

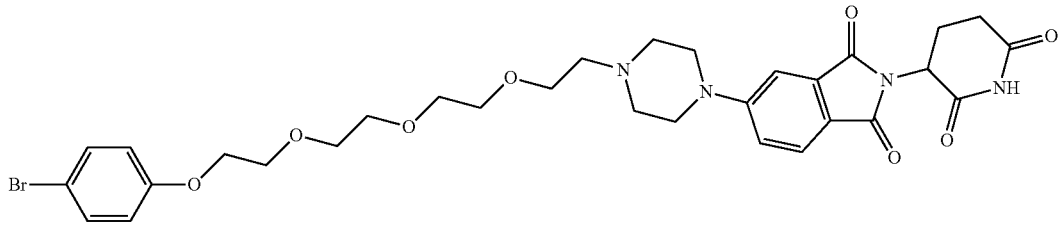 [SMILES: O=C1CCC(N2C(=O)c3ccc(N4CCN(CCOCCOCCOCCOc5ccc(Br)cc5)CC4)cc3C2=O)C(=O)N1]

To a solution of 2-(2-(2-(2-(4-bromophenoxy)ethoxy)ethoxy)ethoxy)acetaldehyde (3.2 g, 9.20 mmol) and 2-(2,6-dioxopiperidin-3-yl)-5-(piperazin-1-yl)isoindoline-1,3-dione hydrochloride (3.1 g, 9.20 mmol) in methanol (100 mL) and two drops AcOH was added NaBH$_3$CN (0.58 g, 9.20 mmol). The mixture was stirred at room temperature overnight. After quenched with water (50 mL), the mixture was extracted with DCM (100 mL×2). The combined organic layer was washed with brine (200 mL), dried over Na$_2$SO$_4$ and filtered. The solvent was evaporated under reduced pressure. The residue was purified by column chromatography (DCM:MeOH=20:1) to afford the desired compound 5-(4-(2-(2-(2-(2-(4-bromophenoxy)ethoxy)ethoxy)ethoxy)ethyl)piperazin-1-yl)-2-(2,6-dioxopiperidin-3-yl)isoindoline-1,3-dione (1.1 g, 18%) as yellow solid. LC-MS: (ES$^+$): m/z 675.1 [M+H]$^+$.

Step C: 2-(2,6-dioxopiperidin-3-yl)-5-(4-(2-(2-(2-(2-(4-(4,4,5,5-tetramethyl-1,3,2-dioxaborolan-2-yl)phenoxy)ethoxy)ethoxy)ethoxy)ethyl)piperazin-1-yl)isoindoline-1,3-dione

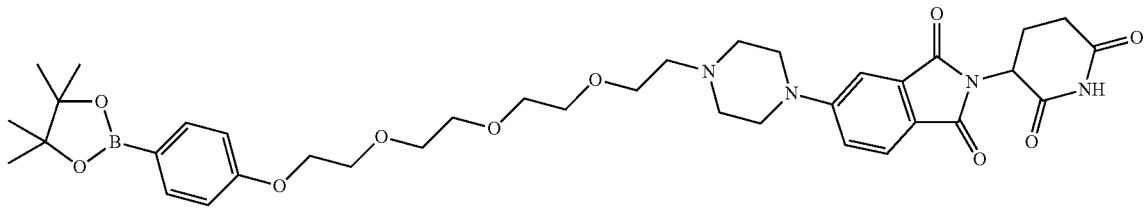 [SMILES: CC1(C)OB(c2ccc(OCCOCCOCCOCCN3CCN(c4ccc5c(c4)C(=O)N(C4CCC(=O)NC4=O)C5=O)CC3)cc2)OC1(C)C]

A solution of 5-(4-(2-(2-(2-(2-(4-bromophenoxy)ethoxy)ethoxy)ethoxy)ethyl)piperazin-1-yl)-2-(2,6-dioxopiperidin-3-yl)isoindoline-1,3-dione (400 mg, 0.60 mmol), 4,4,4',4',5,5,5',5'-octamethyl-2,2'-bi(1,3,2-dioxaborolane) (227 mg, 0.89 mmol), Pd(dppf)Cl$_2$(88 mg, 0.12 mmol) and KOAc (118 mg, 1.20 mmol) in dioxane (10 mL) was heated to 90° C. overnight under N$_2$ atmosphere. After the reaction was quenched with water (15 mL), the mixture was extracted with DCM (50 mL×2). The combined layers were washed with water and brine. The combined organic layer was dried (Na$_2$SO$_4$), filtered, and concentrated under reduced pressure. The residue was purified by silica gel chromatography to afford 2-(2,6-Dioxopiperidin-3-yl)-5-(4-(2-(2-(2-(2-(4-(4,4,5,5-tetramethyl-1,3,2-dioxaborolan-2-yl)phenoxy)ethoxy)ethoxy)ethoxy)ethyl)piperazin-1-yl)isoindoline-1,3-dione (200 mg, 47%) as yellow solid. LCMS (ES$^+$): m/z 721.3 [M+H]$^+$.

Step D: (3R)—N-(3-(5-(4-(2-(2-(2-(2-(4-(2-(2,6-dioxopiperidin-3-yl)-1,3-dioxoisoindolin-5-yl)piperazin-1-yl)ethoxy)ethoxy)ethoxy)ethoxy)phenyl)-1H-pyrrolo[2,3-b]pyridine-3-carbonyl)-2,4-difluorophenyl)-3-fluoropyrrolidine-1-sulfonamide

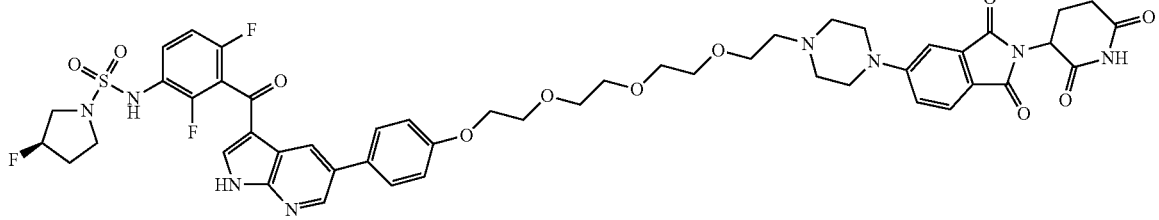

A solution of 2-(2,6-dioxopiperidin-3-yl)-5-(4-(2-(2-(2-(2-(4-(4,4,5,5-tetramethyl-1,3,2-dioxaborolan-2-yl)phenoxy)ethoxy)ethoxy)ethoxy)ethyl)piperazin-1-yl)isoindoline-1,3-dione (200 mg, 0.28 mmol), (R)—N-(3-(5-bromo-1H-pyrrolo[2,3-b]pyridine-3-carbonyl)-2,4-difluorophenyl)-3-fluoropyrrolidine-1-sulfonamide (116 mg, 0.23 mmol), Pd(aMPhos)Cl₂ (66 mg, 0.09 mmol) and CsF (141 mg, 0.93 mmol) in dioxane/H₂O (5 mL/1 mL) was heated to 100° C. for 4 hours under N₂ atmosphere. After the reaction was quenched with water (15 mL), the mixture was extracted with DCM (50 mL×2). The combined layers were washed with water and brine. The combined organic layer was dried (Na₂SO₄), filtered, and concentrated under reduced pressure. The residue was purified by silica gel chromatography to afford (3R)—N-(3-(5-(4-(2-(2-(2-(2-(4-(2-(2,6-dioxopiperidin-3-yl)-1,3-dioxoisoindolin-5-yl)piperazin-1-yl) ethoxy)ethoxy)ethoxy)ethoxy)phenyl)-1H-pyrrolo[2,3-b]pyridine-3-carbonyl)-2,4-difluorophenyl)-3-fluoropyrrolidine-1-sulfonamide (40 mg, 17%) as yellow solid. ¹H NMR (400 MHz, CDCl₃): δ 11.23 (bs, 1H), 10.56 (s, 1H), 8.73 (s, 1H), 8.54 (s, 1H), 7.68-7.62 (m, 3H), 7.44 (s, 1H), 7.28 (s, 1H), 7.09 (d, J=8.8 Hz, 2H), 7.01 (t, J=8.8 Hz, 1H), 6.84 (s, 1H), 6.54 (d, J=7.6 Hz, 1H), 5.17 (s, 1H), 5.11-4.95 (m, 1H), 4.23 (s, 2H), 3.92 (s, 2H), 3.77-3.76 (m, 2H), 3.69-3.67 (m, 4H), 3.64-3.57 (m, 4H), 3.54-3.51 (m, 2H), 3.42-3.39 (m, 2H), 3.13 (s, 4H), 2.93 (s, 3H), 2.50-2.35 (m, 6H), 2.10 (s, 2H); LCMS (ES⁺): m/z 1018.3 [M+H]+.

Example Synthesis of Compound 209

Step A: 3-(tert-butyldimethylsilyloxy)cyclohexanol

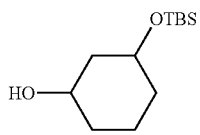

To a solution of 1,3-cyclohexanediol (cis and trans mixture, 25 g, 0.216 mmol) and imidazole (8.8 g, 0.129 mmol)) in a mixture of dichloromethane (150 mL) and tetrahydrofuran (150 mL) was added dropwise a solution of tert-butyldimethylsilyl chloride (16.2 g, 0.107 mmol) in a mixture of dichloromethane (40 mL) and tetrahydrofuran (40 mL) at 0° C. The reaction mixture was allowed to warm to ambient temperature and stirred overnight. Insoluble material was removed by filtration and mother liquor was concentrated under reduced pressure to give residue, which was dissolved in ethyl acetate (300 mL) and washed in turn with 1 N aqueous hydrochloric acid (100 mL), brine (100 mL), saturated sodium hydrogen carbonate in water (100 mL), and saturated sodium chloride (100 mL), and dried over dried over anhydrous sodium sulfate. Evaporation of the solvent gave a residue, which was chromatographed on silica gel (ethyl acetate/n-hexane=1:5) to give 3-(tert-butyldimethylsilyloxy)cyclohexanol (cis and trans mixture) (12.5 g, 51% yield) as colorless oil.

Step B: 3-(pyridin-4-yloxy)cyclohexanol

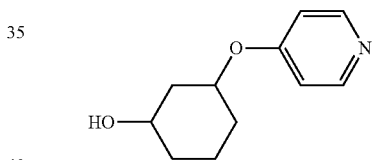

A mixture of 3-(tert-butyldimethylsilyloxy)cyclohexanol (10 g, 43.4 mmol), pyridin-4-ol (3.9 g, 41.2 mmol). tRiphenylphosphine (14.8 g, 56.42 mmol) in THF (40 mL, dry) were added diisopropyl azodicarboxylate(10.5 g, 52.1 mmol) dropwise during a period of 0.5 hours at room temperature under nitrogen atmosphere. The mixture was stirred for 3 h at room temperature under nitrogen atmosphere. HCl aq (70 mL, 1N) was added and stirred for 0.5 hours. The mixture was extracted with DCM (60 mL×3). The liquid layer was basified with KOH and extracted with ethyl acetate (60 mL×4). The combined organic layer was dried over anhydrous sodium sulfate, filtered and concentrated in vacuo to give 3-(pyridin-4-yloxy)cyclohexanol (3.3 g, 40% yield) as yellow oil. LCMS: m/z 194.1 [M+H]⁺.

Step C: 3-(piperidin-4-yloxy)cyclohexanol

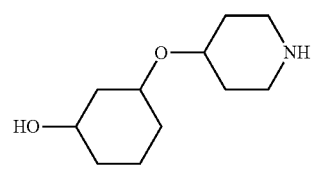

A mixture of solution of 3-(pyridin-4-yloxy)cyclohexanol (3.3 g, 17 mmol) in ethanol (30 mL) was added platinum dioxide (660 mg, 2.9 mmol), sulfuric acid (2.5 g, 26 mmol), then the reaction mixture was stirred at 50° C. for 2 days under hydrogen 2.0 MPa. The mixture was filtrated and concentrated, brine (30 mL×3) was added and extracted with DCM/MeOH(10/1, 30 mL×3). The combined organic layer was dried over anhydrous sodium sulfate, filtered and concentrated in vacuo. The residue was purified by column chromatography on silica (dichloromethane/methanol=10/1) to give 3-(piperidin-4-yloxy)cyclohexanol (330 mg, 10% yield) as pale yellow oil.

Step C: tert-butyl 4-(3-hydroxycyclohexyloxy)piperidine-1-carboxylate

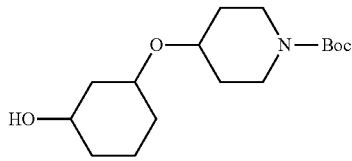 [SMILES: CC(C)(C)OC(=O)N1CCC(OC2CCCC(O)C2)CC1]

To a solution of 3-(piperidin-4-yloxy)cyclohexanol (330 mg, 1.66 mmol) and DIEA (642 mg, 4.9 mmol) in dichloromethane (15 mL) was added Boc₂O (436 mg, 2.0 mmol), then it was stirred at room temperature overnight. The solvent was remove in vacuo at room temperature and the residue was purified by column chromatography on silica gel (ethyl acetate/petroleum ether=1/1) to give tert-butyl 4-(3-hydroxycyclohexyloxy)piperidine-1-carboxylate (352 mg, 71% yield) as yellow oil.

Step D: tert-butyl 4-(3-(methylsulfonyloxy)cyclohexyloxy)piperidine-1-carboxylate

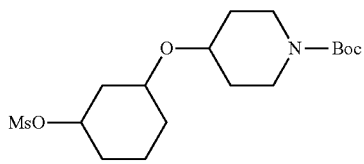

To a solution of tert-butyl 4-(3-hydroxycyclohexyloxy)piperidine-1-carboxylate (352 mg, 1.18 mmol) and DIEA (457 mg, 3.5 mmol) in dichloromethane (15 mL) was added MsCl (162 mg, 1.4 mmol) and the mixture was stirred at 0° C. for 1 hour. It was washed with aqueous NaHCO₃ (15 mL×2), brine (10 mL×2) successively. The organic phase was dried over anhydrous Na₂SO₄, filtered and concentrated in vacuo to give crude tert-butyl 4-(3-(methylsulfonyloxy) cyclohexyloxy)piperidine-1-carboxylate (351 mg, 79% yield) as pale yellow oil.

Step E: cis-tert-butyl -3-(4-bromo-3-(pyridin-4-yl)-1H-pyrazol-1-yl)cyclohexyloxy)piperidine-1-carboxylate and trans-tert-butyl -3-(4-bromo-3-(pyridin-4-yl)-1H-pyrazol-1-yl)cyclohexyloxy)piperidine-1-carboxylate

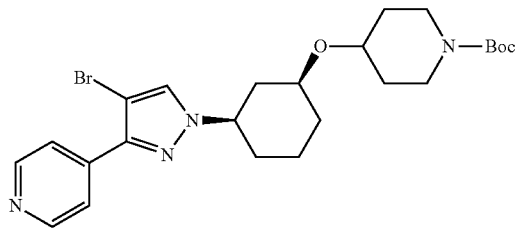

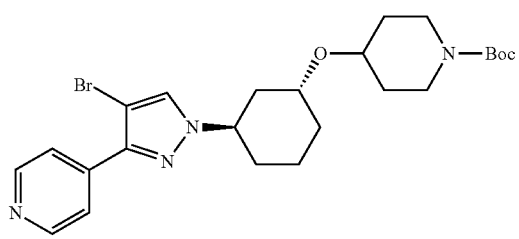

A mixture of tert-butyl 4-(3-(methylsulfonyloxy)cyclohexyloxy)piperidine-1-carboxylate (450 mg, 1.19 mmol), 4-(4-bromo-1H-pyrazol-3-yl)pyridine (252 mg, 1.13 mmol), Cs₂CO₃ (1.16 g, 3.57 mmol) in N,N-dimethylformamide (5 mL) were stirred at 80° C. for two days. It was diluted with brine (15 mL) and extracted with ethyl acetate (15 mL×3). The combined organic layer was washed by brine (15 mL×3), dried over anhydrous sodium sulfate, filtered and concentrated in vacuo. The residue was purified by column chromatography on silica gel (ethyl acetate/petroleum ether=1/1) to give cis-tert-butyl-3-(4-bromo-3-(pyridin-4-yl)-1H-pyrazol-1-yl)cyclohexyloxy)piperidine-1-carboxylate (140 mg) and trans-tert-butyl -3-(4-bromo-3-(pyridin-4-yl)-1H-pyrazol-1-yl)cyclohexyloxy)piperidine-1-carboxylate(130 mg) as pale yellow solid. For cis-tert-butyl -3-(4-bromo-3-(pyridin-4-yl)-1H-pyrazol-1-yl)cyclohexyloxy)piperidine-1-carboxylate: LCMS: m/z 505.3 [M+H]⁺; ¹H NMR (400 MHz, CDCl₃) δ 1.38 (9H, s), 1.53-1.72 (6H, m), 1.89-2.11 (6H, m), 2.97-3.04 (2H, m), 3.41-3.47 (1H, m), 3.53-3.55 (1H, m), 3.69 (2H, brs), 4.09-4.15 (1H, m), 7.52 (1H, s), 7.84 (2H, d, J=6.0 Hz), 8.59 (2H, s). For trans-tert-butyl -3-(4-bromo-3-(pyridin-4-yl)-1H-pyrazol-1-yl)cyclohexyloxy)piperidine-1-carboxylate: LCMS: m/z 505.3 [M+H]⁺; ¹H NMR (400 MHz, CDCl₃) δ 1.39 (9H, s), 1.42-1.92 (9H, m), 2.05-2.18 (3H, m), 3.04-3.11 (2H, m), 3.46-3.50 (1H, m), 3.66 (2H, brs), 3.90 (1H, s), 4.42-4.46 (1H, m), 7.47 (1H, s), 7.85 (2H, d, J=5.6 Hz), 8.58 (2H, s).

Step F: tert-butyl 4-((1S,3R)-3-(4-(1-oxo-2,3-dihydro-1H-inden-5-yl)-3-(pyridin-4-yl)-1H-pyrazol-1-yl)cyclohexyloxy)piperidine-1-carboxylate

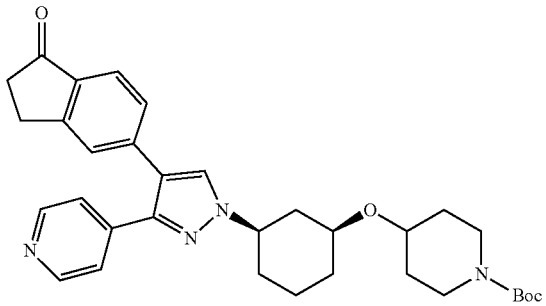 [SMILES: CC(C)(C)OC(=O)N1CCC(O[C@H]2CCC[C@@H](n3cc(-c4ccc5c(c4)CCC5=O)c(-c4ccncc4)n3)C2)CC1]

A mixture of tert-butyl 4-((1S,3R)-3-(4-bromo-3-(pyridin-4-yl)-1H-pyrazol-1-yl)cyclohexyloxy)piperidine-1-carboxylate (40 mg, 0.08 mmol), 5-(4,4,5,5-tetramethyl-1,3,2-dioxaborolan-2-yl)-2,3-dihydro-1H-inden-1-one (26 mg, 0.1 mmol), $K_2CO_3$ (33 mg, 0.24 mmol), tetrakis(triphenylphosphine)palladium (10 mg, 10M %) were stirred in 1,4-dioxane/water (6 mL, 5/1) at 80° C. for 2 hours under nitrogen atmosphere. After the mixture was cooling, it was diluted with water (10 mL), extracted with ethyl acetate (15 mL×3). The combined organic layer was washed by brine (20 mL), dried over anhydrous sodium sulfate, filtered, and concentrated in vacuo. The residue was purified by column chromatography (petroleum ether/ethyl acetate=45/55) to give tert-butyl 4-((1S,3R)-3-(4-(1-oxo-2,3-dihydro-1H-inden-5-yl)-3-(pyridin-4-yl)-1H-pyrazol-1-yl)cyclohexyloxy)piperidine-1-carboxylate (20 mg, 44% yield) as a yellow solid. LCMS: m/z 557.3 [M+H]$^+$.

Step G: 5-(1-((1R,3S)-3-(piperidin-4-yloxy)cyclohexyl)-3-(pyridin-4-yl)-1H-pyrazol-4-yl)-2,3-dihydro-1H-inden-1-one

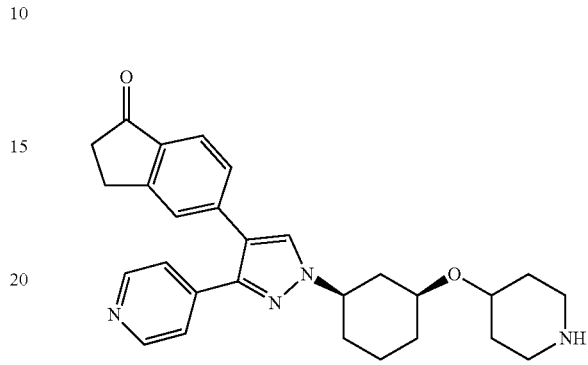

A solution of tert-butyl 4-((1S,3R)-3-(4-(1-oxo-2,3-dihydro-1H-inden-5-yl)-3-(pyridin-4-yl)-1H-pyrazol-1-yl)cyclohexyloxy)piperidine-1-carboxylate (40 mg, 0.08 mmol) in the solution of 4 N HCl in 1,4-dioxane (3 mL) was stirred at 0° C. for 5 hours. Then the solvent was directly removed to give 5-(1-((1R,3S)-3-(piperidin-4-yloxy)cyclohexyl)-3-(pyridin-4-yl)-1H-pyrazol-4-yl)-2,3-dihydro-1H-inden-1-one (38 mg, crude, 100% yield), which was directly used to the next step without further purification.

Step H: 2-(2,6-dioxopiperidin-3-yl)-5-(4-((1S,3R)-3-(4-(1-oxo-2,3-dihydro-1H-inden-5-yl)-3-(pyridin-4-yl)-1H-pyrazol-1-yl)cyclohexyloxy)piperidin-1-yl)isoindoline-1,3-dione

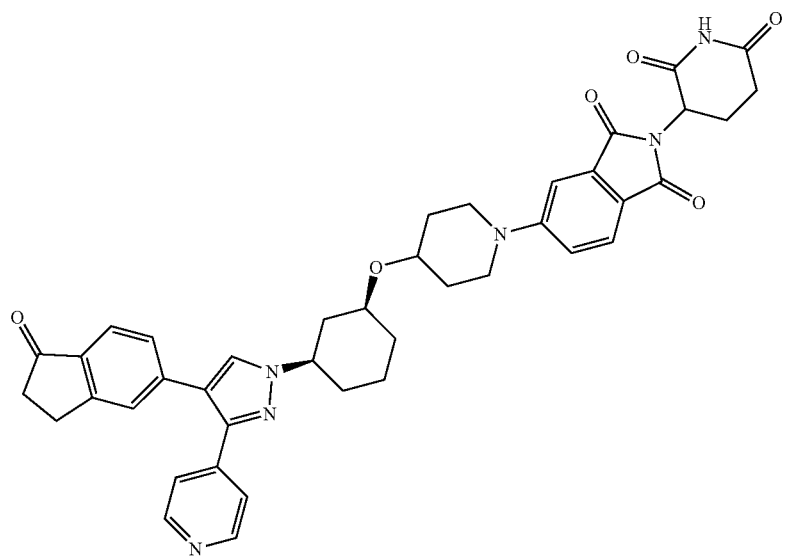 [SMILES: O=C1CCC(N2C(=O)c3ccc(N4CCC(O[C@H]5CCC[C@@H](n6cc(-c7ccc8c(c7)CCC8=O)c(-c7ccncc7)n6)C5)CC4)cc3C2=O)C(=O)N1]

611

A mixture of 5-(1-(((1R,3S)-3-(piperidin-4-yloxy)cyclohexyl)-3-(pyridin-4-yl)-1H-pyrazol-4-yl)-2,3-dihydro-1H-inden-1-one (20 mg, 0.044 mmol), 2-(2,6-dioxopiperidin-3-yl)-5-fluoroisoindoline-1,3-dione (18 mg, 0.066 mmol), DIEA (17 mg, 0.13 mmol) in DMSO (3 mL) were stirred at 80° C. overnight. It was diluted with brine (15 mL) and extracted with ethyl acetate (15 mL×3). The combined organic layer was washed by brine (15 mL×3), dried over anhydrous sodium sulfate, filtered and concentrated in vacuo. The residue was purified by Preparative TLC (DCM/MeOH=20/1) to give 2-(2,6-dioxopiperidin-3-yl)-5-(4-((1S,3R)-3-(4-(1-oxo-2,3-dihydro-1H-inden-5-yl)-3-(pyridin-4-yl)-1H-pyrazol-1-yl)cyclohexyloxy)piperidin-1-yl)isoindoline-1,3-dione (15 mg, 50% yield) as a yellow solid. LCMS: m/z 713.3 [M+H]⁺.

Step I: 2-(2,6-dioxopiperidin-3-yl)-5-(4-((1S,3R)-3-(4-((E)-1-(hydroxyimino)-2,3-dihydro-1H-inden-5-yl)-3-(pyridin-4-yl)-1H-pyrazol-1-yl)cyclohexyloxy)piperidin-1-yl)isoindoline-1,3-dione

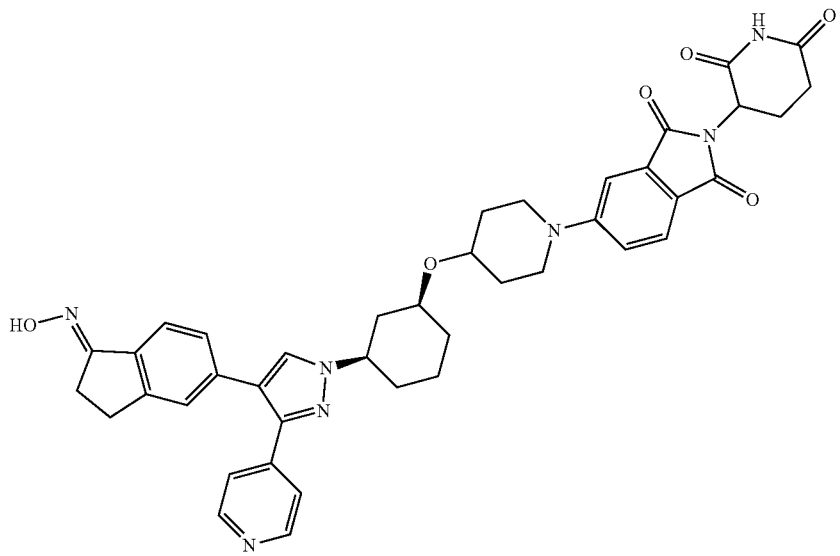 [SMILES: O=C1CCC(N2C(=O)c3ccc(N4CCC(O[C@H]5CCC[C@@H](n6cc(-c7ccc8c(c7)CC/C8=N\O)c(-c7ccncc7)n6)C5)CC4)cc3C2=O)C(=O)N1]

A mixture of 2-(2,6-dioxopiperidin-3-yl)-5-(4-((1S,3R)-3-(4-(1-oxo-2,3-dihydro-1H-inden-5-yl)-3-(pyridin-4-yl)-1H-pyrazol-1-yl)cyclohexyloxy)piperidin-1-yl)isoindoline-1,3-dione (15 mg, 0.021 mmol), hydroxylamine hydrochloride (15 mg, 0.21 mmol) in pyridine (3 mL) was stirred at room temperature overnight. The solvent was directly removed in vacuo at room temperature, and the residue was purified by preparative HPLC to give 2-(2,6-dioxopiperidin-3-yl)-5-(4-((1S,3R)-3-(4-((E)-1-(hydroxyimino)-2,3-dihydro-1H-inden-5-yl)-3-(pyridin-4-yl)-1H-pyrazol-1-yl)cyclohexyloxy)piperidin-1-yl)isoindoline-1,3-dione (2.8 mg, 18% yield) as a yellow solid. LCMS: m/z 728.3 [M+H]⁺; ¹H NMR (400 MHz, CDCl₃) δ 1.73-2.08 (12H, m), 2.17-2.19 (1H, m), 2.51-2.53 (1H, m), 2.66-2.96 (7H, m), 3.17-3.23 (2H, m), 3.48-354 (1H, m), 3.61-3.73 (3H, m), 4.16-4.22 (1H, m), 4.84-4.89 (1H, m), 6.98 (1H, dd, J=8.4, 2.0 Hz), 7.09 (1H, d, J=8.0 Hz), 7.15 (1H, s), 7.21 (1H, d, J=2.4 Hz), 7.45-7.51 (3H, m), 7.59 (2H, t, J=8.8 Hz), 8.14 (1H, d, J=12.8 Hz), 8.46 (1H, d, J=4.8 Hz).

Compound 210 may be prepared in a manner analogous to compound 209.

Example Synthesis of Compound 211: (E)-2-(2,6-dioxopiperidin-3-yl)-5-(3-(1-(2-(4-(4-(1-(hydroxy-imino)-2,3-dihydro-1H-inden-5-yl)-3-(pyridin-4-yl)-1H-pyrazol-1-yl)phenoxy)ethyl)piperidin-4-yl)azetidin-1-yl)isoindoline-1,3-dione

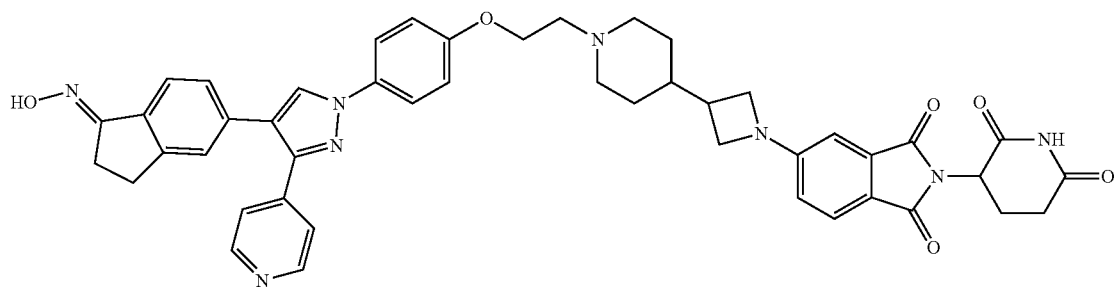 [SMILES: O=C1CCC(N2C(=O)c3ccc(N4CC(C5CCN(CCOc6ccc(-n7cc(-c8ccc9c(c8)CC/C9=N\O)c(-c8ccncc8)n7)cc6)CC5)C4)cc3C2=O)C(=O)N1]

Step A: tert-butyl-3-(1-(2-(4-(4-bromo-3-(pyridin-4-yl)-1H-pyrazol-1-yl)phenoxy)ethyl) piperidin-4-yl) azetidine-1-carboxylate

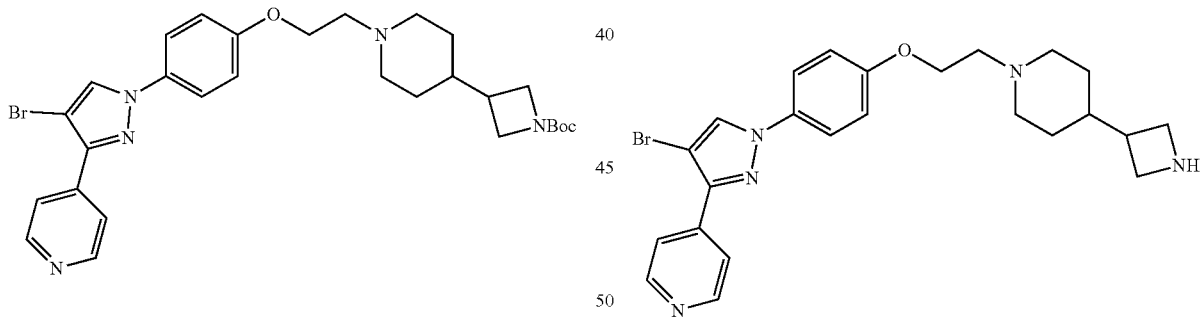

To a solution of 2-(4-(4-bromo-3-(pyridin-4-yl)-1H-pyrazol-1-yl)phenoxy) acetaldehyde (0.34 g, 0.95 mmol) in EtOH/DCM (6 mL/6 mL) were added tert-butyl-3-(piperidin-4-yl)azetidine-1-carboxylate (272 mg, 1.14 mmol) and cat. AcOH. AcOK was added if pH was below 5-6. Then NaBH(OAc)₃ (810 mg, 3.80 mmol) was added. The resulting solution was stirred at 30° C. for 1 hour. After quenched the reaction with aq.NaHCO₃ (20 mL), the mixture was extracted with DCM (30 ml×2). The combined organic layer was dried over anhydrous sodium sulfate and concentrated under vacuum. The residue was applied onto a silica gel column to afford desired product tert-butyl-3-(1-(2-(4-(4-bromo-3-(pyridin-4-yl)-1H-pyrazol-1-yl)phenoxy) ethyl)piperidin-4-yl)azetidine-1-carboxylate (270 mg). LCMS: (ES⁺): m/z 583.3 [M+H]⁺.

Step B: 4-(1-(4-(2-(4-(azetidin-3-yl)piperidin-1-yl)ethoxy)phenyl)-4-bromo-1H-pyrazol-3-yl)pyridine To a solution of tert-butyl 3-(1-(2-(4-(4-bromo-3-(pyridin-4-yl)-1H-pyrazol-1-yl)-phenoxy)ethyl)piperidin-4-yl)azetidine-1-carboxylate (0.27 g, 0.46 mmol) in DCM (6 mL) was added TFA (2 mL). The resulting mixture was stirred at 30° C. for 1 hours. The solvent was removed under vacuum, and the residue was co-evaporated with DCM twice to afford the desired product 4-(1-(4-(2-(4-(azetidin-3-yl)piperidin-1-yl)ethoxy)-phenyl)-4-bromo-1H-pyrazol-3-yl)pyridine (224 mg crude, calculated, 0.46 mmol), which was used into next reaction without further purification. LCMS: (ES⁺): m/z 482.0 [M+H]⁺.

Step C: 5-(3-(1-(2-(4-(4-bromo-3-(pyridin-4-yl)-1H-pyrazol-1-yl)phenoxy)ethyl)piperidin-4-yl)azetidin-1-yl)-2-(2,6-dioxopiperidin-3-yl)isoindoline-1,3-dione

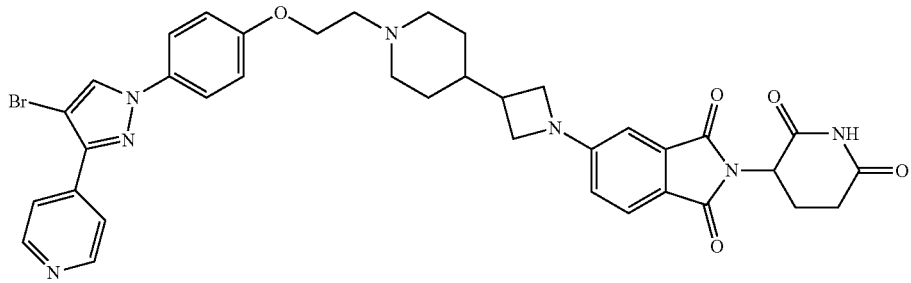 [SMILES: O=C1CCC(N2C(=O)c3ccc(N4CC(C5CCN(CCOc6ccc(-n7cc(Br)c(-c8ccncc8)n7)cc6)CC5)C4)cc3C2=O)C(=O)N1]

To a solution of 4-(1-(4-(2-(4-(azetidin-3-yl)piperidin-1-yl)ethoxy)phenyl)-4-bromo-1H-pyrazol-3-yl)pyridine (224 mg crude, 0.46 mmol) in NMP (5 mL) were added 2-(2,6-dioxopiperidin-3-yl)-5-fluoroisoindoline-1,3-dione (254 mg, 0.92 mmol) and DIEA (0.6 g, 4.6 mmol). The resultant solution was irradiated at 150° C. with microwave for 2 hours. After cooling to room temperature, the mixture was diluted with EA (50 mL). The mixture was washed with brine (10 mL×3). The organic phase was dried over Na$_2$SO$_4$, filtered and concentrated under reduced pressure. The residue was purified by prep-TLC to afford 5-(3-(1-(2-(4-(4-bromo-3-(pyridin-4-yl)-1H-pyrazol-1-yl) phenoxy)ethyl)piperidin-4-yl)azetidin-1-yl)-2-(2,6-dioxopiperidin-3-yl) isoindoline-1,3-dione (60 mg). LCMS: (ES$^+$): m/z 739.3 [M+H]$^+$.

Step D: 2-(2,6-dioxopiperidin-3-yl)-5-(3-(1-(2-(4-(4-(1-oxo-2,3-dihydro-1H-inden-5-yl)-3-(pyridin-4-yl)-1H-pyrazol-1-yl)phenoxy)ethyl)piperidin-4-yl) azetidin-1-yl)isoindoline-1,3-dione

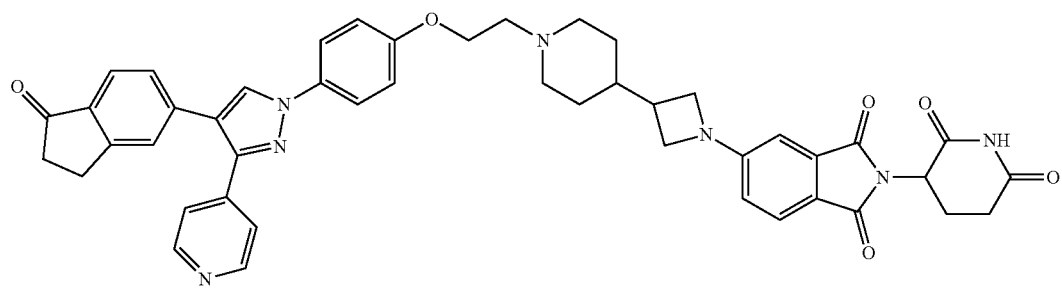 [SMILES: O=C1CCC(N2C(=O)c3ccc(N4CC(C5CCN(CCOc6ccc(-n7cc(-c8ccc9c(c8)CCC9=O)c(-c8ccncc8)n7)cc6)CC5)C4)cc3C2=O)C(=O)N1]

To a solution of 5-(3-(1-(2-(4-(4-bromo-3-(pyridin-4-yl)-1H-pyrazol-1-yl)phenoxy) ethyl)piperidin-4-yl)azetidin-1-yl)-2-(2,6-dioxopiperidin-3-yl)isoindoline-1,3-dione (60 mg, 0.081 mmol) and 5-(4,4,5,5-tetramethyl-1,3,2-dioxaborolan-2-yl)-2,3-dihydro-1H-inden-1-one (84 mg, 0.325 mmol) in dioxane (15 mL)/H$_2$O (3 mL) were added CsF (49 mg, 0.325 mmol), Pd$_2$(dba)$_3$ (30 mg, 0.033 mmol), tri-tert-butylphosphine tetrafluoroborate (20 mg, 0.066 mmol) and two drops of Cy$_2$NCH$_3$ subsequently. The resulting solution was heated to 100° C. for 16 hours under N$_2$ atmosphere. After cooling to room temperature, the reaction was quenched with water (20 mL), and the mixture was extracted with ethyl acetate (30 mL×2). The combined organic layer was dried over anhydrous sodium sulfate and concentrated under vacuum. The residue was purified by prep-TLC to afford desired product 2-(2,6-dioxopiperidin-3-yl)-5-(3-(1-(2-(4-(4-(1-oxo-2,3-dihydro-1H-inden-5-yl)-3-(pyridin-4-yl)-1H-pyrazol-1-yl)phenoxy)ethyl)piperidin-4-yl)azetidin-1-yl)isoindoline-1,3-dione (30 mg, 47% yield) as yellow solid. LCMS: (ES+): m/z 790.3 [M+H]$^+$.

Step E: (E)-2-(2,6-dioxopiperidin-3-yl)-5-(3-(1-(2-(4-(4-(1-(hydroxyimino)-2,3-dihydro-1H-inden-5-yl)-3-(pyridin-4-yl)-1H-pyrazol-1-yl)phenoxy)ethyl)piperidin-4-yl)azetidin-1-yl)isoindoline-1,3-dione

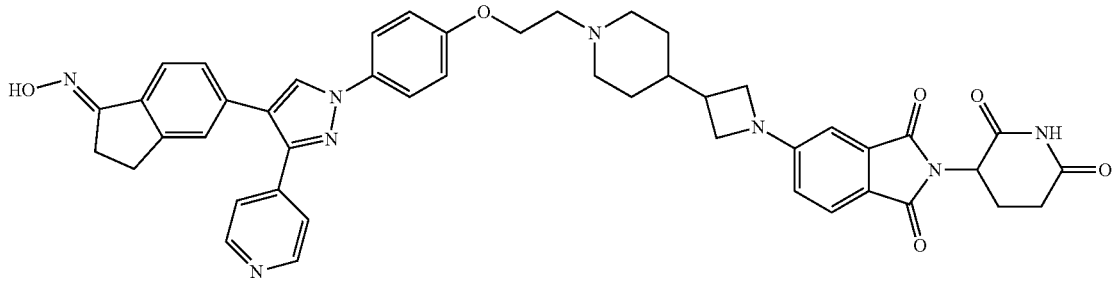 [SMILES: O=C1CCC(N2C(=O)c3ccc(N4CC(C5CCN(CCOc6ccc(-n7cc(-c8ccc9c(c8)CC/C9=N\O)c(-c8ccncc8)n7)cc6)CC5)C4)cc3C2=O)C(=O)N1]

To a solution of 2-(2,6-dioxopiperidin-3-yl)-5-(3-(1-(2-(4-(4-(1-oxo-2,3-dihydro-1H-inden-5-yl)-3-(pyridin-4-yl)-1H-pyrazol-1-yl)phenoxy)ethyl)piperidin-4-yl)azetidin-1-yl)isoindoline-1,3-dione (30 mg, 0.038 mmol) in CH$_3$CN/pyridine (6 mL/3 mL) was added hydroxylamine hydrochloride (26 mg, 0.38 mmol). The mixture was stirred at 50° C. for 1 hour. The solvent was removed under vacuum, and the residue was purified by prep-TLC with DCM/MeOH (15/1) to afford the desired product (E)-2-(2,6-dioxopiperidin-3-yl)-5-(3-(1-(2-(4-(4-(1-(hydroxyimino)-2,3-dihydro-1H-inden-5-yl)-3-(pyridin-4-yl)-1H-pyrazol-1-yl)phenoxy)ethyl)piperidin-4-yl)azetidin-1-yl)isoindoline-1,3-dione (15 mg, 50% yield) as yellow solid. $^1$H NMR (400 MHz, DMSO-d$_6$): δ 11.07 (s, 1H), 10.91 (s, 1H), 8.75 (s, 1H), 8.57 (d, J=5.6 Hz, 2H), 7.87 (d, J=8.8 Hz, 2H), 7.65 (d, J=4.8 Hz, 1H), 7.55 (d, J=4.8 Hz, 1H), 7.49 (d, J=5.6 Hz, 2H), 7.41 (s, 1H), 7.21 (d, J=4.8 Hz, 1H), 7.12 (d, J=9.2 Hz, 2H), 6.77 (s, 1H), 6.63 (d, J=4.4 Hz, 1H), 5.00-5.10 (m, 1H), 4.05-4.20 (m, 4H), 3.70-3.80 (m, 2H), 2.70-3.10 (m, 7H), 2.55-2.65 (m, 4H), 1.70-2.05 (m, 10H); LCMS: (ES+): m/z 806.3 [M+H]$^+$.

Example Synthesis of Compound 213: (E)-2-(2,6-dioxopiperidin-3-yl)-4-(3-(2-(2-((4-(4-(1-(hydroxyimino)-2,3-dihydro-1H-inden-5-yl)-3-(pyridin-4-yl)-1H-pyrazol-1-yl)phenoxy)methyl)phenoxy)ethoxy)propoxy)isoindoline-1,3-dione Step A: (2-(2-(3-((tert-butyldimethylsilyl)oxy)propoxy)ethoxy)phenyl)methanol

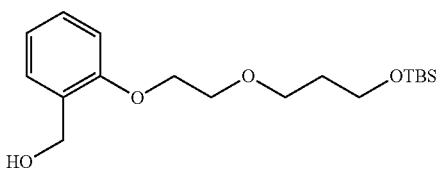

To a solution of 2-(3-((tert-butyldimethylsilyl)oxy)propoxy)ethyl 4-methylbenzenesulfonate (1 g, 2.58 mmol) in DMF (10 mL) were added 2-(hydroxymethyl)phenol (0.38 g, 3.09 mol) and K$_2$CO$_3$ (1.07 g, 2.74 mmol). The resulting solution was stirred at 70° C. for 3 hours. After cooling to room temperature, the reaction was quenched with NH$_4$Cl aq, and the mixture was extracted EtOAc. The organic phase was dried over anhydrous sodium sulfate, concentrated under vacuum. The residue was purified by chromatography column to afford (2-(2-(3-((tert-butyldimethylsilyl)oxy)-propoxy)ethoxy)phenyl)methanol (400 mg, 45.6% yield) as colorless oil. $^1$H NMR (400 MHz, CDCl$_3$): δ 7.36-7.34 (d, J=7.2 Hz, 1H), 7.18-7.14 (t, J=7.2 Hz, 1H), 6.93-6.90 (m, 2H), 4.90-4.87 (t, J=5.6 Hz, 1H), 4.49-4.47

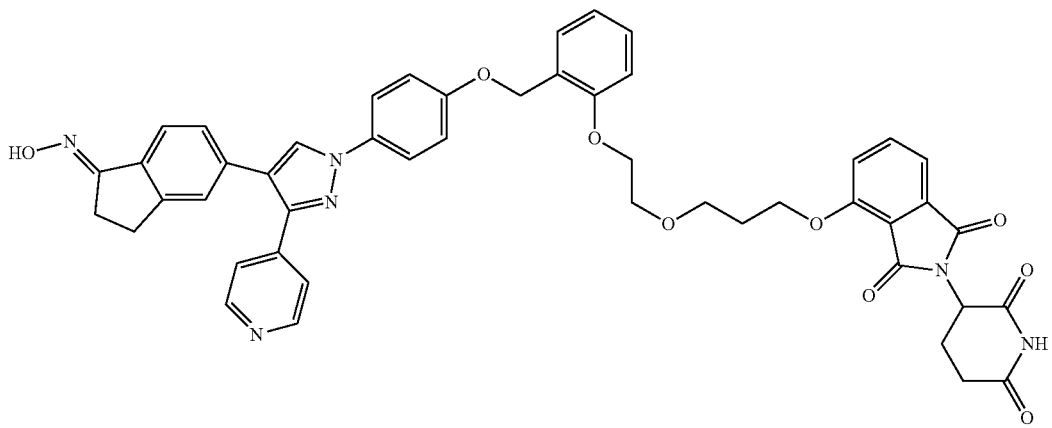 [SMILES: O=C1CCC(N2C(=O)c3cccc(OCCCOCCOc4ccccc4COc4ccc(-n5cc(-c6ccc7c(c6)CC/C7=N\O)c(-c6ccncc6)n5)cc4)c3C2=O)C(=O)N1]

(m, 2H), 4.07-4.05 (m, 2H), 3.68-3.61 (m, 4H), 3.52-2.90 (t, J=6.4 Hz, 2H), 1.70-1.64 (m, 2H), 0.83 (s, 9H), 0.00 (s, 6H).

Step B: 4-(4-bromo-1-(4-((2-(2-(3-((tert-butyldimethylsilyl)oxy)propoxy)ethoxy) benzyl)oxy)phenyl)-1H-pyrazol-3-yl)pyridine

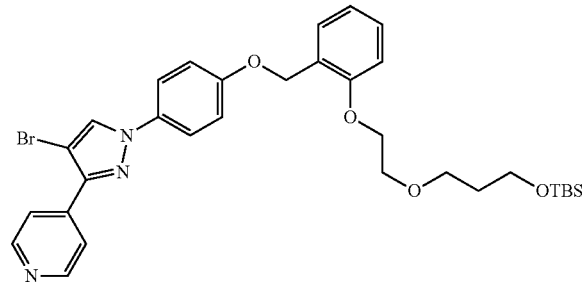 [SMILES: CC(C)(C)[Si](C)(C)OCCCOCCOc1ccccc1COc1ccc(-n2cc(Br)c(-c3ccncc3)n2)cc1]

To a solution of (2-(2-(3-((tert-butyldimethylsilyl)oxy)propoxy)ethoxy)phenyl)-methanol (400 mg, 1.18 mmol) in DCM (20 mL) and DIPEA (457 mg, 3.54 mmol) was added MsCl (268 mg, 2.36 mmol) at 0° C. The resulting solution was stirred at room temperature for 1 hour. The reaction was diluted with DCM (100 mL), washed with water, brine. The organic phase was dried over anhydrous sodium sulfate, concentrated under vacuum to afford crude desired product (320 mg, 100% yield), which was used in next step directly. To a solution of above desired product (320 mg, 0.89 mmol) in dry DMF (20 ml) was added K₂CO₃ (368.5 mg, 2.67 mmol) and 4-(4-bromo-3-(pyridin-4-yl)-1H-pyrazol-1-yl)phenol (309.7 mg, 0.98 mmol). The resulting solution was stirred at 70° C. for 2 hours. After cooled to room temperature, the reaction mixture was diluted with EtOAc (100 mL), washed with water and brine. The organic phase was dried over anhydrous sodium sulfate. The residue was purified by chromatography column to afford 4-(4-bromo-1-(4-((2-(2-(3-((tert-butyldimethylsilyl)oxy)propoxy)ethoxy)benzyl)oxy)phenyl)-1H-pyrazol-3-yl)-pyridine (300 mg, 40.1% yield 2 steps) as red oil. ¹H NMR (400 MHz, CDCl₃): δ 8.73-8.67 (m, 2H), 8.00-7.90 (m, 3H), 7.63-7.59 (d, J=9.2 Hz, 1H), 7.50-7.42 (m, 1H), 7.33-7.27 (m, 2H), 7.12-7.08 (m, 2H), 7.02-6.91 (m, 2H), 5.20 (s, 2H), 4.22-4.17 (t, J=4.8 Hz, 2H), 3.84-3.76 (t, J=5.2 Hz, 2H), 3.70-3.67 (t, J=6.4 Hz, 2H), 3.62-3.59 (t, J=6.4 Hz, 2H), 1.82-1.75 (m, 2H), 0.87 (s, 9H), 0.02 (s, 6H).

Step C: 3-(2-(2-((4-(4-bromo-3-(pyridin-4-yl)-1H-pyrazol-1-yl)phenoxy)methyl)phenoxy)ethoxy)propan-1-ol

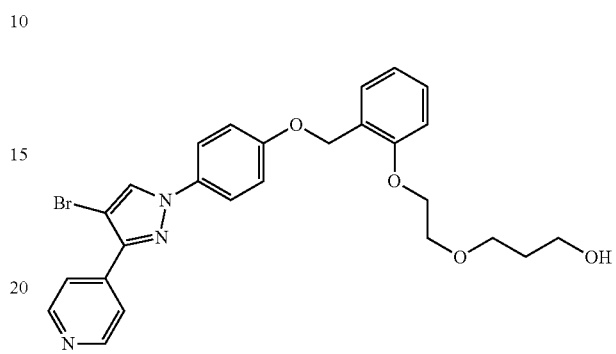

To a solution of 4-(4-bromo-1-(4-((2-(2-(3-((tert-butyldimethylsilyl)oxy)-propoxy)ethoxy)benzyl)oxy)phenyl)-1H-pyrazol-3-yl)pyridine (300 mg, 0.47 mmol) in MeOH (10 mL) was added HCl in 1,4-dioxane(1 mL, 6 M/L, 6 mmol) at room temperature. The resulting solution was stirred at room temperature for 0.5 hours. The solution was concentrated and diluted with 100 ml of DCM, washed with NaHCO₃ (50 mL×3). The organic phase was dried over anhydrous sodium sulfate and concentrated under vacuum. The residue was purified by preparative TLC to afford desired product 3-(2-(2-((4-(4-Bromo-3-(pyridin-4-yl)-1H-pyrazol-1-yl)phenoxy)methyl)phenoxy)ethoxy)propan-1-ol (160 mg, 65% yield) as white solid. LCMS (ES⁺): m/z 524.1 [M+H]⁺.

Step D: tert-butyl 5-amino-4-(4-(3-(2-(2-((4-(4-bromo-3-(pyridin-4-yl)-1H-pyrazol-1-yl)phenoxy)methyl)phenoxy)ethoxy)propoxy)-1,3-dioxoisoindolin-2-yl)-5-oxopentanoate

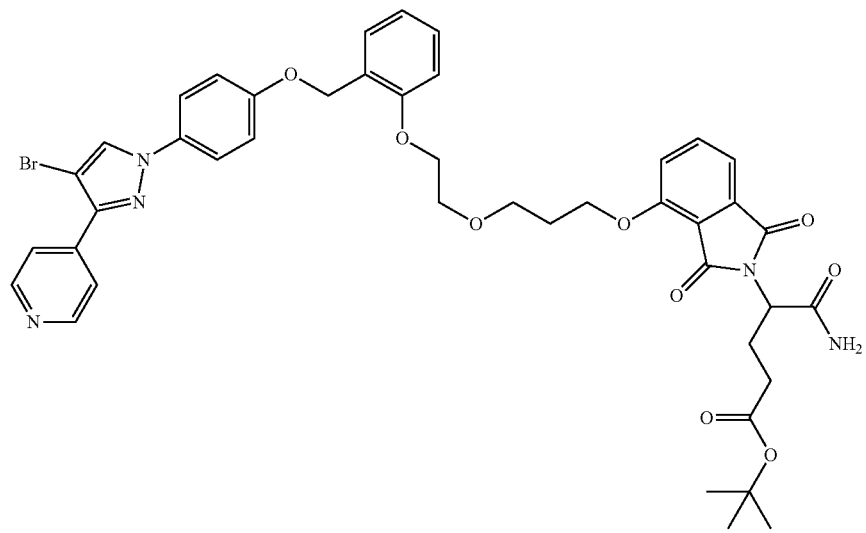 [SMILES: CC(C)(C)OC(=O)CCC(C(N)=O)N1C(=O)c2cccc(OCCCOCCOc3ccccc3COc3ccc(-n4cc(Br)c(-c5ccncc5)n4)cc3)c2C1=O]

To a solution of 3-(2-(2-((4-(4-bromo-3-(pyridin-4-yl)-1H-pyrazol-1-yl)phenoxy) methyl)phenoxy)ethoxy)propan-1-ol (160 mg, 0.31 mmol) PPh₃ (244 mg, 0.93 mmol) and tert-butyl 5-amino-4-(4-hydroxy-1,3-dioxoisoindolin-2-yl)-5-oxopentanoate (159.4 mg, 0.46 mmol) in dry THF (10 mL) was added DIAD (188 mg, 0.93 mmol) under N₂. The resulting solution was stirred at room temperature for 2 hours. After quenched with water, the mixture was extracted with DCM. The combined organic layer was washed with water and brine, dried over anhydrous sodium sulfate and concentrated. The residue was purified by preparative TLC to afford desired product tert-butyl 5-amino-4-(4-(3-(2-(2-((4-(4-bromo-3-(pyridin-4-yl)-1H-pyrazol-1-yl)phenoxy)methyl)phenoxy)ethoxy)-propoxy)-1,3-dioxoisoindolin-2-yl)-5-oxopentanoate (110 mg, 42.2% yield) as white solid. LCMS (ES⁺): m/z 854.2 [M+H]⁺.

Step D: 4-(3-(2-(2-((4-(4-bromo-3-(pyridin-4-yl)-1H-pyrazol-1-yl)phenoxy)methyl) phenoxy)ethoxy) propoxy)-2-(2,6-dioxopiperidin-3-yl)isoindoline-1,3-dione

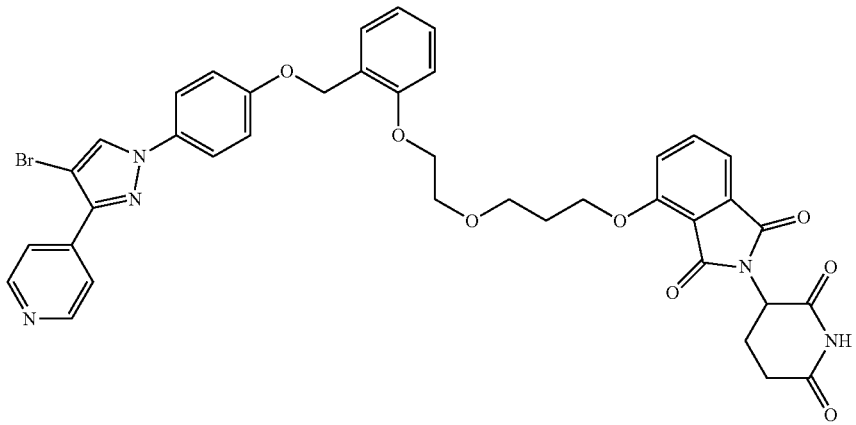 [SMILES: O=C1CCC(N2C(=O)c3cccc(OCCCOCCOc4ccccc4COc4ccc(-n5cc(Br)c(-c6ccncc6)n5)cc4)c3C2=O)C(=O)N1]

To a solution of tert-butyl 5-amino-4-(4-(3-(2-(2-((4-(4-bromo-3-(pyridin-4-yl)-1H-pyrazol-1-yl)phenoxy)methyl)phenoxy)ethoxy)propoxy)-1,3-dioxoisoindolin-2-yl)-5-oxopentanoate (80 mg, 0.094 mmol) in acetonitrile (15 mL), add 4-methylbenzenesulfonic acid (32.3 mg, 0.28 mmol). The solution was stirred at 60° C. for 48 hours. After cooling to room temperature, the reaction was quenched with NaHCO₃ aq. (to pH>7), and the mixture was extracted with DCM (20 mL×3). The combined organic layer was dried over Na₂SO₄ and concentrated under vacuum. The residue was purified by perp-TLC to afford desired product 4-(3-(2-(2-((4-(4-bromo-3-(pyridin-4-yl)-1H-pyrazol-1-yl)phenoxy)methyl) phenoxy)ethoxy)propoxy)-2-(2,6-dioxopiperidin-3-yl)-isoindoline-1,3-dione (40 mg, 54.8% yield) as white solid. LCMS (ES⁺): m/z 781.1 [M+H]⁺.

Step E: 2-(2,6-dioxopiperidin-3-yl)-4-(3-(2-(2-((4-(4-(1-oxo-2,3-dihydro-1H-inden-5-yl)-3-(pyridin-4-yl)-1H-pyrazol-1-yl)phenoxy)methyl)phenoxy)ethoxy)propoxy) isoindoline-1,3-dione

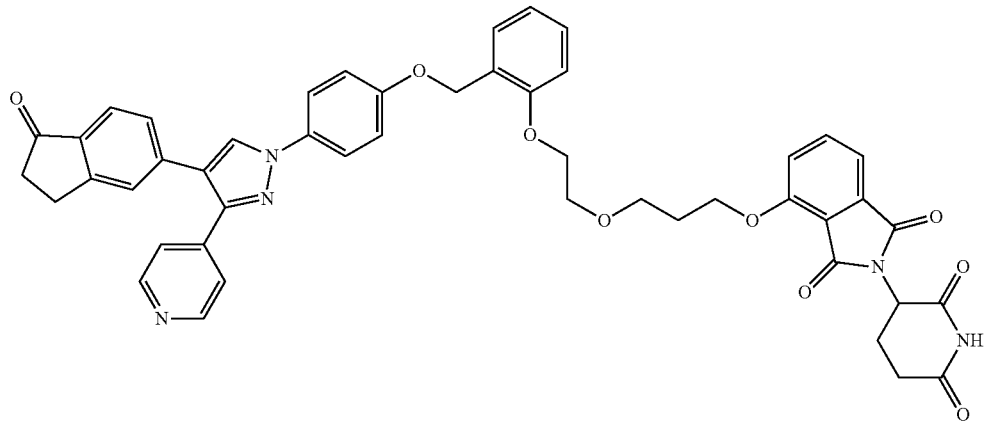 [SMILES: O=C1CCC(N2C(=O)c3cccc(OCCCOCCOc4ccccc4COc4ccc(-n5cc(-c6ccc7c(c6)CCC7=O)c(-c6ccncc6)n5)cc4)c3C2=O)C(=O)N1]

To a solution of 4-(3-(2-(2-((4-(4-bromo-3-(pyridin-4-yl)-1H-pyrazol-1-yl)phenoxy)methyl)phenoxy)ethoxy)propoxy)-2-(2,6-dioxopiperidin-3-yl)isoindoline-1,3-dione (40 mg, 0.051 mmol) in 1,4-dioxane/H$_2$O (5 mL, v/v=10/1) was added 5-(4,4,5,5-tetramethyl-1,3,2-dioxaborolan-2-yl)-2,3-dihydro-1H-inden-1-one (19.87 mg, 0.077 mmol), Pd$_2$(dba)$_3$ (4.67 mg, 0.0051 mmol), CsF(31.0 mg, 0.20 mmol) [(t-Bu)$_3$PH]BF$_4$ (0.59 mg, 0.0020 mmol), N,N-dicyclohexylmethylamine (0.50 mg, 0.0026 mmol). The resulting solution was stirred at 100° C. for 2 hours under N$_2$. After cooling to room temperature, the reaction was diluted with DCM (50 mL), washed with water and brine. The organic phase was dried over anhydrous sodium sulfate, concentrated under vacuum. The residue was purified by preparative TLC to afford desired product 2-(2,6-dioxopiperidin-3-yl)-4-(3-(2-(2-((4-(4-(1-oxo-2,3-dihydro-1H-inden-5-yl)-3-(pyridin-4-yl)-1H-pyrazol-1-yl)phenoxy)methyl)phenoxy)ethoxy)propoxy)isoindoline-1,3-dione (30 mg, 70.3% yield) as white solid. LCMS (ES$^+$): m/z 832.3 [M+H]$^+$.

Step F: (E)-2-(2,6-dioxopiperidin-3-yl)-4-(3-(2-(2-((4-(4-(1-(hydroxyimino)-2,3-dihydro-1H-inden-5-yl)-3-(pyridin-4-yl)-1H-pyrazol-1-yl)phenoxy)methyl)phenoxy)ethoxy)propoxy)isoindoline-1,3-dione was stirred at 40° C. for 20 minutes, the it was diluted with DCM (20 mL), and washed with brine (10 mL). The organic phase was concentrated under vacuum. The residue was purified by preparative TLC to afford (E)-2-(2,6-dioxopiperidin-3-yl)-4-(3-(2-(2-((4-(4-(1-(hydroxyimino)-2,3-dihydro-1H-inden-5-yl)-3-(pyridin-4-yl)-1H-pyrazol-1-yl)phenoxy)methyl)phenoxy)ethoxy)propoxy)isoindoline-1,3-dione (6.2 mg, 20.3% yield) as white solid. $^1$H NMR (400 MHz, CDCl$_3$): δ 8.57-8.56 (m, 2H), 8.32 (s, 1H), 7.93 (s, 1H), 7.69-7.63 (m, 3H), 7.57-7.51 (m, 3H), 7.43-7.41 (m, 1H), 7.38-7.36 (d, J=7.2 Hz, 1H), 7.28 (s, 2H), 7.23 (s, 2H), 7.15-7.13 (d, J=7.6 Hz, 1H), 7.08-7.06 (m, 2H), 7.00-6.97 (m, 1H), 6.91-6.89 (d, J=7.6 Hz, 1H), 5.15 (s, 2H), 4.92-4.88 (m, 1H), 4.26-4.23 (t, J=6.4 Hz, 2H), 4.20-4.17 (t, J=4.4 Hz, 2H), 3.86-3.84 (t, J=4.8 Hz, 2H), 3.79-3.76 (t, J=6.0 Hz, 2H), 3.08-2.96 (m, 4H), 2.90-2.82 (m, 1H), 2.81-2.66 (m, 2H), 2.16-2.05 (m, 3H); LCMS (ES$^+$): m/z 847.3 [M+H]$^+$.

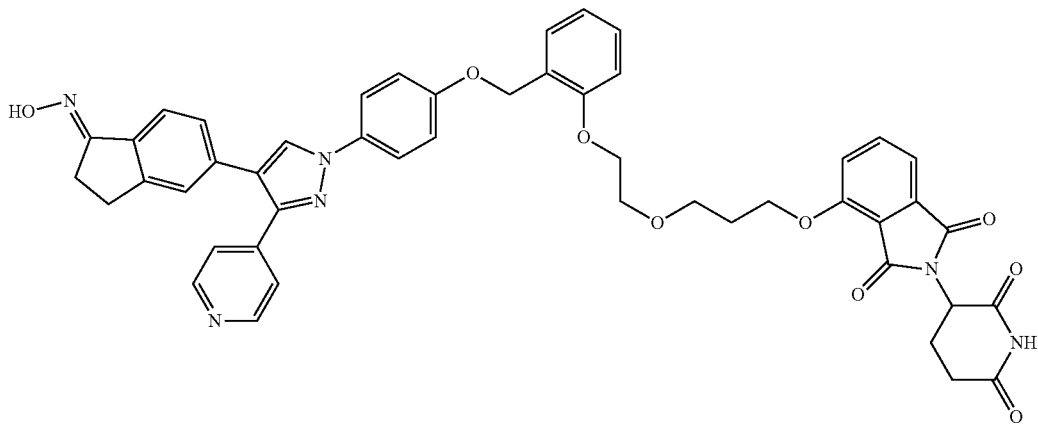 [SMILES: O=C1CCC(N2C(=O)c3cccc(OCCCOCCOc4ccccc4COc4ccc(-n5cc(-c6ccc7c(c6)CC/C7=N\O)c(-c6ccncc6)n5)cc4)c3C2=O)C(=O)N1]

To a solution of 2-(2,6-dioxopiperidin-3-yl)-4-(3-(2-(2-((4-(4-(1-oxo-2,3-dihydro-1H-inden-5-yl)-3-(pyridin-4-yl)-1H-pyrazol-1-yl)phenoxy)methyl)phenoxy)ethoxy)-propoxy)isoindoline-1,3-dione (30 mg, 0.036 mmol) in acetonitrile/pyridine (3 mL, v/v=2/1) was added hydroxylamine hydrochloride (25.1 mg, 0.36 mmol). The mixture Compound 212 may be prepared in a manner analogous to compound 213.

Example Synthesis of Compound 215: (E)-2-(2,6-Dioxopiperidin-3-yl)-4-(3-(3-((4'-(4-(1-(hydroxyimino)-2,3-dihydro-1H-inden-5-yl)-3-(pyridin-4-yl)-1H-pyrazol-1-yl)-[1,1'-biphenyl]-4-yl)oxy)propoxy)propoxy)isoindoline-1,3-dione

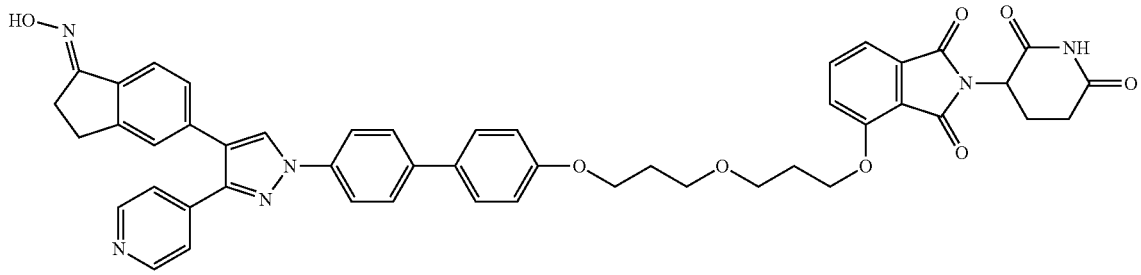 [SMILES: O=C1CCC(N2C(=O)c3cccc(OCCCOCCCOc4ccc(-c5ccc(-n6cc(-c7ccc8c(c7)CC/C8=N\O)c(-c7ccncc7)n6)cc5)cc4)c3C2=O)C(=O)N1]

Step A: 4-bromo-4'-methoxy-1,1'-biphenyl

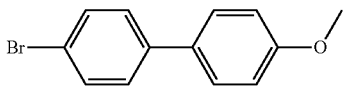

To a solution of (4-methoxyphenyl)boronic acid (5 g, 32.9 mmol) in toluene/MeOH (200 mL/100 mL) was added 1,4-dibromobenzene (11.6 g, 49.4 mmol), Pd(PPh$_3$)$_4$ (1.9 g, 1.65 mmol) and Cs$_2$CO$_3$ (21.4 g, 65.8 mmol). The resulting solution was stirred at 100° C. for 16 hours under N$_2$ atmosphere. TLC showed the reaction was completed. After cooled to room temperature, the reaction mixture was diluted with 50 mL of EA, washed with water, brine. The organic phase was dried over anhydrous sodium sulfate and concentrated in vacuo. The residue was purified by chromatography column to afford 4-bromo-4'-methoxy-1,1'-biphenyl (7.0 g, 80% yield). LCMS (ES+): m/z 263.1 [M+H]$^+$.

Step B: (4'-methoxy-[1,1'-biphenyl]-4-yl)boronic acid

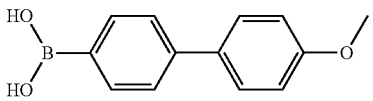

To a solution of 4-bromo-4'-methoxy-1,1'-biphenyl (2 g, 7.63 mmol) in dry THF (30 mL) was added n-BuLi (9.2 ml, 22.9 mmol, 2.5 M in hexane) dropwise at −78° C. under N$_2$ atmosphere. 1 hour later, (CH$_3$O)$_3$B (2.38 g, 22.9 mmol) was added dropwise at −78° C. The resulting solution was stirred for 1 hour at −78° C. and overnight at 5° C. After quenched with saturated NH$_4$Cl solution, the mixture was extracted with EA (30 mL×2.) The combined organic layer was dried over anhydrous sodium sulfate. The residue was purified by chromatography column to afford (4'-methoxy-[1,1'-biphenyl]-4-yl)boronic acid (1.0 g, 58% yield). $^1$H NMR (400 MHz, DMSO-d6): δ 8.06 (s, 2H), 7.84 (d, J=7.6 Hz, 2H), 7.63 (d, J=7.6 Hz, 2H), 7.58 (d, J=7.6 Hz, 2H), 7.02 (d, J=7.6 Hz, 2H), 3.80 (s, 3H).

Step C: 4-(4-bromo-1-(4'-methoxy-[1,1'-biphenyl]-4-yl)-1H-pyrazol-3-yl)pyridine

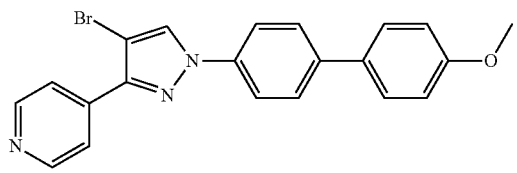 [SMILES: COc1ccc(-c2ccc(-n3cc(Br)c(-c4ccncc4)n3)cc2)cc1]

To a solution of (4'-methoxy-[1,1'-biphenyl]-4-yl)boronic acid (1 g, 4.39 mmol) in DCM/pyridine (40 ml/4 ml) was added Cu(OAc)$_2$ (0.8 g, 4.39 mmol) and 4-(4-bromo-1H-pyrazol-3-yl)pyridine (1.5 g, 6.58 mmol). The resulting solution was stirred at 5° C. for 16 hours under O$_2$ atmosphere. The reaction mixture was washed with ammonia (20 mL×2). The organic phase was dried over Na$_2$SO$_4$, concentrated under vacuum. The residue was applied onto a silica gel column to afford desired product 4-(4-bromo-1-(4'-methoxy-[1,1'-biphenyl]-4-yl)-1H-pyrazol-3-yl)pyridine (1 g crude, 56% yield). LCMS (ES$^+$): m/z 407.4 [M+H]$^+$.

Step D: 4-(1-(4'-(3-(3-(benzyloxy)propoxy)propoxy)-[1,1'-biphenyl]-4-yl)-4-bromo-1H-pyrazol-3-yl)pyridine

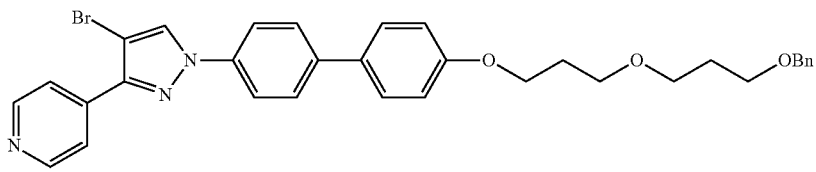 [SMILES: Brc1cn(-c2ccc(-c3ccc(OCCCOCCCOCc4ccccc4)cc3)cc2)nc1-c1ccncc1]

To a solution of 4-(4-Bromo-1-(4'-methoxy-[1,1'-biphenyl]-4-yl)-1H-pyrazol-3-yl) pyridine (1 g, 2.46 mmol) in DCM (40 mL) was added BBr$_3$ (1.85 g, 7.38 mmol) dropwise. The resulting solution was stirred at 10° C. for 2 hour. After quenched with MeOH and concentrated, crude was applied onto a silica gel column to afford desired product 4'-(4-bromo-3-(pyridin-4-yl)-1H-pyrazol-1-yl)-[1,1'-biphenyl]-4-ol (0.6 g, 62% yield). To a solution of 4'-(4-bromo-3-(pyridin-4-yl)-1H-pyrazol-1-yl)-[1,1'-biphenyl]-4-ol (375 mg, 0.96 mmol) in dry DMF (5 mL) was added Cs$_2$CO$_3$ (1.56 g, 4.80 mmol) and 3-(3-(benzyloxy)propoxy)propyl methanesulfonate (0.58 g, 1.92 mmol). The resulting solution was stirred at 75° C. for 2 hours. After cooled to room temperature, the reaction mixture was diluted with EA (50 mL), washed with water and brine. The organic layer was dried over anhydrous sodium sulfate. The residue was purified by chromatography column to afford 4-(1-(4'-(3-(3-(benzyloxy)propoxy)propoxy)-[1,1'-biphenyl]-4-yl)-4-bromo-1H-pyrazol-3-yl)pyridine (400 mg, 70% yield). $^1$H NMR (400 MHz, DMSO-d6): δ 9.02 (s, 1H), 8.73 (br, 2H), 8.00 (m, 2H), 7.80 (d, J=8.0 Hz, 2H), 7.67 (d, J=8.4 Hz, 2H), 7.30 (m, 5H), 7.03 (d, J=8.4 Hz, 2H), 4.45 (m, 2H), 4.06 (t, J=5.6 Hz, 2H), 3.53 (m, 7H), 1.97 (m, 2H), 1.77 (m, 2H).

Step E: 5-(1-(4'-(3-(3-hydroxypropoxy)propoxy)-[1,1'-biphenyl]-4-yl)-3-(pyridin-4-yl)-1H-pyrazol-4-yl)-2,3-dihydro-1H-inden-1-one

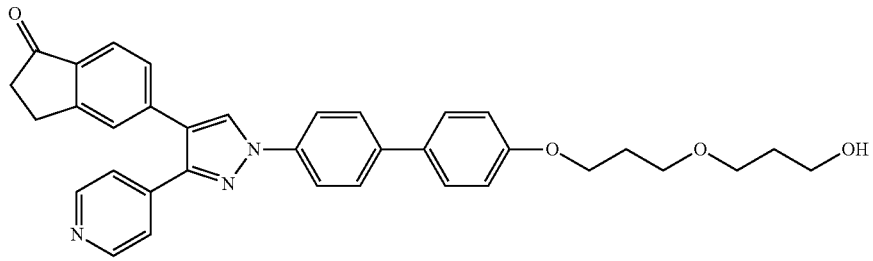 [SMILES: O=C1CCc2cc(-c3cn(-c4ccc(-c5ccc(OCCCOCCCO)cc5)cc4)nc3-c3ccncc3)ccc21]

To a solution of 4-(1-(4'-(3-(3-(benzyloxy)propoxy)propoxy)-[1,1'-biphenyl]-4-yl)-4-bromo-1H-pyrazol-3-yl)pyridine (0.4 g, 0.67 mmol) and 5-(4,4,5,5-tetramethyl-1,3,2-dioxaborolan-2-yl)-2,3-dihydro-1H-inden-1-one (260 mg, 1.01 mmol) in 1,4-dioxane (15 mL)/H$_2$O (1.5 mL) was added CsF (328 mg, 2.16 mmol), Pd$_2$(dba)$_3$(196 mg, 0.216 mmol). tri-tert-butylphosphine tetrafluoroborate (124 mg, 0.43 mmol) and two drops of N-cyclohexyl-N-methylcyclohexanamine subsequently. The reaction was heated to 100° C. for 2 hours under N$_2$ atmosphere. After cooling to room temperature, the reaction was quenched with water (20 mL), and the mixture was extracted with ethyl acetate (30 mL×2). The combined organic layer was dried over anhydrous sodium sulfate and concentrated under vacuum. The residue was applied onto a silica gel column to afford desired product 5-(1-(4'-(3-(3-(benzyloxy)propoxy)propoxy)-[1,1'-biphenyl]-4-yl)-3-(pyridin-4-yl)-1H-pyrazol-4-yl)-2,3-dihydro-1H-inden-1-one (0.4 g, 92% yield) as brown oil. To a solution of 5-(1-(4'-(3-(3-(benzyloxy)propoxy)propoxy)-[1,1'-biphenyl]-4-yl)-3-(pyridin-4-yl)-1H-pyrazol-4-yl)-2,3-dihydro-1H-inden-1-one (400 mg, 0.16 mmol) in THF/MeOH (10 mL/1 mL and two drops of concentrated HCl was added Pd(OH)$_2$ on carbon (200 mg). The mixture was stirred at 5° C. for 1 hour under H$_2$ 1 atm. The mixture was filtered and the solid was washed with THF. The organic layer was concentrated and purified by column to afford 5-(1-(4'-(3-(3-hydroxypropoxy)propoxy)-[1,1'-biphenyl]-4-yl)-3-(pyridin-4-yl)-1H-pyrazol-4-yl)-2,3-dihydro-1H-inden-1-one (250 mg, 72% yield). $^1$H NMR (400 MHz, CDCl$_3$): δ 8.73 (d, J=5.6 Hz, 2H), 8.64 (s, 3H), 8.10 (m, 2H), 7.85 (m, 3H), 7.68 (d, J=6.0 Hz, 2H), 7.55 (m, 4H), 7.28-7.50 (m, 6H), 7.00 (d, J=8.4 Hz, 2H), 5.68 (m, 1H), 4.49 (s, 2H), 4.15 (m, 3H), 3.45-3.70 (m, 6H), 3.18 (m, 2H), 2.78 (m, 2H)

Step F: tert-butyl 5-amino-4-(1,3-dioxo-4-(3-(3-((4'-(4-(1-oxo-2,3-dihydro-1H-inden-5-yl)-3-(pyridin-4-yl)-1H-pyrazol-1-yl)-[1,1'-biphenyl]-4-yl)oxy)propoxy)propoxy)isoindolin-2-yl)-5-oxopentanoate

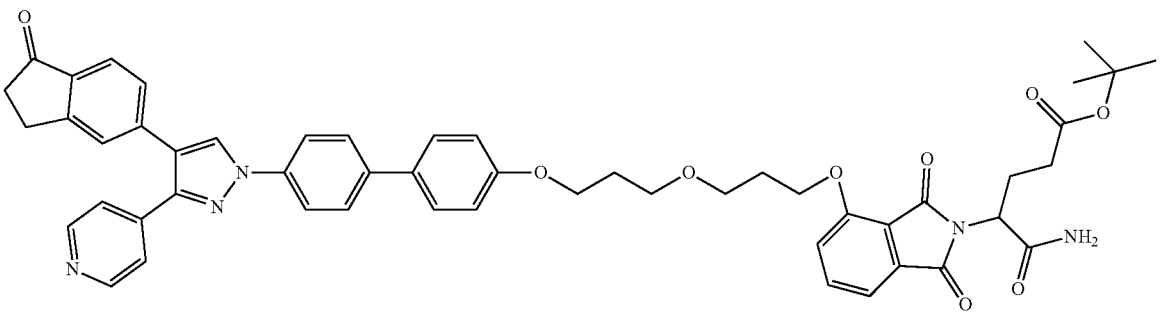 [SMILES: CC(C)(C)OC(=O)CCC(C(N)=O)N1C(=O)c2cccc(OCCCOCCCOc3ccc(-c4ccc(-n5cc(-c6ccc7c(c6)CCC7=O)c(-c6ccncc6)n5)cc4)cc3)c2C1=O]

To a solution of 5-(1-(4'-(3-(3-hydroxypropoxy)propoxy)-[1,1'-biphenyl]-4-yl)-3-(pyridin-4-yl)-1H-pyrazol-4-yl)-2,3-dihydro-1H-inden-1-one (250 mg, 0.45 mmol), Ph$_3$P (351 mg, 1.35 mmol) and tert-butyl 5-amino-4-(4-hydroxy-1,3-dioxoisoindolin-2-yl)-5-oxopentanoate (233 mg, 0.67 mmol) in dry THF (20 mL) was DIAD (266 mg, 1.35 mmol) in THF (3 mL) dropwise at 0° C. The resulting solution was stirred at 0-10° C. for 2 hours. The reaction was diluted with EA (50 mL), washed with water and brine. The organic layer was dried over anhydrous sodium sulfate, concentrated and applied onto a silica gel column to afford tert-butyl 5-amino-4-(1,3-dioxo-4-(3-(3-((4'-(4-(1-oxo-2,3-dihydro-1H-inden-5-yl)-3-(pyridin-4-yl)-1H-pyrazol-1-yl)-[1,1'-biphenyl]-4-yl)oxy)propoxy)propoxy)isoindolin-2-yl)-5-oxopentanoate (150 mg, 38% yield) as oil. LCMS (ES+): m/z 890.4 [M+H]$^+$.

629

Step G: 2-(2,6-dioxopiperidin-3-yl)-4-(3-(3-((4'-(4-(1-oxo-2,3-dihydro-1H-inden-5-yl)-3-(pyridin-4-yl)-1H-pyrazol-1-yl)-[1,1'-biphenyl]-4-yl)oxy)propoxy) propoxy)isoindoline-1,3-dione

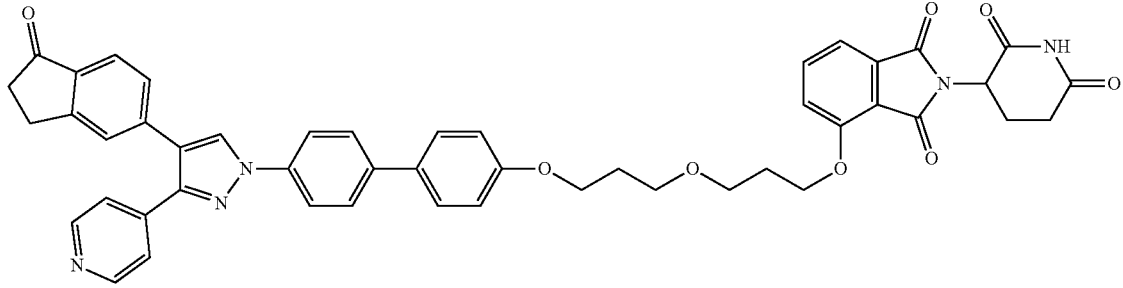 [SMILES: O=C1CCC(N2C(=O)c3cccc(OCCCOCCCOc4ccc(-c5ccc(-n6cc(-c7ccc8c(c7)CCC8=O)c(-c7ccncc7)n6)cc5)cc4)c3C2=O)C(=O)N1]

To a solution of tert-butyl 5-amino-4-(1,3-dioxo-4-(3-(3-((4'-(4-(1-oxo-2,3-dihydro-1H-inden-5-yl)-3-(pyridin-4-yl)-1H-pyrazol-1-yl)-[1,1'-biphenyl]-4-yl)oxy)propoxy) propoxy)isoindolin-2-yl)-5-oxopentanoate (150 mg, 0.168 mmol) in CH$_3$CN (5 mL) was added TsOH (289 mg, 1.68 mmol). The resulting solution was stirred at 80° C. for 3 hours. The reaction was quenched by saturated NaHCO$_3$ and extracted with EA. The organic layer was dried over anhydrous sodium sulfate, concentrated and purified by preparative TLC to afford 2-(2,6-dioxopiperidin-3-yl)-4-(3-(3-((4'-(4-(1-oxo-2,3-dihydro-1H-inden-5-yl)-3-(pyridin-4-yl)-1H-pyrazol-1-yl)-[1,1'-biphenyl]-4-yl)oxy)propoxy)propoxy) isoindoline-1,3-dione (100 mg, 73% yield). LCMS (ES+): m/z 816.3 [M+H]$^+$.

Step H: (E)-2-(2,6-dioxopiperidin-3-yl)-4-(3-(3-((4'-(4-(1-(hydroxyimino)-2,3-dihydro-1H-inden-5-yl)-3-(pyridin-4-yl)-1H-pyrazol-1-yl)-[1,1'-biphenyl]-4-yl) oxy)propoxy)propoxy)isoindoline-1,3-dione

630

To a solution of 2-(2,6-dioxopiperidin-3-yl)-4-(3-(3-((4'-(4-(1-oxo-2,3-dihydro-1H-inden-5-yl)-3-(pyridin-4-yl)-1H-pyrazol-1-yl)-[1,1'-biphenyl]-4-yl)oxy)propoxy)propoxy) isoindoline-1,3-dione (100 mg, 0.123 mmol) and hydroxylamine hydrochloride (256 mg, 3.681 mmol) in MeOH/DCM (4 mL/1 mL) was added NaHCO$_3$ (464 mg, 5.521 mmol) at 50° C. The mixture was stirred at 50° C. for 1 hour. The residue was purified by preparative TLC with DCM/MeOH (20:1) to afford the desired product (E)-2-(2,6-dioxopiperidin-3-yl)-4-(3-(3-((4'-(4-(1-(hydroxyimino)-2,3-dihydro-1H-inden-5-yl)-3-(pyridin-4-yl)-1H-pyrazol-1-yl)-[1,1'-biphenyl]-4-yl)oxy)propoxy)propoxy)isoindoline-1,3-dione (24 mg, 24% yield) as a yellow solid. $^1$H NMR (400 MHz, DMSO-d6): δ 11.09 (s, 1H), 10.90 (s, 1H), 8.90 (s, 1H), 8.59 (d, J=5.6 Hz, 2H), 8.02 (d, J=8.4 Hz, 2H), 7.79 (m, 3H), 7.38-7.70 (m, 8H), 7.25 (d, J=6.0 Hz, 1H), 6.98 (d, J=8.8 Hz, 2H), 5.09 (m, 1H), 4.26 (m, 2H), 4.05 (m, 2H), 3.60 (m, 4H), 3.05 (m, 2H), 2.86 (m, 3H), 2.50 (m, 3H), 2.03 (m, 5H); LCMS (ES$^+$): m/z 831.3 [M+H]$^+$.

Compound 214 may be prepared in a manner analogous to compound 215.

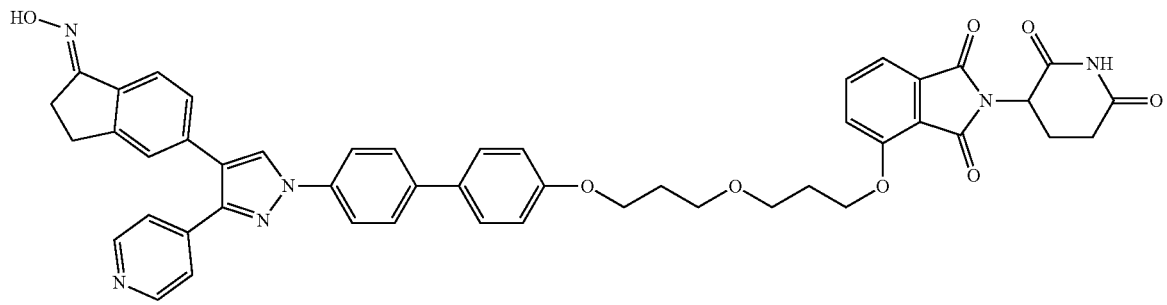 [SMILES: O=C1CCC(N2C(=O)c3cccc(OCCCOCCCOc4ccc(-c5ccc(-n6cc(-c7ccc8c(c7)CC/C8=N\O)c(-c7ccncc7)n6)cc5)cc4)c3C2=O)C(=O)N1]

Example Synthesis of Compound 100: (2S,4R)-1-((S)-2-(2-(3-(4-(4-(3-(2,6-Difluoro-3-((R)-3-fluoropyrrolidine-1-sulfonamido)benzoyl)-1H-pyrrolo[2,3-b]pyridin-5-yl)phenyl)piperazin-1-yl)propoxy)acetamido)-3,3-dimethylbutanoyl)-4-hydroxy-N-(4-(4-methylthiazol-5-yl)benzyl)pyrrolidine-2-carboxamide

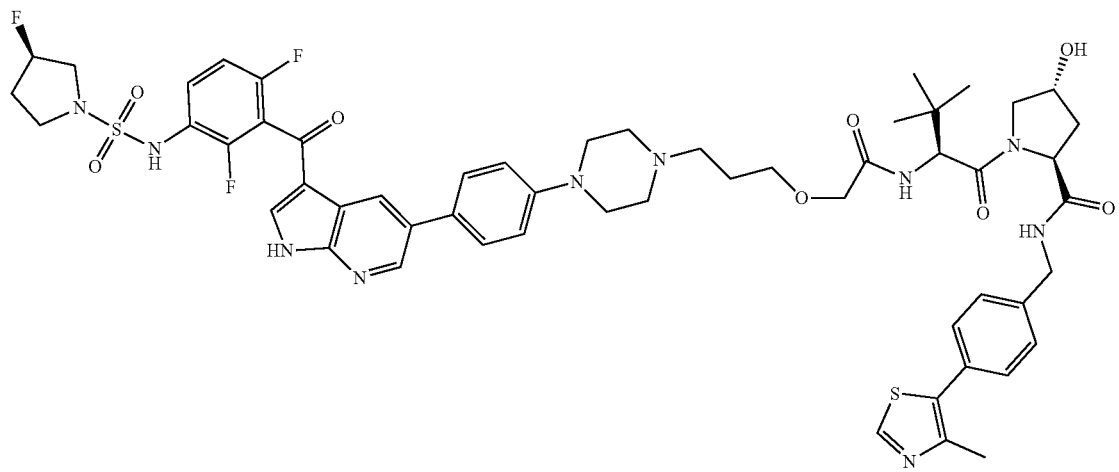 [SMILES: Cc1ncsc1-c1ccc(CNC(=O)[C@@H]2C[C@@H](O)CN2C(=O)[C@@H](NC(=O)COCCCN2CCN(c3ccc(-c4cnc5[nH]cc(C(=O)c6c(F)ccc(NS(=O)(=O)N7CC[C@@H](F)C7)c6F)c5c4)cc3)CC2)C(C)(C)C)cc1]

Step A: tert-butyl 2-(3-chloropropoxy)acetate

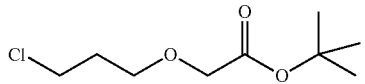

To a solution of tert-butyl 2-bromoacetate (5.0 g, 26 mmol) and 3-chloropropan-1-ol (2.9 g, 31 mmol) in dry DMF (15 mL) was added NaOH (1.2 g, 31 mmol) at 0° C. After stirring for 2 hours at 0° C., it was warmed to room temperature overnight. The reaction was quenched with H$_2$O (20 mL) at 0° C., and the mixture was extracted with PE (20 mL×2). The combined organic layer was washed with water, brine. The organic phase was concentrated under vacuum to afford desired product tert-butyl 2-(3-chloropropoxy)-acetate (2.8 g, 52% yield) as oil, which was used directly in next step. $^1$H NMR (400 MHz, CDCl$_3$): δ 3.97 (s, 2H), 3.65-3.70 (m, 4H), 2.05-2.08 (m, 2H), 1.49 (s, 9H).

Step B: tert-butyl 2-(3-(4-(4-(4,4,5,5-tetramethyl-1,3,2-dioxaborolan-2-yl)phenyl)piperazin-1-yl)propoxy)acetate

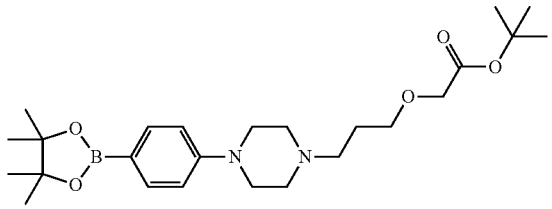 [SMILES: CC(C)(C)OC(=O)COCCCN1CCN(c2ccc(B3OC(C)(C)C(C)(C)O3)cc2)CC1]

To a solution of 1-(4-(4,4,5,5-tetramethyl-1,3,2-dioxaborolan-2-yl)phenyl)piperazine 2,2,2-trifluoroacetate (530 mg, 1.32 mmol) in dry DMF (5 mL) were added K$_2$CO$_3$ (911 mg, 6.60 mmol), KI (438 mg, 2.64 mmol) and tert-butyl 2-(3-chloropropoxy)acetate (550 mg, 2.64 mmol) subsequently. The resulting solution was stirred at 90° C. for 3 hours. After cooling to room temperature, the reaction was diluted with EA (50 mL), and the mixture was washed with water, brine. The organic phase was concentrated under vacuum. The residue was purified by prep-TLC to afford desired product tert-butyl 2-(3-(4-(4-(4,4,5,5-tetramethyl-1,3,2-dioxaborolan-2-yl)phenyl) piperazin-1-yl)propoxy)acetate (300 mg, crude). $^1$H NMR (400 MHz, CDCl$_3$): δ 7.70 (d, J=8.0 Hz, 2H), 6.89 (d, J=8.0 Hz, 2H), 3.96 (br, 2H), 3.27 (br, 4H), 3.21 (br, 2H), 2.60 (br, 4H), 2.51-2.53 (m, 2H), 1.82-1.85 (m, 2H), 1.42 (s, 9H), 1.24 (s, 12H).

Step C: (R)-tert-butyl 2-(3-(4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)propoxy)acetate

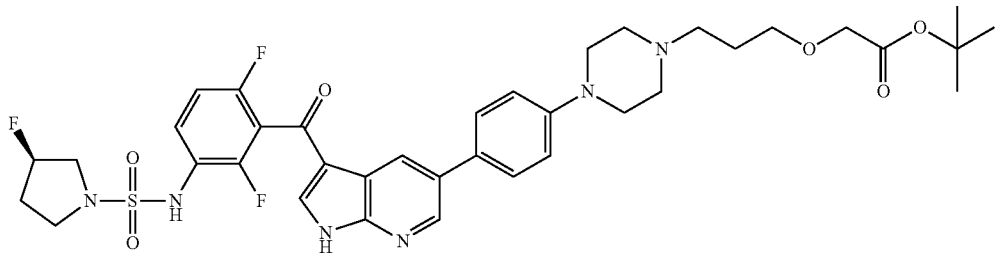 [SMILES: CC(C)(C)OC(=O)COCCCN1CCN(c2ccc(-c3cnc4[nH]cc(C(=O)c5c(F)ccc(NS(=O)(=O)N6CC[C@@H](F)C6)c5F)c4c3)cc2)CC1]

To a solution of (R)—N-(3-(5-bromo-1H-pyrrolo[2,3-b]pyridine-3-carbonyl)-2,4-difluorophenyl)-3-fluoropyrrolidine-1-sulfonamide (100 mg, 0.20 mmol) in dioxane/H$_2$O (10 mL/1 mL) was added tert-Butyl 2-(3-(4-(4-(4,4,5,5-tetramethyl-1,3,2-dioxaborolan-2-yl)phenyl)piperazin-1-yl)propoxy)acetate (200 mg, 0.43 mmol), Pd(aMphos)Cl$_2$ (15 mg, 0.02 mmol) and CsF (121 mg, 0.80 mmol). The resulting solution was stirred at 95° C. for 16 hours under N$_2$ atmosphere. TLC showed completion of the reaction. After cooled to room temperature, the reaction mixture was diluted with 50 ml of EA, washed with water and brine. The organic layer was dried over anhydrous sodium sulfate. The residue was purified by pre-TLC to afford desired product (R)-tert-butyl 2-(3-(4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)propoxy)acetate (80 mg, 53% yield). $^1$H NMR (400 MHz, CDCl$_3$): δ 12.00 (br, 1H), 8.87 (s, 1H), 8.60 (s, 1H), 7.75 (s, 2H), 7.54 (d, J=8.0 Hz, 2H), 6.98-7.05 (m, 3H), 5.15-5.30 (m, 1H), 3.97 (s, 2H), 3.71-3.75 (m, 2H), 3.49-3.65 (m, 6H), 3.28 (s, 4H), 2.58-2.67 (m, 6H), 1.80-2.30 (m, 3H), 1.49 (s, 9H).

Step D: (2S,4R)-1-((S)-2-(2-(3-(4-(4-(3-(2,6-Difluoro-3-((R)-3-fluoropyrrolidine-1-sulfonamido)benzoyl)-1H-pyrrolo[2,3-b]pyridin-5-yl)phenyl)piperazin-1-yl)propoxy)acetamido)-3,3-dimethylbutanoyl)-4-hydroxy-N-(4-(4-methylthiazol-5-yl)benzyl)pyrrolidine-2-carboxamide

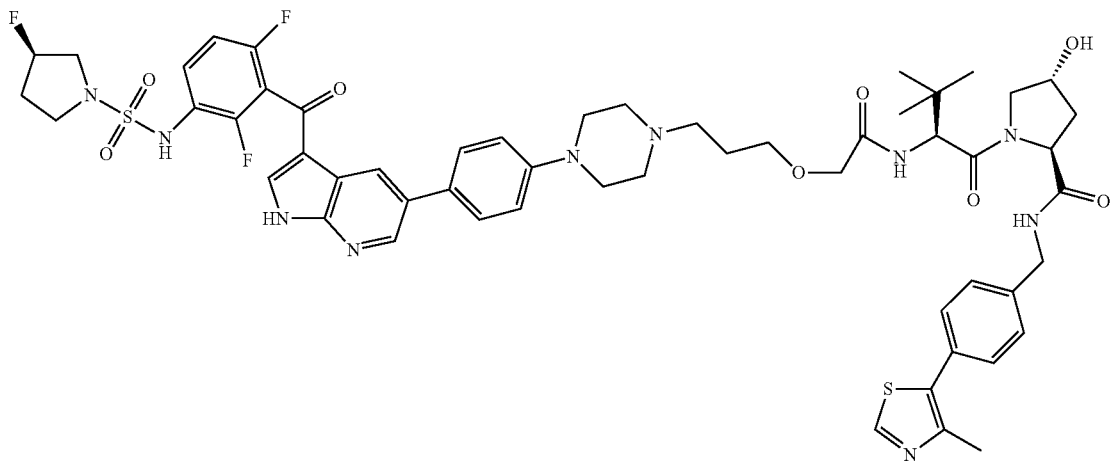 [SMILES: Cc1ncsc1-c1ccc(CNC(=O)[C@@H]2C[C@@H](O)CN2C(=O)[C@@H](NC(=O)COCCCN2CCN(c3ccc(-c4cnc5[nH]cc(C(=O)c6c(F)ccc(NS(=O)(=O)N7CC[C@@H](F)C7)c6F)c5c4)cc3)CC2)C(C)(C)C)cc1]

To a solution of (R)-tert-butyl 2-(3-(4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)propoxy)acetate (80 mg, 0.13 mmol) in dioxane (2 mL) was added HCl in dioxane (2 mL, 8 M). The resulting solution was stirred at 50° C. for 5 hours. After cooling to room temperature, the solvent was removed under vacuum to afford (R)-2-(3-(4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)propoxy)acetic acid (74 mg, 100% yield, calculated). To a solution of (R)-2-(3-(4-(4-(3-(2,6-difluoro-3-(3-fluoropyrrolidine-1-sulfonamido)-benzoyl)-1H-pyrrolo[2,3-b]pyridin-5-yl)phenyl)piperazin-1-yl)propoxy)acetic acid (74 mg, 0.11 mmol) (2S,4R)-1-((S)-2-amino-3,3-dimethylbutanoyl)-4-hydroxy-N-(4-(4-methylthiazol-5-yl)benzyl)pyrrolidine-2-carboxamide hydrochloride (91 mg, 0.19 mmol) and DIEA (142 mg, 1.10 mmol) in dry NMP (5.0 mL) was added PyBOP (172 mg, 0.33 mmol) at room temperature. After stirring at 10° C. for 1 hour, the reaction was quenched with brine (20 mL), and the mixture was taken up with EA. The organic phase was concentrated under vacuum, and the residue was purified by prep-TLC and prep-HPLC to afford desired product (2S,4R)-1-((S)-2-(2-(3-(4-(4-(3-(2,6-difluoro-3-((R)-3-fluoropyrrolidine-1-sulfonamido)benzoyl)-1H-pyrrolo[2,3-b]pyridin-5-yl)phenyl)piperazin-1-yl)propoxy)acetamido)-3,3-dimethylbutanoyl)-4-hydroxy-N-(4-(4-methylthiazol-5-yl)benzyl)pyrrolidine-2-carboxamide (20 mg, 17% yield 2 steps) as white solid. $^1$H NMR (400 MHz, CD$_3$OD): δ 8.82 (s, 1H), 8.65 (s, 1H), 8.59 (s, 1H), 7.89 (s, 1H), 7.74 (m, 1H), 7.59 (d, J=8.8 Hz, 2H), 7.30-7.50 (m, 4H), 7.07-7.20 (m, 3H), 5.15-5.30 (m, 1H), 4.62 (s, 1H), 4.50-4.60 (m, 3H), 4.30 (d, J=7.8 Hz, 1H), 4.12 (m, 2H), 3.78-3.95 (m, 2H), 3.40-3.80 (m, 14H), 3.10 (m, 5H), 2.42 (s, 3H), 1.98-2.30 (m, 8H), 1.03 (s, 9H); LCMS (ES$^+$): m/z 1113.3 [M+H]$^+$.

Example Synthesis of Compound 152: (E)-2-(2,6-dioxopiperidin-3-yl)-5-(4-(2-(4-(4-(1-(hydroxyimino)-2,3-dihydro-1H-inden-5-yl)-3-(pyridin-4-yl)-1H-pyrazol-1-yl)phenoxy)ethyl)piperazin-1-yl)isoindoline-1,3-dione

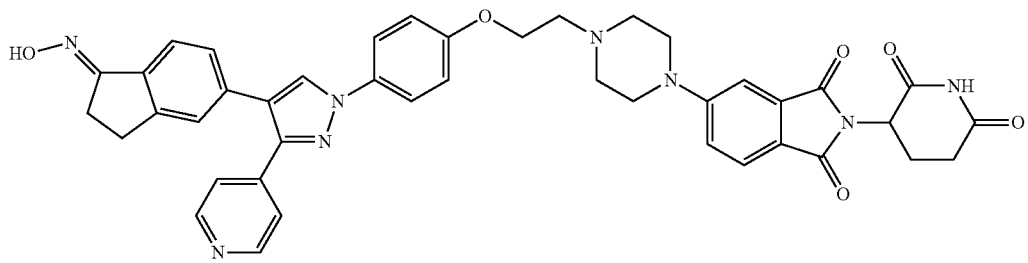 [SMILES: O=C1CCC(N2C(=O)c3ccc(N4CCN(CCOc5ccc(-n6cc(-c7ccc8c(c7)CC/C8=N\O)c(-c7ccncc7)n6)cc5)CC4)cc3C2=O)C(=O)N1]

Step A: 2-(4-(4-bromo-3-(pyridin-4-yl)-1H-pyrazol-1-yl)phenoxy)acetaldehyde

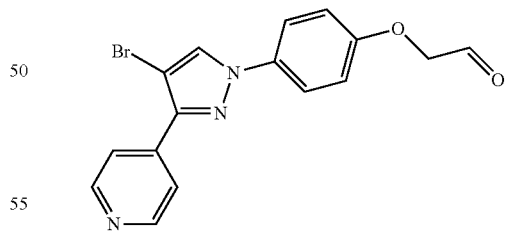

To a solution of 4-(4-bromo-1-(4-(2,2-diethoxyethoxy)phenyl)-1H-pyrazol-3-yl)pyridine (1 g, 2.32 mmol) in CH$_3$CN (10 mL) was added conc. HCl (2 mL, diluted in 6 mL H$_2$O). The resulting solution was stirred at 55° C. for 1 hour. After cooling to 0° C., The pH was adjusted to around 9 by progressively adding saturated NaHCO3 aqueous solution. The solid was filtered and co-evaporated with CH$_3$CN to afford 2-(4-(4-bromo-3-(pyridin-4-yl)-1H-pyrazol-1-yl)phenoxy)acetaldehyde (0.3 g, 66.9% yield) as a white solid. LCMS (ES$^+$): m/z 358.0, 376.0/378.0 [M+H]$^+$, [M+18]$^+$.

Step B: 5-(4-(2-(4-(4-bromo-3-(pyridin-4-yl)-1H-pyrazol-1-yl)phenoxy)ethyl)piperazin-1-yl)-2-(2,6-dioxopiperidin-3-yl)isoindoline-1,3-dione

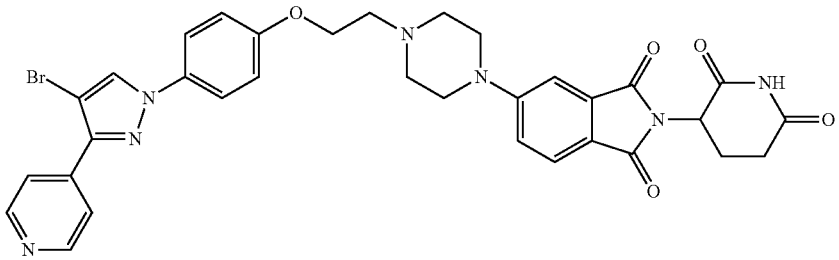 [SMILES: O=C1CCC(N2C(=O)c3ccc(N4CCN(CCOc5ccc(-n6cc(Br)c(-c7ccncc7)n6)cc5)CC4)cc3C2=O)C(=O)N1]

To a solution of 2-(4-(4-bromo-3-(pyridin-4-yl)-1H-pyrazol-1-yl)phenoxy) acetaldehyde (0.1 g, 0.28 mmol) in MeOH (10 mL) were added 2-(2,6-dioxopiperidin-3-yl)-5-(piperazin-1-yl)isoindoline-1,3-dione hydrochloride (127 mg, 0.34 mmol) and cat. HOAc. AcOK was added if pH was below 5-6. Then NaBH$_3$CN (87 mg, 1.40 mmol) was added. The resulting solution was stirred at 20° C. for 1 hour. After quenched with saturated NH$_4$Cl (20 mL), and the mixture was extracted with DCM (30 mL×2). The combined organic layer was dried over anhydrous sodium sulfate and concentrated under vacuum. The residue was purified by prep-TLC to afford desired product 5-(4-(2-(4-(4-bromo-3-(pyridin-4-yl)-1H-pyrazol-1-yl)-phenoxy)ethyl)piperazin-1-yl)-2-(2,6-dioxopiperidin-3-yl)isoindoline-1,3-dione (90 mg, 35% yield). LCMS (ES$^+$): m/z 684.1/686.1 [M+H]$^+$.

Step C: 2-(2,6-dioxopiperidin-3-yl)-5-(4-(2-(4-(4-(1-oxo-2,3-dihydro-1H-inden-5-yl)-3-(pyridin-4-yl)-1H-pyrazol-1-yl)phenoxy)ethyl)piperazin-1-yl)isoindoline-1,3-dione

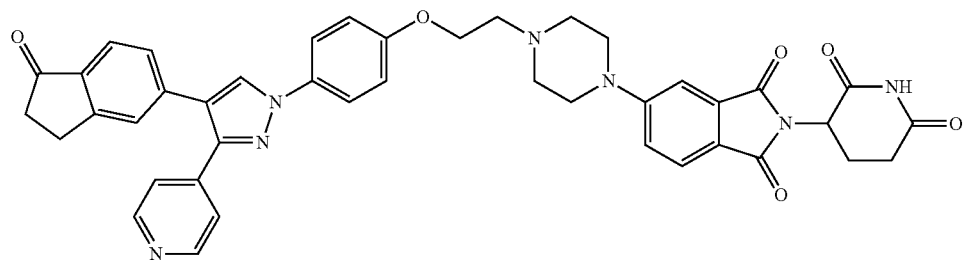 [SMILES: O=C1CCC(N2C(=O)c3ccc(N4CCN(CCOc5ccc(-n6cc(-c7ccc8c(c7)CCC8=O)c(-c7ccncc7)n6)cc5)CC4)cc3C2=O)C(=O)N1]

To a solution of 5-(4-(2-(4-(4-bromo-3-(pyridin-4-yl)-1H-pyrazol-1-yl)phenoxy) ethyl)piperazin-1-yl)-2-(2,6-dioxopiperidin-3-yl)isoindoline-1,3-dione (90 mg, 0.13 mmol) and 5-(4,4,5,5-tetramethyl-1,3,2-dioxaborolan-2-yl)-2,3-dihydro-1H-inden-1-one (37 mg, 0.15 mmol) in dioxane/H$_2$O (10 mL/1 mL) were added t-Bu$_3$PHBF$_4$ (31 mg, 0.11 mmol), CsF (80 mg, 0.53 mmol), Cy$_2$NMe (5 drops) and Pd$_2$(dba)$_3$ (48 mg, 0.05 mmol) subsequently. The resulting mixture was stirred at 90° C. for 2 hours under N$_2$. After cooling to room temperature, the solvent was removed under reduced pressure. The residue was diluted with EA (30 mL), and then the mixture was washed with brine. The organic phase was evaporated under vacuum. The residue was purified by prep-TLC and prep-HPLC to afford desired product 2-(2,6-Dioxopiperidin-3-yl)-5-(4-(2-(4-(4-(1-oxo-2,3-dihydro-1H-inden-5-yl)-3-(pyridin-4-yl)-1H-pyrazol-1-yl)phenoxy) ethyl)piperazin-1-yl)isoindoline-1,3-dione (60 mg, 69% yield). LCMS (ES$^+$): m/z 736.3 [M+H]$^+$.

66Step D: (E)-2-(2,6-dioxopiperidin-3-yl)-5-(4-(2-(4-(4-(1-(hydroxyimino)-2,3-dihydro-1H-inden-5-yl)-3-(pyridin-4-yl)-1H-pyrazol-1-yl)phenoxy)ethyl)piperazin-1-yl)isoindoline-1,3-dione

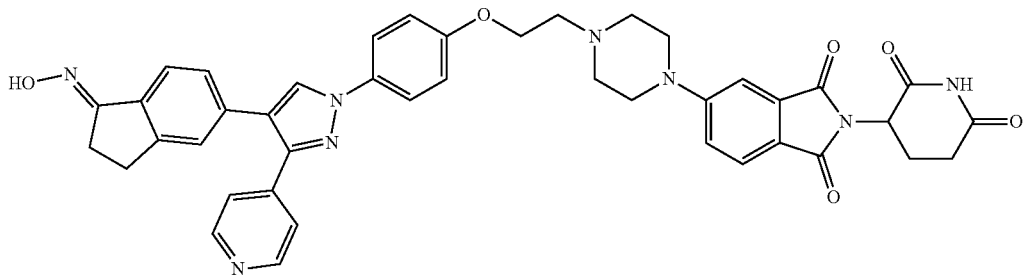 [SMILES: O=C1CCC(N2C(=O)c3ccc(N4CCN(CCOc5ccc(-n6cc(-c7ccc8c(c7)CC/C8=N\O)c(-c7ccncc7)n6)cc5)CC4)cc3C2=O)C(=O)N1]

To a solution of 2-(2,6-dioxopiperidin-3-yl)-5-(4-(2-(4-(4-(1-oxo-2,3-dihydro-1H-inden-5-yl)-3-(pyridin-4-yl)-1H-pyrazol-1-yl)phenoxy)ethyl)piperazin-1-yl)isoindoline-1,3-dione (60 mg, 0.08 mmol) in $CH_3CN$/pyridine (6 mL/3 mL) was added $NH_2OH \cdot HCl$ (57 mg, 0.82 mmol). The mixture was stirred at 45° C. for 0.5 hours. The mixture was diluted with DCM (30 mL) and washed with brine. The organic phase was concentrated under reduced pressure. The residue was purified by prep-TLC (DCM/MeOH 15/1) to afford desired product (E)-2-(2,6-dioxopiperidin-3-yl)-5-(4-(2-(4-(4-(1-(hydroxyimino)-2,3-dihydro-1H-inden-5-yl)-3-(pyridin-4-yl)-1H-pyrazol-1-yl)phenoxy)ethyl)piperazin-1-yl)isoindoline-1,3-dione as a yellow solid (45 mg, 73% yield). $^1H$ NMR (400 MHz, DMSO-$d_6$): δ 11.07 (s, 1H), 10.89 (s, 1H), 8.75 (s, 1H), 8.58 (d, J=5.6 Hz, 2H), 7.87 (d, J=8.8 Hz, 2H), 7.68 (d, J=8.4 Hz, 1H), 7.55 (d, J=8.0 Hz, 1H), 7.48 (d, J=4.4 Hz, 2H), 7.20-7.41 (m, 4H), 7.14 (d, J=9.2 Hz, 2H), 5.08 (m, 1H), 4.21 (t, J=5.6 Hz, 2H), 3.47 (m, 4H), 2.99-3.02 (m, 2H), 2.67-2.89 (m, 10H), 2.05 (m, 1H); LCMS (ES+): m/z 751.3 [M+H]+.

Example Synthesis of Compound 216: (2S,4R)-1-((S)-2-(3-(2-(3-(3-(2,6-difluoro-3-(propylsulfonamido)benzoyl)-1H-pyrrolo[2,3-b]pyridin-5-yl)phenoxy)ethoxy)propanamido)-3,3-dimethylbutanoyl)-4-hydroxy-N-(4-(4-methylthiazol-5-yl)benzyl)pyrrolidine-2-carboxamide To a solution of 3-[2-[3-[3-[2,6-difluoro-3-(propylsulfonyl-amino)benzoyl]-1H-pyrrolo[2,3-b]pyridin-5-yl]phenoxy]ethoxy]-propanoic acid (22.8 mg, 0.04 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (19.93 mg, 0.043 mmol) in DMF(2 ml) was added TEA (0.1 ml, 0.72 mmol) and PyBOP (22.21 mg, 0.043 mmol) at room temperature. The reaction mixture was stirred for 12 h (overnight) at the same temperature. TLC (DCM:MEOH:$NH_4OH$, 90:9:1) shows no starting materials. The DMF was removed under high vacuum. Crude product was filtered over a silica-carbonate cartridge using DCM:MeOH (9:1) as a eluent. Filtrate was evaporated under vacuum and crude product was purified by PTLC (MeOH:DCM, 1:9, 2×) to give 20 mg of product (52% yield). $^1H$ NMR (500 MHz, DMSO-d6) δ 13.00 (bs, 1H), 9.78 (bs, 1H), 8.96 (s, 1H), 8.71 (s, 1H), 8.62 (s, 1H), 8.55 (t, J=5.5 Hz, 1H), 8.23 (s, 1H), 7.96 (d, J=9.2 Hz, 1H), 7.59 (q, J=8.3 Hz, 1H), 7.52-7.18 (m, 8H), 6.99 (d, J=8.2 Hz, 1H), 5.13 (d, J=3.8 Hz, 1H), 4.57 (d, J=9.4 Hz, 1H), 4.48-4.32 (m, 3H), 4.23 (d, J=5.5 Hz, 1H), 4.19 (t, J=5.1 Hz, 2H), 3.86-3.57 (m, 6H), 3.19-3.06 (m, 2H), 2.61 (m, 1H), 2.43 (s, 3H), 2.43-2.37 (m, 1H), 2.08-2.00 (m, 1H), 1.95-1.87 (m, 1H), 1.80-1.69 (m, 2H), 0.94 (s, 9H), 0.95 (t, 3H). $^{13}C$ NMR (151 MHz, dmso) δ 180.64, 171.95, 169.97, 169.57, 159.10, 156.03 (dd, J=246.6, 6.9 Hz), 152.34 (dd, J=249.6, 8.4 Hz), 151.42, 148.97, 147.72, 144.17, 139.67, 139.50, 138.81, 131.46, 131.17, 130.28, 129.64, 128.94-128.71 (m), 128.64, 127.42, 127.17, 121.98 (dd, J=13.6, 3.4 Hz), 119.57, 118.54-117.84 (m), 117.47, 115.72, 113.74, 113.11, 112.53-112.23 (m), 68.91, 68.69, 67.21, 67.13, 58.74, 56.37, 53.46, 41.68, 37.97, 35.70, 35.37, 26.36, 16.86, 15.95, 12.63. LC-MS (ESI); m/z [M+H]+: Calcd. for $C_{50}H_{56}F_2N_7O_9S_2$, 1000.3548. Found 1000.3536.

Example Synthesis of Compound of 217: N1-(4-(3-(2,6-difluoro-3-(propylsulfonamido)benzoyl)-1H-pyrrolo[2,3-b]pyridin-5-yl)phenyl)-N5-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide To a solution of 5-((4-(3-(2,6-difluoro-3-(propylsulfonamido)-benzoyl)-1H-pyrrolo[2,3-b]pyridin-5-yl)phenyl)amino)-5-oxopentanoic acid (9.7 mg, 0.02 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (8.52 mg, 0.02 mmol) in DMF (1 ml) was added TEA (0.1 ml, 0.72 mmol) and PyBOP (9.5 mg, 0.02 mmol) at room temperature. The reaction mixture was stirred for 4 h at the same temperature. TLC (DCM:MEOH:$NH_4OH$, 90:9:1) shows no starting materials. The reaction mixture was diluted with EtOAc (10 mL) and washed with brine (5 mL, 4×), organic phase was dried ($Na_2SO_4$), and evaporated under vacuum. Crude product was purified by PTLC (DCM:MEOH:$NH_4OH$, 90:9:1, 2×) to give 4.8 mg of product (29% yield). $^1H$ NMR (500 MHz, DMSO-d6) δ 10.02 (s, 1H), 8.97 (s, 1H), 8.68 (d, 1H), 8.64-8.52 (m, 2H), 8.21 (s, 1H), 7.95 (d, J=9.2 Hz, 1H), 7.72 (dd, J=36.7, 8.5 Hz, 4H), 7.62-7.54 (m, 1H), 7.40 (dd, 4H), 7.28 (t, J=8.7 Hz, 1H), 5.16 (d, 2H), 4.56 (d, J=9.3 Hz, 1H), 4.50-4.40 (m, 2H), 4.40-4.33 (m, 1H), 4.22 (dd, J=15.8, 5.3 Hz, 1H), 3.76-3.62 (m, 2H), 3.16-3.05 (m, 2H), 2.44 (s, 3H), 2.41-2.17 (m, 4H), 2.09-2.01 (m, 1H), 1.98-1.80 (m, 3H), 1.74 (dq, J=14.9, 7.4 Hz, 2H), 0.96 (s, 9H), 0.95 (t, 3H). $^{13}C$ NMR (151 MHz, dmso) δ 181.06, 172.39, 172.17, 171.46, 170.15, 156.37 (dd, J=246.6, 6.3 Hz), 152.73 (dd, J=249.4, 8.1 Hz), 151.86, 149.05, 148.13, 144.19, 139.91, 139.37, 139.13, 132.97, 131.64, 131.59, 130.05, 129.22 (d, J=14.7 Hz), 129.06, 127.84, 127.74, 126.89, 122.47 (d, J=14.1 Hz), 120.07, 119.02-118.20 (m), 117.95, 116.06, 112.75 (dd, J=23.4, 2.8 Hz), 69.34, 59.15, 56.90, 56.81, 53.87, 42.08, 38.38, 36.36, 35.63, 34.63, 26.85, 21.91, 17.27, 16.37, 13.04. LC-MS (ESI); m/z [M+H]$^+$: Calcd. for $C_{50}H_{55}F_2N_8O_8S_2$, 997.3552. Found 997.3524.

Example Synthesis of Compound 218: (2S,4R)-1-((S)-2-(5-(4-(3-(2,6-difluoro-3-(propylsulfonamido)benzoyl)-1H-pyrrolo[2,3-b]pyridin-5-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide To a solution of 5-(4-(3-(2,6-difluoro-3-(propylsulfonamido)-benzoyl)-1H-pyrrolo[2,3-b]pyridin-5-yl)piperazin-1-yl)-5-oxopentanoic acid (9.3 mg, 0.02 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (8.27 mg, 0.018 mmol) in DMF (1 ml) was added TEA (0.1 ml, 0.72 mmol) and PyBOP (9.22 mg, 0.018 mmol) at room temperature. The reaction mixture was stirred for 4 h at the same temperature. TLC (DCM:MEOH:NH$_4$OH, 90:9:1) shows no starting materials. The reaction mixture was diluted with EtOAc (10 mL) and washed with brine (5 mL, 4×), organic phase was dried (Na$_2$SO$_4$), and evaporated under vacuum. Crude mixture did not show product by TLC, just some starting material (product is soluble in water). Water extracts were lyophilized for overnight, solid residue was filtered using (DCM:MEOH:NH$_4$OH, 90:9:1, 30 mL). Filtrate was evaporated to dryness and crude product was purified by PTLC (DCM:MEOH:NH4OH, 90:9:1, 2×) to give 13 mg of product (81% yield). $^1$H NMR (500 MHz, DMSO-d6) δ 12.64 (bs, 1H), 9.74 (bs, 1H), 8.97 (s, 1H), 8.62-8.52 (m, 3H), 8.28 (d, J=2.0 Hz, 1H), 8.00 (s, 1H), 7.95 (bs, 1H), 7.90 (d, J=9.2 Hz, 1H), 7.59-7.49 (m, 1H), 7.47-7.27 (m, 4H), 7.20 (t, J=8.7 Hz, 1H), 5.13 (bs, 1H), 4.56 (d, J=9.3 Hz, 1H), 4.48-4.32 (m, 3H), 4.22 (dd, J=15.8, 5.3 Hz, 1H), 3.75-3.57 (m, 5H), 3.23-3.02 (m, 7H), 2.44 (s, 3H), 2.41-2.17 (m, 4H), 2.07-2.01 (m, 1H), 1.96-1.87 (m, 1H), 1.81-1.66 (m, 4H), 0.95 (s, 9H), 0.94 (t, 3H). $^{13}$C NMR (151 MHz, dmso) δ 180.70, 171.99, 171.92, 170.44, 169.75, 155.24 (dd, J=248.1, 5.5 Hz), 152.12 (dd, J=248.8, 8.5 Hz), 151.47, 147.73, 144.63, 144.31, 139.52, 138.02, 137.75, 131.19, 129.65, 128.65, 127.98-127.64 (m), 127.44, 123.91-123.09 (m), 118.86-117.72 (m), 117.60, 115.50, 115.23, 112.02 (dd, J=22.6, 3.2 Hz), 68.92, 58.74, 56.47, 56.43, 53.44, 50.31, 50.18, 48.63, 44.86, 41.68, 41.00, 37.99, 34.28, 31.80, 26.43, 21.36, 16.99, 15.97, 12.72. LC-MS (ESI); m/z [M+H]$^+$: Calcd. for $C_{48}H_{58}F_2N_9O_8S_2$, 990.3817. Found 990.3889.

Example Synthesis of Compound 219: (2S,4R)-1-((S)-2-(4-(4-(3-(2,6-difluoro-3-(propylsulfonamido)benzoyl)-1H-pyrrolo[2,3-b]pyridin-5-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide To a solution of 4-(4-(3-(2,6-difluoro-3-(propylsulfonamido)-benzoyl)-1H-pyrrolo[2,3-b]pyridin-5-yl)piperazin-1-yl)-4-oxobutanoic acid (9 mg, 0.016 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (8.2 mg, 0.018 mmol) in DMF (1 ml) was added TEA (0.1 ml, 0.72 mmol) and PyBOP (9.14 mg, 0.018 mmol) at room temperature. The reaction mixture was stirred for 12 h (overnight) at the same temperature. TLC (DCM:MEOH:NH$_4$OH, 90:9:1) shows no starting materials. The reaction mixture was evaporated to dryness. Crude product was filtered over a silica-carbonate cartridge (100 mg) using DCM:MeOH (9:1) as eluent. Filtrate was evaporated under vacuum and crude product was purified by PTLC (DCM:MEOH:NH$_4$OH, 90:9:1, 2×) to give 11 mg of product (75% yield). $^1$H NMR (500 MHz, DMSO-d6) δ 12.66 (bs, 1H), 9.45 (bs, 1H), 8.98 (s, 1H), 8.60 (bs, 1H), 8.29 (s, 1H), 8.04 (s, 1H), 8.01-7.88 (m, 2H), 7.62-7.49 (m, 1H), 7.40 (q, J=8.0 Hz, 4H), 7.26 (t, J=8.8 Hz, 1H), 5.15 (d, J=3.5 Hz, 1H), 4.54 (d, J=9.3 Hz, 1H), 4.49-4.31 (m, 3H), 4.22 (dd, J=16.1, 5.6 Hz, 1H), 3.81-3.53 (m, 6H), 3.26-3.03 (m, 6H), 2.73-2.52 (m, 3H), 2.44 (s, 3H), 2.42-2.33 (m, 1H), 2.09-1.98 (m, 1H), 1.95-1.84 (m, 1H), 1.74 (q, J=7.5 Hz, 2H), 0.96 (t, 3H), 0.94 (s, 9H). $^{13}$C NMR (126 MHz, dmso) δ 180.45, 172.02, 171.35, 170.07, 169.64, 156.00 (dd, J=245.9, 6.5 Hz), 152.34 (dd, J=249.7, 8.3 Hz), 151.52, 147.75, 144.70, 144.30, 139.55, 138.08, 137.91, 131.22, 129.66, 128.69, 128.53 (d, J=2.4 Hz), 127.46, 121.96 (d, J=14.1 Hz), 118.61-117.82 (m), 117.60, 115.44, 115.20, 112.32 (dd, J=23.0, 3.3 Hz), 68.95, 58.78, 56.50, 56.39, 53.46, 50.25, 50.13, 44.76, 41.69, 41.17, 37.99, 35.43, 30.18, 28.05, 26.44, 16.89, 16.00, 12.67. LC-MS (ESI); m/z [M+H]$^+$: Calcd. for $C_{47}H_{56}F_2N_9O_8S_2$, 976.3661. Found 976.3712.

Example Synthesis of Compound 220: N1-(4-(3-(2,6-difluoro-3-(propylsulfonamido)benzoyl)-1H-pyrrolo[2,3-b]pyridin-5-yl)phenyl)-N4-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-succinamide To a solution of 4-((4-(3-(2,6-difluoro-3-(propylsulfonamido)-benzoyl)-1H-pyrrolo[2,3-b]pyridin-5-yl)phenyl)amino)-4-oxobutanoic acid (15 mg, 0.03 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (13.51 mg, 0.03 mmol) in DMF (1 ml) was added TEA (0.1 ml, 0.72 mmol) and PyBOP (15.05 mg, 0.03 mmol) at room temperature. The reaction mixture was stirred for 4 h at the same temperature. TLC (DCM:MEOH:NH4OH, 90:9:1) shows no starting materials. The reaction mixture was evaporated to dryness under high vacuum. Crude product was filtered over a silica-carbonate cartridge (100 mg) using DCM:MeOH (9:1) as eluent. Filtrate was evaporated under vacuum and crude product was purified by PTLC (DCM:MEOH:NH4OH, 90:9:1, 2×) to give 12 mg of product (~85% pure). This product was purified again by PTLC (DCM:MeOH, 9:1) to give 8 mg of product (31% yield). 1H NMR (500 MHz, DMSO-d6) δ 12.97 (bs, 1H), 10.11 (s, 1H), 9.79 (bs, 1H), 8.98 (d, J=2.3 Hz, OH), 8.69 (s, 1H), 8.66-8.49 (m, 2H), 8.23 (s, 1H), 8.02 (d, J=9.0 Hz, 1H), 7.84-7.64 (m, 4H), 7.63-7.53 (m, 1H), 7.51-7.33 (m, 4H), 7.29 (t, J=8.4 Hz, 1H), 5.17 (s, 1H), 4.56 (d, J=7.8 Hz, 1H), 4.50-4.39 (m, 2H), 4.40-4.31 (m, 1H), 4.26-4.16 (m, 1H), 3.66 (q, J=10.1 Hz, 2H), 3.19-3.06 (m, 2H), 2.72-2.52 (m, 4H), 2.44 (s, 3H), 2.12-1.97 (m, 1H), 1.96-1.84 (m, 1H), 1.74 (dq, J=13.2, 8.3, 7.3 Hz, 2H), 0.96 (t, 3H), 0.95 (s, 9H). 13C NMR (126 MHz, dmso) δ 180.66, 172.02, 171.24, 170.67, 169.64, 156.05 (dd, J=246.9, 7.0 Hz), 152.37 (dd, J=249.3, 8.1 Hz), 151.49, 148.66, 147.75, 143.82, 139.53, 139.00, 138.70, 132.54, 131.27, 131.22, 129.68, 129.22-128.38 (m), 128.69, 127.47, 127.39, 126.53, 121.99 (dd, J=12.9, 4.5 Hz), 119.59, 118.72-117.87 (m), 117.57, 115.68, 112.90-112.05 (m), 68.95, 58.79, 56.56, 56.41, 53.51, 41.71, 37.98, 35.45, 31.98, 30.14, 26.43, 16.88, 15.99, 12.65. LC-MS (ESI); m/z [M+H]+: Calcd. for C49H53F2N8O8S2, 983.3395. Found 983.3569.

Example Synthesis of Compound 221: N1-(4-(3-(2,6-difluoro-3-(propylsulfonamido)benzoyl)-1H-pyrrolo[2,3-b]pyridin-5-yl)phenyl)-N3-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-malonamide To a solution 3-((4-(3-(2,6-difluoro-3-(propylsulfonamido)-benzoyl)-1H-pyrrolo[2,3-b]pyridin-5-yl)phenyl)amino)-3-oxopropanoic acid (16.8 mg, 0.03 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (15.5 mg, 0.033 mmol) in DMF (1 ml) was added TEA (0.1 ml, 0.72 mmol) and PyBOP (17.28 mg, 0.033 mmol) at room temperature. The reaction mixture was stirred for 12 h (overnight) at the same temperature. TLC (DCM:MEOH:NH4OH, 90:9:1) shows no starting materials. The reaction mixture was evaporated to dryness under high vacuum. Crude product was filtered over a silica-carbonate cartridge (100 mg) using DCM:MeOH (9:1) as eluent. Filtrate was evaporated under vacuum and crude product was purified by PTLC (DCM:MEOH:NH4OH, 90:9:1, 2×), product was purified again by PTLC (DCM:MeOH, 9:1) to give 19.5 mg of product (67% yield). 1H NMR (400 MHz, DMSO-d6) δ 12.96 (bs, 1H), 10.23 (s, 1H), 9.75 (bs, 1H), 8.97 (s, 1H), 8.69 (s, 1H), 8.66-8.51 (m, 2H), 8.26 (d, J=9.1 Hz, 1H), 8.22 (s, 1H), 7.73 (dd, J=8.5 Hz, 4H), 7.59 (q, J=8.6 Hz, 1H), 7.41 (dd, J=8.0 Hz, 4H), 7.28 (t, J=8.7 Hz, 1H), 5.16 (d, 1H), 4.59 (d, J=9.2 Hz, 1H), 4.52-4.33 (m, 3H), 4.24 (dd, J=15.7, 5.0 Hz, 1H), 3.68 (q, J=10.6 Hz, 2H), 3.44 (q, 2H), 3.20-3.05 (m, 2H), 2.45 (s, 3H), 2.10-2.01 (m, 1H), 1.96-1.89 (m, 1H), 1.74 (dq, J=14.8, 7.3 Hz, 2H), 0.98 (s, 9H), 0.97 (t, J=8.3 Hz, 3H). 13C NMR (101 MHz, dmso) δ 180.62, 171.91, 169.34, 166.16, 166.03, 156.02 (dd, J=246.8, 7.1 Hz), 152.34 (dd, J=249.4, 8.1 Hz), 151.43, 148.69, 147.73, 143.79, 139.50, 138.69, 138.54, 132.98, 131.17, 131.13, 129.68, 129.11-128.65 (m), 128.67, 128.01, 127.45, 126.53, 122.21-121.73 (m), 119.70, 118.63-117.89 (m), 117.54, 115.66, 112.35 (dd, J=23.5, 3.0 Hz), 68.93, 58.79, 56.66, 56.52, 53.49, 44.32, 41.70, 37.97, 35.60, 26.33, 16.85, 15.96, 12.62. LC-MS (ESI); m/z [M+H]+: Calcd. for C48H51F2N8O8S2, 969.3239. Found 969.3272.

Example Synthesis of Compound 222: (2S,4R)-1-((S)-2-(3-(4-(3-(2,6-difluoro-3-(propylsulfonamido)benzoyl)-1H-pyrrolo[2,3-b]pyridin-5-yl)piperazin-1-yl)-3-oxopropanamido)-3,3-dimethylbutanoyl)-4-hydroxy-N-(4-(4-methylthiazol-5-yl)benzyl)pyrrolidine-2-carboxamide To a solution of 3-(4-(3-(2,6-difluoro-3-(propylsulfonamido)-benzoyl)-1H-pyrrolo[2,3-b]pyridin-5-yl)piperazin-1-yl)-3-oxopropanoic acid (12.5 mg, 0.02 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (11.69 mg, 0.03 mmol) in DMF (1 ml) was added TEA (0.1 ml, 0.72 mmol) and PyBOP (13.02 mg, 0.03 mmol) at room temperature. The reaction mixture was stirred for 12 h (overnight) at the same temperature. TLC (DCM:MEOH:NH4OH, 90:9:1) shows no starting materials. The reaction mixture was evaporated to dryness. Crude product was filtered over a silica-carbonate cartridge (100 mg) using DCM:MeOH (9:1) as eluent. Filtrate was evaporated under vacuum and crude product was purified by PTLC (MeOH:DCM, 1:9, 2×) to give 14.1 mg of product (64% yield). 1H NMR (500 MHz, DMSO-d6) δ 12.71 (bs, 1H), 9.74 (bs, 1H), 8.98 (s, 1H), 8.59 (t, J=5.7 Hz, 1H), 8.29 (s, 1H), 8.26 (d, J=9.1 Hz, 1H), 8.03 (s, 1H), 7.96 (bs, 1H), 7.57 (q, J=7.4, 6.3 Hz, 1H), 7.41 (dd, J=8.0 Hz, 4H), 7.26 (t, J=8.7 Hz, 1H), 5.22-5.05 (m, 1H), 4.58 (d, J=9.3 Hz, 1H), 4.51-4.32 (m, 3H), 4.23 (dd, J=15.8, 5.3 Hz, 1H), 3.67 (q, J=12.3, 10.6 Hz, 8H), 3.52 (dd, J=53.7, 15.5 Hz, 2H), 3.27-3.05 (m, 6H), 2.45 (s, 3H), 2.09-2.00 (m, 1H), 1.96-1.86 (m, 1H), 1.74 (h, J=7.3 Hz, 2H), 0.97 (s, 9H), 0.96 (t, 3H). 13C NMR (101 MHz, dmso) δ 180.41, 171.91, 169.38, 166.32, 166.06, 156.01 (dd, J=246.5, 6.7 Hz), 152.34 (dd, J=249.2, 8.3 Hz), 151.44, 147.73, 144.60, 144.28, 139.50, 138.06, 137.84, 131.17, 129.66, 128.75 (d, J=8.0 Hz), 128.65, 127.43, 121.86 (dd, J=13.5, 3.5 Hz), 118.34 (m), 117.58, 115.42, 115.18, 112.28 (dd, J=23.1, 3.5 Hz), 68.89, 58.75, 56.54, 56.43, 53.49, 50.10, 45.56, 41.68, 41.19, 40.95, 37.95, 35.52, 26.36, 16.85, 15.96, 12.62. LC-MS (ESI); m/z [M+H]+: Calcd. for C46H54F2N9O8S2, 962.3504. Found 962.3694.

Example Synthesis of Compound 294: (E)-2-(2,6-dioxopiperidin-3-yl)-5-(3-(4-(4-(1-(hydroxyimino)-2,3-dihydro-1H-inden-5-yl)-3-(pyridin-4-yl)-1H-pyrazol-1-yl)phenoxy)-[1,3'-biazetidin]-1'-yl)isoindoline-1,3-dione

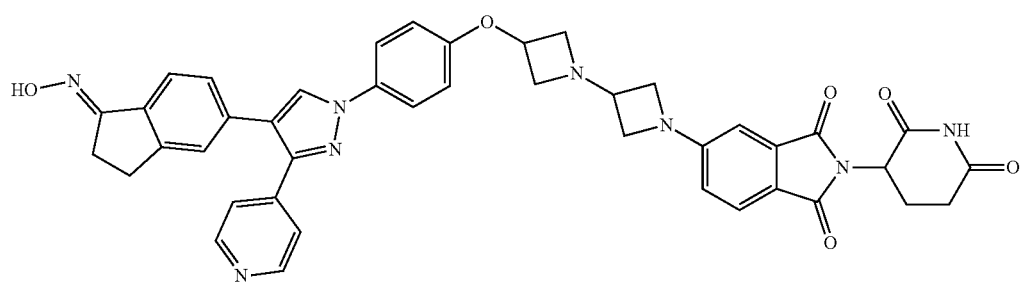 [SMILES: O=C1CCC(N2C(=O)c3ccc(N4CC(N5CC(Oc6ccc(-n7cc(-c8ccc9c(c8)CC/C9=N\O)c(-c8ccncc8)n7)cc6)C5)C4)cc3C2=O)C(=O)N1]

Step A: tert-butyl-3-(4-(4,4,5,5-tetramethyl-1,3,2-dioxaborolan-2-yl) phenoxy) azetidine-1-carboxylate

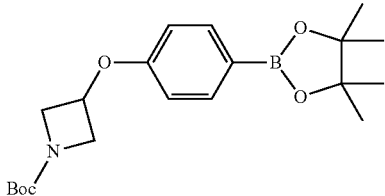 [SMILES: CC(C)(C)OC(=O)N1CC(Oc2ccc(B3OC(C)(C)C(C)(C)O3)cc2)C1]

A mixture of tert-butyl-3-iodoazetidine-1-carboxylate (2.8 g, 12.6 mmol), 4-(4,4,5,5-tetramethyl-1,3,2-dioxaborolan-2-yl) phenol (3.9 g, 13.8 mmol) and $K_2CO_3$ (3.5 g, 25.2 mmol) in dry DMF (20 mL) was stirred at 80° C. overnight. After cooled to room temperature, DCM (50 mL) and water (25 mL) were added. The layers were separated, and the organic phase was washed with water and brine. The organic phase was dried ($Na_2SO_4$), filtered, and concentrated under vacuum. The residue was purified via flash column on silica gel (PE:EA=9:1) to afford desired product (2.4 g, 65% yield).

Step B: tert-butyl3-(4-(4-bromo-3-(pyridin-4-yl)-1H-pyrazol-1-yl) phenoxy) azetidine-1-carboxylate

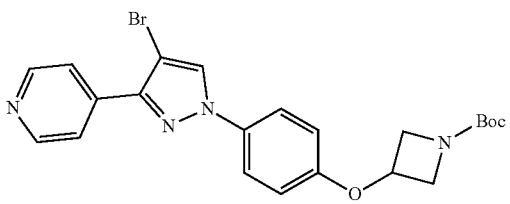 [SMILES: CC(C)(C)OC(=O)N1CC(Oc2ccc(-n3cc(Br)c(-c4ccncc4)n3)cc2)C1]

To a solution of tert-butyl 3-(4-(4,4,5,5-tetramethyl-1,3,2-dioxaborolan-2-yl)phenoxy)azetidine-1-carboxylate (2.4 g, 6.4 mmol) and 4-(4-bromo-1H-pyrazol-3-yl)pyridine (1.71 g, 7.68 mmol) in DCM (20 mL) were added $Et_2NH$ (4.7 g, 64 mmol), Cu(OAc)$_2$ (1.75 g, 9.6 mmol). The resulting mixture was stirred at 30° C. for 16 hours under $O_2$. The mixture was diluted with DCM (30 mL), and the mixture was washed with aqueous ammonia (10 mL×3). The organic phase was evaporated under reduced pressure, and the residue was purified by silica gel column chromatography on silica gel (DCM/MeOH=20/1) to afford tert-butyl 3-(4-(4-bromo-3-(pyridin-4-yl)-1H-pyrazol-1-yl) phenoxy) azetidine-1-carboxylate (1.5 g.50% yield) as a brown oil. LCMS (ES$^+$): m/z 471 [M+H]$^+$.

Step C: 4-(1-(4-(azetidin-3-yloxy) phenyl)-4-bromo-1H-pyrazol-3-yl) pyridine

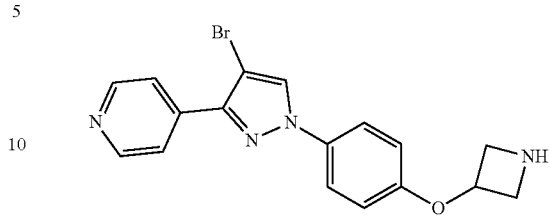

To a solution of tert-butyl 3-(4-(4-bromo-3-(pyridin-4-yl)-1H-pyrazol-1-yl) phenoxy) azetidine-1-carboxylate (700 mg) in DCM (3 mL) was added 3 m HCl in 1,4-dioxane (3 mL). The resulting solution was stirred at room temperature for 2 hours. The solvent was removed under reduced pressure to afford crude desired product (600 mg, crude). LCMS (ES$^+$): m/z 371 [M+H]$^+$.

Step D: tert-butyl-3-(4-(4-bromo-3-(pyridin-4-yl)-1H-pyrazol-1-yl) phenoxy)-[1,3'-biazetidine]-1'-carboxylate

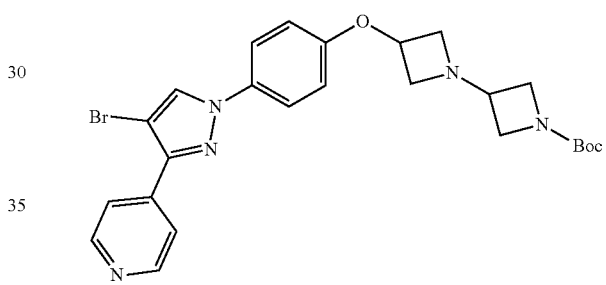

To a solution of 4-(1-(4-(azetidin-3-yloxy) phenyl)-4-bromo-1H-pyrazol-3-yl) pyridine (50 mg, 0.14 mmol) and tert-butyl 3-oxoazetidine-1-carboxylate (48 mg, 0.28 mmol) in DCE (1.0 mL) were added AcOH (1 drop), NaBH(OAc)$_3$ (74 mg, 0.35 mmol). The resulting solution was stirred at 30° C. overnight. The mixture was diluted with EA (5 mL), and the mixture was washed with aq. NaHCO$_3$ thrice. The organic phase was evaporated under reduced pressure, the residue was purified by silica gel column chromatography on silica gel (PE/EA=1/1) to afford tert-butyl 3-(4-(4-bromo-3-(pyridin-4-yl)-1H-pyrazol-1-yl)-phenoxy)-[1,3'-biazetidine]-1'-carboxylate (30 mg, 42% yield) as a brown oil. LCMS (ES$^+$): m/z 526 [M+H]$^+$.

Step E: 5-(3-(4-(4-bromo-3-(pyridin-4-yl)-1H-pyrazol-1-yl) phenoxy)-[1,3'-biazetidin]-1'-yl)-2-(2,6-dioxopiperidin-3-yl) isoindoline-1,3-dione

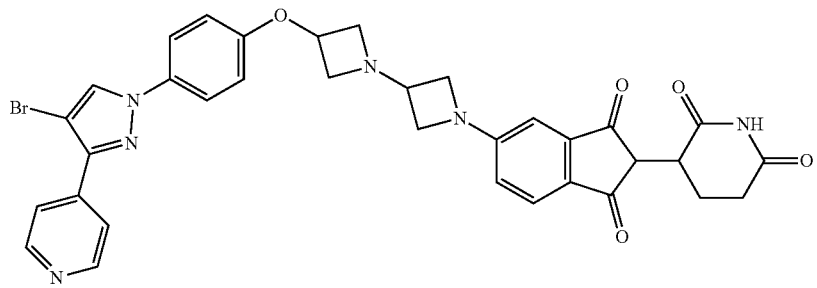 [SMILES: O=C1CCC(C2C(=O)c3ccc(N4CC(N5CC(Oc6ccc(-n7cc(Br)c(-c8ccncc8)n7)cc6)C5)C4)cc3C2=O)C(=O)N1]

To a solution of tert-butyl 3-(4-(4-bromo-3-(pyridin-4-yl)-1H-pyrazol-1-yl) phenoxy)-[1,3'-biazetidine]-1'-carboxylate (160 mg) in DCM (2 mL) was added 3 M HCl in 1,4-dioxane (1 mL). The resulting solution was stirred at room temperature for 2 hours. The solvent was removed under reduced pressure to afford the desired product (150 mg, crude). To a solution of 3-(4-(4-bromo-3-(pyridin-4-yl)-1H-pyrazol-1-yl)phenoxy)-1,3'-biazetidine (7.0 mg, 0.0165 mmol) and 2-(2,6-dioxopiperidin-3-yl)-5-fluoroisoindoline-1,3-dione (9.0 mg, 0.033 mmol) in NMP (1.0 mL) was added DIPEA (1 drop). The resulting solution was stirred at 130° C. for 1 hour under $N_2$. After cooled to rt, the mixture was diluted with EA (3 mL), and the mixture was washed with brine twice. The organic phase was evaporated under reduced pressure, The residue was purified by column chromatography on silica gel (DCM/MeOH=15/1) to afford 5-(3-(4-(4-bromo-3-(pyridin-4-yl)-1H-pyrazol-1-yl)phenoxy)-[1,3'-biazetidin]-1'-yl)-2-(2,6-dioxopiperidin-3-yl) isoindoline-1,3-dione (4 mg, 36% yield). LCMS (ES$^+$): m/z 682 [M+H]$^+$.

Step F: 2-(2,6-dioxopiperidin-3-yl)-5-(3-(4-(4-(1-oxo-2,3-dihydro-1H-inden-5-yl)-3-(pyridin-4-yl)-1H-pyrazol-1-yl)phenoxy)-[1,3'-biazetidin]-1'-yl) isoindoline-1,3-dione

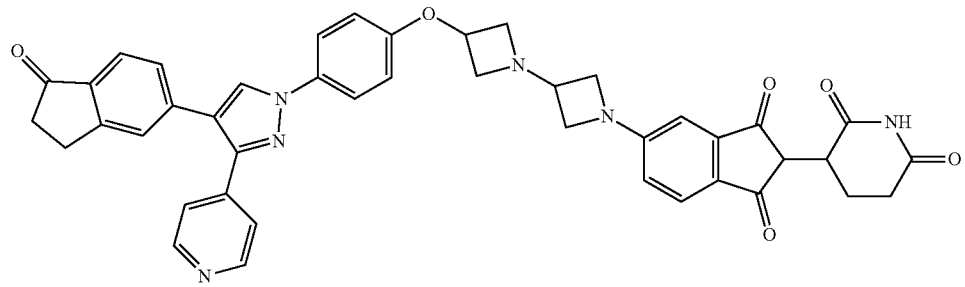 [SMILES: O=C1CCC(C2C(=O)c3ccc(N4CC(N5CC(Oc6ccc(-n7cc(-c8ccc9c(c8)CCC9=O)c(-c8ccncc8)n7)cc6)C5)C4)cc3C2=O)C(=O)N1]

To a solution of 5-(3-(4-(4-bromo-3-(pyridin-4-yl)-1H-pyrazol-1-yl)phenoxy)-[1,3'-biazetidin]-1'-yl)-2-(2,6-dioxopiperidin-3-yl)isoindoline-1,3-dione (200 mg, 0.29 mmol) in 1,4-dioxane/$H_2O$ (v/v=10/1, 5 mL) were added 5-(4,4,5,5-tetramethyl-1,3,2-dioxaborolan-2-yl)-2,3-dihydro-1H-inden-1-one (83 mg, 0.32 mmol), Pd$_2$(dba)$_3$ (110 mg, 0.12 mmol), CsF (176 mg, 1.20 mmol), [(t-Bu)$_3$PH]BF$_4$ (68 mg, 0.12 mmol), and N,N-dicyclohexylmethylamine (2.9 mg, 0.015 mmol) subsequently. The resulting solution was heated to 100° C. for 2 hours under $N_2$. After cooling to room temperature, the reaction was diluted with EA (10 mL), and the mixture was washed with water, brine. The organic phase was dried over anhydrous sodium sulfate, concentrated under vacuum. The residue was purified by prep-HPLC to afford 2-(2,6-dioxopiperidin-3-yl)-5-(3-(4-(4-(1-oxo-2,3-dihydro-1H-inden-5-yl)-3-(pyridin-4-yl)-1H-pyrazol-1-yl)phenoxy)-[1,3'-biazetidin]-1'-yl)isoindoline-1,3-dione (90 mg, 41.9% yield) as yellow solid. LCMS (ES$^+$): m/z 733 [M+H]$^+$.

Step G: (E)-2-(2,6-dioxopiperidin-3-yl)-5-(3-(4-(4-(1-(hydroxyimino)-2,3-dihydro-1H-inden-5-yl)-3-(pyridin-4-yl)-1H-pyrazol-1-yl)phenoxy)-[1,3'-biazetidin]-1'-yl)isoindoline-1,3-dione

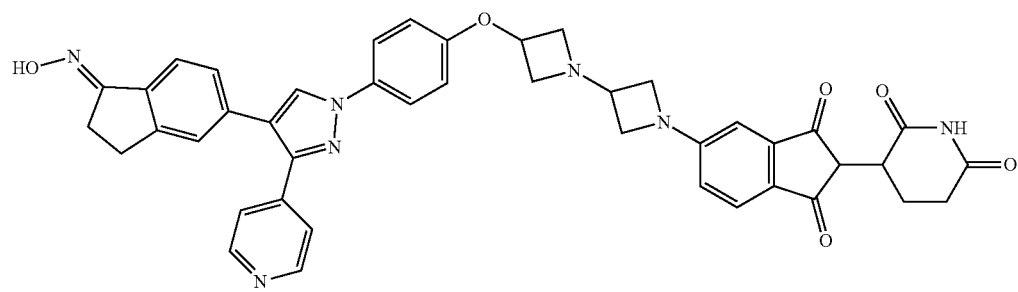 [SMILES: O=C1CCC(C2C(=O)c3ccc(N4CC(N5CC(Oc6ccc(-n7cc(-c8ccc9c(c8)CC/C9=N\O)c(-c8ccncc8)n7)cc6)C5)C4)cc3C2=O)C(=O)N1]

To a solution of 2-(2,6-dioxopiperidin-3-yl)-5-(3-(4-(4-(1-oxo-2,3-dihydro-1H-inden-5-yl)-3-(pyridin-4-yl)-1H-pyrazol-1-yl)phenoxy)-[1,3'-biazetidin]-1'-yl)isoindoline-1,3-dione (90 mg, 0.12 mmol) in acetonitrile/pyridine (v/v=1/1, 6.0 mL) was added hydroxylamine hydrochloride (83.4 mg, 1.2 mmol). The mixture was stirred at 40° C. for 20 minutes. After quenched with DCM (20 mL), the mixture was washed with brine (10 mL×2). The organic phase was concentrated under vacuum, and the residue was purified by prep-TLC to afford (E)-2-(2,6-dioxopiperidin-3-yl)-5-(3-(4-(4-(1-(hydroxyimino)-2,3-Dihydro-1H-inden-5-yl)-3-(pyridin-4-yl)-1H-pyrazol-1-yl)phenoxy)-[1,3'-biazetidin]-1'-yl)isoindoline-1,3-dione(25 mg, 27% yield) as yellow solid.

$^1$H NMR (400 MHz, CDCl$_3$): δ11.06 (s, 1H), 10.89 (s, 1H), 8.73 (s, 1H), 8.57 (d, J=4.8 Hz, 2H), 7.87 (d, J=8.8 Hz, 2H), 7.65 (d, J=8.0 Hz, 1H), 7.56 (d, J=8.0 Hz, 1H), 7.48 (d, J=4.8 Hz, 2H), 7.40 (s, 1H), 7.22 (d, J=8.0 Hz, 1H), 7.03 (d, J=8.8 Hz, 2H), 6.80 (s, 1H), 6.68 (d, J=8.4 Hz, 1H), 5.02-5.07 (m, 1H), 4.96 (t, J=2.4 Hz, 1H), 4.09 (t, J=8.4 Hz, 2H), 3.80-3.87 (m, 4H), 3.73 (s, 1H), 3.22 (s, 4H), 3.01 (d, J=5.2 Hz, 2H), 2.84 (d, J=5.6 Hz, 2H), 2.01 (d, J=9.2 Hz, 2H); LCMS (ES$^+$): m/z 748.79 [M+H]$^+$.

Example Synthesis of Compound 226: (2S,4R)-1-((S)-2-(2-(4-((4-(4-(3-(2,6-difluoro-3-((R)-3-fluoropyrrolidine-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide To a solution of tert-butyl 2-(4-(hydroxymethyl)piperidin-1-yl)acetate (1.5 g, 6.55 mmol) in CH$_3$CN (10 mL) was added IBX (2.7 g, 9.85 mmol). The resulting solution was stirred at 80° C. for 5 hours. After cooling to room tempeature, the reaction mixture was diluted with EA (30 mL), and the solution was washed with sodium sulfite and sodium bicarbonate. The organic layer was dried over anhydrous sodium sulfate. The organic phase was concentrated under vacuum. The residue was purified by silica gel chromatography (PE:EA=5:1) to afford the desired product tert-butyl 2-(4-formylpiperidin-1-yl)acetate (350 mg, 25% yield) as a yellow oil. $^1$H NMR (400 MHz, CDCl$_3$): δ 9.64 (s, 1H), 3.12 (s, 2H), 2.85-2.89 (m, 2H), 2.31-2.37 (m, 2H), 2.20-2.26 (m, 1H), 1.89-1.93 (m, 2H), 1.74-1.77 (m, 2H), 1.47 (s, 9H).

Step B: tert-butyl-2-(4-((4-(4-bromophenyl)piperazin-1-yl)methyl)piperidin-1-yl)acetate

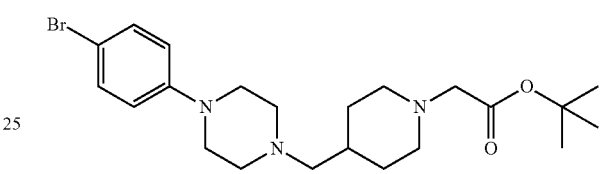

To a solution of tert-butyl 2-(4-formylpiperidin-1-yl)acetate (370 mg, 1.54 mmol) and 1-(4-bromophenyl)piperazine (350 mg, 1.54 mmol) in CH$_3$OH/DCM (v/v=1/1, 10

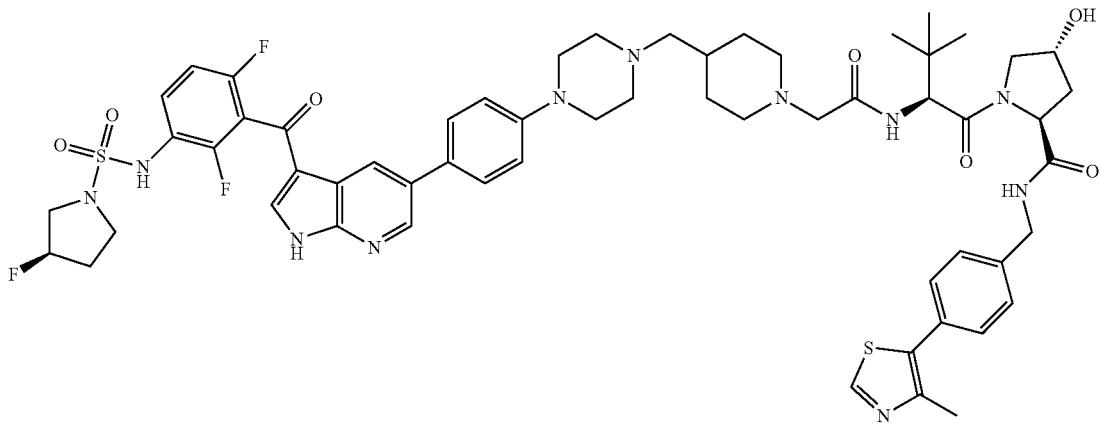 [SMILES: Cc1ncsc1-c1ccc(CNC(=O)[C@@H]2C[C@@H](O)CN2C(=O)[C@@H](NC(=O)CN2CCC(CN3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

Step A: tert-butyl 2-(4-formylpiperidin-1-yl)acetate

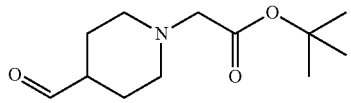 [SMILES: CC(C)(C)OC(=O)CN1CCC(C=O)CC1]

mL) was added catalytic AcOH (0.1 mL) at room temperature. After stirring for 30 minutes, NaBH(OAc)$_3$ (1.3 g, 6.17 mmol) was added. The mixture was stirred at 30° C. for 1 hours. After quenched with aqu.NaHCO$_3$ (20 mL), the mixture was extracted with DCM (10 mL×3). The combined organic layer was washed with brine (20 mL), dried over anhydrous sodium sulfate and concentrated under vacuum. The residue was purified by silica gel (DCM:MeOH=50:1), get tert-butyl 2-(4-((4-(4-bromophenyl)piperazin-1-yl) methyl) piperidin-1-yl)acetate (330 mg, 47% yield) as a yellow oil. LCMS (ES$^+$): m/z 454.2 [M+H]$^+$.

Step C: tert-butyl 2-(4-((4-(4-(4,4,5,5-tetramethyl-1,3,2-dioxaborolan-2-yl)phenyl)piperazin-1-yl)methyl)piperidin-1-yl)acetate

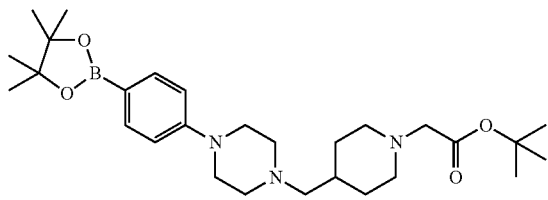 [SMILES: CC(C)(C)OC(=O)CN1CCC(CN2CCN(c3ccc(B4OC(C)(C)C(C)(C)O4)cc3)CC2)CC1]

To a solution of 4,4,4',4',5,5,5',5'-octamethyl-2,2'-bi(1,3,2-dioxaborolane) (242 mg, 0.951 mmol) and tert-butyl 2-(4-((4-(4-bromophenyl)piperazin-1-yl)methyl)-piperidin-1-yl)acetate (330 mg, 0.732 mmol) in 1,4-dioxane (5 mL) were added KOAc (145 mg, 1.46 mmol) and Pd(dppf)Cl$_2$ (54 mg, 0.0732 mmol). After stirring at 90° C. overnight under nitrogen atmosphere, the reaction mixture was diluted with 30 mL of ethyl acetate, and the solution was washed with brine (10 mL×3). The organic phase was dried over anhydrous sodium sulfate and concentrated under vacuum. The residue was purified by silica gel (DCM:MeOH=100:3) to afford the desired product tert-butyl 2-(4-((4-(4-(4,4,5,5-tetramethyl-1,3,2-dioxaborolan-2-yl)phenyl)piperazin-1-yl)methyl)piperidin-1-yl)acetate (100 mg, 27% yield) as yellow solid. LCMS (ES$^+$): m/z 499.4 [M+H]$^+$.

Step D: (R)-tert-butyl-2-(4-((4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)methyl)piperidin-1-yl)acetate

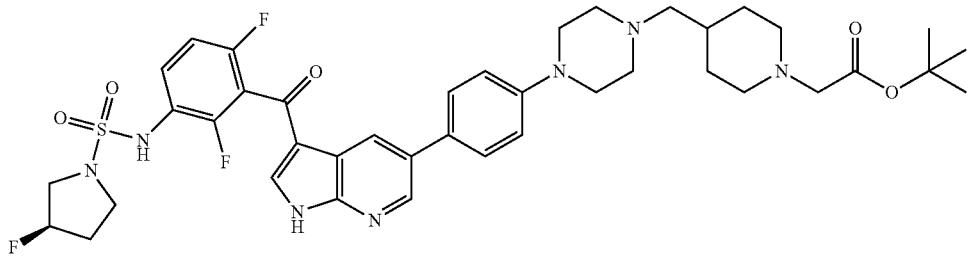 [SMILES: CC(C)(C)OC(=O)CN1CCC(CN2CCN(c3ccc(-c4cnc5[nH]cc(C(=O)c6c(F)ccc(NS(=O)(=O)N7CC[C@@H](F)C7)c6F)c5c4)cc3)CC2)CC1]

To a solution of tert-butyl 2-(4-((4-(4-(4,4,5,5-tetramethyl-1,3,2-dioxaborolan-2-yl)phenyl)piperazin-1-yl)methyl)piperidin-1-yl)acetate (100 mg, 0.199 mmol) in H$_2$O/dioxane (v/v=1/5, 5.0 mL) were added CsF (121 mg, 0.796 mmol), Pd(aMPhos)Cl$_2$ (14 mg, 0.0199 mmol) and (R)—N-(3-(5-bromo-1H-pyrrolo[2,3-b]pyridine-3-carbonyl)-2,4-difluorophenyl)-3-fluoropyrrolidine-1-sulfonamide (100 mg, 0.199 mmol) at room temperature. The solution was purged with N$_2$ at room temperature for 10 minutes to remove the excess O$_2$. The resulting solution was stirred at 100° C. for 4 hours. After cooling to room temperature, the reaction was taken up with EtOAc. The combined organic layers were concentrated under vacuum. The residue was purified by prep-TLC (DCM:CH$_3$OH=20:1) to afford the desired product (R)-tert-butyl 2-(4-((4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)methyl)piperidin-1-yl)acetate (50 mg, 32% yield) as a light yellow solid. LCMS (ES$^+$): m/z 797.6 [M+H]$^+$.

Step E: (R)-2-(4-((4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)methyl)piperidin-1-yl)acetic acid

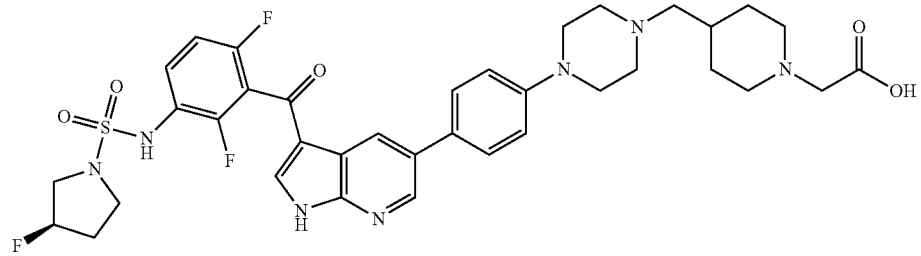 [SMILES: O=C(O)CN1CCC(CN2CCN(c3ccc(-c4cnc5[nH]cc(C(=O)c6c(F)ccc(NS(=O)(=O)N7CC[C@@H](F)C7)c6F)c5c4)cc3)CC2)CC1]

To a solution of (R)-tert-butyl 2-(4-((4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)methyl)piperidin-1-yl)acetate (50 mg, 0.0629 mmol) in DCM (1 mL) was added TFA (0.5 mL). The resulting solution was stirred for 2 hours at room temperature. The solvent was removed under vacuum. The residue is desired product (R)-2-(4-((4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)methyl)piperidin-1-yl)acetic acid (80 mg, crude) as a yellow solid. LCMS (ES$^+$): m/z 740.2 [M+H]$^+$.

Step G: (2S,4R)-1-((S)-2-(2-(4-((4-(4-(3-(2,6-difluoro-3-((R)-3-fluoropyrrolidine-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide

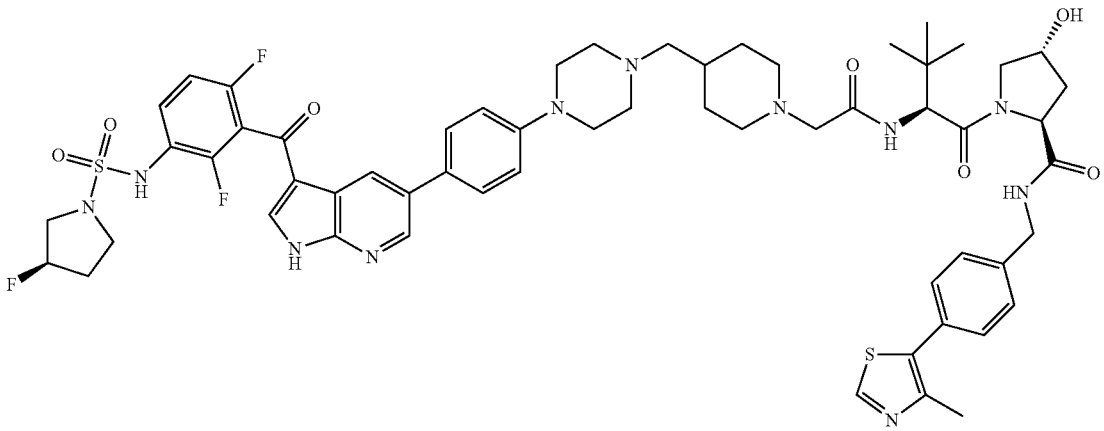 [SMILES: Cc1ncsc1-c1ccc(CNC(=O)[C@@H]2C[C@@H](O)CN2C(=O)[C@@H](NC(=O)CN2CCC(CN3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

To a solution of (R)-2-(4-((4-(4-(3-(2,6-difluoro-3-(3-fluoropyrrolidine-1-sulfonamido)benzoyl)-1H-pyrrolo[2,3-b]pyridin-5-yl)phenyl)piperazin-1-yl)methyl) piperidin-1-yl)acetic acid (47 mg, 0.0629 mmol) in DCM (5.0 mL) were added DIEA (25 mg, 0.189 mmol), (2S,4R)-1-((S)-2-((13-chloranyl)diazenyl)-3,3-dimethylbutanoyl)-4-hydroxy-N-(4-(4-methylthiazol-5-yl)benzyl)pyrrolidine-2-carboxamide (30 mg, 0.0691 mmol) and PyBOP (40 mg, 0.0755 mmol) at room temperature. The resulting solution was stirred at 20° C. for 1 hour. The reaction was quenched with H$_2$O (10 mL), and the mixture was extracted with DCM (20 m×3). The combined organic layer was concentrated under vacuum. The residue was purified by prep-TLC (DCM:CH$_3$OH=10: 1) to afford the desired product (2S,4R)-1-((S)-2-(2-(4-((4-(4-(3-(2,6-difluoro-3-((R)-3-fluoropyrrolidine-1-sulfonamido)benzoyl)-1H-pyrrolo[2,3-b]pyridin-5-yl)phenyl) piperazin-1-yl)methyl)piperidin-1-yl)acetamido)-3,3-dimethylbutanoyl)-4-hydroxy-N-(4-(4-methylthiazol-5-yl) benzyl)pyrrolidine-2-carboxamide (33 mg) as a white solid. $^1$H NMR (400 MHz, CD$_3$OD): δ 8.77 (s, 1H), 8.59 (s, 1H), 8.49 (s, 1H), 7.79 (s, 1H), 7.61-7.69 (m, 1H), 7.49 (d, J=8.8 Hz, 2H), 7.31-7.39 (m, 4H), 6.98-7.04 (m, 3H), 5.18 (s, 0.5H), 5.02 (s, 0.5H), 4.56 (s, 1H), 4.41-4.53 (m, 2H), 4.22-4.29 (m, 1H), 3.76-3.81 (m, 1H), 3.68-3.73 (m, 1H), 3.23-3.52 (m, 4H), 3.16 (s, 4H), 2.94 (s, 2H), 2.90 (s, 1H), 2.72-2.81 (m, 2H), 2.50 (br, 4H), 2.38 (s, 3H), 1.92-2.20 (m, 10H), 1.66-1.79 (m, 2H), 0.95 (s, 9H); LCMS (ES$^+$): m/z 1154.3 [M+H]$^+$.

Example Synthesis of Compound 227: (2S,4R)-1-((S)-2-(2-(4-((1-(4-(3-(2,6-difluoro-3-((R)-3-fluoro-pyrrolidine-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N-(4-(4-methylthiazol-5-yl)benzyl)pyrrolidine-2-carboxamide

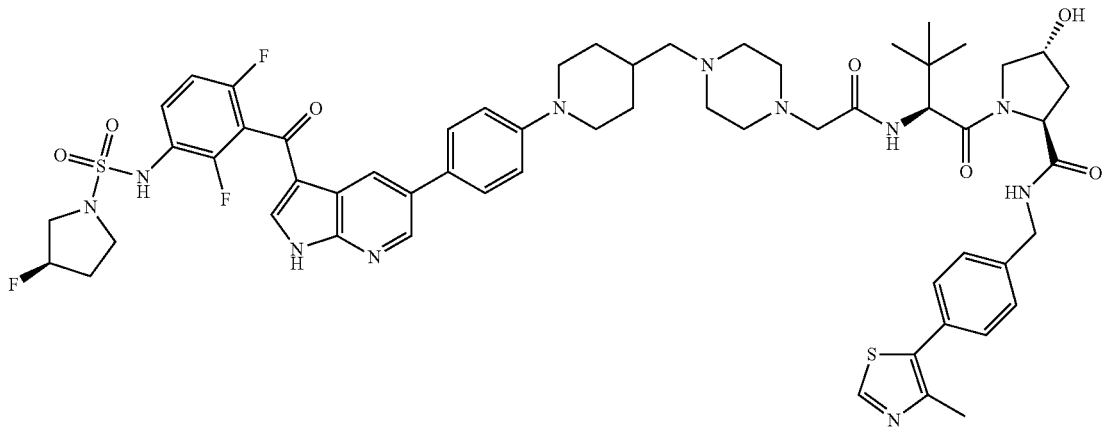 [SMILES: Cc1ncsc1-c1ccc(CNC(=O)[C@@H]2C[C@@H](O)CN2C(=O)[C@@H](NC(=O)CN2CCN(CC3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

Step A:
1-(4-bromophenyl)piperidine-4-carbaldehyde

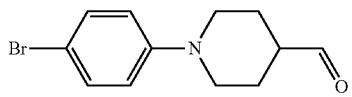 [SMILES: O=CC1CCN(c2ccc(Br)cc2)CC1]

To a solution of 1-(4-bromophenyl)-4-(dimethoxymethyl)piperidine (1 g, 3.18 mmol) in MeCN (10 mL) were added hydrochloric acid (3 N). The resulting solution was stirred at 50° C. for 4 hours. After cooling to room temperature, the pH of the mixture was adjusted to 8-9 with aq. NaHCO$_3$. The reaction mixture was diluted with 30 mL of EA, and the mixture was washed with sodium sulfite, sodium bicarbonate. The organic phase was dried over anhydrous sodium sulfate. The organic phase was concentrated under vacuum. The residue is desired product 1-(4-bromophenyl)piperidine-4-carbaldehyde (1 g crude) as yellow solid. LCMS (ES$^+$): m/z 268.0 [M+H]$^+$.

Step B: tert-butyl 4-((1-(4-bromophenyl)piperidin-4-yl)methyl)piperazine-1-carboxylate

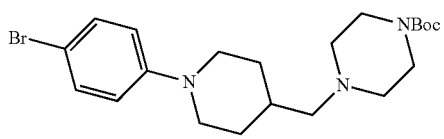 [SMILES: CC(C)(C)OC(=O)N1CCN(CC2CCN(c3ccc(Br)cc3)CC2)CC1]

To a solution of 1-(4-bromophenyl)piperidine-4-carbaldehyde (1 g, crude) and tert-butyl piperazine-1-carboxylate (590 mg, 3.18 mmol) in CH$_3$OH/DCM (v/v=1/1, 10 mL) was added cat. AcOH (0.1 mL) at room temperature. After stirring for 30 minutes, NaBH(OAc)$_3$ (2.7 g, 12.7 mmol) was added. The resulting solution was stirred at 30° C. overnight. After quenched with aq. NaHCO$_3$ (20 mL), the mixture was extracted with DCM (10 mL×3). The combined organic layers were washed with brine (20 mL), dried over anhydrous sodium sulfate and concentrated under vacuum. The residue was purified by silica gel with PE/EA (8/1) tert-butyl 4-((1-(4-bromophenyl)piperidin-4-yl)methyl)piperazine-1-carboxylate (800 mg) as a yellow oil. LCMS (ES$^+$): m/z 440.2 [M+H]$^+$.

Step C: tert-butyl 2-(4-((1-(4-bromophenyl)piperidin-4-yl)methyl)piperazin-1-yl)acetate

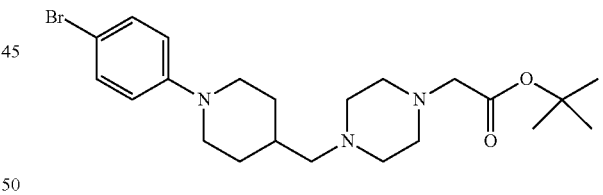

To a solution of tert-butyl 4-((1-(4-bromophenyl)piperidin-4-yl)methyl) piperazine-1-carboxylate (800 mg, 1.83 mmol) in DCM (4 mL) was added TFA (2 mL). The resulting solution was stirred for 2 hours at room temperature. The solvent was removed under vacuum to afford crude desired product (1 g, crude), which was used in next step directly. To a solution of above crude product (500 g, crude) and tert-butyl 2-bromoacetate (176 mg, 0.913 mmol) in dry DMF (5 mL) was added K$_2$CO$_3$ (190 mg, 1.37 mmol). The resulting solution was stirred at room temperature overnight. The reaction mixture was diluted with 40 mL of EA, and the mixture was washed with water, brine. The organic phase was dried over anhydrous sodium sulfate. The residue is desired product tert-butyl-2-(4-((1-(4-bromophenyl)piperidin-4-yl)methyl)piperazin-1-yl) acetate (410 mg, crude) as a yellow oil. LCMS (ES$^+$): m/z 453.2 [M+H]$^+$.

Step D: tert-butyl 2-(4-((1-(4-(4,4,5,5-tetramethyl-1,3,2-dioxaborolan-2-yl)phenyl)piperidin-4-yl)methyl)piperazin-1-yl)acetate

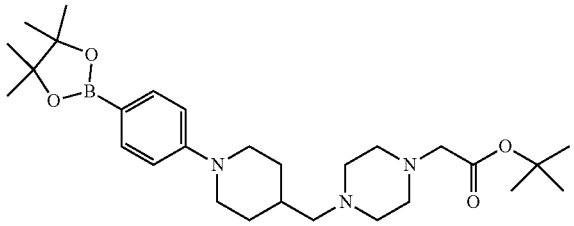 [SMILES: CC(C)(C)OC(=O)CN1CCN(CC2CCN(c3ccc(B4OC(C)(C)C(C)(C)O4)cc3)CC2)CC1]

To a solution of 4,4,4',4',5,5,5',5'-octamethyl-2,2'-bi(1,3,2-dioxaborolane) (300 mg, 1.18 mmol) and tert-butyl 2-(4-((1-(4-bromophenyl)piperidin-4-yl)methyl)-piperazin-1-yl)acetate (410 mg, 0.913 mmol) in 1,4-dioxane (5 mL) were added KOAc (178 mg, 1.82 mmol) and Pd(dppf)Cl$_2$ (67 mg, 0.0913 mmol). After stirring at 90° C. overnight under nitrogen atmosphere, the reaction mixture was diluted with 30 mL of ethyl acetate, and the solution was washed with brine (10 mL×3). The organic phase was dried over anhydrous sodium sulfate and concentrated under vacuum. The residue was purified by silica gel with DCM/MeOH (100/3) to afford the desired product tert-butyl 2-(4-((1-(4-(4,4,5,5-tetramethyl-1,3,2-dioxaborolan-2-yl)phenyl)-piperidin-4-yl)methyl)piperazin-1-yl)acetate (200 mg, crude) as yellow solid. LCMS (ES$^+$): m/z 500.4 [M+H]$^+$.

Step E: (R)-tert-butyl 2-(4-((1-(4-(3-(2,6-difluoro-3-(3-fluoropyrrolidine-1-sulfonamido)benzoyl)-1H-pyrrolo[2,3-b]pyridin-5-yl)phenyl)piperidin-4-yl)methyl)piperazin-1-yl)acetate

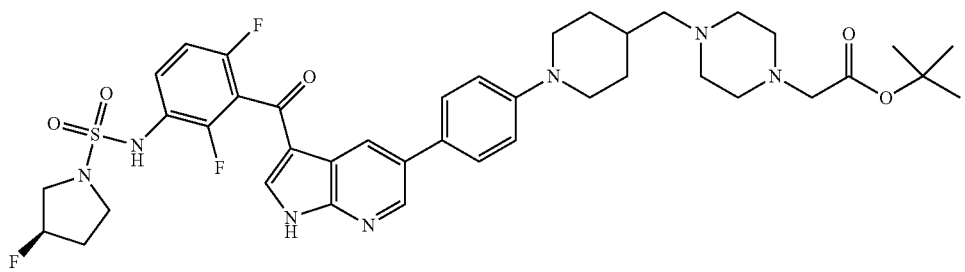 [SMILES: CC(C)(C)OC(=O)CN1CCN(CC2CCN(c3ccc(-c4cnc5[nH]cc(C(=O)c6c(F)ccc(NS(=O)(=O)N7CC[C@@H](F)C7)c6F)c5c4)cc3)CC2)CC1]

To a solution of tert-butyl 2-(4-((1-(4-(4,4,5,5-tetramethyl-1,3,2-dioxaborolan-2-yl)phenyl)piperidin-4-yl)methyl)piperazin-1-yl)acetate (200 mg, crude) in H$_2$O/dioxane (v/v=1/5, 5.0 mL) were added CsF (121 mg, 0.796 mmol), Pd(aMPhos)Cl$_2$ (14 mg, 0.0199 mmol), (R)—N-(3-(5-bromo-1H-pyrrolo[2,3-b]pyridine-3-carbonyl)-2,4-difluorophenyl)-3-fluoropyrrolidine-1-sulfonamide (100 mg, 0.199 mmol) at room temperature. The solution was purged with N$_2$ at room temperature for 10 minutes to remove the excess O$_2$. The resulting solution was stirred at 100° C. for 4 hours. After cooling to room temperature, the reaction was taken up with EtOAc. The combined organic layers were concentrated under vacuum. The residue was purified by prep-TLC with DCM/CH$_3$OH (20/1) to afford the desired product (R)-tert-butyl 2-(4-((1-(4-(3-(2,6-difluoro-3-(3-fluoropyrrolidine-1-sulfonamido)benzoyl)-1H-pyrrolo[2,3-b]pyridin-5-yl)phenyl)piperidin-4-yl)methyl)piperazin-1-yl)acetate (110 mg, 69% yield) as a light yellow solid. LCMS (ES$^+$): m/z 796.3 [M+H]$^+$.

Step F: (2S,4R)-1-((S)-2-(2-(4-((1-(4-(3-(2,6-Difluoro-3-((R)-3-fluoropyrrolidine-1-sulfonamido)benzoyl)-1H-pyrrolo[2,3-b]pyridin-5-yl)phenyl)piperidin-4-yl)methyl)piperazin-1-yl)acetamido)-3,3-dimethylbutanoyl)-4-hydroxy-N-(4-(4-methylthiazol-5-yl)benzyl)pyrrolidine-2-carboxamide

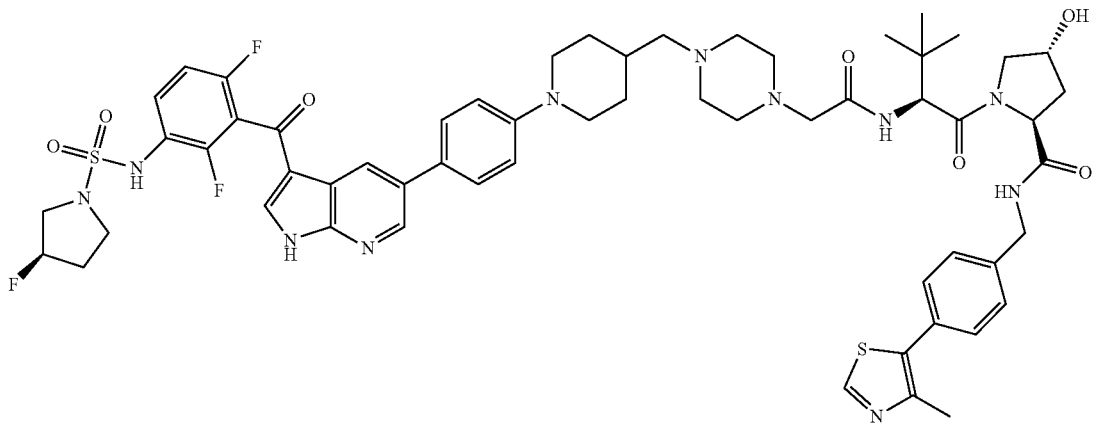 [SMILES: Cc1ncsc1-c1ccc(CNC(=O)[C@@H]2C[C@@H](O)CN2C(=O)[C@@H](NC(=O)CN2CCN(CC3CCN(c4ccc(-c5cnc6[nH]cc(C(=O)c7c(F)ccc(NS(=O)(=O)N8CC[C@@H](F)C8)c7F)c6c5)cc4)CC3)CC2)C(C)(C)C)cc1]

To a solution of (R)-tert-butyl 2-(4-((1-(4-(3-(2,6-difluoro-3-(3-fluoropyrrolidine-1-sulfonamido)benzoyl)-1H-pyrrolo[2,3-b]pyridin-5-yl)phenyl)piperidin-4-yl)methyl)piperazin-1-yl)acetate (110 mg, 0.139 mmol) in DCM (3 mL) was added TFA (1.5 mL). The resulting solution was stirred at room temperature for 2 hours. The solvent was removed under vacuum to afford crude desired product (180 mg, crude), which was used in next step directly. To a solution of above acid (180 mg, crude) in DMF (5.0 mL) were added DIEA (54 mg, 0.418 mmol), (2S,4R)-1-((S)-2-((13-chloranyl)diazenyl)-3,3-dimethyl-butanoyl)-4-hydroxy-N-(4-(4-methylthiazol-5-yl)benzyl)pyrrolidine-2-carboxamide (66 mg, 0.153 mmol) and PyBOP (87 mg, 0.167 mmol) at room temperature. The resulting solution was stirred at 20° C. for 1 hour. After quenched with H$_2$O (10 mL), and the mixture was extracted with EA (20 mL×3). The combined organic layer was concentrated under vacuum. The residue was purified by prep-HPLC to afford the desired product desired product (42 mg) as a yellow solid. $^1$H NMR (400 MHz, MeOD-d$_4$): δ 8.89 (s, 1H), 8.70 (s, 1H), 8.61 (s, 1H), 7.91 (s, 1H), 7.71-7.80 (m, 1H), 7.60 (d, J=8.4 Hz, 2H), 7.43-7.50 (m, 4H), 7.12-7.16 (m, 3H), 5.23 (s, 0.5H), 5.18 (s, 0.5H), 4.95 (m, 4H), 4.56 (s, 1H), 4.53-4.66 (m, 4H), 4.35-4.41 (m, 1H), 3.79-3.90 (m, 4H), 3.44-3.60 (m, 6H), 3.08-3.19 (m, 2H), 2.72-2.81 (m, 10H), 2.50 (s, 3H), 2.03-2.25 (m, 5H), 1.87-1.92 (m, 3H), 1.52-1.63 (m, 2H), 1.04 (s, 9H); LCMS (ES$^+$): m/z 1101.3 [M+H]$^+$.

Example Synthesis of Compound 295: (2S,4R)-1-((S)-2-(2-(4-((4-(4-(3-(2,6-difluoro-3-(((3S,4S)-3-fluoro-4-hydroxypyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide

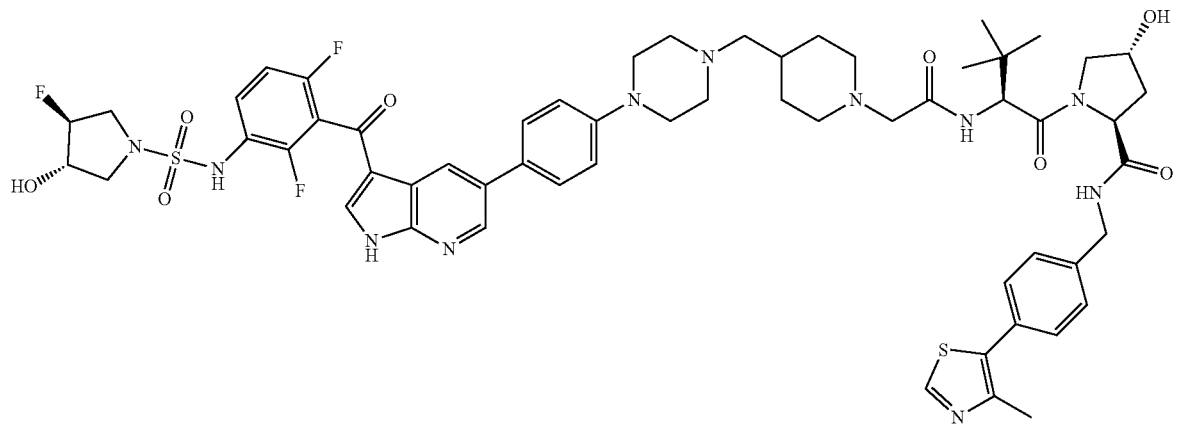 [SMILES: Cc1ncsc1-c1ccc(CNC(=O)[C@@H]2C[C@@H](O)CN2C(=O)[C@@H](NC(=O)CN2CCC(CN3CCN(c4ccc(-c5cnc6[nH]cc(C(=O)c7c(F)ccc(NS(=O)(=O)N8C[C@H](O)[C@@H](F)C8)c7F)c6c5)cc4)CC3)CC2)C(C)(C)C)cc1]

Step A: (3S,4S)-3-[(tert-butyldiphenylsilyfloxy]-4-fluoropyrrolidine

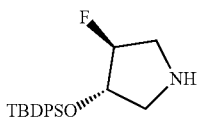

Into a 50 mL round-bottom flask, was placed (3S,4S)-4-fluoropyrrolidin-3-ol (500 mg, 4.76 mmol, 1 equiv), dichloromethane (10 mL), imidazole (323.8 mg, 4.76 mmol, 1 equiv), TBDPSCl (1307.5 mg, 4.76 mmol, 1 equiv). The resulting solution was stirred overnight at room temperature. The resulting mixture was concentrated. The residue was applied onto a silica gel column eluting with dichloromethane/methanol (10/1). This resulted in 470 mg (29%) of (3S,4S)-3-[(tert-butyldiphenylsilyl)oxy]-4-fluoropyrrolidine as yellow oil.

Step B: (3S,4S)-3-[(tert-butyldiphenylsilyl)oxy]-4-fluoropyrrolidine-1-sulfonyl chloride

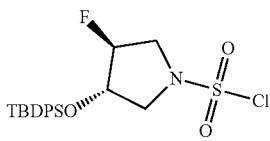

Into a 50 mL round-bottom flask, was placed (3S,4S)-3-[(tert-butyldiphenylsilyl)oxy]-4-fluoropyrrolidine (370 mg, 1 equiv), dichloromethane (5 mL), Diisopropylethylamine (279 mg, 2 equiv), dichloro sulfoxide(290 mg, 2 equiv). The resulting solution was stirred for 4 hours at −30° C. The reaction was then quenched by the addition of water (20 mL). The resulting solution was extracted with dichloromethane (20 mL×3). The resulting mixture was washed with brine (20 mL×1), was dried over anhydrous sodium sulfate and concentrated. This resulted in 450 mg of (3S,4S)-3-[(tert-butyldiphenylsilyl)oxy]-4-fluoropyrrolidine-1-sulfonyl chloride as yellow oil.

Step C: (3S,4S)—N-(3-[5-bromo-1H-pyrrolo[2,3-b]pyridine-3-carbonyl]-2,4-difluorophenyl)-3-[(tert-butyldiphenylsilyl)oxy]-4-fluoropyrrolidine-1-sulfonamide

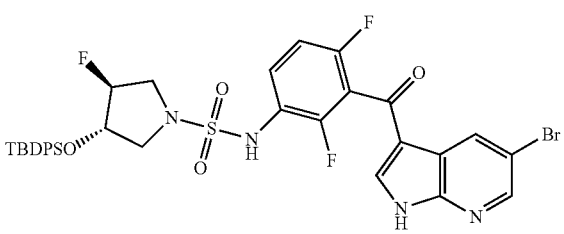

Into a 25 mL round-bottom flask, was placed (3S,4S)-3-[(tert-butyldiphenylsilyl)oxy]-4-fluoropyrrolidine-1-sulfonyl chloride (449.4 mg, 1.02 mmol, 2.00 equiv), pyridine (0.7 mL), 3-[5-bromo-1H-pyrrolo[2,3-b]pyridine-3-carbonyl]-2,4-difluoroaniline (179 mg, 0.51 mmol, 1 equiv), dimethylaminopyridine (18.6 mg, 0.15 mmol, 0.30 equiv). The resulting solution was stirred for 3 hours at 45° C. in an oil bath. The resulting mixture was concentrated. The residue was applied onto a silica gel column eluting with ethyl acetate/petroleum ether (1/1). This resulted in 120 mg (31%) of (3S,4S)—N-(3-[5-bromo-1H-pyrrolo[2,3-b]pyridine-3-carbonyl]-2,4-difluorophenyl)-3-[(tert-butyldiphenylsilyl)oxy]-4-fluoropyrrolidine-1-sulfonamide as yellow oil.

Step D: Synthesis of tert-butyl 2-(4-[[4-(4-[3-[3-([[(3S,4S)-3-[(tert-butyldiphenylsilyl)oxy]-4-fluoropyrrolidin-1-yl]sulfonyl]amino)-2,6-difluorobenzoyl]-1H-pyrrolo[2,3-b]pyridin-5-yl]phenyl)piperazin-1-yl]methyl]piperidine

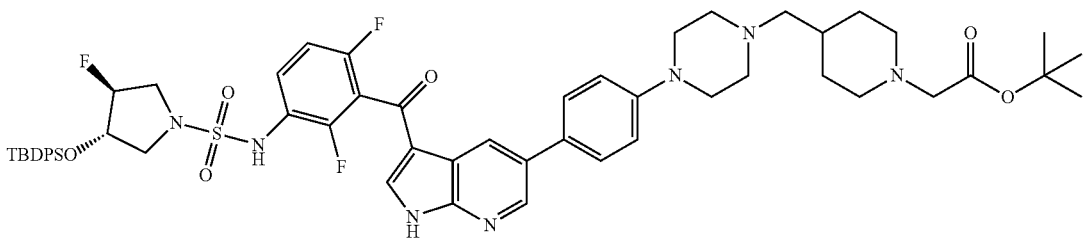

Into a 50 mL round-bottom flask, was placed (3S,4S)—N-(3-[5-bromo-1H-pyrrolo[2,3-b]pyridine-3-carbonyl]-2,4-difluorophenyl)-3-[(tert-butyldiphenylsilyl)oxy]-4-fluoropyrrolidine-1-sulfonamide (120 mg, 0.16 mmol, 1 equiv), 1,4-dioxane (5 mL, 0.06 mmol), water (0.0 mL, 0.06 mmol), tert-butyl 2-[4-(]4-[4-(4,4,5,5-tetramethyl-1,3,2-dioxaborolan-2-yl)phenyl]piperazin-1-yl]methyl)piperidin-1-yl]acetate (79.1 mg, 0.16 mmol, 1 equiv), $Na_2CO_3$ (50.4 mg, 0.48 mmol, 3 equiv), Pd(dppf)$Cl_2$ (39 mg). The resulting solution was stirred for 2 hours at 110° C. in an oil bath. The resulting mixture was concentrated. The residue was applied onto a silica gel column eluting with dichloromethane/methanol (10/1). This resulted in 90 mg (54%) of tert-butyl 2-(4-[[4-(4-[3-[3-([[(3S,4S)-3-[(tert-butyldiphenylsilyl)oxy]-4-fluoropyrrolidin-1-yl]sulfonyl]amino)-2,6-difluorobenzoyl]-1H-pyrrolo[2,3-b]pyridin-5-yl]phenyl)piperazin-1-yl]methyl]piperid as yellow oil.

Step E: Synthesis of 2-(4-[[4-(4-[3-[3-([[(3S,4S)-3-[(tert-butyldiphenylsilyl)oxy]-4-fluoropyrrolidin-1-yl]sulfonyl]amino)-2,6-difluorobenzoyl]-1H-pyrrolo[2,3-b]pyridin-5-yl]phenyl)piperazin-1-yl]methyl]piperidin-1-yl)acetic acid

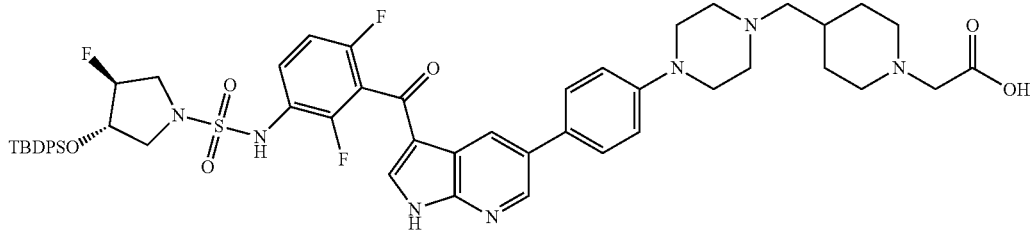

Into a 25 mL round-bottom flask, was placed tert-butyl 2-(4-[[4-(4-[3-[3-([[(3S,4S)-3-[(tert-butyldiphenylsilyl)oxy]-4-fluoropyrrolidin-1-yl]sulfonyl]amino)-2,6-difluorobenzoyl]-1H-pyrrolo[2,3-b]pyridin-5-yl]phenyl)piperazin-1-yl]methyl]piperid (90 mg, 0.09 mmol, 1 equiv), dichloromethane (5 mL), trifluoroacetic acid (2 mL, 0.02 mmol). The resulting solution was stirred overnight at room temperature. The resulting mixture was concentrated under reduced pressure. This resulted in 60 mg (70.43%) of 2-(4-[[4-(4-[3-[3-([[(3S,4S)-3-[(tert-butyldiphenylsilyl)oxy]-4-fluoropyrrolidin-1-yl]sulfonyl]amino)-2,6-difluorobenzoyl]-1H-pyrrolo[2,3-b]pyridin-5-yl]phenyl)piperazin-1-yl]methyl]piperidin-1-yl)acetic acid as a yellow solid.

Step F: Synthesis of 2-(4-[[4-(4-[3-[2,6-difluoro-3-([[(3S,4S)-3-fluoro-4-hydroxypyrrolidin-1-yl]sulfonyl]amino)benzoyl]-1H-pyrrolo[2,3-b]pyridin-5-yl]phenyl)piperazin-1-yl]methyl]piperidin-1-yl)acetic acid

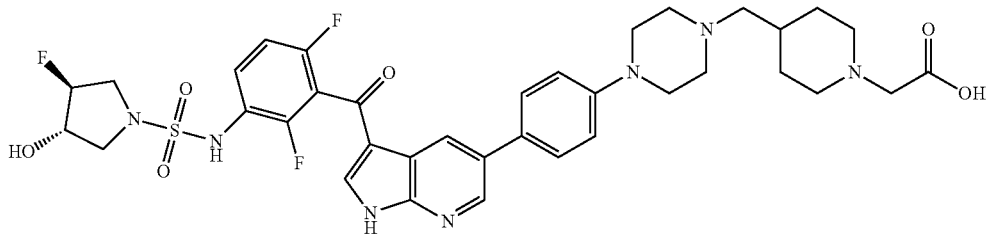 [SMILES: O=C(O)CN1CCC(CN2CCN(c3ccc(-c4cnc5[nH]cc(C(=O)c6c(F)ccc(NS(=O)(=O)N7C[C@H](O)[C@@H](F)C7)c6F)c5c4)cc3)CC2)CC1]

Into a 25 mL round-bottom flask, was placed 2-(4-[[4-(4-[3-[3-([[(3S,4S)-3-[(tert-butyldiphenylsilyl)oxy]-4-fluoropyrrolidin-1-yl]sulfonyl]amino)-2,6-difluorobenzoyl]-1H-pyrrolo[2,3-b]pyridin-5-yl]phenyl)piperazin-1-yl]methyl]piperidin-1-yl)acetic acid (60 mg, 0.06 mmol, 1 equiv), tetrahydrofuran (3 mL), TBAF (1 mL, 0.06 equiv). The resulting solution was stirred for 2 hours at 40° C. The resulting mixture was concentrated under reduced pressure. The residue was applied onto a silica gel column eluting with dichloromethane/methanol (10/1). This resulted in 50 mg (109.62%) of 2-(4-[[4-(4-[3-[2,6-difluoro-3-([[(3S,4S)-3-fluoro-4-hydroxypyrrolidin-1-yl]sulfonyl]amino)benzoyl]-1H-pyrrolo[2,3-b]pyridin-5-yl]phenyl)piperazin-1-yl]methyl]piperidin-1-yl)acetic acid as yellow oil.

Step G: (2S,4R)-1-((S)-2-(2-(4-((4-(4-(3-(2,6-difluoro-3-(((3S,4S)-3-fluoro-4-hydroxypyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide

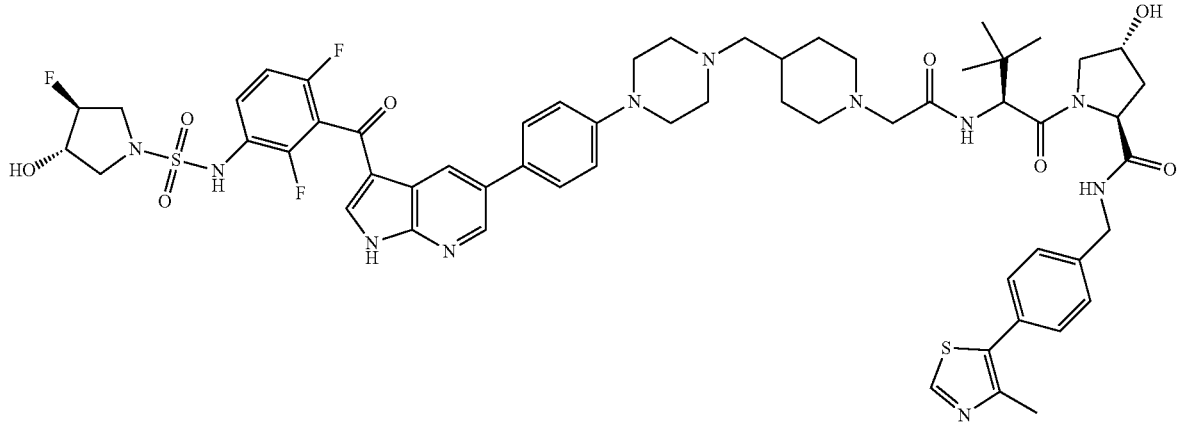 [SMILES: Cc1ncsc1-c1ccc(CNC(=O)[C@@H]2C[C@@H](O)CN2C(=O)[C@@H](NC(=O)CN2CCC(CN3CCN(c4ccc(-c5cnc6[nH]cc(C(=O)c7c(F)ccc(NS(=O)(=O)N8C[C@H](O)[C@@H](F)C8)c7F)c6c5)cc4)CC3)CC2)C(C)(C)C)cc1]

Into a 25 mL round-bottom flask, was placed 2-(4-[[4-(4-[3-[2,6-difluoro-3-([[[(3S,4S)-3-fluoro-4-hydroxypyrrolidin-1-yl]sulfonyl]amino)benzoyl]-1H-pyrrolo[2,3-b]pyridin-5-yl]phenyl)piperazin-1-yl]methyl]piperidin-1-yl)acetic acid (50 mg, 0.066 mmol, 1 equiv), DMF (5 mL), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (30.8 mg, 0.066 mmol, 1 equiv), Diisopropylethylamine (34.1 mg, 0.264 mmol, 4.00 equiv), BOP (35 mg, 0.079 mmol, 1.2 equiv). The resulting solution was stirred for 3 hours at room temperature. The reaction was then quenched by water (30 mL), extracted with dichloromethane (30 mL×3), washed with water (30 mL) and concentrated under reduced pressure. The crude product was purified by prep-HPLC. This resulted in 32.6 mg (42%) of (2S,4R)-1-((S)-2-(2-(4-((4-(4-(3-(2,6-difluoro-3-(((3S,4S)-3-fluoro-4-hydroxypyrrolidine)-1-sulfonamido)benzoyl)-1H-pyrrolo[2,3-b]pyridin-5-yl)phenyl)piperazin-1-yl)methyl)piperidin-1-yl)acetamido)-3,3-dimethylbutanoyl)-4-hydroxy-N-(4-(4-methylthiazol-5-yl)benzyl)pyrrolidine-2-carboxamide as a yellow solid. $^1$H NMR (400 MHz, CD$_3$OD): δ 8.87 (s, 1H), 8.69 (s, 1H), 8.58 (s, 1H), 7.89 (s, 1H), 7.73-7.72 (m, 1H), 7.58 (d, J=8.8 Hz, 2H), 7.48-7.40 (m, 4H), 7.10-7.05 (m, 3H), 4.93 (s, 1H), 4.63 (s, 1H), 4.57 (d, J=6 Hz, 1H), 4.52-4.50 (m, 1H), 4.38-4.34 (m, 2H), 3.87-3.86 (m, 1H), 3.82-3.81 (m, 1H), 3.57-3.50 (m, 3H), 3.36-3.33 (m, 1H), 3.31-3.20 (m, 5H), 3.02 (s, 2H), 3.01-2.90 (m, 2H), 2.56 (s, 3H), 2.74 (s, 3H), 2.26-2.20 (m, 4H), 2.10-2.01 (m, 1H), 1.82-1.71 (m, 2H), 1.67-1.61 (m, 3H), 1.44-1.28 (m, 2H), 1.05-1.02 (m, 9H); LCMS (ES$^+$): m/z 1168.30 [M+H]$^+$.

Example Synthesis of Compound 298: (2S,4R)-1-((S)-2-(2-(4-(3-(2,6-difluoro-3-(propylsulfonamido)benzoyl)-1H-pyrrolo[2,3-b]pyridin-5-yl)phenoxy)acetamido)-3,3-dimethylbutanoyl)-4-hydroxy-N-(4-(4-methylthiazol-5-yl)benzyl)-pyrrolidine-2-carboxamide

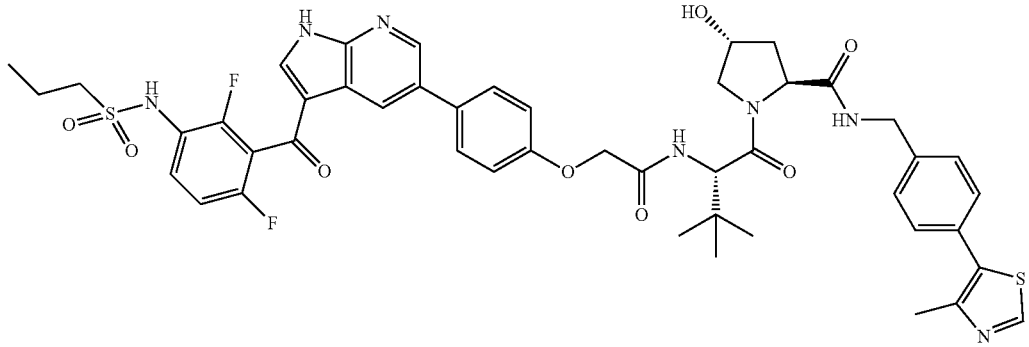 [SMILES: CCCS(=O)(=O)Nc1ccc(F)c(C(=O)c2c[nH]c3ncc(-c4ccc(OCC(=O)N[C@H](C(=O)N5C[C@H](O)C[C@H]5C(=O)NCc5ccc(-c6scnc6C)cc5)C(C)(C)C)cc4)cc23)c1F]

To a solution of 2-[4-[3-[2,6-difluoro-3-(propylsulfonylamino)-benzoyl]-1H-pyrrolo[2,3-b]pyridin-5-yl]phenoxy]acetic acid (10.8 mg, 0.02 mmol) and (2S,4R)-1-[(2S)-2-amino-3,3-dimethyl-butanoyl]-4-hydroxy-N-[[4-(4-methylthiazol-5-yl)-phenyl]methyl]pyrrolidine-2-carboxamide; hydrochloride (9.5 mg, 0.02 mmol) in DMF(1 ml) was added TEA (0.1 ml, 0.717 mmol) and PyBOP (11 mg, 0.021 mmol) at room temperature. The reaction mixture was stirred for 4 hours at the same temperature. TLC (DCM:MeOH:NH4OH, 90:9:1) shows no starting materials. The DMF was removed under high vacuum. Crude product was filtered over a silica-carbonate cartridge (100 mg) using a mixture of DCM:MeOH (90:10) as a eluent. Filtrate was evaporated under vacuum and crude product was purified by PTLC (DCM:MeOH:NH4OH, 90:9:1) to give 8.5 mg of product (44% yield). 1H NMR (500 MHz, DMSO-d6) δ 12.88 (s, 1H), 9.67 (s, 1H), 8.98 (s, 1H), 8.76-8.50 (m, 3H), 8.23 (s, 1H), 7.98 (d, J=9.4 Hz, 1H), 7.69 (d, J=8.6 Hz, 2H), 7.59 (td, J=9.0, 5.8 Hz, 1H), 7.49-7.34 (m, 4H), 7.33-7.20 (m, 1H), 7.10 (d, J=8.7 Hz, 2H), 5.20 (d, J=3.3 Hz, 1H), 4.72 (s, 2H), 4.62 (d, J=9.4 Hz, 1H), 4.54-4.34 (m, 3H), 4.25 (dd, J=15.9, 5.5 Hz, 1H), 3.74-3.59 (m, 2H), 3.19-3.07 (m, 2H), 2.44 (s, 3H), 2.07 (dd, J=12.9, 7.7 Hz, 1H), 1.91 (ddd, J=12.8, 8.8, 4.5 Hz, 1H), 1.80-1.65 (m, 2H), 0.96 (s, 9H), 0.94 (t, 3H). 13C NMR (151 MHz, dmso) δ 180.62, 171.82, 169.13, 167.11, 157.51, 156.02 (dd, J=246.1, 7.0 Hz), 152.34 (dd, J=249.6, 8.5 Hz), 151.45, 148.60, 147.74, 143.80, 139.47, 138.70, 131.16, 129.70, 129.00-128.42 (m), 128.81, 128.69, 128.31, 128.00, 127.48, 126.53, 121.96 (dd, J=13.6, 3.5 Hz), 118.61-117.85 (m), 117.53, 115.63, 115.34, 112.34 (dd, J=22.4, 3.4 Hz), 68.91, 66.58, 58.80, 56.58, 56.17, 53.45, 41.69, 37.95, 35.79, 26.28, 16.85, 15.96, 12.63. LC-MS (ESI); m/z [M+H]+: Calcd. for C47H50F2N7O8S2, 942.3130. Found 942.3134.

Example Synthesis of Compound 299: (2S,4R)-1-((S)-2-(4-(3-(3-(2,6-difluoro-3-(propylsulfonamido)benzoyl)-1H-pyrrolo[2,3-b]pyridin-5-yl)phenoxy)butanamido)-3,3-dimethylbutanoyl)-4-hydroxy-N-(4-(4-methylthiazol-5-yl)benzyl)pyrrolidine-2-carboxamide

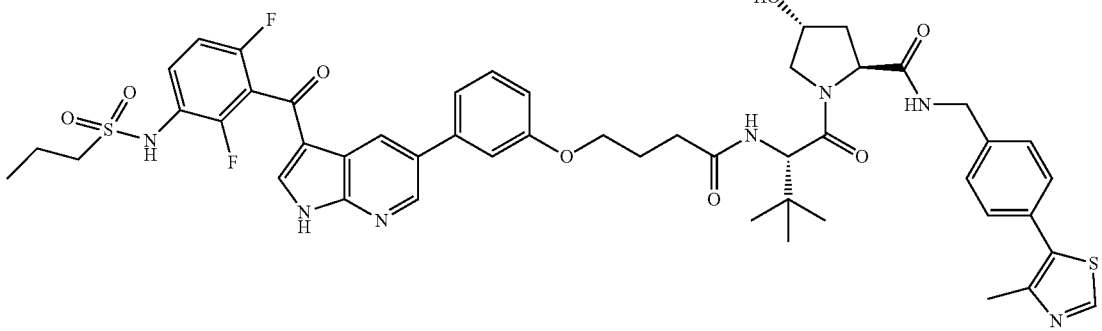

To a solution of 4-[3-[3-[2,6-difluoro-3-(propylsulfonylamino)-benzoyl]-1H-pyrrolo[2,3-b]pyridin-5-yl]phenoxy]butanoic acid (18 mg, 0.03 mmol) and (2S,4R)-1-[(2S)-2-amino-3,3-dimethyl-butanoyl]-4-hydroxy-N-[[4-(4-methylthiazol-5-yl) phenyl]methyl]pyrrolidine-2-carboxamide; hydrochloride (16.8 mg, 0.036 mmol) in DMF (2 ml) was added TEA (0.1 ml, 0.72 mmol) and PyBOP (18.48 mg, 0.04 mmol) at room temperature. The reaction mixture was stirred for 4 hours at the same temperature. TLC (DCM:MeOH:NH₄OH, 90:9:1) shows no starting materials. The DMF was removed under high vacuum (product could be partially soluble in water). Crude product was filtered over a silica-carbonate cartridge using DCM:MeOH (9:1) as a eluent. Filtrate was evaporated under vacuum and crude product was purified by PTLC (DCM:MeOH:NH₄OH, 90:9:1), a second purification was performed by PTLC (DCM:MeOH, 9:1) to give 8 mg of product (25% yield). ¹H NMR (500 MHz, DMSO-d6) δ 12.97 (bs, 1H), 9.72 (bs, 1H), 8.97 (s, 1H), 8.71 (d, J=2.1 Hz, 1H), 8.61 (s, 2H), 8.56 (t, J=6.0 Hz, 2H), 8.23 (s, 1H), 7.99 (d, J=9.3 Hz, 1H), 7.59 (td, J=9.0, 5.9 Hz, 1H), 7.50-7.16 (m, 8H), 6.98 (d, J=8.2 Hz, 1H), 5.13 (d, J=3.4 Hz, 1H), 4.58 (d, J=9.3 Hz, 1H), 4.48-4.40 (m, 2H), 4.35 (s, 1H), 4.22 (dd, J=15.9, 5.5 Hz, 1H), 4.08 (ddt, J=9.6, 7.1, 3.2 Hz, 2H), 3.74-3.62 (m, 2H), 3.15-3.06 (m, 2H), 2.50-2.45 (m, 1H), 2.41-2.33 (m, 1H), 2.09-1.86 (m, 4H), 1.79-1.67 (m, 2H), 0.97 (t, 3H), 0.94 (s, 9H). ¹³C NMR (151 MHz, dmso) δ 181.05, 172.38, 172.05, 170.09, 159.63, 156.44 (dd, J=246.5, 6.8 Hz), 152.74 (dd, J=249.6, 8.6 Hz), 151.86, 149.36, 148.13, 140.05, 139.92, 139.24, 131.87, 131.59, 130.71, 130.05, 129.20 (t, J=5.0 Hz), 129.06, 127.84, 127.52, 122.37 (dd, J=13.5, 3.5 Hz), 119.87, 118.95-118.24 (m), 117.88, 116.11, 114.12, 113.60, 112.91-112.65 (m), 69.32, 67.53, 59.14, 56.88, 56.83, 53.86, 42.08, 38.38, 35.67, 31.76, 26.80, 25.52, 17.26, 16.37, 13.04. LC-MS (ESI); m/z [M+H]⁺: Calcd. for C₄₉H₅₄F₂N₇O₈S₂, 970.3443. Found 970.3787.

Example Synthesis of Compound 300: (2S,4R)-1-((S)-2-(2-(2-(3-(3-(2,6-difluoro-3-(propylsulfonamido)benzoyl)-1H-pyrrolo[2,3-b]pyridin-5-yl)phenoxy)ethoxy)acetamido)-3,3-dimethylbutanoyl)-4-hydroxy-N-(4-(4-methylthiazol-5-yl)benzyl)pyrrolidine-2-carboxamide

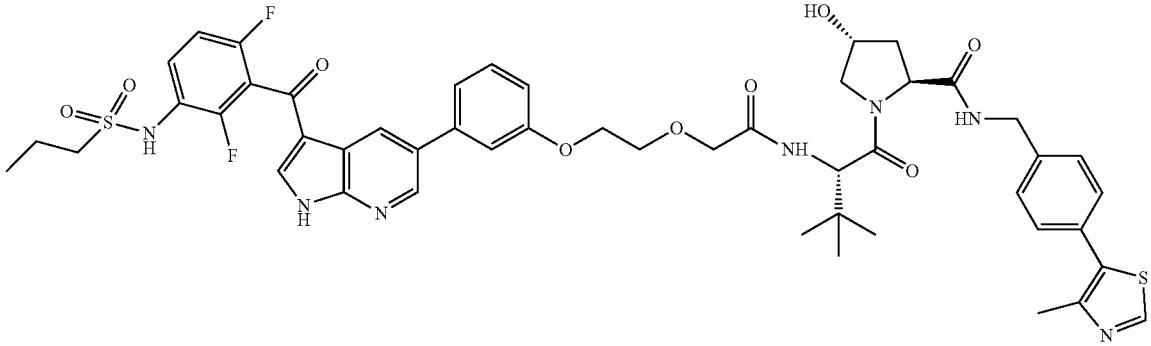 [SMILES: CCCS(=O)(=O)Nc1ccc(F)c(C(=O)c2c[nH]c3ncc(-c4cccc(OCCOCC(=O)N[C@H](C(=O)N5C[C@H](O)C[C@H]5C(=O)NCc5ccc(-c6scnc6C)cc5)C(C)(C)C)c4)cc23)c1F]

To a solution of 2-[2-[3-[3-[2,6-difluoro-3-(propylsulfonylaminobenzoyl]-1H-pyrrolo[2,3-b]pyridin-5-yl]phenoxy]ethoxy]acetic acid (19.1 mg, 0.03 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (17.11 mg, 0.04 mmol) in DMF (2 ml) was added TEA (0.1 ml, 0.72 mmol) and PyBOP (19.06 mg, 0.04 mmol) at room temperature. The reaction mixture was stirred for 2 hours at the same temperature. TLC (DCM:MeOH:NH$_4$OH, 90:9:1) shows no starting materials. The DMF was removed under high vacuum (product could be partially soluble in water). Crude product was filtered over a silica-carbonate cartridge using DCM:MeOH (9:1) as a eluent. Filtrate was evaporated under vacuum and crude product was purified by PTLC (DCM:MeOH:NH$_4$OH, 90:9:1) to give 13 mg of product (40% yield). $^1$H NMR (400 MHz, DMSO-d6) δ 12.95 (bs, 1H), 9.74 (bs, 1H), 8.91 (s, 1H), 8.67 (d, J=2.0 Hz, 1H), 8.55 (dd, J=12.8, 6.8 Hz, 2H), 8.19 (s, 1H), 7.56 (td, J=9.0, 6.0 Hz, 1H), 7.49 (d, J=9.5 Hz, 1H), 7.42-7.20 (m, 8H), 7.07-7.00 (m, 1H), 5.13 (d, J=3.5 Hz, 1H), 4.58 (d, J=9.6 Hz, 1H), 4.44 (t, J=8.1 Hz, 1H), 4.36 (dd, J=15.8, 6.2 Hz, 2H), 4.30-4.16 (m, 3H), 4.06 (s, 2H), 3.86 (t, J=4.3 Hz, 2H), 3.13-3.04 (m, 2H), 2.37 (s, 3H), 2.07-1.99 (m, 1H), 1.94-1.83 (m, 1H), 1.78-1.64 (m, 2H), 0.94 (t, 3H), 0.93 (s, 9H). $^{13}$C NMR (126 MHz, dmso) δ 181.03, 172.20, 169.60, 168.98, 159.52, 156.46 (dd, J=246.7, 7.1 Hz), 152.75 (dd), 151.81, 149.36, 148.14, 144.59, 140.08, 139.80, 139.21, 131.85, 131.56, 130.66, 130.08, 129.62-128.89 (m), 129.08, 127.82, 122.38 (dd, J=13.5, 3.6 Hz), 120.09, 118.98-118.30 (m), 117.89, 116.15, 114.40, 113.50, 112.78 (dd, J=22.9, 3.8 Hz), 70.05, 70.00, 69.34, 67.49, 59.18, 57.04, 56.16, 53.89, 42.12, 38.34, 36.22, 26.65, 17.28, 16.32, 13.05. LC-MS (ESI); m/z [M+H]$^+$: Calcd. for $C_{49}H_{54}F_2N_7O_9S_2$, 986.3392. Found 986.3679.

Example Synthesis of Compound 217: N1-(4-(3-(2,6-difluoro-3-(propylsulfonamido)benzoyl)-1H-pyrrolo[2,3-b]pyridin-5-yl)phenyl)-N5-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide

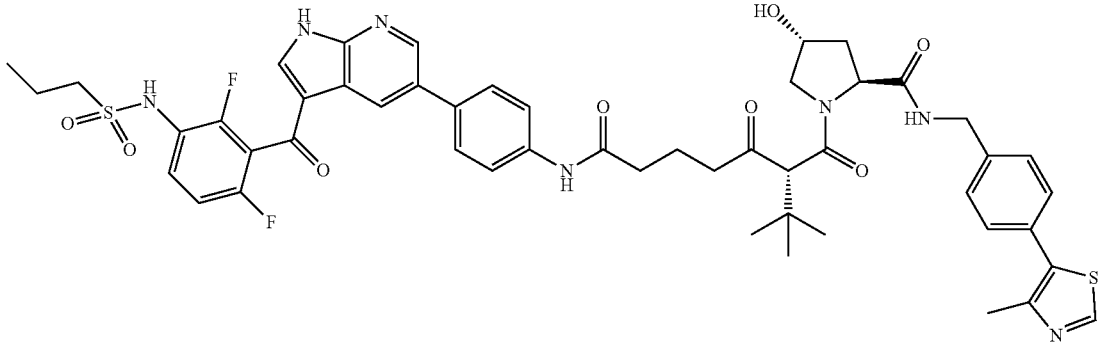 [SMILES: CCCS(=O)(=O)Nc1ccc(F)c(C(=O)c2c[nH]c3ncc(-c4ccc(NC(=O)CCCC(=O)[C@H](C(=O)N5C[C@H](O)C[C@H]5C(=O)NCc5ccc(-c6scnc6C)cc5)C(C)(C)C)cc4)cc23)c1F]

To a solution of 5-((4-(3-(2,6-difluoro-3-(propylsulfonamido)-benzoyl)-1H-pyrrolo[2,3-b]pyridin-5-yl)phenyl)amino)-5-oxopentanoic acid (9.7 mg, 0.02 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (8.52 mg, 0.02 mmol) in DMF (1 ml) was added TEA (0.1 ml, 0.72 mmol) and PyBOP (9.5 mg, 0.02 mmol) at room temperature. The reaction mixture was stirred for 4 hours at the same temperature. TLC (DCM:MeOH:NH$_4$OH, 90:9:1) shows no starting materials.

The reaction mixture was diluted with EtOAc (10 mL) and washed with brine (5 mL, 4×), organic phase was dried (Na$_2$SO$_4$), and evaporated under vacuum. Crude product was purified by PTLC (DCM:MeOH:NH$_4$OH, 90:9:1) to give 4.8 mg of product (29% yield). $^1$H NMR (500 MHz, DMSO-d6) δ 10.02 (s, 1H), 8.97 (s, 1H), 8.68 (d, 1H), 8.64-8.52 (m, 2H), 8.21 (s, 1H), 7.95 (d, J=9.2 Hz, 1H), 7.72 (dd, J=36.7, 8.5 Hz, 4H), 7.62-7.54 (m, 1H), 7.40 (dd, 4H), 7.28 (t, J=8.7 Hz, 1H), 5.16 (d, 2H), 4.56 (d, J=9.3 Hz, 1H), 4.50-4.40 (m, 2H), 4.40-4.33 (m, 1H), 4.22 (dd, J=15.8, 5.3 Hz, 1H), 3.76-3.62 (m, 2H), 3.16-3.05 (m, 2H), 2.44 (s, 3H), 2.41-2.17 (m, 4H), 2.09-2.01 (m, 1H), 1.98-1.80 (m, 3H), 1.74 (dq, J=14.9, 7.4 Hz, 2H), 0.96 (s, 9H), 0.95 (t, 3H). $^{13}$C NMR (151 MHz, dmso) δ 181.06, 172.39, 172.17, 171.46, 170.15, 156.37 (dd, J=246.6, 6.3 Hz), 152.73 (dd, J=249.4, 8.1 Hz), 151.86, 149.05, 148.13, 144.19, 139.91, 139.37, 139.13, 132.97, 131.64, 131.59, 130.05, 129.22 (d, J=14.7 Hz), 129.06, 127.84, 127.74, 126.89, 122.47 (d, J=14.1 Hz), 120.07, 119.02-118.20 (m), 117.95, 116.06, 112.75 (dd, J=23.4, 2.8 Hz), 69.34, 59.15, 56.90, 56.81, 53.87, 42.08, 38.38, 36.36, 35.63, 34.63, 26.85, 21.91, 17.27, 16.37, 13.04. LC-MS (ESI); m/z [M+H]$^+$: Calcd. for C$_{50}$H$_{55}$F$_2$N$_8$O$_8$S$_2$, 997.3552. Found 997.3524.

Example Synthesis of Compound 218: (2S,4R)-1-((S)-2-(5-(4-(3-(2,6-difluoro-3-(propylsulfonamido) benzoyl)-1H-pyrrolo[2,3-b]pyridin-5-yl)piperazin-1-yl)-5-oxopentanamido)-3,3-dimethylbutanoyl)-4-hydroxy-N-(4-(4-methylthiazol-5-yl)benzyl) pyrrolidine-2-carboxamide

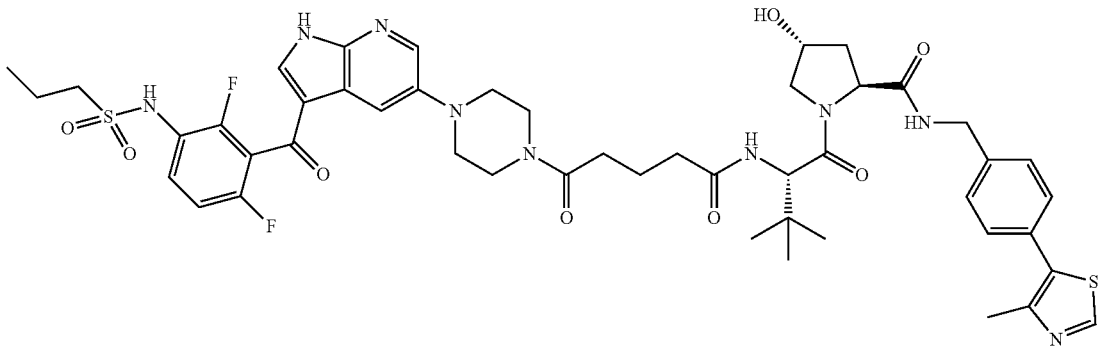 [SMILES: CCCS(=O)(=O)Nc1ccc(F)c(C(=O)c2c[nH]c3ncc(N4CCN(C(=O)CCCC(=O)N[C@H](C(=O)N5C[C@H](O)C[C@H]5C(=O)NCc5ccc(-c6scnc6C)cc5)C(C)(C)C)CC4)cc23)c1F]

To a solution of 5-(4-(3-(2,6-difluoro-3-(propylsulfonamido)-benzoyl)-1H-pyrrolo[2,3-b]pyridin-5-yl)piperazin-1-yl)-5-oxopentanoic acid (9.3 mg, 0.02 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (8.27 mg, 0.018 mmol) in DMF (1 ml) was added TEA (0.1 ml, 0.72 mmol) and PyBOP (9.22 mg, 0.018 mmol) at room temperature. The reaction mixture was stirred for 4 hours at the same temperature. TLC (DCM:MeOH:NH$_4$OH, 90:9:1) shows no starting materials. The reaction mixture was diluted with EtOAc (10 mL) and washed with brine (5 mL, 4×), organic phase was dried (Na$_2$SO$_4$), and evaporated under vacuum. Crude mixture did not show product by TLC, just some VHL starting material (4) (Product is soluble in water). Water extracts were lyophilized for overnight, the solid residue was filtered using a mixture of DCM:MeOH:NH$_4$OH (90:9:1, 30 mL). Filtrate was evaporated to dryness and crude product was purified by PTLC (DCM:MeOH:NH$_4$OH, 90:9:1) to give 13 mg of product (81% yield). $^1$H NMR (500 MHz, DMSO-d6) δ 12.64 (bs, 1H), 9.74 (bs, 1H), 8.97 (s, 1H), 8.62-8.52 (m, 3H), 8.28 (d, J=2.0 Hz, 1H), 8.00 (s, 1H), 7.95 (bs, 1H), 7.90 (d, J=9.2 Hz, 1H), 7.59-7.49 (m, 1H), 7.47-7.27 (m, 4H), 7.20 (t, J=8.7 Hz, 1H), 5.13 (bs, 1H), 4.56 (d, J=9.3 Hz, 1H), 4.48-4.32 (m, 3H), 4.22 (dd, J=15.8, 5.3 Hz, 1H), 3.75-3.57 (m, 5H), 3.23-3.02 (m, 7H), 2.44 (s, 3H), 2.41-2.17 (m, 4H), 2.07-2.01 (m, 1H), 1.96-1.87 (m, 1H), 1.81-1.66 (m, 4H), 0.95 (s, 9H), 0.94 (t, 3H). $^{13}$C NMR (151 MHz, dmso) δ 180.70, 171.99, 171.92, 170.44, 169.75, 155.24 (dd, J=248.1, 5.5 Hz), 152.12 (dd, J=248.8, 8.5 Hz), 151.47, 147.73, 144.63, 144.31, 139.52, 138.02, 137.75, 131.19, 129.65, 128.65, 127.98-127.64 (m), 127.44, 123.91-123.09 (m), 118.86-117.72 (m), 117.60, 115.50, 115.23, 112.02 (dd, J=22.6, 3.2 Hz), 68.92, 58.74, 56.47, 56.43, 53.44, 50.31, 50.18, 48.63, 44.86, 41.68, 41.00, 37.99, 34.28, 31.80, 26.43, 21.36, 16.99, 15.97, 12.72. LC-MS (ESI); m/z [M+H]$^+$: Calcd. for C$_{48}$H$_{58}$F$_2$N$_9$O$_8$S$_2$, 990.3817. Found 990.3889.

Example Synthesis of Compound 219: (2S,4R)-1-((S)-2-(4-(4-(3-(2,6-difluoro-3-(propylsulfonamido)benzoyl)-1H-pyrrolo[2,3-b]pyridin-5-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide

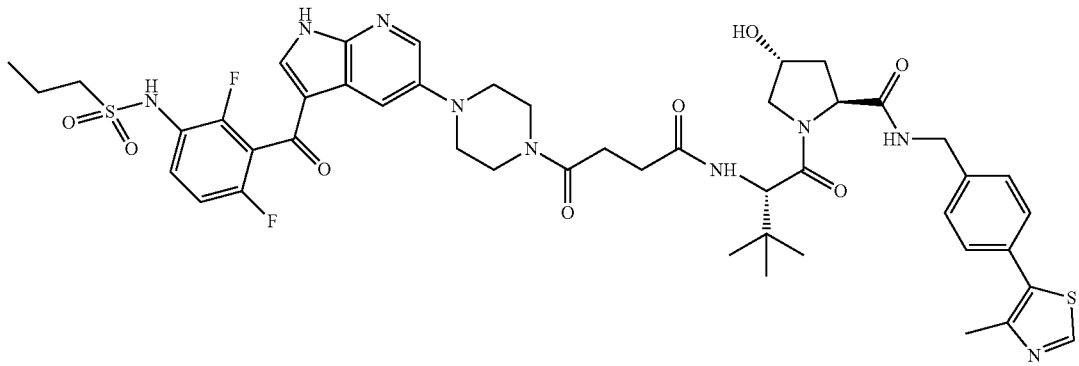 [SMILES: CCCS(=O)(=O)Nc1ccc(F)c(C(=O)c2c[nH]c3ncc(N4CCN(C(=O)CCC(=O)N[C@H](C(=O)N5C[C@H](O)C[C@H]5C(=O)NCc5ccc(-c6scnc6C)cc5)C(C)(C)C)CC4)cc23)c1F]

4-(4-(3-(2,6-difluoro-3-(propylsulfonamido)-benzoyl)-1H-pyrrolo[2,3-b]pyridin-5-yl)piperazin-1-yl)-4-oxobutanoic acid (9 mg, 0.016 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (8.2 mg, 0.018 mmol) in DMF (1 ml) was added TEA (0.1 ml, 0.72 mmol) and PyBOP (9.14 mg, 0.018 mmol) at room temperature. The reaction mixture was stirred for 12 hours (overnight) at the same temperature. TLC (DCM:MeOH:NH$_4$OH, 90:9:1) shows no starting materials. The reaction mixture was evaporated to dryness. Crude product was filtered over a silica-carbonate cartridge (100 mg) using DCM:MeOH (9:1) as eluent. Filtrate was evaporated under vacuum and crude product was purified by PTLC (DCM:MeOH:NH$_4$OH, 90:9:1) to give 11 mg of product (75% yield). $^1$H NMR (500 MHz, DMSO-d6) δ 12.66 (bs, 1H), 9.45 (bs, 1H), 8.98 (s, 1H), 8.60 (bs, 1H), 8.29 (s, 1H), 8.04 (s, 1H), 8.01-7.88 (m, 2H), 7.62-7.49 (m, 1H), 7.40 (q, J=8.0 Hz, 4H), 7.26 (t, J=8.8 Hz, 1H), 5.15 (d, J=3.5 Hz, 1H), 4.54 (d, J=9.3 Hz, 1H), 4.49-4.31 (m, 3H), 4.22 (dd, J=16.1, 5.6 Hz, 1H), 3.81-3.53 (m, 6H), 3.26-3.03 (m, 6H), 2.73-2.52 (m, 3H), 2.44 (s, 3H), 2.42-2.33 (m, 1H), 2.09-1.98 (m, 1H), 1.95-1.84 (m, 1H), 1.74 (q, J=7.5 Hz, 2H), 0.96 (t, 3H), 0.94 (s, 9H). $^{13}$C NMR (126 MHz, dmso) δ 180.45, 172.02, 171.35, 170.07, 169.64, 156.00 (dd, J=245.9, 6.5 Hz), 152.34 (dd, J=249.7, 8.3 Hz), 151.52, 147.75, 144.70, 144.30, 139.55, 138.08, 137.91, 131.22, 129.66, 128.69, 128.53 (d, J=2.4 Hz), 127.46, 121.96 (d, J=14.1 Hz), 118.61-117.82 (m), 117.60, 115.44, 115.20, 112.32 (dd, J=23.0, 3.3 Hz), 68.95, 58.78, 56.50, 56.39, 53.46, 50.25, 50.13, 44.76, 41.69, 41.17, 37.99, 35.43, 30.18, 28.05, 26.44, 16.89, 16.00, 12.67. LC-MS (ESI); m/z [M+H]$^+$: Calcd. for C$_{47}$H$_{56}$F$_2$N$_9$O$_8$S$_2$, 976.3661. Found 976.3712.

Example Synthesis of Compound 220: N$^1$-(4-(3-(2,6-difluoro-3-(propylsulfonamido)benzoyl)-1H-pyrrolo[2,3-b]pyridin-5-yl)phenyl)-N$^4$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide

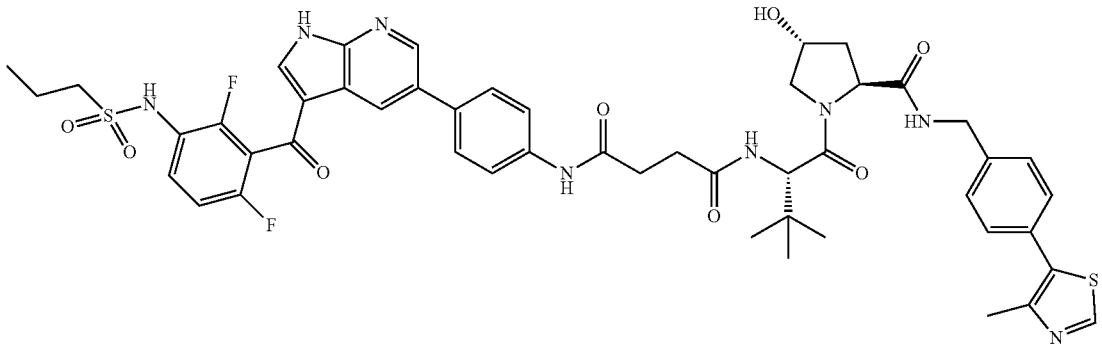 [SMILES: CCCS(=O)(=O)Nc1ccc(F)c(C(=O)c2c[nH]c3ncc(-c4ccc(NC(=O)CCC(=O)N[C@H](C(=O)N5C[C@H](O)C[C@H]5C(=O)NCc5ccc(-c6scnc6C)cc5)C(C)(C)C)cc4)cc23)c1F]

To a solution of the product from the synethesis of compound 218 [(2S,4R)-1-((S)-2-(5-(4-(3-(2,6-difluoro-3-(propylsulfonamido)benzoyl)-1H-pyrrolo[2,3-b]pyridin-5-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide]; 4-((4-(3-(2,6-difluoro-3-(propylsulfonamido)-benzoyl)-1H-pyrrolo[2,3-b]pyridin-5-yl)phenyl)amino)-4-oxobutanoic acid (15 mg, 0.03 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (13.51 mg, 0.03 mmol) in DMF (1 ml) was added TEA (0.1 ml, 0.72 mmol) and PyBOP (15.05 mg, 0.03 mmol) at room temperature. The reaction mixture was stirred for 4 hours at the same temperature. TLC (DCM:MeOH:NH$_4$OH, 90:9:1) shows no starting materials. The reaction mixture was evaporated to dryness under high vacuum. Crude product was filtered over a silica-carbonate cartridge (100 mg) using DCM:MeOH (9:1) as eluent. Filtrate was evaporated under vacuum and crude product was purified by PTLC (DCM:MeOH: NH$_4$OH, 90:9:1) to give 8 mg of product (31% yield). $^1$H NMR (500 MHz, DMSO-d6) δ 12.97 (bs, 1H), 10.11 (s, 1H), 9.79 (bs, 1H), 8.98 (d, J=2.3 Hz, OH), 8.69 (s, 1H), 8.66-8.49 (m, 2H), 8.23 (s, 1H), 8.02 (d, J=9.0 Hz, 1H), 7.84-7.64 (m, 4H), 7.63-7.53 (m, 1H), 7.51-7.33 (m, 4H), 7.29 (t, J=8.4 Hz, 1H), 5.17 (s, 1H), 4.56 (d, J=7.8 Hz, 1H), 4.50-4.39 (m, 2H), 4.40-4.31 (m, 1H), 4.26-4.16 (m, 1H), 3.66 (q, J=10.1 Hz, 2H), 3.19-3.06 (m, 2H), 2.72-2.52 (m, 4H), 2.44 (s, 3H), 2.12-1.97 (m, 1H), 1.96-1.84 (m, 1H), 1.74 (dq, J=13.2, 8.3, 7.3 Hz, 2H), 0.96 (t, 3H), 0.95 (s, 9H). $^{13}$C NMR (126 MHz, dmso) δ 180.66, 172.02, 171.24, 170.67, 169.64, 156.05 (dd, J=246.9, 7.0 Hz), 152.37 (dd, J=249.3, 8.1 Hz), 151.49, 148.66, 147.75, 143.82, 139.53, 139.00, 138.70, 132.54, 131.27, 131.22, 129.68, 129.22-128.38 (m), 128.69, 127.47, 127.39, 126.53, 121.99 (dd, J=12.9, 4.5 Hz), 119.59, 118.72-117.87 (m), 117.57, 115.68, 112.90-112.05 (m), 68.95, 58.79, 56.56, 56.41, 53.51, 41.71, 37.98, 35.45, 31.98, 30.14, 26.43, 16.88, 15.99, 12.65. LC-MS (ESI); m/z [M+H]$^+$: Calcd. for C$_{49}$H$_{53}$F$_2$N$_8$O$_8$S$_2$, 983.3395. Found 983.3569.

Example Synthesis of Compound 221: N1-(4-(3-(2, 6-difluoro-3-(propylsulfonamido)benzoyl)-1H-pyrrolo[2,3-b]pyridin-5-yl)phenyl)-N3-((S)-1-((2S,4R)-4-hydroxy-2-((4-(4-methylthiazol-5-yl)benzyl) carbamoyl)pyrrolidin-1-yl)-3,3-dimethyl-1-oxobutan-2-yl)malonamide

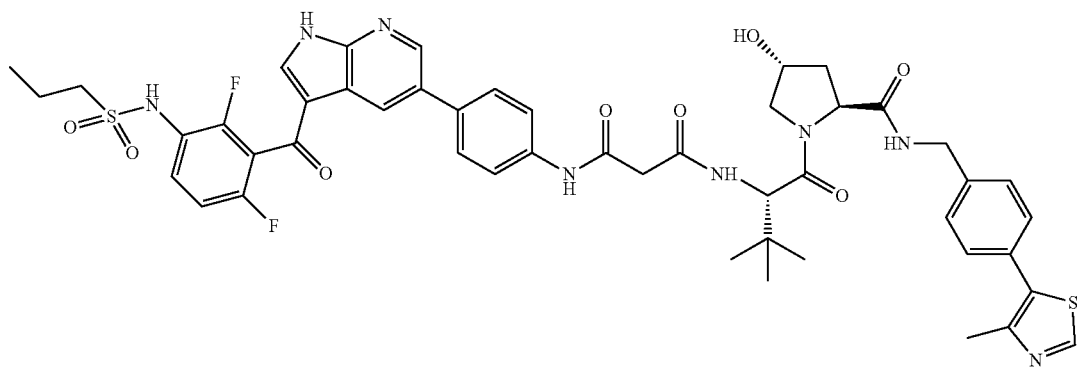 [SMILES: CCCS(=O)(=O)Nc1ccc(F)c(C(=O)c2c[nH]c3ncc(-c4ccc(NC(=O)CC(=O)N[C@H](C(=O)N5C[C@H](O)C[C@H]5C(=O)NCc5ccc(-c6scnc6C)cc5)C(C)(C)C)cc4)cc23)c1F]

To a solution of 3-((4-(3-(2,6-difluoro-3-(propylsulfonamido)-benzoyl)-1H-pyrrolo[2,3-b]pyridin-5-yl)phenyl) amino)-3-oxopropanoic acid (16.8 mg, 0.03 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (15.5 mg, 0.033 mmol) in DMF (1 ml) was added TEA (0.1 ml, 0.72 mmol) and PyBOP (17.28 mg, 0.033 mmol) at room temperature. The reaction mixture was stirred for 12 hours (overnight) at the same temperature. TLC (DCM:MeOH:NH$_4$OH, 90:9:1) shows no starting materials. The reaction mixture was evaporated to dryness under high vacuum. Crude product was filtered over a silica-carbonate cartridge (100 mg) using DCM:MeOH (9:1) as eluent. Filtrate was evaporated under vacuum and crude product was purified by PTLC (DCM: MeOH:NH$_4$OH, 90:9:1) to give 19.5 mg of product (67% yield). $^1$H NMR (400 MHz, DMSO-d6) δ 12.96 (bs, 1H), 10.23 (s, 1H), 9.75 (bs, 1H), 8.97 (s, 1H), 8.69 (s, 1H), 8.66-8.51 (m, 2H), 8.26 (d, J=9.1 Hz, 1H), 8.22 (s, 1H), 7.73 (dd, J=8.5 Hz, 4H), 7.59 (q, J=8.6 Hz, 1H), 7.41 (dd, J=8.0 Hz, 4H), 7.28 (t, J=8.7 Hz, 1H), 5.16 (d, 1H), 4.59 (d, J=9.2 Hz, 1H), 4.52-4.33 (m, 3H), 4.24 (dd, J=15.7, 5.0 Hz, 1H), 3.68 (q, J=10.6 Hz, 2H), 3.44 (q, 2H), 3.20-3.05 (m, 2H), 2.45 (s, 3H), 2.10-2.01 (m, 1H), 1.96-1.89 (m, 1H), 1.74 (dq, J=14.8, 7.3 Hz, 2H), 0.98 (s, 9H), 0.97 (t, J=8.3 Hz, 3H). $^{13}$C NMR (101 MHz, dmso) δ 180.62, 171.91, 169.34, 166.16, 166.03, 156.02 (dd, J=246.8, 7.1 Hz), 152.34 (dd, J=249.4, 8.1 Hz), 151.43, 148.69, 147.73, 143.79, 139.50, 138.69, 138.54, 132.98, 131.17, 131.13, 129.68, 129.11-128.65 (m), 128.67, 128.01, 127.45, 126.53, 122.21-121.73 (m), 119.70, 118.63-117.89 (m), 117.54, 115.66, 112.35 (dd, J=23.5, 3.0 Hz), 68.93, 58.79, 56.66, 56.52, 53.49, 44.32, 41.70, 37.97, 35.60, 26.33, 16.85, 15.96, 12.62. LC-MS (ESI); m/z [M+H]$^+$: Calcd. for C$_{48}$H$_{51}$F$_2$N$_8$O$_8$S$_2$, 969.3239. Found 969.3272.

Example Synthesis of Compound 222: (2S,4R)-1-((S)-2-(3-(4-(3-(2,6-difluoro-3-(propylsulfonamido)benzoyl)-1H-pyrrolo[2,3-b]pyridin-5-yl)piperazin-1-yl)-3-oxopropanamido)-3,3-dimethylbutanoyl)-4-hydroxy-N-(4-(4-methylthiazol-5-yl)benzyl)pyrrolidine-2-carboxamide

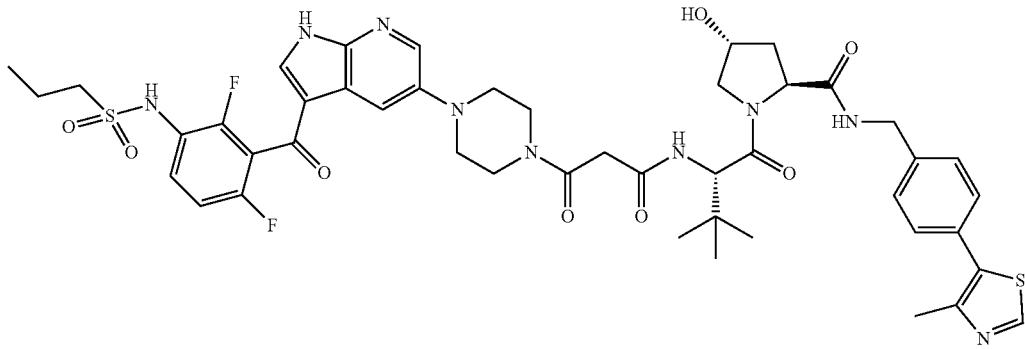 [SMILES: CCCS(=O)(=O)Nc1ccc(F)c(C(=O)c2c[nH]c3ncc(N4CCN(C(=O)CC(=O)N[C@H](C(=O)N5C[C@H](O)C[C@H]5C(=O)NCc5ccc(-c6scnc6C)cc5)C(C)(C)C)CC4)cc23)c1F]

To a solution of 3-(4-(3-(2,6-difluoro-3-(propylsulfonamido)-benzoyl)-1H-pyrrolo[2,3-b]pyridin-5-yl)piperazin-1-yl)-3-oxopropanoic acid (12.5 mg, 0.02 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (11.69 mg, 0.03 mmol) in DMF (1 ml) was added TEA (0.1 ml, 0.72 mmol) and PyBOP (13.02 mg, 0.03 mmol) at room temperature. The reaction mixture was stirred for 12 hours (overnight) at the same temperature. TLC (DCM:MeOH:NH$_4$OH, 90:9:1) shows no starting materials. The reaction mixture was evaporated to dryness. Crude product was filtered over a silica-carbonate cartridge (100 mg) using DCM:MeOH (9:1) as eluent. Filtrate was evaporated under vacuum and crude product was purified by PTLC (DCM:MeOH:NH$_4$OH, 90:9:1) to give 14.1 mg of product (64% yield). $^1$H NMR (500 MHz, DMSO-d6) δ 12.71 (bs, 1H), 9.74 (bs, 1H), 8.98 (s, 1H), 8.59 (t, J=5.7 Hz, 1H), 8.29 (s, 1H), 8.26 (d, J=9.1 Hz, 1H), 8.03 (s, 1H), 7.96 (bs, 1H), 7.57 (q, J=7.4, 6.3 Hz, 1H), 7.41 (dd, J=8.0 Hz, 4H), 7.26 (t, J=8.7 Hz, 1H), 5.22-5.05 (m, 1H), 4.58 (d, J=9.3 Hz, 1H), 4.51-4.32 (m, 3H), 4.23 (dd, J=15.8, 5.3 Hz, 1H), 3.67 (q, J=12.3, 10.6 Hz, 8H), 3.52 (dd, J=53.7, 15.5 Hz, 2H), 3.27-3.05 (m, 6H), 2.45 (s, 3H), 2.09-2.00 (m, 1H), 1.96-1.86 (m, 1H), 1.74 (h, J=7.3 Hz, 2H), 0.97 (s, 9H), 0.96 (t, 3H). $^{13}$C NMR (101 MHz, dmso) δ 180.41, 171.91, 169.38, 166.32, 166.06, 156.01 (dd, J=246.5, 6.7 Hz), 152.34 (dd, J=249.2, 8.3 Hz), 151.44, 147.73, 144.60, 144.28, 139.50, 138.06, 137.84, 131.17, 129.66, 128.75 (d, J=8.0 Hz), 128.65, 127.43, 121.86 (dd, J=13.5, 3.5 Hz), 118.34 (m), 117.58, 115.42, 115.18, 112.28 (dd, J=23.1, 3.5 Hz), 68.89, 58.75, 56.54, 56.43, 53.49, 50.10, 45.56, 41.68, 41.19, 40.95, 37.95, 35.52, 26.36, 16.85, 15.96, 12.62. LC-MS (ESI); m/z [M+H]$^+$: Calcd. for C$_{46}$H$_{54}$F$_2$N$_9$O$_8$S$_2$, 962.3504. Found 962.3694.

Example Synthesis of Compound 301: (2S,4R)-1-((S)-2-(4-(4-(3-(3-butyramido-2,6-difluorobenzoyl)-1H-pyrrolo[2,3-b]pyridin-5-yl)phenoxy)butanamido)-3,3-dimethylbutanoyl)-4-hydroxy-N-(4-(4-methylthiazol-5-yl)benzyl)pyrrolidine-2-carboxamide

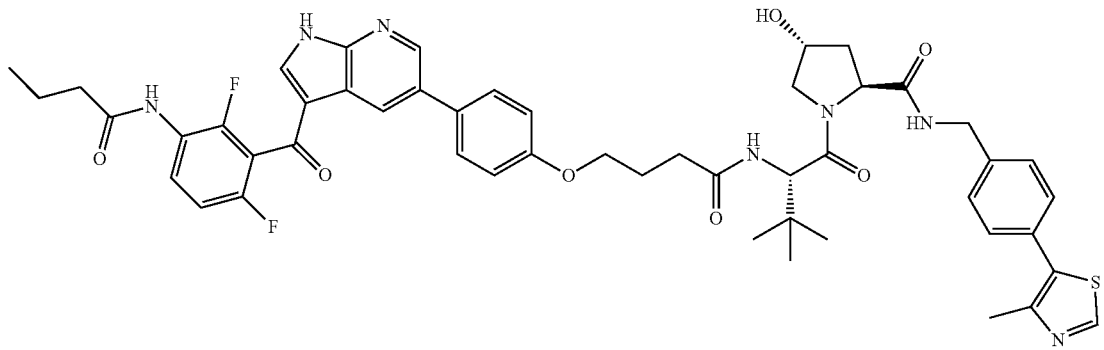 [SMILES: CCCC(=O)Nc1ccc(F)c(C(=O)c2c[nH]c3ncc(-c4ccc(OCCCC(=O)N[C@H](C(=O)N5C[C@H](O)C[C@H]5C(=O)NCc5ccc(-c6scnc6C)cc5)C(C)(C)C)cc4)cc23)c1F]

To a solution of 4-(4-(3-(3-butyramido-2,6-difluorobenzoyl)-1H-pyrrolo[2,3-b]pyridin-5-yl)phenoxy)butanoic acid (27 mg, 0.05 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (26.6 mg, 0.06 mmol) in DMF (2 ml) was added TEA (0.1 ml, 0.72 mmol) and PyBOP (29.64 mg, 0.06 mmol) at room temperature. The reaction mixture was stirred for 4 hours at the same temperature. TLC (DCM:MeOH:NH$_4$OH, 90:9:1) shows no starting materials. The DMF was removed under high vacuum. Crude product was filtered over a silica-carbonate cartridge using DCM:MeOH (9:1) as a eluent. Filtrate was evaporated under vacuum and crude product was purified by PTLC (DCM:MeOH:NH$_4$OH, 90:9:1) to give 37 mg of product (76% yield). $^1$H NMR (400 MHz, DMSO-d6) δ 12.91 (bs, 1H), 9.79 (s, 1H), 8.97 (s, 1H), 8.65 (d, J=2.2 Hz, 1H), 8.62-8.47 (m, 2H), 8.15 (s, 1H), 8.06-7.89 (m, 2H), 7.67 (d, J=8.7 Hz, 2H), 7.40 (dd, J=8.3 Hz, 4H), 7.23 (t, J=8.8 Hz, 1H), 7.07 (d, J=8.8 Hz, 2H), 5.14 (d, J=3.5 Hz, 1H), 4.58 (d, J=9.3 Hz, 1H), 4.49-4.40 (m, 2H), 4.37 (bs, 1H), 4.22 (dd, J=15.9, 5.4 Hz, 1H), 4.03 (t, J=7.2 Hz, 2H), 3.77-3.62 (m, 2H), 2.44 (s, 3H), 2.43-2.30 (m, 4H), 2.09-1.87 (m, 4H), 1.61 (h, J=7.4 Hz, 2H), 0.96 (s, 9H), 0.92 (t, J=7.4 Hz, 3H). $^{13}$C NMR (151 MHz, dmso) δ 180.92, 171.97, 171.67, 171.61, 169.68, 158.33, 154.61 (dd, J=244.6, 7.1 Hz), 151.44, 150.34 (dd, J=248.8, 8.2 Hz), 148.52, 147.72, 143.71, 139.52, 138.48, 131.32, 131.17, 130.42, 129.64, 128.65, 128.28, 127.43, 126.50, 126.06 (d, J=10.1 Hz), 123.23 (dd, J=12.4, 3.6 Hz), 118.47-117.44 (m), 117.55, 115.65, 115.18, 111.60 (d, J=25.0 Hz), 68.92, 67.13, 58.74, 56.48, 56.42, 41.67, 37.99, 37.57, 35.26, 31.32, 26.41, 25.07, 18.56, 15.96, 13.57. LC-MS (ESI); m/z [M+H]$^+$: Calcd. for C$_{50}$H$_{54}$F$_2$N$_7$O$_7$S, 934.3773. Found 934.2690.

Example Synthesis of Compound 302: (2S,4R)-1-((S)-2-(4-(4-(3-(3-amino-2,6-difluorobenzoyl)-1H-pyrrolo[2,3-b]pyridin-5-yl)phenoxy)butanamido)-3,3-dimethylbutanoyl)-4-hydroxy-N-(4-(4-methylthiazol-5-yl)benzyl)pyrrolidine-2-carboxamide

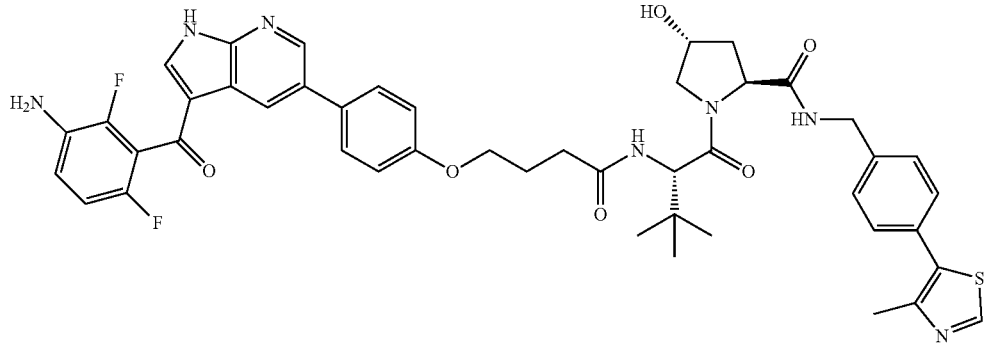 [SMILES: Cc1ncsc1-c1ccc(CNC(=O)[C@@H]2C[C@@H](O)CN2C(=O)[C@@H](NC(=O)CCCOc2ccc(-c3cnc4[nH]cc(C(=O)c5c(F)ccc(N)c5F)c4c3)cc2)C(C)(C)C)cc1]

To a solution of 4-(4-(3-(3-amino-2,6-difluorobenzoyl)-1H-pyrrolo[2,3-b]pyridin-5-yl)phenoxy)butanoic acid (11.5 mg, 0.03 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (23.79 mg, 0.05 mmol) in DMF(2 ml) was added TEA (0.1 ml, 0.72 mmol) and PyBOP (14.58 mg, 0.03 mmol) at room temperature. The reaction mixture was stirred for 4 h at the same temperature. TLC (DCM:MeOH:NH$_4$OH, 90:9:1) shows no starting materials. The DMF was removed under high vacuum. Crude product was filtered over a silica-carbonate cartridge (1 g) using DCM:MeOH (9:1) as a eluent. Filtrate was evaporated under vacuum and crude product was purified by PTLC (MeOH:DCM, 9:1), to give 17.5 mg of product (80% yield). $^1$H NMR (500 MHz, DMSO-d6) δ 12.68 (bs, 1H), 8.97 (s, 1H), 8.64 (d, J=2.2 Hz, 1H), 8.61-8.47 (m, 2H), 8.06 (s, 1H), 8.00 (d, J=9.3 Hz, 1H), 7.65 (d, J=8.6 Hz, 2H), 7.40 (dd, 4H), 7.07 (d, J=8.7 Hz, 2H), 6.99-6.82 (m, 2H), 5.21 (s, 2H), 5.15 (d, J=3.6 Hz, 1H), 4.58 (d, J=9.3 Hz, 1H), 4.50-4.40 (m, 2H), 4.37 (bs, 1H), 4.23 (dd, J=15.8, 5.3 Hz, 1H), 4.10-3.93 (m, 2H), 3.78-3.54 (m, 2H), 2.58-2.26 (m, 2H), 2.44 (s, 3H), 2.11-1.82 (m, 4H), 0.94 (s, 9H). $^{13}$C NMR (126 MHz, dmso) δ 182.20, 171.97, 171.63, 169.69, 158.31, 151.43, 149.20 (dd, J=234.8, 6.5 Hz), 148.45, 147.72, 146.01 (dd, J=241.2, 7.9 Hz), 143.55, 139.51, 137.92, 133.42 (dd, J=12.9, 2.4 Hz), 131.18, 130.49, 129.65, 128.65, 128.24, 127.44, 126.47, 118.32-117.22 (m), 117.57, 116.91-116.23 (m), 115.84, 115.19, 111.36 (dd, J=22.3, 2.9 Hz), 68.92, 67.14, 58.74, 56.50, 56.41, 41.68, 37.97, 35.25, 31.33, 26.41, 25.07, 15.95. LC-MS (ESI); m/z [M+H]$^+$: Calcd. for C$_{46}$H$_{48}$F$_2$N$_7$O$_6$S, 864.3354. Found 864.3437.

Example Synthesis of Compound 303: (2S,4R)-1-((S)-2-(4-(4-(3-(2,6-difluorobenzoyl)-1H-pyrrolo[2,3-b]pyridin-5-yl)phenoxy)butanamido)-3,3-dimethylbutanoyl)-4-hydroxy-N-(4-(4-methylthiazol-5-yl)benzyl)pyrrolidine-2-carboxamide

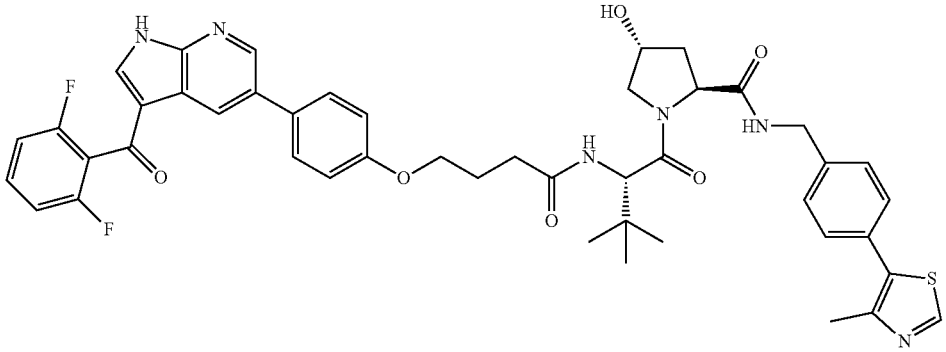 [SMILES: Cc1ncsc1-c1ccc(CNC(=O)[C@@H]2C[C@@H](O)CN2C(=O)[C@@H](NC(=O)CCCOc2ccc(-c3cnc4[nH]cc(C(=O)c5c(F)cccc5F)c4c3)cc2)C(C)(C)C)cc1]

To a solution of 4-(4-(3-(2,6-difluorobenzoyl)-1H-pyrrolo-[2,3-b]pyridin-5-yl)phenoxy)butanoic acid (19.4 mg, 0.04 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (20.76 mg, 0.04 mmol) in DMF(2 ml) was added TEA (0.1 ml, 0.72 mmol) and PyBOP (25.45 mg, 0.05 mmol) at room temperature. The reaction mixture was stirred for 4 hours at the same temperature. TLC (DCM:MeOH:NH$_4$OH, 90:9:1) shows no starting materials. The DMF was removed under high vacuum. Crude product was filtered over a silica-carbonate cartridge (1 g) using DCM:MeOH (9:1) as a eluent. Filtrate was evaporated under vacuum and crude product was purified by PTLC (DCM:MeOH:NH$_4$OH, 90:9:1), to give 29 mg of product (77% yield). $^1$H NMR (500 MHz, DMSO-d6) δ 12.89 (bs, 1H), 8.97 (s, 1H), 8.65 (d, J=1.9 Hz, 1H), 8.62-8.54 (m, 2H), 8.13 (s, 1H), 8.00 (d, J=9.3 Hz, 1H), 7.75-7.55 (m, 3H), 7.43 (d, J=8.1 Hz, 3H), 7.38 (d, J=8.1 Hz, 2H), 7.28 (t, J=7.9 Hz, 2H), 7.07 (d, J=8.6 Hz, 2H), 5.15 (d, J=3.3 Hz, 1H), 4.59 (d, J=9.3 Hz, 1H), 4.49-4.40 (m, 2H), 4.39-4.33 (m, 1H), 4.23 (dd, J=15.9, 5.4 Hz, 1H), 4.09-3.97 (m, 2H), 3.77-3.61 (m, 2H), 1H NMR (500 MHz, DMSO-d6) δ 2.48-2.31 (m, 2H), 2.44 (s, 3H), 2.11-1.86 (m, 4H), 0.96 (s, 9H). $^{13}$C NMR (151 MHz, dmso) δ 181.30, 171.97, 171.61, 169.68, 158.80 (dd, J=247.2, 7.9 Hz), 158.33, 151.44, 148.52, 147.72, 143.70, 139.51, 138.38, 132.14 (t, J=9.9 Hz), 131.30, 131.17, 130.44, 129.64, 128.64, 128.27, 127.43, 126.48, 117.76 (t, J=23.3 Hz), 117.54, 115.78, 115.18, 112.29 (dd, J=21.0, 4.2 Hz), 68.92, 67.13, 58.74, 56.48, 56.42, 41.67, 37.98, 35.26, 31.32, 26.41, 25.06, 15.96. LC-MS (ESI); m/z [M+H]$^+$: Calcd. for C$_{46}$H$_{47}$F$_2$N$_6$O$_6$S, 849.3245. Found 849.3378.

Example Synthesis of Compound 304: (2S,4R)-1-((S)-2-(4-(4-(3-(2,6-difluoro-3-(propylsulfonamido)benzoyl)-1H-pyrrolo[2,3-b]pyridin-5-yl)piperazin-1-yl)butanamido)-3,3-dimethylbutanoyl)-4-hydroxy-N-(4-(4-methylthiazol-5-yl)benzyl)pyrrolidine-2-carboxamide

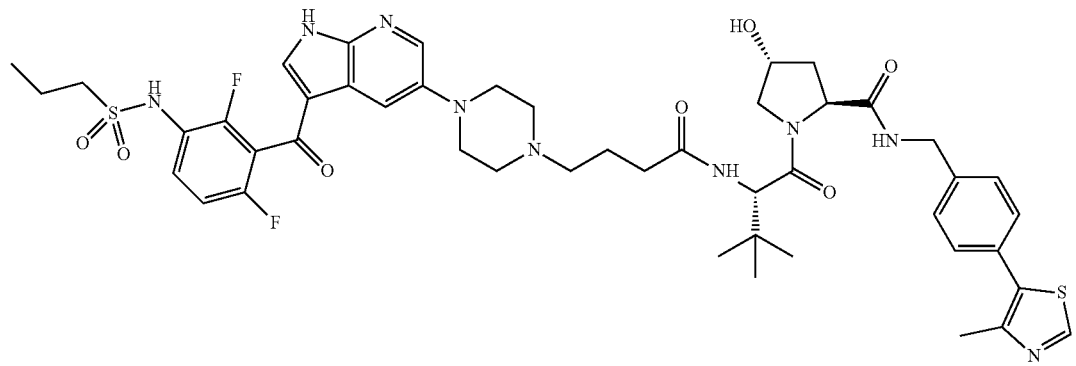 [SMILES: CCCS(=O)(=O)Nc1ccc(F)c(C(=O)c2c[nH]c3ncc(N4CCN(CCCC(=O)N[C@H](C(=O)N5C[C@H](O)C[C@H]5C(=O)NCc5ccc(-c6scnc6C)cc5)C(C)(C)C)CC4)cc23)c1F]

To a solution of 4-[4-[3-[2,6-difluoro-3-(propylsulfonyl-amino)benzoyl]-1H-pyrrolo[2,3-b]pyridin-5-yl]piperazin-1-yl]butanoic acid (7.9 mg, 0.01 mmol) and (2S,4R)-1-[(2S)-2-amino-3,3-dimethyl-butanoyl]-4-hydroxy-N-[[4-(4-methylthiazo-1-5-yl)phenyl]methyl]pyrrolidine-2-carboxamide; hydrochloride (7.38 mg, 0.02 mmol) in DMF (1 ml) was added TEA (0.1 ml, 0.72 mmol) and PyBOP (8.23 mg, 0.02 mmol) at room temperature. The reaction mixture was stirred for 12 hours (overnight) at the same temperature. TLC (DCM:MeOH:NH$_4$OH, 90:9:1) shows no starting materials. The reaction mixture was evaporated to dryness. Crude product was filtered over a silica-carbonate cartridge (1 g) using DCM:MeOH (9:1) as eluent (washed a few times, product has high affinity for the stationary phase). Filtrate was evaporated under vacuum and crude product was purified by PTLC (DCM:MeOH, 9:1) to give 7.2 mg of product (52% yield). $^1$H NMR (500 MHz, DMSO-d6) δ 12.66 (bs, 1H), 9.73 (bs, 1H), 8.96 (s, 1H), 8.61-8.50 (m, 1H), 8.25 (s, 1H), 8.00 (s, 1H), 7.93 (bs, 1H), 7.88 (d, J=9.1 Hz, 1H), 7.63-7.49 (m, 1H), 7.40 (dd, 4H), 7.25 (t, J=8.7 Hz, 1H), 5.14 (s, 1H), 4.56 (d, J=9.1 Hz, 1H), 4.46-4.34 (m, 3H), 4.22 (dd, J=15.8, 4.7 Hz, 1H), 3.75-3.60 (m, 2H), 3.23-3.14 (m, 4H), 3.13-3.08 (m, 2H), 2.65-2.53 (m, 4H), 2.43 (s, 3H), 2.38-2.31 (m, 2H), 2.31-2.25 (m, 1H), 2.24-2.16 (m, 1H), 2.07-1.99 (m, 1H), 1.95-1.87 (m, 1H), 1.72 (dq, J=16.3, 10.5, 8.9 Hz, 4H), 0.95 (t, J=5.3 Hz, 3H), 0.95 (s, 9H). $^{13}$C NMR (151 MHz, DMSO-d6) δ 180.77, 172.43, 172.39, 170.12, 156.38 (dd, J=246.2, 7.1 Hz), 152.75 (dd, J=249.8, 9.0 Hz), 151.87, 148.13, 145.23, 144.35, 139.92, 138.09, 137.78, 131.59, 130.05, 129.21-128.76 (m), 127.84, 122.32 (d, J=13.1 Hz), 119.83-118.25 (m), 118.03, 115.53, 114.96, 112.68 (d, J=22.7 Hz), 69.30, 59.13, 57.62, 56.79, 55.33, 53.88, 53.06, 50.11, 42.07, 38.38, 35.68, 33.27, 26.83, 23.09, 17.26, 16.37, 13.04. LC-MS (ESI); m/z [M+H]$^+$: Calcd. for $C_{47}H_{58}F_2N_9O_7S_2$, 962.3868. Found 962.3986.

Example Synthesis of Compound 305: (2S,4R)-1-((S)-2-(4-(4-(3-benzoyl-1H-pyrrolo[2,3-b]pyridin-5-yl)phenoxy)butanamido)-3,3-dimethylbutanoyl)-4-hydroxy-N-(4-(4-methylthiazol-5-yl)benzyl)pyrrolidine-2-carboxamide PyBOP (37.88 mg, 0.07 mmol) at room temperature. The reaction mixture was stirred for 12 hours (overnight) at the same temperature. TLC (DCM:MeOH:NH$_4$OH, 90:9:1) shows no starting materials. The DMF was removed under high vacuum. Crude product was filtered over a silica-carbonate cartridge (1 g) using DCM:MeOH (9:1) as a eluent. Filtrate was evaporated under vacuum and crude product was purified by PTLC (MeOH:DCM, 9:1), to give 31 mg of product (58% yield). $^1$H NMR (400 MHz, DMSO-d6) δ 12.70 (s, 1H), 8.97 (s, 1H), 8.68 (d, J=2.2 Hz, 1H), 8.62 (d, J=2.3 Hz, 1H), 8.60-8.51 (m, 1H), 8.12 (s, 1H), 8.00 (d, J=9.3 Hz, 1H), 7.90-7.77 (m, 1H), 7.72-7.51 (m, 5H), 7.48-7.29 (m, 4H), 7.07 (d, J=8.7 Hz, 2H), 5.15 (d, J=3.5 Hz, 1H), 4.59 (d, J=9.3 Hz, 1H), 4.50-4.32 (m, 3H), 4.22 (dd, J=15.9, 5.4 Hz, 1H), 4.03 (td, J=6.5, 2.6 Hz, 2H), 3.80-3.60 (m, 2H), 2.44 (s, 3H), 2.48-2.28 (m, 5H), 2.13-1.84 (m, 4H), 0.96 (s, 9H). $^{13}$C NMR (101 MHz, dmso) δ 189.87, 172.00, 171.63, 169.69, 158.23, 151.48, 148.29, 147.73, 143.29, 139.64, 139.53, 136.54, 131.52, 131.19, 130.74, 129.65, 128.66, 128.58, 128.55, 128.21, 127.44, 127.05, 118.81, 115.19, 113.74, 68.93, 67.13, 58.75, 56.47, 48.64, 41.68, 38.01, 35.29, 31.33, 26.43, 25.08, 15.99. LC-MS (ESI); m/z [M+H]$^+$: Calcd. for $C_{46}H_{49}N_6O_6S$, 813.3434. Found 813.3478.

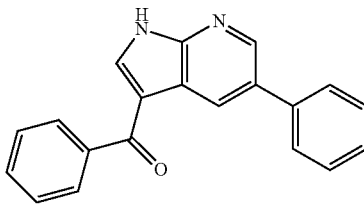
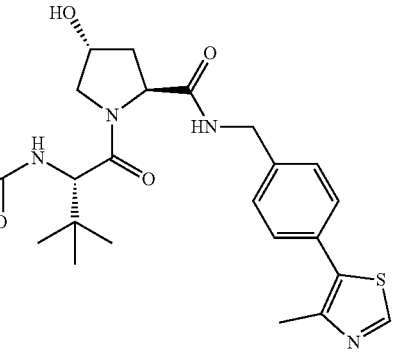

To a solution of 4-[4-(3-benzoyl-1H-pyrrolo[2,3-b]pyridin-5-yl)-phenoxy]butanoic acid (26.5 mg, 0.07 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (30.91 mg, 0.07 mmol) in DMF(2 ml) was added TEA (0.2 ml, 1.43 mmol) and Example Synthesis of Compound 306: (2S,4R)-1-((S)-2-(2-(2-(4-(3-(2,6-difluoro-3-(propylsulfonamido)benzoyl)-1H-pyrrolo[2,3-b]pyridin-5-yl)piperazin-1-yl)ethoxy)acetamido)-3,3-dimethylbutanoyl)-4-hydroxy-N-(4-(4-methylthiazol-5-yl)benzyl)pyrrolidine-2-carboxamide

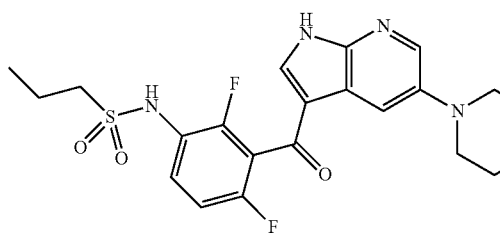
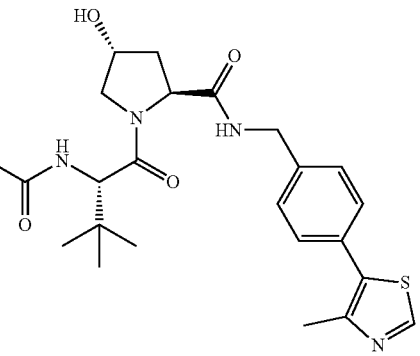

To a solution of 2-[2-[4-[3-[2,6-difluoro-3-(propyl-sulfonylamino)benzoyl]-1H-pyrrolo[2,3-b]pyridin-5-yl]piperazin-1-yl]ethoxy]acetic acid (7.9 mg, 0.01 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide; hydrochloride (7.18 mg, 0.02 mmol) in DMF (1 ml) was added TEA (0.1 ml, 0.72 mmol) and PyBOP (8 mg, 0.02 mmol) at room temperature. The reaction mixture was stirred for 12 hours (overnight) at the same temperature. TLC (DCM:MeOH:NH$_4$OH, 90:9:1) shows no starting materials. The reaction mixture was evaporated to dryness under high vacuum. Crude product was evaporated under vacuum and crude product was purified by PTLC (DCM:MeOH:NH$_4$OH, 90:9:1) to give 8.1 mg of product (59% yield). $^1$H NMR (500 MHz, DMSO-d6) δ 12.66 (bs, 1H), 9.72 (bs, 1H), 8.93 (s, 1H), 8.59 (bs, 1H), 8.22 (s, 1H), 7.99 (s, 1H), 7.89 (bs, 1H), 7.56 (dh, J=9.1, 3.4, 2.9 Hz, 1H), 7.51-7.31 (m, 5H), 7.25 (t, J=8.6 Hz, 1H), 5.17 (s, 1H), 4.57 (dd, J=9.7, 2.4 Hz, 1H), 4.50-4.33 (m, 3H), 4.28-4.19 (m, 1H), 4.07-3.92 (m, 2H), 3.65 (d, J=15.4 Hz, 4H), 3.22-3.05 (m, 6H), 2.64 (d, J=21.6 Hz, 6H), 2.42 (s, 3H), 2.11-2.03 (m, 1H), 1.91 (dd, J=13.3, 5.8 Hz, 1H), 1.80-1.67 (m, 2H), 0.96 (s/t overlapping, 12H). $^{13}$C NMR (151 MHz, DMSO-d6) δ 180.38, 171.80, 169.18, 168.58, 156.01 (dd, J=246.2, 6.8 Hz), 152.34 (dd, J=249.1, 8.7 Hz), 151.39, 147.73, 144.79, 143.97, 139.43, 137.73, 137.38, 131.16, 129.70, 128.68, 128.60 (d), 127.47, 121.93 (dd, J=13.8, 3.7 Hz), 118.89-118.05 (m), 117.64, 115.15, 114.62, 112.29 (dd, J=22.2, 3.2 Hz), 69.65, 68.94, 68.76, 58.81, 57.13, 56.64, 55.73, 53.49, 53.09, 49.72, 41.71, 37.93, 35.87, 26.24, 16.88, 15.95, 12.65. LC-MS (ESI); m/z [M+H]$^+$: Calcd. for C$_{47}$H$_{58}$F$_2$N$_9$O$_8$S$_2$, 978.3817. Found 978.3933.

Protein Level Control

This description also provides methods for the control of protein levels with a cell. This is based on the use of compounds as described herein, which are known to interact with a specific target protein such that degradation of a target protein in vivo will result in the control of the amount of protein in a biological system, prerferably to a particular therapeutic benefit.

The following examples are used to assist in describing the present disclosure, but should not be seen as limiting the present disclosure in any way.

The following examples are used to assist in describing the disclosure, but should not be seen as limiting the disclosure in any way.

EXAMPLES

Assays and Degradation Data

Protocol for a cellular assay of target protein degradation (A375 cells). A375 cells were cultured in ATCC DMEM+10% FBS in 12 well plates, and treated with indicated compound from Tables 1-41 or 0.1% DMSO vehicle control for 16 hours. Cells were harvested in Cell Signaling lysis buffer (Cat #9803) with the addition of Roche protease inhibitor tablets (Cat #11873580001), and lysates clarified by microcentrifugation. Proteins were separated by SDS-PAGE, and transferred onto nitrocellulose membranes using an Invitrogen iBlot system. Immunoblotting was performed for BRAF (Santa Cruz Cat #9002), CRAF (BD Cat #610151), and pErk (Cell Signaling Cat #9106). GAPDH (Cat #) was used as a loading control. Quantification was carried out using the BioRad Image Lab 5 software.

Protocol for an In-Cell Western cellular assay of target protein degradation (A375 cells). A375 cells were cultured in ATCC DMEM+10% FBS in 96-well plates, and treated with indicated compounds from Tables-43 or 0.1% DMSO vehicle control for 72 hours. Cells were washed with PBS 1×, and affixed to plate using 4% PFA in phosphate buffered saline for 15 minutes; washed 1× and permeabilized using 0.1% Triton-X-100 in PBS for 5 minutes; washed 1× and blocked with LICOR blocker (Cat. #927-50000) for 1 hour. Cells were then incubated with B-Raf antibody (Santa Cruz Cat #9002) and tubulin antibody (Sigma # T6074) in LICOR blocker for 18 hours. Cells were washed 3× prior to adding secondary antibodies (LICOR cat #926-32210 and 926-68071) and incubated for 1 hr. Cells were washed 3× and imaged using LICOR Odyssey Software.

Figure 2:
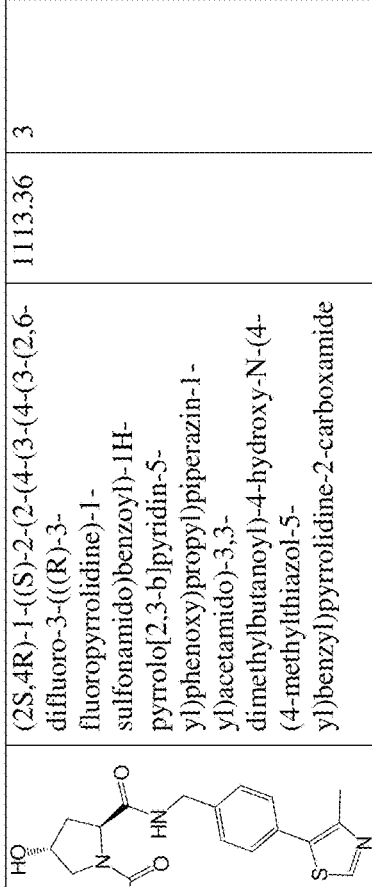
FIG. 2. Table 42. Exemplary protein targeting moieties and compounds of the present disclosure.
Figure 2:
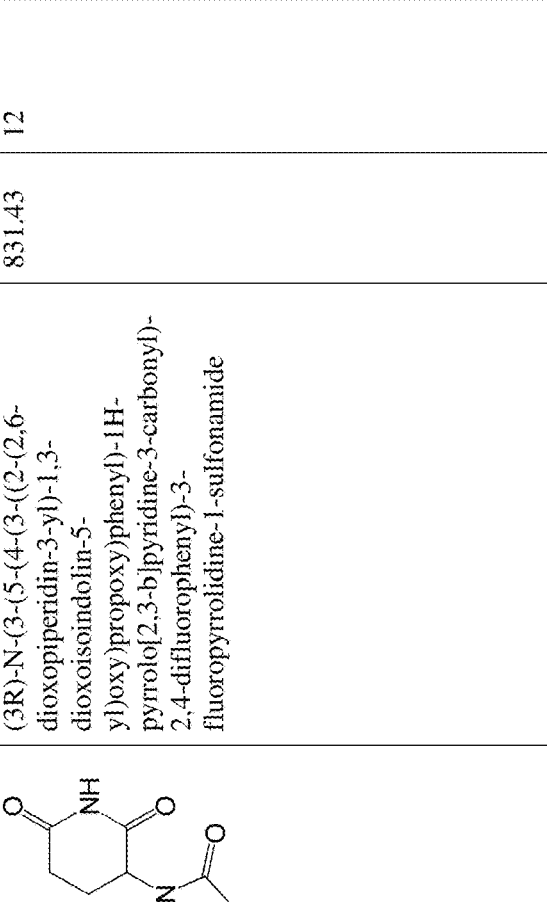
Figure 2:
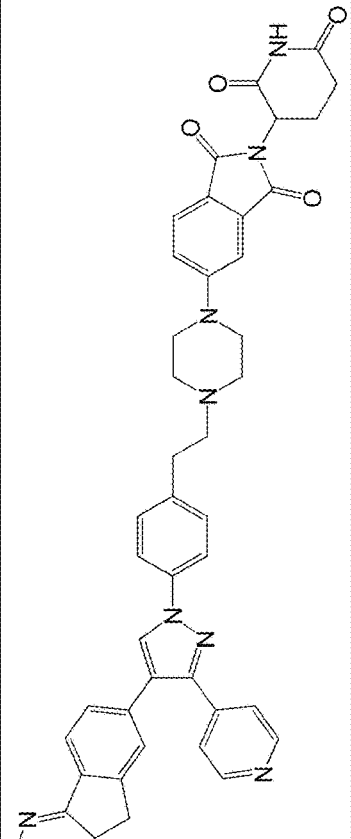
Figure 2:
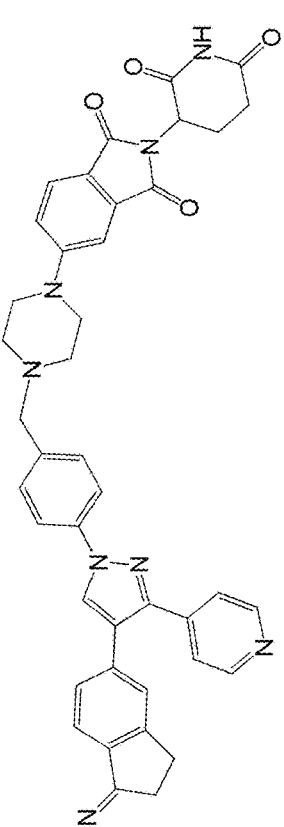
Figure 2:
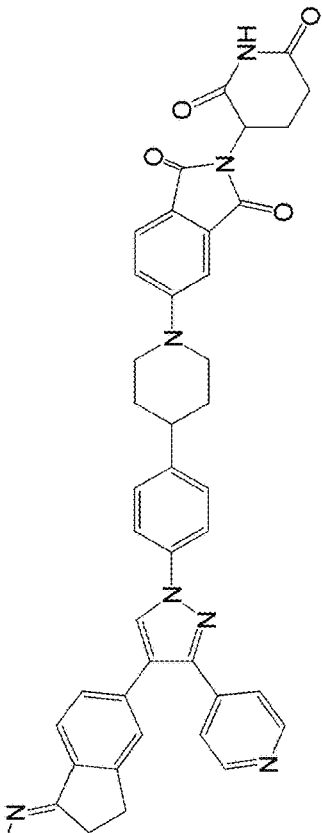
Figure 2:
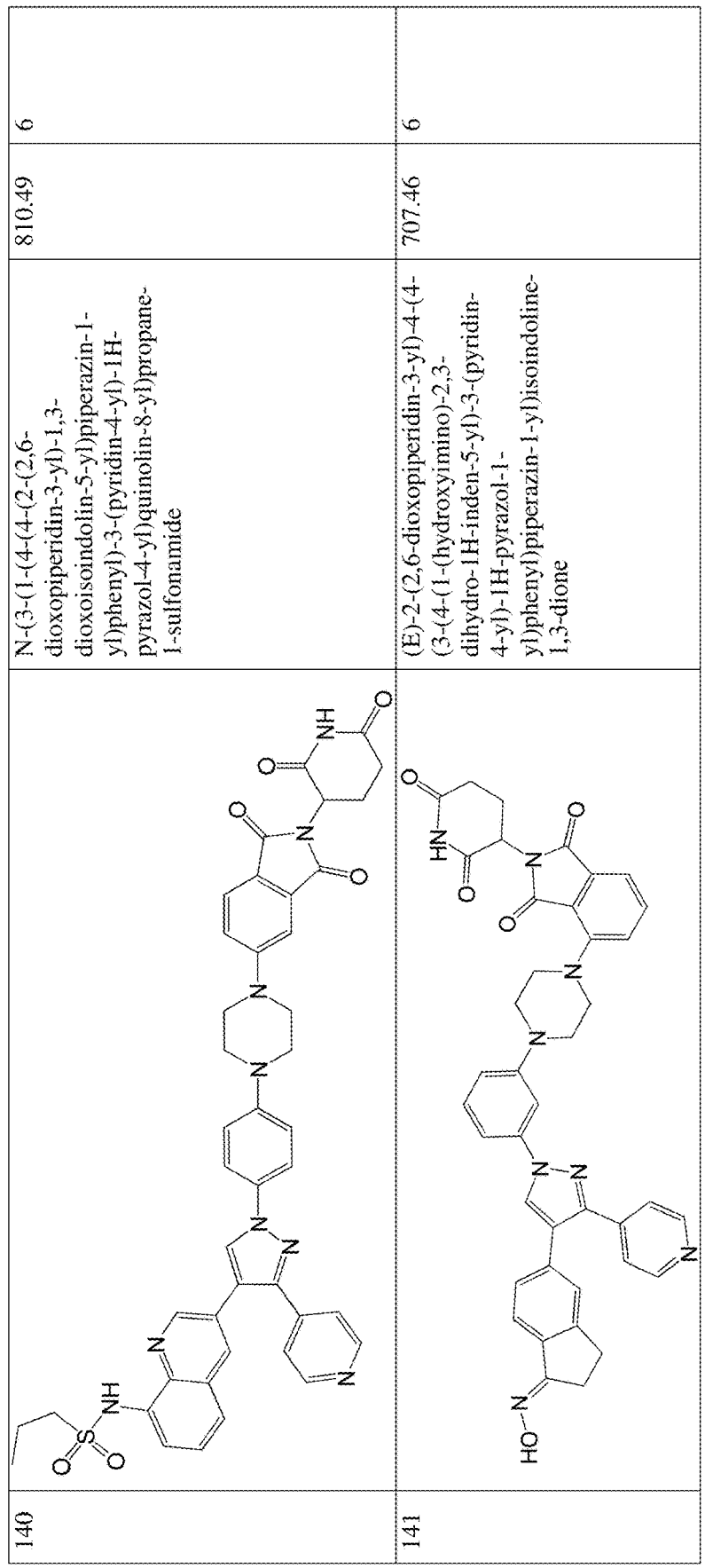
Figure 2:
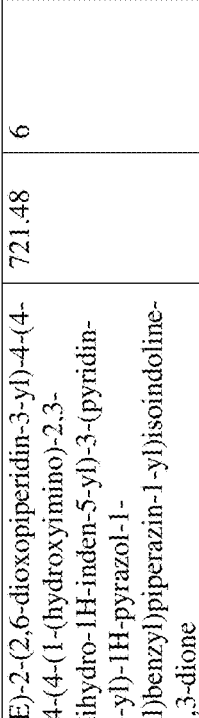
Figure 2:
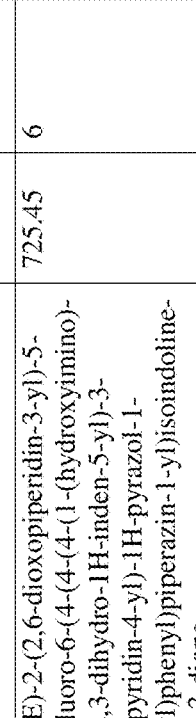
Figure 2:
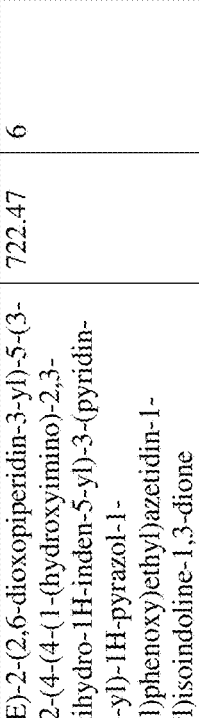
Figure 2:
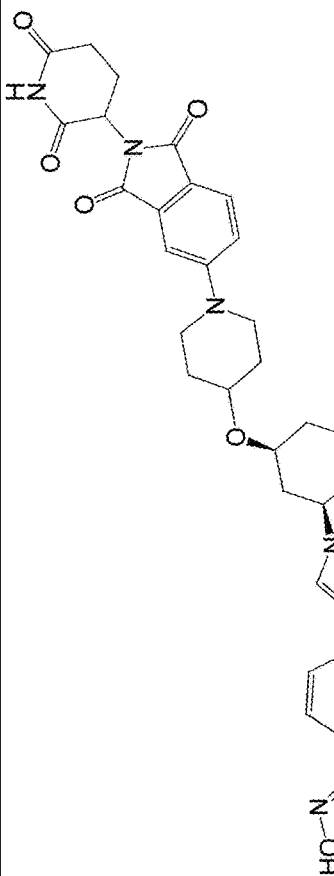
Figure 2:
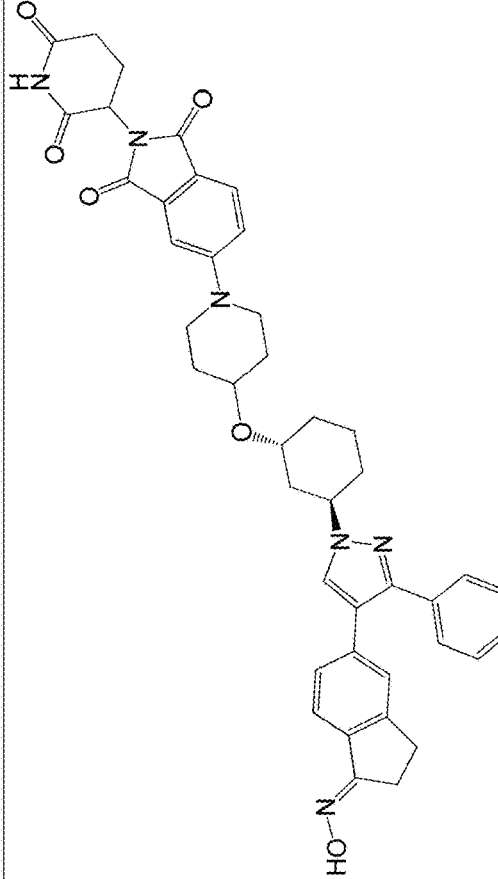
Figure 2:
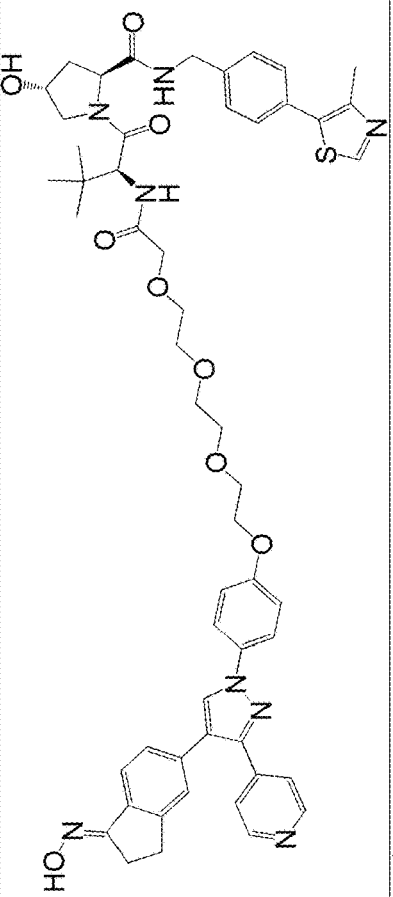
Figure 2:
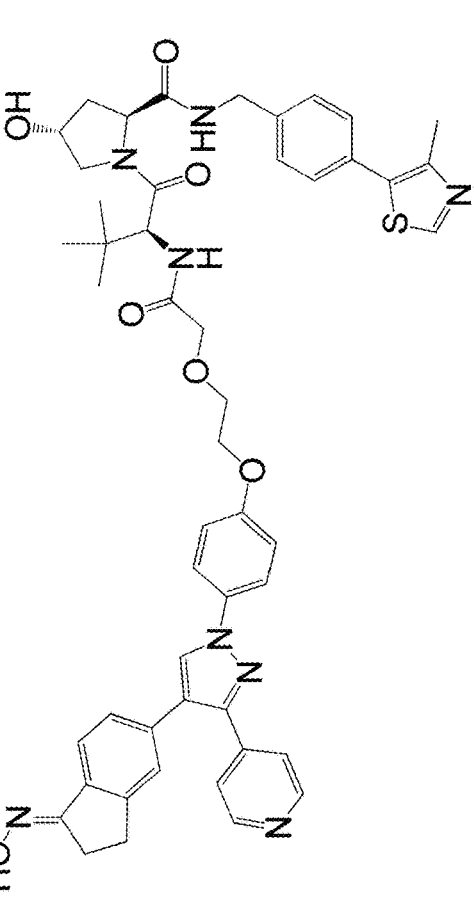
Figure 2:
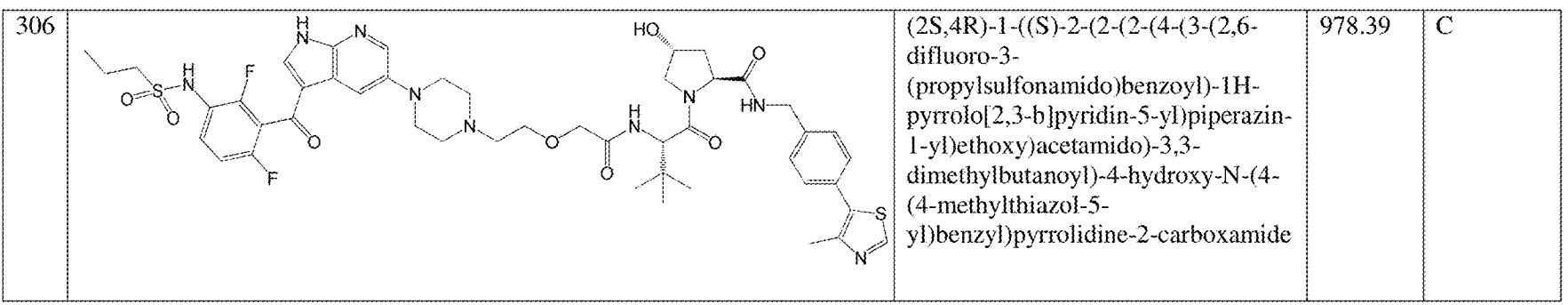

The following PROTACs shown in Tables 1-41 and 42 (FIG. 2) are examples of the bifunctional compounds that are described in the claims of this application. Some of them have been tested to see if they would exhibit the degradation activity of BRAF protein in cells, and their results are given in the columns of DC$_{50}$ and D$_{max}$ in these tables. Herein, DC$_{50}$ is the compound concentration at which the BRAF concentration level reaches a midpoint between the maximum level and the minimum level in the dose-response curve measuring the BRAF protein concentration in a cell as a function of the compound concentration added to the medium incubating the cells with the compound, and D$_{max}$ is the maximum protein degradation level that can be achieved by varying the compound concentration. Many compounds in these tables are not given any values or ranges of DC$_{50}$ and D$_{max}$ because either they have not been tested or synthesized or they are prophetic examples.

TABLE 1

Protacs composed of a type-I Raf ligand and a cereblon ligand with 5-position linkage with the following chemical structure

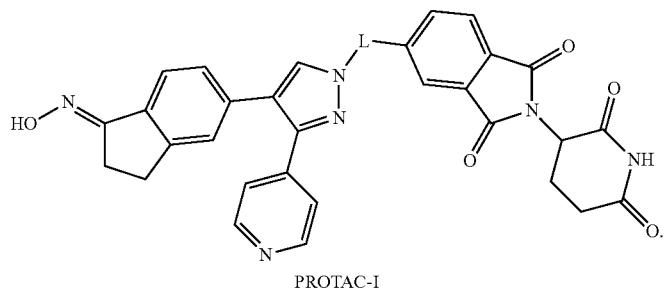

PROTAC-I

| PROTAC-I Compound | L | Mass | DC$_{50}$ (μM) | D$_{max}$ (%) |
|---|---|---|---|---|
| PROTAC-I-1 | —C$_6$H$_4$—O—CH$_2$CH$_2$—O— | 682 | <1 | ≥10 |
| PROTAC-I-2 | —C$_6$H$_4$—O—(CH$_2$CH$_2$O)$_3$— | 770 | <1 | ≥10 |
| PROTAC-I-3 | —C$_6$H$_4$—O—CH$_2$CH$_2$—O—CH$_2$CH$_2$—O— | 726 | <1 | ≥10 |
| PROTAC-I-4 | —C$_6$H$_4$—O—(CH$_2$CH$_2$O)$_4$— | 814 | <1 | ≥10 |
| PROTAC-I-5 | —C$_6$H$_4$—O—(CH$_2$CH$_2$O)$_5$— | 858 | <1 | ≥10 |
| PROTAC-I-6 | —CH$_2$CH$_2$CH$_2$—O—CH$_2$CH$_2$—O— | 648 | | |
| PROTAC-I-7 | —CH$_2$CH$_2$CH$_2$—(OCH$_2$CH$_2$)$_2$—O— | 692 | >1 | <10 |
| PROTAC-I-8 | —CH$_2$CH$_2$CH$_2$—(OCH$_2$CH$_2$)$_3$—O— | 735 | | |
| PROTAC-I-9 | —CH$_2$CH$_2$CH$_2$—(OCH$_2$CH$_2$)$_4$—O— | 779 | >1 | <10 |
| PROTAC-I-10 | —CH$_2$CH$_2$CH$_2$—(OCH$_2$CH$_2$)$_5$—O— | 823 | >1 | <10 |
| PROTAC-I-11 | —(pyridyl)—O—CH$_2$CH$_2$— | 666 | | |
| PROTAC-I-12 | —C$_6$H$_4$—CH$_2$CH$_2$—O— | 666 | | |
| PROTAC-I-13 | —C$_6$H$_4$—CH$_2$—O—CH$_2$— | 666 | | |

TABLE 1-continued
Protacs composed of a type-I Raf ligand and a cereblon ligand with 5-position linkage with the following chemical structure
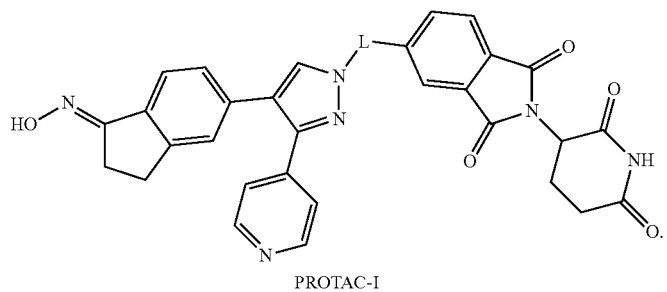
PROTAC-I
| PROTAC-I Compound | L | Mass | DC$_{50}$ (μM) | D$_{max}$ (%) |
|---|---|---|---|---|
| PROTAC-I-14 | | 652 | | |
| PROTAC-I-15 | | 652 | | |
| PROTAC-I-16 | | 636 | | |
| PROTAC-I-17 | | 696 | | |
| PROTAC-I-18 | | 696 | | |
| PROTAC-I-19 | | 696 | | |
| PROTAC-I-20 | | 710 | | |
| PROTAC-I-21 | | 710 | | |
| PROTAC-I-22 | | 710 | | |
| PROTAC-I-23 | | 710 | | |
| PROTAC-I-24 | | 710 | | |
| PROTAC-I-25 | | 710 | | |

TABLE 1-continued
Protacs composed of a type-I Raf ligand and a cereblon ligand with 5-position linkage with the following chemical structure
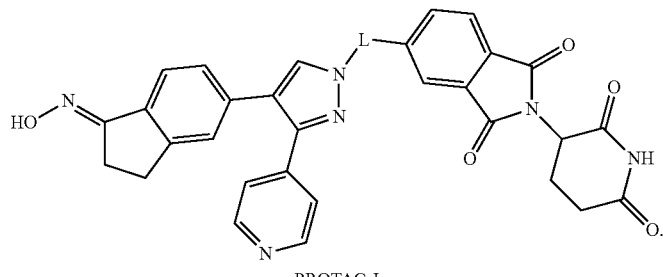
PROTAC-I
| PROTAC-I Compound | L | Mass | DC$_{50}$ (μM) | D$_{max}$ (%) |
|---|---|---|---|---|
| PROTAC-I-26 | | 638 | | |
| PROTAC-I-27 | | 650 | | |
| PROTAC-I-28 | | 664 | | |
| PROTAC-I-29 | | 680 | | |
| PROTAC-I-30 | | 680 | | |
| PROTAC-I-31 | | 678 | | |
| PROTAC-I-32 | | 694 | | |
| PROTAC-I-33 | | 694 | | |
| PROTAC-I-34 | | 694 | | |
| PROTAC-I-35 | | 694 | | |
| PROTAC-I-36 | | 694 | | |
| PROTAC-I-37 | | 692 | | |

TABLE 1-continued
Protacs composed of a type-I Raf ligand and a cereblon ligand with 5-position linkage with the following chemical structure
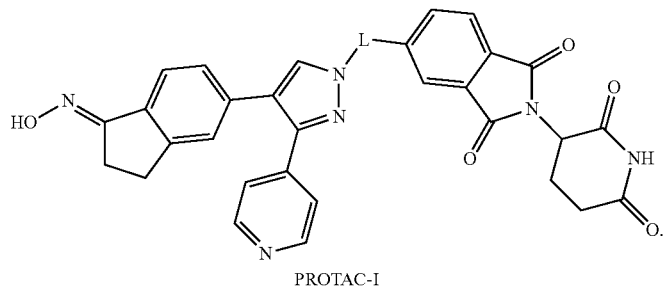
PROTAC-I
| PROTAC-I Compound | L | Mass | DC$_{50}$ (μM) | D$_{max}$ (%) |
|---|---|---|---|---|
| PROTAC-I-38 | | 740 | | |
| PROTAC-I-39 | | 740 | | |
| PROTAC-I-40 | | 738 | | |
| PROTAC-I-41 | | 754 | | |
| PROTAC-I-42 | | 754 | | |
| PROTAC-I-43 | | 754 | | |
| PROTAC-I-44 | | 673 | | |
| PROTAC-I-45 | | 687 | | |
| PROTAC-I-46 | | 701 | | |
| PROTAC-I-47 | | 715 | | |
| PROTAC-I-48 | | 717 | | |
| PROTAC-I-49 | | 731 | | |

TABLE 1-continued

Protacs composed of a type-I Raf ligand and a cereblon ligand with 5-position linkage with the following chemical structure

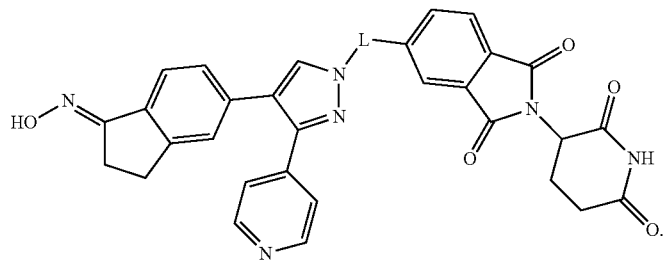

PROTAC-I

| PROTAC-I Compound | L | Mass | $DC_{50}$ (μM) | $D_{max}$ (%) |
|---|---|---|---|---|
| PROTAC-I-50 | ----piperidine-N-CH$_2$CH$_2$-O-CH$_2$CH$_2$CH$_2$CH$_2$-O---- | 745 | | |
| PROTAC-I-51 | ----piperidine-N-CH$_2$CH$_2$-O-CH$_2$CH$_2$CH$_2$CH$_2$CH$_2$-O---- | 759 | | |
| PROTAC-I-52 | ----piperidine-N-CH$_2$CH$_2$-O-CH$_2$CH$_2$CH$_2$-O-CH$_2$CH$_2$-O---- | 775 | | |
| PROTAC-I-53 | ----C$_6$H$_4$-O-CH$_2$CH$_2$-N(piperazine)-N-CH$_3$ | 750 | | |
| PROTAC-I-54 | ----C$_6$H$_4$-O-CH$_2$CH$_2$-N(piperidine)-CH$_3$ | 749 | | |
| PROTAC-I-55 | ----C$_6$H$_4$-O-CH$_2$CH$_2$CH$_2$-N(piperazine)-N---- | 764 | | |
| PROTAC-I-56 | ----C$_6$H$_4$-O-CH$_2$CH$_2$CH$_2$-N(piperazine)-N-CH$_3$ | 778 | | |
| PROTAC-I-57 | ----C$_6$H$_4$-O-CH$_2$CH$_2$CH$_2$CH$_2$-N(piperazine)-N---- | 792 | | |
| PROTAC-I-58 | ----C$_6$H$_4$-O-CH$_2$CH$_2$-O-CH$_2$CH$_2$-N(piperazine)-N---- | 794 | | |

TABLE 1-continued

Protacs composed of a type-I Raf ligand and a cereblon ligand with 5-position linkage with the following chemical structure

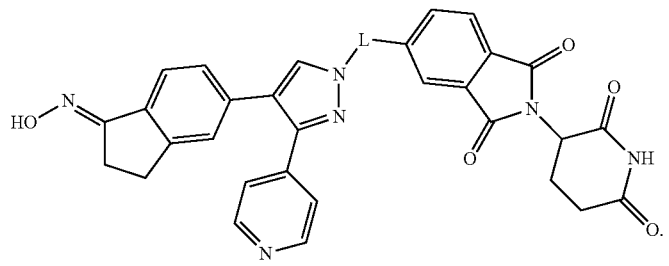

PROTAC-I

| PROTAC-I Compound | L | Mass | DC$_{50}$ (μM) | D$_{max}$ (%) |
|---|---|---|---|---|
| PROTAC-I-59 | ![structure] | 793 | | |
| PROTAC-I-60 | ![structure] | 741 | | |
| PROTAC-I-61 | ![structure] | 740 | | |
| PROTAC-I-62 | ![structure] | 740 | | |
| PROTAC-I-63 | ![structure] | 726 | | |
| PROTAC-I-64 | ![structure] | 712 | | |
| PROTAC-I-65 | ![structure] | 622 | | |
| PROTAC-I-66 | ![structure] | 632 | | |
| PROTAC-I-67 | ![structure] | 618 | | |
| PROTAC-I-68 | ![structure] | 604 | | |
| PROTAC-I-69 | ![structure] | 602 | | |

TABLE 1-continued

Protacs composed of a type-I Raf ligand and a cereblon ligand with 5-position linkage with the following chemical structure

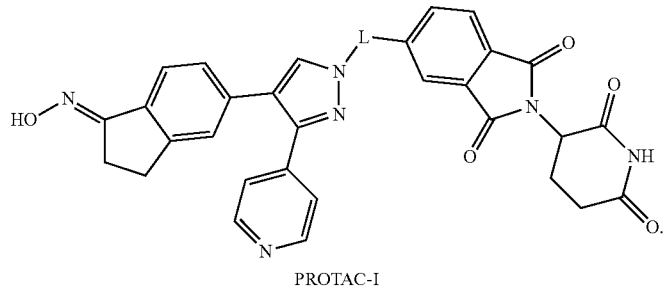

PROTAC-I

| PROTAC-I Compound | L | Mass | $DC_{50}$ (μM) | $D_{max}$ (%) |
|---|---|---|---|---|
| PROTAC-I-70 | | 588 | | |
| PROTAC-I-71 | | 590 | | |
| PROTAC-I-72 | | 706 | | |
| PROTAC-I-73 | | 794 | | |
| PROTAC-I-74 | | 786 | | |

TABLE 2

Protacs composed of a type-I Raf ligand and a cereblon ligand with 5-position linkage with the following chemical structure (PROTAC-II)

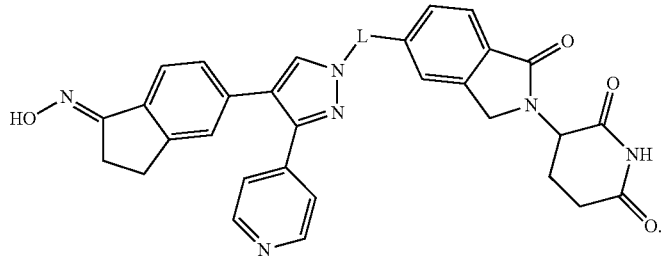

| PROTAC-II Compound | L | Mass | $DC_{50}$ (μM) | $D_{max}$ (%) |
|---|---|---|---|---|
| PROTAC-II-1 | | 668 | | |
| PROTAC-II-2 | | 756 | | |

TABLE 2-continued
Protacs composed of a type-I Raf ligand and a cereblon ligand with 5-position linkage
with the following chemical structure
(PROTAC-II)
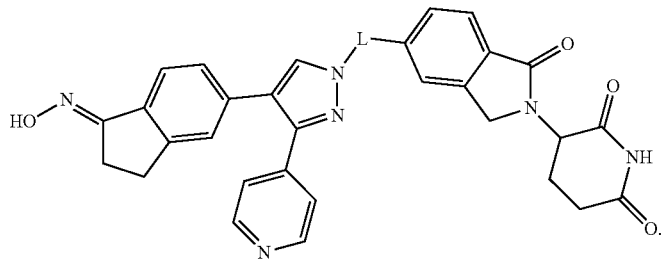
| PROTAC-II Compound | L | Mass | $DC_{50}$ (μM) | $D_{max}$ (%) |
|---|---|---|---|---|
| PROTAC-II-3 | | 712 | | |
| PROTAC-II-4 | | 800 | | |
| PROTAC-II-5 | | | | |
| PROTAC-II-6 | | 634 | | |
| PROTAC-II-7 | | 678 | | |
| PROTAC-II-8 | | 722 | | |
| PROTAC-II-9 | | 766 | | |
| PROTAC-II-10 | | 810 | | |
| PROTAC-II-11 | | 652 | | |
| PROTAC-II-12 | | 652 | | |
| PROTAC-II-13 | | 652 | | |
| PROTAC-II-14 | | 638 | | |
| PROTAC-II-15 | | 638 | | |

TABLE 2-continued
Protacs composed of a type-I Raf ligand and a cereblon ligand with 5-position linkage
with the following chemical structure
(PROTAC-II)
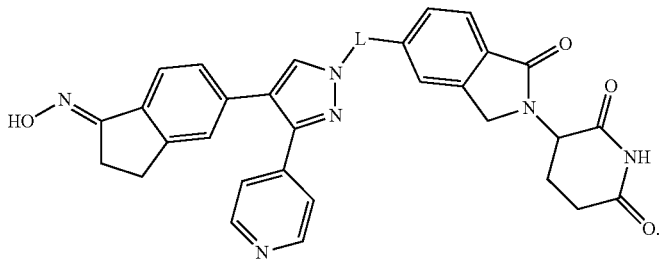
| PROTAC-II Compound | L | Mass | DC$_{50}$ (μM) | D$_{max}$ (%) |
|---|---|---|---|---|
| PROTAC-II-16 | | 622 | | |
| PROTAC-II-17 | | 682 | | |
| PROTAC-II-18 | | 682 | | |
| PROTAC-II-19 | | 682 | | |
| PROTAC-II-20 | | 696 | | |
| PROTAC-II-21 | | 696 | | |
| PROTAC-II-22 | | 696 | | |
| PROTAC-II-23 | | 696 | | |
| PROTAC-II-24 | | 696 | | |
| PROTAC-II-25 | | 696 | | |
| PROTAC-II-26 | | 624 | | |
| PROTAC-II-27 | | 636 | | |

TABLE 2-continued
Protacs composed of a type-I Raf ligand and a cereblon ligand with 5-position linkage
with the following chemical structure
(PROTAC-II)
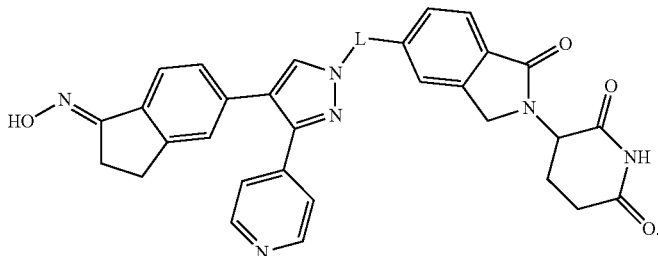
| PROTAC-II Compound | L | Mass | DC$_{50}$ (μM) | D$_{max}$ (%) |
|---|---|---|---|---|
| PROTAC-II-28 | | 650 | | |
| PROTAC-II-29 | | 666 | | |
| PROTAC-II-30 | | 666 | | |
| PROTAC-II-31 | | 654 | | |
| PROTAC-II-32 | | 680 | | |
| PROTAC-II-33 | | 680 | | |
| PROTAC-II-34 | | 680 | | |
| PROTAC-II-35 | | 680 | | |
| PROTAC-II-36 | | 680 | | |
| PROTAC-II-37 | | 678 | | |
| PROTAC-II-38 | | 726 | | |
| PROTAC-II-39 | | 726 | | |

TABLE 2-continued
Protacs composed of a type-I Raf ligand and a cereblon ligand with 5-position linkage
with the following chemical structure
(PROTAC-II)
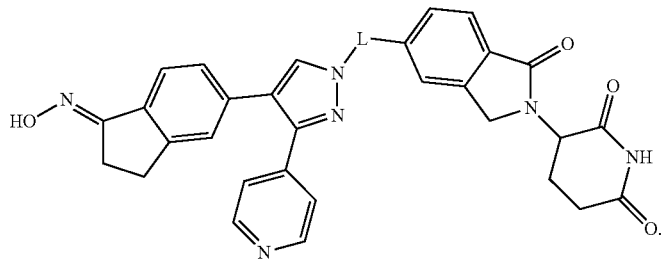
| PROTAC-II Compound | L | Mass | DC$_{50}$ (μM) | D$_{max}$ (%) |
|---|---|---|---|---|
| PROTAC-II-40 | 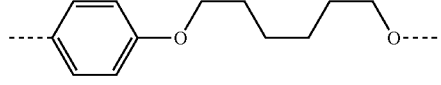 | 724 | | |
| PROTAC-II-41 | 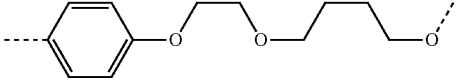 | 740 | | |
| PROTAC-II-42 | 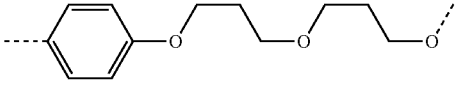 | 740 | | |
| PROTAC-II-43 | 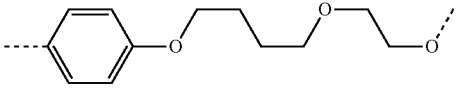 | 740 | | |
| PROTAC-II-44 | 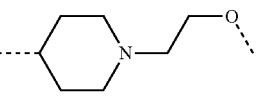 | 659 | | |
| PROTAC-II-45 | 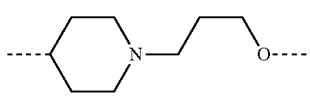 | 673 | | |
| PROTAC-II-46 | 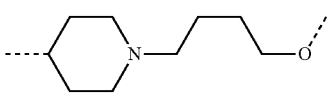 | 687 | | |
| PROTAC-II-47 | | | | |
| PROTAC-II-48 | 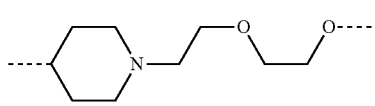 | | | |
| PROTAC-II-49 | 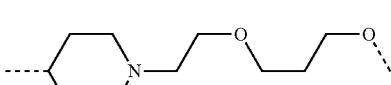 | 717 | | |
| PROTAC-II-50 | 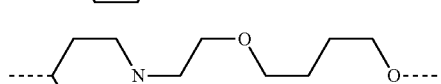 | 731 | | |
| PROTAC-II-51 | 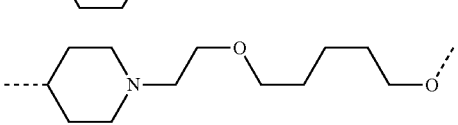 | 745 | | |

TABLE 2-continued
Protacs composed of a type-I Raf ligand and a cereblon ligand with 5-position linkage with the following chemical structure
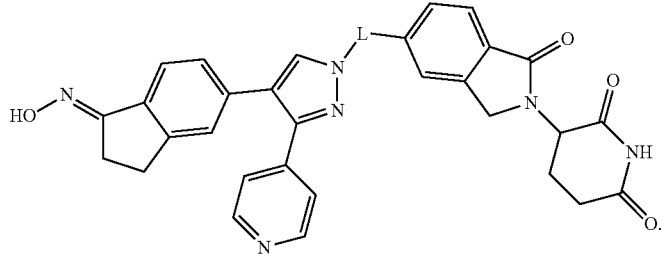
(PROTAC-II)
| PROTAC-II Compound | L | Mass | DC$_{50}$ (μM) | D$_{max}$ (%) |
|---|---|---|---|---|
| PROTAC-II-52 | | 761 | | |
| PROTAC-II-53 | | 736 | | |
| PROTAC-II-54 | | 735 | | |
| PROTAC-II-55 | | 750 | | |
| PROTAC-II-56 | | 764 | | |
| PROTAC-II-57 | | 778 | | |
| PROTAC-II-58 | | 780 | | |
| PROTAC-II-59 | | 779 | | |

TABLE 2-continued
Protacs composed of a type-I Raf ligand and a cereblon ligand with 5-position linkage
with the following chemical structure
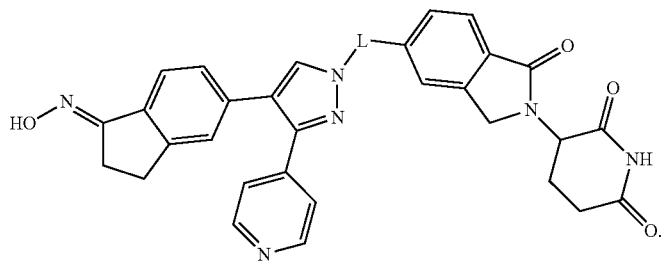
(PROTAC-II)
| PROTAC-II Compound | L | Mass | DC$_{50}$ (μM) | D$_{max}$ (%) |
|---|---|---|---|---|
| PROTAC-II-60 | | 727 | | |
| PROTAC-II-61 | | 726 | | |
| PROTAC-II-62 | | 726 | | |
| PROTAC-II-63 | | 712 | | |
| PROTAC-II-64 | | 698 | | |
| PROTAC-II-65 | | 608 | | |
| PROTAC-II-66 | | 618 | | |
| PROTAC-II-67 | | 604 | | |
| PROTAC-II-68 | | 590 | | |
| PROTAC-II-69 | | 588 | | |
| PROTAC-II-70 | | 574 | | |
| PROTAC-II-71 | | 576 | | |

TABLE 3
Protacs composed of a type-I Raf ligand and a cereblon ligand with 6-position linkage
with the following chemical structure
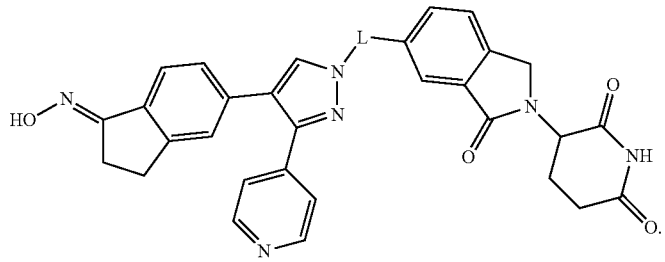
(PROTAC-III)
| PROTAC-III Compound | L | Mass | DC$_{50}$ (μM) | D$_{max}$ (%) |
|---|---|---|---|---|
| PROTAC-III-1 | | 668 | | |
| PROTAC-III-2 | | 756 | | |
| PROTAC-III-3 | | 712 | | |
| PROTAC-III-4 | | 800 | | |
| PROTAC-III-5 | | 844 | | |
| PROTAC-III-6 | | 634 | | |
| PROTAC-III-7 | | 678 | | |
| PROTAC-III-8 | | 722 | | |
| PROTAC-III-9 | | 766 | | |
| PROTAC-III-10 | | 810 | | |
| PROTAC-III-11 | | 652 | | |
| PROTAC-III-12 | | 652 | | |
| PROTAC-III-13 | | 652 | | |

TABLE 3-continued
Protacs composed of a type-I Raf ligand and a cereblon ligand with 6-position linkage with the following chemical structure
(PROTAC-III)
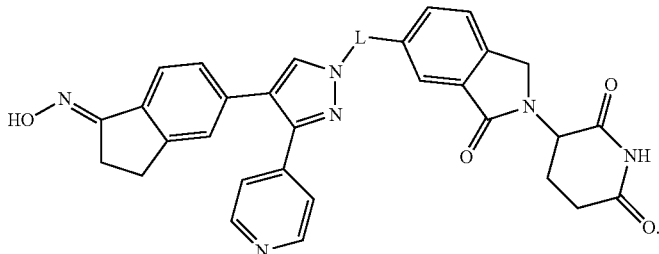
| PROTAC-III Compound | L | Mass | $DC_{50}$ (μM) | $D_{max}$ (%) |
|---|---|---|---|---|
| PROTAC-III-14 |  | 638 | | |
| PROTAC-III-15 |  | 638 | | |
| PROTAC-III-16 |  | 622 | | |
| PROTAC-III-17 |  | 682 | | |
| PROTAC-III-18 |  | 682 | | |
| PROTAC-III-19 |  | 682 | | |
| PROTAC-III-20 |  | 696 | | |
| PROTAC-III-21 |  | 696 | | |
| PROTAC-III-22 |  | 696 | | |
| PROTAC-III-23 |  | 696 | | |
| PROTAC-III-24 |  | 696 | | |
| PROTAC-III-25 |  | 696 | | |

TABLE 3-continued
Protacs composed of a type-I Raf ligand and a cereblon ligand with 6-position linkage
with the following chemical structure
(PROTAC-III)
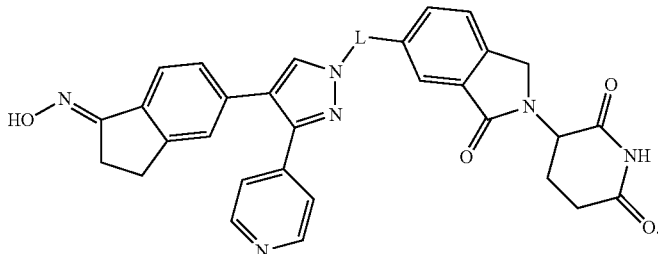
| PROTAC-III Compound | L | Mass | DC$_{50}$ (μM) | D$_{max}$ (%) |
|---|---|---|---|---|
| PROTAC-III-26 | 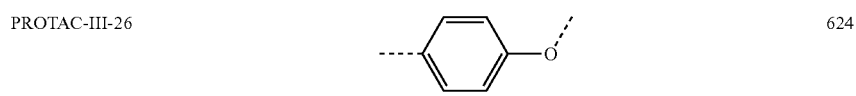 | 624 | | |
| PROTAC-III-27 | 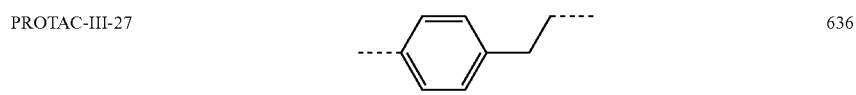 | 636 | | |
| PROTAC-III-28 | 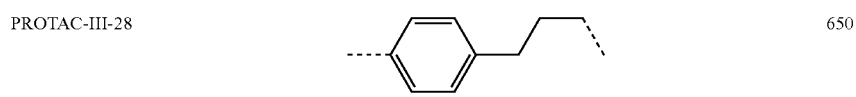 | 650 | | |
| PROTAC-III-29 | 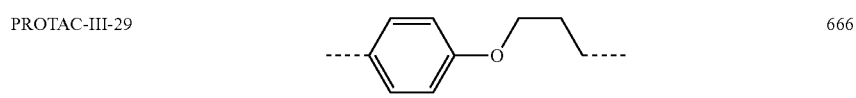 | 666 | | |
| PROTAC-III-30 | 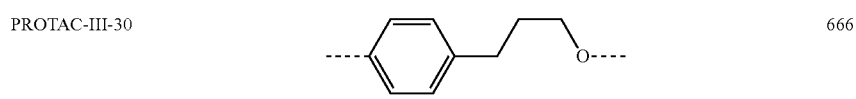 | 666 | | |
| PROTAC-III-31 | 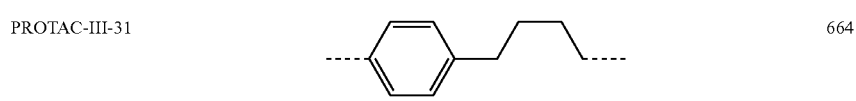 | 664 | | |
| PROTAC-III-32 | 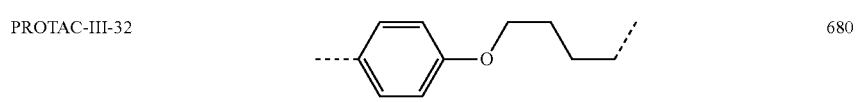 | 680 | | |
| PROTAC-III-33 | 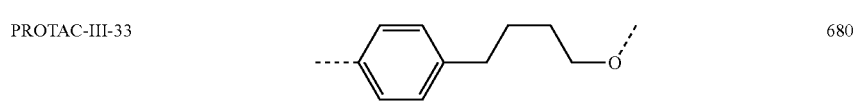 | 680 | | |
| PROTAC-III-34 | 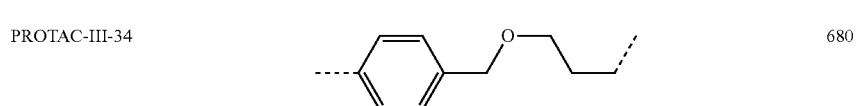 | 680 | | |
| PROTAC-III-35 | 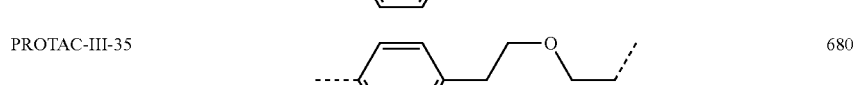 | 680 | | |
| PROTAC-III-36 | 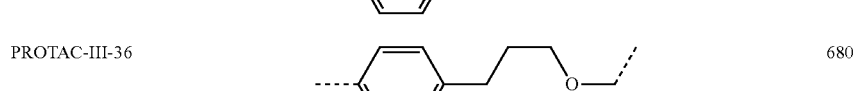 | 680 | | |
| PROTAC-III-37 | 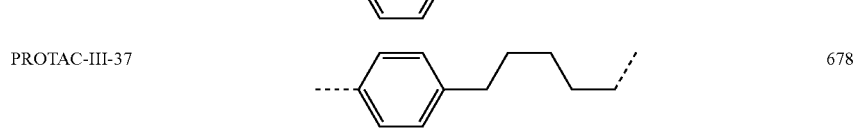 | 678 | | |

TABLE 3-continued
Protacs composed of a type-I Raf ligand and a cereblon ligand with 6-position linkage
with the following chemical structure
(PROTAC-III)
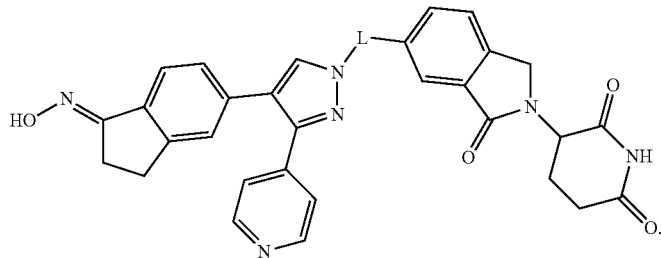
| PROTAC-III Compound | L | Mass | DC$_{50}$ (μM) | D$_{max}$ (%) |
|---|---|---|---|---|
| PROTAC-III-38 | | 726 | | |
| PROTAC-III-39 | | 726 | | |
| PROTAC-III-40 | | 724 | | |
| PROTAC-III-41 | | 740 | | |
| PROTAC-III-42 | | 740 | | |
| PROTAC-III-43 | | 740 | | |
| PROTAC-III-44 | | 659 | | |
| PROTAC-III-45 | | 673 | | |
| PROTAC-III-46 | | 687 | | |
| PROTAC-III-47 | | 701 | | |
| PROTAC-III-48 | | 703 | | |

TABLE 3-continued

Protacs composed of a type-I Raf ligand and a cereblon ligand with 6-position linkage
with the following chemical structure

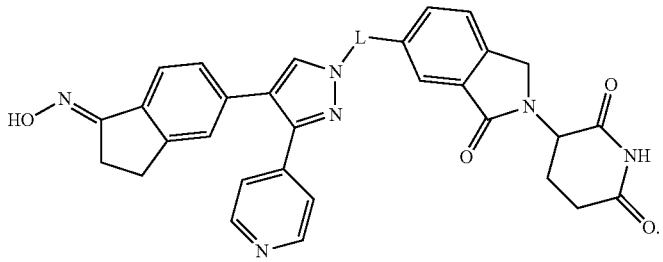

(PROTAC-III)

| PROTAC-III Compound | L | Mass | DC$_{50}$ (µM) | D$_{max}$ (%) |
|---|---|---|---|---|
| PROTAC-III-49 | ![piperidine-N-CH2CH2-O-CH2CH2-O-] | 717 | | |
| PROTAC-III-50 | ![piperidine-N-CH2CH2-O-CH2CH2CH2-O-] | 731 | | |
| PROTAC-III-51 | ![piperidine-N-CH2CH2-O-(CH2)4-O-] | 745 | | |
| PROTAC-III-52 | ![piperidine-N-CH2CH2-O-CH2CH2-O-CH2CH2-O-] | 761 | | |
| PROTAC-III-53 | ![phenyl-O-CH2CH2-piperazine-N-Me] | 736 | | |
| PROTAC-III-54 | ![phenyl-O-CH2CH2-piperidine-Me] | 735 | | |
| PROTAC-III-55 | ![phenyl-O-CH2CH2-piperazine-N-] | 750 | | |
| PROTAC-III-56 | ![phenyl-O-(CH2)3-piperazine-N-Me] | 764 | | |
| PROTAC-III-57 | ![phenyl-O-(CH2)4-piperazine-N-] | 778 | | |

TABLE 3-continued
Protacs composed of a type-I Raf ligand and a cereblon ligand with 6-position linkage
with the following chemical structure
(PROTAC-III)
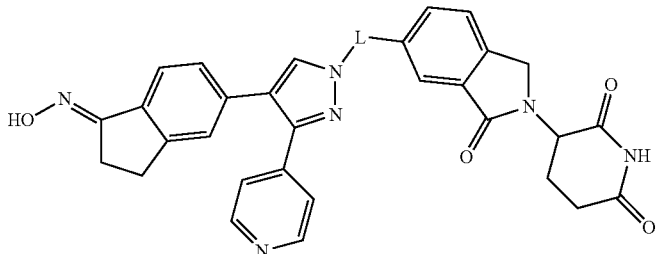
| PROTAC-III Compound | L | Mass | DC$_{50}$ (μM) | D$_{max}$ (%) |
|---|---|---|---|---|
| PROTAC-III-59 | | 779 | | |
| PROTAC-III-60 | | 727 | | |
| PROTAC-III-61 | | 726 | | |
| PROTAC-III-62 | | 726 | | |
| PROTAC-III-63 | | 712 | | |
| PROTAC-III-64 | | 698 | | |
| PROTAC-III-65 | | 608 | | |
| PROTAC-III-66 | | 618 | | |
| PROTAC-III-67 | | 604 | | |
| PROTAC-III-68 | | 590 | | |
| PROTAC-III-69 | | 588 | | |

TABLE 3-continued

Protacs composed of a type-I Raf ligand and a cereblon ligand with 6-position linkage with the following chemical structure (PROTAC-III)

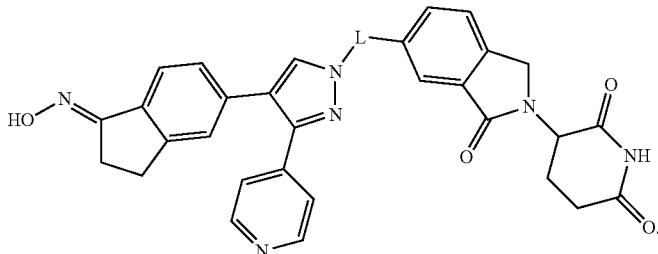

| PROTAC-III Compound | L | Mass | DC$_{50}$ (μM) | D$_{max}$ (%) |
|---|---|---|---|---|
| PROTAC-III-70 | | 574 | | |
| PROTAC-III-71 | | 576 | | |

TABLE 4

Protacs composed of a type-I Raf ligand and a cereblon ligand with 4-position linkage with the following chemical structure (PROTAC-IV)

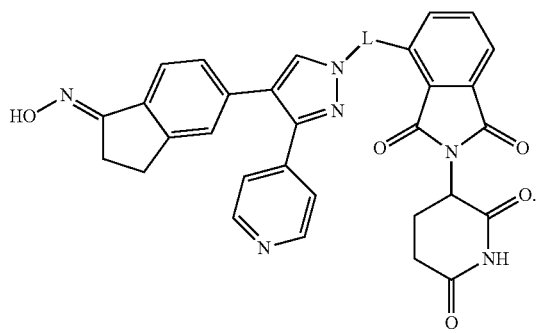

| PROTAC-IV Compound | L | Mass | DC$_{50}$ (μM) | D$_{max}$ (%) |
|---|---|---|---|---|
| PROTAC-IV-1 | | 682 | >1 | <10 |
| PROTAC-IV-2 | | 770 | <1 | ≥10 |
| PROTAC-IV-3 | | 726 | >1 | <10 |
| PROTAC-IV-4 | | 814 | <1 | ≥10 |
| PROTAC-IV-5 | | 858 | <1 | ≥10 |

TABLE 4-continued
Protacs composed of a type-I Raf ligand and a cereblon ligand with 4-position linkage
with the following chemical structure
(PROTAC-IV)
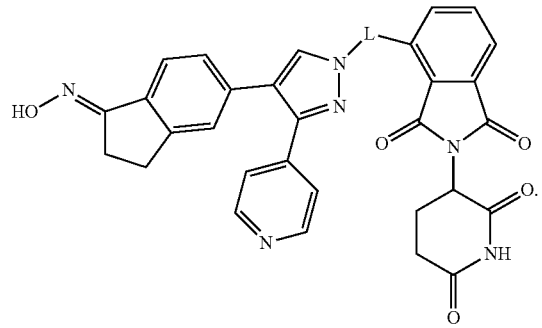
| PROTAC-IV Compound | L | Mass | DC$_{50}$ (μM) | D$_{max}$ (%) |
|---|---|---|---|---|
| PROTAC-IV-6 |  | 647 | >1 | <10 |
| PROTAC-IV-7 |  | 691 | >1 | <10 |
| PROTAC-IV-8 |  | 735 | >1 | <10 |
| PROTAC-IV-9 |  | 779 | >1 | <10 |
| PROTAC-IV-10 |  | 823 | >1 | <10 |
| PROTAC-IV-10a |  | 867 | >1 | <10 |
| PROTAC-IV-11 |  | 666 | | |
| PROTAC-IV-12 |  | 666 | | |
| PROTAC-IV-13 |  | 666 | | |
| PROTAC-IV-14 |  | 652 | | |
| PROTAC-IV-15 |  | 652 | | |
| PROTAC-IV-16 |  | 636 | | |
| PROTAC-IV-17 |  | 696 | | |

TABLE 4-continued
Protacs composed of a type-I Raf ligand and a cereblon ligand with 4-position linkage
with the following chemical structure
(PROTAC-IV)
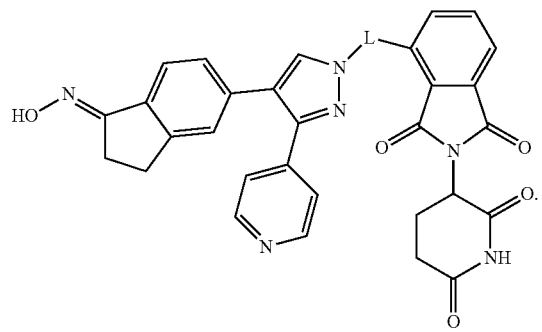
| PROTAC-IV Compound | L | Mass | DC$_{50}$ (μM) | D$_{max}$ (%) |
|---|---|---|---|---|
| PROTAC-IV-18 | | 696 | | |
| PROTAC-IV-19 | | 696 | | |
| PROTAC-IV-20 | | 710 | | |
| PROTAC-IV-21 | | 710 | | |
| PROTAC-IV-22 | | 710 | | |
| PROTAC-IV-23 | | 710 | | |
| PROTAC-IV-24 | | 710 | | |
| PROTAC-IV-25 | | 710 | | |
| PROTAC-IV-26 | | 638 | | |
| PROTAC-IV-27 | | 650 | | |
| PROTAC-IV-28 | | 664 | | |

TABLE 4-continued
Protacs composed of a type-I Raf ligand and a cereblon ligand with 4-position linkage
with the following chemical structure
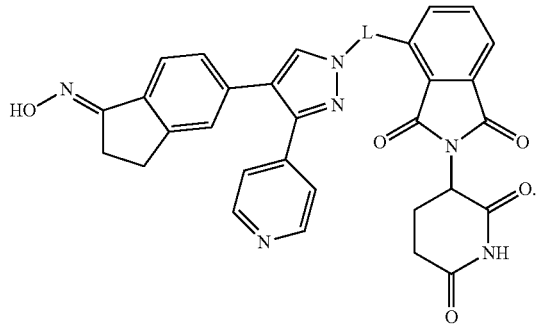
(PROTAC-IV)
| PROTAC-IV Compound | L | Mass | DC$_{50}$ (μM) | D$_{max}$ (%) |
|---|---|---|---|---|
| PROTAC-IV-29 | | 680 | | |
| PROTAC-IV-30 | | 680 | | |
| PROTAC-IV-31 | | 678 | | |
| PROTAC-IV-32 | | 694 | | |
| PROTAC-IV-33 | | 694 | | |
| PROTAC-IV-34 | | 694 | | |
| PROTAC-IV-35 | | 694 | | |
| PROTAC-IV-36 | | 694 | | |
| PROTAC-IV-37 | | 692 | | |
| PROTAC-IV-38 | | 740 | | |
| PROTAC-IV-39 | | 740 | | |

TABLE 4-continued
Protacs composed of a type-I Raf ligand and a cereblon ligand with 4-position linkage
with the following chemical structure
(PROTAC-IV)
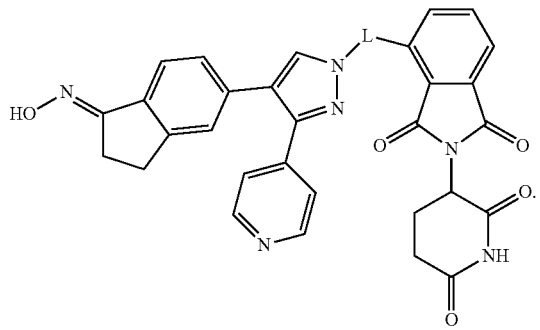
| PROTAC-IV Compound | L | Mass | $DC_{50}$ ($\mu$M) | $D_{max}$ (%) |
|---|---|---|---|---|
| PROTAC-IV-40 | | 738 | | |
| PROTAC-IV-41 | | 754 | | |
| PROTAC-IV-42 | | 754 | | |
| PROTAC-IV-43 | | 754 | | |
| PROTAC-IV-44 | | 673 | | |
| PROTAC-IV-45 | | 687 | | |
| PROTAC-IV-46 | | 701 | | |
| PROTAC-IV-47 | | 715 | | |
| PROTAC-IV-48 | | 717 | | |
| PROTAC-IV-49 | | 731 | | |
| PROTAC-IV-50 | | 745 | | |

TABLE 4-continued
Protacs composed of a type-I Raf ligand and a cereblon ligand with 4-position linkage with the following chemical structure
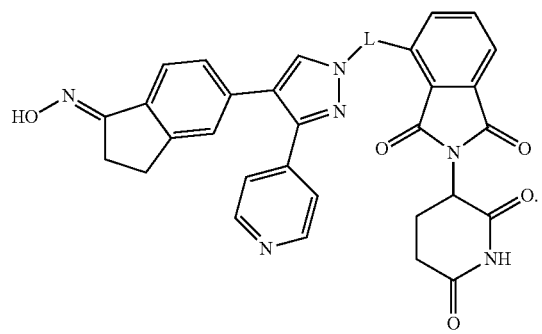
(PROTAC-IV)
| PROTAC-IV Compound | L | Mass | DC$_{50}$ (μM) | D$_{max}$ (%) |
|---|---|---|---|---|
| PROTAC-IV-51 | | 759 | | |
| PROTAC-IV-52 | | 775 | | |
| PROTAC-IV-53 | | 750 | | |
| PROTAC-IV-54 | | 749 | | |
| PROTAC-IV-55 | | 754 | | |
| PROTAC-IV-56 | | 768 | | |
| PROTAC-IV-57 | | 782 | | |
| PROTAC-IV-58 | | 784 | | |

TABLE 4-continued
Protacs composed of a type-I Raf ligand and a cereblon ligand with 4-position linkage
with the following chemical structure
(PROTAC-IV)
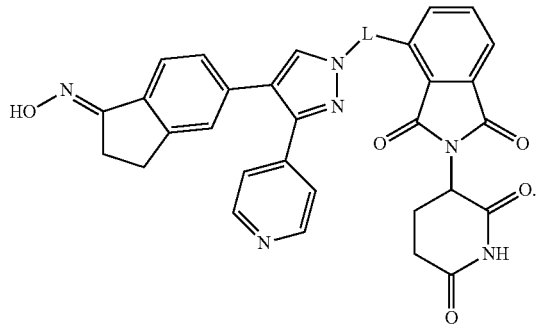
| PROTAC-IV Compound | L | Mass | DC$_{50}$ (μM) | D$_{max}$ (%) |
|---|---|---|---|---|
| PROTAC-IV-59 | | 783 | | |
| PROTAC-IV-60 | | 741 | | |
| PROTAC-IV-61 | | 740 | | |
| PROTAC-IV-62 | | 740 | | |
| PROTAC-IV-63 | | 726 | | |
| PROTAC-IV-64 | | 712 | | |
| PROTAC-IV-65 | | 622 | | |
| PROTAC-IV-66 | | 632 | | |
| PROTAC-IV-67 | | 618 | | |
| PROTAC-IV-68 | | 604 | | |

TABLE 4-continued
Protacs composed of a type-I Raf ligand and a cereblon ligand with 4-position linkage
with the following chemical structure
(PROTAC-IV)
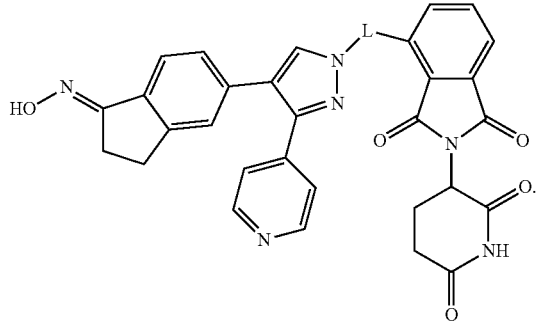
| PROTAC-IV Compound | L | Mass | DC$_{50}$ (μM) | D$_{max}$ (%) |
|---|---|---|---|---|
| PROTAC-IV-69 | 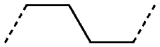 | 602 | | |
| PROTAC-IV-70 | 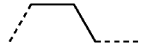 | 588 | | |
| PROTAC-IV-71 | 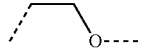 | 590 | | |
| PROTAC-IV-72 |  | 764 | | |
| PROTAC-IV-73 | 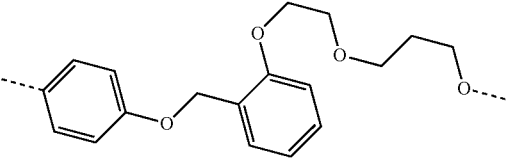 | 846 | | |
| PROTAC-IV-74 | 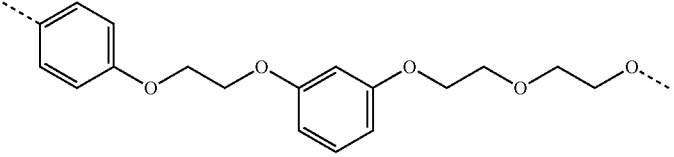 | 862 | | |
| PROTAC-IV-75 | 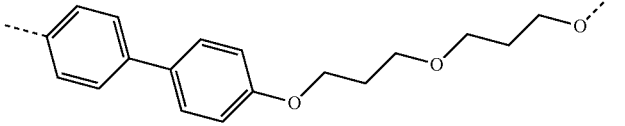 | 830 | | |
| PROTAC-IV-76 | 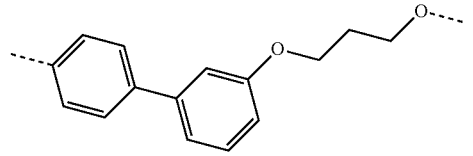 | 772 | | |
| PROTAC-IV-77 | 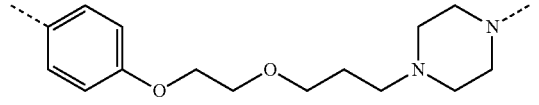 | 808 | | |

TABLE 4-continued

Protacs composed of a type-I Raf ligand and a cereblon ligand with 4-position linkage
with the following chemical structure (PROTAC-IV)

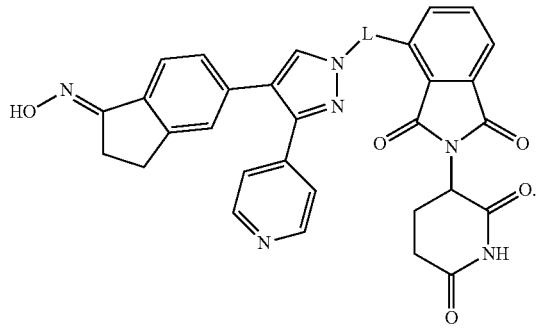

| PROTAC-IV Compound | L | Mass | DC$_{50}$ (μM) | D$_{max}$ (%) |
|---|---|---|---|---|
| PROTAC-IV-78 | 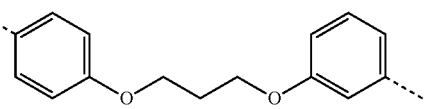 | 772 | | |

TABLE 5

Protacs composed of a type-I Raf ligand and a cereblon ligand with 4-position linkage
with the following chemical structure (PROTAC-V)

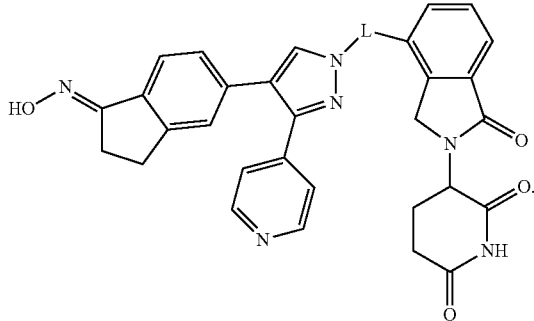

| PROTAC-V Compound | L | Mass | DC$_{50}$ (μM) | D$_{max}$ (%) |
|---|---|---|---|---|
| PROTAC-V-1 | 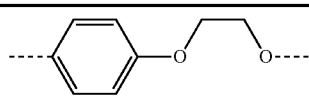 | 668 | | |
| PROTAC-V-2 | 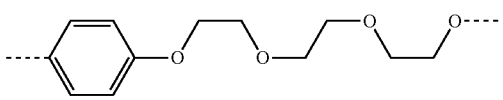 | 756 | | |
| PROTAC-V-3 | 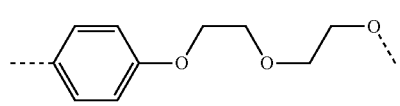 | 712 | | |
| PROTAC-V-4 | 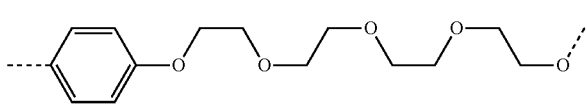 | 800 | | |

TABLE 5-continued
Protacs composed of a type-I Raf ligand and a cereblon ligand with 4-position linkage
with the following chemical structure
(PROTAC-V)
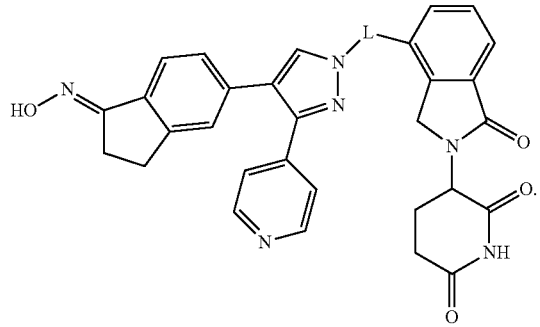
| PROTAC-V Compound | L | Mass | $DC_{50}$ (μM) | $D_{max}$ (%) |
|---|---|---|---|---|
| PROTAC-V-5 | | 844 | | |
| PROTAC-V-6 | | 634 | | |
| PROTAC-V-7 | | 678 | | |
| PROTAC-V-8 | | 722 | | |
| PROTAC-V-9 | | 766 | | |
| PROTAC-V-10 | | 810 | | |
| PROTAC-V-11 | | 652 | | |
| PROTAC-V-12 | | 652 | | |
| PROTAC-V-13 | | 652 | | |
| PROTAC-V-14 | | 638 | | |
| PROTAC-V-15 | | 638 | | |
| PROTAC-V-16 | | 622 | | |

TABLE 5-continued
Protacs composed of a type-I Raf ligand and a cereblon ligand with 4-position linkage
with the following chemical structure
(PROTAC-V)
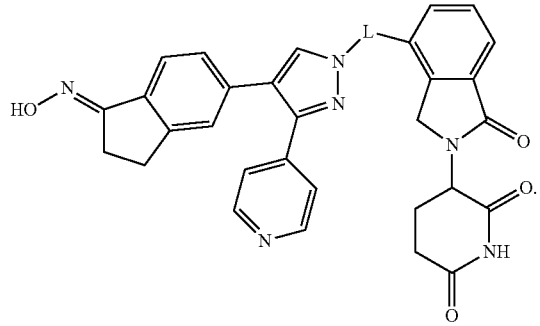
| PROTAC-V Compound | L | Mass | DC$_{50}$ (μM) | D$_{max}$ (%) |
|---|---|---|---|---|
| PROTAC-V-17 | | 682 | | |
| PROTAC-V-18 | | 682 | | |
| PROTAC-V-19 | | 682 | | |
| PROTAC-V-20 | | 696 | | |
| PROTAC-V-21 | | 696 | | |
| PROTAC-V-22 | | 696 | | |
| PROTAC-V-23 | | 696 | | |
| PROTAC-V-24 | | 696 | | |
| PROTAC-V-25 | | 696 | | |
| PROTAC-V-26 | | 624 | | |
| PROTAC-V-27 | | 636 | | |

TABLE 5-continued
Protacs composed of a type-I Raf ligand and a cereblon ligand with 4-position linkage
with the following chemical structure
(PROTAC-V)
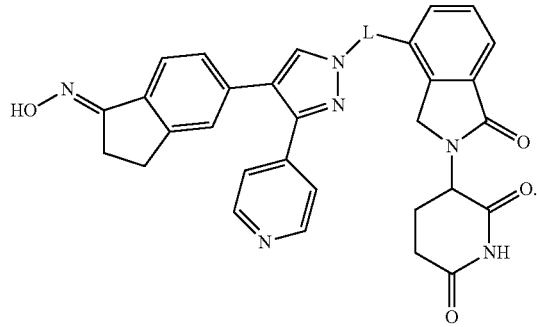
| PROTAC-V Compound | L | Mass | $DC_{50}$ (μM) | $D_{max}$ (%) |
|---|---|---|---|---|
| PROTAC-V-28 | | 650 | | |
| PROTAC-V-29 | | 666 | | |
| PROTAC-V-30 | | 666 | | |
| PROTAC-V-31 | | 664 | | |
| PROTAC-V-32 | | 680 | | |
| PROTAC-V-33 | | 680 | | |
| PROTAC-V-34 | | 680 | | |
| PROTAC-V-35 | | 680 | | |
| PROTAC-V-36 | | 680 | | |
| PROTAC-V-37 | | 678 | | |
| PROTAC-V-38 | | 726 | | |

TABLE 5-continued
Protacs composed of a type-I Raf ligand and a cereblon ligand with 4-position linkage
with the following chemical structure
(PROTAC-V)
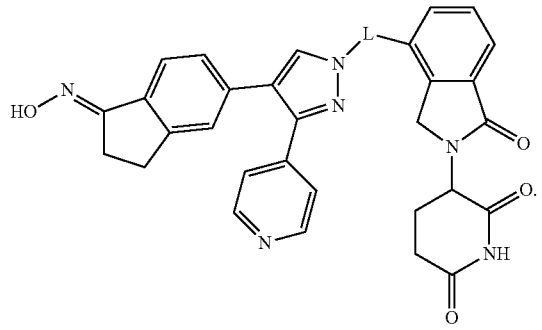
| PROTAC-V Compound | L | Mass | $DC_{50}$ ($\mu M$) | $D_{max}$ (%) |
|---|---|---|---|---|
| PROTAC-V-40 | | 724 | | |
| PROTAC-V-41 | | 740 | | |
| PROTAC-V-42 | | 740 | | |
| PROTAC-V-43 | | 740 | | |
| PROTAC-V-44 | | 659 | | |
| PROTAC-V-45 | | 673 | | |
| PROTAC-V-46 | | 687 | | |
| PROTAC-V-47 | | 701 | | |
| PROTAC-V-48 | | 703 | | |
| PROTAC-V-49 | | 717 | | |
| PROTAC-V-50 | | 731 | | |

TABLE 5-continued

Protacs composed of a type-I Raf ligand and a cereblon ligand with 4-position linkage
with the following chemical structure (PROTAC-V)

| PROTAC-V Compound | L | Mass | DC$_{50}$ (μM) | D$_{max}$ (%) |
|---|---|---|---|---|
| PROTAC-V-51 | | 745 | | |
| PROTAC-V-52 | | 761 | | |
| PROTAC-V-53 | | 736 | | |
| PROTAC-V-54 | | 735 | | |
| PROTAC-V-55 | | 750 | | |
| PROTAC-V-56 | | 764 | | |
| PROTAC-V-57 | | 778 | | |
| PROTAC-V-58 | | 780 | | |

TABLE 5-continued
Protacs composed of a type-I Raf ligand and a cereblon ligand with 4-position linkage with the following chemical structure
(PROTAC-V)
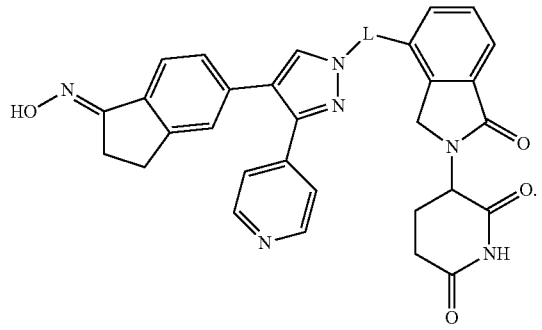
| PROTAC-V Compound | L | Mass | DC$_{50}$ (μM) | D$_{max}$ (%) |
|---|---|---|---|---|
| PROTAC-V-59 | | 779 | | |
| PROTAC-V-60 | | 727 | | |
| PROTAC-V-61 | | 726 | | |
| PROTAC-V-62 | | 726 | | |
| PROTAC-V-63 | | 712 | | |
| PROTAC-V-64 | | 698 | | |
| PROTAC-V-65 | | 608 | | |
| PROTAC-V-66 | | 618 | | |
| PROTAC-V-67 | | 604 | | |
| PROTAC-V-68 | | 590 | | |

TABLE 5-continued

Protacs composed of a type-I Raf ligand and a cereblon ligand with 4-position linkage with the following chemical structure (PROTAC-V)

| PROTAC-V Compound | L | Mass | DC$_{50}$ (μM) | D$_{max}$ (%) |
|---|---|---|---|---|
| PROTAC-V-69 | | 588 | | |
| PROTAC-V-70 | | 574 | | |
| PROTAC-V-71 | | 576 | | |

TABLE 6

Protacs composed of a type-I Raf ligand and a cereblon ligand with 7-position linkage with the following chemical structure (PROTAC-VI)

| PROTAC-VI Compound | L | Mass | DC$_{50}$ (μM) | D$_{max}$ (%) |
|---|---|---|---|---|
| PROTAC-VI-1 | | 668 | | |
| PROTAC-VI-2 | | 756 | | |
| PROTAC-VI-3 | | 712 | | |
| PROTAC-VI-4 | | 800 | | |

TABLE 6-continued
Protacs composed of a type-I Raf ligand and a cereblon ligand with 7-position linkage
with the following chemical structure
(PROTAC-VI)
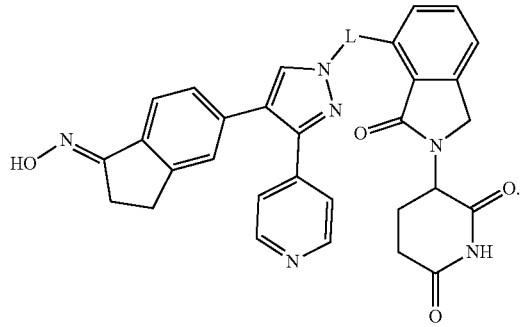
| PROTAC-VI Compound | L | Mass | DC$_{50}$ (μM) | D$_{max}$ (%) |
|---|---|---|---|---|
| PROTAC-VI-5 | 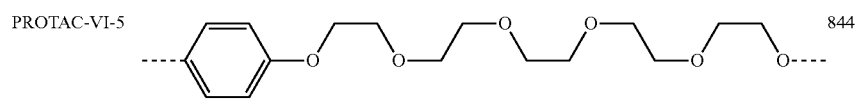 | 844 | | |
| PROTAC-VI-6 | 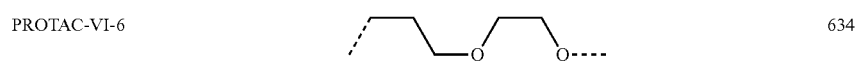 | 634 | | |
| PROTAC-VI-7 | 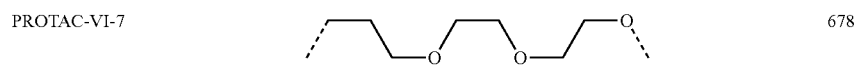 | 678 | | |
| PROTAC-VI-8 | 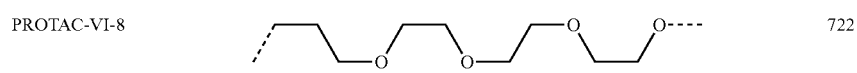 | 722 | | |
| PROTAC-VI-9 | 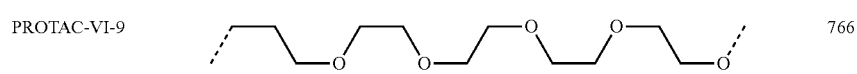 | 766 | | |
| PROTAC-VI-10 | 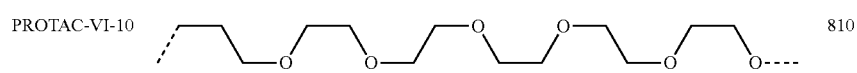 | 810 | | |
| PROTAC-VI-11 |  | 652 | | |
| PROTAC-VI-12 | 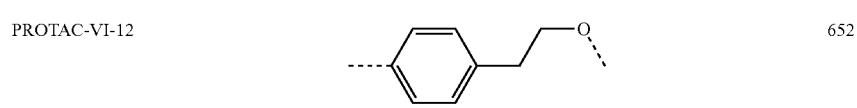 | 652 | | |
| PROTAC-VI-13 | 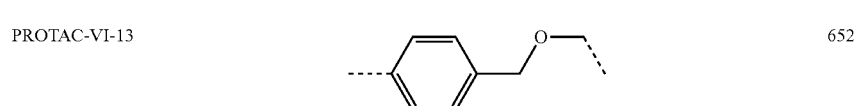 | 652 | | |
| PROTAC-VI-14 | 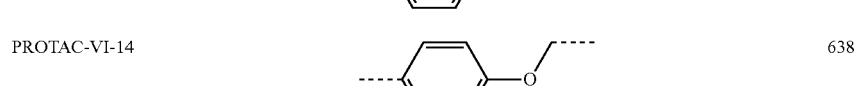 | 638 | | |
| PROTAC-VI-15 | 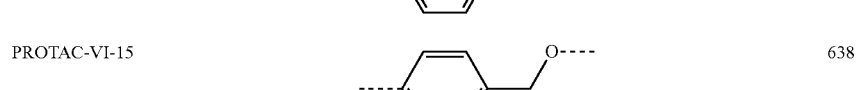 | 638 | | |
| PROTAC-VI-16 | 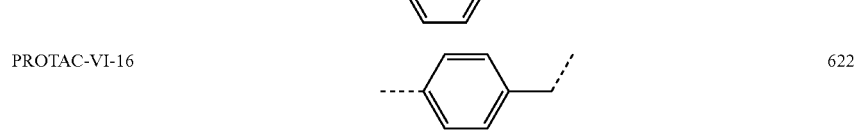 | 622 | | |

TABLE 6-continued
Protacs composed of a type-I Raf ligand and a cereblon ligand with 7-position linkage
with the following chemical structure
(PROTAC-VI)
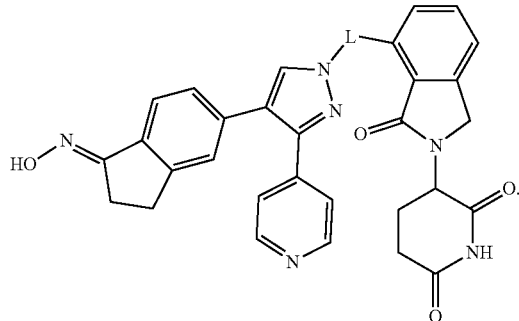
| PROTAC-VI Compound | L | Mass | DC$_{50}$ (μM) | D$_{max}$ (%) |
|---|---|---|---|---|
| PROTAC-VI-17 | | 682 | | |
| PROTAC-VI-18 | | 682 | | |
| PROTAC-VI-19 | | 682 | | |
| PROTAC-VI-20 | | 696 | | |
| PROTAC-VI-21 | | 696 | | |
| PROTAC-VI-22 | | 696 | | |
| PROTAC-VI-23 | | 696 | | |
| PROTAC-VI-24 | | 696 | | |
| PROTAC-VI-25 | | 696 | | |
| PROTAC-VI-26 | | 624 | | |
| PROTAC-VI-27 | | 636 | | |

TABLE 6-continued

Protacs composed of a type-I Raf ligand and a cereblon ligand with 7-position linkage
with the following chemical structure (PROTAC-VI)

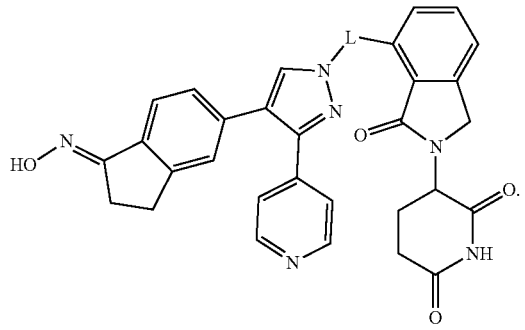

| PROTAC-VI Compound | L | Mass | DC$_{50}$ (μM) | D$_{max}$ (%) |
|---|---|---|---|---|
| PROTAC-VI-28 | ----⟨phenyl⟩-CH$_2$CH$_2$CH$_2$---- | 650 | | |
| PROTAC-VI-29 | ----⟨phenyl⟩-O-CH$_2$CH$_2$CH$_2$---- | 666 | | |
| PROTAC-VI-30 | ----⟨phenyl⟩-CH$_2$CH$_2$-O---- | 666 | | |
| PROTAC-VI-31 | ----⟨phenyl⟩-CH$_2$CH$_2$CH$_2$---- | 664 | | |
| PROTAC-VI-32 | ----⟨phenyl⟩-O-CH$_2$CH$_2$CH$_2$CH$_2$---- | 680 | | |
| PROTAC-VI-33 | ----⟨phenyl⟩-CH$_2$CH$_2$CH$_2$-O---- | 680 | | |
| PROTAC-VI-34 | ----⟨phenyl⟩-CH$_2$-O-CH$_2$CH$_2$---- | 680 | | |
| PROTAC-VI-35 | ----⟨phenyl⟩-CH$_2$CH$_2$-O-CH$_2$---- | 680 | | |
| PROTAC-VI-36 | ----⟨phenyl⟩-CH$_2$CH$_2$CH$_2$-O-CH$_2$---- | 680 | | |
| PROTAC-VI-37 | ----⟨phenyl⟩-CH$_2$CH$_2$CH$_2$CH$_2$---- | 678 | | |
| PROTAC-VI-38 | ----⟨phenyl⟩-O-CH$_2$CH$_2$-O-CH$_2$CH$_2$-O---- | 726 | | |

TABLE 6-continued
Protacs composed of a type-I Raf ligand and a cereblon ligand with 7-position linkage
with the following chemical structure
(PROTAC-VI)
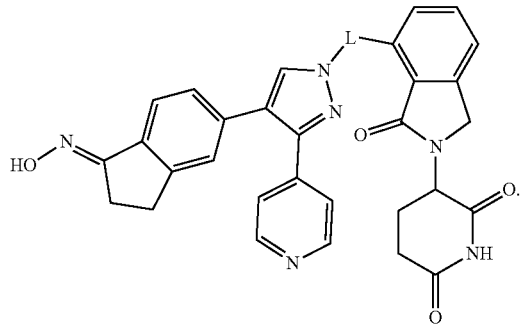
| PROTAC-VI Compound | L | Mass | DC$_{50}$ (μM) | D$_{max}$ (%) |
|---|---|---|---|---|
| PROTAC-VI-39 | | 726 | | |
| PROTAC-VI-40 | | 724 | | |
| PROTAC-VI-41 | | 740 | | |
| PROTAC-VI-42 | | 740 | | |
| PROTAC-VI-43 | | 740 | | |
| PROTAC-VI-44 | | 659 | | |
| PROTAC-VI-45 | | 673 | | |
| PROTAC-VI-46 | | 687 | | |
| PROTAC-VI-47 | | 701 | | |
| PROTAC-VI-48 | | 703 | | |
| PROTAC-VI-49 | | 717 | | |

TABLE 6-continued
Protacs composed of a type-I Raf ligand and a cereblon ligand with 7-position linkage
with the following chemical structure
(PROTAC-VI)
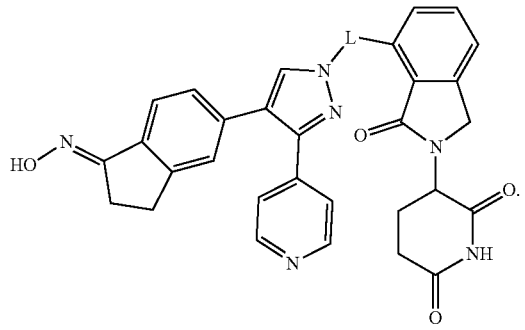
| PROTAC-VI Compound | L | Mass | DC$_{50}$ (μM) | D$_{max}$ (%) |
|---|---|---|---|---|
| PROTAC-VI-50 | | 731 | | |
| PROTAC-VI-51 | | 745 | | |
| PROTAC-VI-52 | | 761 | | |
| PROTAC-VI-53 | | 736 | | |
| PROTAC-VI-54 | | 735 | | |
| PROTAC-VI-55 | | 750 | | |
| PROTAC-VI-56 | | 764 | | |
| PROTAC-VI-57 | | 778 | | |

TABLE 6-continued
Protacs composed of a type-I Raf ligand and a cereblon ligand with 7-position linkage
with the following chemical structure
(PROTAC-VI)
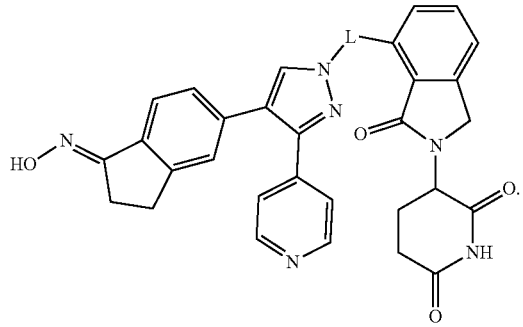
| PROTAC-VI Compound | L | Mass | DC$_{50}$ (μM) | D$_{max}$ (%) |
|---|---|---|---|---|
| PROTAC-VI-58 | | 780 | | |
| PROTAC-VI-59 | | 779 | | |
| PROTAC-VI-60 | | 727 | | |
| PROTAC-VI-61 | | 726 | | |
| PROTAC-VI-62 | | 726 | | |
| PROTAC-VI-63 | | 712 | | |
| PROTAC-VI-64 | | 698 | | |
| PROTAC-VI-65 | | 608 | | |
| PROTAC-VI-66 | | 618 | | |

TABLE 6-continued

Protacs composed of a type-I Raf ligand and a cereblon ligand with 7-position linkage with the following chemical structure

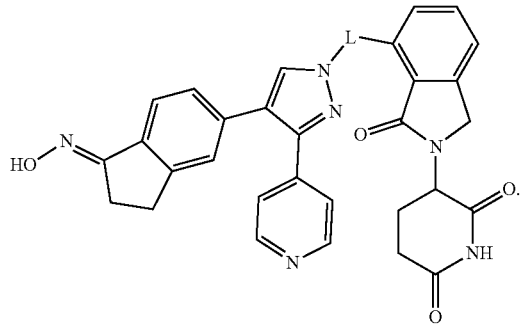

(PROTAC-VI)

| PROTAC-VI Compound | L | Mass | DC$_{50}$ (μM) | D$_{max}$ (%) |
|---|---|---|---|---|
| PROTAC-VI-67 | (propyl-O-) | 604 | | |
| PROTAC-VI-68 | (butyl-O-) | 590 | | |
| PROTAC-VI-69 | (pentyl) | 588 | | |
| PROTAC-VI-70 | (butyl---) | 574 | | |
| PROTAC-VI-71 | (propyl-O---) | 576 | | |

TABLE 7

Protacs composed of a type-I Raf ligand and VHL ligand with left-side linkage having the following chemical structure

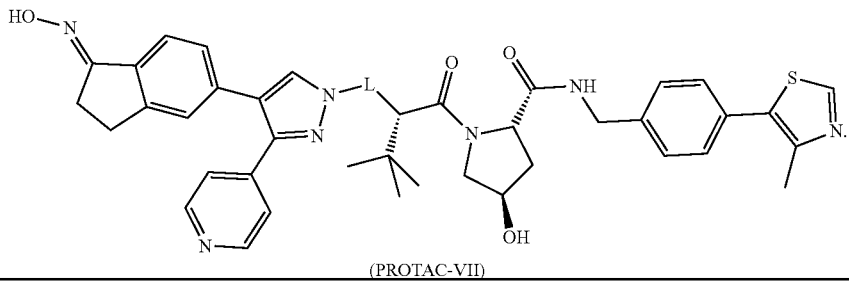

(PROTAC-VII)

| PROTAC-VII Compound | L | Mass | DC$_{50}$ (μM) | D$_{max}$ (%) |
|---|---|---|---|---|
| PROTAC-VII-1 | | 862 | >1 | <10 |
| PROTAC-VII-2 | | 906 | >1 | <10 |
| PROTAC-VII-3 | | 950 | >1 | <10 |

TABLE 7-continued
Protacs composed of a type-I Raf ligand and VHL ligand with left-side linkage having the following chemical structure
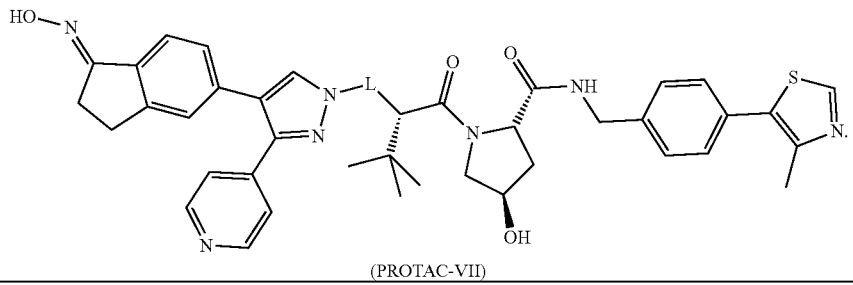
(PROTAC-VII)
| PROTAC-VII Compound | L | Mass | DC$_{50}$ (μM) | D$_{max}$ (%) |
|---|---|---|---|---|
| PROTAC-VII-4 | | 994 | >1 | <10 |
| PROTAC-VII-5 | | 1038 | >1 | <10 |
| PROTAC-VII-6 | | 896 | | |
| PROTAC-VII-7 | | 940 | | |
| PROTAC-VII-8 | | 984 | | |
| PROTAC-VII-9 | | 1028 | | |
| PROTAC-VII-10 | | 1072 | | |
| PROTAC-VII-11 | | 880 | | |
| PROTAC-VII-12 | | 880 | | |
| PROTAC-VII-13 | | 866 | | |

TABLE 7-continued
Protacs composed of a type-I Raf ligand and VHL ligand with left-side linkage having the following chemical structure
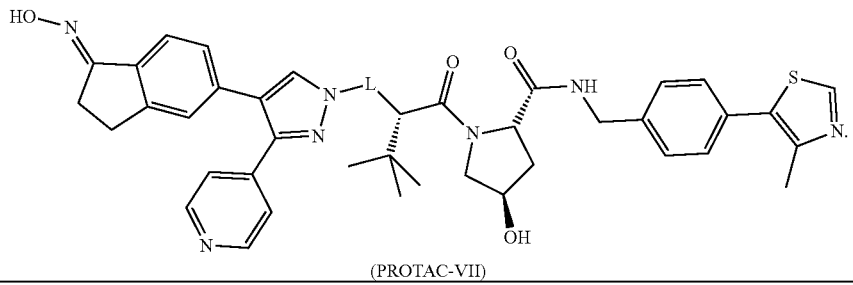
(PROTAC-VII)
| PROTAC-VII Compound | L | Mass | $DC_{50}$ ($\mu$M) | $D_{max}$ (%) |
|---|---|---|---|---|
| PROTAC-VII-14 | | 866 | | |
| PROTAC-VII-15 | | 866 | | |
| PROTAC-VII-16 | | 850 | | |
| PROTAC-VII-17 | | 910 | | |
| PROTAC-VII-18 | | 910 | | |
| PROTAC-VII-19 | | 910 | | |
| PROTAC-VII-20 | | 924 | | |
| PROTAC-VII-21 | | 924 | | |
| PROTAC-VII-22 | | 924 | | |
| PROTAC-VII-23 | | 924 | | |

TABLE 7-continued

Protacs composed of a type-I Raf ligand and VHL ligand with left-side linkage having the following chemical structure

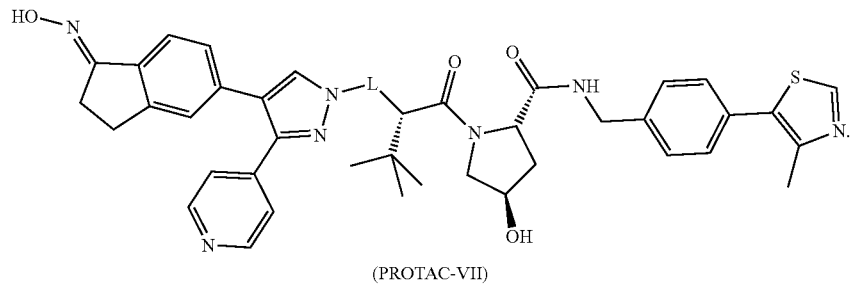

(PROTAC-VII)

| PROTAC-VII Compound | L | Mass | DC$_{50}$ (μM) | D$_{max}$ (%) |
|---|---|---|---|---|
| PROTAC-VII-24 | ----⟨phenyl⟩-CH$_2$CH$_2$-O-CH$_2$CH$_2$-O-CH$_2$-C(=O)-NH---- | 924 | | |
| PROTAC-VII-25 | ----⟨phenyl⟩-CH$_2$-O-CH$_2$CH$_2$-O-CH$_2$CH$_2$-C(=O)-NH---- | 924 | | |
| PROTAC-VII-26 | ----⟨phenyl⟩-O-CH$_2$-C(=O)-HN---- | 852 | | |
| PROTAC-VII-27 | ----⟨phenyl⟩-CH$_2$CH$_2$-C(=O)-NH---- | 864 | | |
| PROTAC-VII-28 | ----⟨phenyl⟩-CH$_2$CH$_2$CH$_2$-C(=O)-HN---- | 850 | | |
| PROTAC-VII-29 | ----⟨phenyl⟩-O-CH$_2$CH$_2$CH$_2$-C(=O)-NH---- | 866 | | |
| PROTAC-VII-30 | ----⟨phenyl⟩-CH$_2$CH$_2$-O-CH$_2$-C(=O)-NH---- | 866 | | |
| PROTAC-VII-31 | ----⟨phenyl⟩-CH$_2$CH$_2$CH$_2$CH$_2$-C(=O)-NH---- | 864 | | |
| PROTAC-VII-32 | ----⟨phenyl⟩-O-CH$_2$CH$_2$CH$_2$-C(=O)-HN---- | 880 | | |

TABLE 7-continued
Protacs composed of a type-I Raf ligand and VHL ligand with left-side linkage having the following chemical structure
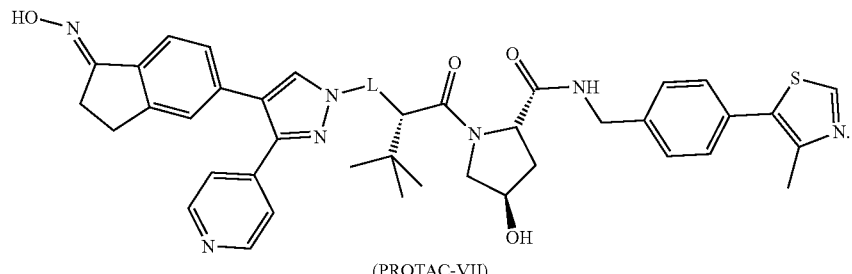
(PROTAC-VII)
| PROTAC-VII Compound | L | Mass | DC$_{50}$ (μM) | D$_{max}$ (%) |
|---|---|---|---|---|
| PROTAC-VII-33 | | 880 | | |
| PROTAC-VII-34 | | 880 | | |
| PROTAC-VII-35 | | 880 | | |
| PROTAC-VII-36 | | 880 | | |
| PROTAC-VII-37 | | 878 | | |
| PROTAC-VII-38 | | 954 | | |
| PROTAC-VII-39 | | 954 | | |
| PROTAC-VII-40 | | 952 | | |
| PROTAC-VII-41 | | 968 | | |

TABLE 7-continued
Protacs composed of a type-I Raf ligand and VHL ligand with left-side linkage having the following chemical structure
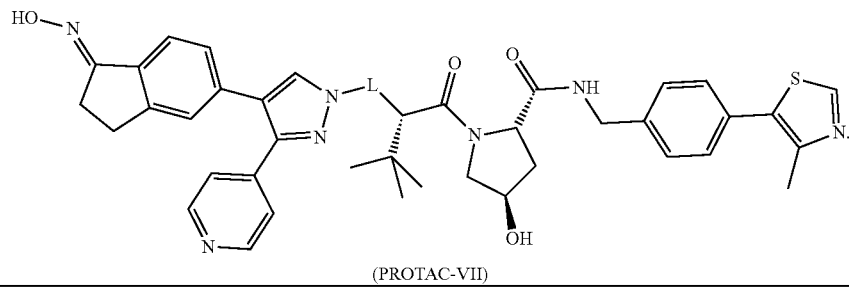
(PROTAC-VII)
| PROTAC-VII Compound | L | Mass | DC$_{50}$ (μM) | D$_{max}$ (%) |
|---|---|---|---|---|
| PROTAC-VII-42 | | 968 | | |
| PROTAC-VII-43 | | 968 | | |
| PROTAC-VII-44 | | 887 | | |
| PROTAC-VII-45 | | 901 | | |
| PROTAC-VII-46 | | 915 | | |
| PROTAC-VII-47 | | 929 | | |
| PROTAC-VII-48 | | 931 | | |
| PROTAC-VII-49 | | 945 | | |
| PROTAC-VII-50 | | 959 | | |

TABLE 7-continued
Protacs composed of a type-I Raf ligand and VHL ligand with left-side linkage having the following chemical structure
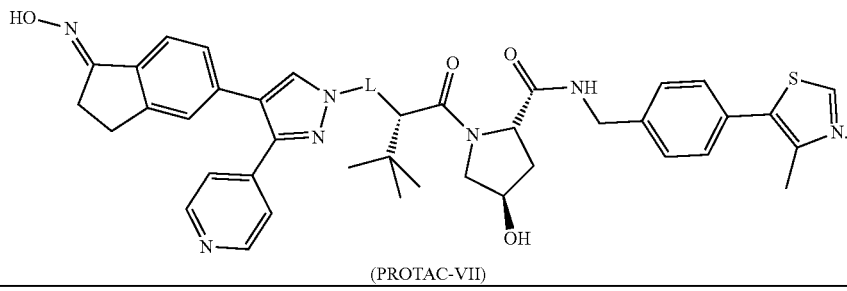
(PROTAC-VII)
| PROTAC-VII Compound | L | Mass | DC$_{50}$ (μM) | D$_{max}$ (%) |
|---|---|---|---|---|
| PROTAC-VII-51 | | 973 | | |
| PROTAC-VII-52 | | 989 | | |
| PROTAC-VII-53 | | 964 | | |
| PROTAC-VII-54 | | 963 | | |
| PROTAC-VII-55 | | 978 | | |
| PROTAC-VII-56 | | 992 | | |
| PROTAC-VII-57 | | 1006 | | |
| PROTAC-VII-58 | | 1008 | | |

TABLE 7-continued
Protacs composed of a type-I Raf ligand and VHL ligand with left-side linkage having the following chemical structure
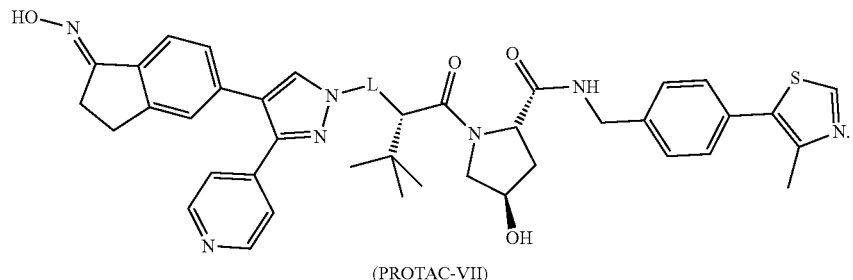
(PROTAC-VII)
| PROTAC-VII Compound | L | Mass | $DC_{50}$ ($\mu M$) | $D_{max}$ (%) |
|---|---|---|---|---|
| PROTAC-VII-59 | | 1007 | | |
| PROTAC-VII-60 | | 955 | | |
| PROTAC-VII-61 | | 954 | | |
| PROTAC-VII-62 | | 954 | | |
| PROTAC-VII-63 | | 940 | | |
| PROTAC-VII-64 | | 926 | | |
| PROTAC-VII-65 | | 836 | | |
| PROTAC-VII-66 | | 846 | | |
| PROTAC-VII-67 | | 832 | | |

TABLE 7-continued
Protacs composed of a type-I Raf ligand and VHL ligand with left-side linkage having the following chemical structure
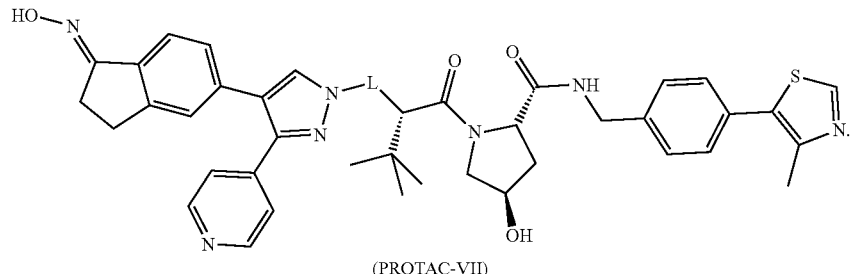
(PROTAC-VII)
| PROTAC-VII Compound | L | Mass | DC$_{50}$ (μM) | D$_{max}$ (%) |
|---|---|---|---|---|
| PROTAC-VII-68 | | 818 | | |
| PROTAC-VII-69 | | 816 | | |
| PROTAC-VII-70 | | 802 | | |
| PROTAC-VII-71 | | 804 | | |
| PROTAC-VII-72 | | 876 | | |
| PROTAC-VII-73 | | 890 | | |
| PROTAC-VII-74 | | 904 | | |
| PROTAC-VII-75 | | 918 | | |
| PROTAC-VII-76 | | 920 | | |
| PROTAC-VII-77 | | 932 | | |
| PROTAC-VII-78 | | 934 | | |

TABLE 7-continued
Protacs composed of a type-I Raf ligand and VHL ligand with left-side linkage having the following chemical structure
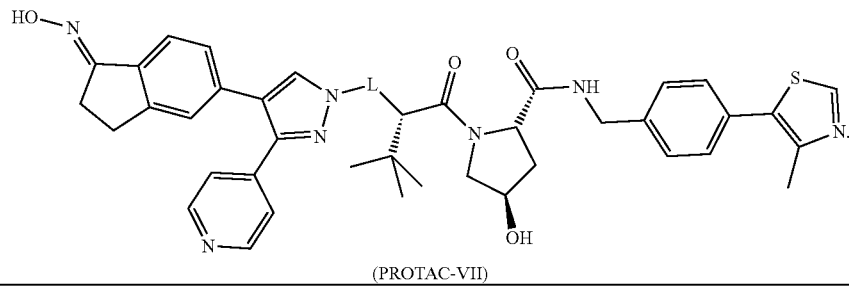
(PROTAC-VII)
| PROTAC-VII Compound | L | Mass | DC$_{50}$ (µM) | D$_{max}$ (%) |
|---|---|---|---|---|
| PROTAC-VII-79 | | 934 | | |
| PROTAC-VII-80 | | 948 | | |
| PROTAC-VII-81 | | 948 | | |
| PROTAC-VII-82 | | 948 | | |
| PROTAC-VII-83 | | 962 | | |
| PROTAC-VII-84 | | 962 | | |
| PROTAC-VII-85 | | 962 | | |
| PROTAC-VII-86 | | 962 | | |
| PROTAC-VII-87 | | 964 | | |
| PROTAC-VII-88 | | 976 | | |

TABLE 7-continued
Protacs composed of a type-I Raf ligand and VHL ligand with left-side linkage having the following chemical structure
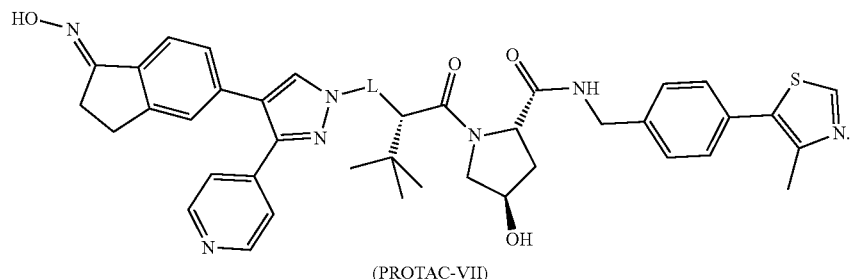
(PROTAC-VII)
| PROTAC-VII Compound | L | Mass | $DC_{50}$ (μM) | $D_{max}$ (%) |
|---|---|---|---|---|
| PROTAC-VII-89 | | 976 | | |
| PROTAC-VII-90 | | 976 | | |
| PROTAC-VII-91 | | 976 | | |
| PROTAC-VII-92 | | 976 | | |
| PROTAC-VII-93 | | 978 | | |
| PROTAC-VII-94 | | 978 | | |
| PROTAC-VII-95 | | 978 | | |
| PROTAC-VII-96 | | 930 | | |
| PROTAC-VII-97 | | 944 | | |
| PROTAC-VII-98 | | 958 | | |

TABLE 7-continued
Protacs composed of a type-I Raf ligand and VHL ligand with left-side linkage having the following chemical structure
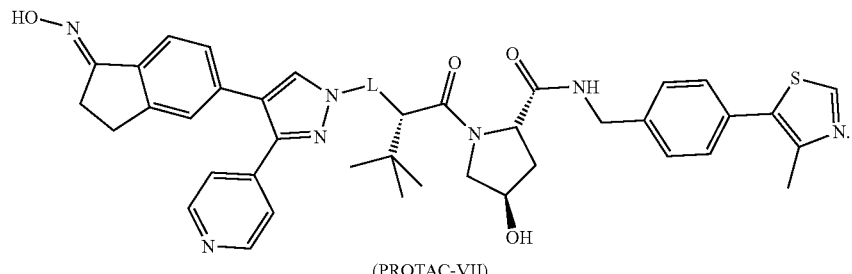
(PROTAC-VII)
| PROTAC-VII Compound | L | Mass | DC$_{50}$ (μM) | D$_{max}$ (%) |
|---|---|---|---|---|
| PROTAC-VII-99 | | 972 | | |
| PROTAC-VII-100 | | 986 | | |
| PROTAC-VII-101 | | 988 | | |
| PROTAC-VII-102 | | 1002 | | |
| PROTAC-VII-103 | | 1002 | | |
| PROTAC-VII-104 | | 1004 | | |
| PROTAC-VII-105 | | 1018 | | |
| PROTAC-VII-106 | | 1020 | | |

TABLE 7-continued

Protacs composed of a type-I Raf ligand and VHL ligand with left-side linkage having the following chemical structure

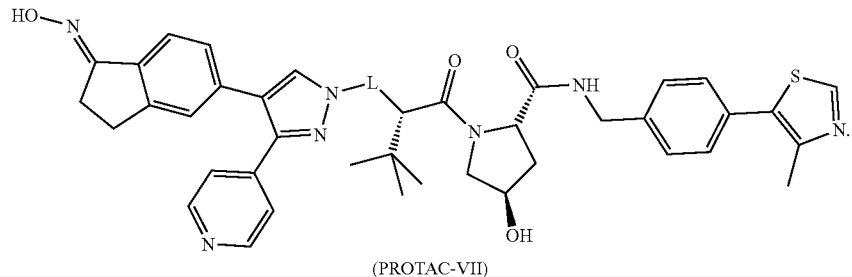

(PROTAC-VII)

| PROTAC-VII Compound | L | Mass | DC$_{50}$ (µM) | D$_{max}$ (%) |
|---|---|---|---|---|
| PROTAC-VII-107 | | 1020 | | |
| PROTAC-VII-108 | | 1020 | | |

TABLE 8

Protacs composed of a type-I Raf ligand and VHL ligand with right-side linkage having the following chemical structure

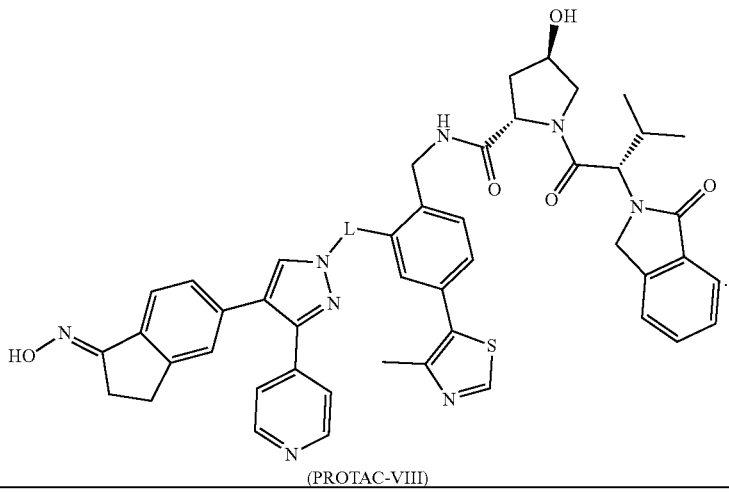

(PROTAC-VIII)

| PROTAC-VIII Compound | L | Mass | DC$_{50}$ (µM) | D$_{max}$ (%) |
|---|---|---|---|---|
| PROTAC-VIII-1 | | 922 | >1 | <10 |
| PROTAC-VIII-2 | | 966 | >1 | <10 |
| PROTAC-VIII-3 | | 1010 | >1 | <10 |
| PROTAC-VIII-4 | | 1054 | >1 | <10 |

TABLE 8-continued

Protacs composed of a type-I Raf ligand and VHL ligand with right-side linkage having the following chemical structure

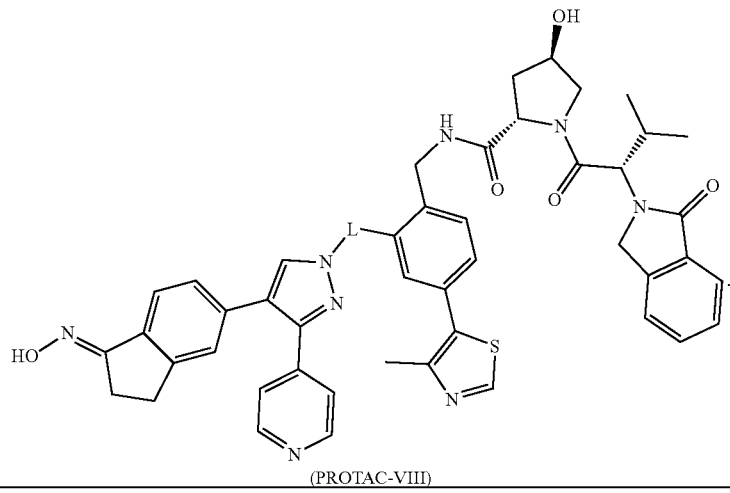

(PROTAC-VIII)

| PROTAC-VIII Compound | L | Mass | DC$_{50}$ (μM) | D$_{max}$ (%) |
|---|---|---|---|---|
| PROTAC-VIII-5 | (PEG-type linker) | 1098 | >1 | <10 |
| PROTAC-VIII-6 | (phenyl-O-CH2CH2-O linker) | 956 | | |
| PROTAC-VIII-7 | (phenyl-O-CH2CH2-O-CH2CH2-O linker) | 1000 | | |
| PROTAC-VIII-8 | (phenyl-O-(CH2CH2O)3 linker) | 1044 | | |
| PROTAC-VIII-9 | (phenyl-O-(CH2CH2O)4 linker) | 1088 | | |
| PROTAC-VIII-10 | (phenyl-O-(CH2CH2O)5 linker) | 1132 | | |
| PROTAC-VIII-11 | (phenyl-O-CH2CH2 linker) | 940 | | |
| PROTAC-VIII-12 | (phenyl-CH2CH2-O linker) | 940 | | |
| PROTAC-VIII-13 | (phenyl-CH2-O-CH2 linker) | 940 | | |
| PROTAC-VIII-14 | (phenyl-O-CH2 linker) | 926 | | |

TABLE 8-continued
Protacs composed of a type-I Raf ligand and VHL ligand with right-side linkage having the following chemical structure
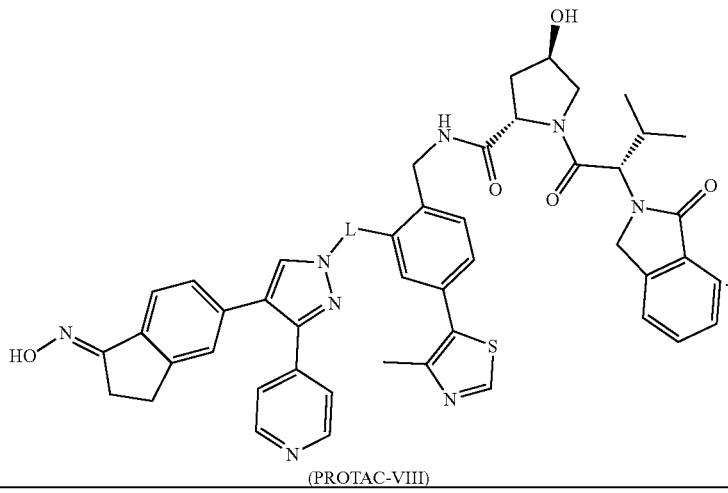
(PROTAC-VIII)
| PROTAC-VIII Compound | L | Mass | $DC_{50}$ (μM) | $D_{max}$ (%) |
|---|---|---|---|---|
| PROTAC-VIII-15 | | 926 | | |
| PROTAC-VIII-16 | | 910 | | |
| PROTAC-VIII-17 | | 970 | | |
| PROTAC-VIII-18 | | 970 | | |
| PROTAC-VIII-19 | | 970 | | |
| PROTAC-VIII-20 | | 984 | | |
| PROTAC-VIII-21 | | 984 | | |
| PROTAC-VIII-22 | | 984 | | |
| PROTAC-VIII-23 | | 984 | | |
| PROTAC-VIII-24 | | 984 | | |

TABLE 8-continued
Protacs composed of a type-I Raf ligand and VHL ligand with right-side linkage having the following chemical structure
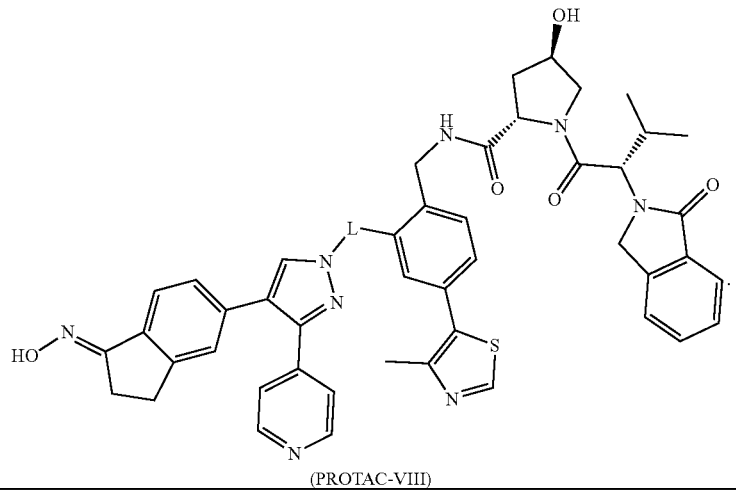
(PROTAC-VIII)
| PROTAC-VIII Compound | L | Mass | $DC_{50}$ (μM) | $D_{max}$ (%) |
|---|---|---|---|---|
| PROTAC-VIII-25 | | 984 | | |
| PROTAC-VIII-26 | | 912 | | |
| PROTAC-VIII-27 | | 924 | | |
| PROTAC-VIII-28 | | 938 | | |
| PROTAC-VIII-29 | | 954 | | |
| PROTAC-VIII-30 | | 954 | | |
| PROTAC-VIII-31 | | 956 | | |
| PROTAC-VIII-32 | | 972 | | |
| PROTAC-VIII-33 | | 972 | | |
| PROTAC-VIII-34 | | 972 | | |

TABLE 8-continued

Protacs composed of a type-I Raf ligand and VHL ligand with right-side linkage having the following chemical structure

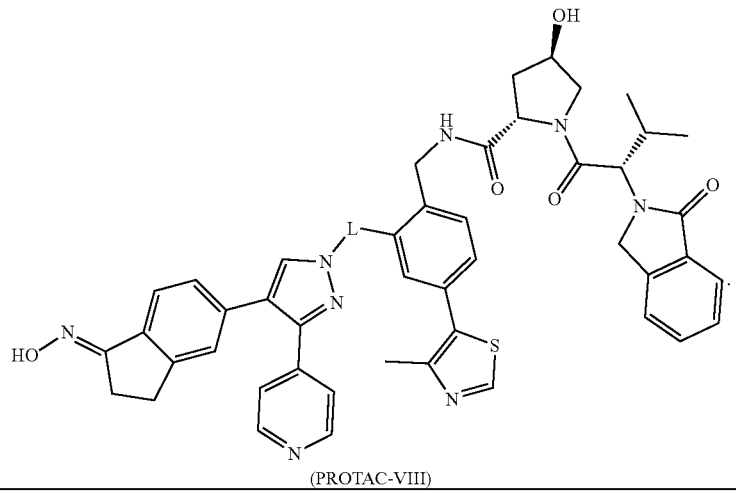

(PROTAC-VIII)

| PROTAC-VIII Compound | L | Mass | $DC_{50}$ ($\mu$M) | $D_{max}$ (%) |
|---|---|---|---|---|
| PROTAC-VIII-35 | [4-substituted phenyl]-CH₂CH₂-O-CH₂- | 972 | | |
| PROTAC-VIII-36 | [4-substituted phenyl]-CH₂CH₂CH₂-O-CH₂- | 972 | | |
| PROTAC-VIII-37 | [4-substituted phenyl]-(CH₂)₄- | 970 | | |
| PROTAC-VIII-38 | [4-substituted phenyl]-O-CH₂CH₂-O-CH₂CH₂-O- | 1014 | | |
| PROTAC-VIII-39 | [4-substituted phenyl]-O-CH₂CH₂-O-CH₂CH₂-O- | 1014 | | |
| PROTAC-VIII-40 | [4-substituted phenyl]-O-(CH₂)₄-O- | 1012 | | |
| PROTAC-VIII-41 | [4-substituted phenyl]-O-CH₂-O-CH₂CH₂CH₂-O- | 1028 | | |
| PROTAC-VIII-42 | [4-substituted phenyl]-O-CH₂CH₂-O-CH₂CH₂-O-CH₂- | 1028 | | |
| PROTAC-VIII-43 | [4-substituted phenyl]-O-CH₂CH₂CH₂-O-CH₂CH₂-O- | 1028 | | |
| PROTAC-VIII-44 | [4-piperidinyl]-N-CH₂CH₂-O- | 947 | | |

TABLE 8-continued
Protacs composed of a type-I Raf ligand and VHL ligand with right-side linkage having the following chemical structure
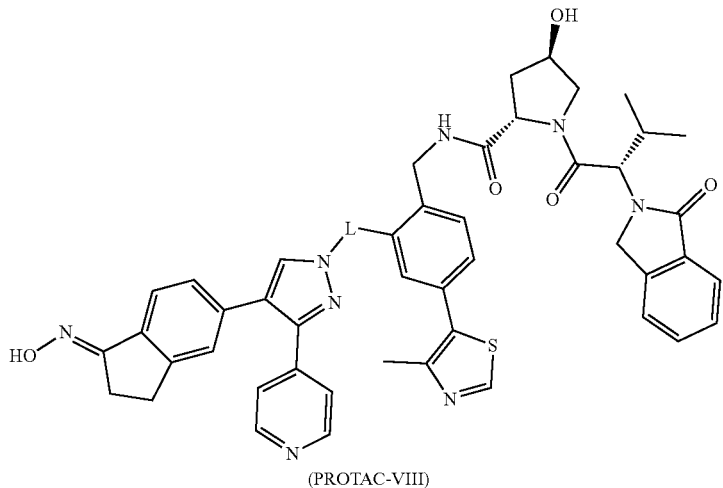
(PROTAC-VIII)
| PROTAC-VIII Compound | L | Mass | DC$_{50}$ (μM) | D$_{max}$ (%) |
|---|---|---|---|---|
| PROTAC-VIII-45 | | 961 | | |
| PROTAC-VIII-46 | | 975 | | |
| PROTAC-VIII-47 | | 989 | | |
| PROTAC-VIII-48 | | 991 | | |
| PROTAC-VIII-49 | | 1005 | | |
| PROTAC-VIII-50 | | 1019 | | |
| PROTAC-VIII-51 | | 1033 | | |
| PROTAC-VIII-52 | | 1049 | | |
| PROTAC-VIII-53 | | 1024 | | |

TABLE 8-continued
Protacs composed of a type-I Raf ligand and VHL ligand with right-side linkage having the following chemical structure
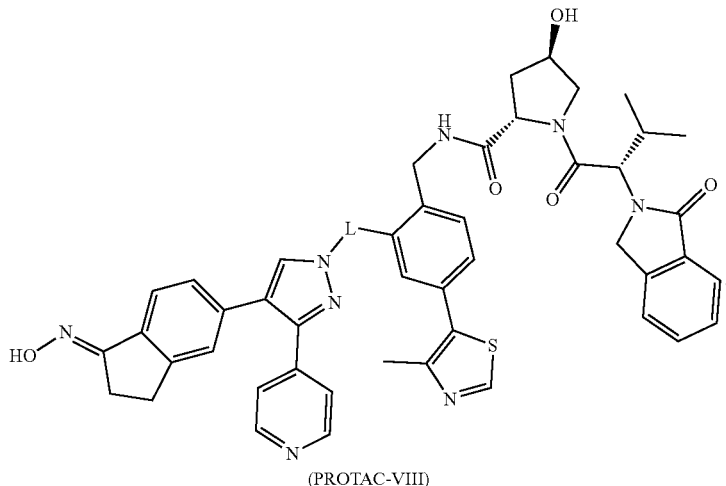
(PROTAC-VIII)
| PROTAC-VIII Compound | L | Mass | DC$_{50}$ (µM) | D$_{max}$ (%) |
|---|---|---|---|---|
| PROTAC-VIII-54 | 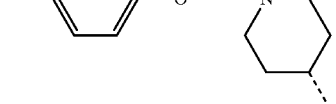 | 1023 | | |
| PROTAC-VIII-55 | 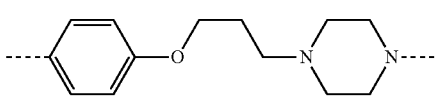 | 1038 | | |
| PROTAC-VIII-56 | 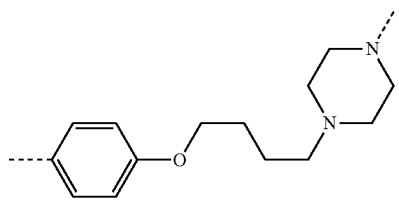 | 1052 | | |
| PROTAC-VIII-57 | 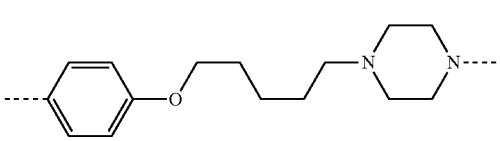 | 1066 | | |
| PROTAC-VIII-58 | 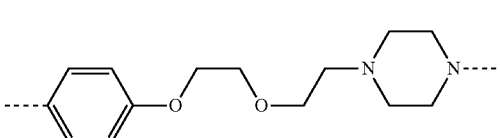 | 1068 | | |
| PROTAC-VIII-59 | 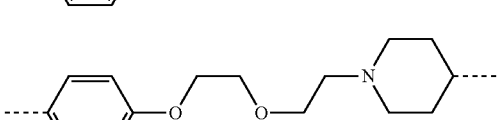 | 1067 | | |
| PROTAC-VIII-60 | 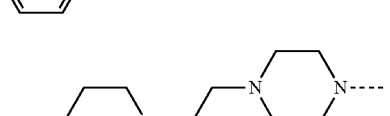 | 1015 | | |

TABLE 8-continued
Protacs composed of a type-I Raf ligand and VHL ligand with right-side linkage having the following chemical structure
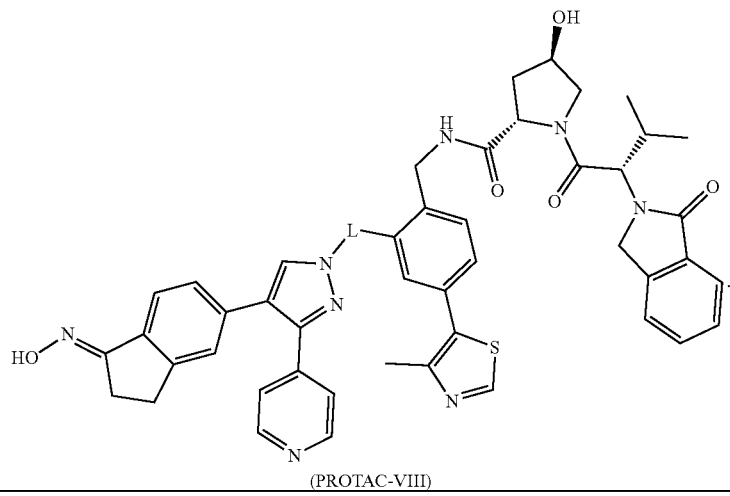
(PROTAC-VIII)
| PROTAC-VIII Compound | L | Mass | DC$_{50}$ (µM) | D$_{max}$ (%) |
|---|---|---|---|---|
| PROTAC-VIII-61 | 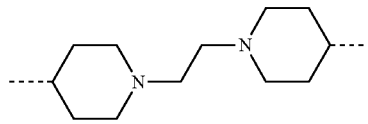 | 1014 | | |
| PROTAC-VIII-62 | 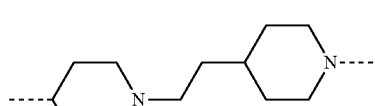 | 1014 | | |
| PROTAC-VIII-63 | 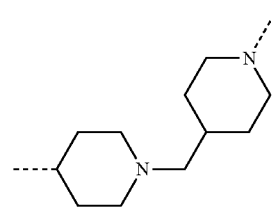 | 1000 | | |
| PROTAC-VIII-64 | 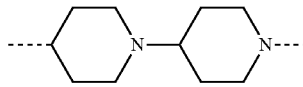 | 986 | | |
| PROTAC-VIII-65 | 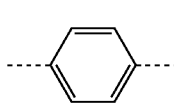 | 896 | | |
| PROTAC-VIII-66 |  | 906 | | |
| PROTAC-VIII-67 | 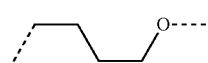 | 892 | | |
| PROTAC-VIII-68 | 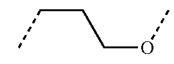 | 878 | | |
| PROTAC-VIII-69 | 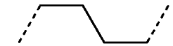 | 876 | | |
| PROTAC-VIII-70 | 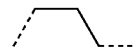 | 862 | | |

TABLE 8-continued

Protacs composed of a type-I Raf ligand and VHL ligand with right-side linkage having the following chemical structure

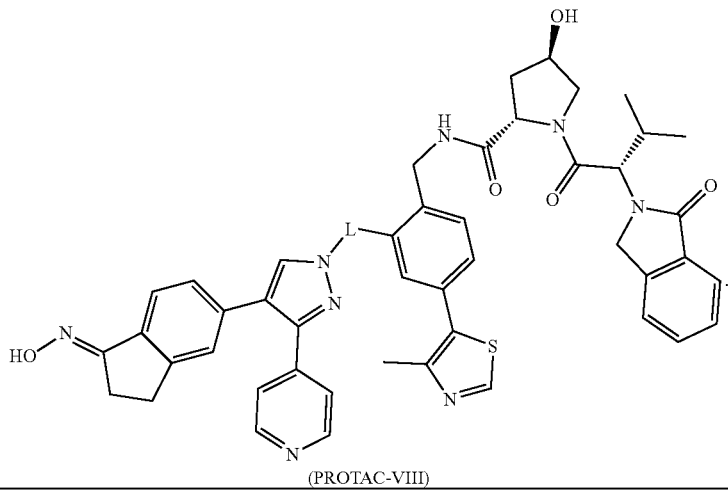

(PROTAC-VIII)

| PROTAC-VIII Compound | L | Mass | $DC_{50}$ (μM) | $D_{max}$ (%) |
|---|---|---|---|---|
| PROTAC-VIII-71 | ⟨linker: -CH2CH2-O-⟩ | 864 | | |

TABLE 9

Protacs composed of a RAF ligand and a cereblon ligand with 5-position linkage having the following chemical structure

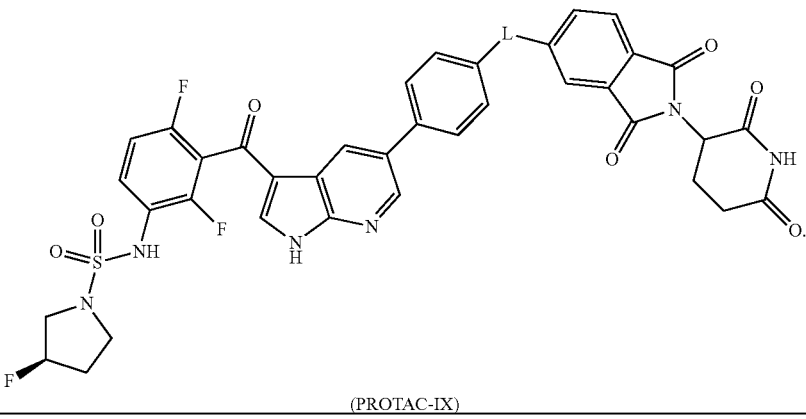

(PROTAC-IX)

| PROTAC-IX Compound | L | Mass | $DC_{50}$ (μM) | $D_{max}$ (%) |
|---|---|---|---|---|
| PROTAC-IX-1 | ⟨linker⟩ | 816 | | |
| PROTAC-IX-2 | ⟨linker⟩ | 860 | <3 | ≥10 |
| PROTAC-IX-3 | ⟨linker⟩ | 904 | <1 | ≥10 |
| PROTAC-IX-4 | ⟨linker⟩ | 948 | <1 | ≥10 |
| PROTAC-IX-5 | ⟨linker⟩ | 992 | | |

TABLE 9-continued
Protacs composed of a RAF ligand and a cereblon ligand with 5-position linkage having the following chemical structure
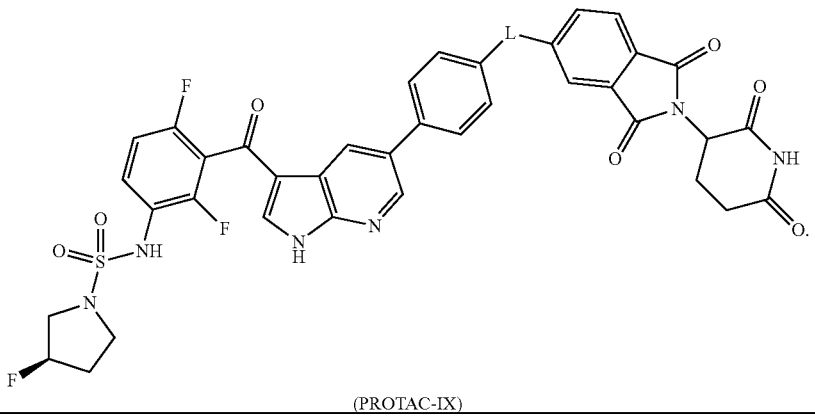
(PROTAC-IX)
| PROTAC-IX Compound | L | Mass | DC$_{50}$ (μM) | D$_{max}$ (%) |
|---|---|---|---|---|
| PROTAC-IX-6 | | 1036 | | |
| PROTAC-IX-7 | | 800 | | |
| PROTAC-IX-8 | | 786 | | |
| PROTAC-IX-9 | | 800 | | |
| PROTAC-IX-10 | | 786 | | |
| PROTAC-IX-11 | | 830 | | |
| PROTAC-IX-12 | | 844 | | |
| PROTAC-IX-13 | | 874 | | |
| PROTAC-IX-14 | | 874 | | |
| PROTAC-IX-15 | | 872 | | |
| PROTAC-IX-16 | | 888 | | |
| PROTAC-IX-17 | | 888 | | |
| PROTAC-IX-18 | | 888 | | |
| PROTAC-IX-19 | | 918 | | |
| PROTAC-IX-20 | | 918 | | |

TABLE 9-continued

Protacs composed of a RAF ligand and a cereblon ligand with 5-position linkage having the following chemical structure

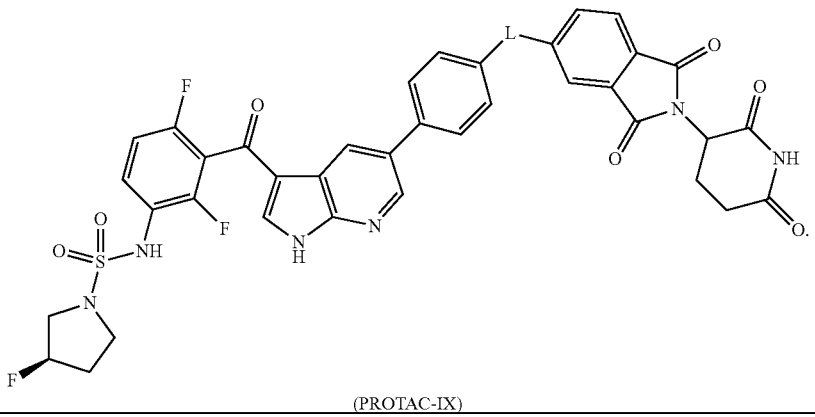

(PROTAC-IX)

| PROTAC-IX Compound | L | Mass | DC$_{50}$ (μM) | D$_{max}$ (%) |
|---|---|---|---|---|
| PROTAC-IX-21 | ----O~O~O~O~O`` | 918 | | |
| PROTAC-IX-22 | ----O~O~O~O`` | 916 | | |
| PROTAC-IX-23 | ----O~O~O~O`` | 916 | | |
| PROTAC-IX-24 | ----O~O~O~O`` | 916 | | |
| PROTAC-IX-25 | ----O~O~O~O`` | 916 | | |
| PROTAC-IX-26 | ----O~O~O~O`` | 916 | | |
| PROTAC-IX-27 | ----O~O~O~O~O---- | 932 | | |
| PROTAC-IX-28 | ----O~O~O~O~O---- | 932 | | |
| PROTAC-IX-29 | ----O~O~O~O~O---- | 932 | | |
| PROTAC-IX-30 | ----O~O~O~O~O---- | 932 | | |
| PROTAC-IX-31 | ----O~O~O~O~O---- | 932 | | |
| PROTAC-IX-32 | ----O~O~O~O---- | 930 | | |
| PROTAC-IX-33 | ----O~O~O~O---- | 930 | | |
| PROTAC-IX-34 | ----O~O~O~O---- | 930 | | |
| PROTAC-IX-35 | ----O~O~O~O---- | 930 | | |

TABLE 9-continued

Protacs composed of a RAF ligand and a cereblon ligand with 5-position linkage having the following chemical structure

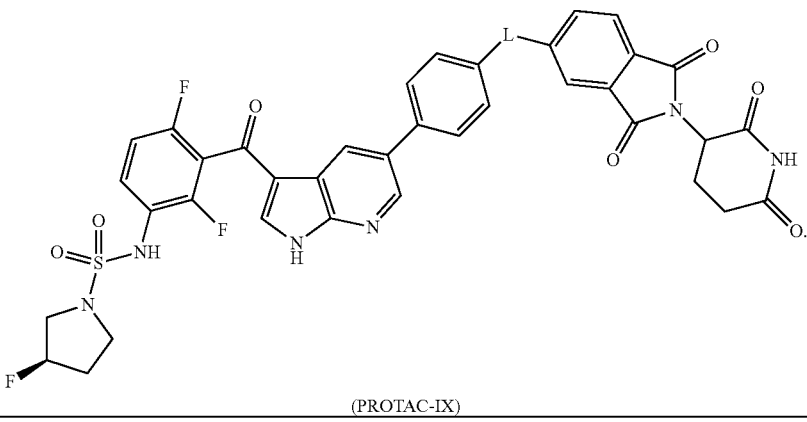

(PROTAC-IX)

| PROTAC-IX Compound | L | Mass | $DC_{50}$ ($\mu$M) | $D_{max}$ (%) |
|---|---|---|---|---|
| PROTAC-IX-36 | ----O~~O~~~~O---- | 930 | | |
| PROTAC-IX-37 | ----O~O~~~~~O---- | 930 | | |
| PROTAC-IX-38 | ----N(piperazine)N---- | 840 | | |
| PROTAC-IX-39 | O~N(piperazine)N---- | 884 | | |
| PROTAC-IX-40 | ----N(piperazine)N~O | 884 | | |
| PROTAC-IX-41 | ----O~N(piperazine)N---- | 898 | | |
| PROTAC-IX-42 | ----N(piperazine)N~O---- | 898 | | |
| PROTAC-IX-43 | O~~N(piperazine)N---- | 912 | | |
| PROTAC-IX-44 | ----N(piperazine)N~~O | 912 | | |
| PROTAC-IX-45 | ----O~O~N(piperazine)N---- | 928 | | |
| PROTAC-IX-46 | ----N(piperazine)N~O~O---- | 928 | | |

TABLE 9-continued

Protacs composed of a RAF ligand and a cereblon ligand with 5-position linkage having the following chemical structure

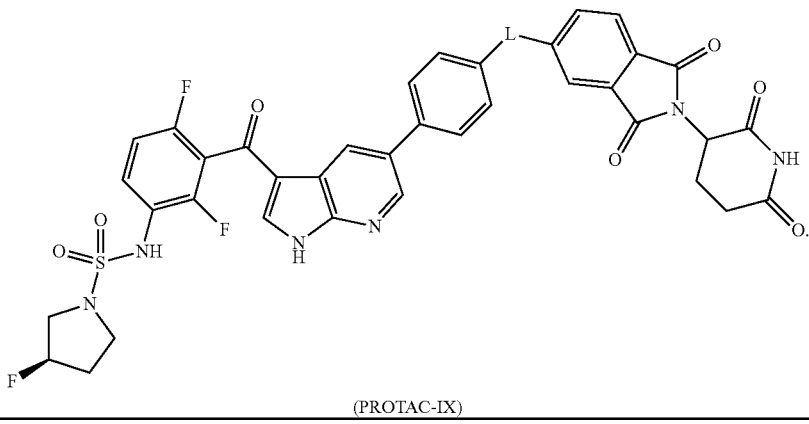

(PROTAC-IX)

| PROTAC-IX Compound | L | Mass | DC$_{50}$ (μM) | D$_{max}$ (%) |
|---|---|---|---|---|
| PROTAC-IX-47 | ----N(piperazine)-CH₂CH₂-N(piperazine)N---- | 952 | | |
| PROTAC-IX-48 | O-CH₂CH₂-N(piperazine)-CH₂CH₂-O | 928 | | |
| PROTAC-IX-49 | O-CH₂CH₂-O-CH₂CH₂-N(piperazine)N---- | 942 | | |
| PROTAC-IX-50 | O-CH₂-O-CH₂CH₂-N(piperazine)N---- | 942 | | |
| PROTAC-IX-51 | O-(CH₂)₄-N(piperazine)N---- | 940 | | |
| PROTAC-IX-52 | ----N(piperazine)N-CH₂CH₂-O-CH₂CH₂CH₂-O | 942 | | |
| PROTAC-IX-53 | ----N(piperazine)N-CH₂CH₂-O-CH₂CH₂-O | 942 | | |
| PROTAC-IX-54 | ----N(piperazine)N-(CH₂)₄-O | 940 | | |
| PROTAC-IX-55 | ----N(piperazine)N-CH₂CH₂-N(piperazine)N---- | 966 | | |

TABLE 9-continued
Protacs composed of a RAF ligand and a cereblon ligand with 5-position linkage having the following chemical structure
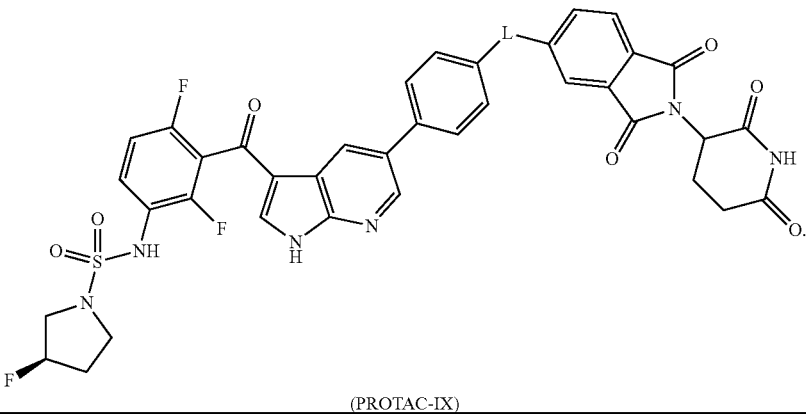
(PROTAC-IX)
| PROTAC-IX Compound | L | Mass | DC$_{50}$ (μM) | D$_{max}$ (%) |
|---|---|---|---|---|
| PROTAC-IX-56 | | 942 | | |
| PROTAC-IX-57 | | 942 | | |
| PROTAC-IX-58 | | 956 | | |
| PROTAC-IX-59 | | 956 | | |
| PROTAC-IX-60 | | 956 | | |
| PROTAC-IX-61 | | 954 | | |
| PROTAC-IX-62 | | 956 | | |
| PROTAC-IX-63 | | 956 | | |
| PROTAC-IX-64 | | 956 | | |
| PROTAC-IX-65 | | 954 | | |
| PROTAC-IX-66 | | 980 | | |

TABLE 9-continued

Protacs composed of a RAF ligand and a cereblon ligand with 5-position linkage having the following chemical structure

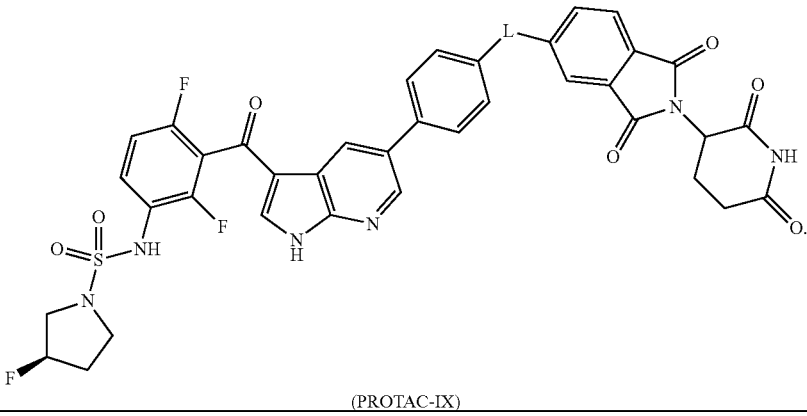

(PROTAC-IX)

| PROTAC-IX Compound | L | Mass | DC$_{50}$ (μM) | D$_{max}$ (%) |
|---|---|---|---|---|
| PROTAC-IX-67 | ----O⁀N(piperazine)N⁀O---- | 956 | | |
| PROTAC-IX-68 | ⋅⋅⋅O⁀⁀N(piperazine)N⁀O⋅⋅⋅ | 956 | | |
| PROTAC-IX-69 | ⋅⋅⋅O⁀N(piperazine)N⁀⁀O⋅⋅⋅ | 956 | | |
| PROTAC-IX-70 | ----O⋅⋅⋅ | 772 | | |

TABLE 10

Protacs composed of a RAF ligand and a cereblon ligand with 5-position linkage having the following chemical structure

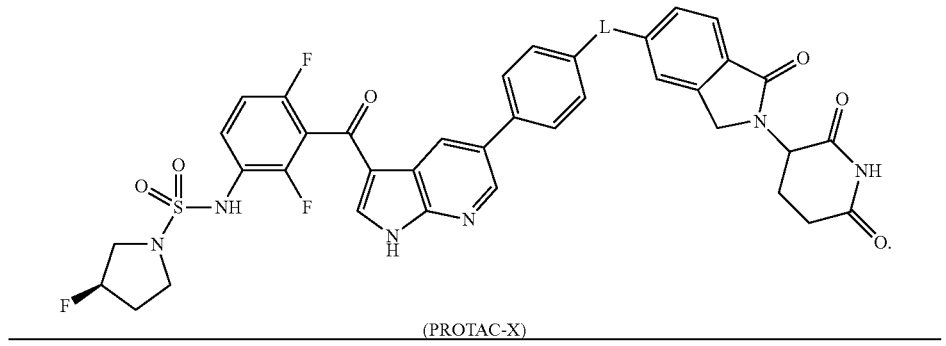

(PROTAC-X)

| PROTAC-X Compound | L | Mass | DC$_{50}$ (μM) | D$_{max}$ (%) |
|---|---|---|---|---|
| PROTAC-X-1 | ----O⁀O---- | 802 | | |
| PROTAC-X-2 | ----O⁀O⁀O⋅⋅⋅ | 846 | | |
| PROTAC-X-3 | ----O⁀O⁀O⁀O---- | 890 | | |

TABLE 10-continued
Protacs composed of a RAF ligand and a cereblon ligand with 5-position linkage having the following chemical structure
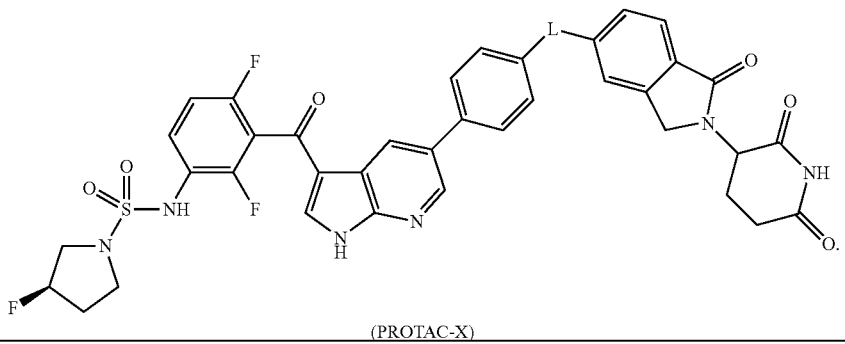
(PROTAC-X)
| PROTAC-X Compound | L | Mass | $DC_{50}$ ($\mu M$) | $D_{max}$ (%) |
|---|---|---|---|---|
| PROTAC-X-4 | | 934 | | |
| PROTAC-X-5 | | 978 | | |
| PROTAC-X-6 | | 1022 | | |
| PROTAC-X-7 | | 786 | | |
| PROTAC-X-8 | | 772 | | |
| PROTAC-X-9 | | 786 | | |
| PROTAC-X-10 | | 772 | | |
| PROTAC-X-11 | | 816 | | |
| PROTAC-X-12 | | 830 | | |
| PROTAC-X-13 | | 860 | | |
| PROTAC-X-14 | | 860 | | |
| PROTAC-X-15 | | 858 | | |
| PROTAC-X-16 | | 874 | | |
| PROTAC-X-17 | | 874 | | |
| PROTAC-X-18 | | 874 | | |
| PROTAC-X-19 | | 904 | | |

TABLE 10-continued

Protacs composed of a RAF ligand and a cereblon ligand with 5-position linkage having the following chemical structure (PROTAC-X)

| PROTAC-X Compound | L | Mass | DC$_{50}$ (μM) | D$_{max}$ (%) |
|---|---|---|---|---|
| PROTAC-X-20 | —O-CH₂CH₂-O-CH₂CH₂-O-CH₂CH₂-O- | 904 | | |
| PROTAC-X-21 | —O-CH₂CH₂-O-CH₂CH₂-O-CH₂CH₂-O- | 904 | | |
| PROTAC-X-22 | —O-CH₂CH₂-O-CH₂CH₂CH₂CH₂-O-CH₂CH₂-O- | 902 | | |
| PROTAC-X-23 | —O-CH₂CH₂CH₂-O-CH₂CH₂-O-CH₂CH₂-O- | 902 | | |
| PROTAC-X-24 | —O-CH₂CH₂CH₂-O-CH₂CH₂CH₂-O- | 902 | | |
| PROTAC-X-25 | —O-CH₂CH₂CH₂CH₂-O-CH₂CH₂-O- | 902 | | |
| PROTAC-X-26 | —O-CH₂CH₂-O-CH₂CH₂CH₂CH₂-O-CH₂CH₂-O- | 902 | | |
| PROTAC-X-27 | —O-CH₂CH₂-O-CH₂CH₂-O-CH₂CH₂CH₂-O- | 918 | | |
| PROTAC-X-28 | —O-CH₂CH₂-O-CH₂CH₂-O-CH₂CH₂-O-CH₂CH₂-O- | 918 | | |
| PROTAC-X-29 | —O-CH₂CH₂-O-CH₂CH₂-O-CH₂CH₂-O-CH₂CH₂-O- | 918 | | |
| PROTAC-X-30 | —O-CH₂CH₂-O-CH₂CH₂-O-CH₂CH₂-O-CH₂CH₂-O- | 918 | | |
| PROTAC-X-31 | —O-CH₂CH₂CH₂-O-CH₂CH₂-O-CH₂CH₂-O- | 918 | | |
| PROTAC-X-32 | —O-CH₂CH₂CH₂-O-CH₂CH₂CH₂-O-CH₂CH₂-O- | 916 | | |
| PROTAC-X-33 | —O-CH₂CH₂CH₂-O-CH₂CH₂CH₂-O-CH₂CH₂-O- | 916 | | |
| PROTAC-X-34 | —O-CH₂CH₂CH₂-O-CH₂CH₂-O-CH₂CH₂-O- | 916 | | |
| PROTAC-X-35 | —O-CH₂CH₂CH₂-O-CH₂CH₂-O-CH₂CH₂-O- | 916 | | |

TABLE 10-continued

Protacs composed of a RAF ligand and a cereblon ligand with 5-position linkage having the following chemical structure

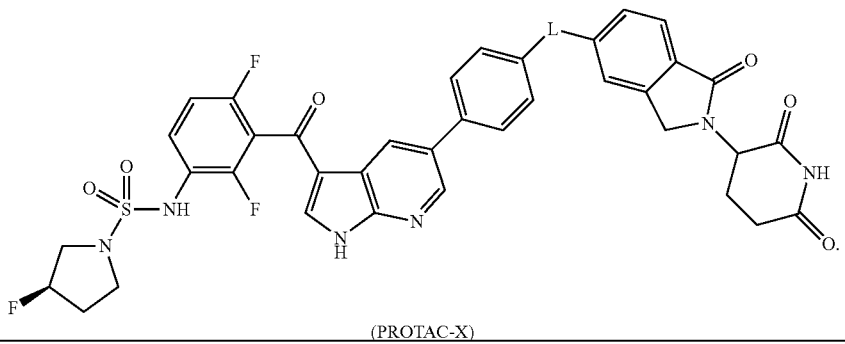

(PROTAC-X)

| PROTAC-X Compound | L | Mass | $DC_{50}$ ($\mu M$) | $D_{max}$ (%) |
|---|---|---|---|---|
| PROTAC-X-36 | ----O~O~~~O---- | 916 | | |
| PROTAC-X-37 | ----O~O~~~~O---- | 916 | | |
| PROTAC-X-38 | ----N(piperazine)N---- | 826 | | |
| PROTAC-X-39 | O~N(piperazine)N---- | 870 | | |
| PROTAC-X-40 | ----N(piperazine)N~O | 870 | | |
| PROTAC-X-41 | ----O~N(piperazine)N---- | 884 | | |
| PROTAC-X-42 | ----N(piperazine)N~O---- | 884 | | |
| PROTAC-X-43 | O~~N(piperazine)N---- | 898 | | |
| PROTAC-X-44 | ----N(piperazine)N~~O | 898 | | |
| PROTAC-X-45 | ----O~O~N(piperazine)N---- | 914 | | |
| PROTAC-X-46 | ----N(piperazine)N~O~O---- | 914 | | |
| PROTAC-X-47 | ----N(piperazine)N~N(piperazine)N---- | 938 | | |

TABLE 10-continued
Protacs composed of a RAF ligand and a cereblon ligand with 5-position linkage having the following chemical structure
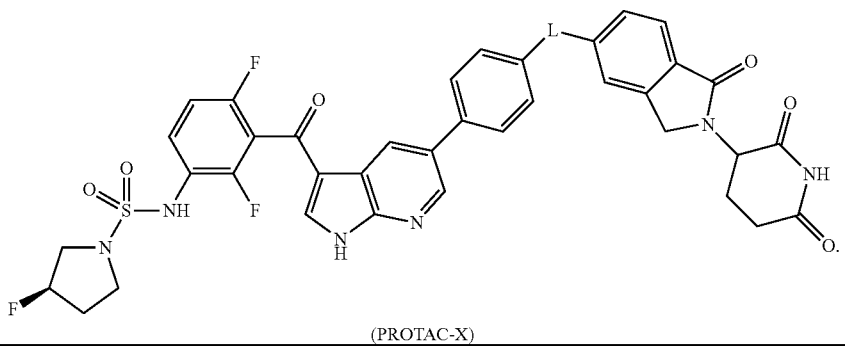
(PROTAC-X)
| PROTAC-X Compound | L | Mass | $DC_{50}$ (μM) | $D_{max}$ (%) |
|---|---|---|---|---|
| PROTAC-X-48 | | 914 | | |
| PROTAC-X-49 | | 928 | | |
| PROTAC-X-50 | | 928 | | |
| PROTAC-X-51 | | 926 | | |
| PROTAC-X-52 | | 928 | | |
| PROTAC-X-53 | | 928 | | |
| PROTAC-X-54 | | 926 | | |
| PROTAC-X-55 | | 952 | | |
| PROTAC-X-56 | | 928 | | |
| PROTAC-X-57 | | 928 | | |

TABLE 10-continued

Protacs composed of a RAF ligand and a cereblon ligand with 5-position linkage having the following chemical structure

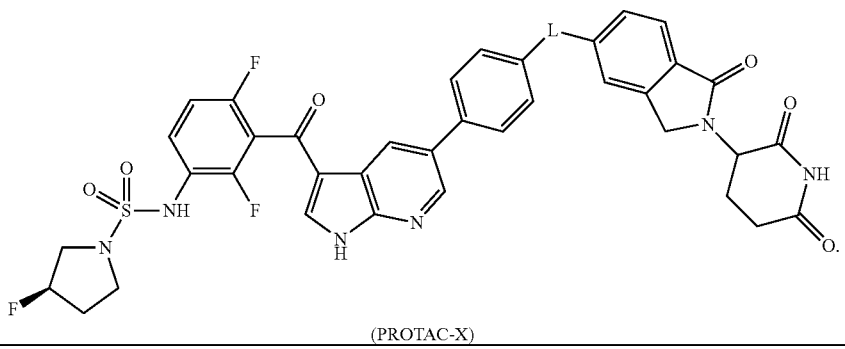

(PROTAC-X)

| PROTAC-X Compound | L | Mass | $DC_{50}$ (μM) | $D_{max}$ (%) |
|---|---|---|---|---|
| PROTAC-X-58 | ----O-CH₂CH₂CH₂-O-CH₂CH₂-N(piperazine)N---- | 942 | | |
| PROTAC-X-59 | ----O-CH₂CH₂-O-CH₂CH₂CH₂-N(piperazine)N---- | 942 | | |
| PROTAC-X-60 | ----O-CH₂-O-CH₂CH₂CH₂CH₂-N(piperazine)N---- | 942 | | |
| PROTAC-X-61 | ----O-(CH₂)₅-N(piperazine)N---- | 940 | | |
| PROTAC-X-62 | ----N(piperazine)N-CH₂CH₂CH₂-O-CH₂CH₂-O---- | 942 | | |
| PROTAC-X-63 | ----N(piperazine)N-CH₂CH₂-O-CH₂CH₂-O---- | 942 | | |
| PROTAC-X-64 | ----N(piperazine)N-CH₂CH₂-O-CH₂CH₂CH₂-O---- | 942 | | |
| PROTAC-X-65 | ----N(piperazine)N-(CH₂)₄-O---- | 940 | | |
| PROTAC-X-66 | ----N(piperazine)N-CH₂CH₂CH₂-N(piperazine)N---- | 966 | | |
| PROTAC-X-67 | ----O-CH₂CH₂-N(piperazine)N-CH₂CH₂-O---- | 942 | | |
| PROTAC-X-68 | ----O-CH₂CH₂CH₂CH₂-N(piperazine)N-CH₂CH₂-O---- | 942 | | |

TABLE 10-continued

Protacs composed of a RAF ligand and a cereblon ligand with 5-position linkage having the following chemical structure (PROTAC-X)

| PROTAC-X Compound | L | Mass | DC$_{50}$ (µM) | D$_{max}$ (%) |
|---|---|---|---|---|
| PROTAC-X-69 | (structure) | 942 | | |
| PROTAC-X-70 | (structure) | 758 | | |

TABLE 11

Protacs composed of a RAF ligand and a cereblon ligand with 6-position linkage having the following chemical structure (PROTAC-XI)

| PROTAC-XI Compound | L | Mass | DC$_{50}$ (µM) | D$_{max}$ (%) |
|---|---|---|---|---|
| PROTAC-XI-1 | (structure) | 802 | | |
| PROTAC-XI-2 | (structure) | 846 | | |
| PROTAC-XI-3 | (structure) | 890 | | |
| PROTAC-XI-4 | (structure) | 934 | | |
| PROTAC-XI-5 | (structure) | 978 | | |
| PROTAC-XI-6 | (structure) | 1022 | | |

TABLE 11-continued
Protacs composed of a RAF ligand and a cereblon ligand with 6-position linkage having the following chemical structure
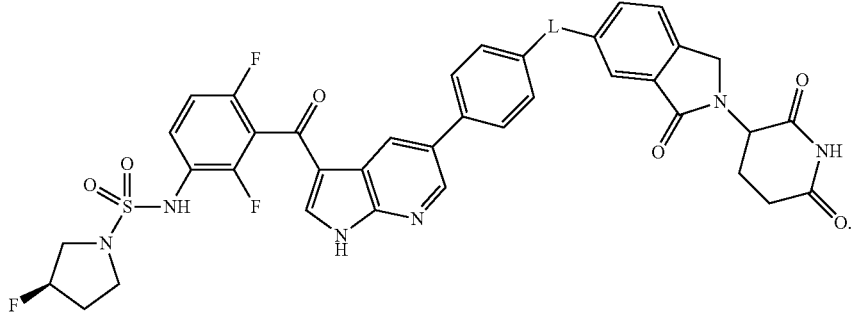
(PROTAC-XI)
| PROTAC-XI Compound | L | Mass | DC$_{50}$ (µM) | D$_{max}$ (%) |
|---|---|---|---|---|
| PROTAC-XI-7 | 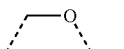 | 786 | | |
| PROTAC-XI-8 | 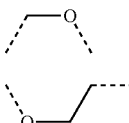 | 772 | | |
| PROTAC-XI-9 | 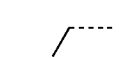 | 786 | | |
| PROTAC-XI-10 | 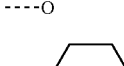 | 772 | | |
| PROTAC-XI-11 | 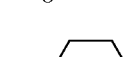 | 816 | | |
| PROTAC-XI-12 | 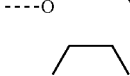 | 830 | | |
| PROTAC-XI-13 | 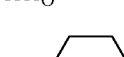 | 860 | | |
| PROTAC-XI-14 | 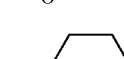 | 860 | | |
| PROTAC-XI-15 | 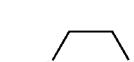 | 858 | | |
| PROTAC-XI-16 | 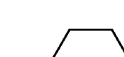 | 874 | | |
| PROTAC-XI-17 | 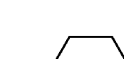 | 874 | | |
| PROTAC-XI-18 | 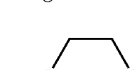 | 874 | | |
| PROTAC-XI-19 | 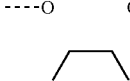 | 904 | | |
| PROTAC-XI-20 | 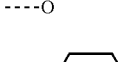 | 904 | | |
| PROTAC-XI-21 | 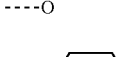 | 904 | | |
| PROTAC-XI-22 | | 902 | | |

TABLE 11-continued
Protacs composed of a RAF ligand and a cereblon ligand with 6-position linkage having the following chemical structure
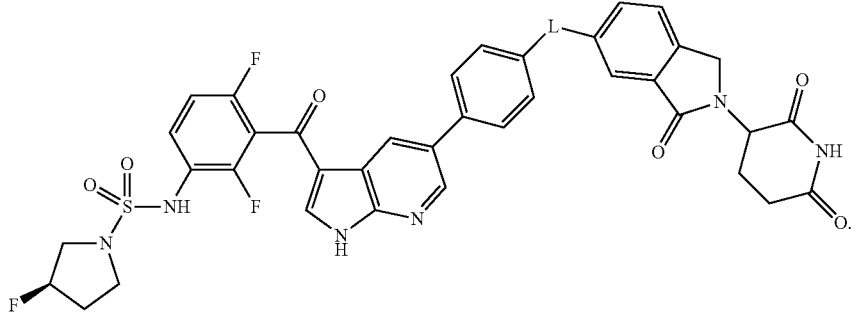
(PROTAC-XI)
| PROTAC-XI Compound | L | Mass | DC$_{50}$ (μM) | D$_{max}$ (%) |
|---|---|---|---|---|
| PROTAC-XI-23 |  | 902 | | |
| PROTAC-XI-24 | 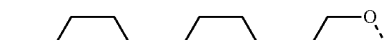 | 902 | | |
| PROTAC-XI-25 | 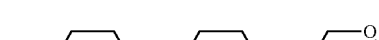 | 902 | | |
| PROTAC-XI-26 | 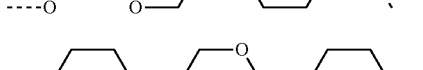 | 902 | | |
| PROTAC-XI-27 | 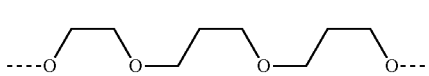 | 918 | | |
| PROTAC-XI-28 | 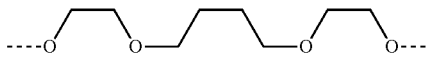 | 918 | | |
| PROTAC-XI-29 | 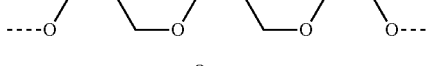 | 918 | | |
| PROTAC-XI-30 | 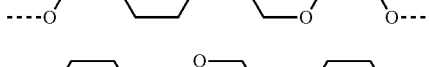 | 918 | | |
| PROTAC-XI-31 | 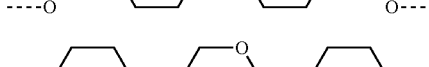 | 918 | | |
| PROTAC-XI-32 | 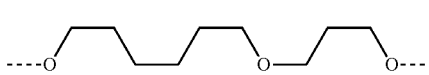 | 916 | | |
| PROTAC-XI-33 | 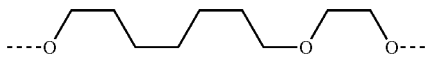 | 916 | | |
| PROTAC-XI-34 |  | 916 | | |
| PROTAC-XI-35 |  | 916 | | |
| PROTAC-XI-36 |  | 916 | | |
| PROTAC-XI-37 |  | 916 | | |
| PROTAC-XI-38 |  | 826 | | |

TABLE 11-continued

Protacs composed of a RAF ligand and a cereblon ligand with 6-position linkage having the following chemical structure

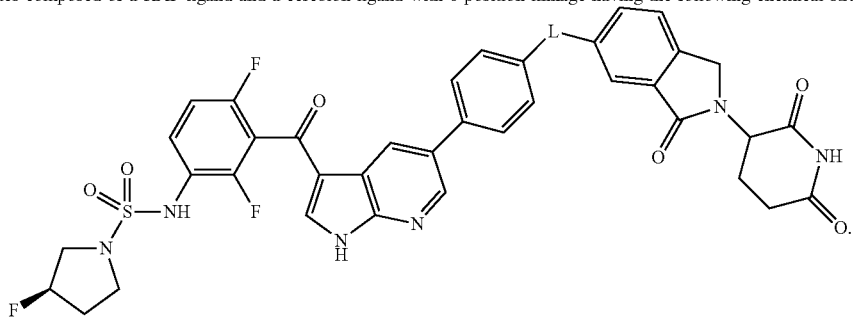

(PROTAC-XI)

| PROTAC-XI Compound | L | Mass | DC$_{50}$ (μM) | D$_{max}$ (%) |
|---|---|---|---|---|
| PROTAC-XI-39 | ![O-CH2CH2-piperazine] | 870 | | |
| PROTAC-XI-40 | ![piperazine-CH2CH2-O] | 870 | | |
| PROTAC-XI-41 | ![O-CH2CH2-piperazine] | 884 | | |
| PROTAC-XI-42 | ![piperazine-CH2CH2-O] | 884 | | |
| PROTAC-XI-43 | ![O-CH2CH2CH2-piperazine] | 898 | | |
| PROTAC-XI-44 | ![piperazine-CH2CH2CH2-O] | 898 | | |
| PROTAC-XI-45 | ![O-CH2CH2-O-CH2CH2-piperazine] | 914 | | |
| PROTAC-XI-46 | ![piperazine-CH2CH2-O-CH2CH2-O] | 914 | | |
| PROTAC-XI-47 | ![piperazine-CH2CH2-piperazine] | 938 | | |
| PROTAC-XI-48 | ![O-CH2CH2-piperazine-CH2CH2-O] | 914 | | |
| PROTAC-XI-49 | ![O-CH2CH2-O-CH2CH2-piperazine] | 928 | | |

TABLE 11-continued
Protacs composed of a RAF ligand and a cereblon ligand with 6-position linkage having the following chemical structure
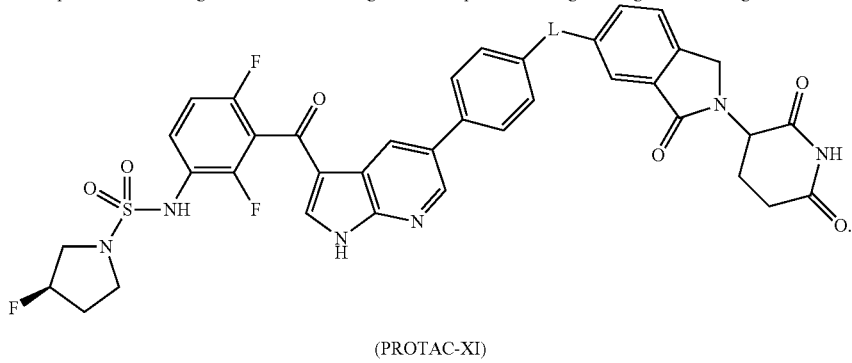
(PROTAC-XI)
| PROTAC-XI Compound | L | Mass | DC$_{50}$ (μM) | D$_{max}$ (%) |
|---|---|---|---|---|
| PROTAC-XI-50 | | 928 | | |
| PROTAC-XI-51 | | 926 | | |
| PROTAC-XI-52 | | 928 | | |
| PROTAC-XI-53 | | 928 | | |
| PROTAC-XI-54 | | 926 | | |
| PROTAC-XI-55 | | 952 | | |
| PROTAC-XI-56 | | 928 | | |
| PROTAC-XI-57 | | 928 | | |
| PROTAC-XI-58 | | 942 | | |
| PROTAC-XI-59 | | 942 | | |

TABLE 11-continued

Protacs composed of a RAF ligand and a cereblon ligand with 6-position linkage having the following chemical structure

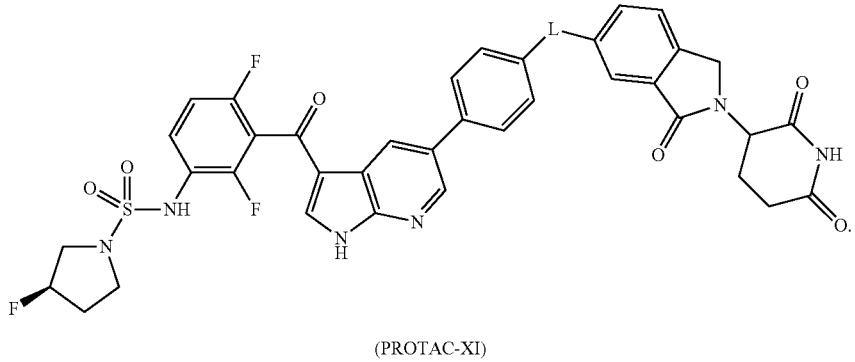

(PROTAC-XI)

| PROTAC-XI Compound | L | Mass | DC$_{50}$ (μM) | D$_{max}$ (%) |
|---|---|---|---|---|
| PROTAC-XI-60 | ----O\_/O\_\_\_/N\_N---- | 942 | | |
| PROTAC-XI-61 | ----O\_\_\_\_\_/N\_N---- | 940 | | |
| PROTAC-XI-62 | ----N\_N\_\_\_O\_/O---- | 942 | | |
| PROTAC-XI-63 | ----N\_N\_\_O\_\_O---- | 942 | | |
| PROTAC-XI-64 | ----N\_N\_\_O\_\_O---- | 942 | | |
| PROTAC-XI-65 | ----N\_N\_\_\_\_O---- | 940 | | |
| PROTAC-XI-66 | ----N\_N\_\_N\_N---- | 966 | | |
| PROTAC-XI-67 | ----O\_\_N\_N\_\_O---- | 942 | | |
| PROTAC-XI-68 | ----O\_\_\_N\_N\_\_O---- | 942 | | |
| PROTAC-XI-69 | ----O\_\_N\_N\_\_\_O---- | 942 | | |
| PROTAC-XI-70 | ----O\ | 758 | | |

TABLE 12

Protacs composed of a RAF ligand and a cereblon ligand with 4-position linkage having the following chemical structure

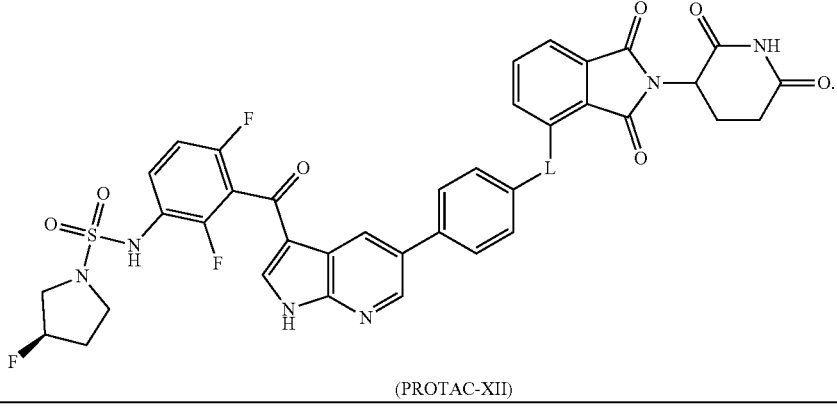

(PROTAC-XII)

| PROTAC-XII Compound | L | Mass | $DC_{50}$ (μM) | $D_{max}$ (%) |
|---|---|---|---|---|
| PROTAC-XII-1 | ----O〜O〜O---- | 816 | | |
| PROTAC-XII-2 | ----O〜O〜O〜 | 860 | | |
| PROTAC-XII-3 | ----O〜O〜O〜O---- | 904 | <3 | ≥10 |
| PROTAC-XII-4 | ----O〜O〜O〜O〜O〜 | 948 | <1 | ≥10 |
| PROTAC-XII-5 | ----O〜O〜O〜O〜O---- | 992 | <1 | ≥10 |
| PROTAC-XII-6 | ----O〜O〜O〜O〜O〜O〜 | 1036 | <1 | ≥10 |
| PROTAC-XII-7 | ----O〜 | 800 | | |
| PROTAC-XII-8 | 〜O〜 | 786 | | |
| PROTAC-XII-9 | 〜O〜 | 800 | | |
| PROTAC-XII-10 | ----O〜 | 786 | | |
| PROTAC-XII-11 | ----O〜O〜 | 830 | | |
| PROTAC-XII-12 | ----O〜O---- | 844 | | |
| PROTAC-XII-13 | ----O〜O〜O---- | 874 | | |
| PROTAC-XII-14 | ----O〜O〜O---- | 874 | | |
| PROTAC-XII-15 | ----O〜O---- | 872 | | |
| PROTAC-XII-16 | ----O〜O〜O〜 | 888 | | |

TABLE 12-continued

Protacs composed of a RAF ligand and a cereblon ligand with 4-position linkage having the following chemical structure

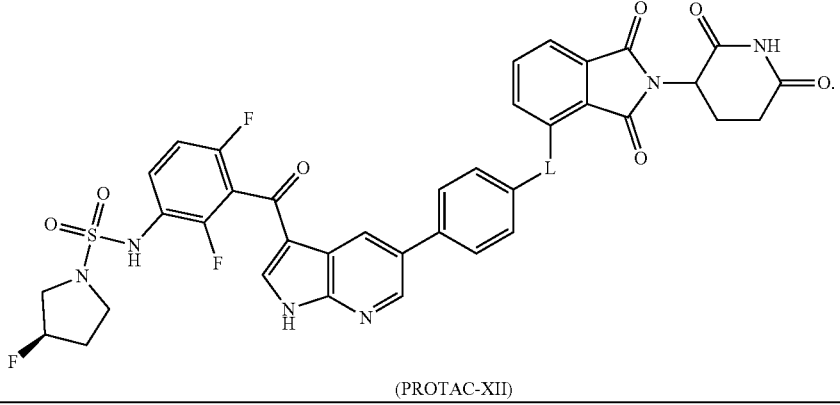

(PROTAC-XII)

| PROTAC-XII Compound | L | Mass | $DC_{50}$ ($\mu$M) | $D_{max}$ (%) |
|---|---|---|---|---|
| PROTAC-XII-17 | ----O~O~O~ | 888 | | |
| PROTAC-XII-18 | ----O~O~O~ | 888 | | |
| PROTAC-XII-19 | ----O~O~O~O~ | 918 | | |
| PROTAC-XII-20 | ----O~O~O~O~ | 918 | | |
| PROTAC-XII-21 | ----O~O~O~O~ | 918 | | |
| PROTAC-XII-22 | ----O~O~O~ | 916 | | |
| PROTAC-XII-23 | ----O~O~O~ | 916 | | |
| PROTAC-XII-24 | ----O~O~O~ | 916 | | |
| PROTAC-XII-25 | ----O~O~O~ | 916 | | |
| PROTAC-XII-26 | ----O~O~O~ | 916 | | |
| PROTAC-XII-27 | ----O~O~O~O---- | 932 | | |
| PROTAC-XII-28 | ----O~O~O~O---- | 932 | | |
| PROTAC-XII-29 | ----O~O~O~O---- | 932 | | |
| PROTAC-XII-30 | ----O~O~O~O---- | 932 | | |
| PROTAC-XII-31 | ----O~O~O~O---- | 932 | | |

TABLE 12-continued

Protacs composed of a RAF ligand and a cereblon ligand with 4-position linkage having the following chemical structure

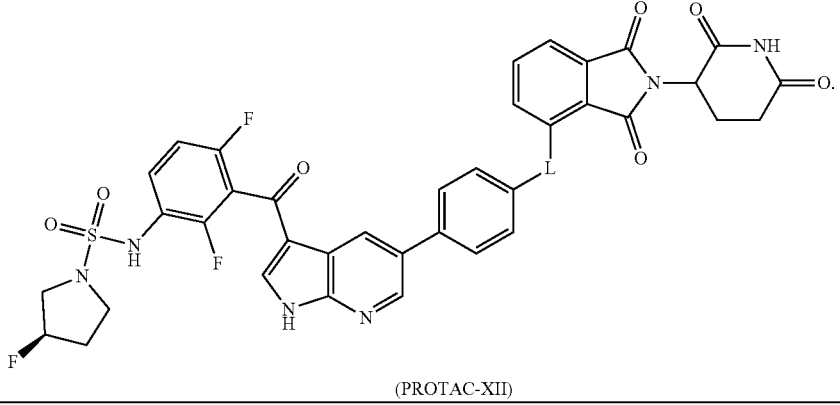

(PROTAC-XII)

| PROTAC-XII Compound | L | Mass | DC$_{50}$ (μM) | D$_{max}$ (%) |
|---|---|---|---|---|
| PROTAC-XII-32 | ----O-CH₂CH₂CH₂-O-CH₂CH₂CH₂CH₂-O---- | 930 | | |
| PROTAC-XII-33 | ----O-CH₂CH₂CH₂CH₂-O-CH₂CH₂CH₂-O---- | 930 | | |
| PROTAC-XII-34 | ----O-CH₂CH₂CH₂-CH₂CH₂-O-CH₂CH₂-O---- | 930 | | |
| PROTAC-XII-35 | ----O-CH₂CH₂CH₂CH₂CH₂-O-CH₂CH₂-O---- | 930 | | |
| PROTAC-XII-36 | ----O-CH₂CH₂-O-CH₂CH₂CH₂CH₂CH₂-O---- | 930 | | |
| PROTAC-XII-37 | ----O-CH₂-O-CH₂CH₂CH₂CH₂CH₂CH₂-O---- | 930 | | |
| PROTAC-XII-38 | ----N(piperazine)N---- | 840 | | |
| PROTAC-XII-39 | O-CH₂CH₂-N(piperazine)N---- | 884 | | |
| PROTAC-XII-40 | ----N(piperazine)N-CH₂CH₂-O | 884 | | |
| PROTAC-XII-41 | ----O-CH₂CH₂-N(piperazine)N---- | 898 | | |
| PROTAC-XII-42 | ----N(piperazine)N-CH₂CH₂-O---- | 898 | | |
| PROTAC-XII-43 | O-CH₂CH₂CH₂-N(piperazine)N---- | 912 | | |
| PROTAC-XII-44 | ----N(piperazine)N-CH₂CH₂CH₂-O | 912 | | |

TABLE 12-continued

Protacs composed of a RAF ligand and a cereblon ligand with 4-position linkage having the following chemical structure

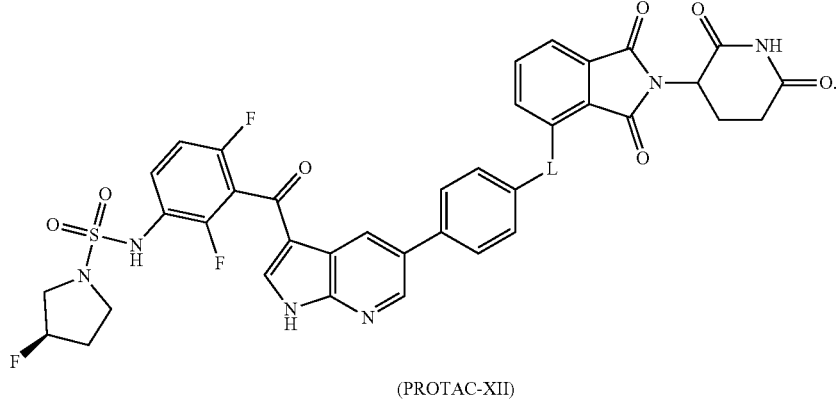

(PROTAC-XII)

| PROTAC-XII Compound | L | Mass | DC$_{50}$ (μM) | D$_{max}$ (%) |
|---|---|---|---|---|
| PROTAC-XII-45 | ----O⁀⁀O⁀⁀N(piperazine)N---- | 928 | | |
| PROTAC-XII-46 | ----N(piperazine)N⁀⁀O⁀⁀O---- | 928 | | |
| PROTAC-XII-47 | ----N(piperazine)N⁀⁀N(piperazine)N---- | 952 | | |
| PROTAC-XII-48 | O⁀⁀N(piperazine)N⁀⁀O | 928 | | |
| PROTAC-XII-49 | O⁀⁀O⁀⁀N(piperazine)N---- | 942 | | |
| PROTAC-XII-50 | O⁀⁀O⁀⁀N(piperazine)N---- | 942 | | |
| PROTAC-XII-51 | O⁀⁀⁀⁀N(piperazine)N---- | 940 | | |
| PROTAC-XII-52 | ----N(piperazine)N⁀⁀O⁀⁀O | 942 | | |
| PROTAC-XII-53 | ----N(piperazine)N⁀⁀O⁀⁀O | 942 | | |
| PROTAC-XII-54 | ----N(piperazine)N⁀⁀⁀⁀O | 940 | | |

TABLE 12-continued

Protacs composed of a RAF ligand and a cereblon ligand with 4-position linkage having the following chemical structure

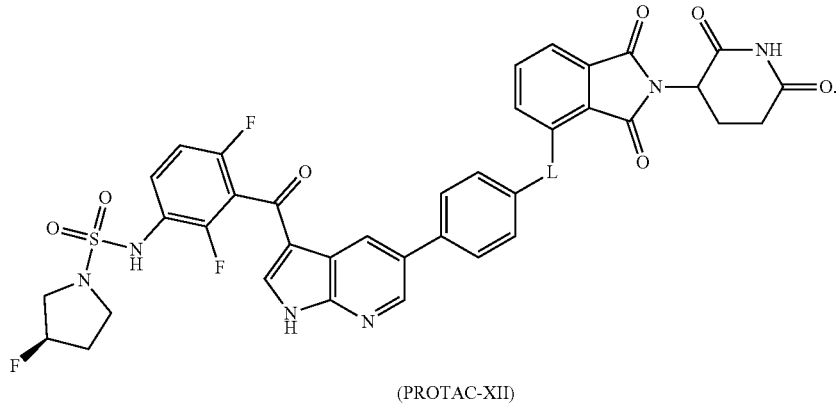

(PROTAC-XII)

| PROTAC-XII Compound | L | Mass | DC$_{50}$ (μM) | D$_{max}$ (%) |
|---|---|---|---|---|
| PROTAC-XII-55 | ![piperazine-CH2CH2-N-methylpiperazine] | 966 | | |
| PROTAC-XII-56 | ![O-CH2CH2-piperazine-CH2CH2-O] | 942 | | |
| PROTAC-XII-57 | ![O-CH2CH2-piperazine-CH2CH2CH2-O] | 942 | | |
| PROTAC-XII-58 | ![O-CH2CH2CH2-O-CH2CH2-piperazine] | 956 | | |
| PROTAC-XII-59 | ![O-CH2CH2-O-CH2CH2-piperazine] | 956 | | |
| PROTAC-XII-60 | ![O-CH2CH2-O-CH2CH2CH2-piperazine] | 956 | | |
| PROTAC-XII-61 | ![O-(CH2)5-piperazine] | 954 | | |
| PROTAC-XII-62 | ![piperazine-CH2CH2CH2-O-CH2CH2-O] | 956 | | |

TABLE 12-continued

Protacs composed of a RAF ligand and a cereblon ligand with 4-position linkage having the following chemical structure

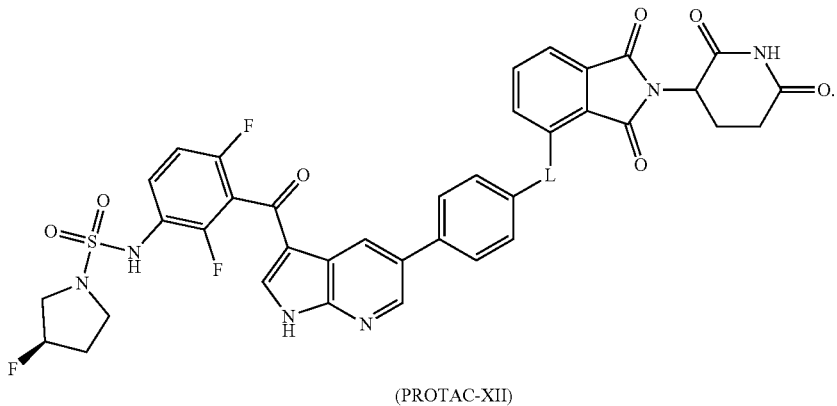

(PROTAC-XII)

| PROTAC-XII Compound | L | Mass | $DC_{50}$ (μM) | $D_{max}$ (%) |
|---|---|---|---|---|
| PROTAC-XII-63 | ----N(piperazine)N-CH2CH2-O-CH2CH2-O---- | 956 | | |
| PROTAC-XII-64 | ----N(piperazine)N-CH2CH2-O-CH2CH2CH2-O---- | 956 | | |
| PROTAC-XII-65 | ----N(piperazine)N-(CH2)4-O---- | 954 | | |
| PROTAC-XII-66 | ----N(piperazine)N-(CH2)3-N(piperazine)N---- | 980 | | |
| PROTAC-XII-67 | ----O-CH2CH2CH2-N(piperazine)N-CH2CH2-O---- | 956 | | |
| PROTAC-XII-68 | ····O-(CH2)4-N(piperazine)N-CH2CH2-O···· | 956 | | |
| PROTAC-XII-69 | ····O-CH2CH2-N(piperazine)N-(CH2)4-O···· | 956 | | |
| PROTAC-XII-70 | ----O···· | 772 | | |

TABLE 13

Protacs composed of a RAF ligand and a cereblon ligand with 4-position linkage having the following chemical structure

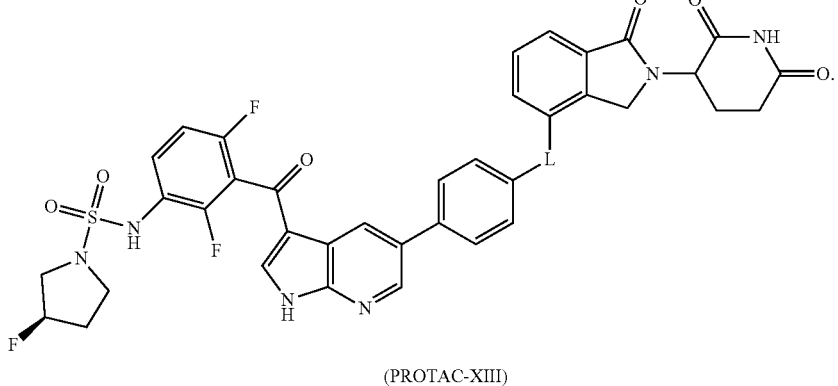

(PROTAC-XIII)

| PROTAC-XIII Compound | L | Mass | DC$_{50}$ (μM) | D$_{max}$ (%) |
|---|---|---|---|---|
| PROTAC-XIII-1 | ----O~~O---- | 802 | | |
| PROTAC-XIII-2 | ----O~~O~~O∙∙ | 846 | | |
| PROTAC-XIII-3 | ----O~~O~~O---- | 890 | | |
| PROTAC-XIII-4 | ----O~~O~~O~~O∙∙ | 934 | | |
| PROTAC-XIII-5 | ----O~~O~~O~~O~~O---- | 978 | | |
| PROTAC-XIII-6 | ----O~~O~~O~~O~~O~~O∙∙ | 1022 | | |
| PROTAC-XIII-7 | ----O~~O∙∙ | 786 | | |
| PROTAC-XIII-8 | ∙∙O~~O∙∙ | 772 | | |
| PROTAC-XIII-9 | ∙∙O~~O---- | 786 | | |
| PROTAC-XIII-10 | ----O~~---- | 772 | | |
| PROTAC-XIII-11 | ----O~~~O∙∙ | 816 | | |
| PROTAC-XIII-12 | ----O~~~O---- | 830 | | |
| PROTAC-XIII-13 | ----O~~O~~O---- | 860 | | |
| PROTAC-XIII-14 | ----O~~O~~O---- | 860 | | |
| PROTAC-XIII-15 | ----O~~~O---- | 858 | | |
| PROTAC-XIII-16 | ----O~~O~~~O∙∙ | 874 | | |

TABLE 13-continued

Protacs composed of a RAF ligand and a cereblon ligand with 4-position linkage having the following chemical structure

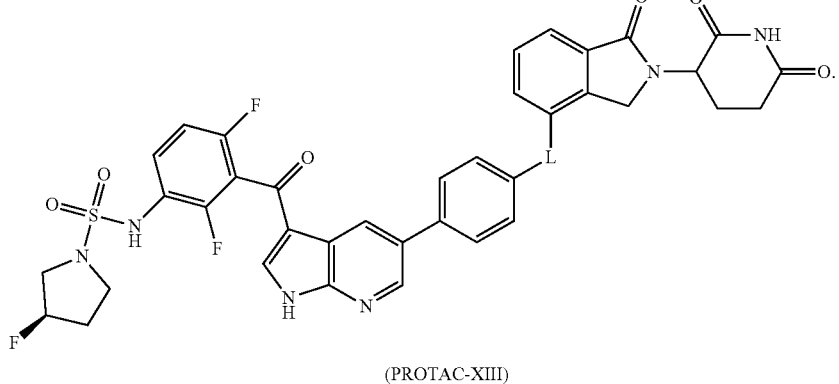

(PROTAC-XIII)

| PROTAC-XIII Compound | L | Mass | DC$_{50}$ (μM) | D$_{max}$ (%) |
|---|---|---|---|---|
| PROTAC-XIII-17 | ----O~~O~~O~ | 874 | | |
| PROTAC-XIII-18 | ----O~~O~~O~ | 874 | | |
| PROTAC-XIII-19 | ----O~O~~O~~O~ | 904 | | |
| PROTAC-XIII-20 | ----O~O~~O~~O~ | 904 | | |
| PROTAC-XIII-21 | ----O~~O~~O~~O~ | 904 | | |
| PROTAC-XIII-22 | ----O~~O~~~O~ | 902 | | |
| PROTAC-XIII-23 | ----O~~O~~~O~ | 902 | | |
| PROTAC-XIII-24 | ----O~~~O~~O~ | 902 | | |
| PROTAC-XIII-25 | ----O~~~O~~O~ | 902 | | |
| PROTAC-XIII-26 | ----O~O~~~O~ | 902 | | |
| PROTAC-XIII-27 | ----O~O~~O~~~O---- | 918 | | |
| PROTAC-XIII-28 | ----O~O~~O~~O~O---- | 918 | | |
| PROTAC-XIII-29 | ----O~O~~O~~O~O---- | 918 | | |
| PROTAC-XIII-30 | ----O~~O~~O~~O~O---- | 918 | | |
| PROTAC-XIII-31 | ----O~~O~~O~~O---- | 918 | | |

TABLE 13-continued

Protacs composed of a RAF ligand and a cereblon ligand with 4-position linkage having the following chemical structure

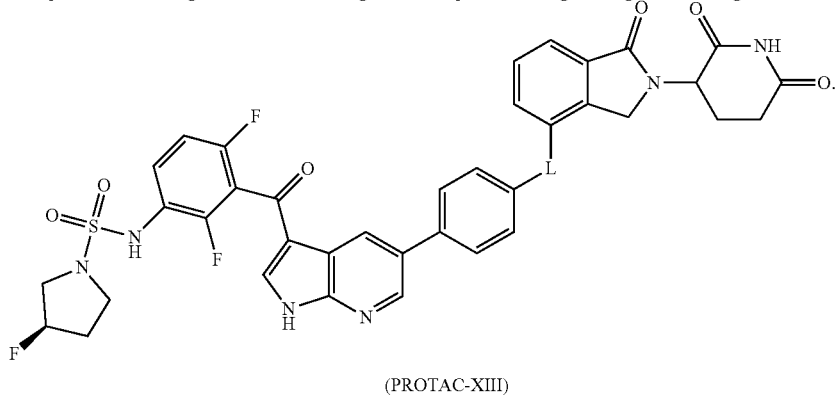

(PROTAC-XIII)

| PROTAC-XIII Compound | L | Mass | DC$_{50}$ (μM) | D$_{max}$ (%) |
|---|---|---|---|---|
| PROTAC-XIII-32 | ----O~~~O~~~O~~~O---- | 916 | | |
| PROTAC-XIII-33 | ----O~~~O~~~O~~~O---- | 916 | | |
| PROTAC-XIII-34 | ----O~~~O~~~O~~~O---- | 916 | | |
| PROTAC-XIII-35 | ----O~~~O~~~O~~~O---- | 916 | | |
| PROTAC-XIII-36 | ----O~~~O~~~O~~~O---- | 916 | | |
| PROTAC-XIII-37 | ----O~~~O~~~O~~~O---- | 916 | | |
| PROTAC-XIII-38 | ----N(piperazine)N---- | 826 | | |
| PROTAC-XIII-39 | O~~N(piperazine)N---- | 870 | | |
| PROTAC-XIII-40 | ----N(piperazine)N~~O | 870 | | |
| PROTAC-XIII-41 | ----O~~N(piperazine)N---- | 884 | | |
| PROTAC-XIII-42 | ----N(piperazine)N~~O---- | 884 | | |
| PROTAC-XIII-43 | O~~~N(piperazine)N---- | 898 | | |
| PROTAC-XIII-44 | ----N(piperazine)N~~~O | 898 | | |

TABLE 13-continued

Protacs composed of a RAF ligand and a cereblon ligand with 4-position linkage having the following chemical structure

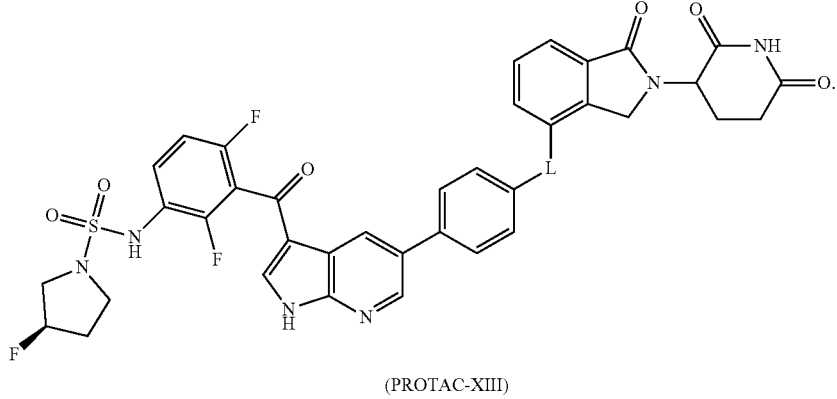

(PROTAC-XIII)

| PROTAC-XIII Compound | L | Mass | DC$_{50}$ (μM) | D$_{max}$ (%) |
|---|---|---|---|---|
| PROTAC-XIII-45 | —O\~\~O\~\~N(piperazine)N— | 914 | | |
| PROTAC-XIII-46 | —N(piperazine)N\~\~O\~\~O— | 914 | | |
| PROTAC-XIII-47 | —N(piperazine)N\~\~N(piperazine)N— | 938 | | |
| PROTAC-XIII-48 | O\~\~N(piperazine)N\~\~O | 914 | | |
| PROTAC-XIII-49 | O\~\~O\~\~N(piperazine)N— | 928 | | |
| PROTAC-XIII-50 | O\~\~O\~\~N(piperazine)N— | 928 | | |
| PROTAC-XIII-51 | O\~\~\~\~N(piperazine)N— | 926 | | |
| PROTAC-XIII-52 | —N(piperazine)N\~\~O\~\~O | 928 | | |
| PROTAC-XIII-53 | —N(piperazine)N\~\~O\~\~O | 928 | | |
| PROTAC-XIII-54 | —N(piperazine)N\~\~\~\~O | 926 | | |

TABLE 13-continued

Protacs composed of a RAF ligand and a cereblon ligand with 4-position linkage having the following chemical structure

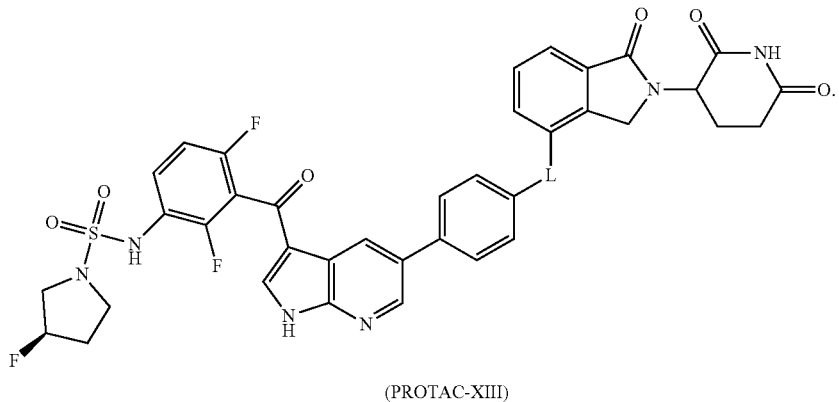

(PROTAC-XIII)

| PROTAC-XIII Compound | L | Mass | DC$_{50}$ (μM) | D$_{max}$ (%) |
|---|---|---|---|---|
| PROTAC-XIII-55 | ----N(piperazine)N—CH₂CH₂CH₂—N(N-methylpiperazine) | 952 | | |
| PROTAC-XIII-56 | ----O—CH₂CH₂CH₂—N(piperazine)N—CH₂CH₂—O.... | 928 | | |
| PROTAC-XIII-57 | ....O—CH₂CH₂—N(piperazine)N—CH₂CH₂CH₂—O---- | 928 | | |
| PROTAC-XIII-58 | ----O—CH₂CH₂CH₂—O—CH₂CH₂—N(piperazine)N---- | 942 | | |
| PROTAC-XIII-59 | ----O—CH₂CH₂—O—CH₂CH₂CH₂—N(piperazine)N---- | 942 | | |
| PROTAC-XIII-60 | ----O—CH₂CH₂—O—CH₂CH₂CH₂CH₂—N(piperazine)N---- | 942 | | |
| PROTAC-XIII-61 | ----O—(CH₂)₅—N(piperazine)N---- | 940 | | |
| PROTAC-XIII-62 | ----N(piperazine)N—CH₂CH₂CH₂—O—CH₂CH₂—O---- | 942 | | |

Protacs composed of a RAF ligand and a cereblon ligand with 4-position linkage having the following chemical structure

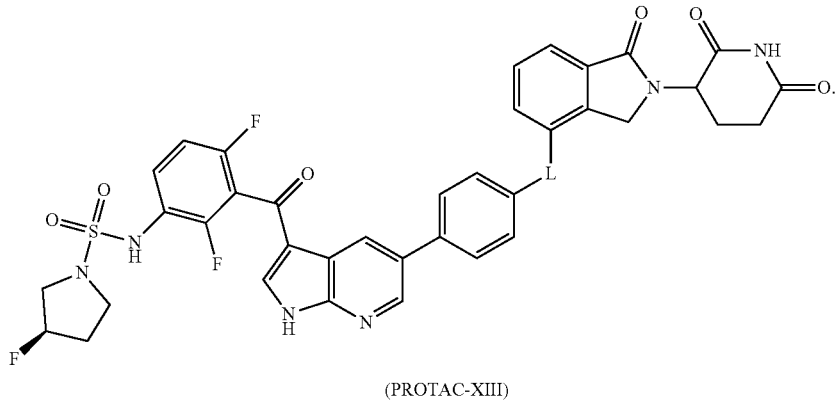

(PROTAC-XIII)

| PROTAC-XIII Compound | L | Mass | DC$_{50}$ (μM) | D$_{max}$ (%) |
|---|---|---|---|---|
| PROTAC-XIII-63 | ----N(piperazine)N-CH2CH2CH2-O-CH2CH2-O---- | 942 | | |
| PROTAC-XIII-64 | ----N(piperazine)N-CH2CH2-O-CH2CH2CH2CH2-O---- | 942 | | |
| PROTAC-XIII-65 | ----N(piperazine)N-(CH2)5-O---- | 940 | | |
| PROTAC-XIII-66 | ----N(piperazine)N-CH2CH2CH2-N(piperazine)N---- | 966 | | |
| PROTAC-XIII-67 | ----O-CH2CH2-N(piperazine)N-CH2CH2-O---- | 942 | | |
| PROTAC-XIII-68 | ----O-(CH2)4-N(piperazine)N-CH2CH2-O---- | 942 | | |
| PROTAC-XIII-69 | ----O-CH2CH2-N(piperazine)N-(CH2)4-O---- | 942 | | |
| PROTAC-XIII-70 | ----O---- | 758 | | |

TABLE 14

Protacs composed of a RAF ligand and a cereblon ligand with 7-position linkage having the following chemical structure

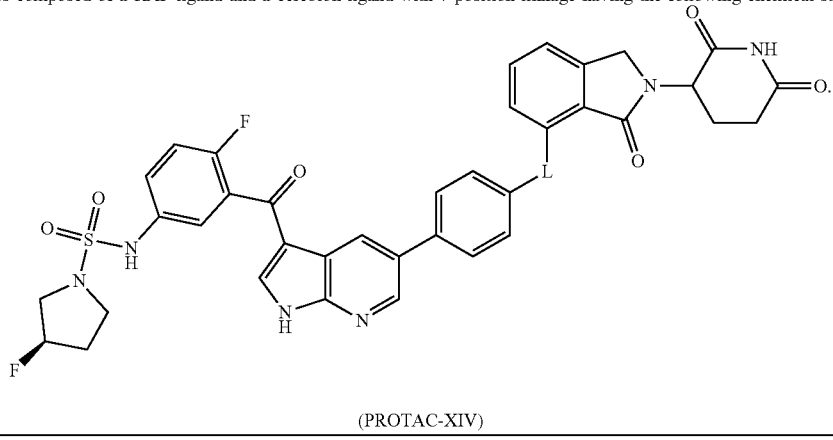

(PROTAC-XIV)

| PROTAC-XIV Compound | L | Mass | $DC_{50}$ (μM) | $D_{max}$ (%) |
|---|---|---|---|---|
| PROTAC-XIV-1 | ----O~~O---- | 802 | | |
| PROTAC-XIV-2 | ----O~O~O⋯ | 846 | | |
| PROTAC-XIV-3 | ----O~O~O~O---- | 890 | | |
| PROTAC-XIV-4 | ----O~O~O~O~O⋯ | 934 | | |
| PROTAC-XIV-5 | ----O~O~O~O~O~O---- | 978 | | |
| PROTAC-XIV-6 | ----O~O~O~O~O~O~O⋯ | 1022 | | |
| PROTAC-XIV-7 | ----~O⋯ | 786 | | |
| PROTAC-XIV-8 | ⋯~O⋯ | 772 | | |
| PROTAC-XIV-9 | ⋯O~---- | 786 | | |
| PROTAC-XIV-10 | ----O~---- | 772 | | |
| PROTAC-XIV-11 | ----O~~O⋯ | 816 | | |
| PROTAC-XIV-12 | ----O~~O---- | 830 | | |
| PROTAC-XIV-13 | ----O~O~~O---- | 860 | | |
| PROTAC-XIV-14 | ----O~~O~O---- | 860 | | |
| PROTAC-XIV-15 | ----O~~~O---- | 858 | | |

TABLE 14-continued
Protacs composed of a RAF ligand and a cereblon ligand with 7-position linkage having the following chemical structure
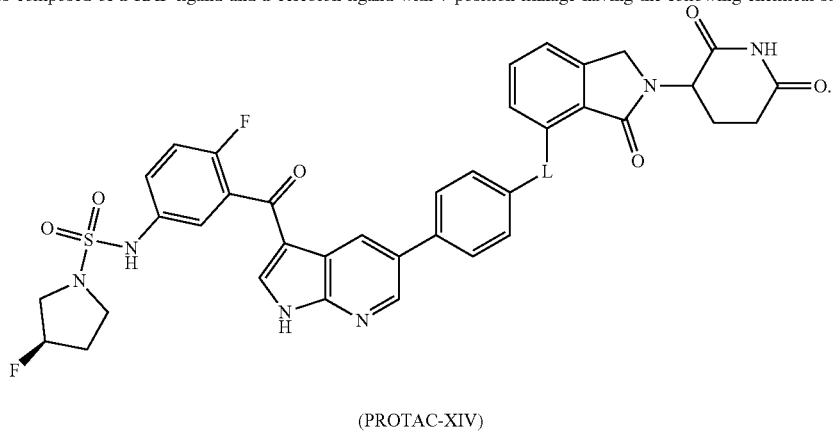
(PROTAC-XIV)
| PROTAC-XIV Compound | L | Mass | DC$_{50}$ (µM) | D$_{max}$ (%) |
|---|---|---|---|---|
| PROTAC-XIV-16 | | 874 | | |
| PROTAC-XIV-17 | | 874 | | |
| PROTAC-XIV-18 | | 874 | | |
| PROTAC-XIV-19 | | 904 | | |
| PROTAC-XIV-20 | | 904 | | |
| PROTAC-XIV-21 | | 904 | | |
| PROTAC-XIV-22 | | 902 | | |
| PROTAC-XIV-23 | | 902 | | |
| PROTAC-XIV-24 | | 902 | | |
| PROTAC-XIV-25 | | 902 | | |
| PROTAC-XIV-26 | | 902 | | |
| PROTAC-XIV-27 | | 918 | | |
| PROTAC-XIV-28 | | 918 | | |
| PROTAC-XIV-29 | | 918 | | |
| PROTAC-XIV-30 | | 918 | | |

TABLE 14-continued
Protacs composed of a RAF ligand and a cereblon ligand with 7-position linkage having the following chemical structure
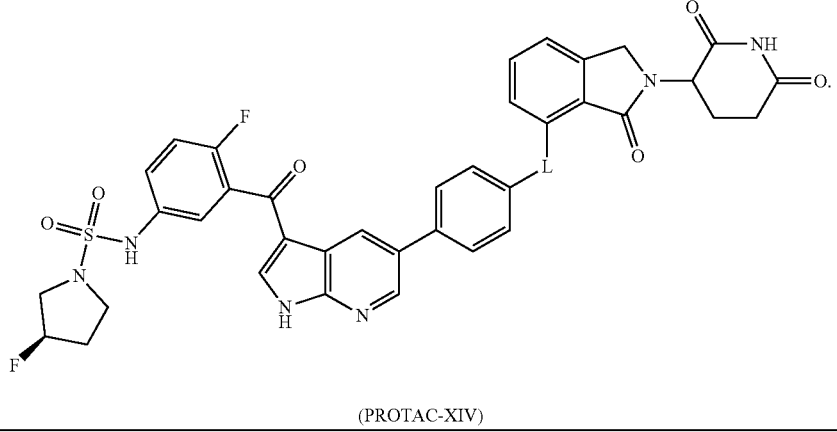
(PROTAC-XIV)
| PROTAC-XIV Compound | L | Mass | DC$_{50}$ (µM) | D$_{max}$ (%) |
|---|---|---|---|---|
| PROTAC-XIV-31 | | 918 | | |
| PROTAC-XIV-32 | | 916 | | |
| PROTAC-XIV-33 | | 916 | | |
| PROTAC-XIV-34 | | 916 | | |
| PROTAC-XIV-35 | | 916 | | |
| PROTAC-XIV-36 | | 916 | | |
| PROTAC-XIV-37 | | 916 | | |
| PROTAC-XIV-38 | | 826 | | |
| PROTAC-XIV-39 | | 870 | | |
| PROTAC-XIV-40 | | 870 | | |
| PROTAC-XIV-41 | | 884 | | |
| PROTAC-XIV-42 | | 884 | | |
| PROTAC-XIV-43 | | 898 | | |

TABLE 14-continued

Protacs composed of a RAF ligand and a cereblon ligand with 7-position linkage having the following chemical structure

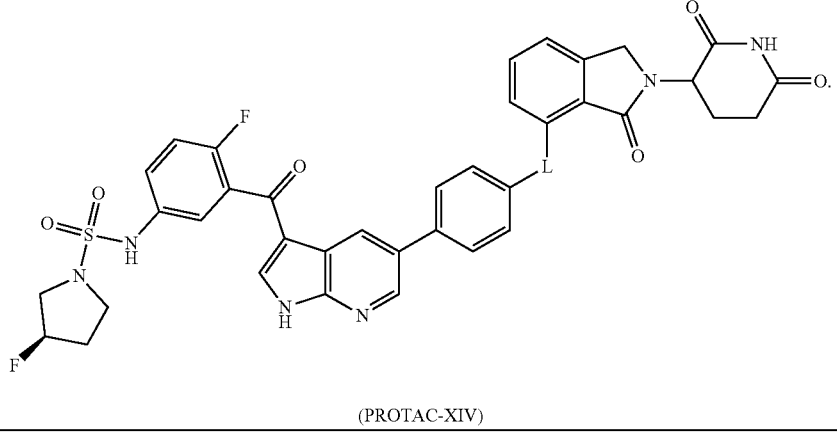

(PROTAC-XIV)

| PROTAC-XIV Compound | L | Mass | DC$_{50}$ (μM) | D$_{max}$ (%) |
|---|---|---|---|---|
| PROTAC-XIV-44 | piperazine-CH$_2$CH$_2$CH$_2$-O- | 898 | | |
| PROTAC-XIV-45 | -O-CH$_2$CH$_2$-O-CH$_2$CH$_2$-piperazine- | 914 | | |
| PROTAC-XIV-46 | piperazine-CH$_2$CH$_2$-O-CH$_2$CH$_2$-O- | 914 | | |
| PROTAC-XIV-47 | piperazine-CH$_2$CH$_2$-piperazine- | 938 | | |
| PROTAC-XIV-48 | -O-CH$_2$CH$_2$-piperazine-CH$_2$CH$_2$-O- | 914 | | |
| PROTAC-XIV-49 | -O-CH$_2$CH$_2$-O-CH$_2$CH$_2$-piperazine- | 928 | | |
| PROTAC-XIV-50 | -O-CH$_2$-O-CH$_2$CH$_2$-piperazine- | 928 | | |
| PROTAC-XIV-51 | -O-CH$_2$CH$_2$CH$_2$CH$_2$-piperazine- | 926 | | |
| PROTAC-XIV-52 | -piperazine-CH$_2$CH$_2$-O-CH$_2$CH$_2$CH$_2$-O- | 928 | | |
| PROTAC-XIV-53 | -piperazine-CH$_2$CH$_2$-O-CH$_2$CH$_2$-O- | 928 | | |

TABLE 14-continued
Protacs composed of a RAF ligand and a cereblon ligand with 7-position linkage having the following chemical structure
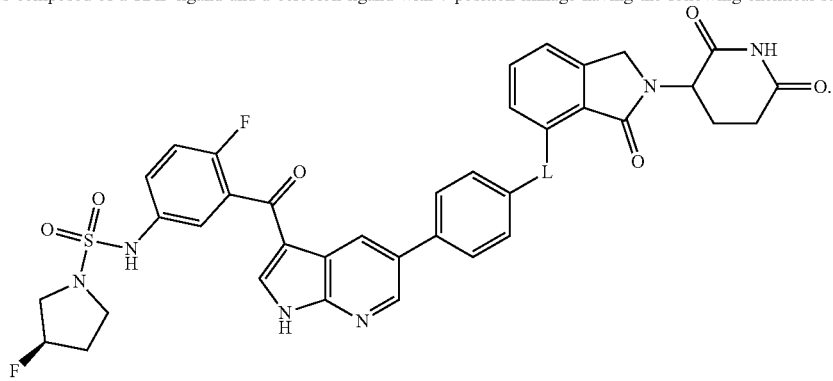
(PROTAC-XIV)
| PROTAC-XIV Compound | L | Mass | $DC_{50}$ (μM) | $D_{max}$ (%) |
|---|---|---|---|---|
| PROTAC-XIV-54 | | 926 | | |
| PROTAC-XIV-55 | | 952 | | |
| PROTAC-XIV-56 | | 928 | | |
| PROTAC-XIV-57 | | 928 | | |
| PROTAC-XIV-58 | | 942 | | |
| PROTAC-XIV-59 | | 942 | | |
| PROTAC-XIV-60 | | 942 | | |
| PROTAC-XIV-61 | | 940 | | |
| PROTAC-XIV-62 | | 942 | | |
| PROTAC-XIV-63 | | 942 | | |

TABLE 14-continued
Protacs composed of a RAF ligand and a cereblon ligand with 7-position linkage having the following chemical structure
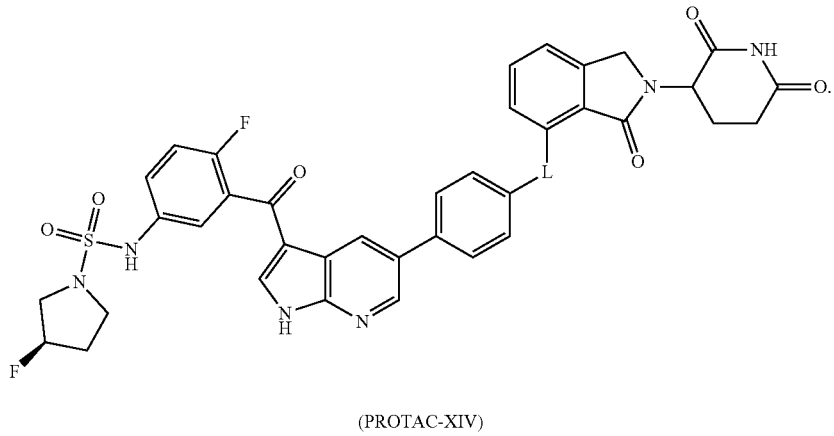
(PROTAC-XIV)
| PROTAC-XIV Compound | L | Mass | DC$_{50}$ (μM) | D$_{max}$ (%) |
|---|---|---|---|---|
| PROTAC-XIV-64 | ----N⌒N-\_\_O\_\_\_\_O---- | 942 | | |
| PROTAC-XIV-65 | ----N⌒N-\_\_\_\_\_O---- | 940 | | |
| PROTAC-XIV-66 | ----N⌒N-\_N⌒N---- | 966 | | |
| PROTAC-XIV-67 | ----O\_\_N⌒N\_\_O---- | 942 | | |
| PROTAC-XIV-68 | ⋯O\_\_\_N⌒N\_\_O⋯ | 942 | | |
| PROTAC-XIV-69 | ⋯O\_\_N⌒N\_\_\_O⋯ | 942 | | |
| PROTAC-XIV-70 | ----O⋯ | 758 | | |

TABLE 15
Protacs composed of a RAF ligand and a VHL ligand with left-side linkage having the following chemical structure
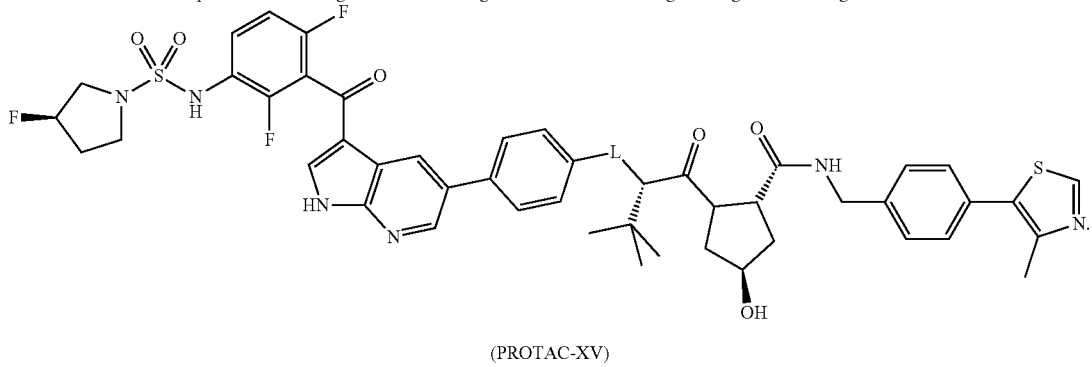
(PROTAC-XV)
| PROTAC-XV Compound | L | Mass | DC$_{50}$ (μM) | D$_{max}$ (%) |
|---|---|---|---|---|
| PROTAC-XV-1 | | 1030 | | |
| PROTAC-XV-2 | | 1074 | <1 | ≥10 |
| PROTAC-XV-3 | | 1118 | <3 | ≥10 |
| PROTAC-XV-4 | | 1162 | <1 | ≥10 |
| PROTAC-XV-5 | | 1206 | <1 | ≥10 |
| PROTAC-XV-6 | | 1250 | <1 | ≥10 |
| PROTAC-XV-7 | | 1014 | | |
| PROTAC-XV-8 | | 1000 | | |
| PROTAC-XV-9 | | 1044 | | |
| PROTAC-XV-10 | | 1044 | | |

TABLE 15-continued

Protacs composed of a RAF ligand and a VHL ligand with left-side linkage having the following chemical structure

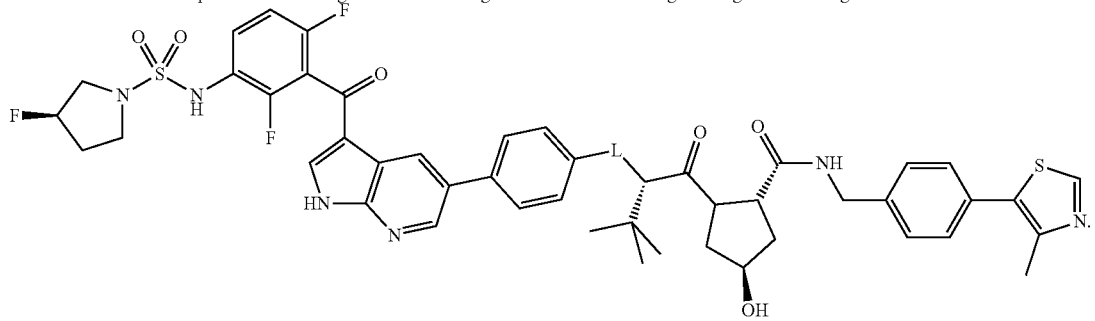

(PROTAC-XV)

| PROTAC-XV Compound | L | Mass | DC$_{50}$ (μM) | D$_{max}$ (%) |
|---|---|---|---|---|
| PROTAC-XV-11 | ----O~~~CO-NH---- | 1042 | | |
| PROTAC-XV-12 | ----O~~~O~~~CO-NH-- | 1058 | | |
| PROTAC-XV-13 | ----O~~~O~~~CO-NH-- | 1058 | | |
| PROTAC-XV-14 | ----O~~~O~~~CO-NH-- | 1058 | | |
| PROTAC-XV-15 | ----O~~~~~CO-NH-- | 1056 | | |
| PROTAC-XV-16 | ----O~CO-HN---- | 986 | | |
| PROTAC-XV-17 | ----O~~~CO-NH-- | 1028 | | |
| PROTAC-XV-18 | --O~~O~~~CO-NH-- | 1072 | | |
| PROTAC-XV-19 | --O~~O~~~CO-NH-- | 1072 | | |
| PROTAC-XV-20 | --O~~~O~~CO-NH-- | 1072 | | |
| PROTAC-XV-21 | --O~~~~O~CO-NH-- | 1072 | | |

TABLE 15-continued

Protacs composed of a RAF ligand and a VHL ligand with left-side linkage having the following chemical structure

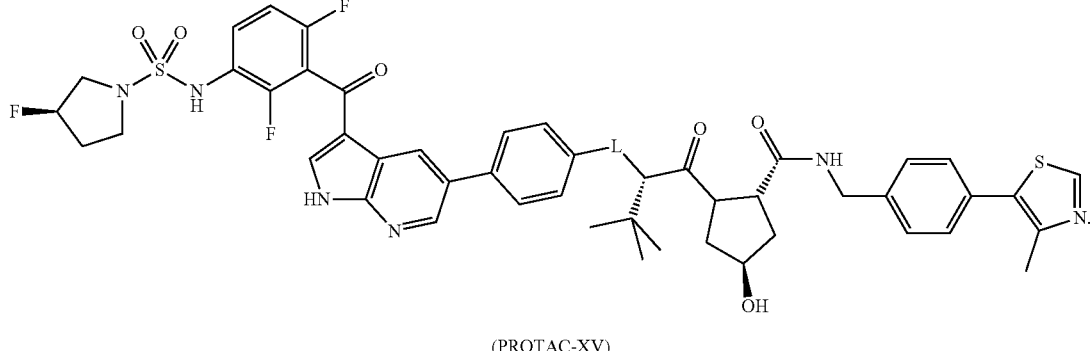

(PROTAC-XV)

| PROTAC-XV Compound | L | Mass | DC$_{50}$ (µM) | D$_{max}$ (%) |
|---|---|---|---|---|
| PROTAC-XV-22 | ----O~O~O~C(O)NH- | 1088 | | |
| PROTAC-XV-23 | ----O~O~O~C(O)NH- | 1088 | | |
| PROTAC-XV-24 | ----O~O~O~C(O)NH- | 1088 | | |
| PROTAC-XV-25 | ----O~~O~C(O)NH- | 1086 | | |
| PROTAC-XV-26 | ----O~~O~C(O)NH- | 1086 | | |
| PROTAC-XV-27 | ----O~~O~C(O)NH- | 1086 | | |
| PROTAC-XV-28 | ----O~O~~C(O)NH- | 1086 | | |
| PROTAC-XV-29 | ----O~O~~C(O)NH- | 1086 | | |
| PROTAC-XV-30 | ----O~O~~O~C(O)HN---- | 1102 | | |
| PROTAC-XV-31 | ----O~O~O~C(O)HN---- | 1102 | <1 | ≥10 |

TABLE 15-continued

Protacs composed of a RAF ligand and a VHL ligand with left-side linkage having the following chemical structure

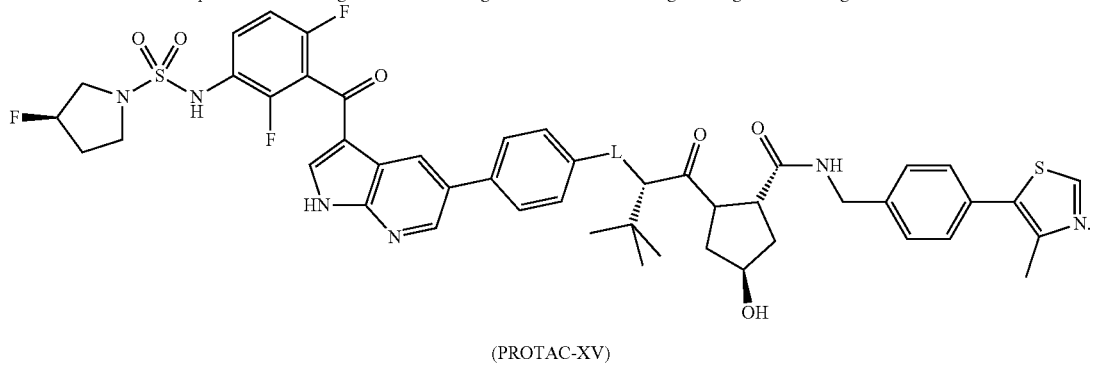

(PROTAC-XV)

| PROTAC-XV Compound | L | Mass | DC$_{50}$ (μM) | D$_{max}$ (%) |
|---|---|---|---|---|
| PROTAC-XV-32 | ----O~~~O~~~O~~~C(O)HN---- | 1102 | | |
| PROTAC-XV-33 | `O~~~O~~~O~~~C(O)HN----` | 1116 | | |
| PROTAC-XV-34 | `O~~~O~~~O~~~C(O)HN----` | 1116 | | |
| PROTAC-XV-35 | `O~~~O~~~O~~~C(O)HN----` | 1116 | | |
| PROTAC-XV-36 | `O~~~O~~~O~~~C(O)HN----` | 1116 | | |
| PROTAC-XV-37 | `O~~~O~~~O~~~C(O)HN----` | 1116 | | |
| PROTAC-XV-38 | `O~~~O~~~O~~~C(O)HN----` | 1116 | | |
| PROTAC-XV-39 | `O~~~O~~~O~~~C(O)HN----` | 1116 | | |
| PROTAC-XV-40 | `O~~~O~~~C(O)HN----` | 1114 | | |
| PROTAC-XV-41 | `O~~~O~~~C(O)HN----` | 1114 | | |

TABLE 15-continued
Protacs composed of a RAF ligand and a VHL ligand with left-side linkage having the following chemical structure
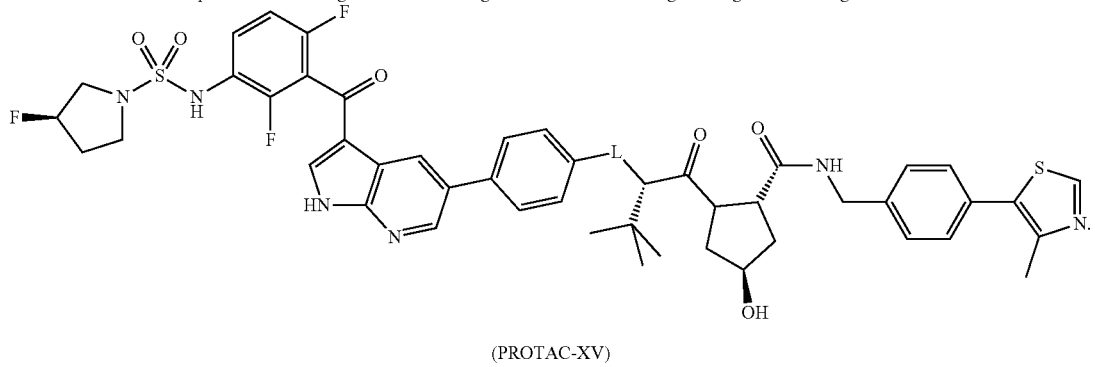
(PROTAC-XV)
| PROTAC-XV Compound | L | Mass | DC$_{50}$ (μM) | D$_{max}$ (%) |
|---|---|---|---|---|
| PROTAC-XV-42 | | 1114 | | |
| PROTAC-XV-43 | | 1114 | | |
| PROTAC-XV-44 | | 1098 | | |
| PROTAC-XV-45 | | 1112 | | |
| PROTAC-XV-46 | | 1126 | | |
| PROTAC-XV-47 | | 1140 | | |
| PROTAC-XV-48 | | 1142 | | |
| PROTAC-XV-49 | | 1156 | | |
| PROTAC-XV-50 | | 1170 | | |

TABLE 15-continued
Protacs composed of a RAF ligand and a VHL ligand with left-side linkage having the following chemical structure
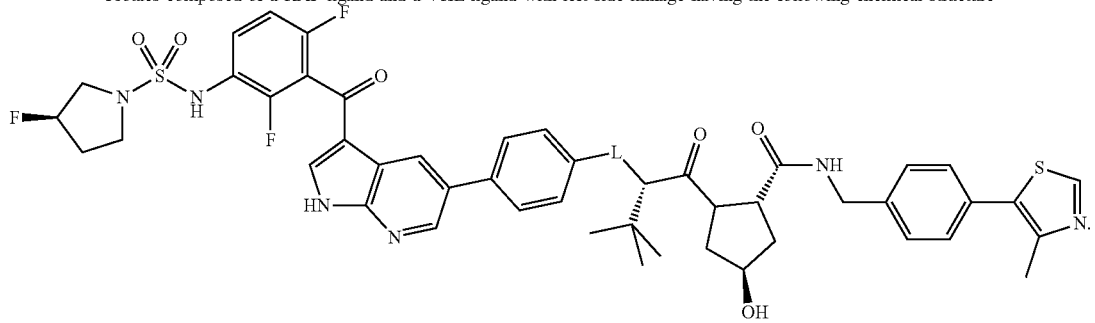
(PROTAC-XV)
| PROTAC-XV Compound | L | Mass | DC$_{50}$ (µM) | D$_{max}$ (%) |
|---|---|---|---|---|
| PROTAC-XV-51 | | 1184 | | |
| PROTAC-XV-52 | | 1186 | | |
| PROTAC-XV-53 | | 1098 | | |
| PROTAC-XV-54 | | 1097 | | |
| PROTAC-XV-55 | | 1112 | | |
| PROTAC-XV-56 | | 1126 | | |
| PROTAC-XV-57 | | 1140 | | |
| PROTAC-XV-58 | | 1142 | | |

TABLE 15-continued
Protacs composed of a RAF ligand and a VHL ligand with left-side linkage having the following chemical structure
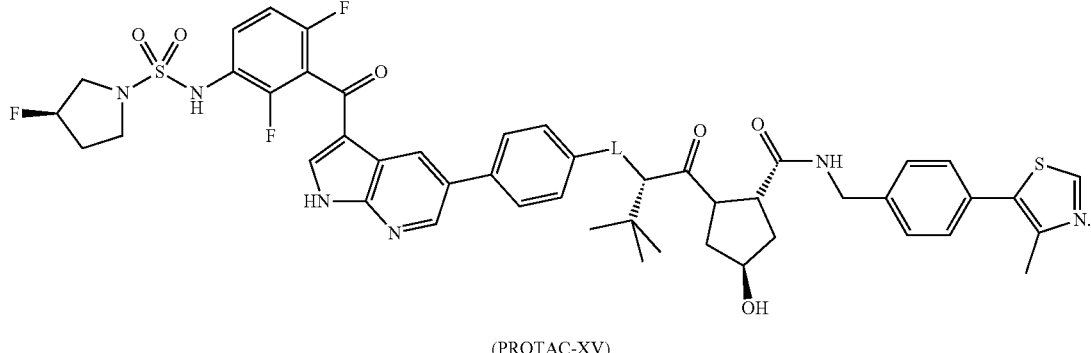
(PROTAC-XV)
| PROTAC-XV Compound | L | Mass | DC$_{50}$ (μM) | D$_{max}$ (%) |
|---|---|---|---|---|
| PROTAC-XV-59 | | 1141 | | |
| PROTAC-XV-60 | | 1166 | | |
| PROTAC-XV-61 | | 1165 | | |
| PROTAC-XV-62 | | 1165 | | |
| PROTAC-XV-63 | | 1151 | | |
| PROTAC-XV-64 | | 1137 | | |
| PROTAC-XV-65 | | 1010 | | |
| PROTAC-XV-66 | | 1024 | | |
| PROTAC-XV-67 | | 1038 | | |

TABLE 15-continued
Protacs composed of a RAF ligand and a VHL ligand with left-side linkage having the following chemical structure
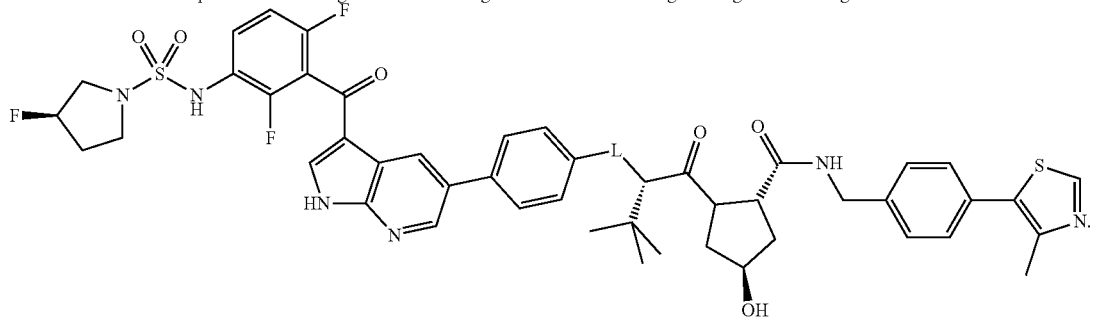
(PROTAC-XV)
| PROTAC-XV Compound | L | Mass | DC$_{50}$ (μM) | D$_{max}$ (%) |
|---|---|---|---|---|
| PROTAC-XV-68 | | 1052 | | |
| PROTAC-XV-69 | | 1054 | | |
| PROTAC-XV-70 | | 1066 | | |
| PROTAC-XV-71 | | 1068 | | |
| PROTAC-XV-72 | | 1068 | | |
| PROTAC-XV-73 | | 1082 | | |
| PROTAC-XV-74 | | 1082 | | |
| PROTAC-XV-75 | | 1082 | | |
| PROTAC-XV-76 | | 1096 | | |
| PROTAC-XV-77 | | 1096 | | |
| PROTAC-XV-78 | | 1096 | | |

TABLE 15-continued
Protacs composed of a RAF ligand and a VHL ligand with left-side linkage having the following chemical structure
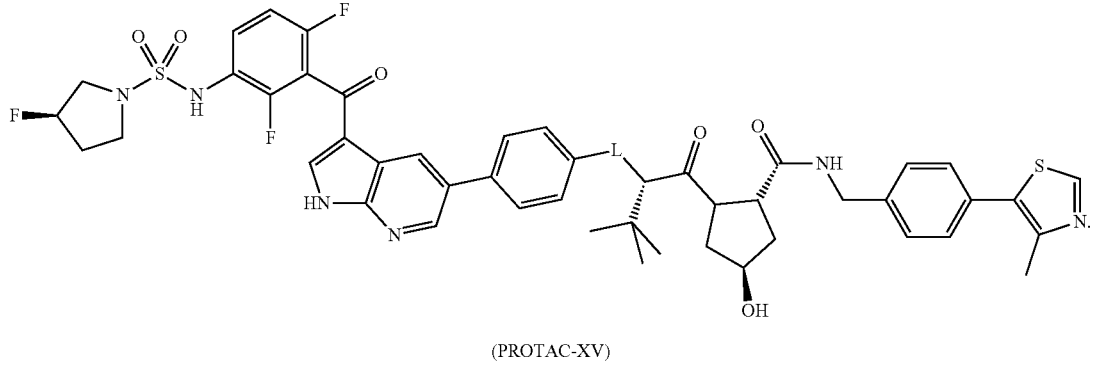
(PROTAC-XV)
| PROTAC-XV Compound | L | Mass | DC$_{50}$ (μM) | D$_{max}$ (%) |
|---|---|---|---|---|
| PROTAC-XV-79 | ![L] | 1096 | | |
| PROTAC-XV-80 | ![L] | 1098 | | |
| PROTAC-XV-81 | ![L] | 1110 | | |
| PROTAC-XV-82 | ![L] | 1110 | | |
| PROTAC-XV-83 | ![L] | 1110 | | |
| PROTAC-XV-84 | ![L] | 1110 | | |
| PROTAC-XV-85 | ![L] | 1110 | | |
| PROTAC-XV-86 | ![L] | 1112 | | |
| PROTAC-XV-87 | ![L] | 1112 | | |
| PROTAC-XV-88 | ![L] | 1112 | | |

TABLE 15-continued
Protacs composed of a RAF ligand and a VHL ligand with left-side linkage having the following chemical structure
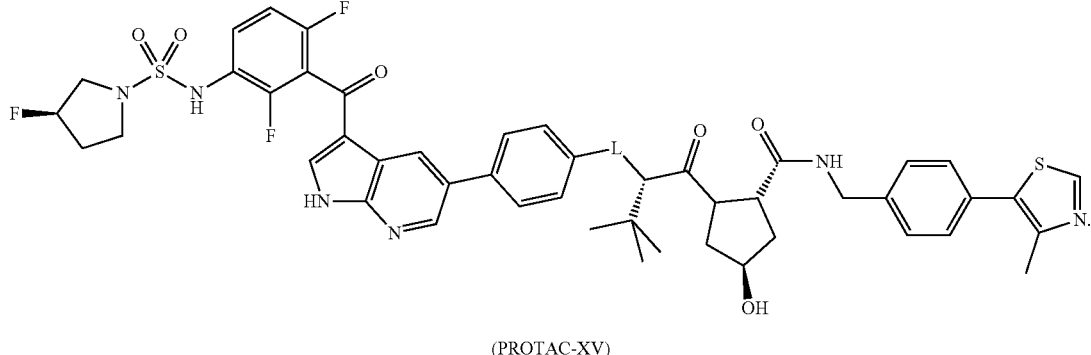
(PROTAC-XV)
| PROTAC-XV Compound | L | Mass | DC$_{50}$ (μM) | D$_{max}$ (%) |
|---|---|---|---|---|
| PROTAC-XV-89 | | 1064 | | |
| PROTAC-XV-90 | | 1078 | | |
| PROTAC-XV-91 | | 1092 | | |
| PROTAC-XV-92 | | 1106 | | |
| PROTAC-XV-93 | | 1120 | | |
| PROTAC-XV-94 | | 1122 | | |
| PROTAC-XV-95 | | 1136 | | |
| PROTAC-XV-96 | | 1136 | | |
| PROTAC-XV-97 | | 1134 | | |
| PROTAC-XV-98 | | 1148 | | |

TABLE 15-continued

Protacs composed of a RAF ligand and a VHL ligand with left-side linkage having the following chemical structure

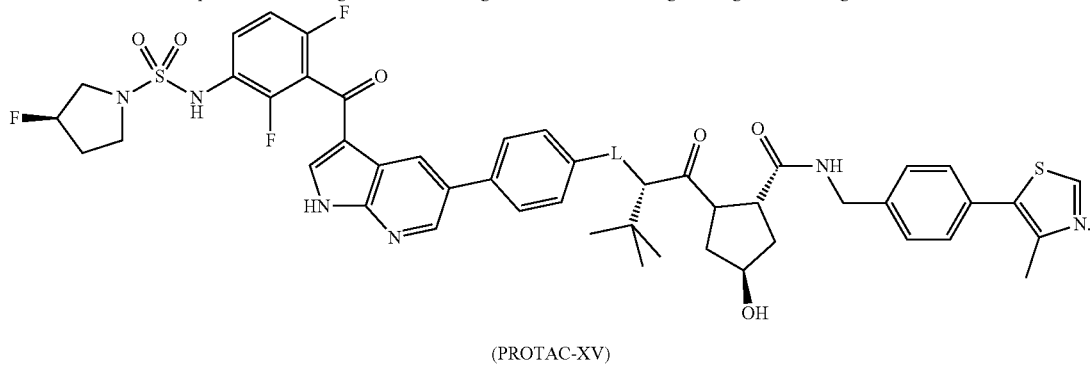

(PROTAC-XV)

| PROTAC-XV Compound | L | Mass | DC$_{50}$ (µM) | D$_{max}$ (%) |
|---|---|---|---|---|
| PROTAC-XV-99 | | 1150 | | |
| PROTAC-XV-100 | | 1150 | | |
| PROTAC-XV-101 | | 1150 | | |

TABLE 16

Protacs composed of a RAF ligand and a VHL ligand with right-side linkage having the following chemical structure

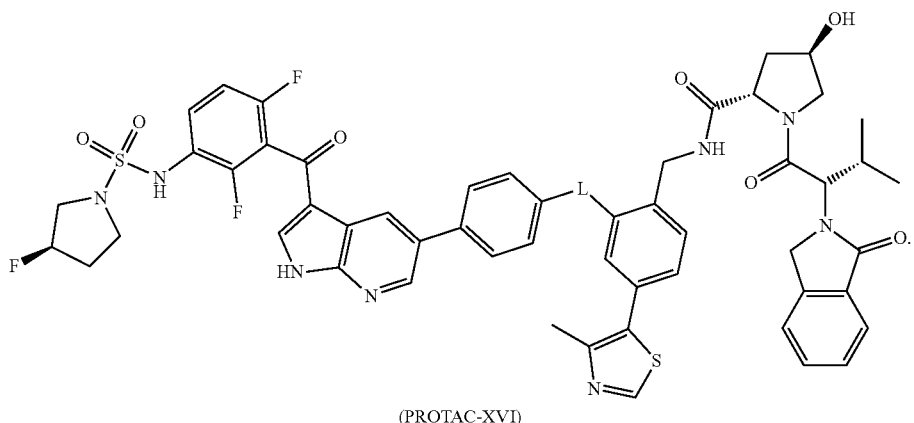

(PROTAC-XVI)

| PROTAC-XVI Compound | L | Mass | DC$_{50}$ (µM) | D$_{max}$ (%) |
|---|---|---|---|---|
| PROTAC-XVI-1 | | 1090 | | |
| PROTAC-XVI-2 | | 1134 | >1 | <10 |

TABLE 16-continued
Protacs composed of a RAF ligand and a VHL ligand with right-side linkage having the following chemical structure
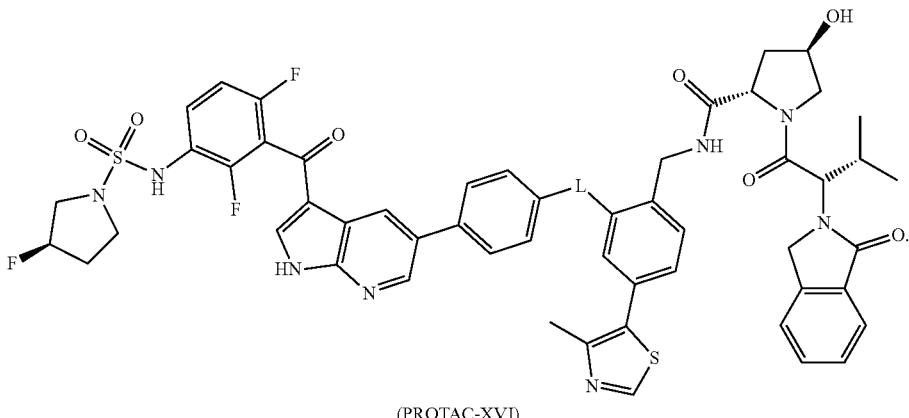
(PROTAC-XVI)
| PROTAC-XVI Compound | L | Mass | DC$_{50}$ (μM) | D$_{max}$ (%) |
|---|---|---|---|---|
| PROTAC-XVI-3 | | 1178 | <1 | ≥10 |
| PROTAC-XVI-4 | | 1222 | <1 | ≥10 |
| PROTAC-XVI-5 | | 1266 | <3 | ≥10 |
| PROTAC-XVI-6 | | 1310 | <3 | ≥10 |
| PROTAC-XVI-7 | | 1074 | | |
| PROTAC-XVI-8 | | 1060 | | |
| PROTAC-XVI-9 | | 1074 | | |
| PROTAC-XVI-10 | | 1060 | | |
| PROTAC-XVI-11 | | 1104 | | |
| PROTAC-XVI-12 | | 1118 | | |
| PROTAC-XVI-13 | | 1148 | | |
| PROTAC-XVI-14 | | 1148 | | |
| PROTAC-XVI-15 | | 1146 | | |
| PROTAC-XVI-16 | | 1162 | | |
| PROTAC-XVI-17 | | 1162 | | |

TABLE 16-continued

Protacs composed of a RAF ligand and a VHL ligand with right-side linkage having the following chemical structure

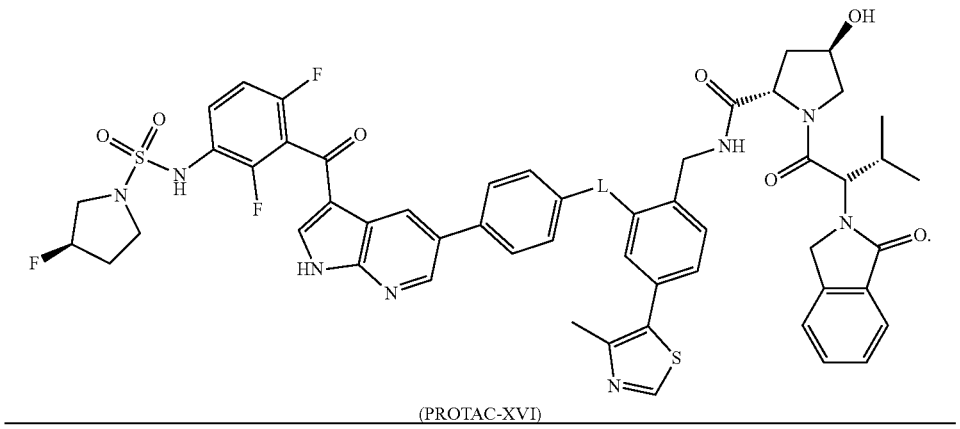

(PROTAC-XVI)

| PROTAC-XVI Compound | L | Mass | DC$_{50}$ (μM) | D$_{max}$ (%) |
|---|---|---|---|---|
| PROTAC-XVI-18 | ----O~~~O~~~O~~~O~ | 1162 | | |
| PROTAC-XVI-19 | ----O~~~O~~~O~~~O~ | 1192 | | |
| PROTAC-XVI-20 | ----O~~~O~~~O~~~O~ | 1192 | | |
| PROTAC-XVI-21 | ----O~~~O~~~O~~~O~ | 1192 | | |
| PROTAC-XVI-22 | ----O~~~O~~~O~ | 1190 | | |
| PROTAC-XVI-23 | ----O~~~O~~~O~ | 1190 | | |
| PROTAC-XVI-24 | ----O~~~O~~~O~ | 1190 | | |
| PROTAC-XVI-25 | ----O~~~O~~~O~ | 1190 | | |
| PROTAC-XVI-26 | ----O~~~O~~~O~ | 1190 | | |
| PROTAC-XVI-27 | ----O~~~O~~~O~~~O---- | 1206 | | |
| PROTAC-XVI-28 | ----O~~~O~~~O~~~O---- | 1206 | | |
| PROTAC-XVI-29 | ----O~~~O~~~O~~~O---- | 1206 | | |
| PROTAC-XVI-30 | ----O~~~O~~~O~~~O---- | 1206 | | |
| PROTAC-XVI-31 | ----O~~~O~~~O~~~O---- | 1206 | | |
| PROTAC-XVI-32 | ----O~~~O~~~O---- | 1204 | | |

TABLE 16-continued
Protacs composed of a RAF ligand and a VHL ligand with right-side linkage having the following chemical structure
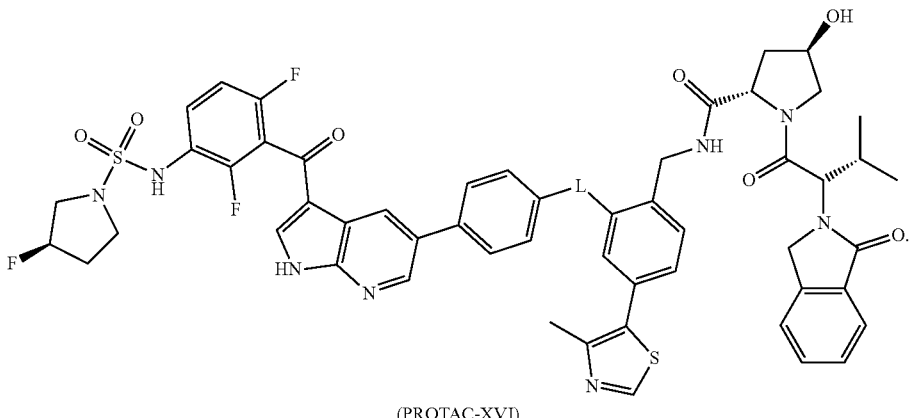
(PROTAC-XVI)
| PROTAC-XVI Compound | L | Mass | DC$_{50}$ (µM) | D$_{max}$ (%) |
|---|---|---|---|---|
| PROTAC-XVI-33 | | 1204 | | |
| PROTAC-XVI-34 | | 1204 | | |
| PROTAC-XVI-35 | | 1204 | | |
| PROTAC-XVI-36 | | 1204 | | |
| PROTAC-XVI-37 | | 1204 | | |
| PROTAC-XVI-38 | | 1114 | | |
| PROTAC-XVI-39 | | 1158 | | |
| PROTAC-XVI-40 | | 1158 | | |
| PROTAC-XVI-41 | | 1172 | | |
| PROTAC-XVI-42 | | 1172 | | |
| PROTAC-XVI-43 | | 1186 | | |
| PROTAC-XVI-44 | | 1186 | | |

TABLE 16-continued

Protacs composed of a RAF ligand and a VHL ligand with right-side linkage having the following chemical structure

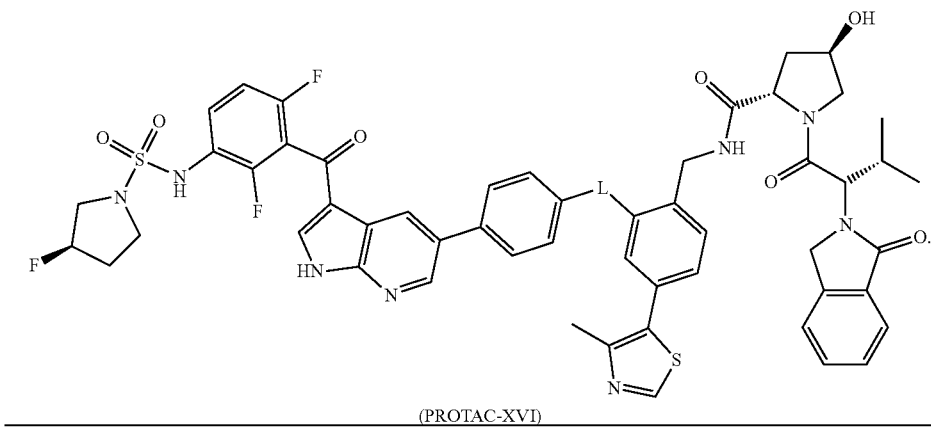

(PROTAC-XVI)

| PROTAC-XVI Compound | L | Mass | DC$_{50}$ (μM) | D$_{max}$ (%) |
|---|---|---|---|---|
| PROTAC-XVI-45 | ----O∼O∼N∼N---- | 1202 | | |
| PROTAC-XVI-46 | ----N∼N∼O∼O---- | 1202 | | |
| PROTAC-XVI-47 | ----N∼N∼N∼N---- | 1226 | | |
| PROTAC-XVI-48 | ∼O∼N∼N∼O∼ | 1202 | | |
| PROTAC-XVI-49 | ∼O∼O∼N∼N---- | 1216 | | |
| PROTAC-XVI-50 | ∼O∼O∼N∼N---- | 1216 | | |
| PROTAC-XVI-51 | ∼O∼∼∼N∼N---- | 1214 | | |
| PROTAC-XVI-52 | ----N∼N∼O∼O∼ | 1216 | | |
| PROTAC-XVI-53 | ----N∼N∼O∼O∼ | 1216 | | |
| PROTAC-XVI-54 | ----N∼N∼∼∼O∼ | 1214 | | |

TABLE 16-continued
Protacs composed of a RAF ligand and a VHL ligand with right-side linkage having the following chemical structure
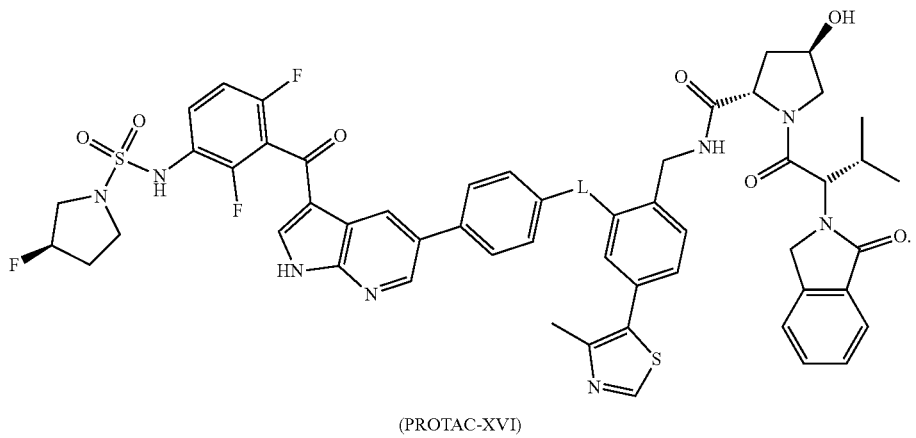
(PROTAC-XVI)
| PROTAC-XVI Compound | L | Mass | DC$_{50}$ (μM) | D$_{max}$ (%) |
|---|---|---|---|---|
| PROTAC-XVI-55 | | 1240 | | |
| PROTAC-XVI-56 | | 1216 | | |
| PROTAC-XVI-57 | | 1216 | | |
| PROTAC-XVI-58 | | 1230 | | |
| PROTAC-XVI-59 | | 1230 | | |
| PROTAC-XVI-60 | | 1230 | | |
| PROTAC-XVI-61 | | 1228 | | |
| PROTAC-XVI-62 | | 1230 | | |

TABLE 16-continued

Protacs composed of a RAF ligand and a VHL ligand with right-side linkage having the following chemical structure

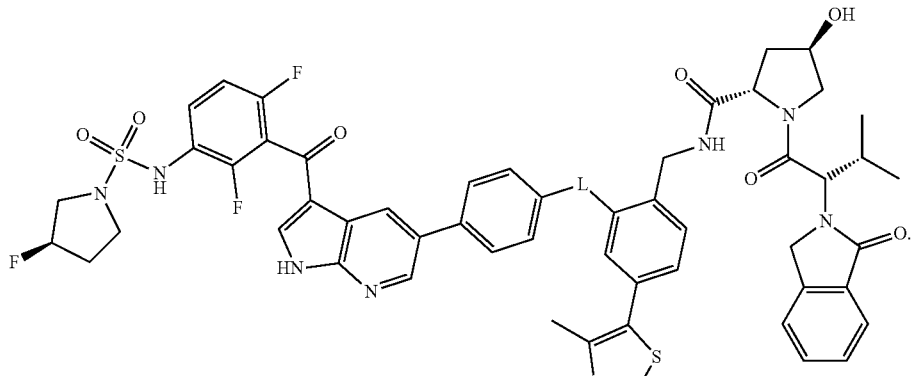

(PROTAC-XVI)

| PROTAC-XVI Compound | L | Mass | DC$_{50}$ (μM) | D$_{max}$ (%) |
|---|---|---|---|---|
| PROTAC-XVI-63 | ----N(piperazine)N-CH$_2$CH$_2$-O-CH$_2$CH$_2$-O---- | 1230 | | |
| PROTAC-XVI-64 | ----N(piperazine)N-CH$_2$CH$_2$-O-CH$_2$CH$_2$CH$_2$-O---- | 1230 | | |
| PROTAC-XVI-65 | ----N(piperazine)N-(CH$_2$)$_4$-O---- | 1228 | | |
| PROTAC-XVI-66 | ----N(piperazine)N-CH$_2$CH$_2$CH$_2$-N(piperazine)N---- | 1254 | | |
| PROTAC-XVI-67 | ----O-CH$_2$CH$_2$CH$_2$-N(piperazine)N-CH$_2$CH$_2$-O---- | 1230 | | |
| PROTAC-XVI-68 | O-CH$_2$CH$_2$CH$_2$CH$_2$-N(piperazine)N-CH$_2$CH$_2$-O | 1230 | | |
| PROTAC-XVI-69 | O-CH$_2$CH$_2$-N(piperazine)N-CH$_2$CH$_2$CH$_2$CH$_2$-O | 1230 | | |
| PROTAC-XVI-70 | ----O---- | 1046 | | |

TABLE 17

Protacs composed of a RAF ligand and a cereblon ligand with 5-position linkage having the following chemical structure

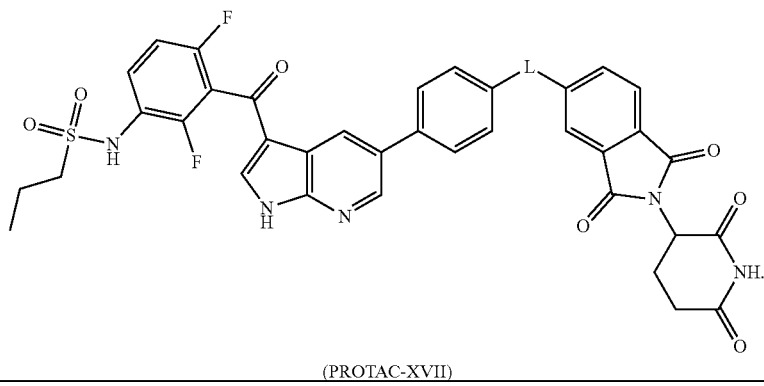

(PROTAC-XVII)

| PROTAC-XVII Compound | L | Mass | DC$_{50}$ (μM) | D$_{max}$ (%) |
|---|---|---|---|---|
| PROTAC-XVII-1 | ----O\_/\_O---- | 771 | | |
| PROTAC-XVII-2 | ----O\_/\_O\_/\_O\_/\` | 815 | | |
| PROTAC-XVII-3 | ----O\_/\_O\_/\_O\_/\_O---- | 859 | | |
| PROTAC-XVII-4 | ----O\_/\_O\_/\_O\_/\_O\_/\_O\` | 903 | | |
| PROTAC-XVII-5 | ----O\_/\_O\_/\_O\_/\_O\_/\_O\_/\_O---- | 947 | | |
| PROTAC-XVII-6 | ----O\_/\_O\_/\_O\_/\_O\_/\_O\_/\_O\_/\` | 991 | | |
| PROTAC-XVII-7 | ----\_/\_O\` | 755 | | |
| PROTAC-XVII-8 | \`\_/\_O\` | 741 | | |
| PROTAC-XVII-9 | \`O\_/\_---- | 755 | | |
| PROTAC-XVII-10 | ----O\_/\` | 741 | | |
| PROTAC-XVII-11 | ----O\_/\_/\_O\` | 785 | | |
| PROTAC-XVII-12 | ----O\_/\_/\_O---- | 799 | | |
| PROTAC-XVII-13 | ----O\_/\_O\_/\_O---- | 829 | | |
| PROTAC-XVII-14 | ----O\_/\_O\_/\_O---- | 829 | | |
| PROTAC-XVII-15 | ----O\_/\_/\_O---- | 827 | | |
| PROTAC-XVII-16 | ----O\_/\_O\_/\_O\` | 843 | | |

TABLE 17-continued

Protacs composed of a RAF ligand and a cereblon ligand with 5-position linkage having the following chemical structure

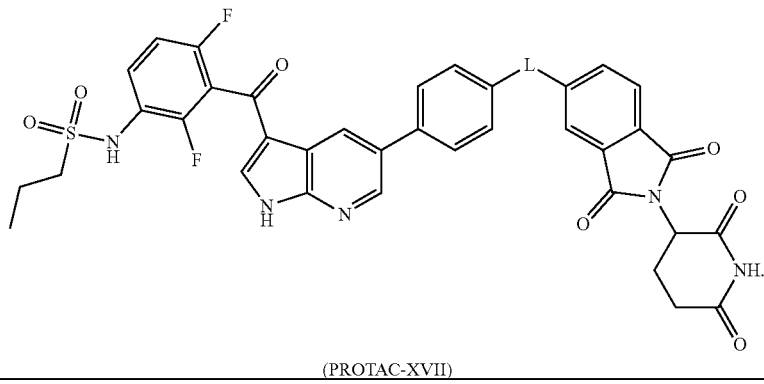

(PROTAC-XVII)

| PROTAC-XVII Compound | L | Mass | DC$_{50}$ (μM) | D$_{max}$ (%) |
|---|---|---|---|---|
| PROTAC-XVII-17 | ----O~O~O~O''' | 843 | | |
| PROTAC-XVII-18 | ----O~O~O~O''' | 843 | | |
| PROTAC-XVII-19 | ----O~O~O~O~O''' | 873 | | |
| PROTAC-XVII-20 | ----O~O~O~O~O''' | 873 | | |
| PROTAC-XVII-21 | ----O~O~O~O~O''' | 873 | | |
| PROTAC-XVII-22 | ----O~O~O~O''' | 871 | | |
| PROTAC-XVII-23 | ----O~O~O~O''' | 871 | | |
| PROTAC-XVII-24 | ----O~O~O~O''' | 871 | | |
| PROTAC-XVII-25 | ----O~O~O~O''' | 871 | | |
| PROTAC-XVII-26 | ----O~O~O~O''' | 871 | | |
| PROTAC-XVII-27 | ----O~O~O~O~O---- | 887 | | |
| PROTAC-XVII-28 | ----O~O~O~O~O---- | 887 | | |
| PROTAC-XVII-29 | ----O~O~O~O~O---- | 887 | | |
| PROTAC-XVII-30 | ----O~O~O~O~O---- | 887 | | |
| PROTAC-XVII-31 | ----O~O~O~O~O---- | 887 | | |

TABLE 17-continued

Protacs composed of a RAF ligand and a cereblon ligand with 5-position linkage having the following chemical structure

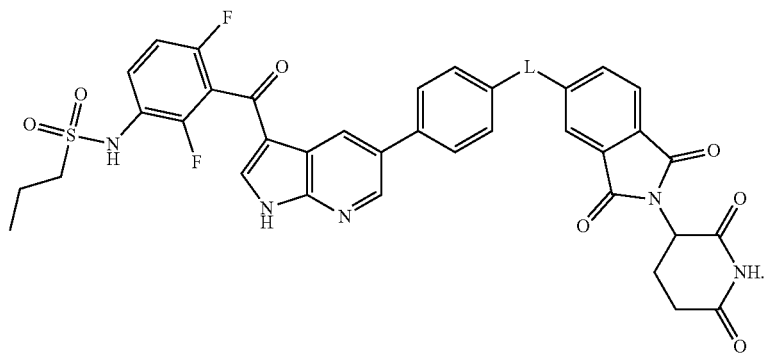

(PROTAC-XVII)

| PROTAC-XVII Compound | L | Mass | DC$_{50}$ (μM) | D$_{max}$ (%) |
|---|---|---|---|---|
| PROTAC-XVII-32 | ----O~~~O~~~O~~~O---- | 885 | | |
| PROTAC-XVII-33 | ----O~~~O~~~O~~~O---- | 885 | | |
| PROTAC-XVII-34 | ----O~~~O~~~O~~~O---- | 885 | | |
| PROTAC-XVII-35 | ----O~~~O~~~O~~~O---- | 885 | | |
| PROTAC-XVII-36 | ----O~~~O~~~O~~~O---- | 885 | | |
| PROTAC-XVII-37 | ----O~~~O~~~O~~~O---- | 885 | | |
| PROTAC-XVII-38 | ----N(piperazine)N---- | 795 | | |
| PROTAC-XVII-39 | O~~~N(piperazine)N---- | 839 | | |
| PROTAC-XVII-40 | ----N(piperazine)N~~~O | 839 | | |
| PROTAC-XVII-41 | ----O~~~N(piperazine)N---- | 853 | | |
| PROTAC-XVII-42 | ----N(piperazine)N~~~O---- | 853 | | |
| PROTAC-XVII-43 | O~~~N(piperazine)N---- | 867 | | |
| PROTAC-XVII-44 | ----N(piperazine)N~~~O | 867 | | |

TABLE 17-continued

Protacs composed of a RAF ligand and a cereblon ligand with 5-position linkage having the following chemical structure

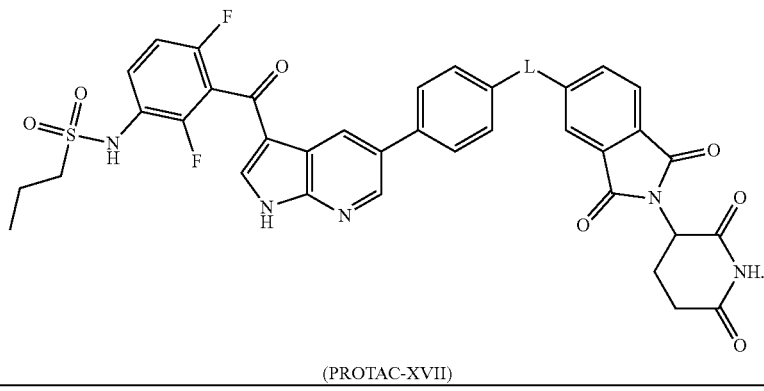

(PROTAC-XVII)

| PROTAC-XVII Compound | L | Mass | DC$_{50}$ (μM) | D$_{max}$ (%) |
|---|---|---|---|---|
| PROTAC-XVII-45 | ----O~~O~~N(piperazine)N---- | 883 | | |
| PROTAC-XVII-46 | ----N(piperazine)N~~O~~O---- | 883 | | |
| PROTAC-XVII-47 | ----N(piperazine)N~~N(piperazine)N---- | 907 | | |
| PROTAC-XVII-48 | O~~N(piperazine)N~~O | 883 | | |
| PROTAC-XVII-49 | O~~O~~N(piperazine)N---- | 897 | | |
| PROTAC-XVII-50 | O~~O~~N(piperazine)N---- | 897 | | |
| PROTAC-XVII-51 | O~~~~N(piperazine)N---- | 895 | | |
| PROTAC-XVII-52 | ----N(piperazine)N~~O~~O | 897 | | |
| PROTAC-XVII-53 | ----N(piperazine)N~~O~~O | 897 | | |
| PROTAC-XVII-54 | ----N(piperazine)N~~~~O | 895 | | |

TABLE 17-continued

Protacs composed of a RAF ligand and a cereblon ligand with 5-position linkage having the following chemical structure

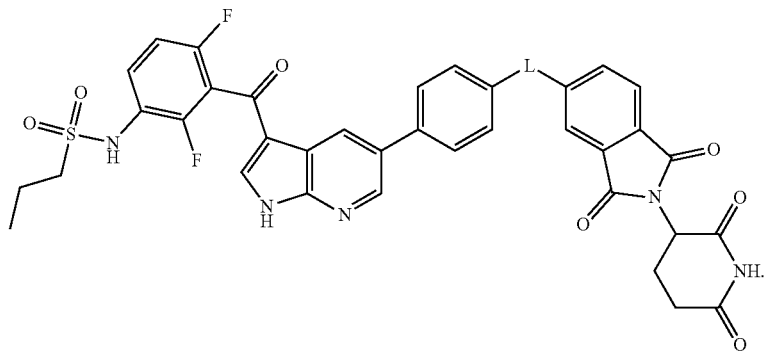

(PROTAC-XVII)

| PROTAC-XVII Compound | L | Mass | DC$_{50}$ (μM) | D$_{max}$ (%) |
|---|---|---|---|---|
| PROTAC-XVII-55 | ----N(piperazine)N-CH$_2$CH$_2$CH$_2$-N(N-methylpiperazine) | 921 | | |
| PROTAC-XVII-56 | ----O-CH$_2$CH$_2$-N(piperazine)N-CH$_2$CH$_2$-O---- | 897 | | |
| PROTAC-XVII-57 | ----O-CH$_2$CH$_2$-N(piperazine)N-CH$_2$CH$_2$-O---- | 897 | | |
| PROTAC-XVII-58 | ----O-CH$_2$CH$_2$CH$_2$CH$_2$-O-CH$_2$CH$_2$-N(piperazine)N---- | 911 | | |
| PROTAC-XVII-59 | ----O-CH$_2$CH$_2$-O-CH$_2$CH$_2$CH$_2$-N(piperazine)N---- | 911 | | |
| PROTAC-XVII-60 | ----O-CH$_2$-O-CH$_2$CH$_2$-CH$_2$CH$_2$CH$_2$-N(piperazine)N---- | 911 | | |
| PROTAC-XVII-61 | ----O-CH$_2$CH$_2$CH$_2$CH$_2$CH$_2$-N(piperazine)N---- | 909 | | |
| PROTAC-XVII-62 | ----N(piperazine)N-CH$_2$CH$_2$CH$_2$-O-CH$_2$CH$_2$-O---- | 911 | | |

TABLE 17-continued

Protacs composed of a RAF ligand and a cereblon ligand with 5-position linkage having the following chemical structure

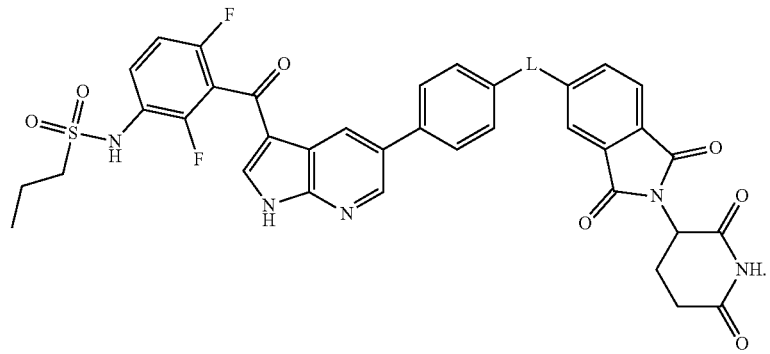

(PROTAC-XVII)

| PROTAC-XVII Compound | L | Mass | DC$_{50}$ (μM) | D$_{max}$ (%) |
|---|---|---|---|---|
| PROTAC-XVII-63 | ----N(piperazine)N-CH₂CH₂-O-CH₂CH₂-O---- | 911 | | |
| PROTAC-XVII-64 | ----N(piperazine)N-CH₂CH₂-O-CH₂CH₂CH₂-O---- | 911 | | |
| PROTAC-XVII-65 | ----N(piperazine)N-(CH₂)₄-O---- | 909 | | |
| PROTAC-XVII-66 | ----N(piperazine)N-(CH₂)₃-N(piperazine)N---- | 935 | | |
| PROTAC-XVII-67 | ----O-CH₂CH₂-N(piperazine)N-CH₂CH₂-O---- | 911 | | |
| PROTAC-XVII-68 | ----O-(CH₂)₄-N(piperazine)N-CH₂CH₂-O---- | 911 | | |
| PROTAC-XVII-69 | ----O-CH₂CH₂-N(piperazine)N-(CH₂)₄-O---- | 911 | | |
| PROTAC-XVII-70 | ----O---- | 727 | | |

TABLE 18

Protacs composed of a RAF ligand and a cereblon ligand with 5-position linkage having the following chemical structure

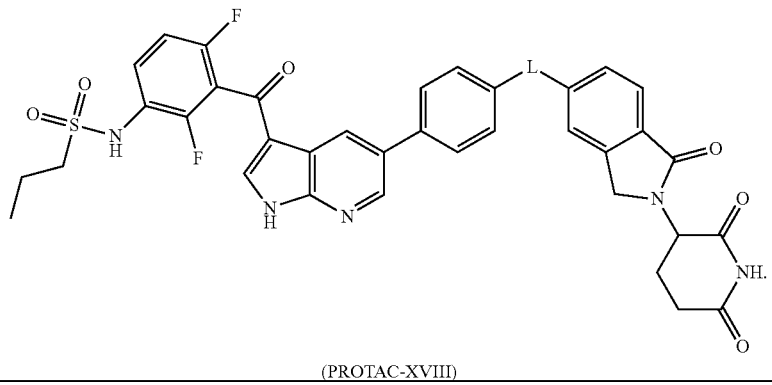

(PROTAC-XVIII)

| PROTAC-XVIII Compound | L | Mass | DC$_{50}$ (μM) | D$_{max}$ (%) |
|---|---|---|---|---|
| PROTAC-XVIII-1 | ----O~~~O---- | 757 | | |
| PROTAC-XVIII-2 | ----O~~~O~~~O--- | 801 | | |
| PROTAC-XVIII-3 | ----O~~~O~~~O~~~O---- | 845 | | |
| PROTAC-XVIII-4 | ----O~~~O~~~O~~~O~~~O--- | 889 | | |
| PROTAC-XVIII-5 | ----O~~~O~~~O~~~O~~~O~~~O---- | 933 | | |
| PROTAC-XVIII-6 | ----O~~~O~~~O~~~O~~~O~~~O~~~O--- | 977 | | |
| PROTAC-XVIII-7 | ----~~~O--- | 741 | | |
| PROTAC-XVIII-8 | ---~~~O--- | 727 | | |
| PROTAC-XVIII-9 | ---O~~~--- | 741 | | |
| PROTAC-XVIII-10 | ----O~~~--- | 727 | | |
| PROTAC-XVIII-11 | ----O~~~O--- | 771 | | |
| PROTAC-XVIII-12 | ----O~~~O---- | 785 | | |
| PROTAC-XVIII-13 | ----O~~O~~O---- | 815 | | |
| PROTAC-XVIII-14 | ----O~~~O~~~O---- | 815 | | |
| PROTAC-XVIII-15 | ----O~~~~O---- | 813 | | |
| PROTAC-XVIII-16 | ----O~~~O~~~O--- | 829 | | |

TABLE 18-continued

Protacs composed of a RAF ligand and a cereblon ligand with 5-position linkage having the following chemical structure

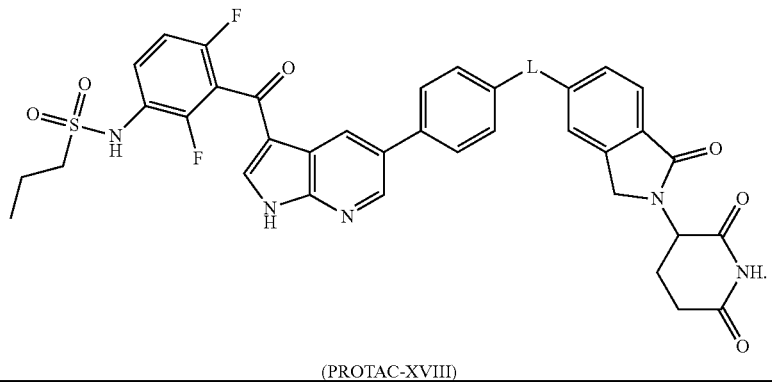

(PROTAC-XVIII)

| PROTAC-XVIII Compound | L | Mass | DC$_{50}$ (μM) | D$_{max}$ (%) |
|---|---|---|---|---|
| PROTAC-XVIII-17 | ----O~~~O~~~O~~~O''' | 829 | | |
| PROTAC-XVIII-18 | ----O~~~O~~~O~~~O''' | 829 | | |
| PROTAC-XVIII-19 | ----O~~~O~~~O~~~O~~~O''' | 859 | | |
| PROTAC-XVIII-20 | ----O~~~O~~~O~~~O~~~O''' | 859 | | |
| PROTAC-XVIII-21 | ----O~~~O~~~O~~~O~~~O''' | 859 | | |
| PROTAC-XVIII-22 | ----O~~~O~~~O~~~O''' | 857 | | |
| PROTAC-XVIII-23 | ----O~~~O~~~O~~~O''' | 857 | | |
| PROTAC-XVIII-24 | ----O~~~O~~~O~~~O''' | 857 | | |
| PROTAC-XVIII-25 | ----O~~~O~~~O~~~O''' | 857 | | |
| PROTAC-XVIII-26 | ----O~~~O~~~O~~~O''' | 857 | | |
| PROTAC-XVIII-27 | ----O~~~O~~~O~~~O---- | 873 | | |
| PROTAC-XVIII-28 | ----O~~~O~~~O~~~O---- | 873 | | |
| PROTAC-XVIII-29 | ----O~~~O~~~O~~~O---- | 873 | | |
| PROTAC-XVIII-30 | ----O~~~O~~~O~~~O---- | 873 | | |
| PROTAC-XVIII-31 | ----O~~~O~~~O~~~O---- | 873 | | |

TABLE 18-continued

Protacs composed of a RAF ligand and a cereblon ligand with 5-position linkage having the following chemical structure

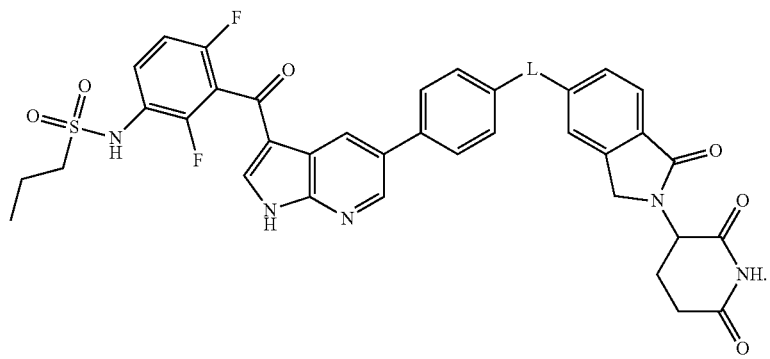

(PROTAC-XVIII)

| PROTAC-XVIII Compound | L | Mass | DC$_{50}$ (μM) | D$_{max}$ (%) |
|---|---|---|---|---|
| PROTAC-XVIII-32 | ----O~~~O~~~O~~~O---- | 871 | | |
| PROTAC-XVIII-33 | ----O~~~O~~~O~~~O---- | 871 | | |
| PROTAC-XVIII-34 | ----O~~~O~~~O~~~O---- | 871 | | |
| PROTAC-XVIII-35 | ----O~~~O~~~O~~~O---- | 871 | | |
| PROTAC-XVIII-36 | ----O~~~O~~~O~~~O---- | 871 | | |
| PROTAC-XVIII-37 | ----O~~~O~~~O~~~O---- | 871 | | |
| PROTAC-XVIII-38 | ----N(piperazine)N---- | 781 | | |
| PROTAC-XVIII-39 | O~~~N(piperazine)N---- | 825 | | |
| PROTAC-XVIII-40 | ----N(piperazine)N~~~O | 825 | | |
| PROTAC-XVIII-41 | ----O~~~N(piperazine)N---- | 839 | | |
| PROTAC-XVIII-42 | ----N(piperazine)N~~~O---- | 839 | | |
| PROTAC-XVIII-43 | O~~~N(piperazine)N---- | 853 | | |
| PROTAC-XVIII-44 | ----N(piperazine)N~~~O | 853 | | |

TABLE 18-continued

Protacs composed of a RAF ligand and a cereblon ligand with 5-position linkage having the following chemical structure

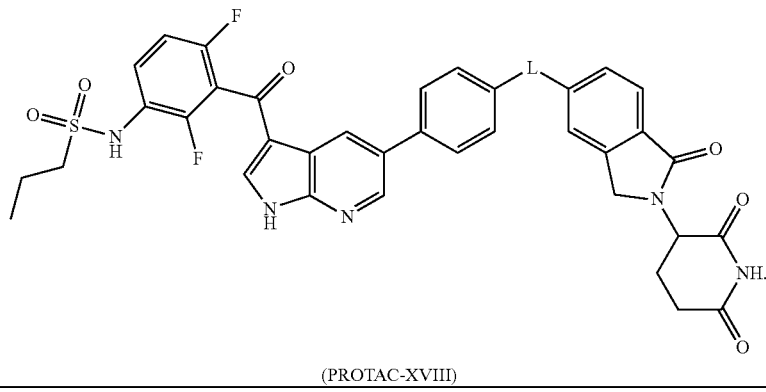

(PROTAC-XVIII)

| PROTAC-XVIII Compound | L | Mass | DC$_{50}$ (μM) | D$_{max}$ (%) |
|---|---|---|---|---|
| PROTAC-XVIII-45 | ----O\~\~O\~\~N(piperazine)N---- | 869 | | |
| PROTAC-XVIII-46 | ----N(piperazine)N\~\~O\~\~O---- | 869 | | |
| PROTAC-XVIII-47 | ----N(piperazine)N\~\~N(piperazine)N---- | 893 | | |
| PROTAC-XVIII-48 | O\~\~N(piperazine)N\~\~O | 869 | | |
| PROTAC-XVIII-49 | O\~\~O\~\~N(piperazine)N---- | 883 | | |
| PROTAC-XVIII-50 | O\~\~O\~\~N(piperazine)N---- | 883 | | |
| PROTAC-XVIII-51 | O\~\~\~\~N(piperazine)N---- | 881 | | |
| PROTAC-XVIII-52 | ----N(piperazine)N\~\~O\~\~O | 883 | | |
| PROTAC-XVIII-53 | ----N(piperazine)N\~\~O\~\~O | 883 | | |
| PROTAC-XVIII-54 | ----N(piperazine)N\~\~\~\~O | 881 | | |

TABLE 18-continued

Protacs composed of a RAF ligand and a cereblon ligand with 5-position linkage having the following chemical structure

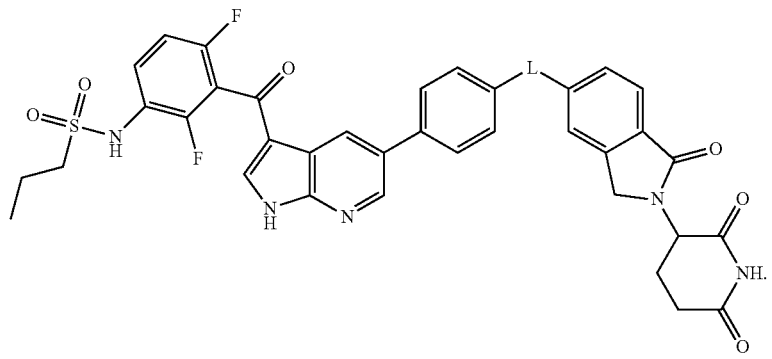

(PROTAC-XVIII)

| PROTAC-XVIII Compound | L | Mass | DC$_{50}$ (μM) | D$_{max}$ (%) |
|---|---|---|---|---|
| PROTAC-XVIII-55 | ----N(piperazine)N-CH$_2$CH$_2$CH$_2$-N(N-methylpiperazine) | 907 | | |
| PROTAC-XVIII-56 | ----O-CH$_2$CH$_2$-N(piperazine)N-CH$_2$CH$_2$-O---- | 883 | | |
| PROTAC-XVIII-57 | ----O-CH$_2$CH$_2$-N(piperazine)N-CH$_2$CH$_2$-O---- | 883 | | |
| PROTAC-XVIII-58 | ----O-CH$_2$CH$_2$CH$_2$-O-CH$_2$CH$_2$-N(piperazine)N---- | 897 | | |
| PROTAC-XVIII-59 | ----O-CH$_2$CH$_2$-O-CH$_2$CH$_2$CH$_2$-N(piperazine)N---- | 897 | | |
| PROTAC-XVIII-60 | ----O-CH$_2$-O-CH$_2$CH$_2$CH$_2$-N(piperazine)N---- | 897 | | |
| PROTAC-XVIII-61 | ----O-(CH$_2$)$_4$-N(piperazine)N---- | 895 | | |
| PROTAC-XVIII-62 | ----N(piperazine)N-CH$_2$CH$_2$CH$_2$-O-CH$_2$CH$_2$-O---- | 897 | | |

TABLE 18-continued

Protacs composed of a RAF ligand and a cereblon ligand with 5-position linkage having the following chemical structure

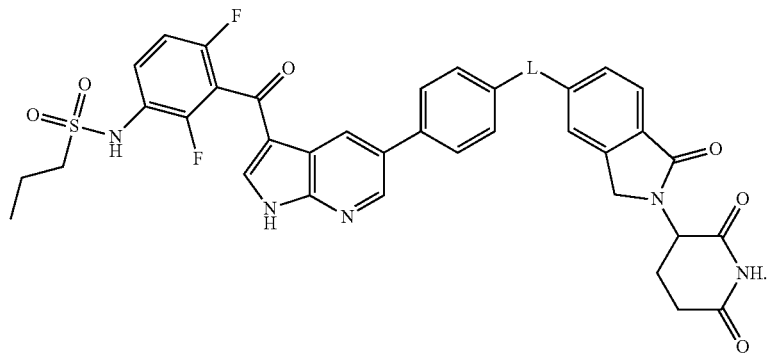

(PROTAC-XVIII)

| PROTAC-XVIII Compound | L | Mass | DC$_{50}$ (μM) | D$_{max}$ (%) |
|---|---|---|---|---|
| PROTAC-XVIII-63 | ----N(piperazine)N-CH$_2$CH$_2$-O-CH$_2$CH$_2$-O---- | 897 | | |
| PROTAC-XVIII-64 | ----N(piperazine)N-CH$_2$CH$_2$-O-CH$_2$CH$_2$CH$_2$-O---- | 897 | | |
| PROTAC-XVIII-65 | ----N(piperazine)N-(CH$_2$)$_4$-O---- | 895 | | |
| PROTAC-XVIII-66 | ----N(piperazine)N-CH$_2$CH$_2$CH$_2$-N(piperazine)N---- | 921 | | |
| PROTAC-XVIII-67 | ----O-CH$_2$CH$_2$-N(piperazine)N-CH$_2$CH$_2$-O---- | 897 | | |
| PROTAC-XVIII-68 | ----O-(CH$_2$)$_4$-N(piperazine)N-CH$_2$CH$_2$-O---- | 897 | | |
| PROTAC-XVIII-69 | ----O-CH$_2$CH$_2$-N(piperazine)N-(CH$_2$)$_4$-O---- | 897 | | |
| PROTAC-XVIII-70 | ----O---- | 713 | | |

TABLE 19

Protacs composed of a RAF ligand and a cereblon ligand with 6-position linkage having the following chemical structure

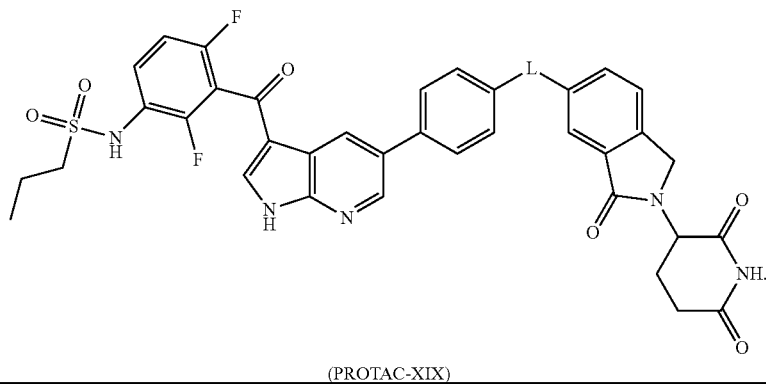

(PROTAC-XIX)

| PROTAC-XIX Compound | L | Mass | DC$_{50}$ (μM) | D$_{max}$ (%) |
|---|---|---|---|---|
| PROTAC-XIX-1 | ----O\_/\_O\_/\_---- | 757 | | |
| PROTAC-XIX-2 | ----O\_/\_O\_/\_O\_/\_ | 801 | | |
| PROTAC-XIX-3 | ----O\_/\_O\_/\_O\_/\_O---- | 845 | | |
| PROTAC-XIX-4 | ----O\_/\_O\_/\_O\_/\_O\_/\_O | 889 | | |
| PROTAC-XIX-5 | ----O\_/\_O\_/\_O\_/\_O\_/\_O\_/\_O---- | 933 | | |
| PROTAC-XIX-6 | ----O\_/\_O\_/\_O\_/\_O\_/\_O\_/\_O\_/\_O | 977 | | |
| PROTAC-XIX-7 | ----/\_O | 741 | | |
| PROTAC-XIX-8 | /\_O\_ | 727 | | |
| PROTAC-XIX-9 | \_/\_O | 741 | | |
| PROTAC-XIX-10 | ----O\_/\_ | 727 | | |
| PROTAC-XIX-11 | ----O\_/\_\_O | 771 | | |
| PROTAC-XIX-12 | ----O\_/\_\_\_O---- | 785 | | |
| PROTAC-XIX-13 | ----O\_/\_O\_/\_O---- | 815 | | |
| PROTAC-XIX-14 | ----O\_/\_O\_/\_O---- | 815 | | |
| PROTAC-XIX-15 | ----O\_/\_\_O\_/\_\_O---- | 813 | | |
| PROTAC-XIX-16 | ----O\_/\_O\_/\_\_O | 829 | | |

TABLE 19-continued

Protacs composed of a RAF ligand and a cereblon ligand with 6-position linkage having the following chemical structure

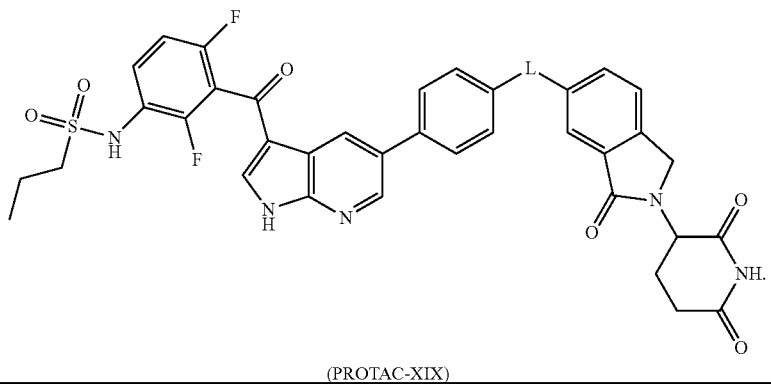

(PROTAC-XIX)

| PROTAC-XIX Compound | L | Mass | DC$_{50}$ (μM) | D$_{max}$ (%) |
|---|---|---|---|---|
| PROTAC-XIX-17 | ----O∼∼O∼∼O∼∼O⋰ | 829 | | |
| PROTAC-XIX-18 | ----O∼∼O∼∼O∼∼O⋰ | 829 | | |
| PROTAC-XIX-19 | ----O∼∼O∼∼O∼∼O⋰ | 859 | | |
| PROTAC-XIX-20 | ----O∼∼O∼∼O∼∼O⋰ | 859 | | |
| PROTAC-XIX-21 | ----O∼∼O∼∼O∼∼O⋰ | 859 | | |
| PROTAC-XIX-22 | ----O∼∼O∼∼O∼∼O⋰ | 857 | | |
| PROTAC-XIX-23 | ----O∼∼O∼∼O∼∼O⋰ | 857 | | |
| PROTAC-XIX-24 | ----O∼∼O∼∼O∼∼O⋰ | 857 | | |
| PROTAC-XIX-25 | ----O∼∼O∼∼O∼∼O⋰ | 857 | | |
| PROTAC-XIX-26 | ----O∼∼O∼∼O∼∼O⋰ | 857 | | |
| PROTAC-XIX-27 | ----O∼∼O∼∼O∼∼O∼∼O---- | 873 | | |
| PROTAC-XIX-28 | ----O∼∼O∼∼O∼∼O∼∼O---- | 873 | | |
| PROTAC-XIX-29 | ----O∼∼O∼∼O∼∼O∼∼O---- | 873 | | |
| PROTAC-XIX-30 | ----O∼∼O∼∼O∼∼O∼∼O---- | 873 | | |
| PROTAC-XIX-31 | ----O∼∼O∼∼O∼∼O∼∼O---- | 873 | | |

TABLE 19-continued

Protacs composed of a RAF ligand and a cereblon ligand with 6-position linkage having the following chemical structure

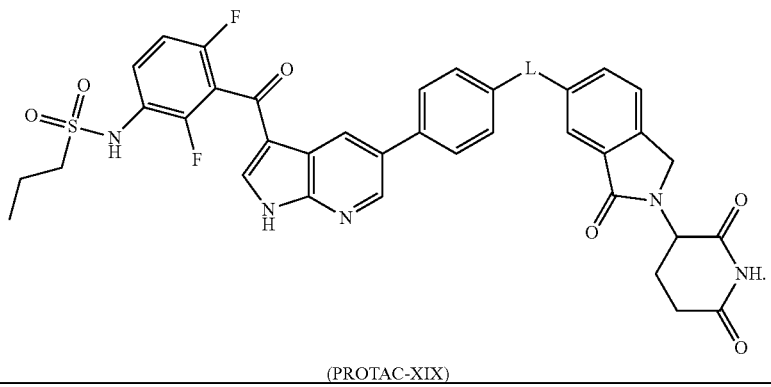

(PROTAC-XIX)

| PROTAC-XIX Compound | L | Mass | DC$_{50}$ (μM) | D$_{max}$ (%) |
|---|---|---|---|---|
| PROTAC-XIX-32 | ----O~~~O~~~O~~~O---- | 871 | | |
| PROTAC-XIX-33 | ----O~~~O~~~O~~~O---- | 871 | | |
| PROTAC-XIX-34 | ----O~~~O~~~O~~~O---- | 871 | | |
| PROTAC-XIX-35 | ----O~~~O~~~O~~~O---- | 871 | | |
| PROTAC-XIX-36 | ----O~~~O~~~O~~~O---- | 871 | | |
| PROTAC-XIX-37 | ----O~~~O~~~O~~~O---- | 871 | | |
| PROTAC-XIX-38 | ----N(piperazine)N---- | 781 | | |
| PROTAC-XIX-39 | O~~N(piperazine)N---- | 825 | | |
| PROTAC-XIX-40 | ----N(piperazine)N~~O | 825 | | |
| PROTAC-XIX-41 | ----O~~N(piperazine)N---- | 839 | | |
| PROTAC-XIX-42 | ----N(piperazine)N~~O---- | 839 | | |
| PROTAC-XIX-43 | O~~~N(piperazine)N---- | 853 | | |
| PROTAC-XIX-44 | ----N(piperazine)N~~~O | 853 | | |

TABLE 19-continued

Protacs composed of a RAF ligand and a cereblon ligand with 6-position linkage having the following chemical structure

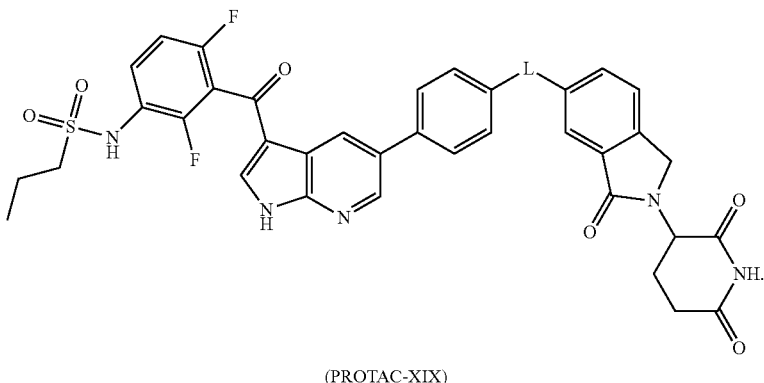

(PROTAC-XIX)

| PROTAC-XIX Compound | L | Mass | DC$_{50}$ (μM) | D$_{max}$ (%) |
|---|---|---|---|---|
| PROTAC-XIX-45 | ----O\_/O\_/N(piperazine)N---- | 869 | | |
| PROTAC-XIX-46 | ----N(piperazine)N\_/O\_/O---- | 869 | | |
| PROTAC-XIX-47 | ----N(piperazine)N\_/N(piperazine)N---- | 893 | | |
| PROTAC-XIX-48 | O\_/N(piperazine)N\_/O | 869 | | |
| PROTAC-XIX-49 | O\_/O\_/N(piperazine)N---- | 883 | | |
| PROTAC-XIX-50 | O\_/O\_/N(piperazine)N---- | 883 | | |
| PROTAC-XIX-51 | O\_/\_/N(piperazine)N---- | 881 | | |
| PROTAC-XIX-52 | ----N(piperazine)N\_/O\_/O | 883 | | |
| PROTAC-XIX-53 | ----N(piperazine)N\_/O\_/O | 883 | | |
| PROTAC-XIX-54 | ----N(piperazine)N\_/\_/O | 881 | | |

TABLE 19-continued

Protacs composed of a RAF ligand and a cereblon ligand with 6-position linkage having the following chemical structure

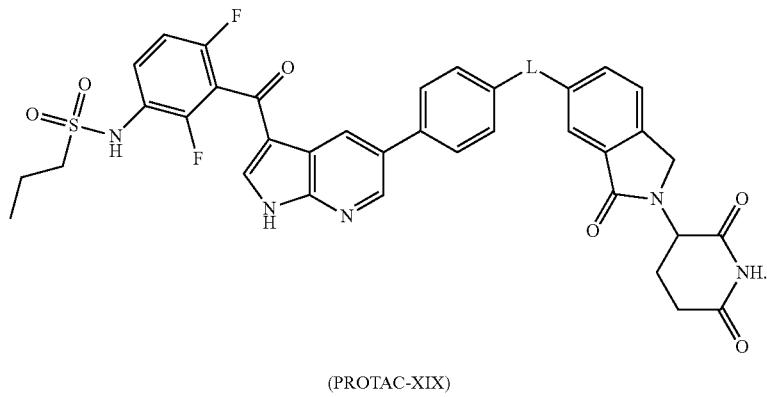

(PROTAC-XIX)

| PROTAC-XIX Compound | L | Mass | DC$_{50}$ (μM) | D$_{max}$ (%) |
|---|---|---|---|---|
| PROTAC-XIX-55 | piperazine-CH$_2$CH$_2$CH$_2$-N-methylpiperazine | 907 | | |
| PROTAC-XIX-56 | -O-CH$_2$CH$_2$-piperazine-CH$_2$CH$_2$-O- | 883 | | |
| PROTAC-XIX-57 | -O-CH$_2$CH$_2$-piperazine-CH$_2$CH$_2$CH$_2$-O- | 883 | | |
| PROTAC-XIX-58 | -O-CH$_2$CH$_2$CH$_2$-O-CH$_2$CH$_2$-piperazine- | 897 | | |
| PROTAC-XIX-59 | -O-CH$_2$CH$_2$-O-CH$_2$CH$_2$CH$_2$-piperazine- | 897 | | |
| PROTAC-XIX-60 | -O-CH$_2$-O-CH$_2$CH$_2$CH$_2$-piperazine- | 897 | | |
| PROTAC-XIX-61 | -O-CH$_2$CH$_2$CH$_2$CH$_2$CH$_2$-piperazine- | 895 | | |
| PROTAC-XIX-62 | -piperazine-CH$_2$CH$_2$CH$_2$-O-CH$_2$CH$_2$-O- | 897 | | |

TABLE 19-continued

Protacs composed of a RAF ligand and a cereblon ligand with 6-position linkage having the following chemical structure

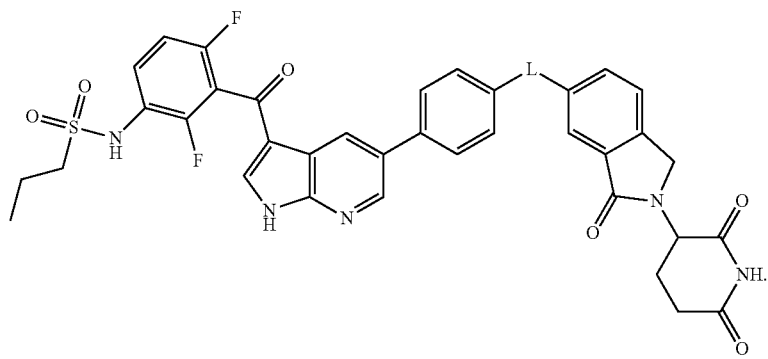

(PROTAC-XIX)

| PROTAC-XIX Compound | L | Mass | DC$_{50}$ (μM) | D$_{max}$ (%) |
|---|---|---|---|---|
| PROTAC-XIX-63 | ----N(piperazine)N-CH₂CH₂-O-CH₂CH₂-O---- | 897 | | |
| PROTAC-XIX-64 | ----N(piperazine)N-CH₂CH₂-O-CH₂CH₂CH₂-O---- | 897 | | |
| PROTAC-XIX-65 | ----N(piperazine)N-(CH₂)₄-O---- | 895 | | |
| PROTAC-XIX-66 | ----N(piperazine)N-CH₂CH₂CH₂-N(piperazine)N---- | 921 | | |
| PROTAC-XIX-67 | ----O-CH₂CH₂CH₂-N(piperazine)N-CH₂CH₂-O---- | 897 | | |
| PROTAC-XIX-68 | ----O-(CH₂)₄-N(piperazine)N-CH₂CH₂-O---- | 897 | | |
| PROTAC-XIX-69 | ----O-CH₂CH₂-N(piperazine)N-(CH₂)₄-O---- | 897 | | |
| PROTAC-XIX-70 | ----O---- | 713 | | |

TABLE 20

Protacs composed of a RAF ligand and a cereblon ligand with 4-posilion linkage having the following chemical structure

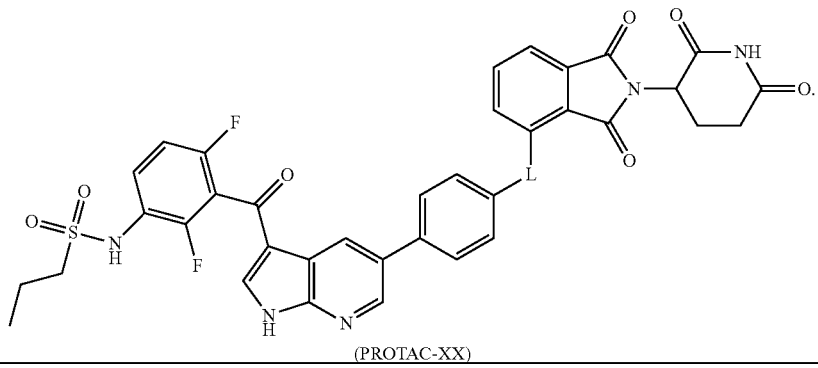

(PROTAC-XX)

| PROTAC-XX Compound | L | Mass | DC$_{50}$ (µM) | D$_{max}$ (%) |
|---|---|---|---|---|
| PROTAC-XX-1 | ----O~~O---- | 771 | | |
| PROTAC-XX-2 | ----O~~O~~O---- | 815 | | |
| PROTAC-XX-3 | ----O~~O~~O~~O---- | 859 | | |
| PROTAC-XX-4 | ----O~~O~~O~~O~~O---- | 903 | | |
| PROTAC-XX-5 | ----O~~O~~O~~O~~O~~O---- | 947 | | |
| PROTAC-XX-6 | ----O~~O~~O~~O~~O~~O~~O---- | 991 | | |
| PROTAC-XX-7 | ----~~O---- | 755 | | |
| PROTAC-XX-8 | ----~O---- | 741 | | |
| PROTAC-XX-9 | ----O~---- | 755 | | |
| PROTAC-XX-10 | ----O~---- | 741 | | |
| PROTAC-XX-11 | ----O~~O---- | 785 | | |
| PROTAC-XX-12 | ----O~~~O---- | 799 | | |
| PROTAC-XX-13 | ----O~~O~~O---- | 829 | | |
| PROTAC-XX-14 | ----O~~O~~O---- | 829 | | |
| PROTAC-XX-15 | ----O~~~O~~O---- | 827 | | |
| PROTAC-XX-16 | ----O~~O~~~O---- | 843 | | |

TABLE 20-continued
Protacs composed of a RAF ligand and a cereblon ligand with 4-posilion linkage having the following chemical structure
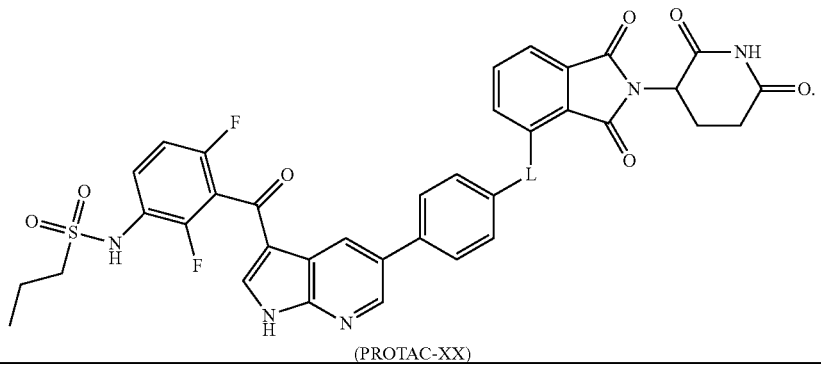
(PROTAC-XX)
| PROTAC-XX Compound | L | Mass | DC$_{50}$ (μM) | D$_{max}$ (%) |
|---|---|---|---|---|
| PROTAC-XX-17 | | 843 | | |
| PROTAC-XX-18 | | 843 | | |
| PROTAC-XX-19 | | 873 | | |
| PROTAC-XX-20 | | 873 | | |
| PROTAC-XX-21 | | 873 | | |
| PROTAC-XX-22 | | 871 | | |
| PROTAC-XX-23 | | 871 | | |
| PROTAC-XX-24 | | 871 | | |
| PROTAC-XX-25 | | 871 | | |
| PROTAC-XX-26 | | 871 | | |
| PROTAC-XX-27 | | 887 | | |
| PROTAC-XX-28 | | 887 | | |
| PROTAC-XX-29 | | 887 | | |
| PROTAC-XX-30 | | 887 | | |
| PROTAC-XX-31 | | 887 | | |
| PROTAC-XX-32 | | 885 | | |

TABLE 20-continued

Protacs composed of a RAF ligand and a cereblon ligand with 4-position linkage having the following chemical structure

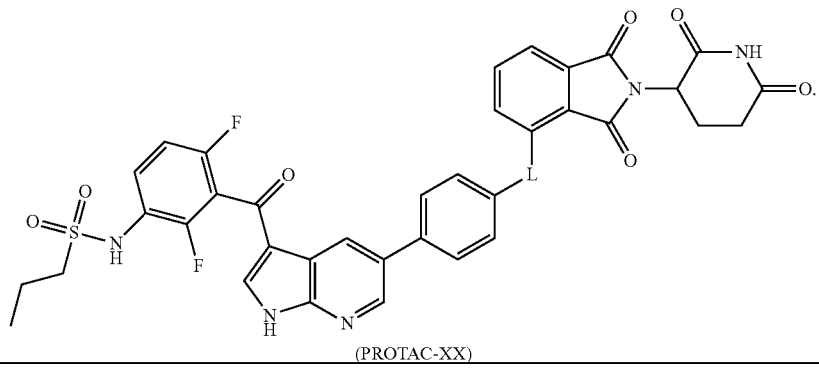

(PROTAC-XX)

| PROTAC-XX Compound | L | Mass | DC$_{50}$ (μM) | D$_{max}$ (%) |
|---|---|---|---|---|
| PROTAC-XX-33 | ----O~~~O~~~O---- | 885 | | |
| PROTAC-XX-34 | ----O~~~O~~~O---- | 885 | | |
| PROTAC-XX-35 | ----O~~~O~~~O---- | 885 | | |
| PROTAC-XX-36 | ----O~~~O~~~O---- | 885 | | |
| PROTAC-XX-37 | ----O~~~O~~~O---- | 885 | | |
| PROTAC-XX-38 | ----N(piperazine)N---- | 795 | | |
| PROTAC-XX-39 | ----O~N(piperazine)N---- | 839 | | |
| PROTAC-XX-40 | ----N(piperazine)N~O---- | 839 | | |
| PROTAC-XX-41 | ----O~~N(piperazine)N---- | 853 | | |
| PROTAC-XX-42 | ----N(piperazine)N~~O---- | 853 | | |
| PROTAC-XX-43 | ----O~~~N(piperazine)N---- | 867 | | |
| PROTAC-XX-44 | ----N(piperazine)N~~~O---- | 867 | | |
| PROTAC-XX-45 | ----O~O~~N(piperazine)N---- | 883 | | |

TABLE 20-continued

Protacs composed of a RAF ligand and a cereblon ligand with 4-posilion linkage having the following chemical structure

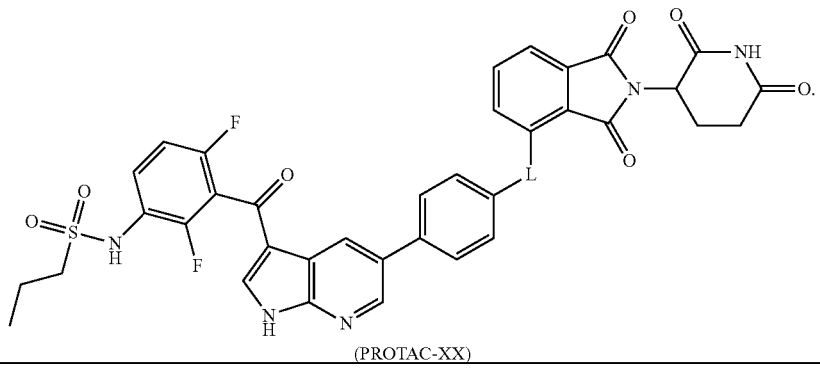

(PROTAC-XX)

| PROTAC-XX Compound | L | Mass | DC$_{50}$ (μM) | D$_{max}$ (%) |
|---|---|---|---|---|
| PROTAC-XX-46 | ----N(piperazine)N-CH$_2$CH$_2$-O-CH$_2$CH$_2$-O---- | 883 | | |
| PROTAC-XX-47 | ----N(piperazine)N-CH$_2$CH$_2$-N(piperazine)N---- | 907 | | |
| PROTAC-XX-48 | O-CH$_2$CH$_2$-N(piperazine)N-CH$_2$CH$_2$-O | 883 | | |
| PROTAC-XX-49 | O-CH$_2$CH$_2$-O-CH$_2$CH$_2$-N(piperazine)N---- | 897 | | |
| PROTAC-XX-50 | O-CH$_2$CH$_2$-O-CH$_2$CH$_2$-N(piperazine)N---- | 897 | | |
| PROTAC-XX-51 | O-(CH$_2$)$_4$-N(piperazine)N---- | 895 | | |
| PROTAC-XX-52 | ----N(piperazine)N-CH$_2$CH$_2$-O-CH$_2$CH$_2$CH$_2$-O | 897 | | |
| PROTAC-XX-53 | ----N(piperazine)N-CH$_2$CH$_2$-O-CH$_2$CH$_2$-O | 897 | | |
| PROTAC-XX-54 | ----N(piperazine)N-(CH$_2$)$_4$-O | 895 | | |
| PROTAC-XX-55 | ----N(piperazine)N-CH$_2$CH$_2$CH$_2$-N(N-methylpiperazine) | 921 | | |

TABLE 20-continued

Protacs composed of a RAF ligand and a cereblon ligand with 4-posilion linkage having the following chemical structure

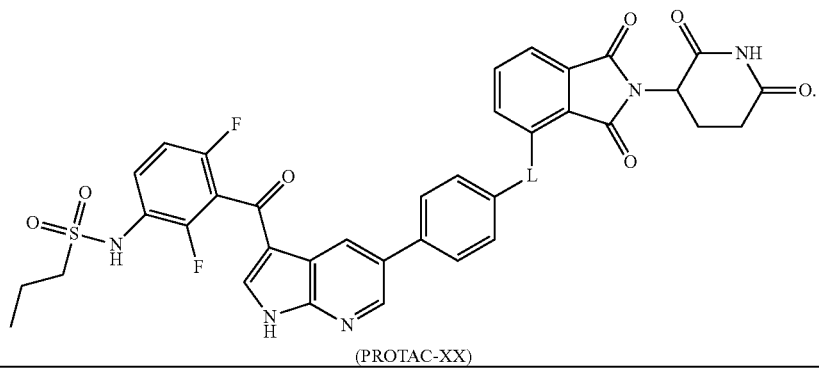

(PROTAC-XX)

| PROTAC-XX Compound | L | Mass | DC$_{50}$ (μM) | D$_{max}$ (%) |
|---|---|---|---|---|
| PROTAC-XX-56 | ----O~~~N(piperazine)N~~~O---- | 897 | | |
| PROTAC-XX-57 | ----O~~~N(piperazine)N~~~O---- | 897 | | |
| PROTAC-XX-58 | ----O~~~O~~~N(piperazine)N---- | 911 | | |
| PROTAC-XX-59 | ----O~~~O~~~N(piperazine)N---- | 911 | | |
| PROTAC-XX-60 | ----O~~~O~~~N(piperazine)N---- | 911 | | |
| PROTAC-XX-61 | ----O~~~~~N(piperazine)N---- | 909 | | |
| PROTAC-XX-62 | ----N(piperazine)N~~~O~~~O---- | 911 | | |
| PROTAC-XX-63 | ----N(piperazine)N~~~O~~~O---- | 911 | | |
| PROTAC-XX-64 | ----N(piperazine)N~~~O~~~O---- | 911 | | |
| PROTAC-XX-65 | ----N(piperazine)N~~~~~O---- | 909 | | |
| PROTAC-XX-66 | ----N(piperazine)N~~~N(piperazine)N---- | 935 | | |

TABLE 20-continued

Protacs composed of a RAF ligand and a cereblon ligand with 4-position linkage having the following chemical structure

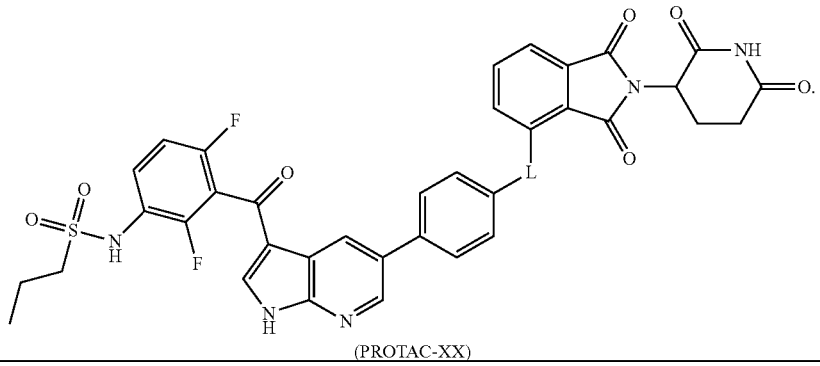

(PROTAC-XX)

| PROTAC-XX Compound | L | Mass | DC$_{50}$ (μM) | D$_{max}$ (%) |
|---|---|---|---|---|
| PROTAC-XX-67 | ----O~~~N(piperazine)N~~~O---- | 911 | | |
| PROTAC-XX-68 | ~O~~~~N(piperazine)N~~O~ | 911 | | |
| PROTAC-XX-69 | ~O~~N(piperazine)N~~~~O~ | 911 | | |
| PROTAC-XX-70 | ----O~ | 727 | | |

TABLE 21

Protacs composed of a RAF ligand and a cereblon ligand with 4-position linkage having the following chemical structure

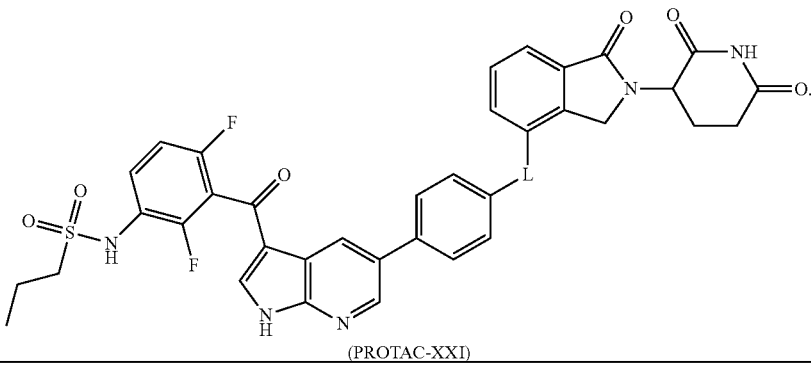

(PROTAC-XXI)

| PROTAC-XXI Compound | L | Mass | DC$_{50}$ (μM) | D$_{max}$ (%) |
|---|---|---|---|---|
| PROTAC-XXI-1 | ----O~~O---- | 757 | | |
| PROTAC-XXI-2 | ----O~~O~~O~ | 801 | | |
| PROTAC-XXI-3 | ----O~~O~~O~~O---- | 845 | | |

TABLE 21-continued

Protacs composed of a RAF ligand and a cereblon ligand with 4-position linkage having the following chemical structure

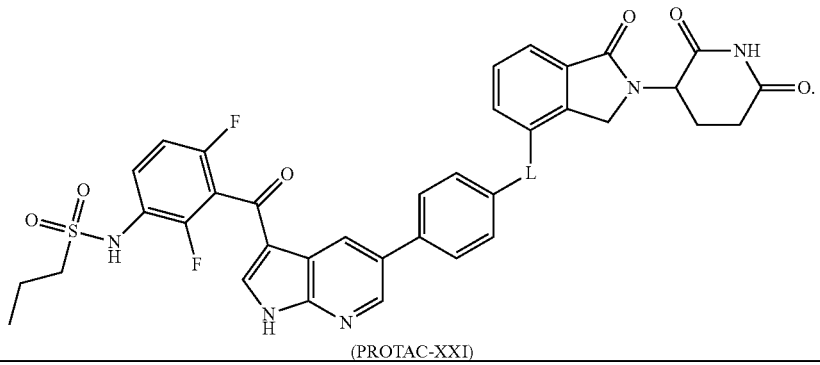

(PROTAC-XXI)

| PROTAC-XXI Compound | L | Mass | DC$_{50}$ (µM) | D$_{max}$ (%) |
|---|---|---|---|---|
| PROTAC-XXI-4 | | 889 | | |
| PROTAC-XXI-5 | | 933 | | |
| PROTAC-XXI-6 | | 977 | | |
| PROTAC-XXI-7 | | 741 | | |
| PROTAC-XXI-8 | | 727 | | |
| PROTAC-XXI-9 | | 741 | | |
| PROTAC-XXI-10 | | 727 | | |
| PROTAC-XXI-11 | | 771 | | |
| PROTAC-XXI-12 | | 785 | | |
| PROTAC-XXI-13 | | 815 | | |
| PROTAC-XXI-14 | | 815 | | |
| PROTAC-XXI-15 | | 813 | | |
| PROTAC-XXI-16 | | 829 | | |
| PROTAC-XXI-17 | | 829 | | |
| PROTAC-XXI-18 | | 829 | | |
| PROTAC-XXI-19 | | 859 | | |

TABLE 21-continued

Protacs composed of a RAF ligand and a cereblon ligand with 4-position linkage having the following chemical structure

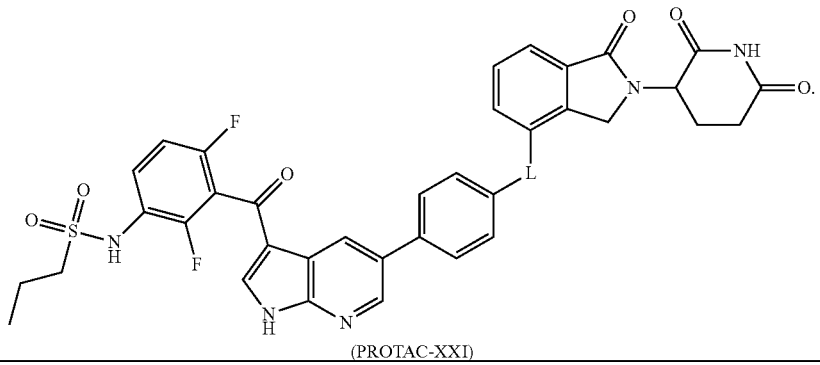

(PROTAC-XXI)

| PROTAC-XXI Compound | L | Mass | DC$_{50}$ (μM) | D$_{max}$ (%) |
|---|---|---|---|---|
| PROTAC-XXI-20 | | 859 | | |
| PROTAC-XXI-21 | | 859 | | |
| PROTAC-XXI-22 | | 857 | | |
| PROTAC-XXI-23 | | 857 | | |
| PROTAC-XXI-24 | | 857 | | |
| PROTAC-XXI-25 | | 857 | | |
| PROTAC-XXI-26 | | 857 | | |
| PROTAC-XXI-27 | | 873 | | |
| PROTAC-XXI-28 | | 873 | | |
| PROTAC-XXI-29 | | 873 | | |
| PROTAC-XXI-30 | | 873 | | |
| PROTAC-XXI-31 | | 873 | | |
| PROTAC-XXI-32 | | 871 | | |
| PROTAC-XXI-33 | | 871 | | |
| PROTAC-XXI-34 | | 871 | | |
| PROTAC-XXI-35 | | 871 | | |

TABLE 21-continued

Protacs composed of a RAF ligand and a cereblon ligand with 4-position linkage having the following chemical structure

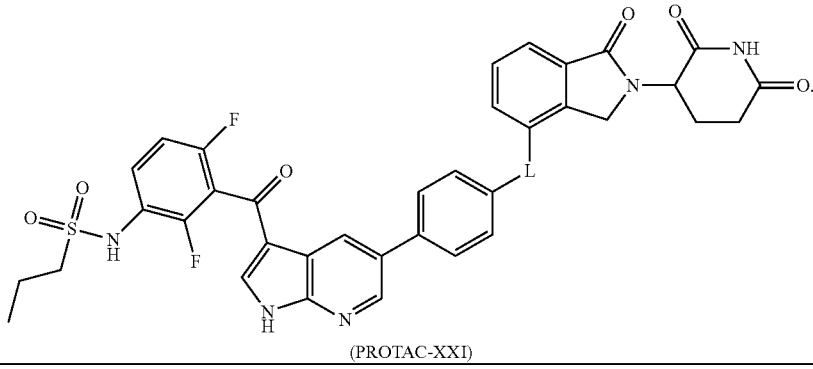

(PROTAC-XXI)

| PROTAC-XXI Compound | L | Mass | DC$_{50}$ (μM) | D$_{max}$ (%) |
|---|---|---|---|---|
| PROTAC-XXI-36 | ----O~~O~~O---- | 871 | | |
| PROTAC-XXI-37 | ----O~~O~~O---- | 871 | | |
| PROTAC-XXI-38 | ----N(piperazine)N---- | 781 | | |
| PROTAC-XXI-39 | O~~N(piperazine)N---- | 825 | | |
| PROTAC-XXI-40 | ----N(piperazine)N~~O | 825 | | |
| PROTAC-XXI-41 | ----O~~N(piperazine)N---- | 839 | | |
| PROTAC-XXI-42 | ----N(piperazine)N~~O---- | 839 | | |
| PROTAC-XXI-43 | O~~N(piperazine)N---- | 853 | | |
| PROTAC-XXI-44 | ----N(piperazine)N~~O | 853 | | |
| PROTAC-XXI-45 | ----O~O~N(piperazine)N---- | 869 | | |
| PROTAC-XXI-46 | ----N(piperazine)N~O~O---- | 869 | | |

TABLE 21-continued
Protacs composed of a RAF ligand and a cereblon ligand with 4-position linkage having the following chemical structure
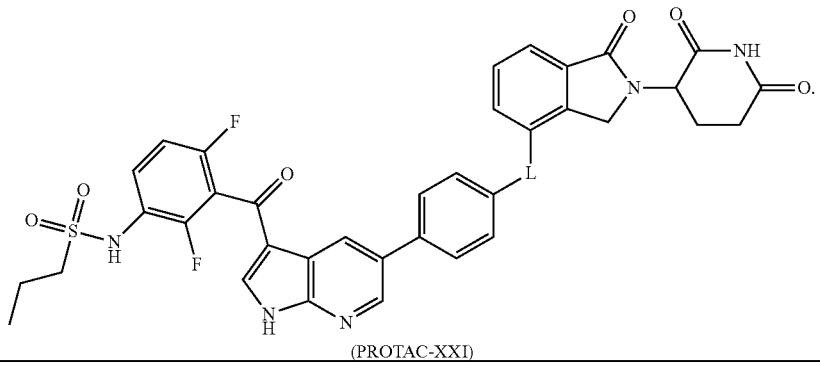
(PROTAC-XXI)
| PROTAC-XXI Compound | L | Mass | DC$_{50}$ (μM) | D$_{max}$ (%) |
|---|---|---|---|---|
| PROTAC-XXI-47 | | 893 | | |
| PROTAC-XXI-48 | | 869 | | |
| PROTAC-XXI-49 | | 883 | | |
| PROTAC-XXI-50 | | 883 | | |
| PROTAC-XXI-51 | | 881 | | |
| PROTAC-XXI-52 | | 883 | | |
| PROTAC-XXI-53 | | 883 | | |
| PROTAC-XXI-54 | | 881 | | |
| PROTAC-XXI-55 | | 907 | | |
| PROTAC-XXI-56 | | 883 | | |

TABLE 21-continued
Protacs composed of a RAF ligand and a cereblon ligand with 4-position linkage having the following chemical structure
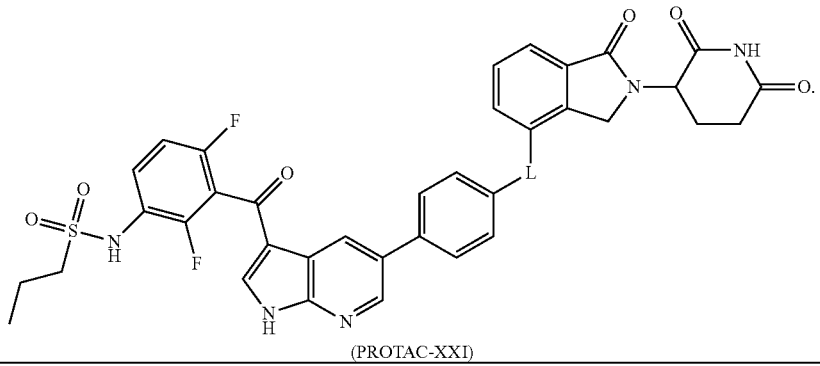
(PROTAC-XXI)
| PROTAC-XXI Compound | L | Mass | DC$_{50}$ (μM) | D$_{max}$ (%) |
|---|---|---|---|---|
| PROTAC-XXI-57 | | 883 | | |
| PROTAC-XXI-58 | | 897 | | |
| PROTAC-XXI-59 | | 897 | | |
| PROTAC-XXI-60 | | 897 | | |
| PROTAC-XXI-61 | | 895 | | |
| PROTAC-XXI-62 | | 897 | | |
| PROTAC-XXI-63 | | 897 | | |
| PROTAC-XXI-64 | | 897 | | |
| PROTAC-XXI-65 | | 895 | | |
| PROTAC-XXI-66 | | 921 | | |
| PROTAC-XXI-67 | | 897 | | |

TABLE 21-continued

Protacs composed of a RAF ligand and a cereblon ligand with 4-position linkage having the following chemical structure

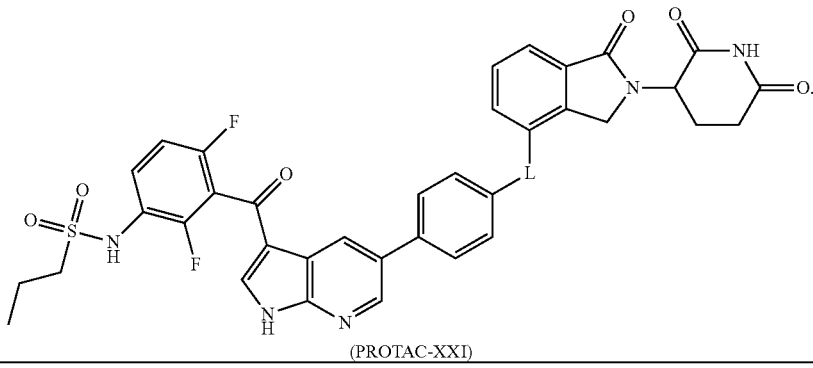

(PROTAC-XXI)

| PROTAC-XXI Compound | L | Mass | DC$_{50}$ (μM) | D$_{max}$ (%) |
|---|---|---|---|---|
| PROTAC-XXI-68 | ⋯O~~~N(piperazine)N~~O⋯ | 897 | | |
| PROTAC-XXI-69 | ⋯O~~N(piperazine)N~~~O⋯ | 897 | | |
| PROTAC-XXI-70 | ⋯O⋯ | 713 | | |

TABLE 22

Protacs composed of a RAF ligand and a cereblon ligand with 7-position linkage having the following chemical structure

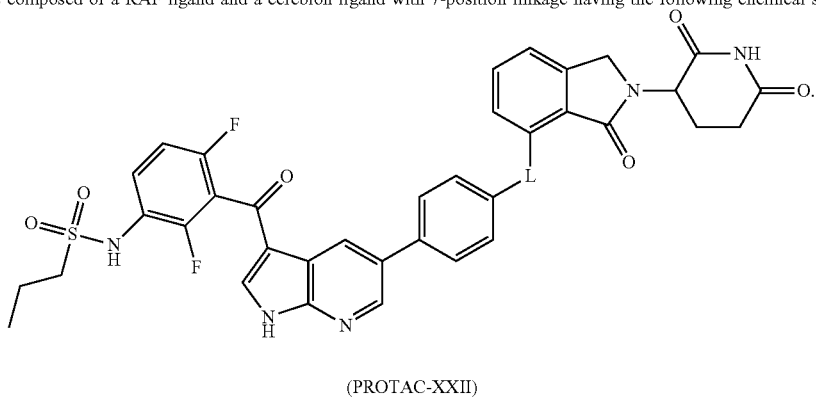

(PROTAC-XXII)

| PROTAC-XXII Compound | L | Mass | DC$_{50}$ (μM) | D$_{max}$ (%) |
|---|---|---|---|---|
| PROTAC-XXII-1 | ⋯O~O⋯ | 757 | | |
| PROTAC-XXII-2 | ⋯O~O~O⋯ | 801 | | |
| PROTAC-XXII-3 | ⋯O~O~O~O⋯ | 845 | | |
| PROTAC-XXII-4 | ⋯O~O~O~O~O⋯ | 889 | | |

TABLE 22-continued

Protacs composed of a RAF ligand and a cereblon ligand with 7-position linkage having the following chemical structure

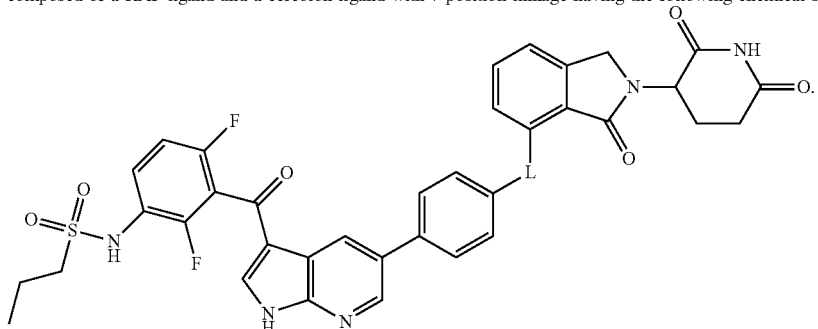

(PROTAC-XXII)

| PROTAC-XXII Compound | L | Mass | DC$_{50}$ (μM) | D$_{max}$ (%) |
|---|---|---|---|---|
| PROTAC-XXII-5 | ----O\_/\O\_/\O\_/\O\_/\O---- | 933 | | |
| PROTAC-XXII-6 | ----O\_/\O\_/\O\_/\O\_/\O\_/\O-- | 977 | | |
| PROTAC-XXII-7 | ----\_/\O-- | 741 | | |
| PROTAC-XXII-8 | ,,/\_O-- | 727 | | |
| PROTAC-XXII-9 | ,,O\_/---- | 741 | | |
| PROTAC-XXII-10 | /---- ----O | 727 | | |
| PROTAC-XXII-11 | ----O\_/\_/O-- | 771 | | |
| PROTAC-XXII-12 | ----O\_/\_/O---- | 785 | | |
| PROTAC-XXII-13 | ----O\_/\O\_/\O---- | 815 | | |
| PROTAC-XXII-14 | ----O\_/\O\_/\O---- | 815 | | |
| PROTAC-XXII-15 | ----O\_/\_/\_/O---- | 813 | | |
| PROTAC-XXII-16 | ----O\_/\O\_/\_/O-- | 829 | | |
| PROTAC-XXII-17 | ----O\_/\_/O\_/O-- | 829 | | |
| PROTAC-XXII-18 | ----O\_/\_/O\_/\_/O-- | 829 | | |
| PROTAC-XXII-19 | ----O\_/\O\_/\O\_/\O-- | 859 | | |
| PROTAC-XXII-20 | ----O\_/\O\_/\O\_/\O-- | 859 | | |

TABLE 22-continued

Protacs composed of a RAF ligand and a cereblon ligand with 7-position linkage having the following chemical structure

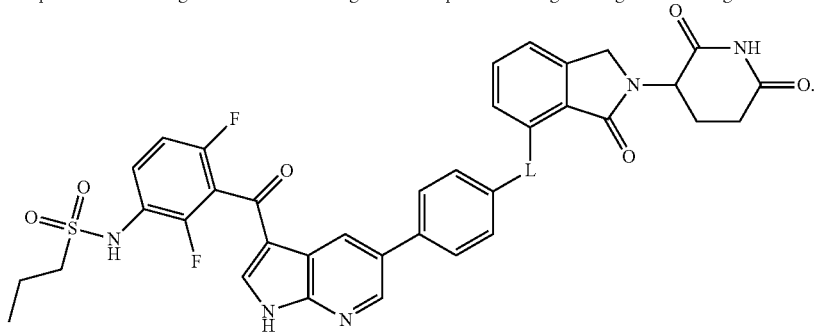

(PROTAC-XXII)

| PROTAC-XXII Compound | L | Mass | DC$_{50}$ (μM) | D$_{max}$ (%) |
|---|---|---|---|---|
| PROTAC-XXII-21 | ----O~~O~~O~~O~~O | 859 | | |
| PROTAC-XXII-22 | ----O~~O~~O~~O | 857 | | |
| PROTAC-XXII-23 | ----O~~O~~O~~O | 857 | | |
| PROTAC-XXII-24 | ----O~~O~~O~~O | 857 | | |
| PROTAC-XXII-25 | ----O~~O~~O~~O | 857 | | |
| PROTAC-XXII-26 | ----O~~O~~O~~O | 857 | | |
| PROTAC-XXII-27 | ----O~~O~~O~~O~~O---- | 873 | | |
| PROTAC-XXII-28 | ----O~~O~~O~~O~~O---- | 873 | | |
| PROTAC-XXII-29 | ----O~~O~~O~~O~~O---- | 873 | | |
| PROTAC-XXII-30 | ----O~~O~~O~~O~~O---- | 873 | | |
| PROTAC-XXII-31 | ----O~~O~~O~~O~~O---- | 873 | | |
| PROTAC-XXII-32 | ----O~~O~~O~~O---- | 871 | | |
| PROTAC-XXII-33 | ----O~~O~~O~~O---- | 871 | | |
| PROTAC-XXII-34 | ----O~~O~~O~~O---- | 871 | | |
| PROTAC-XXII-35 | ----O~~O~~O~~O---- | 871 | | |

TABLE 22-continued

Protacs composed of a RAF ligand and a cereblon ligand with 7-position linkage having the following chemical structure

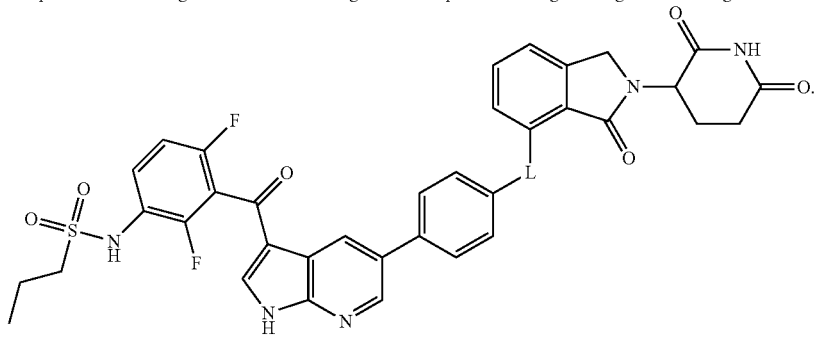

(PROTAC-XXII)

| PROTAC-XXII Compound | L | Mass | DC$_{50}$ (μM) | D$_{max}$ (%) |
|---|---|---|---|---|
| PROTAC-XXII-36 | ----O~~O~~~~O---- | 871 | | |
| PROTAC-XXII-37 | ----O~O~~~~O---- | 871 | | |
| PROTAC-XXII-38 | ----N(piperazine)N---- | 781 | | |
| PROTAC-XXII-39 | O~N(piperazine)N---- | 825 | | |
| PROTAC-XXII-40 | ----N(piperazine)N~O | 825 | | |
| PROTAC-XXII-41 | ----O~N(piperazine)N---- | 839 | | |
| PROTAC-XXII-42 | ----N(piperazine)N~O---- | 839 | | |
| PROTAC-XXII-43 | O~~N(piperazine)N---- | 853 | | |
| PROTAC-XXII-44 | ----N(piperazine)N~~O | 853 | | |
| PROTAC-XXII-45 | ----O~O~N(piperazine)N---- | 869 | | |
| PROTAC-XXII-46 | ----N(piperazine)N~O~O---- | 869 | | |

TABLE 22-continued

Protacs composed of a RAF ligand and a cereblon ligand with 7-position linkage having the following chemical structure

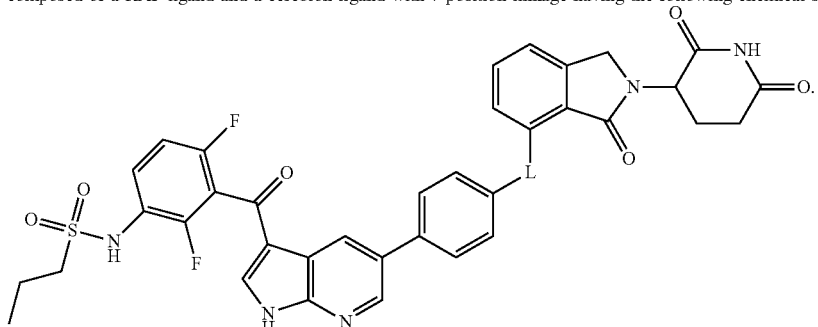

(PROTAC-XXII)

| PROTAC-XXII Compound | L | Mass | DC$_{50}$ (μM) | D$_{max}$ (%) |
|---|---|---|---|---|
| PROTAC-XXII-47 | ----N(piperazine)-CH$_2$CH$_2$-N(piperazine)---- | 893 | | |
| PROTAC-XXII-48 | -O-CH$_2$CH$_2$-N(piperazine)N-CH$_2$CH$_2$-O- | 869 | | |
| PROTAC-XXII-49 | -O-CH$_2$CH$_2$-O-CH$_2$CH$_2$-N(piperazine)N---- | 883 | | |
| PROTAC-XXII-50 | -O-CH$_2$-O-CH$_2$CH$_2$-N(piperazine)N---- | 883 | | |
| PROTAC-XXII-51 | -O-(CH$_2$)$_4$-N(piperazine)N---- | 881 | | |
| PROTAC-XXII-52 | ----N(piperazine)N-CH$_2$CH$_2$-O-CH$_2$CH$_2$-O- | 883 | | |
| PROTAC-XXII-53 | ----N(piperazine)N-CH$_2$CH$_2$CH$_2$-O-CH$_2$CH$_2$-O- | 883 | | |
| PROTAC-XXII-54 | ----N(piperazine)N-(CH$_2$)$_4$-O- | 881 | | |
| PROTAC-XXII-55 | ----N(piperazine)N-CH$_2$CH$_2$-N(N-methylpiperazine)---- | 907 | | |
| PROTAC-XXII-56 | ----O-CH$_2$CH$_2$-N(piperazine)N-CH$_2$CH$_2$-O- | 883 | | |

TABLE 22-continued
Protacs composed of a RAF ligand and a cereblon ligand with 7-position linkage having the following chemical structure
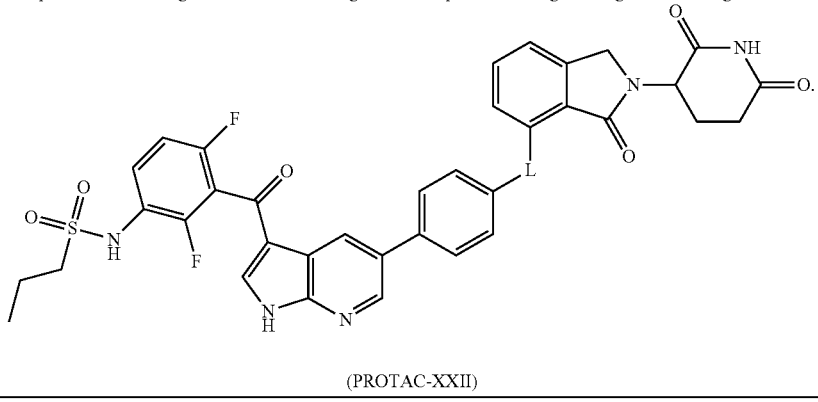
(PROTAC-XXII)
| PROTAC-XXII Compound | L | Mass | DC$_{50}$ (μM) | D$_{max}$ (%) |
|---|---|---|---|---|
| PROTAC-XXII-57 | | 883 | | |
| PROTAC-XXII-58 | | 897 | | |
| PROTAC-XXII-59 | | 897 | | |
| PROTAC-XXII-60 | | 897 | | |
| PROTAC-XXII-61 | | 895 | | |
| PROTAC-XXII-62 | | 897 | | |
| PROTAC-XXII-63 | | 897 | | |
| PROTAC-XXII-64 | | 897 | | |
| PROTAC-XXII-65 | | 895 | | |
| PROTAC-XXII-66 | | 921 | | |
| PROTAC-XXII-67 | | 897 | | |

TABLE 22-continued

Protacs composed of a RAF ligand and a cereblon ligand with 7-position linkage having the following chemical structure

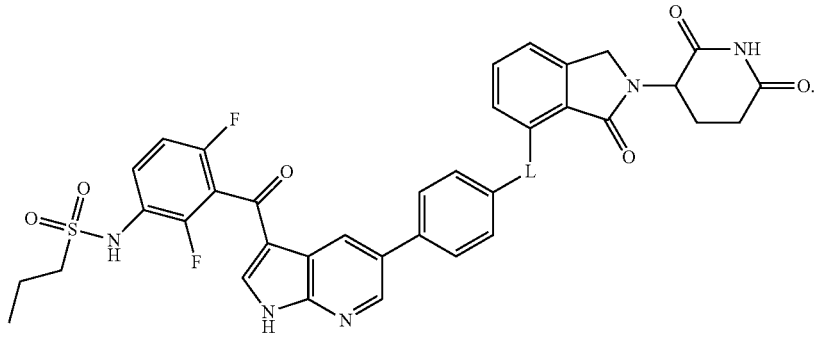

(PROTAC-XXII)

| PROTAC-XXII Compound | L | Mass | DC$_{50}$ (μM) | D$_{max}$ (%) |
|---|---|---|---|---|
| PROTAC-XXII-68 | ⋯O~~~N(piperazine)N~~~O⋯ | 897 | | |
| PROTAC-XXII-69 | ⋯O~~~N(piperazine)N~~~O⋯ | 897 | | |
| PROTAC-XXII-70 | ⋯O⋯ | 713 | | |

TABLE 23

Protacs composed of a RAF ligand and a VHL ligand with left-side linkage having the following chemical structure

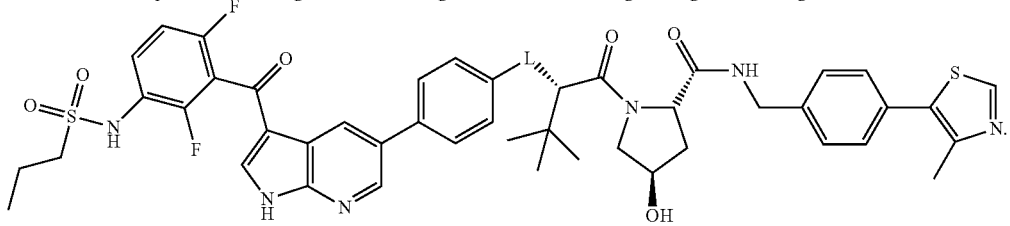

(PROTAC XXIII)

| PROTAC-XXIII Compound | L | Mass | DC$_{50}$ (μM) | D$_{max}$ (%) |
|---|---|---|---|---|
| PROTAC-XXIII-1 | ⋯O~O~C(=O)NH⋯ | 985 | | |
| PROTAC-XXIII-2 | ⋯O~O~O~C(=O)NH⋯ | 1029 | | |
| PROTAC-XXIII-3 | ⋯O~O~O~O~C(=O)NH⋯ | 1073 | | |

TABLE 23-continued
Protacs composed of a RAF ligand and a VHL ligand with left-side linkage having the following chemical structure
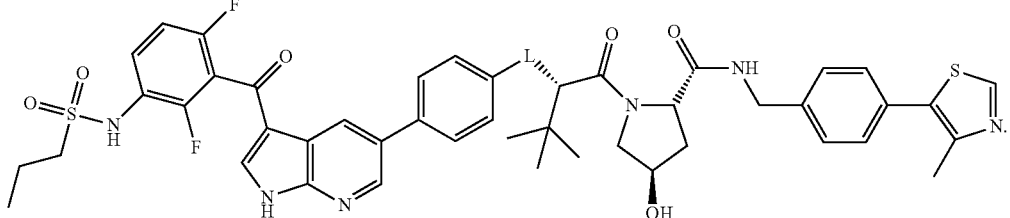
(PROTAC XXIII)
| PROTAC-XXIII Compound | L | Mass | DC$_{50}$ (μM) | D$_{max}$ (%) |
|---|---|---|---|---|
| PROTAC-XXIII-4 | | 1117 | | |
| PROTAC-XXIII-5 | | 1161 | | |
| PROTAC-XXIII-6 | | 1205 | | |
| PROTAC-XXIII-7 | | 969 | | |
| PROTAC-XXIII-8 | | 955 | | |
| PROTAC-XXIII-9 | | 999 | | |
| PROTAC-XXIII-10 | | 999 | | |
| PROTAC-XXIII-11 | | 997 | | |
| PROTAC-XXIII-12 | | 1013 | | |
| PROTAC-XXIII-13 | | 1013 | | |
| PROTAC-XXIII-14 | | 1013 | | |

TABLE 23-continued

Protacs composed of a RAF ligand and a VHL ligand with left-side linkage having the following chemical structure

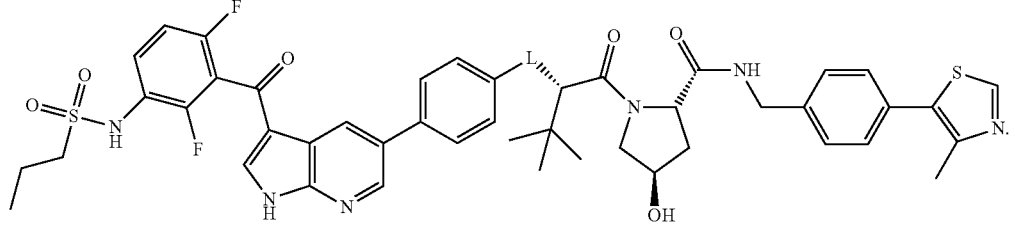

(PROTAC XXIII)

| PROTAC-XXIII Compound | L | Mass | DC$_{50}$ (μM) | D$_{max}$ (%) |
|---|---|---|---|---|
| PROTAC-XXIII-15 | ----O~~~~~C(=O)NH---- | 1011 | | |
| PROTAC-XXIII-16 | ----O-CH2-C(=O)-HN---- | 941 | | |
| PROTAC-XXIII-17 | ----O~~~C(=O)NH---- | 983 | | |
| PROTAC-XXIII-18 | ----O~O~~C(=O)NH---- | 1027 | | |
| PROTAC-XXIII-19 | ----O~~O~C(=O)NH---- | 1027 | | |
| PROTAC-XXIII-20 | ----O~~O~~C(=O)NH---- | 1027 | | |
| PROTAC-XXIII-21 | ----O~~~O-CH2-C(=O)NH---- | 1027 | | |
| PROTAC-XXIII-22 | ----O~O~~O-CH2-C(=O)NH---- | 1043 | | |
| PROTAC-XXIII-23 | ----O~O~O-CH2-C(=O)NH---- | 1043 | | |
| PROTAC-XXIII-24 | ----O~O~~O~C(=O)NH---- | 1043 | | |
| PROTAC-XXIII-25 | ----O~~O~~O-CH2-C(=O)NH---- | 1041 | | |

TABLE 23-continued
Protacs composed of a RAF ligand and a VHL ligand with left-side linkage having the following chemical structure
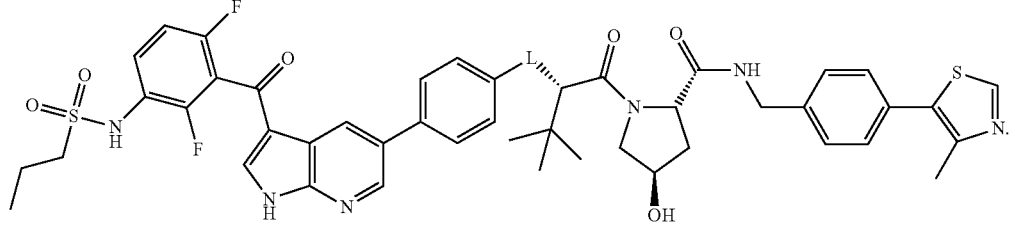
(PROTAC XXIII)
| PROTAC-XXIII Compound | L | Mass | DC$_{50}$ (μM) | D$_{max}$ (%) |
|---|---|---|---|---|
| PROTAC-XXIII-26 | | 1041 | | |
| PROTAC-XXIII-27 | | 1041 | | |
| PROTAC-XXIII-28 | | 1041 | | |
| PROTAC-XXIII-29 | | 1041 | | |
| PROTAC-XXIII-30 | | 1057 | | |
| PROTAC-XXIII-31 | | 1057 | | |
| PROTAC-XXIII-32 | | 1057 | | |
| PROTAC-XXIII-33 | | 1071 | | |
| PROTAC-XXIII-34 | | 1071 | | |
| PROTAC-XXIII-35 | | 1071 | | |
| PROTAC-XXII-36 | | 1071 | | |

TABLE 23-continued
Protacs composed of a RAF ligand and a VHL ligand with left-side linkage having the following chemical structure
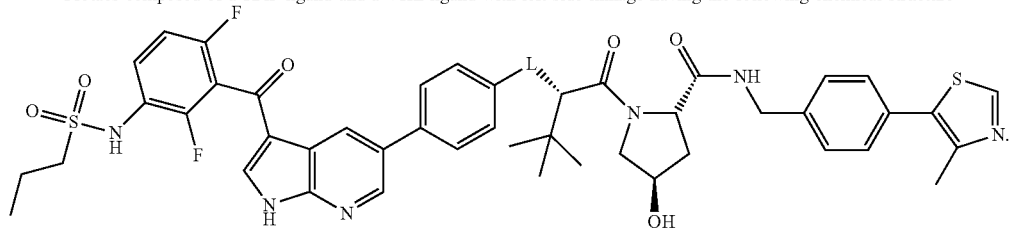
(PROTAC XXIII)
| PROTAC-XXIII Compound | L | Mass | DC$_{50}$ (μM) | D$_{max}$ (%) |
|---|---|---|---|---|
| PROTAC-XXIII-37 | | 1071 | | |
| PROTAC-XXIII-38 | | 1071 | | |
| PROTAC-XXIII-39 | | 1071 | | |
| PROTAC-XXIII-40 | | 1069 | | |
| PROTAC-XXIII-41 | | 1069 | | |
| PROTAC-XXIII-42 | | 1069 | | |
| PROTAC-XXIII-43 | | 1069 | | |
| PROTAC-XXIII-44 | | 1053 | | |
| PROTAC-XXIII-45 | | 1067 | | |
| PROTAC-XXIII-46 | | 1081 | | |

TABLE 23-continued
Protacs composed of a RAF ligand and a VHL ligand with left-side linkage having the following chemical structure
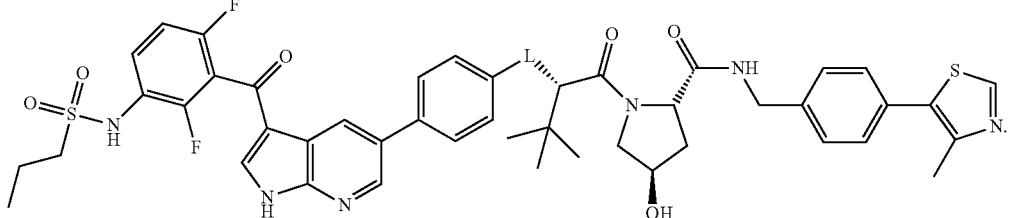
(PROTAC XXIII)
| PROTAC-XXIII Compound | L | Mass | DC$_{50}$ (μM) | D$_{max}$ (%) |
|---|---|---|---|---|
| PROTAC-XXIII-47 | 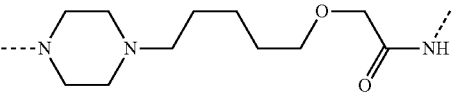 | 1095 | | |
| PROTAC-XXIII-48 | 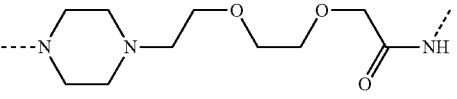 | 1097 | | |
| PROTAC-XXIII-49 | 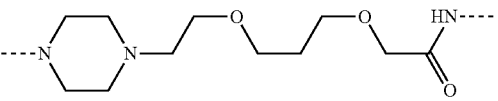 | 1111 | | |
| PROTAC-XXIII-50 | 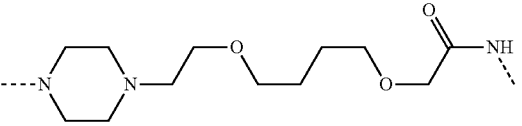 | 1125 | | |
| PROTAC-XXIII-51 | 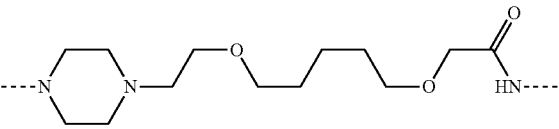 | 1139 | | |
| PROTAC-XXIII-52 | 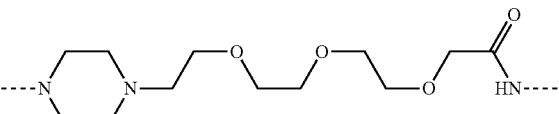 | 1141 | | |
| PROTAC-XXIII-53 | 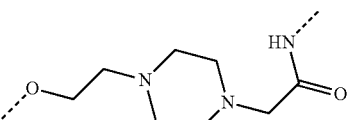 | 1053 | | |
| PROTAC-XXIII-54 | 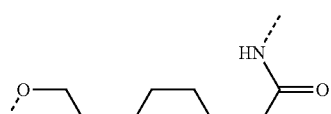 | 1052 | | |
| PROTAC-XXIII-55 | 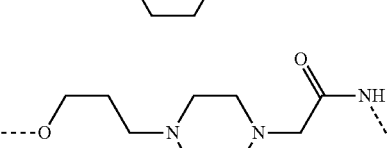 | 1067 | | |

TABLE 23-continued
Protacs composed of a RAF ligand and a VHL ligand with left-side linkage having the following chemical structure
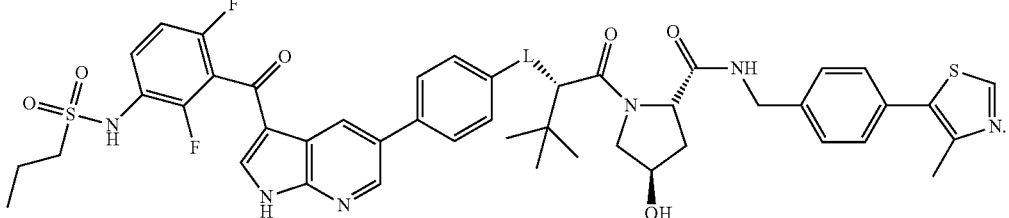
(PROTAC XXIII)
| PROTAC-XXIII Compound | L | Mass | DC$_{50}$ (μM) | D$_{max}$ (%) |
|---|---|---|---|---|
| PROTAC-XXIII-56 | | 1081 | | |
| PROTAC-XXIII-57 | | 1095 | | |
| PROTAC-XXIII-58 | | 1097 | | |
| PROTAC-XXIII-59 | | 1096 | | |
| PROTAC-XXIII-60 | | 1121 | | |
| PROTAC-XXIII-61 | | 1120 | | |
| PROTAC-XXIII-62 | | 1120 | | |
| PROTAC-XXIII-63 | | 1106 | | |
| PROTAC-XXIII-64 | | 1092 | | |

TABLE 23-continued
Protacs composed of a RAF ligand and a VHL ligand with left-side linkage having the following chemical structure
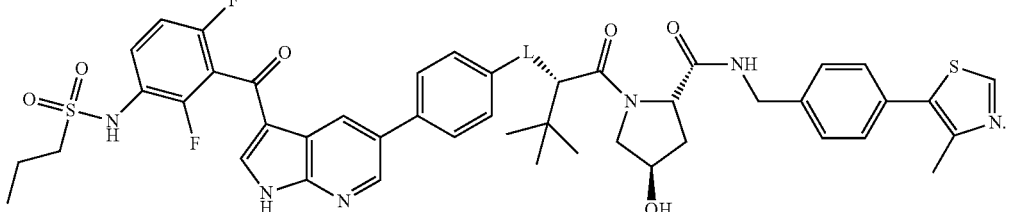
(PROTAC XXIII)
| PROTAC-XXIII Compound | L | Mass | DC$_{50}$ (μM) | D$_{max}$ (%) |
|---|---|---|---|---|
| PROTAC-XXIII-65 | | 965 | | |
| PROTAC-XXIII-66 | | 979 | | |
| PROTAC-XXIII-67 | | 993 | | |
| PROTAC-XXIII-68 | | 1007 | | |
| PROTAC-XXIII-69 | | 1009 | | |
| PROTAC-XXIII-70 | | 1021 | | |
| PROTAC-XXIII-71 | | 1023 | | |
| PROTAC-XXIII-72 | | 1023 | | |
| PROTAC-XXIII-73 | | 1037 | | |
| PROTAC-XXIII-74 | | 1037 | | |
| PROTAC-XXIII-75 | | 1037 | | |

TABLE 23-continued
Protacs composed of a RAF ligand and a VHL ligand with left-side linkage having the following chemical structure
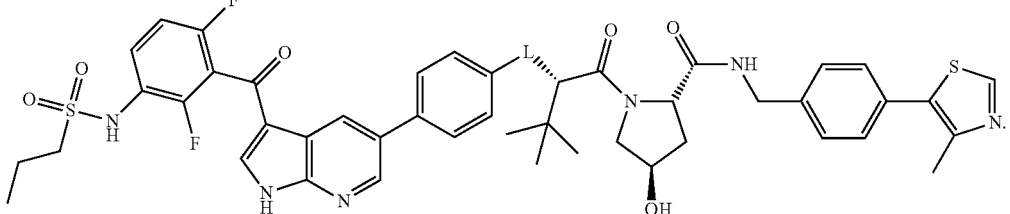
(PROTAC XXIII)
| PROTAC-XXIII Compound | L | Mass | DC$_{50}$ (µM) | D$_{max}$ (%) |
|---|---|---|---|---|
| PROTAC-XXIII-76 | | 1051 | | |
| PROTAC-XXIII-77 | | 1051 | | |
| PROTAC-XXIII-78 | | 1051 | | |
| PROTAC-XXIII-79 | | 1051 | | |
| PROTAC-XXIII-80 | | 1053 | | |
| PROTAC-XXIII-81 | | 1065 | | |
| PROTAC-XXIII-82 | | 1065 | | |
| PROTAC-XXIII-83 | | 1065 | | |
| PROTAC-XXIII-84 | | 1065 | | |
| PROTAC-XXIII-85 | | 1065 | | |
| PROTAC-XXIII-86 | | 1067 | | |

TABLE 23-continued
Protacs composed of a RAF ligand and a VHL ligand with left-side linkage having the following chemical structure
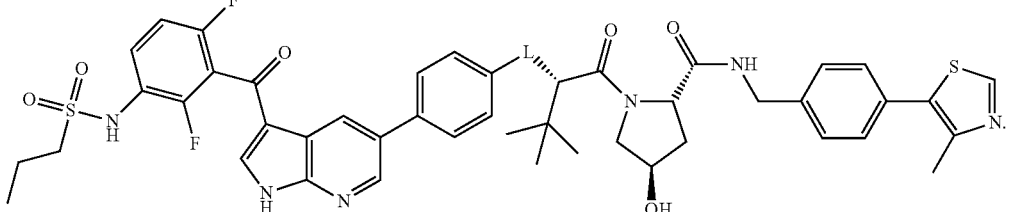
(PROTAC XXIII)
| PROTAC-XXIII Compound | L | Mass | DC$_{50}$ (μM) | D$_{max}$ (%) |
|---|---|---|---|---|
| PROTAC-XXIII-87 | | 1067 | | |
| PROTAC-XXIII-88 | | 1067 | | |
| PROTAC-XXIII-89 | | 1019 | | |
| PROTAC-XXIII-90 | | 1033 | | |
| PROTAC-XXIII-91 | | 1047 | | |
| PROTAC-XXIII-92 | | 1061 | | |
| PROTAC-XXIII-93 | | 1075 | | |
| PROTAC-XXIII-94 | | 1077 | | |
| PROTAC-XXIII-95 | | 1091 | | |
| PROTAC-XXIII-96 | | 1091 | | |
| PROTAC-XXIII-97 | | 1089 | | |

TABLE 23-continued

Protacs composed of a RAF ligand and a VHL ligand with left-side linkage having the following chemical structure

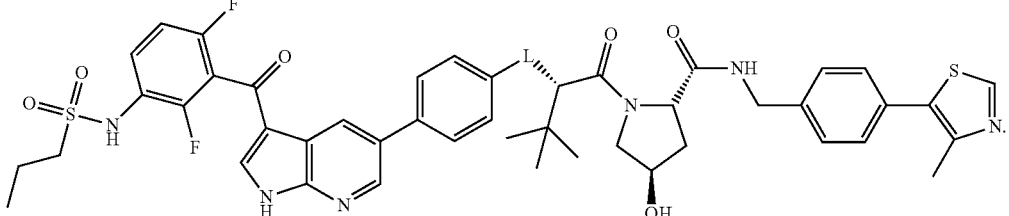

(PROTAC XXIII)

| PROTAC-XXIII Compound | L | Mass | DC$_{50}$ (μM) | D$_{max}$ (%) |
|---|---|---|---|---|
| PROTAC-XXIII-98 | ![structure] | 1103 | | |
| PROTAC-XXIII-99 | ![structure] | 1105 | | |
| PROTAC-XXIII-100 | ![structure] | 1105 | | |
| PROTAC-XXIII-101 | ![structure] | 1105 | | |

TABLE 24

Protacs composed of a RAF ligand and a VHL ligand with right-side linkage having the following chemical structure

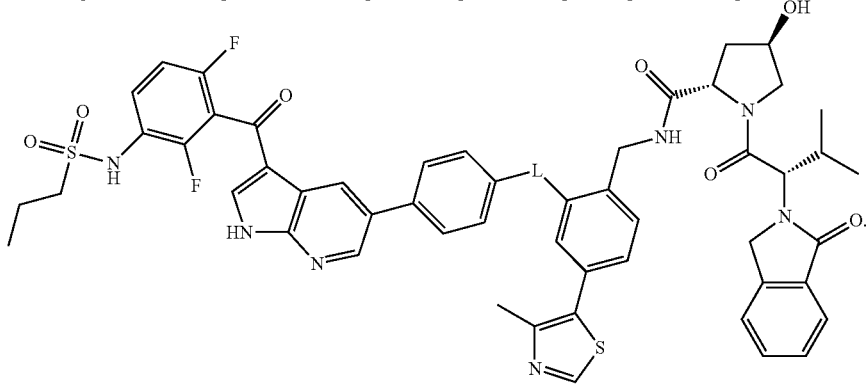

(PROTAC-XXIV)

| PROTAC-XXIV Compound | L | Mass | DC$_{50}$ (μM) | D$_{max}$ (%) |
|---|---|---|---|---|
| PROTAC-XXIV-1 | ----O~~~O---- | 1045 | | |
| PROTAC-XXIV-2 | ----O~~~O~~~O~~~ | 1089 | | |

TABLE 24-continued

Protacs composed of a RAF ligand and a VHL ligand with right-side linkage having the following chemical structure

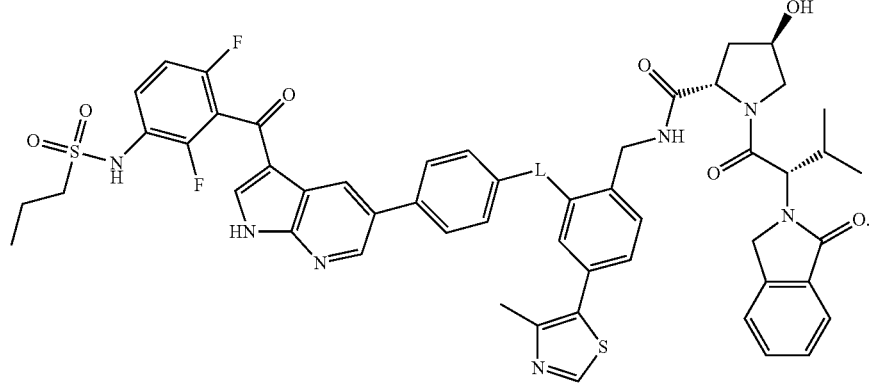

(PROTAC-XXIV)

| PROTAC-XXIV Compound | L | Mass | DC$_{50}$ (µM) | D$_{max}$ (%) |
|---|---|---|---|---|
| PROTAC-XXIV-3 | ----O\_/\O/\_O/\_O---- | 1133 | | |
| PROTAC-XXIV-4 | ----O\_/\O/\_O/\_O/\_O/ | 1177 | | |
| PROTAC-XXIV-5 | ----O\_/\O/\_O/\_O/\_O/\_O---- | 1221 | | |
| PROTAC-XXIV-6 | ----O\_/\O/\_O/\_O/\_O/\_O/\_O | 1265 | | |
| PROTAC-XXIV-7 | ----/\O | 1029 | | |
| PROTAC-XXIV-8 | /\O | 1015 | | |
| PROTAC-XXIV-9 | O/\---- | 1029 | | |
| PROTAC-XXIV-10 | ----O/\ | 1015 | | |
| PROTAC-XXIV-11 | ----O/\_/O/ | 1059 | | |
| PROTAC-XXIV-12 | ----O/\_/O---- | 1073 | | |
| PROTAC-XXIV-13 | ----O/\O/\O---- | 1103 | | |
| PROTAC-XXIV-14 | ----O/\O/\O---- | 1103 | | |
| PROTAC-XXIV-15 | ----O/\_/\O---- | 1101 | | |
| PROTAC-XXIV-16 | ----O/\O/\_/O/ | 1117 | | |
| PROTAC-XXIV-17 | ----O/\O/\O/ | 1117 | | |

TABLE 24-continued

Protacs composed of a RAF ligand and a VHL ligand with right-side linkage having the following chemical structure

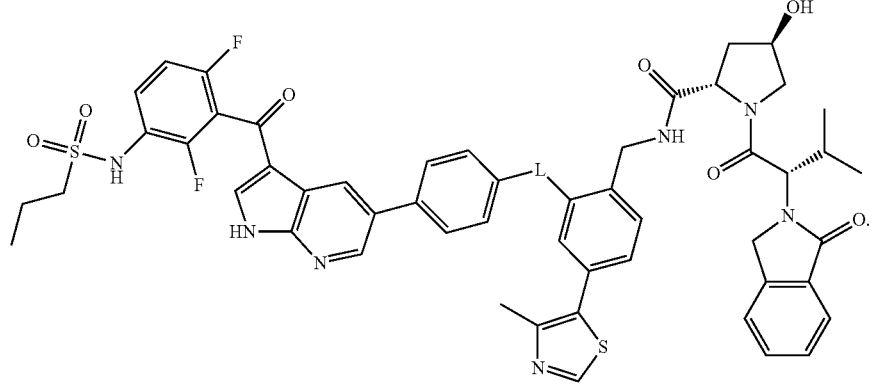

(PROTAC-XXIV)

| PROTAC-XXIV Compound | L | Mass | DC$_{50}$ (μM) | D$_{max}$ (%) |
|---|---|---|---|---|
| PROTAC-XXIV-18 | | 1117 | | |
| PROTAC-XXIV-19 | | 1147 | | |
| PROTAC-XXIV-20 | | 1147 | | |
| PROTAC-XXIV-21 | | 1147 | | |
| PROTAC-XXIV-22 | | 1145 | | |
| PROTAC-XXIV-23 | | 1145 | | |
| PROTAC-XXIV-24 | | 1145 | | |
| PROTAC-XXIV-25 | | 1145 | | |
| PROTAC-XXIV-26 | | 1145 | | |
| PROTAC-XXIV-27 | | 1161 | | |
| PROTAC-XXIV-28 | | 1161 | | |
| PROTAC-XXIV-29 | | 1161 | | |
| PROTAC-XXIV-30 | | 1161 | | |
| PROTAC-XXIV-31 | | 1161 | | |
| PROTAC-XXIV-32 | | 1159 | | |

TABLE 24-continued

Protacs composed of a RAF ligand and a VHL ligand with right-side linkage having the following chemical structure

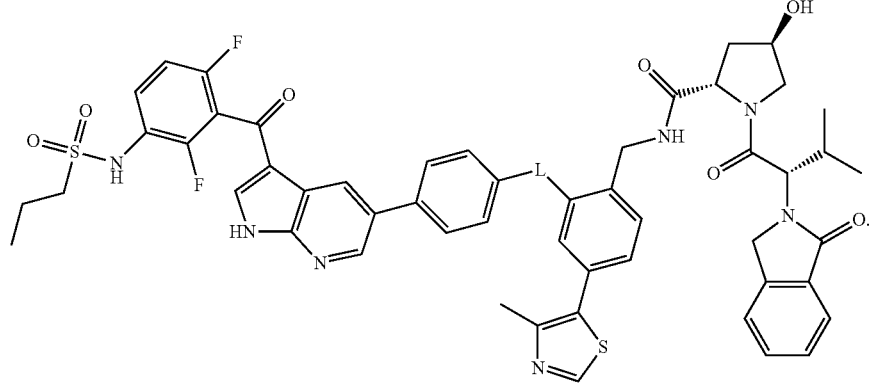

(PROTAC-XXIV)

| PROTAC-XXIV Compound | L | Mass | DC$_{50}$ (µM) | D$_{max}$ (%) |
|---|---|---|---|---|
| PROTAC-XXIV-33 | ----O~~~O~~~O---- | 1159 | | |
| PROTAC-XXIV-34 | ----O~~~O~~~O---- | 1159 | | |
| PROTAC-XXIV-35 | ----O~~~O~~~O---- | 1159 | | |
| PROTAC-XXIV-36 | ----O~~~O~~~O---- | 1159 | | |
| PROTAC-XXIV-37 | ----O~~~O~~~O---- | 1159 | | |
| PROTAC-XXIV-38 | ----N(piperazine)N---- | 1069 | | |
| PROTAC-XXIV-39 | O~~N(piperazine)N---- | 1113 | | |
| PROTAC-XXIV-40 | ----N(piperazine)N~~O | 1113 | | |
| PROTAC-XXIV-41 | ----O~~N(piperazine)N---- | 1127 | | |
| PROTAC-XXIV-42 | ----N(piperazine)N~~O---- | 1127 | | |
| PROTAC-XXIV-43 | O~~~N(piperazine)N---- | 1141 | | |
| PROTAC-XXIV-44 | ----N(piperazine)N~~~O | 1141 | | |

TABLE 24-continued

Protacs composed of a RAF ligand and a VHL ligand with right-side linkage having the following chemical structure

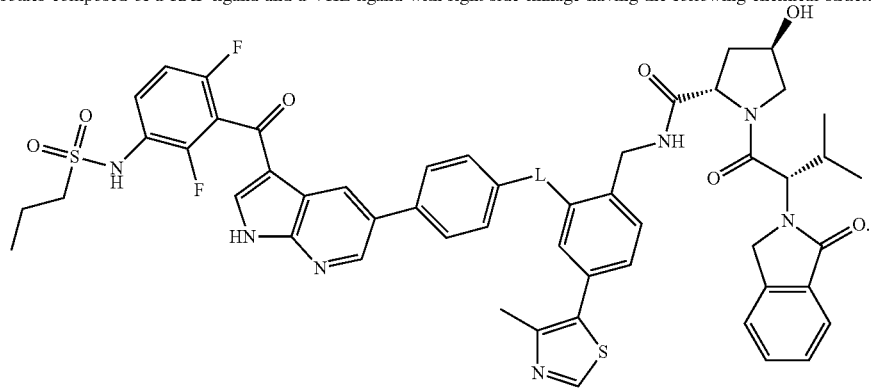

(PROTAC-XXIV)

| PROTAC-XXIV Compound | L | Mass | DC$_{50}$ (µM) | D$_{max}$ (%) |
|---|---|---|---|---|
| PROTAC-XXIV-45 | —O∼O∼N(piperazine)N— | 1157 | | |
| PROTAC-XXIV-46 | —N(piperazine)N∼O∼O— | 1157 | | |
| PROTAC-XXIV-47 | —N(piperazine)N∼N(piperazine)N— | 1181 | | |
| PROTAC-XXIV-48 | O∼N(piperazine)N∼O | 1157 | | |
| PROTAC-XXIV-49 | O∼O∼N(piperazine)N— | 1171 | | |
| PROTAC-XXIV-50 | O∼O∼N(piperazine)N— | 1171 | | |
| PROTAC-XXIV-51 | O∼∼∼N(piperazine)N— | 1169 | | |
| PROTAC-XXIV-52 | —N(piperazine)N∼O∼O | 1171 | | |
| PROTAC-XXIV-53 | —N(piperazine)N∼O∼O | 1171 | | |
| PROTAC-XXIV-54 | —N(piperazine)N∼∼∼O | 1169 | | |

TABLE 24-continued

Protacs composed of a RAF ligand and a VHL ligand with right-side linkage having the following chemical structure

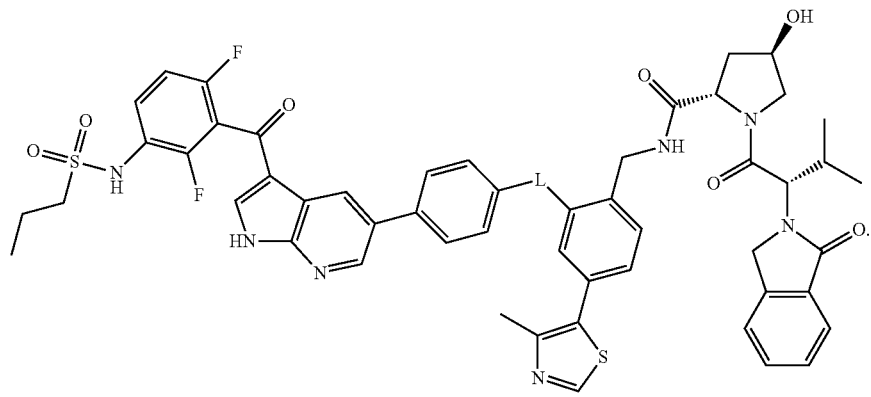

(PROTAC-XXIV)

| PROTAC-XXIV Compound | L | Mass | DC$_{50}$ (μM) | D$_{max}$ (%) |
|---|---|---|---|---|
| PROTAC-XXIV-55 | ----N(piperazine)N-CH₂CH₂CH₂-N(piperazine)N-CH₃ | 1195 | | |
| PROTAC-XXIV-56 | ----O-CH₂CH₂-N(piperazine)N-CH₂CH₂-O---- | 1171 | | |
| PROTAC-XXIV-57 | O-CH₂CH₂-N(piperazine)N-CH₂CH₂-O---- | 1171 | | |
| PROTAC-XXIV-58 | ----O-CH₂CH₂CH₂-O-CH₂CH₂-N(piperazine)N---- | 1185 | | |
| PROTAC-XXIV-59 | ----O-CH₂CH₂-O-CH₂CH₂CH₂-N(piperazine)N---- | 1185 | | |
| PROTAC-XXIV-60 | ----O-CH₂-O-CH₂CH₂-N(piperazine)N---- (with propyl) | 1185 | | |
| PROTAC-XXIV-61 | ----O-(CH₂)₄-N(piperazine)N---- | 1183 | | |
| PROTAC-XXIV-62 | ----N(piperazine)N-CH₂CH₂CH₂-O-CH₂CH₂-O---- | 1185 | | |

TABLE 24-continued

Protacs composed of a RAF ligand and a VHL ligand with right-side linkage having the following chemical structure

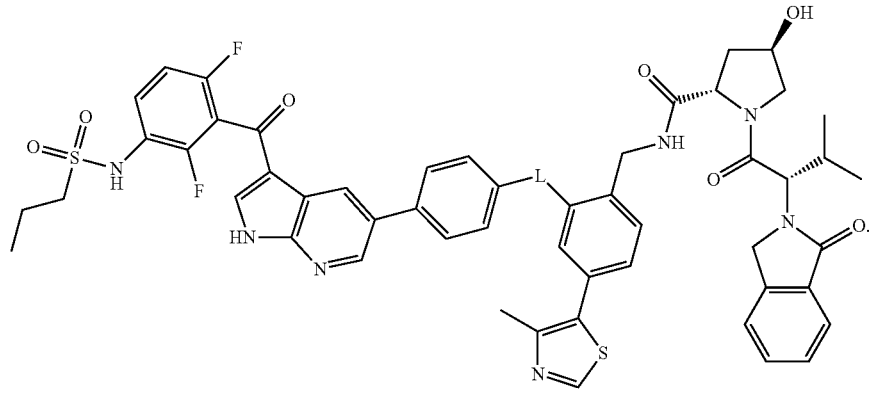

(PROTAC-XXIV)

| PROTAC-XXIV Compound | L | Mass | DC$_{50}$ (μM) | D$_{max}$ (%) |
|---|---|---|---|---|
| PROTAC-XXIV-63 | ----N⌒N-CH₂CH₂-O-CH₂CH₂-O---- | 1185 | | |
| PROTAC-XXIV-64 | ----N⌒N-CH₂CH₂-O-CH₂CH₂CH₂-O---- | 1185 | | |
| PROTAC-XXIV-65 | ----N⌒N-(CH₂)₄-O---- | 1183 | | |
| PROTAC-XXIV-66 | ----N⌒N-CH₂CH₂CH₂-N⌒N---- | 1209 | | |
| PROTAC-XXIV-67 | ----O-CH₂CH₂CH₂-N⌒N-CH₂CH₂CH₂-O---- | 1185 | | |
| PROTAC-XXIV-68 | ·O-(CH₂)₄-N⌒N-CH₂CH₂-O· | 1185 | | |
| PROTAC-XXIV-69 | ·O-CH₂CH₂-N⌒N-(CH₂)₄-O· | 1185 | | |
| PROTAC-XXIV-70 | ----O· | 1001 | | |

TABLE 25

Protacs composed of a RAF ligand and a cereblon ligand with 5-position linkage having the following chemical structure


(PROTAC-XXV)

| PROTAC-XXV Compound | L | Mass | $DC_{50}$ (μM) | $D_{max}$ (%) |
|---|---|---|---|---|
| PROTAC-XXV-1 | ----O\_/\_O---- | 868 | | |
| PROTAC-XXV-2 | ----O\_/\_O\_/\_O---- | 912 | | |
| PROTAC-XXV-3 | ----O\_/\_O\_/\_O\_/\_O---- | 956 | | |
| PROTAC-XXV-4 | ----O\_/\_O\_/\_O\_/\_O\_/\_O---- | 1000 | | |
| PROTAC-XXV-5 | ----O\_/\_O\_/\_O\_/\_O\_/\_O\_/\_O---- | 1044 | | |
| PROTAC-XXV-6 | ----O\_/\_O\_/\_O\_/\_O\_/\_O\_/\_O\_/\_O---- | 1088 | | |
| PROTAC-XXV-7 | ----\_/\_O---- | 852 | | |
| PROTAC-XXV-8 | ----\_O---- | 838 | | |
| PROTAC-XXV-9 | ----O\_/---- | 852 | | |
| PROTAC-XXV-10 | ----O\_/---- | 838 | | |
| PROTAC-XXV-11 | ----O\_/\_\_O---- | 882 | | |
| PROTAC-XXV-12 | ----O\_/\_\_\_O---- | 896 | | |
| PROTAC-XXV-13 | ----O\_/\_O\_/\_O---- | 926 | | |
| PROTAC-XXV-14 | ----O\_\_O\_\_O---- | 926 | | |
| PROTAC-XXV-15 | ----O\_/\_\_O\_/\_\_O---- | 924 | | |
| PROTAC-XXV-16 | ----O\_/\_O\_/\_O\_/\_O---- | 940 | | |

TABLE 25-continued

Protacs composed of a RAF ligand and a cereblon ligand with 5-position linkage having the following chemical structure


(PROTAC-XXV)

| PROTAC-XXV Compound | L | Mass | $DC_{50}$ (μM) | $D_{max}$ (%) |
|---|---|---|---|---|
| PROTAC-XXV-17 | ----O-CH₂CH₂-O-CH₂CH₂CH₂-O-CH₂CH₂-- | 940 | | |
| PROTAC-XXV-18 | ----O-CH₂CH₂CH₂-O-CH₂CH₂-O-CH₂-- | 940 | | |
| PROTAC-XXV-19 | ----O-CH₂CH₂-O-CH₂CH₂-O-CH₂CH₂CH₂-O-- | 970 | | |
| PROTAC-XXV-20 | ----O-CH₂CH₂-O-CH₂CH₂-O-CH₂CH₂-O-CH₂-- | 970 | | |
| PROTAC-XXV-21 | ----O-CH₂CH₂-O-CH₂CH₂-O-CH₂CH₂-O-CH₂-- | 970 | | |
| PROTAC-XXV-22 | ----O-CH₂CH₂-O-CH₂CH₂-O-CH₂CH₂CH₂-O-- | 968 | | |
| PROTAC-XXV-23 | ----O-CH₂CH₂CH₂-O-CH₂CH₂-O-CH₂CH₂-O-- | 968 | | |
| PROTAC-XXV-24 | ----O-CH₂CH₂CH₂-O-CH₂CH₂-O-CH₂CH₂-O-- | 968 | | |
| PROTAC-XXV-25 | ----O-CH₂CH₂CH₂-O-CH₂-O-CH₂CH₂-O-- | 968 | | |
| PROTAC-XXV-26 | ----O-CH₂-O-CH₂CH₂CH₂-O-CH₂CH₂-O-- | 968 | | |
| PROTAC-XXV-27 | ----O-CH₂-O-CH₂CH₂-O-CH₂CH₂CH₂-O---- | 984 | | |
| PROTAC-XXV-28 | ----O-CH₂CH₂-O-CH₂CH₂-O-CH₂CH₂-O---- | 984 | | |
| PROTAC-XXV-29 | ----O-CH₂CH₂-O-CH₂CH₂-O-CH₂CH₂-O---- | 984 | | |
| PROTAC-XXV-30 | ----O-CH₂CH₂-O-CH₂-O-CH₂CH₂-O-CH₂-O---- | 984 | | |
| PROTAC-XXV-31 | ----O-CH₂CH₂CH₂-O-CH₂-O-CH₂CH₂-O---- | 984 | | |

TABLE 25-continued

Protacs composed of a RAF ligand and a cereblon ligand with 5-position linkage having the following chemical structure


(PROTAC-XXV)

| PROTAC-XXV Compound | L | Mass | DC$_{50}$ (μM) | D$_{max}$ (%) |
|---|---|---|---|---|
| PROTAC-XXV-32 | ----O\_/\_O\_/\_O---- | 982 | | |
| PROTAC-XXV-33 | ----O\_/\_O\_/\_O---- | 982 | | |
| PROTAC-XXV-34 | ----O\_/\_O\_/\_O---- | 982 | | |
| PROTAC-XXV-35 | ----O\_/\_O\_/\_O---- | 982 | | |
| PROTAC-XXV-36 | ----O\_/\_O\_/\_O---- | 982 | | |
| PROTAC-XXV-37 | ----O\_/\_O\_/\_O---- | 982 | | |
| PROTAC-XXV-38 | ----N(piperazine)N---- | 892 | | |
| PROTAC-XXV-39 | O\_/\_N(piperazine)N---- | 936 | | |
| PROTAC-XXV-40 | ----N(piperazine)N\_/\_O | 936 | | |
| PROTAC-XXV-41 | ----O\_/\_N(piperazine)N---- | 950 | | |
| PROTAC-XXV-42 | ----N(piperazine)N\_/\_O---- | 950 | | |
| PROTAC-XXV-43 | O\_/\_N(piperazine)N---- | 964 | | |
| PROTAC-XXV-44 | ----N(piperazine)N\_/\_O | 964 | | |

TABLE 25-continued
Protacs composed of a RAF ligand and a cereblon ligand with 5-position linkage having the following chemical structure
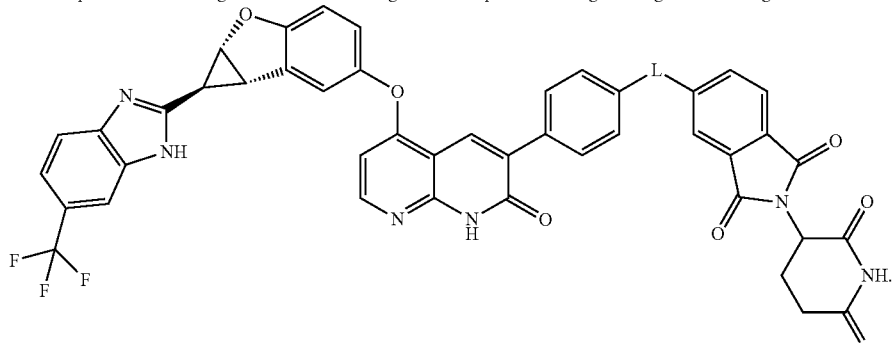
(PROTAC-XXV)
| PROTAC-XXV Compound | L | Mass | DC$_{50}$ (μM) | D$_{max}$ (%) |
|---|---|---|---|---|
| PROTAC-XXV-45 |  | 980 | | |
| PROTAC-XXV-46 |  | 980 | | |
| PROTAC-XXV-47 |  | 1004 | | |
| PROTAC-XXV-48 |  | 980 | | |
| PROTAC-XXV-49 | 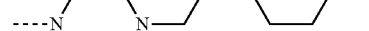 | 994 | | |
| PROTAC-XXV-50 |  | 994 | | |
| PROTAC-XXV-51 |  | 992 | | |
| PROTAC-XXV-52 |  | 994 | | |
| PROTAC-XXV-53 |  | 994 | | |
| PROTAC-XXV-54 |  | 992 | | |

TABLE 25-continued
Protacs composed of a RAF ligand and a cereblon ligand with 5-position linkage having the following chemical structure
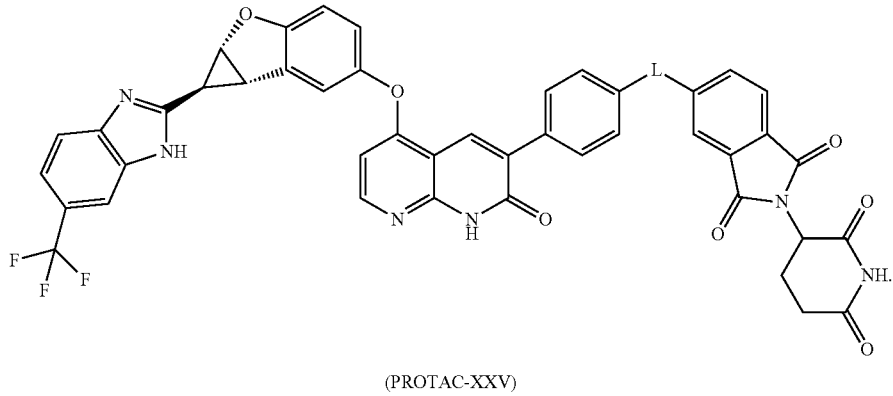
(PROTAC-XXV)
| PROTAC-XXV Compound | L | Mass | DC$_{50}$ (µM) | D$_{max}$ (%) |
|---|---|---|---|---|
| PROTAC-XXV-55 | | 1018 | | |
| PROTAC-XXV-56 | | 994 | | |
| PROTAC-XXV-57 | | 994 | | |
| PROTAC-XXV-58 | | 1008 | | |
| PROTAC-XXV-59 | | 1008 | | |
| PROTAC-XXV-60 | | 1008 | | |
| PROTAC-XXV-61 | | 1006 | | |
| PROTAC-XXV-62 | | 1008 | | |

TABLE 25-continued
Protacs composed of a RAF ligand and a cereblon ligand with 5-position linkage having the following chemical structure
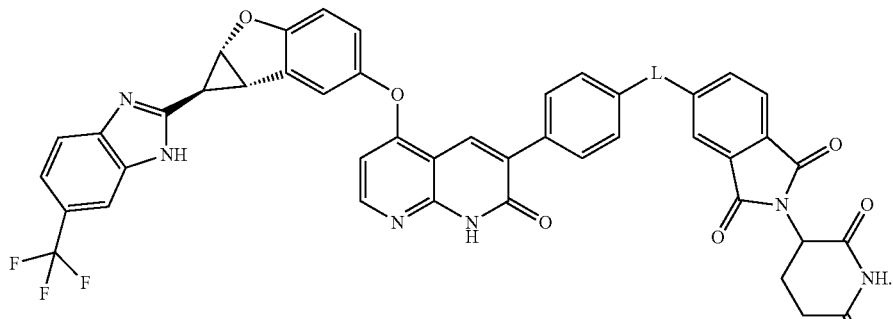
(PROTAC-XXV)
| PROTAC-XXV Compound | L | Mass | DC$_{50}$ (μM) | D$_{max}$ (%) |
|---|---|---|---|---|
| PROTAC-XXV-63 | 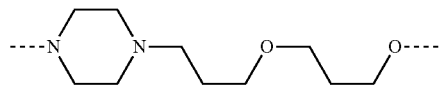 | 1008 | | |
| PROTAC-XXV-64 | 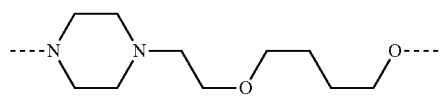 | 1008 | | |
| PROTAC-XXV-65 | 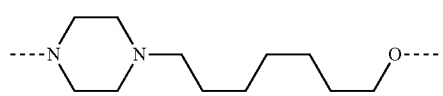 | 1006 | | |
| PROTAC-XXV-66 |  | 1032 | | |
| PROTAC-XXV-67 | 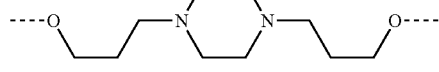 | 1008 | | |
| PROTAC-XXV-68 | 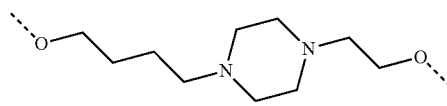 | 1008 | | |
| PROTAC-XXV-69 | 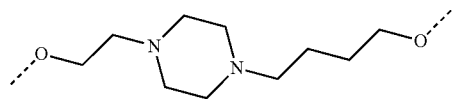 | 1008 | | |
| PROTAC-XXV-70 |  | 824 | | |

TABLE 26

Protacs composed of a RAF ligand and a cereblon ligand
with 5-position linkage having the following chemical structure

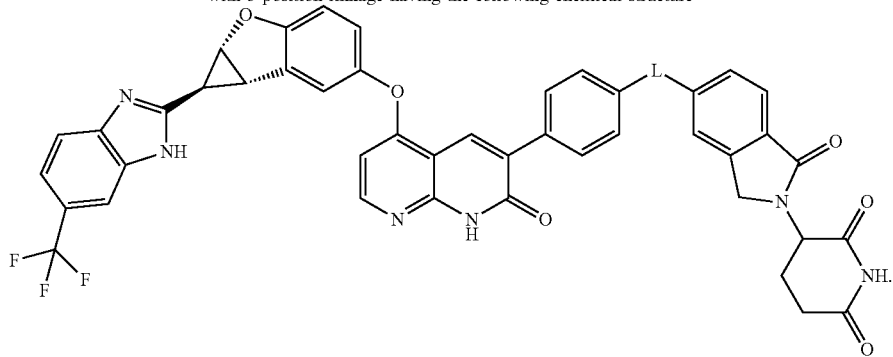

(PROTAC-XXVI).

| PROTAC-XXVI Compound | L | Mass | DC$_{50}$ (μM) | D$_{max}$ (%) |
|---|---|---|---|---|
| PROTAC-XXVI-1 | | 854 | | |
| PROTAC-XXVI-2 | | 898 | | |
| PROTAC-XXVI-3 | | 942 | | |
| PROTAC-XXVI-4 | | 986 | | |
| PROTAC-XXVI-5 | | 1030 | | |
| PROTAC-XXVI-6 | | 1074 | | |
| PROTAC-XXVI-7 | | 838 | | |
| PROTAC-XXVI-8 | | 824 | | |
| PROTAC-XXVI-9 | | 838 | | |
| PROTAC-XXVI-10 | | 824 | | |
| PROTAC-XXVI-11 | | 868 | | |
| PROTAC-XXVI-12 | | 882 | | |
| PROTAC-XXVI-13 | | 912 | | |
| PROTAC-XXVI-14 | | 912 | | |
| PROTAC-XXVI-15 | | 910 | | |
| PROTAC-XXVI-16 | | 926 | | |

TABLE 26-continued

Protacs composed of a RAF ligand and a cereblon ligand
with 5-position linkage having the following chemical structure

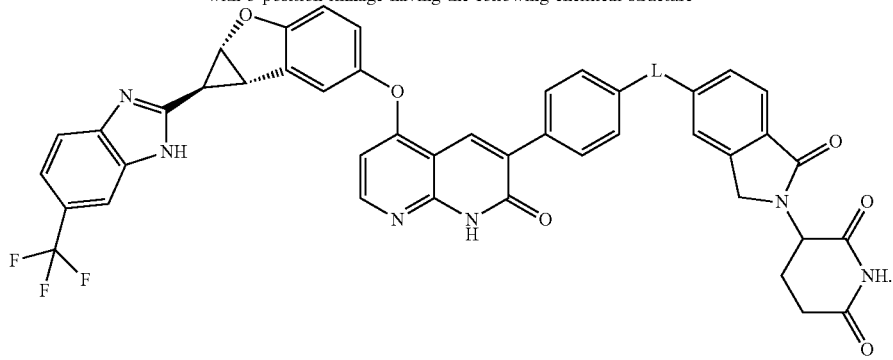

(PROTAC-XXVI).

| PROTAC-XXVI Compound | L | Mass | DC$_{50}$ (μM) | D$_{max}$ (%) |
|---|---|---|---|---|
| PROTAC-XXVI-17 | ----O\_/\O/\_/O\_/ | 926 | | |
| PROTAC-XXVI-18 | ----O\_/\_/O\_/O\_/ | 926 | | |
| PROTAC-XXVI-19 | ----O\_/O\_/\O/\_/O\_/ | 956 | | |
| PROTAC-XXVI-20 | ----O\_/O\_/\_/O\_/\_/O\_/ | 956 | | |
| PROTAC-XXVI-21 | ----O\_/\_/O\_/O\_/\_/O\_/ | 956 | | |
| PROTAC-XXVI-22 | ----O\_/\_/O\_/\_/\_/O\_/ | 954 | | |
| PROTAC-XXVI-23 | ----O\_/\_/O\_/\_/\_/O\_/ | 954 | | |
| PROTAC-XXVI-24 | ----O\_/\_/\_/O\_/\_/O\_/ | 954 | | |
| PROTAC-XXVI-25 | ----O\_/\_/\_/\_/O\_/\_/O\_/ | 954 | | |
| PROTAC-XXVI-26 | ----O\_/O\_/\_/\_/\_/O\_/ | 954 | | |
| PROTAC-XXVI-27 | ----O\_/O\_/\_/O\_/\_/O---- | 970 | | |
| PROTAC-XXVI-28 | ----O\_/O\_/\_/O\_/\_/O---- | 970 | | |
| PROTAC-XXVI-29 | ----O\_/O\_/\_/O\_/\_/O---- | 970 | | |
| PROTAC-XXVI-30 | ----O\_/O\_/O\_/\_/O---- | 970 | | |
| PROTAC-XXVI-31 | ----O\_/\_/O\_/\_/O\_/\_/O---- | 970 | | |

TABLE 26-continued

Protacs composed of a RAF ligand and a cereblon ligand
with 5-position linkage having the following chemical structure

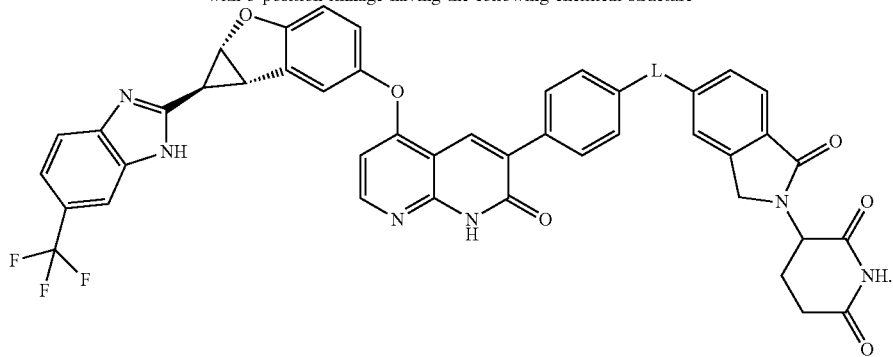

(PROTAC-XXVI).

| PROTAC-XXVI Compound | L | Mass | DC$_{50}$ (μM) | D$_{max}$ (%) |
|---|---|---|---|---|
| PROTAC-XXVI-32 | ----O~~~O~~~O~~~O---- | 968 | | |
| PROTAC-XXVI-33 | ----O~~~~O~~~O---- | 968 | | |
| PROTAC-XXVI-34 | ----O~~~~O~~O---- | 968 | | |
| PROTAC-XXVI-35 | ----O~~~O~~O---- | 968 | | |
| PROTAC-XXVI-36 | ----O~~O~~~O---- | 968 | | |
| PROTAC-XXVI-37 | ----O~O~~~~O---- | 968 | | |
| PROTAC-XXVI-38 | ----N(piperazine)N---- | 878 | | |
| PROTAC-XXVI-39 | O~N(piperazine)N---- | 922 | | |
| PROTAC-XXVI-40 | ----N(piperazine)N~O | 922 | | |
| PROTAC-XXVI-41 | ----O~N(piperazine)N---- | 936 | | |
| PROTAC-XXVI-42 | ----N(piperazine)N~O---- | 936 | | |
| PROTAC-XXVI-43 | O~~N(piperazine)N---- | 950 | | |
| PROTAC-XXVI-44 | ----N(piperazine)N~~O | 950 | | |

TABLE 26-continued

Protacs composed of a RAF ligand and a cereblon ligand
with 5-position linkage having the following chemical structure

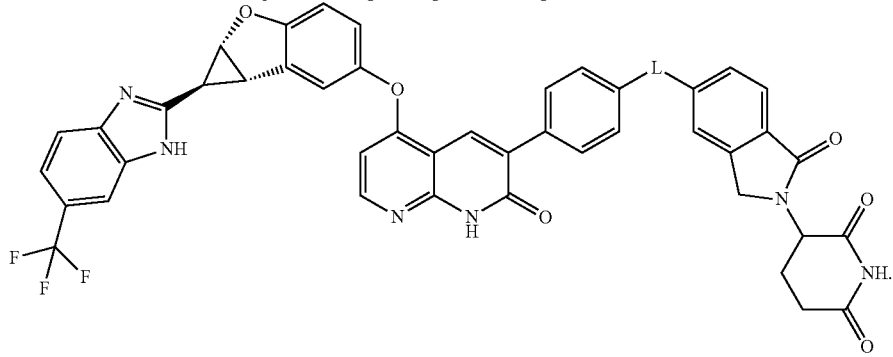

(PROTAC-XXVI).

| PROTAC-XXVI Compound | L | Mass | DC$_{50}$ (μM) | D$_{max}$ (%) |
|---|---|---|---|---|
| PROTAC-XXVI-45 | ----O\_\_O\_\_\_N\_\_N---- | 966 | | |
| PROTAC-XXVI-46 | ----N\_\_N\_\_\_O\_\_O---- | 966 | | |
| PROTAC-XXVI-47 | ----N\_\_N\_\_N\_\_N---- | 990 | | |
| PROTAC-XXVI-48 | O\_\_N\_\_N\_\_O | 966 | | |
| PROTAC-XXVI-49 | O\_\_O\_\_N\_\_N---- | 980 | | |
| PROTAC-XXVI-50 | O\_\_O\_\_N\_\_N---- | 980 | | |
| PROTAC-XXVI-51 | O\_\_\_\_N\_\_N---- | 978 | | |
| PROTAC-XXVI-52 | ----N\_\_N\_\_O\_\_O | 980 | | |
| PROTAC-XXVI-53 | ----N\_\_N\_\_O\_\_O | 980 | | |
| PROTAC-XXVI-54 | ----N\_\_N\_\_\_\_O | 978 | | |

TABLE 26-continued
Protacs composed of a RAF ligand and a cereblon ligand
with 5-position linkage having the following chemical structure
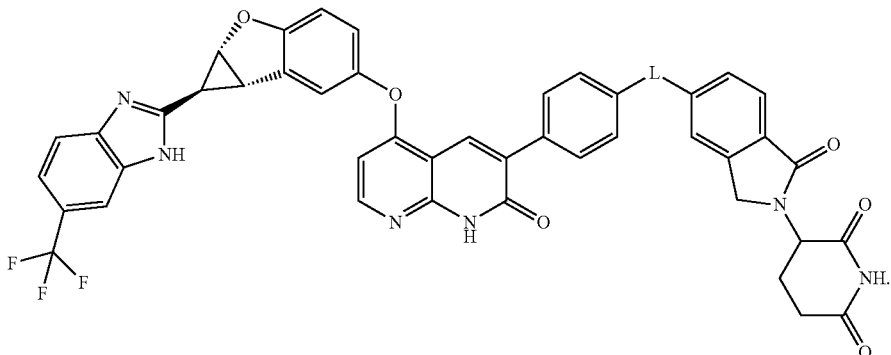
(PROTAC-XXVI).
| PROTAC-XXVI Compound | L | Mass | DC$_{50}$ (µM) | D$_{max}$ (%) |
|---|---|---|---|---|
| PROTAC-XXVI-55 | | 1004 | | |
| PROTAC-XXVI-56 | | 980 | | |
| PROTAC-XXVI-57 | | 980 | | |
| PROTAC-XXVI-58 | | 994 | | |
| PROTAC-XXVI-59 | | 994 | | |
| PROTAC-XXVI-60 | | 994 | | |
| PROTAC-XXVI-61 | | 992 | | |
| PROTAC-XXVI-62 | | 994 | | |

TABLE 26-continued

Protacs composed of a RAF ligand and a cereblon ligand with 5-position linkage having the following chemical structure

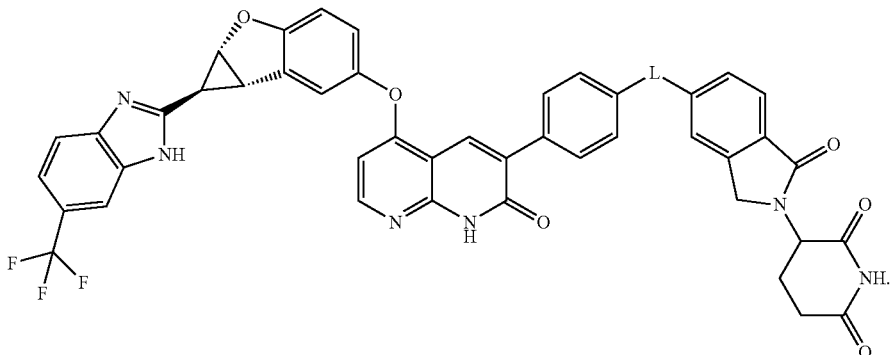

(PROTAC-XXVI).

| PROTAC-XXVI Compound | L | Mass | DC$_{50}$ (μM) | D$_{max}$ (%) |
|---|---|---|---|---|
| PROTAC-XXVI-63 | ----N(piperazine)N-CH₂CH₂-O-CH₂CH₂-O---- | 994 | | |
| PROTAC-XXVI-64 | ----N(piperazine)N-CH₂CH₂-O-CH₂CH₂CH₂-O---- | 994 | | |
| PROTAC-XXVI-65 | ----N(piperazine)N-(CH₂)₄-O---- | 992 | | |
| PROTAC-XXVI-66 | ----N(piperazine)N-CH₂CH₂CH₂-N(piperazine)N---- | 1018 | | |
| PROTAC-XXVI-67 | ----O-CH₂CH₂-N(piperazine)N-CH₂CH₂-O---- | 994 | | |
| PROTAC-XXVI-68 | ----O-(CH₂)₄-N(piperazine)N-CH₂CH₂-O---- | 994 | | |
| PROTAC-XXVI-69 | ----O-CH₂CH₂-N(piperazine)N-(CH₂)₄-O---- | 994 | | |
| PROTAC-XXVI-70 | ----O---- | 810 | | |

TABLE 27

Protacs composed of a RAF ligand and a cereblon ligand with 6-position linkage having the following chemical structure

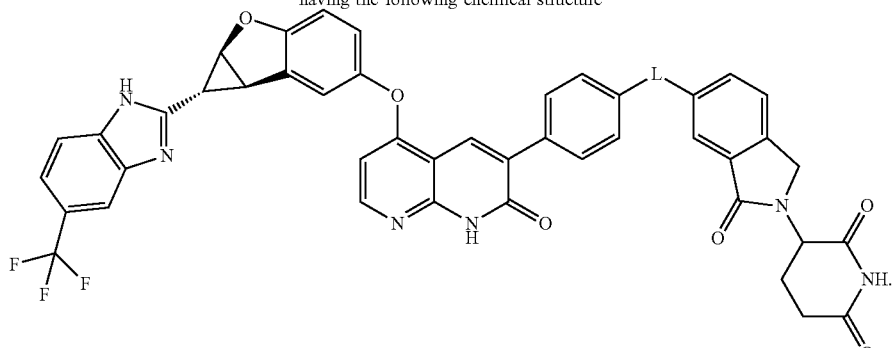

(PROTAC-XXVII).

| PROTAC-XXVII Compound | L | Mass | DC$_{50}$ (μM) | D$_{max}$ (%) |
|---|---|---|---|---|
| PROTAC-XXVII-1 | ----O~~O---- | 854 | | |
| PROTAC-XXVII-2 | ----O~~O~~O''' | 898 | | |
| PROTAC-XXVII-3 | ----O~~O~~O~~O---- | 942 | | |
| PROTAC-XXVII-4 | ----O~~O~~O~~O~~O''' | 986 | | |
| PROTAC-XXVII-5 | ----O~~O~~O~~O~~O~~O---- | 1030 | | |
| PROTAC-XXVII-6 | ----O~~O~~O~~O~~O~~O~~O''' | 1074 | | |
| PROTAC-XXVII-7 | ----O~~O''' | 838 | | |
| PROTAC-XXVII-8 | '''O~~O''' | 824 | | |
| PROTAC-XXVII-9 | '''O~~O---- | 838 | | |
| PROTAC-XXVII-10 | ----O~~O''' | 824 | | |
| PROTAC-XXVII-11 | ----O~~~O''' | 868 | | |
| PROTAC-XXVII-12 | ----O~~~O---- | 882 | | |
| PROTAC-XXVII-13 | ----O~~O~~O---- | 912 | | |
| PROTAC-XXVII-14 | ----O~~O~~O---- | 912 | | |
| PROTAC-XXVII-15 | ----O~~~O---- | 910 | | |
| PROTAC-XXVII-16 | ----O~~O~~O~O''' | 926 | | |

TABLE 27-continued

Protacs composed of a RAF ligand and a cereblon ligand with 6-position linkage having the following chemical structure

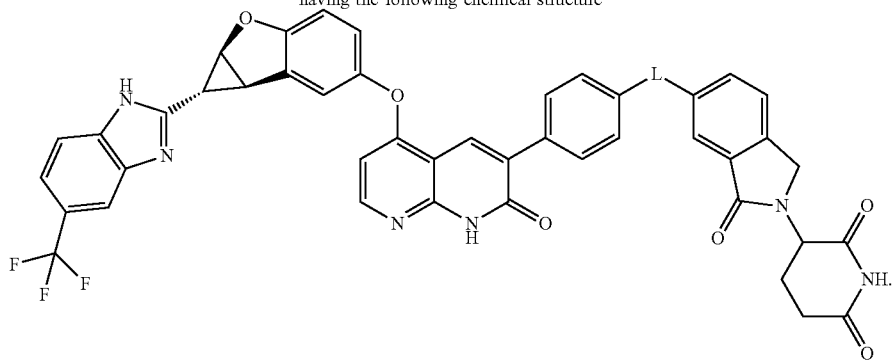

(PROTAC-XXVII).

| PROTAC-XXVII Compound | L | Mass | $DC_{50}$ ($\mu$M) | $D_{max}$ (%) |
|---|---|---|---|---|
| PROTAC-XXVII-17 |  | 926 | | |
| PROTAC-XXVII-18 |  | 926 | | |
| PROTAC-XXVII-19 |  | 956 | | |
| PROTAC-XXVII-20 | 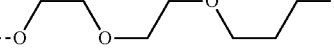 | 956 | | |
| PROTAC-XXVII-21 | 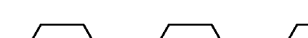 | 956 | | |
| PROTAC-XXVII-22 | 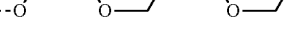 | 954 | | |
| PROTAC-XXVII-23 | 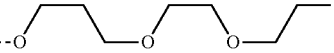 | 954 | | |
| PROTAC-XXVII-24 | 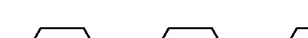 | 954 | | |
| PROTAC-XXVII-25 | 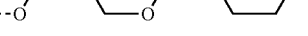 | 954 | | |
| PROTAC-XXVII-26 |  | 954 | | |
| PROTAC-XXVII-27 |  | 970 | | |
| PROTAC-XXVII-28 | 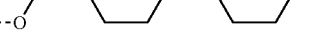 | 970 | | |
| PROTAC-XXVII-29 | 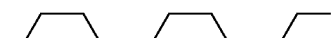 | 970 | | |
| PROTAC-XXVII-30 |  | 970 | | |
| PROTAC-XXVII-31 | 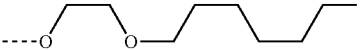 | 970 | | |

TABLE 27-continued

Protacs composed of a RAF ligand and a cereblon ligand with 6-position linkage having the following chemical structure

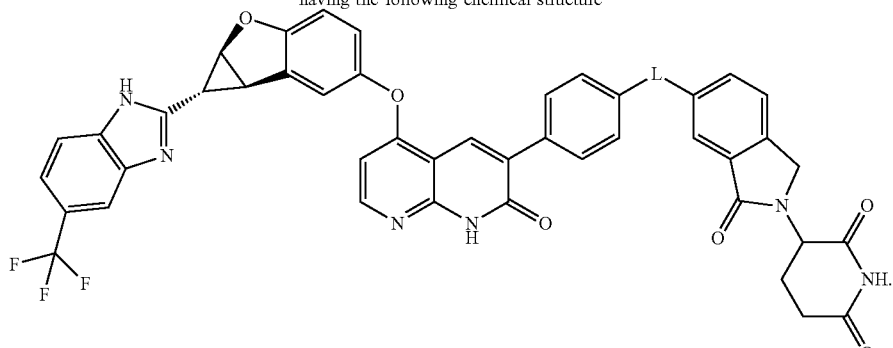

(PROTAC-XXVII).

| PROTAC-XXVII Compound | L | Mass | DC$_{50}$ (μM) | D$_{max}$ (%) |
|---|---|---|---|---|
| PROTAC-XXVII-32 | | 968 | | |
| PROTAC-XXVII-33 | | 968 | | |
| PROTAC-XXVII-34 | | 968 | | |
| PROTAC-XXVII-35 | | 968 | | |
| PROTAC-XXVII-36 | | 968 | | |
| PROTAC-XXVII-37 | | 968 | | |
| PROTAC-XXVII-38 | | 878 | | |
| PROTAC-XXVII-39 | | 922 | | |
| PROTAC-XXVII-40 | | 922 | | |
| PROTAC-XXVII-41 | | 936 | | |
| PROTAC-XXVII-42 | | 936 | | |
| PROTAC-XXVII-43 | | 950 | | |
| PROTAC-XXVII-44 | | 950 | | |

TABLE 27-continued
Protacs composed of a RAF ligand and a cereblon ligand with 6-position linkage having the following chemical structure
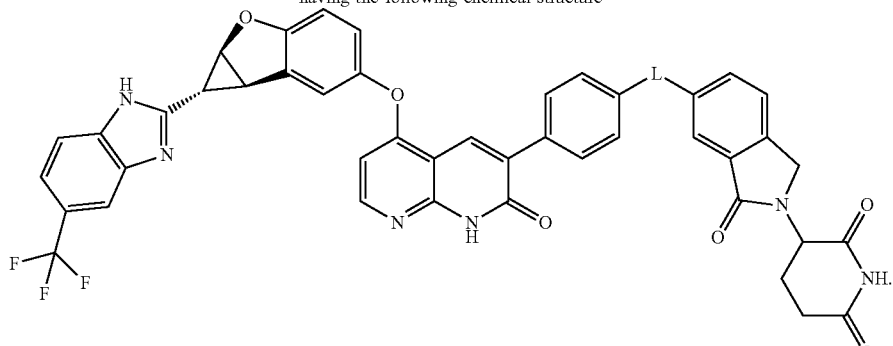
(PROTAC-XXVII).
| PROTAC-XXVII Compound | L | Mass | $DC_{50}$ (μM) | $D_{max}$ (%) |
|---|---|---|---|---|
| PROTAC-XXVII-45 | | 966 | | |
| PROTAC-XXVII-46 | | 966 | | |
| PROTAC-XXVII-47 | | 990 | | |
| PROTAC-XXVII-48 | | 966 | | |
| PROTAC-XXVII-49 | | 980 | | |
| PROTAC-XXVII-50 | | 980 | | |
| PROTAC-XXVII-51 | | 978 | | |
| PROTAC-XXVII-52 | | 980 | | |
| PROTAC-XXVII-53 | | 980 | | |
| PROTAC-XXVII-54 | | 978 | | |

TABLE 27-continued

Protacs composed of a RAF ligand and a cereblon ligand with 6-position linkage having the following chemical structure

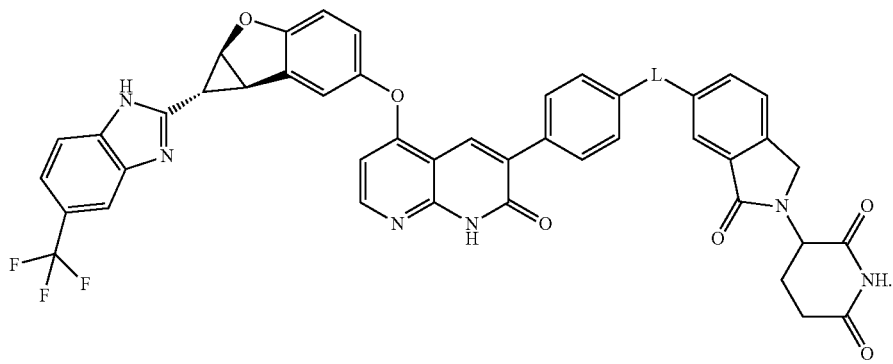

(PROTAC-XXVII).

| PROTAC-XXVII Compound | L | Mass | DC$_{50}$ ($\mu$M) | D$_{max}$ (%) |
|---|---|---|---|---|
| PROTAC-XXVII-55 | ![structure] | 1004 | | |
| PROTAC-XXVII-56 | ![structure] | 980 | | |
| PROTAC-XXVII-57 | ![structure] | 980 | | |
| PROTAC-XXVII-58 | ![structure] | 994 | | |
| PROTAC-XXVII-59 | ![structure] | 994 | | |
| PROTAC-XXVII-60 | ![structure] | 994 | | |
| PROTAC-XXVII-61 | ![structure] | 992 | | |
| PROTAC-XXVII-62 | ![structure] | 994 | | |

TABLE 27-continued
Protacs composed of a RAF ligand and a cereblon ligand with 6-position linkage having the following chemical structure
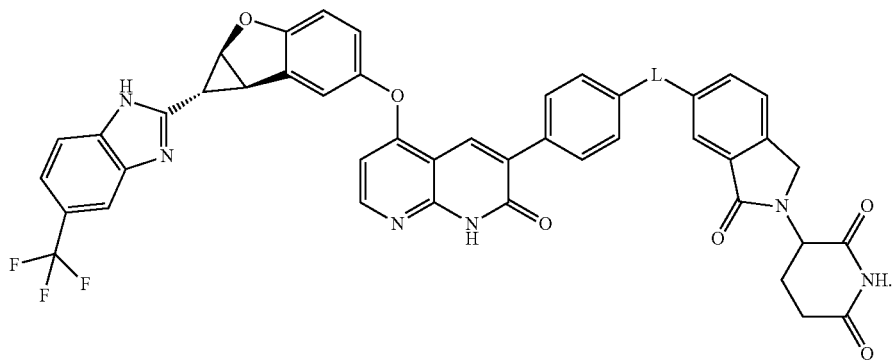
(PROTAC-XXVII).
| PROTAC-XXVII Compound | L | Mass | DC$_{50}$ (μM) | D$_{max}$ (%) |
|---|---|---|---|---|
| PROTAC-XXVII-63 | 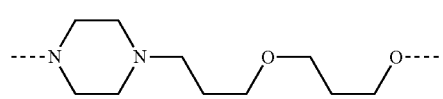 | 994 | | |
| PROTAC-XXVII-64 | 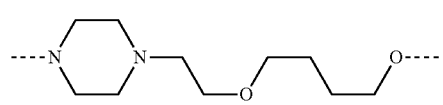 | 994 | | |
| PROTAC-XXVII-65 | 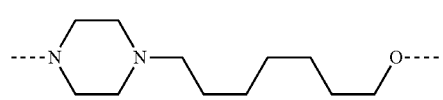 | 992 | | |
| PROTAC-XXVII-66 | 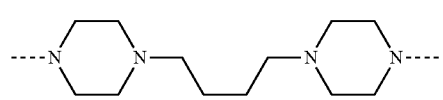 | 1018 | | |
| PROTAC-XXVII-67 | 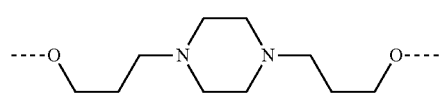 | 994 | | |
| PROTAC-XXVII-68 | 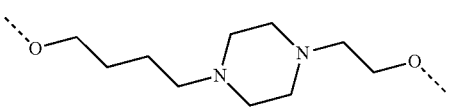 | 994 | | |
| PROTAC-XXVII-69 | 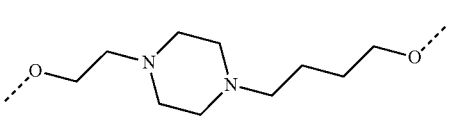 | 994 | | |
| PROTAC-XXVII-70 |  | 810 | | |

TABLE 28

Protacs composed of a RAF ligand and a cereblon ligand with 4-position linkage having the following chemical structure

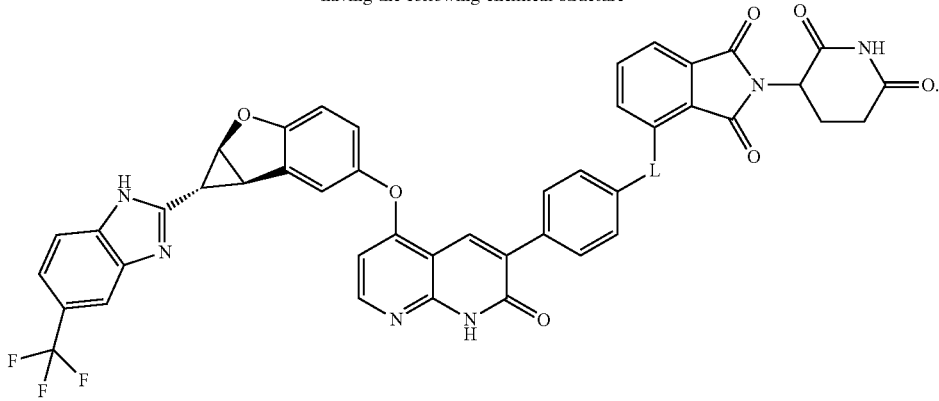

(PROTAC-XXVIII).

| PROTAC-XXVIII Compound | L | Mass | DC$_{50}$ (μM) | D$_{max}$ (%) |
|---|---|---|---|---|
| PROTAC-XXVIII-1 | ----O~~O---- | 868 | | |
| PROTAC-XXVIII-2 | ----O~~O~~O,, | 912 | | |
| PROTAC-XXVIII-3 | ----O~~O~~O~~O---- | 956 | | |
| PROTAC-XXVIII-4 | ----O~~O~~O~~O~~O,, | 1000 | | |
| PROTAC-XXVIII-5 | ----O~~O~~O~~O~~O~~O---- | 1044 | | |
| PROTAC-XXVIII-6 | ----O~~O~~O~~O~~O~~O~~O,, | 1088 | | |
| PROTAC-XXVIII-7 | ----~~O,, | 852 | | |
| PROTAC-XXVIII-8 | ,,~~O,, | 838 | | |
| PROTAC-XXVIII-9 | ,,O~~---- | 852 | | |
| PROTAC-XXVIII-10 | ----O~~ | 838 | | |
| PROTAC-XXVIII-11 | ----O~~O,, | 882 | | |
| PROTAC-XXVIII-12 | ----O~~~O---- | 896 | | |
| PROTAC-XXVIII-13 | ----O~~O~~O---- | 926 | | |
| PROTAC-XXVIII-14 | ----O~~O~~O---- | 926 | | |
| PROTAC-XXVIII-15 | ----O~~~~O---- | 924 | | |

TABLE 28-continued

Protacs composed of a RAF ligand and a cereblon ligand with 4-position linkage having the following chemical structure

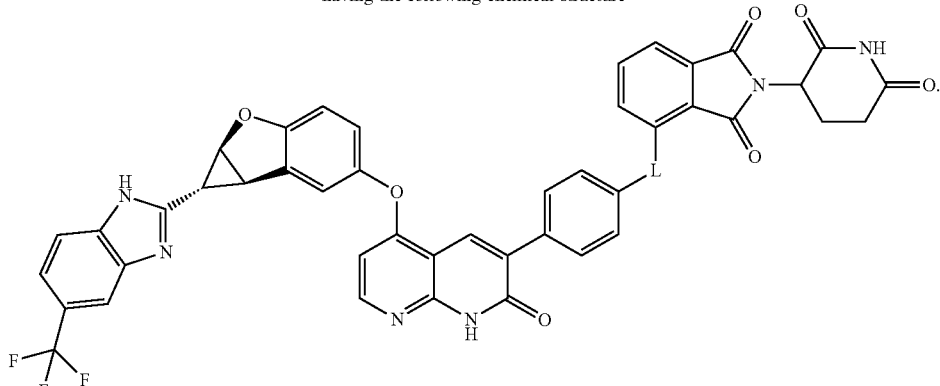

(PROTAC-XXVIII).

| PROTAC-XXVIII Compound | L | Mass | DC$_{50}$ (μM) | D$_{max}$ (%) |
|---|---|---|---|---|
| PROTAC-XXVIII-16 | ----O\_/\O\_/\_/\O\_/\O/ | 940 | | |
| PROTAC-XXVIII-17 | ----O\_/\_/\O\_/\_/\O/ | 940 | | |
| PROTAC-XXVIII-18 | ----O\_/\_/\O\_/\_/\O/ | 940 | | |
| PROTAC-XXVIII-19 | ----O\_/\O\_/\_/\O\_/\_/\O | 970 | | |
| PROTAC-XXVIII-20 | ----O\_/\O\_/\_/\O\_/\_/\O | 970 | | |
| PROTAC-XXVIII-21 | ----O\_/\O\_/\O\_/\_/\O | 970 | | |
| PROTAC-XXVIII-22 | ----O\_/\O\_/\_/\O\_/\_/\O | 968 | | |
| PROTAC-XXVIII-23 | ----O\_/\_/\O\_/\_/\O\_/\_/\O | 968 | | |
| PROTAC-XXVIII-24 | ----O\_/\_/\O\_/\O\_/\_/\O | 968 | | |
| PROTAC-XXVIII-25 | ----O\_/\_/\O\_/\_/\O\_/\O | 968 | | |
| PROTAC-XXVIII-26 | ----O\_/\O\_/\_/\O\_/\_/\O | 968 | | |
| PROTAC-XXVIII-27 | ----O\_/\O\_/\O\_/\_/\O---- | 984 | | |
| PROTAC-XXVIII-28 | ----O\_/\O\_/\O\_/\O---- | 984 | | |
| PROTAC-XXVIII-29 | ----O\_/\O\_/\O\_/\O---- | 984 | | |
| PROTAC-XXVIII-30 | ----O\_/\O\_/\O\_/\O---- | 984 | | |

TABLE 28-continued

Protacs composed of a RAF ligand and a cereblon ligand with 4-position linkage having the following chemical structure

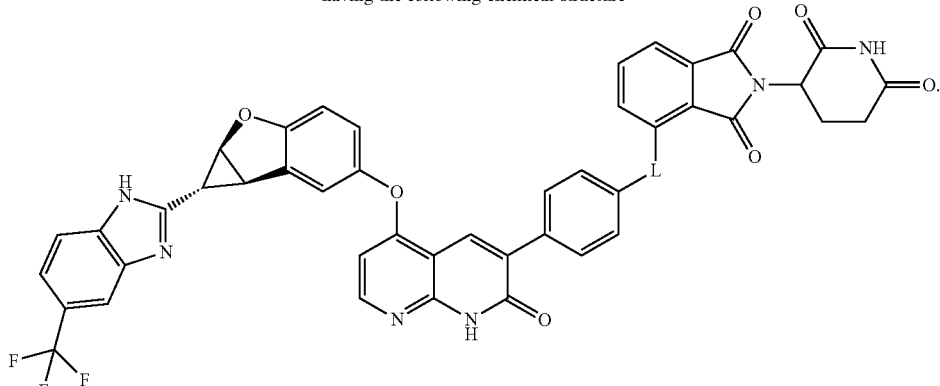

(PROTAC-XXVIII).

| PROTAC-XXVIII Compound | L | Mass | DC$_{50}$ (μM) | D$_{max}$ (%) |
|---|---|---|---|---|
| PROTAC-XXVIII-31 | ----O~~O~~O~~O---- | 984 | | |
| PROTAC-XXVIII-32 | ----O~~O~~O---- | 982 | | |
| PROTAC-XXVIII-33 | ----O~~O~~O---- | 982 | | |
| PROTAC-XXVIII-34 | ----O~~O~~O---- | 982 | | |
| PROTAC-XXVIII-35 | ----O~~O~~O---- | 982 | | |
| PROTAC-XXVIII-36 | ----O~~O~~O---- | 982 | | |
| PROTAC-XXVIII-37 | ----O~~O~~O---- | 982 | | |
| PROTAC-XXVIII-38 | ----N(piperazine)N---- | 892 | | |
| PROTAC-XXVIII-39 | O~~N(piperazine)N---- | 936 | | |
| PROTAC-XXVIII-40 | ----N(piperazine)N~~O | 936 | | |
| PROTAC-XXVIII-41 | ----O~~N(piperazine)N---- | 950 | | |
| PROTAC-XXVIII-42 | ----N(piperazine)N~~O---- | 950 | | |
| PROTAC-XXVIII-43 | O~~N(piperazine)N---- | 964 | | |

TABLE 28-continued
Protacs composed of a RAF ligand and a cereblon ligand with 4-position linkage having the following chemical structure
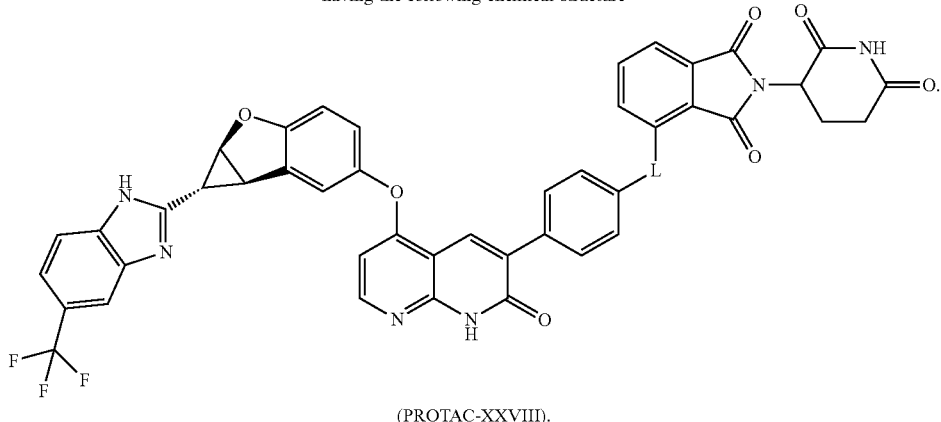
(PROTAC-XXVIII).
| PROTAC-XXVIII Compound | L | Mass | $DC_{50}$ ($\mu M$) | $D_{max}$ (%) |
|---|---|---|---|---|
| PROTAC-XXVIII-44 | | 964 | | |
| PROTAC-XXVIII-45 | | 980 | | |
| PROTAC-XXVIII-46 | | 980 | | |
| PROTAC-XXVIII-47 | | 1004 | | |
| PROTAC-XXVIII-48 | | 980 | | |
| PROTAC-XXVIII-49 | | 994 | | |
| PROTAC-XXVIII-50 | | 994 | | |
| PROTAC-XXVIII-51 | | 992 | | |
| PROTAC-XXVIII-52 | | 994 | | |
| PROTAC-XXVIII-53 | | 994 | | |

TABLE 28-continued

Protacs composed of a RAF ligand and a cereblon ligand with 4-position linkage having the following chemical structure

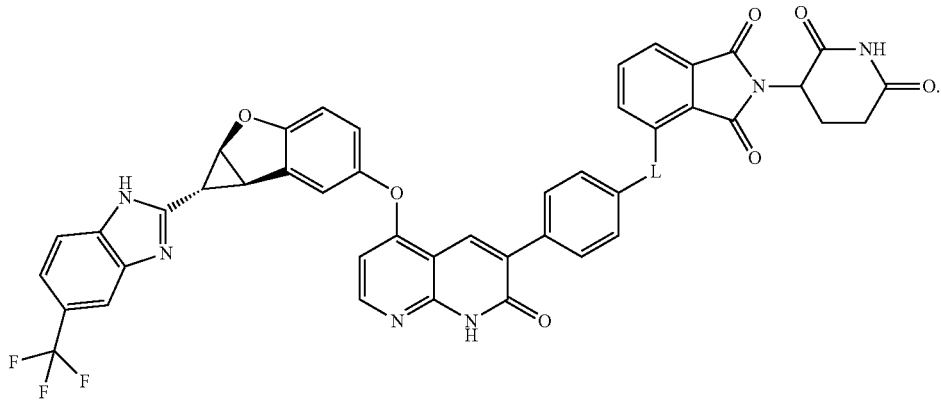

(PROTAC-XXVIII).

| PROTAC-XXVIII Compound | L | Mass | $DC_{50}$ (μM) | $D_{max}$ (%) |
|---|---|---|---|---|
| PROTAC-XXVIII-54 | ----N(piperazine)N—(CH2)5—O\~ | 992 | | |
| PROTAC-XXVIII-55 | ----N(piperazine)N—(CH2)3—N(piperazine)N— | 1018 | | |
| PROTAC-XXVIII-56 | ----O—(CH2)2—N(piperazine)N—(CH2)2—O\~ | 994 | | |
| PROTAC-XXVIII-57 | \~O—(CH2)2—N(piperazine)N—(CH2)2—O---- | 994 | | |
| PROTAC-XXVIII-58 | ----O—(CH2)3—O—(CH2)2—N(piperazine)N---- | 1008 | | |
| PROTAC-XXVIII-59 | ----O—(CH2)2—O—(CH2)2—N(piperazine)N---- | 1008 | | |
| PROTAC-XXVIII-60 | ----O—(CH2)2—O—(CH2)3—N(piperazine)N---- | 1008 | | |
| PROTAC-XXVIII-61 | ----O—(CH2)4—N(piperazine)N---- | 1006 | | |

TABLE 28-continued

Protacs composed of a RAF ligand and a cereblon ligand with 4-position linkage having the following chemical structure

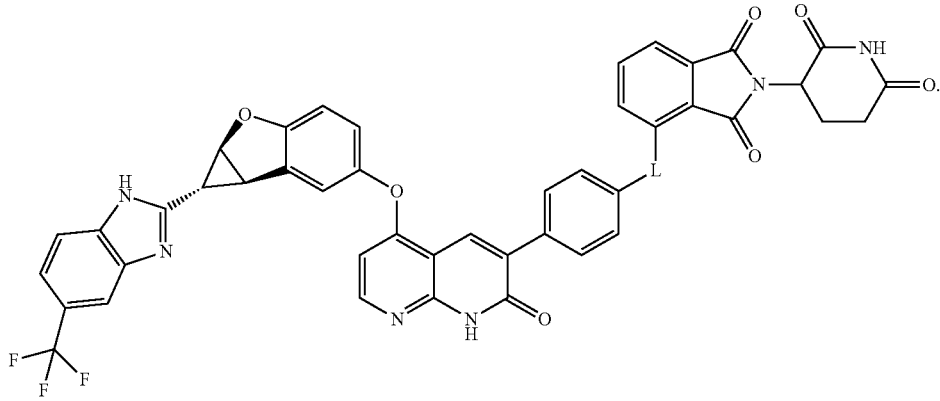

(PROTAC-XXVIII).

| PROTAC-XXVIII Compound | L | Mass | DC$_{50}$ (μM) | D$_{max}$ (%) |
|---|---|---|---|---|
| PROTAC-XXVIII-62 | ----N(piperazine)N—CH$_2$CH$_2$CH$_2$—O—CH$_2$CH$_2$—O---- | 1008 | | |
| PROTAC-XXVIII-63 | ----N(piperazine)N—CH$_2$CH$_2$—O—CH$_2$CH$_2$CH$_2$—O---- | 1008 | | |
| PROTAC-XXVIII-64 | ----N(piperazine)N—CH$_2$CH$_2$—O—CH$_2$CH$_2$CH$_2$—O---- | 1008 | | |
| PROTAC-XXVIII-65 | ----N(piperazine)N—(CH$_2$)$_4$—O---- | 1006 | | |
| PROTAC-XXVIII-66 | ----N(piperazine)N—CH$_2$CH$_2$CH$_2$—N(piperazine)N---- | 1032 | | |
| PROTAC-XXVIII-67 | ----O—CH$_2$CH$_2$—N(piperazine)N—CH$_2$CH$_2$—O---- | 1008 | | |
| PROTAC-XXVIII-68 | ----O—(CH$_2$)$_4$—N(piperazine)N—CH$_2$CH$_2$—O---- | 1008 | | |
| PROTAC-XXVIII-69 | ----O—CH$_2$CH$_2$—N(piperazine)N—(CH$_2$)$_4$—O---- | 1008 | | |
| PROTAC-XXVIII-70 | ----O---- | 824 | | |

TABLE 29

Protacs composed of a RAF ligand and a cereblon ligand with 4-position linkage having the following chemical structure

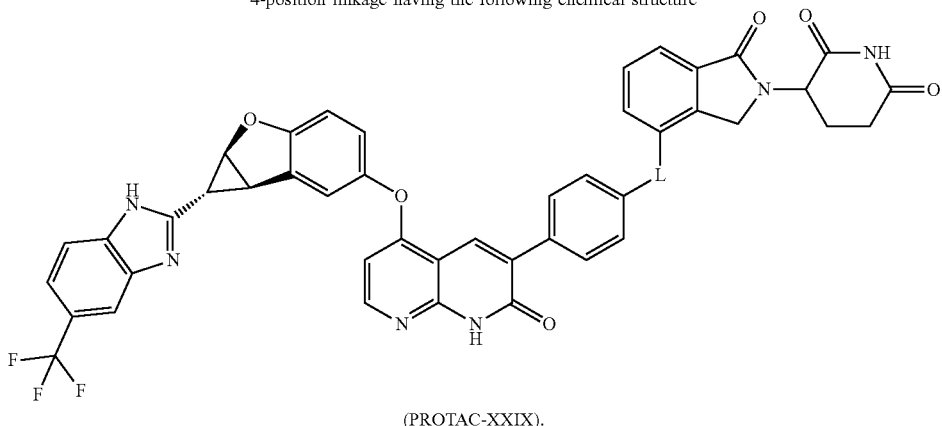

(PROTAC-XXIX).

| PROTAC-XXIX Compound | L | Mass | $DC_{50}$ (μM) | $D_{max}$ (%) |
|---|---|---|---|---|
| PROTAC-XXIX-1 | ----O~~O---- | 854 | | |
| PROTAC-XXIX-2 | ----O~~O~~O--- | 898 | | |
| PROTAC-XXIX-3 | ----O~~O~~O~~O---- | 942 | | |
| PROTAC-XXIX-4 | ----O~~O~~O~~O~~O--- | 986 | | |
| PROTAC-XXIX-5 | ----O~~O~~O~~O~~O~~O---- | 1030 | | |
| PROTAC-XXIX-6 | ----O~~O~~O~~O~~O~~O~~O--- | 1074 | | |
| PROTAC-XXIX-7 | ----~~O--- | 838 | | |
| PROTAC-XXIX-8 | ---~~O--- | 824 | | |
| PROTAC-XXIX-9 | ---~~O---- | 838 | | |
| PROTAC-XXIX-10 | ----O~~--- | 824 | | |
| PROTAC-XXIX-11 | ----O~~O--- | 868 | | |
| PROTAC-XXIX-12 | ----O~~~O--- | 882 | | |
| PROTAC-XXIX-13 | ----O~~O~~O---- | 912 | | |
| PROTAC-XXIX-14 | ----O~~O~~O---- | 912 | | |
| PROTAC-XXIX-15 | ----O~~~O---- | 910 | | |

TABLE 29-continued

Protacs composed of a RAF ligand and a cereblon ligand with 4-position linkage having the following chemical structure

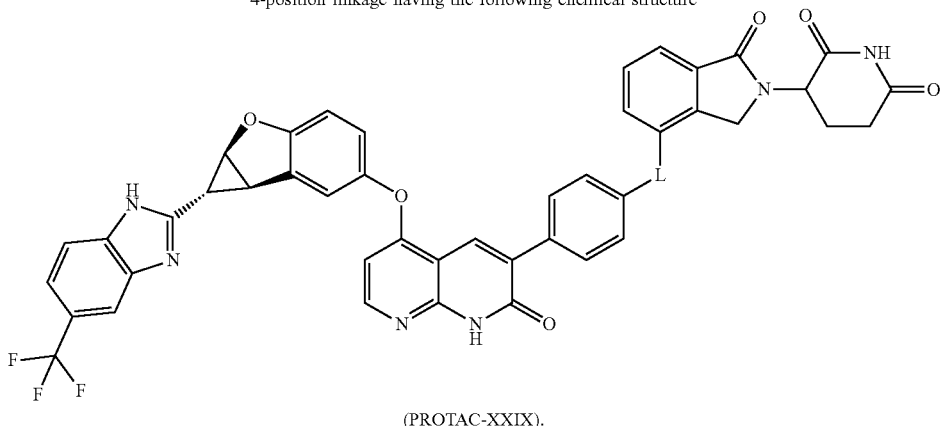

(PROTAC-XXIX).

| PROTAC-XXIX Compound | L | Mass | DC$_{50}$ (μM) | D$_{max}$ (%) |
|---|---|---|---|---|
| PROTAC-XXIX-16 | ----O∽O∽∽O∽ | 926 | | |
| PROTAC-XXIX-17 | ----O∽∽O∽O∽ | 926 | | |
| PROTAC-XXIX-18 | ----O∽∽∽O∽O∽ | 926 | | |
| PROTAC-XXIX-19 | ----O∽O∽∽O∽∽O | 956 | | |
| PROTAC-XXIX-20 | ----O∽O∽O∽∽O | 956 | | |
| PROTAC-XXIX-21 | ----O∽∽O∽O∽O | 956 | | |
| PROTAC-XXIX-22 | ----O∽∽O∽∽O∽O | 954 | | |
| PROTAC-XXIX-23 | ----O∽∽∽O∽∽O∽O | 954 | | |
| PROTAC-XXIX-24 | ----O∽∽∽∽O∽O | 954 | | |
| PROTAC-XXIX-25 | ----O∽∽∽O∽O∽O | 954 | | |
| PROTAC-XXIX-26 | ----O∽O∽∽∽O∽O | 954 | | |
| PROTAC-XXIX-27 | ----O∽O∽∽O∽∽O---- | 970 | | |
| PROTAC-XXIX-28 | ----O∽O∽∽O∽O---- | 970 | | |
| PROTAC-XXIX-29 | ----O∽O∽∽O∽O∽O---- | 970 | | |
| PROTAC-XXIX-30 | ----O∽O∽O∽O---- | 970 | | |

TABLE 29-continued

Protacs composed of a RAF ligand and a cereblon ligand with
4-position linkage having the following chemical structure

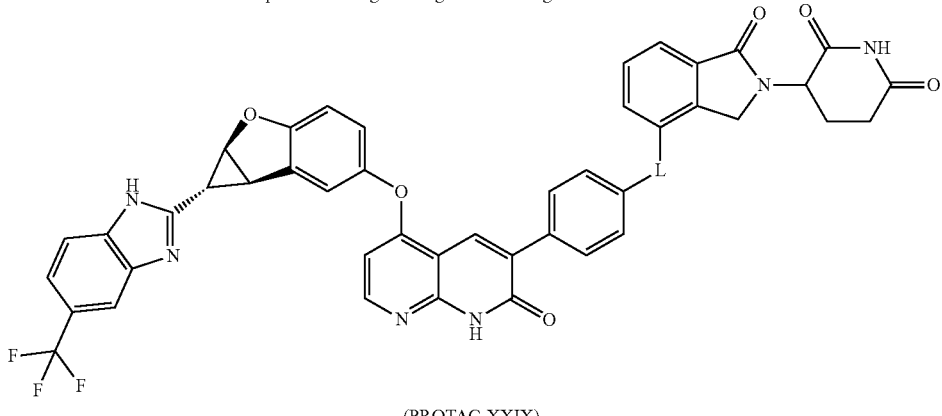

(PROTAC-XXIX).

| PROTAC-XXIX Compound | L | Mass | DC$_{50}$ (μM) | D$_{max}$ (%) |
|---|---|---|---|---|
| PROTAC-XXIX-31 | ----O~~~O~~~O~~~O---- | 970 | | |
| PROTAC-XXIX-32 | ----O~~~O~~~O~~~O---- | 968 | | |
| PROTAC-XXIX-33 | ----O~~~O~~~O~~~O---- | 968 | | |
| PROTAC-XXIX-34 | ----O~~~O~~~O~~~O---- | 968 | | |
| PROTAC-XXIX-35 | ----O~~~O~~~O~~~O---- | 968 | | |
| PROTAC-XXIX-36 | ----O~~~O~~~O~~~O---- | 968 | | |
| PROTAC-XXIX-37 | ----O~~~O~~~O~~~O---- | 968 | | |
| PROTAC-XXIX-38 | ----N(piperazine)N---- | 878 | | |
| PROTAC-XXIX-39 | O~~~N(piperazine)N---- | 922 | | |
| PROTAC-XXIX-40 | ----N(piperazine)N~~~O | 922 | | |
| PROTAC-XXIX-41 | ----O~~~N(piperazine)N---- | 936 | | |
| PROTAC-XXIX-42 | ----N(piperazine)N~~~O---- | 936 | | |

TABLE 29-continued
Protacs composed of a RAF ligand and a cereblon ligand with
4-position linkage having the following chemical structure
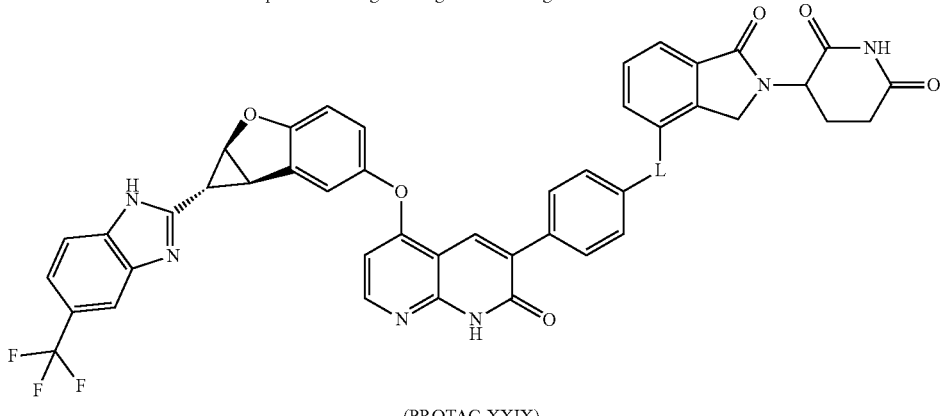
(PROTAC-XXIX).
| PROTAC-XXIX Compound | L | Mass | DC₅₀ (μM) | D_max (%) |
|---|---|---|---|---|
| PROTAC-XXIX-43 | | 950 | | |
| PROTAC-XXIX-44 | | 950 | | |
| PROTAC-XXIX-45 | | 966 | | |
| PROTAC-XXIX-46 | | 966 | | |
| PROTAC-XXIX-47 | | 990 | | |
| PROTAC-XXIX-48 | | 966 | | |
| PROTAC-XXIX-49 | | 980 | | |
| PROTAC-XXIX-50 | | 980 | | |
| PROTAC-XXIX-51 | | 978 | | |
| PROTAC-XXIX-52 | | 980 | | |

TABLE 29-continued

Protacs composed of a RAF ligand and a cereblon ligand with
4-position linkage having the following chemical structure

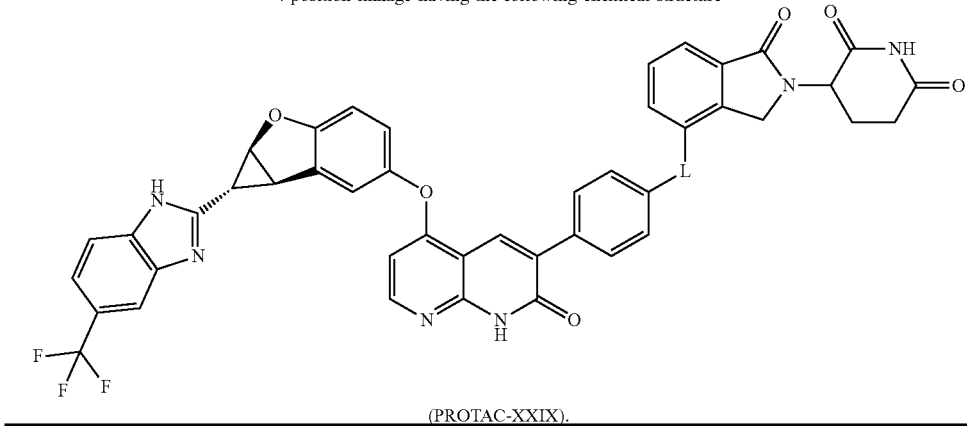

(PROTAC-XXIX).

| PROTAC-XXIX Compound | L | Mass | DC$_{50}$ (μM) | D$_{max}$ (%) |
|---|---|---|---|---|
| PROTAC-XXIX-53 | ----N⌒N−⌒⌒O⌒⌒O⋯ | 980 | | |
| PROTAC-XXIX-54 | ----N⌒N−⌒⌒⌒⌒O⋯ | 978 | | |
| PRO TAC-XXIX-55 | ----N⌒N−⌒⌒N⌒N-CH$_3$ | 1004 | | |
| PRO TAC-XXIX-56 | ----O⌒⌒N⌒N⌒⌒O⋯ | 980 | | |
| PRO TAC-XXIX-57 | ⋯O⌒⌒N⌒N⌒⌒O---- | 980 | | |
| PRO TAC-XXIX-58 | ----O⌒⌒⌒O⌒⌒N⌒N---- | 994 | | |
| PRO TAC-XXIX-59 | ----O⌒⌒O⌒⌒⌒N⌒N---- | 994 | | |
| PRO TAC-XXIX-60 | ----O⌒⌒O⌒⌒⌒N⌒N---- | 994 | | |
| PRO TAC-XXIX-61 | ----O⌒⌒⌒⌒⌒N⌒N---- | 992 | | |
| PRO TAC-XXIX-62 | ----N⌒N⌒⌒⌒O⌒⌒O---- | 994 | | |

TABLE 29-continued

Protacs composed of a RAF ligand and a cereblon ligand with 4-position linkage having the following chemical structure

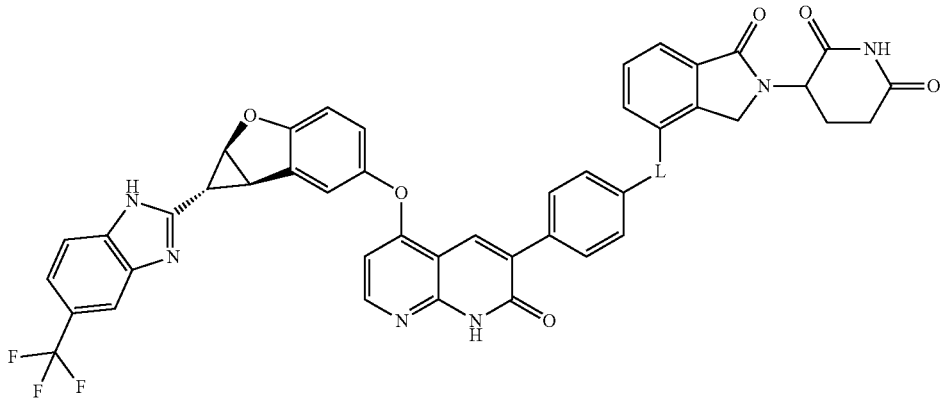

(PROTAC-XXIX).

| PROTAC-XXIX Compound | L | Mass | DC$_{50}$ (µM) | D$_{max}$ (%) |
|---|---|---|---|---|
| PRO TAC-XXIX-63 | ----N⌒N-\_\_\_O\_\_\_\_O---- | 994 | | |
| PRO TAC-XXIX-64 | ----N⌒N-\_\_\_O\_\_\_\_O---- | 994 | | |
| PRO TAC-XXIX-65 | ----N⌒N-_____O---- | 992 | | |
| PRO TAC-XXIX-66 | ----N⌒N-\_\_\_N⌒N---- | 1018 | | |
| PRO TAC-XXIX-67 | ----O\_\_N⌒N\_\_O---- | 994 | | |
| PRO TAC-XXIX-68 | ----O\_\_\_\_N⌒N\_\_O---- | 994 | | |
| PRO TAC-XXIX-69 | ----O\_\_N⌒N\_\_\_\_O---- | 994 | | |
| PROTAC-XXIX-70 | ----O---- | 810 | | |

TABLE 30
Protacs composed of a RAF ligand and a cereblon ligand with
7-position linkage having the following chemical structure
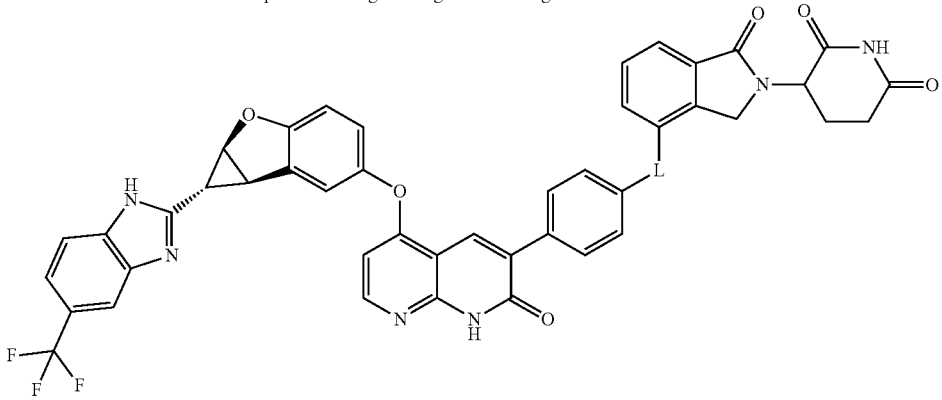
(PROTAC-XXX).
| PROTAC-XXX Compound | L | Mass | DC$_{50}$ (μM) | D$_{max}$ (%) |
|---|---|---|---|---|
| PROTAC-XXX-1 | | 854 | | |
| PROTAC-XXX-2 | | 898 | | |
| PROTAC-XXX-3 | | 942 | | |
| PROTAC-XXX-4 | | 986 | | |
| PROTAC-XXX-5 | | 1030 | | |
| PROTAC-XXX-6 | | 1074 | | |
| PROTAC-XXX-7 | | 838 | | |
| PROTAC-XXX-8 | | 824 | | |
| PROTAC-XXX-9 | | 838 | | |
| PROTAC-XXX-10 | | 824 | | |
| PROTAC-XXX-11 | | 868 | | |
| PROTAC-XXX-12 | | 882 | | |
| PROTAC-XXX-13 | | 912 | | |
| PROTAC-XXX-14 | | 912 | | |
| PROTAC-XXX-15 | | 910 | | |

TABLE 30-continued
Protacs composed of a RAF ligand and a cereblon ligand with 7-position linkage having the following chemical structure
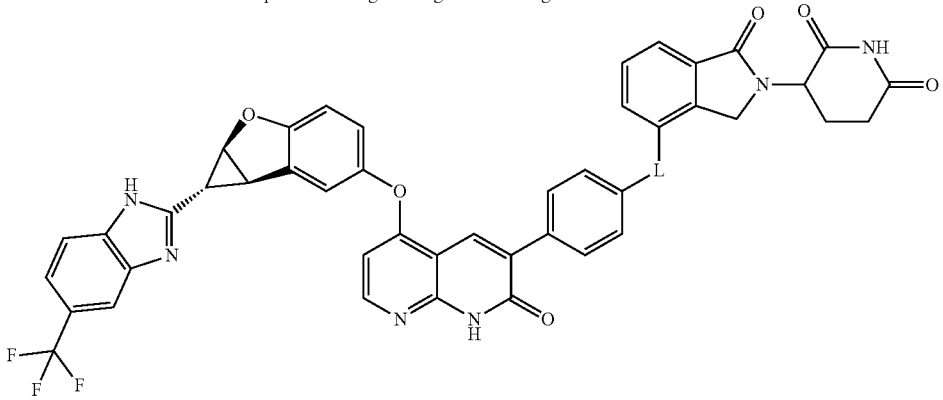
(PROTAC-XXX).
| PROTAC-XXX Compound | L | Mass | DC$_{50}$ (μM) | D$_{max}$ (%) |
|---|---|---|---|---|
| PROTAC-XXX-16 | 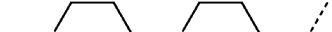 | 926 | | |
| PROTAC-XXX-17 |  | 926 | | |
| PROTAC-XXX-18 | 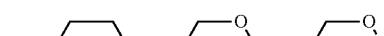 | 926 | | |
| PROTAC-XXX-19 | 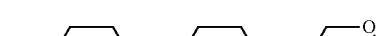 | 956 | | |
| PROTAC-XXX-20 |  | 956 | | |
| PROTAC-XXX-21 |  | 956 | | |
| PROTAC-XXX-22 |  | 954 | | |
| PROTAC-XXX-23 |  | 954 | | |
| PROTAC-XXX-24 | 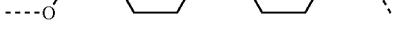 | 954 | | |
| PROTAC-XXX-25 | 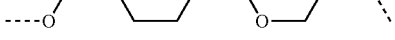 | 954 | | |
| PROTAC-XXX-26 | 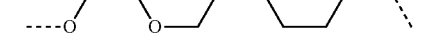 | 954 | | |
| PROTAC-XXX-27 |  | 970 | | |
| PROTAC-XXX-28 |  | 970 | | |
| PROTAC-XXX-29 | 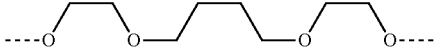 | 970 | | |
| PROTAC-XXX-30 |  | 970 | | |

TABLE 30-continued

Protacs composed of a RAF ligand and a cereblon ligand with
7-position linkage having the following chemical structure

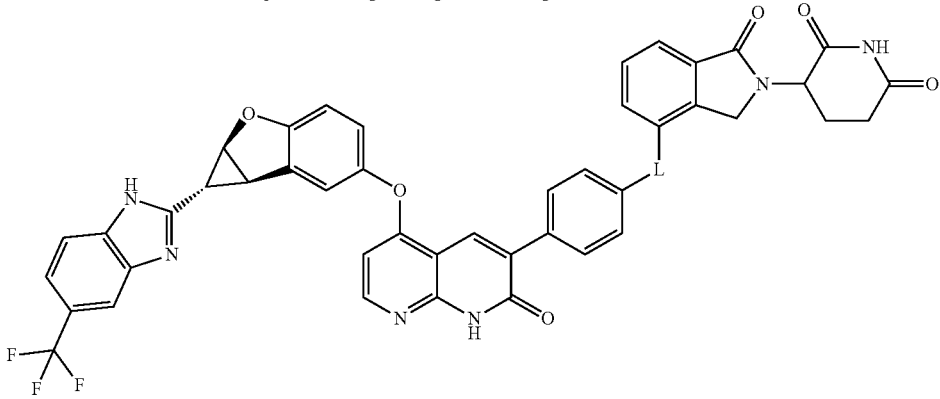

(PROTAC-XXX).

| PROTAC-XXX Compound | L | Mass | DC$_{50}$ (μM) | D$_{max}$ (%) |
|---|---|---|---|---|
| PROTAC-XXX-31 | ----O~~~O~~~O~~~O~~~O---- | 970 | | |
| PROTAC-XXX-32 | ----O~~~O~~~O~~~O---- | 968 | | |
| PROTAC-XXX-33 | ----O~~~O~~~O~~~O---- | 968 | | |
| PROTAC-XXX-34 | ----O~~~O~~~O~~~O---- | 968 | | |
| PROTAC-XXX-35 | ----O~~~O~~~O~~~O---- | 968 | | |
| PROTAC-XXX-36 | ----O~~~O~~~O~~~O---- | 968 | | |
| PROTAC-XXX-37 | ----O~~~O~~~O~~~O---- | 968 | | |
| PROTAC-XXX-38 | ----N(piperazine)N---- | 878 | | |
| PROTAC-XXX-39 | O~~~N(piperazine)N---- | 922 | | |
| PROTAC-XXX-40 | ----N(piperazine)N~~~O | 922 | | |
| PROTAC-XXX-41 | ----O~~~N(piperazine)N---- | 936 | | |
| PROTAC-XXX-42 | ----N(piperazine)N~~~O---- | 936 | | |

TABLE 30-continued
Protacs composed of a RAF ligand and a cereblon ligand with
7-position linkage having the following chemical structure
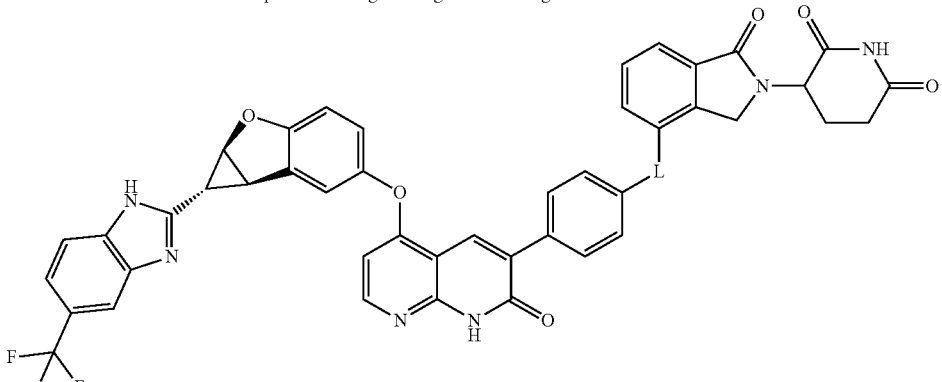
(PROTAC-XXX).
| PROTAC-XXX Compound | L | Mass | DC$_{50}$ (µM) | D$_{max}$ (%) |
|---|---|---|---|---|
| PROTAC-XXX-43 | | 950 | | |
| PROTAC-XXX-44 | | 950 | | |
| PROTAC-XXX-45 | | 966 | | |
| PROTAC-XXX-46 | | 966 | | |
| PROTAC-XXX-47 | | 990 | | |
| PROTAC-XXX-48 | | 966 | | |
| PROTAC-XXX-49 | | 980 | | |
| PROTAC-XXX-50 | | 980 | | |
| PROTAC-XXX-51 | | 978 | | |
| PROTAC-XXX-52 | | 980 | | |

TABLE 30-continued

Protacs composed of a RAF ligand and a cereblon ligand with
7-position linkage having the following chemical structure

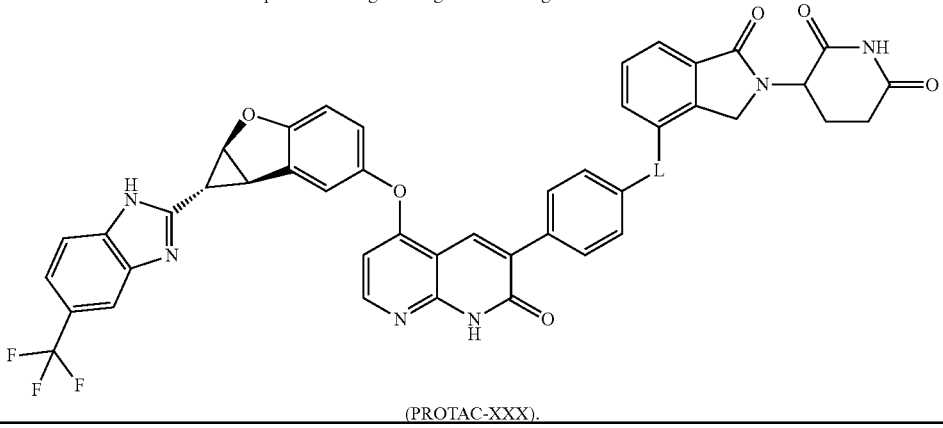

(PROTAC-XXX).

| PROTAC-XXX Compound | L | Mass | DC$_{50}$ (μM) | D$_{max}$ (%) |
|---|---|---|---|---|
| PROTAC-XXX-53 | piperazine-CH$_2$CH$_2$-O-CH$_2$CH$_2$-O | 980 | | |
| PROTAC-XXX-54 | piperazine-(CH$_2$)$_4$-O | 978 | | |
| PROTAC-XXX-55 | piperazine-CH$_2$CH$_2$CH$_2$-N-methylpiperazine | 1004 | | |
| PROTAC-XXX-56 | O-CH$_2$CH$_2$-piperazine-CH$_2$CH$_2$-O | 980 | | |
| PROTAC-XXX-57 | O-CH$_2$CH$_2$-piperazine-CH$_2$CH$_2$-O | 980 | | |
| PROTAC-XXX-58 | O-(CH$_2$)$_3$-O-CH$_2$CH$_2$-piperazine | 994 | | |
| PROTAC-XXX-59 | O-CH$_2$CH$_2$-O-(CH$_2$)$_3$-piperazine | 994 | | |
| PROTAC-XXX-60 | O-CH$_2$CH$_2$-O-(CH$_2$)$_3$-piperazine | 994 | | |
| PROTAC-XXX-61 | O-(CH$_2$)$_5$-piperazine | 992 | | |
| PROTAC-XXX-62 | piperazine-(CH$_2$)$_3$-O-CH$_2$CH$_2$-O | 994 | | |

TABLE 30-continued

Protacs composed of a RAF ligand and a cereblon ligand with
7-position linkage having the following chemical structure

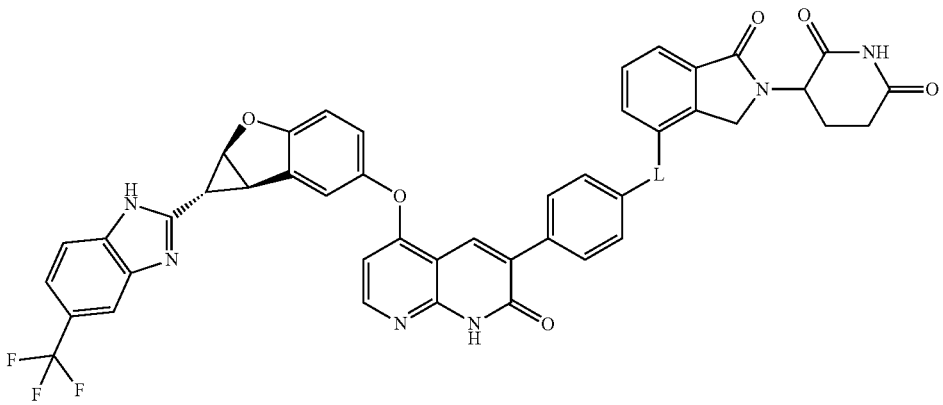

(PROTAC-XXX).

| PROTAC-XXX Compound | L | Mass | DC$_{50}$ (μM) | D$_{max}$ (%) |
|---|---|---|---|---|
| PROTAC-XXX-63 | ----N(piperazine)N-CH₂CH₂-O-CH₂CH₂-O---- | 994 | | |
| PROTAC-XXX-64 | ----N(piperazine)N-CH₂CH₂-O-CH₂CH₂CH₂-O---- | 994 | | |
| PROTAC-XXX-65 | ----N(piperazine)N-(CH₂)₄-O---- | 992 | | |
| PROTAC-XXX-66 | ----N(piperazine)N-CH₂CH₂CH₂-N(piperazine)N---- | 1018 | | |
| PROTAC-XXX-67 | ----O-CH₂CH₂CH₂-N(piperazine)N-CH₂CH₂-O---- | 994 | | |
| PROTAC-XXX-68 | ···O-(CH₂)₄-N(piperazine)N-CH₂CH₂-O··· | 994 | | |
| PROTAC-XXX-69 | ···O-CH₂CH₂-N(piperazine)N-(CH₂)₃-O··· | 994 | | |
| PROTAC-XXX-70 | ----O··· | 810 | | |

TABLE 31
Protacs composed of a RAF ligand and a VHL ligand with left-side linkage having the following chemical structure
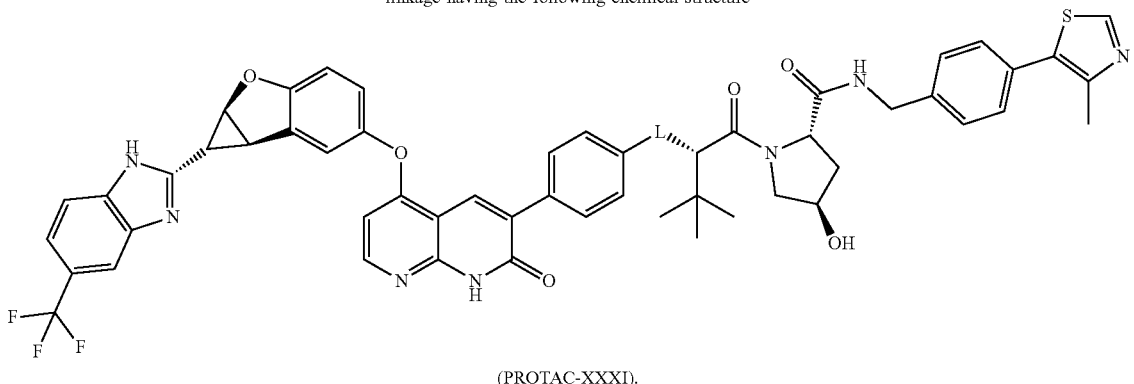
(PROTAC-XXXI).
| PROTAC-XXXI Compound | L | Mass | DC$_{50}$ (µM) | Dmax (%) |
|---|---|---|---|---|
| PROTAC-XXXI-1 | | 1082 | | |
| PROTAC-XXXI-2 | | 1126 | | |
| PROTAC-XXXI-3 | | 1170 | | |
| PROTAC-XXXI-4 | | 1214 | | |
| PROTAC-XXXI-5 | | 1258 | | |
| PROTAC-XXXI-6 | | 1302 | | |
| PROTAC-XXXI-7 | | 1066 | | |
| PROTAC-XXXI-8 | | 1052 | | |
| PROTAC-XXXI-9 | | 1096 | | |
| PROTAC-XXXI-10 | | 1096 | | |

TABLE 31-continued

Protacs composed of a RAF ligand and a VHL ligand with left-side linkage having the following chemical structure

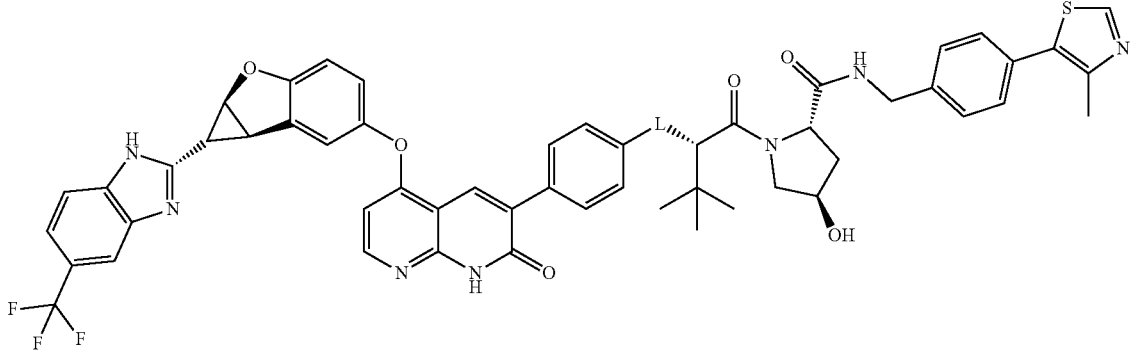

(PROTAC-XXXI).

| PROTAC-XXXI Compound | L | Mass | $DC_{50}$ (μM) | Dmax (%) |
|---|---|---|---|---|
| PROTAC-XXXI-11 | ----O~~~~C(=O)NH---- | 1094 | | |
| PROTAC-XXXI-12 | ----O~~~O~~C(=O)NH--- | 1110 | | |
| PROTAC-XXXI-13 | ----O~~O~~C(=O)NH--- | 1110 | | |
| PROTAC-XXXI-14 | ----O~O~~C(=O)NH--- | 1110 | | |
| PROTAC-XXXI-15 | ----O~~~~~C(=O)NH--- | 1108 | | |
| PROTAC-XXXI-16 | ----O~C(=O)NH---- | 1038 | | |
| PROTAC-XXXI-17 | ----O~~~C(=O)NH--- | 1080 | | |
| PROTAC-XXXI-18 | ---O~~O~~~C(=O)NH--- | 1124 | | |
| PROTAC-XXXI-19 | ---O~~O~~C(=O)NH--- | 1124 | | |
| PROTAC-XXXI-20 | ---O~~~O~~C(=O)NH--- | 1124 | | |

TABLE 31-continued
Protacs composed of a RAF ligand and a VHL ligand with left-side linkage having the following chemical structure
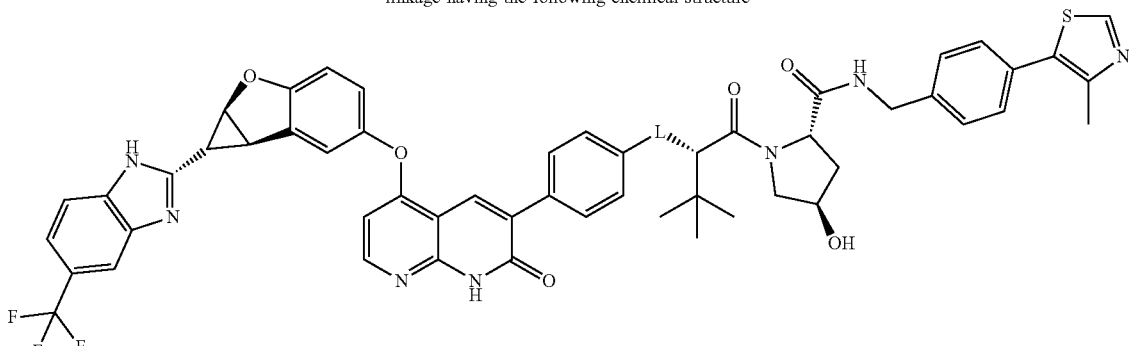
(PROTAC-XXXI).
| PROTAC-XXXI Compound | L | Mass | DC$_{50}$ (μM) | Dmax (%) |
|---|---|---|---|---|
| PROTAC-XXXI-21 | | 1124 | | |
| PROTAC-XXXI-22 | | 1140 | | |
| PROTAC-XXXI-23 | | 1140 | | |
| PROTAC-XXXI-24 | | 1140 | | |
| PROTAC-XXXI-25 | | 1138 | | |
| PROTAC-XXXI-26 | | 1138 | | |
| PROTAC-XXXI-27 | | 1138 | | |
| PROTAC-XXXI-28 | | 1138 | | |
| PROTAC-XXXI-29 | | 1138 | | |
| PROTAC-XXXI-30 | | 1154 | | |

TABLE 31-continued

Protacs composed of a RAF ligand and a VHL ligand with left-side
linkage having the following chemical structure

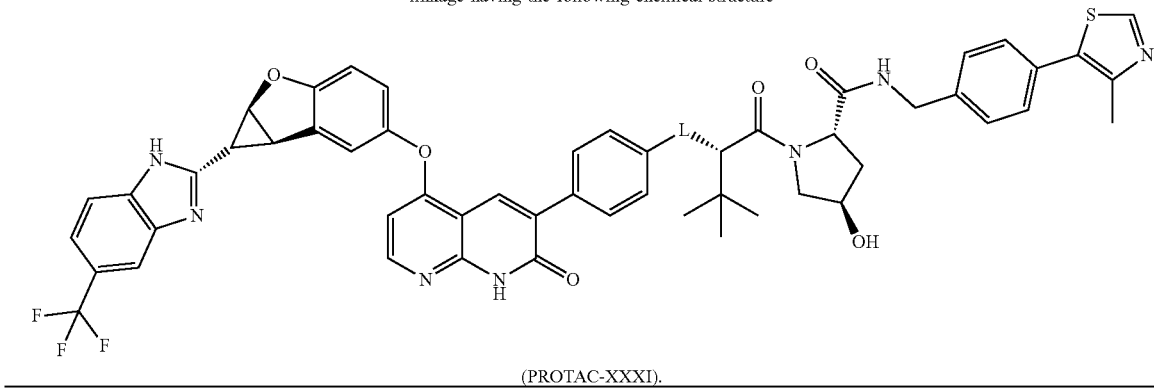

(PROTAC-XXXI).

| PROTAC-XXXI Compound | L | Mass | DC$_{50}$ (μM) | Dmax (%) |
|---|---|---|---|---|
| PROTAC-XXXI-31 | ----O~~O~~O~~O~~C(O)HN---- | 1154 | | |
| PROTAC-XXXI-32 | ----O~~O~~O~~C(O)HN---- | 1154 | | |
| PROTAC-XXXI-33 | ----O~~O~~O~~C(O)HN---- | 1168 | | |
| PROTAC-XXXI-34 | ----O~~O~~O~~C(O)HN---- | 1168 | | |
| PROTAC-XXXI-35 | ----O~~O~~O~~O~~C(O)HN---- | 1168 | | |
| PROTAC-XXXI-36 | ----O~~O~~O~~C(O)HN---- | 1168 | | |
| PROTAC-XXXI-37 | ----O~~O~~O~~C(O)HN---- | 1168 | | |
| PROTAC-XXXI-38 | ----O~~O~~O~~C(O)HN---- | 1168 | | |
| PROTAC-XXXI-39 | ----O~~O~~O~~C(O)HN---- | 1168 | | |
| PROTAC-XXXI-40 | ----O~~O~~C(O)HN---- | 1166 | | |

TABLE 31-continued
Protacs composed of a RAF ligand and a VHL ligand with left-side linkage having the following chemical structure
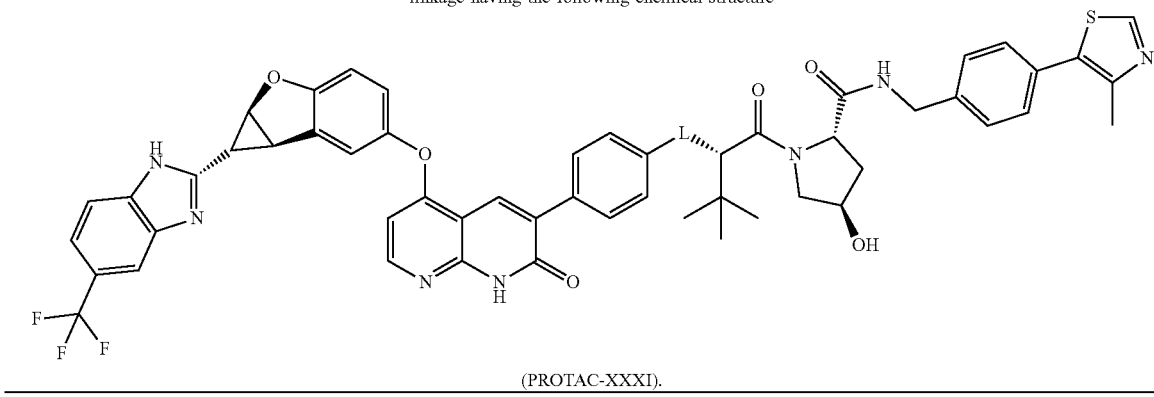
(PROTAC-XXXI).
| PROTAC-XXXI Compound | L | Mass | $DC_{50}$ (μM) | Dmax (%) |
|---|---|---|---|---|
| PROTAC-XXXI-41 | | 1166 | | |
| PROTAC-XXXI-42 | | 1166 | | |
| PROTAC-XXXI-43 | | 1166 | | |
| PROTAC-XXXI-44 | | 1150 | | |
| PROTAC-XXXI-45 | | 1164 | | |
| PROTAC-XXXI-46 | | 1178 | | |
| PROTAC-XXXI-47 | | 1192 | | |
| PROTAC-XXXI-48 | | 1194 | | |
| PROTAC-XXXI-49 | | 1208 | | |

TABLE 31-continued
Protacs composed of a RAF ligand and a VHL ligand with left-side linkage having the following chemical structure
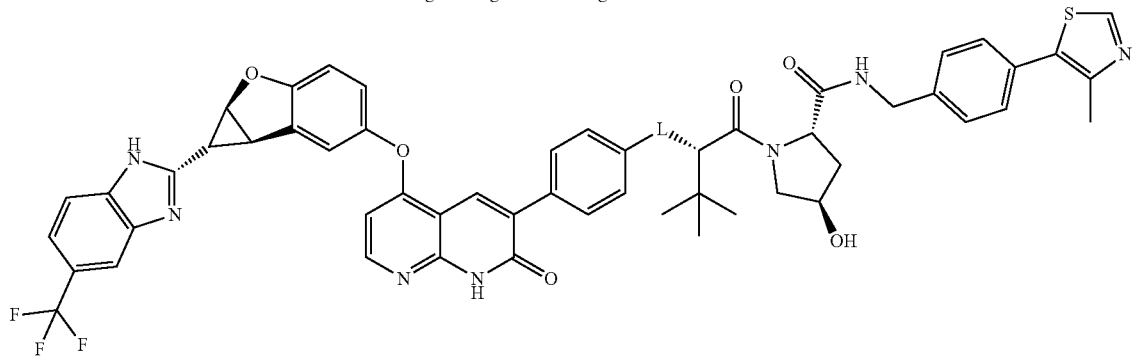
(PROTAC-XXXI).
| PROTAC-XXXI Compound | L | Mass | DC$_{50}$ (μM) | Dmax (%) |
|---|---|---|---|---|
| PROTAC-XXXI-50 | | 1222 | | |
| PROTAC-XXXI-51 | | 1236 | | |
| PROTAC-XXXI-52 | | 1238 | | |
| PROTAC-XXXI-53 | | 1150 | | |
| PROTAC-XXXI-54 | | 1149 | | |
| PROTAC-XXXI-55 | | 1164 | | |
| PROTAC-XXXI-56 | | 1178 | | |

TABLE 31-continued
Protacs composed of a RAF ligand and a VHL ligand with left-side linkage having the following chemical structure
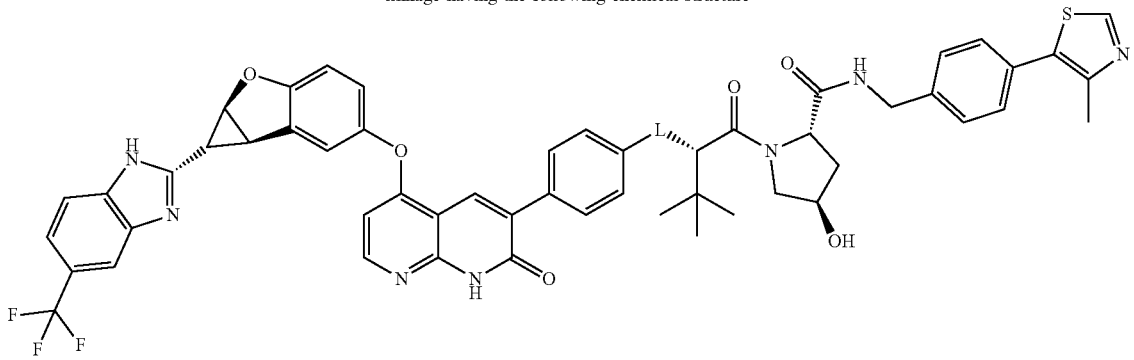
(PROTAC-XXXI).
| PROTAC-XXXI Compound | L | Mass | DC$_{50}$ (μM) | Dmax (%) |
|---|---|---|---|---|
| PROTAC-XXXI-57 | | 1192 | | |
| PROTAC-XXXI-58 | | 1194 | | |
| PROTAC-XXXI-59 | | 1193 | | |
| PROTAC-XXXI-60 | | 1218 | | |
| PROTAC-XXXI-61 | | 1217 | | |
| PROTAC-XXXI-62 | | 1217 | | |
| PROTAC-XXXI-63 | | 1203 | | |
| PROTAC-XXXI-64 | | 1189 | | |

TABLE 31-continued
Protacs composed of a RAF ligand and a VHL ligand with left-side linkage having the following chemical structure
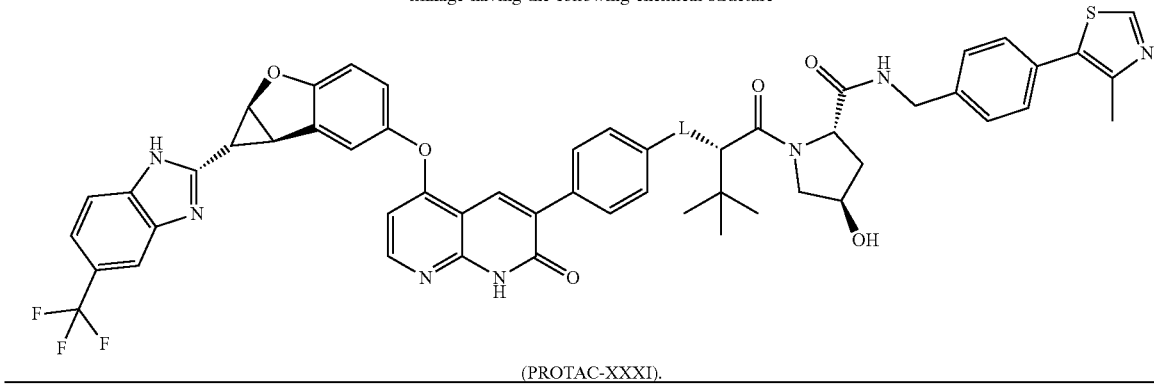
(PROTAC-XXXI).
| PROTAC-XXXI Compound | L | Mass | DC$_{50}$ (μM) | Dmax (%) |
|---|---|---|---|---|
| PROTAC-XXXI-65 | | 1062 | | |
| PROTAC-XXXI-66 | | 1076 | | |
| PROTAC-XXXI-67 | | 1090 | | |
| PROTAC-XXXI-68 | | 1104 | | |
| PROTAC-XXXI-69 | | 1106 | | |
| PROTAC-XXXI-70 | | 1118 | | |
| PROTAC-XXXI-71 | | 1120 | | |
| PROTAC-XXXI-72 | | 1120 | | |
| PROTAC-XXXI-73 | | 1134 | | |
| PROTAC-XXXI-74 | | 1134 | | |
| PROTAC-XXXI-75 | | 1134 | | |

TABLE 31-continued
Protacs composed of a RAF ligand and a VHL ligand with left-side
linkage having the following chemical structure
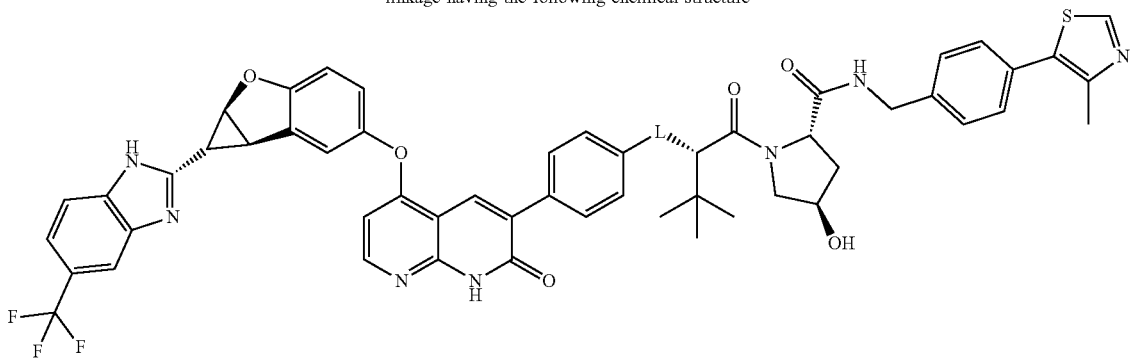
(PROTAC-XXXI).
| PROTAC-XXXI Compound | L | Mass | DC$_{50}$ (μM) | Dmax (%) |
|---|---|---|---|---|
| PROTAC-XXXI-76 | | 1148 | | |
| PROTAC-XXXI-77 | | 1148 | | |
| PROTAC-XXXI-78 | | 1148 | | |
| PROTAC-XXXI-79 | | 1148 | | |
| PROTAC-XXXI-80 | | 1150 | | |
| PROTAC-XXXI-81 | | 1162 | | |
| PROTAC-XXXI-82 | | 1162 | | |
| PROTAC-XXXI-83 | | 1162 | | |
| PROTAC-XXXI-84 | | 1162 | | |
| PROTAC-XXXI-85 | | 1162 | | |

TABLE 31-continued
Protacs composed of a RAF ligand and a VHL ligand with left-side linkage having the following chemical structure
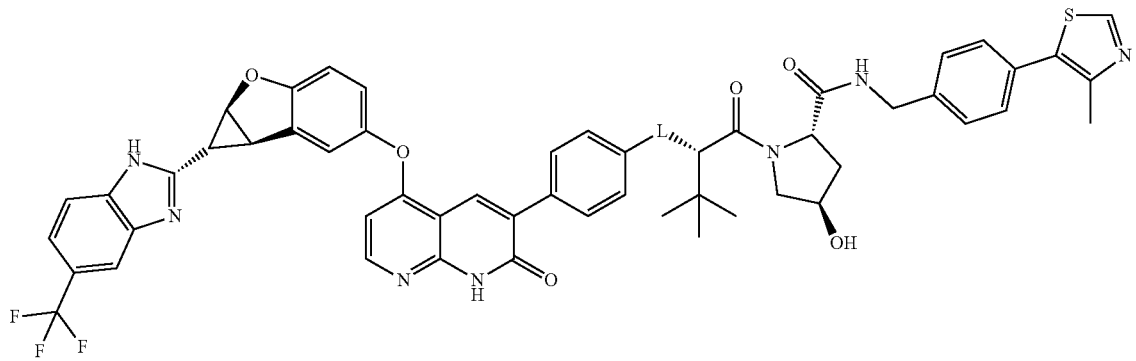
(PROTAC-XXXI).
| PROTAC-XXXI Compound | L | Mass | DC$_{50}$ (μM) | Dmax (%) |
|---|---|---|---|---|
| PROTAC-XXXI-86 |  | 1164 |  |  |
| PROTAC-XXXI-87 |  | 1164 |  |  |
| PROTAC-XXXI-88 |  | 1164 |  |  |
| PROTAC-XXXI-89 |  | 1116 |  |  |
| PROTAC-XXXI-90 |  | 1130 |  |  |
| PROTAC-XXXI-91 |  | 1144 |  |  |
| PROTAC-XXXI-92 |  | 1158 |  |  |
| PROTAC-XXXI-93 |  | 1172 |  |  |

TABLE 31-continued
Protacs composed of a RAF ligand and a VHL ligand with left-side linkage having the following chemical structure
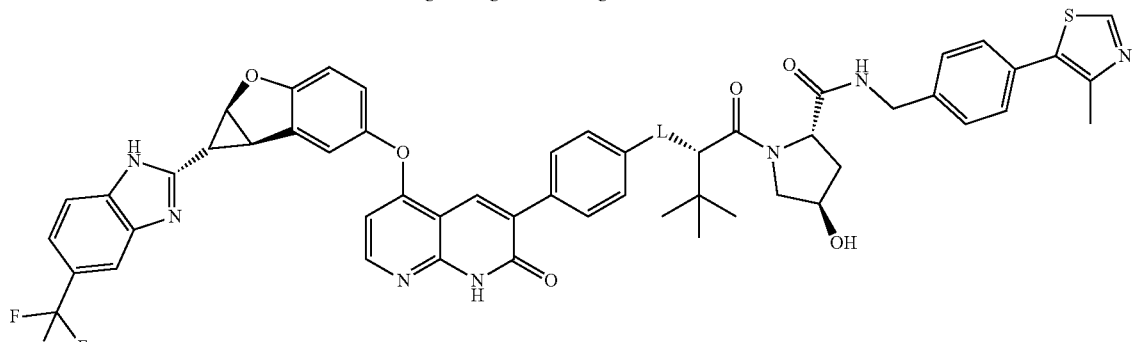
(PROTAC-XXXI).
| PROTAC-XXXI Compound | L | Mass | DC$_{50}$ (μM) | Dmax (%) |
|---|---|---|---|---|
| PROTAC-XXXI-94 | | 1174 | | |
| PROTAC-XXXI-95 | | 1188 | | |
| PROTAC-XXXI-96 | | 1188 | | |
| PROTAC-XXXI-97 | | 1186 | | |
| PROTAC-XXXI-98 | | 1200 | | |
| PROTAC-XXXI-99 | | 1202 | | |
| PROTAC-XXXI-100 | | 1202 | | |
| PROTAC-XXXI-101 | | 1202 | | |

TABLE 32

Protacs composed of a RAF ligand and a VHL ligand with right-side linkage having the following chemical structure

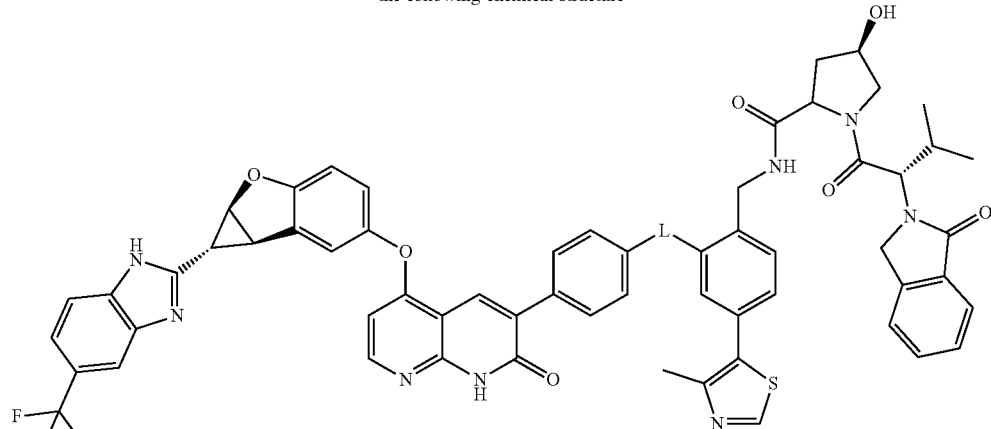

(PROTAC-XXXII).

| PROTAC-XXXII Compound | L | Mass | DC$_{50}$ (μM) | Dmax (%) |
|---|---|---|---|---|
| PROTAC-XXXII-1 | ----O~~O---- | 1142 | | |
| PROTAC-XXXII-2 | ----O~O~O-- | 1186 | | |
| PROTAC-XXXII-3 | ----O~O~O~O---- | 1230 | | |
| PROTAC-XXXII-4 | ----O~O~O~O~O-- | 1274 | | |
| PROTAC-XXXII-5 | ----O~O~O~O~O~O---- | 1318 | | |
| PROTAC-XXXII-6 | ----O~O~O~O~O~O~O-- | 1362 | | |
| PROTAC-XXXII-7 | ----O-- | 1126 | | |
| PROTAC-XXXII-8 | --O-- | 1112 | | |
| PROTAC-XXXII-9 | --O---- | 1126 | | |
| PROTAC-XXXII-10 | ----O---- | 1112 | | |
| PROTAC-XXXII-11 | ----O~O-- | 1156 | | |
| PROTAC-XXXII-12 | ----O~O---- | 1170 | | |
| PROTAC-XXXII-13 | ----O~O~O---- | 1200 | | |
| PROTAC-XXXII-14 | ----O~O~O---- | 1200 | | |

TABLE 32-continued

Protacs composed of a RAF ligand and a VHL ligand with right-side linkage having the following chemical structure

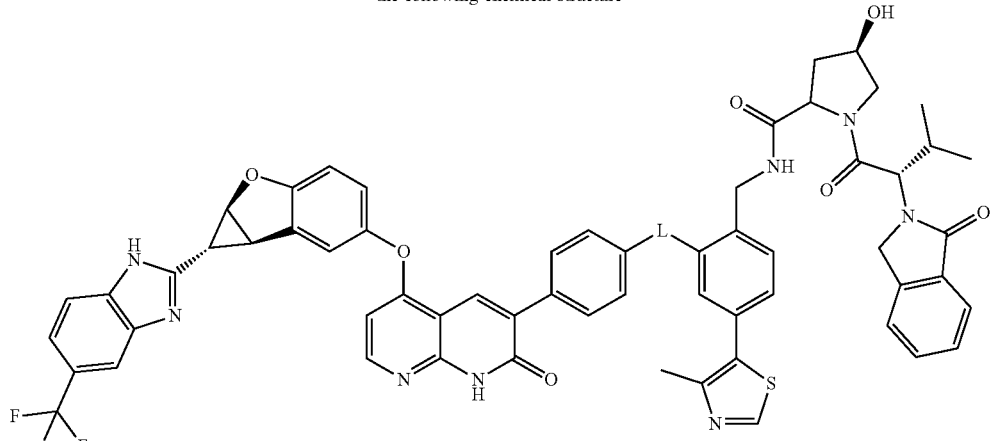

(PROTAC-XXXII).

| PROTAC-XXXII Compound | L | Mass | DC$_{50}$ (μM) | Dmax (%) |
|---|---|---|---|---|
| PROTAC-XXXII-15 | ----O~~~O~~~~ | 1198 | | |
| PROTAC-XXXII-16 | ----O~~O~~~O~~ | 1214 | | |
| PROTAC-XXXII-17 | ----O~~~O~~O~~ | 1214 | | |
| PROTAC-XXXII-18 | ----O~~~O~~O~~ | 1214 | | |
| PROTAC-XXXII-19 | ----O~~O~~~O~~~O~~ | 1244 | | |
| PROTAC-XXXII-20 | ----O~~O~~O~~~O~~ | 1244 | | |
| PROTAC-XXXII-21 | ----O~~~O~~O~~O~~ | 1244 | | |
| PROTAC-XXXII-22 | ----O~~~O~~~O~~~O~~ | 1242 | | |
| PROTAC-XXXII-23 | ----O~~~O~~~O~~~O~~ | 1242 | | |
| PROTAC-XXXII-24 | ----O~~~O~~~O~~~O~~ | 1242 | | |
| PROTAC-XXXII-25 | ----O~~~O~~~O~~O~~ | 1242 | | |
| PROTAC-XXXII-26 | ----O~~O~~~~O~~~O~~ | 1242 | | |
| PROTAC-XXXII-27 | ----O~~O~~O~~~O~~O~~ | 1258 | | |
| PROTAC-XXXII-28 | ----O~~O~~O~~O~~O~~ | 1258 | | |

TABLE 32-continued
Protacs composed of a RAF ligand and a VHL ligand with right-side linkage having the following chemical structure
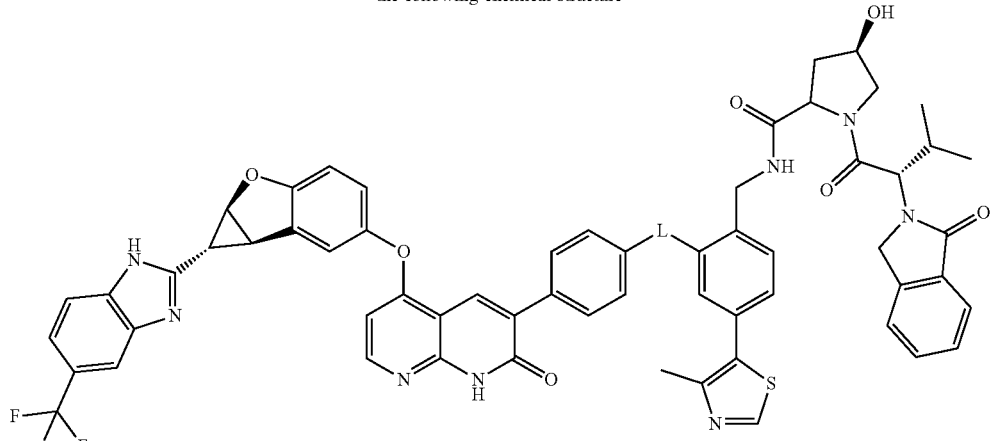
(PROTAC-XXXII).
| PROTAC-XXXII Compound | L | Mass | DC$_{50}$ (μM) | Dmax (%) |
|---|---|---|---|---|
| PROTAC-XXXII-29 | | 1258 | | |
| PROTAC-XXXII-30 | | 1258 | | |
| PROTAC-XXXII-31 | | 1258 | | |
| PROTAC-XXXII-32 | | 1256 | | |
| PROTAC-XXXII-33 | | 1256 | | |
| PROTAC-XXXII-34 | | 1256 | | |
| PROTAC-XXXII-35 | | 1256 | | |
| PROTAC-XXXII-36 | | 1256 | | |
| PROTAC-XXXII-37 | | 1256 | | |
| PROTAC-XXXII-38 | | 1166 | | |
| PROTAC-XXXII-39 | | 1210 | | |
| PROTAC-XXXII-40 | | 1210 | | |
| PROTAC-XXXII-41 | | 1224 | | |

TABLE 32-continued
Protacs composed of a RAF ligand and a VHL ligand with right-side linkage having the following chemical structure
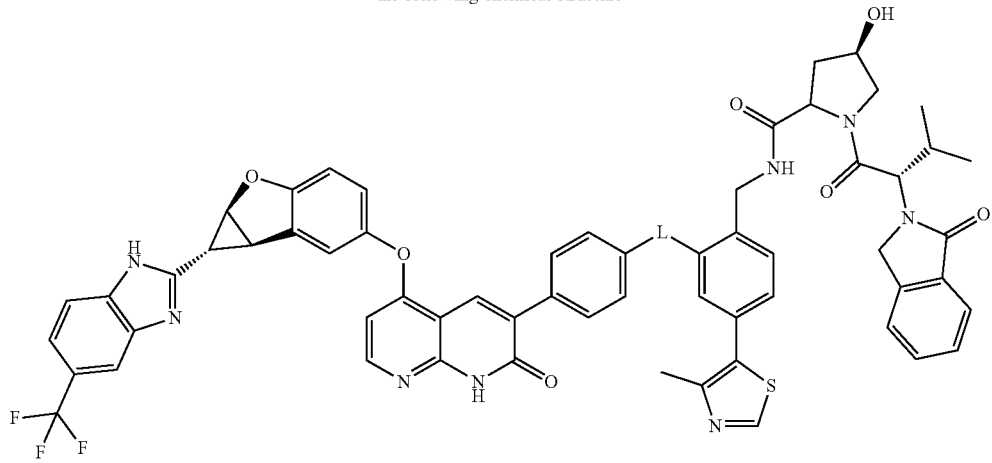
(PROTAC-XXXII).
| PROTAC-XXXII Compound | L | Mass | DC$_{50}$ (μM) | Dmax (%) |
|---|---|---|---|---|
| PROTAC-XXXII-42 | 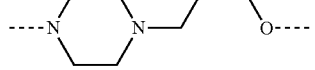 | 1224 | | |
| PROTAC-XXXII-43 |  | 1238 | | |
| PROTAC-XXXII-44 |  | 1238 | | |
| PROTAC-XXXII-45 | 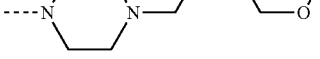 | 1254 | | |
| PROTAC-XXXII-46 | 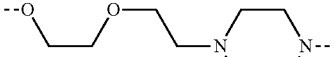 | 1254 | | |
| PROTAC-XXXII-47 | 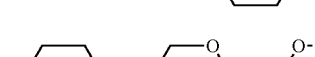 | 1278 | | |
| PROTAC-XXXII-48 | 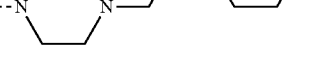 | 1254 | | |
| PROTAC-XXXII-49 | 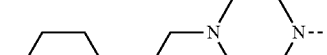 | 1268 | | |
| PROTAC-XXXII-50 |  | 1268 | | |

TABLE 32-continued
Protacs composed of a RAF ligand and a VHL ligand with right-side linkage having the following chemical structure
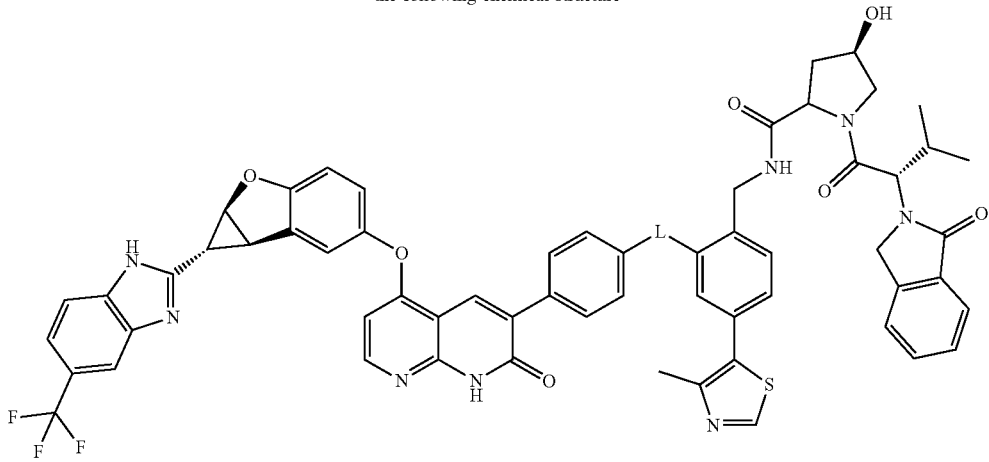
(PROTAC-XXXII).
| PROTAC-XXXII Compound | L | Mass | $DC_{50}$ (μM) | Dmax (%) |
|---|---|---|---|---|
| PROTAC-XXXII-51 | | 1266 | | |
| PROTAC-XXXII-52 | | 1268 | | |
| PROTAC-XXXII-53 | | 1268 | | |
| PROTAC-XXXII-54 | | 1266 | | |
| PROTAC-XXXII-55 | | 1292 | | |
| PROTAC-XXXII-56 | | 1268 | | |
| PROTAC-XXXII-57 | | 1268 | | |
| PROTAC-XXXII-58 | | 1282 | | |
| PROTAC-XXXII-59 | | 1282 | | |

TABLE 32-continued

Protacs composed of a RAF ligand and a VHL ligand with right-side linkage having
the following chemical structure

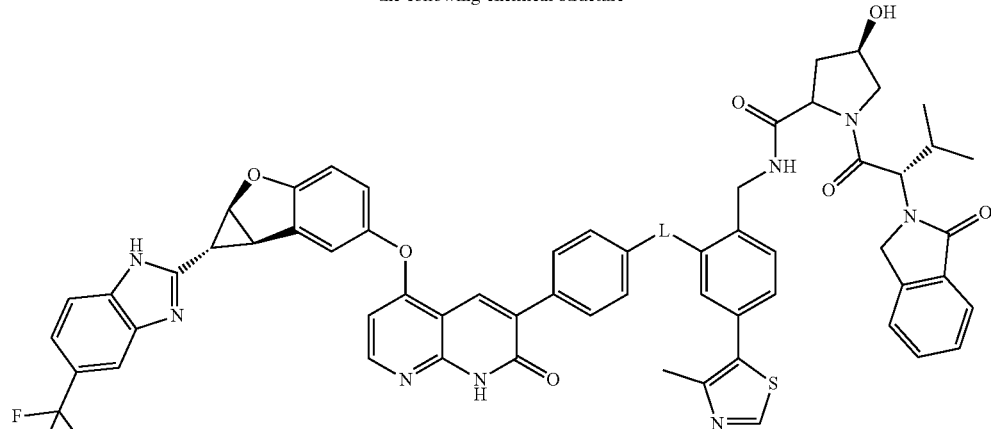

(PROTAC-XXXII).

| PROTAC-XXXII Compound | L | Mass | DC$_{50}$ (μM) | Dmax (%) |
|---|---|---|---|---|
| PROTAC-XXXII-60 | ----O~~~O~~~N(piperazine)N---- | 1282 | | |
| PROTAC-XXXII-61 | ----O~~~~~N(piperazine)N---- | 1280 | | |
| PROTAC-XXXII-62 | ----N(piperazine)N~~~O~~O---- | 1282 | | |
| PROTAC-XXXII-63 | ----N(piperazine)N~~~O~~O---- | 1282 | | |
| PROTAC-XXXII-64 | ----N(piperazine)N~~O~~~O---- | 1282 | | |
| PROTAC-XXXII-65 | ----N(piperazine)N~~~~~O---- | 1280 | | |
| PROTAC-XXXII-66 | ----N(piperazine)N~~N(piperazine)N---- | 1306 | | |
| PROTAC-XXXII-67 | ----O~~N(piperazine)N~~O---- | 1282 | | |
| PROTAC-XXXII-68 | ---O~~~N(piperazine)N~~O--- | 1282 | | |
| PROTAC-XXXII-69 | ---O~~N(piperazine)N~~~O--- | 1282 | | |

TABLE 32-continued

Protacs composed of a RAF ligand and a VHL ligand with right-side linkage having the following chemical structure

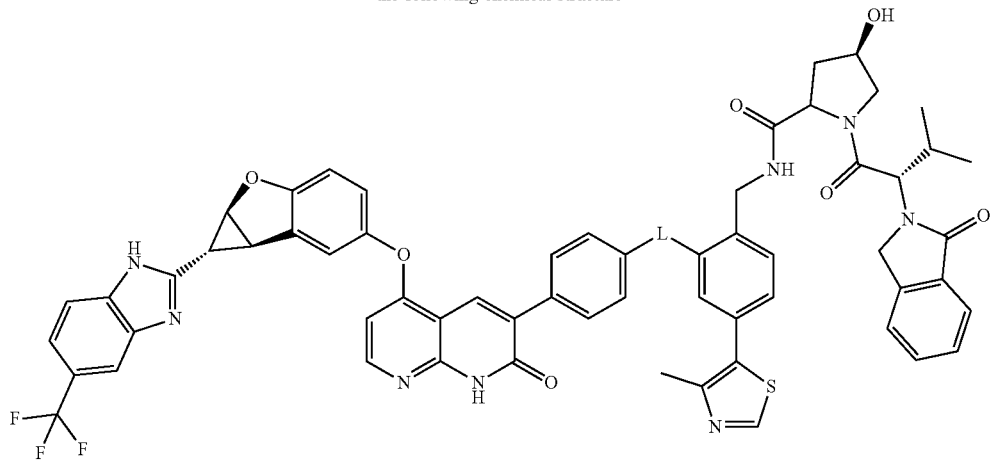

(PROTAC-XXXII).

| PROTAC-XXXII Compound | L | Mass | DC$_{50}$ (μM) | Dmax (%) |
|---|---|---|---|---|
| PROTAC-XXXII-70 | ----O↙ | 1098 | | |

TABLE 33

Protacs composed of a RAF ligand and a cereblon ligand with 5-position linkage having the following chemical structure

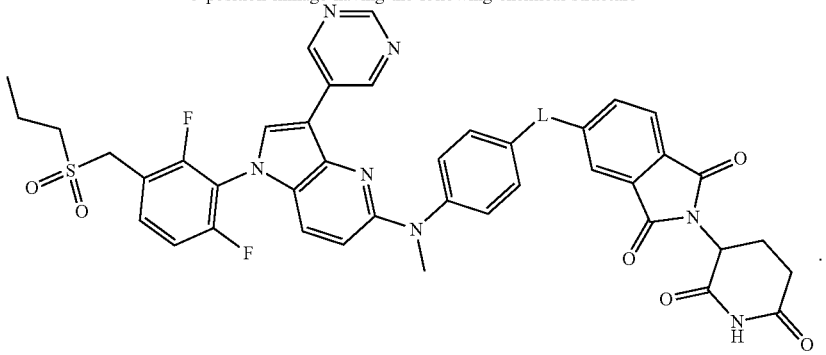

(PROTAC-XXXIII).

| PROTAC-XXXIII Compound | L | Mass | DC$_{50}$ (μM) | Dmax (%) |
|---|---|---|---|---|
| PROTAC-XXXIII-1 | ----O⌢O---- | 850 | | |
| PROTAC-XXXIII-2 | ----O⌢O⌢O⋰ | 894 | | |
| PROTAC-XXXIII-3 | ----O⌢O⌢O⌢O---- | 938 | | |
| PROTAC-XXXIII-4 | ----O⌢O⌢O⌢O⌢O⋰ | 982 | | |
| PROTAC-XXXIII-5 | ----O⌢O⌢O⌢O⌢O⌢O---- | 1026 | | |

TABLE 33-continued

Protacs composed of a RAF ligand and a cereblon ligand with 5-position linkage having the following chemical structure

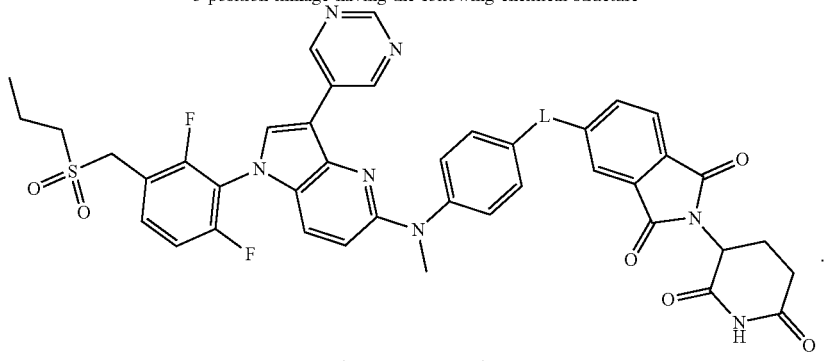

(PROTAC-XXXIII).

| PROTAC-XXXIII Compound | L | Mass | DC$_{50}$ (μM) | Dmax (%) |
|---|---|---|---|---|
| PROTAC-XXXIII-6 | 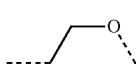 | 1070 | | |
| PROTAC-XXXIII-7 |  | 834 | | |
| PROTAC-XXXIII-8 | 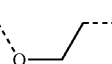 | 820 | | |
| PROTAC-XXXIII-9 | 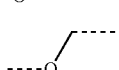 | 834 | | |
| PROTAC-XXXIII-10 | 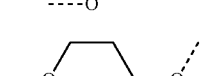 | 820 | | |
| PROTAC-XXXIII-11 |  | 864 | | |
| PROTAC-XXXIII-12 |  | 878 | | |
| PROTAC-XXXIII-13 | 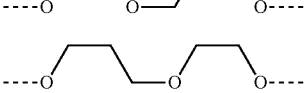 | 908 | | |
| PROTAC-XXXIII-14 |  | 908 | | |
| PROTAC-XXXIII-15 | 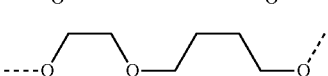 | 906 | | |
| PROTAC-XXXIII-16 | 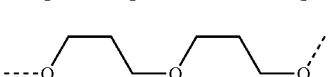 | 922 | | |
| PROTAC-XXXIII-17 | 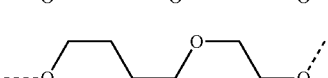 | 922 | | |
| PROTAC-XXXIII-18 | 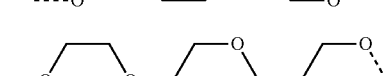 | 922 | | |
| PROTAC-XXXIII-19 | 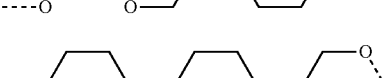 | 952 | | |
| PROTAC-XXXIII-20 | 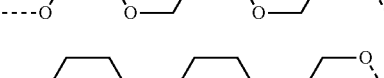 | 952 | | |
| PROTAC-XXXIII-21 | | 952 | | |

TABLE 33-continued

Protacs composed of a RAF ligand and a cereblon ligand with
5-position linkage having the following chemical structure

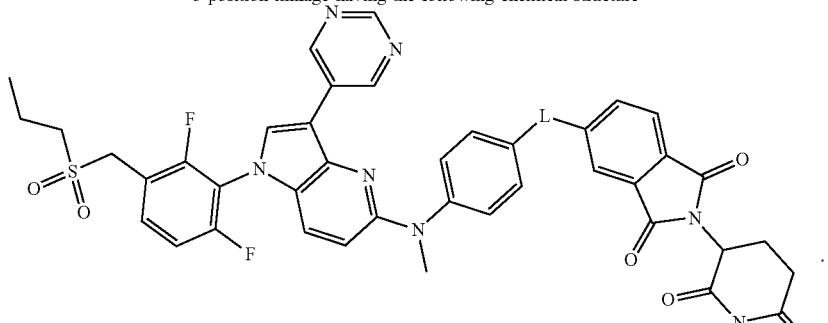

(PROTAC-XXXIII).

| PROTAC-XXXIII Compound | L | Mass | DC$_{50}$ (μM) | Dmax (%) |
|---|---|---|---|---|
| PROTAC-XXXIII-22 | | 950 | | |
| PROTAC-XXXIII-23 | | 950 | | |
| PROTAC-XXXIII-24 | | 950 | | |
| PROTAC-XXXIII-25 | | 950 | | |
| PROTAC-XXXIII-26 | | 950 | | |
| PROTAC-XXXIII-27 | | 966 | | |
| PROTAC-XXXIII-28 | | 966 | | |
| PROTAC-XXXIII-29 | | 966 | | |
| PROTAC-XXXIII-30 | | 966 | | |
| PROTAC-XXXIII-31 | | 966 | | |
| PROTAC-XXXIII-32 | | 964 | | |
| PROTAC-XXXIII-33 | | 964 | | |
| PROTAC-XXXIII-34 | | 964 | | |
| PROTAC-XXXIII-35 | | 964 | | |
| PROTAC-XXXIII-36 | | 964 | | |

TABLE 33-continued

Protacs composed of a RAF ligand and a cereblon ligand with
5-position linkage having the following chemical structure

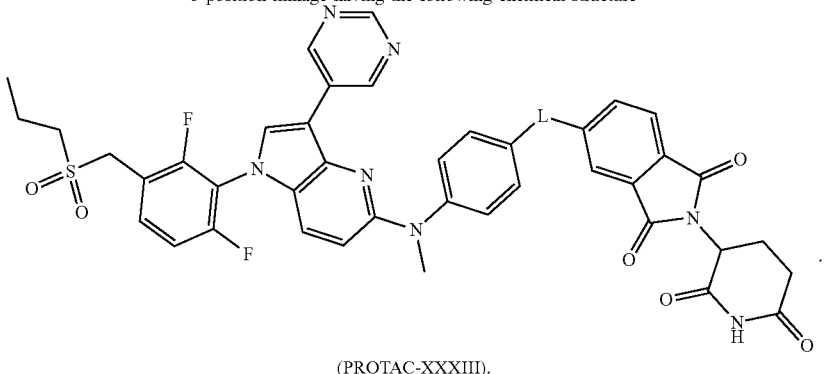

(PROTAC-XXXIII).

| PROTAC-XXXIII Compound | L | Mass | DC$_{50}$ (µM) | Dmax (%) |
|---|---|---|---|---|
| PROTAC-XXXIII-37 | ----O~~O~~~~O---- | 964 | | |
| PROTAC-XXXIII-38 | ----N(piperazine)N---- | 874 | | |
| PROTAC-XXXIII-39 | O~~N(piperazine)N---- | 918 | | |
| PROTAC-XXXIII-40 | ----N(piperazine)N~~O | 918 | | |
| PROTAC-XXXIII-41 | ----O~~N(piperazine)N---- | 932 | | |
| PROTAC-XXXIII-42 | ----N(piperazine)N~~O---- | 932 | | |
| PROTAC-XXXIII-43 | O~~~N(piperazine)N---- | 946 | | |
| PROTAC-XXXIII-44 | ----N(piperazine)N~~~O | 946 | | |
| PROTAC-XXXIII-45 | ----O~~O~~N(piperazine)N---- | 962 | | |
| PROTAC-XXXIII-46 | ----N(piperazine)N~~O~~O---- | 962 | | |
| PROTAC-XXXIII-47 | ----N(piperazine)N~~N(piperazine)N---- | 986 | | |

TABLE 33-continued
Protacs composed of a RAF ligand and a cereblon ligand with
5-position linkage having the following chemical structure
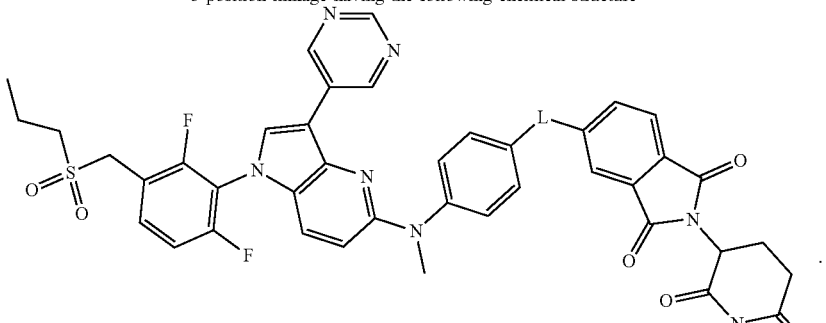
(PROTAC-XXXIII).
| PROTAC-XXXIII Compound | L | Mass | DC$_{50}$ (μM) | Dmax (%) |
|---|---|---|---|---|
| PROTAC-XXXIII-48 | | 962 | | |
| PROTAC-XXXIII-49 | | 976 | | |
| PROTAC-XXXIII-50 | | 976 | | |
| PROTAC-XXXIII-51 | | 974 | | |
| PROTAC-XXXIII-52 | | 976 | | |
| PROTAC-XXXIII-53 | | 976 | | |
| PROTAC-XXXIII-54 | | 974 | | |
| PROTAC-XXXIII-55 | | 1000 | | |
| PROTAC-XXXIII-56 | | 976 | | |
| PROTAC-XXXIII-57 | | 976 | | |

TABLE 33-continued

Protacs composed of a RAF ligand and a cereblon ligand with
5-position linkage having the following chemical structure

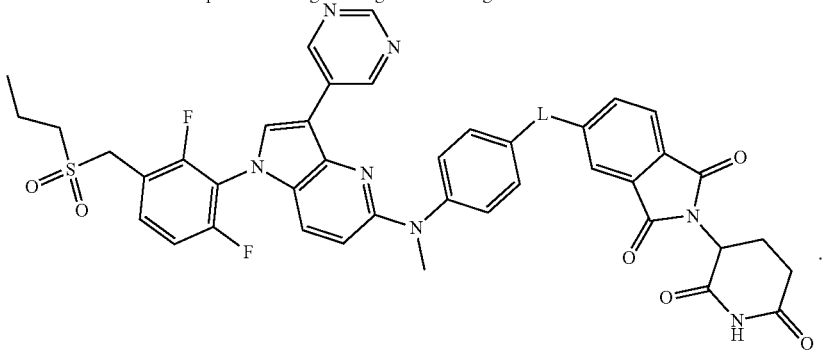

(PROTAC-XXXIII).

| PROTAC-XXXIII Compound | L | Mass | $DC_{50}$ ($\mu M$) | Dmax (%) |
|---|---|---|---|---|
| PROTAC-XXXIII-58 | ----O~~~O~~~N(piperazine)N---- | 990 | | |
| PROTAC-XXXIII-59 | ----O~~~O~~~N(piperazine)N---- | 990 | | |
| PROTAC-XXXIII-60 | ----O~~O~~~N(piperazine)N---- | 990 | | |
| PROTAC-XXXIII-61 | ----O~~~~~N(piperazine)N---- | 988 | | |
| PROTAC-XXXIII-62 | ----N(piperazine)N~~~O~~O---- | 990 | | |
| PROTAC-XXXIII-63 | ----N(piperazine)N~~~O~~O---- | 990 | | |
| PROTAC-XXXIII-64 | ----N(piperazine)N~~O~~~O---- | 990 | | |
| PROTAC-XXXIII-65 | ----N(piperazine)N~~~~O---- | 988 | | |
| PROTAC-XXXIII-66 | ----N(piperazine)N~~~N(piperazine)N---- | 1014 | | |
| PROTAC-XXXIII-67 | ----O~~N(piperazine)N~~O---- | 990 | | |
| PROTAC-XXXIII-68 | ····O~~~~N(piperazine)N~~O···· | 990 | | |

TABLE 33-continued

Protacs composed of a RAF ligand and a cereblon ligand with 5-position linkage having the following chemical structure

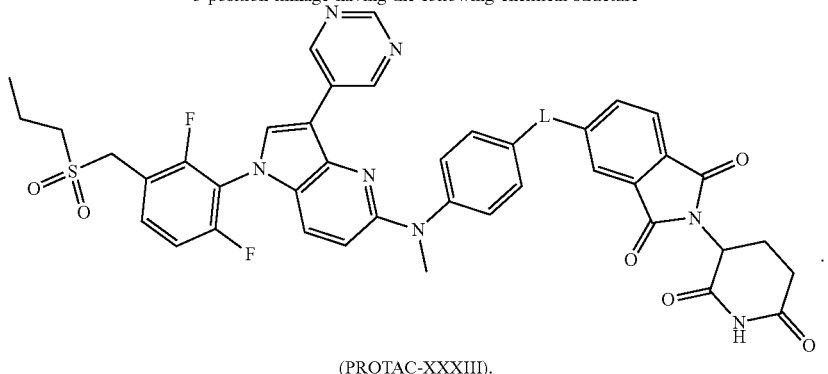

(PROTAC-XXXIII).

| PROTAC-XXXIII Compound | L | Mass | DC$_{50}$ (μM) | Dmax (%) |
|---|---|---|---|---|
| PROTAC-XXXIII-69 | | 990 | | |
| PROTAC-XXXIII-70 | | 806 | | |

TABLE 34

Protacs composed of a RAF ligand and a cereblon ligand with 5-position linkage having the following chemical structure

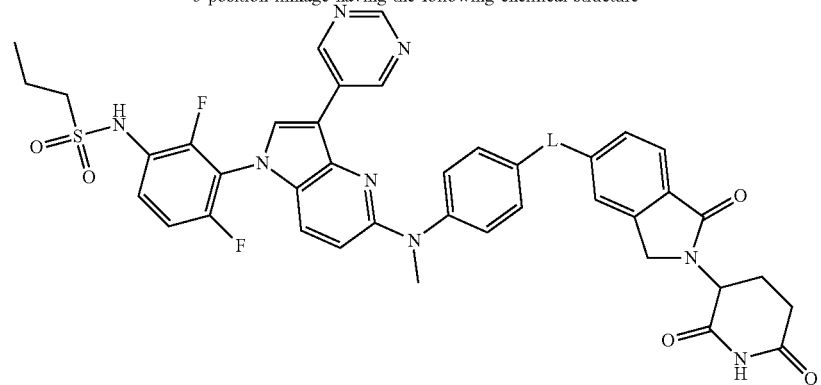

(PROTAC-XXXIV).

| PROTAC-XXXIV Compound | L | Mass | DC$_{50}$ (μM) | Dmax (%) |
|---|---|---|---|---|
| PROTAC-XXXIV-1 | | 836 | | |
| PROTAC-XXXIV-2 | | 880 | | |
| PROTAC-XXXIV-3 | | 924 | | |
| PROTAC-XXXIV-4 | | 968 | | |
| PROTAC-XXXIV-5 | | 1012 | | |

TABLE 34-continued

Protacs composed of a RAF ligand and a cereblon ligand with
5-position linkage having the following chemical structure

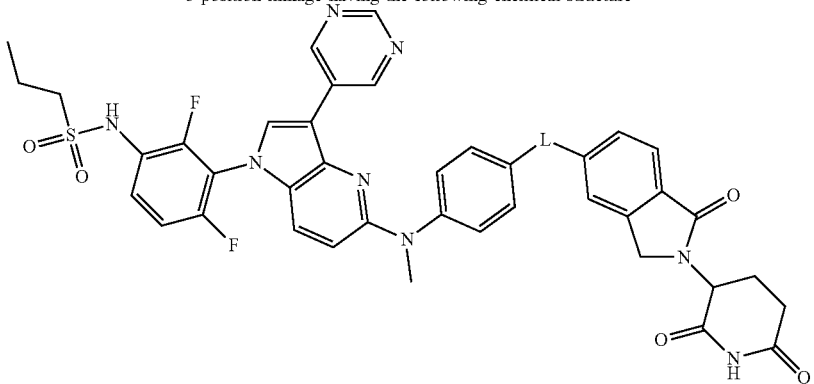

(PROTAC-XXXIV).

| PROTAC-XXXIV Compound | L | Mass | DC$_{50}$ (μM) | Dmax (%) |
|---|---|---|---|---|
| PROTAC-XXXIV-6 | | 1056 | | |
| PROTAC-XXXIV-7 | | 820 | | |
| PROTAC-XXXIV-8 | | 806 | | |
| PROTAC-XXXIV-9 | | 820 | | |
| PROTAC-XXXIV-10 | | 806 | | |
| PROTAC-XXXIV-11 | | 850 | | |
| PROTAC-XXXIV-12 | | 864 | | |
| PROTAC-XXXIV-13 | | 894 | | |
| PROTAC-XXXIV-14 | | 894 | | |
| PROTAC-XXXIV-15 | | 892 | | |
| PROTAC-XXXIV-16 | | 908 | | |
| PROTAC-XXXIV-17 | | 908 | | |
| PROTAC-XXXIV-18 | | 908 | | |
| PROTAC-XXXIV-19 | | 938 | | |
| PROTAC-XXXIV-20 | | 938 | | |

TABLE 34-continued

Protacs composed of a RAF ligand and a cereblon ligand with 5-position linkage having the following chemical structure

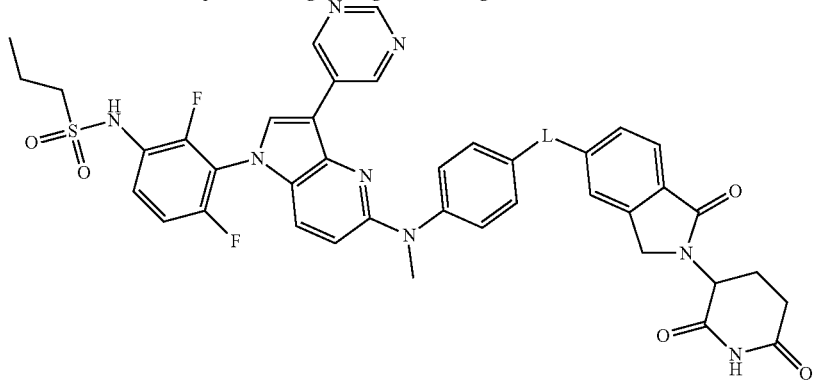

(PROTAC-XXXIV).

| PROTAC-XXXIV Compound | L | Mass | DC$_{50}$ (μM) | Dmax (%) |
|---|---|---|---|---|
| PROTAC-XXXIV-21 | ----O~O~O~O~ | 938 | | |
| PROTAC-XXXIV-22 | ----O~O~O~ | 936 | | |
| PROTAC-XXXIV-23 | ----O~O~O~ | 936 | | |
| PROTAC-XXXIV-24 | ----O~O~O~ | 936 | | |
| PROTAC-XXXIV-25 | ----O~O~O~ | 936 | | |
| PROTAC-XXXIV-26 | ----O~O~O~ | 936 | | |
| PROTAC-XXXIV-27 | ----O~O~O~O---- | 952 | | |
| PROTAC-XXXIV-28 | ----O~O~O~O---- | 952 | | |
| PROTAC-XXXIV-29 | ----O~O~O~O---- | 952 | | |
| PROTAC-XXXIV-30 | ----O~O~O~O---- | 952 | | |
| PROTAC-XXXIV-31 | ----O~O~O~O---- | 952 | | |
| PROTAC-XXXIV-32 | ----O~O~O~O---- | 950 | | |
| PROTAC-XXXIV-33 | ----O~O~O~O---- | 950 | | |
| PROTAC-XXXIV-34 | ----O~O~O~O---- | 950 | | |
| PROTAC-XXXIV-35 | ----O~O~O~O---- | 950 | | |

TABLE 34-continued

Protacs composed of a RAF ligand and a cereblon ligand with
5-position linkage having the following chemical structure

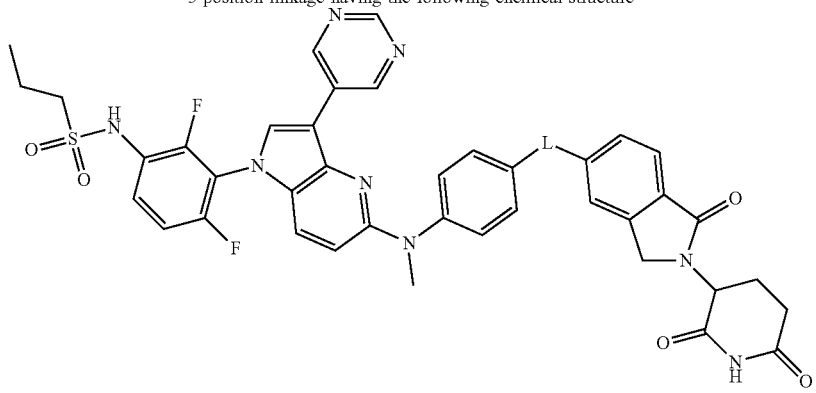

(PROTAC-XXXIV).

| PROTAC-XXXIV Compound | L | Mass | DC$_{50}$ (μM) | Dmax (%) |
|---|---|---|---|---|
| PROTAC-XXXIV-36 | ----O~~O~~O---- | 950 | | |
| PROTAC-XXXIV-37 | ----O~O~~~O---- | 950 | | |
| PROTAC-XXXIV-38 | ----N(piperazine)N---- | 860 | | |
| PROTAC-XXXIV-39 | O~N(piperazine)N---- | 904 | | |
| PROTAC-XXXIV-40 | ----N(piperazine)N~O | 904 | | |
| PROTAC-XXXIV-41 | ----O~N(piperazine)N---- | 918 | | |
| PROTAC-XXXIV-42 | ----N(piperazine)N~O---- | 918 | | |
| PROTAC-XXXIV-43 | O~~N(piperazine)N---- | 932 | | |
| PROTAC-XXXIV-44 | ----N(piperazine)N~~O | 932 | | |
| PROTAC-XXXIV-45 | ----O~O~N(piperazine)N---- | 948 | | |
| PROTAC-XXXIV-46 | ----N(piperazine)N~O~O---- | 948 | | |

TABLE 34-continued

Protacs composed of a RAF ligand and a cereblon ligand with 5-position linkage having the following chemical structure

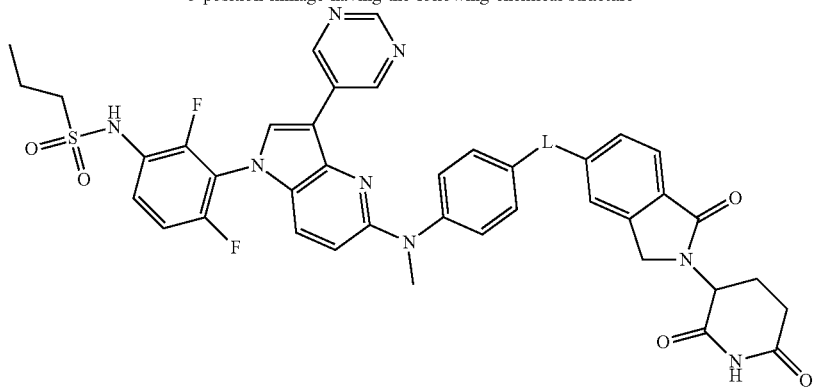

(PROTAC-XXXIV).

| PROTAC-XXXIV Compound | L | Mass | $DC_{50}$ (μM) | Dmax (%) |
|---|---|---|---|---|
| PROTAC-XXXIV-47 | (piperazine-CH₂CH₂-piperazine) | 972 | | |
| PROTAC-XXXIV-48 | (O-CH₂CH₂-piperazine-CH₂CH₂-O) | 948 | | |
| PROTAC-XXXIV-49 | (O-CH₂CH₂-O-CH₂CH₂-piperazine) | 962 | | |
| PROTAC-XXXIV-50 | (O-CH₂CH₂-O-CH₂CH₂-piperazine) | 962 | | |
| PROTAC-XXXIV-51 | (O-(CH₂)₄-piperazine) | 960 | | |
| PROTAC-XXXIV-52 | (piperazine-CH₂CH₂-O-CH₂CH₂-O) | 962 | | |
| PROTAC-XXXIV-53 | (piperazine-CH₂CH₂-O-CH₂CH₂-O) | 962 | | |
| PROTAC-XXXIV-54 | (piperazine-(CH₂)₄-O) | 960 | | |
| PROTAC-XXXIV-55 | (piperazine-CH₂CH₂-piperazine-CH₃) | 986 | | |

TABLE 34-continued

Protacs composed of a RAF ligand and a cereblon ligand with 5-position linkage having the following chemical structure

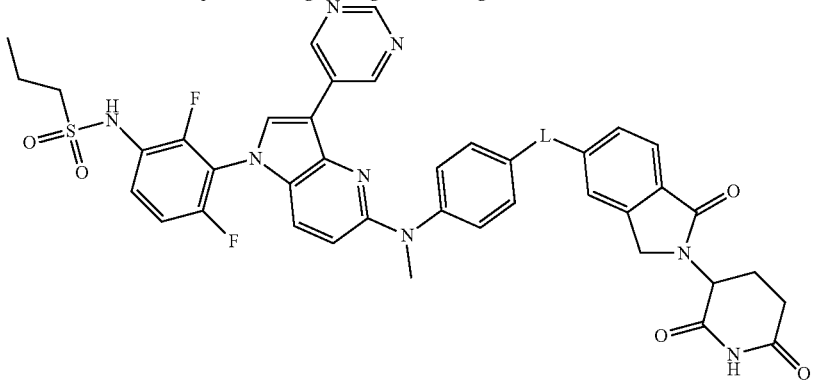

(PROTAC-XXXIV).

| PROTAC-XXXIV Compound | L | Mass | DC$_{50}$ (μM) | Dmax (%) |
|---|---|---|---|---|
| PROTAC-XXXIV-56 | ----O~~~N(piperazine)N~~~O---- | 962 | | |
| PROTAC-XXXIV-57 | O~~~N(piperazine)N~~~O---- | 962 | | |
| PROTAC-XXXIV-58 | ----O~~~O~~~N(piperazine)N---- | 976 | | |
| PROTAC-XXXIV-59 | ----O~~~O~~~N(piperazine)N---- | 976 | | |
| PROTAC-XXXIV-60 | ----O~~~O~~~N(piperazine)N---- | 976 | | |
| PROTAC-XXXIV-61 | ----O~~~~N(piperazine)N---- | 974 | | |
| PROTAC-XXXIV-62 | ----N(piperazine)N~~~O~~~O---- | 976 | | |
| PROTAC-XXXIV-63 | ----N(piperazine)N~~~O~~~O---- | 976 | | |
| PROTAC-XXXIV-64 | ----N(piperazine)N~~~O~~~O---- | 976 | | |
| PROTAC-XXXIV-65 | ----N(piperazine)N~~~~O---- | 974 | | |
| PROTAC-XXXIV-66 | ----N(piperazine)N~~~N(piperazine)N---- | 1000 | | |

TABLE 34-continued

Protacs composed of a RAF ligand and a cereblon ligand with 5-position linkage having the following chemical structure

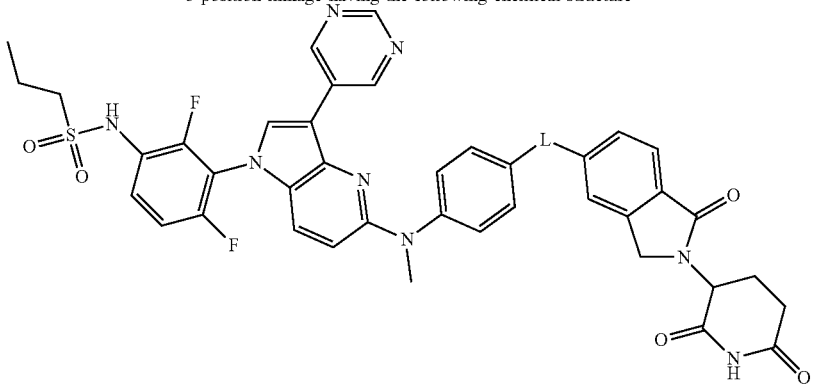

(PROTAC-XXXIV).

| PROTAC-XXXIV Compound | L | Mass | DC$_{50}$ (μM) | Dmax (%) |
|---|---|---|---|---|
| PROTAC-XXXIV-67 | ----O~~~N(piperazine)N~~~O---- | 976 | | |
| PROTAC-XXXIV-68 | ----O~~~~N(piperazine)N~~O---- | 976 | | |
| PROTAC-XXXIV-69 | ----O~~N(piperazine)N~~~~O---- | | | |
| PROTAC-XXXIV-70 | ----O---- | 792 | | |

TABLE 35

Protacs composed of a RAF ligand and a cereblon ligand with 6-position linkage having the following chemical structure

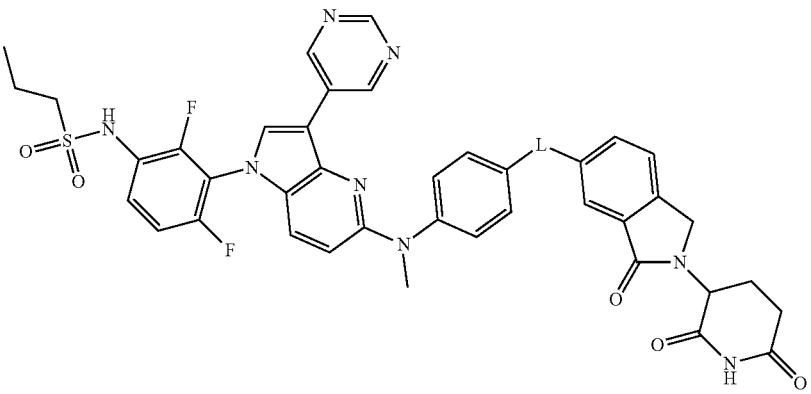

(PROTAC-XXXV)

| PROTAC-XXXV Compound | L | Mass | DC$_{50}$ (μM) | D$_{max}$ (%) |
|---|---|---|---|---|
| PROTAC-XXXV-1 | ----O~~O---- | 836 | | |

TABLE 35-continued

Protacs composed of a RAF ligand and a cereblon ligand with 6-position linkage having the following chemical structure

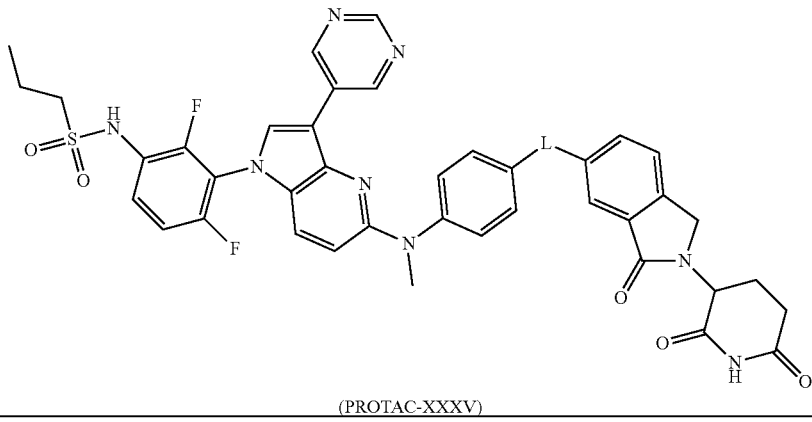

(PROTAC-XXXV)

| PROTAC-XXXV Compound | L | Mass | DC$_{50}$ (μM) | D$_{max}$ (%) |
|---|---|---|---|---|
| PROTAC-XXXV-2 | ----O~~O~~O~~ | 880 | | |
| PROTAC-XXXV-3 | ----O~~O~~O~~O---- | 924 | | |
| PROTAC-XXXV-4 | ----O~~O~~O~~O~~O~~ | 968 | | |
| PROTAC-XXXV-5 | ----O~~O~~O~~O~~O~~O---- | 1012 | | |
| PROTAC-XXXV-6 | ----O~~O~~O~~O~~O~~O~~O~~ | 1056 | | |
| PROTAC-XXXV-7 | ----~~O~~ | 820 | | |
| PROTAC-XXXV-8 | ~~O~~ | 806 | | |
| PROTAC-XXXV-9 | ~~O~~ | 820 | | |
| PROTAC-XXXV-10 | ----O~~ | 806 | | |
| PROTAC-XXXV-11 | ----O~~O~~ | 850 | | |
| PROTAC-XXXV-12 | ----O~~~O---- | 864 | | |
| PROTAC-XXXV-13 | ----O~~O~~O---- | 894 | | |
| PROTAC-XXXV-14 | ----O~~O~~O---- | 894 | | |
| PROTAC-XXXV-15 | ----O~~~~O---- | 892 | | |
| PROTAC-XXXV-16 | ----O~~O~~~O~~ | 908 | | |

TABLE 35-continued

Protacs composed of a RAF ligand and a cereblon ligand with 6-position linkage having the following chemical structure

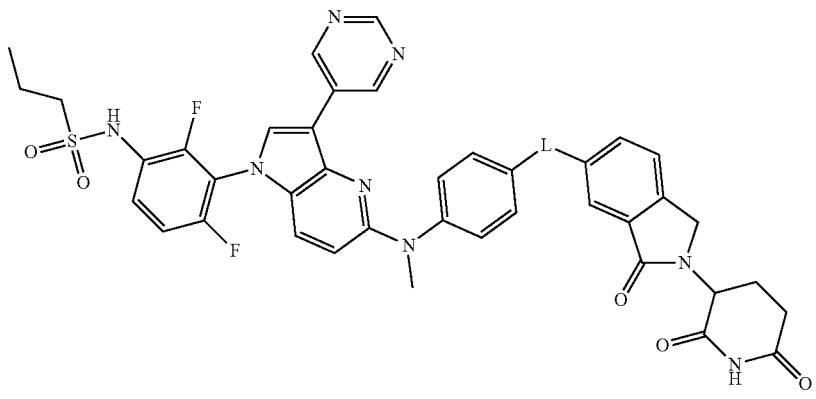

(PROTAC-XXXV)

| PROTAC-XXXV Compound | L | Mass | DC$_{50}$ (μM) | D$_{max}$ (%) |
|---|---|---|---|---|
| PROTAC-XXXV-17 | ----O\_/\O\_/\O\_/' | 908 | | |
| PROTAC-XXXV-18 | ----O\_/\_/O\_/\O\_/ | 908 | | |
| PROTAC-XXXV-19 | ----O\_/\O\_/\_/O\_/\O\_/ | 938 | | |
| PROTAC-XXXV-20 | ----O\_/\O\_/\_/O\_/\O\_/ | 938 | | |
| PROTAC-XXXV-21 | ----O\_/\O\_/\_/O\_/\O\_/ | 938 | | |
| PROTAC-XXXV-22 | ----O\_/\O\_/\_/\_/O\_/ | 936 | | |
| PROTAC-XXXV-23 | ----O\_/\_/O\_/\_/\_/O\_/ | 936 | | |
| PROTAC-XXXV-24 | ----O\_/\_/\_/O\_/\_/O\_/ | 936 | | |
| PROTAC-XXXV-25 | ----O\_/\_/\_/O\_/\_/O\_/ | 936 | | |
| PROTAC-XXXV-26 | ----O\_/O\_/\_/\_/\_/O\_/ | 936 | | |
| PROTAC-XXXV-27 | ----O\_/\O\_/\_/O\_/\_/O---- | 952 | | |
| PROTAC-XXXV-28 | ----O\_/\O\_/\_/O\_/\_/O---- | 952 | | |
| PROTAC-XXXV-29 | ----O\_/\O\_/\_/O\_/O---- | 952 | | |
| PROTAC-XXXV-30 | ----O\_/\_/O\_/\_/O\_/O---- | 952 | | |
| PROTAC-XXXV-31 | ----O\_/\_/O\_/\_/\_/O\_/O---- | 952 | | |

TABLE 35-continued

Protacs composed of a RAF ligand and a cereblon ligand with 6-position linkage having the following chemical structure

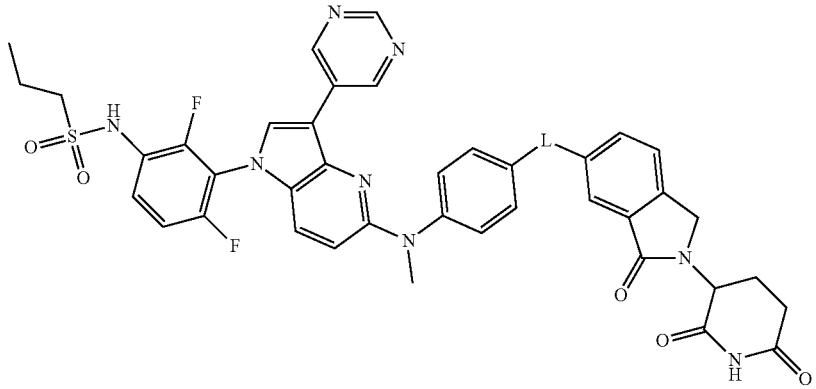

(PROTAC-XXXV)

| PROTAC-XXXV Compound | L | Mass | DC$_{50}$ (μM) | D$_{max}$ (%) |
|---|---|---|---|---|
| PROTAC-XXXV-32 | ----O~~~O~~~O---- | 950 | | |
| PROTAC-XXXV-33 | ----O~~~O~~~O---- | 950 | | |
| PROTAC-XXXV-34 | ----O~~~O~~~O---- | 950 | | |
| PROTAC-XXXV-35 | ----O~~~O~~~O---- | 950 | | |
| PROTAC-XXXV-36 | ----O~~~O~~~O---- | 950 | | |
| PROTAC-XXXV-37 | ----O~~~O~~~O---- | 950 | | |
| PROTAC-XXXV-38 | ----N(piperazine)N---- | 860 | | |
| PROTAC-XXXV-39 | O~piperazine~---- | 904 | | |
| PROTAC-XXXV-40 | ----N~piperazine~O | 904 | | |
| PROTAC-XXXV-41 | ----O~piperazine~---- | 918 | | |
| PROTAC-XXXV-42 | ----piperazine~O---- | 918 | | |
| PROTAC-XXXV-43 | O~piperazine~---- | 932 | | |

TABLE 35-continued
Protacs composed of a RAF ligand and a cereblon ligand with
6-position linkage having the following chemical structure
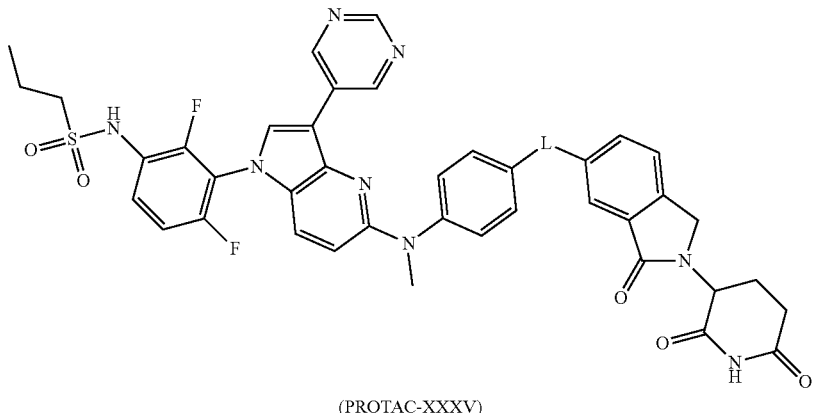
(PROTAC-XXXV)
| PROTAC-XXXV Compound | L | Mass | DC$_{50}$ (μM) | D$_{max}$ (%) |
|---|---|---|---|---|
| PROTAC-XXXV-44 |  | 932 | | |
| PROTAC-XXXV-45 | 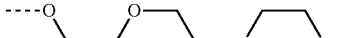 | 948 | | |
| PROTAC-XXXV-46 |  | 948 | | |
| PROTAC-XXXV-47 |  | 972 | | |
| PROTAC-XXXV-48 | 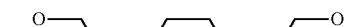 | 948 | | |
| PROTAC-XXXV-49 | 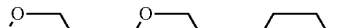 | 962 | | |
| PROTAC-XXXV-50 | 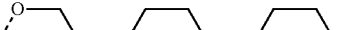 | 962 | | |
| PROTAC-XXXV-51 | 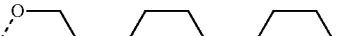 | 960 | | |
| PROTAC-XXXV-52 |  | 962 | | |
| PROTAC-XXXV-53 |  | 962 | | |

TABLE 35-continued
Protacs composed of a RAF ligand and a cereblon ligand with
6-position linkage having the following chemical structure
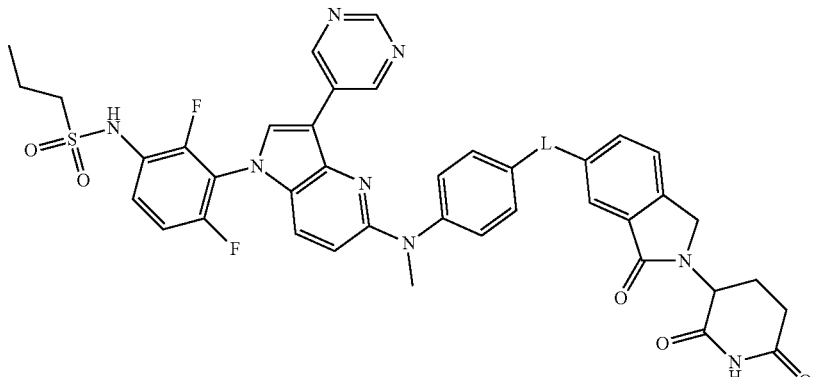
(PROTAC-XXXV)
| PROTAC-XXXV Compound | L | Mass | DC$_{50}$ (µM) | D$_{max}$ (%) |
|---|---|---|---|---|
| PROTAC-XXXV-54 | 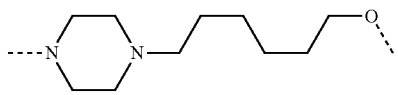 | 960 | | |
| PROTAC-XXXV-55 | 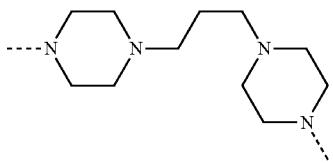 | 986 | | |
| PROTAC-XXXV-56 | 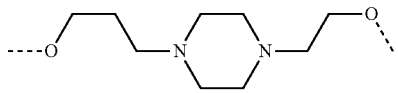 | 962 | | |
| PROTAC-XXXV-57 | 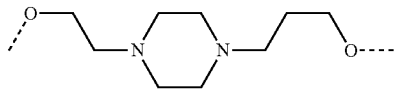 | 962 | | |
| PROTAC-XXXV-58 | 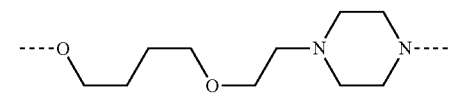 | 976 | | |
| PROTAC-XXXV-59 | 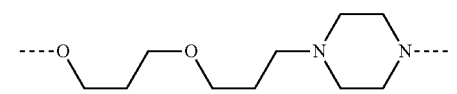 | 976 | | |
| PROTAC-XXXV-60 | 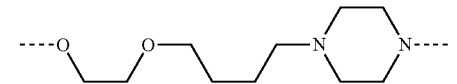 | 976 | | |
| PROTAC-XXXV-61 | 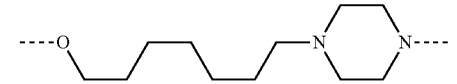 | 974 | | |

TABLE 35-continued

Protacs composed of a RAF ligand and a cereblon ligand with
6-position linkage having the following chemical structure

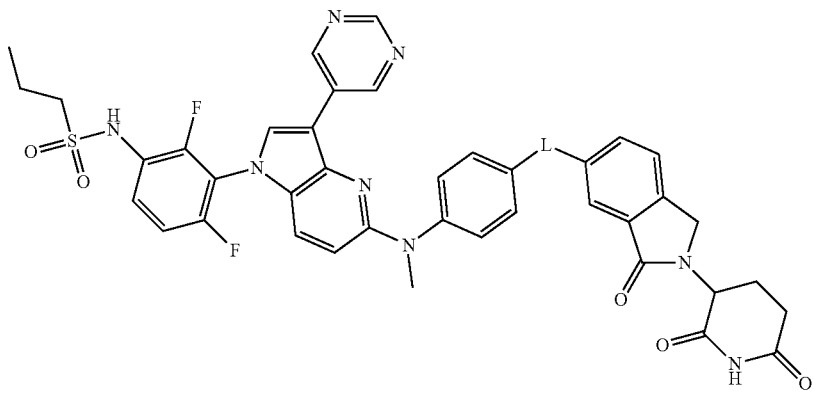

(PROTAC-XXXV)

| PROTAC-XXXV Compound | L | Mass | DC$_{50}$ (µM) | D$_{max}$ (%) |
|---|---|---|---|---|
| PROTAC-XXXV-62 | ----N⌒N–∩–O–∩–O---- | 976 | | |
| PROTAC-XXXV-63 | ----N⌒N–∩–O–∩–O---- | 976 | | |
| PROTAC-XXXV-64 | ----N⌒N–∩–O–∩–O---- | 976 | | |
| PROTAC-XXXV-65 | ----N⌒N–∩–∩–O---- | 974 | | |
| PROTAC-XXXV-66 | ----N⌒N–∩–N⌒N---- | 1000 | | |
| PROTAC-XXXV-67 | ----O–∩–N⌒N–∩–O---- | 976 | | |
| PROTAC-XXXV-68 | O–∩–N⌒N–∩–O | 976 | | |
| PROTAC-XXXV-69 | O–∩–N⌒N–∩–O | 976 | | |
| PROTAC-XXXV-70 | ----O---- | 792 | | |

TABLE 36

Protacs composed of a RAF ligand and a cereblon ligand with 4-position linkage having the following chemical structure

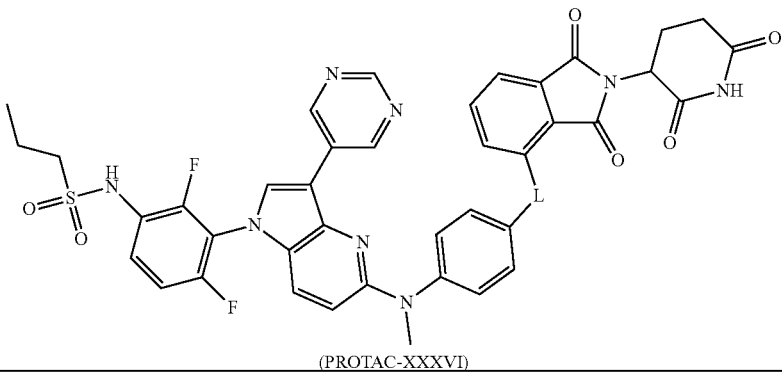

(PROTAC-XXXVI)

| PROTAC-XXXVI Compound | L | Mass | $DC_{50}$ (μM) | max (%) |
|---|---|---|---|---|
| PROTAC-XXXVI-1 | ----O~~O---- | 850 | | |
| PROTAC-XXXVI-2 | ----O~~O~~O-- | 894 | | |
| PROTAC-XXXVI-3 | ----O~~O~~O~~O---- | 938 | | |
| PROTAC-XXXVI-4 | ----O~~O~~O~~O~~O-- | 982 | | |
| PROTAC-XXXVI-5 | ----O~~O~~O~~O~~O~~O---- | 1026 | | |
| PROTAC-XXXVI-6 | ----O~~O~~O~~O~~O~~O~~O-- | 1070 | | |
| PROTAC-XXXVI-7 | ----~~O-- | 834 | | |
| PROTAC-XXXVI-8 | --~~O-- | 820 | | |
| PROTAC-XXXVI-9 | --O~~-- | 834 | | |
| PROTAC-XXXVI-10 | ----O~-- | 820 | | |
| PROTAC-XXXVI-11 | ----O~~O-- | 864 | | |
| PROTAC-XXXVI-12 | ----O~~~O---- | 878 | | |
| PROTAC-XXXVI-13 | ----O~O~O---- | 908 | | |
| PROTAC-XXXVI-14 | ----O~O~O---- | 908 | | |
| PROTAC-XXXVI-15 | ----O~~O---- | 906 | | |
| PROTAC-XXXVI-16 | ----O~O~O-- | 922 | | |

TABLE 36-continued

Protacs composed of a RAF ligand and a cereblon ligand with
4-position linkage having the following chemical structure

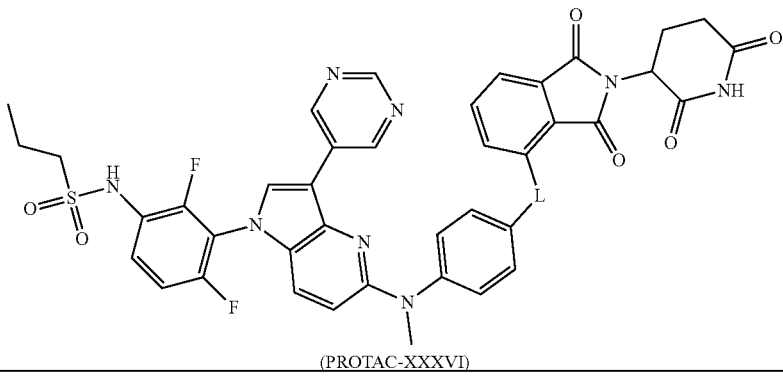

(PROTAC-XXXVI)

| PROTAC-XXXVI Compound | L | Mass | $DC_{50}$ (μM) | max (%) |
|---|---|---|---|---|
| PROTAC-XXXVI-17 | ----O~~O~~O~~O' | 922 | | |
| PROTAC-XXXVI-18 | ----O~~O~~O' | 922 | | |
| PROTAC-XXXVI-19 | ----O~~O~~O~~O~~O\ | 952 | | |
| PROTAC-XXXVI-20 | ----O~~O~~O~~O\ | 952 | | |
| PROTAC-XXXVI-21 | ----O~~O~~O~~O\ | 952 | | |
| PROTAC-XXXVI-22 | ----O~~O~~O\ | 950 | | |
| PROTAC-XXXVI-23 | ----O~~O~~O\ | 950 | | |
| PROTAC-XXXVI-24 | ----O~~O~~O\ | 950 | | |
| PROTAC-XXXVI-25 | ----O~~O~~O\ | 950 | | |
| PROTAC-XXXVI-26 | ----O~~O~~O\ | 950 | | |
| PROTAC-XXXVI-27 | ----O~~O~~O~~O---- | 966 | | |
| PROTAC-XXXVI-28 | ----O~~O~~O~~O---- | 966 | | |
| PROTAC-XXXVI-29 | ----O~~O~~O~~O---- | 966 | | |
| PROTAC-XXXVI-30 | ----O~~O~~O~~O---- | 966 | | |
| PROTAC-XXXVI-31 | ----O~~O~~O~~O---- | 966 | | |

TABLE 36-continued

Protacs composed of a RAF ligand and a cereblon ligand with
4-position linkage having the following chemical structure

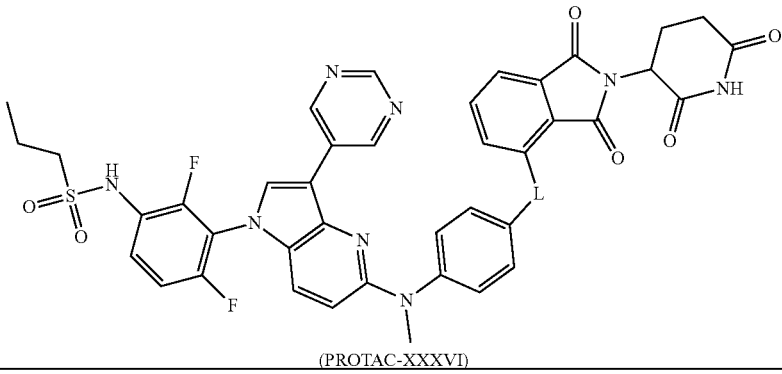

(PROTAC-XXXVI)

| PROTAC-XXXVI Compound | L | Mass | $DC_{50}$ ($\mu M$) | max (%) |
|---|---|---|---|---|
| PROTAC-XXXVI-32 | | 964 | | |
| PROTAC-XXXVI-33 | | 964 | | |
| PROTAC-XXXVI-34 | | 964 | | |
| PROTAC-XXXVI-35 | | 964 | | |
| PROTAC-XXXVI-36 | | 964 | | |
| PROTAC-XXXVI-37 | | 964 | | |
| PROTAC-XXXVI-38 | | 874 | | |
| PROTAC-XXXVI-39 | | 918 | | |
| PROTAC-XXXVI-40 | | 918 | | |
| PROTAC-XXXVI-41 | | 932 | | |
| PROTAC-XXXVI-42 | | 932 | | |
| PROTAC-XXXVI-43 | | 946 | | |
| PROTAC-XXXVI-44 | | 946 | | |

TABLE 36-continued

Protacs composed of a RAF ligand and a cereblon ligand with
4-position linkage having the following chemical structure

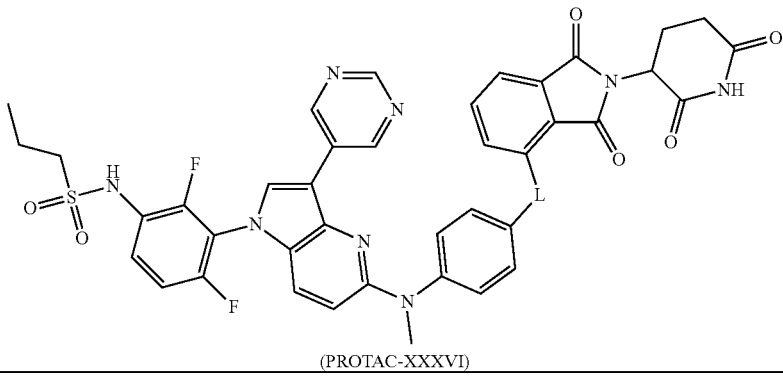

(PROTAC-XXXVI)

| PROTAC-XXXVI Compound | L | Mass | $DC_{50}$ (μM) | max (%) |
|---|---|---|---|---|
| PROTAC-XXXVI-45 | ----O~~O~~N(piperazine)N---- | 962 | | |
| PROTAC-XXXVI-46 | ----N(piperazine)N~~O~~O---- | 962 | | |
| PROTAC-XXXVI-47 | ----N(piperazine)N~~N(piperazine)N---- | 986 | | |
| PROTAC-XXXVI-48 | O~~N(piperazine)N~~O | 962 | | |
| PROTAC-XXXVI-49 | O~~O~~N(piperazine)N---- | 976 | | |
| PROTAC-XXXVI-50 | O~~O~~N(piperazine)N---- | 976 | | |
| PROTAC-XXXVI-51 | O~~~~N(piperazine)N---- | 974 | | |
| PROTAC-XXXVI-52 | ----N(piperazine)N~~O~~O | 976 | | |
| PROTAC-XXXVI-53 | ----N(piperazine)N~~O~~O | 976 | | |
| PROTAC-XXXVI-54 | ----N(piperazine)N~~~~O | 974 | | |

TABLE 36-continued
Protacs composed of a RAF ligand and a cereblon ligand with
4-position linkage having the following chemical structure
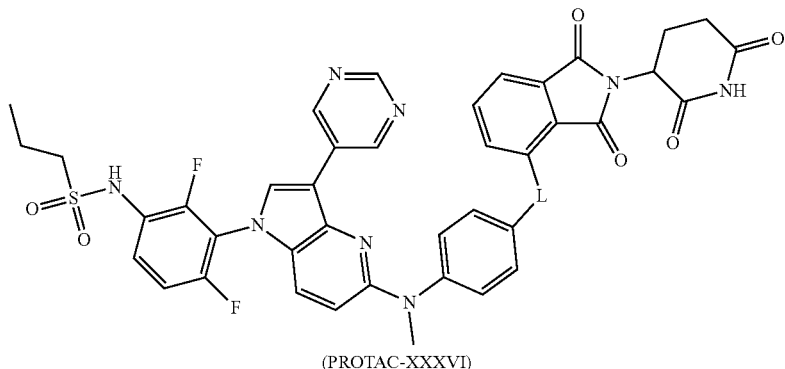
(PROTAC-XXXVI)
| PROTAC-XXXVI Compound | L | Mass | DC$_{50}$ (µM) | max (%) |
|---|---|---|---|---|
| PROTAC-XXXVI-55 | | 1000 | | |
| PROTAC-XXXVI-56 | | 976 | | |
| PROTAC-XXXVI-57 | | 976 | | |
| PROTAC-XXXVI-58 | | 990 | | |
| PROTAC-XXXVI-59 | | 990 | | |
| PROTAC-XXXVI-60 | | 990 | | |
| PROTAC-XXXVI-61 | | 988 | | |
| PROTAC-XXXVI-62 | | 990 | | |

TABLE 36-continued

Protacs composed of a RAF ligand and a cereblon ligand with
4-position linkage having the following chemical structure

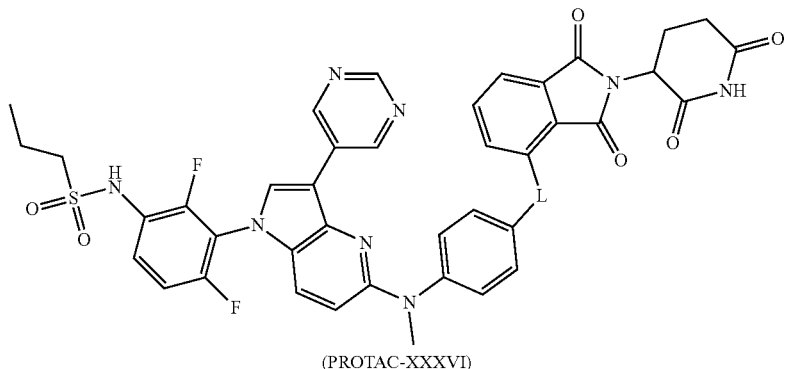

(PROTAC-XXXVI)

| PROTAC-XXXVI Compound | L | Mass | DC$_{50}$ (μM) | max (%) |
|---|---|---|---|---|
| PROTAC-XXXVI-63 | ----N(piperazine)N-CH$_2$CH$_2$-O-CH$_2$CH$_2$-O---- | 990 | | |
| PROTAC-XXXVI-64 | ----N(piperazine)N-CH$_2$CH$_2$-O-CH$_2$CH$_2$CH$_2$-O---- | 990 | | |
| PROTAC-XXXVI-65 | ----N(piperazine)N-(CH$_2$)$_4$-O---- | 988 | | |
| PROTAC-XXXVI-66 | ----N(piperazine)N-(CH$_2$)$_3$-N(piperazine)N---- | 1014 | | |
| PROTAC-XXXVI-67 | ----O-CH$_2$CH$_2$-N(piperazine)N-CH$_2$CH$_2$-O---- | 990 | | |
| PROTAC-XXXVI-68 | ----O-(CH$_2$)$_3$-N(piperazine)N-CH$_2$CH$_2$-O---- | 990 | | |
| PROTAC-XXXVI-69 | ----O-CH$_2$CH$_2$-N(piperazine)N-(CH$_2$)$_3$-O---- | 990 | | |
| PROTAC-XXXVI-70 | ----O---- | 806 | | |

TABLE 37

Protacs composed of a RAF ligand and a cereblon ligand with
4-position linkage having the following chemical structure

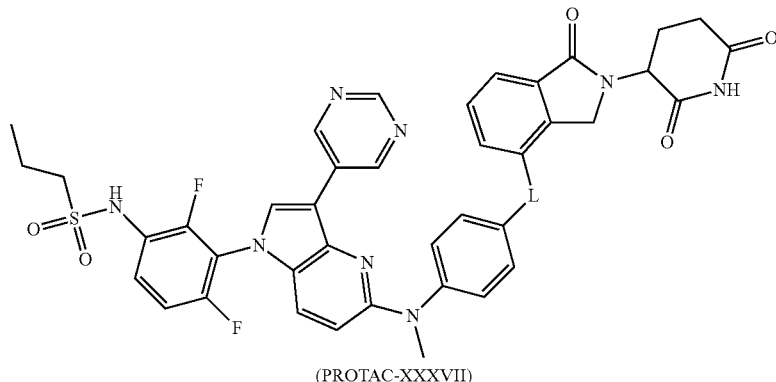

(PROTAC-XXXVII)

| PROTAC-XXXVII Compound | L | Mass | $DC_{50}$ (μM) | $D_{max}$ (%) |
|---|---|---|---|---|
| PROTAC-XXXVII-1 | | 836 | | |
| PROTAC-XXXVII-2 | | 880 | | |
| PROTAC-XXXVII-3 | | 924 | | |
| PROTAC-XXXVII-4 | | 968 | | |
| PROTAC-XXXVII-5 | | 1012 | | |
| PROTAC-XXXVII-6 | | 1056 | | |
| PROTAC-XXXVII-7 | | 820 | | |
| PROTAC-XXXVII-8 | | 806 | | |
| PROTAC-XXXVII-9 | | 820 | | |
| PROTAC-XXXVII-10 | | 806 | | |
| PROTAC-XXXVII-11 | | 850 | | |
| PROTAC-XXXVII-12 | | 864 | | |
| PROTAC-XXXVII-13 | | 894 | | |
| PROTAC-XXXVII-14 | | 894 | | |
| PROTAC-XXXVII-15 | | 892 | | |

TABLE 37-continued

Protacs composed of a RAF ligand and a cereblon ligand with
4-position linkage having the following chemical structure

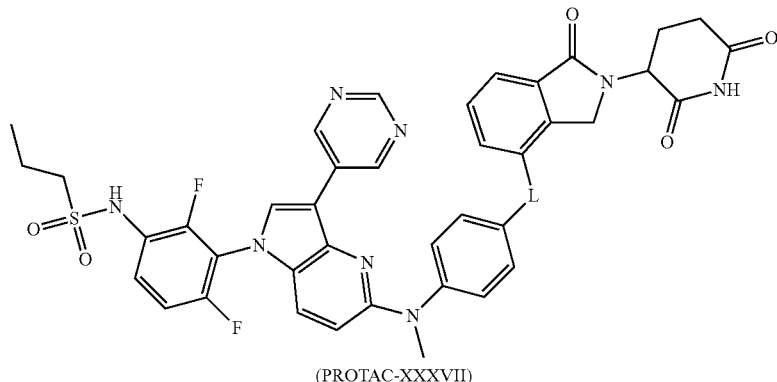

(PROTAC-XXXVII)

| PROTAC-XXXVII Compound | L | Mass | $DC_{50}$ (μM) | $D_{max}$ (%) |
|---|---|---|---|---|
| PROTAC-XXXVII-16 | | 908 | | |
| PROTAC-XXXVII-17 | | 908 | | |
| PROTAC-XXXVII-18 | | 908 | | |
| PROTAC-XXXVII-19 | | 938 | | |
| PROTAC-XXXVII-20 | | 938 | | |
| PROTAC-XXXVII-21 | | 938 | | |
| PROTAC-XXXVII-22 | | 936 | | |
| PROTAC-XXXVII-23 | | 936 | | |
| PROTAC-XXXVII-24 | | 936 | | |
| PROTAC-XXXVII-25 | | 936 | | |
| PROTAC-XXXVII-26 | | 936 | | |
| PROTAC-XXXVII-27 | | 952 | | |
| PROTAC-XXXVII-28 | | 952 | | |
| PROTAC-XXXVII-29 | | 952 | | |
| PROTAC-XXXVII-30 | | 952 | | |

TABLE 37-continued

Protacs composed of a RAF ligand and a cereblon ligand with
4-position linkage having the following chemical structure

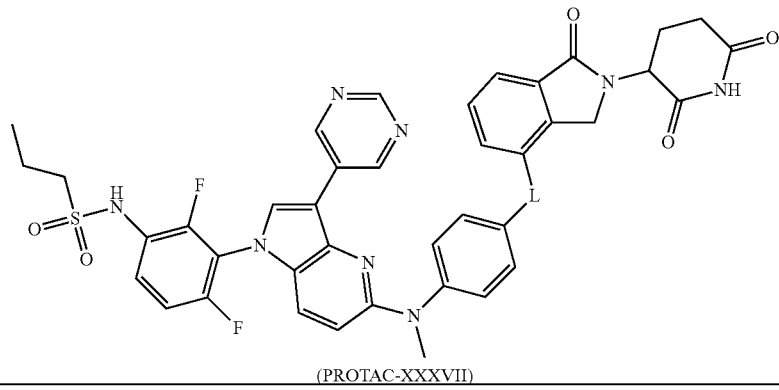

(PROTAC-XXXVII)

| PROTAC-XXXVII Compound | L | Mass | DC$_{50}$ (μM) | D$_{max}$ (%) |
|---|---|---|---|---|
| PROTAC-XXXVII-31 | ----O~~~O~~~O~~~O---- | 952 | | |
| PROTAC-XXXVII-32 | ----O~~~O~~~~O---- | 950 | | |
| PROTAC-XXXVII-33 | ----O~~~~O~~~O---- | 950 | | |
| PROTAC-XXXVII-34 | ----O~~~~~O~~O---- | 950 | | |
| PROTAC-XXXVII-35 | ----O~~~~~O~O---- | 950 | | |
| PROTAC-XXXVII-36 | ----O~~O~~~~O---- | 950 | | |
| PROTAC-XXXVII-37 | ----O~O~~~~~O---- | 950 | | |
| PROTAC-XXXVII-38 | ----N(piperazine)N---- | 860 | | |
| PROTAC-XXXVII-39 | O~~N(piperazine)N---- | 904 | | |
| PROTAC-XXXVII-40 | ----N(piperazine)N~~O | 904 | | |
| PROTAC-XXXVII-41 | ----O~~N(piperazine)N---- | 918 | | |
| PROTAC-XXXVII-42 | ----N(piperazine)N~~O---- | 918 | | |
| PROTAC-XXXVII-43 | O~~~N(piperazine)N---- | 932 | | |

TABLE 37-continued
Protacs composed of a RAF ligand and a cereblon ligand with
4-position linkage having the following chemical structure
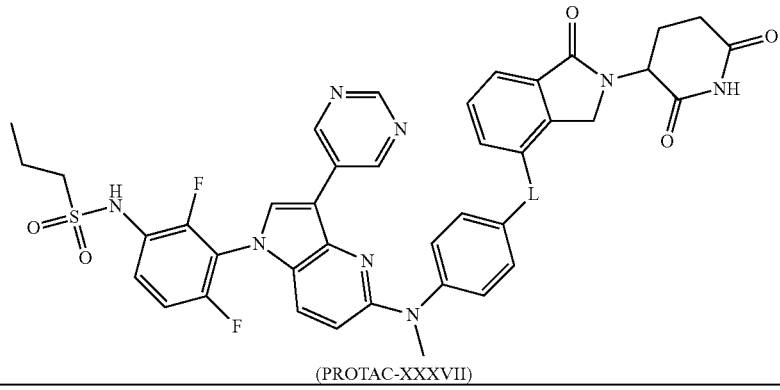
(PROTAC-XXXVII)
| PROTAC-XXXVII Compound | L | Mass | DC$_{50}$ (µM) | D$_{max}$ (%) |
|---|---|---|---|---|
| PROTAC-XXXVII-44 | 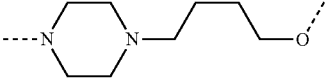 | 932 | | |
| PROTAC-XXXVII-45 | 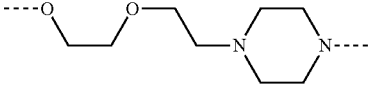 | 948 | | |
| PROTAC-XXXVII-46 | 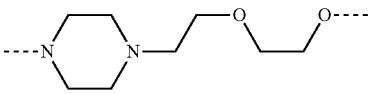 | 948 | | |
| PROTAC-XXXVII-47 | 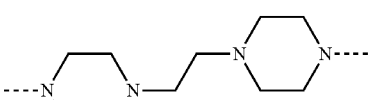 | 972 | | |
| PROTAC-XXXVII-48 | 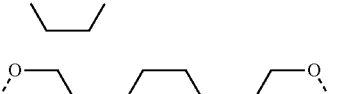 | 948 | | |
| PROTAC-XXXVII-49 | 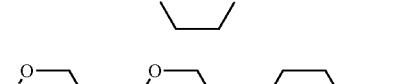 | 962 | | |
| PROTAC-XXXVII-50 |  | 962 | | |
| PROTAC-XXXVII-51 | 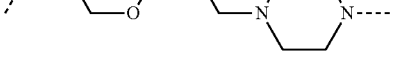 | 960 | | |
| PROTAC-XXXVII-52 | 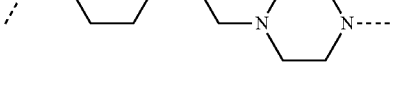 | 962 | | |
| PROTAC-XXXVII-53 | 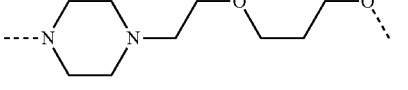 | 962 | | |

TABLE 37-continued
Protacs composed of a RAF ligand and a cereblon ligand with
4-position linkage having the following chemical structure
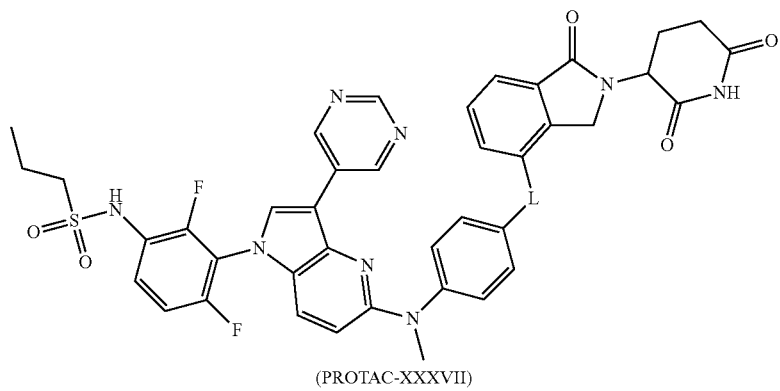
(PROTAC-XXXVII)
| PROTAC-XXXVII Compound | L | Mass | DC$_{50}$ (μM) | D$_{max}$ (%) |
|---|---|---|---|---|
| PROTAC-XXXVII-54 | | 960 | | |
| PROTAC-XXXVII-55 | | 986 | | |
| PROTAC-XXXVII-56 | | 962 | | |
| PROTAC-XXXVII-57 | | 962 | | |
| PROTAC-XXXVII-58 | | 976 | | |
| PROTAC-XXXVII-59 | | 976 | | |
| PROTAC-XXXVII-60 | | 976 | | |
| PROTAC-XXXVII-61 | | 974 | | |

TABLE 37-continued
Protacs composed of a RAF ligand and a cereblon ligand with
4-position linkage having the following chemical structure
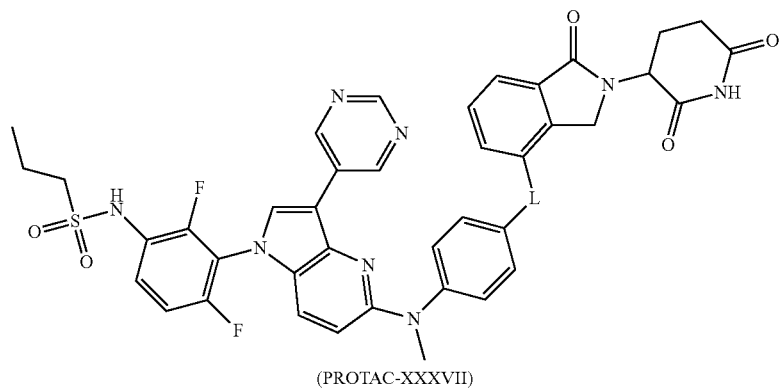
(PROTAC-XXXVII)
| PROTAC-XXXVII Compound | L | Mass | DC$_{50}$ (μM) | D$_{max}$ (%) |
|---|---|---|---|---|
| PROTAC-XXXVII-62 | 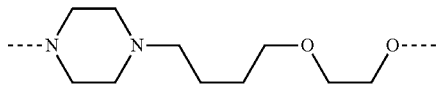 | 976 | | |
| PROTAC-XXXVII-63 | 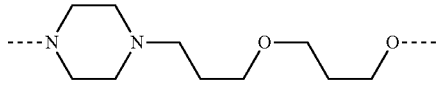 | 976 | | |
| PROTAC-XXXVII-64 | 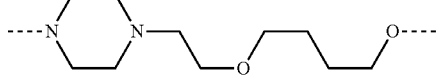 | 976 | | |
| PROTAC-XXXVII-65 | 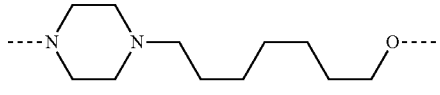 | 974 | | |
| PROTAC-XXXVII-66 | 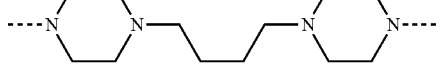 | 1000 | | |
| PROTAC-XXXVII-67 | 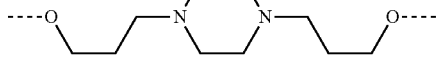 | 976 | | |
| PROTAC-XXXVII-68 | 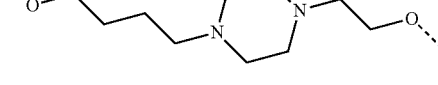 | 976 | | |
| PROTAC-XXXVII-69 | 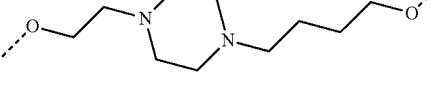 | 976 | | |
| PROTAC-XXXVII-70 | 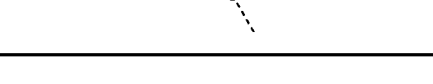 | 792 | | |

TABLE 38

Protacs composed of a RAF ligand and a cereblon ligand with 7-position linkage having the following chemical structure

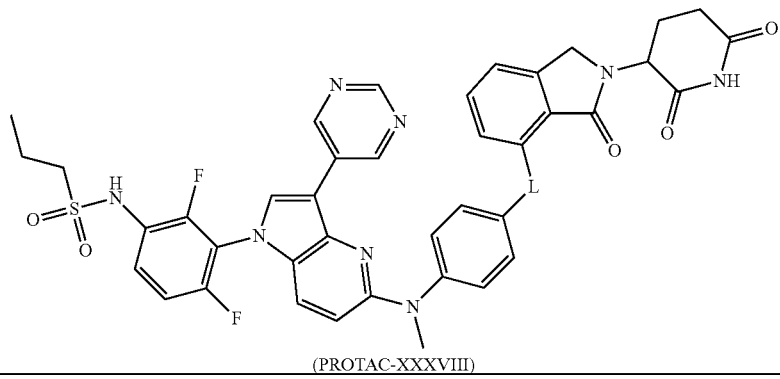

(PROTAC-XXXVIII)

| PROTAC-XXXVIII Compound | L | Mass | DC$_{50}$ (µM) | D$_{max}$ (%) |
|---|---|---|---|---|
| PROTAC-XXXVIII-1 | | 836 | | |
| PROTAC-XXXVIII-2 | | 880 | | |
| PROTAC-XXXVIII-3 | | 924 | | |
| PROTAC-XXXVIII-4 | | 968 | | |
| PROTAC-XXXVIII-5 | | 1012 | | |
| PROTAC-XXXVIII-6 | | 1056 | | |
| PROTAC-XXXVIII-7 | | 820 | | |
| PROTAC-XXXVIII-8 | | 806 | | |
| PROTAC-XXXVIII-9 | | 820 | | |
| PROTAC-XXXVIII-10 | | 806 | | |
| PROTAC-XXXVIII-11 | | 850 | | |
| PROTAC-XXXVIII-12 | | 864 | | |
| PROTAC-XXXVIII-13 | | 894 | | |
| PROTAC-XXXVIII-14 | | 894 | | |
| PROTAC-XXXVIII-15 | | 892 | | |
| PROTAC-XXXVIII-16 | | 908 | | |

TABLE 38-continued

Protacs composed of a RAF ligand and a cereblon ligand with
7-position linkage having the following chemical structure

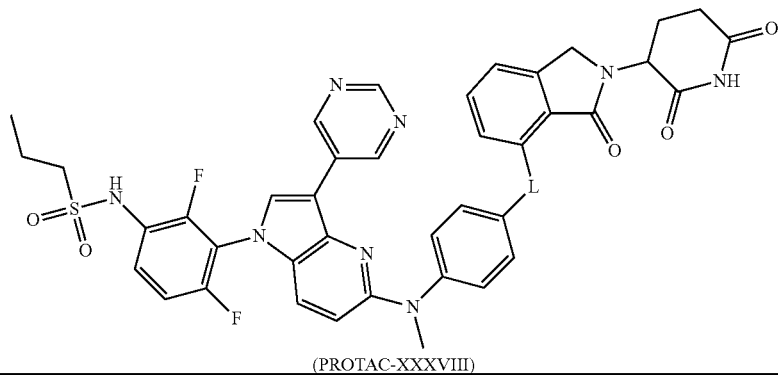

(PROTAC-XXXVIII)

| PROTAC-XXXVIII Compound | L | Mass | $DC_{50}$ (μM) | $D_{max}$ (%) |
|---|---|---|---|---|
| PROTAC-XXXVIII-17 | ----O~~O~~O~~O-- | 908 | | |
| PROTAC-XXXVIII-18 | ----O~~O~~O-- | 908 | | |
| PROTAC-XXXVIII-19 | ----O~O~O~O~O-- | 938 | | |
| PROTAC-XXXVIII-20 | ----O~O~O~O-- | 938 | | |
| PROTAC-XXXVIII-21 | ----O~O~O~O-- | 938 | | |
| PROTAC-XXXVIII-22 | ----O~O~O~O-- | 936 | | |
| PROTAC-XXXVIII-23 | ----O~O~O-- | 936 | | |
| PROTAC-XXXVIII-24 | ----O~O~O-- | 936 | | |
| PROTAC-XXXVIII-25 | ----O~O~O-- | 936 | | |
| PROTAC-XXXVIII-26 | ----O~O~O-- | 936 | | |
| PROTAC-XXXVIII-27 | ----O~O~O~O---- | 952 | | |
| PROTAC-XXXVIII-28 | ----O~O~O~O~O---- | 952 | | |
| PROTAC-XXXVIII-29 | ----O~O~O~O---- | 952 | | |
| PROTAC-XXXVIII-30 | ----O~O~O~O---- | 952 | | |
| PROTAC-XXXVIII-31 | ----O~O~O~O---- | 952 | | |

TABLE 38-continued

Protacs composed of a RAF ligand and a cereblon ligand with
7-position linkage having the following chemical structure

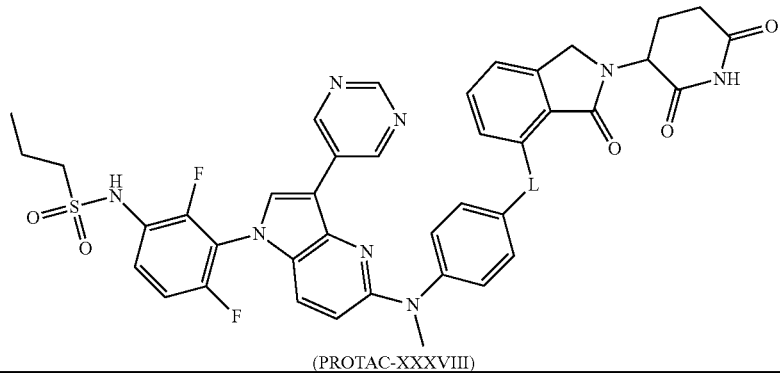

(PROTAC-XXXVIII)

| PROTAC-XXXVIII Compound | L | Mass | $DC_{50}$ ($\mu$M) | $D_{max}$ (%) |
|---|---|---|---|---|
| PROTAC-XXXVIII-32 | | 950 | | |
| PROTAC-XXXVIII-33 | | 950 | | |
| PROTAC-XXXVIII-34 | | 950 | | |
| PROTAC-XXXVIII-35 | | 950 | | |
| PROTAC-XXXVIII-36 | | 950 | | |
| PROTAC-XXXVIII-37 | | 950 | | |
| PROTAC-XXXVIII-38 | | 860 | | |
| PROTAC-XXXVIII-39 | | 904 | | |
| PROTAC-XXXVIII-40 | | 904 | | |
| PROTAC-XXXVIII-41 | | 918 | | |
| PROTAC-XXXVIII-42 | | 918 | | |
| PROTAC-XXXVIII-43 | | 932 | | |
| PROTAC-XXXVIII-44 | | 932 | | |

TABLE 38-continued

Protacs composed of a RAF ligand and a cereblon ligand with
7-position linkage having the following chemical structure

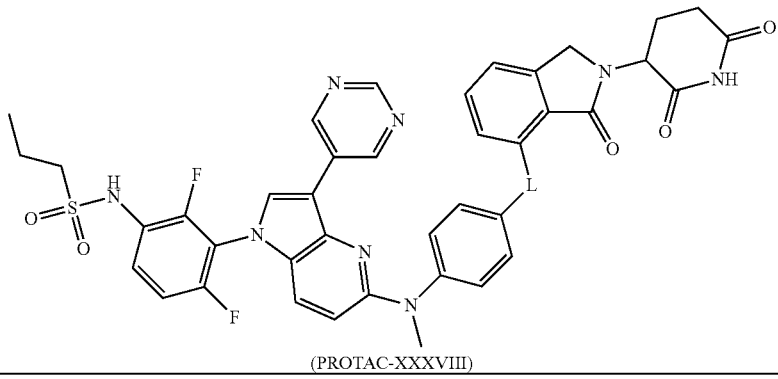

(PROTAC-XXXVIII)

| PROTAC-XXXVIII Compound | L | Mass | DC$_{50}$ (µM) | D$_{max}$ (%) |
|---|---|---|---|---|
| PROTAC-XXXVIII-45 | ----O~~O~~N(piperazine)N---- | 948 | | |
| PROTAC-XXXVIII-46 | ----N(piperazine)N~~O~~O---- | 948 | | |
| PROTAC-XXXVIII-47 | ----N(piperazine)N~~N(piperazine)N---- | 972 | | |
| PROTAC-XXXVIII-48 | O~~N(piperazine)N~~O | 948 | | |
| PROTAC-XXXVIII-49 | O~~O~~N(piperazine)N---- | 962 | | |
| PROTAC-XXXVIII-50 | O~~O~~N(piperazine)N---- | 962 | | |
| PROTAC-XXXVIII-51 | O~~~~N(piperazine)N---- | 960 | | |
| PROTAC-XXXVIII-52 | ----N(piperazine)N~~O~~O | 962 | | |
| PROTAC-XXXVIII-53 | ----N(piperazine)N~~O~~O | 962 | | |
| PROTAC-XXXVIII-54 | ----N(piperazine)N~~~~O | 960 | | |

TABLE 38-continued

Protacs composed of a RAF ligand and a cereblon ligand with
7-position linkage having the following chemical structure

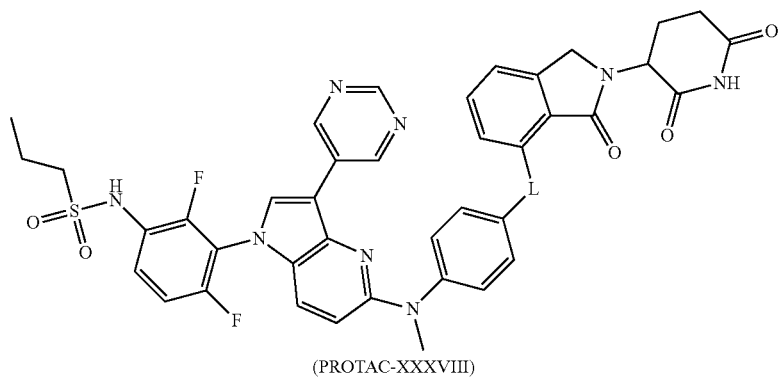

(PROTAC-XXXVIII)

| PROTAC-XXXVIII Compound | L | Mass | DC$_{50}$ (μM) | D$_{max}$ (%) |
|---|---|---|---|---|
| PROTAC-XXXVIII-55 | ![piperazine-propyl-piperazine linker] | 986 | | |
| PROTAC-XXXVIII-56 | ![O-ethyl-piperazine-ethyl-O linker] | 962 | | |
| PROTAC-XXXVIII-57 | ![O-ethyl-piperazine-ethyl-O linker] | 962 | | |
| PROTAC-XXXVIII-58 | ![O-propyl-O-ethyl-piperazine linker] | 976 | | |
| PROTAC-XXXVIII-59 | ![O-ethyl-O-ethyl-piperazine linker] | 976 | | |
| PROTAC-XXXVIII-60 | ![O-ethyl-O-propyl-piperazine linker] | 976 | | |
| PROTAC-XXXVIII-61 | ![O-butyl-piperazine linker] | 974 | | |
| PROTAC-XXXVIII-62 | ![piperazine-propyl-O-ethyl-O linker] | 976 | | |

TABLE 38-continued

Protacs composed of a RAF ligand and a cereblon ligand with
7-position linkage having the following chemical structure

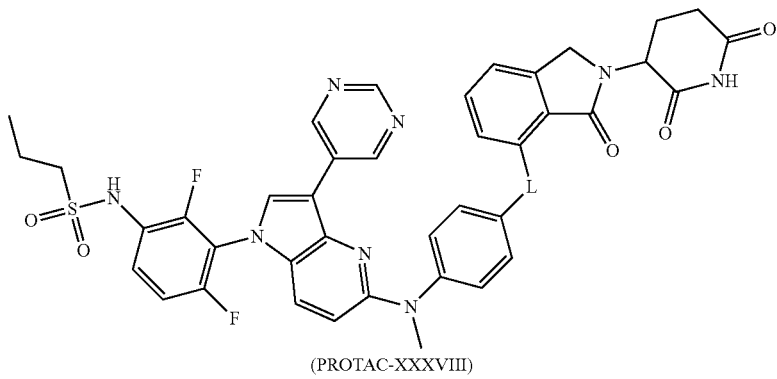

(PROTAC-XXXVIII)

| PROTAC-XXXVIII Compound | L | Mass | DC$_{50}$ (μM) | D$_{max}$ (%) |
|---|---|---|---|---|
| PROTAC-XXXVIII-63 | ![structure] | 976 | | |
| PROTAC-XXXVIII-64 | ![structure] | 976 | | |
| PROTAC-XXXVIII-65 | ![structure] | 974 | | |
| PROTAC-XXXVIII-66 | ![structure] | 1000 | | |
| PROTAC-XXXVIII-67 | ![structure] | 976 | | |
| PROTAC-XXXVIII-68 | ![structure] | 976 | | |
| PROTAC-XXXVIII-69 | ![structure] | 976 | | |
| PROTAC-XXXVIII-70 | ![structure] | 792 | | |

TABLE 39
Protacs composed of a RAF ligand and a VHL ligand with left-side linkage having the following chemical structure
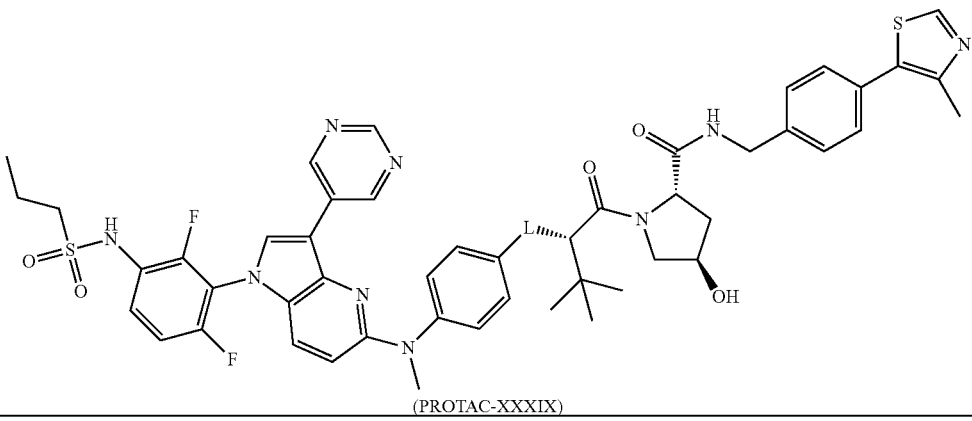
(PROTAC-XXXIX)
| PROTAC-XXXIX Compound | L | Mass | DC50 (PM) | Dmax (%) |
|---|---|---|---|---|
| PROTAC-XXXIX-1 | | 1064 | | |
| PROTAC-XXXIX-2 | | 1108 | | |
| PROTAC-XXXIX-3 | | 1152 | | |
| PROTAC-XXXIX-4 | | 1196 | | |
| PROTAC-XXXIX-5 | | 1240 | | |
| PROTAC-XXXIX-6 | | 1284 | | |
| PROTAC-XXXIX-7 | | 1048 | | |
| PROTAC-XXXIX-8 | | 1034 | | |
| PROTAC-XXXIX-9 | | 1078 | | |
| PROTAC-XXXIX-10 | | 1078 | | |

TABLE 39-continued

Protacs composed of a RAF ligand and a VHL ligand with left-side
linkage having the following chemical structure

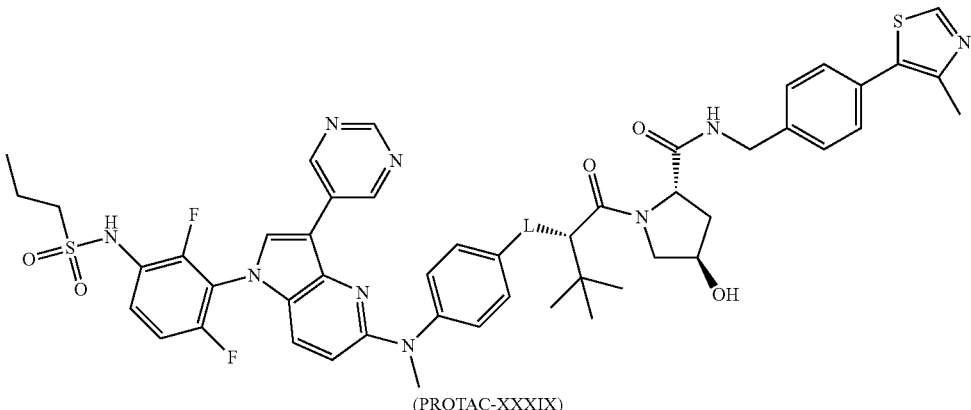

(PROTAC-XXXIX)

| PROTAC-XXXIX Compound | L | Mass | DC50 (PM) | Dmax (%) |
|---|---|---|---|---|
| PROTAC-XXXIX-11 | ----O~~~~~NH---- (with C=O) | 1076 | | |
| PROTAC-XXXIX-12 | ----O~~~O~~NH (with C=O) | 1092 | | |
| PROTAC-XXXIX-13 | ----O~~O~~~NH (with C=O) | 1092 | | |
| PROTAC-XXXIX-14 | ----O~O~~~NH (with C=O) | 1092 | | |
| PROTAC-XXXIX-15 | ----O~~~~~NH (with C=O) | 1090 | | |
| PROTAC-XXXIX-16 | ----O~NH---- (with C=O) | 1020 | | |
| PROTAC-XXXIX-17 | ----O~~~NH (with C=O) | 1062 | | |
| PROTAC-XXXIX-18 | O~~O~~~NH (with C=O) | 1106 | | |
| PROTAC-XXXIX-19 | O~~~O~~NH (with C=O) | 1106 | | |
| PROTAC-XXXIX-20 | O~~~O~~NH (with C=O) | 1106 | | |

TABLE 39-continued
Protacs composed of a RAF ligand and a VHL ligand with left-side
linkage having the following chemical structure
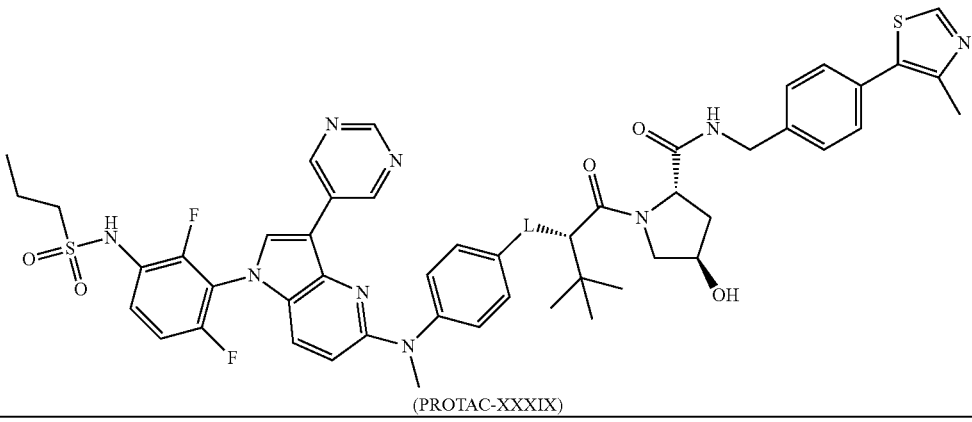
(PROTAC-XXXIX)
| PROTAC-XXXIX Compound | L | Mass | DC50 (PM) | Dmax (%) |
|---|---|---|---|---|
| PROTAC-XXXIX-21 | | 1106 | | |
| PROTAC-XXXIX-22 | | 1122 | | |
| PROTAC-XXXIX-23 | | 1122 | | |
| PROTAC-XXXIX-24 | | 1122 | | |
| PROTAC-XXXIX-25 | | 1120 | | |
| PROTAC-XXXIX-26 | | 1120 | | |
| PROTAC-XXXIX-27 | | 1120 | | |
| PROTAC-XXXIX-28 | | 1120 | | |
| PROTAC-XXXIX-29 | | 1120 | | |

TABLE 39-continued

Protacs composed of a RAF ligand and a VHL ligand with left-side linkage having the following chemical structure

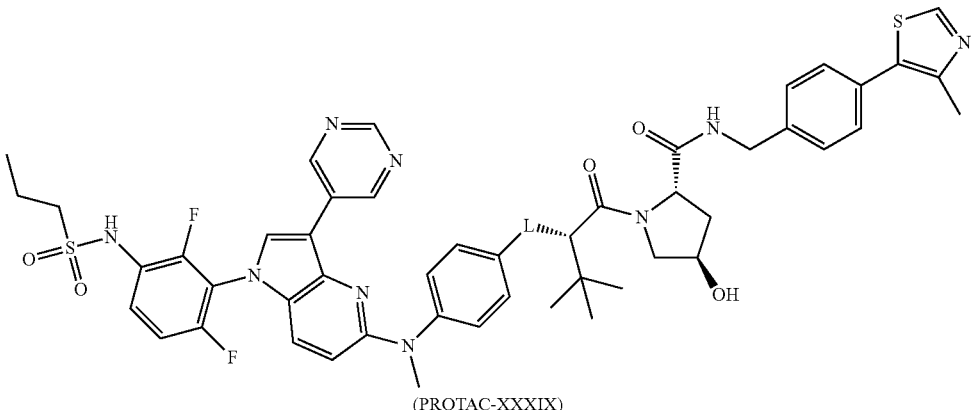

(PROTAC-XXXIX)

| PROTAC-XXXIX Compound | L | Mass | DC50 (PM) | Dmax (%) |
|---|---|---|---|---|
| PROTAC-XXXIX-30 | ----O~~O~~O~~O~~C(O)HN---- | 1136 | | |
| PROTAC-XXXIX-31 | ----O~~O~~O~~O~~C(O)HN---- | 1136 | | |
| PROTAC-XXXIX-32 | ----O~~O~~O~~O~~C(O)HN---- | 1136 | | |
| PROTAC-XXXIX-33 | ---O~~O~~O~~C(O)HN--- | 1150 | | |
| PROTAC-XXXIX-34 | ---O~~O~~O~~C(O)HN--- | 1150 | | |
| PROTAC-XXXIX-35 | ---O~~O~~O~~O~~C(O)HN--- | 1150 | | |
| PROTAC-XXXIX-36 | ---O~~O~~O~~C(O)HN--- | 1150 | | |
| PROTAC-XXXIX-37 | ---O~~O~~O~~C(O)HN--- | 1150 | | |
| PROTAC-XXXIX-38 | ---O~~O~~O~~C(O)HN--- | 1150 | | |
| PROTAC-XXXIX-39 | ---O~~O~~O~~C(O)HN--- | 1150 | | |

TABLE 39-continued
Protacs composed of a RAF ligand and a VHL ligand with left-side linkage having the following chemical structure
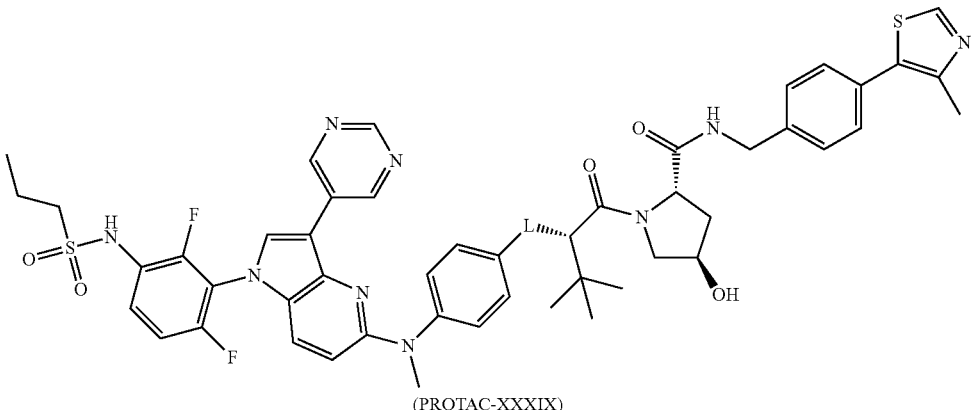
(PROTAC-XXXIX)
| PROTAC-XXXIX Compound | L | Mass | DC50 (PM) | Dmax (%) |
|---|---|---|---|---|
| PROTAC-XXXIX-40 | | 1148 | | |
| PROTAC-XXXIX-41 | | 1148 | | |
| PROTAC-XXXIX-42 | | 1148 | | |
| PROTAC-XXXIX-43 | | 1148 | | |
| PROTAC-XXXIX-44 | | 1132 | | |
| PROTAC-XXXIX-45 | | 1146 | | |
| PROTAC-XXXIX-46 | | 1160 | | |
| PROTAC-XXXIX-47 | | 1174 | | |
| PROTAC-XXXIX-48 | | 1176 | | |

TABLE 39-continued
Protacs composed of a RAF ligand and a VHL ligand with left-side linkage having the following chemical structure
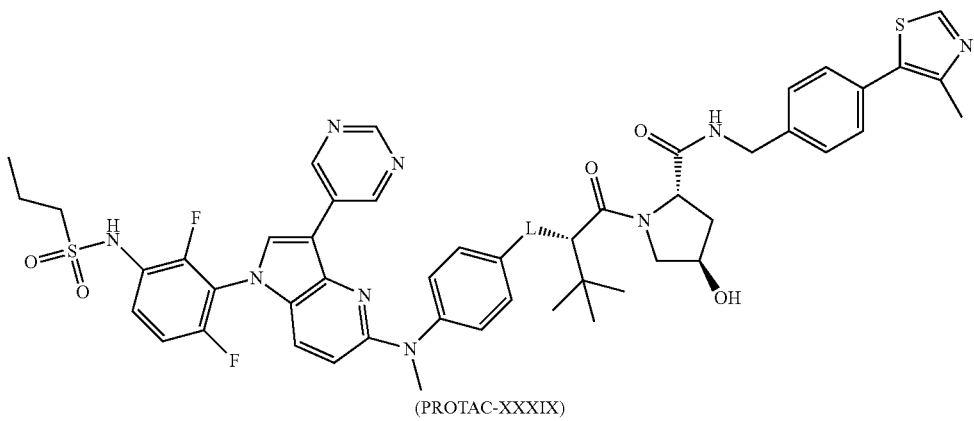
(PROTAC-XXXIX)
| PROTAC-XXXIX Compound | L | Mass | DC50 (PM) | Dmax (%) |
|---|---|---|---|---|
| PROTAC-XXXIX-49 | | 1190 | | |
| PROTAC-XXXIX-50 | | 1204 | | |
| PROTAC-XXXIX-51 | | 1218 | | |
| PROTAC-XXXIX-52 | | 1220 | | |
| PROTAC-XXXIX-53 | | 1132 | | |
| PROTAC-XXXIX-54 | | 1131 | | |
| PROTAC-XXXIX-55 | | 1146 | | |

TABLE 39-continued
Protacs composed of a RAF ligand and a VHL ligand with left-side linkage having the following chemical structure
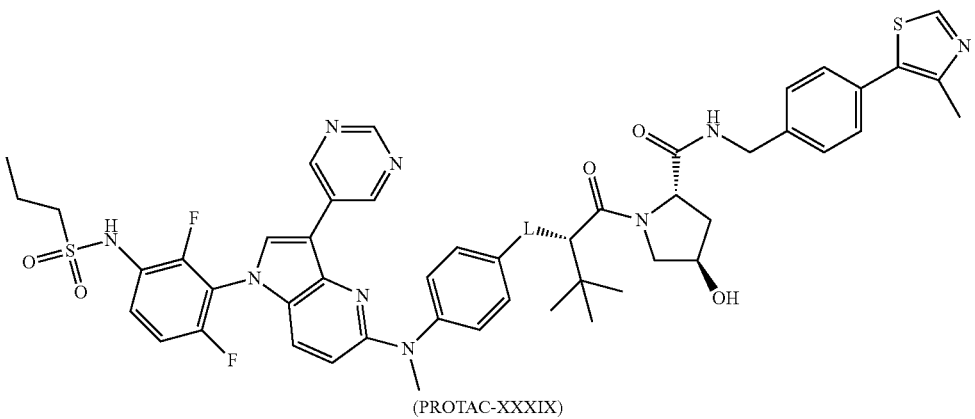
(PROTAC-XXXIX)
| PROTAC-XXXIX Compound | L | Mass | DC50 (PM) | Dmax (%) |
|---|---|---|---|---|
| PROTAC-XXXIX-56 | | 1160 | | |
| PROTAC-XXXIX-57 | | 1174 | | |
| PROTAC-XXXIX-58 | | 1176 | | |
| PROTAC-XXXIX-59 | | 1175 | | |
| PROTAC-XXXIX-60 | | 1200 | | |
| PROTAC-XXXIX-61 | | 1199 | | |
| PROTAC-XXXIX-62 | | 1199 | | |

TABLE 39-continued
Protacs composed of a RAF ligand and a VHL ligand with left-side linkage having the following chemical structure
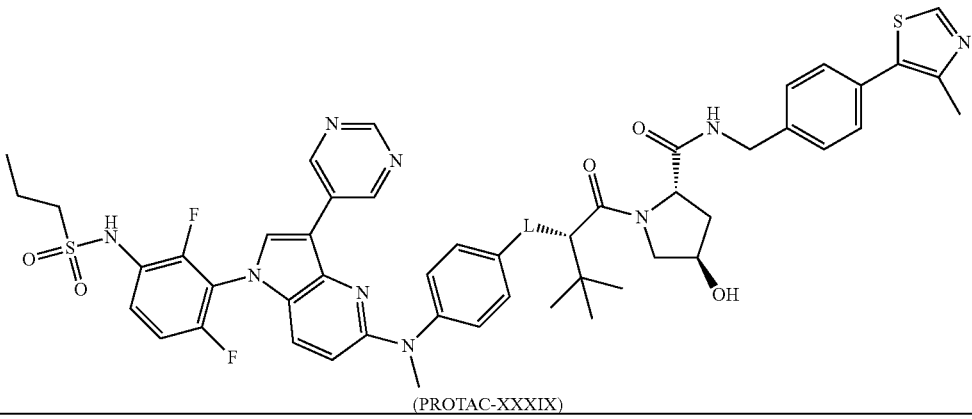
(PROTAC-XXXIX)
| PROTAC-XXXIX Compound | L | Mass | DC50 (PM) | Dmax (%) |
|---|---|---|---|---|
| PROTAC-XXXIX-63 | | 1185 | | |
| PROTAC-XXXIX-64 | | 1171 | | |
| PROTAC-XXXIX-65 | | 1044 | | |
| PROTAC-XXXIX-66 | | 1058 | | |
| PROTAC-XXXIX-67 | | 1072 | | |
| PROTAC-XXXIX-68 | | 1086 | | |
| PROTAC-XXXIX-69 | | 1088 | | |
| PROTAC-XXXIX-70 | | 1100 | | |
| PROTAC-XXXIX-71 | | 1102 | | |
| PROTAC-XXXIX-72 | | 1102 | | |

TABLE 39-continued
Protacs composed of a RAF ligand and a VHL ligand with left-side
linkage having the following chemical structure
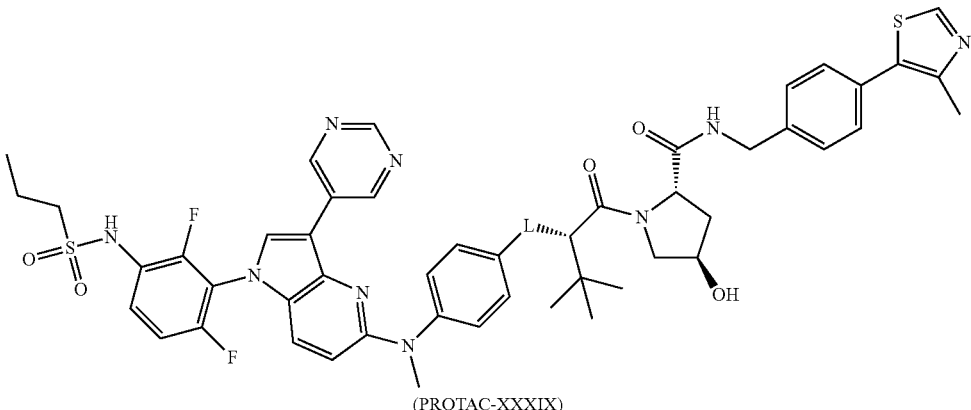
(PROTAC-XXXIX)
| PROTAC-XXXIX Compound | L | Mass | DC50 (PM) | Dmax (%) |
|---|---|---|---|---|
| PROTAC-XXXIX-73 | | 1116 | | |
| PROTAC-XXXIX-74 | | 1116 | | |
| PROTAC-XXXIX-75 | | 1116 | | |
| PROTAC-XXXIX-76 | | 1130 | | |
| PROTAC-XXXIX-77 | | 1130 | | |
| PROTAC-XXXIX-78 | | 1130 | | |
| PROTAC-XXXIX-79 | | 1130 | | |
| PROTAC-XXXIX-80 | | 1132 | | |
| PROTAC-XXXIX-81 | | 1144 | | |
| PROTAC-XXXIX-82 | | 1144 | | |

TABLE 39-continued
Protacs composed of a RAF ligand and a VHL ligand with left-side
linkage having the following chemical structure
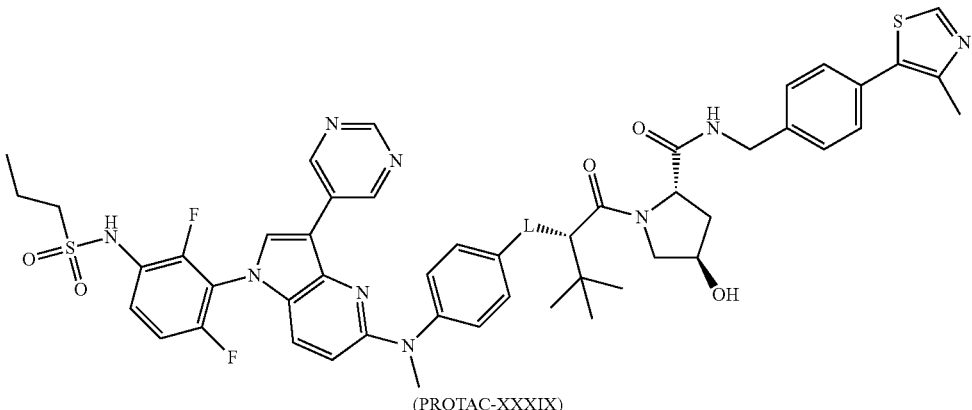
(PROTAC-XXXIX)
| PROTAC-XXXIX Compound | L | Mass | DC50 (PM) | Dmax (%) |
|---|---|---|---|---|
| PROTAC-XXXIX-83 | | 1144 | | |
| PROTAC-XXXIX-84 | | 1144 | | |
| PROTAC-XXXIX-85 | | 1144 | | |
| PROTAC-XXXIX-86 | | 1146 | | |
| PROTAC-XXXIX-87 | | 1146 | | |
| PROTAC-XXXIX-88 | | 1146 | | |
| PROTAC-XXXIX-89 | | 1098 | | |
| PROTAC-XXXIX-90 | | 1112 | | |
| PROTAC-XXXIX-91 | | 1126 | | |
| PROTAC-XXXIX-92 | | 1140 | | |

TABLE 39-continued

Protacs composed of a RAF ligand and a VHL ligand with left-side linkage having the following chemical structure

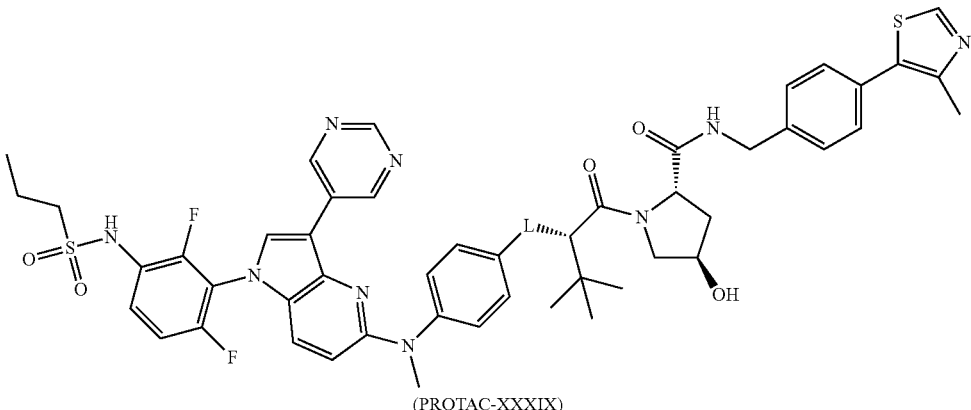

(PROTAC-XXXIX)

| PROTAC-XXXIX Compound | L | Mass | DC50 (PM) | Dmax (%) |
|---|---|---|---|---|
| PROTAC-XXXIX-93 | (piperazine-(CH2)4-isoxazole) | 1154 | | |
| PROTAC-XXXIX-94 | (piperazine-(CH2)2-O-CH2-isoxazole) | 1156 | | |
| PROTAC-XXXIX-95 | (piperazine-(CH2)3-O-CH2-isoxazole) | 1170 | | |
| PROTAC-XXXIX-96 | (piperazine-(CH2)2-O-(CH2)2-isoxazole) | 1170 | | |
| PROTAC-XXXIX-97 | (piperazine-(CH2)5-isoxazole) | 1168 | | |
| PROTAC-XXXIX-98 | (piperazine-(CH2)6-isoxazole) | 1182 | | |
| PROTAC-XXXIX-99 | (piperazine-(CH2)2-O-(CH2)3-isoxazole) | 1184 | | |
| PROTAC-XXXIX-100 | (piperazine-(CH2)3-O-(CH2)2-isoxazole) | 1184 | | |
| PROTAC-XXXIX-101 | (piperazine-(CH2)4-O-CH2-isoxazole) | 1184 | | |

TABLE 40

Protacs composed of a RAF ligand and a VHL ligand with right-side linkage having the following chemical structure

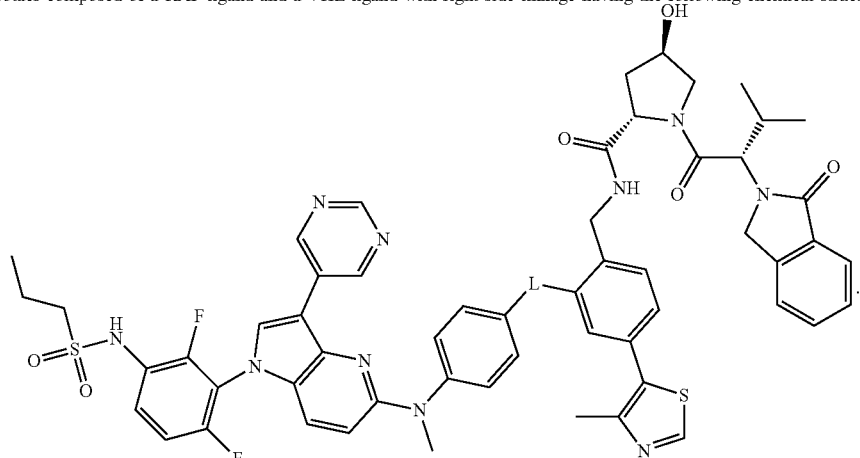

(PROTAC-XXXX)

| PROTAC-XXXX Compound | L | Mass | DC$_{50}$ (μM) | Dmax (%) |
|---|---|---|---|---|
| PROTAC-XXXX-1 | ----O~~O---- | 1124 | | |
| PROTAC-XXXX-2 | ----O~~O~~O---- | 1168 | | |
| PROTAC-XXXX-3 | ----O~~O~~O~~O---- | 1212 | | |
| PROTAC-XXXX-4 | ----O~~O~~O~~O~~O---- | 1256 | | |
| PROTAC-XXXX-5 | ----O~~O~~O~~O~~O~~O---- | 1300 | | |
| PROTAC-XXXX-6 | ----O~~O~~O~~O~~O~~O~~O---- | 1344 | | |
| PROTAC-XXXX-7 | ----O~~~~O---- | 1108 | | |
| PROTAC-XXXX-8 | ----O---- | 1094 | | |
| PROTAC-XXXX-9 | ----O~~---- | 1108 | | |
| PROTAC-XXXX-10 | ----O---- | 1094 | | |
| PROTAC-XXXX-11 | ----O~~O---- | 1138 | | |
| PROTAC-XXXX-12 | ----O~~~O---- | 1152 | | |
| PROTAC-XXXX-13 | ----O~~O~~O---- | 1182 | | |
| PROTAC-XXXX-14 | ----O~~O~~O---- | 1182 | | |

TABLE 40-continued
Protacs composed of a RAF ligand and a VHL ligand with right-side linkage having the following chemical structure
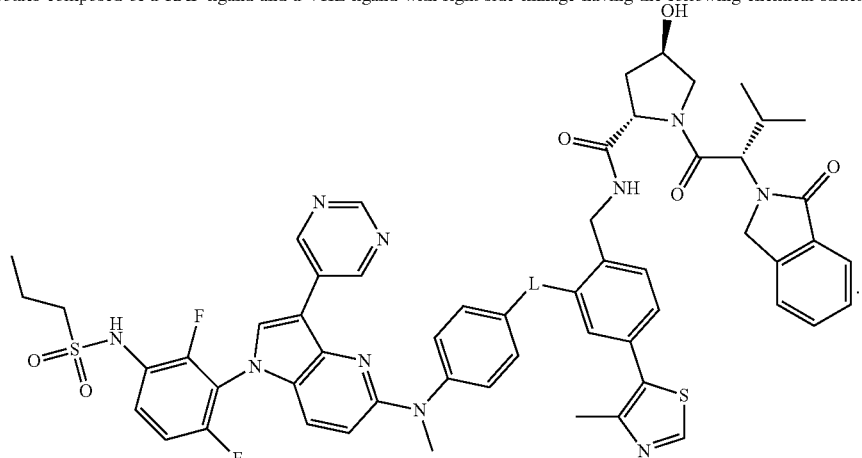
(PROTAC-XXXX)
| PROTAC-XXXX Compound | L | Mass | DC$_{50}$ (μM) | Dmax (%) |
|---|---|---|---|---|
| PROTAC-XXXX-15 | | 1180 | | |
| PROTAC-XXXX-16 | | 1180 | | |
| PROTAC-XXXX-17 | | 1196 | | |
| PROTAC-XXXX-18 | | 1196 | | |
| PROTAC-XXXX-19 | | 1226 | | |
| PROTAC-XXXX-20 | | 1226 | | |
| PROTAC-XXXX-21 | | 1226 | | |
| PROTAC-XXXX-22 | | 1224 | | |
| PROTAC-XXXX-23 | | 1224 | | |
| PROTAC-XXXX-24 | | 1224 | | |
| PROTAC-XXXX-25 | | 1224 | | |
| PROTAC-XXXX-26 | | 1224 | | |
| PROTAC-XXXX-27 | | 1240 | | |
| PROTAC-XXXX-28 | | 1240 | | |

TABLE 40-continued

Protacs composed of a RAF ligand and a VHL ligand with right-side linkage having the following chemical structure

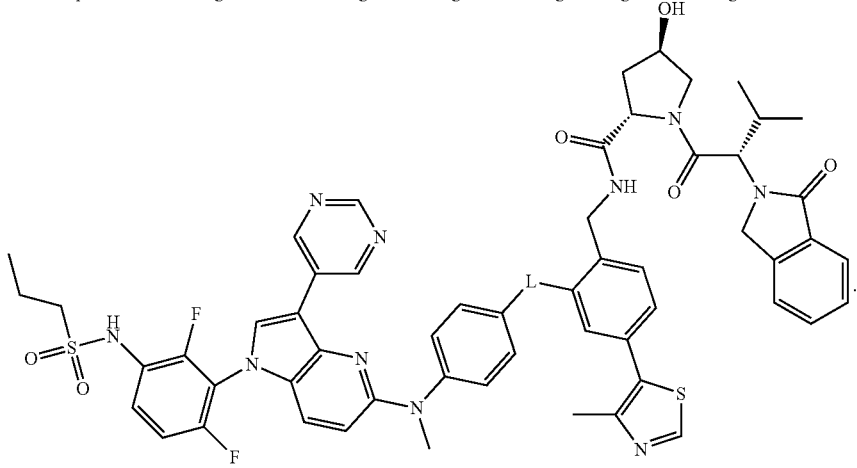

(PROTAC-XXXX)

| PROTAC-XXXX Compound | L | Mass | DC$_{50}$ (μM) | Dmax (%) |
|---|---|---|---|---|
| PROTAC-XXXX-29 | ----O~O~O~O---- | 1240 | | |
| PROTAC-XXXX-30 | ----O~O~O~O---- | 1240 | | |
| PROTAC-XXXX-31 | ----O~O~O~O---- | 1240 | | |
| PROTAC-XXXX-32 | ----O~O~O~O---- | 1238 | | |
| PROTAC-XXXX-33 | ----O~O~O~O---- | 1238 | | |
| PROTAC-XXXX-34 | ----O~O~O~O---- | 1238 | | |
| PROTAC-XXXX-35 | ----O~O~O~O---- | 1238 | | |
| PROTAC-XXXX-36 | ----O~O~O~O---- | 1238 | | |
| PROTAC-XXXX-37 | ----O~O~O~O---- | 1238 | | |
| PROTAC-XXXX-38 | ----N(piperazine)N---- | 1148 | | |
| PROTAC-XXXX-39 | O~N(piperazine)N---- | 1192 | | |
| PROTAC-XXXX-40 | ----N(piperazine)N~O | 1192 | | |

TABLE 40-continued

Protacs composed of a RAF ligand and a VHL ligand with right-side linkage having the following chemical structure

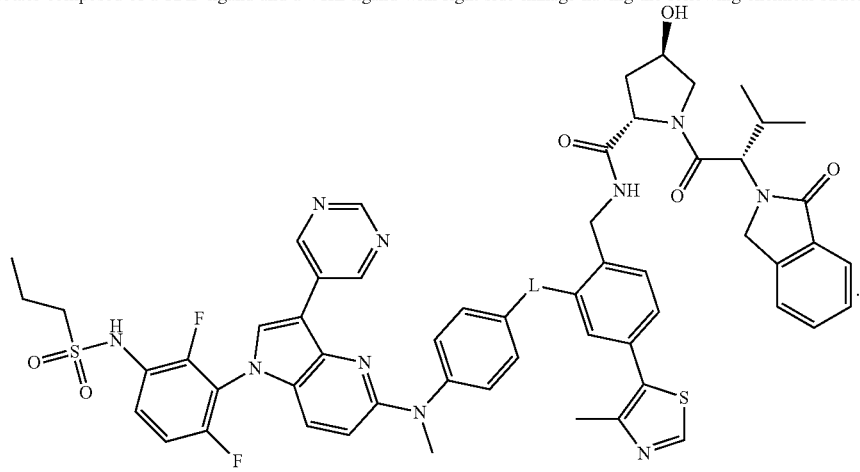

(PROTAC-XXXX)

| PROTAC-XXXX Compound | L | Mass | DC$_{50}$ (μM) | Dmax (%) |
|---|---|---|---|---|
| PROTAC-XXXX-41 | ----O~~~N(piperazine)N---- | 1206 | | |
| PROTAC-XXXX-42 | ----N(piperazine)N~~~O---- | 1206 | | |
| PROTAC-XXXX-43 | ``O~~~N(piperazine)N---- | 1220 | | |
| PROTAC-XXXX-44 | ----N(piperazine)N~~~O`` | 1220 | | |
| PROTAC-XXXX-45 | ----O~O~N(piperazine)N---- | 1236 | | |
| PROTAC-XXXX-46 | ----N(piperazine)N~O~O---- | 1236 | | |
| PROTAC-XXXX-47 | ----N(piperazine)N~N(piperazine)N---- | 1260 | | |
| PROTAC-XXXX-48 | ``O~N(piperazine)N~O`` | 1236 | | |
| PROTAC-XXXX-49 | ``O~O~N(piperazine)N---- | 1250 | | |

TABLE 40-continued

Protacs composed of a RAF ligand and a VHL ligand with right-side linkage having the following chemical structure

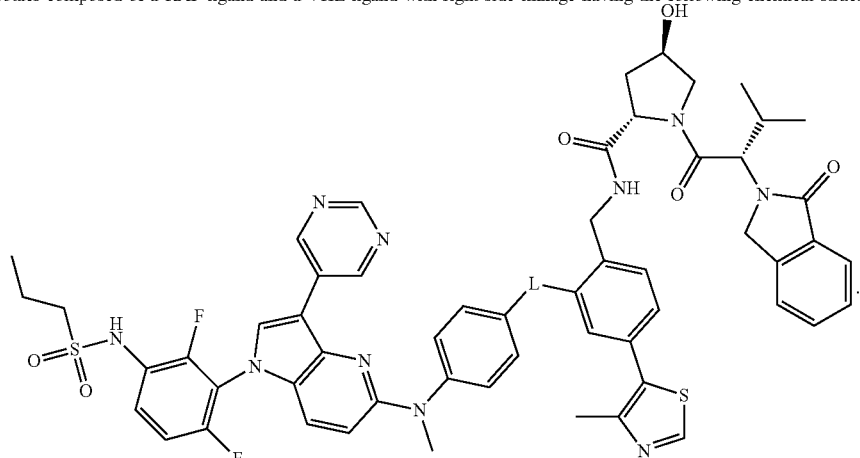

(PROTAC-XXXX)

| PROTAC-XXXX Compound | L | Mass | DC$_{50}$ (μM) | Dmax (%) |
|---|---|---|---|---|
| PROTAC-XXXX-50 | ![](O-CH2CH2-O-CH2CH2-N-piperazine-N) | 1250 | | |
| PROTAC-XXXX-51 | | 1248 | | |
| PROTAC-XXXX-52 | ![](N-piperazine-N-CH2CH2-O-CH2CH2CH2-O) | 1250 | | |
| PROTAC-XXXX-53 | ![](N-piperazine-N-CH2CH2-O-CH2CH2-O) | 1250 | | |
| PROTAC-XXXX-54 | | 1248 | | |
| PROTAC-XXXX-55 | ![](N-piperazine-N-CH2CH2-N-piperazine-N) | 1274 | | |
| PROTAC-XXXX-56 | ![](O-CH2CH2-N-piperazine-N-CH2CH2-O) | 1250 | | |
| PROTAC-XXXX-57 | ![](O-CH2CH2-N-piperazine-N-CH2CH2-O) | 1250 | | |
| PROTAC-XXXX-58 | ![](O-CH2CH2CH2-O-CH2CH2-N-piperazine-N) | 1264 | | |

TABLE 40-continued

Protacs composed of a RAF ligand and a VHL ligand with right-side linkage having the following chemical structure

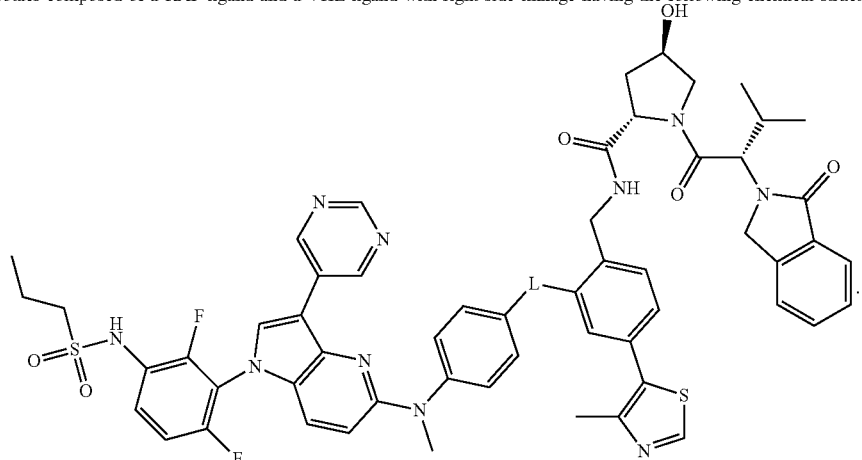

(PROTAC-XXXX)

| PROTAC-XXXX Compound | L | Mass | DC$_{50}$ (μM) | Dmax (%) |
|---|---|---|---|---|
| PROTAC-XXXX-59 | ----O~~~O~~~N(piperazine)N---- | 1264 | | |
| PROTAC-XXXX-60 | ----O~~~O~~~N(piperazine)N---- | 1264 | | |
| PROTAC-XXXX-61 | ----O~~~~~N(piperazine)N---- | 1262 | | |
| PROTAC-XXXX-62 | ----N(piperazine)N~~~O~~O---- | 1264 | | |
| PROTAC-XXXX-63 | ----N(piperazine)N~~O~~O---- | 1264 | | |
| PROTAC-XXXX-64 | ----N(piperazine)N~~O~~~O---- | 1264 | | |
| PROTAC-XXXX-65 | ----N(piperazine)N~~~~O---- | 1262 | | |
| PROTAC-XXXX-66 | ----N(piperazine)N~~~N(piperazine)N---- | 1288 | | |
| PROTAC-XXXX-67 | ----O~~N(piperazine)N~~O---- | 1264 | | |
| PROTAC-XXXX-68 | ----O~~~N(piperazine)N~~O---- | 1264 | | |

TABLE 40-continued

Protacs composed of a RAF ligand and a VHL ligand with right-side linkage having the following chemical structure

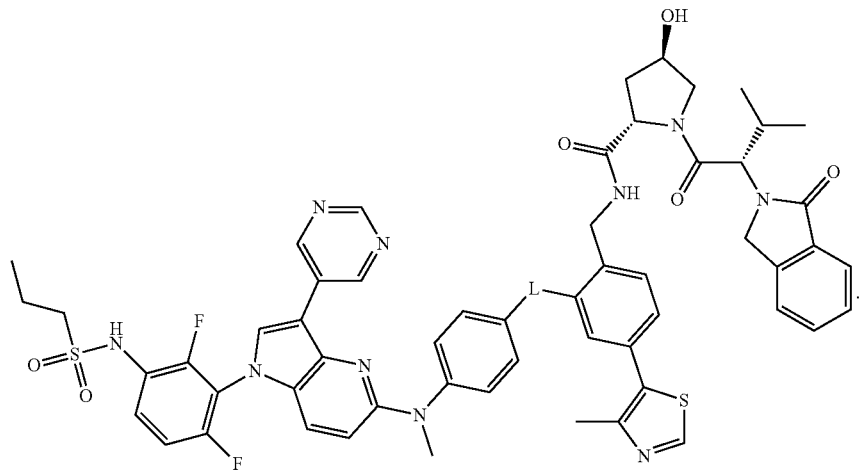

(PROTAC-XXXX)

| PROTAC-XXXX Compound | L | Mass | $DC_{50}$ (μM) | Dmax (%) |
|---|---|---|---|---|
| PROTAC-XXXX-69 | ![](piperazine linker) | 1264 | | |
| PROTAC-XXXX-70 | ![](O linker) | 1080 | | |

TABLE 41

Exemplary protein targeting moieties and compounds of the present disclosure.

| No. | Compounds | Purity | Observed Mass |
|---|---|---|---|
| 1 | | 97.70% | 335.14 |
| 2 | | >98% | 393.18 |

TABLE 41-continued

Exemplary protein targeting moieties and compounds of the present disclosure.

| No. | Compounds | Purity | Observed Mass |
|---|---|---|---|
| 3 | | 93.80% | 378.17 |
| 4 | | >98% | 407.19 |
| 5 | | >98% | 423.19 |
| 6 | | >98% | 421.21 |

TABLE 41-continued
Exemplary protein targeting moieties and compounds of the present disclosure.
| No. | Compounds | Purity | Observed Mass |
|---|---|---|---|
| 7 | 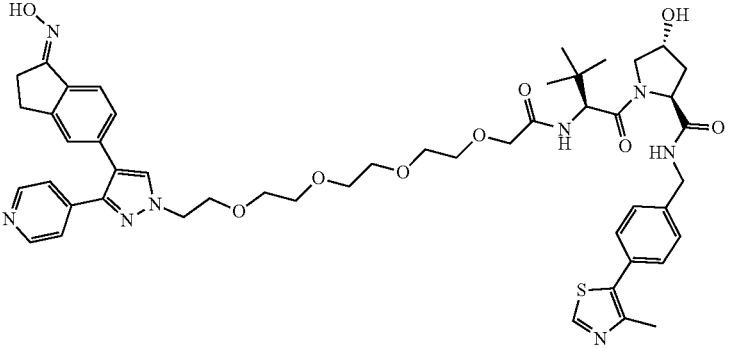 [SMILES: Cc1ncsc1-c1ccc(CNC(=O)[C@@H]2C[C@@H](O)CN2C(=O)[C@@H](NC(=O)COCCOCCOCCOCCn2cc(-c3ccc4c(c3)CC/C4=N\O)c(-c3ccncc3)n2)C(C)(C)C)cc1] | >98% | 937.4 |
| 8 | 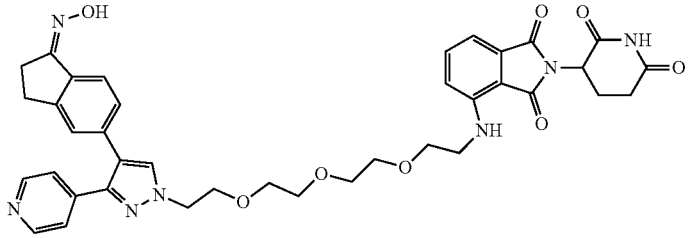 [SMILES: O=C1CCC(N2C(=O)c3cccc(NCCOCCOCCOCCn4cc(-c5ccc6c(c5)CC/C6=N/O)c(-c5ccncc5)n4)c3C2=O)C(=O)N1] | >98% | 722.27 |
| 9 | 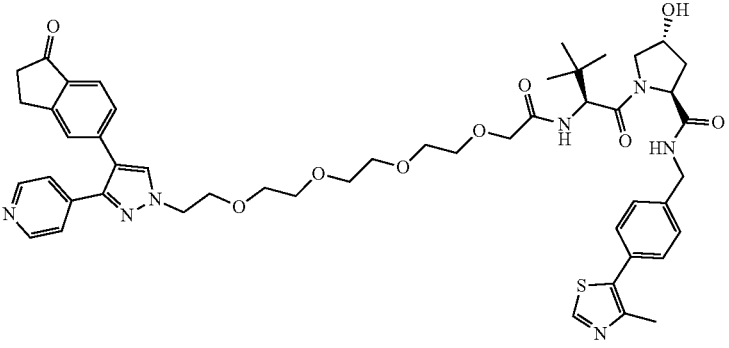 [SMILES: Cc1ncsc1-c1ccc(CNC(=O)[C@@H]2C[C@@H](O)CN2C(=O)[C@@H](NC(=O)COCCOCCOCCOCCn2cc(-c3ccc4c(c3)CCC4=O)c(-c3ccncc3)n2)C(C)(C)C)cc1] | >98% | 922.38 |
| 10 | 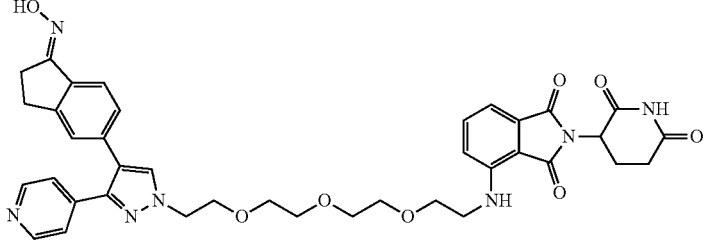 [SMILES: O=C1CCC(N2C(=O)c3cccc(NCCOCCOCCOCCn4cc(-c5ccc6c(c5)CC/C6=N\O)c(-c5ccncc5)n4)c3C2=O)C(=O)N1] | 88.30% | 708.23 |

TABLE 41-continued

Exemplary protein targeting moieties and compounds of the present disclosure.

| No. | Compounds | Purity | Observed Mass |
|---|---|---|---|
| 11 | | >98% | 967.32 |
| 12 | | >98% | 481.1 |
| 13 | | >98% | 863.3 |

TABLE 41-continued
Exemplary protein targeting moieties and compounds of the present disclosure.
| No. | Compounds | Purity | Observed Mass |
|---|---|---|---|
| 14 | 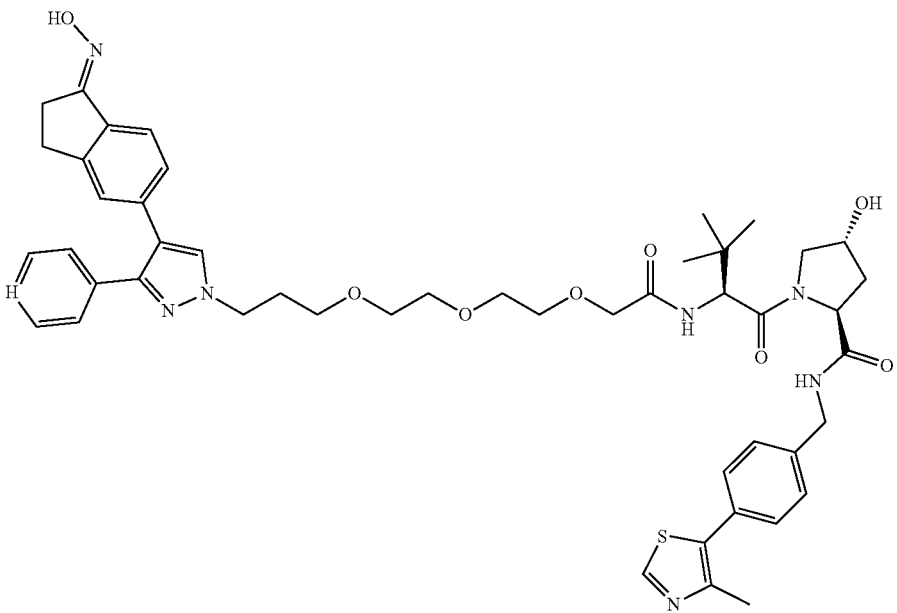 | >98% | 907.32 |
| 15 | 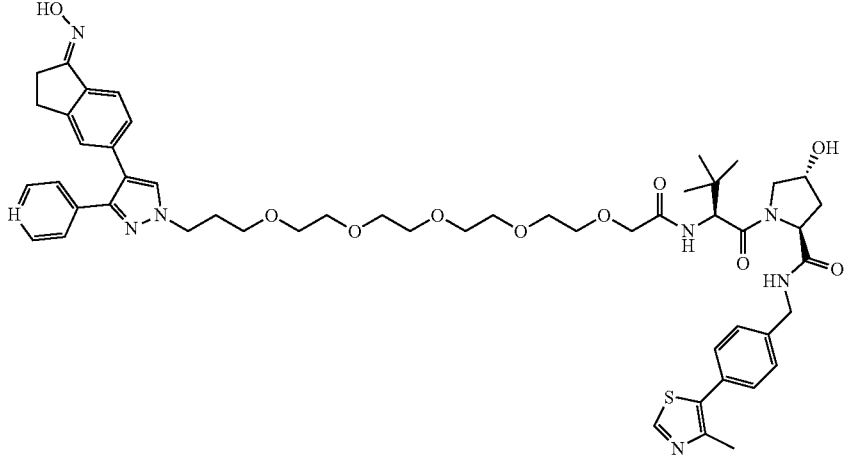 | >98% | 995.37 |
| 16 | 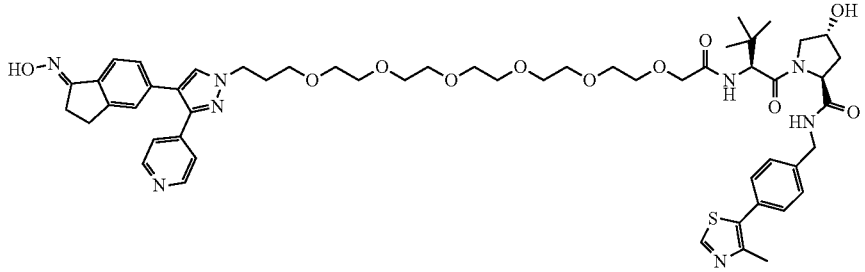 [SMILES: Cc1ncsc1-c1ccc(CNC(=O)[C@@H]2C[C@@H](O)CN2C(=O)[C@@H](NC(=O)COCCOCCOCCOCCOCCOCCCn2cc(-c3ccc4c(c3)CC/C4=N\O)c(-c3ccncc3)n2)C(C)(C)C)cc1] | >98% | 1039.39 |

TABLE 41-continued
Exemplary protein targeting moieties and compounds of the present disclosure.
| No. | Compounds | Purity | Observed Mass |
|---|---|---|---|
| 17 | 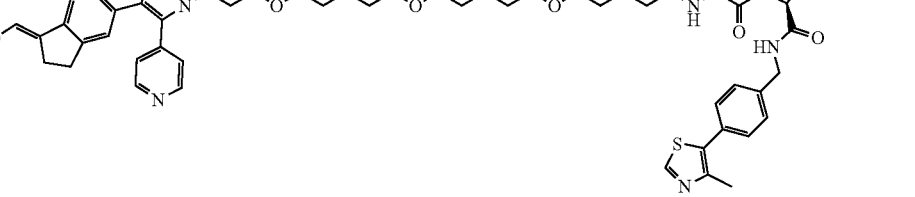 | 97.00% | 1039.39 |
| 18 | 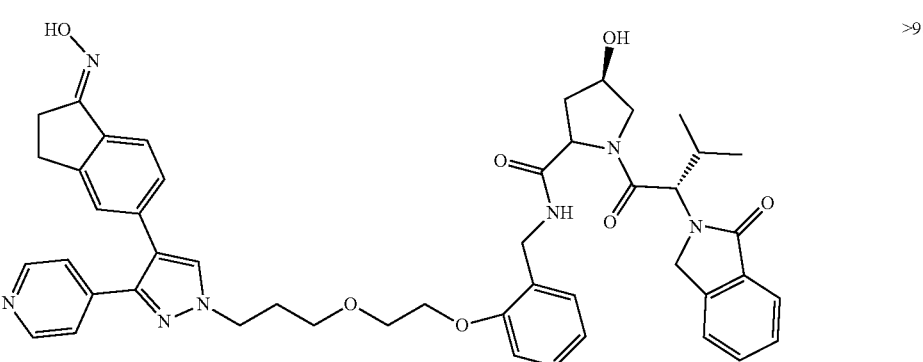 | >98% | 923.29 |
| 19 | 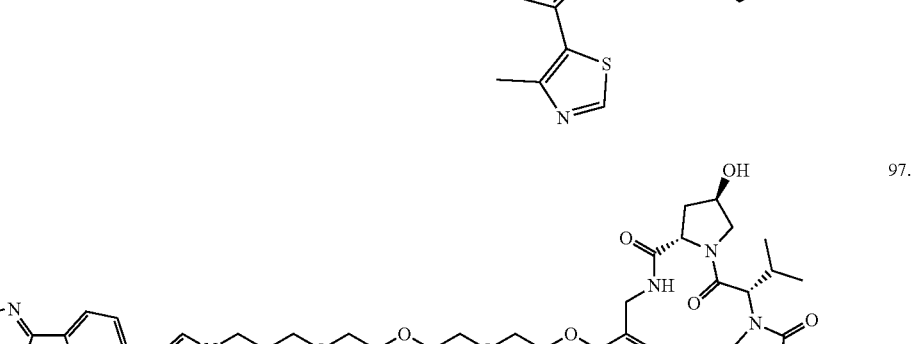 | 97.80% | 1011.34 |
| 20 | 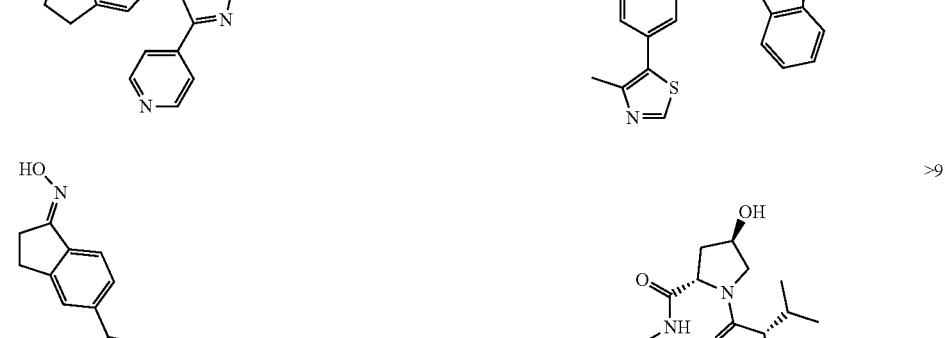 | >98% | 1055.36 |

TABLE 41-continued

Exemplary protein targeting moieties and compounds of the present disclosure.

| No. | Compounds | Purity | Observed Mass |
|---|---|---|---|
| 21 | | >98% | 1099.39 |
| 22 | | 97.80% | 692.2 |
| 23 | | 92% | 736.22 |
| 24 | | >98% | 951.34 |
| 25 | | >98% | 951.34 |

TABLE 41-continued

Exemplary protein targeting moieties and compounds of the present disclosure.

| No. | Compounds | Purity | Observed Mass |
|---|---|---|---|
| 26 | | >98% | 1011.34 |
| 27 | | | |
| 28 | | >98% | 709.21 |
| 29 | | 85% | 648.17 |

TABLE 41-continued
Exemplary protein targeting moieties and compounds of the present disclosure.
| No. | Compounds | Purity | Observed Mass |
|-----|-----------|--------|---------------|
| 30 | 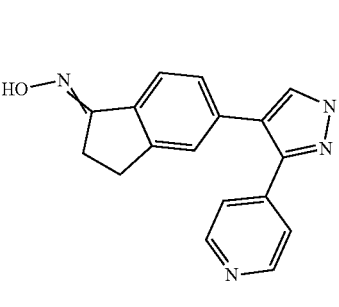 | >98% | 648.17 |
| 31 | 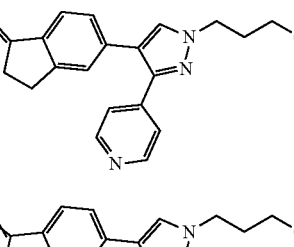 | >98% | 780.24 |
| 32 | 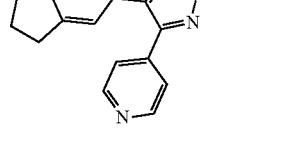 | >98% | 780.24 |
| 33 | 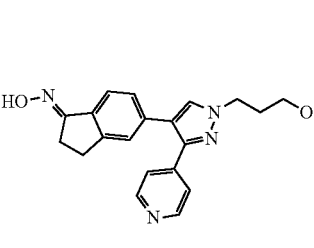 | >98% | 824.26 |
| 34 | 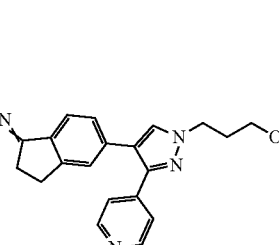 | 85% | 824.26 |
| 35 | 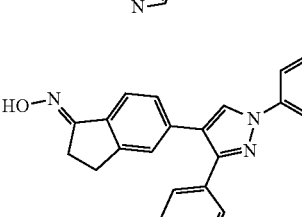 | 96.90% | 771.18 |

TABLE 41-continued

Exemplary protein targeting moieties and compounds of the present disclosure.

| No. | Compounds | Purity | Observed Mass |
|---|---|---|---|
| 36 | | 92.50% | 561.89 |
| 37 | | >98% | 683.14 |
| 38 | | >98% | 683.14 |
| 39 | | 97.50% | 727.16 |
| 40 | | >98% | 868.29 |

TABLE 41-continued
Exemplary protein targeting moieties and compounds of the present disclosure.
| No. | Compounds | Purity | Observed Mass |
|---|---|---|---|
| 41 | 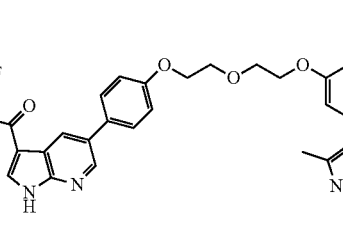 | >98% | 1135.25 |
| 42 | 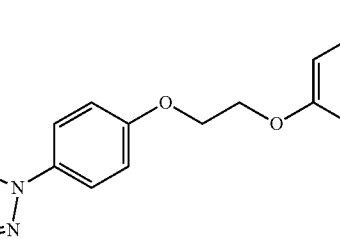 | 96% | 683.14 |
| 43 | 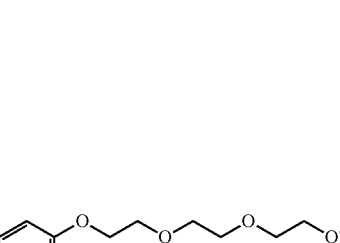 | >98% | 771.19 |
| 44 | 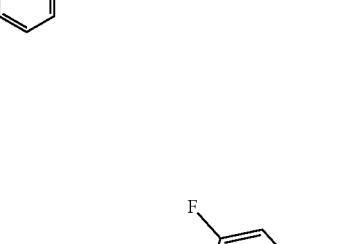 | >98% | 351.93 |
| 45 | 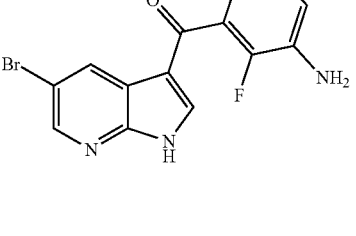 | 96.20% | 815.29 |

TABLE 41-continued

Exemplary protein targeting moieties and compounds of the present disclosure.

| No. | Compounds | Purity | Observed Mass |
|-----|-----------|--------|---------------|
| 46  |           | 95.80% | 859.31        |
| 47  |           | 96.70% | 1179.37       |
| 48  |           | 93.10% | 1267.42       |
| 49  |           | 97%    | 1311.45       |

TABLE 41-continued
Exemplary protein targeting moieties and compounds of the present disclosure.
| No. | Compounds | Purity | Observed Mass |
|---|---|---|---|
| 50 | 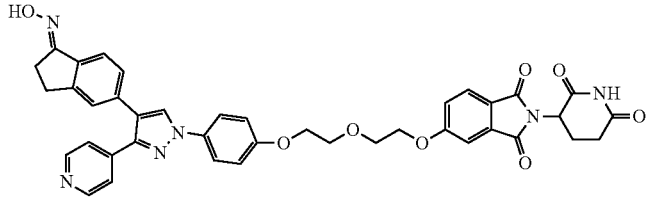 | 98% | 727.23 |
| 51 | 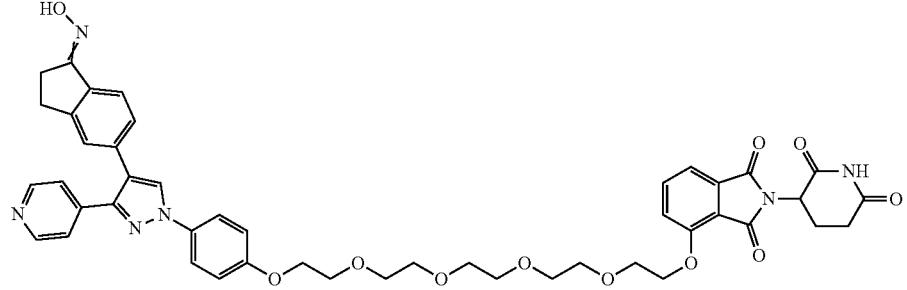 [SMILES: O=C1CCC(N2C(=O)c3cccc(OCCOCCOCCOCCOCCOc4ccc(-n5cc(-c6ccc7c(c6)CC/C7=N\O)c(-c6ccncc6)n5)cc4)c3C2=O)C(=O)N1] | 95% | 859.31 |
| 52 | 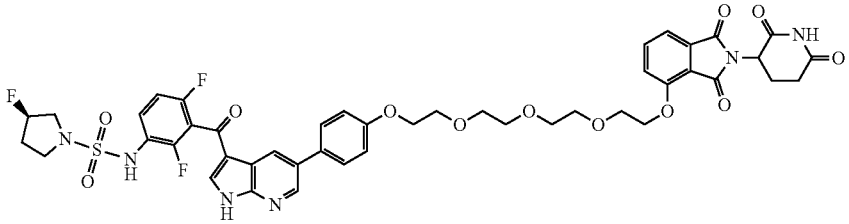 [SMILES: O=C1CCC(N2C(=O)c3cccc(OCCOCCOCCOCCOc4ccc(-c5cnc6[nH]cc(C(=O)c7c(F)ccc(NS(=O)(=O)N8CC[C@@H](F)C8)c7F)c6c5)cc4)c3C2=O)C(=O)N1] | 95.70% | 949.24 |
| 53 | 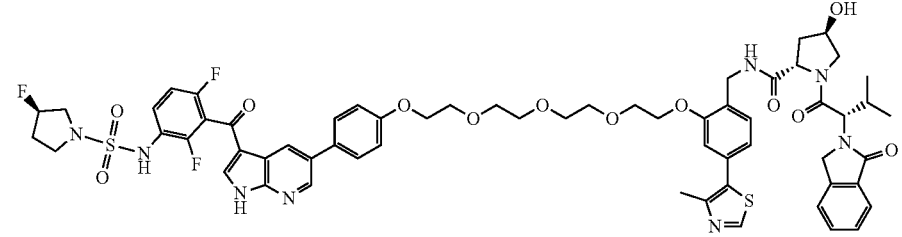 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCOCCOc2ccc(-c3cnc4[nH]cc(C(=O)c5c(F)ccc(NS(=O)(=O)N6CC[C@@H](F)C6)c5F)c4c3)cc2)c1] | >98% | 1223.39 |
| 54 | 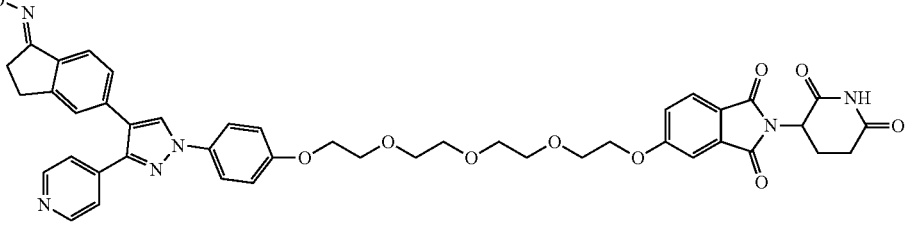 | >98% | 815.28 |
| 55 | 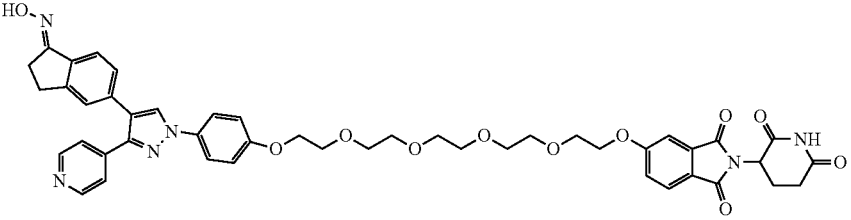 [SMILES: O=C1CCC(N2C(=O)c3ccc(OCCOCCOCCOCCOCCOc4ccc(-n5cc(-c6ccc7c(c6)CC/C7=N\O)c(-c6ccncc6)n5)cc4)cc3C2=O)C(=O)N1] | >98% | 859.31 |

TABLE 41-continued

Exemplary protein targeting moieties and compounds of the present disclosure.

| No. | Compounds | Purity | Observed Mass |
|---|---|---|---|
| 56 | | 96.00% | 1037.29 |
| 57 | | >98% | 1075.33 |
| 58 | | >98% | 1119.36 |
| 59 | | 97.70% | 693.24 |
| 60 | | 97.30% | 781.29 |

TABLE 41-continued

Exemplary protein targeting moieties and compounds of the present disclosure.

| No. | Compounds | Purity | Observed Mass |
|---|---|---|---|
| 61 | | 97.80% | 905.22 |
| 62 | | >98% | 949.24 |
| 63 | | >98% | 905.18 |
| 64 | | >98% | 1163.35 |
| 65 | | 97.80% | 1251.4 |
| 66 | | 95.10% | 825.28 |

TABLE 41-continued
Exemplary protein targeting moieties and compounds of the present disclosure.
| No. | Compounds | Purity | Observed Mass |
|---|---|---|---|
| 67 | 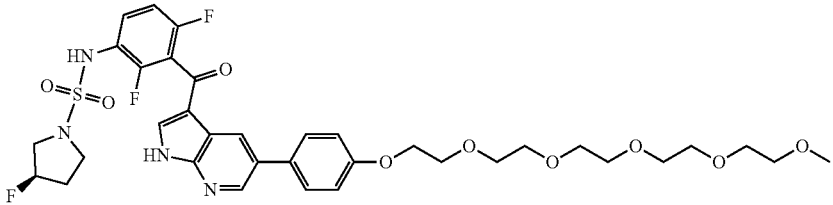 | >98% | 1207.22 |
| 68 | 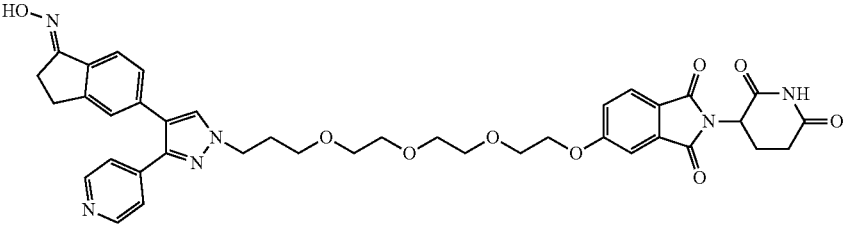 [SMILES: O=C1CCC(N2C(=O)c3ccc(OCCOCCOCCOCCCn4cc(-c5ccc6c(c5)CC/C6=N\O)c(-c5ccncc5)n4)cc3C2=O)C(=O)N1] | >98% | 737.16 |
| 69 | 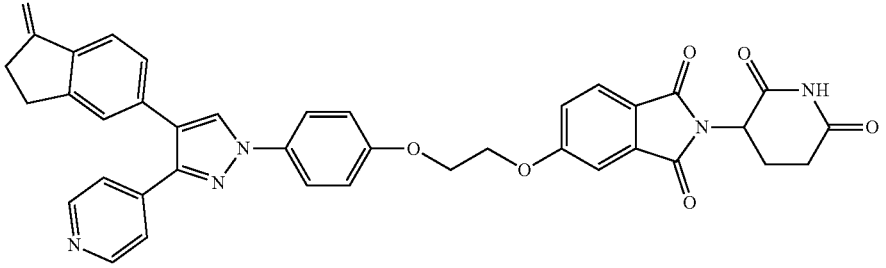 | 97.30% | 669.1 |
| 70 | 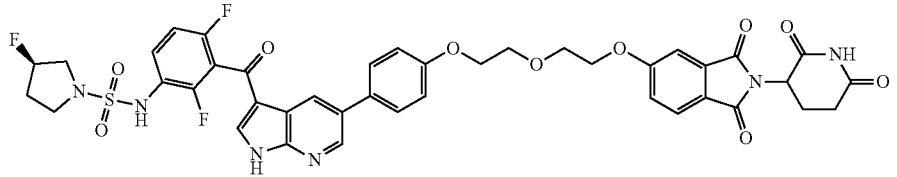 [SMILES: O=C1CCC(N2C(=O)c3ccc(OCCOCCOc4ccc(-c5cnc6[nH]cc(C(=O)c7c(F)ccc(NS(=O)(=O)N8CC[C@@H](F)C8)c7F)c6c5)cc4)cc3C2=O)C(=O)N1] | >98% | 861.01 |
| 71 | 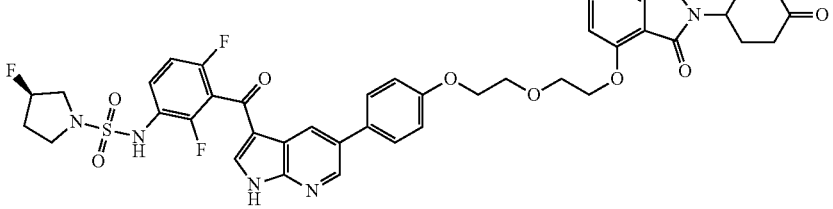 |  | 860.82 |

TABLE 41-continued

Exemplary protein targeting moieties and compounds of the present disclosure.

| No. | Compounds | Purity | Observed Mass |
|---|---|---|---|
| 72 | | | 712.76 |
| 73 | | | 712.76 |
| 74 | | | 992.98 |
| 75 | | | 756.82 |
| 76 | | | 800.87 |
| 77 | | | 844.92 |

TABLE 41-continued
Exemplary protein targeting moieties and compounds of the present disclosure.
| No. | Compounds | Purity | Observed Mass |
|---|---|---|---|
| 78 | 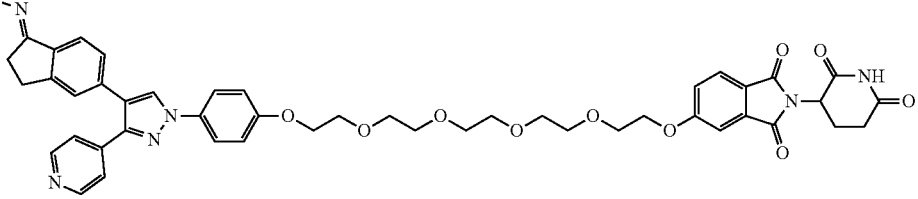 | | 844.92 |
| 79 | 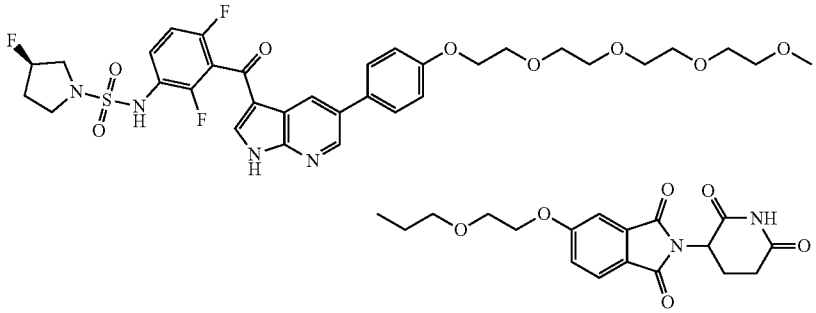 | | 1037.03 |
| 80 | 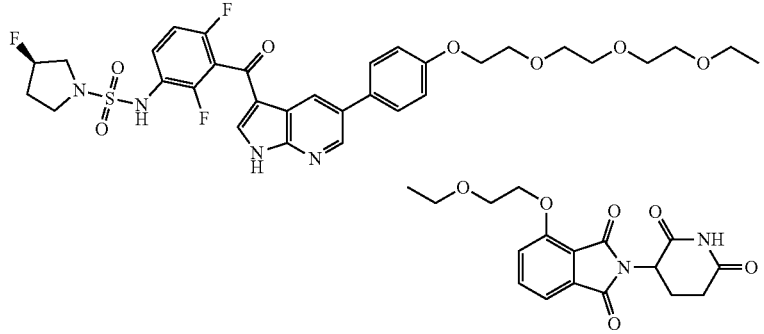 | | 992.97 |
| 81 | 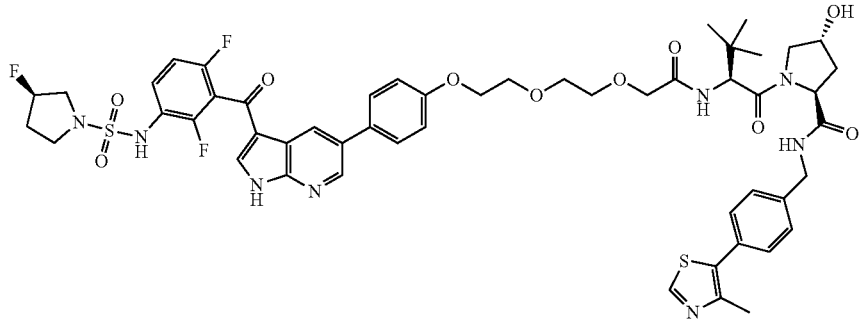 [SMILES: Cc1ncsc1-c1ccc(CNC(=O)[C@@H]2C[C@@H](O)CN2C(=O)[C@@H](NC(=O)COCCOCCOc2ccc(-c3cnc4[nH]cc(C(=O)c5c(F)ccc(NS(=O)(=O)N6CC[C@@H](F)C6)c5F)c4c3)cc2)C(C)(C)C)cc1] | | 1103.23 |
| 82 | 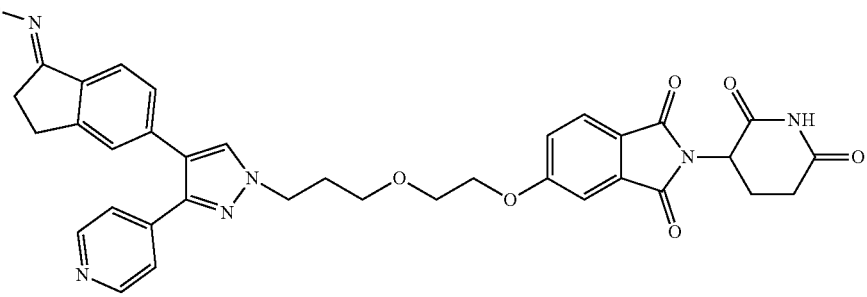 | | 648.66 |

TABLE 41-continued

Exemplary protein targeting moieties and compounds of the present disclosure.

| No. | Compounds | Purity | Observed Mass |
|---|---|---|---|
| 83 | | | 648.66 |
| 84 | | | 1089.22 |
| 85 | | | 1075.19 |

Table 42. Exemplary protein targeting moieties and compounds of the present disclosure (see FIG. 2).
Table 43. Degradation data for the Exemplary Compounds of Table 42 (See FIG. 3).

Specific Embodiments of the Present Disclosure

The present disclosure encompasses the following specific embodiments. These following embodiments may include all of the features recited in a proceeding embodiment, as specified. Where applicable, the following embodiments may also include the features recited in any proceeding embodiment inclusively or in the alternative.

In any aspect or embodiment, the description provides the following exemplary RAF PROTAC molecules (compounds of Tables 1-43, i.e., any one of the compounds of Table 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or a combination thereof), including salts, prodrugs, polymorphs, analogs, derivatives, and deuterated forms thereof.

As such, the description provides a compound comprising the structure of any one of the compounds of Tables 1-43 (i.e., any one of the compounds of Table 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or a combination thereof), therapeutic compositions comprising the same, and methods of use as described herein.

In an aspect, the present disclosure provides a bifunctional compound. The binfuctional compound has the chemical structure:
ULM-L-PTM,
or a pharmaceutically acceptable salt, enantiomer, stereoisomer, solvate, polymorph or prodrug thereof, wherein: the ULM is a small molecule E3 ubiquitin ligase binding moiety that binds an E3 ubiquitin ligase; the PTM is a small molecule comprising a rapidly accelerated fibrosarcoma (RAF) protein targeting moiety; and the L is a bond or a chemical linking moiety connecting the ULM and the PTM.

In any aspect or embodiment described herein, the E3 ubiquitin ligase binding moiety that targets an E3 ubiquitin ligase selected from the group consisting of Von Hippel-Lindau (VLM), cereblon (CLM), mouse double-minute homolog2 (MLM), and IAP (ILM).

In any aspect or embodiment described herein, the PTM is represented by chemical structure PTM-Ia or PTM-Ib:

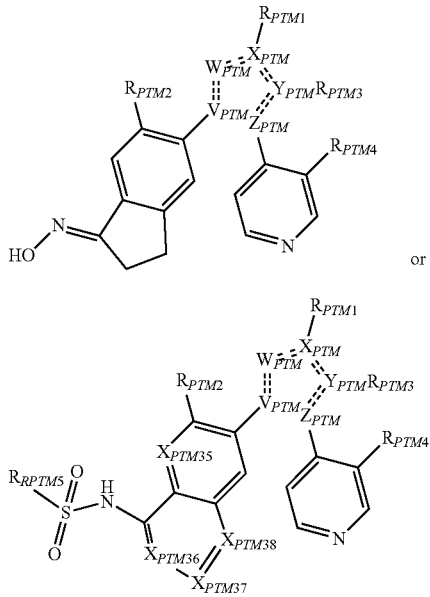

PTM-Ia or

PTM-Ib wherein:
- double dotted bonds are aromaric bonds;
- $V_{PTM}$, $W_{PTM}$, $X_{PTM}$, $Y_{PTM}$, $Z_{PTM}$ is one of the following combinations: C, CH, N, N, C; C, N, N, CH, C; C, O, C, CH, C; C, S, C, CH, C; C, CH, C, O, C; C, CH, C, S, C; C, CH, N, CH, C; N, CH, C, CH, C; C, CH, C, CH, N; N, N, C, CH, C; N, CH, C, N, C; C, CH, C, N, N; C, N, C, CH, N; C, N, C, N, C; and C, N, N, N, C;
- XPTM35, XPTM36, XPTM37, and XPTM38 are independently selected from CH and N;
- $R_{PTM1}$ is covalently joined to a ULM, a chemical linker group (L), a CLM, an ILM, a VLM, MLM, a ULM', a CLM', a ILM', a VLM', a MLM', or combination thereof;
- $R_{PTM2}$ is hydrogen, halogen, aryl, methyl, ethyl, OCH$_3$, NHCH$_3$ or M1-CH$_2$—CH$_2$-M2, wherein M1 is CH$_2$, O and NH, and M2 is hydrogen, alkyl, cyclic alkyl, aryl or heterocycle;
- $R_{PTM3}$ is absent, hydrogen, aryl, methyl, ethyl, other alkyl, cyclic alkyl, OCH$_3$, NHCH$_3$ or M1-CH$_2$—CH$_2$-M2, wherein M1 is CH$_2$, O and NH, and M2 is hydrogen, alkyl, cyclic alkyl, aryl or heterocycle;
- $R_{PTM4}$ is hydrogen, halogen, aryl, methyl, ethyl, OCH$_3$, NHCH$_3$ or M1-CH$_2$—CH$_2$-M2, wherein M1 is CH$_2$, O and NH, and M2 is hydrogen, alkyl, cyclic alkyl, aryl or heterocycle; and
- $R_{PTM5}$ is selected from the group consisting of

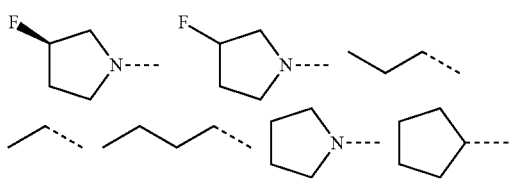

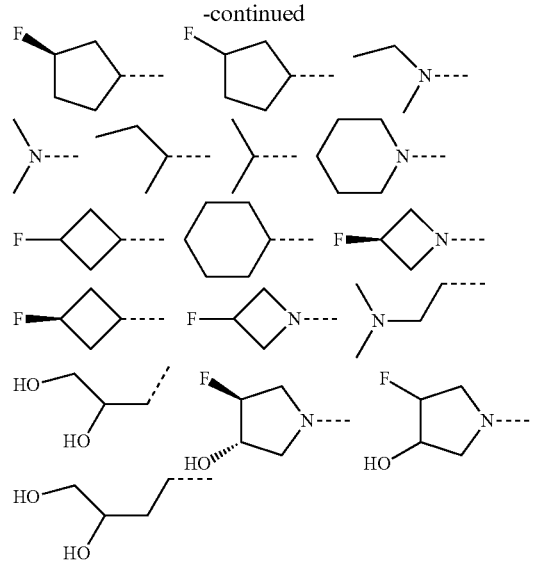

In any aspect or embodiment described herein, the PTM is represented by chemical structure PTM-IIa or PTM-IIb:

PTM-IIa

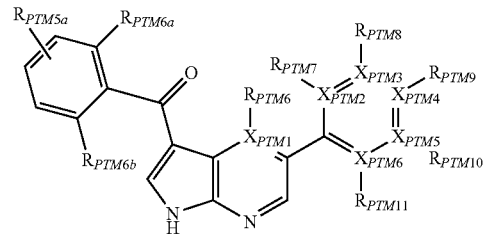

or

PTM-IIb

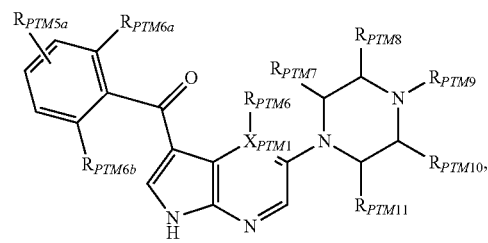

wherein:
- $X_{PTM1}$, $X_{PTM2}$, $X_{PTM3}$, $X_{PTM4}$, $X_{PTM5}$, and $X_{PTM6}$ are independently selected from CH or N;
- $R_{PTM5a}$ is selected from the group consisting of: bond, optionally substituted amine, optionally substituted amide (e.g., optionally substituted with an alkyl, methyl, ethyl, propyl, or butyl group), H, or

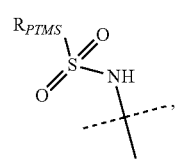

—NHC(O)R$_{PTM5}$;

$R_{PTM5}$ is selected from the group consisting of

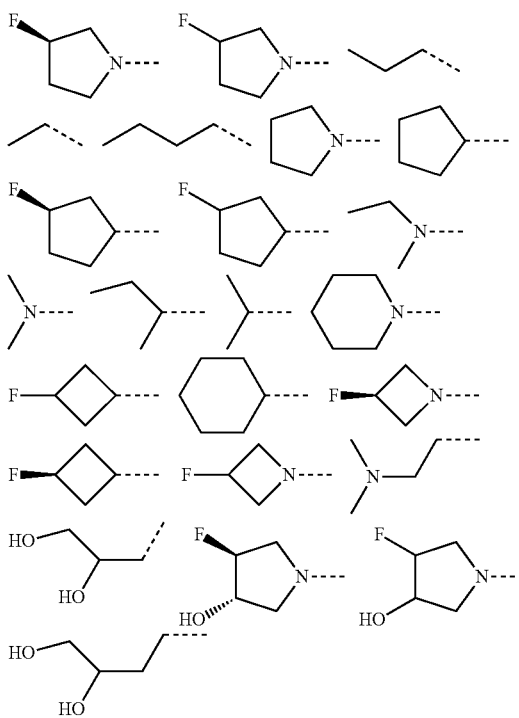

$R_{PTM6a}$ and $R_{PTM6b}$ are each independently selected from hydrogen, halogen, or $C_1$-$C_6$ alkyl (linear, branched, optionally substituted; e.g., optionally substitute methy or ethyl);

$R_{PTM6}$ is either of the following groups: absent, hydrogen, halogen, aryl, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM7}$ is absent, hydrogen, halogen, aryl, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM8}$, $R_{PTM9}$ or $R_{PTM10}$ are independently selected from the group consisting of absent, hydrogen, halogen, aryl, heteroaryl, alkyl, cycloalkyl, heterocycle, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM11}$ is absent, hydrogen, halogen, methyl, ethyl, $OCH_3$, $NHCH_3$ or M1-$CH_2$—$CH_2$-M2 in which M1, wherein $CH_2$, O and NH, and M2 is hydrogen, alkyl, cyclic alkyl, aryl or heterocycle; and at least one of $R_{PTM8}$, $R_{PTM9}$ or $R_{PTM10}$ is modified to be covalently joined to a ULM, a chemical linker group (L), a CLM, an ILM, a VLM, MLM, a ULM', a CLM', a ILM', a VLM', a MLM', or combination thereof.

In any aspect or embodiment described herein, when $R_{PTM9}$ is the covalently joined position, $R_{PTM7}$ and $R_{PTM8}$ are connected together via a covalent bond in a way to form a bicyclic group with the ring to which $R_{PTM7}$ and $R_{PTM8}$ are attached; or when $R_{PTM8}$ is the covalently joined position, $R_{PTM9}$ and $R_{PTM10}$ are connected together via a covalent bond in a way to form a bicyclic group with the ring to which $R_{PTM9}$ and $R_{PTM10}$ are attached; or when RPTM10 is the covalently joined position, RPTM8 and RPTM9 are connected together via a covalent bond in a way to form a bicyclic group with the ring to which RPTM8 and RPTM9 are attached.

In any aspect or embodiment described herein, the PTM is represented by chemical structure:

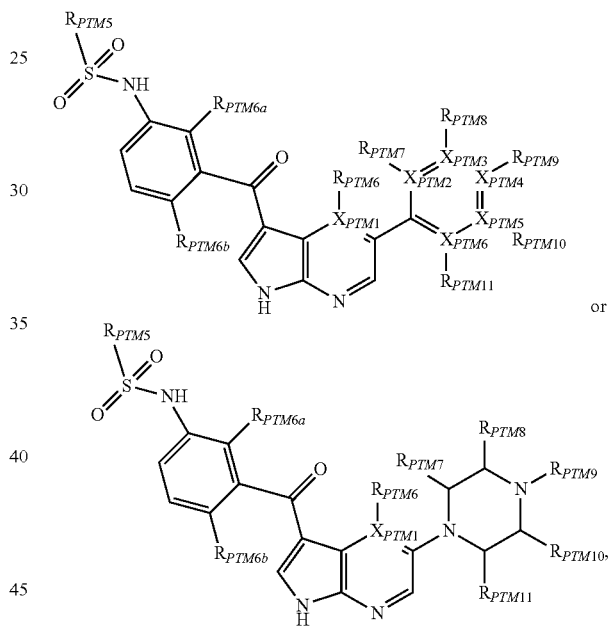

wherein $R_{PTM5}$, $R_{PTM6a}$, $R_{PTM6b}$, $R_{PTM6}$, $R_{PTM7}$, $R_{PTM8}$, $R_{PTM9}$, $R_{PTM10}$, $R_{PTM11}$ are as described herein.

In any aspect or embodiment described herein, the PTM is represented by chemical structure PTM-III:

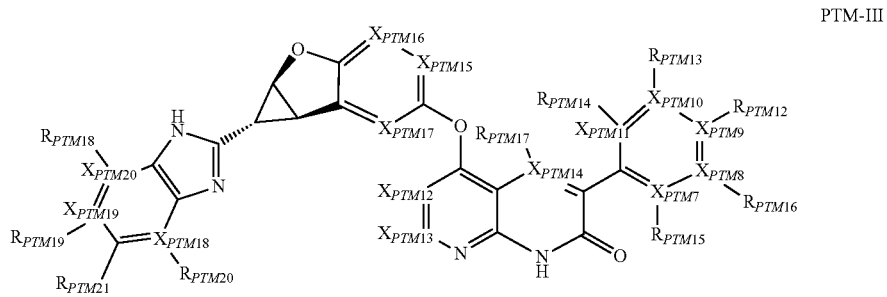

PTM-III wherein:

$X_{PTM7}$, $X_{PTM8}$, $X_{PTM9}$, $X_{PTM10}$, $X_{PTM11}$, $X_{PTM12}$, $X_{PTM13}$, $X_{PTM14}$, $X_{PTM15}$, $X_{PTM16}$, $X_{PTM17}$, $X_{PTM18}$, $X_{PTM19}$, $X_{PTM20}$ are independently CH or N;

$R_{PTM12}$, $R_{PTM13}$, $R_{PTM14}$, $R_{PTM15}$, $R_{PTM16}$, $R_{PTM17}$, $R_{PTM18}$, $R_{PTM19}$ are independently selected from the group consisting of absent, hydrogen, halogen, aryl, heteroaryl, cycloalkyl, heterocycle, methyl, ethyl, other alkyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM20}$ is a small group containing less than four non-hydrogen atoms;

$R_{PTM21}$ is selected from the group consisting of trifluoromethyl, chloro, bromo, fluoro, methyl, ethyl, propyl, isopropyl, tert-butyl, butyl, iso-butyl, cyclopropyl, cyclobutyl, cyclopentyl, cyclohexyl, $OCH_3$, $NHCH_3$, dimethylamino or M1-$CH_2$—$CH_2$-M2, wherein M1 is $CH_2$, O or NH, and M2 is hydrogen, alkyl, cyclic alkyl, aryl or heterocycle; and at least one of $R_{PTM12}$, $R_{PTM13}$ and $R_{PTM16}$ is modified to be covalently joined to a ULM, a chemical linker group (L), a CLM, an ILM, a VLM, MLM, a ULM', a CLM', a ILM', a VLM', a MLM', or combination thereof.

In any aspect or embodiment described herein, when $R_{PTM12}$ is the covalently joined position, $R_{PTM13}$ and $R_{PTM14}$ are connected together via a covalent bond in a way to form a bicyclic group with the ring to which $R_{PTM13}$ and $R_{PTM14}$ are attached, and/or $R_{PTM15}$ and $R_{PTM16}$ are connected together via a covalent bond in a way to form a bicyclic group with the ring to which $R_{PTM15}$ and $R_{PTM16}$ are attached; when $R_{PTM13}$ is the covalently joined position, $R_{PTM12}$ and $R_{PTM16}$ are connected together via a covalent bond in a way to form a bicyclic group with the ring to which $R_{PTM12}$ and $R_{PTM16}$ are attached, and/or $R_{PTM15}$ and $R_{PTM16}$ are connected together via a covalent bond in a way to form a bicyclic group with the ring to which $R_{PTM15}$ and $R_{PTM16}$ are attached; or when $R_{PTM16}$ is the covalently joined position, $R_{PTM12}$ and $R_{PTM13}$ are connected together via a covalent bond in a way to form a bicyclic group with the ring to which $R_{PTM12}$ and $R_{PTM13}$ are attached, and/or $R_{PTM13}$ and $R_{PTM14}$ are connected together via a covalent bond in a way to form a bicyclic group with the ring to which $R_{PTM13}$ and $R_{PTM14}$ are attached In any aspect or embodiment described herein, the PTM is represented by chemical structure PTM-IVa or PTM-IVb:

PTM-IVa

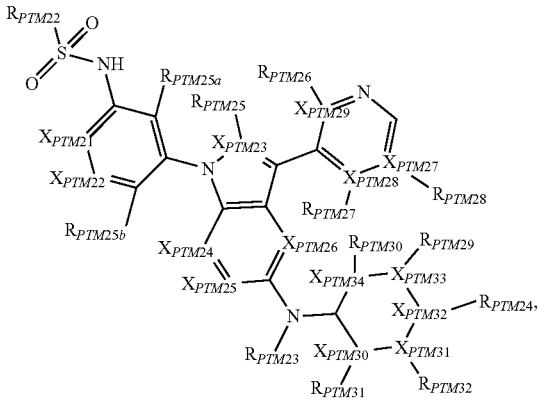

PTM-IVb

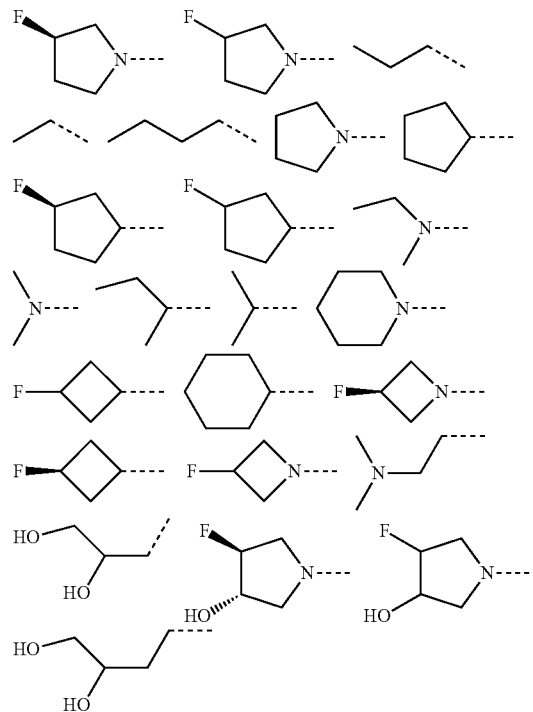

wherein:

$X_{PTM21}$, $X_{PTM22}$, $X_{PTM23}$, $X_{PTM24}$, $X_{PTM25}$, $X_{PTM26}$, $X_{PTM27}$, $X_{PTM28}$, $X_{PTM29}$, $X_{PTM30}$, $X_{PTM31}$, $X_{PTM32}$, $X_{PTM33}$, $X_{PTM34}$ are independently CH or N;

$R_{PTM22}$ is selected from the group consisting of $R_{PTM25a}$ and $R_{PTM125b}$, are each independently selected from hydrogen, halogen, or $C_1$-$C_6$ alkyl (linear, branched, optionally substituted);

$R_{PTM23}$, $R_{PTM24}$, $R_{PTM28}$, $R_{PTM29}$, $R_{PTM30}$, $R_{PTM31}$, $R_{PTM32}$ are independently selected from the group consisting of absent, bond, hydrogen, halogen, aryl (optionally substituted), heteroaryl (optionally substituted), cycloalkyl (optionally substituted), heterocycle (optionally substituted), methyl, ethyl (optionally substituted), other alkyl (linear, branched, optionally substituted), $OCH_3$, $NHCH_3$ or M1-$CH_2$—$CH_2$-M2, wherein M1 is $CH_2$, O and NH, and M2 is hydrogen, alkyl (linear, branched, optionally substituted), cyclic alkyl (optionally substituted), aryl (optionally substituted) or heterocycle (optionally substituted); and $R_{PTM25}$ is absent or a small group containing less than four non-hydrogen atoms (e.g., selected from absent, hydrogen, halogen, $C_1$-$C_6$ alkyl (linear, branched, optionally substituted), $OCH_3$, $NHCH_3$ or $SCH_3$);

$R_{PTM26}$ is absent or a small group containing less than four non-hydrogen atoms (e.g., selected from absent, hydrogen, halogen, $C_1$-$C_6$ alkyl (linear, branched, optionally substituted), $OCH_3$, $NHCH_3$ or $SCH_3$);

$R_{PTM27}$ is selected from the group consisting of absent, hydrogen, halogen, $C_1$-$C_6$ alkyl (linear, branched, optionally substituted; e.g., optionally substituted methyl or ethyl), $OCH_3$, $NHCH_3$ or $SCH_3$; and at least one of $R_{PTM24}$, $R_{PTM29}$, $R_{PTM32}$ is modified to be covalently joined to a ULM, a chemical linker group (L), a CLM, an ILM, a VLM, MLM, a ULM', a CLM', a ILM', a VLM', a MLM', or combination thereof.

In any aspect or embodiment described herein, when $R_{PTM24}$ is the covalently joined position, $R_{PTM31}$ and $R_{PTM32}$ are connected together via a covalent bond in a way to form a bicyclic group with the ring to which $R_{PTM31}$ and $R_{PTM32}$ are attached, or $R_{PTM29}$ and $R_{PTM30}$ are connected together via a covalent bond in a way to form a bicyclic group with the ring to which $R_{PTM29}$ and $R_{PTM30}$ are attached; or when $R_{PTM29}$ is the covalently joined position, $R_{PTM24}$ and $R_{PTM32}$ are connected together via a covalent bond in a way to form a bicyclic group with the ring to which $R_{PTM24}$ and $R_{PTM32}$ are attached, and/or $R_{PTM31}$ and $R_{PTM32}$ are connected together via a covalent bond in a way to form a bicyclic group with the ring to which $R_{PTM31}$ and $R_{PTM32}$ are attached; or when $R_{PTM32}$ is the covalently joined position, $R_{PTM24}$ and $R_{PTM29}$ are connected together via a covalent bond in a way to form a bicyclic group with the ring to which $R_{PTM24}$ and $R_{PTM29}$ are attached, and/or $R_{PTM29}$ and $R_{PTM30}$ are connected together via a covalent bond in a way to form a bicyclic group with the ring to which $R_{PTM29}$ and $R_{PTM30}$ are attached.

In any aspect or embodiment described herein, the PTM is selected from the group consisting of PTM-1, PTM-2, PTM-3, PTM-4, PTM-5, PTM-6, PTM-7, and PTM-8:

PTM-1

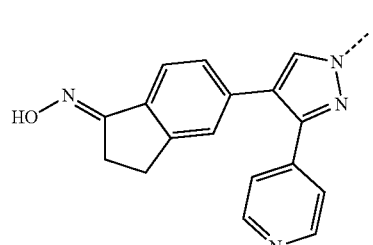

PTM-2

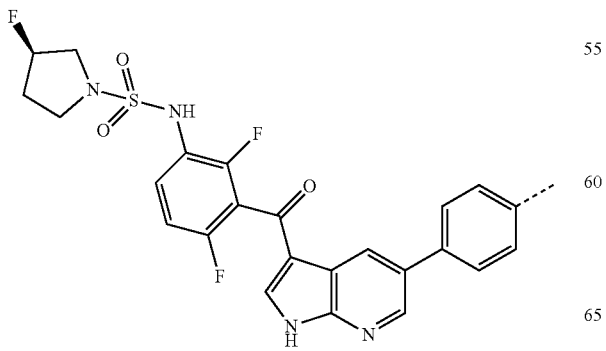

PTM-3

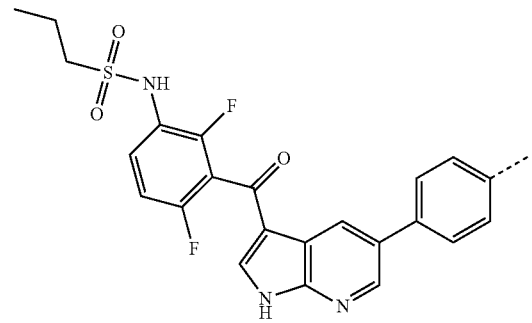

PTM-4

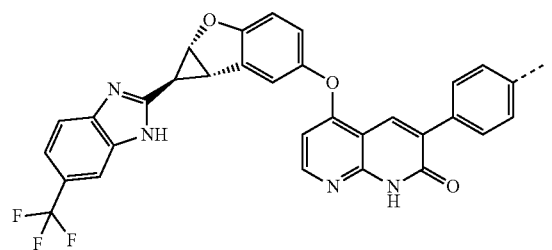

PTM-5

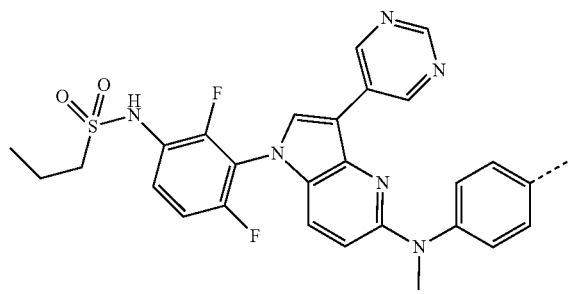

PTM-6

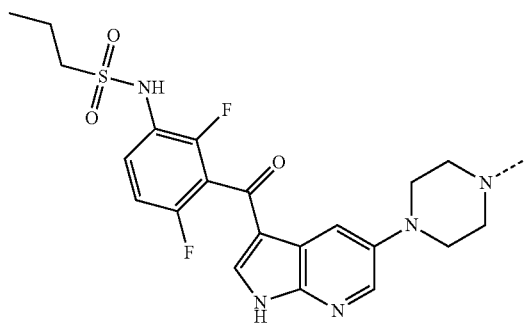

PTM-7

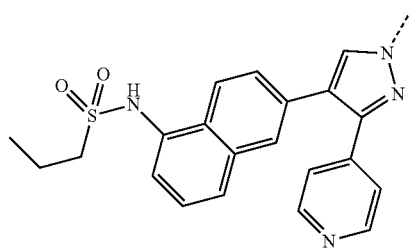

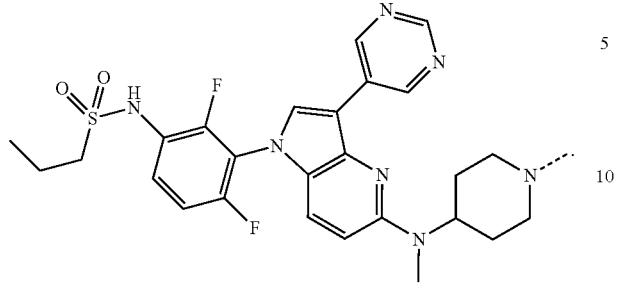
PTM-8
In any aspect or embodiment described herein, the ULM is selected from the group consisting of:
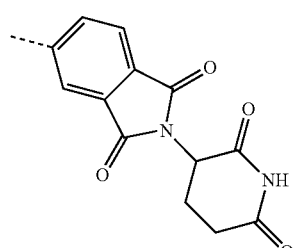
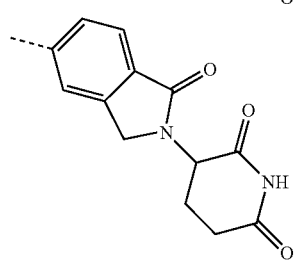
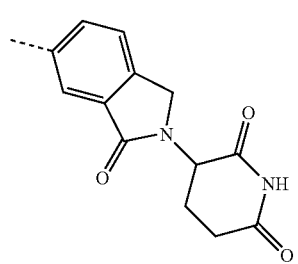
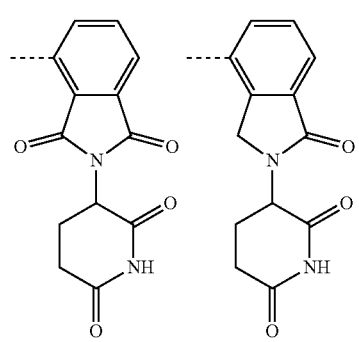
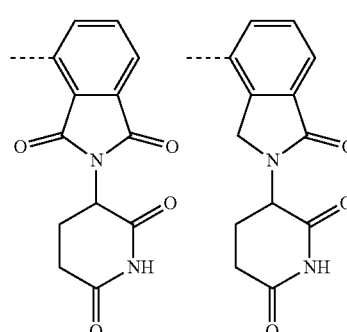
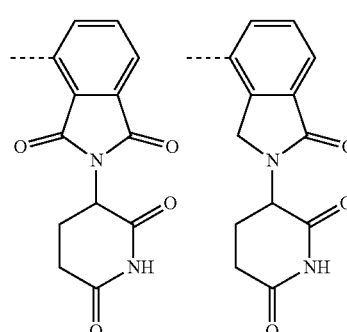
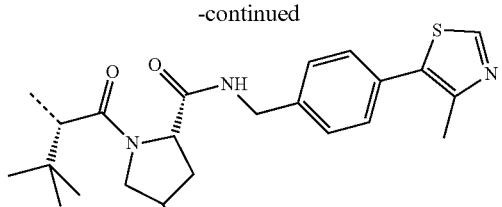
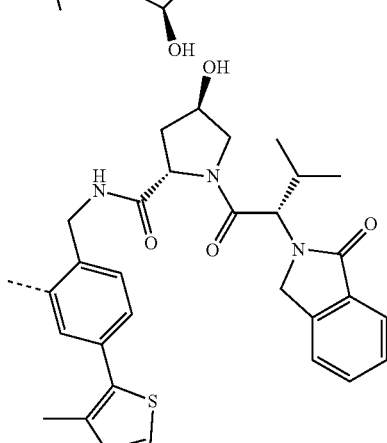
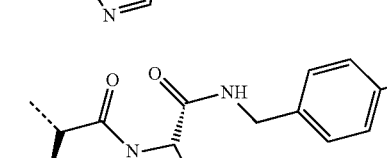
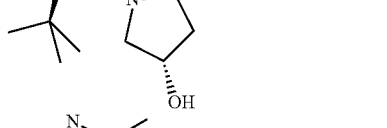
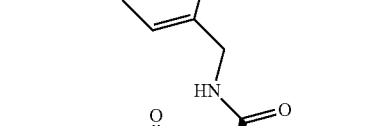
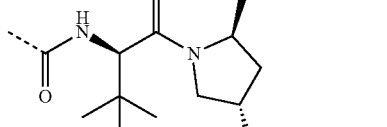
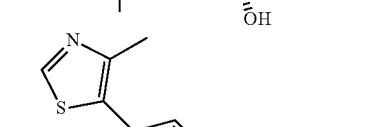

-continued

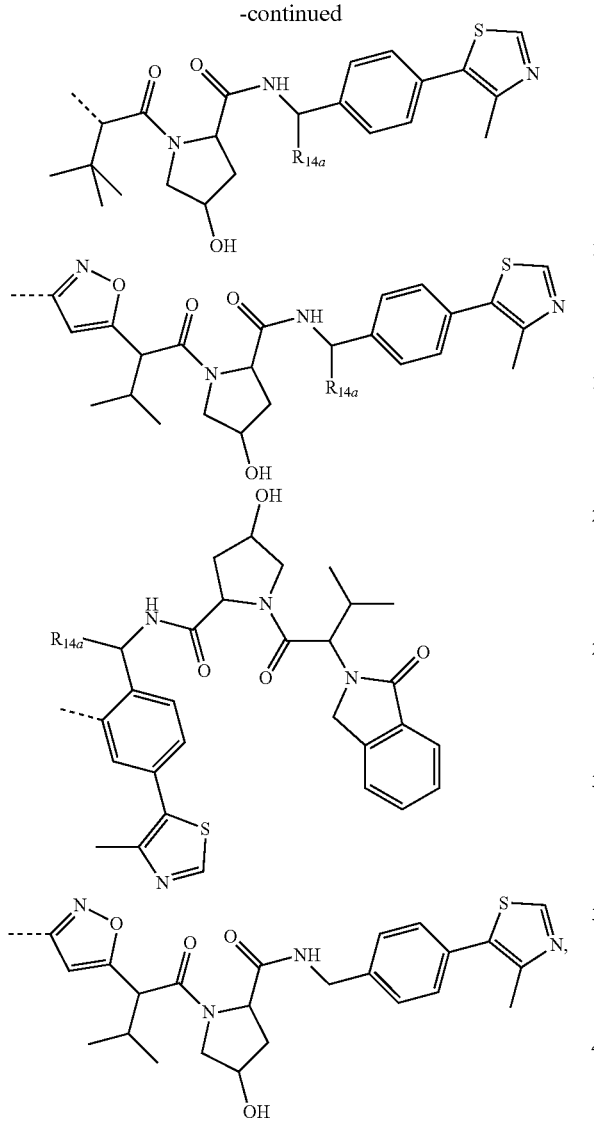

wherein the $R_{14a}$ is a H, methyl or hydroxymethyl.

In any aspect or embodiment described herein, ULM is a Von Hippel-Lindau (VHL) ligase-binding moiety (VLM) with a chemical structure represented by:

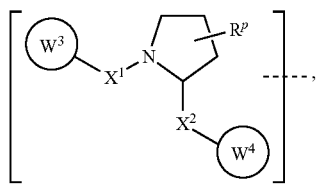

wherein:

$X^1$, $X^2$ are each independently selected from the group of a bond, O, $NR^{Y3}$, $CR^{Y3}R^{Y4}$, C=O, C=S, SO, and $SO_2$;

$R^{Y3}$, $R^{Y4}$ are each independently selected from the group of H, linear or branched $C_{1-6}$ alkyl (optionally substituted by 1 or more halo), optionally substituted $C_{1-6}$ alkoxyl (e.g., optionally substituted by 0-3 $R^P$ groups);

$R^P$ is 0, 1, 2, or 3 groups, each independently selected from H, halo, —OH, $C_{1-3}$ alkyl, C=O;

$W^3$ is selected from the group of an an optionally substituted -T-N($R^{1a}R^{1b}$)$X^3$, optionally substituted -T-N($R^{1a}R^{1a}$) optionally substituted -T-Aryl, an optionally substituted -T-Heteroaryl, an optionally substituted -T-Heterocycle, an optionally substituted —$NR^1$-T-Aryl, an optionally substituted —$NR^1$-T-Heteroaryl or an optionally substituted —$NR^1$-T-Heterocycle;

$X^3$ of Formula ULM-a is C=O, $R^1$, $R^{1a}$, $R^{1b}$;

$R^1$, $R^{1a}$, $R^{1b}$ are each independently selected from the group consisting of H, linear or branched $C_1$-$C_6$ alkyl group optionally substituted by 1 or more halo or —OH groups, $R^{Y3}$C=O, $R^{Y3}$C=S, $R^{Y3}$SO, $R^{Y3}SO_2$, N($R^{Y3}R^{Y4}$)C=O, N($R^{Y3}R^{Y4}$)C=S, N($R^{Y3}R^{Y4}$)SO, and N($R^{Y3}R^{Y4}$)$SO_2$;

T is selected from the group of an optionally substituted alkyl, —$(CH_2)_n$— group, wherein each one of the methylene groups is optionally substituted with one or two substituents selected from the group of halogen, methyl, a linear or branched $C_1$-$C_6$ alkyl group optionally substituted by 1 or more halogen or —OH groups or an amino acid side chain optionally substituted; and n is 0 to 6, $W^4$ is

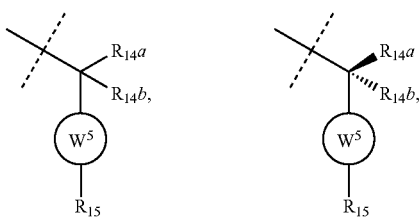

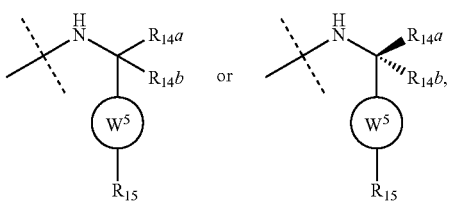

$R_{14a}$, $R_{14b}$, are each independently selected from the group of H, haloalkyl, or optionally substituted alkyl;

$W^5$ is selected from the group of a phenyl or a 5-10 membered heteroaryl, $R_{15}$ is selected from the group of H, halogen, CN, OH, $NO_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; aryl, heteroaryl, cycloalkyl, or cycloheteroalkyl (each optionally substituted);

and wherein the dashed line indicates the site of attachment of at least one PTM, another ULM (ULM') or a chemical linker moiety coupling at least one PTM or a ULM' or both to ULM.

In any aspect or embodiment described herein, the ULM is a Von Hippel-Lindau (VHL) ligase-binding moiety (VLM) with a chemical structure represented by:

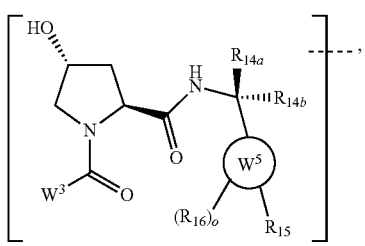

wherein:
W³ is selected from the group of an optionally substituted aryl, optionally substituted heteroaryl, or

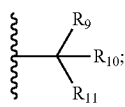

R₉ and R₁₀ are independently hydrogen, optionally substituted alkyl, optionally substituted cycloalkyl, optionally substituted hydroxyalkyl, optionally substituted heteroaryl, or haloalkyl, or R₉, R₁₀, and the carbon atom to which they are attached form an optionally substituted cycloalkyl;
R₁₁ is selected from the group of an optionally substituted heterocyclic, optionally substituted alkoxy, optionally substituted heteroaryl, optionally substituted aryl,

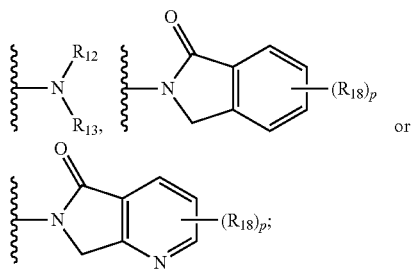

R₁₂ is selected from the group of H or optionally substituted alkyl;
R₁₃ is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;
R₁₄ₐ, R₁₄ᵦ, are each independently selected from the group of H, haloalkyl, or optionally substituted alkyl;
W⁵ is selected from the group of a phenyl or a 5-10 membered heteroaryl,
R₁₅ is selected from the group of H, halogen, CN, OH, NO₂, N R₁₄ₐR₁₄ᵦ, OR₁₄ₐ, CONR₁₄ₐR₁₄ᵦ, NR₁₄ₐCOR₁₄ᵦ, SO₂NR₁₄ₐR₁₄ᵦ, NR₁₄ₐ SO₂R₁₄ᵦ; optionally substituted alkyl, optionally substituted haloalkyl, optionally substituted haloalkoxy; aryl, heteroaryl, cycloalkyl, or cycloheteroalkyl (each optionally substituted);
R₁₆ is independently selected from the group of halo, optionally substituted alkyl, optionally substituted haloalkyl, hydroxy, or optionally substituted haloalkoxy;
o is 0, 1, 2, 3, or 4;
R₁₈ is independently selected from the group of H, halo, optionally substituted alkoxy, cyano, optionally substituted alkyl, haloalkyl, haloalkoxy or a linker; and
p is 0, 1, 2, 3, or 4, and wherein the dashed line indicates the site of attachment of at least one PTM, another ULM (ULM') or a chemical linker moiety coupling at least one PTM or a ULM' or both to ULM.

In any aspect or embodiment described herein, the ULM has a chemical structure selected from the group of:

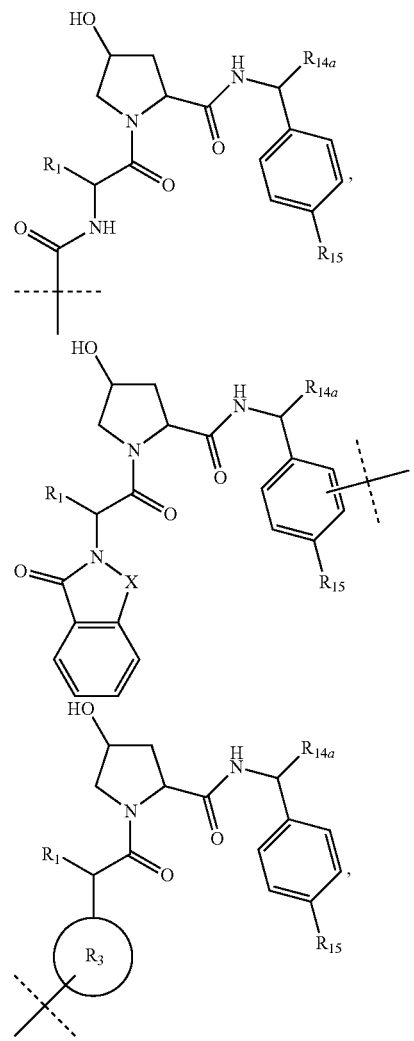

wherein:
R₁ is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;
R₁₄ₐ is H, haloalkyl, optionally substituted alkyl, methyl, fluoromethyl, hydroxymethyl, ethyl, isopropyl, or cyclopropyl;
R₁₅ is selected from the group consisting of H, halogen, CN, OH, NO₂, optionally substituted heteroaryl, optionally substituted aryl; optionally substituted alkyl, optionally substituted haloalkyl, optionally substituted haloalkoxy, cycloalkyl, or cycloheteroalkyl;

X is C, CH₂, or C=O;

R₃ is a bond or an optionally substituted 5 or 6 remembered heteroaryl; and wherein the dashed line indicates the site of attachment of at least one PTM, another ULM (ULM') or a chemical linker moiety coupling at least one PTM or a ULM' or both to the ULM.

In any aspect or embodiment described herein, the ULM comprises a group according to the chemical structure:

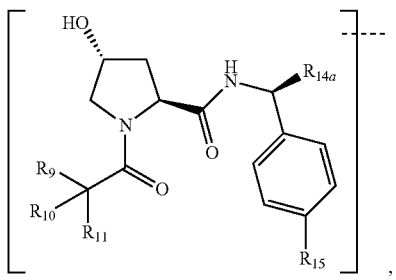

wherein:

R₁₄ₐ is H, haloalkyl, optionally substituted alkyl, methyl, fluoromethyl, hydroxymethyl, ethyl, isopropyl, or cyclopropyl;

R₉ is H;

R₁₀ is H, ethyl, isopropyl, tert-butyl, sec-butyl, cyclopropyl, cyclobutyl, cyclopentyl, or cyclohexyl;

R₁₁ is

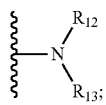

optionally substituted heteroaryl,

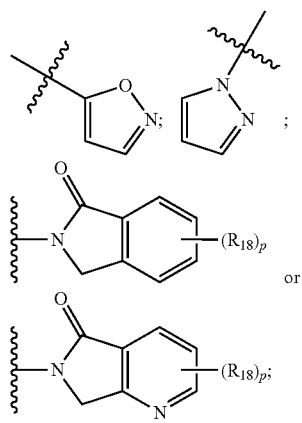

p is 0, 1, 2, 3, or 4; and each R₁₈ is independently halo, optionally substituted alkoxy, cyano, optionally substituted alkyl, haloalkyl, haloalkoxy or a linker;

R₁₂ is H, C=O

R₁₃ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl, R₁₅ is selected from the group consisting of H, halogen, Cl, CN, OH, NO₂, optionally substituted heteroaryl, optionally substituted aryl;

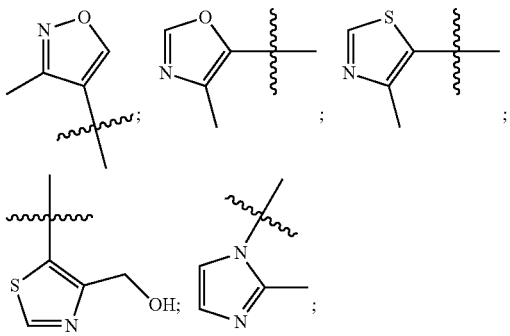

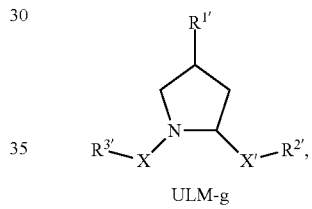

and wherein the dashed line indicates the site of attachment of at least one PTM, another ULM (ULM') or a chemical linker moiety coupling at least one PTM or a ULM' or both to the ULM.

In any aspect or embodiments described herein, the ULM comprises a group according to the chemical structure:

$$R^{3'}-X\underset{\text{ULM-g}}{\overset{R^{1'}}{\diagdown N \diagup}}X'-R^{2'},$$

wherein:

R¹' of ULM-g is an optionally substituted C₁-C₆ alkyl group, an optionally substituted —(CH₂)ₙOH, an optionally substituted —(CH₂)ₙSH, an optionally substituted (CH₂)ₙ—O—(C₁-C₆)alkyl group, an optionally substituted (CH₂)ₙ—WCOCW-(C₀-C₆)alkyl group containing an epoxide moiety WCOCW where each W is independently H or a C₁-C₃ alkyl group, an optionally substituted —(CH₂)ₙCOOH, an optionally substituted —(CH₂)ₙC(O)—(C₁-C₆ alkyl), an optionally substituted —(CH₂)ₙNHC(O)—R₁, an optionally substituted —(CH₂)ₙC(O)—NR₁R₂, an optionally substituted —(CH₂)ₙOC(O)—NR₁R₂, —(CH₂O)ₙH, an optionally substituted —(CH₂)ₙOC(O)—(C₁-C₆ alkyl), an optionally substituted —(CH₂)ₙC(O)—O—(C₁-C₆ alkyl), an optionally substituted —(CH₂O)ₙCOOH, an optionally substituted —(OCH₂)ₙ—O—(C₁-C₆ alkyl), an optionally substituted —(CH₂O)ₙC(O)—(C₁-C₆ alkyl), an optionally substituted —(OCH₂)ₙNHC(O)—R₁, an optionally substituted —(CH₂O)ₙC(O)—NR₁R₂, —(CH₂CH₂O)ₙH, an optionally substituted —(CH₂CH₂O)ₙCOOH, an optionally substituted —(OCH₂CH₂)ₙO—(C₁-C₆alkyl), an optionally substituted —(CH₂CH₂O)ₙC(O)—(C₁-C₆ alkyl), an optionally substituted —(OCH₂CH₂)ₙNHC(O)—R₁, an optionally substituted —(CH₂CH₂O)ₙC(O)—NR₁R₂, an optionally substituted —SO₂Rₛ, an optionally substituted S(O)Rₛ, NO₂, CN or halogen (F, Cl, Br, I, preferably F or Cl);

$R_1$ and $R_2$ of ULM-g are each independently H or a $C_1$-$C_6$ alkyl group which may be optionally substituted with one or two hydroxyl groups or up to three halogen groups (preferably fluorine);

$R_S$ of ULM-g is a $C_1$-$C_6$ alkyl group, an optionally substituted aryl, heteroaryl or heterocycle group or a —$(CH_2)_m NR_1 R_2$ group;

X and X' of ULM-g are each independently C=O, C=S, —S(O), S(O)$_2$, (preferably X and X' are both C=O);

$R^2$ of ULM-g is an optionally substituted —$(CH_2)_n$—(C=O)$_u$(NR$_1$)$_v$(SO$_2$)$_w$alkyl group, an optionally substituted —$(CH_2)_n$—(C=O)$_u$(NR$_1$)$_v$(SO$_2$)$_w$NR$_{1N}$R$_{2N}$ group, an optionally substituted —$(CH_2)$, —(C=O)$_u$(NR$_1$)$_v$(SO$_2$)$_w$-Aryl, an optionally substituted —$(CH_2)_n$ —(C=O)$_u$(NR$_1$)$_v$(SO$_2$)$_w$-Heteroaryl, an optionally substituted —$(CH_2)_n$—(C=O)$_v$NR$_1$(SO$_2$)$_w$-Heterocycle, an optionally substituted —NR$^1$—$(CH_2)_n$—C(O)$_u$(NR$_1$)$_v$(SO$_2$)$_w$-alkyl, an optionally substituted —NR$^1$—$(CH_2)_n$—C(O)$_u$(NR$_1$)$_v$(SO$_2$)$_w$—NR$_{1N}$R$_{2N}$, an optionally substituted —NR$^1$—$(CH_2)_n$—C(O)$_u$(NR$_1$)$_v$(SO$_2$)$_w$—NR$_1$C(O)R$_{1N}$, an optionally substituted —NR$^1$—$(CH_2)_n$—(C=O)$_u$(NR$_1$)$_v$(SO$_2$)$_w$-Aryl, an optionally substituted —NR$^1$—$(CH_2)_n$—(C=O)$_u$(NR$_1$)$_v$(SO$_2$)$_w$-Heteroaryl or an optionally substituted —NR$^1$—$(CH_2)_n$—(C=O)$_v$NR$_1$(SO$_2$)$_w$-Heterocycle, an optionally substituted —X$^{R2'}$-alkyl group; an optionally substituted —X$^{R2'}$-Aryl group; an optionally substituted —X$^{R2'}$-Heteroaryl group; an optionally substituted —X$^{R2'}$-Heterocycle group; an optionally substituted;

$R^{3'}$ of ULM-g is an optionally substituted alkyl, an optionally substituted —$(CH_2)_n$—(O)$_u$(NR$_1$)$_v$(SO$_2$)$_w$-alkyl, an optionally substituted —$(CH_2)_n$—C(O)$_u$(NR$_1$)$_v$(SO$_2$)$_w$—NR$_{1N}$R$_{2N}$, an optionally substituted —$(CH_2)_n$—C(O)$_u$(NR$_1$)$_v$(SO$_2$)$_w$—NR$_1$C(O)R$_{1N}$, an optionally substituted —$(CH_2)_n$—C(O)$_u$(NR$_1$)$_v$(SO$_2$)$_w$—C(O)NR$_1$R$_2$, an optionally substituted —$(CH_2)_n$—C(O)$_u$(NR$_1$)$_v$(SO$_2$)$_w$-Aryl, an optionally substituted —$(CH_2)_n$—C(O)$_u$(NR$_1$)$_v$(SO$_2$)$_w$-Heteroaryl, an optionally substituted —$(CH_2)_n$—C(O)$_u$(NR$_1$)$_v$(SO$_2$)$_w$-Heterocycle, an optionally substituted —NR$^1$—$(CH_2)_n$—C(O)$_u$(NR$_1$)$_v$(SO$_2$)$_w$-alkyl, an optionally substituted —NR$^1$—$(CH_2)_n$—C(O)$_u$(NR$_1$)$_v$(SO$_2$)$_w$—NR$_{1N}$R$_{2N}$, an optionally substituted —NR$^1$—$(CH_2)_n$—C(O)$_u$(NR$_1$)$_v$(SO$_2$)$_w$—NR$_1$C(O)R$_{1N}$, an optionally substituted —NR$^1$—$(CH_2)_n$—C(O)$_u$(NR$_1$)$_v$(SO$_2$)$_w$-Aryl, an optionally substituted —NR$^1$—$(CH_2)_n$—C(O)$_u$(NR$_1$)$_v$(SO$_2$)$_w$-Heteroaryl, an optionally substituted —NR$^1$—$(CH_2)_n$—C(O)$_u$(NR$_1$)$_v$(SO$_2$)$_w$-Heterocycle, an optionally substituted —O—$(CH_2)_n$—(C=O)$_u$(NR$_1$)$_v$(SO$_2$)$_w$-alkyl, an optionally substituted —O—(CH$_2$)n-(C=O)$_u$(NR$_1$)$_v$(SO$_2$)$_w$—NR$_{1N}$R$_{2N}$, an optionally substituted —O—(CH$_2$)n-(C=O)—(NR$_1$)$_v$(SO$_2$)$_w$—NR$_1$C(O)R$_{1N}$, an optionally substituted —O—(CH$_2$)n-(C=O)—(NR$_1$)$_v$(SO$_2$)$_w$-Aryl, an optionally substituted —O—$(CH_2)_n$—(C=O)$_u$ (NR$_1$)$_v$(SO$_2$)$_w$-Heteroaryl or an optionally substituted —O—$(CH_2)_n$—(C=O)$_u$(NR$_1$)$_v$(SO$_2$)$_w$-Heterocycle; —$(CH_2)_n$—(V)$_{n'}$—$(CH_2)_n$—(V)$_{n'}$-alkyl group, an optionally substituted —$(CH_2)_n$—(V)$_{n'}$—$(CH_2)_n$—(V)$_{n'}$-Aryl group, an optionally substituted —$(CH_2)_n$—(V)$_{n'}$—$(CH_2)_n$—(V)$_{n'}$-Heteroaryl group, an optionally substituted —$(CH_2)_n$—(V)$_{n'}$—$(CH_2)_n$—(V)$_{n'}$-Heterocycle group, an optionally substituted —$(CH_2)_n$—N(R$_{1'}$)(C=O)$_m$—(V)$_{n'}$-alkyl group, an optionally substituted —$(CH_2)_n$—N(R$_{1'}$)(C=O)$_{m'}$—(V)$_{n'}$-Aryl group, an optionally substituted —$(CH_2)_n$—N(R$_{1'}$)(C=O)$_{m'}$—(V)$_{n'}$-Heteroaryl group, an optionally substituted —$(CH_2)_n$—NR$_{1'}$)(C=O)$_{m'}$—(V)$_{n'}$-Heterocycle group, an optionally substituted —X$^{R3'}$—alkyl group; an optionally substituted —X$^{R3'}$—Aryl group; an optionally substituted —X$^{R3'}$—Heteroaryl group; an optionally substituted —X$^{R3'}$—Heterocycle group; an optionally substituted;

$R_{1N}$ and $R_{2N}$ of ULM-g are each independently H, $C_1$-$C_6$ alkyl which is optionally substituted with one or two hydroxyl groups and up to three halogen groups or an optionally substituted —$(CH_2)_n$-Aryl, —$(CH_2)_n$-Heteroaryl or —$(CH_2)_n$-Heterocycle group;

V of ULM-g is O, S or NR$_1$;

$R_1$ of ULM-g is the same as above;

$R^1$ and $R_{1'}$ of ULM-g are each independently H or a $C_1$-$C_3$ alkyl group;

$X^{R2'}$ and $X^{R3'}$ of ULM-g are each independently an optionally substituted —$(CH_2)_n$—, —$(CH_2)_n$—CH(X$_v$)=CH(X$_v$)— (cis or trans), —$(CH_2)_n$—CH=CH—, —$(CH_2CH_2O)_n$— or a $C_3$-$C_6$ cycloalkyl group, where X$_v$ is H, a halo or a $C_1$-$C_3$ alkyl group which is optionally substituted;

each m of ULM-g is independently 0, 1, 2, 3, 4, 5, 6;

each m' of ULM-g is independently 0 or 1;

each n of ULM-g is independently 0, 1, 2, 3, 4, 5, 6;

each n' of ULM-g is independently 0 or 1;

each u of ULM-g is independently 0 or 1;

each v of ULM-g is independently 0 or 1;

each w of ULM-g is independently 0 or 1; and any one or more of R$^{1'}$, R$^{2'}$, R$^{3'}$, X and X' of ULM-g is optionally modified to be covalently bonded to the PTM group through a linker group when PTM is not ULM', or when PTM is ULM', any one or more of R$^{1'}$, R$^{2'}$, R$^{3'}$, X and X' of each of ULM and ULM' are optionally modified to be covalently bonded to each other directly or through a linker group, or a pharmaceutically acceptable salt, stereoisomer, solvate or polymorph thereof.

In any aspect or embodiment described herein, the ULM is a cereblon E3 ligase-binding moiety (CLM) selected from the group coinsisting of a thalidomide, lenalidomide, pomalidomide, analogs thereof, isosteres thereof, or derivatives thereof.

In any aspect or embodiment described herein, the CLM has a chemical structure represented by:

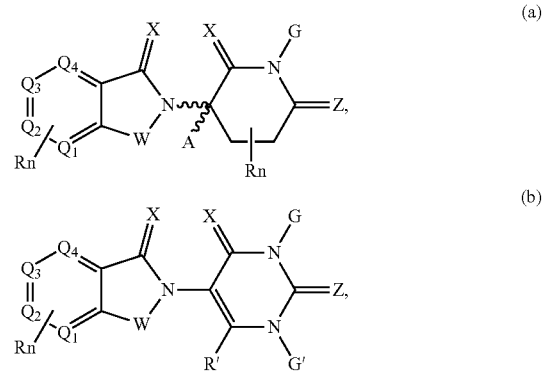

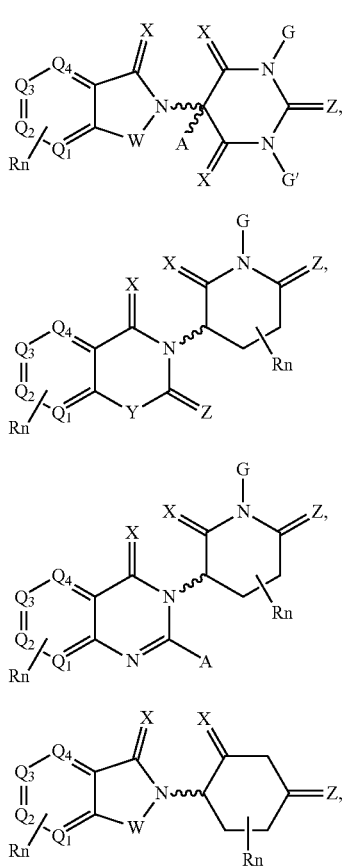

(c)

(d)

(e)

(f)

wherein:
W is selected from the group consisting of CH$_2$, CHR, C=O, SO$_2$, NH, and N-alkyl; each X is independently selected from the group consisting of O, S, and H$_2$,
Y is selected from the group consisting of CH$_2$, —C=CR', NH, N-alkyl, N-aryl, N-hetaryl, N-cycloalkyl, N-heterocyclyl, O, and S;
Z is selected from the group consisting of O, S, and H$_2$;
G and G' are independently selected from the group consisting of H, alkyl (linear, branched, optionally substituted), OH, R'OCOOR, R'OCONRR", CH$_2$-heterocyclyl optionally substituted with R', and benzyl optionally substituted with R';
$Q_1$, $Q_2$, $Q_3$, and $Q_4$ represent a carbon C substituted with a group independently selected from R', N or N-oxide;
A is independently selected from the group H, alkyl (linear, branched, optionally substituted), cycloalkyl, Cl and F;
R comprises —CONR'R", —OR', —NR'R", —SR', —SO$_2$R', —SO$_2$NR'R", —CR'R"—, —CR'NR'R"—, (—CR'O)nR", -aryl, -hetaryl, -alkyl (linear, branched, optionally substituted), -cycloalkyl, -heterocyclyl, —P(O)(OR')R", —P(O)R'R", —OP(O)(OR')R", —OP(O)R'R", —Cl, —F, —Br, —I, —CF$_3$, —CN, —NR'SO$_2$NR'R", —NR'CONR'R", —CONR'COR", —NR'C(=N—CN)NR'R", —C(=N—CN)NR'R", —NR'C(=N—CN)R", —NR'C(=C—NO$_2$)NR'R", —SO$_2$NR'COR", —NO$_2$, —CO$_2$R', —C(C=N—OR')R", —CR'=CR'R", —CCR', —S(C=O)(C=N—R')R", —SF$_5$ and —OCF$_3$;
R' and R" are independently selected from the group consisting of a bond, H, alkyl, cycloalkyl, aryl, heteroaryl, heterocyclic, —C(=O)R, heterocyclyl, each of which is optionally substituted;
∼∼ represents a bond that may be stereospecific ((R) or (S)) or non-stereospecific; and
$R_n$ comprises a functional group, optionally substituted alkoxyl group (e.g., a methoxy, ethoxy, butoxy, propoxy, pentoxy, or hexoxy; wherein the alkoxyl may be substituted with a halogen, a cycloalkyl (e.g., a C3-C6 cycloalkyl), or an aryl (e.g., C5-C7 aryl)), or an atom,
wherein n is an integer from 1-10 (e.g., 1-4), and wherein when n is 1, $R_n$ is modified to be covalently joined to the linker group (L), and
when n is 2, 3, or 4, then one $R_n$ is modified to be covalently joined to the linker group (L), and any other $R_n$ is optionally modified to be covalently joined to a PTM, a CLM, a second CLM having the same chemical structure as the CLM, a CLM', a second linker, or any multiple or combination thereof.

In any aspect or embodiment described herein, the CLM has a chemical structure represented by:

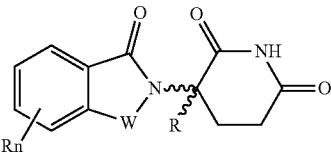

wherein:
W is independently selected from the group CH2, C=O, NH, and N-alkyl;
R is independently selected from a H, methyl, or alkyl (e.g., C1-C6 alkyl (linear, branched, optionally substituted));
∼∼ represents a bond that may be stereospecific ((R) or (S)) or non-stereospecific; and
Rn comprises 1-4 independently selected functional groups, optionally substituted alkoxyl group (e.g., a methoxy, ethoxy, butoxy, propoxy, pentoxy, or hexoxy; wherein the alkoxyl may be substituted with a halogen, a cycloalkyl (e.g., a C3-C6 cycloalkyl), or an aryl (e.g., C5-C7 aryl)), or atoms, and optionally, one of which is modified to be covalently joined to a PTM, a chemical linker group (L), a CLM (or CLM') or combination thereof.

In any aspect or embodiments described herein, the CLM has a chemical structure represented by:

(h)

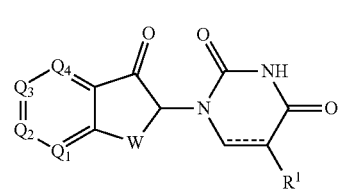

(i)

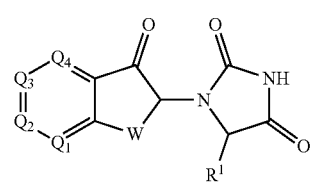

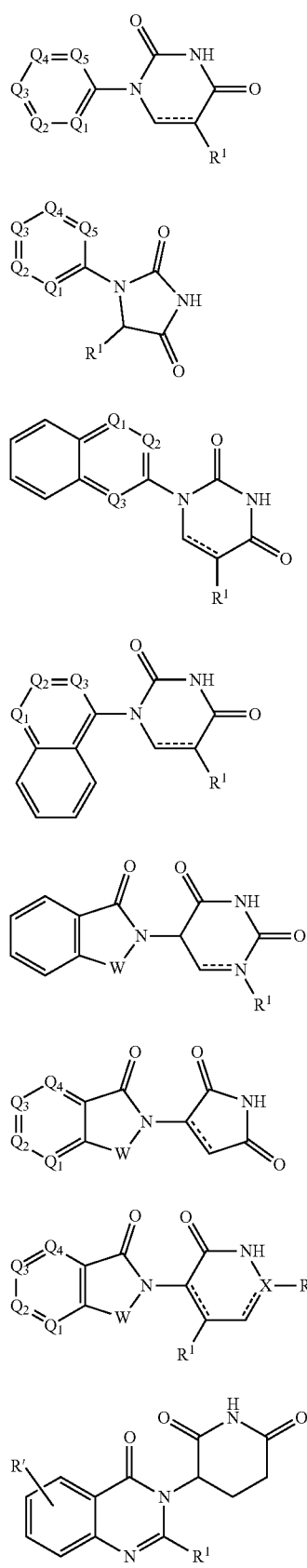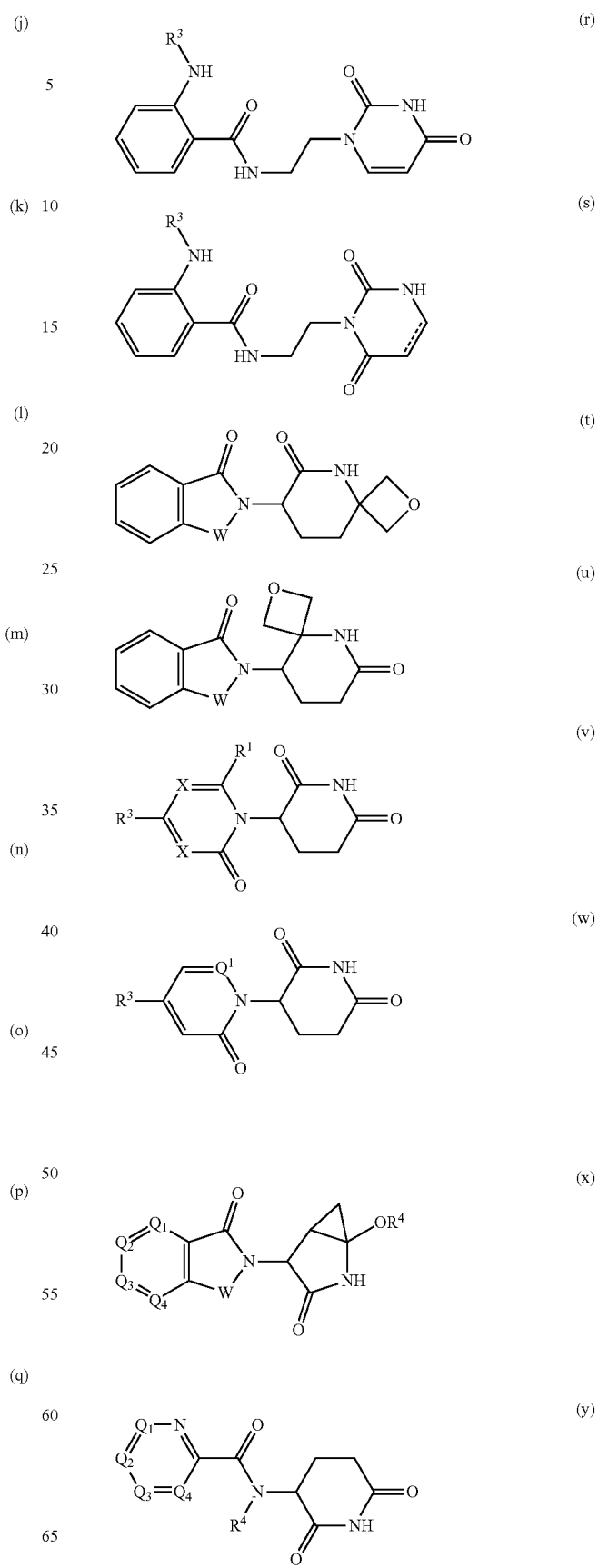

(z)

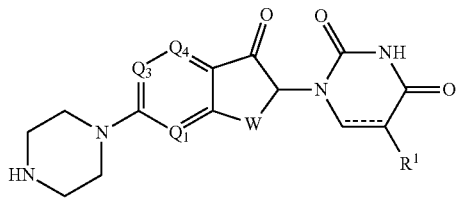

(aa)

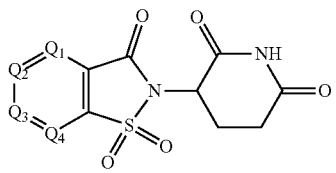

(ab)

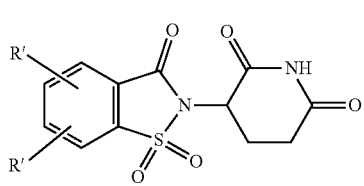

wherein:
W of Formulas (h) through (ab) is independently selected from CH$_2$, CHR, C=O, SO$_2$, NH, and N-alkyl;
Q1, Q2, Q3, Q4, Q5 of Formulas (h) through (ab) are independently represent a carbon C substituted with a group independently selected from R', N or N-oxide;
R$^1$ of Formulas (h) through (ab) is selected from H, CN, C1-C3 alkyl;
R$^2$ of Formulas (h) through (ab) is selected from the group H, CN, C1-C3 alkyl, CHF$_2$, CF$_3$, CHO;
R$^3$ of Formulas (h) through (ab) is selected from H, alkyl, substituted alkyl, alkoxy, substituted alkoxy;
R$^4$ of Formulas (h) through (ab) is selected from H, alkyl, substituted alkyl;
R$^5$ of Formulas (h) through (ab) is H or lower alkyl;
X of Formulas (h) through (ab) is C, CH or N;
R' of Formulas (h) through (ab) is selected from H, halogen, alkyl, substituted alkyl, alkoxy, substituted alkoxy;
R of Formulas (h) through (ab) is H, OH, lower alkyl, lower alkoxy, cyano, halogenated lower alkoxy, or halogenated lower alkyl

 of Formulas (h) through (ab) is a single or double bond; and
the CLM is covalently joined to a PTM, a chemical linker group (L), a ULM, CLM (or CLM') or combination thereof.

In any aspect or embodiment described herein, the ULM is a (MDM2) binding moiety (MLM) with a chemical moiety selected from the group consisting of a substituted imidazolines, a substituted spiro-indolinones, a substituted pyrrolidines, a substituted piperidinones, a substituted morpholinones, a substituted pyrrolopyrimidines, a substituted imidazolopyridines, a substituted thiazoloimidazoline, a substituted pyrrolopyrrolidinones, and a substituted isoquinolinones.

In any aspect or embodiment described herein, the ULM is a IAP E3 ubiquitin ligase binding moiety (ILM) comprising the amino acids alanine (A), valine (V), proline (P), and isoleucine (I) or their unnatural mimetics.

In any aspect or embodiment described herein, the ULM is a IAP E3 ubiquitin ligase binding moiety (ILM) comprising a AVPI tetrapeptide fragment or derivative thereof.

In any aspect or embodiment described herein, the linker (L) comprises a chemical structural unit represented by the formula:

-(A$^L$)$_q$-, wherein:
(A$^L$)$_q$ is a group which is connected to a ULM or PTM moiety;
q is an integer greater than or equal to 1;
wherein each A$^L$ is independently selected from the group consisting of, a bond, CR$^{L1}$R$^{L2}$, O, S, SO, SO$_2$, NW$^{L3}$, SO$_2$NR$^{L3}$, SONR$^{L3}$, CONR$^{L3}$, NR$^{L3}$CONR$^{L4}$, NR$^{L3}$SO$_2$NR$^{L4}$, CO, CR$^{L1}$=CR$^{L2}$, C≡C, SiR$^{L1}$R$^{L2}$, P(O)R$^{L1}$, P(O)OR$^{L1}$, NR$^{L3}$C(=NCN)NR$^{L4}$, NR$^{L3}$C(=NCN), NR$^{L3}$C(=CNO$_2$)NR$^{L4}$, C$_{3-11}$cycloalkyl optionally substituted with 0-6 R$^{L1}$ and/or R$^{L2}$ groups, C$_{3-11}$heterocyclyl optionally substituted with 0-6 R$^{L1}$ and/or R$^{L2}$ groups, aryl optionally substituted with 0-6 R$^{L1}$ and/or R$^{L2}$ groups, heteroaryl optionally substituted with 0-6 R$^{L1}$ and/or R$^{L2}$ groups, where R$^{L1}$ or R$^{L2}$, each independently are optionally linked to other groups to form cycloalkyl and/or heterocyclyl moiety, optionally substituted with 0-4 R$^{L5}$ groups; and
R$^{L1}$, R$^{L2}$, R$^{L3}$, R$^{L4}$ and R$^{L5}$ are, each independently, H, halo, C$_{1-8}$alkyl, OC$_{1-8}$alkyl, SC$_{1-8}$alkyl, NHC$_{1-8}$alkyl, N(C$_{1-8}$alkyl)$_2$, C$_{3-11}$cycloalkyl, aryl, heteroaryl, C$_{3-11}$heterocyclyl, OC$_{1-8}$cycloalkyl, SC$_{1-8}$cycloalkyl, NHC$_{1-8}$cycloalkyl, N(C$_{1-8}$cycloalkyl)$_2$, N(C$_{1-8}$cycloalkyl)(C$_{1-8}$alkyl), OH, NH$_2$, SH, SO$_2$C$_{1-8}$alkyl, P(O)(OC$_{1-8}$alkyl)(C$_{1-8}$alkyl), P(O)(OC$_{1-8}$alkyl)$_2$, CC—C$_{1-8}$alkyl, CCH, CH=CH(C$_{1-8}$alkyl), C(C$_{1-8}$alkyl)=CH(C$_{1-8}$alkyl), C(C$_{1-8}$alkyl)=C(C$_{1-8}$alkyl)$_2$, Si(OH)$_3$, Si(C$_{1-8}$alkyl)$_3$, Si(OH)(C$_{1-8}$alkyl)$_2$, COC$_{1-8}$alkyl, CO$_2$H, halogen, CN, CF$_3$, CHF$_2$, CH$_2$F, NO$_2$, SF$_5$, SO$_2$NHC$_{1-8}$alkyl, SO$_2$N(C$_{1-8}$alkyl)$_2$, SONHC$_{1-8}$alkyl, SON(C$_{1-8}$alkyl)$_2$, CONHC$_{1-8}$alkyl, CON(C$_{1-8}$alkyl)$_2$, N(C$_{1-8}$alkyl)CONH(C$_{1-8}$alkyl), N(C$_{1-8}$alkyl)CON(C$_{1-8}$alkyl)$_2$, NHCONH(C$_{1-8}$alkyl), NHCON(C$_{1-8}$alkyl)$_2$, NHCONH$_2$, N(C$_{1-8}$alkyl)SO$_2$NH(C$_{1-8}$alkyl), N(C$_{1-8}$alkyl) SO$_2$N(C$_{1-8}$alkyl)$_2$, NH SO$_2$NH(C$_{1-8}$alkyl), NH SO$_2$N(C$_{1-8}$alkyl)$_2$, NH SO$_2$NH$_2$.

In any aspect or embodiment described herein, the linker (L) comprises a group represented by a general structure selected from the group consisting of:
—N(R)—(CH2)$_m$—O(CH2)$_n$-O(CH2)$_o$-O(CH2)$_p$-O(CH2)$_q$-O(CH2)$_r$-OCH2-,
—O—(CH2)$_m$-O(CH2)$_n$-O(CH2)$_o$-O(CH2)$_p$-O(CH2)$_q$-O(CH2)$_r$-OCH2-,
—O—(CH2)$_m$-O(CH2)$_n$-O(CH2)$_o$-O(CH2)$_p$-O(CH2)$_q$-O(CH2)$_r$-O—;
—N(R)—(CH2)$_m$-O(CH2)$_n$-O(CH2)$_o$-O(CH2)$_p$-O(CH2)$_q$-O(CH2)$_r$-O—;
—(CH2)$_m$-O(CH2)$_n$-O(CH2)$_o$-O(CH2)$_p$-O(CH2)$_q$-O(CH2)$_r$-O—;
—(CH2)$_m$-O(CH2)$_n$-O(CH2)$_o$-O(CH2)$_p$-O(CH2)$_q$-O(CH2)$_r$-OCH2-;

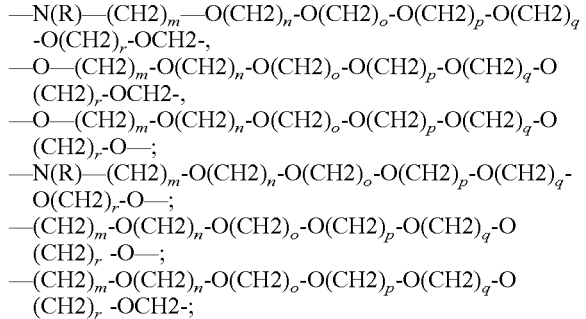

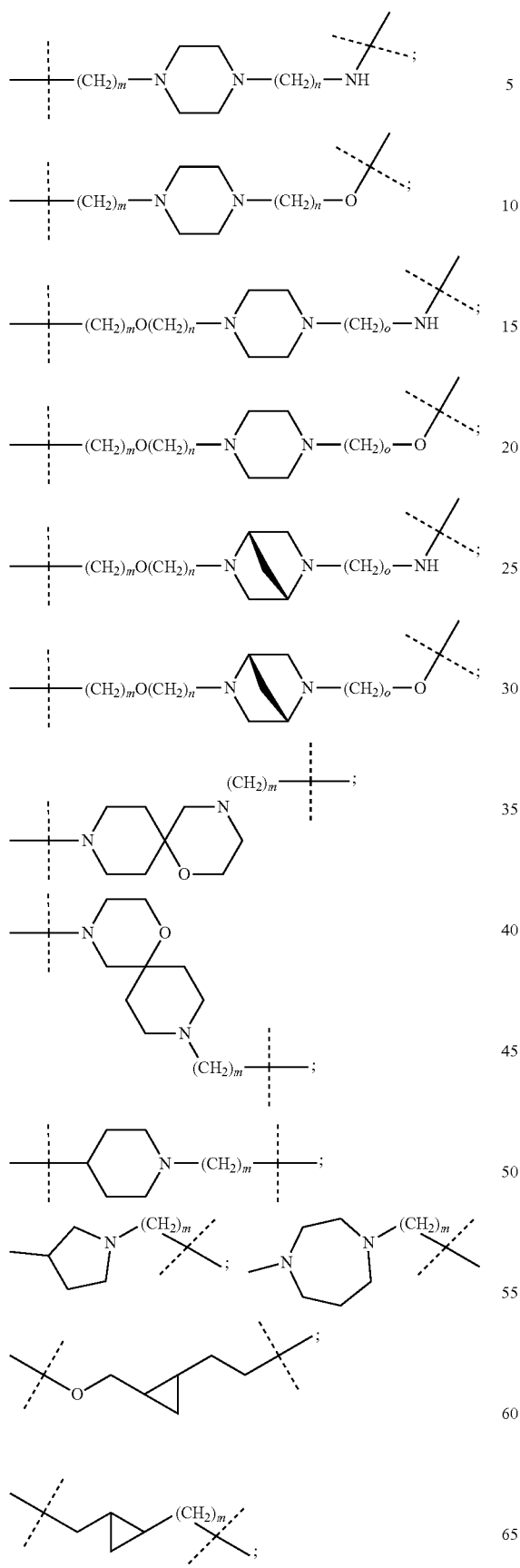
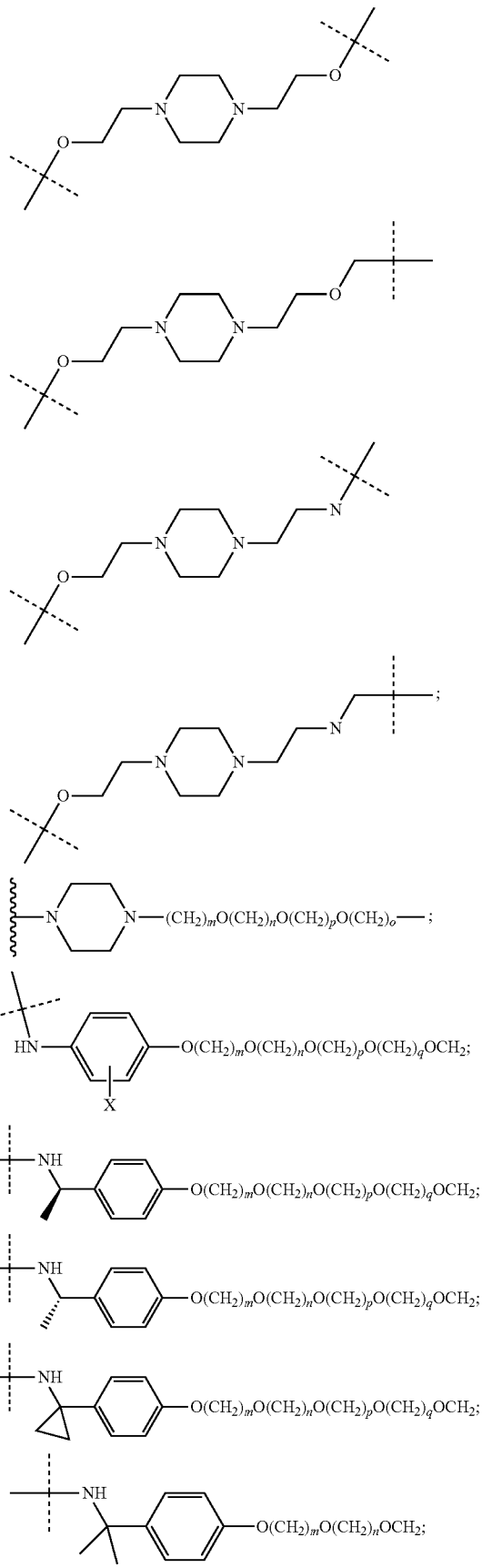

1297
-continued
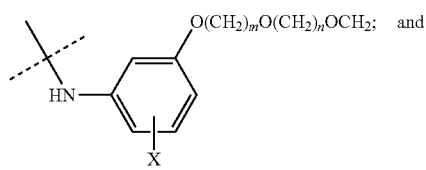
1298
-continued
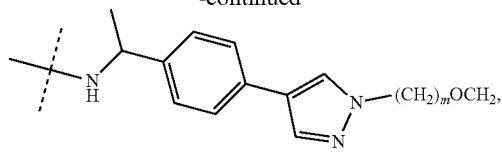
wherein m, n, o, p, q, and r, are independently 0, 1, 2, 3, 4, 5, 6, with the proviso that when the number is zero, there is no N—O or O—O bond, R is selected from the group H, methyl and ethyl, and X is selected from the group H and F;
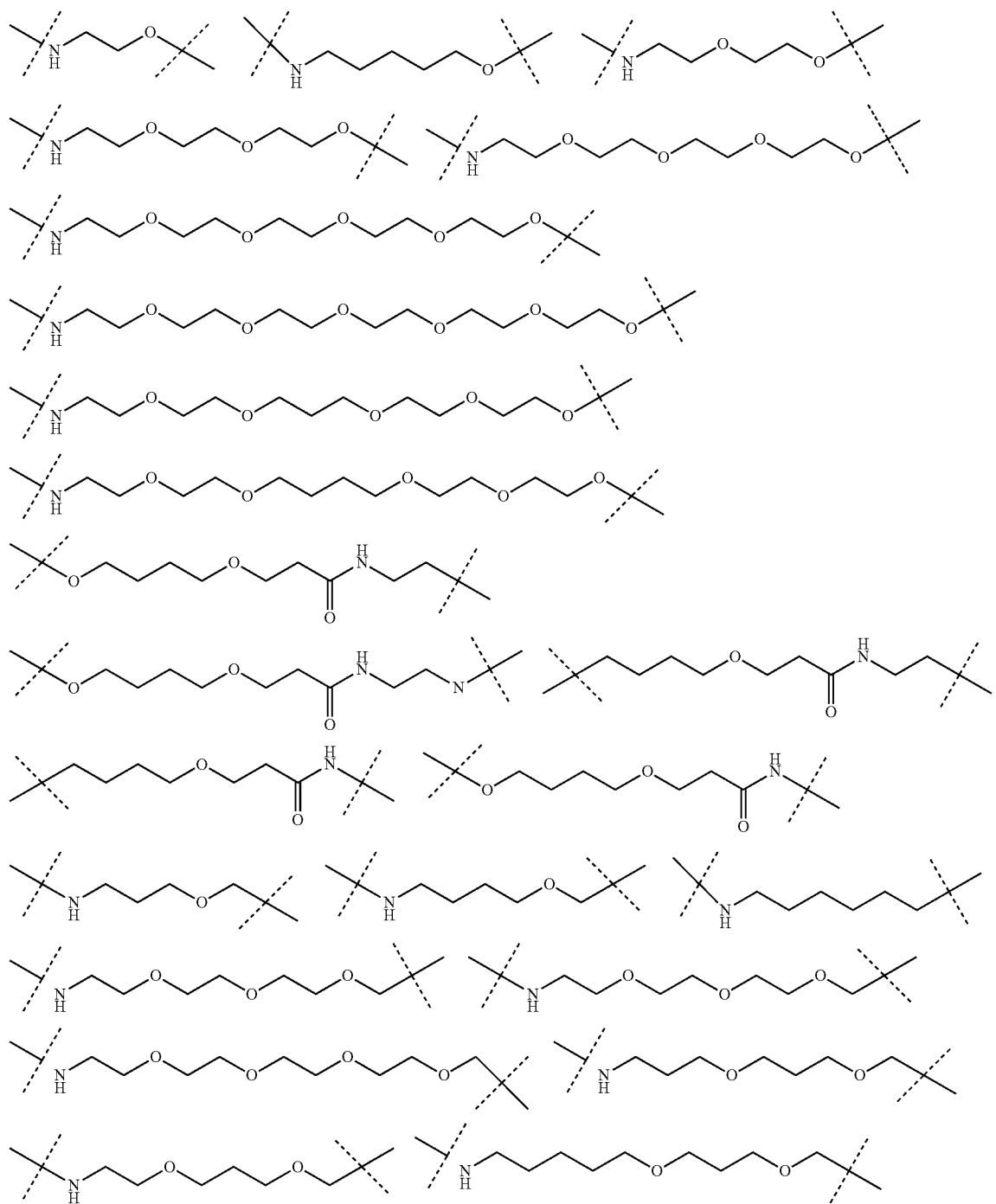

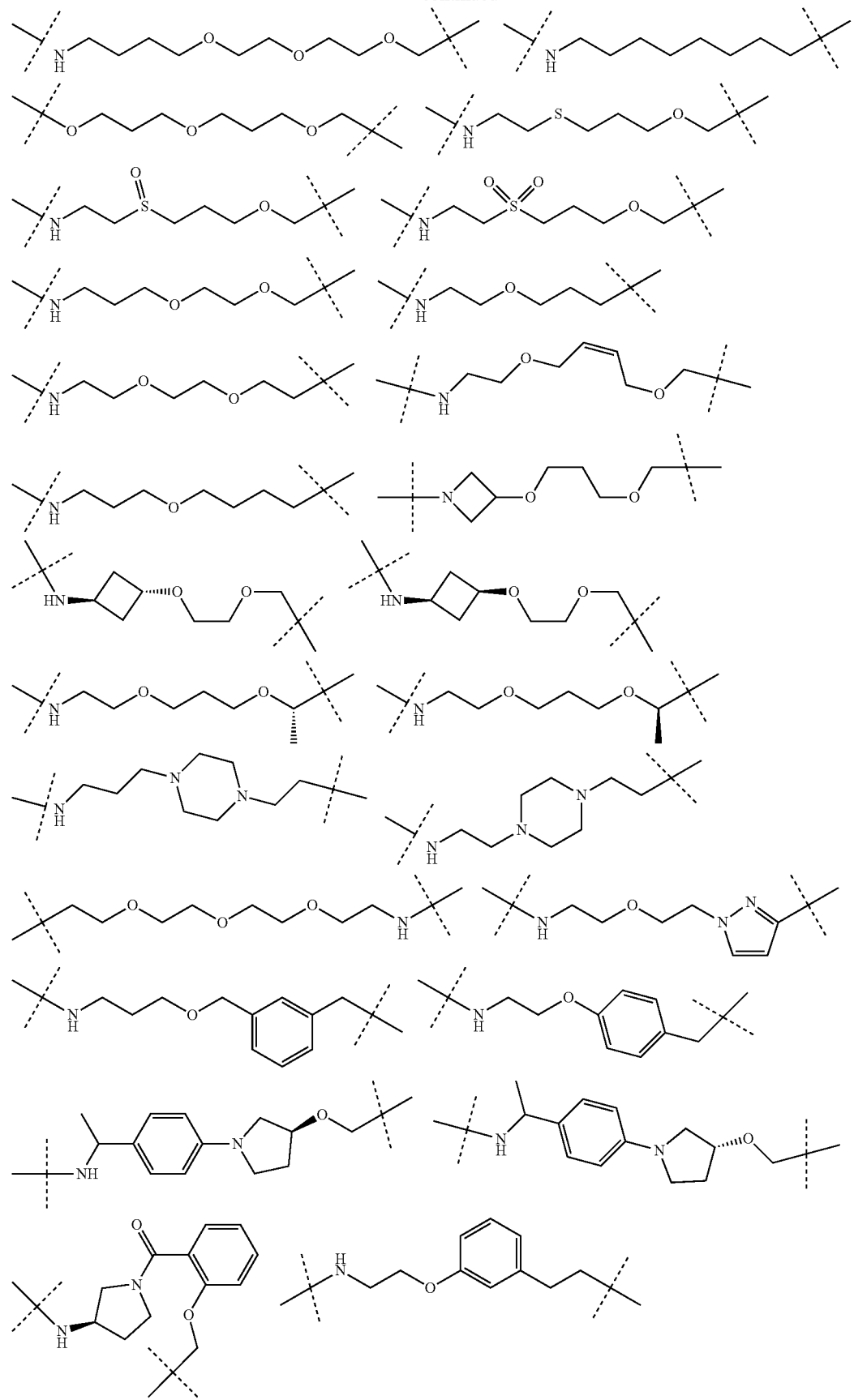

1301
-continued
1302
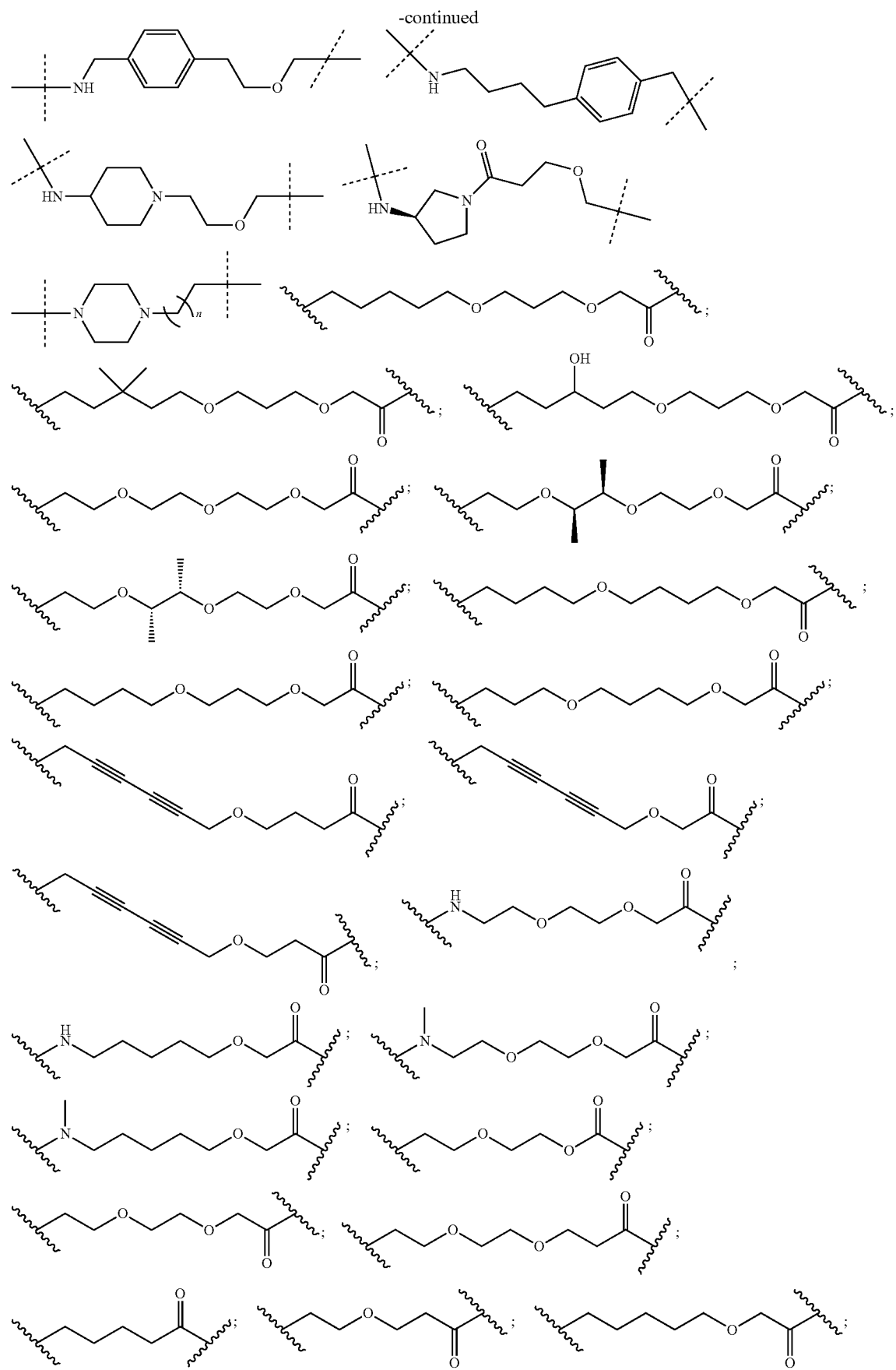

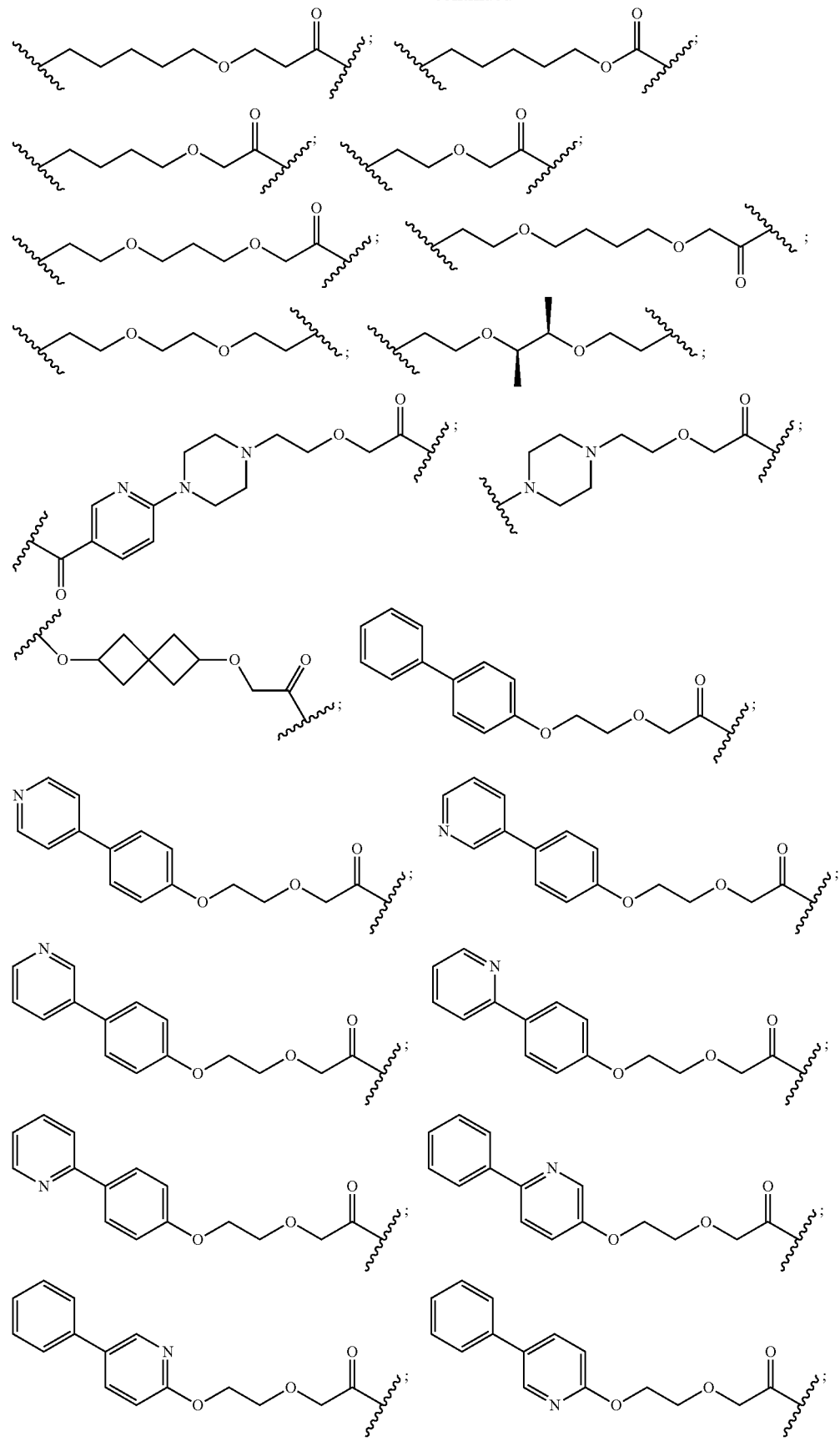

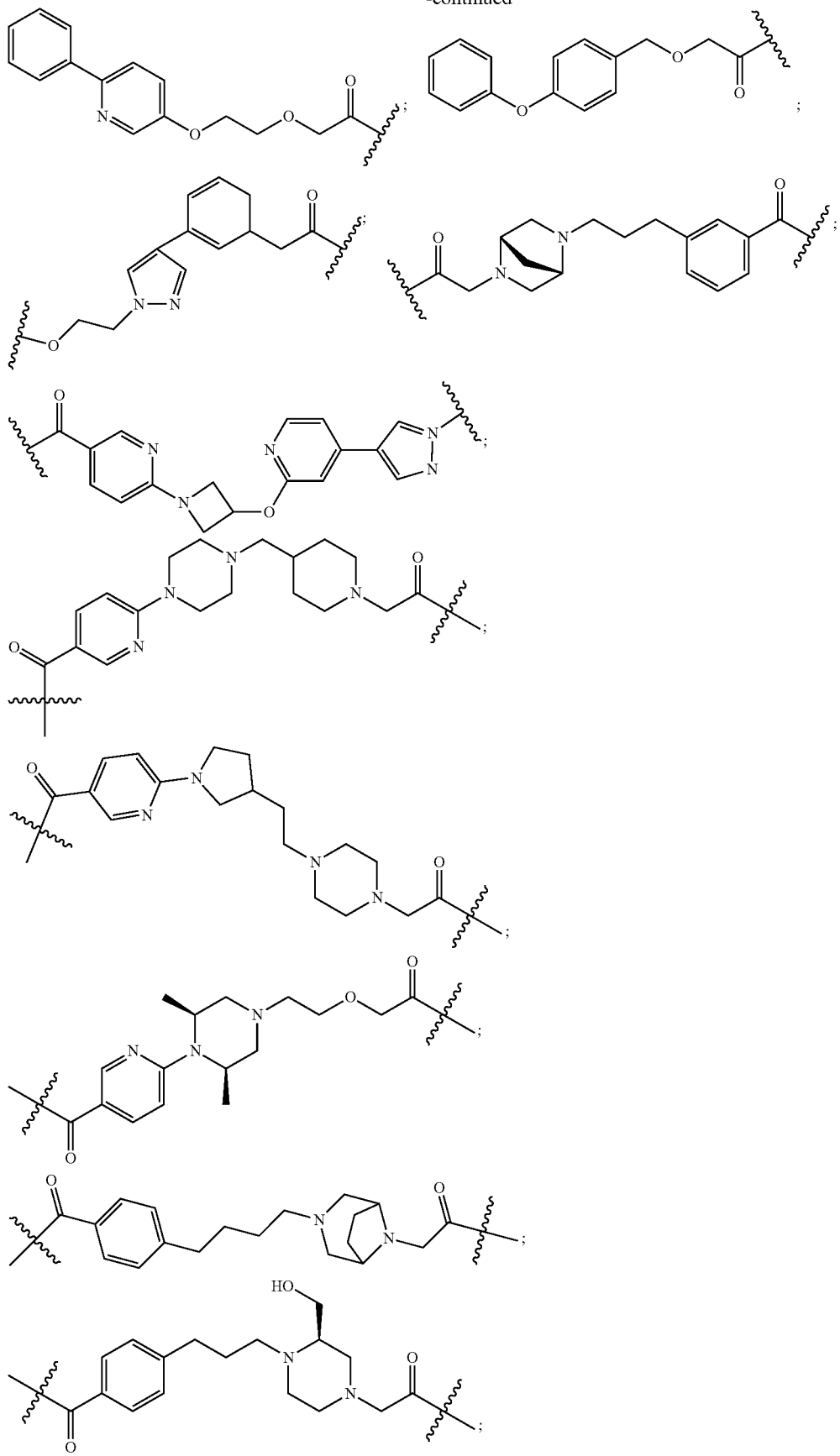

1307 1308
-continued
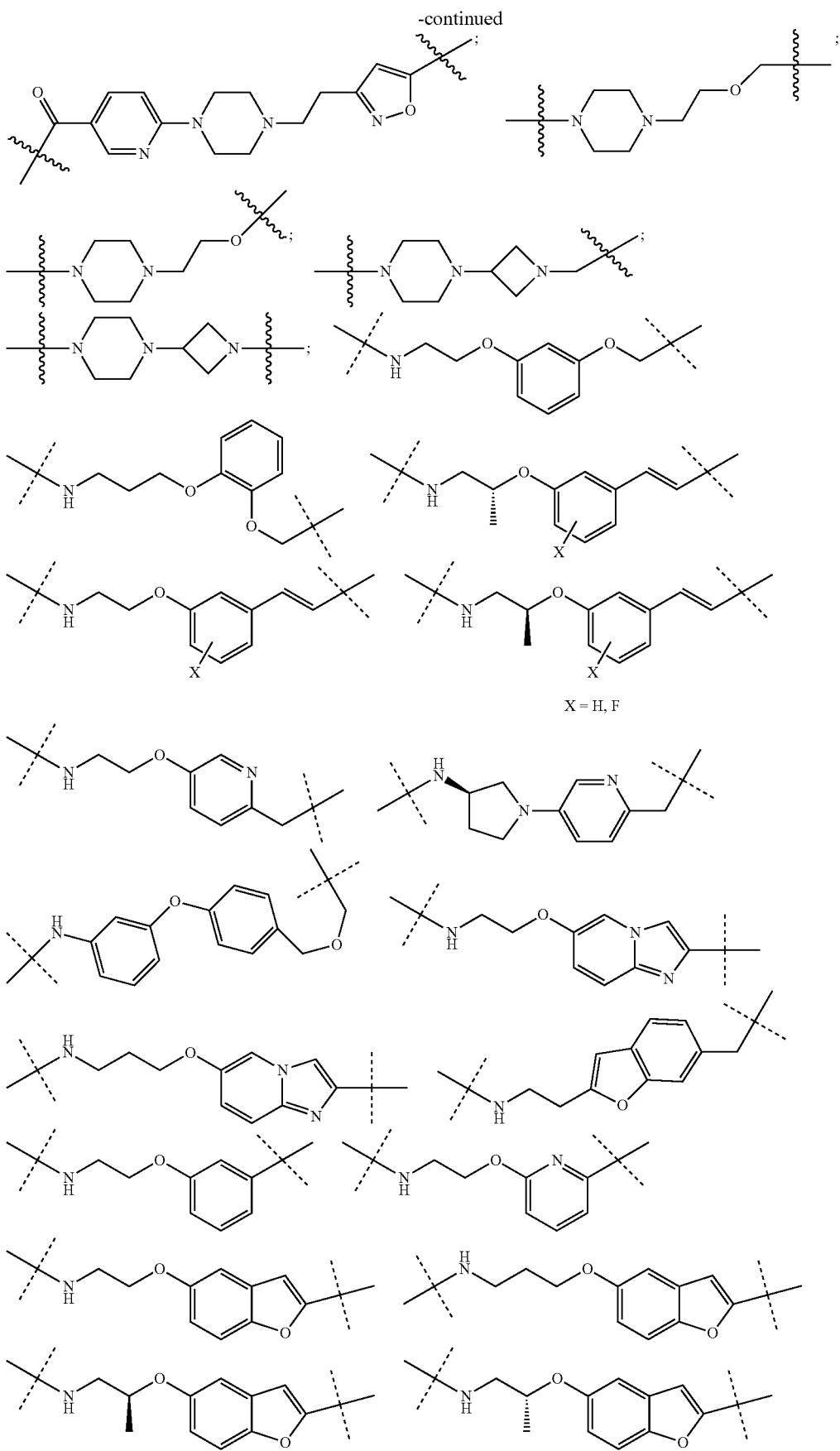

-continued
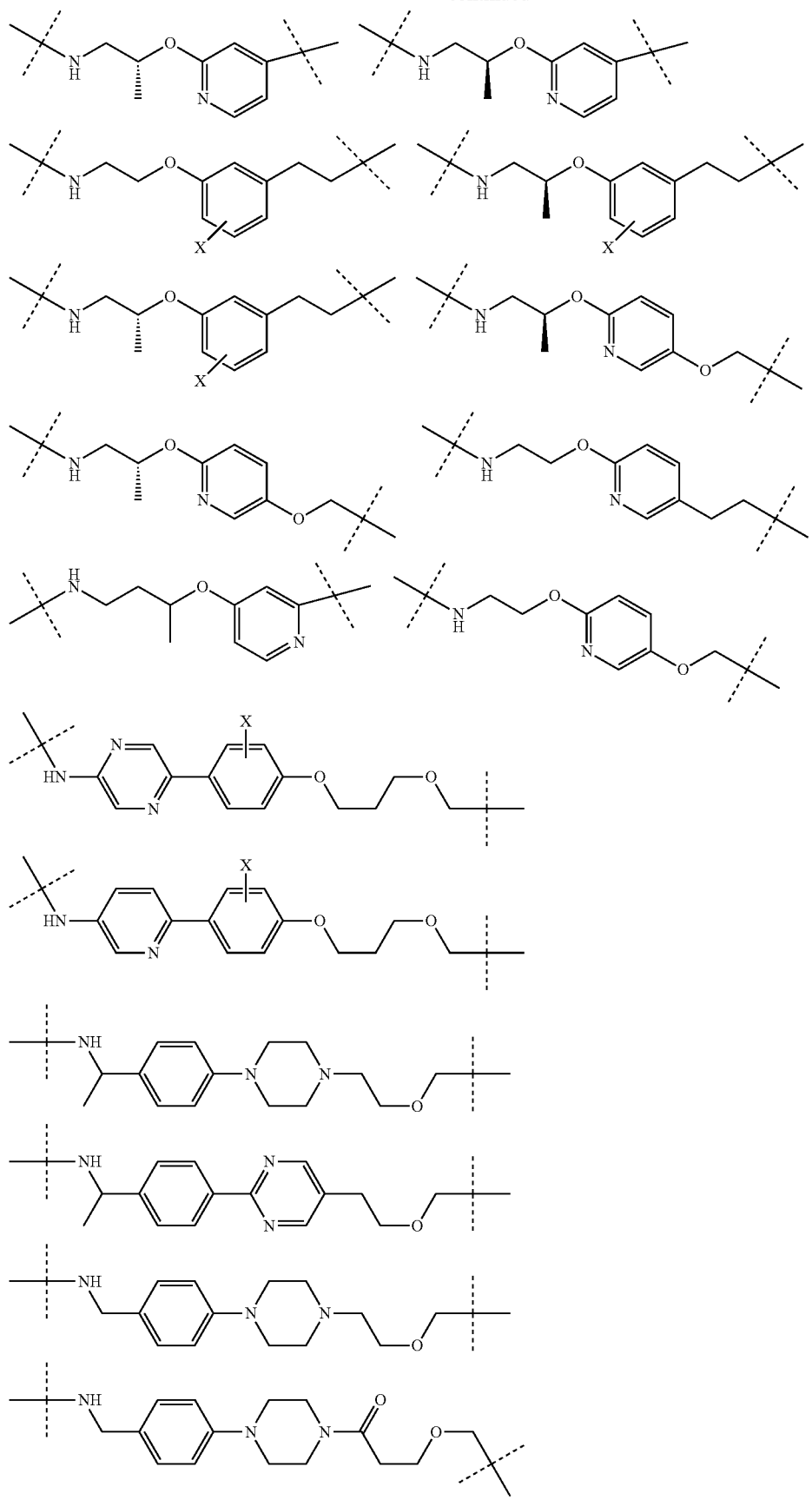

1311 1312
-continued
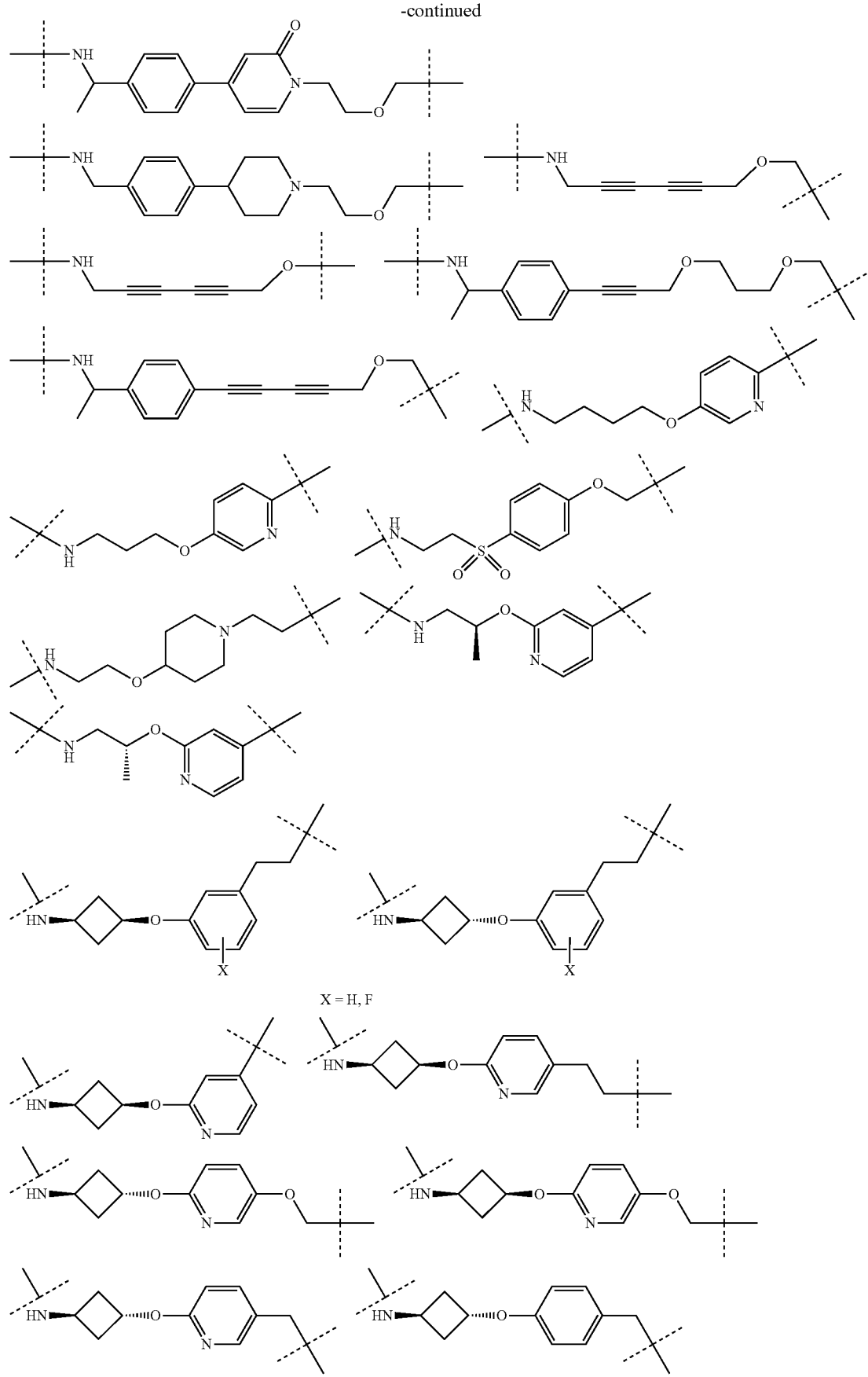
X = H, F

-continued
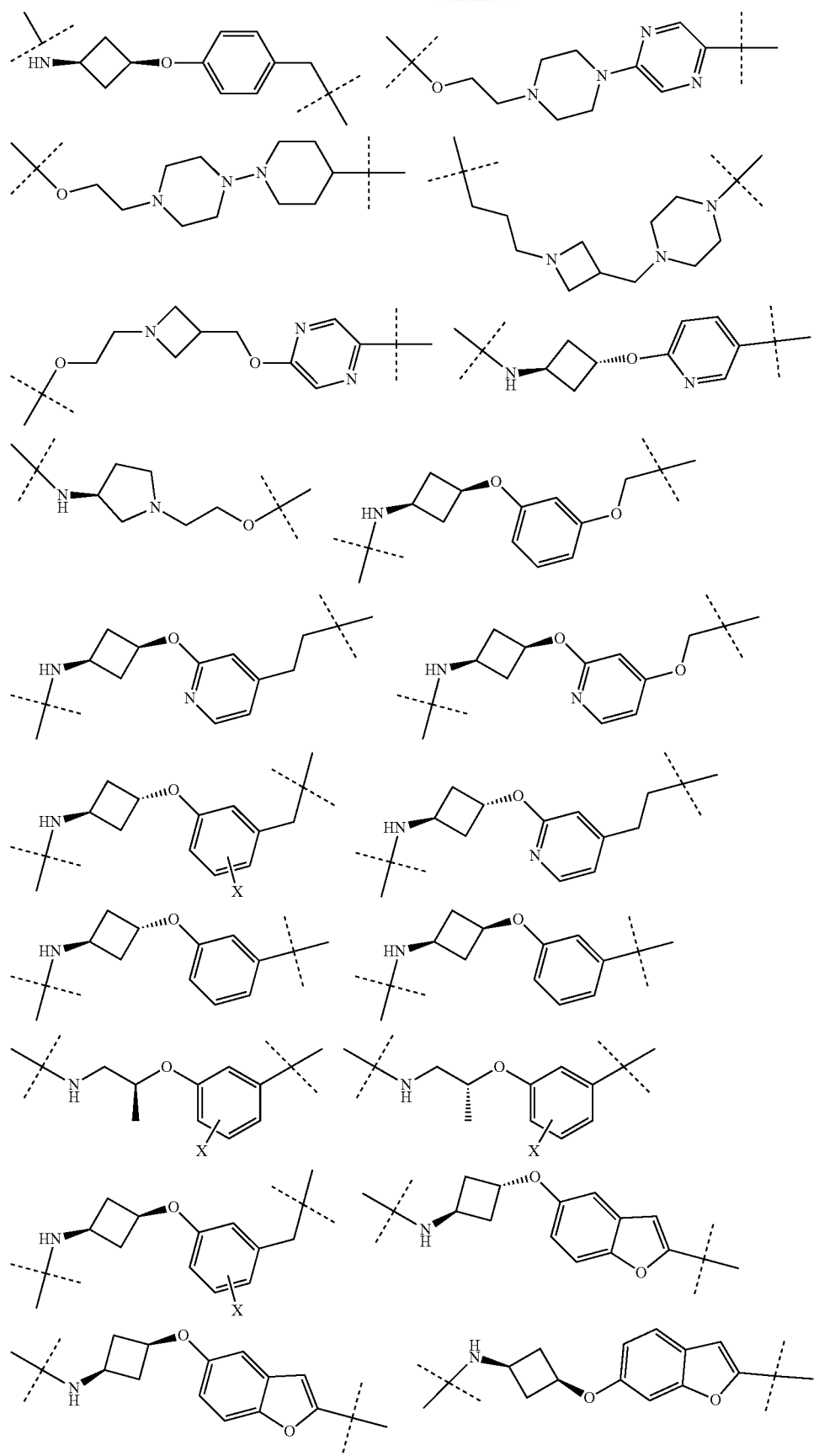

1315 1316
-continued
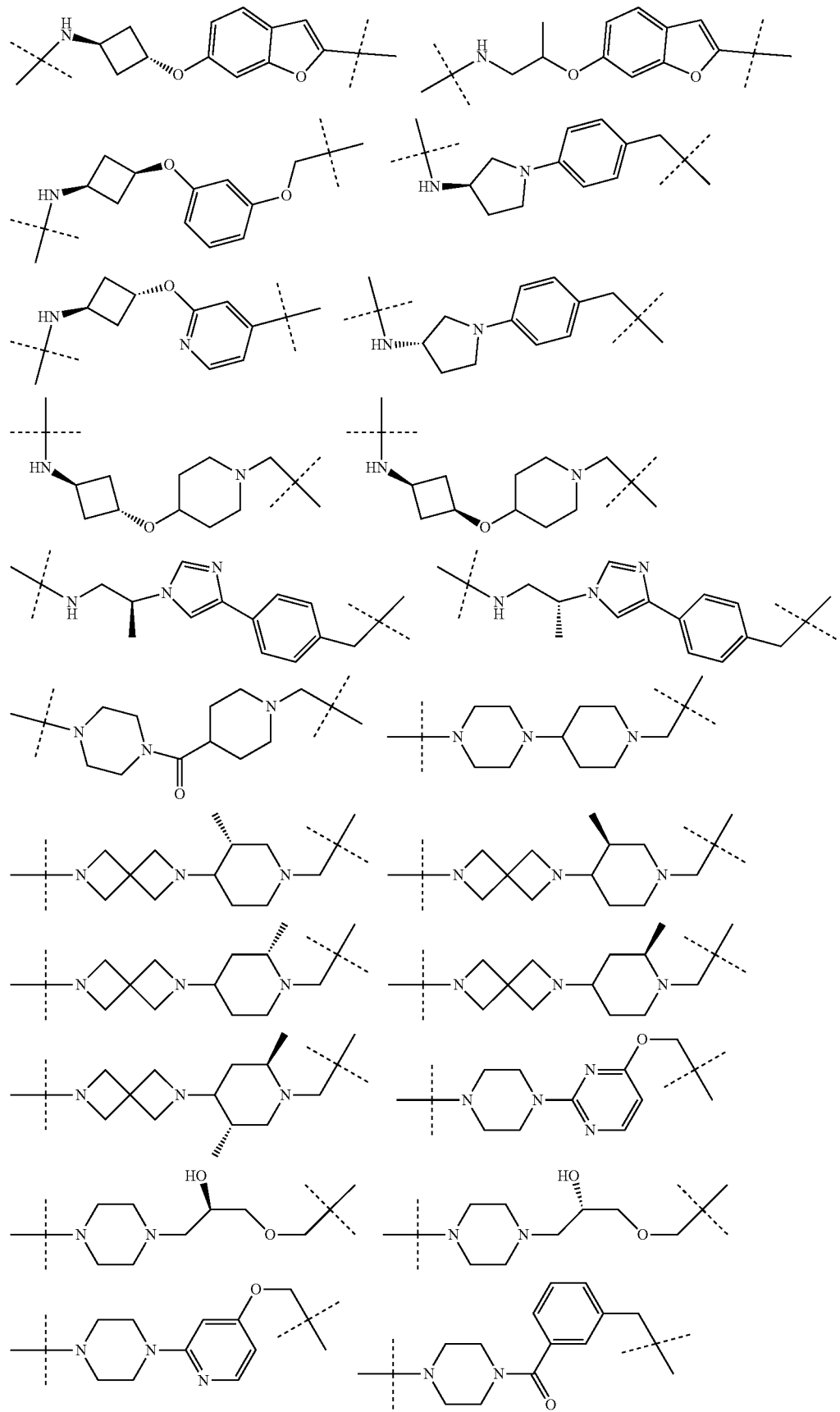

1317 1318
-continued
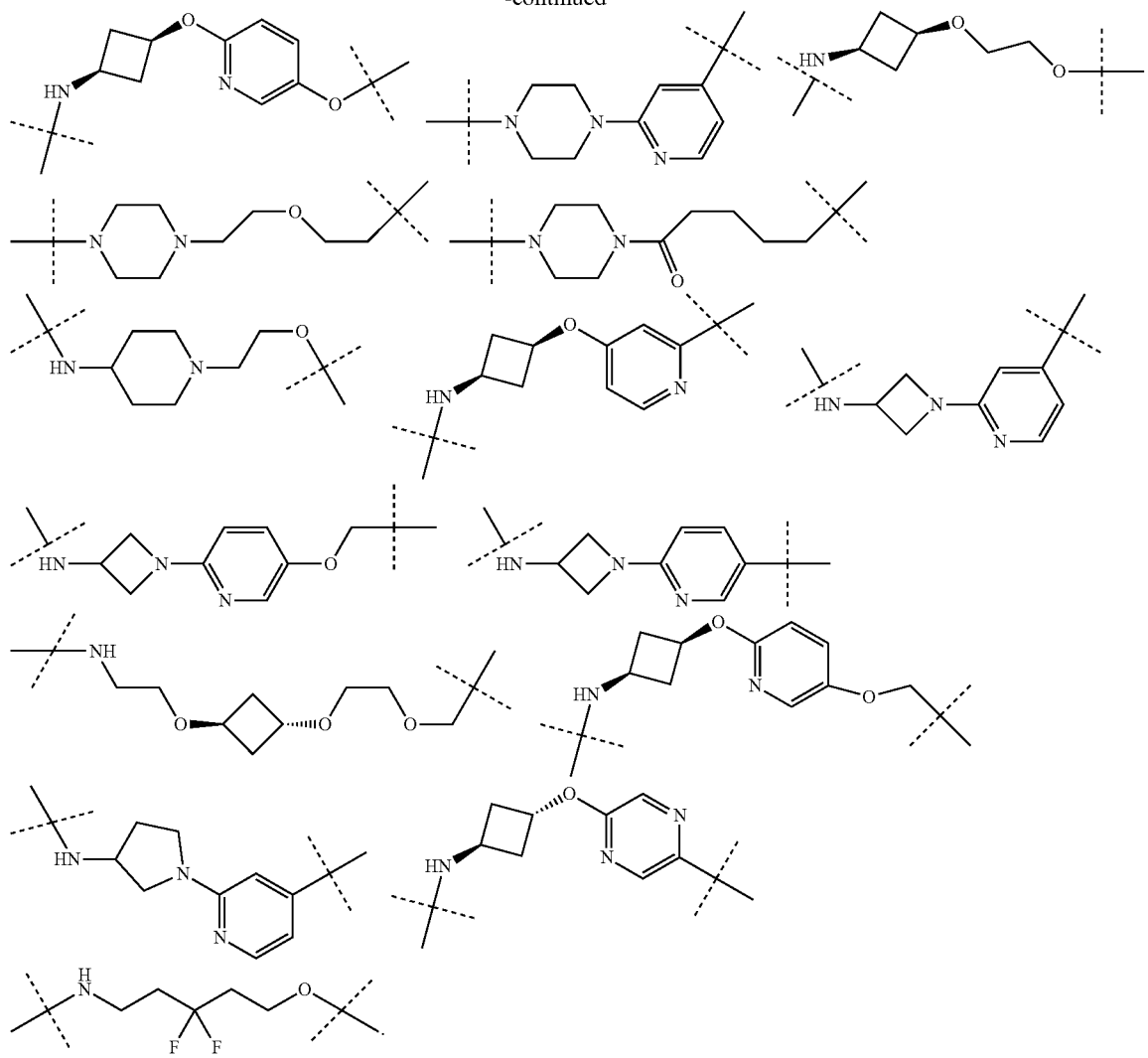
In any aspect or embodiment described herein, the linker (L) is selected from the group consisting of:
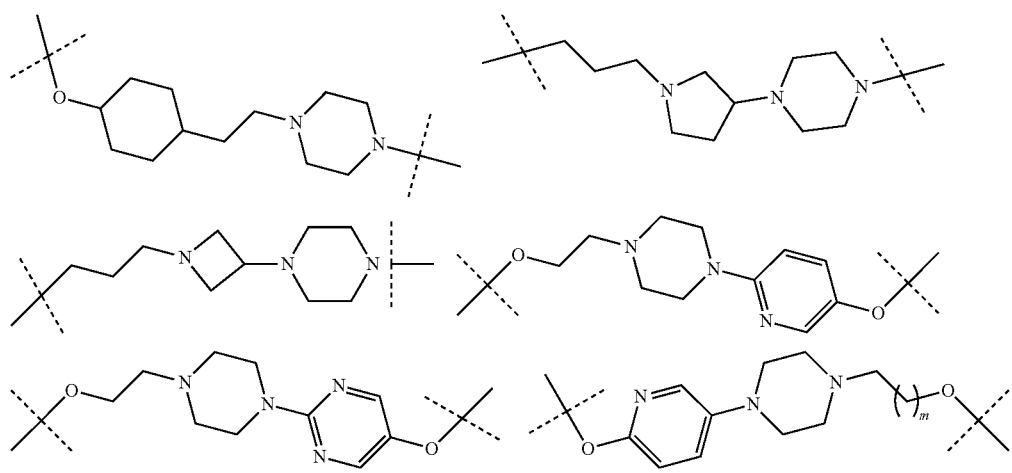

-continued
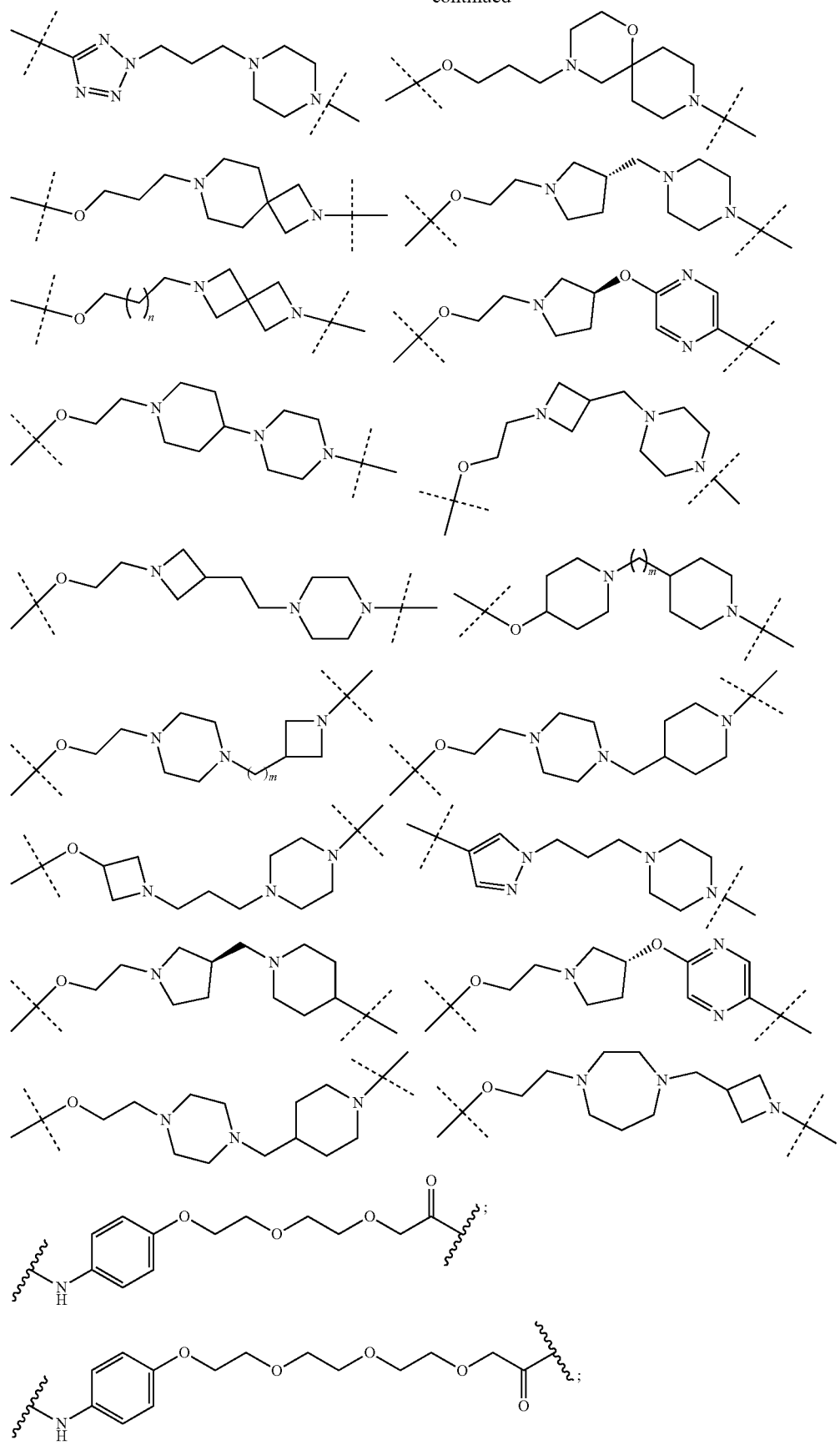

-continued
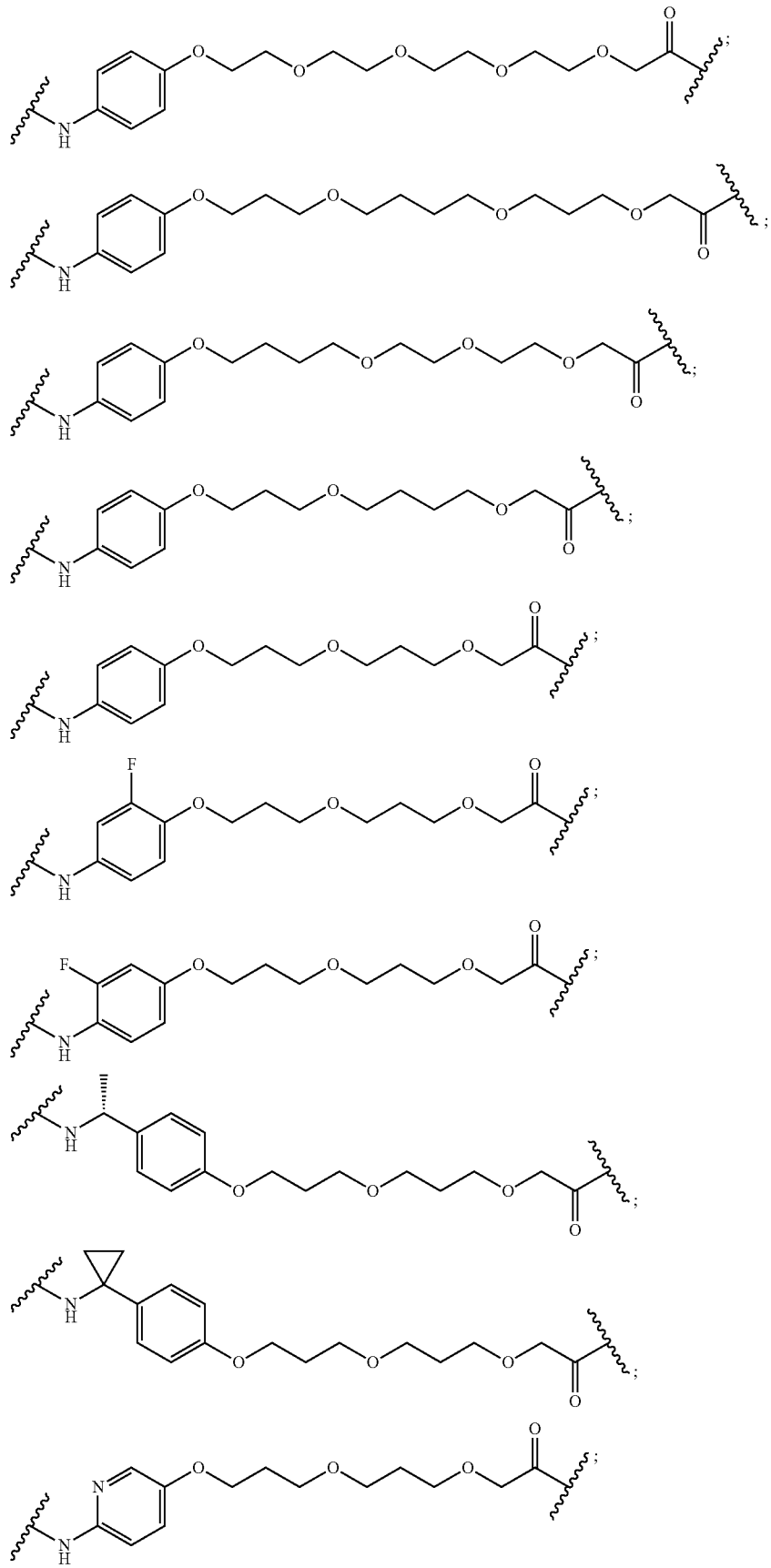

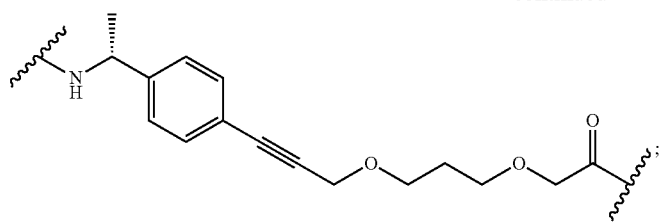
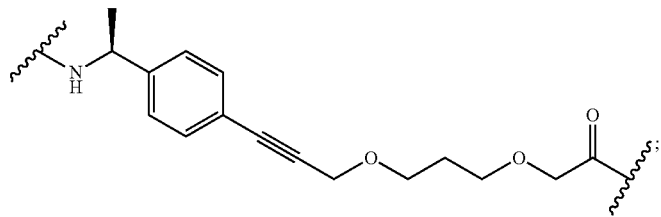
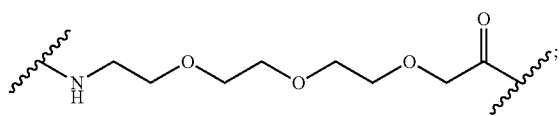
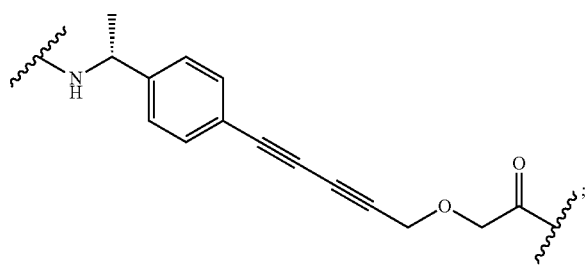
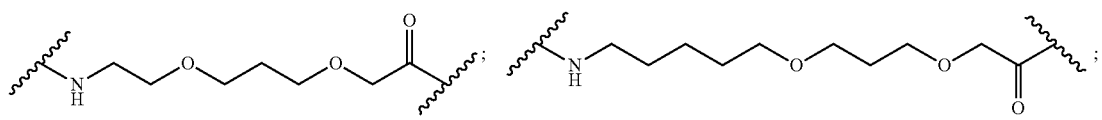
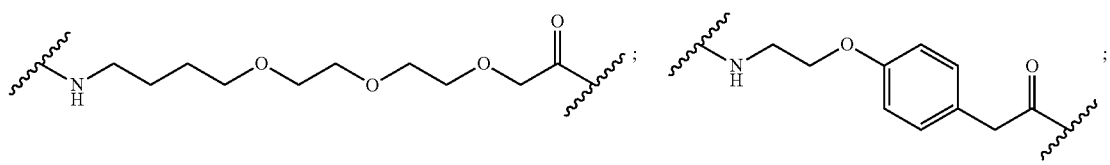
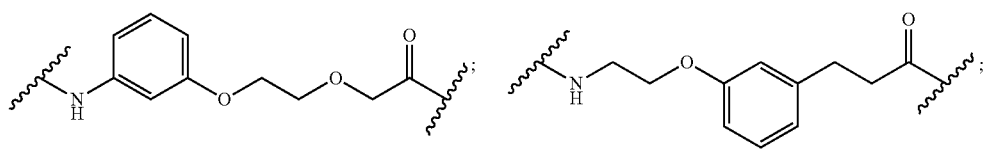
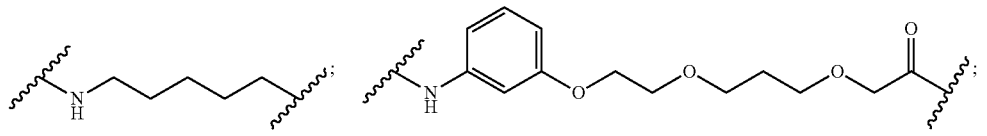
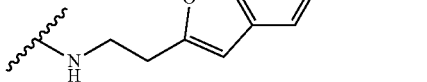

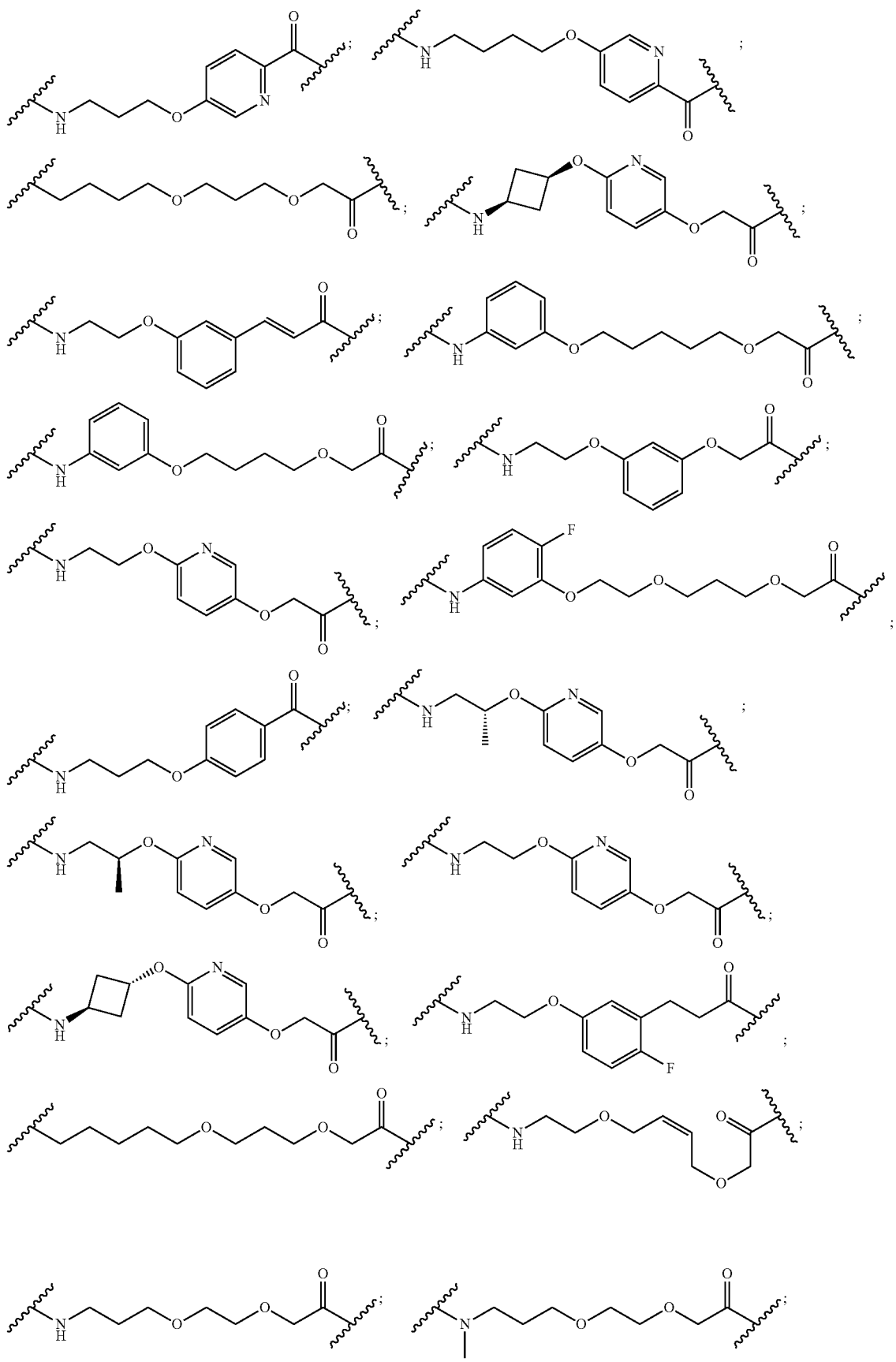

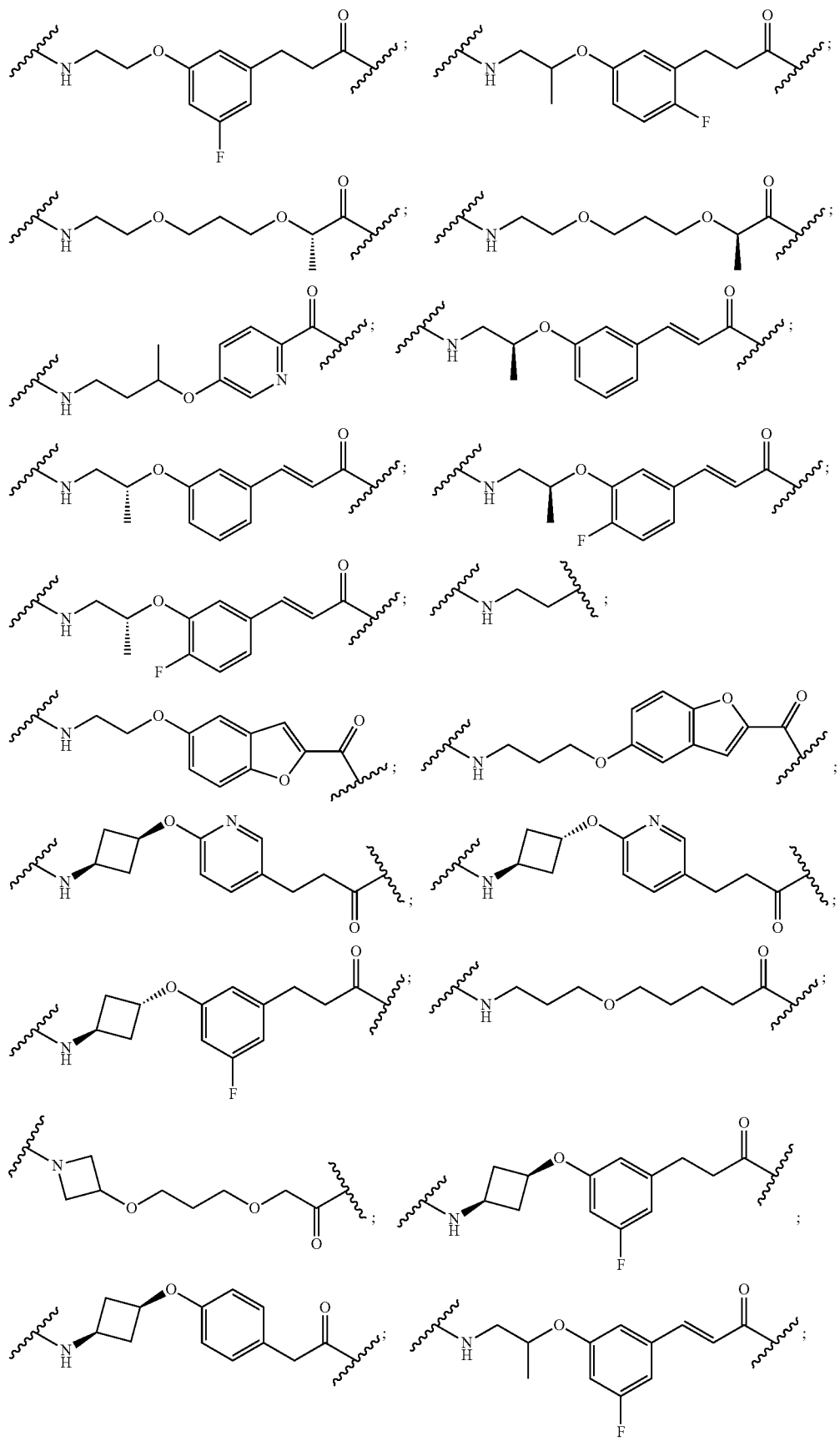

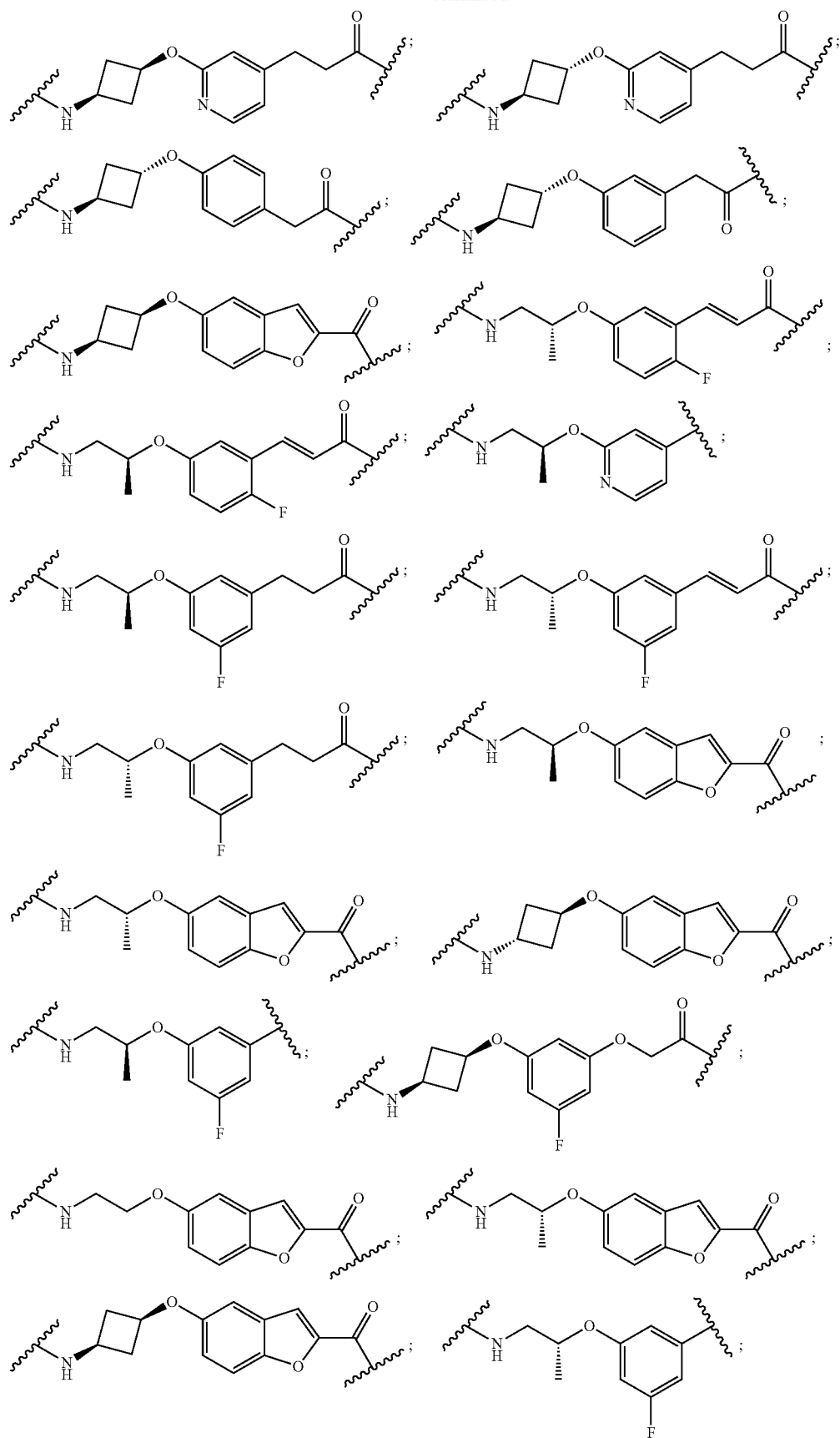

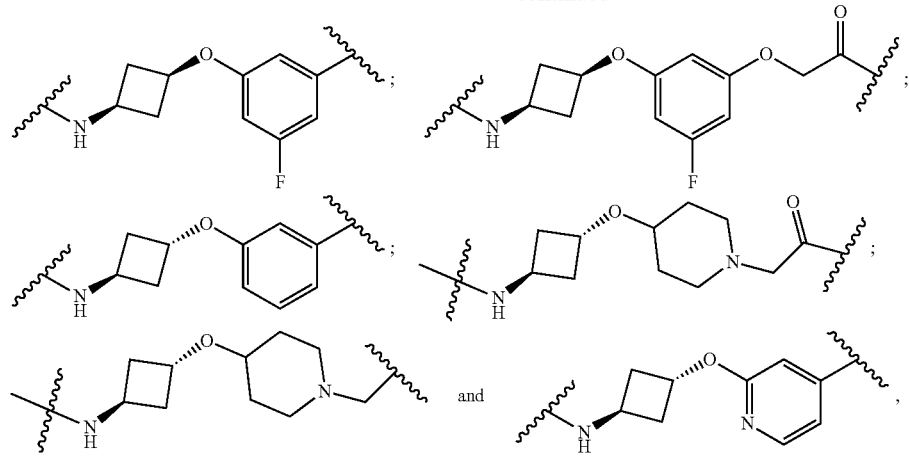
wherein each m and n is independently 0, 1, 2, 3, 4, 5, or 6.
In any aspect or embodiment described herein, the linker (L) is selected from the group consisting of:
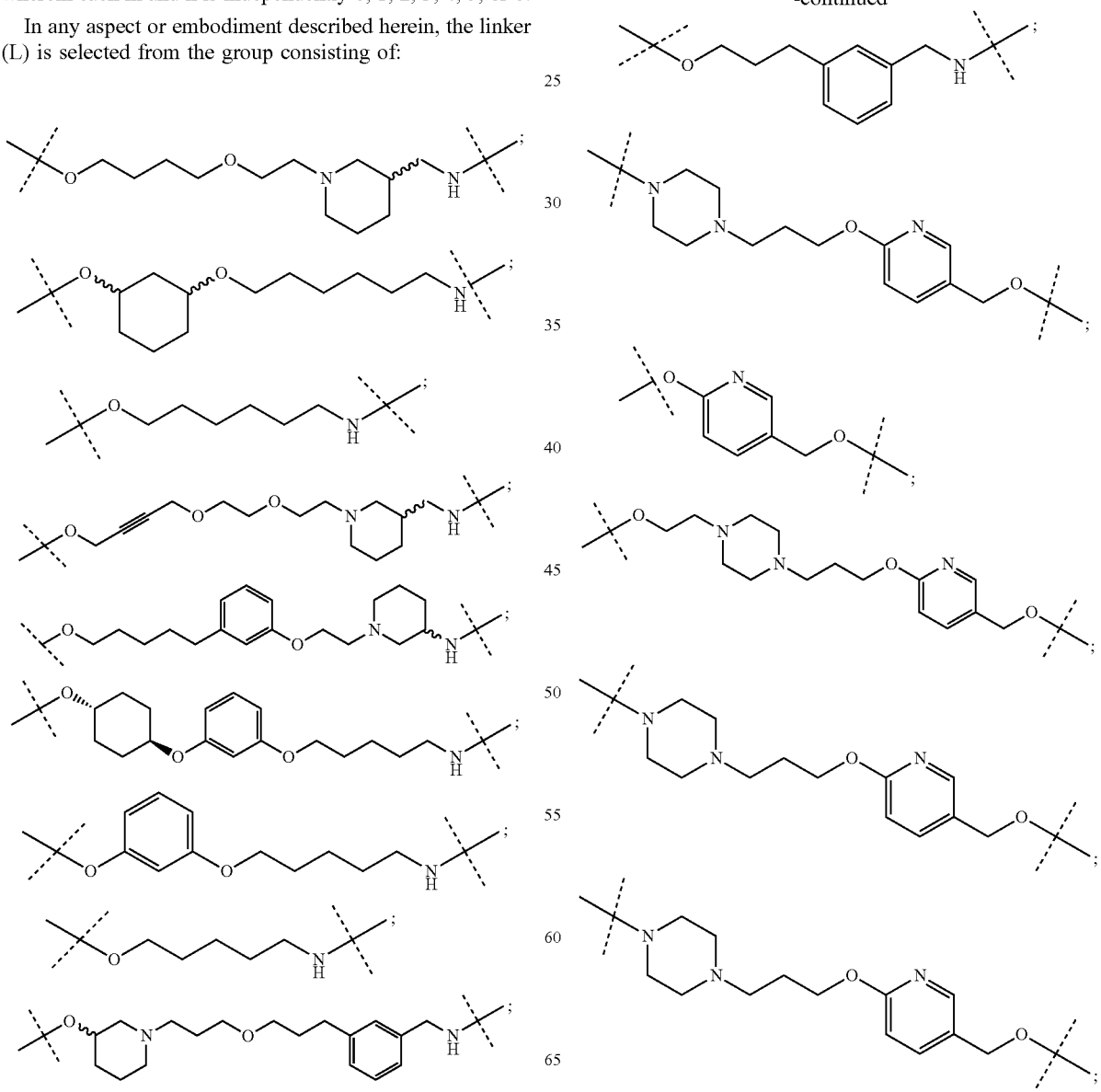

1333
-continued
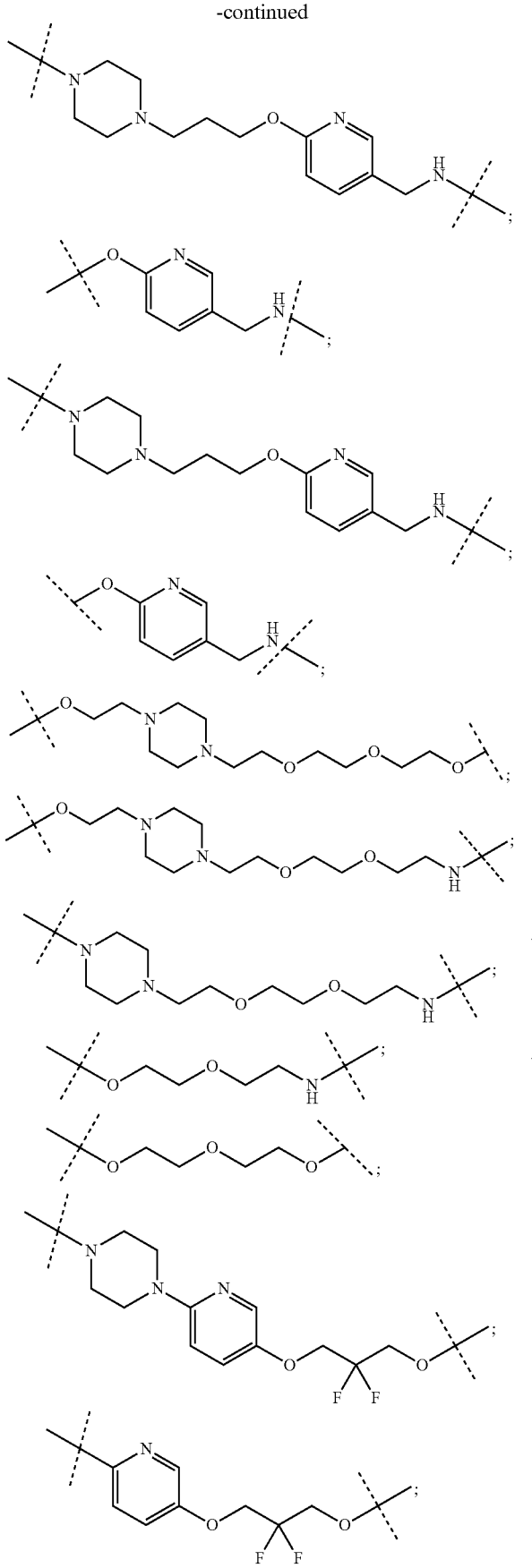
1334
-continued
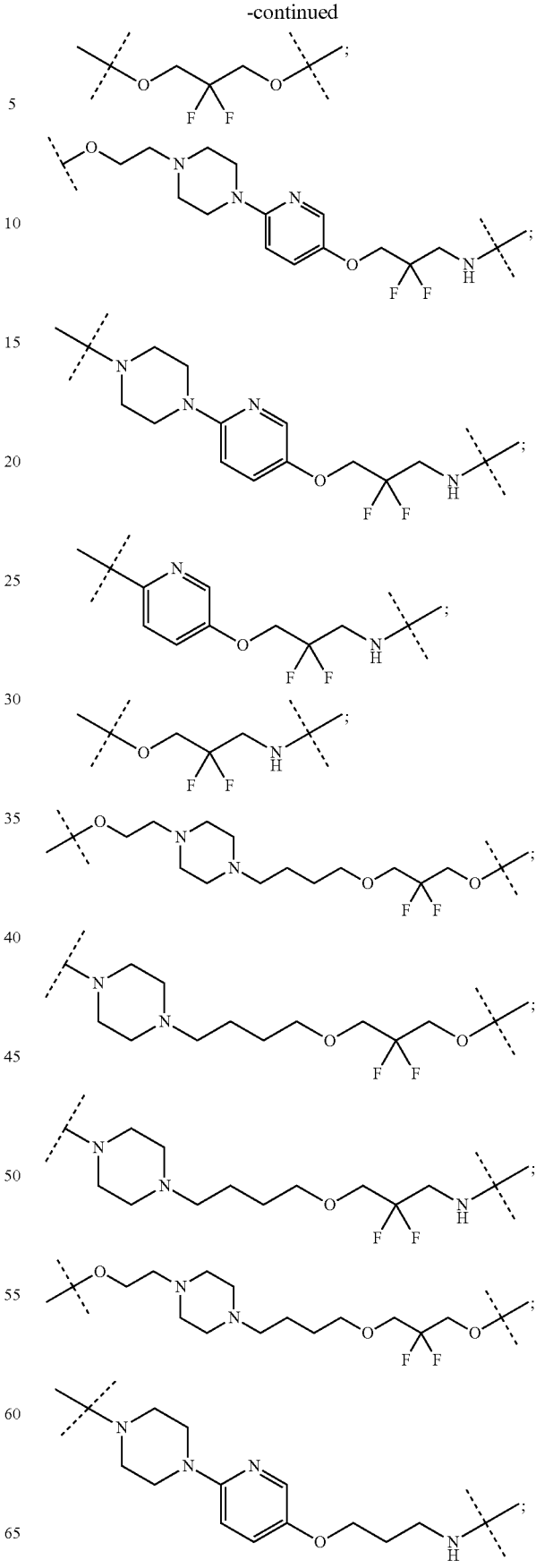

1335
-continued
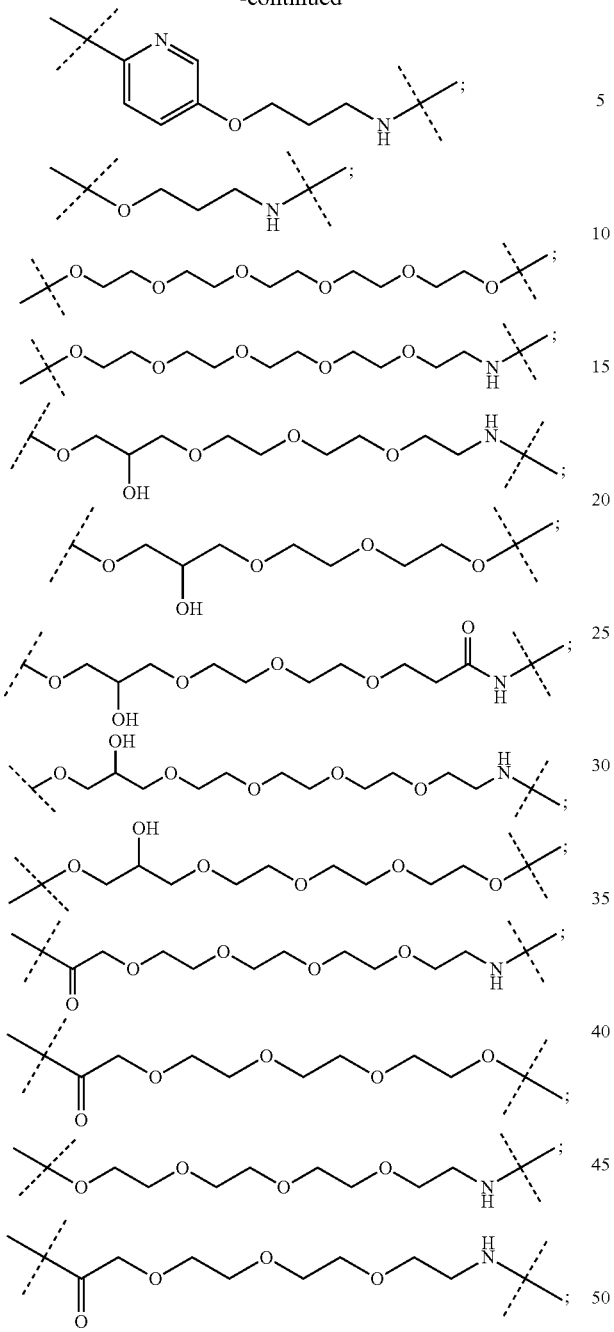
1336
-continued
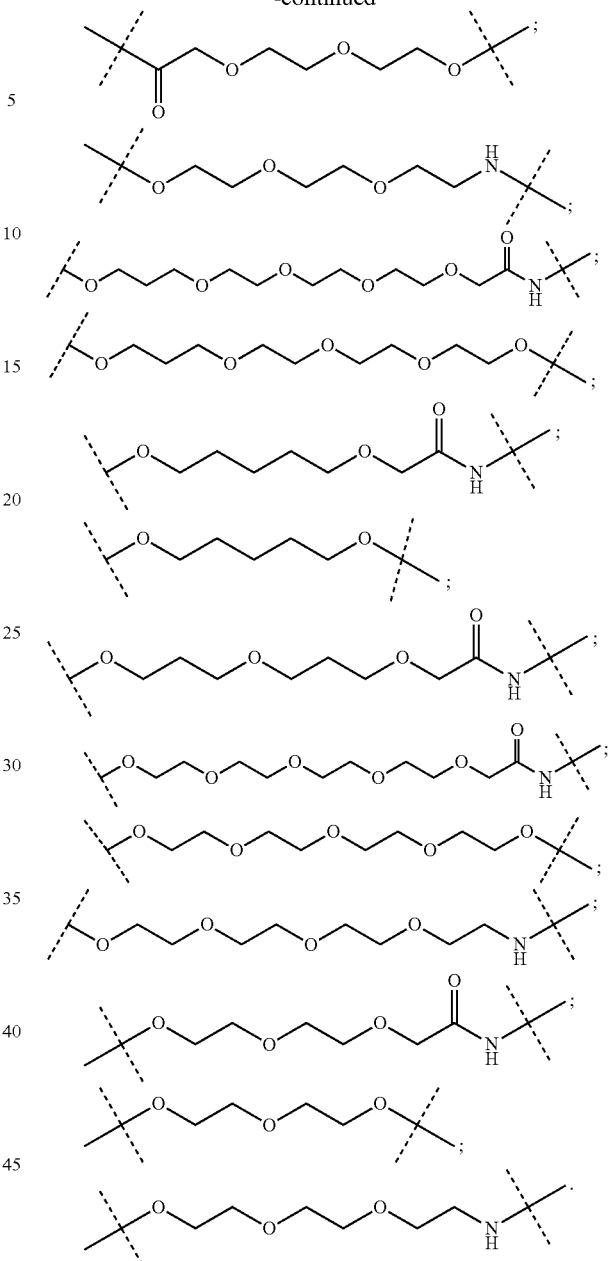
In any aspect or embodiment described herein, the linker (L) is selected from the group consisting of:
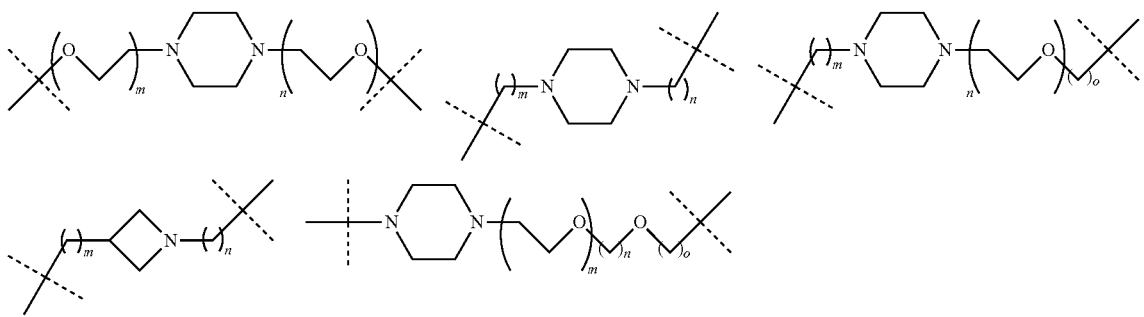

-continued
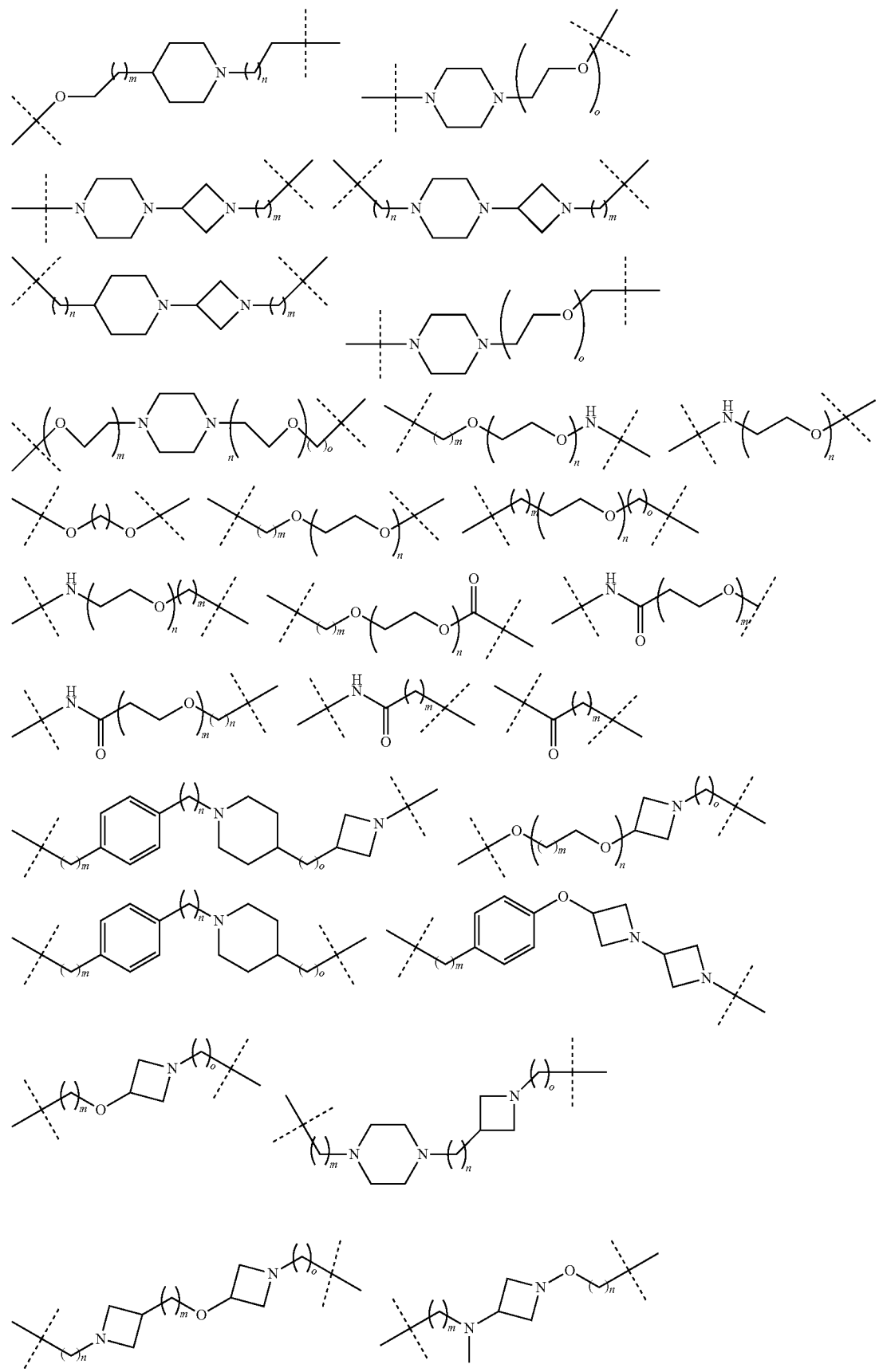

-continued
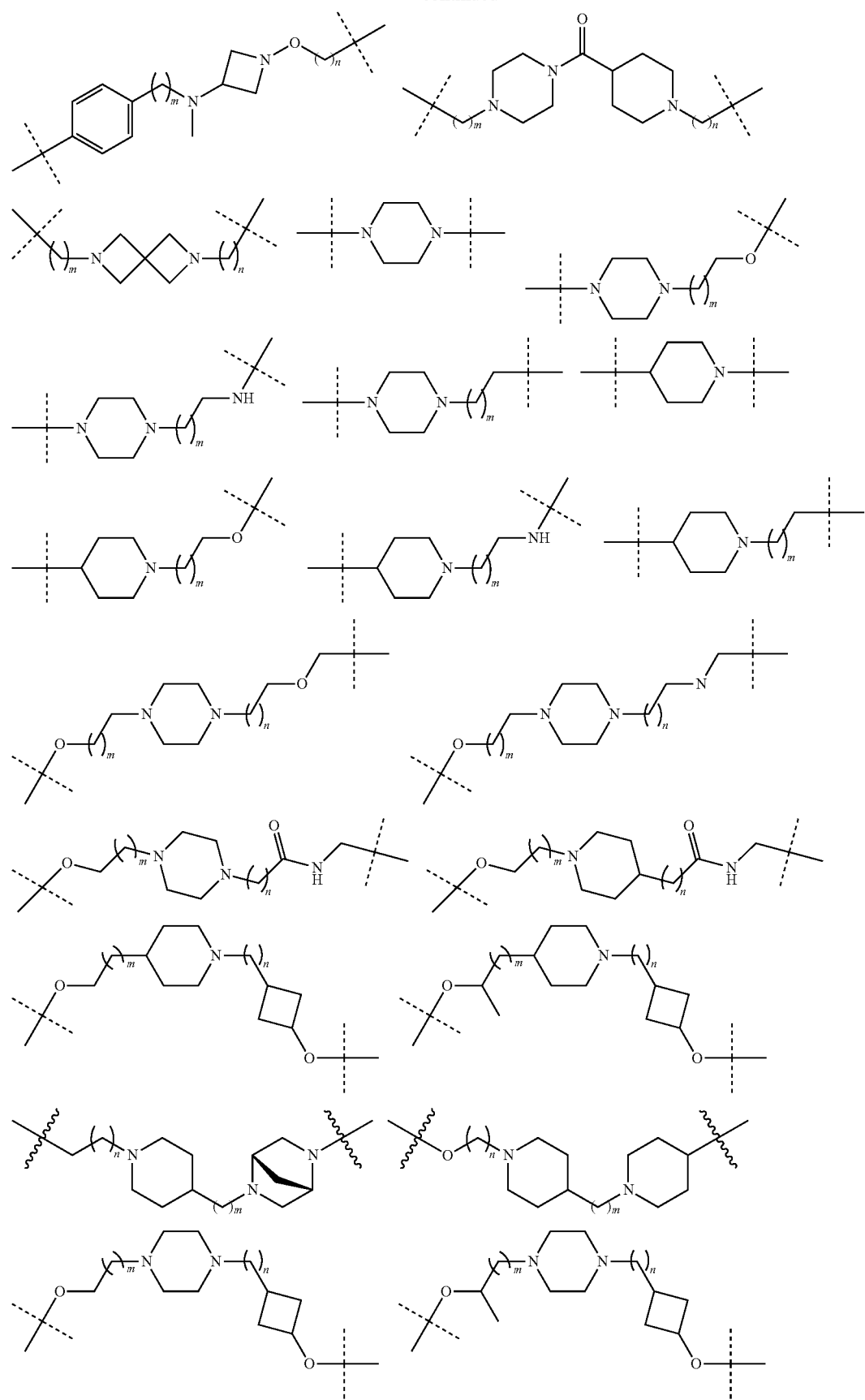

-continued
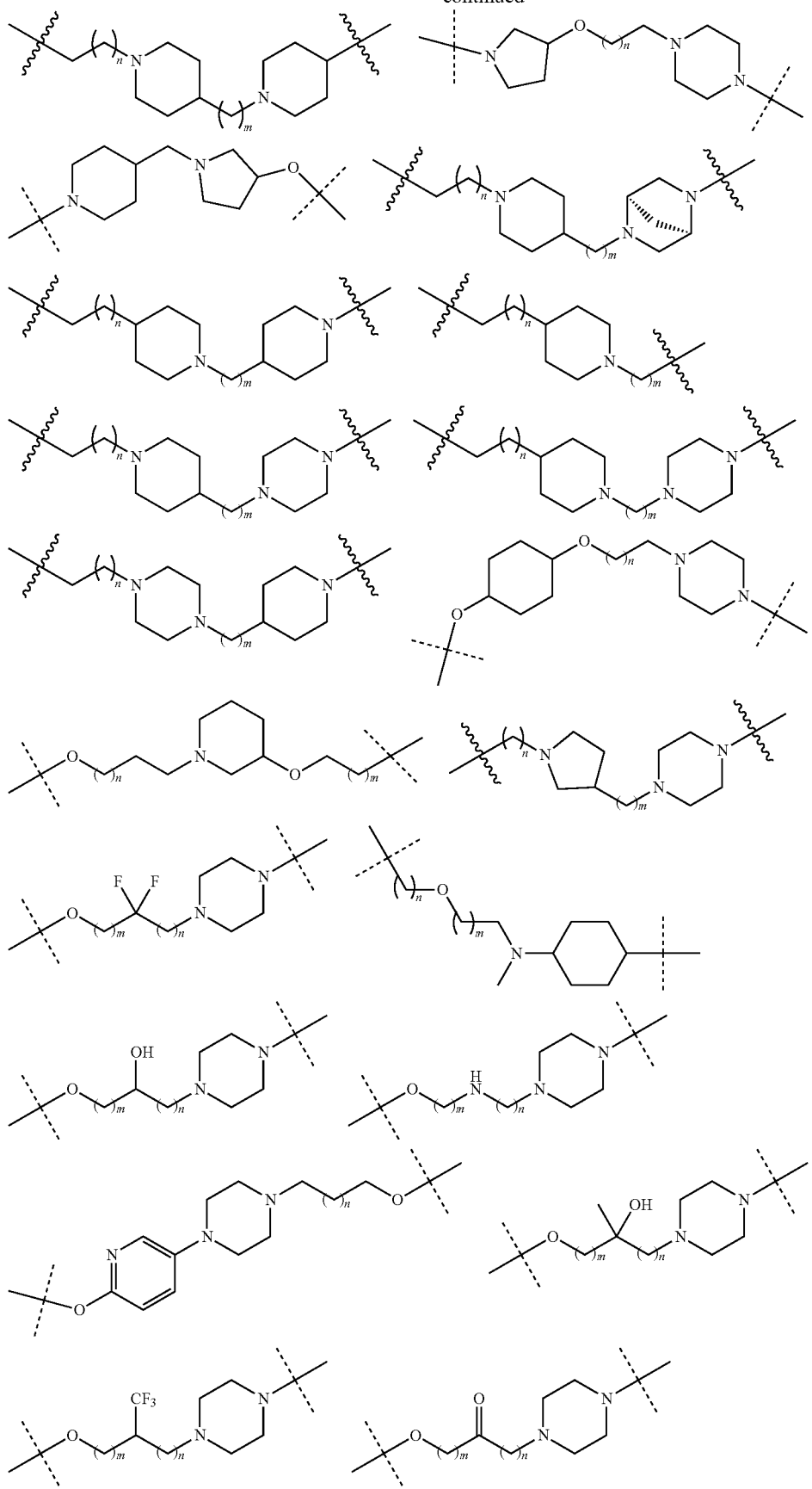

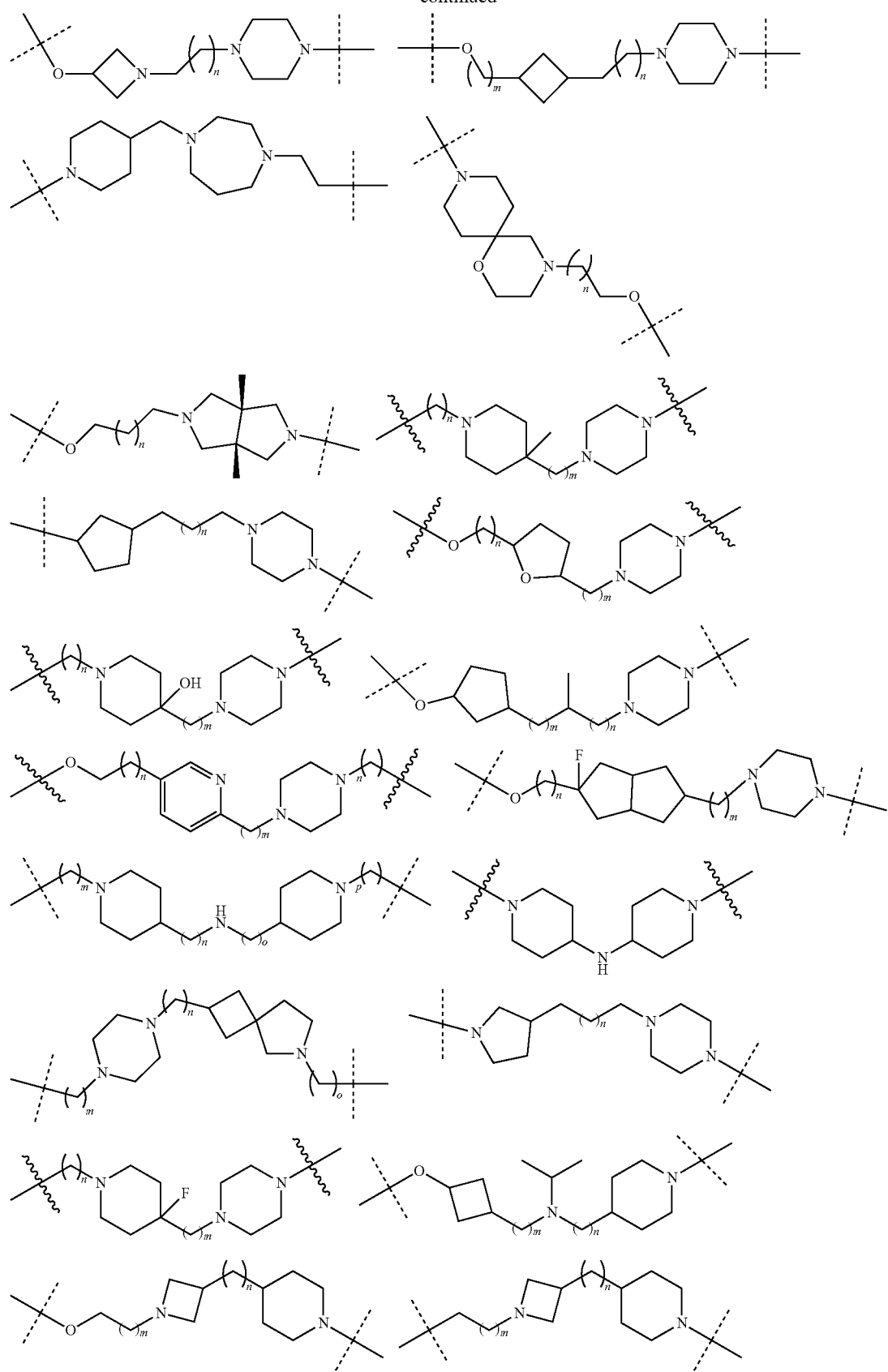

-continued
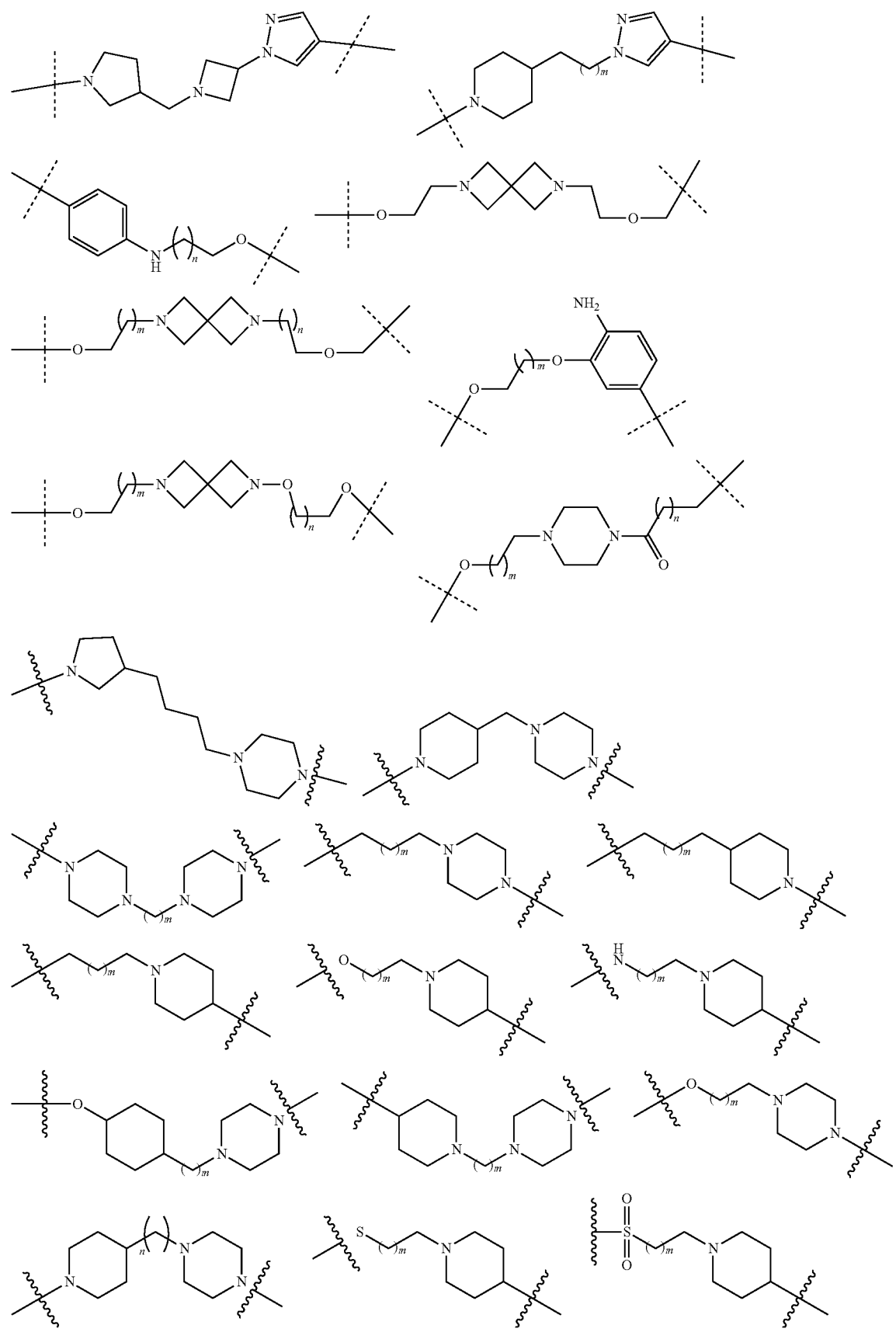

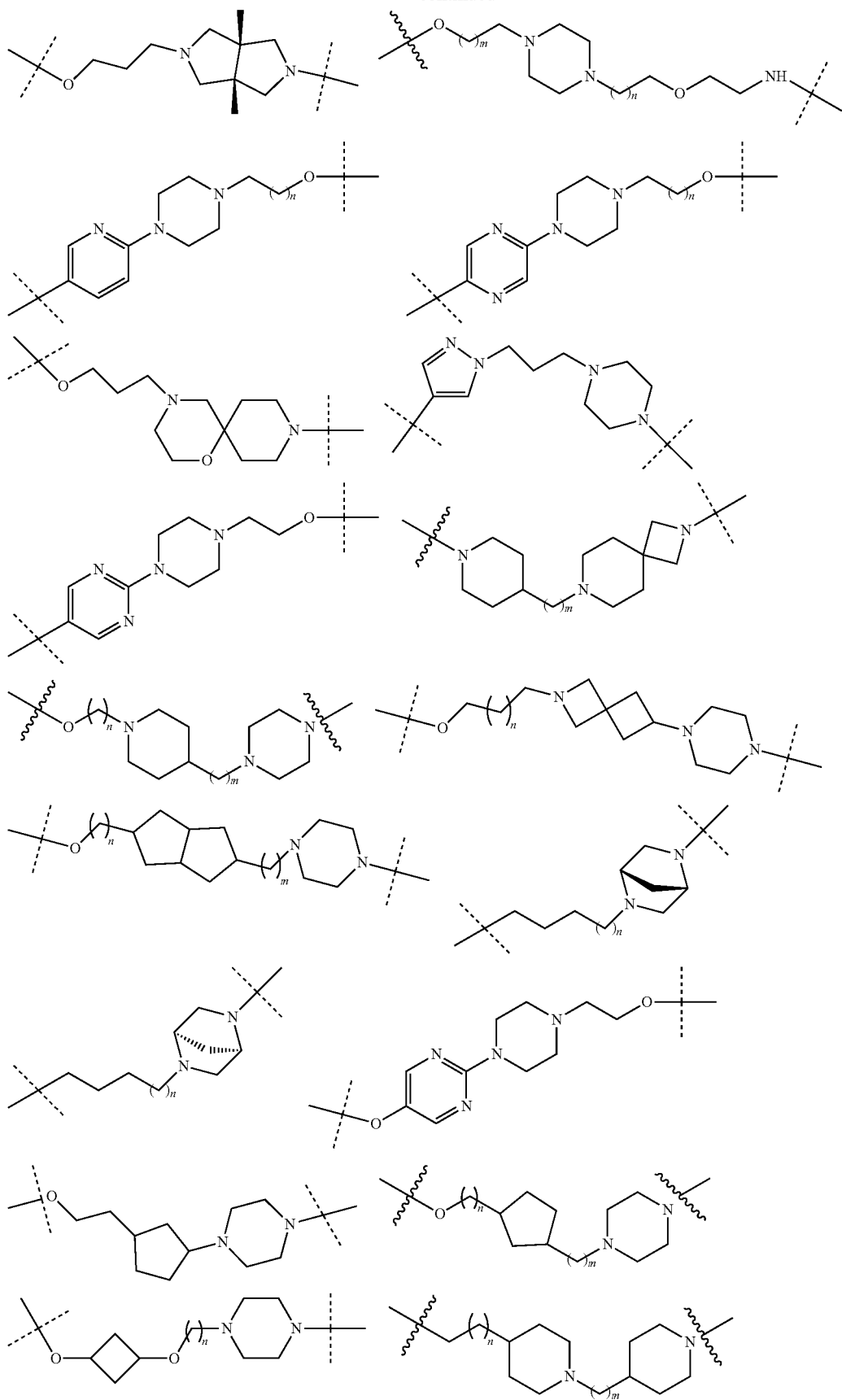
-continued

-continued
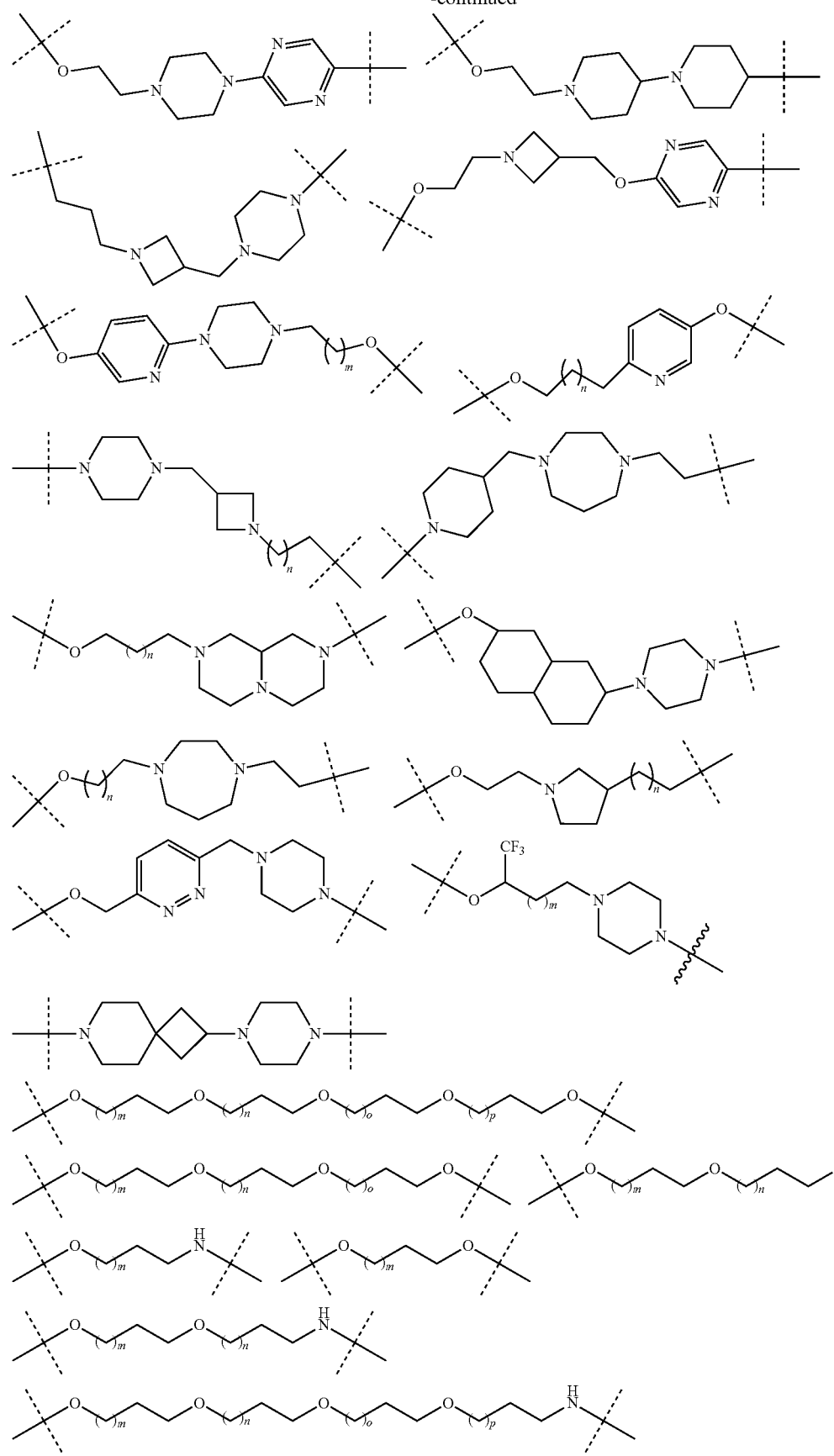

-continued
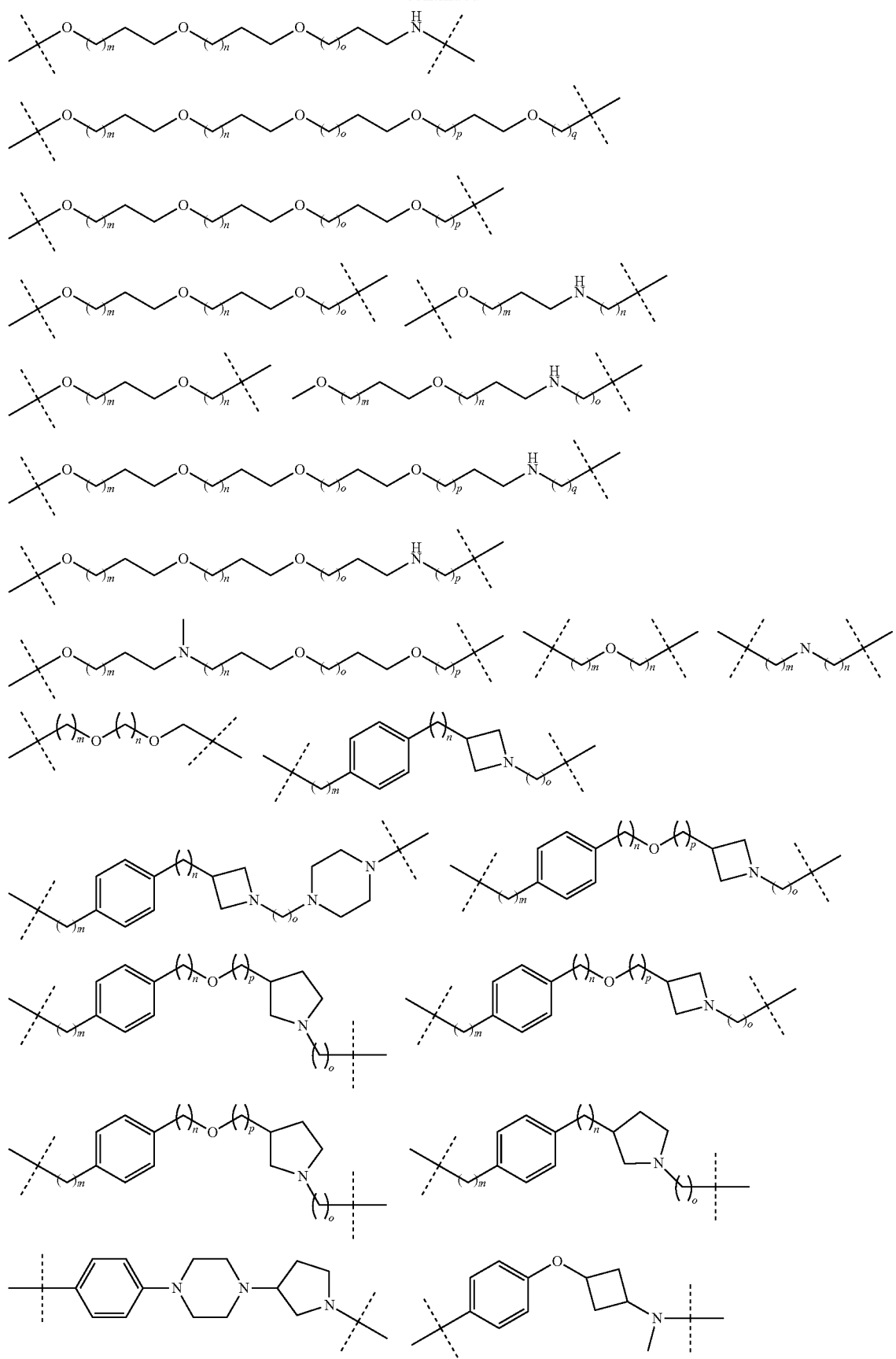

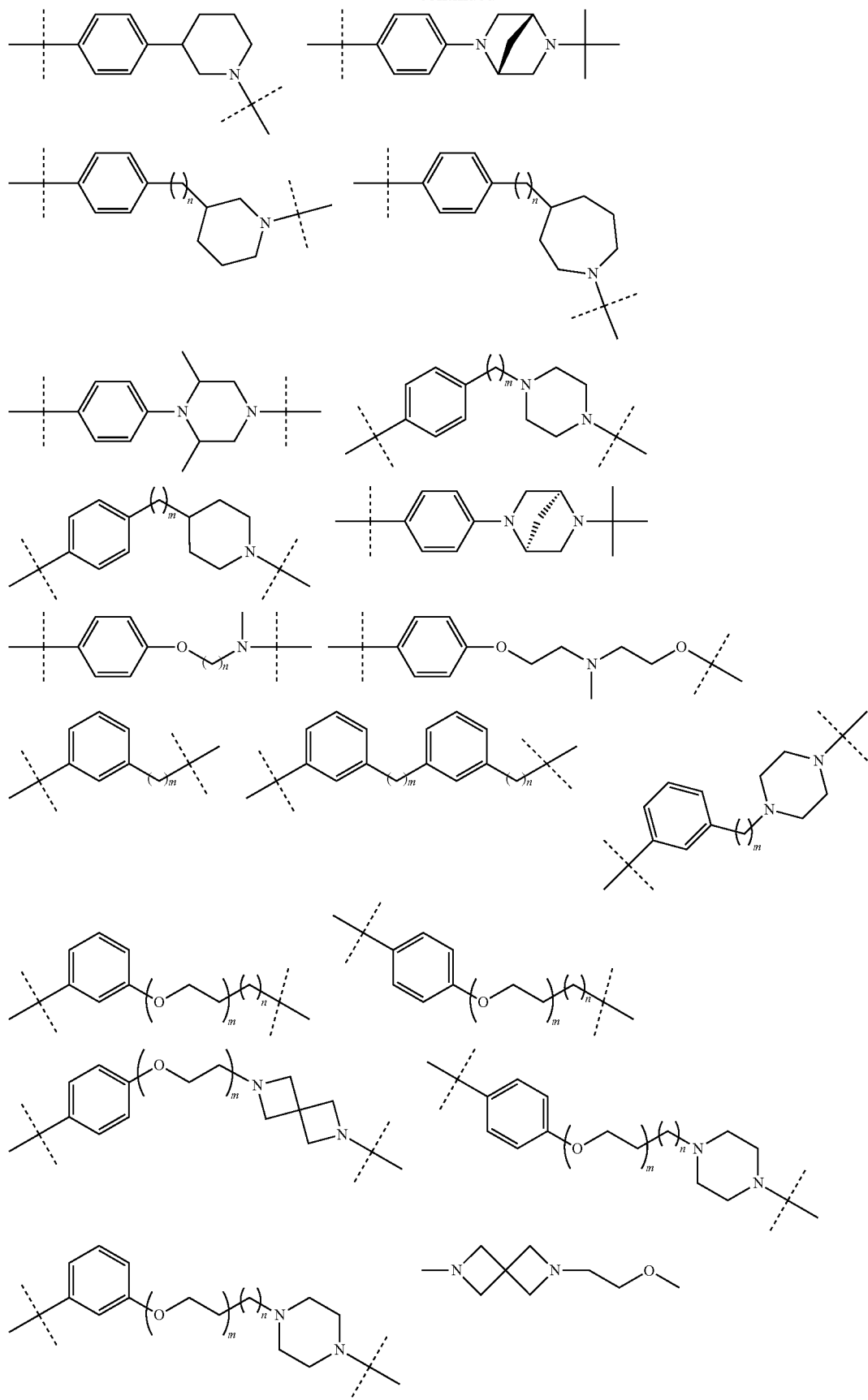

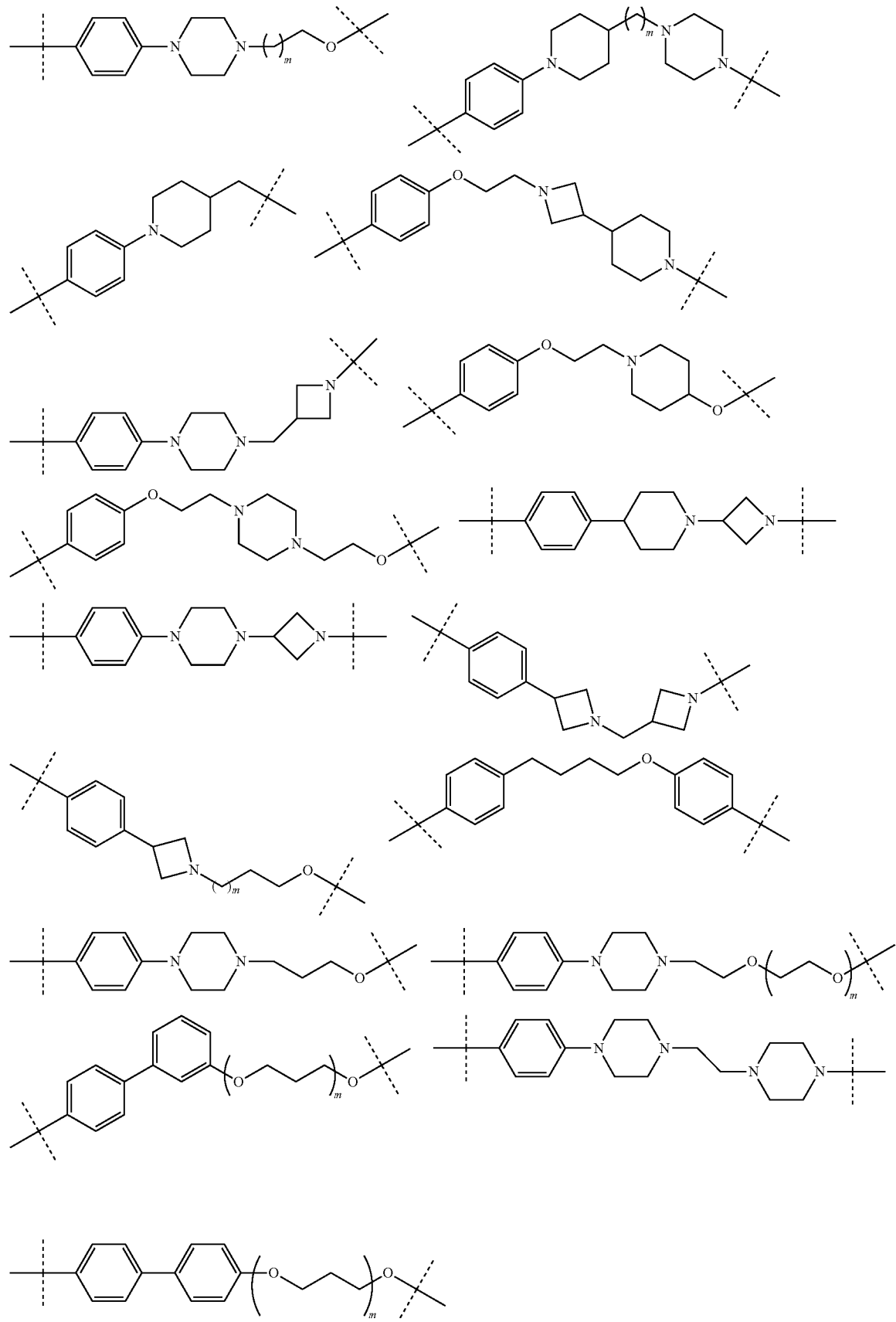

1357 1358
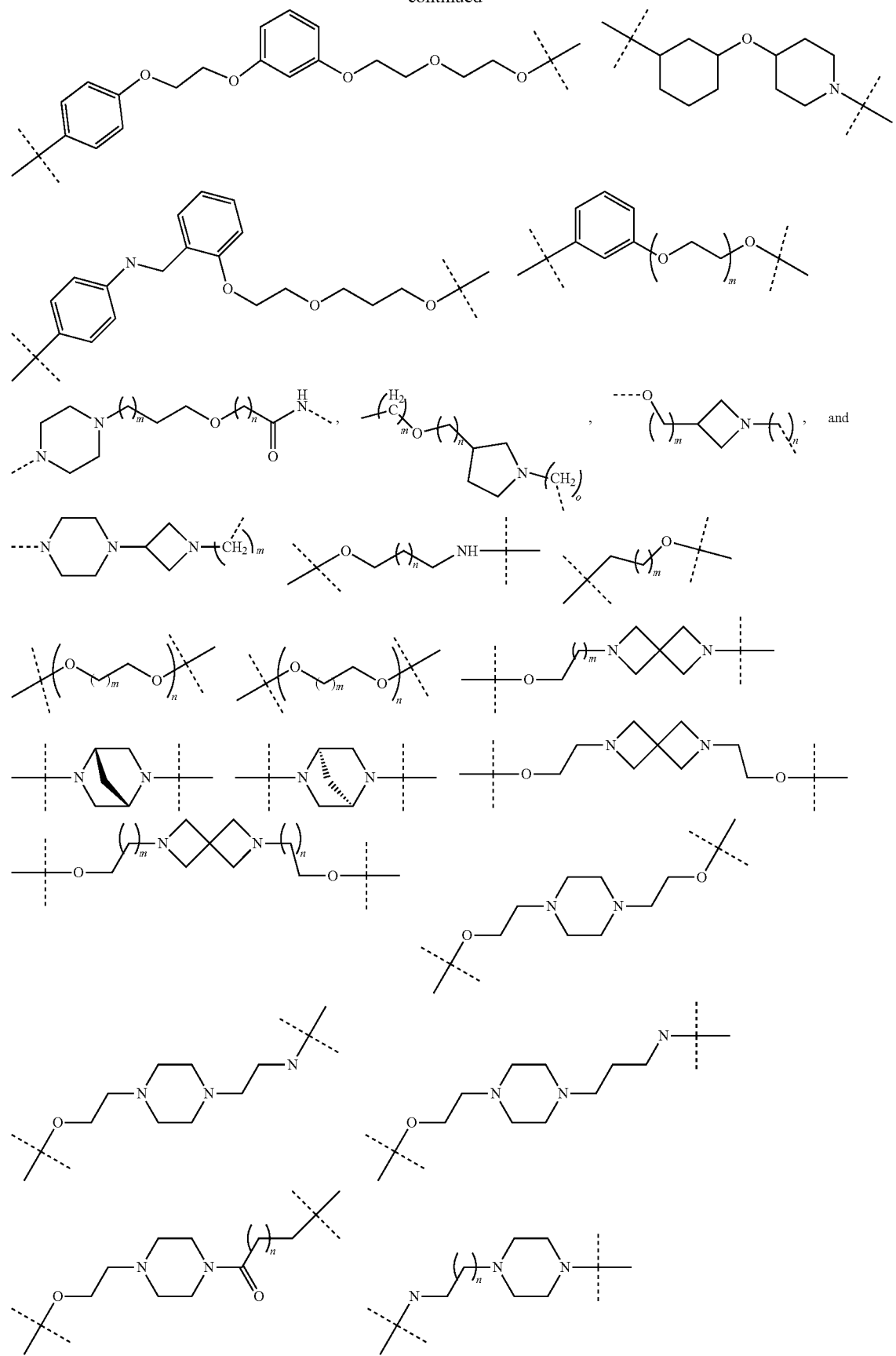

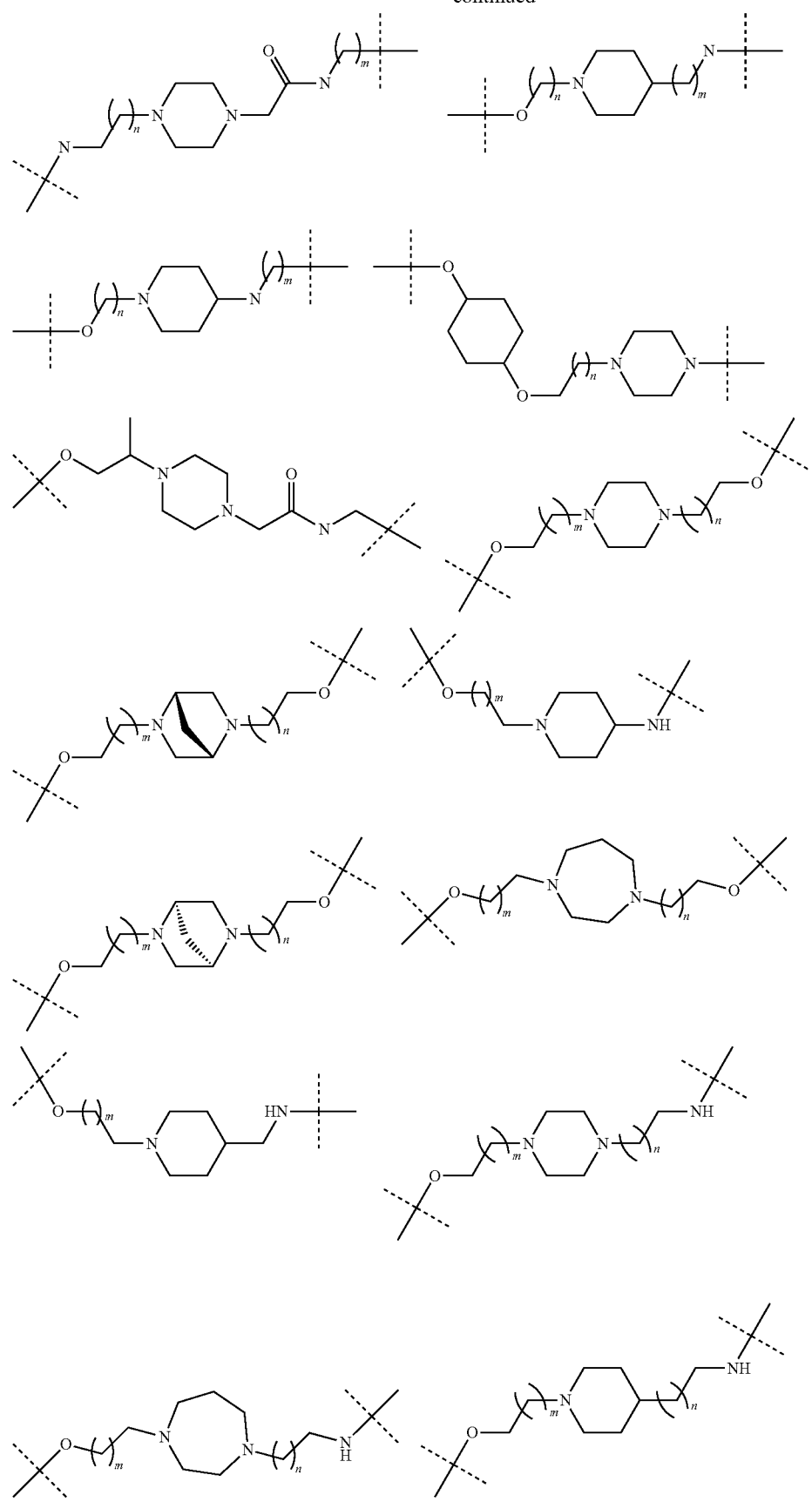

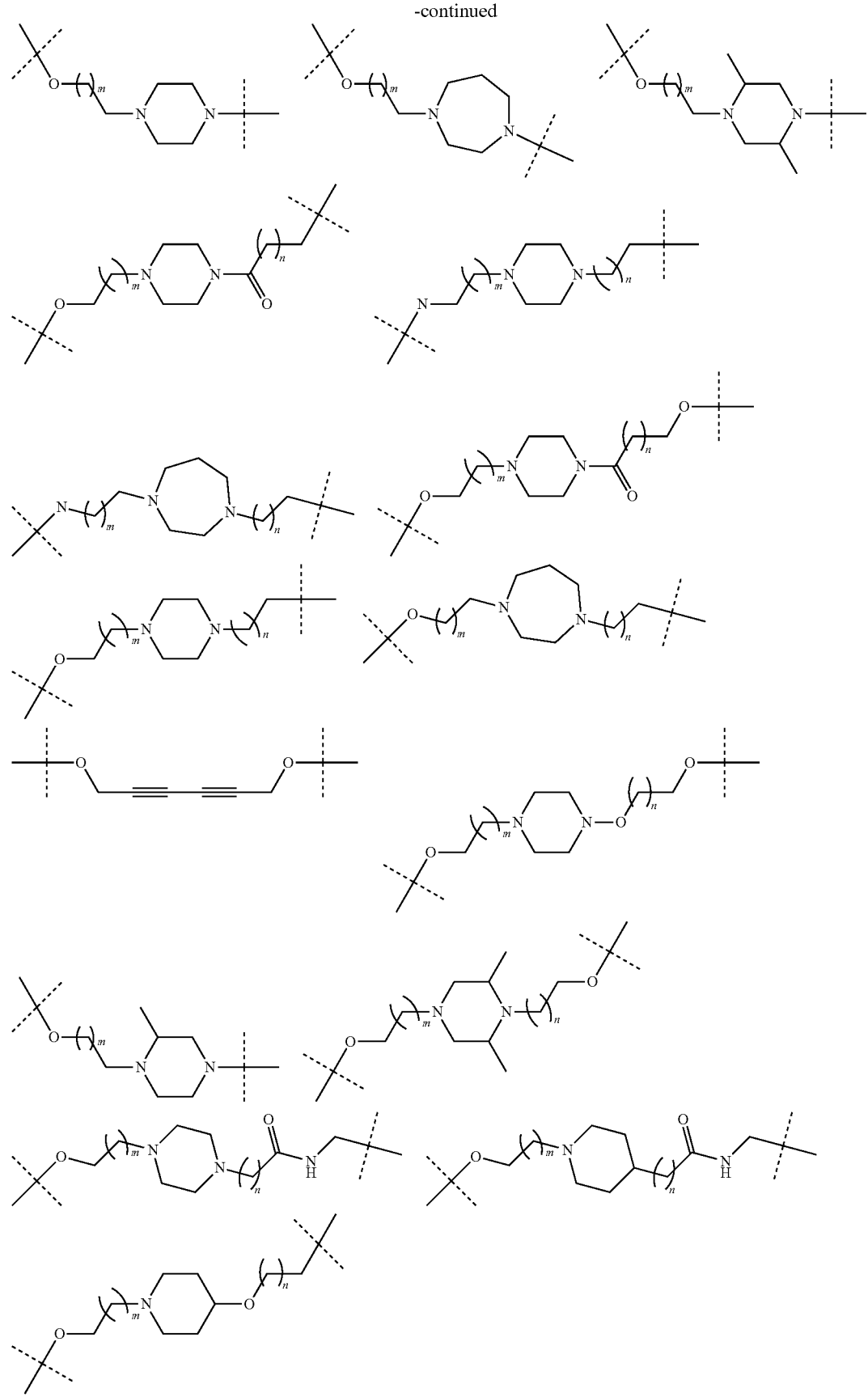

1363 1364
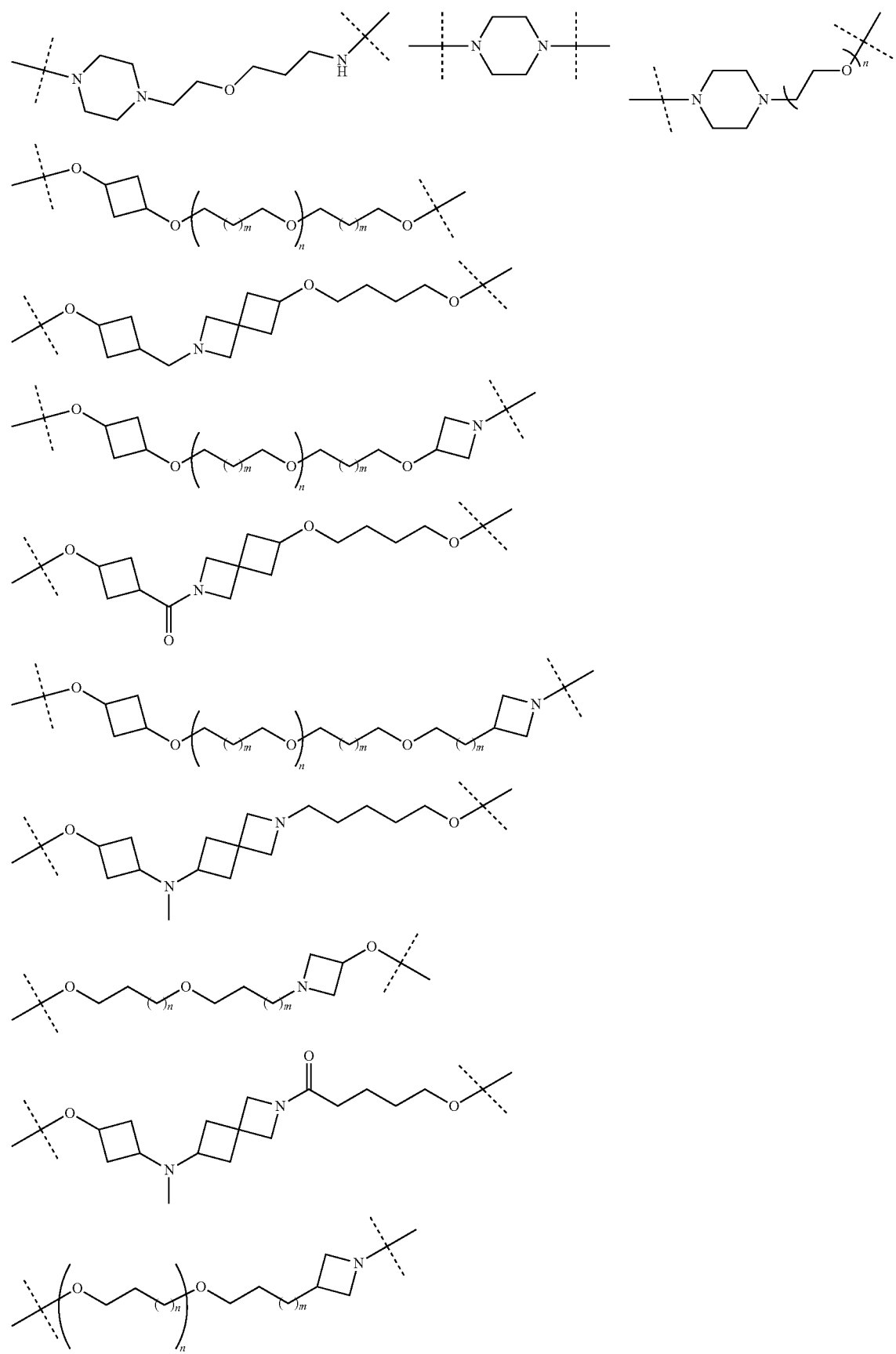

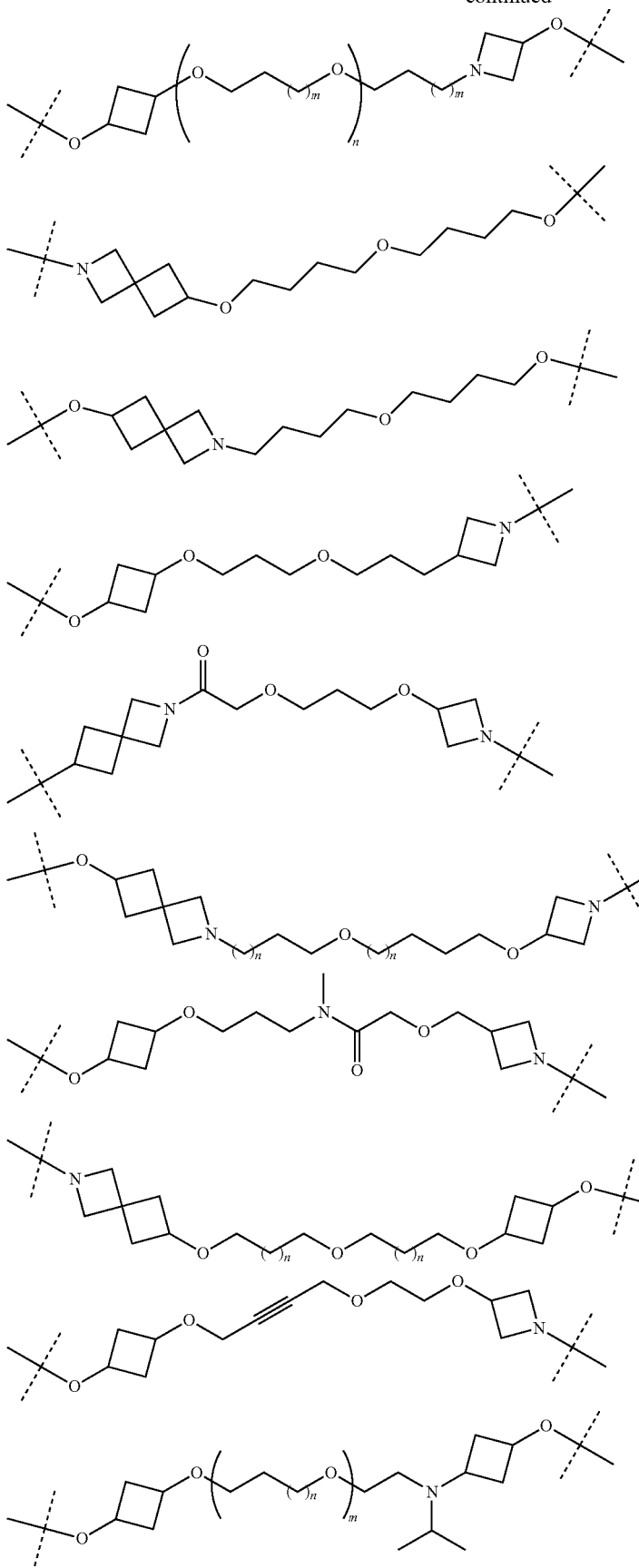
-continued

-continued
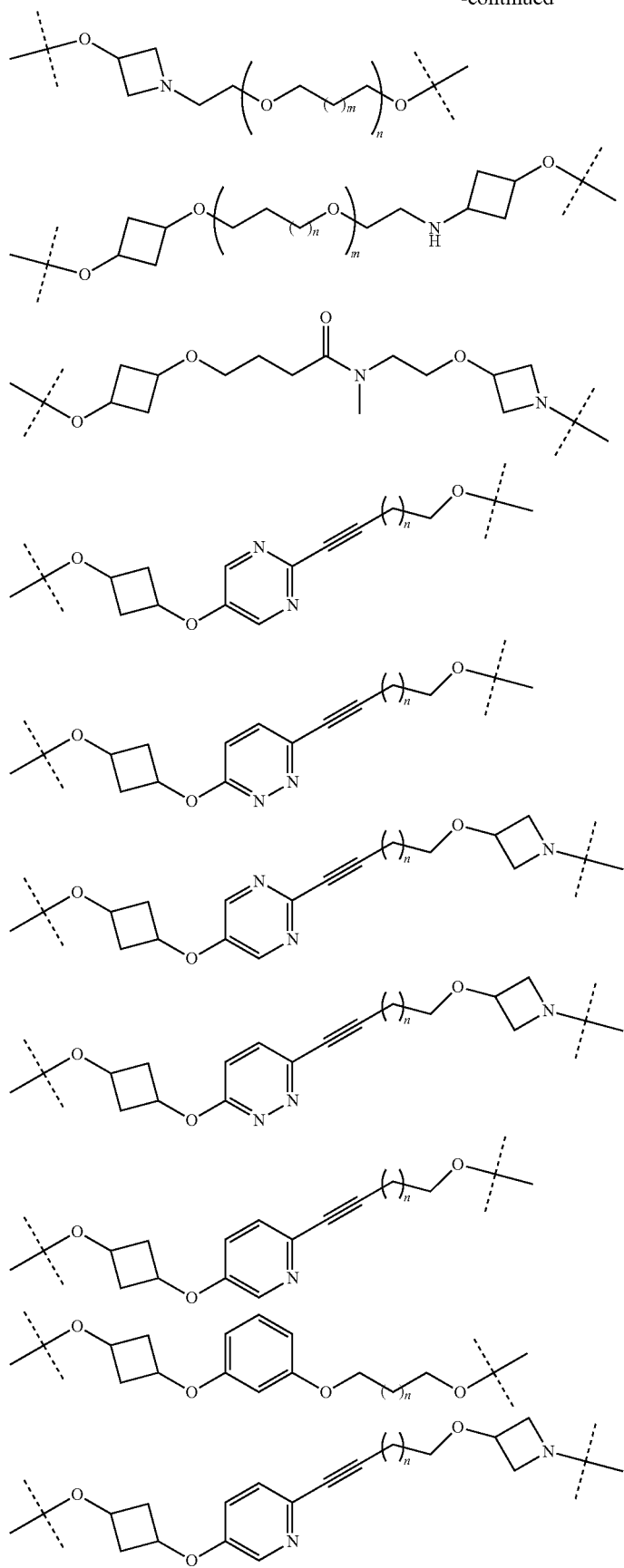

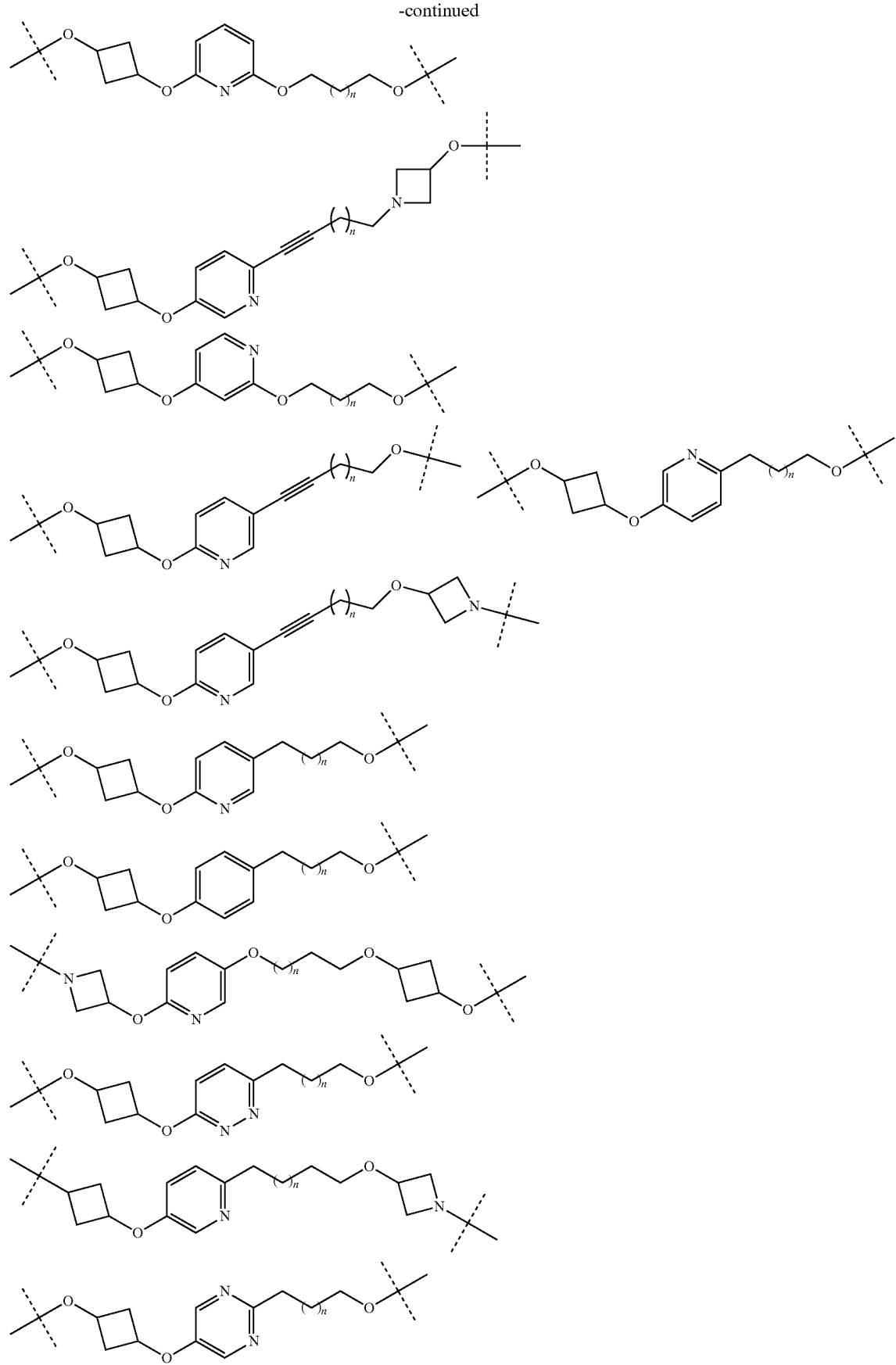

-continued
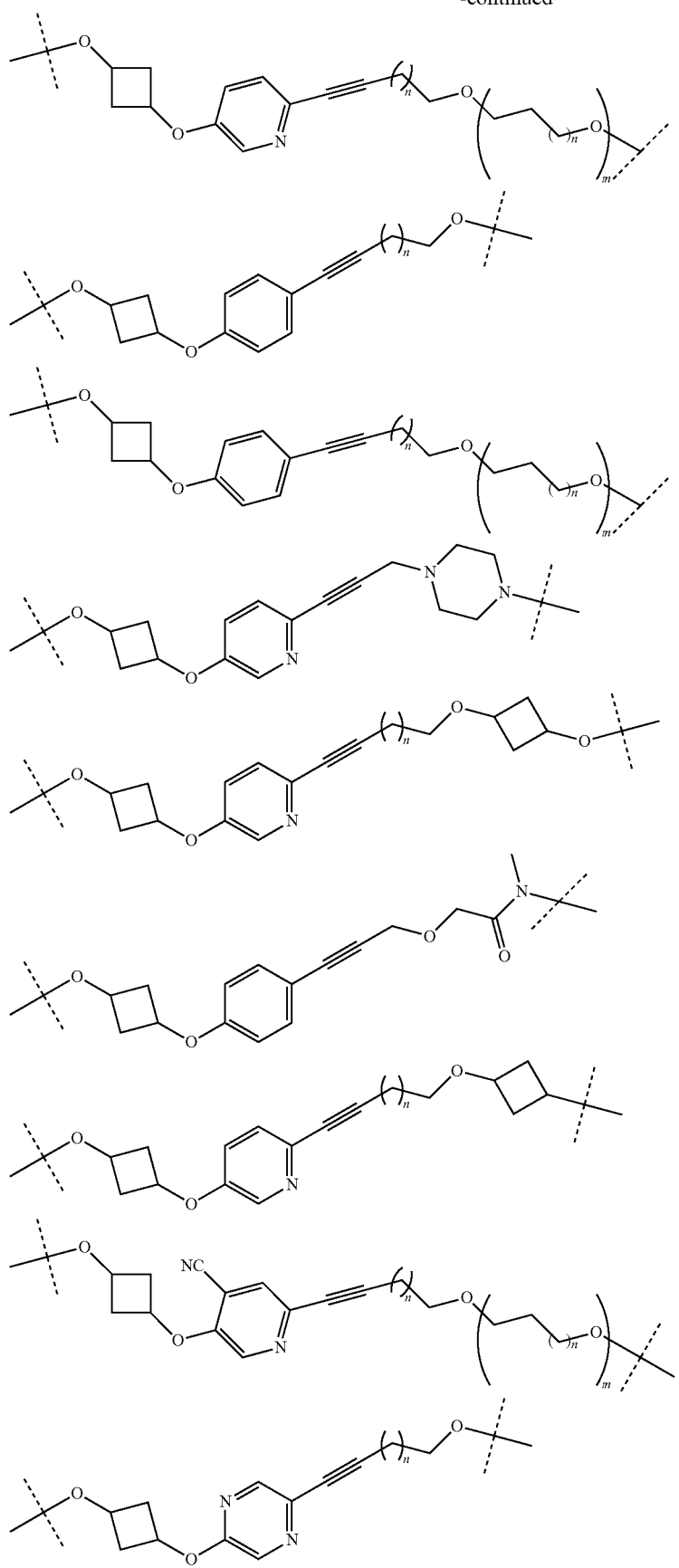

-continued
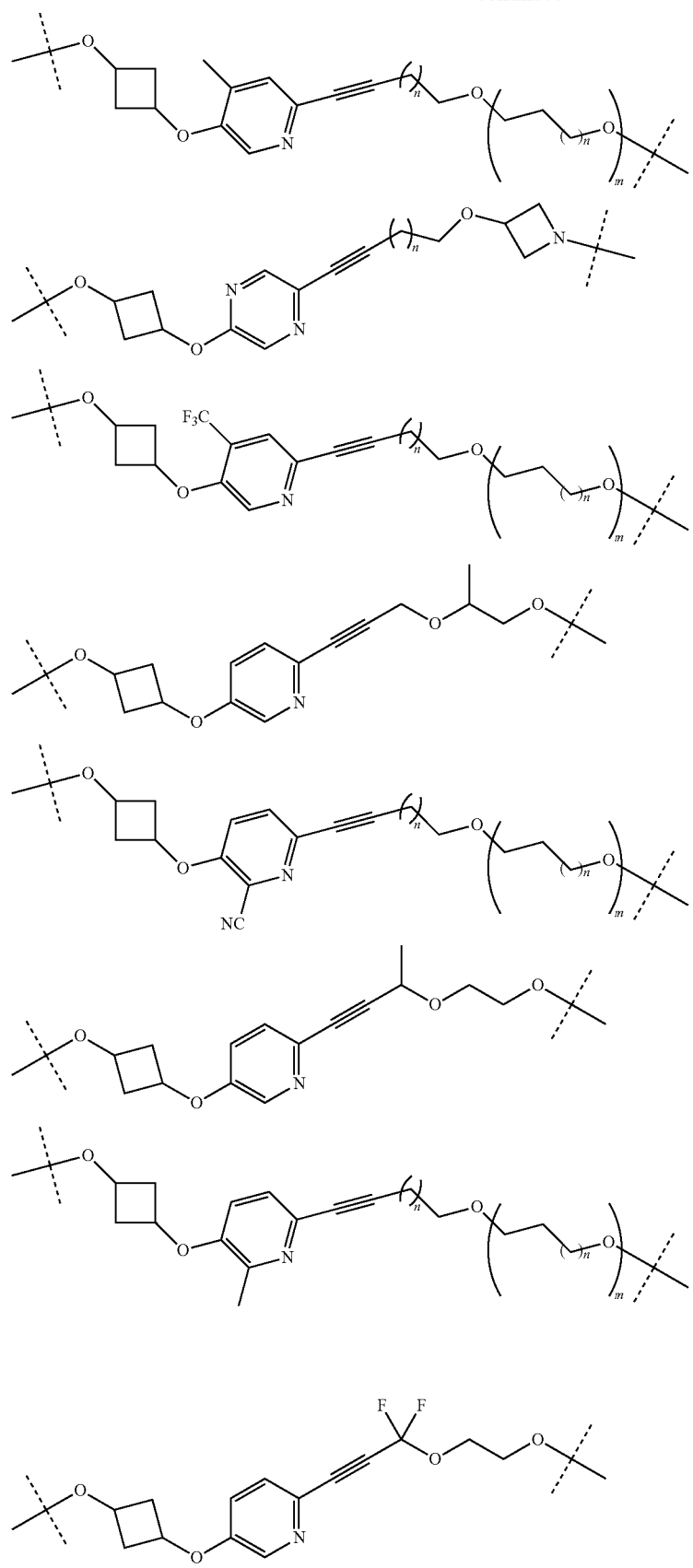

-continued
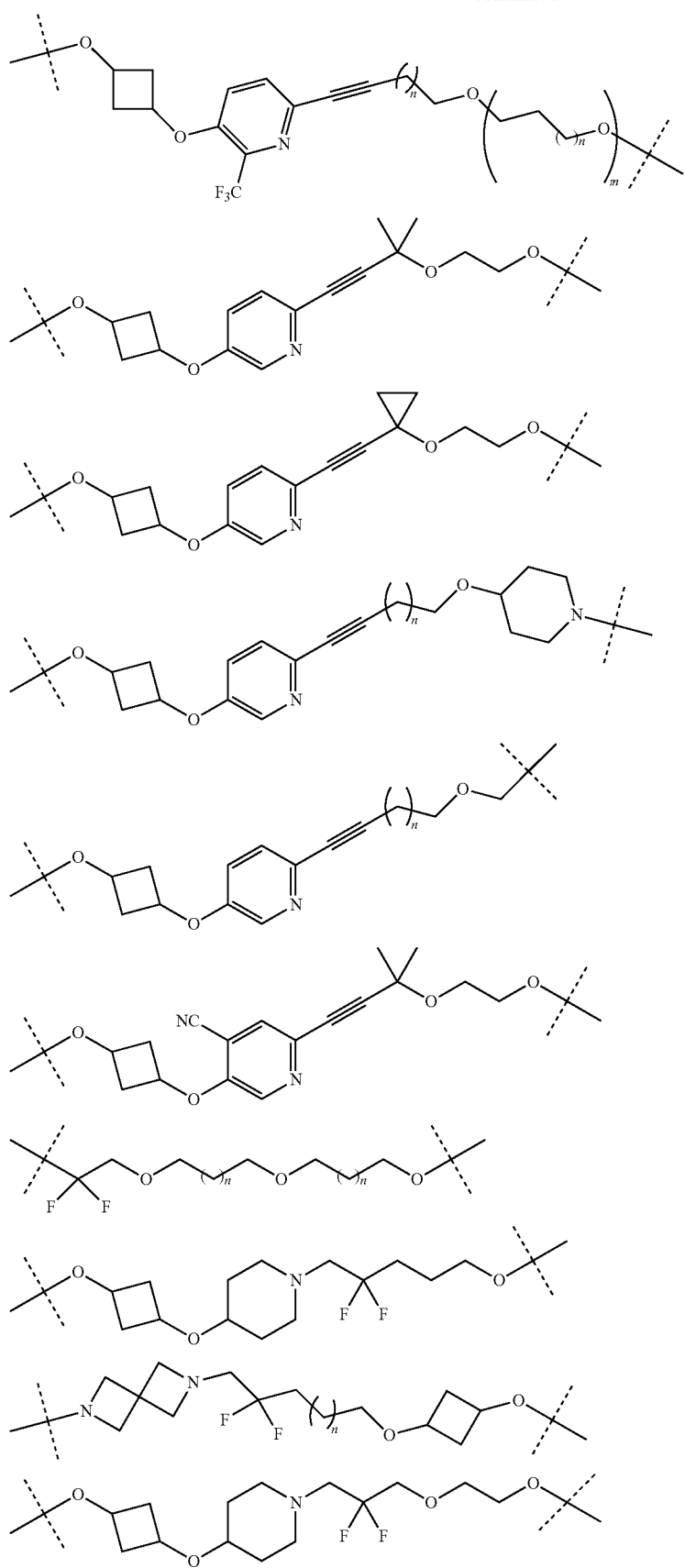

-continued
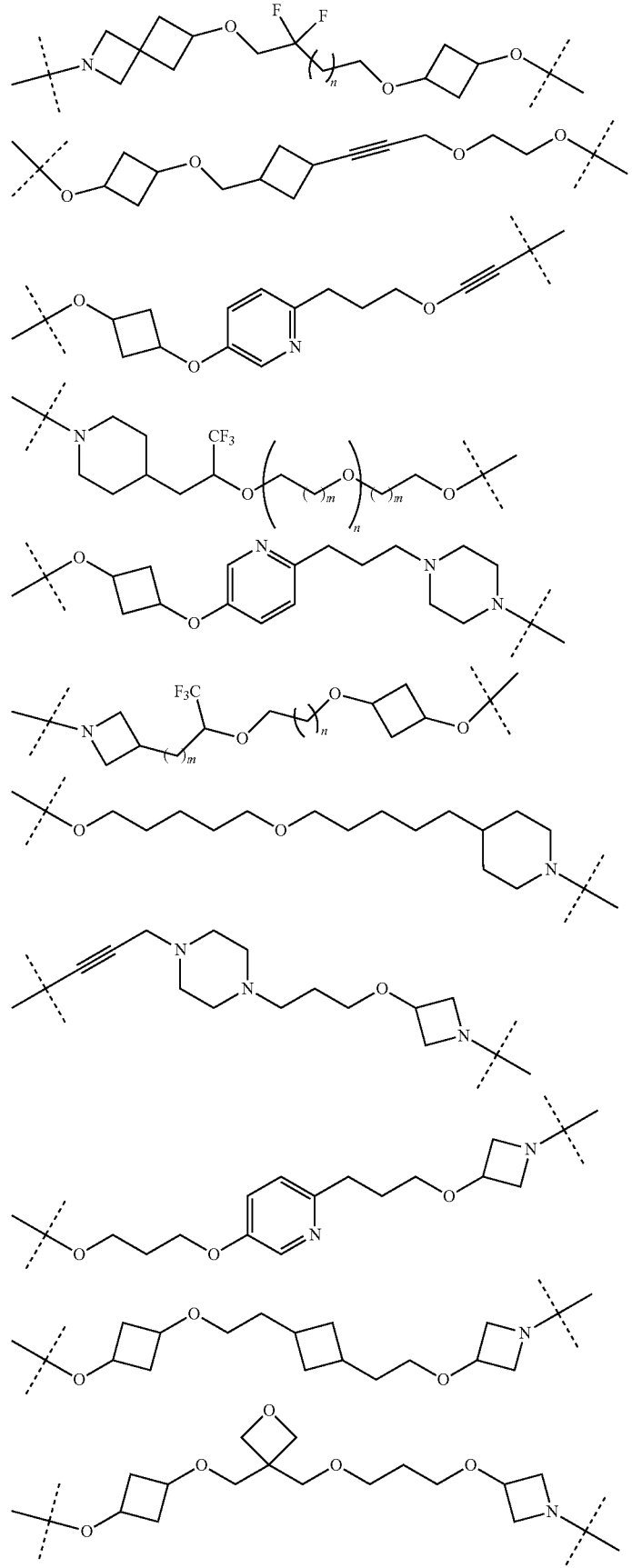

-continued
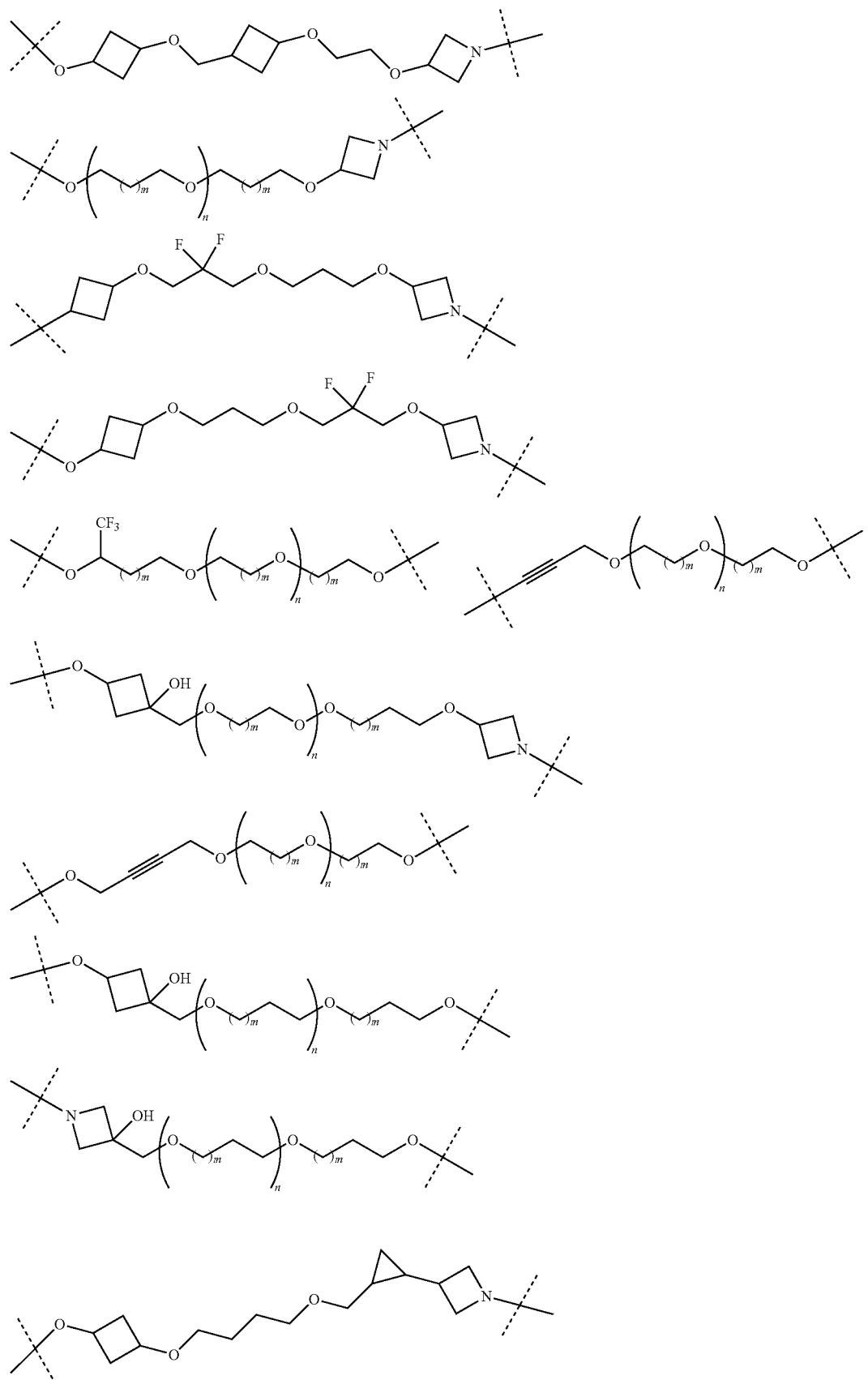

1381    -continued    1382
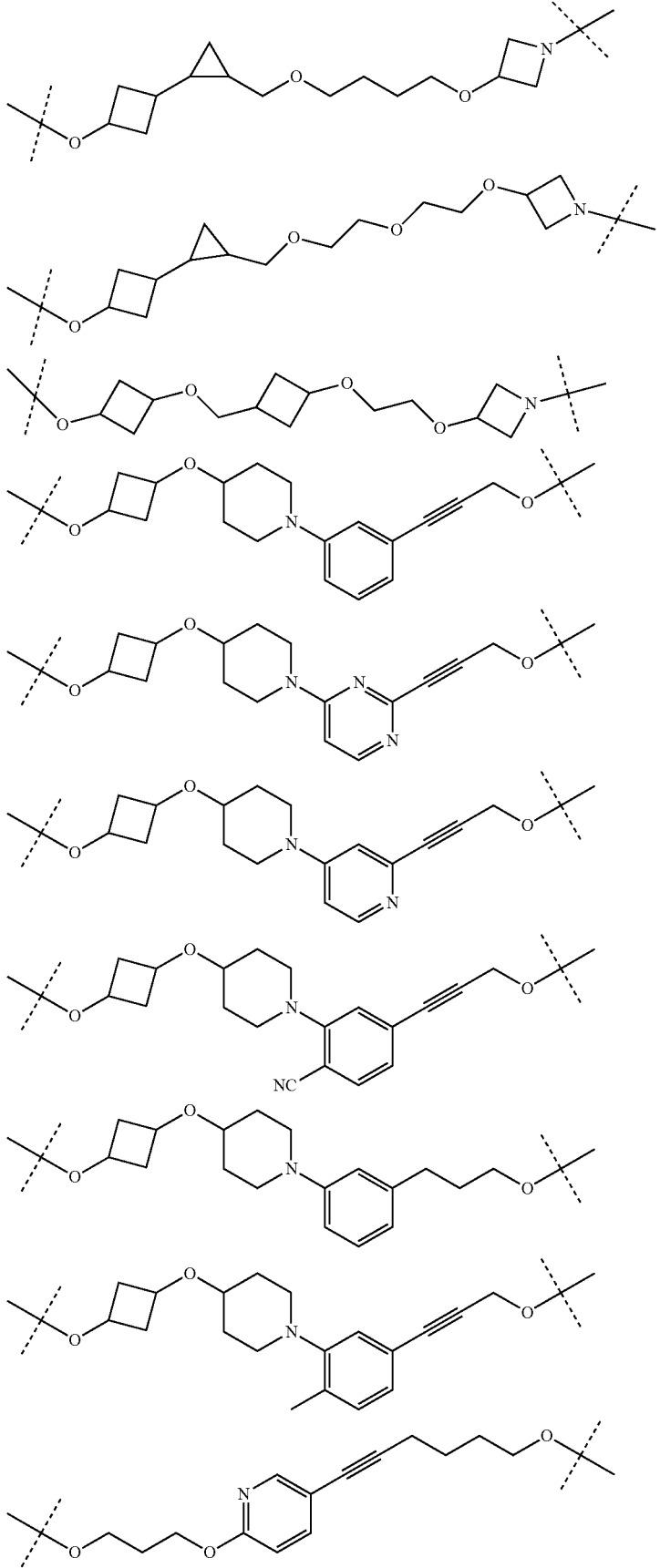

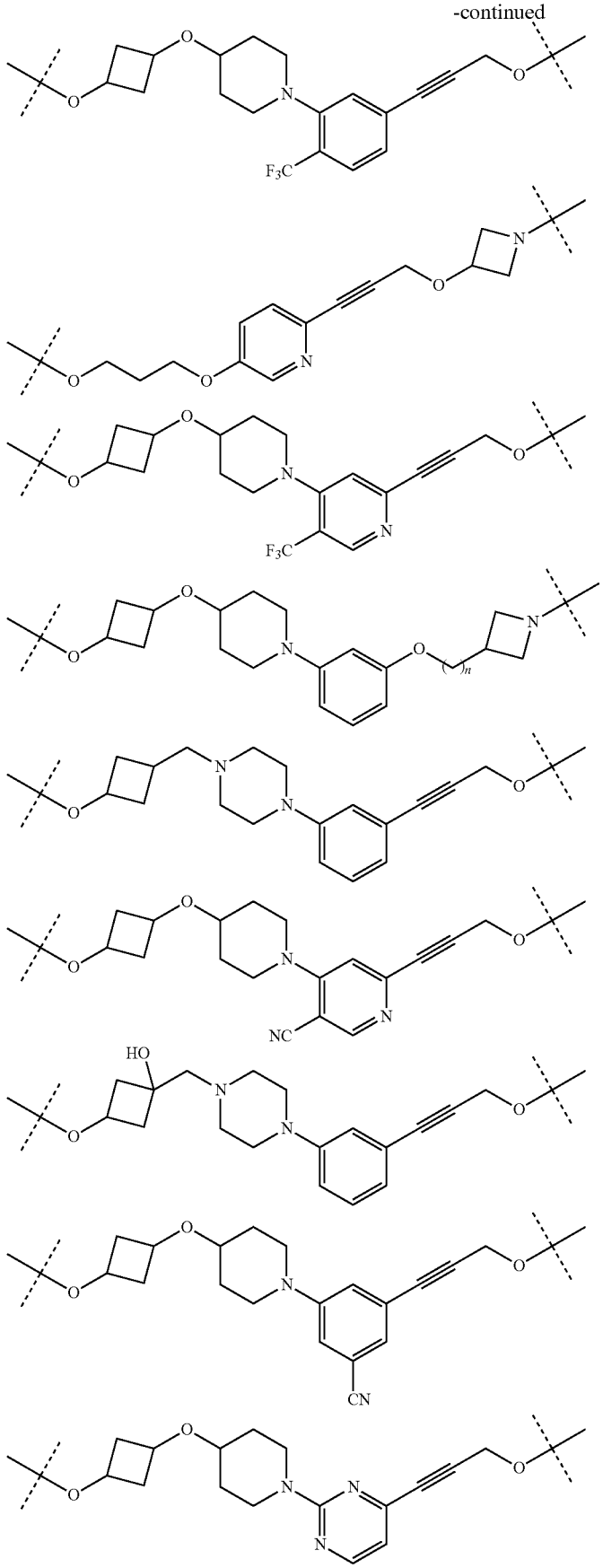

1385
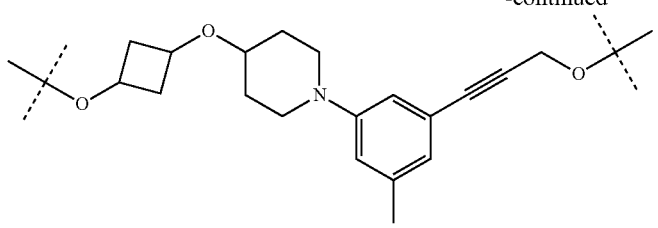
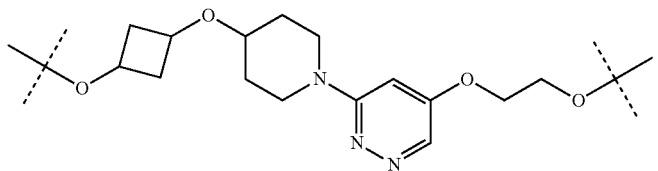
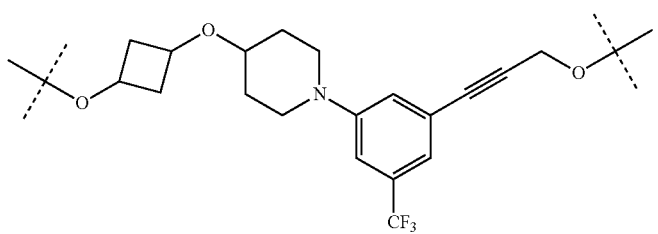
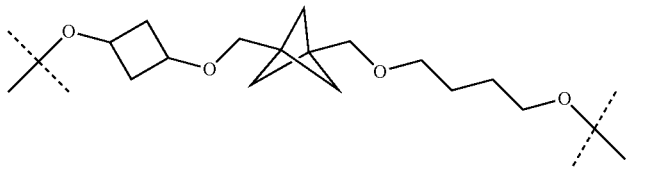
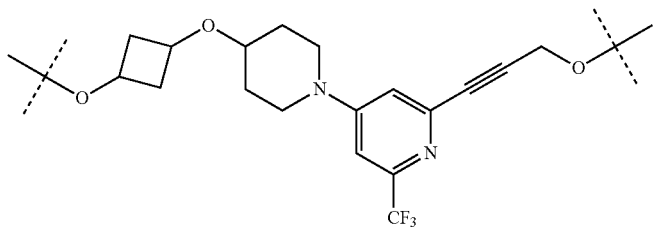
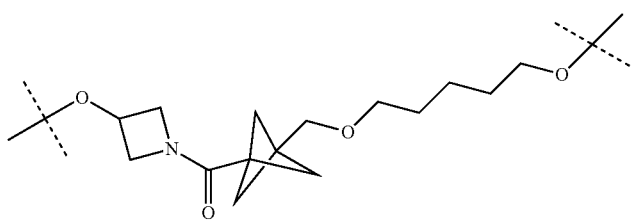
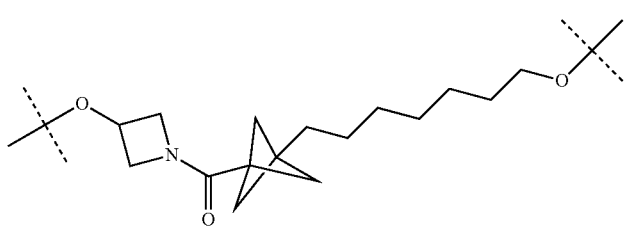
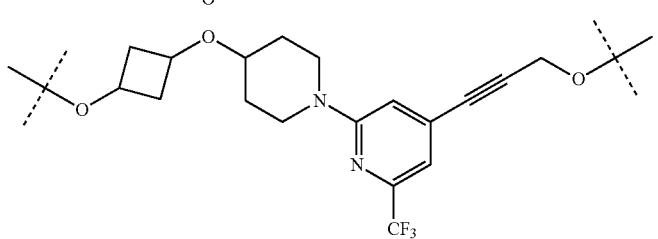
1386

1387
-continued
1388
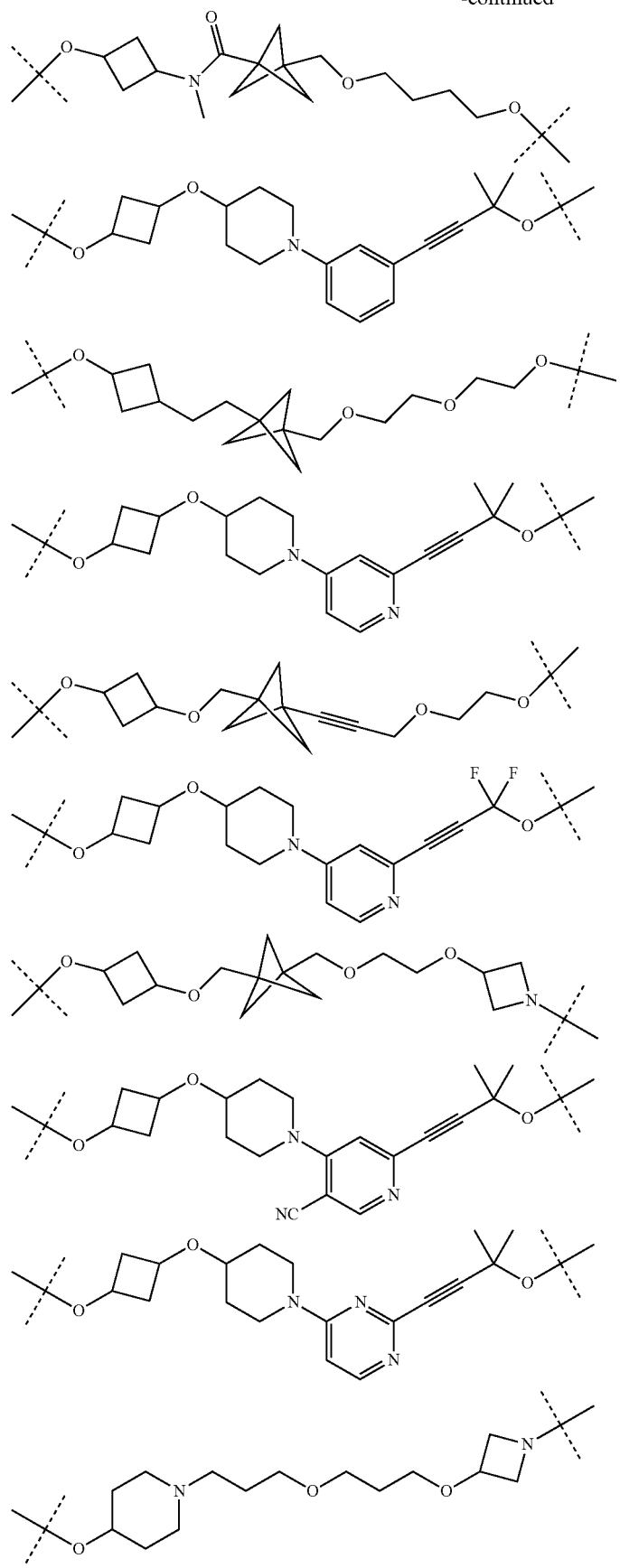

-continued
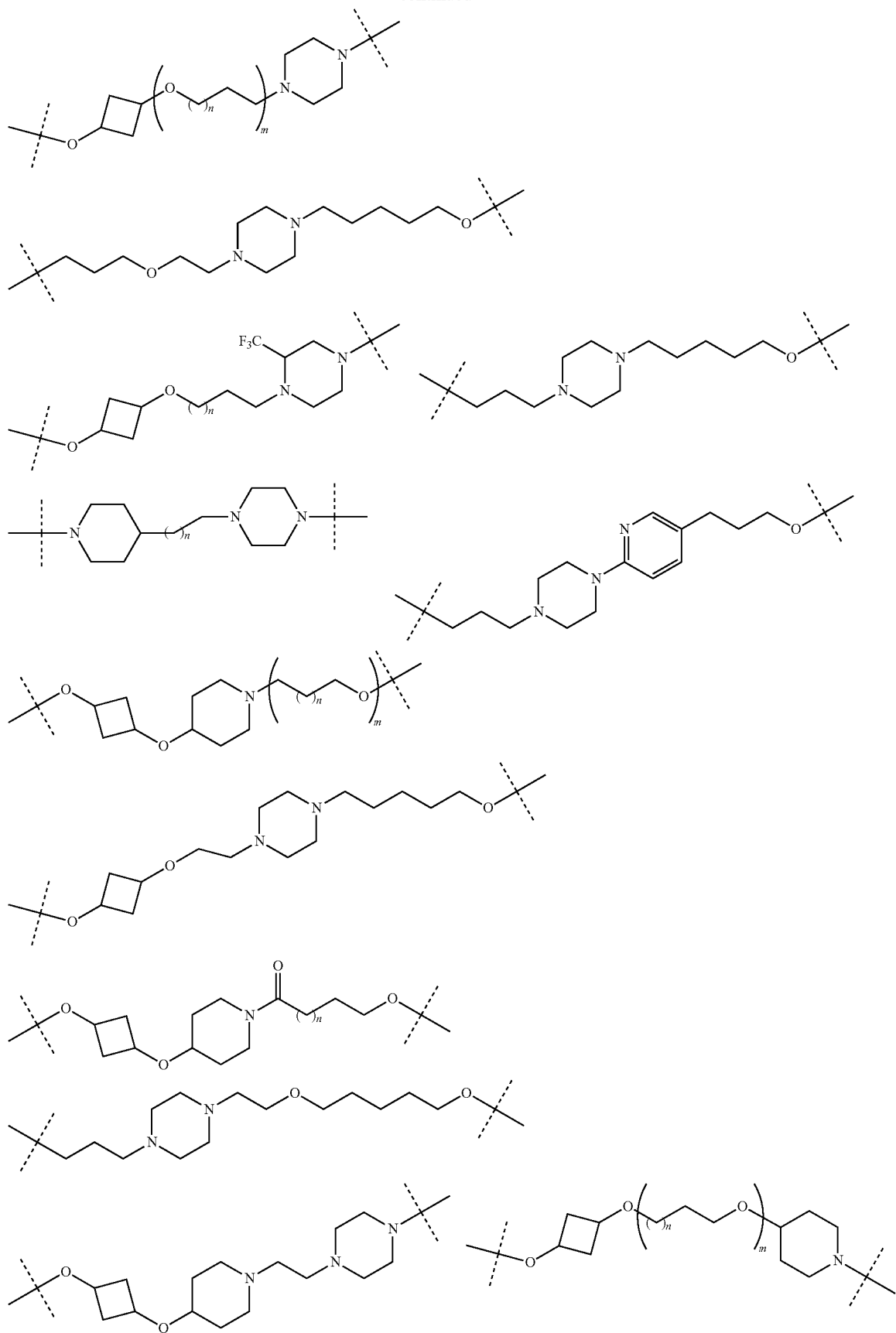

-continued
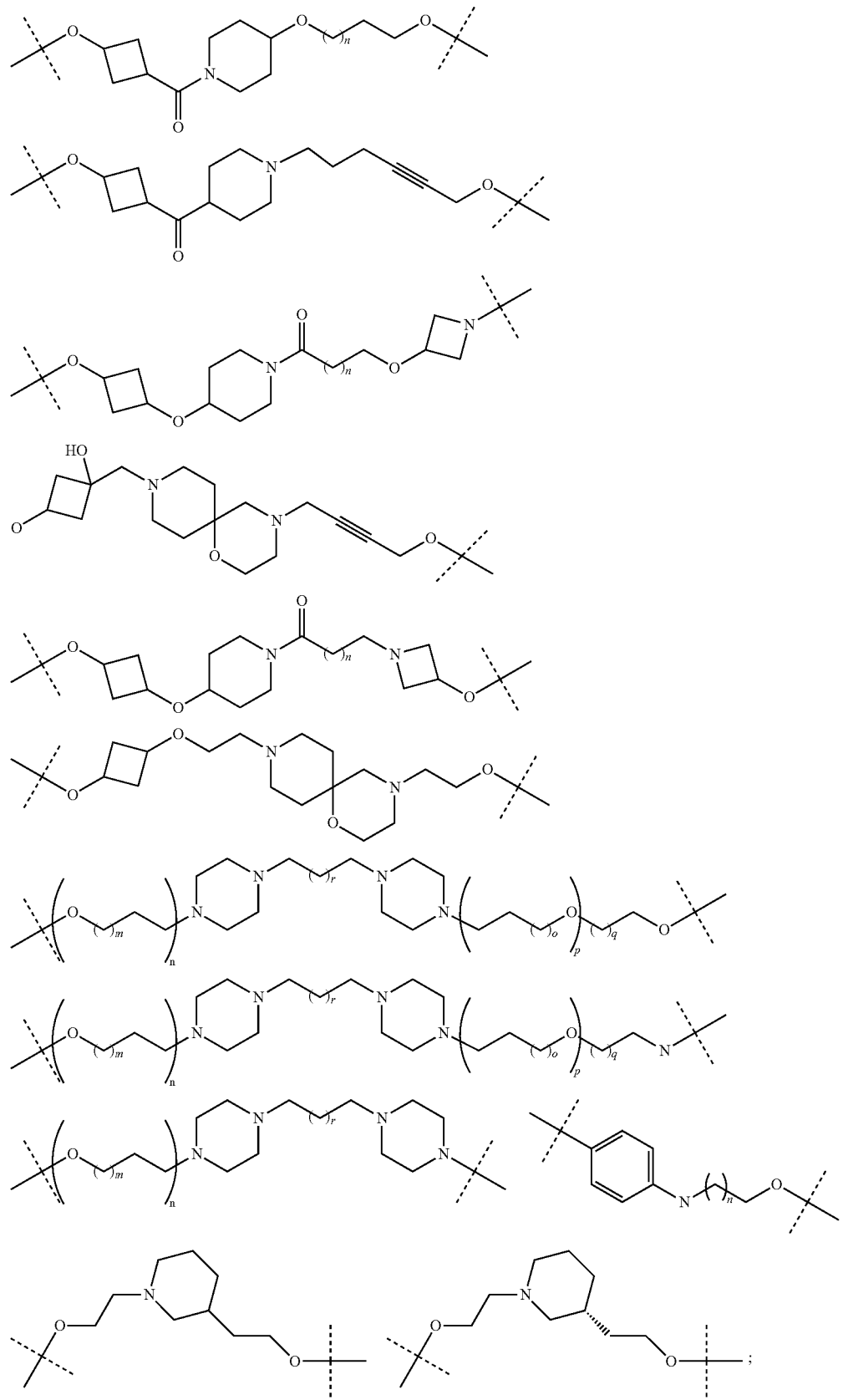

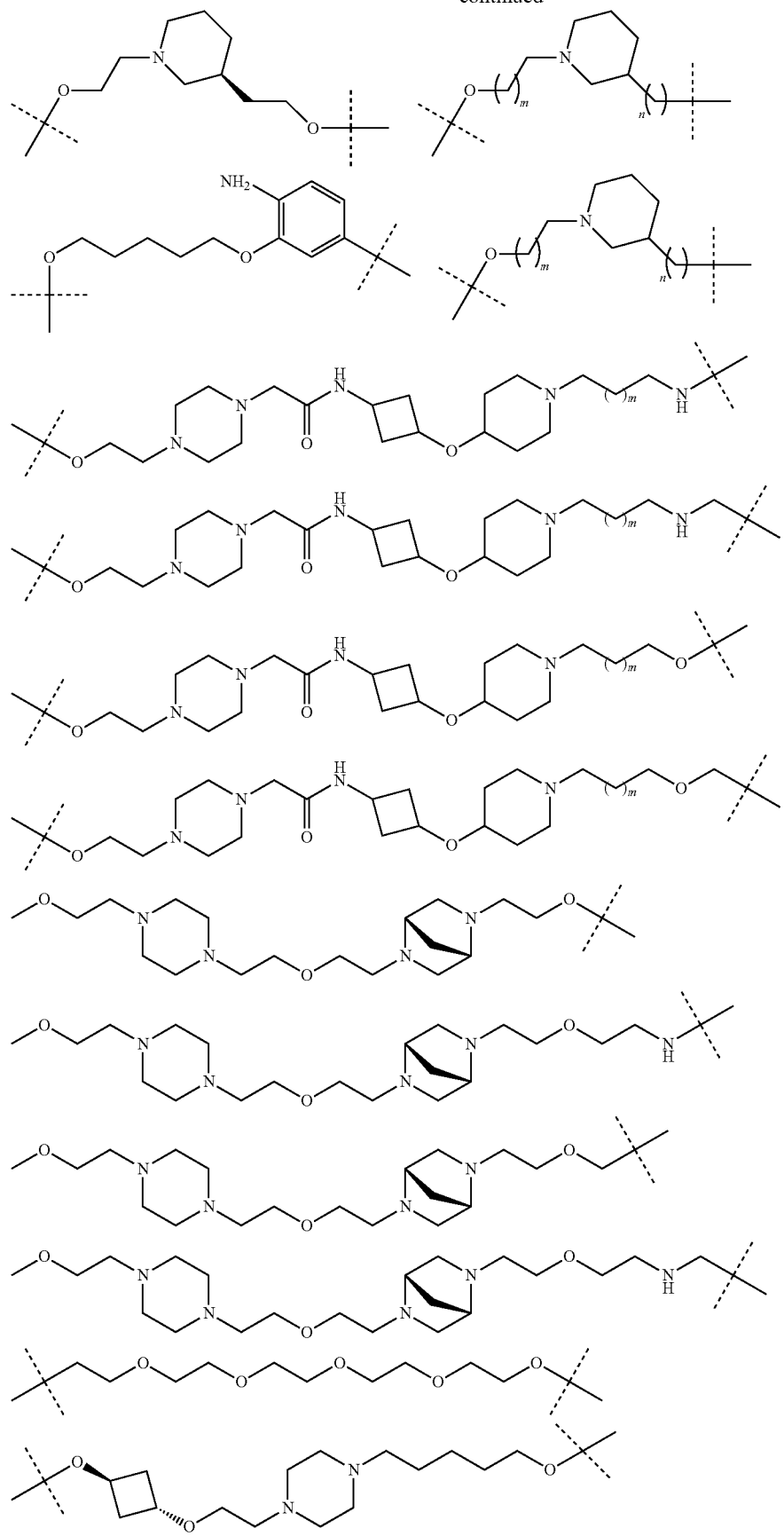

-continued
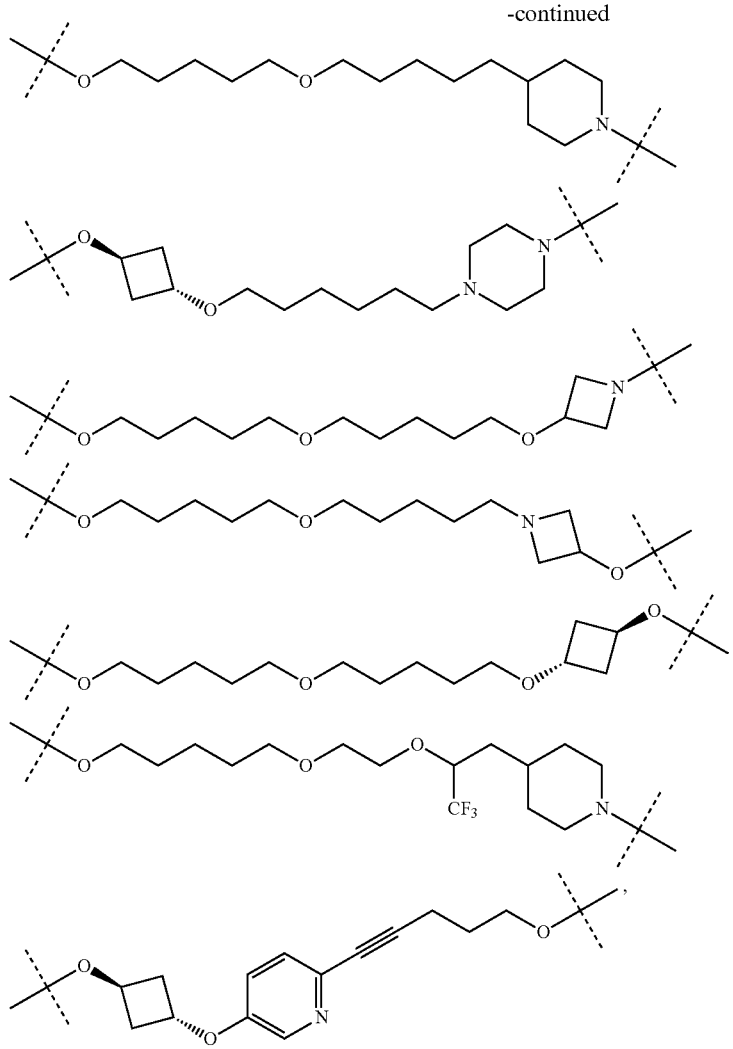
wherein m, n, o, and p are independently 0, 1, 2, 3, 4, 5, 6, or 7.
In any aspect or embodiment described herein, the linker (L) is selected from the group consisting of:
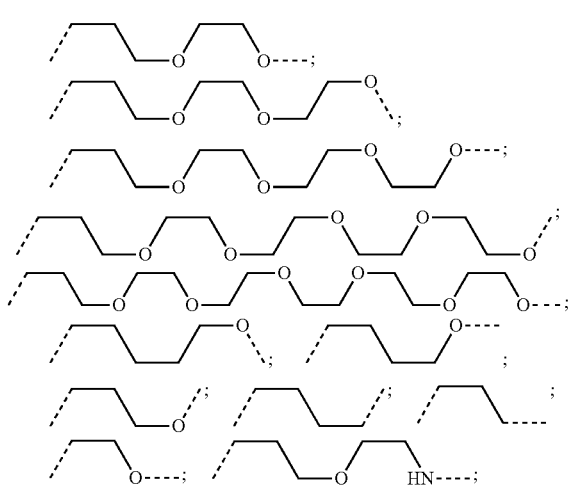
-continued
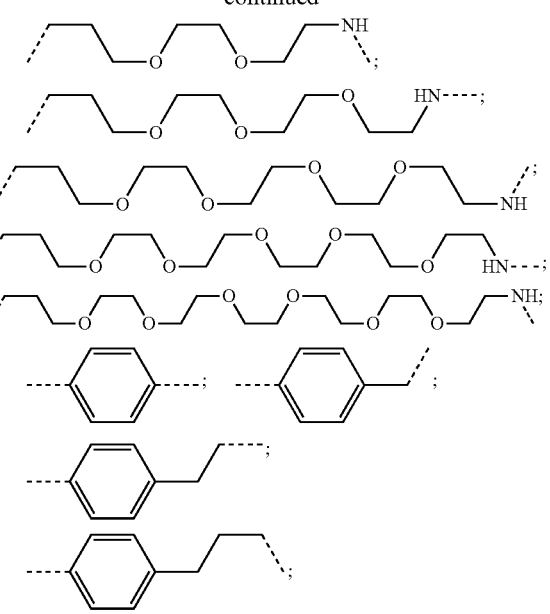

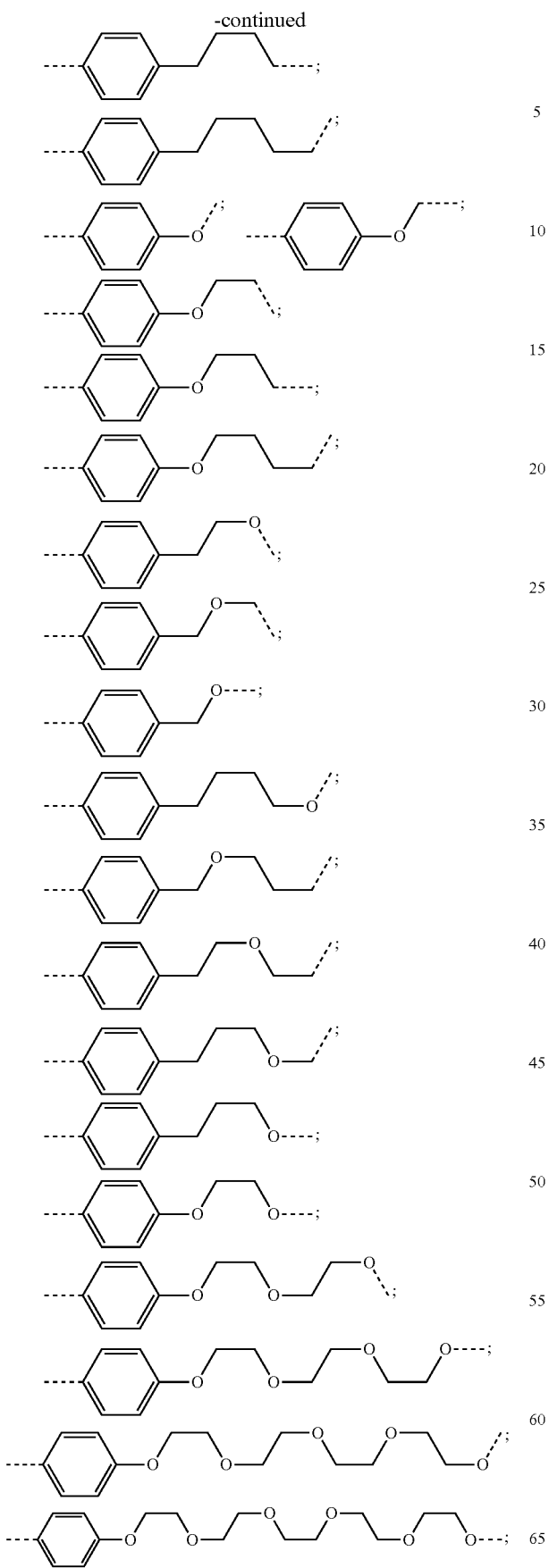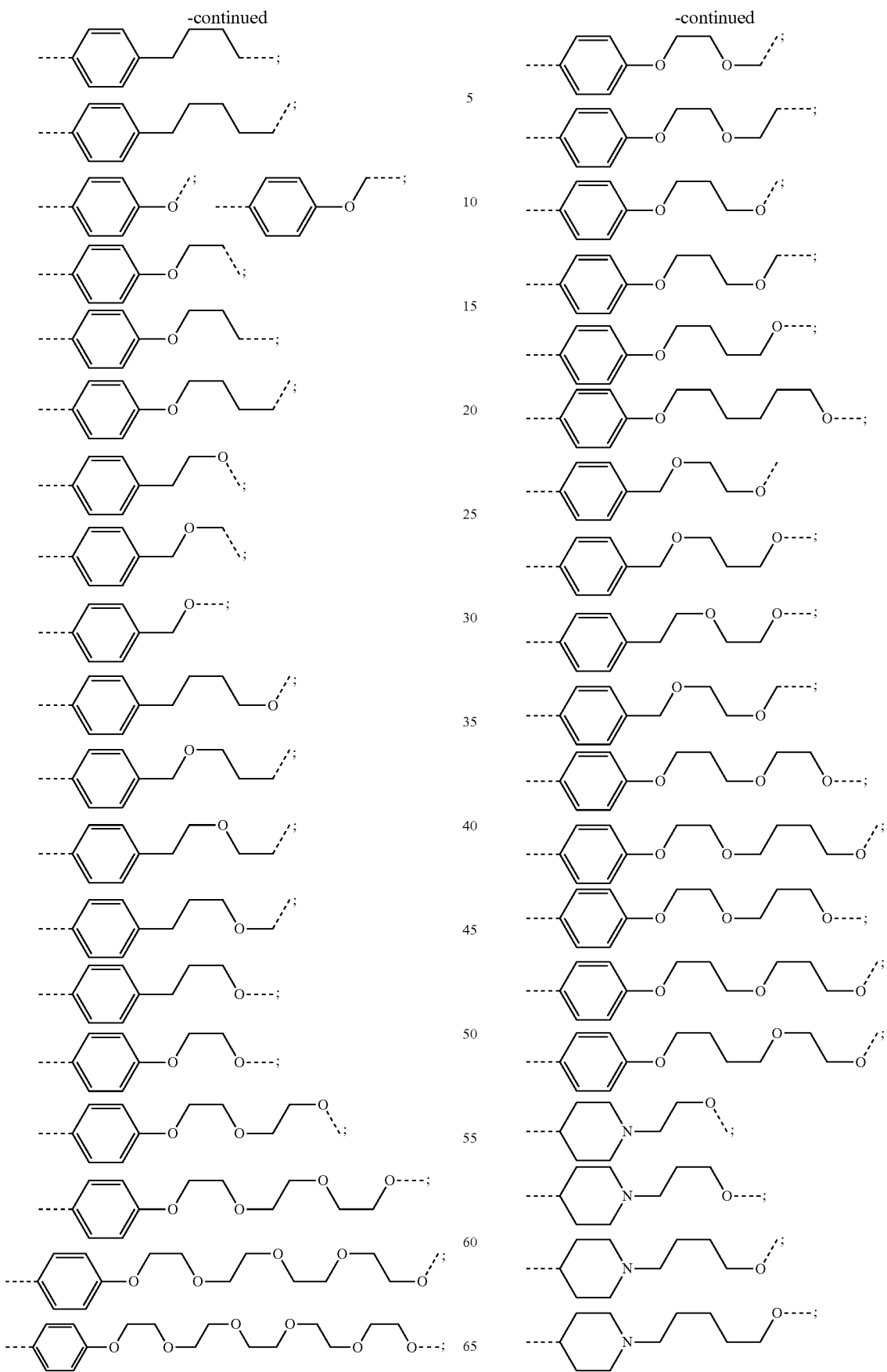

1399
-continued
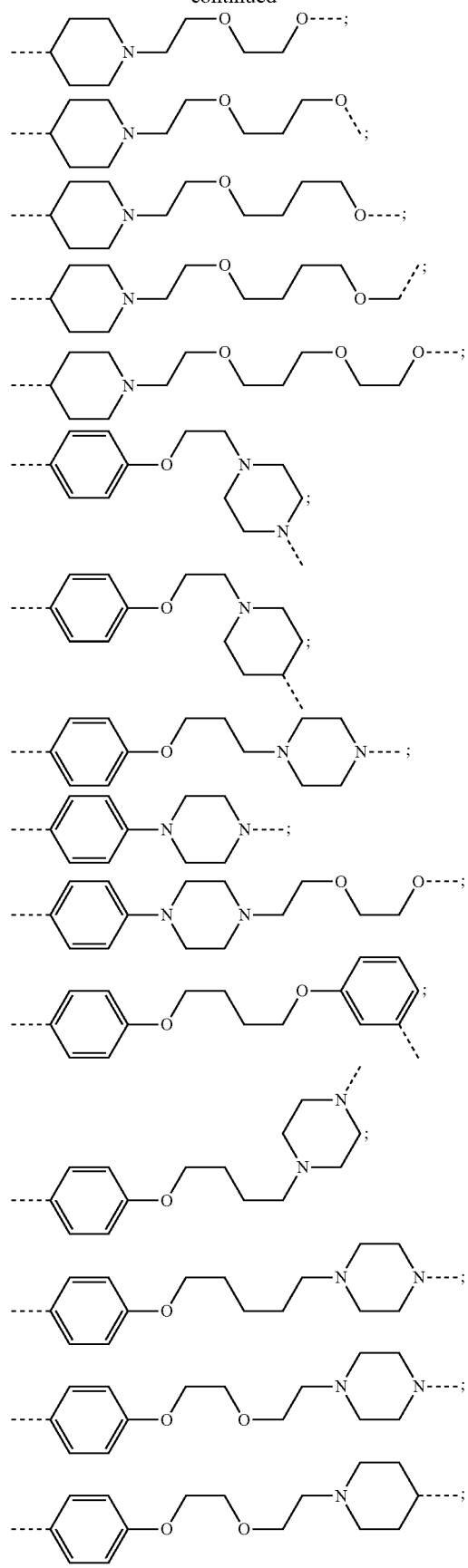
1400
-continued
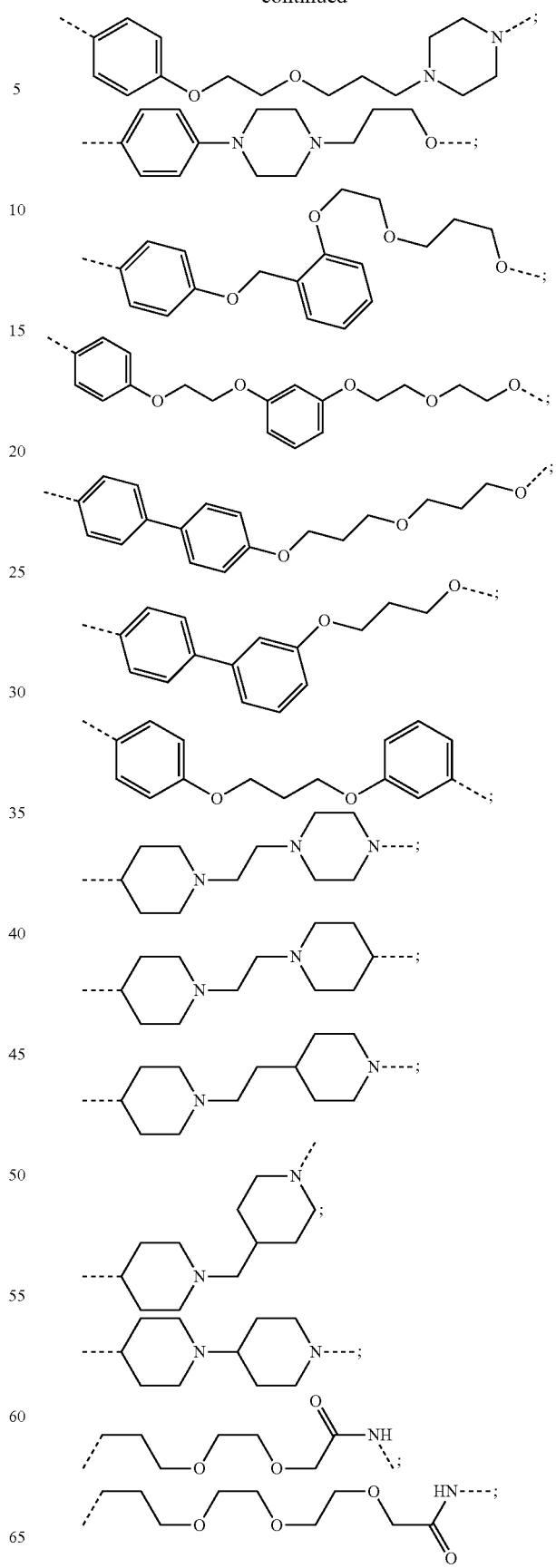

1401
-continued
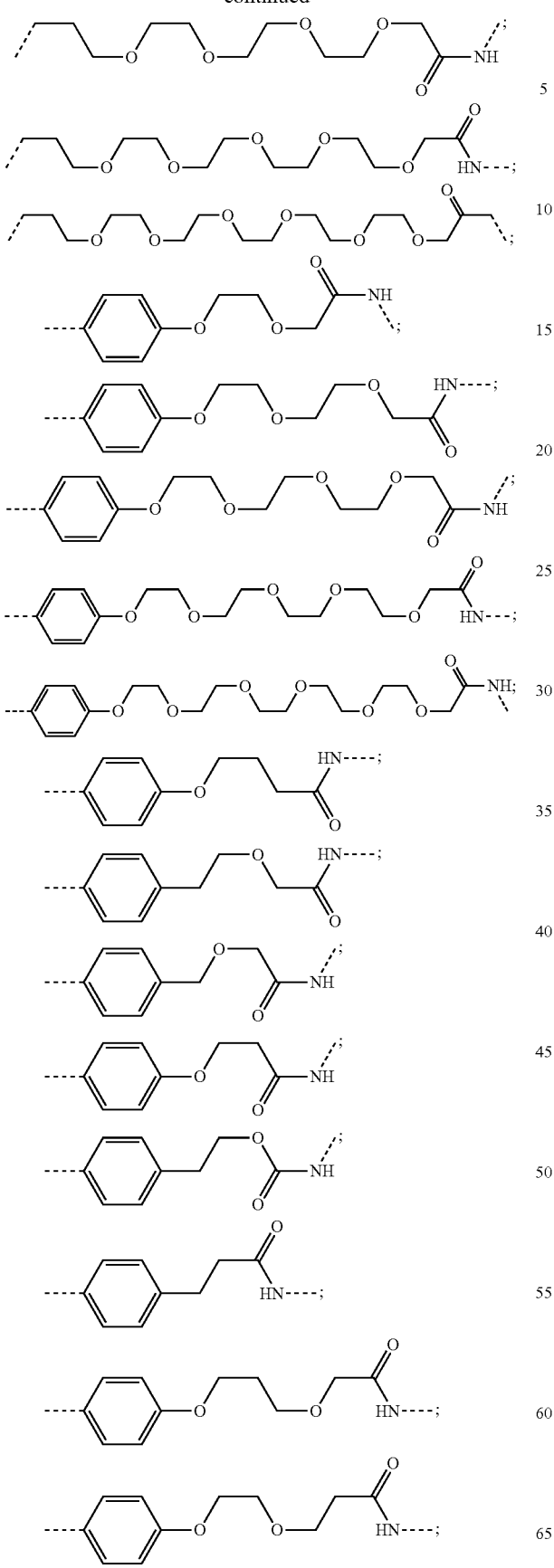
1402
-continued
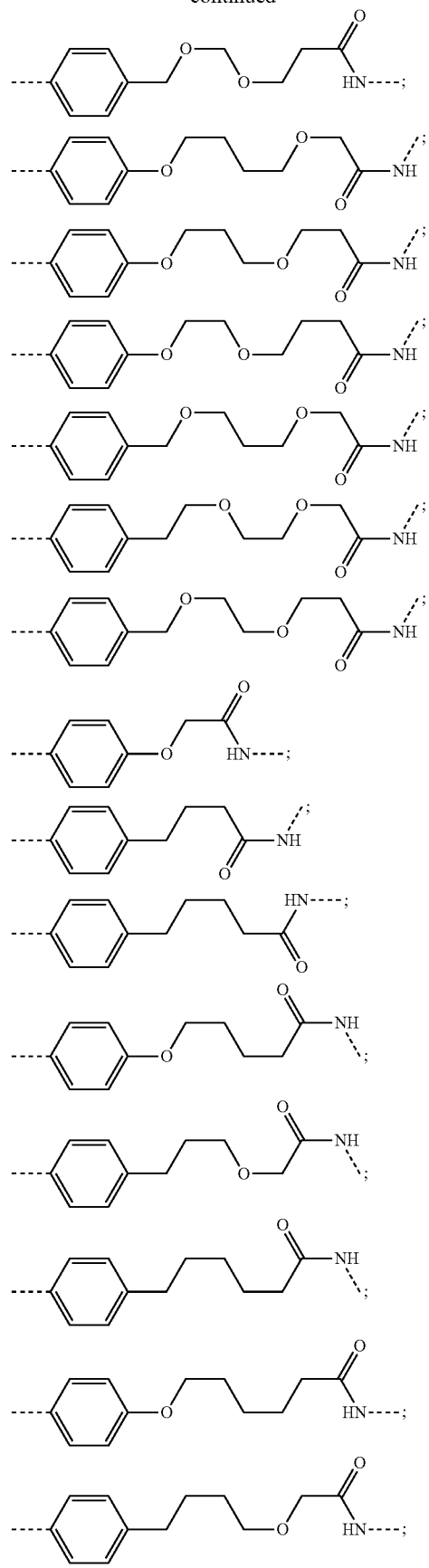

1403
-continued
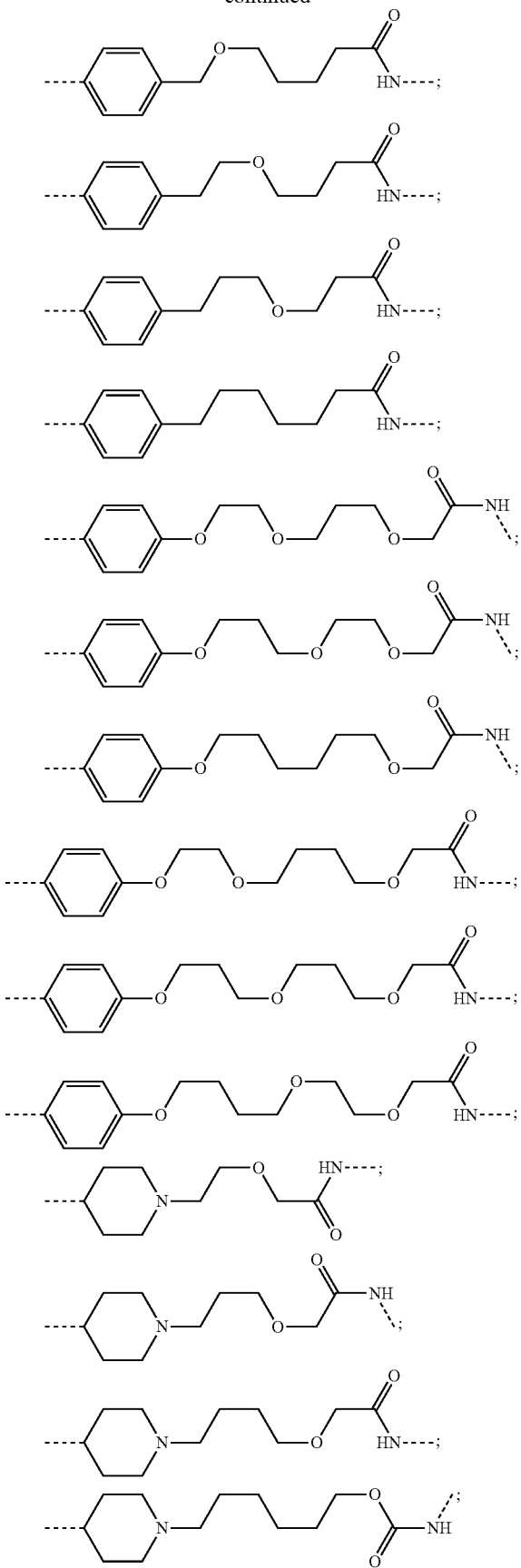
1404
-continued
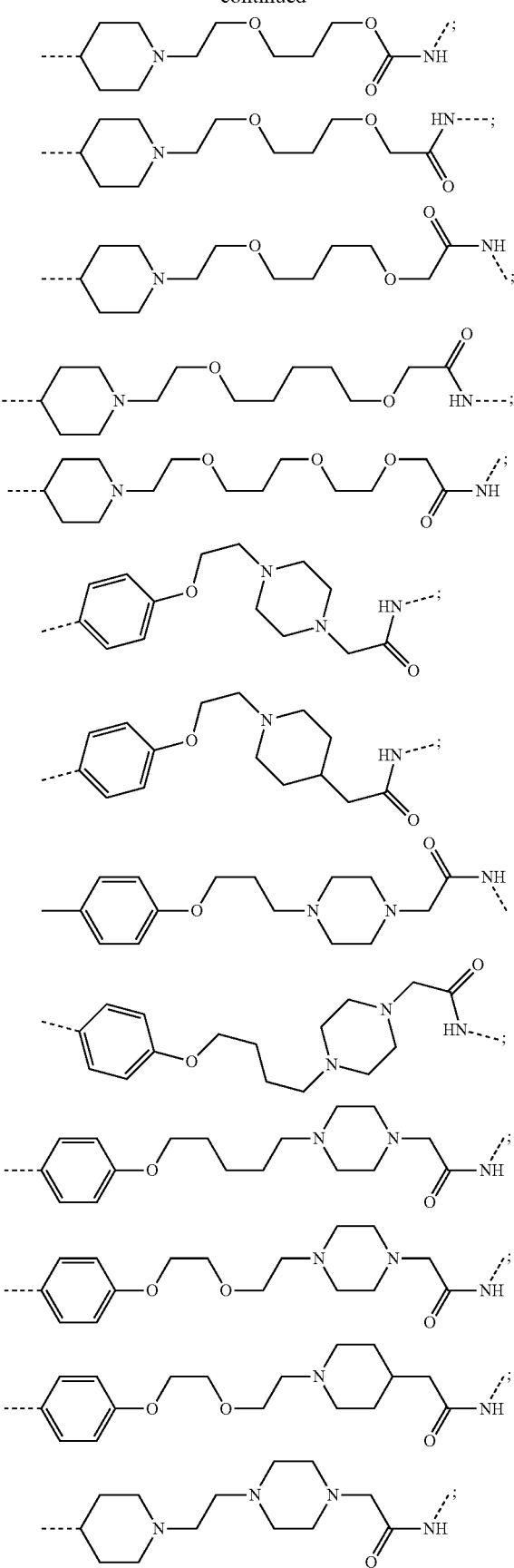

1405
-continued
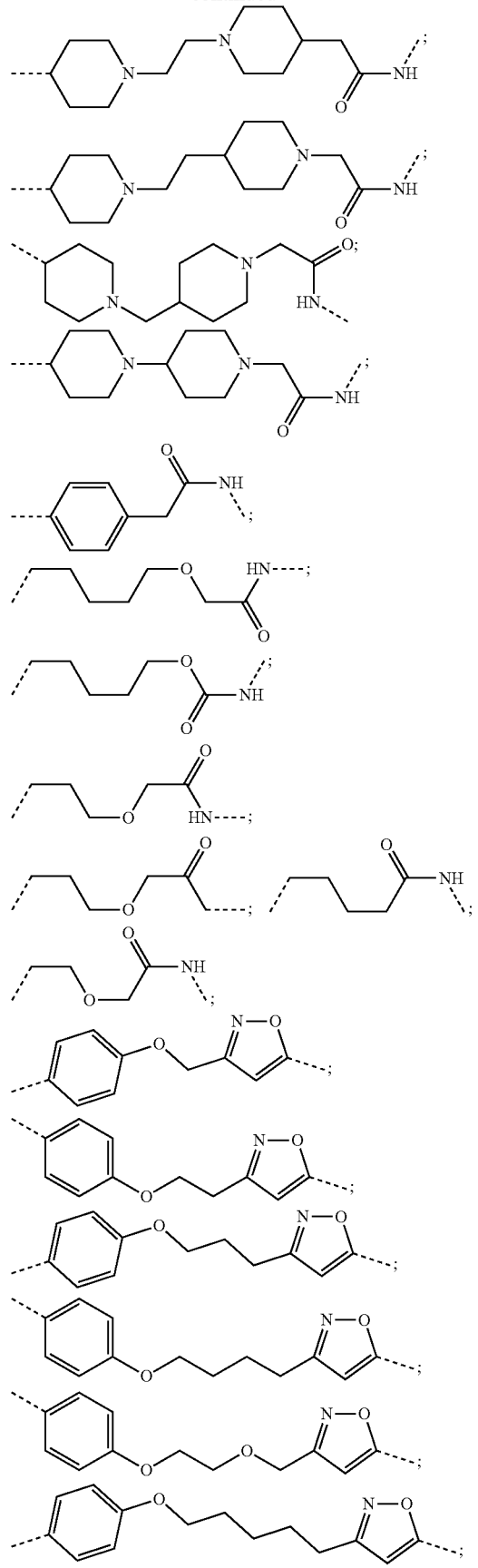
1406
-continued
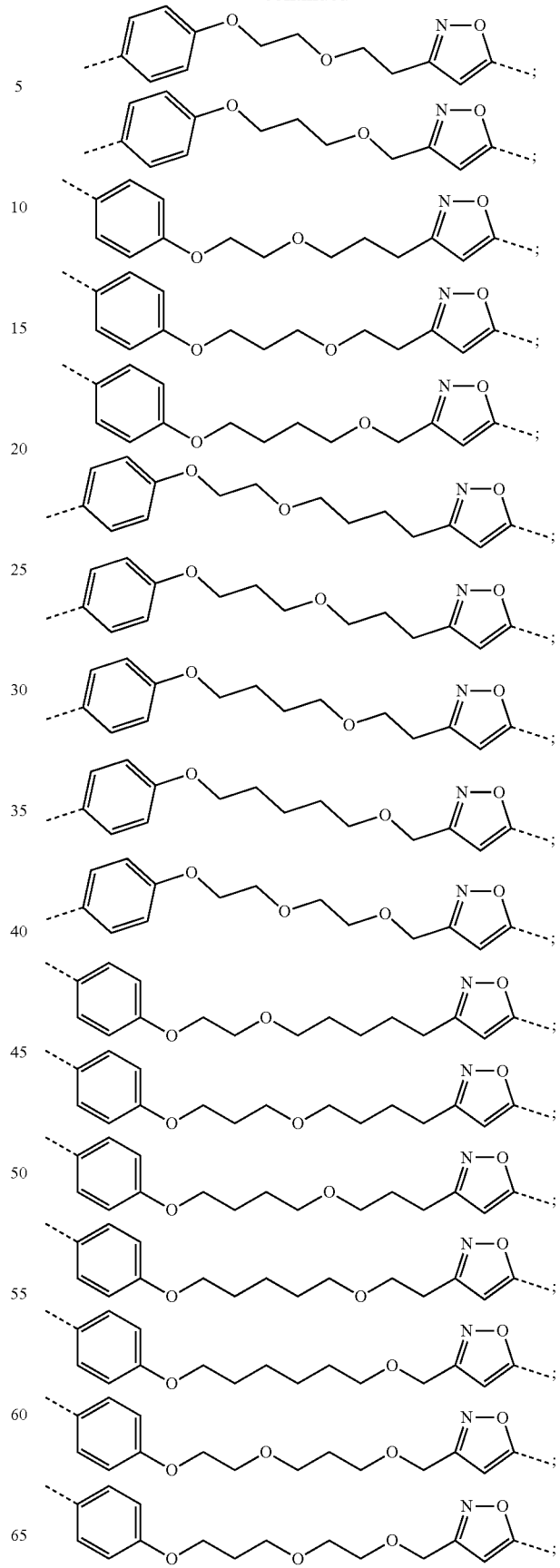

1407
-continued
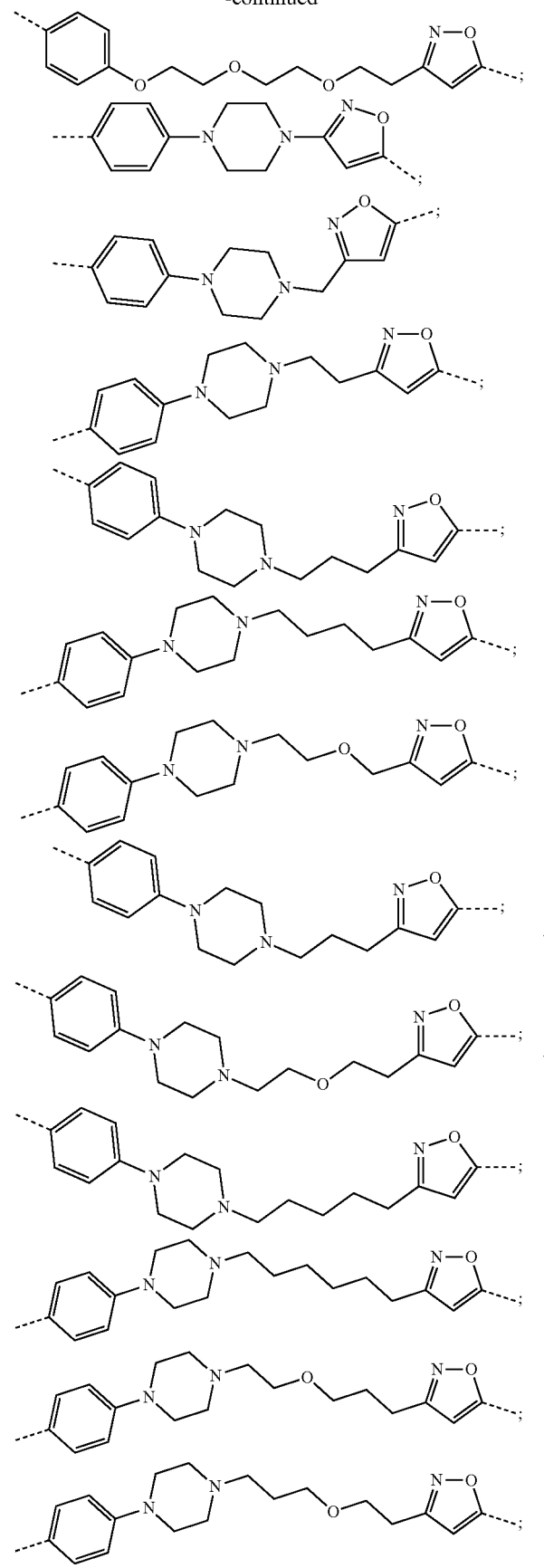
1408
-continued
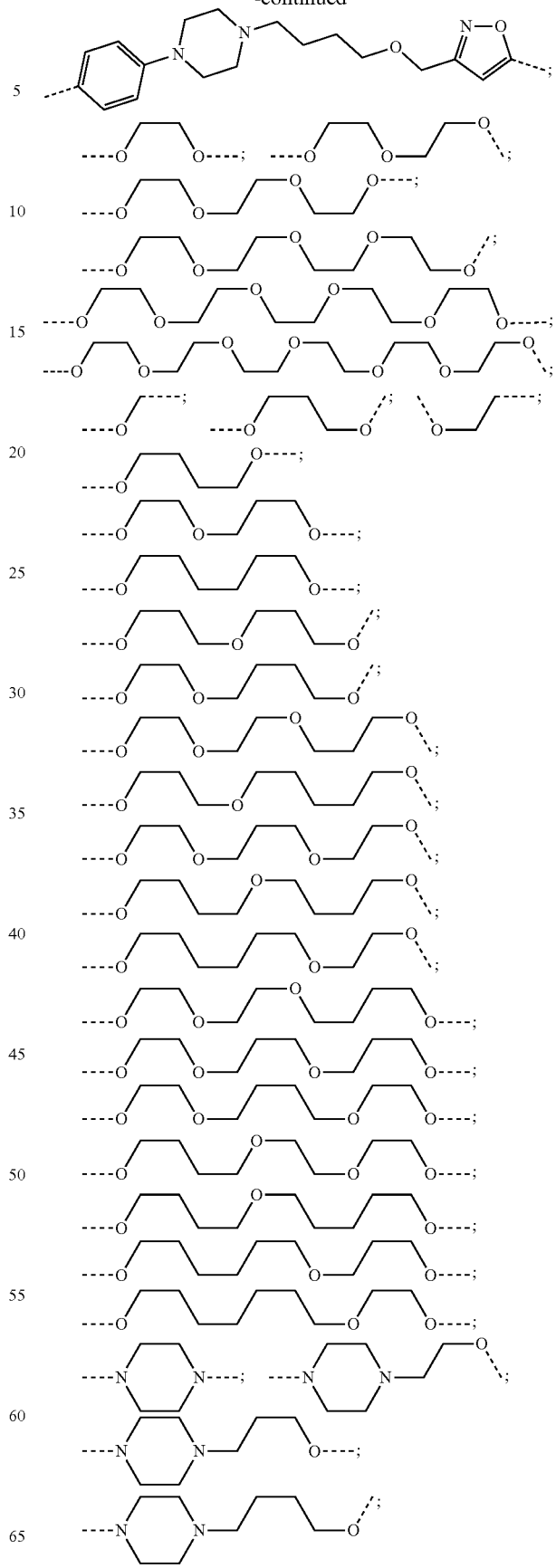

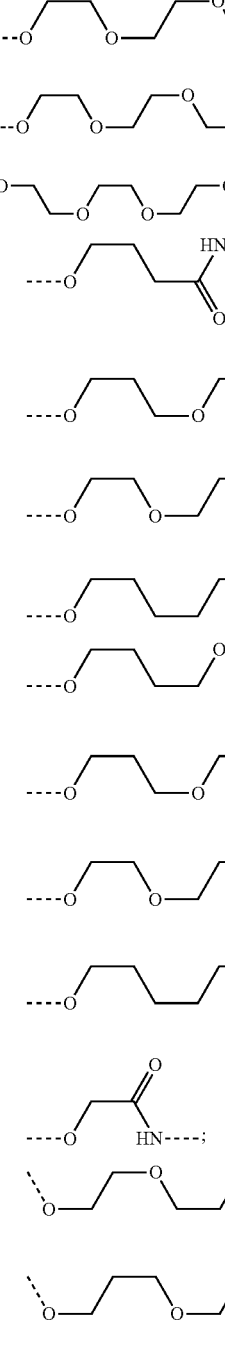

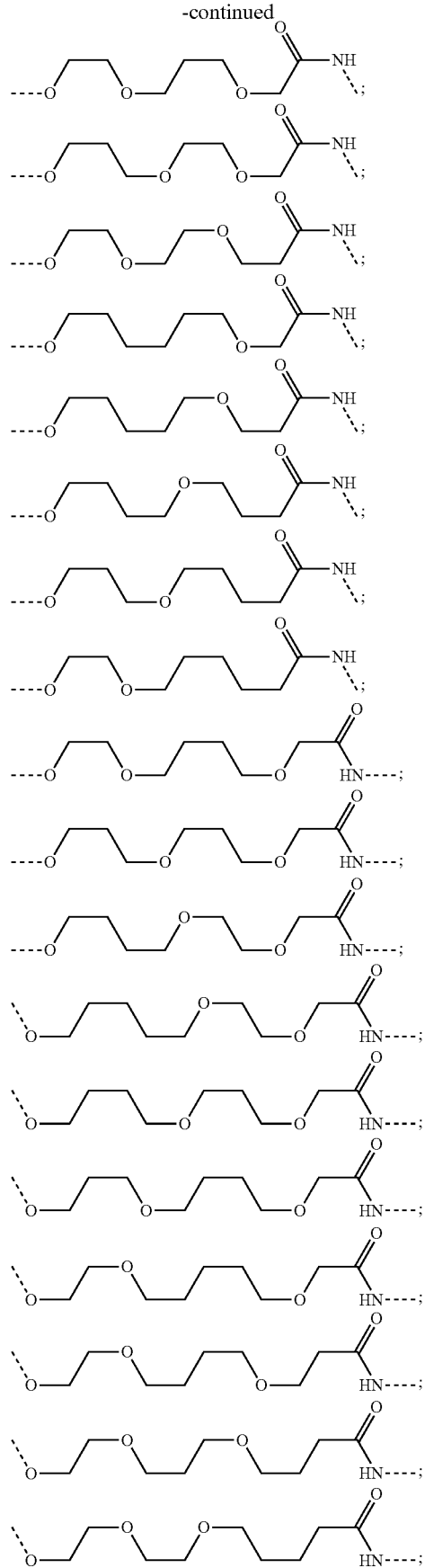
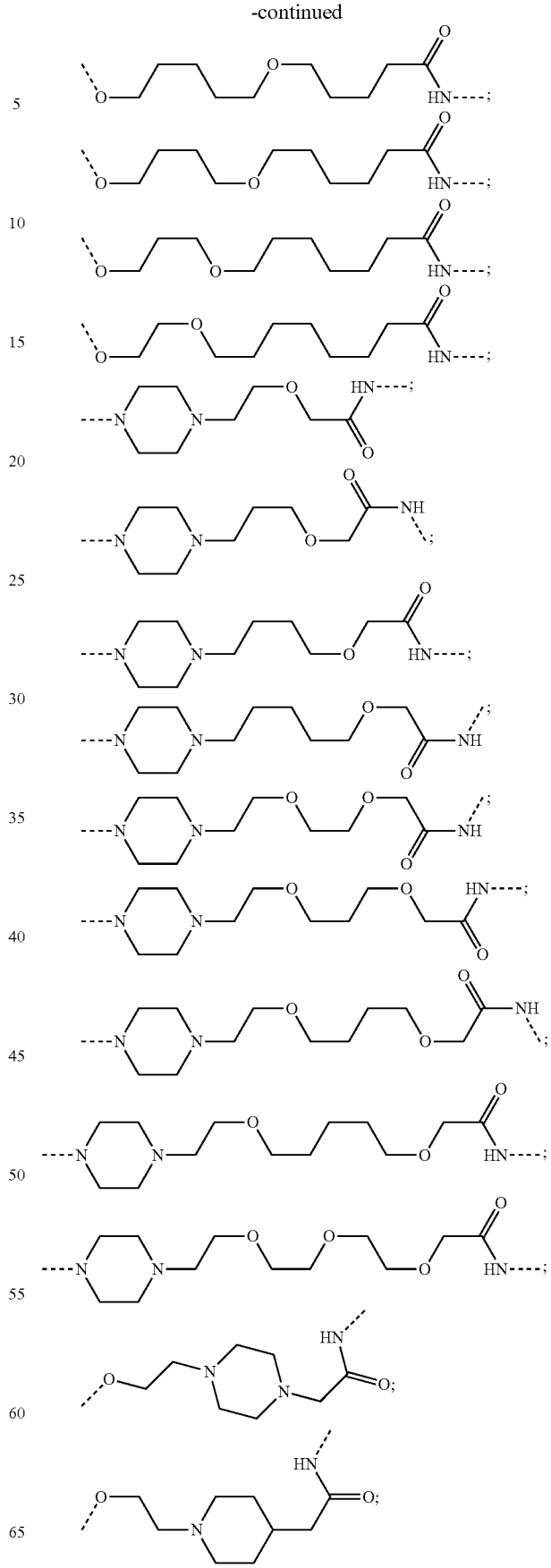

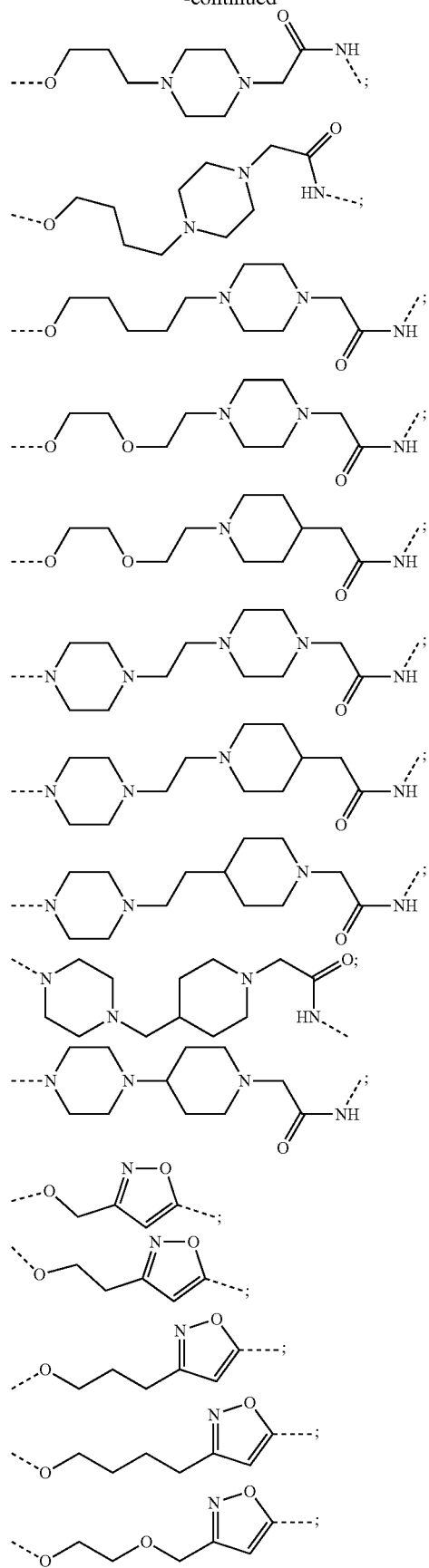
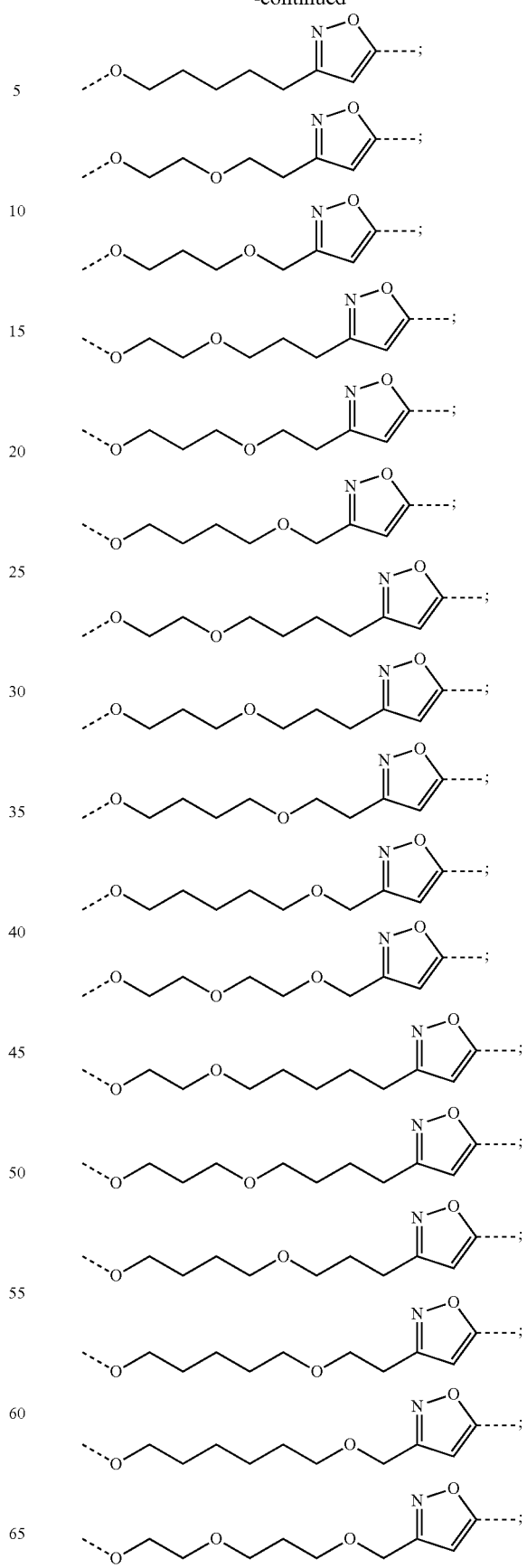

1415
-continued
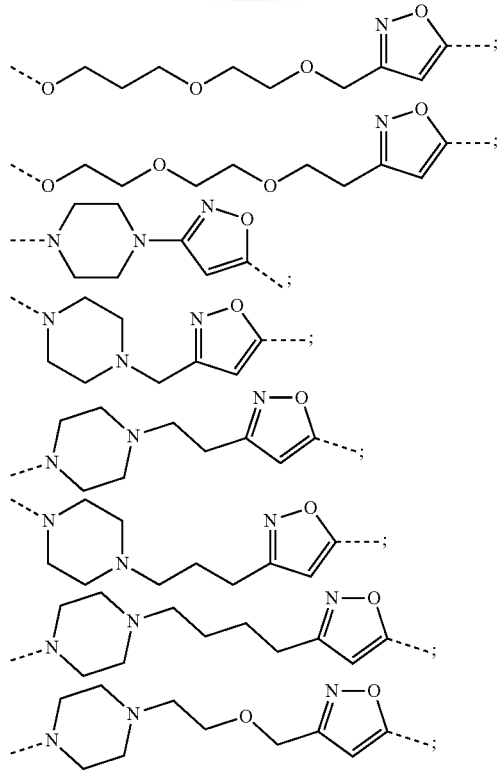
1416
-continued
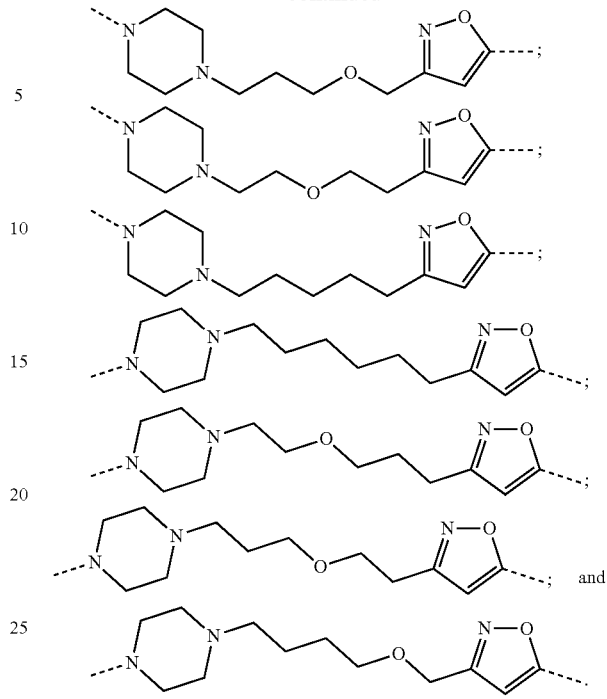
In any aspect or embodiment described herein, the linker (L) is selected from the group consisting of:
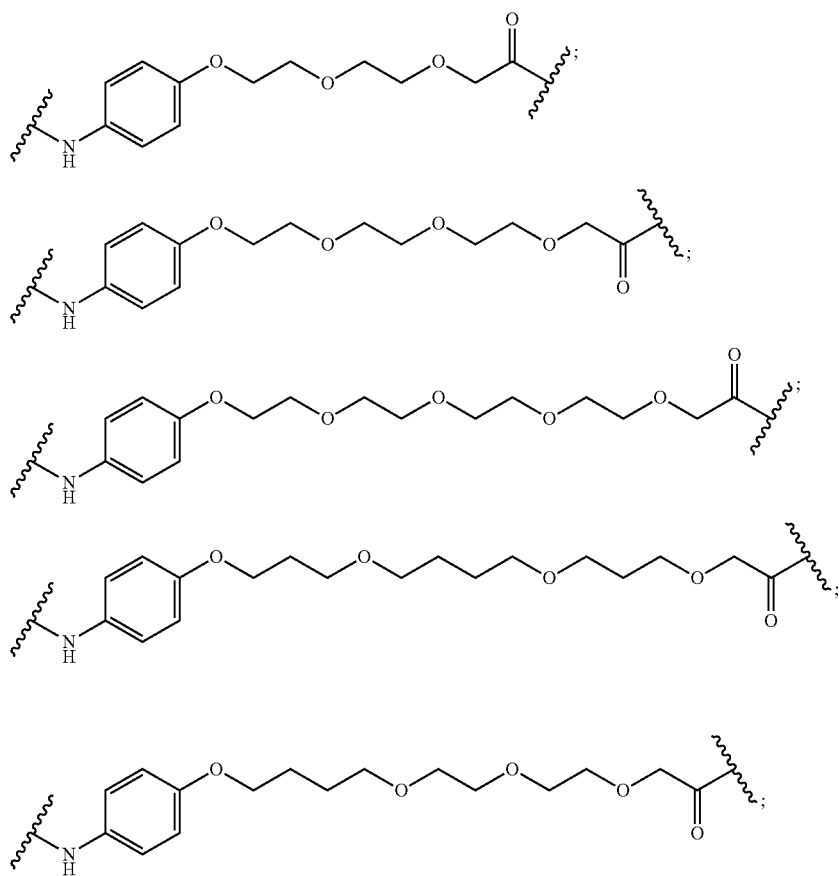

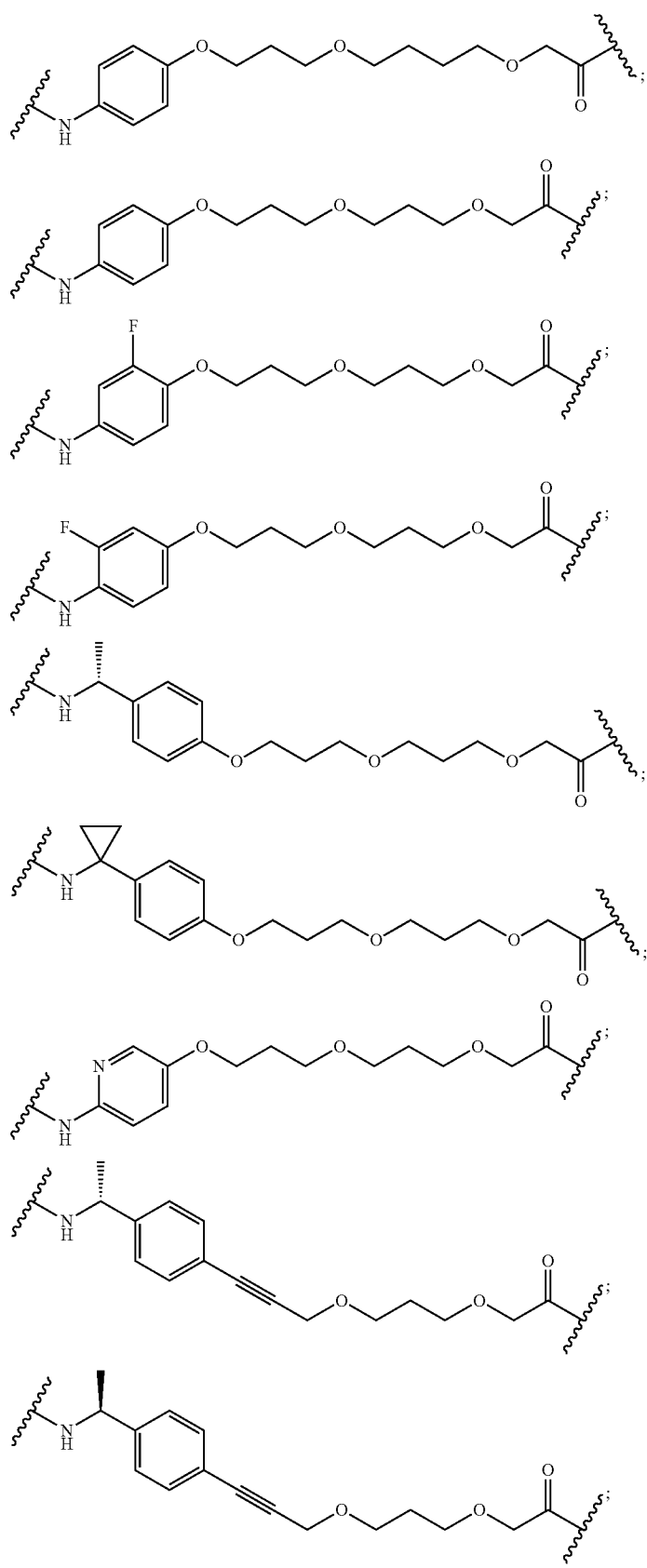

-continued
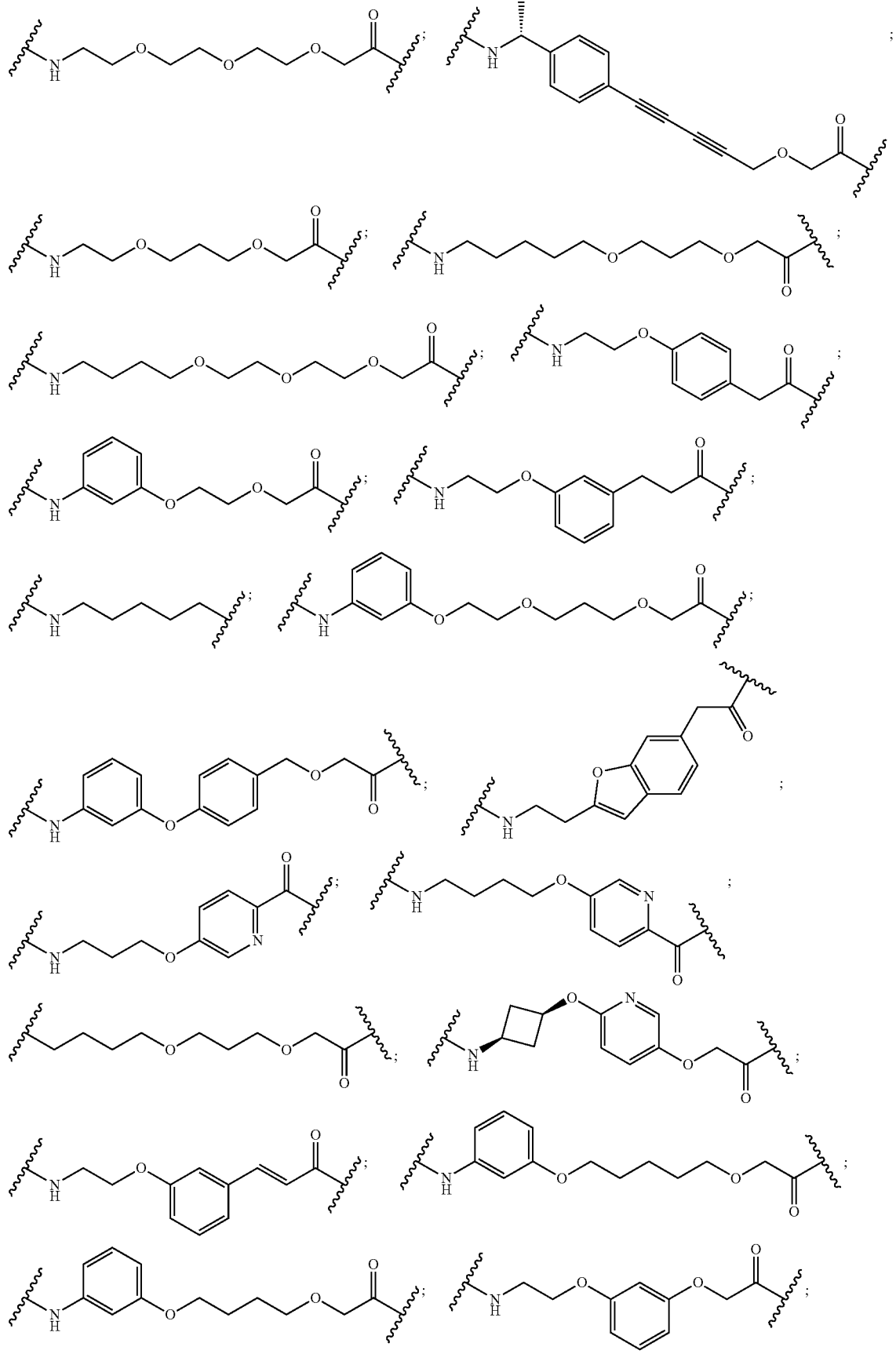

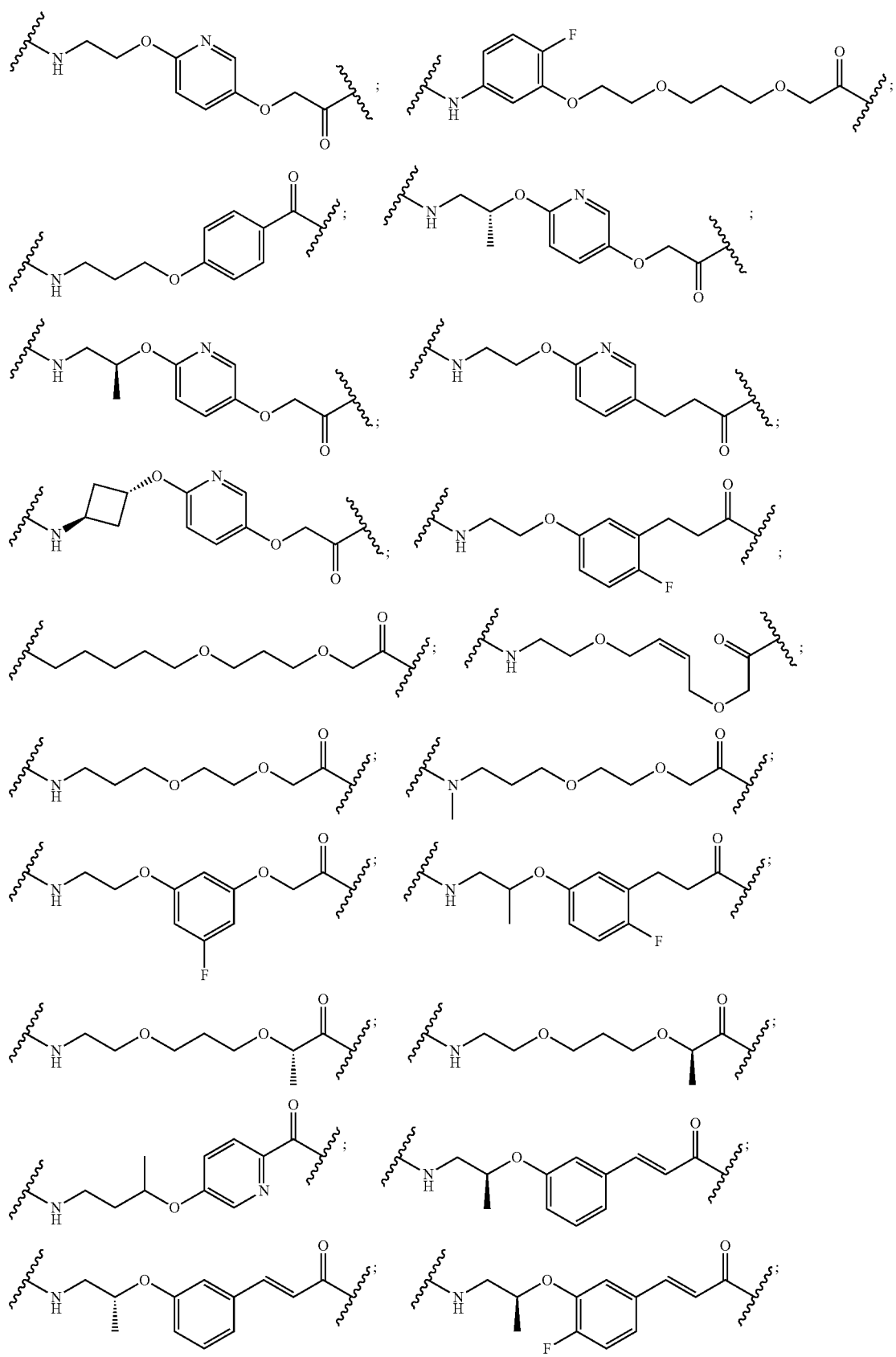

1423 1424
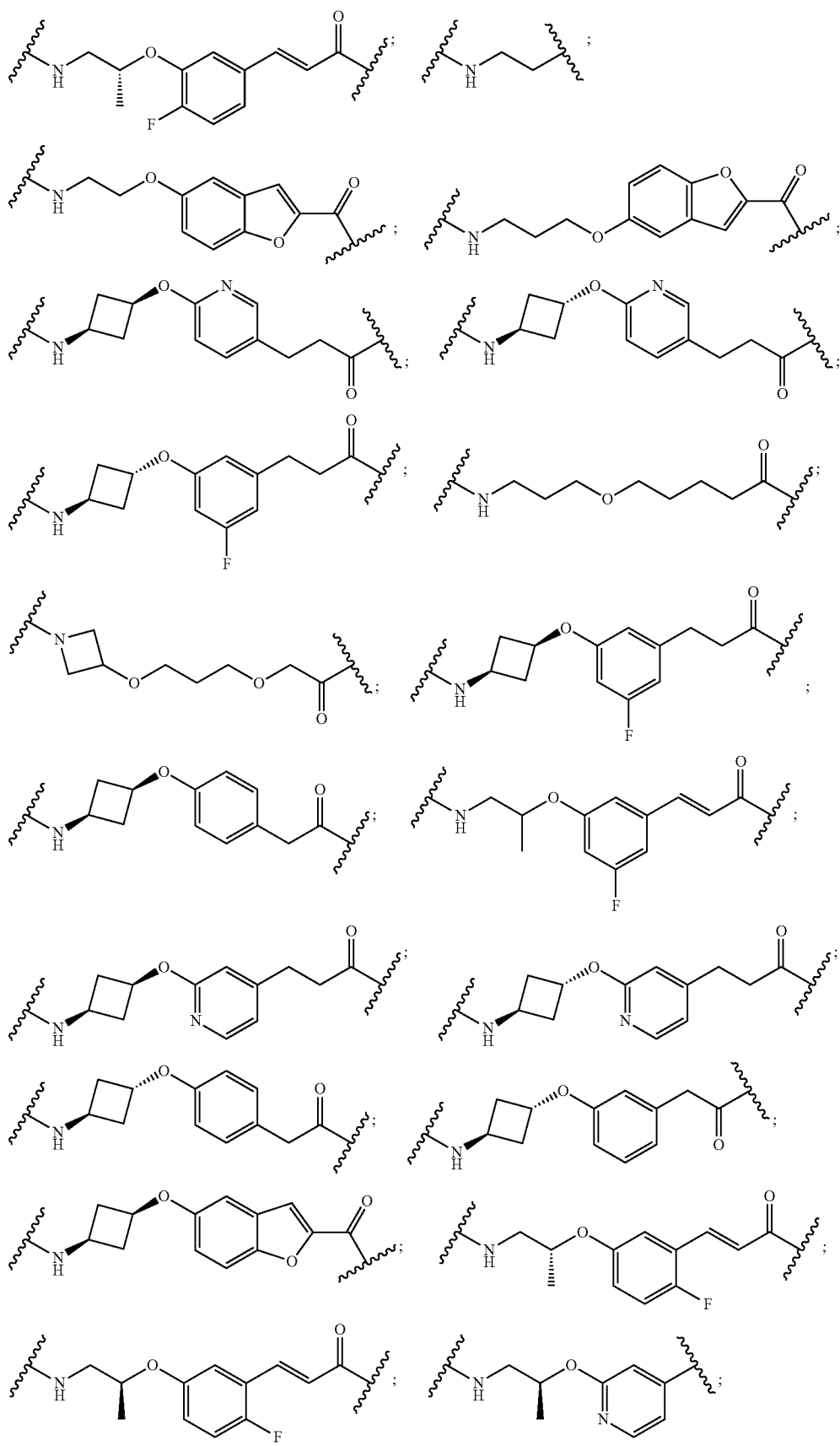

1425              1426
-continued
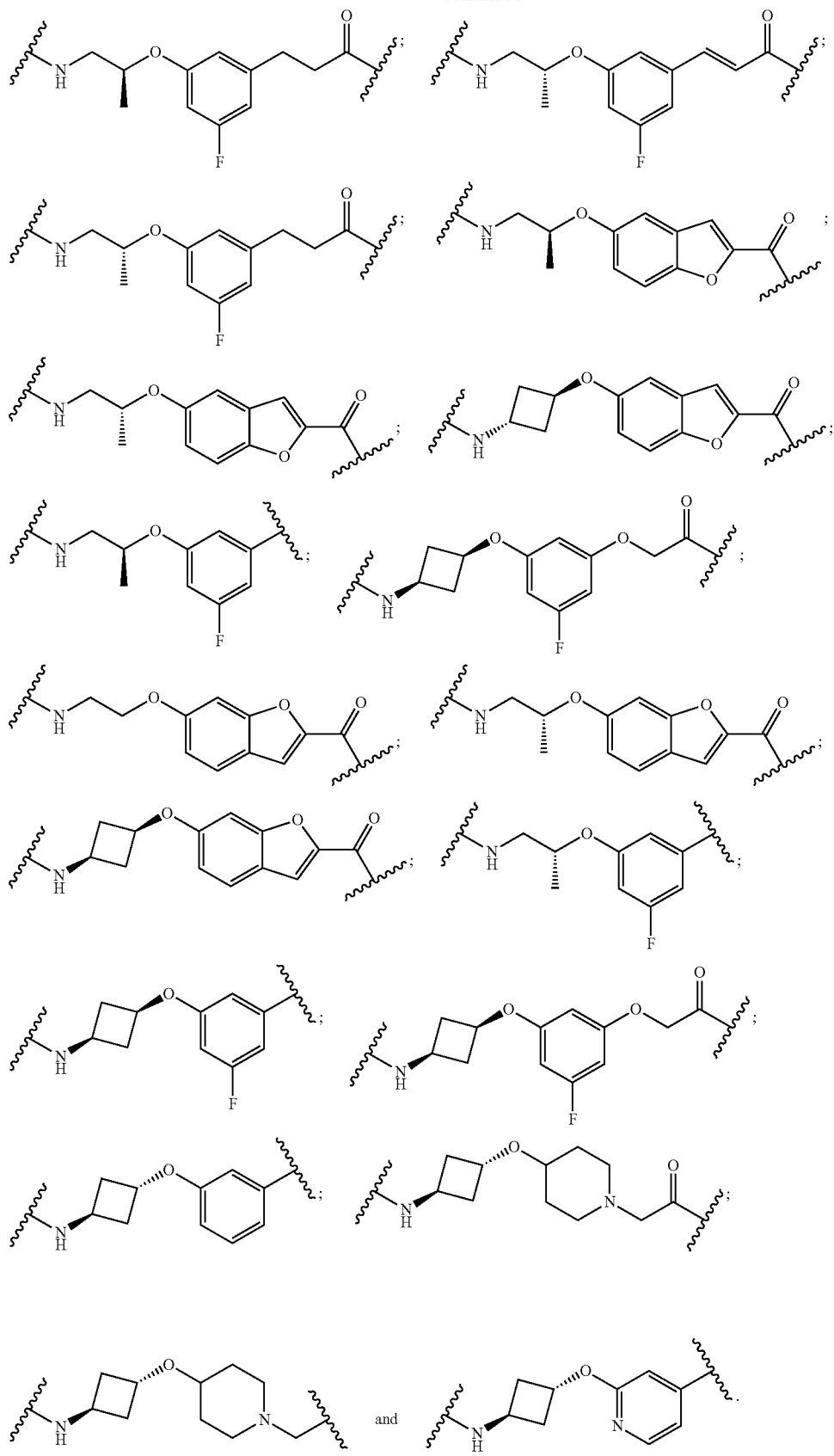

In any aspect or embodiment described herein, the linker (L) is selected from the group consisting of:
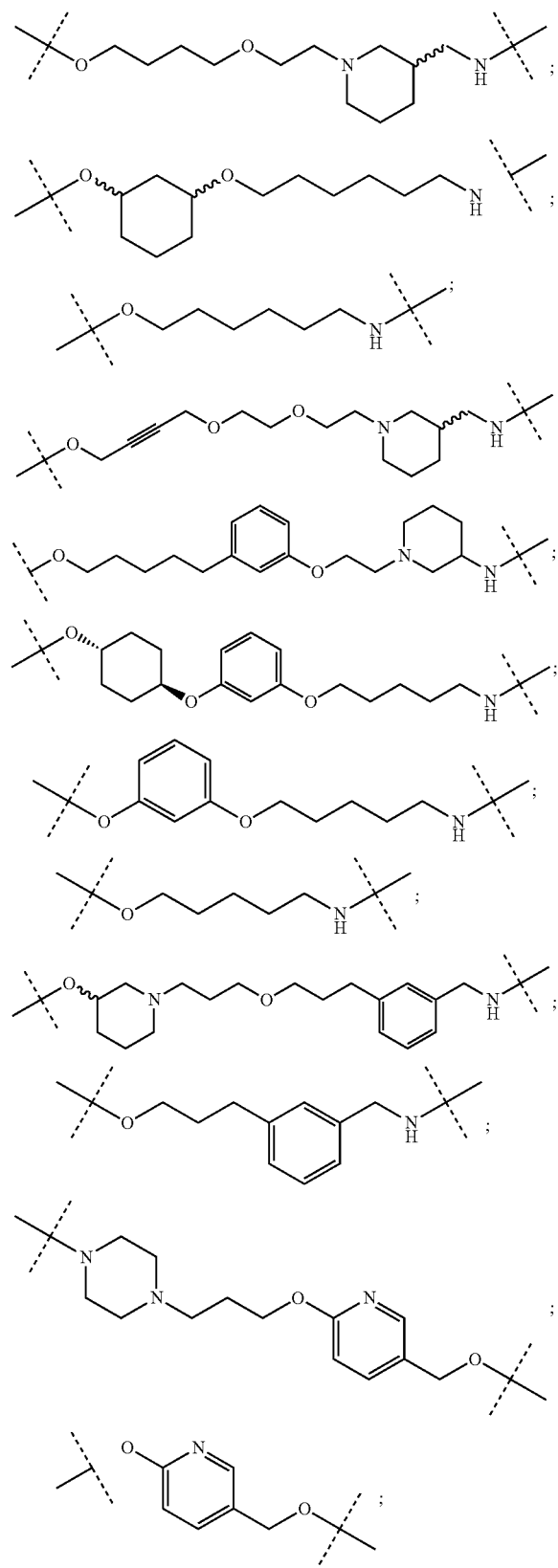
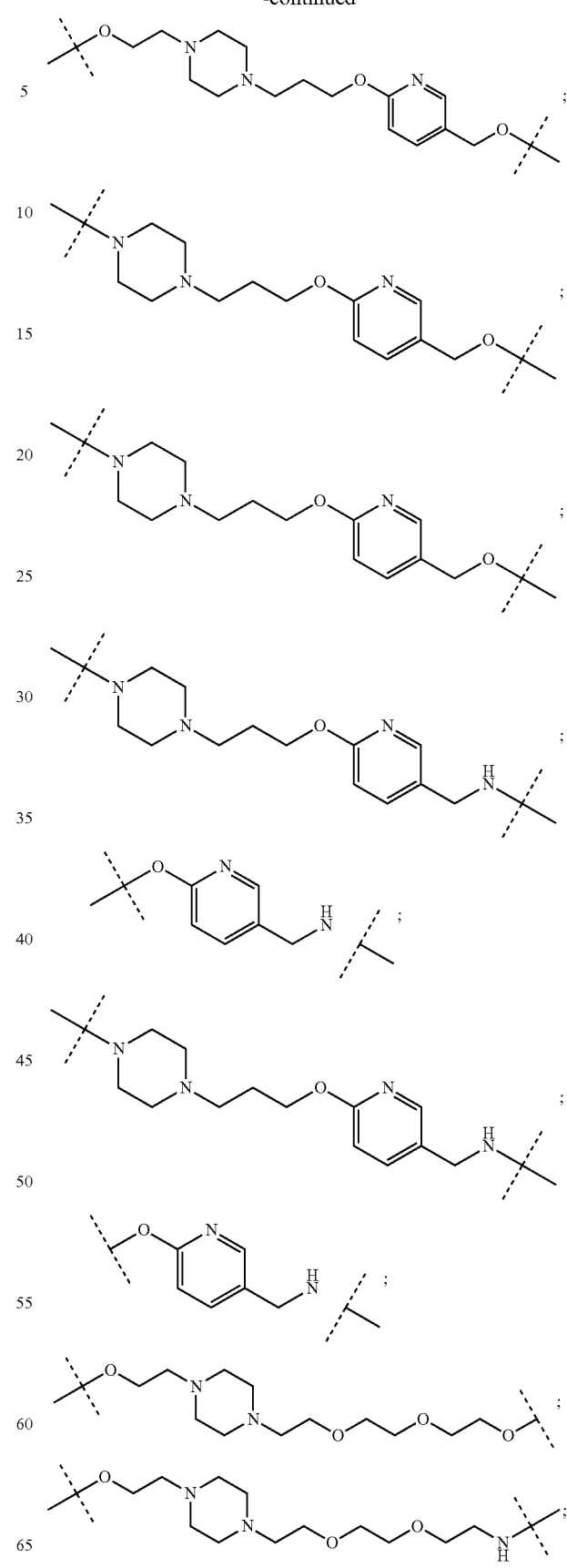

1429
-continued
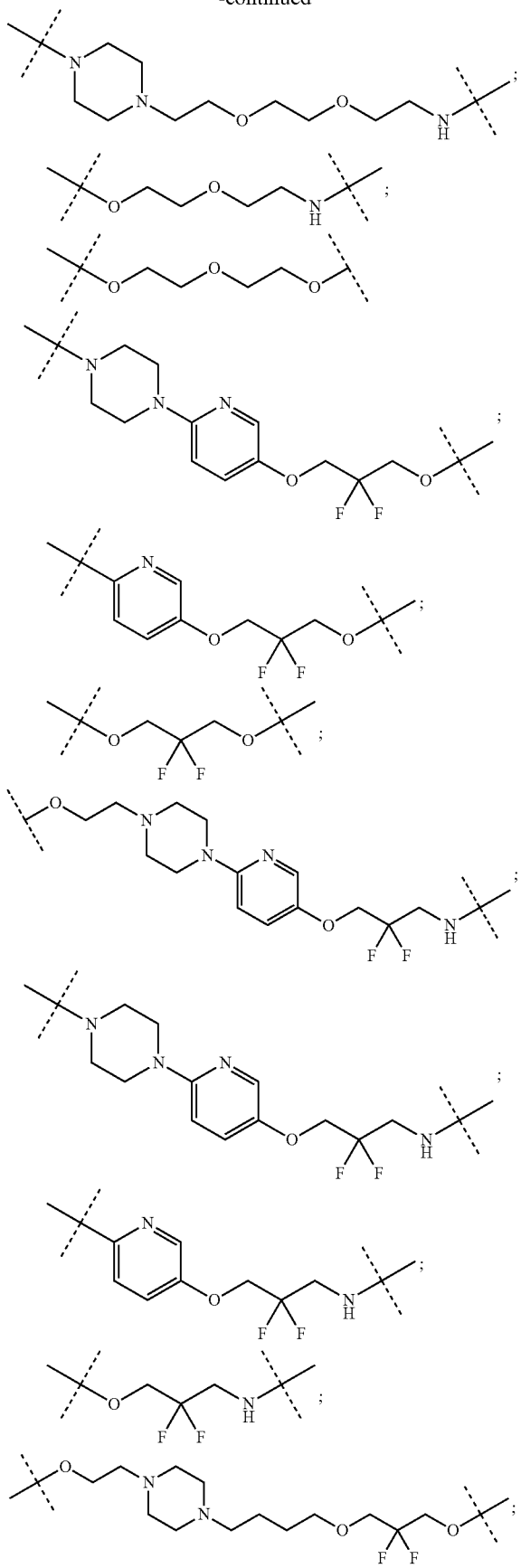
1430
-continued
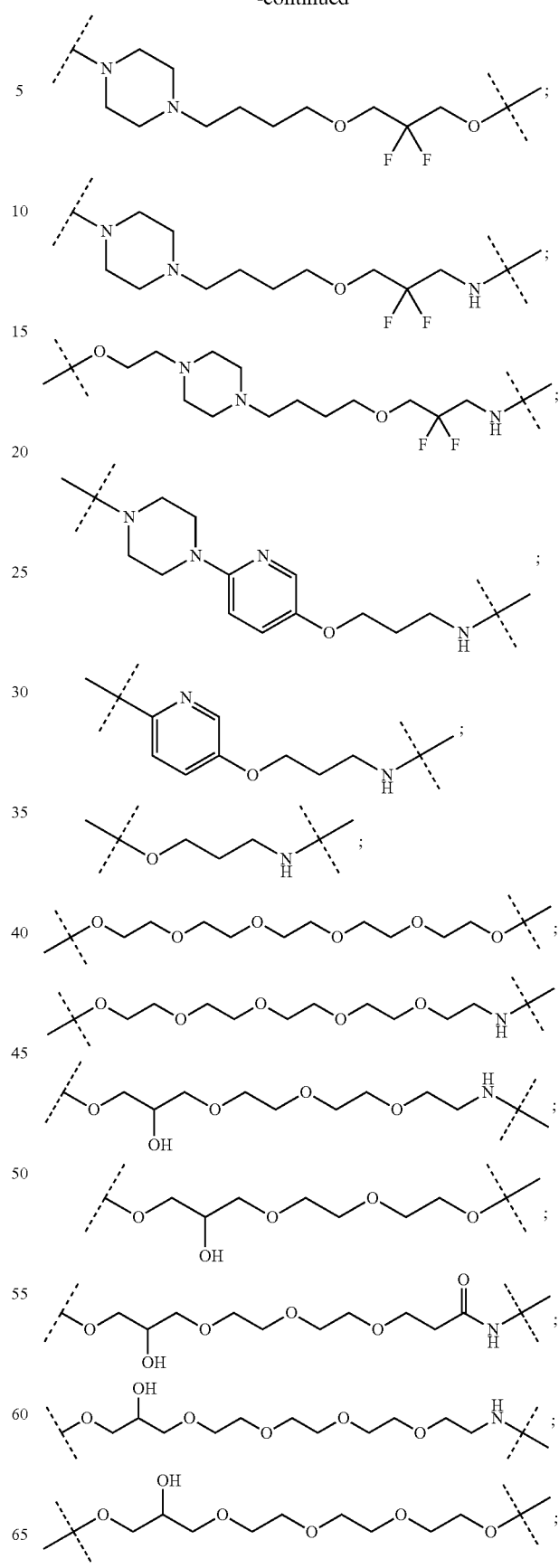

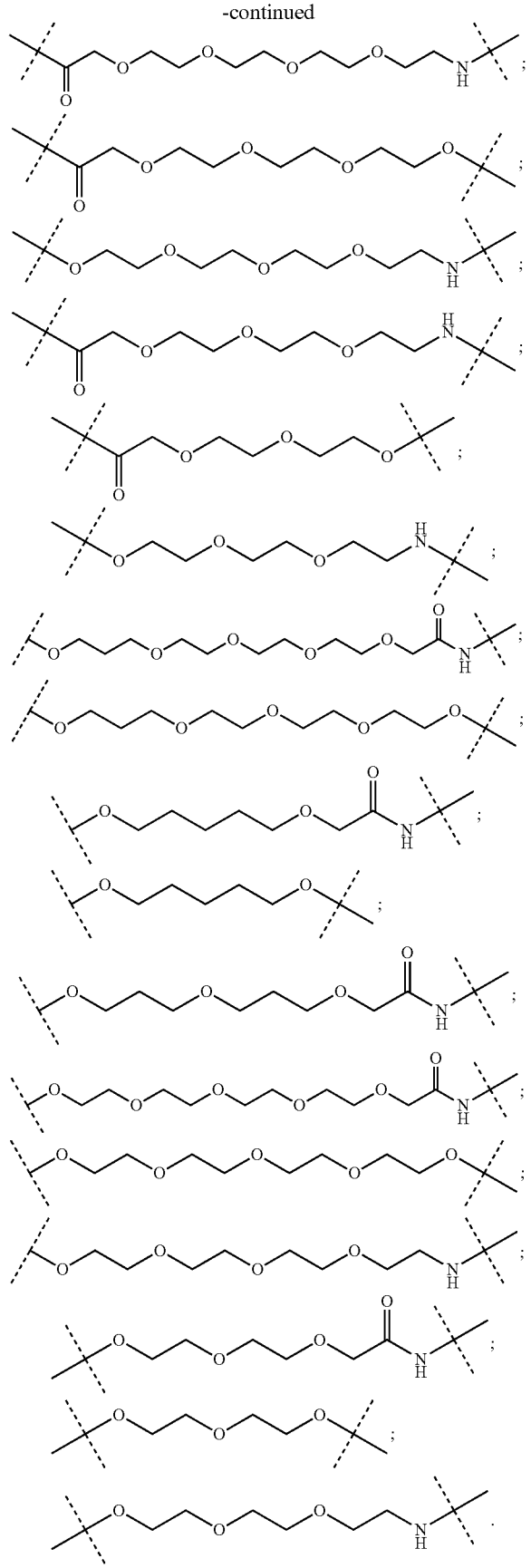

In any aspect or embodiment described herein, the linker (L) comprises the following chemical structure:

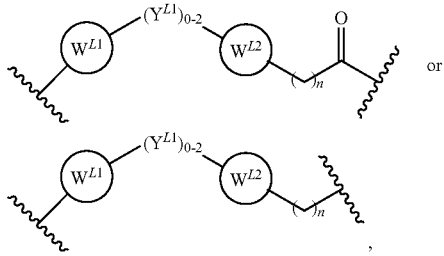

wherein:
$W^{L1}$ and $W^{L2}$ are each independently a 4-8 membered ring with 0-4 heteroatoms, optionally substituted with RQ, each RQ is independently a H, halo, OH, CN, CF3, C1-C6 alkyl (linear, branched, optionally substituted), C1-C6 alkoxy (linear, branched, optionally substituted), or 2 RQ groups taken together with the atom they are attached to, form a 4-8 membered ring system containing 0-4 heteroatoms;
$Y^{L1}$ is each independently a bond, C1-C6 alkyl (linear, branched, optionally substituted) and optionally one or more C atoms are replaced with O; or C1-C6 alkoxy (linear, branched, optionally substituted);
n is 0-10; and
a dashed line indicates the attachment point to the PTM or ULM moieties.

In any aspect or embodiment described herein, the linker (L) comprises the following chemical structure:

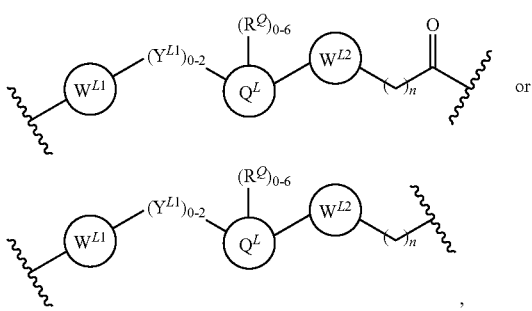

wherein:
$W^{L1}$ and $W^{L2}$ are each independently aryl, heteroaryl, cyclic, heterocyclic, $C_{1-6}$ alkyl, bicyclic, biaryl, biheteroaryl, or biheterocyclic, each optionally substituted with $R^Q$, each $R^Q$ is independently a H, halo, OH, CN, $CF_3$, hydroxyl, nitro, C=CH, $C_{2-6}$ alkenyl, $C_{2-6}$ alkynyl, $C_1$-$C_6$ alkyl (linear, branched, optionally substituted), $C_1$-$C_6$ alkoxy (linear, branched, optionally substituted), $OC_{1-3}$alkyl (optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;
$Y^{L1}$ is each independently a bond, $NR^{YL1}$, O, S, $NR^{YL2}$, $CR^{YL1}R^{YL2}$, C=O, C=S, SO, $SO_2$, $C_1$-$C_6$ alkyl (linear, branched, optionally substituted) and optionally one or more C atoms are replaced with O; $C_1$-$C_6$ alkoxy (linear, branched, optionally substituted);
$Q^L$ is a 3-6 membered alicyclic or aromatic ring with 0-4 heteroatoms, optionally bridged, optionally substituted with 0-6 $R^Q$, each $R^Q$ is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^{YL1}$, $R^{YL2}$ are each independently H, OH, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

n is 0-10; and a dashed line indicates the attachment point to the PTM or ULM moieties.

In any aspect or embodiment described herein, the linker (L) is selected from the group consisting of:

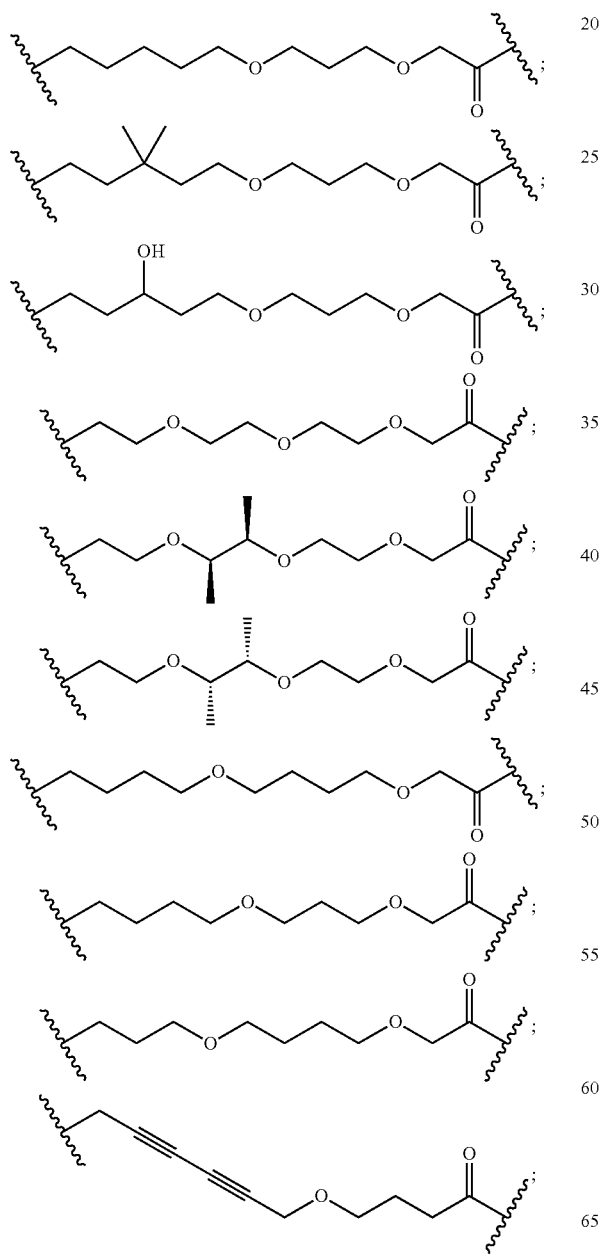
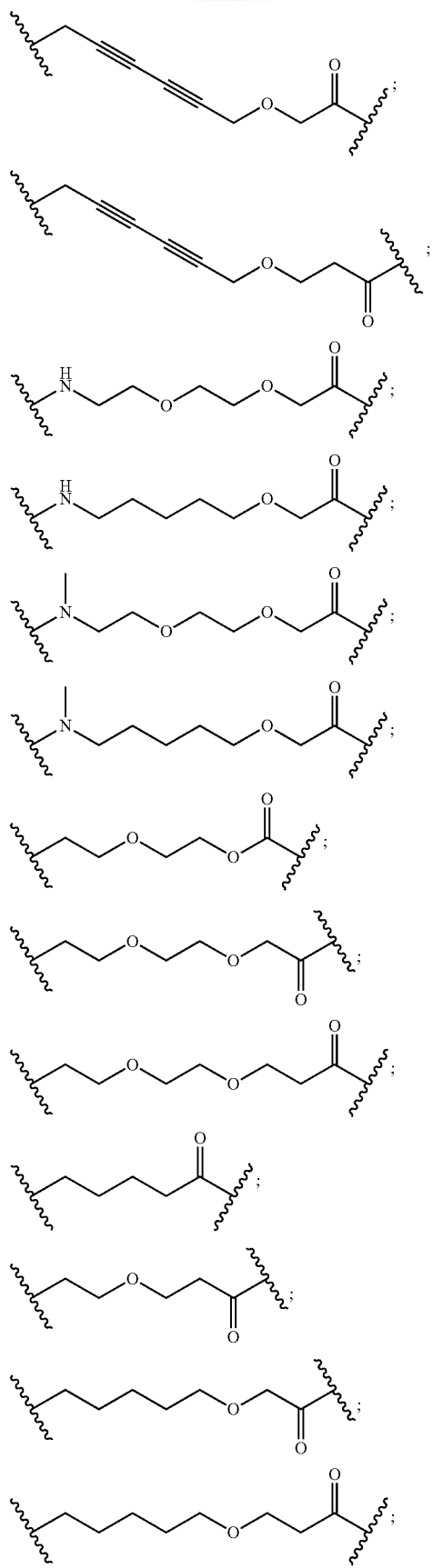

1435
-continued
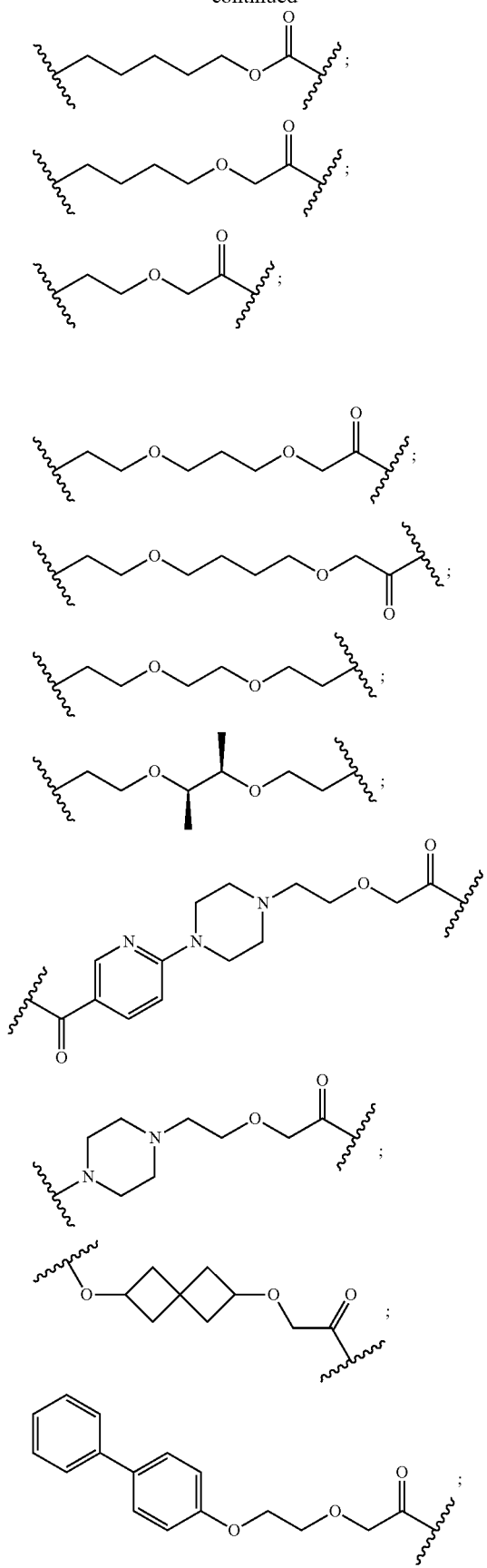
1436
-continued
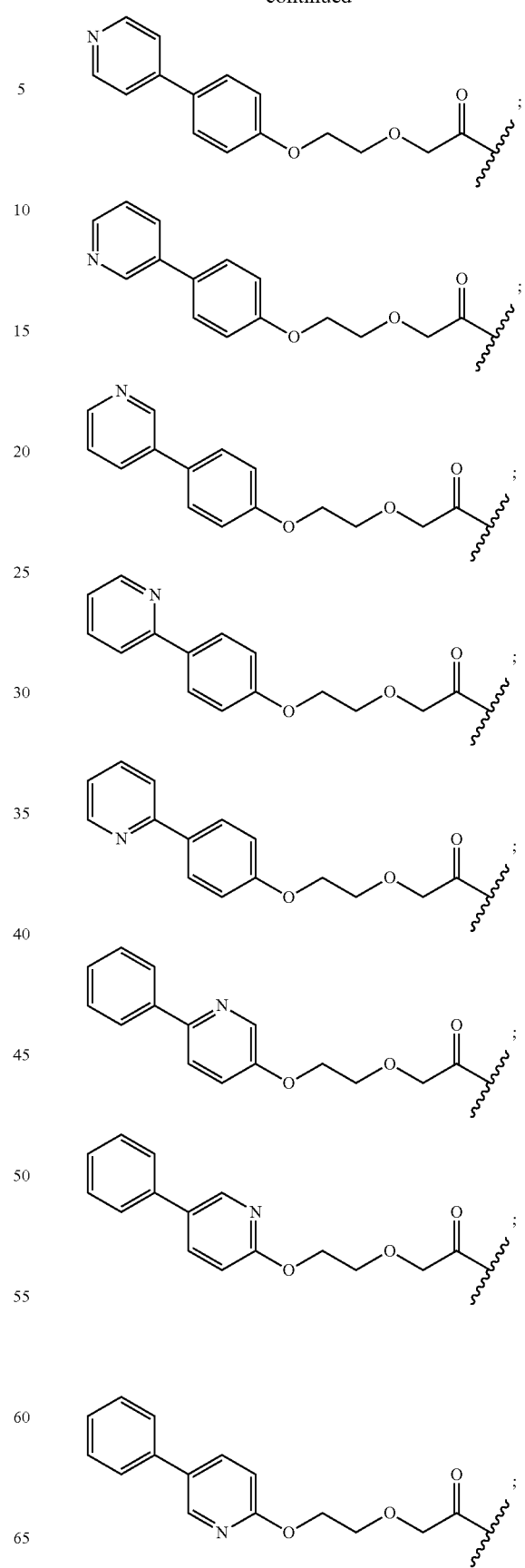

1437
-continued

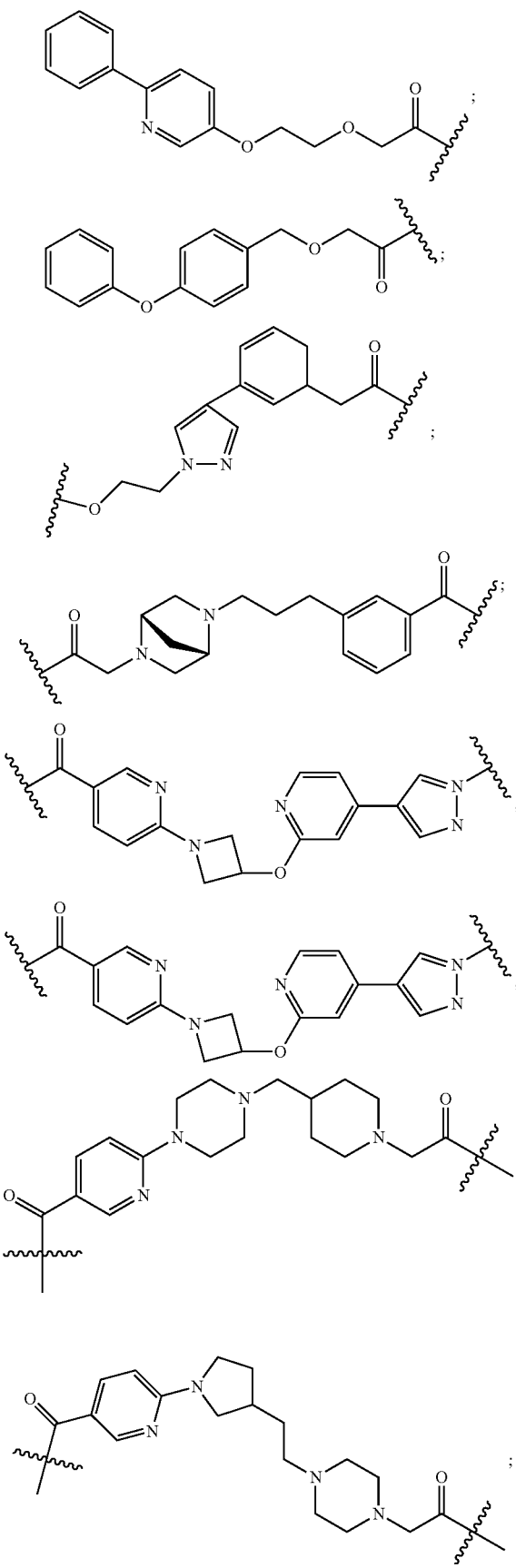

1438
-continued

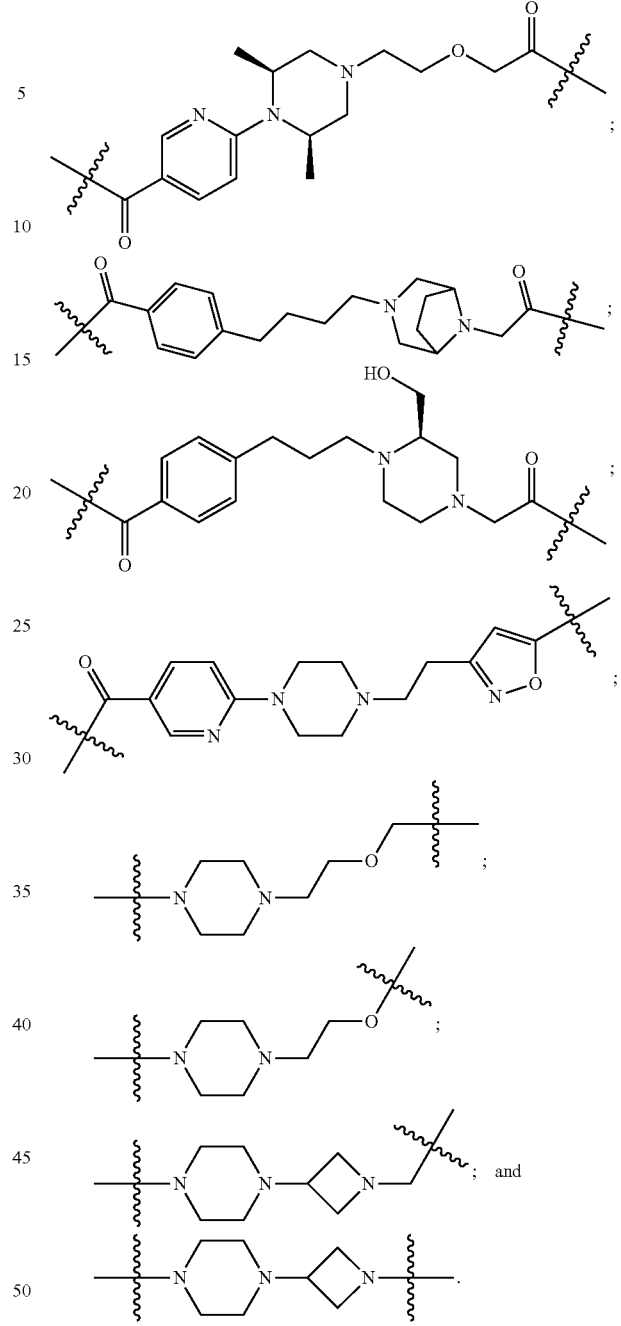

In any aspect or embodiment described herein, the linker (L) is a polyethylenoxy group optionally substituted with aryl or phenyl comprising from 1 to 10 ethylene glycol units.

In any aspect or embodiment described herein, the linker is selected from Tables 1-40.

In any aspect or embodiment described herein, the compound comprises multiple ULMs, multiple PTMs, multiple linkers or any combinations thereof.

In any aspect or embodiment described herein, the compound is selected from Table 1 through Table 43.

In any aspect or embodiment described herein, the PTM is a small molecule comprising a B-RAF protein targeting moiety.

In an additional aspect, the present disclosure provides a composition. The composition comprise an effective amount of a bifunctional compound of the present disclosure, and a pharmaceutically acceptable carrier.

In any aspect or embodiment described herein, the composition further comprises at least one of an additional bioactive agent or another bifunctional compound of the present disclosure.

In any aspect or embodiment described herein, the additional bioactive agent is anti-cancer agent.

In a further aspect, the present disclosure provides a composition comprising a pharmaceutically acceptable carrier and an effective amount of at least one compound of the present disclosure for treating a disease or disorder in a subject, the method comprising administering the composition to a subject in need thereof, wherein the compound is effective in treating or ameliorating at least one symptom of the disease or disorder.

In any aspect or embodiment described herein, the disease or disorder is associated with Raf accumulation and aggregation.

In any aspect or embodiment described herein, the disease or disorder is cancer; cardiofaciocutaneous syndrome; neurofibromatosis type 1; Costello syndrome; Noonan Syndrome; or Lentigo, Electrocardiographic abnormalities, Ocular hypertelorism, Pulmonary stenosis, Abnormal genitalia, Retarded growth, Deafness (LEOPARD) syndrome associated with RAF accumulation and aggregation.

In any aspect or embodiment described herein, the cancer is renal cell carcinoma; pancreatice cancer, colorectal cancer; lung cancer; ovarian cancer; thyroid cancer; pilocytic astrocytoma; prostate cancer; gastric cancer; hepatocellular carcinoma; or melanoma.

What is claimed is:
1. A bifunctional compound having the chemical structure:

ULM-L-PTM, or a pharmaceutically acceptable salt, enantiomer, or stereoisomer thereof,
wherein:
(a) the ULM is a Von Hippel-Lindau (VHL) E3 ubiquitin binding moiety (VLM) with a chemical structure represented by:

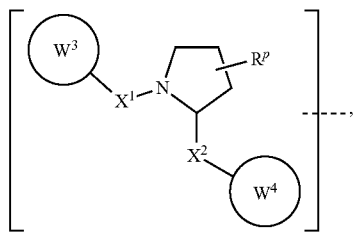

wherein:
$X^1$, $X^2$ are each independently selected from the group of a bond, O, $NR^{Y3}$, $CR^{Y3}R^{Y4}$, C=O, C=S, SO, and $SO_2$;
$R^{Y3}$, $R^{Y4}$ are each independently selected from the group of H, linear or branched $C_{1-6}$ alkyl optionally substituted by 1 or more halo, $C_{1-6}$ alkoxyl optionally substituted by 0-3 $R^P$ groups;
$R^P$ is 0, 1, 2, or 3 groups, each independently selected from H, halo, —OH, $C_{1-3}$ alkyl, and C=O;

$W^3$ is selected from the group consisting of an optionally substituted -T-N($R^{1a}R^{1b}$)$X^3$, optionally substituted -T-N($R^{1a}R^{1b}$), optionally substituted -T-Aryl, an optionally substituted -T-Heteroaryl, an optionally substituted -T-Heterocycle, an optionally substituted —$NR^1$-T-Aryl, an optionally substituted —$NR^1$-T-Heteroaryl, and an optionally substituted -$NR^1$-T-Heterocycle;
$X^3$ of Formula ULM-a is C=O, $R^1$, $R^{1a}$, and $R^{1b}$;
$R^1$, $R^{1a}$, $R^{1b}$ are each independently selected from the group consisting of H, linear or branched $C_1$-$C_6$ alkyl group optionally substituted by 1 or more halo or —OH groups, $R^{Y3}$C=O, $R^{Y3}$C=S, $R^{Y3}$SO, $R^{Y3}$SO$_2$, N($R^{Y3}R^{Y4}$)C=O, N($R^{Y3}R^{Y4}$)C=S, N($R^{Y3}R^{Y4}$)SO, and N($R^{Y3}R^{Y4}$)SO$_2$;
T is selected from the group of an optionally substituted alkyl, —(CH$_2$)$_n$— group, wherein each one of the methylene groups is optionally substituted with one or two substituents selected from the group of halogen, methyl, a linear or branched $C_1$-$C_6$ alkyl group optionally substituted by 1 or more halogen or —OH groups or an amino acid side chain optionally substituted; and
n is 0 to 6,
$W^4$ is

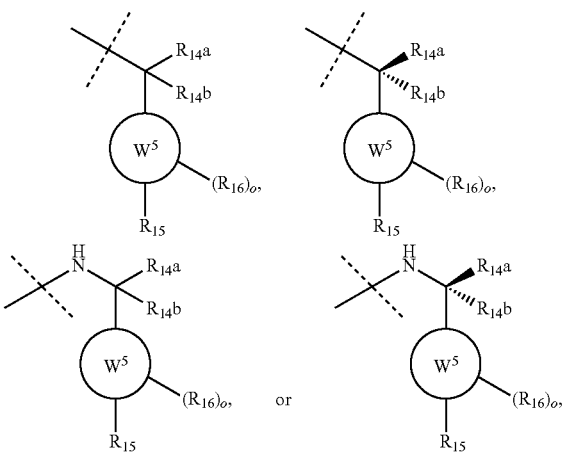

$R_{14a}$, $R_{14b}$ are each independently selected from the group of H, haloalkyl, or optionally substituted alkyl;
$W^5$ is selected from the group of a phenyl or a 5-10 membered heteroaryl,
$R_{15}$ is selected from the group of H, halogen, CN, OH, NO$_2$, N $R_{14a}R_{14b}$, OR$_{14a}$, CONR$_{14a}R_{14b}$, NR$_{14a}$COR$_{14b}$, SO$_2$NR$_{14a}R_{14b}$, NR$_{14a}$SO$_2$R$_{14b}$, optionally substituted alkyl, optionally substituted haloalkyl, optionally substituted haloalkoxy, optionally substituted aryl, optionally substituted heteroaryl, optionally substituted cycloalkyl, or optionally substituted cycloheteroalkyl;
o is an integer from 0-4;
$R_{16}$ is independently selected from the group of halo, optionally substituted alkyl, optionally substituted haloalkyl, hydroxy, or optionally substituted haloalkoxy; and ⟋ indicates the site of attachment of the VLM to the linker (L);

(b) the L is a chemical linking group connecting the ULM and the PTM and that has a chemical structural unit represented by the formula:

-(A$^L$)$_q$-, wherein:

(A$^L$)$_q$ is a group which is connected to a ULM or PTM moiety;

q is an integer greater than or equal to 1;

each A$^L$ is independently selected from the group consisting of CR$^{L1}$R$^{L2}$, O, S, SO, SO$_2$, NR$^{L3}$, SO$_2$NR$^{L3}$, SONR$^{L3}$, CONR$^{L3}$, NR$^{L3}$CONR$^{L4}$, NR$^{L3}$SO$_2$NR$^{L4}$, CO, CR$^{L1}$=CR$^{L2}$, C≡C, SiR$^{L1}$R$^{L2}$, P(O)R$^{L1}$P(O)OR$^{L1}$, NR$^{L3}$C(=NCN) NR$^{L4}$, NR$^{L3}$C(=NCN), NR$^{L3}$C(=CNO$_2$) NR$^{L4}$, C$_{3-11}$cycloalkyl optionally substituted with 0-6 R$^{L1}$ and/or R$^{L2}$ groups, C$_{3-11}$heterocyclyl optionally substituted with 0-6 R$^{L1}$ and/or R$^{L2}$ groups, aryl optionally substituted with 0-6 R$^{L1}$ and/or R$^{L2}$ groups, heteroaryl optionally substituted with 0-6 R$^{L1}$ and/or R$^{L2}$ groups, where R$^{L1}$ or R$^{L2}$, each independently are optionally linked to other groups to form cycloalkyl and/or heterocyclyl moiety, optionally substituted with 0-4 R$^{L5}$ groups; and R$^{L1}$, R$^{L2}$, R$^{L3}$, R$^{L4}$ and R$^{L5}$ are, each independently, H, halo, C$_{1-8}$alkyl, OC$_{1-8}$alkyl, SC$_{1-8}$alkyl, NHC$_{1-8}$alkyl, N(C$_{1-8}$alkyl)$_2$, C$_{3-11}$cycloalkyl, aryl, heteroaryl, C$_{3-11}$heterocyclyl, OC$_{1-8}$cycloalkyl, SC$_{1-8}$cycloalkyl, NHC$_{1-8}$cycloalkyl, N(C$_{1-8}$cycloalkyl)$_2$, N(C$_{1-8}$cycloalkyl)(C$_{1-8}$alkyl), OH, NH$_2$, SH, SO$_2$C$_{1-8}$alkyl, P(O)(OC$_{1-8}$alkyl)(C$_{1-8}$alkyl), P(O) (OC$_{1-8}$ alkyl)$_2$, CC—C$_{1-8}$alkyl, CCH, CH=CH (C$_{1-8}$alkyl), C(C$_{1-8}$alkyl)=CH(C$_{1-8}$alkyl), C(C$_{1-8}$alkyl)=C(C$_{1-8}$alkyl)$_2$, Si(OH)$_3$, Si(C$_{1-8}$alkyl)$_3$, Si(OH)(C$_{1-8}$alkyl)$_2$, COC$_{1-8}$alkyl, CO$_2$H, halogen, CN, CF$_3$, CHF$_2$, CH$_2$F, NO$_2$, SF$_5$, SO$_2$NHC$_{1-8}$alkyl, SO$_2$N(C$_{1-8}$alkyl)$_2$, SONHC$_{1-8}$alkyl, SON(C$_{1-8}$alkyl)$_2$, CONHC$_{1-8}$alkyl, CON(C$_{1-8}$alkyl)$_2$, N(C$_{1-8}$alkyl)CONH (C$_{1-8}$alkyl), N(C$_{1-8}$alkyl)CON(C$_{1-8}$alkyl)$_2$, NHCONH(C$_{1-8}$alkyl), NHCON(C$_{1-8}$alkyl)$_2$, NHCONH$_2$, N(C$_{1-8}$alkyl)SO$_2$NH(C$_{1-8}$alkyl), N(C$_{1-8}$alkyl) SO$_2$N(C$_{1-8}$alkyl)$_2$, NH SO$_2$NH (C$_{1-8}$alkyl), NH SO$_2$N(C$_{1-8}$alkyl)$_2$, NH SO$_2$NH$_2$; and (c) the PTM is a small molecule comprising a rapidly accelerated fibrosarcoma (RAF) protein targeting moiety represented by chemical structure PTM-IIa or PTM-IIb:

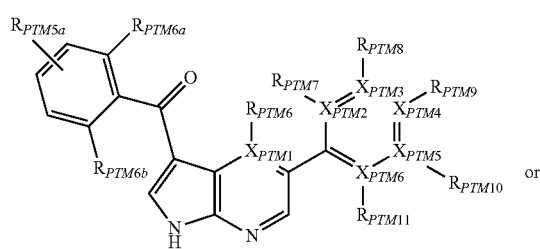

PTM-IIa

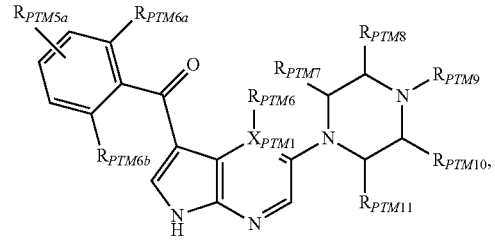

PTM-IIb wherein:

X$_{PTM1}$, X$_{PTM2}$, X$_{PTM3}$, X$_{PTM4}$, X$_{PTM5}$, and X$_{PTM6}$ are independently selected from CH or N;

R$_{PTM5a}$ is selected from the group consisting of: H, optionally substituted amide, optionally substituted amine,

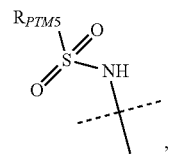

—NHC(O)R$_{PTM5}$;

R$_{PTM5}$ is selected from the group consisting of

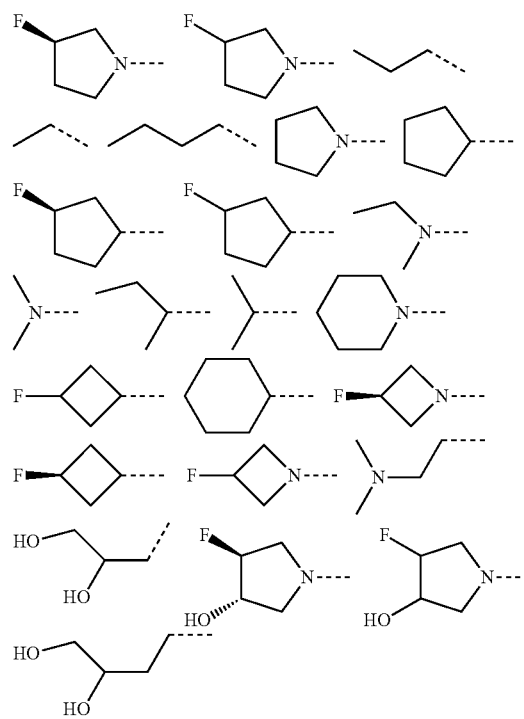

R$_{PTM6a}$ and R$_{PTM6b}$ are each independently selected from hydrogen, halogen, or optionally substituted linear or branched C$_1$-C$_6$ alkyl;

R$_{PTM6}$ is either of the following groups: absent, hydrogen, halogen, aryl, methyl, ethyl, OCH$_3$, NHCH$_3$ or M1-CH$_2$—CH$_2$-M2, wherein M1 is CH$_2$, O and NH, and M2 is hydrogen, alkyl, cyclic alkyl, aryl or heterocycle, R$_{PTM7}$ is absent, hydrogen, halogen, aryl, methyl, ethyl, OCH$_3$, NHCH$_3$ or M1-CH$_2$—CH$_2$-M2, wherein M1 is CH$_2$, O and NH, and M2 is hydrogen, alkyl, cyclic alkyl, aryl or heterocycle, R$_{PTM8}$, R$_{PTM9}$ or R$_{PTM10}$ are independently selected from the group consisting of absent, hydrogen, halogen, aryl, heteroaryl, alkyl, cycloalkyl, heterocycle, methyl, ethyl, OCH$_3$, NHCH$_3$ or M1-CH$_2$—CH$_2$-M2, wherein M1 is CH$_2$, O and NH, and M2 is hydrogen, alkyl, cyclic alkyl, aryl or heterocycle; and R$_{PTM11}$ is absent, hydrogen, halogen, methyl, ethyl, OCH$_3$, NHCH$_3$ or M1-CH$_2$—CH$_2$-M2, wherein M1 is CH$_2$, O and NH, and M2 is hydrogen, alkyl, cyclic alkyl, aryl or heterocycle, wherein at least one of R$_{PTM8}$, R$_{PTM9}$ or R$_{PTM10}$ is modified to be covalently joined to the linker (L).

2. The bifunctional compound according to claim 1, wherein when R$_{PTM9}$ is the covalently joined position, R$_{PTM7}$ and R$_{PTM8}$ are connected together via a covalent bond in a way to form a bicyclic group with the ring to which R$_{PTM7}$ and R$_{PTM8}$ are attached.

3. The bifunctional compound according to claim 1, wherein when R$_{PTM8}$ is the covalently joined position, R$_{PTM9}$ and R$_{PTM10}$ are connected together via a covalent bond in a way to form a bicyclic group with the ring to which R$_{PTM9}$ and R$_{PTM10}$ are attached.

4. The bifunctional compound according to claim 1, wherein when R$_{PTM10}$ is the covalently joined position, R$_{PTM8}$ and R$_{PTM9}$ are connected together via a covalent bond in a way to form a bicyclic group with the ring to which R$_{PTM8}$ and R$_{PTM9}$ are attached.

5. The bifunctional compound according to claim 1, wherein the PTM is selected from the group consisting of:

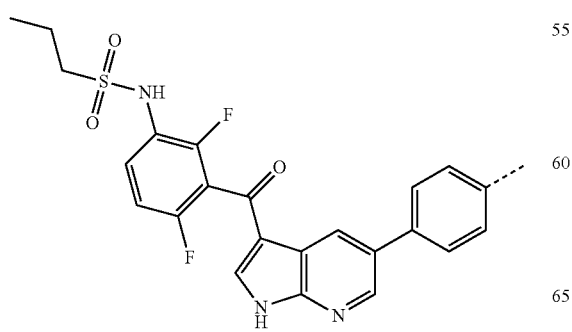

PTM-2

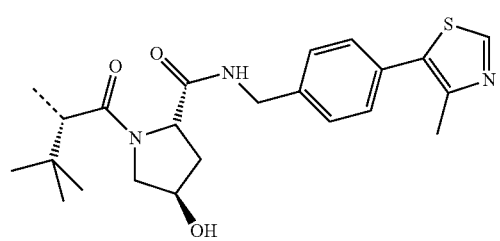

PTM-3

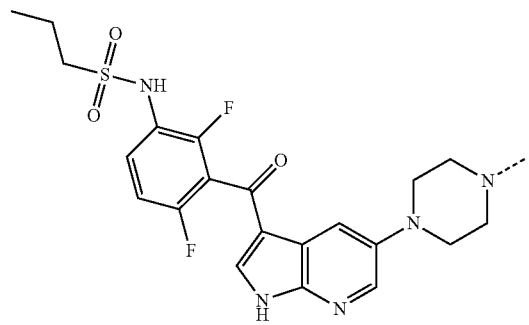

PTM-6

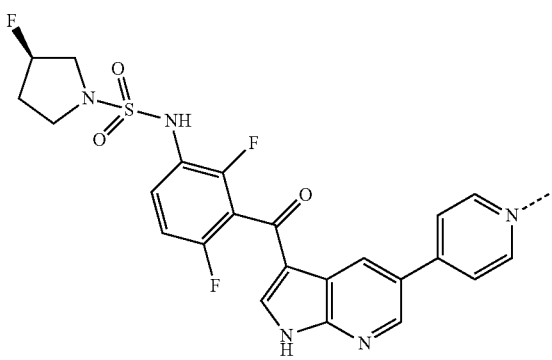

PTM-9

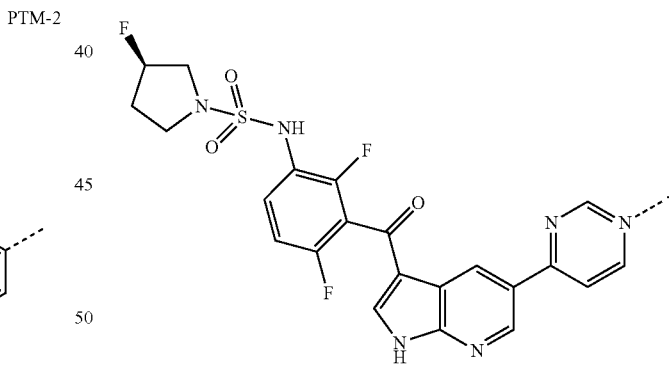

PTM-10

6. The bifunctional compound according to claim 1, wherein the ULM is selected from the group consisting of:

1445

-continued

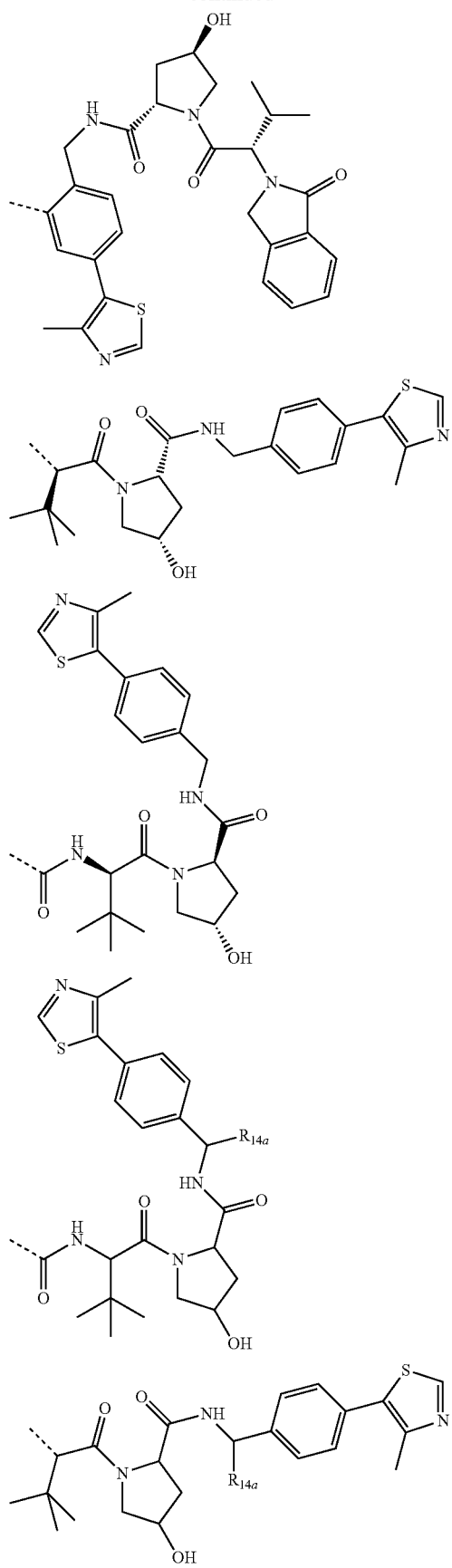

1446

-continued

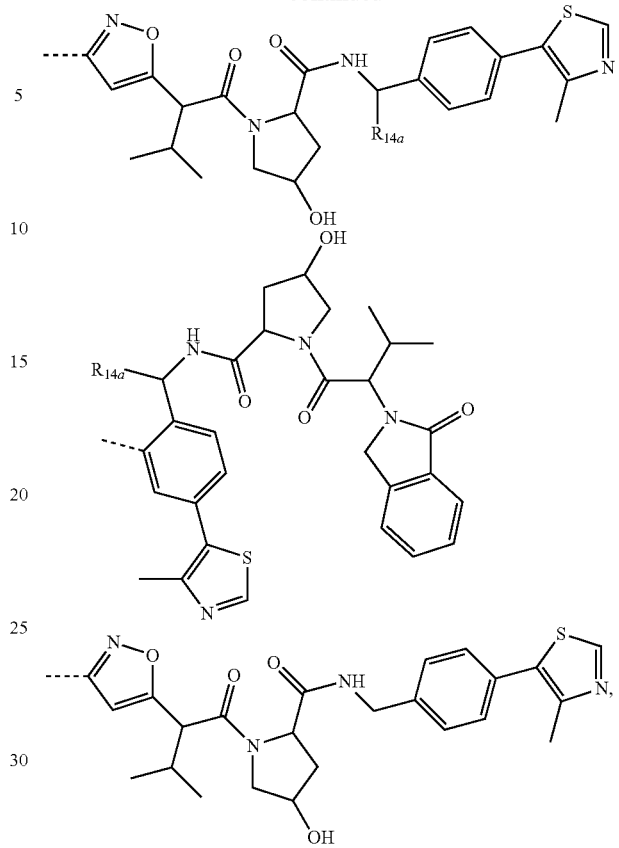

wherein the $R_{14a}$ is a methyl or hydroxymethyl.

7. The bifunctional compound according to claim 1, wherein ULM is a Von Hippel-Lindau (VHL) ligase-binding moiety (VLM) with a chemical structure represented by:

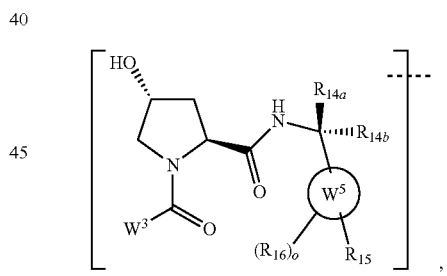

wherein:

W³ is selected from the group of an optionally substituted aryl, optionally substituted heteroaryl, or

$R_9$ and $R_{10}$ are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

1447

R₁₁ is selected from the group of an optionally substituted heterocyclic, optionally substituted alkoxy, optionally substituted heteroaryl, optionally substituted aryl,

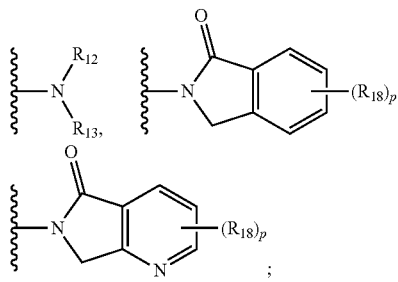

or

R₁₂ is selected from the group of H or optionally substituted alkyl;

R₁₃ is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$, $R_{14b}$, are each independently selected from the group of H, haloalkyl, or optionally substituted alkyl;

$W^5$ is selected from the group of a phenyl or a 5-10 membered heteroaryl,

R₁₅ is selected from the group of H, halogen, CN, OH, NO₂, N$R_{14a}R_{14b}$, O$R_{14a}$, CON$R_{14a}R_{14b}$, N$R_{14a}$CO$R_{14b}$, SO₂N$R_{14a}R_{14b}$, N$R_{14a}$ SO₂$R_{14b}$, optionally substituted alkyl, optionally substituted haloalkyl, optionally substituted haloalkoxy, optionally substituted aryl, optionally substituted heteroaryl, optionally substituted cycloalkyl, or optionally substituted cycloheteroalkyl;

R₁₆ is independently selected from the group of halo, optionally substituted alkyl, optionally substituted haloalkyl, hydroxy, or optionally substituted haloalkoxy;

o is 0, 1, 2, 3, or 4;

R₁₈ is independently selected from the group of H, halo, optionally substituted alkoxy, cyano, optionally substituted alkyl, haloalkyl, haloalkoxy or a linker;

p is 0, 1, 2, 3, or 4; and

⟋ indicates the site of attachment of the VLM to the linker (L).

8. The bifunctional compound according to claim 1, wherein the ULM has a chemical structure selected from the group of:

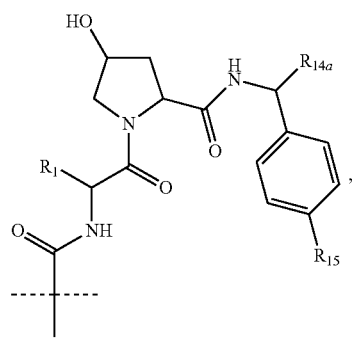

1448

-continued

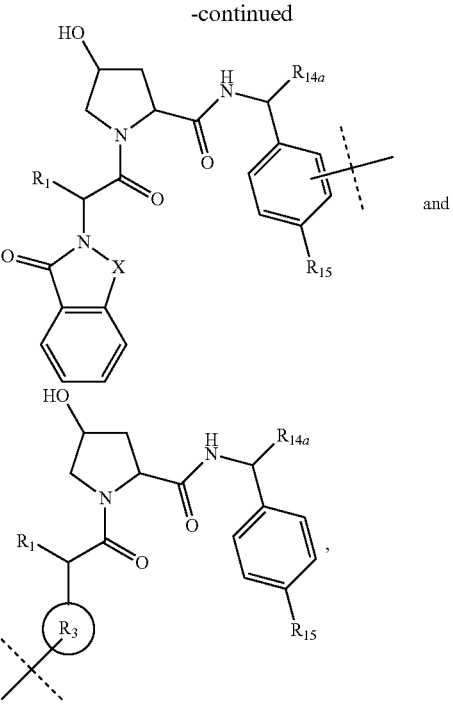

wherein:
R₁ is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;

$R_{14a}$ is H, haloalkyl, optionally substituted alkyl, methyl, fluoromethyl, hydroxymethyl, ethyl, isopropyl, or cyclopropyl;

R₁₅ is selected from the group consisting of H, halogen, CN, OH, NO₂, optionally substituted heteroaryl, optionally substituted aryl, optionally substituted alkyl, optionally substituted haloalkyl, optionally substituted haloalkoxy, optionally substituted cycloalkyl, or optionally substituted cycloheteroalkyl;

X is C or C=O;

R₃ is a bond or an optionally substituted 5 or 6 membered heteroaryl; and the dashed line indicates the site of attachment of the VLM to the linker (L).

9. The bifunctional compound according to claim 1, wherein the ULM comprises a group according to the chemical structure:

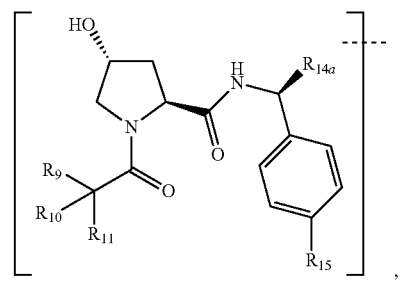

wherein:
$R_{14a}$ is H, haloalkyl, optionally substituted alkyl, methyl, fluoromethyl, hydroxymethyl, ethyl, or isopropyl;

R$_9$ is H;

R$_{10}$ is H, ethyl, isopropyl, tert-butyl, sec-butyl, cyclopropyl, cyclobutyl, cyclopentyl, or cyclohexyl;

R$_{11}$ is

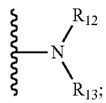

optionally substituted heteroaryl,

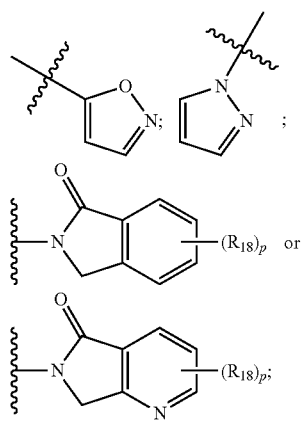

p is 0, 1, 2, 3, or 4; and each R$_{18}$ is independently halo, optionally substituted alkoxy, cyano, optionally substituted alkyl, haloalkyl, haloalkoxy or a linker;

R$_{12}$ is H, C=O

R$_{13}$ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl, R$_{15}$ is selected from the group consisting of H, halogen, Cl, CN, OH, NO$_2$, optionally substituted heteroaryl, optionally substituted aryl;

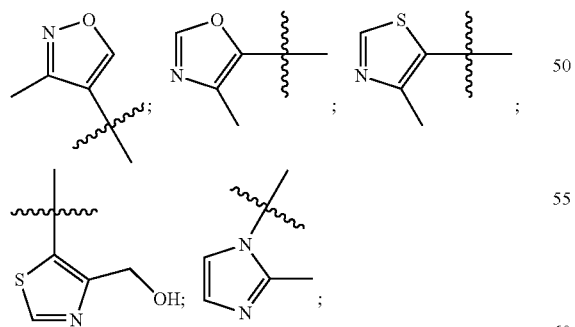

and the dashed line indicates the site of the VLM to the linker (L).

10. The bifunctional compound according to claim 1, wherein the linker (L) comprises a group represented by a general structure selected from the group consisting of:

—N(R)—(CH$_2$)$_m$—O(CH$_2$)$_n$—O(CH$_2$)$_o$—O(CH$_2$)$_p$—O(CH$_2$)$_q$—O(CH$_2$)$_r$—OCH$_2$—,

—O—(CH$_2$)$_m$—O(CH$_2$)$_n$—O(CH$_2$)$_o$—O(CH$_2$)$_p$—O(CH$_2$)$_q$—O(CH$_2$)$_r$—OCH$_2$—,

—O—(CH$_2$)$_m$—O(CH$_2$)$_n$—O(CH$_2$)$_o$—O(CH$_2$)$_p$—O(CH$_2$)$_q$—O(CH$_2$)$_r$—O—;

—N(R)—(CH$_2$)$_m$—O(CH$_2$)$_n$—O(CH$_2$)$_o$—O(CH$_2$)$_p$—O(CH$_2$)$_q$—O(CH$_2$)$_r$—O—;

—(CH$_2$)$_m$—O(CH$_2$)$_n$—O(CH$_2$)$_o$—O(CH$_2$)$_p$—O(CH$_2$)$_q$—O(CH$_2$)$_r$—O—;

—(CH$_2$)$_m$—O(CH$_2$)$_n$—O(CH$_2$)$_o$—O(CH$_2$)$_p$—O(CH$_2$)$_q$—O(CH$_2$)$_r$—OCH$_2$—;

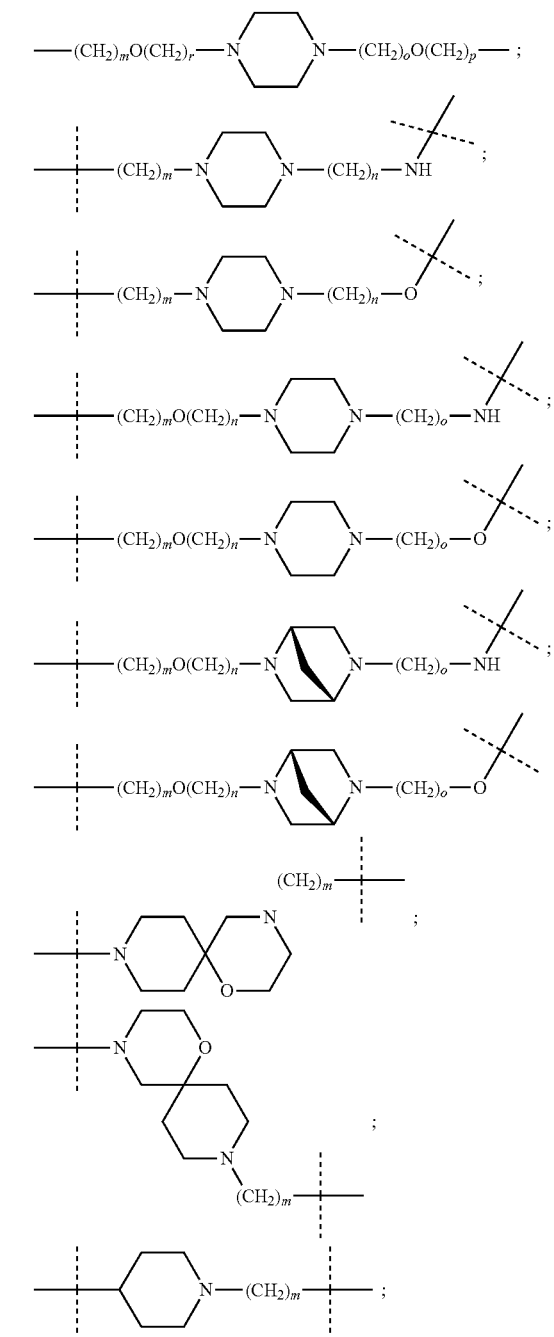

1451
-continued
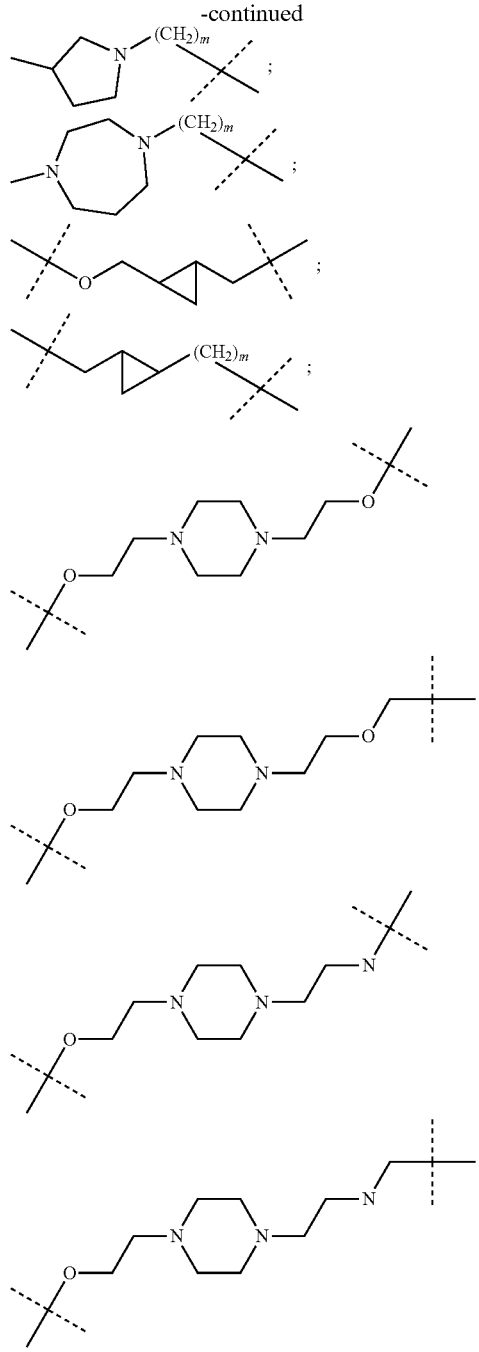
1452
-continued
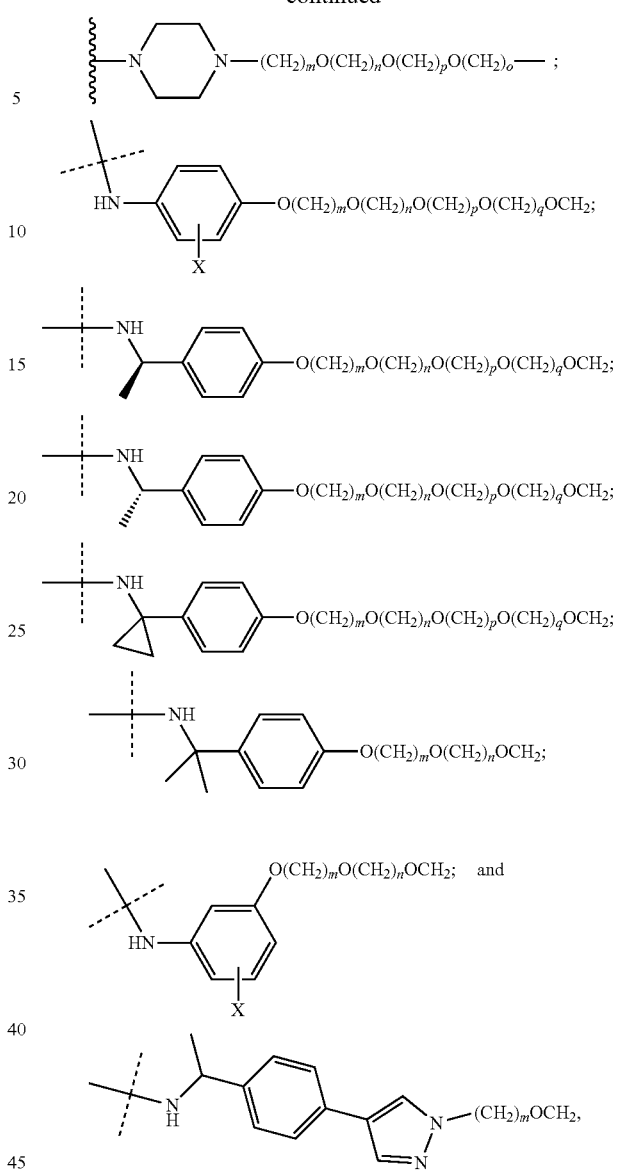
wherein m, n, o, p, q, and r, are independently 0, 1, 2, 3, 4, 5, 6, with the proviso that when the number is zero, there is no N—O or O—O bond, R is selected from the group H, methyl and ethyl, and X is selected from the group H and F;
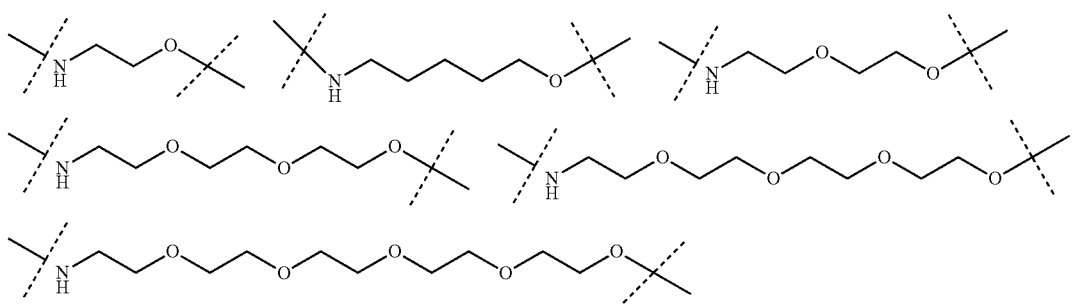

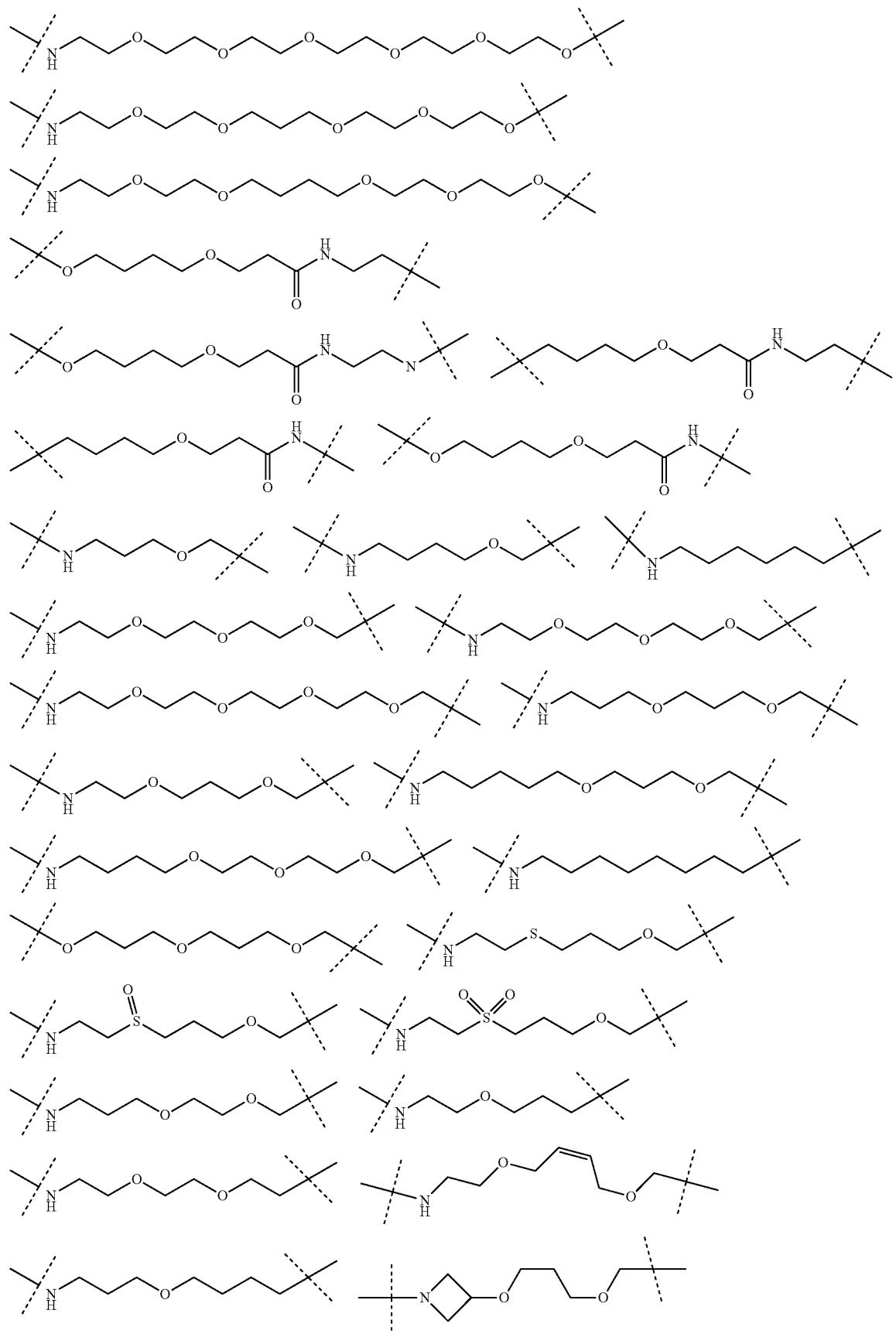

1455 1456
-continued
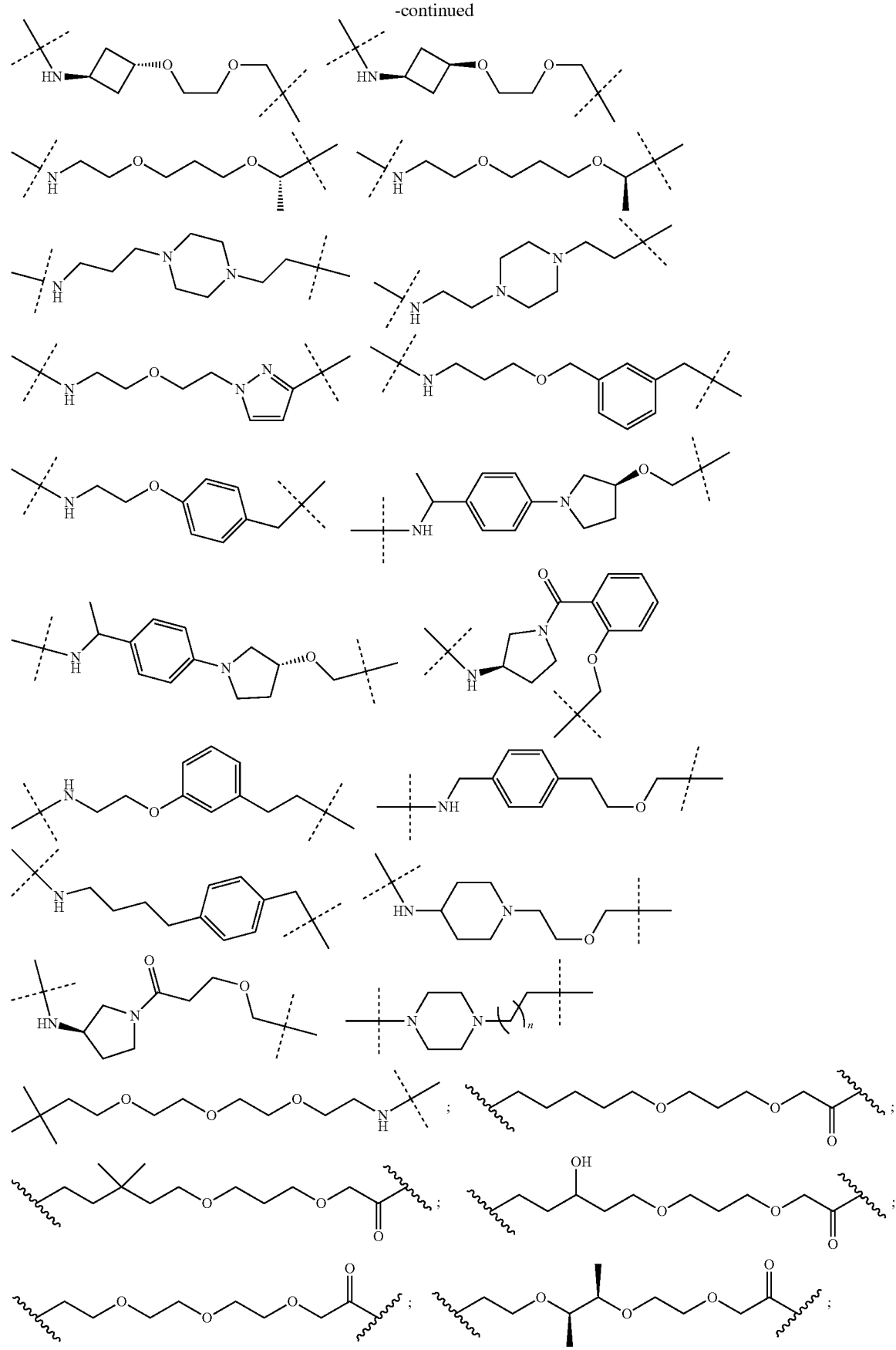

1457 1458
-continued
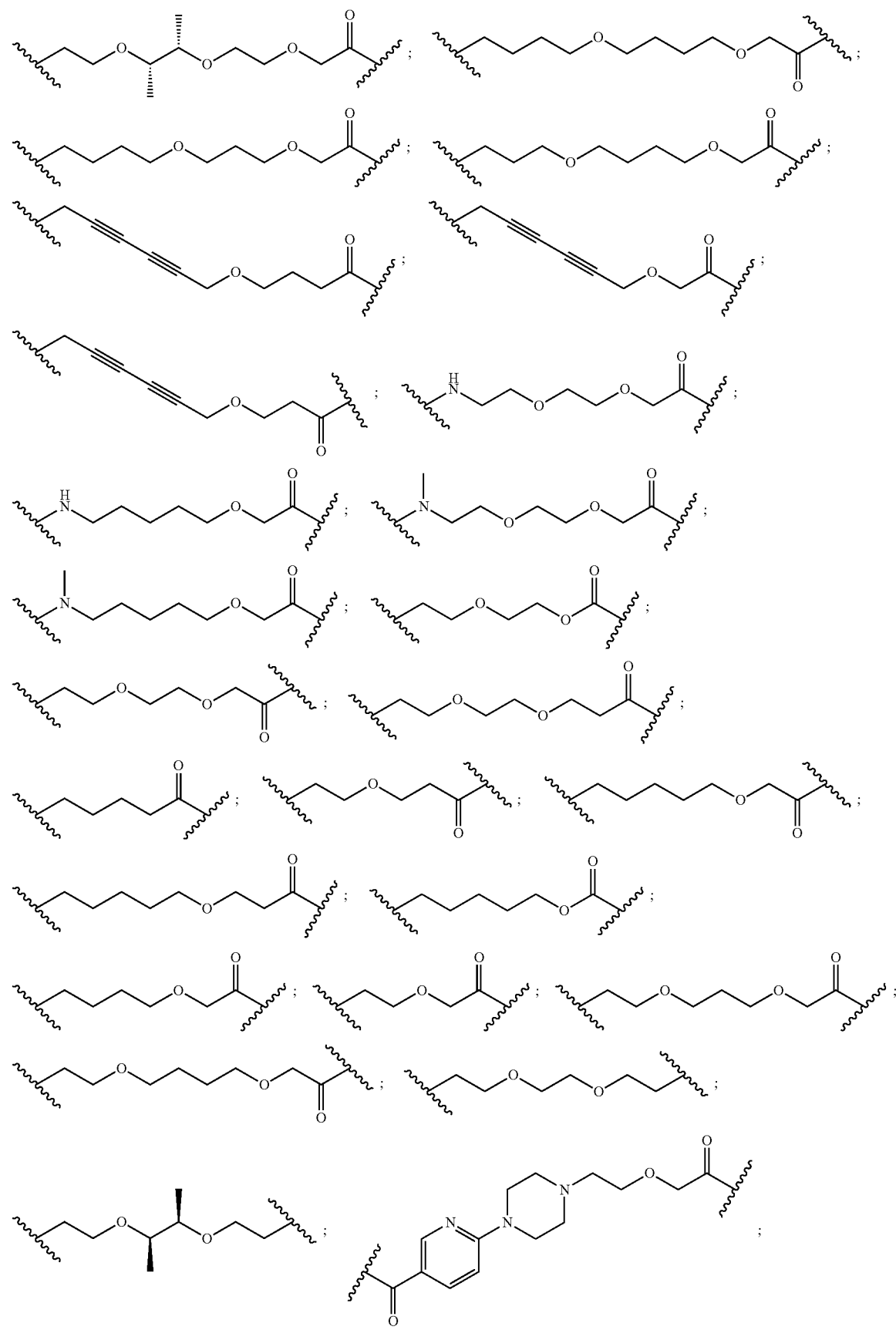

1459
-continued
1460
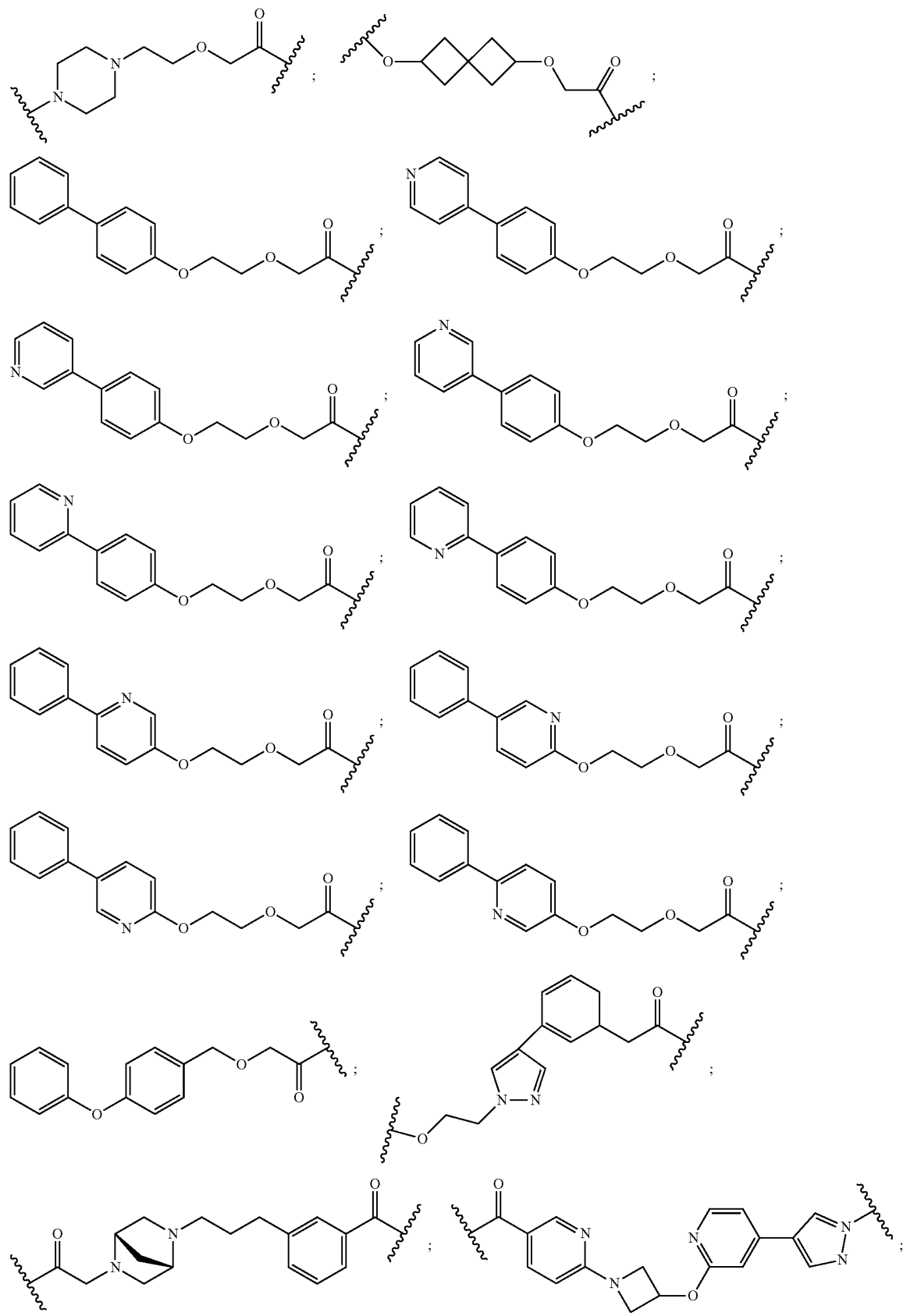

-continued
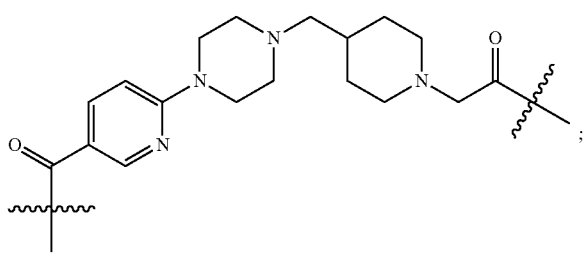
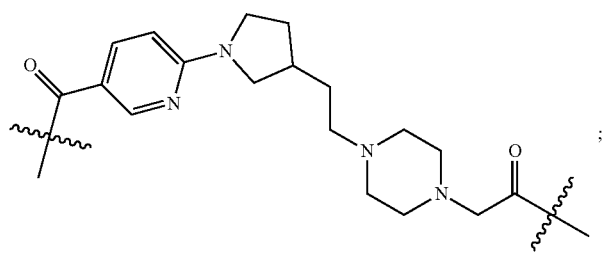
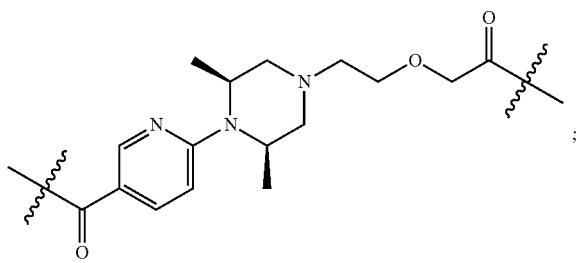
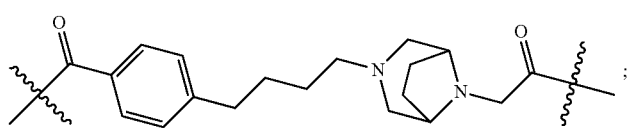
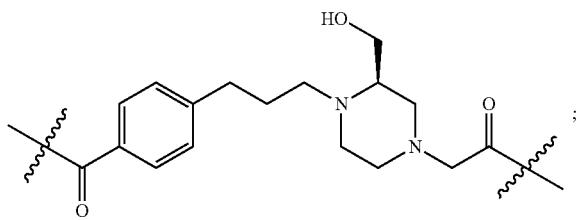
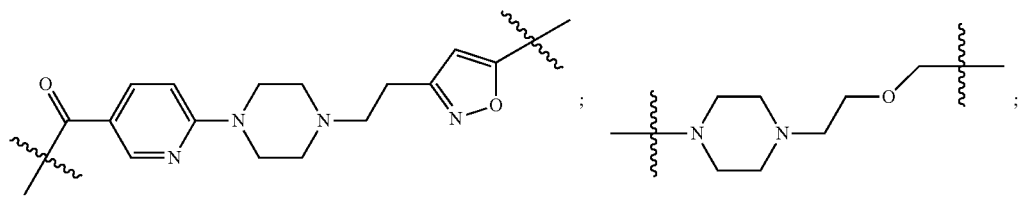
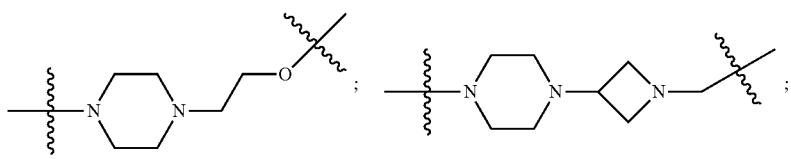
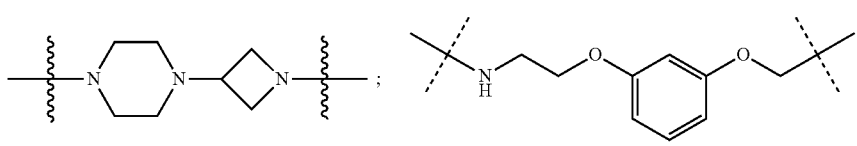

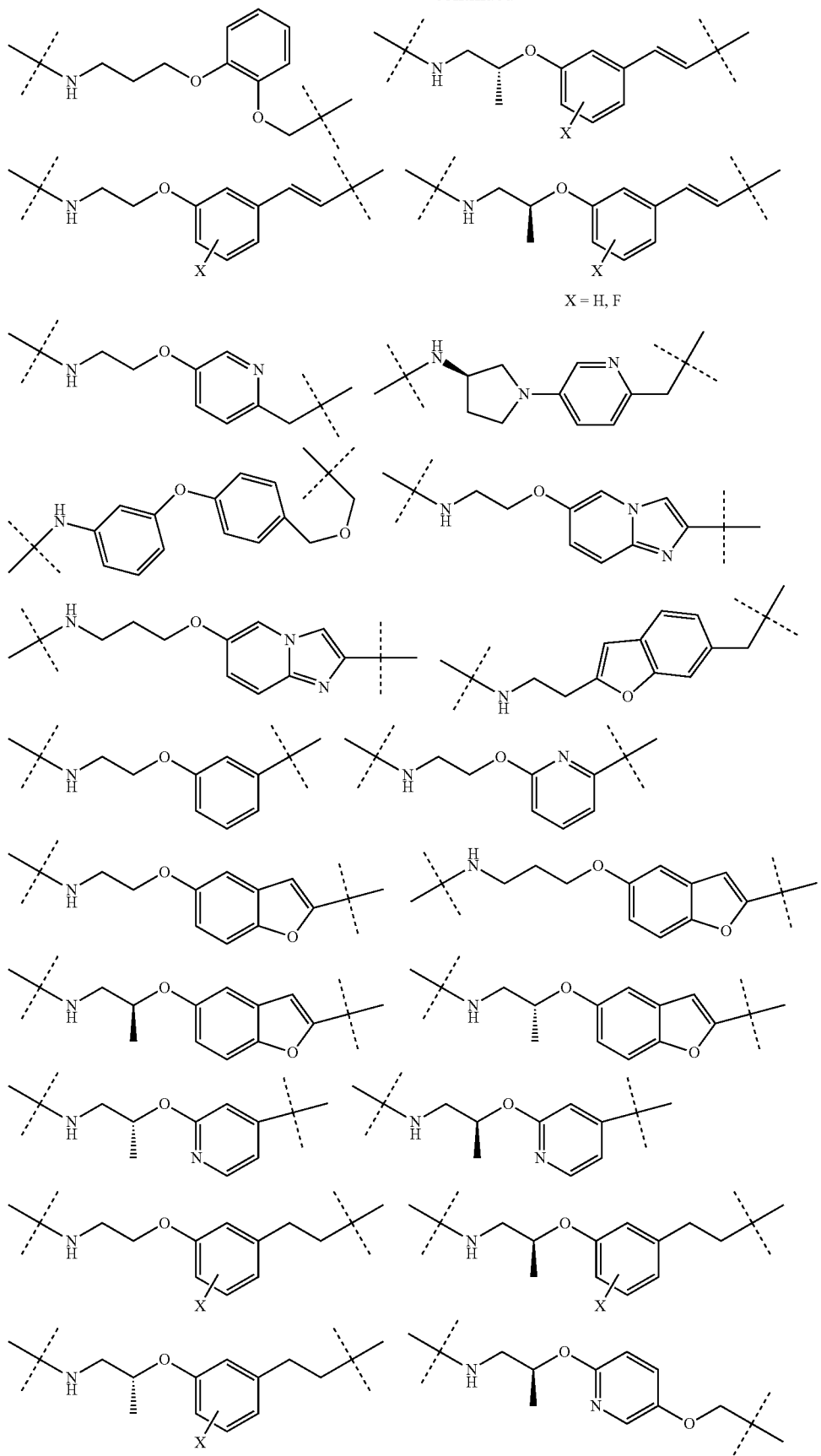

1465
-continued
1466
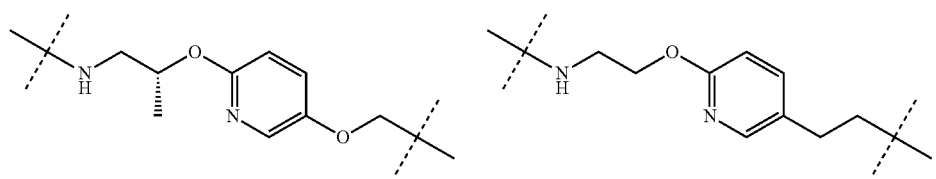
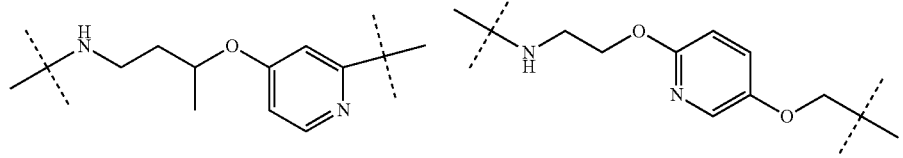
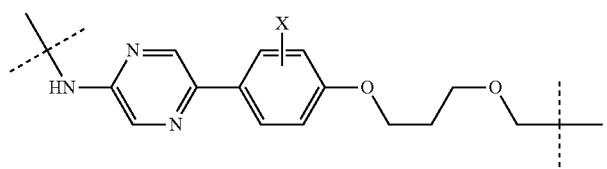
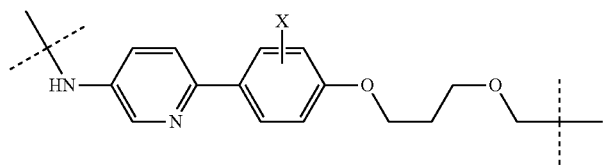
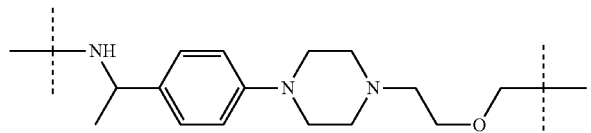
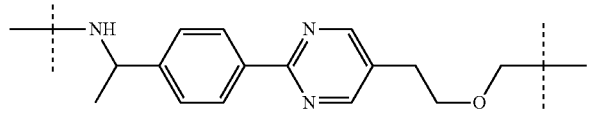
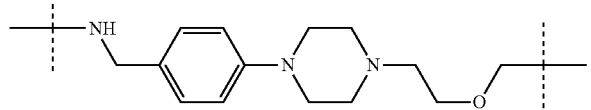
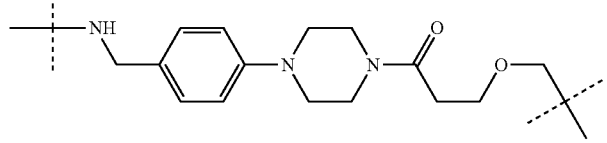
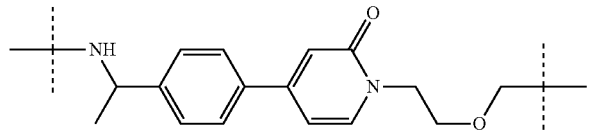
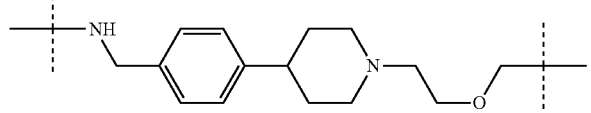
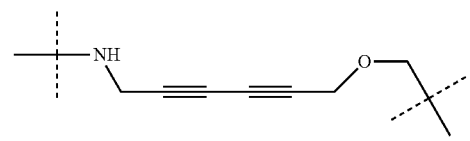
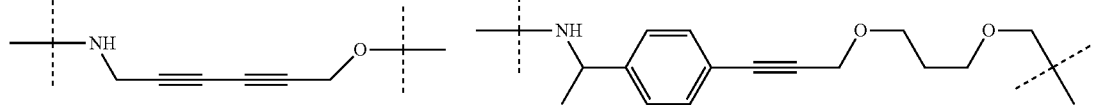

1467 1468
-continued
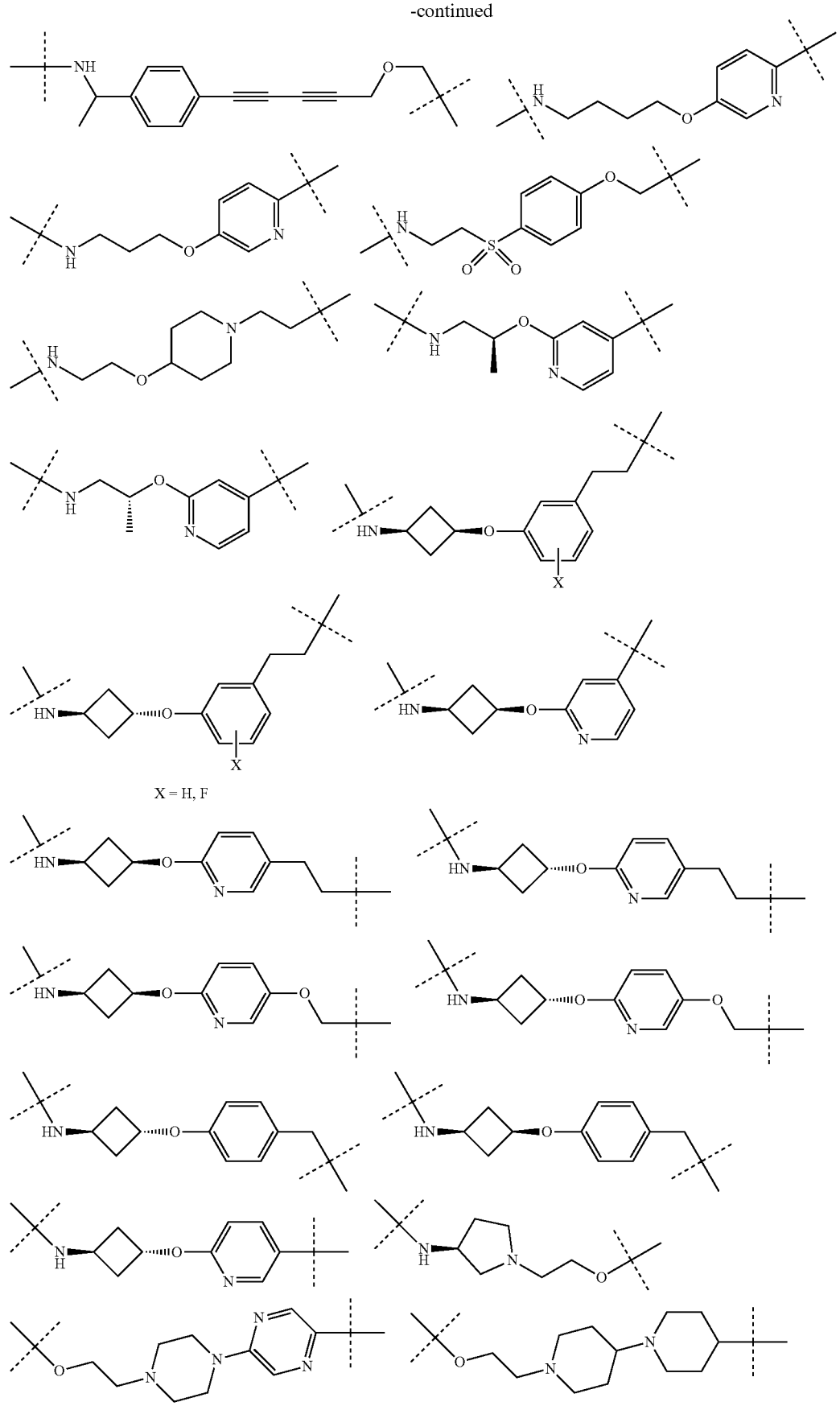
X = H, F 1469 1470
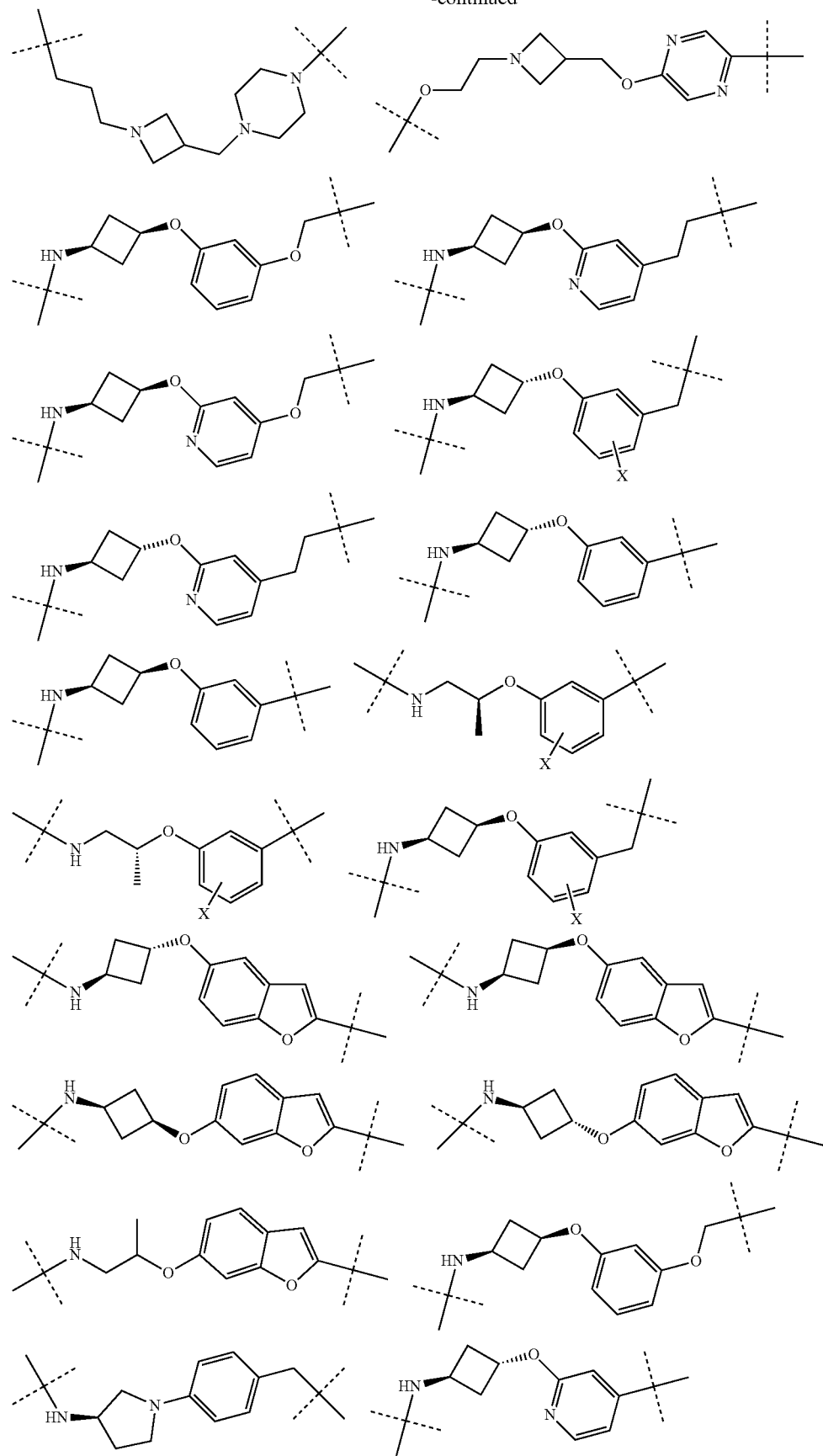

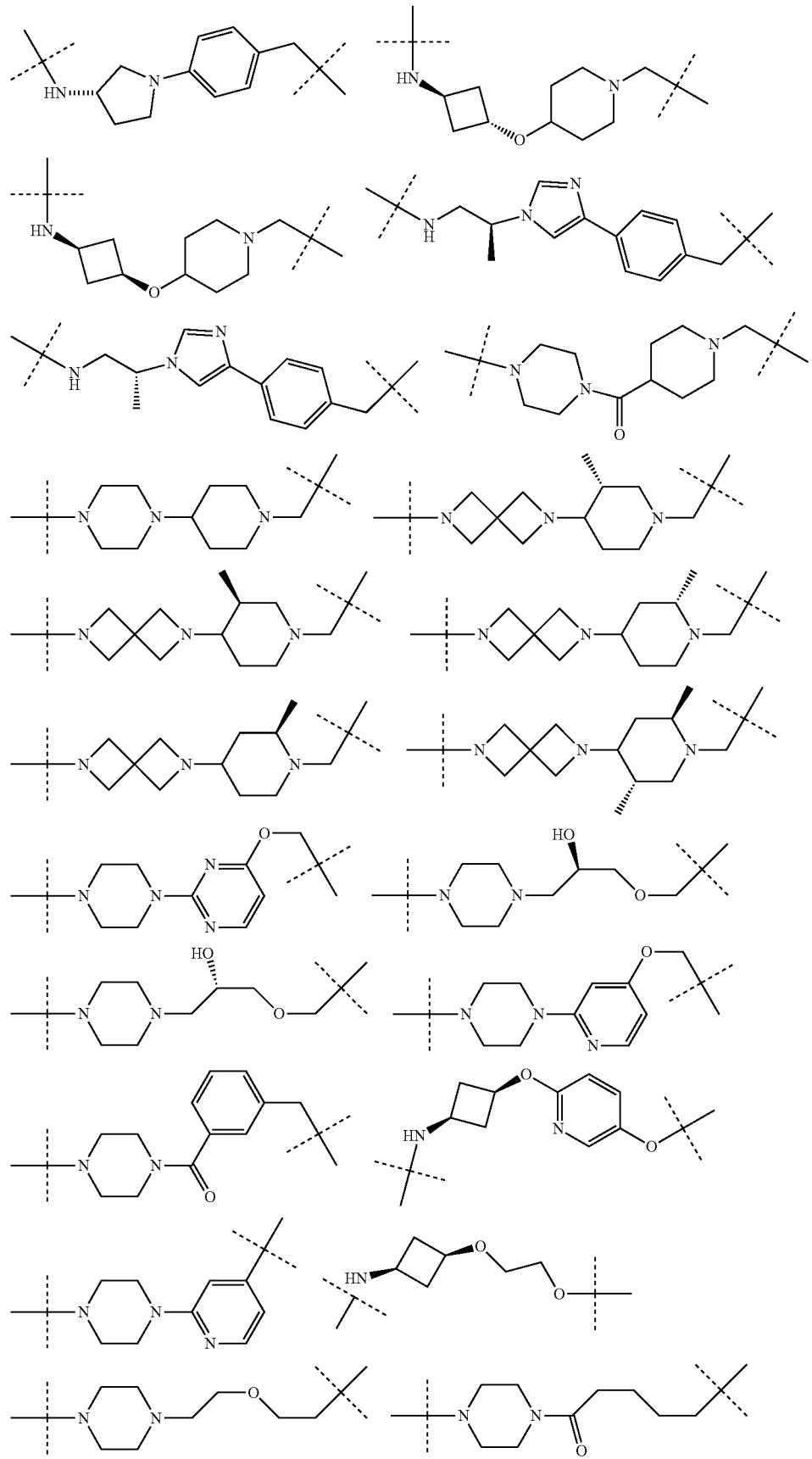

-continued
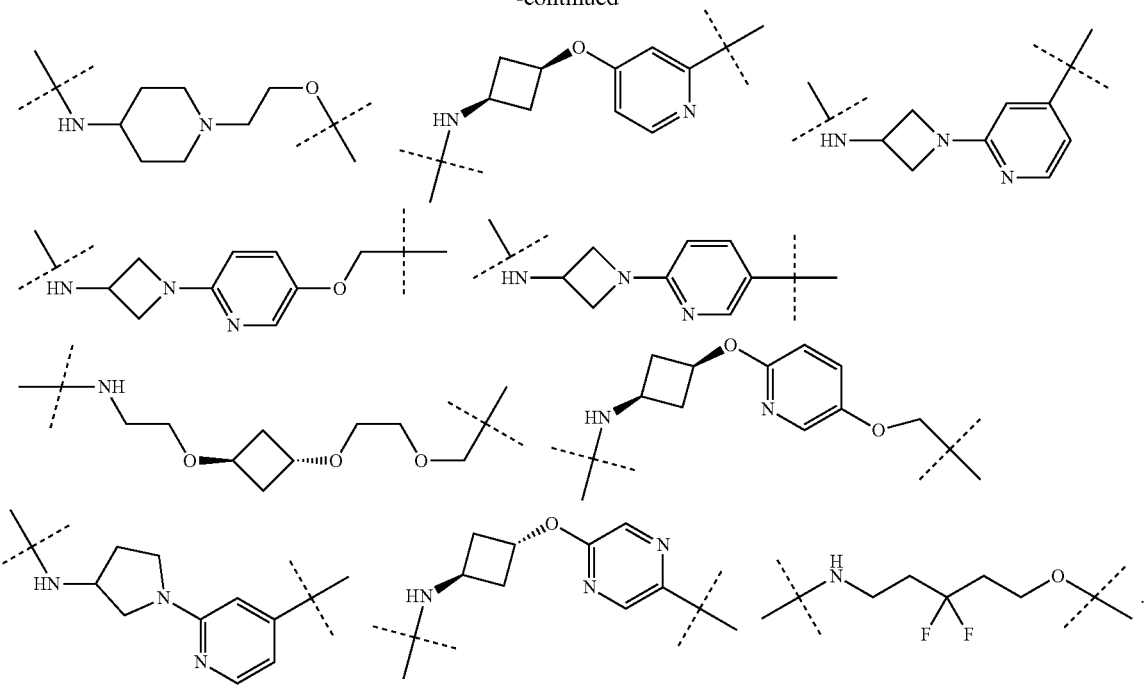
11. The bifunctional compound according to claim 1, wherein the linker (L) is selected from the group consisting of:
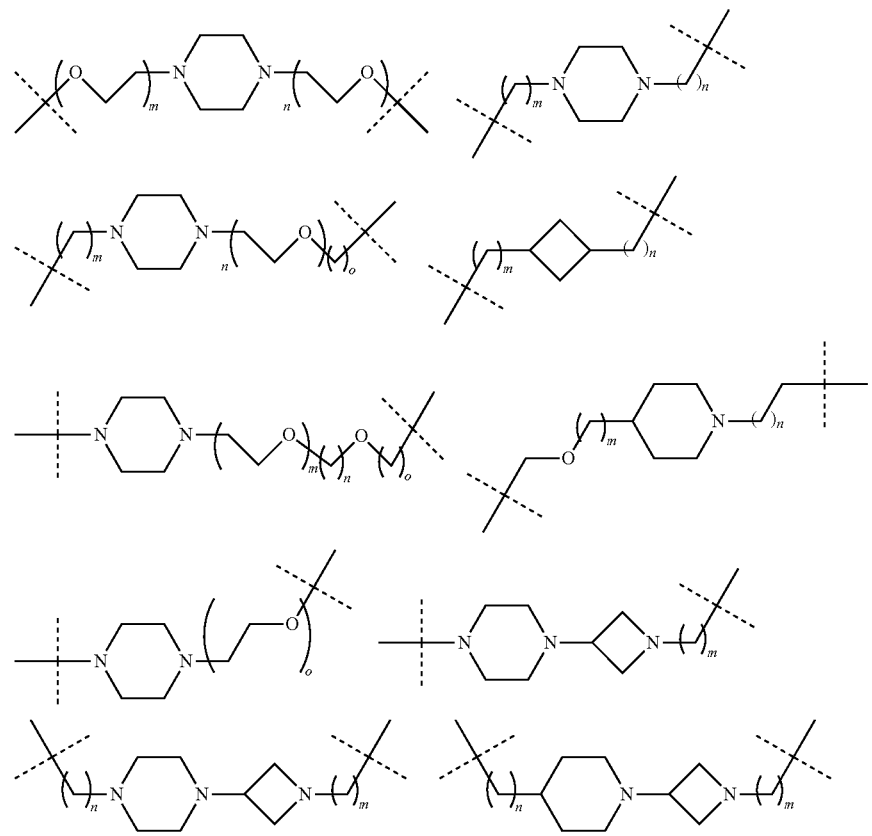

-continued
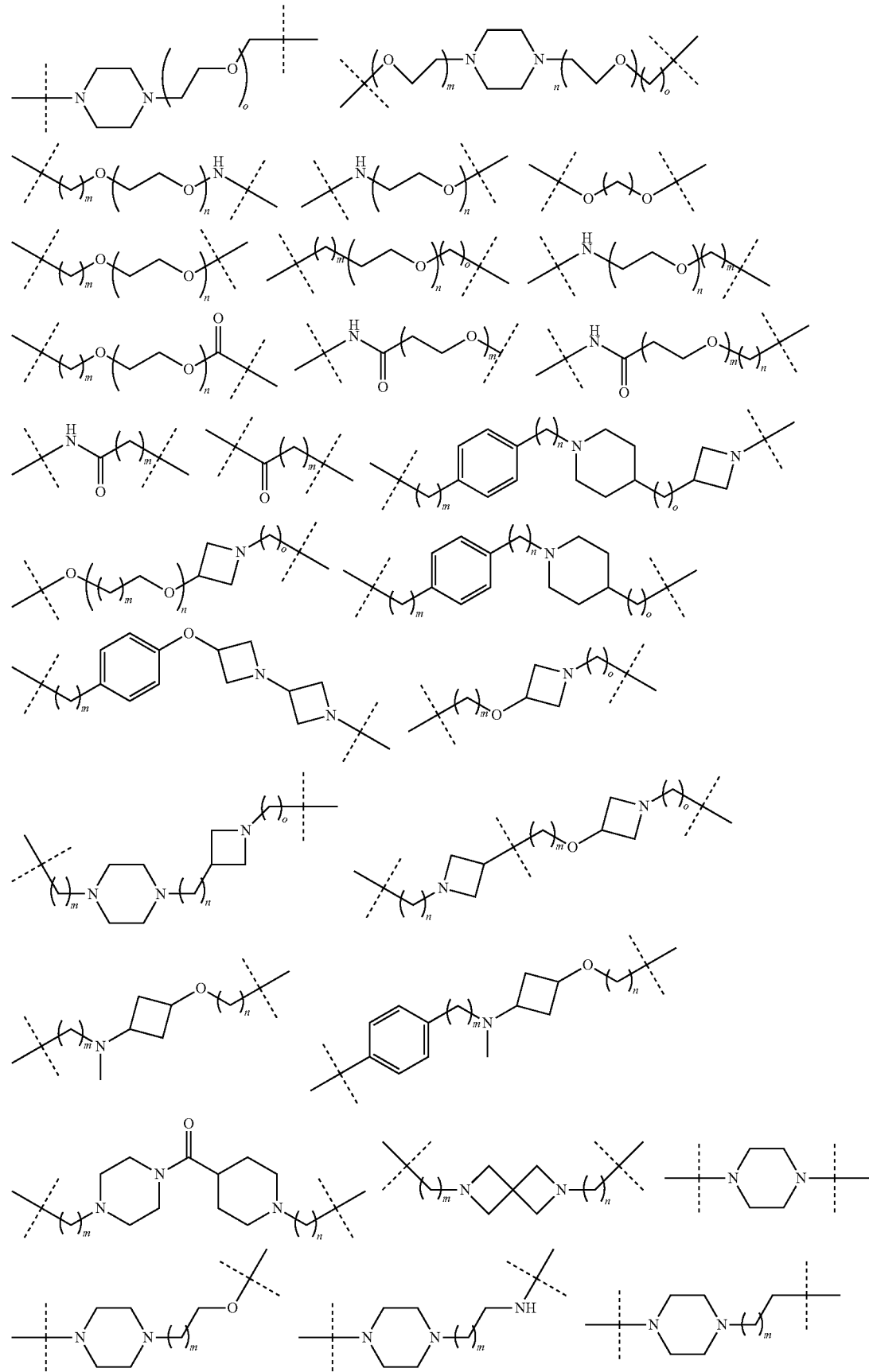

-continued
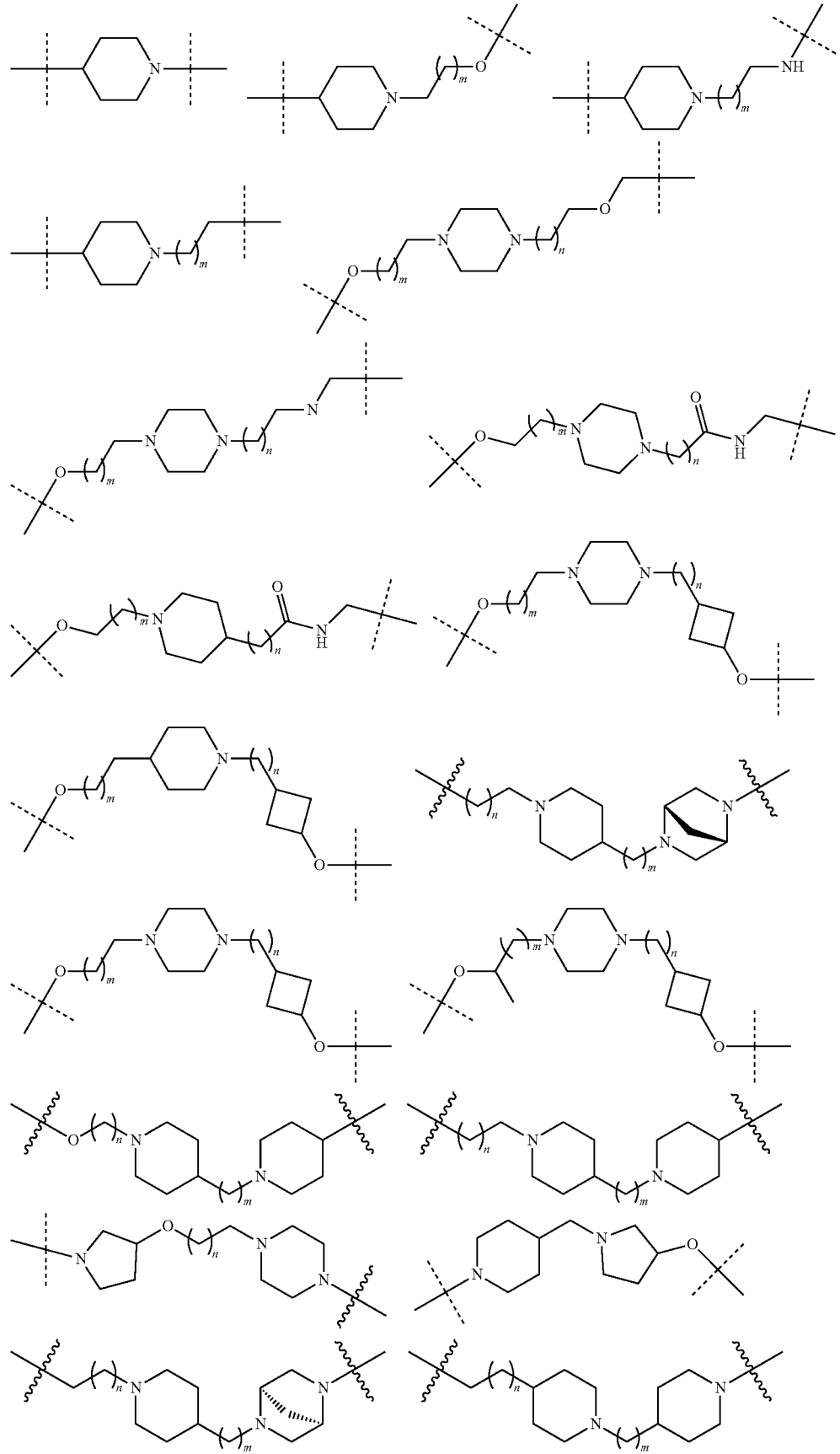

-continued
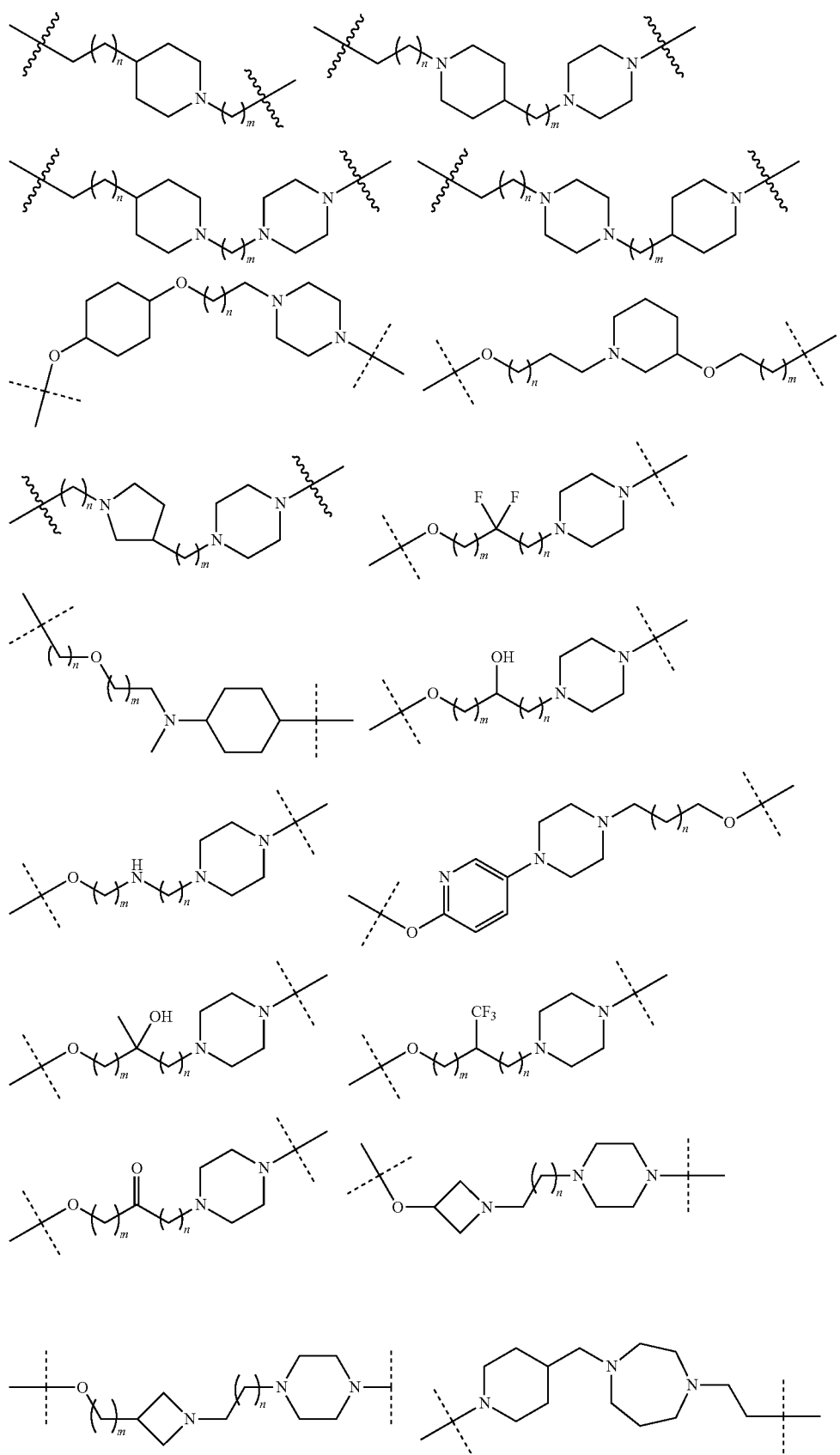

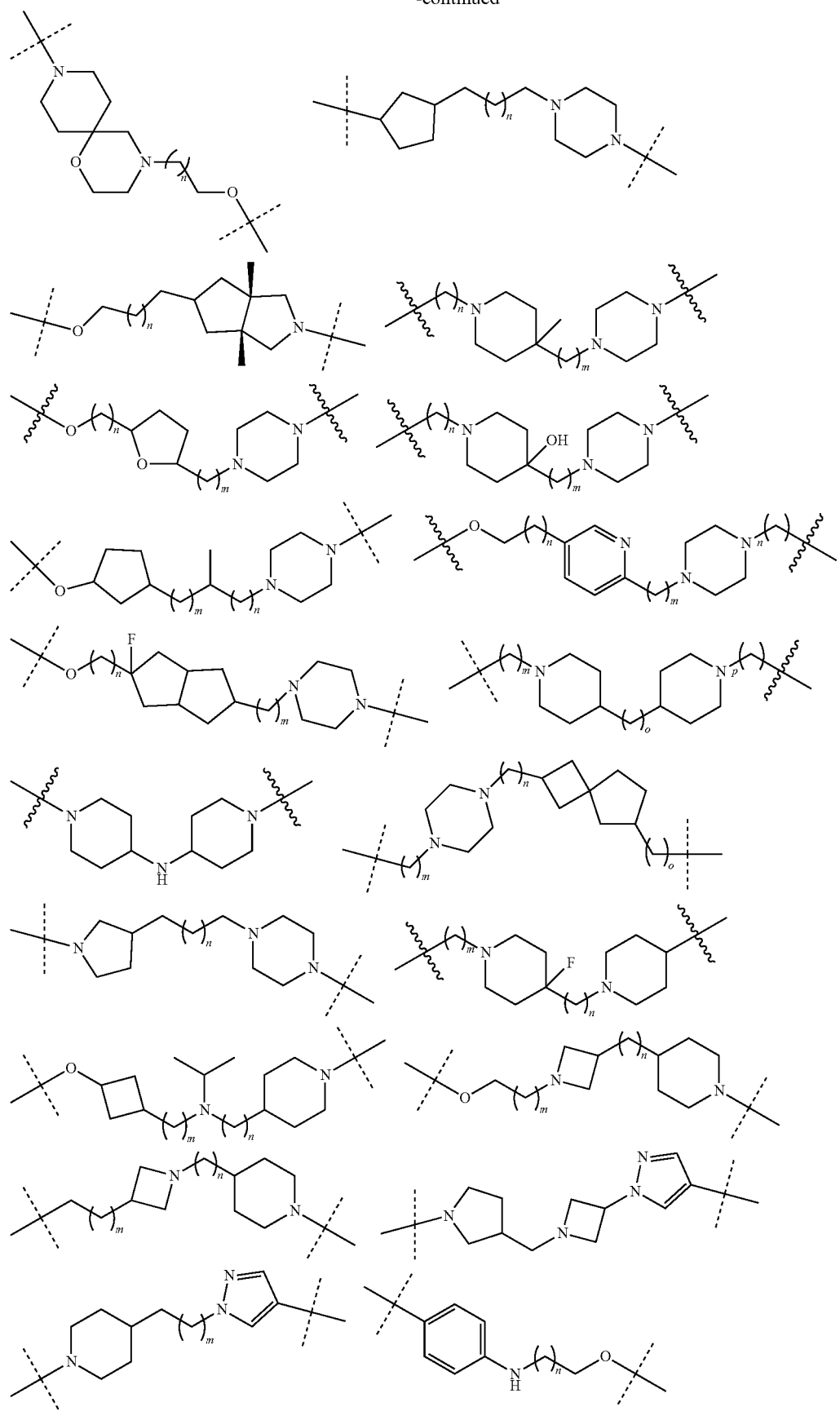

-continued
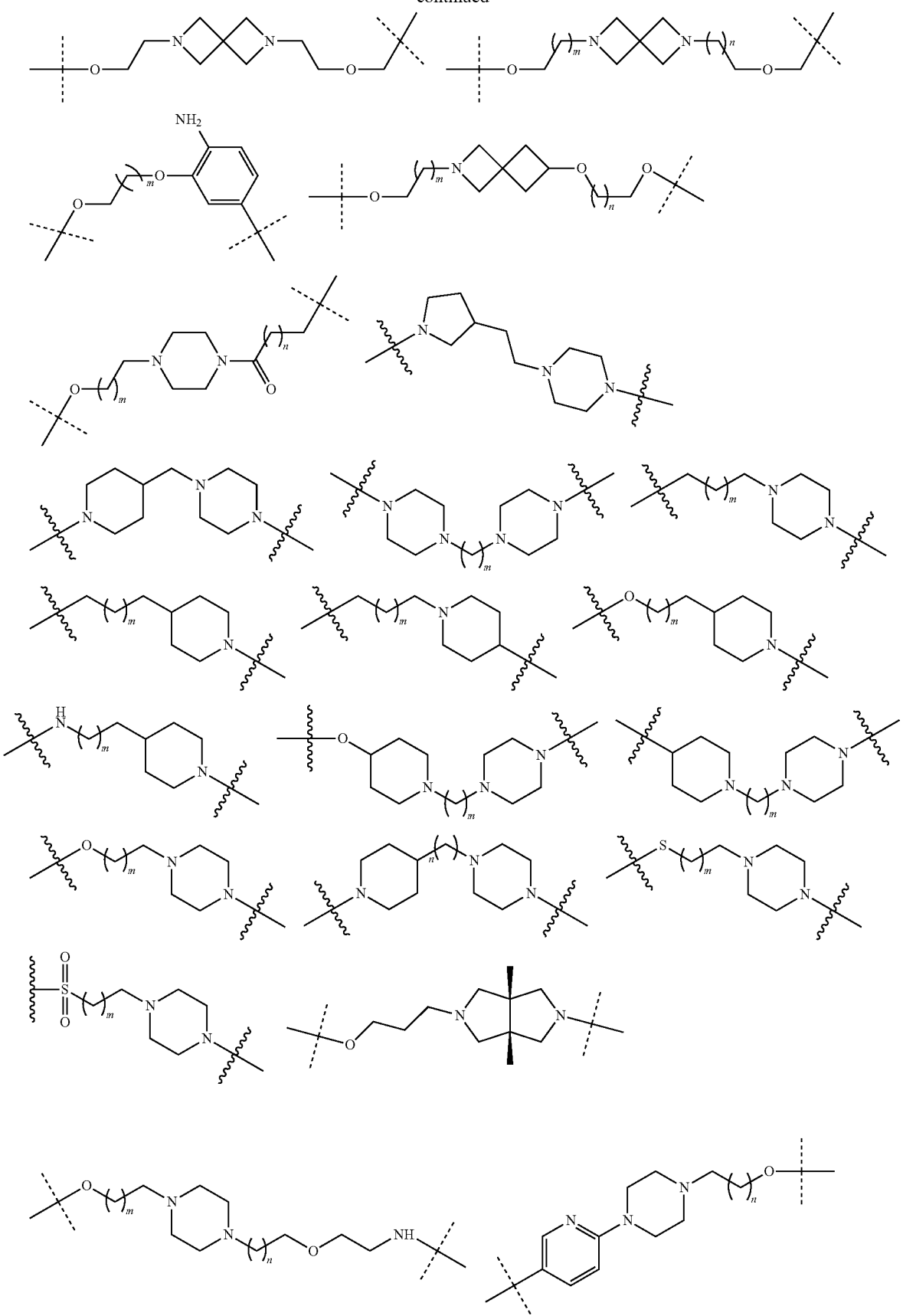

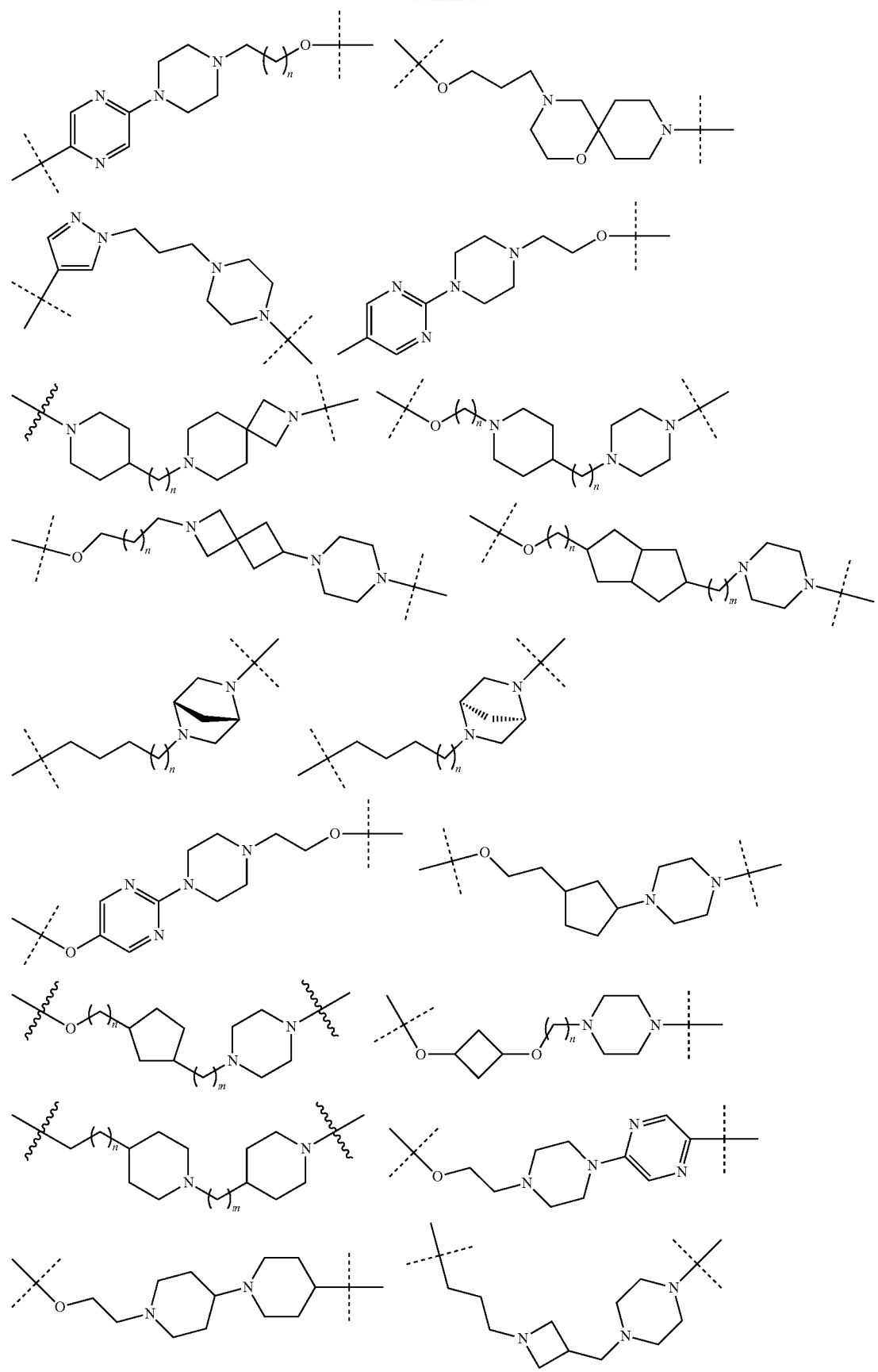

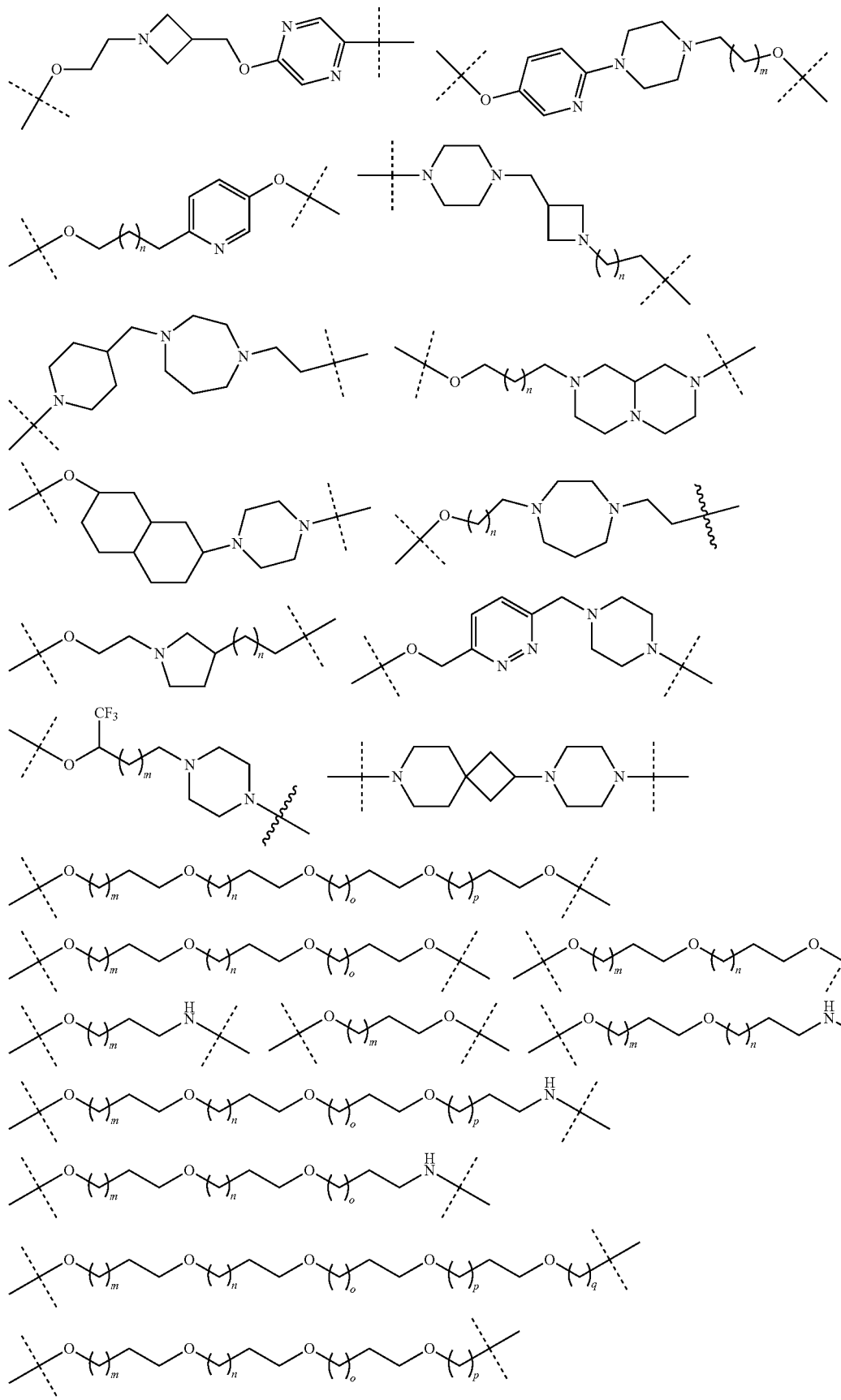

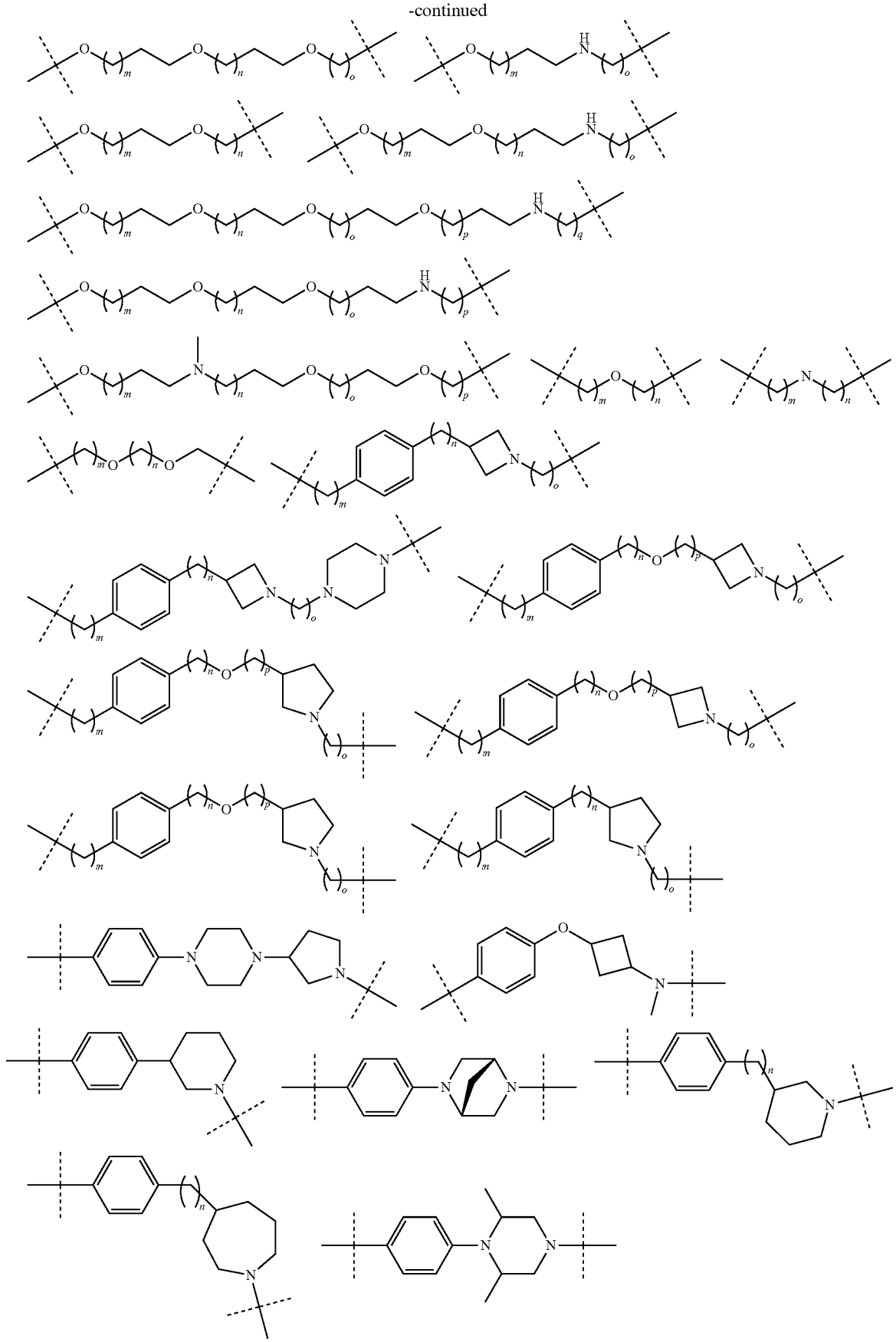

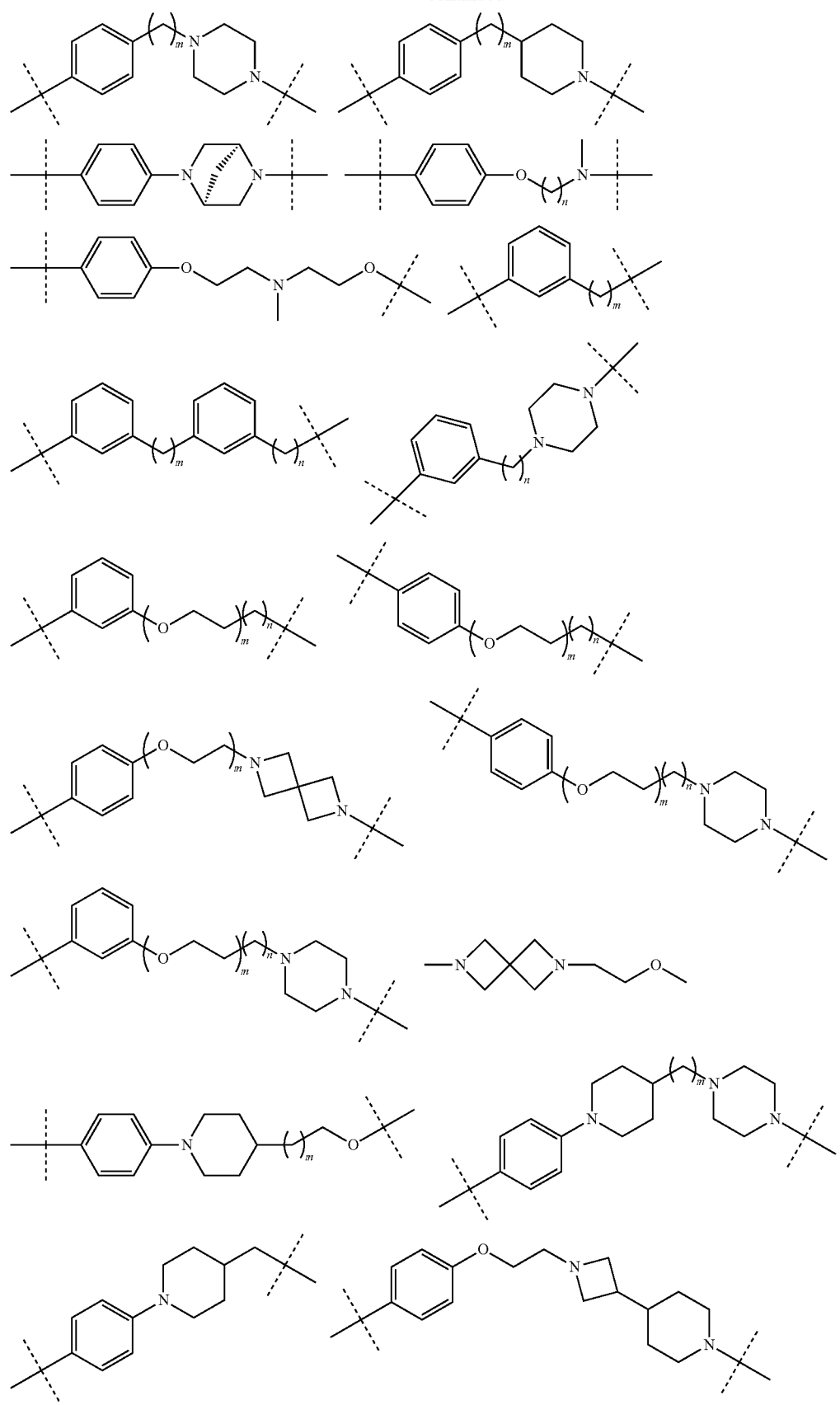

-continued
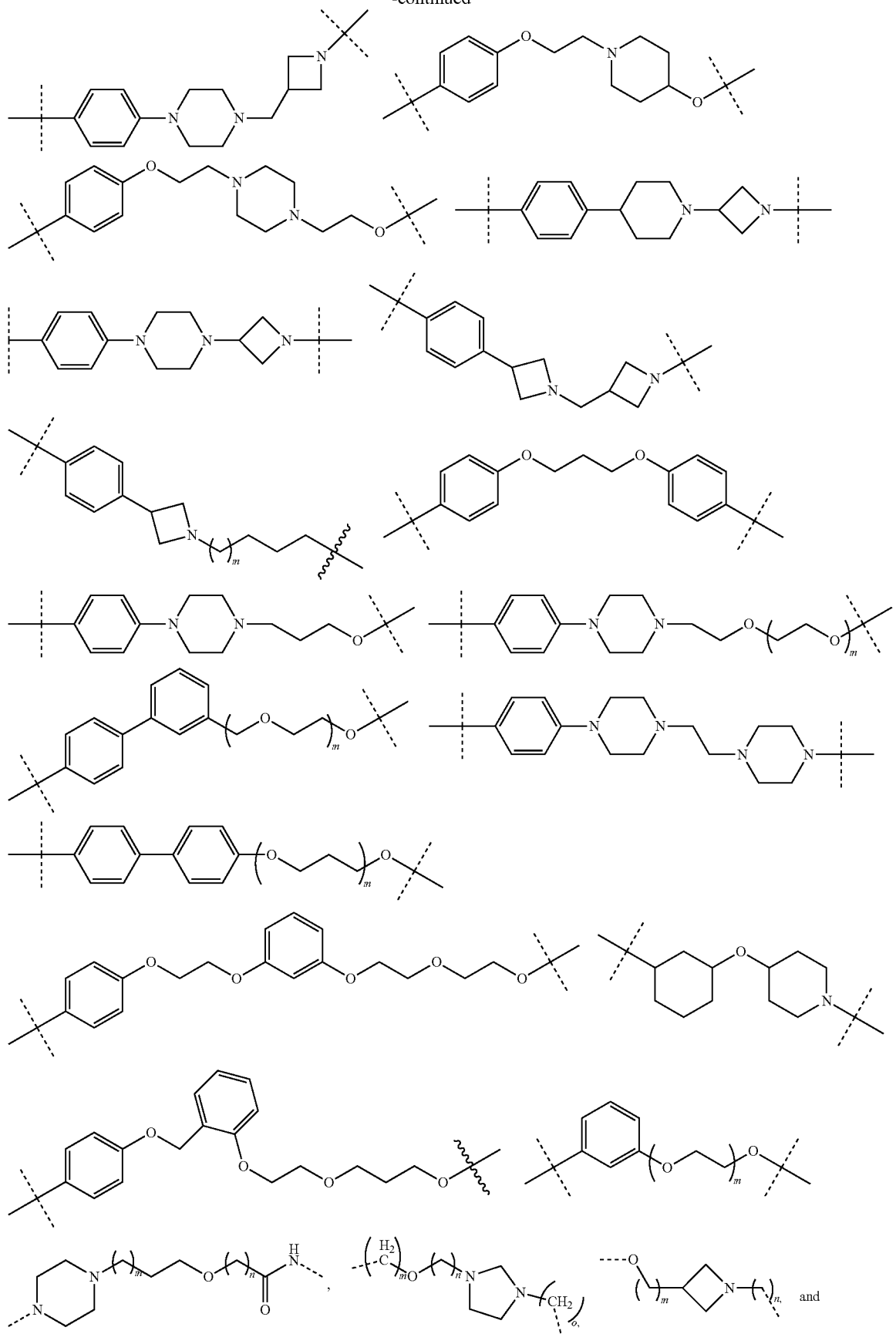

1495                                              1496
-continued
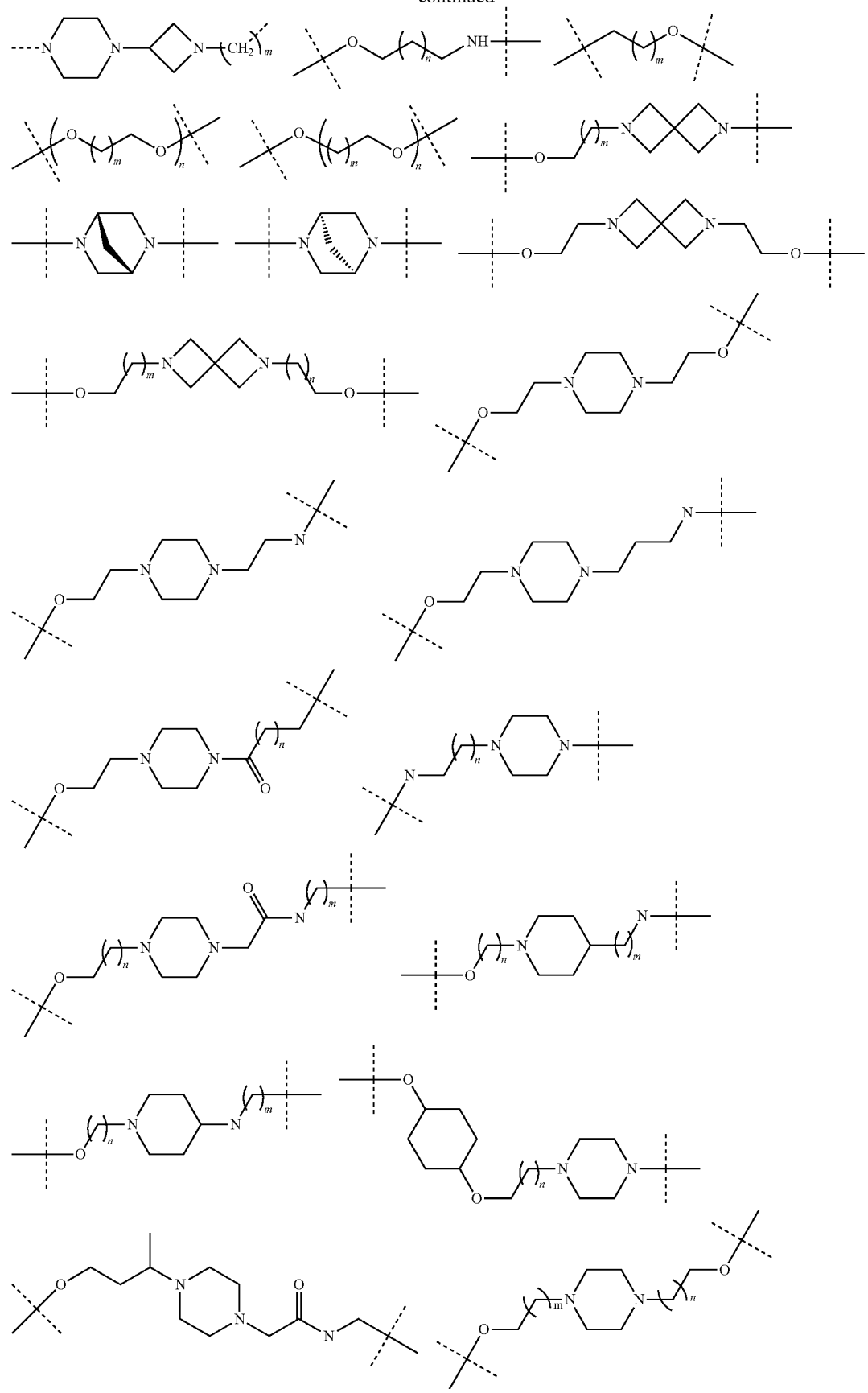

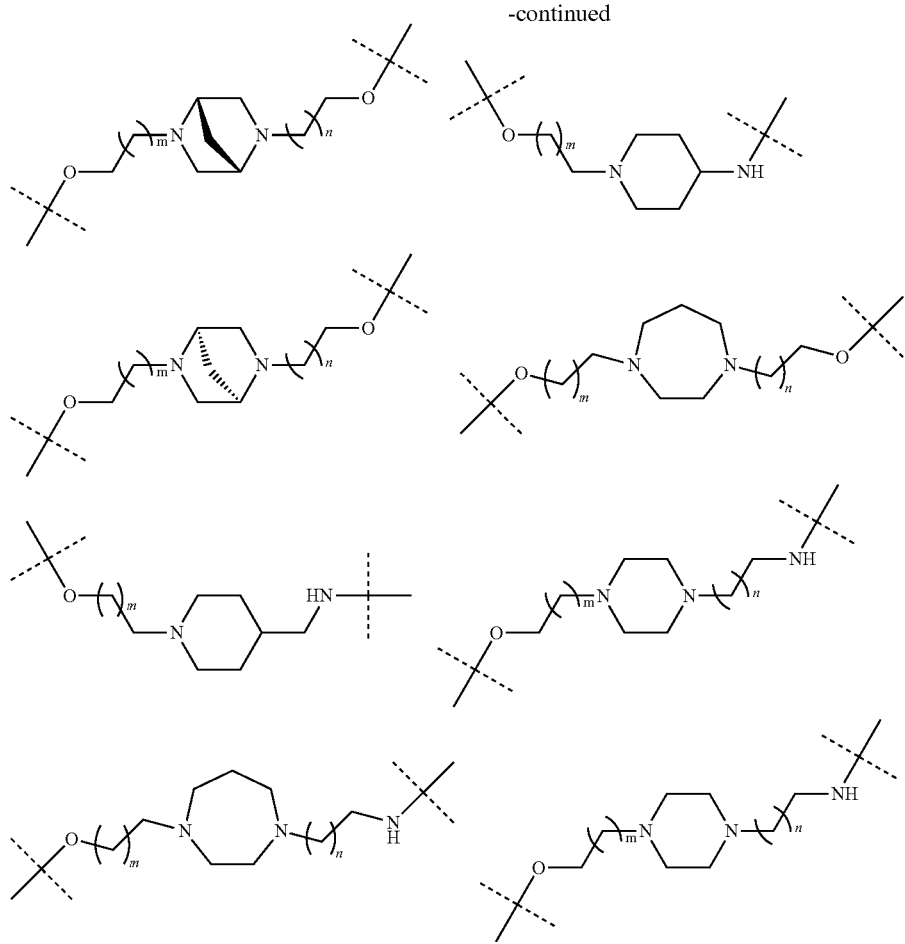
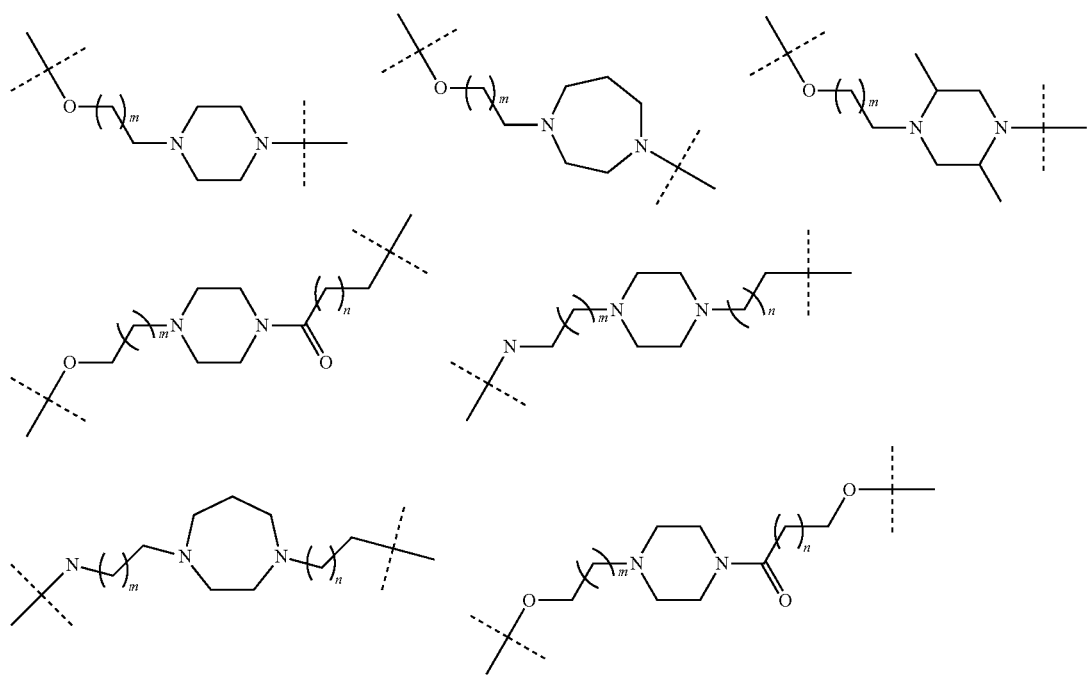

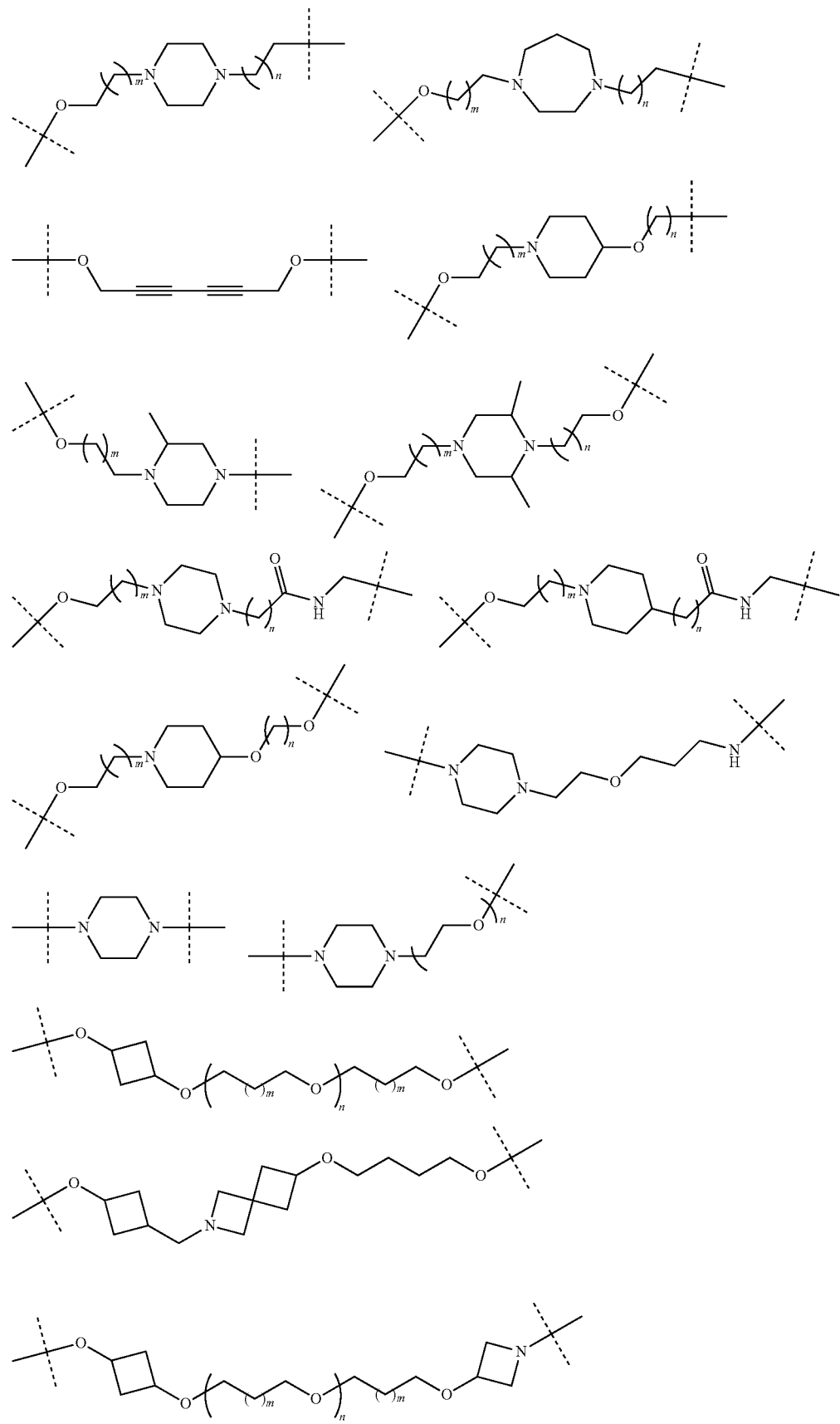

-continued
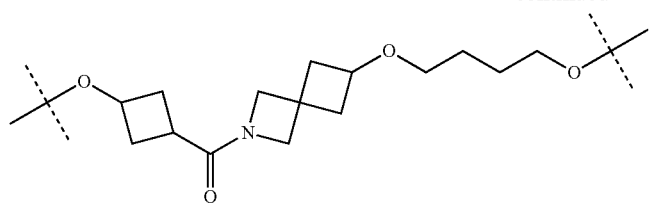
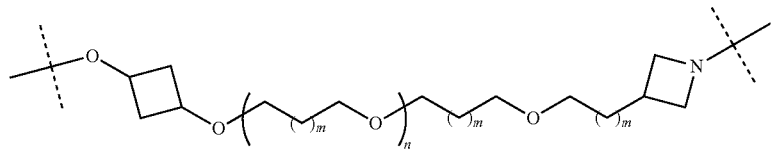
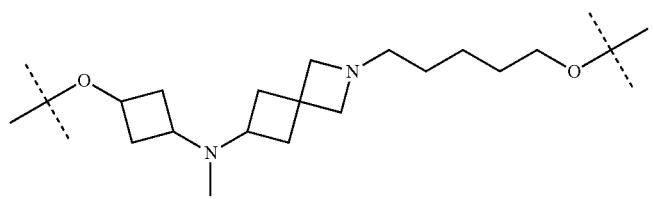
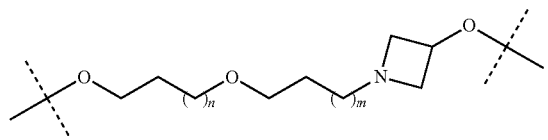
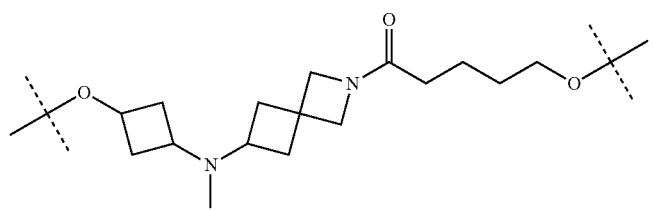
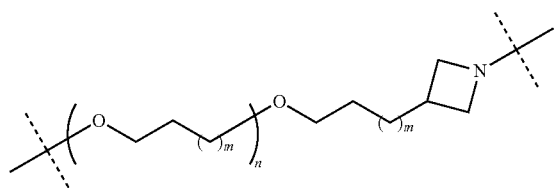
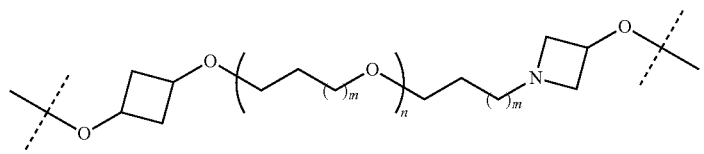
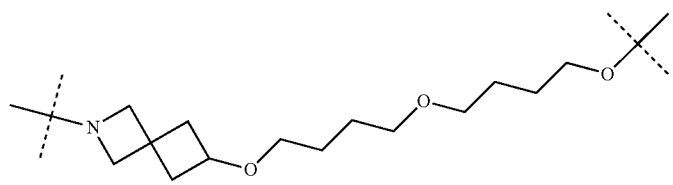
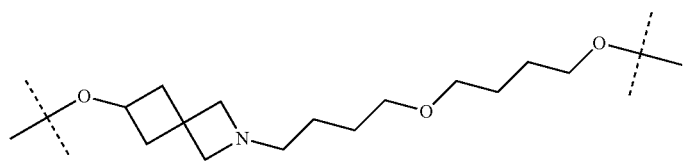

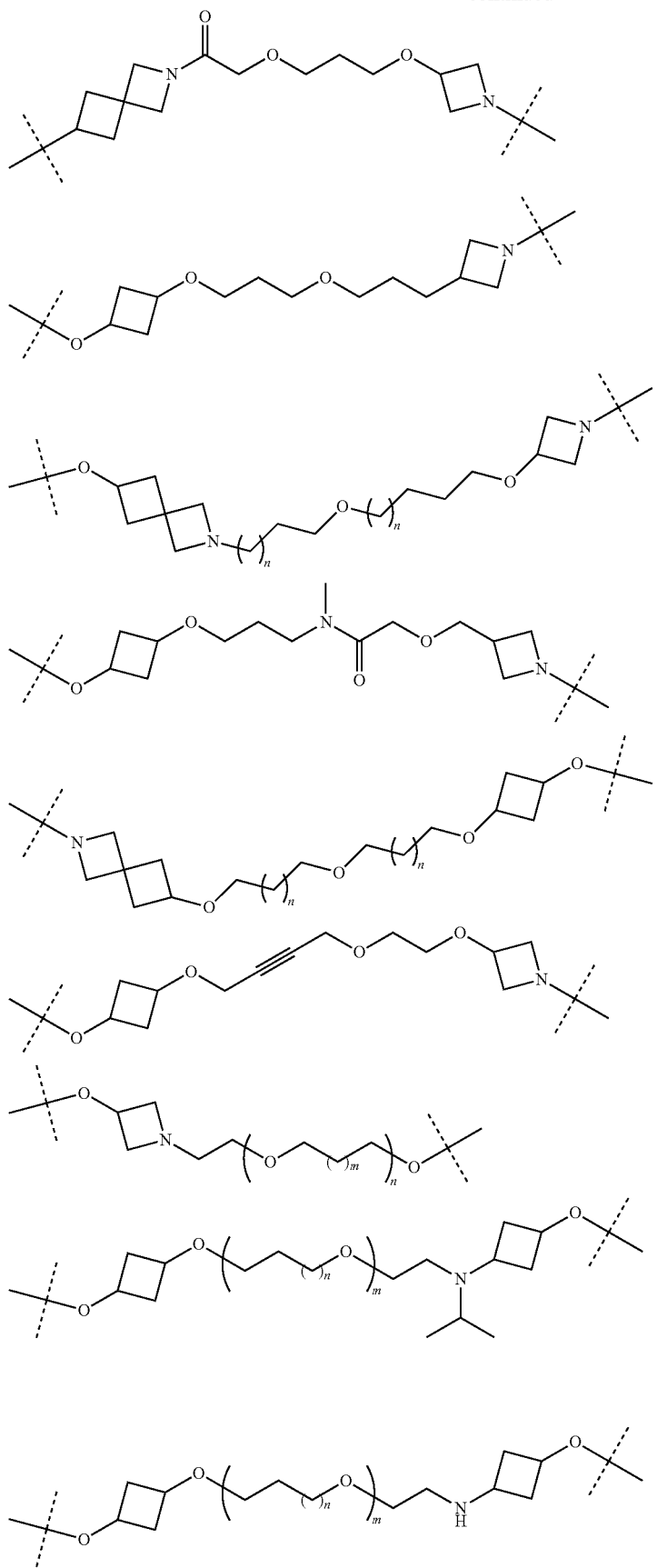

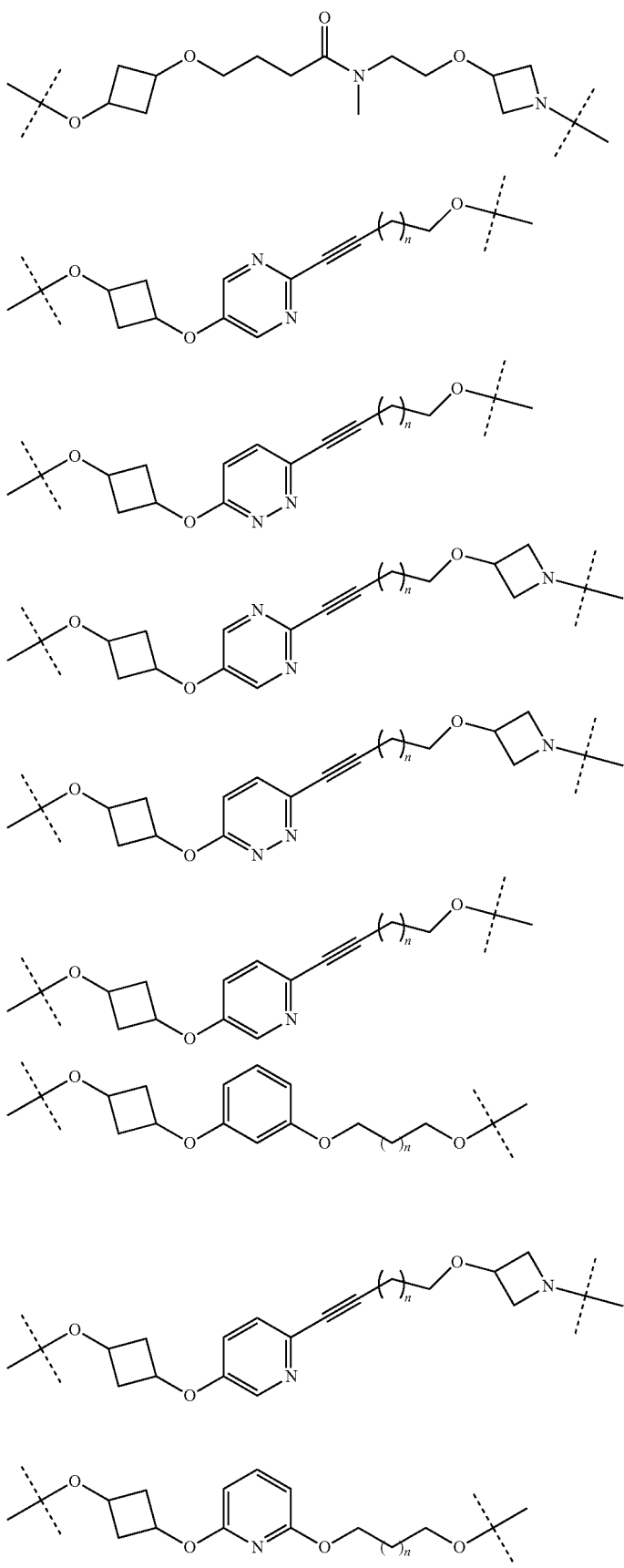

-continued
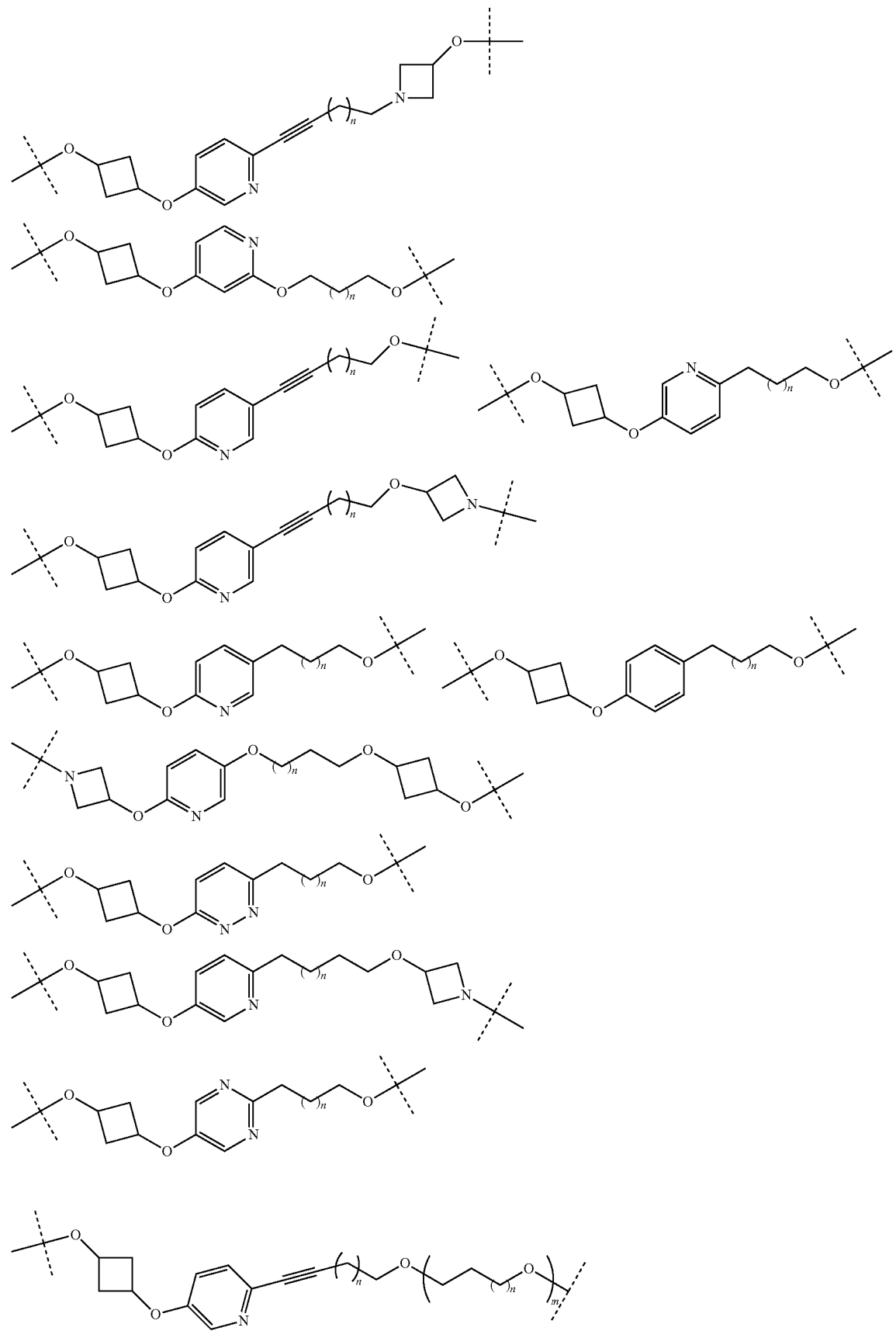

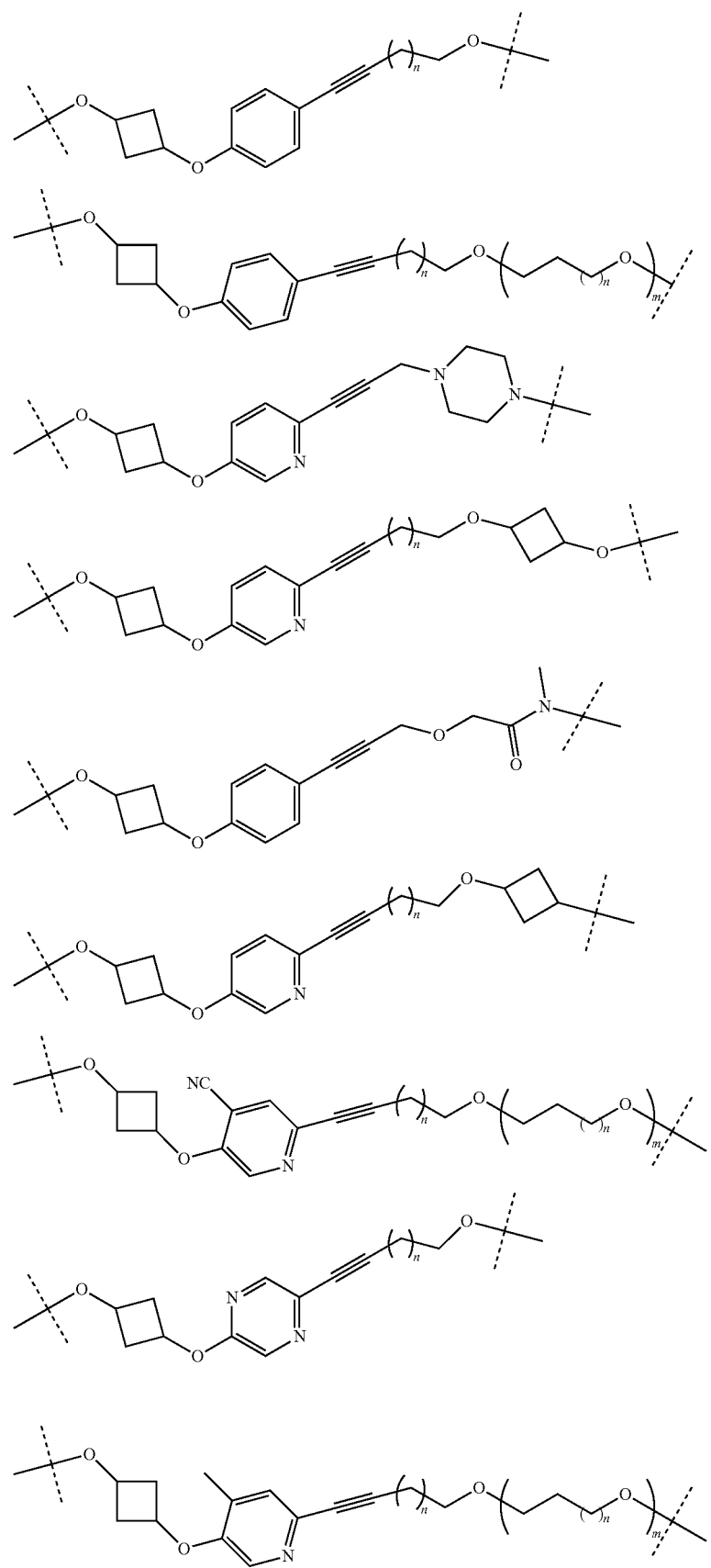

-continued
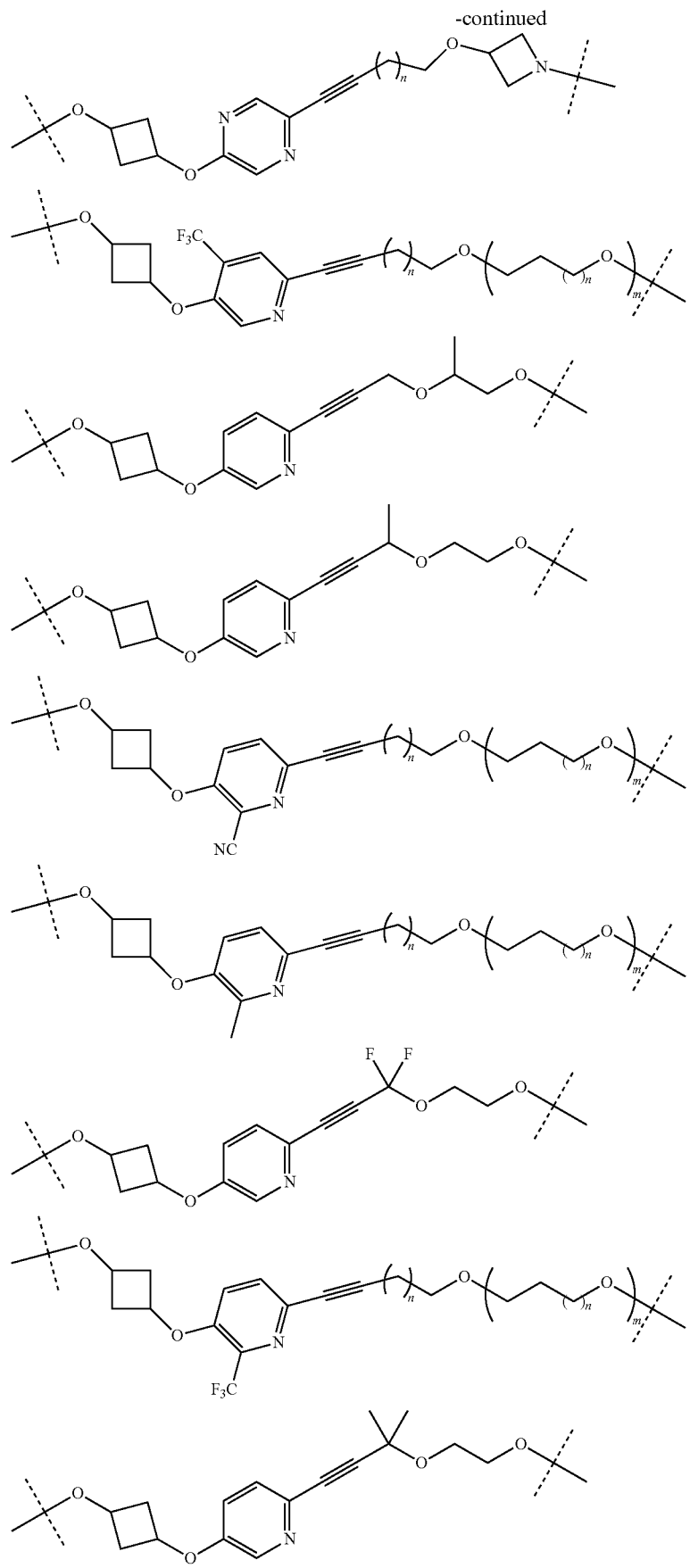

-continued
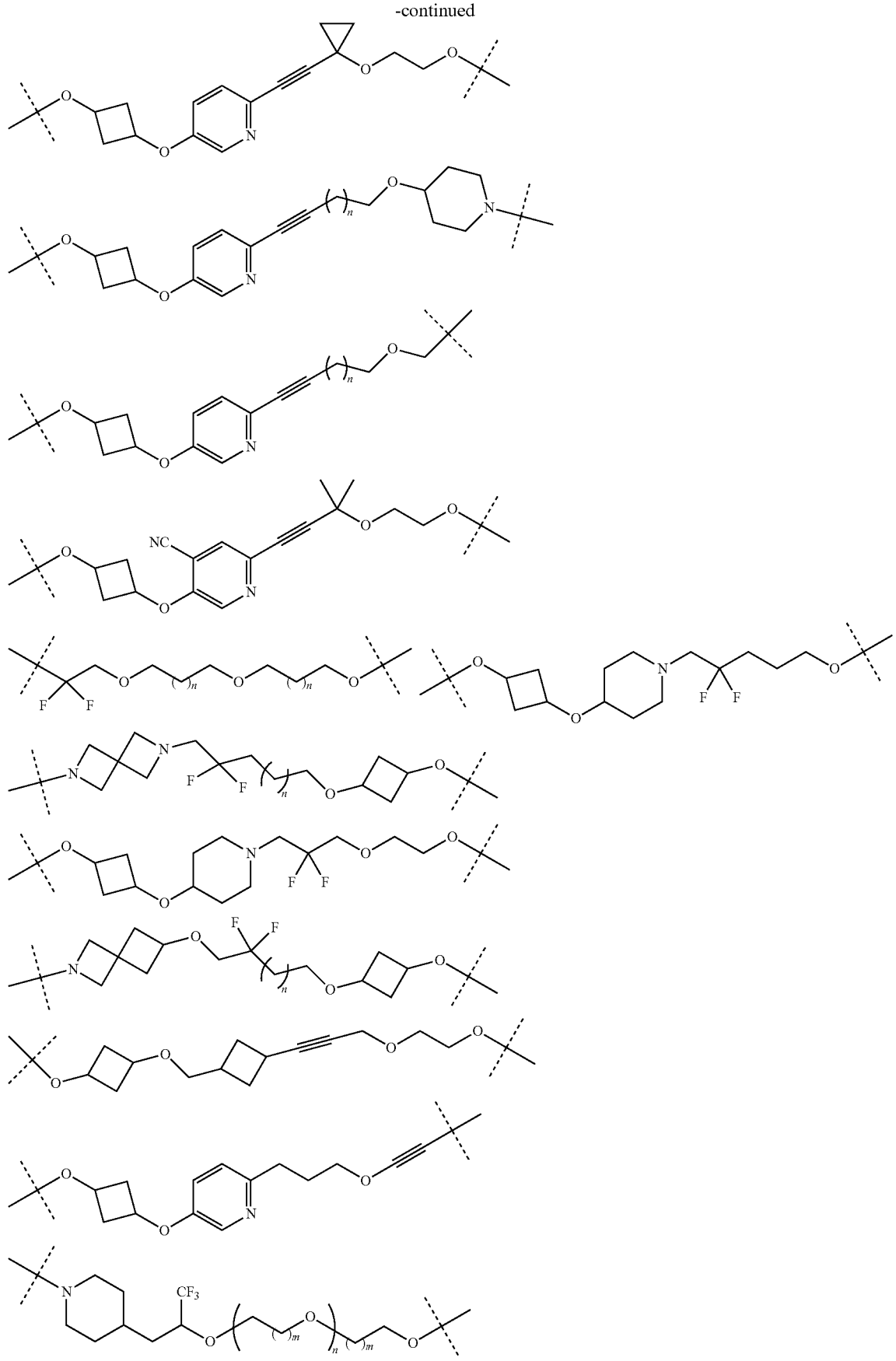

1515 1516
-continued
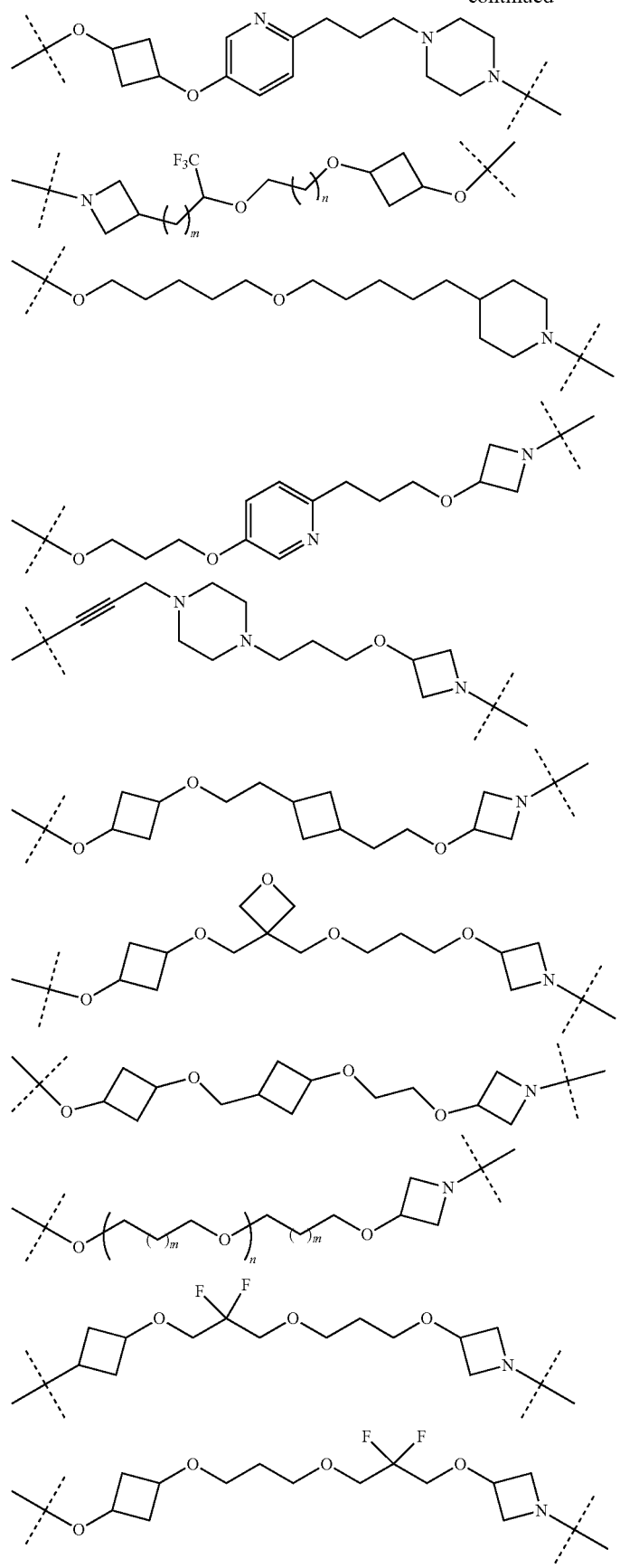

1517 1518
-continued
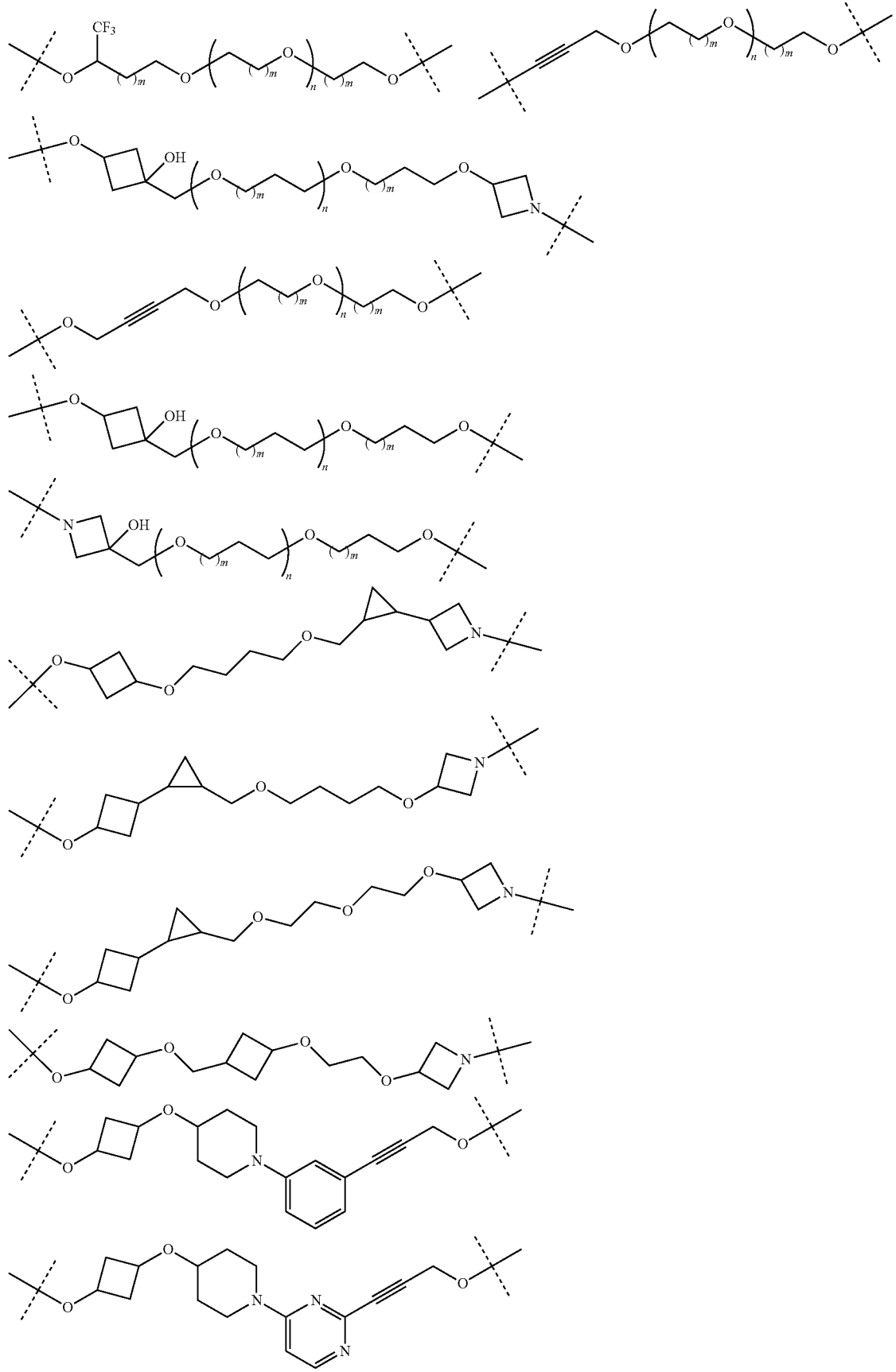

-continued
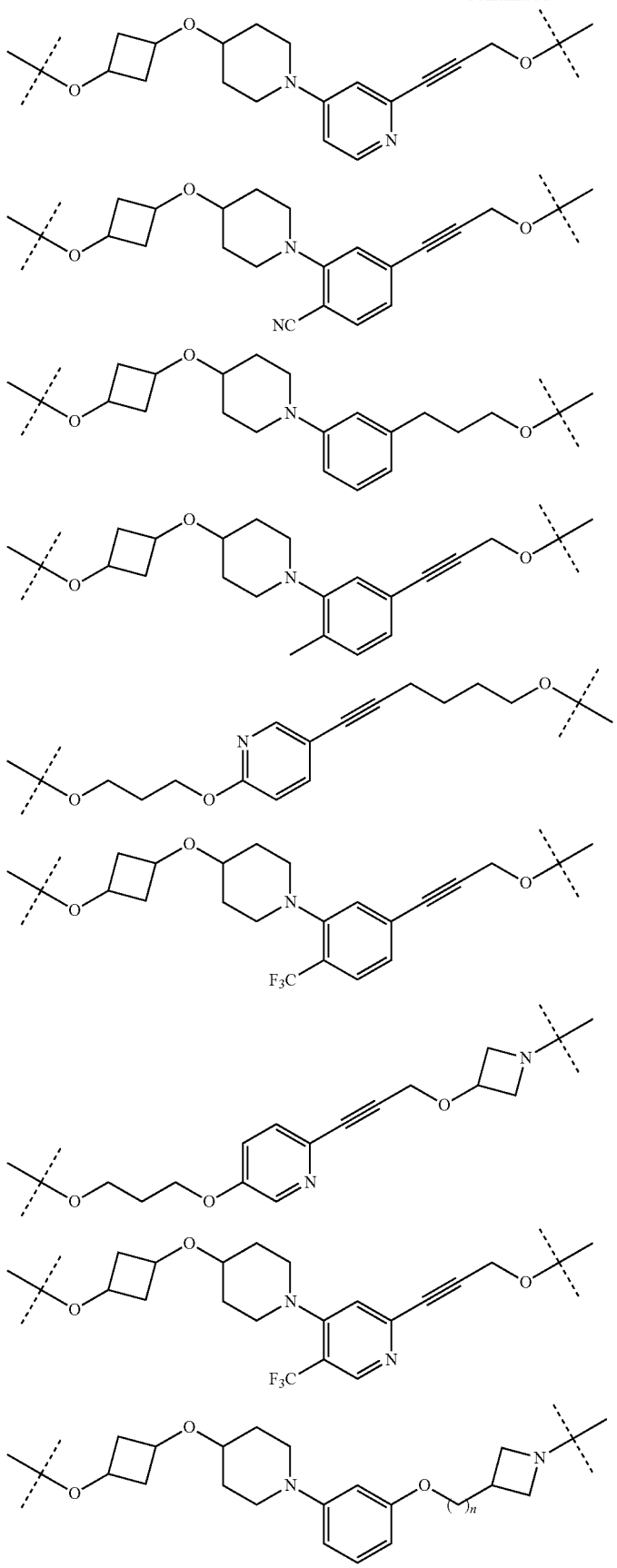

1521
1522
-continued
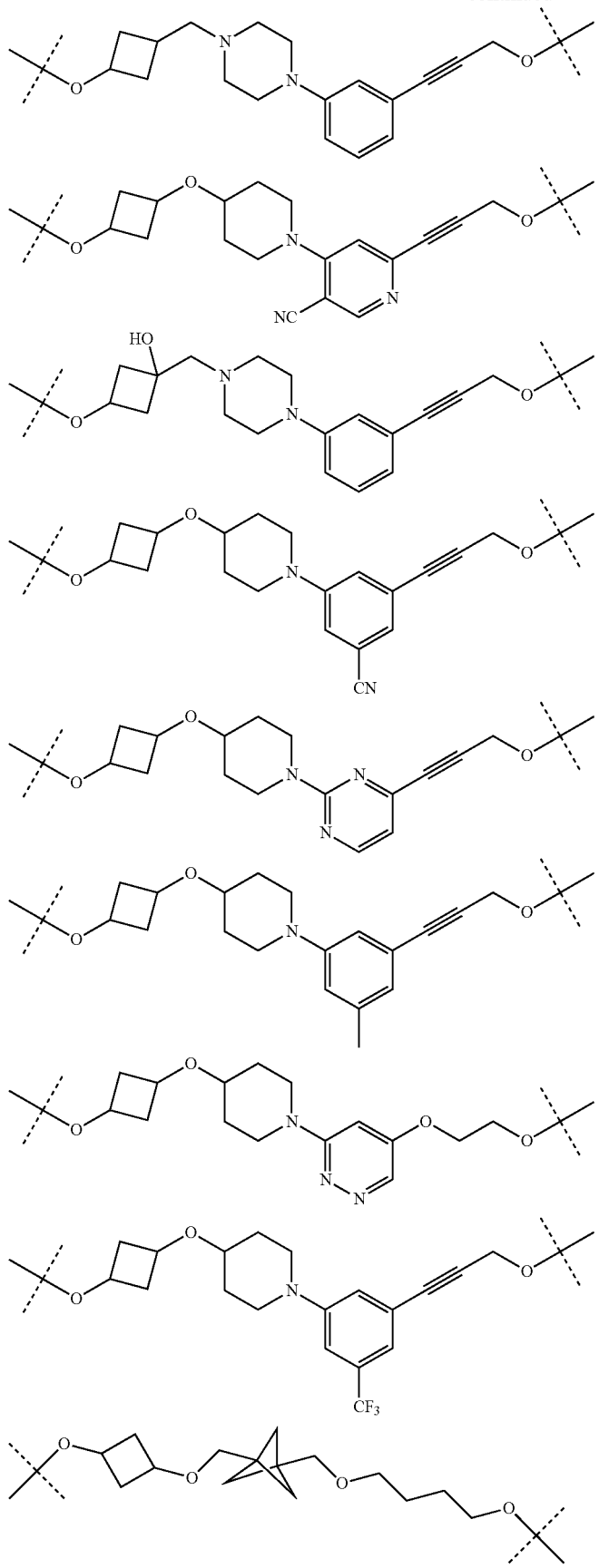

1523    -continued    1524
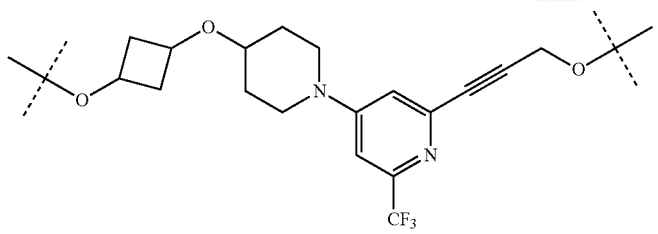
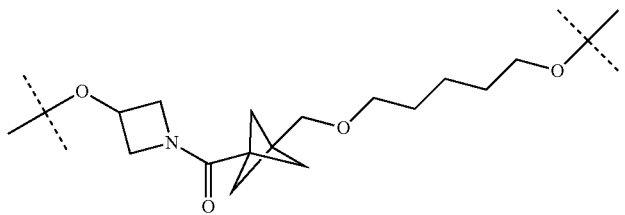
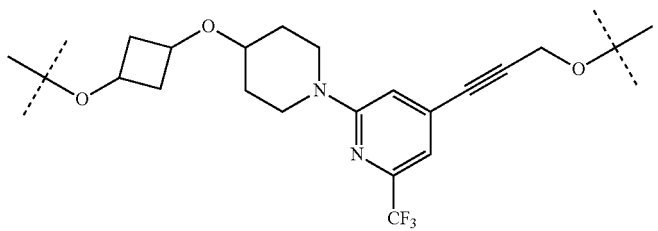
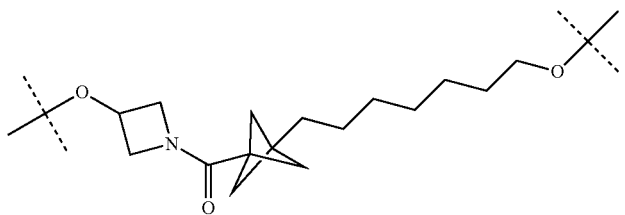
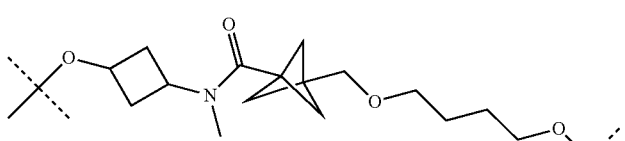
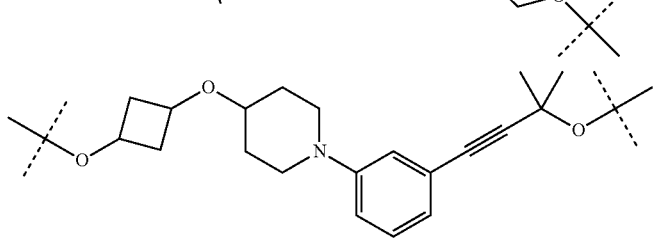
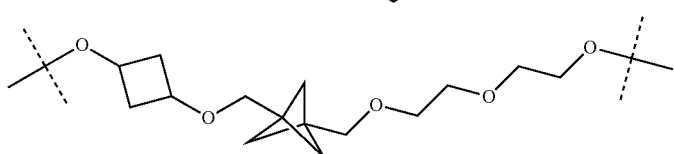
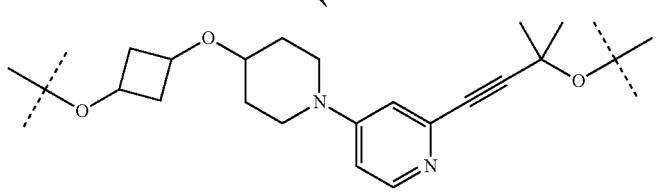

1525 1526
-continued
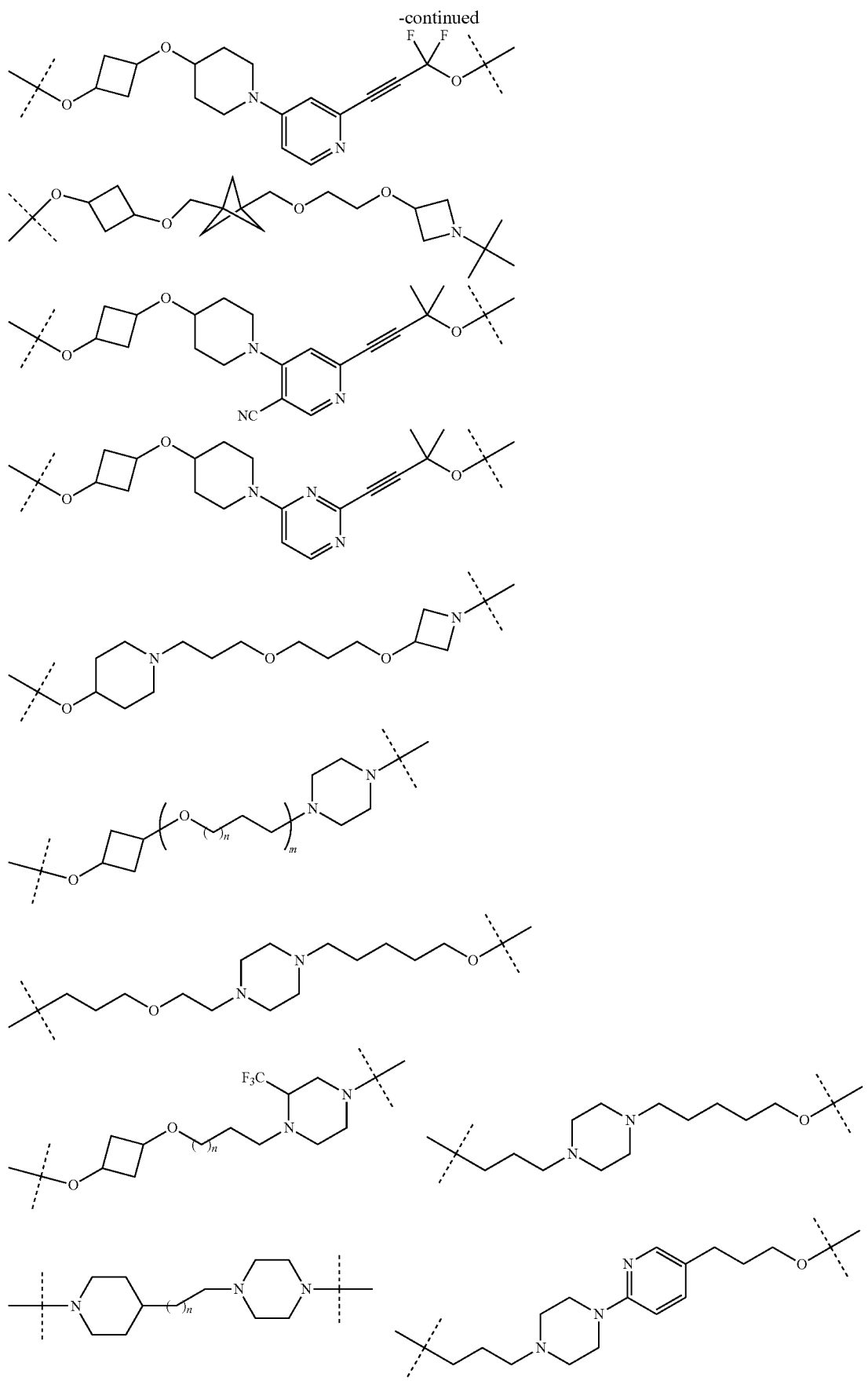

-continued
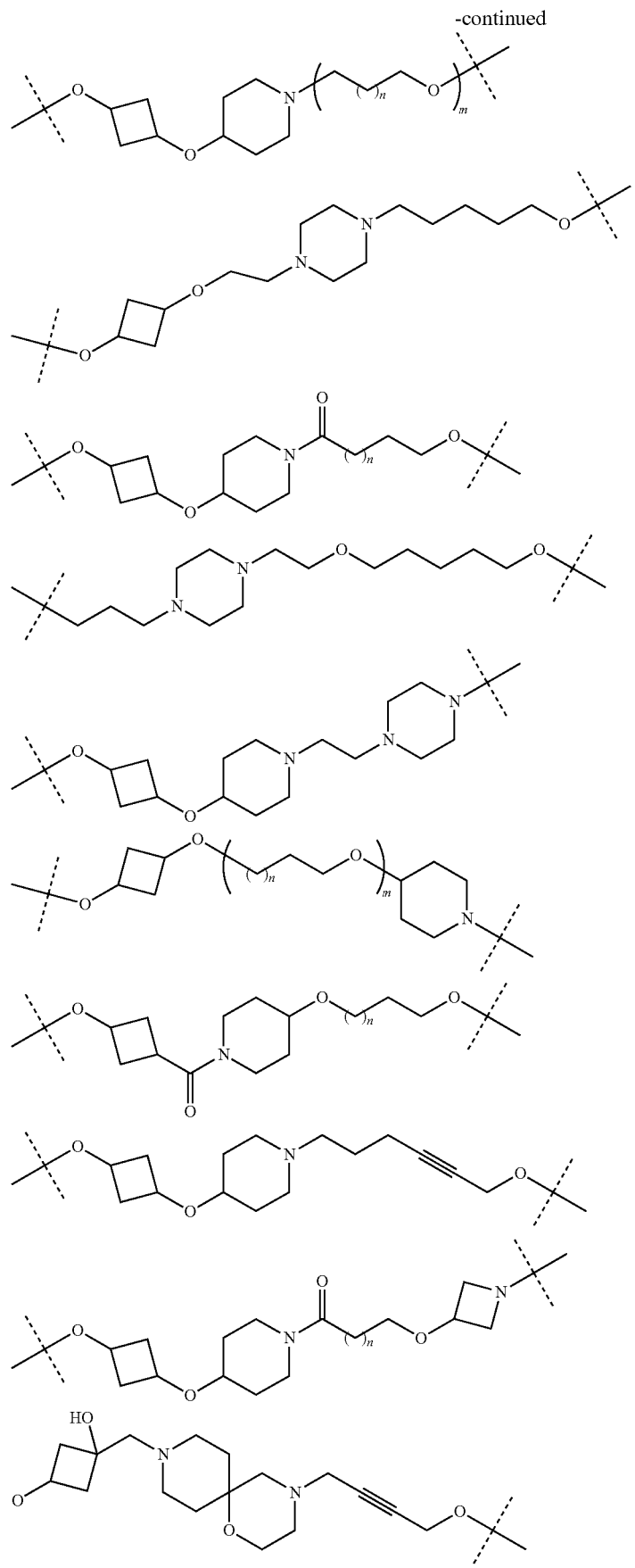

-continued
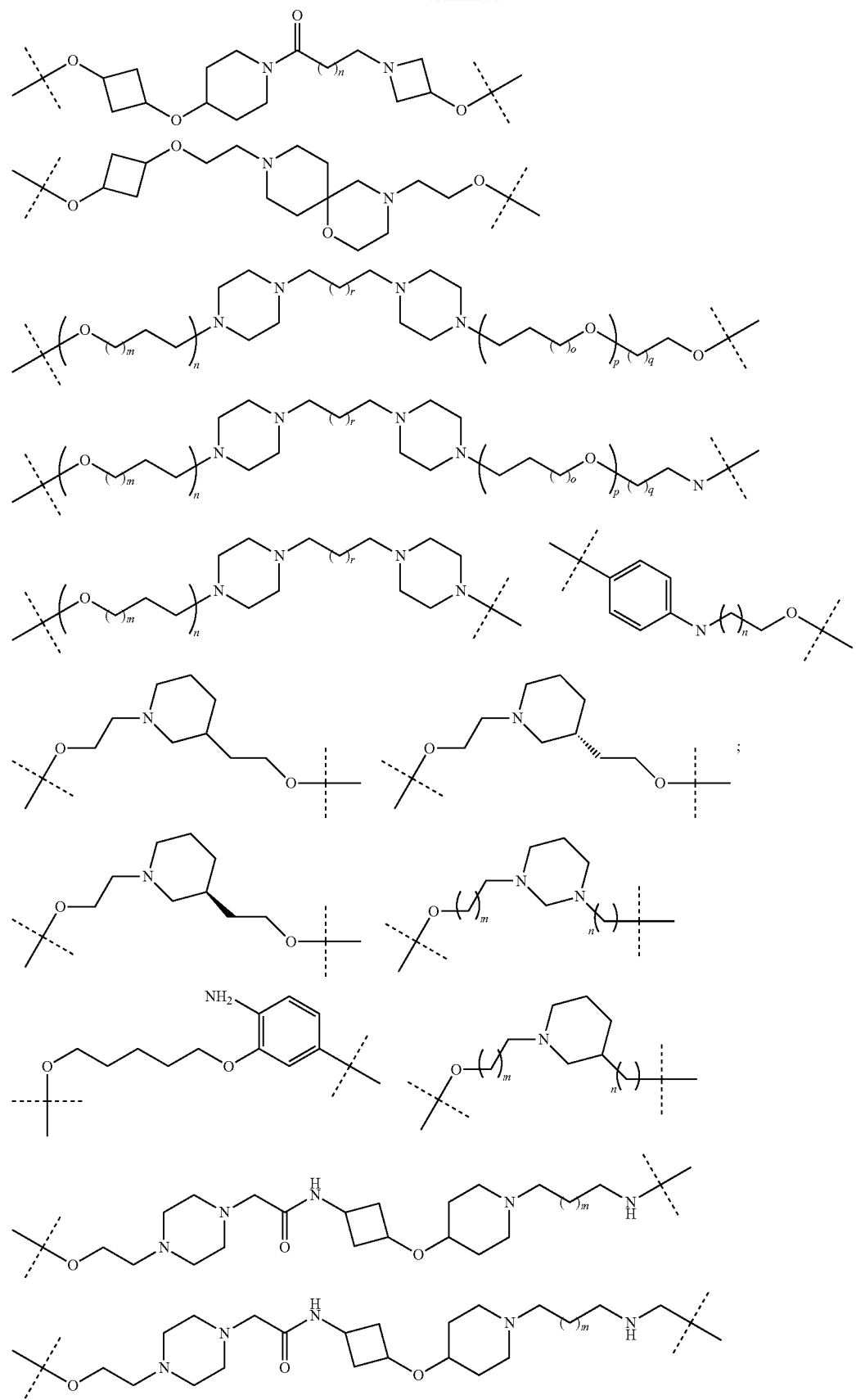

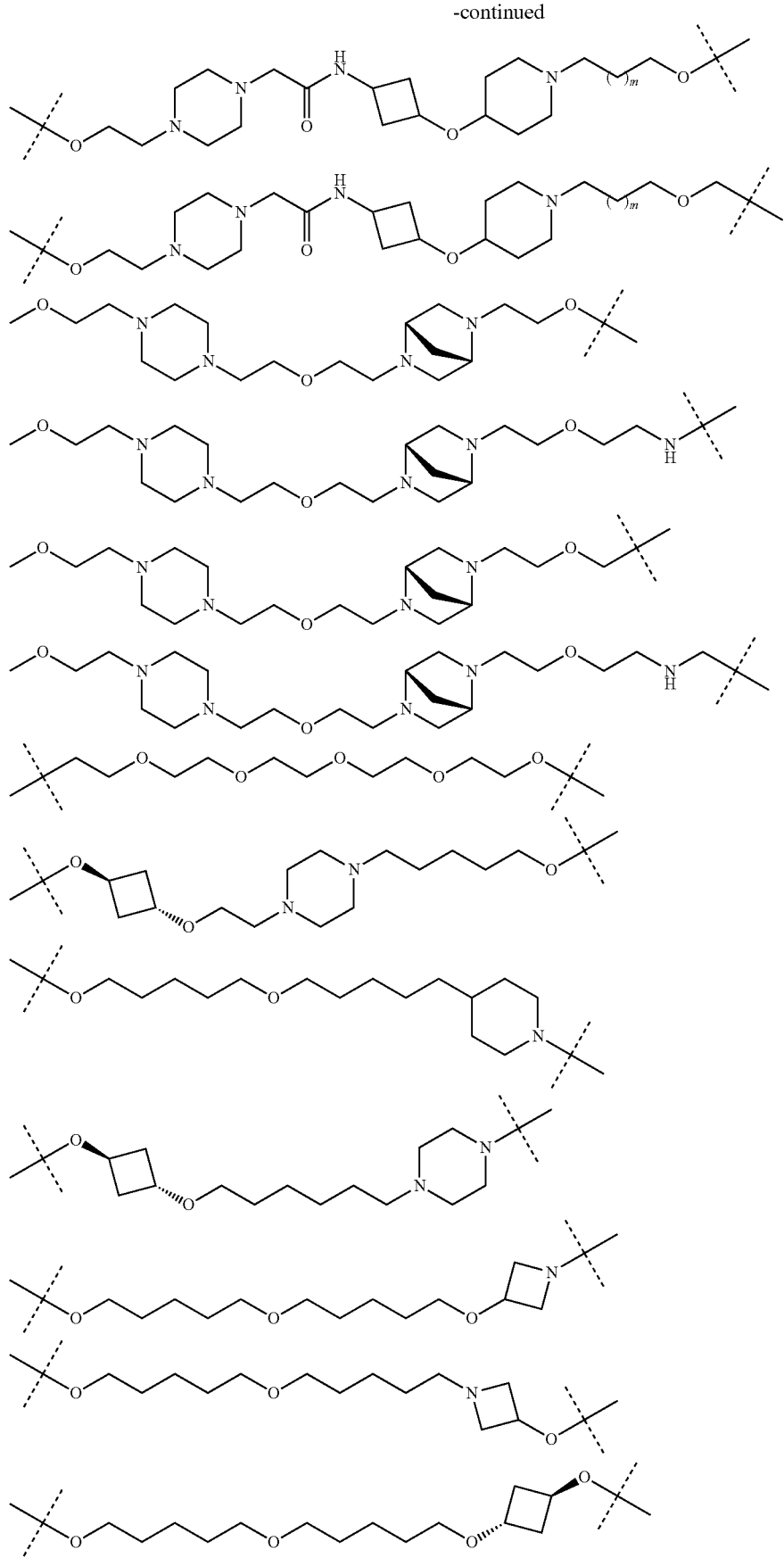

-continued
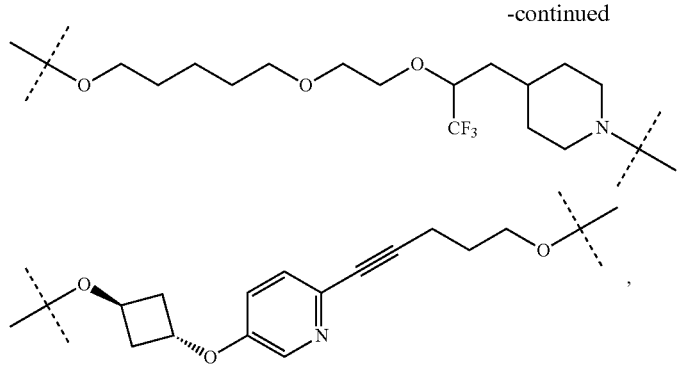
wherein m, n, o, p, q and r are independently 0, 1, 2, 3, 4, 5, 6, or 7.
12. The bifunctional compound according to claim 1, wherein the linker (L) is selected from the group consisting of:
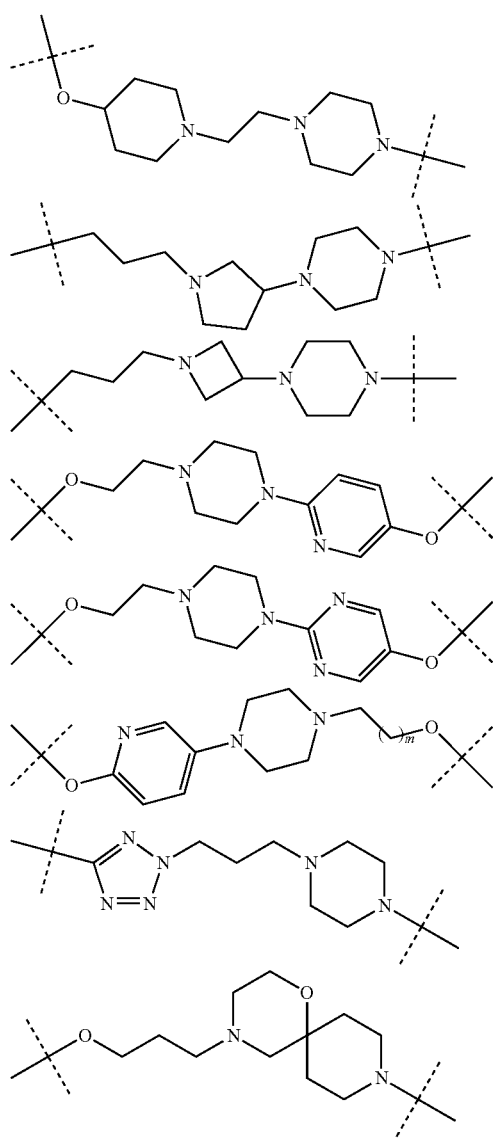
-continued
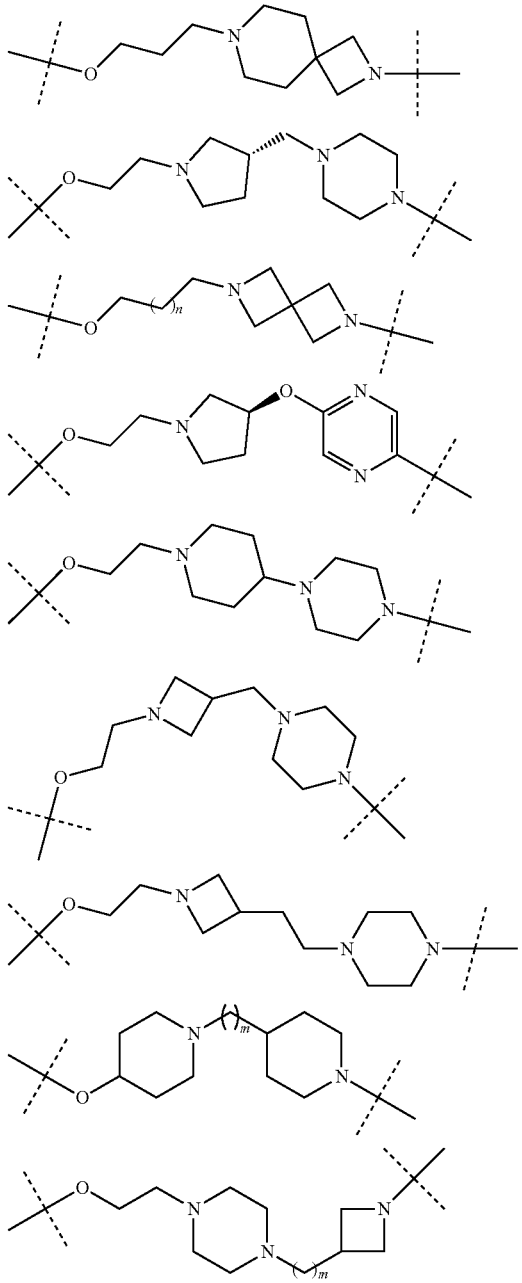

1535
-continued
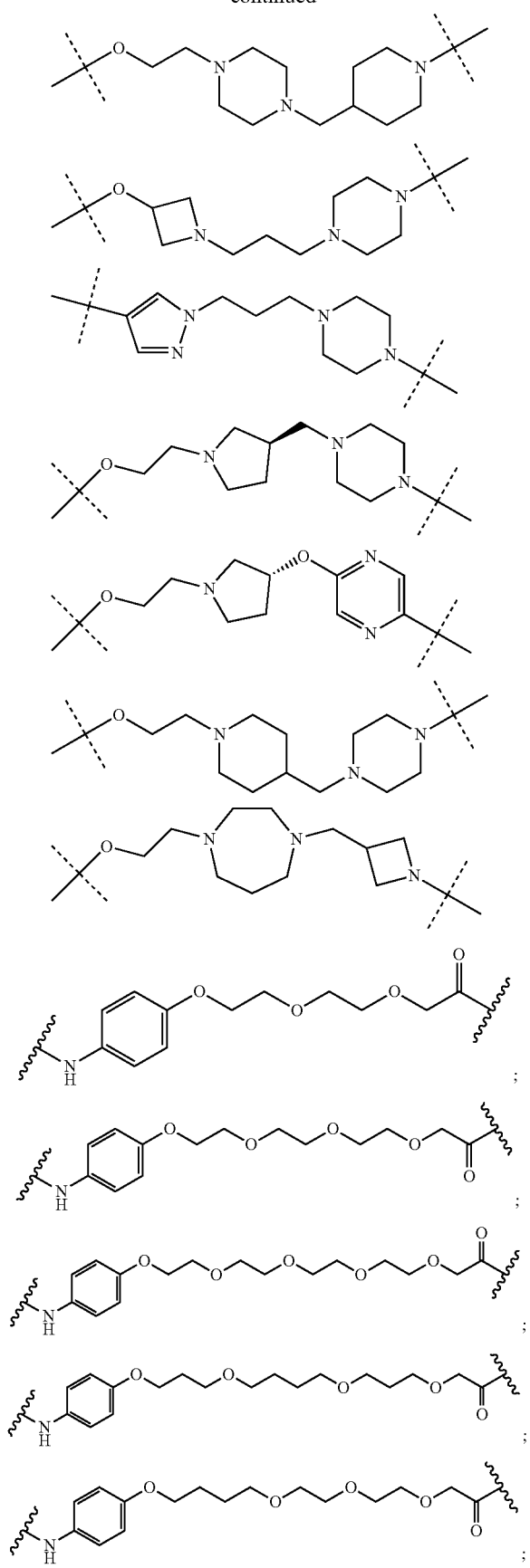
1536
-continued
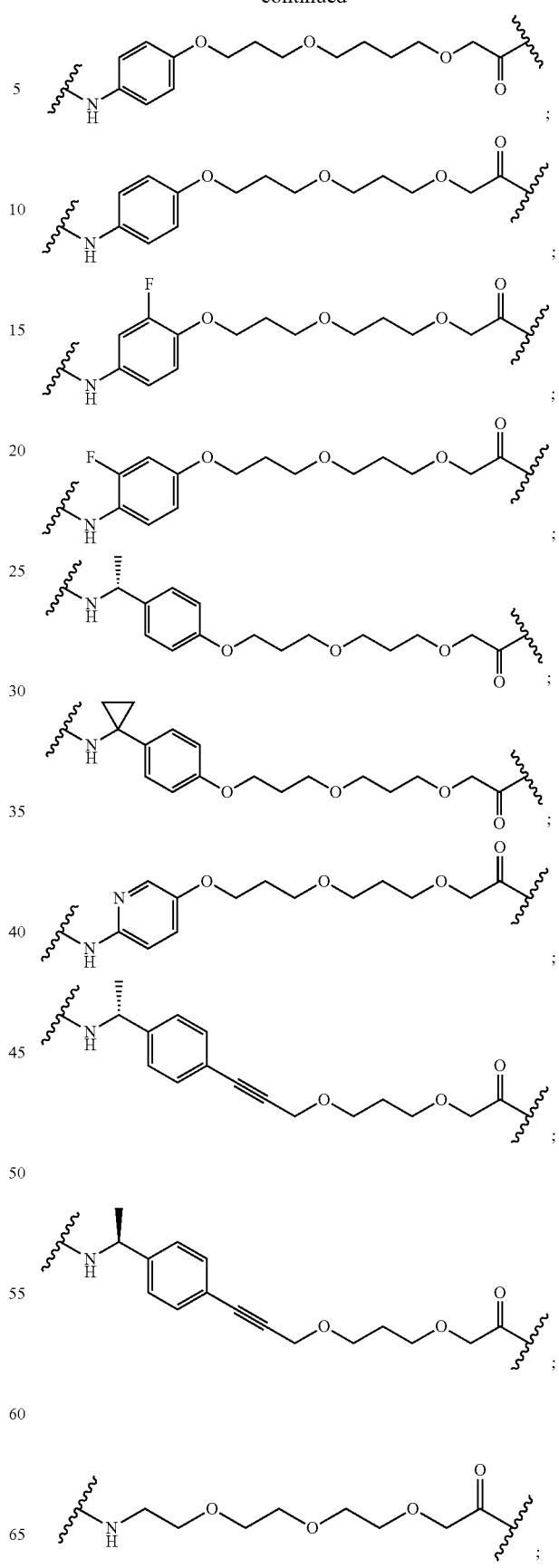

1537
-continued
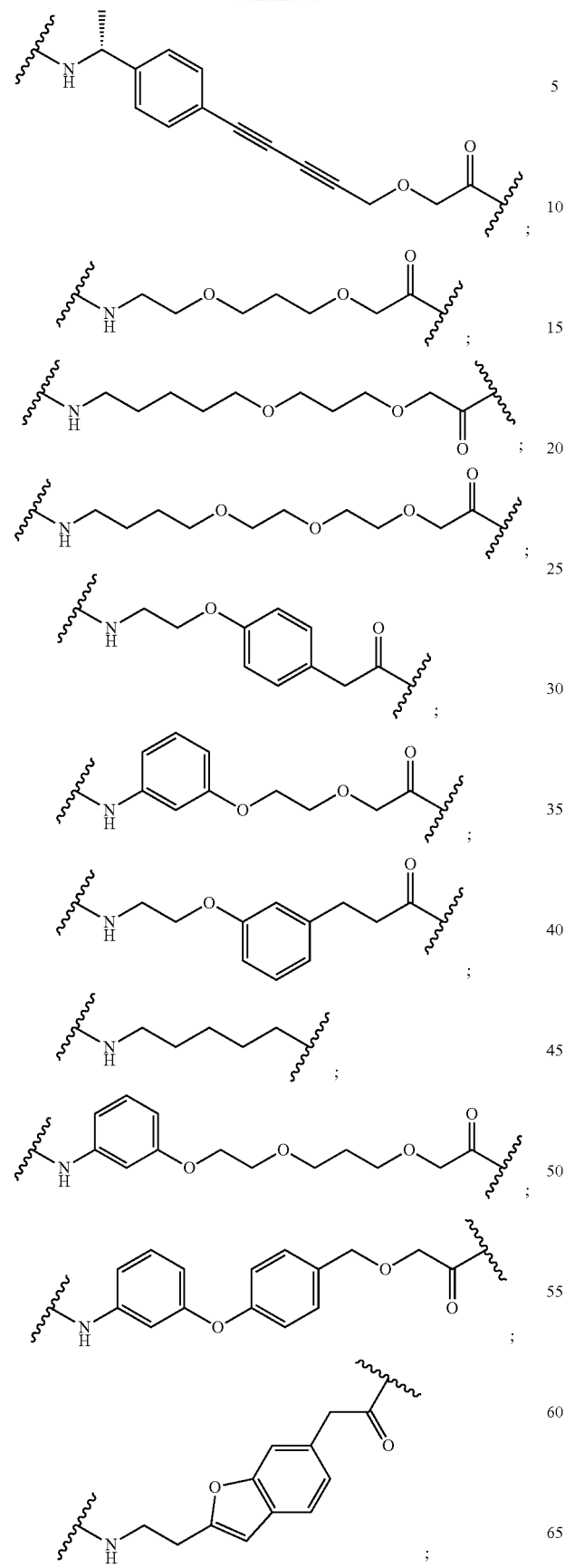
1538
-continued
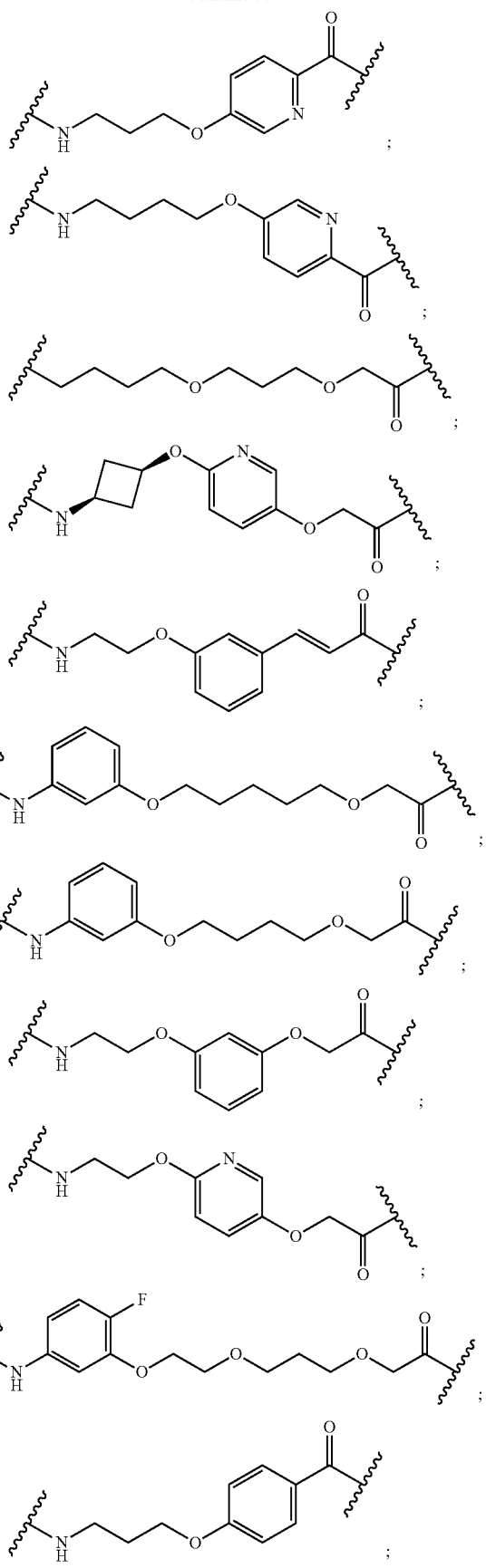

1539
-continued
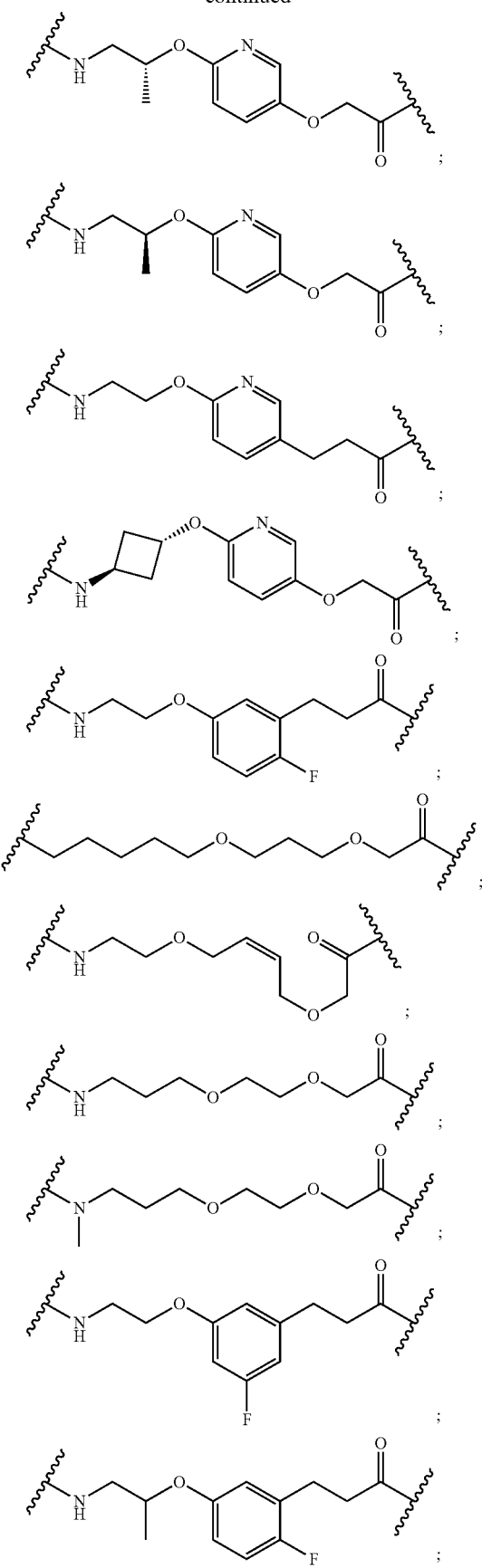
1540
-continued
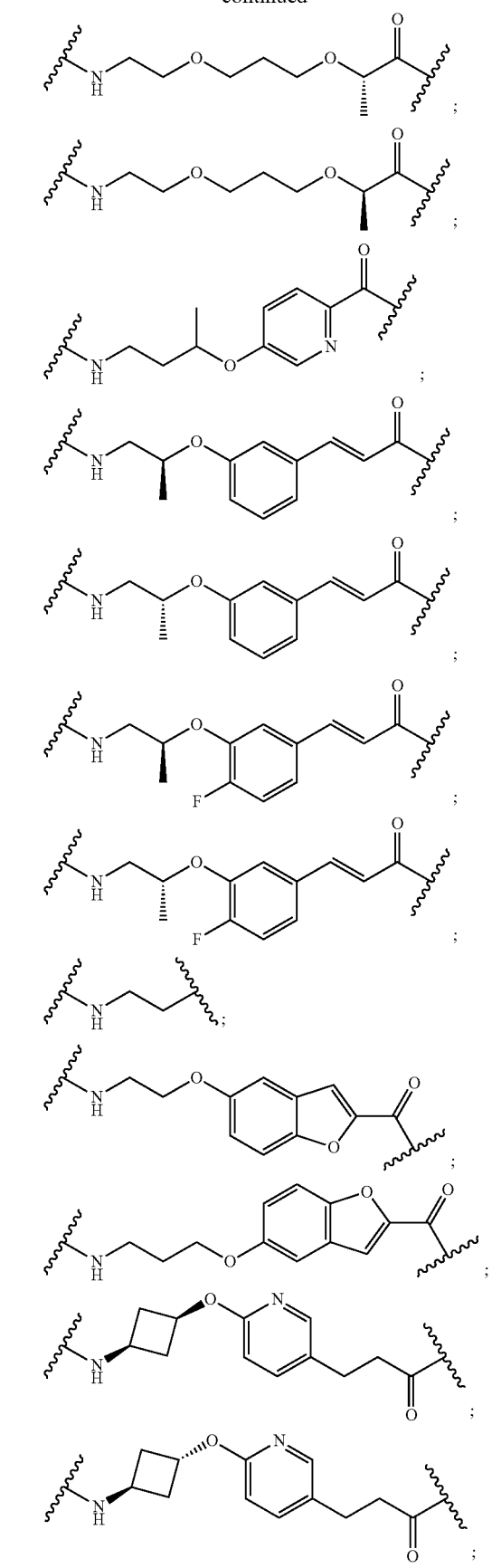

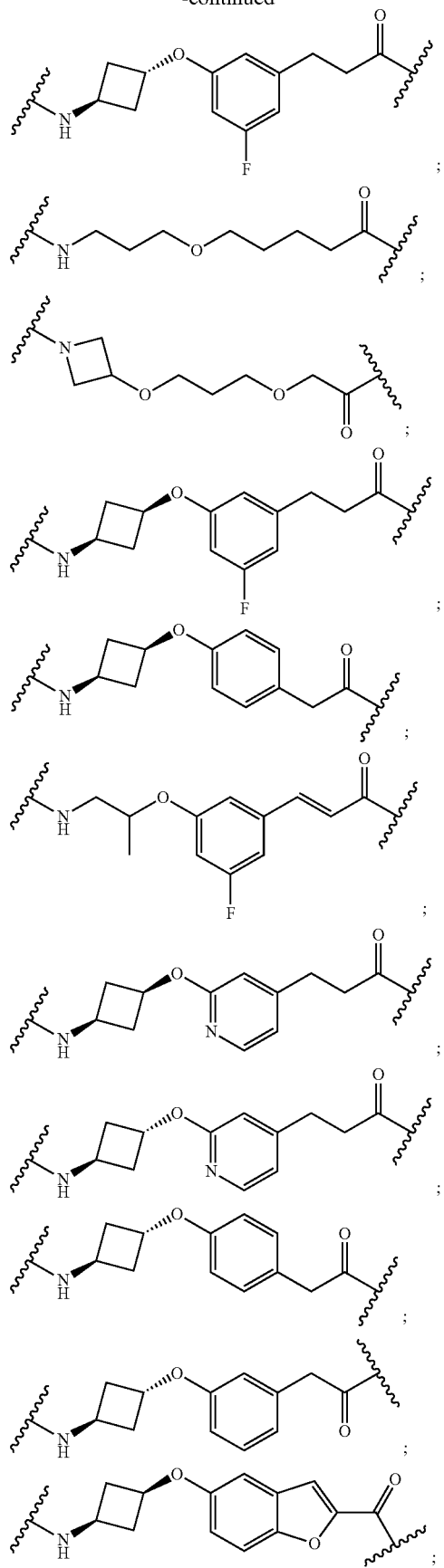
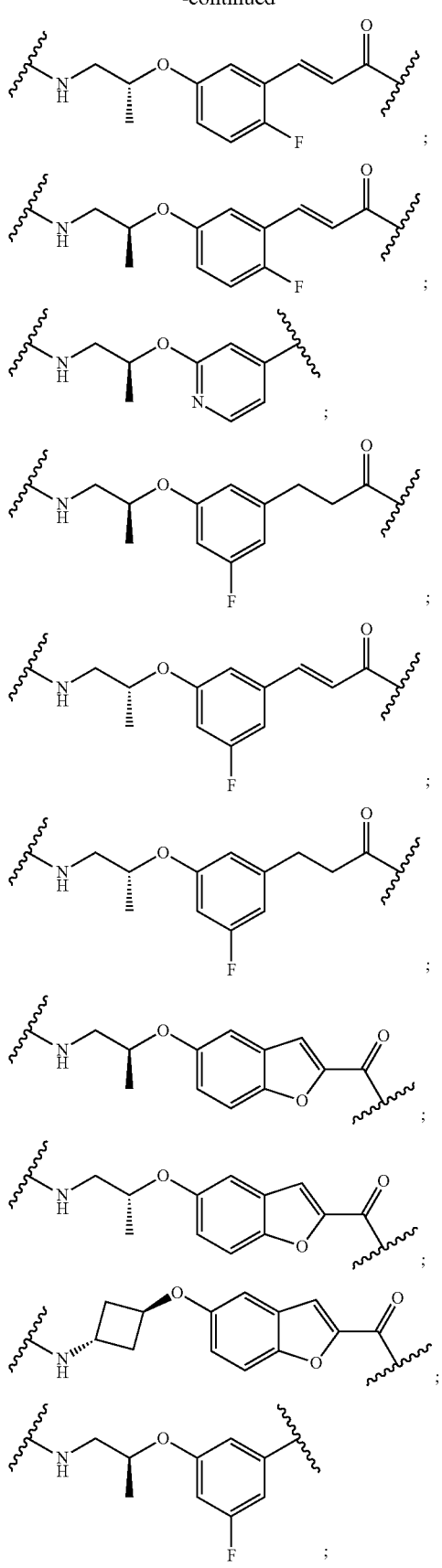

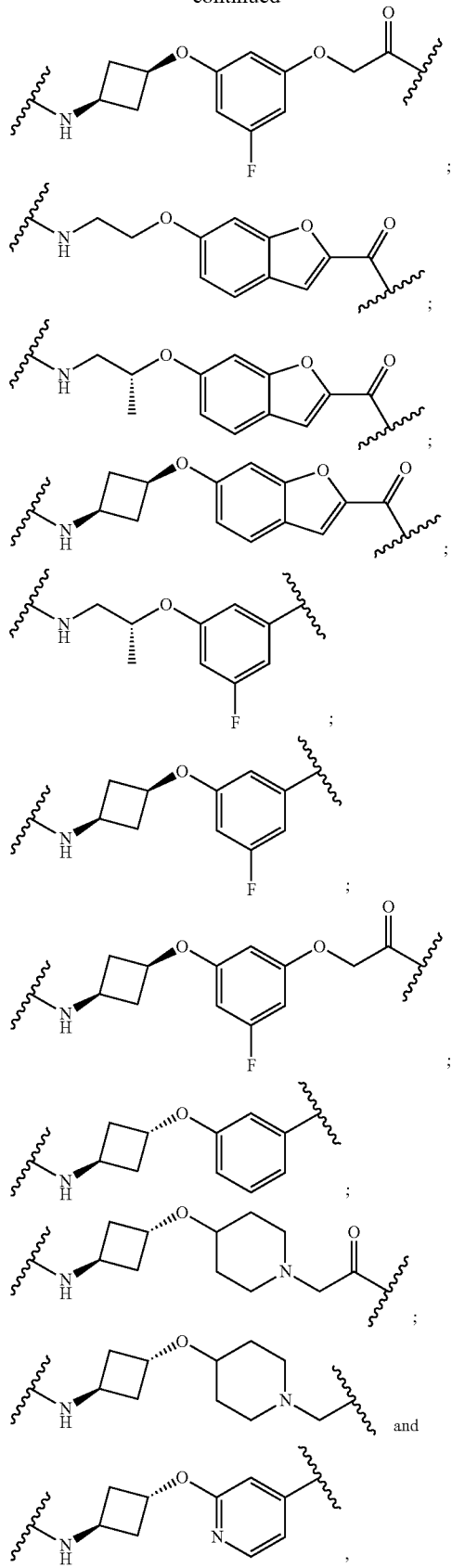
wherein each m and n is independently 0, 1, 2, 3, 4, 5, or 6.
13. The bifunctional compound according to claim 1, wherein the linker (L) is selected from the group consisting of:
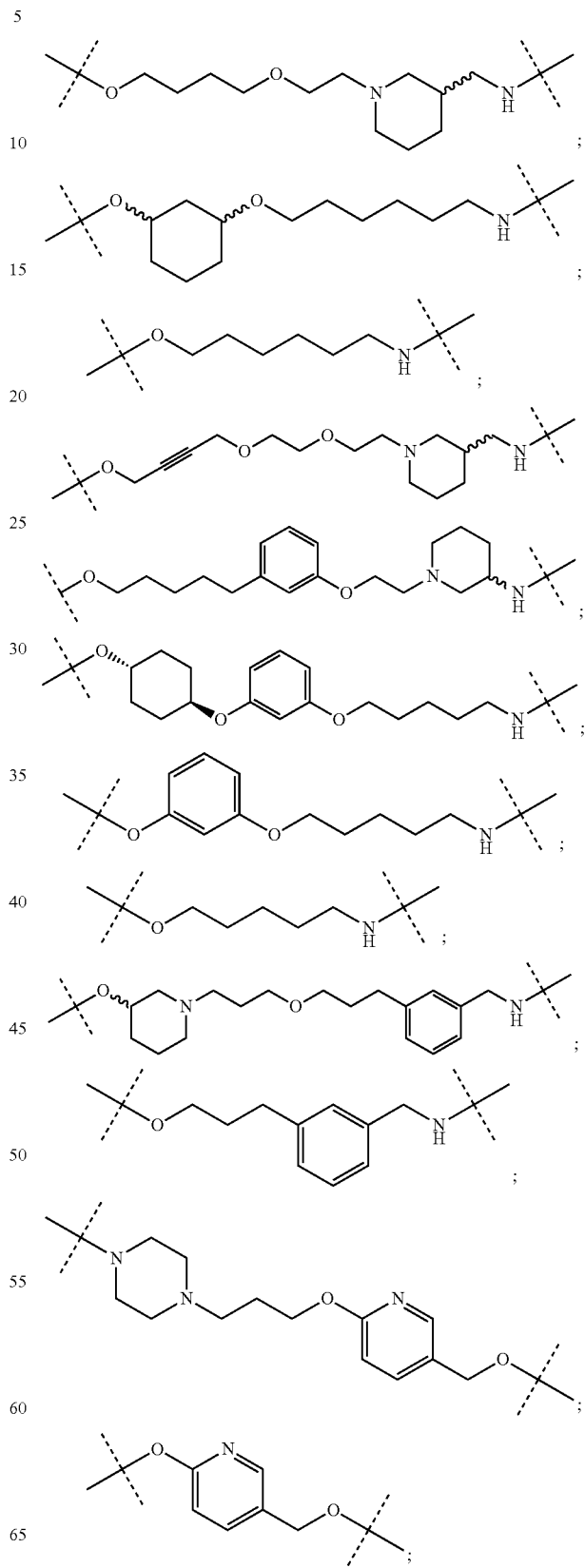

1545
-continued
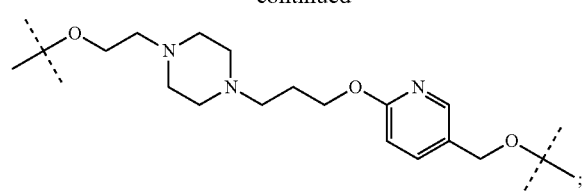
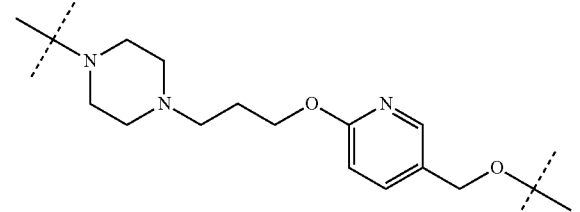
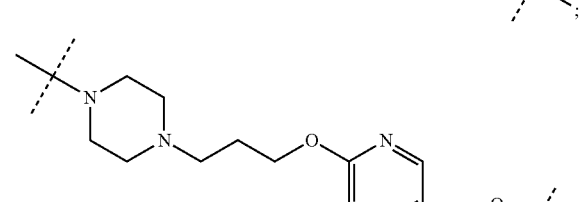
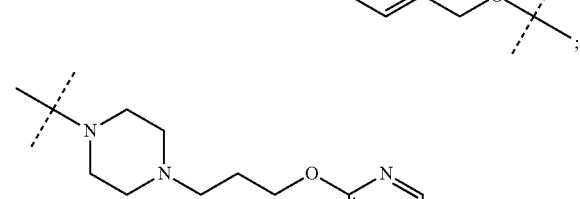
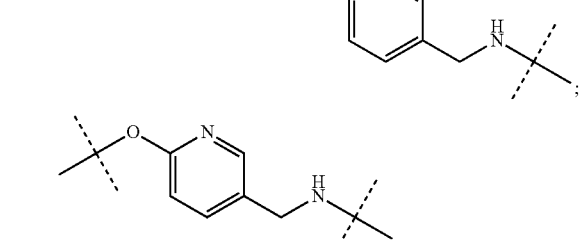
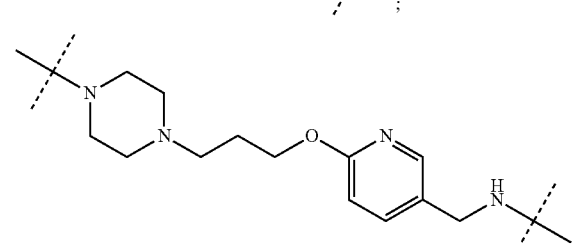
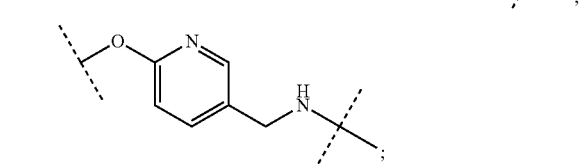
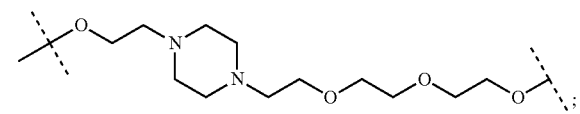
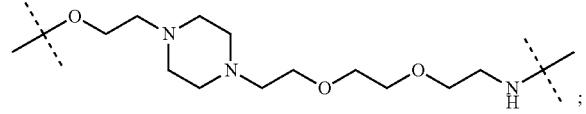
1546
-continued
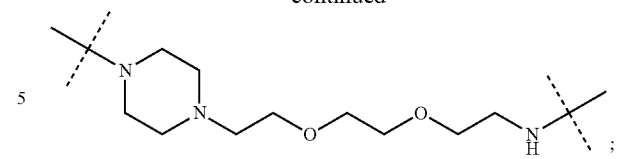
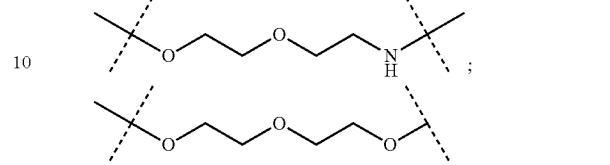
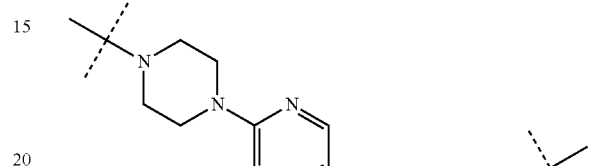
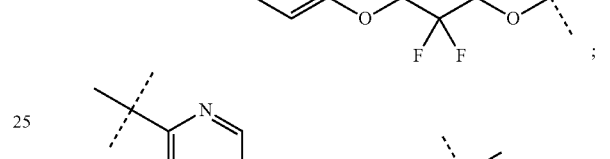
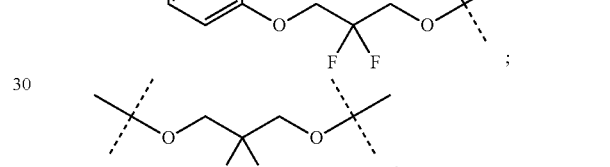
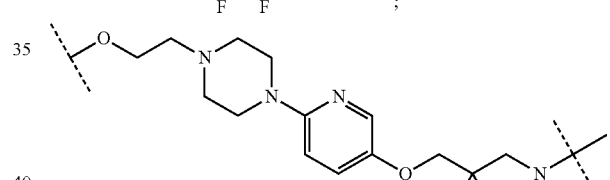
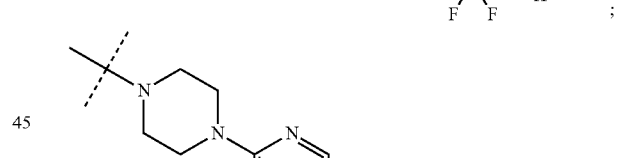
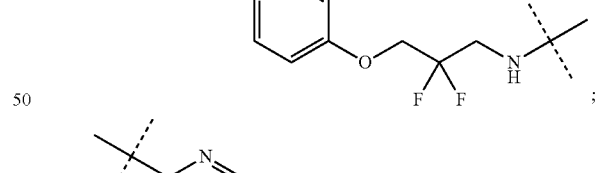
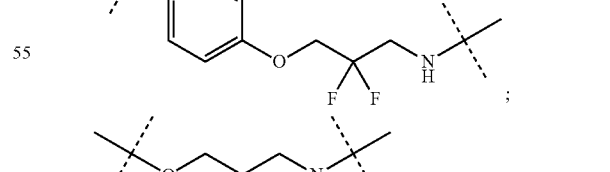
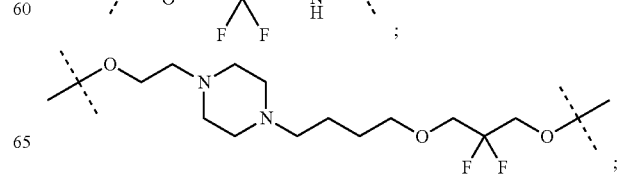

1547
-continued
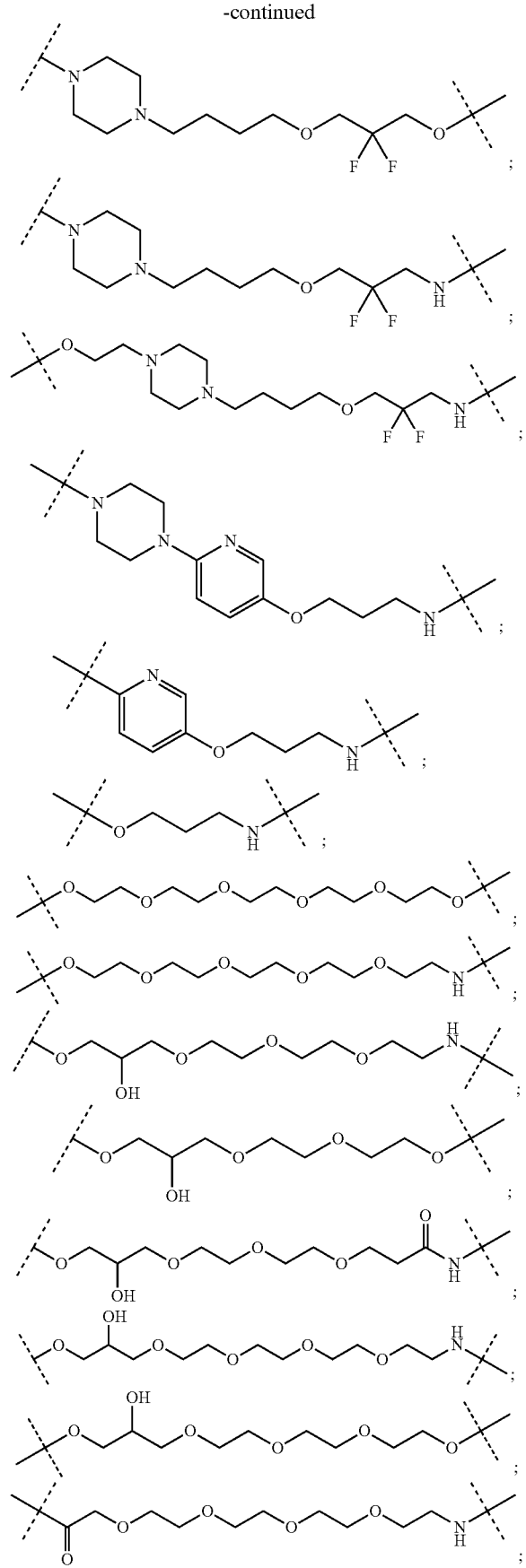
1548
-continued
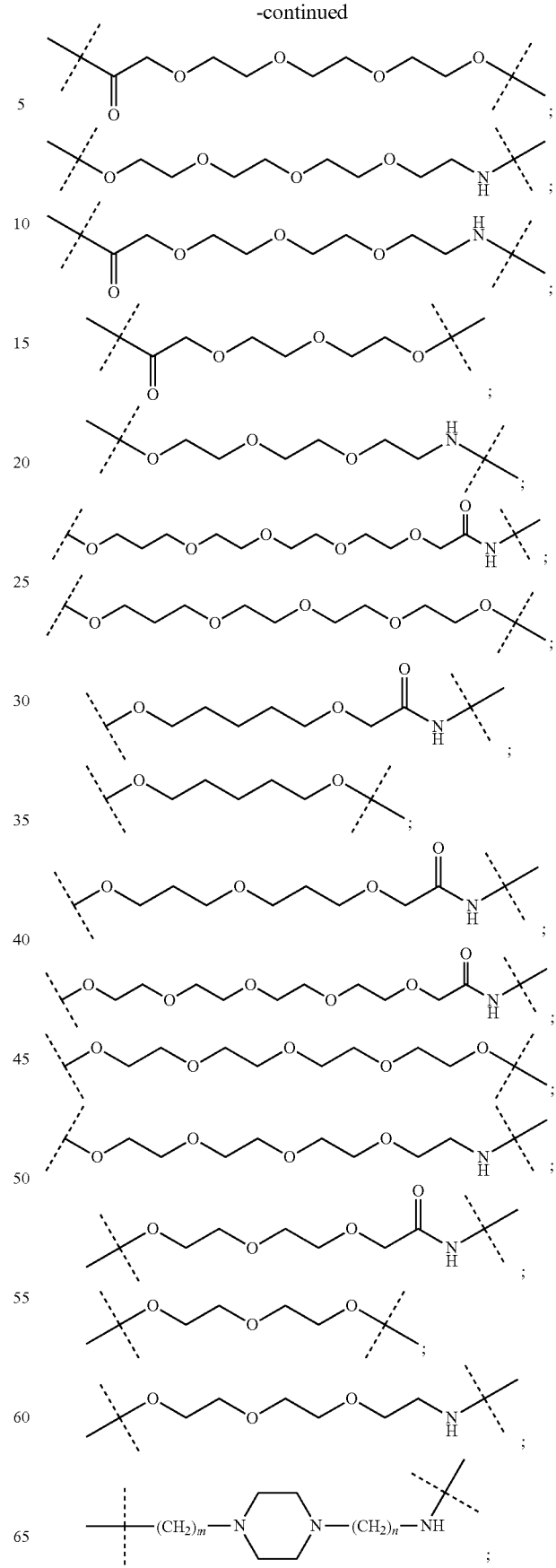

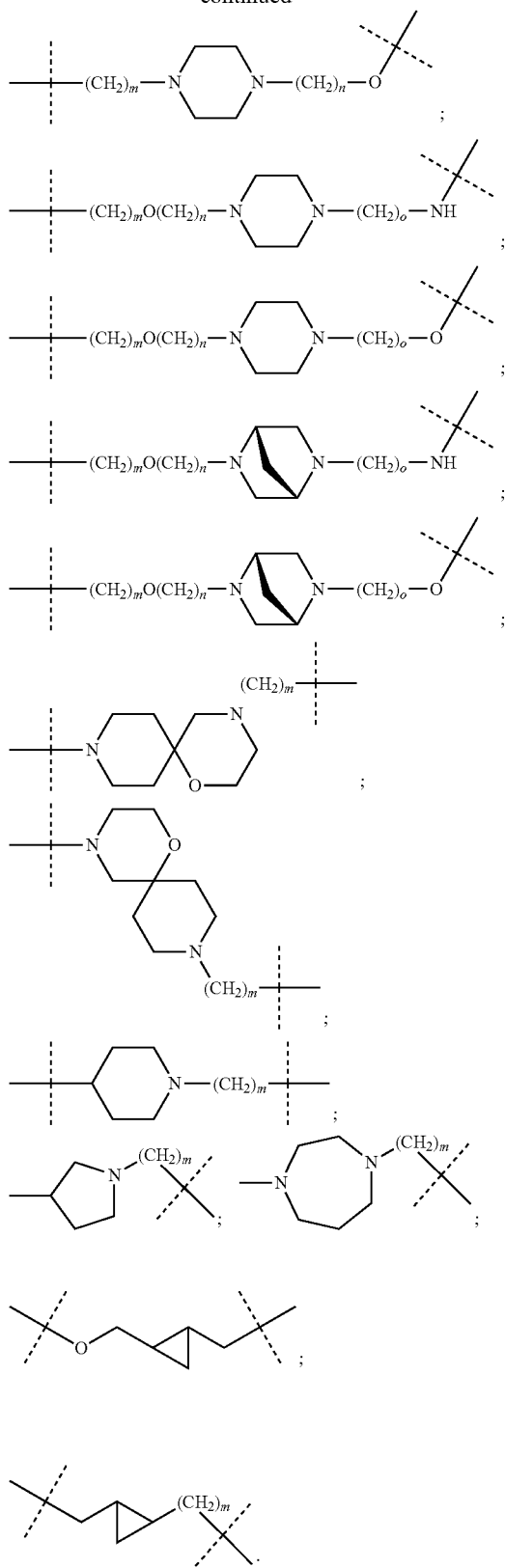

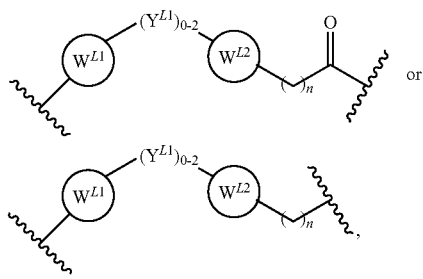

wherein:
W$^{L1}$ and W$^{L2}$ are each independently a 4-8 membered ring with 0-4 heteroatoms, optionally substituted with RQ, each RQ is independently a H, halo, OH, CN, CF3, optionally substituted linear or branched C1-C6 alkyl, optionally substituted linear or branched C1-C6 alkoxy, or 2 RQ groups taken together with the atom they are attached to, form a 4-8 membered ring system containing 0-4 heteroatoms;
Y$^{L1}$ is each independently a bond, optionally substituted linear or branched C1-C6 alkyl and optionally one or more C atoms are replaced with O; or optionally substituted linear or branched C1-C6 alkoxy;
n is 0-10; and
the ⤫ indicates the attachment point to the PTM or ULM moieties.

15. The bifunctional compound according to claim 1, wherein the linker (L) comprises the following chemical structure:

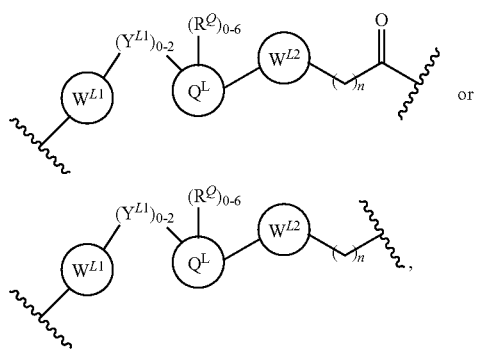

wherein:
W$^{L1}$ and W$^{L2}$ are each independently aryl, heteroaryl, cyclic, heterocyclic, C$_{1-6}$ alkyl, bicyclic, biaryl, biheteroaryl, or biheterocyclic, each optionally substituted with RQ, each R$^Q$ is independently a H, halo, OH, CN, CF$_3$, hydroxyl, nitro, C≡CH, C$_{2-6}$ alkenyl, C$_{2-6}$ alkynyl, optionally substituted linear or branched C1-C6 alkyl, optionally substituted linear or branched C$_1$-C$_6$ alkoxy, OC$_{1-3}$alkyl optionally substituted by 1 or more —F, OH, NH$_2$, NR$^{Y1}$R$^{Y2}$, CN, or 2 R$^Q$ groups taken together with the atom they are attached to, form a 4-8 membered ring system containing 0-4 heteroatoms;
Y$^{L1}$ is each independently a bond, NR$^{YL1}$, O, S, NR$^{YL2}$, CR$^{YL1}$-R$^{YL2}$, C═O, C═S, SO, SO$_2$, optionally substituted linear or branched C$_1$-C$_6$ alkyl and optionally one or more C atoms are replaced with O; optionally substituted linear or branched C$_1$-C$_6$ alkoxy;
Q$^L$ is a 3-6 membered alicyclic or aromatic ring with 0-4 heteroatoms, optionally bridged, optionally substituted 14. The bifunctional compound according to claim 1, wherein the linker (L) comprises the following chemical structure:

with 0-6 $R^Q$, each $R^Q$ is independently H, linear or branched $C_{1-6}$ alkyl optionally substituted by 1 or more halo or $C_{1-6}$ alkoxyl, or 2 $R^Q$ groups taken together with the atom they are attached to, form a 3-8 membered ring system containing 0-2 heteroatoms;

$R^{YL1}$, $R^{YL2}$ are each independently H, OH, linear or branched $C_{1-6}$ alkyl optionally substituted by 1 or more halo or $C_{1-6}$ alkoxyl, or $R^1$, $R^2$ together with the atom they are attached to, form a 3-8 membered ring system containing 0-2 heteroatoms;

n is 0-10; and the ⊰ indicates the attachment point to the PTM or ULM moieties.

16. The bifunctional compounds according to claim 1, wherein the linker (L) is selected from the group consisting of:

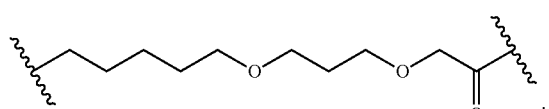

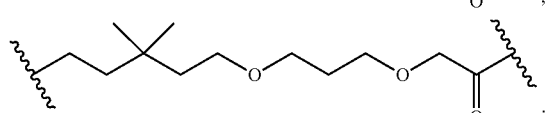

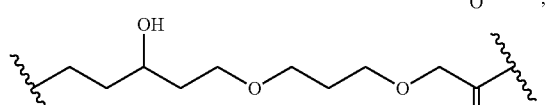

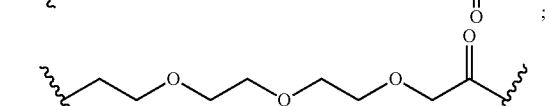

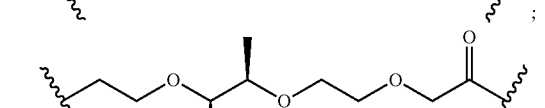

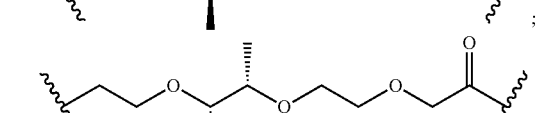

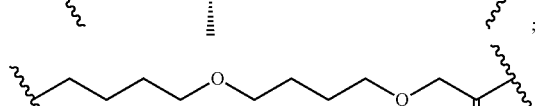

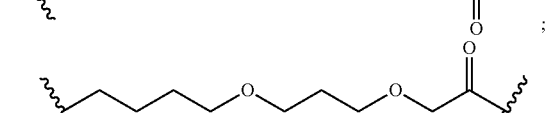

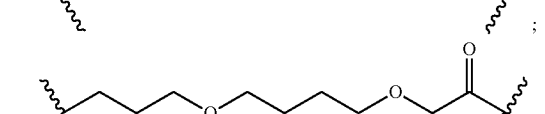

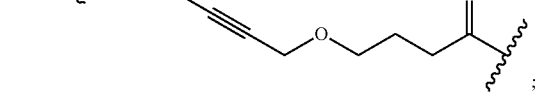

-continued

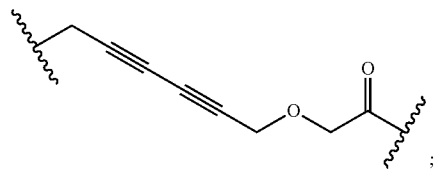

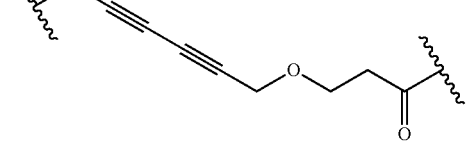

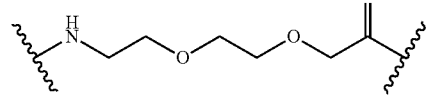

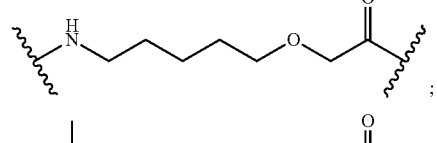

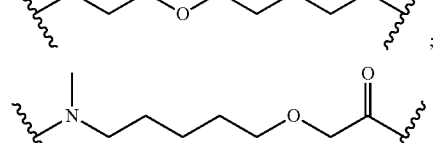

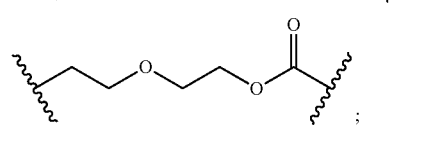

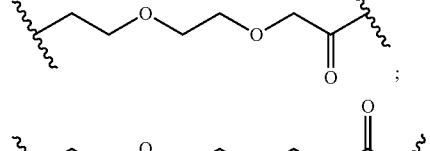

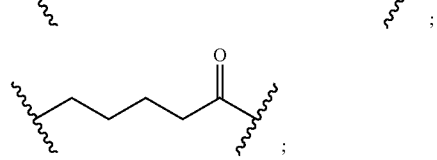

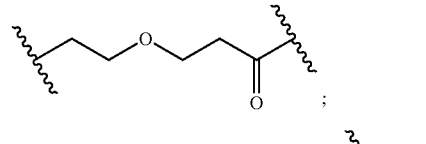

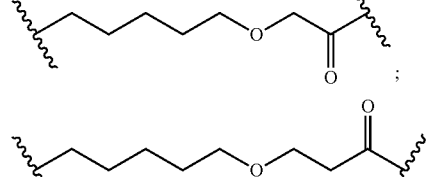

1553
-continued
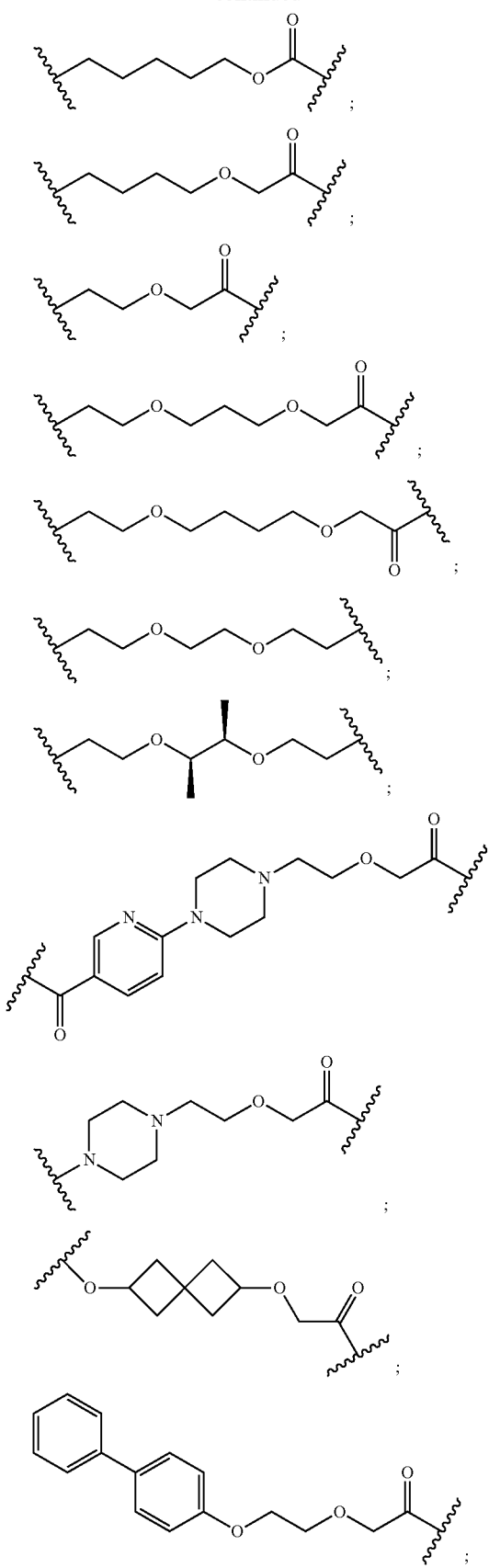
1554
-continued
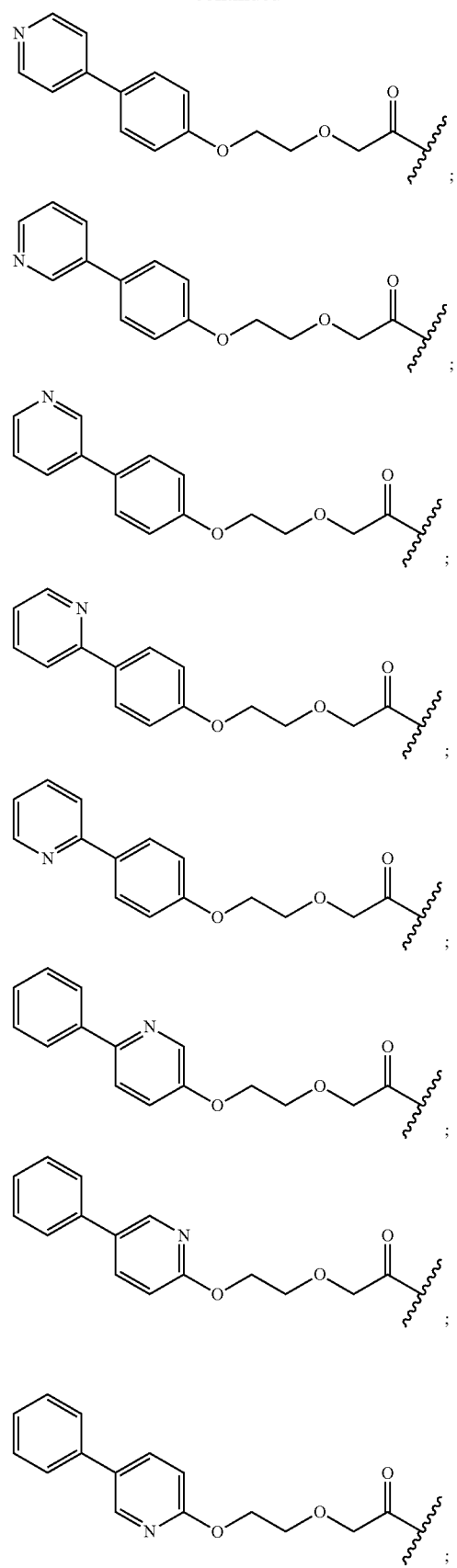

1555
-continued
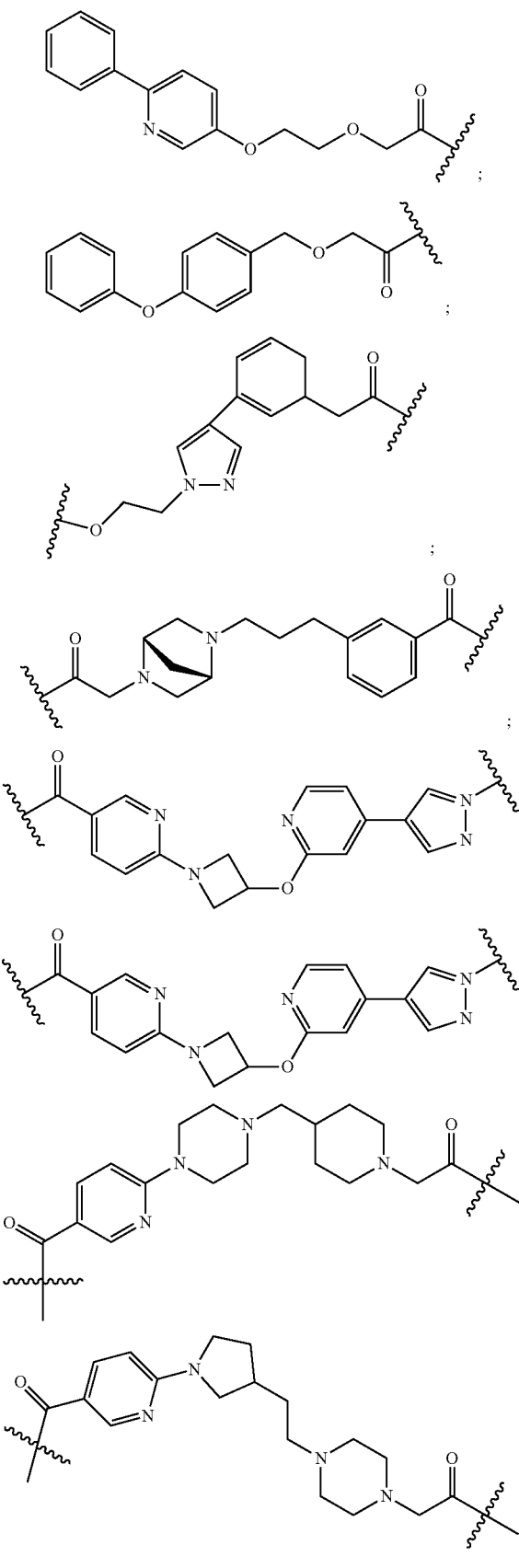
1556
-continued
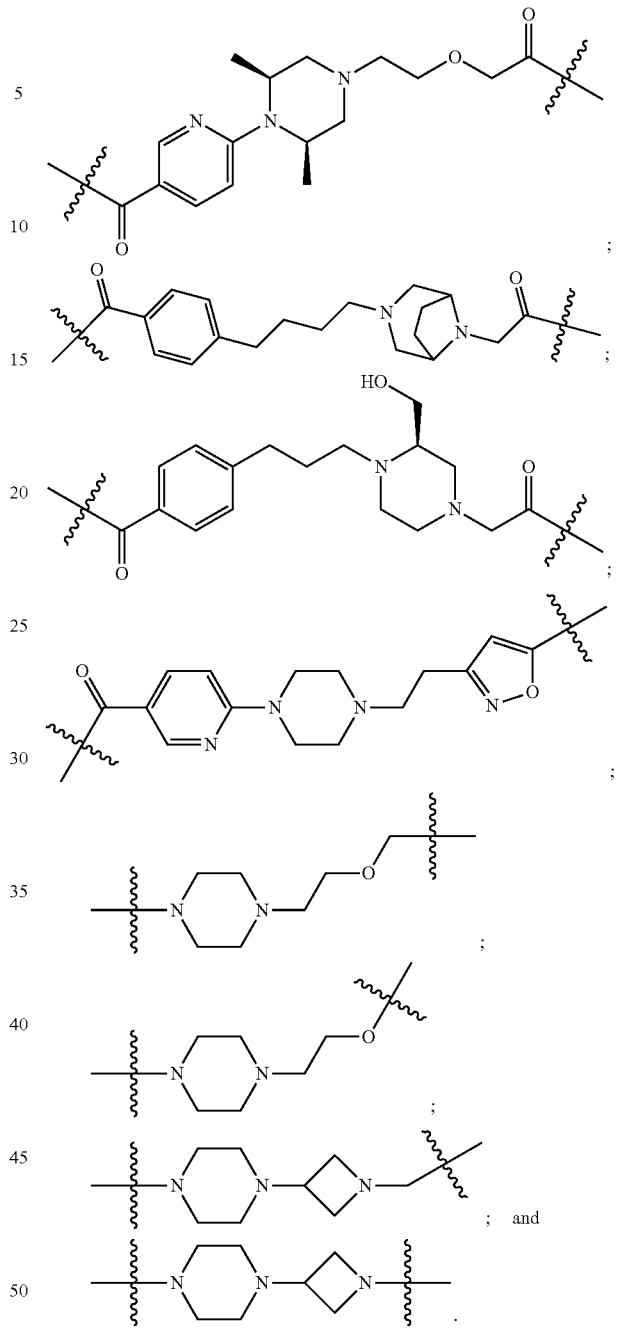
17. The bifunctional compound according to claim 1, wherein the linker (L) is a polyethylenoxy group optionally substituted with aryl or phenyl comprising from 1 to 10 ethylene glycol units.
18. The bifunctional compound according to claim 1, wherein the linker is selected from the group consisting of:
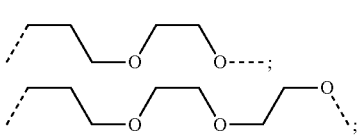

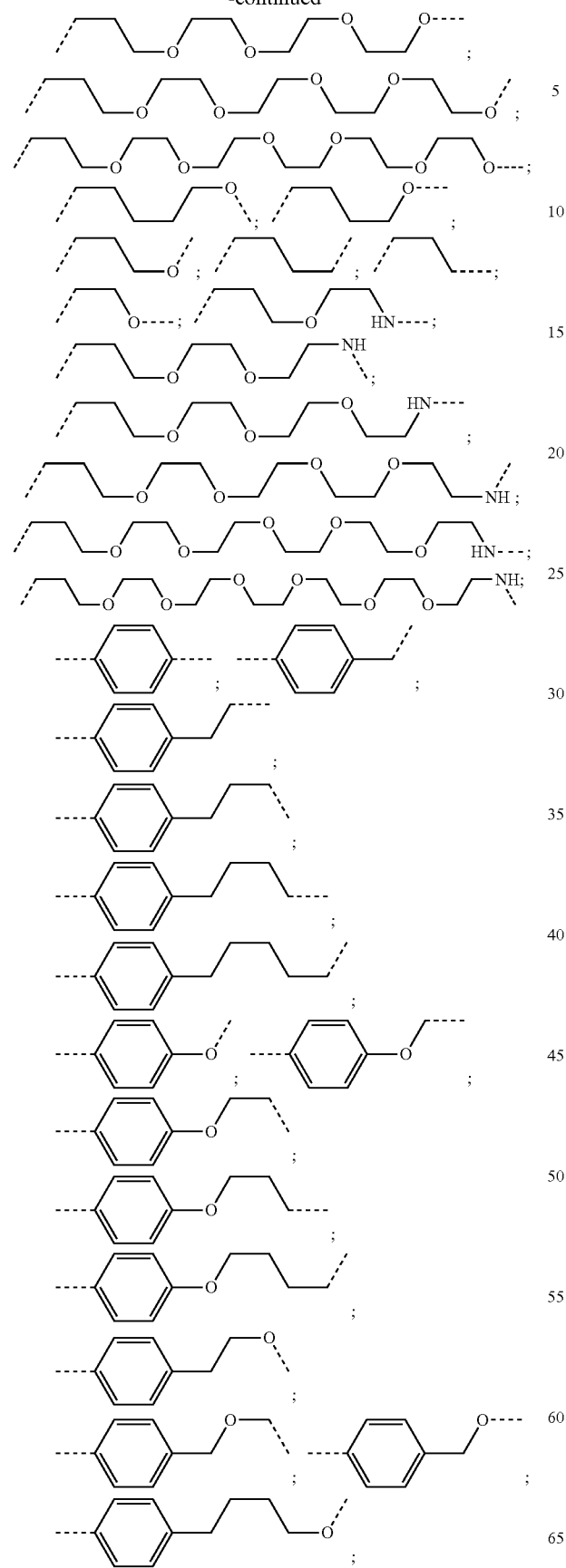
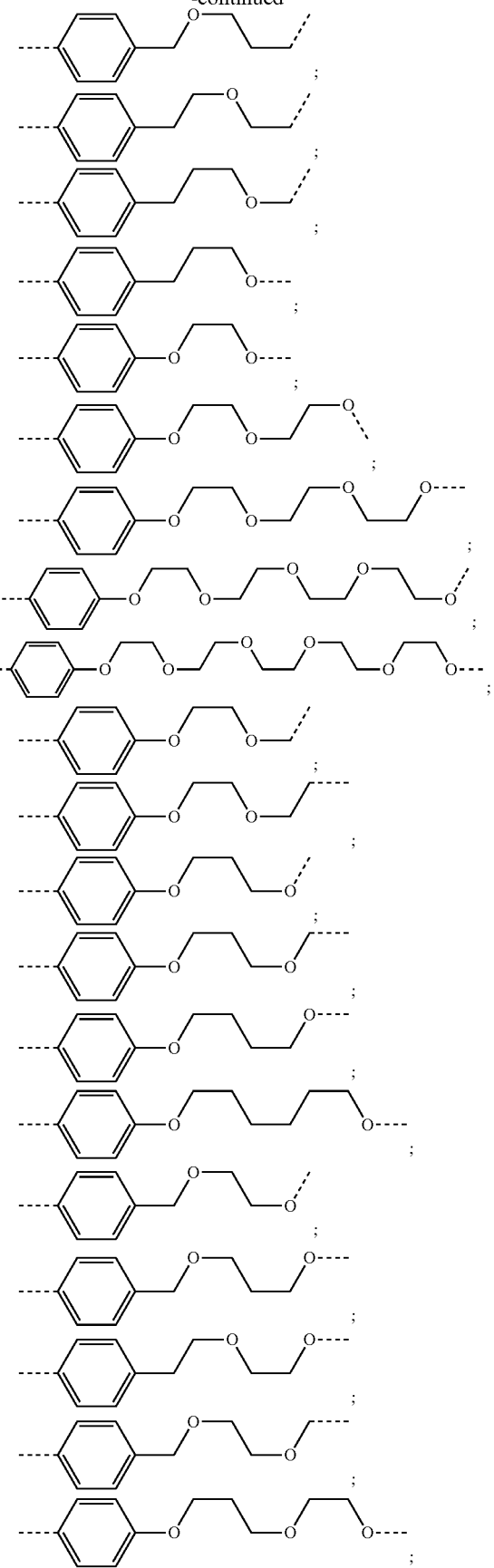

1559
-continued
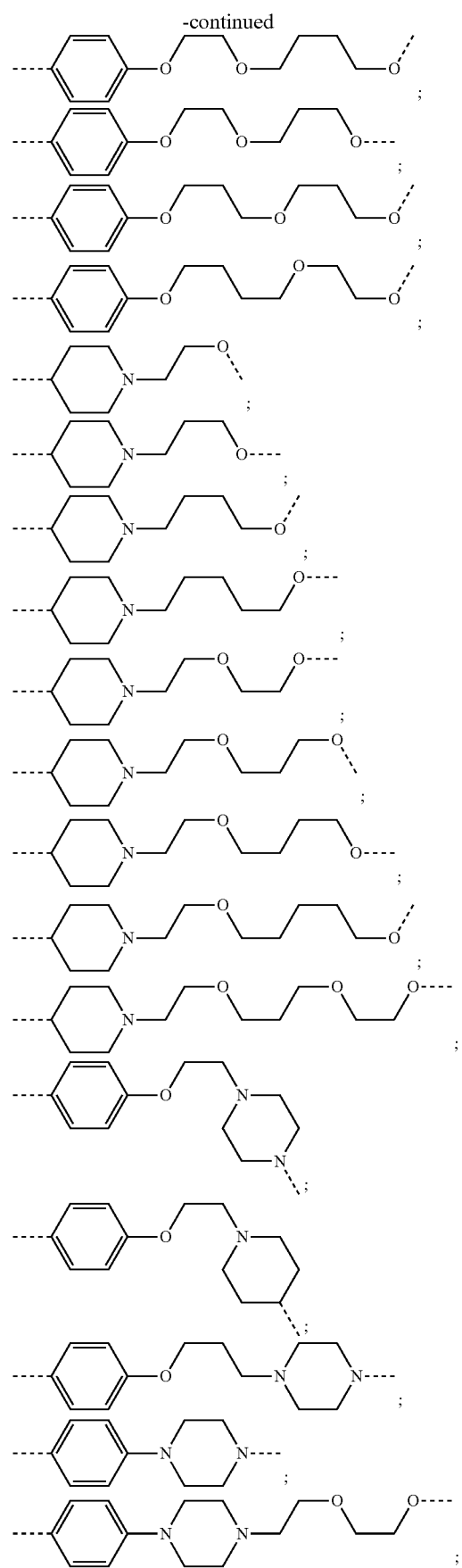
1560
-continued
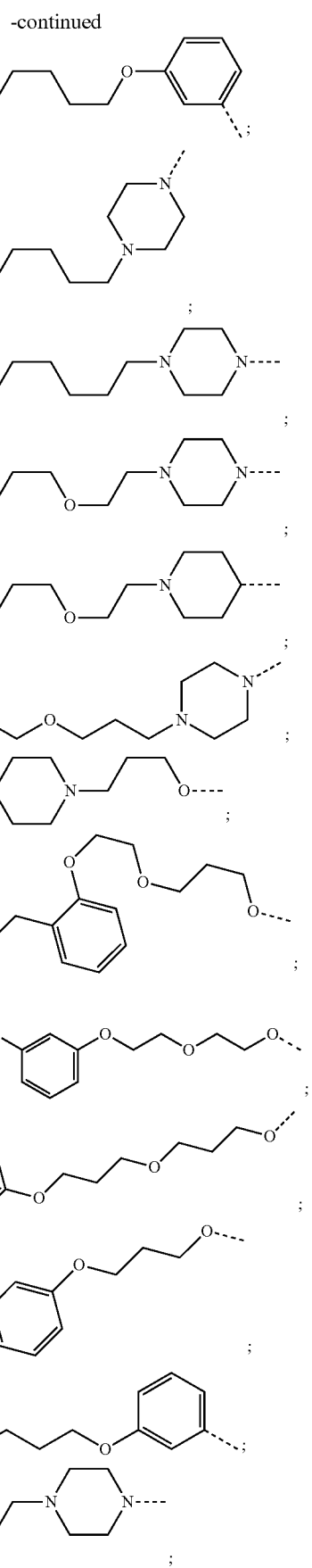

1561
-continued
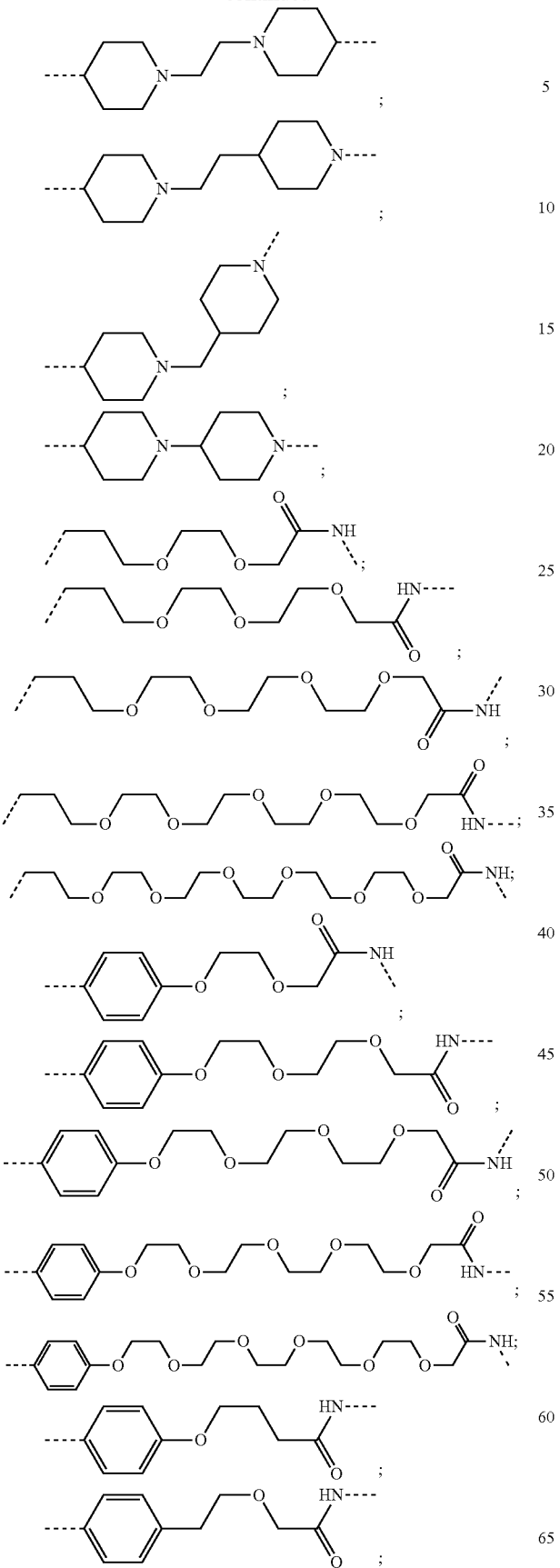
1562
-continued
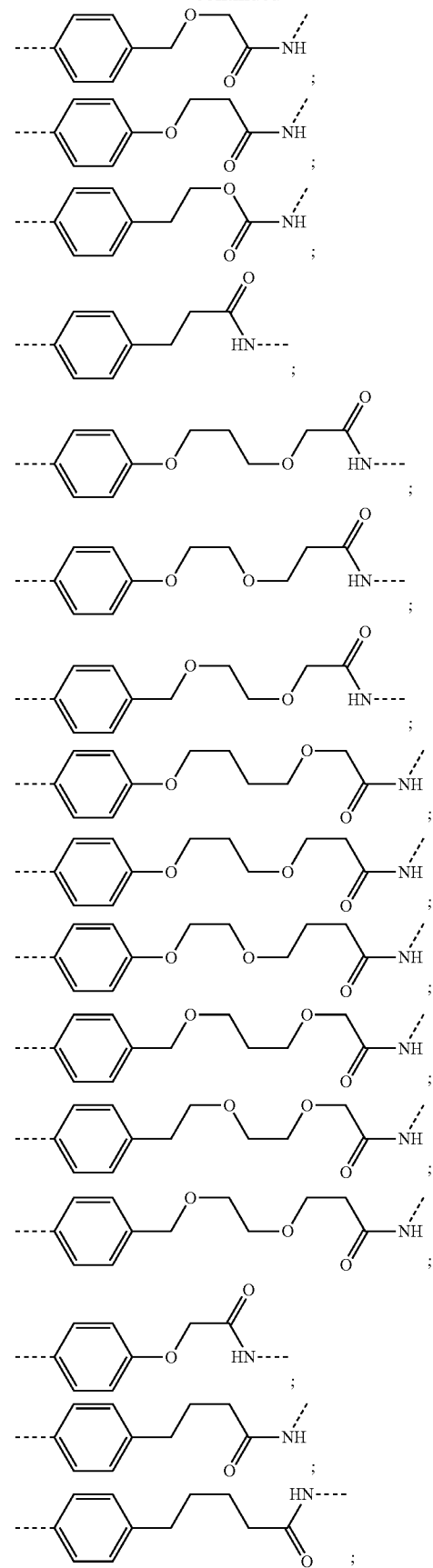

1563
-continued
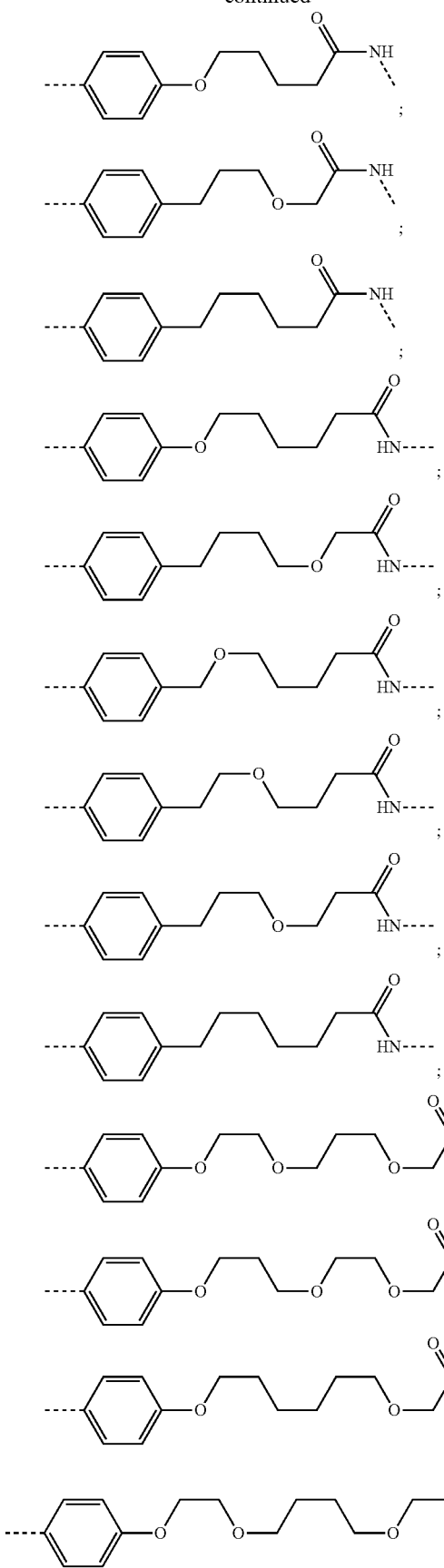
1564
-continued
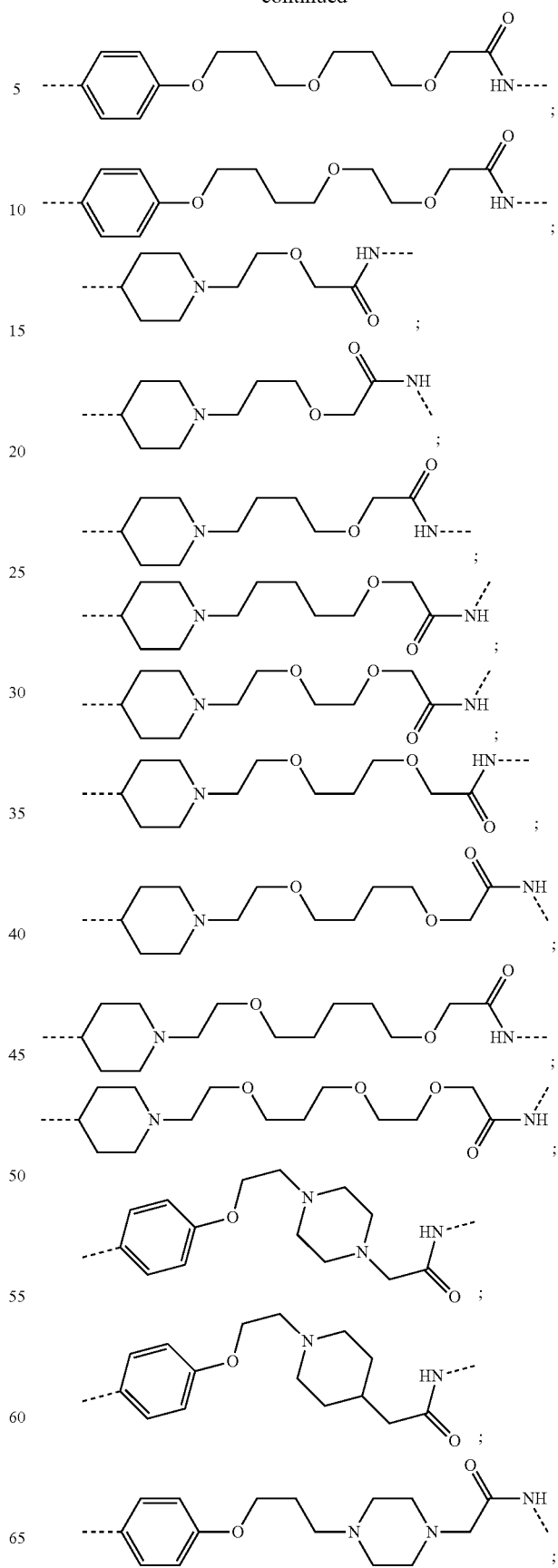

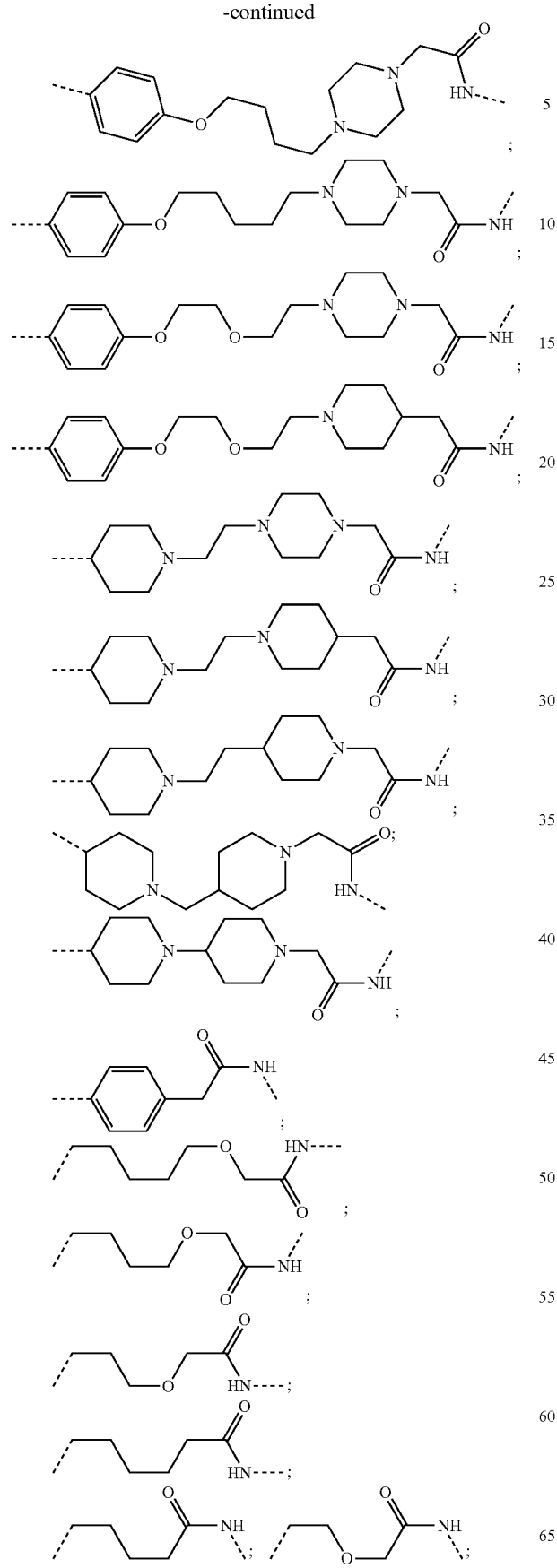
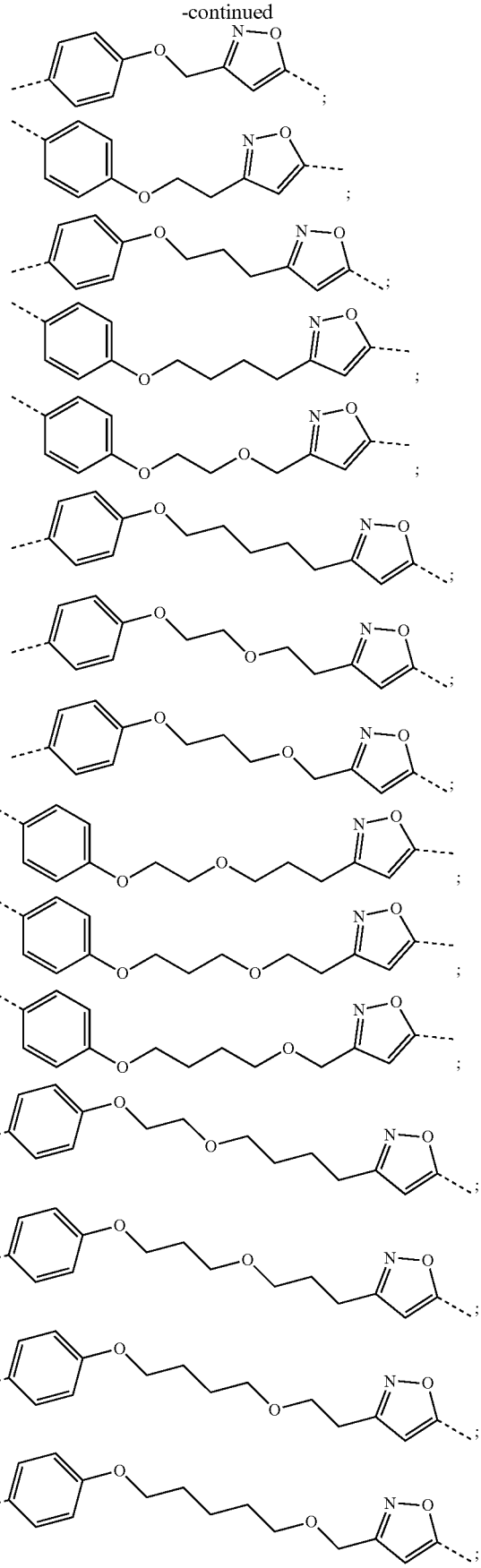

1567
-continued
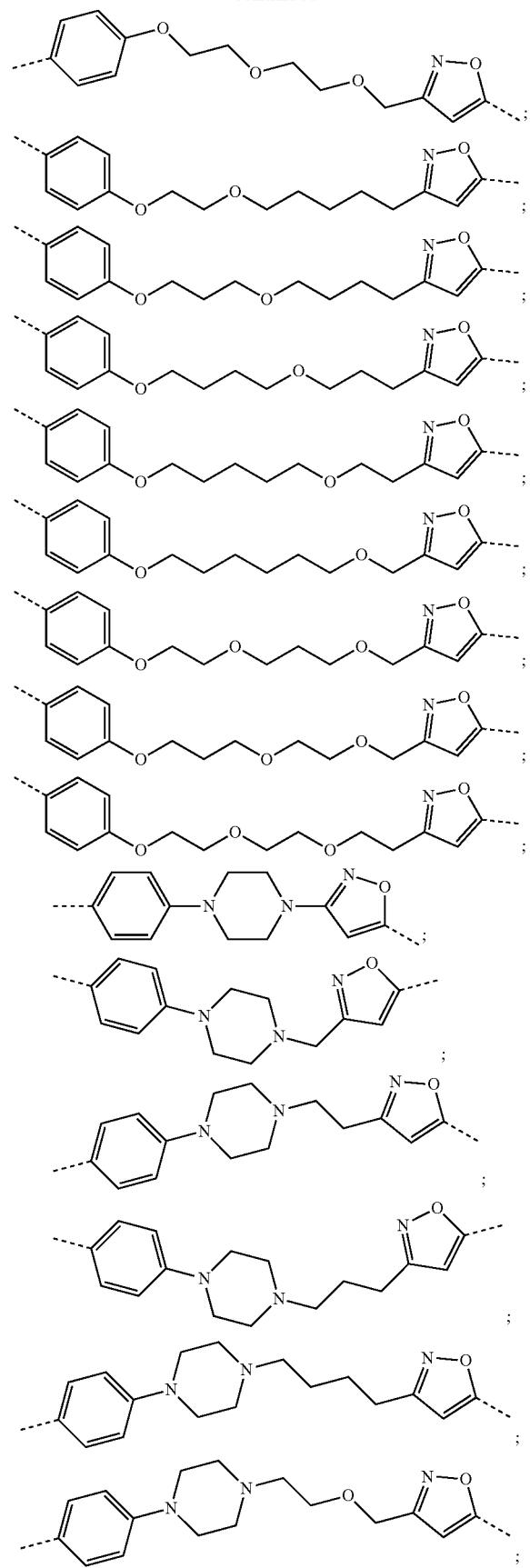
1568
-continued
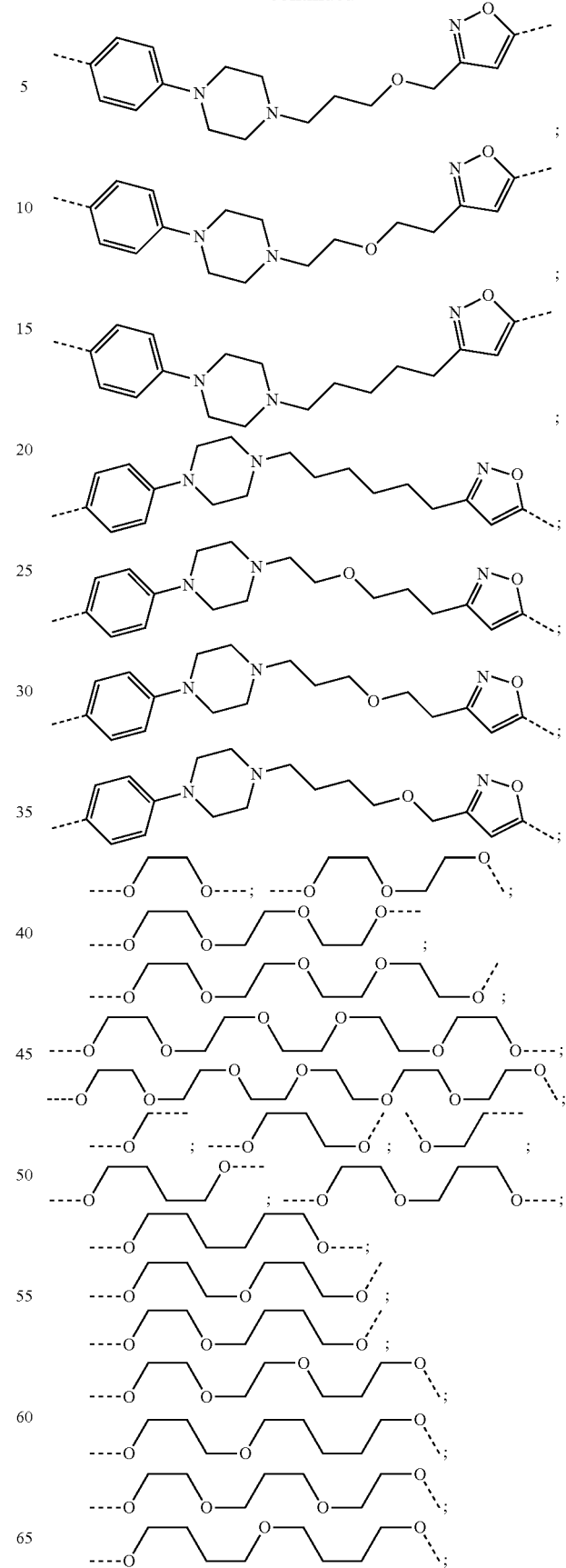

1569
-continued
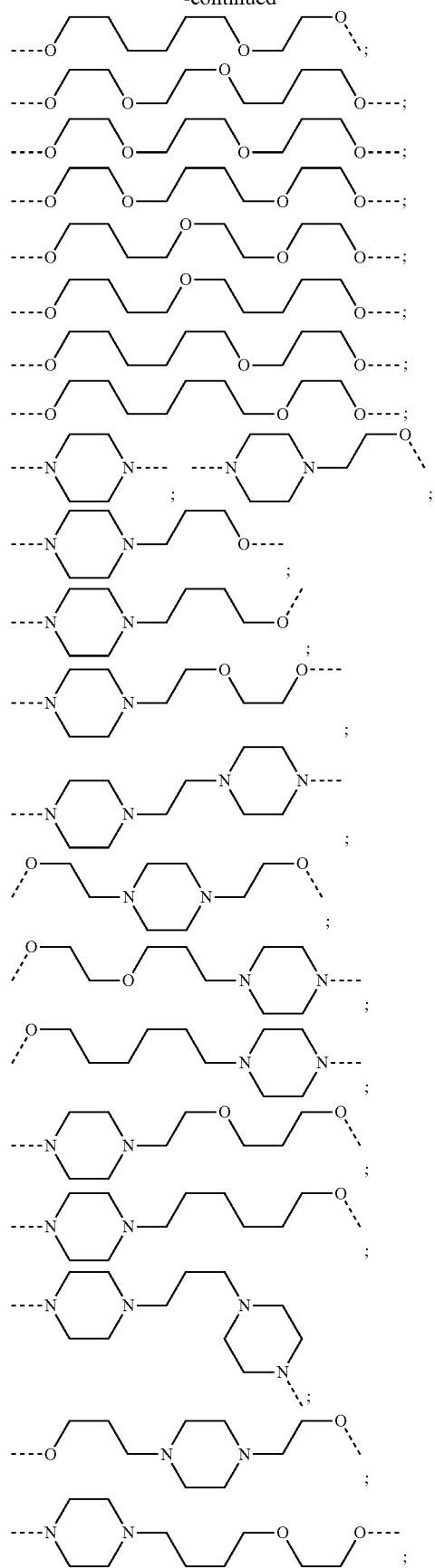
1570
-continued
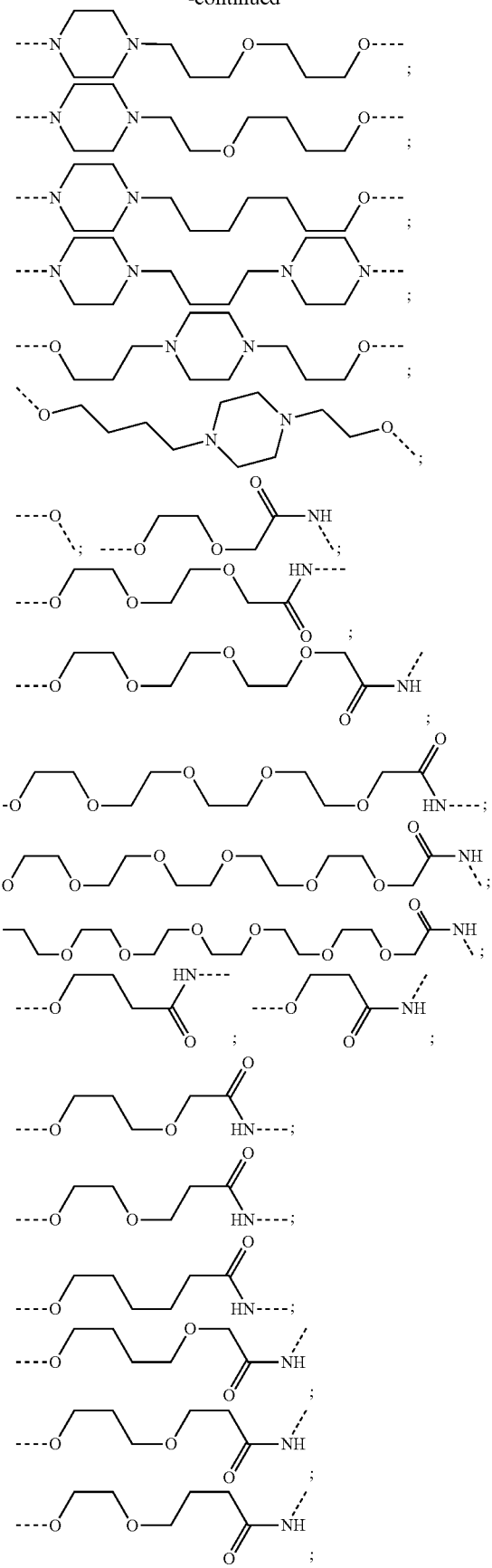

1571
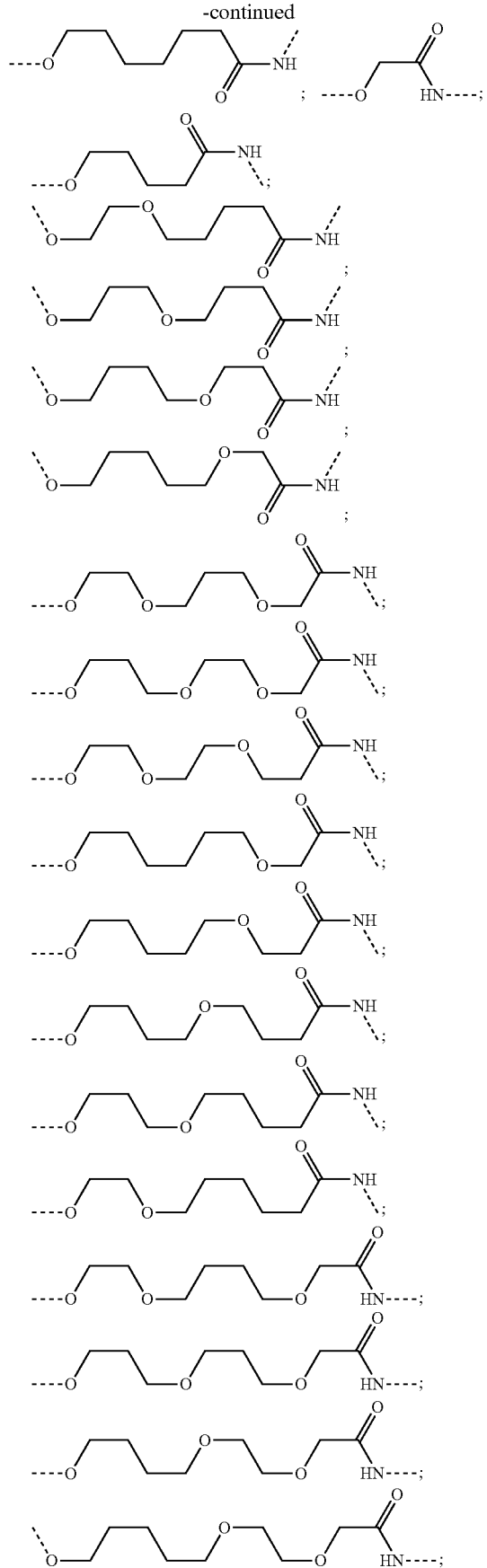
1572
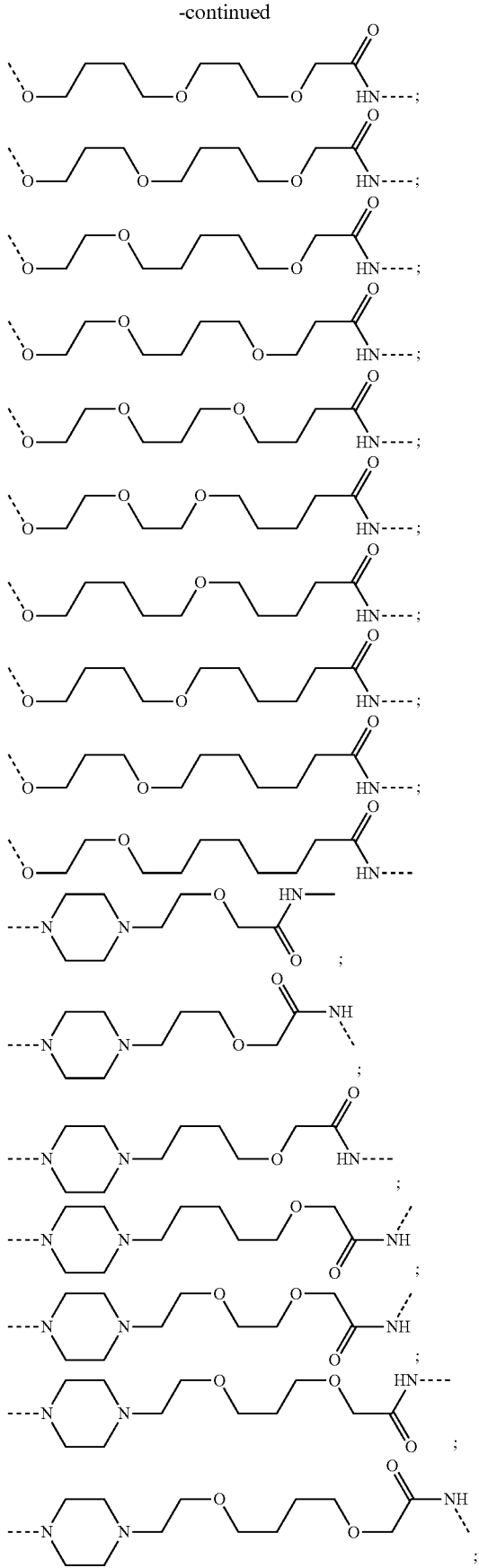

1573
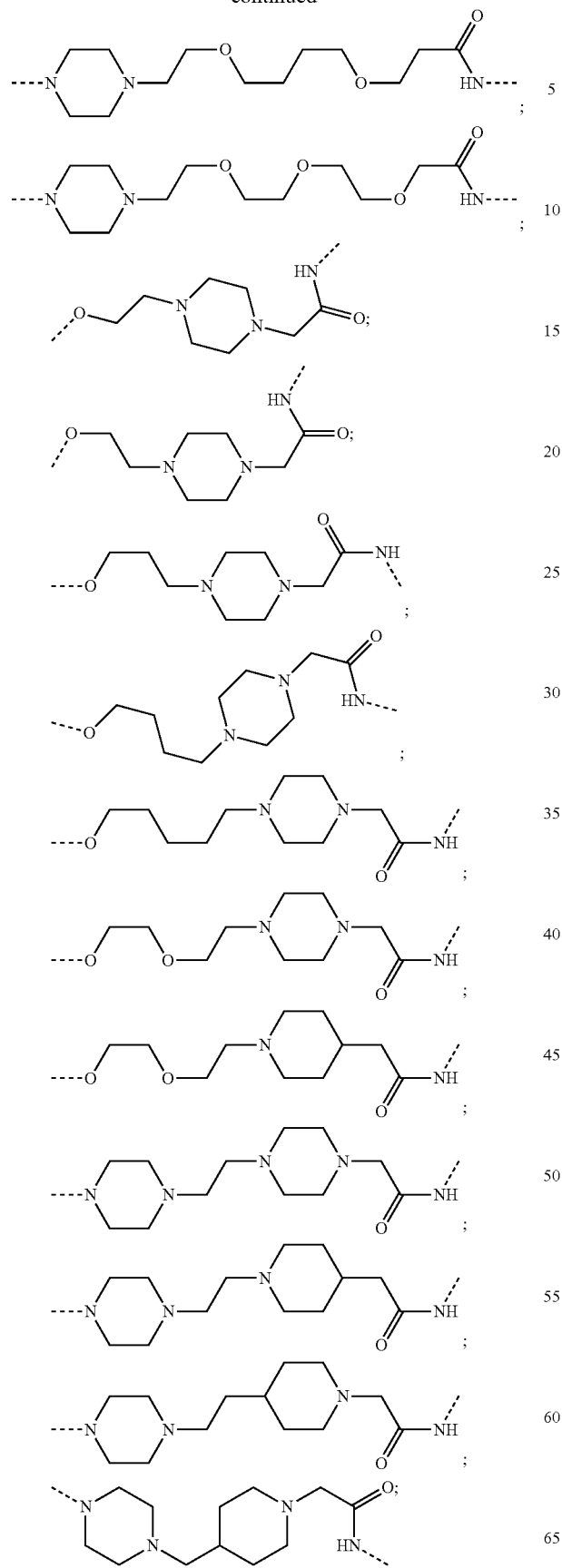
1574
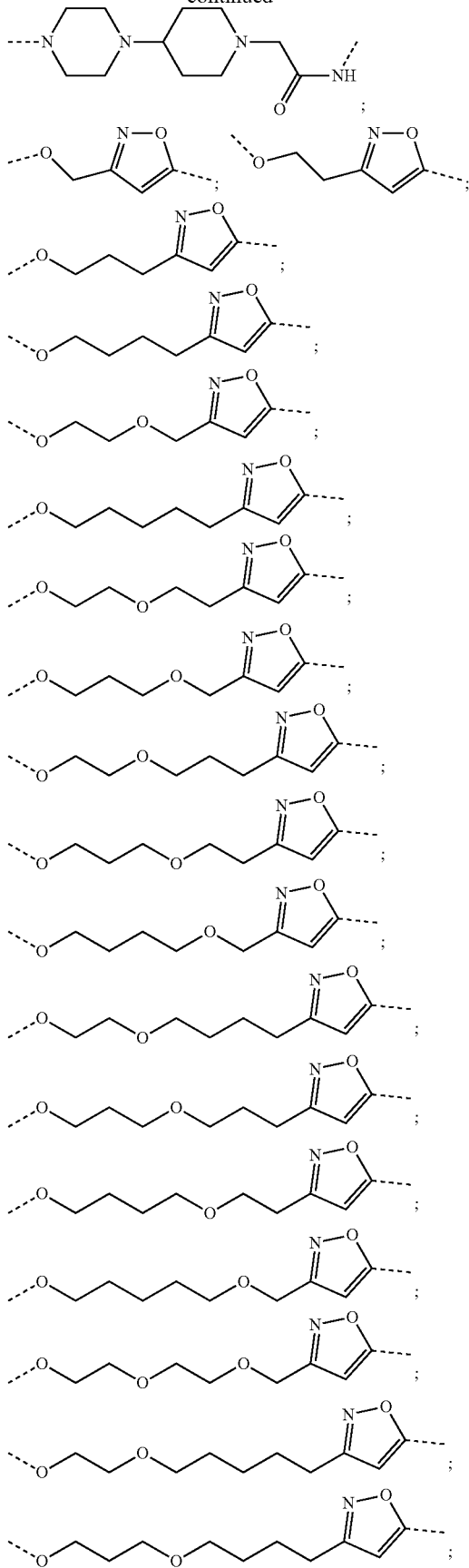

1575
-continued
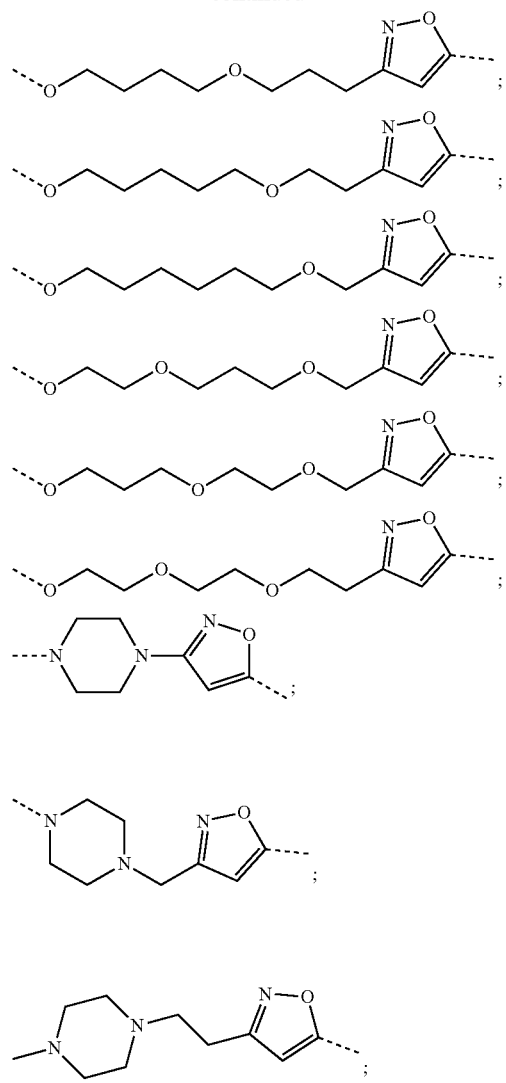
1576
-continued
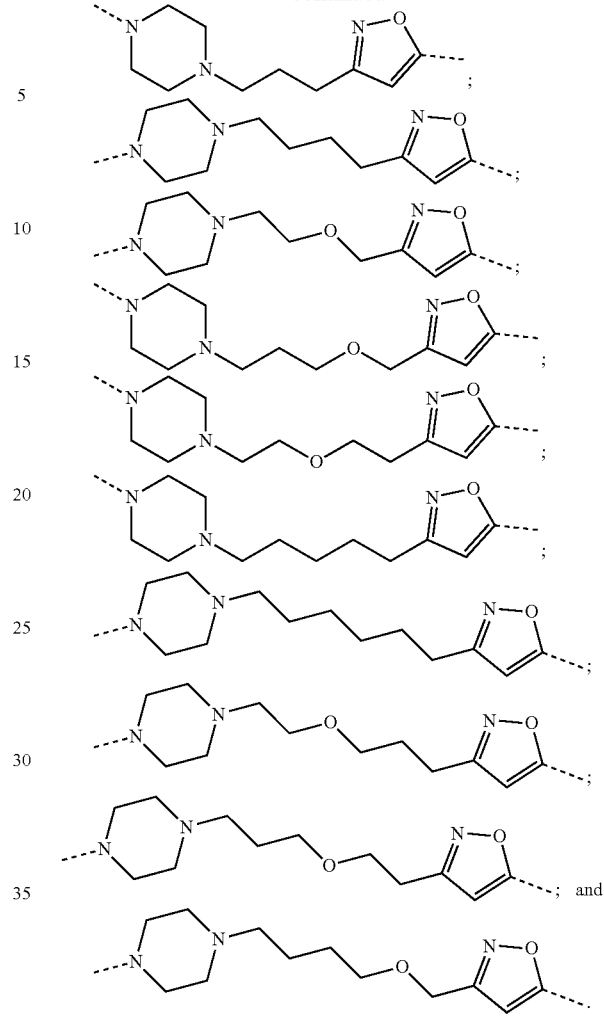
19. The bifunctional compound of claim 1, wherein the compound is selected from Table 1 through Table 12:
(41)
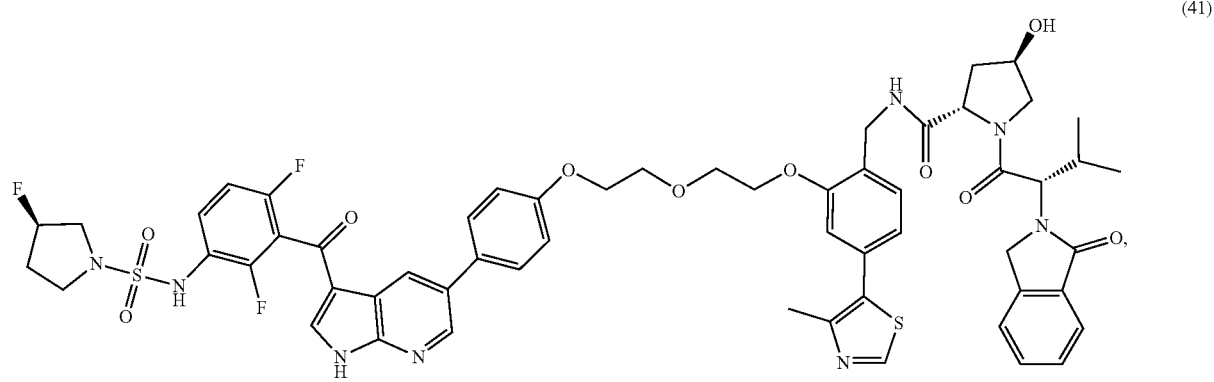

(47)
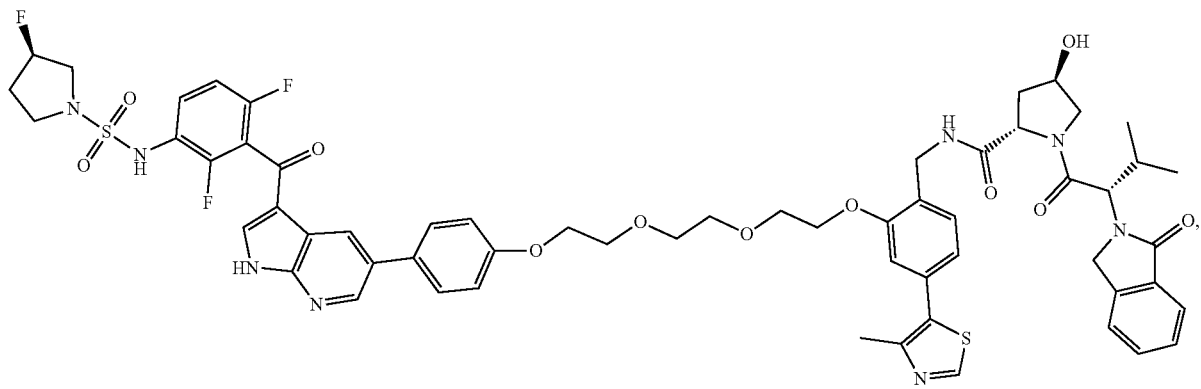
(48)
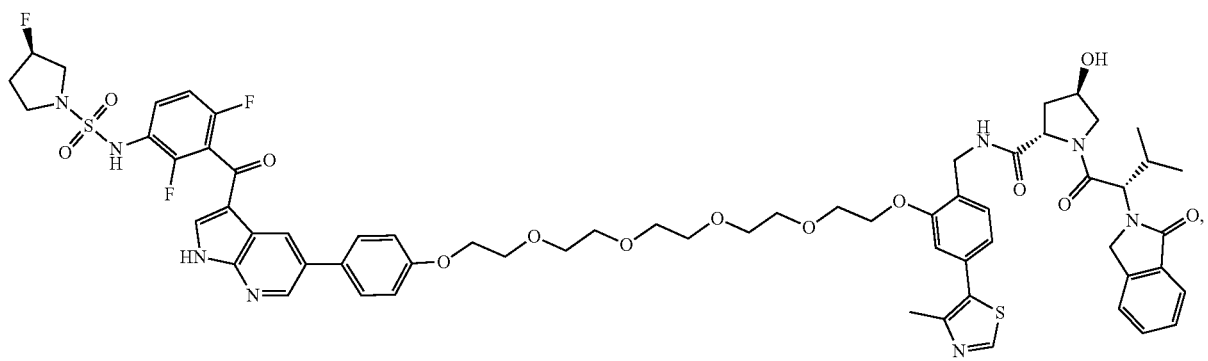
(49)
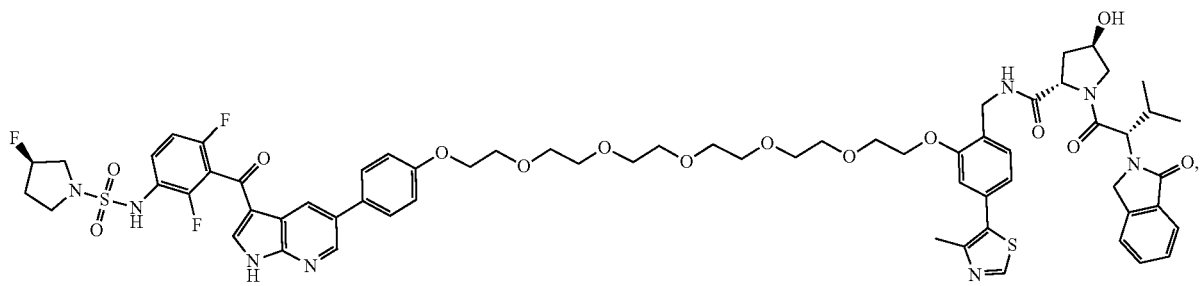
(53)
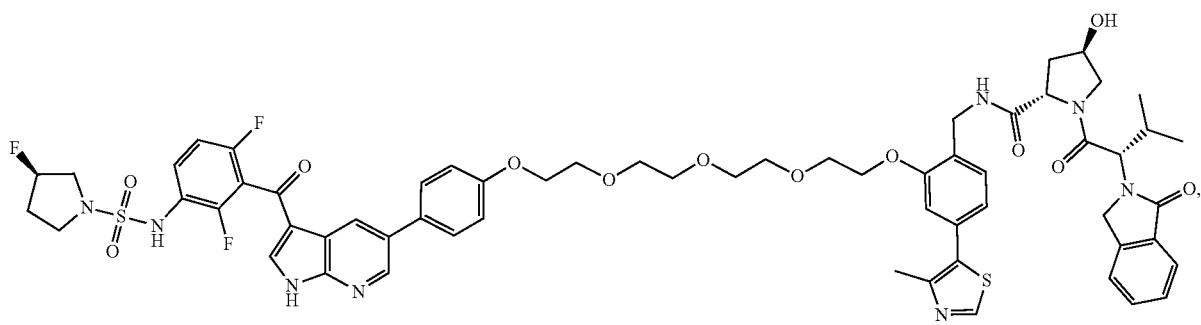

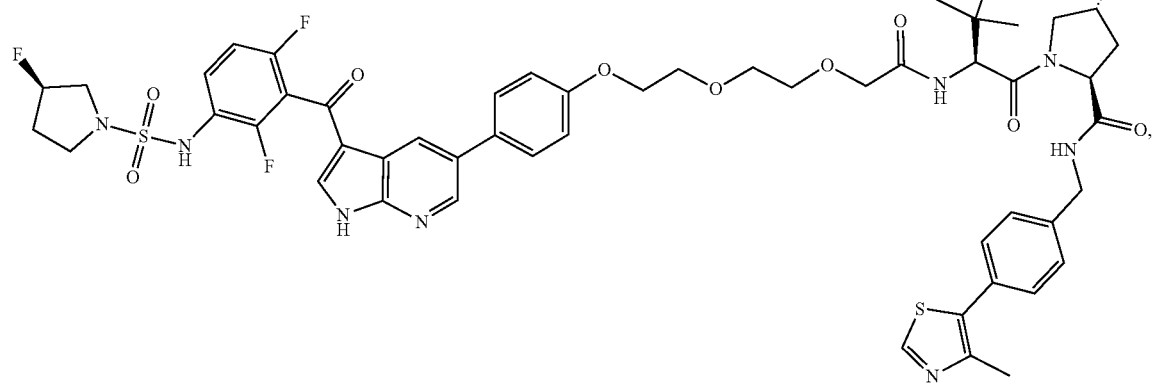
(57)
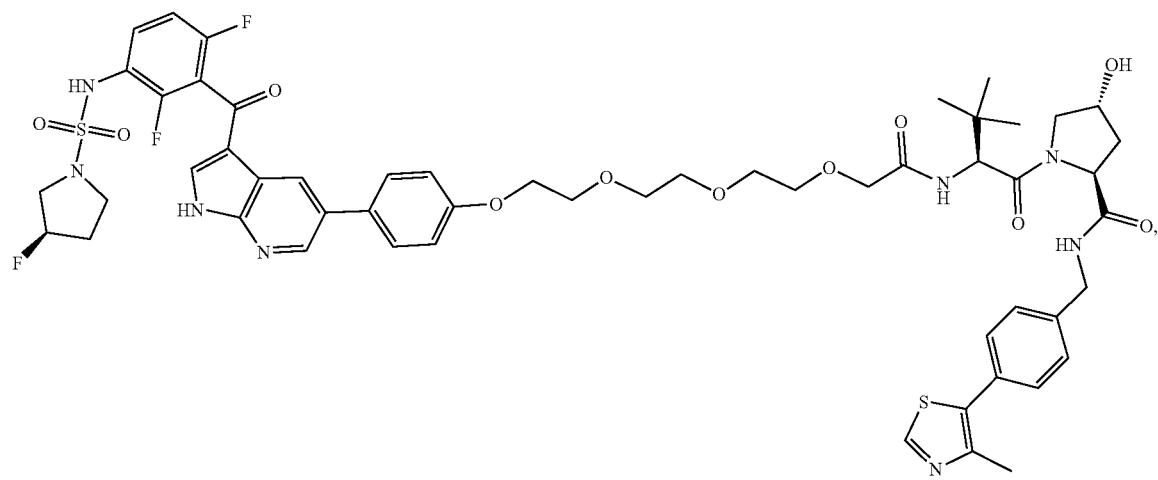
(58)
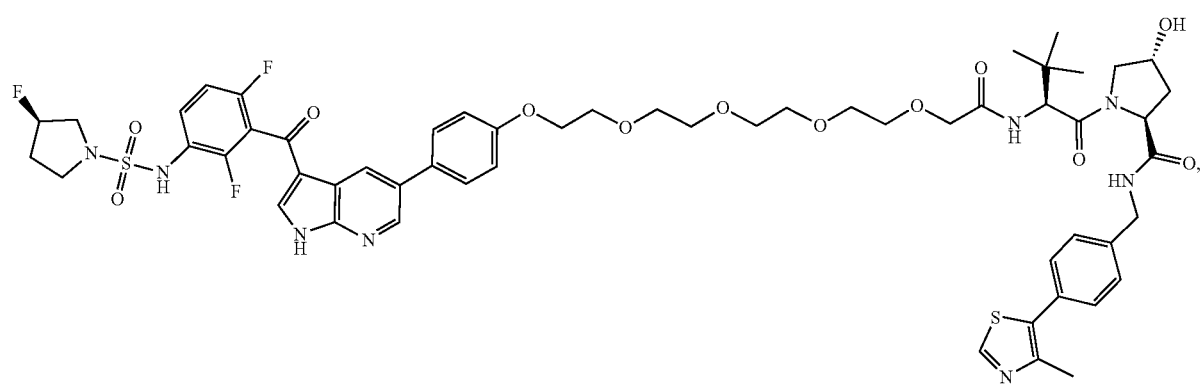
(64)
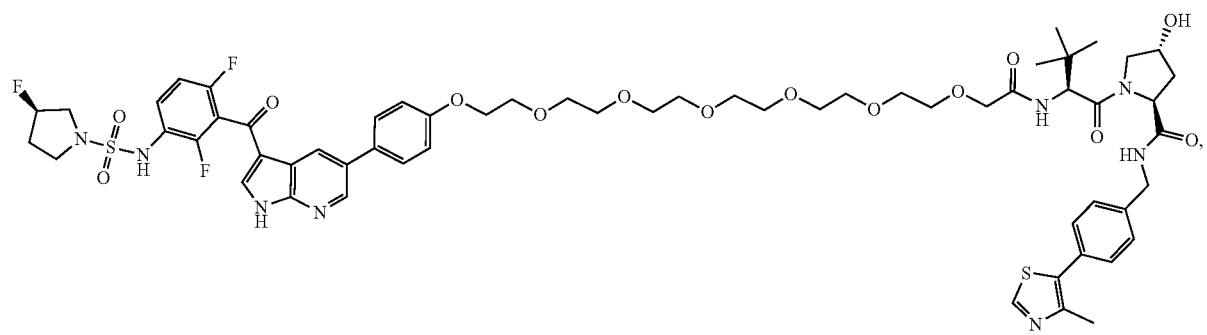
(65)

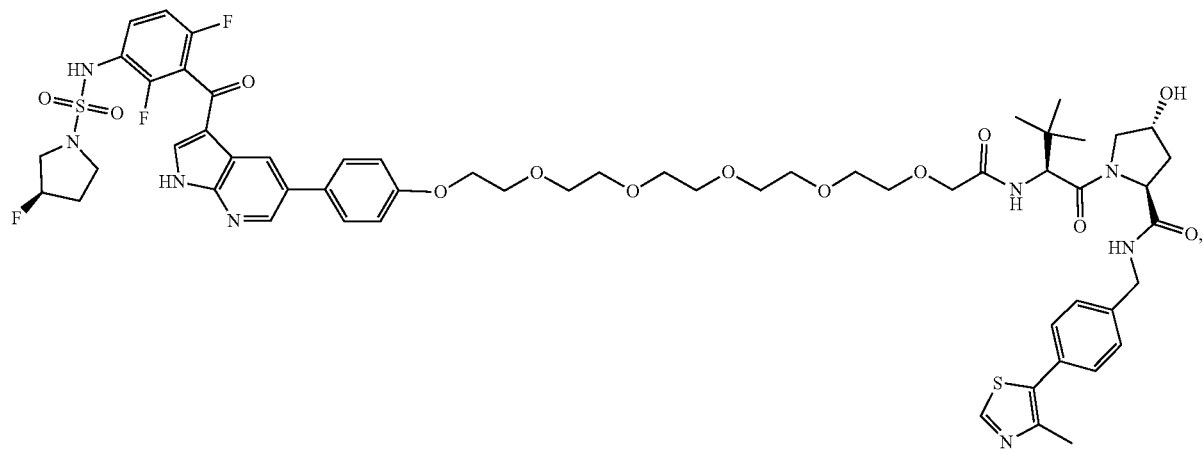
(67)
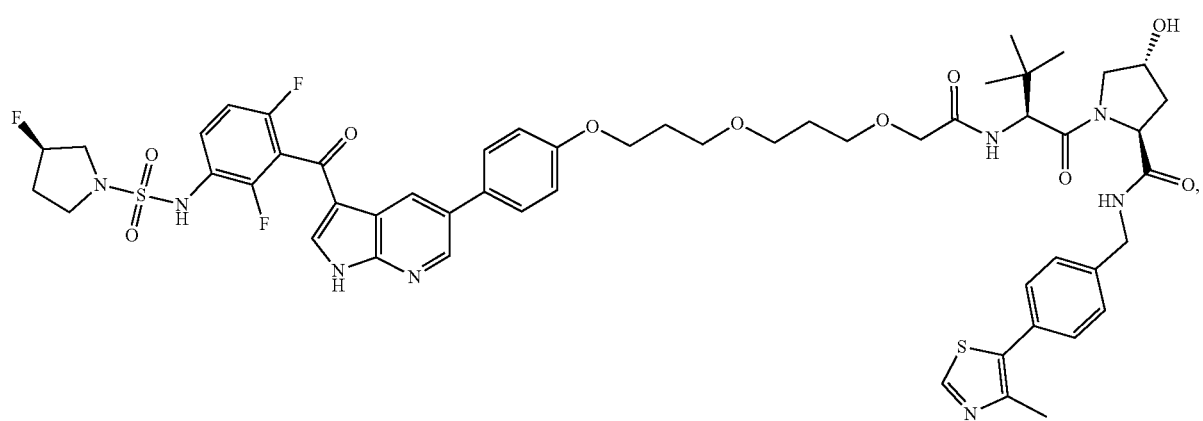
(81)
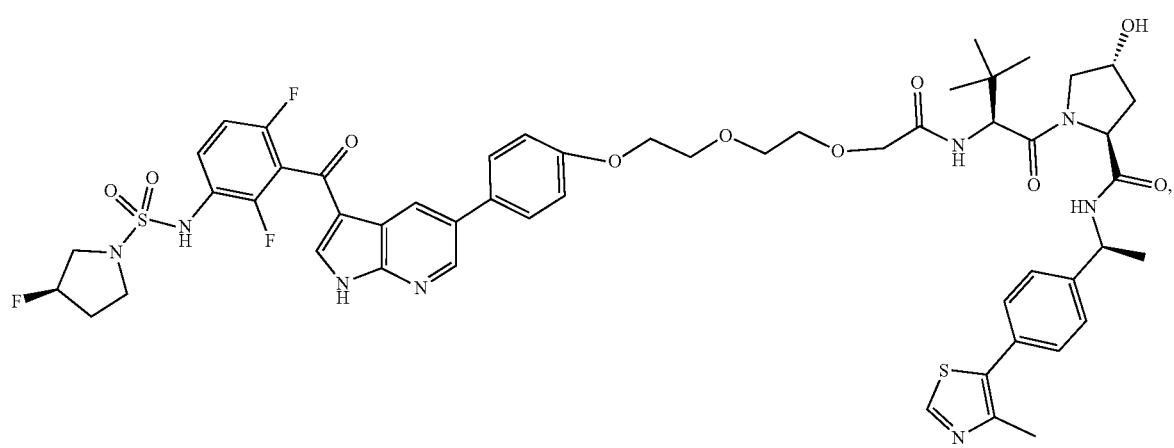
(84)

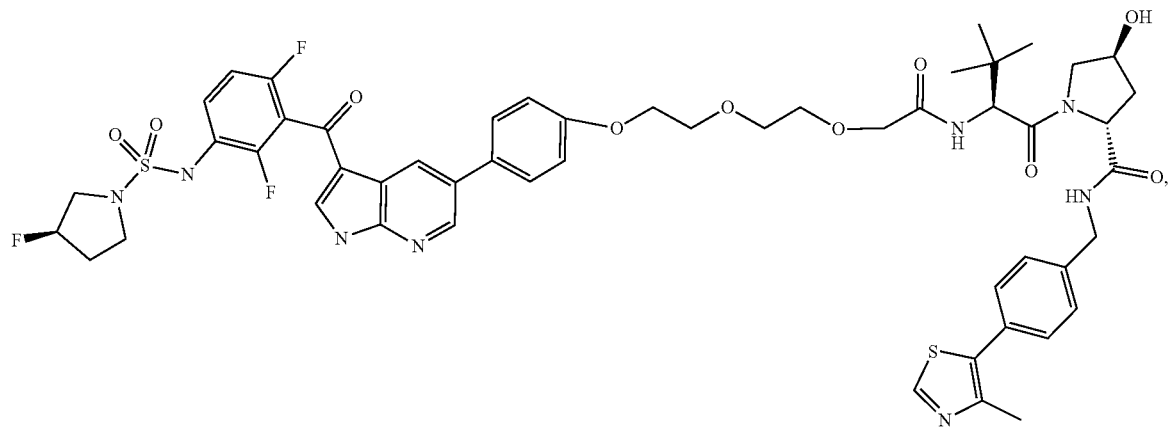
(85)
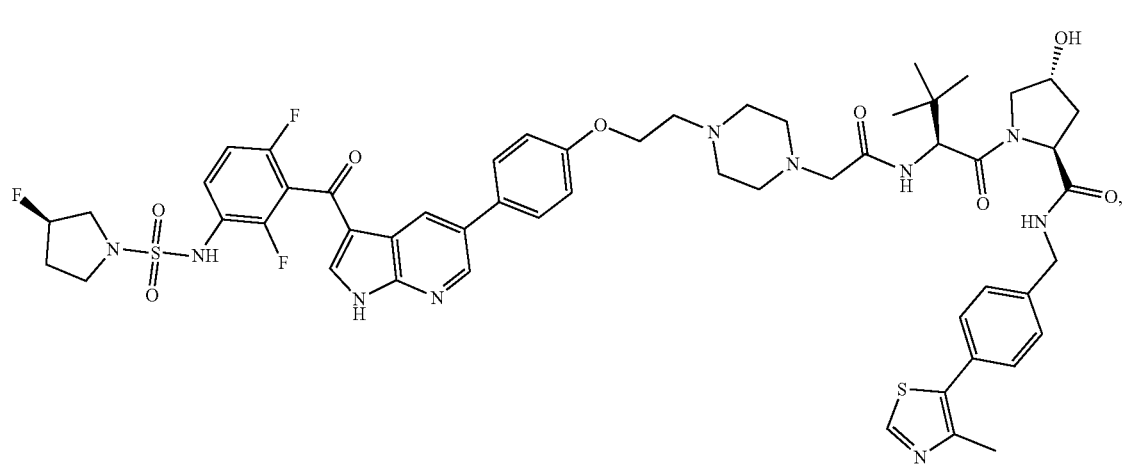
(98)
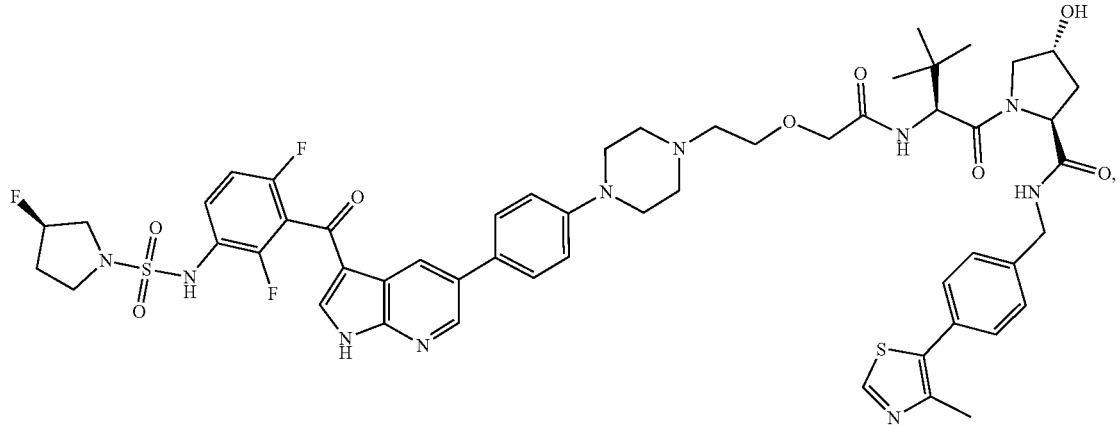
(99)

-continued
(100)
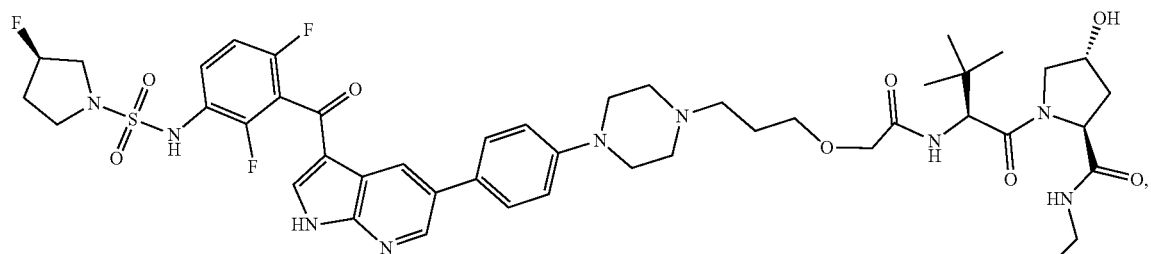
(101)
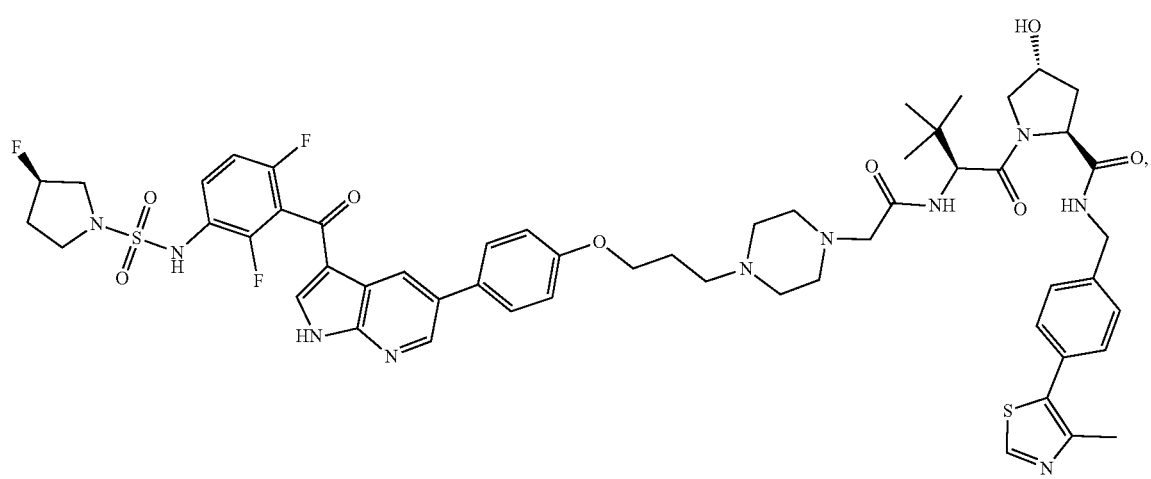
(193)
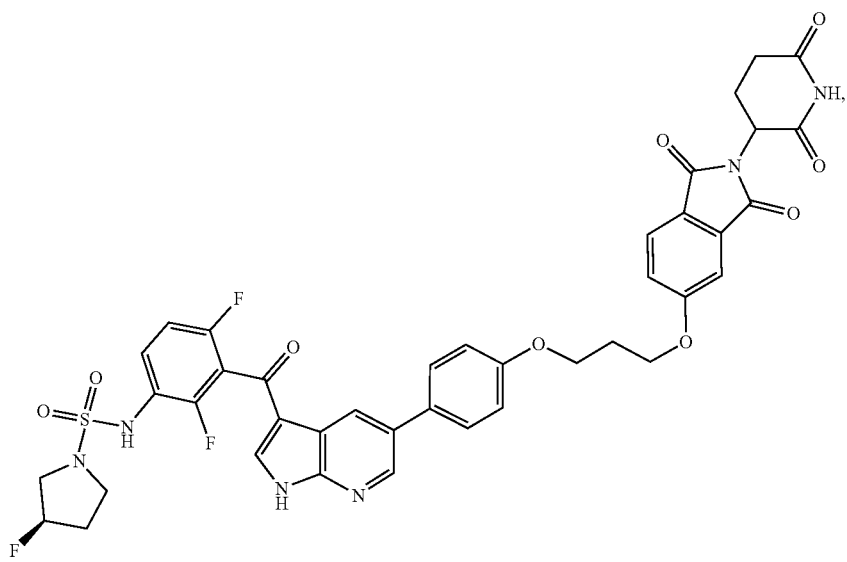

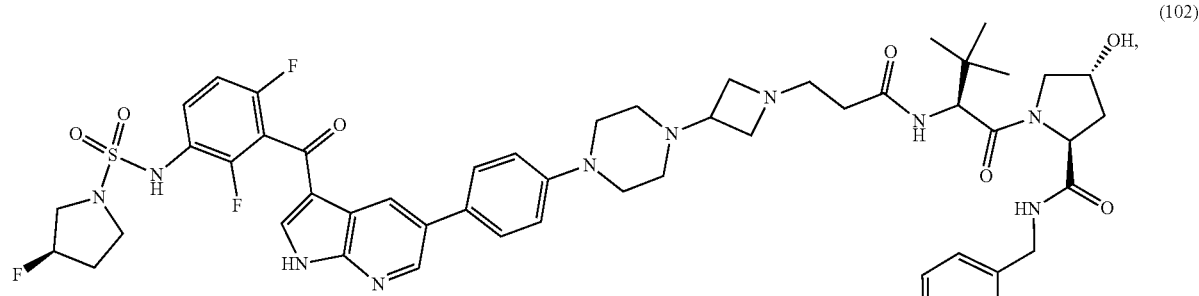
(102)
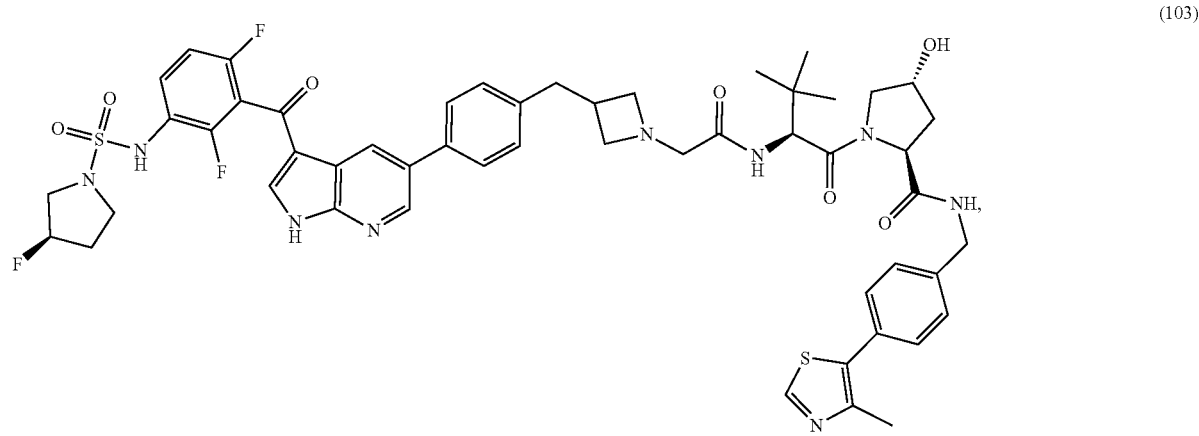
(103)
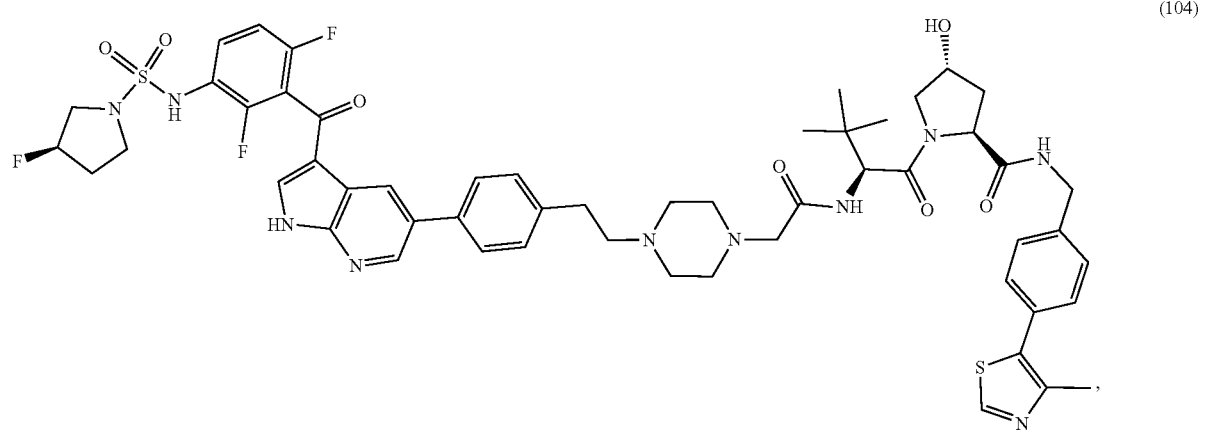
(104)
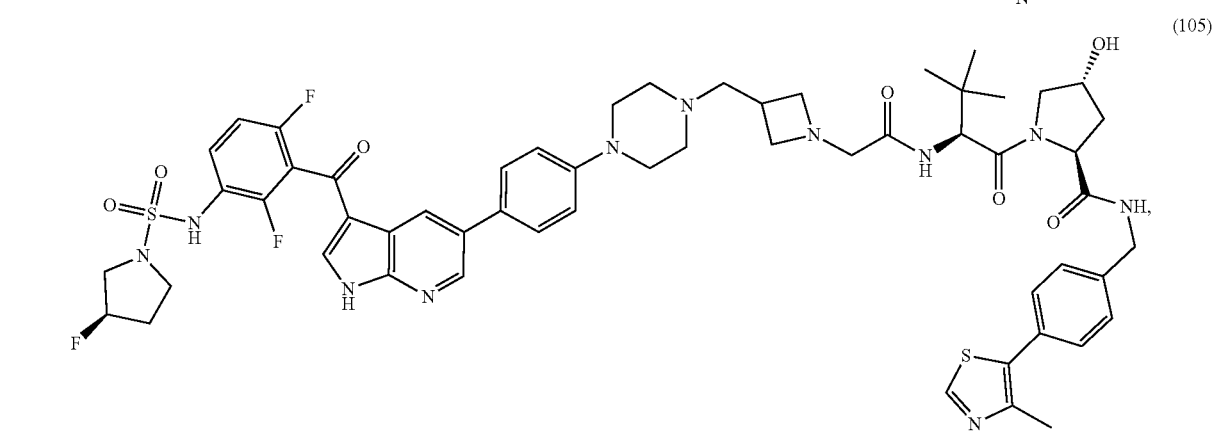
(105)

-continued
(106)
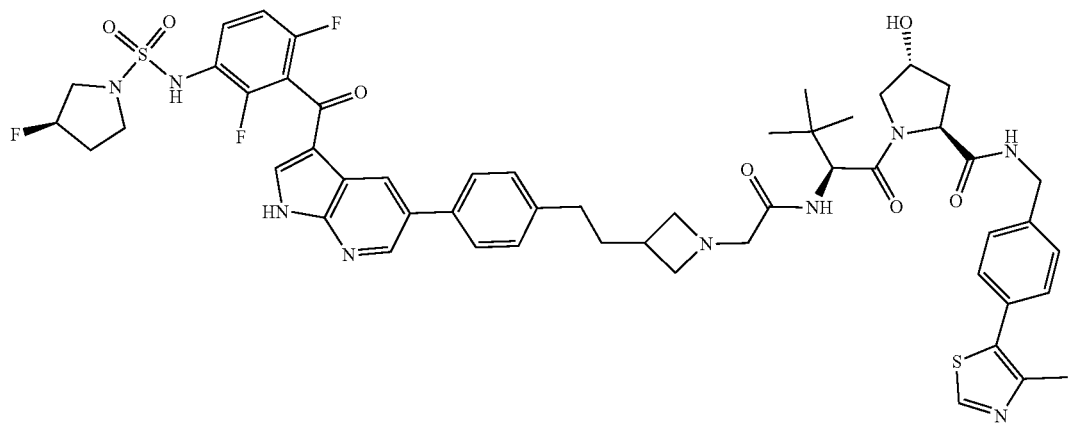
(107)
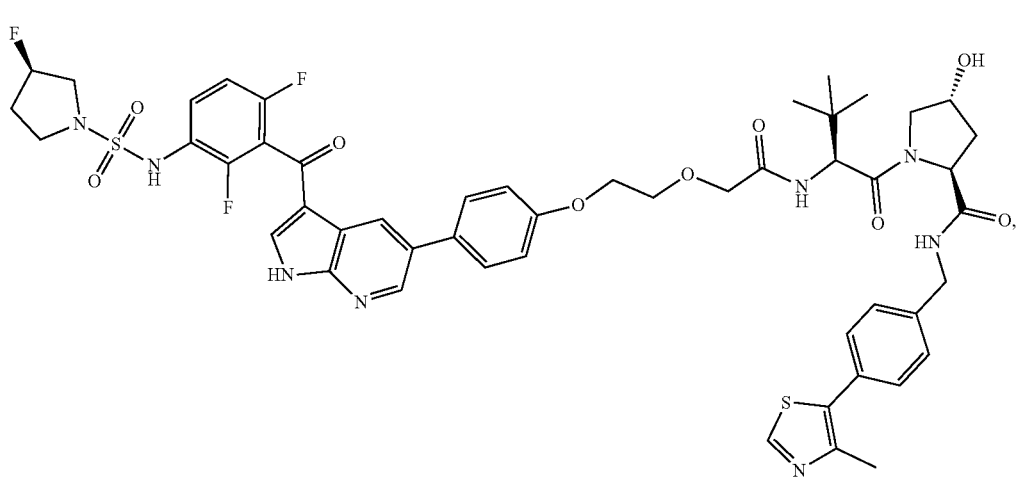
(108)
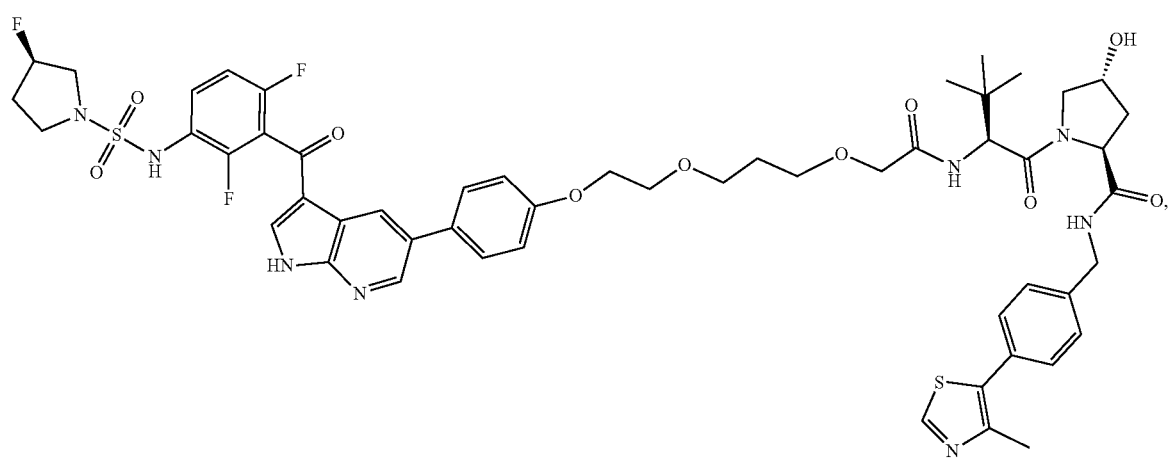

(109)
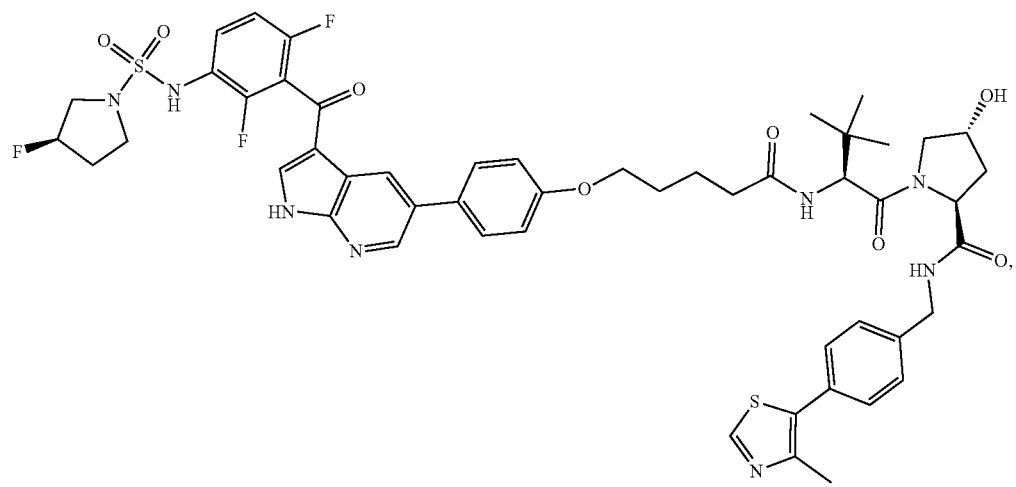
(110)
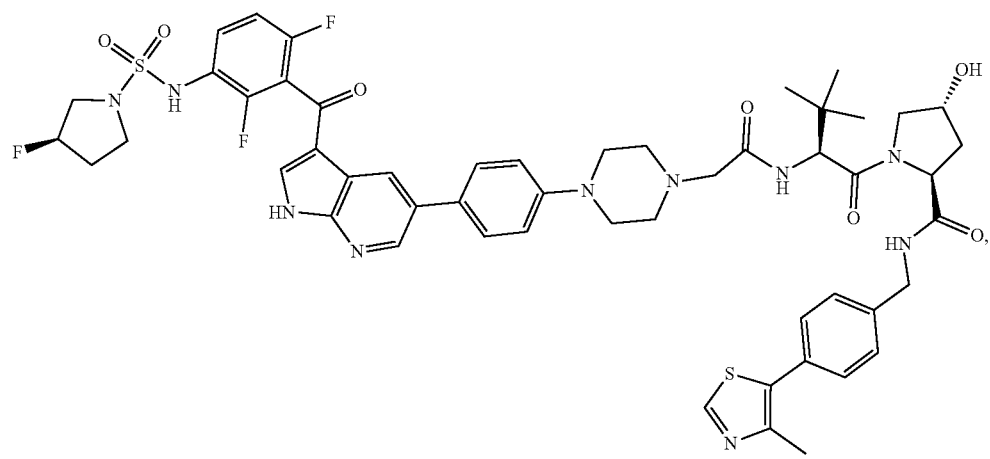
(111)
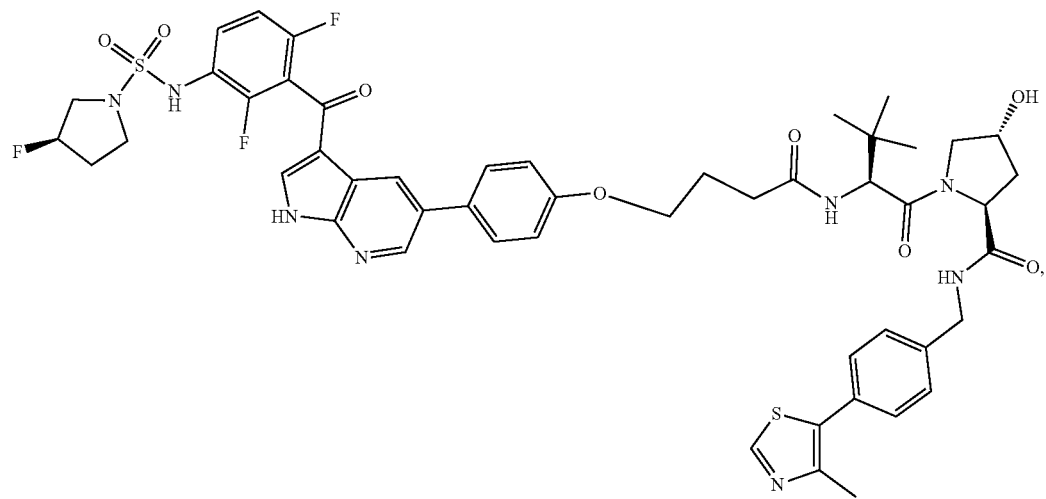

1593 1594
-continued
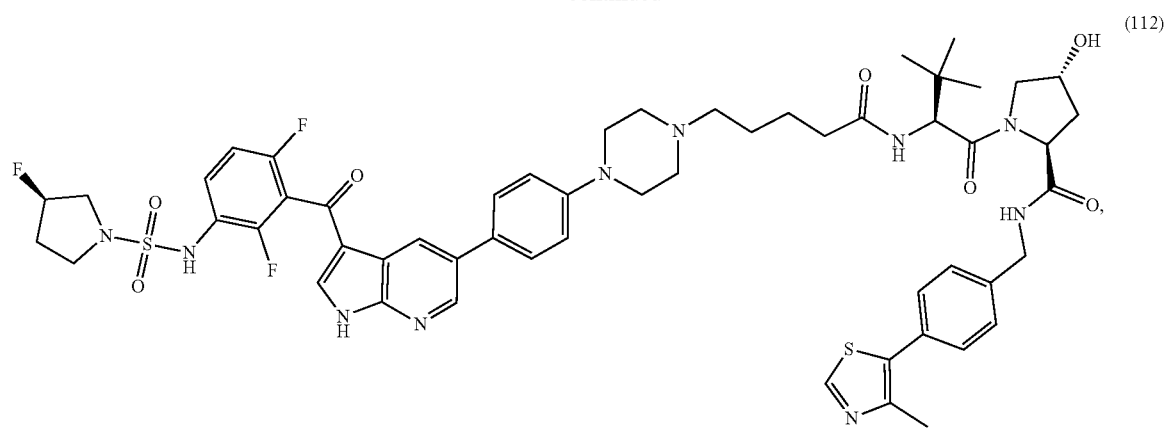
(112)
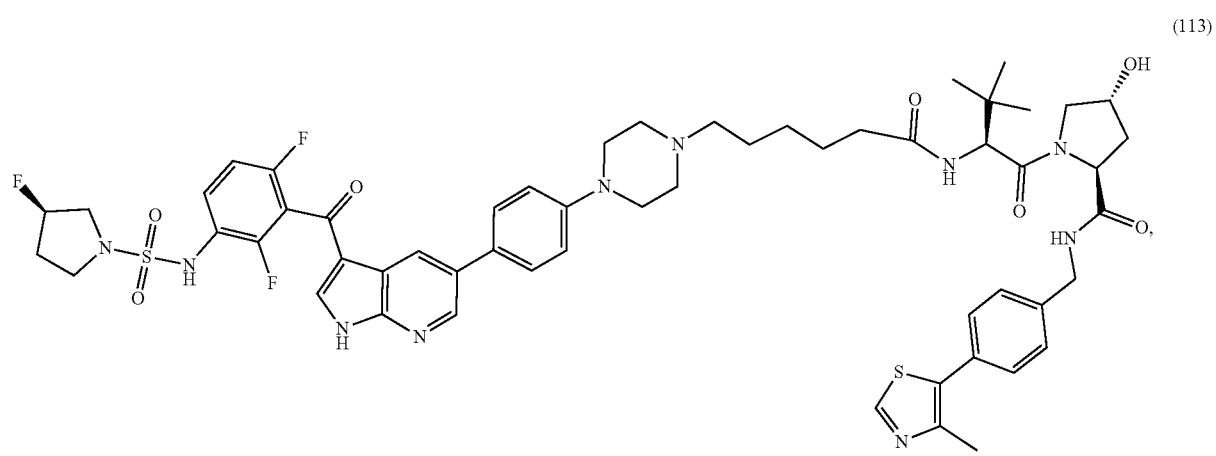
(113)
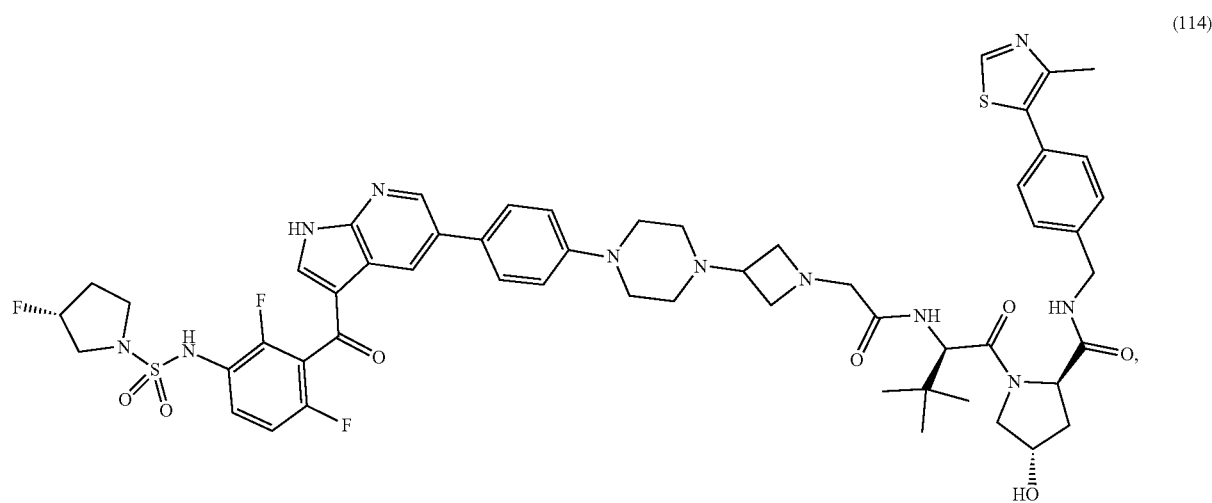
(114)

(115)
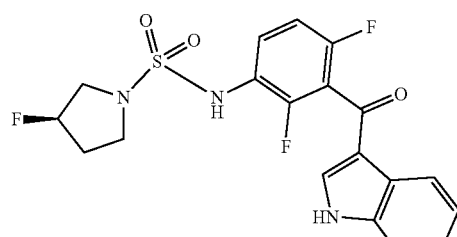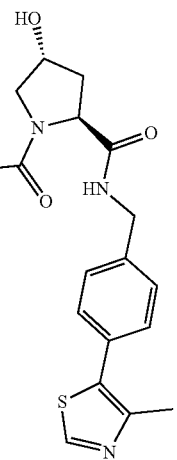
(116)
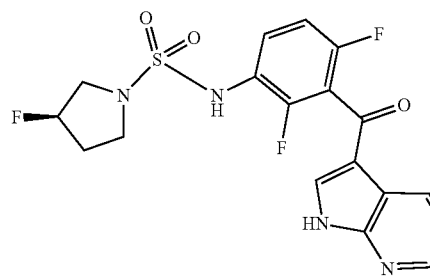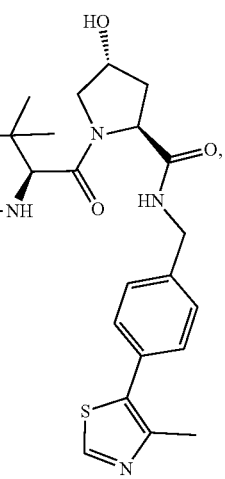
(216)
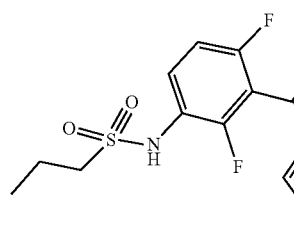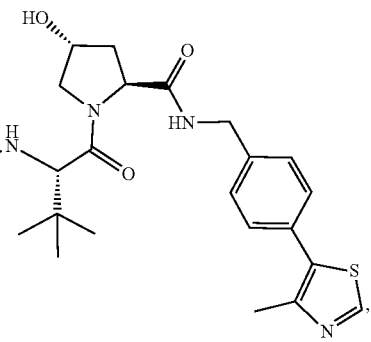
(217)
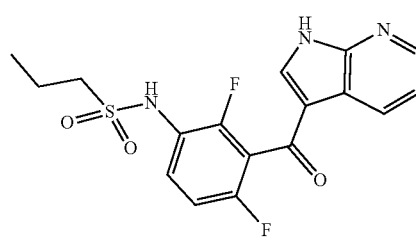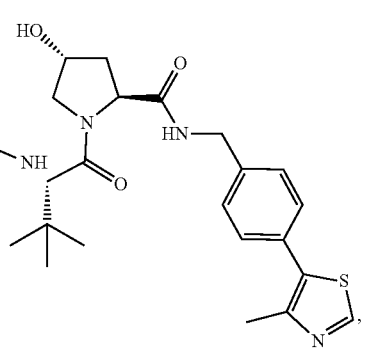

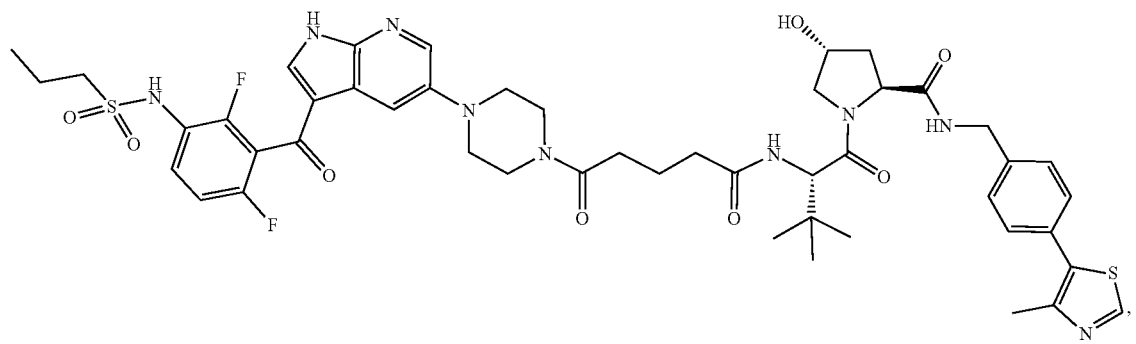
(218)
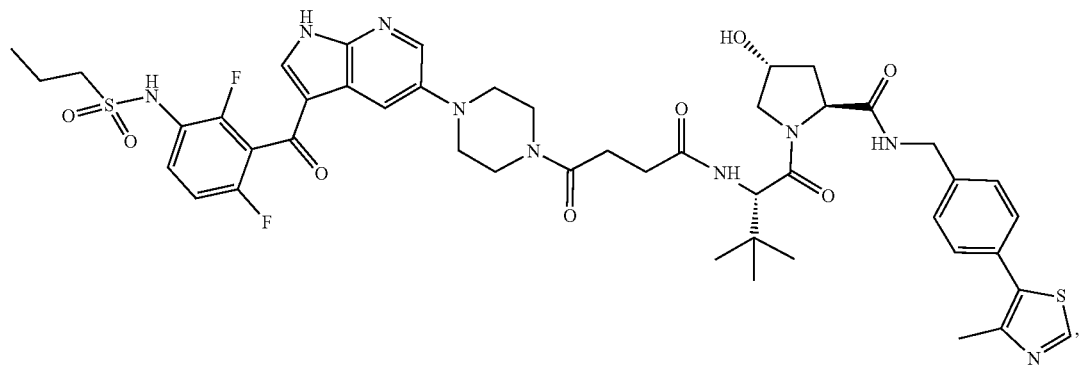
(219)
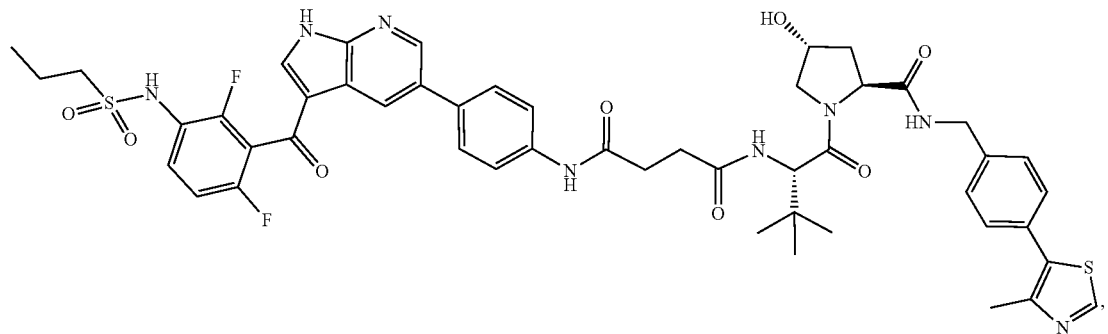
(220)
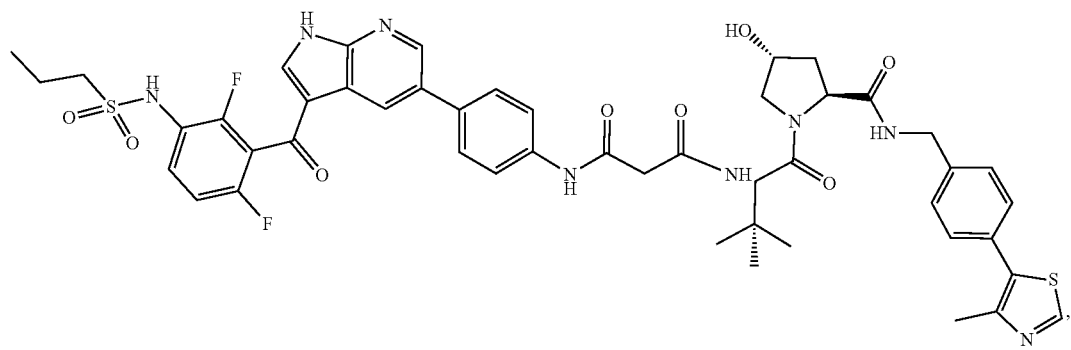
(221)

(222)
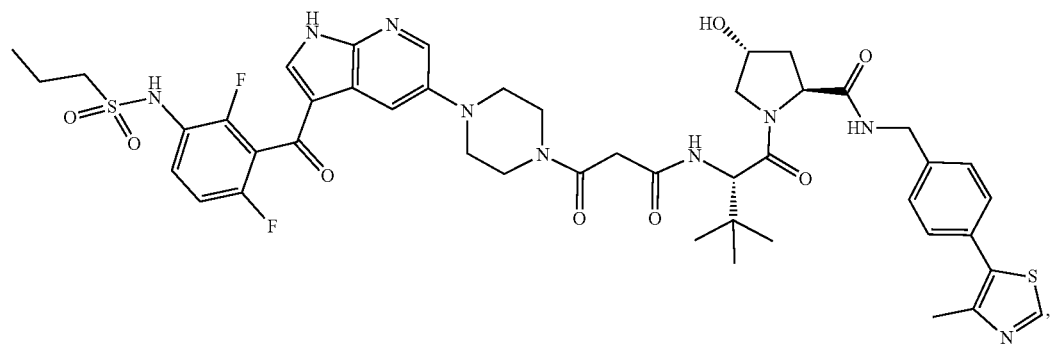
(223)
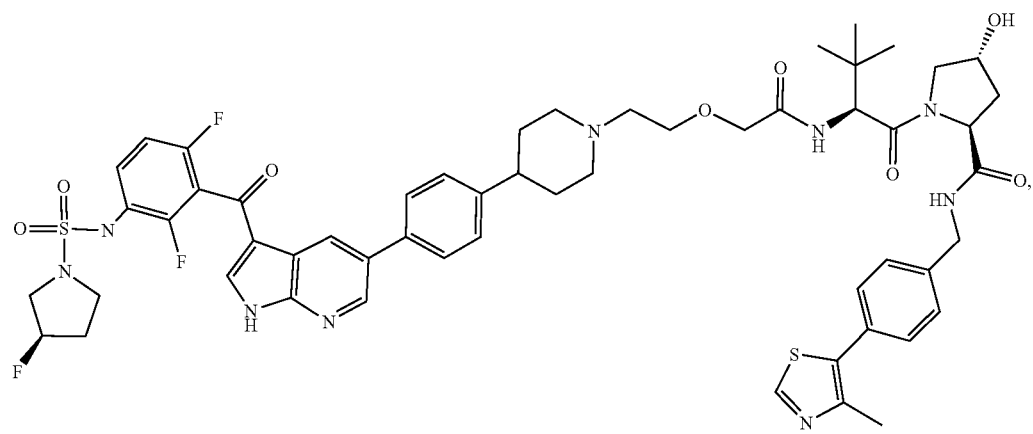
(224)
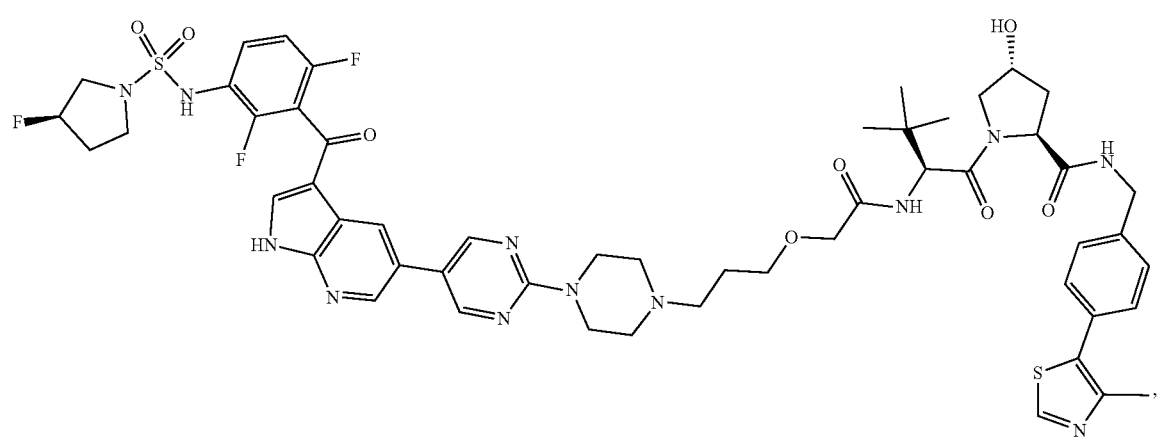
(225)
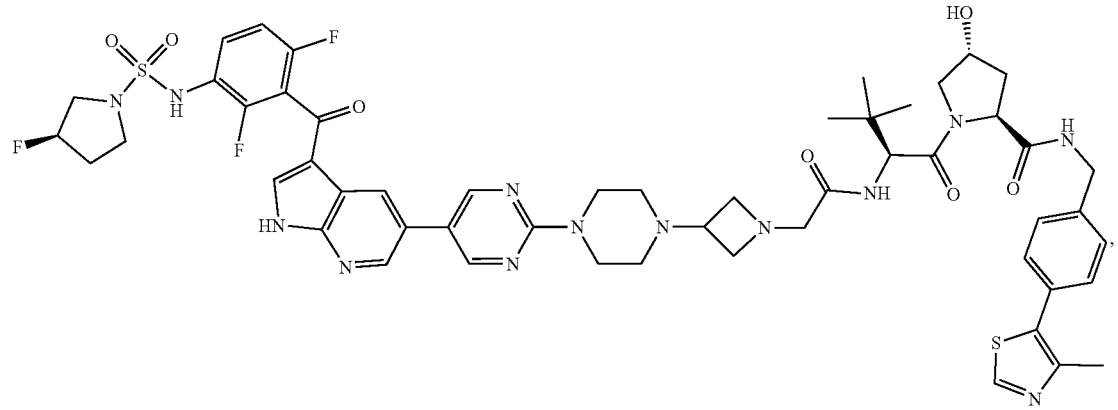

(226)
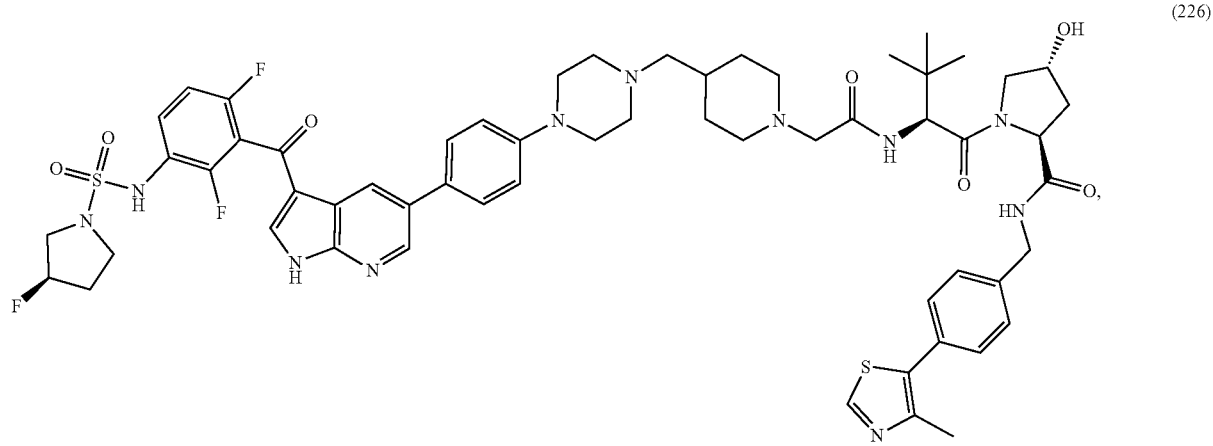
(227)
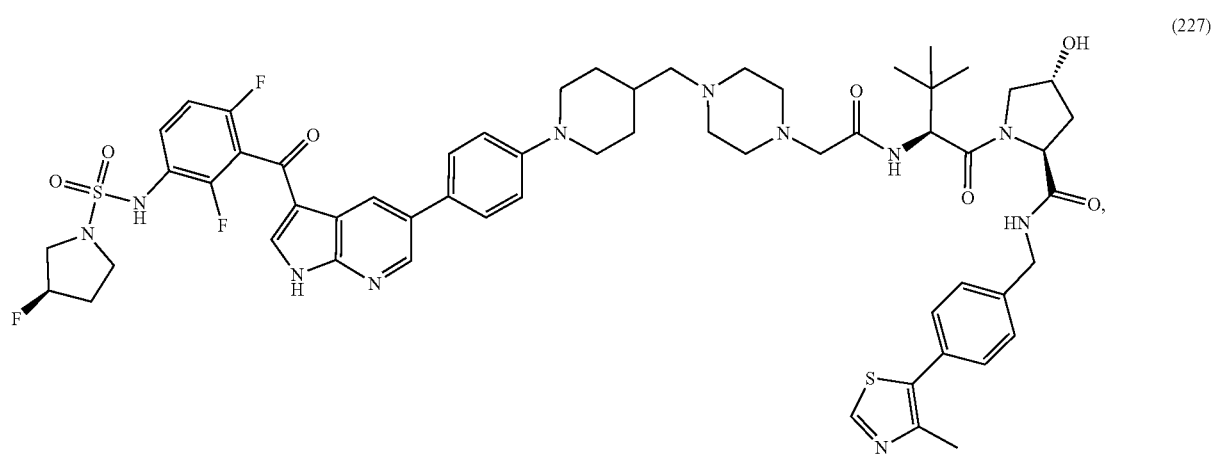
(228)
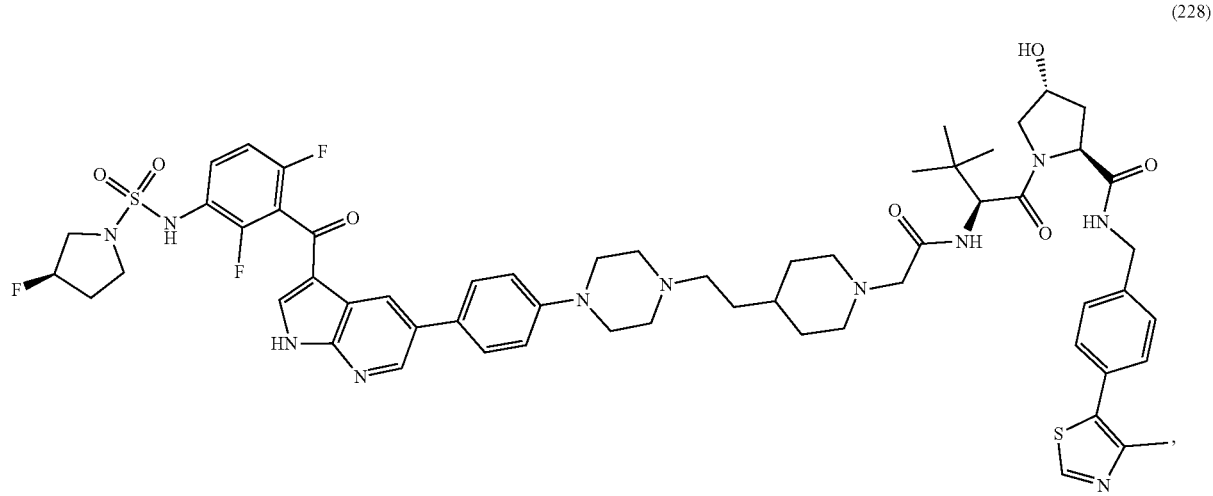

1603
1604
-continued
(229)
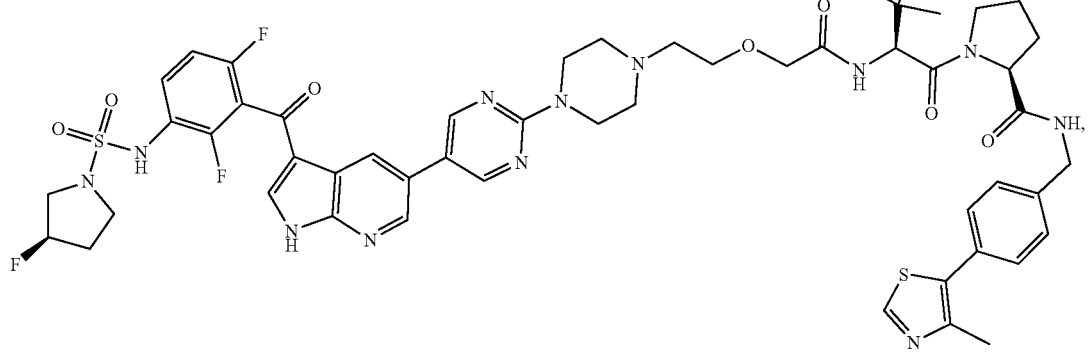
(230)
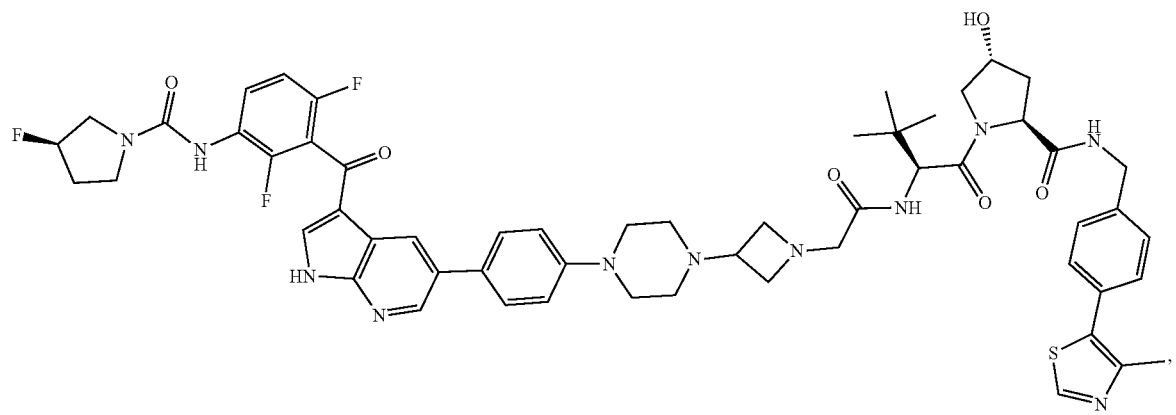
(231)
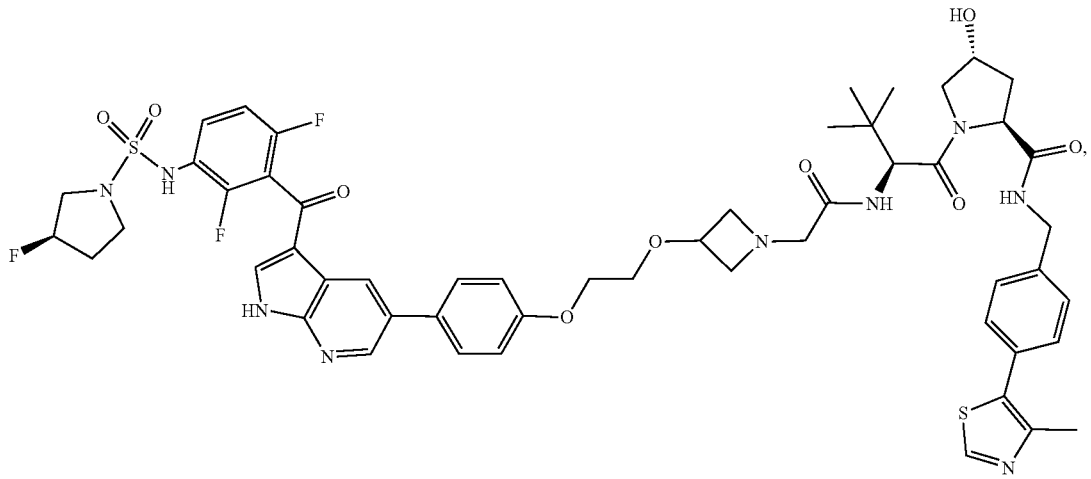

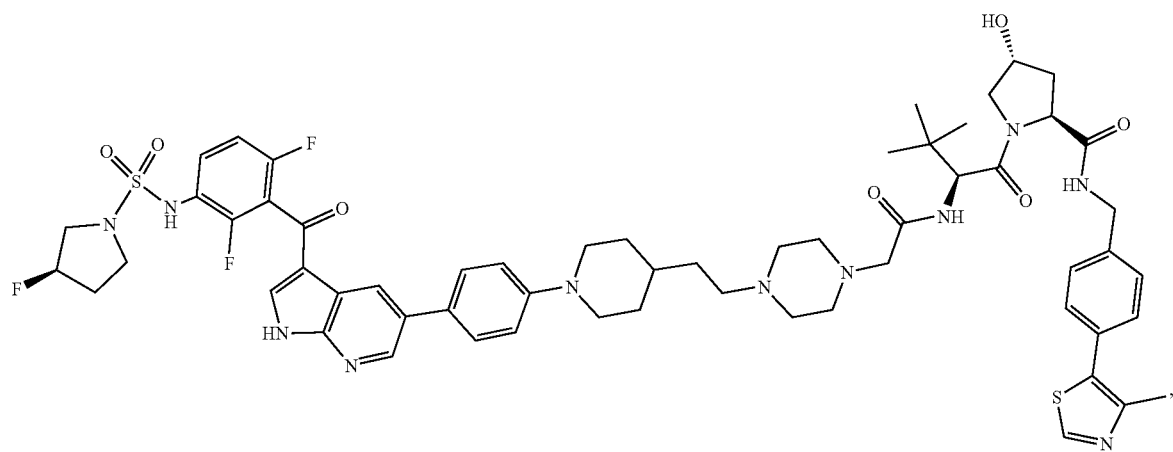
(232)
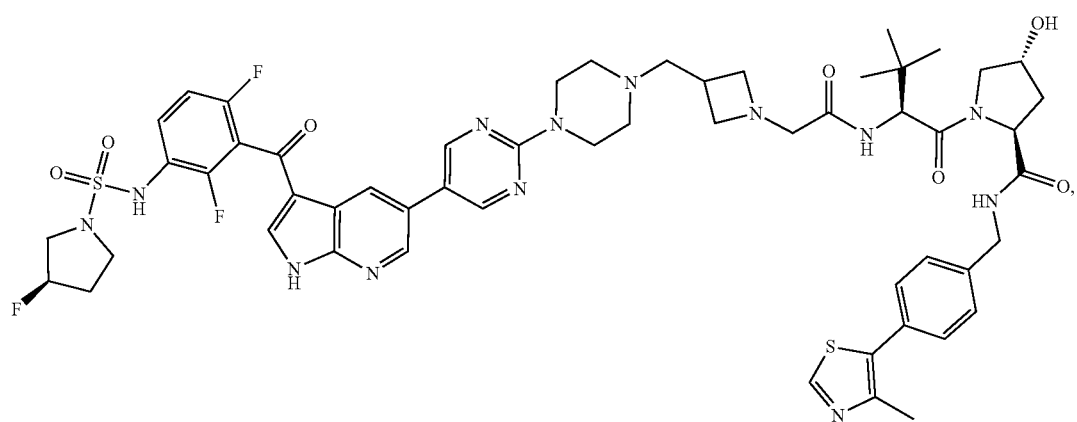
(233)
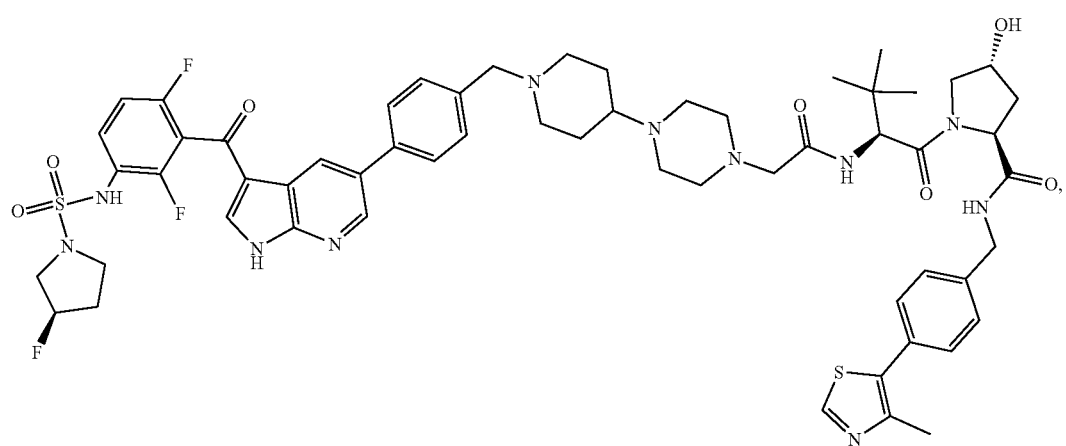
(234)

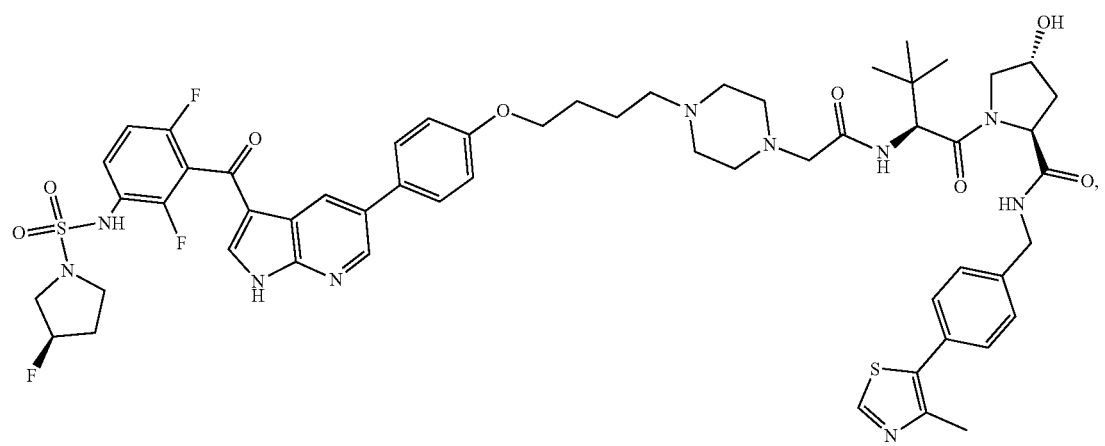
(235)
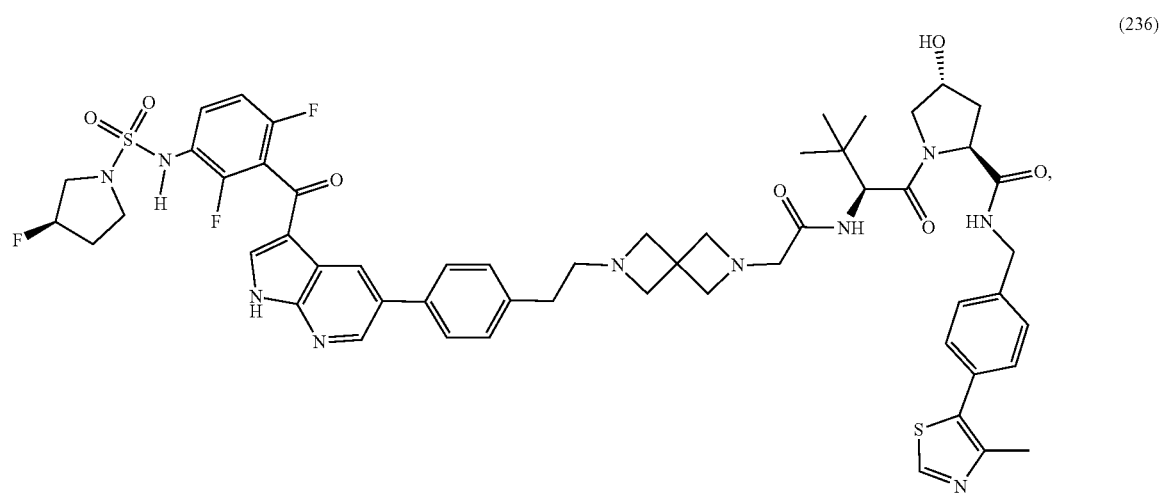
(236)
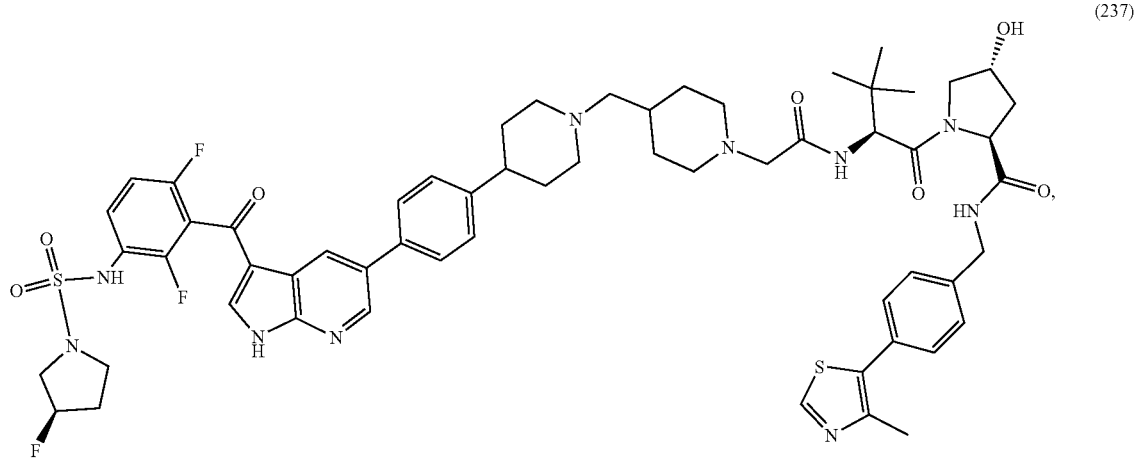
(237)

(238)
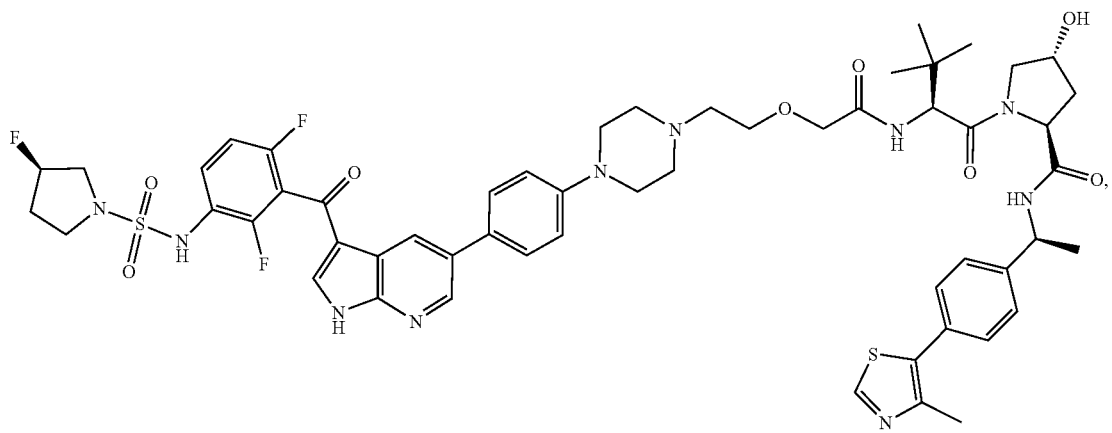
(239)
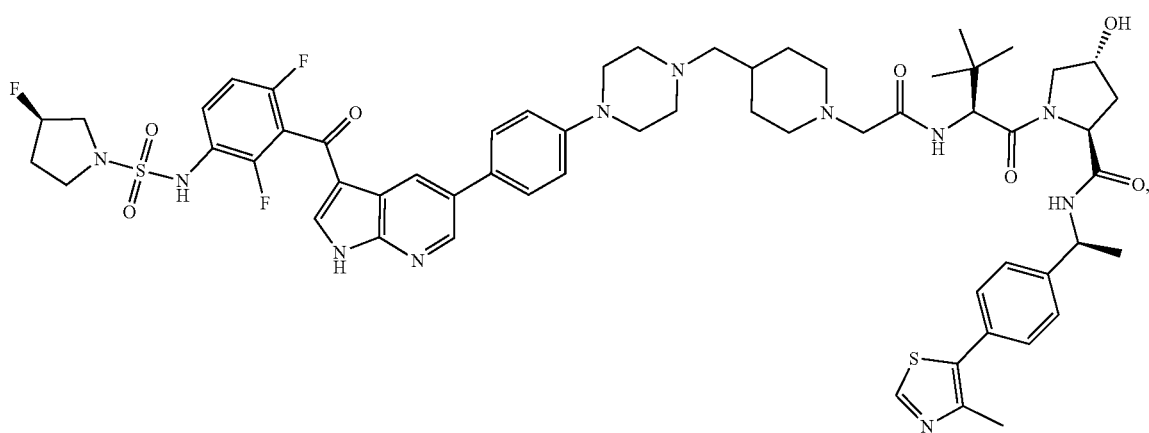
(240)
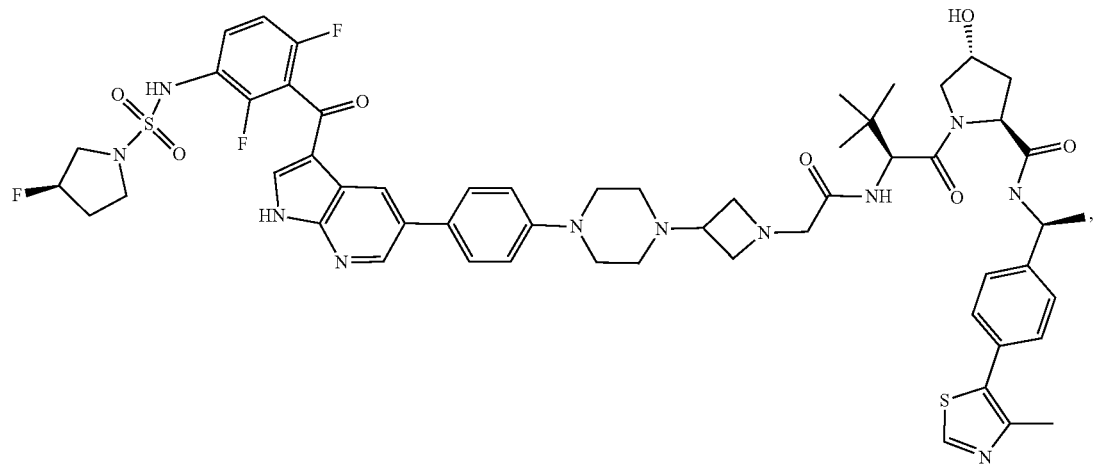

-continued
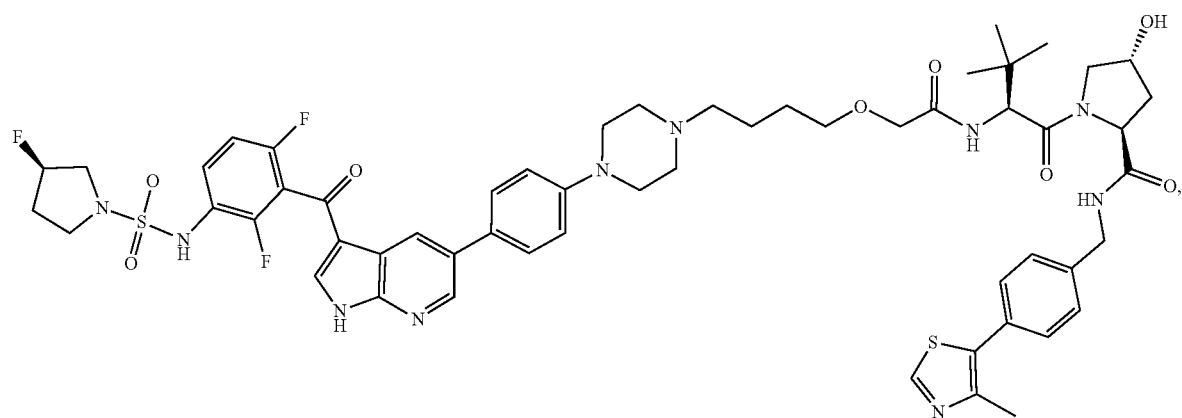
(241)
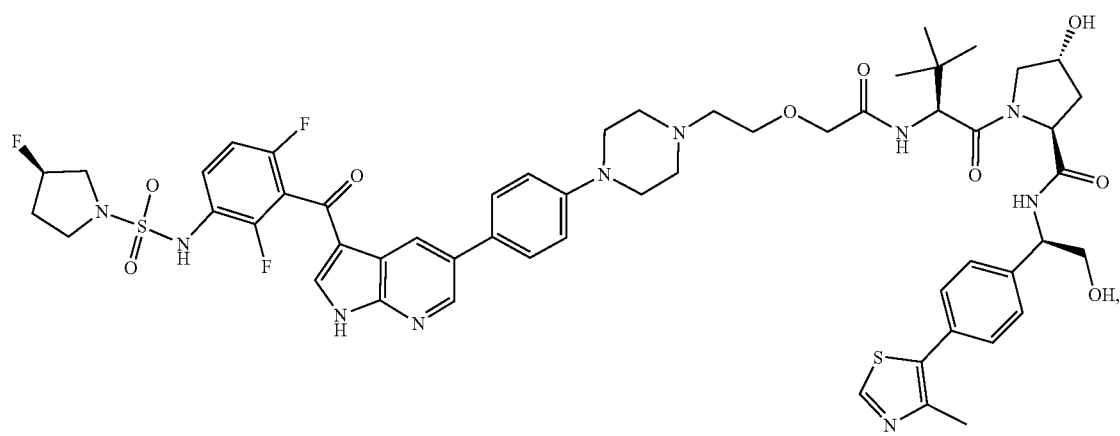
(242)
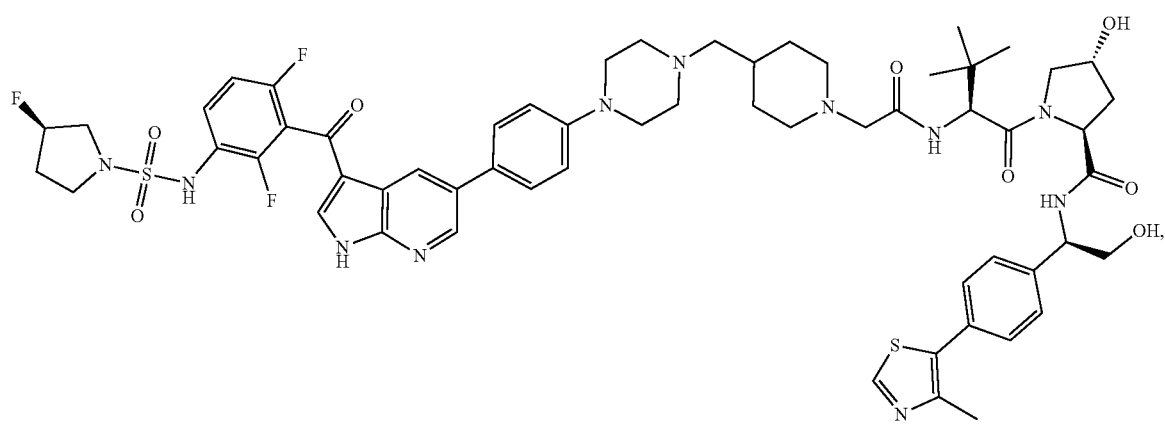
(243)

(244)
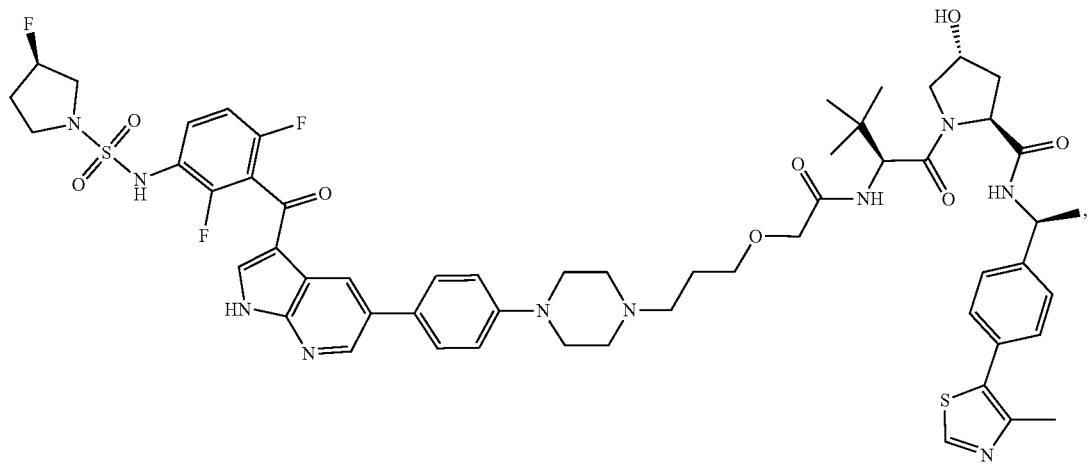
(245)
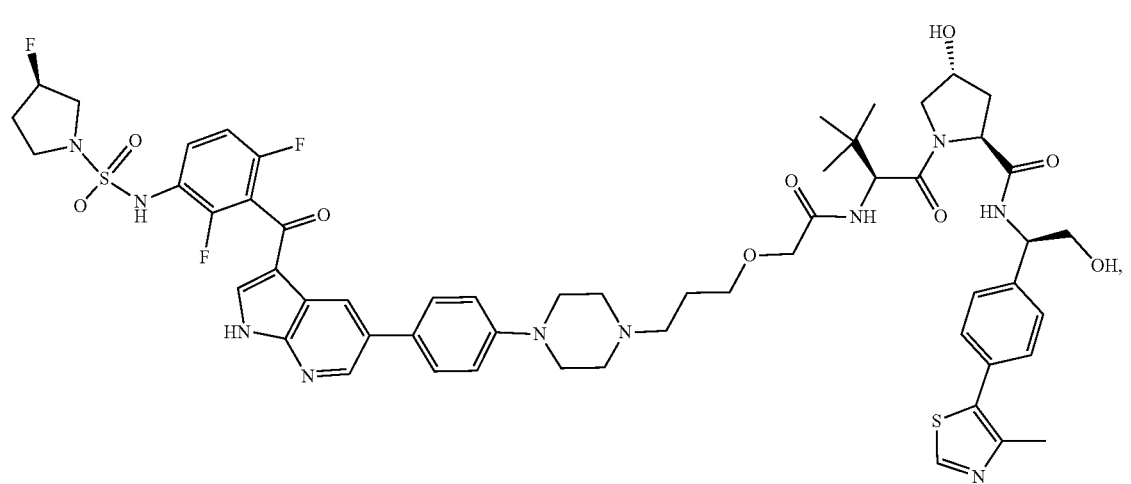
(246)
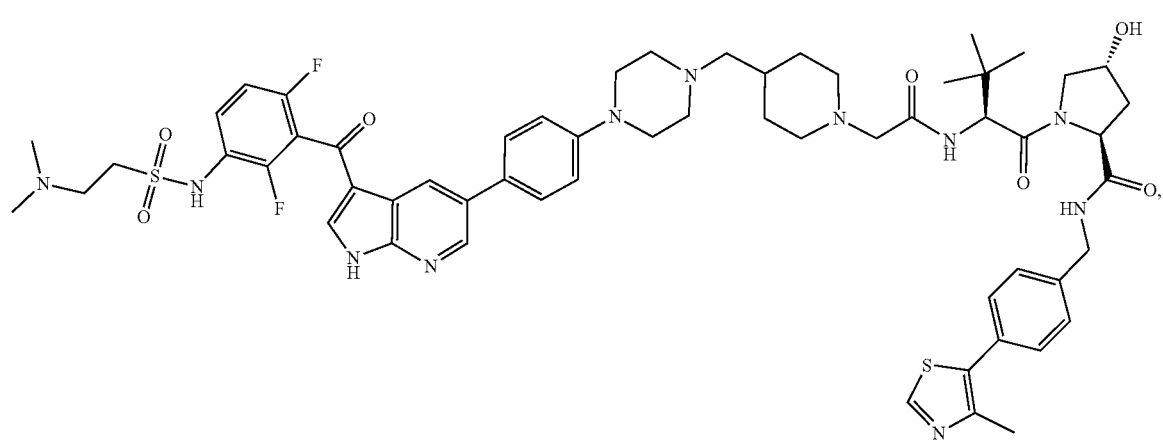

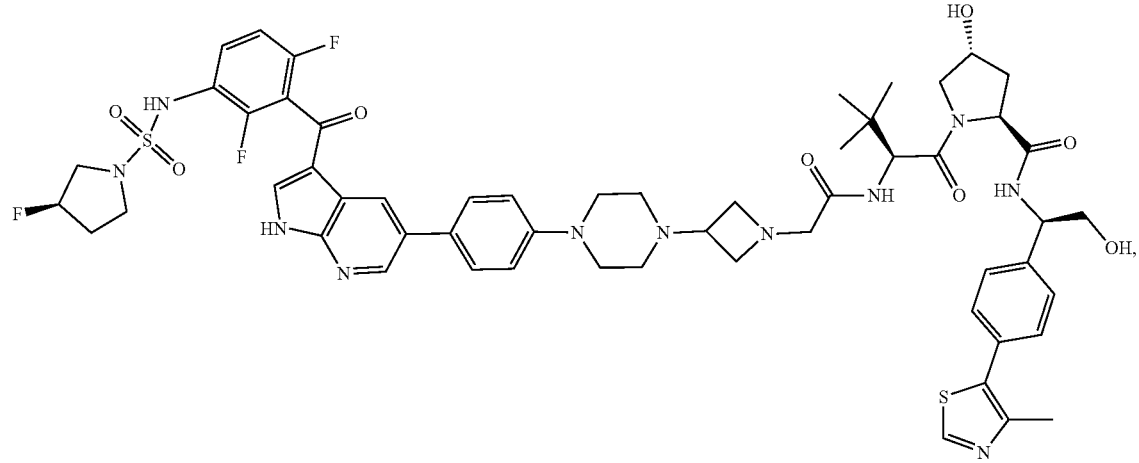
(247)
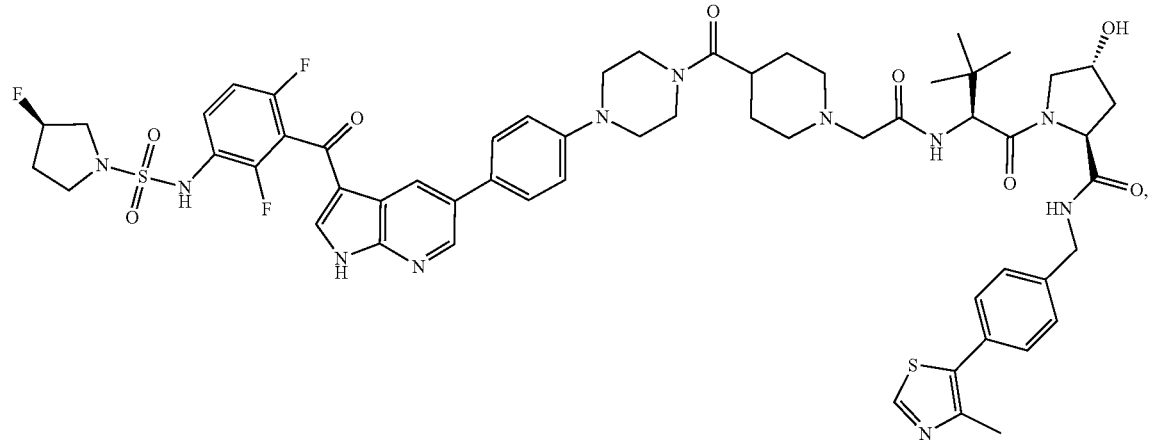
(248)
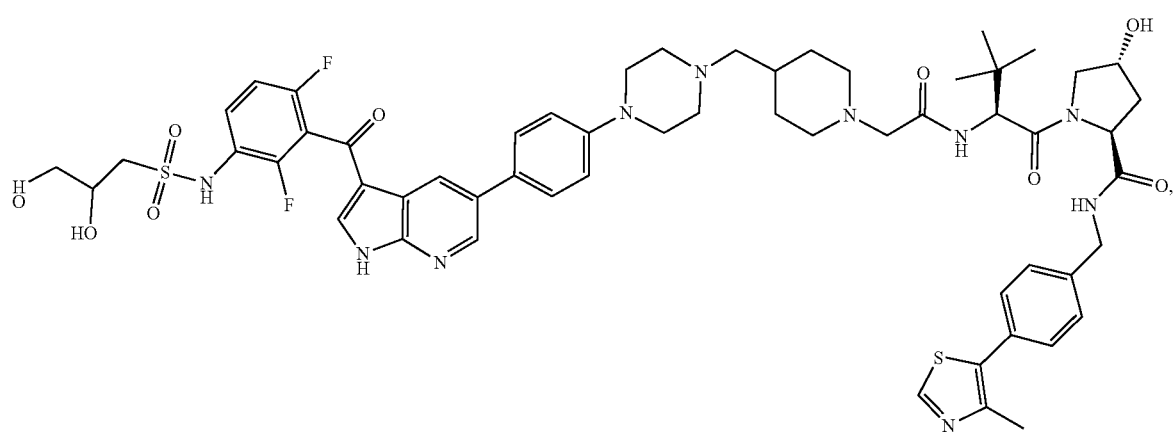
(249)

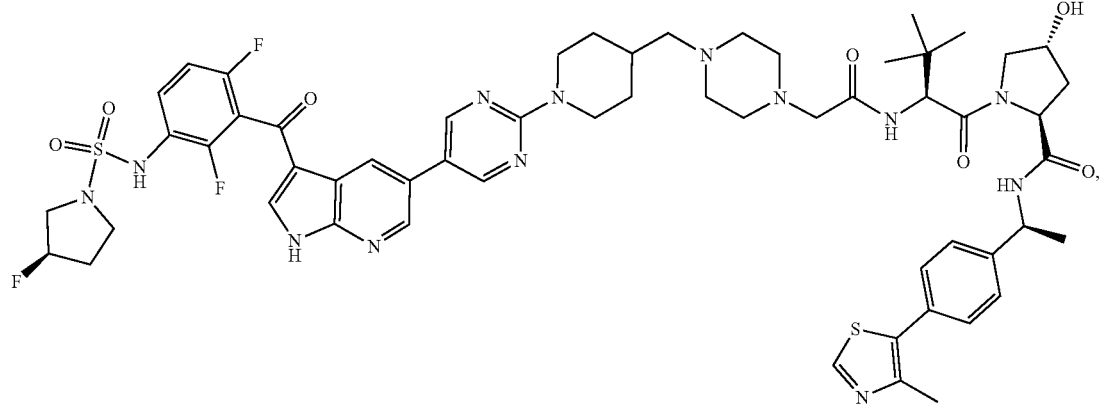
(250)
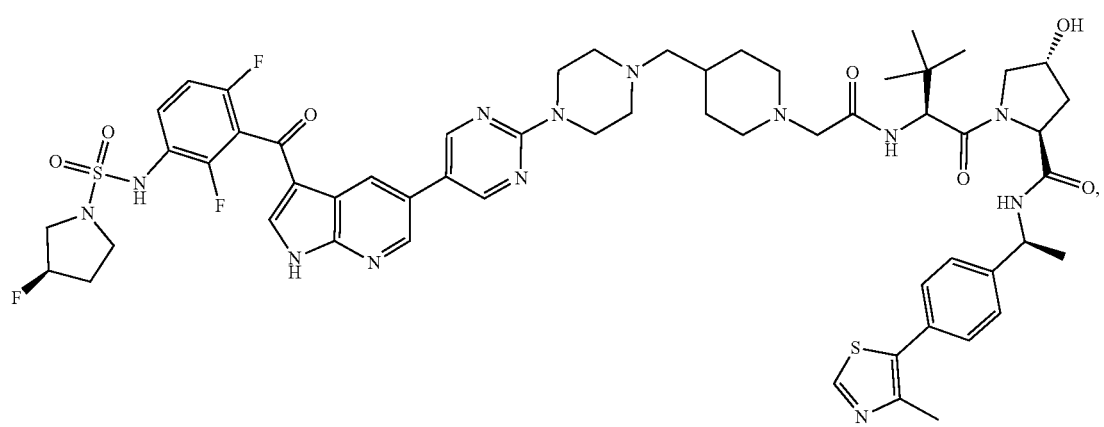
(251)
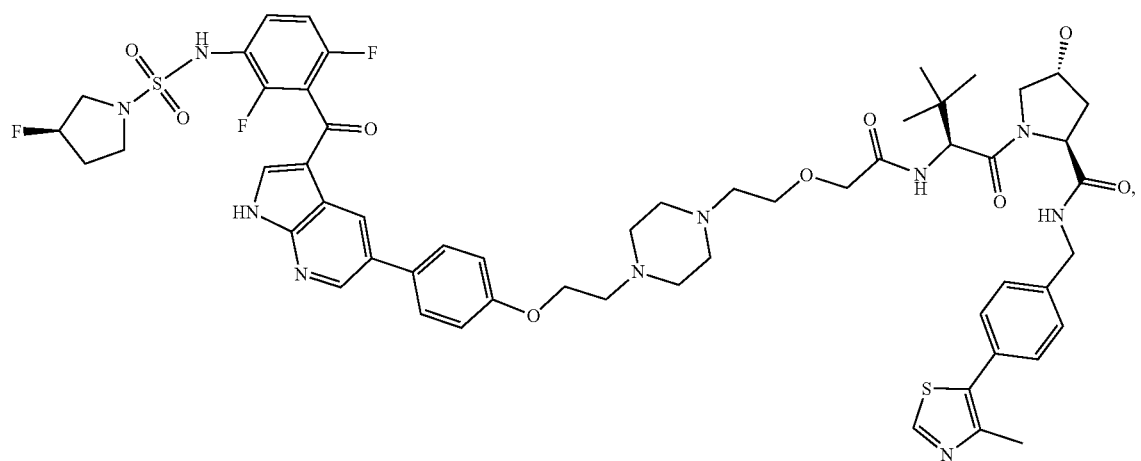
(252)

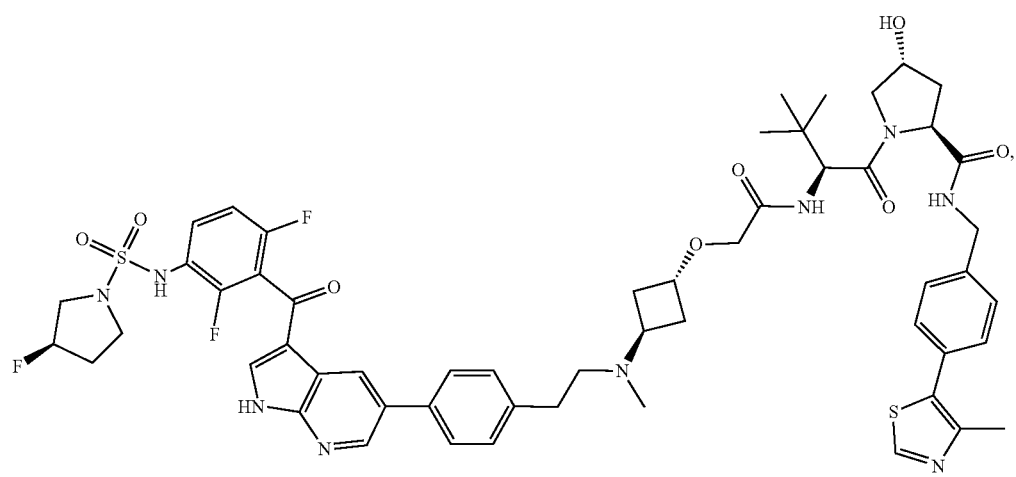
(253)
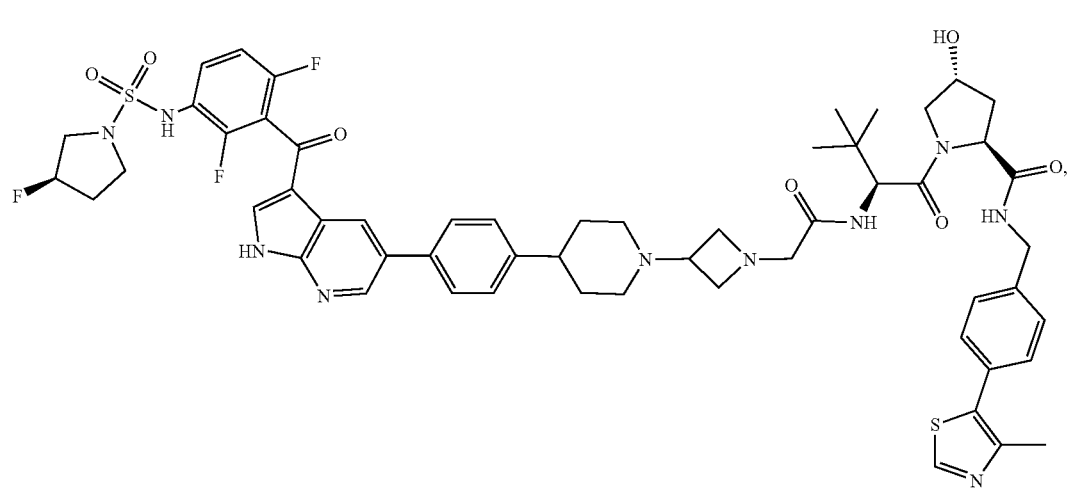
(254)
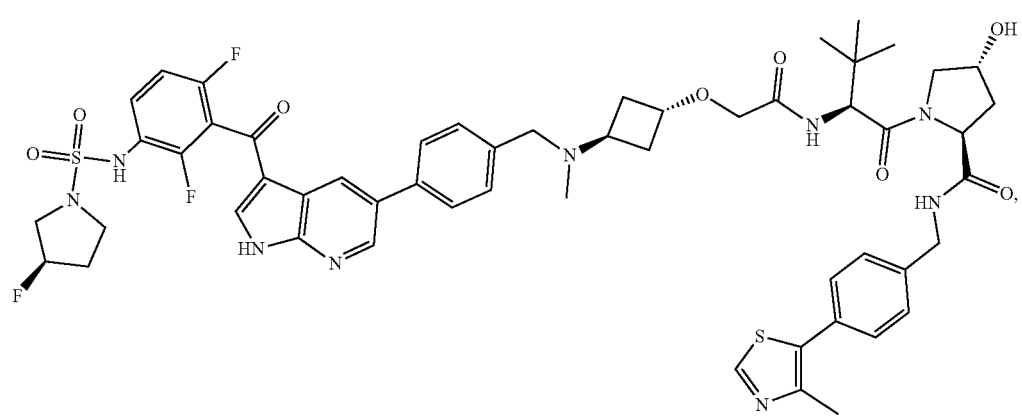
(255)

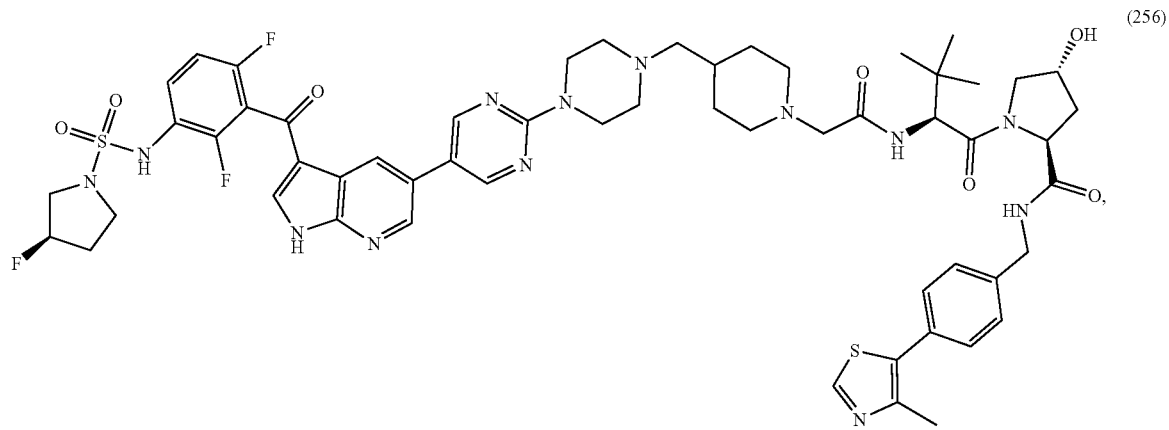
(256)
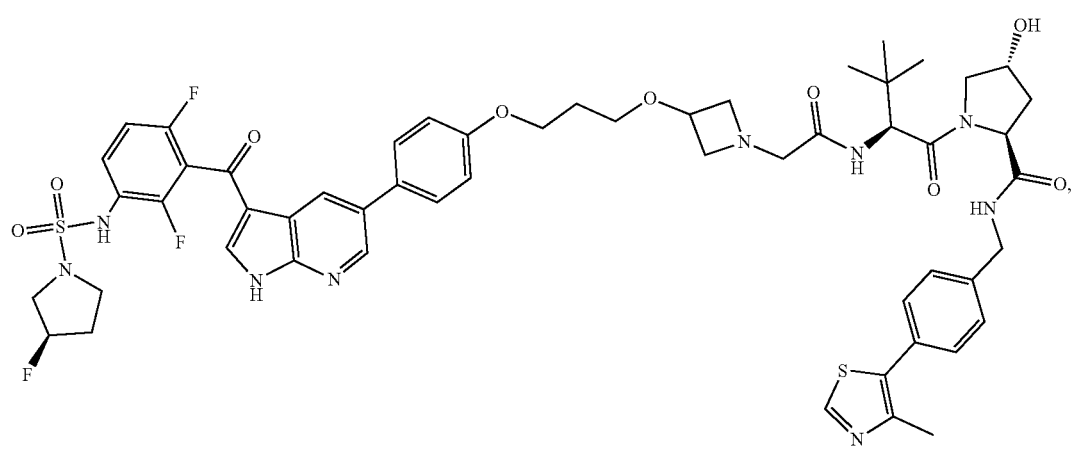
(257)
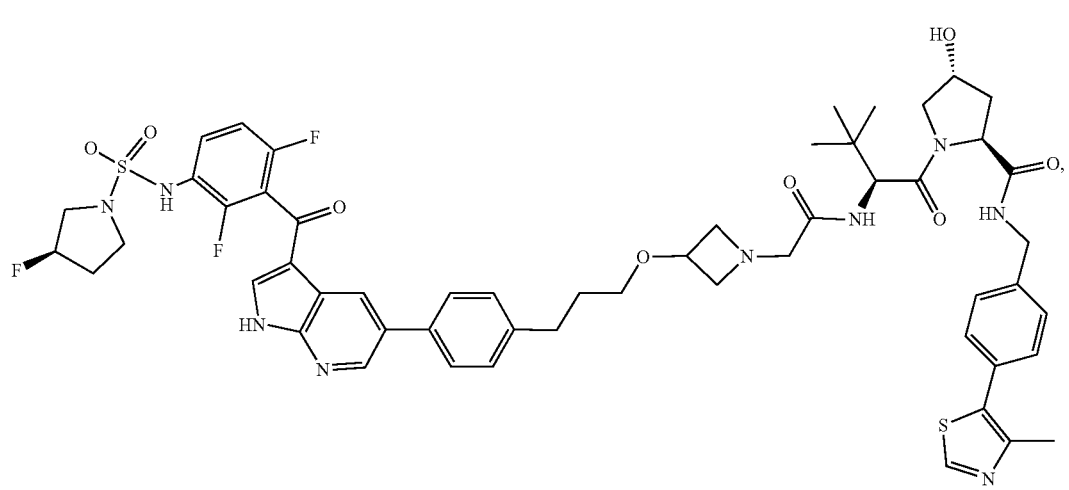
(258)

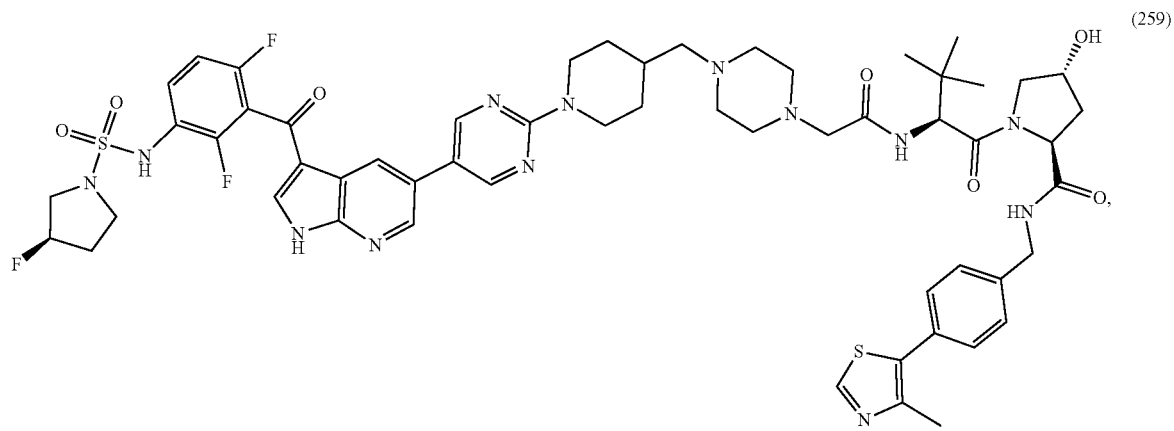
(259)
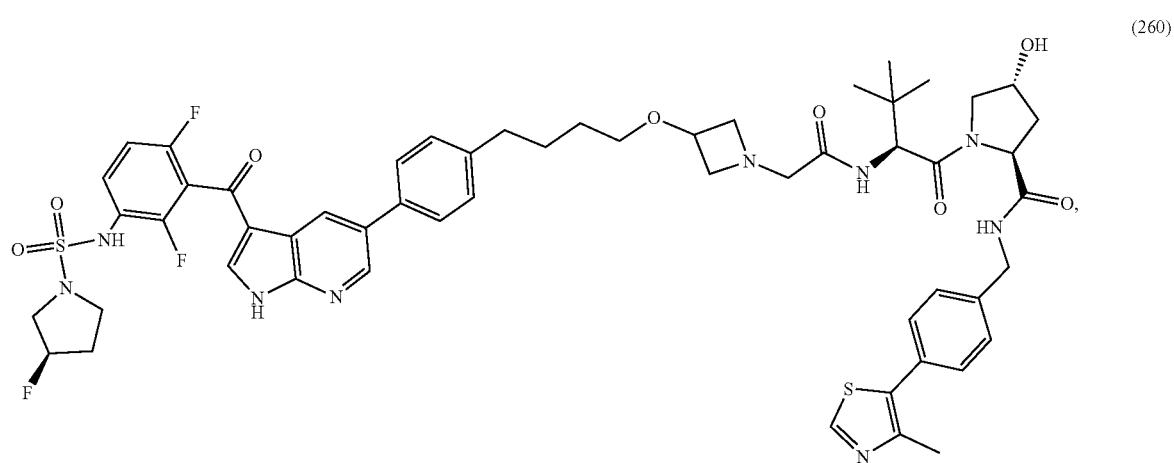
(260)
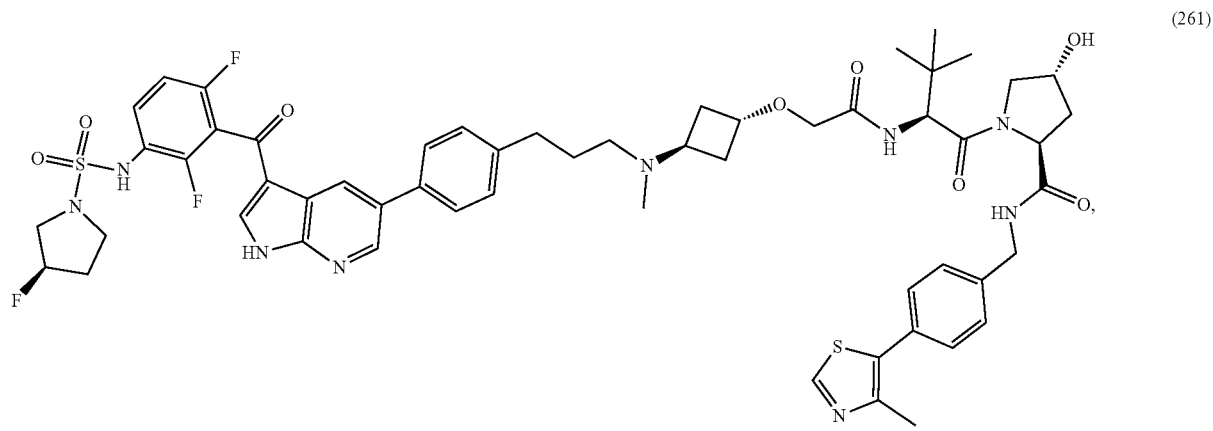
(261)

-continued
(262)
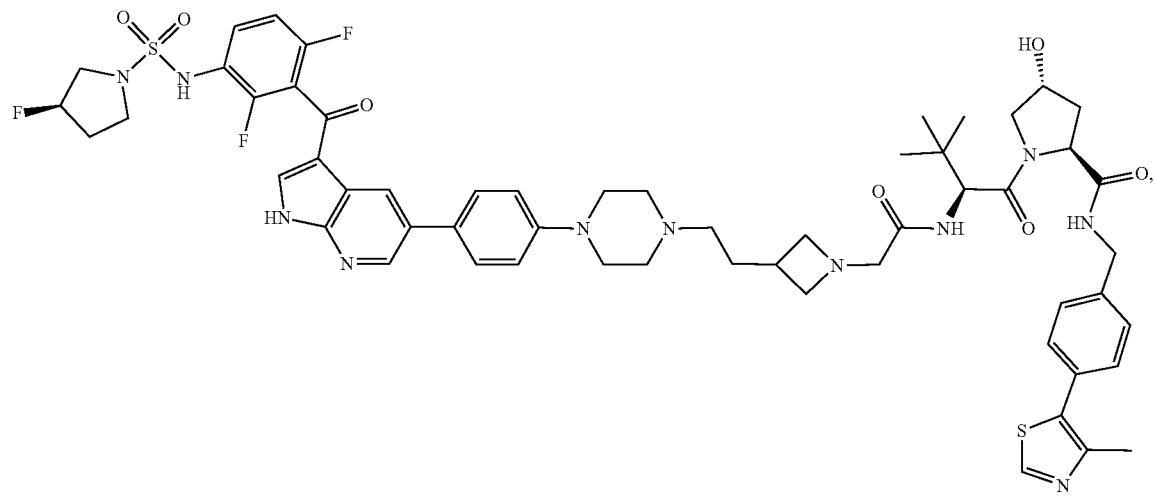
(263)
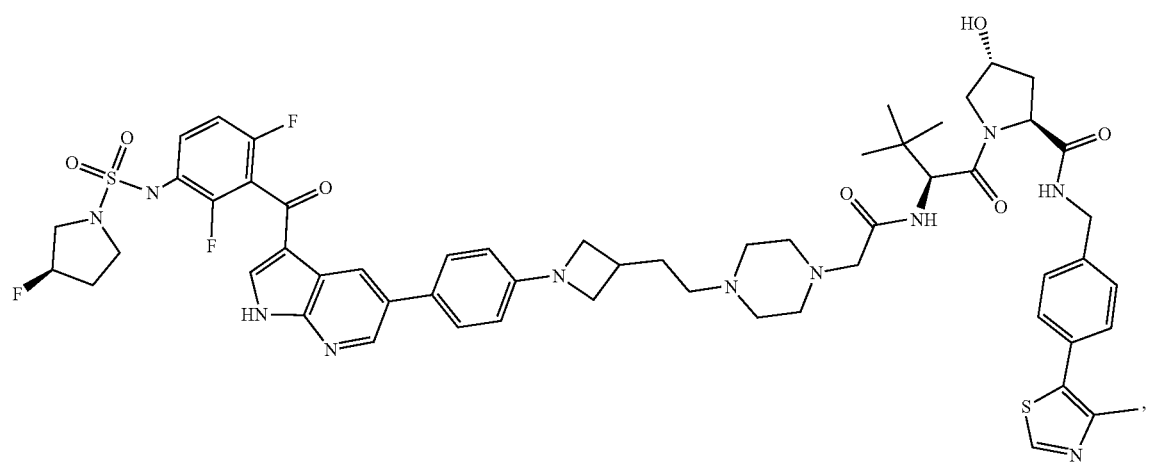
(264)
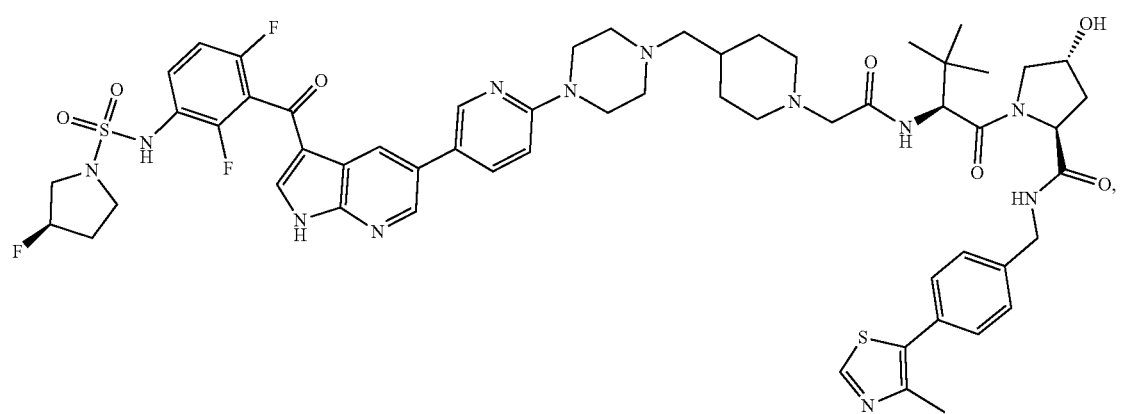

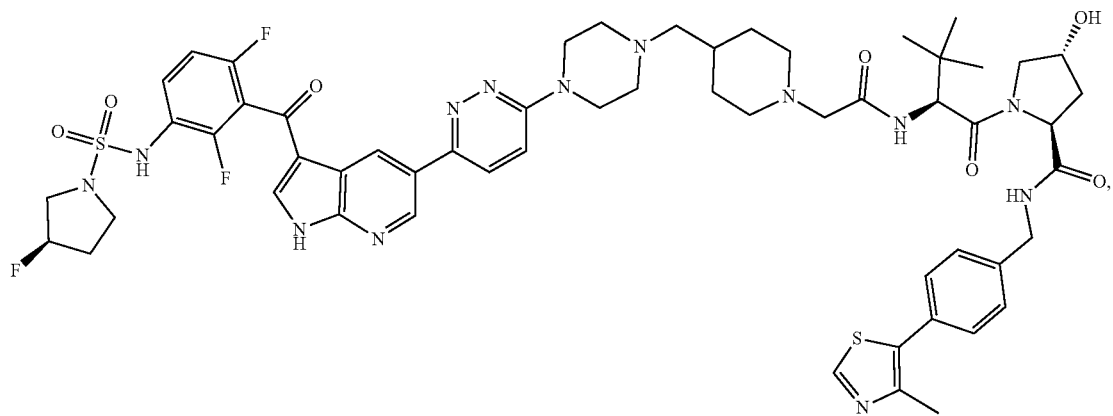
(265)
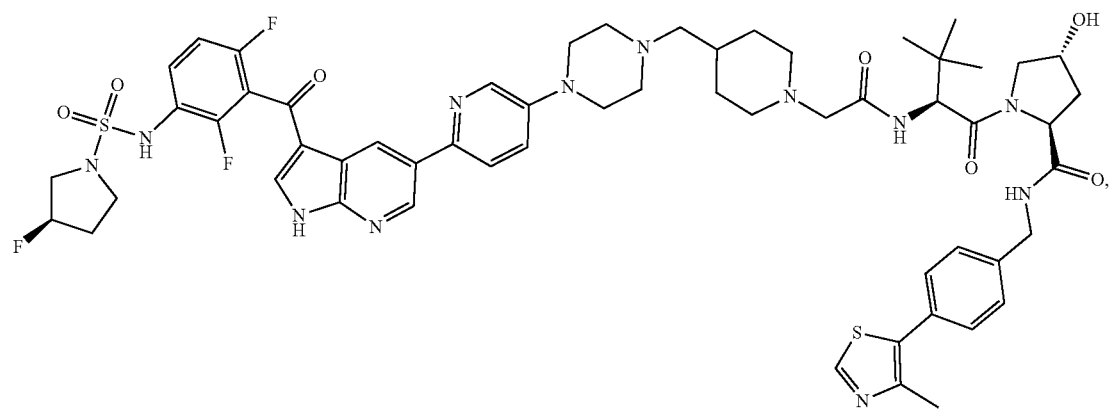
(266)
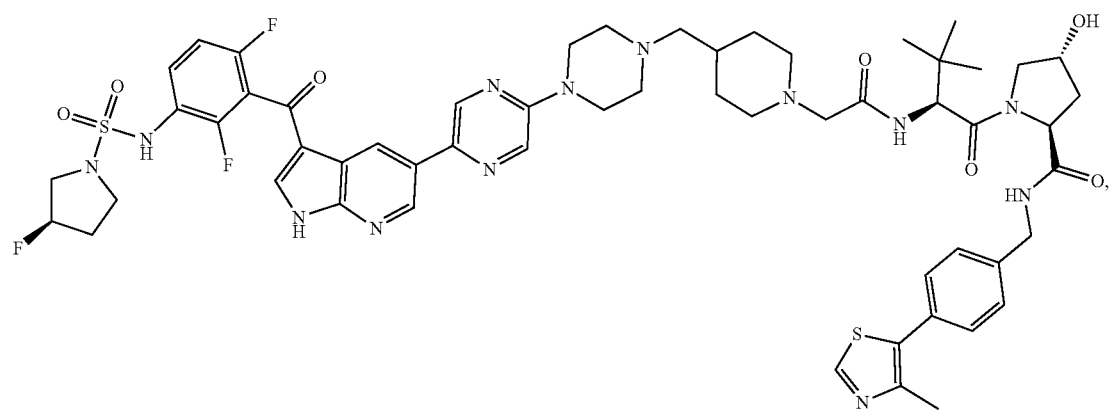
(267)

(268)
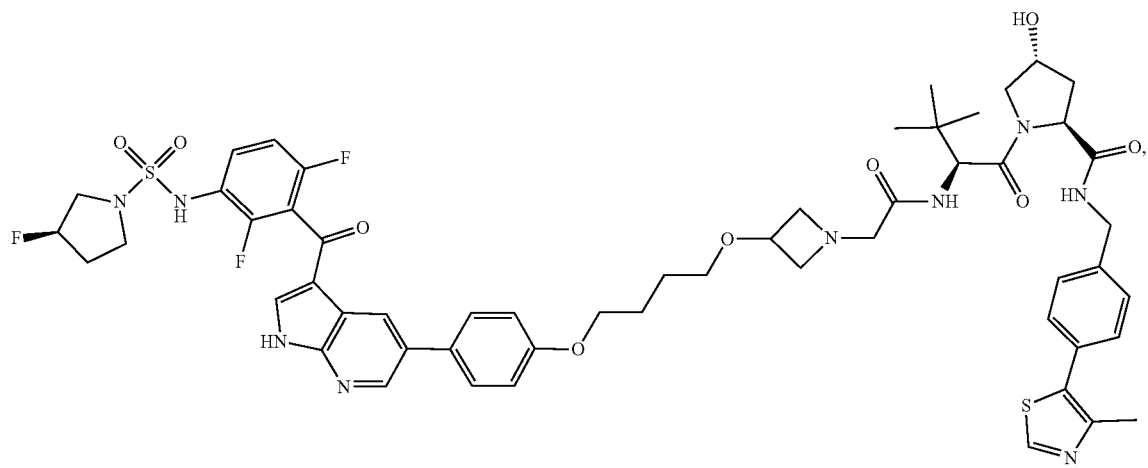
(269)
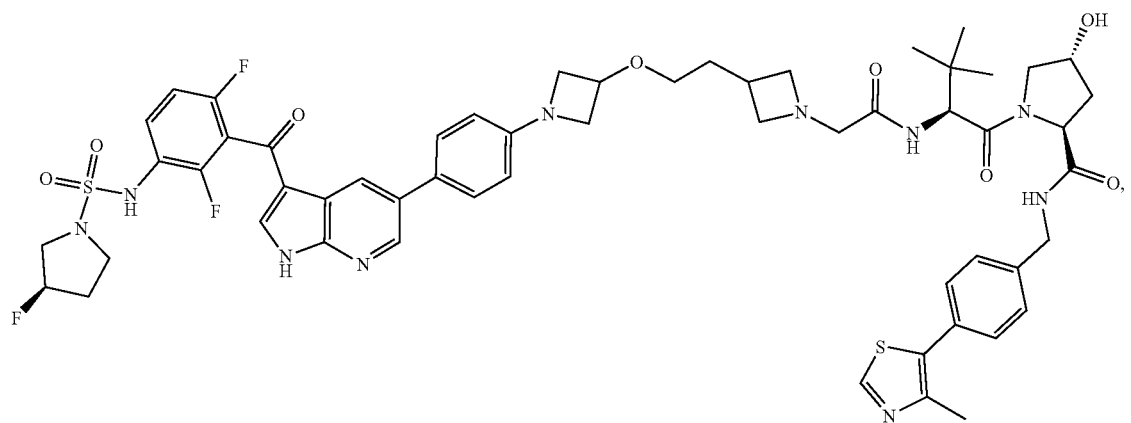
(285)
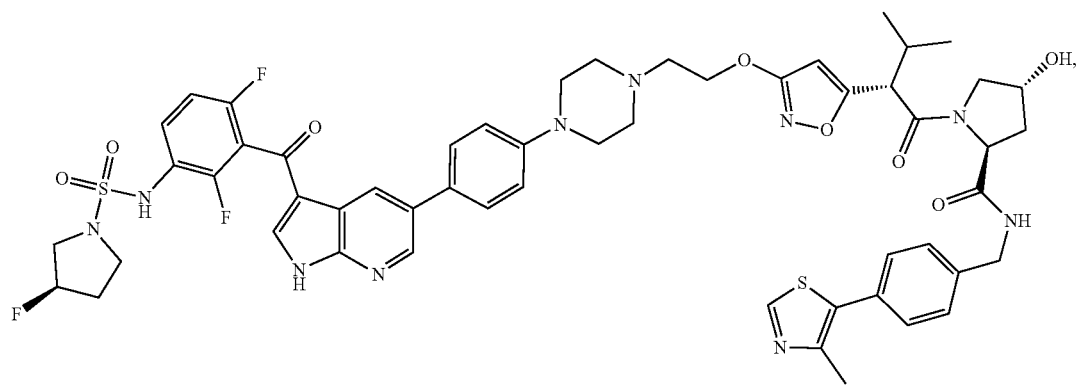

(286)
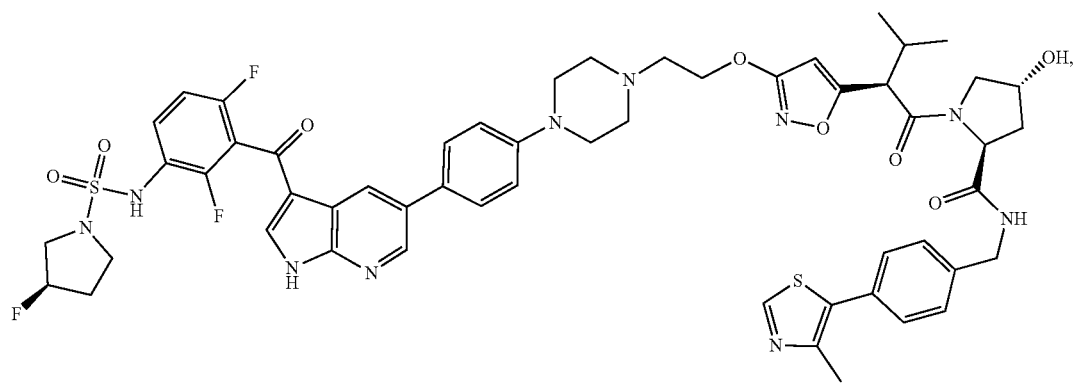
(287)
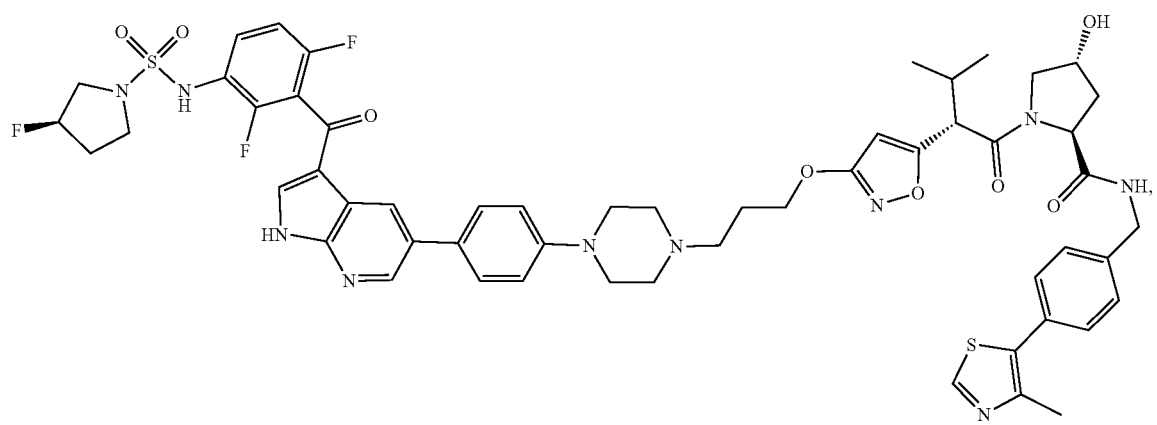
(288)
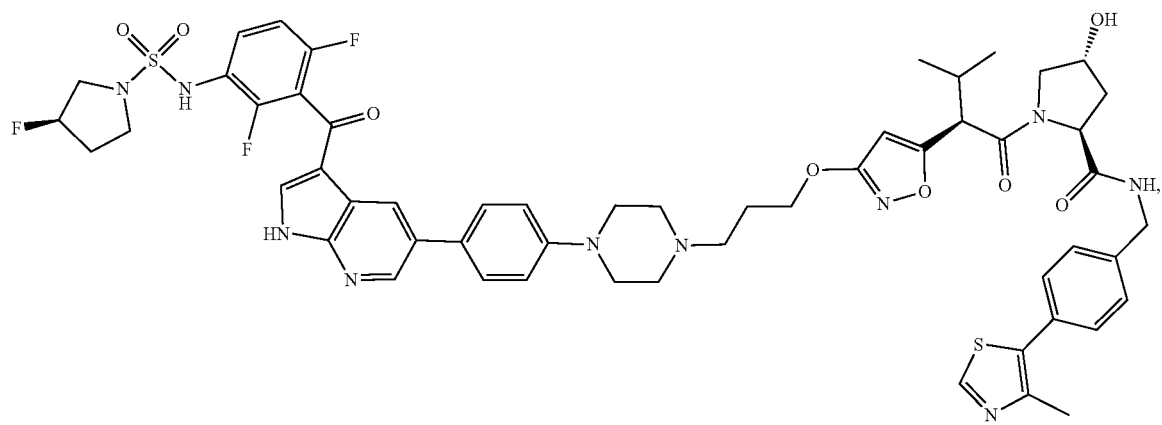

(295)
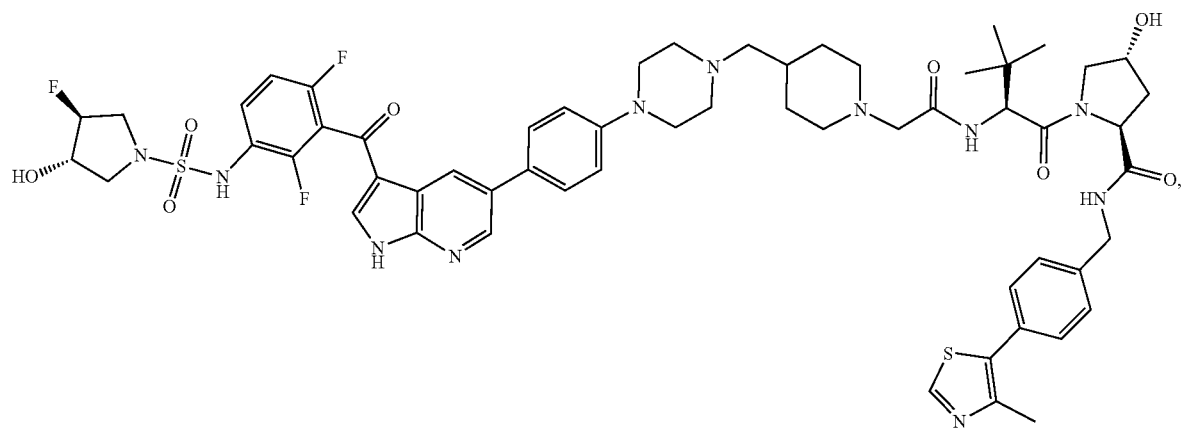
(298)
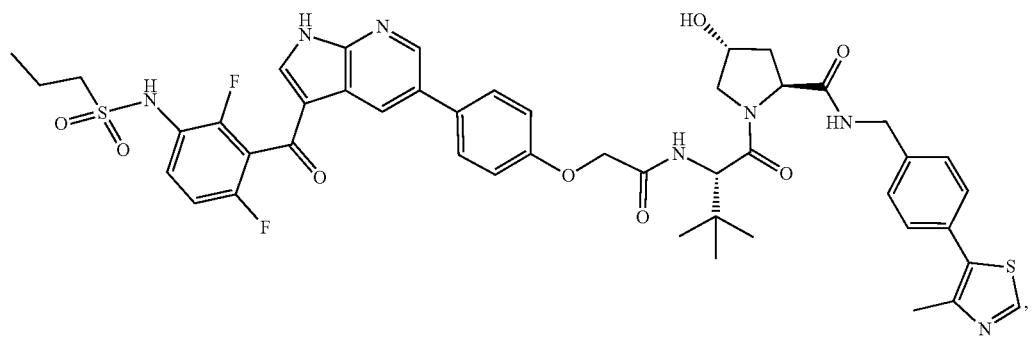
(299)
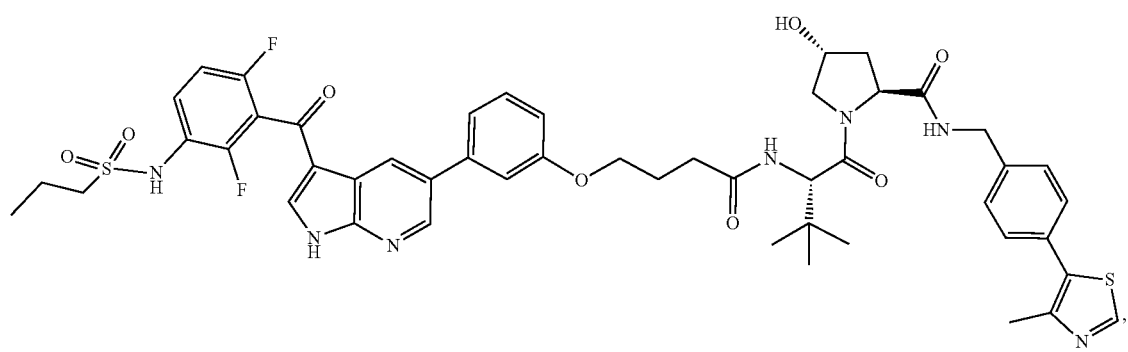
(300)
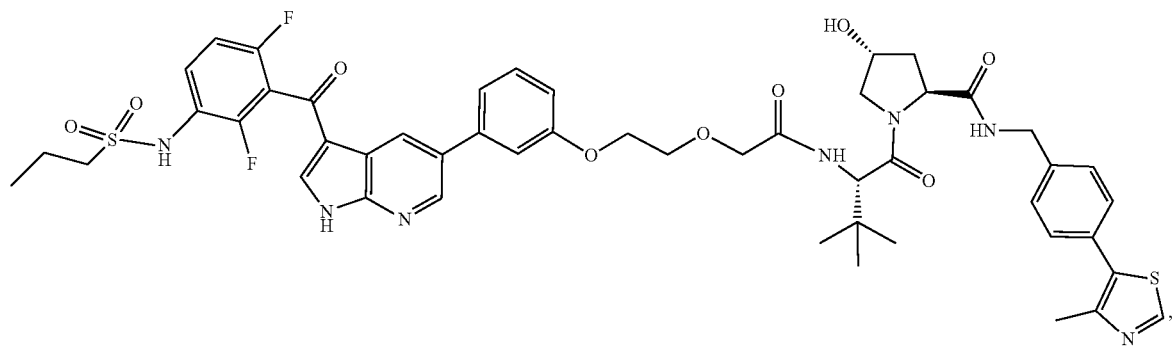

-continued
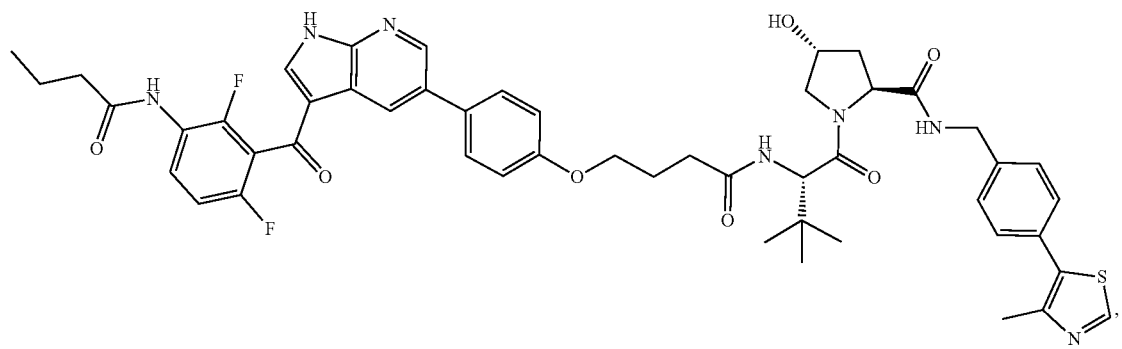
(301)
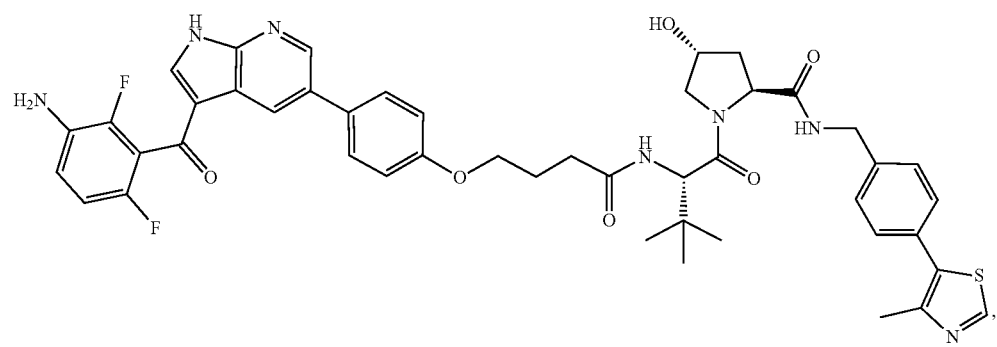
(302)
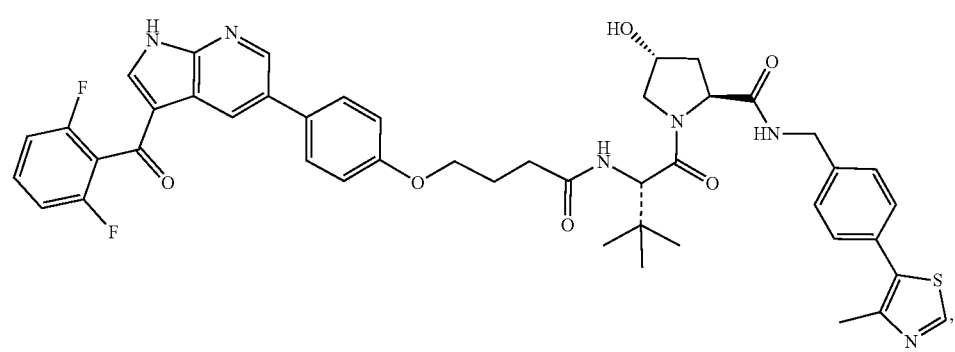
(303)
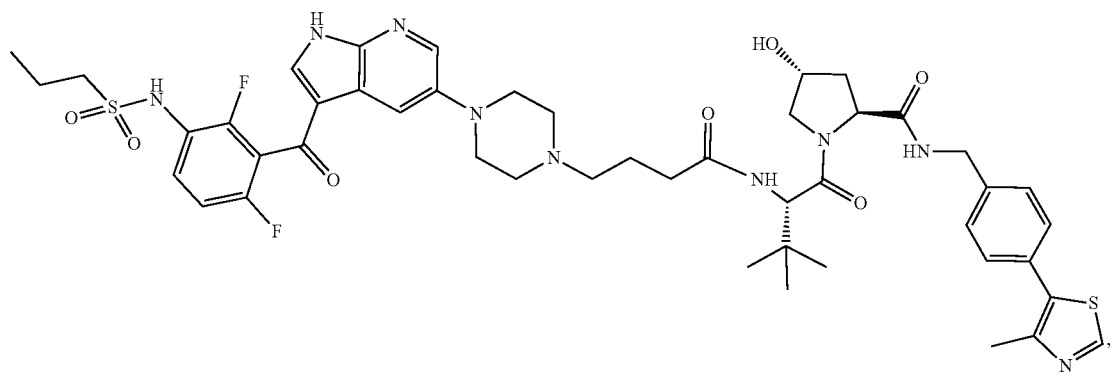
(304)

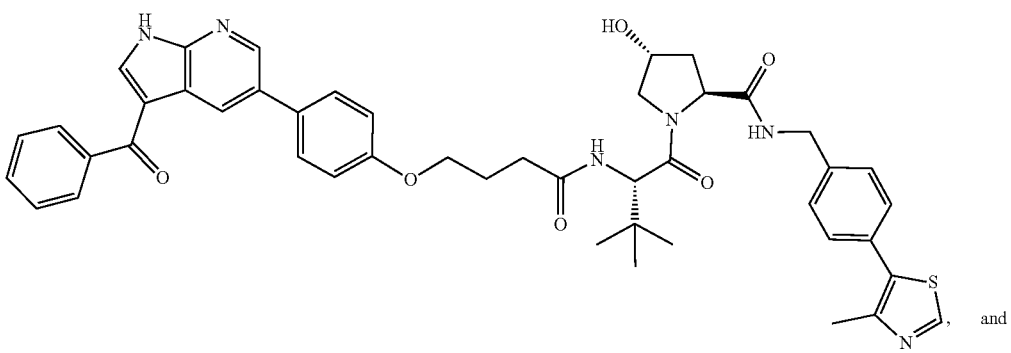

(305)

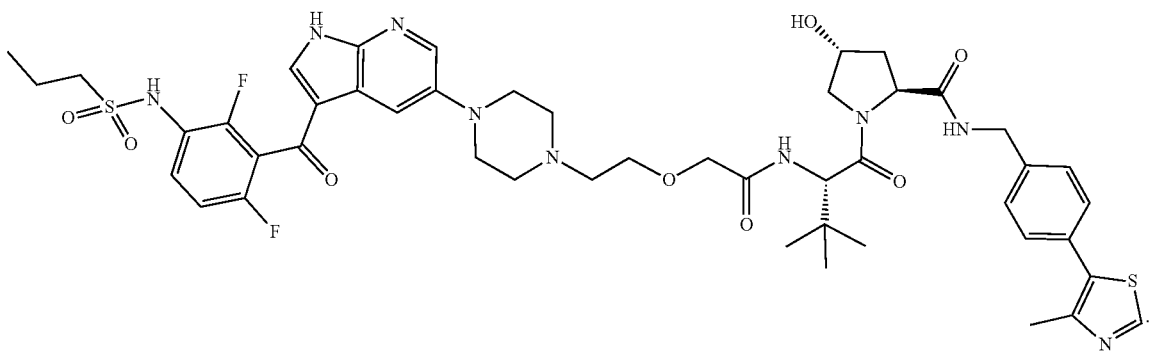

and (306)

20. A pharmaceutical composition comprising an effective amount of a bifunctional compound according to claim 1, and a pharmaceutically acceptable carrier.

21. The pharmaceutical composition according to claim 20, wherein the composition further comprises at least one of an additional bioactive agent or another of the bifunctional compound.

22. The pharmaceutical composition according to claim 21, wherein the additional bioactive agent is anti-cancer agent.

23. A method for treating a disease or disorder associated with overexpression or overactivation of BRaf in a subject, the method comprising administering a composition comprising a pharmaceutically acceptable carrier and an effective amount of at least one compound according to claim 1 to a subject in need thereof, wherein the compound is effective in treating or ameliorating at least one symptom of the disease or disorder, wherein the disease or disorder is: cardiofaciocutaneous syndrome; neurofibromatosis type 1; Costello syndrome; Noonan Syndrome; Lentigo, Electrocardiographic abnormalities, Ocular hypertelorism, Pulmonary stenosis, Abnormal genitalia, Retarded growth, Deafness (LEOPARD) syndrome associated with RAF accumulation and aggregation; renal cell carcinoma; pancreatic cancer; colorectal cancer; lung cancer; ovarian cancer; thyroid cancer; pilocytic astrocytoma; prostate cancer; gastric cancer; hepatocellular carcinoma; or melanoma.

24. The method according to claim 23, wherein the disease or disorder is neurofibromatosis type 1.

25. The method according to claim 23, wherein the disease or disorder is cardiofaciocutaneous syndrome.

26. The method according to claim 23, wherein the disease or disorder is renal cell carcinoma.

27. The method according to claim 23, wherein the disease or disorder is Costello syndrome.

28. The method according to claim 23, wherein the disease or disorder is Noonan Syndrome.

29. The method according to claim 23, wherein the disease or disorder is Lentigo, Electrocardiographic abnormalities, Ocular hypertelorism, Pulmonary stenosis, Abnormal genitalia, Retarded growth, Deafness (LEOPARD) syndrome associated with RAF.

30. The method according to claim 23, wherein the disease or disorder is pancreatic cancer.

31. The method according to claim 23, wherein the disease or disorder is colorectal cancer.

32. The method according to claim 23, wherein the disease or disorder is lung cancer.

33. The method according to claim 23, wherein the disease or disorder is ovarian cancer.

34. The method according to claim 23, wherein the disease or disorder is thyroid cancer.

35. The method according to claim 23, wherein the disease or disorder is pilocytic astrocytoma.

36. The method according to claim 23, wherein the disease or disorder is prostate cancer.

37. The method according to claim 23, wherein the disease or disorder is gastric cancer.

38. The method according to claim 23, wherein the disease or disorder is hepatocellular carcinoma.

39. The method according to claim 23, wherein the disease or disorder is melanoma.

40. The bifunctional compound of claim 1, wherein the compound is represented by the chemical structure:
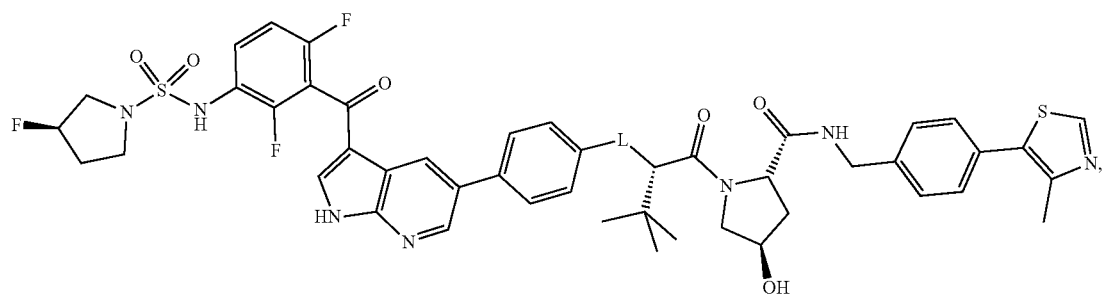
wherein the chemical linker group (L) is selected from the group consisting of:
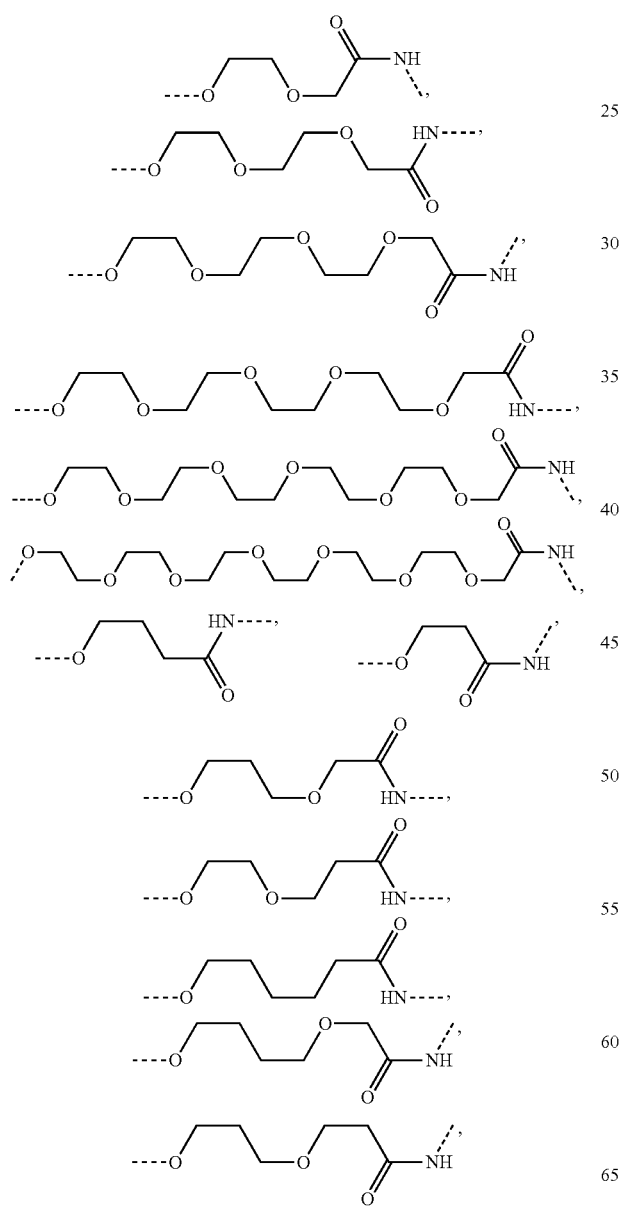
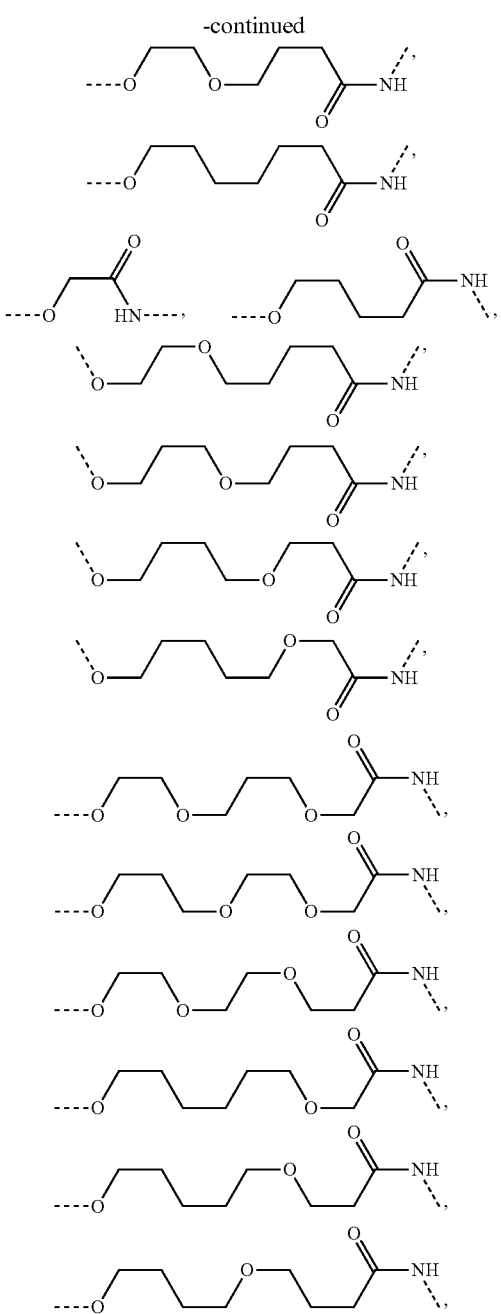

1641
-continued
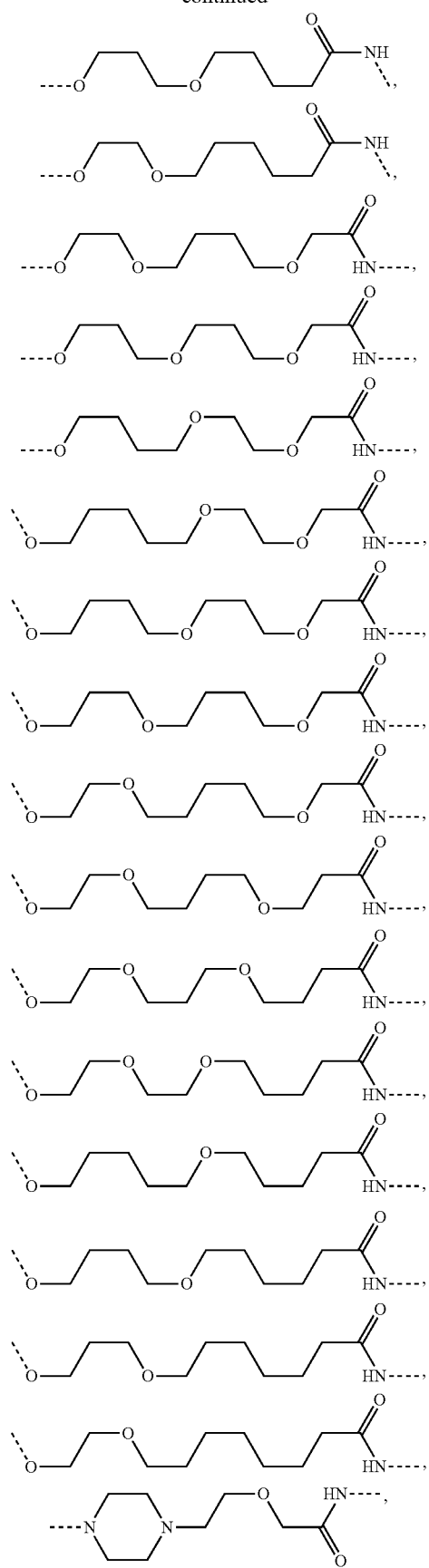
1642
-continued
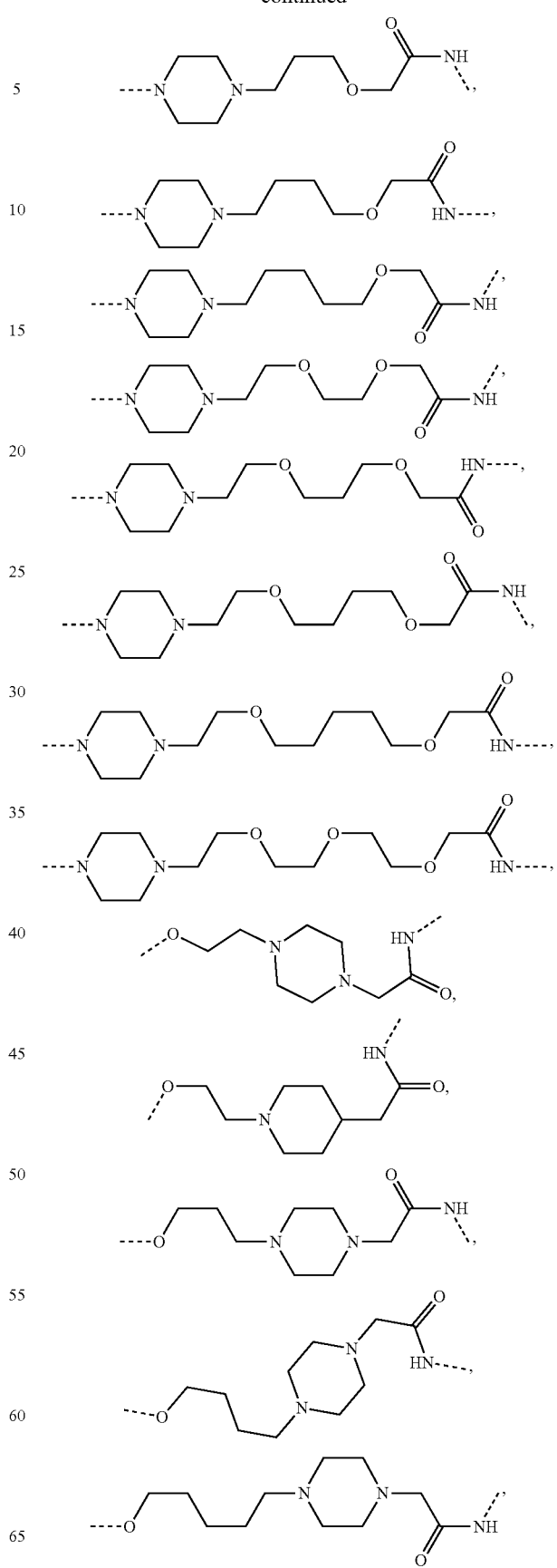

1643
-continued
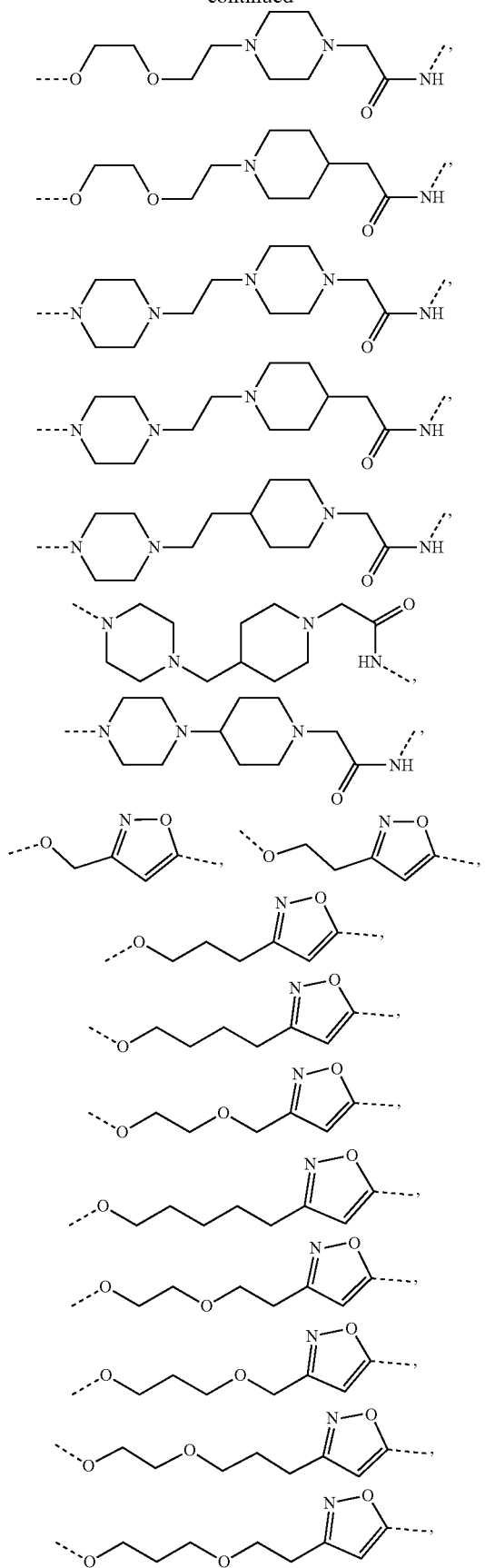
1644
-continued
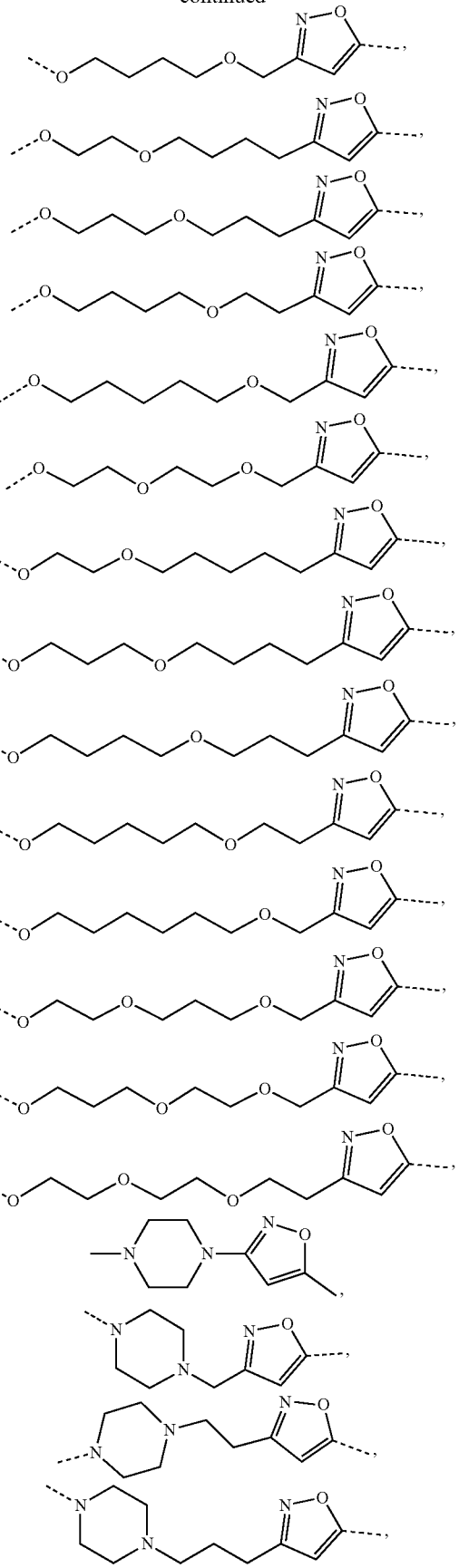

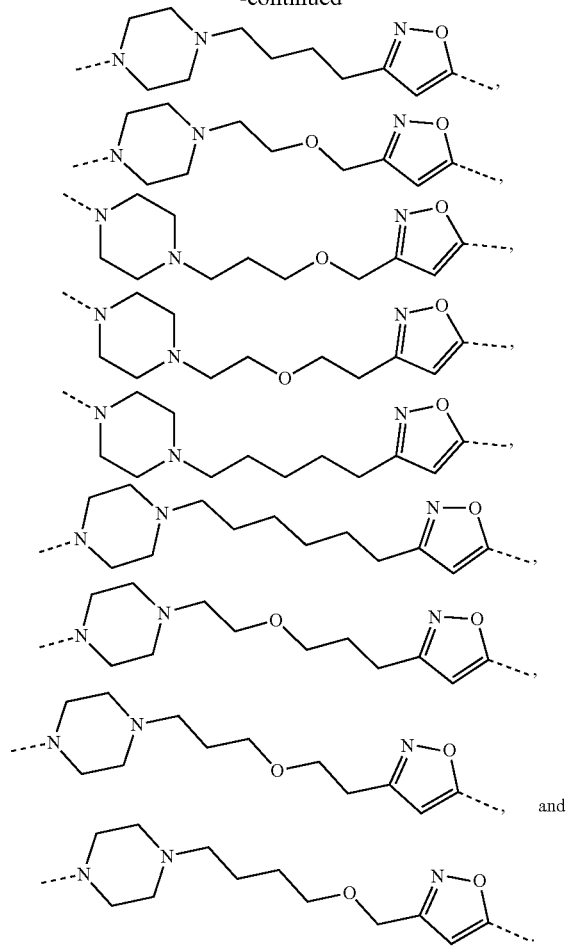
41. The bifunctional compound of claim 1, wherein the compound is represented by the chemical structure:
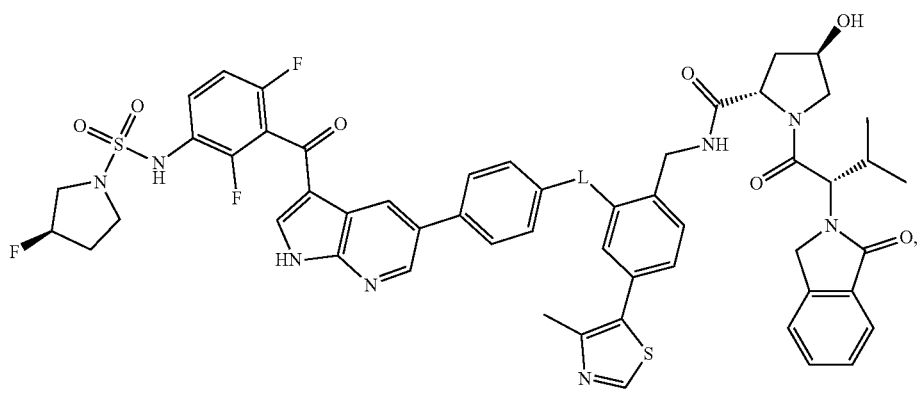
wherein the chemical linker group (L) is selected from the group consisting of:
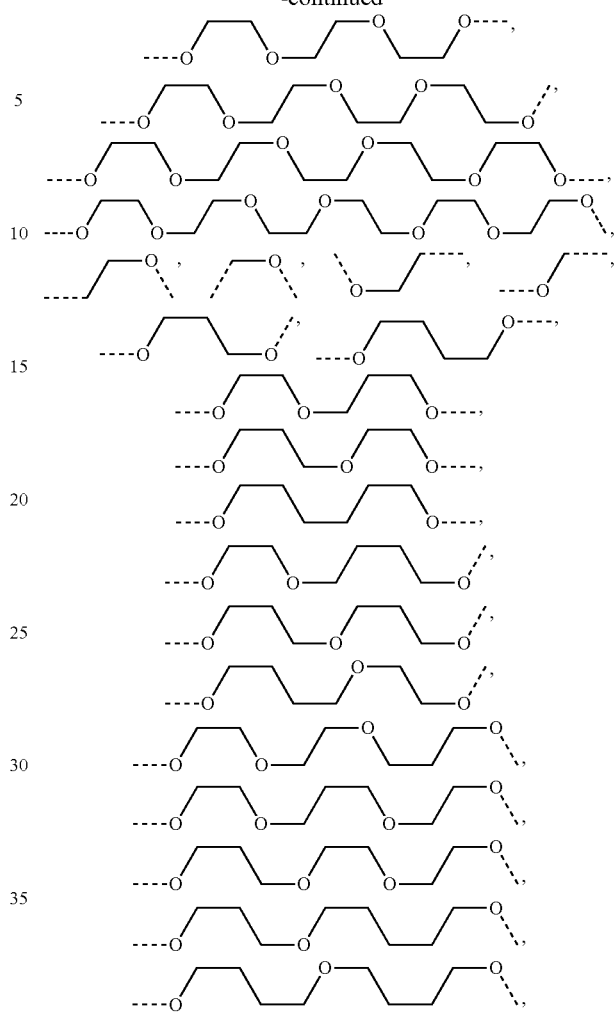
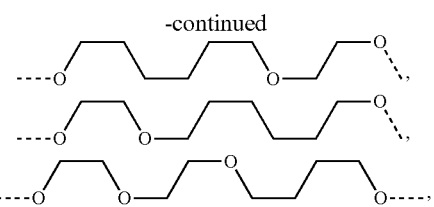

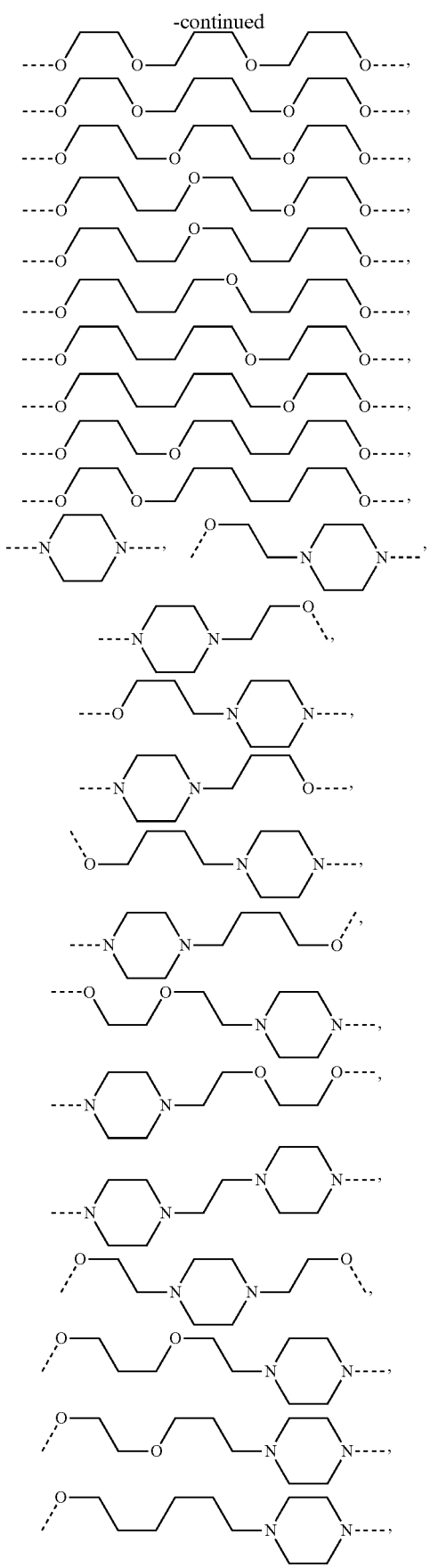

42. The bifunctional compound of claim 1, wherein the compound is represented by the chemical structure:
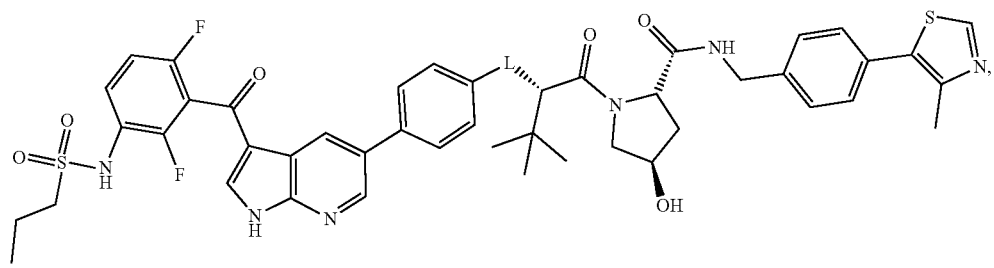
wherein the chemical linker group (L) is selected from the group consisting of:
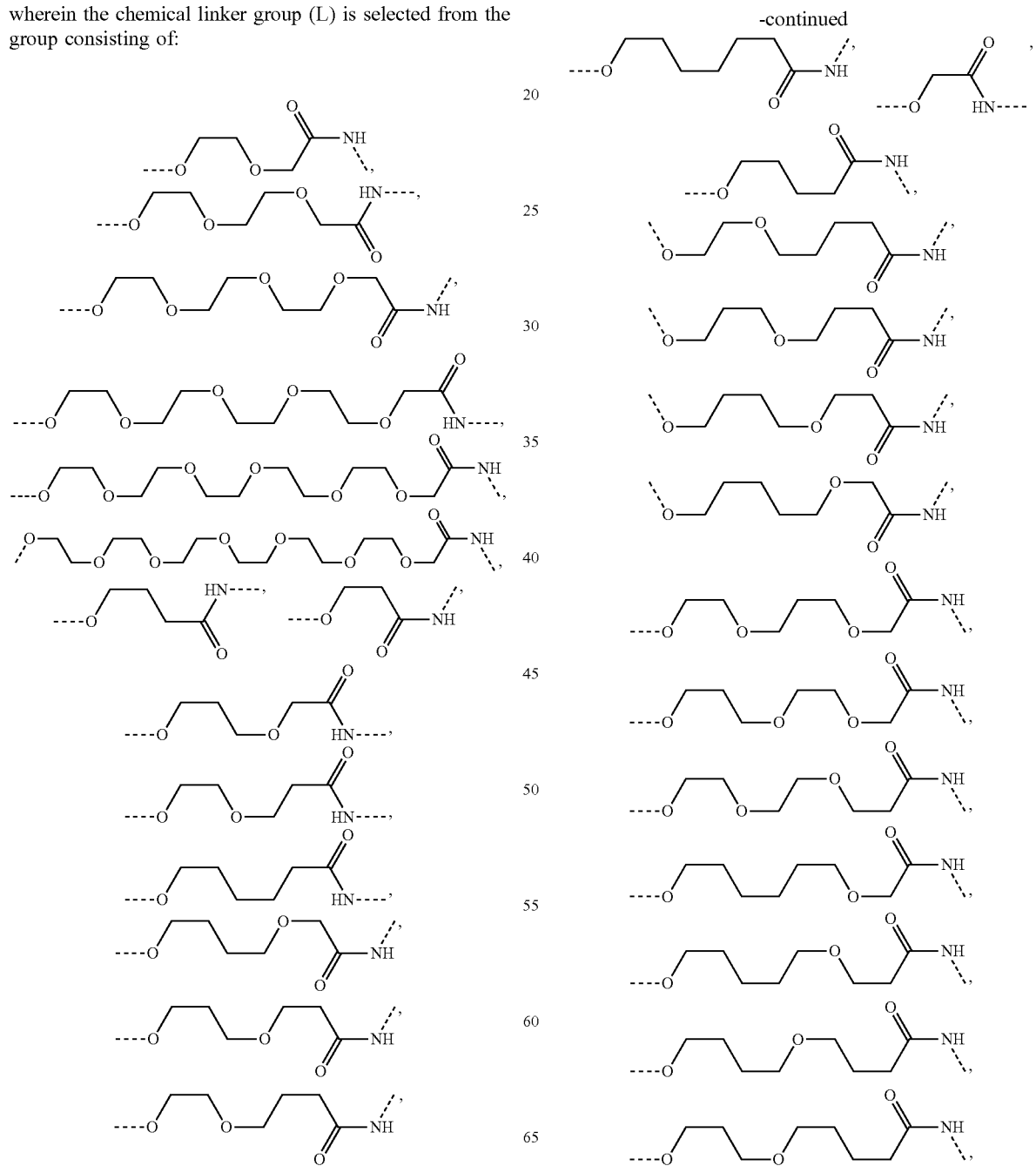

1651
-continued
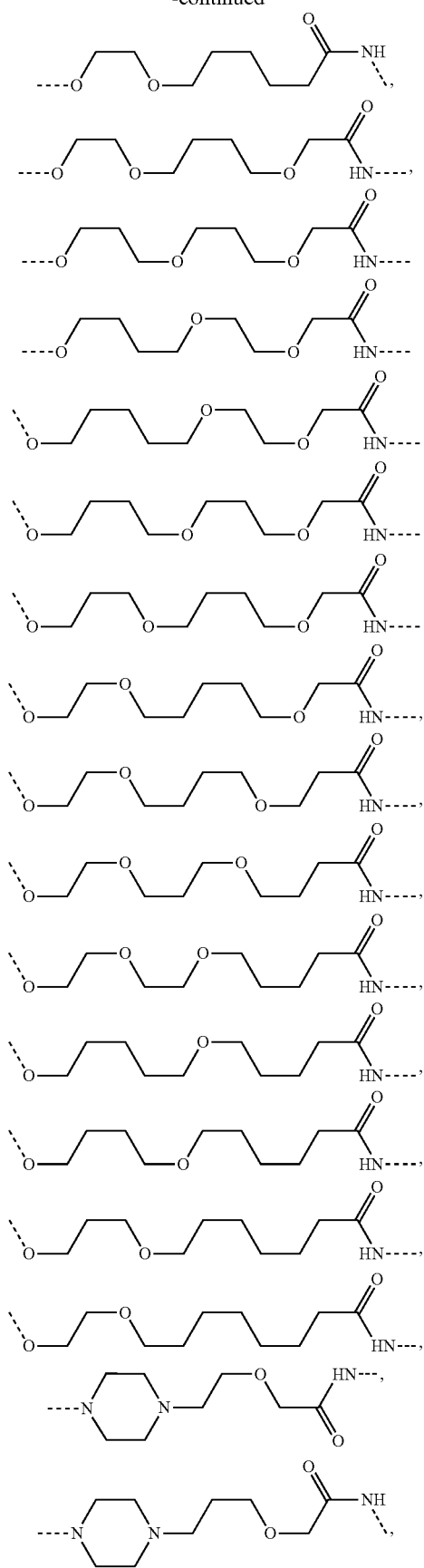
1652
-continued
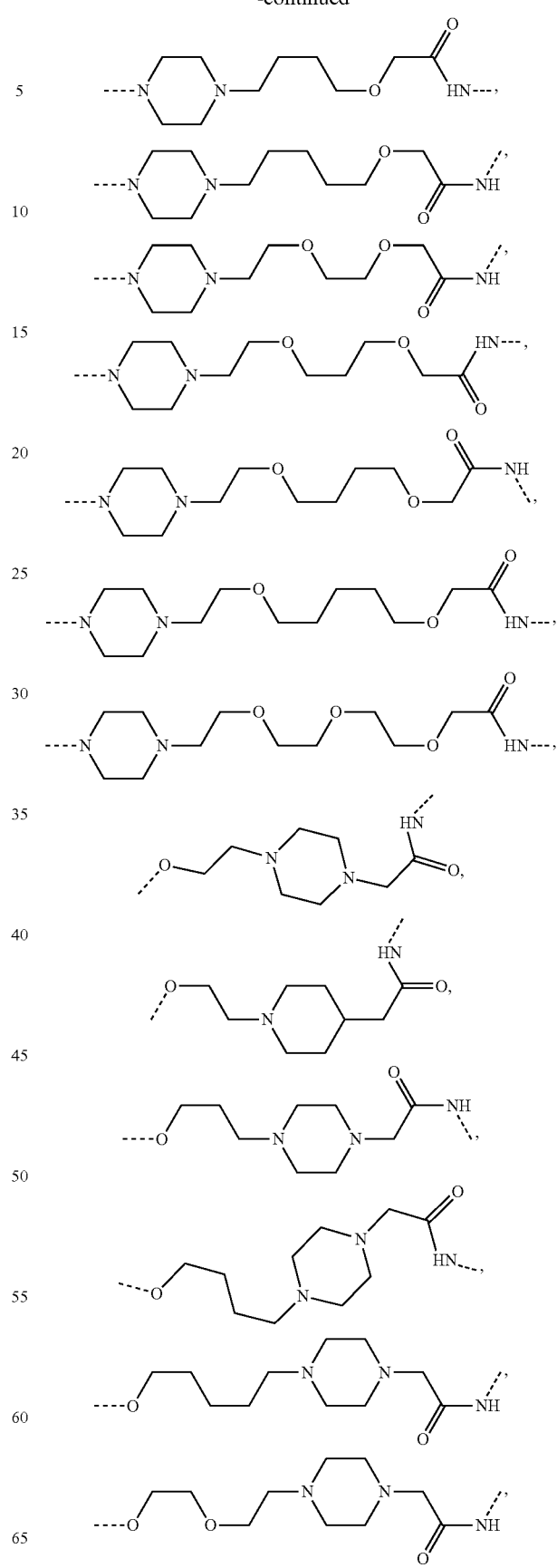

-continued
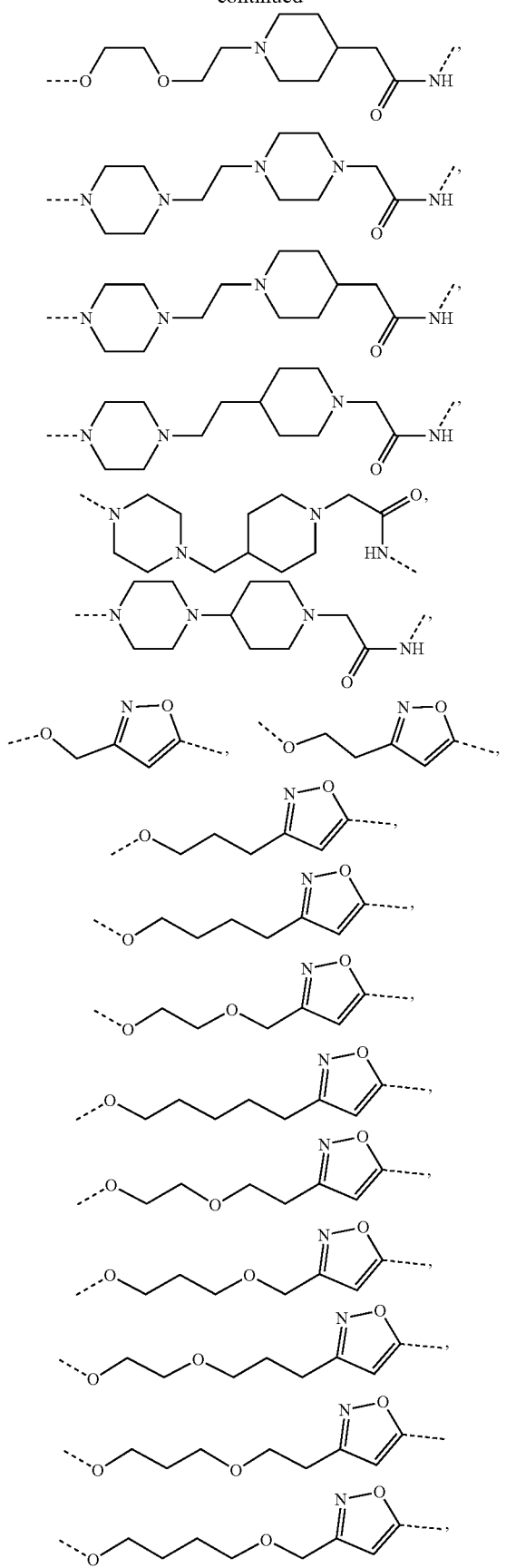
-continued
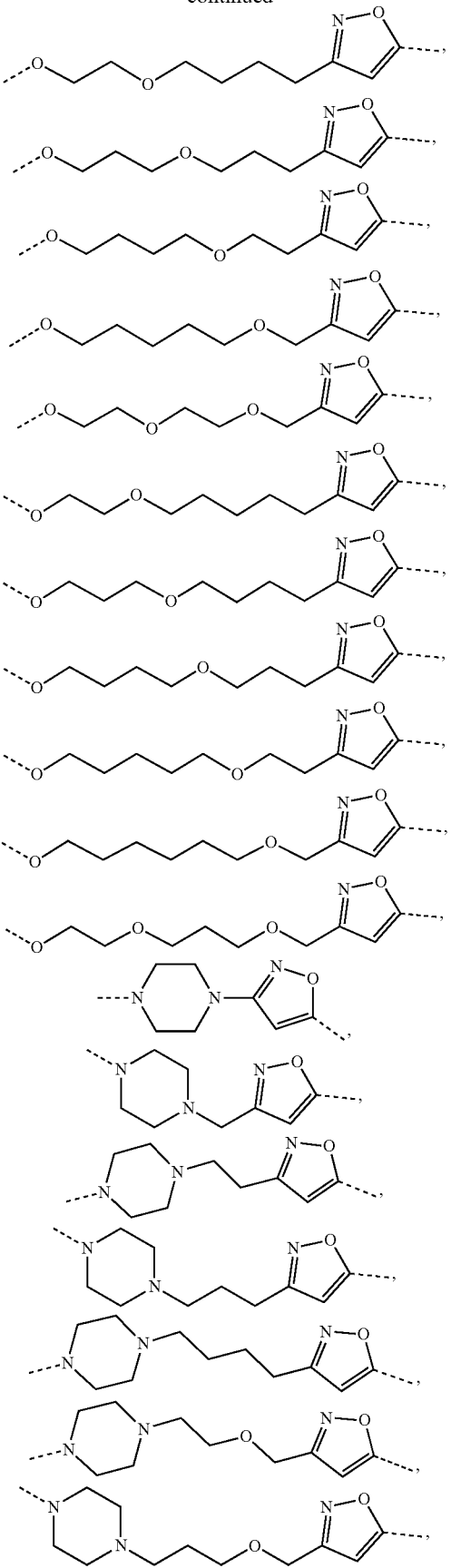

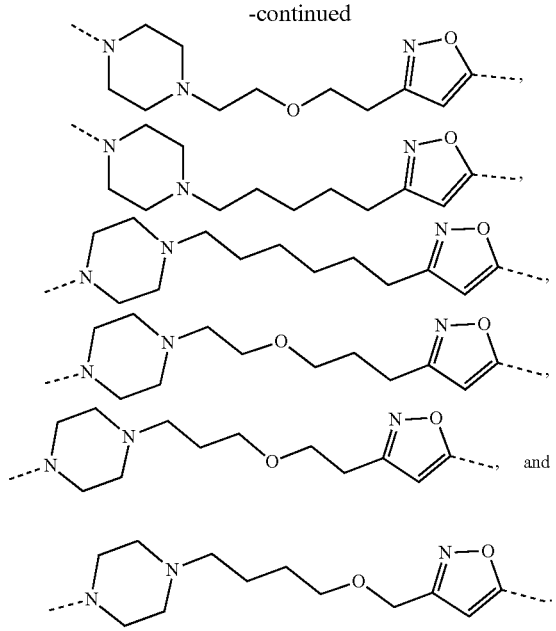
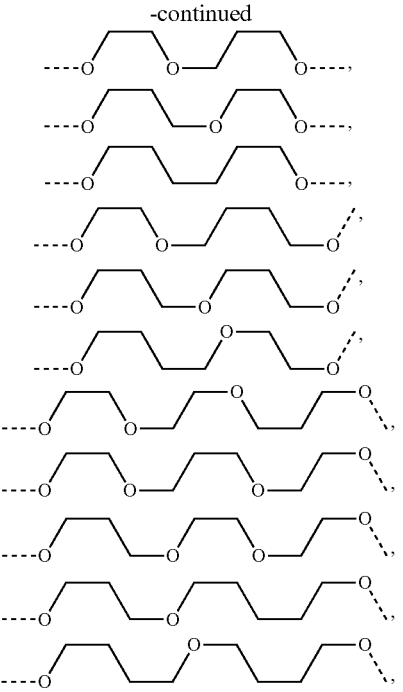
43. The bifunctional compound of claim 1, wherein the compound is represented by the chemical structure:
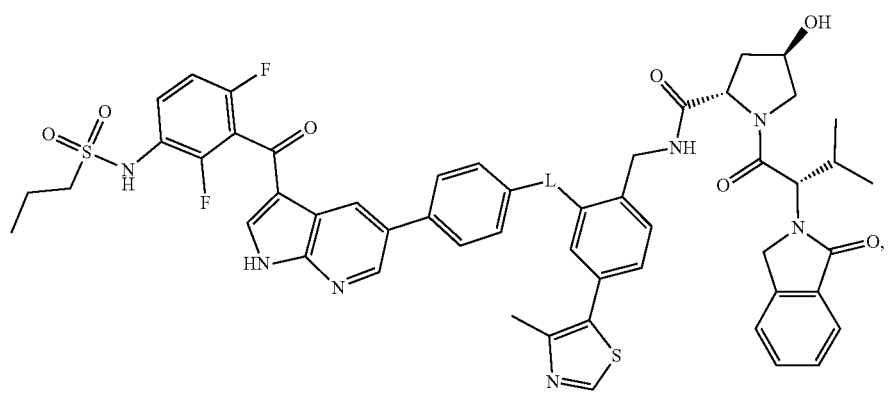
wherein the chemical linker group (L) is selected from the group consisting of:
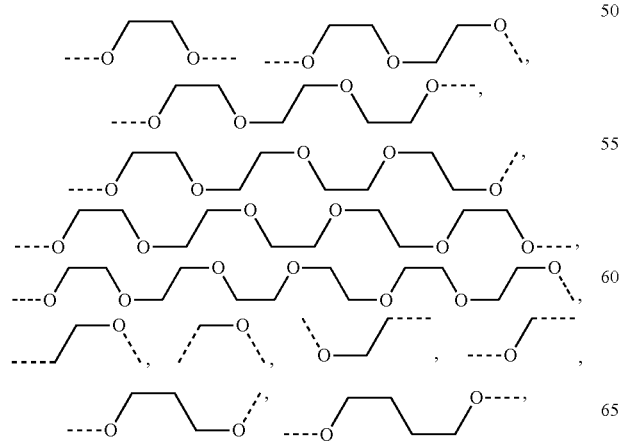
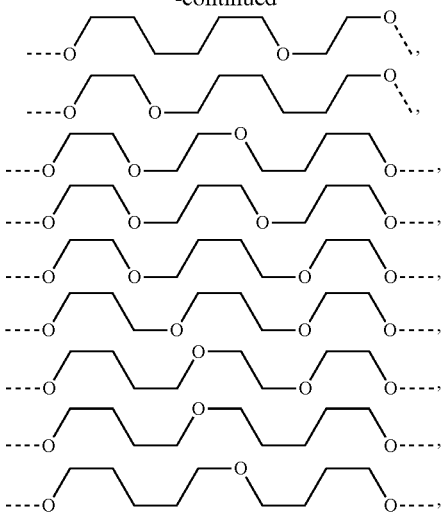

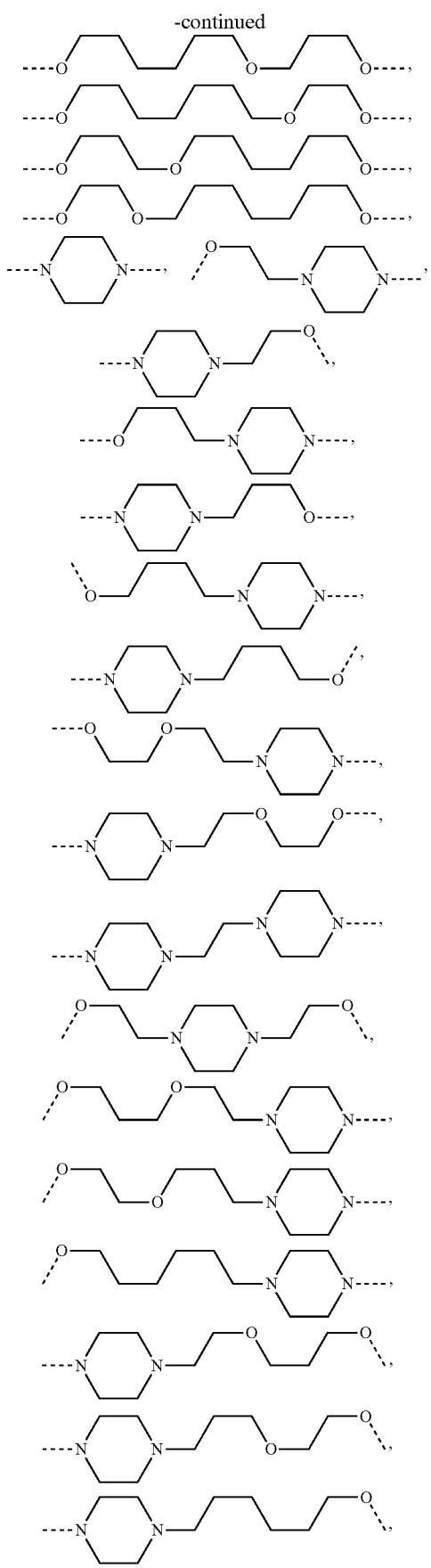
44. The bifunctional compound according to claim 1, wherein the bifunctional compound is represented by the chemical structure:

1659 1660
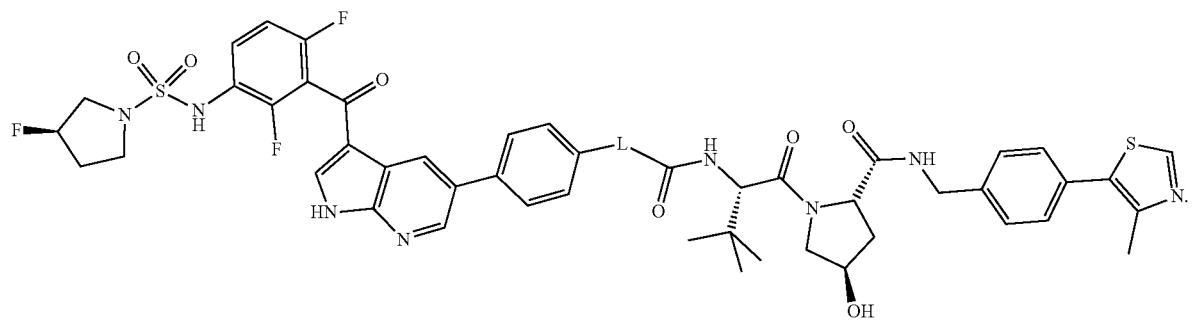
* * * * *